United States Patent
Lee et al.

(10) Patent No.: US 12,344,610 B2
(45) Date of Patent: *Jul. 1, 2025

(54) APOL1 INHIBITORS AND METHODS OF USE

(71) Applicant: Maze Therapeutics, Inc., South San Francisco, CA (US)

(72) Inventors: Patrick Sang Tae Lee, Walnut Creek, CA (US); Todd Jonathan August Ewing, Walnut Creek, CA (US); Adam Neil Reid, San Francisco, CA (US); Christopher Joseph Sinz, Walnut Creek, CA (US); Birong Zhang, Union City, CA (US); Sarah M. Bronner, Oakland, CA (US); David John Morgans, Jr., Los Altos, CA (US); Maarten Hoek, Belmont, CA (US); Victoria Anne Assimon, San Francisco, CA (US); Chris Ziebenhaus, San Francisco, CA (US); Alexander Wayne Schammel, San Diego, CA (US)

(73) Assignee: Maze Therapeutics, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/617,266

(22) Filed: Mar. 26, 2024

(65) Prior Publication Data
US 2024/0400565 A1    Dec. 5, 2024

Related U.S. Application Data

(63) Continuation of application No. 18/098,070, filed on Jan. 17, 2023, now Pat. No. 11,976,067.

(60) Provisional application No. 63/422,341, filed on Nov. 3, 2022, provisional application No. 63/400,359, filed on Aug. 23, 2022, provisional application No. 63/332,553, filed on Apr. 19, 2022, provisional application No. 63/311,668, filed on Feb. 18, 2022, provisional application No. 63/300,592, filed on Jan. 18, 2022.

(51) Int. Cl.
| C07D 471/10 | (2006.01) |
| A61K 31/438 | (2006.01) |
| C07D 487/10 | (2006.01) |
| C07D 519/00 | (2006.01) |
| C07F 9/53 | (2006.01) |

(52) U.S. Cl.
CPC ......... *C07D 471/10* (2013.01); *C07D 487/10* (2013.01); *C07D 519/00* (2013.01); *C07F 9/5333* (2013.01); *C07B 2200/05* (2013.01)

(58) Field of Classification Search
CPC ..... C07D 471/10; A61K 31/438; A61P 13/12; C12Q 1/001

USPC ............................ 546/17; 514/278; 435/184
See application file for complete search history.

(56) References Cited

U.S. PATENT DOCUMENTS

| 4,233,307 A | 11/1980 | Ono et al. |
| 5,731,317 A | 3/1998 | Lu et al. |
| 6,013,652 A | 1/2000 | Maccoss et al. |
| 7,834,000 B2 | 11/2010 | Gutierrez et al. |

(Continued)

FOREIGN PATENT DOCUMENTS

| CA | 3134585 A1 | 10/2020 |
| CN | 101851237 A | 10/2010 |

(Continued)

OTHER PUBLICATIONS

Aghajan, M. et al. (Jun. 20, 2019). "Antisense Oligonucleotide Treatment Ameliorates IFN-γ-Induced Proteinuria In APOL1-Transgenic Mice," JCI Insight 4(12):e126124, 20 pages.

(Continued)

*Primary Examiner* — Charanjit Aulakh
(74) *Attorney, Agent, or Firm* — Morrison & Foerster LLP

(57) ABSTRACT

Provided herein are compounds of formula (II):

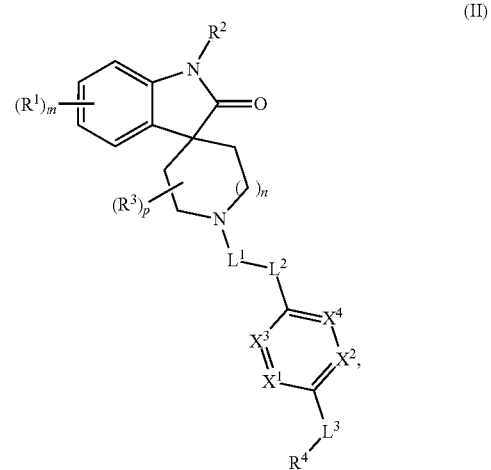

or a stereoisomer or tautomer thereof, or a pharmaceutically acceptable salt of any of the foregoing, wherein wherein m, n, p, $R^1$, $R^2$, $R^3$, $L^1$, $L^2$, $L^3$, $R^4$, $X^1$, $X^2$, $X^3$, and $X^4$ are as defined herein. Also provided are methods of preparing compounds of formula (II), or a stereoisomer or tautomer thereof, or a pharmaceutically acceptable salt of any of the foregoing. Also provided are methods of inhibiting APOL1 and methods of treating an APOL1-mediated disease, disorder, or condition in an individual.

20 Claims, No Drawings

(56) References Cited

U.S. PATENT DOCUMENTS

| | | | |
|---|---|---|---|
| 8,163,737 | B2 | 4/2012 | Anderson et al. |
| 8,383,629 | B2 | 2/2013 | Claremon et al. |
| 9,023,355 | B2 | 5/2015 | Friedman et al. |
| 9,957,229 | B2 | 5/2018 | Yao |
| 11,130,738 | B2 | 9/2021 | Cowley et al. |
| 11,672,800 | B2 | 6/2023 | Campbell |
| 11,976,067 | B2 | 5/2024 | Lee |
| 2003/0171370 | A1 | 9/2003 | Tsushima |
| 2008/0027067 | A1 | 1/2008 | Martinborough |
| 2008/0306102 | A1 | 12/2008 | Nakashima et al. |
| 2010/0280049 | A1 | 11/2010 | Stearns et al. |
| 2011/0201635 | A1 | 8/2011 | Liu et al. |
| 2012/0010402 | A1 | 1/2012 | Leahy et al. |
| 2016/0272600 | A1 | 9/2016 | Cacatian |
| 2022/0152031 | A1 | 5/2022 | Reilly |
| 2023/0011118 | A1 | 1/2023 | Dakin et al. |
| 2023/0014907 | A1 | 1/2023 | Dakin et al. |
| 2023/0201201 | A1 | 6/2023 | Skorecki et al. |
| 2023/0265096 | A1 | 8/2023 | Lee |
| 2023/0265428 | A1 | 8/2023 | Freier |
| 2023/0271945 | A1 | 8/2023 | Cao et al. |

FOREIGN PATENT DOCUMENTS

| | | |
|---|---|---|
| CN | 102516263 A | 6/2012 |
| EP | 0444945 A2 | 9/1991 |
| EP | 0450761 A1 | 10/1991 |
| WO | 2004072025 A2 | 8/2004 |
| WO | 2005046682 A1 | 5/2005 |
| WO | 2006099268 A2 | 9/2006 |
| WO | 2007136605 A2 | 11/2007 |
| WO | 2007146349 A2 | 12/2007 |
| WO | 2008142859 A1 | 11/2008 |
| WO | 2009020470 A2 | 2/2009 |
| WO | 2009061676 A2 | 5/2009 |
| WO | 2009108332 A1 | 9/2009 |
| WO | 2010054189 A1 | 5/2010 |
| WO | 2011101297 A1 | 8/2011 |
| WO | 2012112743 A1 | 8/2012 |
| WO | 2012162394 A2 | 11/2012 |
| WO | 2014085154 A1 | 6/2014 |
| WO | 2016022644 A1 | 2/2016 |
| WO | 2016071293 A2 | 5/2016 |
| WO | 2016205581 A1 | 12/2016 |
| WO | 2019115586 A1 | 6/2019 |
| WO | 2019226611 A1 | 11/2019 |
| WO | 2020131807 A1 | 6/2020 |
| WO | 2020216378 A1 | 10/2020 |
| WO | 2021133723 A2 | 7/2021 |
| WO | 2021145401 A1 | 7/2021 |
| WO | 2021154997 A1 | 8/2021 |
| WO | 2021158666 A1 | 8/2021 |
| WO | 2021178768 A1 | 9/2021 |
| WO | 2021224927 A1 | 11/2021 |
| WO | 2021252849 A1 | 12/2021 |
| WO | 2021252859 A1 | 12/2021 |
| WO | 2021252863 A1 | 12/2021 |
| WO | 2022047031 A1 | 3/2022 |
| WO | 2022067114 A1 | 3/2022 |
| WO | 2022109161 A1 | 5/2022 |
| WO | 2022125524 A1 | 6/2022 |
| WO | 2022178315 A1 | 8/2022 |
| WO | 2022251561 A2 | 12/2022 |
| WO | 2023028237 A1 | 3/2023 |
| WO | 2023086399 A1 | 5/2023 |
| WO | 2023091561 A1 | 5/2023 |
| WO | 2023101981 A1 | 6/2023 |
| WO | 2023102022 A1 | 6/2023 |
| WO | 2023141432 A2 | 7/2023 |
| WO | 2023154309 A1 | 8/2023 |
| WO | 2023154310 A1 | 8/2023 |
| WO | 2023154314 A1 | 8/2023 |
| WO | 2023154344 A1 | 8/2023 |
| WO | 2023183540 A1 | 9/2023 |
| WO | 2023194895 A1 | 10/2023 |
| WO | 2024249254 A2 | 12/2024 |
| WO | 2025015104 A2 | 1/2025 |
| WO | 2025015106 A2 | 1/2025 |
| WO | 2025019479 A1 | 1/2025 |

OTHER PUBLICATIONS

Ashley-Koch, A.E et al. (2011, e-pub. Sep. 13, 2011). "MYH9 And APOL1 Are Both Associated With Sickle Cell Disease Nephropathy," British Journal of Haematology 155(3):386-394.

Chang, J.-H. et al. (Jan. 2019). "Donor's APOL1 Risk Genotype And "Second Hits" Associated With De Novo Collapsing Glomerulopathy In Deceased Donor Kidney Transplant Recipients: A Report Of 5 Cases," American Journal of Kidney Diseases 73(1):134-139.

Chaudhary, N.S. et al. (Dec. 2019). "APOL1 Nephropathy Risk Alleles And Risk Of Sepsis In Blacks," CJASN 14:1733-1740.

Egbuna, O. et al. (Mar. 16, 2023). "Inaxaplin For Proteinuric Kidney Disease In Persons With Two APOL1 Variants," N Engl J Med 388(11):969-979.

Fleming, F.F. et al. (2010, e-pub. Aug. 30, 2010). "Nitrile-Containing Pharmaceuticals: Efficacious Roles Of The Nitrile Pharmacophore," J. Med. Chem. 53(22):7902-7917.

Freedman, B.I. et al. (Feb. 2014). "End-Stage Renal Disease In African Americans With Lupus Nephritis Is Associated With APOL1," Arthritis & Rheumatology 66(2):390-396.

Freedman, B.I. et al. (Jan. 2016). "APOL1 Genotype And Kidney Transplantation Outcomes From Deceased African American Donors," Transplantation 100(1):194-202.

Genovese, G. et al. (Aug. 13, 2010). "Association Of Trypanolytic ApoL1 Variants With Kidney Disease In African Americans," Science 329:841-845.

International Search Report and Written Opinion mailed on Jul. 11, 2023, for PCT Application No. PCT/US2023/060787, filed on Jan. 17, 2023, 12 pages.

Kopp, J.B. et al. (2011). "APOL1 Genetic Variants In Focal Segmental Glomerulosclerosis And HIV-Associated Nephropathy," J Am Soc Nephrol 22:2129-2137.

Lipkowitz, M.S. et al. (Jan. 2013, e-pub. Jul. 1, 2013). "Apolipoprotein L1 Gene Variants Associate With Hypertension-Attributed Nephropathy And The Rate Of Kidney Function Decline In African Americans," Kidney International 83(1):114-120, 16 pages.

McCarthy, G.M. et al. (2021). "Recessive, Gain-Of-Function Toxicity In An APOL1 Bac Transgenic Mouse Model Mirrors Human APOL1 Kidney Disease," Disease Models & Mechanisms 14(8):1-17.

Parsa, A. et al. (Dec. 5, 2013, e-pub. Nov. 9, 2013). "APOL1 Risk Variants, Race, And Progression Of Chronic Kidney Disease," New England Journal of Medicine 369(23):2183-2196.

Pays, E. et al. (Aug. 2014). "The Molecular Arms Race Between African Trypanosomes And Humans," Nature Reviews Microbiology 12:575-584.

Powe, N.R. (Mar. 16, 2023). "A Step Forward for Precision Equity in Kidney Disease," N Engl J Med 388 (11):1043-1044.

PubChem Substance Record. (May 25, 2018). "SID 365369291," 5 pages.

Reidy, K.J. et al. (Sep. 6, 2018). "Fetal-Not Maternal-APOL1 Genotype Associated With Risk For Preeclampsia In Those With African Ancestry," The American Journal of Human Genetics 103:367-376.

Shetty, A.A. et al. (2021). "COVID-19-Associated Glomerular Disease," Journal of the American Society of Nephrology 32(1):33-40.

Tzur, S. et al. (2010, e-pub. Jul. 16, 2020). "Missense Mutations In The APOL1 Gene Are Highly Associated With End Stage Kidney Disease Risk Previously Attributed To The MYH9 Gene," Human Genetics 128:345-350.

U.S. Appl. No. 18/603,187, Lee et al., filed Mar. 12, 2024.

Wakashin, H. et al. (2020, e-pub. Aug. 27, 2020). "APOL1 Renal Risk Variants Exacerbate Podocyte Injury By Increasing Inflammatory Stress," BMC Nephrology 21(371):1-13.

(56) References Cited

OTHER PUBLICATIONS

Williams, W.W. et al. (Mar. 16, 2023). "Inhibiting APOL1 to Treat Kidney Disease," N Engl J Med 388 (11):1045-1049.

Zhao, K. (2016). "Asymmetric Synthesis of 3,3'-pyrrolidinyl-dispirooxindoles via a One-Pot Organocatalytic Mannich/Deprotection/aza-Michael Sequence," Chem. Commun. 52:2249-2252.

Zhou, Y. (Feb. 7, 2017). "Highly Diastereo- and Enantioselective Synthesis of Spirooxindole-Cyclohexaneamides Through N,N'-dioxide/Ni(ii)-catalyzed Diels-Alder Reactions," Chemical Communications 53(12):2060-2063.

International Search Report and Written Opinion mailed on Aug. 28, 2024, for PCT Application No. PCT/US2024/030772, filed on May 23, 2024, 15 pages.

PubChem. (Dec. 1, 2012). "1'-(2-Phenoxyethyl)-1-methyl-2-oxo-indoline-3-spiro-4'-piperidine hydrochloride," PubChem CID 70594460, 10 pages.

PubChem. (Mar. 21, 2013). "1'-ethylspiro[1H-pyrrolo[2,3-b]pyridine-3,4'-piperidine]-2-one," PubChem CID 71056499, 9 pages.

PubChem. (Mar. 30, 2012). "1'-[2-(4-fluorophenoxy)ethyl]spiro[indole-3,4'-piperidin]-2(1H)-one," PubChem CID 56910835, 8 pages.

International Preliminary Report on Patentability issued Jul. 23, 2024, mailed on Jul. 11, 2023, for International Application No. PCT/US2023/060787, filed on Jan. 17, 2023, 7 pages.

International Search Report and Written Opinion mailed on Dec. 10, 2024, for PCT Application No. PCT/US2024/037472, filed on Jul. 10, 2024, 13 pages.

International Search Report and Written Opinion mailed on Dec. 30, 2024, for PCT Application No. PCT/US2024/037470, filed on Jul. 10, 2024, 12 pages.

International Search Report and Written Opinion mailed on Oct. 25, 2024, for PCT Application No. PCT/US2024/038170, filed on Jul. 16, 2024, 12 pages.

APOL1 INHIBITORS AND METHODS OF USE

CROSS-REFERENCE TO RELATED APPLICATIONS

This application is a continuation application of U.S. patent application Ser. No. 18/098,070, filed Jan. 17, 2023, which claims priority to U.S. Provisional Application Ser. No. 63/300,592, filed Jan. 18, 2022, U.S. Provisional Application Ser. No. 63/311,668, filed Feb. 18, 2022, U.S. Provisional Application Ser. No. 63/332,553, filed Apr. 19, 2022, U.S. Provisional Application Ser. No. 63/400,359, filed Aug. 23, 2022, and U.S. Provisional Application Ser. No. 63/422,341, filed Nov. 3, 2022, each of which is hereby incorporated herein by reference in its entirety.

BACKGROUND OF THE INVENTION

Apolipoprotein L1 (APOL1) is a pore forming innate immunity factor, protecting individuals from trypanosome parasites (Vanhamme, L. et al. *Nature* (2003) 422, 83-87). The secreted form of APOL1 circulates in blood as part of distinct high-density lipoprotein (HDL) complexes, known as trypanosome lytic factors (TLFs) (Rifkin, M. R. *Proc. Natl. Acad. Sci. USA*. (1978) 75, 3450-3454; Raper, J. et al. *Infect. Immun.* (1999) 67, 1910-1916). TLFs are internalized by the parasites through endocytosis (Hager, K. M. et al. *J. Cell Biol.* (1994) 126, 155-167). Within trypanosomes, APOL1 forms cation pores, causing ion flux, swelling, and eventual lysis (Rifkin, M. R. *Exp. Parasitol.* (1984) 58, 81-93; Molina-Portela, M. P. et al. *Mol. Biochem. Parasitol.* (2005) 144, 218-226; Pérez-Morga, D. et al. *Science*. (2005) 309, 469-472; Thomson, R. & Finkelstein, A. *Proc. Natl. Acad. Sci. USA*. (2015) 112, 2894-2899).

Several *Trypanosoma brucei* subspecies (*T.b. rhodesiense* and *T.b. gambiense*) developed resistance mechanisms to APOL1-dependent killing (Pays, E. et al. *Nat. Rev. Microbiol.* (2014) 12, 575-584). Positive selection resulted in APOL1 variants, G1 (S342G, I384M) and G2 (N388Δ, Y389Δ), capable of interfering with these resistance mechanisms (Genovese, G. et al. *Science*. (2010) 329, 841-845). However, individuals with any binary combination of these variants (G1/G1, G2/G2, or G1/G2), have a greater risk of developing a variety of chronic kidney diseases, including focal segmental glomerulosclerosis (FSGS), hypertension-attributed kidney disease, human immunodeficiency virus-associated nephropathy (HIVAN) (Genovese, G. et al. *Science*. (2010) 329, 841-845; Tzur, S. et al. *Hum. Genet.* (2010) 128, 345-350; Kopp, J. B. et al. *J. Am. Soc. Nephrol.* (2011) 22, 2129-2137), sickle cell nephropathy (Ashley-Koch, A. E. et al. *Br. J. Haematol.* (2011) 155, 386-394), lupus nephritis (Freedman, B. I. et al. *Arthritis Rheumatol.* (2014) 66, 390-396), and an increased rate of Glomerular Filtration Rate (GFR) decline in diabetic kidney disease (Parsa, A. et al. *N. Engl. J. Med.* (2013) 369, 2183-2196). The APOL1 high-risk genotype has also been associated with COVID-19 associated nephropathy and other viral nephropathies (Shetty, A. et al. *J. Am. Soc. Nephrol.* (2021) 32, 33-40; Chang, J. H. et al. *Am. J. Kidney Dis.* (2019) 73, 134-139). Moreover, decreased renal allograft survival has been observed after deceased-donor kidney transplantations from APOL1 high-risk genotype donors (Freedman, B. I. et al. *Transplantation*. (2016) 100, 194-202). In addition, having two APOL1 risk alleles increases risk for preeclampsia (Reidy, K. J. et al. *Am. J. Hum. Genet.* (2018) 103, 367-376) and sepsis (Chaudhary, N. S. et al. *Clin. J. Am. Soc. Nephrol.* (2019) 14, 1733-1740). There are no approved therapies for APOL1-associated nephropathy, and patients are treated based on the standard of care for their underlying form of chronic kidney disease. This presents a clear unmet need for therapies targeted to people with the APOL1 high-risk genotype.

Numerous studies have shown that APOL1 risk variants are toxic when overexpressed in human cells (Wan, G. et al. *J. Biol. Chem.* (2008) 283, 21540-21549; Lan, X. et al. *Am. J. Physiol. Renal Physiol.* (2014) 307, F326-F336; Olabisi, O. A. et al. *Proc. Natl. Acad. Sci. USA*. (2016) 113, 830-837; Ma, L. et al. *J. Am. Soc. Nephrol.* (2017) 28, 1093-1105; Lannon, H. et al. *Kidney Int.* (2019) 96, 1303-1307). Recent findings suggest that this toxicity is associated with APOL1 pore function (Giovinazzo, J. A. et al. *eLife*. (2020) 9, e51185). Thus, there is a need to develop compounds suitable for inhibiting APOL1 activity and methods for inhibiting the activity of APOL1 using such compounds.

BRIEF SUMMARY OF THE INVENTION

This disclosure describes compounds and compositions that may be useful for the treatment of APOL1-mediated diseases, including a variety of chronic kidney diseases such as FSGS, hypertension-attributed kidney disease, HIVAN, sickle cell nephropathy, lupus nephritis, diabetic kidney disease, viral nephropathy, COVID-19 associated nephropathy, and APOL1-associated nephropathy. The compounds and compositions may treat other APOL1-mediated disorders such as preeclampsia and sepsis. Additionally, for individuals with the APOL1 high-risk genotype, the disclosed compounds and may prevent the onset of non-diabetic renal disease and/or delaying the progression of any form of chronic kidney disease. The disclosed chemical matter may also prevent and/or delay progressive renal allograft loss in patients who have received a kidney transplant from a high-risk APOL1 genotype donor.

In one aspect, provided is a compound of formula (II):

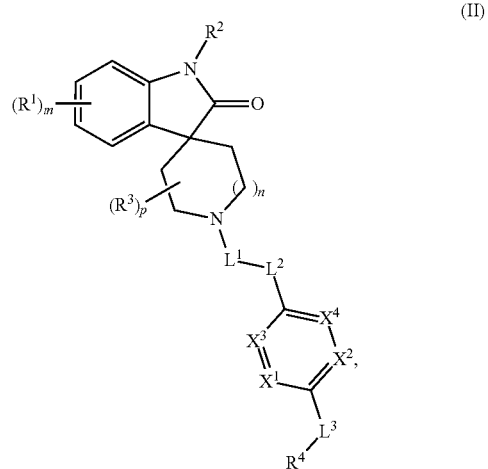

or a stereoisomer or tautomer thereof, or a pharmaceutically acceptable salt of any of the foregoing, wherein:

m is an integer from 0 to 4;

n is an integer from 0 to 2;

p is an integer from 0 to 10;

$R^1$, if present is, independently at each occurrence selected from the group consisting of halo, —CN, $C_{1-6}$alkoxy, and $C_{1-6}$alkyl, wherein the $C_{1-6}$alkoxy of $R^1$ is optionally substituted with one or more halo, and the $C_{1-6}$alkyl of $R^1$ is optionally substituted with one or more halo;

$R^2$ is H, $C_{1-6}$alkyl, $C_{3-10}$cycloalkyl, or 3-15 membered heterocyclyl, wherein the $C_{1-6}$alkyl of $R^2$ is optionally substituted with one or more deuterium, halo, —OH, —NH$_2$, or $C_{1-6}$alkoxy, and the $C_{3-10}$cycloalkyl of $R^2$ is optionally substituted with one or more —OH;

$R^3$, if present, is $C_{1-6}$alkyl;

$L^1$ is $C_{1-6}$alkylene, wherein the $C_{1-6}$alkylene of $L^1$ is optionally substituted with one or more deuterium or $C_{1-6}$alkyl, and wherein the $C_{1-6}$alkyl is further optionally substituted with one or more —OH or $C_{1-6}$alkoxy;

$L^2$ is O or N($R^x$), wherein $R^x$ is H or $C_{1-6}$alkyl; and either (1) $L^3$ is absent or is O, $C_{3-10}$cycloalkyl, 3-10 membered heterocyclyl, or $C_{1-6}$alkylene, wherein the $C_{3-10}$cycloalkyl of $L^3$ is optionally substituted with one or more —OH or $C_{1-6}$alkyl, the $C_{1-6}$alkylene of $L^3$ is optionally substituted with one or more —OH or $C_{1-6}$alkyl, wherein the $C_{1-6}$alkyl is optionally substituted with one or more —OH, and the 3-10 membered heterocyclyl of $L^3$ is optionally substituted with one or more —OH or $C_{1-6}$alkyl;

$X^1$ and $X^2$ are each independently N or C($R^5$); and $R^4$ is:

(i) —S(O)$_2$—$R^a$;

(ii) 5-20 membered heteroaryl, wherein the 5-20 membered heteroaryl of $R^4$ is optionally substituted with one or more $C_{1-6}$alkyl;

(iii) —N($R^d$)$_2$, wherein $R^d$ is independently at each occurrence H, $C_{1-6}$ alkyl, or —S(O)$_2$—$R^a$, wherein the $C_{1-6}$alkyl of $R^d$ is optionally substituted with one or more —OH, (iv) —NS(O)—($C_{1-6}$alkyl)$_2$, wherein the $C_{1-6}$alkyl is optionally substituted with one or more —OH, (v) —C(O)—N($R^e$)$_2$ wherein $R^e$ is independently at each occurrence H, $C_{1-6}$ alkyl, or 3-10 membered heterocycle, wherein the 3-10 membered heterocycle of $R^e$ is optionally substituted with one or more oxo, or both $R^e$ together with the N to which they are attached are taken together to form a 3-10 membered heterocyclyl, wherein the 3-10 membered heterocyclyl is optionally substituted with one or more halo, oxo, —OH, NH$_2$, —NH—S(O)$_2$—$R^a$, or —S(O)$_2$—$R^a$, (vi) 3-10 membered heterocyclyl optionally substituted with one or more $C_{1-6}$alkyl, —OH, oxo or —S(O)$_2$$R^a$, (vii) —S(O)—N($C_{1-6}$alkyl)-($C_{1-6}$alkyl), (viii) —CN, (ix) —(CH$_2$)$_q$OH, wherein q is an integer from 0-6, (x) —C(O)—$C_{1-6}$alkyl, or (xi) —P(O)($C_{1-6}$alkyl)$_2$;

or (2) $L^3$ is absent; and one of $X^1$ and $X^2$ is N or C($R^5$); and the other of $X^1$ and $X^2$ is N or C that is taken together with $R^4$, and the atoms to which they are attached, to form a 5-10 membered heterocyclyl or a 5-20 membered heteroaryl, wherein the 5-10 membered heterocyclyl is optionally substituted with one or more $R^b$, wherein $R^b$ is, independently at each occurrence, selected from the group consisting of —OH, halo, oxo, $C_{1-6}$alkyl, —C(O)—$C_{1-6}$alkyl, —C(O)—NH$_2$, —C(O)—NH($C_{1-6}$alkyl), —C(O)—N($C_{1-6}$alkyl)$_2$, —S(O)$_2$—$R^a$, $C_{3-10}$cycloalkyl, and 3-10 membered heterocyclyl, wherein the $C_{1-6}$alkyl of $R^b$ is optionally substituted with one or more halo, OH, —S(O)$_2$—$C_{1-6}$alkyl, or $C_{3-10}$cycloalkyl, and wherein the $C_{3-10}$cycloalkyl of the $C_{1-6}$alkyl of $R^b$ is further optionally substituted with one or more $C_{1-6}$alkyl or —OH and the $C_{3-10}$cycloalkyl of $R^b$ is optionally substituted with one or more —OH, $C_{3-10}$cycloalkyl, or $C_{1-6}$alkyl, and wherein the $C_{1-6}$alkyl of the $C_{3-10}$cycloalkyl of $R^b$ is further optionally substituted with one or more —OH, deuterium, or halo, and the 5-20 membered heteroaryl is optionally substituted with one or more $R^c$, wherein $R^c$ is, independently at each occurrence, selected from the group consisting of halo, $C_{1-6}$alkyl, —C(O)—$C_{1-6}$alkyl, —C(O)—NH$_2$, —C(O)—NH($C_{1-6}$alkyl), —C(O)—N($C_{1-6}$alkyl)$_2$, —S(O)$_2$—$R^a$, $C_{3-10}$cycloalkyl, and 3-10 membered heterocyclyl, wherein the $C_{1-6}$alkyl of $R^c$ is optionally substituted with one or more —S(O)$_2$—$C_{1-6}$alkyl, the $C_{3-10}$cycloalkyl of $R^c$ is optionally substituted with one or more —OH or $C_{1-6}$alkyl, and the 3-10 membered heterocyclyl of $R^c$ is optionally substituted with one or more —OH or $C_{1-6}$alkyl, and wherein the $C_{1-6}$alkyl of the 3-10 membered heterocyclyl of $R^c$ is further optionally substituted with one or more —OH;

$R^a$ is, independently at each occurrence:

(i) $C_{1-6}$alkyl optionally substituted with one or more halo, —OH, —S(O)$_2$—$C_{1-6}$alkyl, or —N($C_{1-6}$alkyl)-C(O)—$C_{1-6}$alkyl, (ii) $C_{3-10}$cycloalkyl optionally substituted with one or more —OH, —C(O)$_2$—$C_{1-6}$alkyl, —C(O)—NH($C_{1-6}$alkyl), —C(O)—N($C_{1-6}$alkyl)$_2$, or —C(O)—$C_{3-10}$heterocyclyl, or $C_{1-6}$alkyl, wherein the $C_{1-6}$alkyl is optionally substituted with one or more —OH, (iii) 3-10 membered heterocyclyl optionally substituted with one or more $C_{1-6}$alkyl, or (iv) NH($C_{1-6}$alkyl);

$R^5$ is, independently at each occurrence, H, halo, —CN, 3-10 membered heterocyclyl, $C_{1-6}$alkyl, or $C_{1-6}$alkoxy, wherein the $C_{1-6}$alkyl of $R^5$ is optionally substituted with one or more halo or —OH, and the $C_{1-6}$alkoxy of $R^5$ is optionally substituted with one or more halo;

$X^3$ is N or C($R^6$)

$X^4$ is N or C($R^7$);

and $R^6$ and $R^7$ are each independently H or halo.

In one aspect, provided is a compound of formula (I'):

(I')

or a stereoisomer or tautomer thereof, or a pharmaceutically acceptable salt of any of the foregoing, wherein:
m is an integer from 0 to 4;
n is an integer from 0 to 2;
p is an integer from 0 to 10;
$R^1$, if present is, independently at each occurrence selected from the group consisting of halo, —CN, $C_{1-6}$alkoxy, or $C_{1-6}$alkyl, wherein
  the $C_{1-6}$alkoxy of $R^1$ is optionally substituted with one or more halo, and
  the $C_{1-6}$alkyl of $R^1$ is optionally substituted with one or more halo;
$R^2$ is H, $C_{1-6}$alkyl, $C_{3-10}$cycloalkyl, or 3-15 membered heterocyclyl, wherein
  the $C_{1-6}$alkyl of $R^2$ is optionally substituted with one or more halo, —OH, —NH$_2$, or $C_{1-6}$alkoxy, and
  the $C_{3-10}$cycloalkyl of $R^2$ is optionally substituted with one or more —OH;
$R^3$, if present, is $C_{1-6}$alkyl;
$L^1$ is $C_{1-6}$alkylene, wherein the $C_{1-6}$alkylene of $L^1$ is optionally substituted with one or more $C_{1-6}$alkyl, and wherein the $C_{1-6}$alkyl is further optionally substituted with one or more —OH or $C_{1-6}$alkoxy;
$L^2$ is O or N($R^x$), wherein $R^x$ is H or $C_{1-6}$alkyl; and
either
(1) $L^3$ is absent or is O, $C_{3-10}$cycloalkyl, 3-10 membered heterocyclyl, or $C_{1-6}$alkylene, wherein
  the $C_{3-10}$cycloalkyl is optionally substituted with one or more —OH or $C_{1-6}$alkyl,
  the $C_{1-6}$alkylene of $L^3$ is optionally substituted with one or more —OH or $C_{1-6}$alkyl, and
  the 3-10 membered heterocyclyl is optionally substituted with one or more —OH;
$X^1$ and $X^2$ are each independently N or C($R^5$); and
$R^4$ is:
(i) —S(O)$_2$—$R^a$;
(ii) 5-20 membered heteroaryl, wherein the 5-20 membered heteroaryl of $R^4$ is optionally substituted with one or more $C_{1-6}$alkyl;
(iii) —N($R^d$)$_2$, wherein $R^d$ is independently at each occurrence H, $C_{1-6}$ alkyl, or —S(O)$_2$—$R^a$, wherein the $C_{1-6}$alkyl of $R^d$ is optionally substituted with one or more —OH,
(iv) —NS(O)—($C_{1-6}$alkyl)$_2$, wherein the $C_{1-6}$alkyl is optionally substituted with one or more —OH,
(v) —C(O)—N($R^e$)$_2$ wherein $R^e$ is independently at each occurrence H, $C_{1-6}$ alkyl, or 3-10 membered heterocycle, wherein the 3-10 membered heterocycle is optionally substituted with one or more oxo, or both $R^e$ together with the N to which they are attached are taken together to form a 3-10 membered heterocyclyl, wherein the 3-10 membered heterocyclyl is optionally substituted with one or more halo, oxo, —OH, NH$_2$, —NH—S(O)$_2$—$R^a$, or —S(O)$_2$—$R^a$,
(vi) 3-10 membered heterocyclyl optionally substituted with one or more $C_{1-6}$alkyl, —OH, oxo, or —S(O)$_2R^a$,
(vii) —S(O)—N($C_{1-6}$alkyl)-($C_{1-6}$alkyl),
(viii) —CN,
(ix) —(CH$_2$)$_q$OH, wherein q is an integer from 0-6,
(x) —C(O)—$C_{1-6}$alkyl, or
(xi) —P(O)($C_{1-6}$alkyl)$_2$;
or
(2) $L^3$ is absent; and
  one of $X^1$ and $X^2$ is N or C($R^5$); and
  the other of $X^1$ and $X^2$ is N or C that is taken together with $R^4$ and the atoms to which they are attached to form a 5-10 membered heterocyclyl or a 5-20 membered heteroaryl, wherein
    the 5-10 membered heterocyclyl is optionally substituted with one or more $R^b$, wherein $R^b$ is, independently at each occurrence, selected from the group consisting of halo, oxo, $C_{1-6}$alkyl, —C(O)—$C_{1-6}$alkyl, —C(O)—NH$_2$, —C(O)—NH($C_{1-6}$alkyl), —C(O)—N($C_{1-6}$alkyl)$_2$, —S(O)$_2$—$R^a$, $C_{3-10}$cycloalkyl, and 3-10 membered heterocyclyl, wherein
      the $C_{1-6}$alkyl of $R^b$ is optionally substituted with one or more halo, OH, —S(O)$_2$—$C_{1-6}$alkyl, or $C_{3-10}$cycloalkyl, and
      wherein the $C_{3-10}$cycloalkyl of the $C_{1-6}$alkyl of $R^b$ is further optionally substituted with one or more $C_{1-6}$alkyl or —OH and
      the $C_{3-10}$cycloalkyl of $R^b$ is optionally substituted with one or more —OH, $C_{3-10}$cycloalkyl, or $C_{1-6}$alkyl, and
      wherein the $C_{1-6}$alkyl of the $C_{3-10}$cycloalkyl of $R^b$ is further optionally substituted with one or more —OH, and
    the 5-20 membered heteroaryl is optionally substituted with one or more $R^c$, wherein $R^c$ is, independently at each occurrence, selected from the group consisting of halo, $C_{1-6}$alkyl, —C(O)—$C_{1-6}$alkyl, —C(O)—NH$_2$, —C(O)—NH($C_{1-6}$alkyl), —C(O)—N($C_{1-6}$alkyl)$_2$, —S(O)$_2$—$R^a$, $C_{3-10}$cycloalkyl, and 3-10 membered heterocyclyl, wherein
      the $C_{1-6}$alkyl of $R^c$ is optionally substituted with one or more —S(O)$_2$—$C_{1-6}$alkyl,
      the $C_{3-10}$cycloalkyl of $R^c$ is optionally substituted with one or more —OH or $C_{1-6}$alkyl,
      and the 3-10 membered heterocyclyl of $R^c$ is optionally substituted with one or more —OH or $C_{1-6}$alkyl, and
      wherein the $C_{1-6}$alkyl of the 3-10 membered heterocyclyl of $R^c$ is further optionally substituted with one or more —OH;
$R^a$ is, independently at each occurrence:
(i) $C_{1-6}$alkyl optionally substituted with one or more halo, —OH, —S(O)$_2$—$C_{1-6}$alkyl, or —N($C_{1-6}$alkyl)-C(O)—$C_{1-6}$alkyl, (ii) $C_{3-10}$cycloalkyl optionally substituted with one or more —OH, —C(O)$_2$—$C_{1-6}$alkyl, —C(O)—NH($C_{1-6}$alkyl), —C(O)—N($C_{1-6}$alkyl)$_2$, or —C(O)—$C_{3-10}$heterocyclyl, or $C_{1-6}$alkyl, wherein the $C_{1-6}$alkyl is optionally substituted with one or more —OH, or (iii) 3-10 membered heterocyclyl optionally substituted with one or more $C_{1-6}$alkyl;

$R^5$ is, independently at each occurrence, H, halo, —CN, 3-10 membered heterocyclyl, $C_{1-6}$alkyl, or $C_{1-6}$alkoxy, wherein the $C_{1-6}$alkyl of $R^5$ is optionally substituted with one or more halo, or —OH and wherein the $C_{1-6}$alkoxy of $R^5$ is optionally substituted with one or more halo; and $R^6$ and $R^7$ are each independently H or halo.

In one aspect, provided is a compound of formula (I):

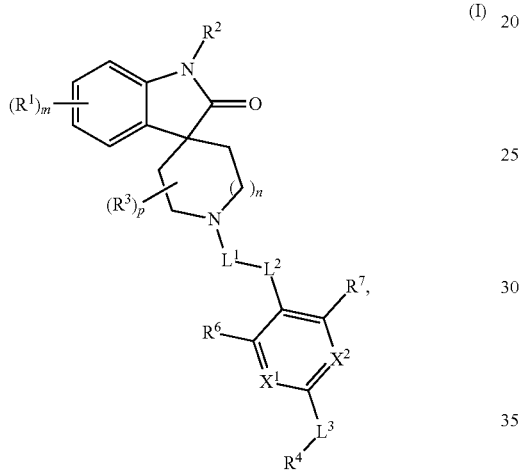

or a stereoisomer or tautomer thereof, or a pharmaceutically acceptable salt of any of the foregoing, wherein:

m is an integer from 0 to 4;
n is an integer from 0 to 2;
p is an integer from 0 to 10;
$R^1$ if present is, independently at each occurrence, selected from the group consisting of halo, —CN, $C_{1-6}$alkoxy or —$C_{1-6}$alkyl, wherein
  the $C_{1-6}$alkoxy of $R^1$ is optionally substituted with one or more halo, and
  the $C_{1-6}$alkyl of $R^1$ is optionally substituted with one or more halo;
$R^2$ is H, $C_{1-6}$alkyl, $C_{3-10}$cycloalkyl, or 3-15 membered heterocyclyl, wherein
  the $C_{1-6}$alkyl of $R^2$ is optionally substituted with one or more halo, —OH, —NH$_2$, or $C_{1-6}$alkoxy, and
  the $C_{3-10}$cycloalkyl of $R^2$ is optionally substituted with one or more —OH;
$R^3$, if present, is $C_{1-6}$alkyl;
$L^1$ is $C_{1-6}$alkylene, wherein the $C_{1-6}$alkylene of $L^1$ is optionally substituted with one or more $C_{1-6}$alkyl, and wherein the $C_{1-6}$alkyl is further optionally substituted with one or more —OH or $C_{1-6}$alkoxy;
$L^2$ is O or N($R^x$), wherein $R^x$ is H or $C_{1-6}$alkyl; and either
(1) $L^3$ is absent or is O, $C_{3-10}$cycloalkyl, 3-10 membered heterocyclyl, or $C_{1-6}$alkylene, wherein
  the $C_{1-6}$alkylene of $L^3$ is optionally substituted with one or more $C_{1-6}$alkyl, and
  the 3-10 membered heterocyclyl is optionally substituted with one or more —OH;

$X^1$ and $X^2$ are each independently N or C($R^5$); and
$R^4$ is:
(i) —S(O)$_2$—$R^a$,
(ii) 5-20 membered heteroaryl, wherein the 5-20 membered heteroaryl of $R^4$ is optionally substituted with one or more $C_{1-6}$alkyl,
(iii) —N($R^d$)$_2$, wherein $R^d$ is independently at each occurrence H, $C_{1-6}$ alkyl, or —S(O)$_2$—$R^a$, wherein the $C_{1-6}$alkyl of $R^d$ is optionally substituted with one or more —OH,
(iv) —NS(O)—($C_{1-6}$alkyl)$_2$, wherein the $C_{1-6}$alkyl of $R^d$ is optionally substituted with one or more —OH,
(v) —C(O)—N($R^e$)$_2$ wherein $R^e$ is independently at each occurrence H, $C_{1-6}$ alkyl, or 3-10 membered heterocycle, wherein the 3-10 membered heterocycle is optionally substituted with one or more oxo, or both $R^e$ together with the N to which they are attached are taken together to form a 3-10 membered heterocyclyl, wherein the 3-10 membered heterocyclyl is optionally substituted with one or more halo, oxo, —OH, NH$_2$, NH—S(O)$_2$—$R^a$, or —S(O)$_2$—$R^a$,
(vi) 3-10 membered heterocyclyl optionally substituted with one or more $C_{1-6}$alkyl or oxo,
(vii) —S(O)—N($C_{1-6}$alkyl)-($C_{1-6}$alkyl), or
(viii) —CN;

or
(2) $L^3$ is absent; and
one of $X^1$ and $X^2$ is N or C($R^5$); and
the other of $X^1$ and $X^2$ is N or C that is taken together with $R^4$, and the atoms to which they are attached, to form a 5-10 membered heterocyclyl or a 5-20 membered heteroaryl, wherein
  the 5-10 membered heterocyclyl is optionally substituted with one or more $R^b$, wherein $R^b$ is, independently at each occurrence, selected from the group consisting of halo, oxo, $C_{1-6}$alkyl, —C(O)—$C_{1-6}$alkyl, —C(O)—NH$_2$, —C(O)—NH($C_{1-6}$alkyl), —C(O)—N($C_{1-6}$alkyl)$_2$, —S(O)$_2$—$R^a$, $C_{3-10}$cycloalkyl, and 3-10 membered heterocyclyl, wherein
    the $C_{1-6}$alkyl of $R^b$ is optionally substituted with one or more halo, OH, or —S(O)$_2$—$C_{1-6}$alkyl, and
    the $C_{3-10}$cycloalkyl of $R^b$ is optionally substituted with one or more —OH, and
  the 5-20 membered heteroaryl is optionally substituted with one or more $R^c$, wherein $R^c$ is, independently at each occurrence, selected from the group consisting of halo, $C_{1-6}$alkyl, —C(O)—$C_{1-6}$alkyl, —C(O)—NH$_2$, —C(O)—NH($C_{1-6}$alkyl), —C(O)—N($C_{1-6}$alkyl)$_2$, —S(O)$_2$—$R^a$, $C_{3-10}$cycloalkyl, and 3-10 membered heterocyclyl, wherein
    the $C_{1-6}$alkyl of $R^c$ is optionally substituted with one or more —S(O)$_2$—$C_{1-6}$alkyl, and
    the $C_{3-10}$cycloalkyl of $R^c$ is optionally substituted with one or more —OH;

$R^a$ is, independently at each occurrence:
(i) $C_{1-6}$alkyl optionally substituted with one or more halo, —OH, —S(O)$_2$—$C_{1-6}$alkyl, or —N($C_{1-6}$alkyl)-C(O)—$C_{1-6}$alkyl, or
(ii) $C_{3-10}$cycloalkyl optionally substituted with one or more —OH, —C(O)$_2$—$C_{1-6}$alkyl, —C(O)—NH ($C_{1-6}$alkyl), —C(O)—N($C_{1-6}$alkyl)$_2$, —C(O)—$C_{3-10}$heterocyclyl, or $C_{1-6}$alkyl, wherein the $C_{1-6}$alkyl is optionally substituted with one or more —OH, or (iii) 3-10 membered heterocyclyl optionally substituted with one or more $C_{1-6}$alkyl;

$R^5$ is, independently at each occurrence, H, halo, —CN, 3-10 membered heterocyclyl, $C_{1-6}$alkyl, or $C_{1-6}$alkoxy, wherein the $C_{1-6}$alkyl of $R^5$ is optionally substituted with one or more halo or —OH, and wherein the $C_{1-6}$alkoxy is optionally substituted with one or more halo; and $R^6$ and $R^7$ are each independently H or halo.

Any embodiments provided herein of a compound of formula (I), or a stereoisomer or tautomer thereof, or a pharmaceutically acceptable salt of any of the foregoing, or any variation or embodiment thereof, are also embodiments of a compound of formula (I'), or a stereoisomer or tautomer thereof, or a pharmaceutically acceptable salt of any of the foregoing, or any variation or embodiment thereof.

Any embodiments provided herein of a compound of formula (I) or (I'), or a stereoisomer or tautomer thereof, or a pharmaceutically acceptable salt of any of the foregoing, or any variation or embodiment thereof, are also embodiments of a compound of formula (II), or a stereoisomer or tautomer thereof, or a pharmaceutically acceptable salt of any of the foregoing, or any variation or embodiment thereof.

In one aspect, provided herein is a compound of formula (I-A):

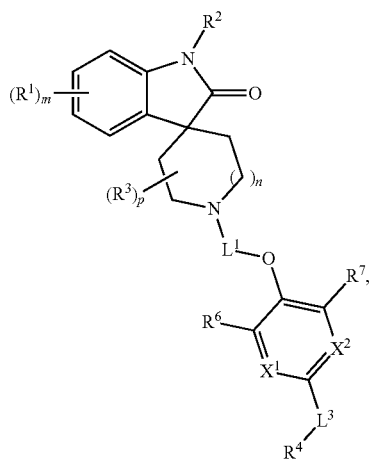

or a stereoisomer or tautomer thereof, or a pharmaceutically acceptable salt of any of the foregoing, wherein: n is 1 or 2; and wherein m, p, $R^1$, $R^2$, $R^3$, $L^1$, $L^3$, $R^4$, $X^1$, $X^2$, $R^6$, and $R^7$ are as defined elsewhere herein. In another variation, m, p, $R^1$, $R^2$, $R^3$, $L^1$, $L^3$, $R^4$, $X^1$, $X^2$, $R^6$, and $R^7$ of formula (I-A) are as defined for a compound of formula (I'), or (II), or a stereoisomer or tautomer thereof, or a pharmaceutically acceptable salt of any of the foregoing, or any variation or embodiment thereof.

In one aspect, provided herein is a compound of formula (I-B):

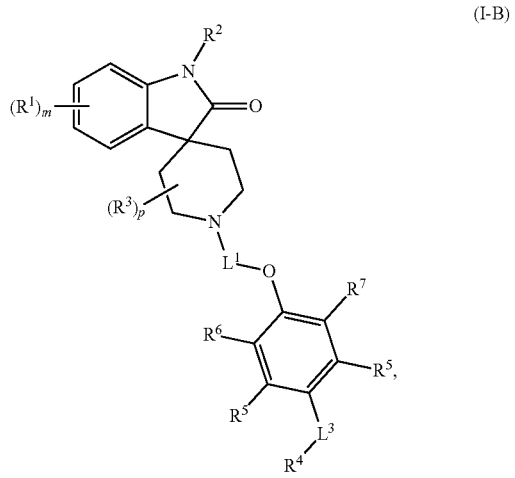

or a stereoisomer or tautomer thereof, or a pharmaceutically acceptable salt of any of the foregoing, wherein: m, p, $R^1$, $R^2$, $R^3$, $L^1$, $L^3$, $R^4$, $R^5$, $R^6$, and $R^7$ are as defined elsewhere herein. In another variation, m, p, $R^1$, $R^2$, $R^3$, $L^1$, $L^3$, $R^4$, $R^5$, $R^6$, and $R^7$ of formula (I-B) are as defined for a compound of formula (I'), or (II), or a stereoisomer or tautomer thereof, or a pharmaceutically acceptable salt of any of the foregoing, or any variation or embodiment thereof.

In one aspect, provided herein is a compound of formula (I-C):

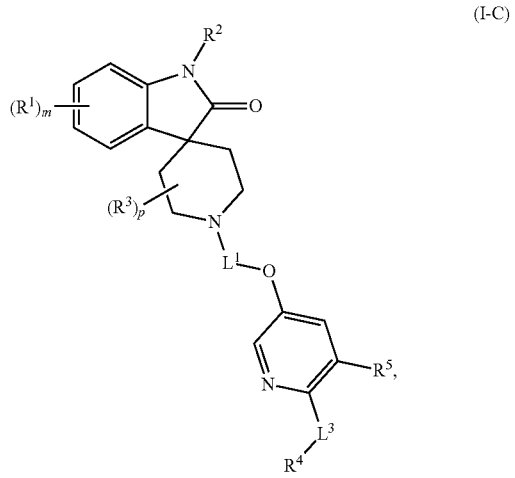

or a stereoisomer or tautomer thereof, or a pharmaceutically acceptable salt of any of the foregoing, wherein m, p, $R^1$, $R^2$, $R^3$, $L^1$, $L^3$, $R^4$, and $R^5$ are as defined elsewhere herein. In another variation, m, p, $R^1$, $R^2$, $R^3$, $L^1$, $L^3$, $R^4$, and $R^5$ of formula (I-C) are as defined for a compound of formula (I'), or (II), or a stereoisomer or tautomer thereof, or a pharmaceutically acceptable salt of any of the foregoing, or any variation or embodiment thereof.

In one aspect, provided herein is a compound of formula (I-D):

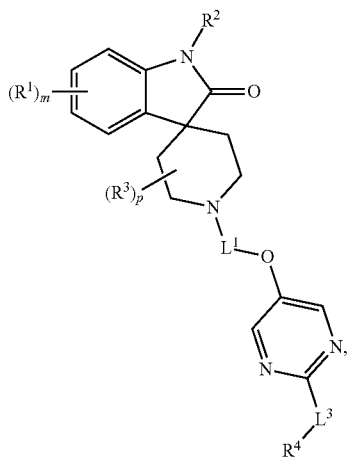

(I-D)

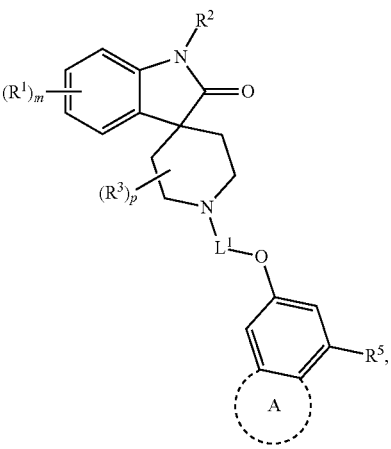

(I-F)

or a stereoisomer or tautomer thereof, or a pharmaceutically acceptable salt of any of the foregoing, wherein m, p, $R^1$, $R^2$, $R^3$, $L^1$, $L^3$, and $R^4$ are as defined elsewhere herein. In another variation, m, p, $R^1$, $R^2$, $R^3$, $L^1$, $L^3$, and $R^4$ of formula (I-D) are as defined for a compound of formula (I'), or (II), or a stereoisomer or tautomer thereof, or a pharmaceutically acceptable salt of any of the foregoing, or any variation or embodiment thereof.

In one aspect, provided herein is a compound of formula (I-E):

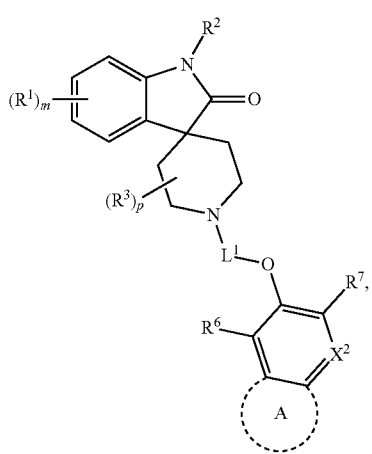

(I-E)

or a stereoisomer or tautomer thereof, or a pharmaceutically acceptable salt of any of the foregoing, wherein m, p, $R^1$, $R^2$, $R^3$, $L^1$, $X^2$, $R^6$, $R^7$, and ring A are as defined elsewhere herein. In another variation, m, p, $R^1$, $R^2$, $R^3$, $L^1$, $X^2$, $R^6$, $R^7$, and ring A of formula (I-E) are as defined for a compound of formula (I'), or (II), or a stereoisomer or tautomer thereof, or a pharmaceutically acceptable salt of any of the foregoing, or any variation or embodiment thereof.

In one aspect, provided herein is a compound of formula (I-F):

or a stereoisomer or tautomer thereof, or a pharmaceutically acceptable salt of any of the foregoing, wherein m, p, $R^1$, $R^2$, $R^3$, $L^1$, $R^5$, and ring A are as defined elsewhere herein. In another variation, m, p, $R^1$, $R^2$, $R^3$, $L^1$, $R^5$, and ring A of formula (I-F) are as defined for a compound of formula (I'), or (II), or a stereoisomer or tautomer thereof, or a pharmaceutically acceptable salt of any of the foregoing, or any variation or embodiment thereof.

In one aspect, provided herein is a compound of formula (I-G):

(I-G)

or a stereoisomer or tautomer thereof, or a pharmaceutically acceptable salt of any of the foregoing, wherein m, p, $R^1$, $R^2$, $R^3$, $L^1$, and ring A are as defined elsewhere herein. In another variation, m, p, $R^1$, $R^2$, $R^3$, $L^1$, and ring A of formula (I-G) are as defined for a compound of formula (I'), or (II), or a stereoisomer or tautomer thereof, or a pharmaceutically acceptable salt of any of the foregoing, or any variation or embodiment thereof.

In one aspect, provided herein is a compound of formula (II-A):

(II-A)

or a stereoisomer or tautomer thereof, or a pharmaceutically acceptable salt of any of the foregoing, wherein m, p, $R^1$, $R^2$, $R^3$, $L^1$, $X^2$, $X^3$, $X^4$, and ring A are as defined elsewhere herein.

In one aspect, provided herein is a pharmaceutical composition, comprising (i) a compound of formula (I), or any embodiment or variation thereof, such as a compound of formula (I), (I-A) (I-B), (I-C), (I-D), (I-E), (I-F), or (I-G), or a stereoisomer or tautomer thereof, or a pharmaceutically acceptable salt of any of the foregoing, and (ii) one or more pharmaceutically acceptable excipients. In another variation, provided herein is a pharmaceutical composition, comprising (i) a compound of formula (I'), or any embodiment or variation thereof, such as a compound of formula (I), (I-A) (I-B), (I-C), (I-D), (I-E), (I-F), or (I-G), or a stereoisomer or tautomer thereof, or a pharmaceutically acceptable salt of any of the foregoing, and (ii) one or more pharmaceutically acceptable excipients. In another variation, provided herein is a pharmaceutical composition, comprising (i) a compound of formula (II), or any embodiment or variation thereof, such as a compound of formula (I), (I'), (I-A) (I-B), (I-C), (I-D), (I-E), (I-F), (I-G), or (II-A), or a stereoisomer or tautomer thereof, or a pharmaceutically acceptable salt of any of the foregoing, and (ii) one or more pharmaceutically acceptable excipients.

In one aspect, provided herein is a method of modulating APOL1 in a cell, comprising exposing the cell to a composition comprising an effective amount of a compound of formula (I), or any embodiment or variation thereof, such as a compound of formula (I), (I-A) (I-B), (I-C), (I-D), (I-E), (I-F), or (I-G), or a stereoisomer or tautomer thereof, or a pharmaceutically acceptable salt of any of the foregoing, or a pharmaceutical composition comprising (i) a compound of formula (I), or any embodiment or variation thereof, such as a compound of formula (I), (I-A) (I-B), (I-C), (I-D), (I-E), (I-F), or (I-G), or a stereoisomer or tautomer thereof, or a pharmaceutically acceptable salt of any of the foregoing, and (ii) one or more pharmaceutically acceptable excipients. In another variation, provided herein is a method of modulating APOL1 in a cell, comprising exposing the cell to a composition comprising an effective amount of a compound of formula (I'), or any embodiment or variation thereof, such as a compound of formula (I), (I-A) (I-B), (I-C), (I-D), (I-E), (I-F), or (I-G), or a stereoisomer or tautomer thereof, or a pharmaceutically acceptable salt of any of the foregoing, or a pharmaceutical composition comprising (i) a compound of formula (I'), or any embodiment or variation thereof, such as a compound of formula (I), (I-A) (I-B), (I-C), (I-D), (I-E), (I-F), or (I-G), or a stereoisomer or tautomer thereof, or a pharmaceutically acceptable salt of any of the foregoing, and (ii) one or more pharmaceutically acceptable excipients. In another variation, provided herein is a method of modulating APOL1 in a cell, comprising exposing the cell to a composition comprising an effective amount of a compound of formula (II), or any embodiment or variation thereof, such as a compound of formula (I), (I'), (I-A) (I-B), (I-C), (I-D), (I-E), (I-F), (I-G), or (II-A), or a stereoisomer or tautomer thereof, or a pharmaceutically acceptable salt of any of the foregoing, or a pharmaceutical composition comprising (i) a compound of formula (II), or any embodiment or variation thereof, such as a compound of formula (I), (II), (I-A) (I-B), (I-C), (I-D), (I-E), (I-F), (I-G), or (II-A), or a stereoisomer or tautomer thereof, or a pharmaceutically acceptable salt of any of the foregoing, and (ii) one or more pharmaceutically acceptable excipients.

In one aspect, provided herein is a method of inhibiting APOL1 in a cell, comprising exposing the cell to a composition comprising an effective amount of a compound of formula (I), or any embodiment or variation thereof, such as a compound of formula (I), (I-A) (I-B), (I-C), (I-D), (I-E), (I-F), or (I-G), or a stereoisomer or tautomer thereof, or a pharmaceutically acceptable salt of any of the foregoing, or a pharmaceutical composition comprising (i) a compound of formula (I), or any embodiment or variation thereof, such as a compound of formula (I), (I-A) (I-B), (I-C), (I-D), (I-E), (I-F), or (I-G), or a stereoisomer or tautomer thereof, or a pharmaceutically acceptable salt of any of the foregoing, and (ii) one or more pharmaceutically acceptable excipients. In another variation, provided herein is a method of inhibiting APOL1 in a cell, comprising exposing the cell to a composition comprising an effective amount of a compound of formula (I'), or any embodiment or variation thereof, such as a compound of formula (I), (I-A) (I-B), (I-C), (I-D), (I-E), (I-F), or (I-G), or a stereoisomer or tautomer thereof, or a pharmaceutically acceptable salt of any of the foregoing, or a pharmaceutical composition comprising (i) a compound of formula (I), or any embodiment or variation thereof, such as a compound of formula (I), (I-A) (I-B), (I-C), (I-D), (I-E), (I-F), or (I-G), or a stereoisomer or tautomer thereof, or a pharmaceutically acceptable salt of any of the foregoing, and (ii) one or more pharmaceutically acceptable excipients. In another variation, provided herein is a method of inhibiting APOL1 in a cell, comprising exposing the cell to a composition comprising an effective amount of a compound of formula (II), or any embodiment or variation thereof, such as a compound of formula (I), (I'), (I-A) (I-B), (I-C), (I-D), (I-E), (I-F), (I-G), or (II-A), or a stereoisomer or tautomer thereof, or a pharmaceutically acceptable salt of any of the foregoing, or a pharmaceutical composition comprising (i) a compound of formula (II), or any embodiment or variation thereof, such as a compound of formula (I), (I'), (I-A) (I-B), (I-C), (I-D), (I-E), (I-F), (I-G), or (II-A), or a stereoisomer or tautomer thereof, or a pharmaceutically acceptable salt of any of the foregoing, and (ii) one or more pharmaceutically acceptable excipients.

In one aspect, provided herein is a method of treating an APOL1-mediated disease, disorder, or condition in an individual in need thereof, comprising administering to the individual an effective amount of a compound of formula (I), or any embodiment or variation thereof, such as a compound of formula (I), (I-A) (I-B), (I-C), (I-D), (I-E), (I-F), or (I-G), or a stereoisomer or tautomer thereof, or a pharmaceutically acceptable salt of any of the foregoing, or a pharmaceutical composition comprising (i) a compound of formula (I), or any embodiment or variation thereof, such as a compound of formula (I), (I-A) (I-B), (I-C), (I-D), (I-E), (I-F), or (I-G), or a stereoisomer or tautomer thereof, or a pharmaceutically acceptable salt of any of the foregoing, and (ii) one or more pharmaceutically acceptable excipients. In another variation, provided herein is a method of treating an APOL1-mediated disease, disorder, or condition in an individual in need thereof, comprising administering to the individual an effective amount of a compound of formula (I'), or any embodiment or variation thereof, such as a compound of formula (I), (I-A) (I-B), (I-C), (I-D), (I-E), (I-F), or (I-G), or a stereoisomer or tautomer thereof, or a pharmaceutically acceptable salt of any of the foregoing, or a pharmaceutical composition comprising (i) a compound of formula (I'), or any embodiment or variation thereof, such as a compound of formula (I), (I-A) (I-B), (I-C), (I-D), (I-E), (I-F), or (I-G), or a stereoisomer or tautomer thereof, or a pharmaceutically acceptable salt of any of the foregoing, and (ii) one or more pharmaceutically acceptable excipients. In another variation, provided herein is a method of treating an APOL1-mediated disease, disorder, or condition in an individual in need thereof, comprising administering to the individual an effective amount of a compound of formula (II), or any embodiment or variation thereof, such as a compound of formula (I), (I'), (I-A) (I-B), (I-C), (I-D), (I-E), (I-F), (I-G), or (II-A), or a stereoisomer or tautomer thereof, or a pharmaceutically acceptable salt of any of the foregoing, or a pharmaceutical composition comprising (i) a compound of formula (II), or any embodiment or variation thereof, such as a compound of formula (I), (I'), (I-A) (I-B), (I-C), (I-D), (I-E), (I-F), (I-G), or (II-A), or a stereoisomer or tautomer thereof, or a pharmaceutically acceptable salt of any of the foregoing, and (ii) one or more pharmaceutically acceptable excipients.

In one aspect, provided herein is a kit, comprising (i) a compound of formula (I), or any embodiment or variation thereof, such as a compound of formula (I), (I-A) (I-B), (I-C), (I-D), (I-E), (I-F), or (I-G), or a stereoisomer or tautomer thereof, or a pharmaceutically acceptable salt of any of the foregoing, and (ii) instructions for use in treating an APOL1-mediated disease, disorder, or condition in an individual in need thereof. In another variation, provided herein is a kit, comprising (i) a compound of formula (I'), or any embodiment or variation thereof, such as a compound of formula (I), (I-A) (I-B), (I-C), (I-D), (I-E), (I-F), or (I-G), or a stereoisomer or tautomer thereof, or a pharmaceutically acceptable salt of any of the foregoing, and (ii) instructions for use in treating an APOL1-mediated disease, disorder, or condition in an individual in need thereof. In another variation, provided herein is a kit, comprising (i) a compound of formula (II), or any embodiment or variation thereof, such as a compound of (I), (I'), (I-A) (I-B), (I-C), (I-D), (I-E), (I-F), (I-G), or (II-A), or a stereoisomer or tautomer thereof, or a pharmaceutically acceptable salt of any of the foregoing, and (ii) instructions for use in treating an APOL1-mediated disease, disorder, or condition in an individual in need thereof.

In some aspect, provided herein are methods of preparing a compound of formula (I), or any embodiment or variation thereof, such as a compound of formula (I), (I-A) (I-B), (I-C), (I-D), (I-E), (I-F), or (I-G), or a stereoisomer or tautomer thereof, or a pharmaceutically acceptable salt of any of the foregoing. In another variation, provided herein are methods of preparing a compound of formula (I'), or any embodiment or variation thereof, such as a compound of formula (I), (I-A) (I-B), (I-C), (I-D), (I-E), (I-F), or (I-G), or a stereoisomer or tautomer thereof, or a pharmaceutically acceptable salt of any of the foregoing. In another variation, provided herein are methods of preparing a compound of formula (I'), or any embodiment or variation thereof, such as a compound of formula (I), (I'), (I-A) (I-B), (I-C), (I-D), (I-E), (I-F), (I-G), or (II-A), or a stereoisomer or tautomer thereof, or a pharmaceutically acceptable salt of any of the foregoing.

DETAILED DESCRIPTION OF THE INVENTION

Unless clearly indicated otherwise, the terms "a," "an," and the like, refer to one or more.

As used herein, "about" a parameter or value includes and describes that parameter or value per se. For example, "about X" includes and describes X per se.

"Individual" refers to mammals and includes humans and non-human mammals. Examples of individuals include, but are not limited to, some primates and humans. In some embodiments, individual refers to a human.

As used herein, an "at risk" individual is an individual who is at risk of developing a disease or condition. An individual "at risk" may or may not have a detectable disease or condition, and may or may not have displayed detectable disease prior to the treatment methods described herein. "At risk" denotes that an individual has one or more so-called risk factors, which are measurable parameters that correlate with development of a disease or condition and are known in the art. An individual having one or more of these risk factors has a higher probability of developing the disease or condition than an individual without these risk factor(s).

"Treatment" or "treating" is an approach for obtaining beneficial or desired results including clinical results. Beneficial or desired results may include one or more of the following: decreasing one or more symptom resulting from the disease or condition; diminishing the extent of the disease or condition; slowing or arresting the development of one or more symptom associated with the disease or condition (e.g., stabilizing the disease or condition, preventing or delaying the worsening or progression of the disease or condition); and relieving the disease, such as by causing the regression of clinical symptoms (e.g., ameliorating the disease state, enhancing the effect of another medication, delaying the progression of the disease, increasing the quality of life, and/or prolonging survival).

As used herein, "delaying" development of a disease or condition means to defer, hinder, slow, retard, stabilize and/or postpone development of the disease or condition. This delay can be of varying lengths of time, depending on the history of the disease and/or individual being treated. As is evident to one skilled in the art, a sufficient or significant delay can, in effect, encompass prevention, in that the individual does not develop the disease or condition.

As used herein, the term "therapeutically effective amount" or "effective amount" intends such amount of a compound of the disclosure or a pharmaceutically salt thereof sufficient to effect treatment when administered to an individual. As is understood in the art, an effective amount may be in one or more doses, e.g., a single dose or multiple doses may be required to achieve the desired treatment endpoint. An effective amount may be considered in the context of administering one or more therapeutic agents, and a single agent may be considered to be given in an effective amount if, in conjunction with one or more other agents, a desirable or beneficial result may be or is achieved.

As used herein, "unit dosage form" refers to physically discrete units, suitable as unit dosages, each unit containing a predetermined quantity of active ingredient, or compound, which may be in a pharmaceutically acceptable carrier.

As used herein, by "pharmaceutically acceptable" is meant a material that is not biologically or otherwise undesirable, e.g., the material may be incorporated into a pharmaceutical composition administered to an individual without causing significant undesirable biological effects.

The term "alkyl", as used herein, refers to an unbranched or branched saturated hydrocarbon chain. As used herein, alkyl has 1-20 carbons (i.e., $C_{1-20}$alkyl), 1-16 carbons (i.e., $C_{1-16}$alkyl), 1-12 carbons (i.e., $C_{1-12}$alkyl), 1-10 carbons (i.e., $C_{1-10}$alkyl), 1-8 carbons (i.e., $C_{1-8}$alkyl), 1-6 carbons (i.e., $C_{1-6}$alkyl), 1-4 carbons (i.e., $C_{1-4}$alkyl), or 1-3 carbons (i.e., $C_{1-3}$alkyl). Examples of alkyl groups include, but are not limited to, methyl, ethyl, propyl, iso-propyl, n-butyl, sec-butyl, iso-butyl, tert-butyl, pentyl, 2-pentyl, iso-pentyl, neo-pentyl, hexyl, 2-hexyl, 3-hexyl, and 3-methylpentyl. When an alkyl residue having a specific number of carbons is named by chemical name or molecular formula, all positional isomers having that number of carbon atoms may be encompassed—for example, "butyl" includes n-butyl, sec-butyl, iso-butyl, and tert-butyl; and "propyl" includes n-propyl and iso-propyl. Certain commonly used alternative names may be used and will be understood by those of ordinary skill in the art. For instance, a divalent group, such as a divalent "alkyl" group, may be referred to as an "alkylene".

The term "alkoxy", as used herein, refers to an —O-alkyl moiety. Examples of alkoxy groups include, but are not limited to, methoxy, ethoxy, n-propoxy, iso-propoxy, n-butoxy, tert-butoxy, sec-butoxy, n-pentoxy, n-hexoxy, and 1,2-dimethylbutoxy.

The term "aryl", as used herein, refers to a fully unsaturated carbocyclic ring moiety. The term "aryl" encompasses monocyclic and polycyclic fused-ring moieties. As used herein, aryl encompasses ring moieties comprising, for example, 6 to 20 annular carbon atoms (i.e., $C_{6-20}$aryl), 6 to 16 annular carbon atoms (i.e., $C_{6-16}$aryl), 6 to 12 annular carbon atoms (i.e., $C_{6-12}$aryl), or 6 to 10 annular carbon atoms (i.e., $C_{6-10}$aryl). Examples of aryl moieties include, but are not limited to, phenyl, naphthyl, fluorenyl, and anthryl.

The term "cycloalkyl", as used herein, refers to a saturated or partially unsaturated carbocyclic ring moiety. The term "cycloalkyl" encompasses monocyclic and polycyclic ring moieties, wherein the polycyclic moieties may be fused, branched, or spiro. Cycloalkyl includes cycloalkenyl groups, wherein the ring moiety comprises at least one annular double bond. Cycloalkyl includes any polycyclic carbocyclic ring moiety comprising at least one non-aromatic ring, regardless of the point of attachment to the remainder of the molecule. As used herein, cycloalkyl includes rings comprising, for example, 3 to 20 annular carbon atoms (i.e., a $C_{3-20}$cycloalkyl), 3 to 16 annular carbon atoms (i.e., a $C_{3-16}$cycloalkyl), 3 to 12 annular carbon atoms (i.e., a $C_{3-12}$cycloalkyl), 3 to 10 annular carbon atoms (i.e., a $C_{3-10}$cycloalkyl), 3 to 8 annular carbon atoms (i.e., a $C_{3-8}$cycloalkyl), 3 to 6 annular carbon atoms (i.e., a $C_{3-6}$cycloalkyl), or 3 to 5 annular carbon atoms (i.e., a $C_{3-5}$cycloalkyl). Monocyclic cycloalkyl ring moieties include, for example, cyclopropyl, cyclobutyl, cyclopentyl, cyclohexyl, cycloheptyl, and cyclooctyl. Polycyclic groups include, for example, bicyclo[2.2.1]heptanyl, bicyclo[2.2.2]octanyl, adamantyl, norbomyl, decalinyl, 7,7-dimethyl-bicyclo [2.2.1]heptanyl, and the like. Still further, cycloalkyl also includes spiro cycloalkyl ring moieties, for example, spiro[2.5]octanyl, spiro[4.5]decanyl, or spiro [5.5]undecanyl.

The term "halo", as used herein, refers to atoms occupying group VIIA of The Periodic Table and includes fluorine (fluoro), chlorine (chloro), bromine (bromo), and iodine (iodo).

The term "heteroaryl", as used herein, refers to an aromatic (fully unsaturated) ring moiety that comprises one or more annular heteroatoms independently selected from the group consisting of nitrogen, oxygen, and sulfur. The term "heteroaryl" includes both monocyclic and polycyclic fused-ring moieties. As used herein, a heteroaryl comprises, for example, 5 to 20 annular atoms (i.e., a 5-20 membered heteroaryl), 5 to 16 annular atoms (i.e., a 5-16 membered heteroaryl), 5 to 12 annular atoms (i.e., a 5-12 membered heteroaryl), 5 to 10 annular atoms (i.e., a 5-10 membered heteroaryl), 5 to 8 annular atoms (i.e., a 5-8 membered heteroaryl), or 5 to 6 annular atoms (i.e., a 5-6 membered heteroaryl). Any monocyclic or polycyclic aromatic ring moiety comprising one or more annular heteroatoms is considered a heteroaryl, regardless of the point of attachment to the remainder of the molecule (i.e., the heteroaryl moiety may be attached to the remainder of the molecule through any annular carbon or any annular heteroatom of the heteroaryl moiety). Examples of heteroaryl groups include, but are not limited to, acridinyl, benzimidazolyl, benzindolyl, benzofuranyl, benzonaphthofuranyl, benzoxazolyl, benzotriazolyl, benzo[4,6]imidazo[1,2-a]pyridyl, carbazolyl, dibenzofuranyl, dibenzothiophenyl, furanyl, imidazolyl, indazolyl, indolyl, indazolyl, isoindolyl, isoquinolyl, isoxazolyl, naphthyridinyl, oxadiazolyl, oxazolyl, 1-oxidopyridinyl, 1-oxidopyrimidinyl, 1-oxidopyrazinyl, 1-oxidopyridazinyl, phenazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, triazolyl, tetrazolyl, and triazinyl. Examples of the fused-heteroaryl rings include, but are not limited to, quinolinyl, isoquinolinyl, benzo[b]thiophenyl, indazolyl, benzo[d]imidazolyl, pyrazolo[1,5-a]pyridinyl, and imidazo[1,5-a]pyridinyl, wherein the heteroaryl can be bound via either ring of the fused system.

The term "heterocyclyl", as used herein, refers to a saturated or partially unsaturated cyclic moiety that encompasses one or more annular heteroatoms independently selected from the group consisting of nitrogen, oxygen, and sulfur. The term "heterocyclyl" includes both monocyclic and polycyclic ring moieties, wherein the polycyclic ring moieties may be fused, bridged, or spiro. Any non-aromatic monocyclic or polycyclic ring moiety comprising at least one annular heteroatom is considered a heterocyclyl, regardless of the point of attachment to the remainder of the molecule (i.e., the heterocyclyl moiety may be attached to the remainder of the molecule through any annular carbon or any annular heteroatom of the heterocyclyl moiety). Further, the term heterocyclyl is intended to encompass any polycyclic ring moiety comprising at least one annular heteroatom wherein the polycyclic ring moiety comprises at least one non-aromatic ring, regardless of the point of attachment to the remainder of the molecule. As used herein, a heterocyclyl comprises, for example, 3 to 20 annular atoms (i.e., a 3-20 membered heterocyclyl), 3 to 16 annular atoms (i.e., a 3-16 membered heterocyclyl), 3 to 12 annular atoms (i.e., a 3-12 membered heterocyclyl), 3 to 10 annular atoms (i.e., a 3-10 membered heterocyclyl), 3 to 8 annular atoms (i.e., a 3-8 membered heterocyclyl), 3 to 6 annular atoms (i.e., a 3-6 membered heterocyclyl), 3 to 5 annular atoms (i.e., a 3-5 membered heterocyclyl), 5 to 8 annular atoms (i.e., a 5-8 membered heterocyclyl), or 5 to 6 annular atoms (i.e., a 5-6 membered heterocyclyl). Examples of heterocyclyl groups include, e.g., azetidinyl, azepinyl, benzodioxolyl, benzo[b][1,4]dioxepinyl, 1,4-benzodioxanyl, benzopyranyl, benzodioxinyl, benzopyranonyl, benzofuranonyl, dioxolanyl, dihydropyranyl, hydropyranyl, thienyl[1,3]dithianyl, decahydroisoquinolyl, furanonyl, imidazolinyl, imidazolidinyl, indolinyl, indolizinyl, isoindolinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, oxiranyl, oxetanyl, phenothiazinyl, phenoxazinyl, piperidinyl, piperazinyl, 4-piperidonyl, pyrrolidinyl, pyrazolidinyl, quinuclidinyl, thiazolidinyl, tetrahydrofuryl, tetrahydropyranyl, trithianyl, tetrahydroquinolinyl, thiophenyl (i.e., thienyl), thiomorpholinyl, thiamorpholinyl, 1-oxo-thiomorpholinyl, and 1,1-dioxothiomorpholinyl. Examples of spiro heterocyclyl rings include, but are not limited to, bicyclic and tricyclic ring systems, such as oxabicyclo[2.2.2]octanyl, 2-oxa-7-azaspiro[3.5]nonanyl, 2-oxa-6-azaspiro[3.4]octanyl, and 6-oxa-1-azaspiro[3.3]heptanyl. Examples of fused heterocyclyl rings include, but are not limited to, 1,2,3,4-tetrahydroisoquinolinyl, 4,5,6,7-tetrahydrothieno[2,3-c]pyridinyl, indolinyl, and isoindolinyl, where the heterocyclyl can be bound via either ring of the fused system.

The terms "optional" and "optionally", as used herein, mean that the subsequently described event or circumstance may or may not occur and that the description includes instances where the event or circumstance occurs and instances where it does not. Accordingly, the term "optionally substituted" infers that any one or more (e.g., 1, 2, 1 to 5, 1 to 3, 1 to 2, etc.) hydrogen atoms on the designated atom or moiety or group may be replaced or not replaced by an atom or moiety or group other than hydrogen. By way of illustration and not limitation, the phrase "methyl optionally substituted with one or more chloro" encompasses —$CH_3$, —$CH_2Cl$, —$CHCl_2$, and —$CCl_3$ moieties.

It is understood that aspects and embodiments described herein as "comprising" include "consisting of" and "consisting essentially of" embodiments.

The term "pharmaceutically acceptable salt", as used herein, of a given compound refers to salts that retain the biological effectiveness and properties of the given compound and which are not biologically or otherwise undesirable. "Pharmaceutically acceptable salts" include, for example, salts with inorganic acids, and salts with an organic acid. In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Such compositions are well known in the pharmaceutical art. See, e.g., *Handbook of Pharmaceutical Salts Properties, Selection, and Use*, International Union of Pure and Applied Chemistry, John Wiley & Sons (2008), which is incorporated herein by reference. Those skilled in the art will recognize various synthetic methodologies that may be used to prepare nontoxic pharmaceutically acceptable addition salts. Pharmaceutically acceptable acid addition salts may be prepared from inorganic or organic acids. Salts derived from inorganic acids include, e.g., hydrochloric acid, hydrobromic acid, sulfuric acid, nitric acid, phosphoric acid, and the like. Salts derived from organic acids include, e.g., acetic acid, propionic acid, gluconic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, trifluoroacetic acid, and the like. Likewise, pharmaceutically acceptable base addition salts can be prepared from inorganic or organic bases. Salts derived from inorganic bases include, by way of example only, sodium, potassium, lithium, aluminum, ammonium, calcium, and magnesium salts. Salts derived from organic bases include, but are not limited to, salts of primary, secondary, and tertiary amines. Specific examples of suitable amines include, by way of example only, isopropylamine, trimethyl amine, diethyl amine, tri(iso-propyl), amine, tri(n-propyl) amine, ethanolamine, 2-dimethylaminoethanol, piperazine, piperidine, morpholine, N-ethylpiperidine, and the like.

Isotopically labeled forms of the compounds depicted herein may be prepared. Isotopically labeled compounds have structures depicted herein, except that one or more atoms are replaced by an atom having a selected atomic mass or mass number. Examples of isotopes that can be incorporated into the disclosed compounds include isotopes of hydrogen, carbon, nitrogen, oxygen, phosphorous, fluorine, chlorine, and iodine, such as $^2H$, $^3H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. In some embodiments, a compound of formula (I), or formula (I') is provided wherein one or more hydrogen is replaced by deuterium or tritium.

Some of the compounds provided herein may exist as tautomers. Tautomers are in equilibrium with one another. By way of illustration, amide containing compounds may exist in equilibrium with imidic acid tautomers. Regardless of which tautomer is shown and regardless of the nature of the equilibrium among tautomers, the compounds of this disclosure are understood by one of ordinary skill in the art to comprise both amide and imidic acid tautomers. Thus, for example, amide-containing compounds are understood to include their imidic acid tautomers. Likewise, imidic-acid containing compounds are understood to include their amide tautomers.

Also provided herein are prodrugs of the compounds depicted herein, or a pharmaceutically acceptable salt thereof. Prodrugs are compounds that may be administered to an individual and release, in vivo, a compound depicted herein as the parent drug compound. It is understood that prodrugs may be prepared by modifying a functional group on a parent drug compound in such a way that the modification is cleaved in vivo to release the parent drug compound. The development of prodrug compounds is well known in the pharmaceutical art. See, e.g., Rautio, J., Kumpulainen, H., Heimbach, T. et al. Prodrugs: design and clinical applications. *Nat. Rev. Drug. Discov.* 7, 255-270 (2008), which is incorporated herein by reference.

The compounds of the present disclosure, or their pharmaceutically acceptable salts, may include an asymmetric center and may thus give rise to enantiomers, diastereomers, and other stereoisomeric forms that may be defined, in terms of absolute stereochemistry, as (R)- or (S)- (or as (D)- or (L)- for amino acids). The present disclosure is meant to include all such possible isomers, as well as their racemic and optically pure forms and mixtures thereof in any ratio. Optically active (+) and (−), (R)- and (S)-, or (D)- and (L)-isomers may be prepared using chiral synthons or chiral reagents, or may be resolved using conventional techniques, for example, chromatography and/or fractional crystallization. Conventional techniques for the preparation/isolation of individual enantiomers include chiral synthesis from a suitable optically pure precursor or the resolution of the racemate (or the racemate of a salt or derivative) using, for example, chiral high pressure liquid chromatography (HPLC) or chiral supercritical fluid chromatography (SFC). When the compounds described herein contain olefinic double bonds or other centers of geometric asymmetry, unless specified otherwise, it is intended that the present disclosure includes both E and Z geometric isomers. Likewise, cis- and trans- are used in their conventional sense to describe relative spatial relationships.

A "stereoisomer" refers to a compound made up of the same atoms bonded by the same bonds, but having different three-dimensional structures, which are not interchangeable. The present disclosure contemplates various stereoisomers, or mixtures thereof, and includes "enantiomers," which refers to two stereoisomers whose structures are non-superimposable mirror images of one another. "Diastereomers" are stereoisomers that have at least two asymmetric atoms, but which are not mirror images of each other.

Where enantiomeric and/or diastereomeric forms exist of a given structure, flat bonds indicate that all stereoisomeric forms of the depicted structure may be present, e.g.,

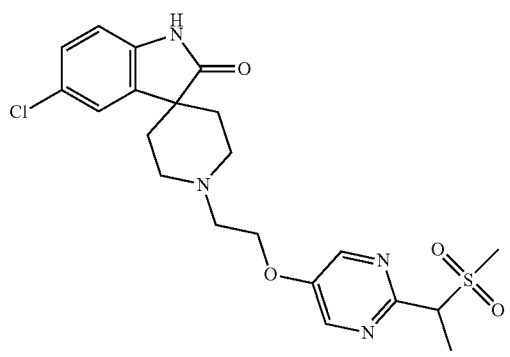

Where enantiomeric forms exist of a given structure, flat bonds and the presence of a "*" symbol indicate that the composition is made up of at least 90%, by weight, of a single isomer with unknown absolute stereochemistry, e.g.,

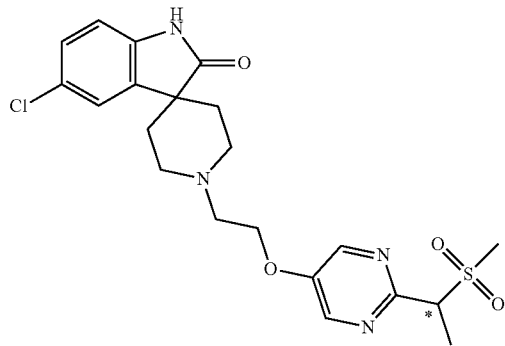

Where enantiomeric and/or diastereomeric forms exist of a given structure with two or more stereocenters, flat bonds and the presence of two or more "*" symbols indicate the composition is made up of at least 90%, by weight, of a single enantiomer or diastereomer with unknown absolute stereochemistry, e.g.,

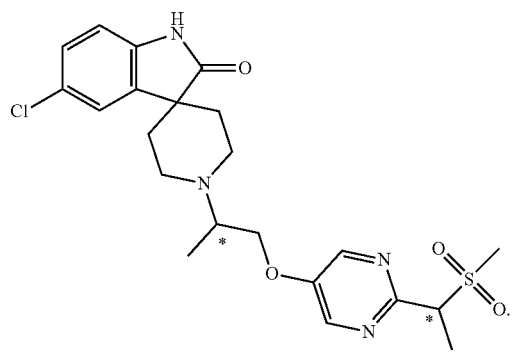 [SMILES: CC(COc1cnc(C(C)S(C)(=O)=O)nc1)N1CCC2(CC1)C(=O)Nc1ccc(Cl)cc12]

Where enantiomeric and/or diastereomeric forms exist of a given structure, the composition is made up of at least 90%, by weight, dashes or wedges indicate a single enantiomer or diastereomer with known relative or absolute stereochemistry, e.g

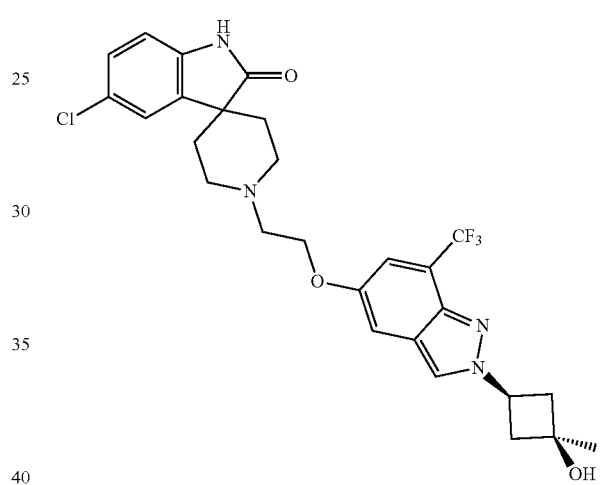

Abbreviations used are those conventional in the art and are in accordance with the Periodic Table of the Elements, CAS version, *Handbook of Chemistry and Physics, 75$^{th}$ Ed*, hereby incorporated herein by reference in its entirety. The following examples are intended to be illustrative only and not limiting in any way.

| | |
|---|---|
| ° C. | degrees Celsius |
| μL | microliter |
| μW | microwave |
| [M + XX]$^+$ | observed mass |
| AC$_{50}$ | half-maximal activity concentration |
| Ac$_2$O | acetic anhydride |
| AIBN | azobisisobutyronitrile |
| app | apparent (NMR) |
| br | broad (NMR) |
| BH$_3$•THF | borane-tetrahydrofuran complex |
| BBr$_3$ | boron tribromide |
| BnCl | benzyl chloride |
| B(Pin)$_2$ | bis(pinacolato)diboron |
| Calc'd | calculated |
| Cbz-Cl | benzyl chloroformate |
| CCl$_4$ | carbontetrachloride |
| CDI | carbonyldiimidazole |
| CHCl$_3$ | chloroform |
| CO$_2$ | carbon dioxide |
| CS$_2$CO$_3$ | cesium carbonate |

| | |
|---|---|
| CuI | copper iodide |
| d | deuterated (NMR solvents) |
| d | doublet (NMR) |
| dd | doublet of doublets (NMR) |
| DAST | diethylaminosulfur trifluoride |
| DMA | N,N-dimethylacetamide |
| DCE | 1,2-dichloroethane |
| DCM | dichloromethane |
| DIAD | diisopropyl azodicarboxylate |
| DIEA | N,N-diisopropylethylamine |
| DME | dimethoxyethane |
| DMEDA | N,N-dimethylethylenediamine |
| DMA | dimethylacetamide |
| DMF | N,N-dimethylformamide |
| DPPF | 1,1'-bis(diphenylphosphino)ferrocene |
| $EC_{50}$ | half-maximal effective concentration |
| EDCI | 1-ethyl-3-(3-dimethylamino-propyl)carbodiimide |
| $Et_3N$ | triethyl amine |
| EtOAc | ethyl acetate |
| EtOH | ethanol |
| g | grams |
| h | hours |
| H | hydrogen |
| $H_2$ | hydrogen gas |
| $H_2O$ | water |
| $H_2O_2$ | hydrogen peroxide |
| HATU | N-[(Dimethylamino)-1H-1,2,3-triazolo-[4,5-b]pyridin-1-ylmethylene]-N-methylmethanaminium hexafluorophosphate N-oxide |
| HCl | hydrochloric acid |
| HOBt | hydroxybenzotriazole |
| HPLC | high-performance liquid chromatography |
| In vacuo | in a vacuum |
| $(Ir[dF(CF_3)ppy]_2(dtbpy))PF_6$ | [4,4'-Bis(1,1-dimethylethyl)-2,2'-bipyridine-N1,N1']bis[3,5-difluoro-2-[5-(trifluoromethyl)-2-pyridinyl-N]phenyl-C] Iridium(III) hexafluorophosphate |
| IUPAC | International Union of Pure and Applied Chemistry |
| J | J-coupling value (NMR) |
| $K_2CO_3$ | potassium carbonate |
| KI | potassium iodide |
| KOAc | potassium acetate |
| KOH | potassium hydroxide |
| $LiAlH_4$ | lithium aluminum hydride |
| LiHMDS | lithium bis(trimethylsilyl)amide |
| LiOH | lithium hydroxide |
| MeOH | methanol |
| MeCN | acetonitrile |
| MHz | megahertz |
| m | multiplet (NMR) |
| mg | milligrams |
| min | minutes |
| mL | milliliter |
| mmol | millimole |
| mM | millimolar |
| M | molarity or molar |
| m-CPBA | meta-chloroperoxybenzoic acid |
| MeCN | acetonitrile |
| $MeSO_2Na$ | sodium methanesulfinate |
| MS | mass spectrometry |
| MsCl | methanesulfonyl chloride |
| $Ms_2O$ | methanesulfonic anhydride |
| MTBE | methyl tert-butyl ether |
| n/a | not applicable |
| $NaBH(OAc)_3$ | sodium triacetoxyborohydride |
| NaH | sodium hydride |
| NBS | N-bromosuccinimide |
| $NH_4$ | ammonium |
| $NH_4OH$ | ammonium hydroxide |
| $NH_4HCO_3$ | ammonium bicarbonate |
| $Na_2SO_4$ | sodium sulfate |
| $NaBH_3CN$ | sodium cyanoborohydride |
| NMP | 1-methyl-2-pyrrolidinone |
| NMR | nuclear magnetic resonance |
| $NaIO_4$ | sodium periodate |
| NaOH | sodium hydroxide |
| $OsO_4$ | osmium tetraoxide |
| Pd/C | palladium on carbon |
| $PCy_3$ | tricyclohexylphosphine |
| $Pd_2(dba)_3$ | tris(dibenzylideneacetone) dipalladium(0) |
| $Pd(PPh_3)_2$ | bis(triphenylphosphine) palladium(II) chloride |
| $Pd(dba)3$ | tris(dibenzylideneacetone) dipalladium(0) |
| pH | potential of hydrogen |
| $PPh_3$ | triphenyl phosphine |
| PSI | pounds per square inch |
| s | singlet (NMR) |
| SEMCl | (2-chloromethoxyethyl) trimethylsilane |
| SFC | super fluid chromatography |
| $SOCl_2$ | thionyl chloride |
| t | triplet (NMR) |
| T3P | propanephosphonic acid anhydride |
| TBAB | tetrabutylammonium bromide |
| TBAI | tetrabutylammonium iodide |
| TEA | triethylamine |
| TFA | trifluoroacetic acid |
| THF | tetrahydrofuran |
| TMSCl | trimethylsilyl chloride |
| Xantphos | 4,5-bis(diphenylphosphino)-9,9-dimethylxanthene |
| $Zn(CN)_2$ | zinc cyanide |

Compounds

Provided herein is a compound of formula (II):

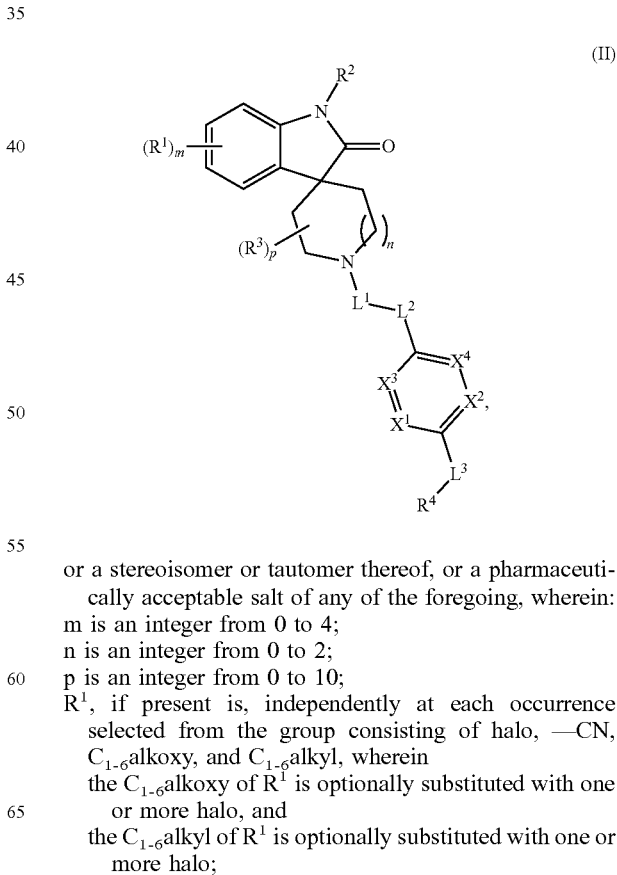

or a stereoisomer or tautomer thereof, or a pharmaceutically acceptable salt of any of the foregoing, wherein:
m is an integer from 0 to 4;
n is an integer from 0 to 2;
p is an integer from 0 to 10;
$R^1$, if present is, independently at each occurrence selected from the group consisting of halo, —CN, $C_{1-6}$alkoxy, and $C_{1-6}$alkyl, wherein
the $C_{1-6}$alkoxy of $R^1$ is optionally substituted with one or more halo, and
the $C_{1-6}$alkyl of $R^1$ is optionally substituted with one or more halo;

$R^2$ is H, $C_{1-6}$alkyl, $C_{3-10}$cycloalkyl, or 3-15 membered heterocyclyl, wherein
  the $C_{1-6}$alkyl of $R^2$ is optionally substituted with one or more deuterium, halo, —OH, —NH$_2$, or $C_{1-6}$alkoxy, and
  the $C_{3-10}$cycloalkyl of $R^2$ is optionally substituted with one or more —OH;

$R^3$, if present, is $C_{1-6}$alkyl;

$L^1$ is $C_{1-6}$alkylene, wherein
  the $C_{1-6}$alkylene of $L^1$ is optionally substituted with one or more deuterium or $C_{1-6}$alkyl, and wherein
  the $C_{1-6}$alkyl is further optionally substituted with one or more —OH or $C_{1-6}$alkoxy;

$L^2$ is O or N($R^x$), wherein $R^x$ is H or $C_{1-6}$alkyl; and either (1) $L^3$ is absent or is O, $C_{3-10}$cycloalkyl, 3-10 membered heterocyclyl, or $C_{1-6}$alkylene, wherein
  the $C_{3-10}$cycloalkyl of $L^3$ is optionally substituted with one or more —OH or $C_{1-6}$alkyl,
  the $C_{1-6}$alkylene of $L^3$ is optionally substituted with one or more —OH or $C_{1-6}$alkyl, wherein
    the $C_{1-6}$alkyl is optionally substituted with one or more —OH, and
  the 3-10 membered heterocyclyl of $L^3$ is optionally substituted with one or more —OH or $C_{1-6}$alkyl;

$X^1$ and $X^2$ are each independently N or C($R^5$); and $R^4$ is:

(i) —S(O)$_2$—$R^a$;

(ii) 5-20 membered heteroaryl, wherein the 5-20 membered heteroaryl of $R^4$ is optionally substituted with one or more $C_{1-6}$alkyl;

(iii) —N($R^d$)$_2$, wherein $R^d$ is independently at each occurrence H, $C_{1-6}$ alkyl, or —S(O)$_2$—$R^a$, wherein
  the $C_{1-6}$alkyl of $R^d$ is optionally substituted with one or more —OH, (iv) —NS(O)—($C_{1-6}$alkyl)$_2$, wherein the $C_{1-6}$alkyl is optionally substituted with one or more —OH, (v) —C(O)—N($R^e$)$_2$ wherein $R^e$ is independently at each occurrence H, $C_{1-6}$ alkyl, or 3-10 membered heterocycle, wherein
  the 3-10 membered heterocycle of $R^e$ is optionally substituted with one or more oxo, or both $R^e$ together with the N to which they are attached are taken together to form a 3-10 membered heterocyclyl, wherein
    the 3-10 membered heterocyclyl is optionally substituted with one or more halo, oxo, —OH, NH$_2$, —NH—S(O)$_2$—$R^a$, or —S(O)$_2$—$R^a$, (vi) 3-10 membered heterocyclyl optionally substituted with one or more $C_{1-6}$alkyl, —OH, oxo or —S(O)$_2R^a$, (vii) —S(O)—N($C_{1-6}$alkyl)-($C_{1-6}$alkyl), (viii) —CN, (ix) —(CH$_2$)$_q$OH, wherein q is an integer from 0-6, (x) —C(O)—$C_{1-6}$alkyl, or (xi) —P(O)($C_{1-6}$alkyl)$_2$;

or (2) $L^3$ is absent; and one of $X^1$ and $X^2$ is N or C($R^5$); and the other of $X^1$ and $X^2$ is N or C that is taken together with $R^4$, and the atoms to which they are attached, to form a 5-10 membered heterocyclyl or a 5-20 membered heteroaryl, wherein the 5-10 membered heterocyclyl is optionally substituted with one or more $R^b$, wherein $R^b$ is, independently at each occurrence, selected from the group consisting of —OH, halo, oxo, $C_{1-6}$alkyl, —C(O)—$C_{1-6}$alkyl, —C(O)—NH$_2$, —C(O)—NH($C_{1-6}$alkyl), —C(O)—N($C_{1-6}$alkyl)$_2$, —S(O)$_2$—$R^a$, $C_{3-10}$cycloalkyl, and 3-10 membered heterocyclyl, wherein the $C_{1-6}$alkyl of $R^b$ is optionally substituted with one or more halo, OH, —S(O)$_2$—$C_{1-6}$alkyl, or $C_{3-10}$cycloalkyl, and wherein the $C_{3-10}$cycloalkyl of the $C_{1-6}$alkyl of $R^b$ is further optionally substituted with one or more $C_{1-6}$alkyl or —OH and the $C_{3-10}$cycloalkyl of $R^b$ is optionally substituted with one or more —OH, $C_{3-10}$cycloalkyl, or $C_{1-6}$alkyl, and wherein the $C_{1-6}$alkyl of the $C_{3-10}$cycloalkyl of $R^b$ is further optionally substituted with one or more —OH, deuterium, or halo, and the 5-20 membered heteroaryl is optionally substituted with one or more $R^c$, wherein $R^c$ is, independently at each occurrence, selected from the group consisting of halo, $C_{1-6}$alkyl, —C(O)—$C_{1-6}$alkyl, —C(O)—NH$_2$, —C(O)—NH($C_{1-6}$alkyl), —C(O)—N($C_{1-6}$alkyl)$_2$, —S(O)$_2$—$R^a$, $C_{3-10}$cycloalkyl, and 3-10 membered heterocyclyl, wherein the $C_{1-6}$alkyl of $R^c$ is optionally substituted with one or more —S(O)$_2$—$C_{1-6}$alkyl, the $C_{3-10}$cycloalkyl of $R^c$ is optionally substituted with one or more —OH or $C_{1-6}$alkyl, and the 3-10 membered heterocyclyl of $R^c$ is optionally substituted with one or more —OH or $C_{1-6}$alkyl, and wherein the $C_{1-6}$alkyl of the 3-10 membered heterocyclyl of $R^c$ is further optionally substituted with one or more —OH;

$R^a$ is, independently at each occurrence:

(i) $C_{1-6}$alkyl optionally substituted with one or more halo, —OH, —S(O)$_2$—$C_{1-6}$alkyl, or —N($C_{1-6}$alkyl)-C(O)—$C_{1-6}$alkyl, (ii) $C_{3-10}$cycloalkyl optionally substituted with one or more —OH, —C(O)$_2$—$C_{1-6}$alkyl, —C(O)—NH($C_{1-6}$alkyl), —C(O)—N($C_{1-6}$alkyl)$_2$, or —C(O)—$C_{3-10}$heterocyclyl, or $C_{1-6}$alkyl, wherein the $C_{1-6}$alkyl is optionally substituted with one or more —OH, (iii) 3-10 membered heterocyclyl optionally substituted with one or more $C_{1-6}$alkyl, or (iv) NH($C_{1-6}$alkyl);

$R^5$ is, independently at each occurrence, H, halo, —CN, 3-10 membered heterocyclyl, $C_{1-6}$alkyl, or $C_{1-6}$alkoxy, wherein the $C_{1-6}$alkyl of $R^5$ is optionally substituted with one or more halo or —OH, and the $C_{1-6}$alkoxy of $R^5$ is optionally substituted with one or more halo;

$X^3$ is N or C($R^6$);

$X^4$ is N or C($R^7$);

and $R^6$ and $R^7$ are each independently H or halo.

Provided herein is a compound of formula (I'):

(I')

[Chemical structure showing a spirocyclic compound with substituents $(R^1)_m$, $R^2$, $(R^3)_p$, $L^1$, $L^2$, $L^3$, $R^4$, $R^6$, $R^7$, $X^1$, $X^2$, and N-containing rings]

or a stereoisomer or tautomer thereof, or a pharmaceutically acceptable salt of any of the foregoing, wherein:
m is an integer from 0 to 4;
n is an integer from 0 to 2;
p is an integer from 0 to 10;
$R^1$, if present is, independently at each occurrence selected from the group consisting of halo, —CN, $C_{1-6}$alkoxy, or $C_{1-6}$alkyl, wherein
  the $C_{1-6}$alkoxy of $R^1$ is optionally substituted with one or more halo, and
  the $C_{1-6}$alkyl of $R^1$ is optionally substituted with one or more halo;
$R^2$ is H, $C_{1-6}$alkyl, $C_{3-10}$cycloalkyl, or 3-15 membered heterocyclyl, wherein
  the $C_{1-6}$alkyl of $R^2$ is optionally substituted with one or more halo, —OH, —NH$_2$, or $C_{1-6}$alkoxy, and
  the $C_{3-10}$cycloalkyl of $R^2$ is optionally substituted with one or more —OH;
$R^3$, if present, is $C_{1-6}$alkyl;
$L^1$ is $C_{1-6}$alkylene, wherein the $C_{1-6}$alkylene of $L^1$ is optionally substituted with one or more $C_{1-6}$alkyl, and wherein the $C_{1-6}$alkyl is further optionally substituted with one or more —OH or $C_{1-6}$alkoxy;
$L^2$ is O or N($R^x$), wherein $R^x$ is H or $C_{1-6}$alkyl; and
either
(1) $L^3$ is absent or is O, $C_{3-10}$cycloalkyl, 3-10 membered heterocyclyl, or $C_{1-6}$alkylene, wherein
  the $C_{3-10}$cycloalkyl is optionally substituted with one or more —OH or $C_{1-6}$alkyl,
  the $C_{1-6}$alkylene of $L^3$ is optionally substituted with one or more —OH or $C_{1-6}$alkyl, and
  the 3-10 membered heterocyclyl is optionally substituted with one or more —OH;
$X^1$ and $X^2$ are each independently N or C($R^5$); and
$R^4$ is:
(i) —S(O)$_2$—$R^a$;
(ii) 5-20 membered heteroaryl, wherein the 5-20 membered heteroaryl of $R^4$ is optionally substituted with one or more $C_{1-6}$alkyl;
(iii) —N($R^d$)$_2$, wherein $R^d$ is independently at each occurrence H, $C_{1-6}$ alkyl, or —S(O)$_2$—$R^a$, wherein the $C_{1-6}$alkyl of $R^d$ is optionally substituted with one or more —OH,
(iv) —NS(O)—($C_{1-6}$alkyl)$_2$, wherein the $C_{1-6}$alkyl is optionally substituted with one or more —OH,
(v) —C(O)—N($R^e$)$_2$ wherein $R^e$ is independently at each occurrence H, $C_{1-6}$ alkyl, or 3-10 membered heterocycle, wherein the 3-10 membered heterocycle is optionally substituted with one or more oxo, or both $R^e$ together with the N to which they are attached are taken together to form a 3-10 membered heterocyclyl, wherein the 3-10 membered heterocyclyl is optionally substituted with one or more halo, oxo, —OH, NH$_2$, —NH—S(O)$_2$—$R^a$, or —S(O)$_2$—$R^a$,
(vi) 3-10 membered heterocyclyl optionally substituted with one or more $C_{1-6}$alkyl, —OH, oxo or —S(O)$_2R^a$,
(vii) —S(O)—N($C_{1-6}$alkyl)-($C_{1-6}$alkyl),
(viii) —CN,
(ix) —(CH$_2$)$_q$OH, wherein q is an integer from 0-6,
(x) —C(O)—$C_{1-6}$alkyl, or
(xi) —P(O)($C_{1-6}$alkyl)$_2$;
or
(2) $L^3$ is absent; and
one of $X^1$ and $X^2$ is N or C($R^5$); and
the other of $X^1$ and $X^2$ is N or C that is taken together with $R^4$ and the atoms to which they are attached to form a 5-10 membered heterocyclyl or a 5-20 membered heteroaryl, wherein
  the 5-10 membered heterocyclyl is optionally substituted with one or more $R^b$, wherein $R^b$ is, independently at each occurrence, selected from the group consisting of halo, oxo, $C_{1-6}$alkyl, —C(O)—$C_{1-6}$alkyl, —C(O)—NH$_2$, —C(O)—NH($C_{1-6}$alkyl), —C(O)—N($C_{1-6}$alkyl)$_2$, —S(O)$_2$—$R^a$, $C_{3-10}$cycloalkyl, and 3-10 membered heterocyclyl, wherein
    the $C_{1-6}$alkyl of $R^b$ is optionally substituted with one or more halo, OH, —S(O)$_2$—$C_{1-6}$alkyl, or $C_{3-10}$cycloalkyl, and
    wherein the $C_{3-10}$cycloalkyl of the $C_{1-6}$alkyl of $R^b$ is further optionally substituted with one or more $C_{1-6}$alkyl or —OH and
    the $C_{3-10}$cycloalkyl of $R^b$ is optionally substituted with one or more —OH, $C_{3-10}$cycloalkyl, or $C_{1-6}$alkyl, and
    wherein the $C_{1-6}$alkyl of the $C_{3-10}$cycloalkyl of $R^b$ is further optionally substituted with one or more —OH, and
  the 5-20 membered heteroaryl is optionally substituted with one or more $R^c$, wherein $R^c$ is, independently at each occurrence, selected from the group consisting of halo, $C_{1-6}$alkyl, —C(O)—$C_{1-6}$alkyl, —C(O)—NH$_2$, —C(O)—NH($C_{1-6}$alkyl), —C(O)—N($C_{1-6}$alkyl)$_2$, —S(O)$_2$—$R^a$, $C_{3-10}$cycloalkyl, and 3-10 membered heterocyclyl, wherein
    the $C_{1-6}$alkyl of $R^c$ is optionally substituted with one or more —S(O)$_2$—$C_{1-6}$alkyl,
    the $C_{3-10}$cycloalkyl of $R^c$ is optionally substituted with one or more —OH or $C_{1-6}$alkyl,
    and the 3-10 membered heterocyclyl of $R^c$ is optionally substituted with one or more —OH or $C_{1-6}$alkyl, and
    wherein the $C_{1-6}$alkyl of the 3-10 membered heterocyclyl of $R^c$ is further optionally substituted with one or more —OH;
$R^a$ is, independently at each occurrence:
(i) $C_{1-6}$alkyl optionally substituted with one or more halo, —OH, —S(O)$_2$—$C_{1-6}$alkyl, or —N($C_{1-6}$alkyl)-C(O)—$C_{1-6}$alkyl, (ii) $C_{3-10}$cycloalkyl optionally substituted with one or more —OH, —C(O)$_2$—C$_{1-6}$alkyl, —C(O)—NH(C$_{1-6}$alkyl), —C(O)—N(C$_{1-6}$alkyl)$_2$, or —C(O)—C$_{3-10}$heterocyclyl, or C$_{1-6}$alkyl, wherein the C$_{1-6}$alkyl is optionally substituted with one or more —OH, or (iii) 3-10 membered heterocyclyl optionally substituted with one or more C$_{1-6}$alkyl;

$R^5$ is, independently at each occurrence, H, halo, —CN, 3-10 membered heterocyclyl, C$_{1-6}$alkyl, or C$_{1-6}$alkoxy, wherein the C$_{1-6}$alkyl of $R^5$ is optionally substituted with one or more halo, or —OH and wherein the C$_{1-6}$alkoxy of $R^5$ is optionally substituted with one or more halo; and $R^6$ and $R^7$ are each independently H or halo.

Provided herein is a compound of formula (I):

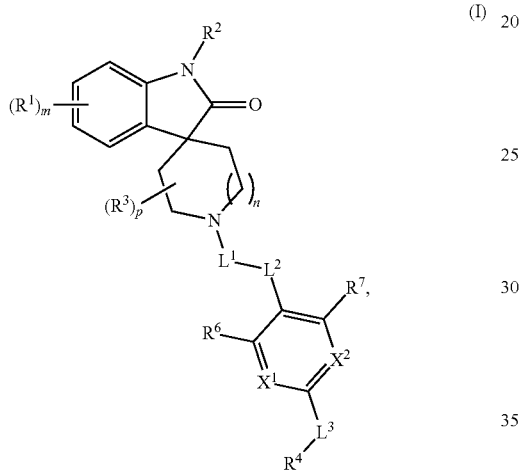

or a stereoisomer or tautomer thereof, or a pharmaceutically acceptable salt of any of the foregoing, wherein:

m is an integer from 0 to 4;

n is an integer from 0 to 2;

p is an integer from 0 to 10;

$R^1$, if present is, independently at each occurrence selected from the group consisting of halo, —CN, C$_{1-6}$alkoxy or —C$_{1-6}$alkyl, wherein
the C$_{1-6}$alkoxy of $R^1$ is optionally substituted with one or more halo, and
the C$_{1-6}$alkyl of $R^1$ is optionally substituted with one or more halo;

$R^2$ is H, C$_{1-6}$alkyl, C$_{3-10}$cycloalkyl, or 3-15 membered heterocyclyl, wherein
the C$_{1-6}$alkyl of $R^2$ is optionally substituted with one or more halo, —OH, —NH$_2$, or C$_{1-6}$alkoxy, and
the C$_{3-10}$cycloalkyl of $R^2$ is optionally substituted with one or more —OH;

$R^3$, if present, is C$_{1-6}$alkyl;

$L^1$ is C$_{1-6}$alkylene, wherein the C$_{1-6}$alkylene of $L^1$ is optionally substituted with one or more C$_{1-6}$alkyl, and wherein the C$_{1-6}$alkyl is further optionally substituted with one or more —OH or C$_{1-6}$alkoxy;

$L^2$ is O or N($R^x$), wherein $R^x$ is H or C$_{1-6}$alkyl; and either (1) $L^3$ is absent or is O, C$_{3-10}$cycloalkyl, 3-10 membered heterocyclyl, or C$_{1-6}$alkylene, wherein
the C$_{1-6}$alkylene of $L^3$ is optionally substituted with one or more C$_{1-6}$alkyl, and
the 3-10 membered heterocyclyl is optionally substituted with one or more —OH;

$X^1$ and $X^2$ are each independently N or C($R^5$); and $R^4$ is:

(i) —S(O)$_2$—$R^a$, (ii) 5-20 membered heteroaryl, wherein the 5-20 membered heteroaryl of $R^4$ is optionally substituted with one or more C$_{1-6}$alkyl, (iii) —N($R^d$)$_2$, wherein $R^d$ is independently at each occurrence H, C$_{1-6}$ alkyl, or —S(O)$_2$—$R^a$, wherein the C$_{1-6}$alkyl of $R^d$ is optionally substituted with one or more —OH, (iv) —NS(O)—(C$_{1-6}$alkyl)$_2$, wherein the C$_{1-6}$alkyl of $R^d$ is optionally substituted with one or more —OH, (v) —C(O)—N($R^e$)$_2$ wherein $R^e$ is independently at each occurrence H, C$_{1-6}$ alkyl, or 3-10 membered heterocycle, wherein the 3-10 membered heterocycle is optionally substituted with one or more oxo, or both $R^e$ together with the N to which they are attached are taken together to form a 3-10 membered heterocyclyl, wherein the 3-10 membered heterocyclyl is optionally substituted with one or more halo, oxo, —OH, NH$_2$, NH—S(O)$_2$—$R^a$, or —S(O)$_2$—$R^a$, (vi) 3-10 membered heterocyclyl optionally substituted with one or more C$_{1-6}$alkyl or oxo, (vii) —S(O)—N(C$_{1-6}$alkyl)-(C$_{1-6}$alkyl), or (viii) —CN;

or (2) $L^3$ is absent; and one of $X^1$ and $X^2$ is N or C($R^5$); and the other of $X^1$ and $X^2$ is N or C that is taken together with $R^4$ and the atoms to which they are attached to form a 5-10 membered heterocyclyl or a 5-20 membered heteroaryl, wherein
the 5-10 membered heterocyclyl is optionally substituted with one or more $R^b$, wherein $R^b$ is, independently at each occurrence, selected from the group consisting of halo, oxo, C$_{1-6}$alkyl, —C(O)—C$_{1-6}$alkyl, —C(O)—NH$_2$, —C(O)—NH(C$_{1-6}$alkyl), —C(O)—N(C$_{1-6}$alkyl)$_2$, —S(O)$_2$—$R^a$, C$_{3-10}$cycloalkyl, and 3-10 membered heterocyclyl, wherein
the C$_{1-6}$alkyl of $R^b$ is optionally substituted with one or more halo, OH, or —S(O)$_2$—C$_{1-6}$alkyl, and
the C$_{3-10}$cycloalkyl of $R^b$ is optionally substituted with one or more —OH, and
the 5-20 membered heteroaryl is optionally substituted with one or more $R^c$, wherein $R^c$ is, independently at each occurrence, selected from the group consisting of halo, C$_{1-6}$alkyl, —C(O)—C$_{1-6}$alkyl, —C(O)—NH$_2$, —C(O)—NH(C$_{1-6}$alkyl), —C(O)—N(C$_{1-6}$alkyl)$_2$, —S(O)$_2$—$R^a$, C$_{3-10}$cycloalkyl, and 3-10 membered heterocyclyl, wherein
the C$_{1-6}$alkyl of $R^c$ is optionally substituted with one or more —S(O)$_2$—C$_{1-6}$alkyl, and
the C$_{3-10}$cycloalkyl of $R^c$ is optionally substituted with one or more —OH;

$R^a$ is, independently at each occurrence:

(i) C$_{1-6}$alkyl optionally substituted with one or more halo, —OH, —S(O)$_2$—C$_{1-6}$alkyl, or —N(C$_{1-6}$alkyl)-C(O)—C$_{1-6}$alkyl, or (ii) C$_{3-10}$cycloalkyl optionally substituted with one or more —OH, —C(O)$_2$—C$_{1-6}$alkyl, —C(O)—NH(C$_{1-6}$alkyl), —C(O)—N(C$_{1-6}$alkyl)$_2$, or —C(O)—C$_{3-10}$heterocyclyl, or C$_{1-6}$alkyl, wherein the C$_{1-6}$alkyl is optionally substituted with one or more —OH, or (iii) 3-10 membered heterocyclyl optionally substituted with one or more C$_{1-6}$alkyl;

R$^5$ is, independently at each occurrence, H, halo, —CN, 3-10 membered heterocyclyl, C$_{1-6}$alkyl, or C$_{1-6}$alkoxy, wherein the C$_{1-6}$alkyl of R$^5$ is optionally substituted with one or more halo, or —OH and wherein the C$_{1-6}$alkoxy is optionally substituted with one or more halo; and R$^6$ and R$^7$ are each independently H or halo.

Any embodiments provided herein of a compound of formula (I), or a stereoisomer or tautomer thereof, or a pharmaceutically acceptable salt of any of the foregoing, or any variation or embodiment thereof, are also embodiments of a compound of formula (I'), or (II), or a stereoisomer or tautomer thereof, or a pharmaceutically acceptable salt of any of the foregoing, or any variation or embodiment thereof.

In some embodiments of a compound of formula (I), or a stereoisomer or tautomer thereof, or a pharmaceutically acceptable salt of any of the foregoing, n is an integer from 0 to 2. In some embodiments, n is 0. In some embodiments, n is 1. In some embodiments, n is 2. In some variations, the embodiments provided herein also apply to a compound of formula (I'), or (II), or a stereoisomer or tautomer thereof, or a pharmaceutically acceptable salt of any of the foregoing, or any variation or embodiment thereof. In some embodiments of a compound of formula (I), or a stereoisomer or tautomer thereof, or a pharmaceutically acceptable salt of any of the foregoing, R$^2$ is H, C$_{1-6}$alkyl, C$_{3-10}$cycloalkyl, or 3-15 membered heterocyclyl, wherein the C$_{1-6}$alkyl of R$^2$ is optionally substituted with one or more halo, —OH, —NH$_2$, or C$_{1-6}$alkoxy, and the C$_{3-10}$cycloalkyl of R$^2$ is optionally substituted with one or more —OH. In some embodiments, R$^2$ is H, C$_{1-3}$alkyl, C$_{3-6}$cycloalkyl, or 3-6 membered heterocyclyl, wherein the C$_{1-3}$alkyl of R$^2$ is optionally substituted with one or more halo, —OH, —NH$_2$, or C$_{1-3}$alkoxy, and the C$_{3-6}$cycloalkyl of R$^2$ is optionally substituted with one or more —OH. In some embodiments, R$^2$ is selected from the group consisting of H,

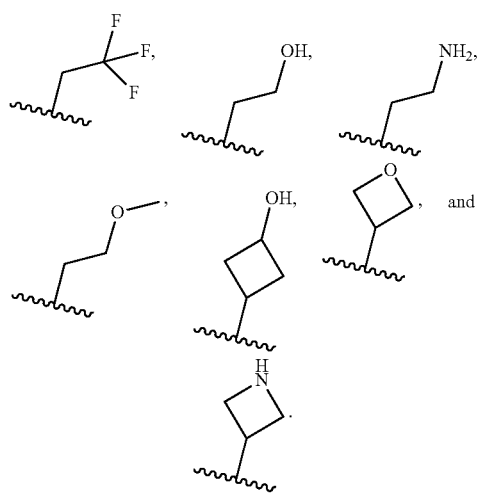

In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (II), or a stereoisomer or tautomer thereof, or a pharmaceutically acceptable salt of any of the foregoing, R$^2$ is H, C$_{1-6}$alkyl, C$_{3-10}$cycloalkyl, or 3-15 membered heterocyclyl, wherein the C$_{1-6}$alkyl of R$^2$ is optionally substituted with one or more deuterieum, halo, —OH, —NH$_2$, or C$_{1-6}$alkoxy, and the C$_{3-10}$cycloalkyl of R$^2$ is optionally substituted with one or more —OH. In some embodiments, R$^2$ is H, C$_{1-3}$alkyl, C$_{3-6}$cycloalkyl, or 3-6 membered heterocyclyl, wherein the C$_{1-3}$alkyl of R$^2$ is optionally substituted with one or more deuterieum, halo, —OH, —NH$_2$, or C$_{1-3}$alkoxy, and the C$_{3-6}$cycloalkyl of R$^2$ is optionally substituted with one or more —OH. In some embodiments, R$^2$ is selected from the group consisting of H,

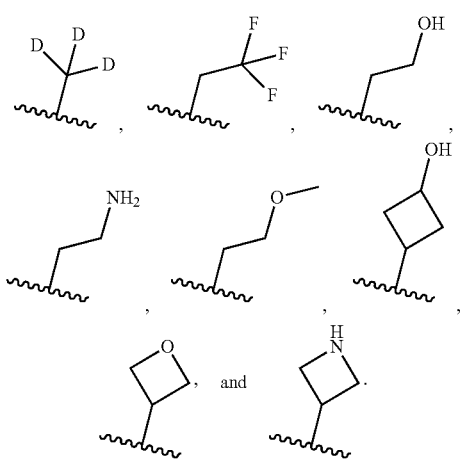

In some embodiments of a compound of formula (I), or a stereoisomer or tautomer thereof, or a pharmaceutically acceptable salt of any of the foregoing, R$^2$ is H. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), formula (I'), or a stereoisomer or tautomer thereof, or a pharmaceutically acceptable salt of any of the foregoing, R$^2$ is C$_{1-6}$alkyl. In some embodiments, R$^2$ is C$_{1-3}$alkyl. In some embodiments R$^2$ is methyl or ethyl. In some embodiments, R$^2$ is methyl. In some variations, the embodiments provided herein also apply to a compound of formula (II), or a stereoisomer or tautomer thereof, or a pharmaceutically acceptable salt of any of the foregoing, or any variation or embodiment thereof.

In some embodiments of a compound of formula (I), or a stereoisomer or tautomer thereof, or a pharmaceutically acceptable salt of any of the foregoing, R$^2$ is C$_{1-6}$alkyl optionally substituted with one or more halo, —OH, —NH$_2$, or C$_{1-6}$alkoxy. In some embodiments, R$^2$ is C$_{1-3}$alkyl optionally substituted with one or more halo, —OH, —NH$_2$, or C$_{1-3}$alkoxy. In some embodiments, R$^2$ is methyl. In some embodiments, R$^2$ is ethyl optionally substituted with one or more halo, —OH, —NH$_2$, or C$_{1-6}$alkoxy. In some embodiments, R$^2$ is selected from the group consisting of

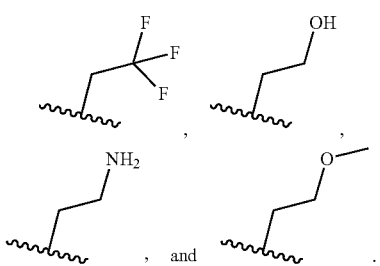

In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), or a stereoisomer or tautomer thereof, or a pharmaceutically acceptable salt of any of the foregoing, $R^2$ is $C_{1-6}$alkyl optionally substituted with one or more deuterium, halo, —OH, —NH$_2$, or $C_{1-6}$alkoxy. In some embodiments, $R^2$ is $C_{1-3}$alkyl optionally substituted with one or more deuterium, halo, —OH, —NH$_2$, or $C_{1-3}$alkoxy. In some embodiments, $R^2$ is methyl. In some embodiments, $R^2$ is ethyl optionally substituted with one or more halo, —OH, —NH$_2$, or $C_{1-6}$alkoxy. In some embodiments, $R^2$ is selected from the group consisting of

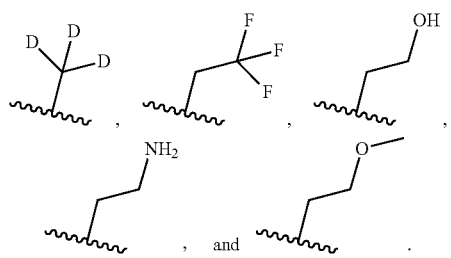

In some embodiments of a compound of formula (I), or a stereoisomer or tautomer thereof, or a pharmaceutically acceptable salt of any of the foregoing, $R^2$ is $C_{3-10}$cycloalkyl, wherein the $C_{3-10}$cycloalkyl of $R^2$ is optionally substituted with one or more —OH. In some embodiments, $R^2$ is $C_{3-6}$cycloalkyl, wherein the $C_{3-6}$cycloalkyl of $R^2$ is optionally substituted with one or more —OH. In some embodiments, $R^2$ is

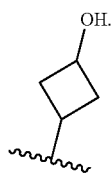

In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), or a stereoisomer or tautomer thereof, or a pharmaceutically acceptable salt of any of the foregoing, $R^2$ is 3-15 membered heterocyclyl. In some embodiments, $R^2$ is 3-6 membered heterocyclyl. In some embodiments, $R^2$ is

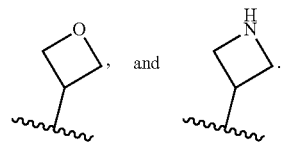 [SMILES: *C1COC1 ; *C1CNC1]

In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), or a stereoisomer or tautomer thereof, or a pharmaceutically acceptable salt of any of the foregoing, m is an integer from 0 to 4. In some embodiments, m is an integer from 0 to 2. In some embodiments, m is 0. In some embodiments m is 1. In some embodiments, m is 2. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), or a stereoisomer or tautomer thereof, or a pharmaceutically acceptable salt of any of the foregoing, $R^1$ is halo, —CN, $C_{1-6}$alkoxy or —$C_{1-6}$alkyl, wherein the $C_{1-6}$alkoxy or $R^1$ is optionally substituted with one or more halo, and wherein the $C_{1-6}$alkyl of $R^1$ is optionally substituted with one or more halo. In some embodiments, $R^1$ is halo, —CN, $C_{1-3}$alkoxy, or —$C_{1-3}$alkyl, wherein the $C_{1-3}$alkoxy of $R^1$ is optionally substituted with one or more halo, and wherein the $C_{1-3}$alkyl of $R^1$ is optionally substituted with one or more halo. In some embodiments, $R^1$ is selected from the group consisting of Cl, Br, —CN, methyl,

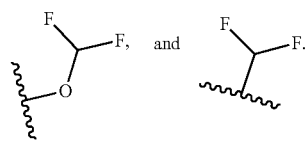

In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I'), or a stereoisomer or tautomer thereof, or a pharmaceutically acceptable salt of any of the foregoing, $R^1$ is halo, —CN, $C_{1-6}$alkoxy or —$C_{1-6}$alkyl, wherein the $C_{1-6}$alkoxy or $R^1$ is optionally substituted with one or more halo, and wherein the $C_{1-6}$alkyl of $R^1$ is optionally substituted with one or more halo. In some embodiments, $R^1$ is halo, —CN, $C_{1-3}$alkoxy, or —$C_{1-3}$alkyl, wherein the $C_{1-3}$alkoxy of $R^1$ is optionally substituted with one or more halo, and wherein the $C_{1-3}$alkyl of $R^1$ is optionally substituted with one or more halo. In some embodiments, $R^1$ is selected from the group consisting of Cl, Br, F, I, —CN, methyl,

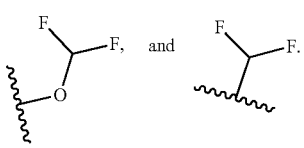

In some variations, the embodiments provided herein also apply to a compound of formula (II), or a stereoisomer or tautomer thereof, or a pharmaceutically acceptable salt of any of the foregoing, or any variation or embodiment thereof.

In some embodiments of a compound of formula (I), or a stereoisomer or tautomer thereof, or a pharmaceutically acceptable salt of any of the foregoing, $R^1$ is halo. In some embodiments $R^1$ is Cl. In some embodiments, $R^1$ is Br. In some embodiments, $R^1$ is F. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I'), or a stereoisomer or tautomer thereof, or a pharmaceutically acceptable salt of any of the foregoing, $R^1$ is halo. In some embodiments $R^1$ is Cl. In some embodiments, $R^1$ is Br. In some embodiments, $R^1$ is F. In some embodiments $R^1$ is I. In some variations, the embodiments provided herein also apply to a compound of formula (II), or a stereoisomer or tautomer thereof, or a pharmaceutically acceptable salt of any of the foregoing, or any variation or embodiment thereof.

In some embodiments of a compound of formula (I), or a stereoisomer or tautomer thereof, or a pharmaceutically acceptable salt of any of the foregoing, $R^1$ is $C_{1-6}$alkyl, wherein the $C_{1-6}$alkyl of $R^1$ is optionally substituted with one or more halo. In some embodiments, $R^1$ is $C_{1-3}$alkyl, wherein the $C_{1-3}$alkyl of $R^1$ is optionally substituted with one or more halo. In some embodiments, $R^1$ is $C_{1-3}$alkyl, wherein the $C_{1-3}$alkyl of $R^1$ is optionally substituted with one or more F. In some embodiments, $R^1$ is methyl, wherein the methyl of $R^1$ is optionally substituted with one or more F. In some embodiments, $R^1$ is methyl. In some embodiments, $R^1$ is

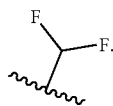 [SMILES: *C(F)F]

In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), or a stereoisomer or tautomer thereof, or a pharmaceutically acceptable salt of any of the foregoing, $R^1$ is —CN. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I'), or a stereoisomer or tautomer thereof, or a pharmaceutically acceptable salt of any of the foregoing, $R^1$ is $C_{1-6}$alkoxy, wherein the $C_{1-6}$alkoxy of $R^1$ is optionally substituted with one or more halo. In some embodiments, $R^1$ is $C_{1-3}$alkoxy, wherein the $C_{1-3}$alkoxy of $R^1$ is optionally substituted with one or more halo. In some embodiments, $R^1$ is $C_{1-3}$alkoxy, wherein the $C_{1-3}$alkoxy of $R^1$ is optionally substituted with one or more F. In some embodiments, $R^1$ is methoxy, wherein the methoxy of $R^1$ is optionally substituted with one or more F. In some embodiments, $R^1$ is

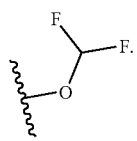

In some variations, the embodiments provided herein also apply to a compound of formula (II), or a stereoisomer or tautomer thereof, or a pharmaceutically acceptable salt of any of the foregoing, or any variation or embodiment thereof.

In some embodiments of a compound of formula (I), or a stereoisomer or tautomer thereof, or a pharmaceutically acceptable salt of any of the foregoing, p is an integer from 0 to 10. In some embodiments, p is 0 or 1. In some embodiments, p is 0. In some embodiments, p is 1. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), or a stereoisomer or tautomer thereof, or a pharmaceutically acceptable salt of any of the foregoing, $R^3$ is $C_{1-6}$alkyl. In some embodiments, $R^3$ is $C_{1-3}$alkyl. In some embodiments, $R^3$ is methyl. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), or a stereoisomer or tautomer thereof, or a pharmaceutically acceptable salt of any of the foregoing, the ring bearing $(R^1)_m$ and $R^2$ is a 2-indolinone optionally substituted at one or more of positions 1, 5, and 7. In some embodiments, the 2-indolinone ring is unsubstituted. In some embodiments, the 2-indolinone ring is substituted at position 1. In some embodiments, the 2-indolinone ring is substituted at position 5. In some embodiments, the 2-indolinone ring is substituted at position 7. In some embodiments, the 2-indolinone ring is substituted at positions 1, and 5. In some embodiments, the 2-indolinone ring is substituted at positions 5 and 7. In some embodiments, the 2-indolinone ring is substituted at positions 1, 5, and 7. In some embodiments positions 1, 5 and 7 are defined as indicated in the structure,

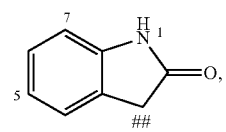

wherein position 1 is a N atom, each of positions 5 and 7 is a C atom, and ## represent the point of attachment to the remainder of the molecule. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), or a stereoisomer or tautomer thereof, or a pharmaceutically acceptable salt of any of the foregoing, the ring bearing $(R^1)_m$ and $R^2$ is selected from the group consisting of

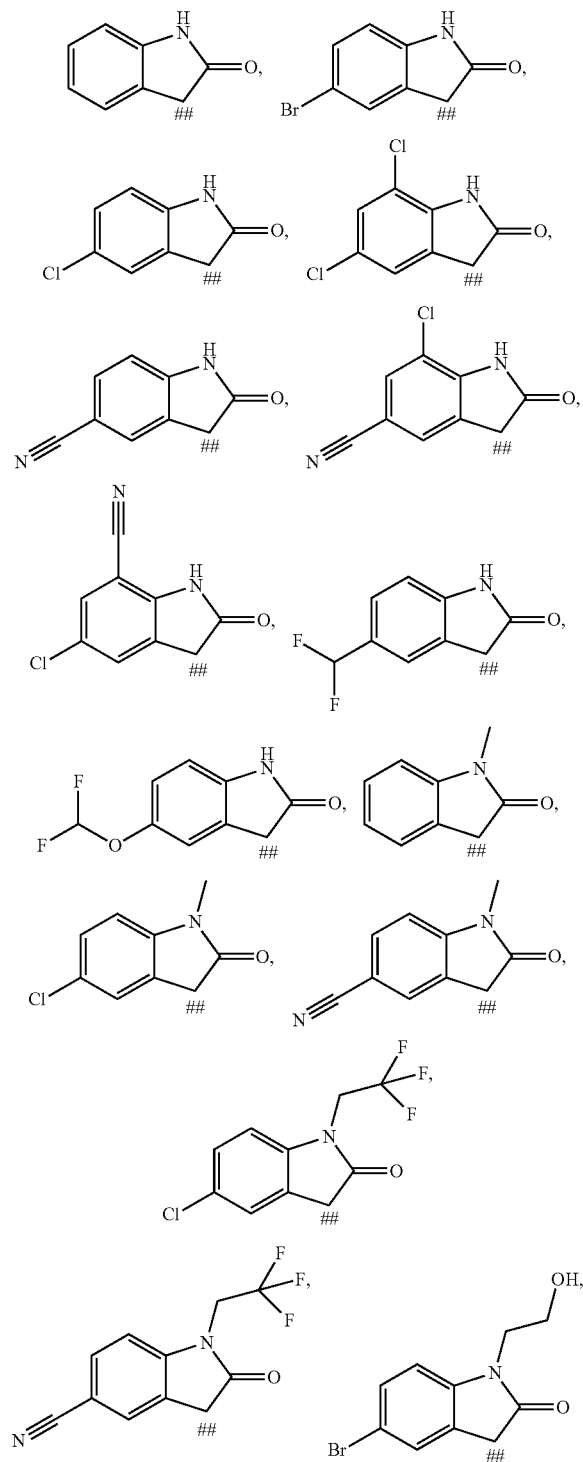

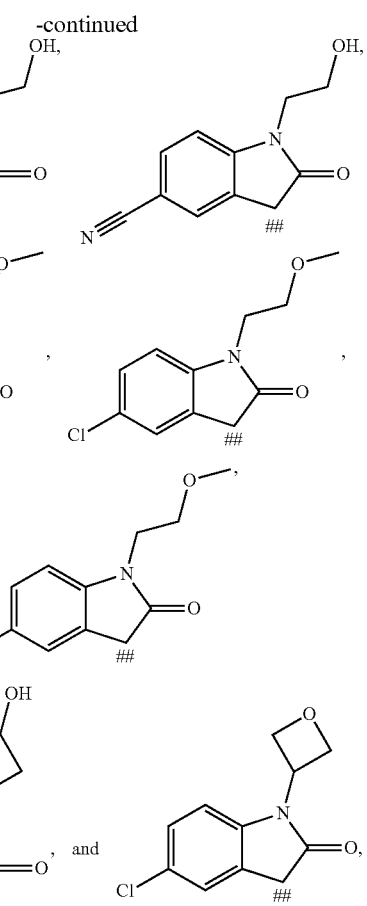

wherein ## represents the point of attachment to the remainder of the molecule. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), formula (I'), or a stereoisomer or tautomer thereof, or a pharmaceutically acceptable salt of any of the foregoing, the ring bearing $(R^1)_m$ and $R^2$ is selected from the group consisting of

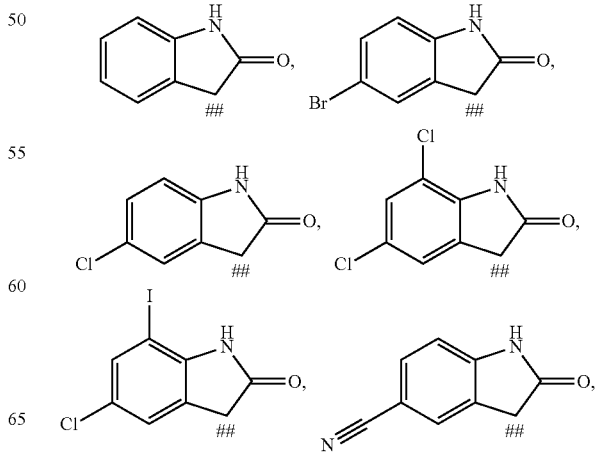

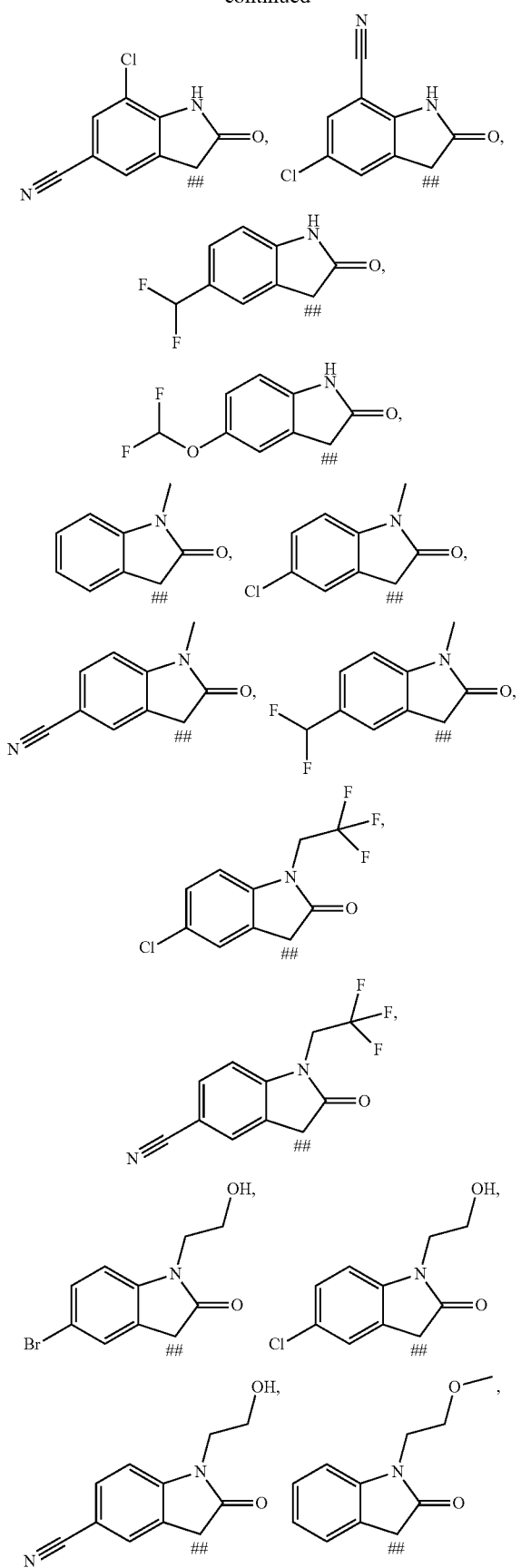
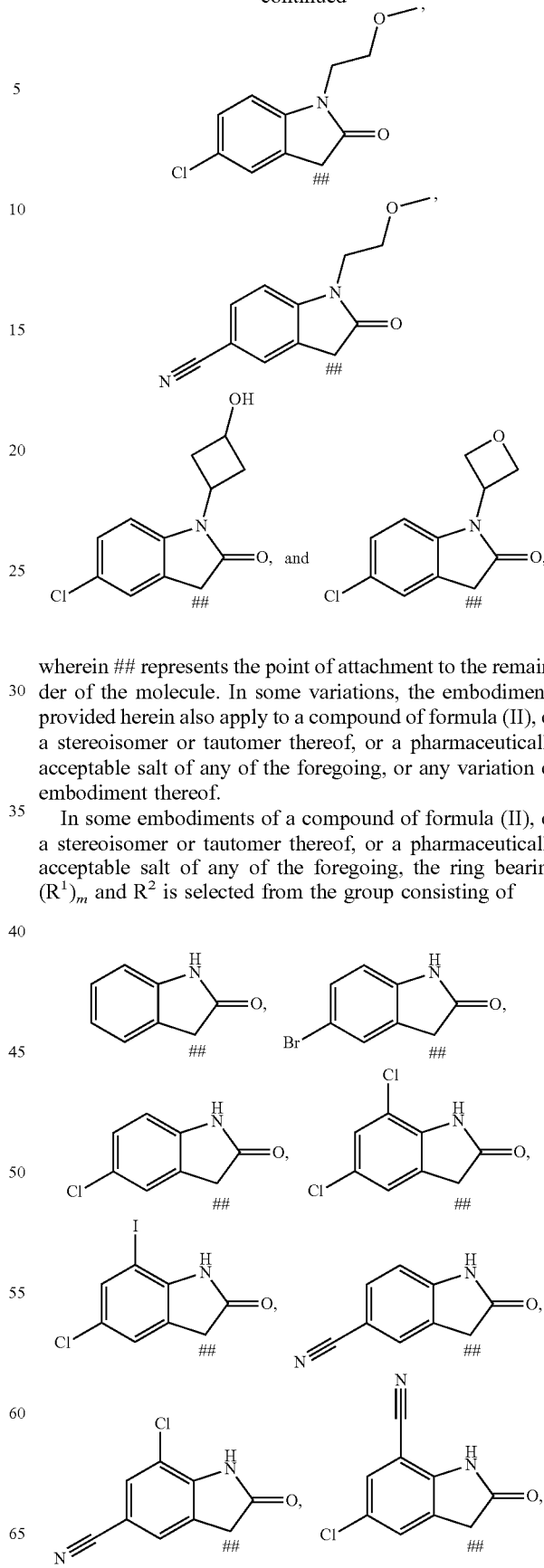

wherein ## represents the point of attachment to the remainder of the molecule. In some variations, the embodiments provided herein also apply to a compound of formula (II), or a stereoisomer or tautomer thereof, or a pharmaceutically acceptable salt of any of the foregoing, or any variation or embodiment thereof.

In some embodiments of a compound of formula (II), or a stereoisomer or tautomer thereof, or a pharmaceutically acceptable salt of any of the foregoing, the ring bearing $(R^1)_m$ and $R^2$ is selected from the group consisting of

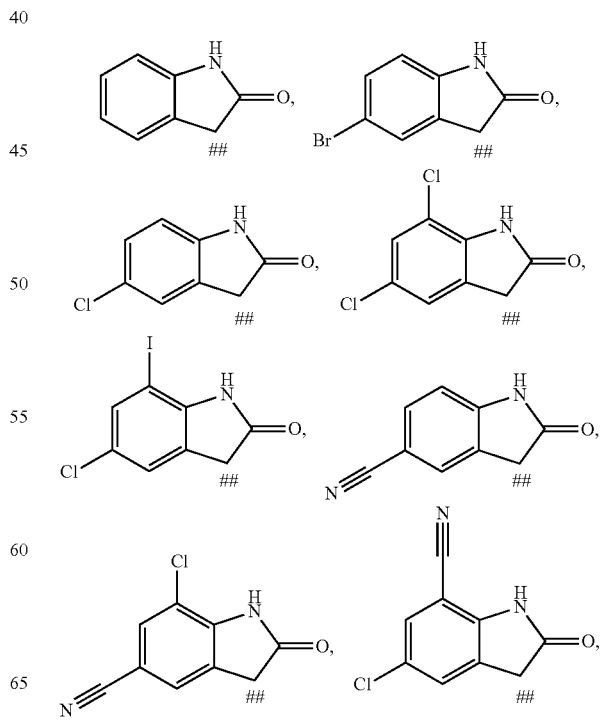

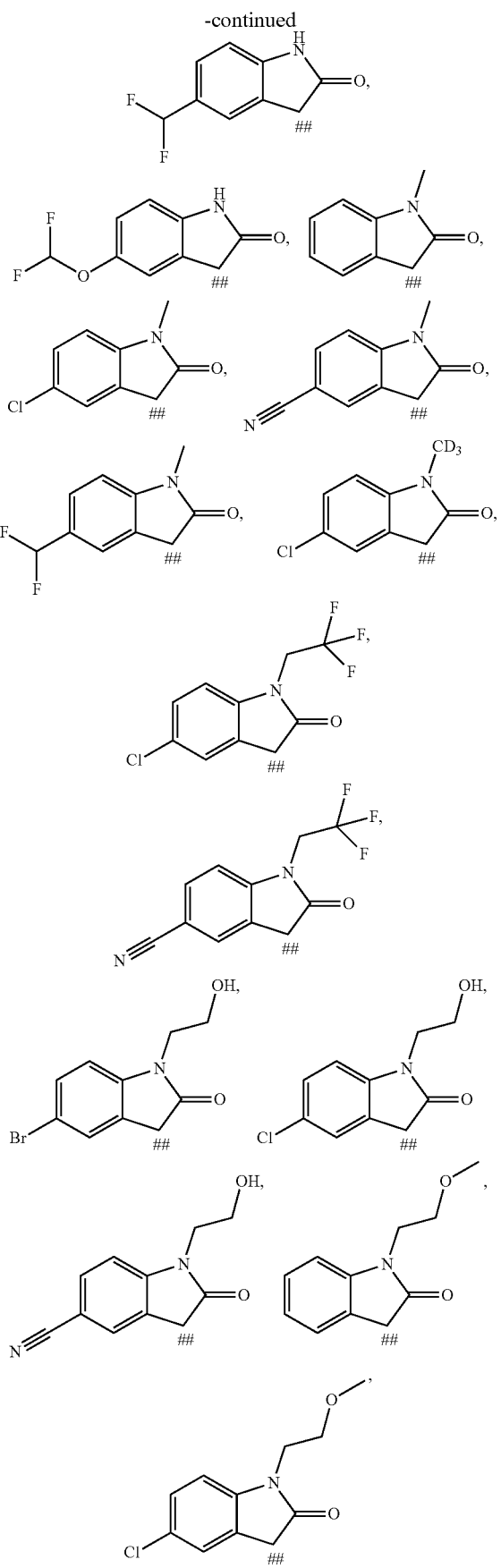

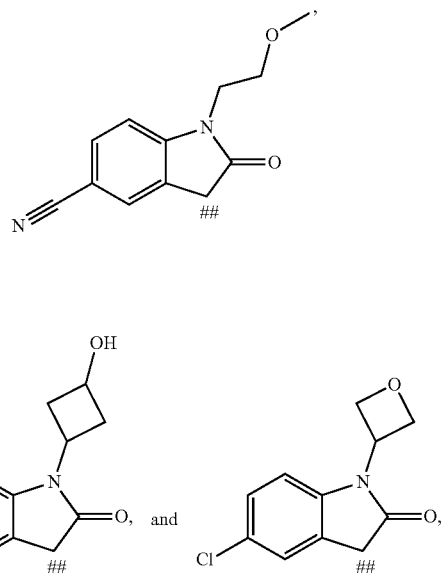

wherein ## represents the point of attachment to the remainder of the molecule.

In some embodiments of a compound of formula (I), or a stereoisomer or tautomer thereof, or a pharmaceutically acceptable salt of any of the foregoing, the ring bearing $(R^3)_p$ is selected from the group consisting of

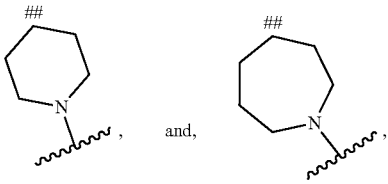 [SMILES: *N1CCCCC1 ; *N1CCCCCC1]

wherein ## represents the point of attachment to the remainder of the molecule. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), or a stereoisomer or tautomer thereof, or a pharmaceutically acceptable salt of any of the foregoing, the ring bearing $(R^1)_m$, $R^2$, and $(R^3)_p$ is selected from the group consisting of

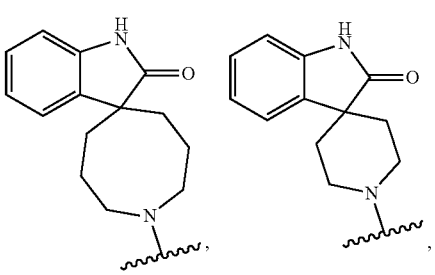

43
-continued
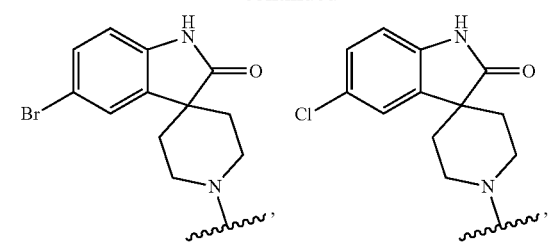
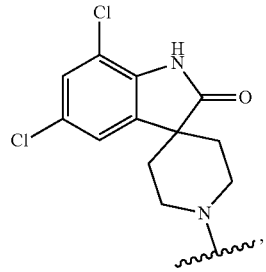
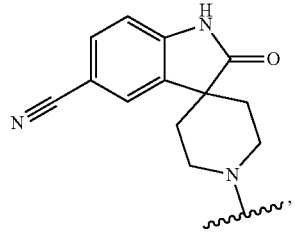
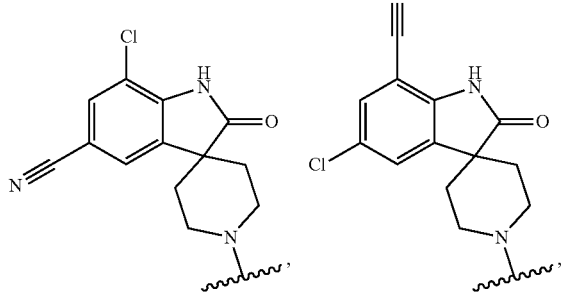
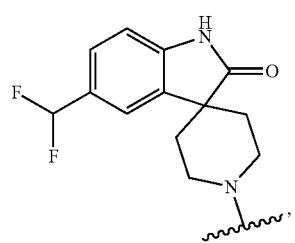
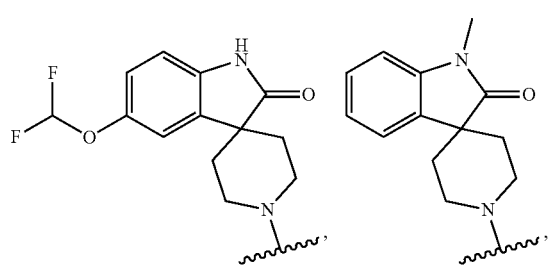
44
-continued
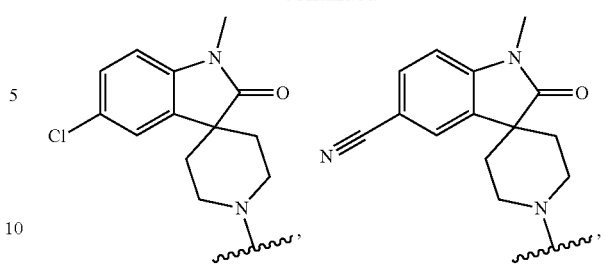
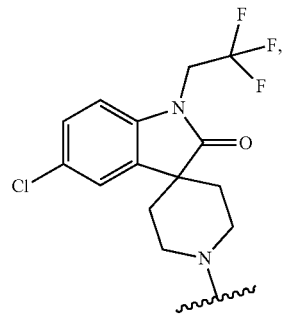
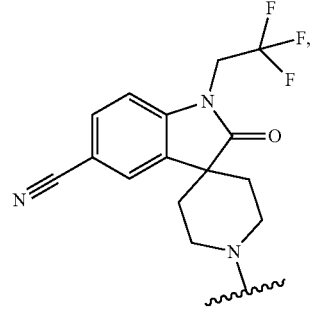
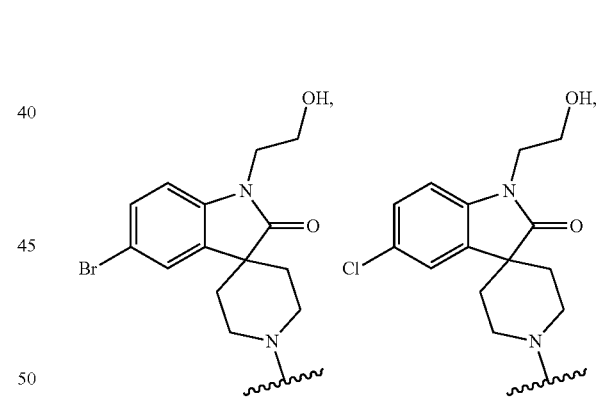
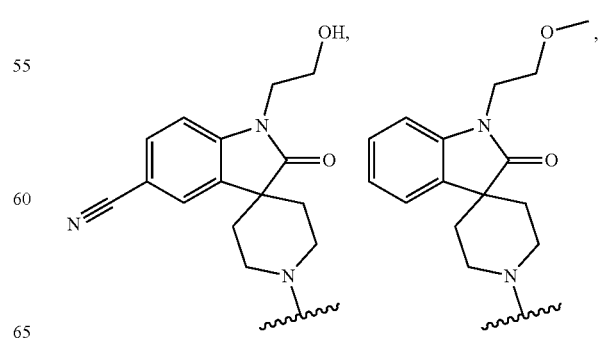

45

-continued

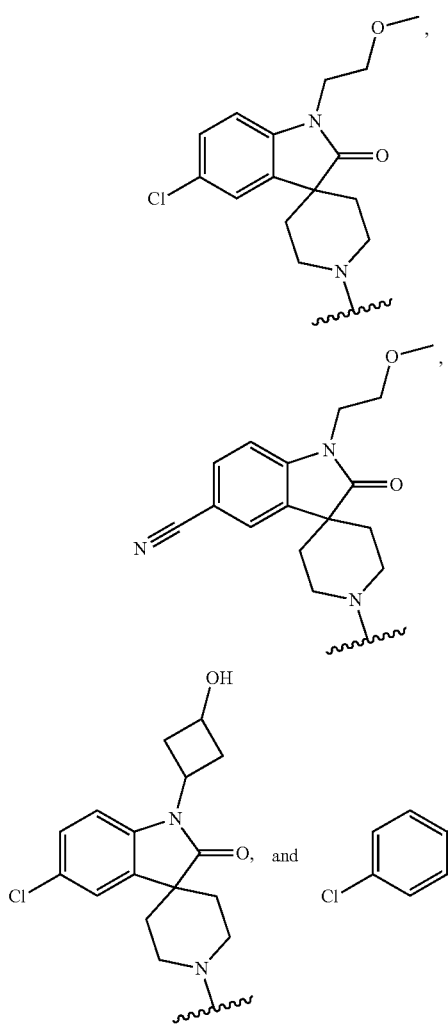

46

-continued

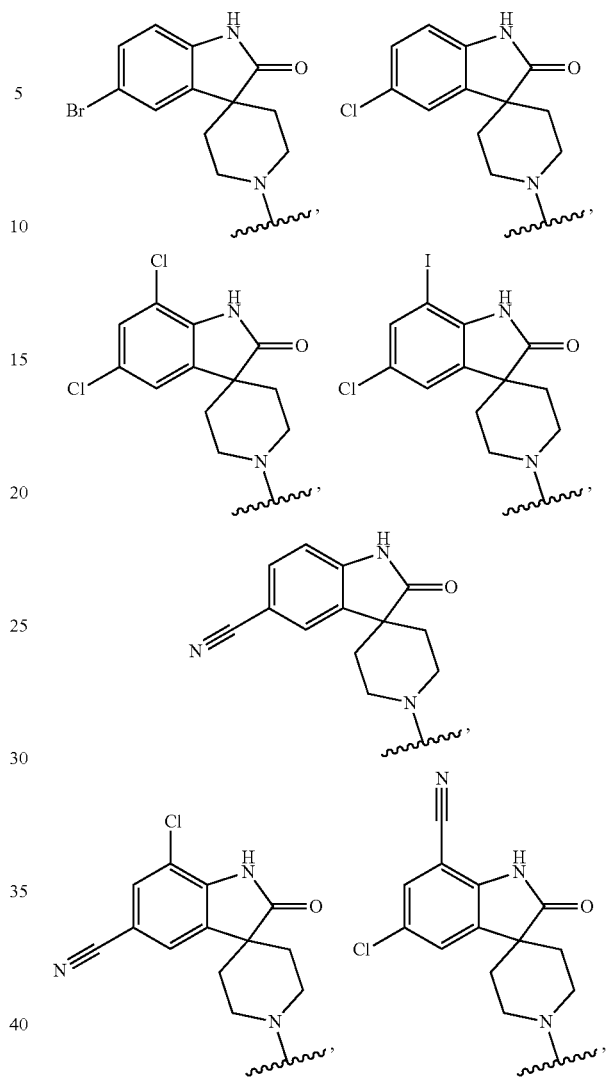

In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I'), or a stereoisomer or tautomer thereof, or a pharmaceutically acceptable salt of any of the foregoing, the ring bearing $(R^1)_m$, $R^2$, and $(R^3)_p$ is selected from the group consisting of

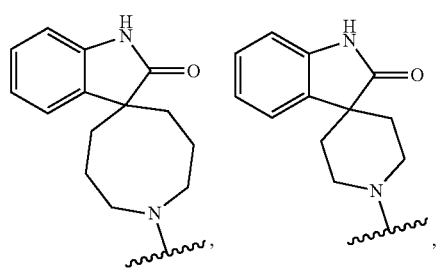

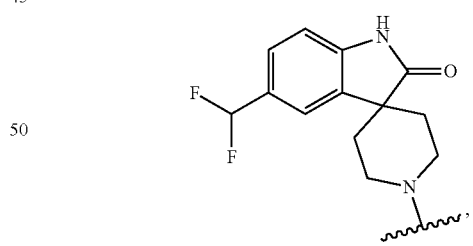

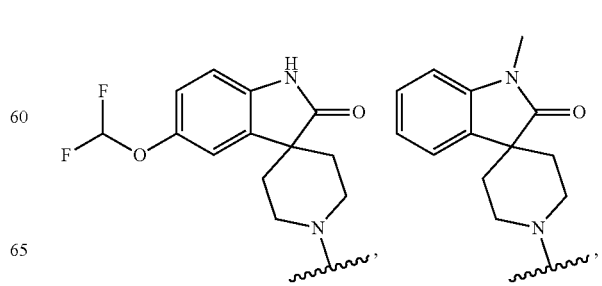

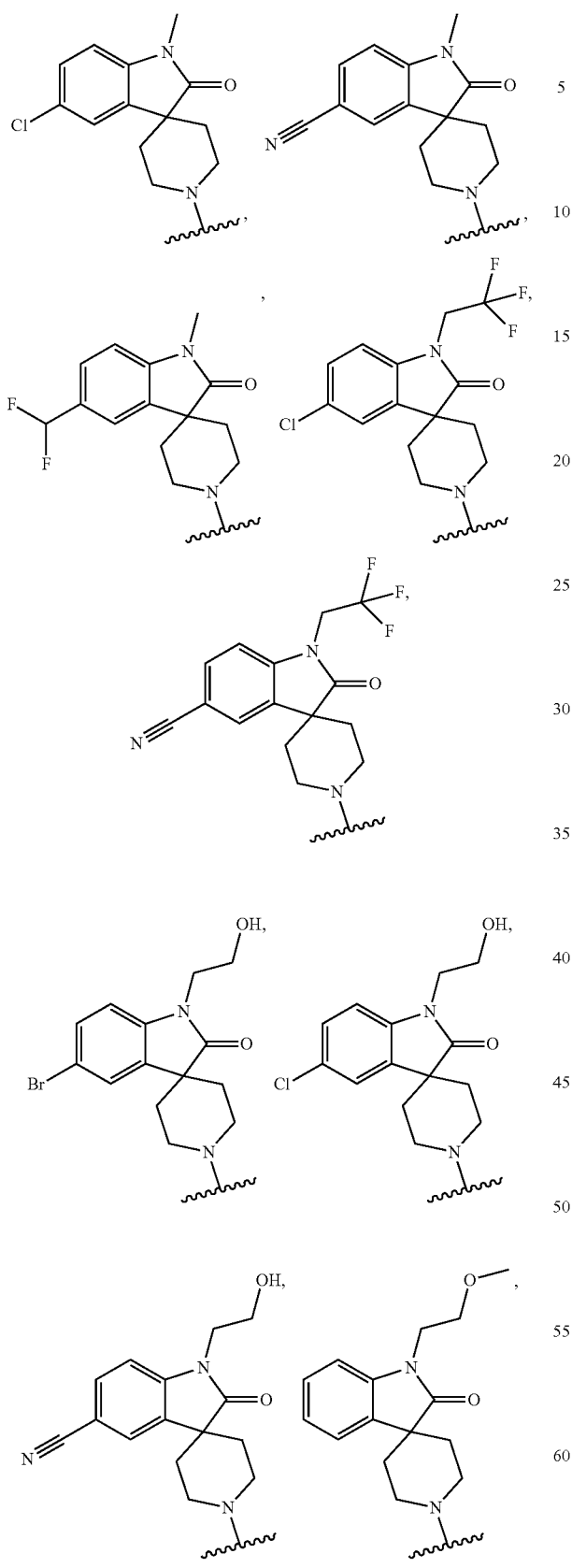
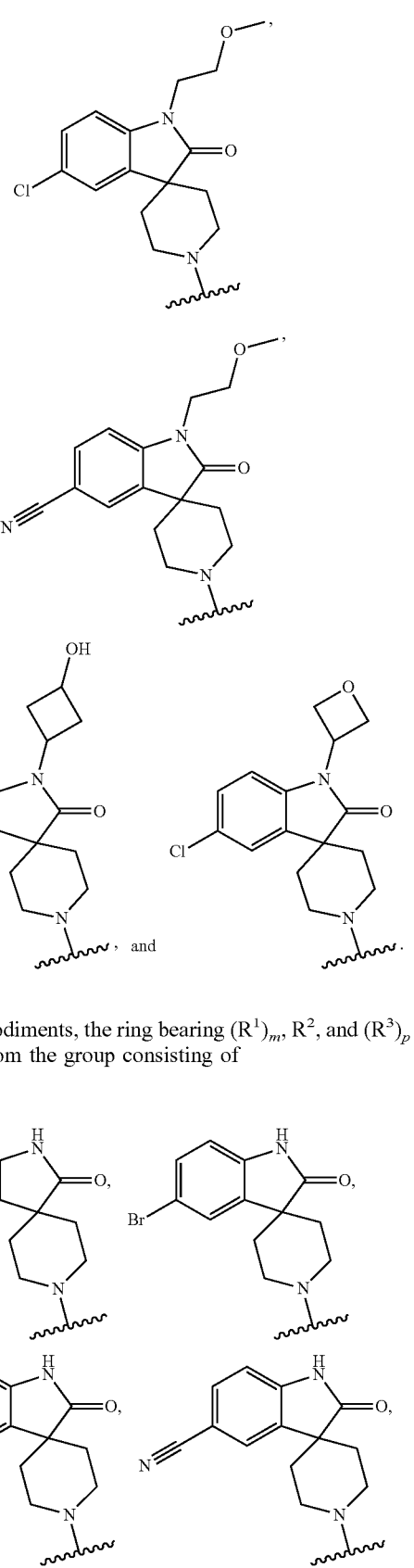
In some embodiments, the ring bearing $(R^1)_m$, $R^2$, and $(R^3)_p$ is selected from the group consisting of -continued

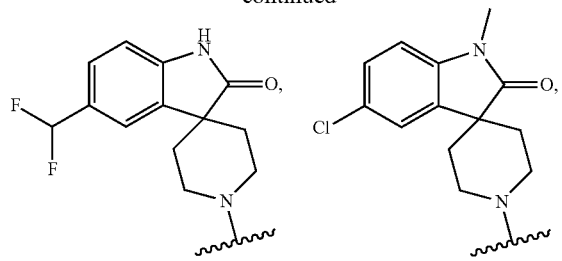

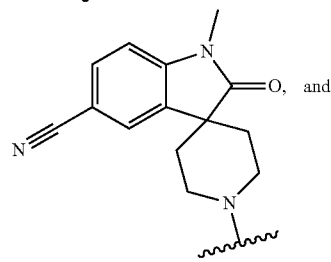

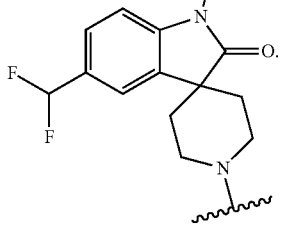

In some embodiments, the ring bearing $(R^1)_m$, $R^2$, and $(R^3)_p$ is selected from the group consisting of

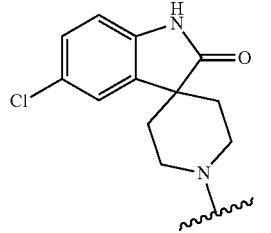

and

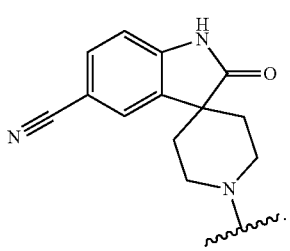

In some embodiments, the ring bearing $(R^1)_m$, $R^2$, and $(R^3)_p$ is

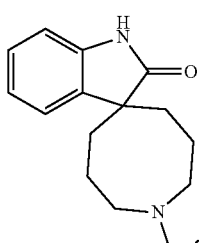

In some embodiments, the ring bearing $(R^1)_m$, $R^2$, and $(R^3)_p$ is

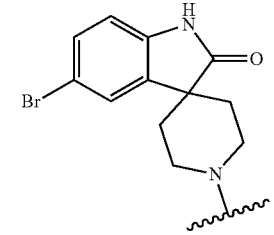 [SMILES: *N1CCC2(CC1)C(=O)Nc1ccc(Cl)cc12]

In some variations, the embodiments provided herein also apply to a compound of formula (II), or a stereoisomer or tautomer thereof, or a pharmaceutically acceptable salt of any of the foregoing, or any variation or embodiment thereof.

In some embodiments of a compound of formula (II), or a stereoisomer or tautomer thereof, or a pharmaceutically acceptable salt of any of the foregoing, the ring bearing $(R^1)_m$, $R^2$, and $(R^3)_p$ is selected from the group consisting of

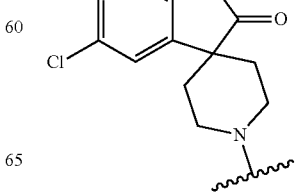

51
-continued
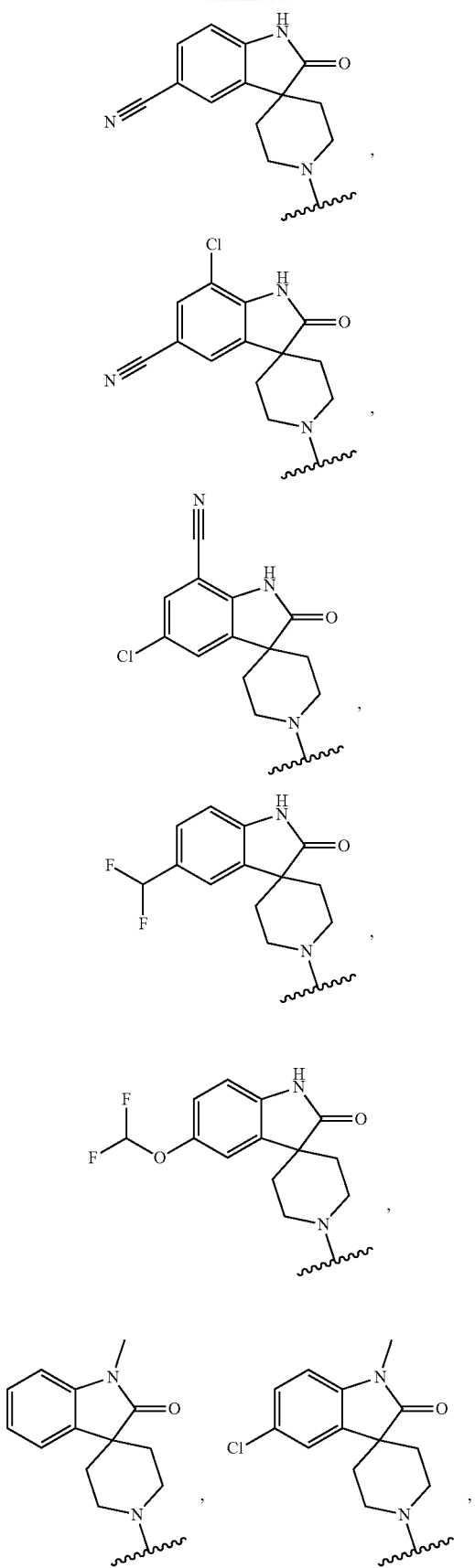
52
-continued
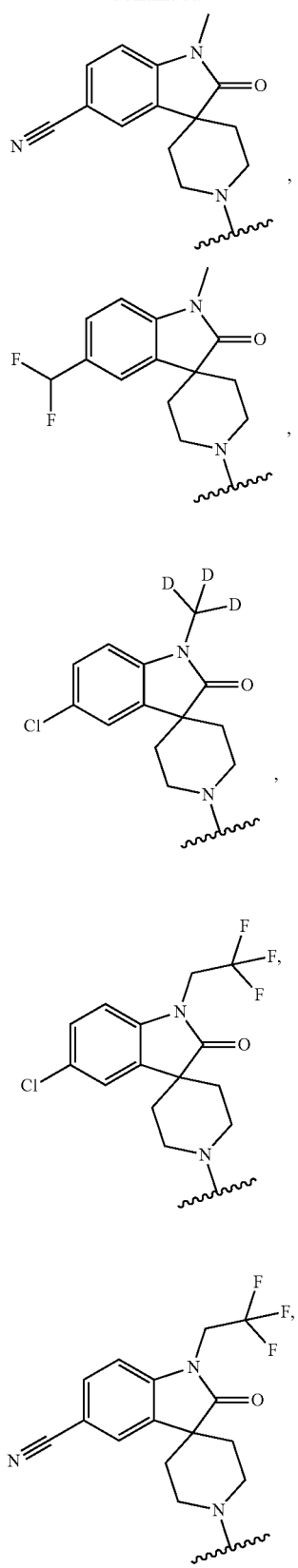

-continued
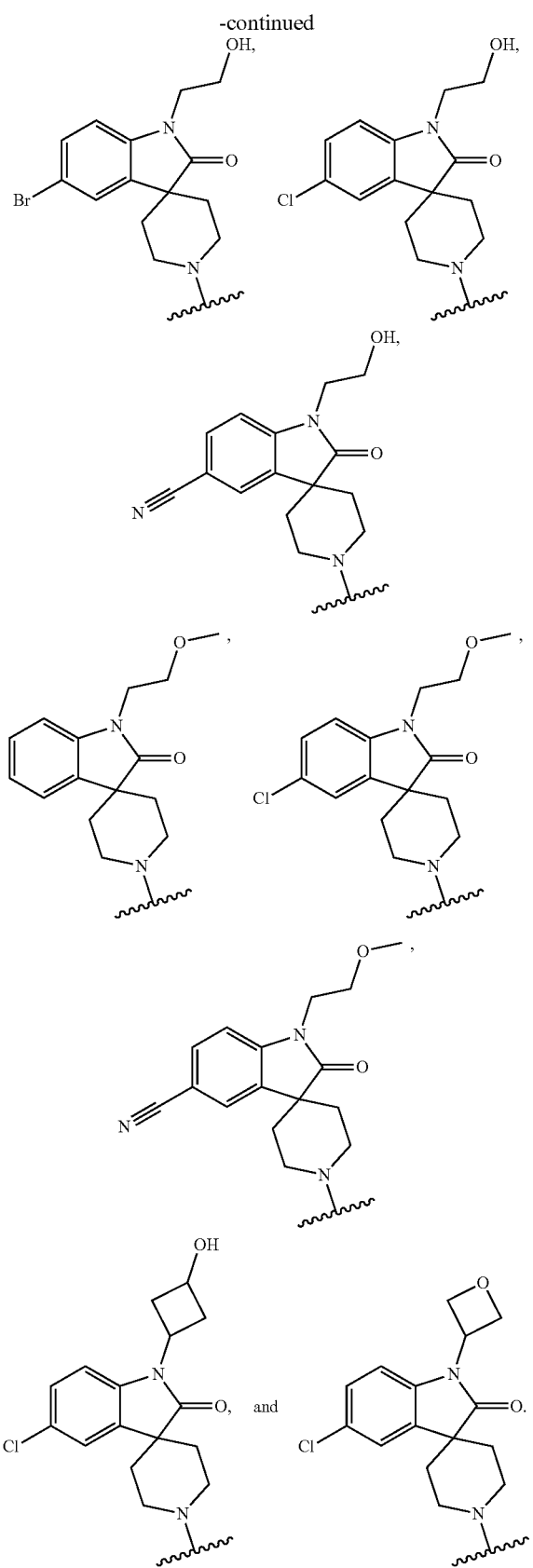
In some embodiments, the ring bearing $(R^1)_m$, $R^2$, and $(R^3)_p$ is selected from the group consisting of
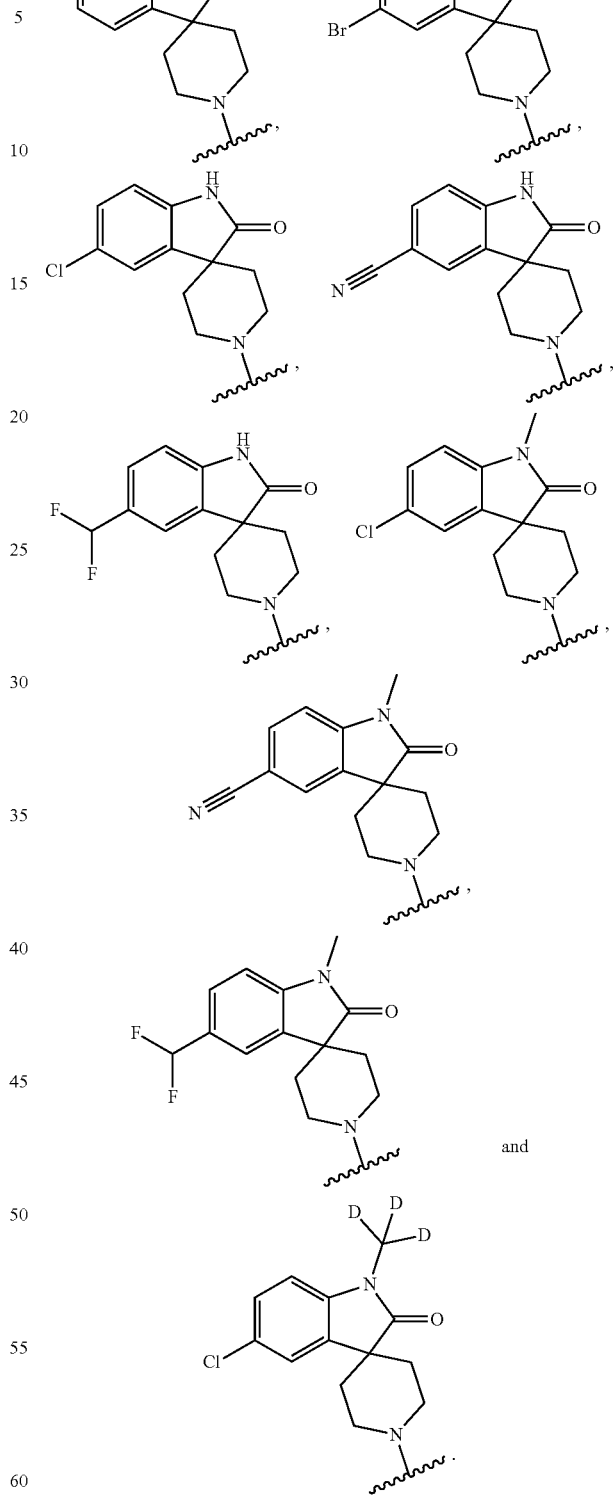
In some embodiments, the ring bearing $(R^1)_m$, $R^2$, and $(R^3)_p$ is selected from the group consisting of

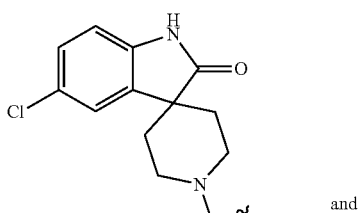

and

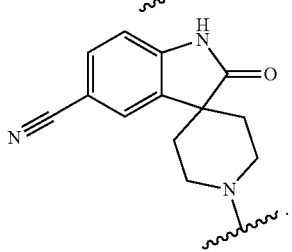

In some embodiments, the ring bearing $(R^1)_m$, $R^2$, and $(R^3)_p$ is

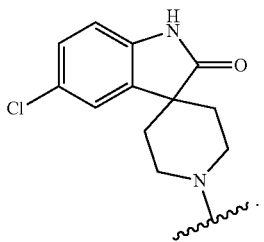 [SMILES: *N1CCC2(CC1)C(=O)Nc1ccc(Cl)cc12]

In some embodiments, the ring bearing $(R^1)_m$, $R^2$, and $(R^3)_p$ is

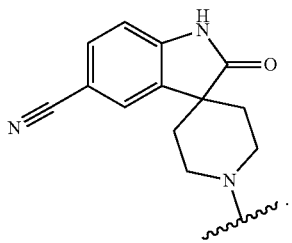 [SMILES: *N1CCC2(CC1)C(=O)Nc1ccc(C#N)cc12]

In some embodiments, the ring bearing $(R^1)_m$, $R^2$, and $(R^3)_p$ is

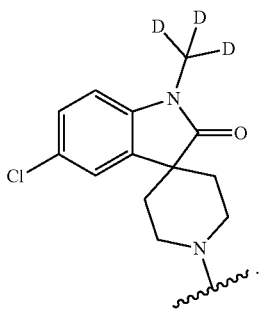 [SMILES: *N1CCC2(CC1)C(=O)N(C([2H])([2H])[2H])c1ccc(Cl)cc12]

In some embodiments of a compound of formula (I), or a stereoisomer or tautomer thereof, or a pharmaceutically acceptable salt of any of the foregoing, $L^1$ is $C_{1-6}$alkylene optionally substituted with one or more $C_{1-6}$alkyl, wherein the $C_{1-6}$alkyl is optionally substituted with —OH or $C_{1-6}$alkoxy. In some embodiments, $L^1$ is $C_{1-3}$alkylene optionally substituted with one or more $C_{1-3}$alkyl, wherein the $C_{1-3}$alkyl is optionally substituted with —OH or $C_{1-3}$alkoxy. In some embodiments, $L^1$ is methylene. In some embodiments, $L^1$ is ethylene. In some embodiments, $L^1$ is ethylene optionally substituted with one or more $C_{1-3}$alkyl, wherein the $C_{1-3}$alkyl is optionally substituted with one or more —OH or $C_{1-3}$alkoxy. In some embodiments, $L^1$ is selected from the group consisting of

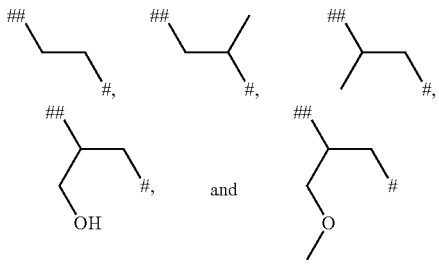

wherein, for each $L^1$, # denotes the point of attachment to $L^2$ and ## denotes the point of attachment to the remainder of the molecule. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (II), or a stereoisomer or tautomer thereof, or a pharmaceutically acceptable salt of any of the foregoing, $L^1$ is $C_{1-6}$alkylene optionally substituted with one or more deuterieum, or $C_{1-6}$alkyl, wherein the $C_{1-6}$alkyl is optionally substituted with —OH or $C_{1-6}$alkoxy. In some embodiments, $L^1$ is $C_{1-3}$alkylene optionally substituted with one or more deuterium, or $C_{1-3}$alkyl, wherein the $C_{1-3}$alkyl is optionally substituted with —OH or $C_{1-3}$alkoxy. In some embodiments, $L^1$ is methylene. In some embodiments, $L^1$ is ethylene. In some embodiments, $L^1$ is ethylene optionally substituted with one or more deuterium, or $C_{1-3}$alkyl, wherein the $C_{1-3}$alkyl is optionally substituted with one or more —OH or $C_{1-3}$alkoxy. In some embodiments, $L^1$ is selected from the group consisting of

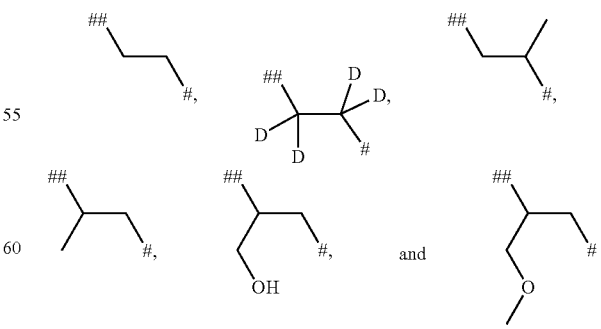

wherein, for each $L^1$, # denotes the point of attachment to $L^2$ and ## denotes the point of attachment to the remainder of the molecule.

In some embodiments of a compound of formula (I), or a stereoisomer or tautomer thereof, or a pharmaceutically acceptable salt of any of the foregoing, $L^2$ is O or $N(R^x)$, wherein $R^x$ is H or $C_{1-6}$alkyl. In some embodiments, $L^2$ is O or $N(R^x)$, wherein $R^x$ is H or $C_{1-3}$alkyl. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), or a stereoisomer or tautomer thereof, or a pharmaceutically acceptable salt of any of the foregoing, $L^2$ is O. In some variations, the embodiments provided herein also apply to a compound of formula (I') or a stereoisomer or tautomer thereof, or a pharmaceutically acceptable salt of any of the foregoing, or any variation or embodiment thereof.

In some embodiments of a compound of formula (I), or a stereoisomer or tautomer thereof, or a pharmaceutically acceptable salt of any of the foregoing, $L^3$ is absent or is O, $C_{3-10}$cycloalkyl, 3-10 membered heterocyclyl, or $C_{1-6}$alkylene, wherein the $C_{1-6}$alkylene of $L^3$ is optionally substituted with one or more $C_{1-6}$alkyl, the $C_{3-10}$cycloalkyl of $L^3$ is optionally substituted with one or more —OH, and the 3-10 membered heterocyclyl of $L^3$ is optionally substituted with one or more —OH. In some embodiments, $L^3$ absent or is selected from the group consisting of O,

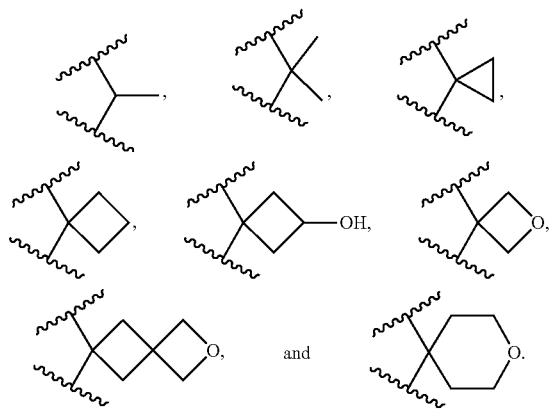

In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I'), or a stereoisomer or tautomer thereof, or a pharmaceutically acceptable salt of any of the foregoing, $L^3$ is absent or is O, $C_{3-10}$cycloalkyl, 3-10 membered heterocyclyl, or $C_{1-6}$alkylene, wherein the $C_{3-10}$cycloalkyl is optionally substituted with one or more —OH, or $C_{1-6}$alkyl, the $C_{1-6}$alkylene of $L^3$ is optionally substituted with one or more —OH, or $C_{1-6}$alkyl, and the 3-10 membered heterocyclyl is optionally substituted with one or more —OH. In some embodiments, $L^3$ absent or is selected from the group consisting of O,

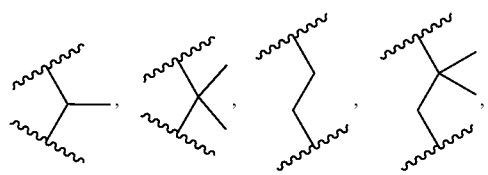

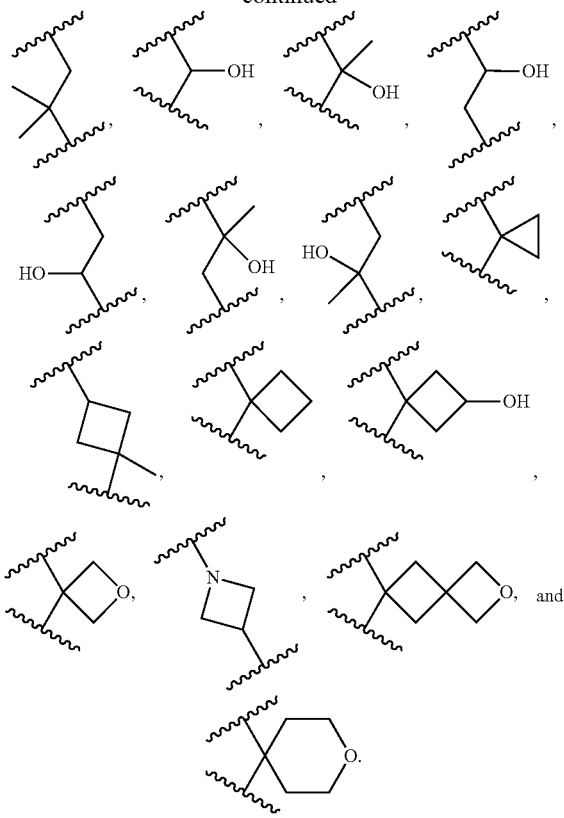

In some variations, the embodiments provided herein also apply to a compound of formula (II), or a stereoisomer or tautomer thereof, or a pharmaceutically acceptable salt of any of the foregoing, or any variation or embodiment thereof.

In some embodiments of a compound of formula (II), or a stereoisomer or tautomer thereof, or a pharmaceutically acceptable salt of any of the foregoing, $L^3$ is absent or is O, $C_{3-10}$cycloalkyl, 3-10 membered heterocyclyl, or $C_{1-6}$alkylene, wherein the $C_{3-10}$cycloalkyl of $L^3$ is optionally substituted with one or more —OH, or $C_{1-6}$alkyl; the $C_{1-6}$alkylene of $L^3$ is optionally substituted with one or more —OH, or $C_{1-6}$alkyl wherein the $C_{1-6}$alkyl is optionally substituted with one or more —OH; and the 3-10 membered heterocyclyl is optionally substituted with one or more —OH or $C_{1-6}$alkyl. In some embodiments, $L^3$ absent or is selected from the group consisting of O,

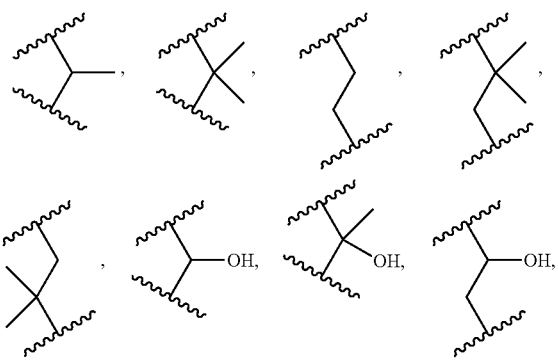

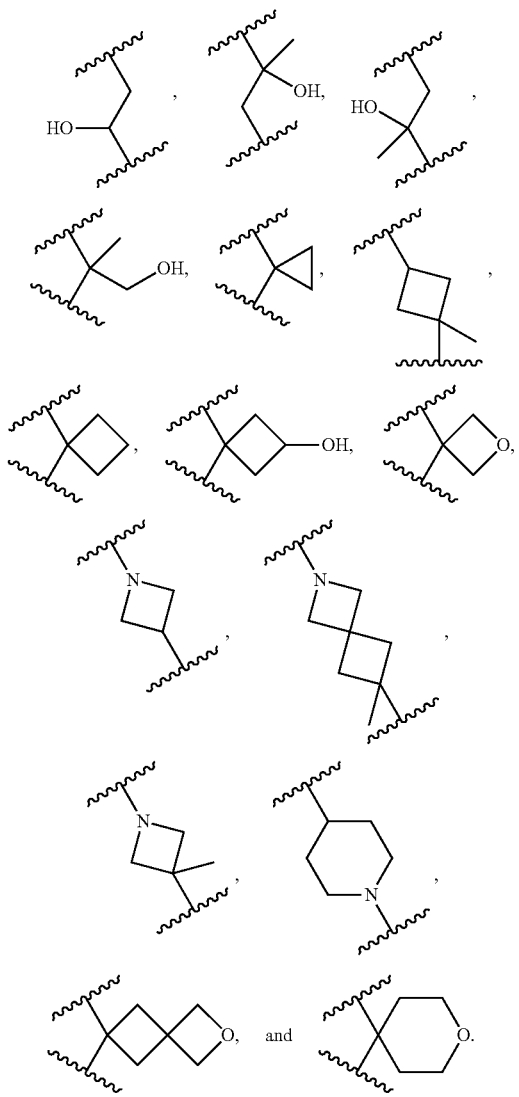

In some embodiments of a compound of formula (I), or a stereoisomer or tautomer thereof, or a pharmaceutically acceptable salt of any of the foregoing, L³ is absent. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), or a stereoisomer or tautomer thereof, or a pharmaceutically acceptable salt of any of the foregoing, L³ is O. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), or a stereoisomer or tautomer thereof, or a pharmaceutically acceptable salt of any of the foregoing, L³ is C$_{1-6}$alkylene. In some embodiments, L³ is C$_{1-3}$alkylene. In some embodiments, L³ is selected from the group consisting of

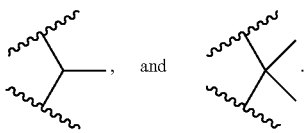

In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), formula (I'), or a stereoisomer or tautomer thereof, or a pharmaceutically acceptable salt of any of the foregoing, L³ is C$_{1-6}$alkylene, wherein the C$_{1-6}$alkylene of L³ is optionally substituted with one or more —OH, or C$_{1-6}$alkyl. In some embodiments, L³ is C$_{1-3}$alkylene, wherein the C$_{1-6}$alkylene of L³ is optionally substituted with one or more —OH, or C$_{1-6}$alkyl. In some embodiments, L³ is selected from the group consisting of

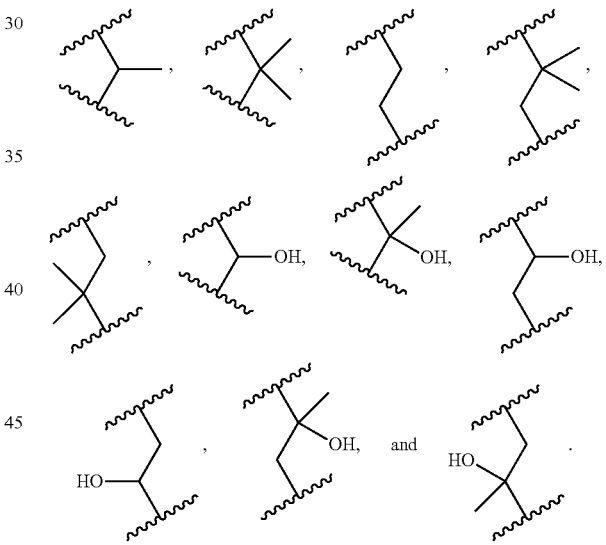

In some variations, the embodiments provided herein also apply to a compound of formula (II), or a stereoisomer or tautomer thereof, or a pharmaceutically acceptable salt of any of the foregoing, or any variation or embodiment thereof.

In some embodiments of a compound of formula (II) or a stereoisomer or tautomer thereof, or a pharmaceutically acceptable salt of any of the foregoing, L³ is C$_{1-6}$alkylene, wherein the C$_{1-6}$alkylene of L³ is optionally substituted with one or more —OH, or C$_{1-6}$alkyl wherein the C$_{1-6}$alkyl is optionally substituted with one or more —OH. In some embodiments, L³ is C$_{1-3}$alkylene, wherein the C$_{1-6}$alkylene of L³ is optionally substituted with one or more —OH, or C$_{1-6}$alkyl. In some embodiments, L³ is selected from the group consisting of

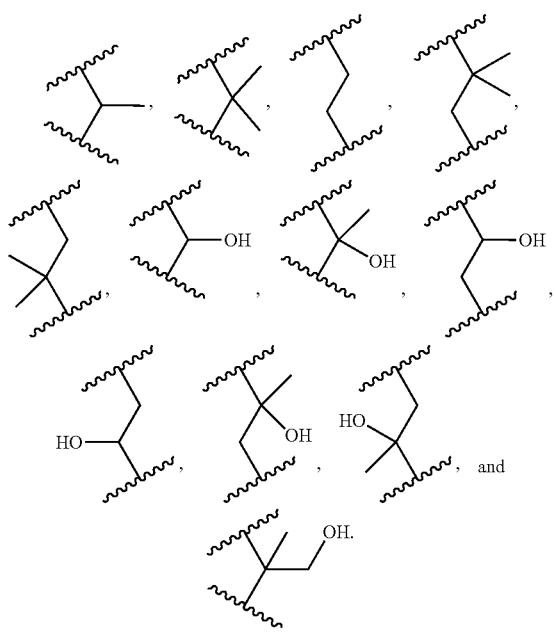

In some embodiments of a compound of formula (I), (I-A), (I-A2), (I-B), or (I-B1), or a stereoisomer or tautomer thereof, or a pharmaceutically acceptable salt of any of the foregoing, $L^3$ is $C_{3-10}$cycloalkyl, wherein the $C_{3-10}$cycloalkyl of $L^3$ is optionally substituted with one or more —OH. In some embodiments, $L^3$ is $C_{3-8}$cycloalkyl, wherein the $C_{3-8}$cycloalkyl of $L^3$ is optionally substituted with one or more —OH. In some embodiments, $L^3$ is selected from the group consisting of

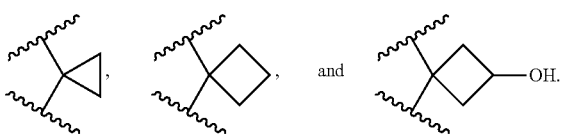 [SMILES: *C1(*)CC1 ; *C1(*)CCC1 ; *C1(*)CC(O)C1]

In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I'), (I), (I-A), (I-A2), (I-B), or (I-B1), or a stereoisomer or tautomer thereof, or a pharmaceutically acceptable salt of any of the foregoing, $L^3$ is $C_{3-10}$cycloalkyl, wherein the $C_{3-10}$cycloalkyl of $L^3$ is optionally substituted with one or more —OH. In some embodiments, $L^3$ is $C_{3-8}$cycloalkyl, wherein the $C_{3-8}$cycloalkyl of $L^3$ is optionally substituted with one or more —OH. In some embodiments, $L^3$ is selected from the group consisting of

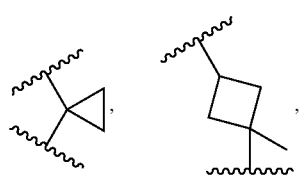

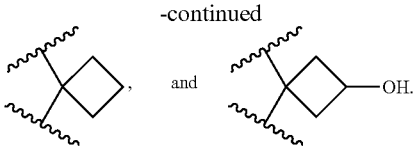

In some variations, the embodiments provided herein also apply to a compound of formula (II), or a stereoisomer or tautomer thereof, or a pharmaceutically acceptable salt of any of the foregoing, or any variation or embodiment thereof.

In some embodiments of a compound of formula (I), or a stereoisomer or tautomer thereof, or a pharmaceutically acceptable salt of any of the foregoing, $L^3$ is 3-10 membered heterocyclyl. In some embodiments, $L^3$ is 3-6 membered heterocyclyl. In some embodiments, $L^3$ is selected from the group consisting of

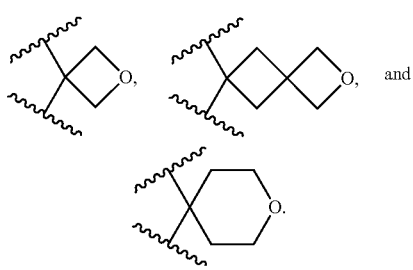

In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), formula (I') or a stereoisomer or tautomer thereof, or a pharmaceutically acceptable salt of any of the foregoing, L3 is 3-10 membered heterocyclyl. In some embodiments, $L^3$ is 3-6 membered heterocyclyl. In some embodiments, L3 is selected from the group consisting of

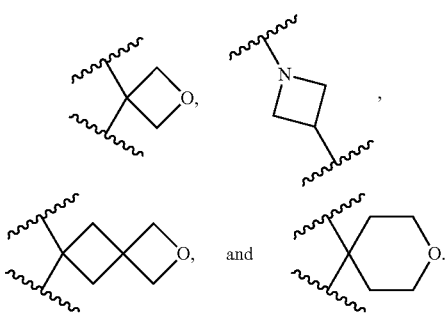

In some variations, the embodiments provided herein also apply to a compound of formula (II), or a stereoisomer or tautomer thereof, or a pharmaceutically acceptable salt of any of the foregoing, or any variation or embodiment thereof.

In some embodiments of a compound of formula (II), or a stereoisomer or tautomer thereof, or a pharmaceutically acceptable salt of any of the foregoing, L3 is 3-10 membered heterocyclyl. In some embodiments, $L^3$ is 3-6 membered heterocyclyl. In some embodiments, L3 is selected from the group consisting of

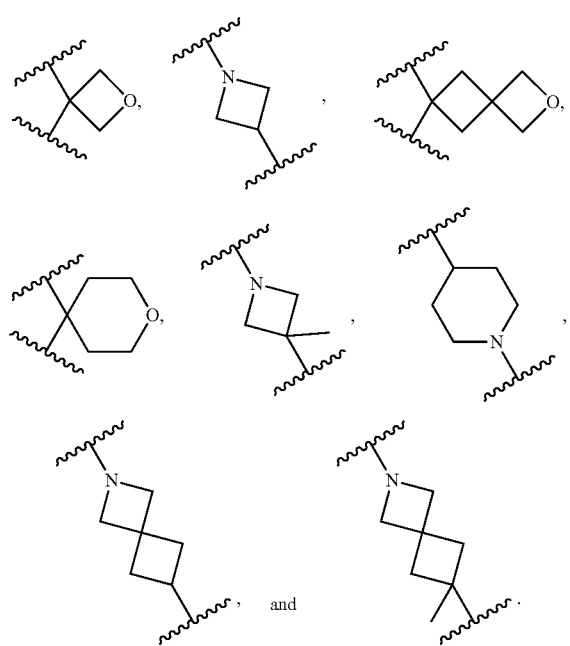

In some embodiments of a compound of formula (I), or a stereoisomer or tautomer thereof, or a pharmaceutically acceptable salt of any of the foregoing $R^4$ is —S(O)$_2$—$R^a$, 5-20 membered heteroaryl, —N($R^d$)$_2$, —NS(O)—(C$_{1-6}$alkyl)$_2$, —C(O)—N($R^e$)$_2$, 3-10 membered heterocyclyl, —S(O)(N—C$_{1-6}$alkyl)-(C$_{1-6}$alkyl), or —CN. In some embodiments, $R^4$ is S(O)$_2$—$R^a$, 5-10 membered heteroaryl, —N($R^d$)$_2$, —NS(O)—(C$_{1-3}$alkyl)$_2$, —C(O)—N($R^e$)$_2$, 3-6 membered heterocyclyl, —S(O)(N—C$_{1-3}$alkyl)-(C$_{1-3}$alkyl), or —CN. In some embodiments, $R^4$ is selected from the group consisting of —NH$_2$, —CN, —C(O)—N(CH$_3$)$_2$,

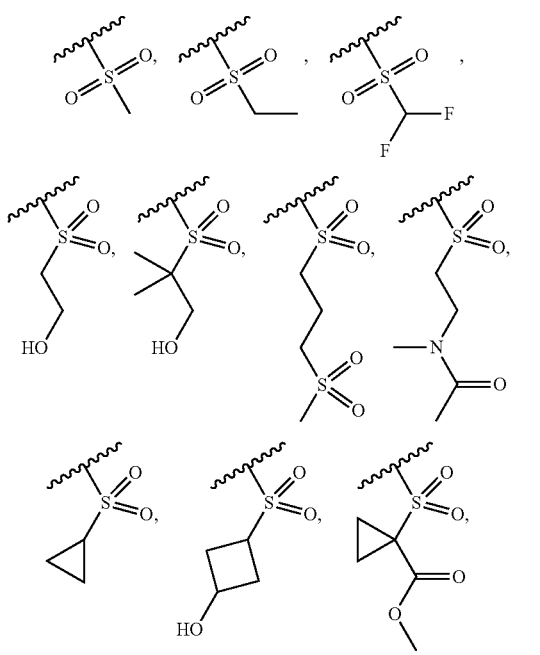

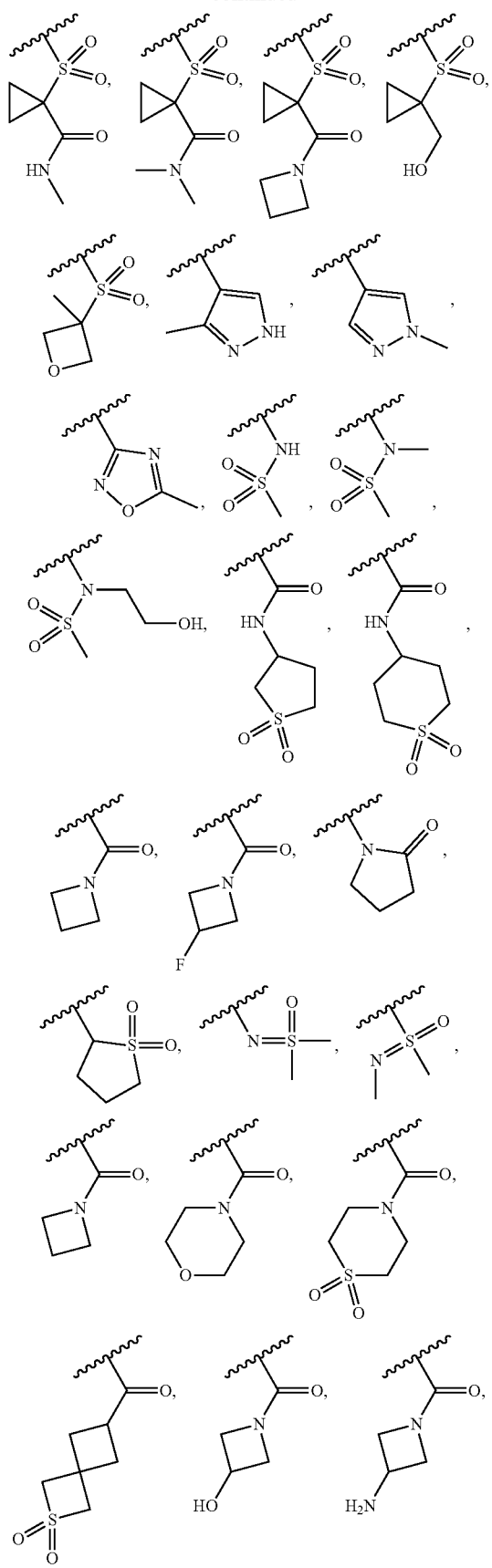

-continued

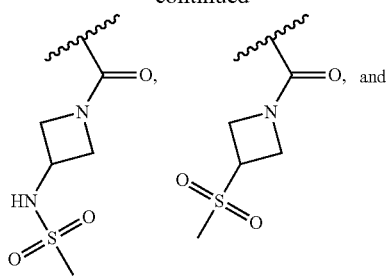

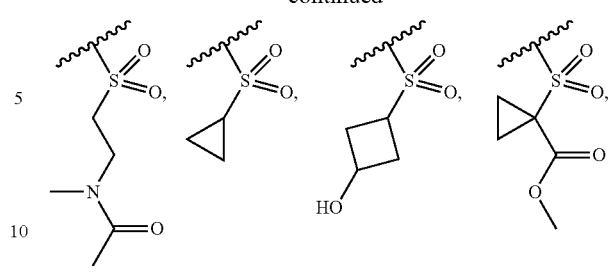

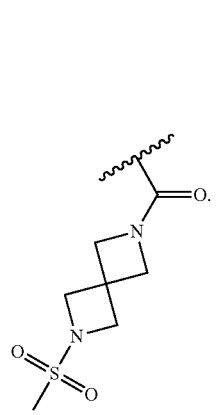

In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (II), or a stereoisomer or tautomer thereof, or a pharmaceutically acceptable salt of any of the foregoing $R^4$ is —S(O)$_2$—R$^a$, 5-20 membered heteroaryl, —N(R$^d$)$_2$, —NS(O)—(C$_{1-6}$alkyl)$_2$, —C(O)—N(R$^e$)$_2$, 3-10 membered heterocyclyl, —S(O)—N(C$_{1-6}$alkyl)-(C$_{1-6}$alkyl), —CN, —(CH$_2$)$_q$OH, —C(O)—C$_{1-6}$alkyl, or —P(O)(C$_{1-6}$alkyl)$_2$. In some embodiments, $R^4$ is S(O)$_2$—R$^a$, 5-10 membered heteroaryl, —N(R$^d$)$_2$, —NS(O)—(C$_{1-3}$alkyl)$_2$, —C(O)—N(R$^e$)$_2$, 3-6 membered heterocyclyl, —S(O)(N—C$_{1-3}$alkyl)-(C$_{1-3}$alkyl), —CN, —OH, —CH$_2$OH, —C(O)—C$_{1-3}$alkyl, or —P(O)(C$_{1-3}$alkyl)$_2$. In some embodiments, $R^4$ is selected from the group consisting of —NH$_2$—CN, —OH, —CH$_2$OH, —C(O)—N(CH$_3$)$_2$,

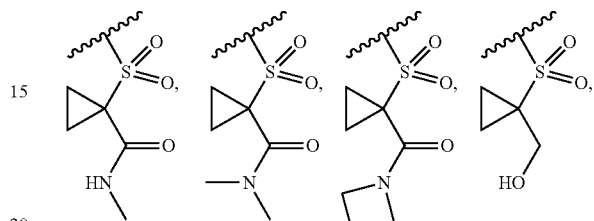

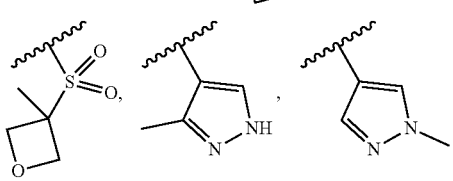

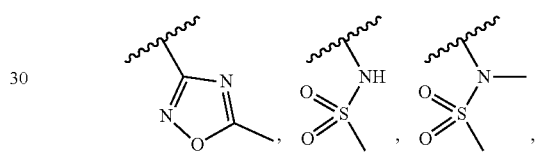

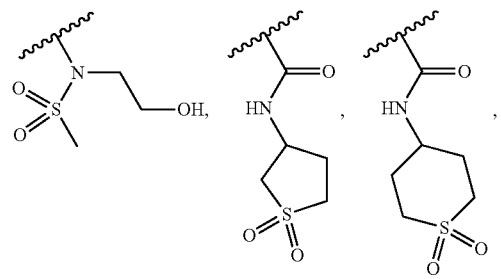

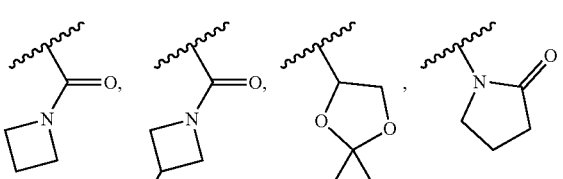

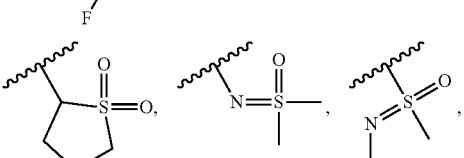

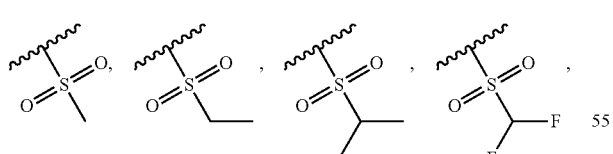

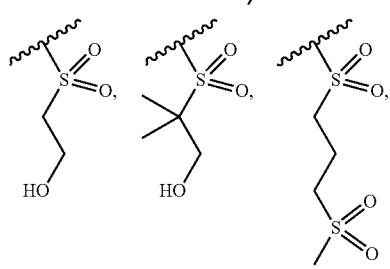

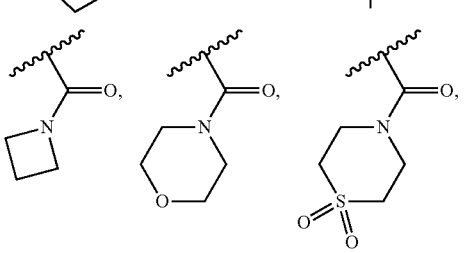

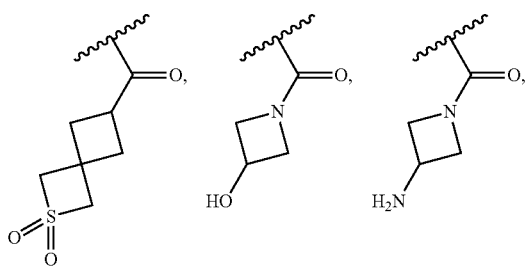

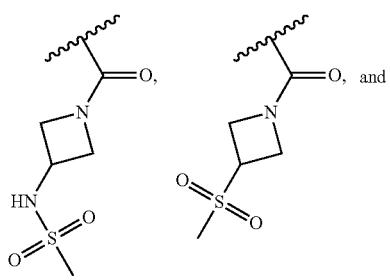

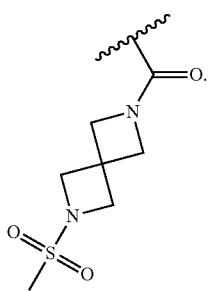

In some embodiments of a compound of formula (I), or a stereoisomer or tautomer thereof, or a pharmaceutically acceptable salt of any of the foregoing, $R^4$ is —S(O)$_2$—$R^a$, wherein $R^a$ is C$_{1-6}$alkyl. In some embodiments, $R^4$ is —S(O)$_2$—$R^a$, wherein $R^a$ is C$_{1-6}$alkyl optionally substituted with one or more halo, —OH, —S(O)$_2$—C$_{1-6}$alkyl, or —N(C$_{1-6}$alkyl)-C(O)—C$_{1-6}$alkyl. In some embodiments, $R^4$ is —S(O)$_2$—$R^a$, wherein $R^a$ is C$_{1-3}$alkyl optionally substituted with one or more halo, —OH, —S(O)$_2$—C$_{1-3}$alkyl, or —N(C$_{1-3}$alkyl)-C(O)—C$_{1-3}$alkyl. In some embodiments, $R^4$ is selected from the group consisting of

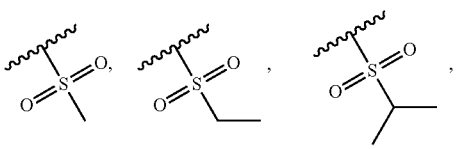

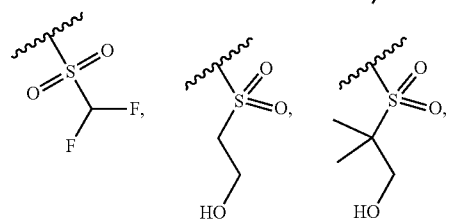

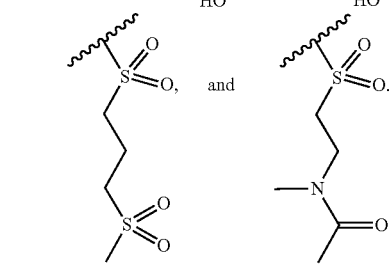

In some embodiments of a compound of formula (I'), or (II), or a stereoisomer or tautomer thereof, or a pharmaceutically acceptable salt of any of the foregoing, or any variation or embodiment thereof.

In some embodiments of a compound of formula (II), or a stereoisomer or tautomer thereof, or a pharmaceutically acceptable salt of any of the foregoing, $R^4$ is —S(O)$_2$—$R^a$, wherein $R^a$ is C$_{1-6}$alkyl. In some embodiments, $R^4$ is —S(O)$_2$—$R^a$, wherein $R^a$ is C$_{1-6}$alkyl optionally substituted with one or more halo, —OH, —S(O)$_2$—C$_{1-6}$alkyl, or —N(C$_{1-6}$alkyl)-C(O)—C$_{1-6}$alkyl. In some embodiments, $R^4$ is —S(O)$_2$—$R^a$, wherein $R^a$ is C$_{1-3}$alkyl optionally substituted with one or more halo, —OH, —S(O)$_2$—C$_{1-3}$alkyl, or —N(C$_{1-3}$alkyl)-C(O)—C$_{1-3}$alkyl. In some embodiments, $R^4$ is selected from the group consisting of

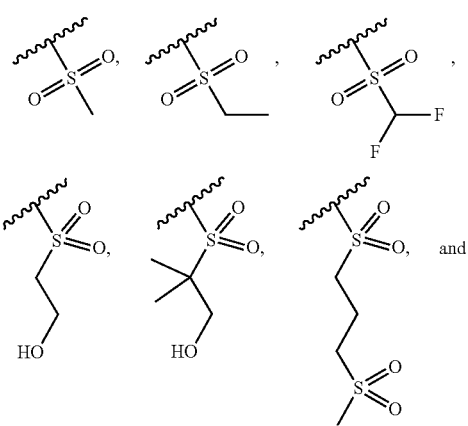

In some embodiments of a compound of formula (I), or a stereoisomer or tautomer thereof, or a pharmaceutically acceptable salt of any of the foregoing, $R^4$ is —S(O)$_2$—$R^a$, wherein $R^a$ is C$_{3-10}$cycloalkyl. In some embodiments, $R^4$ is —S(O)$_2$—$R^a$, wherein $R^a$ is C$_{3-10}$cycloalkyl optionally substituted with one or more —OH, C(O)$_2$—C$_{1-6}$alkyl, —C(O)—NH(C$_{1-6}$alkyl), —C(O)—N(C$_{1-6}$alkyl)$_2$, —C(O)—C$_{3-10}$heterocyclyl or C$_{1-6}$alkyl, wherein the C$_{1-6}$alkyl is optionally substituted with one or more —OH. In some embodiments, $R^4$ is —S(O)$_2$—$R^a$, wherein $R^a$ is C$_{3-6}$cycloalkyl optionally substituted with one or more —OH, C(O)$_2$—C$_{1-6}$alkyl, —C(O)—NH(C$_{1-6}$alkyl), —C(O)—N(C$_{1-6}$alkyl)$_2$, —C(O)—C$_{3-10}$heterocyclyl, or C$_{1-6}$alkyl, wherein the C$_{1-6}$alkyl is optionally substituted with one or more —OH. In some embodiments, R$^4$ is —S(O)$_2$—R$^a$, wherein R$^a$ is C$_{3-6}$cycloalkyl optionally substituted with one or more —OH, C(O)$_2$—C$_{1-3}$alkyl, —C(O)—NH(C$_{1-3}$alkyl), —C(O)—N(C$_{1-3}$alkyl)$_2$, —C(O)—C$_{3-6}$heterocyclyl, or C$_{1-3}$alkyl, wherein the C$_{1-3}$alkyl is optionally substituted with one or more —OH. In some embodiments, R$^4$ is selected from the group consisting of

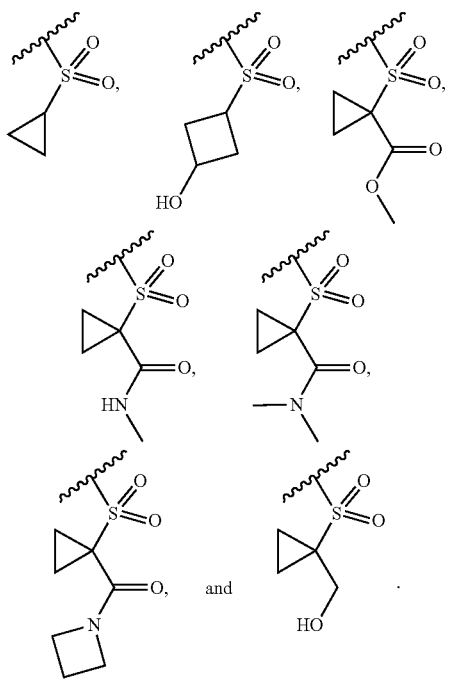

In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), or a stereoisomer or tautomer thereof, or a pharmaceutically acceptable salt of any of the foregoing, R$^4$ is —S(O)$_2$—R$^a$, wherein R$^a$ is 3-10 membered heterocyclyl. In some embodiments R$^4$ is —S(O)$_2$—R$^a$, wherein R$^a$ is 3-10 membered heterocyclyl optionally substituted with one or more C$_{1-6}$alkyl. In some embodiments, R$^4$ is —S(O)$_2$—R$^a$, wherein R$^a$ is 3-6 membered heterocyclyl optionally substituted with one or more C$_{1-6}$alkyl. In some embodiments, wherein R$^4$ is —S(O)$_2$—R$^a$, wherein R$^a$ is 3-6 membered heterocyclyl optionally substituted with one or more C$_{1-3}$alkyl. In some embodiments, R$^4$ is

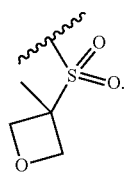 [SMILES: *S(=O)(=O)C1(C)COC1]

In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), or a stereoisomer or tautomer thereof, or a pharmaceutically acceptable salt of any of the foregoing, R$^4$ is 5-20 membered heteroaryl. In some embodiments, R$^4$ is 5-20 membered heteroaryl optionally substituted with one or more C$_{1-6}$alkyl. In some embodiments, R$^4$ is 5-6 membered heteroaryl optionally substituted with one or more C$_{1-6}$alkyl. In some embodiments, R$^4$ is 5-6 membered heteroaryl optionally substituted with one or more C$_{1-3}$alkyl. In some embodiments, R$^4$ is 5-6 membered heteroaryl optionally substituted with one or more methyl. In some embodiments, R$^4$ is selected from the group consisting of

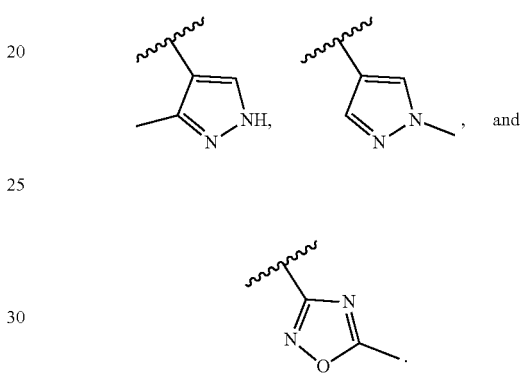

In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), or a stereoisomer or tautomer thereof, or a pharmaceutically acceptable salt of any of the foregoing, R$^4$ is —N(R$^d$)$_2$, wherein each of R$^d$ is independently H, C$_{1-6}$ alkyl, or —S(O)$_2$—R$^a$, wherein the C$_{1-6}$alkyl of R$^d$ is optionally substituted with one or more —OH, and wherein R$^a$ is C$_{1-6}$alkyl. In some embodiments, R$^4$ is —N(R$^d$)$_2$, wherein each of R$^d$ is independently H, C$_{1-3}$ alkyl, or —S(O)$_2$—R$^a$, wherein the C$_{1-3}$alkyl of R$^d$ is optionally substituted with one or more —OH, and wherein R$^a$ is C$_{1-3}$alkyl. In some embodiments, R$^4$ is —N(R$^d$)$_2$, wherein each of R$^d$ is independently H, C$_{1-6}$ alkyl, or —S(O)$_2$—R$^a$, wherein the C$_{1-3}$alkyl of R$^d$ is optionally substituted with one or more —OH, and wherein R$^a$ is methyl. In some embodiments, R$^4$ is selected from the group consisting of —NH$_2$,

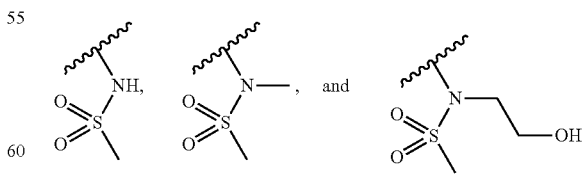

In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), formula (I'), or a stereoisomer or tautomer thereof, or a pharmaceutically acceptable salt of any of the foregoing, $R^4$ is —N($R^d$)$_2$, wherein each of $R^d$ is independently H, $C_{1-6}$ alkyl, or —S(O)$_2$—$R^a$, wherein the $C_{1-6}$alkyl of $R^d$ is optionally substituted with one or more —OH, and wherein $R^a$ is $C_{1-6}$alkyl. In some embodiments, $R^4$ is —N($R^d$)$_2$, wherein each of $R^d$ is independently H, $C_{1-3}$ alkyl, or —S(O)$_2$—$R^a$, wherein the $C_{1-3}$alkyl of $R^d$ is optionally substituted with one or more —OH, and wherein $R^a$ is $C_{1-3}$alkyl. In some embodiments, $R^4$ is —N($R^d$)$_2$, wherein each of $R^d$ is independently H, $C_{1-6}$ alkyl, or —S(O)$_2$—$R^a$, wherein the $C_{1-3}$alkyl of $R^d$ is optionally substituted with one or more —OH, and wherein $R^a$ is methyl. In some embodiments, $R^4$ is selected from the group consisting of —NH$_2$,

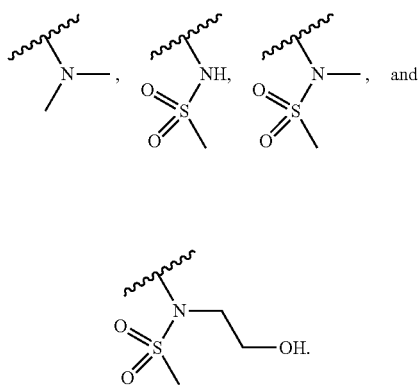

In some variations, the embodiments provided herein also apply to a compound of formula (II), or a stereoisomer or tautomer thereof, or a pharmaceutically acceptable salt of any of the foregoing, or any variation or embodiment thereof.

In some embodiments of a compound of formula (I), or a stereoisomer or tautomer thereof, or a pharmaceutically acceptable salt of any of the foregoing, $R^4$ is —C(O)—N($R^e$)$_2$, wherein each of $R^e$ is independently H or $C_{1-6}$ alkyl. In some embodiments, $R^4$ is —C(O)—N($R^e$)$_2$, wherein each of $R^e$ is independently H or $C_{1-3}$ alkyl. In some embodiments, $R^4$ is —C(O)—N($R^e$)$_2$, wherein each of $R^e$ is independently H or methyl. In some embodiments, $R^4$ is —C(O)—NH$_2$. In some embodiments, $R^4$ is —C(O)—NH(CH$_3$). In some embodiments, $R^4$ is —C(O)—N(CH$_3$)$_2$. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), or a stereoisomer or tautomer thereof, or a pharmaceutically acceptable salt of any of the foregoing, $R^4$ is —C(O)—N($R^e$)$_2$, wherein each of $R^e$ is independently H or 3-10 membered heterocycle, wherein the 3-10 membered heterocycle is optionally substituted with one or more oxo. In some embodiments, $R^4$ is —C(O)—N($R^e$)$_2$, wherein each of $R^e$ is independently H or 3-6 membered heterocycle, wherein the 3-6 membered heterocycle is optionally substituted with one or more oxo. In some embodiments, $R^4$ is selected from the group consisting of

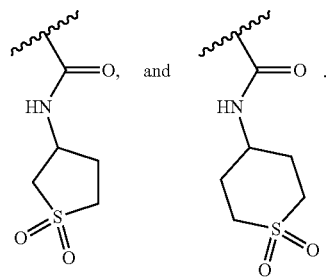 [SMILES: *C(=O)NC1CCS(=O)(=O)C1 ; "and" ; *C(=O)NC1CCS(=O)(=O)CC1]

In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), or a stereoisomer or tautomer thereof, or a pharmaceutically acceptable salt of any of the foregoing, $R^4$ is —C(O)—N($R^e$)$_2$, wherein both $R^e$ together with the N to which they are attached are taken together to form a 3-10 membered heterocyclyl. In some embodiments $R^4$ is —C(O)—N($R^e$)$_2$, wherein both $R^e$ together with the N to which they are attached are taken together to form a 3-10 membered heterocyclyl, wherein the 3-10 membered heterocyclyl is optionally substituted with one or more halo, oxo, —OH, —NH$_2$, —NH—S(O)$_2$—$R^a$, or —S(O)$_2$—$R^a$, wherein $R^a$ is $C_{1-6}$alkyl. In some embodiments $R^4$ is —C(O)—N($R^e$)$_2$, wherein both $R^e$ together with the N to which they are attached are taken together to form a 3-7 membered heterocyclyl, wherein the 3-7 membered heterocyclyl is optionally substituted with one or more halo, oxo, —OH, NH$_2$, NH—S(O)$_2$—$R^a$, or —S(O)$_2$—$R^a$, wherein $R^a$ is $C_{1-3}$alkyl. In some embodiments $R^4$ is —C(O)—N($R^e$)$_2$, wherein both $R^e$ together with the N to which they are attached are taken together to form a 3-7 membered heterocyclyl, wherein the 3-7 membered heterocyclyl is optionally substituted with one or more halo, oxo, —OH, —NH$_2$, —NH—S(O)$_2$—$R^a$, or —S(O)$_2$—$R^a$, wherein $R^a$ is methyl. In some embodiments, $R^4$ is selected from the group consisting of

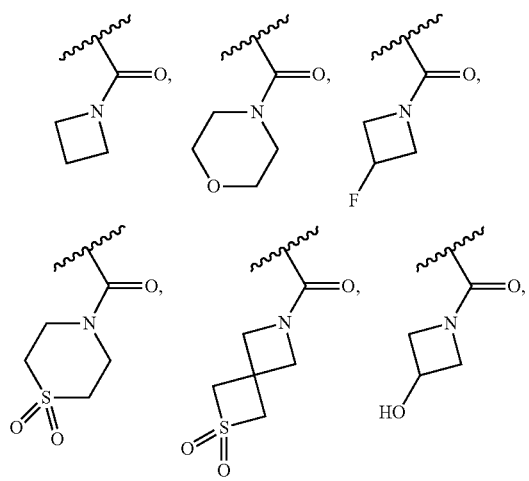

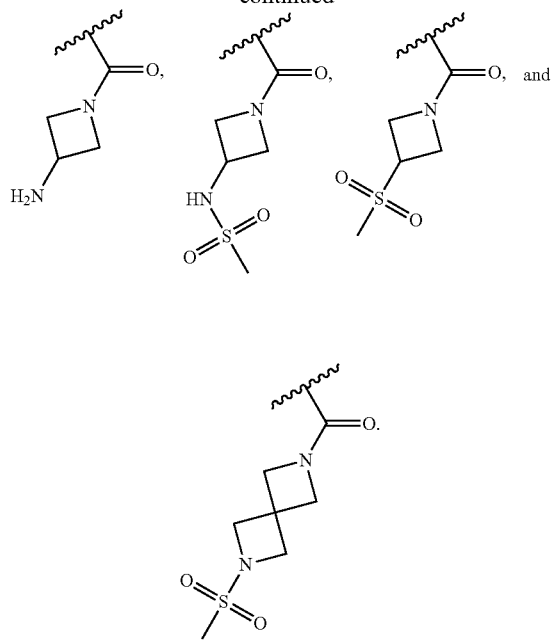

In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), or a stereoisomer or tautomer thereof, or a pharmaceutically acceptable salt of any of the foregoing, $R^4$ is 3-10 membered heterocyclyl optionally substituted with one or more oxo or $C_{1-6}$alkyl. In some embodiments, $R^4$ is 3-7 membered heterocyclyl optionally substituted with one or more oxo or $C_{1-6}$alkyl. In some embodiments, $R^4$ is 3-7 membered heterocyclyl optionally substituted with one or more oxo or $C_{1-3}$alkyl. In some embodiments, $R^4$ is selected from the group consisting of

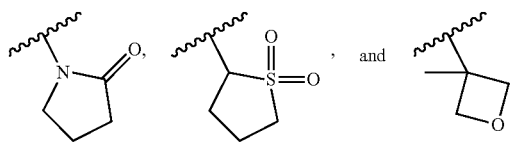

In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I'), or a stereoisomer or tautomer thereof, or a pharmaceutically acceptable salt of any of the foregoing, $R^4$ is 3-10 membered heterocyclyl optionally substituted with one or more $C_{1-6}$alkyl, —OH, oxo or —S(O)$_2$R$^a$. In some embodiments, $R^4$ is 3-7 membered heterocyclyl optionally substituted with one or more $C_{1-6}$alkyl, —OH, oxo or —S(O)$_2$R$^a$. In some embodiments, $R^4$ is 3-7 membered heterocyclyl optionally substituted with one or more $C_{1-3}$alkyl, —OH, oxo or —S(O)$_2$R$^a$. In some embodiments, $R^4$ is selected from the group consisting of

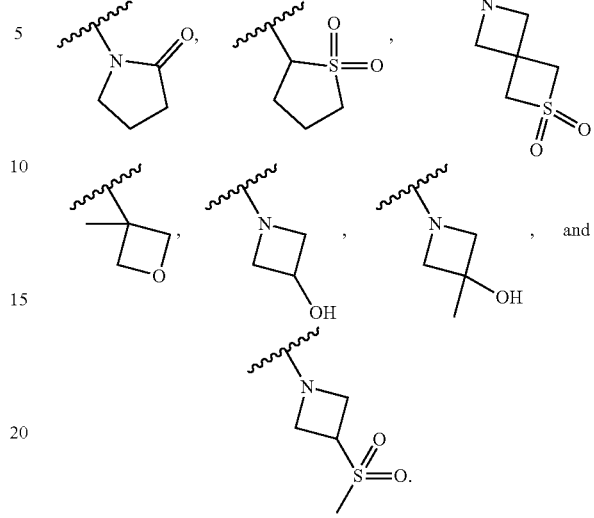

In some variations, the embodiments provided herein also apply to a compound of formula (II), or a stereoisomer or tautomer thereof, or a pharmaceutically acceptable salt of any of the foregoing, or any variation or embodiment thereof.

In some embodiments of a compound of formula (I'), or a stereoisomer or tautomer thereof, or a pharmaceutically acceptable salt of any of the foregoing, $R^4$ is 3-10 membered heterocyclyl optionally substituted with one or more $C_{1-6}$alkyl, —OH, oxo or —S(O)$_2$R$^a$. In some embodiments, $R^4$ is 3-7 membered heterocyclyl optionally substituted with one or more $C_{1-6}$alkyl, —OH, oxo or —S(O)$_2$R$^a$. In some embodiments, $R^4$ is 3-7 membered heterocyclyl optionally substituted with one or more $C_{1-3}$alkyl, —OH, oxo or —S(O)$_2$R$^a$. In some embodiments, $R^4$ is selected from the group consisting of

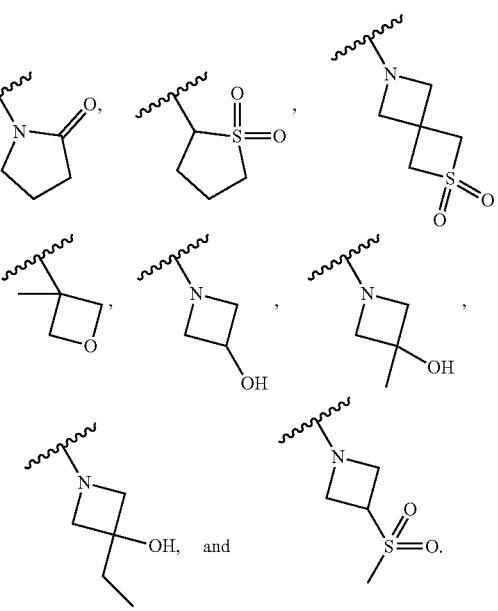

In some variations, the embodiments provided herein also apply to a compound of formula (II), or a stereoisomer or tautomer thereof, or a pharmaceutically acceptable salt of any of the foregoing, or any variation or embodiment thereof.

In some embodiments of a compound of formula (II), or a stereoisomer or tautomer thereof, or a pharmaceutically acceptable salt of any of the foregoing, $R^4$ is 3-10 membered heterocyclyl optionally substituted with one or more $C_{1-6}$alkyl, —OH, oxo or —S(O)$_2$R$^a$. In some embodiments, $R^4$ is 3-7 membered heterocyclyl optionally substituted with one or more $C_{1-6}$alkyl, —OH, oxo or —S(O)$_2$R$^a$. In some embodiments, $R^4$ is 3-7 membered heterocyclyl optionally substituted with one or more $C_{1-3}$alkyl, —OH, oxo or —S(O)$_2$R$^a$. In some embodiments, $R^4$ is selected from the group consisting of

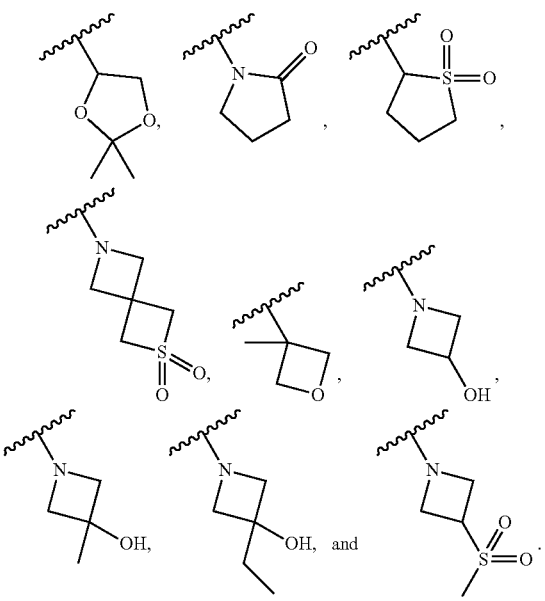

In some embodiments of a compound of formula (I), or a stereoisomer or tautomer thereof, or a pharmaceutically acceptable salt of any of the foregoing, $R^4$ is —NS(O)—(C$_{1-6}$alkyl)$_2$. In some embodiments, $R^4$ is —NS(O)—(C$_{1-3}$alkyl)$_2$. In some embodiments, $R^4$ is

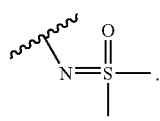 [SMILES: *N=S(C)(C)=O]

In some embodiments of a compound of formula (I), or a stereoisomer or tautomer thereof, or a pharmaceutically acceptable salt of any of the foregoing, $R^4$ is —S(O)(N—C$_{1-6}$alkyl)-(C$_{1-6}$alkyl). In some embodiments, $R^4$ is —S(O)(N—C$_{1-3}$alkyl)-(C$_{1-3}$alkyl). In some embodiments, $R^4$ is

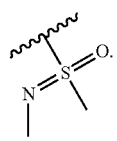

In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), or a stereoisomer or tautomer thereof, or a pharmaceutically acceptable salt of any of the foregoing, $R^4$ is —CN. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I'), or a stereoisomer or tautomer thereof, or a pharmaceutically acceptable salt of any of the foregoing, $R^4$ is —(CH$_2$)$_q$OH, wherein q is an integer from 0-6. $R^4$ is —(CH$_2$)$_q$OH, wherein q is an integer from 0-2. In some embodiments, $R^4$ is —OH. In some embodiments, $R^4$ is selected from the group consisting of

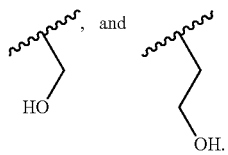

In some variations, the embodiments provided herein also apply to a compound of formula (II), or a stereoisomer or tautomer thereof, or a pharmaceutically acceptable salt of any of the foregoing, or any variation or embodiment thereof.

In some embodiments of a compound of formula (I'), or a stereoisomer or tautomer thereof, or a pharmaceutically acceptable salt of any of the foregoing, $R^4$ is —C(O)—C$_{1-6}$alkyl. In some embodiments, $R^4$ is —C(O)—C$_{1-3}$alkyl. In some embodiments, $R^4$ is —C(O)CH$_3$. In some variations, the embodiments provided herein also apply to a compound of formula (II), or a stereoisomer or tautomer thereof, or a pharmaceutically acceptable salt of any of the foregoing, or any variation or embodiment thereof.

In some embodiments of a compound of formula (I'), or a stereoisomer or tautomer thereof, or a pharmaceutically acceptable salt of any of the foregoing, $R^4$ is —P(O)(C$_{1-6}$alkyl)$_2$. In some embodiments, $R^4$ is —P(O)(C$_{1-3}$alkyl)$_2$. In some embodiments, $R^4$ is —P(O)(CH$_3$)$_2$. In some variations, the embodiments provided herein also apply to a compound of formula (II), or a stereoisomer or tautomer thereof, or a pharmaceutically acceptable salt of any of the foregoing, or any variation or embodiment thereof.

In some embodiments of a compound of formula (I), or a stereoisomer or tautomer thereof, or a pharmaceutically acceptable salt of any of the foregoing, each of $X^1$ and $X^2$ is independently N or C(R$^5$). In some embodiments, each of $X^1$ and $X^2$ is N. In some embodiments, each of $X^1$ and $X^2$ is C(R$^5$). In some embodiments, one of $X^1$ and $X^2$ is CR$^5$, and the other of $X^1$ and $X^2$ is N. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), or a stereoisomer or tautomer thereof, or a pharmaceutically acceptable salt of any of the foregoing, one of $X^1$ and $X^2$ is CR$^5$, and the other of $X^1$ and $X^2$ is C that is taken together with $R^4$, and the atoms to which they are attached, to form a 5-10 membered heterocyclyl optionally substituted with one or more of $R^b$. In some embodiments, one of $X^1$ and $X^2$ is $CR^5$, and the other of $X^1$ and $X^2$ is C that is taken together with $R^4$, and the atoms to which they are attached, to form a 5-8 membered heterocyclyl optionally substituted with one or more of $R^b$. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), or a stereoisomer or tautomer thereof, or a pharmaceutically acceptable salt of any of the foregoing, $R^b$ is halo, oxo, $C_{1-6}$alkyl, —C(O)—$C_{1-6}$alkyl, —C(O)—NH$_2$, —C(O)—NH($C_{1-6}$alkyl), —C(O)—N($C_{1-6}$alkyl)$_2$, —S(O)$_2$—$R^a$, $C_{3-10}$cycloalkyl, and 3-10 membered heterocyclyl, wherein the $C_{1-6}$alkyl of $R^b$ is optionally substituted with one or more halo, OH, or —S(O)$_2$—$C_{1-6}$alkyl, and the $C_{3-10}$cycloalkyl of $R^b$ is optionally substituted with one or more —OH. In some embodiments, $R^b$ is halo, oxo, $C_{1-3}$alkyl, —C(O)—$C_{1-3}$alkyl, —C(O)—NH$_2$, —C(O)—NH($C_{1-3}$alkyl), —C(O)—N($C_{1-3}$alkyl)$_2$, —S(O)$_2$—$R^a$, $C_{3-6}$cycloalkyl, and 3-6 membered heterocyclyl, wherein the $C_{1-3}$alkyl of $R^b$ is optionally substituted with one or more halo, OH, or —S(O)$_2$—$C_{1-3}$alkyl, and the $C_{3-6}$cycloalkyl of $R^b$ is optionally substituted with one or more —OH. In some embodiments, $R^b$ is selected from the group consisting of oxo, —S(O)$_2$CH$_3$,

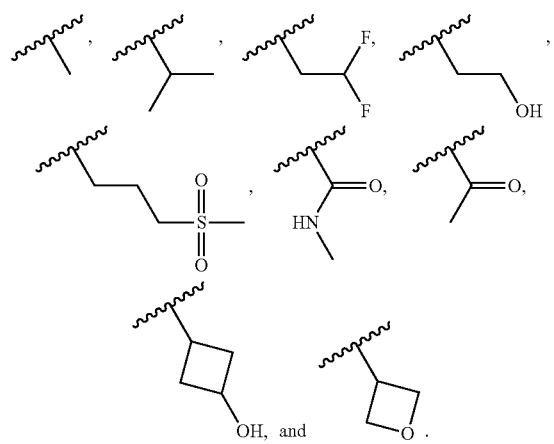

In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I'), or a stereoisomer or tautomer thereof, or a pharmaceutically acceptable salt of any of the foregoing, $R^b$ is, independently at each occurrence, selected from the group consisting of halo, oxo, $C_{1-6}$alkyl, —C(O)—$C_{1-6}$alkyl, —C(O)—NH$_2$, —C(O)—NH($C_{1-6}$alkyl), —C(O)—N($C_{1-6}$alkyl)$_2$, —S(O)$_2$—$R^a$, $C_{3-10}$cycloalkyl, and 3-10 membered heterocyclyl, wherein the $C_{1-6}$alkyl of $R^b$ is optionally substituted with one or more halo, OH, —S(O)$_2$—$C_{1-6}$alkyl, or $C_{3-10}$cycloalkyl, wherein the $C_{3-10}$cycloalkyl of the $C_{1-6}$alkyl of $R^b$ is further optionally substituted with one or more $C_{1-6}$alkyl or —OH, and the $C_{3-10}$cycloalkyl of $R^b$ is optionally substituted with one or more —OH, $C_{3-6}$cycloalkyl, or $C_{1-6}$alkyl, wherein the $C_{1-6}$alkyl of the $C_{3-10}$cycloalkyl of $R^b$ is further optionally substituted with one or more —OH. In some embodiments, $R^b$ is, independently at each occurrence, selected from the group consisting of halo, oxo, $C_{1-3}$alkyl, —C(O)—$C_{1-3}$alkyl, —C(O)—NH$_2$, —C(O)—NH($C_{1-3}$alkyl), —C(O)—N($C_{1-3}$alkyl)$_2$, —S(O)$_2$—$R^a$, $C_{3-6}$cycloalkyl, and 3-6 membered heterocyclyl, wherein the $C_{1-3}$alkyl of $R^b$ is optionally substituted with one or more halo, OH, —S(O)$_2$—$C_{1-3}$alkyl, or $C_{3-6}$cycloalkyl, wherein the $C_{3-6}$cycloalkyl of the $C_{1-3}$alkyl of $R^b$ is further optionally substituted with one or more $C_{1-3}$alkyl or —OH, and the $C_{3-6}$cycloalkyl of $R^b$ is optionally substituted with one or more —OH, $C_{3-6}$cycloalkyl, or $C_{1-3}$alkyl, wherein the $C_{1-3}$alkyl of the $C_{3-6}$cycloalkyl of $R^b$ is further optionally substituted with one or more —OH. In some embodiments, $R^b$ is selected from the group consisting of oxo, —S(O)$_2$CH$_3$,

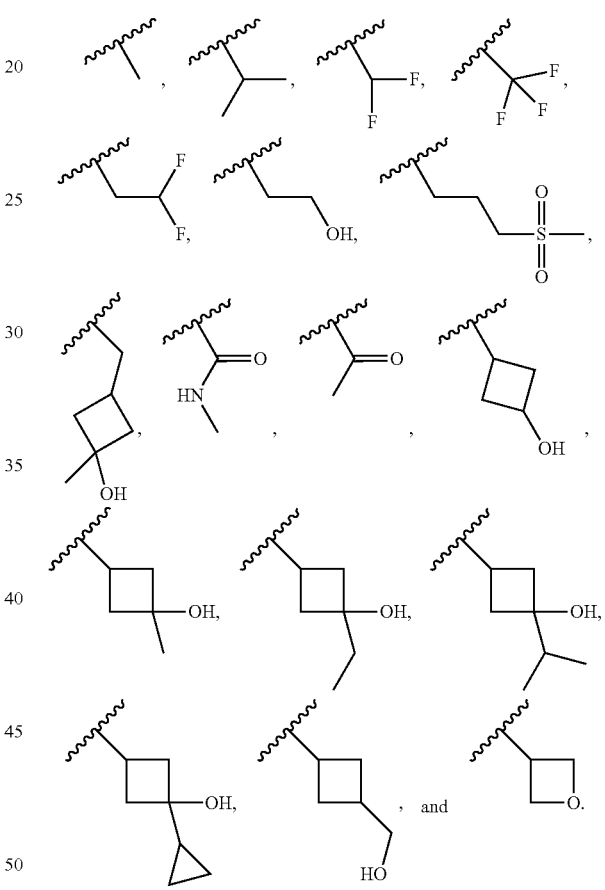

In some variations, the embodiments provided herein also apply to a compound of formula (II), or a stereoisomer or tautomer thereof, or a pharmaceutically acceptable salt of any of the foregoing, or any variation or embodiment thereof.

In some embodiments of a compound of formula (II), or a stereoisomer or tautomer thereof, or a pharmaceutically acceptable salt of any of the foregoing, $R^b$ is, independently at each occurrence, selected from the group consisting of —OH, halo, oxo, $C_{1-6}$alkyl, —C(O)—$C_{1-6}$alkyl, —C(O)—NH$_2$, —C(O)—NH($C_{1-6}$alkyl), —C(O)—N($C_{1-6}$alkyl)$_2$, —S(O)$_2$—$R^a$, $C_{3-10}$cycloalkyl, and 3-10 membered heterocyclyl, wherein the $C_{1-6}$alkyl of $R^b$ is optionally substituted with one or more halo, OH, —S(O)$_2$—$C_{1-6}$alkyl, or $C_{3-10}$cycloalkyl, wherein the $C_{3-10}$cycloalkyl of the $C_{1-6}$alkyl of $R^b$ is further optionally substituted with one or more $C_{1-6}$alkyl or —OH, and the $C_{3-10}$cycloalkyl of $R^b$ is optionally substituted with one or more —OH, $C_{3-10}$cycloalkyl, or $C_{1-6}$alkyl, wherein the $C_{1-6}$alkyl of the $C_{3-10}$cycloalkyl of $R^b$ is further optionally substituted with one or more —OH, deuterium, or halo. In some embodiments, $R^b$ is, independently at each occurrence, selected from the group consisting of —OH, halo, oxo, $C_{1-3}$alkyl, —C(O)—$C_{1-3}$alkyl, —C(O)—NH$_2$, —C(O)—NH($C_{1-3}$alkyl), —C(O)—N($C_{1-3}$alkyl)$_2$, —S(O)$_2$—$R^a$, $C_{3-6}$cycloalkyl, and 3-6 membered heterocyclyl, wherein the $C_{1-3}$alkyl of $R^b$ is optionally substituted with one or more halo, OH, —S(O)$_2$—$C_{1-3}$alkyl, or $C_{3-6}$cycloalkyl, wherein the $C_{3-6}$cycloalkyl of the $C_{1-3}$alkyl of $R^b$ is further optionally substituted with one or more $C_{1-3}$alkyl or —OH, and the $C_{3-6}$cycloalkyl of $R^b$ is optionally substituted with one or more —OH, $C_{3-6}$cycloalkyl, or $C_{1-3}$alkyl, wherein the $C_{1-3}$alkyl of the $C_{3-6}$cycloalkyl of $R^b$ is further optionally substituted with one or more —OH, deuterium or halo. In some embodiments, $R^b$ is selected from the group consisting of —OH, oxo, —S(O)$_2$CH$_3$,

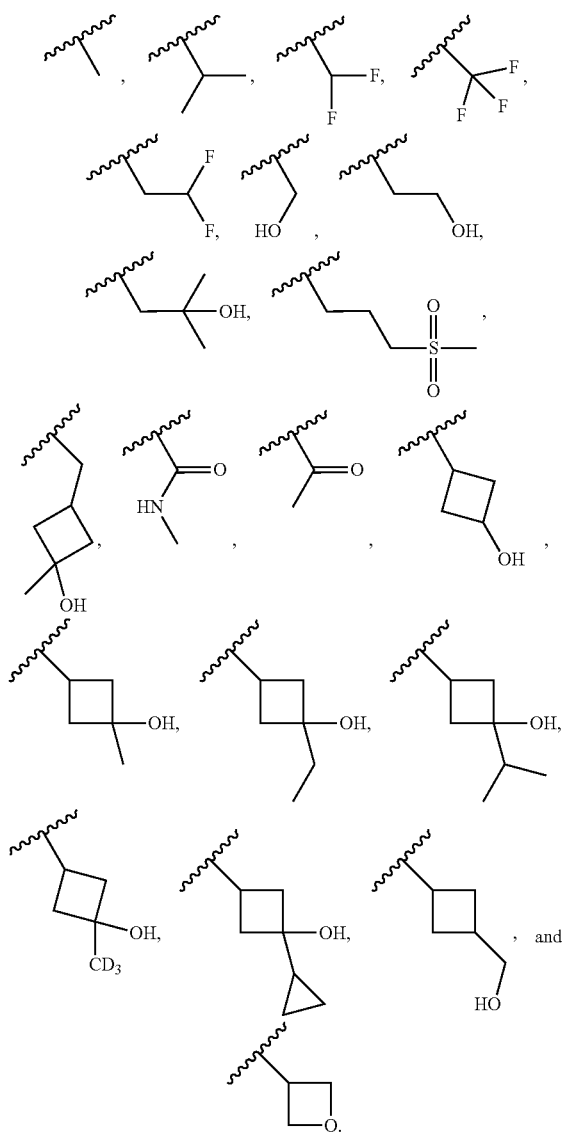

In some embodiments of a compound of formula (I), or a stereoisomer or tautomer thereof, or a pharmaceutically acceptable salt of any of the foregoing, $R^b$ is oxo. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), or a stereoisomer or tautomer thereof, or a pharmaceutically acceptable salt of any of the foregoing, $R^b$ is $C_{1-6}$alkyl. In some embodiments, $R^b$ is $C_{1-6}$alkyl optionally substituted with one or more halo, OH, or —S(O)$_2$—$C_{1-6}$alkyl. In some embodiments, $R^b$ is $C_{1-3}$alkyl optionally substituted with one or more more halo, OH, or —S(O)$_2$—$C_{1-3}$alkyl. In some embodiments, $R^b$ is selected from the group consisting of

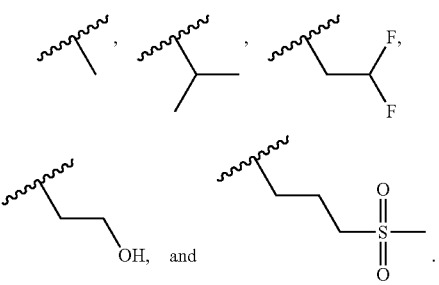

In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I'), or a stereoisomer or tautomer thereof, or a pharmaceutically acceptable salt of any of the foregoing, $R^b$ is $C_{1-6}$alkyl. In some embodiments, the $C_{1-6}$alkyl of $R^b$ is optionally substituted with one or more halo, OH, —S(O)$_2$—$C_{1-6}$alkyl, or $C_{3-10}$cycloalkyl, wherein the $C_{3-10}$cycloalkyl of the $C_{1-6}$alkyl of $R^b$ is further optionally substituted with one or more $C_{1-6}$alkyl or —OH. In some embodiments, $R^b$ is $C_{1-3}$alkyl optionally substituted with one or more halo, OH, —S(O)$_2$—$C_{1-3}$alkyl, or $C_{3-6}$cycloalkyl, wherein the $C_{3-6}$cycloalkyl of the $C_{1-3}$alkyl of $R^b$ is further optionally substituted with one or more $C_{1-3}$alkyl or —OH. In some embodiments, $R^b$ is selected from the group consisting of

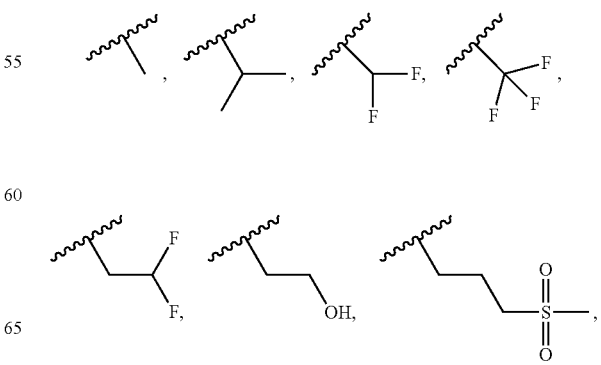

-continued

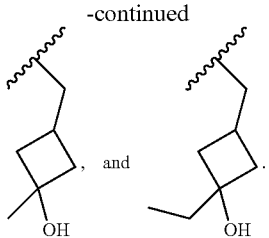

In some variations, the embodiments provided herein also apply to a compound of formula (II), or a stereoisomer or tautomer thereof, or a pharmaceutically acceptable salt of any of the foregoing, or any variation or embodiment thereof.

In some embodiments of a compound of formula (II), or a stereoisomer or tautomer thereof, or a pharmaceutically acceptable salt of any of the foregoing, $R^b$ is $C_{1-6}$alkyl. In some embodiments, the $C_{1-6}$alkyl of $R^b$ is optionally substituted with one or more halo, OH, —S(O)$_2$—C$_{1-6}$alkyl, or $C_{3-10}$cycloalkyl, wherein the $C_{3-10}$cycloalkyl of the $C_{1-6}$alkyl of $R^b$ is further optionally substituted with one or more $C_{1-6}$alkyl or —OH. In some embodiments, $R^b$ is $C_{1-3}$alkyl optionally substituted with one or more halo, OH, —S(O)$_2$—C$_{1-3}$alkyl, or $C_{3-6}$cycloalkyl, wherein the $C_{3-6}$cycloalkyl of the $C_{1-3}$alkyl of $R^b$ is further optionally substituted with one or more $C_{1-3}$alkyl or —OH. In some embodiments, $R^b$ is selected from the group consisting of

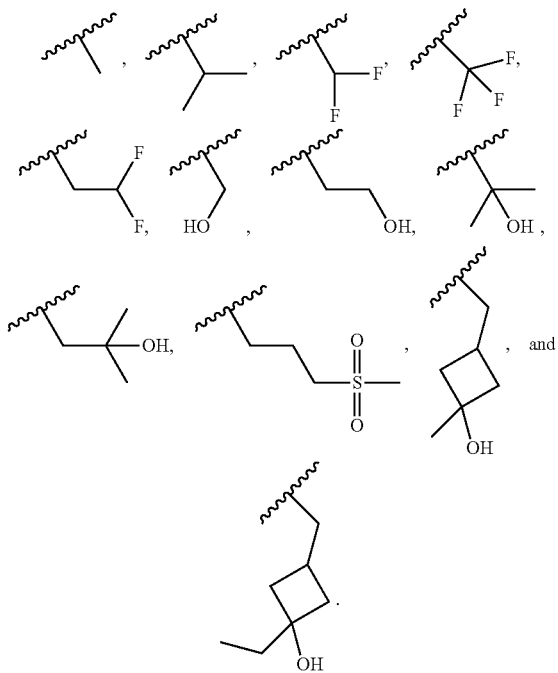

In some embodiments of a compound of formula (I), or a stereoisomer or tautomer thereof, or a pharmaceutically acceptable salt of any of the foregoing, $R^b$ is —C(O)—NH(C$_{1-6}$alkyl). In some embodiments, $R^b$ is —C(O)—NH(C$_{1-3}$alkyl). In some embodiments, $R^b$ is

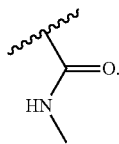

In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), or a stereoisomer or tautomer thereof, or a pharmaceutically acceptable salt of any of the foregoing, $R^b$ is —C(O)—C$_{1-6}$alkyl. In some embodiments, $R^b$ is —C(O)—C$_{1-3}$alkyl. In some embodiments, $R^b$ is

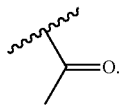

In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), or a stereoisomer or tautomer thereof, or a pharmaceutically acceptable salt of any of the foregoing $R^b$ is —S(O)$_2$—R$^a$, wherein R$^a$ is $C_{1-6}$alkyl. In some embodiments, $R^b$ is —S(O)$_2$—R$^a$, wherein R$^a$ is $C_{1-3}$alkyl. In some embodiments, $R^b$ is —S(O)$_2$—R$^a$, R$^a$ is methyl. In some embodiments, $R^b$ is —S(O)$_2$CH$_3$. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), or a stereoisomer or tautomer thereof, or a pharmaceutically acceptable salt of any of the foregoing, $R^b$ is $C_{3-10}$cycloalkyl optionally substituted with one or more —OH. In some embodiments, $R^b$ is $C_{3-6}$cycloalkyl optionally substituted with one or more —OH. In some embodiments, $R^b$ is

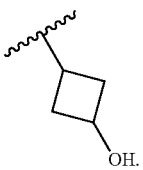

In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I'), or a stereoisomer or tautomer thereof, or a pharmaceutically acceptable salt of any of the foregoing, $R^b$ is $C_{3-10}$cycloalkyl optionally substituted with one or more —OH, $C_{3-10}$cycloalkyl, or $C_{1-6}$alkyl, wherein the $C_{1-6}$alkyl is further optionally substituted with one or more —OH. In some embodiments, $R^b$ is $C_{3-6}$cycloalkyl optionally substituted with one or more —OH, $C_{3-6}$cycloalkyl, or $C_{1-3}$alkyl, wherein the $C_{1-3}$alkyl is further optionally substituted with one or more —OH. In some embodiments, $R^b$ is selected from the group consisting of

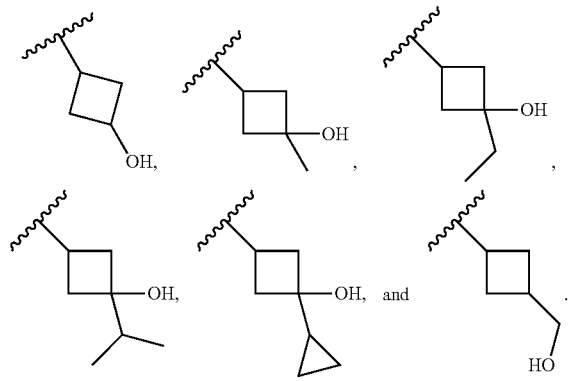

In some variations, the embodiments provided herein also apply to a compound of formula (II), or a stereoisomer or tautomer thereof, or a pharmaceutically acceptable salt of any of the foregoing, or any variation or embodiment thereof.

In some embodiments of a compound of formula (II), or a stereoisomer or tautomer thereof, or a pharmaceutically acceptable salt of any of the foregoing, $R^b$ is $C_{3-10}$cycloalkyl optionally substituted with one or more —OH, $C_{3-10}$cycloalkyl, or $C_{1-6}$alkyl, wherein the $C_{1-6}$alkyl is further optionally substituted with one or more —OH, deuterium, or halo. In some embodiments, $R^b$ is $C_{3-6}$cycloalkyl optionally substituted with one or more —OH, $C_{3-6}$cycloalkyl, or $C_{1-3}$alkyl, wherein the $C_{1-3}$alkyl is further optionally substituted with one or more —OH, deuterium, or halo. In some embodiments, $R^b$ is selected from the group consisting of

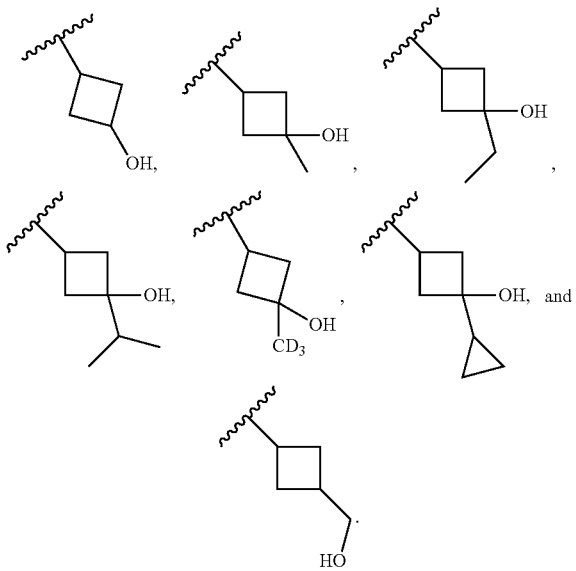

In some embodiments of a compound of formula (I), or a stereoisomer or tautomer thereof, or a pharmaceutically acceptable salt of any of the foregoing, $R^b$ is 3-10 membered heterocyclyl. In some embodiments, $R^b$ is 3-6 membered heterocyclyl. In some embodiments, $R^b$ is

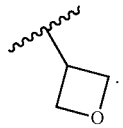 [SMILES: *C1COC1]

In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), or a stereoisomer or tautomer thereof, or a pharmaceutically acceptable salt of any of the foregoing, one of $X^1$ and $X^2$ is $CR^5$, and the other of $X^1$ and $X^2$ is C that is taken together with $R^4$, and the atoms to which they are attached, to form a 5-10 membered heteroaryl. In some embodiments, one of $X^1$ and $X^2$ is $CR^5$, and the other of $X^1$ and $X^2$ is C that is taken together with $R^4$, and the atoms to which they are attached, to form a 5-6 membered heteroaryl. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), or a stereoisomer or tautomer thereof, or a pharmaceutically acceptable salt of any of the foregoing, one of $X^1$ and $X^2$ is $CR^5$, and the other of $X^1$ and $X^2$ is C that is taken together with $R^4$, and the atoms to which they are attached, to form a 5-10 membered heteroaryl optionally substituted with one or more $R^c$. In some embodiments one of $X^1$ and $X^2$ is $CR^5$, and the other of $X^1$ and $X^2$ is C that is taken together with $R^4$, and the atoms to which they are attached, to form a 5-6 membered heteroaryl optionally substituted with one or more $R^c$. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), or a stereoisomer or tautomer thereof, or a pharmaceutically acceptable salt of any of the foregoing, $R^c$ is halo, $C_{1-6}$alkyl, —C(O)—$C_{1-6}$alkyl, —C(O)—$NH_2$, —C(O)—NH($C_{1-6}$alkyl), —C(O)—N($C_{1-6}$alkyl)$_2$, —S(O)$_2$—$R^a$, $C_{3-10}$cycloalkyl, and 3-10 membered heterocyclyl, wherein the $C_{1-6}$alkyl of $R^c$ is optionally substituted with one or more —S(O)$_2$—$C_{1-6}$alkyl, and the $C_{3-10}$cycloalkyl of $R^c$ is optionally substituted with one or more —OH. In some embodiments, $R^c$ is halo, $C_{1-3}$alkyl, —C(O)—$C_{1-3}$alkyl, —C(O)—$NH_2$, —C(O)—NH($C_{1-3}$alkyl), —C(O)—N($C_{1-3}$alkyl)$_2$, —S(O)$_2$—$R^a$, $C_{3-6}$cycloalkyl, and 3-6 membered heterocyclyl, wherein the $C_{1-6}$alkyl of $R^c$ is optionally substituted with one or more —S(O)$_2$—$C_{1-3}$alkyl, and the $C_{3-6}$cycloalkyl of $R^c$ is optionally substituted with one or more —OH. In some embodiments, $R^c$ is selected from the group consisting of methyl, isopropyl, —S(O)$_2$CH$_3$, and

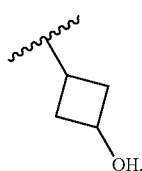 [SMILES: *C1CC(O)C1]

In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I'), or a stereoisomer or tautomer thereof, or a pharmaceutically acceptable salt of any of the foregoing, $R^c$ is independently at each occurrence, selected from the group consisting of halo, $C_{1-6}$alkyl, —C(O)—$C_{1-6}$alkyl, —C(O)—$NH_2$, —C(O)—NH($C_{1-6}$alkyl), —C(O)—N($C_{1-6}$alkyl)$_2$, —S(O)$_2$—$R^a$, $C_{3-10}$cycloalkyl, and 3-10 membered heterocyclyl, wherein the $C_{1-6}$alkyl of $R^c$ is optionally substituted with one or more —S(O)$_2$—$C_{1-6}$alkyl, the $C_{3-10}$cycloalkyl of $R^c$ is optionally substituted with one or more —OH, or $C_{1-6}$alkyl, and the 3-10 membered heterocyclyl of $R^c$ is optionally substituted with one or more —OH, or $C_{1-6}$alkyl, wherein the $C_{1-6}$alkyl is further optionally substituted with one or more —OH. In some embodiments, $R^c$ is independently at each occurrence, selected from the group consisting of halo, $C_{1-3}$alkyl, —C(O)—$C_{1-3}$alkyl, —C(O)—$NH_2$, —C(O)—NH($C_{1-3}$alkyl), —C(O)—N($C_{1-3}$alkyl)$_2$, —S(O)$_2$—$R^a$, $C_{3-6}$cycloalkyl, and 3-6 membered heterocyclyl, wherein the $C_{1-3}$alkyl of $R^c$ is optionally substituted with one or more —S(O)$_2$—$C_{1-3}$alkyl, the $C_{3-6}$cycloalkyl of $R^c$ is optionally substituted with one or more —OH, or $C_{1-3}$alkyl, and the 3-6 membered heterocyclyl of $R^c$ is optionally substituted with one or more —OH, or $C_{1-3}$alkyl, wherein the $C_{1-3}$alkyl is further optionally substituted with one or more —OH. In some embodiments, $R^c$ is selected from the group consisting of methyl, isopropyl, —S(O)$_2$CH$_3$, and

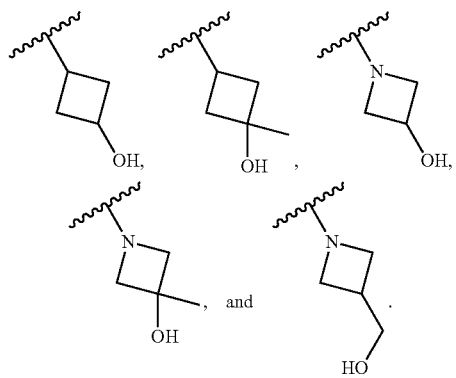

In some variations, the embodiments provided herein also apply to a compound of formula (II), or a stereoisomer or tautomer thereof, or a pharmaceutically acceptable salt of any of the foregoing, or any variation or embodiment thereof.

In some embodiments of a compound of formula (I), or a stereoisomer or tautomer thereof, or a pharmaceutically acceptable salt of any of the foregoing, $R^c$ is $C_{1-6}$alkyl, —S(O)$_2$—$R^a$. In some embodiments, $R^c$ is $C_{1-3}$alkyl. In some embodiments, $R^c$ is methyl. In some embodiments, $R^c$ is isopropyl. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), or a stereoisomer or tautomer thereof, or a pharmaceutically acceptable salt of any of the foregoing, $R^c$ is $C_{1-6}$alkyl optionally substituted with one or more —S(O)$_2$—$R^a$, wherein $R^a$ is $C_{1-6}$alkyl. In some embodiments, $R^c$ is $C_{1-3}$alkyl optionally substituted with one or more —S(O)$_2$—$R^a$, wherein $R^a$ is $C_{1-3}$alkyl. In some embodiments, $R^c$ is $C_{1-3}$alkyl optionally substituted with one or more —S(O)$_2$—$R^a$, wherein $R^a$ is methyl. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), or a stereoisomer or tautomer thereof, or a pharmaceutically acceptable salt of any of the foregoing, $R^c$ is $C_{3-10}$cycloalkyl optionally substituted with one or more —OH. In some embodiments, $R^c$ is $C_{3-6}$cycloalkyl optionally substituted with one or more —OH. In some embodiments, $R^c$ is

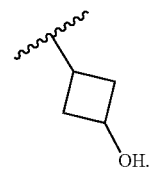 [SMILES: *C1CC(O)C1]

In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I'), or a stereoisomer or tautomer thereof, or a pharmaceutically acceptable salt of any of the foregoing, $R^c$ is $C_{3-10}$cycloalkyl optionally substituted with one or more —OH, or $C_{1-6}$alkyl. In some embodiments, $R^c$ is $C_{3-6}$cycloalkyl optionally substituted with one or more —OH, or $C_{1-3}$alkyl. In some embodiments, $R^c$ is selected from the group consisting of

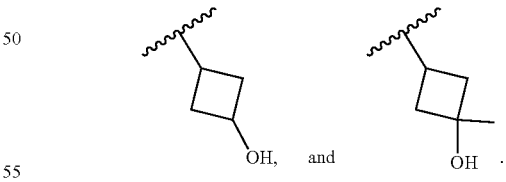

In some variations, the embodiments provided herein also apply to a compound of formula (II), or a stereoisomer or tautomer thereof, or a pharmaceutically acceptable salt of any of the foregoing, or any variation or embodiment thereof.

In some embodiments of a compound of formula (I'), or a stereoisomer or tautomer thereof, or a pharmaceutically acceptable salt of any of the foregoing, $R^c$ is 3-10 membered heterocyclyl optionally substituted with one or more —OH, or $C_{1-6}$alkyl, wherein the $C_{1-6}$alkyl is further optionally substituted with one or more —OH. In some embodiments, $R^c$ is 3-6 membered heterocyclyl optionally substituted with one or more —OH, or $C_{1-3}$alkyl, wherein the $C_{1-3}$alkyl is further optionally substituted with one or more —OH. In some embodiments, $R^c$ is selected from the group consisting of

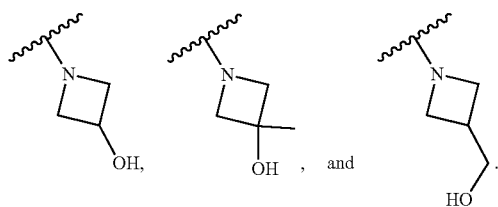

In some variations, the embodiments provided herein also apply to a compound of formula (II), or a stereoisomer or tautomer thereof, or a pharmaceutically acceptable salt of any of the foregoing, or any variation or embodiment thereof.

In some embodiments of a compound of formula (I), or a stereoisomer or tautomer thereof, or a pharmaceutically acceptable salt of any of the foregoing, $R^5$ is independently at each occurrence, H, halo, —CN, 3-10 membered heterocyclyl, $C_{1-6}$alkyl, or $C_{1-6}$alkoxy, wherein the $C_{1-6}$alkyl of $R^5$ is optionally substituted with one or more halo, or —OH and wherein the $C_{1-6}$alkoxy is optionally substituted with one or more halo. In some embodiments, $R^5$ is independently at each occurrence, H, halo, —CN, 3-6 membered heterocyclyl, $C_{1-3}$alkyl, or $C_{1-3}$alkoxy, wherein the $C_{1-3}$alkyl of $R^5$ is optionally substituted with one or more halo, or —OH and wherein the $C_{1-3}$alkoxy is optionally substituted with one or more halo. In some embodiments, $R^5$ is selected from the group consisting of H, Cl, F, —CN,

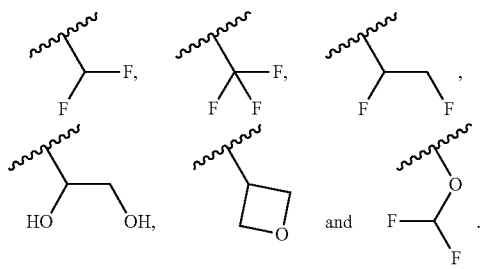

In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), or a stereoisomer or tautomer thereof, or a pharmaceutically acceptable salt of any of the foregoing, $R^5$ is H. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), or a stereoisomer or tautomer thereof, or a pharmaceutically acceptable salt of any of the foregoing, $R^5$ is halo. In some embodiments, $R^5$ is Cl, or F. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), or a stereoisomer or tautomer thereof, or a pharmaceutically acceptable salt of any of the foregoing, $R^5$ is —CN. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), or a stereoisomer or tautomer thereof, or a pharmaceutically acceptable salt of any of the foregoing, $R^5$ is $C_{1-6}$alkyl. In some embodiments, $R^5$ is $C_{1-3}$alkyl. In some embodiments, $R^5$ is methyl. In some embodiments, $R^5$ is $C_{1-6}$alkyl, wherein the $C_{1-6}$alkyl of $R^5$ is optionally substituted with one or more halo, or —OH. In some embodiments, $R^5$ is $C_{1-3}$alkyl, wherein the $C_{1-3}$alkyl of $R^5$ is optionally substituted with one or more halo, or —OH. In some embodiments, $R^5$ is $C_{1-3}$alkyl, wherein the $C_{1-3}$alkyl of $R^5$ is optionally substituted with one or more fluoro, or —OH. In some embodiments, $R^5$ is independently selected from the group consisting of methyl,

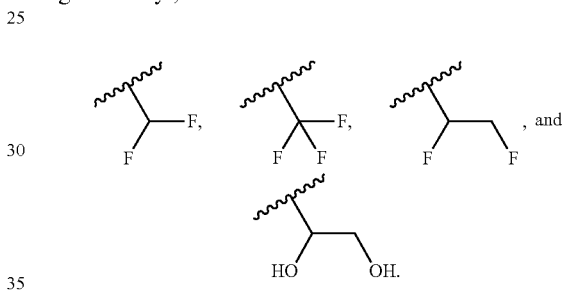

In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), or a stereoisomer or tautomer thereof, or a pharmaceutically acceptable salt of any of the foregoing, $R^5$ is 3-10 membered heterocyclyl. In some embodiments, $R^5$ is 3-6 membered heterocyclyl. In some embodiments, $R^5$ is

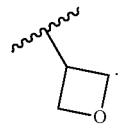

In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), or a stereoisomer or tautomer thereof, or a pharmaceutically acceptable salt of any of the foregoing, $R^5$ is $C_{1-6}$alkoxy optionally substituted with one or more halo. In some embodiments, $R^5$ is $C_{1-3}$alkoxy optionally substituted with one or more halo. In some embodiments, $R^5$ is $C_{1-3}$alkoxy optionally substituted with one or more fluoro. In some embodiments, $R^5$ is

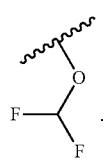

In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), or a stereoisomer or tautomer thereof, or a pharmaceutically acceptable salt of any of the foregoing, $R^6$ and $R^7$ are each independently H or halo. In some embodiments, $R^6$ and $R^7$ are each independently H or fluoro. In some embodiments, each of $R^6$ and $R^7$ is H. In some embodiments, each of $R^6$ and $R^7$ is fluoro. In some embodiments, one of $R^6$ and $R^7$ is H and the other of $R^6$ and $R^7$ is fluoro. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), or a stereoisomer or tautomer thereof, or a pharmaceutically acceptable salt of any of the foregoing, $L^1$, $L^2$, and the ring bearing $L^3$, $R^4$, $R^6$, and $R^7$ together form a bi-substituted phenyl with one group bound at the para position relative to the phenyl's attachment to $L^2$. In some embodiments, the bi-substituted phenyl is selected from the group consisting of

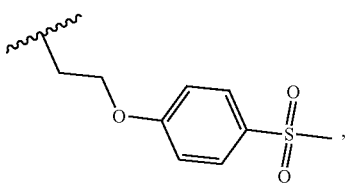

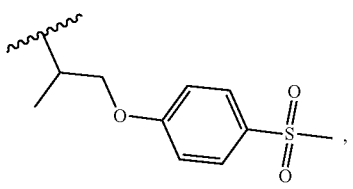

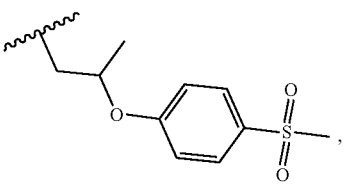

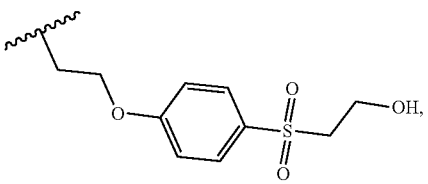

-continued

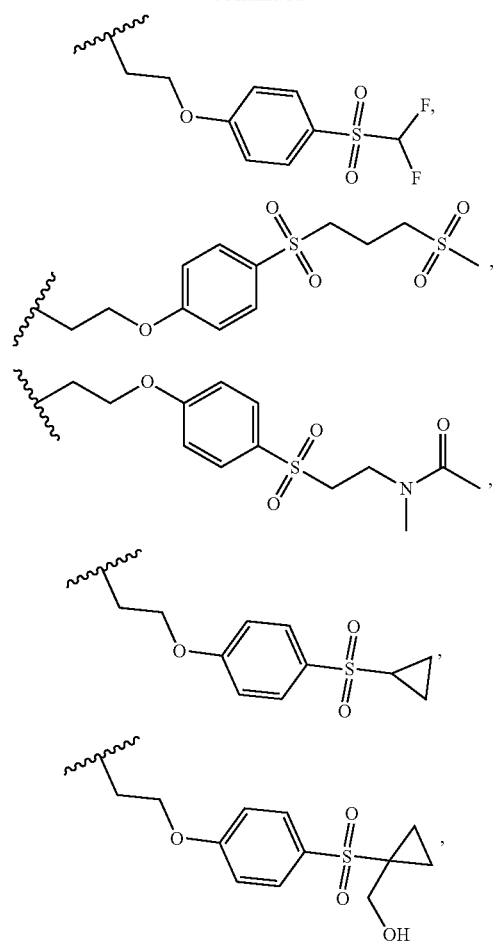

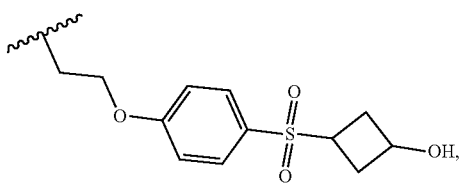

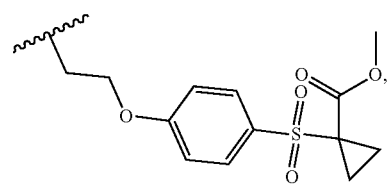

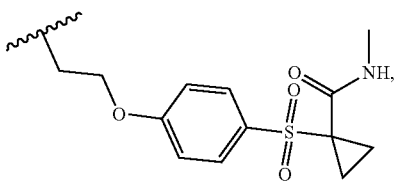

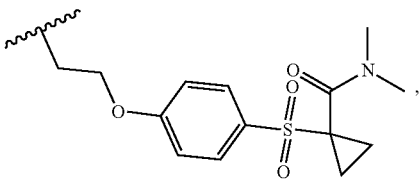

91
-continued
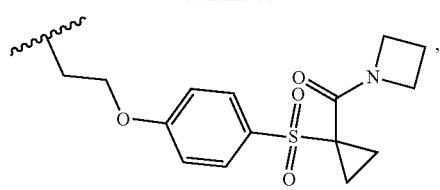
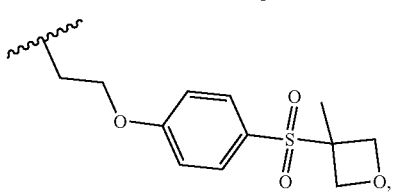
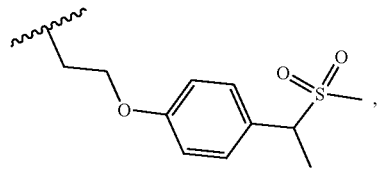
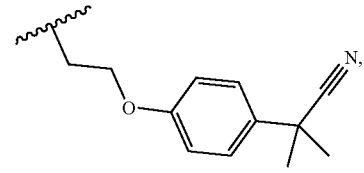
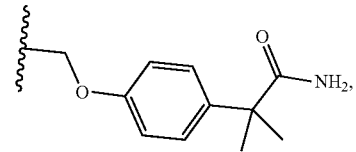
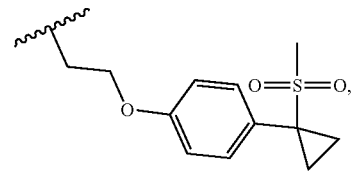
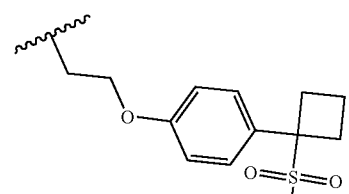
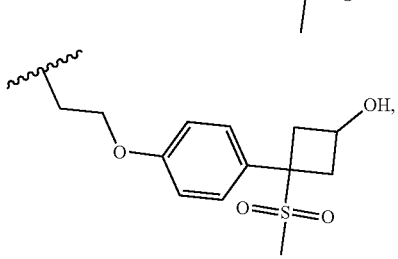
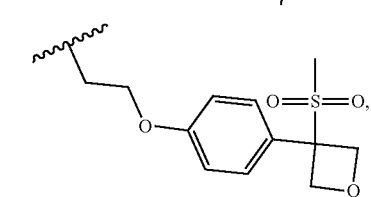
92
-continued
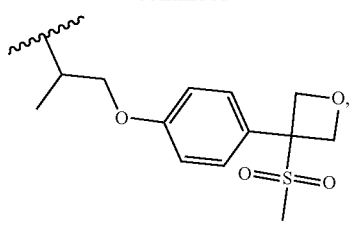
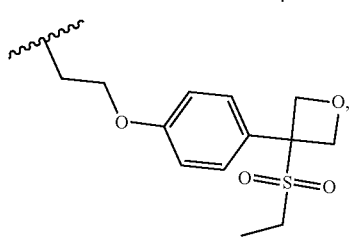
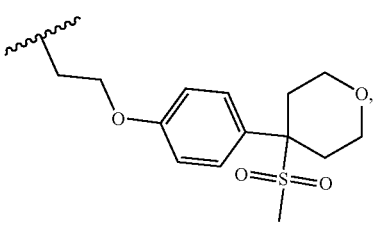
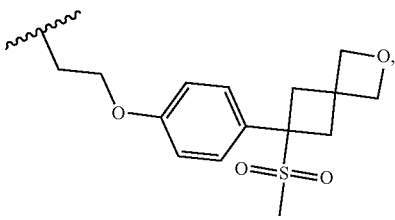
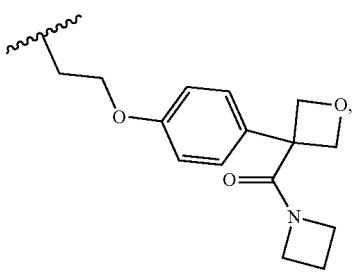
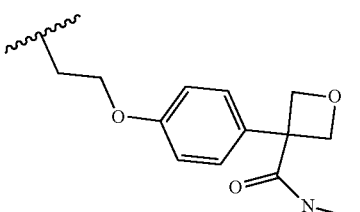
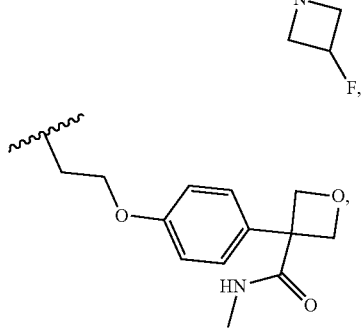

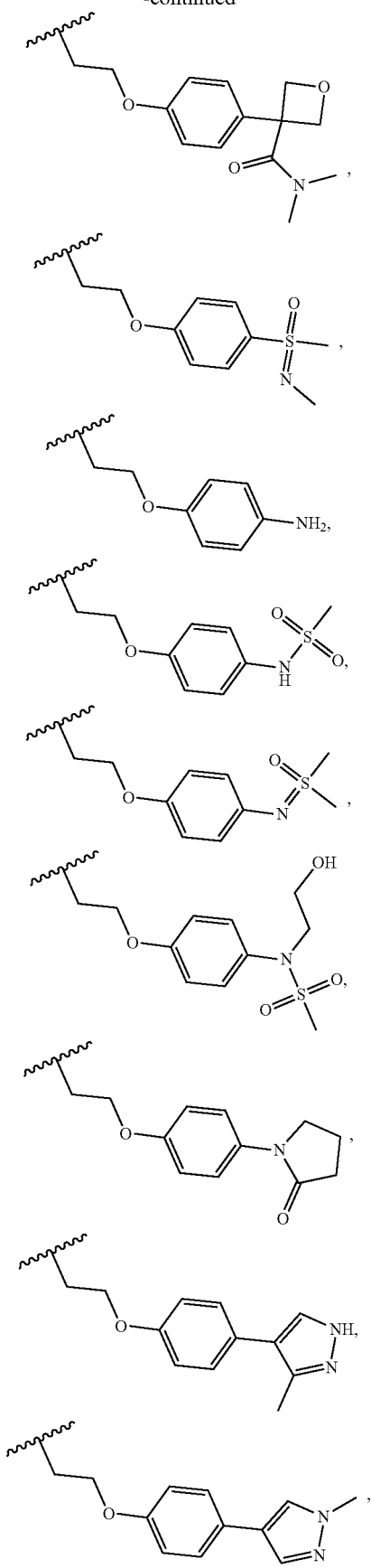

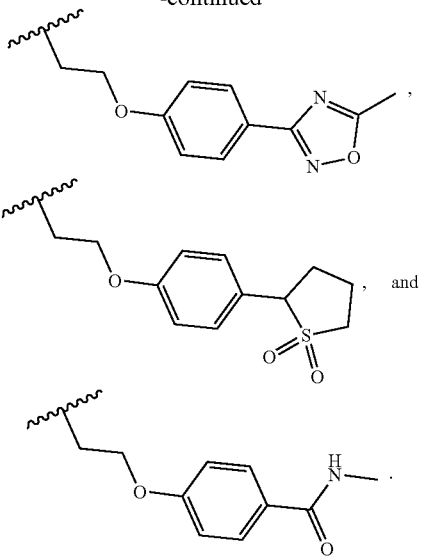

In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I'), or a stereoisomer or tautomer thereof, or a pharmaceutically acceptable salt of any of the foregoing, $L^1$, $L^2$, and the ring bearing $L^3$, $R^4$, $R^6$, and $R^7$ together form a bi-substituted phenyl with one group bound at the para position relative to the phenyl's attachment to $L^2$. In some embodiments, the bi-substituted phenyl is selected from the group consisting of

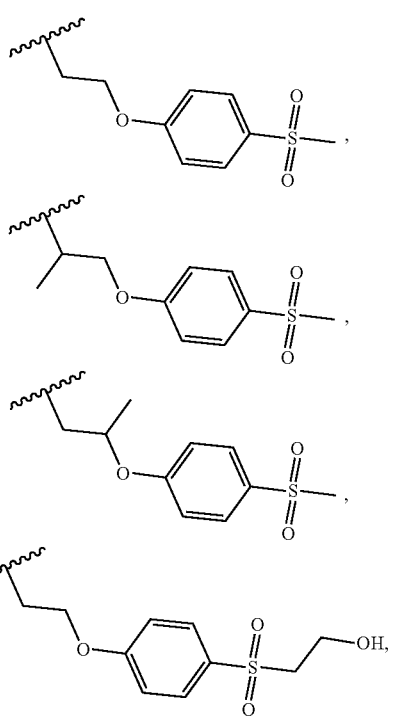

-continued
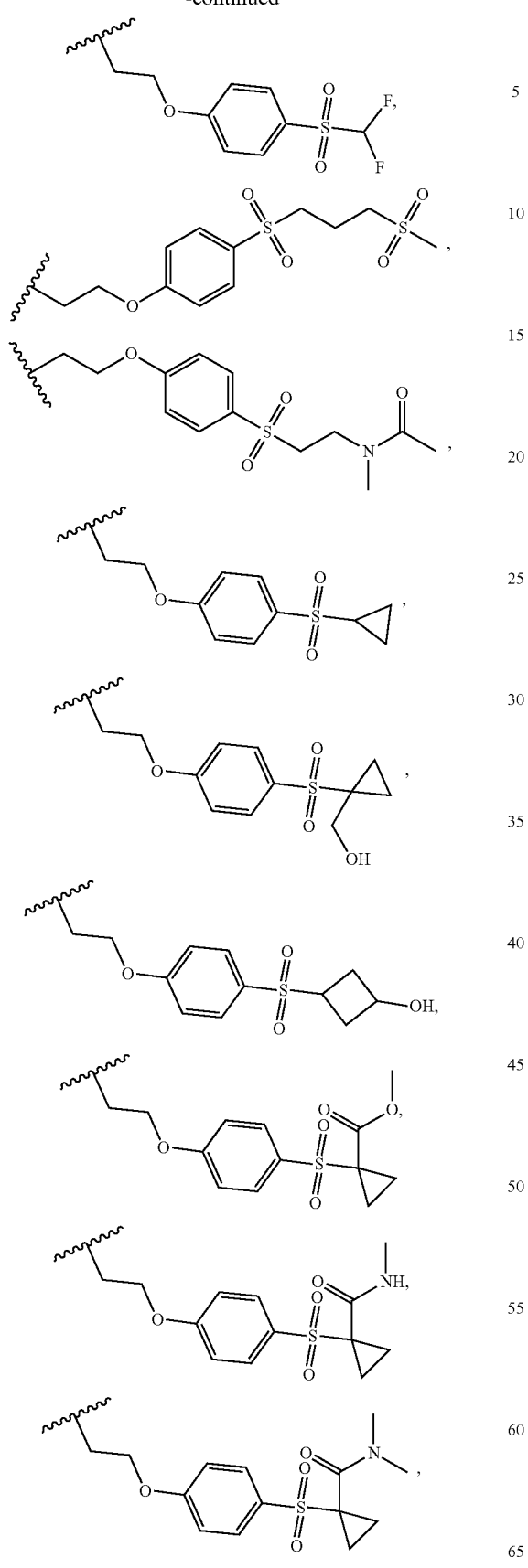
-continued
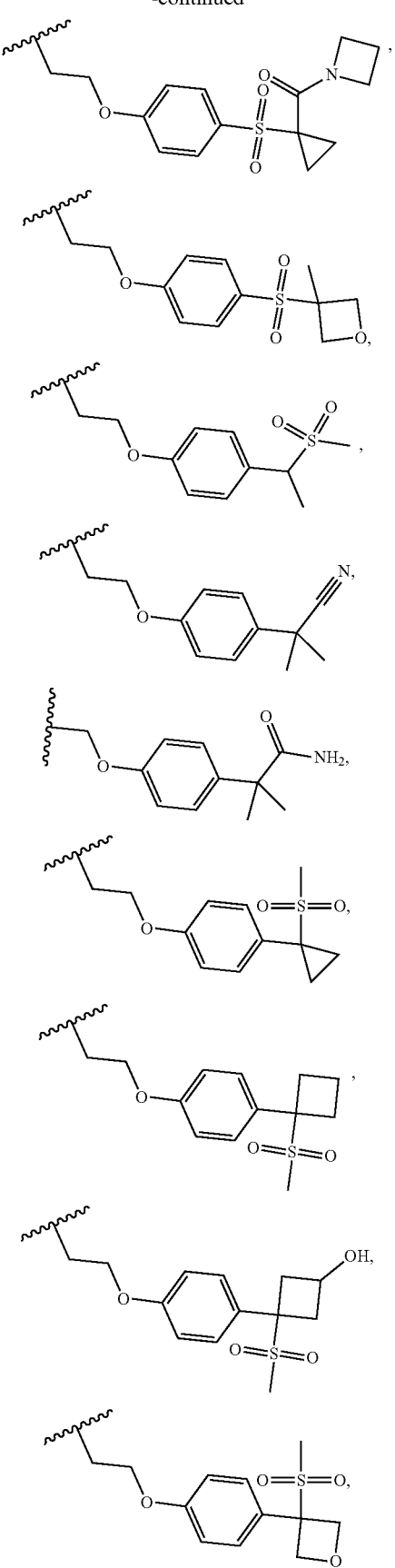

97
-continued
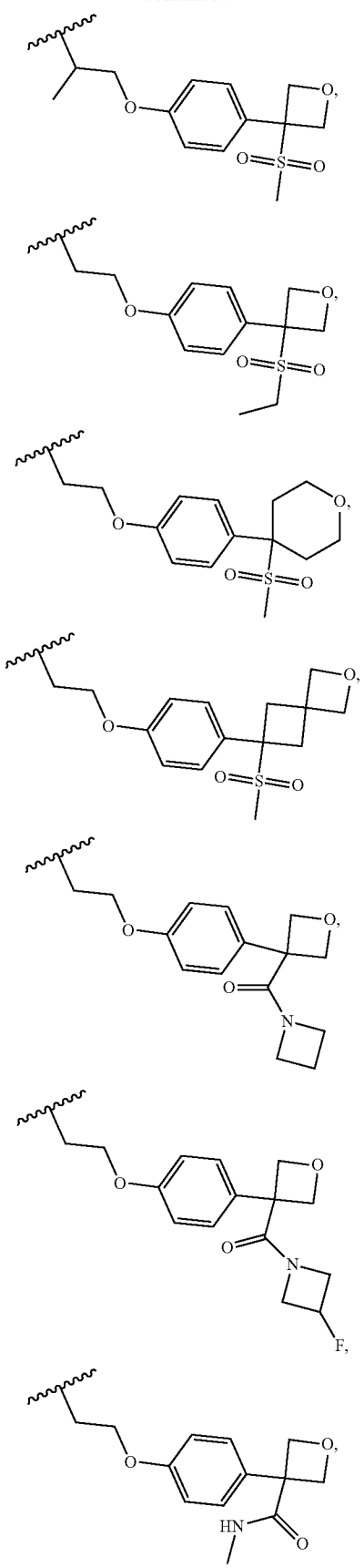
98
-continued
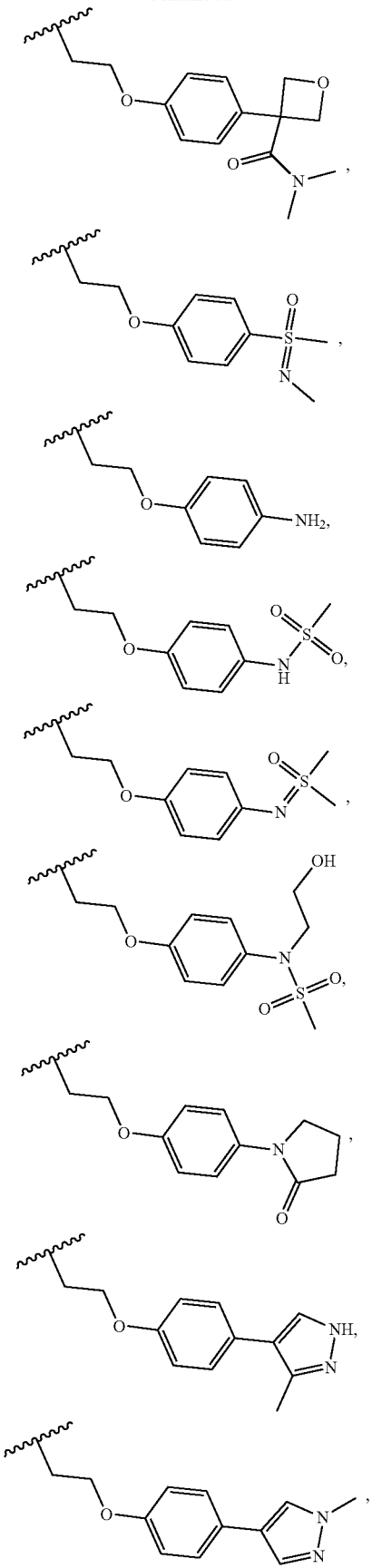

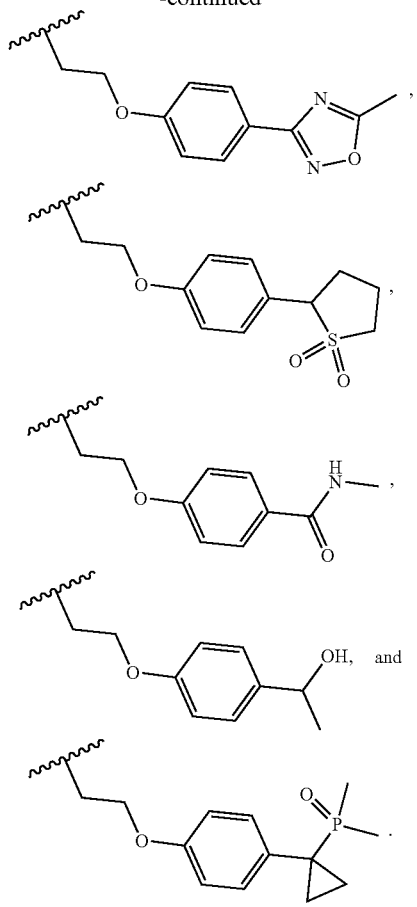

In some variations, the embodiments provided herein also apply to a compound of formula (II), or a stereoisomer or tautomer thereof, or a pharmaceutically acceptable salt of any of the foregoing, or any variation or embodiment thereof.

In some embodiments of a compound of formula (II), or a stereoisomer or tautomer thereof, or a pharmaceutically acceptable salt of any of the foregoing, $L^1$, $L^2$, and the ring bearing $L^3$, $R^4$, $R^6$, and $R^7$ together form a bi-substituted phenyl with one group bound at the para position relative to the phenyl's attachment to $L^2$. In some embodiments, the bi-substituted phenyl is selected from the group consisting of

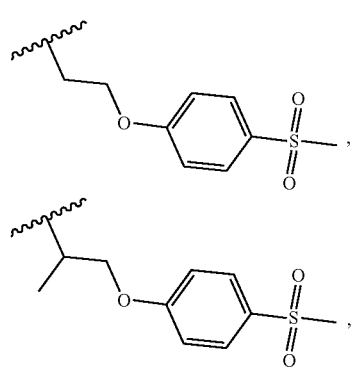

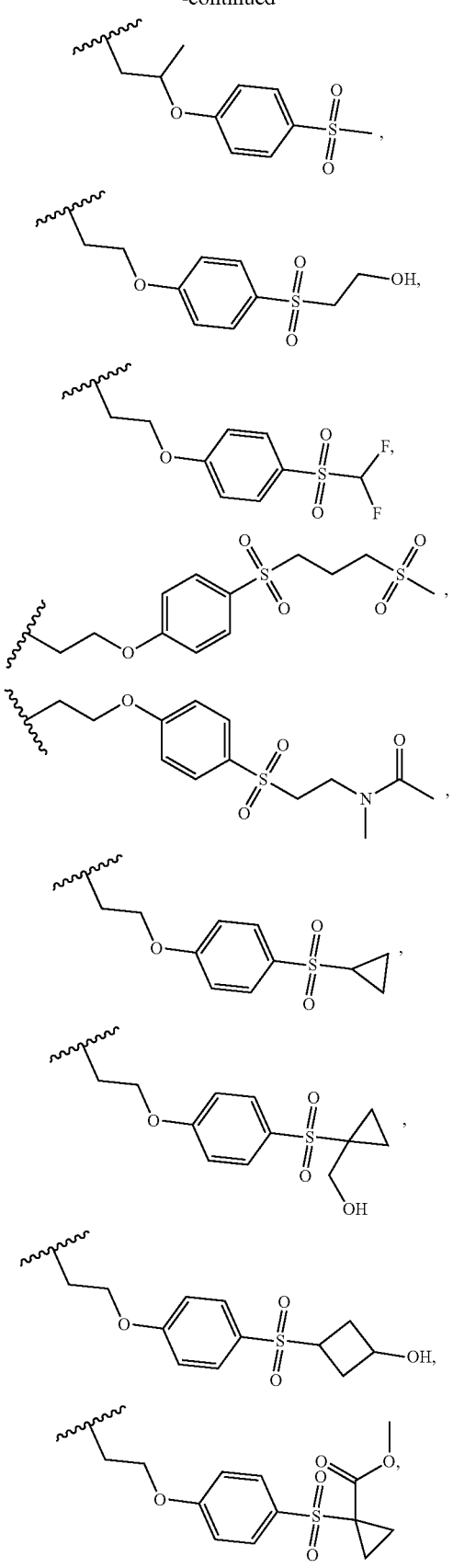

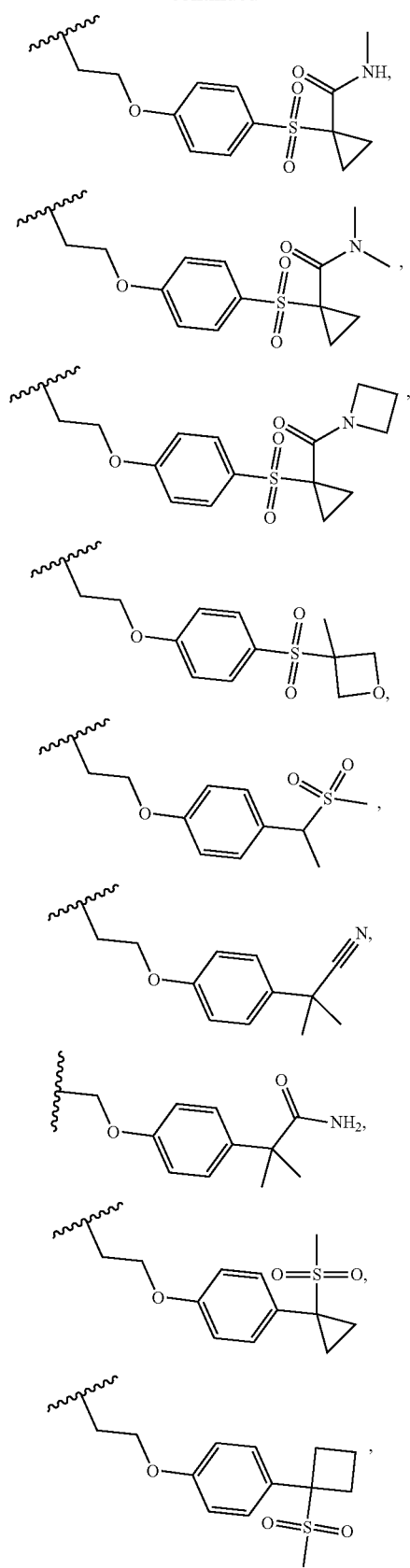
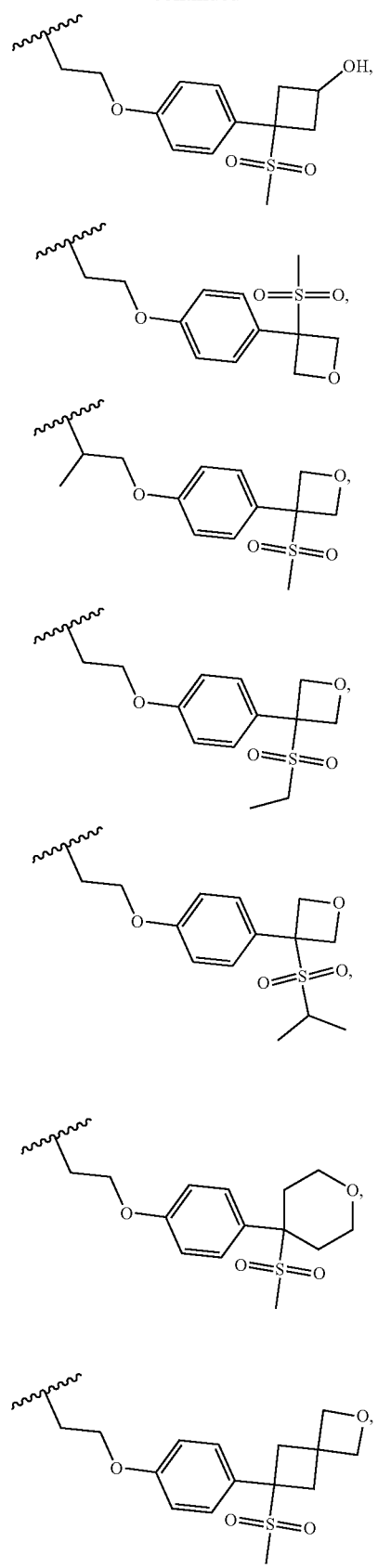

103
-continued
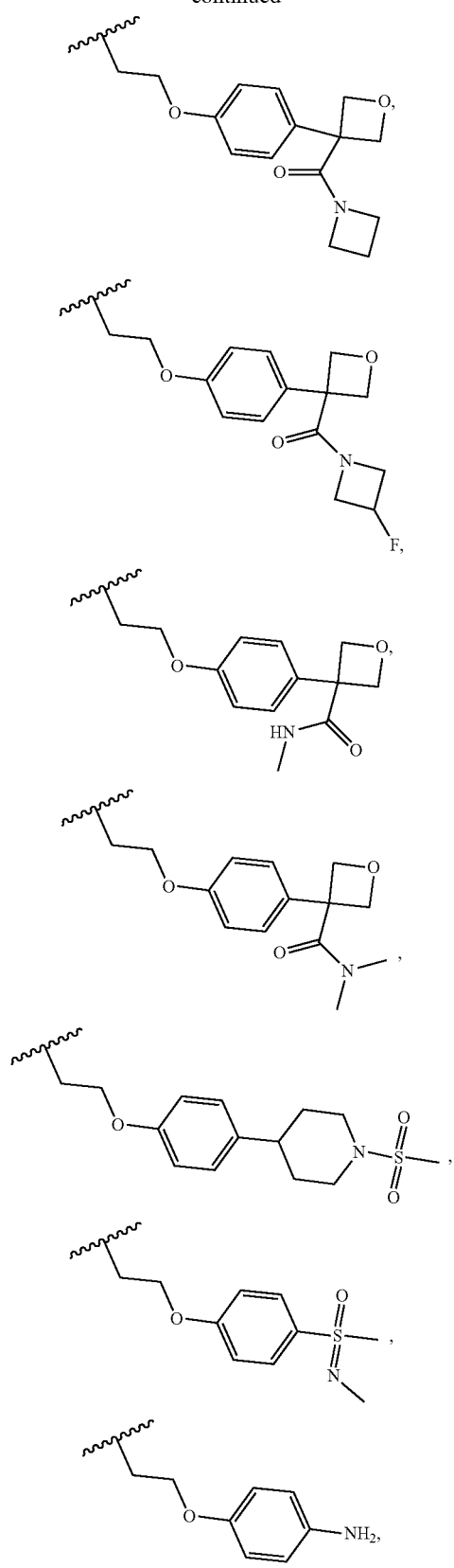
104
-continued
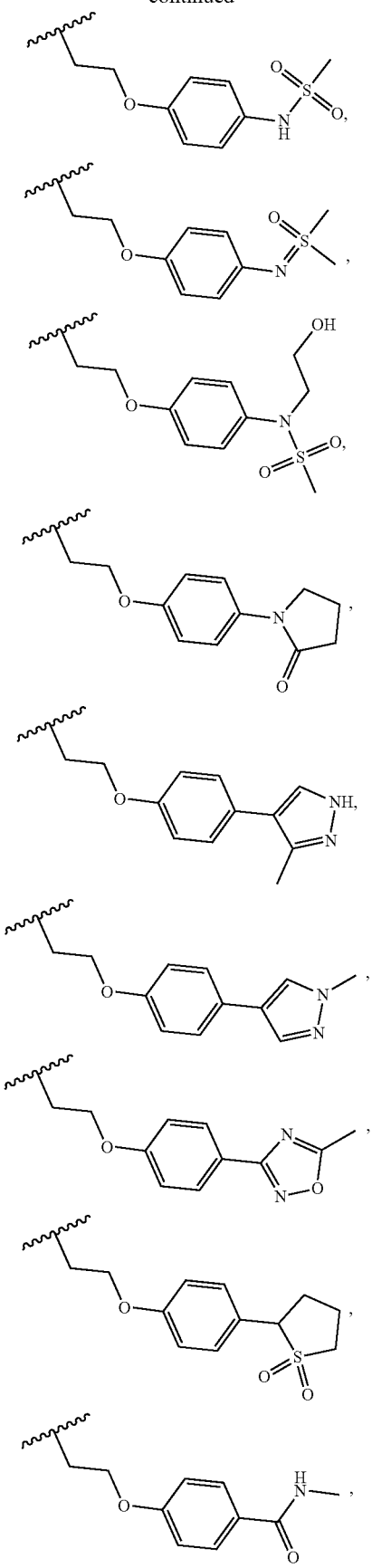

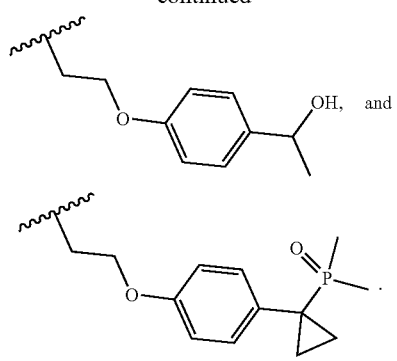

In some embodiments of a compound of formula (I), or a stereoisomer or tautomer thereof, or a pharmaceutically acceptable salt of any of the foregoing, $L^1$, $L^2$, and the ring bearing $L^3$, $R^4$, $R^6$, and $R^7$ together form a tri-substituted phenyl with two groups bound at a meta, and the para positions relative to the phenyl's attachment to $L^2$. In some embodiments, the tri-substituted phenyl is selected from the group consisting of

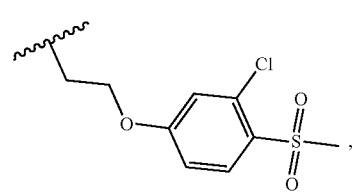

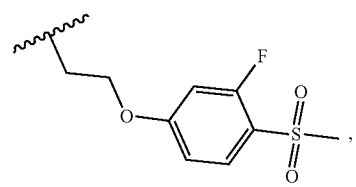

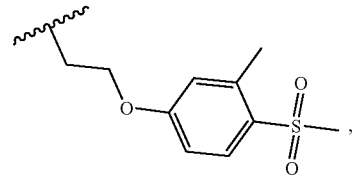

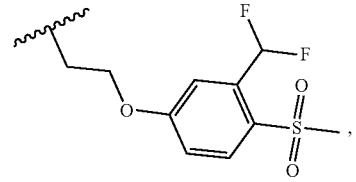

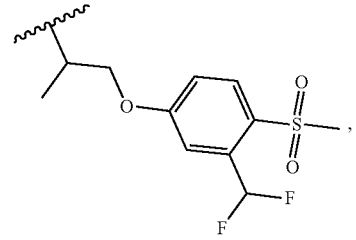

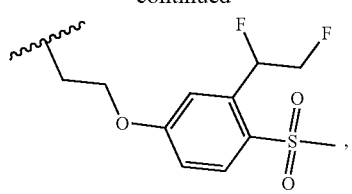

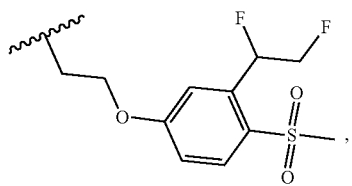

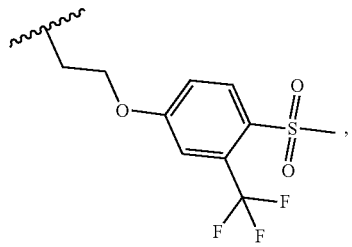

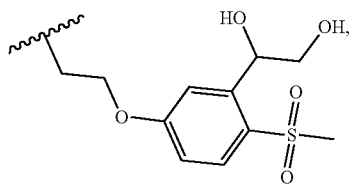

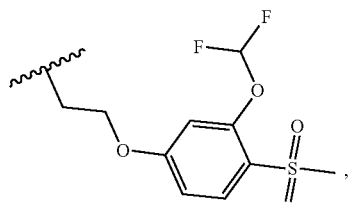

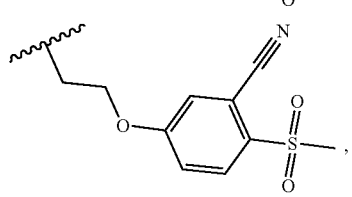

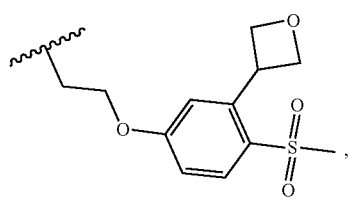

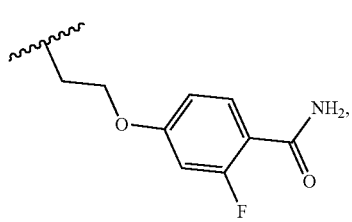

107
-continued
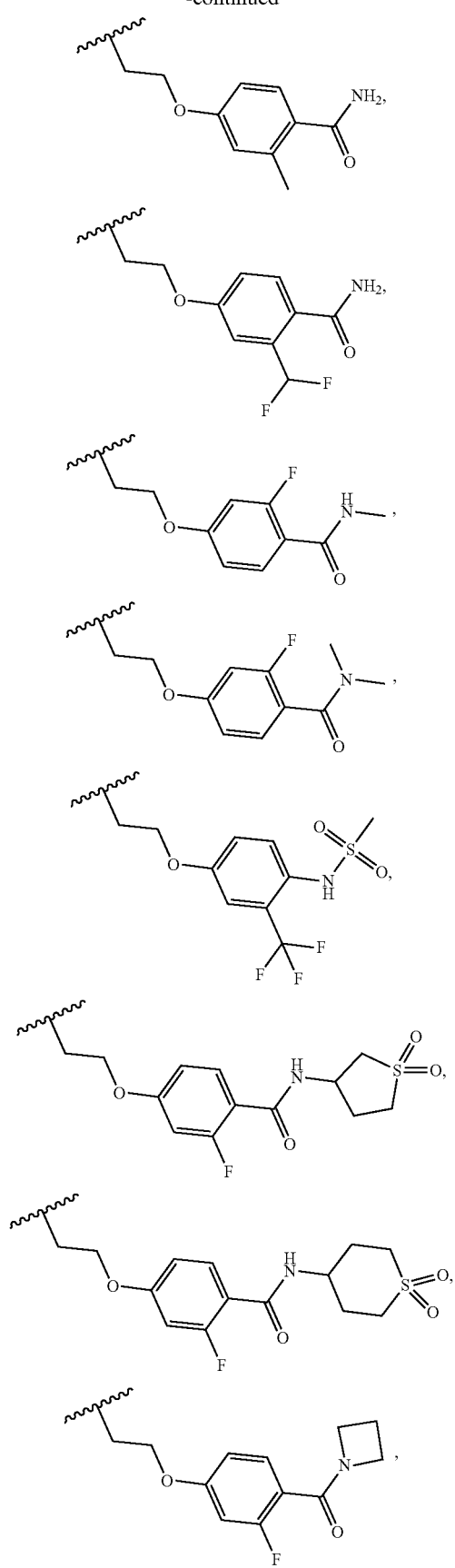
108
-continued
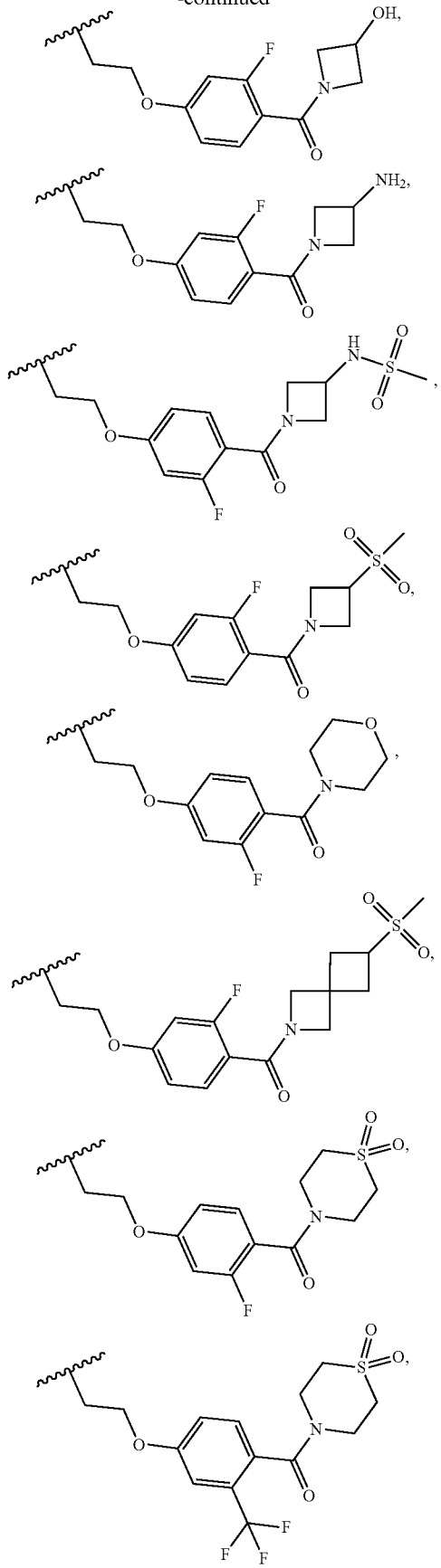

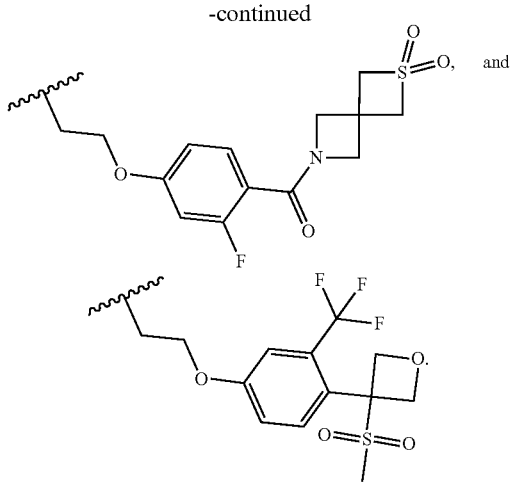

In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (II), or a stereoisomer or tautomer thereof, or a pharmaceutically acceptable salt of any of the foregoing, $L^1$, $L^2$, and the ring bearing $L^3$, $R^4$, $R^6$, and $R^7$ together form a tri-substituted phenyl with two groups bound at a meta, and the para positions relative to the phenyl's attachment to $L^2$. In some embodiments, the tri-substituted phenyl is selected from the group consisting of

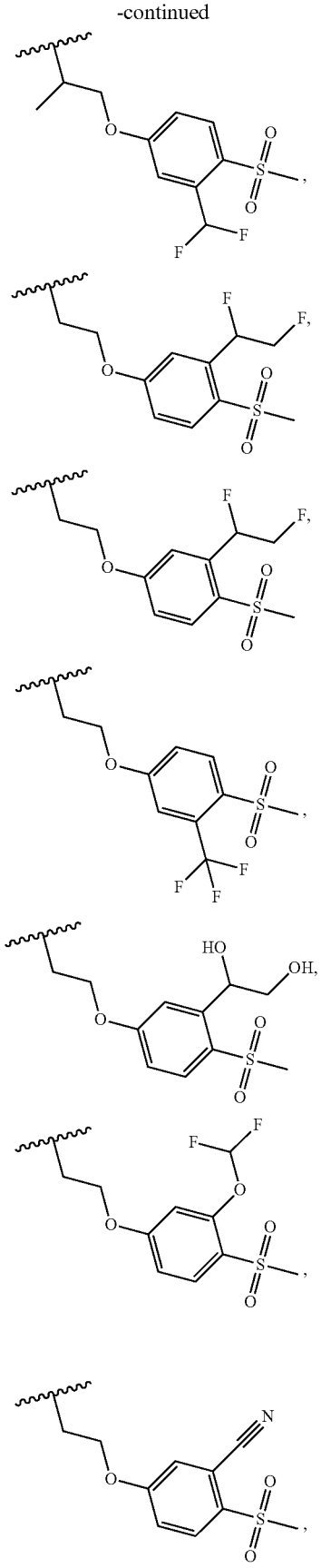

111
-continued
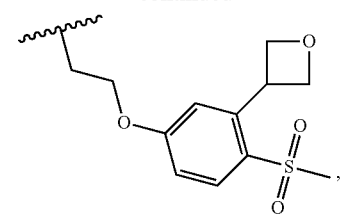
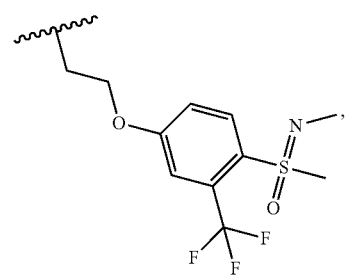
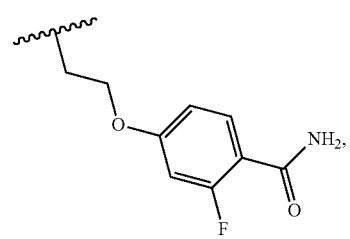
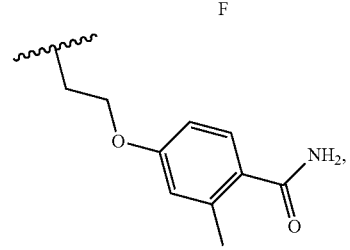
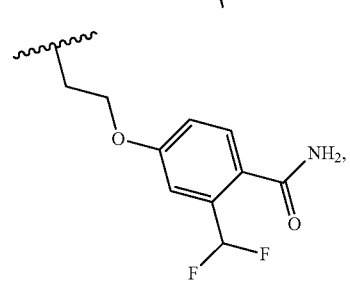
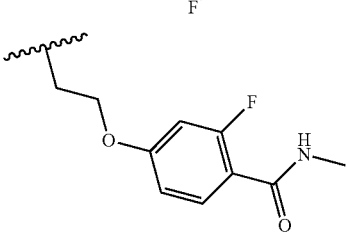
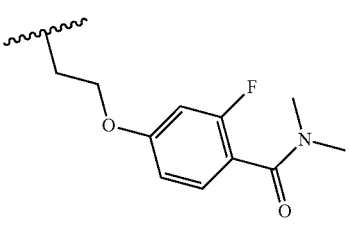
112
-continued
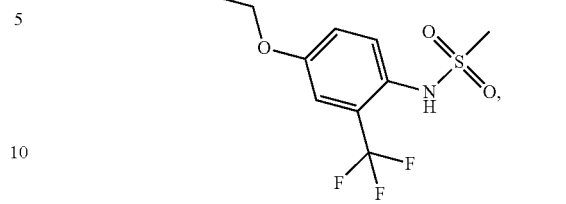
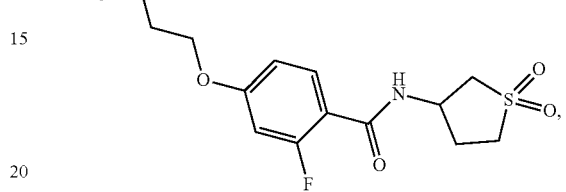

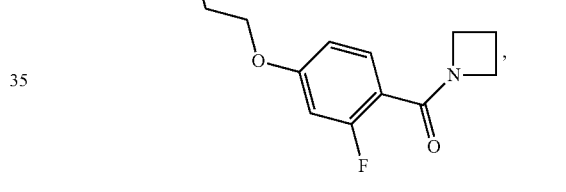
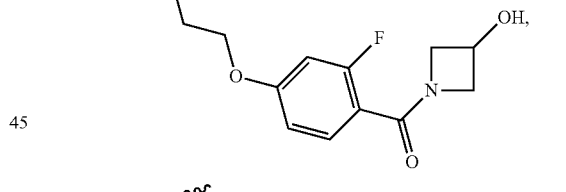

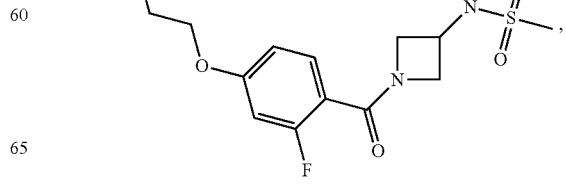

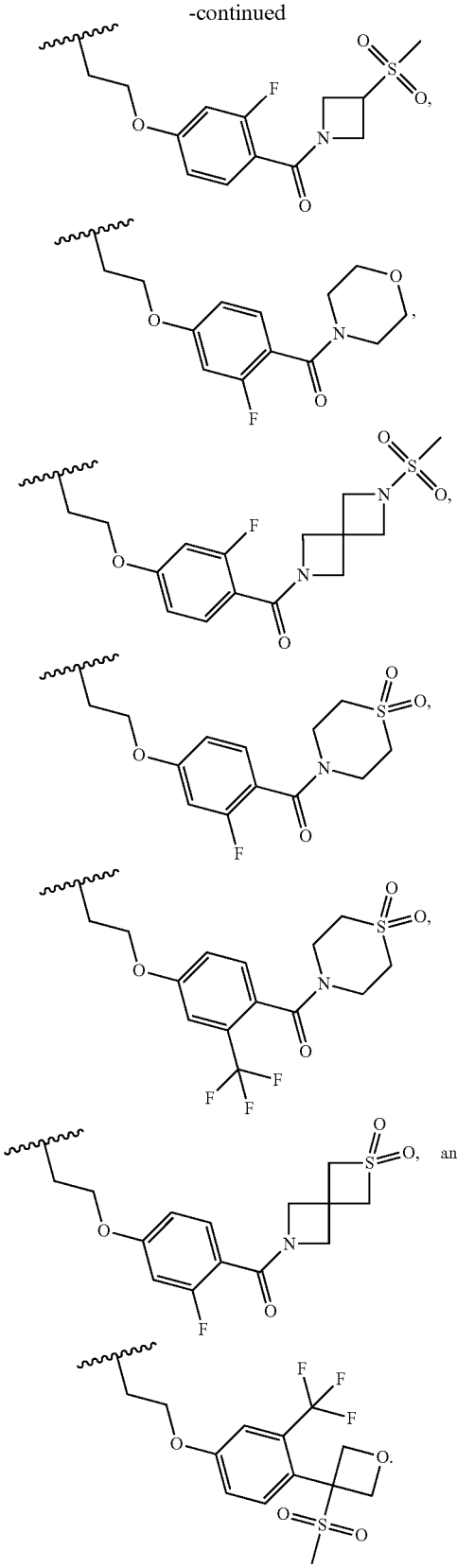

bearing $L^3$, $R^4$, $R^6$, and $R^7$ together form a tetra-substituted phenyl with three groups bound at the meta, and para positions relative to the phenyl's attachment to $L^2$. In some embodiments, the tetra-substituted phenyl is selected from the group consisting of In some embodiments of a compound of formula (I), or a stereoisomer or tautomer thereof, or a pharmaceutically acceptable salt of any of the foregoing, $L^1$, $L^2$, and the ring -continued

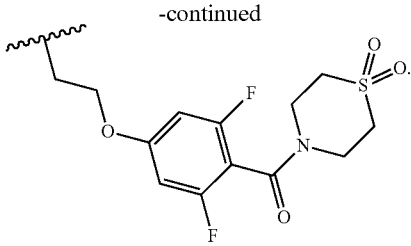

In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), or a stereoisomer or tautomer thereof, or a pharmaceutically acceptable salt of any of the foregoing, $L^1$, $L^2$, and the ring bearing $L^3$, $R^4$, $R^6$, and $R^7$ together form a bi-substituted pyridine with one group bound at the para position relative to the pyridine's attachment to $L^2$. In some embodiments, the bi-substituted pyridine is selected from the group consisting of

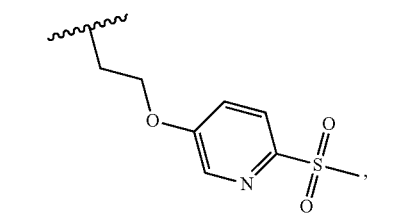

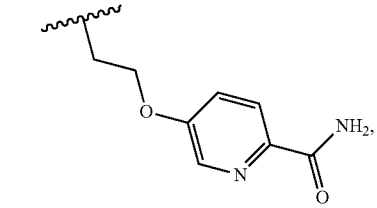

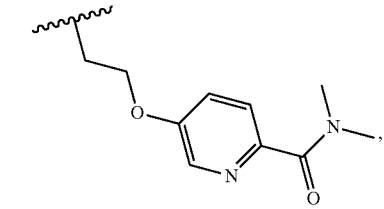

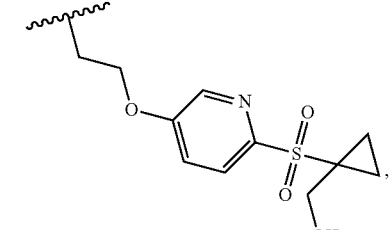

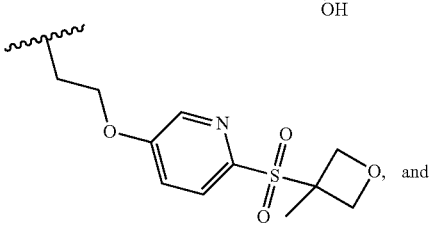

-continued

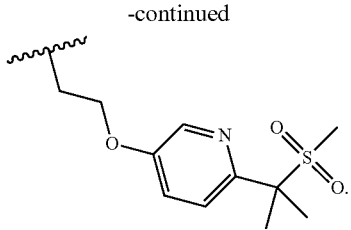

In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), or a stereoisomer or tautomer thereof, or a pharmaceutically acceptable salt of any of the foregoing, $L^1$, $L^2$, and the ring bearing $L^3$, $R^4$, $R^6$, and $R^7$ together form a tri-substituted pyridine with two groups bound at the meta, and para positions relative to the pyridine's attachment to $L^2$. In some embodiments, the tri-substituted pyridine is

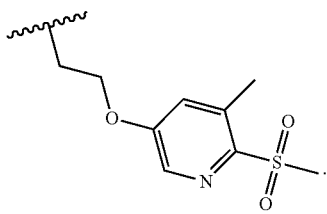 [SMILES: *CCOc1cnc(S(C)(=O)=O)c(C)c1]

In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I'), or a stereoisomer or tautomer thereof, or a pharmaceutically acceptable salt of any of the foregoing, $L^1$, $L^2$, and the ring bearing $L^3$, $R^4$, $R^6$, and $R^7$ together form a tri-substituted pyridine with two groups bound at the meta, and para positions relative to the pyridine's attachment to $L^2$. In some embodiments, the tri-substituted pyridine is selected from the group consisting of

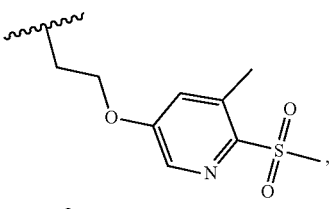

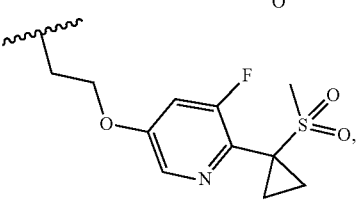

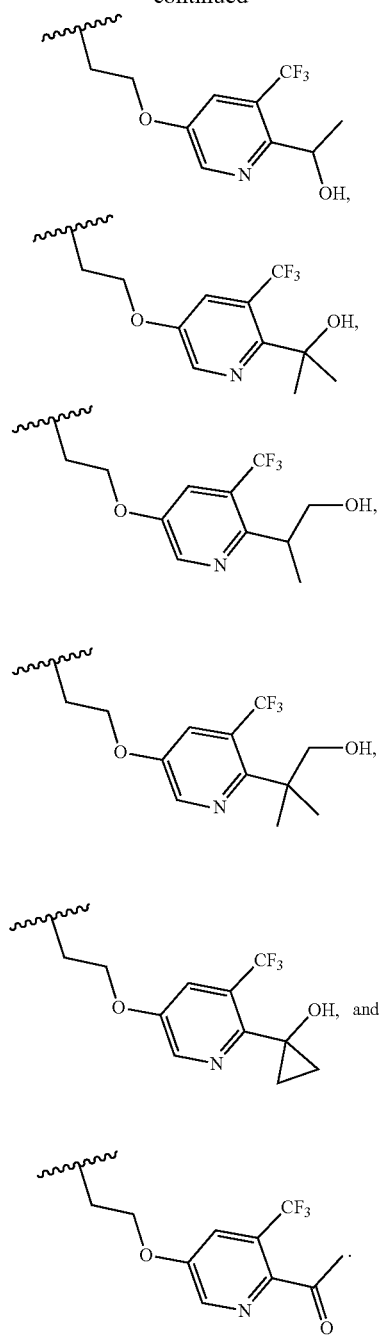
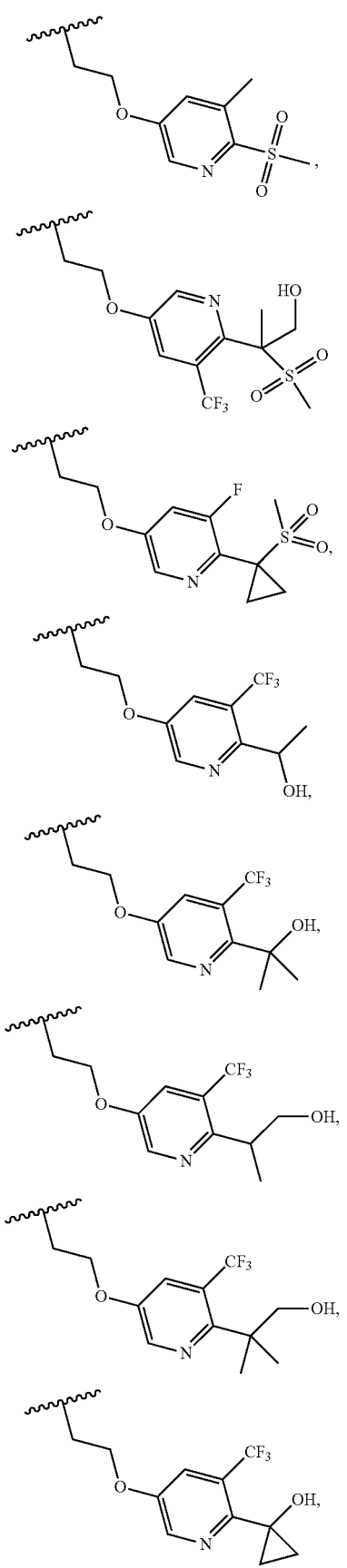

In some variations, the embodiments provided herein also apply to a compound of formula (II), or a stereoisomer or tautomer thereof, or a pharmaceutically acceptable salt of any of the foregoing, or any variation or embodiment thereof.

In some embodiments of a compound of formula (II), or a stereoisomer or tautomer thereof, or a pharmaceutically acceptable salt of any of the foregoing, $L^1$, $L^2$, and the ring bearing $L^3$, $R^4$, $R^6$, and $R^7$ together form a tri-substituted pyridine with two groups bound at the meta, and para positions relative to the pyridine's attachment to $L^2$. In some embodiments, the tri-substituted pyridine is selected from the group consisting of

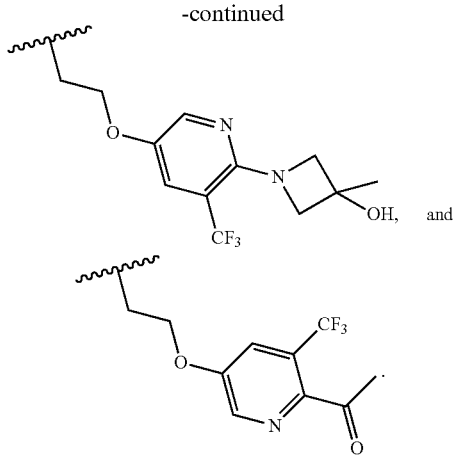

In some embodiments of a compound of formula (I), or a stereoisomer or tautomer thereof, or a pharmaceutically acceptable salt of any of the foregoing, $L^1$, $L^2$, and the ring bearing $L^3$, $R^4$, $R^6$, and $R^7$ together form a bi-substituted pyrimidine with two groups bound at the para position relative to the pyrimidine's attachment to $L^2$. In some embodiments, the bi-substituted pyrimidine is selected from the group consisting of

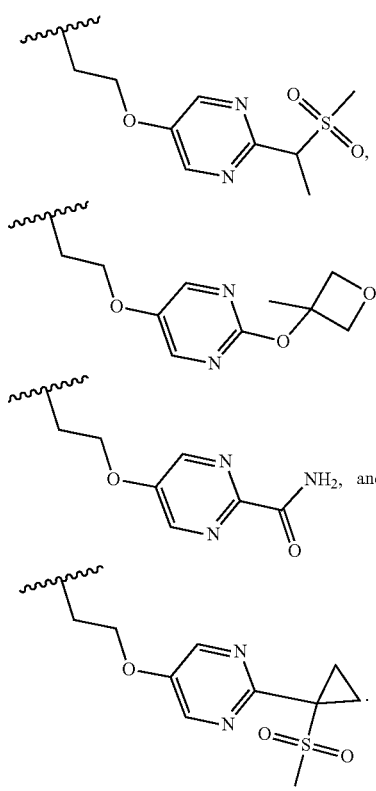

In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I'), or a stereoisomer or tautomer thereof, or a pharmaceutically acceptable salt of any of the foregoing, $L^1$, $L^2$, and the ring bearing $L^3$, $R^4$, $R^6$, and $R^7$ together form a bi-substituted pyrimidine with two groups bound at the para position relative to the pyrimidine's attachment to $L^2$. In some embodiments, the bi-substituted pyrimidine is selected from the group consisting of

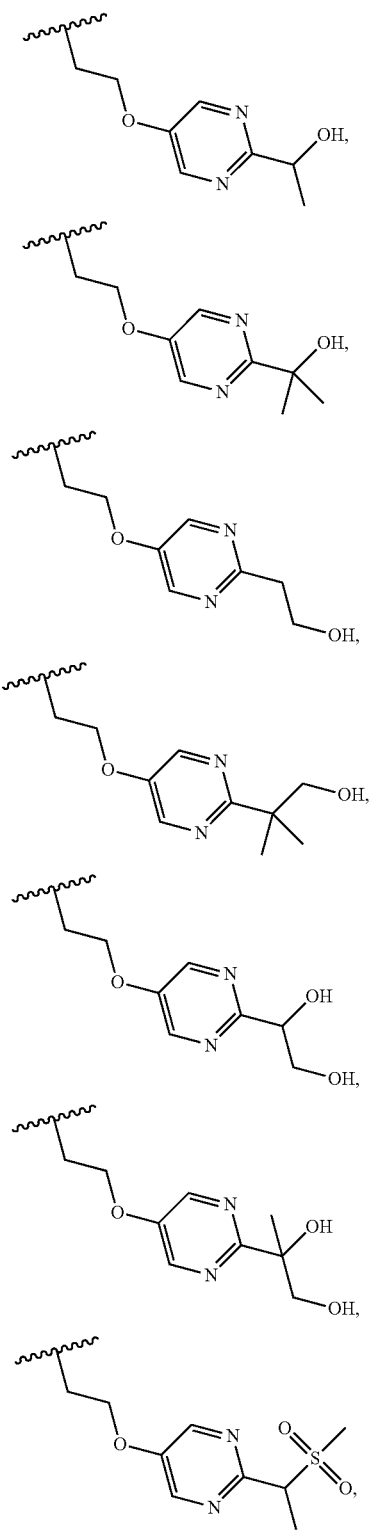

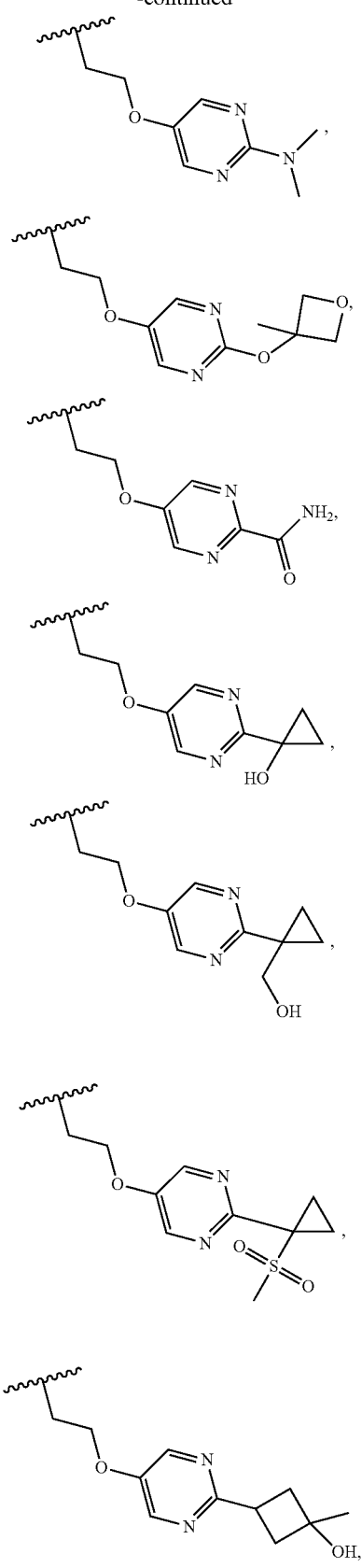
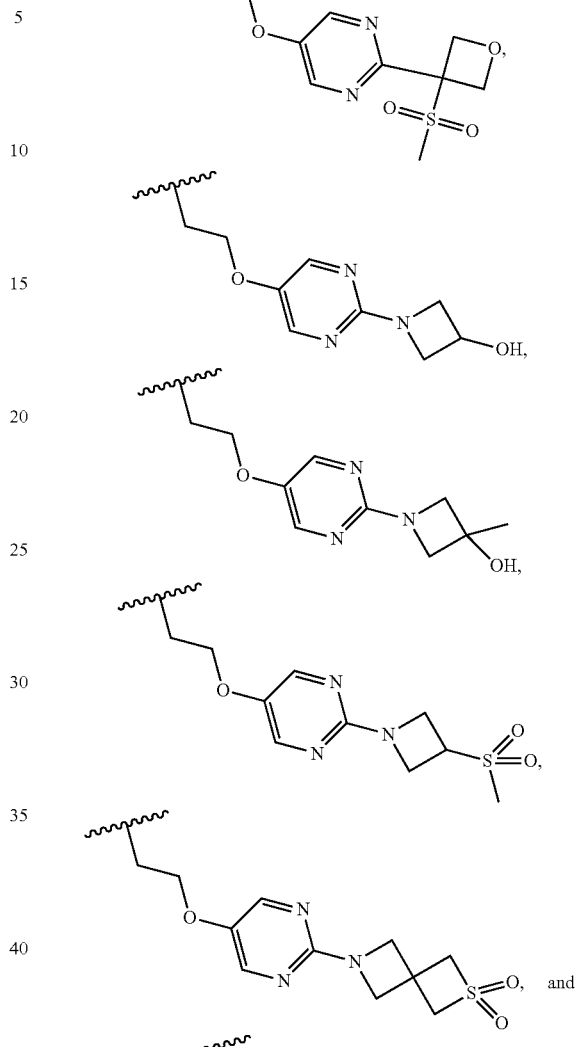

In some variations, the embodiments provided herein also apply to a compound of formula (II), or a stereoisomer or tautomer thereof, or a pharmaceutically acceptable salt of any of the foregoing, or any variation or embodiment thereof.

In some embodiments of a compound of formula (I'), or a stereoisomer or tautomer thereof, or a pharmaceutically acceptable salt of any of the foregoing, $L^1$, $L^2$, and the ring bearing $L^3$, $R^4$, $R^6$, and $R^7$ together form a bi-substituted pyrimidine with two groups bound at the para position relative to the pyrimidine's attachment to $L^2$. In some embodiments, the bi-substituted pyrimidine is selected from the group consisting of

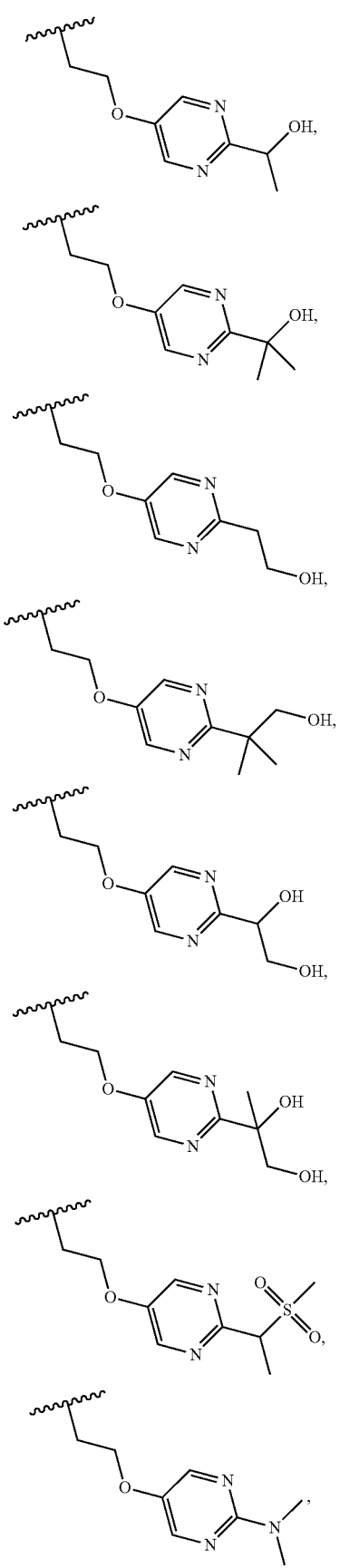
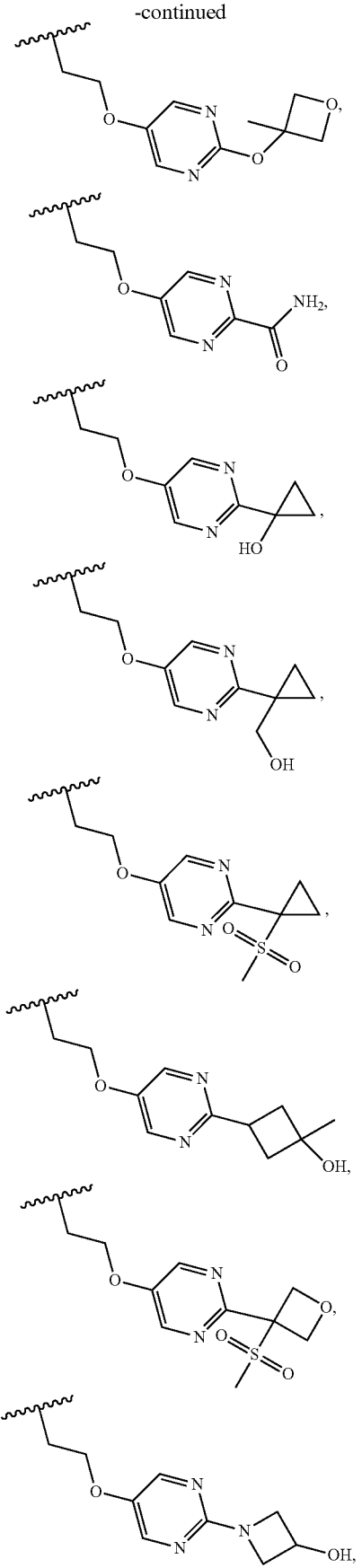

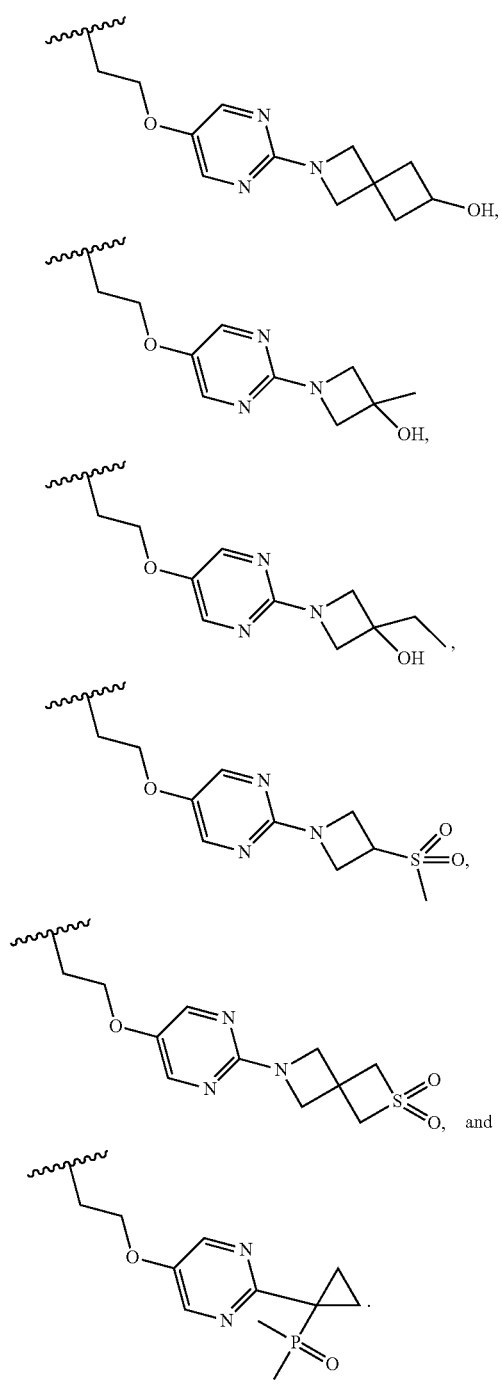
In some embodiments, the bi-substituted pyrimidine is selected from the group consisting of
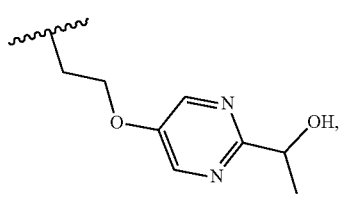
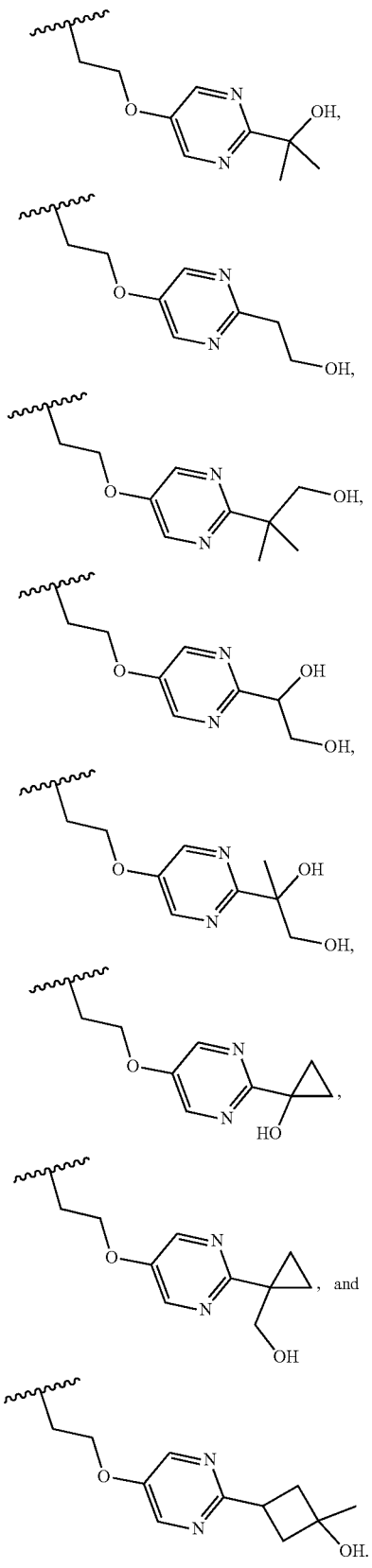
In some variations, the embodiments provided herein also apply to a compound of formula (II), or a stereoisomer or tautomer thereof, or a pharmaceutically acceptable salt of any of the foregoing, or any variation or embodiment thereof.

In some embodiments of a compound of formula (II), or a stereoisomer or tautomer thereof, or a pharmaceutically acceptable salt of any of the foregoing, $L^1$, $L^2$, and the ring bearing $L^3$, $R^4$, $R^6$, and $R^7$ together form a bi-substituted pyrimidine with two groups bound at the para position relative to the pyrimidine's attachment to $L^2$. In some embodiments, the bi-substituted pyrimidine is selected from the group consisting of

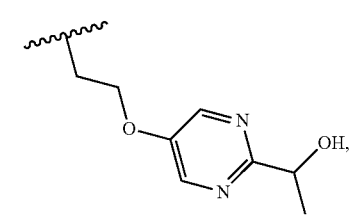

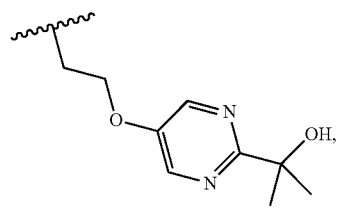

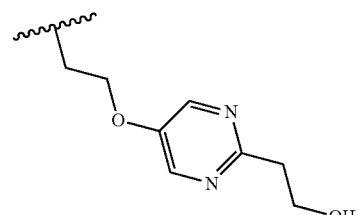

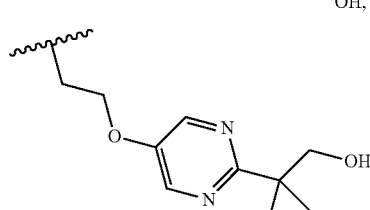

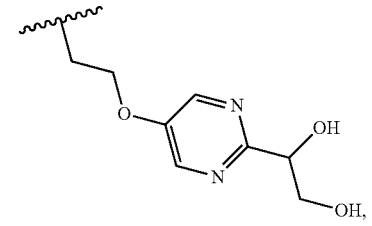

-continued

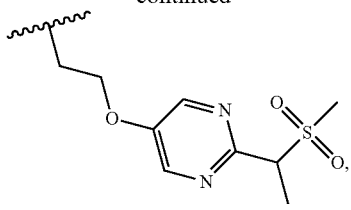

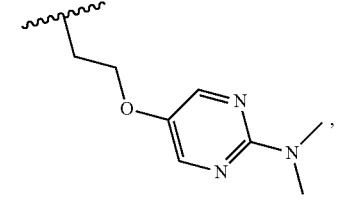

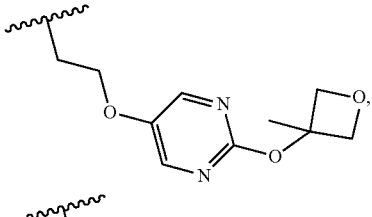

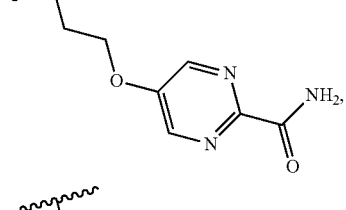

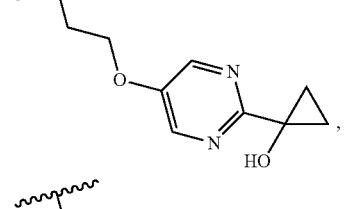

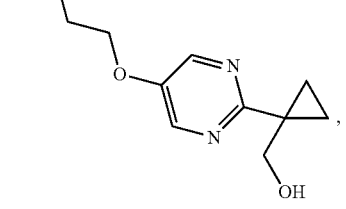

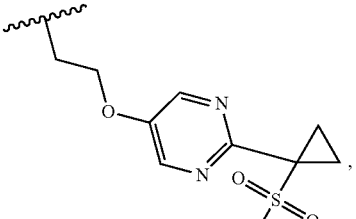

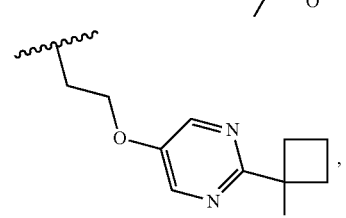

-continued
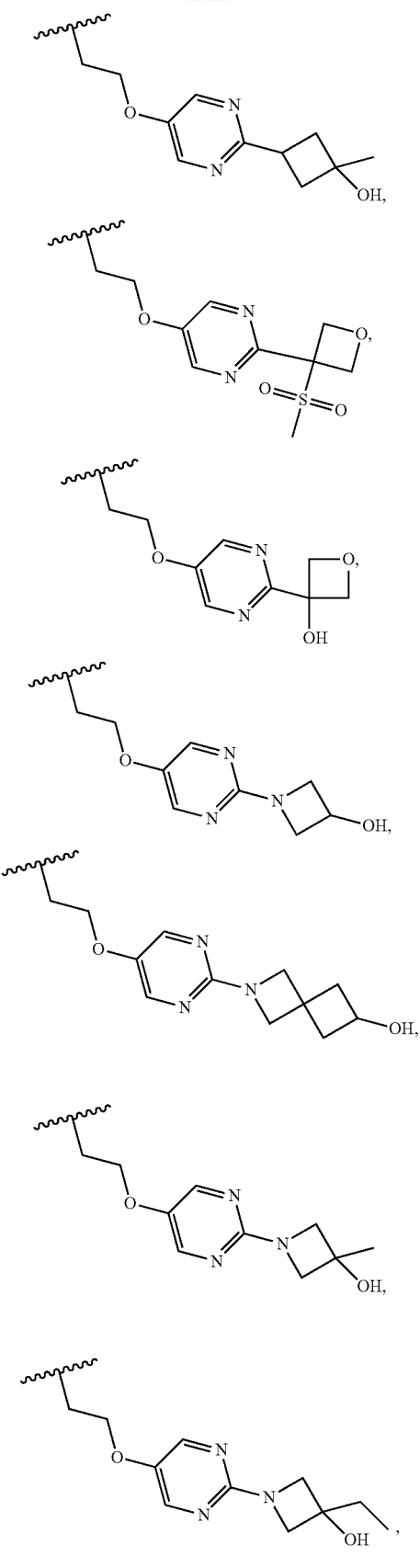
-continued
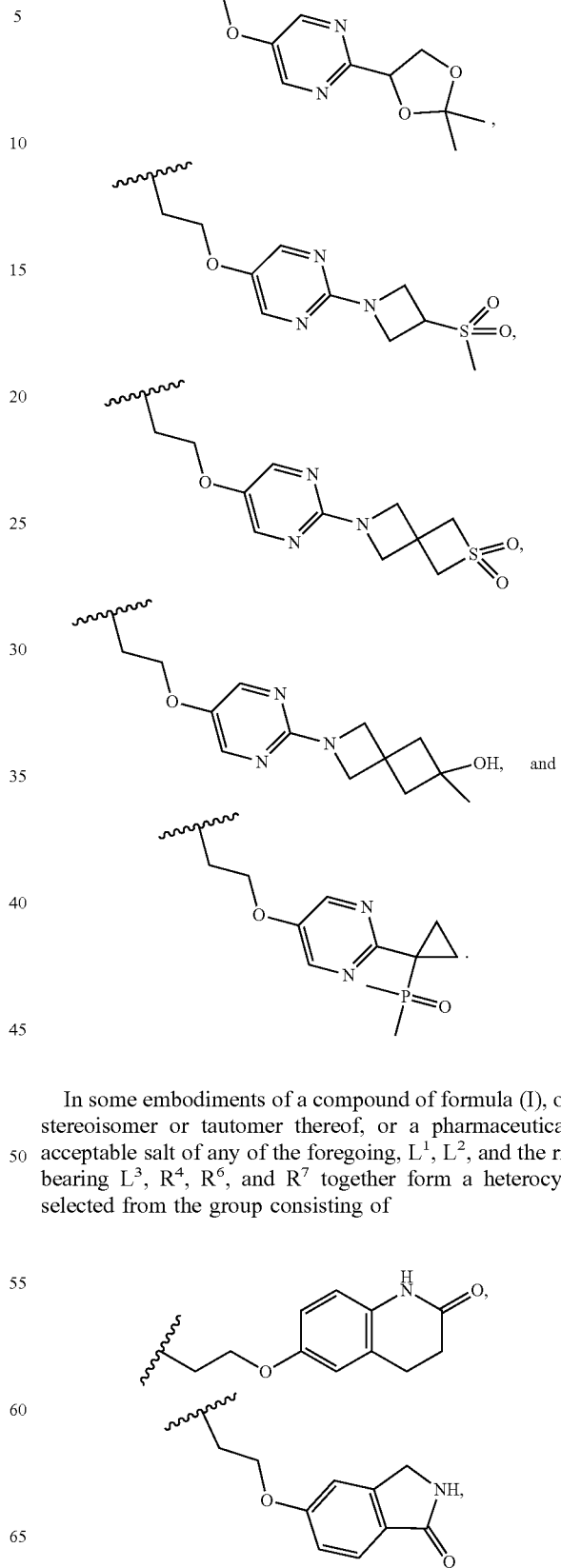
In some embodiments of a compound of formula (I), or a stereoisomer or tautomer thereof, or a pharmaceutically acceptable salt of any of the foregoing, $L^1$, $L^2$, and the ring bearing $L^3$, $R^4$, $R^6$, and $R^7$ together form a heterocycle selected from the group consisting of
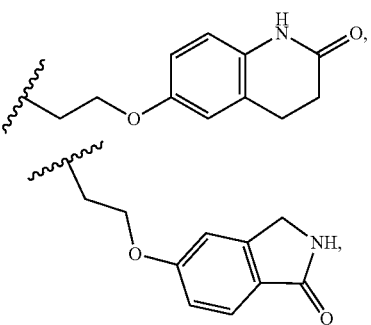

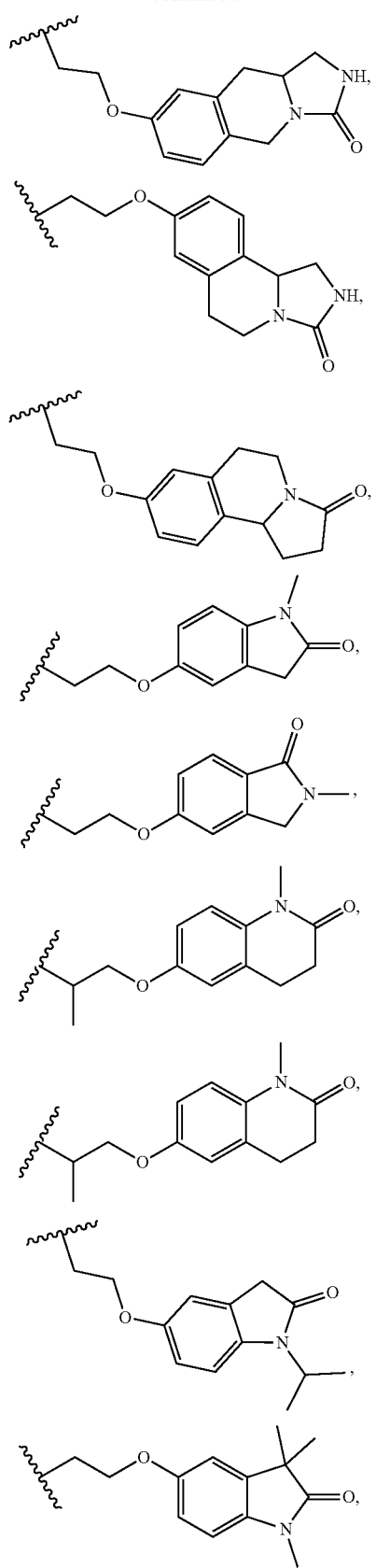
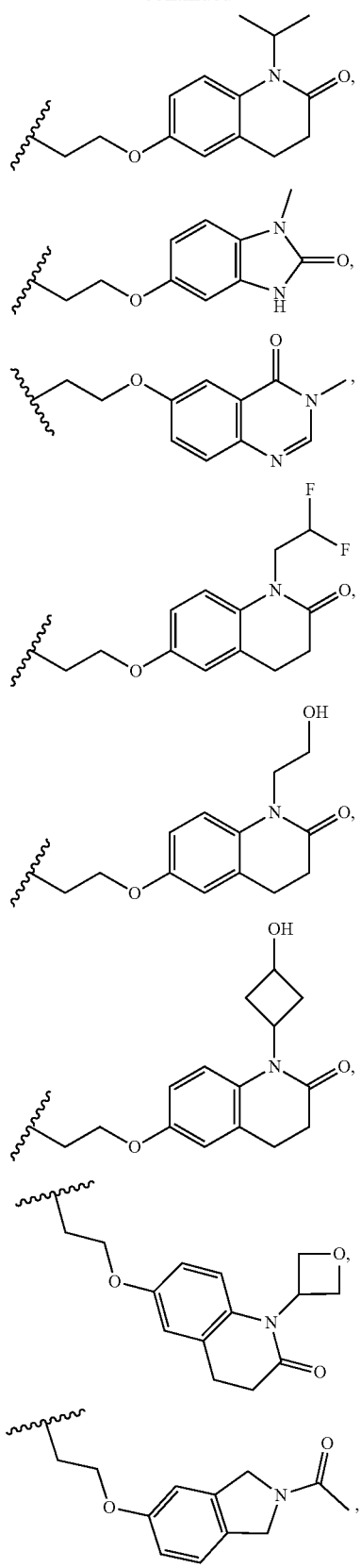

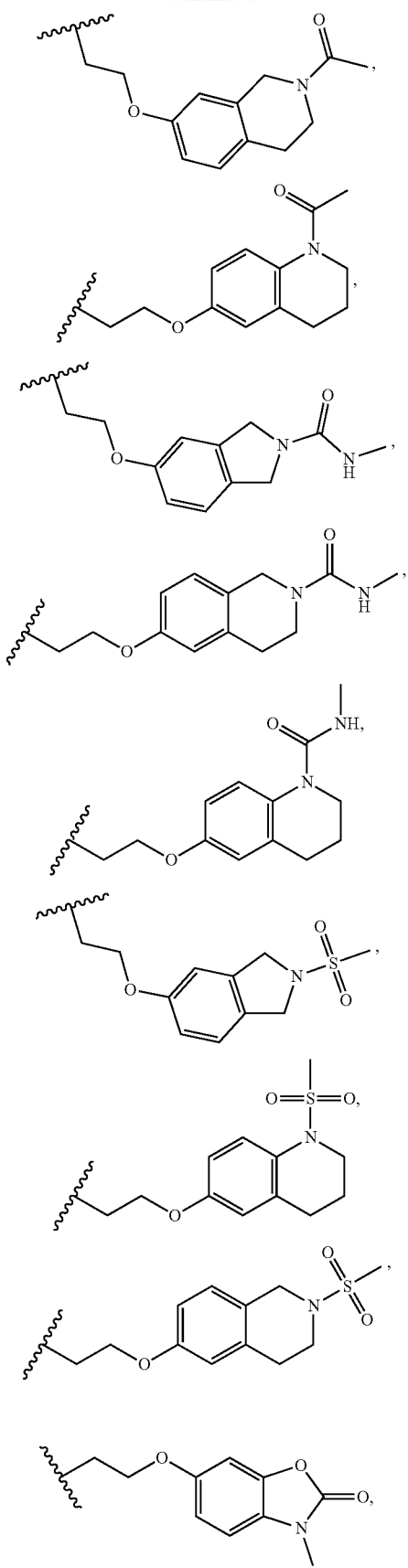
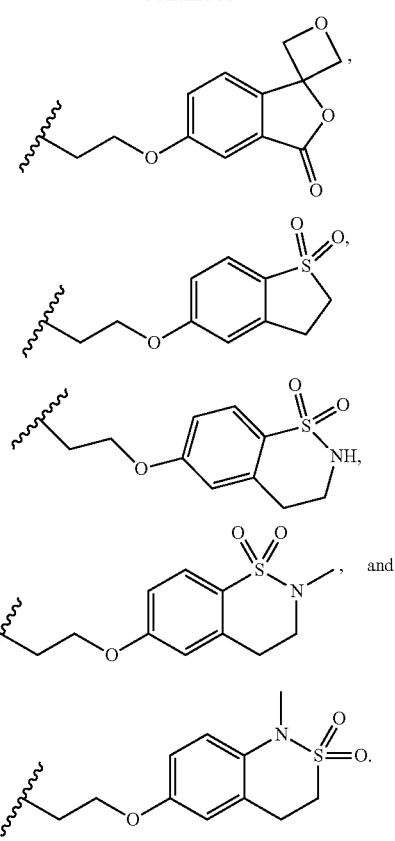

In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I'), or a stereoisomer or tautomer thereof, or a pharmaceutically acceptable salt of any of the foregoing, $L^1$, $L^2$, and the ring bearing $L^3$, $R^4$, $R^6$, and $R^7$ together form a heterocycle selected from the group consisting of

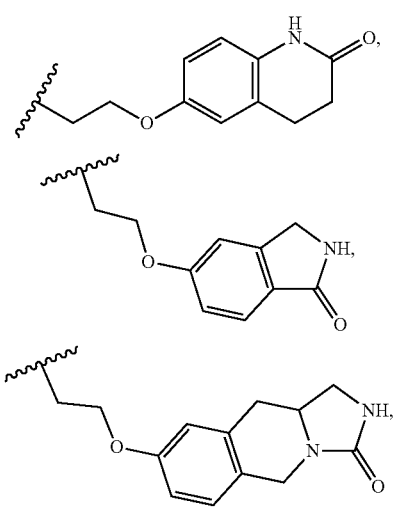

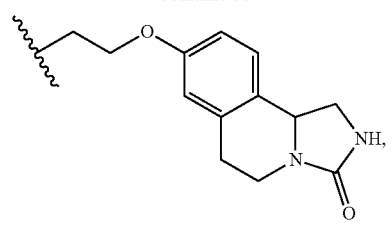
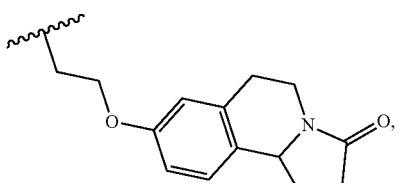
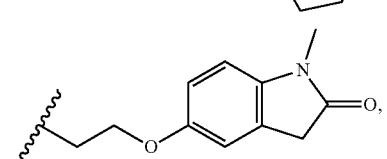
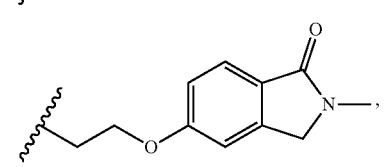
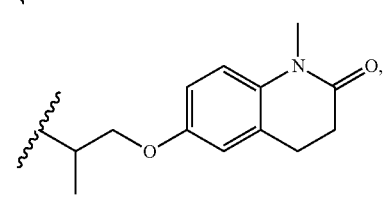
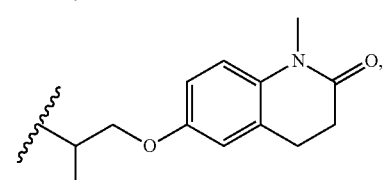
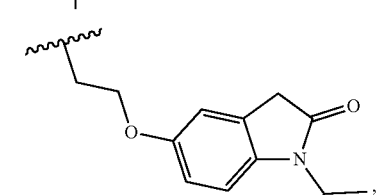
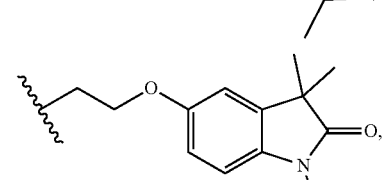
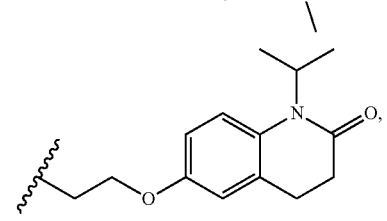
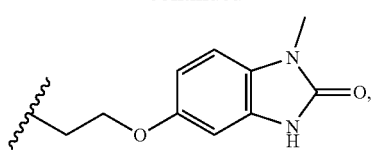
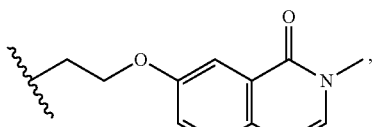
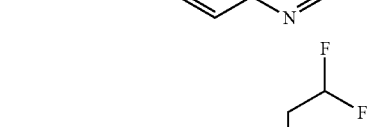
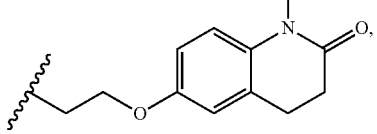
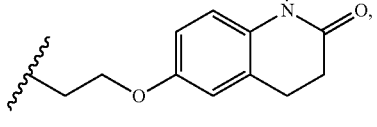
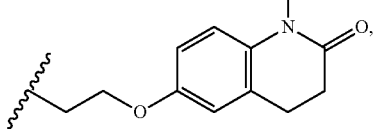
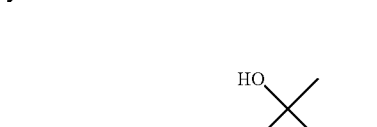
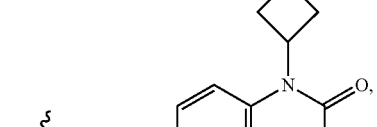
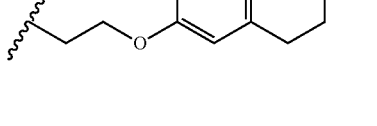
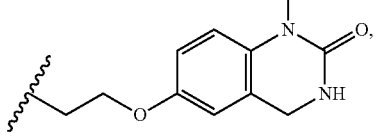

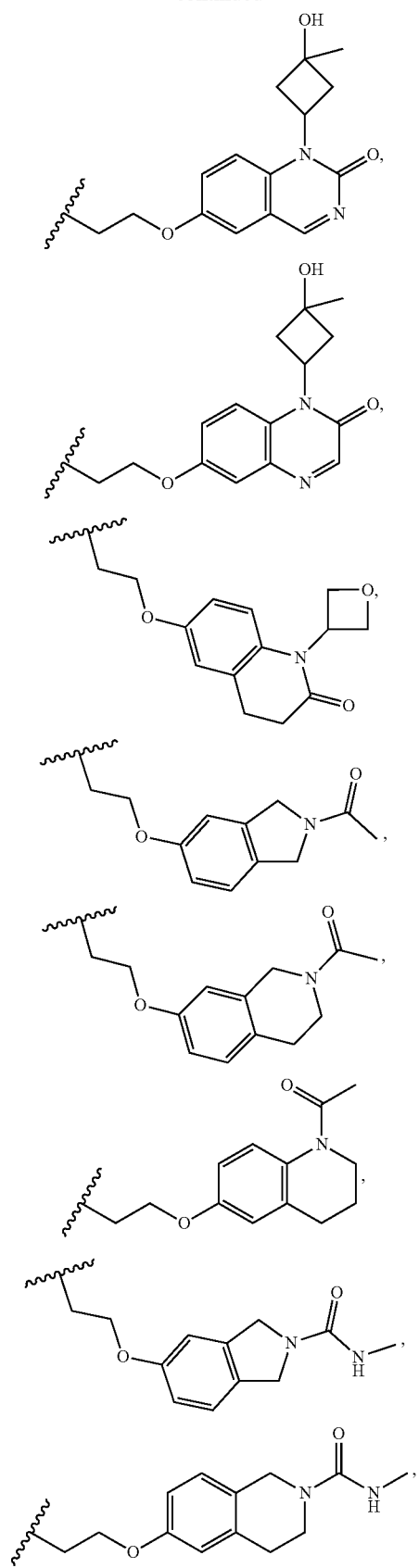
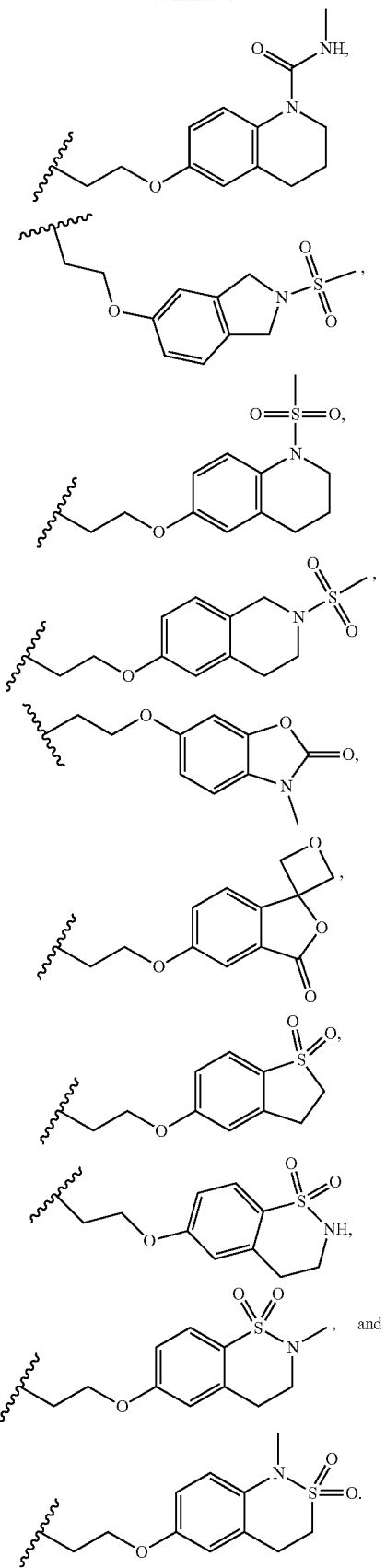

In some embodiments, $L^1$, $L^2$, and the ring bearing $L^3$, $R^4$, $R^6$, and $R^7$ together form a heterocycle selected from the group consisting of

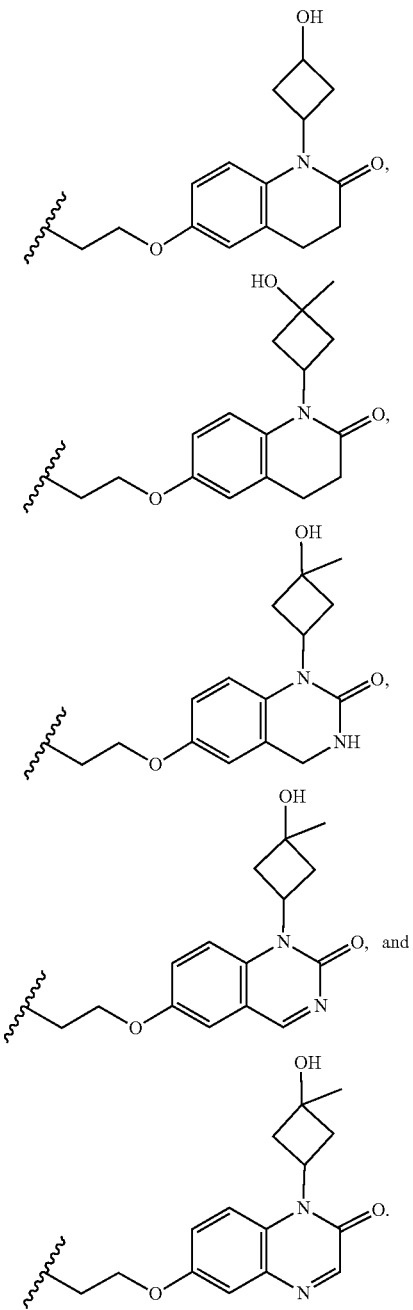

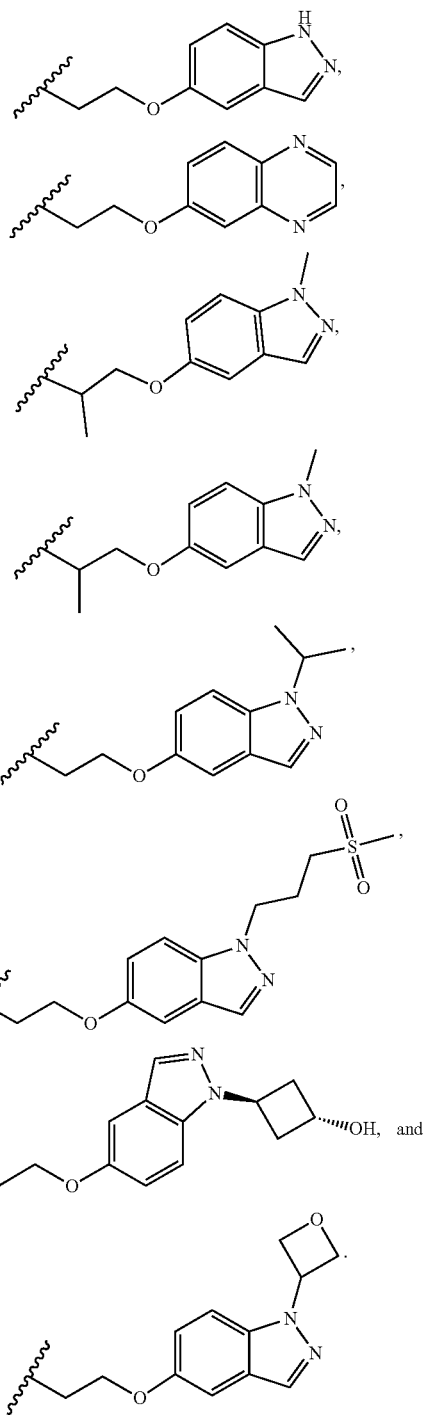

In some variations, the embodiments provided herein also apply to a compound of formula (II), or a stereoisomer or tautomer thereof, or a pharmaceutically acceptable salt of any of the foregoing, or any variation or embodiment thereof.

In some embodiments of a compound of formula (I), or a stereoisomer or tautomer thereof, or a pharmaceutically acceptable salt of any of the foregoing, $L^1$, $L^2$, and the ring bearing $L^3$, $R^4$, $R^6$, and $R^7$ together form a heteroaryl selected from the group consisting of In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I'), or a stereoisomer or tautomer thereof, or a pharmaceutically acceptable salt of any of the foregoing, $L^1$, $L^2$, and the ring bearing $L^3$, $R^4$, $R^6$, and $R^7$ together form a heteroaryl selected from the group consisting of

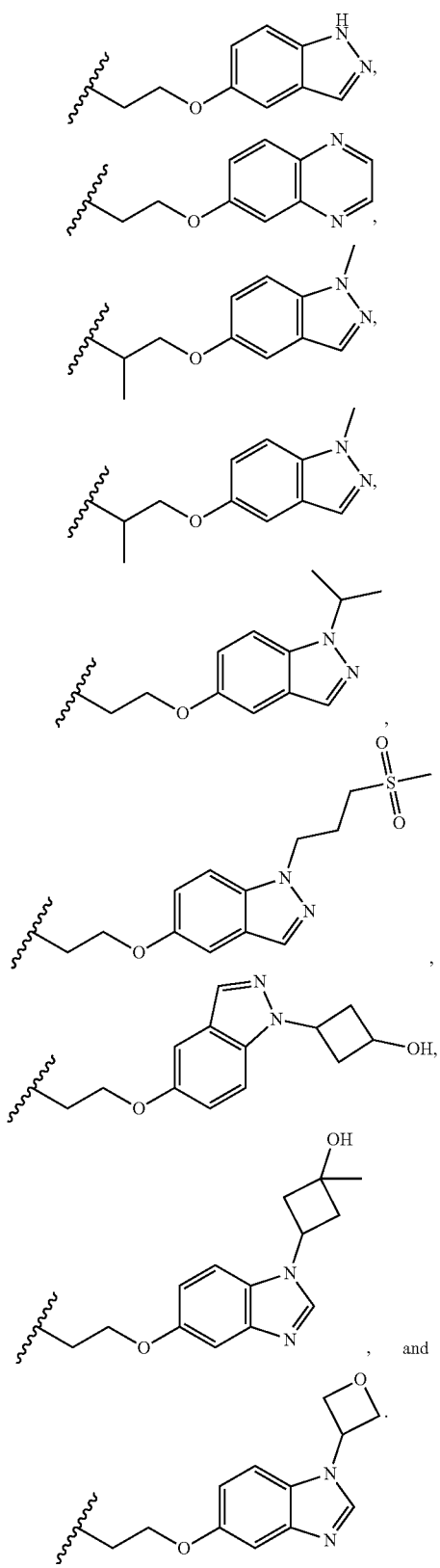

In some embodiments, $L^1$, $L^2$, and the ring bearing $L^3$, $R^4$, $R^6$, and $R^7$ together form a heteroaryl selected from the group consisting of

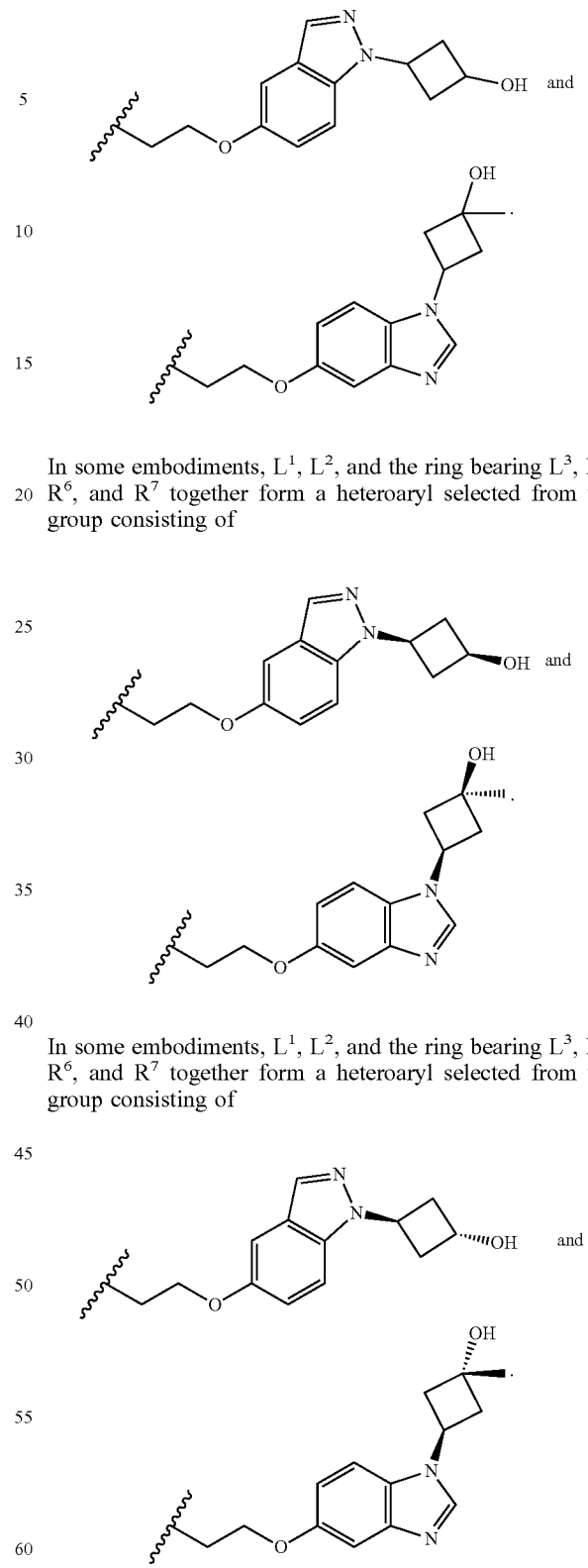

In some embodiments, $L^1$, $L^2$, and the ring bearing $L^3$, $R^4$, $R^6$, and $R^7$ together form a heteroaryl selected from the group consisting of In some embodiments, $L^1$, $L^2$, and the ring bearing $L^3$, $R^4$, $R^6$, and $R^7$ together form a heteroaryl selected from the group consisting of In some variations, the embodiments provided herein also apply to a compound of formula (II), or a stereoisomer or tautomer thereof, or a pharmaceutically acceptable salt of any of the foregoing, or any variation or embodiment thereof.

In some embodiments of a compound of formula (I), or a stereoisomer or tautomer thereof, or a pharmaceutically acceptable salt of any of the foregoing, $L^1$, $L^2$, and the ring bearing $L^3$, $R^4$, $R^6$, and $R^7$ together form a heterocycle selected from the group consisting of

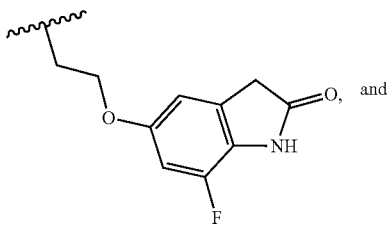, and

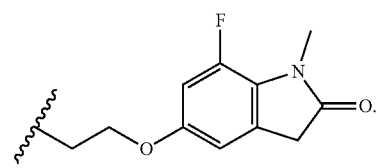

In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I'), or a stereoisomer or tautomer thereof, or a pharmaceutically acceptable salt of any of the foregoing, $L^1$, $L^2$, and the ring bearing $L^3$, $R^4$, $R^6$, and $R^7$ together form a heterocycle selected from the group consisting of

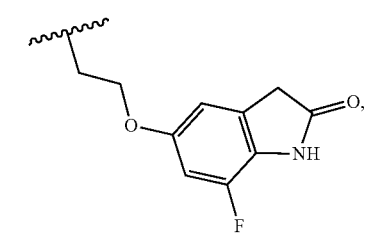

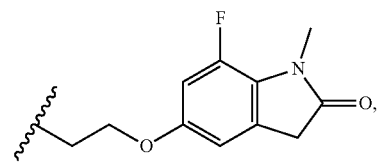

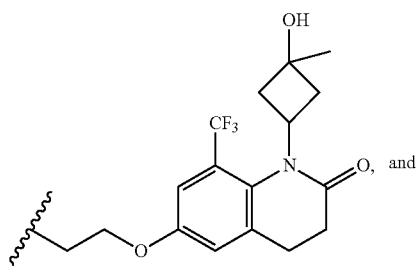, and

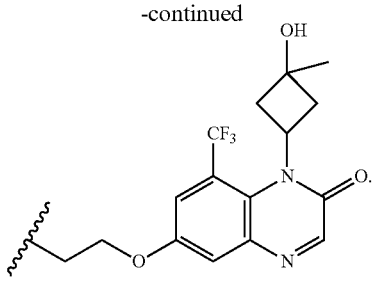

In some variations, the embodiments provided herein also apply to a compound of formula (II), or a stereoisomer or tautomer thereof, or a pharmaceutically acceptable salt of any of the foregoing, or any variation or embodiment thereof.

In some embodiments of a compound of formula (II), or a stereoisomer or tautomer thereof, or a pharmaceutically acceptable salt of any of the foregoing, $L^1$, $L^2$, and the ring bearing $L^3$, $R^4$, $R^6$, and $R^7$ together form a heterocycle selected from the group consisting of

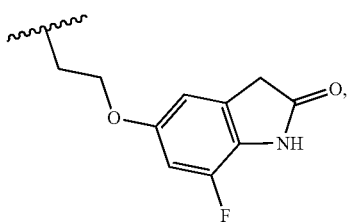

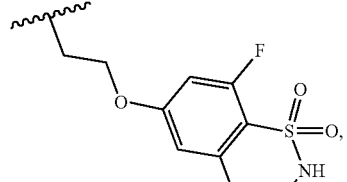

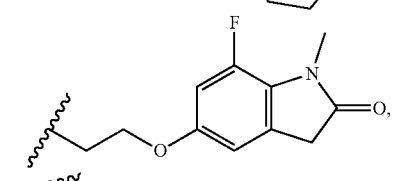

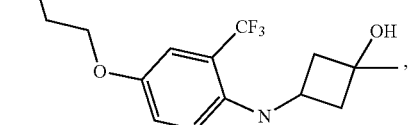

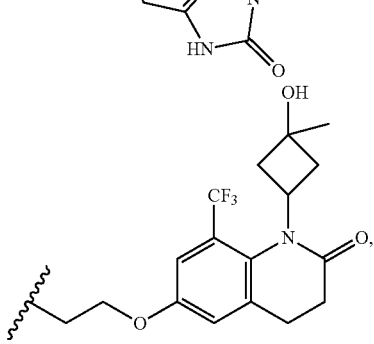

-continued
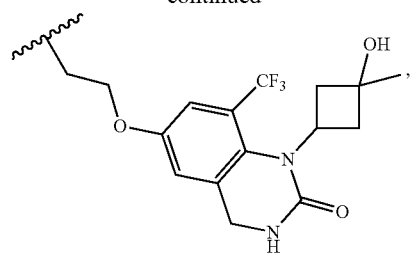
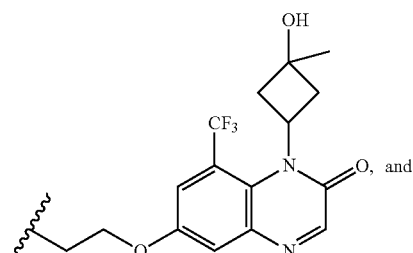
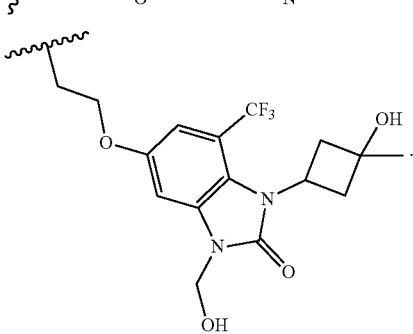
In some embodiments, $L^1$, $L^2$, and the ring bearing $L^3$, $R^4$, $R^6$, and $R^7$ together form a heterocycle selected from the group consisting of
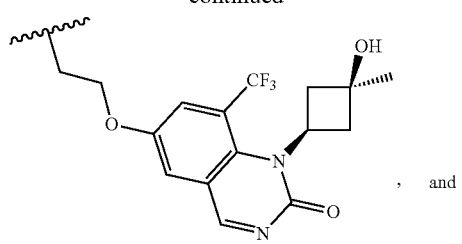
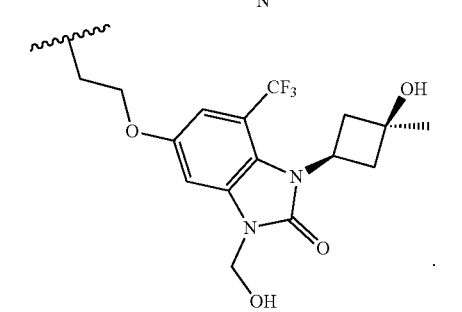
-continued
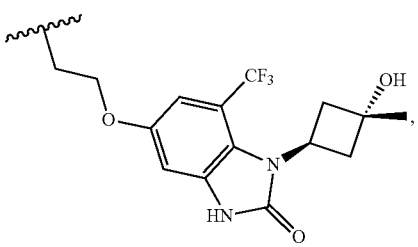
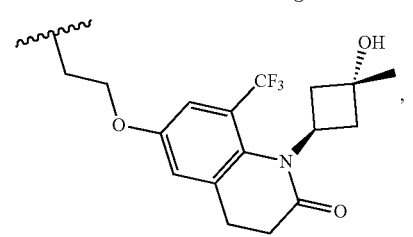
In some embodiments, $L^1$, $L^2$, and the ring bearing $L^3$, $R^4$, $R^6$, and $R^7$ together form a heterocycle selected from the group consisting of
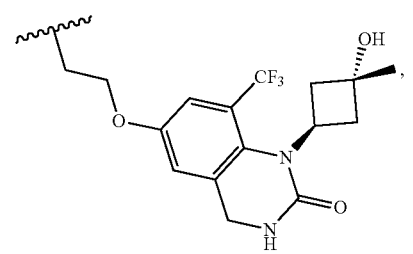
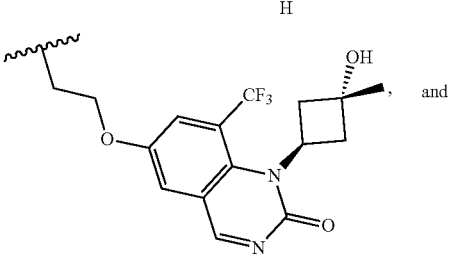

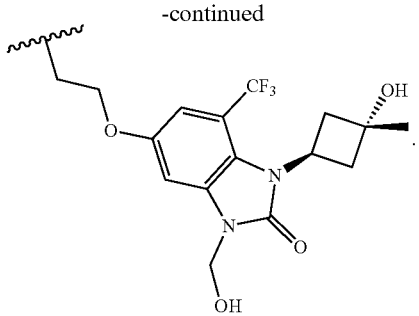

In some embodiments of a compound of formula (I'), or a stereoisomer or tautomer thereof, or a pharmaceutically acceptable salt of any of the foregoing, $L^1$, $L^2$, and the ring bearing $L^3$, $R^4$, $R^6$, and $R^7$ together form

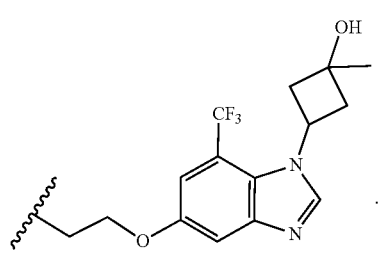 [SMILES: *CCOc1cc(C(F)(F)F)c2c(c1)ncn2C1CC(C)(O)C1]

In some embodiments, $L^1$, $L^2$, and the ring bearing $L^3$, $R^4$, $R^6$, and $R^7$ together form

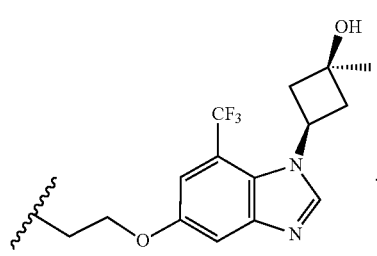 [SMILES: *CCOc1cc(C(F)(F)F)c2c(c1)ncn2[C@H]1C[C@@](C)(O)C1]

In some embodiments, $L^1$, $L^2$, and the ring bearing $L^3$, $R^4$, $R^6$, and $R^7$ together form

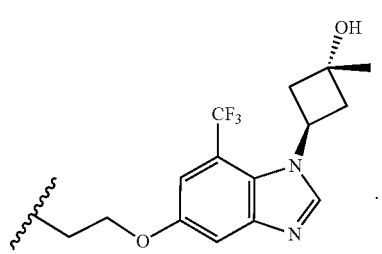 [SMILES: *CCOc1cc(C(F)(F)F)c2c(c1)ncn2[C@H]1C[C@](C)(O)C1]

In some variations, the embodiments provided herein also apply to a compound of formula (II), or a stereoisomer or tautomer thereof, or a pharmaceutically acceptable salt of any of the foregoing, or any variation or embodiment thereof.

In some embodiments of a compound of formula (II), or a stereoisomer or tautomer thereof, or a pharmaceutically acceptable salt of any of the foregoing, $L^1$, $L^2$, and the ring bearing $L^3$, $R^4$, $R^6$, and $R^7$ together form

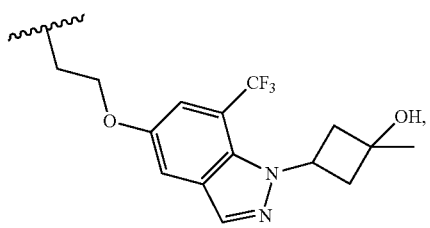

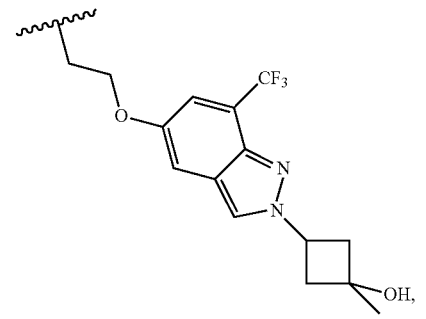

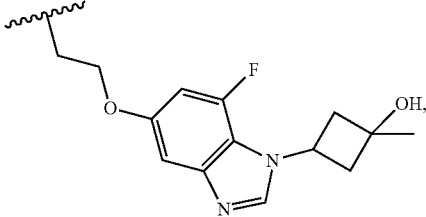

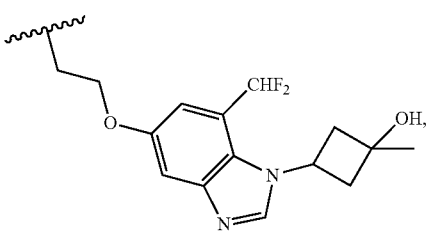

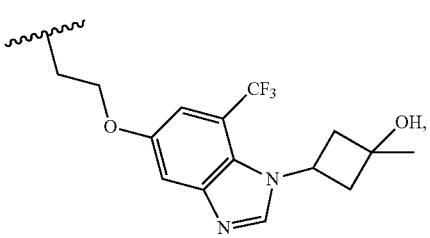

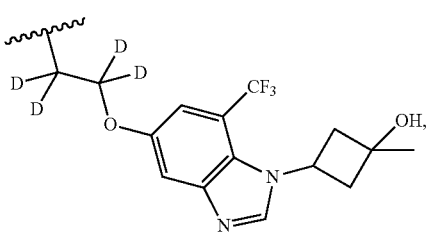

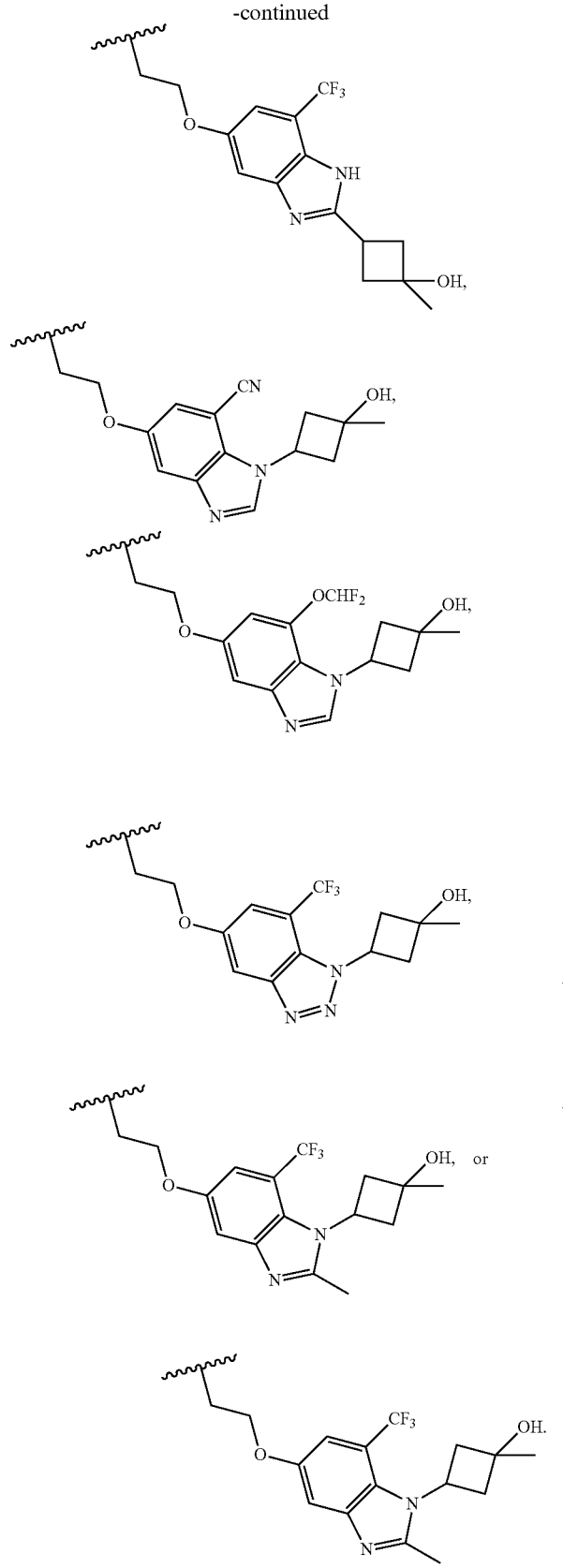
In some embodiments, $L^1$, $L^2$, and the ring bearing $L^3$, $R^4$, $R^6$, and $R^7$ together form

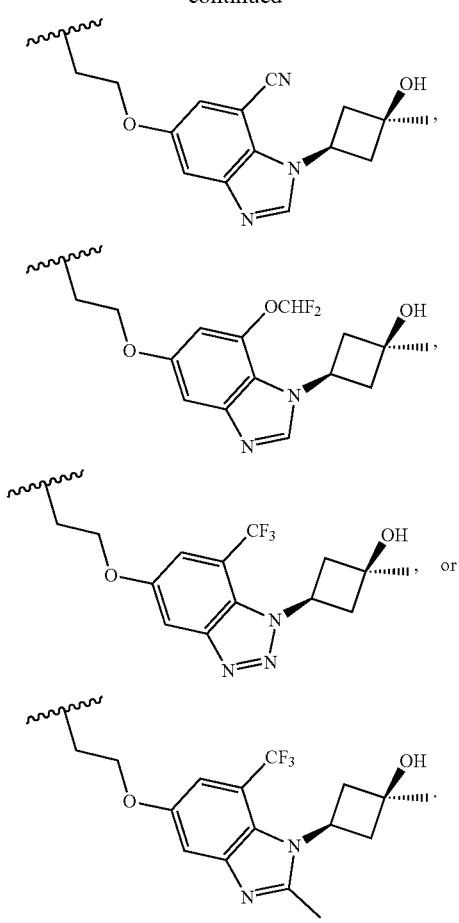
In some embodiments, $L^1$, $L^2$, and the ring bearing $L^3$, $R^4$, $R^6$, and $R^7$ together form
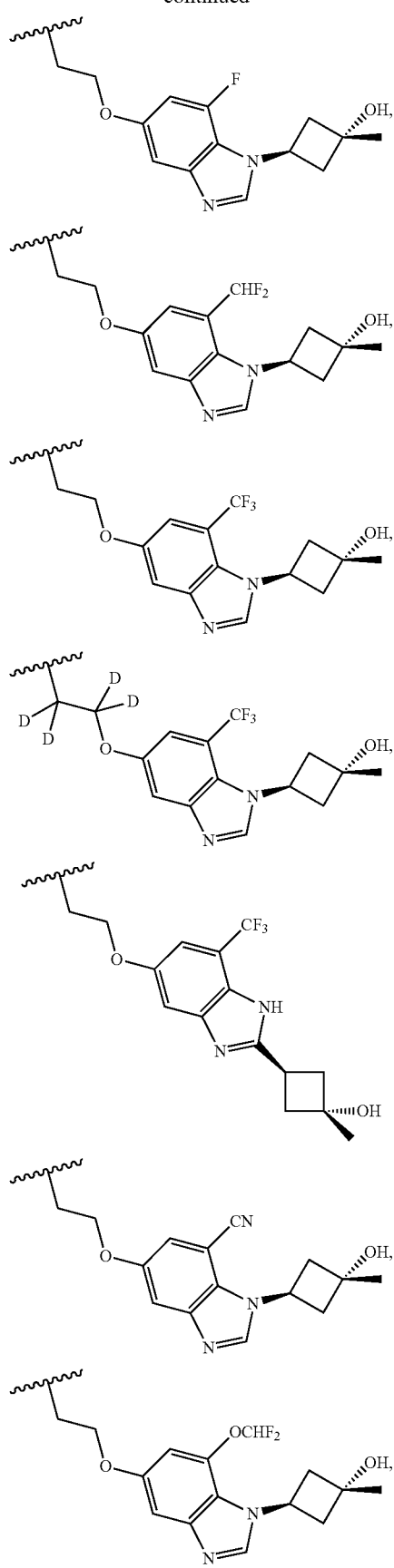

-continued

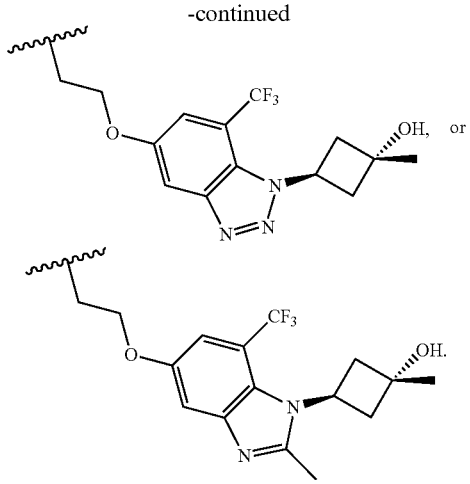

In some embodiments of a compound of formula (I), or a stereoisomer or tautomer thereof, or a pharmaceutically acceptable salt of any of the foregoing, $L^1$, $L^2$, and the ring bearing $L^3$, $R^4$, $R^6$, and $R^7$ together form a heterocycle selected from the group consisting of

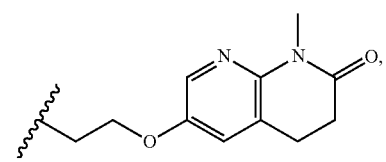

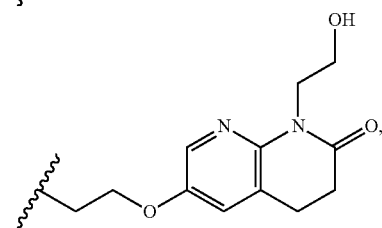

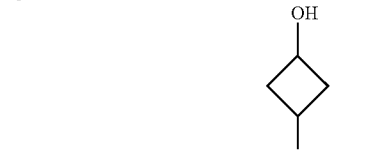

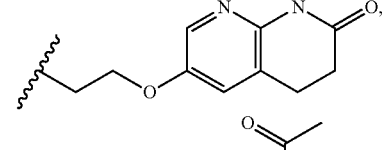

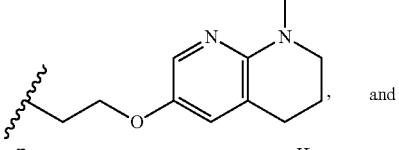

In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I'), or a stereoisomer or tautomer thereof, or a pharmaceutically acceptable salt of any of the foregoing, $L^1$, $L^2$, and the ring bearing $L^3$, $R^4$, $R^6$, and $R^7$ together form a heterocycle selected from the group consisting of

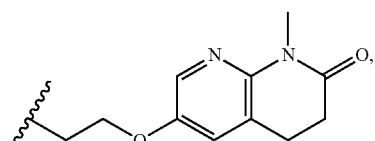

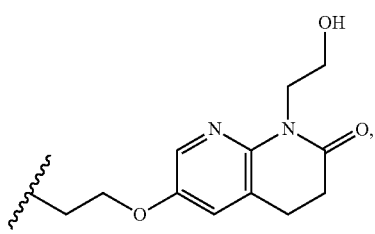

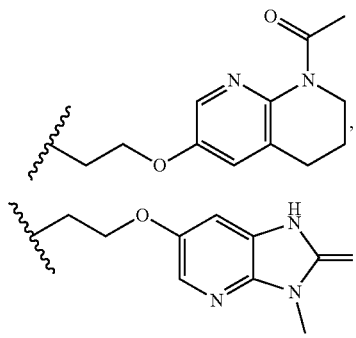

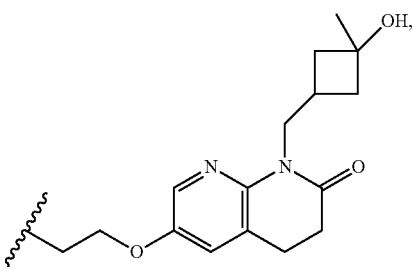

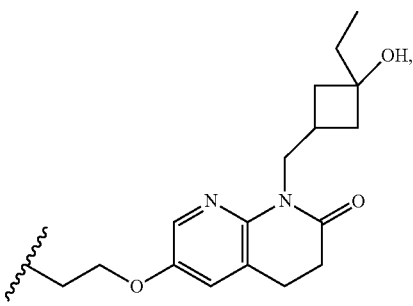

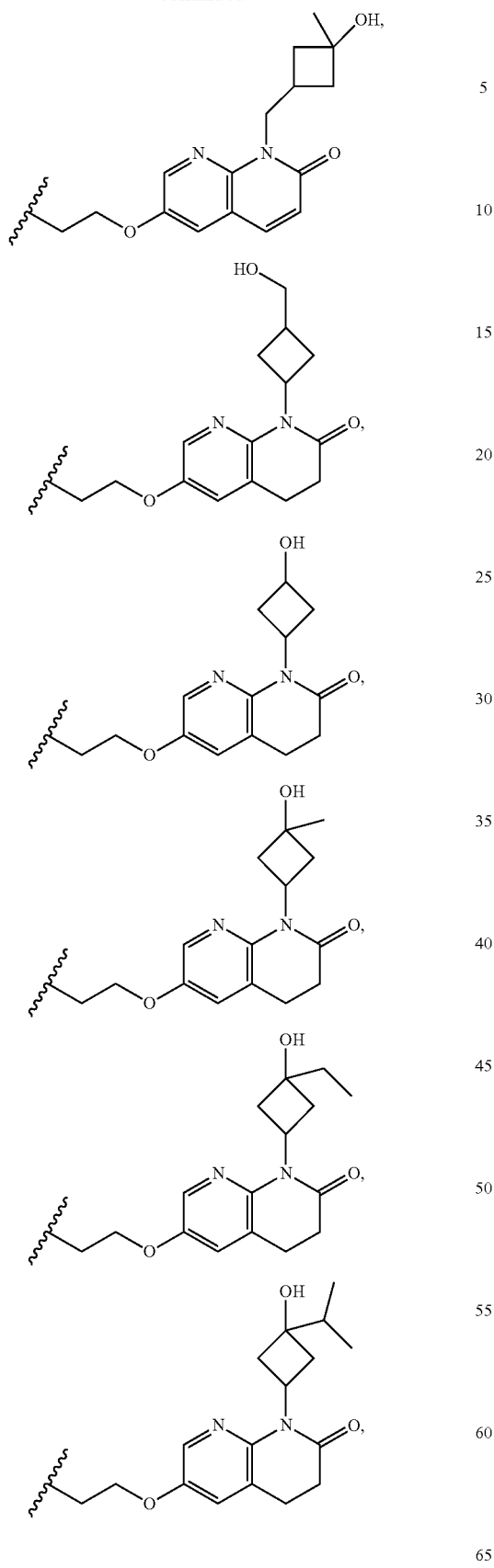
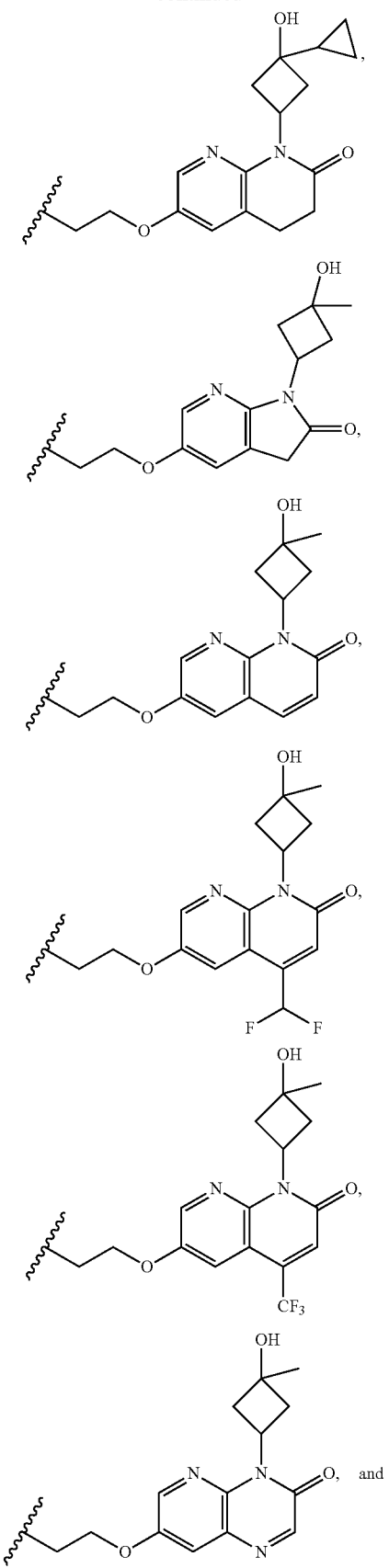

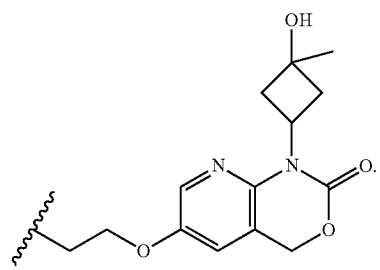
In some embodiments, $L^1$, $L^2$, and the ring bearing $L^3$, $R^4$, $R^6$, and $R^7$ together form a heterocycle selected from the group consisting of
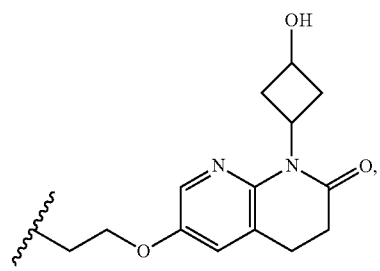
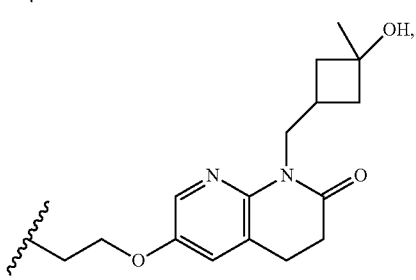
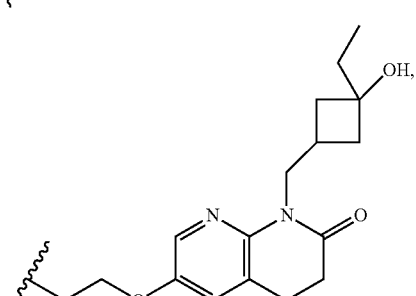
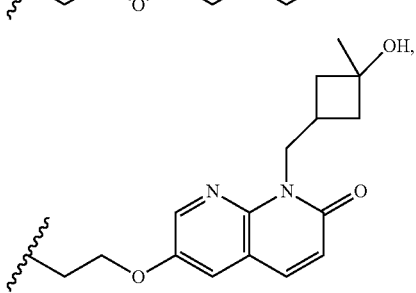
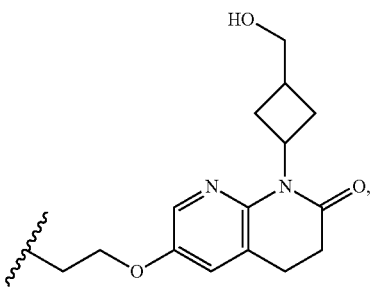
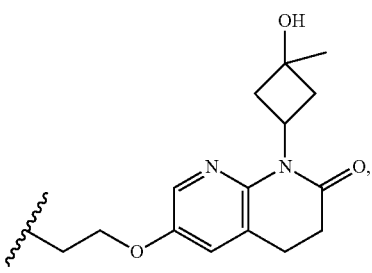
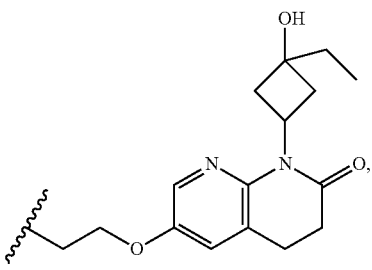
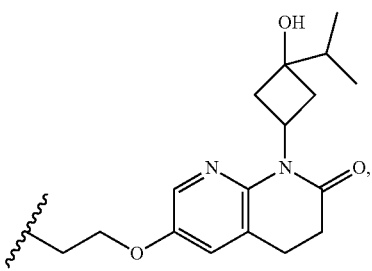
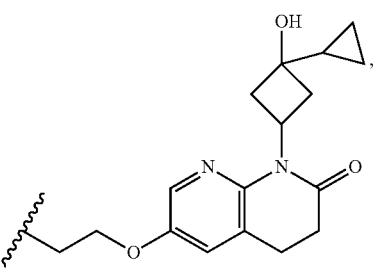
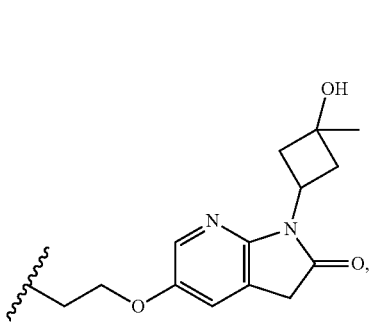

159
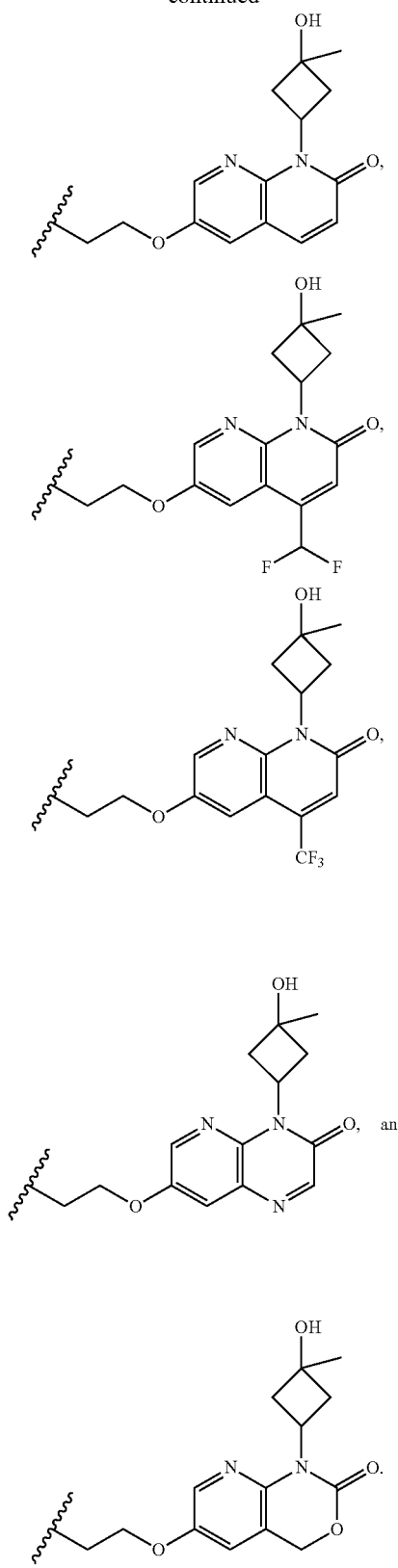
160
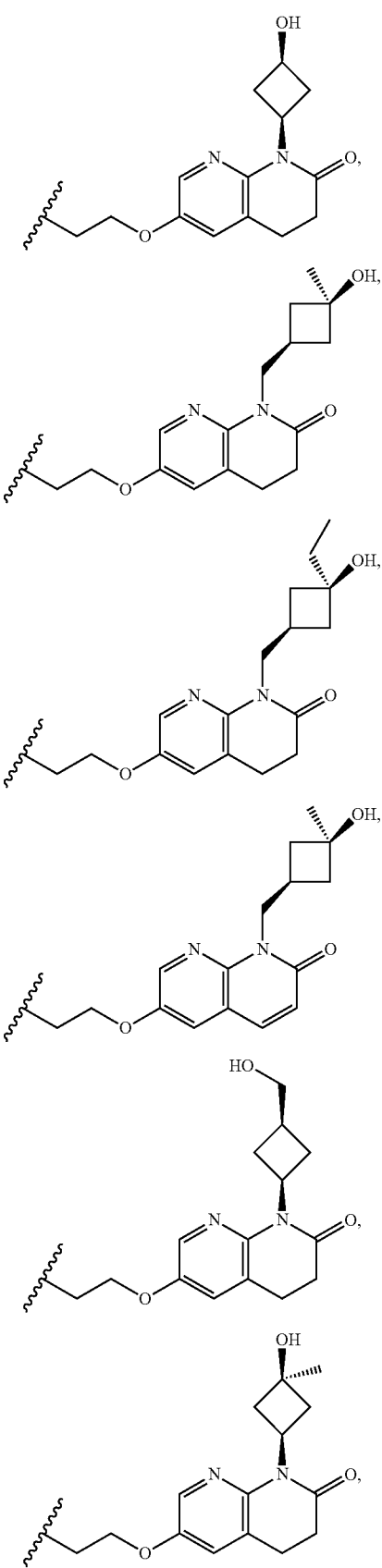
In some embodiments, L¹, L², and the ring bearing L³, R⁴, R⁶, and R⁷ together form a heterocycle selected from the group consisting of

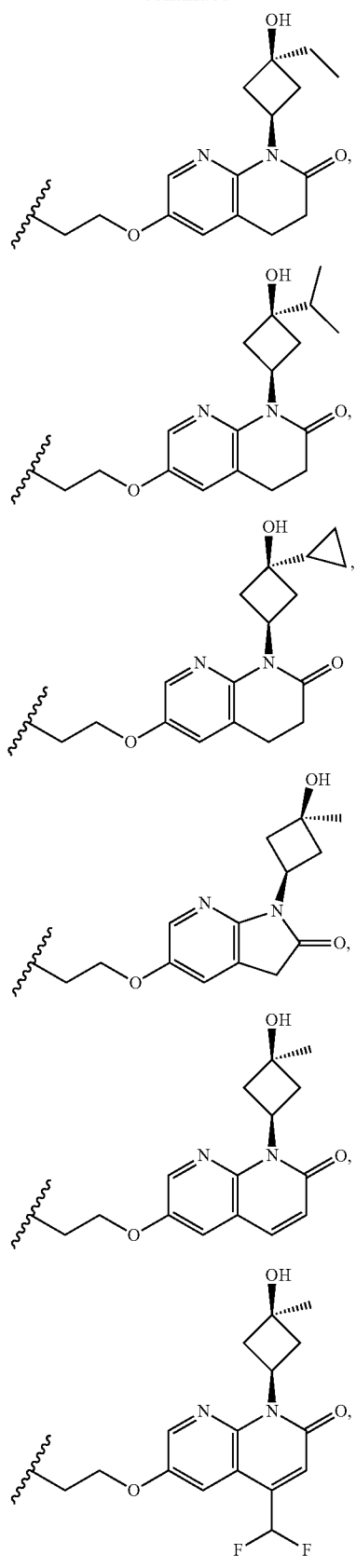
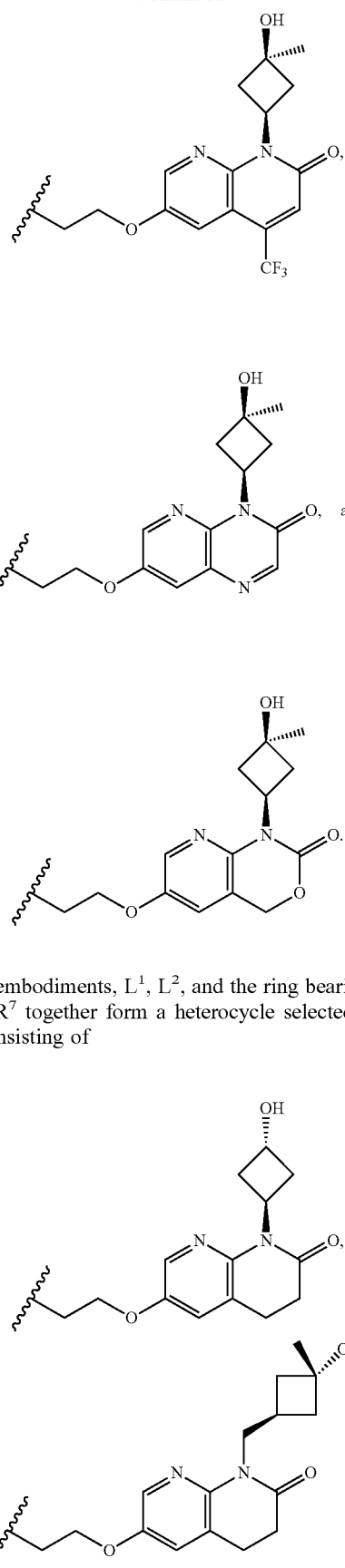
In some embodiments, $L^1$, $L^2$, and the ring bearing $L^3$, $R^4$, $R^6$, and $R^7$ together form a heterocycle selected from the group consisting of

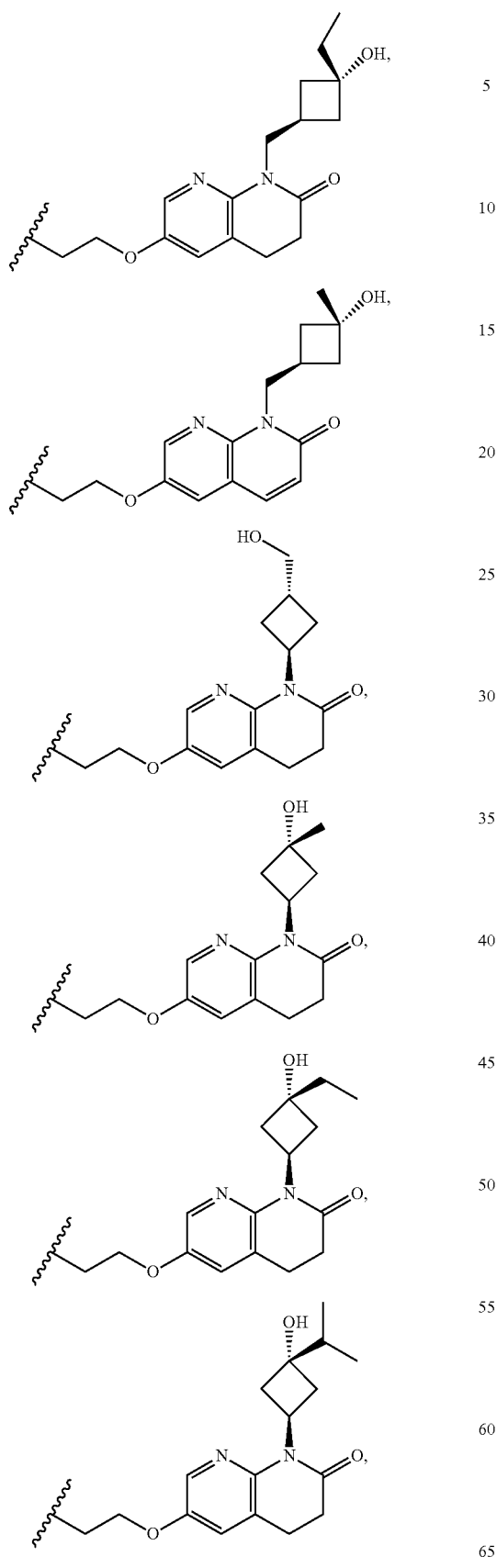
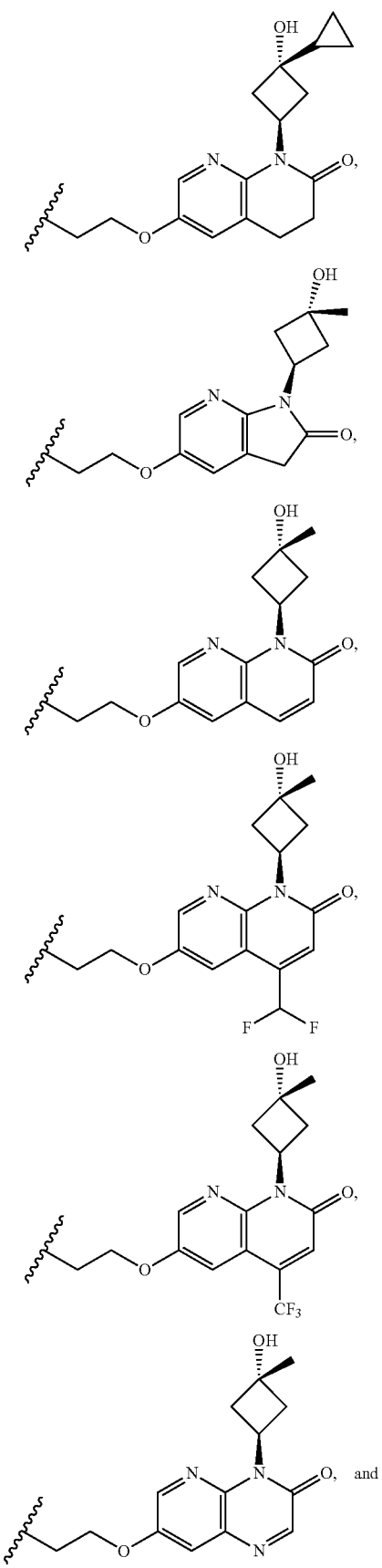

-continued

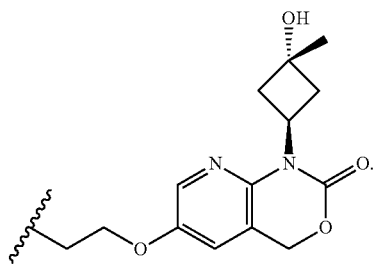

In some variations, the embodiments provided herein also apply to a compound of formula (II), or a stereoisomer or tautomer thereof, or a pharmaceutically acceptable salt of any of the foregoing, or any variation or embodiment thereof.

In some embodiments of a compound of formula (I'), or a stereoisomer or tautomer thereof, or a pharmaceutically acceptable salt of any of the foregoing, $L^1$, $L^2$, and the ring bearing $L^3$, $R^4$, $R^6$, and $R^7$ together form a heterocycle selected from the group consisting of

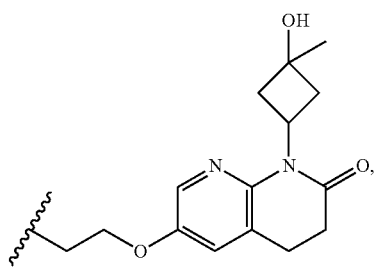

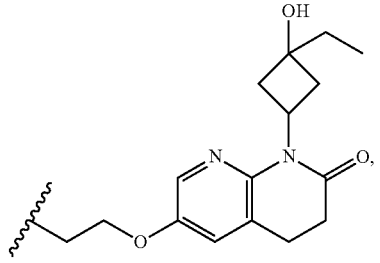

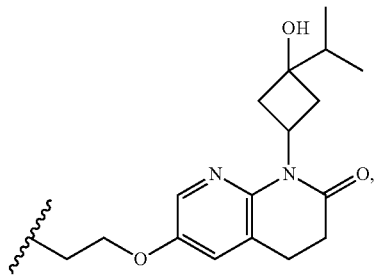

-continued

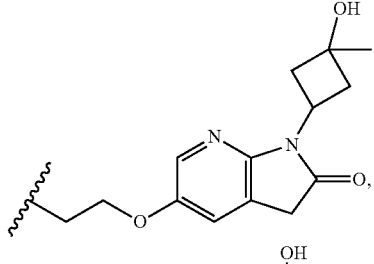

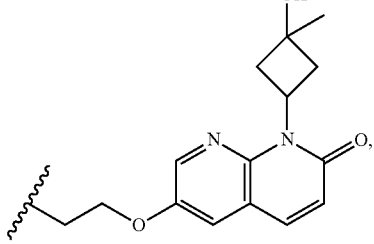

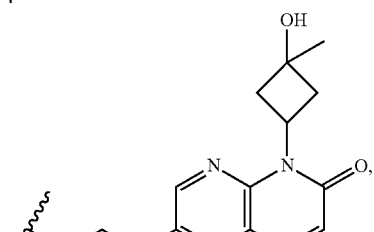

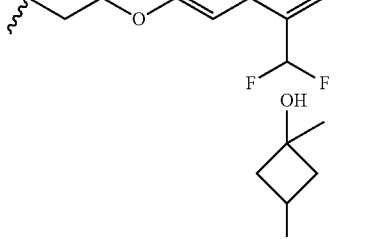

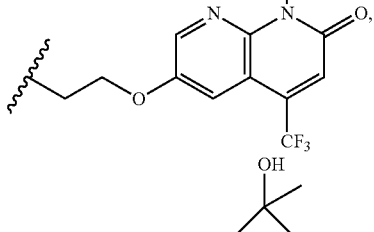

In some embodiments, $L^1$, $L^2$, and the ring bearing $L^3$, $R^4$, $R^6$ and $R^7$ together form a heterocycle selected from the group consisting of

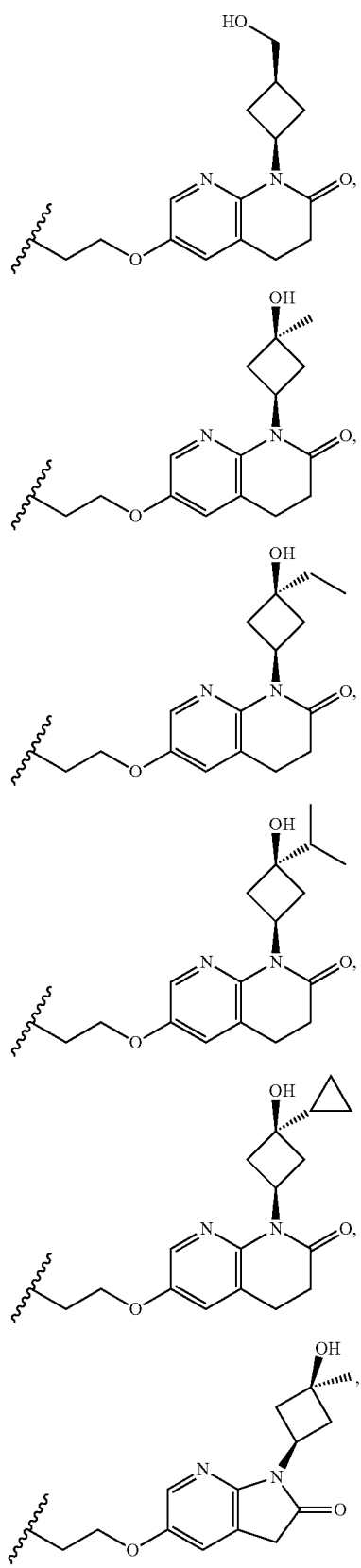
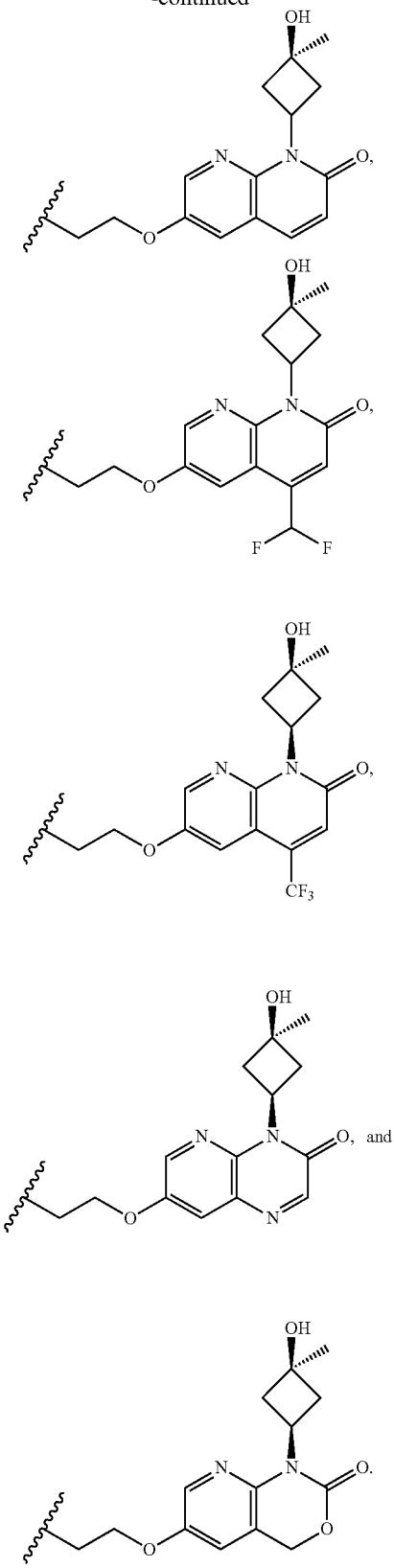
In some embodiments, $L^1$, $L^2$, and the ring bearing $L^3$, $R^4$, $R^6$, and $R^7$ together form a heterocycle selected from the group consisting of

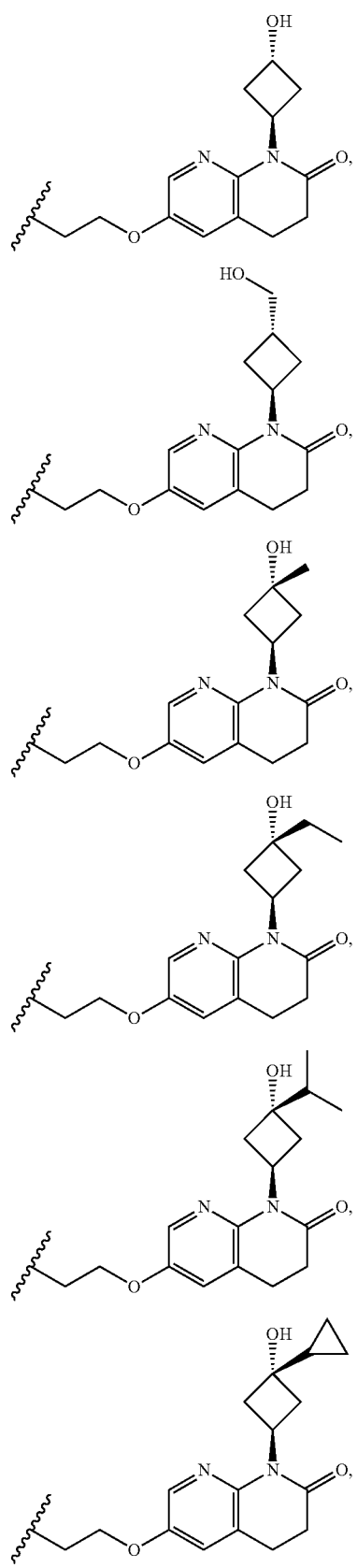
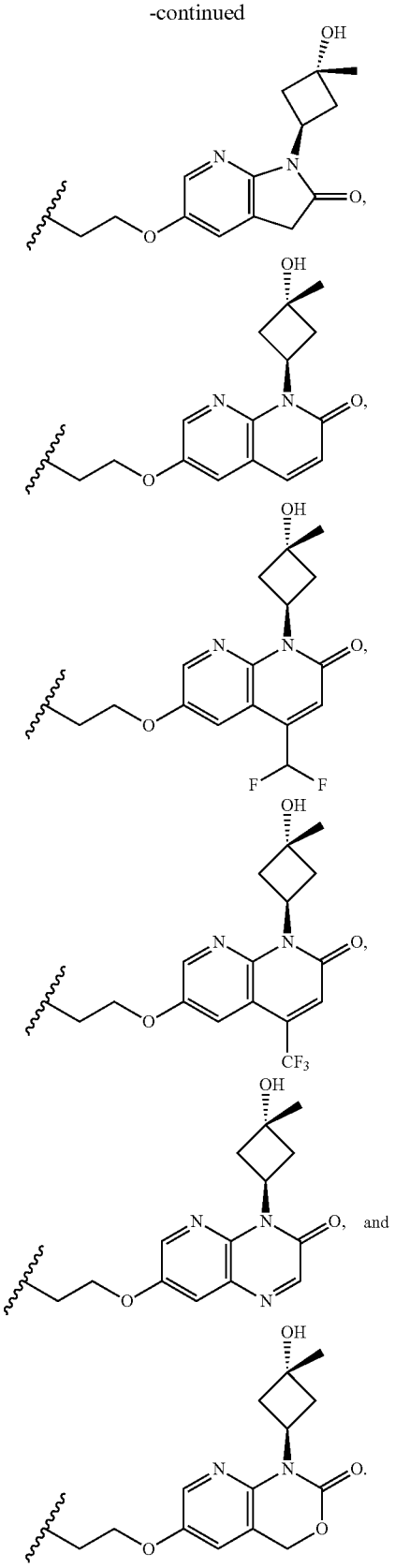
In some embodiments, L¹, L², and the ring bearing L³, R⁴, R⁶, and R⁷ together form

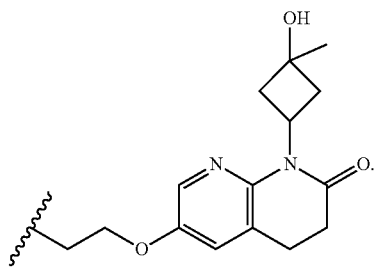 [SMILES: *CCOc1cnc2c(c1)CCC(=O)N2C1CC(C)(O)C1]

In some variations, $L^1$, $L^2$, and the ring bearing $L^3$, $R^4$, $R^6$, and $R^7$ together form a heterocycle selected from the group consisting of

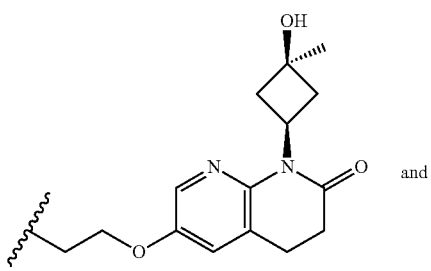 and

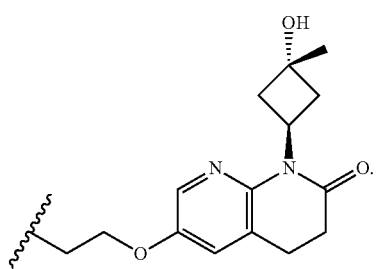

In certain variations, $L^1$, $L^2$, and the ring bearing $L^3$, $R^4$, $R^6$, and $R^7$ together form

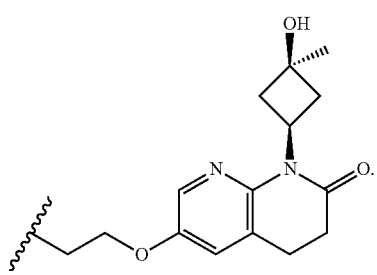 [SMILES: *CCOc1cnc2c(c1)CCC(=O)N2[C@H]1C[C@@](C)(O)C1]

In certain variations, $L^1$, $L^2$, and the ring bearing $L^3$, $R^4$, $R^6$, and $R^7$ together form

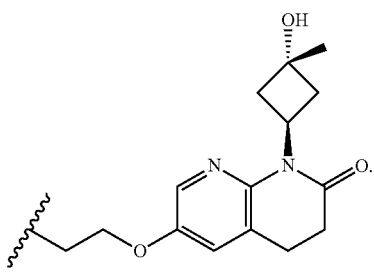 [SMILES: *CCOc1cnc2c(c1)CCC(=O)N2[C@H]1C[C@](C)(O)C1]

In some variations, the embodiments provided herein also apply to a compound of formula (II), or a stereoisomer or tautomer thereof, or a pharmaceutically acceptable salt of any of the foregoing, or any variation or embodiment thereof.

In some embodiments of a compound of formula (II), or a stereoisomer or tautomer thereof, or a pharmaceutically acceptable salt of any of the foregoing, $L^1$, $L^2$, and the ring bearing $L^3$, and $R^4$ together form a heterocycle selected from the group consisting of

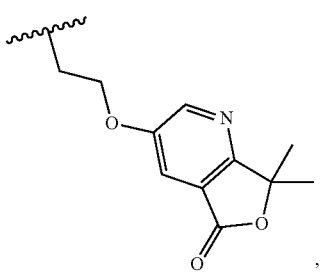

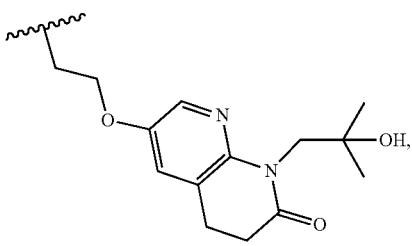

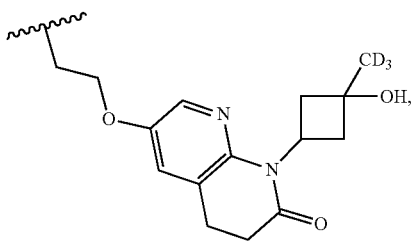

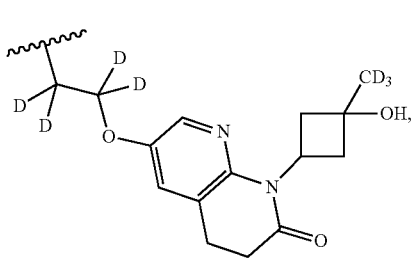

-continued

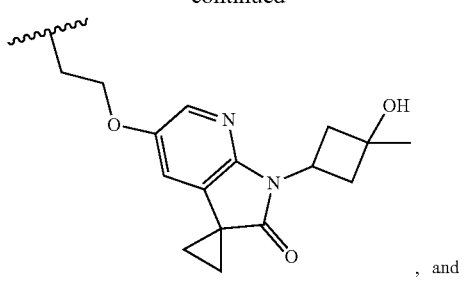
, and

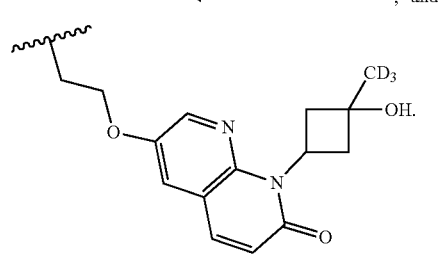

In certain variations, $L^1$, $L^2$, and the ring bearing $L^3$, and $R^4$ together form

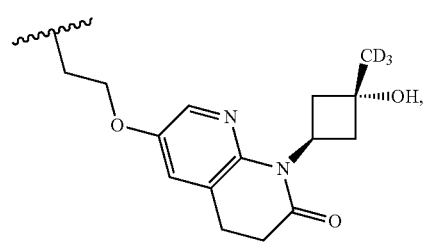

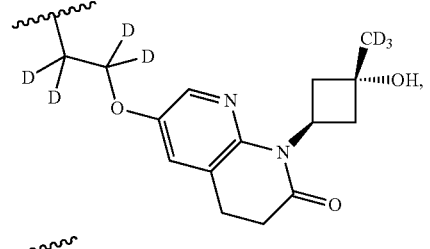

, or

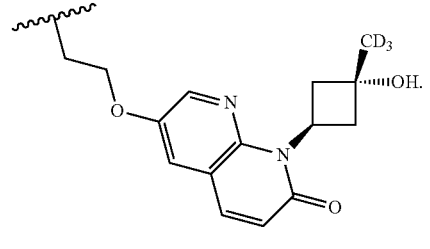

In certain variations, $L^1$, $L^2$, and the ring bearing $L^3$, and $R^7$ together form

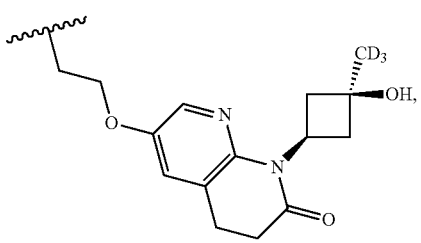

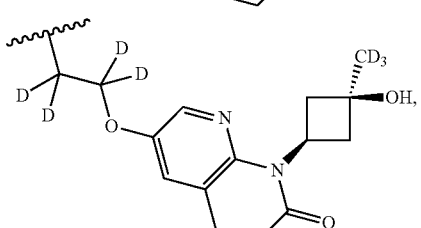

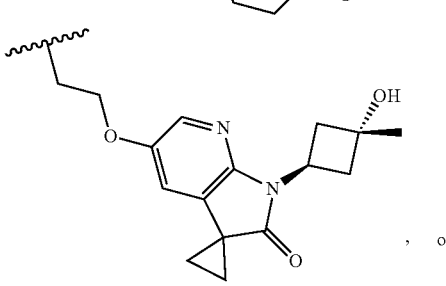

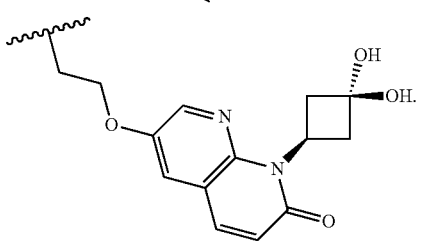
, or

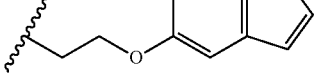

In some embodiments of a compound of formula (I'), or a stereoisomer or tautomer thereof, or a pharmaceutically acceptable salt of any of the foregoing, $L^1$, $L^2$, and the ring bearing $L^3$, $R^4$, $R^6$, and $R^7$ together form a heteroaryl selected from the group consisting of

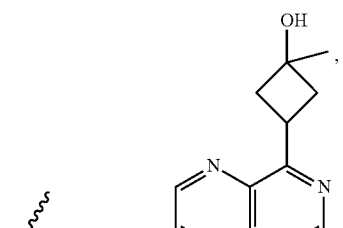

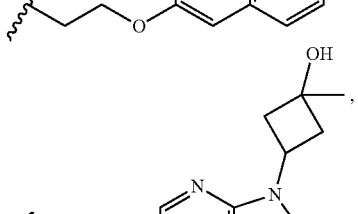

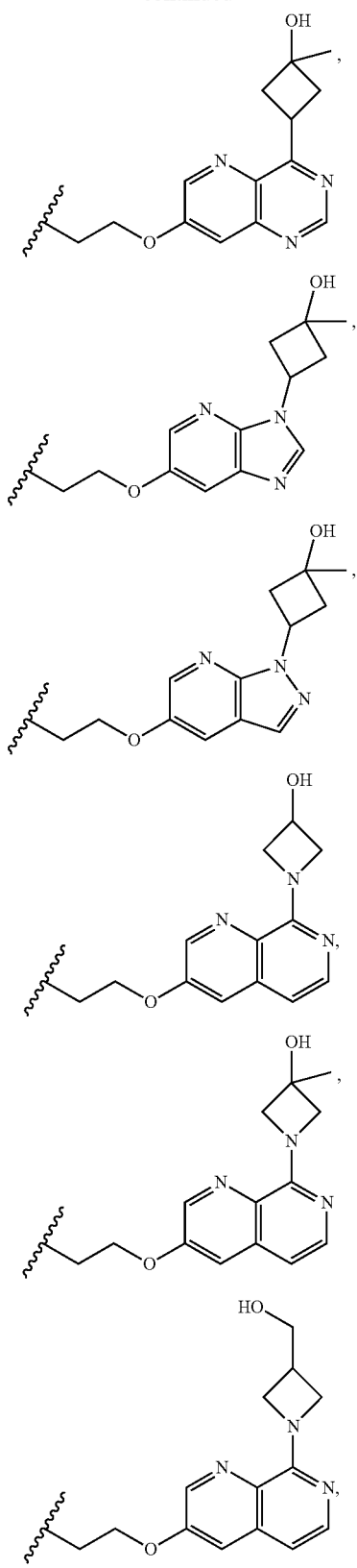
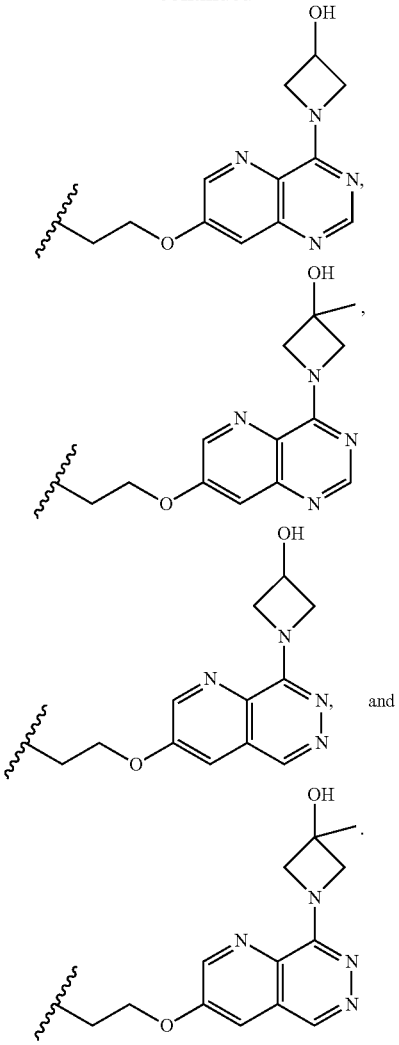
In some embodiments, $L^1$, $L^2$, and the ring bearing $L^3$, $R^4$, $R^6$, and $R^7$ together form a heteroaryl selected from the group consisting of
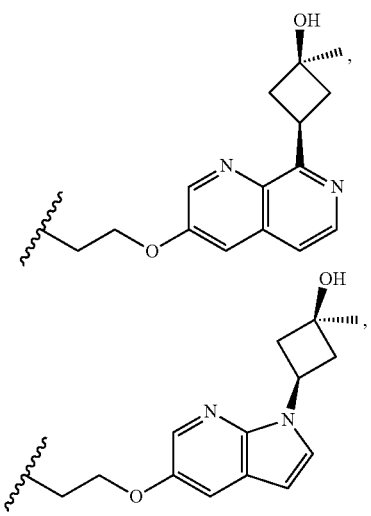

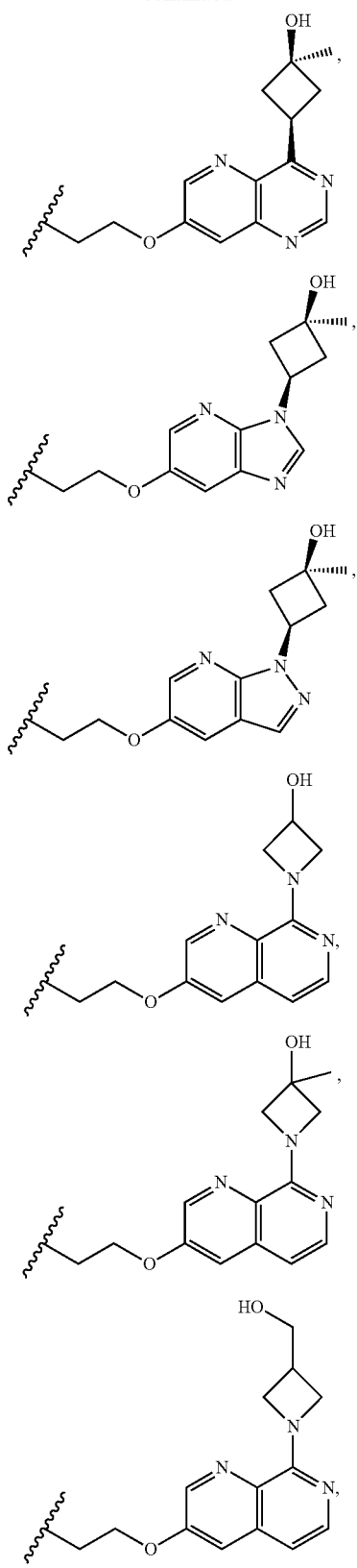
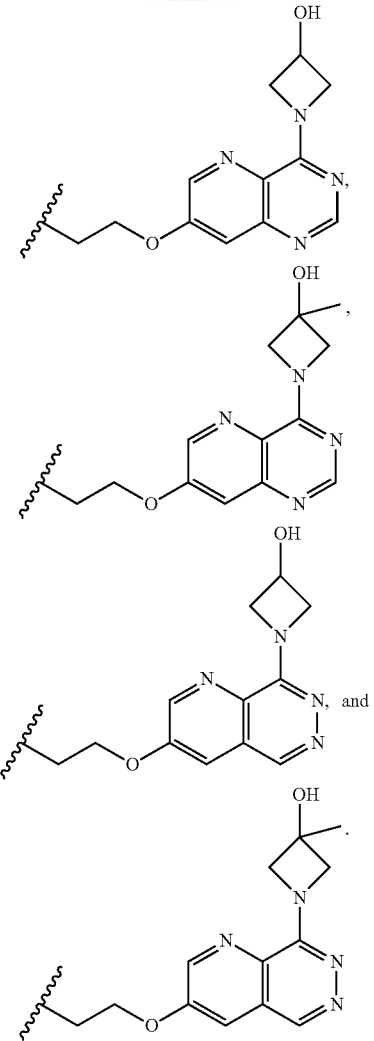
In some embodiments, $L^1$, $L^2$, and the ring bearing $L^3$, $R^4$, $R^6$, and $R^7$ together form a heteroaryl selected from the group consisting of
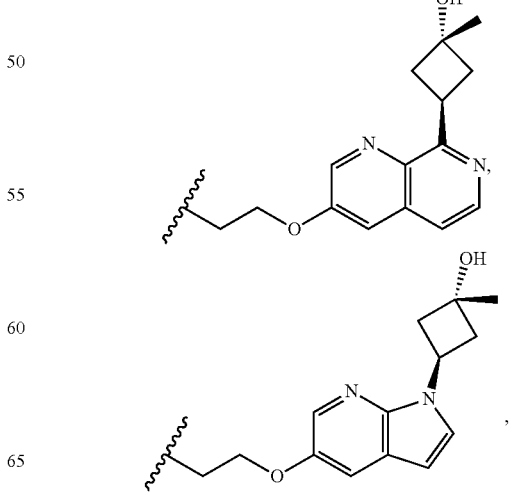

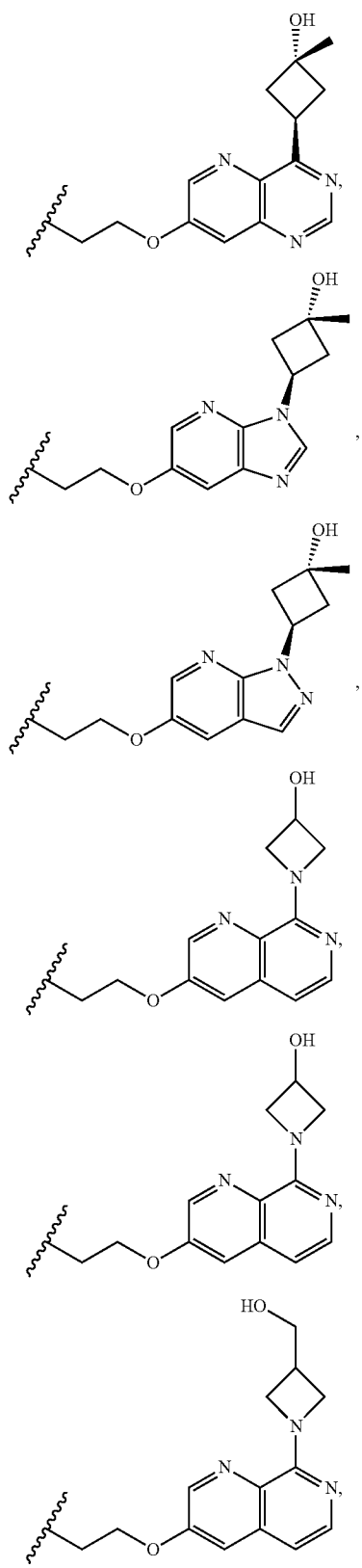

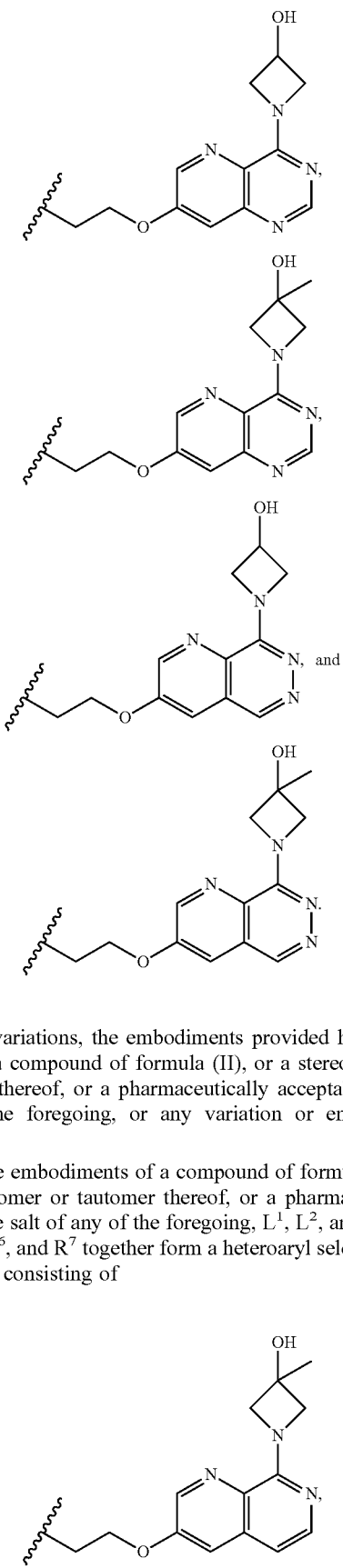

In some variations, the embodiments provided herein also apply to a compound of formula (II), or a stereoisomer or tautomer thereof, or a pharmaceutically acceptable salt of any of the foregoing, or any variation or embodiment thereof.

In some embodiments of a compound of formula (II), or a stereoisomer or tautomer thereof, or a pharmaceutically acceptable salt of any of the foregoing, $L^1$, $L^2$, and the ring bearing $R^6$, and $R^7$ together form a heteroaryl selected from the group consisting of

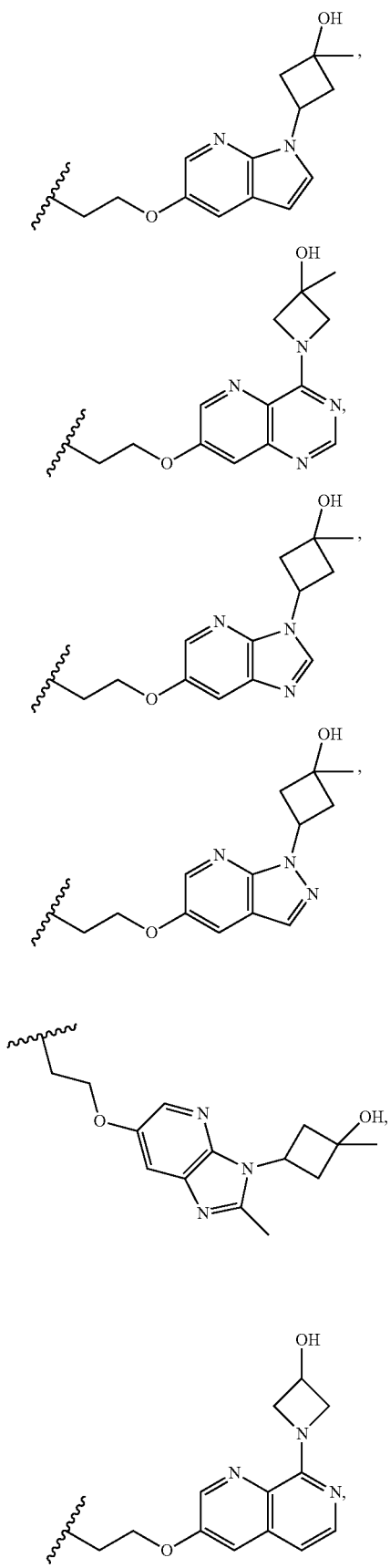
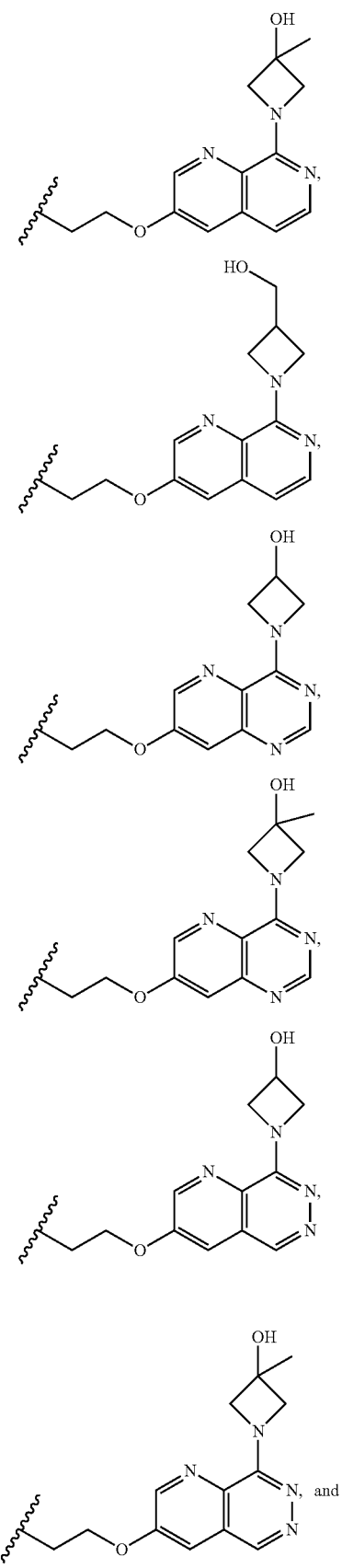

-continued

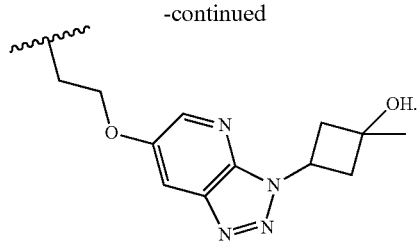

In some embodiments, $L^1$, $L^2$, and the ring bearing $R^6$, and $R^7$ together form

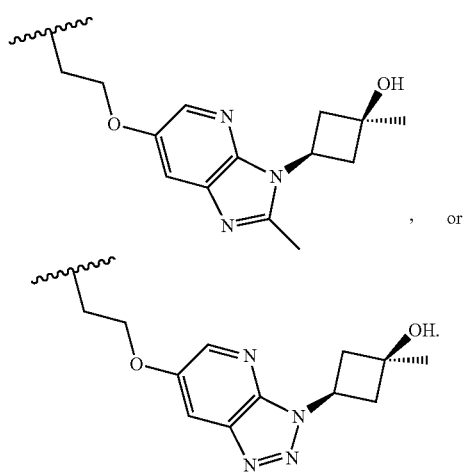

In some embodiments, $L^1$, $L^2$, and the ring bearing $R^6$, and $R^7$ together form

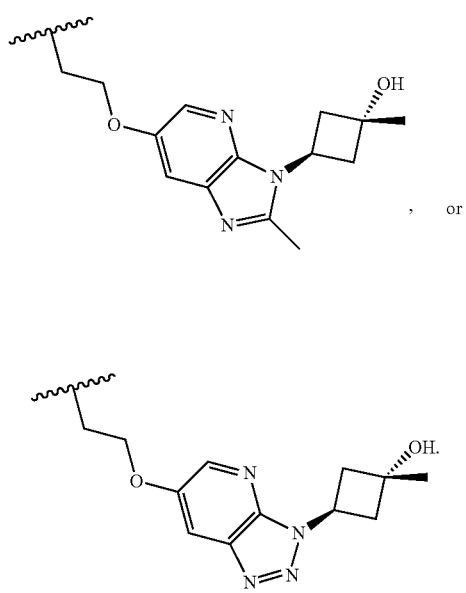

In some embodiments of a compound of formula (II), or a stereoisomer or tautomer thereof, or a pharmaceutically acceptable salt of any of the foregoing, $L^1$, $L^2$, and the ring bearing $R^6$, and $R^7$ together form a heteroaryl selected from the group consisting of

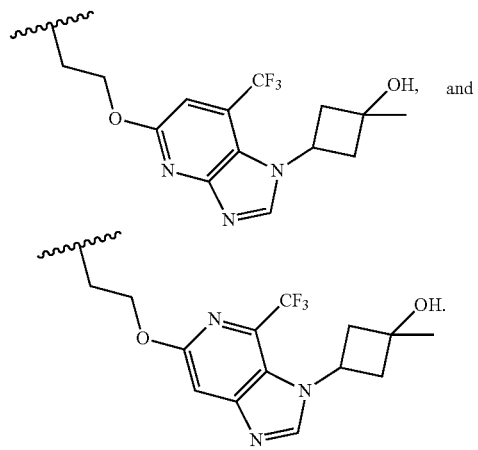

In some embodiments, $L^1$, $L^2$, and the ring bearing $R^6$, and $R^7$ together form

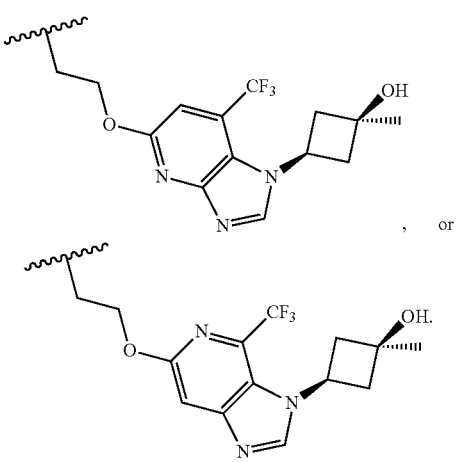

In some embodiments, $L^1$, $L^2$, and the ring bearing $R^6$, and $R^7$ together

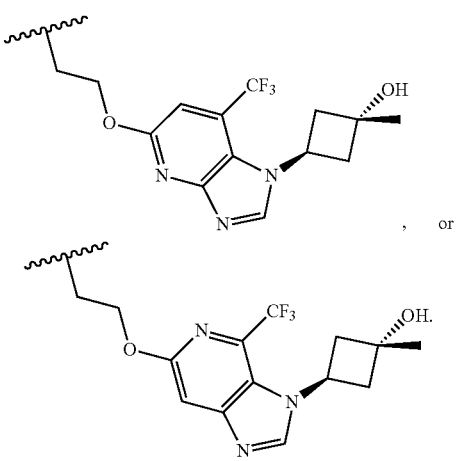

In some embodiments of a compound of formula (I), or a stereoisomer or tautomer thereof, or a pharmaceutically acceptable salt of any of the foregoing, n is 1 or 2, and $L^2$ is —O—. In some embodiments, n is 2, and $L^2$ is —O—. In some embodiments, n is 1, and $L^2$ is O. In some embodiments, n is 1 or 2, $L^2$ is —O— and $R^4$ is —S(O)$_2$—$R^a$. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), or a stereoisomer or tautomer thereof, or a pharmaceutically acceptable salt of any of the foregoing, n is 1, p is 0, $L^2$ is O and each of $X^1$ and $X^2$ is C($R^5$), wherein each $R^5$ is independently H, halo, —CN, 3-10 membered heterocyclyl, $C_{1-6}$alkyl, or $C_{1-6}$alkoxy, wherein the $C_{1-6}$alkyl of $R^5$ is optionally substituted with one or more halo, or —OH, and wherein the $C_{1-6}$alkoxy of $R^5$ is optionally substituted with one or more halo. In some embodiments, n is 1, p is 0, $L^2$ is O and each of $X^1$ and $X^2$ is C($R^5$), wherein each $R^5$ is independently H. In some embodiments, n is 1, p is 0, $L^2$ is O and each of $X^1$ and $X^2$ is C($R^5$), wherein one of $R^5$ is H and the other of $R^5$ is halo, —CN, 3-10 membered heterocyclyl, $C_{1-6}$alkyl, or $C_{1-6}$alkoxy, wherein the $C_{1-6}$alkyl of $R^5$ is optionally substituted with one or more halo, or —OH, and wherein the $C_{1-6}$alkoxy is optionally substituted with one or more halo. In some embodiments, n is 1, p is 0, $L^2$ is O and each of $X^1$ and $X^2$ is C($R^5$), wherein each $R^5$ is independently halo, —CN, 3-10 membered heterocyclyl, $C_{1-6}$alkyl, or $C_{1-6}$alkoxy, wherein the $C_{1-6}$alkyl of $R^5$ is optionally substituted with one or more halo, or —OH, and wherein the $C_{1-6}$alkoxy is optionally substituted with one or more halo. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), or a stereoisomer or tautomer thereof, or a pharmaceutically acceptable salt of any of the foregoing, n is 1, p is 0, $L^2$ is O, one of $X^1$ and $X^2$ is N, and the other of $X^1$ and $X^2$ is C($R^5$), wherein $R^5$ is H, halo, —CN, 3-10 membered heterocyclyl, $C_{1-6}$alkyl, or $C_{1-6}$alkoxy, wherein the $C_{1-6}$alkyl of $R^5$ is optionally substituted with one or more halo, or —OH, and wherein the $C_{1-6}$alkoxy of $R^5$ is optionally substituted with one or more halo. In some embodiments, n is 1, p is 0, $L^2$ is O, one of $X^1$ and $X^2$ is N, and the other of $X^1$ and $X^2$ is C($R^5$), wherein $R^5$ is H. In some embodiments, n is 1, p is 0, $L^2$ is O, one of $X^1$ and $X^2$ is N, and the other of $X^1$ and $X^2$ is C($R^5$), wherein $R^5$ is halo, —CN, 3-10 membered heterocyclyl, $C_{1-6}$alkyl, or $C_{1-6}$alkoxy, wherein the $C_{1-6}$alkyl of $R^5$ is optionally substituted with one or more halo, or —OH, and wherein the $C_{1-6}$alkoxy of $R^5$ is optionally substituted with one or more halo. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), or a stereoisomer or tautomer thereof, or a pharmaceutically acceptable salt of any of the foregoing, n is 1, $L^2$ is O, and each of $X^1$ and $X^2$ is N. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), or a stereoisomer or tautomer thereof, or a pharmaceutically acceptable salt of any of the foregoing, n is 1, p is 0, $L^2$ is O, one of $X^1$ and $X^2$ is C($R^5$), wherein $R^5$ is H, the other of $X^1$ and $X^2$ is C that is taken together with $R^4$, and the atoms to which they are attached, to form (i) a 5-10 membered heterocyclyl, wherein the 5-10 membered heterocyclyl is optionally substituted with one or more of $R^b$, or (ii) a 5-10 membered heteroaryl, wherein the 5-10 membered heteroaryl is optionally substituted with one or more $R^c$, and each of $R^6$ and $R^7$ is H. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), or a stereoisomer or tautomer thereof, or a pharmaceutically acceptable salt of any of the foregoing, n is 1, $L^2$ is O, one of $X^1$ and $X^2$ is C($R^5$), wherein $R^5$ is H, halo, —CN, 3-10 membered heterocyclyl, $C_{1-6}$alkyl, or $C_{1-6}$alkoxy, wherein the $C_{1-6}$alkyl of $R^5$ is optionally substituted with one or more halo, or —OH, and wherein the $C_{1-6}$alkoxy of $R^5$ is optionally substituted with one or more halo, the other of $X^1$ and $X^2$ is C that is taken together with $R^4$, and the atoms to which they are attached, to form (i) a 5-10 membered heterocyclyl, wherein the 5-10 membered heterocyclyl is optionally substituted with one or more of $R^b$, or (ii) a 5-10 membered heteroaryl, wherein the 5-10 membered heteroaryl is optionally substituted with one or more $R^c$, and each of $R^6$ and $R^7$ is H. In some embodiments, n is 1, $L^2$ is O, one of $X^1$ and $X^2$ is C($R^5$), wherein $R^5$ is H, the other of $X^1$ and $X^2$ is C that is taken together with $R^4$, and the atoms to which they are attached, to form (i) a 5-10 membered heterocyclyl, wherein the 5-10 membered heterocyclyl is optionally substituted with one or more of $R^b$, or (ii) a 5-10 membered heteroaryl, wherein the 5-10 membered heteroaryl is optionally substituted with one or more $R^c$, and each of $R^6$ and $R^7$ is H. In some embodiments, n is 1, $L^2$ is O, one of $X^1$ and $X^2$ is C($R^5$), wherein $R^5$ is halo, —CN, 3-10 membered heterocyclyl, $C_{1-6}$alkyl, or $C_{1-6}$alkoxy, wherein the $C_{1-6}$alkyl of $R^5$ is optionally substituted with one or more halo, or —OH, and wherein the $C_{1-6}$alkoxy of $R^5$ is optionally substituted with one or more halo, the other of $X^1$ and $X^2$ is C that is taken together with $R^4$, and the atoms to which they are attached, to form (i) a 5-10 membered heterocyclyl, wherein the 5-10 membered heterocyclyl is optionally substituted with one or more of $R^b$, or (ii) a 5-10 membered heteroaryl, wherein the 5-10 membered heteroaryl is optionally substituted with one or more $R^c$, and each of $R^6$ and $R^7$ is H. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), or a stereoisomer or tautomer thereof, or a pharmaceutically acceptable salt of any of the foregoing, n is 1, p is 0, $L^2$ is O, one of $X^1$ and $X^2$ is N, the other of $X^1$ and $X^2$ is C that is taken together with $R^4$, and the atoms to which they are attached, to form (i) a 5-10 membered heterocyclyl, wherein the 5-10 membered heterocyclyl is optionally substituted with one or more of $R^b$, or (ii) a 5-10 membered heteroaryl, wherein the 5-10 membered heteroaryl is optionally substituted with one or more $R^c$, and each of $R^6$ and $R^7$ is H. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I'), or a stereoisomer or tautomer thereof, or a pharmaceutically acceptable salt of any of the foregoing:
m is an integer from 0 to 2;
n is an integer from 1 to 2;
p is an integer from 0 to 2;
$R^1$, if present is, independently at each occurrence selected from the group consisting of halo, —CN, $C_{1-3}$alkoxy, or $C_{1-3}$alkyl, wherein
  the $C_{1-3}$alkoxy of $R^1$ is optionally substituted with one or more halo, and
  the $C_{1-3}$alkyl of $R^1$ is optionally substituted with one or more halo;
$R^2$ is H, $C_{1-3}$alkyl, $C_{3-6}$cycloalkyl, or 3-10 membered heterocyclyl, wherein
  the $C_{1-3}$alkyl of $R^2$ is optionally substituted with one or more halo, —OH, —NH$_2$, or $C_{1-3}$alkoxy, and
  the $C_{3-6}$cycloalkyl of $R^2$ is optionally substituted with one or more —OH;
$R^3$, if present, is $C_{1-3}$alkyl;
$L^1$ is $C_{1-3}$alkylene, wherein the $C_{1-3}$alkylene of $L^1$ is optionally substituted with one or more $C_{1-3}$alkyl, and wherein the $C_{1-3}$alkyl is further optionally substituted with one or more —OH or $C_{1-3}$alkoxy;
$L^2$ is O or N($R^x$), wherein $R^x$ is H or $C_{1-3}$alkyl; and
either
(1) $L^3$ is absent or is O, $C_{3-6}$cycloalkyl, 3-10 membered heterocyclyl, or $C_{1-6}$alkylene, wherein
  the $C_{3-6}$cycloalkyl is optionally substituted with one or more —OH, or $C_{1-3}$alkyl,
  the $C_{1-3}$alkylene of $L^3$ is optionally substituted with one or more —OH or $C_{1-3}$alkyl, and
  the 3-10 membered heterocyclyl is optionally substituted with one or more —OH;
$X^1$ and $X^2$ are each independently N or —C($R^5$); and
$R^4$ is:
  (i) —S(O)$_2$—$R^a$;
  (ii) 5-10 membered heteroaryl, wherein the 5-10 membered heteroaryl of $R^4$ is optionally substituted with one or more $C_{1-3}$alkyl;
  (iii) —N($R^d$)$_2$, wherein $R^d$ is independently at each occurrence H, $C_{1-3}$alkyl, or —S(O)$_2$—$R^a$, wherein the $C_{1-3}$alkyl of $R^d$ is optionally substituted with one or more —OH,
  (iv) —NS(O)—($C_{1-3}$alkyl)$_2$, wherein the $C_{1-3}$alkyl is optionally substituted with one or more —OH,
  (v) —C(O)—N($R^e$)$_2$ wherein $R^e$ is independently at each occurrence H, $C_{1-3}$alkyl, or 3-10 membered heterocycle, wherein the 3-10 membered heterocycle is optionally substituted with one or more oxo, or both $R^e$ together with the N to which they are attached are taken together to form a 3-10 membered heterocyclyl, wherein the 3-10 membered heterocyclyl is optionally substituted with one or more halo, oxo, —OH, NH$_2$, —NH—S(O)$_2$—$R^a$, or —S(O)$_2$—$R^a$,
  (vi) 3-10 membered heterocyclyl optionally substituted with one or more $C_{1-3}$alkyl, —OH, oxo or —S(O)$_2R^a$,
  (vii) —S(O)—N($C_{1-3}$alkyl)-($C_{1-3}$alkyl),
  (viii) —CN,
  (ix) —(CH$_2$)$_q$OH, wherein q is an integer from 0-4,
  (x) —C(O)—$C_{1-3}$alkyl, or
  (xi) —P(O)($C_{1-3}$alkyl)$_2$;

or
(2) $L^3$ is absent; and
  one of $X^1$ and $X^2$ is N or C($R^5$); and
  the other of $X^1$ and $X^2$ is N or C that is taken together with $R^4$ and the atoms to which they are attached to form a 5-10 membered heterocyclyl or a 5-10 membered heteroaryl, wherein
    the 5-10 membered heterocyclyl is optionally substituted with one or more $R^b$, wherein $R^b$ is, independently at each occurrence, selected from the group consisting of halo, oxo, $C_{1-3}$alkyl, —C(O)—$C_{1-3}$alkyl, —C(O)—NH$_2$, —C(O)—NH($C_{1-3}$alkyl), —C(O)—N($C_{1-3}$alkyl)$_2$, —S(O)$_2$—$R^a$, $C_{3-6}$cycloalkyl, and 3-6 membered heterocyclyl, wherein
      the $C_{1-3}$alkyl of $R^b$ is optionally substituted with one or more halo, OH, —S(O)$_2$—$C_{1-3}$alkyl, or $C_{3-6}$cycloalkyl, and
      wherein the $C_{3-6}$cycloalkyl of the $C_{1-3}$alkyl of $R^b$ is further optionally substituted with one or more $C_{1-3}$alkyl or —OH and
      the $C_{3-6}$cycloalkyl of $R^b$ is optionally substituted with one or more —OH, $C_{3-6}$cycloalkyl, or $C_{1-3}$alkyl, and
      wherein the $C_{1-3}$alkyl of the $C_{3-6}$cycloalkyl of $R^b$ is further optionally substituted with one or more —OH, and
    the 5-10 membered heteroaryl is optionally substituted with one or more $R^c$, wherein $R^c$ is, independently at each occurrence, selected from the group consisting of halo, $C_{1-3}$alkyl, —C(O)—$C_{1-3}$alkyl, —C(O)—NH$_2$, —C(O)—NH($C_{1-3}$alkyl), —C(O)—N($C_{1-3}$alkyl)$_2$, —S(O)$_2$—$R^a$, $C_{3-6}$cycloalkyl, and 3-6 membered heterocyclyl, wherein
      the $C_{1-3}$alkyl of $R^c$ is optionally substituted with one or more —S(O)$_2$—$C_{1-6}$alkyl,
      the $C_{3-6}$cycloalkyl of $R^c$ is optionally substituted with one or more —OH or $C_{1-6}$alkyl,
      and the 3-6 membered heterocyclyl of $R^c$ is optionally substituted with one or more —OH or $C_{1-3}$alkyl, and
      wherein the $C_{1-3}$alkyl of the 3-6 membered heterocyclyl of $R^c$ is further optionally substituted with one or more —OH;
$R^a$ is, independently at each occurrence:
  (i) $C_{1-3}$alkyl optionally substituted with one or more halo, —OH, —S(O)$_2$—$C_{1-3}$alkyl, or —N($C_{1-3}$alkyl)-C(O)—$C_{1-3}$alkyl,
  (ii) $C_{3-6}$cycloalkyl optionally substituted with one or more —OH, —C(O)$_2$—$C_{1-3}$alkyl, —C(O)—NH($C_{1-3}$alkyl), —C(O)—N($C_{1-3}$alkyl)$_2$, or —C(O)—$C_{3-6}$heterocyclyl, or $C_{1-3}$alkyl, wherein the $C_{1-3}$alkyl is optionally substituted with one or more —OH, or
  (iii) 3-6 membered heterocyclyl optionally substituted with one or more $C_{1-3}$alkyl;
$R^5$ is, independently at each occurrence, H, halo, —CN, 3-6 membered heterocyclyl, $C_{1-3}$alkyl, or $C_{1-3}$alkoxy, wherein the $C_{1-3}$alkyl of $R^5$ is optionally substituted with one or more halo or —OH, and wherein the $C_{1-3}$alkoxy of $R^5$ is optionally substituted with one or more halo; and
$R^6$ and $R^7$ are each independently H or halo. In some variations, the embodiments provided herein also apply to a compound of formula (II), or a stereoisomer or tautomer thereof, or a pharmaceutically acceptable salt of any of the foregoing, or any variation or embodiment thereof.

In some embodiments of a compound of formula (I'), or a stereoisomer or tautomer thereof, or a pharmaceutically acceptable salt of any of the foregoing:

m is an integer from 0 to 2;
n is an integer from 1 to 2;
p is an integer from 0 to 1;
$R^1$, if present is, independently at each occurrence selected from the group consisting of Cl, Br, F, I, —CN, $C_{1-3}$alkoxy, or $C_{1-3}$alkyl, wherein
the $C_{1-3}$alkoxy of $R^1$ is optionally substituted with one or more F, and
the $C_{1-3}$alkyl of $R^1$ is optionally substituted with one or more F;
$R^2$ is H, $C_{1-3}$alkyl, $C_{3-4}$cycloalkyl, or 3-4 membered heterocyclyl, wherein
the $C_{1-3}$alkyl of $R^2$ is optionally substituted with one or more F, —OH, —NH$_2$, or —OCH$_3$, and
the $C_{3-4}$cycloalkyl of $R^2$ is optionally substituted with one or more —OH;
$R^3$, if present, is $C_{1-3}$alkyl;
$L^1$ is $C_{1-3}$alkylene, wherein the $C_{13}$alkylene of $L^1$ is optionally substituted with one or more methyl, and wherein the methyl is further optionally substituted with one or more —OH or —OCH$_3$;
$L^2$ is O; and
either
(1) $L^3$ is absent or is O, $C_{3-4}$cycloalkyl, 3-7 membered heterocyclyl, or $C_{1-4}$alkylene, wherein
the $C_{3-4}$cycloalkyl is optionally substituted with one or more —OH, or —CH$_3$,
the $C_{1-6}$alkylene of $L^3$ is optionally substituted with one or more —OH, —CH$_3$, and
$X^1$ and $X^2$ are each independently N or C($R^5$); and
$R^4$ is:
(i) —S(O)$_2$—$R^a$;
(ii) 5-6 membered heteroaryl, wherein the 5-6 membered heteroaryl of $R^4$ is optionally substituted with one or more —CH$_3$;
(iii) —N($R^d$)$_2$, wherein $R^d$ is independently at each occurrence H, $C_{1-3}$alkyl, or —S(O)$_2$—$R^a$, wherein the $C_{1-3}$alkyl of $R^d$ is optionally substituted with one or more —OH,
(iv) —NS(O)—(CH$_3$)$_2$
(v) —C(O)—N($R^e$)$_2$ wherein $R^e$ is independently at each occurrence H, CH$_3$, or 3-6 membered heterocycle, wherein the 3-6 membered heterocycle is optionally substituted with one or more oxo, or both $R^e$ together with the N to which they are attached are taken together to form a 3-7 membered heterocyclyl, wherein the 3-7 membered heterocyclyl is optionally substituted with one or more F, oxo, —OH, NH$_2$, —NH—S(O)$_2$—$R^a$, or —S(O)$_2$—$R^a$,
(vi) 3-7 membered heterocyclyl optionally substituted with one or more $C_{1-3}$alkyl, —OH, oxo or —S(O)$_2R^a$,
(vii) —S(O)—N(CH$_3$)—(CH$_3$),
(viii) —CN,
(ix) —(CH$_2$)$_q$OH, wherein q is an integer from 0-2, or
(x) —C(O)—CH$_3$, or
(xi) —P(O)(CH$_3$)$_2$;
or
(2) $L^3$ is absent; and
one of $X^1$ and $X^2$ is N or C($R^5$); and
the other of $X^1$ and $X^2$ is N or C that is taken together with $R^4$ and the atoms to which they are attached to form a 5-8 membered heterocyclyl or a 5-6 membered heteroaryl, wherein
the 5-8 membered heterocyclyl is optionally substituted with one or more $R^b$, wherein $R^b$ is, independently at each occurrence, selected from the group consisting of oxo, $C_{1-3}$alkyl, —C(O)—CH$_3$, —C(O)—NH$_2$, —C(O)—NH(CH$_3$), —C(O)—N(CH$_3$)$_2$, —S(O)$_2$—$R^a$, $C_{3-4}$cycloalkyl, and 3-4 membered heterocyclyl, wherein
the $C_{1-3}$alkyl of $R^b$ is optionally substituted with one or more F, OH, —S(O)$_2$—CH$_3$, or $C_{3-4}$cycloalkyl, and
wherein the $C_{3-4}$cycloalkyl of the $C_{1-3}$alkyl of $R^b$ is further optionally substituted with one or more CH$_3$ or —OH and
the $C_{3-4}$cycloalkyl of $R^b$ is optionally substituted with one or more —OH, $C_{3-4}$cycloalkyl, or $C_{1-3}$alkyl, and
wherein the $C_{1-3}$alkyl of the $C_{3-4}$cycloalkyl of $R^b$ is further optionally substituted with one or more —OH, and
the 5-6 membered heteroaryl is optionally substituted with one or more $R^c$, wherein $R^c$ is, independently at each occurrence, selected from the group consisting of $C_{1-3}$alkyl, —S(O)$_2$—$R^a$, $C_{3-4}$cycloalkyl, and 3-4 membered heterocyclyl, wherein
the $C_{1-6}$alkyl of $R^c$ is optionally substituted with one or more —S(O)$_2$—CH$_3$
the $C_{3-4}$cycloalkyl of $R^c$ is optionally substituted with one or more —OH or $C_{1-3}$alkyl,
and the 3-4 membered heterocyclyl of $R^c$ is optionally substituted with one or more —OH or methyl, and
wherein the methyl of the 3-4 membered heterocyclyl of $R^c$ is further optionally substituted with one or more —OH;
$R^a$ is, independently at each occurrence:
(i) $C_{1-3}$alkyl optionally substituted with one or more F, —OH, —S(O)$_2$—CH$_3$, or —N(CH$_3$)—C(O)—CH$_3$,
(ii) $C_{34}$cycloalkyl optionally substituted with one or more —OH, —C(O)$_2$—CH$_3$, —C(O)—NH(CH$_3$), —C(O)—N(CH$_3$)$_2$, or —C(O)—$C_{3-4}$heterocyclyl, or methyl, wherein the methyl is optionally substituted with one or more —OH, or
(iii) 3-4 membered heterocyclyl optionally substituted with one or more methyl;
$R^5$ is, independently at each occurrence, H, Cl, F, —CN, 3-4 membered heterocyclyl, $C_{1-3}$alkyl, or $C_{1-3}$alkoxy, wherein the $C_{1-3}$alkyl of $R^5$ is optionally substituted with one or more F or —OH and wherein the $C_{1-3}$alkoxy of $R^5$ is optionally substituted with one or more F; and
$R^6$ and $R^7$ are each independently H or F. In some variations, the embodiments provided herein also apply to a compound of formula (II), or a stereoisomer or tautomer thereof, or a pharmaceutically acceptable salt of any of the foregoing, or any variation or embodiment thereof.

In some embodiments of a compound of formula (II), or a stereoisomer or tautomer thereof, or a pharmaceutically acceptable salt of any of the foregoing,
m is an integer from 0 to 2;
n is an integer from 1 to 2;
p is an integer from 0 to 1;
$R^1$, if present is, independently at each occurrence selected from the group consisting of halo, —CN, $C_{1-3}$alkoxy, and $C_{1-3}$alkyl, wherein
the $C_{1-3}$alkoxy of $R^1$ is optionally substituted with one or more halo, and
the $C_{1-3}$alkyl of $R^1$ is optionally substituted with one or more halo;

$R^2$ is H, $C_{1-3}$alkyl, $C_{3-6}$cycloalkyl, or 3-6 membered heterocyclyl, wherein
  the $C_{1-6}$alkyl of $R^2$ is optionally substituted with one or more deuterium, halo, —OH, —NH$_2$, or $C_{1-3}$alkoxy, and
  the $C_{3-6}$cycloalkyl of $R^2$ is optionally substituted with one or more —OH;
$R^3$, if present, is $C_{1-3}$alkyl;
$L^1$ is $C_{1-3}$alkylene, wherein
  the $C_{1-6}$alkylene of $L^1$ is optionally substituted with one or more deuterium or $C_{1-3}$alkyl, and wherein
    the $C_{1-3}$alkyl is further optionally substituted with one or more —OH or $C_{1-3}$alkoxy;
$L^2$ is O; and
either
(1) $L^3$ is absent or is O, $C_{3-6}$cycloalkyl, 3-6 membered heterocyclyl, or $C_{1-3}$alkylene, wherein
  the $C_{3-6}$cycloalkyl of $L^3$ is optionally substituted with one or more —OH or $C_{1-3}$alkyl,
  the $C_{1-3}$alkylene of $L^3$ is optionally substituted with one or more —OH or $C_{1-3}$alkyl, wherein
    the $C_{1-3}$alkyl is optionally substituted with one or more —OH, and
  the 3-6 membered heterocyclyl of $L^3$ is optionally substituted with one or more —OH or $C_{1-3}$alkyl;
$X^1$ and $X^2$ are each independently N or $C(R^5)$; and
$R^4$ is:
(i) —S(O)$_2$—$R^a$;
(ii) 5-10 membered heteroaryl, wherein the 5-10 membered heteroaryl of $R^4$ is optionally substituted with one or more $C_{1-3}$alkyl;
(iii) —N($R^d$)$_2$, wherein $R^d$ is independently at each occurrence H, $C_{1-3}$alkyl, or —S(O)$_2$—$R^a$, wherein
  the $C_{1-3}$alkyl of $R^d$ is optionally substituted with one or more —OH,
(iv) —NS(O)—$(C_{1-3}$alkyl)$_2$, wherein the $C_{1-3}$alkyl is optionally substituted with one or more —OH,
(v) —C(O)—N($R^e$)$_2$ wherein $R^e$ is independently at each occurrence H, $C_{1-3}$alkyl, or 3-6 membered heterocycle, wherein
  the 3-6 membered heterocycle of $R^e$ is optionally substituted with one or more oxo, or both $R^e$ together with the N to which they are attached are taken together to form a 3-6 membered heterocyclyl, wherein
    the 3-6 membered heterocyclyl is optionally substituted with one or more halo, oxo, —OH, NH$_2$, —NH—S(O)$_2$—$R^a$, or —S(O)$_2$—$R^a$,
(vi) 3-6 membered heterocyclyl optionally substituted with one or more $C_{1-3}$alkyl, —OH, oxo or —S(O)$_2R^a$,
(vii) —S(O)—N($C_{1-3}$alkyl)-($C_{1-3}$alkyl),
(viii) —CN,
(ix) —(CH$_2$)$_q$OH, wherein q is an integer from 0-3,
(x) —C(O)—$C_{1-3}$alkyl, or
(xi) —P(O)($C_{1-3}$alkyl)$_2$;
or
(2) $L^3$ is absent; and
one of $X^1$ and $X^2$ is N or $C(R^5)$; and
the other of $X^1$ and $X^2$ is N or C that is taken together with $R^4$, and the atoms to which they are attached, to form a 5-8 membered heterocyclyl or a 5-10 membered heteroaryl, wherein
  the 5-8 membered heterocyclyl is optionally substituted with one or more $R^b$, wherein
    $R^b$ is, independently at each occurrence, selected from the group consisting of —OH, halo, oxo, $C_{1-3}$alkyl, —C(O)—$C_{1-3}$alkyl, —C(O)—NH$_2$, —C(O)—NH($C_{1-3}$alkyl), —C(O)—N($C_{1-3}$alkyl)$_2$, —S(O)$_2$—$R^a$, $C_{3-6}$cycloalkyl, and 3-6 membered heterocyclyl, wherein
      the $C_{1-3}$alkyl of $R^b$ is optionally substituted with one or more halo, OH, —S(O)$_2$—$C_{1-3}$alkyl, or $C_{3-6}$cycloalkyl, and wherein
        the $C_{3-6}$cycloalkyl of the $C_{1-3}$alkyl of $R^b$ is further optionally substituted with one or more $C_{1-3}$alkyl or —OH and
      the $C_{3-6}$cycloalkyl of $R^b$ is optionally substituted with one or more —OH, $C_{3-6}$cycloalkyl, or $C_{1-3}$alkyl, and wherein
        the $C_{1-3}$alkyl of the $C_{3-6}$cycloalkyl of $R^b$ is further optionally substituted with one or more —OH, deuterium, or halo, and
  the 5-10 membered heteroaryl is optionally substituted with one or more $R^c$, wherein
    $R^c$ is, independently at each occurrence, selected from the group consisting of halo, $C_{1-3}$alkyl, —C(O)—$C_{1-3}$alkyl, —C(O)—NH$_2$, —C(O)—NH($C_{1-3}$alkyl), —C(O)—N($C_{1-3}$alkyl)$_2$, —S(O)$_2$—$R^a$, $C_{3-6}$cycloalkyl, and 3-6 membered heterocyclyl, wherein
      the $C_{1-3}$alkyl of $R^c$ is optionally substituted with one or more —S(O)$_2$—$C_{1-3}$alkyl, the $C_{3-6}$cycloalkyl of $R^c$ is optionally substituted with one or more —OH or $C_{1-3}$alkyl, and
      the 3-6 membered heterocyclyl of $R^c$ is optionally substituted with one or more —OH or $C_{1-3}$alkyl, and wherein
        the $C_{1-3}$alkyl of the 3-6 membered heterocyclyl of $R^c$ is further optionally substituted with one or more —OH;
$R^a$ is, independently at each occurrence:
(i) $C_{1-3}$alkyl optionally substituted with one or more halo, —OH, —S(O)$_2$—$C_{1-3}$alkyl, or —N($C_{1-3}$alkyl)-C(O)—$C_{1-3}$alkyl,
(ii) $C_{3-6}$cycloalkyl optionally substituted with one or more —OH, —C(O)$_2$—$C_{1-3}$alkyl, —C(O)—NH($C_{1-3}$alkyl), —C(O)—N($C_{1-3}$alkyl)$_2$, or —C(O)—$C_{3-6}$heterocyclyl, or $C_{1-3}$alkyl, wherein the $C_{1-3}$alkyl is optionally substituted with one or more —OH,
(iii) 3-6 membered heterocyclyl optionally substituted with one or more $C_{1-3}$alkyl, or
(iv) NH($C_{1-3}$alkyl);
$R^5$ is, independently at each occurrence, H, halo, —CN, 3-6 membered heterocyclyl, $C_{1-3}$alkyl, or $C_{1-3}$alkoxy, wherein
  the $C_{1-3}$alkyl of $R^5$ is optionally substituted with one or more halo or —OH, and
  the $C_{1-3}$alkoxy of $R^5$ is optionally substituted with one or more halo;
$X^3$ is N or $C(R^6)$;
$X^4$ is N or $C(R^7)$;
and
$R^6$ and $R^7$ are each independently H or halo.
In some embodiments of a compound of formula (II), or a stereoisomer or tautomer thereof, or a pharmaceutically acceptable salt of any of the foregoing,
m is an integer from 0 to 2;
n is 1;
p is an integer from 0;
$R^1$, if present is, independently at each occurrence selected from the group consisting of halo, —CN, $C_{1-3}$alkoxy, and $C_{1-3}$alkyl, wherein
  the $C_{1-3}$alkoxy of $R^1$ is optionally substituted with one or more halo, and the $C_{1-3}$alkyl of $R^1$ is optionally substituted with one or more halo;

$R^2$ is H, $C_{1-3}$alkyl, $C_{3-6}$cycloalkyl, or 3-6 membered heterocyclyl, wherein
  the $C_{1-6}$alkyl of $R^2$ is optionally substituted with one or more deuterium, halo, —OH, —NH$_2$, or $C_{1-3}$alkoxy, and
  the $C_{3-6}$cycloalkyl of $R^2$ is optionally substituted with one or more —OH;

$L^1$ is $C_{1-3}$alkylene, wherein
  the $C_{1-6}$alkylene of $L^1$ is optionally substituted with one or more deuterium;

$L^2$ is O; and
either
(1) $L^3$ is absent or is O, $C_{3-6}$cycloalkyl, 3-6 membered heterocyclyl, or $C_{1-3}$alkylene, wherein
  the $C_{3-6}$cycloalkyl of $L^3$ is optionally substituted with one or more —OH or $C_{1-3}$alkyl,
  the $C_{1-3}$alkylene of $L^3$ is optionally substituted with one or more —OH or $C_{1-3}$alkyl, wherein
    the $C_{1-3}$alkyl is optionally substituted with one or more —OH, and
  the 3-6 membered heterocyclyl of $L^3$ is optionally substituted with one or more —OH or $C_{1-3}$alkyl;

$X^1$ and $X^2$ are each independently N or $C(R^5)$; and $R^4$ is:
(i) —S(O)$_2$—$R^a$;
(ii) 5-10 membered heteroaryl, wherein the 5-10 membered heteroaryl of $R^4$ is optionally substituted with one or more $C_{1-3}$alkyl;
(iii) —N($R^d$)$_2$, wherein $R^d$ is independently at each occurrence H, $C_{1-3}$alkyl, or —S(O)$_2$—$R^a$, wherein
  the $C_{1-3}$alkyl of $R^d$ is optionally substituted with one or more —OH,
(iv) —NS(O)—(C$_{1-3}$alkyl)$_2$, wherein the $C_{1-3}$alkyl is optionally substituted with one or more —OH,
(v) —C(O)—N($R^e$)$_2$ wherein $R^e$ is independently at each occurrence H, $C_{1-3}$alkyl, or 3-6 membered heterocycle, wherein
  the 3-6 membered heterocycle of $R^c$ is optionally substituted with one or more oxo, or both $R^e$ together with the N to which they are attached are taken together to form a 3-6 membered heterocyclyl, wherein
    the 3-6 membered heterocyclyl is optionally substituted with one or more halo, oxo, —OH, NH$_2$, —NH—S(O)$_2$—$R^a$, or —S(O)$_2$—$R^a$,
(vi) 3-6 membered heterocyclyl optionally substituted with one or more $C_{1-3}$alkyl, —OH, oxo or —S(O)$_2 R^a$,
(ix) —(CH$_2$)$_q$OH, wherein q is an integer from 0-3;
or
(2) $L^3$ is absent; and
one of $X^1$ and $X^2$ is N or $C(R^5)$; and
the other of $X^1$ and $X^2$ is N or C that is taken together with $R^4$, and the atoms to which they are attached, to form a 5-8 membered heterocyclyl or a 5-10 membered heteroaryl, wherein
  the 5-10 membered heterocyclyl is optionally substituted with one or more $R^b$, wherein
    $R^b$ is, independently at each occurrence, selected from the group consisting of —OH, halo, oxo, $C_{1-3}$alkyl, —C(O)—C$_{1-3}$alkyl, —C(O)—NH$_2$, —C(O)—NH(C$_{1-3}$alkyl), —C(O)—N(C$_{1-3}$alkyl)$_2$, —S(O)$_2$—$R^a$, $C_{3-6}$cycloalkyl, and 3-6 membered heterocyclyl, wherein the $C_{1-3}$alkyl of $R^b$ is optionally substituted with one or more halo, OH, —S(O)$_2$—C$_{1-3}$alkyl, or $C_{3-6}$cycloalkyl, and wherein
  the $C_{3-6}$cycloalkyl of the $C_{1-3}$alkyl of $R^b$ is further optionally substituted with one or more $C_{1-3}$alkyl or —OH and
the $C_{3-6}$cycloalkyl of $R^b$ is optionally substituted with one or more —OH, $C_{3-6}$cycloalkyl, or $C_{1-3}$alkyl, and wherein
  the $C_{1-3}$alkyl of the $C_{3-6}$cycloalkyl of $R^b$ is further optionally substituted with one or more —OH, deuterium, or halo, and
the 5-10 membered heteroaryl is optionally substituted with one or more $R^c$, wherein
  $R^c$ is, independently at each occurrence, selected from the group consisting of halo, $C_{1-3}$alkyl, —C(O)—C$_{1-3}$alkyl, —C(O)—NH$_2$, —C(O)—NH(C$_{1-3}$alkyl), —C(O)—N(C$_{1-3}$alkyl)$_2$, —S(O)$_2$—$R^a$, $C_{3-6}$cycloalkyl, and 3-6 membered heterocyclyl, wherein
    the $C_{1-3}$alkyl of $R^c$ is optionally substituted with one or more —S(O)$_2$—C$_{1-3}$alkyl,
    the $C_{3-6}$cycloalkyl of $R^c$ is optionally substituted with one or more —OH or $C_{1-3}$alkyl, and
    the 3-6 membered heterocyclyl of $R^c$ is optionally substituted with one or more —OH or $C_{1-3}$alkyl, and wherein
      the $C_{1-3}$alkyl of the 3-6 membered heterocyclyl of $R^c$ is further optionally substituted with one or more —OH;

$R^a$ is, independently at each occurrence:
(i) $C_{1-3}$alkyl optionally substituted with one or more halo, —OH, —S(O)$_2$—C$_{1-3}$alkyl, or —N(C$_{1-3}$alkyl)-C(O)—C$_{1-3}$alkyl,
(ii) $C_{3-6}$cycloalkyl optionally substituted with one or more —OH, —C(O)$_2$—C$_{1-3}$alkyl, —C(O)—NH(C$_{1-3}$alkyl), —C(O)—N(C$_{1-3}$alkyl)$_2$, or —C(O)—C$_{3-6}$heterocyclyl, or $C_{1-3}$alkyl, wherein
  the $C_{1-3}$alkyl is optionally substituted with one or more —OH,
(iii) 3-6 membered heterocyclyl optionally substituted with one or more $C_{1-3}$alkyl, or
(iv) NH(C$_{1-3}$alkyl);

$R^5$ is, independently at each occurrence, H, halo, —CN, 3-6 membered heterocyclyl, $C_{1-3}$alkyl, or $C_{1-3}$alkoxy, wherein
  the $C_{1-3}$alkyl of $R^5$ is optionally substituted with one or more halo or —OH, and
  the $C_{1-3}$alkoxy of $R^5$ is optionally substituted with one or more halo;

$X^3$ is N or $C(R^6)$;
$X^4$ is N or $C(R^7)$;
and
$R^6$ and $R^7$ are each independently H or halo.

In some embodiments of a compound of formula (II), or a stereoisomer or tautomer thereof, or a pharmaceutically acceptable salt of any of the foregoing,
m is an integer from 0 to 2;
n is 1;
p is an integer from 0;

$R^1$, if present is, independently at each occurrence selected from the group consisting of halo, —CN, $C_{1-3}$alkoxy, and $C_{1-3}$alkyl, wherein
  the $C_{1-3}$alkoxy of $R^1$ is optionally substituted with one or more halo, and
  the $C_{1-3}$alkyl of $R^1$ is optionally substituted with one or more halo;
$R^2$ is H;
$L^1$ is $C_{1-3}$alkylene, wherein
  the $C_{1-6}$alkylene of $L^1$ is optionally substituted with one or more deuterium;
$L^2$ is O; and
either
(1) $L^3$ is absent or is $C_{1-3}$alkylene, wherein
  the $C_{1-3}$alkylene of $L^3$ is optionally substituted with one or more —OH or $C_{1-3}$alkyl;
$X^1$ and $X^2$ are each independently N or $C(R^5)$; and
$R^4$ is:
(i) —$S(O)_2$—$R^a$;
(ii) —$(CH_2)_q$OH, wherein q is an integer from 0-3;
or
(2) $L^3$ is absent; and
one of $X^1$ and $X^2$ is N or $C(R^5)$; and
the other of $X^1$ and $X^2$ is N or C that is taken together with $R^4$, and the atoms to which they are attached, to form a 5-8 membered heterocyclyl or a 5-20 membered heteroaryl, wherein
  the 5-10 membered heterocyclyl is optionally substituted with one or more $R^b$, wherein
    $R^b$ is, independently at each occurrence oxo, or $C_{3-6}$cycloalkyl, wherein the $C_{3-6}$cycloalkyl is optionally substituted with one or more —OH, $C_{3-6}$cycloalkyl, or $C_{1-3}$alkyl, and
  the 5-10 membered heteroaryl is optionally substituted with one or more $R^c$, wherein
    $R^c$ is, independently at each occurrence, selected from the group consisting of $C_{1-3}$alkyl, $C_{3-6}$cycloalkyl, wherein the $C_{3-6}$cycloalkyl of $R^c$ is optionally substituted with one or more —OH or $C_{1-3}$alkyl;
$R^a$ is, independently at each occurrence:
(i) $C_{1-3}$alkyl optionally substituted with one or more halo, —OH, —$S(O)_2$—$C_{1-3}$alkyl, or —$N(C_{1-3}$alkyl$)$-$C(O)$—$C_{1-3}$alkyl;
$R^5$ is, independently at each occurrence, H, halo, $C_{1-3}$alkyl, or $C_{1-3}$alkoxy, wherein
  the $C_{1-3}$alkyl of $R^5$ is optionally substituted with one or more halo or —OH, and
  the $C_{1-3}$alkoxy of $R^5$ is optionally substituted with one or more halo;
$X^3$ is N or $C(R^6)$;
$X^4$ is N or $C(R^7)$;
and
$R^6$ and $R^7$ are each independently H or halo.

In some embodiments, provided herein is a compound of formula (I), or a stereoisomer or tautomer thereof, or a pharmaceutically acceptable salt of any of the foregoing, wherein the compound is a compound of formula (I-A):

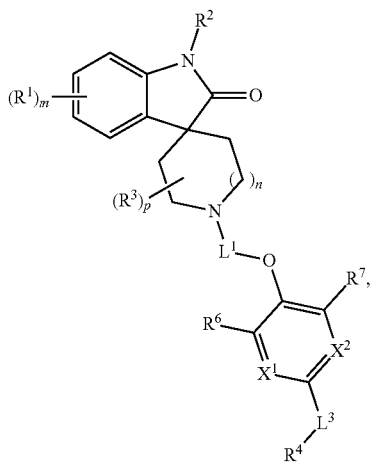

or a stereoisomer or tautomer thereof, or a pharmaceutically acceptable salt of any of the foregoing, wherein: n is 1 or 2; and m, p, $R^1$, $R^2$, $R^3$, $L^1$, $L^3$, $R^4$, $X^1$, $X^2$, $R^6$, and $R^7$ are as defined for formula (I). In some variations m, p, $R^1$, $R^2$, $R^3$, $L^1$, $L^3$, $R^4$, $X^1$, $X^2$, $R^6$, and $R^7$ of formula (I-A) are as defined for a compound of formula (I'), or (II), or a stereoisomer or tautomer thereof, or a pharmaceutically acceptable salt of any of the foregoing, or any variation or embodiment thereof.

In some embodiments, provided herein is a compound of formula (I) or formula (I-A), or a stereoisomer or tautomer thereof, or a pharmaceutically acceptable salt of any of the foregoing, wherein the compound is a compound of formula (I-A1):

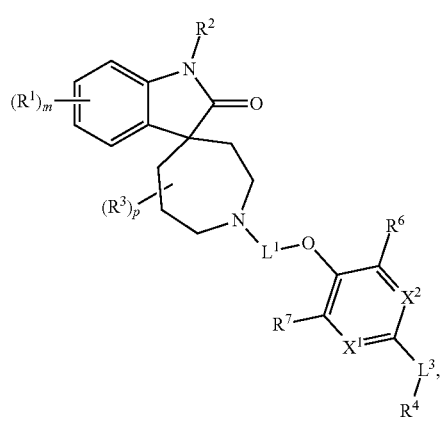

or a stereoisomer or tautomer thereof, or a pharmaceutically acceptable salt of any of the foregoing, wherein: m, p, $R^1$, $R^2$, $R^3$, $L^1$, $L^3$, $R^4$, $X^1$, $X^2$, $R^6$, and $R^7$ are as defined for formula (I). In some variations m, p, $R^1$, $R^2$, $R^3$, $L^1$, $L^3$, $R^4$, $X^1$, $X^2$, $R^6$, and $R^7$ of formula (I-A1) are as defined for a compound of formula (I'), or (II), or a stereoisomer or tautomer thereof, or a pharmaceutically acceptable salt of any of the foregoing, or any variation or embodiment thereof.

In some embodiments of a compound of formula (I), (I-A) or (I-A1), or a stereoisomer or tautomer thereof, or a pharmaceutically acceptable salt of any of the foregoing, $R^2$ is H. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), (I-A) or (I-A1), or a stereoisomer or tautomer thereof, or a pharmaceutically acceptable salt of any of the foregoing, m is an integer from 0 to 4. In some embodiments, m is an integer from 0 to 2. In some embodiments, m is 0. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), (I-A) or (I-A1), or a stereoisomer or tautomer thereof, or a pharmaceutically acceptable salt of any of the foregoing, p is an integer from 0 to 10. In some embodiments, p is 0 or 1. In some embodiments, p is 0. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), (I-A) or (I-A1), or a stereoisomer or tautomer thereof, or a pharmaceutically acceptable salt of any of the foregoing, $L^1$ is $C_{1-6}$alkylene. In some embodiments, $L^1$ is $C_{1-3}$alkylene. In some embodiments, $L^1$ is ethylene. In some embodiments, $L^1$ is

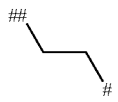

wherein, # denotes the point of attachment to —O— and ## denotes the point of attachment to the remainder of the molecule. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), (I-A) or (I-A1), or a stereoisomer or tautomer thereof, or a pharmaceutically acceptable salt of any of the foregoing, $L^3$ is absent. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), (I-A) or (I-A1), or a stereoisomer or tautomer thereof, or a pharmaceutically acceptable salt of any of the foregoing, $R^4$ is —S(O)$_2$—$R^a$, wherein $R^a$ is $C_{1-6}$alkyl. In some embodiments, $R^4$ is —S(O)$_2$—$R^a$, wherein $R^a$ is $C_{1-3}$alkyl. In some embodiments, $R^4$ is —S(O)$_2$—$R^a$, wherein $R^a$ is methyl. In some embodiments, $R^4$ is

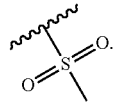

In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), (I-A) or (I-A1), or a stereoisomer or tautomer thereof, or a pharmaceutically acceptable salt of any of the foregoing, each of $X^1$ and $X^2$ is $C(R^5)$. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), (I-A) or (I-A1), or a stereoisomer or tautomer thereof, or a pharmaceutically acceptable salt of any of the foregoing, $R^5$ is H. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), (I-A) or (I-A1), or a stereoisomer or tautomer thereof, or a pharmaceutically acceptable salt of any of the foregoing, each of $R^6$ and $R^7$ is H. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments, provided herein is a compound of formula (I) or formula (I-A), or a stereoisomer or tautomer thereof, or a pharmaceutically acceptable salt of any of the foregoing, wherein the compound is a compound of formula (I-A2):

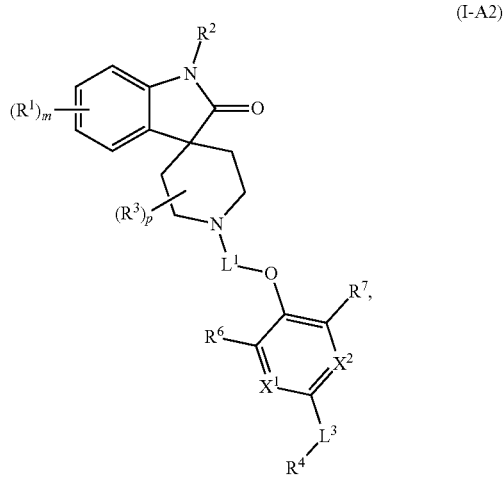

(I-A2)

or a stereoisomer or tautomer thereof, or a pharmaceutically acceptable salt of any of the foregoing, wherein m, p, $R^1$, $R^2$, $R^3$, $L^1$, $L^3$, $R^4$, $X^1$, $X^2$, $R^6$, and $R^7$ are as defined for formula (I). In some variations, m, p, $R^1$, $R^2$, $R^3$, $L^1$, $L^3$, $R^4$, $X^1$, $X^2$, $R^6$, and $R^7$ of formula (I-A2) are as defined for a compound of formula (I'), or (II), or a stereoisomer or tautomer thereof, or a pharmaceutically acceptable salt of any of the foregoing, or any variation or embodiment thereof.

In some embodiments, provided herein is a compound of formula (I) or formula (I-A), or a stereoisomer or tautomer thereof, or a pharmaceutically acceptable salt of any of the foregoing, wherein the compound is a compound of formula (I-A3):

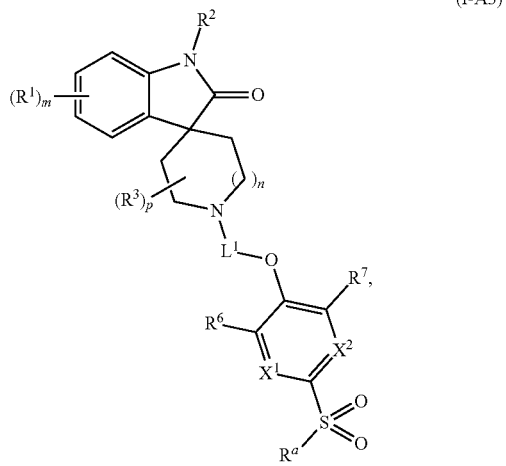

or a stereoisomer or tautomer thereof, or a pharmaceutically acceptable salt of any of the foregoing, wherein: n is 1 or 2; and wherein m, n, p, $R^1$, $R^2$, $R^3$, $L^1$, $X^1$, $X^2$, $R^6$, $R^7$, and $R^a$ are as defined for formula (I). In some variations, m, n, p, $R^1$, $R^2$, $R^3$, $L^1$, $X^1$, $X^2$, $R^6$, $R^7$, and $R^a$ of formula (I-A3) are as defined for a compound of formula (I'), or (II), or a stereoisomer or tautomer thereof, or a pharmaceutically acceptable salt of any of the foregoing, or any variation or embodiment thereof.

In some embodiments, provided herein is a compound of formula (I), (I-A), or (I-A2), or a stereoisomer or tautomer thereof, or a pharmaceutically acceptable salt thereof, wherein the compound is a compound of formula (I-B):

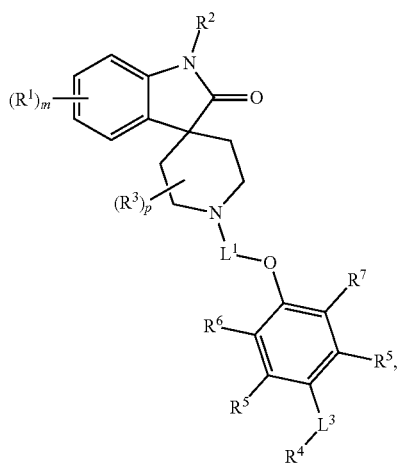

or a stereoisomer or tautomer thereof, or a pharmaceutically acceptable salt of any of the foregoing, wherein: m, p, $R^1$, $R^2$, $R^3$, $L^1$, $L^3$, $R^4$, $R^5$, $R^6$, and $R^7$ are as defined for formula (I). In some variations, m, p, $R^1$, $R^2$, $R^3$, $L^1$, $L^3$, $R^4$, $R^5$, $R^6$, and $R^7$ of formula (I-B) are as defined for a compound of formula (I'), or (II), or a stereoisomer or tautomer thereof, or a pharmaceutically acceptable salt of any of the foregoing, or any variation or embodiment thereof.

In some embodiments, provided herein is a compound of formula (I), (I-A), (I-A2), or (I-B), or a stereoisomer or tautomer thereof, or a pharmaceutically acceptable salt thereof, wherein the compound is a compound of formula (I-B1):

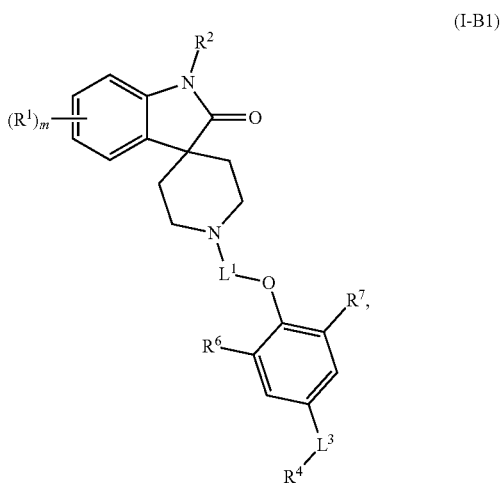

or a stereoisomer or tautomer thereof, or a pharmaceutically acceptable salt of any of the foregoing, wherein: m, $R^1$, $R^2$, $L^1$, $L^3$, $R^4$, $R^6$, and $R^7$ are as defined for formula (I). In some variations, m, $R^1$, $R^2$, $L^1$, $L^3$, $R^4$, $R^6$, and $R^7$ of formula (I-B1) are as defined for a compound of formula (I'), or (II), or a stereoisomer or tautomer thereof, or a pharmaceutically acceptable salt of any of the foregoing, or any variation or embodiment thereof.

In some embodiments of a compound of formula (I), (I-A), (I-A2), (I-B), or (I-B1), or a stereoisomer or tautomer thereof, or a pharmaceutically acceptable salt of any of the foregoing, $R^2$ is H. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), (I-A), (I-A2), (I-B), or (I-B1), or a stereoisomer or tautomer thereof, or a pharmaceutically acceptable salt of any of the foregoing, $R^2$ is $C_{1-6}$alkyl. In some embodiments, $R^2$ is $C_{1-3}$alkyl. In some embodiments, $R^2$ is methyl. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), (I-A), (I-A2), (I-B), or (I-B1), or a stereoisomer or tautomer thereof, or a pharmaceutically acceptable salt of any of the foregoing, $R^2$ is $C_{1-6}$alkyl optionally substituted with one or more halo, —OH, or $C_{1-6}$alkoxy. In some embodiments, $R^2$ is $C_{1-3}$alkyl optionally substituted with one or more halo, —OH, or $C_{1-3}$alkoxy. In some embodiments, $R^2$ is ethyl optionally substituted with one or more halo, —OH, $NH_2$, or $C_{1-3}$alkoxy. In some embodiments, $R^2$ is selected from the group consisting of

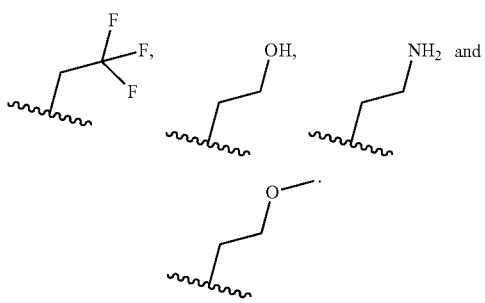

In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (II), such as a compound of formula (I-A), (I-A2), (I-B), or (I-B1), or a stereoisomer or tautomer thereof, or a pharmaceutically acceptable salt of any of the foregoing, $R^2$ is $C_{1-6}$alkyl optionally substituted with one or more deuterium, halo, —OH, or $C_{1-6}$alkoxy. In some embodiments, $R^2$ is $C_{1-3}$alkyl optionally substituted with one or more deuterium, halo, —OH, or $C_{1-3}$alkoxy. In some embodiments, $R^2$ is methyl optionally substituted with one or more deuterium halo, —OH, $NH_2$, or $C_{1-3}$alkoxy. In some embodiments, $R^2$ is ethyl optionally substituted with one or more deuterium halo, —OH, $NH_2$, or $C_{1-3}$alkoxy. In some embodiments, $R^2$ is selected from the group consisting of

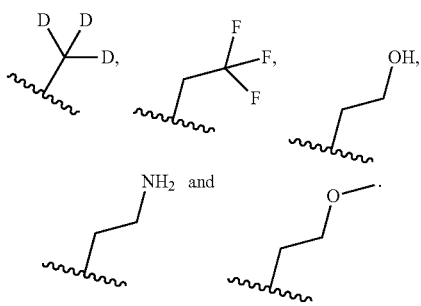

In some embodiments of a compound of formula (I), (I-A), (I-A2), (I-B), or (I-B1), or a stereoisomer or tautomer thereof, or a pharmaceutically acceptable salt of any of the foregoing, $R^2$ is $C_{3-10}$cycloalkyl optionally substituted with one or more —OH. In some embodiments, $R^2$ is $C_{3-6}$cycloalkyl optionally substituted with one or more —OH. In some embodiments, $R^2$ is

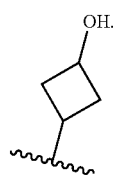 [SMILES: *C1CC(O)C1]

In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), (I-A), (I-A2), (I-B), or (I-B1), or a stereoisomer or tautomer thereof, or a pharmaceutically acceptable salt of any of the foregoing, $R^2$ is 3-15 membered heterocyclyl. In some embodiments, $R^2$ is 3-6 membered heterocyclyl. In some embodiments, $R^2$ is

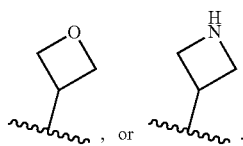 [SMILES: *C1COC1 ; *C1CNC1]

In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), (I-A), (I-A2), (I-B), or (I-B1), or a stereoisomer or tautomer thereof, or a pharmaceutically acceptable salt of any of the foregoing, m is an integer from 0 to 4. In some embodiments, m is an integer from 0 to 2. In some embodiments, m is 0. In some embodiments m is 1. In some embodiments, m is 2. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), (I-A), (I-A2), (I-B), or (I-B1), or a stereoisomer or tautomer thereof, or a pharmaceutically acceptable salt of any of the foregoing, $R^1$ is halo. In some embodiments $R^1$ is Cl. In some embodiments, $R^1$ is Br. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), (I-A), (I-A2), (I-B), or (I-B1), or a stereoisomer or tautomer thereof, or a pharmaceutically acceptable salt of any of the foregoing, $R^1$ is $C_{1-6}$alkyl. In some embodiments, $R^1$ is methyl. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I'), (I-A), (I-A2), (I-B), or (I-B1), or a stereoisomer or tautomer thereof, or a pharmaceutically acceptable salt of any of the foregoing, $R^1$ is $C_{1-6}$alkyl, wherein the $C_{1-6}$alkyl of $R^1$ is optionally substituted with one or more halo. In some embodiments, $R^1$ is $C_{1-3}$alkyl, wherein the $C_{1-3}$alkyl of $R^1$ is optionally substituted with one or more halo. In some embodiments, $R^1$ is methyl, wherein the methyl of $R^1$ is optionally substituted with one or more F. In some embodiments. $R^1$ is

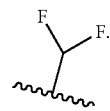

In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), (I-A), (I-A2), (I-B), or (I-B1), or a stereoisomer or tautomer thereof, or a pharmaceutically acceptable salt of any of the foregoing, $R^1$ is —CN. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), or a stereoisomer or tautomer thereof, or a pharmaceutically acceptable salt of any of the foregoing, p is an integer from 0 to 10. In some embodiments, p is 0. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), (I-A), (I-A2), (I-B), or (I-B1), or a stereoisomer or tautomer thereof, or a pharmaceutically acceptable salt of any of the foregoing, $L^1$ is $C_{1-6}$alkylene, wherein the $C_{1-6}$alkylene of $L^1$ is optionally substituted with one or more $C_{1-6}$alkyl. In some embodiments, $L^1$ is $C_{1-3}$alkylene optionally substituted with one or more $C_{1-3}$alkyl. In some embodiments, $L^1$ is ethylene optionally substituted with one or more $C_{1-6}$alkyl. In some embodiments, $L^1$ is selected from the group consisting of

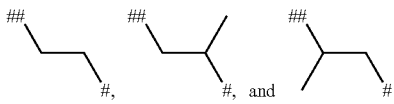

wherein, for each $L^1$, # denotes the point of attachment to —O— and ## denotes the point of attachment to the remainder of the molecule. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), (I-A), (I-A2), (I-B), or (I-B1), or a stereoisomer or tautomer thereof, or a pharmaceutically acceptable salt of any of the foregoing, $L^3$ is absent. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), (I-A), (I-A2), (I-B), or (I-B1), or a stereoisomer or tautomer thereof, or a pharmaceutically acceptable salt of any of the foregoing, $L^3$ is $C_{1-6}$alkylene. In some embodiments, $L^3$ is $C_{1-3}$alkylene. In some embodiments, $L^3$ is selected from the group consisting of

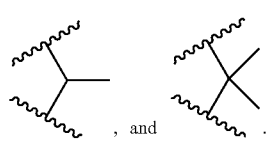

In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), (I-A), (I-A2), (I-B), or (I-B1), or a stereoisomer or tautomer thereof, or a pharmaceutically acceptable salt of any of the foregoing, $L^3$ is $C_{3-10}$cycloalkyl, wherein the $C_{3-10}$cycloalkyl of $L^3$ is optionally substituted with one or more —OH. In some embodiments, $L^3$ is $C_{3-8}$cycloalkyl, wherein the $C_{3-8}$cycloalkyl of $L^3$ is optionally substituted with one or more —OH. In some embodiments, $L^3$ is selected from the group consisting of

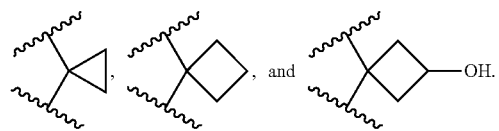 [SMILES: *C1(*)CC1 ; *C1(*)CCC1 ; *C1(*)CC(O)C1]

In some variations, the embodiments provided herein also apply to a compound of formula (I') or (II), or a stereoisomer or tautomer thereof, or a pharmaceutically acceptable salt of any of the foregoing, or any variation or embodiment thereof.

In some embodiments of a compound of formula (I), (I-A), (I-A2), (I-B), or (I-B1), or a stereoisomer or tautomer thereof, or a pharmaceutically acceptable salt of any of the foregoing, $L^3$ is 3-10 membered heterocyclyl. In some embodiments, $L^3$ is 3-6 membered heterocyclyl. In some embodiments, $L^3$ is selected from the group consisting of

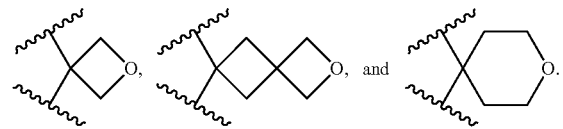 [SMILES: *C1(*)COC1 ; *C1(*)CC2(COC2)C1 ; *C1(*)CCOCC1]

In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (II), such as a compound of formula (I), (I-A), (I-A2), (I-B), or (I-B1), or a stereoisomer or tautomer thereof, or a pharmaceutically acceptable salt of any of the foregoing, $L^3$ is 3-10 membered heterocyclyl. In some embodiments, $L^3$ is 3-6 membered heterocyclyl. In some embodiments, $L^3$ is selected from the group consisting of

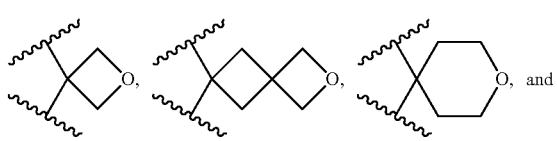

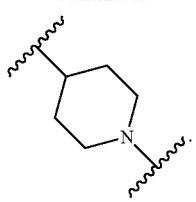

In some embodiments of a compound of formula (I), (I-A), (I-A2), (I-B), or (I-B1), or a stereoisomer or tautomer thereof, or a pharmaceutically acceptable salt of any of the foregoing, $R^4$ is —S(O)$_2$—$R^a$, wherein $R^a$ is $C_{1-6}$alkyl. In some embodiments, $R^4$ is —S(O)$_2$—$R^a$, wherein $R^a$ is $C_{1-6}$alkyl, wherein the $C_{1-6}$alkyl of $R^a$ is optionally substituted with one or more halo, —OH, —S(O)$_2$—$C_{1-6}$alkyl, or —N($C_{1-6}$alkyl)-C(O)—$C_{1-6}$alkyl. In some embodiments, $R^4$ is —S(O)$_2$—$R^a$, wherein $R^a$ is $C_{1-3}$alkyl, wherein the $C_{1-3}$alkyl of $R^a$ is optionally substituted with one or more halo, —OH, —S(O)$_2$—$C_{1-3}$alkyl, or —N($C_{1-3}$alkyl)-C(O)—$C_{1-3}$alkyl. In some embodiments, $R^4$ is selected from the group consisting of

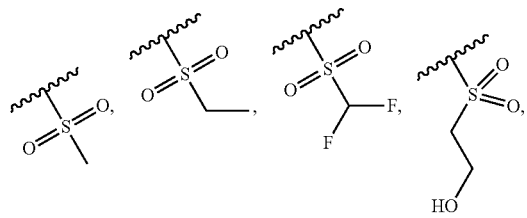

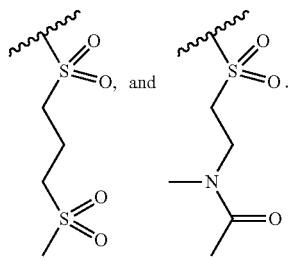

In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (II), such as a compound of formula (I), (I-A), (I-A2), (I-B), or (I-B1), or a stereoisomer or tautomer thereof, or a pharmaceutically acceptable salt of any of the foregoing, $R^4$ is selected from the group consisting of

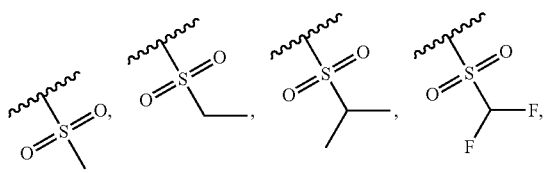

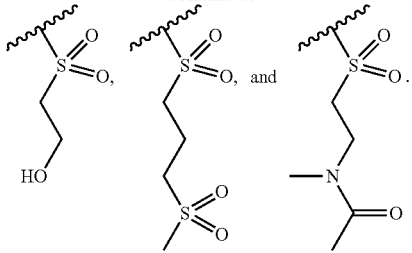

In some embodiments of a compound of formula (I), (I-A), (I-A2), (I-B), or (I-B1), or a stereoisomer or tautomer thereof, or a pharmaceutically acceptable salt of any of the foregoing, $R^4$ is —S(O)$_2$—$R^a$, wherein $R^a$ is $C_{3-10}$cycloalkyl. $R^4$ is —S(O)$_2$—$R^a$, wherein $R^a$ is $C_{3-10}$cycloalkyl, wherein the $C_{3-10}$cycloalkyl of $R^a$ is optionally substituted with one or more —OH, C(O)$_2$—$C_{1-6}$alkyl, —C(O)—NH($C_{1-6}$alkyl), —C(O)—N($C_{1-6}$alkyl)$_2$, —C(O)—$C_{3-10}$heterocyclyl or $C_{1-6}$alkyl, wherein the $C_{1-6}$alkyl is optionally substituted with one or more —OH. In some embodiments, $R^4$ is —S(O)$_2$—$R^a$, wherein $R^a$ is $C_{3-6}$cycloalkyl, wherein the $C_{3-6}$cycloalkyl of $R^a$ is optionally substituted with one or more —OH, C(O)$_2$—$C_{1-6}$alkyl, —C(O)—NH($C_{1-6}$alkyl), —C(O)—N($C_{1-6}$alkyl)$_2$, —C(O)—$C_{3-10}$heterocyclyl, or $C_{1-6}$alkyl, wherein the $C_{1-6}$alkyl is optionally substituted with one or more —OH. In some embodiments, $R^4$ is —S(O)$_2$—$R^a$, wherein $R^a$ is $C_{3-6}$cycloalkyl, wherein the $C_{3-6}$cycloalkyl of $R^a$ is optionally substituted with one or more —OH, C(O)$_2$—$C_{1-3}$alkyl, —C(O)—NH($C_{1-3}$alkyl), —C(O)—N($C_{1-3}$alkyl)$_2$, —C(O)—$C_{3-6}$heterocyclyl, or $C_{1-3}$alkyl, wherein the $C_{1-3}$alkyl is optionally substituted with one or more —OH. In some embodiments, $R^4$ is selected from the group consisting of

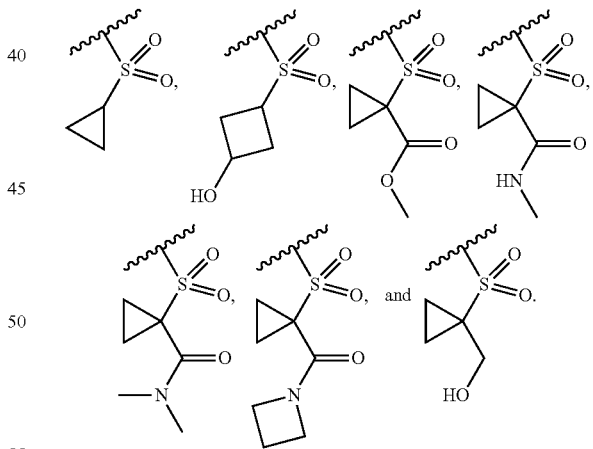

In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), (I-A), (I-A2), (I-B), or (I-B1), or a stereoisomer or tautomer thereof, or a pharmaceutically acceptable salt of any of the foregoing, $R^4$ is —S(O)$_2$—$R^a$, wherein $R^a$ is 3-10 membered heterocyclyl. In some embodiments $R^4$ is —S(O)$_2$—$R^a$, wherein $R^a$ is 3-10 membered heterocyclyl, wherein the 3-10 membered heterocyclyl of $R^a$ is optionally substituted with one or more $C_{1-6}$alkyl. In some embodiments, $R^4$ is —$S(O)_2$—$R^a$, wherein $R^a$ is 3-6 membered heterocyclyl, wherein the 3-6 membered heterocyclyl of $R^a$ is optionally substituted with one or more $C_{1-6}$alkyl. In some embodiments, wherein $R^4$ is —$S(O)_2$—$R^a$, wherein $R^a$ is 3-6 membered heterocyclyl, wherein the 3-6 membered heterocyclyl of $R^a$ is optionally substituted with one or more $C_{1-3}$alkyl. In some embodiments, $R^4$ is

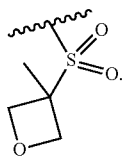

In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), (I-A), (I-A2), (I-B), or (I-B1) or a stereoisomer or tautomer thereof, or a pharmaceutically acceptable salt of any of the foregoing, $R^4$ is 5-20 membered heteroaryl. In some embodiments, $R^4$ is 5-20 membered heteroaryl optionally substituted with one or more $C_{1-6}$alkyl. In some embodiments, $R^4$ is 5-6 membered heteroaryl optionally substituted with one or more $C_{1-6}$alkyl. In some embodiments, $R^4$ is 5-6 membered heteroaryl optionally substituted with one or more $C_{1-3}$alkyl. In some embodiments, $R^4$ is 5-6 membered heteroaryl optionally substituted with one or more methyl. In some embodiments, $R^4$ is selected from the group consisting of

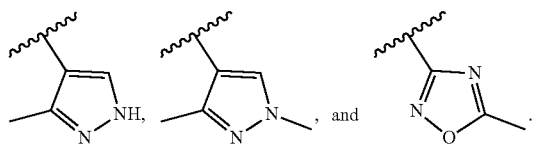

In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), (I-A), (I-A2), (I-B), or (I-B1), or a stereoisomer or tautomer thereof, or a pharmaceutically acceptable salt of any of the foregoing, $R^4$ is —$N(R^d)_2$, wherein each of $R^d$ is independently H, or $C_{1-6}$ alkyl, wherein the $C_{1-6}$alkyl of $R^d$ is optionally substituted with one or more —OH or —$S(O)_2$—$R^a$, wherein $R^a$ is $C_{1-6}$alkyl. In some embodiments, $R^4$ is —$N(R^d)_2$, wherein each of $R^d$ is independently H, or $C_{1-3}$ alkyl, wherein the $C_{1-3}$alkyl of $R^d$ is optionally substituted with one or more —OH, or —$S(O)_2$—$R^a$, wherein $R^a$ is $C_{1-3}$alkyl. In some embodiments, $R^4$ is —$N(R^d)_2$, wherein each of $R^d$ is independently H, or $C_{1-3}$alkyl, wherein the $C_{1-3}$alkyl of $R^d$ is optionally substituted with one or more —OH or —$S(O)_2$—$R^a$, wherein $R^a$ is methyl. In some embodiments, $R^4$ is selected from the group consisting of —$NH_2$,

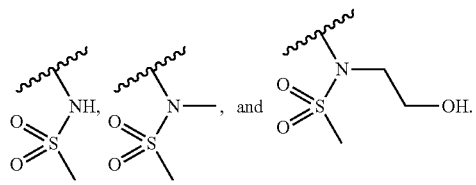

In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), (I-A), (I-A2), (I-B), or (I-B1), or a stereoisomer or tautomer thereof, or a pharmaceutically acceptable salt of any of the foregoing, $R^4$ is —$C(O)$—$N(R^e)_2$, wherein each of $R^e$ is independently H or $C_{1-6}$ alkyl. In some embodiments, $R^4$ is —$C(O)$—$N(R^e)_2$, wherein each of $R^e$ is independently H or $C_{1-3}$ alkyl. In some embodiments, $R^4$ is —$C(O)$—$N(R^e)_2$, wherein each of $R^e$ is independently H or methyl. In some embodiments, $R^4$ is —$C(O)$—$NH_2$. In some embodiments, $R^4$ is —$C(O)$—$NH(CH_3)$. In some embodiments, $R^4$ is —$C(O)$—$N(CH_3)_2$. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), (I-A), (I-A2), (I-B), or (I-B1), or a stereoisomer or tautomer thereof, or a pharmaceutically acceptable salt of any of the foregoing, $R^4$ is —$C(O)$—$N(R^e)_2$, wherein both $R^e$ together with the N to which they are attached are taken together to form a 3-10 membered heterocyclyl. In some embodiments $R^4$ is —$C(O)$—$N(R^e)_2$, wherein both $R^e$ together with the N to which they are attached are taken together to form a 3-10 membered heterocyclyl, wherein the 3-10 membered heterocyclyl is optionally substituted with one or more halo, oxo, —OH, $NH_2$, NH—$S(O)_2$—$R^a$, or —$S(O)_2$—$R^a$, wherein $R^a$ is $C_{1-6}$alkyl. In some embodiments $R^4$ is —$C(O)$—$N(R^e)_2$, wherein both $R^e$ together with the N to which they are attached are taken together to form a 3-7 membered heterocyclyl, wherein the 3-7 membered heterocyclyl is optionally substituted with one or more halo, oxo, —OH, $NH_2$, NH—$S(O)_2$—$R^a$, or —$S(O)_2$—$R^a$, wherein $R^a$ is $C_{1-3}$alkyl. In some embodiments $R^4$ is —$C(O)$—$N(R^e)_2$, wherein both $R^e$ together with the N to which they are attached are taken together to form a 3-7 membered heterocyclyl, wherein the 3-7 membered heterocyclyl is optionally substituted with one or more halo, oxo, —OH, $NH_2$, NH—$S(O)_2$—$R^a$, or —$S(O)_2$—$R^a$, wherein $R^a$ is methyl. In some embodiments, $R^4$ is selected from the group consisting of

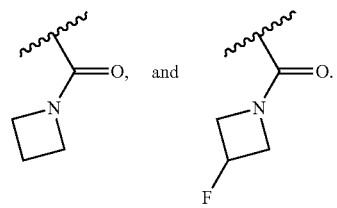 [SMILES: *C(=O)N1CCC1 ; *C(=O)N1CC(F)C1]

In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), (I-A), (I-A2), (I-B), or (I-B1), or a stereoisomer or tautomer thereof, or a pharmaceutically acceptable salt of any of the foregoing, $R^4$ is 3-10 membered heterocyclyl optionally substituted with one or more oxo. In some embodiments, $R^4$ is 3-7 membered heterocyclyl optionally substituted with one or more oxo. In some embodiments, $R^4$ is selected from the group consisting of

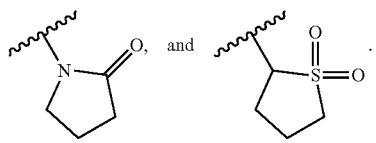 [SMILES: *N1CCCC1=O ; *C1CCCS1(=O)=O]

In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), (I-A), (I-A2), (I-B), or (I-B1), or a stereoisomer or tautomer thereof, or a pharmaceutically acceptable salt of any of the foregoing, $R^4$ is —NS(O)—$(C_{1-6}alkyl)_2$. In some embodiments, $R^4$ is —NS(O)—$(C_{1-3}alkyl)_2$. In some embodiments, wherein $R^4$ is

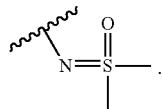 [SMILES: *N=S(C)(C)=O]

In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), (I-A), (I-A2), (I-B), or (I-B1), or a stereoisomer or tautomer thereof, or a pharmaceutically acceptable salt of any of the foregoing, $R^4$ is —S(O)—N$(C_{1-6}alkyl)$-$(C_{1-6}alkyl)$. In some embodiments, $R^4$ is —S(O)—N$(C_{1-3}alkyl)$-$(C_{1-3}alkyl)$. In some embodiments, $R^4$ is

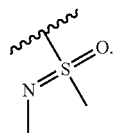 [SMILES: *S(C)(=O)=NC]

In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), (I-A), (I-A2), (I-B), or (I-B1), or a stereoisomer or tautomer thereof, or a pharmaceutically acceptable salt of any of the foregoing, $R^4$ is —CN. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), or a stereoisomer or tautomer thereof, or a pharmaceutically acceptable salt of any of the foregoing, $R^4$ is —P(O)$(C_{1-6}alkyl)_2$. In some embodiments, $R^4$ is —P(O)$(C_{1-3}alkyl)_2$. In some embodiments, $R^4$ is —P(O)$(CH_3)_2$. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments, provided herein is a compound of formula (I), (I-A), (I-A2), or (I-B), or a stereoisomer or tautomer thereof, or a pharmaceutically acceptable salt thereof, wherein the compound is a compound of formula (I-B2):

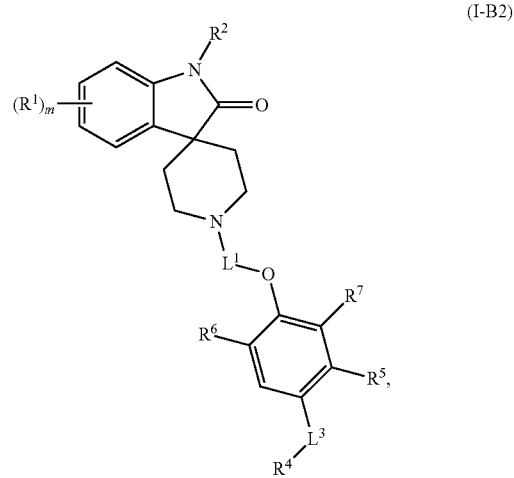

or a stereoisomer or tautomer thereof, or a pharmaceutically acceptable salt of any of the foregoing, wherein: $R^5$ is halo, —CN, 3-10 membered heterocyclyl, $C_{1-6}$alkyl, or $C_{1-6}$alkoxy, wherein the $C_{1-6}$alkyl of $R^5$ is optionally substituted with one or more halo, or —OH and wherein the $C_{1-6}$alkoxy is optionally substituted with one or more halo; and m, $R^1$, $R^2$, $L^1$, $L^3$, $R^4$, $R^6$, and $R^7$ are as defined for formula (I). In some variations, m, $R^1$, $R^2$, $L^1$, $L^3$, $R^4$, $R^6$, and $R^7$ of formula (I-B2) are as defined for a compound of formula (I'), or (II), or a stereoisomer or tautomer thereof, or a pharmaceutically acceptable salt of any of the foregoing, or any variation or embodiment thereof.

In some embodiments of a compound of formula (I), (I-A), (I-A2), (I-B), or (I-B2), or a stereoisomer or tautomer thereof, or a pharmaceutically acceptable salt of any of the foregoing, $R^2$ is H. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), (I-A), (I-A2), (I-B), or (I-B2), or a stereoisomer or tautomer thereof, or a pharmaceutically acceptable salt of any of the foregoing, $R^2$ is $C_{1-6}$alkyl, wherein the $C_{1-6}$alkyl of $R^2$ is optionally substituted with one or more halo, —OH. In some embodiments, $R^2$ is $C_{1-3}$alkyl, wherein the $C_{1-3}$alkyl of $R^2$ is optionally substituted with one or more halo, —OH. In some embodiments, $R^2$ is methyl. In some embodiments, $R^2$ is ethyl, wherein the ethyl of $R^2$ is optionally substituted with one or more halo, —OH. In some embodiments, $R^2$ is

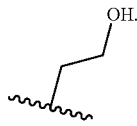

In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (II), such as a compound of formula (I), (I-A), (I-A2), (I-B), or (I-B2), or a stereoisomer or tautomer thereof, or a pharmaceutically acceptable salt of any of the foregoing, $R^2$ is $C_{1-6}$alkyl, wherein the $C_{1-6}$alkyl of $R^2$ is optionally substituted with one or more deuterium. In some embodiments, $R^2$ is $C_{1-3}$alkyl, wherein the $C_{1-3}$alkyl of $R^2$ is optionally substituted with one or more deuterium. In some embodiments, $R^2$ is methyl, wherein the methyl of $R^2$ is optionally substituted with one of more deuterium. In some embodiments, $R^2$ is

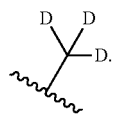

In some embodiments of a compound of formula (I), (I-A), (I-A2), (I-B), or (I-B2), or a stereoisomer or tautomer thereof, or a pharmaceutically acceptable salt of any of the foregoing, m is 1. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), (I-A), (I-A2), (I-B), or (I-B2), or a stereoisomer or tautomer thereof, or a pharmaceutically acceptable salt of any of the foregoing, $R^1$ is halo. In some embodiments $R^1$ is Cl. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), (I-A), (I-A2), (I-B), or (I-B2), or a stereoisomer or tautomer thereof, or a pharmaceutically acceptable salt of any of the foregoing, $R^1$ is —CN. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), (I-A), (I-A2), (I-B), or (I-B2), or a stereoisomer or tautomer thereof, or a pharmaceutically acceptable salt of any of the foregoing, $L^1$ is $C_{1-6}$alkylene optionally substituted with one or more $C_{1-6}$alkyl, wherein the $C_{1-6}$alkyl is optionally substituted with —OH or $C_{1-6}$alkoxy. In some embodiments, $L^1$ is methylene. In some embodiments, $L^1$ is ethylene optionally substituted with one or more $C_{1-6}$alkyl, wherein the $C_{1-6}$alkyl is optionally substituted with one or more —OH or $C_{1-6}$alkoxy. In some embodiments, $L^1$ is selected from the group consisting of

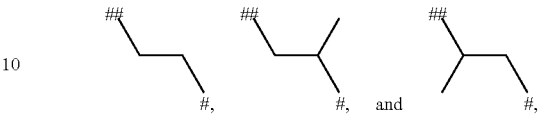

wherein, for each $L^1$, # denotes the point of attachment to —O— and ## denotes the point of attachment to the remainder of the molecule. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), (I-A), (I-A2), (I-B), or (I-B2), or a stereoisomer or tautomer thereof, or a pharmaceutically acceptable salt of any of the foregoing, $L^3$ is absent. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), (I-A), (I-A2), (I-B), or (I-B2), or a stereoisomer or tautomer thereof, or a pharmaceutically acceptable salt of any of the foregoing, $L^3$ is 3-10 membered heterocyclyl. In some embodiments, $L^3$ is 3-6 membered heterocyclyl. In some embodiments, $L^3$ is

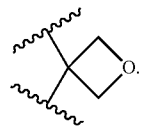 [SMILES: *C1(*)COC1]

In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), (I-A), (I-A2), (I-B), or (I-B2), or a stereoisomer or tautomer thereof, or a pharmaceutically acceptable salt of any of the foregoing, $R^4$ is —S(O)$_2$—$R^a$, wherein $R^a$ is $C_{1-6}$alkyl. In some embodiments, $R^4$ is —S(O)$_2$—$R^a$, wherein $R^a$ is $C_{1-6}$alkyl. In some embodiments, $R^4$ is —S(O)$_2$—$R^a$, wherein $R^a$ is $C_{1-3}$alkyl. In some embodiments, $R^4$ is

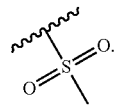

In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (II) such as a compound of formula (I), (I-A), (I-A2), (I-B), or (I-B2), or a stereoisomer or tautomer thereof, or a pharmaceutically acceptable salt of any of the foregoing, R⁴ is —NS(O)—(C₁₋₆alkyl)₂. In some embodiments, R⁴ is —NS(O)—(C₁₋₆alkyl)₂. In some embodiments, R⁴ is —NS(O)—(C₁₋₃alkyl)₂. In some embodiments, R⁴ is

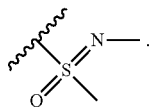

In some embodiments of a compound of formula (I), (I-A), (I-A2), (I-B), or (I-B2), or a stereoisomer or tautomer thereof, or a pharmaceutically acceptable salt of any of the foregoing, R⁴ is —N(Rᵈ)₂, wherein each of Rᵈ is independently H, C₁₋₆ alkyl, or —S(O)₂—Rᵃ, wherein Rᵃ is C₁₋₆alkyl. In some embodiments, R⁴ is —N(Rᵈ)₂, wherein each of Rᵈ is independently H, C₁₋₃ alkyl, or —S(O)₂—Rᵃ, wherein Rᵃ is C₁₋₃alkyl. In some embodiments, R⁴ is —N(Rᵈ)₂, wherein each of Rᵈ is independently H, C₁₋₆ alkyl, or —S(O)₂—Rᵃ, wherein Rᵃ is methyl. In some embodiments, R⁴ is selected from the group consisting of —NH₂, and

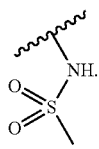

In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), (I-A), (I-A2), (I-B), or (I-B2), or a stereoisomer or tautomer thereof, or a pharmaceutically acceptable salt of any of the foregoing, R⁴ is —C(O)—N(Rᵉ)₂, wherein each of Rᵉ is independently H or C₁₋₆ alkyl. In some embodiments, R⁴ is —C(O)—N(Rᵉ)₂, wherein each of Rᵉ is independently H or C₁₋₃ alkyl. In some embodiments, R⁴ is —C(O)—N(Rᵉ)₂, wherein each of Rᵉ is independently H or methyl. In some embodiments, R⁴ is —C(O)—NH₂. In some embodiments, R⁴ is —C(O)—NH(CH₃). In some embodiments, R⁴ is —C(O)—N(CH₃)₂. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), (I-A), (I-A2), (I-B), or (I-B2), or a stereoisomer or tautomer thereof, or a pharmaceutically acceptable salt of any of the foregoing, R⁴ is —C(O)—N(Rᵉ)₂, wherein each of Rᵉ is independently H or 3-10 membered heterocycle, wherein the 3-10 membered heterocycle is optionally substituted with one or more oxo. In some embodiments, R⁴ is —C(O)—N(Rᵉ)₂, wherein each of Rᵉ is independently H or 3-6 membered heterocycle, wherein the 3-6 membered heterocycle is optionally substituted with one or more oxo. In some embodiments, R⁴ is selected from the group consisting of

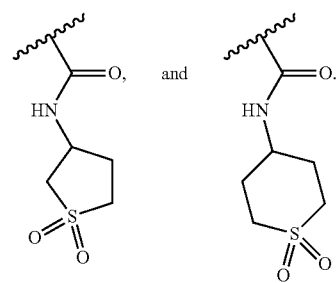 [SMILES: *C(=O)NC1CCS(=O)(=O)C1 ; *C(=O)NC1CCS(=O)(=O)CC1]

In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), (I-A), (I-A2), (I-B), or (I-B2), or a stereoisomer or tautomer thereof, or a pharmaceutically acceptable salt of any of the foregoing, R⁴ is —C(O)—N(Rᵉ)₂, wherein both Rᵉ together with the N to which they are attached are taken together to form a 3-10 membered heterocyclyl. In some embodiments R⁴ is —C(O)—N(Rᵉ)₂, wherein both Rᵉ together with the N to which they are attached are taken together to form a 3-10 membered heterocyclyl, wherein the 3-10 membered heterocyclyl is optionally substituted with one or more oxo, —OH, NH₂, or —S(O)₂—Rᵃ, wherein Rᵃ is C₁₋₆alkyl. In some embodiments R⁴ is —C(O)—N(Rᵉ)₂, wherein both Rᵉ together with the N to which they are attached are taken together to form a 3-7 membered heterocyclyl, wherein the 3-7 membered heterocyclyl is optionally substituted with one or more halo, oxo, —OH, NH₂, NH—S(O)₂—Rᵃ, or —S(O)₂—Rᵃ, wherein Rᵃ is C₁₋₃alkyl. In some embodiments R⁴ is —C(O)—N(Rᵉ)₂, wherein both Rᵉ together with the N to which they are attached are taken together to form a 3-7 membered heterocyclyl, wherein the 3-7 membered heterocyclyl is optionally substituted with one or more halo, oxo, —OH, NH₂, NH—S(O)₂—Rᵃ, or —S(O)₂—Rᵃ, wherein Rᵃ is methyl. In some embodiments, R⁴ is selected from the group consisting of

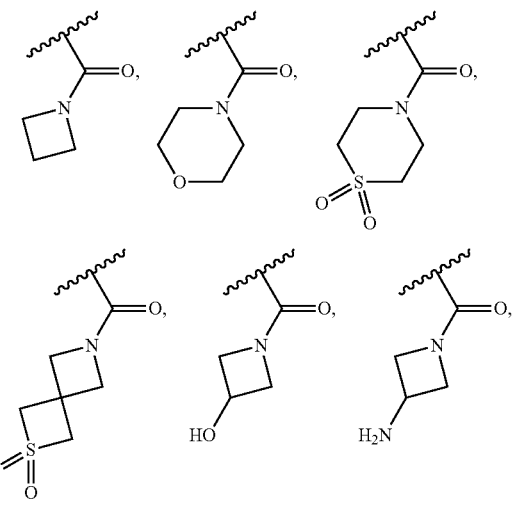

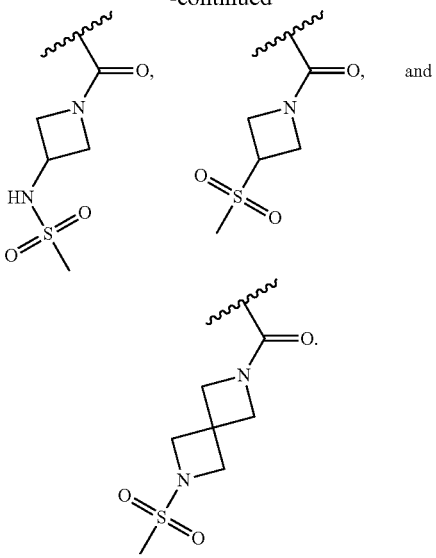

In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), (I-A), (I-A2), (I-B), or (I-B2), or a stereoisomer or tautomer thereof, or a pharmaceutically acceptable salt of any of the foregoing, $R^5$ is halo. In some embodiments, $R^5$ is Cl, or F. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), (I-A), (I-A2), (I-B), or (I-B2), or a stereoisomer or tautomer thereof, or a pharmaceutically acceptable salt of any of the foregoing, $R^5$ is —CN. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), (I-A), (I-A2), (I-B), or (I-B2), or a stereoisomer or tautomer thereof, or a pharmaceutically acceptable salt of any of the foregoing, $R^5$ is $C_{1-6}$alkyl, wherein the $C_{1-6}$alkyl of $R^5$ is optionally substituted with one or more halo, or —OH. In some embodiments, $R^5$ is $C_{1-3}$alkyl, wherein the $C_{1-3}$alkyl of $R^5$ is optionally substituted with one or more halo, or —OH. In some embodiments, $R^5$ is $C_{1-3}$alkyl, wherein the $C_{1-3}$alkyl of $R^5$ is optionally substituted with one or more fluoro, or —OH. In some embodiments, $R^5$ is selected from the group consisting of methyl

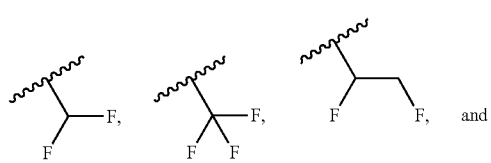

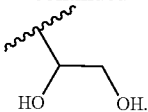

In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), (I-A), (I-A2), (I-B), or (I-B2), or a stereoisomer or tautomer thereof, or a pharmaceutically acceptable salt of any of the foregoing, $R^5$ is 3-10 membered heterocyclyl. In some embodiments, $R^5$ is 3-6 membered heterocyclyl. In some embodiments, $R^5$ is

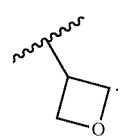 [SMILES: *C1COC1]

In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), (I-A), (I-A2), (I-B), or (I-B2), or a stereoisomer or tautomer thereof, or a pharmaceutically acceptable salt of any of the foregoing, $R^5$ is $C_{1-6}$alkoxy, wherein the $C_{1-6}$alkoxy is optionally substituted with one or more halo. In some embodiments $R^5$ is $C_{1-3}$alkoxy, wherein the $C_{1-3}$alkoxy is optionally substituted with one or more halo. In some embodiments, $R^5$ is $C_{1-3}$alkoxy, wherein the $C_{1-3}$alkoxy is optionally substituted with one or more fluoro. In some embodiments, $R^5$ is

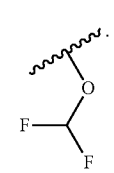

In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), (I-A), (I-A2), (I-B), or (I-B2), or a stereoisomer or tautomer thereof, or a pharmaceutically acceptable salt of any of the foregoing, $R^6$ and $R^7$ are each independently H or halo. In some embodiments, $R^6$ and $R^7$ are each independently H or fluoro. In some embodiments, each of $R^6$ and $R^7$ is H. In some embodiments, one of $R^6$ and $R^7$ is H and the other of $R^6$ and $R^7$ is fluoro. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments, provided herein is a compound of formula (I), (I-A), (I-A2), or (I-B), or a stereoisomer or tautomer thereof, or a pharmaceutically acceptable salt thereof, wherein the compound is a compound of formula (I-B3):

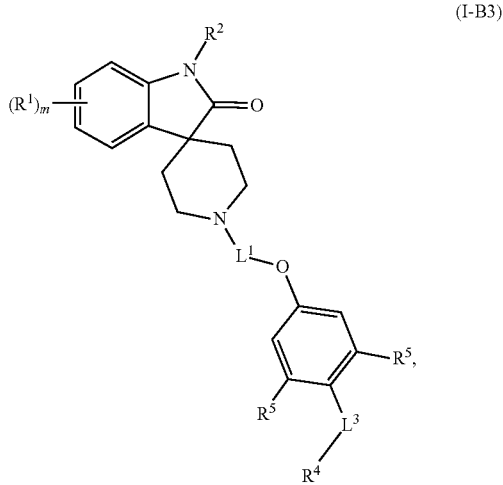
(I-B3)

or a stereoisomer or tautomer thereof, or a pharmaceutically acceptable salt of any of the foregoing, wherein: each $R^5$ is, independently at each occurrence, halo, —CN, 3-10 membered heterocyclyl, $C_{1-6}$alkyl, or $C_{1-6}$alkoxy, wherein the $C_{1-6}$alkyl of $R^5$ is optionally substituted with one or more halo, or —OH and wherein the $C_{1-6}$alkoxy is optionally substituted with one or more halo; and m, $R^1$, $R^2$, $L^1$, $L^3$, $R^4$, $R^6$, and $R^7$ are as defined for formula (I). In some variations, m, $R^1$, $R^2$, $L^1$, $L^3$, $R^4$, $R^6$, and $R^7$ of formula (I-B3) are as defined for a compound of formula (I'), or (II), or a stereoisomer or tautomer thereof, or a pharmaceutically acceptable salt of any of the foregoing, or any variation or embodiment thereof.

In some embodiments of a compound of formula (I), (I-A), (I-A2), (I-B), or (I-B3), or a stereoisomer or tautomer thereof, or a pharmaceutically acceptable salt of any of the foregoing, $R^2$ is H. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), (I-A), (I-A2), (I-B), or (I-B3), or a stereoisomer or tautomer thereof, or a pharmaceutically acceptable salt of any of the foregoing, $R^2$ is $C_{1-6}$alkyl. In some embodiments, $R^2$ is methyl. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), (I-A), (I-A2), (I-B), or (I-B3), or a stereoisomer or tautomer thereof, or a pharmaceutically acceptable salt of any of the foregoing, m is an integer from 0 to 4. In some embodiments, m is 0 or 1. In some embodiments, m is 0. In some embodiments m is 1. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), (I-A), (I-A2), (I-B), or (I-B3), or a stereoisomer or tautomer thereof, or a pharmaceutically acceptable salt of any of the foregoing, $R^1$ is halo. In some embodiments $R^1$ is Cl. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), (I-A), (I-A2), (I-B), or (I-B3), or a stereoisomer or tautomer thereof, or a pharmaceutically acceptable salt of any of the foregoing, $R^1$ is —CN. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), (I-A), (I-A2), (I-B), or (I-B3), or a stereoisomer or tautomer thereof, or a pharmaceutically acceptable salt of any of the foregoing, $L^1$ is $C_{1-6}$alkylene optionally substituted with one or more $C_{1-6}$alkyl, wherein the $C_{1-6}$alkyl is optionally substituted with —OH or $C_{1-6}$alkoxy. In some embodiments, $L^1$ is methylene. In some embodiments, $L^1$ is ethylene optionally substituted with one or more $C_{1-6}$alkyl, wherein the $C_{1-6}$alkyl is optionally substituted with one or more —OH or $C_{1-6}$alkoxy. In some embodiments, $L^1$ is selected from the group consisting of

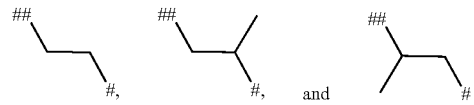

wherein, for each $L^1$, # denotes the point of attachment to —O— and ## denotes the point of attachment to the remainder of the molecule. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), (I-A), (I-A2), (I-B), or (I-B3), or a stereoisomer or tautomer thereof, or a pharmaceutically acceptable salt of any of the foregoing, $L^3$ is absent. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), (I-A), (I-A2), (I-B), or (I-B3), or a stereoisomer or tautomer thereof, or a pharmaceutically acceptable salt of any of the foregoing, $L^3$ is $C_{1-6}$alkylene. In some embodiments, $L^3$ is $C_{1-3}$alkylene. In some embodiments, $L^3$ is

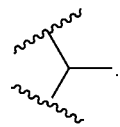

In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), (I-A), (I-A2), (I-B), or (I-B3), or a stereoisomer or tautomer thereof, or a pharmaceutically acceptable salt of any of the foregoing, $L^3$ is 3-10 membered heterocyclyl. In some embodiments, $L^3$ is 3-6 membered heterocyclyl. In some embodiments, $L^3$ is

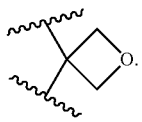

In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), (I-A), (I-A2), (I-B), or (I-B3), or a stereoisomer or tautomer thereof, or a pharmaceutically acceptable salt of any of the foregoing, $R^4$ is —S(O)$_2$—R$^a$, wherein R$^a$ is C$_{1-6}$alkyl. In some embodiments, $R^4$ is —S(O)$_2$—R$^a$, wherein R$^a$ is C$_{1-6}$alkyl. In some embodiments, $R^4$ is —S(O)$_2$—R$^a$, wherein R$^a$ is C$_{1-3}$alkyl. In some embodiments, $R^4$ is

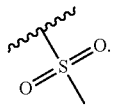

In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), (I-A), (I-A2), (I-B), or (I-B3), or a stereoisomer or tautomer thereof, or a pharmaceutically acceptable salt of any of the foregoing, $R^4$ is —N(R$^d$)$_2$, wherein each of R$^d$ is independently C$_{1-6}$ alkyl, or —S(O)$_2$—R$^a$, and wherein R$^a$ is C$_{1-6}$alkyl. In some embodiments, $R^4$ is —N(R$^d$)$_2$, wherein each of R$^d$ is independently C$_{1-3}$ alkyl, or —S(O)$_2$—R$^a$, wherein R$^a$ is C$_{1-3}$alkyl. In some embodiments, $R^4$ is —N(R$^d$)$_2$, wherein each of R$^d$ is methyl, or —S(O)$_2$—R$^a$, wherein R$^a$ is methyl. In some embodiments, $R^4$ is

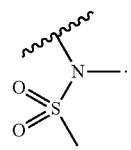 [SMILES: *N(C)S(C)(=O)=O]

In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), (I-A), (I-A2), (I-B), or (I-B3), or a stereoisomer or tautomer thereof, or a pharmaceutically acceptable salt of any of the foregoing, $R^4$ is —C(O)—N(R$^e$)$_2$, wherein both R$^e$ together with the N to which they are attached are taken together to form a 3-10 membered heterocyclyl, wherein the 3-10 membered heterocyclyl is optionally substituted with one or more oxo. In some embodiments $R^4$ is —C(O)—N(R$^e$)$_2$, wherein both R$^e$ together with the N to which they are attached are taken together to form a 3-7 membered heterocyclyl, wherein the 3-7 membered heterocyclyl is optionally substituted with one or more oxo. In some embodiments, $R^4$ is

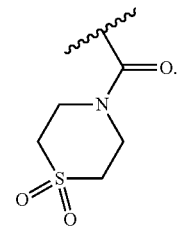 [SMILES: *C(=O)N1CCS(=O)(=O)CC1]

In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), (I-A), (I-A2), (I-B), or (I-B3), or a stereoisomer or tautomer thereof, or a pharmaceutically acceptable salt of any of the foregoing, $R^5$ is, independently at each occurrence selected from the group consisting of, halo and C$_{1-6}$alkyl. In some embodiments, $R^5$ is, independently at each occurrence selected from the group consisting of halo and C$_{1-3}$alkyl. In some embodiments, $R^5$ is, independently at each occurrence, selected from the group consisting of F and methyl. In some embodiments, each $R^5$ is F. In some embodiments, each $R^5$ is methyl. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments, provided herein is a compound of formula (I), (I-A), or (I-A2), or a stereoisomer or tautomer thereof, or a pharmaceutically acceptable salt thereof, wherein the compound is a compound of formula (I-C):

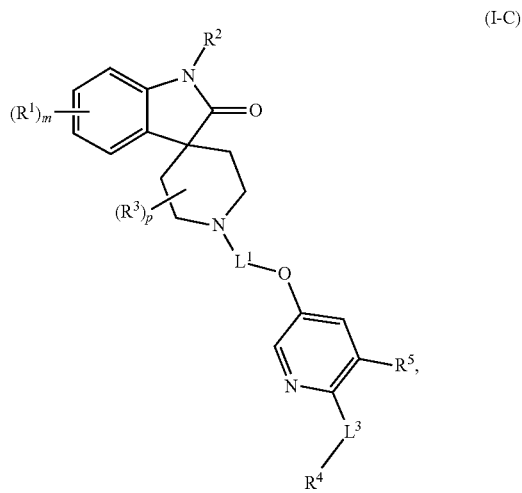

(I-C)

or a stereoisomer or tautomer thereof, or a pharmaceutically acceptable salt of any of the foregoing, wherein: m, p, $R^1$, $R^2$, $R^3$, $L^1$, $L^3$, $R^4$, and $R^5$ are as defined for formula (I). In some variations m, p, $R^1$, $R^2$, $R^3$, $L^1$, $L^3$, $R^4$, and $R^5$ of formula (I-C) are as defined for a compound of formula (I'), or (II), or a stereoisomer or tautomer thereof, or a pharmaceutically acceptable salt of any of the foregoing, or any variation or embodiment thereof.

In some embodiments, provided herein is a compound of formula (I), (I-A), (I-A2), or (I-C), or a stereoisomer or tautomer thereof, or a pharmaceutically acceptable salt thereof, wherein the compound is a compound of formula (I-C1):

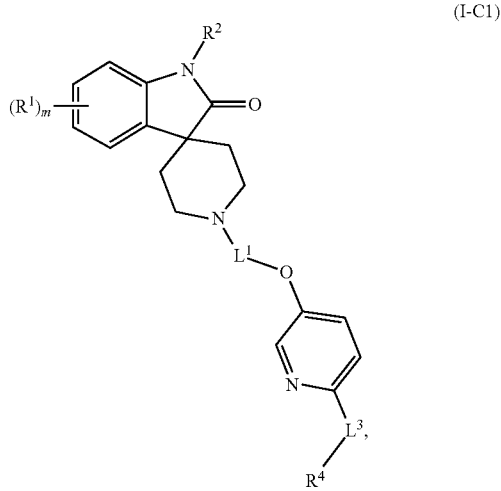

(I-C1)

or a stereoisomer or tautomer thereof, or a pharmaceutically acceptable salt of any of the foregoing, wherein: m, $R^1$, $R^2$, $R^3$, $L^1$, $L^3$, and $R^4$, are as defined for formula (I). In some variations m, $R^1$, $R^2$, $R^3$, $L^1$, $L^3$, and $R^4$ of formula (I-C) are as defined for a compound of formula (I'), or (II), or a stereoisomer or tautomer thereof, or a pharmaceutically acceptable salt of any of the foregoing, or any variation or embodiment thereof.

In some embodiments of a compound of formula (I), (I-A), (I-A2), (I-C), or (I-C1), or a stereoisomer or tautomer thereof, or a pharmaceutically acceptable salt of any of the foregoing, $R^2$ is H. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), (I-A), (I-A2), (I-C), or (I-C1), or a stereoisomer or tautomer thereof, or a pharmaceutically acceptable salt of any of the foregoing, m is an integer from 0 to 4. In some embodiments, m is an integer from 0 to 2. In some embodiments m is 1. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), (I-A), (I-A2), (I-C), or (I-C1), or a stereoisomer or tautomer thereof, or a pharmaceutically acceptable salt of any of the foregoing, $R^1$ is halo. In some embodiments $R^1$ is Cl. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), (I-A), (I-A2), (I-C), or (I-C1), or a stereoisomer or tautomer thereof, or a pharmaceutically acceptable salt of any of the foregoing, $R^1$ is —CN. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), (I-A), (I-A2), (I-C), or (I-C1), or a stereoisomer or tautomer thereof, or a pharmaceutically acceptable salt of any of the foregoing, $L^1$ is $C_{1-6}$alkylene. In some embodiments, $L^1$ is ethylene. In some embodiments, $L^1$ is wherein, # denotes the point of attachment to —O— and ## denotes the point of attachment to the remainder of the molecule. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), (I-A), (I-A2), (I-C), or (I-C1), or a stereoisomer or tautomer thereof, or a pharmaceutically acceptable salt of any of the foregoing, $L^3$ is absent. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), (I-A), (I-A2), (I-C), or (I-C1), or a stereoisomer or tautomer thereof, or a pharmaceutically acceptable salt of any of the foregoing, $L^3$ is $C_{1-6}$alkylene. In some embodiments, $L^3$ is $C_{1-3}$alkylene. In some embodiments, $L^3$ is In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), (I-A), (I-A2), (I-C), or (I-C1), or a stereoisomer or tautomer thereof, or a pharmaceutically acceptable salt of any of the foregoing, $R^4$ is —S(O)$_2$—$R^a$, wherein $R^a$ is $C_{1-6}$alkyl. In some embodiments, $R^4$ is —S(O)$_2$—$R^a$, wherein $R^a$ is $C_{1-3}$alkyl. In some embodiments, $R^4$ is

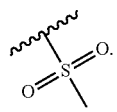

In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), (I-A), (I-A2), (I-C), or (I-C1), or a stereoisomer or tautomer thereof, or a pharmaceutically acceptable salt of any of the foregoing, $R^4$ is —S(O)$_2$—$R^a$, wherein $R^a$ is $C_{3-10}$cycloalkyl. $R^4$ is —S(O)$_2$—$R^a$, wherein $R^a$ is $C_{3-10}$cycloalkyl, wherein the $C_{3-10}$cycloalkyl of $R^a$ is optionally substituted with one or more $C_{1-6}$alkyl, and wherein the $C_{1-6}$alkyl is optionally substituted with one or more —OH. In some embodiments, $R^4$ is —S(O)$_2$—$R^a$, wherein $R^a$ is $C_{3-6}$cycloalkyl, wherein the $C_{3-6}$cycloalkyl of $R^a$ is optionally substituted with one or more $C_{1-6}$alkyl, and wherein the $C_{1-6}$alkyl is optionally substituted with one or more —OH. In some embodiments, $R^4$ is —S(O)$_2$—$R^a$, wherein $R^a$ is $C_{3-6}$cycloalkyl, wherein the $C_{3-6}$cycloalkyl of $R^a$ is optionally substituted with one or more $C_{1-3}$alkyl, wherein the $C_{1-3}$alkyl is optionally substituted with one or more —OH. In some embodiments, $R^4$ is

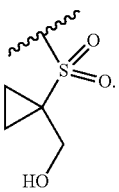 [SMILES: *S(=O)(=O)C1(CO)CC1]

In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), (I-A), (I-A2), (I-C), or (I-C1), or a stereoisomer or tautomer thereof, or a pharmaceutically acceptable salt of any of the foregoing, $R^4$ is —S(O)$_2$—$R^a$, wherein $R^a$ is 3-10 membered heterocyclyl. In some embodiments $R^4$ is —S(O)$_2$—$R^a$, wherein $R^a$ is 3-10 membered heterocyclyl, wherein the 3-10 membered heterocyclyl of $R^a$ is optionally substituted with one or more $C_{1-6}$alkyl. In some embodiments, $R^4$ is —S(O)$_2$—$R^a$, wherein $R^a$ is 3-6 membered heterocyclyl, wherein the 3-6 membered heterocyclyl of $R^a$ is optionally substituted with one or more $C_{1-6}$alkyl. In some embodiments, wherein $R^4$ is —S(O)$_2$—$R^a$, wherein $R^a$ is 3-6 membered heterocyclyl, wherein the 3-6 membered heterocyclyl of $R^a$ is optionally substituted with one or more $C_{1-3}$alkyl. In some embodiments, $R^4$ is

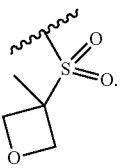 [SMILES: *S(=O)(=O)C1(C)COC1]

In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), (I-A), (I-A2), (I-C), or (I-C1), or a stereoisomer or tautomer thereof, or a pharmaceutically acceptable salt of any of the foregoing, $R^4$ is —C(O)—N($R^e$)$_2$, wherein each of $R^e$ is independently H or $C_{1-6}$ alkyl. In some embodiments, $R^4$ is —C(O)—N($R^e$)$_2$, wherein each of $R^e$ is independently H or $C_{1-3}$ alkyl. In some embodiments, $R^4$ is —C(O)—N($R^e$)$_2$, wherein each of $R^e$ is independently H or methyl. In some embodiments, $R^4$ is —C(O)—NH$_2$. In some embodiments, $R^4$ is —C(O)—N(CH$_3$)$_2$. In some embodiments, $R^4$ is —C(O)—NH$_2$. In some embodiments, $R^4$ is —C(O)—NH(CH$_3$). In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments, provided herein is a compound of formula (I), (I-A), or (I-A2), or a stereoisomer or tautomer thereof, or a pharmaceutically acceptable salt thereof, wherein the compound is a compound of formula (I-C2):

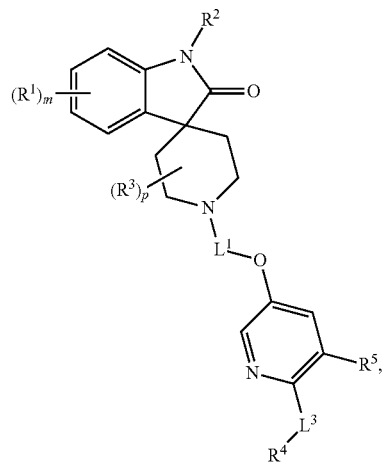

(I-C2)

or a stereoisomer or tautomer thereof, or a pharmaceutically acceptable salt of any of the foregoing, wherein: $R^5$ is, halo, —CN, 3-10 membered heterocyclyl, $C_{1-6}$alkyl, or $C_{1-6}$alkoxy, wherein the $C_{1-6}$alkyl of $R^5$ is optionally substituted with one or more halo, or —OH and wherein the $C_{1-6}$alkoxy is optionally substituted with one or more halo; m, p, $R^1$, $R^2$, $R^3$, $L^1$, $L^3$, and $R^4$, are as defined for formula (I). In some variations, $R^5$ is halo, —CN, 3-10 membered heterocyclyl, $C_{1-6}$alkyl, or $C_{1-6}$alkoxy, wherein the $C_{1-6}$alkyl of $R^5$ is optionally substituted with one or more halo, or —OH and wherein the $C_{1-6}$alkoxy of $R^5$ is optionally substituted with one or more halo; m, p, $R^1$, $R^2$, $R^3$, $L^1$, $L^3$, and $R^4$ of formula (I-C$_2$) are as defined for a compound of formula (I'), or (II), or a stereoisomer or tautomer thereof, or a pharmaceutically acceptable salt of any of the foregoing, or any variation or embodiment thereof.

In some embodiments of a compound of formula (I), (I-A), (I-A2), (I-C), or (I-C2), or a stereoisomer or tautomer thereof, or a pharmaceutically acceptable salt of any of the foregoing, $R^2$ is H. In some variations, the embodiments provided herein also apply to a compound of formula (I'). or (II), or a stereoisomer or tautomer thereof, or a pharmaceutically acceptable salt of any of the foregoing, or any variation or embodiment thereof.

In some embodiments of a compound of formula (I), (I-A), (I-A2), (I-C), or (I-C2), or a stereoisomer or tautomer thereof, or a pharmaceutically acceptable salt of any of the foregoing, m is an integer from 0 to 4. In some embodiments, m is an integer from 0 to 2. In some embodiments m is 1. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), (I-A), (I-A2), (I-C), or (I-C2), or a stereoisomer or tautomer thereof, or a pharmaceutically acceptable salt of any of the foregoing, $R^1$ is halo. In some embodiments $R^1$ is Cl. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), (I-A), (I-A2), (I-C), or (I-C2), or a stereoisomer or tautomer thereof, or a pharmaceutically acceptable salt of any of the foregoing, $R^1$ is —CN. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I'), (I-A), (I-A2), (I-C), or (I-C2), or a stereoisomer or tautomer thereof, or a pharmaceutically acceptable salt of any of the foregoing, $R^1$ is $C_{1-6}$alkyl, wherein the $C_{1-6}$alkyl of $R^1$ is optionally substituted with one or more halo. In some embodiments, $R^1$ is $C_{1-3}$alkyl, wherein the $C_{1-3}$alkyl of $R^1$ is optionally substituted with one or more halo. In some embodiments, $R^1$ is methyl, wherein the methyl of $R^1$ is optionally substituted with one or more F. In some embodiments. $R^1$ is

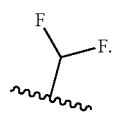

In some variations, the embodiments provided herein also apply to a compound of formula (II), or a stereoisomer or tautomer thereof, or a pharmaceutically acceptable salt of any of the foregoing, or any variation or embodiment thereof.

In some embodiments of a compound of formula (I), (I-A), (I-A2), (I-C), or (I-C2), or a stereoisomer or tautomer thereof, or a pharmaceutically acceptable salt of any of the foregoing, $L^1$ is $C_{1-6}$alkylene. In some embodiments, $L^1$ is ethylene. In some embodiments, $L^1$ is

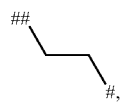

wherein, # denotes the point of attachment to —O— and ## denotes the point of attachment to the remainder of the molecule. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), (I-A), (I-A2), (I-C), or (I-C2), or a stereoisomer or tautomer thereof, or a pharmaceutically acceptable salt of any of the foregoing, $L^3$ is absent. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound formula (I'), (I-A), (I-A2), (I-C), or (I-C2), or a stereoisomer or tautomer thereof, or a pharmaceutically acceptable salt of any of the foregoing, $L^3$ is $C_{1-6}$alkylene, wherein the $C_{1-6}$alkylene of $L^3$ is optionally substituted with one or more —OH, or $C_{1-6}$alkyl. In some embodiments, $L^3$ is $C_{1-3}$alkylene, wherein the $C_{1-6}$alkylene of $L^3$ is optionally substituted with one or more —OH, or $C_{1-6}$alkyl. In some embodiments, $L^3$ is selected from the group consisting of

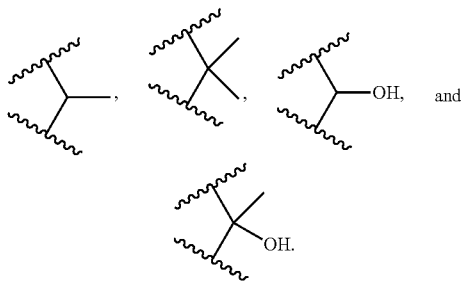

In some variations, the embodiments provided herein also apply to a compound of formula (II), or a stereoisomer or tautomer thereof, or a pharmaceutically acceptable salt of any of the foregoing, or any variation or embodiment thereof.

In some embodiments of a compound formula (II), such as a compound of formula (I'), (I-A), (I-A2), (I-C), or (I-C2), or a stereoisomer or tautomer thereof, or a pharmaceutically acceptable salt of any of the foregoing, $L^3$ is $C_{1-6}$alkylene, wherein the $C_{1-6}$alkylene of $L^3$ is optionally substituted with one or more —OH, or $C_{1-6}$alkyl, wherein the $C_{1-6}$alkyl is optionally substituted with one or more —OH. In some embodiments, $L^3$ is $C_{1-3}$alkylene, wherein the $C_{1-6}$alkylene of $L^3$ is optionally substituted with one or more —OH, or $C_{1-3}$alkyl, wherein the $C_{1-3}$alkyl is optionally substituted with one or more —OH. In some embodiments, $L^3$ is selected from the group consisting of

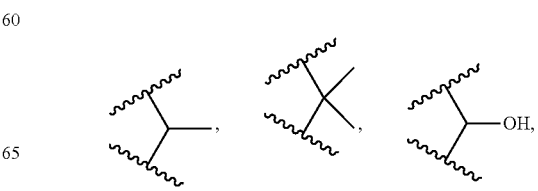

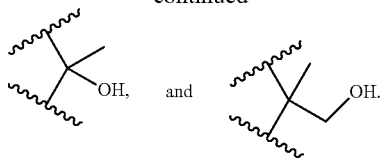

In some embodiments of a compound of formula (I'), (I), (I-A), (I-A2), (I-B), or (I-B1), or a stereoisomer or tautomer thereof, or a pharmaceutically acceptable salt of any of the foregoing, $L^3$ is $C_{3-10}$cycloalkyl, wherein the $C_{3-10}$cycloalkyl of $L^3$ is optionally substituted with one or more —OH. In some embodiments, $L^3$ is $C_{3-8}$cycloalkyl, wherein the $C_{3-8}$cycloalkyl of $L^3$ is optionally substituted with one or more —OH. In some embodiments, $L^3$ is

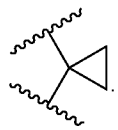 [SMILES: *C1(*)CC1]

In some variations, the embodiments provided herein also apply to a compound of formula (II), or a stereoisomer or tautomer thereof, or a pharmaceutically acceptable salt of any of the foregoing, or any variation or embodiment thereof.

In some embodiments of a compound formula (II), such as a compound of formula (I'), (I-A), (I-A2), (I-C), or (I-C2), or a stereoisomer or tautomer thereof, or a pharmaceutically acceptable salt of any of the foregoing, $L^3$ is 3-10 membered heterocyclyl, optionally substituted with one or more —OH or $C_{1-6}$alkyl. In some embodiments, $L^3$ is 3-6 membered heterocyclyl, optionally substituted with one or more —OH or $C_{1-3}$alkyl. In some embodiments, $L^3$ is

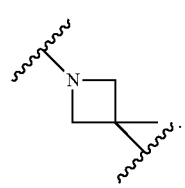 [SMILES: *N1CC(*)(C)C1]

In some embodiments of a compound of formula (I), (I-A), (I-A2), (I-C), or (I-C2), or a stereoisomer or tautomer thereof, or a pharmaceutically acceptable salt of any of the foregoing, $R^4$ is —S(O)$_2$—$R^a$, wherein $R^a$ is $C_{1-6}$alkyl. In some embodiments, $R^4$ is —S(O)$_2$—$R^a$, wherein $R^a$ is $C_{1-3}$alkyl. In some embodiments, $R^4$ is

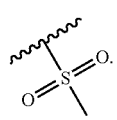

In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), (I-A), (I-A2), (I-C), or (I-C2), or a stereoisomer or tautomer thereof, or a pharmaceutically acceptable salt of any of the foregoing, $R^4$ is —(CH$_2$)$_q$OH, wherein q is an integer from 0-6. $R^4$ is —(CH$_2$)$_q$OH, wherein q is an integer from 0-2. In some embodiments, $R^4$ is —OH. In some embodiments, $R^4$ is selected from the group consisting of

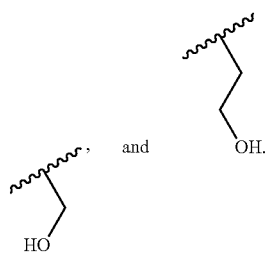

In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I'), (I-A), (I-A2), (I-C), or (I-C2), or a stereoisomer or tautomer thereof, or a pharmaceutically acceptable salt of any of the foregoing, $R^4$ is —C(O)—$C_{1-6}$alkyl. In some embodiments, $R^4$ is —C(O)—$C_{1-3}$alkyl. In some embodiments, $R^4$ is —C(O)CH$_3$. In some variations, the embodiments provided herein also apply to a compound of formula (II), or a stereoisomer or tautomer thereof, or a pharmaceutically acceptable salt of any of the foregoing, or any variation or embodiment thereof.

In some embodiments of a compound of formula (I), (I-A), (I-A2), (I-C), or (I-C2), or a stereoisomer or tautomer thereof, or a pharmaceutically acceptable salt of any of the foregoing, $R^5$ is $C_{1-6}$alkyl. In some embodiments, $R^5$ is $C_{1-3}$alkyl. In some embodiments, $R^5$ is methyl. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I'), (I-A), (I-A2), (I-C), or (I-C2) or a stereoisomer or tautomer thereof, or a pharmaceutically acceptable salt of any of the foregoing, $R^5$ is $C_{1-6}$alkyl, wherein the $C_{1-6}$alkyl of $R^5$ is optionally substituted with one or more halo. In some embodiments, $R^5$ is $C_{1-3}$alkyl, wherein the $C_{1-3}$alkyl of $R^5$ is optionally substituted with one or more halo. In some embodiments, $R^5$ is $C_{1-3}$alkyl, wherein the $C_{1-3}$alkyl of $R^5$ is optionally substituted with one or more fluoro. In some embodiments, $R^5$ is

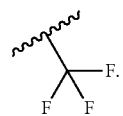

In some embodiments, $R^5$ is methyl. In some variations, the embodiments provided herein also apply to a compound of formula (II), or a stereoisomer or tautomer thereof, or a pharmaceutically acceptable salt of any of the foregoing, or any variation or embodiment thereof.

In some embodiments of a compound of formula (I'), (I-A), (I-A2), (I-C), or (I-C2), or a stereoisomer or tautomer thereof, or a pharmaceutically acceptable salt of any of the foregoing, $R^5$ is halo. In some embodiments, $R^5$ is Cl, or F. In some variations, the embodiments provided herein also apply to a compound of formula (II), or a stereoisomer or tautomer thereof, or a pharmaceutically acceptable salt of any of the foregoing, or any variation or embodiment thereof.

In some embodiments, provided herein is a compound of formula (I), (I-A), or (I-A2), or a stereoisomer or tautomer thereof, or a pharmaceutically acceptable salt thereof, wherein the compound is a compound of formula (I-D):

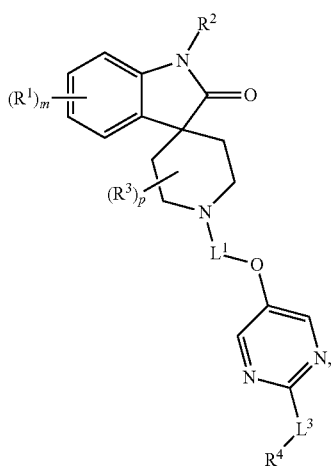

(I-D)

or a stereoisomer or tautomer thereof, or a pharmaceutically acceptable salt of any of the foregoing, wherein: m, p, $R^1$, $R^2$, $R^3$, $L^1$, $L^3$, and $R^4$, are as defined for formula (I). In some variations, m, p, $R^1$, $R^2$, $R^3$, $L^1$, $L^3$, and $R^4$ of formula (I-D) are as defined for a compound of formula (I'), or (II), or a stereoisomer or tautomer thereof, or a pharmaceutically acceptable salt of any of the foregoing, or any variation or embodiment thereof.

In some embodiments of a compound of formula (I), (I-A), (I-A2), or (I-D), or a stereoisomer or tautomer thereof, or a pharmaceutically acceptable salt of any of the foregoing, $R^2$ is H. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (II), such as a compound of formula (I), (I-A), (I-A2), or (I-D), or a stereoisomer or tautomer thereof, or a pharmaceutically acceptable salt of any of the foregoing, $R^2$ is $C_{1-6}$alkyl optionally substituted with one or more deuterium. In some embodiments, $R^2$ is $C_{1-3}$alkyl optionally substituted with one or more deuterium. In some embodiments, $R^2$ is methyl optionally substituted with one or more deuterium. In some embodiments, $R^2$ is

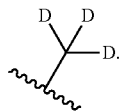

In some embodiments of a compound of formula (I), (I-A), (I-A2), or (I-D), or a stereoisomer or tautomer thereof, or a pharmaceutically acceptable salt of any of the foregoing, m is an integer from 0 to 4. In some embodiments, m is an integer from 0 to 2. In some embodiments m is 1. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), (I-A), (I-A2), or (I-D), or a stereoisomer or tautomer thereof, or a pharmaceutically acceptable salt of any of the foregoing, $R^1$ is halo. In some embodiments $R^1$ is Cl. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (II), such as a compound of formula (I), (I-A), (I-A2), or (I-D), or a stereoisomer or tautomer thereof, or a pharmaceutically acceptable salt of any of the foregoing, $R^1$ is Cl, or I.

In some embodiments of a compound of formula (I), (I-A), (I-A2), or (I-D), or a stereoisomer or tautomer thereof, or a pharmaceutically acceptable salt of any of the foregoing, $R^1$ is —CN. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), (I-A), (I-A2), or (I-D), or a stereoisomer or tautomer thereof, or a pharmaceutically acceptable salt of any of the foregoing, $R^1$ is $C_{1-6}$alkyl, wherein the $C_{1-6}$alkyl of $R^1$ is optionally substituted with one or more halo. In some embodiments, $R^1$ is $C_{1-3}$alkyl, wherein the $C_{1-3}$alkyl of $R^1$ is optionally substituted with one or more halo. In some embodiments, $R^1$ is $C_{1-3}$alkyl, wherein the $C_{1-3}$alkyl of $R^1$ is optionally substituted with one or more F. In some embodiments, $R^1$ is methyl, wherein the methyl of $R^1$ is optionally substituted with one or more F. In some embodiments, $R^1$ is

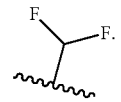

In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), (I-A), (I-A2), or (I-D), or a stereoisomer or tautomer thereof, or a pharmaceutically acceptable salt of any of the foregoing, $L^1$ is $C_{1-6}$alkylene optionally substituted with one or more $C_{1-6}$alkyl. In some embodiments, $L^1$ is ethylene optionally substituted with one or more $C_{1-6}$alkyl. In some embodiments, $L^1$ is selected from the group consisting of

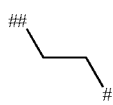

wherein, for each $L^1$, # denotes the point of attachment to —O— and ## denotes the point of attachment to the remainder of the molecule. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), (I-A), (I-A2), or (I-D), or a stereoisomer or tautomer thereof, or a pharmaceutically acceptable salt of any of the foregoing, $L^3$ is absent. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), (I-A), (I-A2), or (I-D), or a stereoisomer or tautomer thereof, or a pharmaceutically acceptable salt of any of the foregoing, $L^3$ is —O—. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), (I-A), (I-A2), or (I-D), or a stereoisomer or tautomer thereof, or a pharmaceutically acceptable salt of any of the foregoing, $L^3$ is $C_{1-6}$alkylene. In some embodiments, $L^3$ is $C_{1-3}$alkylene. In some embodiments, $L^3$ is

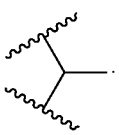 [SMILES: *C(*)C]

In some variations, the embodiments provided herein also apply to a compound of formula (I') or a stereoisomer or tautomer thereof, or a pharmaceutically acceptable salt of any of the foregoing, or any variation or embodiment thereof.

In some embodiments of a compound of formula (I'), (I-A), (I-A2), or (I-D), or a stereoisomer or tautomer thereof, or a pharmaceutically acceptable salt of any of the foregoing, $L^3$ is $C_{1-6}$alkylene, wherein the $C_{1-6}$alkylene of $L^3$ is optionally substituted with one or more —OH, or $C_{1-6}$alkyl. In some embodiments, $L^3$ is $C_{1-3}$alkylene, wherein the $C_{1-6}$alkylene of $L^3$ is optionally substituted with one or more —OH, or $C_{1-6}$alkyl. In some embodiments, $L^3$ is selected from the group consisting of

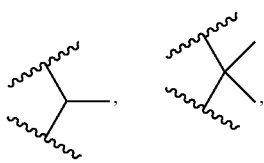

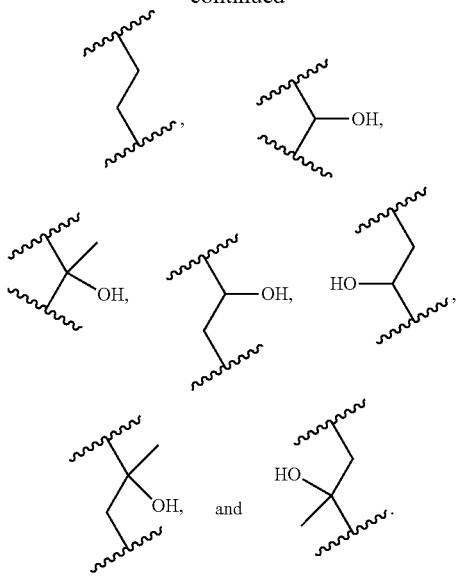

In some embodiments of a compound of formula (I), (I-A), (I-A2), or (I-D), or a stereoisomer or tautomer thereof, or a pharmaceutically acceptable salt of any of the foregoing, $L^3$ is $C_{3-10}$cycloalkyl. In some embodiments, $L^3$ is $C_{3-8}$cycloalkyl. In some embodiments, $L^3$ is

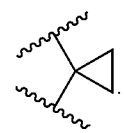 [SMILES: *C1(*)CC1]

In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I'), (I-A), (I-A2), or (I-D), or a stereoisomer or tautomer thereof, or a pharmaceutically acceptable salt of any of the foregoing, $L^3$ is $C_{3-10}$cycloalkyl, wherein the $C_{3-10}$cycloalkyl of $L^3$ is optionally substituted with one or more —OH. In some embodiments, $L^3$ is $C_{3-8}$cycloalkyl, wherein the $C_{3-8}$cycloalkyl of $L^3$ is optionally substituted with one or more —OH. In some embodiments, $L^3$ is selected from the group consisting of

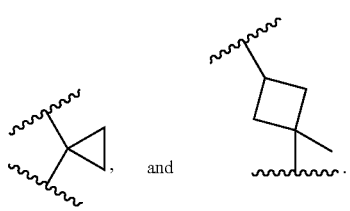

In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (II), such as a compound of formula (I'), (I-A), (I-A2), or (I-D), or a stereoisomer or tautomer thereof, or a pharmaceutically acceptable salt of any of the foregoing, $L^3$ is $C_{3-10}$cycloalkyl, wherein the $C_{3-10}$cycloalkyl of $L^3$ is optionally substituted with one or more —OH. In some embodiments, $L^3$ is $C_{3-8}$cycloalkyl, wherein the $C_{3-8}$-cycloalkyl of $L^3$ is optionally substituted with one or more —OH. In some embodiments, $L^3$ is selected from the group consisting of

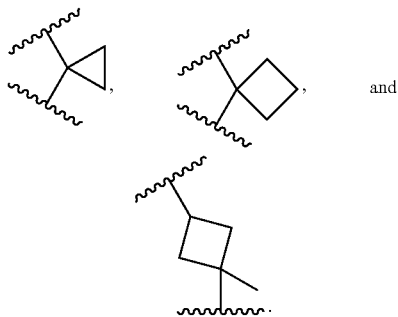

In some embodiments of a compound of formula (I'), (I-A), (I-A2), or (I-D) or a stereoisomer or tautomer thereof, or a pharmaceutically acceptable salt of any of the foregoing, $L^3$ is 3-10 membered heterocyclyl. In some embodiments, $L^3$ is 3-6 membered heterocyclyl. In some embodiments, $L^3$ is selected from the group consisting of

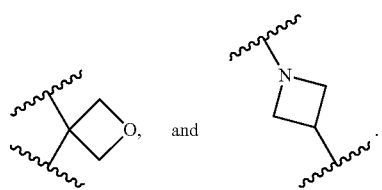 [SMILES: *C1(*)COC1 ; *C1CN(*)C1]

In some variations, the embodiments provided herein also apply to a compound of formula (II), or a stereoisomer or tautomer thereof, or a pharmaceutically acceptable salt of any of the foregoing, or any variation or embodiment thereof.

In some embodiments of a compound of formula (II), such as a compound of (I'), (I-A), (I-A2), or (I-D) or a stereoisomer or tautomer thereof, or a pharmaceutically acceptable salt of any of the foregoing, $L^3$ is 3-10 membered heterocyclyl. In some embodiments, $L^3$ is 3-6 membered heterocyclyl. In some embodiments, $L^3$ is selected from the group consisting of

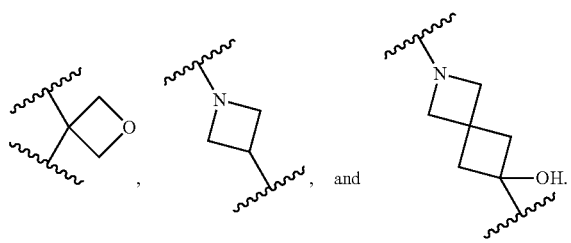 [SMILES: *C1(*)COC1 ; *C1CN(*)C1 ; *N1CC2(C1)CC(*)(O)C2]

In some embodiments of a compound of formula (I), (I-A), (I-A2), or (I-D), or a stereoisomer or tautomer thereof, or a pharmaceutically acceptable salt of any of the foregoing, $R^4$ is —S(O)$_2$—R$^a$, wherein R$^a$ is $C_{1-6}$alkyl. In some embodiments, $R^4$ is —S(O)$_2$—R$^a$, wherein R$^a$ is $C_{1-3}$alkyl. In some embodiments, $R^4$ is

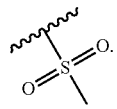

In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), (I-A), (I-A2), or (I-D), or a stereoisomer or tautomer thereof, or a pharmaceutically acceptable salt of any of the foregoing, $R^4$ is —C(O)—N(R$^e$)$_2$, wherein each of R$^e$ is H. In some embodiments, $R^4$ is —C(O)—NH$_2$. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), (I-A), (I-A2), or (I-D), or a stereoisomer or tautomer thereof, or a pharmaceutically acceptable salt of any of the foregoing, $R^4$ is 3-10 membered heterocyclyl optionally substituted with one or more $C_{1-6}$ alkyl. In some embodiments, $R^4$ is 3-6 membered heterocyclyl optionally substituted with one or more $C_{1-6}$ alkyl. In some embodiments, $R^4$ is 3-6 membered heterocyclyl optionally substituted with one or more $C_{1-3}$ alkyl. In some embodiments, $R^4$ is 3-6 membered heterocyclyl optionally substituted with one or more methyl. In some embodiments, $R^4$ is

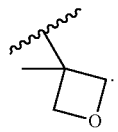 [SMILES: *C1(C)COC1]

In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (II), such as a compound of formula (I), (I-A), (I-A2), or (I-D), or a stereoisomer or tautomer thereof, or a pharmaceutically acceptable salt of any of the foregoing, $R^4$ is

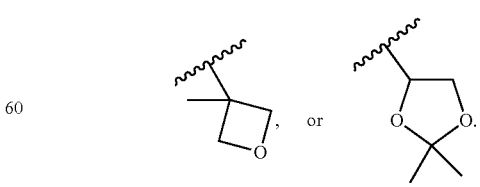

In some embodiments of a compound of formula (I'), (I-A), (I-A2), or (I-D), or a stereoisomer or tautomer thereof, or a pharmaceutically acceptable salt of any of the foregoing, $R^4$ is 3-10 membered heterocyclyl optionally substituted with one or more $C_{1-6}$ alkyl. In some embodiments, $R^4$ is 3-6 membered heterocyclyl optionally substituted with one or more $C_{1-6}$ alkyl. In some embodiments, $R^4$ is 3-6 membered heterocyclyl optionally substituted with one or more $C_{1-3}$ alkyl. In some embodiments, $R^4$ is 3-6 membered heterocyclyl optionally substituted with one or more methyl. In some embodiments, $R^4$ is selected from the group consisting of

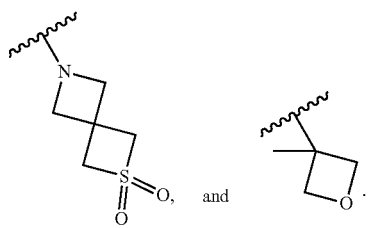

In some variations, the embodiments provided herein also apply to a compound of formula (II), or a stereoisomer or tautomer thereof, or a pharmaceutically acceptable salt of any of the foregoing, or any variation or embodiment thereof.

In some embodiments of a compound of formula (I'), (I-A), (I-A2), or (I-D) or a stereoisomer or tautomer thereof, or a pharmaceutically acceptable salt of any of the foregoing, $R^4$ is —$(CH_2)_qOH$, wherein q is an integer from 0-6. $R^4$ is —$(CH_2)_qOH$, wherein q is an integer from 0-2. In some embodiments, $R^4$ is —OH. In some embodiments, $R^4$ is selected from the group consisting of

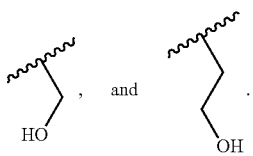

In some variations, the embodiments provided herein also apply to a compound of formula (II), or a stereoisomer or tautomer thereof, or a pharmaceutically acceptable salt of any of the foregoing, or any variation or embodiment thereof.

In some embodiments of a compound of formula (I'), (I-A), (I-A2), or (I-D) or a stereoisomer or tautomer thereof, or a pharmaceutically acceptable salt of any of the foregoing, $R^4$ is —$N(R^d)_2$, wherein each of $R^d$ is independently H. In some embodiments, $R^4$ is —$NH_2$. In some variations, the embodiments provided herein also apply to a compound of formula (II), or a stereoisomer or tautomer thereof, or a pharmaceutically acceptable salt of any of the foregoing, or any variation or embodiment thereof.

In some embodiments of a compound of formula (I'), (I-A), (I-A2), or (I-D) or a stereoisomer or tautomer thereof, or a pharmaceutically acceptable salt of any of the foregoing, $R^4$ is —$P(O)(C_{1-6}alkyl)_2$. In some embodiments, $R^4$ is —$P(O)(C_{1-3}alkyl)_2$. In some embodiments, $R^4$ is —$P(O)(CH_3)_2$. In some variations, the embodiments provided herein also apply to a compound of formula (II), or a stereoisomer or tautomer thereof, or a pharmaceutically acceptable salt of any of the foregoing, or any variation or embodiment thereof.

In some embodiments, provided herein is a compound of formula (I), (I-A) or (I-A2), or a stereoisomer or tautomer thereof, or a pharmaceutically acceptable salt thereof, wherein the compound is a compound of formula (I-E):

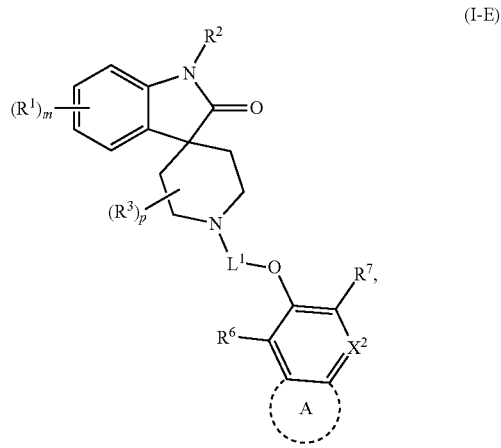

(I-E)

or a stereoisomer or tautomer thereof, or a pharmaceutically acceptable salt of any of the foregoing, wherein: ring A is 5-10 membered heterocyclyl or a 5-10 membered heteroaryl, wherein the 5-10 membered heterocyclyl of ring A is optionally substituted with one or more $R^b$, and wherein the 5-10 membered heteroaryl of ring A is optionally substituted with one or more $R^c$; and m, p, $R^1$, $R^2$, $R^3$ $L^1$, $X^2$, $R^b$, $R^c$, $R^6$, and $R^7$ are as defined for formula (I). In some variations, ring A is 5-10 membered heterocyclyl or a 5-10 membered heteroaryl, wherein the 5-10 membered heterocyclyl of ring A is optionally substituted with one or more $R^b$, and wherein the 5-10 membered heteroaryl of ring A is optionally substituted with one or more $R^c$; and m, p, $R^1$, $R^2$, $R^3$ $L^1$, $X^2$, $R^b$, $R^c$, $R^6$, and $R^7$ of formula (I-E) are as defined for a compound of formula (I'), or (II), or a stereoisomer or tautomer thereof, or a pharmaceutically acceptable salt of any of the foregoing, or any variation or embodiment thereof.

In some embodiments, provided herein is a compound of formula (I), (I-A) or (I-A2), or a stereoisomer or tautomer thereof, or a pharmaceutically acceptable salt thereof, wherein the compound is a compound of formula (I-E1):

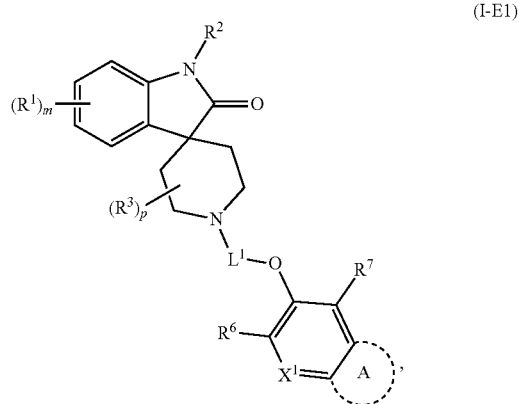

(I-E1)

or a stereoisomer or tautomer thereof, or a pharmaceutically acceptable salt of any of the foregoing, wherein: ring A is 5-10 membered heterocyclyl or a 5-10 membered heteroaryl, wherein the 5-10 membered heterocyclyl of ring A is optionally substituted with one or more $R^b$, and wherein the 5-10 membered heteroaryl of ring A is optionally substituted with one or more $R^c$; and m, p, $R^1$, $R^2$, $R^3$, $L^1$, $X^1$, $R^b$, $R^c$, $R^6$, and $R^7$ are as defined for formula (I). In some variations, ring A is 5-10 membered heterocyclyl or a 5-10 membered heteroaryl, wherein the 5-10 membered heterocyclyl of ring A is optionally substituted with one or more $R^b$, and wherein the 5-10 membered heteroaryl of ring A is optionally substituted with one or more $R^c$; and m, p, $R^1$, $R^2$, $R^3$, $L^1$, $X^1$, $R^b$, $R^c$, $R^6$, and $R^7$ of formula (I-E1) are as defined for a compound of formula (I'), or (II), or a stereoisomer or tautomer thereof, or a pharmaceutically acceptable salt of any of the foregoing, or any variation or embodiment thereof.

In some embodiments, provided herein is a compound of formula (I'), (I-A), (I-A2), or (I-E) or a stereoisomer or tautomer thereof, or a pharmaceutically acceptable salt thereof, wherein the compound is a compound of formula (I-E2):

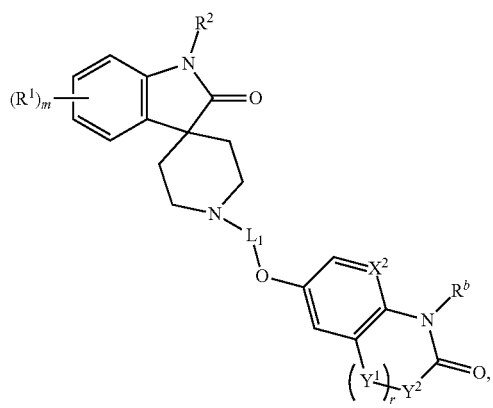

(I-E2)

or a stereoisomer or tautomer thereof, or a pharmaceutically acceptable salt of any of the foregoing, wherein: r is an integer from 0-1; $Y^1$ and $Y^2$ are each independently C or N, optionally substituted by one or more H or $R^b$; and m, $R^1$, $R^2$, $L^1$, $X^2$, and $R^b$ are as defined for formula (I'), or (II); and wherein the dashed line represents a single or double bond.

In some embodiments, provided herein is a compound of formula (I'), (I-A), (I-A2), or (I-E) or a stereoisomer or tautomer thereof, or a pharmaceutically acceptable salt thereof, wherein the compound is a compound of formula (I-E3):

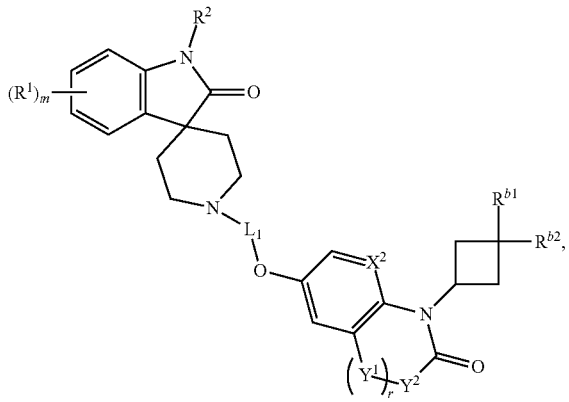

(I-E3)

or a stereoisomer or tautomer thereof, or a pharmaceutically acceptable salt of any of the foregoing, wherein: r is an integer from 0-1; $Y^1$ and $Y^2$ are each independently C or N, optionally substituted by one or more H or $R^b$; $R^{b1}$ is OH; $R^{b2}$ is H, $C_{1-6}$alkyl, or $C_{3-10}$cycloalkyl, wherein the $C_{1-6}$alkyl of $R^{b2}$ is optionally substituted with one or more OH; and m, $R^1$, $R^2$, $L^1$, $X^2$, and $R^b$ are as defined for formula (I'), or (II); and wherein the dashed line represents a single or double bond.

In some embodiments of a compound of formula (I'), (I-A) (I-A2), or (I-E3) or a stereoisomer or tautomer thereof, or a pharmaceutically acceptable salt of any of the foregoing, the moiety represented by

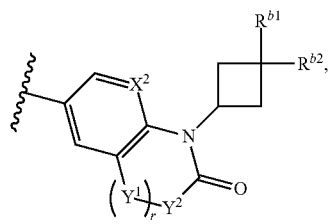

has a stereochemical configuration represented by

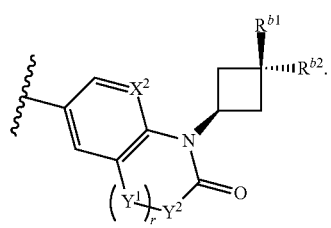

In some variations, the embodiments provided herein also apply to a compound of formula (II), or a stereoisomer or tautomer thereof, or a pharmaceutically acceptable salt of any of the foregoing, or any variation or embodiment thereof.

In some embodiments of a compound of formula (I'), (I-A) (I-A2), or (I-E3) or a stereoisomer or tautomer thereof, or a pharmaceutically acceptable salt of any of the foregoing, the moiety represented by

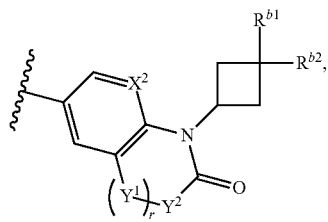

has a stereochemical configuration represented by

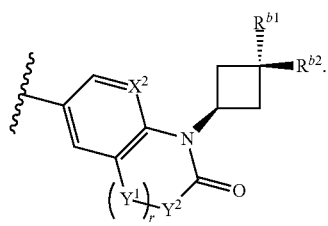

In some variations, the embodiments provided herein also apply to a compound of formula (II), or a stereoisomer or tautomer thereof, or a pharmaceutically acceptable salt of any of the foregoing, or any variation or embodiment thereof.

In some embodiments, provided herein is a compound of formula (I'), (I-A), (I-A2), or (I-E) or a stereoisomer or tautomer thereof, or a pharmaceutically acceptable salt thereof, wherein the compound is a compound of formula (I-E4):

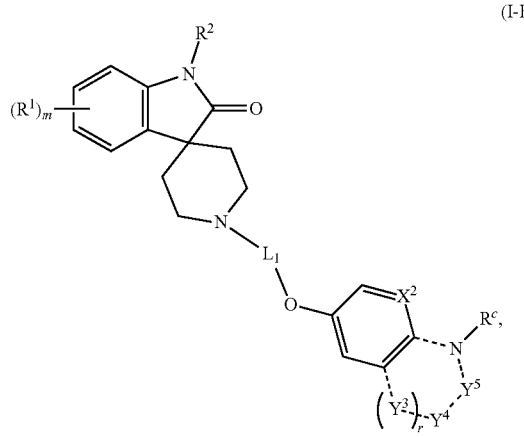

(I-E4)

or a stereoisomer or tautomer thereof, or a pharmaceutically acceptable salt of any of the foregoing, wherein: r is an integer from 0-1; $Y^3$, $Y^4$, and $Y^5$ are each independently C or N, optionally substituted by one or more H or $R^c$; and m, $R^1$, $R^2$, $L^1$, $X^2$, and $R^c$ are as defined for formula (I'), or (II); and wherein the dashed line represents a single or double bond.

In some embodiments, provided herein is a compound of formula (I'), (I-A), (I-A2), or (I-E) or a stereoisomer or tautomer thereof, or a pharmaceutically acceptable salt thereof, wherein the compound is a compound of formula (I-E5):

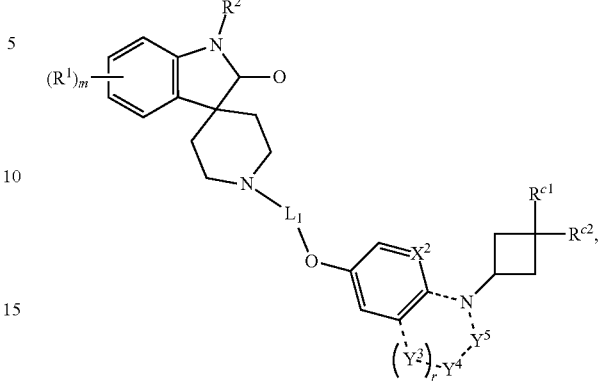

(I-E5)

or a stereoisomer or tautomer thereof, or a pharmaceutically acceptable salt of any of the foregoing, wherein: r is an integer from 0-1; $Y^3$, $Y^4$ and $Y^5$ are each independently C or N, optionally substituted by one or more H or $R^c$; $R^{c1}$ is OH; $R^{c2}$ is H, $C_{1-6}$alkyl, or $C_{3-10}$cycloalkyl, wherein the $C_{1-6}$alkyl of $R^{c2}$ is optionally substituted with one or more OH; and m, $R^1$, $R^2$, $L^1$, $X^2$, and $R^c$ are as defined for formula (I'), or (II); and wherein the dashed line represents a single or double bond.

In some embodiments of a compound of formula (I'), (I-A) (I-A2), or (I-E5) or a stereoisomer or tautomer thereof, or a pharmaceutically acceptable salt of any of the foregoing, the moiety represented by

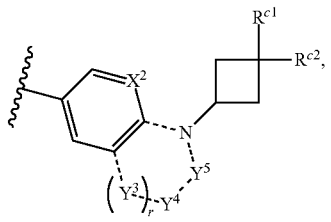

has a stereochemical configuration represented by

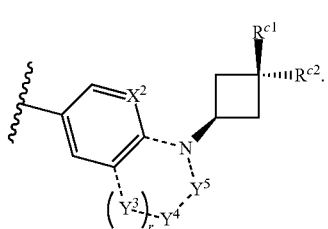

In some variations, the embodiments provided herein also apply to a compound of formula (II), or a stereoisomer or tautomer thereof, or a pharmaceutically acceptable salt of any of the foregoing, or any variation or embodiment thereof.

In some embodiments of a compound of formula (I'), (I-A) (I-A2), or (I-E) or a stereoisomer or tautomer thereof, or a pharmaceutically acceptable salt of any of the foregoing, the moiety represented by

241

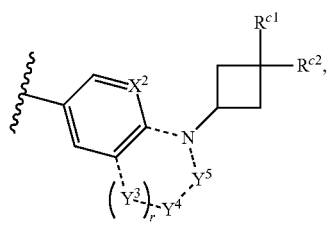

has a stereochemical configuration represented by

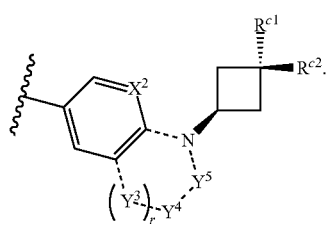

In some variations, the embodiments provided herein also apply to a compound of formula (II), or a stereoisomer or tautomer thereof, or a pharmaceutically acceptable salt of any of the foregoing, or any variation or embodiment thereof.

In some embodiments, provided herein is a compound of formula (I), (I-A) or (I-A2), (I-E), or (I-E1), or a stereoisomer or tautomer thereof, or a pharmaceutically acceptable salt thereof, wherein the compound is a compound of formula (I-F):

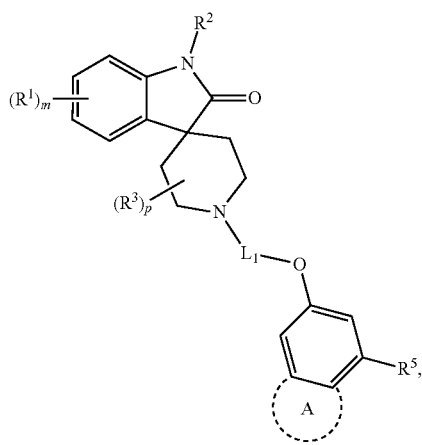

(I-F)

or a stereoisomer or tautomer thereof, or a pharmaceutically acceptable salt of any of the foregoing, wherein: ring A is 5-10 membered heterocyclyl or a 5-10 membered heteroaryl, wherein the 5-10 membered heterocyclyl of ring A is optionally substituted with one or more $R^b$, and wherein the 5-10 membered heteroaryl of ring A is optionally substituted with one or more $R^c$; and m, p, $R^1$, $R^2$, $R^3$, $L^1$, $R^5$, $R^b$, and $R^c$, are as defined for formula (I). In some variations, ring A is 5-10 membered heterocyclyl or a 5-10 membered heteroaryl, wherein the 5-10 membered heterocyclyl of ring A is optionally substituted with one or more $R^b$, and wherein the 5-10 membered heteroaryl of ring A is

242 optionally substituted with one or more $R^c$; and m, p, $R^1$, $R^2$, $R^3$, $L^1$, $R^5$, $R^b$, and $R^c$ of formula (I-F) are as defined for a compound of formula (I'), or (II), or a stereoisomer or tautomer thereof, or a pharmaceutically acceptable salt of any of the foregoing, or any variation or embodiment thereof.

In some embodiments, provided herein is a compound of formula (I), (I-A) or (I-A2), (I-E), (I-E1), or (I-F), or a stereoisomer or tautomer thereof, or a pharmaceutically acceptable salt thereof, wherein the compound is a compound of formula (I-F1):

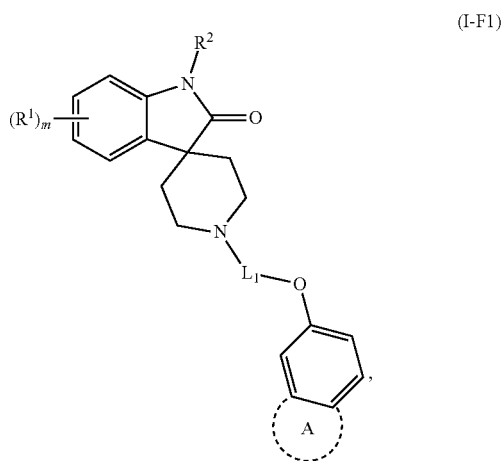

(I-F1)

or a stereoisomer or tautomer thereof, or a pharmaceutically acceptable salt of any of the foregoing, wherein: ring A is 5-10 membered heterocyclyl or a 5-10 membered heteroaryl, wherein the 5-10 membered heterocyclyl of ring A is optionally substituted with one or more $R^b$, and wherein the 5-10 membered heteroaryl of ring A is optionally substituted with one or more $R^c$; and m, $R^1$, $R^2$, $L^1$, $R^b$, and $R^c$, are as defined for formula (I). In some variations, ring A is 5-10 membered heterocyclyl or a 5-10 membered heteroaryl, wherein the 5-10 membered heterocyclyl of ring A is optionally substituted with one or more $R^b$, and wherein the 5-10 membered heteroaryl of ring A is optionally substituted with one or more $R^c$; and m, $R^1$, $R^2$, $L^1$, $R^b$, and $R^c$ of formula (I-F1) are as defined for a compound of formula (I'), or (II), or a stereoisomer or tautomer thereof, or a pharmaceutically acceptable salt of any of the foregoing, or any variation or embodiment thereof.

In some embodiments of a compound of formula (I), (I-A) or (I-A2), (I-E), (I-E1), (I-F), or (I-F1), or a stereoisomer or tautomer thereof, or a pharmaceutically acceptable salt of any of the foregoing, $R^2$ is H. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), (I-A) or (I-A2), (I-E), (I-E1), (I-F), or (I-F1), or a stereoisomer or tautomer thereof, or a pharmaceutically acceptable salt of any of the foregoing, $R^2$ is $C_{1-6}$alkyl, wherein the $C_{1-6}$alkyl of $R^2$ is optionally substituted with one or more —OH, —NH$_2$, or $C_{1-6}$alkoxy. In some embodiments, $R^2$ is methyl. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (II), such as a compound of formula (I'), (I), (I-A) or (I-A2), (I-E), (I-E1), (I-F), or (I-F1), or a stereoisomer or tautomer thereof, or a pharmaceutically acceptable salt of any of the foregoing, $R^2$ is $C_{1-6}$alkyl, wherein the $C_{1-6}$alkyl of $R^2$ is optionally substituted with one or more deuterium, —OH, —NH$_2$, or $C_{1-6}$alkoxy. In some embodiments, $R^2$ is methyl optionally substituted with one or more deuterium. In some embodiments, $R^2$ is

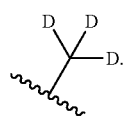

In some embodiments of a compound of formula (I), (I-A) or (I-A2), (I-E), (I-E1), (I-F), or (I-F1), or a stereoisomer or tautomer thereof, or a pharmaceutically acceptable salt of any of the foregoing, $R^2$ is $C_{3-10}$cycloalkyl, wherein the $C_{3-10}$cycloalkyl of $R^2$ is optionally substituted with one or more —OH. In some embodiments, $R^2$ is $C_{3-6}$cycloalkyl, wherein the $C_{3-6}$cycloalkyl of $R^2$ is optionally substituted with one or more —OH. In some embodiments, $R^2$ is

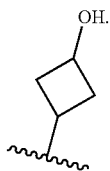

In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), (I-A) or (I-A2), (I-E), (I-E1), (I-F), or (I-F1), or a stereoisomer or tautomer thereof, or a pharmaceutically acceptable salt of any of the foregoing, m is an integer from 0 to 4. In some embodiments, m is an integer from 0 to 2. In some embodiments, m is 0 or 1. In some embodiments, m is 0. In some embodiments m is 1. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), (I-A) or (I-A2), (I-E), (I-E1), (I-F), or (I-F1), or a stereoisomer or tautomer thereof, or a pharmaceutically acceptable salt of any of the foregoing, $R^1$ is halo. In some embodiments $R^1$ is Cl. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), (I-A) or (I-A2), (I-E), (I-E1), (I-F), or (I-F1), or a stereoisomer or tautomer thereof, or a pharmaceutically acceptable salt of any of the foregoing, $R^1$ is —CN. In some variations, the embodiments provided herein also apply to a compound of formula (I') or a stereoisomer or tautomer thereof, or a pharmaceutically acceptable salt of any of the foregoing, or any variation or embodiment thereof. In some embodiments of a compound of formula (I), (I-A) or (I-A2), (I-E), (I-E1), (I-F), or (I-F1), or a stereoisomer or tautomer thereof, or a pharmaceutically acceptable salt of any of the foregoing, $L^1$ is $C_{1-6}$alkylene, wherein the $C_{1-6}$alkylene of $L^1$ is optionally substituted with one or more $C_{1-6}$alkyl. In some embodiments, $L^1$ is ethylene, wherein the ethylene of $L^1$ is optionally substituted with one or more $C_{1-6}$alkyl. In some embodiments, $L^1$ is selected from the group consisting of

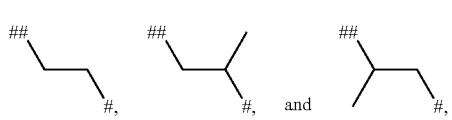

wherein, for each $L^1$, # denotes the point of attachment to —O— and ## denotes the point of attachment to the remainder of the molecule. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), (I-A) or (I-A2), (I-E), (I-E1), (I-F), or (I-F1), or a stereoisomer or tautomer thereof, or a pharmaceutically acceptable salt of any of the foregoing, ring A is a 5-10 membered heterocyclyl, wherein the 5-10 membered heterocyclyl is optionally substituted with one or more of $R^b$, wherein $R^b$ is oxo. In some embodiments, ring A is a 5-10 membered heterocyclyl, wherein the 5-10 membered heterocyclyl is optionally substituted with one or more of $R^b$, wherein $R^b$ is oxo. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), (I-A) or (I-A2), (I-E), (I-E1), (I-F), or (I-F1), or a stereoisomer or tautomer thereof, or a pharmaceutically acceptable salt of any of the foregoing, ring A is selected from the group consisting of

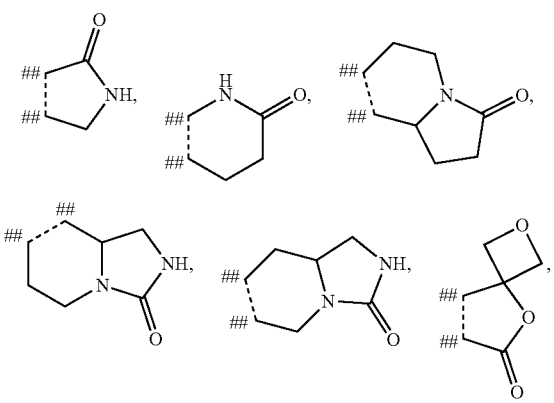

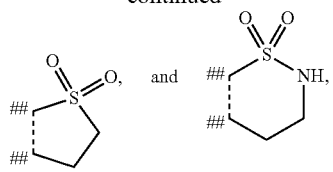

wherein ## represent a point of attachment to the remainder of the molecule and the dashed line represents a single or double bond. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), (I-A) or (I-A2), (I-E1), (I-E2), (I-F), or (I-F1), or a stereoisomer or tautomer thereof, or a pharmaceutically acceptable salt of any of the foregoing, ring A is a 5-10 membered heterocyclyl, wherein the 5-10 membered heterocyclyl is optionally substituted with one or more $R^b$, wherein each $R^b$ is independently oxo, or $C_{1-6}$alkyl. In some embodiments, ring A is a 5-10 membered heterocyclyl, wherein the 5-10 membered heterocyclyl is optionally substituted with one or more $R^b$, wherein each $R^b$ is independently oxo, or $C_{1-6}$alkyl, wherein the $C_{1-6}$alkyl of $R^b$ is optionally substituted with one or more halo, OH, or —$S(O)_2$—$C_{1-6}$alkyl. In some embodiments, ring A is a 5-10 membered heterocyclyl, wherein the 5-10 membered heterocyclyl is optionally substituted with one or more $R^b$, wherein wherein each $R^b$ is independently oxo, or $C_{1-3}$alkyl, wherein the $C_{1-3}$alkyl of $R^b$ is optionally substituted with one or more more halo, —OH, or —$S(O)_2$—$C_{1-3}$alkyl. In some embodiments, ring A is a 5-10 membered heterocyclyl, wherein the 5-10 membered heterocyclyl is optionally substituted with one or more $R^b$, wherein each $R^b$ is independently selected from the group consisting of oxo,

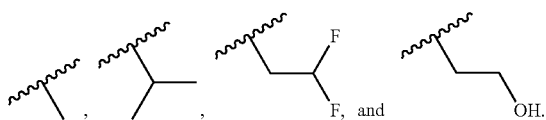

In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), (I-A) or (I-A2), (I-E1), (I-E2), (I-F), or (I-F1), or a stereoisomer or tautomer thereof, or a pharmaceutically acceptable salt of any of the foregoing, ring A is selected from the group consisting of

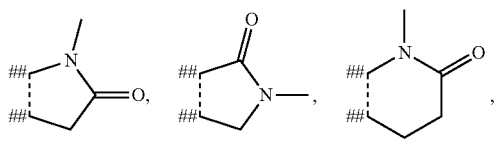

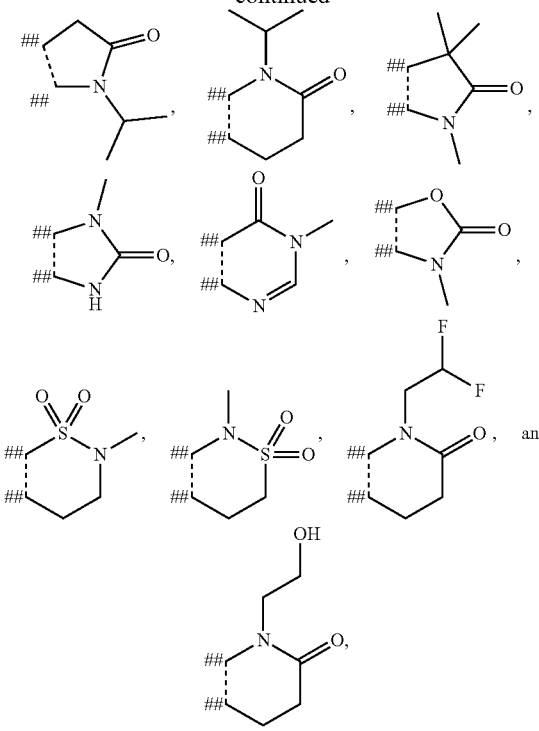

wherein ## represent a point of attachment to the remainder of the molecule and the dashed line represents a single or double bond. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), (I-A) or (I-A2), (I-E1), (I-E2), (I-F), or (I-F1), or a stereoisomer or tautomer thereof, or a pharmaceutically acceptable salt of any of the foregoing, ring A is a 5-10 membered heterocyclyl, wherein the 5-10 membered heterocyclyl is optionally substituted with one or more $R^b$, wherein one or more of $R^b$ is —C(O)—NH($C_{1-6}$alkyl). In some embodiments, ring A is a 5-10 membered heterocyclyl, wherein the 5-10 membered heterocyclyl is optionally substituted with one or more $R^b$, wherein one or more of $R^b$ is —C(O)—NH($C_{1-3}$alkyl). In some embodiments, ring A is a 5-10 membered heterocyclyl, wherein the 5-10 membered heterocyclyl is optionally substituted with one or more $R^b$, wherein one or more of $R^b$ is

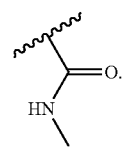

In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), (I-A) or (I-A2), (I-E1), (I-E2), (I-F), or (I-F1), or a stereoisomer or tautomer thereof, or a pharmaceutically acceptable salt of any of the foregoing, ring A is selected from the group consisting of

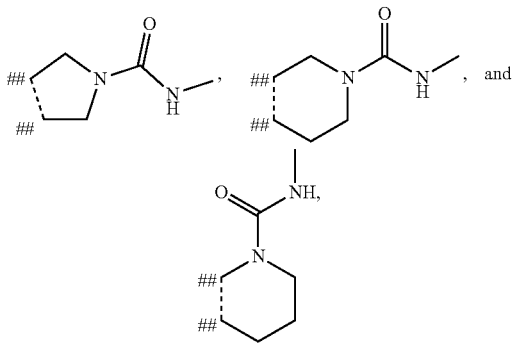

wherein ## represent a point of attachment to the remainder of the molecule and the dashed line represents a single or double bond. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), (I-A) or (I-A2), (I-E1), (I-E2), (I-F), or (I-F1), or a stereoisomer or tautomer thereof, or a pharmaceutically acceptable salt of any of the foregoing, ring A is a 5-10 membered heterocyclyl, wherein the 5-10 membered heterocyclyl is optionally substituted with one or more $R^b$, wherein one or more of $R^b$ is —C(O)—$C_{1-6}$alkyl. In some embodiments, ring A is a 5-10 membered heterocyclyl, wherein the 5-10 membered heterocyclyl is optionally substituted with one or more $R^b$, wherein one or more of $R^b$ is —C(O)—$C_{1-3}$alkyl. In some embodiments, ring A is a 5-10 membered heterocyclyl, wherein the 5-10 membered heterocyclyl is optionally substituted with one or more $R^b$, wherein one or more of $R^b$ is

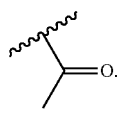

In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), (I-A) or (I-A2), (I-E1), (I-E2), (I-F), or (I-F1), or a stereoisomer or tautomer thereof, or a pharmaceutically acceptable salt of any of the foregoing, ring A is selected from the group consisting of

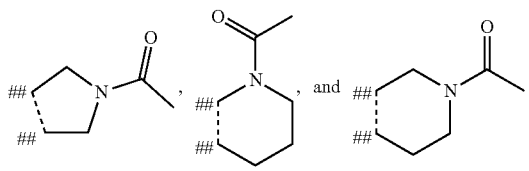

wherein ## represent a point of attachment to the remainder of the molecule and the dashed line represents a single or double bond. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), (I-A) or (I-A2), (I-E1), (I-E2), (I-F), or (I-F1), or a stereoisomer or tautomer thereof, or a pharmaceutically acceptable salt of any of the foregoing, ring A is a 5-10 membered heterocyclyl, wherein the 5-10 membered heterocyclyl is optionally substituted with one or more $R^b$, wherein one or more of $R^b$ is —S(O)$_2$—$R^a$, wherein $R^a$ is $C_{1-6}$alkyl. In some embodiments, ring A is a 5-10 membered heterocyclyl, wherein the 5-10 membered heterocyclyl is optionally substituted with one or more $R^b$, wherein one or more of $R^b$ is —S(O)$_2$—$R^a$, wherein $R^a$ is $C_{1-3}$alkyl. In some embodiments, ring A is a 5-10 membered heterocyclyl, wherein the 5-10 membered heterocyclyl is optionally substituted with one or more $R^b$, wherein one or more of $R^b$ is —S(O)$_2$—$R^a$, wherein $R^a$ is methyl. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), (I-A) or (I-A2), (I-E1), (I-E2), (I-F), or (I-F1), or a stereoisomer or tautomer thereof, or a pharmaceutically acceptable salt of any of the foregoing, ring A is selected from the group consisting of

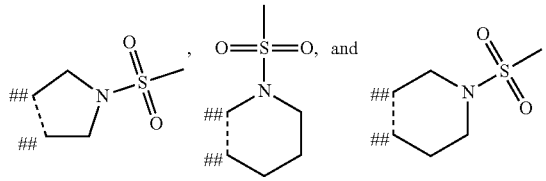

wherein ## represent a point of attachment to the remainder of the molecule and the dashed line represents a single or double bond. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), (I-A) or (I-A2), (I-E1), (I-E2), (I-F), or (I-F1), or a stereoisomer or tautomer thereof, or a pharmaceutically acceptable salt of any of the foregoing, ring A is a 5-10 membered heterocyclyl, wherein the 5-10 membered heterocyclyl is optionally substituted with one or more $R^b$, wherein $R^b$ is $C_{3-10}$cycloalkyl, wherein the $C_{3-10}$cycloalkyl of $R^b$ is optionally substituted with one or more —OH. In some embodiments, ring A is a 5-10 membered heterocyclyl, wherein the 5-10 membered heterocyclyl is optionally substituted with one or more $R^b$, wherein $R^b$ is $C_{3-6}$cycloalkyl, wherein the $C_{3-6}$cycloalkyl of $R^b$ is optionally substituted with one or more —OH. In some embodiments, ring A is a 5-10 membered heterocyclyl, wherein the 5-10 membered heterocyclyl is optionally substituted with one or more $R^b$, wherein one or more of $R^b$ is

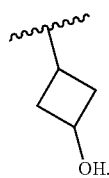

In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I'), (I-A) or (I-A2), (I-E1), (I-E2), (I-F), or (I-F1), or a stereoisomer or tautomer thereof, or a pharmaceutically acceptable salt of any of the foregoing, ring A is a 5-10 membered heterocyclyl, wherein the 5-10 membered heterocyclyl is optionally substituted with one or more $R^b$, wherein $R^b$ is $C_{3-10}$cycloalkyl, wherein the $C_{3-10}$cycloalkyl of $R^b$ is optionally substituted with one or more —OH or $C_{1-6}$alkyl. In some embodiments, ring A is a 5-10 membered heterocyclyl, wherein the 5-10 membered heterocyclyl is optionally substituted with one or more $R^b$, wherein $R^b$ is $C_{3-6}$cycloalkyl, wherein the $C_{3-6}$cycloalkyl of $R^b$ is optionally substituted with one or more —OH or $C_{1-3}$alkyl. In some embodiments, ring A is a 5-10 membered heterocyclyl, wherein the 5-10 membered heterocyclyl is optionally substituted with one or more $R^b$, wherein one or more of $R^b$ is selected from the group consisting of

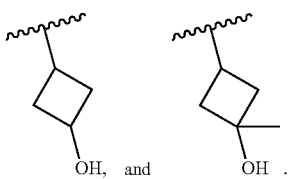

In some variations, the embodiments provided herein also apply to a compound of formula (II), or a stereoisomer or tautomer thereof, or a pharmaceutically acceptable salt of any of the foregoing, or any variation or embodiment thereof.

In some embodiments of a compound of formula (I), (I-A) or (I-A2), (I-E1), (I-E2), (I-F), or (I-F1), or a stereoisomer or tautomer thereof, or a pharmaceutically acceptable salt of any of the foregoing, ring A is

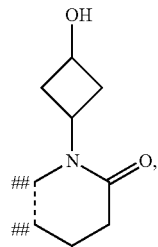

wherein ## represent a point of attachment to the remainder of the molecule and the dashed line represents a single or double bond. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I'), (I-A) or (I-A2), (I-E1), (I-E2), (I-F), or (I-F1), or a stereoisomer or tautomer thereof, or a pharmaceutically acceptable salt of any of the foregoing, ring A is selected from the group consisting of

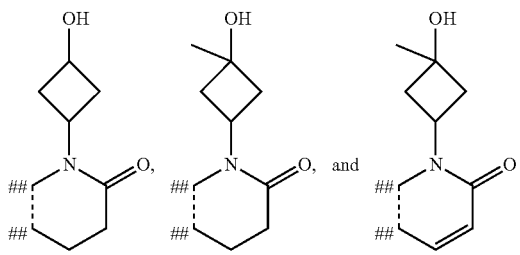

wherein ## represent a point of attachment to the remainder of the molecule and the dashed line represents a single or double bond. In some variations, the embodiments provided herein also apply to a compound of formula (II), or a stereoisomer or tautomer thereof, or a pharmaceutically acceptable salt of any of the foregoing, or any variation or embodiment thereof.

In some embodiments of a compound of formula (I), (I-A) or (I-A2), (I-E1), (I-E2), (I-F), or (I-F1), or a stereoisomer or tautomer thereof, or a pharmaceutically acceptable salt of any of the foregoing, ring A is a 5-10 membered heterocyclyl, wherein the 5-10 membered heterocyclyl is optionally substituted with one or more $R^b$, wherein $R^b$ is 3-10 membered heterocyclyl. In some embodiments, ring A is a 5-10 membered heterocyclyl, wherein the 5-10 membered heterocyclyl is optionally substituted with one or more $R^b$, wherein $R^b$ is 3-6 membered heterocyclyl. In some embodiments, ring A is a 5-10 membered heterocyclyl, wherein the 5-10 membered heterocyclyl is optionally substituted with one or more $R^b$, wherein one or more of $R^b$ is

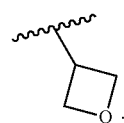 [SMILES: *C1COC1]

In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), (I-A) or (I-A2), (I-E1), (I-E2), (I-F), or (I-F1), or a stereoisomer or tautomer thereof, or a pharmaceutically acceptable salt of any of the foregoing, ring A is

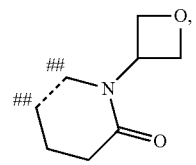

wherein ## represent a point of attachment to the remainder of the molecule and the dashed line represents a single or double bond. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), (I-A) or (I-A2), (I-E1), (I-E2), (I-F), or (I-F1), or a stereoisomer or tautomer thereof, or a pharmaceutically acceptable salt of any of the foregoing, ring A is a 5-10 membered heteroaryl. In some embodiments, ring A is a 5-6 membered heteroaryl. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), (I-A) or (I-A2), (I-E1), (I-E2), (I-F), or (I-F1), or a stereoisomer or tautomer thereof, or a pharmaceutically acceptable salt of any of the foregoing, ring A is selected from the group consisting of

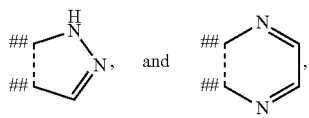

wherein ## represent a point of attachment to the remainder of the molecule and the dashed line represents a single or double bond. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), or a stereoisomer or tautomer thereof, or a pharmaceutically acceptable salt of any of the foregoing, ring A is a 5-10 membered heteroaryl, wherein the 5-10 membered heteroaryl is optionally substituted with one or more $R^c$, wherein one or more $R^c$ is $C_{1-6}$alkyl. In some embodiments ring A is a 5-6 membered heteroaryl, wherein the 5-6 membered heteroaryl is optionally substituted with one or more $R^c$, wherein one or more $R^c$ is $C_{1-3}$alkyl. In some embodiments, ring A is a 5-6 membered heteroaryl, wherein the 5-6 membered heteroaryl is optionally substituted with one or more $R^c$, wherein one or more $R^c$ is methyl. In some embodiments, ring A is a 5-6 membered heteroaryl, wherein the 5-6 membered heteroaryl is optionally substituted with one or more $R^c$, wherein one or more $R^c$ is isopropyl. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), (I-A) or (I-A2), (I-E1), (I-E2), (I-F), or (I-F1), or a stereoisomer or tautomer thereof, or a pharmaceutically acceptable salt of any of the foregoing, ring A is selected from the group consisting of

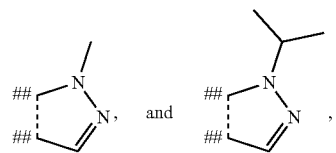

wherein ## represent a point of attachment to the remainder of the molecule and the dashed line represents a single or double bond. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), (I-A) or (I-A2), (I-E1), (I-E2), (I-F), or (I-F1), or a stereoisomer or tautomer thereof, or a pharmaceutically acceptable salt of any of the foregoing, ring A is a 5-10 membered heteroaryl, wherein the 5-10 membered heteroaryl is optionally substituted with one or more $R^c$, wherein one or more $R^c$ is $C_{1-6}$alkyl, wherein the $C_{1-6}$ alkyl of $R^c$ is optionally substituted with one or more —$S(O)_2$—$R^a$, wherein $R^a$ is $C_{1-6}$alkyl. In some embodiments, ring A is a 5-6 membered heteroaryl, wherein the 5-6 membered heteroaryl is optionally substituted with one or more $R^c$, wherein one or more $R^c$ is $C_{1-3}$alkyl, wherein the $C_{1-3}$alkyl of $R^c$ is optionally substituted with one or more —$S(O)_2$—$R^a$, wherein $R^a$ is $C_{1-3}$alkyl. In some embodiments, ring A is a 5-6 membered heteroaryl, wherein the 5-6 membered heteroaryl is optionally substituted with one or more $R^c$, wherein one or more $R^c$ is $C_{1-3}$alkyl, wherein the $C_{1-3}$alkyl of $R^c$ is optionally substituted with one or more —$S(O)_2$—$R^a$, wherein $R^a$ is methyl. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), (I-A) or (I-A2), (I-E1), (I-E2), (I-F), or (I-F1), or a stereoisomer or tautomer thereof, or a pharmaceutically acceptable salt of any of the foregoing, ring A is

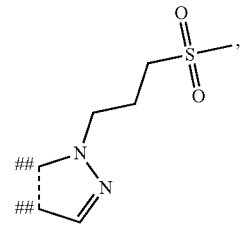

wherein ## represent a point of attachment to the remainder of the molecule and the dashed line represents a single or double bond. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), (I-A) or (I-A2), (I-E1), (I-E2), (I-F), or (I-F1), or a stereoisomer or tautomer thereof, or a pharmaceutically acceptable salt of any of the foregoing, ring A is a 5-10 membered heteroaryl, wherein the 5-10 membered heteroaryl is optionally substituted with one or more $R^c$, wherein one or more $R^c$ is $C_{3-10}$cycloalkyl, wherein the $C_{3-10}$cycloalkyl of $R^c$ is optionally substituted with one or more —OH. In some embodiments, ring A is a 5-10 membered heteroaryl, wherein the 5-6 membered heteroaryl is optionally substituted with one or more $R^c$, wherein one or more $R^c$ is $C_{3-6}$cycloalkyl, wherein the $C_{3-6}$cycloalkyl of $R^c$ is optionally substituted with one or more —OH. In some embodiments, ring A is a 5-10 membered heteroaryl, wherein the 5-6 membered heteroaryl is optionally substituted with one or more $R^c$, wherein one or more $R^c$ is

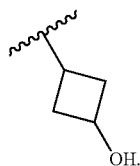 [SMILES: *C1CC(O)C1]

In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I'), (I-A) or (I-A2), (I-E1), (I-E2), (I-F), or (I-F1), or a stereoisomer or tautomer thereof, or a pharmaceutically acceptable salt of any of the foregoing, ring A is a 5-10 membered heteroaryl, wherein the 5-10 membered heteroaryl is optionally substituted with one or more $R^c$, wherein one or more $R^c$ is $C_{3-10}$cycloalkyl, wherein the $C_{3-10}$cycloalkyl of $R^c$ is optionally substituted with one or more —OH, or $C_{1-6}$alkyl. In some embodiments, ring A is a 5-10 membered heteroaryl, wherein the 5-6 membered heteroaryl is optionally substituted with one or more $R^c$, wherein one or more $R^c$ is $C_{3-6}$cycloalkyl, wherein the $C_{3-6}$cycloalkyl of $R^c$ is optionally substituted with one or more —OH, or $C_{1-3}$alkyl. In some embodiments, ring A is a 5-10 membered heteroaryl, wherein the 5-6 membered heteroaryl is optionally substituted with one or more $R^c$, wherein one or more $R^c$ is selected from the group consisting of

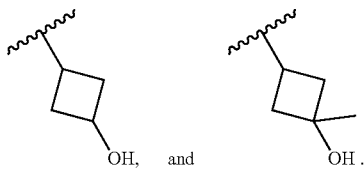

In some variations, the embodiments provided herein also apply to a compound of formula (II), or a stereoisomer or tautomer thereof, or a pharmaceutically acceptable salt of any of the foregoing, or any variation or embodiment thereof.

In some embodiments of a compound of formula (I), (I-A) or (I-A2), (I-E1), (I-E2), (I-F), or (I-F1), or a stereoisomer or tautomer thereof, or a pharmaceutically acceptable salt of any of the foregoing, ring A is

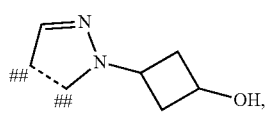

wherein ## represent a point of attachment to the remainder of the molecule and the dashed line represents a single or double bond. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I'), (I-A) or (I-A2), (I-E1), (I-E2), (I-F), or (I-F1), or a stereoisomer or tautomer thereof, or a pharmaceutically acceptable salt of any of the foregoing, ring A is selected from the group consisting of

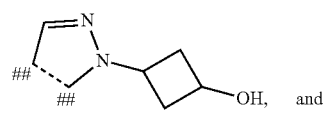

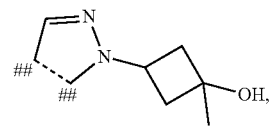

wherein ## represent a point of attachment to the remainder of the molecule and the dashed line represents a single or double bond. In some variations, the embodiments provided herein also apply to a compound of formula (II), or a stereoisomer or tautomer thereof, or a pharmaceutically acceptable salt of any of the foregoing, or any variation or embodiment thereof.

In some embodiments of a compound of formula (I), (I-A) or (I-A2), (I-E1), (I-E2), (I-F), or (I-F1), or a stereoisomer or tautomer thereof, or a pharmaceutically acceptable salt of any of the foregoing, ring A is a 5-10 membered heteroaryl, wherein the 5-10 membered heteroaryl is optionally substituted with one or more $R^b$, wherein $R^b$ is 3-10 membered heterocyclyl. In some embodiments, ring A is a 5-10 membered heteroaryl, wherein the 5-10 membered heteroaryl is optionally substituted with one or more $R^b$, wherein $R^b$ is 3-6 membered heterocyclyl. In some embodiments, ring A is a 5-10 membered heteroaryl, wherein the 5-10 membered heterocyclyl is optionally substituted with one or more $R^b$, wherein one or more of $R^b$ is

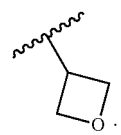

In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), (I-A) or (I-A2), (I-E1), (I-E2), (I-F), or (I-F1), or a stereoisomer or tautomer thereof, or a pharmaceutically acceptable salt of any of the foregoing, ring A is

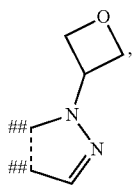

wherein ## represent a point of attachment to the remainder of the molecule and the dashed line represents a single or double bond. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments, provided herein is a compound of formula (I), (I-A) or (I-A2), (I-E), (I-E1), or (I-F), or a stereoisomer or tautomer thereof, or a pharmaceutically acceptable salt thereof, wherein the compound is a compound of formula (I-F2):

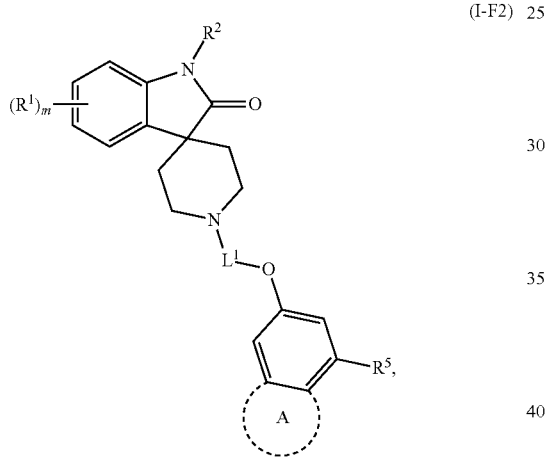

(I-F2)

or a stereoisomer or tautomer thereof, or a pharmaceutically acceptable salt of any of the foregoing, wherein: $R^5$ is halo, —CN, 3-10 membered heterocyclyl, $C_{1-6}$alkyl, or $C_{1-6}$alkoxy, wherein the $C_{1-6}$alkyl of $R^5$ is optionally substituted with one or more halo, or —OH and wherein the $C_{1-6}$alkoxy is optionally substituted with one or more halo; ring A is 5-10 membered heterocyclyl or a 5-10 membered heteroaryl, wherein the 5-10 membered heterocyclyl of ring A is optionally substituted with one or more $R^b$, and wherein the 5-10 membered heteroaryl of ring A is optionally substituted with one or more $R^c$; and m, $R^1$, $R^2$, $L^1$, $R^b$, and $R^c$, are as defined for formula (I). In some variations, $R^5$ is halo, —CN, 3-10 membered heterocyclyl, $C_{1-6}$alkyl, or $C_{1-6}$alkoxy, wherein the $C_{1-6}$alkyl of $R^5$ is optionally substituted with one or more halo, or —OH and wherein the $C_{1-6}$alkoxy of $R^5$ is optionally substituted with one or more halo; ring A is 5-10 membered heterocyclyl or a 5-10 membered heteroaryl, wherein the 5-10 membered heterocyclyl of ring A is optionally substituted with one or more $R^b$, and wherein the 5-10 membered heteroaryl of ring A is optionally substituted with one or more $R^c$; and m, $R^1$, $R^2$, $L^1$, $R^b$, and $R^c$, of formula (I-F2) are as defined for a compound of formula (I'), or (II), or a stereoisomer or tautomer thereof, or a pharmaceutically acceptable salt of any of the foregoing, or any variation or embodiment thereof.

In some embodiments of a compound of formula (I), (I-A) or (I-A2), (I-E), (I-E1), (I-F), or (I-F2), or a stereoisomer or tautomer thereof, or a pharmaceutically acceptable salt of any of the foregoing, $R^2$ is H. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (II), such as a compound of formula (I), (I-A) or (I-A2), (I-E), (I-E1), (I-F), or (I-F2), or a stereoisomer or tautomer thereof, or a pharmaceutically acceptable salt of any of the foregoing, $R^2$ is $C_{1-6}$alkyl, wherein the $C_{1-6}$alkyl of $R^2$ is optionally substituted with one or more deuterium, —OH, —NH$_2$, or $C_{1-6}$alkoxy. In some embodiments, $R^2$ is methyl optionally substituted with one or more deuterium. In some embodiments, $R^2$ is

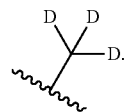

In some embodiments of a compound of formula (I), (I-A) or (I-A2), (I-E), (I-E1), (I-F), or (I-F2), or a stereoisomer or tautomer thereof, or a pharmaceutically acceptable salt of any of the foregoing, m is an integer from 0 to 4. In some embodiments, m is an integer from 0 to 2. In some embodiments m is 1. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), (I-A) or (I-A2), (I-E), (I-E1), (I-F), or (I-F2), or a stereoisomer or tautomer thereof, or a pharmaceutically acceptable salt of any of the foregoing, $R^1$ is halo. In some embodiments $R^1$ is Cl. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (II), such as a compound of formula (I'), (I), (I-A) or (I-A2), (I-E), (I-E1), (I-F), or (I-F2), or a stereoisomer or tautomer thereof, or a pharmaceutically acceptable salt of any of the foregoing, $R^1$ is halo. In some embodiments $R^1$ is Cl, Br, or I.

In some embodiments of a compound of formula (I), (I-A) or (I-A2), (I-E), (I-E1), (I-F), or (I-F2), or a stereoisomer or tautomer thereof, or a pharmaceutically acceptable salt of any of the foregoing, $R^1$ is —CN. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (II), such as a compound of formula (I), (I-A) or (I-A2), (I-E), (I-E1), (I-F), or (I-F2), or a stereoisomer or tautomer thereof, or a pharmaceutically acceptable salt of any of the foregoing, $R^1$ is $C_{1-6}$alkyl, wherein the $C_{1-6}$alkyl of $R^1$ is optionally substituted with one or more halo. In some embodiments, $R^1$ is $C_{1-3}$alkyl, wherein the $C_{1-3}$alkyl of $R^1$ is optionally substituted with one or more halo. In some embodiments, $R^1$ is $C_{1-3}$alkyl, wherein the $C_{1-3}$alkyl of $R^1$ is optionally substituted with one or more F. In some embodiments, $R^1$ is methyl, wherein the methyl of $R^1$ is optionally substituted with one or more F. In some embodiments, $R^1$ is

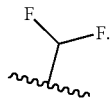

In some embodiments of a compound of formula (I), (I-A) or (I-A2), (I-E), (I-E1), (I-F), or (I-F2), or a stereoisomer or tautomer thereof, or a pharmaceutically acceptable salt of any of the foregoing, $L^1$ is $C_{1-6}$alkylene. In some embodiments, $L^1$ is ethylene. In some variations, the embodiments provided herein also apply to a compound of formula (I') or a stereoisomer or tautomer thereof, or a pharmaceutically acceptable salt of any of the foregoing, or any variation or embodiment thereof. In some embodiments, $L^1$ is

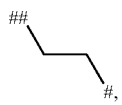

wherein, for each $L^1$, # denotes the point of attachment to $L^2$ and ## denotes the point of attachment to the remainder of the molecule. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (II), such as a compound of formula (I'), (I), (I-A) or (I-A2), (I-E), (I-E1), (I-F), or (I-F2), or a stereoisomer or tautomer thereof, or a pharmaceutically acceptable salt of any of the foregoing, $L^1$ is $C_{1-6}$alkylene, optionally substituted with one or more deuterium. In some embodiments, $L^1$ is ethylene optionally substituted with one or more deuterium. In some embodiments, $L^1$ is

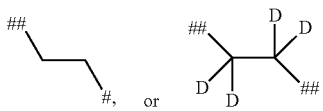

wherein, for each $L^1$, # denotes the point of attachment to $L^2$ and ## denotes the point of attachment to the remainder of the molecule.

In some embodiments of a compound of formula (I), (I-A) or (I-A2), (I-E), (I-E1), (I-F), or (I-F2), or a stereoisomer or tautomer thereof, or a pharmaceutically acceptable salt of any of the foregoing, ring A is a 5-10 membered heterocyclyl, wherein the 5-10 membered heterocyclyl is optionally substituted with one or more of $R^b$, wherein one or more $R^b$ is oxo. In some embodiments, ring A is a 5-10 membered heterocyclyl, wherein the 5-10 membered heterocyclyl is optionally substituted with one or more of $R^b$, wherein one or more $R^b$ is oxo. In some variations, the embodiments provided herein also apply to a compound of the formula (I'), or (II), or a stereoisomer or tautomer thereof, or a pharmaceu-
tically acceptable salt of any of the foregoing, or any variation or embodiment thereof.

In some embodiments of a compound of formula (I), (I-A) or (I-A2), (I-E), (I-E1), (I-F), or (I-F2), or a stereoisomer or tautomer thereof, or a pharmaceutically acceptable salt of any of the foregoing, ring A is

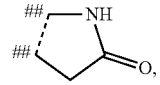

wherein ## represent a point of attachment to the remainder of the molecule and the dashed line represents a single or double bond. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (II), such as a compound of formula (I), (I-A) or (I-A2), (I-E), (I-E1), (I-F), or (I-F2), or a stereoisomer or tautomer thereof, or a pharmaceutically acceptable salt of any of the foregoing, ring A is

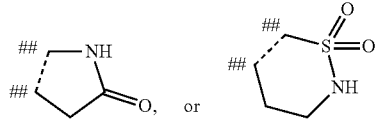

wherein ## represent a point of attachment to the remainder of the molecule and the dashed line represents a single or double bond.

In some embodiments of a compound of formula (I), (I-A) or (I-A2), (I-E), (I-E1), (I-F), or (I-F2), or a stereoisomer or tautomer thereof, or a pharmaceutically acceptable salt of any of the foregoing, ring A is a 5-10 membered heterocyclyl, wherein the 5-10 membered heterocyclyl is optionally substituted with one or more $R^b$, wherein each $R^b$ is independently oxo, or $C_{1-6}$alkyl. In some embodiments, ring A is a 5-10 membered heterocyclyl, wherein the 5-10 membered heterocyclyl is optionally substituted with one or more $R^b$, wherein each $R^b$ is independently oxo, or $C_{1-6}$alkyl, wherein the $C_{1-6}$alkyl of $R^b$ is optionally substituted with one or more halo, OH, or —S(O)$_2$—$C_{1-6}$alkyl. In some embodiments, ring A is a 5-10 membered heterocyclyl, wherein the 5-10 membered heterocyclyl is optionally substituted with one or more $R^b$, wherein each $R^b$ is independently oxo, or $C_{1-3}$alkyl. In some embodiments, ring A is a 5-10 membered heterocyclyl, wherein the 5-10 membered heterocyclyl is optionally substituted with one or more $R^b$, wherein each $R^b$ is independently selected from the group consisting of oxo, and

In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), (I-A) or (I-A2), (I-E), (I-E1), (I-F), or (I-F2), or a stereoisomer or tautomer thereof, or a pharmaceutically acceptable salt of any of the foregoing, ring A is

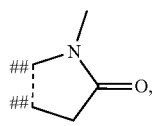

wherein ## represent a point of attachment to the remainder of the molecule and the dashed line represents a single or double bond. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I'), (I-A) or (I-A2), (I-E), (I-E1), (I-F), or (I-F2), or a stereoisomer or tautomer thereof, or a pharmaceutically acceptable salt of any of the foregoing, ring A is a 5-10 membered heterocyclyl, wherein the 5-10 membered heterocyclyl is optionally substituted with one or more $R^b$, wherein $R^b$ is $C_{3-10}$cycloalkyl, wherein the $C_{3-10}$cycloalkyl of $R^b$ is optionally substituted with one or more —OH or $C_{1-6}$alkyl. In some embodiments, ring A is a 5-10 membered heterocyclyl, wherein the 5-10 membered heterocyclyl is optionally substituted with one or more $R^b$, wherein $R^b$ is $C_{3-6}$cycloalkyl, wherein the $C_{3-6}$cycloalkyl of $R^b$ is optionally substituted with one or more —OH or $C_{1-3}$alkyl. In some embodiments, ring A is a 5-10 membered heterocyclyl, wherein the 5-10 membered heterocyclyl is optionally substituted with one or more $R^b$, wherein one or more of $R^b$ is selected from the group consisting of

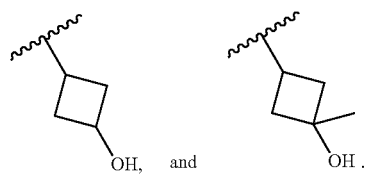

In some variations, the embodiments provided herein also apply to a compound of formula (II), or a stereoisomer or tautomer thereof, or a pharmaceutically acceptable salt of any of the foregoing, or any variation or embodiment thereof.

In some embodiments of a compound of formula (I'), (I-A) or (I-A2), (I-E), (I-E1), (I-F), or (I-F2), or a stereoisomer or tautomer thereof, or a pharmaceutically acceptable salt of any of the foregoing, ring A is selected from the group consisting of

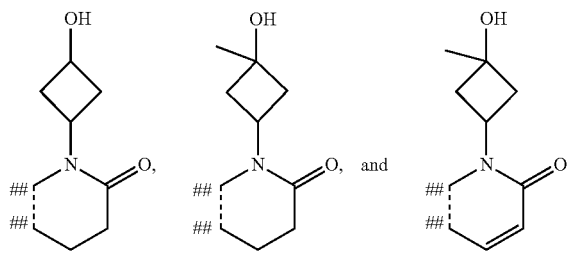

wherein ## represent a point of attachment to the remainder of the molecule and the dashed line represents a single or double bond. In some variations, the embodiments provided herein also apply to a compound of formula (II), or a stereoisomer or tautomer thereof, or a pharmaceutically acceptable salt of any of the foregoing, or any variation or embodiment thereof.

In some embodiments of a compound of formula (II), such as a compound of formula (I'), (I-A) or (I-A2), (I-E), (I-E1), (I-F), or (I-F2), or a stereoisomer or tautomer thereof, or a pharmaceutically acceptable salt of any of the foregoing, ring A is a 5-10 membered heterocyclyl, wherein the 5-10 membered heterocyclyl is optionally substituted with one or more $R^b$, wherein $R^b$ is $C_{1-6}$alkyl and wherein, the $C_{1-6}$alkyl of $R^b$ is optionally substituted with one or more —OH. In some embodiments, ring A is 5-6 membered heterocyclyl, wherein the 5-6 membered heterocyclyl is optionally substituted with one or more $R^b$, wherein $R^b$ is $C_{1-3}$alkyl and wherein, the $C_{1-3}$alkyl of $R^b$ is optionally substituted with one or more —OH. In some embodiments, ring A is a 5-10 membered heterocyclyl, wherein the 5-6 membered heterocyclyl is optionally substituted with one or more $R^b$, wherein one or more of $R^b$ is —CH$_2$OH.

In some embodiments of a compound of formula (II), such as a compound of formula (I'), (I-A) or (I-A2), (I-E), (I-E1), (I-F), or (I-F2), or a stereoisomer or tautomer thereof, or a pharmaceutically acceptable salt of any of the foregoing, ring A is selected from the group consisting of

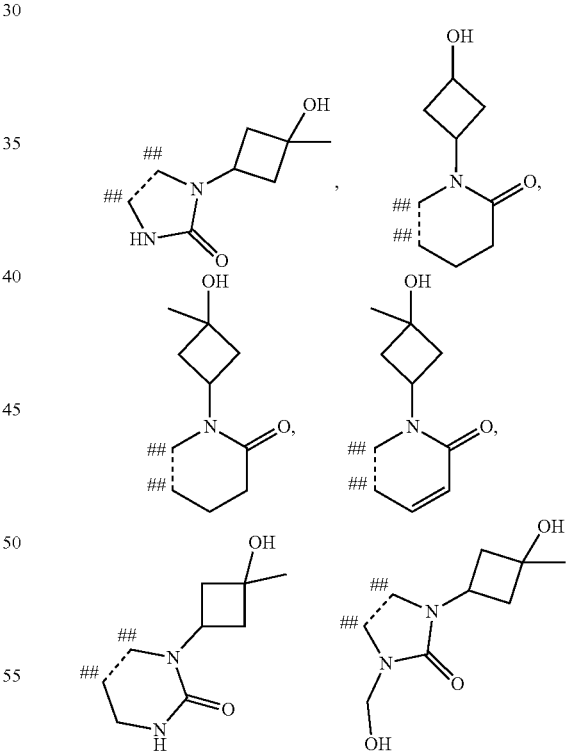

wherein ## represent a point of attachment to the remainder of the molecule and the dashed line represents a single or double bond.

In some embodiments of a compound of formula (I'), (I-A) or (I-A2), (I-E), (I-E1), (I-F), or (I-F2), or a stereoisomer or tautomer thereof, or a pharmaceutically acceptable salt of any of the foregoing, ring A is a 5-10 membered heteroaryl, wherein the 5-10 membered heteroaryl is optionally substituted with one or more $R^c$, wherein one or more $R^c$ is $C_{3-10}$cycloalkyl, wherein the $C_{3-10}$cycloalkyl of $R^c$ is optionally substituted with one or more —OH, or $C_{1-6}$alkyl. In some embodiments, ring A is a 5-10 membered heteroaryl, wherein the 5-6 membered heteroaryl is optionally substituted with one or more $R^c$, wherein one or more $R^c$ is $C_{3-6}$cycloalkyl, wherein the $C_{3-6}$cycloalkyl of $R^c$ is optionally substituted with one or more —OH, or $C_{1-3}$alkyl. In some embodiments, ring A is a 5-10 membered heteroaryl, wherein the 5-6 membered heteroaryl is optionally substituted with one or more $R^c$, wherein one or more $R^c$ is selected from the group consisting of

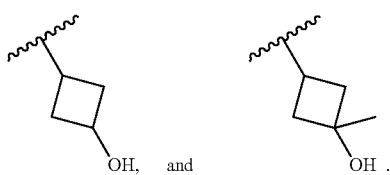

In some variations, the embodiments provided herein also apply to a compound of formula (II), or a stereoisomer or tautomer thereof, or a pharmaceutically acceptable salt of any of the foregoing, or any variation or embodiment thereof.

In some embodiments of a compound of formula (I'), (I-A) or (I-A2), (I-E), (I-E1), (I-F), or (I-F2), or a stereoisomer or tautomer thereof, or a pharmaceutically acceptable salt of any of the foregoing, ring A is selected from the group consisting of

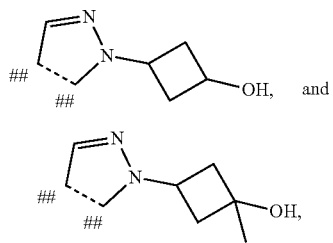

wherein ## represent a point of attachment to the remainder of the molecule and the dashed line represents a single or double bond. In some variations, the embodiments provided herein also apply to a compound of formula (II), or a stereoisomer or tautomer thereof, or a pharmaceutically acceptable salt of any of the foregoing, or any variation or embodiment thereof.

In some embodiments of a compound of formula (II), such as a compound of formula (I'), (I-A) or (I-A2), (I-E), (I-E1), (I-F), or (I-F2), or a stereoisomer or tautomer thereof, or a pharmaceutically acceptable salt of any of the foregoing, ring A is selected from the group consisting of

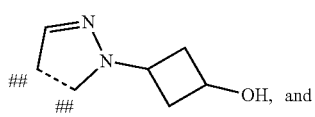

-continued

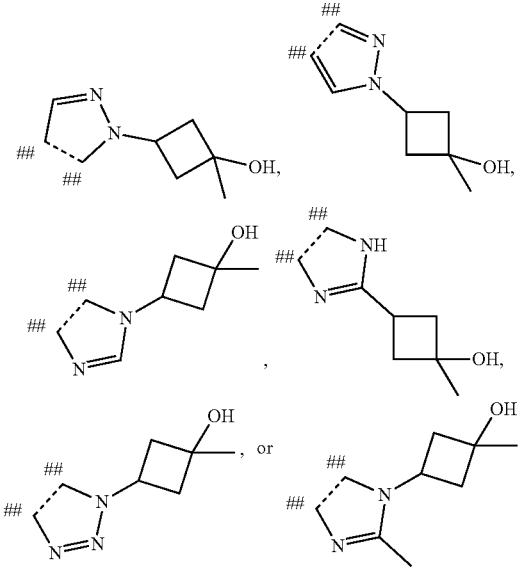

wherein ## represent a point of attachment to the remainder of the molecule and the dashed line represents a single or double bond.

In some embodiments of a compound of formula (I), (I-A) or (I-A2), (I-E), (I-E1), (I-F), or (I-F2), or a stereoisomer or tautomer thereof, or a pharmaceutically acceptable salt of any of the foregoing, $R^5$ is halo. In some embodiments, $R^5$ is fluoro. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), (I-A) or (I-A2), (I-E), (I-E1), (I-F), or (I-F2), or a stereoisomer or tautomer thereof, or a pharmaceutically acceptable salt of any of the foregoing, $R^5$ is $C_{1-6}$alkyl. In some embodiments, $R^5$ is $C_{1-3}$alkyl. In some embodiments, $R^5$ is methyl. In some embodiments, $R^5$ is $C_{1-6}$alkyl, wherein the $C_{1-6}$alkyl of $R^5$ is optionally substituted with one or more halo. In some embodiments, $R^5$ is $C_{1-3}$alkyl, wherein the $C_{1-3}$alkyl of $R^5$ is optionally substituted with one or more halo. In some embodiments, $R^5$ is $C_{1-3}$alkyl, wherein the $C_{1-3}$alkyl of $R^5$ is optionally substituted with one or more fluoro. In some embodiments, $R^5$ is

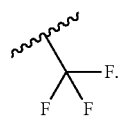

In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (II), such as a compound of formula (I'), (I-A) or (I-A2), (I-E), (I-E1), (I-F), or (I-F2), or a stereoisomer or tautomer thereof, or a pharmaceutically acceptable salt of any of the foregoing, $R^5$ is halo, —CN, or $C_{1-6}$alkoxy, wherein the $C_{1-6}$alkoxy of $R^5$ is optionally substituted with one or more halo. In some embodiments, $R^5$ F, —CN, or $C_{1-3}$alkoxy, wherein the $C_{1-3}$alkoxy of $R^5$ is optionally substituted with one or more F. In some embodiments, $R^5$ is —OCHF$_2$.

In some embodiments, provided herein is a compound of formula (I), (I-A) or (I-A2), (I-E1), or (I-E2), or a stereoisomer or tautomer thereof, or a pharmaceutically acceptable salt thereof, wherein the compound is a compound of formula (I-G):

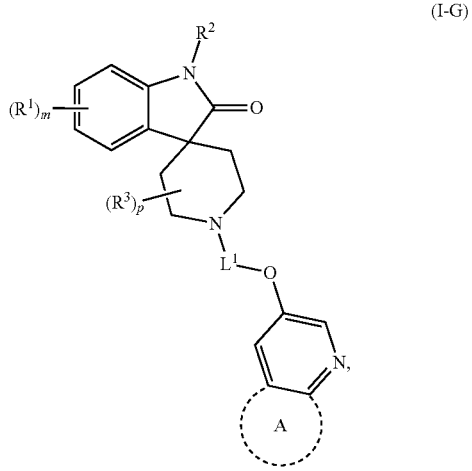

(I-G)

or a stereoisomer or tautomer thereof, or a pharmaceutically acceptable salt of any of the foregoing, wherein: ring A is 5-10 membered heterocyclyl or a 5-10 membered heteroaryl, wherein the 5-10 membered heterocyclyl of ring A is optionally substituted with one or more $R^b$, and wherein the 5-10 membered heteroaryl of ring A is optionally substituted with one or more $R^c$; and m, $R^1$, $R^2$, $L^1$, $R^b$, and $R^c$, are as defined for formula (I). In some variations, ring A is 5-10 membered heterocyclyl or a 5-10 membered heteroaryl, wherein the 5-10 membered heterocyclyl of ring A is optionally substituted with one or more $R^b$, and wherein the 5-10 membered heteroaryl of ring A is optionally substituted with one or more $R^c$; and m, $R^1$, $R^2$, $L^1$, $R^b$, and $R^c$ of formula (I-G) are as defined for a compound of formula (I'), or (II), or a stereoisomer or tautomer thereof, or a pharmaceutically acceptable salt of any of the foregoing, or any variation or embodiment thereof.

In some embodiments of a compound of formula (I), (I-A) or (I-A2), (I-E), (I-E1), or (I-G), or a stereoisomer or tautomer thereof, or a pharmaceutically acceptable salt of any of the foregoing, $R^2$ is H. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (II), such as a compound of formula (I), (I-A) or (I-A2), (I-E), (I-E1), or (I-G), or a stereoisomer or tautomer thereof, or a pharmaceutically acceptable salt of any of the foregoing, $R^2$ is $C_{1-6}$alkyl, wherein the $C_{1-6}$alkyl of $R^2$ is optionally substituted with one or more deuterium. In some embodiments, $R^2$ is methyl optionally substituted with one or more deuterium. In some embodiments, $R^2$ is

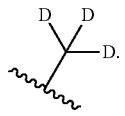

In some embodiments of a compound of formula (I), (I-A) or (I-A2), (I-E), (I-E1), or (I-G), or a stereoisomer or tautomer thereof, or a pharmaceutically acceptable salt of any of the foregoing, m is an integer from 0 to 4. In some embodiments, m is an integer from 0 to 2. In some embodiments, m is 0 or 1. In some embodiments m is 1. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), (I-A) or (I-A2), (I-E), (I-E1), or (I-G), or a stereoisomer or tautomer thereof, or a pharmaceutically acceptable salt of any of the foregoing, $R^1$ is halo. In some embodiments $R^1$ is Cl. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), (I-A) or (I-A2), (I-E), (I-E1), or (I-G), or a stereoisomer or tautomer thereof, or a pharmaceutically acceptable salt of any of the foregoing, $R^1$ is —CN. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I'), (I-A) or (I-A2), (I-E), (I-E1), or (I-G), or a stereoisomer or tautomer thereof, or a pharmaceutically acceptable salt of any of the foregoing, $R^1$ is $C_{1-6}$alkyl, wherein the $C_{1-6}$alkyl of $R^1$ is optionally substituted with one or more halo. In some embodiments, $R^1$ is $C_{1-3}$alkyl, wherein the $C_{1-3}$alkyl of $R^1$ is optionally substituted with one or more halo. In some embodiments, $R^1$ is $C_{1-3}$alkyl, wherein the $C_{1-3}$alkyl of $R^1$ is optionally substituted with one or more F. In some embodiments, $R^1$ is methyl, wherein the methyl of $R^1$ is optionally substituted with one or more F. In some embodiments, $R^1$ is methyl. In some embodiments, $R^1$ is

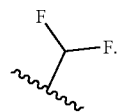 [SMILES: *C(F)F]

In some variations, the embodiments provided herein also apply to a compound of formula (II), or a stereoisomer or tautomer thereof, or a pharmaceutically acceptable salt of any of the foregoing, or any variation or embodiment thereof.

In some embodiments of a compound of formula (I), (I-A) or (I-A2), (I-E), (I-E1), or (I-G), or a stereoisomer or tautomer thereof, or a pharmaceutically acceptable salt of any of the foregoing, $L^1$ is $C_{1-6}$alkylene. In some embodiments, $L^1$ is $C_{1-3}$alkylene. In some embodiments, $L^1$ is ethylene. In some embodiments, $L^1$ is

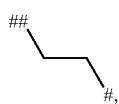

wherein, for each L¹, # denotes the point of attachment to —O— and ## denotes the point of attachment to the remainder of the molecule. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), (I-A) or (I-A2), (I-E), (I-E1), or (I-G), or a stereoisomer or tautomer thereof, or a pharmaceutically acceptable salt of any of the foregoing, ring A is a 5-10 membered heterocyclyl, wherein the 5-10 membered heterocyclyl is optionally substituted with one or more $R^b$, wherein each $R^b$ is independently oxo, or $C_{1-6}$alkyl. In some embodiments, ring A is a 5-10 membered heterocyclyl, wherein the 5-10 membered heterocyclyl is optionally substituted with one or more $R^b$, wherein each $R^b$ is independently oxo, or $C_{1-6}$alkyl, wherein the $C_{1-6}$alkyl of $R^b$ is optionally substituted with one or more —OH. In some embodiments, ring A is a 5-10 membered heterocyclyl, wherein the 5-10 membered heterocyclyl is optionally substituted with one or more $R^b$, wherein wherein each $R^b$ is independently oxo, or $C_{1-3}$alkyl, wherein the $C_{1-3}$alkyl of $R^b$ is optionally substituted with one or more —OH. In some embodiments, ring A is a 5-10 membered heterocyclyl, wherein the 5-10 membered heterocyclyl is optionally substituted with one or more $R^b$, wherein each $R^b$ is independently selected from the group consisting of oxo,

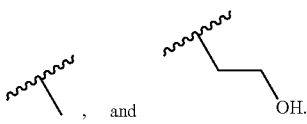

In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I'), (I-A) or (I-A2), (I-E), (I-E1), or (I-G), or a stereoisomer or tautomer thereof, or a pharmaceutically acceptable salt of any of the foregoing, ring A is a 5-10 membered heterocyclyl, wherein the 5-10 membered heterocyclyl is optionally substituted with one or more $R^b$, wherein each $R^b$ is independently oxo, or $C_{1-6}$alkyl. In some embodiments, ring A is a 5-10 membered heterocyclyl, wherein the 5-10 membered heterocyclyl is optionally substituted with one or more $R^b$, wherein each $R^b$ is independently oxo, or $C_{1-6}$alkyl. In some embodiments, the $C_{1-6}$alkyl of $R^b$ is optionally substituted with one or more halo, OH, —S(O)₂—$C_{1-6}$alkyl, or $C_{3-10}$cycloalkyl, wherein the $C_{3-10}$cycloalkyl of the $C_{1-6}$alkyl of $R^b$ is further optionally substituted with one or more $C_{1-6}$alkyl or —OH. In some embodiments, each $R^b$ is independently oxo, or $C_{1-3}$alkyl. In some embodiments the $C_{1-3}$alkyl of $R^b$ is optionally substituted with one or more halo, OH, —S(O)₂—$C_{1-3}$alkyl, or $C_{3-6}$cycloalkyl, wherein the $C_{3-6}$cycloalkyl of the $C_{1-3}$alkyl of $R^b$ is further optionally substituted with one or more $C_{1-3}$alkyl or —OH. In some embodiments, ring A is a 5-10 membered heterocyclyl, wherein the 5-10 membered heterocyclyl is optionally substituted with one or more $R^b$, wherein each $R^b$ is independently selected from the group consisting of oxo

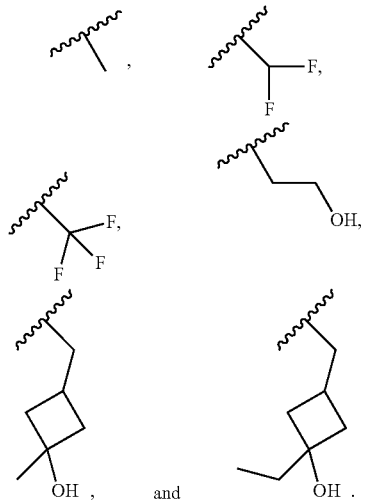

In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (II), such as a compound of formula (I'), (I-A) or (I-A2), (I-E), (I-E1), or (I-G), or a stereoisomer or tautomer thereof, or a pharmaceutically acceptable salt of any of the foregoing, ring A is a 5-10 membered heterocyclyl, wherein the 5-10 membered heterocyclyl is optionally substituted with one or more $R^b$, wherein each $R^b$ is independently selected from the group consisting of oxo,

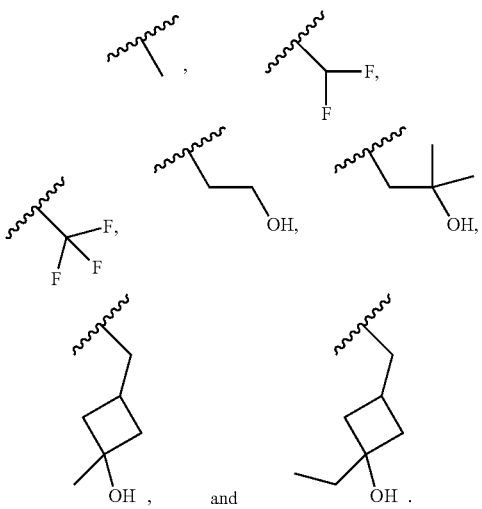

In some embodiments of a compound of formula (I), (I-A) or (I-A2), (I-E), (I-E1), or (I-G), or a stereoisomer or tautomer thereof, or a pharmaceutically acceptable salt of any of the foregoing, ring A is selected from the group consisting of

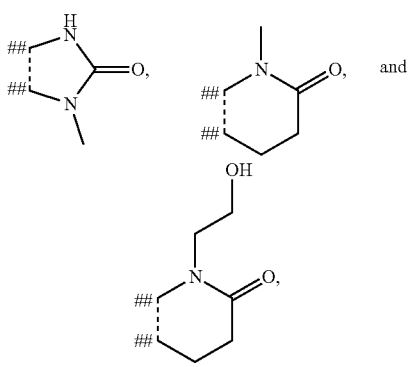

wherein ## represent a point of attachment to the remainder of the molecule and the dashed line represents a single or double bond. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I'), (I-A) or (I-A2), (I-E), (I-E1), or (I-G), or a stereoisomer or tautomer thereof, or a pharmaceutically acceptable salt of any of the foregoing, ring A is selected from the group consisting of

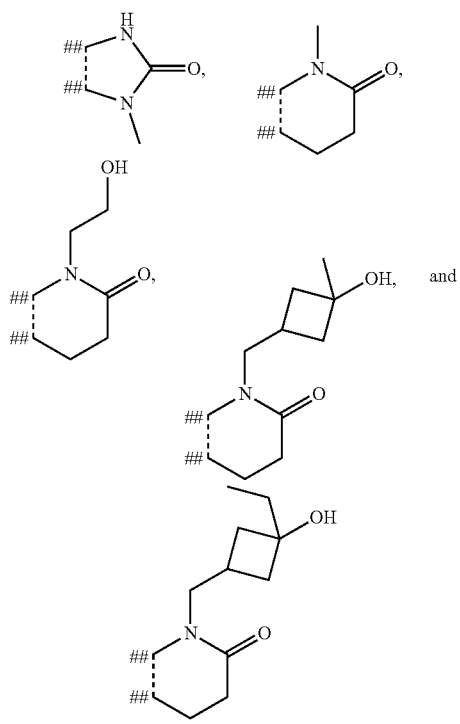

wherein ## represent a point of attachment to the remainder of the molecule and the dashed line represents a single or double bond. In some variations, the embodiments provided herein also apply to a compound of formula (II), or a stereoisomer or tautomer thereof, or a pharmaceutically acceptable salt of any of the foregoing, or any variation or embodiment thereof.

In some embodiments of a compound of formula (II), such as a compound of formula (I'), (I-A) or (I-A2), (I-E), (I-E1), or (I-G), or a stereoisomer or tautomer thereof, or a pharmaceutically acceptable salt of any of the foregoing, ring A is selected from the group consisting of

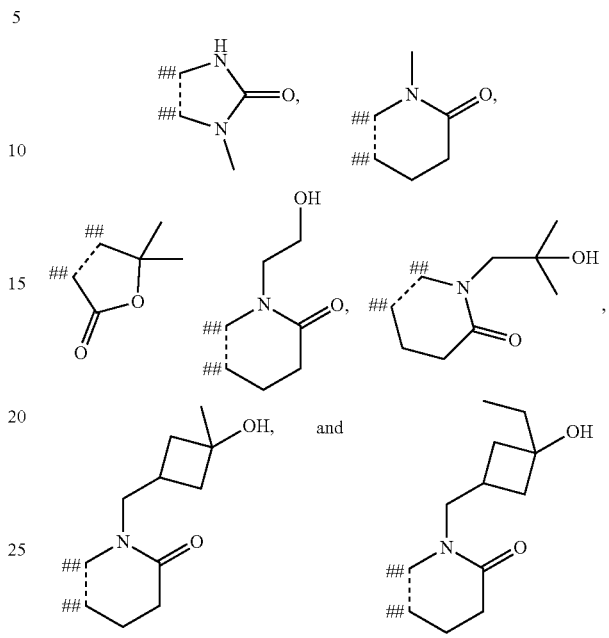

wherein ## represent a point of attachment to the remainder of the molecule and the dashed line represents a single or double bond.

In some embodiments of a compound of formula (I), (I-A) or (I-A2), (I-E), (I-E1), or (I-G), or a stereoisomer or tautomer thereof, or a pharmaceutically acceptable salt of any of the foregoing, ring A is a 5-10 membered heterocyclyl, wherein the 5-10 membered heterocyclyl is optionally substituted with one or more $R^b$, wherein one or more of $R^b$ is —C(O)—$C_{1-6}$alkyl. In some embodiments, ring A is a 5-10 membered heterocyclyl, wherein the 5-10 membered heterocyclyl is optionally substituted with one or more $R^b$, wherein one or more of $R^b$ is —C(O)—$C_{1-3}$alkyl. In some embodiments, ring A is a 5-10 membered heterocyclyl, wherein the 5-10 membered heterocyclyl is optionally substituted with one or more $R^b$, wherein one or more of $R^b$ is

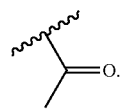

In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), (I-A) or (I-A2), (I-E), (I-E1), or (I-G), or a stereoisomer or tautomer thereof, or a pharmaceutically acceptable salt of any of the foregoing, ring A is

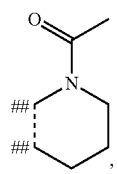

wherein ## represent a point of attachment to the remainder of the molecule and the dashed line represents a single or double bond. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I), (I-A) or (I-A2), (I-E), (I-E1), or (I-G), or a stereoisomer or tautomer thereof, or a pharmaceutically acceptable salt of any of the foregoing, ring A is a 5-10 membered heterocyclyl, wherein the 5-10 membered heterocyclyl is optionally substituted with one or more $R^b$, wherein $R^b$ is $C_{3-10}$cycloalkyl, wherein the $C_{3-10}$cycloalkyl of $R^b$ is optionally substituted with one or more —OH. In some embodiments, ring A is a 5-10 membered heterocyclyl, wherein the 5-10 membered heterocyclyl is optionally substituted with one or more $R^b$, wherein $R^b$ is $C_{3-6}$cycloalkyl, wherein the $C_{3-6}$cycloalkyl of $R^b$ is optionally substituted with one or more —OH. In some embodiments, ring A is a 5-10 membered heterocyclyl, wherein the 5-10 membered heterocyclyl is optionally substituted with one or more $R^b$, wherein one or more of $R^b$ is

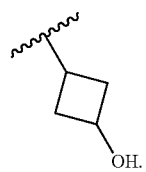 [SMILES: *C1CC(O)C1]

In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I'), (I-A) or (I-A2), (I-E), (I-E1), or (I-G), or a stereoisomer or tautomer thereof, or a pharmaceutically acceptable salt of any of the foregoing, $R^b$ is $C_{3-10}$cycloalkyl optionally substituted with one or more —OH, $C_{3-10}$cycloalkyl, or $C_{1-6}$alkyl, wherein the $C_{1-6}$alkyl is further optionally substituted with one or more —OH. In some embodiments, $R^b$ is $C_{3-6}$cycloalkyl optionally substituted with one or more —OH, $C_{3-6}$cycloalkyl, or $C_{1-3}$alkyl, wherein the $C_{1-3}$alkyl is further optionally substituted with one or more —OH. In some embodiments, $R^b$ is selected from the group consisting of

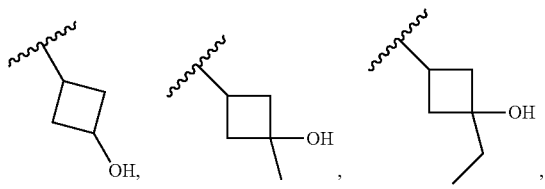

In some variations, the embodiments provided herein also apply to a compound of formula (II), or a stereoisomer or tautomer thereof, or a pharmaceutically acceptable salt of any of the foregoing, or any variation or embodiment thereof.

In some embodiments of a compound of formula (II), such as a compound of formula (I'), (I-A) or (I-A2), (I-E), (I-E1), or (I-G), or a stereoisomer or tautomer thereof, or a pharmaceutically acceptable salt of any of the foregoing, $R^b$ is $C_{3-10}$cycloalkyl optionally substituted with one or more —OH, $C_{3-10}$cycloalkyl, or $C_{1-6}$alkyl, wherein the $C_{1-6}$alkyl is further optionally substituted with one or more —OH or deuterium. In some embodiments, $R^b$ is $C_{3-6}$cycloalkyl optionally substituted with one or more —OH, $C_{3-6}$cycloalkyl, or $C_{1-3}$alkyl, wherein the $C_{1-3}$alkyl is further optionally substituted with one or more —OH or deuterium. In some embodiments $R^b$ is selected from the group consisting of

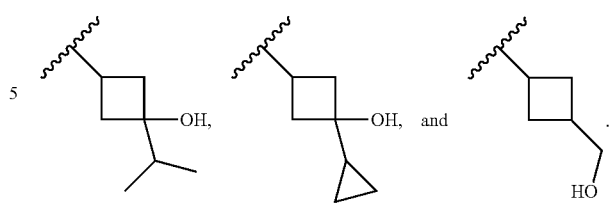

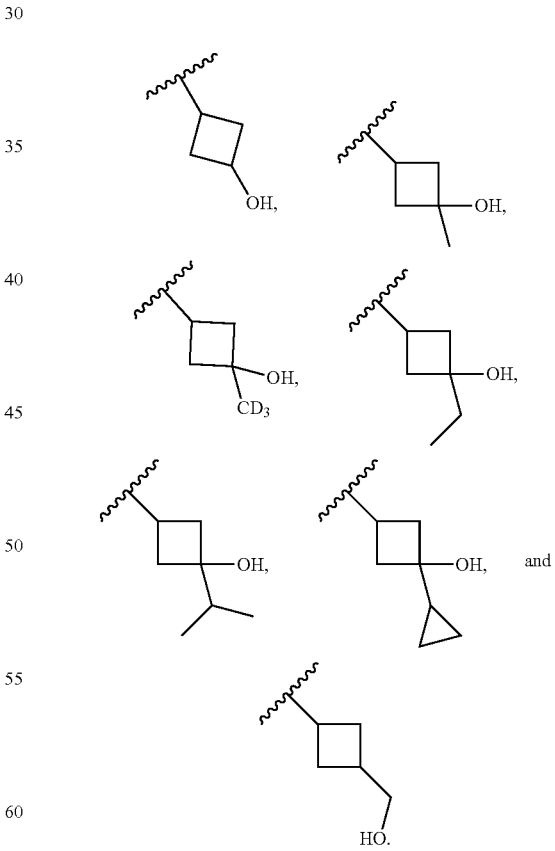

In some embodiments of a compound of formula (I), (I-A) or (I-A2), (I-E), (I-E1), or (I-G), or a stereoisomer or tautomer thereof, or a pharmaceutically acceptable salt of any of the foregoing, ring A is

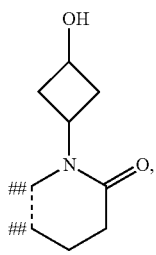

wherein ## represent a point of attachment to the remainder of the molecule and the dashed line represents a single or double bond. In some variations, the embodiments provided herein also apply to a compound of formula (I'), or (II), or a stereoisomer or tautomer thereof, or a pharmaceutically acceptable salt of any of the foregoing, or any variation or embodiment thereof.

In some embodiments of a compound of formula (I'), (I-A) or (I-A2), (I-E), (I-E1), or (I-G), or a stereoisomer or tautomer thereof, or a pharmaceutically acceptable salt of any of the foregoing, ring A is selected from the group consisting of

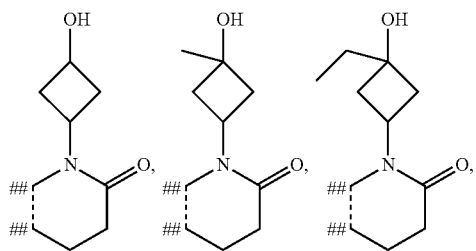

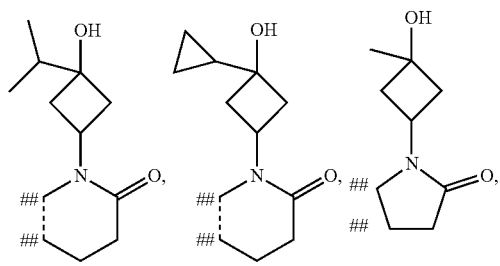

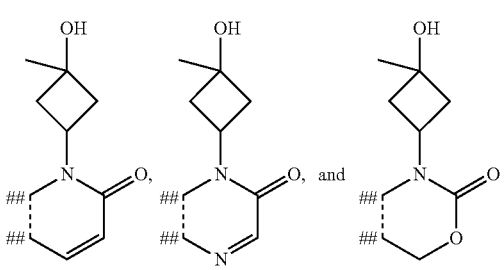

wherein ## represent a point of attachment to the remainder of the molecule and the dashed line represents a single or double bond. In some embodiments, ring A is selected from the group consisting of

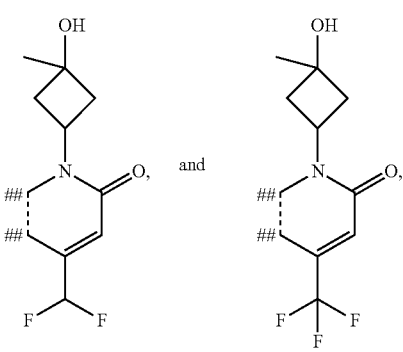

wherein ## represent a point of attachment to the remainder of the molecule and the dashed line represents a single or double bond. In some variations, the embodiments provided herein also apply to a compound of formula (II), or a stereoisomer or tautomer thereof, or a pharmaceutically acceptable salt of any of the foregoing, or any variation or embodiment thereof.

In some embodiments of a compound of formula (II), such as a compound of formula (I'), (I-A) or (I-A2), (I-E), (I-E1), or (I-G), or a stereoisomer or tautomer thereof, or a pharmaceutically acceptable salt of any of the foregoing, ring A is selected from the group consisting

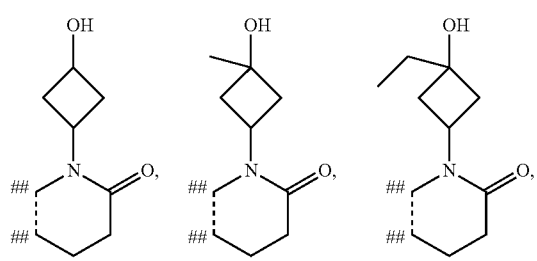

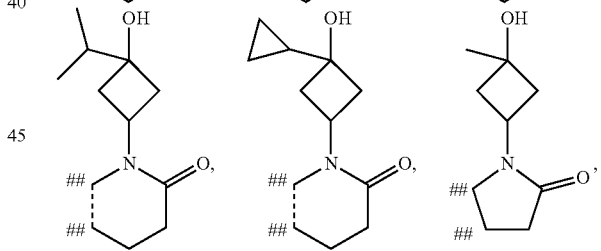

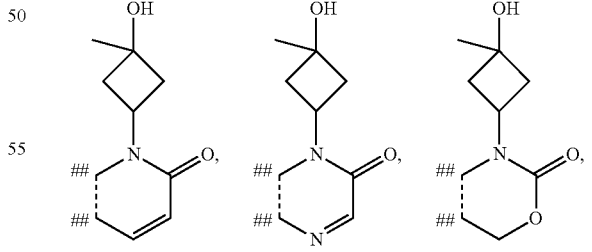

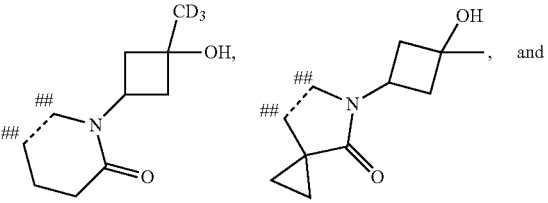

-continued

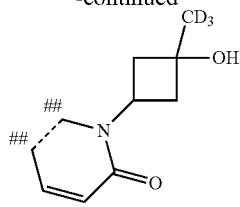

wherein ## represent a point of attachment to the remainder of the molecule and the dashed line represents a single or double bond.

In some embodiments of a compound of formula (I'), or a stereoisomer or tautomer thereof, or a pharmaceutically acceptable salt of any of the foregoing, $R^c$ is independently at each occurrence, selected from the group consisting of halo, $C_{1-6}$alkyl, —C(O)—$C_{1-6}$alkyl, —C(O)—$NH_2$, —C(O)—NH($C_{1-6}$alkyl), —C(O)—N($C_{1-6}$alkyl)$_2$, —S(O)$_2$—$R^a$, $C_{3-10}$cycloalkyl, and 3-10 membered heterocyclyl, wherein the $C_{1-6}$alkyl of $R^c$ is optionally substituted with one or more —S(O)$_2$—$C_{1-6}$alkyl, the $C_{3-10}$cycloalkyl of $R^c$ is optionally substituted with one or more —OH, or $C_{1-6}$alkyl, and the 3-10 membered heterocyclyl of $R^c$ is optionally substituted with one or more —OH, or $C_{1-6}$alkyl, wherein the $C_{1-6}$alkyl is further optionally substituted with one or more —OH. In some embodiments, $R^c$ is independently at each occurrence, selected from the group consisting of halo, $C_{1-3}$alkyl, —C(O)—$C_{1-3}$alkyl, —C(O)—$NH_2$, —C(O)—NH($C_{1-3}$alkyl), —C(O)—N($C_{1-3}$alkyl)$_2$, —S(O)$_2$—$R^a$, $C_{3-6}$cycloalkyl, and 3-6 membered heterocyclyl, wherein the $C_{1-3}$alkyl of $R^c$ is optionally substituted with one or more —S(O)$_2$—$C_{1-3}$alkyl, the $C_{3-6}$cycloalkyl of $R^c$ is optionally substituted with one or more —OH, or $C_{1-3}$alkyl, and the 3-6 membered heterocyclyl of $R^c$ is optionally substituted with one or more —OH, or $C_{1-3}$alkyl, wherein the $C_{1-3}$alkyl is further optionally substituted with one or more —OH. In some embodiments, $R^c$ is selected from the group consisting of methyl, isopropyl, —S(O)$_2$CH$_3$, and

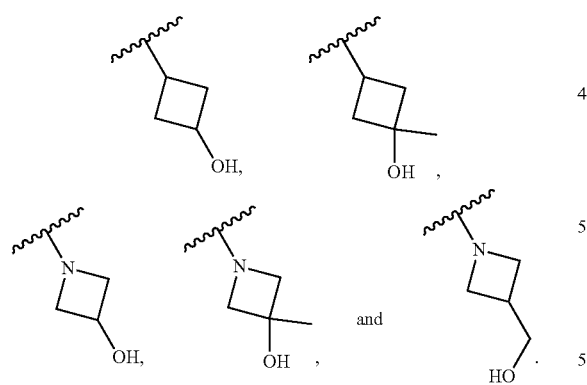

In some variations, the embodiments provided herein also apply to a compound of formula (II), or a stereoisomer or tautomer thereof, or a pharmaceutically acceptable salt of any of the foregoing, or any variation or embodiment thereof.

In some embodiments of a compound of formula (I'), (I-A) or (I-A2), (I-E), (I-E1), or (I-G), or a stereoisomer or tautomer thereof, or a pharmaceutically acceptable salt of any of the foregoing, ring A is selected from the group consisting of

wherein ## represent a point of attachment to the remainder of the molecule and the dashed line represents a single or double bond. In some variations, the embodiments provided herein also apply to a compound of formula (II), or a stereoisomer or tautomer thereof, or a pharmaceutically acceptable salt of any of the foregoing, or any variation or embodiment thereof.

In some embodiments of a compound of formula (II), such as a compound of formula (I'), (I-A) or (I-A2), (I-E), (I-E1), or (I-G), or a stereoisomer or tautomer thereof, or a pharmaceutically acceptable salt of any of the foregoing, ring A is selected from the group consisting of

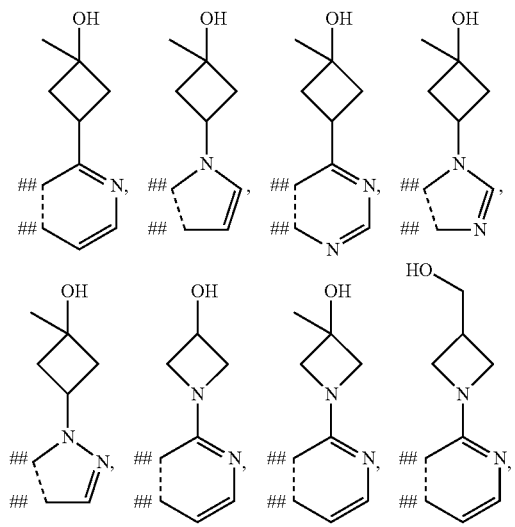

-continued

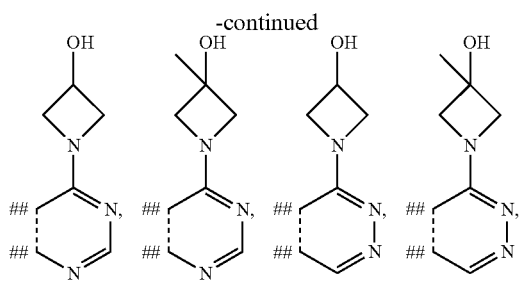

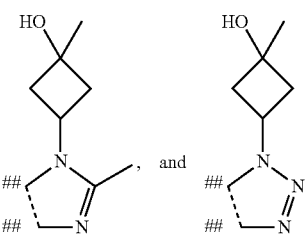

wherein ## represent a point of attachment to the remainder of the molecule and the dashed line represents a single or double bond.

In some embodiments, provided herein is a compound of formula (II), or a stereoisomer or tautomer thereof, or a pharmaceutically acceptable salt thereof, wherein the compound is a compound of formula (II-A):

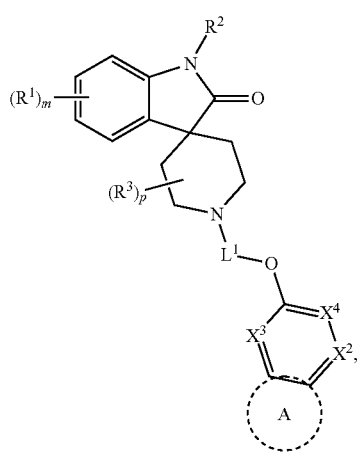

or a stereoisomer or tautomer thereof, or a pharmaceutically acceptable salt of any of the foregoing, wherein: ring A is 5-10 membered heterocyclyl or a 5-10 membered heteroaryl, wherein the 5-10 membered heterocyclyl of ring A is optionally substituted with one or more $R^b$, and wherein the 5-10 membered heteroaryl of ring A is optionally substituted with one or more $R^c$; and m, p, $R^1$, $R^2$, $R^3$, $L^1$, $R^b$, $R^c$, $X^2$, $X^3$, and $X^4$ are as defined for formula (II).

In some embodiments, provided herein is a compound of formula (II), or (II-A), or a stereoisomer or tautomer thereof, or a pharmaceutically acceptable salt thereof, wherein the compound is a compound of formula (II-A1):

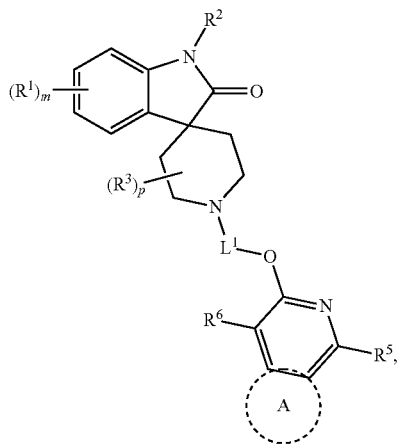

or a stereoisomer or tautomer thereof, or a pharmaceutically acceptable salt of any of the foregoing, wherein: ring A is 5-10 membered heterocyclyl or a 5-10 membered heteroaryl, wherein the 5-10 membered heterocyclyl of ring A is optionally substituted with one or more $R^b$, and wherein the 5-10 membered heteroaryl of ring A is optionally substituted with one or more $R^c$; and m, $R^1$, $R^2$, $R^6$, $L^1$, $R^b$, and $R^c$ are as defined for formula (II).

In some embodiments, provided herein is a compound of formula (II), or (II-A), or a stereoisomer or tautomer thereof, or a pharmaceutically acceptable salt thereof, wherein the compound is a compound of formula (II-A2):

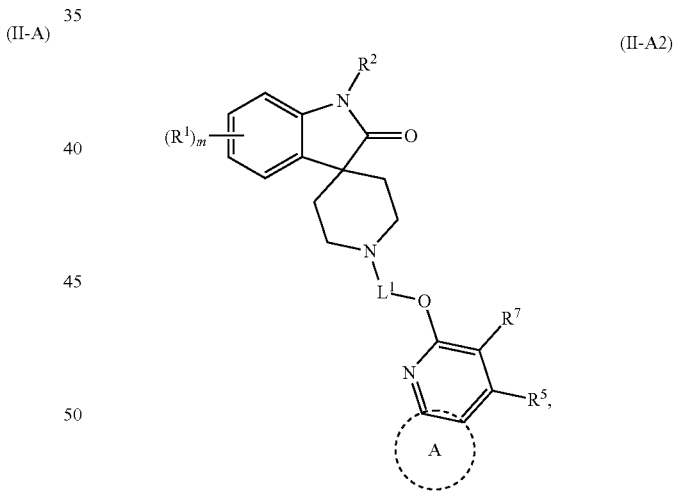

or a stereoisomer or tautomer thereof, or a pharmaceutically acceptable salt of any of the foregoing, wherein: ring A is 5-10 membered heterocyclyl or a 5-10 membered heteroaryl, wherein the 5-10 membered heterocyclyl of ring A is optionally substituted with one or more $R^b$, and wherein the 5-10 membered heteroaryl of ring A is optionally substituted with one or more $R^c$; and m, $R^1$, $R^2$, $R^7$, $L^1$, $R^b$, and $R^c$ are as defined for formula (II).

In some embodiments of a compound of formula (II), (II-A), (II-A1), or (II-A2), or a stereoisomer or tautomer thereof, or a pharmaceutically acceptable salt of any of the foregoing, $R^2$ is H.

In some embodiments of a compound of formula (II), (II-A), (II-A1), or (II-A2), or a stereoisomer or tautomer thereof, or a pharmaceutically acceptable salt of any of the foregoing, m is an integer from 0 to 4. In some embodiments, m is an integer from 0 to 2. In some embodiments, m is 0 or 1. In some embodiments m is 1.

In some embodiments of a compound of formula (II), (II-A), (II-A1), or (II-A2), or a stereoisomer or tautomer thereof, or a pharmaceutically acceptable salt of any of the foregoing, $R^1$ is halo. In some embodiments $R^1$ is Cl.

In some embodiments of a compound of formula (II), (II-A), (II-A1), or (II-A2), or a stereoisomer or tautomer thereof, or a pharmaceutically acceptable salt of any of the foregoing, $L^1$ is $C_{1-6}$alkylene. In some embodiments, $L^1$ is $C_{1-3}$alkylene. In some embodiments, $L^1$ is ethylene. In some embodiments, $L^1$ is

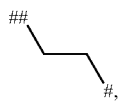

wherein, for each $L^1$, # denotes the point of attachment to —O— and ## denotes the point of attachment to the remainder of the molecule.

In some embodiments of a compound of formula (II), (II-A), (II-A1), or (II-A2), or a stereoisomer or tautomer thereof, or a pharmaceutically acceptable salt of any of the foregoing, $R^c$ is independently at each occurrence $C_{3-10}$cycloalkyl optionally substituted with one or more —OH, or $C_{1-6}$alkyl. In some embodiments, $R^c$ is independently at each occurrence, $C_{3-6}$cycloalkyl optionally substituted with one or more —OH, or $C_{1-3}$alkyl. In some embodiments, $R^c$ is

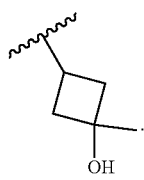 [SMILES: *C1CC(C)(O)C1]

In some embodiments of a compound of formula (II), (II-A), (II-A1), or (II-A2), or a stereoisomer or tautomer thereof, or a pharmaceutically acceptable salt of any of the foregoing, ring A is

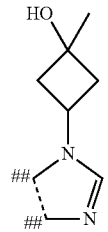

wherein ## represent a point of attachment to the remainder of the molecule and the dashed line represents a single or double bond.

In some embodiments of a compound of formula (II), (II-A), (II-A1), or (II-A2), or a stereoisomer or tautomer thereof, or a pharmaceutically acceptable salt of any of the foregoing, $R^5$ is $C_{1-6}$alkyl optionally substituted with one or more halo. In some embodiments $R^5$ is $CF_3$.

In some embodiments of a compound of formula (II), (II-A), or (II-A1), or a stereoisomer or tautomer thereof, or a pharmaceutically acceptable salt of any of the foregoing, $R^6$ is H.

In some embodiments of a compound of formula (II), (II-A), or (II-A2), or a stereoisomer or tautomer thereof, or a pharmaceutically acceptable salt of any of the foregoing, $R^7$ is H.

It is to be understood that any variation or embodiment of m, n, p, $R^1$, $R^2$, $R^3$, $L^1$, $L^2$ $L^3$, $X^1$, $X^2$, $X^3$, $X^4$, $R^4$, $R^5$, $R^6$, $R^7$, $R^a$, $R^b$, $R^c$, $Y^1$, $Y^2$, and $Y^3$ provided herein can be combined with every other variation or embodiment of m, n, p, $R^1$, $R^2$, $R^3$, $L^1$, $L^2$ $L^3$, $X^1$, $X^2$, $X^3$, $X^4$, $R^4$, $R^5$, $R^6$, $R^7$, $R^a$, $R^b$, $R^c$, $Y^1$, $Y^2$, and $Y^3$, the same as if each and every combination had been individually and specifically described. For example, embodiments where m is 1, n is 1, p is 0, $R^1$ is Cl, $R^2$ is H, $L^1$ is ethylene, $L^2$ is O, $L^3$ is $C_{1-6}$alkyl, $R^4$ is $SO_2R^a$ wherein $R^a$ is $C_{1-6}$alkyl, X is N, $X^2$ is N, $R^6$ is H, and $R^7$ is H, can be combined to give

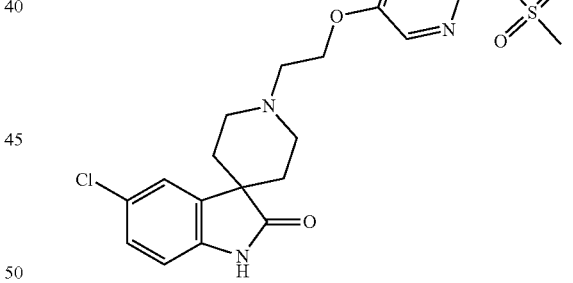

In some embodiments, provided herein is a compound of formula (I), or any variation of embodiment thereof, or a stereoisomer or tautomer thereof, or a pharmaceutically acceptable salt of any of the foregoing, wherein the compound is a compound of Table 1, or a stereoisomer or tautomer thereof, or a pharmaceutically acceptable salt of any of the foregoing.

TABLE 1

| Compound Number | Structure | Name |
|---|---|---|
| 1 | 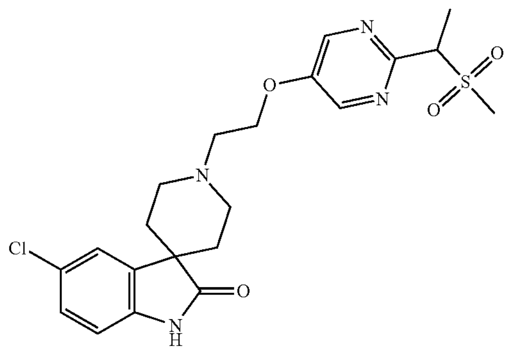 [SMILES: CC(c1ncc(OCCN2CCC3(CC2)C(=O)Nc2ccc(Cl)cc23)cn1)S(C)(=O)=O] | 5-chloro-1'-(2-{[2-(1-methanesulfonylethyl)pyrimidin-5-yl]oxy}ethyl)-1,2-dihydrospiro[indole-3,4'-piperidin]-2-one |
| 2 | 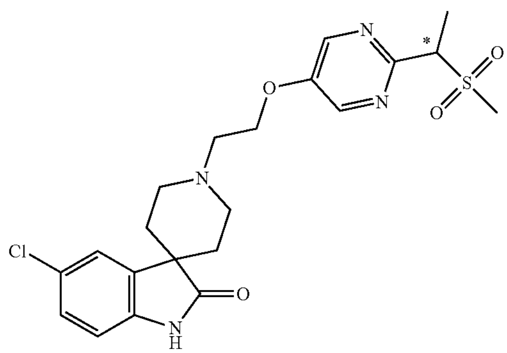 [SMILES: CC(c1ncc(OCCN2CCC3(CC2)C(=O)Nc2ccc(Cl)cc23)cn1)S(C)(=O)=O] | 5-chloro-1'-[2-({2-[(1S) or (1R)-1-methanesulfonylethyl]pyrimidin-5-yl}oxy)ethyl]-1,2-dihydrospiro[indole-3,4'-piperidin]-2-one |
| 3 | 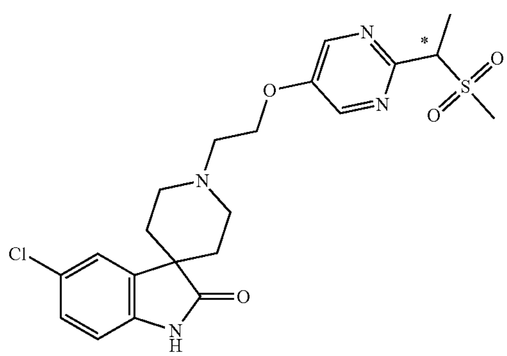 [SMILES: CC(c1ncc(OCCN2CCC3(CC2)C(=O)Nc2ccc(Cl)cc23)cn1)S(C)(=O)=O] | 5-chloro-1'-[2-({2-[(1R) or (1S)-1-methanesulfonylethyl]pyrimidin-5-yl}oxy)ethyl]-1,2-dihydrospiro[indole-3,4'-piperidin]-2-one |
| 4 | 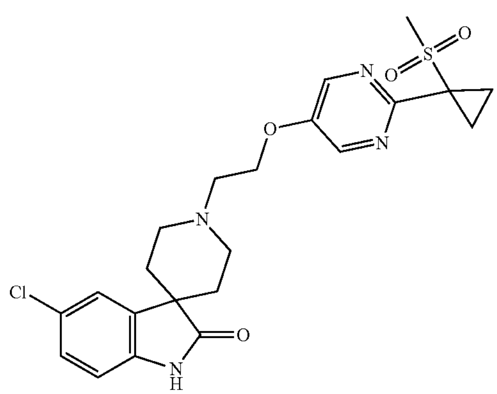 [SMILES: CS(=O)(=O)C1(c2ncc(OCCN3CCC4(CC3)C(=O)Nc3ccc(Cl)cc34)cn2)CC1] | 5-chloro-1'-(2-{[2-(1-methanesulfonylcyclopropyl)pyrimidin-5-yl]oxy}ethyl)-1,2-dihydrospiro[indole-3,4'-piperidin]-2-one |

TABLE 1-continued

| Compound Number | Structure | Name |
|---|---|---|
| 5 | 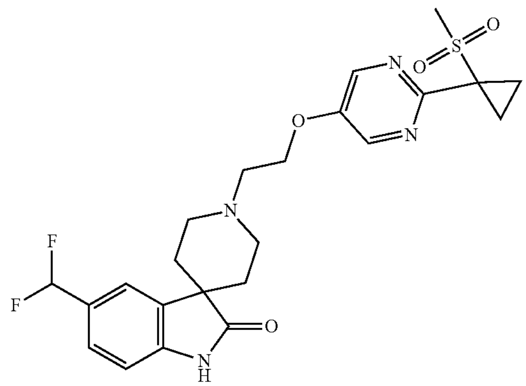 [SMILES: CS(=O)(=O)C1(c2ncc(OCCN3CCC4(CC3)C(=O)Nc3ccc(C(F)F)cc34)cn2)CC1] | 5-(difluoromethyl)-1'-(2-{[2-(1-methanesulfonylcyclopropyl)pyrimidin-5-yl]oxy}ethyl)-1,2-dihydrospiro[indole-3,4'-piperidin]-2-one |
| 6 | 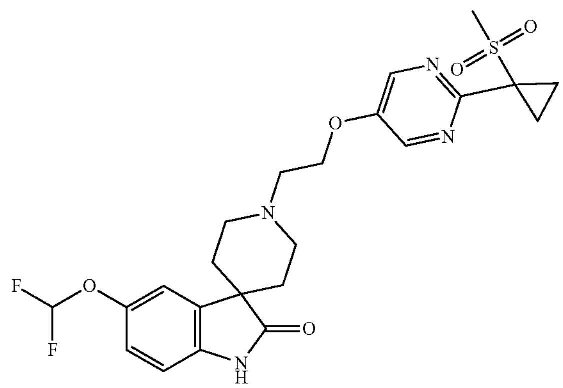 [SMILES: CS(=O)(=O)C1(c2ncc(OCCN3CCC4(CC3)C(=O)Nc3ccc(OC(F)F)cc34)cn2)CC1] | 5-(difluoromethoxy)-1'-(2-{[2-(1-methanesulfonylcyclopropyl)pyrimidin-5-yl]oxy}ethyl)-1,2-dihydrospiro[indole-3,4'-piperidin]-2-one |
| 7 | 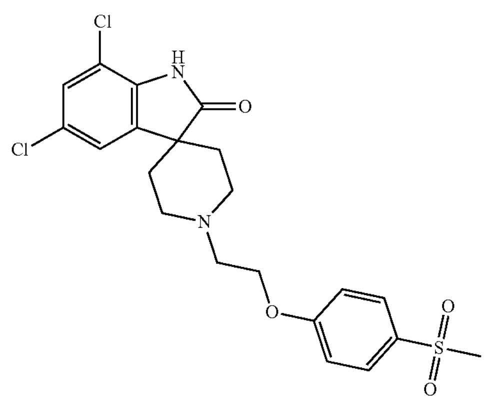 [SMILES: CS(=O)(=O)c1ccc(OCCN2CCC3(CC2)C(=O)Nc2c(Cl)cc(Cl)cc23)cc1] | 5,7-dichloro-1'-[2-(4-methanesulfonylphenoxy)ethyl]-1,2-dihydrospiro[indole-3,4'-piperidin]-2-one |
| 8 | 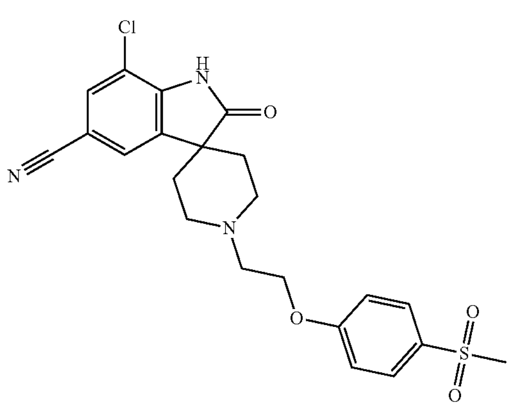 [SMILES: CS(=O)(=O)c1ccc(OCCN2CCC3(CC2)C(=O)Nc2c(Cl)cc(C#N)cc23)cc1] | 7-chloro-1'-[2-(4-methanesulfonylphenoxy)ethyl]-2-oxo-1,2-dihydrospiro[indole-3,4'-piperidine]-5-carbonitrile |

TABLE 1-continued

| Compound Number | Structure | Name |
|---|---|---|
| 9 | 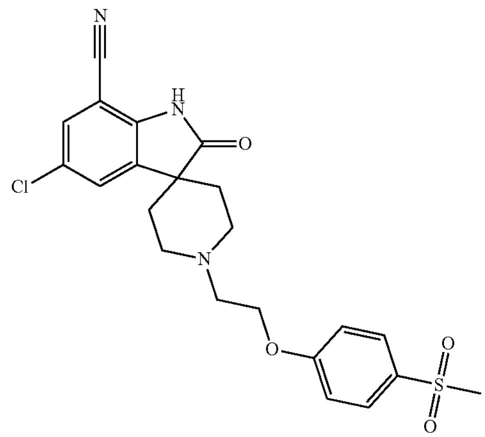 [SMILES: CS(=O)(=O)c1ccc(OCCN2CCC3(CC2)C(=O)Nc2c(C#N)cc(Cl)cc23)cc1] | 5-chloro-1'-[2-(4-methanesulfonylphenoxy)ethyl]-2-oxo-1,2-dihydrospiro[indole-3,4'-piperidine]-7-carbonitrile |
| 10 | 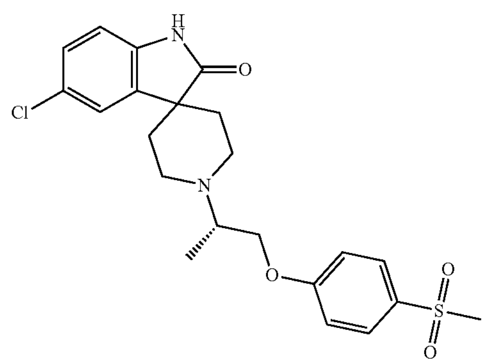 [SMILES: C[C@@H](COc1ccc(S(C)(=O)=O)cc1)N1CCC2(CC1)C(=O)Nc1ccc(Cl)cc12] | 5-chloro-1'-[(2S)-1-(4-methanesulfonylphenoxy)propan-2-yl]-1,2-dihydrospiro[indole-3,4'-piperidin]-2-one |
| 11 | 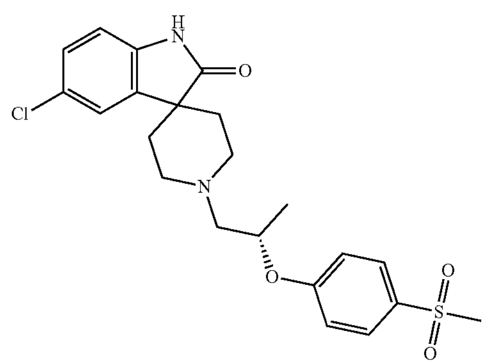 [SMILES: C[C@@H](CN1CCC2(CC1)C(=O)Nc1ccc(Cl)cc12)Oc1ccc(S(C)(=O)=O)cc1] | 5-chloro-1'-[(2S)-2-(4-methanesulfonylphenoxy)propyl]-1,2-dihydrospiro[indole-3,4'-piperidin]-2-one |
| 12 | 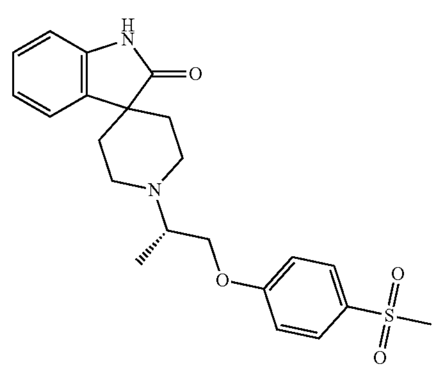 [SMILES: C[C@@H](COc1ccc(S(C)(=O)=O)cc1)N1CCC2(CC1)C(=O)Nc1ccccc12] | 1'-[(2S)-1-(4-methanesulfonylphenoxy)propan-2-yl]-1,2-dihydrospiro[indole-3,4'-piperidin]-2-one |

TABLE 1-continued

| Compound Number | Structure | Name |
|---|---|---|
| 13 | 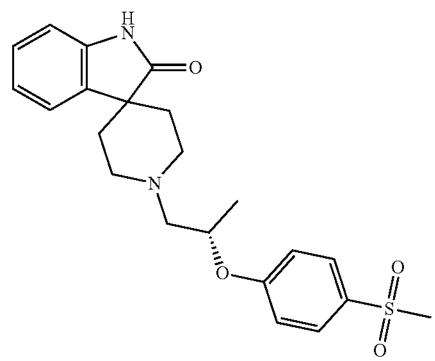 [SMILES: C[C@@H](CN1CCC2(CC1)C(=O)Nc1ccccc12)Oc1ccc(S(C)(=O)=O)cc1] | 1'-[(2S)-2-(4-methanesulfonylphenoxy)propyl]-1,2-dihydrospiro[indole-3,4'-piperidin]-2-one |
| 14 | 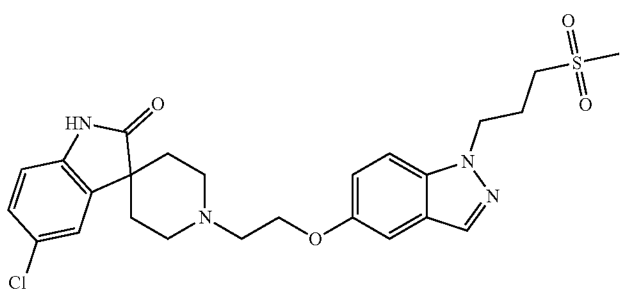 [SMILES: CS(=O)(=O)CCCn1ncc2cc(OCCN3CCC4(CC3)C(=O)Nc3ccc(Cl)cc34)ccc21] | 5-chloro-1'-(2-{[1-(3-methanesulfonylpropyl)-1H-indazol-5-yl]oxy}ethyl)-1,2-dihydrospiro[indole-3,4'-piperidin]-2-one |
| 15 | 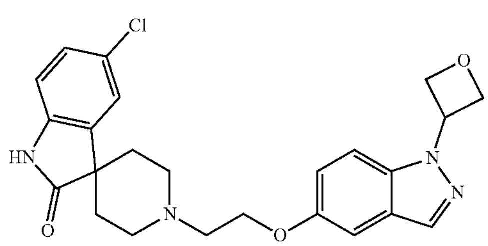 [SMILES: O=C1Nc2ccc(Cl)cc2C12CCN(CCOc1ccc3c(cnn3C3COC3)c1)CC2] | 5-chloro-1'-(2-{[1-(oxetan-3-yl)-1H-indazol-5-yl]oxy}ethyl)-1,2-dihydrospiro[indole-3,4'-piperidin]-2-one |
| 16 | 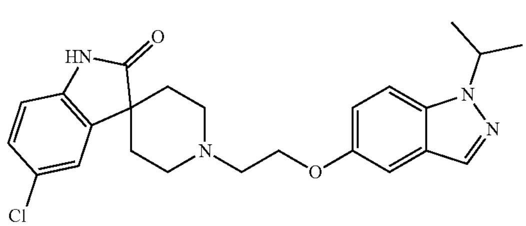 [SMILES: CC(C)n1ncc2cc(OCCN3CCC4(CC3)C(=O)Nc3ccc(Cl)cc34)ccc21] | 5-chloro-1'-(2-{[1-(propan-2-yl)-1H-indazol-5-yl]oxy}ethyl)-1,2-dihydrospiro[indole-3,4'-piperidin]-2-one |
| 17 | 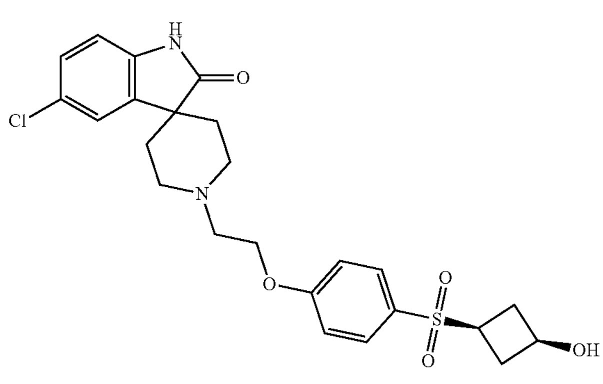 [SMILES: O=C1Nc2ccc(Cl)cc2C12CCN(CCOc1ccc(S(=O)(=O)[C@H]3C[C@@H](O)C3)cc1)CC2] | 5-chloro-1'-[2-(4-{[(cis)-3-hydroxycyclobutyl]sulfonyl}phenoxy)ethyl]-1,2-dihydrospiro[indole-3,4'-piperidin]-2-one |

TABLE 1-continued

| Compound Number | Structure | Name |
|---|---|---|
| 18 | 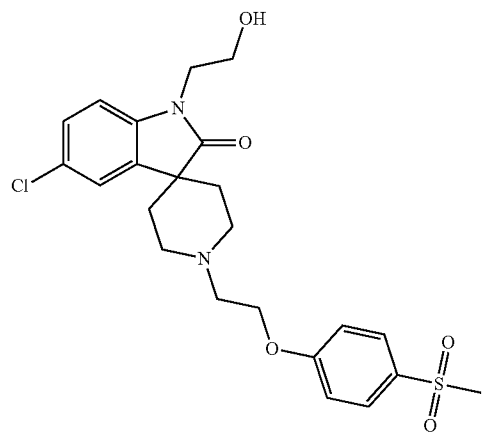 [SMILES: CS(=O)(=O)c1ccc(OCCN2CCC3(CC2)C(=O)N(CCO)c2ccc(Cl)cc23)cc1] | 5-chloro-1-(2-hydroxyethyl)-1'-[2-(4-methanesulfonylphenoxy)ethyl]-1,2-dihydrospiro[indole-3,4'-piperidin]-2-one |
| 19 | 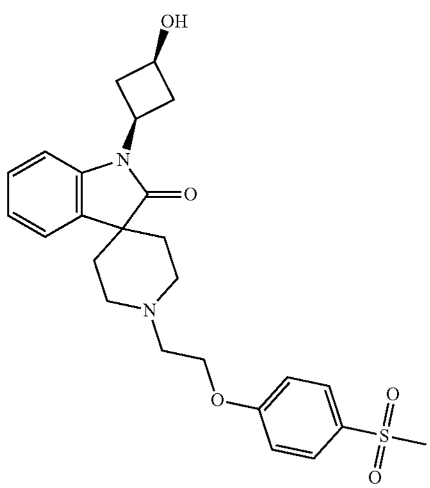 [SMILES: CS(=O)(=O)c1ccc(OCCN2CCC3(CC2)C(=O)N([C@H]2C[C@@H](O)C2)c2ccccc23)cc1] | 1'-2-(4-methanesulfonylphenoxy)ethyl]-1-[(cis)-3-hydroxycyclobutyl]-1,2-dihydrospiro[indole-3,4'-piperidin]-2-one |
| 20 | 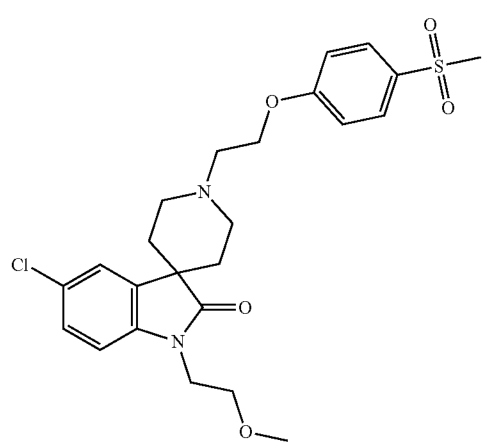 [SMILES: COCCN1C(=O)C2(CCN(CCOc3ccc(S(C)(=O)=O)cc3)CC2)c2cc(Cl)ccc21] | 5-chloro-1'-[2-(4-methanesulfonylphenoxy)ethyl]-1-(2-methoxyethyl)-1,2-dihydrospiro[indole-3,4'-piperidin]-2-one |

TABLE 1-continued

| Compound Number | Structure | Name |
|---|---|---|
| 21 | 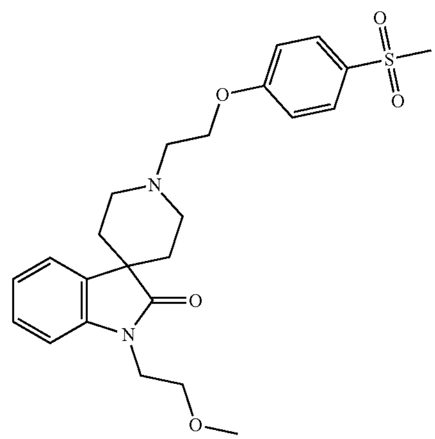 [SMILES: COCCN1C(=O)C2(CCN(CCOc3ccc(S(C)(=O)=O)cc3)CC2)c2ccccc21] | 1'-[2-(4-methanesulfonylphenoxy)ethyl]-1-(2-methoxyethyl)-1,2-dihydrospiro[indole-3,4'-piperidin]-2-one |
| 22 | 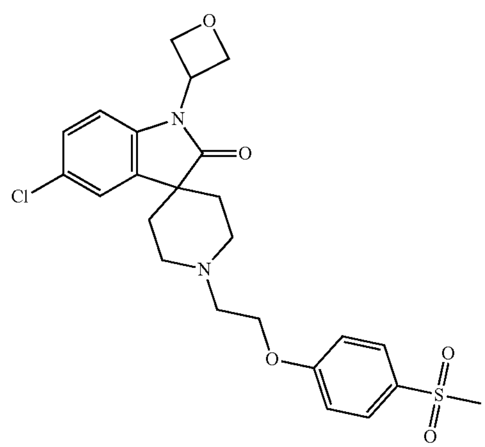 [SMILES: CS(=O)(=O)c1ccc(OCCN2CCC3(CC2)C(=O)N(C2COC2)c2ccc(Cl)cc23)cc1] | 5-chloro-1'-[2-(4-methanesulfonylphenoxy)ethyl]-1-(oxetan-3-yl)-1,2-dihydrospiro[indole-3,4'-piperidin]-2-one |
| 23 | 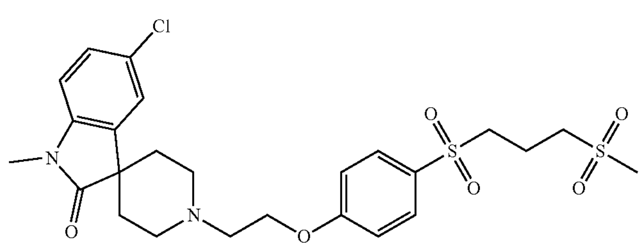 | 5-chloro-1'-{2-[4-(3-methanesulfonylpropanesulfonyl)phenoxy]ethyl}-1-methyl-1,2-dihydrospiro[indole-3,4'-piperidin]-2-one |
| 24 | 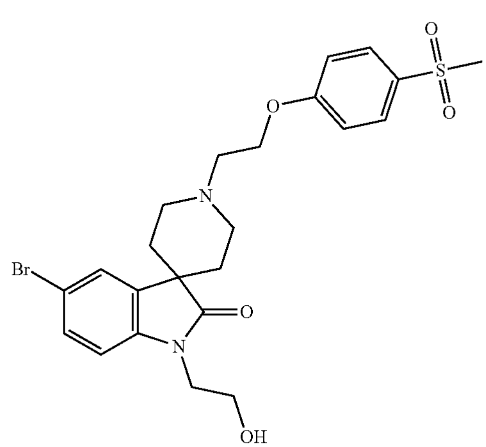 [SMILES: CS(=O)(=O)c1ccc(OCCN2CCC3(CC2)C(=O)N(CCO)c2ccc(Br)cc23)cc1] | 5-bromo-1-(2-hydroxyethyl)-1'-[2-(4-methanesulfonylphenoxy)ethyl]-1,2-dihydrospiro[indole-3,4'-piperidin]-2-one |

TABLE 1-continued

| Compound Number | Structure | Name |
|---|---|---|
| 25 | 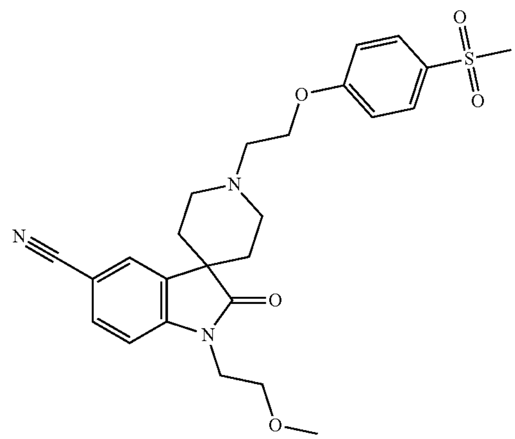 [SMILES: COCCN1C(=O)C2(CCN(CCOc3ccc(S(C)(=O)=O)cc3)CC2)c2cc(C#N)ccc21] | 1'-[2-(4-methanesulfonylphenoxy)ethyl]-1-(2-methoxyethyl)-2-oxo-1,2-dihydrospiro[indole-3,4'-piperidine]-5-carbonitrile |
| 26 | 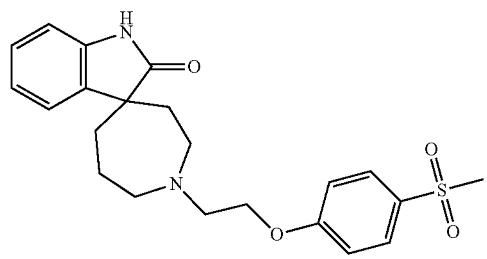 [SMILES: CS(=O)(=O)c1ccc(OCCN2CCCC3(CC2)C(=O)Nc2ccccc23)cc1] | 1-[2-(4-methanesulfonylphenoxy)ethyl]-1',2'-dihydrospiro[azepane-4,3'-indol]-2'-one |
| 27 | 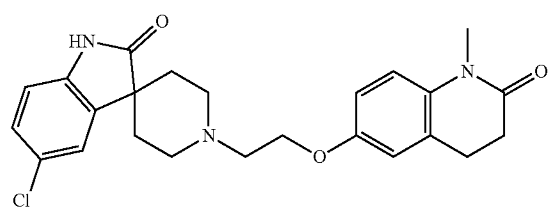 [SMILES: CN1C(=O)CCc2cc(OCCN3CCC4(CC3)C(=O)Nc3ccc(Cl)cc34)ccc21] | 5-chloro-1'-{2-[(1-methyl-2-oxo-1,2,3,4-tetrahydroquinolin-6-yl)oxy]ethyl}-1,2-dihydrospiro[indole-3,4'-piperidin]-2-one |
| 28 | 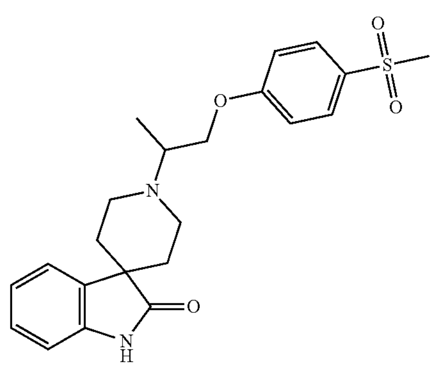 [SMILES: CC(COc1ccc(S(C)(=O)=O)cc1)N1CCC2(CC1)C(=O)Nc1ccccc12] | 1'-[1-(4-methanesulfonylphenoxy)propan-2-yl]-1,2-dihydrospiro[indole-3,4'-piperidin]-2-one |
| 29 | 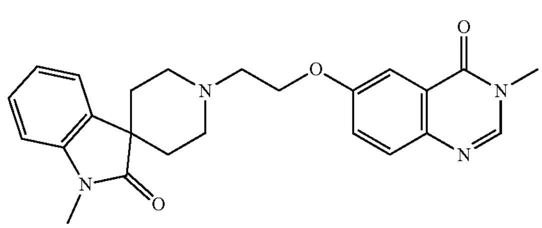 [SMILES: CN1C(=O)C2(CCN(CCOc3ccc4ncn(C)c(=O)c4c3)CC2)c2ccccc21] | 1-methyl-1'-{2-[(3-methyl-4-oxo-3,4-dihydroquinazolin-6-yl)oxy]ethyl}-1,2-dihydrospiro[indole-3,4'-piperidin]-2-one |

| Compound Number | Structure | Name |
|---|---|---|
| 30 | 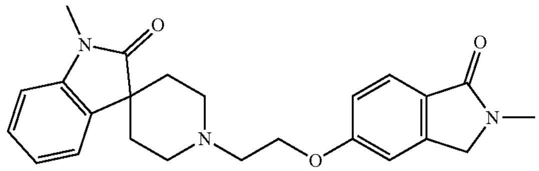 [SMILES: CN1Cc2cc(OCCN3CCC4(CC3)C(=O)N(C)c3ccccc34)ccc2C1=O] | 1-methyl-1'-{2-[(2-methyl-1-oxo-2,3-dihydro-1H-isoindol-5-yl)oxy]ethyl}-1,2-dihydrospiro[indole-3,4'-piperidin]-2-one |
| 31 | 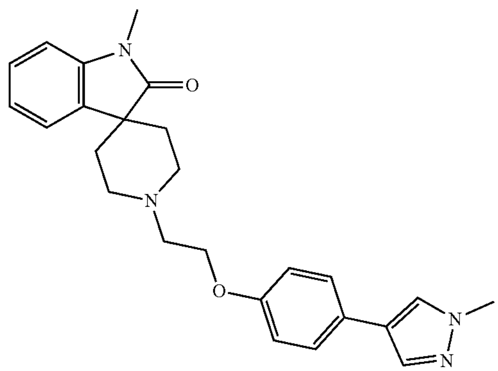 [SMILES: CN1C(=O)C2(CCN(CCOc3ccc(-c4cnn(C)c4)cc3)CC2)c2ccccc21] | 1-methyl-1'-{2-[4-(1-methyl-1H-pyrazol-4-yl)phenoxy]ethyl}-1,2-dihydrospiro[indole-3,4'-piperidin]-2-one |
| 32 | 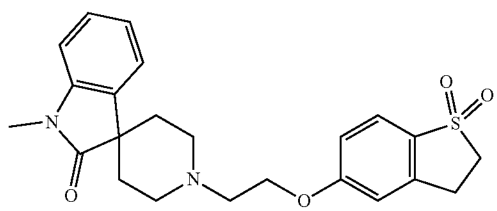 [SMILES: CN1C(=O)C2(CCN(CCOc3ccc4c(c3)CCS4(=O)=O)CC2)c2ccccc21] | 5-(2-{1-methyl-2-oxo-1,2-dihydrospiro[indole-3,4'-piperidin]-1'-yl}ethoxy)-2,3-dihydro-1λ⁶-benzothiophene-1,1-dione |
| 33 | 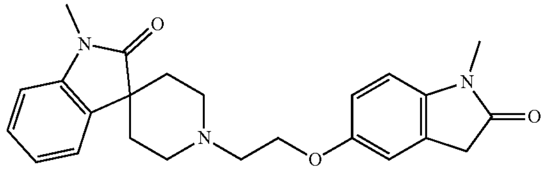 [SMILES: CN1C(=O)Cc2cc(OCCN3CCC4(CC3)C(=O)N(C)c3ccccc34)ccc21] | 1-methyl-1'-{2-[(1-methyl-2-oxo-2,3-dihydro-1H-indol-5-yl)oxy]ethyl}-1,2-dihydrospiro[indole-3,4'-piperidin]-2-one |
| 34 | 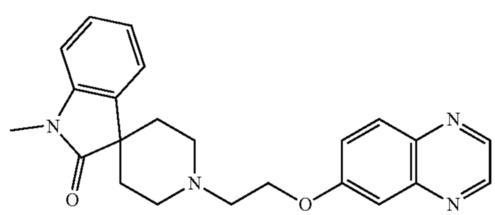 [SMILES: CN1C(=O)C2(CCN(CCOc3ccc4nccnc4c3)CC2)c2ccccc21] | 1-methyl-1'-[2-(quinoxalin-6-yloxy)ethyl]-1,2-dihydrospiro[indole-3,4'-piperidin]-2-one |
| 35 | 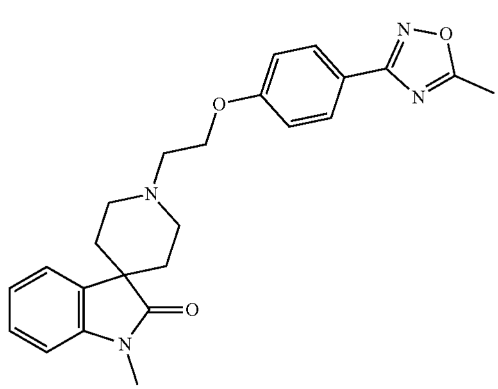 [SMILES: Cc1nc(-c2ccc(OCCN3CCC4(CC3)C(=O)N(C)c3ccccc34)cc2)no1] | 1-methyl-1'-{2-[4-(5-methyl-1,2,4-oxadiazol-3-yl)phenoxy]ethyl}-1,2-dihydrospiro[indole-3,4'-piperidin]-2-one |

TABLE 1-continued

| Compound Number | Structure | Name |
| --- | --- | --- |
| 36 | 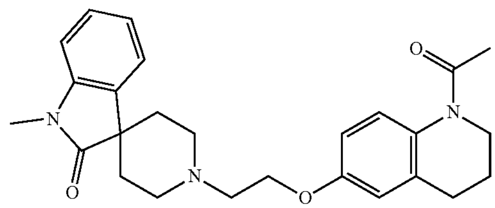 [SMILES: CC(=O)N1CCCc2cc(OCCN3CCC4(CC3)C(=O)N(C)c3ccccc34)ccc21] | 1'-{2-[(1-acetyl-1,2,3,4-tetrahydroquinolin-6-yl)oxy]ethyl}-1-methyl-1,2-dihydrospiro[indole-3,4'-piperidin]-2-one |
| 37 | 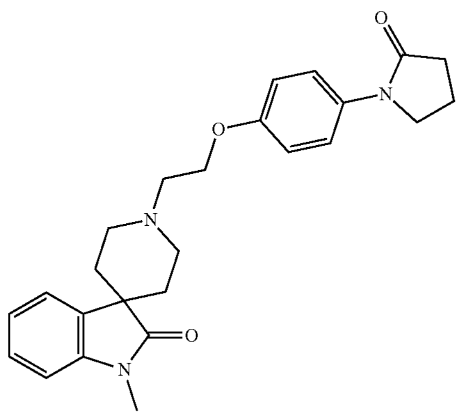 [SMILES: CN1C(=O)C2(CCN(CCOc3ccc(N4CCCC4=O)cc3)CC2)c2ccccc21] | 1-methyl-1'-{2-[4-(2-oxopyrrolidin-1-yl)phenoxy]ethyl}-1,2-dihydrospiro[indole-3,4'-piperidin]-2-one |
| 38 | 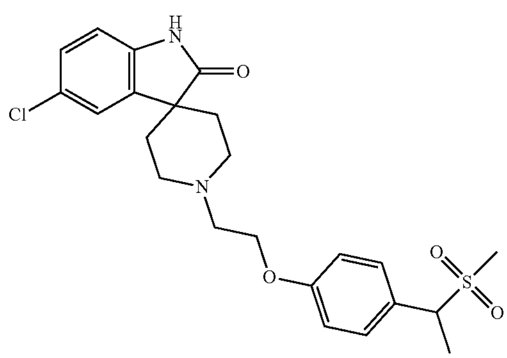 [SMILES: CC(c1ccc(OCCN2CCC3(CC2)C(=O)Nc2ccc(Cl)cc23)cc1)S(C)(=O)=O] | 5-chloro-1'-{2-[4-(1-methanesulfonylethyl)phenoxy]ethyl}-1,2-dihydrospiro[indole-3,4'-piperidin]-2-one |
| 39 | 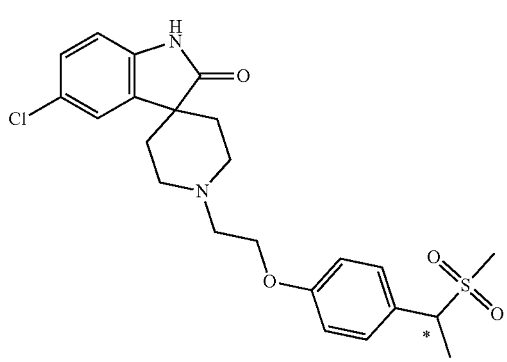 [SMILES: CC(c1ccc(OCCN2CCC3(CC2)C(=O)Nc2ccc(Cl)cc23)cc1)S(C)(=O)=O] | 5-chloro-1'-(2-{4-[(1S or 1R)-1-methanesulfonylethyl]phenoxy}ethyl)-1,2-dihydrospiro[indole-3,4'-piperidin]-2-one |

TABLE 1-continued

| Compound Number | Structure | Name |
|---|---|---|
| 40 | 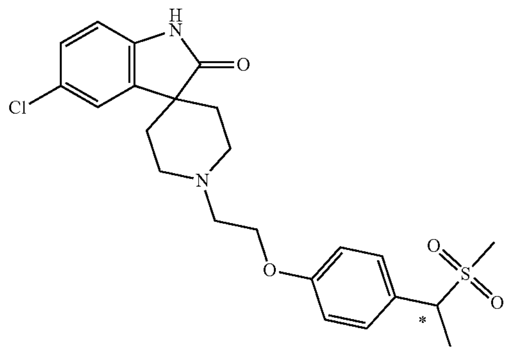 [SMILES: CC(c1ccc(OCCN2CCC3(CC2)C(=O)Nc2ccc(Cl)cc23)cc1)S(C)(=O)=O] | 5-chloro-1'-(2-{4-[(1R or 1S)-1-methanesulfonylethyl]phenoxy}ethyl)-1,2-dihydrospiro[indole-3,4'-piperidin]-2-one |
| 41 | 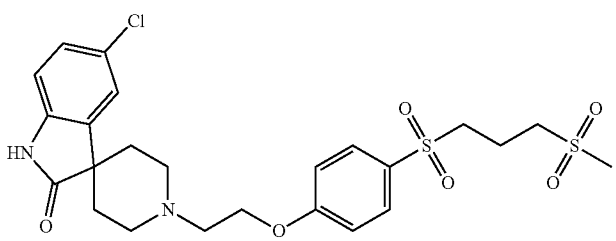 [SMILES: CS(=O)(=O)CCCS(=O)(=O)c1ccc(OCCN2CCC3(CC2)C(=O)Nc2ccc(Cl)cc23)cc1] | 5-chloro-1'-{2-[4-(3-methanesulfonylpropanesulfonyl)phenoxy]ethyl}-1,2-dihydrospiro[indole-3,4'-piperidin]-2-one |
| 42 | 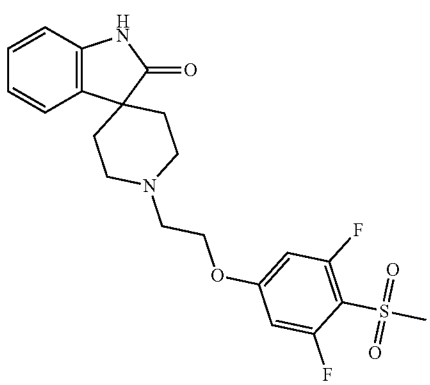 [SMILES: CS(=O)(=O)c1c(F)cc(OCCN2CCC3(CC2)C(=O)Nc2ccccc23)cc1F] | 1'-[2-(3,5-difluoro-4-methanesulfonylphenoxy)ethyl]-1,2-dihydrospiro[indole-3,4'-piperidin]-2-one |
| 43 | 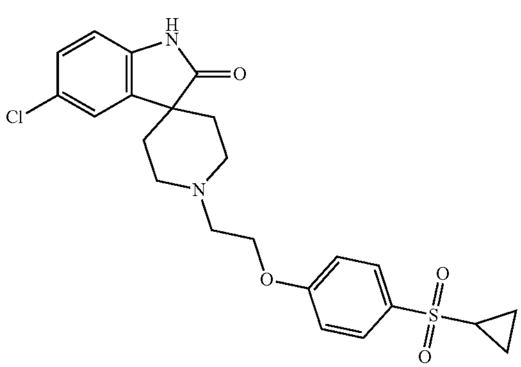 [SMILES: O=C1Nc2ccc(Cl)cc2C12CCN(CCOc1ccc(S(=O)(=O)C3CC3)cc1)CC2] | 5-chloro-1'-{2-[4-(cyclopropanesulfonyl)phenoxy]ethyl}-1,2-dihydrospiro[indole-3,4'-piperidin]-2-one |

TABLE 1-continued
| Compound Number | Structure | Name |
|---|---|---|
| 44 | 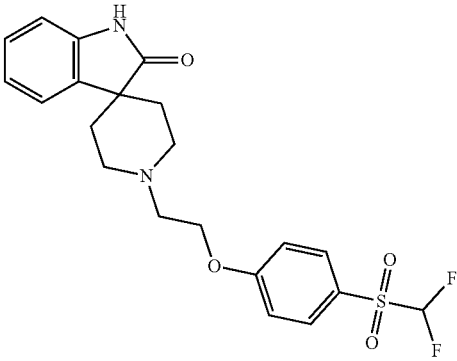 [SMILES: O=C1Nc2ccccc2C12CCN(CCOc1ccc(S(=O)(=O)C(F)F)cc1)CC2] | 1'-[2-(4-difluoromethanesulfonyl-phenoxy)ethyl]-1,2-dihydrospiro[indole-3,4'-piperidin]-2-one |
| 45 | 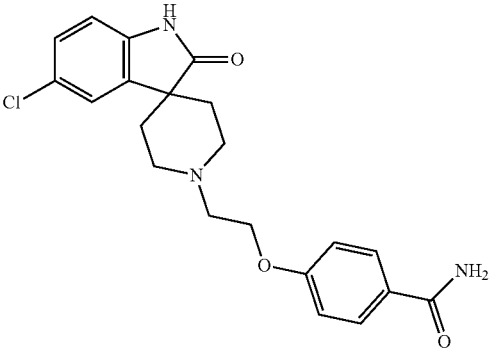 [SMILES: NC(=O)c1ccc(OCCN2CCC3(CC2)C(=O)Nc2ccc(Cl)cc23)cc1] | 4-(2-{5-chloro-2-oxo-1,2-dihydrospiro[indole-3,4'-piperidin]-1'-yl}ethoxy)benzamide |
| 46 | 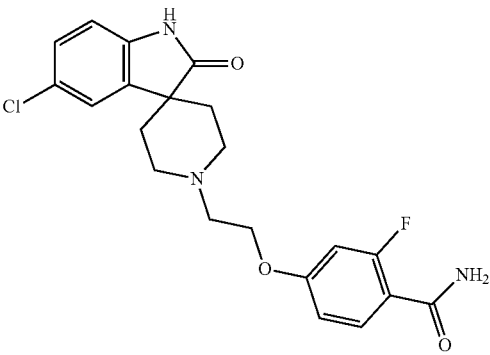 [SMILES: NC(=O)c1ccc(OCCN2CCC3(CC2)C(=O)Nc2ccc(Cl)cc23)cc1F] | 4-(2-{5-chloro-2-oxo-1,2-dihydrospiro[indole-3,4'-piperidin]-1'-yl}ethoxy)-2-fluorobenzamide |
| 47 | 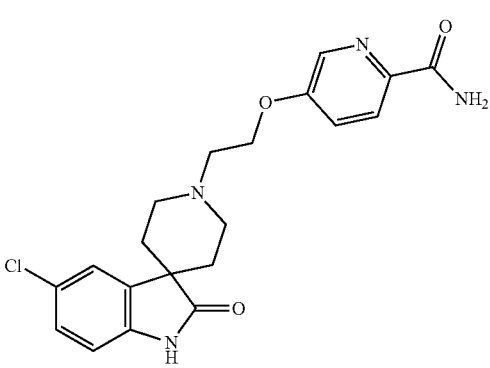 [SMILES: NC(=O)c1ccc(OCCN2CCC3(CC2)C(=O)Nc2ccc(Cl)cc23)cn1] | 5-(2-{5-chloro-2-oxo-1,2-dihydrospiro[indole-3,4'-piperidin]-1'-yl}ethoxy)pyridine-2-carboxamide |

TABLE 1-continued

| Compound Number | Structure | Name |
|---|---|---|
| 48 | 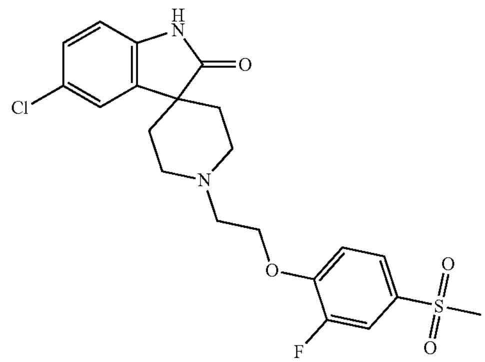 [SMILES: CS(=O)(=O)c1ccc(OCCN2CCC3(CC2)C(=O)Nc2ccc(Cl)cc23)c(F)c1] | 5-chloro-1'-[2-(2-fluoro-4-methanesulfonylphenoxy)ethyl]-1,2-dihydrospiro[indole-3,4'-piperidin]-2-one |
| 49 | 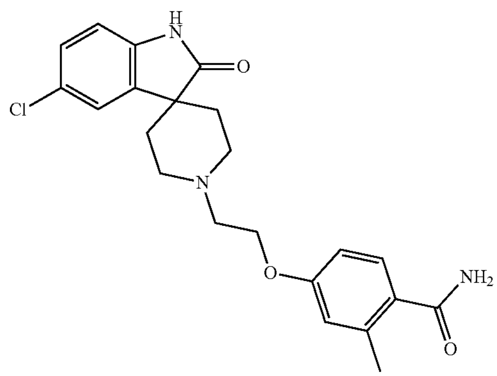 [SMILES: Cc1cc(OCCN2CCC3(CC2)C(=O)Nc2ccc(Cl)cc23)ccc1C(N)=O] | 4-(2-{5-chloro-2-oxo-1,2-dihydrospiro[indole-3,4'-piperidin]-1'-yl}ethoxy)-2-methylbenzamide |
| 50 | 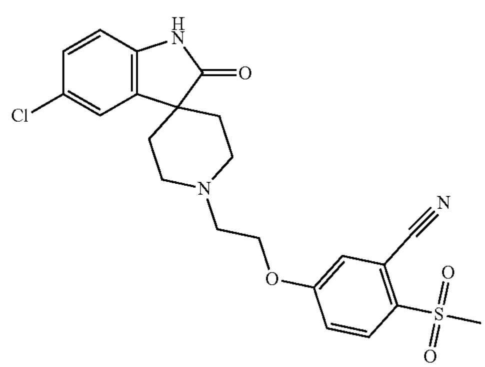 [SMILES: CS(=O)(=O)c1ccc(OCCN2CCC3(CC2)C(=O)Nc2ccc(Cl)cc23)cc1C#N] | 5-(2-{5-chloro-2-oxo-1,2-dihydrospiro[indole-3,4'-piperidin]-1'-yl}ethoxy)-2-methanesulfonylbenzonitrile |
| 51 | 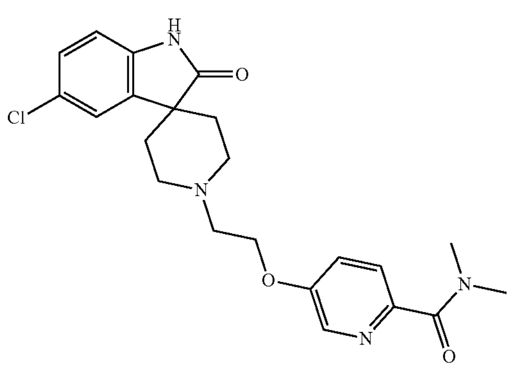 [SMILES: CN(C)C(=O)c1ccc(OCCN2CCC3(CC2)C(=O)Nc2ccc(Cl)cc23)cn1] | 5-(2-{5-chloro-2-oxo-1,2-dihydrospiro[indole-3,4'-piperidin]-1'-yl}ethoxy)-N,N-dimethylpyridine-2-carboxamide |

TABLE 1-continued

| Compound Number | Structure | Name |
|---|---|---|
| 52 | 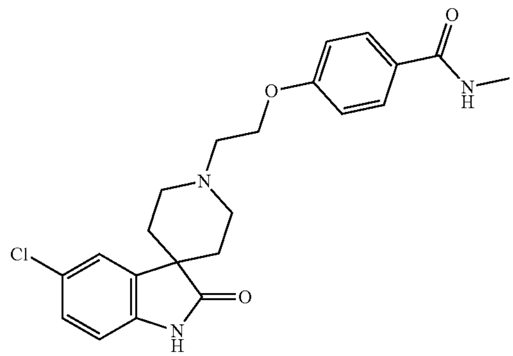 [SMILES: CNC(=O)c1ccc(OCCN2CCC3(CC2)C(=O)Nc2ccc(Cl)cc23)cc1] | 4-(2-{5-chloro-2-oxo-1,2-dihydrospiro[indole-3,4'-piperidin]-1'-yl}ethoxy)-N-methylbenzamide |
| 53 | 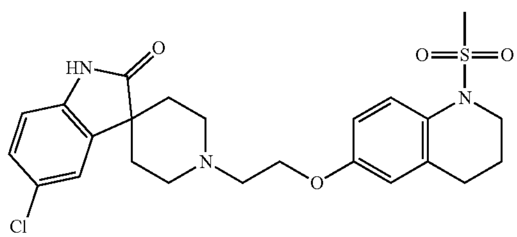 [SMILES: CS(=O)(=O)N1CCCc2cc(OCCN3CCC4(CC3)C(=O)Nc3ccc(Cl)cc34)ccc21] | 5-chloro-1'-{2-[(1-methanesulfonyl-1,2,3,4-tetrahydroquinolin-6-yl)oxy]ethyl}-1,2-dihydrospiro[indole-3,4'-piperidin]-2-one |
| 54 | 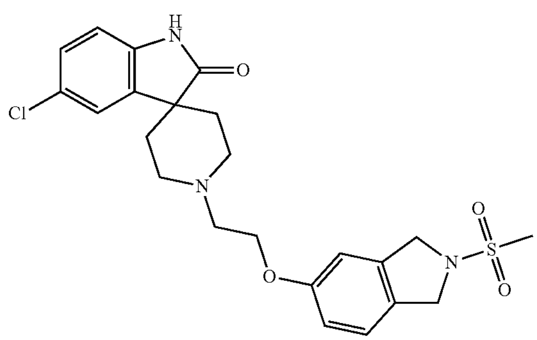 [SMILES: CS(=O)(=O)N1Cc2ccc(OCCN3CCC4(CC3)C(=O)Nc3ccc(Cl)cc34)cc2C1] | 5-chloro-1'-{2-[(2-methanesulfonyl-2,3-dihydro-1H-isoindol-5-yl)oxy]ethyl}-1,2-dihydrospiro[indole-3,4'-piperidin]-2-one |
| 55 | 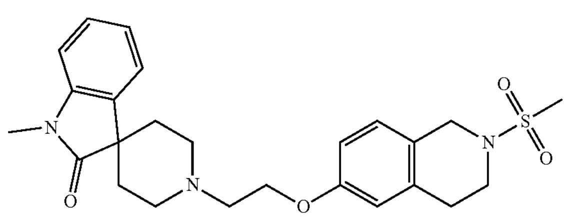 | 1'-{2-[(2-methanesulfonyl-1,2,3,4-tetrahydroisoquinolin-6-yl)oxy]ethyl}-1-methyl-1,2-dihydrospiro[indole-3,4'-piperidin]-2-one |
| 56 | 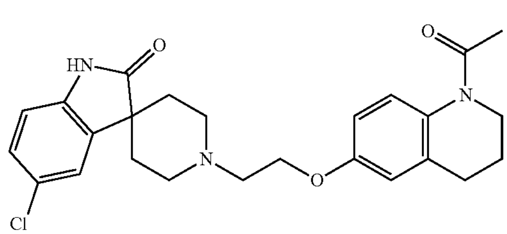 [SMILES: CC(=O)N1CCCc2cc(OCCN3CCC4(CC3)C(=O)Nc3ccc(Cl)cc34)ccc21] | 1'-{2-[(1-acetyl-1,2,3,4-tetrahydroquinolin-6-yl)oxy]ethyl}-5-chloro-1,2-dihydrospiro[indole-3,4'-piperidin]-2-one |

TABLE 1-continued

| Compound Number | Structure | Name |
|---|---|---|
| 57 | 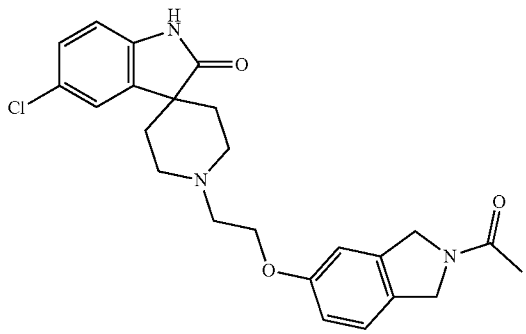 [SMILES: CC(=O)N1Cc2ccc(OCCN3CCC4(CC3)C(=O)Nc3ccc(Cl)cc34)cc2C1] | 1'-{2-[(2-acetyl-2,3-dihydro-1H-isoindol-5-yl)oxy]ethyl}-5-chloro-1,2-dihydrospiro[indole-3,4'-piperidin]-2-one |
| 58 | 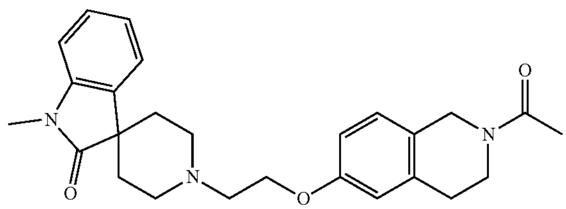 [SMILES: CC(=O)N1CCc2cc(OCCN3CCC4(CC3)C(=O)N(C)c3ccccc34)ccc2C1] | 1'-(2-[(2-acetyl-1,2,3,4-tetrahydroisoquinolin-6-yl)oxy]ethyl}-1-methyl-1,2-dihydrospiro[indole-3,4'-piperidin]-2-one |
| 59 | 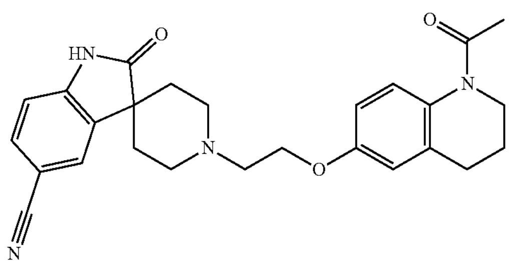 [SMILES: CC(=O)N1CCCc2cc(OCCN3CCC4(CC3)C(=O)Nc3ccc(C#N)cc34)ccc21] | 1'-{2-[(1-acetyl-1,2,3,4-tetrahydroquinolin-6-yl)oxy]ethyl}-2-oxo-1,2-dihydrospiro[indole-3,4'-piperidine]-5-carbonitrile |
| 60 | 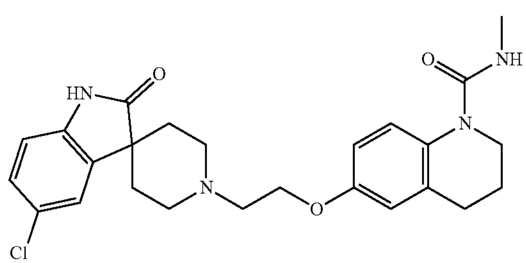 [SMILES: CNC(=O)N1CCCc2cc(OCCN3CCC4(CC3)C(=O)Nc3ccc(Cl)cc34)ccc21] | 6-(2-{5-chloro-2-oxo-1,2-dihydrospiro[indole-3,4'-piperidin]-1'-yl}ethoxy)-N-methyl-1,2,3,4-tetrahydroquinoline-1-carboxamide |
| 61 | 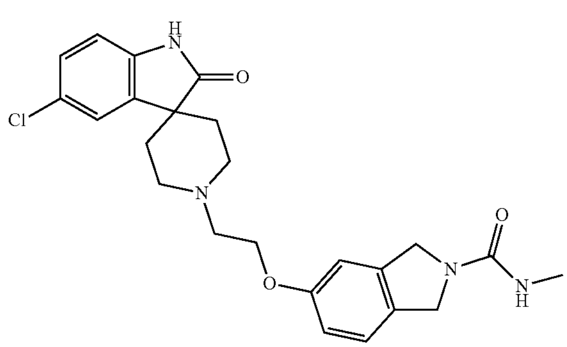 [SMILES: CNC(=O)N1Cc2ccc(OCCN3CCC4(CC3)C(=O)Nc3ccc(Cl)cc34)cc2C1] | 5-(2-{5-chloro-2-oxo-1,2-dihydrospiro[indole-3,4'-piperidin]-1'-yl}ethoxy)-N-methyl-2,3-dihydro-1H-isoindole-2-carboxamide |

TABLE 1-continued

| Compound Number | Structure | Name |
|---|---|---|
| 62 | 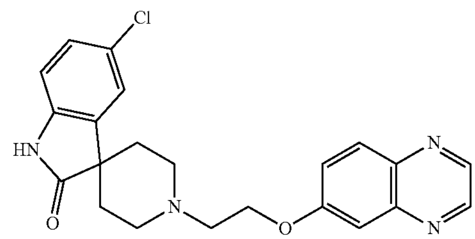 [SMILES: O=C1Nc2ccc(Cl)cc2C12CCN(CCOc1ccc3nccnc3c1)CC2] | 5-chloro-1'-[2-(quinoxalin-6-yloxy)ethyl]-1,2-dihydrospiro[indole-3,4'-piperidin]-2-one |
| 63 | 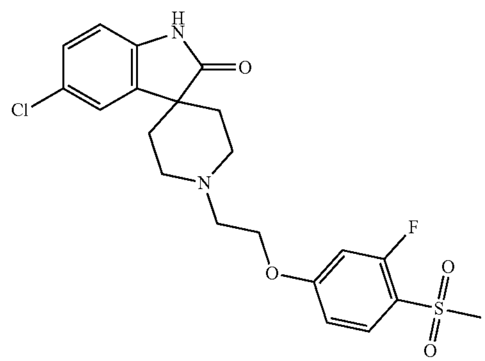 [SMILES: CS(=O)(=O)c1ccc(OCCN2CCC3(CC2)C(=O)Nc2ccc(Cl)cc23)cc1F] | 5-chloro-1'-[2-(3-fluoro-4-methanesulfonylphenoxy)ethyl]-1,2-dihydrospiro[indole-3,4'-piperidin]-2-one |
| 64 | 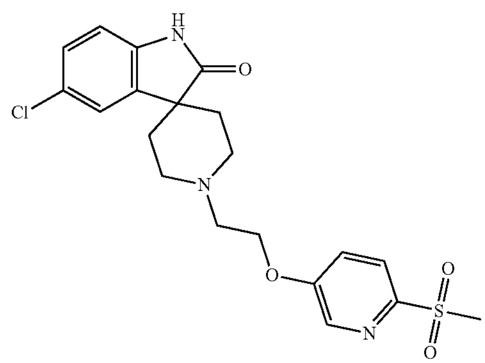 [SMILES: CS(=O)(=O)c1ccc(OCCN2CCC3(CC2)C(=O)Nc2ccc(Cl)cc23)cn1] | 5-chloro-1'-{2-[(6-methanesulfonylpyridin-3-yl)oxy]ethyl}-1,2-dihydrospiro[indole-3,4'-piperidin]-2-one |
| 65 | 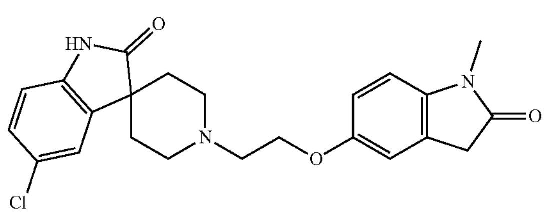 [SMILES: CN1C(=O)Cc2cc(OCCN3CCC4(CC3)C(=O)Nc3ccc(Cl)cc34)ccc21] | 5-chloro-1'-{2-[(1-methyl-2-oxo-2,3-dihydro-1H-indol-5-yl)oxy]ethyl}-1,2-dihydrospiro[indole-3,4'-piperidin]-2-one |
| 66 | 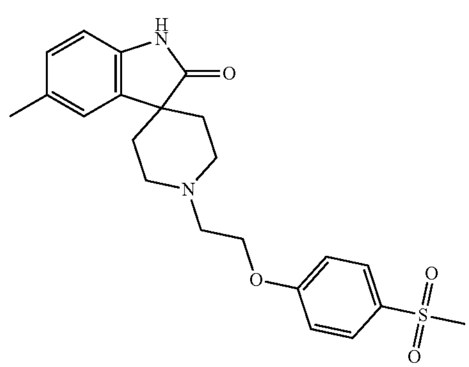 | 1'-[2-(4-methanesulfonylphenoxy)ethyl]-5-methyl-1,2-dihydrospiro[indole-3,4'-piperidin]-2-one |

TABLE 1-continued

| Compound Number | Structure | Name |
|---|---|---|
| 67 | 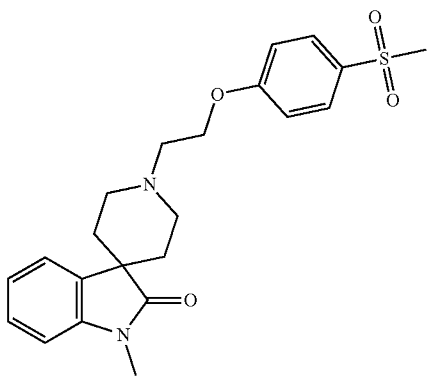 [SMILES: CN1C(=O)C2(CCN(CCOc3ccc(S(C)(=O)=O)cc3)CC2)c2ccccc21] | 1-2-(4-methanesulfonylphenoxy)ethyl]-1-methyl-1,2-dihydrospiro[indole-3,4'-piperidin]-2-one |
| 68 | 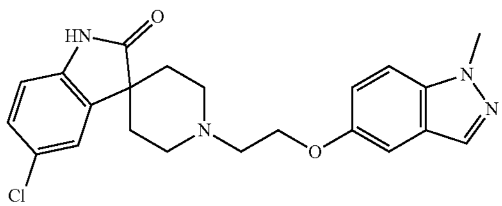 [SMILES: Cn1ncc2cc(OCCN3CCC4(CC3)C(=O)Nc3ccc(Cl)cc34)ccc21] | 5-chloro-1'-{2-[(1-methyl-1H-indazol-5-yl)oxy]ethyl}-1,2-dihydrospiro[indole-3,4'-piperidin]-2-one |
| 69 | 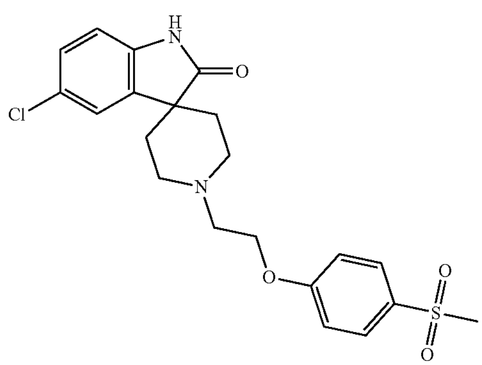 [SMILES: CS(=O)(=O)c1ccc(OCCN2CCC3(CC2)C(=O)Nc2ccc(Cl)cc23)cc1] | 5-chloro-1'-[2-(4-methanesulfonylphenoxy)ethyl]-1,2-dihydrospiro[indole-3,4'-piperidin]-2-one |
| 70 | 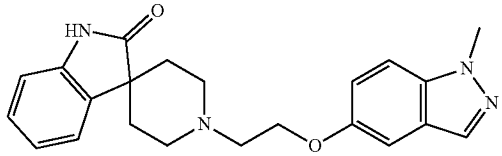 [SMILES: Cn1ncc2cc(OCCN3CCC4(CC3)C(=O)Nc3ccccc34)ccc21] | 1'-{2-[(1-methyl-1H-indazol-5-yl)oxy]ethyl}-1,2-dihydrospiro[indole-3,4'-piperidin]-2-one |
| 71 | 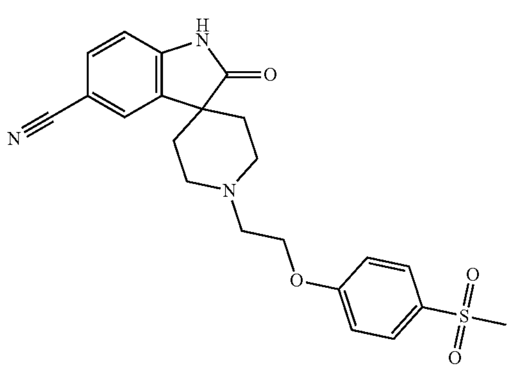 [SMILES: CS(=O)(=O)c1ccc(OCCN2CCC3(CC2)C(=O)Nc2ccc(C#N)cc23)cc1] | 1'-[2-(4-methanesulfonylphenoxy)ethyl]-2-oxo-1,2-dihydrospiro[indole-3,4'-piperidine]-5-carbonitrile |

TABLE 1-continued

| Compound Number | Structure | Name |
|---|---|---|
| 72 | 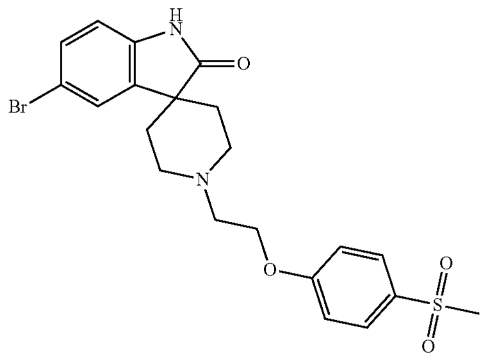 | 5-bromo-1'-[2-(4-methanesulfonylphenoxy)ethyl]-1,2-dihydrospiro[indole-3,4'-piperidin]-2-one |
| 73 | 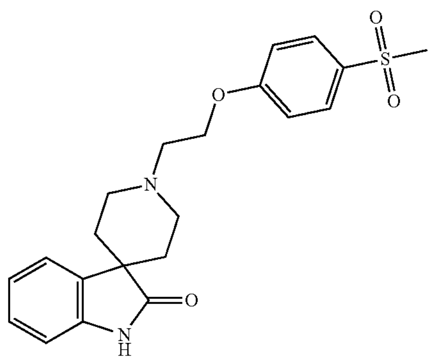 [SMILES: CS(=O)(=O)c1ccc(OCCN2CCC3(CC2)C(=O)Nc2ccccc23)cc1] | 1'-[2-(4-methanesulfonylphenoxy)ethyl]-1,2-dihydrospiro[indole-3,4'-piperidin]-2-one |
| 74 | 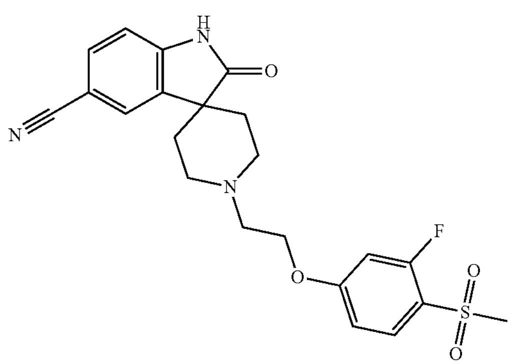 [SMILES: CS(=O)(=O)c1ccc(OCCN2CCC3(CC2)C(=O)Nc2ccc(C#N)cc23)cc1F] | 1'-[2-(3-fluoro-4-methanesulfonylphenoxy)ethyl]-2-oxo-1,2-dihydrospiro[indole-3,4'-piperidine]-5-carbonitrile |
| 75 | 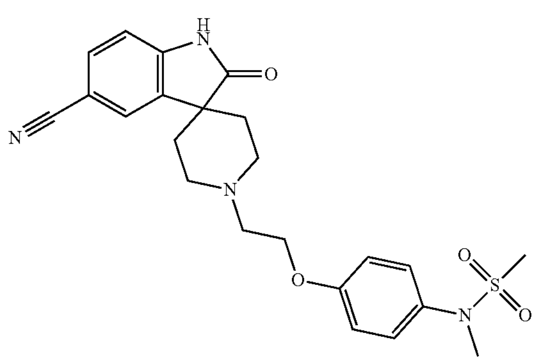 [SMILES: CN(c1ccc(OCCN2CCC3(CC2)C(=O)Nc2ccc(C#N)cc23)cc1)S(C)(=O)=O] | N-[4-(2-{5-cyano-2-oxo-1,2-dihydrospiro[indole-3,4'-piperidin]-1'-yl}ethoxy)phenyl]-N-methylmethanesulfonamide |

TABLE 1-continued

| Compound Number | Structure | Name |
|---|---|---|
| 76 | 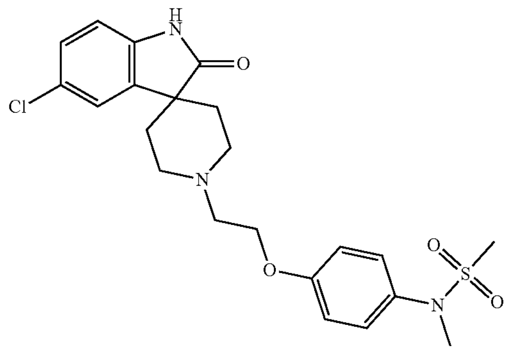 [SMILES: CN(c1ccc(OCCN2CCC3(CC2)C(=O)Nc2ccc(Cl)cc23)cc1)S(C)(=O)=O] | N-[4-(2-{5-chloro-2-oxo-1,2-dihydrospiro[indole-3,4'-piperidin]-1'-yl}ethoxy)phenyl]-N-methylmethanesulfonamide |
| 77 | 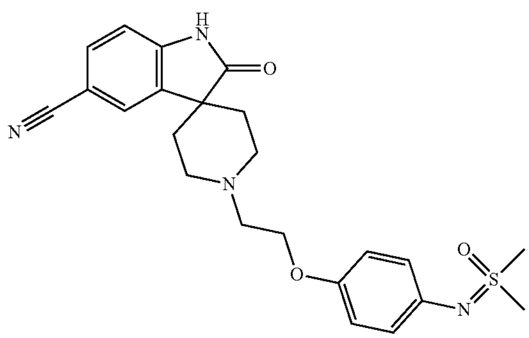 [SMILES: CS(C)(=O)=Nc1ccc(OCCN2CCC3(CC2)C(=O)Nc2ccc(C#N)cc23)cc1] | 1'-[2-(4-{[dimethyl(oxo)-λ⁶-sulfanylidene]amino}phenoxy)ethyl]-2-oxo-1,2-dihydrospiro[indole-3,4'-piperidine]-5-carbonitrile |
| 78 | 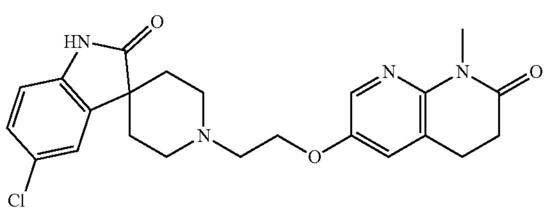 [SMILES: CN1C(=O)CCc2cc(OCCN3CCC4(CC3)C(=O)Nc3ccc(Cl)cc34)cnc21] | 5-chloro-1'-{2-[(8-methyl-7-oxo-5,6,7,8-tetrahydro-1,8-naphthyridin-3-yl)oxy]ethyl}-1,2-dihydrospiro[indole-3,4'-piperidin]-2-one |
| 79 | 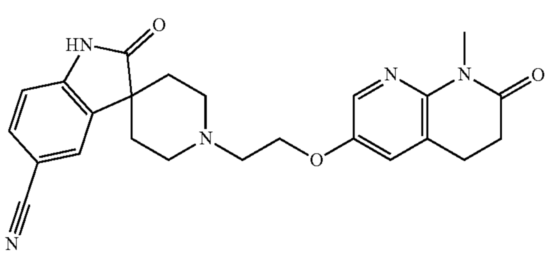 [SMILES: CN1C(=O)CCc2cc(OCCN3CCC4(CC3)C(=O)Nc3ccc(C#N)cc34)cnc21] | 1'-{2-[(8-methyl-7-oxo-5,6,7,8-tetrahydro-1,8-naphthyridin-3-yl)oxy]ethyl}-2-oxo-1,2-dihydrospiro[indole-3,4'-piperidine]-5-carbonitrile |
| 80 | 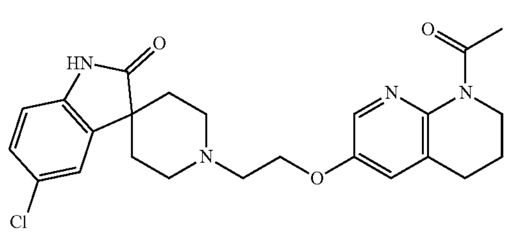 [SMILES: CC(=O)N1CCCc2cc(OCCN3CCC4(CC3)C(=O)Nc3ccc(Cl)cc34)cnc21] | 1'-{2-[(8-acetyl-5,6,7,8-tetrahydro-1,8-naphthyridin-3-yl)oxy]ethyl}-5-chloro-1,2-dihydrospiro[indole-3,4'-piperidin]-2-one |

TABLE 1-continued

| Compound Number | Structure | Name |
|---|---|---|
| 81 | 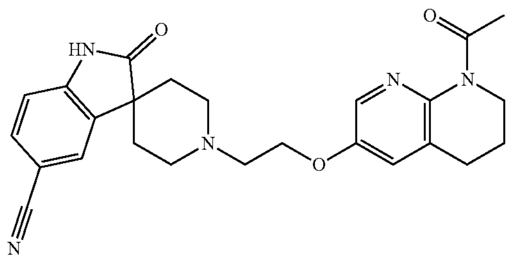 [SMILES: CC(=O)N1CCCc2cc(OCCN3CCC4(CC3)C(=O)Nc3ccc(C#N)cc34)cnc21] | 1'-(2-[(8-acetyl-5,6,7,8-tetrahydro-1,8-naphthyridin-3-yl)oxy]ethyl}-2-oxo-1,2-dihydrospiro[indole-3,4'-piperidine]-5-carbonitrile |
| 82 | 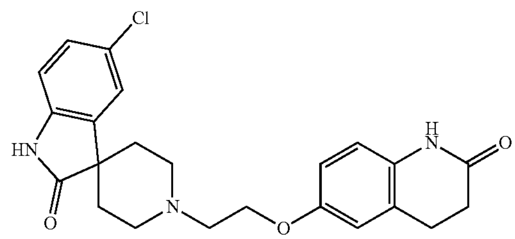 [SMILES: O=C1CCc2cc(OCCN3CCC4(CC3)C(=O)Nc3ccc(Cl)cc34)ccc2N1] | 5-chloro-1'-[2-([2-oxo-1,2,3,4-tetrahydroquinolin-6-yl)oxy]ethyl}-1,2-dihydrospiro[indole-3,4'-piperidin]-2-one |
| 83 | 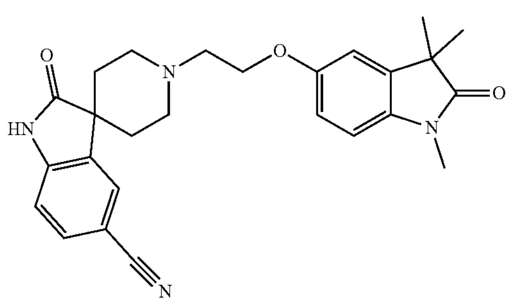 [SMILES: CN1C(=O)C(C)(C)c2cc(OCCN3CCC4(CC3)C(=O)Nc3ccc(C#N)cc34)ccc21] | 2-oxo-1'-{2-[(1,3,3-trimethyl-2-oxo-2,3-dihydro-1H-indol-5-yl)oxy]ethyl}-1,2-dihydrospiro[indole-3,4'-piperidine]-5-carbonitrile |
| 84 | 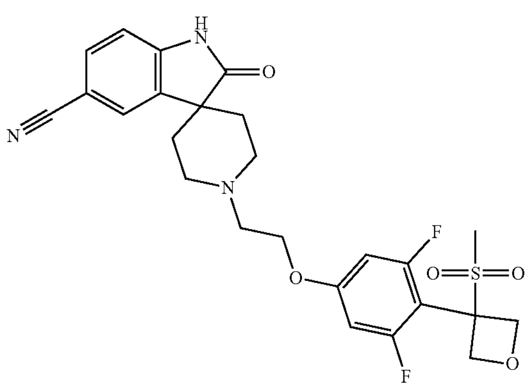 [SMILES: CS(=O)(=O)C1(c2c(F)cc(OCCN3CCC4(CC3)C(=O)Nc3ccc(C#N)cc34)cc2F)COC1] | 1'-{2-(3,5-difluoro-4-(3-methanesulfonyloxetan-3-yl)phenoxy]ethyl}-2-oxo-1,2-dihydrospiro[indole-3,4'-piperidine]-5-carbonitrile |
| 85 | 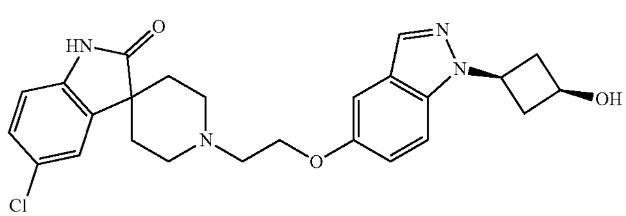 [SMILES: O=C1Nc2ccc(Cl)cc2C12CCN(CCOc1ccc3c(cnn3[C@H]3C[C@@H](O)C3)c1)CC2] | 5-chloro-1'-[2-({1-[(cis)-3-hydroxycyclobutyl]-1H-indazol-5-yl}oxy)ethyl]-1,2-dihydrospiro[indole-3,4'-piperidin]-2-one |

TABLE 1-continued

| Compound Number | Structure | Name |
|---|---|---|
| 86 | 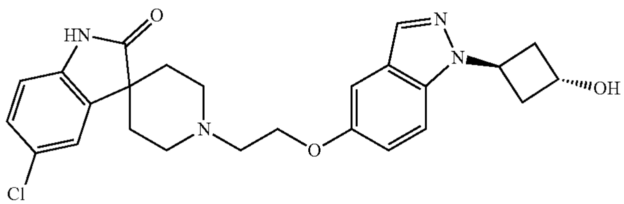 [SMILES: O=C1Nc2ccc(Cl)cc2C12CCN(CCOc1ccc3c(cnn3[C@H]3C[C@H](O)C3)c1)CC2] | 5-chloro-1'-[2-({1-[(trans)-3-hydroxycyclobutyl]-1H-indazol-5-yl}oxy)ethyl]-1,2-dihydrospiro[indole-3,4'-piperidin]-2-one |
| 87 | 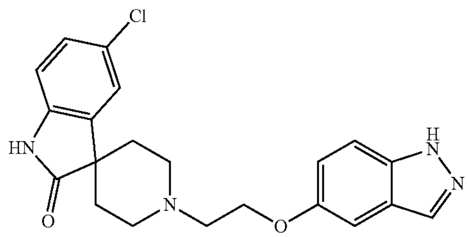 [SMILES: O=C1Nc2ccc(Cl)cc2C12CCN(CCOc1ccc3[nH]ncc3c1)CC2] | 5-chloro-1'-[2-(1H-indazol-5-yloxy)ethyl]-1,2-dihydrospiro[indole-3,4'-piperidin]-2-one |
| 88 | 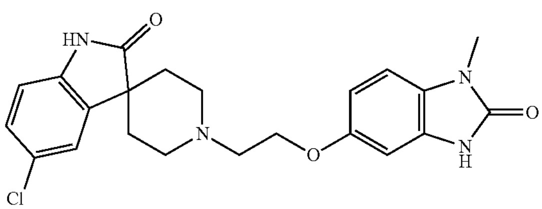 [SMILES: Cn1c(=O)[nH]c2cc(OCCN3CCC4(CC3)C(=O)Nc3ccc(Cl)cc34)ccc21] | 5-chloro-1'-{2-[(1-methyl-2-oxo-2,3-dihydro-1H-1,3-benzodiazol-5-yl)oxy]ethyl}-1,2-dihydrospiro[indole-3,4'-piperidin]-2-one |
| 89 | 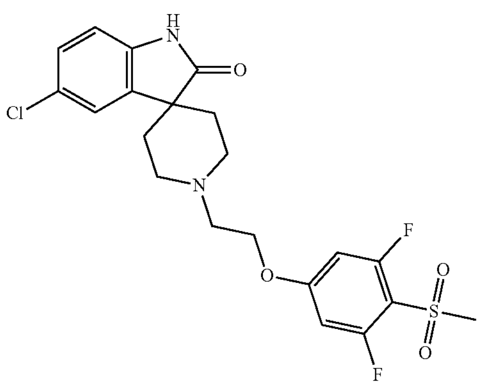 [SMILES: CS(=O)(=O)c1c(F)cc(OCCN2CCC3(CC2)C(=O)Nc2ccc(Cl)cc23)cc1F] | 5-chloro-1'-[2-(3,5-difluoro-4-methanesulfonylphenoxy)ethyl]-1,2-dihydrospiro[indole-3,4'-piperidin]-2-one |
| 90 | 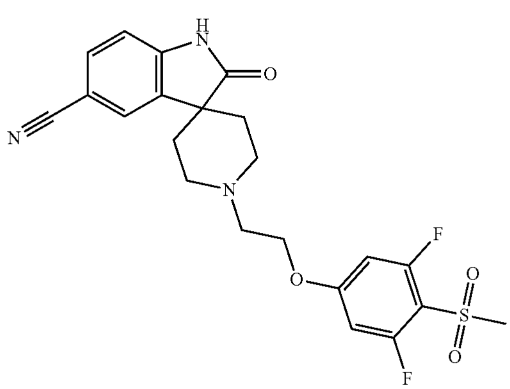 [SMILES: CS(=O)(=O)c1c(F)cc(OCCN2CCC3(CC2)C(=O)Nc2ccc(C#N)cc23)cc1F] | 1'-[2-(3,5-difluoro-4-methanesulfonylphenoxy)ethyl]-2-oxo-1,2-dihydrospiro[indole-3,4'-piperidine]-5-carbonitrile |

TABLE 1-continued

| Compound Number | Structure | Name |
|---|---|---|
| 91 | 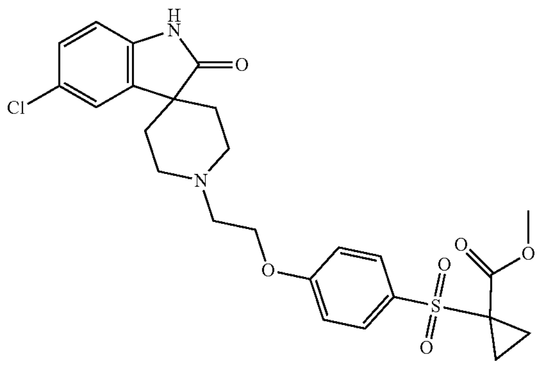 [SMILES: COC(=O)C1(S(=O)(=O)c2ccc(OCCN3CCC4(CC3)C(=O)Nc3ccc(Cl)cc34)cc2)CC1] | methyl 1-[4-(2-{5-chloro-2-oxo-1,2-dihydrospiro[indole-3,4'-piperidin]-1'-yl}ethoxy)benzenesulfonyl]cyclopropane-1-carboxylate |
| 92 | 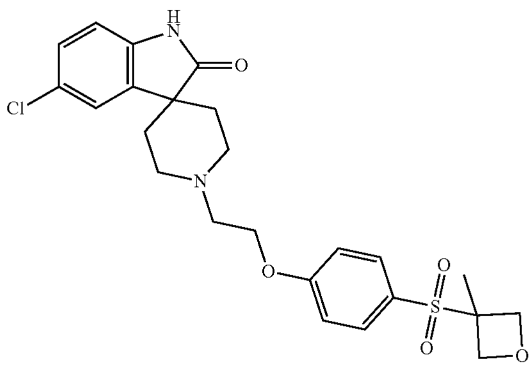 [SMILES: CC1(S(=O)(=O)c2ccc(OCCN3CCC4(CC3)C(=O)Nc3ccc(Cl)cc34)cc2)COC1] | 5-chloro-1'-(2-{4-[(3-methyloxetan-3-yl)sulfonyl]phenoxy}ethyl)-1,2-dihydrospiro[indole-3,4'-piperidin]-2-one |
| 93 | 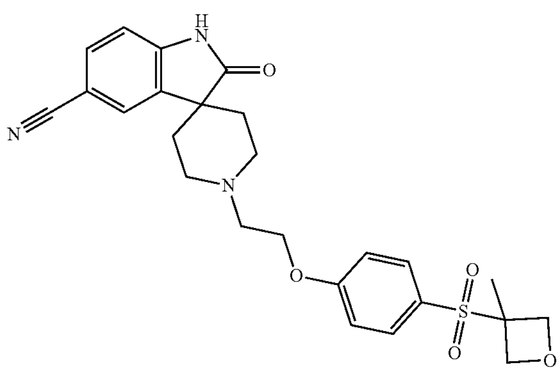 [SMILES: CC1(S(=O)(=O)c2ccc(OCCN3CCC4(CC3)C(=O)Nc3ccc(C#N)cc34)cc2)COC1] | 1'-(2-{4-[(3-methyloxetan-3-yl)sulfonyl]phenoxy}ethyl)-2-oxo-1,2-dihydrospiro[indole-3,4'-piperidine]-5-carbonitrile |
| 94 | 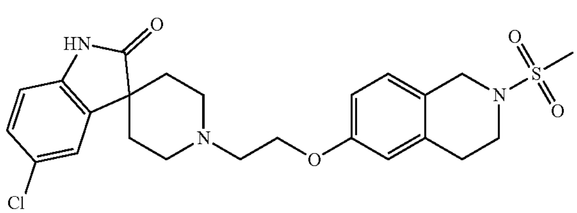 [SMILES: CS(=O)(=O)N1CCc2cc(OCCN3CCC4(CC3)C(=O)Nc3ccc(Cl)cc34)ccc2C1] | 5-chloro-1'-{2-[(2-methanesulfonyl-1,2,3,4-tetrahydroisoquinolin-6-yl)oxy]ethyl}-1,2-dihydrospiro[indole-3,4'-piperidin]-2-one |
| 95 | 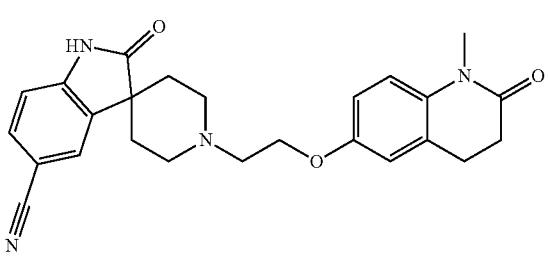 [SMILES: CN1C(=O)CCc2cc(OCCN3CCC4(CC3)C(=O)Nc3ccc(C#N)cc34)ccc21] | 1'-{2-[(1-methyl-2-oxo-1,2,3,4-tetrahydroquinolin-6-yl)oxy]ethyl}-2-oxo-1,2-dihydrospiro[indole-3,4'-piperidine]-5-carbonitrile |

TABLE 1-continued

| Compound Number | Structure | Name |
|---|---|---|
| 96 | 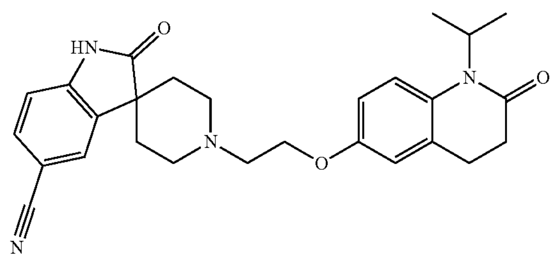 [SMILES: CC(C)N1C(=O)CCc2cc(OCCN3CCC4(CC3)C(=O)Nc3ccc(C#N)cc34)ccc21] | 2-oxo-1'-(2-{[2-oxo-1-(propan-2-yl)-1,2,3,4-tetrahydroquinolin-6-yl]oxy}ethyl)-1,2-dihydrospiro[indole-3,4'-piperidine]-5-carbonitrile |
| 97 | 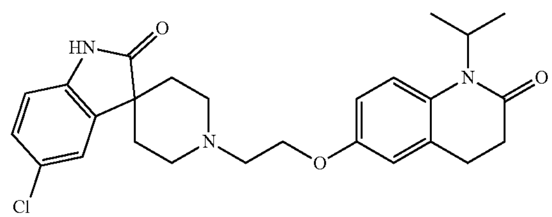 [SMILES: CC(C)N1C(=O)CCc2cc(OCCN3CCC4(CC3)C(=O)Nc3ccc(Cl)cc34)ccc21] | 5-chloro-1'-(2-{[2-oxo-1-(propan-2-yl)-1,2,3,4-tetrahydroquinolin-6-yl]oxy}ethyl)-1,2-dihydrospiro[indole-3,4'-piperidin]-2-one |
| 98 | 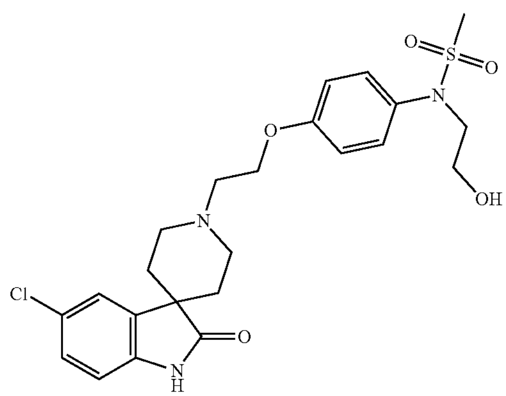 [SMILES: CS(=O)(=O)N(CCO)c1ccc(OCCN2CCC3(CC2)C(=O)Nc2ccc(Cl)cc23)cc1] | N-[4-(2-{5-chloro-2-oxo-1,2-dihydrospiro[indole-3,4'-piperidin]-1'-yl}ethoxy)phenyl]-N-(2-hydroxyethyl)methanesulfonamide |
| 99 | 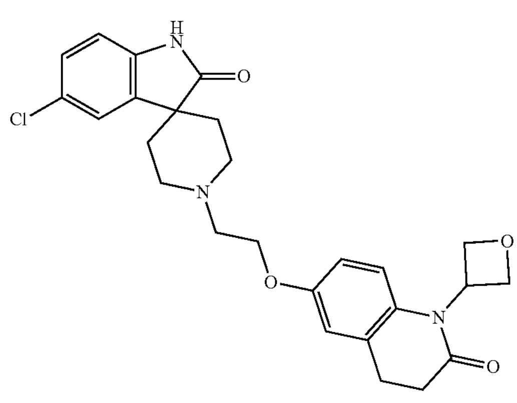 [SMILES: O=C1CCc2cc(OCCN3CCC4(CC3)C(=O)Nc3ccc(Cl)cc34)ccc2N1C1COC1] | 5-chloro-1'-(2-{[1-(oxetan-3-yl)-2-oxo-1,2,3,4-tetrahydroquinolin-6-yl]oxy}ethyl)-1,2-dihydrospiro[indole-3,4'-piperidin]-2-one |

TABLE 1-continued

| Compound Number | Structure | Name |
|---|---|---|
| 100 | 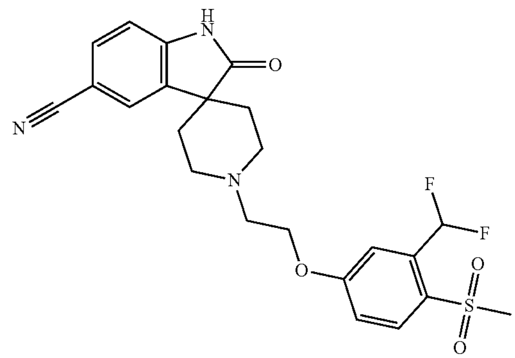 [SMILES: CS(=O)(=O)c1ccc(OCCN2CCC3(CC2)C(=O)Nc2ccc(C#N)cc23)cc1C(F)F] | 1'-{2-[3-(difluoromethyl)-4-methanesulfonylphenoxy]ethyl}-2-oxo-1,2-dihydrospiro[indole-3,4'-piperidine]-5-carbonitrile |
| 101 | 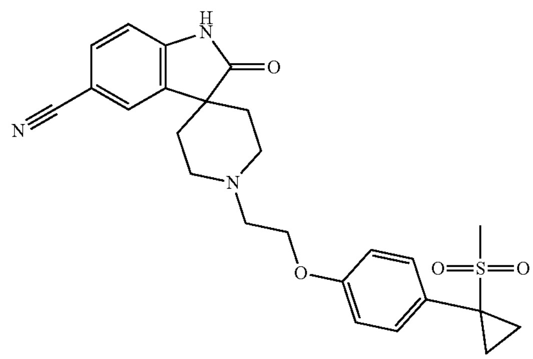 [SMILES: CS(=O)(=O)C1(c2ccc(OCCN3CCC4(CC3)C(=O)Nc3ccc(C#N)cc34)cc2)CC1] | 1'-{2-[4-(1-methanesulfonylcyclopropyl)phenoxy]ethyl}-2-oxo-1,2-dihydrospiro[indole-3,4'-piperidine]-5-carbonitrile |
| 102 | 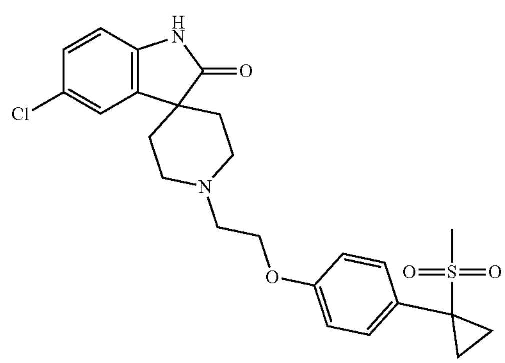 [SMILES: CS(=O)(=O)C1(c2ccc(OCCN3CCC4(CC3)C(=O)Nc3ccc(Cl)cc34)cc2)CC1] | 5-chloro-1'-{2-[4-(1-methanesulfonylcyclopropyl)phenoxy]ethyl}-1,2-dihydrospiro[indole-3,4'-piperidin]-2-one |
| 103 | 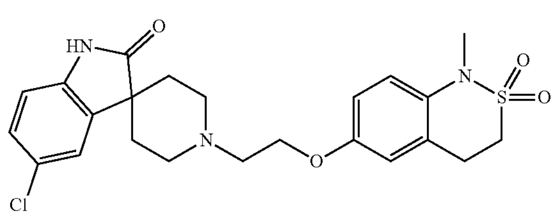 [SMILES: CN1c2ccc(OCCN3CCC4(CC3)C(=O)Nc3ccc(Cl)cc34)cc2CCS1(=O)=O] | 6-(2-{5-chloro-2-oxo-1,2-dihydrospiro[indole-3,4'-piperidin]-1'-yl}ethoxy)-1-methyl-3,4-dihydro-1H-2$\lambda^6$,1-benzothiazine-2,2-dione |
| 104 | 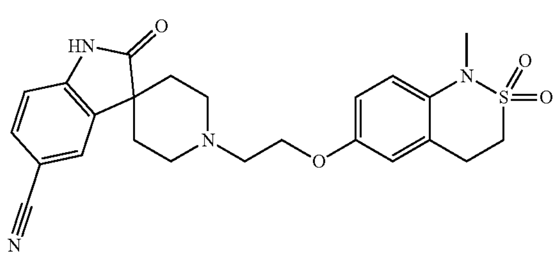 [SMILES: CN1c2ccc(OCCN3CCC4(CC3)C(=O)Nc3ccc(C#N)cc34)cc2CCS1(=O)=O] | 1'-{2-[(1-methyl-2,2-dioxo-3,4-dihydro-1H-2$\lambda^6$,1-benzothiazin-6-yl)oxy]ethyl}-2-oxo-1,2-dihydrospiro[indole-3,4'-piperidine]-5-carbonitrile |

TABLE 1-continued

| Compound Number | Structure | Name |
|---|---|---|
| 105 | 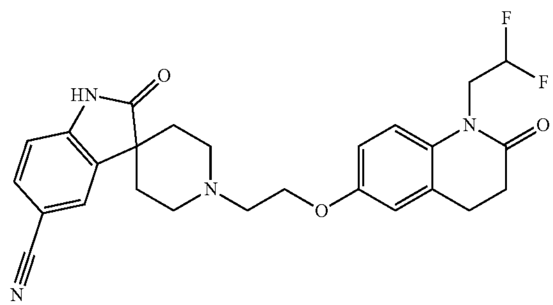 [SMILES: N#Cc1ccc2c(c1)C1(CCN(CCOc3ccc4c(c3)CCC(=O)N4CC(F)F)CC1)C(=O)N2] | 1'-(2-{[1-(2,2-difluoroethyl)-2-oxo-1,2,3,4-tetrahydroquinolin-6-yl]oxy}ethyl)-2-oxo-1,2-dihydrospiro[indole-3,4'-piperidine]-5-carbonitrile |
| 106 | 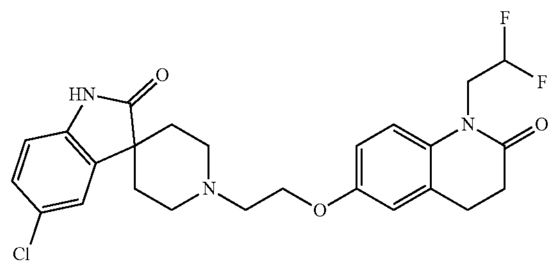 [SMILES: O=C1CCc2cc(OCCN3CCC4(CC3)C(=O)Nc3ccc(Cl)cc34)ccc2N1CC(F)F] | 5-chloro-1'-(2-{[1-(2,2-difluoroethyl)-2-oxo-1,2,3,4-tetrahydroquinolin-6-yl]oxy}ethyl)-1,2-dihydrospiro[indole-3,4'-piperidin]-2-one |
| 107 | 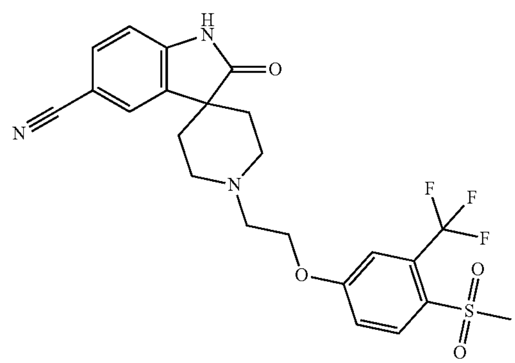 [SMILES: CS(=O)(=O)c1ccc(OCCN2CCC3(CC2)C(=O)Nc2ccc(C#N)cc23)cc1C(F)(F)F] | 1'-{2-[4-methanesulfonyl-3-(trifluoromethyl)phenoxy]ethyl}-2-oxo-1,2-dihydrospiro[indole-3,4'-piperidine]-5-carbonitrile |
| 108 | 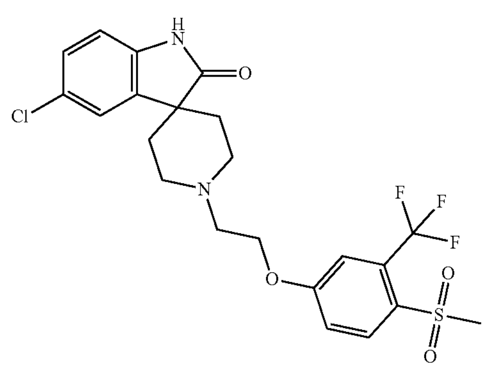 [SMILES: CS(=O)(=O)c1ccc(OCCN2CCC3(CC2)C(=O)Nc2ccc(Cl)cc23)cc1C(F)(F)F] | 5-chloro-1'-{2-[4-methanesulfonyl-3-(trifluoromethyl)phenoxy]ethyl}-1,2-dihydrospiro[indole-3,4'-piperidin]-2-one |

TABLE 1-continued

| Compound Number | Structure | Name |
|---|---|---|
| 109 | 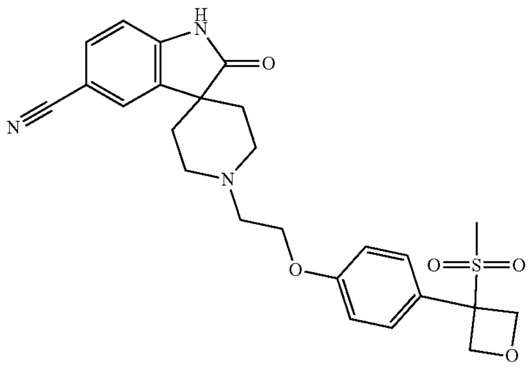 [SMILES: CS(=O)(=O)C1(c2ccc(OCCN3CCC4(CC3)C(=O)Nc3ccc(C#N)cc34)cc2)COC1] | 1'-{2-[4-(3-methanesulfonyloxetan-3-yl)phenoxy]ethyl}-2-oxo-1,2-dihydrospiro[indole-3,4'-piperidine]-5-carbonitrile |
| 110 | 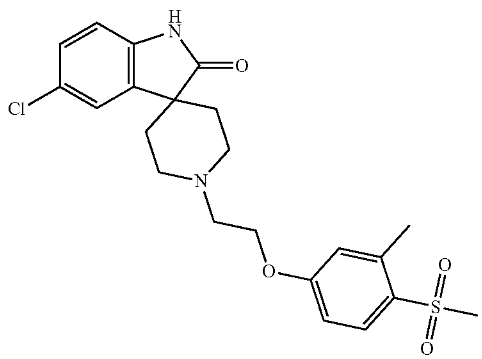 [SMILES: Cc1cc(OCCN2CCC3(CC2)C(=O)Nc2ccc(Cl)cc23)ccc1S(C)(=O)=O] | 5-chloro-1'-[2-(4-methanesulfonyl-3-methylphenoxy)ethyl]-1,2-dihydrospiro[indole-3,4'-piperidin]-2-one |
| 111 | 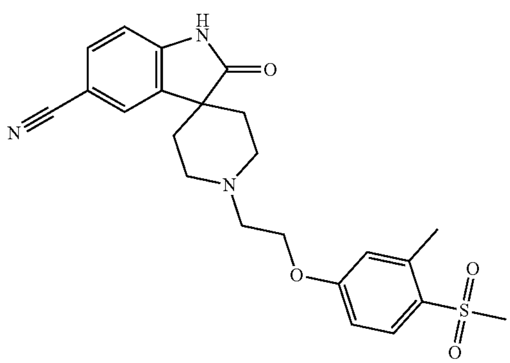 | 1'-[2-(4-methanesulfonyl-3-methylphenoxy)ethyl]-2-oxo-1,2-dihydrospiro[indole-3,4'-piperidine]-5-carbonitrile |
| 112 | 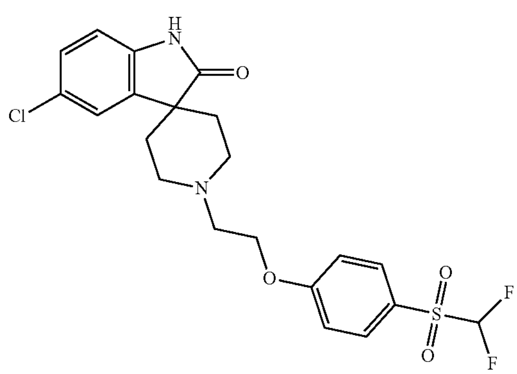 [SMILES: O=C1Nc2ccc(Cl)cc2C12CCN(CCOc1ccc(S(=O)(=O)C(F)F)cc1)CC2] | 5-chloro-1'-[2-(4-difluoromethanesulfonylphenoxy)ethyl]-1,2-dihydrospiro[indole-3,4'-piperidin]-2-one |

TABLE 1-continued

| Compound Number | Structure | Name |
|---|---|---|
| 113 | 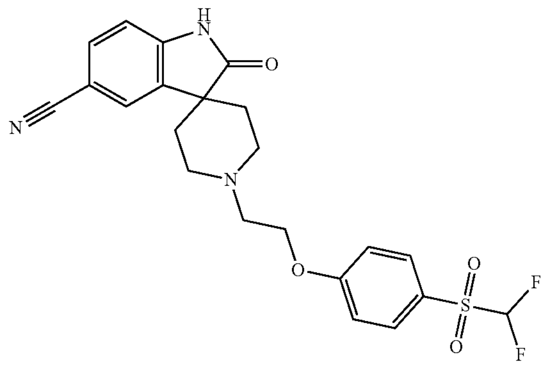 [SMILES: N#Cc1ccc2c(c1)C1(CCN(CCOc3ccc(S(=O)(=O)C(F)F)cc3)CC1)C(=O)N2] | 1'-[2-(4-difluoromethanesulfonylphenoxy)ethyl]-2-oxo-1,2-dihydrospiro[indole-3,4'-piperidine]-5-carbonitrile |
| 114 | 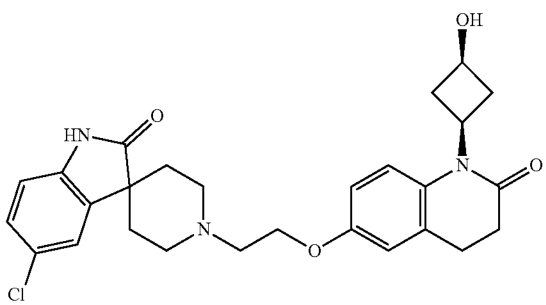 [SMILES: O=C1CCc2cc(OCCN3CCC4(CC3)C(=O)Nc3ccc(Cl)cc34)ccc2N1[C@H]1C[C@@H](O)C1] | 5-chloro-1'-[2-({2-oxo-1-[(cis)-3-hydroxycyclobutyl]-1,2,3,4-tetrahydroquinolin-6-yl}oxy)ethyl]-1,2-dihydrospiro[indole-3,4'-piperidin]-2-one |
| 115 | 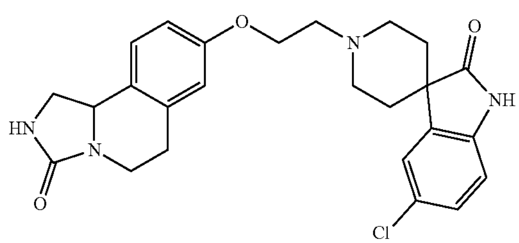 [SMILES: O=C1NCC2c3ccc(OCCN4CCC5(CC4)C(=O)Nc4ccc(Cl)cc45)cc3CCN12] | 5-chloro-1'-[2-({3-oxo-1H,2H,3H,5H,6H,10bH-imidazo[4,3-a]isoquinolin-8-yl}oxy)ethyl]-1,2-dihydrospiro[indole-3,4'-piperidin]-2-one |
| 116 | 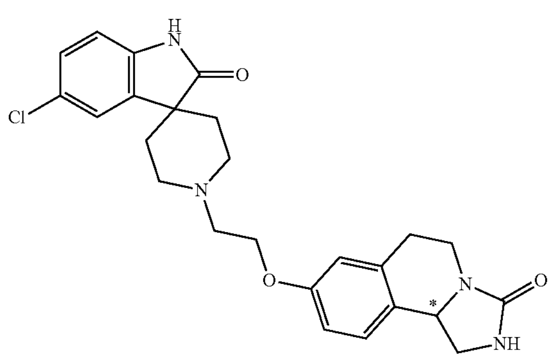 [SMILES: O=C1NCC2c3ccc(OCCN4CCC5(CC4)C(=O)Nc4ccc(Cl)cc45)cc3CCN12] | (S) or (R)-5-chloro-1'-[2-({3-oxo-1H,2H,3H,5H,6H,10bH-imidazo[4,3-a]isoquinolin-8-yl}oxy)ethyl]-1,2-dihydrospiro[indole-3,4'-piperidin]-2-one |

TABLE 1-continued

| Compound Number | Structure | Name |
|---|---|---|
| 117 | 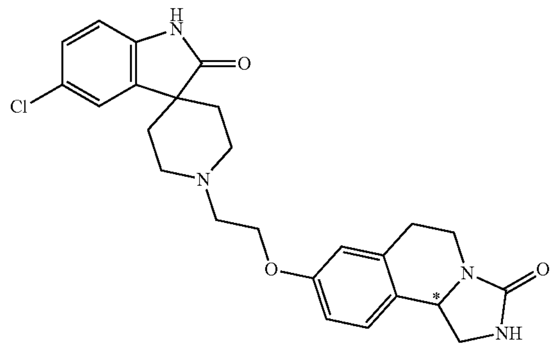 [SMILES: O=C1NCC2c3ccc(OCCN4CCC5(CC4)C(=O)Nc4ccc(Cl)cc45)cc3CCN12] | (R) or (S)-5-chloro-1'-[2-({3-oxo-1H,2H,3H,5H,6H,10bH-imidazo[4,3-a]isoquinolin-8-yl}oxy)ethyl]-1,2-dihydrospiro[indole-3,4'-piperidin]-2-one |
| 118 | 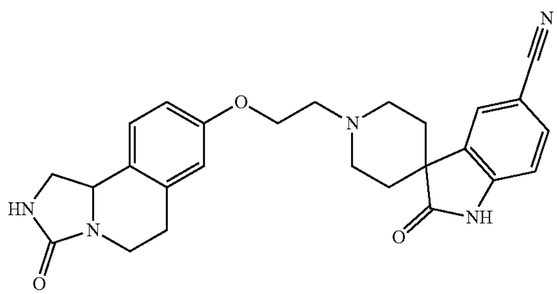 [SMILES: N#Cc1ccc2c(c1)C1(CCN(CCOc3ccc4c(c3)CCN3C(=O)NCC43)CC1)C(=O)N2] | 2-oxo-1'-[2-({3-oxo-1H,2H,3H,5H,6H,10bH-imidazo[4,3-a]isoquinolin-8-yl}oxy)ethyl]-1,2-dihydrospiro[indole-3,4'-piperidine]-5-carbonitrile |
| 119 | 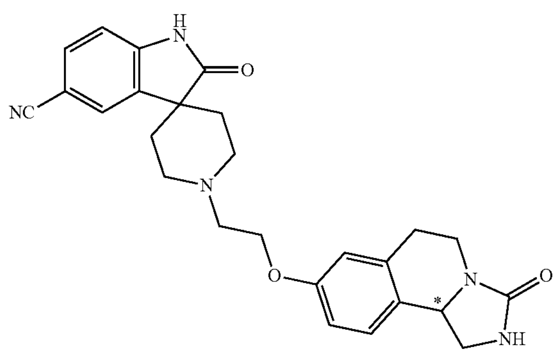 [SMILES: N#Cc1ccc2c(c1)C1(CCN(CCOc3ccc4c(c3)CCN3C(=O)NCC43)CC1)C(=O)N2] | (S) or (R)-2-oxo-1'-[2-({3-oxo-1H,2H,3H,5H,6H,10bH-imidazo[4,3-a]isoquinolin-8-yl}oxy)ethyl]-1,2-dihydrospiro[indole-3,4'-piperidine]-5-carbonitrile |
| 120 | 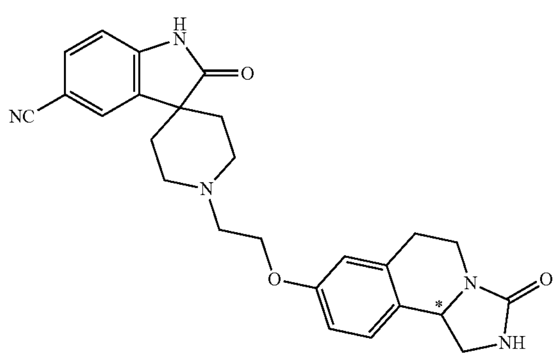 [SMILES: N#Cc1ccc2c(c1)C1(CCN(CCOc3ccc4c(c3)CCN3C(=O)NCC43)CC1)C(=O)N2] | (R) or (S)-2-oxo-1'-[2-({3-oxo-1H,2H,3H,5H,6H,10bH-imidazo[4,3-a]isoquinolin-8-yl}oxy)ethyl]-1,2-dihydrospiro[indole-3,4'-piperidine]-5-carbonitrile |
| 121 | 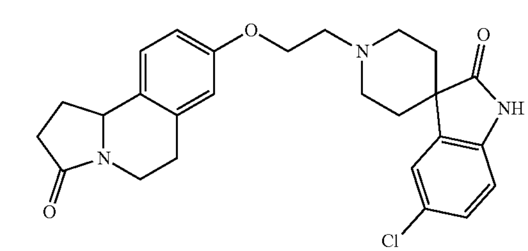 [SMILES: O=C1CCC2c3ccc(OCCN4CCC5(CC4)C(=O)Nc4ccc(Cl)cc45)cc3CCN12] | 5-chloro-1'-[2-({3-oxo-1H,2H,3H,5H,6H,10bH-pyrrolo[2,1-a]isoquinolin-8-yl}oxy)ethyl]-1,2-dihydrospiro[indole-3,4'-piperidin]-2-one |

TABLE 1-continued

| Compound Number | Structure | Name |
|---|---|---|
| 122 | 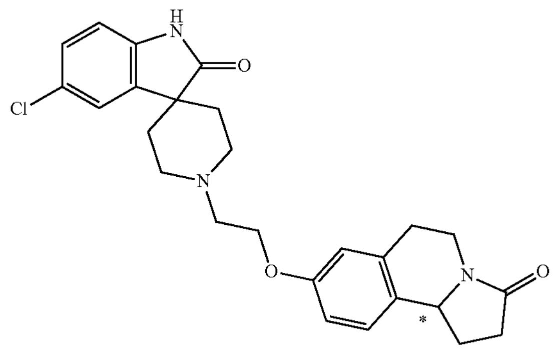 [SMILES: O=C1CCC2c3ccc(OCCN4CCC5(CC4)C(=O)Nc4ccc(Cl)cc45)cc3CCN12] | (S) or (R)-5-chloro-1'-[2-({3-oxo-1H,2H,3H,5H,6H,10bH-pyrrolo[2,1-a]isoquinolin-8-yl}oxy)ethyl]-1,2-dihydrospiro[indole-3,4'-piperidin]-2-one |
| 123 | 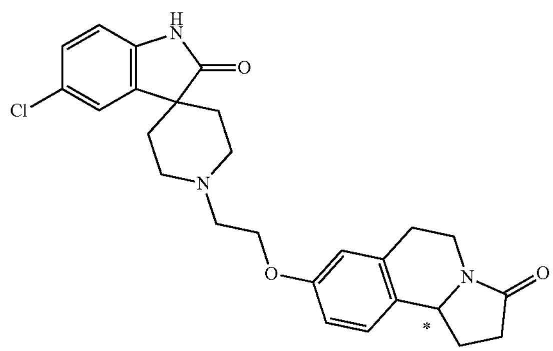 [SMILES: O=C1CCC2c3ccc(OCCN4CCC5(CC4)C(=O)Nc4ccc(Cl)cc45)cc3CCN12] | (R) or (S)-5-chloro-1'-[2-({3-oxo-1H,2H,3H,5H,6H,10bH-pyrrolo[2,1-a]isoquinolin-8-yl}oxy)ethyl]-1,2-dihydrospiro[indole-3,4'-piperidin]-2-one |
| 124 | 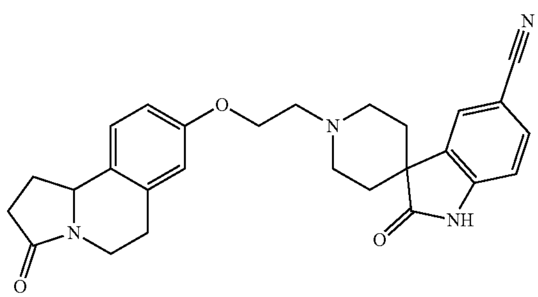 [SMILES: N#Cc1ccc2c(c1)C1(CCN(CCOc3ccc4c(c3)CCN3C(=O)CCC43)CC1)C(=O)N2] | 2-oxo-1'-(2-({3-oxo-1H,2H,3H,5H,6H,10bH-pyrrolo[2,1-a]isoquinolin-8-yl}oxy)ethyl]-1,2-dihydrospiro[indole-3,4'-piperidine]-5-carbonitrile |
| 125 | 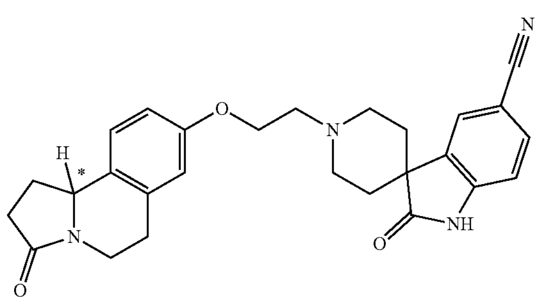 [SMILES: N#Cc1ccc2c(c1)C1(CCN(CCOc3ccc4c(c3)CCN3C(=O)CCC43)CC1)C(=O)N2] | (S) or (R)-2-oxo-1'-(2-((3-oxo-1,2,3,5,6,10b-hexahydropyrrolo[2,1-a]isoquinolin-8-yl)oxy)ethyl)spiro[indoline-3,4'-piperidine]-5-carbonitrile |
| 126 | 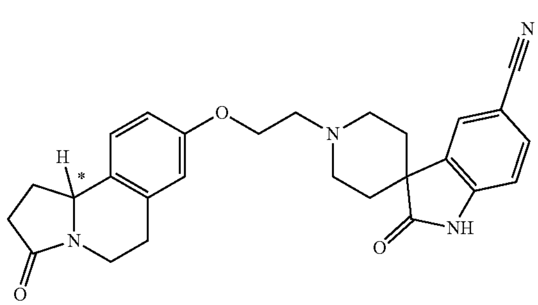 [SMILES: N#Cc1ccc2c(c1)C1(CCN(CCOc3ccc4c(c3)CCN3C(=O)CCC43)CC1)C(=O)N2] | (R) or (S)-2-oxo-1'-(2-((3-oxo-1,2,3,5,6,10b-hexahydropyrrolo[2,1-a]isoquinolin-8-yl)oxy)ethyl)spiro[indoline-3,4'-piperidine]-5-carbonitrile |

TABLE 1-continued

| Compound Number | Structure | Name |
|---|---|---|
| 127 | 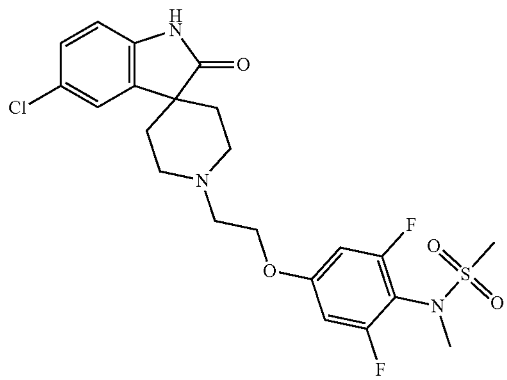 [SMILES: CN(c1c(F)cc(OCCN2CCC3(CC2)C(=O)Nc2ccc(Cl)cc23)cc1F)S(C)(=O)=O] | N-[4-(2-{5-chloro-2-oxo-1,2-dihydrospiro[indole-3,4'-piperidin]-1'-yl}ethoxy)-2,6-difluorophenyl]-N-methylmethanesulfonamide |
| 128 | 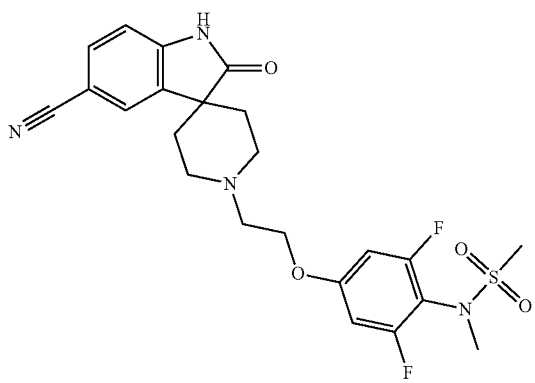 [SMILES: CN(c1c(F)cc(OCCN2CCC3(CC2)C(=O)Nc2ccc(C#N)cc23)cc1F)S(C)(=O)=O] | N-[4-(2-{5-cyano-2-oxo-1,2-dihydrospiro[indole-3,4'-piperidin]-1'-yl}ethoxy)-2,6-difluorophenyl]-N-methylmethanesulfonamide |
| 129 | 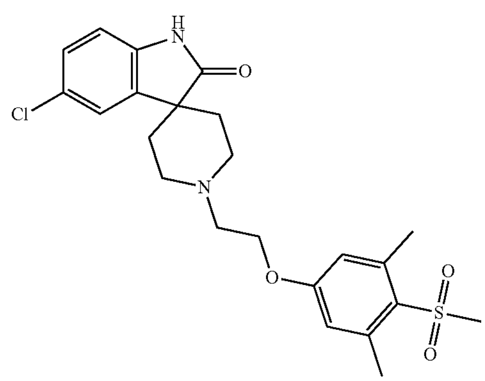 [SMILES: Cc1cc(OCCN2CCC3(CC2)C(=O)Nc2ccc(Cl)cc23)cc(C)c1S(C)(=O)=O] | 5-chloro-1'-[2-(4-methanesulfonyl-3,5-dimethylphenoxy)ethyl]-1,2-dihydrospiro[indole-3,4'-piperidin]-2-one |
| 130 | 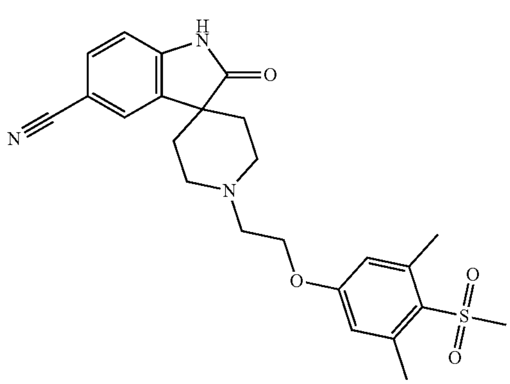 [SMILES: Cc1cc(OCCN2CCC3(CC2)C(=O)Nc2ccc(C#N)cc23)cc(C)c1S(C)(=O)=O] | 1'-[2-(4-methanesulfonyl-3,5-dimethylphenoxy)ethyl]-2-oxo-1,2-dihydrospiro[indole-3,4'-piperidine]-5-carbonitrile |

TABLE 1-continued

| Compound Number | Structure | Name |
|---|---|---|
| 131 | 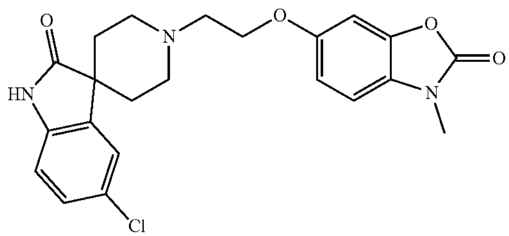 [SMILES: Cn1c(=O)oc2cc(OCCN3CCC4(CC3)C(=O)Nc3ccc(Cl)cc34)ccc21] | 5-chloro-1'-{2-[(3-methyl-2-oxo-2,3-dihydro-1,3-benzoxazol-6-yl)oxy]ethyl]-1,2-dihydrospiro[indole-3,4'-piperidin]-2-one |
| 132 | 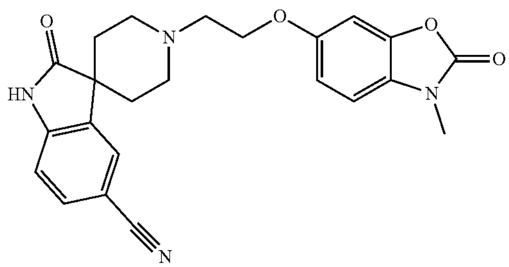 [SMILES: Cn1c(=O)oc2cc(OCCN3CCC4(CC3)C(=O)Nc3ccc(C#N)cc34)ccc21] | 1'-{2-[(3-methyl-2-oxo-2,3-dihydro-1,3-benzoxazol-6-yl)oxy]ethyl}-2-oxo-1,2-dihydrospiro[indole-3,4'-piperidine]-5-carbonitrile |
| 133 | 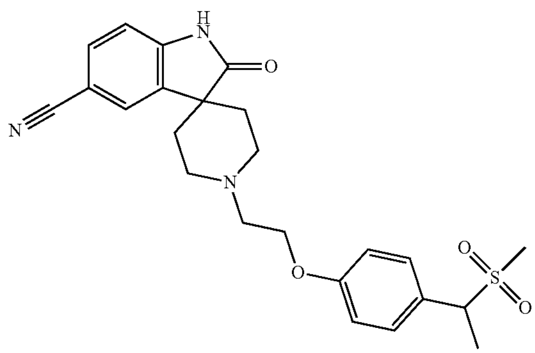 [SMILES: CC(c1ccc(OCCN2CCC3(CC2)C(=O)Nc2ccc(C#N)cc23)cc1)S(C)(=O)=O] | 1'-(2-[4-(1-methanesulfonylethyl)phenoxy]ethyl}-2-oxo-1,2-dihydrospiro[indole-3,4'-piperidine]-5-carbonitrile |
| 134 | 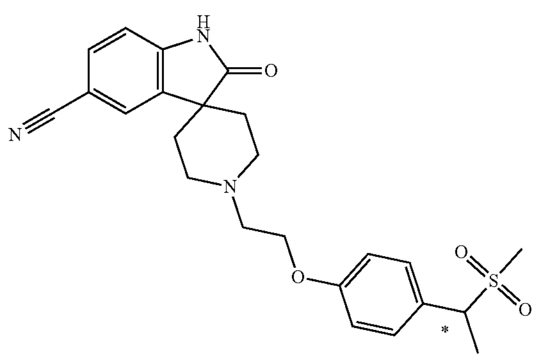 [SMILES: CC(c1ccc(OCCN2CCC3(CC2)C(=O)Nc2ccc(C#N)cc23)cc1)S(C)(=O)=O] | (S) or (R)-1'-{2-[4-(1-methanesulfonylethyl)phenoxy]ethyl}-2-oxo-1,2-dihydrospiro[indole-3,4'-piperidine]-5-carbonitrile |
| 135 | 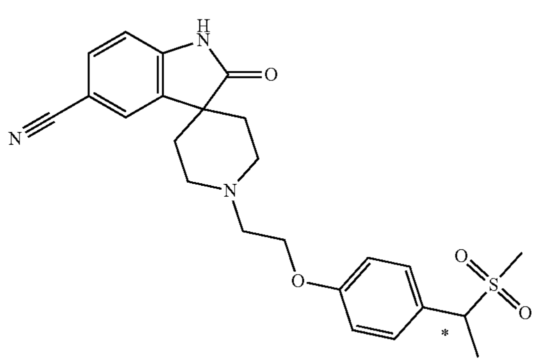 [SMILES: CC(c1ccc(OCCN2CCC3(CC2)C(=O)Nc2ccc(C#N)cc23)cc1)S(C)(=O)=O] | (R) or (S)-1'-{2-[4-(1-methanesulfonylethyl)phenoxy]ethyl}-2-oxo-1,2-dihydrospiro[indole-3,4'-piperidine]-5-carbonitrile |

| Compound Number | Structure | Name |
|---|---|---|
| 136 | 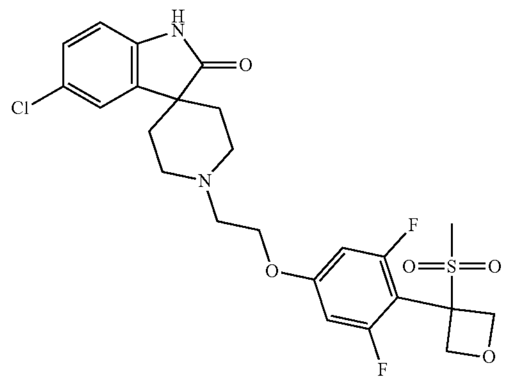 [SMILES: CS(=O)(=O)C1(c2c(F)cc(OCCN3CCC4(CC3)C(=O)Nc3ccc(Cl)cc34)cc2F)COC1] | 5-chloro-1'-{2-[3,5-difluoro-4-(3-methanesulfonyloxetan-3-yl)phenoxy]ethyl}-1,2-dihydrospiro[indole-3,4'-piperidin]-2-one |
| 137 | 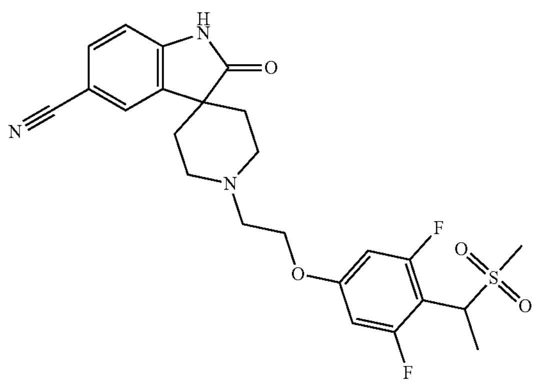 | 1'-(2-[3,5-difluoro-4-(1-methanesulfonylethyl)phenoxy]ethyl}-2-oxo-1,2-dihydrospiro[indole-3,4'-piperidine]-5-carbonitrile |
| 138 | 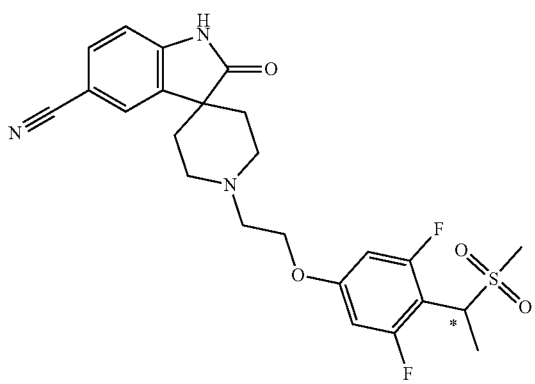 | (S) or (R)-1'-{2-[3,5-difluoro-4-(1-methanesulfonylethyl)phenoxy]ethyl}-2-oxo-1,2-dihydrospiro[indole-3,4'-piperidine]-5-carbonitrile |
| 139 | 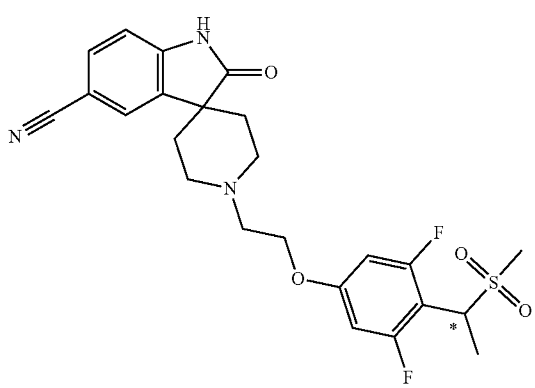 [SMILES: CC(c1c(F)cc(OCCN2CCC3(CC2)C(=O)Nc2ccc(C#N)cc23)cc1F)S(C)(=O)=O] | (R) or (S)-1'-{2-[3,5-difluoro-4-(1-methanesulfonylethyl)phenoxy]ethyl}-2-oxo-1,2-dihydrospiro[indole-3,4'-piperidine]-5-carbonitrile |

TABLE 1-continued

| Compound Number | Structure | Name |
|---|---|---|
| 140 | 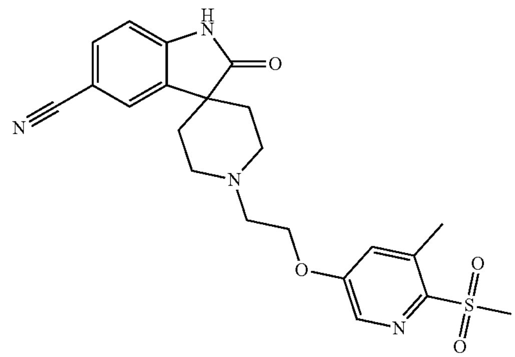 [SMILES: Cc1cc(OCCN2CCC3(CC2)C(=O)Nc2ccc(C#N)cc23)cnc1S(C)(=O)=O] | 1'-{2-[(6-methanesulfonyl-5-methylpyridin-3-yl)oxy]ethyl}-2-oxo-1,2-dihydrospiro[indole-3,4'-piperidine]-5-carbonitrile |
| 141 | 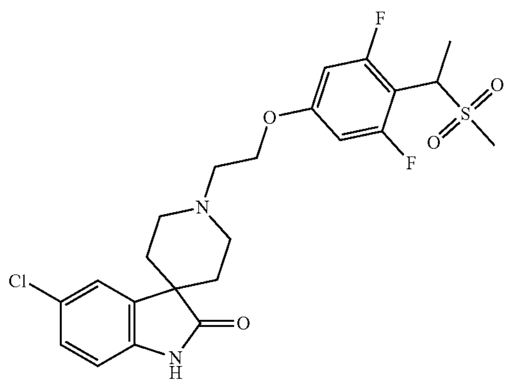 [SMILES: CC(c1c(F)cc(OCCN2CCC3(CC2)C(=O)Nc2ccc(Cl)cc23)cc1F)S(C)(=O)=O] | 5-chloro-1'-{2-[3,5-difluoro-4-(1-methanesulfonylethyl)phenoxy]ethyl}-1,2-dihydrospiro[indole-3,4'-piperidin]-2-one |
| 142 | 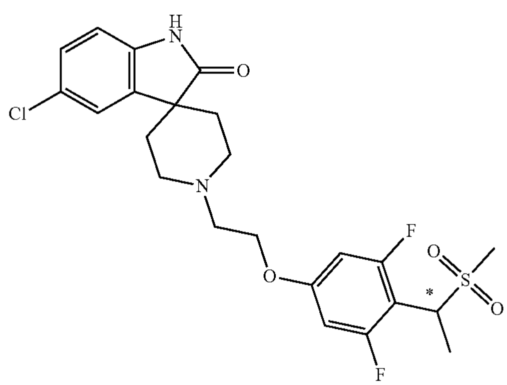 | (S) or (R)-5-chloro-1'-{2-[3,5-difluoro-4-(1-methanesulfonylethyl)phenoxy]ethyl}-1,2-dihydrospiro[indole-3,4'-piperidin]-2-one |
| 143 | 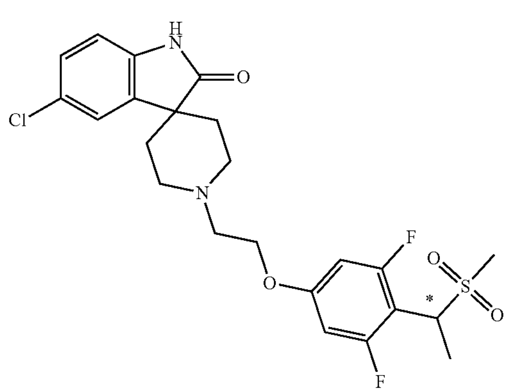 | (R) or (S)-5-chloro-1'-{2-[3,5-difluoro-4-(1-methanesulfonylethyl)phenoxy]ethyl}-1,2-dihydrospiro[indole-3,4'-piperidin]-2-one |

TABLE 1-continued

| Compound Number | Structure | Name |
|---|---|---|
| 144 | 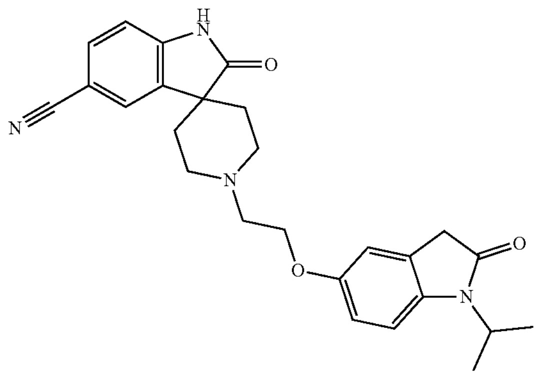 [SMILES: CC(C)N1C(=O)Cc2cc(OCCN3CCC4(CC3)C(=O)Nc3ccc(C#N)cc34)ccc21] | 2-oxo-1'-(2-{[2-oxo-1-(propan-2-yl)-2,3-dihydro-1H-indol-5-yl]oxy}ethyl)-1,2-dihydrospiro[indole-3,4'-piperidine]-5-carbonitrile |
| 145 | 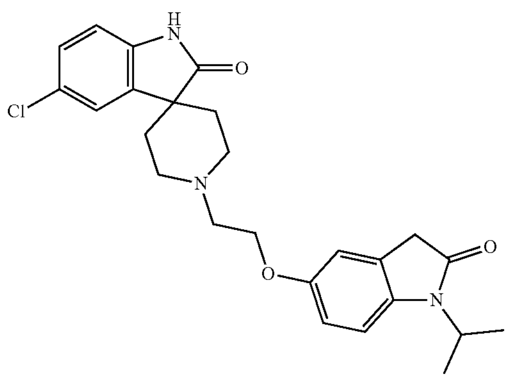 [SMILES: CC(C)N1C(=O)Cc2cc(OCCN3CCC4(CC3)C(=O)Nc3ccc(Cl)cc34)ccc21] | 5-chloro-1'-(2-{[2-oxo-1-(propan-2-yl)-2,3-dihydro-1H-indol-5-yl]oxy}ethyl)-1,2-dihydrospiro[indole-3,4'-piperidin]-2-one |
| 146 | 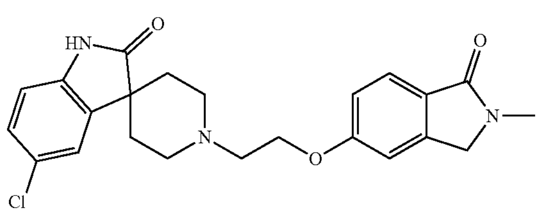 [SMILES: CN1Cc2cc(OCCN3CCC4(CC3)C(=O)Nc3ccc(Cl)cc34)ccc2C1=O] | 5-chloro-1'-{2-[(2-methyl-1-oxo-2,3-dihydro-1H-isoindol-5-yl)oxy]ethyl}-1,2-dihydrospiro[indole-3,4'-piperidin]-2-one |
| 147 | 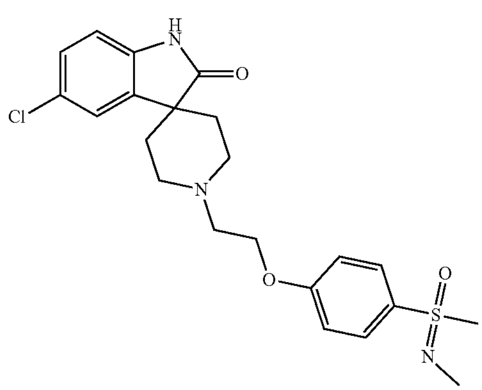 [SMILES: CN=S(C)(=O)c1ccc(OCCN2CCC3(CC2)C(=O)Nc2ccc(Cl)cc23)cc1] | 5-chloro-1'-(2-{4-[methyl(methylimino)oxo-$\lambda^6$-sulfanyl]phenoxy}ethyl)-1,2-dihydrospiro[indole-3,4'-piperidin]-2-one |

TABLE 1-continued

| Compound Number | Structure | Name |
|---|---|---|
| 148 | 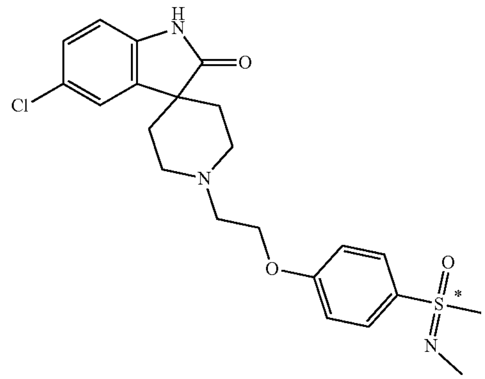 [SMILES: CN=S(C)(=O)c1ccc(OCCN2CCC3(CC2)C(=O)Nc2ccc(Cl)cc23)cc1] | (S) or (R)-5-chloro-1'-(2-{4-[methyl(methylimino)oxo-$\lambda^6$-sulfanyl]phenoxy}ethyl)-1,2-dihydrospiro[indole-3,4'-piperidin]-2-one |
| 149 | 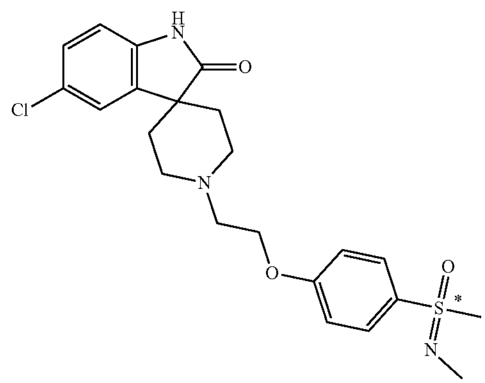 [SMILES: CN=S(C)(=O)c1ccc(OCCN2CCC3(CC2)C(=O)Nc2ccc(Cl)cc23)cc1] | (R) or (S)-5-chloro-1'-(2-{4-[methyl(methylimino)oxo-$\lambda^6$-sulfanyl]phenoxy}ethyl)-1,2-dihydrospiro[indole-3,4'-piperidin]-2-one |
| 150 | 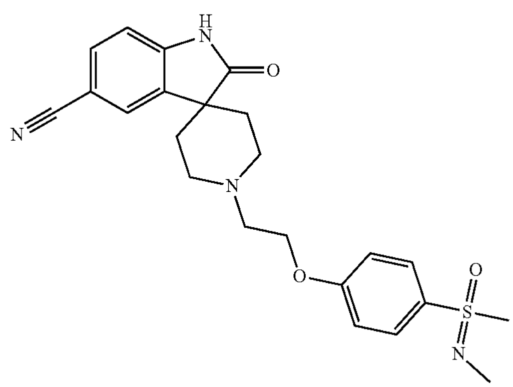 [SMILES: CN=S(C)(=O)c1ccc(OCCN2CCC3(CC2)C(=O)Nc2ccc(C#N)cc23)cc1] | 1'-(2-{4-[methyl(methylimino)oxo-$\lambda^6$-sulfanyl]phenoxy}ethyl)-2-oxo-1,2-dihydrospiro[indole-3,4'-piperidine]-5-carbonitrile |
| 151 | 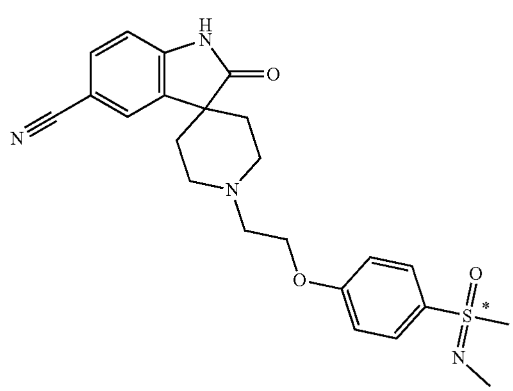 [SMILES: CN=S(C)(=O)c1ccc(OCCN2CCC3(CC2)C(=O)Nc2ccc(C#N)cc23)cc1] | (S) or (R)-1'-(2-{4-[methyl(methylimino)oxo-$\lambda^6$-sulfanyl]phenoxy}ethyl)-2-oxo-1,2-dihydrospiro[indole-3,4'-piperidine]-5-carbonitrile |

TABLE 1-continued

| Compound Number | Structure | Name |
|---|---|---|
| 152 | 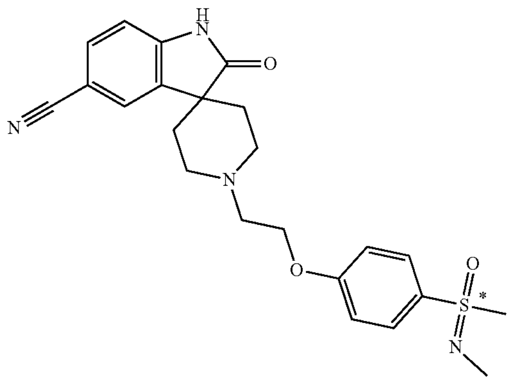 [SMILES: CN=S(C)(=O)c1ccc(OCCN2CCC3(CC2)C(=O)Nc2ccc(C#N)cc23)cc1] | (R) or (S)-1'-(2-{4-[methyl(methylimino)oxo-$\lambda^6$-sulfanyl]phenoxy}ethyl)-2-oxo-1,2-dihydrospiro[indole-3,4'-piperidine]-5-carbonitrile |
| 153 | 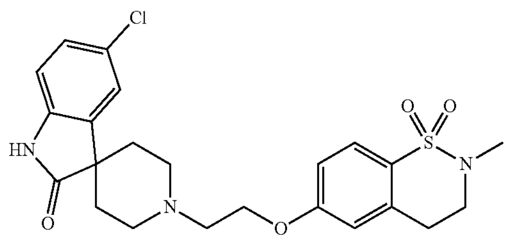 [SMILES: CN1CCc2cc(OCCN3CCC4(CC3)C(=O)Nc3ccc(Cl)cc34)ccc2S1(=O)=O] | 6-(2-{5-chloro-2-oxo-1,2-dihydrospiro[indole-3,4'-piperidin]-1'-yl}ethoxy)-2-methyl-3,4-dihydro-2H-1$\lambda^6$,2-benzothiazine-1,1-dione |
| 154 | 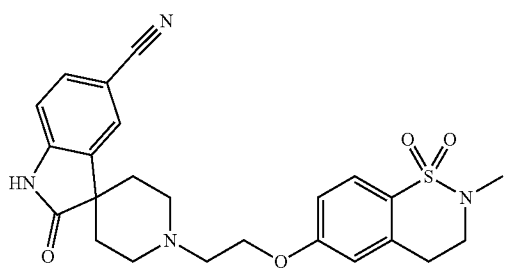 [SMILES: CN1CCc2cc(OCCN3CCC4(CC3)C(=O)Nc3ccc(C#N)cc34)ccc2S1(=O)=O] | 1'-{2-[(2-methyl-1,1-dioxo-3,4-dihydro-2H-1$\lambda^6$,2-benzothiazin-6-yl)oxy]ethyl}-2-oxo-1,2-dihydrospiro[indole-3,4'-piperidine]-5-carbonitrile |
| 155 | 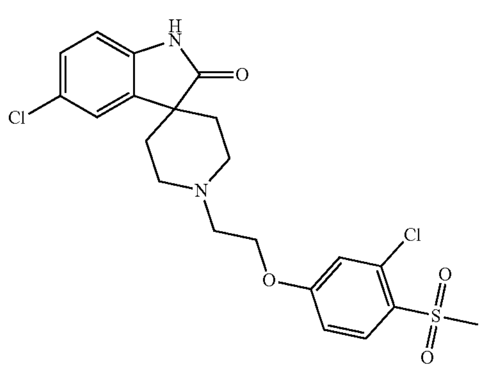 [SMILES: CS(=O)(=O)c1ccc(OCCN2CCC3(CC2)C(=O)Nc2ccc(Cl)cc23)cc1Cl] | 5-chloro-1'-[2-(3-chloro-4-methanesulfonylphenoxy)ethyl]-1,2-dihydrospiro[indole-3,4'-piperidin]-2-one |

| Compound Number | Structure | Name |
|---|---|---|
| 156 | 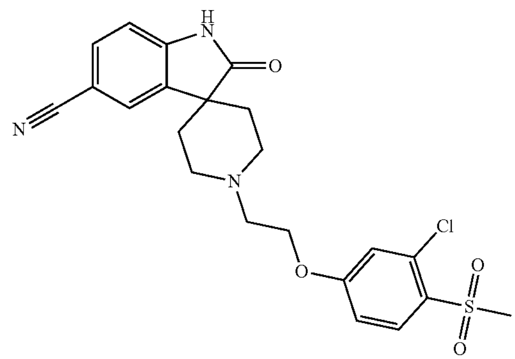 [SMILES: CS(=O)(=O)c1ccc(OCCN2CCC3(CC2)C(=O)Nc2ccc(C#N)cc23)cc1Cl] | 1'-[2-(3-chloro-4-methanesulfonylphenoxy)ethyl]-2-oxo-1,2-dihydrospiro[indole-3,4'-piperidine]-5-carbonitrile |
| 157 | 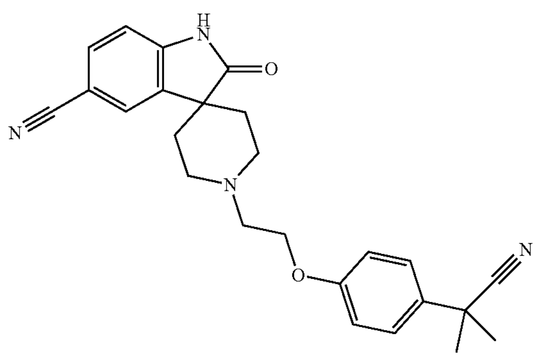 [SMILES: CC(C)(C#N)c1ccc(OCCN2CCC3(CC2)C(=O)Nc2ccc(C#N)cc23)cc1] | 1'-{2-[4-(1-cyano-1-methylethyl)phenoxy]ethyl}-2-oxo-1,2-dihydrospiro[indole-3,4'-piperidine]-5-carbonitrile |
| 158 | 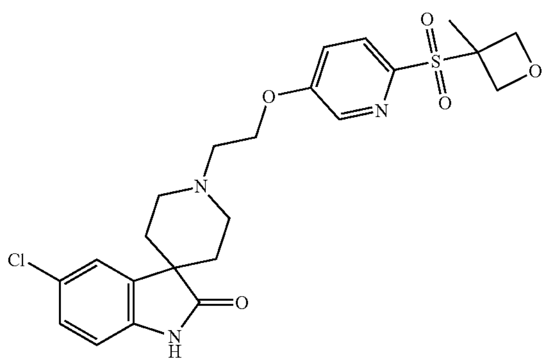 [SMILES: CC1(S(=O)(=O)c2ccc(OCCN3CCC4(CC3)C(=O)Nc3ccc(Cl)cc34)cn2)COC1] | 5-chloro-1'-[2-({6-[(3-methyloxetan-3-yl)sulfonyl]pyridin-3-yl}oxy)ethyl]-1,2-dihydrospiro[indole-3,4'-piperidin]-2-one |
| 159 | 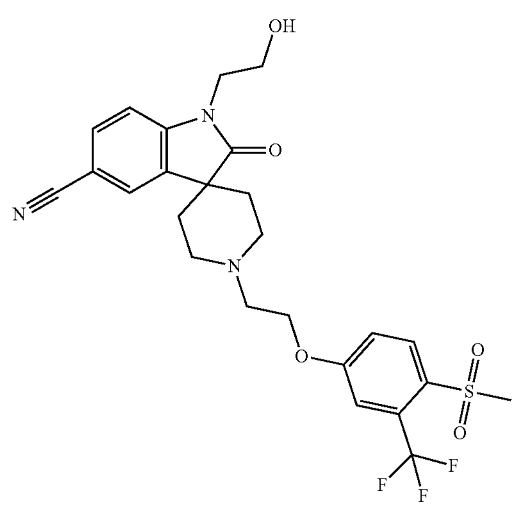 [SMILES: CS(=O)(=O)c1ccc(OCCN2CCC3(CC2)C(=O)N(CCO)c2ccc(C#N)cc23)cc1C(F)(F)F] | 1-(2-hydroxyethyl)-1'-{2-[4-methanesulfonyl-3-(trifluoromethyl)phenoxy]ethyl}-2-oxo-1,2-dihydrospiro[indole-3,4'-piperidine]-5-carbonitrile |

TABLE 1-continued

| Compound Number | Structure | Name |
|---|---|---|
| 160 | 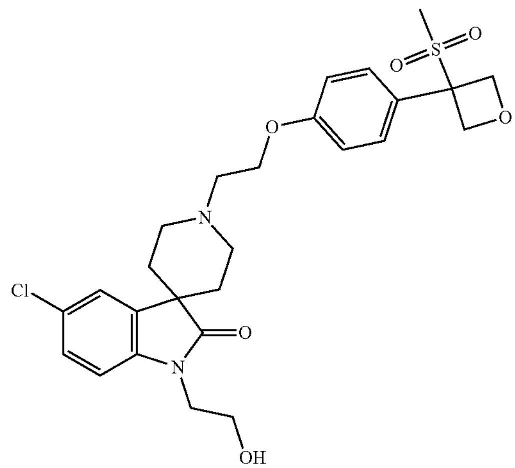 [SMILES: CS(=O)(=O)C1(c2ccc(OCCN3CCC4(CC3)C(=O)N(CCO)c3ccc(Cl)cc34)cc2)COC1] | 5-chloro-1-(2-hydroxyethyl)-1'-{2-[4-(3-methanesulfonyloxetan-3-yl)phenoxy]ethyl}-1,2-dihydrospiro[indole-3,4'-piperidin]-2-one |
| 161 | 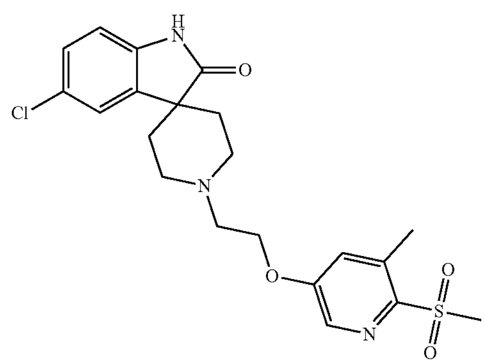 [SMILES: Cc1cc(OCCN2CCC3(CC2)C(=O)Nc2ccc(Cl)cc23)cnc1S(C)(=O)=O] | 5-chloro-1'-{2-[(6-methanesulfonyl-5-methylpyridin-3-yl)oxy]ethyl}-1,2-dihydrospiro[indole-3,4'-piperidin]-2-one |
| 162 | 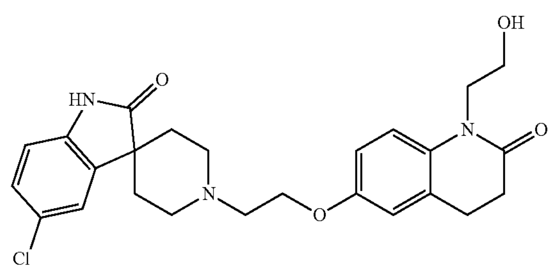 [SMILES: O=C1CCc2cc(OCCN3CCC4(CC3)C(=O)Nc3ccc(Cl)cc34)ccc2N1CCO] | 5-chloro-1'-(2-{[1-(2-hydroxyethyl)-2-oxo-1,2,3,4-tetrahydroquinolin-6-yl]oxy}ethyl)-1,2-dihydrospiro[indole-3,4'-piperidin]-2-one |
| 163 | 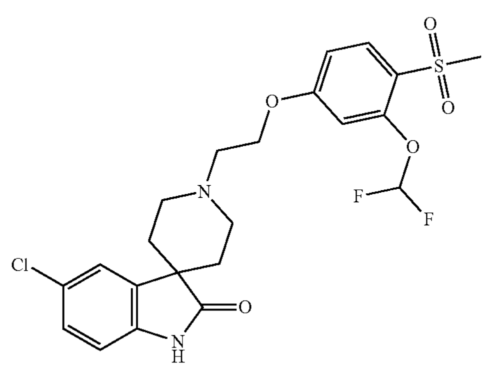 [SMILES: CS(=O)(=O)c1ccc(OCCN2CCC3(CC2)C(=O)Nc2ccc(Cl)cc23)cc1OC(F)F] | 5-chloro-1'-{2-[3-(difluoromethoxy)-4-methanesulfonylphenoxy]ethyl}-1,2-dihydrospiro[indole-3,4'-piperidin]-2-one |

TABLE 1-continued

| Compound Number | Structure | Name |
|---|---|---|
| 164 | 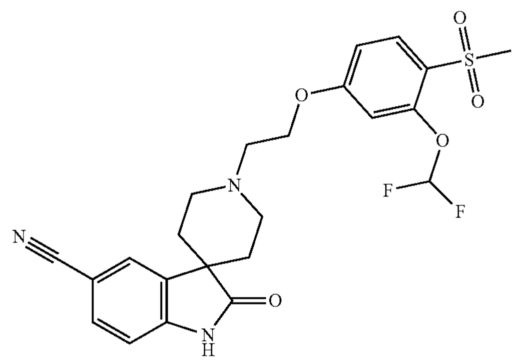 [SMILES: CS(=O)(=O)c1ccc(OCCN2CCC3(CC2)C(=O)Nc2ccc(C#N)cc23)cc1OC(F)F] | 1'-{2-[3-(difluoromethoxy)-4-methanesulfonylphenoxy]ethyl}-2-oxo-1,2-dihydrospiro[indole-3,4'-piperidine]-5-carbonitrile |
| 165 | 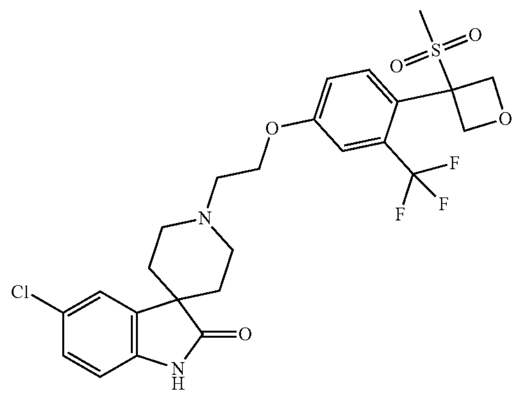 [SMILES: CS(=O)(=O)C1(c2ccc(OCCN3CCC4(CC3)C(=O)Nc3ccc(Cl)cc34)cc2C(F)(F)F)COC1] | 5-chloro-1'-{2-[4-(3-methanesulfonyloxetan-3-yl)-3-(trifluoromethyl)phenoxy]ethyl}-1,2-dihydrospiro[indole-3,4'-piperidin]-2-one |
| 166 | 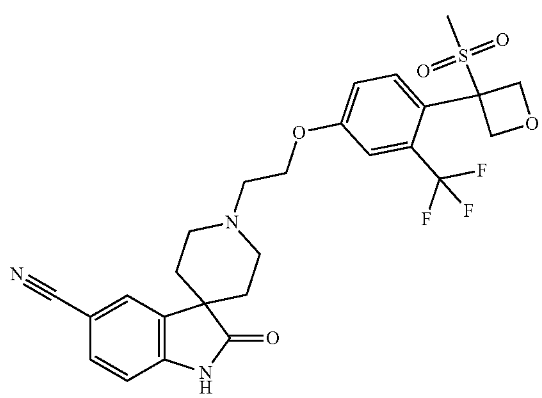 [SMILES: CS(=O)(=O)C1(c2ccc(OCCN3CCC4(CC3)C(=O)Nc3ccc(C#N)cc34)cc2C(F)(F)F)COC1] | 1'-(2-[4-(3-methanesulfonyloxetan-3-yl)-3-(trifluoromethyl)phenoxy]ethyl}-2-oxo-1,2-dihydrospiro[indole-3,4'-piperidine]-5-carbonitrile |
| 167 | 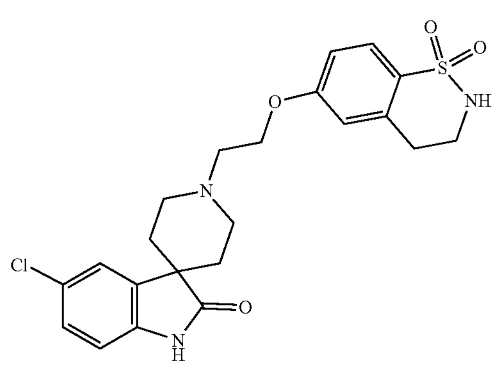 [SMILES: O=C1Nc2ccc(Cl)cc2C12CCN(CCOc1ccc3c(c1)CCNS3(=O)=O)CC2] | 6-(2-{5-chloro-2-oxo-1,2-dihydrospiro[indole-3,4'-piperidin]-1'-yl}ethoxy)-3,4-dihydro-2H-1$\lambda^6$,2-benzothiazine-1,1-dione |

TABLE 1-continued

| Compound Number | Structure | Name |
|---|---|---|
| 168 | 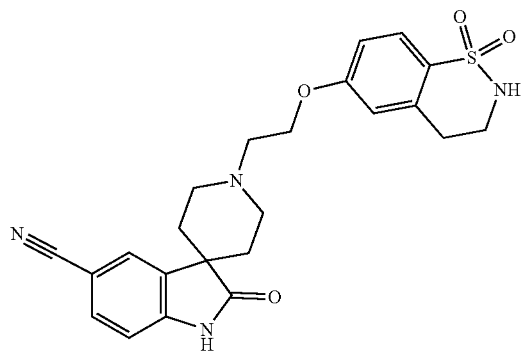 [SMILES: N#Cc1ccc2c(c1)C1(CCN(CCOc3ccc4c(c3)CCNS4(=O)=O)CC1)C(=O)N2] | 1'-{2-[(1,1-dioxo-3,4-dihydro-2H-1λ⁶,2-benzothiazin-6-yl)oxy]ethyl}-2-oxo-1,2-dihydrospiro[indole-3,4'-piperidine]-5-carbonitrile |
| 169 | 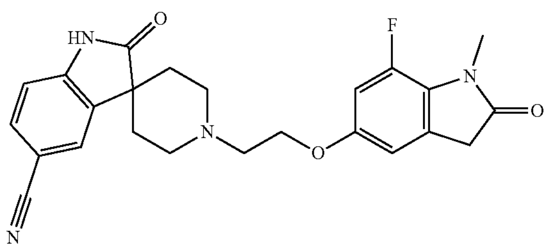 [SMILES: CN1C(=O)Cc2cc(OCCN3CCC4(CC3)C(=O)Nc3ccc(C#N)cc34)cc(F)c21] | 1'-{2-[(7-fluoro-1-methyl-2-oxo-2,3-dihydro-1H-indol-5-yl)oxy]ethyl}-2-oxo-1,2-dihydrospiro[indole-3,4'-piperidine]-5-carbonitrile |
| 170 | 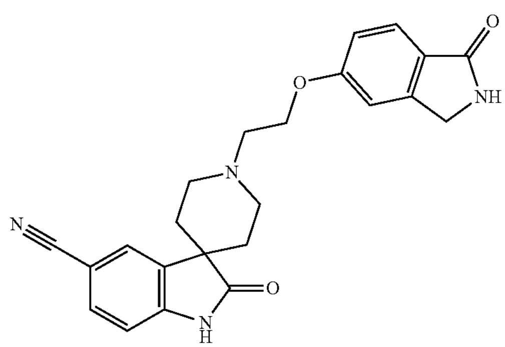 [SMILES: N#Cc1ccc2c(c1)C1(CCN(CCOc3ccc4c(c3)CNC4=O)CC1)C(=O)N2] | 2-oxo-1'-{2-[(1-oxo-2,3-dihydro-1H-isoindol-5-yl)oxy]ethyl}-1,2-dihydrospiro[indole-3,4'-piperidine]-5-carbonitrile |
| 171 | 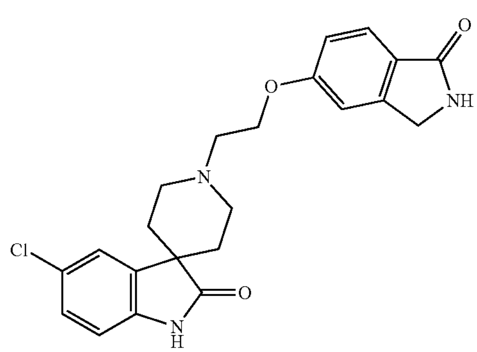 [SMILES: O=C1NCc2cc(OCCN3CCC4(CC3)C(=O)Nc3ccc(Cl)cc34)ccc21] | 5-chloro-1'-{2-[(1-oxo-2,3-dihydro-1H-isoindol-5-yl)oxy]ethyl}-1,2-dihydrospiro[indole-3,4'-piperidin]-2-one |

TABLE 1-continued

| Compound Number | Structure | Name |
|---|---|---|
| 172 | 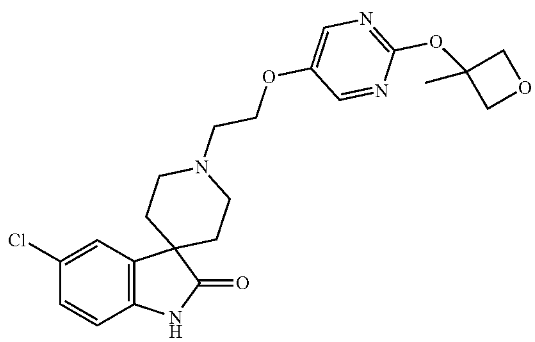 [SMILES: CC1(Oc2ncc(OCCN3CCC4(CC3)C(=O)Nc3ccc(Cl)cc34)cn2)COC1] | 5-chloro-1'-[2-({2-[(3-methyloxetan-3-yl)oxy]pyrimidin-5-yl}oxy)ethyl]-1,2-dihydrospiro[indole-3,4'-piperidin]-2-one |
| 173 | 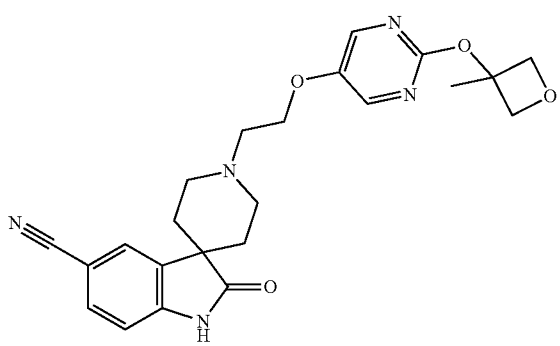 [SMILES: CC1(Oc2ncc(OCCN3CCC4(CC3)C(=O)Nc3ccc(C#N)cc34)cn2)COC1] | 1'-[2-({2-[(3-methyloxetan-3-yl)oxy]pyrimidin-5-yl}oxy)ethyl]-2-oxo-1,2-dihydrospiro[indole-3,4'-piperidine]-5-carbonitrile |
| 174 | 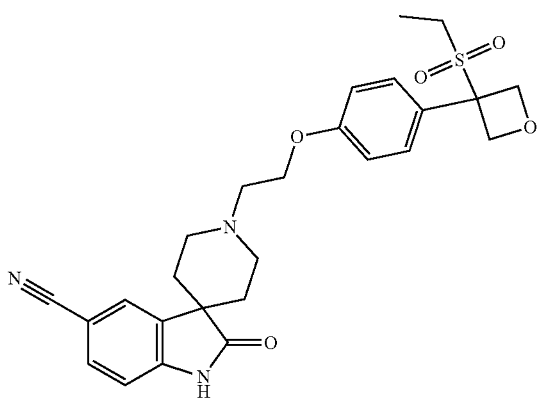 [SMILES: CCS(=O)(=O)C1(c2ccc(OCCN3CCC4(CC3)C(=O)Nc3ccc(C#N)cc34)cc2)COC1] | 1'-(2-{4-[3-(ethanesulfonyl)oxetan-3-yl]phenoxy}ethyl)-2-oxo-1,2-dihydrospiro[indole-3,4'-piperidine]-5-carbonitrile |
| 175 | 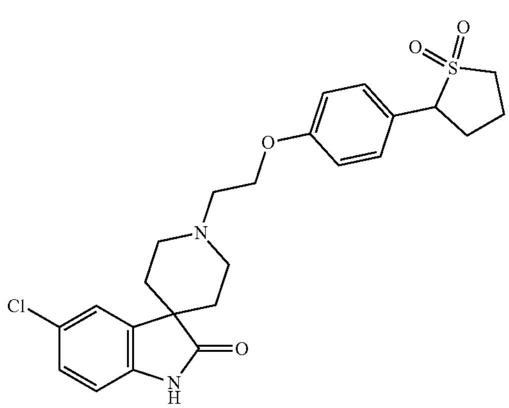 [SMILES: O=C1Nc2ccc(Cl)cc2C12CCN(CCOc1ccc(C3CCCS3(=O)=O)cc1)CC2] | 2-[4-(2-{5-chloro-2-oxo-1,2-dihydrospiro[indole-3,4'-piperidin]-1'-yl}ethoxy)phenyl]-1$\lambda^6$-thiolane-1,1-dione |

TABLE 1-continued

| Compound Number | Structure | Name |
|---|---|---|
| 176 | 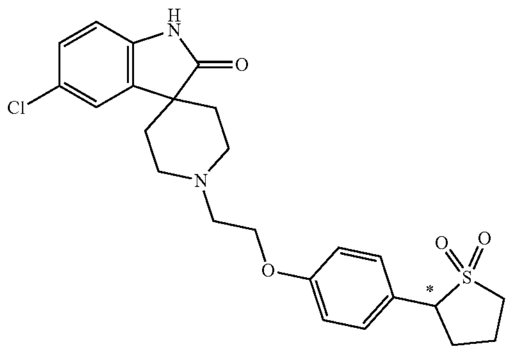 [SMILES: O=C1Nc2ccc(Cl)cc2C12CCN(CCOc1ccc(C3CCCS3(=O)=O)cc1)CC2] | (S) or (R)-2-[4-(2-{5-chloro-2-oxo-1,2-dihydrospiro[indole-3,4'-piperidin]-1'-yl}ethoxy)phenyl]-1$\lambda^6$-thiolane-1,1-dione |
| 177 | 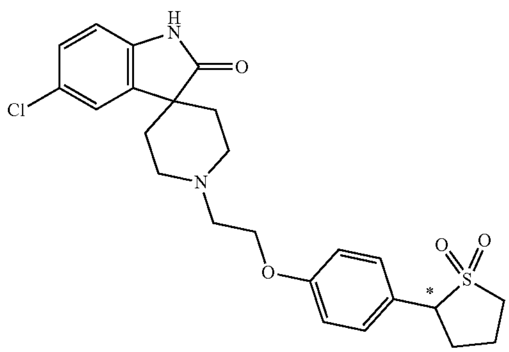 [SMILES: O=C1Nc2ccc(Cl)cc2C12CCN(CCOc1ccc(C3CCCS3(=O)=O)cc1)CC2] | (R) or (S)-2-[4-(2-{5-chloro-2-oxo-1,2-dihydrospiro[indole-3,4'-piperidin]-1'-yl}ethoxy)phenyl]-1$\lambda^6$-thiolane-1,1-dione |
| 178 | 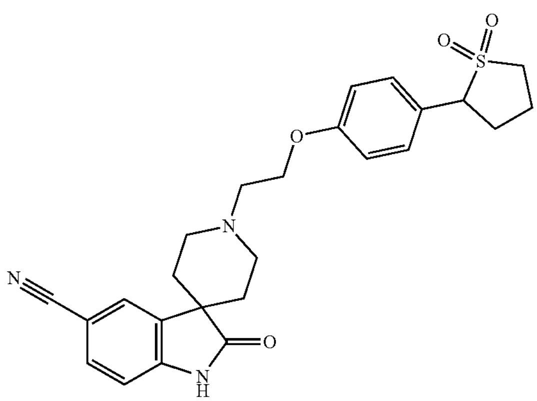 [SMILES: N#Cc1ccc2c(c1)C1(CCN(CCOc3ccc(C4CCCS4(=O)=O)cc3)CC1)C(=O)N2] | 1'-{2-[4-(1,1-dioxo-1$\lambda^6$-thiolan-2-yl)phenoxy]ethyl}-2-oxo-1,2-dihydrospiro[indole-3,4'-piperidine]-5-carbonitrile |
| 179 | 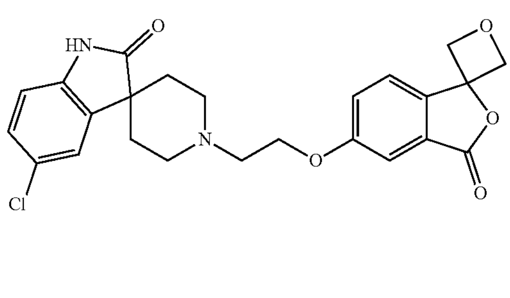 [SMILES: O=C1OC2(COC2)c2ccc(OCCN3CCC4(CC3)C(=O)Nc3ccc(Cl)cc34)cc21] | 5-chloro-1'-(2-{3-oxo-3H-spiro[2-benzofuran-1,3'-oxetan]-5-yloxy}ethyl)-1,2-dihydrospiro[indole-3,4'-piperidin]-2-one |

TABLE 1-continued

| Compound Number | Structure | Name |
|---|---|---|
| 180 | 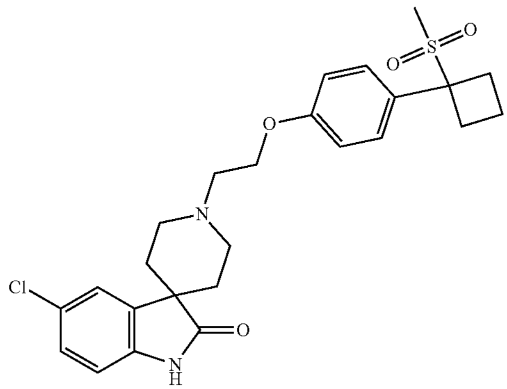 [SMILES: CS(=O)(=O)C1(c2ccc(OCCN3CCC4(CC3)C(=O)Nc3ccc(Cl)cc34)cc2)CCC1] | 5-chloro-1'-{2-[4-(1-methanesulfonylcyclobutyl)phenoxy]ethyl}-1,2-dihydrospiro[indole-3,4'-piperidin]-2-one |
| 181 | 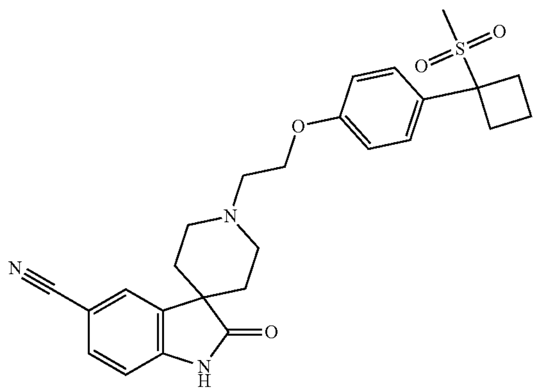 [SMILES: CS(=O)(=O)C1(c2ccc(OCCN3CCC4(CC3)C(=O)Nc3ccc(C#N)cc34)cc2)CCC1] | 1'-{2-[4-(1-methanesulfonylcyclobutyl)phenoxy]ethyl}-2-oxo-1,2-dihydrospiro[indole-3,4'-piperidine]-5-carbonitrile |
| 182 | 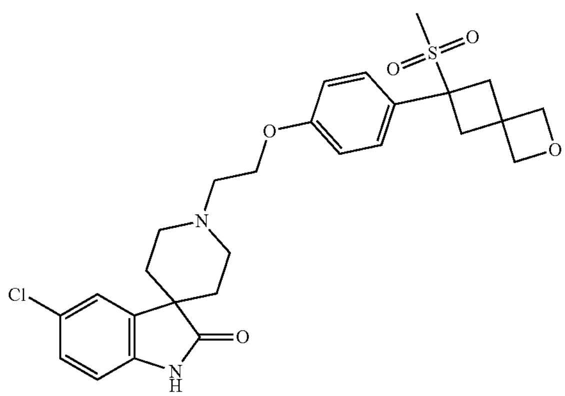 [SMILES: CS(=O)(=O)C1(c2ccc(OCCN3CCC4(CC3)C(=O)Nc3ccc(Cl)cc34)cc2)CC2(COC2)C1] | 5-chloro-1'-[2-(4-{6-methanesulfonyl-2-oxaspiro[3.3]heptan-6-yl}phenoxy)ethyl]-1,2-dihydrospiro[indole-3,4'-piperidin]-2-one |
| 183 | 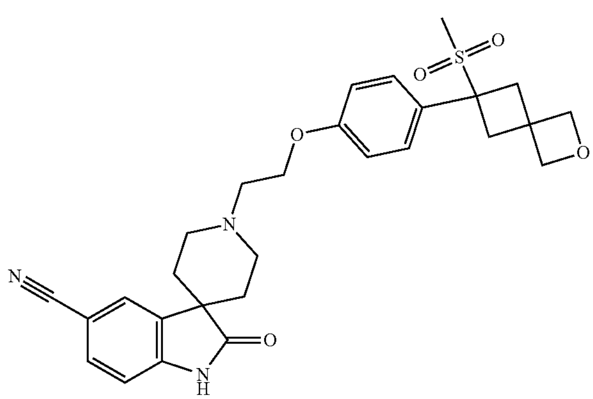 [SMILES: CS(=O)(=O)C1(c2ccc(OCCN3CCC4(CC3)C(=O)Nc3ccc(C#N)cc34)cc2)CC2(COC2)C1] | 1'-[2-(4-{6-methanesulfonyl-2-oxaspiro[3.3]heptan-6-yl}phenoxy)ethyl]-2-oxo-1,2-dihydrospiro[indole-3,4'-piperidine]-5-carbonitrile |

TABLE 1-continued

| Compound Number | Structure | Name |
|---|---|---|
| 184 | 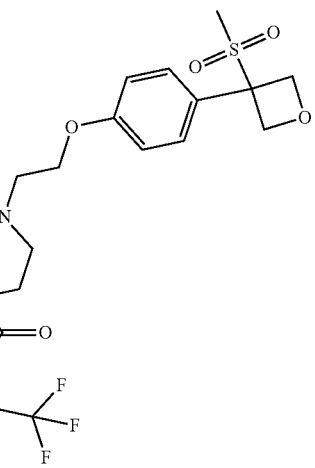 | 1'-{2-[4-(3-methanesulfonyloxetan-3-yl)phenoxy]ethyl}-2-oxo-1-(2,2,2-trifluoroethyl)-1,2-dihydrospiro[indole-3,4'-piperidine]-5-carbonitrile |
| 185 | 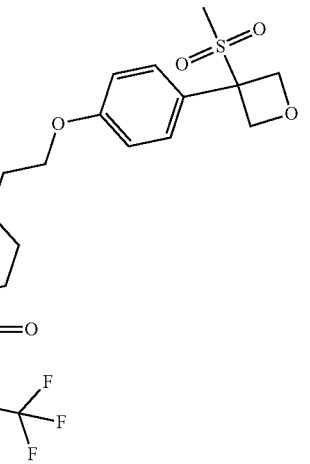 | 5-chloro-1'-{2-[4-(3-methanesulfonyloxetan-3-yl)phenoxy]ethyl}-1-(2,2,2-trifluoroethyl)-1,2-dihydrospiro[indole-3,4'-piperidin]-2-one |
| 186 | 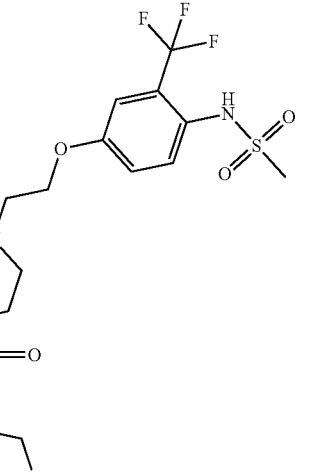 | N-(4-{2-[5-chloro-1-(2-hydroxyethyl)-2-oxo-1,2-dihydrospiro[indole-3,4'-piperidin]-1'-yl]ethoxy}-2-(trifluoromethyl)phenyl)methanesulfonamide |

TABLE 1-continued

| Compound Number | Structure | Name |
|---|---|---|
| 187 | 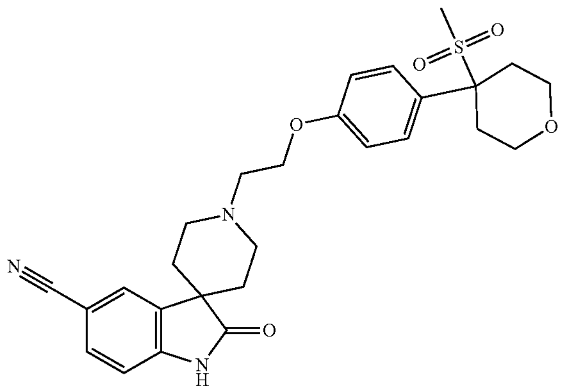 [SMILES: CS(=O)(=O)C1(c2ccc(OCCN3CCC4(CC3)C(=O)Nc3ccc(C#N)cc34)cc2)CCOCC1] | 1'-{2-[4-(4-methanesulfonyloxan-4-yl)phenoxy]ethyl}-2-oxo-1,2-dihydrospiro[indole-3,4'-piperidine]-5-carbonitrile |
| 188 | 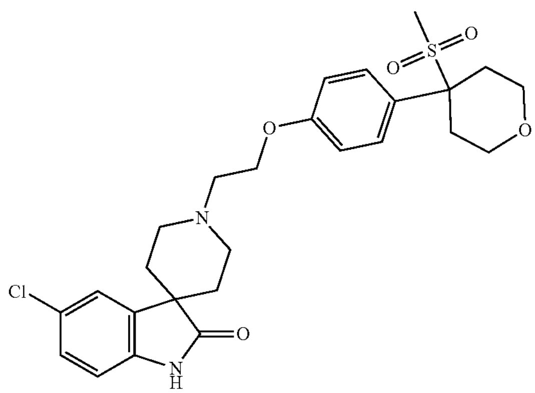 [SMILES: CS(=O)(=O)C1(c2ccc(OCCN3CCC4(CC3)C(=O)Nc3ccc(Cl)cc34)cc2)CCOCC1] | 5-chloro-1'-{2-[4-(4-methanesulfonyloxan-4-yl)phenoxy]ethyl}-1,2-dihydrospiro[indole-3,4'-piperidin]-2-one |
| 189 | 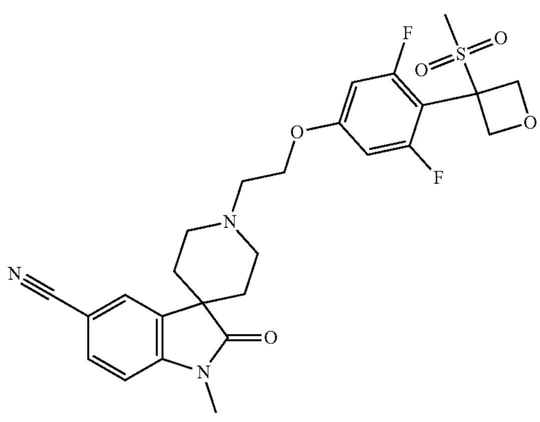 [SMILES: CN1C(=O)C2(CCN(CCOc3cc(F)c(C4(S(C)(=O)=O)COC4)c(F)c3)CC2)c2cc(C#N)ccc21] | 1'-{2-[3,5-difluoro-4-(3-methanesulfonyloxetan-3-yl)phenoxy]ethyl}-1-methyl-2-oxo-1,2-dihydrospiro[indole-3,4'-piperidine]-5-carbonitrile |
| 190 | 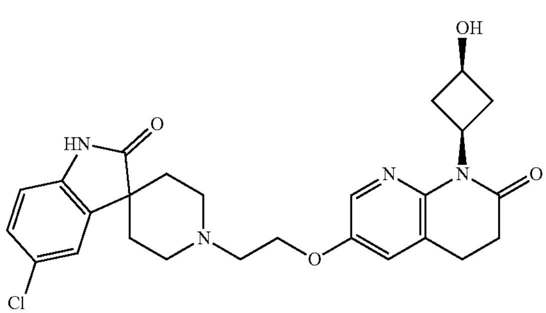 [SMILES: O=C1CCc2cc(OCCN3CCC4(CC3)C(=O)Nc3ccc(Cl)cc34)cnc2N1[C@H]1C[C@@H](O)C1] | 5-chloro-1'-[2-({7-oxo-8-[(cis)-3-hydroxycyclobutyl]-5,6,7,8-tetrahydro-1,8-naphthyridin-3-yl}oxy)ethyl]-1,2-dihydrospiro[indole-3,4'-piperidin]-2-one |

TABLE 1-continued

| Compound Number | Structure | Name |
|---|---|---|
| 191 | 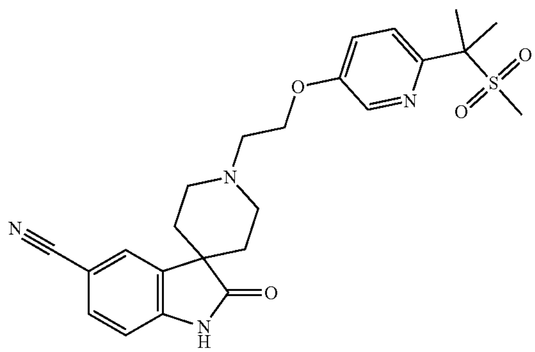 [SMILES: CC(C)(c1ccc(OCCN2CCC3(CC2)C(=O)Nc2ccc(C#N)cc23)cn1)S(C)(=O)=O] | 1'-(2-{[(6-(2-methanesulfonylpropan-2-yl)pyridin-3-yl]oxy}ethyl)-2-oxo-1,2-dihydrospiro[indole-3,4'-piperidine]-5-carbonitrile |
| 192 | 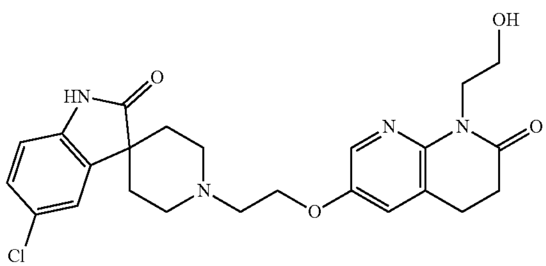 [SMILES: O=C1CCc2cc(OCCN3CCC4(CC3)C(=O)Nc3ccc(Cl)cc34)cnc2N1CCO] | 5-chloro-1'-(2-{[8-(2-hydroxyethyl)-7-oxo-5,6,7,8-tetrahydro-1,8-naphthyridin-3-yl]oxy}ethyl)-1,2-dihydrospiro[indole-3,4'-piperidin]-2-one |
| 193 | 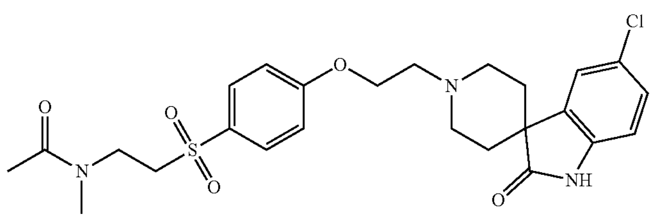 [SMILES: CC(=O)N(C)CCS(=O)(=O)c1ccc(OCCN2CCC3(CC2)C(=O)Nc2ccc(Cl)cc23)cc1] | N-{2-[4-(2-{5-chloro-2-oxo-1,2-dihydrospiro[indole-3,4'-piperidin]-1'-yl}ethoxy)benzenesulfonyl]ethyl}-N-methylacetamide |
| 194 | 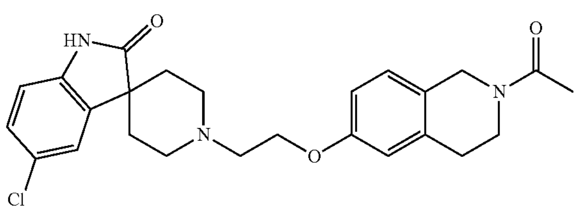 [SMILES: CC(=O)N1CCc2cc(OCCN3CCC4(CC3)C(=O)Nc3ccc(Cl)cc34)ccc2C1] | 1'-(2-[(2-acetyl-1,2,3,4-tetrahydroisoquinolin-6-yl)oxy]ethyl)-5-chloro-1,2-dihydrospiro[indole-3,4'-piperidin]-2-one |
| 195 | 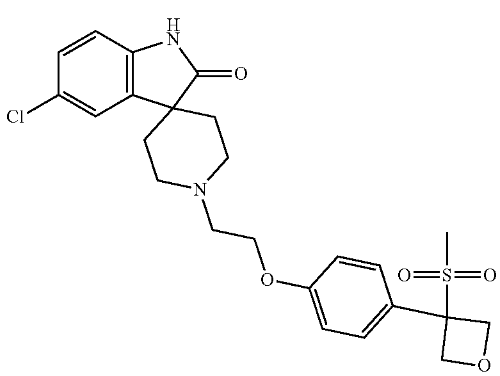 [SMILES: CS(=O)(=O)C1(c2ccc(OCCN3CCC4(CC3)C(=O)Nc3ccc(Cl)cc34)cc2)COC1] | 5-chloro-1'-{2-[4-(3-methanesulfonyloxetan-3-yl)phenoxy]ethyl}-1,2-dihydrospiro[indole-3,4'-piperidin]-2-one |

TABLE 1-continued

| Compound Number | Structure | Name |
| --- | --- | --- |
| 196 | 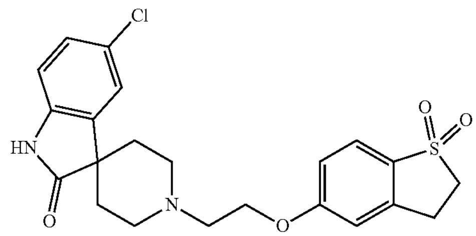 [SMILES: O=C1Nc2ccc(Cl)cc2C12CCN(CCOc1ccc3c(c1)CCS3(=O)=O)CC2] | 5-(2-{5-chloro-2-oxo-1,2-dihydrospiro[indole-3,4'-piperidin]-1'-yl}ethoxy)-2,3-dihydro-1$\lambda^6$-benzothiophene-1,1-dione |
| 197 | 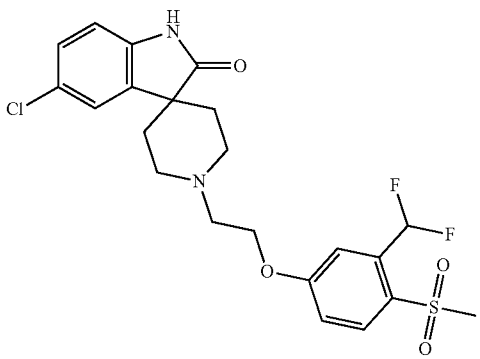 [SMILES: CS(=O)(=O)c1ccc(OCCN2CCC3(CC2)C(=O)Nc2ccc(Cl)cc23)cc1C(F)F] | 5-chloro-1'-{2-[3-(difluoromethyl)-4-methanesulfonylphenoxy]ethyl}-1,2-dihydrospiro[indole-3,4'-piperidin]-2-one |
| 198 | 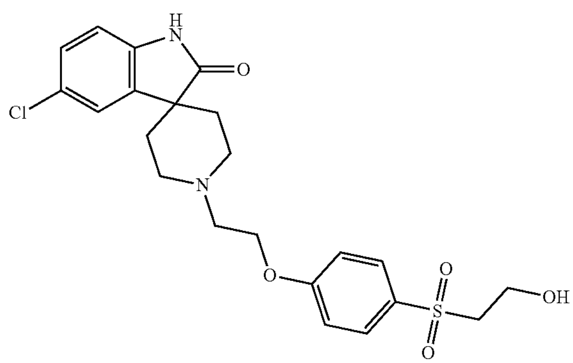 [SMILES: O=C1Nc2ccc(Cl)cc2C12CCN(CCOc1ccc(S(=O)(=O)CCO)cc1)CC2] | 5-chloro-1'-{2-[4-(2-hydroxyethanesulfonyl)phenoxy]ethyl}-1,2-dihydrospiro[indole-3,4'-piperidin]-2-one |
| 199 | 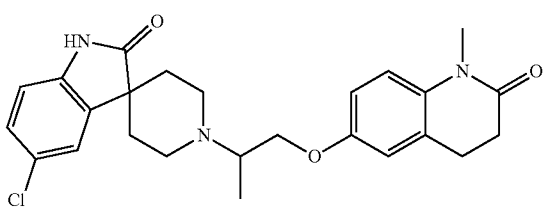 [SMILES: CC(COc1ccc2c(c1)CCC(=O)N2C)N1CCC2(CC1)C(=O)Nc1ccc(Cl)cc12] | 5-chloro-1'-{1-[(1-methyl-2-oxo-1,2,3,4-tetrahydroquinolin-6-yl)oxy]propan-2-yl}-1,2-dihydrospiro[indole-3,4'-piperidin]-2-one |
| 200 | 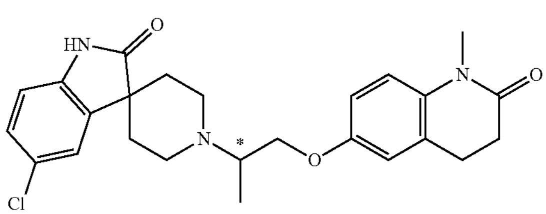 [SMILES: CC(COc1ccc2c(c1)CCC(=O)N2C)N1CCC2(CC1)C(=O)Nc1ccc(Cl)cc12] | chloro-1'-[(2S) or (2R)-1-[(1-methyl-2-oxo-1,2,3,4-tetrahydroquinolin-6-yl)oxy]propan-2-yl]-1,2-dihydrospiro[indole-3,4'-piperidin]-2-one |
| 201 | 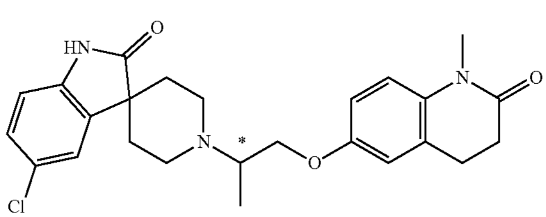 [SMILES: CC(COc1ccc2c(c1)CCC(=O)N2C)N1CCC2(CC1)C(=O)Nc1ccc(Cl)cc12] | chloro-1'-[(2R) or (2S)-1-[(1-methyl-2-oxo-1,2,3,4-tetrahydroquinolin-6-yl)oxy]propan-2-yl]-1,2-dihydrospiro[indole-3,4'-piperidin]-2-one |

TABLE 1-continued

| Compound Number | Structure | Name |
|---|---|---|
| 202 | 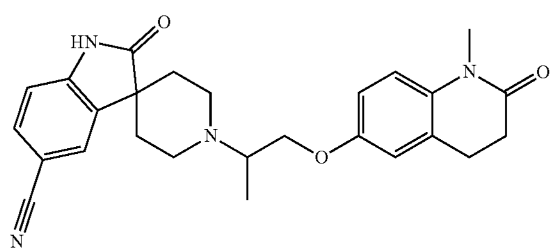 [SMILES: CC(COc1ccc2c(c1)CCC(=O)N2C)N1CCC2(CC1)C(=O)Nc1ccc(C#N)cc12] | 1'-{1-[(1-methyl-2-oxo-1,2,3,4-tetrahydroquinolin-6-yl)oxy]propan-2-yl}-2-oxo-1,2-dihydrospiro[indole-3,4'-piperidine]-5-carbonitrile |
| 203 | 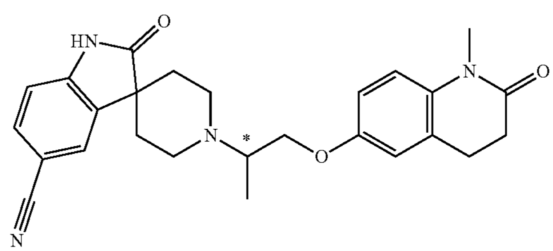 [SMILES: CC(COc1ccc2c(c1)CCC(=O)N2C)N1CCC2(CC1)C(=O)Nc1ccc(C#N)cc12] | (S) or (R)-1'-{1-[(1-methyl-2-oxo-1,2,3,4-tetrahydroquinolin-6-yl)oxy]propan-2-yl}-2-oxo-1,2-dihydrospiro[indole-3,4'-piperidine]-5-carbonitrile |
| 204 | 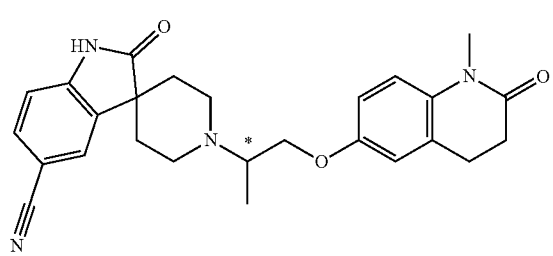 [SMILES: CC(COc1ccc2c(c1)CCC(=O)N2C)N1CCC2(CC1)C(=O)Nc1ccc(C#N)cc12] | (R) or (S)-1'-{1-[(1-methyl-2-oxo-1,2,3,4-tetrahydroquinolin-6-yl)oxy]propan-2-yl}-2-oxo-1,2-dihydrospiro[indole-3,4'-piperidine]-5-carbonitrile |
| 205 | 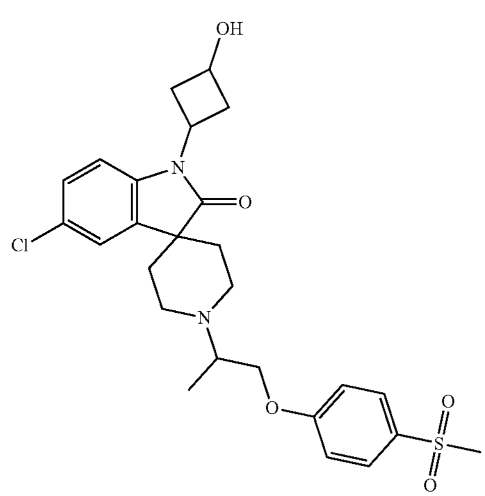 [SMILES: CC(COc1ccc(S(C)(=O)=O)cc1)N1CCC2(CC1)C(=O)N(C1CC(O)C1)c1ccc(Cl)cc12] | 5-chloro-1'-[1-(4-methanesulfonylphenoxy)propan-2-yl]-1-[3-hydroxycyclobutyl]-1,2-dihydrospiro[indole-3,4'-piperidin]-2-one |

TABLE 1-continued

| Compound Number | Structure | Name |
|---|---|---|
| 206 | 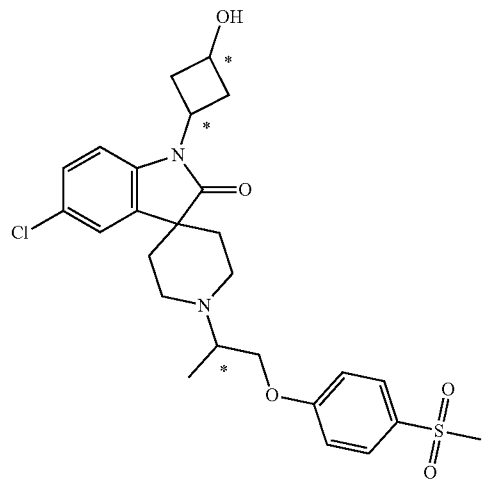 [SMILES: CC(COc1ccc(S(C)(=O)=O)cc1)N1CCC2(CC1)C(=O)N(C1CC(O)C1)c1ccc(Cl)cc12] | 5-chloro-1'-[(2S) or (2R)-1-(4-methanesulfonylphenoxy)propan-2-yl]-1-[(cis) or (trans)-3-hydroxycyclobutyl]-1,2-dihydrospiro[indole-3,4'-piperidin]-2-one |
| 207 | 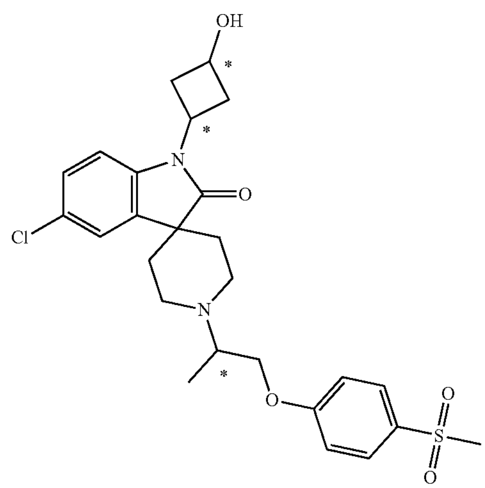 [SMILES: CC(COc1ccc(S(C)(=O)=O)cc1)N1CCC2(CC1)C(=O)N(C1CC(O)C1)c1ccc(Cl)cc12] | 5-chloro-1'-[(2S) or (2R)-1-(4-methanesulfonylphenoxy)propan-2-yl]-1-[(trans) or (cis)-3-hydroxycyclobutyl]-1,2-dihydrospiro[indole-3,4'-piperidin]-2-one |
| 208 | 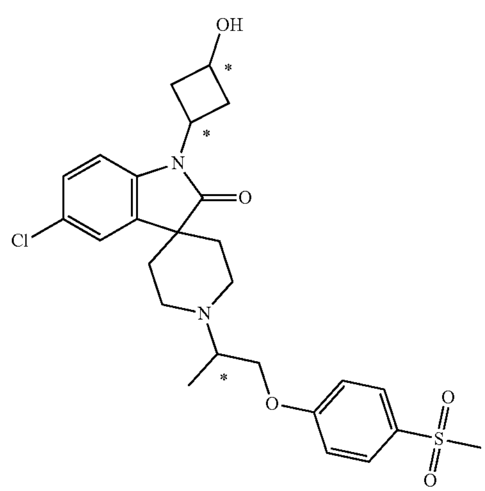 [SMILES: CC(COc1ccc(S(C)(=O)=O)cc1)N1CCC2(CC1)C(=O)N(C1CC(O)C1)c1ccc(Cl)cc12] | 5-chloro-1'-[(2R) or (2S)-1-(4-methanesulfonylphenoxy)propan-2-yl]-1-[(cis) or (trans)-3-hydroxycyclobutyl]-1,2-dihydrospiro[indole-3,4'-piperidin]-2-one |

TABLE 1-continued

| Compound Number | Structure | Name |
|---|---|---|
| 209 | 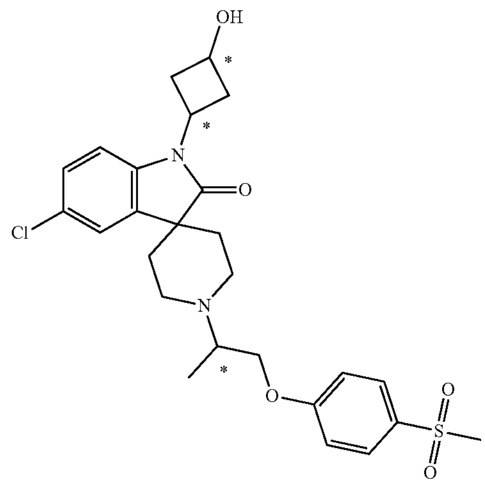 [SMILES: CC(COc1ccc(S(C)(=O)=O)cc1)N1CCC2(CC1)C(=O)N(C1CC(O)C1)c1ccc(Cl)cc12] | 5-chloro-1'-[(2R) or (2S)-1-(4-methanesulfonylphenoxy)propan-2-yl]-1-[(trans) or (cis)-3-hydroxycyclobutyl]-1,2-dihydrospiro[indole-3,4'-piperidin]-2-one |
| 210 | 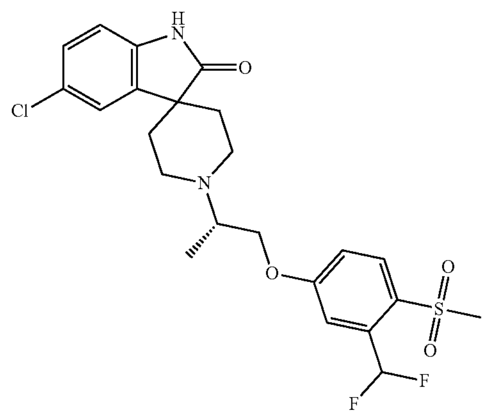 [SMILES: C[C@@H](COc1ccc(S(C)(=O)=O)c(C(F)F)c1)N1CCC2(CC1)C(=O)Nc1ccc(Cl)cc12] | 5-chloro-1'-[(2S)-1-[3-(difluoromethyl)-4-methanesulfonylphenoxy]propan-2-yl]-1,2-dihydrospiro[indole-3,4'-piperidin]-2-one |
| 211 | 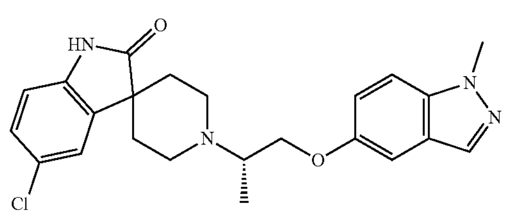 | 5-chloro-1'-[(2S)-1-[(1-methyl-1H-indazol-5-yl)oxy]propan-2-yl]-1,2-dihydrospiro[indole-3,4'-piperidin]-2-one |
| 212 | 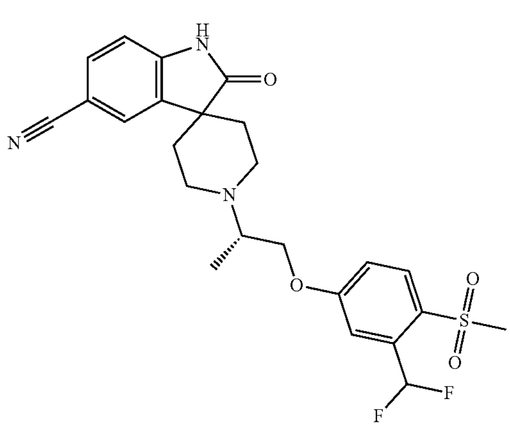 [SMILES: C[C@@H](COc1ccc(S(C)(=O)=O)c(C(F)F)c1)N1CCC2(CC1)C(=O)Nc1ccc(C#N)cc12] | 1'-[(2S)-1-[3-(difluoromethyl)-4-methanesulfonylphenoxy]propan-2-yl]-2-oxo-1,2-dihydrospiro[indole-3,4'-piperidine]-5-carbonitrile |

TABLE 1-continued

| Compound Number | Structure | Name |
|---|---|---|
| 213 | 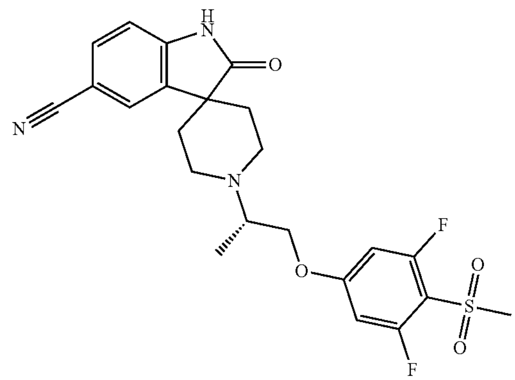 [SMILES: C[C@@H](COc1cc(F)c(S(C)(=O)=O)c(F)c1)N1CCC2(CC1)C(=O)Nc1ccc(C#N)cc12] | 1'-[(2S)-1-(3,5-difluoro-4-methanesulfonylphenoxy)propan-2-yl]-2-oxo-1,2-dihydrospiro[indole-3,4'-piperidine]-5-carbonitrile |
| 214 | 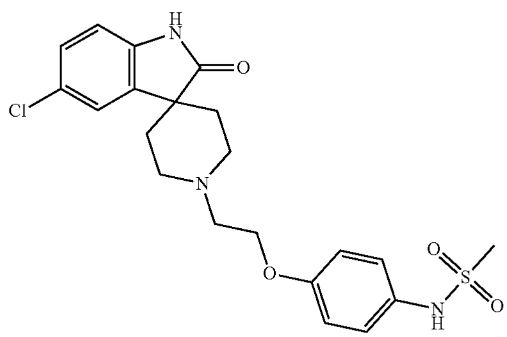 [SMILES: CS(=O)(=O)Nc1ccc(OCCN2CCC3(CC2)C(=O)Nc2ccc(Cl)cc23)cc1] | N-[4-(2-{5-chloro-2-oxo-1,2-dihydrospiro[indole-3,4'-piperidin]-1'-yl}ethoxy)phenyl]methanesulfonamide |
| 215 | 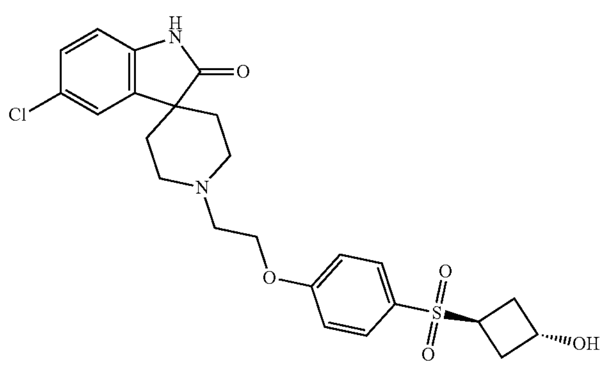 [SMILES: O=C1Nc2ccc(Cl)cc2C12CCN(CCOc1ccc(S(=O)(=O)[C@H]3C[C@H](O)C3)cc1)CC2] | 5-chloro-1'-[2-(4-{[(trans)-3-hydroxycyclobutyl]sulfonyl}phenoxy)ethyl]-1,2-dihydrospiro[indole-3,4'-piperidin]-2-one |
| 216 | 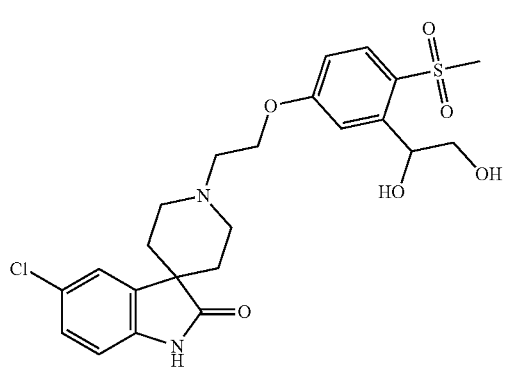 [SMILES: CS(=O)(=O)c1ccc(OCCN2CCC3(CC2)C(=O)Nc2ccc(Cl)cc23)cc1C(O)CO] | 5-chloro-1'-(2-[3-(1,2-dihydroxyethyl)-4-methanesulfonylphenoxy]ethyl}-1,2-dihydrospiro[indole-3,4'-piperidin]-2-one |

TABLE 1-continued

| Compound Number | Structure | Name |
|---|---|---|
| 217 | 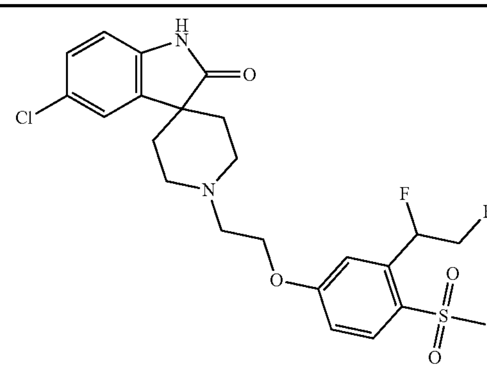 | 5-chloro-1'-{2-[3-(1,2-difluoroethyl)-4-methanesulfonylphenoxy]ethyl}-1,2-dihydrospiro[indole-3,4'-piperidin]-2-one |
| 218 | 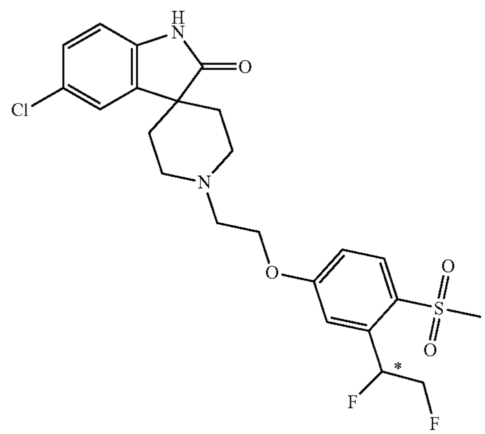 [SMILES: CS(=O)(=O)c1ccc(OCCN2CCC3(CC2)C(=O)Nc2ccc(Cl)cc23)cc1C(F)CF] | 5-chloro-1'-(2-{3-[(1S or 1R)-1,2-difluoroethyl]-4-methanesulfonylphenoxy}ethyl)-1,2-dihydrospiro[indole-3,4'-piperidin]-2-one |
| 219 | 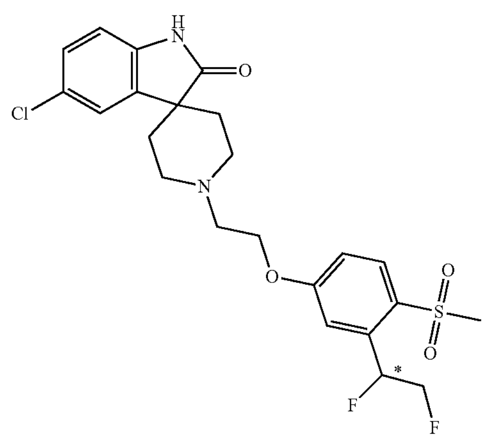 [SMILES: CS(=O)(=O)c1ccc(OCCN2CCC3(CC2)C(=O)Nc2ccc(Cl)cc23)cc1C(F)CF] | 5-chloro-1'-(2-{3-[(1R or 1S)-1,2-difluoroethyl]-4-methanesulfonylphenoxy}ethyl)-1,2-dihydrospiro[indole-3,4'-piperidin]-2-one |
| 220 | 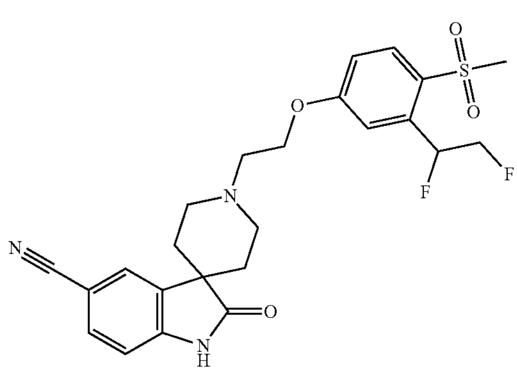 [SMILES: CS(=O)(=O)c1ccc(OCCN2CCC3(CC2)C(=O)Nc2ccc(C#N)cc23)cc1C(F)CF] | 1'-{2-[3-(1,2-difluoroethyl)-4-methanesulfonylphenoxy]ethyl}-2-oxo-1,2-dihydrospiro[indole-3,4'-piperidine]-5-carbonitrile |

TABLE 1-continued

| Compound Number | Structure | Name |
| --- | --- | --- |
| 221 | 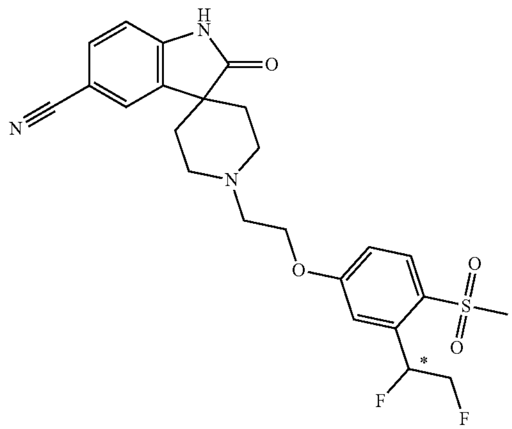 [SMILES: CS(=O)(=O)c1ccc(OCCN2CCC3(CC2)C(=O)Nc2ccc(C#N)cc23)cc1C(F)CF] | 1'-(2-(3-[(1S or 1R)-1,2-difluoroethyl]-4-methanesulfonylphenoxy}ethyl)-2-oxo-1,2-dihydrospiro[indole-3,4'-piperidine]-5-carbonitrile |
| 222 | 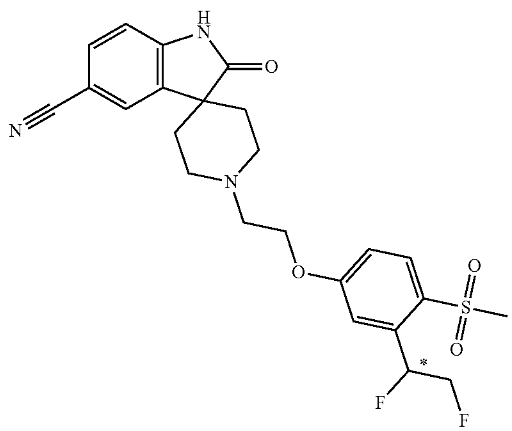 [SMILES: CS(=O)(=O)c1ccc(OCCN2CCC3(CC2)C(=O)Nc2ccc(C#N)cc23)cc1C(F)CF] | 1'-(2-(3-[(1R or 1S)-1,2-difluoroethyl]-4-methanesulfonylphenoxy}ethyl)-2-oxo-1,2-dihydrospiro[indole-3,4'-piperidine]-5-carbonitrile |
| 223 | 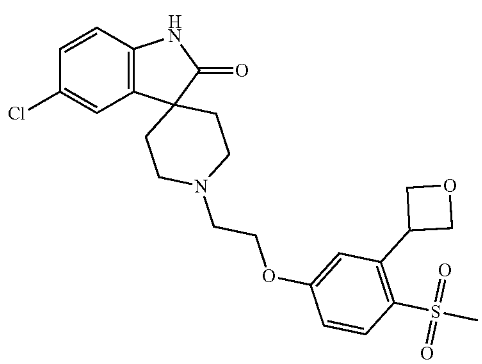 [SMILES: CS(=O)(=O)c1ccc(OCCN2CCC3(CC2)C(=O)Nc2ccc(Cl)cc23)cc1C1COC1] | 5-chloro-1'-{2-[4-methanesulfonyl-3-(oxetan-3-yl)phenoxy]ethyl}-1,2-dihydrospiro[indole-3,4'-piperidin]-2-one |
| 224 | 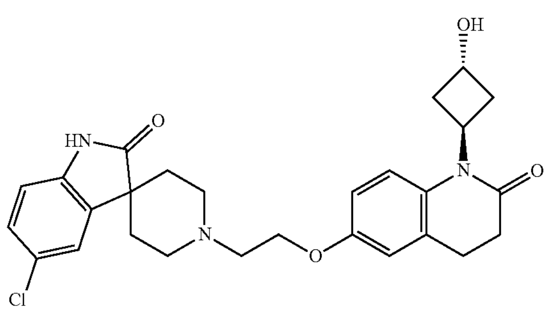 [SMILES: O=C1CCc2cc(OCCN3CCC4(CC3)C(=O)Nc3ccc(Cl)cc34)ccc2N1[C@H]1C[C@H](O)C1] | 5-chloro-1'-[2-({2-oxo-1-[(trans)-3-hydroxycyclobutyl]-1,2,3,4-tetrahydroquinolin-6-yl}oxy)ethyl]-1,2-dihydrospiro[indole-3,4'-piperidin]-2-one |

TABLE 1-continued

| Compound Number | Structure | Name |
|---|---|---|
| 225 | 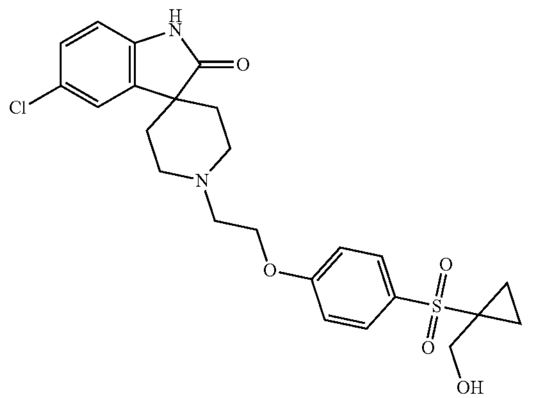 [SMILES: O=C1Nc2ccc(Cl)cc2C12CCN(CCOc1ccc(S(=O)(=O)C3(CO)CC3)cc1)CC2] | 5-chloro-1'-[2-(4-{[1-(hydroxymethyl)cyclopropyl]sulfonyl}phenoxy)ethyl]-1,2-dihydrospiro[indole-3,4'-piperidin]-2-one |
| 226 | 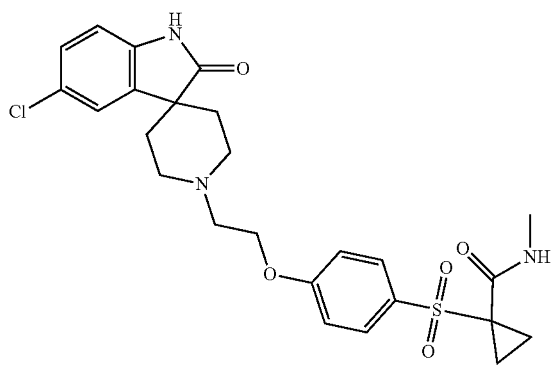 [SMILES: CNC(=O)C1(S(=O)(=O)c2ccc(OCCN3CCC4(CC3)C(=O)Nc3ccc(Cl)cc34)cc2)CC1] | 1-[4-(2-{5-chloro-2-oxo-1,2-dihydrospiro[indole-3,4'-piperidin]-1'-yl}ethoxy)benzenesulfonyl]-N-methylcyclopropane-1-carboxamide |
| 227 | 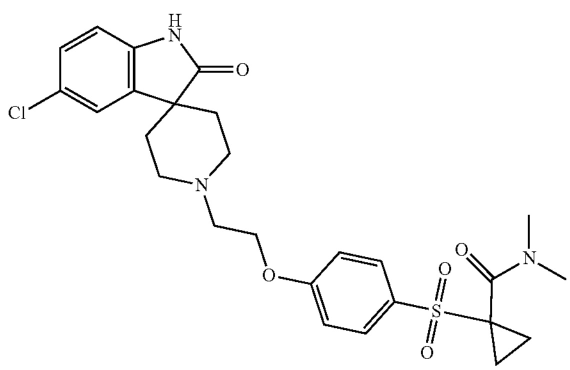 [SMILES: CN(C)C(=O)C1(S(=O)(=O)c2ccc(OCCN3CCC4(CC3)C(=O)Nc3ccc(Cl)cc34)cc2)CC1] | 1-[4-(2-{5-chloro-2-oxo-1,2-dihydrospiro[indole-3,4'-piperidin]-1'-yl}ethoxy)benzenesulfonyl]-N,N-dimethylcyclopropane-1-carboxamide |
| 228 | 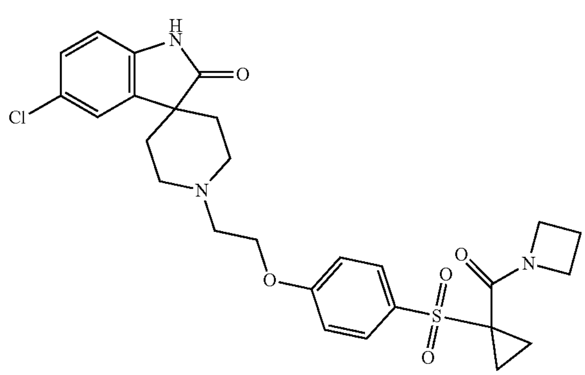 [SMILES: O=C1Nc2ccc(Cl)cc2C12CCN(CCOc1ccc(S(=O)(=O)C3(C(=O)N4CCC4)CC3)cc1)CC2] | 1'-[2-(4-{[1-(azetidine-1-carbonyl)cyclopropyl]sulfonyl}phenoxy)ethyl]-5-chloro-1,2-dihydrospiro[indole-3,4'-piperidin]-2-one |

TABLE 1-continued

| Compound Number | Structure | Name |
|---|---|---|
| 229 | 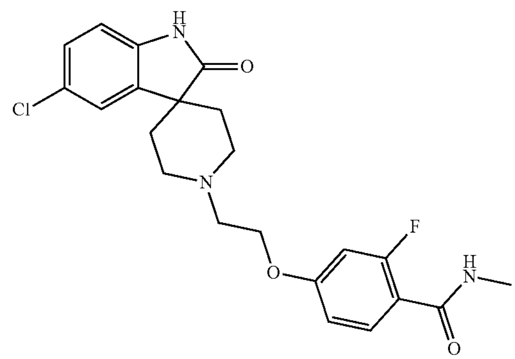 [SMILES: CNC(=O)c1ccc(OCCN2CCC3(CC2)C(=O)Nc2ccc(Cl)cc23)cc1F] | 4-(2-{5-chloro-2-oxo-1,2-dihydrospiro[indole-3,4'-piperidin]-1'-yl}ethoxy)-2-fluoro-N-methylbenzamide |
| 230 | 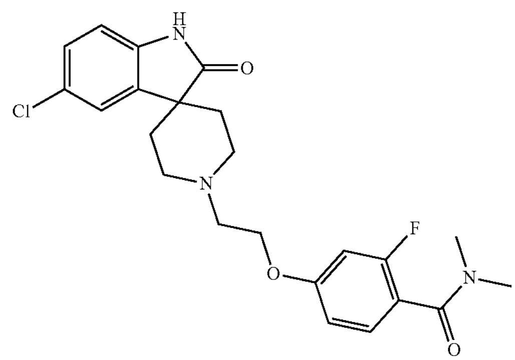 [SMILES: CN(C)C(=O)c1ccc(OCCN2CCC3(CC2)C(=O)Nc2ccc(Cl)cc23)cc1F] | 4-(2-{5-chloro-2-oxo-1,2-dihydrospiro[indole-3,4'-piperidin]-1'-yl}ethoxy)-2-fluoro-N,N-dimethylbenzamide |
| 231 | 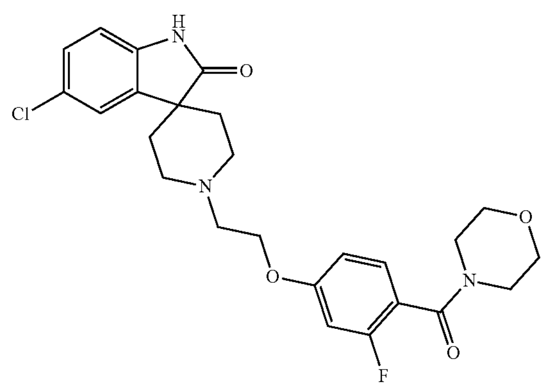 [SMILES: O=C(c1ccc(OCCN2CCC3(CC2)C(=O)Nc2ccc(Cl)cc23)cc1F)N1CCOCC1] | 5-chloro-1'-{2-[3-fluoro-4-(morpholine-4-carbonyl)phenoxy]ethyl}-1,2-dihydrospiro[indole-3,4'-piperidin]-2-one |
| 232 | 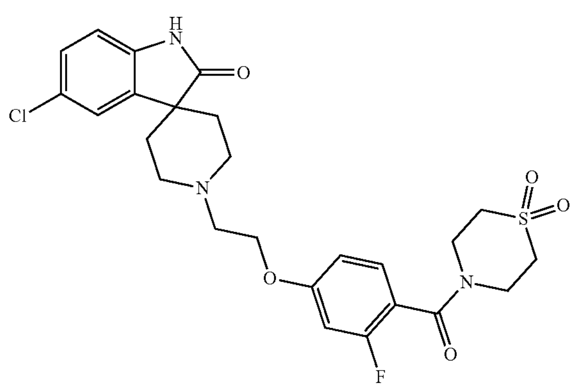 [SMILES: O=C(c1ccc(OCCN2CCC3(CC2)C(=O)Nc2ccc(Cl)cc23)cc1F)N1CCS(=O)(=O)CC1] | 4-[4-(2-{5-chloro-2-oxo-1,2-dihydrospiro[indole-3,4'-piperidin]-1'-yl}ethoxy)-2-fluorobenzoyl]-1$\lambda^6$-thiomorpholine-1,1-dione |

TABLE 1-continued

| Compound Number | Structure | Name |
|---|---|---|
| 233 | 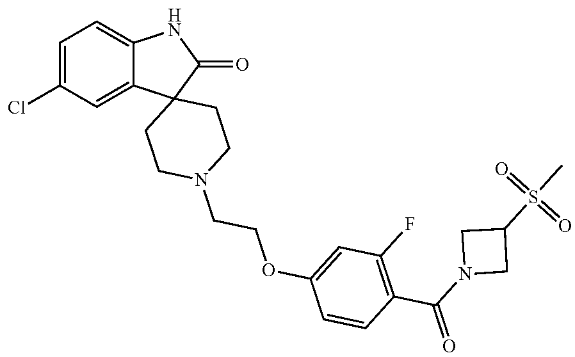 [SMILES: CS(=O)(=O)C1CN(C(=O)c2ccc(OCCN3CCC4(CC3)C(=O)Nc3ccc(Cl)cc34)cc2F)C1] | 5-chloro-1'-(2-[3-fluoro-4-(3-methanesulfonylazetidine-1-carbonyl)phenoxy]ethyl}-1,2-dihydrospiro[indole-3,4'-piperidin]-2-one |
| 234 | 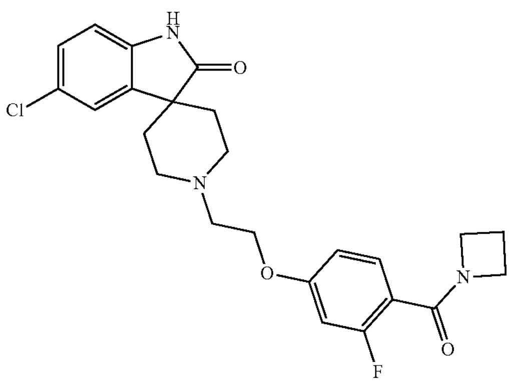 [SMILES: O=C(c1ccc(OCCN2CCC3(CC2)C(=O)Nc2ccc(Cl)cc23)cc1F)N1CCC1] | 1'-{2-[4-(azetidine-1-carbonyl)-3-fluorophenoxy]ethyl}-5-chloro-1,2-dihydrospiro[indole-3,4'-piperidin]-2-one |
| 235 | 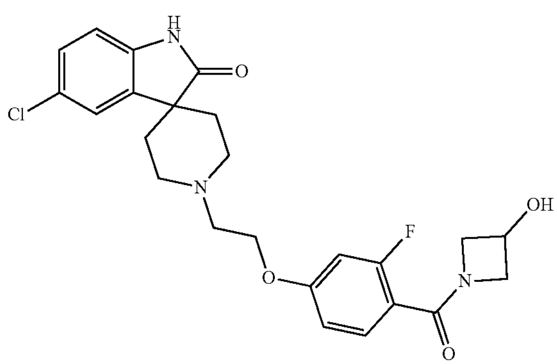 [SMILES: O=C(c1ccc(OCCN2CCC3(CC2)C(=O)Nc2ccc(Cl)cc23)cc1F)N1CC(O)C1] | 5-chloro-1'-{2-[3-fluoro-4-(3-hydroxyazetidine-1-carbonyl)phenoxy]ethyl}-1,2-dihydrospiro[indole-3,4'-piperidin]-2-one |
| 236 | 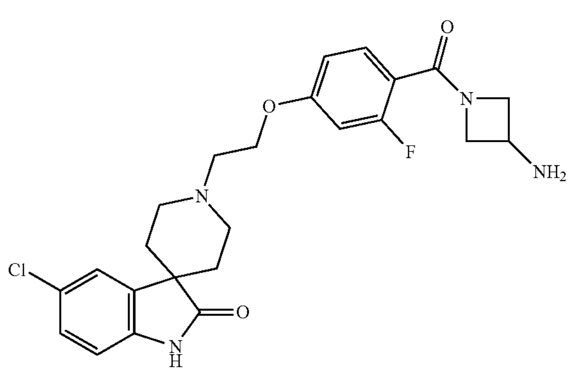 [SMILES: NC1CN(C(=O)c2ccc(OCCN3CCC4(CC3)C(=O)Nc3ccc(Cl)cc34)cc2F)C1] | 1'-{2-[4-(3-aminoazetidine-1-carbonyl)-3-fluorophenoxy]ethyl}-5-chloro-1,2-dihydrospiro[indole-3,4'-piperidin]-2-one |

TABLE 1-continued

| Compound Number | Structure | Name |
|---|---|---|
| 237 | 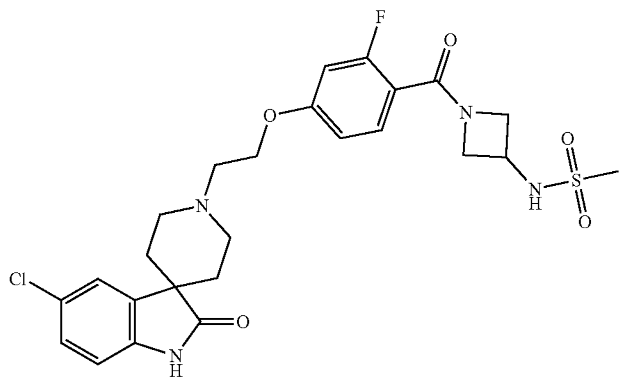 [SMILES: CS(=O)(=O)NC1CN(C(=O)c2ccc(OCCN3CCC4(CC3)C(=O)Nc3ccc(Cl)cc34)cc2F)C1] | N-{1-[4-(2-{5-chloro-2-oxo-1,2-dihydrospiro[indole-3,4'-piperidin]-1'-yl}ethoxy)-2-fluorobenzoyl]azetidin-3-yl}methanesulfonamide |
| 238 | 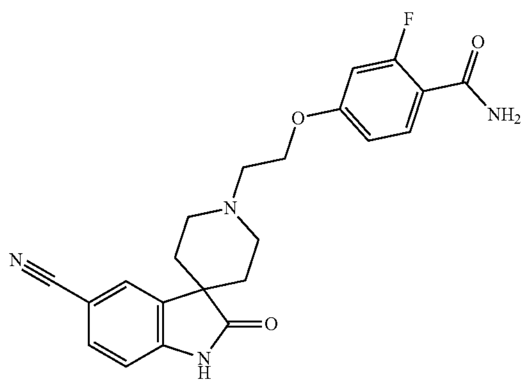 [SMILES: N#Cc1ccc2c(c1)C1(CCN(CCOc3ccc(C(N)=O)c(F)c3)CC1)C(=O)N2] | 4-(2-{5-cyano-2-oxo-1,2-dihydrospiro[indole-3,4'-piperidin]-1'-yl}ethoxy)-2-fluorobenzamide |
| 239 | 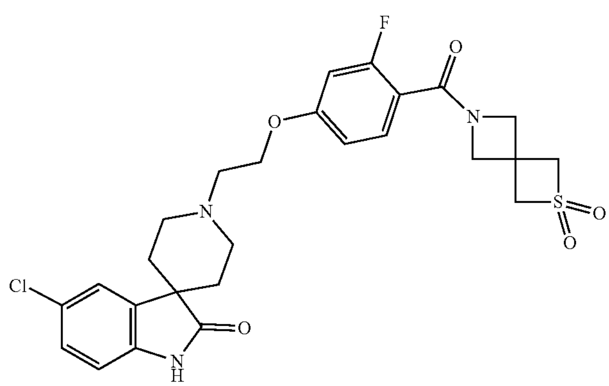 [SMILES: O=C(c1ccc(OCCN2CCC3(CC2)C(=O)Nc2ccc(Cl)cc23)cc1F)N1CC2(C1)CS(=O)(=O)C2] | 6-[4-(2-{5-chloro-2-oxo-1,2-dihydrospiro[indole-3,4'-piperidin]-1'-yl}ethoxy)-2-fluorobenzoyl]-2$\lambda^6$-thia-6-azaspiro[3.3]heptane-2,2-dione |
| 240 | 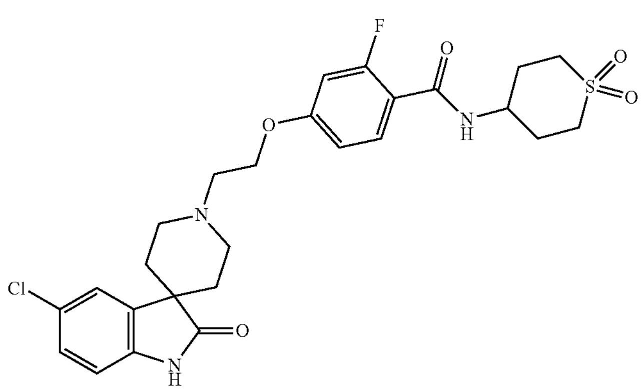 [SMILES: O=C(NC1CCS(=O)(=O)CC1)c1ccc(OCCN2CCC3(CC2)C(=O)Nc2ccc(Cl)cc23)cc1F] | 4-(2-{5-chloro-2-oxo-1,2-dihydrospiro[indole-3,4'-piperidin]-1'-yl}ethoxy)-N-(1,1-dioxo-1$\lambda^6$-thian-4-yl)-2-fluorobenzamide |

TABLE 1-continued

| Compound Number | Structure | Name |
|---|---|---|
| 241 | 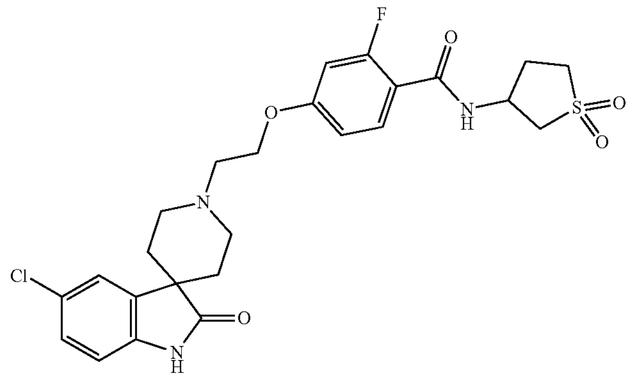 [SMILES: O=C(NC1CCS(=O)(=O)C1)c1ccc(OCCN2CCC3(CC2)C(=O)Nc2ccc(Cl)cc23)cc1F] | 4-(2-{5-chloro-2-oxo-1,2-dihydrospiro[indole-3,4'-piperidin]-1'-yl}ethoxy)-N-(,1-dioxo-1λ⁶-thiolan-3-yl)-2-fluorobenzamide |
| 242 | 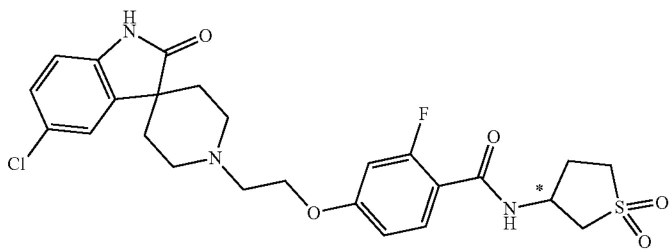 [SMILES: O=C(NC1CCS(=O)(=O)C1)c1ccc(OCCN2CCC3(CC2)C(=O)Nc2ccc(Cl)cc23)cc1F] | 4-(2-{5-chloro-2-oxo-1,2-dihydrospiro[indole-3,4'-piperidin]-1'-yl}ethoxy)-N-[(3S) or (3R)-1,1-dioxo-1λ⁶-thiolan-3-yl]-2-fluorobenzamide |
| 243 | 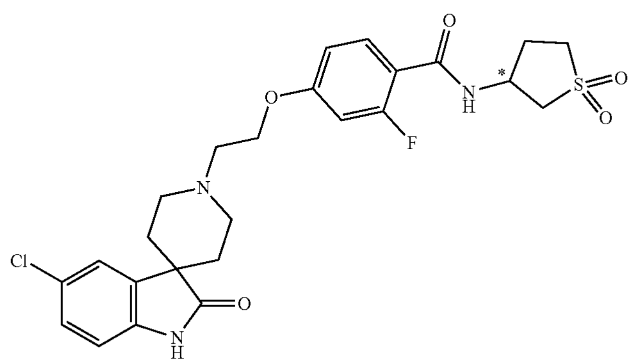 [SMILES: O=C(NC1CCS(=O)(=O)C1)c1ccc(OCCN2CCC3(CC2)C(=O)Nc2ccc(Cl)cc23)cc1F] | 4-(2-{5-chloro-2-oxo-1,2-dihydrospiro[indole-3,4'-piperidin]-1'-yl}ethoxy)-N-[(3R) or (3S)-1,1-dioxo-1λ⁶-thiolan-3-yl]-2-fluorobenzamide |
| 244 | 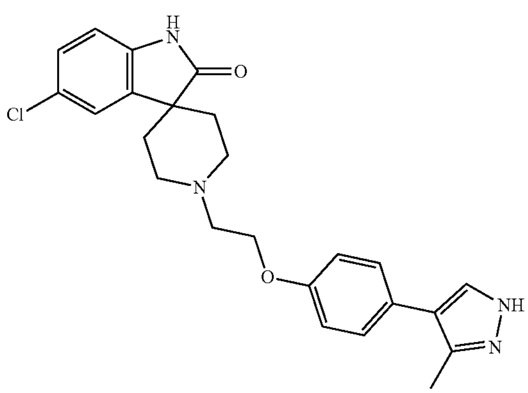 [SMILES: Cc1n[nH]cc1-c1ccc(OCCN2CCC3(CC2)C(=O)Nc2ccc(Cl)cc23)cc1] | 5-chloro-1'-{2-[4-(3-methyl-1H-pyrazol-4-yl)phenoxy]ethyl}-1,2-dihydrospiro[indole-3,4'-piperidin]-2-one |
| 245 | 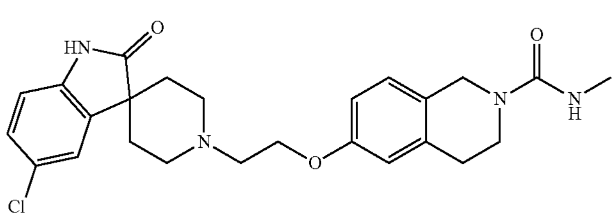 [SMILES: CNC(=O)N1CCc2cc(OCCN3CCC4(CC3)C(=O)Nc3ccc(Cl)cc34)ccc2C1] | 6-(2-{5-chloro-2-oxo-1,2-dihydrospiro[indole-3,4'-piperidin]-1'-yl}ethoxy)-N-methyl-1,2,3,4-tetrahydroisoquinoline-2-carboxamide |

TABLE 1-continued

| Compound Number | Structure | Name |
|---|---|---|
| 246 | 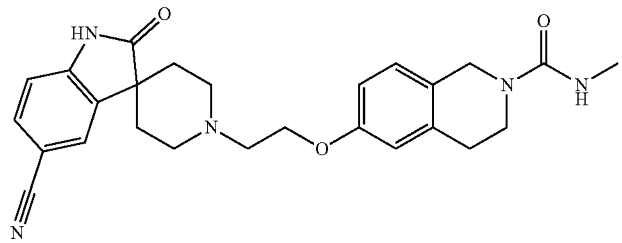 [SMILES: CNC(=O)N1CCc2cc(OCCN3CCC4(CC3)C(=O)Nc3ccc(C#N)cc34)ccc2C1] | 6-(2-{5-cyano-2-oxo-1,2-dihydrospiro[indole-3,4'-piperidin]-1'-yl}ethoxy)-N-methyl-1,2,3,4-tetrahydroisoquinoline-2-carboxamide |
| 247 | 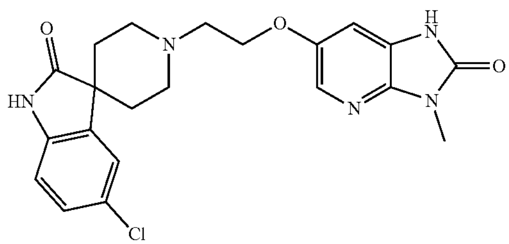 [SMILES: Cn1c(=O)[nH]c2cc(OCCN3CCC4(CC3)C(=O)Nc3ccc(Cl)cc34)cnc21] | 5-chloro-1'-[2-({3-methyl-2-oxo-1H,2H,3H-imidazo[4,5-b]pyridin-6-yl}oxy)ethyl]-1,2-dihydrospiro[indole-3,4'-piperidin]-2-one |
| 248 | 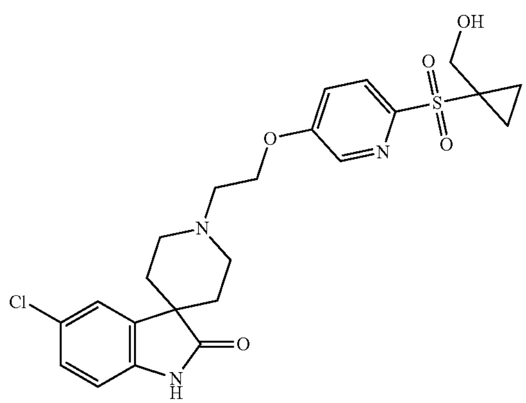 [SMILES: O=C1Nc2ccc(Cl)cc2C12CCN(CCOc1ccc(S(=O)(=O)C3(CO)CC3)nc1)CC2] | 5-chloro-1'-(2-[(6-{[1-(hydroxymethyl)cyclopropyl]sulfonyl}pyridin-3-yl)oxy]ethyl}-1,2-dihydrospiro[indole-3,4'-piperidin]-2-one |
| 249 | 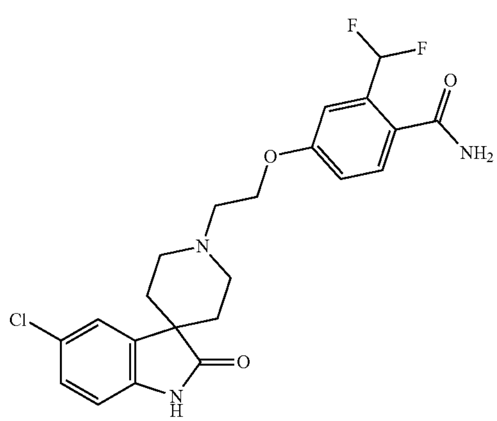 [SMILES: NC(=O)c1ccc(OCCN2CCC3(CC2)C(=O)Nc2ccc(Cl)cc23)cc1C(F)F] | 4-(2-{5-chloro-2-oxo-1,2-dihydrospiro[indole-3,4'-piperidin]-1'-yl}ethoxy)-2-(difluoromethyl)benzamide |

TABLE 1-continued

| Compound Number | Structure | Name |
|---|---|---|
| 250 | 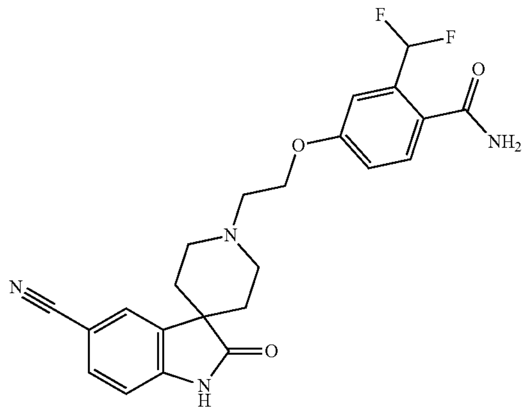 [SMILES: N#Cc1ccc2c(c1)C1(CCN(CCOc3ccc(C(N)=O)c(C(F)F)c3)CC1)C(=O)N2] | 4-(2-{5-cyano-2-oxo-1,2-dihydrospiro[indole-3,4'-piperidin]-1'-yl}ethoxy)-2-(difluoromethyl)benzamide |
| 251 | 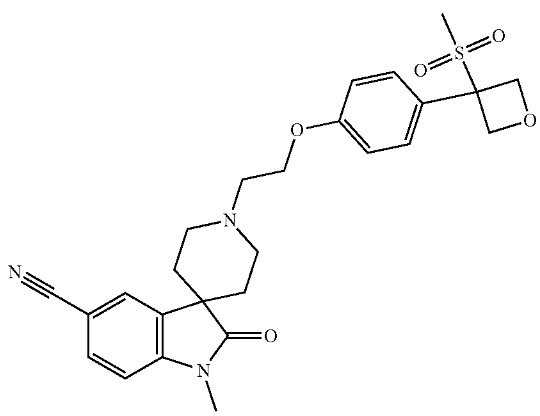 [SMILES: CN1C(=O)C2(CCN(CCOc3ccc(C4(S(C)(=O)=O)COC4)cc3)CC2)c2cc(C#N)ccc21] | 1'-{2-[4-(3-methanesulfonyloxetan-3-yl)phenoxy]ethyl}-1-methyl-2-oxo-1,2-dihydrospiro[indole-3,4'-piperidine]-5-carbonitrile |
| 252 | 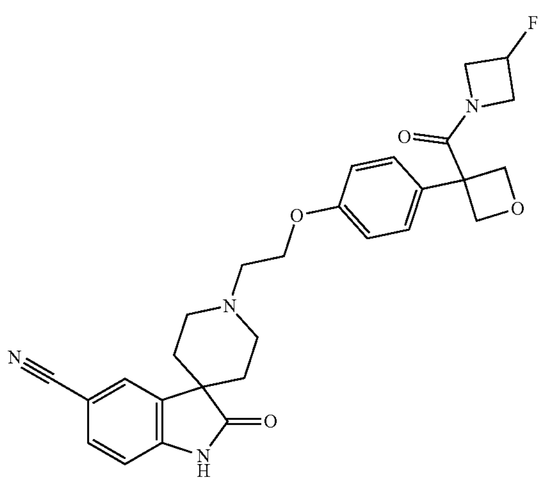 [SMILES: N#Cc1ccc2c(c1)C1(CCN(CCOc3ccc(C4(C(=O)N5CC(F)C5)COC4)cc3)CC1)C(=O)N2] | 1'-(2-{4-[3-(3-fluoroazetidine-1-carbonyl)oxetan-3-yl]phenoxy}ethyl)-2-oxo-1,2-dihydrospiro[indole-3,4'-piperidine]-5-carbonitrile |

TABLE 1-continued

| Compound Number | Structure | Name |
|---|---|---|
| 253 | 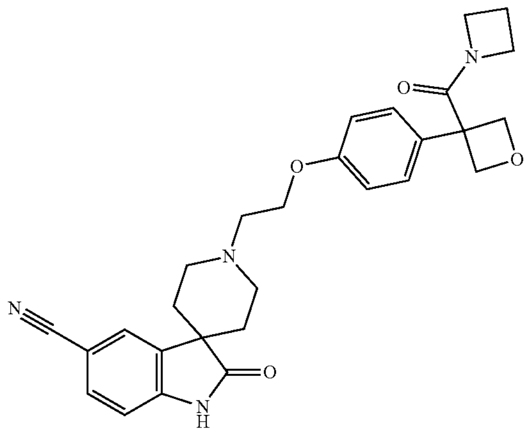 [SMILES: N#Cc1ccc2c(c1)C1(CCN(CCOc3ccc(C4(C(=O)N5CCC5)COC4)cc3)CC1)C(=O)N2] | 1'-(2-{4-[3-(azetidine-1-carbonyl)oxetan-3-yl]phenoxy}ethyl)-2-oxo-1,2-dihydrospiro[indole-3,4'-piperidine]-5-carbonitrile |
| 254 | 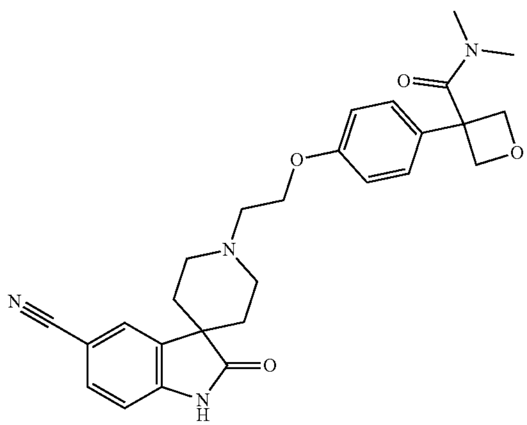 [SMILES: CN(C)C(=O)C1(c2ccc(OCCN3CCC4(CC3)C(=O)Nc3ccc(C#N)cc34)cc2)COC1] | 3-[4-(2-{5-cyano-2-oxo-1,2-dihydrospiro[indole-3,4'-piperidin]-1'-yl}ethoxy)phenyl]-N,N-dimethyloxetane-3-carboxamide |
| 255 | 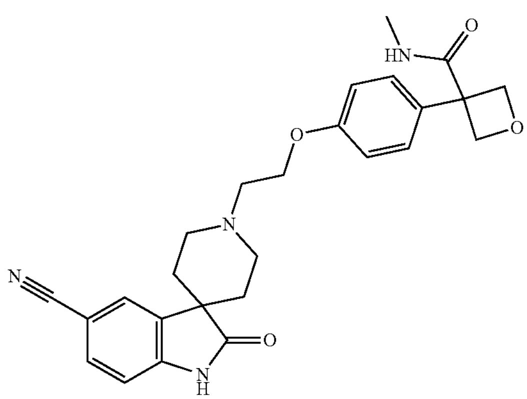 [SMILES: CNC(=O)C1(c2ccc(OCCN3CCC4(CC3)C(=O)Nc3ccc(C#N)cc34)cc2)COC1] | 3-[4-(2-{5-cyano-2-oxo-1,2-dihydrospiro[indole-3,4'-piperidin]-1'-yl}ethoxy)phenyl]-N-methyloxetane-3-carboxamide |

TABLE 1-continued

| Compound Number | Structure | Name |
| --- | --- | --- |
| 256 | 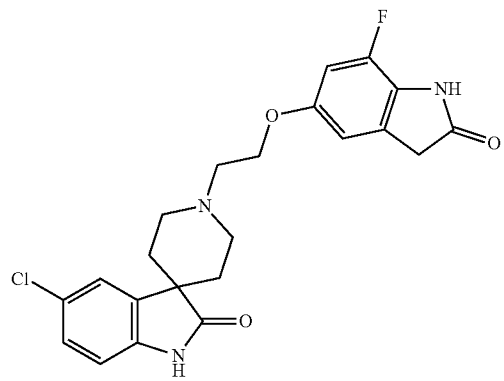 [SMILES: O=C1Cc2cc(OCCN3CCC4(CC3)C(=O)Nc3ccc(Cl)cc34)cc(F)c2N1] | 5-chloro-1'-{2-[(7-fluoro-2-oxo-2,3-dihydro-1H-indol-5-yl)oxy]ethyl}-1,2-dihydrospiro[indole-3,4'-piperidin]-2-one |
| 257 | 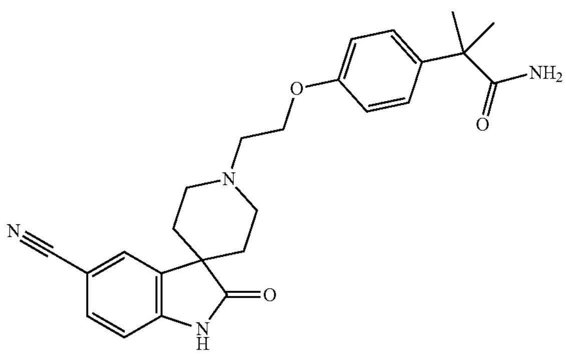 [SMILES: CC(C)(C(N)=O)c1ccc(OCCN2CCC3(CC2)C(=O)Nc2ccc(C#N)cc23)cc1] | 2-[4-(2-{5-cyano-2-oxo-1,2-dihydrospiro[indole-3,4'-piperidin]-1'-yl}ethoxy)phenyl]-2-methylpropanamide |
| 258 | 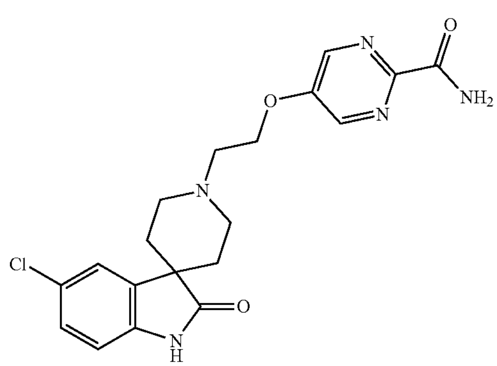 [SMILES: NC(=O)c1ncc(OCCN2CCC3(CC2)C(=O)Nc2ccc(Cl)cc23)cn1] | 5-(2-{5-chloro-2-oxo-1,2-dihydrospiro[indole-3,4'-piperidin]-1'-yl}ethoxy)pyrimidine-2-carboxamide |
| 259 | 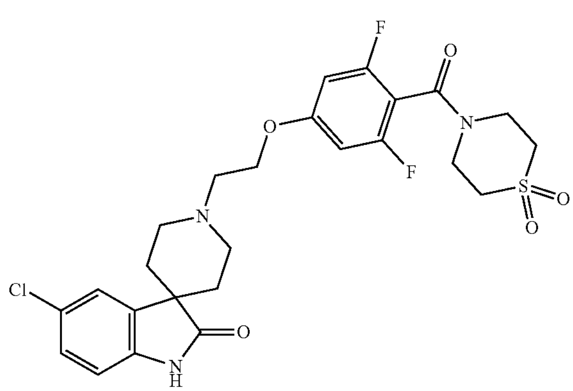 [SMILES: O=C(c1c(F)cc(OCCN2CCC3(CC2)C(=O)Nc2ccc(Cl)cc23)cc1F)N1CCS(=O)(=O)CC1] | 4-[4-(2-{5-chloro-2-oxo-1,2-dihydrospiro[indole-3,4'-piperidin]-1'-yl}ethoxy)-2,6-difluorobenzoyl]-1$\lambda^6$-thiomorpholine-1,1-dione |

TABLE 1-continued

| Compound Number | Structure | Name |
|---|---|---|
| 260 | 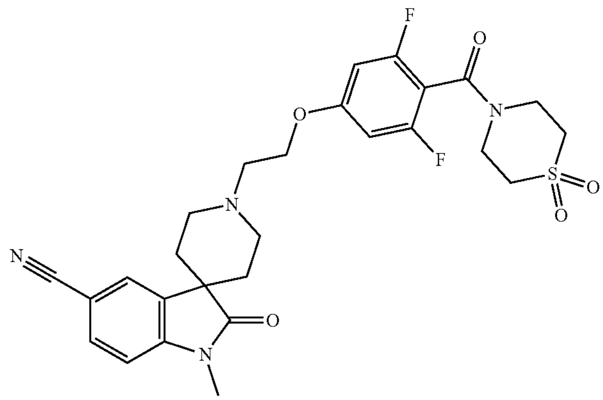 [SMILES: CN1C(=O)C2(CCN(CCOc3cc(F)c(C(=O)N4CCS(=O)(=O)CC4)c(F)c3)CC2)c2cc(C#N)ccc21] | 1'-{2-[4-(1,1-dioxo-1λ⁶-thiomorpholine-4-carbonyl)-3,5-difluorophenoxy]ethyl}-1-methyl-2-oxo-1,2-dihydrospiro[indole-3,4'-piperidine]-5-carbonitrile |
| 261 | 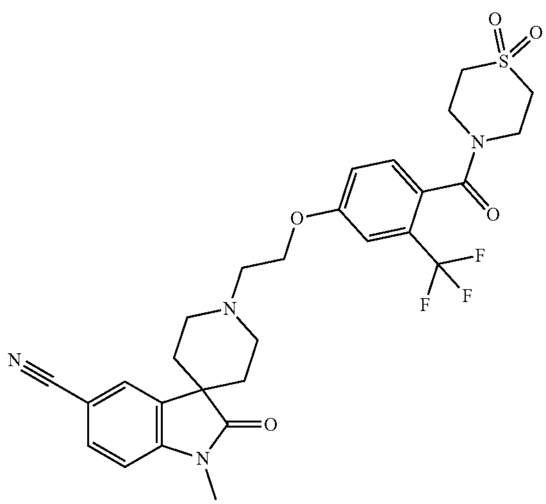 [SMILES: CN1C(=O)C2(CCN(CCOc3ccc(C(=O)N4CCS(=O)(=O)CC4)c(C(F)(F)F)c3)CC2)c2cc(C#N)ccc21] | 1'-{2-[4-(1,1-dioxo-1λ⁶-thiomorpholine-4-carbonyl)-3-(trifluoromethyl)phenoxy]ethyl}-1-methyl-2-oxo-1,2-dihydrospiro[indole-3,4'-piperidine]-5-carbonitrile |
| 262 | 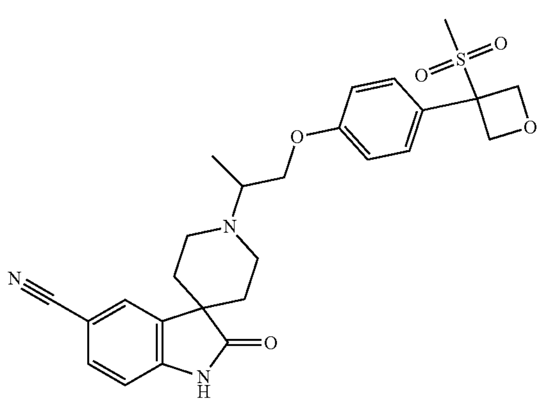 [SMILES: CC(COc1ccc(C2(S(C)(=O)=O)COC2)cc1)N1CCC2(CC1)C(=O)Nc1ccc(C#N)cc12] | 1'-{1-[4-(3-methanesulfonyloxetan-3-yl)phenoxy]propan-2-yl}-2-oxo-1,2-dihydrospiro[indole-3,4'-piperidine]-5-carbonitrile |

TABLE 1-continued

| Compound Number | Structure | Name |
|---|---|---|
| 263 | 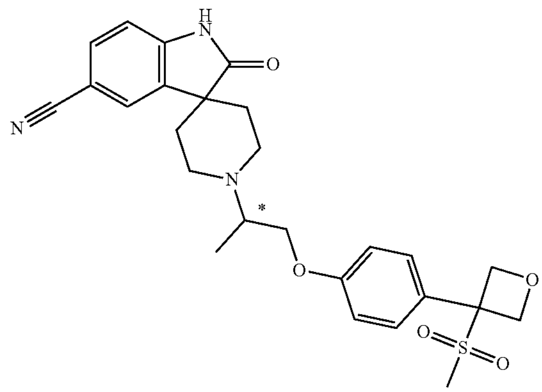 [SMILES: CC(COc1ccc(C2(S(C)(=O)=O)COC2)cc1)N1CCC2(CC1)C(=O)Nc1ccc(C#N)cc12] | (S) or (R)-1'-{1-[4-(3-methanesulfonyloxetan-3-yl)phenoxy]propan-2-yl}-2-oxo-1,2-dihydrospiro[indole-3,4'-piperidine]-5-carbonitrile |
| 264 | 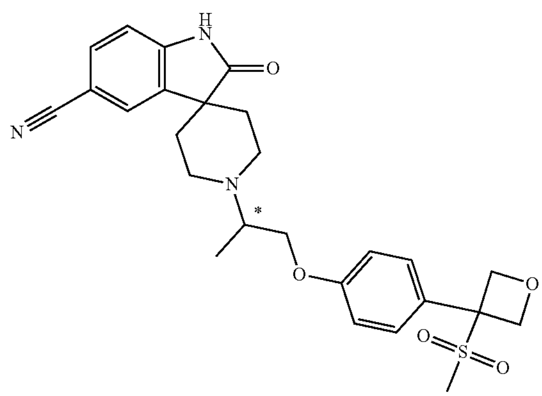 [SMILES: CC(COc1ccc(C2(S(C)(=O)=O)COC2)cc1)N1CCC2(CC1)C(=O)Nc1ccc(C#N)cc12] | (R) or (S)-1'-(1-[4-(3-methanesulfonyloxetan-3-yl)phenoxy]propan-2-yl}-2-oxo-1,2-dihydrospiro[indole-3,4'-piperidine]-5-carbonitrile |
| 265 | 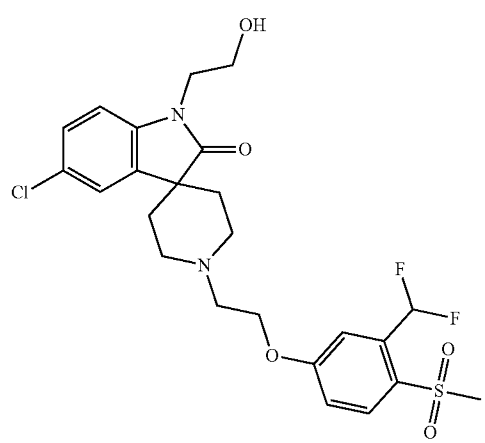 [SMILES: CS(=O)(=O)c1ccc(OCCN2CCC3(CC2)C(=O)N(CCO)c2ccc(Cl)cc23)cc1C(F)F] | 5-chloro-1'-(2-[3-(difluoromethyl)-4-methanesulfonylphenoxy]ethyl}-1-(2-hydroxyethyl)-1,2-dihydrospiro[indole-3,4'-piperidin]-2-one |

TABLE 1-continued

| Compound Number | Structure | Name |
|---|---|---|
| 266 | 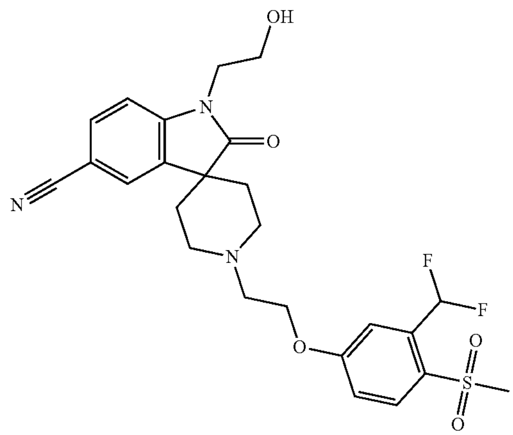 [SMILES: CS(=O)(=O)c1ccc(OCCN2CCC3(CC2)C(=O)N(CCO)c2ccc(C#N)cc23)cc1C(F)F] | 1'-{2-[3-(difluoromethyl)-4-methanesulfonylphenoxy]ethyl}-1-(2-hydroxyethyl)-2-oxo-1,2-dihydrospiro[indole-3,4'-piperidine]-5-carbonitrile |
| 267 | 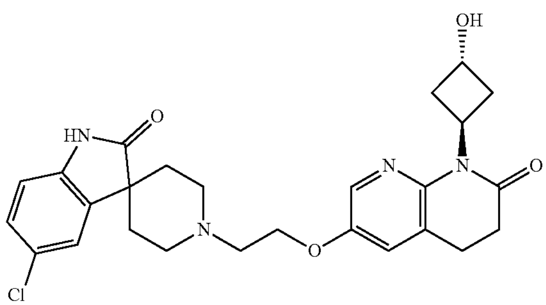 | 5-chloro-1'-[2-({7-oxo-8-[(trans)-3-hydroxycyclobutyl]-5,6,7,8-tetrahydro-1,8-naphthyridin-3-yl}oxy)ethyl]-1,2-dihydrospiro[indole-3,4'-piperidin]-2-one |
| 268 | 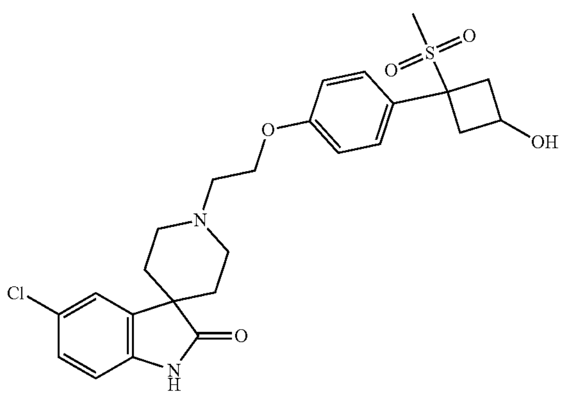 [SMILES: CS(=O)(=O)C1(c2ccc(OCCN3CCC4(CC3)C(=O)Nc3ccc(Cl)cc34)cc2)CC(O)C1] | 5-chloro-1'-{2-[4-(3-hydroxy-1-methanesulfonylcyclobutyl)phenoxy]ethyl}-1,2-dihydrospiro[indole-3,4'-piperidin]-2-one |
| 269 | 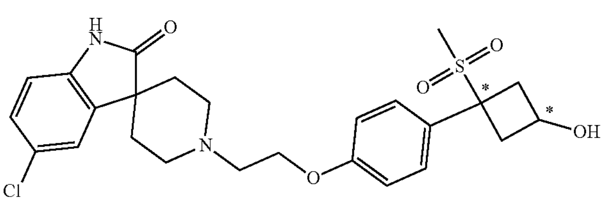 [SMILES: CS(=O)(=O)C1(c2ccc(OCCN3CCC4(CC3)C(=O)Nc3ccc(Cl)cc34)cc2)CC(O)C1] | 5-chloro-1'-(2-{4-[(cis) or (trans)-3-hydroxy-1-methanesulfonylcyclobutyl]phenoxy}ethyl)-1,2-dihydrospiro[indole-3,4'-piperidin]-2-one |
| 270 | 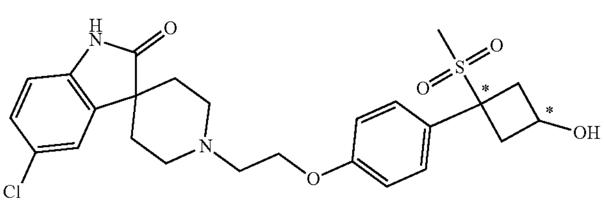 [SMILES: CS(=O)(=O)C1(c2ccc(OCCN3CCC4(CC3)C(=O)Nc3ccc(Cl)cc34)cc2)CC(O)C1] | 5-chloro-1'-(2-{4-[(trans) or (cis)-3-hydroxy-1-methanesulfonylcyclobutyl]phenoxy}ethyl)-1,2-dihydrospiro[indole-3,4'-piperidin]-2-one |

TABLE 1-continued

| Compound Number | Structure | Name |
|---|---|---|
| 271 | 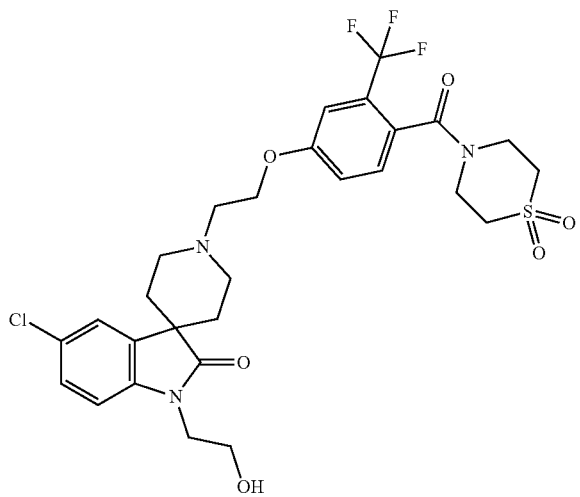 [SMILES: O=C(c1ccc(OCCN2CCC3(CC2)C(=O)N(CCO)c2ccc(Cl)cc23)cc1C(F)(F)F)N1CCS(=O)(=O)CC1] | 4-(4-{2-[5-chloro-1-(2-hydroxyethyl)-2-oxo-1,2-dihydrospiro[indole-3,4'-piperidin]-1'-yl]ethoxy}-2-(trifluoromethyl)benzoyl)-1$\lambda^6$-thiomorpholine-1,1-dione |
| 272 | 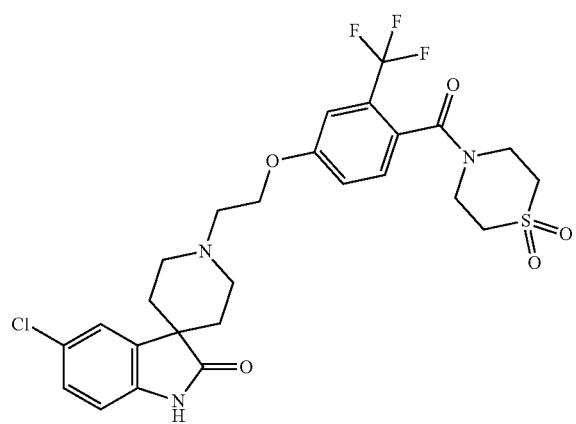 [SMILES: O=C(c1ccc(OCCN2CCC3(CC2)C(=O)Nc2ccc(Cl)cc23)cc1C(F)(F)F)N1CCS(=O)(=O)CC1] | 4-[4-(2-{5-chloro-2-oxo-1,2-dihydrospiro[indole-3,4'-piperidin]-1'-yl}ethoxy)-2-(trifluoromethyl)benzoyl]-1$\lambda^6$-thiomorpholine-1,1-dione |
| 273 | 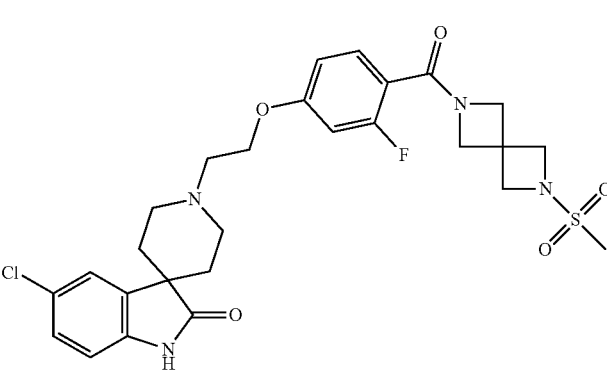 [SMILES: CS(=O)(=O)N1CC2(CN(C(=O)c3ccc(OCCN4CCC5(CC4)C(=O)Nc4ccc(Cl)cc45)cc3F)C2)C1] | 5-chloro-1'-[2-(3-fluoro-4-{6-methanesulfonyl-2,6-diazaspiro[3.3]heptane-2-carbonyl}phenoxy)ethyl]-1,2-dihydrospiro[indole-3,4'-piperidin]-2-one |

TABLE 1-continued

| Compound Number | Structure | Name |
|---|---|---|
| 274 | 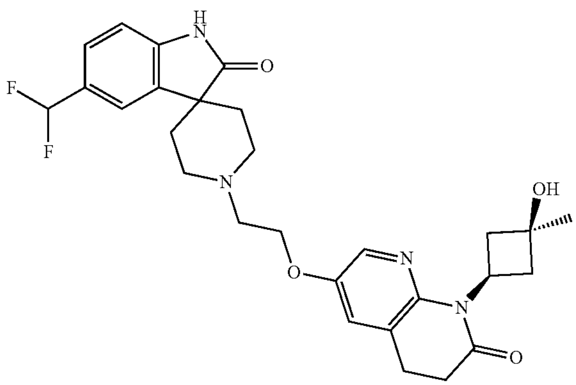 [SMILES: C[C@]1(O)C[C@@H](N2C(=O)CCc3cc(OCCN4CCC5(CC4)C(=O)Nc4ccc(C(F)F)cc45)cnc32)C1] | 5-(difluoromethyl)-1'-[2-({7-oxo-8-[(cis)-3-hydroxy-3-methylcyclobutyl]-5,6,7,8-tetrahydro-1,8-naphthyridin-3-yl}oxy)ethyl]-1,2-dihydrospiro[indole-3,4'-piperidin]-2-one |
| 275 | 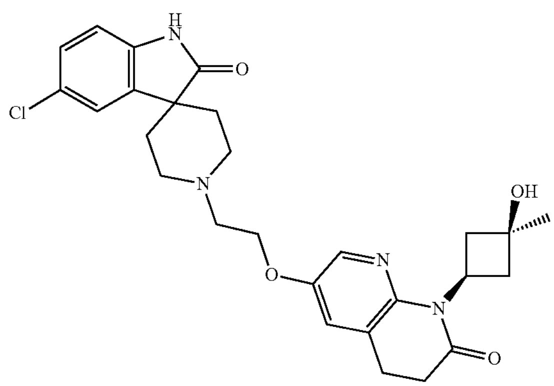 [SMILES: C[C@]1(O)C[C@@H](N2C(=O)CCc3cc(OCCN4CCC5(CC4)C(=O)Nc4ccc(Cl)cc45)cnc32)C1] | 5-chloro-1'-[2-({7-oxo-8-[(cis)-3-hydroxy-3-methylcyclobutyl]-5,6,7,8-tetrahydro-1,8-naphthyridin-3-yl}oxy)ethyl]-1,2-dihydrospiro[indole-3,4'-piperidin]-2-one |
| 276 | 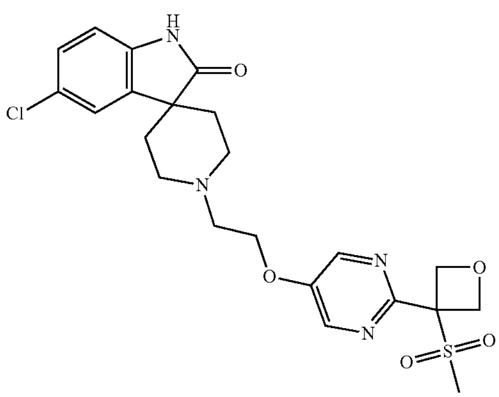 [SMILES: CS(=O)(=O)C1(c2ncc(OCCN3CCC4(CC3)C(=O)Nc3ccc(Cl)cc34)cn2)COC1] | 5-chloro-1'-(2-{[2-(3-methanesulfonyloxetan-3-yl)pyrimidin-5-yl]oxy}ethyl)-1,2-dihydrospiro[indole-3,4'-piperidin]-2-one |
| 277 | 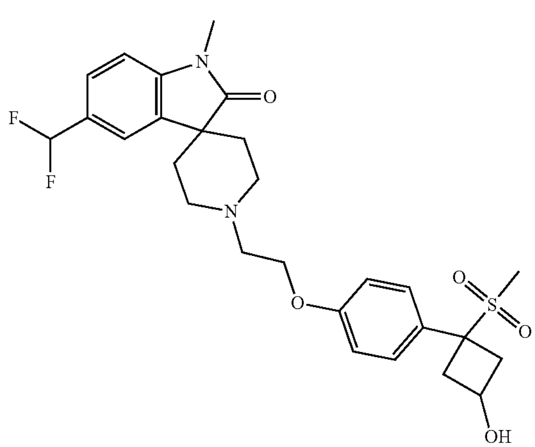 [SMILES: CN1C(=O)C2(CCN(CCOc3ccc(C4(S(C)(=O)=O)CC(O)C4)cc3)CC2)c2cc(C(F)F)ccc21] | 5-(difluoromethyl)-1'-{2-[4-(3-hydroxy-1-methanesulfonylcyclobutyl)phenoxy]ethyl}-1-methyl-1,2-dihydrospiro[indole-3,4'-piperidin]-2-one |

TABLE 1-continued

| Compound Number | Structure | Name |
|---|---|---|
| 278 | 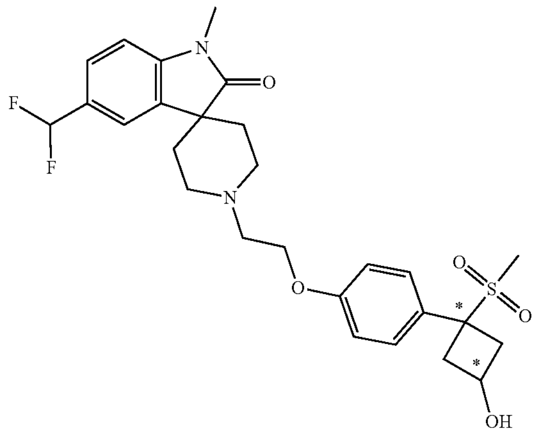 [SMILES: CN1C(=O)C2(CCN(CCOc3ccc(C4(S(C)(=O)=O)CC(O)C4)cc3)CC2)c2cc(C(F)F)ccc21] | 5-(difluoromethyl)-1-methyl-1'-(2-{4-[(cis) or (trans)-3-hydroxy-1-methanesulfonylcyclobutyl]phenoxy}ethyl)-1,2-dihydrospiro[indole-3,4'-piperidin]-2-one |
| 279 | 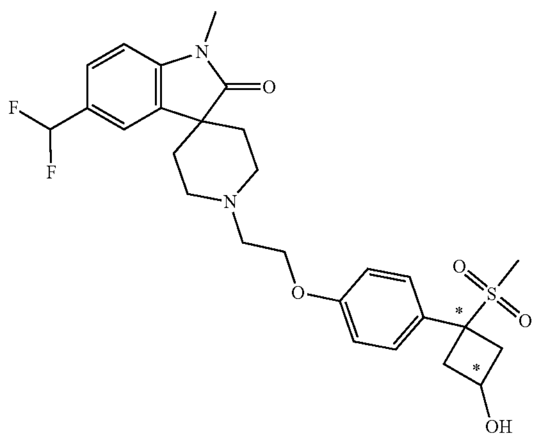 [SMILES: CN1C(=O)C2(CCN(CCOc3ccc(C4(S(C)(=O)=O)CC(O)C4)cc3)CC2)c2cc(C(F)F)ccc21] | 5-(difluoromethyl)-1-methyl-1'-(2-{4-[(trans) or (cis)-3-hydroxy-1-methanesulfonylcyclobutyl]phenoxy}ethyl)-1,2-dihydrospiro[indole-3,4'-piperidin]-2-one |
| 280 | 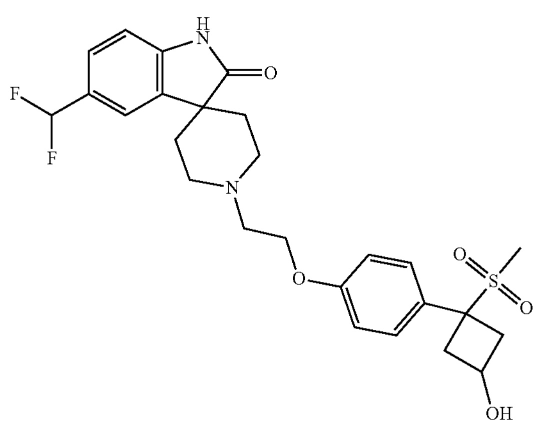 [SMILES: CS(=O)(=O)C1(c2ccc(OCCN3CCC4(CC3)C(=O)Nc3ccc(C(F)F)cc34)cc2)CC(O)C1] | 5-(difluoromethyl)-1'-{2-[4-(3-hydroxy-1-methanesulfonylcyclobutyl)phenoxy]ethyl}-1,2-dihydrospiro[indole-3,4'-piperidin]-2-one |

TABLE 1-continued

| Compound Number | Structure | Name |
|---|---|---|
| 281 | 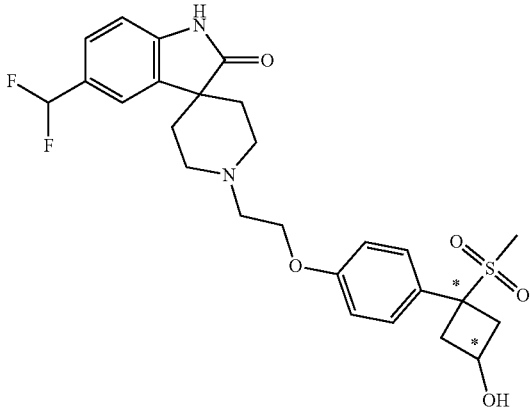 [SMILES: CS(=O)(=O)C1(c2ccc(OCCN3CCC4(CC3)C(=O)Nc3ccc(C(F)F)cc34)cc2)CC(O)C1] | 5-(difluoromethyl)-1'-(2-{4-[(cis) or (trans)-3-hydroxy-1-methanesulfonylcyclobutyl]phenoxy}ethyl)-1,2-dihydrospiro[indole-3,4'-piperidin]-2-one |
| 282 | 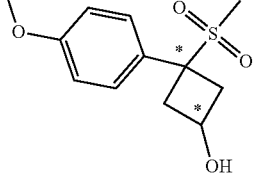 | 5-(difluoromethyl)-1'-(2-{4-[(trans) or (cis)-3-hydroxy-1-methanesulfonylcyclobutyl]phenoxy}ethyl)-1,2-dihydrospiro[indole-3,4'-piperidin]-2-one |
| 283 | 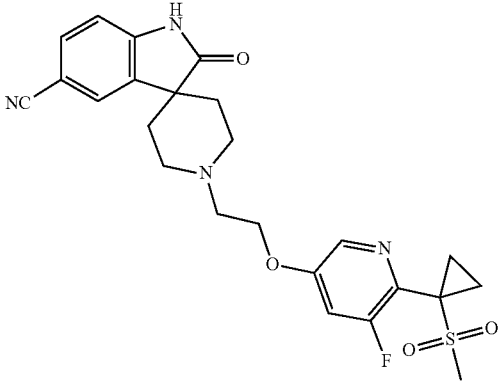 [SMILES: CS(=O)(=O)C1(c2ncc(OCCN3CCC4(CC3)C(=O)Nc3ccc(C#N)cc34)cc2F)CC1] | 1'-(2-{[5-fluoro-6-(1-methanesulfonylcyclopropyl)pyridin-3-yl]oxy}ethyl)-2-oxo-1,2-dihydrospiro[indole-3,4'-piperidine]-5-carbonitrile |
| 284 | 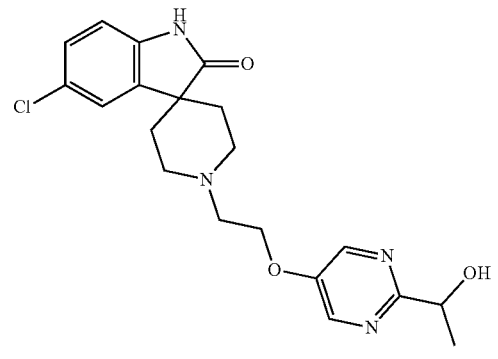 [SMILES: CC(O)c1ncc(OCCN2CCC3(CC2)C(=O)Nc2ccc(Cl)cc23)cn1] | 5-chloro-1'-(2-{[2-(1-hydroxyethyl)pyrimidin-5-yl]oxy}ethyl)-1,2-dihydrospiro[indole-3,4'-piperidin]-2-one |

TABLE 1-continued

| Compound Number | Structure | Name |
|---|---|---|
| 285 | 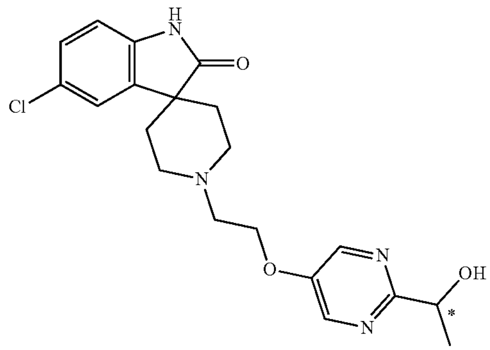 [SMILES: CC(O)c1ncc(OCCN2CCC3(CC2)C(=O)Nc2ccc(Cl)cc23)cn1] | 5-chloro-1'-[2-({2-[(1S) or (1R)-1-hydroxyethyl]pyrimidin-5-yl}oxy)ethyl]-1,2-dihydrospiro[indole-3,4'-piperidin]-2-one |
| 286 | 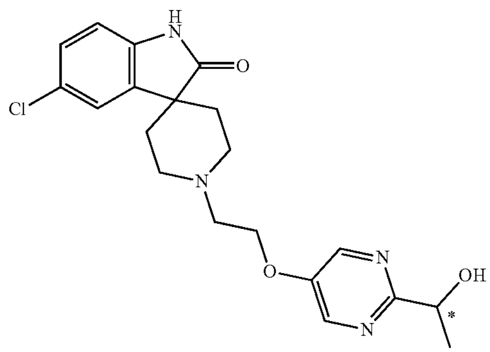 [SMILES: CC(O)c1ncc(OCCN2CCC3(CC2)C(=O)Nc2ccc(Cl)cc23)cn1] | 5-chloro-1'-[2-((2-[(1R) or (1S)-1-hydroxyethyl]pyrimidin-5-yl}oxy)ethyl]-1,2-dihydrospiro[indole-3,4'-piperidin]-2-one |
| 287 | 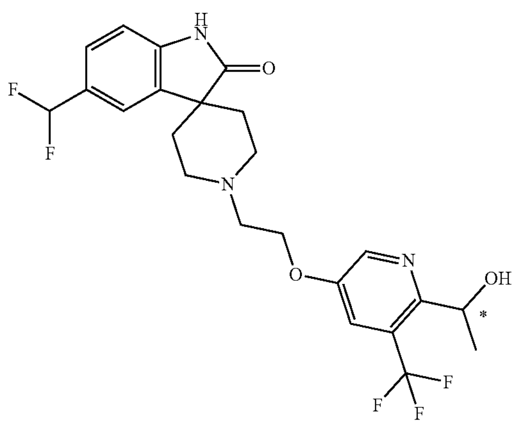 [SMILES: CC(O)c1ncc(OCCN2CCC3(CC2)C(=O)Nc2ccc(C(F)F)cc23)cc1C(F)(F)F] | 5-(difluoromethyl)-1'-[2-({6-[(1S) or (1R)-1-hydroxyethyl]-5-(trifluoromethyl)pyridin-3-yl}oxy)ethyl]-1,2-dihydrospiro[indole-3,4'-piperidin]-2-one |
| 288 | 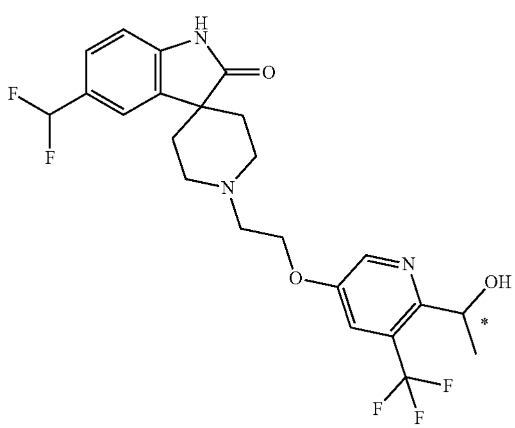 [SMILES: CC(O)c1ncc(OCCN2CCC3(CC2)C(=O)Nc2ccc(C(F)F)cc23)cc1C(F)(F)F] | 5-(difluoromethyl)-1'-[2-({6-[(1R) or (1S)-1-hydroxyethyl]-5-(trifluoromethyl)pyridin-3-yl}oxy)ethyl]-1,2-dihydrospiro[indole-3,4'-piperidin]-2-one |

TABLE 1-continued

| Compound Number | Structure | Name |
|---|---|---|
| 289 | 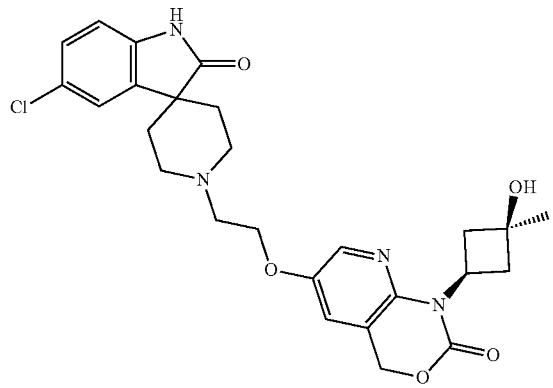 [SMILES: C[C@]1(O)C[C@@H](N2C(=O)OCc3cc(OCCN4CCC5(CC4)C(=O)Nc4ccc(Cl)cc45)cnc32)C1] | 5-chloro-1'-[2-({2-oxo-1-[(cis)-3-hydroxy-3-methylcyclobutyl]-1H,2H,4H-pyrido[2,3-d][1,3]oxazin-6-yl}oxy)ethyl]-1,2-dihydrospiro[indole-3,4'-piperidin]-2-one |
| 290 | 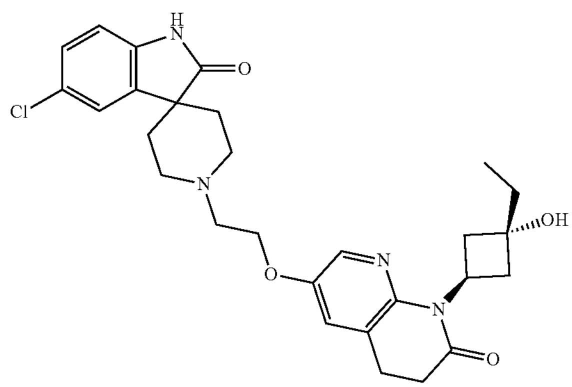 [SMILES: CC[C@]1(O)C[C@H](N2C(=O)CCc3cc(OCCN4CCC5(CC4)C(=O)Nc4ccc(Cl)cc45)cnc32)C1] | 5-chloro-1'-[2-({7-oxo-8-[(trans)-3-ethyl-3-hydroxycyclobutyl]-5,6,7,8-tetrahydro-1,8-naphthyridin-3-yl}oxy)ethyl]-1,2-dihydrospiro[indole-3,4'-piperidin]-2-one |
| 291 | 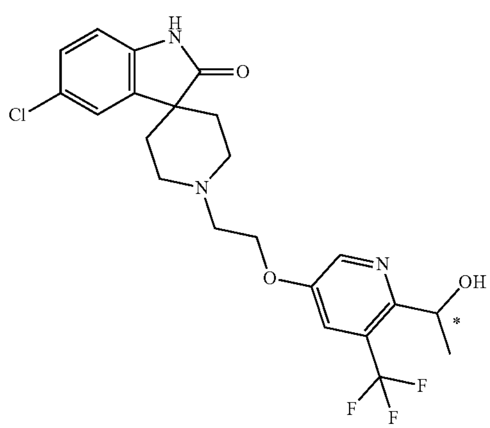 [SMILES: CC(O)c1ncc(OCCN2CCC3(CC2)C(=O)Nc2ccc(Cl)cc23)cc1C(F)(F)F] | 5-chloro-1'-[2-({6-[(1S) or (1R)-1-hydroxyethyl]-5-(trifluoromethyl)pyridin-3-yl]oxy)ethyl]-1,2-dihydrospiro[indole-3,4'-piperidin]-2-one |

| Compound Number | Structure | Name |
|---|---|---|
| 292 | 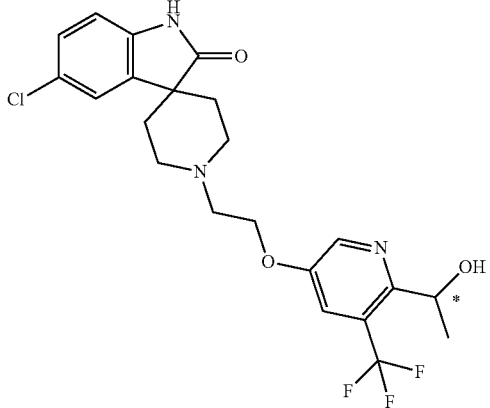 [SMILES: CC(O)c1ncc(OCCN2CCC3(CC2)C(=O)Nc2ccc(Cl)cc23)cc1C(F)(F)F] | 5-chloro-1'-[2-({6-[(1R) or (1S)-1-hydroxyethyl]-5-(trifluoromethyl)pyridin-3-yl}oxy)ethyl]-1,2-dihydrospiro[indole-3,4'-piperidin]-2-one |
| 293 | 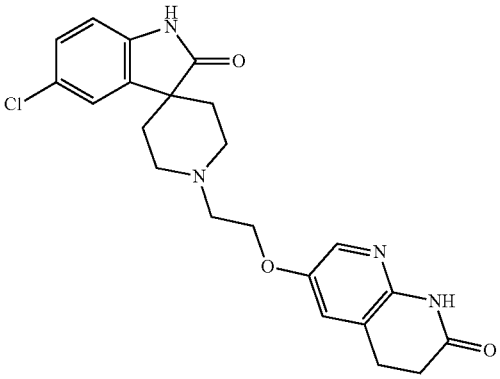 [SMILES: O=C1CCc2cc(OCCN3CCC4(CC3)C(=O)Nc3ccc(Cl)cc34)cnc2N1] | 5-chloro-1'-{2-[(7-oxo-5,6,7,8-tetrahydro-1,8-naphthyridin-3-yl)oxy]ethyl}-1,2-dihydrospiro[indole-3,4'-piperidin]-2-one |
| 294 | 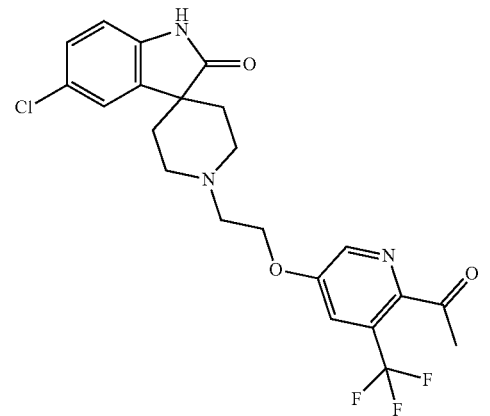 [SMILES: CC(=O)c1ncc(OCCN2CCC3(CC2)C(=O)Nc2ccc(Cl)cc23)cc1C(F)(F)F] | 1'-(2-{[6-acetyl-5-(trifluoromethyl)pyridin-3-yl]oxy}ethyl)-5-chloro-1,2-dihydrospiro[indole-3,4'-piperidin]-2-one |

TABLE 1-continued

| Compound Number | Structure | Name |
|---|---|---|
| 295 | 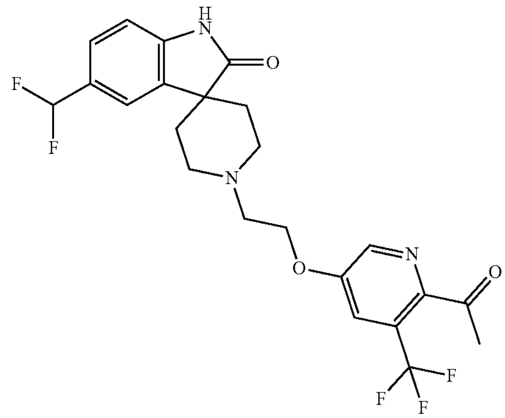 [SMILES: CC(=O)c1ncc(OCCN2CCC3(CC2)C(=O)Nc2ccc(C(F)F)cc23)cc1C(F)(F)F] | 1'-(2-{[6-acetyl-5-(trifluoromethyl)pyridin-3-yl]oxy}ethyl)-5-(difluoromethyl)-1,2-dihydrospiro[indole-3,4'-piperidin]-2-one |
| 296 | 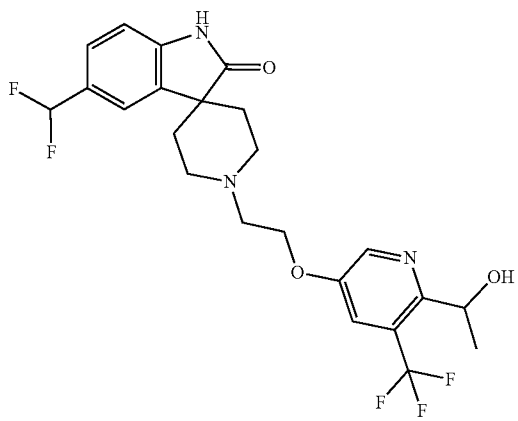 [SMILES: CC(O)c1ncc(OCCN2CCC3(CC2)C(=O)Nc2ccc(C(F)F)cc23)cc1C(F)(F)F] | 5-(difluoromethyl)-1'-(2-{[6-(1-hydroxyethyl)-5-(trifluoromethyl)pyridin-3-yl]oxy}ethyl)-1,2-dihydrospiro[indole-3,4'-piperidin]-2-one |
| 297 | 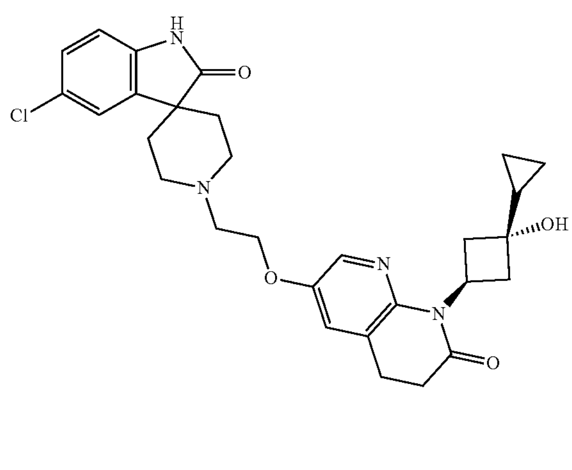 [SMILES: O=C1CCc2cc(OCCN3CCC4(CC3)C(=O)Nc3ccc(Cl)cc34)cnc2N1[C@H]1C[C@@](O)(C2CC2)C1] | 5-chloro-1'-[2-({7-oxo-8-[(trans)-3-cyclopropyl-3-hydroxycyclobutyl]-5,6,7,8-tetrahydro-1,8-naphthyridin-3-yl}oxy)ethyl]-1,2-dihydrospiro[indole-3,4'-piperidin]-2-one |

TABLE 1-continued

| Compound Number | Structure | Name |
|---|---|---|
| 298 | 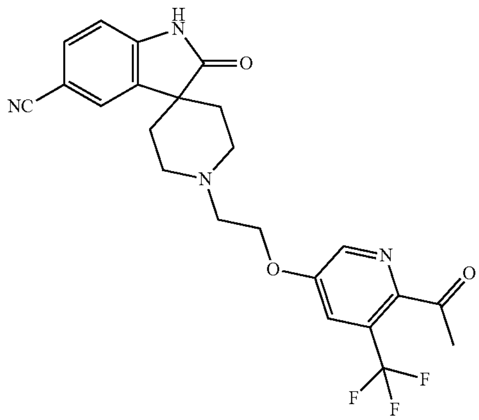 [SMILES: CC(=O)c1ncc(OCCN2CCC3(CC2)C(=O)Nc2ccc(C#N)cc23)cc1C(F)(F)F] | 1'-(2-{[6-acetyl-5-(trifluoromethyl)pyridin-3-yl]oxy}ethyl)-2-oxo-1,2-dihydrospiro[indole-3,4'-piperidine]-5-carbonitrile |
| 299 | 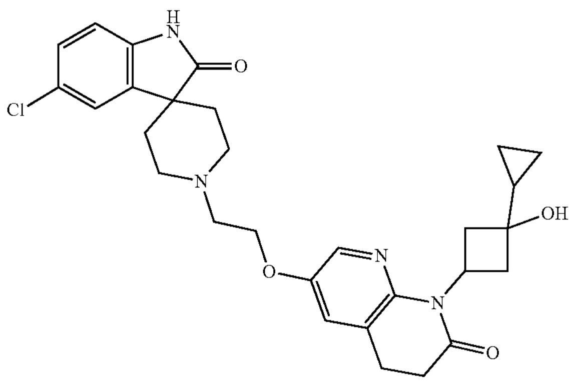 [SMILES: O=C1CCc2cc(OCCN3CCC4(CC3)C(=O)Nc3ccc(Cl)cc34)cnc2N1C1CC(O)(C2CC2)C1] | 5-chloro-1'-(2-{[8-(3-cyclopropyl-3-hydroxycyclobutyl)-7-oxo-5,6,7,8-tetrahydro-1,8-naphthyridin-3-yl]oxy}ethyl)-1,2-dihydrospiro[indole-3,4'-piperidin]-2-one |
| 300 | 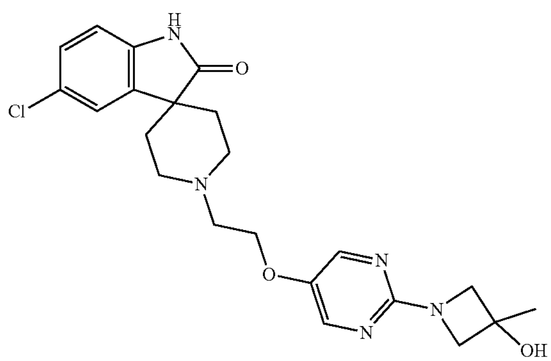 [SMILES: CC1(O)CN(c2ncc(OCCN3CCC4(CC3)C(=O)Nc3ccc(Cl)cc34)cn2)C1] | 5-chloro-1'-(2-{[2-(3-hydroxy-3-methylazetidin-1-yl)pyrimidin-5-yl]oxy}ethyl)-1,2-dihydrospiro[indole-3,4'-piperidin]-2-one |
| 301 | 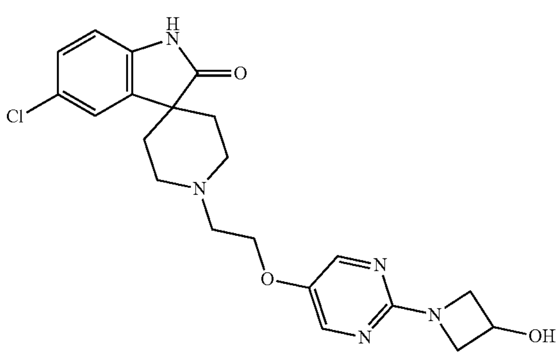 [SMILES: O=C1Nc2ccc(Cl)cc2C12CCN(CCOc1cnc(N3CC(O)C3)nc1)CC2] | 5-chloro-1'-(2-{[2-(3-hydroxyazetidin-1-yl)pyrimidin-5-yl]oxy}ethyl)-1,2-dihydrospiro[indole-3,4'-piperidin]-2-one |

TABLE 1-continued

| Compound Number | Structure | Name |
|---|---|---|
| 302 | 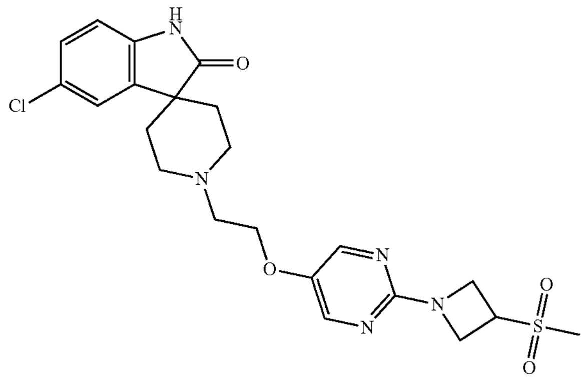 [SMILES: CS(=O)(=O)C1CN(c2ncc(OCCN3CCC4(CC3)C(=O)Nc3ccc(Cl)cc34)cn2)C1] | 5-chloro-1'-(2-{[2-(3-methanesulfonylazetidin-1-yl)pyrimidin-5-yl]oxy}ethyl)-1,2-dihydrospiro[indole-3,4'-piperidin]-2-one |
| 303 | 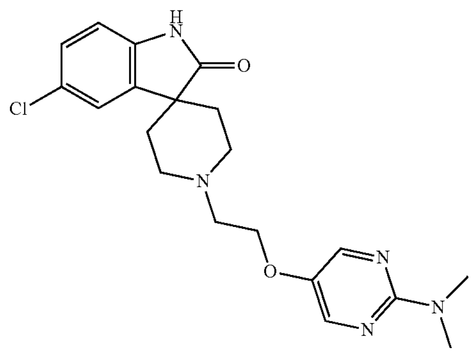 [SMILES: CN(C)c1ncc(OCCN2CCC3(CC2)C(=O)Nc2ccc(Cl)cc23)cn1] | 5-chloro-1'-(2-{[2-(dimethylamino)pyrimidin-5-yl]oxy}ethyl)-1,2-dihydrospiro[indole-3,4'-piperidin]-2-one |
| 304 | 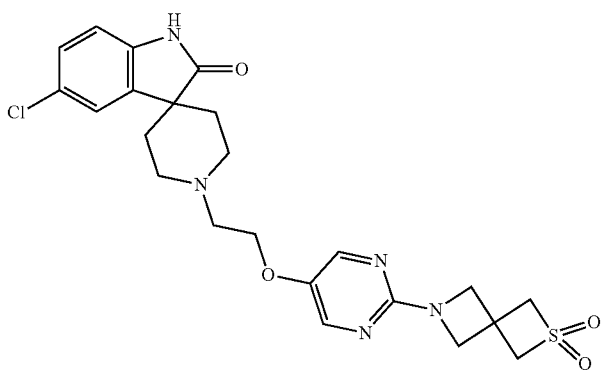 [SMILES: O=C1Nc2ccc(Cl)cc2C12CCN(CCOc1cnc(N3CC4(C3)CS(=O)(=O)C4)nc1)CC2] | 6-[5-(2-{5-chloro-2-oxo-1,2-dihydrospiro[indole-3,4'-piperidin]-1'-yl}ethoxy)pyrimidin-2-yl]-2$\lambda^6$-thia-6-azaspiro[3.3]heptane-2,2-dione |
| 305 | 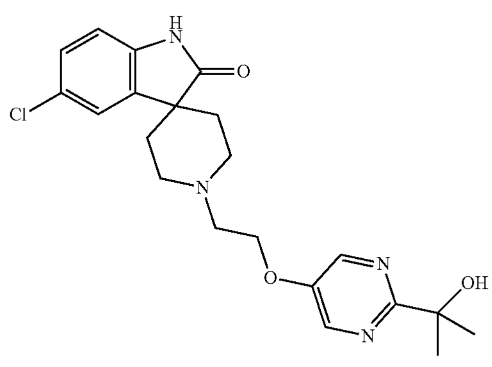 [SMILES: CC(C)(O)c1ncc(OCCN2CCC3(CC2)C(=O)Nc2ccc(Cl)cc23)cn1] | 5-chloro-1'-(2-{[2-(2-hydroxypropan-2-yl)pyrimidin-5-yl]oxy}ethyl)-1,2-dihydrospiro[indole-3,4'-piperidin]-2-one |

TABLE 1-continued

| Compound Number | Structure | Name |
|---|---|---|
| 306 | 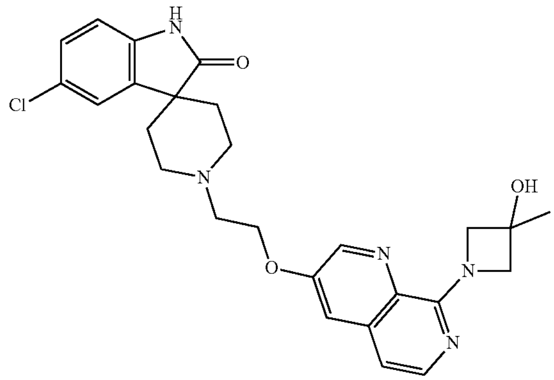 [SMILES: CC1(O)CN(c2nccc3cc(OCCN4CCC5(CC4)C(=O)Nc4ccc(Cl)cc45)cnc23)C1] | 5-chloro-1'-(2-{[8-(3-hydroxy-3-methylazetidin-1-yl)-1,7-naphthyridin-3-yl]oxy}ethyl)-1,2-dihydrospiro[indole-3,4'-piperidin]-2-one |
| 307 | 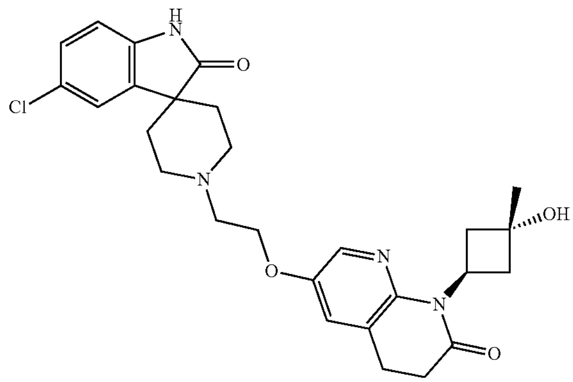 [SMILES: C[C@]1(O)C[C@H](N2C(=O)CCc3cc(OCCN4CCC5(CC4)C(=O)Nc4ccc(Cl)cc45)cnc32)C1] | 5-chloro-1'-[2-({7-oxo-8-[(trans)-3-hydroxy-3-methylcyclobutyl]-5,6,7,8-tetrahydro-1,8-naphthyridin-3-yl}oxy)ethyl]-1,2-dihydrospiro[indole-3,4'-piperidin]-2-one |
| 308 | 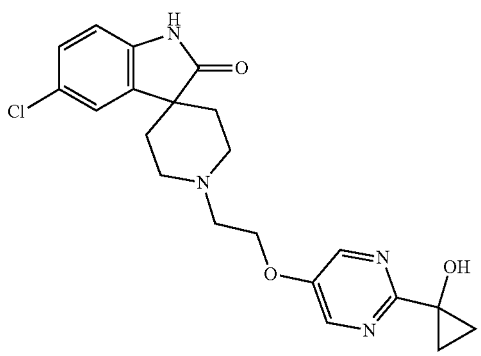 [SMILES: O=C1Nc2ccc(Cl)cc2C12CCN(CCOc1cnc(C3(O)CC3)nc1)CC2] | 5-chloro-1'-(2-{[2-(1-hydroxycyclopropyl)pyrimidin-5-yl]oxy}ethyl)-1,2-dihydrospiro[indole-3,4'-piperidin]-2-one |
| 309 | 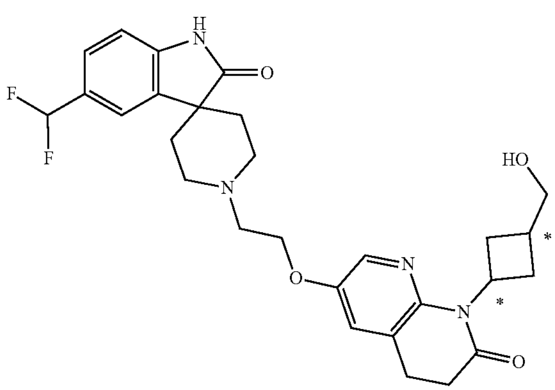 [SMILES: O=C1CCc2cc(OCCN3CCC4(CC3)C(=O)Nc3ccc(C(F)F)cc34)cnc2N1C1CC(CO)C1] | 5-(difluoromethyl)-1'-[2-({7-oxo-8-[(cis) or (trans)-3-(hydroxymethyl)cyclobutyl]-5,6,7,8-tetrahydro-1,8-naphthyridin-3-yl}oxy)ethyl]-1,2-dihydrospiro[indole-3,4'-piperidin]-2-one |

TABLE 1-continued

| Compound Number | Structure | Name |
|---|---|---|
| 310 | 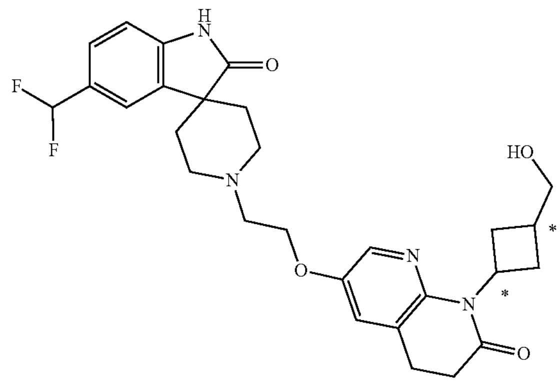 [SMILES: O=C1CCc2cc(OCCN3CCC4(CC3)C(=O)Nc3ccc(C(F)F)cc34)cnc2N1C1CC(CO)C1] | 5-(difluoromethyl)-1'-[2-({7-oxo-8-[(trans) or (cis)-3-(hydroxymethyl)cyclobutyl]-5,6,7,8-tetrahydro-1,8-naphthyridin-3-yl}oxy)ethyl]-1,2-dihydrospiro[indole-3,4'-piperidin]-2-one |
| 311 | 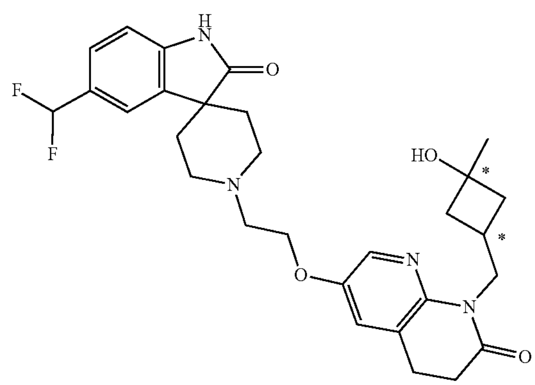 [SMILES: CC1(O)CC(CN2C(=O)CCc3cc(OCCN4CCC5(CC4)C(=O)Nc4ccc(C(F)F)cc45)cnc32)C1] | 5-(difluoromethyl)-1'-{2-[(7-oxo-8-{[(cis) or (trans)-3-hydroxy-3-methylcyclobutyl]methyl}-5,6,7,8-tetrahydro-1,8-naphthyridin-3-yl)oxy]ethyl}-1,2-dihydrospiro[indole-3,4'-piperidin]-2-one |
| 312 | 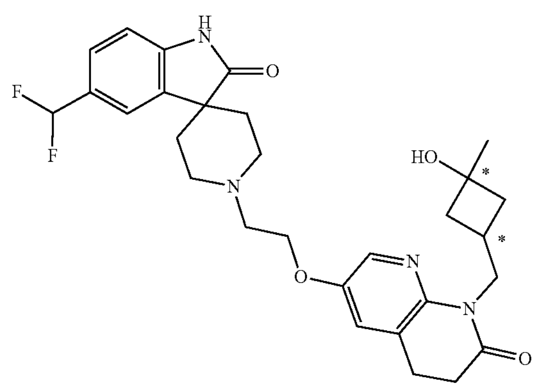 [SMILES: CC1(O)CC(CN2C(=O)CCc3cc(OCCN4CCC5(CC4)C(=O)Nc4ccc(C(F)F)cc45)cnc32)C1] | 5-(difluoromethyl)-1'-{2-[(7-oxo-8-{[(trans) or (cis)-3-hydroxy-3-methylcyclobutyl]methyl}-5,6,7,8-tetrahydro-1,8-naphthyridin-3-yl)oxy]ethyl}-1,2-dihydrospiro[indole-3,4'-piperidin]-2-one |
| 313 | 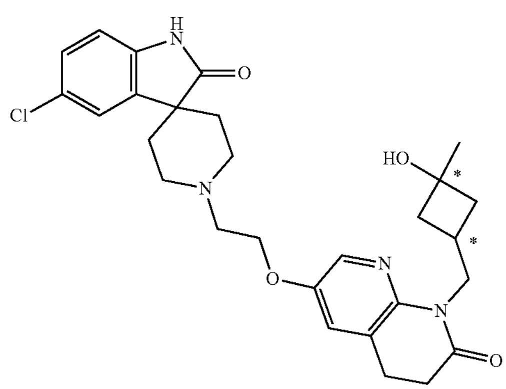 [SMILES: CC1(O)CC(CN2C(=O)CCc3cc(OCCN4CCC5(CC4)C(=O)Nc4ccc(Cl)cc45)cnc32)C1] | 5-chloro-1'-{2-[(7-oxo-8-{[(cis) or (trans)-3-hydroxy-3-methylcyclobutyl]methyl}-5,6,7,8-tetrahydro-1,8-naphthyridin-3-yl)oxy]ethyl}-1,2-dihydrospiro[indole-3,4'-piperidin]-2-one |

TABLE 1-continued

| Compound Number | Structure | Name |
|---|---|---|
| 314 | 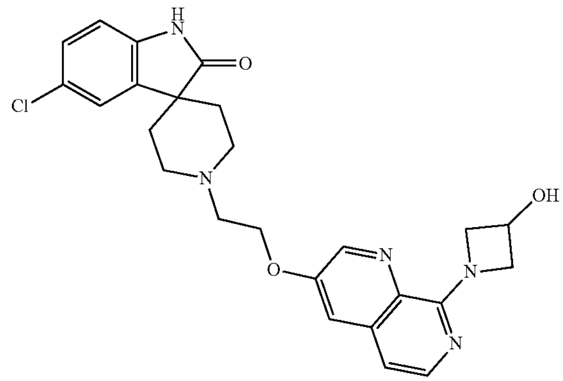 [SMILES: O=C1Nc2ccc(Cl)cc2C12CCN(CCOc1cnc3c(N4CC(O)C4)nccc3c1)CC2] | 5-chloro-1'-(2-{[8-(3-hydroxyazetidin-1-yl)-1,7-naphthyridin-3-yl]oxy}ethyl)-1,2-dihydrospiro[indole-3,4'-piperidin]-2-one |
| 315 | 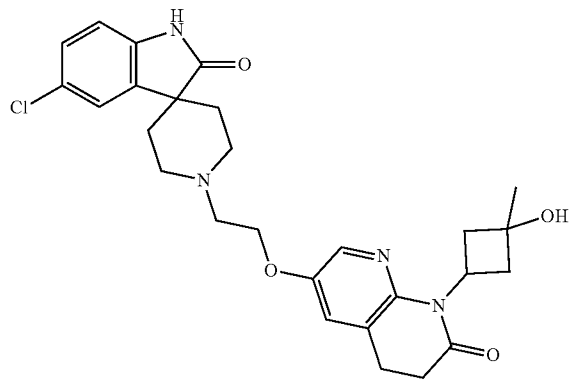 [SMILES: CC1(O)CC(N2C(=O)CCc3cc(OCCN4CCC5(CC4)C(=O)Nc4ccc(Cl)cc45)cnc32)C1] | 5-chloro-1'-(2-{[8-(3-hydroxy-3-methylcyclobutyl)-7-oxo-5,6,7,8-tetrahydro-1,8-naphthyridin-3-yl]oxy}ethyl)-1,2-dihydrospiro[indole-3,4'-piperidin]-2-one |
| 316 | 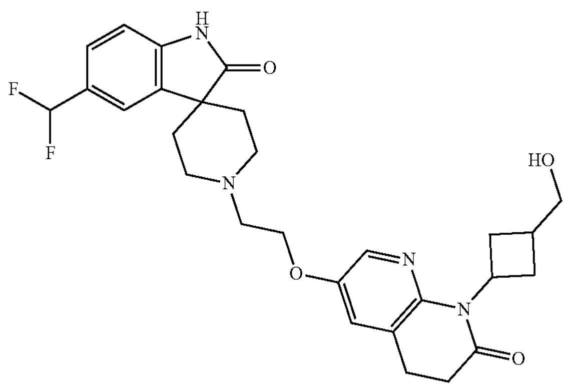 [SMILES: O=C1CCc2cc(OCCN3CCC4(CC3)C(=O)Nc3ccc(C(F)F)cc34)cnc2N1C1CC(CO)C1] | 5-(difluoromethyl)-1'-[2-({8-[3-(hydroxymethyl)cyclobutyl]-7-oxo-5,6,7,8-tetrahydro-1,8-naphthyridin-3-yl}oxy)ethyl]-1,2-dihydrospiro[indole-3,4'-piperidin]-2-one |
| 317 | 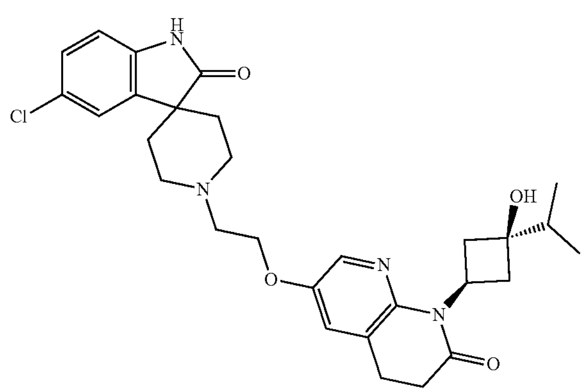 [SMILES: CC(C)[C@]1(O)C[C@@H](N2C(=O)CCc3cc(OCCN4CCC5(CC4)C(=O)Nc4ccc(Cl)cc45)cnc32)C1] | 5-chloro-1'-[2-({7-oxo-8-[(cis)-3-hydroxy-3-(propan-2-yl)cyclobutyl]-5,6,7,8-tetrahydro-1,8-naphthyridin-3-yl}oxy)ethyl]-1,2-dihydrospiro[indole-3,4'-piperidin]-2-one |

TABLE 1-continued

| Compound Number | Structure | Name |
|---|---|---|
| 318 | 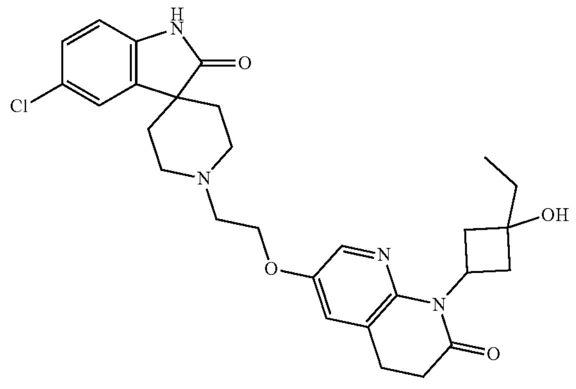 [SMILES: CCC1(O)CC(N2C(=O)CCc3cc(OCCN4CCC5(CC4)C(=O)Nc4ccc(Cl)cc45)cnc32)C1] | 5-chloro-1'-(2-{[8-(3-ethyl-3-hydroxycyclobutyl)-7-oxo-5,6,7,8-tetrahydro-1,8-naphthyridin-3-yl]oxy}ethyl)-1,2-dihydrospiro[indole-3,4'-piperidin]-2-one |
| 319 | 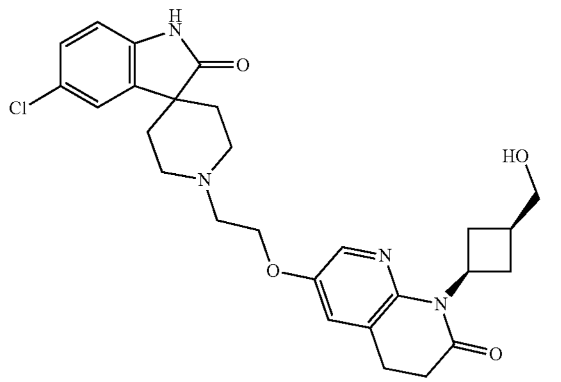 [SMILES: O=C1CCc2cc(OCCN3CCC4(CC3)C(=O)Nc3ccc(Cl)cc34)cnc2N1[C@H]1C[C@@H](CO)C1] | 5-chloro-1'-[2-({7-oxo-8-[(cis)-3-(hydroxymethyl)cyclobutyl]cyclobutyl]-5,6,7,8-tetrahydro-1,8-naphthyridin-3-yl}oxy)ethyl]-1,2-dihydrospiro[indole-3,4'-piperidin]-2-one |
| 320 | 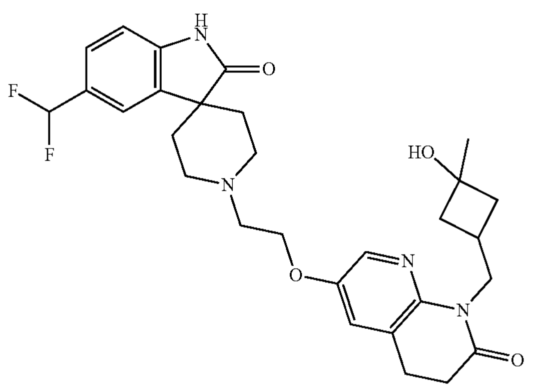 [SMILES: CC1(O)CC(CN2C(=O)CCc3cc(OCCN4CCC5(CC4)C(=O)Nc4ccc(C(F)F)cc45)cnc32)C1] | 5-(difluoromethyl)-1'-[2-({8-[(3-hydroxy-3-methylcyclobutyl)methyl]-7-oxo-5,6,7,8-tetrahydro-1,8-naphthyridin-3-yl}oxy)ethyl]-1,2-dihydrospiro[indole-3,4'-piperidin]-2-one |
| 321 | 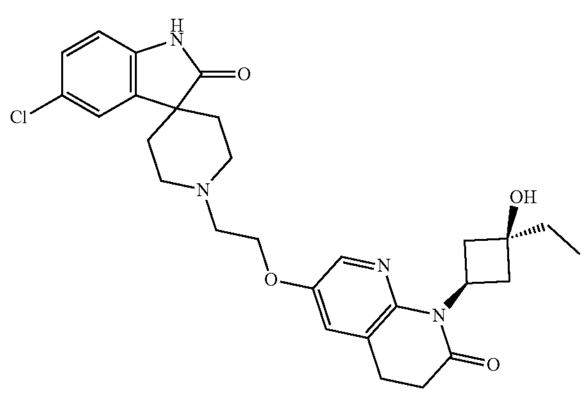 [SMILES: CC[C@]1(O)C[C@@H](N2C(=O)CCc3cc(OCCN4CCC5(CC4)C(=O)Nc4ccc(Cl)cc45)cnc32)C1] | 5-chloro-1'-[2-({7-oxo-8-[(cis)-3-ethyl-3-hydroxycyclobutyl]-5,6,7,8-tetrahydro-1,8-naphthyridin-3-yl}oxy)ethyl]-1,2-dihydrospiro[indole-3,4'-piperidin]-2-one |

TABLE 1-continued

| Compound Number | Structure | Name |
|---|---|---|
| 322 | 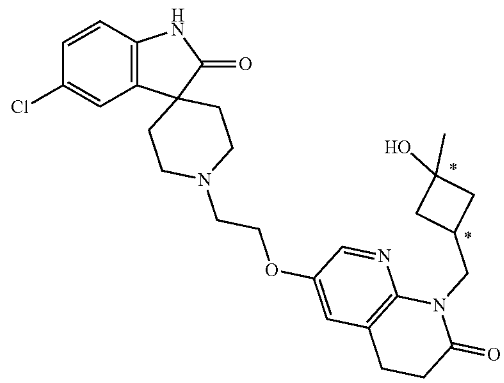 [SMILES: CC1(O)CC(CN2C(=O)CCc3cc(OCCN4CCC5(CC4)C(=O)Nc4ccc(Cl)cc45)cnc32)C1] | 5-chloro-1'-{2-[(7-oxo-8-{[(trans) or (cis)-3-hydroxy-3-methylcyclobutyl]methyl}-5,6,7,8-tetrahydro-1,8-naphthyridin-3-yl)oxy]ethyl}-1,2-dihydrospiro[indole-3,4'-piperidin]-2-one |
| 323 | 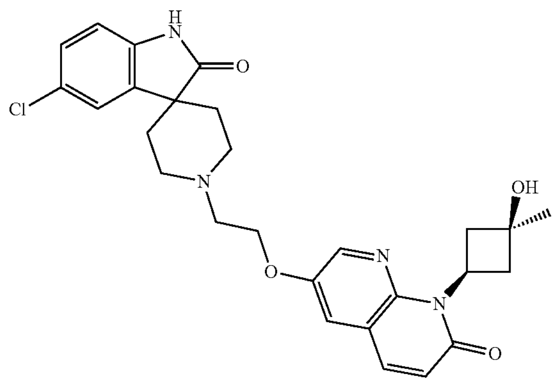 [SMILES: C[C@]1(O)C[C@@H](n2c(=O)ccc3cc(OCCN4CCC5(CC4)C(=O)Nc4ccc(Cl)cc45)cnc32)C1] | 5-chloro-1'-[2-({7-oxo-8-[(cis)-3-hydroxy-3-methylcyclobutyl]-7,8-dihydro-1,8-naphthyridin-3-yl}oxy)ethyl]-1,2-dihydrospiro[indole-3,4'-piperidin]-2-one |
| 324 | 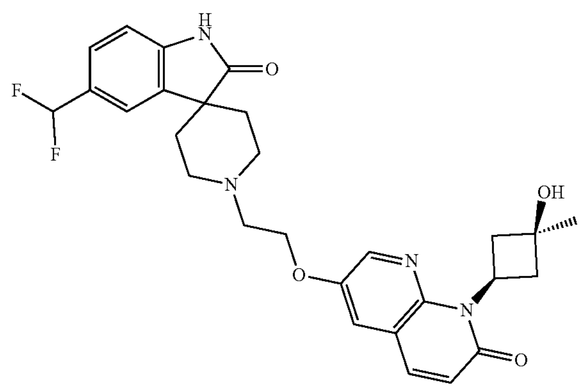 [SMILES: C[C@]1(O)C[C@@H](n2c(=O)ccc3cc(OCCN4CCC5(CC4)C(=O)Nc4ccc(C(F)F)cc45)cnc32)C1] | 5-(difluoromethyl)-1'-[2-({7-oxo-8-[(cis)-3-hydroxy-3-methylcyclobutyl]-7,8-dihydro-1,8-naphthyridin-3-yl}oxy)ethyl]-1,2-dihydrospiro[indole-3,4'-piperidin]-2-one |
| 325 | 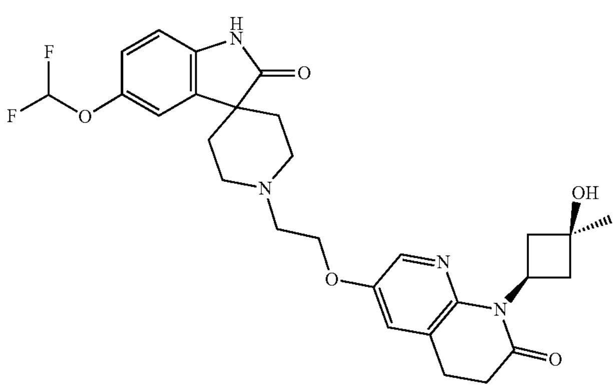 [SMILES: C[C@]1(O)C[C@@H](N2C(=O)CCc3cc(OCCN4CCC5(CC4)C(=O)Nc4ccc(OC(F)F)cc45)cnc32)C1] | 5-(difluoromethoxy)-1'-[2-({7-oxo-8-[(cis)-3-hydroxy-3-methylcyclobutyl]-5,6,7,8-tetrahydro-1,8-naphthyridin-3-yl}oxy)ethyl]-1,2-dihydrospiro[indole-3,4'-piperidin]-2-one |

TABLE 1-continued

| Compound Number | Structure | Name |
|---|---|---|
| 326 | 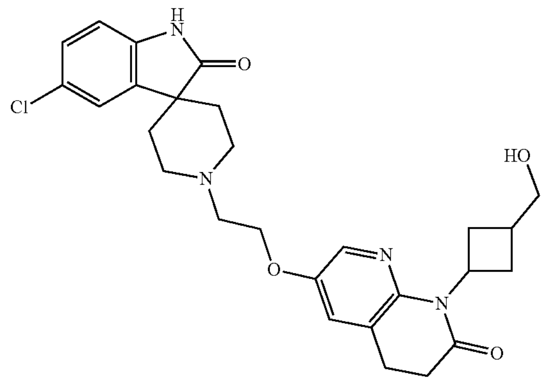 [SMILES: O=C1CCc2cc(OCCN3CCC4(CC3)C(=O)Nc3ccc(Cl)cc34)cnc2N1C1CC(CO)C1] | 5-chloro-1'-[2-({8-[3-(hydroxymethyl)cyclobutyl]-7-oxo-5,6,7,8-tetrahydro-1,8-naphthyridin-3-yl}oxy)ethyl]-1,2-dihydrospiro[indole-3,4'-piperidin]-2-one |
| 327 | 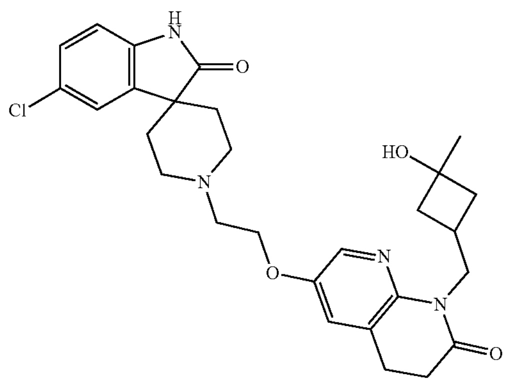 [SMILES: CC1(O)CC(CN2C(=O)CCc3cc(OCCN4CCC5(CC4)C(=O)Nc4ccc(Cl)cc45)cnc32)C1] | 5-chloro-1'-[2-({8-[(3-hydroxy-3-methylcyclobutyl)methyl]-7-oxo-5,6,7,8-tetrahydro-1,8-naphthyridin-3-yl}oxy)ethyl]-1,2-dihydrospiro[indole-3,4'-piperidin]-2-one |
| 328 | 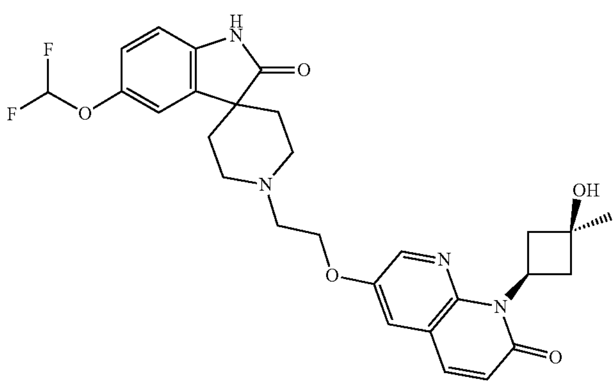 [SMILES: C[C@]1(O)C[C@@H](n2c(=O)ccc3cc(OCCN4CCC5(CC4)C(=O)Nc4ccc(OC(F)F)cc45)cnc32)C1] | 5-(difluoromethoxy)-1'-[2-({7-oxo-8-[(cis)-3-hydroxy-3-methylcyclobutyl]-7,8-dihydro-1,8-naphthyridin-3-yl}oxy)ethyl]-1,2-dihydrospiro[indole-3,4'-piperidin]-2-one |
| 329 | 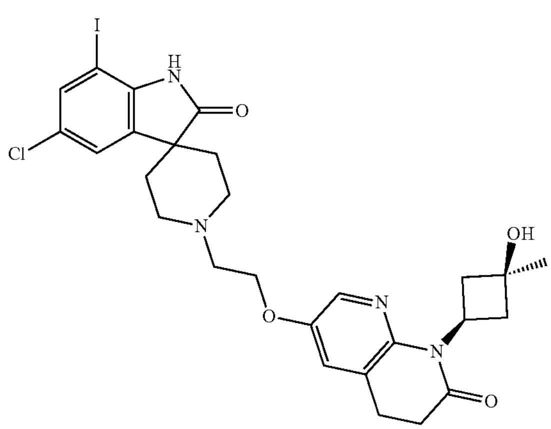 [SMILES: C[C@]1(O)C[C@@H](N2C(=O)CCc3cc(OCCN4CCC5(CC4)C(=O)Nc4c(I)cc(Cl)cc45)cnc32)C1] | 5-chloro-7-iodo-1'-[2-({7-oxo-8-[(cis)-3-hydroxy-3-methylcyclobutyl]-5,6,7,8-tetrahydro-1,8-naphthyridin-3-yl}oxy)ethyl]-1,2-dihydrospiro[indole-3,4'-piperidin]-2-one |

TABLE 1-continued

| Compound Number | Structure | Name |
|---|---|---|
| 330 | 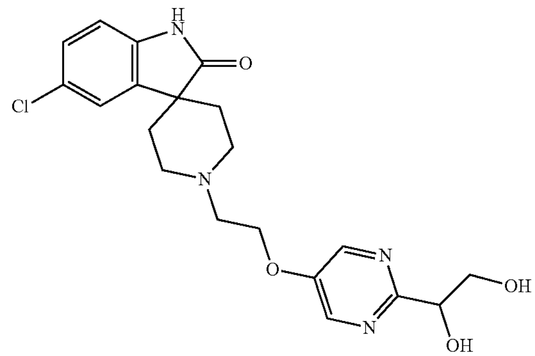 [SMILES: O=C1Nc2ccc(Cl)cc2C12CCN(CCOc1cnc(C(O)CO)nc1)CC2] | 5-chloro-1'-(2-{[2-(1,2-dihydroxyethyl)pyrimidin-5-yl]oxy]ethyl)-1,2-dihydrospiro[indole-3,4'-piperidin]-2-one |
| 331 | 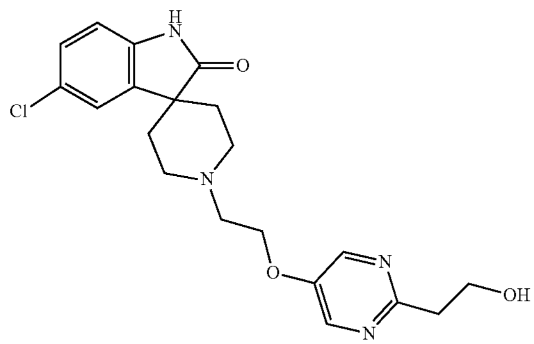 [SMILES: O=C1Nc2ccc(Cl)cc2C12CCN(CCOc1cnc(CCO)nc1)CC2] | 5-chloro-1'-(2-{[2-(2-hydroxyethyl)pyrimidin-5-yl]oxy}ethyl)-1,2-dihydrospiro[indole-3,4'-piperidin]-2-one |
| 332 | 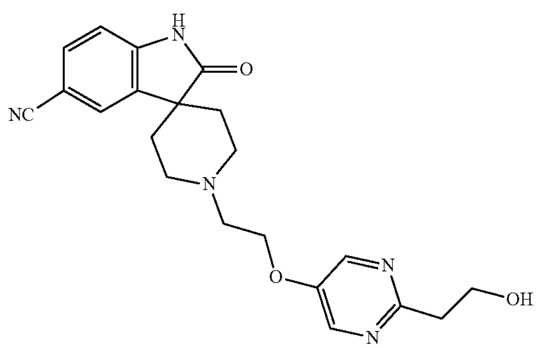 [SMILES: N#Cc1ccc2c(c1)C1(CCN(CCOc3cnc(CCO)nc3)CC1)C(=O)N2] | 1'-(2-{[2-(2-hydroxyethyl)pyrimidin-5-yl]oxy}ethyl)-2-oxo-1,2-dihydrospiro[indole-3,4'-piperidine]-5-carbonitrile |
| 333 | 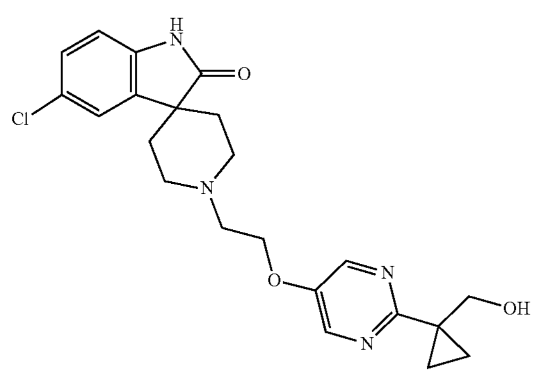 [SMILES: O=C1Nc2ccc(Cl)cc2C12CCN(CCOc1cnc(C3(CO)CC3)nc1)CC2] | 5-chloro-1'-[2-({2-[1-(hydroxymethyl)cyclopropyl]pyrimidin-5-yl}oxy)ethyl]-1,2-dihydrospiro[indole-3,4'-piperidin]-2-one |

| Compound Number | Structure | Name |
|---|---|---|
| 334 | 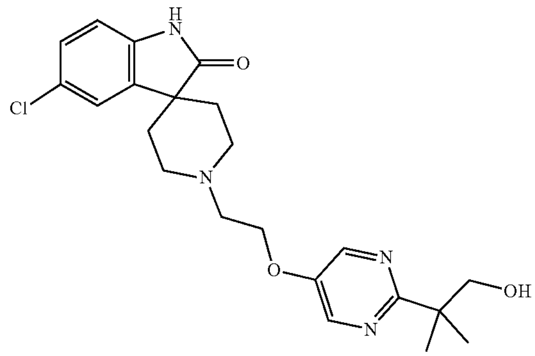 [SMILES: CC(C)(CO)c1ncc(OCCN2CCC3(CC2)C(=O)Nc2ccc(Cl)cc23)cn1] | 5-chloro-1'-(2-{[2-(1-hydroxy-2-methylpropan-2-yl)pyrimidin-5-yl]oxy}ethyl)-1,2-dihydrospiro[indole-3,4'-piperidin]-2-one |
| 335 | 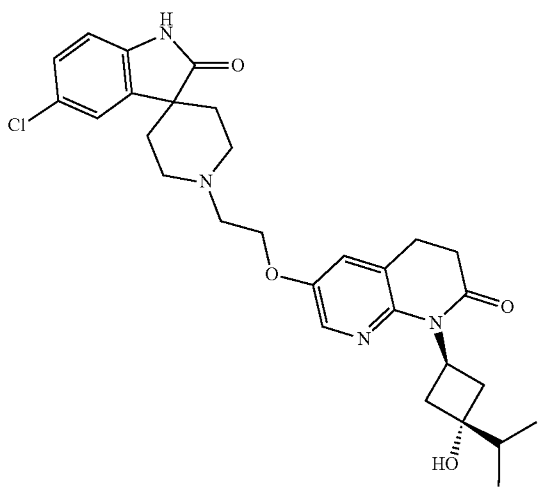 [SMILES: CC(C)[C@]1(O)C[C@H](N2C(=O)CCc3cc(OCCN4CCC5(CC4)C(=O)Nc4ccc(Cl)cc45)cnc32)C1] | 5-chloro-1'-[2-({7-oxo-8-[(trans)-3-hydroxy-3-(propan-2-yl)cyclobutyl]-5,6,7,8-tetrahydro-1,8-naphthyridin-3-yl}oxy)ethyl]-1,2-dihydrospiro[indole-3,4'-piperidin]-2-one |
| 336 | 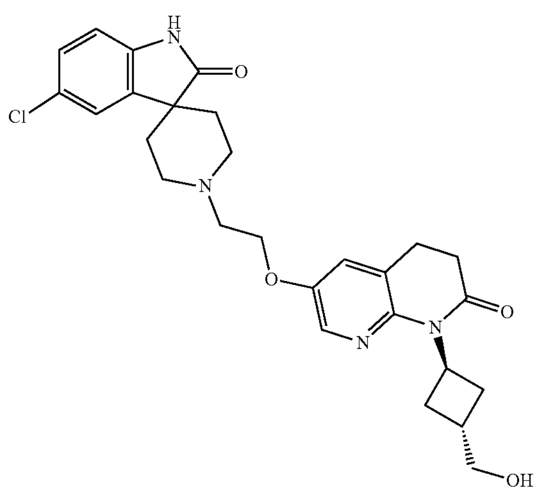 [SMILES: O=C1CCc2cc(OCCN3CCC4(CC3)C(=O)Nc3ccc(Cl)cc34)cnc2N1[C@H]1C[C@H](CO)C1] | 5-chloro-1'-[2-({7-oxo-8-[(trans)-3-(hydroxymethyl)cyclobutyl]-5,6,7,8-tetrahydro-1,8-naphthyridin-3-yl}oxy)ethyl]-1,2-dihydrospiro[indole-3,4'-piperidin]-2-one |

TABLE 1-continued

| Compound Number | Structure | Name |
|---|---|---|
| 338 | 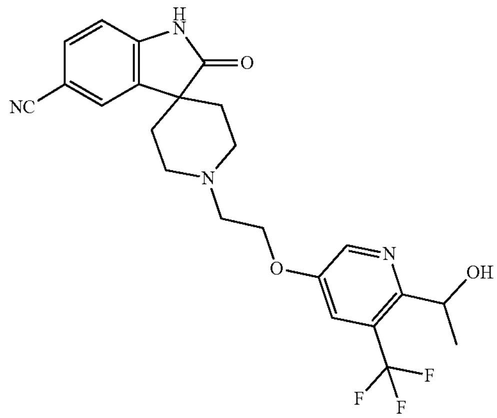 [SMILES: CC(O)c1ncc(OCCN2CCC3(CC2)C(=O)Nc2ccc(C#N)cc23)cc1C(F)(F)F] | 1'-(2-{[6-(1-hydroxyethyl)-5-(trifluoromethyl)pyridin-3-yl]oxy}ethyl)-2-oxo-1,2-dihydrospiro[indole-3,4'-piperidine]-5-carbonitrile |
| 339 | 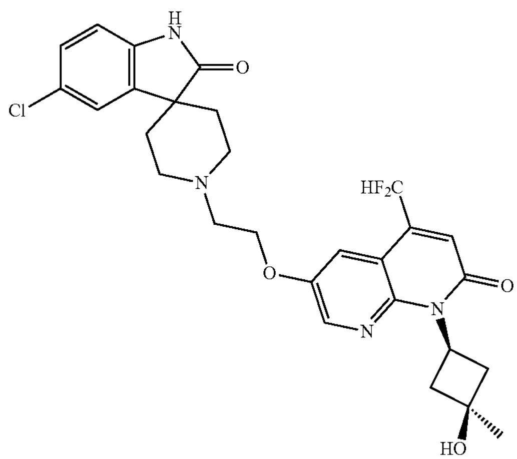 | 5-chloro-1'-(2-{[5-(difluoromethyl)-7-oxo-8-[(cis)-3-hydroxy-3-methylcyclobutyl]-7,8-dihydro-1,8-naphthyridin-3-yl]oxy}ethyl)-1,2-dihydrospiro[indole-3,4'-piperidin]-2-one |
| 340 | 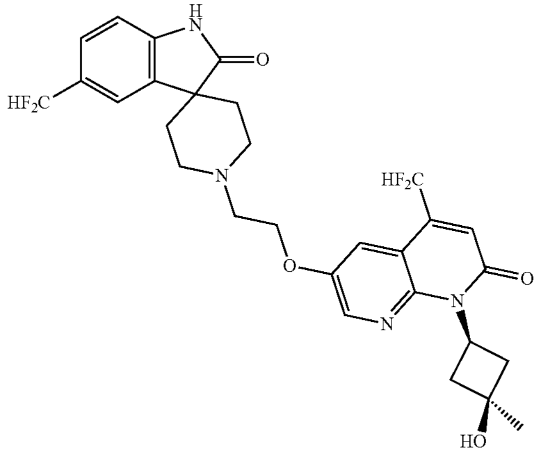 | 5-(difluoromethyl)-1'-(2-{[5-(difluoromethyl)-7-oxo-8-[(cis)-3-hydroxy-3-methylcyclobutyl]-7,8-dihydro-1,8-naphthyridin-3-yl]oxy}ethyl)-1,2-dihydrospiro[indole-3,4'-piperidin]-2-one |

TABLE 1-continued

| Compound Number | Structure | Name |
|---|---|---|
| 341 | 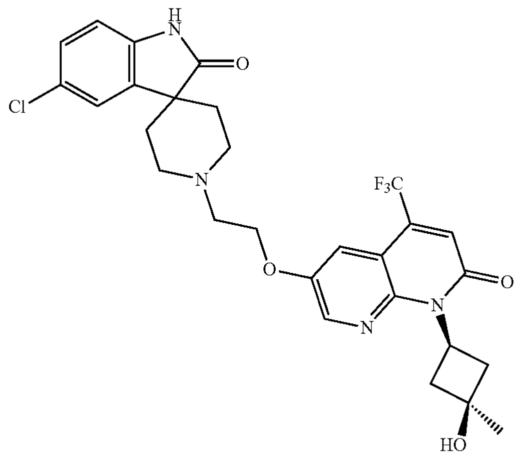 [SMILES: C[C@]1(O)C[C@@H](n2c(=O)cc(C(F)(F)F)c3cc(OCCN4CCC5(CC4)C(=O)Nc4ccc(Cl)cc45)cnc32)C1] | 5-chloro-1'-[2-({7-oxo-8-[(cis)-3-hydroxy-3-methylcyclobutyl]-5-(trifluoromethyl)-7,8-dihydro-1,8-naphthyridin-3-yl}oxy)ethyl]-1,2-dihydrospiro[indole-3,4'-piperidin]-2-one |
| 342 | 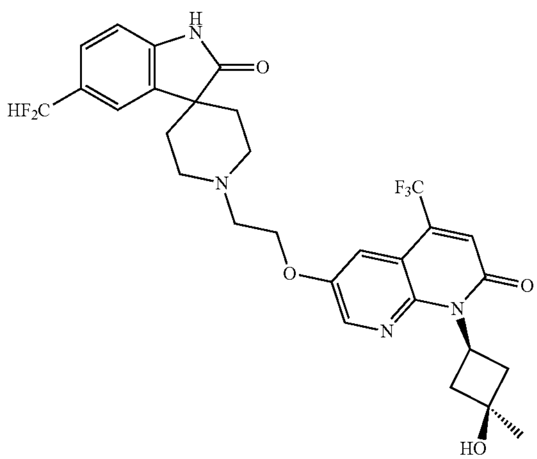 | 5-(difluoromethyl)-1'-[2-({7-oxo-8-[(cis)-3-hydroxy-3-methylcyclobutyl]-5-(trifluoromethyl)-7,8-dihydro-1,8-naphthyridin-3-yl}oxy)ethyl]-1,2-dihydrospiro[indole-3,4'-piperidin]-2-one |
| 343 | 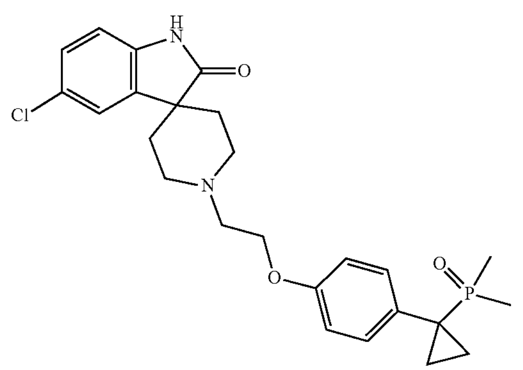 [SMILES: CP(C)(=O)C1(c2ccc(OCCN3CCC4(CC3)C(=O)Nc3ccc(Cl)cc34)cc2)CC1] | 5-chloro-1'-(2-{4-[1-(dimethylphosphoryl)cyclopropyl]phenoxy}ethyl)-1,2-dihydrospiro[indole-3,4'-piperidin]-2-one |

TABLE 1-continued

| Compound Number | Structure | Name |
|---|---|---|
| 344 | 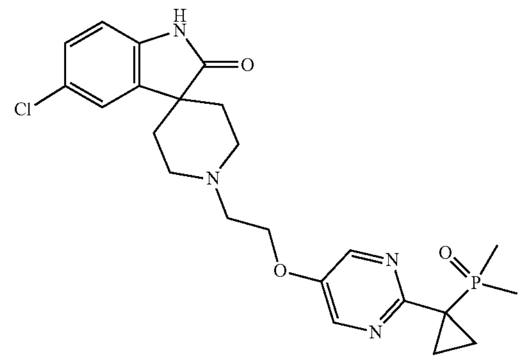 [SMILES: CP(C)(=O)C1(c2ncc(OCCN3CCC4(CC3)C(=O)Nc3ccc(Cl)cc34)cn2)CC1] | 5-chloro-1'-[2-({2-[1-(dimethylphosphoryl)cyclopropyl]pyrimidin-5-yl}oxy)ethyl]-1,2-dihydrospiro[indole-3,4'-piperidin]-2-one |
| 345 | 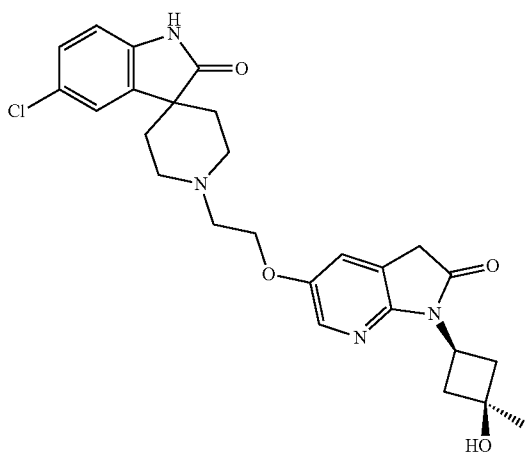 [SMILES: C[C@]1(O)C[C@@H](N2C(=O)Cc3cc(OCCN4CCC5(CC4)C(=O)Nc4ccc(Cl)cc45)cnc32)C1] | 5-chloro-1'-[2-({2-oxo-1-[(cis)-3-hydroxy-3-methylcyclobutyl]-1H,2H,3H-pyrrolo[2,3-b]pyridin-5-yl}oxy)ethyl]-1,2-dihydrospiro[indole-3,4'-piperidin]-2-one |
| 346 | 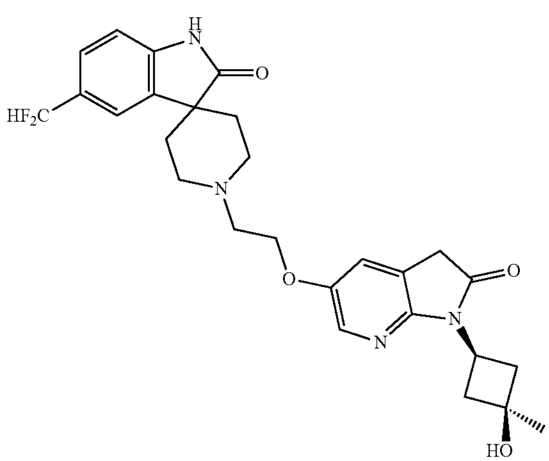 | 5-(difluoromethyl)-1'-[2-({2-oxo-1-[(cis)-3-hydroxy-3-methylcyclobutyl]-1H,2H,3H-pyrrolo[2,3-b]pyridin-5-yl]oxy)ethyl]-1,2-dihydrospiro[indole-3,4'-piperidin]-2-one |

TABLE 1-continued

| Compound Number | Structure | Name |
|---|---|---|
| 347 | 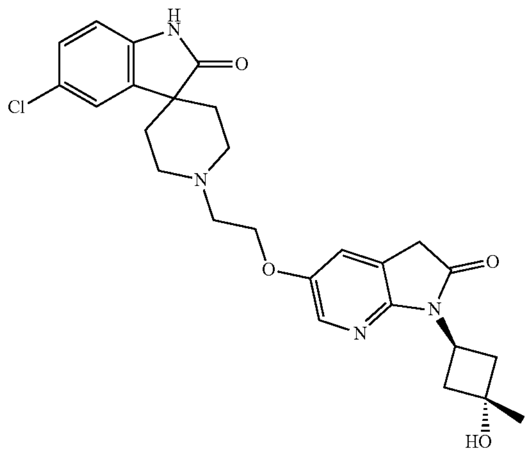 [SMILES: C[C@]1(O)C[C@H](N2C(=O)Cc3cc(OCCN4CCC5(CC4)C(=O)Nc4ccc(Cl)cc45)cnc32)C1] | 5-chloro-1'-[2-({2-oxo-1-[(trans)-3-hydroxy-3-methylcyclobutyl]-1H,2H,3H-pyrrolo[2,3-b]pyridin-5-yl}oxy)ethyl]-1,2-dihydrospiro[indole-3,4'-piperidin]-2-one |
| 348 | 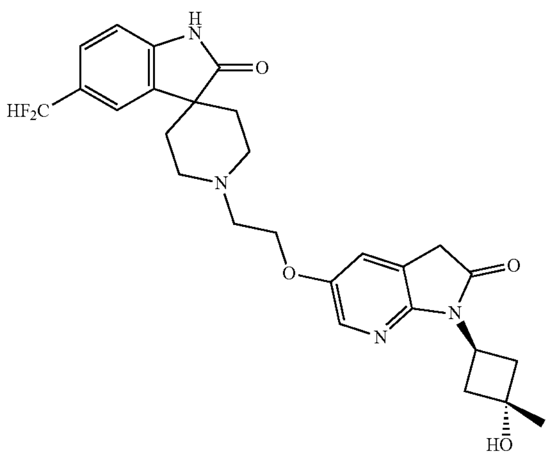 | 5-(difluoromethyl)-1'-[2-({2-oxo-1-[(trans)-3-hydroxy-3-methylcyclobutyl]-1H,2H,3H-pyrrolo[2,3-b]pyridin-5-yl}oxy)ethyl]-1,2-dihydrospiro[indole-3,4'-piperidin]-2-one |
| 349 | 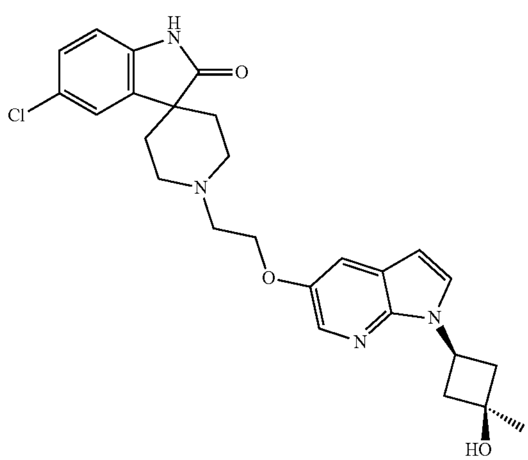 [SMILES: C[C@]1(O)C[C@@H](n2ccc3cc(OCCN4CCC5(CC4)C(=O)Nc4ccc(Cl)cc45)cnc32)C1] | 5-chloro-1'-[2-({1-[(cis)-3-hydroxy-3-methylcyclobutyl]-1H-pyrrolo[2,3-b]pyridin-5-yl}oxy)ethyl]-1,2-dihydrospiro[indole-3,4'-piperidin]-2-one |

TABLE 1-continued

| Compound Number | Structure | Name |
|---|---|---|
| 350 | 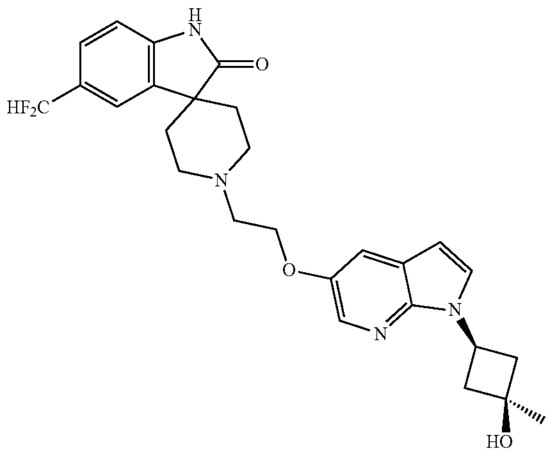 | 5-(difluoromethyl)-1'-[2-({1-[(cis)-3-hydroxy-3-methylcyclobutyl]-1H-pyrrolo[2,3-b]pyridin-5-yl}oxy)ethyl]-1,2-dihydrospiro[indole-3,4'-piperidin]-2-one |
| 351 | 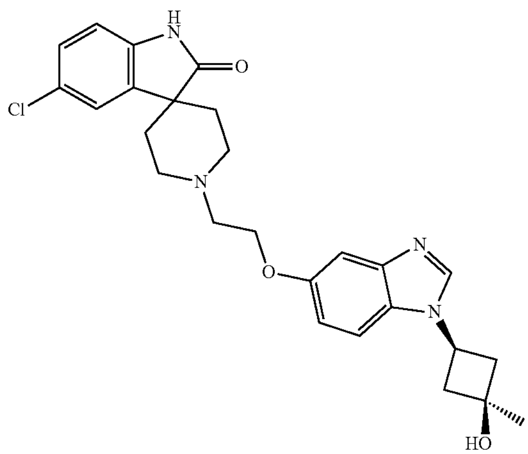 [SMILES: C[C@]1(O)C[C@@H](n2cnc3cc(OCCN4CCC5(CC4)C(=O)Nc4ccc(Cl)cc45)ccc32)C1] | 5-chloro-1'-[2-({1-[(cis)-3-hydroxy-3-methylcyclobutyl]-1H-1,3-benzodiazol-5-yl}oxy)ethyl]-1,2-dihydrospiro[indole-3,4'-piperidin]-2-one |
| 352 | 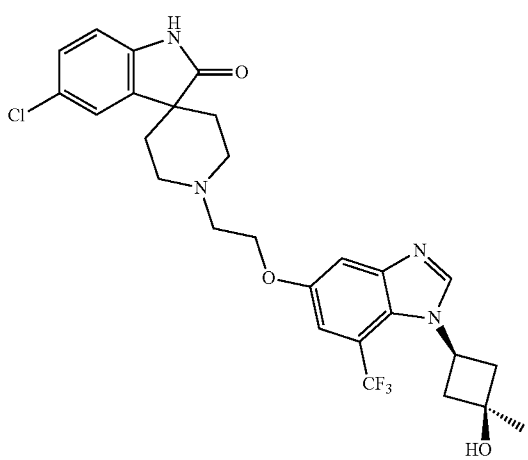 [SMILES: C[C@]1(O)C[C@@H](n2cnc3cc(OCCN4CCC5(CC4)C(=O)Nc4ccc(Cl)cc45)cc(C(F)(F)F)c32)C1] | 5-chloro-1'-[2-({1-[(cis)-3-hydroxy-3-methylcyclobutyl]-7-(trifluoromethyl)-1H-1,3-benzodiazol-5-yl}oxy)ethyl]-1,2-dihydrospiro[indole-3,4'-piperidin]-2-one |

TABLE 1-continued

| Compound Number | Structure | Name |
|---|---|---|
| 353 | 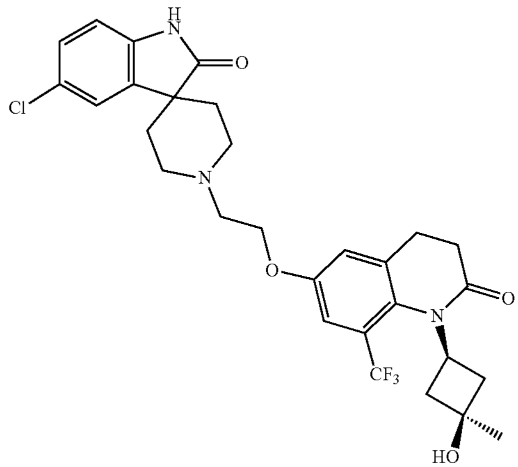 [SMILES: C[C@]1(O)C[C@@H](N2C(=O)CCc3cc(OCCN4CCC5(CC4)C(=O)Nc4ccc(Cl)cc45)cc(C(F)(F)F)c32)C1] | 5-chloro-1'-[2-({2-oxo-1-[(cis)-3-hydroxy-3-methylcyclobutyl]-8-(trifluoromethyl)-1,2,3,4-tetrahydroquinolin-6-yl}oxy)ethyl]-1,2-dihydrospiro[indole-3,4'-piperidin]-2-one |
| 354 | 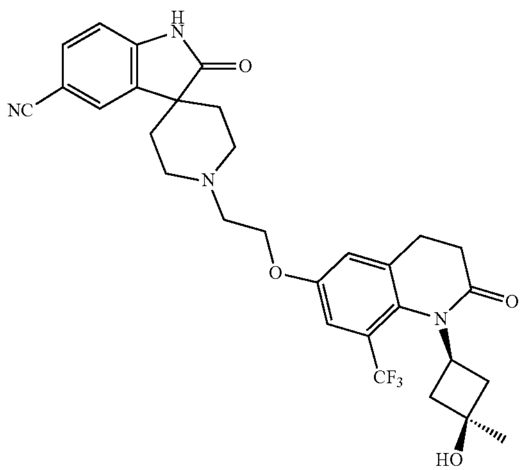 [SMILES: C[C@]1(O)C[C@@H](N2C(=O)CCc3cc(OCCN4CCC5(CC4)C(=O)Nc4ccc(C#N)cc45)cc(C(F)(F)F)c32)C1] | 2-oxo-1'-[2-({2-oxo-1-[(cis)-3-hydroxy-3-methylcyclobutyl]-8-(trifluoromethyl)-1,2,3,4-tetrahydroquinolin-6-yl}oxy)ethyl]-1,2-dihydrospiro[indole-3,4'-piperidine]-5-carbonitrile |
| 355 | 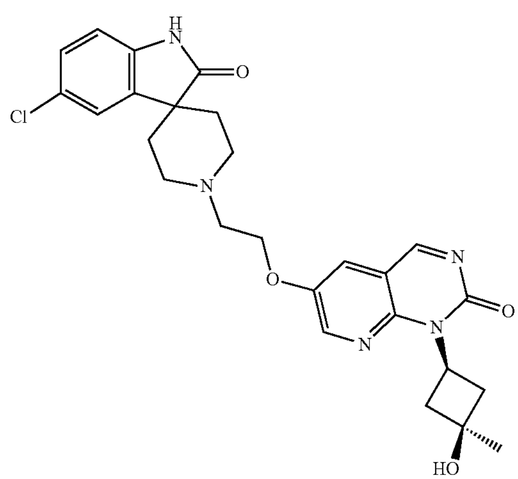 [SMILES: C[C@]1(O)C[C@@H](n2c(=O)ncc3cc(OCCN4CCC5(CC4)C(=O)Nc4ccc(Cl)cc45)cnc32)C1] | 5-chloro-1'-[2-({2-oxo-1-[(cis)-3-hydroxy-3-methylcyclobutyl]-1H,2H-pyrido[2,3-d]pyrimidin-6-yl}oxy)ethyl]-1,2-dihydrospiro[indole-3,4'-piperidin]-2-one |

TABLE 1-continued

| Compound Number | Structure | Name |
|---|---|---|
| 356 | 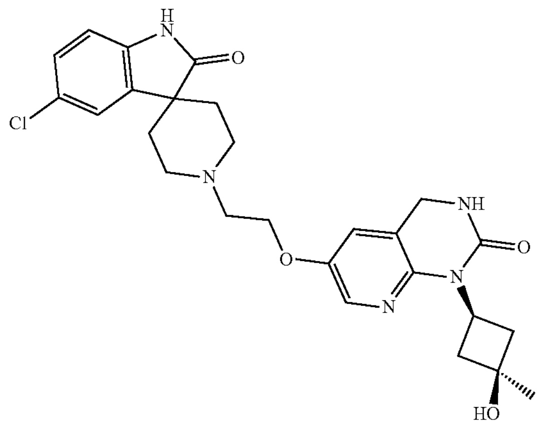 [SMILES: C[C@]1(O)C[C@@H](N2C(=O)NCc3cc(OCCN4CCC5(CC4)C(=O)Nc4ccc(Cl)cc45)cnc32)C1] | 5-chloro-1'-[2-({2-oxo-1-[(cis)-3-hydroxy-3-methylcyclobutyl]-1H,2H,3H,4H-pyrido[2,3-d]pyrimidin-6-yl}oxy)ethyl]-1,2-dihydrospiro[indole-3,4'-piperidin]-2-one |
| 357 | 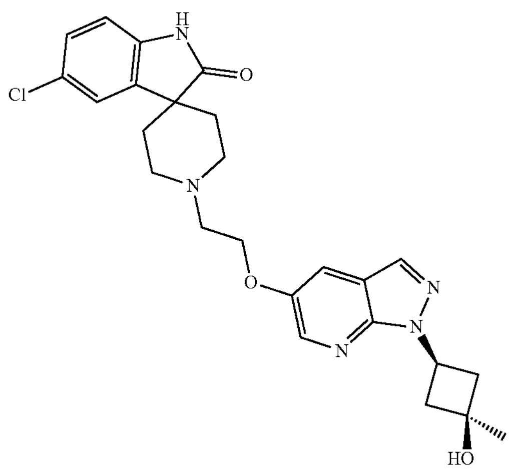 [SMILES: C[C@]1(O)C[C@@H](n2ncc3cc(OCCN4CCC5(CC4)C(=O)Nc4ccc(Cl)cc45)cnc32)C1] | 5-chloro-1'-[2-({1-[(cis)-3-hydroxy-3-methylcyclobutyl]-1H-pyrazolo[3,4-b]pyridin-5-yl}oxy)ethyl]-1,2-dihydrospiro[indole-3,4'-piperidin]-2-one |
| 358 | 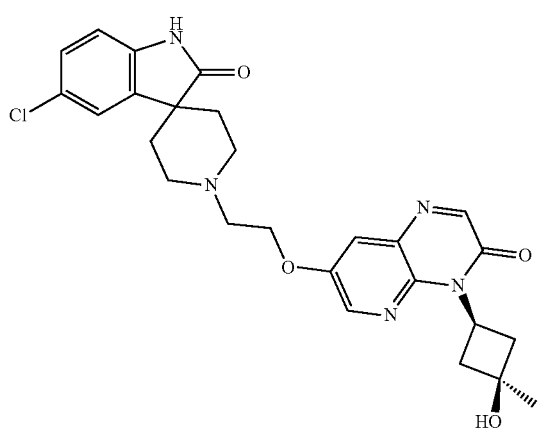 [SMILES: C[C@]1(O)C[C@@H](n2c(=O)cnc3cc(OCCN4CCC5(CC4)C(=O)Nc4ccc(Cl)cc45)cnc32)C1] | 5-chloro-1'-[2-({3-oxo-4-[(cis)-3-hydroxy-3-methylcyclobutyl]-3H,4H-pyrido[2,3-b]pyrazin-7-yl}oxy)ethyl]-1,2-dihydrospiro[indole-3,4'-piperidin]-2-one |

TABLE 1-continued

| Compound Number | Structure | Name |
|---|---|---|
| 359 | 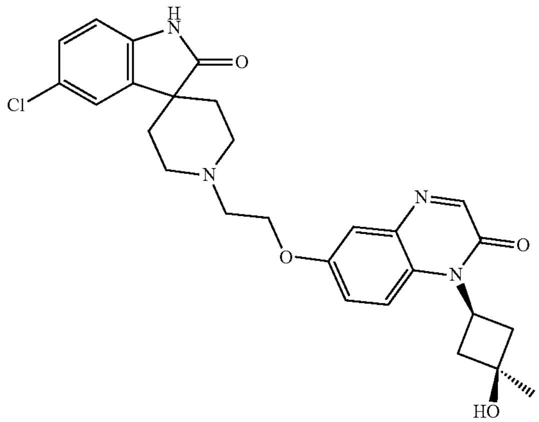 [SMILES: C[C@]1(O)C[C@@H](n2c(=O)cnc3cc(OCCN4CCC5(CC4)C(=O)Nc4ccc(Cl)cc45)ccc32)C1] | 5-chloro-1'-[2-({2-oxo-1-[(cis)-3-hydroxy-3-methylcyclobutyl]-1,2-dihydroquinoxalin-6-yl}oxy)ethyl]-1,2-dihydrospiro[indole-3,4'-piperidin]-2-one |
| 360 | 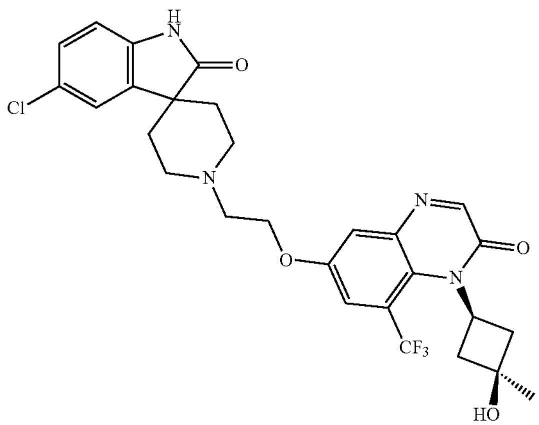 [SMILES: C[C@]1(O)C[C@@H](n2c(=O)cnc3cc(OCCN4CCC5(CC4)C(=O)Nc4ccc(Cl)cc45)cc(C(F)(F)F)c32)C1] | 5-chloro-1'-[2-({2-oxo-1-[(cis)-3-hydroxy-3-methylcyclobutyl]-8-(trifluoromethyl)-1,2-dihydroquinoxalin-6-yl]oxy)ethyl]-1,2-dihydrospiro[indole-3,4'-piperidin]-2-one |
| 361 | 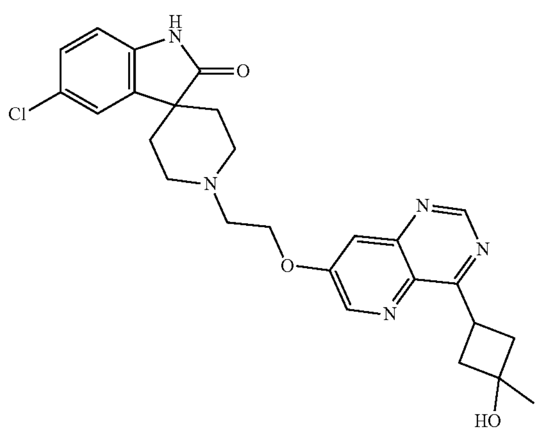 | 5-chloro-1'-(2-{[4-(3-hydroxy-3-methylcyclobutyl)pyrido[3,2-d]pyrimidin-7-yl]oxy}ethyl)-1,2-dihydrospiro[indole-3,4'-piperidin]-2-one |

| Compound Number | Structure | Name |
|---|---|---|
| 362 | 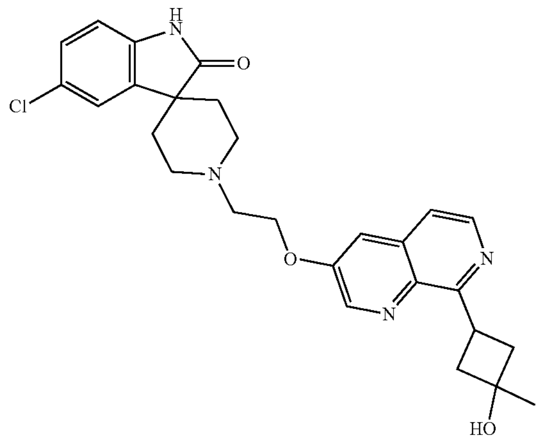 | 5-chloro-1'-(2-{[8-(3-hydroxy-3-methylcyclobutyl)-1,7-naphthyridin-3-yl]oxy}ethyl)-1,2-dihydrospiro[indole-3,4'-piperidin]-2-one |
| 363 | 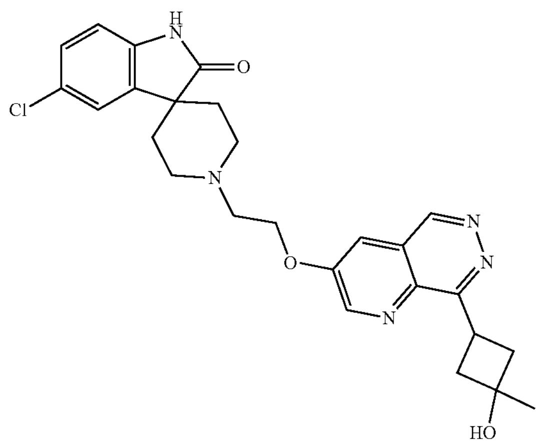 [SMILES: CC1(O)CC(c2nncc3cc(OCCN4CCC5(CC4)C(=O)Nc4ccc(Cl)cc45)cnc23)C1] | 5-chloro-1'-(2-{[8-(3-hydroxy-3-methylazetidin-1-yl)pyrido[2,3-d]pyridazin-3-yl]oxy}ethyl)-1,2-dihydrospiro[indole-3,4'-piperidin]-2-one |
| 364 | 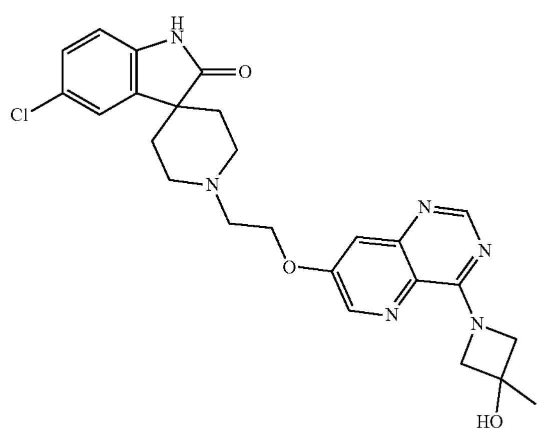 [SMILES: CC1(O)CN(c2ncnc3cc(OCCN4CCC5(CC4)C(=O)Nc4ccc(Cl)cc45)cnc23)C1] | 5-chloro-1'-(2-{[4-(3-hydroxy-3-methylazetidin-1-yl)pyrido[3,2-d]pyrimidin-7-yl]oxy}ethyl)-1,2-dihydrospiro[indole-3,4'-piperidin]-2-one |

| Compound Number | Structure | Name |
|---|---|---|
| 365 | 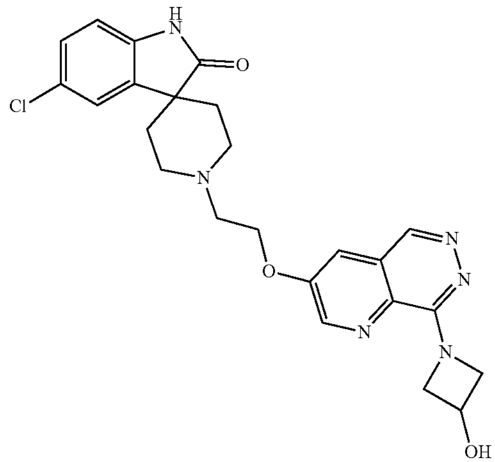 [SMILES: O=C1Nc2ccc(Cl)cc2C12CCN(CCOc1cnc3c(N4CC(O)C4)nncc3c1)CC2] | 5-chloro-1'-(2-{[8-(3-hydroxyazetidin-1-yl)pyrido[2,3-d]pyridazin-3-yl]oxy}ethyl)-1,2-dihydrospiro[indole-3,4'-piperidin]-2-one |
| 366 | 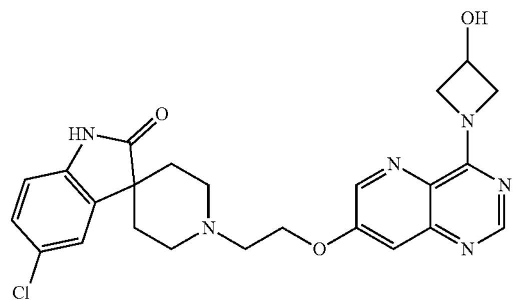 [SMILES: O=C1Nc2ccc(Cl)cc2C12CCN(CCOc1cnc3c(N4CC(O)C4)ncnc3c1)CC2] | 5-chloro-1'-(2-{[4-(3-hydroxyazetidin-1-yl)pyrido[3,2-d]pyrimidin-7-yl]oxy}ethyl)-1,2-dihydrospiro[indole-3,4'-piperidin]-2-one |
| 367 | 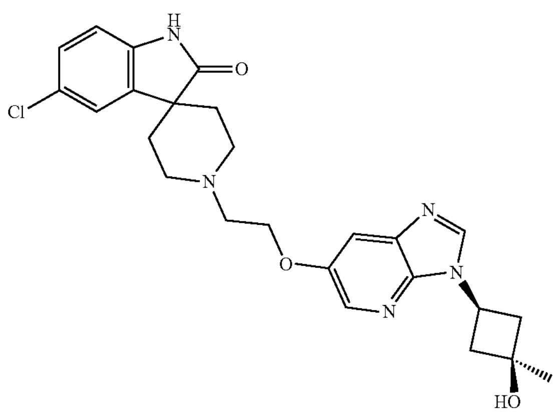 [SMILES: C[C@]1(O)C[C@@H](n2cnc3cc(OCCN4CCC5(CC4)C(=O)Nc4ccc(Cl)cc45)cnc32)C1] | 5-chloro-1'-[2-((3-[(cis)-3-hydroxy-3-methylcyclobutyl]-3H-imidazo[4,5-b]pyridin-6-yl}oxy)ethyl]-1,2-dihydrospiro[indole-3,4'-piperidin]-2-one |
| 368 | 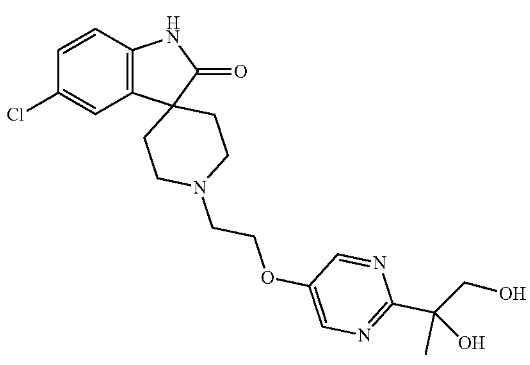 [SMILES: CC(O)(CO)c1ncc(OCCN2CCC3(CC2)C(=O)Nc2ccc(Cl)cc23)cn1] | 5-chloro-1'-(2-{[2-(1,2-dihydroxypropan-2-yl)pyrimidin-5-yl]oxy}ethyl)-1,2-dihydrospiro[indole-3,4'-piperidin]-2-one |

| Compound Number | Structure | Name |
|---|---|---|
| 369 | 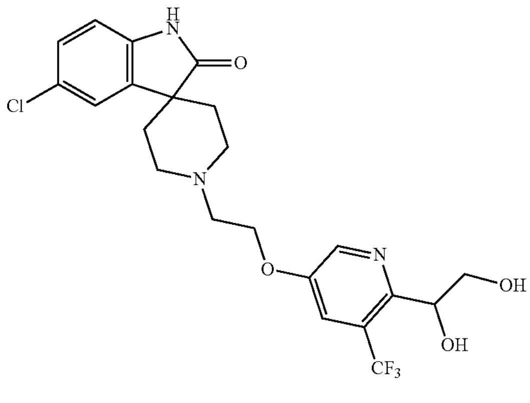 [SMILES: O=C1Nc2ccc(Cl)cc2C12CCN(CCOc1cnc(C(O)CO)c(C(F)(F)F)c1)CC2] | 5-chloro-1'-(2-((6-(1,2-dihydroxyethyl)-5-(trifluoromethyl)pyridin-3-yl)oxy)ethyl)spiro[indoline-3,4'-piperidin]-2-one |
| 370 | 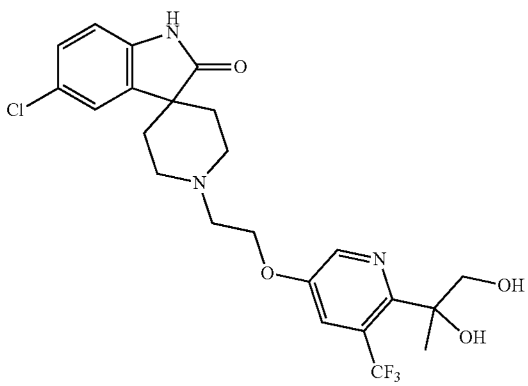 [SMILES: CC(O)(CO)c1ncc(OCCN2CCC3(CC2)C(=O)Nc2ccc(Cl)cc23)cc1C(F)(F)F] | 5-chloro-1'-(2-{[6-(1,2-dihydroxypropan-2-yl)-5-(trifluoromethyl)pyridin-3-yl]oxy}ethyl)-1,2-dihydrospiro[indole-3,4'-piperidin]-2-one |
| 371 | 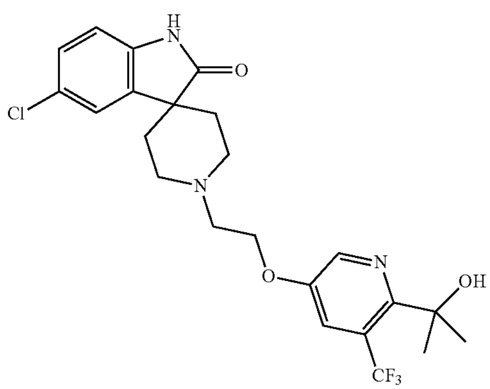 [SMILES: CC(C)(O)c1ncc(OCCN2CCC3(CC2)C(=O)Nc2ccc(Cl)cc23)cc1C(F)(F)F] | 5-chloro-1'-(2-{[6-(2-hydroxypropan-2-yl)-5-(trifluoromethyl)pyridin-3-yl]oxy}ethyl)-1,2-dihydrospiro[indole-3,4'-piperidin]-2-one |
| 372 | 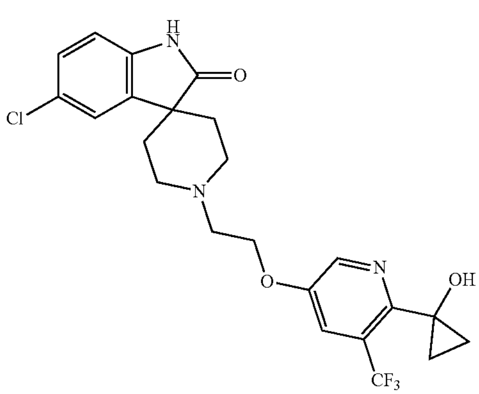 [SMILES: O=C1Nc2ccc(Cl)cc2C12CCN(CCOc1cnc(C3(O)CC3)c(C(F)(F)F)c1)CC2] | 5-chloro-1'-(2-{[6-(1-hydroxycyclopropyl)-5-(trifluoromethyl)pyridin-3-yl]oxy}ethyl)-1,2-dihydrospiro[indole-3,4'-piperidin]-2-one |

TABLE 1-continued

| Compound Number | Structure | Name |
|---|---|---|
| 373 | 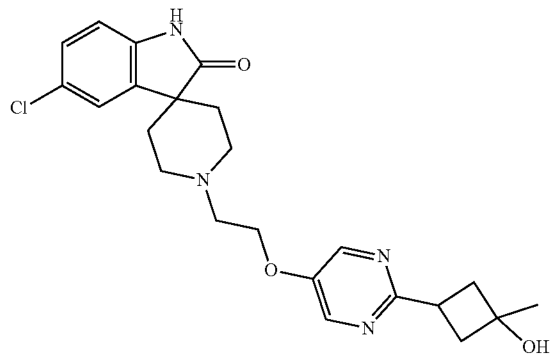 | 5-chloro-1'-(2-{[2-(3-hydroxy-3-methylcyclobutyl)pyrimidin-5-yl]oxy}ethyl)-1,2-dihydrospiro[indole-3,4'-piperidin]-2-one |
| 374 | 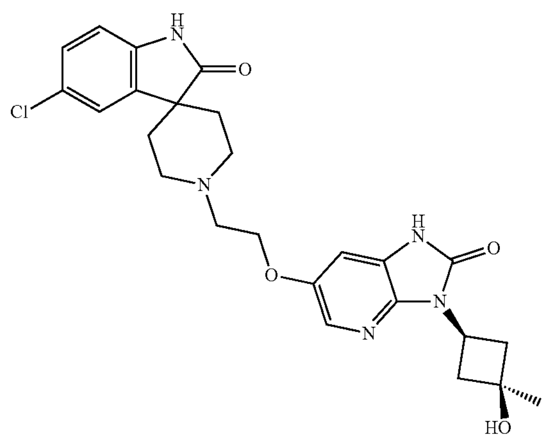 [SMILES: C[C@]1(O)C[C@@H](n2c(=O)[nH]c3cc(OCCN4CCC5(CC4)C(=O)Nc4ccc(Cl)cc45)cnc32)C1] | 5-chloro-1'-[2-({2-oxo-3-[(cis)-3-hydroxy-3-methylcyclobutyl]-1H,2H,3H-imidazo[4,5-b]pyridin-6-yl}oxy)ethyl]-1,2-dihydrospiro[indole-3,4'-piperidin]-2-one |
| 375 | 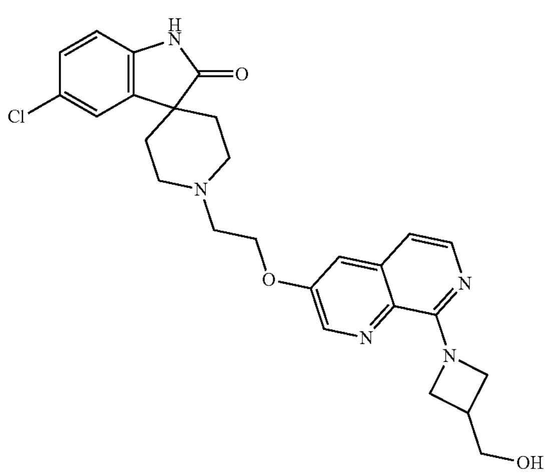 [SMILES: O=C1Nc2ccc(Cl)cc2C12CCN(CCOc1cnc3c(N4CC(CO)C4)nccc3c1)CC2] | 5-chloro-1'-[2-((8-[3-(hydroxymethyl)azetidin-1-yl]-1,7-naphthyridin-3-yl}oxy)ethyl]-1,2-dihydrospiro[indole-3,4'-piperidin]-2-one |

TABLE 1-continued

| Compound Number | Structure | Name |
|---|---|---|
| 376 | 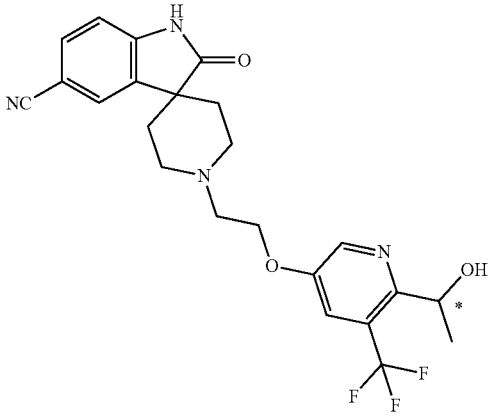 [SMILES: CC(O)c1ncc(OCCN2CCC3(CC2)C(=O)Nc2ccc(C#N)cc23)cc1C(F)(F)F] | 1'-[2-({6-[(1S) or (1R)-1-hydroxyethyl]-5-(trifluoromethyl)pyridin-3-yl}oxy)ethyl]-2-oxo-1,2-dihydrospiro[indole-3,4'-piperidine]-5-carbonitrile |
| 377 | 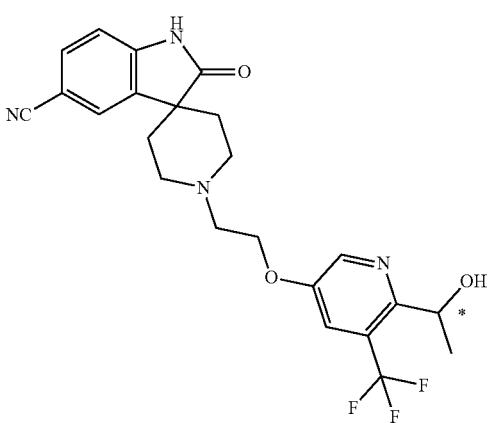 [SMILES: CC(O)c1ncc(OCCN2CCC3(CC2)C(=O)Nc2ccc(C#N)cc23)cc1C(F)(F)F] | 1'-[2-({6-[(1R) or (1S)-1-hydroxyethyl]-5-(trifluoromethyl)pyridin-3-yl}oxy)ethyl]-2-oxo-1,2-dihydrospiro[indole-3,4'-piperidine]-5-carbonitrile |
| 378 | 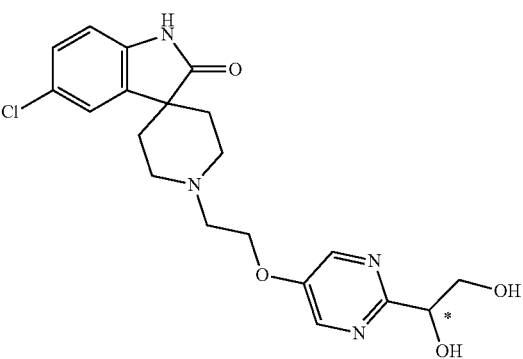 [SMILES: O=C1Nc2ccc(Cl)cc2C12CCN(CCOc1cnc(C(O)CO)nc1)CC2] | 5-chloro-1'-[2-({2-[(1S) or (1R)-1,2-dihydroxyethyl]pyrimidin-5-yl}oxy)ethyl]-1,2-dihydrospiro[indole-3,4'-piperidin]-2-one |
| 379 | 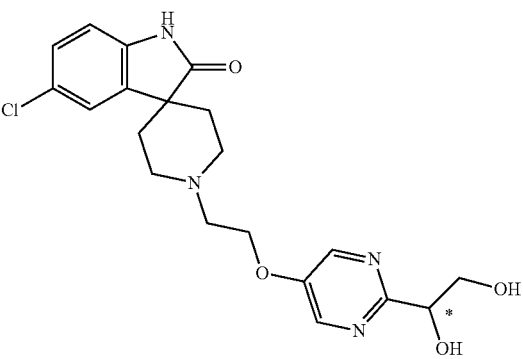 [SMILES: O=C1Nc2ccc(Cl)cc2C12CCN(CCOc1cnc(C(O)CO)nc1)CC2] | 5-chloro-1'-[2-((2-[(1R) or (1S)-1,2-dihydroxyethyl]pyrimidin-5-yl}oxy)ethyl]-1,2-dihydrospiro[indole-3,4'-piperidin]-2-one |

TABLE 1-continued

| Compound Number | Structure | Name |
|---|---|---|
| 380 | 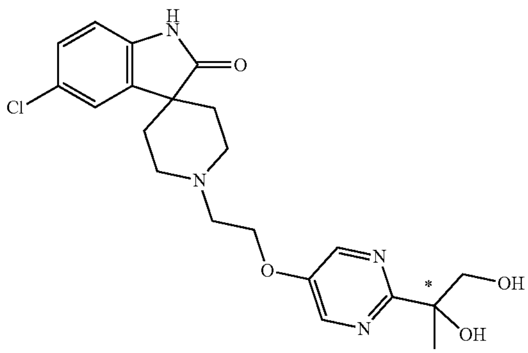 [SMILES: CC(O)(CO)c1ncc(OCCN2CCC3(CC2)C(=O)Nc2ccc(Cl)cc23)cn1] | 5-chloro-1'-[2-({2-[(2S) or (2R)-1,2-dihydroxypropan-2-yl]pyrimidin-5-yl}oxy)ethyl]-1,2-dihydrospiro[indole-3,4'-piperidin]-2-one |
| 381 | 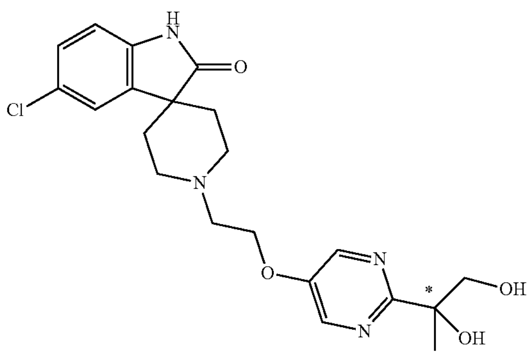 [SMILES: CC(O)(CO)c1ncc(OCCN2CCC3(CC2)C(=O)Nc2ccc(Cl)cc23)cn1] | 5-chloro-1'-[2-({2-[(2R) or (2S)-1,2-dihydroxypropan-2-yl]pyrimidin-5-yl}oxy)ethyl]-1,2-dihydrospiro[indole-3,4'-piperidin]-2-one |
| 382 | 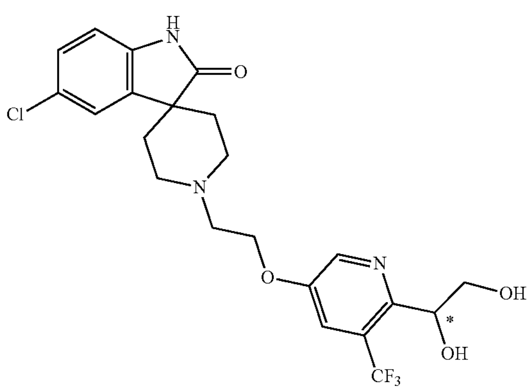 [SMILES: O=C1Nc2ccc(Cl)cc2C12CCN(CCOc1cnc(C(O)CO)c(C(F)(F)F)c1)CC2] | 5-chloro-1'-[2-({6-[(1S) or (1R)-1,2-dihydroxyethyl]-5-(trifluoromethyl)pyridin-3-yl}oxy)ethyl]-1,2-dihydrospiro[indole-3,4'-piperidin]-2-one |
| 383 | 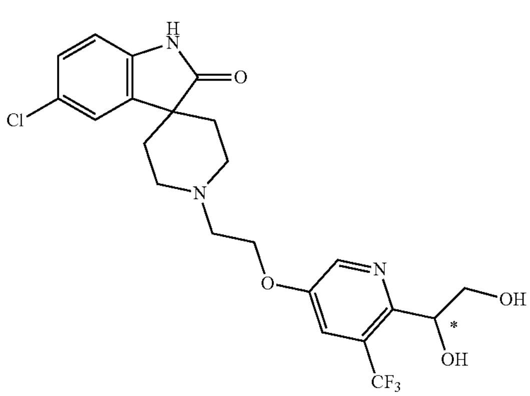 [SMILES: O=C1Nc2ccc(Cl)cc2C12CCN(CCOc1cnc(C(O)CO)c(C(F)(F)F)c1)CC2] | 5-chloro-1'-[2-({6-[(1R) or (1S)-1,2-dihydroxyethyl]-5-(trifluoromethyl)pyridin-3-yl}oxy)ethyl]-1,2-dihydrospiro[indole-3,4'-piperidin]-2-one |

TABLE 1-continued

| Compound Number | Structure | Name |
| --- | --- | --- |
| 384 | 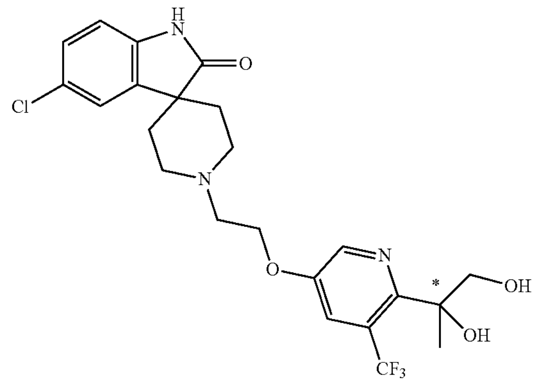 [SMILES: CC(O)(CO)c1ncc(OCCN2CCC3(CC2)C(=O)Nc2ccc(Cl)cc23)cc1C(F)(F)F] | 5-chloro-1'-[2-({6-[(2S) or (2R)-1,2-dihydroxypropan-2-yl]-5-(trifluoromethyl)pyridin-3-yl]oxy)ethyl]-1,2-dihydrospiro[indole-3,4'-piperidin]-2-one |
| 385 | 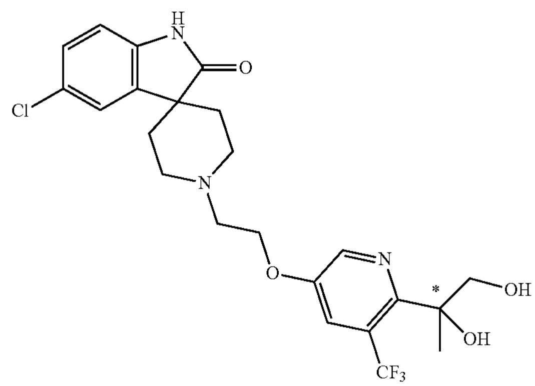 [SMILES: CC(O)(CO)c1ncc(OCCN2CCC3(CC2)C(=O)Nc2ccc(Cl)cc23)cc1C(F)(F)F] | 5-chloro-1'-[2-({6-[(2R) or (2S)-1,2-dihydroxypropan-2-yl]-5-(trifluoromethyl)pyridin-3-yl}oxy)ethyl]-1,2-dihydrospiro[indole-3,4'-piperidin]-2-one |
| 386 | 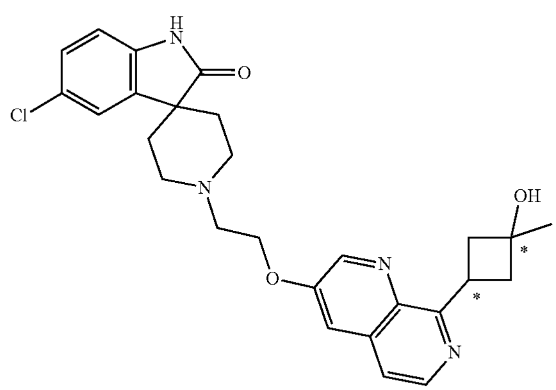 [SMILES: CC1(O)CC(c2nccc3cc(OCCN4CCC5(CC4)C(=O)Nc4ccc(Cl)cc45)cnc23)C1] | 5-chloro-1'-[2-({8-[(cis) or (trans)-3-hydroxy-3-methylcyclobutyl]-1,7-naphthyridin-3-yl}oxy)ethyl]-1,2-dihydrospiro[indole-3,4'-piperidin]-2-one |
| 387 | 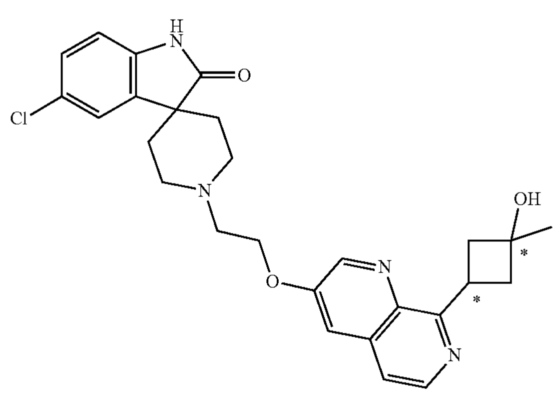 [SMILES: CC1(O)CC(c2nccc3cc(OCCN4CCC5(CC4)C(=O)Nc4ccc(Cl)cc45)cnc23)C1] | 5-chloro-1'-[2-({8-[(trans) or (cis)-3-hydroxy-3-methylcyclobutyl]-1,7-naphthyridin-3-yl}oxy)ethyl]-1,2-dihydrospiro[indole-3,4'-piperidin]-2-one |

TABLE 1-continued

| Compound Number | Structure | Name |
|---|---|---|
| 388 | 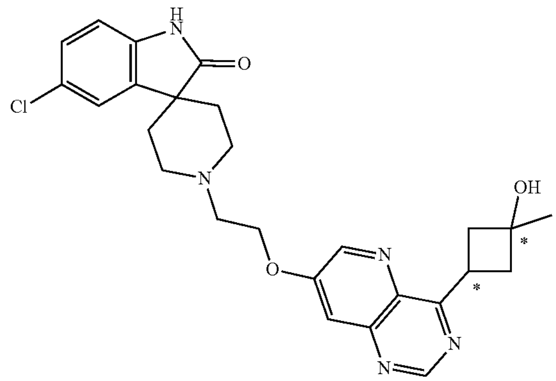 [SMILES: CC1(O)CC(c2ncnc3cc(OCCN4CCC5(CC4)C(=O)Nc4ccc(Cl)cc45)cnc23)C1] | 5-chloro-1'-[2-({4-[(cis) or (trans)-3-hydroxy-3-methylcyclobutyl]pyrido[3,2-d]pyrimidin-7-yl}oxy)ethyl]-1,2-dihydrospiro[indole-3,4'-piperidin]-2-one |
| 389 | 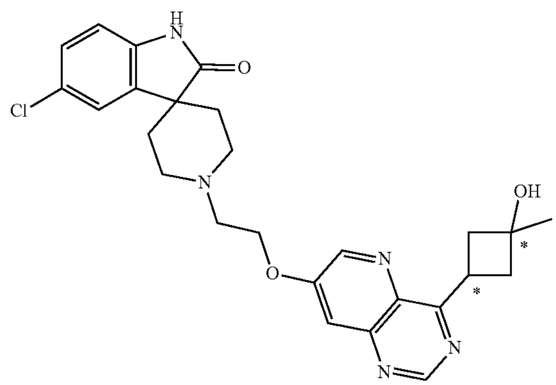 [SMILES: CC1(O)CC(c2ncnc3cc(OCCN4CCC5(CC4)C(=O)Nc4ccc(Cl)cc45)cnc23)C1] | 5-chloro-1'-[2-({4-[(trans) or (cis)-3-hydroxy-3-methylcyclobutyl]pyrido[3,2-d]pyrimidin-7-yl}oxy)ethyl]-1,2-dihydrospiro[indole-3,4'-piperidin]-2-one |
| 390 | 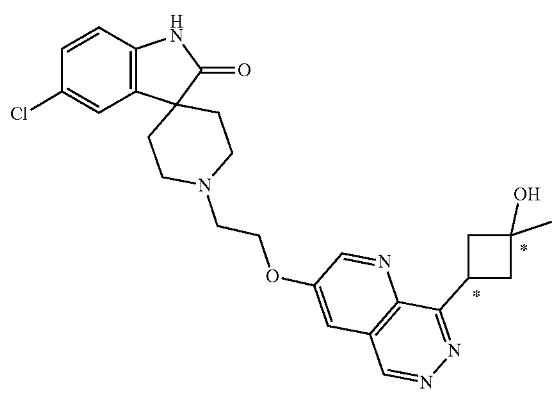 [SMILES: CC1(O)CC(c2nncc3cc(OCCN4CCC5(CC4)C(=O)Nc4ccc(Cl)cc45)cnc23)C1] | 5-chloro-1'-[2-({8-[(cis) or (trans)-3-hydroxy-3-methylcyclobutyl]pyrido[2,3-d]pyridazin-3-yl}oxy)ethyl]-1,2-dihydrospiro[indole-3,4'-piperidin]-2-one |
| 391 | 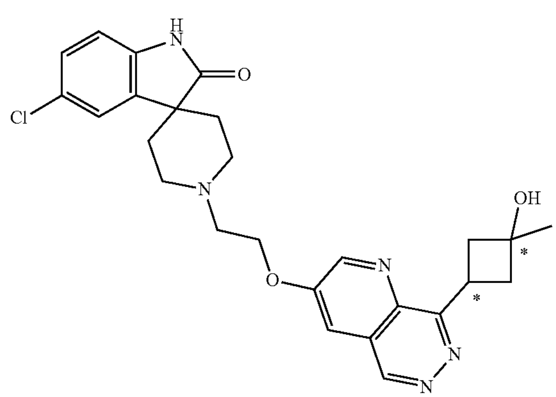 [SMILES: CC1(O)CC(c2nncc3cc(OCCN4CCC5(CC4)C(=O)Nc4ccc(Cl)cc45)cnc23)C1] | 5-chloro-1'-[2-({8-[(trans) or (cis)-3-hydroxy-3-methylcyclobutyl]pyrido[2,3-d]pyridazin-3-yl}oxy)ethyl]-1,2-dihydrospiro[indole-3,4'-piperidin]-2-one |

TABLE 1-continued

| Compound Number | Structure | Name |
|---|---|---|
| 392 | 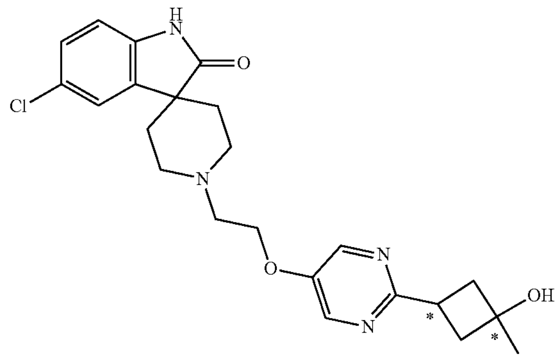 [SMILES: CC1(O)CC(c2ncc(OCCN3CCC4(CC3)C(=O)Nc3ccc(Cl)cc34)cn2)C1] | 5-chloro-1'-[2-({2-[(cis) or (trans)-3-hydroxy-3-methylcyclobutyl]pyrimidin-5-yl}oxy)ethyl]-1,2-dihydrospiro[indole-3,4'-piperidin]-2-one |
| 393 | 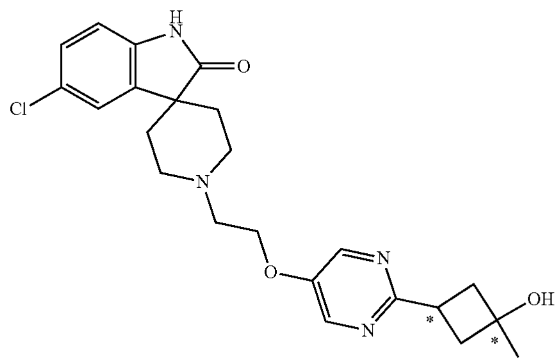 [SMILES: CC1(O)CC(c2ncc(OCCN3CCC4(CC3)C(=O)Nc3ccc(Cl)cc34)cn2)C1] | 5-chloro-1'-[2-({2-[(trans) or (cis)-3-hydroxy-3-methylcyclobutyl]pyrimidin-5-yl}oxy)ethyl]-1,2-dihydrospiro[indole-3,4'-piperidin]-2-one |
| 394 | 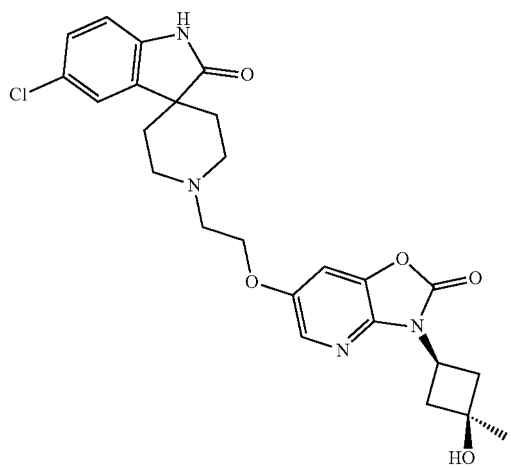 [SMILES: C[C@]1(O)C[C@@H](n2c(=O)oc3cc(OCCN4CCC5(CC4)C(=O)Nc4ccc(Cl)cc45)cnc32)C1] | 5-chloro-1'-[2-({2-oxo-3-[(cis)-3-hydroxy-3-methylcyclobutyl]-2H,3H-[1,3]oxazolo[4,5-b]pyridin-6-yl}oxy)ethyl]-1,2-dihydrospiro[indole-3,4'-piperidin]-2-one |
| 395 | 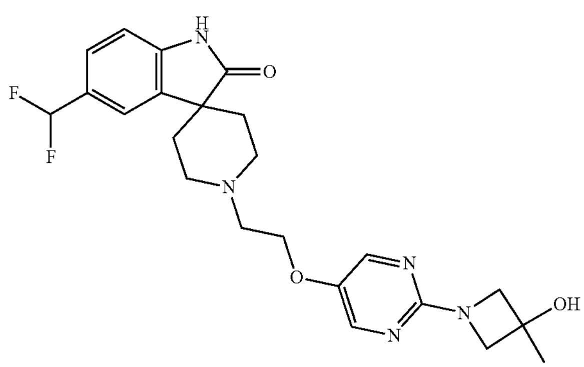 [SMILES: CC1(O)CN(c2ncc(OCCN3CCC4(CC3)C(=O)Nc3ccc(C(F)F)cc34)cn2)C1] | 5-(difluoromethyl)-1'-(2-{[2-(3-hydroxy-3-methylazetidin-1-yl)pyrimidin-5-yl]oxy}ethyl)-1,2-dihydrospiro[indole-3,4'-piperidin]-2-one |

TABLE 1-continued

| Compound Number | Structure | Name |
|---|---|---|
| 396 | 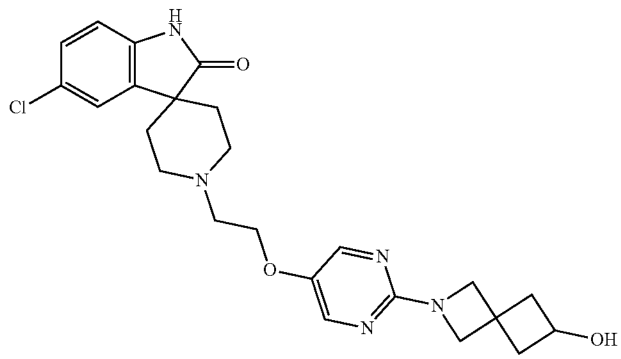 [SMILES: O=C1Nc2ccc(Cl)cc2C12CCN(CCOc1cnc(N3CC4(CC(O)C4)C3)nc1)CC2] | 5-chloro-1'-{2-[(2-{6-hydroxy-2-azaspiro[3.3]heptan-2-yl}pyrimidin-5-yl)oxy]ethyl}-1,2-dihydrospiro[indole-3,4'-piperidin]-2-one |
| 397 | 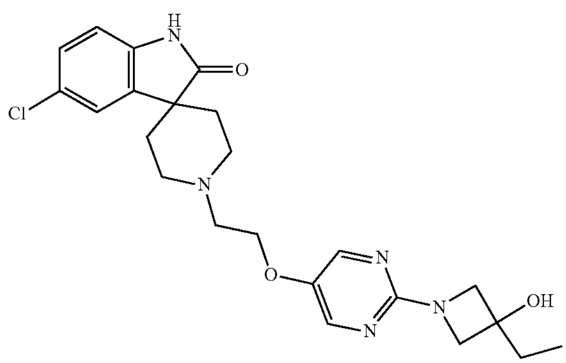 [SMILES: CCC1(O)CN(c2ncc(OCCN3CCC4(CC3)C(=O)Nc3ccc(Cl)cc34)cn2)C1] | 5-chloro-1'-(2-{[2-(3-ethyl-3-hydroxyazetidin-1-yl)pyrimidin-5-yl]oxy}ethyl)-1,2-dihydrospiro[indole-3,4'-piperidin]-2-one |
| 398 | 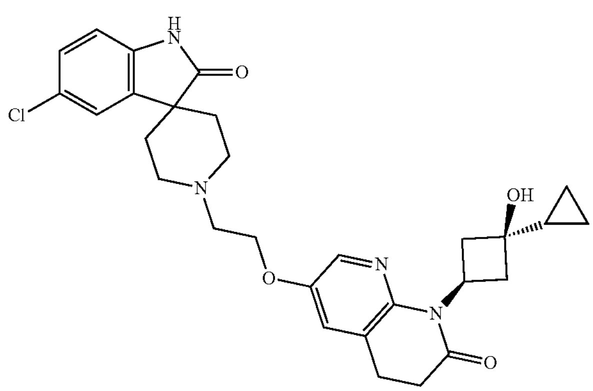 [SMILES: O=C1CCc2cc(OCCN3CCC4(CC3)C(=O)Nc3ccc(Cl)cc34)cnc2N1[C@H]1C[C@](O)(C2CC2)C1] | 5-chloro-1'-[2-({7-oxo-8-[(cis)-3-cyclopropyl-3-hydroxycyclobutyl]-5,6,7,8-tetrahydro-1,8-naphthyridin-3-yl}oxy)ethyl]-1,2-dihydrospiro[indole-3,4'-piperidin]-2-one |
| 399 | 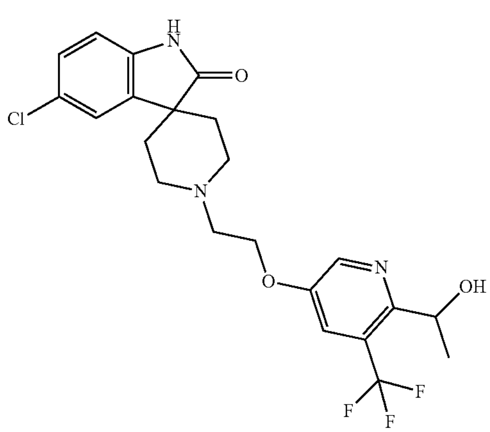 [SMILES: CC(O)c1ncc(OCCN2CCC3(CC2)C(=O)Nc2ccc(Cl)cc23)cc1C(F)(F)F] | 5-chloro-1'-(2-{[6-(1-hydroxyethyl)-5-(trifluoromethyl)pyridin-3-yl]oxy}ethyl)-1,2-dihydrospiro[indole-3,4'-piperidin]-2-one |

TABLE 1-continued

| Compound Number | Structure | Name |
|---|---|---|
| 400 | 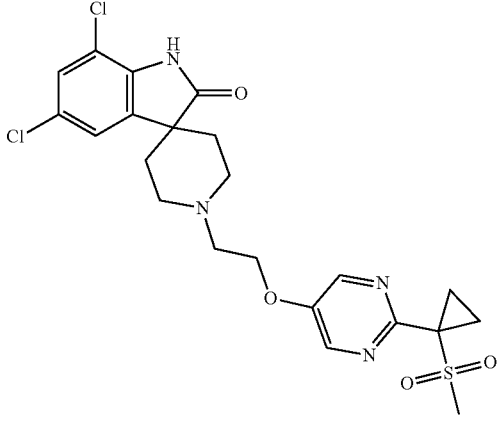 [SMILES: CS(=O)(=O)C1(c2ncc(OCCN3CCC4(CC3)C(=O)Nc3c(Cl)cc(Cl)cc34)cn2)CC1] | 5,7-dichloro-1'-(2-{[2-(1-methanesulfonylcyclopropyl)pyrimidin-5-yl]oxy}ethyl)-1,2-dihydrospiro[indole-3,4'-piperidin]-2-one |
| 401 | 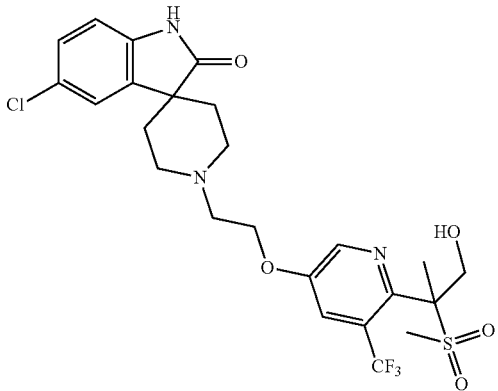 [SMILES: CC(CO)(c1ncc(OCCN2CCC3(CC2)C(=O)Nc2ccc(Cl)cc23)cc1C(F)(F)F)S(C)(=O)=O] | 5-chloro-1'-(2-{[6-(1-hydroxy-2-methanesulfonylpropan-2-yl)-5-(trifluoromethyl)pyridin-3-yl]oxy}ethyl)-1,2-dihydrospiro[indole-3,4'-piperidin]-2-one |
| 402 | 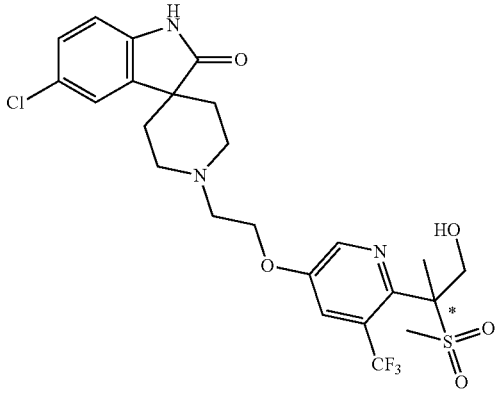 [SMILES: CC(CO)(c1ncc(OCCN2CCC3(CC2)C(=O)Nc2ccc(Cl)cc23)cc1C(F)(F)F)S(C)(=O)=O] | 5-chloro-1'-[2-({6-[(2S or 2R)-1-hydroxy-2-methanesulfonylpropan-2-yl]-5-(trifluoromethyl)pyridin-3-yl}oxy)ethyl]-1,2-dihydrospiro[indole-3,4'-piperidin]-2-one |

TABLE 1-continued

| Compound Number | Structure | Name |
| --- | --- | --- |
| 403 | 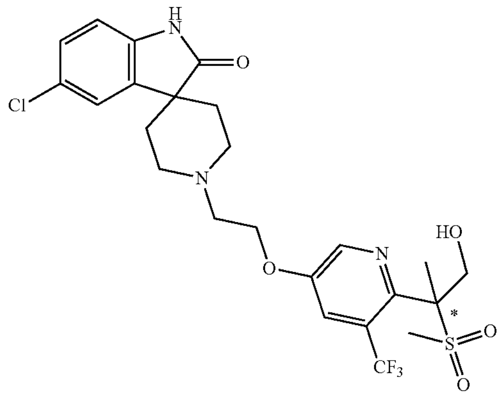 [SMILES: CC(CO)(c1ncc(OCCN2CCC3(CC2)C(=O)Nc2ccc(Cl)cc23)cc1C(F)(F)F)S(C)(=O)=O] | 5-chloro-1'-[2-({6-[(2R or 2S)-1-hydroxy-2-methanesulfonylpropan-2-yl]-5-(trifluoromethyl)pyridin-3-yl}oxy)ethyl]-1,2-dihydrospiro[indole-3,4'-piperidin]-2-one |
| 404 | 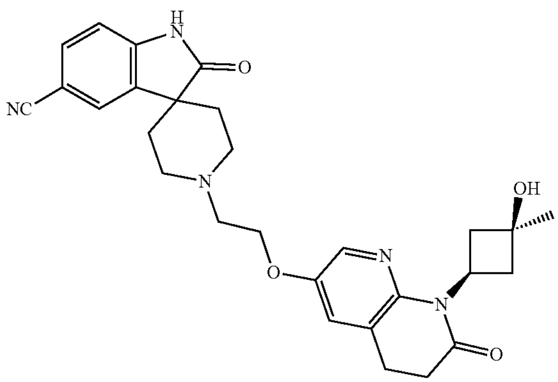 [SMILES: C[C@]1(O)C[C@@H](N2C(=O)CCc3cc(OCCN4CCC5(CC4)C(=O)Nc4ccc(C#N)cc45)cnc32)C1] | 2-oxo-1'-[2-({7-oxo-8-[(cis)-3-hydroxy-3-methylcyclobutyl]-5,6,7,8-tetrahydro-1,8-naphthyridin-3-yl}oxy)ethyl]-1,2-dihydrospiro[indole-3,4'-piperidine]-5-carbonitrile |
| 405 | 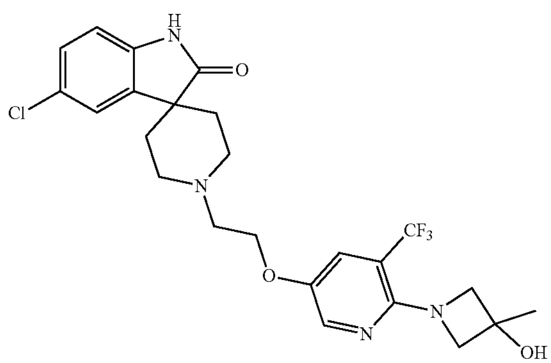 [SMILES: CC1(O)CN(c2ncc(OCCN3CCC4(CC3)C(=O)Nc3ccc(Cl)cc34)cc2C(F)(F)F)C1] | 5-chloro-1'-(2-{[6-(3-hydroxy-3-methylazetidin-1-yl)-5-(trifluoromethyl)pyridin-3-yl]oxy}ethyl)-1,2-dihydrospiro[indole-3,4'-piperidin]-2-one |
| 406 | 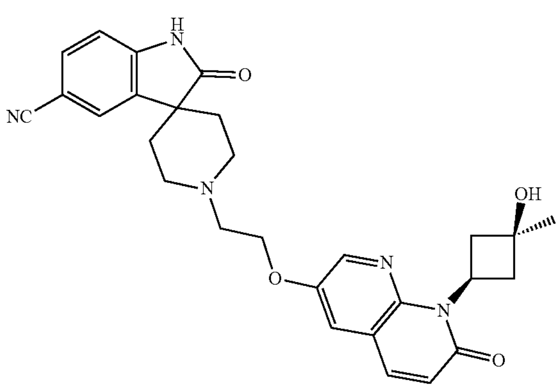 [SMILES: C[C@]1(O)C[C@@H](n2c(=O)ccc3cc(OCCN4CCC5(CC4)C(=O)Nc4ccc(C#N)cc45)cnc32)C1] | 2-oxo-1'-[2-({7-oxo-8-[(cis)-3-hydroxy-3-methylcyclobutyl]-7,8-dihydro-1,8-naphthyridin-3-yl]oxy)ethyl]-1,2-dihydrospiro[indole-3,4'-piperidine]-5-carbonitrile |

TABLE 1-continued

| Compound Number | Structure | Name |
|---|---|---|
| 407 | 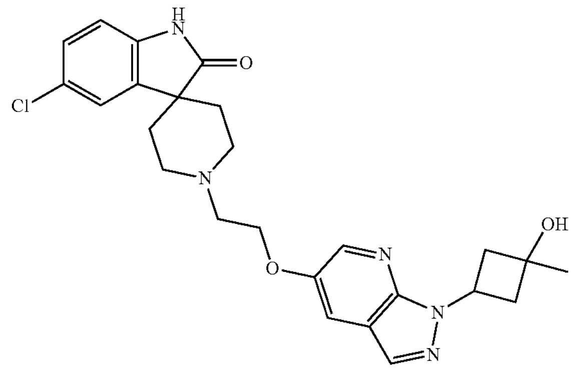 [SMILES: CC1(O)CC(n2ncc3cc(OCCN4CCC5(CC4)C(=O)Nc4ccc(Cl)cc45)cnc32)C1] | 5-chloro-1'-(2-{[1-(3-hydroxy-3-methylcyclobutyl)-1H-pyrazolo[3,4-b]pyridin-5-yl]oxy}ethyl)-1,2-dihydrospiro[indole-3,4'-piperidin]-2-one |
| 408 | 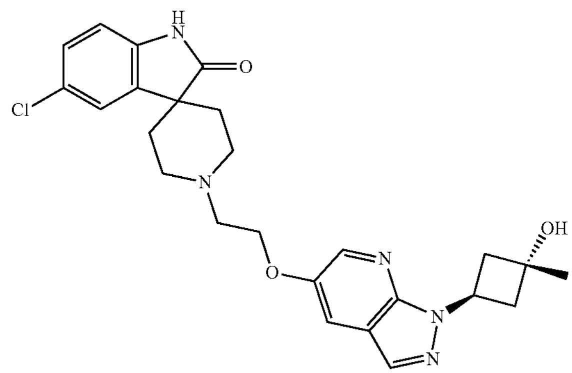 [SMILES: C[C@]1(O)C[C@H](n2ncc3cc(OCCN4CCC5(CC4)C(=O)Nc4ccc(Cl)cc45)cnc32)C1] | 5-chloro-1'-[2-({1-[(trans)-3-hydroxy-3-methylcyclobutyl]-1H-pyrazolo[3,4-b]pyridin-5-yl}oxy)ethyl]-1,2-dihydrospiro[indole-3,4'-piperidin]-2-one |
| 409 | 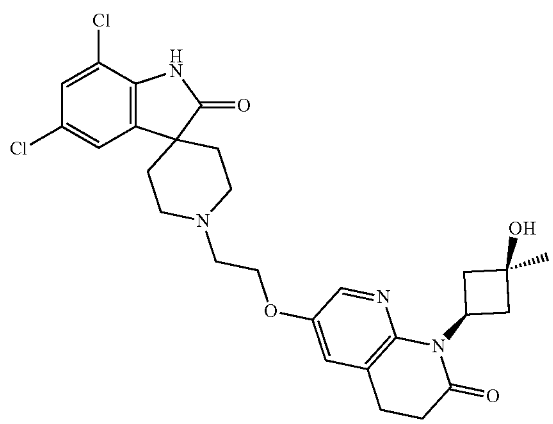 | 5,7-dichloro-1'-[2-({7-oxo-8-[(cis)-3-hydroxy-3-methylcyclobutyl]-5,6,7,8-tetrahydro-1,8-naphthyridin-3-yl}oxy)ethyl]-1,2-dihydrospiro[indole-3,4'-piperidin]-2-one |
| 410 | 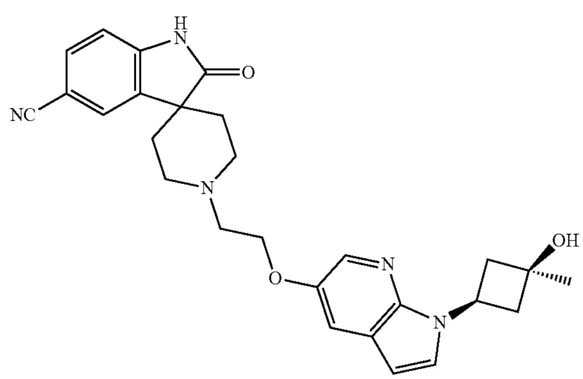 [SMILES: C[C@]1(O)C[C@@H](n2ccc3cc(OCCN4CCC5(CC4)C(=O)Nc4ccc(C#N)cc45)cnc32)C1] | 2-oxo-1'-[2-({1-[(cis)-3-hydroxy-3-methylcyclobutyl]-1H-pyrrolo[2,3-b]pyridin-5-yl}oxy)ethyl]-1,2-dihydrospiro[indole-3,4'-piperidine]-5-carbonitrile |

TABLE 1-continued

| Compound Number | Structure | Name |
|---|---|---|
| 411 | 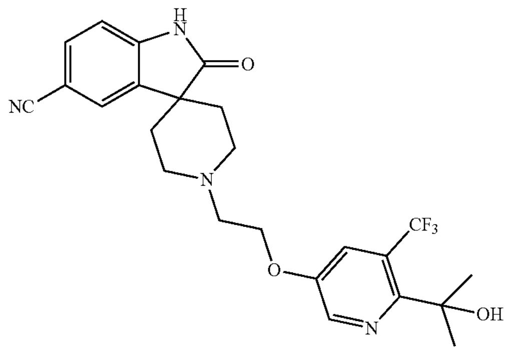 [SMILES: CC(C)(O)c1ncc(OCCN2CCC3(CC2)C(=O)Nc2ccc(C#N)cc23)cc1C(F)(F)F] | 1'-(2-{[6-(2-hydroxypropan-2-yl)-5-(trifluoromethyl)pyridin-3-yl]oxy}ethyl)-2-oxo-1,2-dihydrospiro[indole-3,4'-piperidine]-5-carbonitrile |
| 412 | 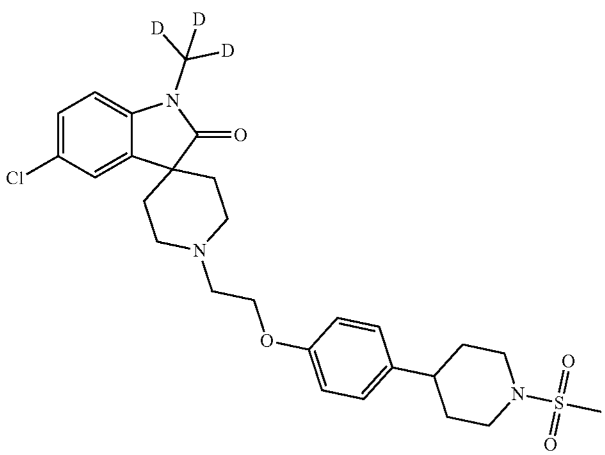 [SMILES: [2H]C([2H])([2H])N1C(=O)C2(CCN(CCOc3ccc(C4CCN(S(C)(=O)=O)CC4)cc3)CC2)c2cc(Cl)ccc21] | 5-chloro-1'-{2-[4-(1-methanesulfonylpiperidin-4-yl)phenoxy]ethyl}-1-($^2$H$_3$)methyl-1,2-dihydrospiro[indole-3,4'-piperidin]-2-one |
| 413 | 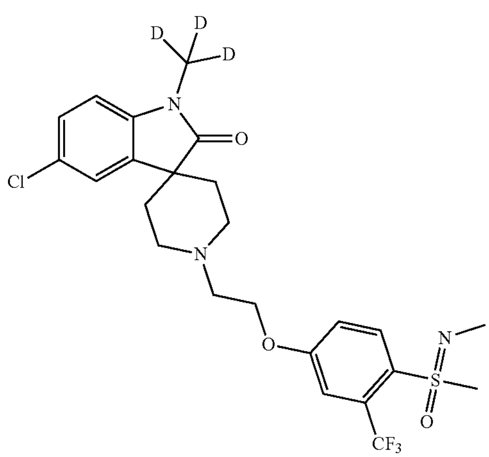 [SMILES: [2H]C([2H])([2H])N1C(=O)C2(CCN(CCOc3ccc(S(C)(=O)=NC)c(C(F)(F)F)c3)CC2)c2cc(Cl)ccc21] | 5-chloro-1-($^2$H$_3$)methyl-1'-(2-{4-[methyl(methylimino)oxo-λ$^6$-sulfanyl]-3-(trifluoromethyl)phenoxy}ethyl)-1,2-dihydrospiro[indole-3,4'-piperidin]-2-one |

TABLE 1-continued

| Compound Number | Structure | Name |
|---|---|---|
| 414 | 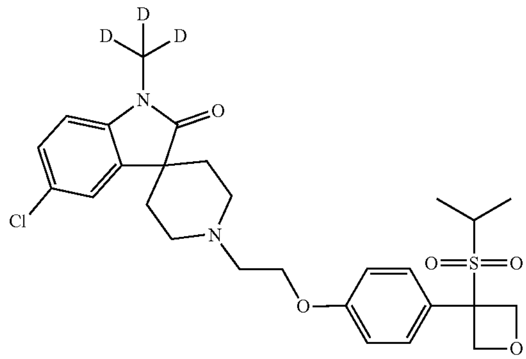 [SMILES: [2H]C([2H])([2H])N1C(=O)C2(CCN(CCOc3ccc(C4(S(=O)(=O)C(C)C)COC4)cc3)CC2)c2cc(Cl)ccc21] | 5-chloro-1-($^2$H$_3$)methyl-1'-(2-{4-[3-(propane-2-sulfonyl)oxetan-3-yl]phenoxy}ethyl)-1,2-dihydrospiro[indole-3,4'-piperidin]-2-one |
| 415 | 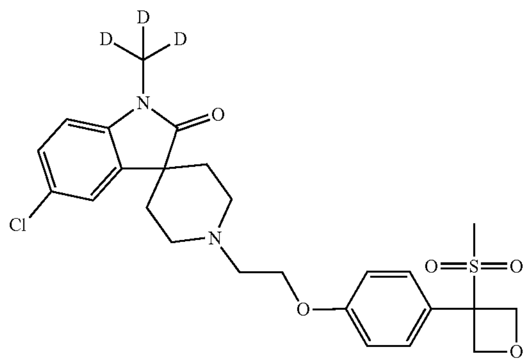 [SMILES: [2H]C([2H])([2H])N1C(=O)C2(CCN(CCOc3ccc(C4(S(C)(=O)=O)COC4)cc3)CC2)c2cc(Cl)ccc21] | 5-chloro-1'-{2-[4-(1-methanesulfonylcyclobutyl)phenoxy]ethyl}-1-($^2$H$_3$)methyl-1,2-dihydrospiro[indole-3,4'-piperidin]-2-one |
| 416 | 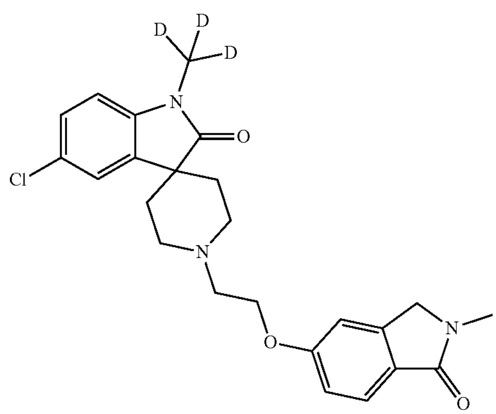 [SMILES: [2H]C([2H])([2H])N1C(=O)C2(CCN(CCOc3ccc4c(c3)CN(C)C4=O)CC2)c2cc(Cl)ccc21] | 5-chloro-1-($^2$H$_3$)methyl-1'-{2-[(2-methyl-1-oxo-2,3-dihydro-1H-isoindol-5-yl)oxy]ethyl}-1,2-dihydrospiro[indole-3,4'-piperidin]-2-one |
| 417 | 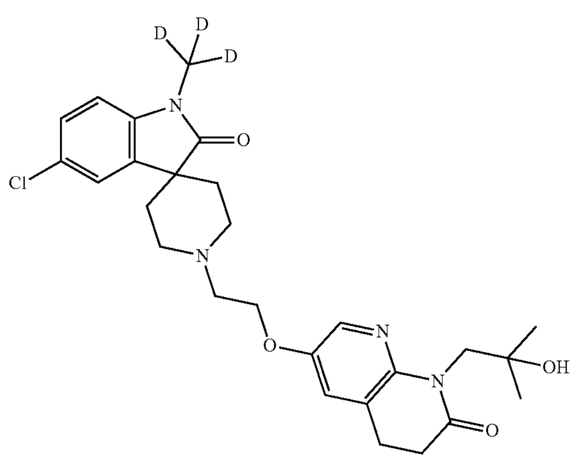 [SMILES: [2H]C([2H])([2H])N1C(=O)C2(CCN(CCOc3cnc4c(c3)CCC(=O)N4CC(C)(C)O)CC2)c2cc(Cl)ccc21] | 5-chloro-1'-(2-{[8-(2-hydroxy-2-methylpropyl)-7-oxo-5,6,7,8-tetrahydro-1,8-naphthyridin-3-yl]oxy}ethyl)-1-($^2$H$_3$)methyl-1,2-dihydrospiro[indole-3,4'-piperidin]-2-one |

| Compound Number | Structure | Name |
|---|---|---|
| 418 | 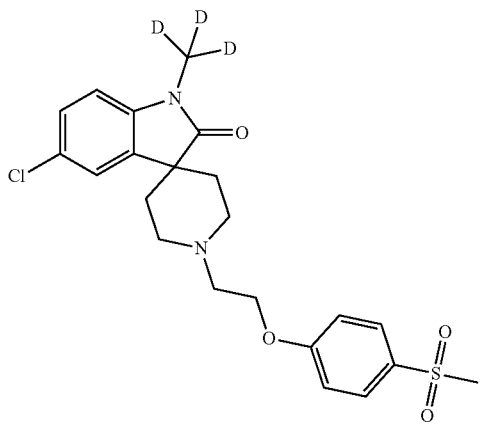 [SMILES: [2H]C([2H])([2H])N1C(=O)C2(CCN(CCOc3ccc(S(C)(=O)=O)cc3)CC2)c2cc(Cl)ccc21] | 5-chloro-1'-[2-(4-methanesulfonylphenoxy)ethyl]-1-($^2H_3$)methyl-1,2-dihydrospiro[indole-3,4'-piperidin]-2-one |
| 419 | 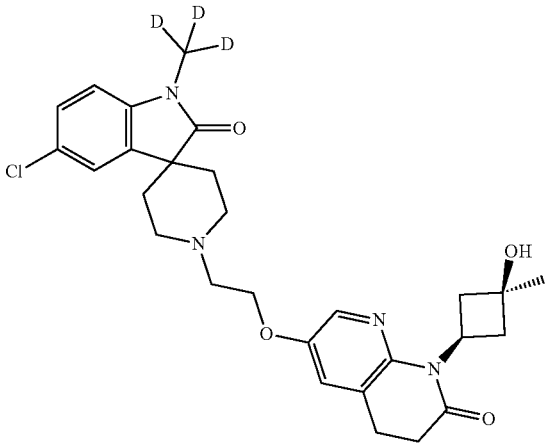 [SMILES: [2H]C([2H])([2H])N1C(=O)C2(CCN(CCOc3cnc4c(c3)CCC(=O)N4[C@H]3C[C@@](C)(O)C3)CC2)c2cc(Cl)ccc21] | 5-chloro-1-($^2H_3$)methyl-1'-[2-({7-oxo-8-[(cis)-3-hydroxy-3-methylcyclobutyl]-5,6,7,8-tetrahydro-1,8-naphthyridin-3-yl}oxy)ethyl]-1,2-dihydrospiro[indole-3,4'-piperidin]-2-one |
| 420 | 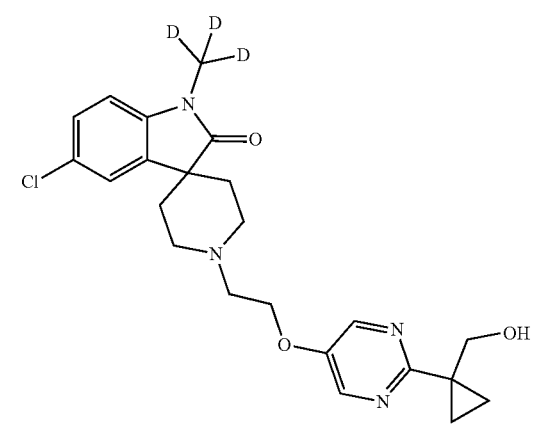 [SMILES: [2H]C([2H])([2H])N1C(=O)C2(CCN(CCOc3cnc(C4(CO)CC4)nc3)CC2)c2cc(Cl)ccc21] | 5-chloro-1'-[2-({2-[1-(hydroxymethyl)cyclopropyl]pyrimidin-5-yl}oxy)ethyl]-1-($^2H_3$)methyl-1,2-dihydrospiro[indole-3,4'-piperidin]-2-one |

TABLE 1-continued

| Compound Number | Structure | Name |
|---|---|---|
| 421 | 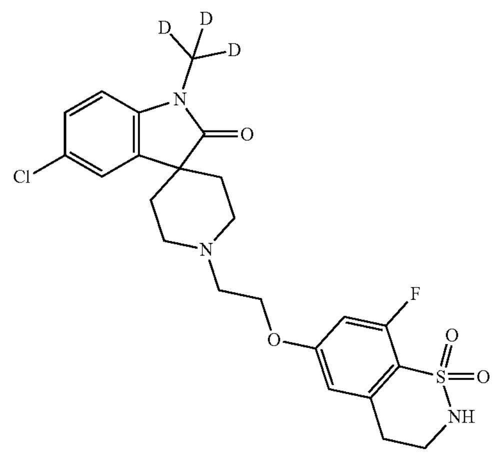 | 6-{2-[5-chloro-1-($^2$H$_3$)methyl-2-oxo-1,2-dihydrospiro[indole-3,4'-piperidin]-1'-yl]ethoxy}-8-fluoro-3,4-dihydro-2H-1λ$^6$,2-benzothiazine-1,1-dione |
| 422 | 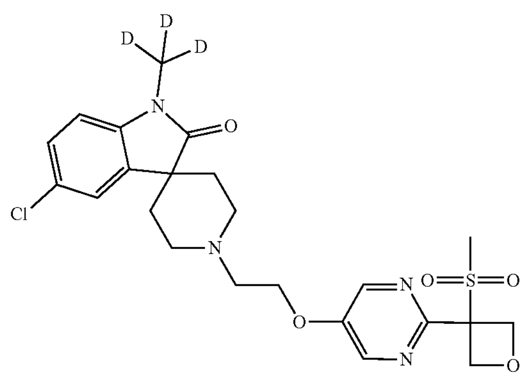 [SMILES: [2H]C([2H])([2H])N1C(=O)C2(CCN(CCOc3cnc(C4(S(C)(=O)=O)COC4)nc3)CC2)c2cc(Cl)ccc21] | 5-chloro-1'-(2-{[2-(3-methanesulfonyloxetan-3-yl)pyrimidin-5-yl]oxy}ethyl)-1-($^2$H$_3$)methyl-1,2-dihydrospiro[indole-3,4'-piperidin]-2-one |
| 423 | 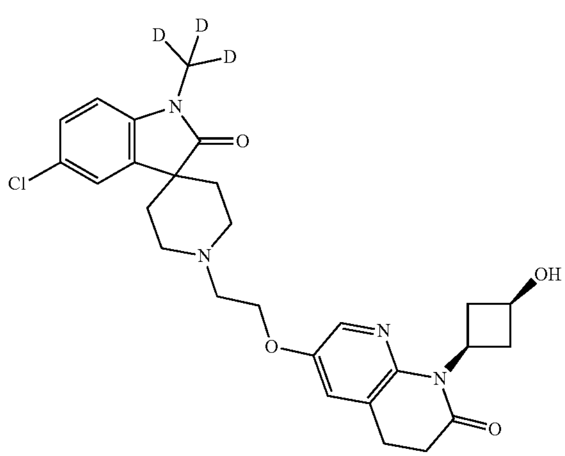 [SMILES: [2H]C([2H])([2H])N1C(=O)C2(CCN(CCOc3cnc4c(c3)CCC(=O)N4[C@H]3C[C@@H](O)C3)CC2)c2cc(Cl)ccc21] | 5-chloro-1-($^2$H$_3$)methyl-1'-[2-({7-oxo-8-[(cis)-3-hydroxycyclobutyl]-5,6,7,8-tetrahydro-1,8-naphthyridin-3-yl}oxy)ethyl]-1,2-dihydrospiro[indole-3,4'-piperidin]-2-one |

TABLE 1-continued

| Compound Number | Structure | Name |
|---|---|---|
| 424 | 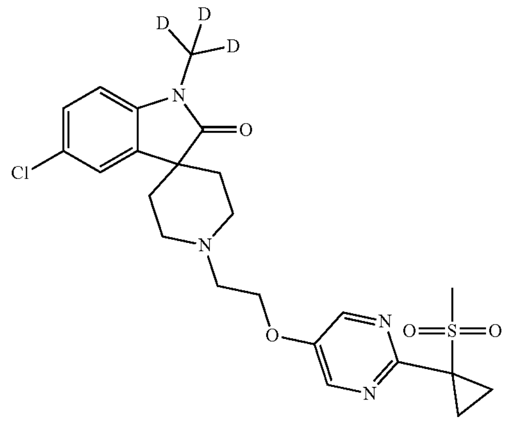 [SMILES: [2H]C([2H])([2H])N1C(=O)C2(CCN(CCOc3cnc(C4(S(C)(=O)=O)CC4)nc3)CC2)c2cc(Cl)ccc21] | 5-chloro-1'-(2-{[2-(1-methanesulfonylcyclopropyl)pyrimidin-5-yl]oxy}ethyl)-1-($^2$H$_3$)methyl-1,2-dihydrospiro[indole-3,4'-piperidin]-2-one |
| 425 | 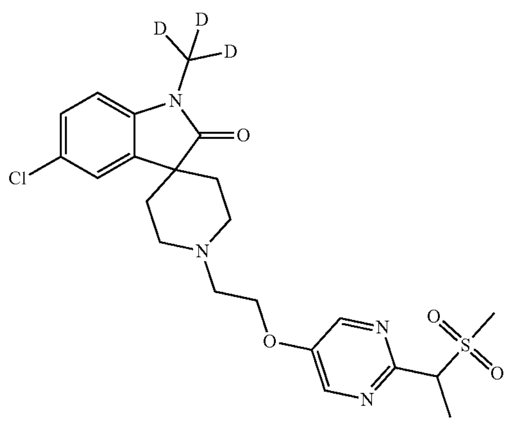 [SMILES: [2H]C([2H])([2H])N1C(=O)C2(CCN(CCOc3cnc(C(C)S(C)(=O)=O)nc3)CC2)c2cc(Cl)ccc21] | 5-chloro-1'-(2-{[2-(1-methanesulfonylethyl)pyrimidin-5-yl]oxy}ethyl)-1-($^2$H$_3$)methyl-1,2-dihydrospiro[indole-3,4'-piperidin]-2-one |
| 426 | 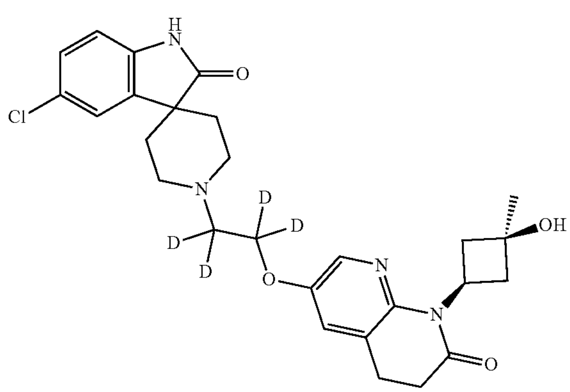 [SMILES: [2H]C([2H])(Oc1cnc2c(c1)CCC(=O)N2[C@H]1C[C@@](C)(O)C1)C([2H])([2H])N1CCC2(CC1)C(=O)Nc1ccc(Cl)cc12] | 5-chloro-1'-[2-({7-oxo-8-[(cis)-3-hydroxy-3-methylcyclobutyl]-5,6,7,8-tetrahydro-1,8-naphthyridin-3-yl}oxy)(1,1,2,2-$^2$H$_4$)ethyl]-1,2-dihydrospiro[indole-3,4'-piperidin]-2-one |

TABLE 1-continued

| Compound Number | Structure | Name |
|---|---|---|
| 427 | 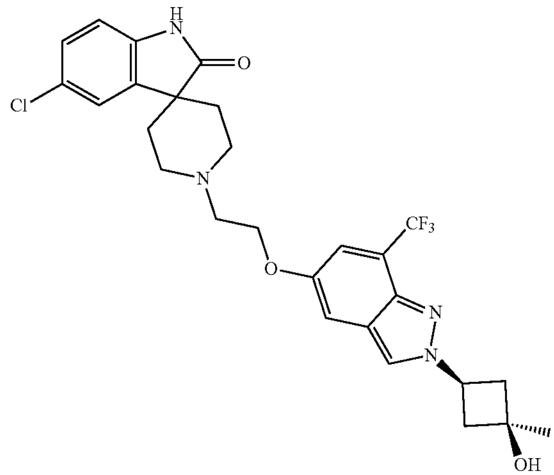 [SMILES: C[C@]1(O)C[C@@H](n2cc3cc(OCCN4CCC5(CC4)C(=O)Nc4ccc(Cl)cc45)cc(C(F)(F)F)c3n2)C1] | 5-chloro-1'-[2-({2-(cis)-3-hydroxy-3-methylcyclobutyl]-7-(trifluoromethyl)-2H-indazol-5-yl}oxy)ethyl]-1,2-dihydrospiro[indole-3,4'-piperidin]-2-one |
| 428 | 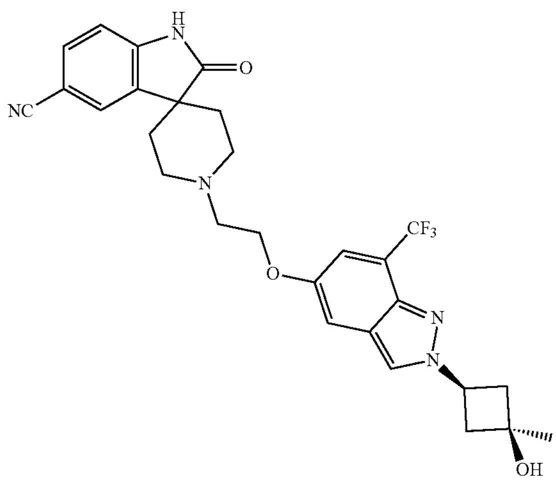 [SMILES: C[C@]1(O)C[C@@H](n2cc3cc(OCCN4CCC5(CC4)C(=O)Nc4ccc(C#N)cc45)cc(C(F)(F)F)c3n2)C1] | 2-oxo-1'-[2-({2-[(cis)-3-hydroxy-3-methylcyclobutyl]-7-(trifluoromethyl)-2H-indazol-5-yl}oxy)ethyl]-1,2-dihydrospiro[indole-3,4'-piperidine]-5-carbonitrile |
| 429 | 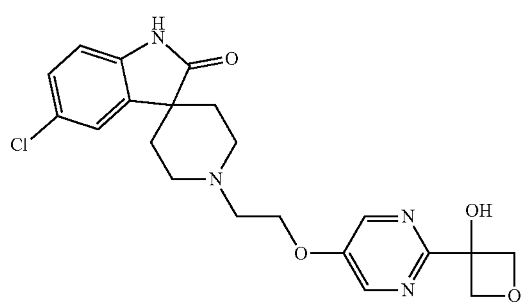 [SMILES: O=C1Nc2ccc(Cl)cc2C12CCN(CCOc1cnc(C3(O)COC3)nc1)CC2] | 5-chloro-1'-(2-{[2-(3-hydroxyoxetan-3-yl)pyrimidin-5-yl]oxy}ethyl)-1,2-dihydrospiro[indole-3,4'-piperidin]-2-one |
| 430 | 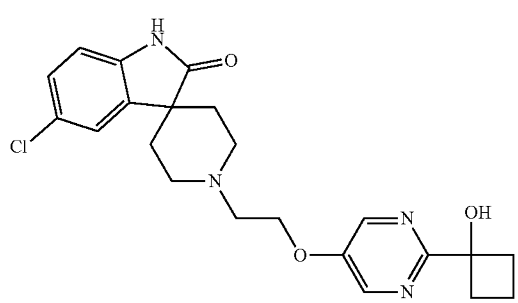 [SMILES: O=C1Nc2ccc(Cl)cc2C12CCN(CCOc1cnc(C3(O)CCC3)nc1)CC2] | 5-chloro-1'-(2-{[2-(1-hydroxycyclobutyl)pyrimidin-5-yl]oxy}ethyl)-1,2-dihydrospiro[indole-3,4'-piperidin]-2-one |

TABLE 1-continued

| Compound Number | Structure | Name |
|---|---|---|
| 431 | 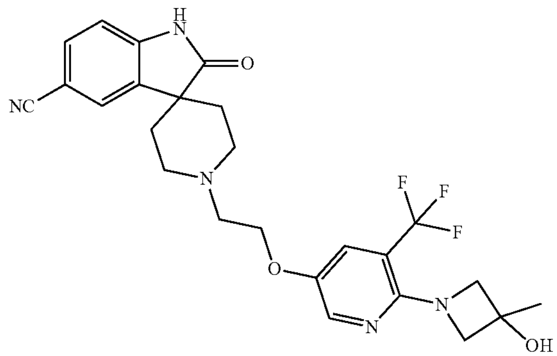 [SMILES: CC1(O)CN(c2ncc(OCCN3CCC4(CC3)C(=O)Nc3ccc(C#N)cc34)cc2C(F)(F)F)C1] | 1'-(2-{[6-(3-hydroxy-3-methylazetidin-1-yl)-5-(trifluoromethyl)pyridin-3-yl]oxy}ethyl)-2-oxo-1,2-dihydrospiro[indole-3,4'-piperidine]-5-carbonitrile |
| 432 | 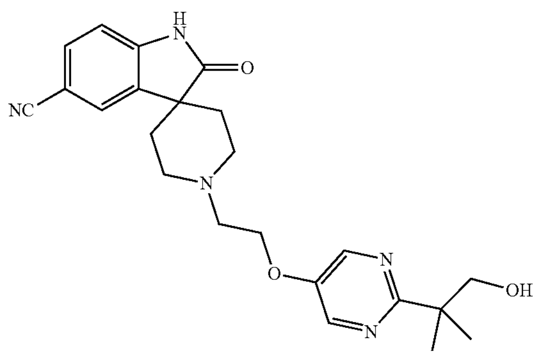 [SMILES: CC(C)(CO)c1ncc(OCCN2CCC3(CC2)C(=O)Nc2ccc(C#N)cc23)cn1] | 1'-(2-{[2-(1-hydroxy-2-methylpropan-2-yl)pyrimidin-5-yl]oxy}ethyl)-2-oxo-1,2-dihydrospiro[indole-3,4'-piperidine]-5-carbonitrile |
| 433 | 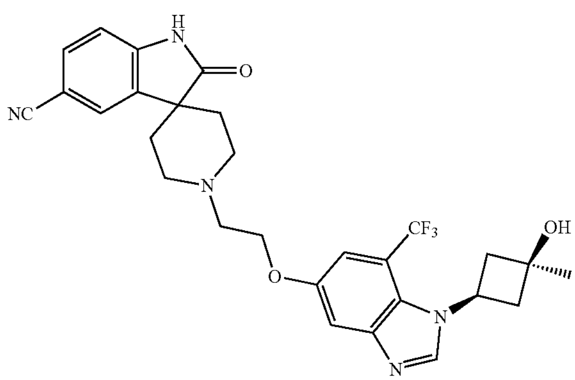 [SMILES: C[C@]1(O)C[C@@H](n2cnc3cc(OCCN4CCC5(CC4)C(=O)Nc4ccc(C#N)cc45)cc(C(F)(F)F)c32)C1] | 2-oxo-1'-[2-({1-[(cis)-3-hydroxy-3-methylcyclobutyl]-7-(trifluoromethyl)-1H-1,3-benzodiazol-5-yl}oxy)ethyl]-1,2-dihydrospiro[indole-3,4'-piperidine]-5-carbonitrile |
| 434 | 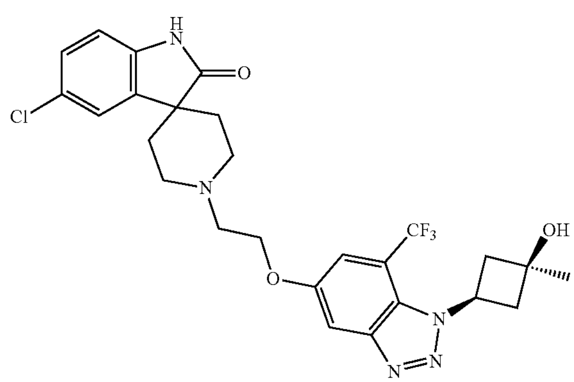 [SMILES: C[C@]1(O)C[C@@H](n2nnc3cc(OCCN4CCC5(CC4)C(=O)Nc4ccc(Cl)cc45)cc(C(F)(F)F)c32)C1] | 5-chloro-1'-[2-({1-[(cis)-3-hydroxy-3-methylcyclobutyl]-7-(trifluoromethyl)-1H-1,2,3-benzotriazol-5-yl}oxy)ethyl]-1,2-dihydrospiro[indole-3,4'-piperidin]-2-one |

TABLE 1-continued

| Compound Number | Structure | Name |
|---|---|---|
| 435 | 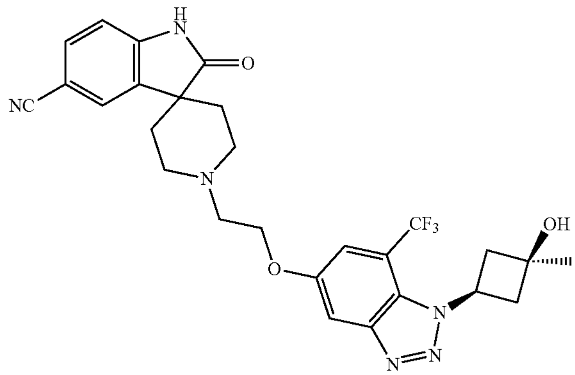 [SMILES: C[C@]1(O)C[C@@H](n2nnc3cc(OCCN4CCC5(CC4)C(=O)Nc4ccc(C#N)cc45)cc(C(F)(F)F)c32)C1] | 2-oxo-1'-[2-({1-[(cis)-3-hydroxy-3-methylcyclobutyl]-7-(trifluoromethyl)-1H-1,2,3-benzotriazol-5-yl}oxy)ethyl]-1,2-dihydrospiro[indole-3,4'-piperidine]-5-carbonitrile |
| 436 | 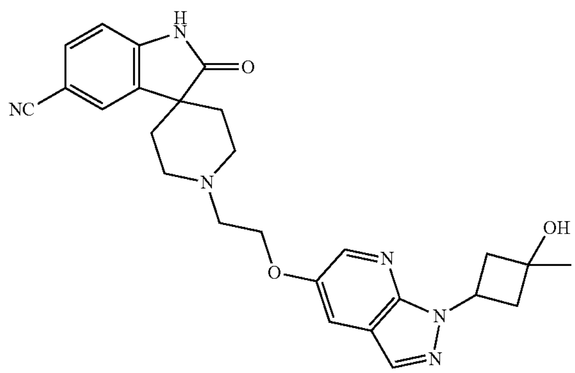 [SMILES: CC1(O)CC(n2ncc3cc(OCCN4CCC5(CC4)C(=O)Nc4ccc(C#N)cc45)cnc32)C1] | 1'-(2-{[1-(3-hydroxy-3-methylcyclobutyl)-1H-pyrazolo[3,4-b]pyridin-5-yl]oxy}ethyl)-2-oxo-1,2-dihydrospiro[indole-3,4'-piperidine]-5-carbonitrile |
| 437 | 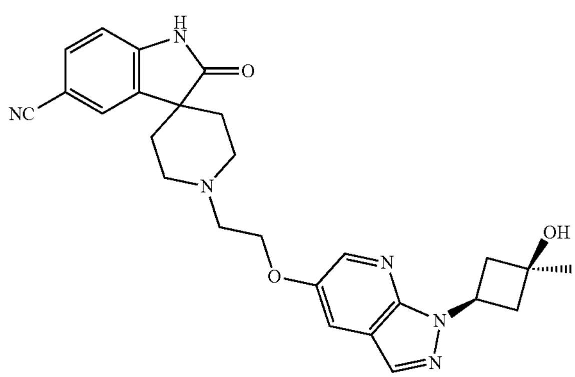 [SMILES: C[C@]1(O)C[C@@H](n2ncc3cc(OCCN4CCC5(CC4)C(=O)Nc4ccc(C#N)cc45)cnc32)C1] | 2-oxo-1'-[2-({1-[(cis)-3-hydroxy-3-methylcyclobutyl]-1H-pyrazolo[3,4-b]pyridin-5-yl}oxy)ethyl]-1,2-dihydrospiro[indole-3,4'-piperidine]-5-carbonitrile |
| 438 | 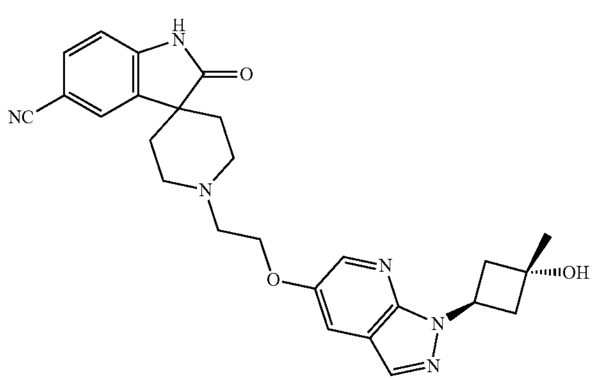 [SMILES: C[C@]1(O)C[C@H](n2ncc3cc(OCCN4CCC5(CC4)C(=O)Nc4ccc(C#N)cc45)cnc32)C1] | 1'-(2-{[1-(3-hydroxy-3-methylcyclobutyl)-1H-pyrazolo[3,4-b]pyridin-5-yl]oxy}ethyl)-2-oxo-1,2-dihydrospiro[indole-3,4'-piperidine]-5-carbonitrile |

TABLE 1-continued

| Compound Number | Structure | Name |
|---|---|---|
| 439 | 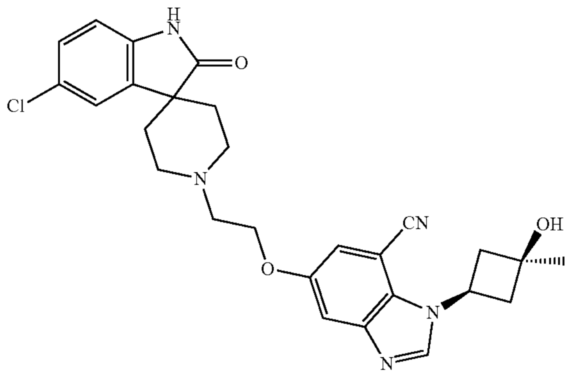 [SMILES: C[C@]1(O)C[C@@H](n2cnc3cc(OCCN4CCC5(CC4)C(=O)Nc4ccc(Cl)cc45)cc(C#N)c32)C1] | 5-(2-{5-chloro-2-oxo-1,2-dihydrospiro[indole-3,4'-piperidin]-1'-yl}ethoxy)-1-[(cis)-3-hydroxy-3-methylcyclobutyl]-1H-1,3-benzodiazole-7-carbonitrile |
| 440 | 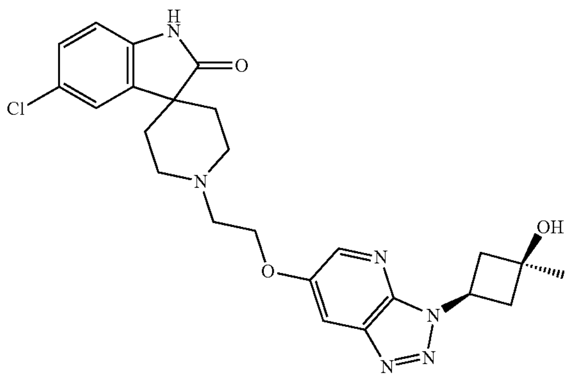 [SMILES: C[C@]1(O)C[C@@H](n2nnc3cc(OCCN4CCC5(CC4)C(=O)Nc4ccc(Cl)cc45)cnc32)C1] | 5-chloro-1'-[2-({3-[(cis)-3-hydroxy-3-methylcyclobutyl]-3H-[1,2,3]triazolo[4,5-b]pyridin-6-yl}oxy)ethyl]-1,2-dihydrospiro[indole-3,4'-piperidin]-2-one |
| 441 | 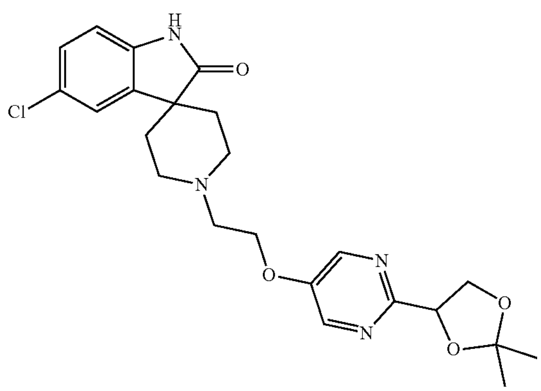 [SMILES: CC1(C)OCC(c2ncc(OCCN3CCC4(CC3)C(=O)Nc3ccc(Cl)cc34)cn2)O1] | 5-chloro-1'-(2-{[2-(2,2-dimethyl-1,3-dioxolan-4-yl)pyrimidin-5-yl]oxy}ethyl)-1,2-dihydrospiro[indole-3,4'-piperidin]-2-one |
| 442 | 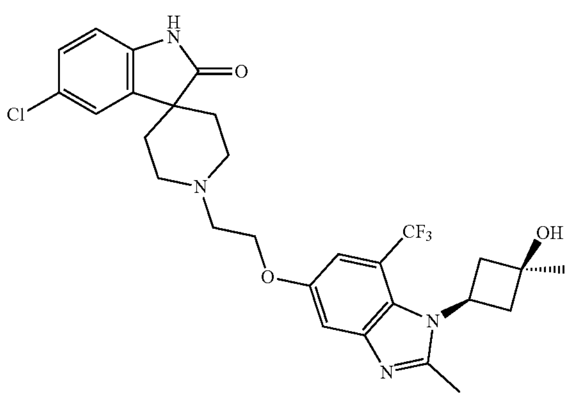 [SMILES: Cc1nc2cc(OCCN3CCC4(CC3)C(=O)Nc3ccc(Cl)cc34)cc(C(F)(F)F)c2n1[C@H]1C[C@@](C)(O)C1] | 5-chloro-1'-[2-({2-methyl-1-[(cis)-3-hydroxy-3-methylcyclobutyl]-7-(trifluoromethyl)-1H-1,3-benzodiazol-5-yl}oxy)ethyl]-1,2-dihydrospiro[indole-3,4'-piperidin]-2-one |

TABLE 1-continued

| Compound Number | Structure | Name |
|---|---|---|
| 443 | 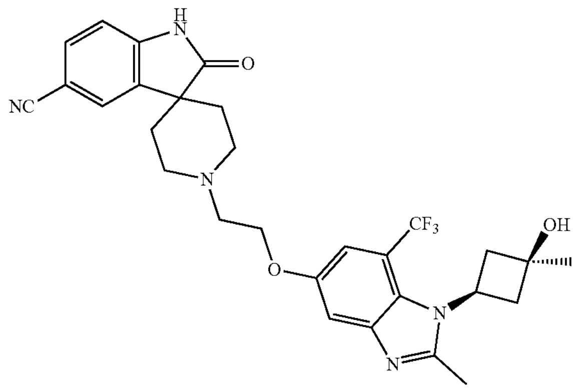 [SMILES: Cc1nc2cc(OCCN3CCC4(CC3)C(=O)Nc3ccc(C#N)cc34)cc(C(F)(F)F)c2n1[C@H]1C[C@@](C)(O)C1] | 1'-[2-({2-methyl-1-[(cis)-3-hydroxy-3-methylcyclobutyl]-7-(trifluoromethyl)-1H-1,3-benzodiazol-5-yl}oxy)ethyl]-2-oxo-1,2-dihydrospiro[indole-3,4'-piperidine]-5-carbonitrile |
| 444 | 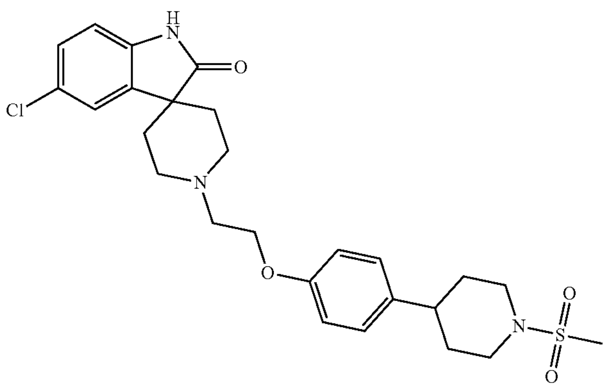 [SMILES: CS(=O)(=O)N1CCC(c2ccc(OCCN3CCC4(CC3)C(=O)Nc3ccc(Cl)cc34)cc2)CC1] | 5-chloro-1'-{2-[4-(1-methanesulfonylpiperidin-4-yl)phenoxy]ethyl}-1,2-dihydrospiro[indole-3,4'-piperidin]-2-one |
| 445 | 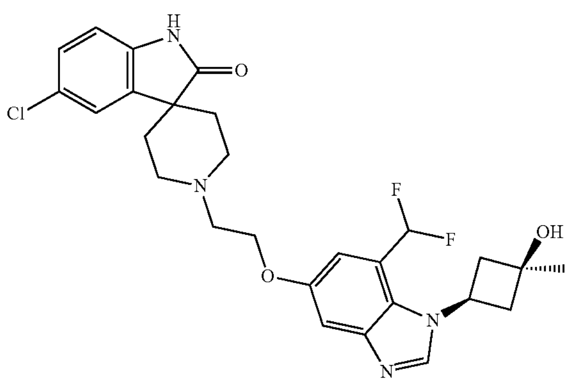 [SMILES: C[C@]1(O)C[C@@H](n2cnc3cc(OCCN4CCC5(CC4)C(=O)Nc4ccc(Cl)cc45)cc(C(F)F)c32)C1] | 5-chloro-1'-(2-{[7-(difluoromethyl)-1-[(cis)-3-hydroxy-3-methylcyclobutyl]-1H-1,3-benzodiazol-5-yl]oxy}ethyl)-1,2-dihydrospiro[indole-3,4'-piperidin]-2-one |
| 446 | 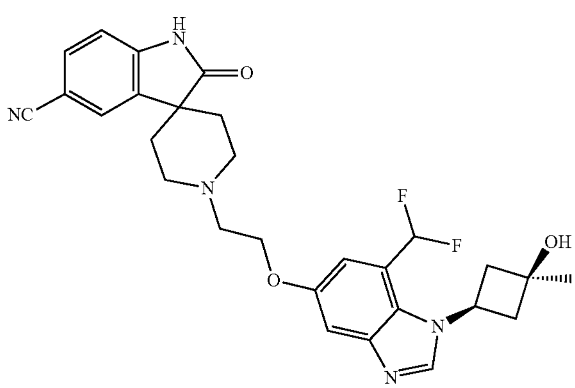 [SMILES: C[C@]1(O)C[C@@H](n2cnc3cc(OCCN4CCC5(CC4)C(=O)Nc4ccc(C#N)cc45)cc(C(F)F)c32)C1] | 1'-(2-{[7-(difluoromethyl)-1-[(cis)-3-hydroxy-3-methylcyclobutyl]-1H-1,3-benzodiazol-5-yl]oxy}ethyl)-2-oxo-1,2-dihydrospiro[indole-3,4'-piperidine]-5-carbonitrile |

TABLE 1-continued

| Compound Number | Structure | Name |
|---|---|---|
| 447 | 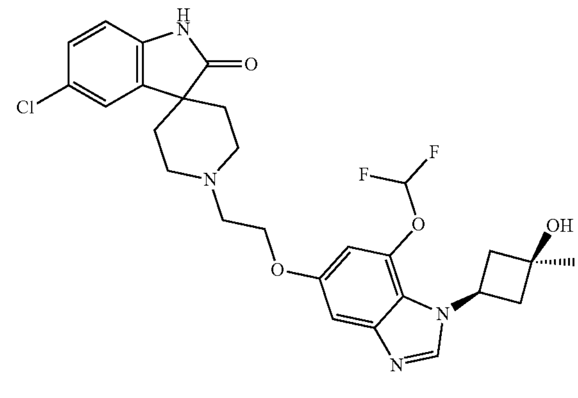 [SMILES: C[C@]1(O)C[C@@H](n2cnc3cc(OCCN4CCC5(CC4)C(=O)Nc4ccc(Cl)cc45)cc(OC(F)F)c32)C1] | 5-chloro-1'-(2-{[7-(difluoromethoxy)-1-[(cis)-3-hydroxy-3-methylcyclobutyl]-1H-1,3-benzodiazol-5-yl]oxy}ethyl)-1,2-dihydrospiro[indole-3,4'-piperidin]-2-one |
| 448 | 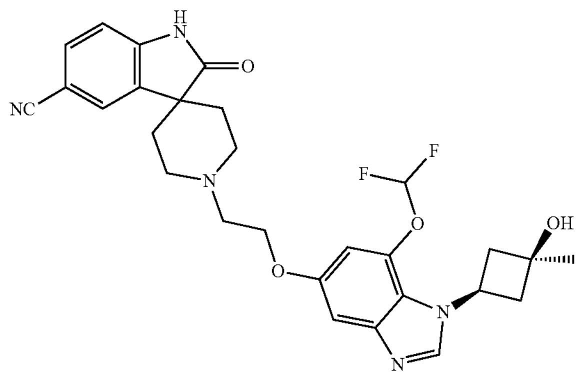 [SMILES: C[C@]1(O)C[C@@H](n2cnc3cc(OCCN4CCC5(CC4)C(=O)Nc4ccc(C#N)cc45)cc(OC(F)F)c32)C1] | 1'-(2-{[7-(difluoromethoxy)-1-[(cis)-3-hydroxy-3-methylcyclobutyl]-1H-1,3-benzodiazol-5-yl]oxy}ethyl)-2-oxo-1,2-dihydrospiro[indole-3,4'-piperidine]-5-carbonitrile |
| 449 | 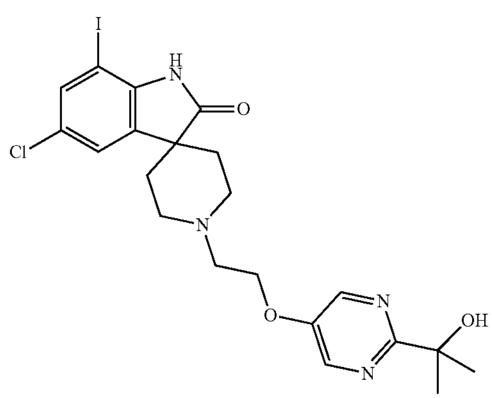 [SMILES: CC(C)(O)c1ncc(OCCN2CCC3(CC2)C(=O)Nc2c(I)cc(Cl)cc23)cn1] | 5-chloro-1'-(2-{[2-(2-hydroxypropan-2-yl)pyrimidin-5-yl]oxy}ethyl)-7-iodo-1,2-dihydrospiro[indole-3,4'-piperidin]-2-one |
| 450 | 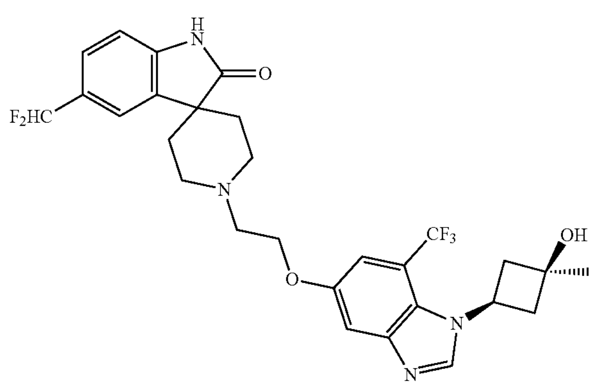 [SMILES: C[C@]1(O)C[C@@H](n2cnc3cc(OCCN4CCC5(CC4)C(=O)Nc4ccc(C(F)F)cc45)cc(C(F)(F)F)c32)C1] | 5-(difluoromethyl)-1'-[2-({1-[(cis)-3-hydroxy-3-methylcyclobutyl]-7-(trifluoromethyl)-1H-1,3-benzodiazol-5-yl}oxy)ethyl]-1,2-dihydrospiro[indole-3,4'-piperidin]-2-one |

TABLE 1-continued

| Compound Number | Structure | Name |
|---|---|---|
| 451 | 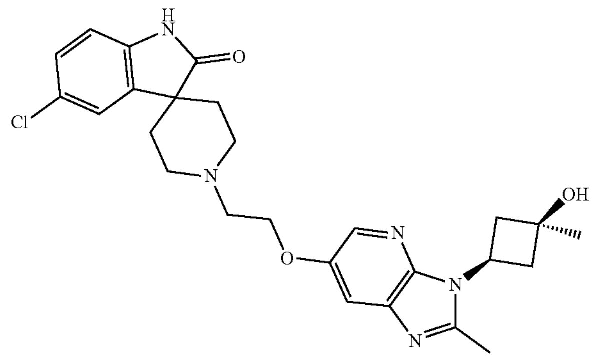 [SMILES: Cc1nc2cc(OCCN3CCC4(CC3)C(=O)Nc3ccc(Cl)cc34)cnc2n1[C@H]1C[C@@](C)(O)C1] | 5-chloro-1'-[2-({2-methyl-3-[(cis)-3-hydroxy-3-methylcyclobutyl]-3H-imidazo[4,5-b]pyridin-6-yl]oxy)ethyl]-1,2-dihydrospiro[indole-3,4'-piperidin]-2-one |
| 452 | 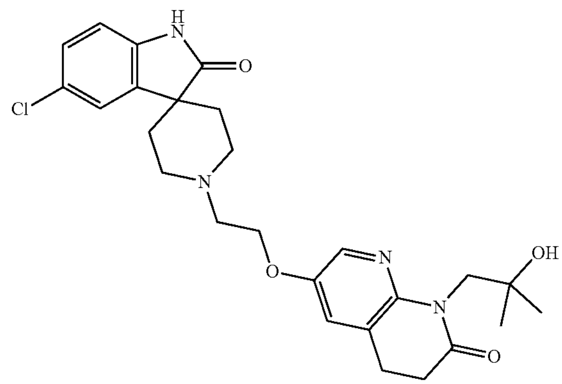 [SMILES: CC(C)(O)CN1C(=O)CCc2cc(OCCN3CCC4(CC3)C(=O)Nc3ccc(Cl)cc34)cnc21] | 5-chloro-1'-(2-{[8-(2-hydroxy-2-methylpropyl)-7-oxo-5,6,7,8-tetrahydro-1,8-naphthyridin-3-yl]oxy}ethyl)-1,2-dihydrospiro[indole-3,4'-piperidin]-2-one |
| 453 | 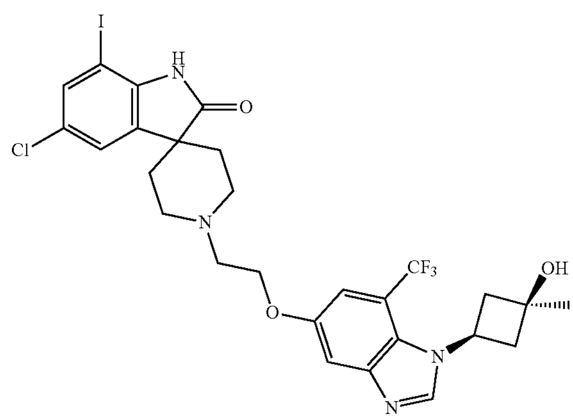 [SMILES: C[C@]1(O)C[C@@H](n2cnc3cc(OCCN4CCC5(CC4)C(=O)Nc4c(I)cc(Cl)cc45)cc(C(F)(F)F)c32)C1] | 5-chloro-7-iodo-1'-[2-({1-[(cis)-3-hydroxy-3-methylcyclobutyl]-7-(trifluoromethyl)-1H-1,3-benzodiazol-5-yl}oxy)ethyl]-1,2-dihydrospiro[indole-3,4'-piperidin]-2-one |
| 454 | 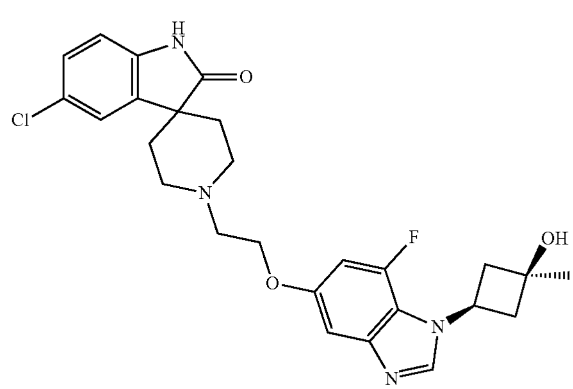 [SMILES: C[C@]1(O)C[C@@H](n2cnc3cc(OCCN4CCC5(CC4)C(=O)Nc4ccc(Cl)cc45)cc(F)c32)C1] | 5-chloro-1'-[2-({7-fluoro-1-[(cis)-3-hydroxy-3-methylcyclobutyl]-1H-1,3-benzodiazol-5-yl]oxy)ethyl]-1,2-dihydrospiro[indole-3,4'-piperidin]-2-one |

TABLE 1-continued

| Compound Number | Structure | Name |
|---|---|---|
| 455 | 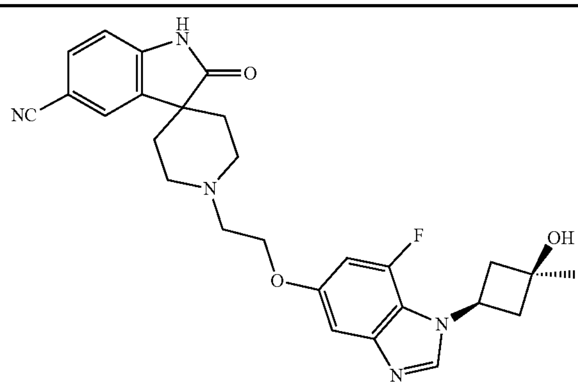 | 1'-[2-({7-fluoro-1-[(cis)-3-hydroxy-3-methylcyclobutyl]-1H-1,3-benzodiazol-5-yl}oxy)ethyl]-2-oxo-1,2-dihydrospiro[indole-3,4'-piperidine]-5-carbonitrile |
| 456 | 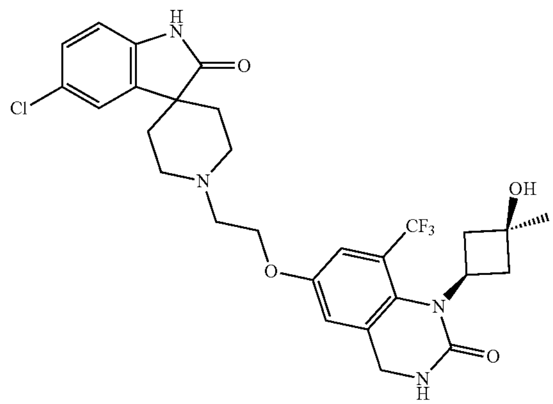 [SMILES: C[C@]1(O)C[C@@H](N2C(=O)NCc3cc(OCCN4CCC5(CC4)C(=O)Nc4ccc(Cl)cc45)cc(C(F)(F)F)c32)C1] | 5-chloro-1'-[2-({2-oxo-1-[(cis)-3-hydroxy-3-methylcyclobutyl]-8-(trifluoromethyl)-1,2,3,4-tetrahydroquinazolin-6-yl}oxy)ethyl]-1,2-dihydrospiro[indole-3,4'-piperidin]-2-one |
| 457 | 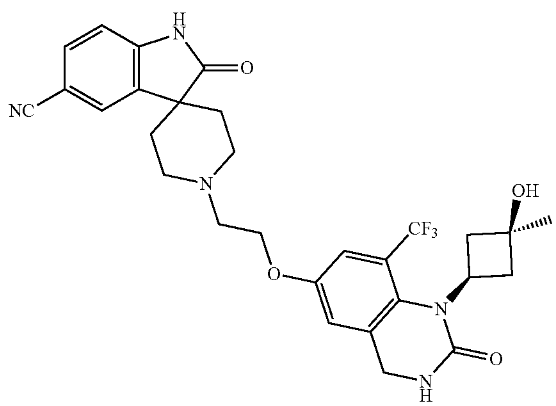 [SMILES: C[C@]1(O)C[C@@H](N2C(=O)NCc3cc(OCCN4CCC5(CC4)C(=O)Nc4ccc(C#N)cc45)cc(C(F)(F)F)c32)C1] | 2-oxo-1'-[2-({2-oxo-1-[(cis)-3-hydroxy-3-methylcyclobutyl]-8-(trifluoromethyl)-1,2,3,4-tetrahydroquinazolin-6-yl}oxy)ethyl]-1,2-dihydrospiro[indole-3,4'-piperidine]-5-carbonitrile |
| 458 | 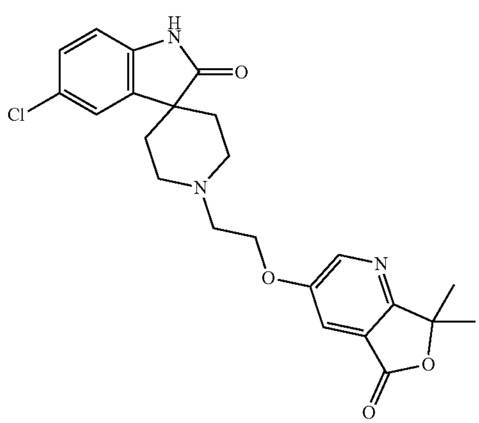 [SMILES: CC1(C)OC(=O)c2cc(OCCN3CCC4(CC3)C(=O)Nc3ccc(Cl)cc34)cnc21] | 5-chloro-1'-[2-({7,7-dimethyl-5-oxo-5H,7H-furo[3,4-b]pyridin-3-yl}oxy)ethyl]-1,2-dihydrospiro[indole-3,4'-piperidin]-2-one |

| Compound Number | Structure | Name |
|---|---|---|
| 459 | 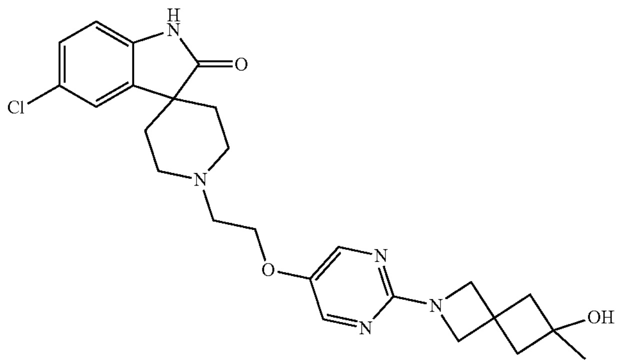 [SMILES: CC1(O)CC2(CN(c3ncc(OCCN4CCC5(CC4)C(=O)Nc4ccc(Cl)cc45)cn3)C2)C1] | 5-chloro-1'-{2-[(2-{6-hydroxy-6-methyl-2-azaspiro[3.3]heptan-2-yl}pyrimidin-5-yl)oxy]ethyl}-1,2-dihydrospiro[indole-3,4'-piperidin]-2-one |
| 460 | 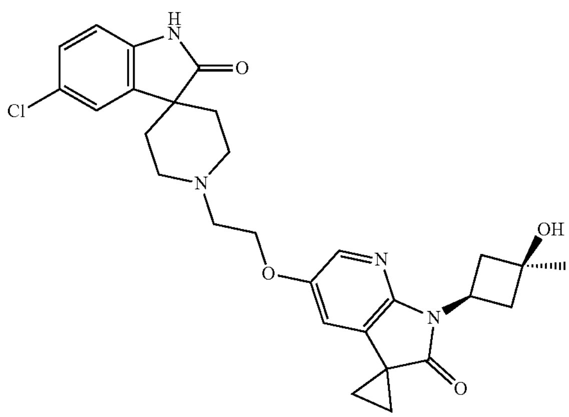 [SMILES: C[C@]1(O)C[C@@H](N2C(=O)C3(CC3)c3cc(OCCN4CCC5(CC4)C(=O)Nc4ccc(Cl)cc45)cnc32)C1] | 5-chloro-1'-(2-{2'-oxo-1'-[(cis)-3-hydroxy-3-methylcyclobutyl]-1',2'-dihydrospiro[cyclopropane-1,3'-pyrrolo[2,3-b]pyridin]-5'-yloxy}ethyl)-1,2-dihydrospiro[indole-3,4'-piperidin]-2-one |
| 461 | 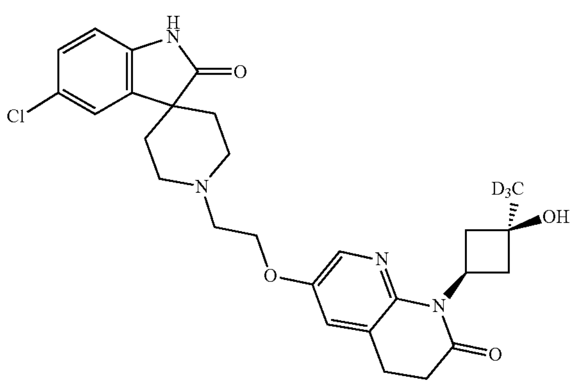 [SMILES: [2H]C([2H])([2H])[C@]1(O)C[C@@H](N2C(=O)CCc3cc(OCCN4CCC5(CC4)C(=O)Nc4ccc(Cl)cc45)cnc32)C1] | 5-chloro-1'-[2-({7-oxo-8-[(cis)-3-hydroxy-3-($^2$H$_3$)methylcyclobutyl]-5,6,7,8-tetrahydro-1,8-naphthyridin-3-yl}oxy)ethyl]-1,2-dihydrospiro[indole-3,4'-piperidin]-2-one |
| 462 | 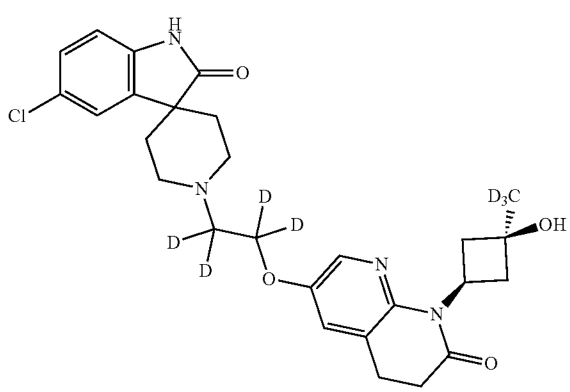 [SMILES: [2H]C([2H])(Oc1cnc2c(c1)CCC(=O)N2[C@H]1C[C@](O)(C([2H])([2H])[2H])C1)C([2H])([2H])N1CCC2(CC1)C(=O)Nc1ccc(Cl)cc12] | 5-chloro-1'-[2-({7-oxo-8-[(cis)-3-hydroxy-3-($^2$H$_3$)methylcyclobutyl]-5,6,7,8-tetrahydro-1,8-naphthyridin-3-yl}oxy)(1,1,2,2-$^2$H$_4$)ethyl]-1,2-dihydrospiro[indole-3,4'-piperidin]-2-one |

TABLE 1-continued

| Compound Number | Structure | Name |
|---|---|---|
| 463 | 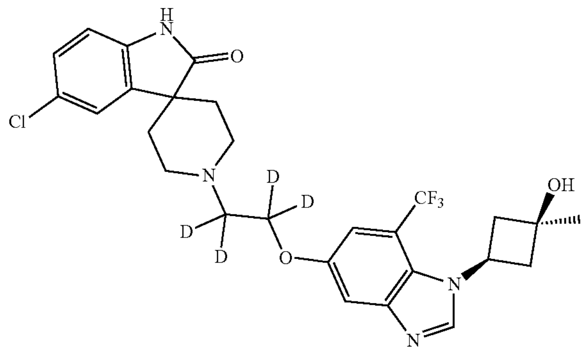 [SMILES: [2H]C([2H])(Oc1cc(C(F)(F)F)c2c(c1)ncn2[C@H]1C[C@@](C)(O)C1)C([2H])([2H])N1CCC2(CC1)C(=O)Nc1ccc(Cl)cc12] | 5-chloro-1'-[2-({1-[(cis)-3-hydroxy-3-methylcyclobutyl]-7-(trifluoromethyl)-1H-1,3-benzodiazol-5-yl}oxy)(1,1,2,2-$^2$H$_4$)ethyl]-1,2-dihydrospiro[indole-3,4'-piperidin]-2-one |
| 464 | 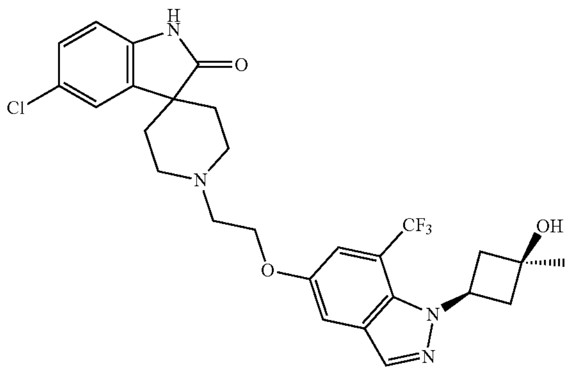 [SMILES: C[C@]1(O)C[C@@H](n2ncc3cc(OCCN4CCC5(CC4)C(=O)Nc4ccc(Cl)cc45)cc(C(F)(F)F)c32)C1] | 5-chloro-1'-[2-({1-[(cis)-3-hydroxy-3-methylcyclobutyl]-7-(trifluoromethyl)-1H-indazol-5-yl}oxy)ethyl]-1,2-dihydrospiro[indole-3,4'-piperidin]-2-one |
| 465 | 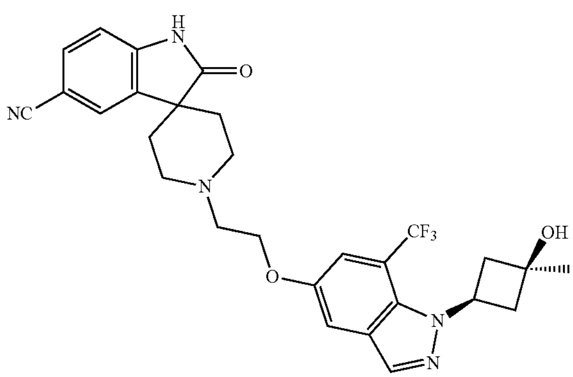 [SMILES: C[C@]1(O)C[C@@H](n2ncc3cc(OCCN4CCC5(CC4)C(=O)Nc4ccc(C#N)cc45)cc(C(F)(F)F)c32)C1] | 2-oxo-1'-[2-({1-[(cis)-3-hydroxy-3-methylcyclobutyl]-7-(trifluoromethyl)-1H-indazol-5-yl}oxy)ethyl]-1,2-dihydrospiro[indole-3,4'-piperidine]-5-carbonitrile |
| 466 | 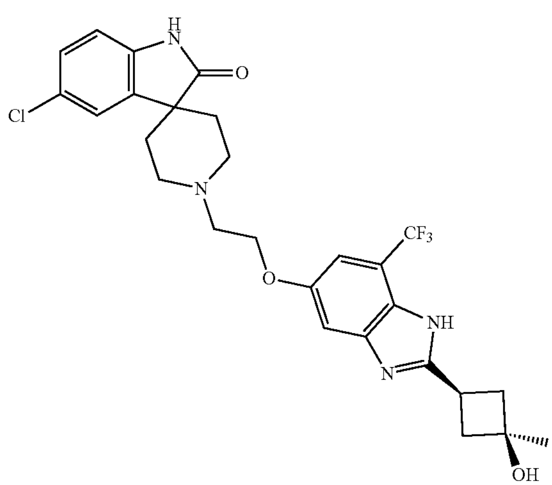 [SMILES: C[C@]1(O)C[C@@H](c2nc3cc(OCCN4CCC5(CC4)C(=O)Nc4ccc(Cl)cc45)cc(C(F)(F)F)c3[nH]2)C1] | 5-chloro-1'-[2-({2-[(cis)-3-hydroxy-3-methylcyclobutyl]-7-(trifluoromethyl)-1H-1,3-benzodiazol-5-yl}oxy)ethyl]-1,2-dihydrospiro[indole-3,4'-piperidin]-2-one |

TABLE 1-continued

| Compound Number | Structure | Name |
|---|---|---|
| 467 | 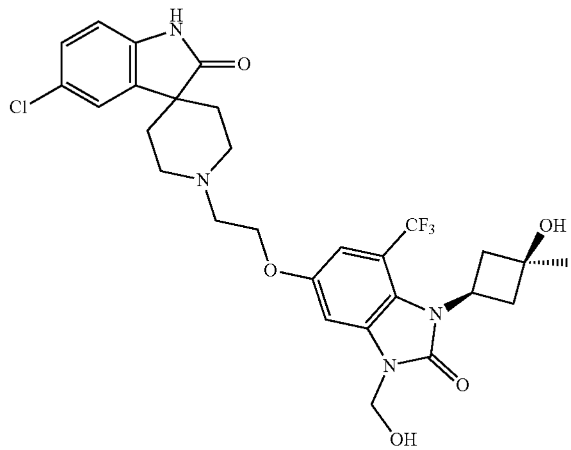 [SMILES: C[C@]1(O)C[C@@H](n2c(=O)n(CO)c3cc(OCCN4CCC5(CC4)C(=O)Nc4ccc(Cl)cc45)cc(C(F)(F)F)c32)C1] | 5-chloro-1'-(2-{[3-(hydroxymethyl)-2-oxo-1-[(cis)-3-hydroxy-3-methylcyclobutyl]-7-(trifluoromethyl)-2,3-dihydro-1H-1,3-benzodiazol-5-yl]oxy}ethyl)-1,2-dihydrospiro[indole-3,4'-piperidin]-2-one |
| 468 | 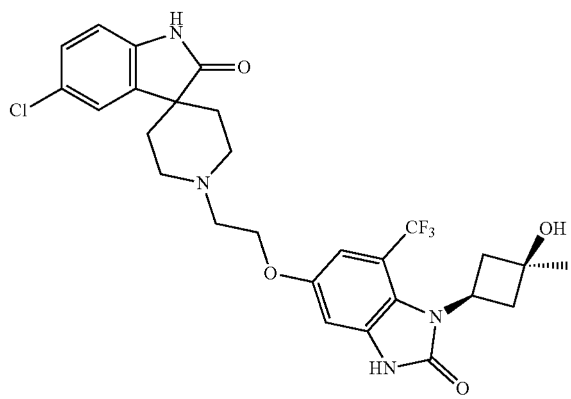 [SMILES: C[C@]1(O)C[C@@H](n2c(=O)[nH]c3cc(OCCN4CCC5(CC4)C(=O)Nc4ccc(Cl)cc45)cc(C(F)(F)F)c32)C1] | 5-chloro-1'-[2-({2-oxo-1-[(cis)-3-hydroxy-3-methylcyclobutyl]-7-(trifluoromethyl)-2,3-dihydro-1H-1,3-benzodiazol-5-yl}oxy)ethyl]-1,2-dihydrospiro[indole-3,4'-piperidin]-2-one |
| 469 | 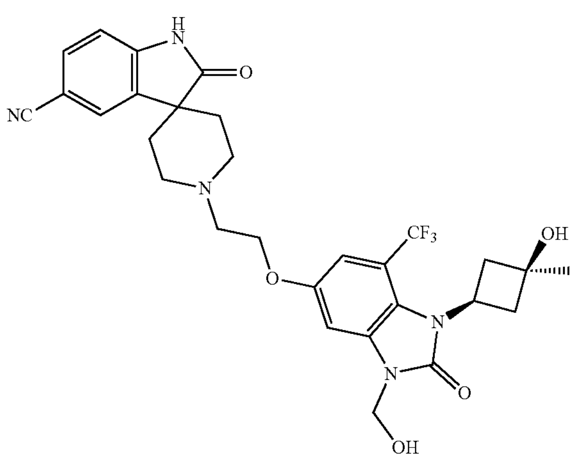 [SMILES: C[C@]1(O)C[C@@H](n2c(=O)n(CO)c3cc(OCCN4CCC5(CC4)C(=O)Nc4ccc(C#N)cc45)cc(C(F)(F)F)c32)C1] | 1'-(2-{[3-(hydroxymethyl)-2-oxo-1-[(cis)-3-hydroxy-3-methylcyclobutyl]-7-(trifluoromethyl)-2,3-dihydro-1H-1,3-benzodiazol-5-yl]oxy}ethyl)-2-oxo-1,2-dihydrospiro[indole-3,4'-piperidine]-5-carbonitrile |

| Compound Number | Structure | Name |
|---|---|---|
| 470 | 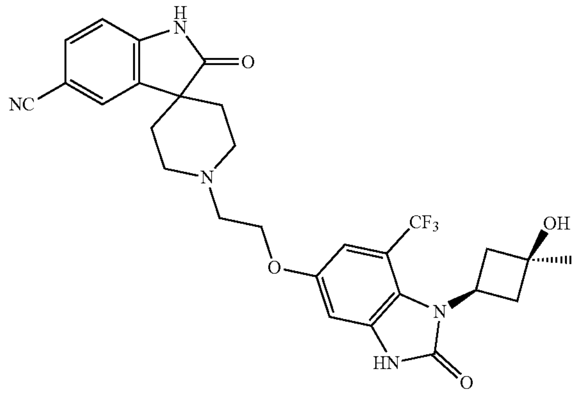 [SMILES: C[C@]1(O)C[C@@H](n2c(=O)[nH]c3cc(OCCN4CCC5(CC4)C(=O)Nc4ccc(C#N)cc45)cc(C(F)(F)F)c32)C1] | 2-oxo-1'-[2-({2-oxo-1-[(cis)-3-hydroxy-3-methylcyclobutyl]-7-(trifluoromethyl)-2,3-dihydro-1H-1,3-benzodiazol-5-yl}oxy)ethyl]-1,2-dihydrospiro[indole-3,4'-piperidine]-5-carbonitrile |
| 471 | 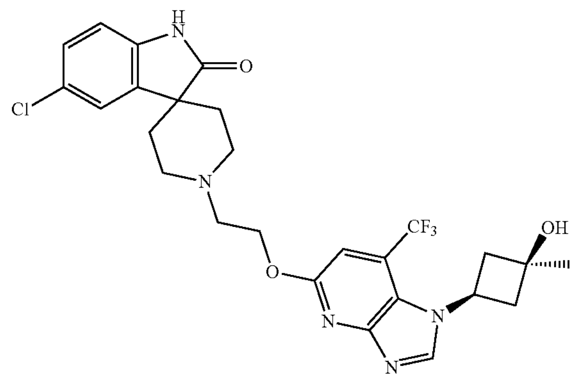 [SMILES: C[C@]1(O)C[C@@H](n2cnc3nc(OCCN4CCC5(CC4)C(=O)Nc4ccc(Cl)cc45)cc(C(F)(F)F)c32)C1] | 5-chloro-1'-[2-({1-[(cis)-3-hydroxy-3-methylcyclobutyl]-7-(trifluoromethyl)-1H-imidazo[4,5-b]pyridin-5-yl}oxy)ethyl]-1,2-dihydrospiro[indole-3,4'-piperidin]-2-one |
| 472 | 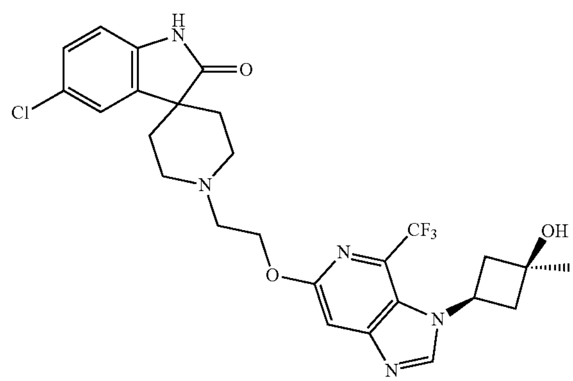 [SMILES: C[C@]1(O)C[C@@H](n2cnc3cc(OCCN4CCC5(CC4)C(=O)Nc4ccc(Cl)cc45)nc(C(F)(F)F)c32)C1] | 5-chloro-1'-(2-{3-[(cis)-3-hydroxy-3-methylcyclobutyl]-4-(trifluoromethyl)-3H-1,3,5-triazainden-6-yloxy}ethyl)spiro[indoline-3,4'-piperidin]-2-one |

In some embodiments, a compound of formula (I) is selected from the group consisting of:

1'-[2-(4-methanesulfonylphenoxy)ethyl]-1,2-dihydrospiro[indole-3,4'-piperidin]-2-one;

1'-[2-(4-methanesulfonylphenoxy)ethyl]-1-(2-methoxyethyl)-1,2-dihydrospiro[indole-3,4'-piperidin]-2-one;

5-bromo-1'-[2-(4-methanesulfonylphenoxy)ethyl]-1,2-dihydrospiro[indole-3,4'-piperidin]-2-one;

1'-[2-(4-methanesulfonylphenoxy)ethyl]-2-oxo-1,2-dihydrospiro[indole-3,4'-piperidine]-5-carbonitrile;

1'-{2-[(1-methyl-1H-indazol-5-yl)oxy]ethyl}-1,2-dihydrospiro[indole-3,4'-piperidin]-2-one;

5-bromo-1-(2-hydroxyethyl)-1'-[2-(4-methanesulfonylphenoxy)ethyl]-1,2-dihydrospiro[indole-3,4'-piperidin]-2-one;

5-chloro-1'-[2-(4-methanesulfonylphenoxy)ethyl]-1,2-dihydrospiro[indole-3,4'-piperidin]-2-one;

5-chloro-1'-[2-(4-methanesulfonylphenoxy)ethyl]-1-(2-methoxyethyl)-1,2-dihydrospiro[indole-3,4'-piperidin]-2-one;

1'-[2-(4-methanesulfonylphenoxy)ethyl]-1-(2-methoxyethyl)-2-oxo-1,2-dihydrospiro[indole-3,4'-piperidine]-5-carbonitrile;

1'-{2-[(2-methanesulfonyl-1,2,3,4-tetrahydroisoquinolin-6-yl)oxy]ethyl}-1-methyl-1,2-dihydrospiro[indole-3,4'-piperidin]-2-one;

1'-{2-[(2-acetyl-1,2,3,4-tetrahydroisoquinolin-6-yl)oxy]ethyl}-1-methyl-1,2-dihydrospiro[indole-3,4'-piperidin]-2-one;

1'-[1-(4-methanesulfonylphenoxy)propan-2-yl]-1,2-dihydrospiro[indole-3,4'-piperidin]-2-one;

1-[2-(4-methanesulfonylphenoxy)ethyl]-1',2'-dihydrospiro[azepane-4,3'-indol]-2'-one;

1'-[1-(4-methanesulfonylphenoxy)propan-2-yl]-1,2-dihydrospiro[indole-3,4'-piperidin]-2-one;

1'-[2-(4-methanesulfonylphenoxy)propyl]-1,2-dihydrospiro[indole-3,4'-piperidin]-2-one;

5-chloro-1'-{2-[(1-methyl-1H-indazol-5-yl)oxy]ethyl}-1,2-dihydrospiro[indole-3,4'-piperidin]-2-one;

1'-[2-(4-difluoromethanesulfonylphenoxy)ethyl]-1,2-dihydrospiro[indole-3,4'-piperidin]-2-one;

1'-[2-(3,5-difluoro-4-methanesulfonylphenoxy)ethyl]-1,2-dihydrospiro[indole-3,4'-piperidin]-2-one;

1-(3-hydroxycyclobutyl)-1'-[2-(4-methanesulfonylphenoxy)ethyl]-1,2-dihydrospiro[indole-3,4'-piperidin]-2-one;

5-chloro-1'-{2-[4-(3-methanesulfonylpropanesulfonyl)phenoxy]ethyl}-1,2-dihydrospiro[indole-3,4'-piperidin]-2-one;

5-chloro-1'-{2-[4-(cyclopropanesulfonyl)phenoxy]ethyl}-1,2-dihydrospiro[indole-3,4'-piperidin]-2-one;

5,7-dichloro-1'-[2-(4-methanesulfonylphenoxy)ethyl]-1,2-dihydrospiro[indole-3,4'-piperidin]-2-one;

1-methyl-1'-{2-[4-(2-oxopyrrolidin-1-yl)phenoxy]ethyl}-1,2-dihydrospiro[indole-3,4'-piperidin]-2-one;

1'-{2-[(1-acetyl-1,2,3,4-tetrahydroquinolin-6-yl)oxy]ethyl}-1-methyl-1,2-dihydrospiro[indole-3,4'-piperidin]-2-one;

1-methyl-1'-{2-[4-(5-methyl-1,2,4-oxadiazol-3-yl)phenoxy]ethyl}-1,2-dihydrospiro[indole-3,4'-piperidin]-2-one;

1-methyl-1'-[2-(quinoxalin-6-yloxy)ethyl]-1,2-dihydrospiro[indole-3,4'-piperidin]-2-one;

1-methyl-1'-{2-[(1-methyl-2-oxo-2,3-dihydro-1H-indol-5-yl)oxy]ethyl}-1,2-dihydrospiro[indole-3,4'-piperidin]-2-one;

5-(2-{1-methyl-2-oxo-1,2-dihydrospiro[indole-3,4'-piperidin]-1'-yl}ethoxy)-2,3-dihydro-1lambda6-benzothiophene-1,1-dione;

5-chloro-1-(2-hydroxyethyl)-1'-[2-(4-methanesulfonylphenoxy)ethyl]-1,2-dihydrospiro[indole-3,4'-piperidin]-2-one;

5-chloro-1'-{2-[4-(1-methanesulfonylethyl)phenoxy]ethyl}-1,2-dihydrospiro[indole-3,4'-piperidin]-2-one;

5-chloro-1'-[2-(4-methanesulfonylphenoxy)ethyl]-1-(oxetan-3-yl)-1,2-dihydrospiro[indole-3,4'-piperidin]-2-one;

7-chloro-1'-[2-(4-methanesulfonylphenoxy)ethyl]-2-oxo-1,2-dihydrospiro[indole-3,4'-piperidine]-5-carbonitrile;

5-chloro-1'-{2-[4-(1-methanesulfonylethyl)phenoxy]ethyl}-1,2-dihydrospiro[indole-3,4'-piperidin]-2-one;

5-chloro-1'-{2-[4-(1-methanesulfonylethyl)phenoxy]ethyl}-1,2-dihydrospiro[indole-3,4'-piperidin]-2-one;

5-chloro-1'-(2-{[1-(propan-2-yl)-1H-indazol-5-yl]oxy}ethyl)-1,2-dihydrospiro[indole-3,4'-piperidin]-2-one;

5-chloro-1'-(2-{[1-(3-methanesulfonylpropyl)-1H-indazol-5-yl]oxy}ethyl)-1,2-dihydrospiro[indole-3,4'-piperidin]-2-one;

5-chloro-1'-{2-[(6-methanesulfonylpyridin-3-yl)oxy]ethyl}-1,2-dihydrospiro[indole-3,4'-piperidin]-2-one;

5-chloro-1'-{2-[(2-methanesulfonyl-2,3-dihydro-1H-isoindol-5-yl)oxy]ethyl}-1,2-dihydrospiro[indole-3,4'-piperidin]-2-one;

5-chloro-1'-[1-(4-methanesulfonylphenoxy)propan-2-yl]-1,2-dihydrospiro[indole-3,4'-piperidin]-2-one;

5-chloro-1'-[2-(4-methanesulfonylphenoxy)propyl]-1,2-dihydrospiro[indole-3,4'-piperidin]-2-one;

5-chloro-1'-{2-[4-(3-methanesulfonylpropanesulfonyl)phenoxy]ethyl}-1-methyl-1,2-dihydrospiro[indole-3,4'-piperidin]-2-one;

5-chloro-1'-{2-[(1-methyl-2-oxo-1,2,3,4-tetrahydroquinolin-6-yl)oxy]ethyl}-1,2-dihydrospiro[indole-3,4'-piperidin]-2-one;

1-methyl-1'-{2-[4-(1-methyl-1H-pyrazol-4-yl)phenoxy]ethyl}-1,2-dihydrospiro[indole-3,4'-piperidin]-2-one;

1-methyl-1'-{2-[(2-methyl-1-oxo-2,3-dihydro-1H-isoindol-5-yl)oxy]ethyl}-1,2-dihydrospiro[indole-3,4'-piperidin]-2-one;

1-methyl-1'-{2-[(3-methyl-4-oxo-3,4-dihydroquinazolin-6-yl)oxy]ethyl}-1,2-dihydrospiro[indole-3,4'-piperidin]-2-one;

5-chloro-1'-[2-(3-fluoro-4-methanesulfonylphenoxy)ethyl]-1,2-dihydrospiro[indole-3,4'-piperidin]-2-one;

1'-[2-(4-methanesulfonylphenoxy)ethyl]-1-methyl-1,2-dihydrospiro[indole-3,4'-piperidin]-2-one;

5-chloro-1'-[2-(4-methanesulfonylphenoxy)ethyl]-2-oxo-1,2-dihydrospiro[indole-3,4'-piperidine]-7-carbonitrile;

5-chloro-1'-(2-{4-[(3-hydroxycyclobutyl)sulfonyl]phenoxy}ethyl)-1,2-dihydrospiro[indole-3,4'-piperidin]-2-one;

5-chloro-1'-(2-{[1-(oxetan-3-yl)-1H-indazol-5-yl]oxy}ethyl)-1,2-dihydrospiro[indole-3,4'-piperidin]-2-one;

5-chloro-1'-{2-[4-(2-hydroxyethanesulfonyl)phenoxy]ethyl}-1,2-dihydrospiro[indole-3,4'-piperidin]-2-one;

5-chloro-1'-{1-[(1-methyl-1H-indazol-5-yl)oxy]propan-2-yl}-1,2-dihydrospiro[indole-3,4'-piperidin]-2-one;

1'-[2-(4-methanesulfonylphenoxy)ethyl]-5-methyl-1,2-dihydrospiro[indole-3,4'-piperidin]-2-one;

5-chloro-1'-[2-(quinoxalin-6-yloxy)ethyl]-1,2-dihydrospiro[indole-3,4'-piperidin]-2-one;

5-chloro-1'-{2-[(1-methyl-2-oxo-2,3-dihydro-1H-indol-5-yl)oxy]ethyl}-1,2-dihydrospiro[indole-3,4'-piperidin]-2-one;

1'-[2-(3,5-difluoro-4-methanesulfonylphenoxy)ethyl]-2-oxo-1,2-dihydrospiro[indole-3,4'-piperidine]-5-carbonitrile;

5-chloro-1'-{2-[4-(3-methyl-1H-pyrazol-4-yl)phenoxy]ethyl}-1,2-dihydrospiro[indole-3,4'-piperidin]-2-one;

5-chloro-1'-[2-(3,5-difluoro-4-methanesulfonylphenoxy)ethyl]-1,2-dihydrospiro[indole-3,4'-piperidin]-2-one;

5-chloro-1'-{2-[(1-methyl-2-oxo-2,3-dihydro-1H-1,3-benzodiazol-5-yl)oxy]ethyl}-1,2-dihydrospiro[indole-3,4'-piperidin]-2-one;

5-chloro-1'-{2-[3-(difluoromethyl)-4-methanesulfonylphenoxy]ethyl}-1,2-dihydrospiro[indole-3,4'-piperidin]-2-one;

5-chloro-1'-{2-[(1-methanesulfonyl-1,2,3,4-tetrahydroquinolin-6-yl)oxy]ethyl}-1,2-dihydrospiro[indole-3,4'-piperidin]-2-one;

1'-{2-[(1-acetyl-1,2,3,4-tetrahydroquinolin-6-yl)oxy]ethyl}-5-chloro-1,2-dihydrospiro[indole-3,4'-piperidin]-2-one;

5-chloro-1'-[2-(1H-indazol-5-yloxy)ethyl]-1,2-dihydrospiro[indole-3,4'-piperidin]-2-one;

6-(2-{5-chloro-2-oxo-1,2-dihydrospiro[indole-3,4'-piperidin]-1'-yl}ethoxy)-N-methyl-1,2,3,4-tetrahydroquinoline-1-carboxamide;

1'-{2-[(2-acetyl-2,3-dihydro-1H-isoindol-5-yl)oxy]ethyl}-5-chloro-1,2-dihydrospiro[indole-3,4'-piperidin]-2-one;

5-chloro-1'-[2-(4-methanesulfonyl-3-methylphenoxy)ethyl]-1,2-dihydrospiro[indole-3,4'-piperidin]-2-one;

5-chloro-1'-[2-(4-difluoromethanesulfonylphenoxy)ethyl]-1,2-dihydrospiro[indole-3,4'-piperidin]-2-one;

1'-[2-(4-difluoromethanesulfonylphenoxy)ethyl]-2-oxo-1,2-dihydrospiro[indole-3,4'-piperidine]-5-carbonitrile;

N-{2-[4-(2-{5-chloro-2-oxo-1,2-dihydrospiro[indole-3,4'-piperidin]-1'-yl}ethoxy)benzenesulfonyl]ethyl}-N-methylacetamide;

5-chloro-1'-{2-[4-(3-methanesulfonyloxetan-3-yl)phenoxy]ethyl}-1,2-dihydrospiro[indole-3,4'-piperidin]-2-one;

1'-[2-(4-methanesulfonyl-3-methylphenoxy)ethyl]-2-oxo-1,2-dihydrospiro[indole-3,4'-piperidine]-5-carbonitrile;

1'-{2-[(1-methyl-2-oxo-1,2,3,4-tetrahydroquinolin-6-yl)oxy]ethyl}-2-oxo-1,2-dihydrospiro[indole-3,4'-piperidine]-5-carbonitrile;

5-chloro-1'-{2-[(2-methanesulfonyl-1,2,3,4-tetrahydroisoquinolin-6-yl)oxy]ethyl}-1,2-dihydrospiro[indole-3,4'-piperidin]-2-one;

5-chloro-1'-(2-{4-[(3-methyloxetan-3-yl)sulfonyl]phenoxy}ethyl)-1,2-dihydrospiro[indole-3,4'-piperidin]-2-one;

6-(2-{5-chloro-2-oxo-1,2-dihydrospiro[indole-3,4'-piperidin]-1'-yl}ethoxy)-N-methyl-1,2,3,4-tetrahydroisoquinoline-2-carboxamide;

5-chloro-1'-(2-{[1-(3-hydroxycyclobutyl)-1H-indazol-5-yl]oxy}ethyl)-1,2-dihydrospiro[indole-3,4'-piperidin]-2-one;

5-(2-{5-chloro-2-oxo-1,2-dihydrospiro[indole-3,4'-piperidin]-1'-yl}ethoxy)-2,3-dihydro-1lambda6-benzothiophene-1,1-dione;

1'-{2-[3-(difluoromethyl)-4-methanesulfonylphenoxy]ethyl}-2-oxo-1,2-dihydrospiro[indole-3,4'-piperidine]-5-carbonitrile;

1'-{2-[(2-acetyl-1,2,3,4-tetrahydroisoquinolin-6-yl)oxy]ethyl}-5-chloro-1,2-dihydrospiro[indole-3,4'-piperidin]-2-one;

5-chloro-1'-(2-{4-[(3-hydroxycyclobutyl)sulfonyl]phenoxy}ethyl)-1,2-dihydrospiro[indole-3,4'-piperidin]-2-one;

5-chloro-1'-(2-{[1-(3-hydroxycyclobutyl)-1H-indazol-5-yl]oxy}ethyl)-1,2-dihydrospiro[indole-3,4'-piperidin]-2-one;

5-(2-{5-chloro-2-oxo-1,2-dihydrospiro[indole-3,4'-piperidin]-1'-yl}ethoxy)-N-methyl-2,3-dihydro-1H-isoindole-2-carboxamide;

1'-(2-{4-[(3-methyloxetan-3-yl)sulfonyl]phenoxy}ethyl)-2-oxo-1,2-dihydrospiro[indole-3,4'-piperidine]-5-carbonitrile;

1'-{1-[(1-methyl-2-oxo-1,2,3,4-tetrahydroquinolin-6-yl)oxy]propan-2-yl}-2-oxo-1,2-dihydrospiro[indole-3,4'-piperidine]-5-carbonitrile;

5-chloro-1'-[2-(2-fluoro-4-methanesulfonylphenoxy)ethyl]-1,2-dihydrospiro[indole-3,4'-piperidin]-2-one;

2-oxo-1'-(2-{[2-oxo-1-(propan-2-yl)-1,2,3,4-tetrahydroquinolin-6-yl]oxy}ethyl)-1,2-dihydrospiro[indole-3,4'-piperidine]-5-carbonitrile;

1'-{2-[4-(1-methanesulfonylcyclopropyl)phenoxy]ethyl}-2-oxo-1,2-dihydrospiro[indole-3,4'-piperidine]-5-carbonitrile;

5-chloro-1'-(2-{[1-(2-hydroxyethyl)-2-oxo-1,2,3,4-tetrahydroquinolin-6-yl]oxy}ethyl)-1,2-dihydrospiro[indole-3,4'-piperidin]-2-one;

5-chloro-1'-(2-{[2-oxo-1-(propan-2-yl)-1,2,3,4-tetrahydroquinolin-6-yl]oxy}ethyl)-1,2-dihydrospiro[indole-3,4'-piperidin]-2-one;

1'-{1-[(1-methyl-2-oxo-1,2,3,4-tetrahydroquinolin-6-yl)oxy]propan-2-yl}-2-oxo-1,2-dihydrospiro[indole-3,4'-piperidine]-5-carbonitrile;

1'-{1-[(1-methyl-2-oxo-1,2,3,4-tetrahydroquinolin-6-yl)oxy]propan-2-yl}-2-oxo-1,2-dihydrospiro[indole-3,4'-piperidine]-5-carbonitrile;

5-chloro-1'-{1-[3-(difluoromethyl)-4-methanesulfonylphenoxy]propan-2-yl}-1,2-dihydrospiro[indole-3,4'-piperidin]-2-one;

5-chloro-1'-{1-[(1-methyl-2-oxo-1,2,3,4-tetrahydroquinolin-6-yl)oxy]propan-2-yl}-1,2-dihydrospiro[indole-3,4'-piperidin]-2-one;

5-chloro-1'-{2-[4-(1-methanesulfonylcyclopropyl)phenoxy]ethyl}-1,2-dihydrospiro[indole-3,4'-piperidin]-2-one;

1'-{1-[3-(difluoromethyl)-4-methanesulfonylphenoxy]propan-2-yl}-2-oxo-1,2-dihydrospiro[indole-3,4'-piperidine]-5-carbonitrile;

5-chloro-1-(3-hydroxycyclobutyl)-1'-[1-(4-methanesulfonylphenoxy)propan-2-yl]-1,2-dihydrospiro[indole-3,4'-piperidin]-2-one;

5-chloro-1'-{1-[(1-methyl-2-oxo-1,2,3,4-tetrahydroquinolin-6-yl)oxy]propan-2-yl}-1,2-dihydrospiro[indole-3,4'-piperidin]-2-one;

5-chloro-1'-{1-[(1-methyl-2-oxo-1,2,3,4-tetrahydroquinolin-6-yl)oxy]propan-2-yl}-1,2-dihydrospiro[indole-3,4'-piperidin]-2-one;

N-[4-(2-{5-chloro-2-oxo-1,2-dihydrospiro[indole-3,4'-piperidin]-1'-yl}ethoxy)phenyl]-N-methylmethanesulfonamide;

N-[4-(2-{5-cyano-2-oxo-1,2-dihydrospiro[indole-3,4'-piperidin]-1'-yl}ethoxy)phenyl]-N-methylmethanesulfonamide;

5-(2-{5-chloro-2-oxo-1,2-dihydrospiro[indole-3,4'-piperidin]-1'-yl}ethoxy)-2-methanesulfonylbenzonitrile;

5-chloro-1'-(2-{[1-(2,2-difluoroethyl)-2-oxo-1,2,3,4-tetrahydroquinolin-6-yl]oxy}ethyl)-1,2-dihydrospiro[indole-3,4'-piperidin]-2-one;

1'-{2-[4-methanesulfonyl-3-(trifluoromethyl)phenoxy]ethyl}-2-oxo-1,2-dihydrospiro[indole-3,4'-piperidine]-5-carbonitrile;

5-chloro-1'-{2-[4-methanesulfonyl-3-(trifluoromethyl)phenoxy]ethyl}-1,2-dihydrospiro[indole-3,4'-piperidin]-2-one;

methyl 1-[4-(2-{5-chloro-2-oxo-1,2-dihydrospiro[indole-3,4'-piperidin]-1'-yl}ethoxy)benzenesulfonyl]cyclopropane-1-carboxylate;

1'-{2-[3-(difluoromethyl)-4-methanesulfonylphenoxy]ethyl}-1-(2-hydroxyethyl)-2-oxo-1,2-dihydrospiro[indole-3,4'-piperidine]-5-carbonitrile;

5-chloro-1'-{2-[3-(difluoromethyl)-4-methanesulfonylphenoxy]ethyl}-1-(2-hydroxyethyl)-1,2-dihydrospiro[indole-3,4'-piperidin]-2-one;

1'-(2-{[1-(2,2-difluoroethyl)-2-oxo-1,2,3,4-tetrahydroquinolin-6-yl]oxy}ethyl)-2-oxo-1,2-dihydrospiro[indole-3,4'-piperidine]-5-carbonitrile;

5-chloro-1-(3-hydroxycyclobutyl)-1'-[1-(4-methanesulfonylphenoxy)propan-2-yl]-1,2-dihydrospiro[indole-3,4'-piperidin]-2-one;

2-oxo-1'-{2-[(1,3,3-trimethyl-2-oxo-2,3-dihydro-1H-indol-5-yl)oxy]ethyl}-1,2-dihydrospiro[indole-3,4'-piperidine]-5-carbonitrile;

4-(2-{5-chloro-2-oxo-1,2-dihydrospiro[indole-3,4'-piperidin]-1'-yl}ethoxy)benzamide;

4-(2-{5-chloro-2-oxo-1,2-dihydrospiro[indole-3,4'-piperidin]-1'-yl}ethoxy)-2-fluorobenzamide;

5-(2-{5-chloro-2-oxo-1,2-dihydrospiro[indole-3,4'-piperidin]-1'-yl}ethoxy)pyridine-2-carboxamide;

6-(2-{5-chloro-2-oxo-1,2-dihydrospiro[indole-3,4'-piperidin]-1'-yl}ethoxy)-1-methyl-3,4-dihydro-1H-2lambda6,1-benzothiazine-2,2-dione;

N-[4-(2-{5-chloro-2-oxo-1,2-dihydrospiro[indole-3,4'-piperidin]-1'-yl}ethoxy)phenyl]methanesulfonamide;

1'-{2-[(1-methyl-2,2-dioxo-3,4-dihydro-1H-2lambda6,1-benzothiazin-6-yl)oxy]ethyl}-2-oxo-1,2-dihydrospiro[indole-3,4'-piperidine]-5-carbonitrile;

5-chloro-1'-(2-{[1-(oxetan-3-yl)-2-oxo-1,2,3,4-tetrahydroquinolin-6-yl]oxy}ethyl)-1,2-dihydrospiro[indole-3,4'-piperidin]-2-one;

5-chloro-1-(3-hydroxycyclobutyl)-1'-[1-(4-methanesulfonylphenoxy)propan-2-yl]-1,2-dihydrospiro[indole-3,4'-piperidin]-2-one;

1'-{2-[4-(3-methanesulfonyloxetan-3-yl)phenoxy]ethyl}-2-oxo-1,2-dihydrospiro[indole-3,4'-piperidine]-5-carbonitrile;

5-chloro-1-(3-hydroxycyclobutyl)-1'-[1-(4-methanesulfonylphenoxy)propan-2-yl]-1,2-dihydrospiro[indole-3,4'-piperidin]-2-one;

5-chloro-1-(3-hydroxycyclobutyl)-1'-[1-(4-methanesulfonylphenoxy)propan-2-yl]-1,2-dihydrospiro[indole-3,4'-piperidin]-2-one;

5-chloro-1'-[2-(4-{[1-(hydroxymethyl)cyclopropyl]sulfonyl}phenoxy)ethyl]-1,2-dihydrospiro[indole-3,4'-piperidin]-2-one;

1'-[2-(3-fluoro-4-methanesulfonylphenoxy)ethyl]-2-oxo-1,2-dihydrospiro[indole-3,4'-piperidine]-5-carbonitrile;

1'-{2-[(1-acetyl-1,2,3,4-tetrahydroquinolin-6-yl)oxy]ethyl}-2-oxo-1,2-dihydrospiro[indole-3,4'-piperidine]-5-carbonitrile;

5-chloro-1'-{2-[(8-methyl-7-oxo-5,6,7,8-tetrahydro-1,8-naphthyridin-3-yl)oxy]ethyl}-1,2-dihydrospiro[indole-3,4'-piperidin]-2-one;

1'-{2-[(8-methyl-7-oxo-5,6,7,8-tetrahydro-1,8-naphthyridin-3-yl)oxy]ethyl}-2-oxo-1,2-dihydrospiro[indole-3,4'-piperidine]-5-carbonitrile;

1'-[2-(4-methanesulfonyl-3,5-dimethylphenoxy)ethyl]-2-oxo-1,2-dihydrospiro[indole-3,4'-piperidine]-5-carbonitrile;

5-chloro-1'-[2-({3-oxo-1H,2H,3H,5H,6H,10bH-pyrrolo[2,1-a]isoquinolin-8-yl}oxy)ethyl]-1,2-dihydrospiro[indole-3,4'-piperidin]-2-one;

2-oxo-1'-[2-({3-oxo-1H,2H,3H,5H,6H,10bH-pyrrolo[2,1-a]isoquinolin-8-yl}oxy)ethyl]-1,2-dihydrospiro[indole-3,4'-piperidine]-5-carbonitrile;

6-(2-{5-cyano-2-oxo-1,2-dihydrospiro[indole-3,4'-piperidin]-1'-yl}ethoxy)-N-methyl-1,2,3,4-tetrahydroisoquinoline-2-carboxamide;

5-chloro-1'-(2-{[1-(3-hydroxycyclobutyl)-2-oxo-1,2,3,4-tetrahydroquinolin-6-yl]oxy}ethyl)-1,2-dihydrospiro[indole-3,4'-piperidin]-2-one;

5-chloro-1'-[2-(4-methanesulfonyl-3,5-dimethylphenoxy)ethyl]-1,2-dihydrospiro[indole-3,4'-piperidin]-2-one;

5-chloro-1'-{2-[(3-methyl-2-oxo-2,3-dihydro-1,3-benzoxazol-6-yl)oxy]ethyl}-1,2-dihydrospiro[indole-3,4'-piperidin]-2-one;

2-oxo-1'-[2-({3-oxo-1H,2H,3H,5H,6H,10bH-pyrrolo[2,1-a]isoquinolin-8-yl}oxy)ethyl]-1,2-dihydrospiro[indole-3,4'-piperidine]-5-carbonitrile;

2-oxo-1'-[2-({3-oxo-1H,2H,3H,5H,6H,10bH-pyrrolo[2,1-a]isoquinolin-8-yl}oxy)ethyl]-1,2-dihydrospiro[indole-3,4'-piperidine]-5-carbonitrile;

1'-{2-[4-(1-methanesulfonylethyl)phenoxy]ethyl}-2-oxo-1,2-dihydrospiro[indole-3,4'-piperidine]-5-carbonitrile;

5-chloro-1'-[2-({3-oxo-1H,2H,3H,5H,6H,10bH-pyrrolo[2,1-a]isoquinolin-8-yl}oxy)ethyl]-1,2-dihydrospiro[indole-3,4'-piperidin]-2-one;

1'-{2-[(3-methyl-2-oxo-2,3-dihydro-1,3-benzoxazol-6-yl)oxy]ethyl}-2-oxo-1,2-dihydrospiro[indole-3,4'-piperidine]-5-carbonitrile;

5-chloro-1'-[2-({3-oxo-1H,2H,3H,5H,6H,10bH-pyrrolo[2,1-a]isoquinolin-8-yl}oxy)ethyl]-1,2-dihydrospiro[indole-3,4'-piperidin]-2-one;

1'-{2-[4-(1-cyano-1-methylethyl)phenoxy]ethyl}-2-oxo-1,2-dihydrospiro[indole-3,4'-piperidine]-5-carbonitrile;

2-oxo-1'-(2-{[2-oxo-1-(propan-2-yl)-2,3-dihydro-1H-indol-5-yl]oxy}ethyl)-1,2-dihydrospiro[indole-3,4'-piperidine]-5-carbonitrile;

5-chloro-1'-{2-[(6-methanesulfonyl-5-methylpyridin-3-yl)oxy]ethyl}-1,2-dihydrospiro[indole-3,4'-piperidin]-2-one;

1'-{2-[4-(1-methanesulfonylethyl)phenoxy]ethyl}-2-oxo-1,2-dihydrospiro[indole-3,4'-piperidine]-5-carbonitrile;

1'-{2-[4-(1-methanesulfonylethyl)phenoxy]ethyl}-2-oxo-1,2-dihydrospiro[indole-3,4'-piperidine]-5-carbonitrile;

5-chloro-1'-[2-({3-methyl-2-oxo-1H,2H,3H-imidazo[4,5-b]pyridin-6-yl}oxy)ethyl]-1,2-dihydrospiro[indole-3,4'-piperidin]-2-one;

1'-{2-[(6-methanesulfonyl-5-methylpyridin-3-yl)oxy]ethyl}-2-oxo-1,2-dihydrospiro[indole-3,4'-piperidine]-5-carbonitrile;

5-chloro-1'-(2-{4-[methyl(methylimino)oxo-lambda6-sulfanyl]phenoxy}ethyl)-1,2-dihydrospiro[indole-3,4'-piperidin]-2-one;

1'-(2-{4-[methyl(methylimino)oxo-lambda6-sulfanyl]phenoxy}ethyl)-2-oxo-1,2-dihydrospiro[indole-3,4'-piperidine]-5-carbonitrile;

1'-{2-[(8-acetyl-5,6,7,8-tetrahydro-1,8-naphthyridin-3-yl)oxy]ethyl}-5-chloro-1,2-dihydrospiro[indole-3,4'-piperidin]-2-one;

1'-{2-[(8-acetyl-5,6,7,8-tetrahydro-1,8-naphthyridin-3-yl)oxy]ethyl}-2-oxo-1,2-dihydrospiro[indole-3,4'-piperidine]-5-carbonitrile;

5-chloro-1'-{2-[4-methanesulfonyl-3-(oxetan-3-yl)phenoxy]ethyl}-1,2-dihydrospiro[indole-3,4'-piperidin]-2-one;

5-chloro-1'-[2-({3-oxo-1H,2H,3H,5H,6H,10bH-imidazo[4,3-a]isoquinolin-8-yl}oxy)ethyl]-1,2-dihydrospiro[indole-3,4'-piperidin]-2-one;

1'-{2-[3,5-difluoro-4-(1-methanesulfonylethyl)phenoxy]ethyl}-2-oxo-1,2-dihydrospiro[indole-3,4'-piperidine]-5-carbonitrile;

5-chloro-1'-[2-(3-chloro-4-methanesulfonylphenoxy)ethyl]-1,2-dihydrospiro[indole-3,4'-piperidin]-2-one;

1'-[2-(3-chloro-4-methanesulfonylphenoxy)ethyl]-2-oxo-1,2-dihydrospiro[indole-3,4'-piperidine]-5-carbonitrile;

5-chloro-1'-(2-{[2-oxo-1-(propan-2-yl)-2,3-dihydro-1H-indol-5-yl]oxy}ethyl)-1,2-dihydrospiro[indole-3,4'-piperidin]-2-one;

5-chloro-1'-{2-[(2-methyl-1-oxo-2,3-dihydro-1H-isoindol-5-yl)oxy]ethyl}-1,2-dihydrospiro[indole-3,4'-piperidin]-2-one;

2-oxo-1'-[2-({3-oxo-1H,2H,3H,5H,6H,10bH-imidazo[4,3-a]isoquinolin-8-yl}oxy)ethyl]-1,2-dihydrospiro[indole-3,4'-piperidine]-5-carbonitrile;

1'-[1-(3,5-difluoro-4-methanesulfonylphenoxy)propan-2-yl]-2-oxo-1,2-dihydrospiro[indole-3,4'-piperidine]-5-carbonitrile;

2-oxo-1'-[2-({3-oxo-1H,2H,3H,5H,6H,10bH-imidazo[4,3-a]isoquinolin-8-yl}oxy)ethyl]-1,2-dihydrospiro[indole-3,4'-piperidine]-5-carbonitrile;

5-chloro-1'-[2-({3-oxo-1H,2H,3H,5H,6H,10bH-imidazo[4,3-a]isoquinolin-8-yl}oxy)ethyl]-1,2-dihydrospiro[indole-3,4'-piperidin]-2-one;

2-oxo-1'-[2-({3-oxo-1H,2H,3H,5H,6H,10bH-imidazo[4,3-a]isoquinolin-8-yl}oxy)ethyl]-1,2-dihydrospiro[indole-3,4'-piperidine]-5-carbonitrile;

5-chloro-1'-[2-({3-oxo-1H,2H,3H,5H,6H,10bH-imidazo[4,3-a]isoquinolin-8-yl}oxy)ethyl]-1,2-dihydrospiro[indole-3,4'-piperidin]-2-one;

4-(2-{5-chloro-2-oxo-1,2-dihydrospiro[indole-3,4'-piperidin]-1'-yl}ethoxy)-2-methylbenzamide;

5-chloro-1'-{2-[(2-oxo-1,2,3,4-tetrahydroquinolin-6-yl)oxy]ethyl}-1,2-dihydrospiro[indole-3,4'-piperidin]-2-one;

4-(2-{5-chloro-2-oxo-1,2-dihydrospiro[indole-3,4'-piperidin]-1'-yl}ethoxy)-2-fluoro-N,N-dimethylbenzamide;

5-chloro-1'-{2-[3-fluoro-4-(morpholine-4-carbonyl)phenoxy]ethyl}-1,2-dihydrospiro[indole-3,4'-piperidin]-2-one;

4-[4-(2-{5-chloro-2-oxo-1,2-dihydrospiro[indole-3,4'-piperidin]-1'-yl}ethoxy)-2-fluorobenzoyl]-1lambda6-thiomorpholine-1,1-dione;

1'-[2-(4-{[1-(azetidine-1-carbonyl)cyclopropyl]sulfonyl}phenoxy)ethyl]-5-chloro-1,2-dihydrospiro[indole-3,4'-piperidin]-2-one;

5-chloro-1'-{2-[3-fluoro-4-(3-methanesulfonylazetidine-1-carbonyl)phenoxy]ethyl}-1,2-dihydrospiro[indole-3,4'-piperidin]-2-one;

6-(2-{5-chloro-2-oxo-1,2-dihydrospiro[indole-3,4'-piperidin]-1'-yl}ethoxy)-2-methyl-3,4-dihydro-2H-1lambda6,2-benzothiazine-1,1-dione;

1'-{2-[(2-methyl-1,1-dioxo-3,4-dihydro-2H-1lambda6,2-benzothiazin-6-yl)oxy]ethyl}-2-oxo-1,2-dihydrospiro[indole-3,4'-piperidine]-5-carbonitrile;

1'-{2-[4-(azetidine-1-carbonyl)-3-fluorophenoxy]ethyl}-5-chloro-1,2-dihydrospiro[indole-3,4'-piperidin]-2-one;

5-chloro-1'-{2-[3,5-difluoro-4-(3-methanesulfonyloxetan-3-yl)phenoxy]ethyl}-1,2-dihydrospiro[indole-3,4'-piperidin]-2-one;

5-chloro-1'-{2-[3-fluoro-4-(3-hydroxyazetidine-1-carbonyl)phenoxy]ethyl}-1,2-dihydrospiro[indole-3,4'-piperidin]-2-one;

1'-{2-[3,5-difluoro-4-(1-methanesulfonylethyl)phenoxy]ethyl}-2-oxo-1,2-dihydrospiro[indole-3,4'-piperidine]-5-carbonitrile;

1'-{2-[3,5-difluoro-4-(1-methanesulfonylethyl)phenoxy]ethyl}-2-oxo-1,2-dihydrospiro[indole-3,4'-piperidine]-5-carbonitrile;

N-[4-(2-{5-chloro-2-oxo-1,2-dihydrospiro[indole-3,4'-piperidin]-1'-yl}ethoxy)-2,6-difluorophenyl]-N-methylmethanesulfonamide;

4-(2-{5-chloro-2-oxo-1,2-dihydrospiro[indole-3,4'-piperidin]-1'-yl}ethoxy)-2-fluoro-N-methylbenzamide;

1-(2-hydroxyethyl)-1'-{2-[4-methanesulfonyl-3-(trifluoromethyl)phenoxy]ethyl}-2-oxo-1,2-dihydrospiro[indole-3,4'-piperidine]-5-carbonitrile;

N-[4-(2-{5-cyano-2-oxo-1,2-dihydrospiro[indole-3,4'-piperidin]-1'-yl}ethoxy)-2,6-difluorophenyl]-N-methylmethanesulfonamide;

1-[4-(2-{5-chloro-2-oxo-1,2-dihydrospiro[indole-3,4'-piperidin]-1'-yl}ethoxy)benzenesulfonyl]-N-methylcyclopropane-1-carboxamide;

5-chloro-1'-{2-[3-(1,2-difluoroethyl)-4-methanesulfonylphenoxy]ethyl}-1,2-dihydrospiro[indole-3,4'-piperidin]-2-one;

1-[4-(2-{5-chloro-2-oxo-1,2-dihydrospiro[indole-3,4'-piperidin]-1'-yl}ethoxy)benzenesulfonyl]-N,N-dimethylcyclopropane-1-carboxamide;

1'-{2-[3,5-difluoro-4-(3-methanesulfonyloxetan-3-yl)phenoxy]ethyl}-2-oxo-1,2-dihydrospiro[indole-3,4'-piperidine]-5-carbonitrile;

5-chloro-1'-{2-[3-(1,2-dihydroxyethyl)-4-methanesulfonylphenoxy]ethyl}-1,2-dihydrospiro[indole-3,4'-piperidin]-2-one;

5-(2-{5-chloro-2-oxo-1,2-dihydrospiro[indole-3,4'-piperidin]-1'-yl}ethoxy)-N,N-dimethylpyridine-2-carboxamide;

4-(2-{5-cyano-2-oxo-1,2-dihydrospiro[indole-3,4'-piperidin]-1'-yl}ethoxy)-2-fluorobenzamide;

1'-{2-[4-(3-aminoazetidine-1-carbonyl)-3-fluorophenoxy]ethyl}-5-chloro-1,2-dihydrospiro[indole-3,4'-piperidin]-2-one;

5-chloro-1'-[2-({6-[(3-methyloxetan-3-yl)sulfonyl]pyridin-3-yl}oxy)ethyl]-1,2-dihydrospiro[indole-3,4'-piperidin]-2-one;

5-chloro-1'-{2-[3,5-difluoro-4-(1-methanesulfonylethyl)phenoxy]ethyl}-1,2-dihydrospiro[indole-3,4'-piperidin]-2-one;

5-chloro-1'-{2-[3,5-difluoro-4-(1-methanesulfonylethyl)phenoxy]ethyl}-1,2-dihydrospiro[indole-3,4'-piperidin]-2-one;

5-chloro-1'-{2-[3,5-difluoro-4-(1-methanesulfonylethyl)phenoxy]ethyl}-1,2-dihydrospiro[indole-3,4'-piperidin]-2-one;

5-chloro-1'-{2-[3-(1,2-difluoroethyl)-4-methanesulfonylphenoxy]ethyl}-1,2-dihydrospiro[indole-3,4'-piperidin]-2-one;

5-chloro-1'-(2-{[1-(3-hydroxycyclobutyl)-2-oxo-1,2,3,4-tetrahydroquinolin-6-yl]oxy}ethyl)-1,2-dihydrospiro[indole-3,4'-piperidin]-2-one;

5-chloro-1'-{2-[3-(1,2-difluoroethyl)-4-methanesulfonylphenoxy]ethyl}-1,2-dihydrospiro[indole-3,4'-piperidin]-2-one;

N-{1-[4-(2-{5-chloro-2-oxo-1,2-dihydrospiro[indole-3,4'-piperidin]-1'-yl}ethoxy)-2-fluorobenzoyl]azetidin-3-yl}methanesulfonamide;

1'-{2-[3-(1,2-difluoroethyl)-4-methanesulfonylphenoxy]ethyl}-2-oxo-1,2-dihydrospiro[indole-3,4'-piperidine]-5-carbonitrile;

4-(2-{5-chloro-2-oxo-1,2-dihydrospiro[indole-3,4'-piperidin]-1'-yl}ethoxy)-N-methylbenzamide;

1'-(2-{4-[methyl(methylimino)oxo-lambda6-sulfanyl]phenoxy}ethyl)-2-oxo-1,2-dihydrospiro[indole-3,4'-piperidine]-5-carbonitrile;

1'-{1-[4-(3-methanesulfonyloxetan-3-yl)phenoxy]propan-2-yl}-2-oxo-1,2-dihydrospiro[indole-3,4'-piperidine]-5-carbonitrile;

5-chloro-1'-(2-{4-[methyl(methylimino)oxo-lambda6-sulfanyl]phenoxy}ethyl)-1,2-dihydrospiro[indole-3,4'-piperidin]-2-one;

5-chloro-1-(2-hydroxyethyl)-1'-{2-[4-(3-methanesulfonyloxetan-3-yl)phenoxy]ethyl}-1,2-dihydrospiro[indole-3,4'-piperidin]-2-one;

5-chloro-1'-(2-{4-[methyl(methylimino)oxo-lambda6-sulfanyl]phenoxy}ethyl)-1,2-dihydrospiro[indole-3,4'-piperidin]-2-one;

1'-(2-{4-[methyl(methylimino)oxo-lambda6-sulfanyl]phenoxy}ethyl)-2-oxo-1,2-dihydrospiro[indole-3,4'-piperidine]-5-carbonitrile;

1'-[2-(4-{[dimethyl(oxo)-lambda6-sulfanylidene]amino}phenoxy)ethyl]-2-oxo-1,2-dihydrospiro[indole-3,4'-piperidine]-5-carbonitrile;

1'-{2-[4-(3-methanesulfonyloxetan-3-yl)phenoxy]ethyl}-2-oxo-1-(2,2,2-trifluoroethyl)-1,2-dihydrospiro[indole-3,4'-piperidine]-5-carbonitrile;

5-chloro-1'-{2-[4-(3-methanesulfonyloxetan-3-yl)phenoxy]ethyl}-1-(2,2,2-trifluoroethyl)-1,2-dihydrospiro[indole-3,4'-piperidin]-2-one;

1'-{2-[4-(1-methanesulfonylcyclobutyl)phenoxy]ethyl}-2-oxo-1,2-dihydrospiro[indole-3,4'-piperidine]-5-carbonitrile;

1'-{2-[3-(difluoromethoxy)-4-methanesulfonylphenoxy]ethyl}-2-oxo-1,2-dihydrospiro[indole-3,4'-piperidine]-5-carbonitrile;

5-chloro-1'-{2-[3-(difluoromethoxy)-4-methanesulfonylphenoxy]ethyl}-1,2-dihydrospiro[indole-3,4'-piperidin]-2-one;

5-chloro-1'-{2-[(6-{[1-(hydroxymethyl)cyclopropyl]sulfonyl}pyridin-3-yl)oxy]ethyl}-1,2-dihydrospiro[indole-3,4'-piperidin]-2-one;

1'-{1-[4-(3-methanesulfonyloxetan-3-yl)phenoxy]propan-2-yl}-2-oxo-1,2-dihydrospiro[indole-3,4'-piperidine]-5-carbonitrile;

1'-{2-[3-(1,2-difluoroethyl)-4-methanesulfonylphenoxy]ethyl}-2-oxo-1,2-dihydrospiro[indole-3,4'-piperidine]-5-carbonitrile;

1'-{1-[4-(3-methanesulfonyloxetan-3-yl)phenoxy]propan-2-yl}-2-oxo-1,2-dihydrospiro[indole-3,4'-piperidine]-5-carbonitrile;

5-chloro-1'-{2-[4-(1-methanesulfonylcyclobutyl)phenoxy]ethyl}-1,2-dihydrospiro[indole-3,4'-piperidin]-2-one;

1'-{2-[(7-fluoro-1-methyl-2-oxo-2,3-dihydro-1H-indol-5-yl)oxy]ethyl}-2-oxo-1,2-dihydrospiro[indole-3,4'-piperidine]-5-carbonitrile;

1'-{2-[3-(1,2-difluoroethyl)-4-methanesulfonylphenoxy]ethyl}-2-oxo-1,2-dihydrospiro[indole-3,4'-piperidine]-5-carbonitrile;

1'-{2-[4-(4-methanesulfonyloxan-4-yl)phenoxy]ethyl}-2-oxo-1,2-dihydrospiro[indole-3,4'-piperidine]-5-carbonitrile;

5-chloro-1'-{2-[4-(4-methanesulfonyloxan-4-yl)phenoxy]ethyl}-1,2-dihydrospiro[indole-3,4'-piperidin]-2-one;

1'-{2-[4-(3-methanesulfonyloxetan-3-yl)phenoxy]ethyl}-1-methyl-2-oxo-1,2-dihydrospiro[indole-3,4'-piperidine]-5-carbonitrile;

5-chloro-1'-(2-{3-oxo-3H-spiro[2-benzofuran-1,3'-oxetan]-5-yloxy}ethyl)-1,2-dihydrospiro[indole-3,4'-piperidin]-2-one;

5-chloro-1'-{2-[4-(3-methanesulfonyloxetan-3-yl)-3-(trifluoromethyl)phenoxy]ethyl}-1,2-dihydrospiro[indole-3,4'-piperidin]-2-one;

N-(4-{2-[5-(2-hydroxyethyl)-2-oxo-1,2-dihydrospiro[indole-3,4'-piperidin]-1'-yl]ethoxy}-2-(trifluoromethyl)phenyl)methanesulfonamide;

1'-{2-[4-(3-methanesulfonyloxetan-3-yl)-3-(trifluoromethyl)phenoxy]ethyl}-2-oxo-1,2-dihydrospiro[indole-3,4'-piperidine]-5-carbonitrile;

6-(2-{5-chloro-2-oxo-1,2-dihydrospiro[indole-3,4'-piperidin]-1'-yl}ethoxy)-3,4-dihydro-2H-1lambda6,2-benzothiazine-1,1-dione;

2-oxo-1'-{2-[(1-oxo-2,3-dihydro-1H-isoindol-5-yl)oxy]ethyl}-1,2-dihydrospiro[indole-3,4'-piperidine]-5-carbonitrile;

5-chloro-1'-{2-[(1-oxo-2,3-dihydro-1H-isoindol-5-yl)oxy]ethyl}-1,2-dihydrospiro[indole-3,4'-piperidin]-2-one;

5-chloro-1'-{2-[(7-fluoro-2-oxo-2,3-dihydro-1H-indol-5-yl)oxy]ethyl}-1,2-dihydrospiro[indole-3,4'-piperidin]-2-one;

1'-{2-[(1,1-dioxo-3,4-dihydro-2H-1lambda6,2-benzothiazin-6-yl)oxy]ethyl}-2-oxo-1,2-dihydrospiro[indole-3,4'-piperidine]-5-carbonitrile;

5-chloro-1'-[2-({2-[(3-methyloxetan-3-yl)oxy]pyrimidin-5-yl}oxy)ethyl]-1,2-dihydrospiro[indole-3,4'-piperidin]-2-one;

3-[4-(2-{5-cyano-2-oxo-1,2-dihydrospiro[indole-3,4'-piperidin]-1'-yl}ethoxy)phenyl]-N-methyloxetane-3-carboxamide;

3-[4-(2-{5-cyano-2-oxo-1,2-dihydrospiro[indole-3,4'-piperidin]-1'-yl}ethoxy)phenyl]-N,N-dimethyloxetane-3-carboxamide;

2-[4-(2-{5-chloro-2-oxo-1,2-dihydrospiro[indole-3,4'-piperidin]-1'-yl}ethoxy)phenyl]-1lambda6-thiolane-1,1-dione;

2-[4-(2-{5-chloro-2-oxo-1,2-dihydrospiro[indole-3,4'-piperidin]-1'-yl}ethoxy)phenyl]-1lambda6-thiolane-1,1-dione;

1'-[2-(4-{6-methanesulfonyl-2-oxaspiro[3.3]heptan-6-yl}phenoxy)ethyl]-2-oxo-1,2-dihydrospiro[indole-3,4'-piperidine]-5-carbonitrile;

1'-(2-{4-[3-(azetidine-1-carbonyl)oxetan-3-yl]phenoxy}ethyl)-2-oxo-1,2-dihydrospiro[indole-3,4'-piperidine]-5-carbonitrile;

5-(2-{5-chloro-2-oxo-1,2-dihydrospiro[indole-3,4'-piperidin]-1'-yl}ethoxy)pyrimidine-2-carboxamide;

2-[4-(2-{5-chloro-2-oxo-1,2-dihydrospiro[indole-3,4'-piperidin]-1'-yl}ethoxy)phenyl]-1lambda6-thiolane-1,1-dione;

1'-(2-{4-[3-(ethanesulfonyl)oxetan-3-yl]phenoxy}ethyl)-2-oxo-1,2-dihydrospiro[indole-3,4'-piperidine]-5-carbonitrile;

2-[4-(2-{5-cyano-2-oxo-1,2-dihydrospiro[indole-3,4'-piperidin]-1'-yl}ethoxy)phenyl]-2-methylpropanamide;

1'-{2-[4-(1,1-dioxo-1lambda6-thiolan-2-yl)phenoxy]ethyl}-2-oxo-1,2-dihydrospiro[indole-3,4'-piperidine]-5-carbonitrile;

4-(2-{5-chloro-2-oxo-1,2-dihydrospiro[indole-3,4'-piperidin]-1'-yl}ethoxy)-2-(difluoromethyl)benzamide;

1'-{2-[3,5-difluoro-4-(3-methanesulfonyloxetan-3-yl)phenoxy]ethyl}-1-methyl-2-oxo-1,2-dihydrospiro[indole-3,4'-piperidine]-5-carbonitrile;

1'-[2-({2-[(3-methyloxetan-3-yl)oxy]pyrimidin-5-yl}oxy)ethyl]-2-oxo-1,2-dihydrospiro[indole-3,4'-piperidine]-5-carbonitrile;

1'-(2-{4-[3-(3-fluoroazetidine-1-carbonyl)oxetan-3-yl]phenoxy}ethyl)-2-oxo-1,2-dihydrospiro[indole-3,4'-piperidine]-5-carbonitrile;

4-(2-{5-cyano-2-oxo-1,2-dihydrospiro[indole-3,4'-piperidin]-1'-yl}ethoxy)-2-(difluoromethyl)benzamide;

5-chloro-1'-[2-(4-{6-methanesulfonyl-2-oxaspiro[3.3]heptan-6-yl}phenoxy)ethyl]-1,2-dihydrospiro[indole-3,4'-piperidin]-2-one;

5-chloro-1'-(2-{[2-(1-methanesulfonylethyl)pyrimidin-5-yl]oxy}ethyl)-1,2-dihydrospiro[indole-3,4'-piperidin]-2-one;

N-[4-(2-{5-chloro-2-oxo-1,2-dihydrospiro[indole-3,4'-piperidin]-1'-yl}ethoxy)phenyl]-N-(2-hydroxyethyl)methanesulfonamide;

6-[4-(2-{5-chloro-2-oxo-1,2-dihydrospiro[indole-3,4'-piperidin]-1'-yl}ethoxy)-2-fluorobenzoyl]-2lambda6-thia-6-azaspiro[3.3]heptane-2,2-dione;

5-chloro-1'-{2-[3-fluoro-4-{6-methanesulfonyl-2,6-diazaspiro[3.3]heptane-2-carbonyl}phenoxy)ethyl]-1,2-dihydrospiro[indole-3,4'-piperidin]-2-one;

4-[4-(2-{5-chloro-2-oxo-1,2-dihydrospiro[indole-3,4'-piperidin]-1'-yl}ethoxy)-2,6-difluorobenzoyl]-1lambda6-thiomorpholine-1,1-dione;

5-chloro-1'-(2-{[8-(2-hydroxyethyl)-7-oxo-5,6,7,8-tetrahydro-1,8-naphthyridin-3-yl]oxy}ethyl)-1,2-dihydrospiro[indole-3,4'-piperidin]-2-one;

5-chloro-1'-(2-{[2-(1-methanesulfonylcyclopropyl)pyrimidin-5-yl]oxy}ethyl)-1,2-dihydrospiro[indole-3,4'-piperidin]-2-one;

1'-{2-[4-(1,1-dioxo-1lambda6-thiomorpholine-4-carbonyl)-3,5-difluorophenoxy]ethyl}-1-methyl-2-oxo-1,2-dihydrospiro[indole-3,4'-piperidine]-5-carbonitrile;

4-[4-(2-{5-chloro-2-oxo-1,2-dihydrospiro[indole-3,4'-piperidin]-1'-yl}ethoxy)-2-(trifluoromethyl)benzoyl]-1lambda6-thiomorpholine-1,1-dione;

1'-{2-[4-(1,1-dioxo-1lambda6-thiomorpholine-4-carbonyl)-3-(trifluoromethyl)phenoxy]ethyl}-1-methyl-2-oxo-1,2-dihydrospiro[indole-3,4'-piperidine]-5-carbonitrile;

1'-(2-{[6-(2-methanesulfonylpropan-2-yl)pyridin-3-yl]oxy}ethyl)-2-oxo-1,2-dihydrospiro[indole-3,4'-piperidine]-5-carbonitrile;

5-chloro-1'-{2-[4-(3-hydroxy-1-methanesulfonylcyclobutyl)phenoxy]ethyl}-1,2-dihydrospiro[indole-3,4'-piperidin]-2-one;

5-(difluoromethyl)-1'-(2-{[2-(1-methanesulfonylcyclopropyl)pyrimidin-5-yl]oxy}ethyl)-1,2-dihydrospiro[indole-3,4'-piperidin]-2-one;

5-chloro-1'-(2-{[8-(3-hydroxycyclobutyl)-7-oxo-5,6,7,8-tetrahydro-1,8-naphthyridin-3-yl]oxy}ethyl)-1,2-dihydrospiro[indole-3,4'-piperidin]-2-one;

4-(4-{2-[5-chloro-1-(2-hydroxyethyl)-2-oxo-1,2-dihydrospiro[indole-3,4'-piperidin]-1'-yl]ethoxy}-2-(trifluoromethyl)benzoyl]-1lambda6-thiomorpholine-1,1-dione;

4-(2-{5-chloro-2-oxo-1,2-dihydrospiro[indole-3,4'-piperidin]-1'-yl}ethoxy)-N-(1,1-dioxo-1lambda6-thiolan-3-yl)-2-fluorobenzamide;

5-chloro-1'-{2-[4-(3-hydroxy-1-methanesulfonylcyclobutyl)phenoxy]ethyl}-1,2-dihydrospiro[indole-3,4'-piperidin]-2-one;

5-chloro-1'-{2-[4-(3-hydroxy-1-methanesulfonylcyclobutyl)phenoxy]ethyl}-1,2-dihydrospiro[indole-3,4'-piperidin]-2-one;

4-(2-{5-chloro-2-oxo-1,2-dihydrospiro[indole-3,4'-piperidin]-1'-yl}ethoxy)-N-(1,1-dioxo-1lambda6-thian-4-yl)-2-fluorobenzamide;

4-(2-{5-chloro-2-oxo-1,2-dihydrospiro[indole-3,4'-piperidin]-1'-yl}ethoxy)-N-(1,1-dioxo-1lambda6-thiolan-3-yl)-2-fluorobenzamide;

4-(2-{5-chloro-2-oxo-1,2-dihydrospiro[indole-3,4'-piperidin]-1'-yl}ethoxy)-N-(1,1-dioxo-1lambda6-thiolan-3-yl)-2-fluorobenzamide;

5-chloro-1'-(2-{[8-(3-hydroxycyclobutyl)-7-oxo-5,6,7,8-tetrahydro-1,8-naphthyridin-3-yl]oxy}ethyl)-1,2-dihydrospiro[indole-3,4'-piperidin]-2-one;

5-(difluoromethoxy)-1'-(2-{[2-(1-methanesulfonylcyclopropyl)pyrimidin-5-yl]oxy}ethyl)-1,2-dihydrospiro[indole-3,4'-piperidin]-2-one;

5-chloro-1'-(2-{[2-(1-methanesulfonylethyl)pyrimidin-5-yl]oxy}ethyl)-1,2-dihydrospiro[indole-3,4'-piperidin]-2-one;

5-chloro-1'-(2-{[2-(1-methanesulfonylethyl)pyrimidin-5-yl]oxy}ethyl)-1,2-dihydrospiro[indole-3,4'-piperidin]-2-one;

5-(difluoromethyl)-1'-[2-({7-oxo-8-[3-hydroxy-3-methylcyclobutyl]-5,6,7,8-tetrahydro-1,8-naphthyridin-3-yl}oxy)ethyl]-1,2-dihydrospiro[indole-3,4'-piperidin]-2-one;

5-chloro-1'-[2-({7-oxo-8-[3-hydroxy-3-methylcyclobutyl]-5,6,7,8-tetrahydro-1,8-naphthyridin-3-yl}oxy)ethyl]-1,2-dihydrospiro[indole-3,4'-piperidin]-2-one;

5-chloro-1'-[2-({2-oxo-1-[3-hydroxy-3-methylcyclobutyl]-1H,2H,4H-pyrido[2,3-d][1,3]oxazin-6-yl}oxy)ethyl]-1,2-dihydrospiro[indole-3,4'-piperidin]-2-one;

5-chloro-1'-[2-({7-oxo-8-[3-ethyl-3-hydroxycyclobutyl]-5,6,7,8-tetrahydro-1,8-naphthyridin-3-yl}oxy)ethyl]-1,2-dihydrospiro[indole-3,4'-piperidin]-2-one;

5-chloro-1'-{2-[(7-oxo-5,6,7,8-tetrahydro-1,8-naphthyridin-3-yl)oxy]ethyl}-1,2-dihydrospiro[indole-3,4'-piperidin]-2-one;

5-chloro-1'-[2-({7-oxo-8-[3-cyclopropyl-3-hydroxycyclobutyl]-5,6,7,8-tetrahydro-1,8-naphthyridin-3-yl}oxy)ethyl]-1,2-dihydrospiro[indole-3,4'-piperidin]-2-one;

5-chloro-1'-(2-{[8-(3-cyclopropyl-3-hydroxycyclobutyl)-7-oxo-5,6,7,8-tetrahydro-1,8-naphthyridin-3-yl]oxy}ethyl)-1,2-dihydrospiro[indole-3,4'-piperidin]-2-one;

5-chloro-1'-(2-{[8-(3-hydroxy-3-methylazetidin-1-yl)-1,7-naphthyridin-3-yl]oxy}ethyl)-1,2-dihydrospiro[indole-3,4'-piperidin]-2-one;

5-chloro-1'-[2-({7-oxo-8-[3-hydroxy-3-methylcyclobutyl]-5,6,7,8-tetrahydro-1,8-naphthyridin-3-yl}oxy)ethyl]-1,2-dihydrospiro[indole-3,4'-piperidin]-2-one;

5-(difluoromethyl)-1'-[2-({7-oxo-8-[3-(hydroxymethyl)cyclobutyl]-5,6,7,8-tetrahydro-1,8-naphthyridin-3-yl}oxy)ethyl]-1,2-dihydrospiro[indole-3,4'-piperidin]-2-one;

5-(difluoromethyl)-1'-{2-[(7-oxo-8-{[3-hydroxy-3-methylcyclobutyl]methyl}-5,6,7,8-tetrahydro-1,8-naphthyridin-3-yl)oxy]ethyl}-1,2-dihydrospiro[indole-3,4'-piperidin]-2-one;

5-chloro-1'-{2-[(7-oxo-8-{[3-hydroxy-3-methylcyclobutyl]methyl}-5,6,7,8-tetrahydro-1,8-naphthyridin-3-yl)oxy]ethyl}-1,2-dihydrospiro[indole-3,4'-piperidin]-2-one;

5-chloro-1'-(2-{[8-(3-hydroxyazetidin-1-yl)-1,7-naphthyridin-3-yl]oxy}ethyl)-1,2-dihydrospiro[indole-3,4'-piperidin]-2-one;

5-chloro-1'-(2-{[8-(3-hydroxy-3-methylcyclobutyl)-7-oxo-5,6,7,8-tetrahydro-1,8-naphthyridin-3-yl]oxy}ethyl)-1,2-dihydrospiro[indole-3,4'-piperidin]-2-one;

5-(difluoromethyl)-1'-[2-({8-[3-(hydroxymethyl)cyclobutyl]-7-oxo-5,6,7,8-tetrahydro-1,8-naphthyridin-3-yl}oxy)ethyl]-1,2-dihydrospiro[indole-3,4'-piperidin]-2-one;

5-chloro-1'-[2-({7-oxo-8-[3-hydroxy-3-(propan-2-yl)cyclobutyl]-5,6,7,8-tetrahydro-1,8-naphthyridin-3-yl}oxy)ethyl]-1,2-dihydrospiro[indole-3,4'-piperidin]-2-one;

5-chloro-1'-(2-{[8-(3-ethyl-3-hydroxycyclobutyl)-7-oxo-5,6,7,8-tetrahydro-1,8-naphthyridin-3-yl]oxy}ethyl)-1,2-dihydrospiro[indole-3,4'-piperidin]-2-one;

5-chloro-1'-[2-({7-oxo-8-[3-(hydroxymethyl)cyclobutyl]-5,6,7,8-tetrahydro-1,8-naphthyridin-3-yl}oxy)ethyl]-1,2-dihydrospiro[indole-3,4'-piperidin]-2-one;

5-(difluoromethyl)-1'-[2-({8-[(3-hydroxy-3-methylcyclobutyl)methyl]-7-oxo-5,6,7,8-tetrahydro-1,8-naphthyridin-3-yl}oxy)ethyl]-1,2-dihydrospiro[indole-3,4'-piperidin]-2-one;

5-chloro-1'-[2-({7-oxo-8-[3-ethyl-3-hydroxycyclobutyl]-5,6,7,8-tetrahydro-1,8-naphthyridin-3-yl}oxy)ethyl]-1,2-dihydrospiro[indole-3,4'-piperidin]-2-one;

5-chloro-1'-[2-({7-oxo-8-[3-hydroxy-3-methylcyclobutyl]-7,8-dihydro-1,8-naphthyridin-3-yl}oxy)ethyl]-1,2-dihydrospiro[indole-3,4'-piperidin]-2-one;

5-(difluoromethyl)-1'-[2-({7-oxo-8-[3-hydroxy-3-methylcyclobutyl]-7,8-dihydro-1,8-naphthyridin-3-yl}oxy)ethyl]-1,2-dihydrospiro[indole-3,4'-piperidin]-2-one;

5-(difluoromethoxy)-1'-[2-({7-oxo-8-[3-hydroxy-3-methylcyclobutyl]-5,6,7,8-tetrahydro-1,8-naphthyridin-3-yl}oxy)ethyl]-1,2-dihydrospiro[indole-3,4'-piperidin]-2-one;

5-chloro-1'-[2-({8-[3-(hydroxymethyl)cyclobutyl]-7-oxo-5,6,7,8-tetrahydro-1,8-naphthyridin-3-yl}oxy)ethyl]-1,2-dihydrospiro[indole-3,4'-piperidin]-2-one;

5-chloro-1'-[2-({8-[(3-hydroxy-3-methylcyclobutyl)methyl]-7-oxo-5,6,7,8-tetrahydro-1,8-naphthyridin-3-yl}oxy)ethyl]-1,2-dihydrospiro[indole-3,4'-piperidin]-2-one;

5-(difluoromethoxy)-1'-[2-({7-oxo-8-[3-hydroxy-3-methylcyclobutyl]-7,8-dihydro-1,8-naphthyridin-3-yl}oxy)ethyl]-1,2-dihydrospiro[indole-3,4'-piperidin]-2-one;

5-chloro-7-iodo-1'-[2-({7-oxo-8-[3-hydroxy-3-methylcyclobutyl]-5,6,7,8-tetrahydro-1,8-naphthyridin-3-yl}oxy)ethyl]-1,2-dihydrospiro[indole-3,4'-piperidin]-2-one;

5-chloro-1'-[2-({7-oxo-8-[3-hydroxy-3-(propan-2-yl)cyclobutyl]-5,6,7,8-tetrahydro-1,8-naphthyridin-3-yl}oxy)ethyl]-1,2-dihydrospiro[indole-3,4'-piperidin]-2-one;

5-chloro-1'-[2-({7-oxo-8-[3-(hydroxymethyl)cyclobutyl]-5,6,7,8-tetrahydro-1,8-naphthyridin-3-yl}oxy)ethyl]-1,2-dihydrospiro[indole-3,4'-piperidin]-2-one;

5-(difluoromethyl)-1'-(2-{[6-(1-hydroxyethyl)-5-(trifluoromethyl)pyridin-3-yl]oxy}ethyl)-1,2-dihydrospiro[indole-3,4'-piperidin]-2-one;

1'-(2-{[6-(1-hydroxyethyl)-5-(trifluoromethyl)pyridin-3-yl]oxy}ethyl)-2-oxo-1,2-dihydrospiro[indole-3,4'-piperidine]-5-carbonitrile;

5-chloro-1'-(2-{[5-(difluoromethyl)-7-oxo-8-[(cis)-3-hydroxy-3-methylcyclobutyl]-7,8-dihydro-1,8-naphthyridin-3-yl]oxy}ethyl)-1,2-dihydrospiro[indole-3,4'-piperidin]-2-one;

5-(difluoromethyl)-1'-(2-{[5-(difluoromethyl)-7-oxo-8-[(cis)-3-hydroxy-3-methylcyclobutyl]-7,8-dihydro-1,8-naphthyridin-3-yl]oxy}ethyl)-1,2-dihydrospiro[indole-3,4'-piperidin]-2-one;

5-chloro-1'-[2-({7-oxo-8-[3-hydroxy-3-methylcyclobutyl]-5-(trifluoromethyl)-7,8-dihydro-1,8-naphthyridin-3-yl}oxy)ethyl]-1,2-dihydrospiro[indole-3,4'-piperidin]-2-one;

5-(difluoromethyl)-1'-[2-({7-oxo-8-[3-hydroxy-3-methylcyclobutyl]-5-(trifluoromethyl)-7,8-dihydro-1,8-naphthyridin-3-yl}oxy)ethyl]-1,2-dihydrospiro[indole-3,4'-piperidin]-2-one;

5-chloro-1'-[2-({2-oxo-1-[3-hydroxy-3-methylcyclobutyl]-1H,2H,3H-pyrrolo[2,3-b]pyridin-5-yl}oxy)ethyl]-1,2-dihydrospiro[indole-3,4'-piperidin]-2-one;

5-(difluoromethyl)-1'-[2-({2-oxo-1-[3-hydroxy-3-methylcyclobutyl]-1H,2H,3H-pyrrolo[2,3-b]pyridin-5-yl}oxy)ethyl]-1,2-dihydrospiro[indole-3,4'-piperidin]-2-one;

5-chloro-1'-[2-({2-oxo-1-[3-hydroxy-3-methylcyclobutyl]-1H,2H,3H-pyrrolo[2,3-b]pyridin-5-yl}oxy)ethyl]-1,2-dihydrospiro[indole-3,4'-piperidin]-2-one;

5-(difluoromethyl)-1'-[2-({2-oxo-1-[3-hydroxy-3-methylcyclobutyl]-1H,2H,3H-pyrrolo[2,3-b]pyridin-5-yl}oxy)ethyl]-1,2-dihydrospiro[indole-3,4'-piperidin]-2-one;

5-chloro-1'-[2-({1-[3-hydroxy-3-methylcyclobutyl]-1H-pyrrolo[2,3-b]pyridin-5-yl}oxy)ethyl]-1,2-dihydrospiro[indole-3,4'-piperidin]-2-one;

5-(difluoromethyl)-1'-[2-({1-[3-hydroxy-3-methylcyclobutyl]-1H-pyrrolo[2,3-b]pyridin-5-yl}oxy)ethyl]-1,2-dihydrospiro[indole-3,4'-piperidin]-2-one;

5-chloro-1'-[2-({2-oxo-1-[3-hydroxy-3-methylcyclobutyl]-1H,2H-pyrido[2,3-d]pyrimidin-6-yl}oxy)ethyl]-1,2-dihydrospiro[indole-3,4'-piperidin]-2-one;

5-chloro-1'-[2-({2-oxo-1-[3-hydroxy-3-methylcyclobutyl]-1H,2H,3H,4H-pyrido[2,3-d]pyrimidin-6-yl}oxy)ethyl]-1,2-dihydrospiro[indole-3,4'-piperidin]-2-one;

5-chloro-1'-[2-({1-[3-hydroxy-3-methylcyclobutyl]-1H-pyrazolo[3,4-b]pyridin-5-yl}oxy)ethyl]-1,2-dihydrospiro[indole-3,4'-piperidin]-2-one;

5-chloro-1'-[2-({3-oxo-4-[3-hydroxy-3-methylcyclobutyl]-3H,4H-pyrido[2,3-b]pyrazin-7-yl}oxy)ethyl]-1,2-dihydrospiro[indole-3,4'-piperidin]-2-one;

5-chloro-1'-(2-{[4-(3-hydroxy-3-methylcyclobutyl)pyrido[3,2-d]pyrimidin-7-yl]oxy}ethyl)-1,2-dihydrospiro[indole-3,4'-piperidin]-2-one;

5-chloro-1'-(2-{[8-(3-hydroxy-3-methylcyclobutyl)-1,7-naphthyridin-3-yl]oxy}ethyl)-1,2-dihydrospiro[indole-3,4'-piperidin]-2-one;

5-chloro-1'-(2-{[8-(3-hydroxy-3-methylazetidin-1-yl)pyrido[2,3-d]pyridazin-3-yl]oxy}ethyl)-1,2-dihydrospiro[indole-3,4'-piperidin]-2-one;

5-chloro-1'-(2-{[4-(3-hydroxy-3-methylazetidin-1-yl)pyrido[3,2-d]pyrimidin-7-yl]oxy}ethyl)-1,2-dihydrospiro[indole-3,4'-piperidin]-2-one;

5-chloro-1'-(2-{[8-(3-hydroxyazetidin-1-yl)pyrido[2,3-d]pyridazin-3-yl]oxy}ethyl)-1,2-dihydrospiro[indole-3,4'-piperidin]-2-one;

5-chloro-1'-(2-{[4-(3-hydroxyazetidin-1-yl)pyrido[3,2-d]pyrimidin-7-yl]oxy}ethyl)-1,2-dihydrospiro[indole-3,4'-piperidin]-2-one;

5-chloro-1'-[2-({3-[3-hydroxy-3-methylcyclobutyl]-3H-imidazo[4,5-b]pyridin-6-yl}oxy)ethyl]-1,2-dihydrospiro[indole-3,4'-piperidin]-2-one;

5-chloro-1'-[2-({2-oxo-3-[3-hydroxy-3-methylcyclobutyl]-1H,2H,3H-imidazo[4,5-b]pyridin-6-yl}oxy)ethyl]-1,2-dihydrospiro[indole-3,4'-piperidin]-2-one;

5-chloro-1'-[2-({8-[3-(hydroxymethyl)azetidin-1-yl]-1,7-naphthyridin-3-yl}oxy)ethyl]-1,2-dihydrospiro[indole-3,4'-piperidin]-2-one;

5-chloro-1'-[2-({2-oxo-3-[(cis)-3-hydroxy-3-methylcyclobutyl]-2H,3H-[1,3]oxazolo[4,5-b]pyridin-6-yl}oxy)ethyl]-1,2-dihydrospiro[indole-3,4'-piperidin]-2-one;

5-(difluoromethyl)-1'-(2-{[2-(3-hydroxy-3-methylazetidin-1-yl)pyrimidin-5-yl]oxy}ethyl)-1,2-dihydrospiro[indole-3,4'-piperidin]-2-one;

5-chloro-1'-{2-[(2-{6-hydroxy-2-azaspiro[3.3]heptan-2-yl}pyrimidin-5-yl)oxy]ethyl}-1,2-dihydrospiro[indole-3,4'-piperidin]-2-one;

5-chloro-1'-(2-{[2-(3-ethyl-3-hydroxyazetidin-1-yl)pyrimidin-5-yl]oxy}ethyl)-1,2-dihydrospiro[indole-3,4'-piperidin]-2-one;

5-chloro-1'-[2-({7-oxo-8-[(cis)-3-cyclopropyl-3-hydroxycyclobutyl]-5,6,7,8-tetrahydro-1,8-naphthyridin-3-yl}oxy)ethyl]-1,2-dihydrospiro[indole-3,4'-piperidin]-2-one;

5-chloro-1'-(2-{[6-(1-hydroxyethyl)-5-(trifluoromethyl)pyridin-3-yl]oxy}ethyl)-1,2-dihydrospiro[indole-3,4'-piperidin]-2-one;

5,7-dichloro-1'-(2-{[2-(1-methanesulfonylcyclopropyl)pyrimidin-5-yl]oxy}ethyl)-1,2-dihydrospiro[indole-3,4'-piperidin]-2-one;

5-chloro-1'-(2-{[6-(1-hydroxy-2-methanesulfonylpropan-2-yl)-5-(trifluoromethyl)pyridin-3-yl]oxy}ethyl)-1,2-dihydrospiro[indole-3,4'-piperidin]-2-one;

5-chloro-1'-(2-{[6-(1-hydroxy-2-methanesulfonylpropan-2-yl)-5-(trifluoromethyl)pyridin-3-yl]oxy}ethyl)-1,2-dihydrospiro[indole-3,4'-piperidin]-2-one;

5-chloro-1'-(2-{[6-(1-hydroxy-2-methanesulfonylpropan-2-yl)-5-(trifluoromethyl)pyridin-3-yl]oxy}ethyl)-1,2-dihydrospiro[indole-3,4'-piperidin]-2-one;

1'-(2-{[8-(3-hydroxy-3-methylcyclobutyl)-7-oxo-5,6,7,8-tetrahydro-1,8-naphthyridin-3-yl]oxy}ethyl)-2-oxo-1,2-dihydrospiro[indole-3,4'-piperidine]-5-carbonitrile;

5-chloro-1'-(2-{[6-(3-hydroxy-3-methylazetidin-1-yl)-5-(trifluoromethyl)pyridin-3-yl]oxy}ethyl)-1,2-dihydrospiro[indole-3,4'-piperidin]-2-one;

1'-(2-{[8-(3-hydroxy-3-methylcyclobutyl)-7-oxo-7,8-dihydro-1,8-naphthyridin-3-yl]oxy}ethyl)-2-oxo-1,2-dihydrospiro[indole-3,4'-piperidine]-5-carbonitrile;

5-chloro-1'-(2-{[1-(3-hydroxy-3-methylcyclobutyl)-1H-pyrazolo[3,4-b]pyridin-5-yl]oxy}ethyl)-1,2-dihydrospiro[indole-3,4'-piperidin]-2-one;

5-chloro-1'-(2-{[1-(3-hydroxy-3-methylcyclobutyl)-1H-pyrazolo[3,4-b]pyridin-5-yl]oxy}ethyl)-1,2-dihydrospiro[indole-3,4'-piperidin]-2-one;

5,7-dichloro-1'-(2-{[8-(3-hydroxy-3-methylcyclobutyl)-7-oxo-5,6,7,8-tetrahydro-1,8-naphthyridin-3-yl]oxy}ethyl)-1,2-dihydrospiro[indole-3,4'-piperidin]-2-one;

1'-(2-{[1-(3-hydroxy-3-methylcyclobutyl)-1H-pyrrolo[2,3-b]pyridin-5-yl]oxy}ethyl)-2-oxo-1,2-dihydrospiro[indole-3,4'-piperidine]-5-carbonitrile;

1'-(2-{[6-(2-hydroxypropan-2-yl)-5-(trifluoromethyl)pyridin-3-yl]oxy}ethyl)-2-oxo-1,2-dihydrospiro[indole-3,4'-piperidine]-5-carbonitrile;

5-chloro-1'-{2-[4-(1-methanesulfonylpiperidin-4-yl)phenoxy]ethyl}-1-(2H3)methyl-1,2-dihydrospiro[indole-3,4'-piperidin]-2-one;

5-chloro-1-(2H3)methyl-1'-(2-{4-[methyl(methylimino)oxo-lambda6-sulfanyl]-3-(trifluoromethyl)phenoxy}ethyl)-1,2-dihydrospiro[indole-3,4'-piperidin]-2-one;

5-chloro-1-(2H3)methyl-1'-(2-{4-[3-(propane-2-sulfonyl)oxetan-3-yl]phenoxy}ethyl)-1,2-dihydrospiro[indole-3,4'-piperidin]-2-one;

5-chloro-1'-{2-[4-(1-methanesulfonylcyclobutyl)phenoxy]ethyl}-1-(2H3)methyl-1,2-dihydrospiro[indole-3,4'-piperidin]-2-one;

5-chloro-1-(2H3)methyl-1'-{2-[(2-methyl-1-oxo-2,3-dihydro-1H-isoindol-5-yl)oxy]ethyl}-1,2-dihydrospiro[indole-3,4'-piperidin]-2-one;

5-chloro-1'-(2-{[8-(2-hydroxy-2-methylpropyl)-7-oxo-5,6,7,8-tetrahydro-1,8-naphthyridin-3-yl]oxy}ethyl)-1-(2H3)methyl-1,2-dihydrospiro[indole-3,4'-piperidin]-2-one;

5-chloro-1'-[2-(4-methanesulfonylphenoxy)ethyl]-1-(2H3)methyl-1,2-dihydrospiro[indole-3,4'-piperidin]-2-one;

5-chloro-1'-(2-{[8-(3-hydroxy-3-methylcyclobutyl)-7-oxo-5,6,7,8-tetrahydro-1,8-naphthyridin-3-yl]oxy}ethyl)-1-(2H3)methyl-1,2-dihydrospiro[indole-3,4'-piperidin]-2-one;

5-chloro-1'-[2-({2-[1-(hydroxymethyl)cyclopropyl]pyrimidin-5-yl}oxy)ethyl]-1-(2H3)methyl-1,2-dihydrospiro[indole-3,4'-piperidin]-2-one;

6-{2-[5-chloro-1-(2H3)methyl-2-oxo-1,2-dihydrospiro[indole-3,4'-piperidin]-1'-yl]ethoxy}-8-fluoro-3,4-dihydro-2H-1lambda6,2-benzothiazine-1,1-dione;

5-chloro-1'-(2-{[2-(3-methanesulfonyloxetan-3-yl)pyrimidin-5-yl]oxy}ethyl)-1-(2H3)methyl-1,2-dihydrospiro[indole-3,4'-piperidin]-2-one;

5-chloro-1'-(2-{[8-(3-hydroxycyclobutyl)-7-oxo-5,6,7,8-tetrahydro-1,8-naphthyridin-3-yl]oxy}ethyl)-1-(2H3)methyl-1,2-dihydrospiro[indole-3,4'-piperidin]-2-one;

5-chloro-1'-(2-{[2-(1-methanesulfonylcyclopropyl)pyrimidin-5-yl]oxy}ethyl)-1-(2H3)methyl-1,2-dihydrospiro[indole-3,4'-piperidin]-2-one;

5-chloro-1'-(2-{[2-(1-methanesulfonylethyl)pyrimidin-5-yl]oxy}ethyl)-1-(2H3)methyl-1,2-dihydrospiro[indole-3,4'-piperidin]-2-one;

5-chloro-1'-(2-{[8-(3-hydroxy-3-methylcyclobutyl)-7-oxo-5,6,7,8-tetrahydro-1,8-naphthyridin-3-yl]oxy}(1,1,2,2-2H4)ethyl)-1,2-dihydrospiro[indole-3,4'-piperidin]-2-one;

5-chloro-1'-(2-{[2-(3-hydroxy-3-methylcyclobutyl)-7-(trifluoromethyl)-2H-indazol-5-yl]oxy}ethyl)-1,2-dihydrospiro[indole-3,4'-piperidin]-2-one;

1'-(2-{[2-(3-hydroxy-3-methylcyclobutyl)-7-(trifluoromethyl)-2H-indazol-5-yl]oxy}ethyl)-2-oxo-1,2-dihydrospiro[indole-3,4'-piperidine]-5-carbonitrile;

5-chloro-1'-(2-{[2-(3-hydroxyoxetan-3-yl)pyrimidin-5-yl]oxy}ethyl)-1,2-dihydrospiro[indole-3,4'-piperidin]-2-one;

5-chloro-1'-(2-{[2-(1-hydroxycyclobutyl)pyrimidin-5-yl]oxy}ethyl)-1,2-dihydrospiro[indole-3,4'-piperidin]-2-one;

1'-(2-{[6-(3-hydroxy-3-methylazetidin-1-yl)-5-(trifluoromethyl)pyridin-3-yl]oxy}ethyl)-2-oxo-1,2-dihydrospiro[indole-3,4'-piperidine]-5-carbonitrile;

1'-(2-{[2-(1-hydroxy-2-methylpropan-2-yl)pyrimidin-5-yl]oxy}ethyl)-2-oxo-1,2-dihydrospiro[indole-3,4'-piperidine]-5-carbonitrile;

1'-(2-{[1-(3-hydroxy-3-methylcyclobutyl)-7-(trifluoromethyl)-1H-1,3-benzodiazol-5-yl]oxy}ethyl)-2-oxo-1,2-dihydrospiro[indole-3,4'-piperidine]-5-carbonitrile;

5-chloro-1'-(2-{[1-(3-hydroxy-3-methylcyclobutyl)-7-(trifluoromethyl)-1H-1,2,3-benzotriazol-5-yl]oxy}ethyl)-1,2-dihydrospiro[indole-3,4'-piperidin]-2-one;

1'-(2-{[1-(3-hydroxy-3-methylcyclobutyl)-7-(trifluoromethyl)-1H-1,2,3-benzotriazol-5-yl]oxy}ethyl)-2-oxo-1,2-dihydrospiro[indole-3,4'-piperidine]-5-carbonitrile;

1'-(2-{[1-(3-hydroxy-3-methylcyclobutyl)-1H-pyrazolo[3,4-b]pyridin-5-yl]oxy}ethyl)-2-oxo-1,2-dihydrospiro[indole-3,4'-piperidine]-5-carbonitrile;

1'-(2-{[1-(3-hydroxy-3-methylcyclobutyl)-1H-pyrazolo[3,4-b]pyridin-5-yl]oxy}ethyl)-2-oxo-1,2-dihydrospiro[indole-3,4'-piperidine]-5-carbonitrile;

1'-(2-{[1-(3-hydroxy-3-methylcyclobutyl)-1H-pyrazolo[3,4-b]pyridin-5-yl]oxy}ethyl)-2-oxo-1,2-dihydrospiro[indole-3,4'-piperidine]-5-carbonitrile;

5-(2-{5-chloro-2-oxo-1,2-dihydrospiro[indole-3,4'-piperidin]-1'-yl}ethoxy)-1-(3-hydroxy-3-methylcyclobutyl)-1H-1,3-benzodiazole-7-carbonitrile;

5-chloro-1'-(2-{[3-(3-hydroxy-3-methylcyclobutyl)-3H-[1,2,3]triazolo[4,5-b]pyridin-6-yl]oxy}ethyl)-1,2-dihydrospiro[indole-3,4'-piperidin]-2-one;

5-chloro-1'-(2-{[2-(2,2-dimethyl-1,3-dioxolan-4-yl)pyrimidin-5-yl]oxy}ethyl)-1,2-dihydrospiro[indole-3,4'-piperidin]-2-one;

5-chloro-1'-(2-{[1-(3-hydroxy-3-methylcyclobutyl)-2-methyl-7-(trifluoromethyl)-1H-1,3-benzodiazol-5-yl]oxy}ethyl)-1,2-dihydrospiro[indole-3,4'-piperidin]-2-one;

1'-(2-{[1-(3-hydroxy-3-methylcyclobutyl)-2-methyl-7-(trifluoromethyl)-1H-1,3-benzodiazol-5-yl]oxy}ethyl)-2-oxo-1,2-dihydrospiro[indole-3,4'-piperidine]-5-carbonitrile;

5-chloro-1'-{2-[4-(1-methanesulfonylpiperidin-4-yl)phenoxy]ethyl}-1,2-dihydrospiro[indole-3,4'-piperidin]-2-one;

5-chloro-1'-(2-{[7-(difluoromethyl)-1-(3-hydroxy-3-methylcyclobutyl)-1H-1,3-benzodiazol-5-yl]oxy}ethyl)-1,2-dihydrospiro[indole-3,4'-piperidin]-2-one;

1'-(2-{[7-(difluoromethyl)-1-(3-hydroxy-3-methylcyclobutyl)-1H-1,3-benzodiazol-5-yl]oxy}ethyl)-2-oxo-1,2-dihydrospiro[indole-3,4'-piperidine]-5-carbonitrile;

5-chloro-1'-(2-{[7-(difluoromethoxy)-1-(3-hydroxy-3-methylcyclobutyl)-1H-1,3-benzodiazol-5-yl]oxy}ethyl)-1,2-dihydrospiro[indole-3,4'-piperidin]-2-one;

1'-(2-{[7-(difluoromethoxy)-1-(3-hydroxy-3-methylcyclobutyl)-1H-1,3-benzodiazol-5-yl]oxy}ethyl)-2-oxo-1,2-dihydrospiro[indole-3,4'-piperidine]-5-carbonitrile;

5-chloro-1'-(2-{[2-(2-hydroxypropan-2-yl)pyrimidin-5-yl]oxy}ethyl)-7-iodo-1,2-dihydrospiro[indole-3,4'-piperidin]-2-one;

5-(difluoromethyl)-1'-(2-{[1-(3-hydroxy-3-methylcyclobutyl)-7-(trifluoromethyl)-1H-1,3-benzodiazol-5-yl]oxy}ethyl)-1,2-dihydrospiro[indole-3,4'-piperidin]-2-one;

5-chloro-1'-(2-{[3-(3-hydroxy-3-methylcyclobutyl)-2-methyl-3H-imidazo[4,5-b]pyridin-6-yl]oxy}ethyl)-1,2-dihydrospiro[indole-3,4'-piperidin]-2-one;

5-chloro-1'-(2-{[8-(2-hydroxy-2-methylpropyl)-7-oxo-5,6,7,8-tetrahydro-1,8-naphthyridin-3-yl]oxy}ethyl)-1,2-dihydrospiro[indole-3,4'-piperidin]-2-one;

5-chloro-1'-(2-{[1-(3-hydroxy-3-methylcyclobutyl)-7-(trifluoromethyl)-1H-1,3-benzodiazol-5-yl]oxy}ethyl)-7-iodo-1,2-dihydrospiro[indole-3,4'-piperidin]-2-one;

5-chloro-1'-(2-{[7-fluoro-1-(3-hydroxy-3-methylcyclobutyl)-1H-1,3-benzodiazol-5-yl]oxy}ethyl)-1,2-dihydrospiro[indole-3,4'-piperidin]-2-one;

1'-(2-{[7-fluoro-1-(3-hydroxy-3-methylcyclobutyl)-1H-1,3-benzodiazol-5-yl]oxy}ethyl)-2-oxo-1,2-dihydrospiro[indole-3,4'-piperidine]-5-carbonitrile;

5-chloro-1'-(2-{[1-(3-hydroxy-3-methylcyclobutyl)-2-oxo-8-(trifluoromethyl)-1,2,3,4-tetrahydroquinazolin-6-yl]oxy}ethyl)-1,2-dihydrospiro[indole-3,4'-piperidin]-2-one;

1'-(2-{[1-(3-hydroxy-3-methylcyclobutyl)-2-oxo-8-(trifluoromethyl)-1,2,3,4-tetrahydroquinazolin-6-yl]oxy}ethyl)-2-oxo-1,2-dihydrospiro[indole-3,4'-piperidine]-5-carbonitrile;

5-chloro-1'-[2-({7,7-dimethyl-5-oxo-5H,7H-furo[3,4-b]pyridin-3-yl}oxy)ethyl]-1,2-dihydrospiro[indole-3,4'-piperidin]-2-one;

5-chloro-1'-{2-[(2-{6-hydroxy-6-methyl-2-azaspiro[3.3]heptan-2-yl}pyrimidin-5-yl)oxy]ethyl}-1,2-dihydrospiro[indole-3,4'-piperidin]-2-one;

5-chloro-1'-{2-[1'-(3-hydroxy-3-methylcyclobutyl)-2'-oxo-1',2'-dihydrospiro[cyclopropane-1,3'-pyrrolo[2,3-b]pyridin]-5'-yloxy]ethyl}-1,2-dihydrospiro[indole-3,4'-piperidin]-2-one;

5-chloro-1'-[2-({8-[3-hydroxy-3-(2H3)methylcyclobutyl]-7-oxo-5,6,7,8-tetrahydro-1,8-naphthyridin-3-yl}oxy)ethyl]-1,2-dihydrospiro[indole-3,4'-piperidin]-2-one;

5-chloro-1'-[2-({8-[3-hydroxy-3-(2H3)methylcyclobutyl]-7-oxo-5,6,7,8-tetrahydro-1,8-naphthyridin-3-yl}oxy)(1,1,2,2-2H4)ethyl]-1,2-dihydrospiro[indole-3,4'-piperidin]-2-one;

5-chloro-1'-(2-{[1-(3-hydroxy-3-methylcyclobutyl)-7-(trifluoromethyl)-1H-1,3-benzodiazol-5-yl]oxy}(1,1,2,2-2H4)ethyl)-1,2-dihydrospiro[indole-3,4'-piperidin]-2-one;

5-chloro-1'-(2-{[1-(3-hydroxy-3-methylcyclobutyl)-7-(trifluoromethyl)-1H-indazol-5-yl]oxy}ethyl)-1,2-dihydrospiro[indole-3,4'-piperidin]-2-one;

1'-(2-{[1-(3-hydroxy-3-methylcyclobutyl)-7-(trifluoromethyl)-1H-indazol-5-yl]oxy}ethyl)-2-oxo-1,2-dihydrospiro[indole-3,4'-piperidine]-5-carbonitrile;

5-chloro-1'-(2-{[2-(3-hydroxy-3-methylcyclobutyl)-7-(trifluoromethyl)-1H-1,3-benzodiazol-5-yl]oxy}ethyl)-1,2-dihydrospiro[indole-3,4'-piperidin]-2-one;

5-chloro-1'-(2-{[1-(3-hydroxy-3-methylcyclobutyl)-3-(hydroxymethyl)-2-oxo-7-(trifluoromethyl)-2,3-dihydro-1H-1,3-benzodiazol-5-yl]oxy}ethyl)-1,2-dihydrospiro[indole-3,4'-piperidin]-2-one;

5-chloro-1'-(2-{[1-(3-hydroxy-3-methylcyclobutyl)-2-oxo-7-(trifluoromethyl)-2,3-dihydro-1H-1,3-benzodiazol-5-yl]oxy}ethyl)-1,2-dihydrospiro[indole-3,4'-piperidin]-2-one;

1'-(2-{[1-(3-hydroxy-3-methylcyclobutyl)-3-(hydroxymethyl)-2-oxo-7-(trifluoromethyl)-2,3-dihydro-1H-1,3-benzodiazol-5-yl]oxy}ethyl)-2-oxo-1,2-dihydrospiro[indole-3,4'-piperidine]-5-carbonitrile;

1'-(2-{[1-(3-hydroxy-3-methylcyclobutyl)-2-oxo-7-(trifluoromethyl)-2,3-dihydro-1H-1,3-benzodiazol-5-yl]oxy}ethyl)-2-oxo-1,2-dihydrospiro[indole-3,4'-piperidine]-5-carbonitrile;

5-chloro-1'-(2-{[1-(3-hydroxy-3-methylcyclobutyl)-7-(trifluoromethyl)-1H-imidazo[4,5-b]pyridin-5-yl]oxy}ethyl)-1,2-dihydrospiro[indole-3,4'-piperidin]-2-one; and 5-chloro-1'-(2-{3-[(3-hydroxy-3-methylcyclobutyl]-4-(trifluoromethyl)-3H-1,3,5-triazainden-6-yloxy}ethyl)spiro[indoline-3,4'-piperidin]-2-one.

In some embodiments, a compound of formula (I) is selected from the group consisting of:

5-chloro-1'-(2-{[2-(1-methanesulfonylethyl)pyrimidin-5-yl]oxy}ethyl)-1,2-dihydrospiro[indole-3,4'-piperidin]-2-one;

5-chloro-1'-[2-({2-[(1S)-1-methanesulfonylethyl]pyrimidin-5-yl}oxy)ethyl]-1,2-dihydrospiro[indole-3,4'-piperidin]-2-one;

5-chloro-1'-[2-({2-[(1R)-1-methanesulfonylethyl]pyrimidin-5-yl}oxy)ethyl]-1,2-dihydrospiro[indole-3,4'-piperidin]-2-one;

5-chloro-1'-(2-{[2-(1-methanesulfonylcyclopropyl)pyrimidin-5-yl]oxy}ethyl)-1,2-dihydrospiro[indole-3,4'-piperidin]-2-one;

5-(difluoromethyl)-1'-(2-{[2-(1-methanesulfonylcyclopropyl)pyrimidin-5-yl]oxy}ethyl)-1,2-dihydrospiro[indole-3,4'-piperidin]-2-one;

5-(difluoromethoxy)-1'-(2-{[2-(1-methanesulfonylcyclopropyl)pyrimidin-5-yl]oxy}ethyl)-1,2-dihydrospiro[indole-3,4'-piperidin]-2-one;

5,7-dichloro-1'-[2-(4-methanesulfonylphenoxy)ethyl]-1,2-dihydrospiro[indole-3,4'-piperidin]-2-one;

7-chloro-1'-[2-(4-methanesulfonylphenoxy)ethyl]-2-oxo-1,2-dihydrospiro[indole-3,4'-piperidine]-5-carbonitrile;

5-chloro-1'-[2-(4-methanesulfonylphenoxy)ethyl]-2-oxo-1,2-dihydrospiro[indole-3,4'-piperidine]-7-carbonitrile;

5-chloro-1'-[(2S)-1-(4-methanesulfonylphenoxy)propan-2-yl]-1,2-dihydrospiro[indole-3,4'-piperidin]-2-one;

5-chloro-1'-[(2S)-2-(4-methanesulfonylphenoxy)propyl]-1,2-dihydrospiro[indole-3,4'-piperidin]-2-one;

1'-[(2S)-1-(4-methanesulfonylphenoxy)propan-2-yl]-1,2-dihydrospiro[indole-3,4'-piperidin]-2-one;

1'-[(2S)-2-(4-methanesulfonylphenoxy)propyl]-1,2-dihydrospiro[indole-3,4'-piperidin]-2-one;

5-chloro-1'-(2-{[1-(3-methanesulfonylpropyl)-1H-indazol-5-yl]oxy}ethyl)-1,2-dihydrospiro[indole-3,4'-piperidin]-2-one;

5-chloro-1'-(2-{[1-(oxetan-3-yl)-1H-indazol-5-yl]oxy}ethyl)-1,2-dihydrospiro[indole-3,4'-piperidin]-2-one;

5-chloro-1'-(2-{[1-(propan-2-yl)-1H-indazol-5-yl]oxy}ethyl)-1,2-dihydrospiro[indole-3,4'-piperidin]-2-one;

5-chloro-1'-[2-(4-{[(cis)-3-hydroxycyclobutyl]sulfonyl}phenoxy)ethyl]-1,2-dihydrospiro[indole-3,4'-piperidin]-2-one;

5-chloro-1-(2-hydroxyethyl)-1'-[2-(4-methanesulfonylphenoxy)ethyl]-1,2-dihydrospiro[indole-3,4'-piperidin]-2-one;

1'-[2-(4-methanesulfonylphenoxy)ethyl]-1-[(cis)-3-hydroxycyclobutyl]-1,2-dihydrospiro[indole-3,4'-piperidin]-2-one;
5-chloro-1'-[2-(4-methanesulfonylphenoxy)ethyl]-1-(2-methoxyethyl)-1,2-dihydrospiro[indole-3,4'-piperidin]-2-one;
1'-[2-(4-methanesulfonylphenoxy)ethyl]-1-(2-methoxyethyl)-1,2-dihydrospiro[indole-3,4'-piperidin]-2-one;
5-chloro-1'-[2-(4-methanesulfonylphenoxy)ethyl]-1-(oxetan-3-yl)-1,2-dihydrospiro[indole-3,4'-piperidin]-2-one;
5-chloro-1'-{2-[4-(3-methanesulfonylpropanesulfonyl)phenoxy]ethyl}-1-methyl-1,2-dihydrospiro[indole-3,4'-piperidin]-2-one;
5-bromo-1-(2-hydroxyethyl)-1'-[2-(4-methanesulfonylphenoxy)ethyl]-1,2-dihydrospiro[indole-3,4'-piperidin]-2-one;
1'-[2-(4-methanesulfonylphenoxy)ethyl]-1-(2-methoxyethyl)-2-oxo-1,2-dihydrospiro[indole-3,4'-piperidine]-5-carbonitrile;
1-[2-(4-methanesulfonylphenoxy)ethyl]-1',2'-dihydrospiro[azepane-4,3'-indol]-2'-one;
5-chloro-1'-{2-[(1-methyl-2-oxo-1,2,3,4-tetrahydroquinolin-6-yl)oxy]ethyl}-1,2-dihydrospiro[indole-3,4'-piperidin]-2-one;
1'-[1-(4-methanesulfonylphenoxy)propan-2-yl]-1,2-dihydrospiro[indole-3,4'-piperidin]-2-one;
1-methyl-1'-{2-[(3-methyl-4-oxo-3,4-dihydroquinazolin-6-yl)oxy]ethyl}-1,2-dihydrospiro[indole-3,4'-piperidin]-2-one;
1-methyl-1'-{2-[(2-methyl-1-oxo-2,3-dihydro-1H-isoindol-5-yl)oxy]ethyl}-1,2-dihydrospiro[indole-3,4'-piperidin]-2-one;
1-methyl-1'-{2-[4-(1-methyl-1H-pyrazol-4-yl)phenoxy]ethyl}-1,2-dihydrospiro[indole-3,4'-piperidin]-2-one;
5-(2-{1-methyl-2-oxo-1,2-dihydrospiro[indole-3,4'-piperidin]-1'-yl}ethoxy)-2,3-dihydro-1λ6-benzothiophene-1,1-dione;
1-methyl-1'-{2-[(1-methyl-2-oxo-2,3-dihydro-1H-indol-5-yl)oxy]ethyl}-1,2-dihydrospiro[indole-3,4'-piperidin]-2-one;
1-methyl-1'-[2-(quinoxalin-6-yloxy)ethyl]-1,2-dihydrospiro[indole-3,4'-piperidin]-2-one;
1-methyl-1'-{2-[4-(5-methyl-1,2,4-oxadiazol-3-yl)phenoxy]ethyl}-1,2-dihydrospiro[indole-3,4'-piperidin]-2-one;
1'-{2-[(1-acetyl-1,2,3,4-tetrahydroquinolin-6-yl)oxy]ethyl}-1-methyl-1,2-dihydrospiro[indole-3,4'-piperidin]-2-one;
1-methyl-1'-{2-[4-(2-oxopyrrolidin-1-yl)phenoxy]ethyl}-1,2-dihydrospiro[indole-3,4'-piperidin]-2-one;
5-chloro-1'-{2-[4-(1-methanesulfonylethyl)phenoxy]ethyl}-1,2-dihydrospiro[indole-3,4'-piperidin]-2-one;
5-chloro-1'-(2-{4-[(1S)-1-methanesulfonylethyl]phenoxy}ethyl)-1,2-dihydrospiro[indole-3,4'-piperidin]-2-one;
5-chloro-1'-(2-{4-[(1R)-1-methanesulfonylethyl]phenoxy}ethyl)-1,2-dihydrospiro[indole-3,4'-piperidin]-2-one;
5-chloro-1'-{2-[4-(3-methanesulfonylpropanesulfonyl)phenoxy]ethyl}-1,2-dihydrospiro[indole-3,4'-piperidin]-2-one;
1'-[2-(3,5-difluoro-4-methanesulfonylphenoxy)ethyl]-1,2-dihydrospiro[indole-3,4'-piperidin]-2-one;
5-chloro-1'-{2-[4-(cyclopropanesulfonyl)phenoxy]ethyl}-1,2-dihydrospiro[indole-3,4'-piperidin]-2-one;
1'-[2-(4-difluoromethanesulfonylphenoxy)ethyl]-1,2-dihydrospiro[indole-3,4'-piperidin]-2-one;
4-(2-{5-chloro-2-oxo-1,2-dihydrospiro[indole-3,4'-piperidin]-1'-yl}ethoxy)benzamide;
4-(2-{5-chloro-2-oxo-1,2-dihydrospiro[indole-3,4'-piperidin]-1'-yl}ethoxy)-2-fluorobenzamide;
5-(2-{5-chloro-2-oxo-1,2-dihydrospiro[indole-3,4'-piperidin]-1'-yl}ethoxy)pyridine-2-carboxamide;
5-chloro-1'-[2-(2-fluoro-4-methanesulfonylphenoxy)ethyl]-1,2-dihydrospiro[indole-3,4'-piperidin]-2-one;
4-(2-{5-chloro-2-oxo-1,2-dihydrospiro[indole-3,4'-piperidin]-1'-yl}ethoxy)-2-methylbenzamide;
5-(2-{5-chloro-2-oxo-1,2-dihydrospiro[indole-3,4'-piperidin]-1'-yl}ethoxy)-2-methanesulfonylbenzonitrile;
5-(2-{5-chloro-2-oxo-1,2-dihydrospiro[indole-3,4'-piperidin]-1'-yl}ethoxy)-N,N-dimethylpyridine-2-carboxamide;
4-(2-{5-chloro-2-oxo-1,2-dihydrospiro[indole-3,4'-piperidin]-1'-yl}ethoxy)-N-methylbenzamide;
5-chloro-1'-{2-[(1-methanesulfonyl-1,2,3,4-tetrahydroquinolin-6-yl)oxy]ethyl}-1,2-dihydrospiro[indole-3,4'-piperidin]-2-one;
5-chloro-1'-{2-[(2-methanesulfonyl-2,3-dihydro-1H-isoindol-5-yl)oxy]ethyl}-1,2-dihydrospiro[indole-3,4'-piperidin]-2-one;
1'-{2-[(2-methanesulfonyl-1,2,3,4-tetrahydroisoquinolin-6-yl)oxy]ethyl}-1-methyl-1,2-dihydrospiro[indole-3,4'-piperidin]-2-one;
1'-{2-[(1-acetyl-1,2,3,4-tetrahydroquinolin-6-yl)oxy]ethyl}-5-chloro-1,2-dihydrospiro[indole-3,4'-piperidin]-2-one;
1'-{2-[(2-acetyl-2,3-dihydro-1H-isoindol-5-yl)oxy]ethyl}-5-chloro-1,2-dihydrospiro[indole-3,4'-piperidin]-2-one;
1'-{2-[(2-acetyl-1,2,3,4-tetrahydroisoquinolin-6-yl)oxy]ethyl}-1-methyl-1,2-dihydrospiro[indole-3,4'-piperidin]-2-one;
1'-{2-[(1-acetyl-1,2,3,4-tetrahydroquinolin-6-yl)oxy]ethyl}-2-oxo-1,2-dihydrospiro[indole-3,4'-piperidine]-5-carbonitrile;
6-(2-{5-chloro-2-oxo-1,2-dihydrospiro[indole-3,4'-piperidin]-1'-yl}ethoxy)-N-methyl-1,2,3,4-tetrahydroquinoline-1-carboxamide;
5-(2-{5-chloro-2-oxo-1,2-dihydrospiro[indole-3,4'-piperidin]-1'-yl}ethoxy)-N-methyl-2,3-dihydro-1H-isoindole-2-carboxamide;
5-chloro-1'-[2-(quinoxalin-6-yloxy)ethyl]-1,2-dihydrospiro[indole-3,4'-piperidin]-2-one;
5-chloro-1'-[2-(3-fluoro-4-methanesulfonylphenoxy)ethyl]-1,2-dihydrospiro[indole-3,4'-piperidin]-2-one;
5-chloro-1'-{2-[(6-methanesulfonylpyridin-3-yl)oxy]ethyl}-1,2-dihydrospiro[indole-3,4'-piperidin]-2-one;
5-chloro-1'-{2-[(1-methyl-2-oxo-2,3-dihydro-1H-indol-5-yl)oxy]ethyl}-1,2-dihydrospiro[indole-3,4'-piperidin]-2-one;
1'-[2-(4-methanesulfonylphenoxy)ethyl]-5-methyl-1,2-dihydrospiro[indole-3,4'-piperidin]-2-one;
1'-[2-(4-methanesulfonylphenoxy)ethyl]-1-methyl-1,2-dihydrospiro[indole-3,4'-piperidin]-2-one;
5-chloro-1'-{2-[(1-methyl-1H-indazol-5-yl)oxy]ethyl}-1,2-dihydrospiro[indole-3,4'-piperidin]-2-one;
5-chloro-1'-[2-(4-methanesulfonylphenoxy)ethyl]-1,2-dihydrospiro[indole-3,4'-piperidin]-2-one;
1'-{2-[(1-methyl-1H-indazol-5-yl)oxy]ethyl}-1,2-dihydrospiro[indole-3,4'-piperidin]-2-one;
1'-[2-(4-methanesulfonylphenoxy)ethyl]-2-oxo-1,2-dihydrospiro[indole-3,4'-piperidine]-5-carbonitrile;
5-bromo-1'-[2-(4-methanesulfonylphenoxy)ethyl]-1,2-dihydrospiro[indole-"one;
1'-[2-(4-methanesulfonylphenoxy)ethyl]-1,2-dihydrospiro[indole-3,4'-piperidin]-2-one;

1'-[2-(3-fluoro-4-methanesulfonylphenoxy)ethyl]-2-oxo-1,2-dihydrospiro[indole-3,4'-piperidine]-5-carbonitrile;
N-[4-(2-{5-cyano-2-oxo-1,2-dihydrospiro[indole-3,4'-piperidin]-1'-yl}ethoxy)phenyl]-N-methylmethanesulfonamide;
N-[4-(2-{5-chloro-2-oxo-1,2-dihydrospiro[indole-3,4'-piperidin]-1'-yl}ethoxy)phenyl]-N-methylmethanesulfonamide;
1'-[2-(4-{[dimethyl(oxo)-$\lambda^6$-sulfanylidene]amino}phenoxy)ethyl]-2-oxo-1,2-dihydrospiro[indole-3,4'-piperidine]-5-carbonitrile;
5-chloro-1'-{2-[(8-methyl-7-oxo-5,6,7,8-tetrahydro-1,8-naphthyridin-3-yl)oxy]ethyl}-1,2-dihydrospiro[indole-3,4'-piperidin]-2-one;
1'-{2-[(8-methyl-7-oxo-5,6,7,8-tetrahydro-1,8-naphthyridin-3-yl)oxy]ethyl}-2-oxo-1,2-dihydrospiro[indole-3,4'-piperidine]-5-carbonitrile;
1'-{2-[(8-acetyl-5,6,7,8-tetrahydro-1,8-naphthyridin-3-yl)oxy]ethyl}-5-chloro-1,2-dihydrospiro[indole-3,4'-piperidin]-2-one;
1'-{2-[(8-acetyl-5,6,7,8-tetrahydro-1,8-naphthyridin-3-yl)oxy]ethyl}-2-oxo-1,2-dihydrospiro[indole-3,4'-piperidine]-5-carbonitrile;
5-chloro-1'-{2-[(2-oxo-1,2,3,4-tetrahydroquinolin-6-yl)oxy]ethyl}-1,2-dihydrospiro[indole-3,4'-piperidin]-2-one;
2-oxo-1'-{2-[(1,3,3-trimethyl-2-oxo-2,3-dihydro-1H-indol-5-yl)oxy]ethyl}-1,2-dihydrospiro[indole-3,4'-piperidine]-5-carbonitrile;
1'-{2-[3,5-difluoro-4-(3-methanesulfonyloxetan-3-yl)phenoxy]ethyl}-2-oxo-1,2-dihydrospiro[indole-3,4'-piperidine]-5-carbonitrile;
5-chloro-1'-[2-({1-[(cis)-3-hydroxycyclobutyl]-1H-indazol-5-yl}oxy)ethyl]-1,2-dihydrospiro[indole-3,4'-piperidin]-2-one;
5-chloro-1'-[2-({1-[(trans)-3-hydroxycyclobutyl]-1H-indazol-5-yl}oxy)ethyl]-1,2-dihydrospiro[indole-3,4'-piperidin]-2-one;
5-chloro-1'-[2-(1H-indazol-5-yloxy)ethyl]-1,2-dihydrospiro[indole-3,4'-piperidin]-2-one;
5-chloro-1'-{2-[(1-methyl-2-oxo-2,3-dihydro-1H-1,3-benzodiazol-5-yl)oxy]ethyl}-1,2-dihydrospiro[indole-3,4'-piperidin]-2-one;
5-chloro-1'-[2-(3,5-difluoro-4-methanesulfonylphenoxy)ethyl]-1,2-dihydrospiro[indole-3,4'-piperidin]-2-one;
1'-[2-(3,5-difluoro-4-methanesulfonylphenoxy)ethyl]-2-oxo-1,2-dihydrospiro[indole-3,4'-piperidine]-5-carbonitrile;
methyl 1-[4-(2-{5-chloro-2-oxo-1,2-dihydrospiro[indole-3,4'-piperidin]-1'-yl}ethoxy)benzenesulfonyl]cyclopropane-1-carboxylate;
5-chloro-1'-(2-{4-[(3-methyloxetan-3-yl)sulfonyl]phenoxy}ethyl)-1,2-dihydrospiro[indole-3,4'-piperidin]-2-one;
1'-(2-{4-[(3-methyloxetan-3-yl)sulfonyl]phenoxy}ethyl)-2-oxo-1,2-dihydrospiro[indole-3,4'-piperidine]-5-carbonitrile;
5-chloro-1'-{2-[(2-methanesulfonyl-1,2,3,4-tetrahydroisoquinolin-6-yl)oxy]ethyl}-1,2-dihydrospiro[indole-3,4'-piperidin]-2-one;
1'-{2-[(1-methyl-2-oxo-1,2,3,4-tetrahydroquinolin-6-yl)oxy]ethyl}-2-oxo-1,2-dihydrospiro[indole-3,4'-piperidine]-5-carbonitrile;
2-oxo-1'-(2-{[2-oxo-1-(propan-2-yl)-1,2,3,4-tetrahydroquinolin-6-yl]oxy}ethyl)-1,2-dihydrospiro[indole-3,4'-piperidine]-5-carbonitrile;
5-chloro-1'-(2-{[2-oxo-1-(propan-2-yl)-1,2,3,4-tetrahydroquinolin-6-yl]oxy}ethyl)-1,2-dihydrospiro[indole-3,4'-piperidin]-2-one;
N-[4-(2-{5-chloro-2-oxo-1,2-dihydrospiro[indole-3,4'-piperidin]-1'-yl}ethoxy)phenyl]-N-(2-hydroxyethyl)methanesulfonamide;
5-chloro-1'-(2-{[1-(oxetan-3-yl)-2-oxo-1,2,3,4-tetrahydroquinolin-6-yl]oxy}ethyl)-1,2-dihydrospiro[indole-3,4'-piperidin]-2-one;
1'-{2-[3-(difluoromethyl)-4-methanesulfonylphenoxy]ethyl}-2-oxo-1,2-dihydrospiro[indole-3,4'-piperidine]-5-carbonitrile;
1'-{2-[4-(1-methanesulfonylcyclopropyl)phenoxy]ethyl}-2-oxo-1,2-dihydrospiro[indole-3,4'-piperidine]-5-carbonitrile;
5-chloro-1'-{2-[4-(1-methanesulfonylcyclopropyl)phenoxy]ethyl}-1,2-dihydrospiro[indole-3,4'-piperidin]-2-one;
6-(2-{5-chloro-2-oxo-1,2-dihydrospiro[indole-3,4'-piperidin]-1'-yl}ethoxy)-1-methyl-3,4-dihydro-1H-2$\lambda^6$,1-benzothiazine-2,2-dione;
1'-{2-[(1-methyl-2,2-dioxo-3,4-dihydro-1H-2$\lambda^6$,1-benzothiazin-6-yl)oxy]ethyl}-2-oxo-1,2-dihydrospiro[indole-3,4'-piperidine]-5-carbonitrile;
1'-(2-{[1-(2,2-difluoroethyl)-2-oxo-1,2,3,4-tetrahydroquinolin-6-yl]oxy}ethyl)-2-oxo-1,2-dihydrospiro[indole-3,4'-piperidine]-5-carbonitrile;
5-chloro-1'-(2-{[1-(2,2-difluoroethyl)-2-oxo-1,2,3,4-tetrahydroquinolin-6-yl]oxy}ethyl)-1,2-dihydrospiro[indole-3,4'-piperidin]-2-one;
1'-{2-[4-methanesulfonyl-3-(trifluoromethyl)phenoxy]ethyl}-2-oxo-1,2-dihydrospiro[indole-3,4'-piperidine]-5-carbonitrile;
5-chloro-1'-{2-[4-methanesulfonyl-3-(trifluoromethyl)phenoxy]ethyl}-1,2-dihydrospiro[indole-3,4'-piperidin]-2-one;
1'-{2-[4-(3-methanesulfonyloxetan-3-yl)phenoxy]ethyl}-2-oxo-1,2-dihydrospiro[indole-3,4'-piperidine]-5-carbonitrile;
5-chloro-1'-[2-(4-methanesulfonyl-3-methylphenoxy)ethyl]-1,2-dihydrospiro[indole-3,4'-piperidin]-2-one;
1'-[2-(4-methanesulfonyl-3-methylphenoxy)ethyl]-2-oxo-1,2-dihydrospiro[indole-3,4'-piperidine]-5-carbonitrile;
5-chloro-1'-[2-(4-difluoro-methanesulfonylphenoxy)ethyl]-1,2-dihydrospiro[indole-3,4'-piperidin]-2-one;
1'-[2-(4-difluoromethanesulfonylphenoxy)ethyl]-2-oxo-1,2-dihydrospiro[indole-3,4'-piperidine]-5-carbonitrile;
5-chloro-1'-[2-({2-oxo-1-[(cis)-3-hydroxycyclobutyl]-1,2,3,4-tetrahydroquinolin-6-yl}oxy)ethyl]-1,2-dihydrospiro[indole-3,4'-piperidin]-2-one;
5-chloro-1'-[2-({3-oxo-1H,2H,3H,5H,6H,10bH-imidazo[4,3-a]isoquinolin-8-yl}oxy)ethyl]-1,2-dihydrospiro[indole-3,4'-piperidin]-2-one;
(S)-5-chloro-1'-[2-({3-oxo-1H,2H,3H,5H,6H,10bH-imidazo[4,3-a]isoquinolin-8-yl}oxy)ethyl]-1,2-dihydrospiro[indole-3,4'-piperidin]-2-one;
(R)-5-chloro-1'-[2-({3-oxo-1H,2H,3H,5H,6H,10bH-imidazo[4,3-a]isoquinolin-8-yl}oxy)ethyl]-1,2-dihydrospiro[indole-3,4'-piperidin]-2-one;
2-oxo-1'-[2-({3-oxo-1H,2H,3H,5H,6H,10bH-imidazo[4,3-a]isoquinolin-8-yl}oxy)ethyl]-1,2-dihydrospiro[indole-3,4'-piperidine]-5-carbonitrile;
(S)-2-oxo-1'-[2-({3-oxo-1H,2H,3H,5H,6H,10bH-imidazo[4,3-a]isoquinolin-8-yl}oxy)ethyl]-1,2-dihydrospiro[indole-3,4'-piperidine]-5-carbonitrile;
(R)-2-oxo-1'-[2-({3-oxo-1H,2H,3H,5H,6H,10bH-imidazo[4,3-a]isoquinolin-8-yl}oxy)ethyl]-1,2-dihydrospiro[indole-3,4'-piperidine]-5-carbonitrile;

5-chloro-1'-[2-({3-oxo-1H,2H,3H,5H,6H,10bH-pyrrolo[2,1-a]isoquinolin-8-yl}oxy)ethyl]-1,2-dihydrospiro[indole-3,4'-piperidin]-2-one;

(S)-5-chloro-1'-[2-({3-oxo-1H,2H,3H,5H,6H,10bH-pyrrolo[2,1-a]isoquinolin-8-yl}oxy)ethyl]-1,2-dihydrospiro[indole-3,4'-piperidin]-2-one;

(R)-5-chloro-1'-[2-({3-oxo-1H,2H,3H,5H,6H,10bH-pyrrolo[2,1-a]isoquinolin-8-yl}oxy)ethyl]-1,2-dihydrospiro[indole-3,4'-piperidin]-2-one;

2-oxo-1'-[2-({3-oxo-1H,2H,3H,5H,6H,10bH-pyrrolo[2,1-a]isoquinolin-8-yl}oxy)ethyl]-1,2-dihydrospiro[indole-3,4'-piperidine]-5-carbonitrile;

(S)-2-oxo-1'-(2-((3-oxo-1,2,3,5,6,10b-hexahydropyrrolo[2,1-a]isoquinolin-8-yl)oxy)ethyl)spiro[indoline-3,4'-piperidine]-5-carbonitrile;

(R)-2-oxo-1'-(2-((3-oxo-1,2,3,5,6,10b-hexahydropyrrolo[2,1-a]isoquinolin-8-yl)oxy)ethyl)spiro[indoline-3,4'-piperidine]-5-carbonitrile;

N-[4-(2-{5-chloro-2-oxo-1,2-dihydrospiro[indole-3,4'-piperidin]-1'-yl}ethoxy)-2,6-difluorophenyl]-N-methylmethanesulfonamide;

N-[4-(2-{5-cyano-2-oxo-1,2-dihydrospiro[indole-3,4'-piperidin]-1'-yl}ethoxy)-2,6-difluorophenyl]-N-methylmethanesulfonamide;

5-chloro-1'-[2-(4-methanesulfonyl-3,5-dimethylphenoxy)ethyl]-1,2-dihydrospiro[indole-3,4'-piperidin]-2-one;

1'-[2-(4-methanesulfonyl-3,5-dimethylphenoxy)ethyl]-2-oxo-1,2-dihydrospiro[indole-3,4'-piperidine]-5-carbonitrile;

5-chloro-1'-{2-[(3-methyl-2-oxo-2,3-dihydro-1,3-benzoxazol-6-yl)oxy]ethyl}-1,2-dihydrospiro[indole-3,4'-piperidin]-2-one;

1'-{2-[(3-methyl-2-oxo-2,3-dihydro-1,3-benzoxazol-6-yl)oxy]ethyl}-2-oxo-1,2-dihydrospiro[indole-3,4'-piperidine]-5-carbonitrile;

1'-{2-[4-(1-methanesulfonylethyl)phenoxy]ethyl}-2-oxo-1,2-dihydrospiro[indole-3,4'-piperidine]-5-carbonitrile;

(S)-1'-{2-[4-(1-methanesulfonylethyl)phenoxy]ethyl}-2-oxo-1,2-dihydrospiro[indole-3,4'-piperidine]-5-carbonitrile;

(R)-1'-{2-[4-(1-methanesulfonylethyl)phenoxy]ethyl}-2-oxo-1,2-dihydrospiro[indole-3,4'-piperidine]-5-carbonitrile;

5-chloro-1'-{2-[3,5-difluoro-4-(3-methanesulfonyloxetan-3-yl)phenoxy]ethyl}-1,2-dihydrospiro[indole-3,4'-piperidin]-2-one;

1'-{2-[3,5-difluoro-4-(1-methanesulfonylethyl)phenoxy]ethyl}-2-oxo-1,2-dihydrospiro[indole-3,4'-piperidine]-5-carbonitrile;

(S)-1'-{2-[3,5-difluoro-4-(1-methanesulfonylethyl)phenoxy]ethyl}-2-oxo-1,2-dihydrospiro[indole-3,4'-piperidine]-5-carbonitrile;

(R)-1'-{2-[3,5-difluoro-4-(1-methanesulfonylethyl)phenoxy]ethyl}-2-oxo-1,2-dihydrospiro[indole-3,4'-piperidine]-5-carbonitrile;

1'-{2-[(6-methanesulfonyl-5-methylpyridin-3-yl)oxy]ethyl}-2-oxo-1,2-dihydrospiro[indole-3,4'-piperidine]-5-carbonitrile;

5-chloro-1'-{2-[3,5-difluoro-4-(1-methanesulfonylethyl)phenoxy]ethyl}-1,2-dihydrospiro[indole-3,4'-piperidin]-2-one;

(S)-5-chloro-1'-{2-[3,5-difluoro-4-(1-methanesulfonylethyl)phenoxy]ethyl}-1,2-dihydrospiro[indole-3,4'-piperidin]-2-one;

(R)-5-chloro-1'-{2-[3,5-difluoro-4-(1-methanesulfonylethyl)phenoxy]ethyl}-1,2-dihydrospiro[indole-3,4'-piperidin]-2-one;

2-oxo-1'-(2-{[2-oxo-1-(propan-2-yl)-2,3-dihydro-1H-indol-5-yl]oxy}ethyl)-1,2-dihydrospiro[indole-3,4'-piperidine]-5-carbonitrile;

5-chloro-1'-(2-{[2-oxo-1-(propan-2-yl)-2,3-dihydro-1H-indol-5-yl]oxy}ethyl)-1,2-dihydrospiro[indole-3,4'-piperidin]-2-one;

5-chloro-1'-{2-[(2-methyl-1-oxo-2,3-dihydro-1H-isoindol-5-yl)oxy]ethyl}-1,2-dihydrospiro[indole-3,4'-piperidin]-2-one;

5-chloro-1'-(2-{4-[methyl(methylimino)oxo-$\lambda^6$-sulfanyl]phenoxy}ethyl)-1,2-dihydrospiro[indole-3,4'-piperidin]-2-one;

(S)-5-chloro-1'-(2-{4-[methyl(methylimino)oxo-$\lambda^6$-sulfanyl]phenoxy}ethyl)-1,2-dihydrospiro[indole-3,4'-piperidin]-2-one;

(R)-5-chloro-1'-(2-{4-[methyl(methylimino)oxo-$\lambda^6$-sulfanyl]phenoxy}ethyl)-1,2-dihydrospiro[indole-3,4'-piperidin]-2-one;

1'-(2-{4-[methyl(methylimino)oxo-$\lambda^6$-sulfanyl]phenoxy}ethyl)-2-oxo-1,2-dihydrospiro[indole-3,4'-piperidine]-5-carbonitrile;

(S)-1'-(2-{4-[methyl(methylimino)oxo-$\lambda^6$-sulfanyl]phenoxy}ethyl)-2-oxo-1,2-dihydrospiro[indole-3,4'-piperidine]-5-carbonitrile;

(R)-1'-(2-{4-[methyl(methylimino)oxo-$\lambda^6$-sulfanyl]phenoxy}ethyl)-2-oxo-1,2-dihydrospiro[indole-3,4'-piperidine]-5-carbonitrile;

6-(2-{5-chloro-2-oxo-1,2-dihydrospiro[indole-3,4'-piperidin]-1'-yl}ethoxy)-2-methyl-3,4-dihydro-2H-1$\lambda^6$,2-benzothiazine-1,1-dione;

1'-{2-[(2-methyl-1,1-dioxo-3,4-dihydro-2H-1$\lambda^6$,2-benzothiazin-6-yl)oxy]ethyl}-2-oxo-1,2-dihydrospiro[indole-3,4'-piperidine]-5-carbonitrile;

5-chloro-1'-[2-(3-chloro-4-methanesulfonylphenoxy)ethyl]-1,2-dihydrospiro[indole-3,4'-piperidin]-2-one;

1'-[2-(3-chloro-4-methanesulfonylphenoxy)ethyl]-2-oxo-1,2-dihydrospiro[indole-3,4'-piperidine]-5-carbonitrile;

1'-{2-[4-(1-cyano-1-methylethyl)phenoxy]ethyl}-2-oxo-1,2-dihydrospiro[indole-3,4'-piperidine]-5-carbonitrile;

5-chloro-1'-[2-({6-[(3-methyloxetan-3-yl)sulfonyl]pyridin-3-yl}oxy)ethyl]-1,2-dihydrospiro[indole-3,4'-piperidin]-2-one;

1-(2-hydroxyethyl)-1'-{2-[4-methanesulfonyl-3-(trifluoromethyl)phenoxy]ethyl}-2-oxo-1,2-dihydrospiro[indole-3,4'-piperidine]-5-carbonitrile;

5-chloro-1-(2-hydroxyethyl)-1'-{2-[4-(3-methanesulfonyloxetan-3-yl)phenoxy]ethyl}-1,2-dihydrospiro[indole-3,4'-piperidin]-2-one;

5-chloro-1'-{2-[(6-methanesulfonyl-5-methylpyridin-3-yl)oxy]ethyl}-1,2-dihydrospiro[indole-3,4'-piperidin]-2-one;

5-chloro-1'-(2-{[1-(2-hydroxyethyl)-2-oxo-1,2,3,4-tetrahydroquinolin-6-yl]oxy}ethyl)-1,2-dihydrospiro[indole-3,4'-piperidin]-2-one;

5-chloro-1'-{2-[3-(difluoromethoxy)-4-methanesulfonylphenoxy]ethyl}-1,2-dihydrospiro[indole-3,4'-piperidin]-2-one;

1'-{2-[3-(difluoromethoxy)-4-methanesulfonylphenoxy]ethyl}-2-oxo-1,2-dihydrospiro[indole-3,4'-piperidine]-5-carbonitrile;

5-chloro-1'-{2-[4-(3-methanesulfonyloxetan-3-yl)-3-(trifluoromethyl)phenoxy]ethyl}-1,2-dihydrospiro[indole-3,4'-piperidin]-2-one;

1'-{2-[4-(3-methanesulfonyloxetan-3-yl)-3-(trifluoromethyl)phenoxy]ethyl}-2-oxo-1,2-dihydrospiro[indole-3,4'-piperidine]-5-carbonitrile;

6-(2-{5-chloro-2-oxo-1,2-dihydrospiro[indole-3,4'-piperidin]-1'-yl}ethoxy)-3,4-dihydro-2H-1λ⁶,2-benzothiazine-1,1-dione;

1'-{2-[(1,1-dioxo-3,4-dihydro-2H-1λ⁶,2-benzothiazin-6-yl)oxy]ethyl}-2-oxo-1,2-dihydrospiro[indole-3,4'-piperidine]-5-carbonitrile;

1'-{2-[(7-fluoro-1-methyl-2-oxo-2,3-dihydro-1H-indol-5-yl)oxy]ethyl}-2-oxo-1,2-dihydrospiro[indole-3,4'-piperidine]-5-carbonitrile;

2-oxo-1'-{2-[(1-oxo-2,3-dihydro-1H-isoindol-5-yl)oxy]ethyl}-1,2-dihydrospiro[indole-3,4'-piperidine]-5-carbonitrile;

5-chloro-1'-{2-[(1-oxo-2,3-dihydro-1H-isoindol-5-yl)oxy]ethyl}-1,2-dihydrospiro[indole-3,4'-piperidin]-2-one;

5-chloro-1'-[2-({2-[(3-methyloxetan-3-yl)oxy]pyrimidin-5-yl}oxy)ethyl]-1,2-dihydrospiro[indole-3,4'-piperidin]-2-one;

1'-[2-({2-[(3-methyloxetan-3-yl)oxy]pyrimidin-5-yl}oxy)ethyl]-2-oxo-1,2-dihydrospiro[indole-3,4'-piperidine]-5-carbonitrile;

1'-(2-{4-[3-(ethanesulfonyl)oxetan-3-yl]phenoxy}ethyl)-2-oxo-1,2-dihydrospiro[indole-3,4'-piperidine]-5-carbonitrile;

2-[4-(2-{5-chloro-2-oxo-1,2-dihydrospiro[indole-3,4'-piperidin]-1'-yl}ethoxy)phenyl]-1λ⁶-thiolane-1,1-dione;

(S)-2-[4-(2-{5-chloro-2-oxo-1,2-dihydrospiro[indole-3,4'-piperidin]-1'-yl}ethoxy)phenyl]-1λ⁶-thiolane-1,1-dione;

(R)-2-[4-(2-{5-chloro-2-oxo-1,2-dihydrospiro[indole-3,4'-piperidin]-1'-yl}ethoxy)phenyl]-1λ⁶-thiolane-1,1-dione;

1'-{2-[4-(1,1-dioxo-1λ⁶-thiolan-2-yl)phenoxy]ethyl}-2-oxo-1,2-dihydrospiro[indole-3,4'-piperidine]-5-carbonitrile;

5-chloro-1'-(2-{3-oxo-3H-spiro[2-benzofuran-1,3'-oxetan]-5-yloxy}ethyl)-1,2-dihydrospiro[indole-3,4'-piperidin]-2-one;

5-chloro-1'-{2-[4-(1-methanesulfonylcyclobutyl)phenoxy]ethyl}-1,2-dihydrospiro[indole-3,4'-piperidin]-2-one;

1'-{2-[4-(1-methanesulfonylcyclobutyl)phenoxy]ethyl}-2-oxo-1,2-dihydrospiro[indole-3,4'-piperidine]-5-carbonitrile;

5-chloro-1'-[2-(4-{6-methanesulfonyl-2-oxaspiro[3.3]heptan-6-yl}phenoxy)ethyl]-1,2-dihydrospiro[indole-3,4'-piperidin]-2-one;

1'-[2-(4-{6-methanesulfonyl-2-oxaspiro[3.3]heptan-6-yl}phenoxy)ethyl]-2-oxo-1,2-dihydrospiro[indole-3,4'-piperidine]-5-carbonitrile;

1'-{2-[4-(3-methanesulfonyloxetan-3-yl)phenoxy]ethyl}-2-oxo-1-(2,2,2-trifluoroethyl)-1,2-dihydrospiro[indole-3,4'-piperidine]-5-carbonitrile;

5-chloro-1'-{2-[4-(3-methanesulfonyloxetan-3-yl)phenoxy]ethyl}-1-(2,2,2-trifluoroethyl)-1,2-dihydrospiro[indole-3,4'-piperidin]-2-one;

N-(4-{2-[5-chloro-1-(2-hydroxyethyl)-2-oxo-1,2-dihydrospiro[indole-3,4'-piperidin]-1'-yl]ethoxy}-2-(trifluoromethyl)phenyl)methanesulfonamide;

1'-{2-[4-(4-methanesulfonyloxan-4-yl)phenoxy]ethyl}-2-oxo-1,2-dihydrospiro[indole-3,4'-piperidine]-5-carbonitrile;

5-chloro-1'-{2-[4-(4-methanesulfonyloxan-4-yl)phenoxy]ethyl}-1,2-dihydrospiro[indole-3,4'-piperidin]-2-one;

1'-{2-[3,5-difluoro-4-(3-methanesulfonyloxetan-3-yl)phenoxy]ethyl}-1-methyl-2-oxo-1,2-dihydrospiro[indole-3,4'-piperidine]-5-carbonitrile;

5-chloro-1'-[2-({7-oxo-8-[(cis)-3-hydroxycyclobutyl]-5,6,7,8-tetrahydro-1,8-naphthyridin-3-yl}oxy)ethyl]-1,2-dihydrospiro[indole-3,4'-piperidin]-2-one;

1'-(2-{[6-(2-methanesulfonylpropan-2-yl)pyridin-3-yl]oxy}ethyl)-2-oxo-1,2-dihydrospiro[indole-3,4'-piperidine]-5-carbonitrile;

5-chloro-1'-(2-{[8-(2-hydroxyethyl)-7-oxo-5,6,7,8-tetrahydro-1,8-naphthyridin-3-yl]oxy}ethyl)-1,2-dihydrospiro[indole-3,4'-piperidin]-2-one;

N-{2-[4-(2-{5-chloro-2-oxo-1,2-dihydrospiro[indole-3,4'-piperidin]-1'-yl}ethoxy)benzenesulfonyl]ethyl}-N-methylacetamide;

1'-{2-[(2-acetyl-1,2,3,4-tetrahydroisoquinolin-6-yl)oxy]ethyl}-5-chloro-1,2-dihydrospiro[indole-3,4'-piperidin]-2-one;

5-chloro-1'-{2-[4-(3-methanesulfonyloxetan-3-yl)phenoxy]ethyl}-1,2-dihydrospiro[indole-3,4'-piperidin]-2-one;

5-(2-{5-chloro-2-oxo-1,2-dihydrospiro[indole-3,4'-piperidin]-1'-yl}ethoxy)-2,3-dihydro-1λ⁶-benzothiophene-1,1-dione;

5-chloro-1'-{2-[3-(difluoromethyl)-4-methanesulfonylphenoxy]ethyl}-1,2-dihydrospiro[indole-3,4'-piperidin]-2-one;

5-chloro-1'-{2-[4-(2-hydroxyethanesulfonyl)phenoxy]ethyl}-1,2-dihydrospiro[indole-3,4'-piperidin]-2-one;

5-chloro-1'-{1-[(1-methyl-2-oxo-1,2,3,4-tetrahydroquinolin-6-yl)oxy]propan-2-yl}-1,2-dihydrospiro[indole-3,4'-piperidin]-2-one;

chloro-1'-[(2S)-1-[(1-methyl-2-oxo-1,2,3,4-tetrahydroquinolin-6-yl)oxy]propan-2-yl]-1,2-dihydrospiro[indole-3,4'-piperidin]-2-one;

chloro-1'-[(2R)-1-[(1-methyl-2-oxo-1,2,3,4-tetrahydroquinolin-6-yl)oxy]propan-2-yl]-1,2-dihydrospiro[indole-3,4'-piperidin]-2-one;

1'-{1-[(1-methyl-2-oxo-1,2,3,4-tetrahydroquinolin-6-yl)oxy]propan-2-yl}-2-oxo-1,2-dihydrospiro[indole-3,4'-piperidine]-5-carbonitrile;

(S)-1'-{1-[(1-methyl-2-oxo-1,2,3,4-tetrahydroquinolin-6-yl)oxy]propan-2-yl}-2-oxo-1,2-dihydrospiro[indole-3,4'-piperidine]-5-carbonitrile;

(R)-1'-{1-[(1-methyl-2-oxo-1,2,3,4-tetrahydroquinolin-6-yl)oxy]propan-2-yl}-2-oxo-1,2-dihydrospiro[indole-3,4'-piperidine]-5-carbonitrile;

5-chloro-1'-[1-(4-methanesulfonylphenoxy)propan-2-yl]-1-[3-hydroxycyclobutyl]-1,2-dihydrospiro[indole-3,4'-piperidin]-2-one;

5-chloro-1'-[(2S)-1-(4-methanesulfonylphenoxy)propan-2-yl]-1-[(cis)-3-hydroxycyclobutyl]-1,2-dihydrospiro[indole-3,4'-piperidin]-2-one;

5-chloro-1'-[(2S)-1-(4-methanesulfonylphenoxy)propan-2-yl]-1-[(trans)-3-hydroxycyclobutyl]-1,2-dihydrospiro[indole-3,4'-piperidin]-2-one;

5-chloro-1'-[(2R)-1-(4-methanesulfonylphenoxy)propan-2-yl]-1-[(cis)-3-hydroxycyclobutyl]-1,2-dihydrospiro[indole-3,4'-piperidin]-2-one;

5-chloro-1'-[(2R)-1-(4-methanesulfonylphenoxy)propan-2-yl]-1-[(trans)-3-hydroxycyclobutyl]-1,2-dihydrospiro[indole-3,4'-piperidin]-2-one;

5-chloro-1'-[(2S)-1-[3-(difluoromethyl)-4-methanesulfonylphenoxy]propan-2-yl]-1,2-dihydrospiro[indole-3,4'-piperidin]-2-one;

5-chloro-1'-[(2S)-1-[(1-methyl-1H-indazol-5-yl)oxy]propan-2-yl]-1,2-dihydrospiro[indole-3,4'-piperidin]-2-one;

1'-[(2S)-1-[3-(difluoromethyl)-4-methanesulfonylphenoxy]propan-2-yl]-2-oxo-1,2-dihydrospiro[indole-3,4'-piperidine]-5-carbonitrile;

1'-[(2S)-1-(3,5-difluoro-4-methanesulfonylphenoxy)propan-2-yl]-2-oxo-1,2-dihydrospiro[indole-3,4'-piperidine]-5-carbonitrile;

N-[4-(2-{5-chloro-2-oxo-1,2-dihydrospiro[indole-3,4'-piperidin]-1'-yl}ethoxy)phenyl]methanesulfonamide;

5-chloro-1'-[2-(4-{[(trans)-3-hydroxycyclobutyl]sulfonyl}phenoxy)ethyl]-1,2-dihydrospiro[indole-3,4'-piperidin]-2-one;

5-chloro-1'-{2-[3-(1,2-dihydroxyethyl)-4-methanesulfonylphenoxy]ethyl}-1,2-dihydrospiro[indole-3,4'-piperidin]-2-one;

5-chloro-1'-{2-[3-(1,2-difluoroethyl)-4-methanesulfonylphenoxy]ethyl}-1,2-dihydrospiro[indole-3,4'-piperidin]-2-one;

5-chloro-1'-(2-{3-[(1S)-1,2-difluoroethyl]-4-methanesulfonylphenoxy}ethyl)-1,2-dihydrospiro[indole-3,4'-piperidin]-2-one;

5-chloro-1'-(2-{3-[(1R)-1,2-difluoroethyl]-4-methanesulfonylphenoxy}ethyl)-1,2-dihydrospiro[indole-3,4'-piperidin]-2-one;

1'-{2-[3-(1,2-difluoroethyl)-4-methanesulfonylphenoxy]ethyl}-2-oxo-1,2-dihydrospiro[indole-3,4'-piperidine]-5-carbonitrile;

1'-(2-{3-[(1S)-1,2-difluoroethyl]-4-methanesulfonylphenoxy}ethyl)-2-oxo-1,2-dihydrospiro[indole-3,4'-piperidine]-5-carbonitrile;

1'-(2-{3-[(1R)-1,2-difluoroethyl]-4-methanesulfonylphenoxy}ethyl)-2-oxo-1,2-dihydrospiro[indole-3,4'-piperidine]-5-carbonitrile;

5-chloro-1'-{2-[4-methanesulfonyl-3-(oxetan-3-yl)phenoxy]ethyl}-1,2-dihydrospiro[indole-3,4'-piperidin]-2-one;

5-chloro-1'-[2-({2-oxo-1-[(trans)-3-hydroxycyclobutyl]-1,2,3,4-tetrahydroquinolin-6-yl}oxy)ethyl]-1,2-dihydrospiro[indole-3,4'-piperidin]-2-one;

5-chloro-1'-[2-(4-{[1-(hydroxymethyl)cyclopropyl]sulfonyl}phenoxy)ethyl]-1,2-dihydrospiro[indole-3,4'-piperidin]-2-one;

1-[4-(2-{5-chloro-2-oxo-1,2-dihydrospiro[indole-3,4'-piperidin]-1'-yl}ethoxy)benzenesulfonyl]-N-methylcyclopropane-1-carboxamide;

1-[4-(2-{5-chloro-2-oxo-1,2-dihydrospiro[indole-3,4'-piperidin]-1'-yl}ethoxy)benzenesulfonyl]-N,N-dimethylcyclopropane-1-carboxamide;

1'-[2-(4-{[1-(azetidine-1-carbonyl)cyclopropyl]sulfonyl}phenoxy)ethyl]-5-chloro-1,2-dihydrospiro[indole-3,4'-piperidin]-2-one;

4-(2-{5-chloro-2-oxo-1,2-dihydrospiro[indole-3,4'-piperidin]-1'-yl}ethoxy)-2-fluoro-N-methylbenzamide;

4-(2-{5-chloro-2-oxo-1,2-dihydrospiro[indole-3,4'-piperidin]-1'-yl}ethoxy)-2-fluoro-N,N-dimethylbenzamide;

5-chloro-1'-{2-[3-fluoro-4-(morpholine-4-carbonyl)phenoxy]ethyl}-1,2-dihydrospiro[indole-3,4'-piperidin]-2-one;

4-[4-(2-{5-chloro-2-oxo-1,2-dihydrospiro[indole-3,4'-piperidin]-1'-yl}ethoxy)-2-fluorobenzoyl]-1λ$^6$-thiomorpholine-1,1-dione;

5-chloro-1'-{2-[3-fluoro-4-(3-methanesulfonylazetidine-1-carbonyl)phenoxy]ethyl}-1,2-dihydrospiro[indole-3,4'-piperidin]-2-one;

1'-{2-[4-(azetidine-1-carbonyl)-3-fluorophenoxy]ethyl}-5-chloro-1,2-dihydrospiro[indole-3,4'-piperidin]-2-one;

5-chloro-1'-{2-[3-fluoro-4-(3-hydroxyazetidine-1-carbonyl)phenoxy]ethyl}-1,2-dihydrospiro[indole-3,4'-piperidin]-2-one;

1'-{2-[4-(3-aminoazetidine-1-carbonyl)-3-fluorophenoxy]ethyl}-5-chloro-1,2-dihydrospiro[indole-3,4'-piperidin]-2-one;

N-{1-[4-(2-{5-chloro-2-oxo-1,2-dihydrospiro[indole-3,4'-piperidin]-1'-yl}ethoxy)-2-fluorobenzoyl]azetidin-3-yl}methanesulfonamide;

4-(2-{5-cyano-2-oxo-1,2-dihydrospiro[indole-3,4'-piperidin]-1'-yl}ethoxy)-2-fluorobenzamide;

6-[4-(2-{5-chloro-2-oxo-1,2-dihydrospiro[indole-3,4'-piperidin]-1'-yl}ethoxy)-2-fluorobenzoyl]-2λ$^6$-thia-6-azaspiro[3.3]heptane-2,2-dione;

4-(2-{5-chloro-2-oxo-1,2-dihydrospiro[indole-3,4'-piperidin]-1'-yl}ethoxy)-N-(1,1-dioxo-1λ$^6$-thian-4-yl)-2-fluorobenzamide;

4-(2-{5-chloro-2-oxo-1,2-dihydrospiro[indole-3,4'-piperidin]-1'-yl}ethoxy)-N-(1,1-dioxo-1λ$^6$-thiolan-3-yl)-2-fluorobenzamide;

4-(2-{5-chloro-2-oxo-1,2-dihydrospiro[indole-3,4'-piperidin]-1'-yl}ethoxy)-N-[(3S)-1,1-dioxo-1,6-thiolan-3-yl]-2-fluorobenzamide;

4-(2-{5-chloro-2-oxo-1,2-dihydrospiro[indole-3,4'-piperidin]-1'-yl}ethoxy)-N-[(3R)-1,1-dioxo-1λ$^6$-thiolan-3-yl]-2-fluorobenzamide;

5-chloro-1'-{2-[4-(3-methyl-1H-pyrazol-4-yl)phenoxy]ethyl}-1,2-dihydrospiro[indole-3,4'-piperidin]-2-one;

6-(2-{5-chloro-2-oxo-1,2-dihydrospiro[indole-3,4'-piperidin]-1'-yl}ethoxy)-N-methyl-1,2,3,4-tetrahydroisoquinoline-2-carboxamide;

6-(2-{5-cyano-2-oxo-1,2-dihydrospiro[indole-3,4'-piperidin]-1'-yl}ethoxy)-N-methyl-1,2,3,4-tetrahydroisoquinoline-2-carboxamide;

5-chloro-1'-[2-({3-methyl-2-oxo-1H,2H,3H-imidazo[4,5-b]pyridin-6-yl}oxy)ethyl]-1,2-dihydrospiro[indole-3,4'-piperidin]-2-one;

5-chloro-1'-{2-[(6-{[1-(hydroxymethyl)cyclopropyl]sulfonyl}pyridin-3-yl)oxy]ethyl}-1,2-dihydrospiro[indole-3,4'-piperidin]-2-one;

4-(2-{5-chloro-2-oxo-1,2-dihydrospiro[indole-3,4'-piperidin]-1'-yl}ethoxy)-2-(difluoromethyl)benzamide;

4-(2-{5-cyano-2-oxo-1,2-dihydrospiro[indole-3,4'-piperidin]-1'-yl}ethoxy)-2-(difluoromethyl)benzamide;

1'-{2-[4-(3-methanesulfonyloxetan-3-yl)phenoxy]ethyl}-1-methyl-2-oxo-1,2-dihydrospiro[indole-3,4'-piperidine]-5-carbonitrile;

1'-(2-{4-[3-(3-fluoroazetidine-1-carbonyl)oxetan-3-yl]phenoxy}ethyl)-2-oxo-1,2-dihydrospiro[indole-3,4'-piperidine]-5-carbonitrile;

1'-(2-{4-[3-(azetidine-1-carbonyl)oxetan-3-yl]phenoxy}ethyl)-2-oxo-1,2-dihydrospiro[indole-3,4'-piperidine]-5-carbonitrile;

3-[4-(2-{5-cyano-2-oxo-1,2-dihydrospiro[indole-3,4'-piperidin]-1'-yl}ethoxy)phenyl]-N,N-dimethyloxetane-3-carboxamide;

3-[4-(2-{5-cyano-2-oxo-1,2-dihydrospiro[indole-3,4'-piperidin]-1'-yl}ethoxy)phenyl]-N-methyloxetane-3-carboxamide;

5-chloro-1'-{2-[(7-fluoro-2-oxo-2,3-dihydro-1H-indol-5-yl)oxy]ethyl}-1,2-dihydrospiro[indole-3,4'-piperidin]-2-one;

2-[4-(2-{5-cyano-2-oxo-1,2-dihydrospiro[indole-3,4'-piperidin]-1'-yl}ethoxy)phenyl]-2-methylpropanamide;

5-(2-{5-chloro-2-oxo-1,2-dihydrospiro[indole-3,4'-piperidin]-1'-yl}ethoxy)pyrimidine-2-carboxamide;

4-[4-(2-{5-chloro-2-oxo-1,2-dihydrospiro[indole-3,4'-piperidin]-1'-yl}ethoxy)-2,6-difluorobenzoyl]-1λ$^6$-thiomorpholine-1,1-dione;

1'-{2-[4-(1,1-dioxo-1λ$^6$-thiomorpholine-4-carbonyl)-3,5-difluorophenoxy]ethyl}-1-methyl-2-oxo-1,2-dihydrospiro[indole-3,4'-piperidine]-5-carbonitrile;

1'-{2-[4-(1,1-dioxo-1λ⁶-thiomorpholine-4-carbonyl)-3-(trifluoromethyl)phenoxy]ethyl}-1-methyl-2-oxo-1,2-dihydrospiro[indole-3,4'-piperidine]-5-carbonitrile;

1'-{1-[4-(3-methanesulfonyloxetan-3-yl)phenoxy]propan-2-yl}-2-oxo-1,2-dihydrospiro[indole-3,4'-piperidine]-5-carbonitrile;

(S)-1'-{1-[4-(3-methanesulfonyloxetan-3-yl)phenoxy]propan-2-yl}-2-oxo-1,2-dihydrospiro[indole-3,4'-piperidine]-5-carbonitrile;

(R)-1'-{1-[4-(3-methanesulfonyloxetan-3-yl)phenoxy]propan-2-yl}-2-oxo-1,2-dihydrospiro[indole-3,4'-piperidine]-5-carbonitrile;

5-chloro-1'-{2-[3-(difluoromethyl)-4-methanesulfonylphenoxy]ethyl}-1-(2-hydroxyethyl)-1,2-dihydrospiro[indole-3,4'-piperidin]-2-one;

1'-{2-[3-(difluoromethyl)-4-methanesulfonylphenoxy]ethyl}-1-(2-hydroxyethyl)-2-oxo-1,2-dihydrospiro[indole-3,4'-piperidine]-5-carbonitrile;

5-chloro-1'-[2-({7-oxo-8-[(trans)-3-hydroxycyclobutyl]-5,6,7,8-tetrahydro-1,8-naphthyridin-3-yl}oxy)ethyl]-1,2-dihydrospiro[indole-3,4'-piperidin]-2-one;

5-chloro-1'-{2-[4-(3-hydroxy-1-methanesulfonylcyclobutyl)phenoxy]ethyl}-1,2-dihydrospiro[indole-3,4'-piperidin]-2-one;

5-chloro-1'-(2-{4-[(cis)-3-hydroxy-1-methanesulfonylcyclobutyl]phenoxy}ethyl)-1,2-dihydrospiro[indole-3,4'-piperidin]-2-one;

5-chloro-1'-(2-{4-[(trans)-3-hydroxy-1-methanesulfonylcyclobutyl]phenoxy}ethyl)-1,2-dihydrospiro[indole-3,4'-piperidin]-2-one;

4-(4-{2-[5-chloro-1-(2-hydroxyethyl)-2-oxo-1,2-dihydrospiro[indole-3,4'-piperidin]-1'-yl]ethoxy}-2-(trifluoromethyl)benzoyl)-1λ⁶-thiomorpholine-1,1-dione;

4-[4-(2-{5-chloro-2-oxo-1,2-dihydrospiro[indole-3,4'-piperidin]-1'-yl}ethoxy)-2-(trifluoromethyl)benzoyl]-1λ⁶-thiomorpholine-1,1-dione;

5-chloro-1'-[2-(3-fluoro-4-{6-methanesulfonyl-2,6-diazaspiro[3.3]heptane-2-carbonyl}phenoxy)ethyl]-1,2-dihydrospiro[indole-3,4'-piperidin]-2-one;

5-(difluoromethyl)-1'-[2-({7-oxo-8-[(cis)-3-hydroxy-3-methylcyclobutyl]-5,6,7,8-tetrahydro-1,8-naphthyridin-3-yl}oxy)ethyl]-1,2-dihydrospiro[indole-3,4'-piperidin]-2-one;

5-chloro-1'-[2-({7-oxo-8-[(cis)-3-hydroxy-3-methylcyclobutyl]-5,6,7,8-tetrahydro-1,8-naphthyridin-3-yl}oxy)ethyl]-1,2-dihydrospiro[indole-3,4'-piperidin]-2-one;

5-chloro-1'-[2-({2-oxo-1-[(cis)-3-hydroxy-3-methylcyclobutyl]-1H,2H,4H-pyrido[2,3-d][1,3]oxazin-6-yl}oxy)ethyl]-1,2-dihydrospiro[indole-3,4'-piperidin]-2-one;

5-chloro-1'-[2-({7-oxo-8-[(trans)-3-ethyl-3-hydroxycyclobutyl]-5,6,7,8-tetrahydro-1,8-naphthyridin-3-yl}oxy)ethyl]-1,2-dihydrospiro[indole-3,4'-piperidin]-2-one;

5-chloro-1'-{2-[(7-oxo-5,6,7,8-tetrahydro-1,8-naphthyridin-3-yl)oxy]ethyl}-1,2-dihydrospiro[indole-3,4'-piperidin]-2-one;

5-chloro-1'-[2-({7-oxo-8-[(trans)-3-cyclopropyl-3-hydroxycyclobutyl]-5,6,7,8-tetrahydro-1,8-naphthyridin-3-yl}oxy)ethyl]-1,2-dihydrospiro[indole-3,4'-piperidin]-2-one;

5-chloro-1'-(2-{[8-(3-cyclopropyl-3-hydroxycyclobutyl)-7-oxo-5,6,7,8-tetrahydro-1,8-naphthyridin-3-yl]oxy}ethyl)-1,2-dihydrospiro[indole-3,4'-piperidin]-2-one;

5-chloro-1'-(2-{[8-(3-hydroxy-3-methylazetidin-1-yl)-1,7-naphthyridin-3-yl]oxy}ethyl)-1,2-dihydrospiro[indole-3,4'-piperidin]-2-one;

5-chloro-1'-[2-({7-oxo-8-[(trans)-3-hydroxy-3-methylcyclobutyl]-5,6,7,8-tetrahydro-1,8-naphthyridin-3-yl}oxy)ethyl]-1,2-dihydrospiro[indole-3,4'-piperidin]-2-one;

5-(difluoromethyl)-1'-[2-({7-oxo-8-[(cis)-3-(hydroxymethyl)cyclobutyl]-5,6,7,8-tetrahydro-1,8-naphthyridin-3-yl}oxy)ethyl]-1,2-dihydrospiro[indole-3,4'-piperidin]-2-one;

5-(difluoromethyl)-1'-[2-({7-oxo-8-[(trans)-3-(hydroxymethyl)cyclobutyl]-5,6,7,8-tetrahydro-1,8-naphthyridin-3-yl}oxy)ethyl]-1,2-dihydrospiro[indole-3,4'-piperidin]-2-one;

5-(difluoromethyl)-1'-{2-[(7-oxo-8-{[(cis)-3-hydroxy-3-methylcyclobutyl]methyl}-5,6,7,8-tetrahydro-1,8-naphthyridin-3-yl)oxy]ethyl}-1,2-dihydrospiro[indole-3,4'-piperidin]-2-one;

5-(difluoromethyl)-1'-{2-[(7-oxo-8-{[(trans)-3-hydroxy-3-methylcyclobutyl]methyl}-5,6,7,8-tetrahydro-1,8-naphthyridin-3-yl)oxy]ethyl}-1,2-dihydrospiro[indole-3,4'-piperidin]-2-one;

5-chloro-1'-{2-[(7-oxo-8-{[(cis)-3-hydroxy-3-methylcyclobutyl]methyl}-5,6,7,8-tetrahydro-1,8-naphthyridin-3-yl)oxy]ethyl}-1,2-dihydrospiro[indole-3,4'-piperidin]-2-one;

5-chloro-1'-(2-{[8-(3-hydroxyazetidin-1-yl)-1,7-naphthyridin-3-yl]oxy}ethyl)-1,2-dihydrospiro[indole-3,4'-piperidin]-2-one;

5-chloro-1'-(2-{[8-(3-hydroxy-3-methylcyclobutyl)-7-oxo-5,6,7,8-tetrahydro-1,8-naphthyridin-3-yl]oxy}ethyl)-1,2-dihydrospiro[indole-3,4'-piperidin]-2-one;

5-(difluoromethyl)-1'-[2-({8-[3-(hydroxymethyl)cyclobutyl]-7-oxo-5,6,7,8-tetrahydro-1,8-naphthyridin-3-yl}oxy)ethyl]-1,2-dihydrospiro[indole-3,4'-piperidin]-2-one;

5-chloro-1'-[2-({7-oxo-8-[(cis)-3-hydroxy-3-(propan-2-yl)cyclobutyl]-5,6,7,8-tetrahydro-1,8-naphthyridin-3-yl}oxy)ethyl]-1,2-dihydrospiro[indole-3,4'-piperidin]-2-one;

5-chloro-1'-(2-{[8-(3-ethyl-3-hydroxycyclobutyl)-7-oxo-5,6,7,8-tetrahydro-1,8-naphthyridin-3-yl]oxy}ethyl)-1,2-dihydrospiro[indole-3,4'-piperidin]-2-one;

5-chloro-1'-[2-({7-oxo-8-[(cis)-3-(hydroxymethyl)cyclobutyl]-5,6,7,8-tetrahydro-1,8-naphthyridin-3-yl}oxy)ethyl]-1,2-dihydrospiro[indole-3,4'-piperidin]-2-one;

5-(difluoromethyl)-1'-[2-({8-[(3-hydroxy-3-methylcyclobutyl)methyl]-7-oxo-5,6,7,8-tetrahydro-1,8-naphthyridin-3-yl}oxy)ethyl]-1,2-dihydrospiro[indole-3,4'-piperidin]-2-one;

5-chloro-1'-[2-({7-oxo-8-[(cis)-3-ethyl-3-hydroxycyclobutyl]-5,6,7,8-tetrahydro-1,8-naphthyridin-3-yl}oxy)ethyl]-1,2-dihydrospiro[indole-3,4'-piperidin]-2-one;

5-chloro-1'-{2-[(7-oxo-8-{[(trans)-3-hydroxy-3-methylcyclobutyl]methyl}-5,6,7,8-tetrahydro-1,8-naphthyridin-3-yl)oxy]ethyl}-1,2-dihydrospiro[indole-3,4'-piperidin]-2-one;

5-chloro-1'-[2-({7-oxo-8-[(cis)-3-hydroxy-3-methylcyclobutyl]-7,8-dihydro-1,8-naphthyridin-3-yl}oxy)ethyl]-1,2-dihydrospiro[indole-3,4'-piperidin]-2-one;

5-(difluoromethyl)-1'-[2-({7-oxo-8-[(cis)-3-hydroxy-3-methylcyclobutyl]-7,8-dihydro-1,8-naphthyridin-3-yl}oxy)ethyl]-1,2-dihydrospiro[indole-3,4'-piperidin]-2-one;

5-(difluoromethoxy)-1'-[2-({7-oxo-8-[(cis)-3-hydroxy-3-methylcyclobutyl]-5,6,7,8-tetrahydro-1,8-naphthyridin-3-yl}oxy)ethyl]-1,2-dihydrospiro[indole-3,4'-piperidin]-2-one;

5-chloro-1'-[2-({8-[3-(hydroxymethyl)cyclobutyl]-7-oxo-5,6,7,8-tetrahydro-1,8-naphthyridin-3-yl}oxy)ethyl]-1,2-dihydrospiro[indole-3,4'-piperidin]-2-one;

5-chloro-1'-[2-({8-[(3-hydroxy-3-methylcyclobutyl)methyl]-7-oxo-5,6,7,8-tetrahydro-1,8-naphthyridin-3-yl}oxy)ethyl]-1,2-dihydrospiro[indole-3,4'-piperidin]-2-one;

5-(difluoromethoxy)-1'-[2-({7-oxo-8-[(cis)-3-hydroxy-3-methylcyclobutyl]-7,8-dihydro-1,8-naphthyridin-3-yl}oxy)ethyl]-1,2-dihydrospiro[indole-3,4'-piperidin]-2-one;

5-chloro-7-iodo-1'-[2-({7-oxo-8-[(cis)-3-hydroxy-3-methylcyclobutyl]-5,6,7,8-tetrahydro-1,8-naphthyridin-3-yl}oxy)ethyl]-1,2-dihydrospiro[indole-3,4'-piperidin]-2-one;

5-chloro-1'-[2-({7-oxo-8-[(trans)-3-hydroxy-3-(propan-2-yl)cyclobutyl]-5,6,7,8-tetrahydro-1,8-naphthyridin-3-yl}oxy)ethyl]-1,2-dihydrospiro[indole-3,4'-piperidin]-2-one;

5-chloro-1'-[2-({7-oxo-8-[(trans)-3-(hydroxymethyl)cyclobutyl]-5,6,7,8-tetrahydro-1,8-naphthyridin-3-yl}oxy)ethyl]-1,2-dihydrospiro[indole-3,4'-piperidin]-2-one;

5-(difluoromethyl)-1'-(2-{[6-(1-hydroxyethyl)-5-(trifluoromethyl)pyridin-3-yl]oxy}ethyl)-1,2-dihydrospiro[indole-3,4'-piperidin]-2-one;

1'-(2-{[6-(1-hydroxyethyl)-5-(trifluoromethyl)pyridin-3-yl]oxy}ethyl)-2-oxo-1,2-dihydrospiro[indole-3,4'-piperidine]-5-carbonitrile;

5-chloro-1'-(2-{[5-(difluoromethyl)-7-oxo-8-[(cis)-3-hydroxy-3-methylcyclobutyl]-7,8-dihydro-1,8-naphthyridin-3-yl]oxy}ethyl)-1,2-dihydrospiro[indole-3,4'-piperidin]-2-one;

5-(difluoromethyl)-1'-(2-{[5-(difluoromethyl)-7-oxo-8-[(cis)-3-hydroxy-3-methylcyclobutyl]-7,8-dihydro-1,8-naphthyridin-3-yl]oxy}ethyl)-1,2-dihydrospiro[indole-3,4'-piperidin]-2-one;

5-chloro-1'-[2-({7-oxo-8-[(cis)-3-hydroxy-3-methylcyclobutyl]-5-(trifluoromethyl)-7,8-dihydro-1,8-naphthyridin-3-yl}oxy)ethyl]-1,2-dihydrospiro[indole-3,4'-piperidin]-2-one;

5-(difluoromethyl)-1'-[2-({7-oxo-8-[(cis)-3-hydroxy-3-methylcyclobutyl]-5-(trifluoromethyl)-7,8-dihydro-1,8-naphthyridin-3-yl}oxy)ethyl]-1,2-dihydrospiro[indole-3,4'-piperidin]-2-one;

5-chloro-1'-[2-({2-oxo-1-[(cis)-3-hydroxy-3-methylcyclobutyl]-1H,2H,3H-pyrrolo[2,3-b]pyridin-5-yl}oxy)ethyl]-1,2-dihydrospiro[indole-3,4'-piperidin]-2-one;

5-(difluoromethyl)-1'-[2-({2-oxo-1-[(cis)-3-hydroxy-3-methylcyclobutyl]-1H,2H,3H-pyrrolo[2,3-b]pyridin-5-yl}oxy)ethyl]-1,2-dihydrospiro[indole-3,4'-piperidin]-2-one;

5-chloro-1'-[2-({2-oxo-1-[(trans)-3-hydroxy-3-methylcyclobutyl]-1H,2H,3H-pyrrolo[2,3-b]pyridin-5-yl}oxy)ethyl]-1,2-dihydrospiro[indole-3,4'-piperidin]-2-one;

5-(difluoromethyl)-1'-[2-({2-oxo-1-[(trans)-3-hydroxy-3-methylcyclobutyl]-1H,2H,3H-pyrrolo[2,3-b]pyridin-5-yl}oxy)ethyl]-1,2-dihydrospiro[indole-3,4'-piperidin]-2-one;

5-chloro-1'-[2-({1-[(cis)-3-hydroxy-3-methylcyclobutyl]-1H-pyrrolo[2,3-b]pyridin-5-yl}oxy)ethyl]-1,2-dihydrospiro[indole-3,4'-piperidin]-2-one;

5-(difluoromethyl)-1'-[2-({1-[(cis)-3-hydroxy-3-methylcyclobutyl]-1H-pyrrolo[2,3-b]pyridin-5-yl}oxy)ethyl]-1,2-dihydrospiro[indole-3,4'-piperidin]-2-one;

5-chloro-1'-[2-({2-oxo-1-[(cis)-3-hydroxy-3-methylcyclobutyl]-1H,2H-pyrido[2,3-d]pyrimidin-6-yl}oxy)ethyl]-1,2-dihydrospiro[indole-3,4'-piperidin]-2-one;

5-chloro-1'-[2-({2-oxo-1-[(cis)-3-hydroxy-3-methylcyclobutyl]-1H,2H,3H,4H-pyrido[2,3-d]pyrimidin-6-yl}oxy)ethyl]-1,2-dihydrospiro[indole-3,4'-piperidin]-2-one;

5-chloro-1'-[2-({1-[(cis)-3-hydroxy-3-methylcyclobutyl]-1H-pyrazolo[3,4-b]pyridin-5-yl}oxy)ethyl]-1,2-dihydrospiro[indole-3,4'-piperidin]-2-one;

5-chloro-1'-[2-({3-oxo-4-[(cis)-3-hydroxy-3-methylcyclobutyl]-3H,4H-pyrido[2,3-b]pyrazin-7-yl}oxy)ethyl]-1,2-dihydrospiro[indole-3,4'-piperidin]-2-one;

5-chloro-1'-(2-{[4-(3-hydroxy-3-methylcyclobutyl)pyrido[3,2-d]pyrimidin-7-yl]oxy}ethyl)-1,2-dihydrospiro[indole-3,4'-piperidin]-2-one;

5-chloro-1'-(2-{[8-(3-hydroxy-3-methylcyclobutyl)-1,7-naphthyridin-3-yl]oxy}ethyl)-1,2-dihydrospiro[indole-3,4'-piperidin]-2-one;

5-chloro-1'-(2-{[8-(3-hydroxy-3-methylazetidin-1-yl)pyrido[2,3-d]pyridazin-3-yl]oxy}ethyl)-1,2-dihydrospiro[indole-3,4'-piperidin]-2-one;

5-chloro-1'-(2-{[4-(3-hydroxy-3-methylazetidin-1-yl)pyrido[3,2-d]pyrimidin-7-yl]oxy}ethyl)-1,2-dihydrospiro[indole-3,4'-piperidin]-2-one;

5-chloro-1'-(2-{[8-(3-hydroxyazetidin-1-yl)pyrido[2,3-d]pyridazin-3-yl]oxy}ethyl)-1,2-dihydrospiro[indole-3,4'-piperidin]-2-one;

5-chloro-1'-(2-{[4-(3-hydroxyazetidin-1-yl)pyrido[3,2-d]pyrimidin-7-yl]oxy}ethyl)-1,2-dihydrospiro[indole-3,4'-piperidin]-2-one;

5-chloro-1'-[2-({3-[(cis)-3-hydroxy-3-methylcyclobutyl]-3H-imidazo[4,5-b]pyridin-6-yl}oxy)ethyl]-1,2-dihydrospiro[indole-3,4'-piperidin]-2-one;

5-chloro-1'-[2-({2-oxo-3-[(cis)-3-hydroxy-3-methylcyclobutyl]-1H,2H,3H-imidazo[4,5-b]pyridin-6-yl}oxy)ethyl]-1,2-dihydrospiro[indole-3,4'-piperidin]-2-one;

5-chloro-1'-[2-({8-[3-(hydroxymethyl)azetidin-1-yl]-1,7-naphthyridin-3-yl}oxy)ethyl]-1,2-dihydrospiro[indole-3,4'-piperidin]-2-one;

1'-[2-({6-[(1S)-1-hydroxyethyl]-5-(trifluoromethyl)pyridin-3-yl}oxy)ethyl]-2-oxo-1,2-dihydrospiro[indole-3,4'-piperidine]-5-carbonitrile;

1'-[2-({6-[(1R)-1-hydroxyethyl]-5-(trifluoromethyl)pyridin-3-yl}oxy)ethyl]-2-oxo-1,2-dihydrospiro[indole-3,4'-piperidine]-5-carbonitrile;

5-chloro-1'-[2-({2-[(1S)-1,2-dihydroxyethyl]pyrimidin-5-yl}oxy)ethyl]-1,2-dihydrospiro[indole-3,4'-piperidin]-2-one;

5-chloro-1'-[2-({2-[(1R)-1,2-dihydroxyethyl]pyrimidin-5-yl}oxy)ethyl]-1,2-dihydrospiro[indole-3,4'-piperidin]-2-one;

5-chloro-1'-[2-({2-[(2S)-1,2-dihydroxypropan-2-yl]pyrimidin-5-yl}oxy)ethyl]-1,2-dihydrospiro[indole-3,4'-piperidin]-2-one;

5-chloro-1'-[2-({2-[(2R)-1,2-dihydroxypropan-2-yl]pyrimidin-5-yl}oxy)ethyl]-1,2-dihydrospiro[indole-3,4'-piperidin]-2-one;

5-chloro-1'-[2-({6-[(1S)-1,2-dihydroxyethyl]-5-(trifluoromethyl)pyridin-3-yl}oxy)ethyl]-1,2-dihydrospiro[indole-3,4'-piperidin]-2-one;

5-chloro-1'-[2-({6-[(1R)-1,2-dihydroxyethyl]-5-(trifluoromethyl)pyridin-3-yl}oxy)ethyl]-1,2-dihydrospiro[indole-3,4'-piperidin]-2-one;

5-chloro-1'-[2-({6-[(2S)-1,2-dihydroxypropan-2-yl]-5-(trifluoromethyl)pyridin-3-yl}oxy)ethyl]-1,2-dihydrospiro[indole-3,4'-piperidin]-2-one;

5-chloro-1'-[2-({6-[(2R)-1,2-dihydroxypropan-2-yl]-5-(trifluoromethyl)pyridin-3-yl}oxy)ethyl]-1,2-dihydrospiro[indole-3,4'-piperidin]-2-one;

5-chloro-1'-[2-({8-[(cis)-3-hydroxy-3-methylcyclobutyl]-1,7-naphthyridin-3-yl}oxy)ethyl]-1,2-dihydrospiro[indole-3,4'-piperidin]-2-one;

5-chloro-1'-[2-({8-[(trans)-3-hydroxy-3-methylcyclobutyl]-1,7-naphthyridin-3-yl}oxy)ethyl]-1,2-dihydrospiro[indole-3,4'-piperidin]-2-one;

5-chloro-1'-[2-({4-[(cis)-3-hydroxy-3-methylcyclobutyl]pyrido[3,2-d]pyrimidin-7-yl}oxy)ethyl]-1,2-dihydrospiro[indole-3,4'-piperidin]-2-one;

5-chloro-1'-[2-({4-[(trans)-3-hydroxy-3-methylcyclobutyl]pyrido[3,2-d]pyrimidin-7-yl}oxy)ethyl]-1,2-dihydrospiro[indole-3,4'-piperidin]-2-one;

5-chloro-1'-[2-({8-[(cis)-3-hydroxy-3-methylcyclobutyl]pyrido[2,3-d]pyridazin-3-yl}oxy)ethyl]-1,2-dihydrospiro[indole-3,4'-piperidin]-2-one;

5-chloro-1'-[2-({8-[(trans)-3-hydroxy-3-methylcyclobutyl]pyrido[2,3-d]pyridazin-3-yl}oxy)ethyl]-1,2-dihydrospiro[indole-3,4'-piperidin]-2-one;

5-chloro-1'-[2-({2-[(cis)-3-hydroxy-3-methylcyclobutyl]pyrimidin-5-yl}oxy)ethyl]-1,2-dihydrospiro[indole-3,4'-piperidin]-2-one;

5-chloro-1'-[2-({2-[(trans)-3-hydroxy-3-methylcyclobutyl]pyrimidin-5-yl}oxy)ethyl]-1,2-dihydrospiro[indole-3,4'-piperidin]-2-one;

5-chloro-1'-[2-({2-oxo-3-[(cis)-3-hydroxy-3-methylcyclobutyl]-2H,3H-[1,3]oxazolo[4,5-b]pyridin-6-yl}oxy)ethyl]-1,2-dihydrospiro[indole-3,4'-piperidin]-2-one;

5-(difluoromethyl)-1'-(2-{[2-(3-hydroxy-3-methylazetidin-1-yl)pyrimidin-5-yl]oxy}ethyl)-1,2-dihydrospiro[indole-3,4'-piperidin]-2-one;

5-chloro-1'-{2-[(2-{6-hydroxy-2-azaspiro[3.3]heptan-2-yl}pyrimidin-5-yl)oxy]ethyl}-1,2-dihydrospiro[indole-3,4'-piperidin]-2-one;

5-chloro-1'-(2-{[2-(3-ethyl-3-hydroxyazetidin-1-yl)pyrimidin-5-yl]oxy}ethyl)-1,2-dihydrospiro[indole-3,4'-piperidin]-2-one;

5-chloro-1'-[2-({7-oxo-8-[(cis)-3-cyclopropyl-3-hydroxycyclobutyl]-5,6,7,8-tetrahydro-1,8-naphthyridin-3-yl}oxy)ethyl]-1,2-dihydrospiro[indole-3,4'-piperidin]-2-one;

5-chloro-1'-(2-{[6-(1-hydroxyethyl)-5-(trifluoromethyl)pyridin-3-yl]oxy}ethyl)-1,2-dihydrospiro[indole-3,4'-piperidin]-2-one;

5,7-dichloro-1'-(2-{[2-(1-methanesulfonylcyclopropyl)pyrimidin-5-yl]oxy}ethyl)-1,2-dihydrospiro[indole-3,4'-piperidin]-2-one;

5-chloro-1'-(2-{[2-(1,2-dihydroxyethyl)pyrimidin-5-yl]oxy}ethyl)-1,2-dihydrospiro[indole-3,4'-piperidin]-2-one;

5-chloro-1'-[2-({2-[1-(hydroxymethyl)cyclopropyl]pyrimidin-5-yl}oxy)ethyl]-1,2-dihydrospiro[indole-3,4'-piperidin]-2-one;

5-chloro-1'-(2-{[2-(1-hydroxy-2-methylpropan-2-yl)pyrimidin-5-yl]oxy}ethyl)-1,2-dihydrospiro[indole-3,4'-piperidin]-2-one;

5-chloro-1'-(2-{[5-(difluoromethyl)-7-oxo-8-[(cis)-3-hydroxy-3-methylcyclobutyl]-7,8-dihydro-1,8-naphthyridin-3-yl]oxy}ethyl)-1,2-dihydrospiro[indole-3,4'-piperidin]-2-one;

5-(difluoromethyl)-1'-(2-{[5-(difluoromethyl)-7-oxo-8-[(cis)-3-hydroxy-3-methylcyclobutyl]-7,8-dihydro-1,8-naphthyridin-3-yl]oxy}ethyl)-1,2-dihydrospiro[indole-3,4'-piperidin]-2-one;

5-chloro-1'-[2-({7-oxo-8-[(cis)-3-hydroxy-3-methylcyclobutyl]-5-(trifluoromethyl)-7,8-dihydro-1,8-naphthyridin-3-yl}oxy)ethyl]-1,2-dihydrospiro[indole-3,4'-piperidin]-2-one;

5-(difluoromethyl)-1'-[2-({7-oxo-8-[(cis)-3-hydroxy-3-methylcyclobutyl]-5-(trifluoromethyl)-7,8-dihydro-1,8-naphthyridin-3-yl}oxy)ethyl]-1,2-dihydrospiro[indole-3,4'-piperidin]-2-one;

5-chloro-1'-(2-{4-[1-(dimethylphosphoryl)cyclopropyl]phenoxy}ethyl)-1,2-dihydrospiro[indole-3,4'-piperidin]-2-one;

5-chloro-1'-[2-({2-[1-(dimethylphosphoryl)cyclopropyl]pyrimidin-5-yl}oxy)ethyl]-1,2-dihydrospiro[indole-3,4'-piperidin]-2-one;

5-chloro-1'-[2-({2-oxo-1-[(1r,3s)-3-hydroxy-3-methylcyclobutyl]-1H,2H,3H-pyrrolo[2,3-b]pyridin-5-yl}oxy)ethyl]-1,2-dihydrospiro[indole-3,4'-piperidin]-2-one;

5-(difluoromethyl)-1'-[2-({2-oxo-1-[(cis)-3-hydroxy-3-methylcyclobutyl]-1H,2H,3H-pyrrolo[2,3-b]pyridin-5-yl}oxy)ethyl]-1,2-dihydrospiro[indole-3,4'-piperidin]-2-one;

5-chloro-1'-[2-({1-[(cis)-3-hydroxy-3-methylcyclobutyl]-1H-pyrrolo[2,3-b]pyridin-5-yl}oxy)ethyl]-1,2-dihydrospiro[indole-3,4'-piperidin]-2-one;

5-chloro-1'-[2-({1-[(cis)-3-hydroxy-3-methylcyclobutyl]-1H-1,3-benzodiazol-5-yl}oxy)ethyl]-1,2-dihydrospiro[indole-3,4'-piperidin]-2-one;

5-chloro-1'-[2-({2-oxo-1-[(cis)-3-hydroxy-3-methylcyclobutyl]-8-(trifluoromethyl)-1,2,3,4-tetrahydroquinolin-6-yl}oxy)ethyl]-1,2-dihydrospiro[indole-3,4'-piperidin]-2-one;

2-oxo-1'-[2-({2-oxo-1-[(cis)-3-hydroxy-3-methylcyclobutyl]-8-(trifluoromethyl)-1,2,3,4-tetrahydroquinolin-6-yl}oxy)ethyl]-1,2-dihydrospiro[indole-3,4'-piperidine]-5-carbonitrile;

5-chloro-1'-[2-({2-oxo-1-[(1r,3s)-3-hydroxy-3-methylcyclobutyl]-1H,2H,3H,4H-pyrido[2,3-d]pyrimidin-6-yl}oxy)ethyl]-1,2-dihydrospiro[indole-3,4'-piperidin]-2-one;

5-chloro-1'-[2-({1-[(cis)-3-hydroxy-3-methylcyclobutyl]-1H-pyrazolo[3,4-b]pyridin-5-yl}oxy)ethyl]-1,2-dihydrospiro[indole-3,4'-piperidin]-2-one;

5-chloro-1'-[2-({3-oxo-4-[(cis)-3-hydroxy-3-methylcyclobutyl]-3H,4H-pyrido[2,3-b]pyrazin-7-yl}oxy)ethyl]-1,2-dihydrospiro[indole-3,4'-piperidin]-2-one;

5-chloro-1'-[2-({3-[(cis)-3-hydroxy-3-methylcyclobutyl]-3H-imidazo[4,5-b]pyridin-6-yl}oxy)ethyl]-1,2-dihydrospiro[indole-3,4'-piperidin]-2-one;

5-chloro-1'-(2-{[6-(2-hydroxypropan-2-yl)-5-(trifluoromethyl)pyridin-3-yl]oxy}ethyl)-1,2-dihydrospiro[indole-3,4'-piperidin]-2-one;

5-chloro-1'-(2-{[2-(3-hydroxy-3-methylcyclobutyl)pyrimidin-5-yl]oxy}ethyl)-1,2-dihydrospiro[indole-3,4'-piperidin]-2-one;

5-chloro-1'-[2-({2-oxo-3-[(cis)-3-hydroxy-3-methylcyclobutyl]-1H,2H,3H-imidazo[4,5-b]pyridin-6-yl}oxy)ethyl]-1,2-dihydrospiro[indole-3,4'-piperidin]-2-one;

5-chloro-1'-[2-({2-[(1R or 1S)-1,2-dihydroxyethyl]pyrimidin-5-yl}oxy)ethyl]-1,2-dihydrospiro[indole-3,4'-piperidin]-2-one;

5-chloro-1'-[2-({2-[(1S or 1R)-1,2-dihydroxyethyl]pyrimidin-5-yl}oxy)ethyl]-1,2-dihydrospiro[indole-3,4'-piperidin]-2-one;

5-chloro-1'-[2-({2-[(cis)-3-hydroxy-3-methylcyclobutyl]pyrimidin-5-yl}oxy)ethyl]-1,2-dihydrospiro[indole-3,4'-piperidin]-2-one;

5-chloro-1'-[2-({2-[(cis) or (trans)-3-hydroxy-3-methylcyclobutyl]pyrimidin-5-yl}oxy)ethyl]-1,2-dihydrospiro[indole-3,4'-piperidin]-2-one;

5-chloro-1'-(2-{[6-(1-hydroxy-2-methanesulfonylpropan-2-yl)-5-(trifluoromethyl)pyridin-3-yl]oxy}ethyl)-1,2-dihydrospiro[indole-3,4'-piperidin]-2-one;

5-chloro-1'-[2-({6-[(2S or 2R)-1-hydroxy-2-methanesulfonylpropan-2-yl]-5-(trifluoromethyl)pyridin-3-yl}oxy)ethyl]-1,2-dihydrospiro[indole-3,4'-piperidin]-2-one;

5-chloro-1'-[2-({6-[(2R or 2S)-1-hydroxy-2-methanesulfonylpropan-2-yl]-5-(trifluoromethyl)pyridin-3-yl}oxy)ethyl]-1,2-dihydrospiro[indole-3,4'-piperidin]-2-one;

2-oxo-1'-[2-({7-oxo-8-[(cis)-3-hydroxy-3-methylcyclobutyl]-5,6,7,8-tetrahydro-1,8-naphthyridin-3-yl}oxy)ethyl]-1,2-dihydrospiro[indole-3,4'-piperidine]-5-carbonitrile;

5-chloro-1'-(2-{[6-(3-hydroxy-3-methylazetidin-1-yl)-5-(trifluoromethyl)pyridin-3-yl]oxy}ethyl)-1,2-dihydrospiro[indole-3,4'-piperidin]-2-one;

2-oxo-1'-[2-({7-oxo-8-[(cis)-3-hydroxy-3-methylcyclobutyl]-7,8-dihydro-1,8-naphthyridin-3-yl}oxy)ethyl]-1,2-dihydrospiro[indole-3,4'-piperidine]-5-carbonitrile;

5-chloro-1'-(2-{[1-(3-hydroxy-3-methylcyclobutyl)-1H-pyrazolo[3,4-b]pyridin-5-yl]oxy}ethyl)-1,2-dihydrospiro[indole-3,4'-piperidin]-2-one;

5-chloro-1'-[2-({1-[(trans)-3-hydroxy-3-methylcyclobutyl]-1H-pyrazolo[3,4-b]pyridin-5-yl}oxy)ethyl]-1,2-dihydrospiro[indole-3,4'-piperidin]-2-one;

5,7-dichloro-1'-[2-({7-oxo-8-[(cis)-3-hydroxy-3-methylcyclobutyl]-5,6,7,8-tetrahydro-1,8-naphthyridin-3-yl}oxy)ethyl]-1,2-dihydrospiro[indole-3,4'-piperidin]-2-one;

2-oxo-1'-[2-({1-[(cis)-3-hydroxy-3-methylcyclobutyl]-1H-pyrrolo[2,3-b]pyridin-5-yl}oxy)ethyl]-1,2-dihydrospiro[indole-3,4'-piperidine]-5-carbonitrile;

1'-(2-{[6-(2-hydroxypropan-2-yl)-5-(trifluoromethyl)pyridin-3-yl]oxy}ethyl)-2-oxo-1,2-dihydrospiro[indole-3,4'-piperidine]-5-carbonitrile;

5-chloro-1'-{2-[4-(1-methanesulfonylpiperidin-4-yl)phenoxy]ethyl}-1-($^{2}$H$_{3}$)methyl-1,2-dihydrospiro[indole-3,4'-piperidin]-2-one;

5-chloro-1-($^{2}$H$_{3}$)methyl-1'-(2-{4-[methyl(methylimino)oxo-$\lambda^{6}$-sulfanyl]-3-(trifluoromethyl)phenoxy}ethyl)-1,2-dihydrospiro[indole-3,4'-piperidin]-2-one;

5-chloro-1-($^{2}$H$_{3}$)methyl-1'-(2-{4-[3-(propane-2-sulfonyl)oxetan-3-yl]phenoxy}ethyl)-1,2-dihydrospiro[indole-3,4'-piperidin]-2-one;

5-chloro-1'-{2-[4-(1-methanesulfonylcyclobutyl)phenoxy]ethyl}-1-($^{2}$H$_{3}$)methyl-1,2-dihydrospiro[indole-3,4'-piperidin]-2-one;

5-chloro-1-($^{2}$H$_{3}$)methyl-1'-{2-[(2-methyl-1-oxo-2,3-dihydro-1H-isoindol-5-yl)oxy]ethyl}-1,2-dihydrospiro[indole-3,4'-piperidin]-2-one;

5-chloro-1'-(2-{[8-(2-hydroxy-2-methylpropyl)-7-oxo-5,6,7,8-tetrahydro-1,8-naphthyridin-3-yl]oxy}ethyl)-1-($^{2}$H$_{3}$)methyl-1,2-dihydrospiro[indole-3,4'-piperidin]-2-one;

5-chloro-1'-[2-(4-methanesulfonylphenoxy)ethyl]-1-($^{2}$H$_{3}$)methyl-1,2-dihydrospiro[indole-3,4'-piperidin]-2-one;

5-chloro-1-($^{2}$H$_{3}$)methyl-1'-[2-({7-oxo-8-[(cis)-3-hydroxy-3-methylcyclobutyl]-5,6,7,8-tetrahydro-1,8-naphthyridin-3-yl}oxy)ethyl]-1,2-dihydrospiro[indole-3,4'-piperidin]-2-one;

5-chloro-1'-[2-({2-[1-(hydroxymethyl)cyclopropyl]pyrimidin-5-yl}oxy)ethyl]-1-($^{2}$H$_{3}$)methyl-1,2-dihydrospiro[indole-3,4'-piperidin]-2-one;

6-{2-[5-chloro-1-($^{2}$H$_{3}$)methyl-2-oxo-1,2-dihydrospiro[indole-3,4'-piperidin]-1'-yl]ethoxy}-8-fluoro-3,4-dihydro-2H-1$\lambda^{6}$,2-benzothiazine-1,1-dione;

5-chloro-1'-(2-{[2-(3-methanesulfonyloxetan-3-yl)pyrimidin-5-yl]oxy}ethyl)-1-($^{2}$H$_{3}$)methyl-1,2-dihydrospiro[indole-3,4'-piperidin]-2-one;

5-chloro-1-($^{2}$H$_{3}$)methyl-1'-[2-({7-oxo-8-[(cis)-3-hydroxycyclobutyl]-5,6,7,8-tetrahydro-1,8-naphthyridin-3-yl}oxy)ethyl]-1,2-dihydrospiro[indole-3,4'-piperidin]-2-one;

5-chloro-1'-(2-{[2-(1-methanesulfonylcyclopropyl)pyrimidin-5-yl]oxy}ethyl)-1-($^{2}$H$_{3}$)methyl-1,2-dihydrospiro[indole-3,4'-piperidin]-2-one;

5-chloro-1'-(2-{[2-(1-methanesulfonylethyl)pyrimidin-5-yl]oxy}ethyl)-1-($^{2}$H$_{3}$)methyl-1,2-dihydrospiro[indole-3,4'-piperidin]-2-one;

5-chloro-1'-[2-({7-oxo-8-[(cis)-3-hydroxy-3-methylcyclobutyl]-5,6,7,8-tetrahydro-1,8-naphthyridin-3-yl}oxy)(1,1,2,2-$^{2}$H$_{4}$)ethyl]-1,2-dihydrospiro[indole-3,4'-piperidin]-2-one;

5-chloro-1'-[2-({2-[(cis)-3-hydroxy-3-methylcyclobutyl]-7-(trifluoromethyl)-2H-indazol-5-yl}oxy)ethyl]-1,2-dihydrospiro[indole-3,4'-piperidin]-2-one;

2-oxo-1'-[2-({2-[(cis)-3-hydroxy-3-methylcyclobutyl]-7-(trifluoromethyl)-2H-indazol-5-yl}oxy)ethyl]-1,2-dihydrospiro[indole-3,4'-piperidine]-5-carbonitrile;

5-chloro-1'-(2-{[2-(3-hydroxyoxetan-3-yl)pyrimidin-5-yl]oxy}ethyl)-1,2-dihydrospiro[indole-3,4'-piperidin]-2-one;

5-chloro-1'-(2-{[2-(1-hydroxycyclobutyl)pyrimidin-5-yl]oxy}ethyl)-1,2-dihydrospiro[indole-3,4'-piperidin]-2-one;

1'-(2-{[6-(3-hydroxy-3-methylazetidin-1-yl)-5-(trifluoromethyl)pyridin-3-yl]oxy}ethyl)-2-oxo-1,2-dihydrospiro[indole-3,4'-piperidine]-5-carbonitrile;

1'-(2-{[2-(1-hydroxy-2-methylpropan-2-yl)pyrimidin-5-yl]oxy}ethyl)-2-oxo-1,2-dihydrospiro[indole-3,4'-piperidine]-5-carbonitrile;

2-oxo-1'-[2-({1-[(cis)-3-hydroxy-3-methylcyclobutyl]-7-(trifluoromethyl)-1H-1,3-benzodiazol-5-yl}oxy)ethyl]-1,2-dihydrospiro[indole-3,4'-piperidine]-5-carbonitrile;

5-chloro-1'-[2-({1-[(cis)-3-hydroxy-3-methylcyclobutyl]-7-(trifluoromethyl)-1H-1,2,3-benzotriazol-5-yl}oxy)ethyl]-1,2-dihydrospiro[indole-3,4'-piperidin]-2-one;

2-oxo-1'-[2-({1-[(cis)-3-hydroxy-3-methylcyclobutyl]-7-(trifluoromethyl)-1H-1,2,3-benzotriazol-5-yl}oxy)ethyl]-1,2-dihydrospiro[indole-3,4'-piperidine]-5-carbonitrile;

1'-(2-{[1-(3-hydroxy-3-methylcyclobutyl)-1H-pyrazolo[3,4-b]pyridin-5-yl]oxy}ethyl)-2-oxo-1,2-dihydrospiro[indole-3,4'-piperidine]-5-carbonitrile;

2-oxo-1'-[2-({1-[(cis)-3-hydroxy-3-methylcyclobutyl]-1H-pyrazolo[3,4-b]pyridin-5-yl}oxy)ethyl]-1,2-dihydrospiro[indole-3,4'-piperidine]-5-carbonitrile;

1'-(2-{[1-(3-hydroxy-3-methylcyclobutyl)-1H-pyrazolo[3,4-b]pyridin-5-yl]oxy}ethyl)-2-oxo-1,2-dihydrospiro[indole-3,4'-piperidine]-5-carbonitrile;

5-(2-{5-chloro-2-oxo-1,2-dihydrospiro[indole-3,4'-piperidin]-1'-yl}ethoxy)-1-[(cis)-3-hydroxy-3-methylcyclobutyl]-1H-1,3-benzodiazole-7-carbonitrile;

5-chloro-1'-[2-({3-[(cis)-3-hydroxy-3-methylcyclobutyl]-3H-[1,2,3]triazolo[4,5-b]pyridin-6-yl}oxy)ethyl]-1,2-dihydrospiro[indole-3,4'-piperidin]-2-one;

5-chloro-1'-(2-{[2-(2,2-dimethyl-1,3-dioxolan-4-yl)pyrimidin-5-yl]oxy}ethyl)-1,2-dihydrospiro[indole-3,4'-piperidin]-2-one;

5-chloro-1'-[2-({2-methyl-1-[(cis)-3-hydroxy-3-methylcyclobutyl]-7-(trifluoromethyl)-1H-1,3-benzodiazol-5-yl}oxy)ethyl]-1,2-dihydrospiro[indole-3,4'-piperidin]-2-one;

1'-[2-({2-methyl-1-[(cis)-3-hydroxy-3-methylcyclobutyl]-7-(trifluoromethyl)-1H-1,3-benzodiazol-5-yl}oxy)ethyl]-2-oxo-1,2-dihydrospiro[indole-3,4'-piperidine]-5-carbonitrile;

5-chloro-1'-{2-[4-(1-methanesulfonylpiperidin-4-yl)phenoxy]ethyl}-1,2-dihydrospiro[indole-3,4'-piperidin]-2-one;

5-chloro-1'-(2-{[7-(difluoromethyl)-1-[(cis)-3-hydroxy-3-methylcyclobutyl]-1H-1,3-benzodiazol-5-yl]oxy}ethyl)-1,2-dihydrospiro[indole-3,4'-piperidin]-2-one;

1'-(2-{[7-(difluoromethyl)-1-[(cis)-3-hydroxy-3-methylcyclobutyl]-1H-1,3-benzodiazol-5-yl]oxy}ethyl)-2-oxo-1,2-dihydrospiro[indole-3,4'-piperidine]-5-carbonitrile;

5-chloro-1'-(2-{[7-(difluoromethoxy)-1-[(cis)-3-hydroxy-3-methylcyclobutyl]-1H-1,3-benzodiazol-5-yl]oxy}ethyl)-1,2-dihydrospiro[indole-3,4'-piperidin]-2-one;

1'-(2-{[7-(difluoromethoxy)-1-[(cis)-3-hydroxy-3-methylcyclobutyl]-1H-1,3-benzodiazol-5-yl]oxy}ethyl)-2-oxo-1,2-dihydrospiro[indole-3,4'-piperidine]-5-carbonitrile;

5-chloro-1'-(2-{[2-(2-hydroxypropan-2-yl)pyrimidin-5-yl]oxy}ethyl)-7-iodo-1,2-dihydrospiro[indole-3,4'-piperidin]-2-one;

5-(difluoromethyl)-1'-[2-({1-[(cis)-3-hydroxy-3-methylcyclobutyl]-7-(trifluoromethyl)-1H-1,3-benzodiazol-5-yl}oxy)ethyl]-1,2-dihydrospiro[indole-3,4'-piperidin]-2-one;

5-chloro-1'-[2-({2-methyl-3-[(cis)-3-hydroxy-3-methylcyclobutyl]-3H-imidazo[4,5-b]pyridin-6-yl}oxy)ethyl]-1,2-dihydrospiro[indole-3,4'-piperidin]-2-one;

5-chloro-1'-(2-{[8-(2-hydroxy-2-methylpropyl)-7-oxo-5,6,7,8-tetrahydro-1,8-naphthyridin-3-yl]oxy}ethyl)-1,2-dihydrospiro[indole-3,4'-piperidin]-2-one;

5-chloro-7-iodo-1'-[2-({1-[(cis)-3-hydroxy-3-methylcyclobutyl]-7-(trifluoromethyl)-1H-1,3-benzodiazol-5-yl}oxy)ethyl]-1,2-dihydrospiro[indole-3,4'-piperidin]-2-one;

5-chloro-1'-[2-({7-fluoro-1-[(cis)-3-hydroxy-3-methylcyclobutyl]-1H-1,3-benzodiazol-5-yl}oxy)ethyl]-1,2-dihydrospiro[indole-3,4'-piperidin]-2-one;

1'-[2-({7-fluoro-1-[(cis)-3-hydroxy-3-methylcyclobutyl]-1H-1,3-benzodiazol-5-yl}oxy)ethyl]-2-oxo-1,2-dihydrospiro[indole-3,4'-piperidine]-5-carbonitrile;

5-chloro-1'-[2-({2-oxo-1-[(cis)-3-hydroxy-3-methylcyclobutyl]-8-(trifluoromethyl)-1,2,3,4-tetrahydroquinazolin-6-yl}oxy)ethyl]-1,2-dihydrospiro[indole-3,4'-piperidin]-2-one;

2-oxo-1'-[2-({2-oxo-1-[(cis)-3-hydroxy-3-methylcyclobutyl]-8-(trifluoromethyl)-1,2,3,4-tetrahydroquinazolin-6-yl}oxy)ethyl]-1,2-dihydrospiro[indole-3,4'-piperidine]-5-carbonitrile;

5-chloro-1'-[2-({7,7-dimethyl-5-oxo-5H,7H-furo[3,4-b]pyridin-3-yl}oxy)ethyl]-1,2-dihydrospiro[indole-3,4'-piperidin]-2-one;

5-chloro-1'-{2-[(2-{6-hydroxy-6-methyl-2-azaspiro[3.3]heptan-2-yl}pyrimidin-5-yl)oxy]ethyl}-1,2-dihydrospiro[indole-3,4'-piperidin]-2-one;

5-chloro-1'-(2-{2'-oxo-1'-[(cis)-3-hydroxy-3-methylcyclobutyl]-1',2'-dihydrospiro[cyclopropane-1,3'-pyrrolo[2,3-b]pyridin]-5'-yloxy}ethyl)-1,2-dihydrospiro[indole-3,4'-piperidin]-2-one;

5-chloro-1'-[2-({7-oxo-8-[(cis)-3-hydroxy-3-($^2H_3$)methylcyclobutyl]-5,6,7,8-tetrahydro-1,8-naphthyridin-3-yl}oxy)ethyl]-1,2-dihydrospiro[indole-3,4'-piperidin]-2-one;

5-chloro-1'-[2-({7-oxo-8-[(cis)-3-hydroxy-3-($^2H_3$)methylcyclobutyl]-5,6,7,8-tetrahydro-1,8-naphthyridin-3-yl}oxy)(1,1,2,2-$^2H_4$)ethyl]-1,2-dihydrospiro[indole-3,4'-piperidin]-2-one;

5-chloro-1'-[2-({1-[(cis)-3-hydroxy-3-methylcyclobutyl]-7-(trifluoromethyl)-1H-1,3-benzodiazol-5-yl}oxy)(1,1,2,2-$^2H_4$)ethyl]-1,2-dihydrospiro[indole-3,4'-piperidin]-2-one;

5-chloro-1'-[2-({1-[(cis)-3-hydroxy-3-methylcyclobutyl]-7-(trifluoromethyl)-1H-indazol-5-yl}oxy)ethyl]-1,2-dihydrospiro[indole-3,4'-piperidin]-2-one;

2-oxo-1'-[2-({1-[(cis)-3-hydroxy-3-methylcyclobutyl]-7-(trifluoromethyl)-1H-indazol-5-yl}oxy)ethyl]-1,2-dihydrospiro[indole-3,4'-piperidine]-5-carbonitrile;

5-chloro-1'-[2-({2-[(1r,3s)-3-hydroxy-3-methylcyclobutyl]-7-(trifluoromethyl)-1H-1,3-benzodiazol-5-yl}oxy)ethyl]-1,2-dihydrospiro[indole-3,4'-piperidin]-2-one;

5-chloro-1'-(2-{[3-(hydroxymethyl)-2-oxo-1-[(cis)-3-hydroxy-3-methylcyclobutyl]-7-(trifluoromethyl)-2,3-dihydro-1H-1,3-benzodiazol-5-yl]oxy}ethyl)-1,2-dihydrospiro[indole-3,4'-piperidin]-2-one;

5-chloro-1'-[2-({2-oxo-1-[(cis)-3-hydroxy-3-methylcyclobutyl]-7-(trifluoromethyl)-2,3-dihydro-1H-1,3-benzodiazol-5-yl}oxy)ethyl]-1,2-dihydrospiro[indole-3,4'-piperidin]-2-one;

1'-(2-{[3-(hydroxymethyl)-2-oxo-1-[(cis)-3-hydroxy-3-methylcyclobutyl]-7-(trifluoromethyl)-2,3-dihydro-1H-1,3-benzodiazol-5-yl]oxy}ethyl)-2-oxo-1,2-dihydrospiro[indole-3,4'-piperidine]-5-carbonitrile;

2-oxo-1'-[2-({2-oxo-1-[(cis)-3-hydroxy-3-methylcyclobutyl]-7-(trifluoromethyl)-2,3-dihydro-1H-1,3-benzodiazol-5-yl}oxy)ethyl]-1,2-dihydrospiro[indole-3,4'-piperidine]-5-carbonitrile;

5-chloro-1'-[2-({1-[(cis)-3-hydroxy-3-methylcyclobutyl]-7-(trifluoromethyl)-1H-imidazo[4,5-b]pyridin-5-yl}oxy)ethyl]-1,2-dihydrospiro[indole-3,4'-piperidin]-2-one;

5-chloro-1'-(2-{3-[(cis)-3-hydroxy-3-methylcyclobutyl]-4-(trifluoromethyl)-3H-1,3,5-triazainden-6-yloxy}ethyl)spiro[indoline-3,4'-piperidin]-2-one, or a stereoisomer or tautomer thereof, or a pharmaceutically acceptable salt of any of the foregoing.

Isotopically labeled forms of any of the foregoing are also embraced, such as deuterated or tritiated forms (wherein at least one hydrogen is replaced by at least one deuterium or tritium) of any of the specific compounds detailed herein. Mixtures of any of the foregoing are also embraced and described. Prodrugs of any of the foregoing are also embraced herein.

As a non-limiting example, compounds of formula (II), formula (I'), or formula (I), or any embodiment or variation thereof, are provided, wherein any one or more H atoms are replaced with deuterium. For example, compounds of formula (II), formula (I'), or formula (I), or any embodiment or variation thereof, are provided wherein $L^1$ is $C_{1-6}$alkylene, wherein one or more H atoms of the $C_{1-6}$alkylene are replaced with deuterium. For example, compounds of formula (II), formula (I'), or formula (I), or any embodiment or variation thereof, are provided wherein $L^1$ is —$(CD_2)_{1-6}$-. In some embodiments of formula (II), formula (I'), or formula (I), or any embodiment or variation thereof, $L^1$ is —$(CD_2)$-$(CD_2)$-.

In some embodiments, compounds of formula (II), formula (I'), or formula (I) contain one or more hydrogen atoms that are replaced with deuterium, wherein deuterium is present in an amount that is greater than its natural abundance. Thus, as used herein, designation of an atom as deuterium at a position indicates that the abundance of deuterium is significantly greater than the natural abundance of deuterium. Unless otherwise stated, when a position is designated specifically as "H" or "hydrogen," the position is understood to have hydrogen at its naturally abundant isotopic composition. Also, unless otherwise stated, when a position is designated specifically as "D" or "deuterium," the position is understood to have deuterium at an abundance that is significantly greater than the natural abundance of deuterium, e.g., at least 3000 times greater than the natural abundance of deuterium, which is about 0.015% (i.e., the term "D" or "deuterium" indicates at least about 45% incorporation of deuterium).

Compound Names included in Table 1 and in the list in the paragraph above were generated ChemDraw® software version 18.1.0.458, ChemDraw® software version 18.0.0.231, or Collaborative Drug Discovery Inc. (CDD) CDD Vault update #3.

Compositions

Provided herein are pharmaceutical compositions comprising one or more compounds of formula (II), formula (I), formula (I'), or any variation or embodiment thereof, as described elsewhere herein, or a stereoisomer or tautomer thereof, or a pharmaceutically acceptable salt of any of the foregoing. In some embodiments, provided herein is a pharmaceutical composition comprising (i) a compound of formula (II), formula (I), formula (I') or any variation or embodiment thereof, as described elsewhere herein, or a stereoisomer or tautomer thereof, or a pharmaceutically acceptable salt of any of the foregoing, and (ii) one or more pharmaceutically acceptable excipients.

Suitable pharmaceutically acceptable excipients may include, for example, fillers, diluents, sterile aqueous solutions and various organic solvents, permeation enhancers, solubilizers, and adjuvants. Various substances may be embraced by the term excipient, including without limitation any substance used as a binder, disintegrant, coating, compression/encapsulation aid, cream or lotion, lubricant, solutions for parenteral administration, materials for chewable tablets, sweetener or flavoring, suspending/gelling agent, or wet granulation agent. Examples of suitable excipients are well-known to those skilled in the art. Such compositions are prepared in a manner well known in the pharmaceutical art. See, e.g., Remington's Pharmaceutical Sciences, Academic Press, $23^{rd}$ ed. (2020), which is incorporated herein by reference.

The pharmaceutical compositions may be administered in either single or multiple doses. The pharmaceutical composition may be administered by various methods including, for example, oral, rectal, buccal, intranasal, and transdermal routes. In certain embodiments, the pharmaceutical composition may be administered by intra-arterial injection, intravenously, intraperitoneally, parenterally, intramuscularly, subcutaneously, orally, topically, or as an inhalant.

Compounds as described herein may be administered to individuals in a form of generally accepted oral compositions, such as tablets, coated tablets, gel capsules in a hard or in soft shell, emulsions or suspensions. Examples of carriers, which may be used for the preparation of such compositions, are lactose, corn starch or its derivatives, talc, stearate or its salts, etc. Acceptable carriers for gel capsules with soft shell are, for instance, plant oils, wax, fats, semisolid and liquid poly-ols, and so on. In addition, pharmaceutical formulations may contain preservatives, solubilizers, stabilizers, re-wetting agents, emulgators, sweeteners, dyes, adjusters, salts for the adjustment of osmotic pressure, buffers, coating agents or antioxidants.

The specific dose level of a compound as described herein will depend upon a variety of factors such as the age, body weight and sex of the individual as well as the route of administration and other factors. In some embodiments, a dosage is expressed as a number of milligrams of a compound described herein per kilogram of the individual's body weight (mg/kg). Dosages of between about 0.1 mg/kg and 100-150 mg/kg may be appropriate.

The compound may be administered to an individual in accordance with an effective dosing regimen for a desired period of time or duration, such as at least about one month, at least about 2 months, at least about 3 months, at least about 6 months, or at least about 12 months or longer, which in some variations may be for the duration of the individual's life.

Methods of Treatment

Provided herein is a method of modulating APOL1 in a cell, comprising exposing the cell to an effective amount of a compound of formula (I), formula (I'), formula (II), or any variation or embodiment thereof, as described elsewhere herein, or a stereoisomer or tautomer thereof, or a pharmaceutically acceptable salt of any of the foregoing. Also provided herein is a method of modulating APOL1 in a cell, comprising exposing the cell to a composition comprising an effective amount of a compound of formula (I), formula (I'), formula (II), or any variation or embodiment thereof, as described elsewhere herein, or a stereoisomer or tautomer thereof, or a pharmaceutically acceptable salt of any of the foregoing, and one or more pharmaceutically acceptable excipients. Isotopically labeled forms of any of the foregoing are also embraced, including, but not limited to, deuterated or tritiated forms (wherein at least one hydrogen is replaced by at least one deuterium, or tritium) of any of the specific compounds detailed herein.

Provided herein is a method of inhibiting APOL1 in a cell, comprising exposing the cell to an effective amount of a compound of formula (I), formula (I'), formula (II), or any variation or embodiment thereof, as described elsewhere herein, or a stereoisomer or tautomer thereof, or a pharmaceutically acceptable salt of any of the foregoing. Also provided herein is a method of inhibiting APOL1 in a cell, comprising exposing the cell to a pharmaceutical composition comprising an effective amount of a compound of formula (I), formula (I'), formula (II), or any variation or embodiment thereof, as described elsewhere herein, or a stereoisomer or tautomer thereof, or a pharmaceutically acceptable salt of any of the foregoing, and one or more pharmaceutically acceptable excipients.

Provided herein is a method of inhibiting APOL1 in an individual, comprising administering to the individual an effective amount of a compound of formula (I), formula (I'), or any variation or embodiment thereof, as described elsewhere herein, or a stereoisomer or tautomer thereof, or a pharmaceutically acceptable salt of any of the foregoing. Also provided herein is a method of inhibiting APOL1 in an individual, comprising administering to the individual a pharmaceutical composition comprising an effective amount of a compound of formula (I), formula (I'), formula (II), or any variation or embodiment thereof, as described elsewhere herein, or a stereoisomer or tautomer thereof, or a pharmaceutically acceptable salt of any of the foregoing, and one or more pharmaceutically acceptable excipients.

In some embodiments, the compounds provided herein inhibit APOL1 at a concentration of less than 10 µM, less than 1 µM, less than 0.5 µM, or less than 0.1 µM. In some embodiments, the compounds provided herein inhibit APOL1 at a concentration of 1 to 10 µM, 0.01 to 1 µM, or 0.01 to 10 µM.

In some embodiments, the compounds provided herein reduce cell death caused by overexpression of APOL1. In some embodiments, the compounds provided herein reduce cell death caused by overexpression APOL1 at a concentration of less than 10 µM, less than 1 µM, less than 0.5 µM, or less than 0.1 µM. In some embodiments, the compounds provided herein reduce cell death caused by APOL1 overexpression at a concentration of 1 to 10 μM, 0.01 to 1 μM, or 0.01 to 10 μM.

In some embodiments, compounds provided herein have an $EC_{50}$ of less than 1 μM, less than 0.5 μM, or less than 0.1 μM. In some embodiments, the compounds provided herein have an $EC_{50}$ of 1 to 10 μM, 0.01 to 1 μM, or 0.01 to 10 μM.

In some embodiments, compounds provided herein have an $AC_{50}$ of less than 1 μM, less than 0.5 μM, or less than 0.1 μM. In some embodiments, the compounds provided herein have an $AC_{50}$ of 1 to 10 μM, 0.01 to 1 μM, or 0.01 to 10 μM. In some embodiments, the $AC_{50}$ value reflects the compound's ability to prevent calcium influx by inhibiting APOL1.

In some embodiments, the compounds provided herein inhibit a cation channel. In some embodiments, the compounds of the present disclosure inhibit a calcium channel. In some embodiments, the compounds of the present disclosure reduce calcium transport.

Provided herein is a method of treating an APOL1-mediated disease, disorder, or condition in an individual in need thereof, comprising administering to the individual a therapeutically effective amount of a compound of formula (I), formula (I'), formula (II), or any variation or embodiment thereof, as described elsewhere herein, or a stereoisomer or tautomer thereof, or a pharmaceutically acceptable salt of any of the foregoing. Also provided herein is a method of treating an APOL1-mediated disease, disorder, or condition in an individual in need thereof, comprising administering to the individual a pharmaceutical composition comprising a therapeutically effective amount of a compound of formula (I), formula (I'), formula (II), or any variation or embodiment thereof, as described elsewhere herein, or a stereoisomer or tautomer thereof, or a pharmaceutically acceptable salt of any of the foregoing, and one or more pharmaceutically acceptable excipients.

Provided herein is a method of treating a kidney disease, disorder, or condition in an individual in need thereof, comprising administering to the individual a therapeutically effective amount of a compound of formula (I), formula (I'), formula (II), or any variation or embodiment thereof, as described elsewhere herein, or a stereoisomer or tautomer thereof, or a pharmaceutically acceptable salt of any of the foregoing. Also provided herein is a method of treating a kidney disease, disorder, or condition in an individual in need thereof, comprising administering to the individual a pharmaceutical composition comprising a therapeutically effective amount of a compound of formula (I), formula (I'), formula (II), or any variation or embodiment thereof, as described elsewhere herein, or a stereoisomer or tautomer thereof, or a pharmaceutically acceptable salt of any of the foregoing, and one or more pharmaceutically acceptable excipients.

In some embodiments, the individual has a chronic kidney disease. In some embodiments, the individual has hypertension-attributed kidney disease. In some embodiments, the kidney disease, disorder, or condition is an APOL1-mediated kidney disease, disorder, or condition. In some embodiments, the kidney disease, disorder, or condition is selected from the group consisting of focal segmental glomerulosclerosis (FSGS), hypertension-attributed kidney disease, viral nephropathy, COVID-19 associated nephropathy, human immunodeficiency virus-associated nephropathy (HIVAN), sickle-cell nephropathy, lupus nephritis, and diabetic kidney disease.

Also provided herein is a method of treating an APOL1-mediated disorder, such as preeclampsia and sepsis, comprising administering to an individual in need thereof a therapeutically effective amount of a compound of formula (I), formula (I'), formula (II), or any variation or embodiment thereof, as described elsewhere herein, or a stereoisomer or tautomer thereof, or a pharmaceutically acceptable salt of any of the foregoing. In some embodiments, the individual is genetically predisposed to developing the APOL1-mediated disorder.

Also provided herein is a method of delaying development of progressive renal allograft loss in a kidney transplant recipient comprising administering to the kidney transplant recipient a therapeutically effective amount of a compound of formula (I), formula (I'), or any variation or embodiment thereof, as described elsewhere herein, or a stereoisomer or tautomer thereof, or a pharmaceutically acceptable salt of any of the foregoing. In some embodiments, the kidney transplant recipient receives a kidney from a high-risk APOL1 genotype donor. In some embodiments, the kidney transplant recipient is administered a therapeutically effective amount of the compound for a period of time before receiving the kidney transplant. In some embodiments, the kidney transplant recipient is administered a therapeutically effective amount of the compound subsequent to receiving the kidney transplant.

Provided herein is a method of treating a kidney disease, disorder, or condition in an individual in need thereof, comprising administering to the individual a therapeutically effective amount of a compound of formula (I), formula (I), formula (II), or any variation or embodiment thereof, as described elsewhere herein, or a stereoisomer or tautomer thereof, or a pharmaceutically acceptable salt of any of the foregoing, wherein the individual has an APOL1 mutation. Also provided herein is a method of treating a kidney disease, disorder, or condition in an individual in need thereof, comprising administering to the individual a pharmaceutical composition comprising a therapeutically effective amount of a compound of formula (I), formula (I'), formula (II), or any variation or embodiment thereof, as described elsewhere herein, or a stereoisomer or tautomer thereof, or a pharmaceutically acceptable salt of any of the foregoing, and one or more pharmaceutically acceptable excipients, wherein the individual has an APOL1 mutation.

The compounds provided herein may also be used in a method of delaying the development of an APOL1-mediated disease, disorder, or condition, comprising administering a compound of formula (I), formula (I'), formula (II), or any variation or embodiment thereof, as described elsewhere herein, or a stereoisomer or tautomer thereof, or a pharmaceutically acceptable salt of any of the foregoing, to an individual who is at risk of developing an APOL1-mediated disease, disorder, or condition. In some embodiments, the APOL1-mediated disease, disorder, or condition is preeclampsia or sepsis and the individual has two APOL1 risk alleles. In some embodiments, the APOL1-mediated disease, disorder, or condition is a chronic kidney disease and the individual has any binary combination of G1 and G2 APOL1 risk alleles. In some embodiments, the chronic kidney disease is focal segmental glomerulosclerosis (FSGS), hypertension-attributed kidney disease, human immunodeficiency virus-associated nephropathy (HIVAN), hypertension-attributed kidney disease, sickle cell nephropathy, viral nephropathy, COVID-19 associated nephropathy, lupus nephritis, diabetic kidney disease, or APOL1-associated nephropathy. The compounds as provided herein may also be used in a method of delaying the development of progressive renal allograft loss in an individual who has received a kidney transplantation from a high-risk APOL1 genotype donor.

In some embodiments, the individual has a gain-of-function mutation in APOL1. In some embodiments, the individual has an APOL1 risk allele. In some embodiments, the APOL1 risk allele is a missense variant. In some embodiments, the APOL1 risk allele is a G1 variant. In some embodiments, the G1 variant is G1$^G$ (p.S342 G) or G1M (p.I384 M). In some embodiments, the APOL1 risk allele is the G2 variant. In some embodiments, the G2 variant is NYK388-389K. In some embodiments, the APOL1 risk variant is a mutation in the serum resistance-associated (SRA) binding domain of the APOL1 protein. In some embodiments, the individual has two APOL1 risk alleles.

Also provided herein is a method of inhibiting APOL1 in an individual comprising administering to the individual a therapeutically effective amount of a compound of formula (I), formula (I'), formula (II), or any variation or embodiment thereof, as described elsewhere herein, or a stereoisomer or tautomer thereof, or a pharmaceutically acceptable salt of any of the foregoing.

Also provided herein is method of preventing kidney failure in an individual comprising administering a therapeutically effective amount of a compound of formula (I), formula (I'), formula (II), or any variation or embodiment thereof, as described elsewhere herein, or a stereoisomer or tautomer thereof, or a pharmaceutically acceptable salt of any of the foregoing to the individual. In some embodiments, the compound prevents tissue necrosis. In some embodiments, the compound prevents apoptosis. In some embodiments, the compound reduces inflammation.

In some embodiments, the compounds provided herein reduce or eliminate one or more symptoms of a kidney disease. In some embodiments, the compounds reduce nausea, vomiting, loss of appetite, fatigue and weakness, sleep problems, urinary frequency issues, muscle twinges and cramps, swelling, itching, chest pain, shortness of breath, and/or high blood pressure.

In some embodiments, the compounds provided herein reduce the rate of kidney damage and/or progression of kidney damage. In some embodiments, the compounds provided herein reduce the rate of kidney failure. In some embodiments, the compounds provided herein reverse kidney damage. In some embodiments, the compounds reduce the need for dialysis. In some embodiments, the compounds provided herein delay the need for dialysis at least one month, at least two months, at least three months, or at least one year.

In some embodiments, the compounds reduce the rate of or delay the need for a kidney transplant. For example, in some embodiments, the compounds provided herein delay the need for a kidney transplant at least one month, at least two months, at least three months, at least six months, or at least one year. In some embodiments, the compounds provided herein eliminate the need for a kidney transplant.

In some embodiments, the individual has stage 1, stage 2, stage 3A, stage 3B, stage 4, or stage 5 chronic kidney disease. In some embodiments, kidney function is evaluated using an estimated glomerular filtration rate (eGFR) kidney function test.

The compounds and compositions comprising the compounds provided herein may also be used in a method of delaying or preventing proteinuria, the method comprising administering the compound, or any variation or embodiment thereof, as described elsewhere herein, or a stereoisomer or tautomer thereof, or a pharmaceutically acceptable salt of any of the foregoing, to an individual. In one aspect, the methods herein comprise preventing or reducing protein in the urine, e.g., proteinuria. In some embodiments, the methods provided herein prevent proteinuria. In some embodiments, the methods reduce proteinuria. In some embodiments, the methods provided herein prevent albuminuria. In some embodiments, the methods reduce albuminuria. In some embodiments, the methods reduce urine albumin. In some embodiments, urine albumin is reduced by at least about 50%, about 60%, about 70%, about 80%, or about 90%, or greater. In some embodiments, urine albumin is reduced by at least about 50%. In some embodiments, urine albumin is reduced by at least about 60%. In some embodiments, urine albumin is reduced by at least about 70%. In some embodiments, urine albumin is reduced by at least about 80%. In some embodiments, urine albumin is reduced by at least about 90%. In some embodiments, reduction of urine albumin is dose-dependent. In some embodiments, the methods provided herein reduce urine albumin/creatine ratio. In some embodiments, urine albumin/creatine ratio is reduced by at least about 50%, about 60%, about 70%, about 80%, or about 90%, or greater. In some embodiments, urine albumin/creatine ratio is reduced by at least about 50%. In some embodiments, urine albumin/creatine ratio is reduced by at least about 60%. In some embodiments, urine albumin/creatine ratio is reduced by at least about 70%. In some embodiments, urine albumin/creatine ratio is reduced by at least about 80%. In some embodiments, urine albumin/creatine ratio is reduced by at least about 90%. In some embodiments, reduction of urine albumin/creatine ratio is dose-dependent. In some embodiments, the reduction and/or ratios are measured according to assays detailed herein. In any of the aforementioned methods, the individual is an individual in need thereof, such as an individual having an APOL1-mediated disease, disorder, or condition. In some embodiments, the APOL1-mediated disease, disorder, or condition is a kidney disease. In some embodiments, the APOL1-mediated disease, disorder, or condition is a chronic kidney disease. In some embodiments, the individual has hypertension-attributed kidney disease. In some embodiments, the kidney disease, disorder, or condition is selected from the group consisting of focal segmental glomerulosclerosis (FSGS), hypertension-attributed kidney disease, viral nephropathy, COVID-19 associated nephropathy, human immunodeficiency virus-associated nephropathy (HIVAN), sickle-cell nephropathy, lupus nephritis, and diabetic kidney disease.

In some embodiments, the administration is oral administration.

Kits

The present disclosure further provides kits for carrying out the methods of the invention. The kits may comprise a compound or pharmaceutically acceptable salt thereof as described herein and suitable packaging. The kits may comprise one or more containers comprising any compound described herein. In one aspect, a kit includes a compound of the disclosure or a pharmaceutically acceptable salt thereof, and a label and/or instructions for use of the compound in the treatment of a disease or disorder described herein. The kits may comprise a unit dosage form of the compound.

Provided herein are kits, comprising (i) a compound of formula (I), formula (I'), formula (II), or any variation or embodiment thereof, as described elsewhere herein, or a stereoisomer or tautomer thereof, or a pharmaceutically acceptable salt of any of the foregoing, and (ii) instructions for use in treating an APOL1-mediated disease, disorder, or condition in an individual in need thereof. Also provided herein are kits, comprising (i) a pharmaceutical composition comprising a compound of formula (I), or any variation or embodiment thereof, as described elsewhere herein, or a stereoisomer or tautomer thereof, or a pharmaceutically acceptable salt of any of the foregoing, and one or more pharmaceutically acceptable excipients; and (ii) instructions for use in treating an APOL1-mediated disease, disorder, or condition in an individual in need thereof.

Articles of manufacture are also provided, wherein the article of manufacture comprises a compound of formula (I), formula (I'), formula (II), or any variation or embodiment thereof, as described elsewhere herein, or a stereoisomer or tautomer thereof, or a pharmaceutically acceptable salt of any of the foregoing, in a suitable container. Also provided herein are articles of manufacture, comprising a pharmaceutical composition comprising a compound of formula (I), formula (I'), formula (II), or any variation or embodiment thereof, as described elsewhere herein, or a stereoisomer or tautomer thereof, or a pharmaceutically acceptable salt of any of the foregoing, in a suitable container. The container may be a vial, jar, ampoule, preloaded syringe, or intravenous bag.

ENUMERATED EMBODIMENTS

Embodiment 1A. A compound of formula (I):

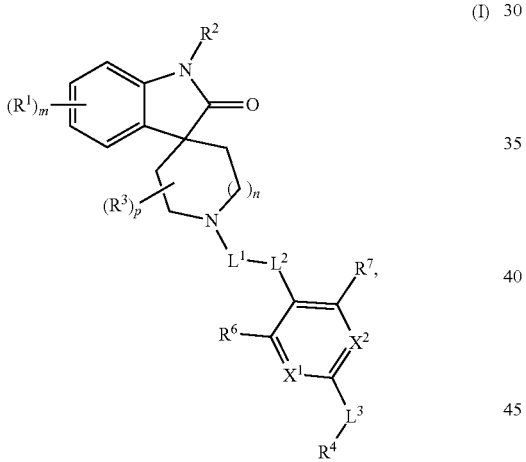

or a stereoisomer or tautomer thereof, or a pharmaceutically acceptable salt of any of the foregoing, wherein:

m is an integer from 0 to 4;
n is an integer from 0 to 2;
p is an integer from 0 to 10;
$R^1$, if present is, independently at each occurrence selected from the group consisting of halo, —CN, $C_{1-6}$alkoxy, or —$C_{1-6}$alkyl, wherein
  the $C_{1-6}$alkoxy of $R^1$ is optionally substituted with one or more halo, and
  the $C_{1-6}$alkyl of $R^1$ is optionally substituted with one or more halo;
$R^2$ is H, $C_{1-6}$alkyl, $C_{3-10}$cycloalkyl, or 3-15 membered heterocyclyl, wherein
  the $C_{1-6}$alkyl of $R^2$ is optionally substituted with one or more halo, —OH, —$NH_2$, or $C_{1-6}$alkoxy, and
  the $C_{3-10}$cycloalkyl of $R^2$ is optionally substituted with one or more —OH;
$R^3$, if present, is $C_{1-6}$alkyl;

$L^1$ is $C_{1-6}$alkylene, wherein the $C_{1-6}$alkylene of $L^1$ is optionally substituted with one or more $C_{1-6}$alkyl, and wherein the $C_{1-6}$alkyl is further optionally substituted with one or more —OH or $C_{1-6}$alkoxy;
$L^2$ is O or $N(R^x)$, wherein $R^x$ is H or $C_{1-6}$alkyl; and
either
(1) $L^3$ is absent or is O, $C_{3-10}$cycloalkyl, 3-10 membered heterocyclyl, or $C_{1-6}$alkylene, wherein
  the $C_{1-6}$alkylene of $L^3$ is optionally substituted with one or more $C_{1-6}$alkyl, and
  the 3-10 membered heterocyclyl is optionally substituted with one or more —OH;
$X^1$ and $X^2$ are each independently N or $C(R^5)$; and
$R^4$ is:
  (i) —$S(O)_2$—$R^a$;
  (ii) 5-20 membered heteroaryl, wherein the 5-20 membered heteroaryl of $R^4$ is optionally substituted with one or more $C_{1-6}$alkyl;
  (iii) —$N(R^d)_2$, wherein $R^d$ is independently at each occurrence H, $C_{1-6}$ alkyl, or —$S(O)_2$—$R^a$, wherein the $C_{1-6}$alkyl of $R^d$ is optionally substituted with one or more —OH,
  (iv) —NS(O)—$(C_{1-6}$alkyl$)_2$, wherein the $C_{1-6}$alkyl of $R^d$ is optionally substituted with one or more —OH,
  (v) —C(O)—$N(R^e)_2$ wherein $R^e$ is independently at each occurrence H, $C_{1-6}$ alkyl, or 3-10 membered heterocycle, wherein the 3-10 membered heterocycle is optionally substituted with one or more oxo, or both $R^e$ together with the N to which they are attached are taken together to form a 3-10 membered heterocyclyl, wherein the 3-10 membered heterocyclyl is optionally substituted with one or more halo, oxo, —OH, $NH_2$, NH—$S(O)_2$—$R^a$, or —$S(O)_2$—$R^a$,
  (vi) 3-10 membered heterocyclyl optionally substituted with one or more $C_{1-6}$alkyl or oxo,
  (vii) —S(O)—N($C_{1-6}$alkyl)-($C_{1-6}$alkyl),
  (viii) —CN;
or
(2) $L^3$ is absent; and
  one of $X^1$ and $X^2$ is N or $C(R^5)$; and
  the other of $X^1$ and $X^2$ is N or C that is taken together with $R^4$, and the atoms to which they are attached, to form a 5-10 membered heterocyclyl or a 5-20 membered heteroaryl, wherein
    the 5-10 membered heterocyclyl is optionally substituted with one or more $R^b$, wherein $R^b$ is, independently at each occurrence, selected from the group consisting of halo, oxo, $C_{1-6}$alkyl, —C(O)—$C_{1-6}$alkyl, —C(O)—$NH_2$, —C(O)—NH($C_{1-6}$alkyl), —C(O)—N($C_{1-6}$alkyl$)_2$, —$S(O)_2$—$R^a$, $C_{3-10}$cycloalkyl, and 3-10 membered heterocyclyl, wherein
      the $C_{1-6}$alkyl of $R^b$ is optionally substituted with one or more halo, OH, or —$S(O)_2$—$C_{1-6}$alkyl, and
      the $C_{3-10}$cycloalkyl of $R^b$ is optionally substituted with one or more —OH, and
    the 5-20 membered heteroaryl is optionally substituted with one or more $R^c$, wherein $R^c$ is, independently at each occurrence, selected from the group consisting of halo, $C_{1-6}$alkyl, —C(O)—$C_{1-6}$alkyl, —C(O)—$NH_2$, —C(O)—NH($C_{1-6}$alkyl), —C(O)—N($C_{1-6}$alkyl$)_2$, —$S(O)_2$—$R^a$, $C_{3-10}$cycloalkyl, and 3-10 membered heterocyclyl, wherein the C$_{1-6}$alkyl of R$^c$ is optionally substituted with one or more —S(O)$_2$—C$_{1-6}$alkyl, and the C$_{3-10}$cycloalkyl of R$^c$ is optionally substituted with one or more —OH;

R$^a$ is, independently at each occurrence:
(i) C$_{1-6}$alkyl optionally substituted with one or more halo, —OH, —S(O)$_2$—C$_{1-6}$alkyl, or —N(C$_{1-6}$alkyl)-C(O)—C$_{1-6}$alkyl, or
(ii) C$_{3-10}$cycloalkyl optionally substituted with one or more —OH, —C(O)$_2$—C$_{1-6}$alkyl, —C(O)—NH(C$_{1-6}$alkyl), —C(O)—N(C$_{1-6}$alkyl)$_2$, or —C(O)—C$_{3-10}$heterocyclyl, or C$_{1-6}$alkyl, wherein the C$_{1-6}$alkyl is optionally substituted with one or more —OH, or
(iii) 3-10 membered heterocyclyl optionally substituted with one or more C$_{1-6}$alkyl;

R$^5$ is, independently at each occurrence, H, halo, —CN, 3-10 membered heterocyclyl, C$_{1-6}$alkyl, or C$_{1-6}$alkoxy, wherein the C$_{1-6}$alkyl of R$^5$ is optionally substituted with one or more halo, or —OH and wherein the C$_{1-6}$alkoxy is optionally substituted with one or more halo; and R$^6$ and R$^7$ are each independently H or halo.

Embodiment 2A. The compound of embodiment 1A, or a stereoisomer or tautomer thereof, or a pharmaceutically acceptable salt of any of the foregoing, wherein L$^2$ is O, such that the compound is of formula (I-A):

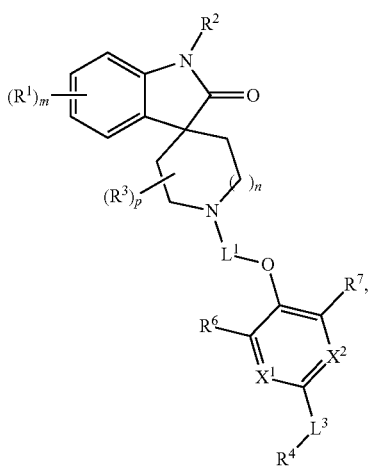

(I-A)

or a stereoisomer or tautomer thereof, or a pharmaceutically acceptable salt of any of the foregoing.

Embodiment 3A. The compound of embodiment 1A or embodiment 2A, or a stereoisomer or tautomer thereof, or a pharmaceutically acceptable salt of any of the foregoing, wherein n is 1, or 2.

Embodiment 4A. The compound of any one of embodiments 1A-3A, or a stereoisomer or tautomer thereof, or a pharmaceutically acceptable salt of any of the foregoing, wherein R$^2$ is H, C$_{1-6}$alkyl, C$_{3-10}$cycloalkyl, or 3-15 membered heterocyclyl, wherein the C$_{1-6}$alkyl of R$^2$ is optionally substituted with one or more halo, —OH, —NH$_2$, or C$_{1-6}$alkoxy, and the C$_{3-10}$cycloalkyl of R$^2$ is optionally substituted with one or more —OH.

Embodiment 5A. The compound of any one of embodiments 1A-4A, or a stereoisomer or tautomer thereof, or a pharmaceutically acceptable salt of any of the foregoing, wherein m is 0, 1, or 2.

Embodiment 6A. The compound of any one of embodiments 1A-5A, or a stereoisomer or tautomer thereof, or a pharmaceutically acceptable salt of any of the foregoing, wherein R$^1$ is halo, —CN, or —C$_{1-6}$alkyl, wherein the C$_{1-6}$alkyl of R$^1$ is optionally substituted with one or more halo.

Embodiment 7A. The compound of any one of embodiments 1A-6A, or a stereoisomer or tautomer thereof, or a pharmaceutically acceptable salt of any of the foregoing, wherein p is 0 or 1.

Embodiment 8A. The compound of any one of embodiments 1A-7A, or a stereoisomer or tautomer thereof, or a pharmaceutically acceptable salt of any of the foregoing, wherein R$^3$ is C$_{1-6}$alkyl.

Embodiment 9A. The compound of any one of embodiments 1A-8A, or a stereoisomer or tautomer thereof, or a pharmaceutically acceptable salt of any of the foregoing, wherein L$^1$ is C$_{1-6}$alkylene, wherein the C$_{1-6}$alkylene of L$^1$ is optionally substituted with one or more C$_{1-6}$alkyl, wherein the C$_{1-6}$alkyl is optionally substituted with —OH or C$_{1-6}$alkoxy.

Embodiment 10A. The compound of any one of embodiments 1A-9A, or a stereoisomer or tautomer thereof, or a pharmaceutically acceptable salt of any of the foregoing, wherein L$^1$ is selected from the group consisting of

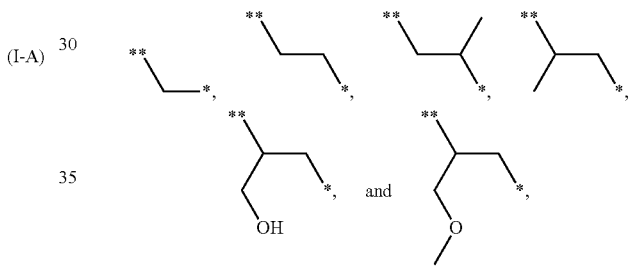

wherein, for each L$^1$, * denotes the point of attachment to L$^2$ and ** denotes the point of attachment to the remainder of the molecule.

Embodiment 11A. The compound of any one of embodiments 1A-10A, or a stereoisomer or tautomer thereof, or a pharmaceutically acceptable salt of any of the foregoing, wherein L$^2$ is O.

Embodiment 12A. The compound of any one of embodiments 1A-11A, or a stereoisomer or tautomer thereof, or a pharmaceutically acceptable salt of any of the foregoing, wherein L$^3$ is absent.

Embodiment 13A. The compound of any one of embodiments 1A-12A, or a stereoisomer or tautomer thereof, or a pharmaceutically acceptable salt of any of the foregoing, wherein L$^3$ is —O—, C$_{3-10}$cycloalkyl, 3-10 membered heterocyclyl, or C$_{1-6}$alkylene, wherein
the C$_{1-6}$alkylene of L$^3$ is optionally substituted with one or more C$_{1-6}$alkyl,
the C$_{3-10}$cycloalkyl membered heterocyclyl of L$^3$ is optionally substituted with one or more —OH, and
the 3-10 membered heterocyclyl of L$^3$ is optionally substituted with one or more —OH.

Embodiment 14A. The compound of any one of embodiments 1A-11A, and 13A or a stereoisomer or tautomer thereof, or a pharmaceutically acceptable salt of any of the foregoing, wherein L$^3$ is selected from the group consisting of —O—,

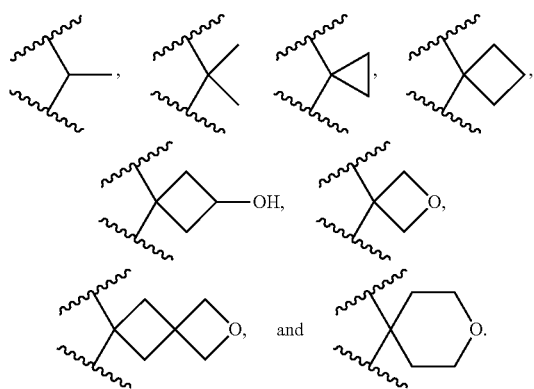

Embodiment 15A. The compound of any one of embodiments 1A-14A or a stereoisomer or tautomer thereof, or a pharmaceutically acceptable salt of any of the foregoing, wherein $R^4$ is $S(O)_2$—$R^a$, 5-10 membered heteroaryl, —$N(R^d)_2$, —NS(O)—$(C_{1-3}alkyl)_2$, —C(O)—$N(R^e)_2$, 3-6 membered heterocyclyl, —S(O)(N—$C_{1-3}$alkyl)-$(C_{1-3}$alkyl), or —CN, wherein
 the 5-20 membered heteroaryl of $R^4$ is optionally substituted with one or more $C_{1-6}$alkyl, and
 the 3-6 membered heterocyclyl optionally substituted with one or more oxo or $C_{1-6}$alkyl.

Embodiment 16A. The compound of embodiment 15A or a stereoisomer or tautomer thereof, or a pharmaceutically acceptable salt of any of the foregoing, wherein $R^a$ is $C_{1-6}$alkyl, is $C_{3-10}$cycloalkyl, or is 3-10 membered heterocyclyl, wherein
 the $C_{1-6}$alkyl of $R^a$ is optionally substituted with one or more halo, —OH, —$S(O)_2$—$C_{1-6}$alkyl, or —$N(C_{1-6}alkyl)$-$C(O)$—$C_{1-6}$alkyl,
 the $C_{3-10}$cycloalkyl of $R^a$ is optionally substituted with one or more —OH, $C(O)_2$—$C_{1-6}$alkyl, —C(O)—NH$(C_{1-6}alkyl)$, —C(O)—$N(C_{1-6}alkyl)_2$, —C(O)—$C_{3-10}$heterocyclyl or $C_{1-6}$alkyl, wherein the $C_{1-6}$alkyl is optionally substituted with one or more —OH, and
 the 3-10 membered heterocyclyl of $R^a$ is optionally substituted with one or more $C_{1-6}$alkyl.

Embodiment 17A. The compound of embodiment 15A, or a stereoisomer or tautomer thereof, or a pharmaceutically acceptable salt of any of the foregoing, wherein each of $R^d$ is independently H, $C_{1-6}$ alkyl, or —$S(O)_2$—$R^a$, wherein the $C_{1-6}$alkyl of $R^d$ is optionally substituted with one or more —OH, and wherein $R^a$ is $C_{1-6}$alkyl.

Embodiment 18A. The compound of embodiment 15A, or a stereoisomer or tautomer thereof, or a pharmaceutically acceptable salt of any of the foregoing, wherein each of $R^e$ is independently H, $C_{1-6}$alkyl, or 3-10 membered heterocycle, wherein the 3-6 membered heterocycle is optionally substituted with one or more oxo.

Embodiment 19A. The compound of embodiment 15A or a stereoisomer or tautomer thereof, or a pharmaceutically acceptable salt of any of the foregoing, wherein both $R^e$ together with the N to which they are attached are taken together to form a 3-10 membered heterocyclyl, wherein the 3-10 membered heterocyclyl is optionally substituted with one or more halo, oxo, —OH, —$NH_2$, —NH—$S(O)_2$—$R^a$, or —$S(O)_2$—$R^a$, wherein $R^a$ is $C_{1-6}$alkyl.

Embodiment 20A. The compound of any one of embodiments 1A-19A, or a stereoisomer or tautomer thereof, or a pharmaceutically acceptable salt of any of the foregoing, wherein each of $X^1$ and $X^2$ is $C(R^5)$.

Embodiment 21A. The compound of any one of embodiments 1A-19A, or a stereoisomer or tautomer thereof, or a pharmaceutically acceptable salt of any of the foregoing, wherein one of $X^1$ and $X^2$ is N and the other is $C(R^5)$.

Embodiment 22A. The compound of any one of embodiments 1A-19A, or a stereoisomer or tautomer thereof, or a pharmaceutically acceptable salt of any of the foregoing, wherein one of $X^1$ and $X^2$ is $CR^5$, and the other of $X^1$ and $X^2$ is C that is taken together with $R^4$, and the atoms to which they are attached, to form a 5-10 membered heterocyclyl optionally substituted with one or more of $R^b$.

Embodiment 23A. The compound of embodiment 22A, or a stereoisomer or tautomer thereof, or a pharmaceutically acceptable salt of any of the foregoing, wherein $R^b$ is halo, oxo, $C_{1-6}$alkyl, —C(O)—$C_{1-6}$alkyl, —C(O)—$NH_2$, —C(O)—$NH(C_{1-6}alkyl)$, —C(O)—$N(C_{1-6}alkyl)_2$, —$S(O)_2$—$R^a$, $C_{3-10}$cycloalkyl, and 3-10 membered heterocyclyl, wherein the $C_{1-6}$alkyl of $R^b$ is optionally substituted with one or more halo, OH, or —$S(O)_2$—$C_{1-6}$alkyl, and the $C_{3-10}$cycloalkyl of $R^b$ is optionally substituted with one or more —OH.

Embodiment 24A. The compound of any one of embodiments 1A-19A, or a stereoisomer or tautomer thereof, or a pharmaceutically acceptable salt of any of the foregoing, wherein one of $X^1$ and $X^2$ is $CR^5$, and the other of $X^1$ and $X^2$ is C that is taken together with $R^4$, and the atoms to which they are attached, to form a 5-10 membered heteroaryl optionally substituted with one or more $R^c$.

Embodiment 25A. The compound of embodiment 24A, or a stereoisomer or tautomer thereof, or a pharmaceutically acceptable salt of any of the foregoing, wherein $R^c$ is halo, $C_{1-6}$alkyl, —C(O)—$C_{1-6}$alkyl, —C(O)—$NH_2$, —C(O)—$NH(C_{1-6}alkyl)$, —C(O)—$N(C_{1-6}alkyl)_2$, —$S(O)_2$—$R^a$, $C_{3-10}$cycloalkyl, and 3-10 membered heterocyclyl, wherein the $C_{1-6}$alkyl of $R^c$ is optionally substituted with one or more —$S(O)_2$—$C_{1-6}$alkyl, and the $C_{3-10}$cycloalkyl of $R^c$ is optionally substituted with one or more —OH.

Embodiment 26A. The compound of any one of embodiments 1A-25A, or a stereoisomer or tautomer thereof, or a pharmaceutically acceptable salt of any of the foregoing, wherein $R^5$ is independently at each occurrence, H, halo, —CN, 3-10 membered heterocyclyl, $C_{1-6}$alkyl, or $C_{1-6}$alkoxy, wherein the $C_{1-6}$alkyl of $R^5$ is optionally substituted with one or more halo, or —OH and wherein the $C_{1-6}$alkoxy is optionally substituted with one or more halo.

Embodiment 27A. The compound of embodiment 1A, or a stereoisomer or tautomer thereof, or a pharmaceutically acceptable salt of any of the foregoing, wherein the compound, or a stereoisomer or tautomer thereof, or a pharmaceutically acceptable salt of any of the foregoing, is selected from Compounds 1-273 of Table 1.

Embodiment 29A. A method for preparing a compound of embodiment 1A, or a stereoisomer or tautomer thereof, or a pharmaceutically acceptable salt of any of the foregoing, comprising a step of reacting a compound of formula I'-A:

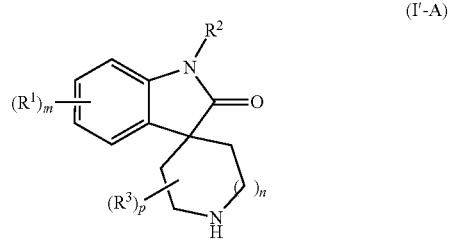

(I'-A)

wherein:
m is an integer from 0 to 4;
n is an integer from 0 to 2;
p is an integer from 0 to 10;
$R^1$, if present is, independently at each occurrence selected from the group consisting of halo, —CN, $C_{1-6}$alkoxy or —$C_{1-6}$alkyl, wherein
the $C_{1-6}$alkoxy of $R^1$ is optionally substituted with one or more halo, and
the $C_{1-6}$alkyl of $R^1$ is optionally substituted with one or more halo;
$R^2$ is H, $C_{1-6}$alkyl, $C_{3-10}$cycloalkyl, or 3-15 membered heterocyclyl, wherein
the $C_{1-6}$alkyl of $R^2$ is optionally substituted with one or more halo, —OH, —$NH_2$, or $C_{1-6}$alkoxy, and
the $C_{3-10}$cycloalkyl of $R^2$ is optionally substituted with one or more —OH; and
$R^3$, if present, is $C_{1-6}$alkyl;
with:
a compound of formula (I'—B):

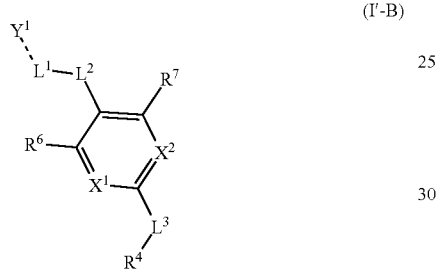

wherein:
the dashed line represents a single or double bond;
$Y^1$ is halo, oxo, or a sulfonate ester
$L^1$ is $C_{1-6}$alkylene, wherein the $C_{1-6}$alkylene of $L^1$ is optionally substituted with one or more $C_{1-6}$alkyl, and wherein the $C_{1-6}$alkyl is further optionally substituted with one or more —OH or $C_{1-6}$alkoxy;
$L^2$ is O or N($R^x$), wherein $R^x$ is H or $C_{1-6}$alkyl; and
either
(1) $L^3$ is absent or is O, $C_{3-10}$cycloalkyl, 3-10 membered heterocyclyl, or $C_{1-6}$alkylene, wherein
the $C_{1-6}$alkylene of $L^3$ is optionally substituted with one or more $C_{1-6}$alkyl, and
the 3-10 membered heterocyclyl is optionally substituted with one or more —OH;
$X^1$ and $X^2$ are each independently N or C($R^5$); and
$R^4$ is:
(i) —$S(O)_2$—$R^a$;
(ii) 5-20 membered heteroaryl, wherein the 5-20 membered heteroaryl of $R^4$ is optionally substituted with one or more $C_{1-6}$alkyl;
(iii) —N($R^d$)$_2$, wherein $R^d$ is independently at each occurrence H, $C_{1-6}$ alkyl, or —$S(O)_2$—$R^a$, wherein the $C_{1-6}$alkyl of $R^d$ is optionally substituted with one or more —OH,
(iv) —NS(O)—($C_{1-6}$alkyl)$_2$, wherein the $C_{1-6}$alkyl of $R^d$ is optionally substituted with one or more —OH,
(v) —C(O)—N($R^e$)$_2$ wherein $R^e$ is independently at each occurrence H, $C_{1-6}$ alkyl, or 3-10 membered heterocycle, wherein the 3-10 membered heterocycle is optionally substituted with one or more oxo, or both $R^e$ together with the N to which they are attached are taken together to form a 3-10 membered heterocyclyl, wherein the 3-10 membered heterocyclyl is optionally substituted with one or more halo, oxo, —OH, $NH_2$, NH—$S(O)_2$—$R^a$, or —$S(O)_2$—$R^a$,
(vi) 3-10 membered heterocyclyl optionally substituted with one or more $C_{1-6}$alkyl or oxo,
(vii) —S(O)—N($C_{1-6}$alkyl)-($C_{1-6}$alkyl),
(viii) —CN
or
(2) $L^3$ is absent; and
one of $X^1$ and $X^2$ is N or C($R^5$); and
the other of $X^1$ and $X^2$ is N or C that is taken together with $R^4$, and the atoms to which they are attached, to form a 5-10 membered heterocyclyl or a 5-20 membered heteroaryl, wherein
the 5-10 membered heterocyclyl is optionally substituted with one or more $R^b$, wherein $R^b$ is, independently at each occurrence, selected from the group consisting of halo, oxo, $C_{1-6}$alkyl, —C(O)—$C_{1-6}$alkyl, —C(O)—$NH_2$, —C(O)—NH($C_{1-6}$alkyl), —C(O)—N($C_{1-6}$alkyl)$_2$, —$S(O)_2$—$R^a$, $C_{3-10}$cycloalkyl, and 3-10 membered heterocyclyl, wherein
the $C_{1-6}$alkyl of $R^b$ is optionally substituted with one or more halo, OH, or —$S(O)_2$—$C_{1-6}$alkyl, and
the $C_{3-10}$cycloalkyl of $R^b$ is optionally substituted with one or more —OH, and
the 5-20 membered heteroaryl is optionally substituted with one or more $R^c$, wherein $R^c$ is, independently at each occurrence, selected from the group consisting of halo, $C_{1-6}$alkyl, —C(O)—$C_{1-6}$alkyl, —C(O)—$NH_2$, —C(O)—NH($C_{1-6}$alkyl), —C(O)—N($C_{1-6}$alkyl)$_2$, —$S(O)_2$—$R^a$, $C_{3-10}$cycloalkyl, and 3-10 membered heterocyclyl, wherein
the $C_{1-6}$alkyl of $R^c$ is optionally substituted with one or more —$S(O)_2$—$C_{1-6}$alkyl, and
the $C_{3-10}$cycloalkyl of $R^c$ is optionally substituted with one or more —OH;
$R^a$ is, independently at each occurrence:
(i) $C_{1-6}$alkyl optionally substituted with one or more halo, —OH, —$S(O)_2$—$C_{1-6}$alkyl, or —N($C_{1-6}$alkyl)-C(O)—$C_{1-6}$alkyl, or
(ii) $C_{3-10}$cycloalkyl optionally substituted with one or more —OH, —$C(O)_2$—$C_{1-6}$alkyl, —C(O)—NH($C_{1-6}$alkyl), —C(O)—N($C_{1-6}$alkyl)$_2$, or —C(O)—$C_{3-10}$heterocyclyl, or $C_{1-6}$alkyl, wherein the $C_{1-6}$alkyl is optionally substituted with one or more —OH, or
(iii) 3-10 membered heterocyclyl optionally substituted with one or more $C_{1-6}$alkyl;
$R^5$ is, independently at each occurrence, H, halo, —CN, 3-10 membered heterocyclyl, $C_{1-6}$alkyl, or $C_{1-6}$alkoxy, wherein the $C_{1-6}$alkyl of $R^5$ is optionally substituted with one or more halo, or —OH and wherein the $C_{1-6}$alkoxy is optionally substituted with one or more halo;
$R^6$ and $R^7$ are each independently H or halo;
to give a compound of embodiment 1, or a stereoisomer or tautomer thereof, or a pharmaceutically acceptable salt of any of the foregoing.
Embodiment 30A. The method of embodiment 29A, wherein the compound of embodiment 1 is prepared by a step comprising:

a) alkylation of an amine of formula (I'-A) with an alkyl halide, or sulfonate ester compound of formula (I'—B) in the presence of an inorganic base; or b) reductive amination of a ketone of formula (I'—B) with an amine of formula (I'-A).

Embodiment 31A. The method of embodiment 30A, wherein the inorganic base is selected from the group consisting of potassium carbonate, and sodium bicarbonate.

Embodiment 32A. The method of embodiment 30A, wherein the reductive amination proceeds under the action of sodium triacetoxyborohydride, titanium tetraiopropoxide and acetic acid.

Embodiment 33A. A method for preparing a compound of embodiment 1A, or a stereoisomer or tautomer thereof, or a pharmaceutically acceptable salt of any of the foregoing, comprising a step of reacting a compound of formula I'—C:

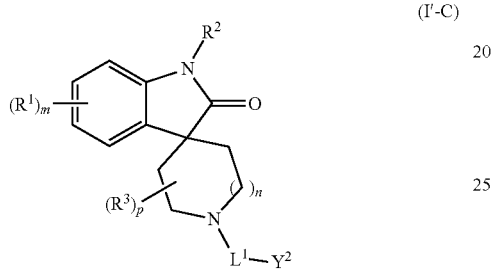
(I'-C)

wherein:
m is an integer from 0 to 4;
n is an integer from 0 to 2;
p is an integer from 0 to 10;
$R^1$, if present is, independently at each occurrence selected from the group consisting of halo, —CN, $C_{1-6}$alkoxy or —$C_{1-6}$alkyl, wherein
  the $C_{1-6}$alkoxy of $R^1$ is optionally substituted with one or more halo, and
  the $C_{1-6}$alkyl of $R^1$ is optionally substituted with one or more halo;
$R^2$ is H, $C_{1-6}$alkyl, $C_{3-10}$cycloalkyl, or 3-15 membered heterocyclyl, wherein
  the $C_{1-6}$alkyl of $R^2$ is optionally substituted with one or more halo, —OH, —$NH_2$, or $C_{1-6}$alkoxy, and
  the $C_{3-10}$cycloalkyl of $R^2$ is optionally substituted with one or more —OH;
$R^3$, if present, is $C_{1-6}$alkyl;
$L^1$ is $C_{1-6}$alkylene, wherein the $C_{1-6}$alkylene of $L^1$ is optionally substituted with one or more $C_{1-6}$alkyl, and wherein the $C_{1-6}$alkyl is further optionally substituted with one or more —OH or $C_{1-6}$alkoxy; and
$Y^2$ is halo, —OH or $NH_2$;
with:
a compound of formula (I'-D):

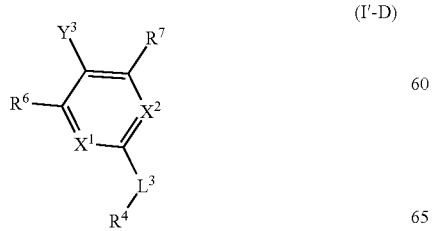
(I'-D)

wherein:
$Y^3$ is —OH or $NH(R^x)$, wherein $R^x$ is H or $C_{1-6}$alkyl; and
either
(1) $L^3$ is absent or is O, $C_{3-10}$cycloalkyl, 3-10 membered heterocyclyl, or $C_{1-6}$alkylene, wherein
  the $C_{1-6}$alkylene of $L^3$ is optionally substituted with one or more $C_{1-6}$alkyl, and
  the 3-10 membered heterocyclyl is optionally substituted with one or more —OH;
$X^1$ and $X^2$ are each independently N or $C(R^5)$; and
$R^4$ is:
  (i) —$S(O)_2$—$R^a$;
  (ii) 5-20 membered heteroaryl, wherein the 5-20 membered heteroaryl of $R^4$ is optionally substituted with one or more $C_{1-6}$alkyl;
  (iii) —$N(R^d)_2$, wherein $R^d$ is independently at each occurrence H, $C_{1-6}$ alkyl, or —$S(O)_2$—$R^a$, wherein the $C_{1-6}$alkyl of $R^d$ is optionally substituted with one or more —OH,
  (iv) —NS(O)—$(C_{1-6}$alkyl$)_2$, wherein the $C_{1-6}$alkyl of $R^d$ is optionally substituted with one or more —OH,
  (v) —C(O)—$N(R^e)_2$ wherein $R^e$ is independently at each occurrence H, $C_{1-6}$ alkyl, or 3-10 membered heterocycle, wherein the 3-10 membered heterocycle is optionally substituted with one or more oxo, or both $R^e$ together with the N to which they are attached are taken together to form a 3-10 membered heterocyclyl, wherein the 3-10 membered heterocyclyl is optionally substituted with one or more halo, oxo, —OH, $NH_2$, NH—$S(O)_2$—$R^a$, or —$S(O)_2$—$R^a$,
  (vi) 3-10 membered heterocyclyl optionally substituted with one or more $C_{1-6}$alkyl or oxo,
  (vii) —S(O)—$N(C_{1-6}$alkyl$)$-$(C_{1-6}$alkyl$)$,
  (viii) —CN;
or
(2) $L^3$ is absent; and
one of $X^1$ and $X^2$ is N or $C(R^5)$; and
the other of $X^1$ and $X^2$ is N or C that is taken together with $R^4$, and the atoms to which they are attached, to form a 5-10 membered heterocyclyl or a 5-20 membered heteroaryl, wherein
  the 5-10 membered heterocyclyl is optionally substituted with one or more $R^b$, wherein $R^b$ is, independently at each occurrence, selected from the group consisting of halo, oxo, $C_{1-6}$alkyl, —C(O)—$C_{1-6}$alkyl, —C(O)—$NH_2$, —C(O)—$NH(C_{1-6}$alkyl$)$, —C(O)—$N(C_{1-6}$alkyl$)_2$, —$S(O)_2$—$R^a$, $C_{3-10}$cycloalkyl, and 3-10 membered heterocyclyl, wherein
    the $C_{1-6}$alkyl of $R^b$ is optionally substituted with one or more halo, OH, or —$S(O)_2$—$C_{1-6}$alkyl, and
    the $C_{3-10}$cycloalkyl of $R^b$ is optionally substituted with one or more —OH, and
  the 5-20 membered heteroaryl is optionally substituted with one or more $R^c$, wherein $R^c$ is, independently at each occurrence, selected from the group consisting of halo, $C_{1-6}$alkyl, —C(O)—$C_{1-6}$alkyl, —C(O)—$NH_2$, —C(O)—$NH(C_{1-6}$alkyl$)$, —C(O)—$N(C_{1-6}$alkyl$)_2$, —$S(O)_2$—$R^a$, $C_{3-10}$cycloalkyl, and 3-10 membered heterocyclyl, wherein
    the $C_{1-6}$alkyl of $R^c$ is optionally substituted with one or more —$S(O)_2$—$C_{1-6}$alkyl, and the $C_{3-10}$cycloalkyl of $R^c$ is optionally substituted with one or more —OH;

$R^a$ is, independently at each occurrence:
(i) $C_{1-6}$alkyl optionally substituted with one or more halo, —OH, —S(O)$_2$—$C_{1-6}$alkyl, or —N($C_{1-6}$alkyl)-C(O)—$C_{1-6}$alkyl, or
(ii) $C_{3-10}$cycloalkyl optionally substituted with one or more —OH, —C(O)$_2$—$C_{1-6}$alkyl, —C(O)—NH($C_{1-6}$alkyl), —C(O)—N($C_{1-6}$alkyl)$_2$, or —C(O)—$C_{3-10}$heterocyclyl, or $C_{1-6}$alkyl, wherein the $C_{1-6}$alkyl is optionally substituted with one or more —OH, or
(iii) 3-10 membered heterocyclyl optionally substituted with one or more $C_{1-6}$alkyl;

$R^5$ is, independently at each occurrence, H, halo, —CN, 3-10 membered heterocyclyl, $C_{1-6}$alkyl, or $C_{1-6}$alkoxy, wherein the $C_{1-6}$alkyl of $R^5$ is optionally substituted with one or more halo, or —OH and wherein the $C_{1-6}$alkoxy is optionally substituted with one or more halo; and $R^6$ and $R^7$ are each independently H or halo;

to give a compound of embodiment 1, or a stereoisomer or tautomer thereof, or a pharmaceutically acceptable salt of any of the foregoing.

Embodiment 34A. The method of embodiment 33A, wherein the compound of embodiment 1 is prepared by a step comprising:
a) coupling of an alcohol compound of formula (I'—C) with a phenol compound of formula (I'-D), or a heterocyclic variant, under Mitsunobu-type reaction conditions; or
b) reacting an alkyl halide compound of formula (I'—C) with a phenol or amine compound of formula (I'-D), in the presence of a catalyst.

Embodiment 35A. The method of embodiment 34A, wherein the Mitsunobi-type reaction conditions comprises coupling of an alcohol compound of formula (I'—C) with a phenol compound of formula (I'-D), or a heterocyclic variant, in the presence of triphenylphosphine and diisopropyl azodicarboxylate.

Embodiment 36A. The method of embodiment 34A, wherein the catalyst is silver oxide or potassium carbonate.

Embodiment 37A. A pharmaceutical composition, comprising (i) a compound of any one of embodiments 1A-28A, or a stereoisomer or tautomer thereof, or a pharmaceutically acceptable salt of any of the foregoing, and (ii) one or more pharmaceutically acceptable excipients.

Embodiment 38A. A method of modulating APOL1 in a cell, comprising exposing the cell to a composition comprising an effective amount of a compound of any one or embodiments 1A-28A, or a stereoisomer or tautomer thereof, or a pharmaceutically acceptable salt of any of the foregoing, or a pharmaceutical composition of embodiment 37A.

Embodiment 39A. A method of inhibiting APOL1 in a cell, comprising exposing the cell to a composition comprising an effective amount of a compound of any one or embodiments 1A-28A or a stereoisomer or tautomer thereof, or a pharmaceutically acceptable salt of any of the foregoing, or a pharmaceutical composition of embodiment 37A.

Embodiment 40A. A method of treating an APOL1-mediated disease, disorder, or condition in an individual in need thereof, comprising administering to the individual a compound of any one of embodiments 1A-28A, or a stereoisomer or tautomer thereof, or a pharmaceutically acceptable salt of any of the foregoing, or a pharmaceutical composition of embodiment 37A.

Embodiment 41A. The method of embodiment 40A, wherein the disease, disorder, or condition is selected from the group consisting of chronic kidney disease, focal segmental glomerulosclerosis (FSGS), hypertension-attributed kidney disease, human immunodeficiency virus-associated nephropathy (HIVAN), sickle-cell nephropathy, lupus nephritis, diabetic kidney disease, APOL1-associated nephropathy, viral nephropathy, COVID-19 associated nephropathy, preeclampsia, and sepsis.

Embodiment 42A. The method of embodiment 40A or embodiment 41A, wherein the disease, disorder, or condition is a kidney disease.

Embodiment 43A. The method of any one of embodiments 40A-42A, wherein the disease, disorder, or condition is a chronic kidney disease (CKD).

Embodiment 44A. A method of delaying the development of an APOL1-mediated disease, disorder, or condition, comprising administering a compound of any one of embodiments 1A-28A, or a stereoisomer or tautomer thereof, or a pharmaceutically acceptable salt of any of the foregoing, or a pharmaceutical composition of embodiment 37A, to an individual who is at risk of developing an APOL1-mediated disease, disorder, or condition.

Embodiment 45A. The method of embodiment 44A, wherein the APOL1-mediated disease, disorder, or condition is a kidney disease.

Embodiment 46A. The method of embodiment 44A or embodiment 45A, wherein the APOL1-mediated disease, disorder, or condition is a chronic kidney disease.

Embodiment 47A. The method of embodiment 44A, wherein the APOL1-mediated disease, disorder, or condition is selected from the group consisting of chronic kidney disease, focal segmental glomerulosclerosis (FSGS), hypertension-attributed kidney disease, human immunodeficiency virus-associated nephropathy (HIVAN), sickle-cell nephropathy, lupus nephritis, diabetic kidney disease, APOL1-associated nephropathy, viral nephropathy, COVID-19 associated nephropathy, preeclampsia, and sepsis.

Embodiment 48A. The method of any one of embodiments 40A-47A, wherein the individual has an APOL1 mutation.

Embodiment 49A. The method of embodiment 48A, wherein the APOL1 mutation is a gain-of-function mutation.

Embodiment 50A. The method of any one of embodiments 40A-49A, wherein a therapeutically effective amount of a compound of any one of embodiments 1A-28A, or a stereoisomer or tautomer thereof, or a pharmaceutically acceptable salt of any of the foregoing, or a pharmaceutical composition of embodiment 37A, is administered.

Embodiment 51A. A kit, comprising (i) a compound of any one of embodiments 1A-28A, or a stereoisomer or tautomer thereof, or a pharmaceutically acceptable salt of any of the foregoing, or a pharmaceutical composition of embodiment 37A, and (ii) instructions for use in treating an APOL1-mediated disease, disorder, or condition in an individual in need thereof.

Embodiment 52A. The kit of embodiment 51A, wherein the disease, disorder, or condition is a kidney disease.

Embodiment 53A. The kit of embodiment 51A or embodiment 52A, wherein the disease, disorder, or condition is a chronic kidney disease (CKD).

Embodiment 54A. The kit of any one of embodiments 51A-53A, wherein the disease, disorder, or condition is selected from the group consisting of chronic kidney disease, focal segmental glomerulosclerosis (FSGS), hypertension-attributed kidney disease, human immunodeficiency virus-associated nephropathy (HIVAN), sickle-cell nephropathy, lupus nephritis, diabetic kidney disease, APOL1-associated nephropathy, viral nephropathy, COVID-19 associated nephropathy, preeclampsia, and sepsis.

Embodiment 55A. The kit of any one of embodiments 51A-54A, wherein the individual has an APOL1 mutation.

Embodiment 56A. The kit of embodiment 55A, wherein the APOL1 mutation is a gain-of-function mutation.

Embodiment 1B. A compound of formula (I'):

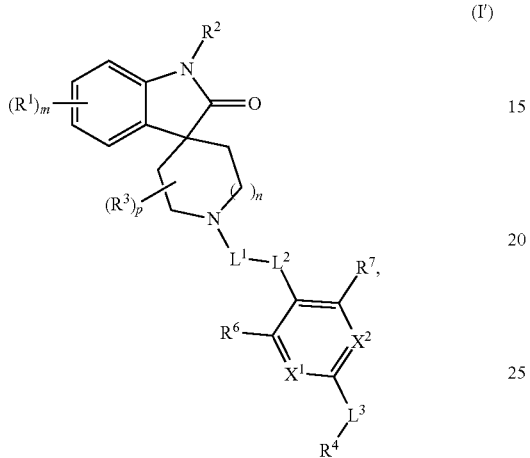

or a stereoisomer or tautomer thereof, or a pharmaceutically acceptable salt of any of the foregoing, wherein:

m is an integer from 0 to 4;

n is an integer from 0 to 2;

p is an integer from 0 to 10;

$R^1$, if present is, independently at each occurrence selected from the group consisting of halo, —CN, $C_{1-6}$alkoxy, or $C_{1-6}$alkyl, wherein
  the $C_{1-6}$alkoxy of $R^1$ is optionally substituted with one or more halo, and
  the $C_{1-6}$alkyl of $R^1$ is optionally substituted with one or more halo;

$R^2$ is H, $C_{1-6}$alkyl, $C_{3-10}$cycloalkyl, or 3-15 membered heterocyclyl, wherein
  the $C_{1-6}$alkyl of $R^2$ is optionally substituted with one or more halo, —OH, —NH$_2$, or $C_{1-6}$alkoxy, and
  the $C_{3-10}$cycloalkyl of $R^2$ is optionally substituted with one or more —OH;

$R^3$, if present, is $C_{1-6}$alkyl;

$L^1$ is $C_{1-6}$alkylene, wherein the $C_{1-6}$alkylene of $L^1$ is optionally substituted with one or more $C_{1-6}$alkyl, and wherein the $C_{1-6}$alkyl is further optionally substituted with one or more —OH or $C_{1-6}$alkoxy;

$L^2$ is O or $N(R^x)$, wherein $R^x$ is H or $C_{1-6}$alkyl; and either (1) $L^3$ is absent or is O, $C_{3-10}$cycloalkyl, 3-10 membered heterocyclyl, or $C_{1-6}$alkylene, wherein
  the $C_{3-10}$cycloalkyl is optionally substituted with one or more —OH, or $C_{1-6}$alkyl,
  the $C_{1-6}$alkylene of $L^3$ is optionally substituted with one or more —OH, or $C_{1-6}$alkyl, and
  the 3-10 membered heterocyclyl is optionally substituted with one or more —OH;

$X^1$ and $X^2$ are each independently N or $C(R^5)$; and $R^4$ is:
  (i) —S(O)$_2$—$R^a$;
  (ii) 5-20 membered heteroaryl, wherein the 5-20 membered heteroaryl of $R^4$ is optionally substituted with one or more $C_{1-6}$alkyl;
  (iii) —N(R$^d$)$_2$, wherein R$^d$ is independently at each occurrence H, $C_{1-6}$ alkyl, or —S(O)$_2$—$R^a$, wherein the $C_{1-6}$alkyl of R$^d$ is optionally substituted with one or more —OH,
  (iv) —NS(O)—(C$_{1-6}$alkyl)$_2$, wherein the $C_{1-6}$alkyl is optionally substituted with one or more —OH,
  (v) —C(O)—N(R$^e$)$_2$ wherein R$^e$ is independently at each occurrence H, $C_{1-6}$ alkyl, or 3-10 membered heterocycle, wherein the 3-10 membered heterocycle is optionally substituted with one or more oxo, or both R$^e$ together with the N to which they are attached are taken together to form a 3-10 membered heterocyclyl, wherein the 3-10 membered heterocyclyl is optionally substituted with one or more halo, oxo, —OH, NH$_2$, —NH—S(O)$_2$—$R^a$, or —S(O)$_2$—$R^a$,
  (vi) 3-10 membered heterocyclyl optionally substituted with one or more $C_{1-6}$alkyl, —OH, oxo or —S(O)$_2$R$^a$,
  (vii) —S(O)—N(C$_{1-6}$alkyl)-(C$_{1-6}$alkyl),
  (viii) —CN,
  (ix) —(CH$_2$)$_q$OH, wherein q is an integer from 0-6,
  (x) —C(O)—C$_{1-6}$alkyl, or
  (xi) —P(O)(C$_{1-6}$alkyl)$_2$;

or (2) $L^3$ is absent; and
  one of $X^1$ and $X^2$ is N or $C(R^5)$; and
  the other of $X^1$ and $X^2$ is N or C that is taken together with $R^4$, and the atoms to which they are attached, to form a 5-10 membered heterocyclyl or a 5-20 membered heteroaryl, wherein
    the 5-10 membered heterocyclyl is optionally substituted with one or more R$^b$, wherein R$^b$ is, independently at each occurrence, selected from the group consisting of halo, oxo, $C_{1-6}$alkyl, —C(O)—$C_{1-6}$alkyl, —C(O)—NH$_2$, —C(O)—NH(C$_{1-6}$alkyl), —C(O)—N(C$_{1-6}$alkyl)$_2$, —S(O)$_2$—$R^a$, $C_{3-10}$cycloalkyl, and 3-10 membered heterocyclyl, wherein
      the $C_{1-6}$alkyl of R$^b$ is optionally substituted with one or more halo, OH, —S(O)$_2$—$C_{1-6}$alkyl, or $C_{3-10}$cycloalkyl, and
      wherein the $C_{3-10}$cycloalkyl of the $C_{1-6}$alkyl of R$^b$ is further optionally substituted with one or more $C_{1-6}$alkyl or —OH and
      the $C_{3-10}$cycloalkyl of R$^b$ is optionally substituted with one or more —OH, $C_{3-10}$cycloalkyl, or $C_{1-6}$alkyl, and
      wherein the $C_{1-6}$alkyl of the $C_{3-10}$cycloalkyl of R$^b$ is further optionally substituted with one or more —OH, and
    the 5-20 membered heteroaryl is optionally substituted with one or more R$^c$, wherein R$^c$ is, independently at each occurrence, selected from the group consisting of halo, $C_{1-6}$alkyl, —C(O)—$C_{1-6}$alkyl, —C(O)—NH$_2$, —C(O)—NH(C$_{1-6}$alkyl), —C(O)—N(C$_{1-6}$alkyl)$_2$, —S(O)$_2$—$R^a$, $C_{3-10}$cycloalkyl, and 3-10 membered heterocyclyl, wherein
      the $C_{1-6}$alkyl of R$^c$ is optionally substituted with one or more —S(O)$_2$—$C_{1-6}$alkyl,
      the $C_{3-10}$cycloalkyl of R$^c$ is optionally substituted with one or more —OH, or $C_{1-6}$alkyl, and the 3-10 membered heterocyclyl of $R^c$ is optionally substituted with one or more —OH, or $C_{1-6}$alkyl, and
wherein the $C_{1-6}$alkyl of 3-10 membered heterocyclyl of $R^c$ is further optionally substituted with one or more —OH;
$R^a$ is, independently at each occurrence:
(i) $C_{1-6}$alkyl optionally substituted with one or more halo, —OH, —S(O)$_2$—C$_{1-6}$alkyl, or —N(C$_{1-6}$alkyl)-C(O)—C$_{1-6}$alkyl,
(ii) $C_{3-10}$cycloalkyl optionally substituted with one or more —OH, —C(O)$_2$—C$_{1-6}$alkyl, —C(O)—NH(C$_{1-6}$alkyl), —C(O)—N(C$_{1-6}$alkyl)$_2$, or —C(O)—C$_{3-10}$heterocyclyl, or C$_{1-6}$alkyl, wherein the C$_{1-6}$alkyl is optionally substituted with one or more —OH, or
(iii) 3-10 membered heterocyclyl optionally substituted with one or more C$_{1-6}$alkyl;
$R^5$ is, independently at each occurrence, H, halo, —CN, 3-10 membered heterocyclyl, C$_{1-6}$alkyl, or C$_{1-6}$alkoxy, wherein the C$_{1-6}$alkyl of $R^5$ is optionally substituted with one or more halo, or —OH and wherein the C$_{1-6}$alkoxy of $R^5$ is optionally substituted with one or more halo; and
$R^6$ and $R^7$ are each independently H or halo.

Embodiment 15B. The compound of embodiments 1B or a stereoisomer or tautomer thereof, or a pharmaceutically acceptable salt of any of the foregoing, wherein $R^4$ is S(O)$_2$—R$^a$, 5-10 membered heteroaryl, —N(R$^d$)$_2$, —NS(O)—(C$_{1-3}$alkyl)$_2$, —C(O)—N(R$^e$)$_2$, 3-6 membered heterocyclyl, —S(O)(N—C$_{1-3}$alkyl)-(C$_{1-3}$alkyl), —CN, or —OH, wherein
the 5-20 membered heteroaryl of $R^4$ is optionally substituted with one or more C$_{1-6}$alkyl, and
the 3-6 membered heterocyclyl optionally substituted with one or more oxo or C$_{1-6}$alkyl.

Embodiment 23B. The compound of embodiment 1B, or a stereoisomer or tautomer thereof, or a pharmaceutically acceptable salt of any of the foregoing, wherein one of $X^1$ and $X^2$ is CR$^5$, and the other of $X^1$ and $X^2$ is C that is taken together with $R^4$, and the atoms to which they are attached, to form a 5-10 membered heterocyclyl optionally substituted with one or more of $R^b$.

Embodiments 24B. The compound of embodiment 23B, or a stereoisomer or tautomer thereof, or a pharmaceutically acceptable salt of any of the foregoing, wherein $R^b$ is halo, oxo, C$_{1-6}$alkyl, —C(O)—C$_{1-6}$alkyl, —C(O)—NH$_2$, —C(O)—NH(C$_{1-6}$alkyl), —C(O)—N(C$_{1-6}$alkyl)$_2$, —S(O)$_2$—R$^a$, C$_{3-10}$cycloalkyl, and 3-10 membered heterocyclyl, wherein the C$_{1-6}$alkyl of $R^b$ is optionally substituted with one or more halo, OH, or —S(O)$_2$—C$_{1-6}$alkyl, and the C$_{3-10}$cycloalkyl of $R^b$ is optionally substituted with one or more —OH, C$_{3-10}$cycloalkyl, or C$_{1-6}$alkyl.

Embodiments 25B. The compound of embodiment 24B, or a stereoisomer or tautomer thereof, or a pharmaceutically acceptable salt of any of the foregoing, wherein, $R^c$ is halo, C$_{1-6}$alkyl, —C(O)—C$_{1-6}$alkyl, —C(O)—NH$_2$, —C(O)—NH(C$_{1-6}$alkyl), —C(O)—N(C$_{1-6}$alkyl)$_2$, —S(O)$_2$—R$^a$, C$_{3-10}$cycloalkyl, and 3-10 membered heterocyclyl, wherein the C$_{1-6}$alkyl of R$^c$ is optionally substituted with one or more —S(O)$_2$—C$_{1-6}$alkyl, and the C$_{3-10}$cycloalkyl of R$^c$ is optionally substituted with one or more —OH, or C$_{1-6}$alkyl.

Methods of Preparing

The present disclosure further provides methods for preparing the compounds of present invention. In some aspect, provided herein are methods of preparing a compound of formula (II), or any embodiment or variation thereof, such as a compound of formula (I'), (I), (I-A) (I-B), (I-C), (I-D), (I-E), (I-F), (I-G), or (II-A), or a stereoisomer or tautomer thereof, or a pharmaceutically acceptable salt of any of the foregoing.

In some embodiments, a method for preparing a compound of formula (I), or a stereoisomer or tautomer thereof, or a pharmaceutically acceptable salt of any of the foregoing, comprises a step of reacting a compound of formula I'-A:

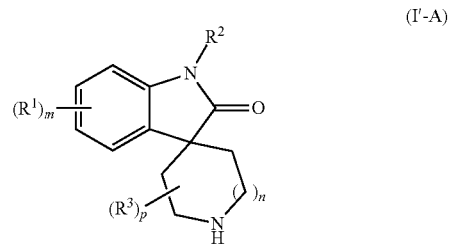

(I'-A)

wherein:
m is an integer from 0 to 4;
n is an integer from 0 to 2;
p is an integer from 0 to 10;
$R^1$, if present is, independently at each occurrence selected from the group consisting of halo, —CN, C$_{1-6}$alkoxy, or —C$_{1-6}$alkyl, wherein
the C$_{1-6}$alkoxy of $R^1$ is optionally substituted with one or more halo, and
the C$_{1-6}$alkyl of $R^1$ is optionally substituted with one or more halo;
$R^2$ is H, C$_{1-6}$alkyl, C$_{3-10}$cycloalkyl, or 3-15 membered heterocyclyl, wherein
the C$_{1-6}$alkyl of $R^2$ is optionally substituted with one or more halo, —OH, —NH$_2$, or C$_{1-6}$alkoxy, and
the C$_{3-10}$cycloalkyl of $R^2$ is optionally substituted with one or more —OH; and
$R^3$, if present, is C$_{1-6}$alkyl;
with:
a compound of formula (I'—B):

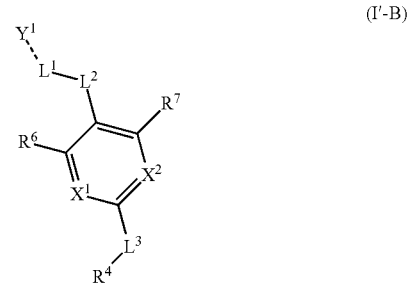

(I'-B)

wherein:
the dashed line represents a single or double bond;
$Y^1$ is halo, oxo, or a sulfonate ester
$L^1$ is C$_{1-6}$alkylene, wherein the C$_{1-6}$alkylene of $L^1$ is optionally substituted with one or more C$_{1-6}$alkyl, and wherein the C$_{1-6}$alkyl is further optionally substituted with one or more —OH or C$_{1-6}$alkoxy;
$L^2$ is O or N(R$^x$), wherein R$^x$ is H or C$_{1-6}$alkyl; and either
(1) $L^3$ is absent or is O, C$_{3-10}$cycloalkyl, 3-10 membered heterocyclyl, or C$_{1-6}$alkylene, wherein the C$_{1-6}$alkylene of L$^3$ is optionally substituted with one or more C$_{1-6}$alkyl, and the 3-10 membered heterocyclyl is optionally substituted with one or more —OH;

X$^1$ and X$^2$ are each independently N or C(R$^5$); and R$^4$ is:
(i) —S(O)$_2$—R$^a$,
(ii) 5-20 membered heteroaryl, wherein the 5-20 membered heteroaryl of R$^4$ is optionally substituted with one or more C$_{1-6}$alkyl,
(iii) —N(R$^d$)$_2$, wherein R$^d$ is independently at each occurrence H, C$_{1-6}$ alkyl, or —S(O)$_2$—R$^a$, wherein the C$_{1-6}$alkyl of R$^d$ is optionally substituted with one or more —OH,
(iv) —NS(O)—(C$_{1-6}$alkyl)$_2$, wherein the C$_{1-6}$alkyl of R$^d$ is optionally substituted with one or more —OH,
(v) —C(O)—N(R$^e$)$_2$ wherein R$^e$ is independently at each occurrence H, C$_{1-6}$ alkyl, or 3-10 membered heterocycle, wherein the 3-10 membered heterocycle is optionally substituted with one or more oxo, or both R$^e$ together with the N to which they are attached are taken together to form a 3-10 membered heterocyclyl, wherein the 3-10 membered heterocyclyl is optionally substituted with one or more halo, oxo, —OH, NH$_2$, NH—S(O)$_2$—R$^a$, or —S(O)$_2$—R$^a$,
(vi) 3-10 membered heterocyclyl optionally substituted with one or more C$_{1-6}$alkyl or oxo,
(vii) —S(O)—N(C$_{1-6}$alkyl)-(C$_{1-6}$alkyl), or
(viii) —CN;

or (2) L$^3$ is absent; and
one of X$^1$ and X$^2$ is N or C(R$^5$); and
the other of X$^1$ and X$^2$ is N or C that is taken together with R$^4$, and the atoms to which they are attached, to form a 5-10 membered heterocyclyl or a 5-20 membered heteroaryl, wherein
the 5-10 membered heterocyclyl is optionally substituted with one or more R$^b$, wherein R$^b$ is, independently at each occurrence, selected from the group consisting of halo, oxo, C$_{1-6}$alkyl, —C(O)—C$_{1-6}$alkyl, —C(O)—NH$_2$, —C(O)—NH(C$_{1-6}$alkyl), —C(O)—N(C$_{1-6}$alkyl)$_2$, —S(O)$_2$—R$^a$, C$_{3-10}$cycloalkyl, and 3-10 membered heterocyclyl, wherein
the C$_{1-6}$alkyl of R$^b$ is optionally substituted with one or more halo, OH, or —S(O)$_2$—C$_{1-6}$alkyl, and
the C$_{3-10}$cycloalkyl of R$^b$ is optionally substituted with one or more —OH, and
the 5-20 membered heteroaryl is optionally substituted with one or more R$^c$, wherein R$^c$ is, independently at each occurrence, selected from the group consisting of halo, C$_{1-6}$alkyl, —C(O)—C$_{1-6}$alkyl, —C(O)—NH$_2$, —C(O)—NH(C$_{1-6}$alkyl), —C(O)—N(C$_{1-6}$alkyl)$_2$, —S(O)$_2$—R$^a$, C$_{3-10}$cycloalkyl, and 3-10 membered heterocyclyl, wherein
the C$_{1-6}$alkyl of R$^c$ is optionally substituted with one or more —S(O)$_2$—C$_{1-6}$alkyl, and
the C$_{3-10}$cycloalkyl of R$^c$ is optionally substituted with one or more —OH;

R$^a$ is, independently at each occurrence:
(i) C$_{1-6}$alkyl optionally substituted with one or more halo, —OH, —S(O)$_2$—C$_{1-6}$alkyl, or —N(C$_{1-6}$alkyl)-C(O)—C$_{1-6}$alkyl, or (ii) C$_{3-10}$cycloalkyl optionally substituted with one or more —OH, —C(O)$_2$—C$_{1-6}$alkyl, —C(O)—NH(C$_{1-6}$alkyl), —C(O)—N(C$_{1-6}$alkyl)$_2$, or —C(O)—C$_{3-10}$heterocyclyl, or C$_{1-6}$alkyl, wherein the C$_{1-6}$alkyl is optionally substituted with one or more —OH, or
(iii) 3-10 membered heterocyclyl optionally substituted with one or more C$_{1-6}$alkyl;

R$^5$ is, independently at each occurrence, H, halo, —CN, 3-10 membered heterocyclyl, C$_{1-6}$alkyl, or C$_{1-6}$alkoxy, wherein the C$_{1-6}$alkyl of R$^5$ is optionally substituted with one or more halo, or —OH and wherein the C$_{1-6}$alkoxy is optionally substituted with one or more halo;

R$^6$ and R$^7$ are each independently H or halo;

to give a compound of formula (I), or a stereoisomer or tautomer thereof, or a pharmaceutically acceptable salt of any of the foregoing.

In some embodiments, a method for preparing a compound of formula (I'), or a stereoisomer or tautomer thereof, or a pharmaceutically acceptable salt of any of the foregoing, comprises a step of reacting a compound of formula I'-A':

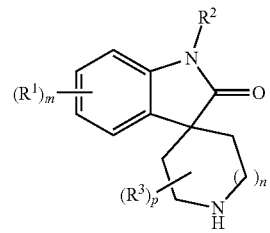

(I'-A')

wherein:

m is an integer from 0 to 4;

n is an integer from 0 to 2;

p is an integer from 0 to 10;

R$^1$, if present is, independently at each occurrence selected from the group consisting of halo, —CN, C$_{1-6}$alkoxy, or —C$_{1-6}$alkyl, wherein
the C$_{1-6}$alkoxy of R$^1$ is optionally substituted with one or more halo, and
the C$_{1-6}$alkyl of R$^1$ is optionally substituted with one or more halo;

R$^2$ is H, C$_{1-6}$alkyl, C$_{3-10}$cycloalkyl, or 3-15 membered heterocyclyl, wherein
the C$_{1-6}$alkyl of R$^2$ is optionally substituted with one or more halo, —OH, —NH$_2$, or C$_{1-6}$alkoxy, and
the C$_{3-10}$cycloalkyl of R$^2$ is optionally substituted with one or more —OH; and R$^3$, if present, is C$_{1-6}$alkyl;

with:
a compound of formula (I'—B'):

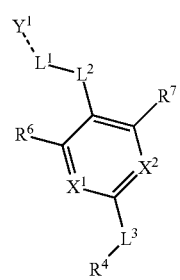

(I'-B')

wherein:
the dashed line represents a single or double bond;
$Y^1$ is halo, oxo, or a sulfonate ester
$L^1$ is $C_{1-6}$alkylene, wherein the $C_{1-6}$alkylene of $L^1$ is optionally substituted with one or more $C_{1-6}$alkyl, and wherein the $C_{1-6}$alkyl is further optionally substituted with one or more —OH or $C_{1-6}$alkoxy;
$L^2$ is O or $N(R^x)$, wherein $R^x$ is H or $C_{1-6}$alkyl; and
either
(1) $L^3$ is absent or is O, $C_{3-10}$cycloalkyl, 3-10 membered heterocyclyl, or $C_{1-6}$alkylene, wherein
the $C_{3-10}$cycloalkyl is optionally substituted with one or more —OH, or $C_{1-6}$alkyl,
the $C_{1-6}$alkylene of $L^3$ is optionally substituted with one or more —OH, or $C_{1-6}$alkyl, and
the 3-10 membered heterocyclyl is optionally substituted with one or more —OH;
$X^1$ and $X^2$ are each independently N or $C(R^5)$; and
$R^4$ is:
(i) —$S(O)_2$—$R^a$;
(ii) 5-20 membered heteroaryl, wherein the 5-20 membered heteroaryl of $R^4$ is optionally substituted with one or more $C_{1-6}$alkyl;
(iii) —$N(R^d)_2$, wherein $R^d$ is independently at each occurrence H, $C_{1-6}$ alkyl, or —$S(O)_2$—$R^a$, wherein the $C_{1-6}$alkyl of $R^d$ is optionally substituted with one or more —OH,
(iv) —NS(O)—$(C_{1-6}$alkyl$)_2$, wherein the $C_{1-6}$alkyl is optionally substituted with one or more —OH,
(v) —C(O)—$N(R^e)_2$ wherein $R^e$ is independently at each occurrence H, $C_{1-6}$ alkyl, or 3-10 membered heterocycle, wherein the 3-10 membered heterocycle is optionally substituted with one or more oxo, or both $R^e$ together with the N to which they are attached are taken together to form a 3-10 membered heterocyclyl, wherein the 3-10 membered heterocyclyl is optionally substituted with one or more halo, oxo, —OH, $NH_2$, —NH—$S(O)_2$—$R^a$, or —$S(O)_2$—$R^a$,
(vi) 3-10 membered heterocyclyl optionally substituted with one or more $C_{1-6}$alkyl, —OH, oxo or —$S(O)_2R^a$,
(vii) —S(O)—N($C_{1-6}$alkyl)-($C_{1-6}$alkyl),
(viii) —CN,
(ix) —$(CH_2)_q$OH, wherein q is an integer from 0-6,
(x) —C(O)—$C_{1-6}$alkyl, or
(xi) —$P(O)(C_{1-6}$alkyl$)_2$;
or
(2) $L^3$ is absent; and
one of $X^1$ and $X^2$ is N or $C(R^5)$; and
the other of $X^1$ and $X^2$ is N or C that is taken together with $R^4$, and the atoms to which they are attached, to form a 5-10 membered heterocyclyl or a 5-20 membered heteroaryl, wherein
the 5-10 membered heterocyclyl is optionally substituted with one or more $R^b$, wherein $R^b$ is, independently at each occurrence, selected from the group consisting of halo, oxo, $C_{1-6}$alkyl, —C(O)—$C_{1-6}$alkyl, —C(O)—$NH_2$, —C(O)—NH($C_{1-6}$alkyl), —C(O)—$N(C_{1-6}$alkyl$)_2$, —$S(O)_2$—$R^a$, $C_{3-10}$cycloalkyl, and 3-10 membered heterocyclyl, wherein
the $C_{1-6}$alkyl of $R^b$ is optionally substituted with one or more halo, OH, —$S(O)_2$—$C_{1-6}$alkyl, or $C_{3-10}$cycloalkyl, and
wherein the $C_{3-10}$cycloalkyl of the $C_{1-6}$alkyl of $R^b$ is further optionally substituted with one or more $C_{1-6}$alkyl or —OH and
the $C_{3-10}$cycloalkyl of $R^b$ is optionally substituted with one or more —OH, $C_{3-10}$cycloalkyl, or $C_{1-6}$alkyl, and
wherein the $C_{1-6}$alkyl of the $C_{3-10}$cycloalkyl of $R^b$ is further optionally substituted with one or more —OH, and
the 5-20 membered heteroaryl is optionally substituted with one or more $R^c$, wherein $R^c$ is, independently at each occurrence, selected from the group consisting of halo, $C_{1-6}$alkyl, —C(O)—$C_{1-6}$alkyl, —C(O)—$NH_2$, —C(O)—NH($C_{1-6}$alkyl), —C(O)—$N(C_{1-6}$alkyl$)_2$, —$S(O)_2$—$R^a$, $C_{3-10}$cycloalkyl, and 3-10 membered heterocyclyl, wherein
the $C_{1-6}$alkyl of $R^c$ is optionally substituted with one or more —$S(O)_2$—$C_{1-6}$alkyl,
the $C_{3-10}$cycloalkyl of $R^c$ is optionally substituted with one or more —OH, or $C_{1-6}$alkyl,
and the 3-10 membered heterocyclyl of $R^c$ is optionally substituted with one or more —OH, or $C_{1-6}$alkyl, and
wherein the $C_{1-6}$alkyl of the 3-10 membered heterocyclyl of $R^c$ is further optionally substituted with one or more —OH;
$R^a$ is, independently at each occurrence:
(i) $C_{1-6}$alkyl optionally substituted with one or more halo, —OH, —$S(O)_2$—$C_{1-6}$alkyl, or —$N(C_{1-6}$alkyl$)$-C(O)—$C_{1-6}$alkyl,
(ii) $C_{3-10}$cycloalkyl optionally substituted with one or more —OH, —$C(O)_2$—$C_{1-6}$alkyl, —C(O)—NH($C_{1-6}$alkyl), —C(O)—$N(C_{1-6}$alkyl$)_2$, or —C(O)—$C_{3-10}$heterocyclyl, or $C_{1-6}$alkyl, wherein the $C_{1-6}$alkyl is optionally substituted with one or more —OH, or
(iii) 3-10 membered heterocyclyl optionally substituted with one or more $C_{1-6}$alkyl;
$R^5$ is, independently at each occurrence, H, halo, —CN, 3-10 membered heterocyclyl, $C_{1-6}$alkyl, or $C_{1-6}$alkoxy, wherein the $C_{1-6}$alkyl of $R^5$ is optionally substituted with one or more halo, or —OH and wherein the $C_{1-6}$alkoxy of $R^5$ is optionally substituted with one or more halo; and
$R^6$ and $R^7$ are each independently H or halo;
to give a compound of formula (I'), or a stereoisomer or tautomer thereof, or a pharmaceutically acceptable salt of any of the foregoing.

In some embodiments, the compound of formula (I) is prepared by a step comprising:
a) alkylation of an amine of formula (I'-A) with an alkyl halide, or sulfonate ester compound of formula (I'—B) in the presence of an inorganic base; or
b) reductive amination of a ketone of formula (I'—B) with an amine of formula (I'-A).

In some embodiments, the compound of formula (I') is prepared by a step comprising:
a) alkylation of an amine of formula (I'-A') with an alkyl halide, or sulfonate ester compound of formula (I'—B') in the presence of an inorganic base; or
b) reductive amination of a ketone of formula (I'—B') with an amine of formula (I'-A').

In some embodiments, the compound of formula (I) is prepared by a step comprising alkylation of an amine of formula (I'-A) with an alkyl halide, or sulfonate ester compound of formula (I'—B) in the presence of an inorganic base. In some embodiments, the inorganic base is selected from the group consisting of potassium carbonate, and sodium bicarbonate.

In some embodiments, the compound of formula (I') is prepared by a step comprising alkylation of an amine of formula (I'-A') with an alkyl halide, or sulfonate ester compound of formula (I'—B') in the presence of an inorganic base. In some embodiments, the inorganic base is selected from the group consisting of potassium carbonate, and sodium bicarbonate.

In some embodiments, the sulfonate ester compound of formula (I'—B) is a mesylate or a tosylate. In some embodiments, the sulfonate ester compound of formula (I'—B) is a mesylate, or $CH_3SO_3$—. In some embodiments, the sulfonate ester compound of formula (I'—B) is a tosylate or $CH_3C_6H_4SO_3$—.

In some embodiments, the sulfonate ester compound of formula (I'—B') is a mesylate or a tosylate. In some embodiments, the sulfonate ester compound of formula (I'—B') is a mesylate, or $CH_3SO_3$—. In some embodiments, the sulfonate ester compound of formula (I'—B') is a tosylate or $CH_3C_6H_4SO_3$—.

In some embodiments, the compound of formula (I) is prepared by a step comprising reductive amination of a ketone of formula (I'—B) with an amine of formula (I'-A). In some embodiments, the reductive amination proceeds under the action of sodium triacetoxyborohydride, titanium tetraiopropoxide and acetic acid.

In some embodiments, the compound of formula (I') is prepared by a step comprising reductive amination of a ketone of formula (I'—B') with an amine of formula (I'-A'). In some embodiments, the reductive amination proceeds under the action of sodium triacetoxyborohydride, titanium tetraiopropoxide and acetic acid.

It is understood that the present disclosure also provides for methods of preparing compounds of formula (II). For example, compounds of formula (II) may be prepared by reacting a compound of formula (II'-A):

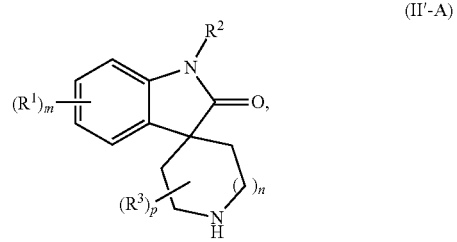

(II'-A)

wherein and m, n, p, $R^1$, and $R^2$ are as defined for a compound of formula (II), with a compound of formula (II'—B):

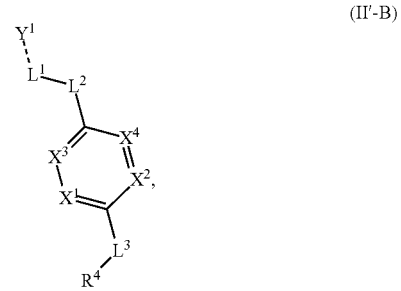

(II'-B)

wherein $Y^1$ is halo, oxo, or a sulfonate ester; and $L^1$, $L^2$, $L^3$, $R^4$, $X^1$, $X^2$, $X^3$, and $X^4$ are as defined for a compound of formula (II),
  to give a compound of formula (II), or a stereoisomer or tautomer thereof, or a pharmaceutically acceptable salt of any of the foregoing.

In some embodiments, a method for preparing a compound of formula (I), or a stereoisomer or tautomer thereof, or a pharmaceutically acceptable salt of any of the foregoing, comprises a step of reacting a compound of formula (I'—C):

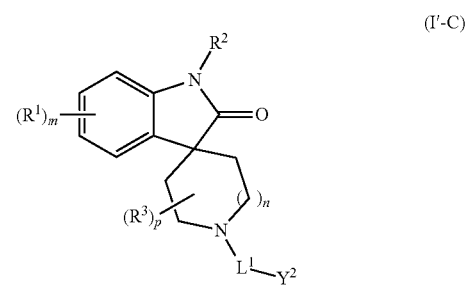

(I'-C)

wherein:
m is an integer from 0 to 4;
n is an integer from 0 to 2;
p is an integer from 0 to 10;
$R^1$, if present is, independently at each occurrence selected from the group consisting of halo, —CN, $C_{1-6}$alkoxy, or —$C_{1-6}$alkyl, wherein
  the $C_{1-6}$alkoxy of $R^1$ is optionally substituted with one or more halo, and
  the $C_{1-6}$alkyl of $R^1$ is optionally substituted with one or more halo;
$R^2$ is H, $C_{1-6}$alkyl, $C_{3-10}$cycloalkyl, or 3-15 membered heterocyclyl, wherein
  the $C_{1-6}$alkyl of $R^2$ is optionally substituted with one or more halo, —OH, —$NH_2$, or $C_{1-6}$alkoxy, and
  the $C_{3-10}$cycloalkyl of $R^2$ is optionally substituted with one or more —OH;
$R^3$, if present, is $C_{1-6}$alkyl;
$L^1$ is $C_{1-6}$alkylene, wherein the $C_{1-6}$alkylene of $L^1$ is optionally substituted with one or more $C_{1-6}$alkyl, and wherein the $C_{1-6}$alkyl is further optionally substituted with one or more —OH or $C_{1-6}$alkoxy; and
$Y^2$ is halo, —OH or —$NH_2$;

with:
a compound of formula (I'-D):

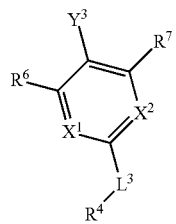

(I'-D)

wherein:
Y³ is —OH or —NH(Rˣ), wherein each Rˣ is independently H or C₁₋₆alkyl; and
either
(1) L³ is absent or is O, C₃₋₁₀cycloalkyl, 3-10 membered heterocyclyl, or C₁₋₆alkylene, wherein
  the C₁₋₆alkylene of L³ is optionally substituted with one or more C₁₋₆alkyl, and
  the 3-10 membered heterocyclyl is optionally substituted with one or more —OH;
  X¹ and X² are each independently N or C(R⁵); and
  R⁴ is:
  (i) —S(O)₂—Rᵃ;
  (ii) 5-20 membered heteroaryl, wherein the 5-20 membered heteroaryl of R⁴ is optionally substituted with one or more C₁₋₆alkyl;
  (iii) N(Rᵈ)₂, wherein Rᵈ is independently at each occurrence H, C₁₋₆ alkyl, or —S(O)₂—Rᵃ, wherein the C₁₋₆alkyl of Rᵈ is optionally substituted with one or more —OH,
  (iv) —NS(O)—(C₁₋₆alkyl)₂, wherein the C₁₋₆alkyl of Rᵈ is optionally substituted with one or more —OH,
  (v) —C(O)—N(Rᵉ)₂ wherein Rᵉ is independently at each occurrence H, C₁₋₆ alkyl, or 3-10 membered heterocycle, wherein the 3-10 membered heterocycle is optionally substituted with one or more oxo, or both Rᵉ together with the N to which they are attached are taken together to form a 3-10 membered heterocyclyl, wherein the 3-10 membered heterocyclyl is optionally substituted with one or more halo, oxo, —OH, NH₂, NH—S(O)₂—Rᵃ, or —S(O)₂—Rᵃ,
  (vi) 3-10 membered heterocyclyl optionally substituted with one or more C₁₋₆alkyl or oxo,
  (vii) —S(O)—N(C₁₋₆alkyl)-(C₁₋₆alkyl),
  (viii) —CN;
or
(2) L³ is absent; and
  one of X¹ and X² is N or C(R⁵); and
  the other of X¹ and X² is N or C that is taken together with R⁴, and the atoms to which they are attached, to form a 5-10 membered heterocyclyl or a 5-20 membered heteroaryl, wherein
    the 5-10 membered heterocyclyl is optionally substituted with one or more Rᵇ, wherein Rᵇ is, independently at each occurrence, selected from the group consisting of halo, oxo, C₁₋₆alkyl, —C(O)—C₁₋₆alkyl, —C(O)—NH₂, —C(O)—NH(C₁₋₆alkyl), —C(O)—N(C₁₋₆alkyl)₂, —S(O)₂—Rᵃ, C₃₋₁₀cycloalkyl, and 3-10 membered heterocyclyl, wherein
      the C₁₋₆alkyl of Rᵇ is optionally substituted with one or more halo, OH, or —S(O)₂—C₁₋₆alkyl, and
      the C₃₋₁₀cycloalkyl of Rᵇ is optionally substituted with one or more —OH, and
    the 5-20 membered heteroaryl is optionally substituted with one or more Rᶜ, wherein Rᶜ is, independently at each occurrence, selected from the group consisting of halo, C₁₋₆alkyl, —C(O)—C₁₋₆alkyl, —C(O)—NH₂, —C(O)—NH(C₁₋₆alkyl), —C(O)—N(C₁₋₆alkyl)₂, —S(O)₂—Rᵃ, C₃₋₁₀cycloalkyl, and 3-10 membered heterocyclyl, wherein
      the C₁₋₆alkyl of Rᶜ is optionally substituted with one or more —S(O)₂—C₁₋₆alkyl, and
      the C₃₋₁₀cycloalkyl of Rᶜ is optionally substituted with one or more —OH;
Rᵃ is, independently at each occurrence:
  (i) C₁₋₆alkyl optionally substituted with one or more halo, —OH, —S(O)₂—C₁₋₆alkyl, or —N(C₁₋₆alkyl)-C(O)—C₁₋₆alkyl, or
  (ii) C₃₋₁₀cycloalkyl optionally substituted with one or more —OH, —C(O)₂—C₁₋₆alkyl, —C(O)—NH(C₁₋₆alkyl), —C(O)—N(C₁₋₆alkyl)₂, or —C(O)—C₃₋₁₀heterocyclyl, or C₁₋₆alkyl, wherein the C₁₋₆alkyl is optionally substituted with one or more —OH, or
  (iii) 3-10 membered heterocyclyl optionally substituted with one or more C₁₋₆alkyl;
R⁵ is, independently at each occurrence, H, halo, —CN, 3-10 membered heterocyclyl, C₁₋₆alkyl, or C₁₋₆alkoxy, wherein the C₁₋₆alkyl of R⁵ is optionally substituted with one or more halo, or —OH and wherein the C₁₋₆alkoxy is optionally substituted with one or more halo; and
R⁶ and R⁷ are each independently H or halo;
to give a compound of formula (I), or a stereoisomer or tautomer thereof, or a pharmaceutically acceptable salt of any of the foregoing.

In some embodiments, a method for preparing a compound of formula (I'), or a stereoisomer or tautomer thereof, or a pharmaceutically acceptable salt of any of the foregoing, comprises a step of reacting a compound of formula (I'—C'):

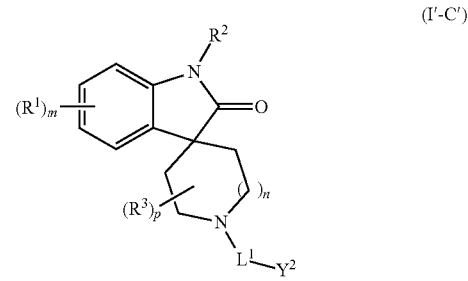

(I'-C')

wherein:
m is an integer from 0 to 4;
n is an integer from 0 to 2;
p is an integer from 0 to 10;
R¹, if present is, independently at each occurrence selected from the group consisting of halo, —CN, C₁₋₆alkoxy, or —C₁₋₆alkyl, wherein
  the C₁₋₆alkoxy of R¹ is optionally substituted with one or more halo, and the $C_{1-6}$alkyl of $R^1$ is optionally substituted with one or more halo;

$R^2$ is H, $C_{1-6}$alkyl, $C_{3-10}$cycloalkyl, or 3-15 membered heterocyclyl, wherein
the $C_{1-6}$alkyl of $R^2$ is optionally substituted with one or more halo, —OH, —$NH_2$, or $C_{1-6}$alkoxy, and
the $C_{3-10}$cycloalkyl of $R^2$ is optionally substituted with one or more —OH;

$R^3$, if present, is $C_{1-6}$alkyl;

$L^1$ is $C_{1-6}$alkylene, wherein the $C_{1-6}$alkylene of $L^1$ is optionally substituted with one or more $C_{1-6}$alkyl, and wherein the $C_{1-6}$alkyl is further optionally substituted with one or more —OH or $C_{1-6}$alkoxy; and $Y^2$ is halo, —OH or —$NH_2$;

with:

a compound of formula (I'-D'):

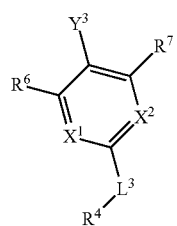

wherein:

$Y^3$ is —OH or NH($R^x$), wherein each $R^x$ is independently H or $C_{1-6}$alkyl; and either (1) $L^3$ is absent or is O, $C_{3-10}$cycloalkyl, 3-10 membered heterocyclyl, or $C_{1-6}$alkylene, wherein
the $C_{3-10}$cycloalkyl is optionally substituted with one or more —OH, or $C_{1-6}$alkyl,
the $C_{1-6}$alkylene of $L^3$ is optionally substituted with one or more —OH, or $C_{1-6}$alkyl, and
the 3-10 membered heterocyclyl is optionally substituted with one or more —OH;

$X^1$ and $X^2$ are each independently N or C($R^5$); and $R^4$ is:
(i) —S(O)$_2$—$R^a$;
(ii) 5-20 membered heteroaryl, wherein the 5-20 membered heteroaryl of $R^4$ is optionally substituted with one or more $C_{1-6}$alkyl;
(iii) —N($R^d$)$_2$, wherein $R^d$ is independently at each occurrence H, $C_{1-6}$ alkyl, or —S(O)$_2$—$R^a$, wherein the $C_{1-6}$alkyl of $R^d$ is optionally substituted with one or more —OH,
(iv) —NS(O)—($C_{1-6}$alkyl)$_2$, wherein the $C_{1-6}$alkyl is optionally substituted with one or more —OH,
(v) —C(O)—N($R^e$)$_2$ wherein $R^e$ is independently at each occurrence H, $C_{1-6}$ alkyl, or 3-10 membered heterocycle, wherein the 3-10 membered heterocycle is optionally substituted with one or more oxo, or both $R^e$ together with the N to which they are attached are taken together to form a 3-10 membered heterocyclyl, wherein the 3-10 membered heterocyclyl is optionally substituted with one or more halo, oxo, —OH, $NH_2$, —NH—S(O)$_2$—$R^a$, or —S(O)$_2$—$R^a$,
(vi) 3-10 membered heterocyclyl optionally substituted with one or more $C_{1-6}$alkyl, —OH, oxo or —S(O)$_2R^a$,
(vii) —S(O)—N($C_{1-6}$alkyl)-($C_{1-6}$alkyl),
(viii) —CN;
(ix) —(CH$_2$)$_q$OH, wherein q is an integer from 0-6; or
(x) —C(O)—$C_{1-6}$alkyl
(xi) —P(O)($C_{1-6}$alkyl)$_2$ or (2) $L^3$ is absent; and
one of $X^1$ and $X^2$ is N or C($R^5$); and
the other of $X^1$ and $X^2$ is N or C that is taken together with $R^4$, and the atoms to which they are attached, to form a 5-10 membered heterocyclyl or a 5-20 membered heteroaryl, wherein
the 5-10 membered heterocyclyl is optionally substituted with one or more $R^b$, wherein $R^b$ is, independently at each occurrence, selected from the group consisting of halo, oxo, $C_{1-6}$alkyl, —C(O)—$C_{1-6}$alkyl, —C(O)—$NH_2$, —C(O)—NH($C_{1-6}$alkyl), —C(O)—N($C_{1-6}$alkyl)$_2$, —S(O)$_2$—$R^a$, $C_{3-10}$cycloalkyl, and 3-10 membered heterocyclyl, wherein
the $C_{1-6}$alkyl of $R^b$ is optionally substituted with one or more halo, OH, —S(O)$_2$—$C_{1-6}$alkyl, or $C_{3-10}$cycloalkyl, and
wherein the $C_{3-10}$cycloalkyl of the $C_{1-6}$alkyl of $R^b$ is further optionally substituted with one or more $C_{1-6}$alkyl or —OH and
the $C_{3-10}$cycloalkyl of $R^b$ is optionally substituted with one or more —OH, $C_{3-10}$cycloalkyl, or $C_{1-6}$alkyl, and
wherein the $C_{1-6}$alkyl of the $C_{3-10}$cycloalkyl of $R^b$ is further optionally substituted with one or more —OH, and
the 5-20 membered heteroaryl is optionally substituted with one or more $R^c$, wherein $R^c$ is, independently at each occurrence, selected from the group consisting of halo, $C_{1-6}$alkyl, —C(O)—$C_{1-6}$alkyl, —C(O)—$NH_2$, —C(O)—NH($C_{1-6}$alkyl), —C(O)—N($C_{1-6}$alkyl)$_2$, —S(O)$_2$—$R^a$, $C_{3-10}$cycloalkyl, and 3-10 membered heterocyclyl, wherein
the $C_{1-6}$alkyl of $R^c$ is optionally substituted with one or more —S(O)$_2$—$C_{1-6}$alkyl,
the $C_{3-10}$cycloalkyl of $R^c$ is optionally substituted with one or more —OH, or $C_{1-6}$alkyl,
and the 3-10 membered heterocyclyl of $R^c$ is optionally substituted with one or more —OH, or $C_{1-6}$alkyl, and
wherein the $C_{1-6}$alkyl of the 3-10 membered heterocyclyl of $R^c$ is further optionally substituted with one or more —OH;

$R^a$ is, independently at each occurrence:
(i) $C_{1-6}$alkyl optionally substituted with one or more halo, —OH, —S(O)$_2$—$C_{1-6}$alkyl, or —N($C_{1-6}$alkyl)-C(O)—$C_{1-6}$alkyl,
(ii) $C_{3-10}$cycloalkyl optionally substituted with one or more —OH, —C(O)$_2$—$C_{1-6}$alkyl, —C(O)—NH($C_{1-6}$alkyl), —C(O)—N($C_{1-6}$alkyl)$_2$, or —C(O)—$C_{3-10}$heterocyclyl, or $C_{1-6}$alkyl, wherein the $C_{1-6}$alkyl is optionally substituted with one or more —OH, or
(iii) 3-10 membered heterocyclyl optionally substituted with one or more $C_{1-6}$alkyl;

$R^5$ is, independently at each occurrence, H, halo, —CN, 3-10 membered heterocyclyl, $C_{1-6}$alkyl, or $C_{1-6}$alkoxy, wherein the $C_{1-6}$alkyl of $R^5$ is optionally substituted with one or more halo, or —OH and wherein the $C_{1-6}$alkoxy of $R^5$ is optionally substituted with one or more halo; and $R^6$ and $R^7$ are each independently H or halo;

to give a compound of formula (I'), or a stereoisomer or tautomer thereof, or a pharmaceutically acceptable salt of any of the foregoing.

In some embodiments, the compound of formula (I) is prepared by a step comprising:
a) coupling of an alcohol compound of formula (I'—C) with a phenol compound of formula (I'-D), or a heterocyclic variant, under Mitsunobu-type reaction conditions; or
b) reacting an alkyl halide compound of formula (I'—C) with a phenol or amine compound of formula (I'-D), in the presence of a catalyst.

In some embodiments, the compound of formula (I') is prepared by a step comprising:
a) coupling of an alcohol compound of formula (I'—C') with a phenol compound of formula (I'-D'), or a heterocyclic variant, under Mitsunobu-type reaction conditions; or
b) reacting an alkyl halide compound of formula (I'—C') with a phenol or amine compound of formula (I'-D'), in the presence of a catalyst.

In some embodiments, the compound of formula (I) is prepared by a step comprising coupling of an alcohol compound of formula (I'—C) with a phenol compound of formula (I'-D), or a heterocyclic variant, under Mitsunobu-type reaction conditions. In some embodiments, the Mitsunobu-type reaction conditions comprises coupling of an alcohol compound of formula (I'—C) with a phenol compound of formula (I'-D), or a heterocyclic variant, in the presence of triphenylphosphine and diisopropyl azodicarboxylate.

In some embodiments, the compound of formula (I') is prepared by a step comprising coupling of an alcohol compound of formula (I'—C') with a phenol compound of formula (I'-D'), or a heterocyclic variant, under Mitsunobu-type reaction conditions. In some embodiments, the Mitsunobu-type reaction conditions comprises coupling of an alcohol compound of formula (I'—C') with a phenol compound of formula (I'-D'), or a heterocyclic variant, in the presence of triphenylphosphine and diisopropyl azodicarboxylate.

In some embodiments, the compound of formula (I) is prepared by a step comprising reacting an alkyl halide compound of formula (I'—C) with a phenol compound of formula (I'-D), in the presence of a base. In some embodiments, the base is silver oxide or potassium carbonate.

In some embodiments, the compound of formula (I') is prepared by a step comprising reacting an alkyl halide compound of formula (I'—C') with a phenol compound of formula (I'-D'), in the presence of a base. In some embodiments, the base is silver oxide or potassium carbonate.

It is understood that the present disclosure also provides for methods of preparing compounds of formula (II). For example, compounds of formula (II) may be prepared by reacting a compound of formula (II'—C):

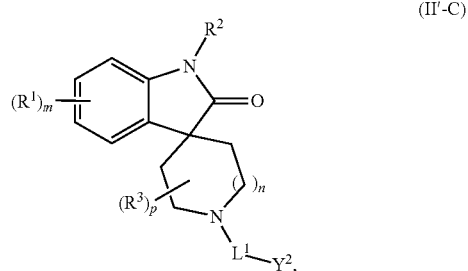

(II'-C)

wherein $Y^2$ is halo, —OH or —NH$_2$; and m, n, p, $R^1$, $R^2$, $R^3$, and $L^1$ are as defined for a compound of formula (II), with a compound of formula (II'-D):

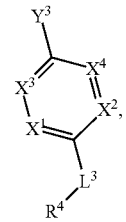

(II'-D)

wherein $Y^3$ is —OH or —NH($R^x$), wherein each $R^x$ is independently H or $C_{1-6}$alkyl; $L^3$, $R^4$, $X^1$, $X^2$, $X^3$, and $X^4$ are as defined for a compound of formula (II),
to give a compound of formula (II), or a stereoisomer or tautomer thereof, or a pharmaceutically acceptable salt of any of the foregoing.

In further examples, the compound of formula (II), formula (I'), formula (I), or any embodiment or variation thereof, such as a compound of formula (I), (I-A) (I-B), (I-C), (I-D), (I-E), (I-F), (I-G), or (II-A), or a stereoisomer or tautomer thereof, or a pharmaceutically acceptable salt of any of the foregoing is prepared by methods shown in the examples below.

EXAMPLES

The following synthetic reaction schemes, which are detailed in the Schemes, General Procedures, and Examples, are merely illustrative of some of the methods by which the compounds of the present disclosure, or an embodiment or aspect thereof, can be synthesized. Various modifications to these synthetic reaction schemes can be made, as will be apparent to those of ordinary skill in the art.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Although certain exemplary embodiments are depicted and described herein, the compounds of the present disclosure, or any variation or embodiment thereof, may be prepared using appropriate starting materials according to the methods described generally herein and/or by methods available to one of ordinary skill in the art.

Synthetic Examples

As depicted in the Schemes, General Procedures, and Examples below, in certain exemplary embodiments, compounds of formula (I), formula (I), formula (II), or any variation or embodiment thereof, as described elsewhere herein, or a stereoisomer or tautomer thereof, or a pharmaceutically acceptable salt of any of the foregoing, are prepared according to the general procedures. The general methods below, and other methods known to synthetic chemists of ordinary skill in the art, can be applied to all formulae, variations, embodiments, and species described herein.

Scheme 1

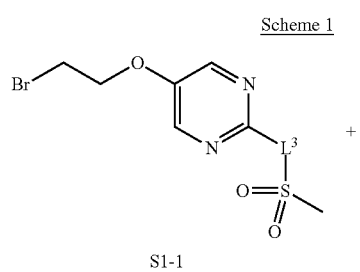

S1-1

+

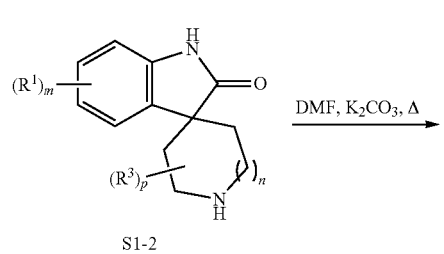

S1-2

DMF, K₂CO₃, Δ

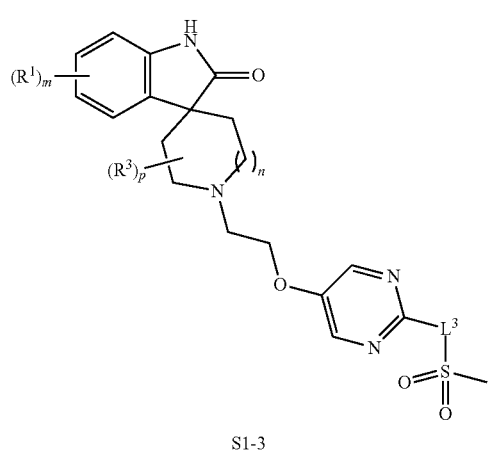

S1-3

Compounds of formula S1-3 may be prepared according to Scheme 1. Alkylation of amine S1-2 with an alkyl halide such as S1-1 in the presence of an inorganic base such as potassium carbonate and a polar aprotic solvent such as DMF provides compound S1-3. In cases where L3 represents a chiral atom, compound S1-3 may be further purified by chiral SFC to deliver single stereoisomers.

Scheme 2

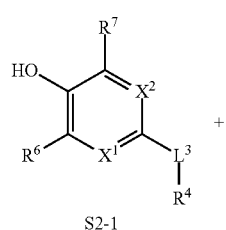

S2-1

+

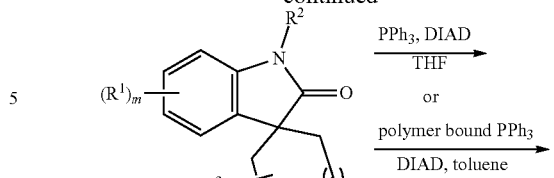

S2-2

PPh₃, DIAD
THF
or
polymer bound PPh₃
DIAD, toluene

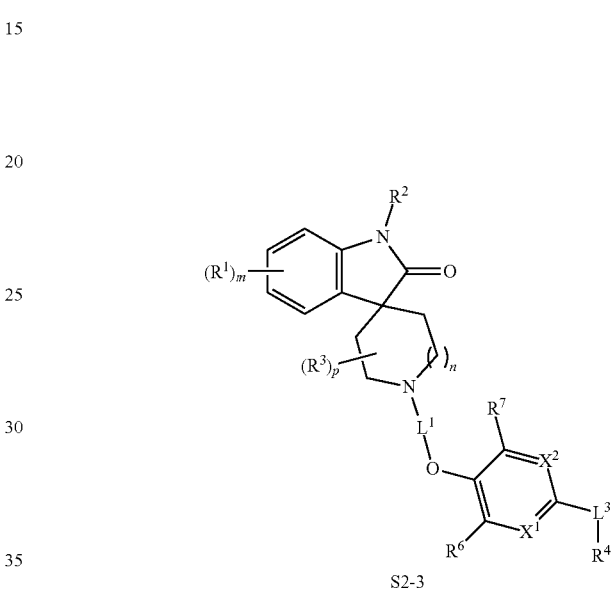

S2-3

Compounds of formula S2-3 may be prepared may also be prepared by coupling a phenol or heterocyclic variant such as S2-1 with an alcohol such as S2-2 in the presence of triphenylphosphine and DIAD in an aprotic solvent such as THF, as depicted in Scheme 2. Alternative Mitsunobu-type reaction conditions with polymer-bound triphenylphosphine and DIAD in toluene may also be used to generate compounds of formula S2-3.

Scheme 3

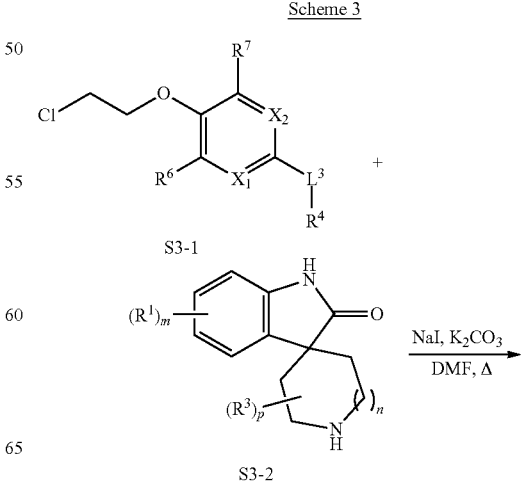

S3-1

+

S3-2

NaI, K₂CO₃
DMF, Δ

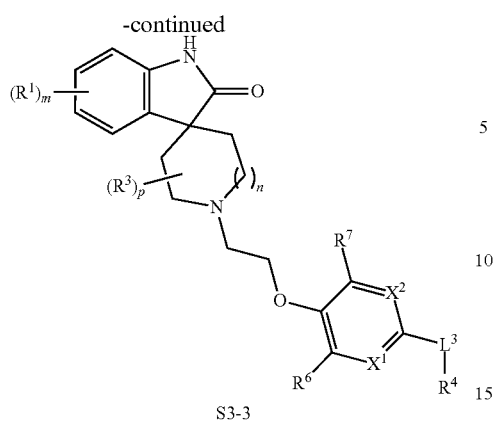

S3-3

As outlined in Scheme 3, compounds of formula S3-3 may be prepared from alkyl chlorides such as S3-1 and amine S3-2 by heating in an aprotic solvent such as DMF in the presence of sodium iodide and an inorganic base such as potassium carbonate.

Scheme 4

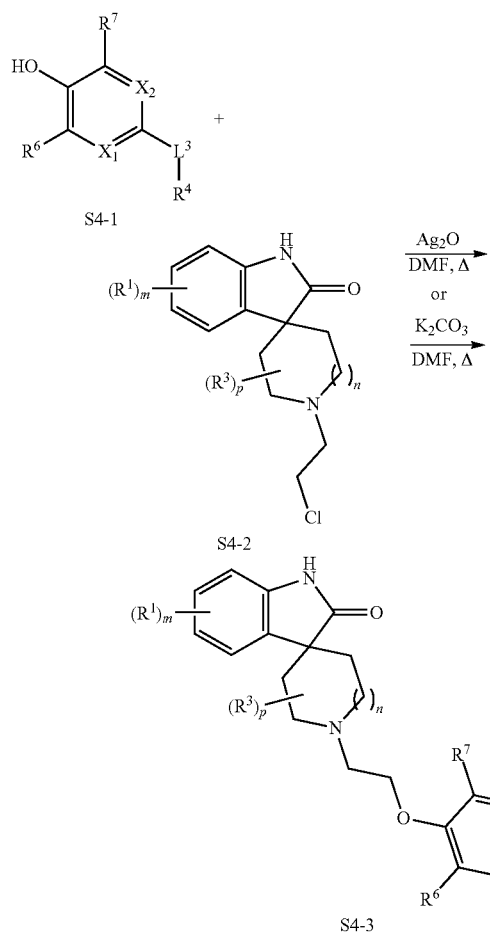

Compounds of formula S4-3 may also be prepared from phenol S4-1 and alkyl halide S4-2 by heating in an aprotic solvent such as DMF in the presence of silver oxide, as shown in Scheme 4. Alternative reaction conditions involving potassium carbonate in DMF may also be used to generate compounds of formula S4-3.

Scheme 5

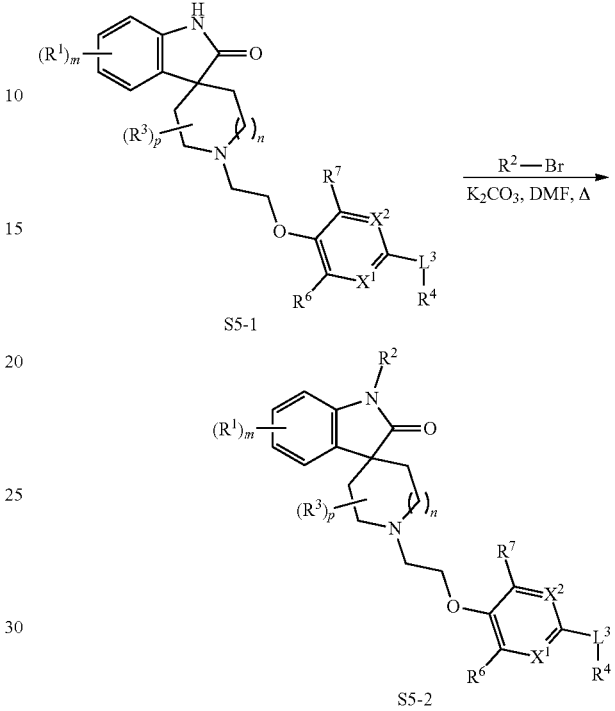

Oxindoles such as S5-1 may be elaborated by reaction with an alkyl halide in the presence of an inorganic base such as potassium carbonate in DMF, at elevated temperature. This provides compounds such as S5-2, as depicted in Scheme 5.

Scheme 6

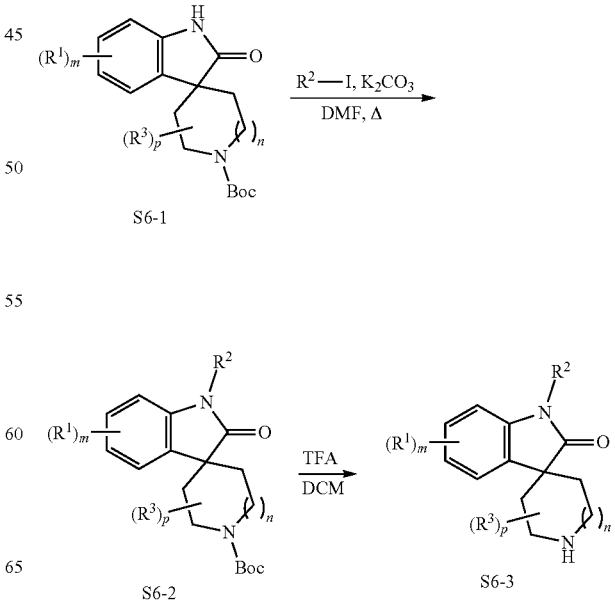

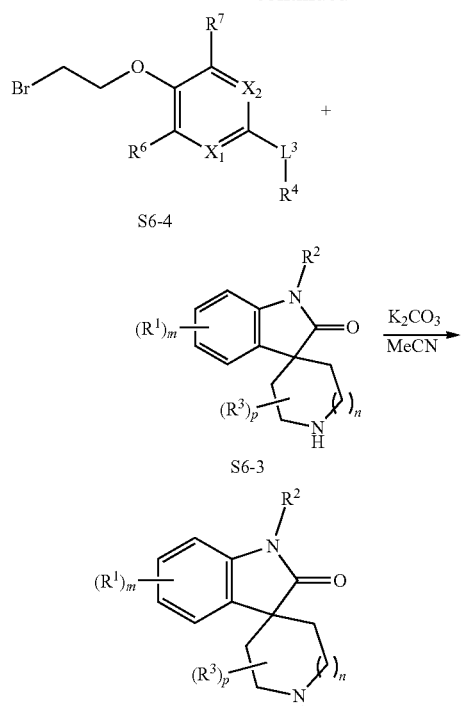

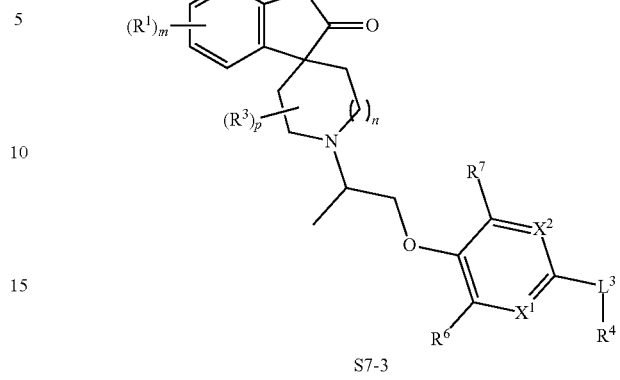

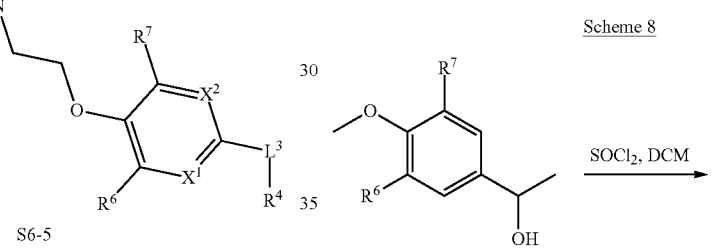

An alternative approach to compounds of formula S7-3 involving reductive amination of ketone S7-2 with amine S7-2 under the action of sodium triacetoxyborohydride, titanium tetraisopropoxide and acetic acid, is depicted in Scheme 7.

Scheme 6 depicts an approach to compounds of formula S6-5. Alkylation of oxindole S6-1 with an alkyl halide in the presence of a base such as potassium carbonate generates S6-2. Removal of the Boc group by treatment with a protic acid such as TFA in an aprotic solvent such as DCM generates amine S6-3, which can be further elaborated by coupling with an alkyl halide such as S6-4, according to procedures shown in Scheme 1.

Scheme 7

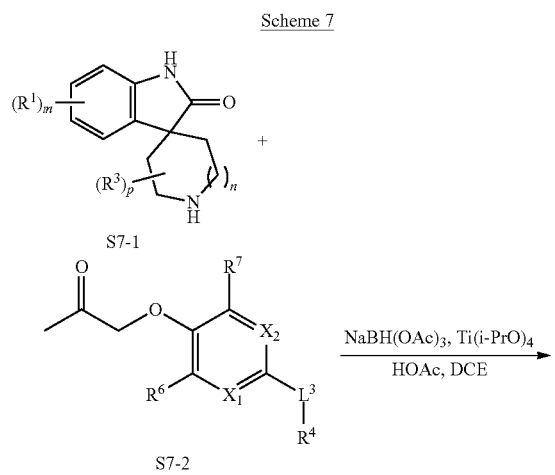

Scheme 8

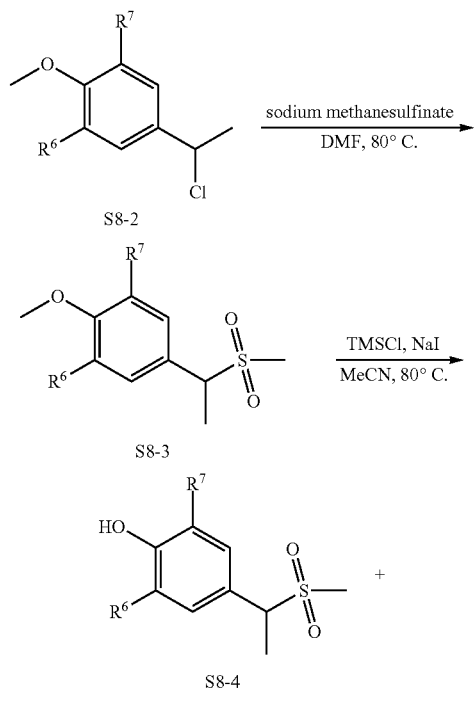

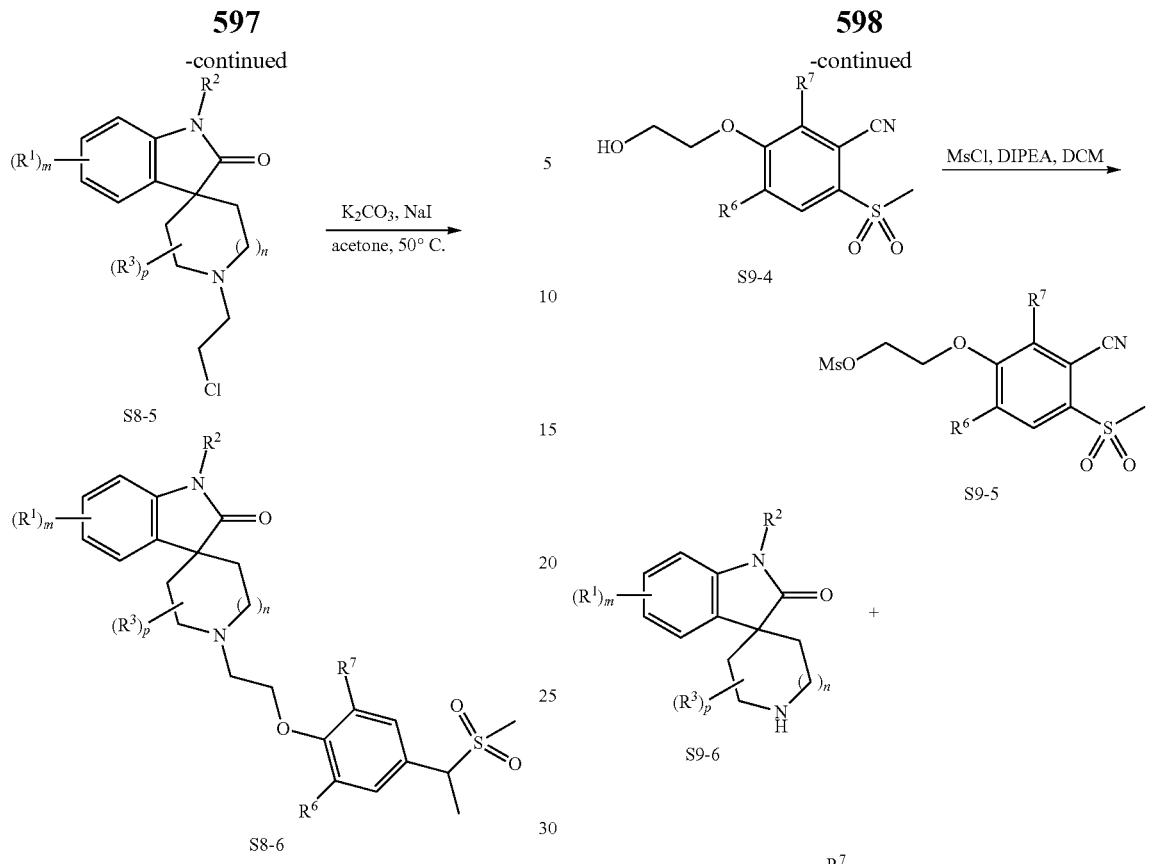

Scheme 8 depicts an alternative approach to compounds of formula S8-6. Generation of benzylic chloride S8-2 from benzylic alcohol S8-1, followed by introduction of a sulfonyl group, gives rise to compound S8-3. Deprotection of S8-3 with in situ-formed TMSI gives phenol S8-4, which can be coupled with alkyl chloride S8-5 in the presence of potassium carbonate and sodium iodide in acetone at elevated temperature. Single stereoisomers may be obtained by chiral SFC purification of S8-6.

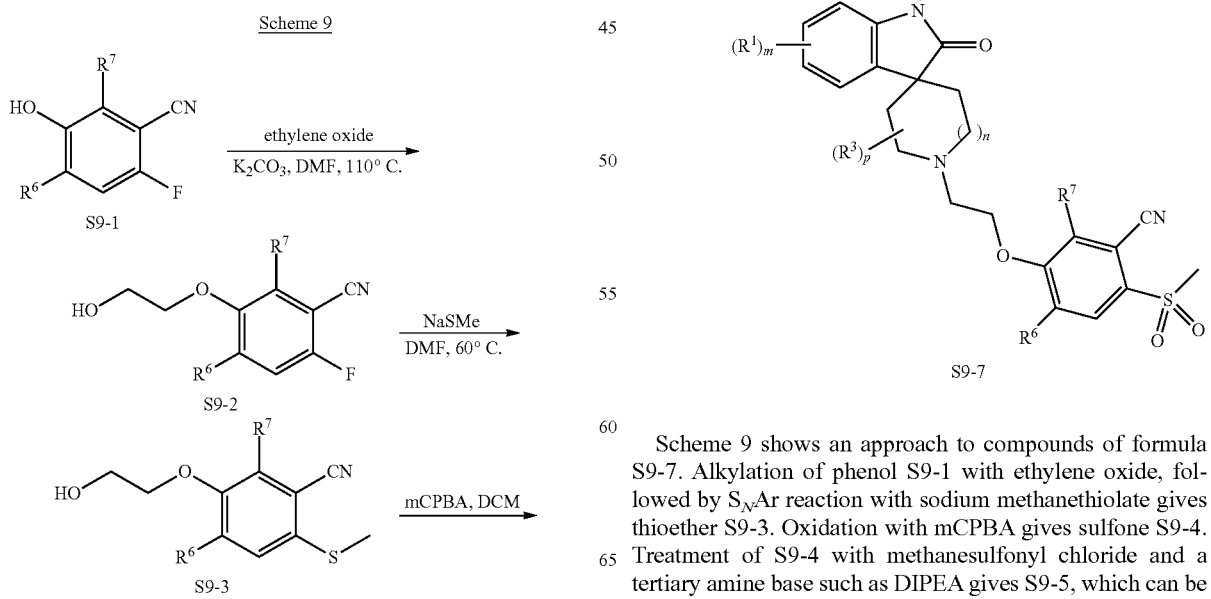

Scheme 9 shows an approach to compounds of formula S9-7. Alkylation of phenol S9-1 with ethylene oxide, followed by S$_N$Ar reaction with sodium methanethiolate gives thioether S9-3. Oxidation with mCPBA gives sulfone S9-4. Treatment of S9-4 with methanesulfonyl chloride and a tertiary amine base such as DIPEA gives S9-5, which can be converted to S9-7 under conditions similar to Scheme 1.

Scheme 10

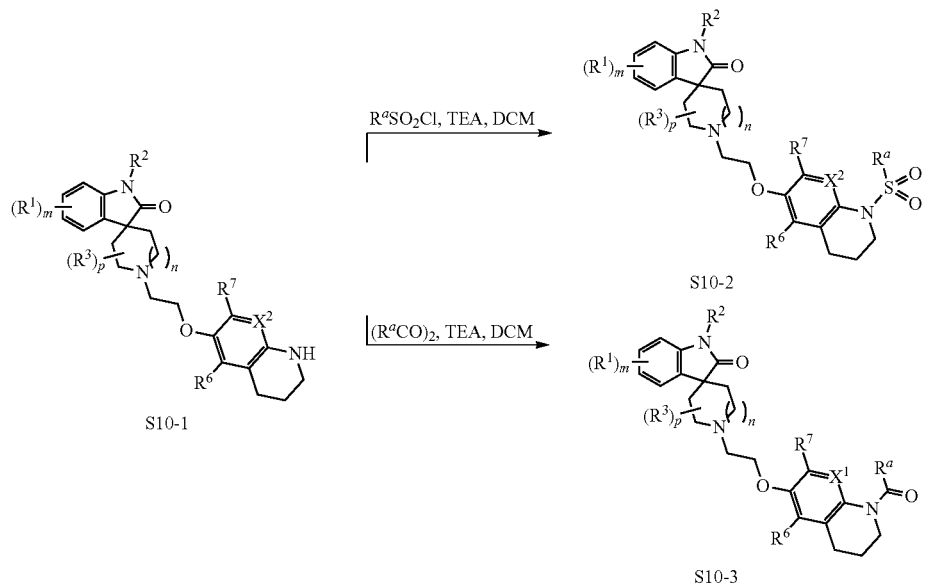

As shown in Scheme 10, compounds of formula S10-1 may be further elaborated via coupling with a sulfonyl chloride such as methanesulfonyl chloride in the presence of triethylamine in DCM to provide S10-2. Compound S10-1 may also be acylated with an anhydride such as acetic anhydride and triethylamine to generate S10-3.

Scheme 11

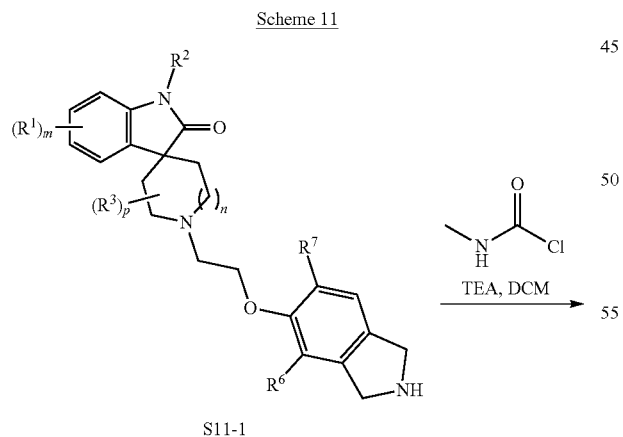

-continued

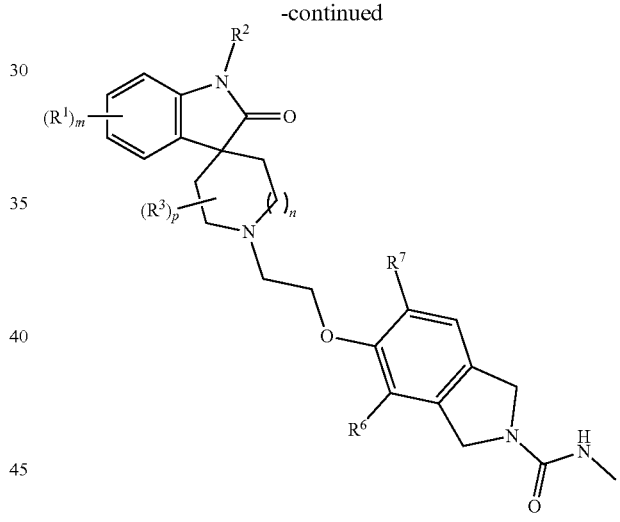

As shown in Scheme 11, compounds of formula S11-1 may be elaborated via coupling with a carbamoyl chloride such as N-methylcarbamoyl chloride in the presence of triethylamine to give a urea of the formula S11-2.

Scheme 12

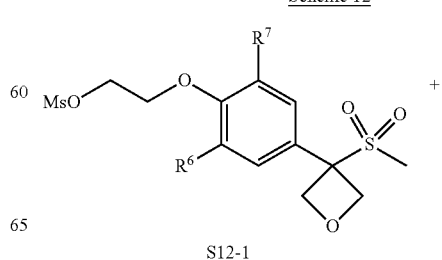

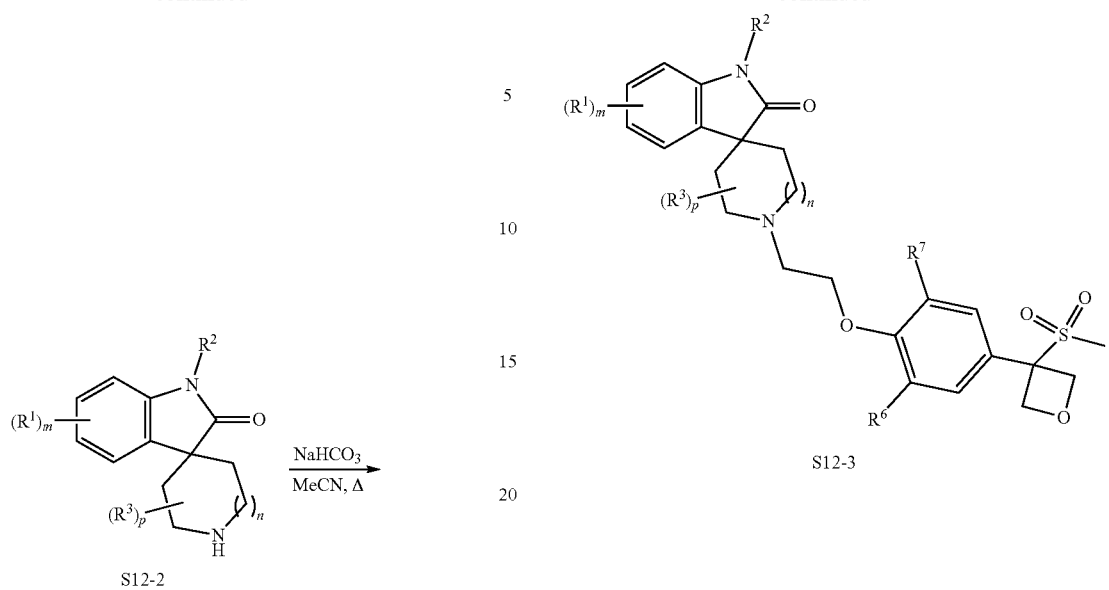
S12-2
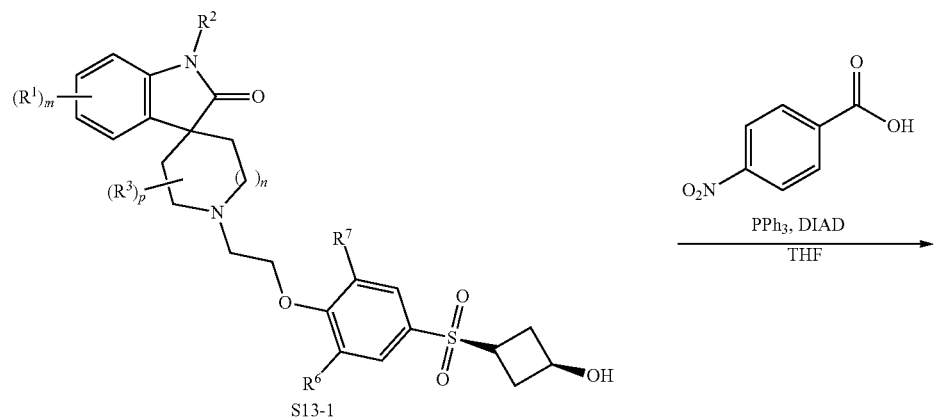
S12-3
An alternative approach to compounds of formula S12-3 is depicted in Scheme 12, via coupling of a mesylate such as S12-1 and amine such as S12-2 in acetonitrile using sodium bicarbonate as base.
Scheme 13
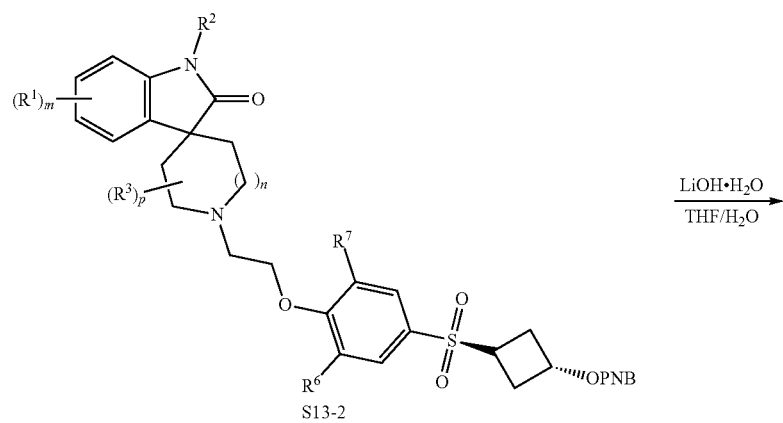
S13-1
S13-2

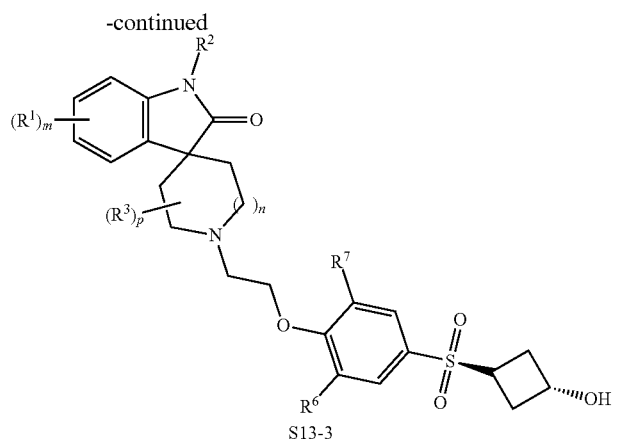
S13-3
Scheme 13 depicts the conversion of cis isomer S13-1 to trans isomer S13-3. Mitsunobu coupling with p-nitrobenzoic acid generates ester S13-2, which can undergo hydrolysis with lithium hydroxide to generate the trans isomer S13-3.
Scheme 14
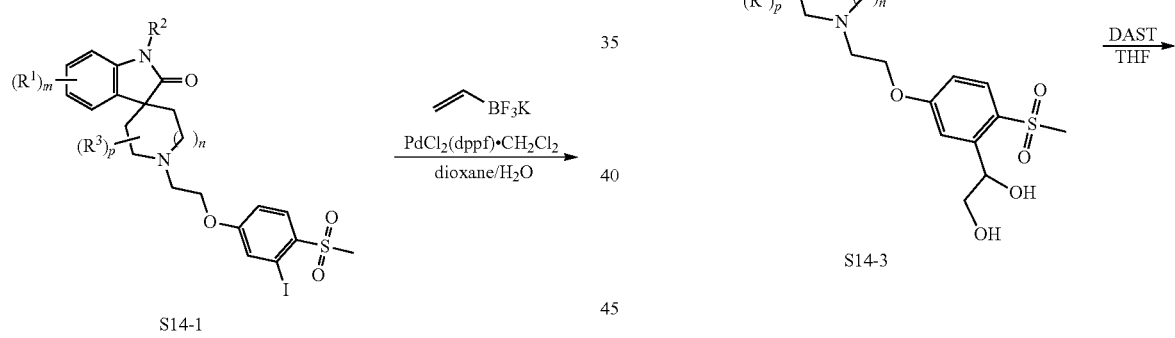
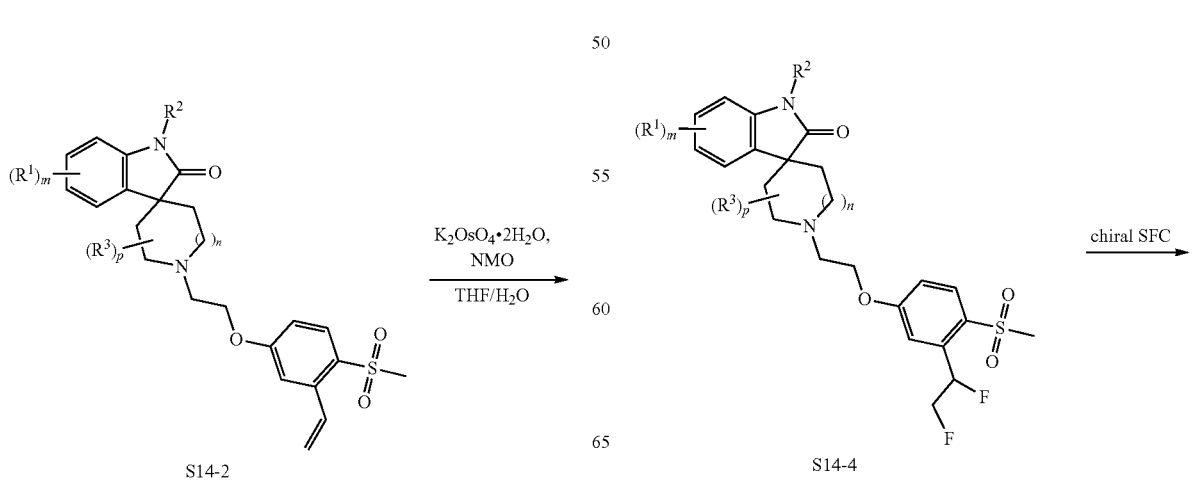

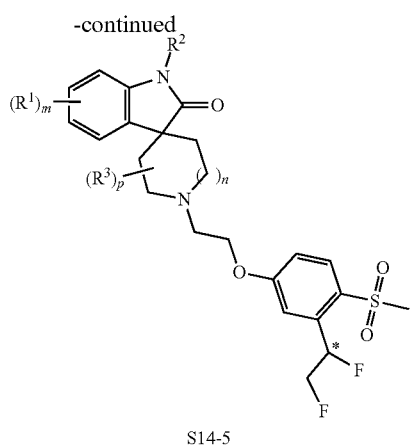

S14-5

Elaboration of compounds of formula S14-1 (generated using methods described in Scheme 1) is depicted in Scheme 14. Cross coupling of S14-1 with potassium vinyltrifluoroborate using a palladium catalyst and an inorganic base provides olefin S14-2. Dihydroxylation with an osmium catalyst and NMO gives S14-3. Diol S14-3 may be further modified by treatment with DAST, giving rise to difluoride S14-4 as an isomeric mixture. Single isomer analogs such as S14-5 may be obtained by chiral SFC purification.

Iodide S15-1 may be elaborated using photoredox methods outlined in Scheme 15. Coupling of S15-1 and 3-iodooxetane can be achieved with nickel(II) chloride ethylene glycol dimethyl ether complex, ligand S15-2, (Ir[dF(CF$_3$)ppy]$_2$(dtbpy))PF$_6$, bis(trimethylsilyl)silyl-trimethylsilane, Na$_2$CO$_3$ and blue LED to generate S15-3.

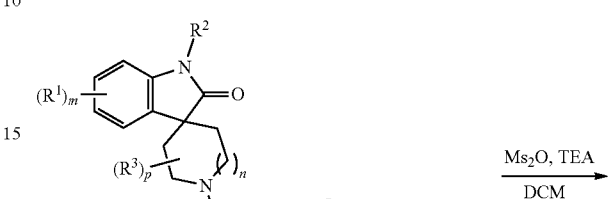

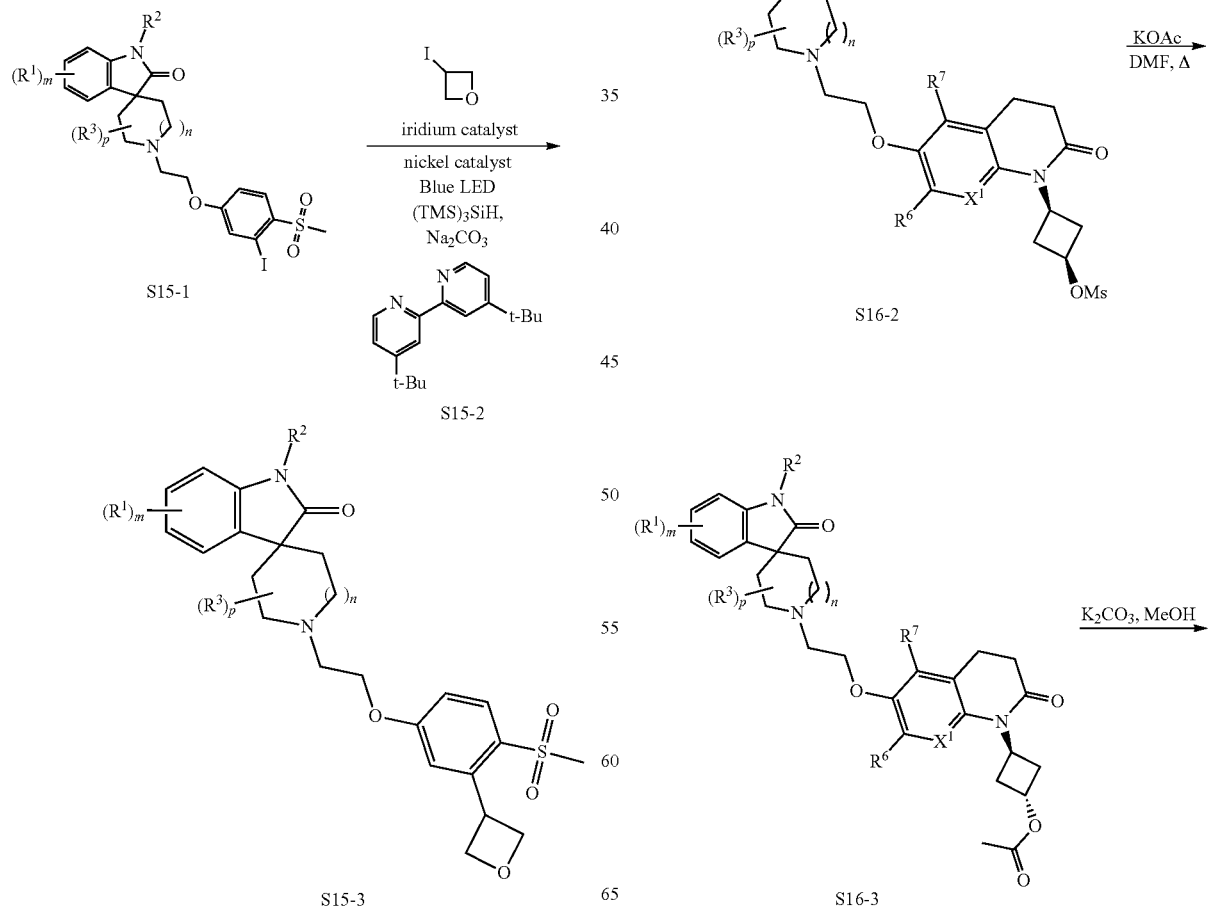

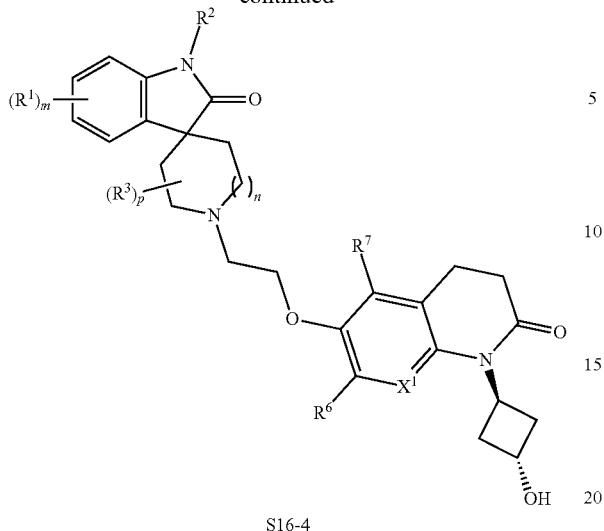

S16-4

Conversion of cis-disubstituted cyclobutanol S16-1 to the trans isomer S16-4 is depicted in Scheme 16. Treatment with methanesulfonic anhydride and TEA generates mesylate S16-2. Heating with potassium acetate generates ester S16-3, which can be converted to the alcohol under the action of potassium carbonate in MeOH to give S16-4.

Scheme 17

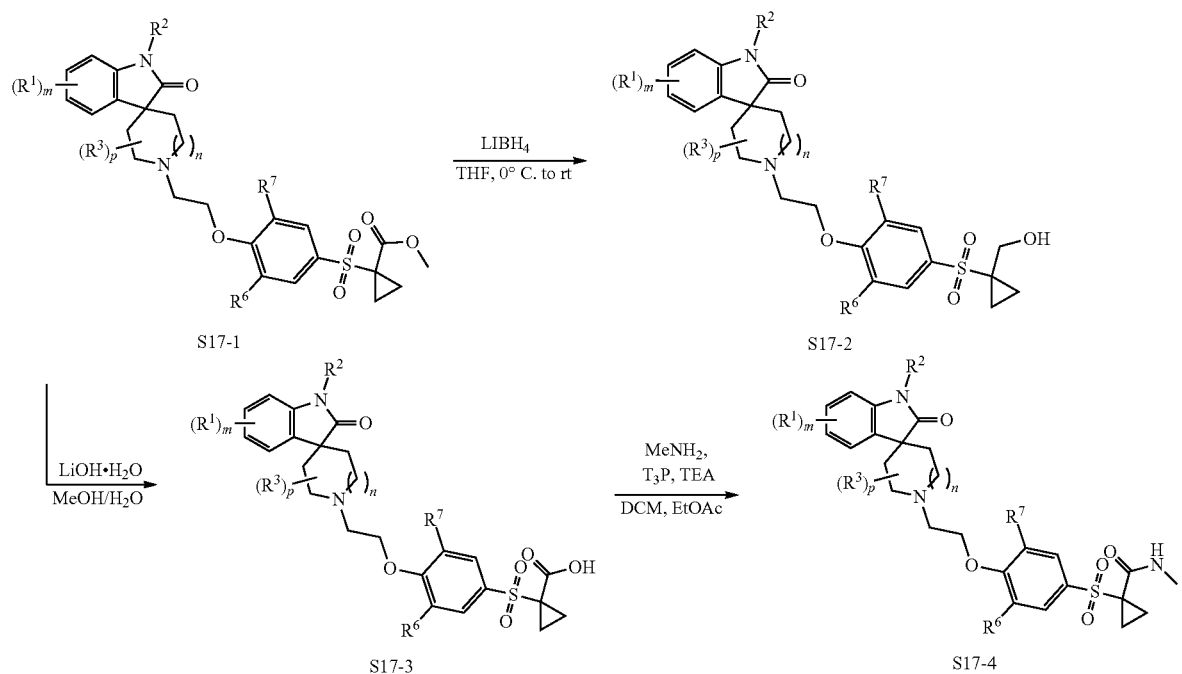

Compounds of the formula S17-1 can be converted to the corresponding alcohol by treatment with a reducing agent such as LiBH$_4$, as depicted in Scheme 17. Alternatively, S17-1 can undergo hydrolysis with lithium hydroxide to give acid S17-3. Amide bond formation with an amine such as methylamine under the action of T3P and TEA generates amide S17-4.

Scheme 18
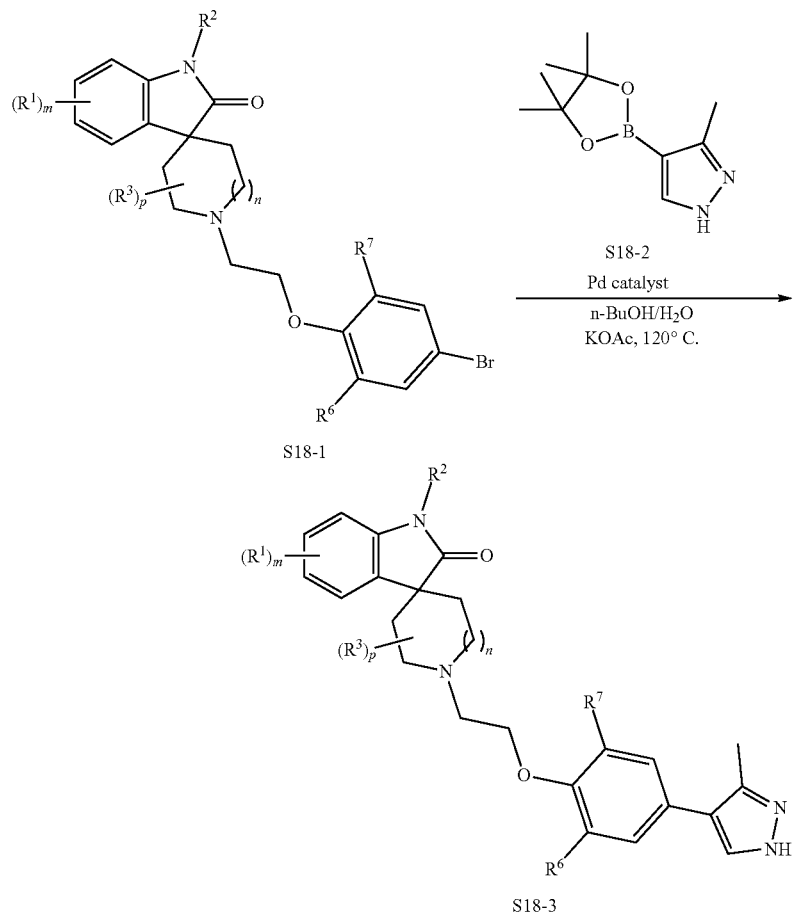
Compounds of formula S18-1 can be elaborated by Suzuki couplings of boronate esters such as S18-2, a catalyst such as bis(4-(di-tert-butylphosphanyl)-N,N-dimethylaniline) dichloropalladium, and a base such as KOAc, as depicted in Scheme 18.
Scheme 19
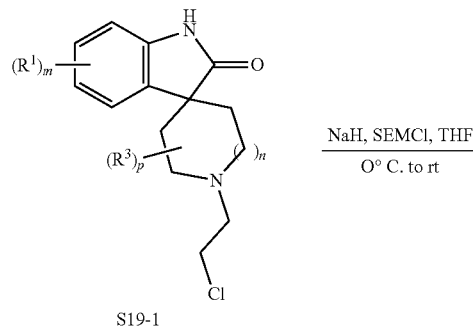
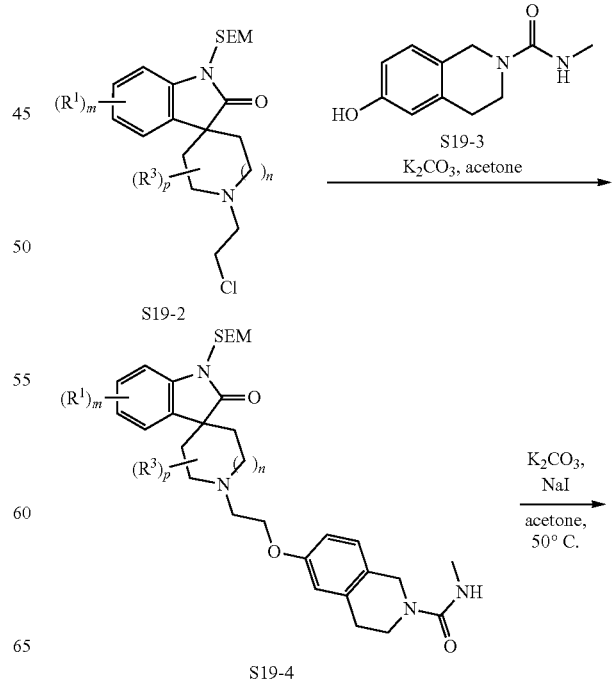

611

-continued

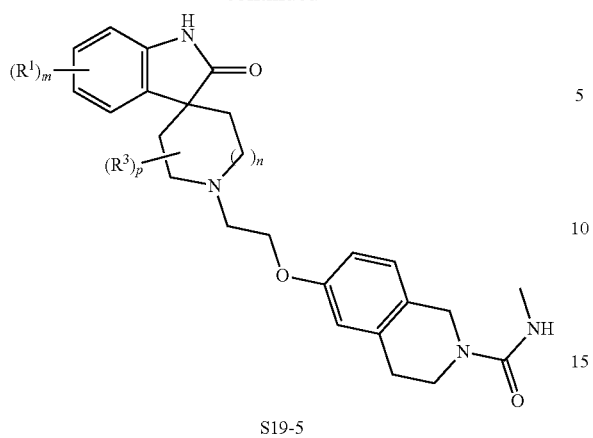

S19-5

Scheme 19 begins with protection of an oxindole nitrogen using sodium hydride and SEMCl to give S19-2. Coupling with a phenol such as S19-3 gives S19-4. Removal of the SEM group is achieved by heating a mixture of S19-4, potassium carbonate, and NaI in acetone to give compound of formula S19-5.

612

-continued

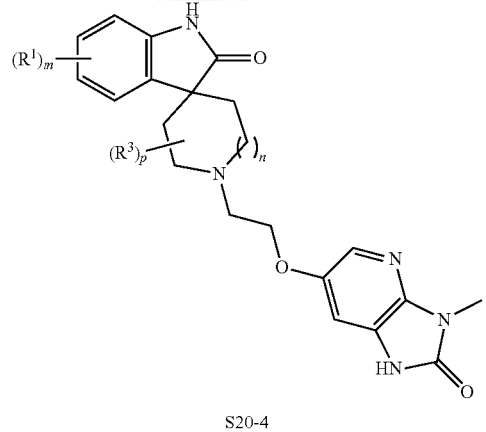

S20-4

Heterocyclic electrophiles bearing protecting groups such as compound S20-1 may be coupled with amine nucleophiles such as S20-2 under the conditions shown in Scheme 20. Deprotection of a protecting group such as a SEM N—O acetal may be achieved by treatment of S20-3 with a protic acid such as TFA to deliver S20-4.

Scheme 20

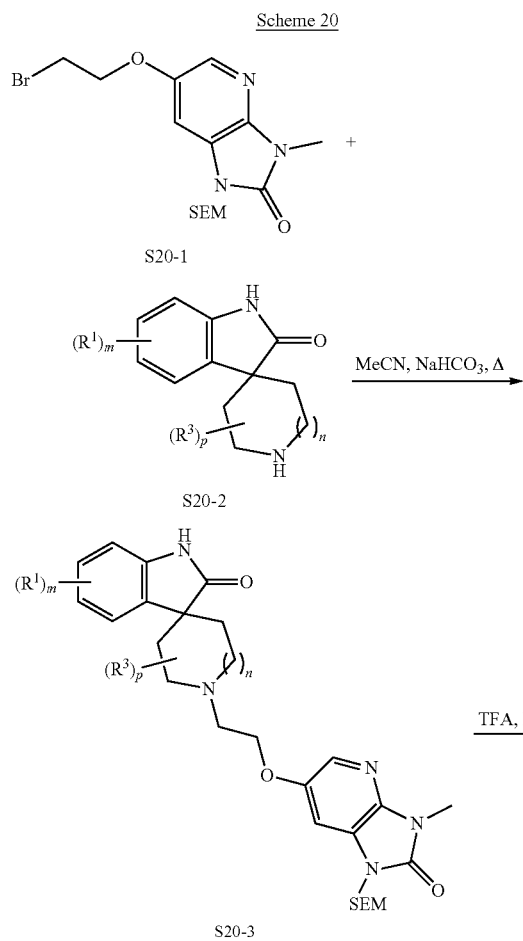

Scheme 21

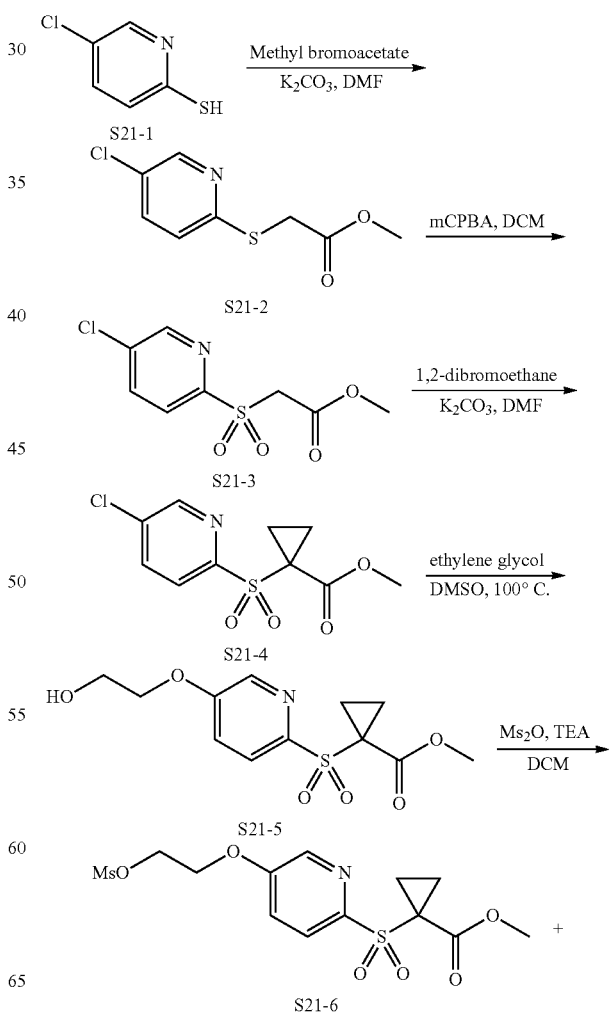

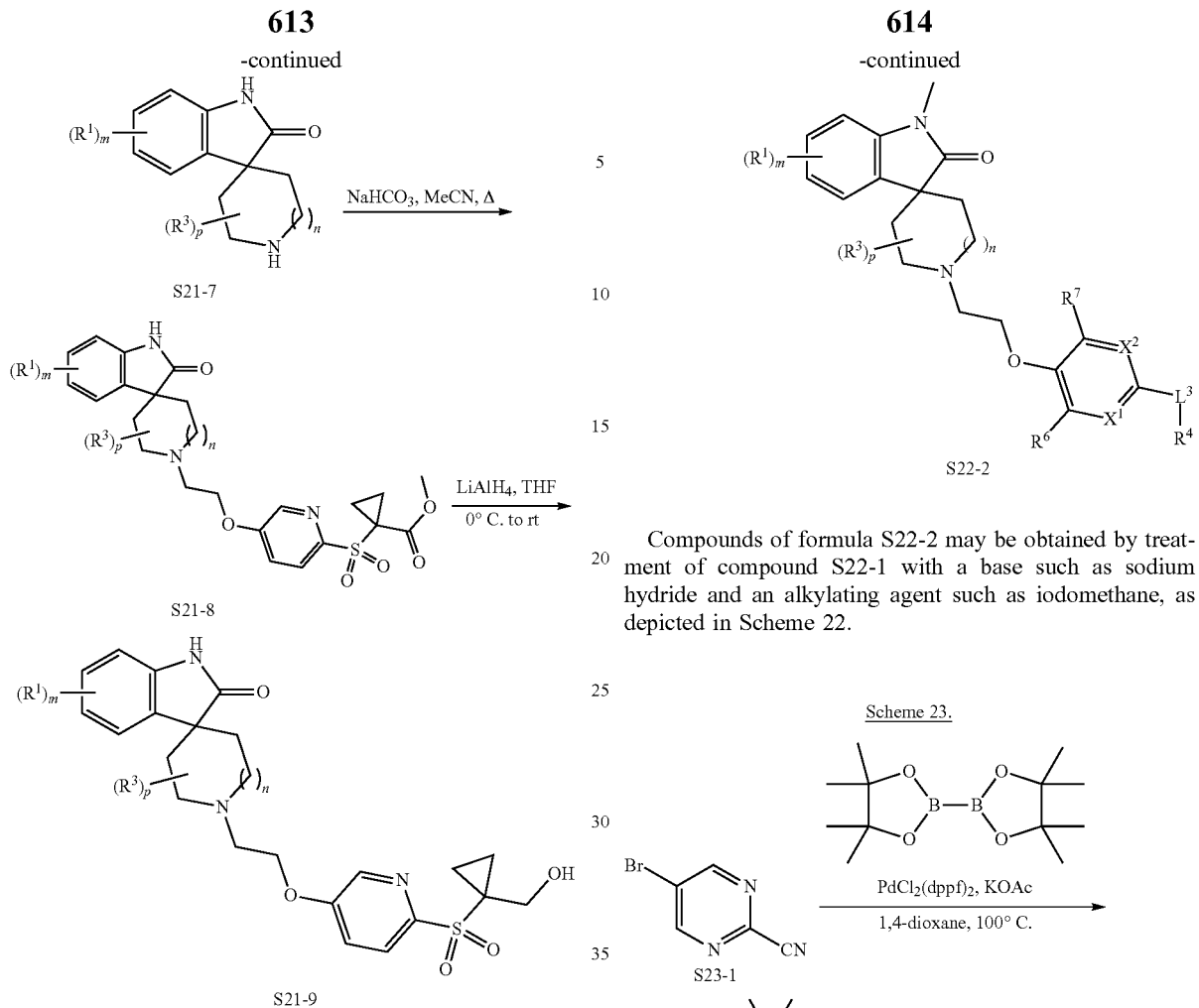

An approach to compounds of formula S21-9 is shown in Scheme 21. Alkylation of thiol S21-1 followed by oxidation to the sulfone generates compound S21-3. Cyclopropane formation via double alkylation in the presence of potassium carbonate gives S21-4. $S_NAr$ reaction with ethylene glycol and mesylation of S21-5 provides compound S21-6, which can be coupled with amine S21-7 under standard conditions (Scheme 12). Treatment of compound S21-8 with a reducing agent such as LiAlH$_4$ gives compound S21-9.

Compounds of formula S22-2 may be obtained by treatment of compound S22-1 with a base such as sodium hydride and an alkylating agent such as iodomethane, as depicted in Scheme 22.

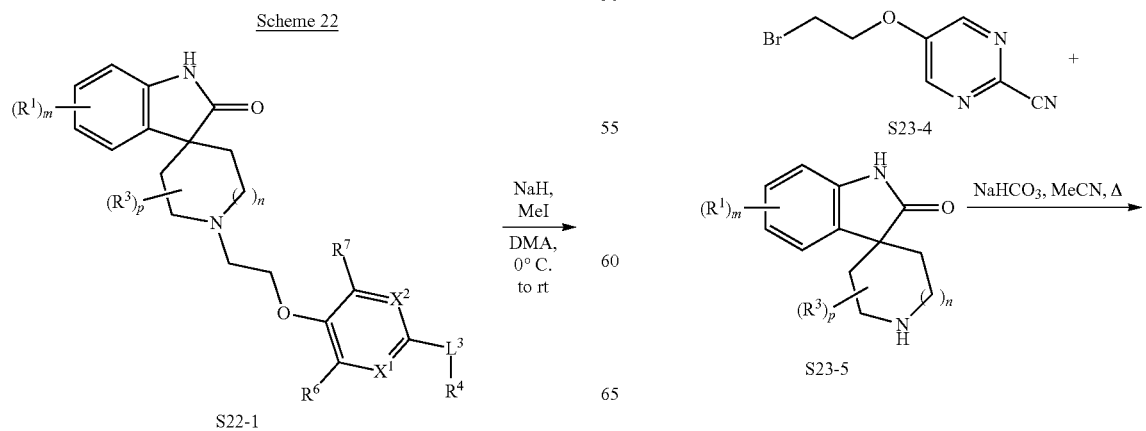

615
-continued

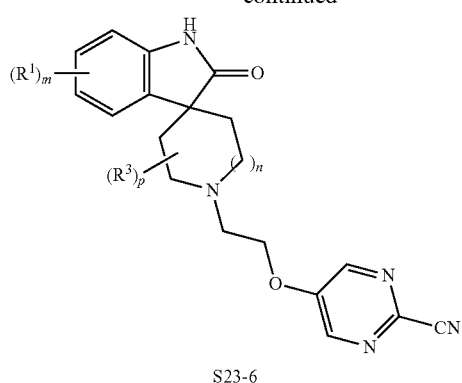
S23-6

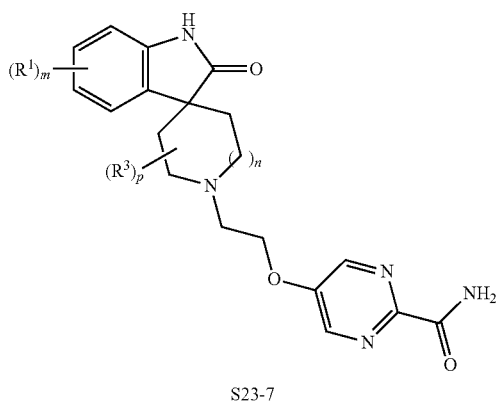
S23-7

Primary amides of formula S23-7 can be generated according to Scheme 23. Palladium-catalyzed borylation of pyrimidine S23-1 followed by oxidation gives compound S23-3. Alkylation with 1,2-dibromoethane to provide S23-4 and coupling with amine S23-5 under conditions outlined above (Scheme 12) generates compound S23-6. Conversion of the nitrile to the primary amide S23-7 occurs upon treatment with potassium carbonate and aqueous $H_2O_2$.

Scheme 24

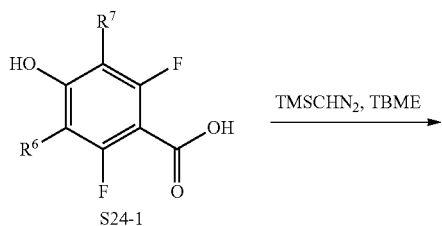
S24-1

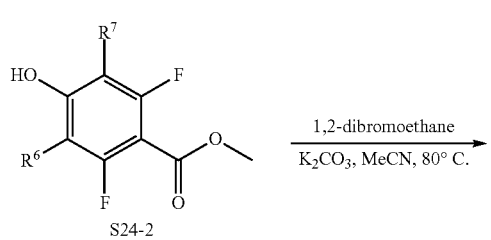
S24-2

616
-continued

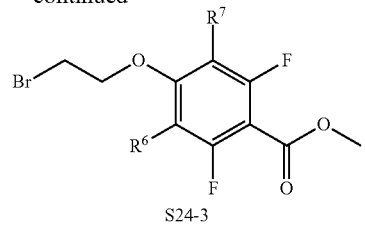
S24-3

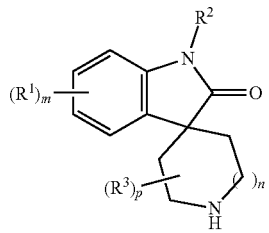
S24-4

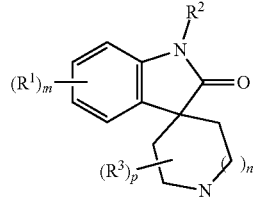
S24-5

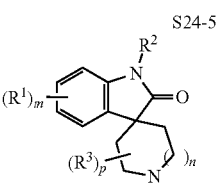
S24-6

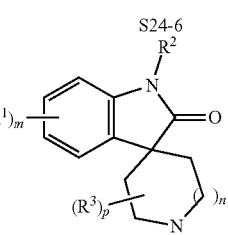

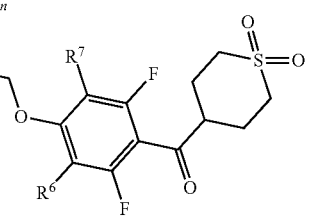
S24-8

Compounds of formula S24-8 can be synthesized according to Scheme 24. Esterification and alkylation of carboxylic acid S24-1 provides alkyl bromide S24-3. Coupling with amine S24-4 under standard conditions (Scheme 12) gives S24-5. Hydrolysis followed by amide bond formation with amine S24-7, using N-methyl imidazole and TCFH, gives S24-8.

Scheme 25

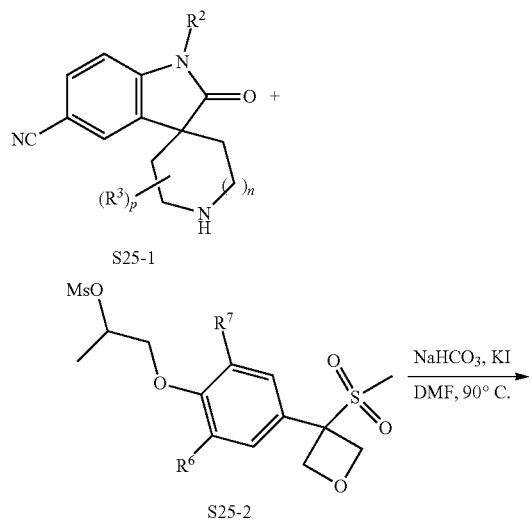

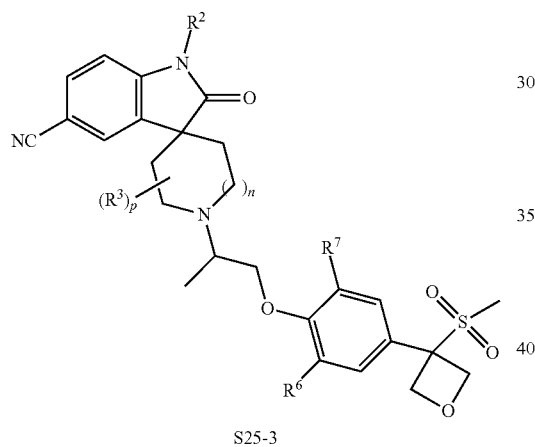

Compounds of formula S25-3 may also be prepared by reaction of an amine such as S25-1 with a secondary mesylate such as S25-2 in the presence of NaHCO$_3$ and potassium iodide in DMF at elevated temperature, as depicted in Scheme 25. Compounds of formula S25-3 may be further purified by chiral SFC to generate isomerically pure analogs.

Scheme 26

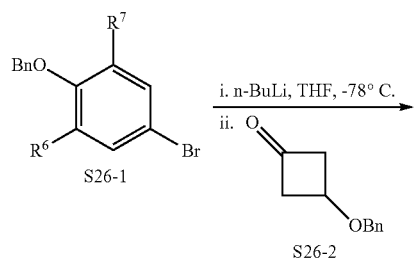

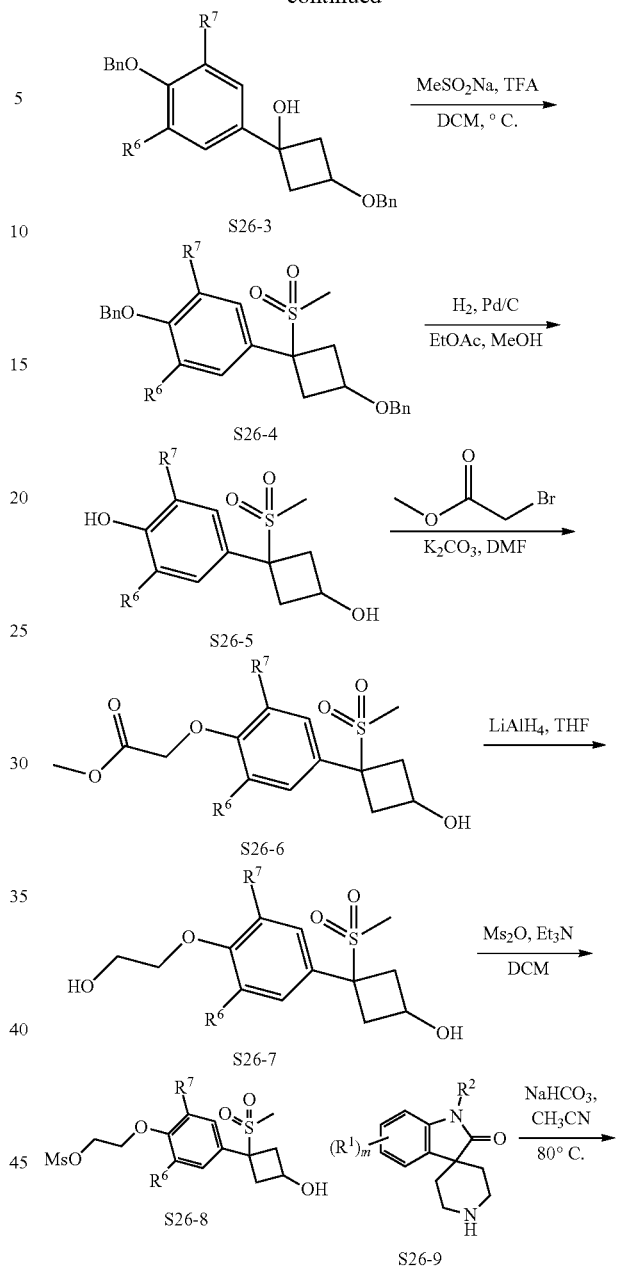

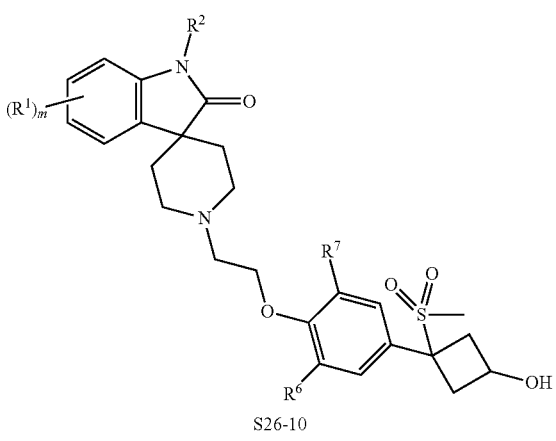

Compounds of formula S26-10 may be prepared according to Scheme 26. Lithium-halogen exchange with aryl bromide S26-1, followed by addition to a ketone such as S26-2, gives alcohol S26-3 as a mixture of cis and trans isomers. Reaction with sodium methanesulfinate and TFA gives sulfone S26-4. Removal of benzyl ethers by hydrogenation gives diol S26-5. Selective alkylation of the phenol moiety with bromoethyl acetate gives ester S26-6. Reduction with LiAlH$_4$ gives alcohol S26-7, which can be converted to S26-8 and coupled with amine S26-9 using procedures described above (Scheme 12). Further purification of S26-10 to obtain single stereoiosmers may be achieved by methods such as reverse phase HPLC or chiral SFC.

Scheme 27

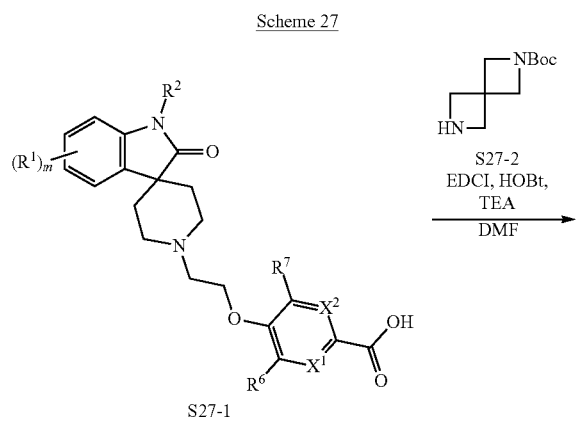

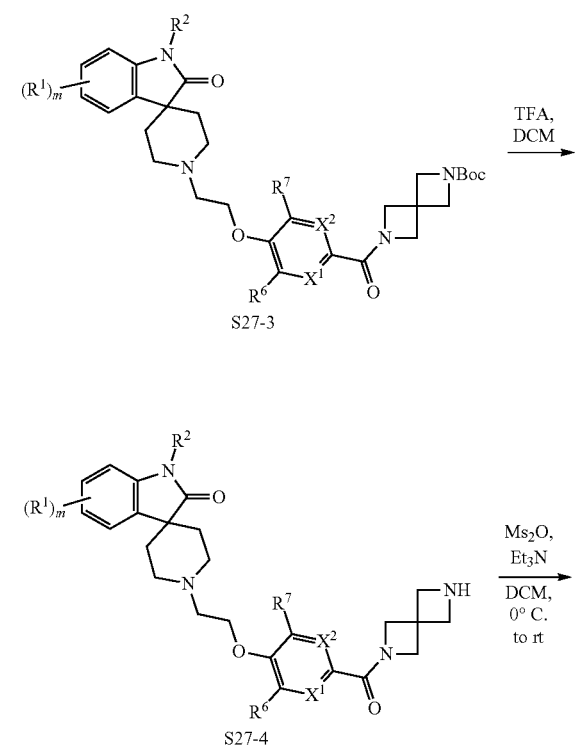

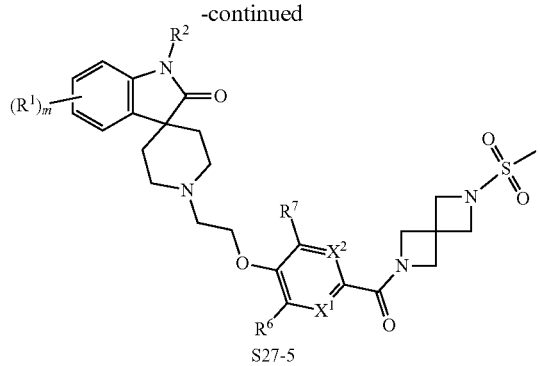

Compounds of formula S27-5 can be prepared according to Scheme 27. Coupling of acid S27-1 with an amine such as S27-2 under the action of EDCI and HOBt gives amide S27-3. Treatment with a protic acid such as TFA gives amine S27-4. Amine S27-4 may be further elaborated, such as by reaction with methanesulfonic anhydride and TEA, to give compounds such as S27-5.

Scheme 28

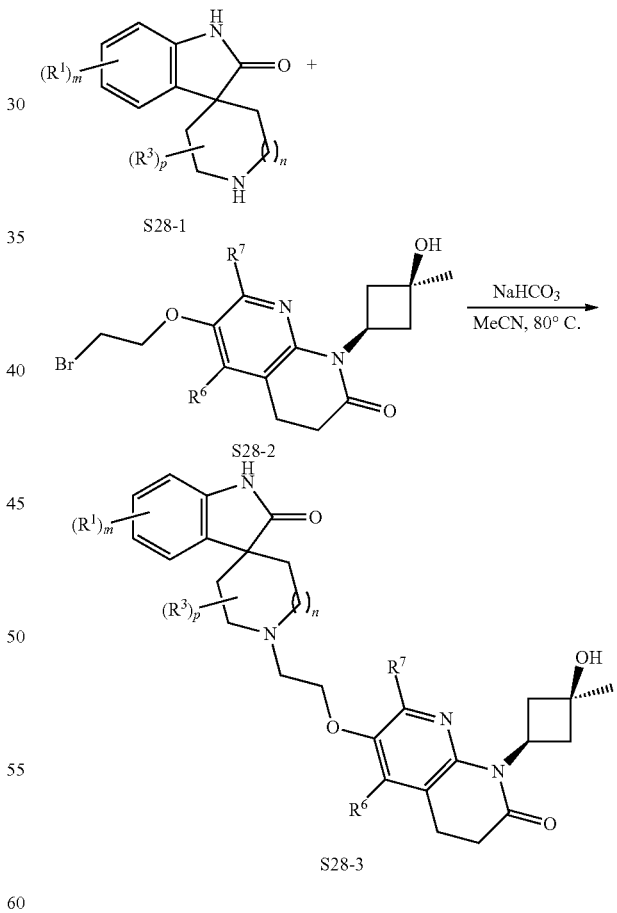

Compounds of formula S28-3 can be prepared according to Scheme 28, using reaction conditions similar to those described above. Coupling of amine S28-1 with azatetrahydronaphthyridinones bearing tertiary alcohol moieties such as S28-2 occurs upon heating in an aprotic solvent such as acetonitrile in the presence of an inorganic base such as sodium bicarbonate to give compounds of formula S28-3.

Scheme 29

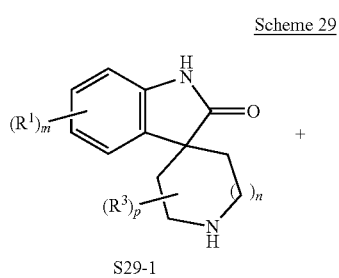

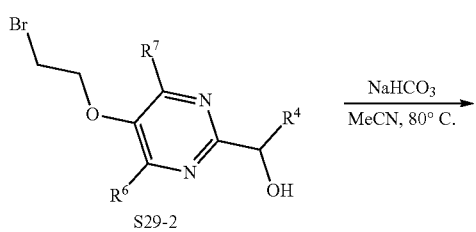

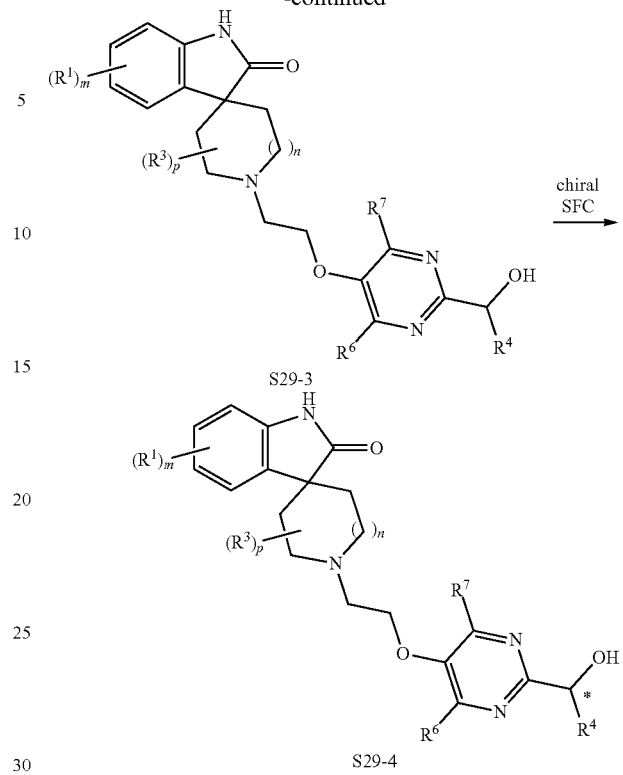

Compounds of formula S29-4 may can be prepared according to Scheme 29. Reaction of amine S29-1 with an alkyl bromide bearing a secondary alcohol such as S29-2 occurs upon heating in an aprotic solvent such as acetonitrile in the presence of an inorganic base such as sodium bicarbonate to give compounds of formula S29-3. Further purification using methods such as chiral SFC may be used to generate single isomer analogs such as S29-4.

Scheme 30

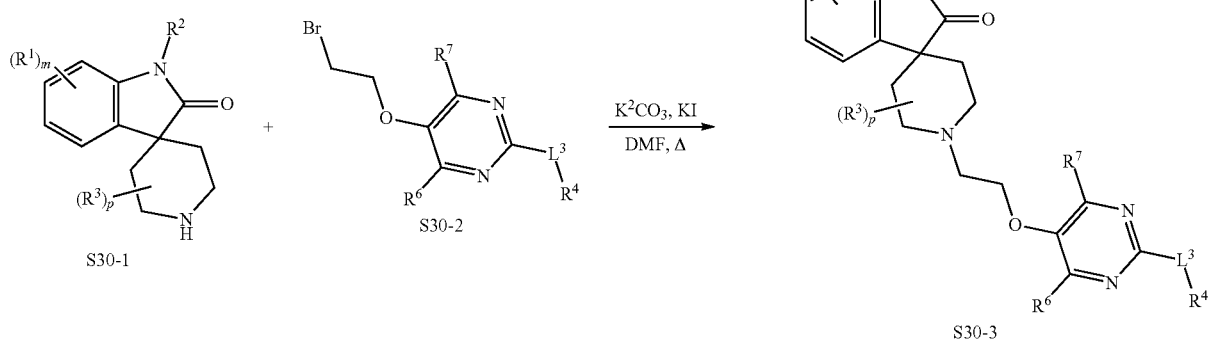

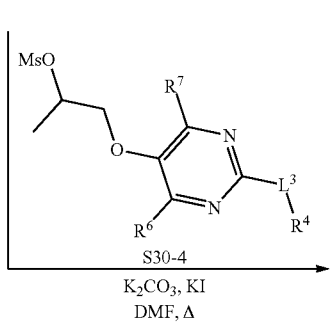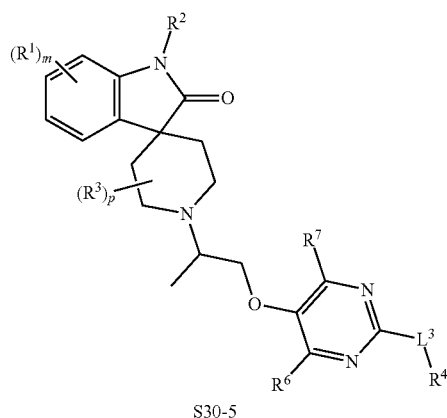

Compounds of formula S30-3 and S30-5, which bear multiple substituents on the pyrimidine moiety, are depicted in Scheme 30. Thus, coupling of the amine HCl salt S30-1 with alkyl halide S30-2 may be achieved upon heating in an aprotic solvent such as DMF, in the presence of potassium carbonate and potassium iodide, to deliver compounds of formula 30-3. Alternatively, coupling under identical reaction conditions as those described above with amine S30-1 and a chiral center bearing intermediate such as S30-4, may give rise to compounds of the formula S30-5. If desired, further purification of S30-5 may be achieved using methods such as chiral SFC.

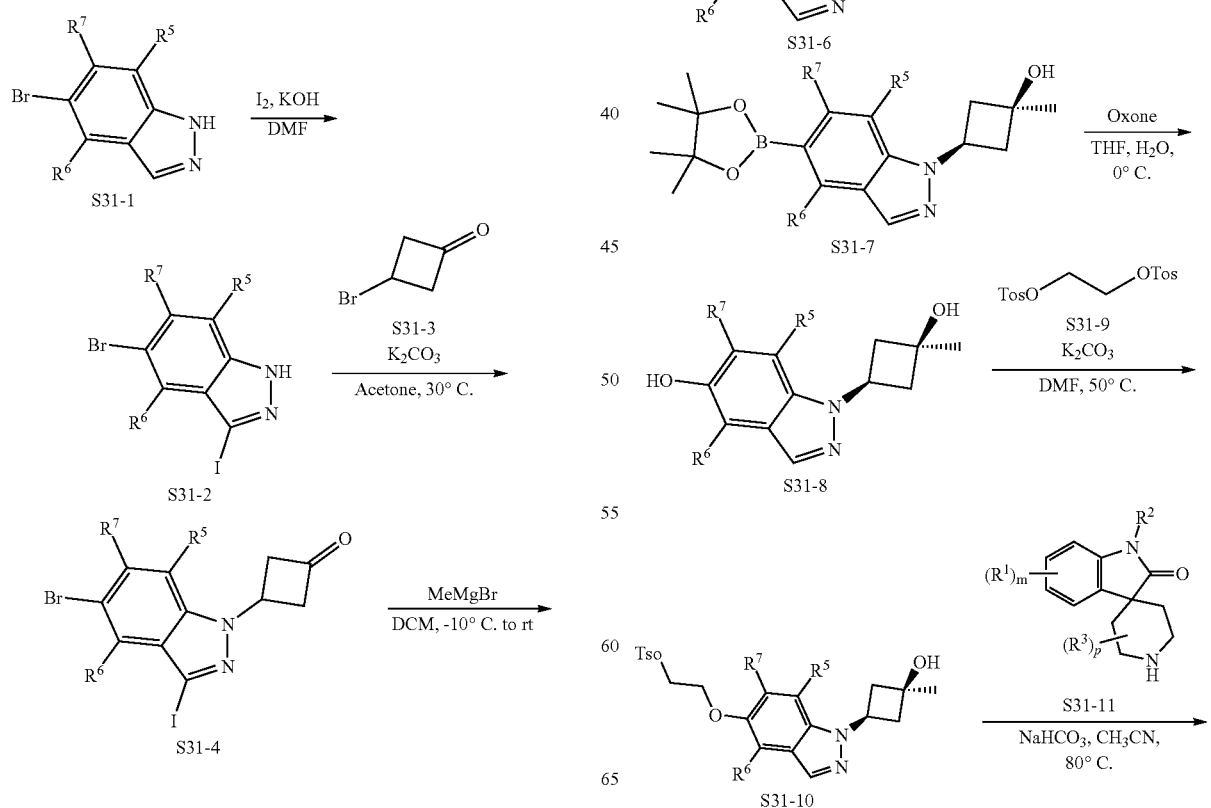

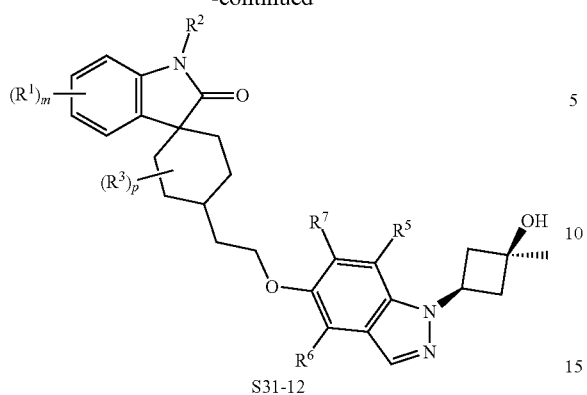

S31-12

Compounds of formula S31-12 may be prepared according to Scheme 31. Treatment of indazole S31-1 with iodine and potassium hydroxide in a solvent such as DMF provides S31-2. Alkylation of S31-2 with an electrophile such as S31-3 occurs in the presence of an inorganic base such as potassium carbonate in warm acetone to give S31-4. Treatment with a Grignard reagent such as methylmagnesium bromide at −10° C. in a solvent such as DCM gives tertiary alcohol S31-5. Protodeiodination occurs on treatment with Zn metal and acetic acid in methanol to give S31-6. Palladium catalyzed borylation may be conducted in a solvent such as 1,4-dioxane by reaction with Bis(pinacolato)diboron, potassium acetate as base, and a palladium catalyst such as [1,1'-Bis(diphenylphosphino)ferrocene]dichloropalladium(II) to give S31-7. Reaction with Oxone gives rise to alcohol S31-8. Phenol alkylation occurs on treatment with an electrophile such as bis-tosylate S31-9 to give S31-10. Heating a mixture of S31-10, an amine nucleophile such as S31-11, and an inorganic base such as sodium bicarbonate in a solvent such as acetonitrile gives compounds of formula S31-12.

Scheme 32

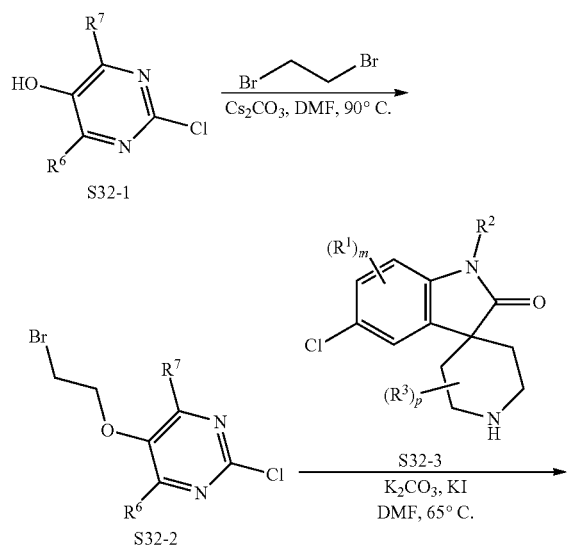

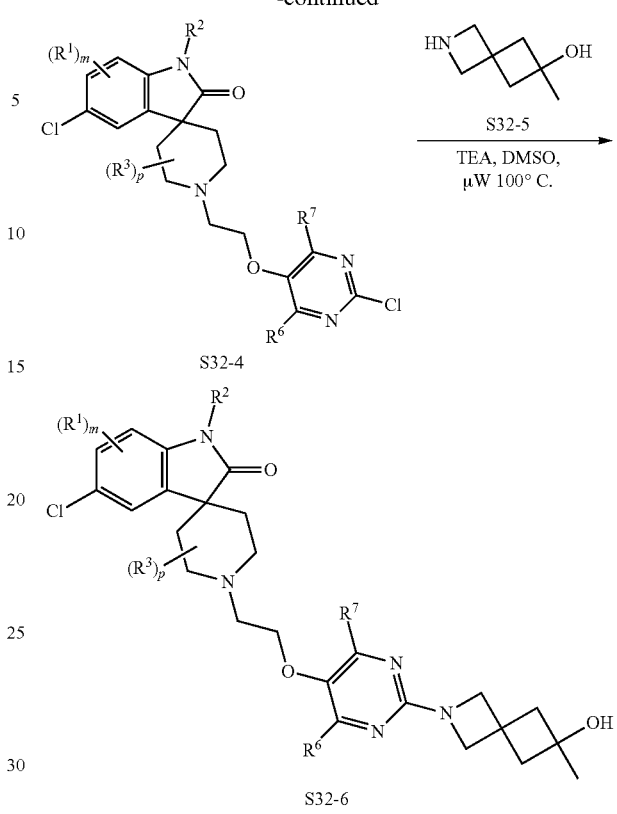

Compounds of formula S32-6 may be prepared according to Scheme 32. Heating a mixture of S32-1, 1,2-dibromoethane, and an inorganic base such as cesium carbonate gives S32-2. Heating a mixture of S32-2, an amine nucleophile such as S32-3, an inorganic base such as potassium bicarbonate, and potassium iodide in a solvent such as DMF gives compounds of formula S32-4. Compounds of formula S32-4 may be further elaborated by $S_NAr$ reaction with an amine such as S32-5, a tertiary amine base such as triethylamine, in DMSO at 100° C. in a microwave reactor to give compounds of formula S32-6.

Scheme 33

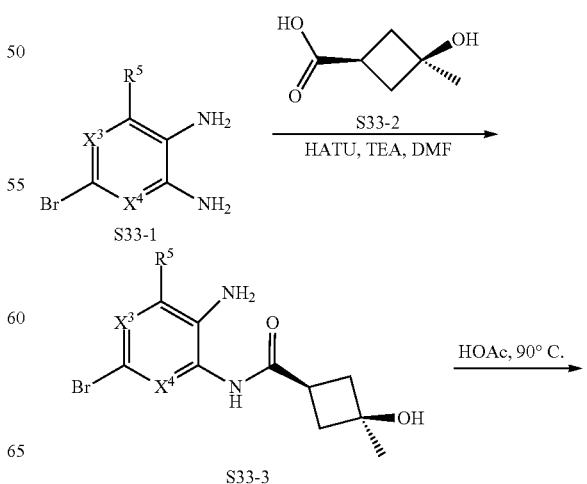

-continued

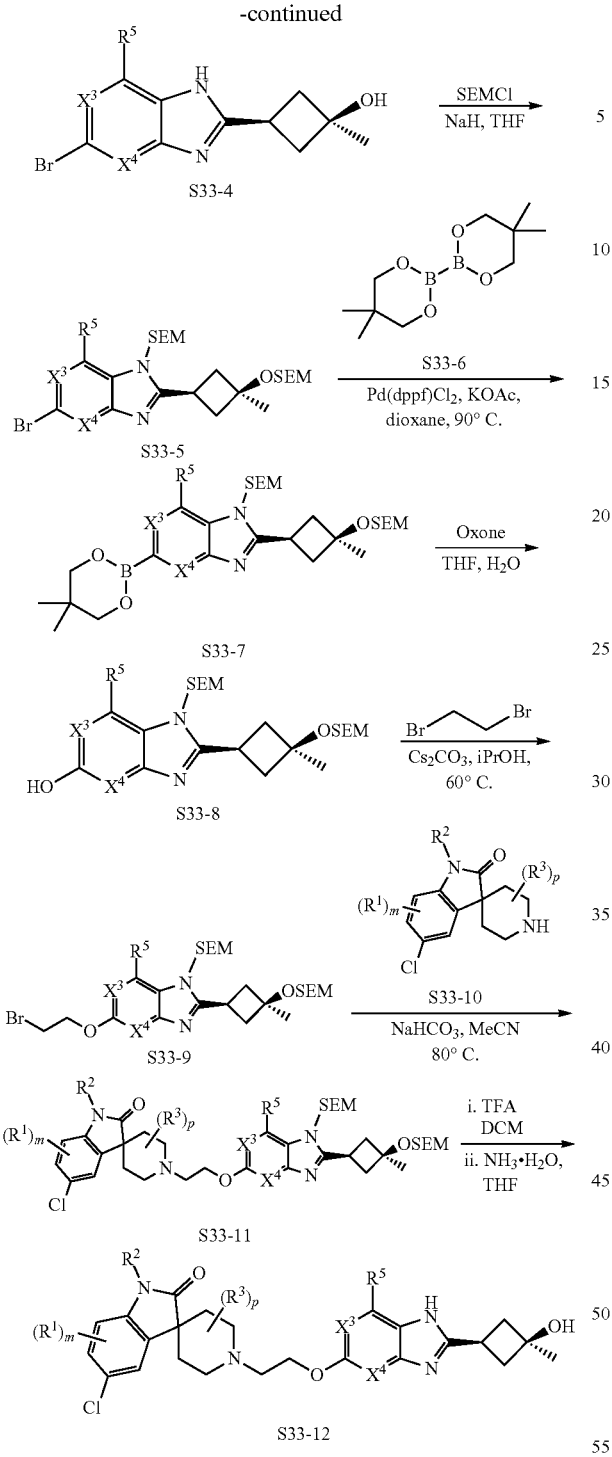

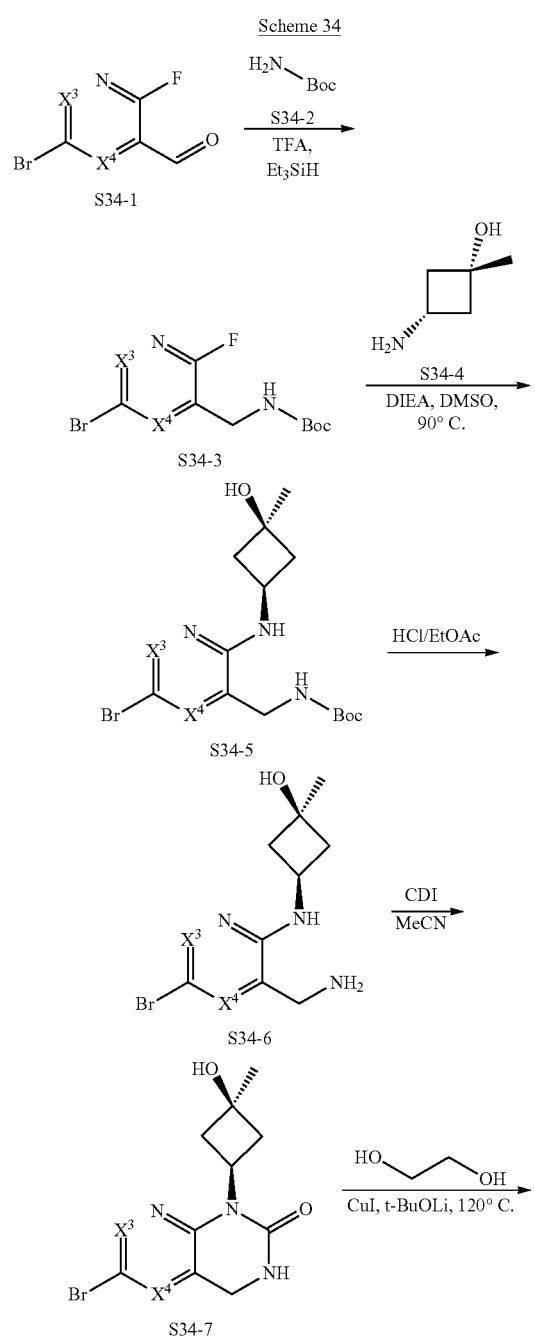

chloropalladium(II) to give S33-7. Treatment with Oxone in a mixed solvent such as THF and water gives S33-8. Alkylation with 1,2-dibromoethane in the presence of an inorganic base such as cesium carbonate gives S33-9. S33-9 may be coupled with amine S33-10 in hot acetonitrile in the presence of a base such as sodium bicarbonate to give S33-11. SEM-protecting group removal is achieved by treatment with a protic acid such as TFA, to give a benzimidazole which may then be converted to the free base by treatment with aqueous ammonia to deliver compounds of formula S33-12.

Compounds of formula S33-12 may be prepared according to Scheme 33. Reaction of diamine derivative S33-1 with a carboxylic acid such as S33-2 gives amide S33-3. Cyclization to benzimidazole S33-4 may be achieved by heating S33-3 in acetic acid. Treatment of S33-4 with an excess of 2-(Trimethylsilyl)ethoxymethyl chloride and sodium hydride in an aprotic solvent such as THF gives S33-5. Palladium catalyzed borylation may be conducted in a solvent such as 1,4-dioxane by reaction with diboron reagent S33-6, potassium acetate as base, and a palladium catalyst such as [1,1'-Bis(diphenylphosphino)ferrocene]di-

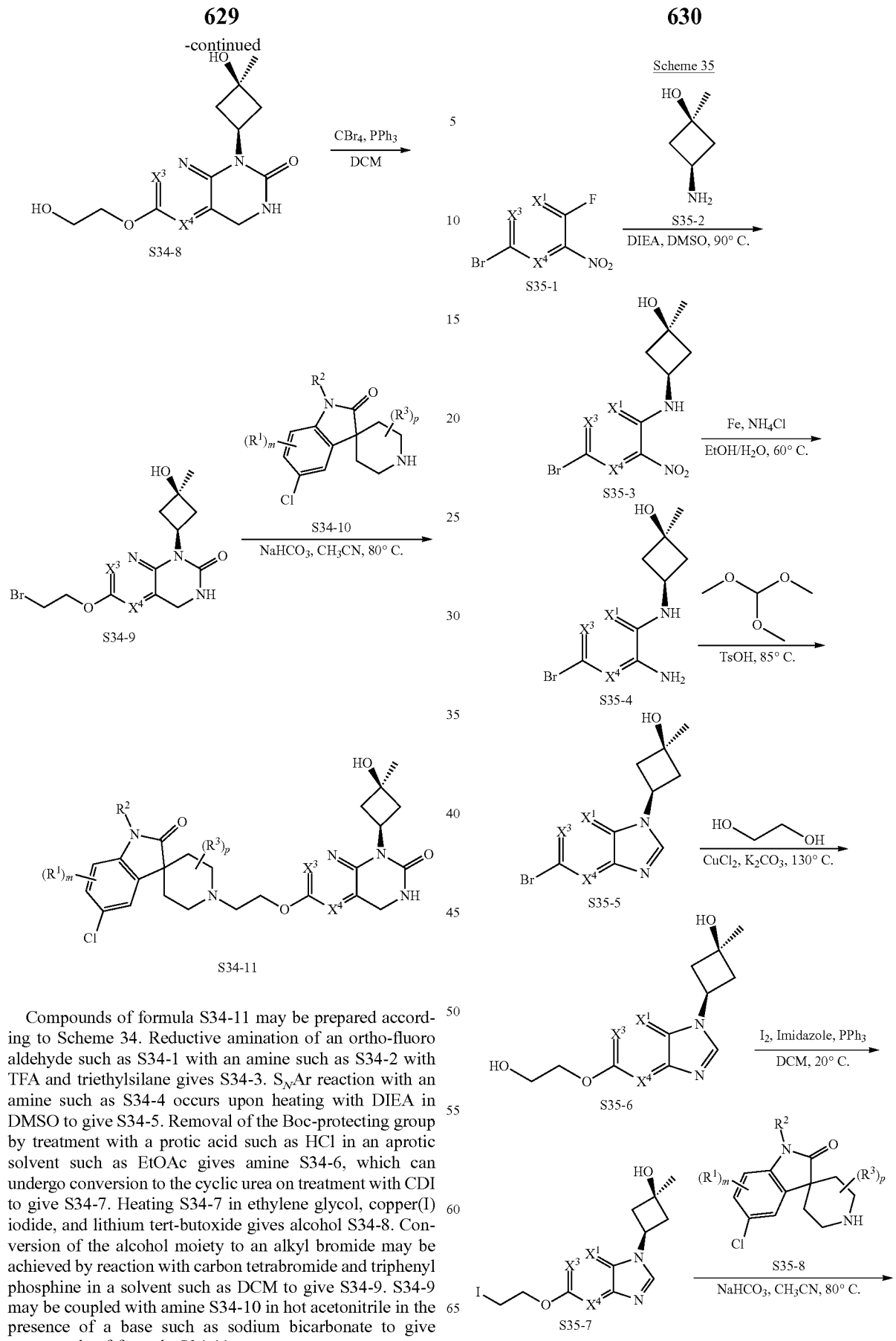

Compounds of formula S34-11 may be prepared according to Scheme 34. Reductive amination of an ortho-fluoro aldehyde such as S34-1 with an amine such as S34-2 with TFA and triethylsilane gives S34-3. S$_N$Ar reaction with an amine such as S34-4 occurs upon heating with DIEA in DMSO to give S34-5. Removal of the Boc-protecting group by treatment with a protic acid such as HCl in an aprotic solvent such as EtOAc gives amine S34-6, which can undergo conversion to the cyclic urea on treatment with CDI to give S34-7. Heating S34-7 in ethylene glycol, copper(I) iodide, and lithium tert-butoxide gives alcohol S34-8. Conversion of the alcohol moiety to an alkyl bromide may be achieved by reaction with carbon tetrabromide and triphenyl phosphine in a solvent such as DCM to give S34-9. S34-9 may be coupled with amine S34-10 in hot acetonitrile in the presence of a base such as sodium bicarbonate to give compounds of formula S34-11.

-continued

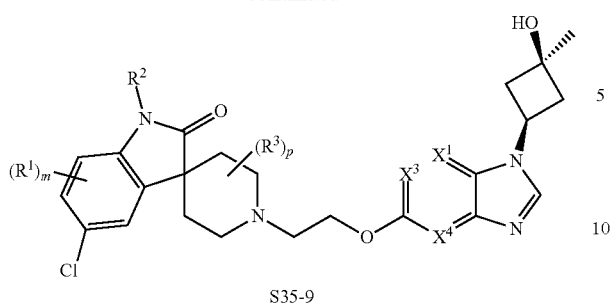

S35-9

Compounds of formula S35-9 may be prepared according to Scheme 35. S$_N$Ar reaction between S35-1 and amine S35-2 occurs upon heating with a tertiary amine base such as DIEA in DMSO solvent to give S35-3. Nitro group reduction by heating with iron and ammonium chloride in a mixed solvent such as ethanol and water gives S35-4. S35-4 is then converted to benzimidazole derivative S35-5 by heating in trimethyl orthoformate in the presence of p-toluene sulfonic acid. Heating S35-5 in ethylene glycol in the presence of copper (II) chloride and potassium carbonate gives the primary alcohol S35-6. Conversion to the alkyl iodide by treatment with iodine, imidazole, and triphenyl phosphine provides S35-7. S35-7 may be coupled with amine S35-8 in hot acetonitrile in the presence of a base such as sodium bicarbonate to give compounds of formula S35-9.

Scheme 36

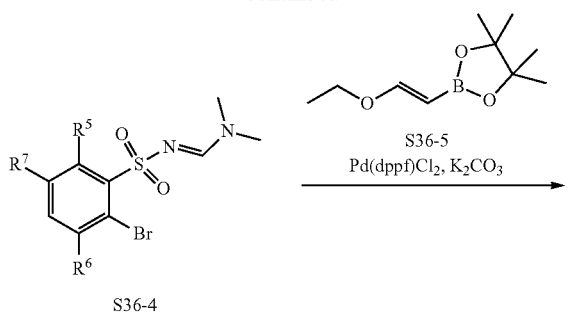

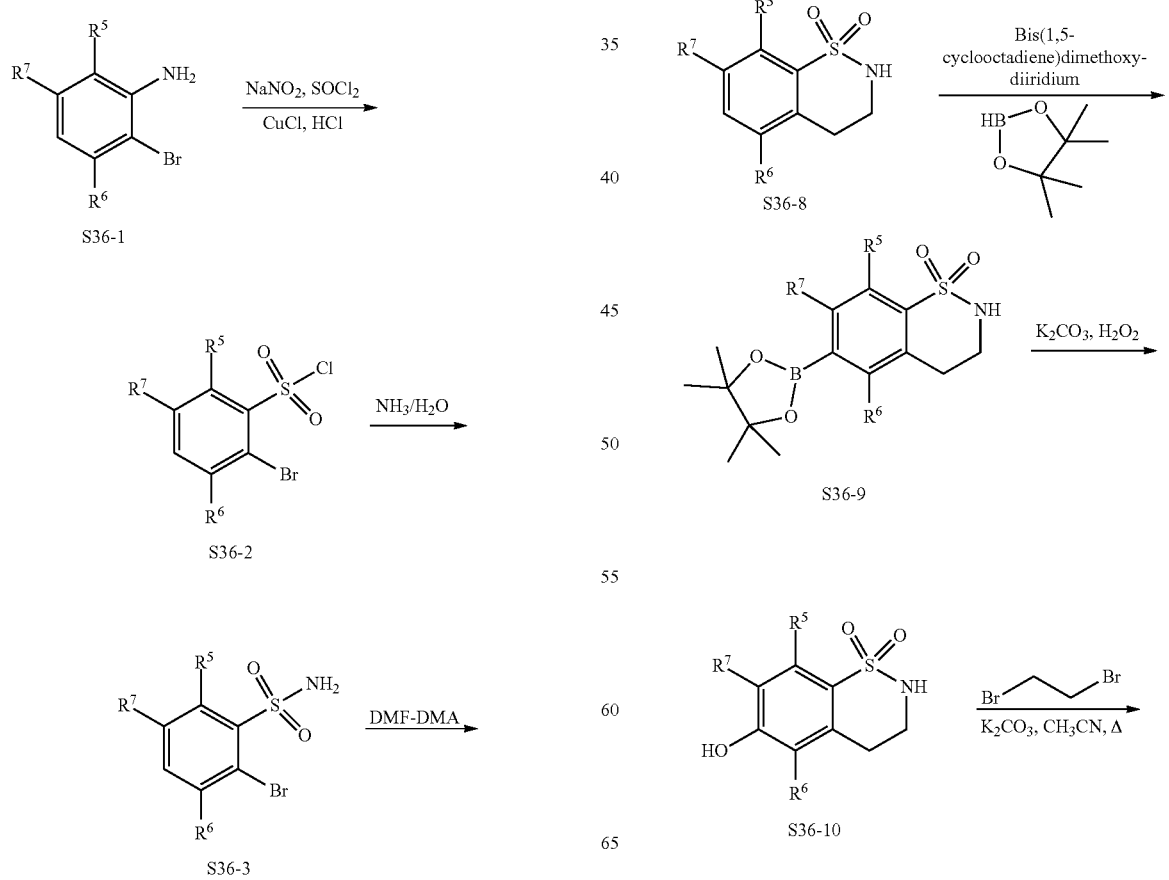

633
-continued

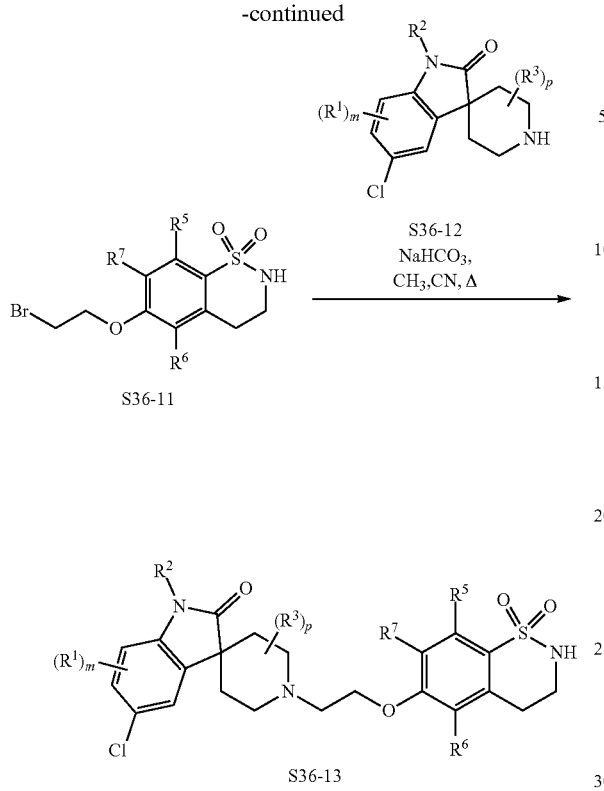

Compounds of formula S36-13 may be prepared according to Scheme 36. Conversion of anilne S36-1 to corresponding sulfonyl chloride S36-2 occurs upon treatment with sodium nitrite, thionyl chloride, copper(I) chloride, and HCl. Reaction of S36-2 with aqueous ammonia provides sulfonamide S36-3. Reaction with N,N-dimethylformamide dimethyl acetal then generates N-sulfonylformamidine S36-4. Suzuki coupling with a vinyl boronate ester such as S36-5 gives enol ether S36-6. Treatment with HCl leads to hydrolysis of the formamidine and enol ether and cyclization to give S36-7. Hydrogenation of S36-7 with Pd/C as catalyst gives S36-8. C—H oxidation of S36-8 with pinacol borane in the presence of catalyst Bis(1,5-cyclooctadiene)dimethoxydiiridium gives S36-9, which may undergo oxidation upon treatment with $H_2O_2$ and potassium carbonate to give phenol derivative S36-10. S36-10 undergoes alkylation with 1,2-dibromoethane under conditions described above to deliver S36-11. Coupling of S36-11 with amine S36-12 under conditions described above gives compounds of formula S36-13.

634

General Procedure for Intermediate A-1

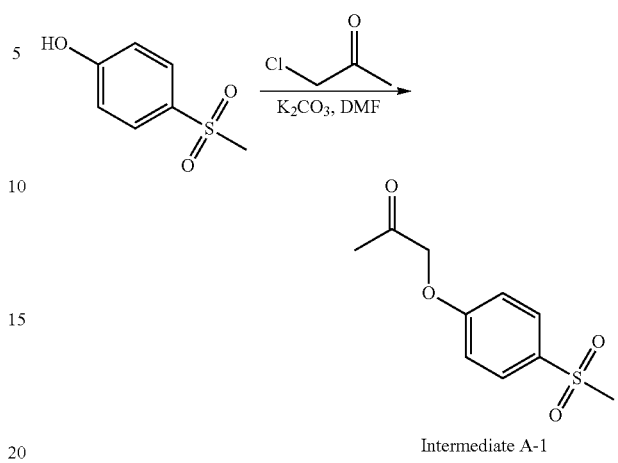

Step 1: 1-(4-methanesulfonylphenoxy)propan-2-one

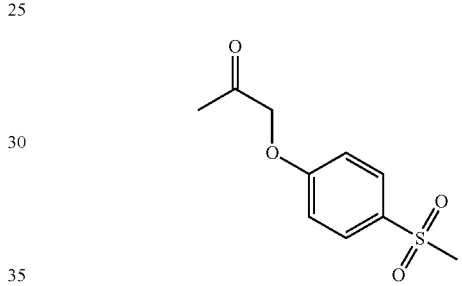

A mixture of 4-methylsulfonylphenol (500 mg, 2.90 mmol), 1-chloropropan-2-one (268 mg, 2.90 mmol) and $K_2CO_3$ (521 mg, 3.77 mmol) in DMF (10 mL) was stirred for 3 h. The reaction mixture was cooled to 0° C. and $H_2O$ (20 mL) was added. The biphasic mixture was extracted with EtOAc (3×20 mL). The combined organic layers were washed with $H_2O$ (20 mL), brine (20 mL), dried over $Na_2SO_4$, filtered, and concentrated in vacuo to give 1-(4-methylsulfonylphenoxy)propan-2-one (Intermediate A-1), which was taken to the next step without further purification. MS=229.1 [M+H]+.

The following intermediate in Table 2 was prepared according to procedures similar those described for Intermediate A-1 using the appropriate starting materials.

General Procedure for Intermediate A-2

TABLE 2

| Intermediate # | Structure | IUPAC Name | Exact Mass [M + H]+ |
|---|---|---|---|
| A-2 | ![structure] | 1-methyl-6-(2-oxopropoxy)-1,2,3,4-tetrahydroquinolin-2-one | Calc'd 234.1 Found 234.2 |

General Procedure for Intermediate A-3

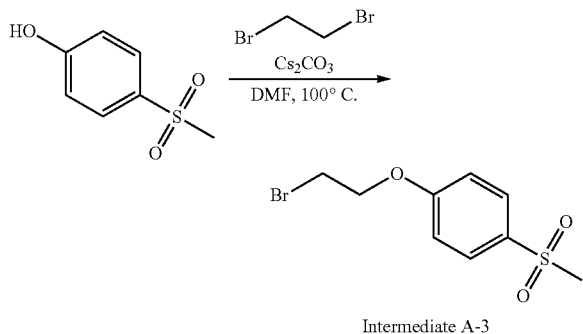

Step 1:
1-(2-bromoethoxy)-4-methanesulfonylbenzene

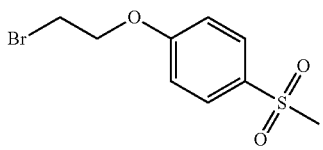

To a solution of 4-(methylsulfonyl)phenol (5.00 g, 29.0 mmol) in DMF (50 mL) were added $Cs_2CO_3$ (18.9 g, 58.1 mmol) and 1,2-dibromoethane (11.0 mL, 145 mmol). The mixture was stirred at 100° C. for 4 h. After cooling to room temperature, the reaction mixture was diluted with $H_2O$ (250 mL) and extracted with EtOAc (3×50 mL). The combined organic layers were washed with brine (30 mL), dried over $Na_2SO_4$, and concentrated in vacuo. The crude residue was purified by normal phase silica gel chromatography (Biotage 40 g cartridge, 0-60% EtOAc:petroleum ether). The crude product was triturated with MTBE (10 mL) to give 1-(2-bromoethoxy)-4-methanesulfonylbenzene (Intermediate A-3). $^1$H NMR (400 MHz, DMSO-$d_6$): δ 7.85 (d, J=7.2 Hz, 2H), 7.19 (d, J=6.8 Hz, 2H), 4.44 (t, J=4.2 Hz, 2H), 3.84 (t, J=4.2 Hz, 2H), 3.16 (s, 3H). MS=279.0/281.0 $[M+H]^+$.

The following intermediates in Table 3 were prepared according to procedures similar to steps described for Intermediate A-3 using the appropriate starting materials.
General Procedure for Intermediates A-4 to A-8 & A-83

TABLE 3

| Intermediate # | Structure | IUPAC Name | Exact Mass $[M + H]^+$ |
|---|---|---|---|
| A-4 | 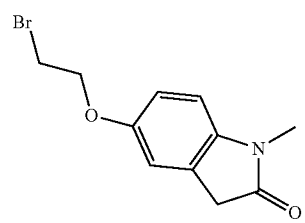 | 5-(2-bromoethoxy)-1-methyl-2,3-dihydro-1H-indol-2-one | Calc'd 270.0 Found 270.0 |
| A-5 | 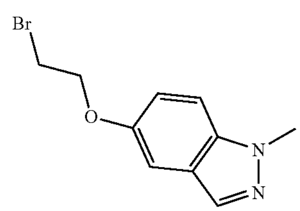 | 5-(2-bromoethoxy)-1-methyl-1H-indazole | Calc'd 255.0 Found 255.0 |
| A-6 | 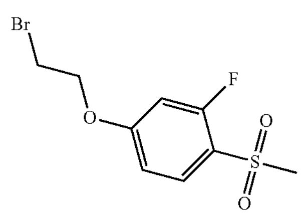 | 4-(2-bromoethoxy)-2-fluoro-1-methanesulfonylbenzene | No charge in LCMS |

TABLE 3-continued

| Intermediate # | Structure | IUPAC Name | Exact Mass [M + H]+ |
|---|---|---|---|
| A-7 | (structure) | N-[4-(2-bromoethoxy)phenyl]-N-methylmethanesulfonamide | Calc'd 308.0 Found 308.0 |
| A-8 | (structure) | {[4-(2-bromoethoxy)phenyl]imino}dimethyl-λ6-sulfanone | Calc'd 292.0 Found 292.0 |
| A-83 | (structure) | 6-(2-bromoethoxy)-1,2,3,4-tetrahydroquinolin-2-one | Calc'd 270.0/ 272.0 Found 270.0/ 271.9 |

General Procedure for Intermediates A-9 and A-10

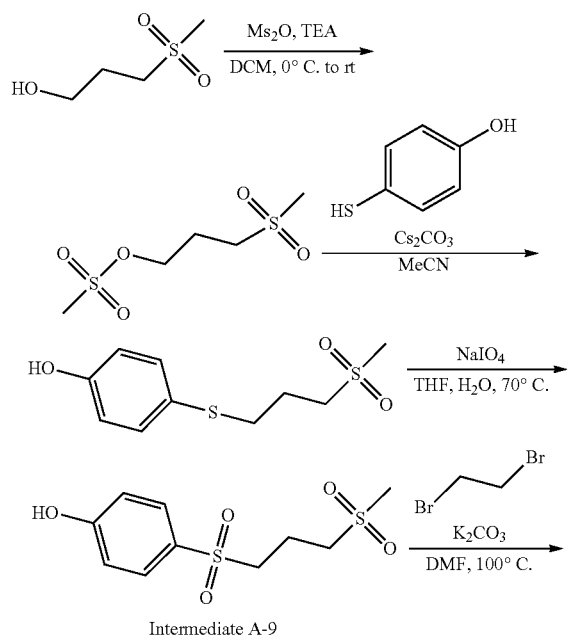

Intermediate A-9

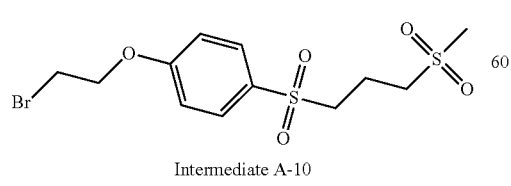

Intermediate A-10

Step 1: 3-methanesulfonylpropyl methanesulfonate

To a 0° C. solution of 3-methanesulfonylpropan-1-ol (500 mg, 3.62 mmol) in DCM (5 mL) were added TEA (1.01 mL, 7.24 mmol) and methanesulfonic anhydride (945 mg, 5.43 mmol). The mixture was warmed to room temperature and stirred for 2 h. The reaction mixture was quenched with $H_2O$ (20 mL) and extracted with DCM (3×10 mL). The combined organic layers were washed with brine (15 mL), dried over $Na_2SO_4$, filtered, and concentrated in vacuo to give 3-methanesulfonylpropyl methanesulfonate, which was used in the next step without further purification.

Step 2: 4-[(3-methanesulfonylpropyl)sulfanyl]phenol

To a mixture of 4-sulfanylphenol (319 mg, 2.52 mmol) and 3-methanesulfonylpropyl methanesulfonate (390 mg, 1.80 mmol) in MeCN (10 mL) was added $Cs_2CO_3$ (705 mg, 2.16 mmol). The mixture was stirred for 2 h, then was diluted with H₂O (10 mL) and extracted with EtOAc (3×10 mL). The combined organic layers were washed with brine (12 mL), dried over Na₂SO₄, filtered, and concentrated in vacuo. The crude residue was purified by normal phase silica gel chromatography (Biotage 4 g cartridge, 0-60% EtOAc: petroleum ether) to give 4-[(3-methanesulfonylpropyl)sulfanyl]phenol. MS=245.1 [M−H]⁻.

Step 3:
4-(3-methanesulfonylpropanesulfonyl)phenol

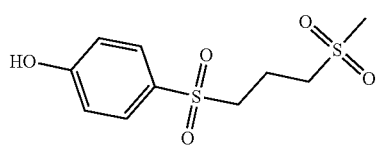 [SMILES: CS(=O)(=O)CCCS(=O)(=O)c1ccc(O)cc1]

To a solution of 4-[(3-methanesulfonylpropyl)sulfanyl]phenol (370 mg, 1.50 mmol) in THF (3 mL) and H₂O (3 mL) was added NaIO₄ (250 μL, 4.51 mmol). The mixture was stirred at 70° C. for 12 h. After cooling to room temperature, the reaction mixture was quenched with saturated aqueous Na₂SO₃ (20 mL), then extracted with EtOAc (3×10 mL). The combined organic layers were washed with brine (10 mL), dried over Na₂SO₄, filtered, and concentrated in vacuo. The crude residue was purified by normal phase silica gel chromatography (Biotage 4 g cartridge, 0-60% EtOAc: petroleum ether) to give 4-(3-methanesulfonylpropanesulfonyl)phenol (Intermediate A-9). MS=277.1 [M−H]⁻.

Step 4: 1-(2-bromoethoxy)-4-(3-methanesulfonylpropanesulfonyl)benzene

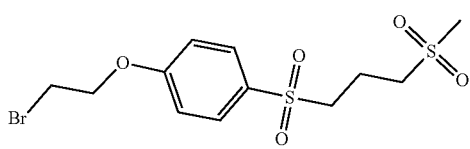 [SMILES: CS(=O)(=O)CCCS(=O)(=O)c1ccc(OCCBr)cc1]

To a solution of 4-(3-methanesulfonylpropanesulfonyl)phenol (Intermediate A-9) (300 mg, 1.08 mmol) in DMF (3 mL) were added K₂CO₃ (223 mg, 1.62 mmol) and 1,2-dibromoethane (407 μL, 5.39 mmol). The mixture was stirred at 100° C. for 12 h. After cooling to room temperature, the reaction mixture was diluted with H₂O (20 mL) and extracted with EtOAc (3×10 mL). The combined organic layers were washed with brine (8 mL), dried over Na₂SO₄, filtered, and concentrated in vacuo. The crude residue was purified by preparative TLC (SiO₂, 1:1 EtOAc:petroleum ether) to give 1-(2-bromoethoxy)-4-(3-methanesulfonylpropanesulfonyl)benzene (Intermediate A-10). ¹H NMR (400 MHz, DMSO-d₆): δ 7.84 (d, J=8.8 Hz, 2H), 7.24 (d, J=8.8 Hz, 2H), 4.47 (t, J=4.8 Hz, 2H), 3.86 (t, J=5.2 Hz, 2H), 3.43 (t, J=5.2 Hz, 2H), 3.22 (t, J=7.6 Hz, 2H), 2.98 (s, 3H), 2.00-1.92 (m, 2H).

General Procedure for Intermediate A-11

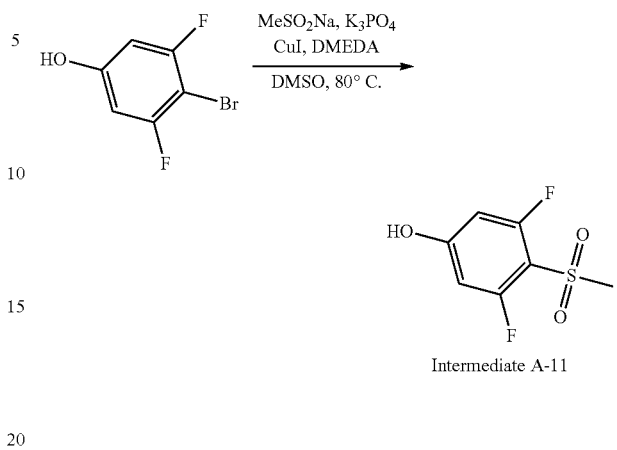

Step 1: 3,5-difluoro-4-methanesulfonylphenol

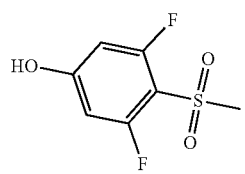

To a solution of 4-bromo-3,5-difluorophenol (1.00 g, 4.78 mmol) and MeSO₂Na (4.88 g, 47.8 mmol) in DMSO (15 mL) were added CuI (91.1 mg, 0.478 mmol), DMEDA (84 mg, 0.956 mmol) and K₃PO₄ (203 mg, 0.956 mmol). The mixture was stirred at 80° C. for 16 h. After cooling to room temperature, the reaction mixture was diluted with H₂O (20 mL) and extracted with EtOAc (3×10 mL). The combined organic layers were washed with brine (10 mL), dried over Na₂SO₄, filtered, and concentrated in vacuo. The crude residue was purified by normal phase silica gel chromatography (Biotage 12 g cartridge, 0-50% EtOAc:petroleum ether) to give the crude product. The product was further purified by reverse phase preparative HPLC (Agela C₁₈ column, 5-35% Methanol: 0.04% HCl in H₂O) to give 3,5-difluoro-4-methanesulfonylphenol (Intermediate A-11). MS=207.1 [M−H]⁻.

General Procedure for Intermediates A-12 and A-13

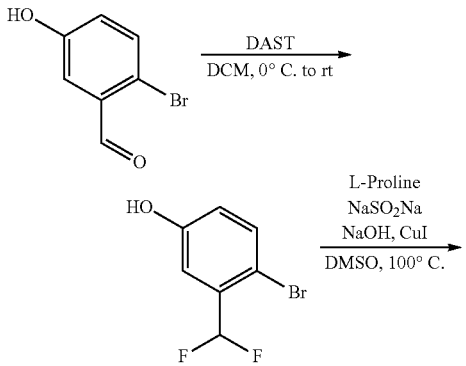

-continued

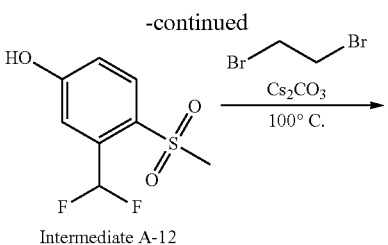

Intermediate A-12

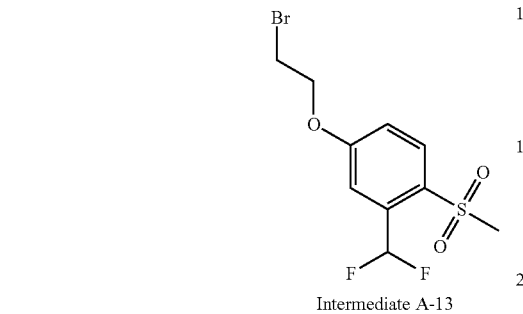

Intermediate A-13

Step 1: 4-bromo-3-(difluoromethyl)phenol

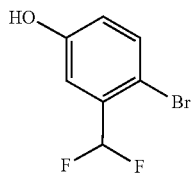 [SMILES: Oc1ccc(Br)c(C(F)F)c1]

To a 0° C. solution of 2-bromo-5-hydroxybenzaldehyde (17.6 g, 87.5 mmol) in DCM (170 mL) was added DAST (14.1 g, 87.6 mmol) in one portion. The mixture was allowed to warm to room temperature and stirred for 3 h. The reaction mixture was cooled to 0° C., quenched with saturated aqueous NaHCO₃ (150 mL), and extracted with DCM (2×100 mL). The combined organic layers were washed with brine (300 mL), dried over Na₂SO₄, filtered, and concentrated in vacuo. The crude residue was purified by normal phase silica gel chromatography (Biotage 120 g cartridge, 8-15% EtOAc:petroleum ether) to give 4-bromo-3-(difluoromethyl)phenol.

Step 2: 3-(difluoromethyl)-4-methanesulfonylphenol

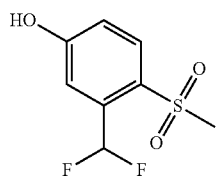

A mixture of 4-bromo-3-(difluoromethyl)phenol (3.60 g, 16.1 mmol), sodium methanesulfinate (16.5 g, 161 mmol), NaOH (323 mg, 8.07 mmol), (2S)-pyrrolidine-2-carboxylic acid (929 mg, 8.07 mmol) and copper(I) iodide (3.07 g, 16.1 mmol) in DMSO (40 mL) was degassed and purged with N₂ (3×). The mixture was stirred at 100° C. for 48 h. The reaction mixture was poured into ice water (200 mL) and then extracted with EtOAc (3×150 mL). The combined organic layers were washed with brine (2×300 mL), dried over Na₂SO₄, filtered, and concentrated in vacuo. The crude residue was purified by normal phase silica gel chromatography (Biotage 80 g cartridge, 0-30% EtOAc:petroleum ether) to give 3-(difluoromethyl)-4-methanesulfonylphenol (Intermediate A-12). ¹H NMR (400 MHz, DMSO-d₆): δ 11.04 (s, 1H), 7.87 (d, J=8.4 Hz, 1H), 7.67-7.40 (m, 1H), 7.20 (s, 1H), 7.11 (d, J=4.2 Hz, 1H), 3.21 (s, 3H).

Step 3: 4-(2-bromoethoxy)-2-(difluoromethyl)-1-methanesulfonylbenzene

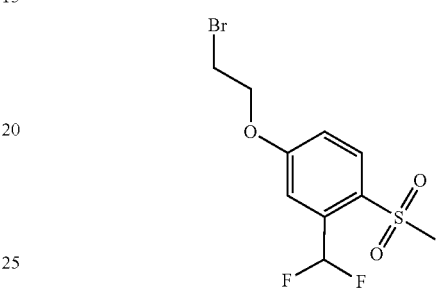

To a solution of 3-(difluoromethyl)-4-methanesulfonylphenol (300 mg, 1.35 mmol) in 1, 2-dibromoethane (7.5 mL) was added Cs₂CO₃ (1.32 g, 4.05 mmol). The mixture was stirred at 100° C. for 12 h. After cooling to room temperature, solids were removed by filtration and the filtrate was concentrated in vacuo. The crude residue was purified by normal phase silica gel chromatography (Biotage 20 g cartridge, 0-30% EtOAc:petroleum ether) to give 4-(2-bromoethoxy)-2-(difluoromethyl)-1-methanesulfonylbenzene (Intermediate A-13). ¹H NMR (400 MHz, DMSO-d₆): δ 7.99 (d, J=8.8 Hz, 1H), 7.74-7.55 (m, 1H), 7.47-7.32 (m, 2H), 4.56-4.49 (m, 2H), 3.87-3.82 (m, 2H), 3.26 (s, 3H).

General Procedure for Intermediate A-14

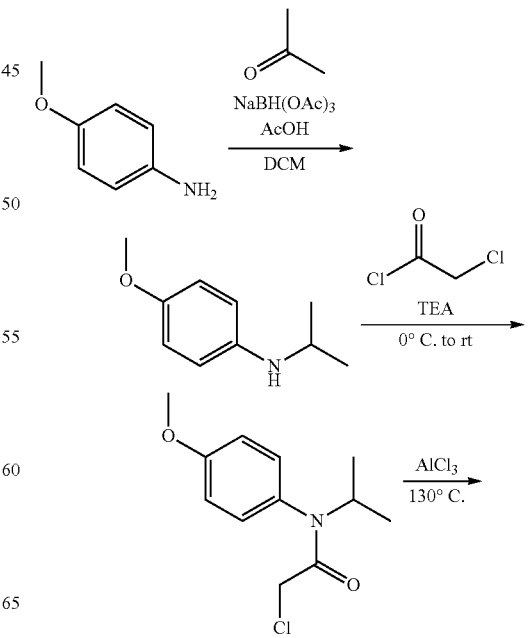

-continued

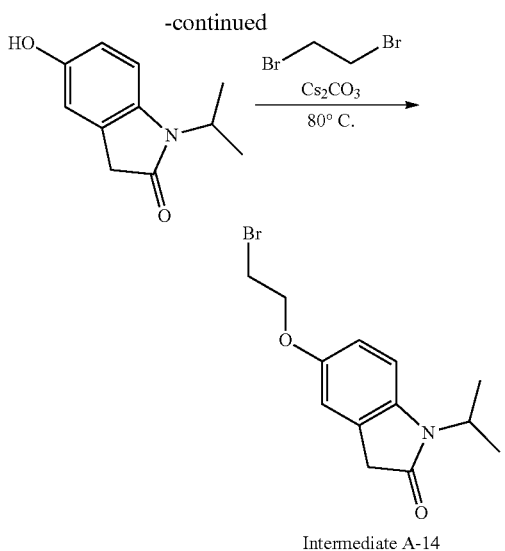

Intermediate A-14

Step 1: 4-methoxy-N-(propan-2-yl)aniline

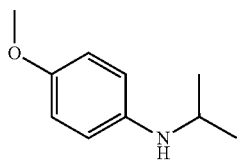

To a solution of 4-methoxyaniline (500 mg, 4.06 mmol) in DCM (10 mL) was added dropwise acetone (943 mg, 16.2 mmol) and AcOH (975 mg, 16.2 mmol). The mixture was stirred at room temperature for 1 h, and then NaBH(OAc)$_3$ (1.08 g, 5.08 mmol) was added. The resulting mixture was stirred at room temperature for 2 h. The reaction mixture was diluted with H$_2$O (10 mL) and extracted with EtOAc (3×10 mL). The combined organic layers were washed with brine (30 mL), dried over Na$_2$SO$_4$, filtered, and concentrated in vacuo. The crude residue was purified by normal phase silica gel chromatography (Biotage 12 g cartridge, 0-30% EtOAc:petroleum ether) to give 4-methoxy-N-(propan-2-yl)aniline. $^1$H NMR (400 MHz, DMSO-d$_6$): δ 6.72-6.61 (m, 2H), 6.54-6.45 (m, 2H), 4.81 (s, 1H), 3.62 (s, 3H), 3.49-3.39 (m, 1H), 1.08 (d, J=6.4 Hz, 6H). MS=166.2 [M+H]$^+$.

Step 2: 2-chloro-N-(4-methoxyphenyl)-N-(propan-2-yl)acetamide

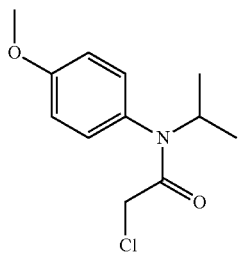 [SMILES: COc1ccc(N(C(=O)CCl)C(C)C)cc1]

A mixture of 4-methoxy-N-(propan-2-yl)aniline (200 mg, 1.21 mmol), TEA (253 μL, 1.82 mmol) in DCM (3 mL) was degassed and purged with N$_2$ (3×). The mixture was cooled to 0° C. and 2-chloroacetyl chloride (273 mg, 2.42 mmol) was added dropwise. The reaction was allowed to warm to room temperature and stirred for 12 h under N2 atmosphere. The reaction mixture was quenched with H$_2$O (15 mL) and extracted with EtOAc (3×10 mL). The combined organic layers were washed with saturated aqueous NaHCO$_3$ (20 ml) followed by brine (20 mL), dried over Na$_2$SO$_4$, filtered, and concentrated in vacuo. The crude residue was purified by normal phase silica gel chromatography (Isco 4 g cartridge, 0-40% EtOAc:petroleum ether) to give 2-chloro-N-(4-methoxyphenyl)-N-(propan-2-yl)acetamide. MS=242.1 [M+H]$^+$.

Step 3: 5-hydroxy-1-(propan-2-yl)-2,3-dihydro-1H-indol-2-one

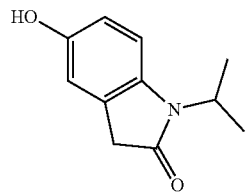

To 2-chloro-N-(4-methoxyphenyl)-N-(propan-2-yl)acetamide (1.00 g, 4.14 mmol) was slowly added aluminum chloride (2.21 g, 16.6 mmol). The mixture was stirred at 130° C. for 3 h. After cooling to room temperature, the reaction mixture was quenched with aqueous 1.0 M NaOH (20 mL), diluted with H$_2$O (10 mL), and extracted with EtOAc (3×30 mL). The combined organic layers were washed with brine (20 mL), dried over Na$_2$SO$_4$, filtered, and concentrated in vacuo. The crude residue was purified by normal phase silica gel chromatography (Isco 12 g cartridge, 0-40% EtOAc:petroleum ether) to give 5-hydroxy-1-(propan-2-yl)-2,3-dihydro-1H-indol-2-one. MS=192.2 [M+H]$^+$.

Step 4: 5-(2-bromoethoxy)-1-(propan-2-yl)-2,3-dihydro-1H-indol-2-one

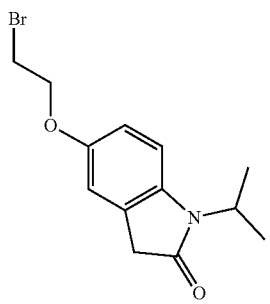 [SMILES: CC(C)N1C(=O)Cc2cc(OCCBr)ccc21]

To a solution of 5-hydroxy-1-(propan-2-yl)-2,3-dihydro-1H-indol-2-one (500 mg, 2.61 mmol) in 1,2-dibromoethane (8 mL) was added Cs$_2$CO$_3$ (2.56 g, 7.84 mmol). The mixture was stirred at 80° C. for 12 h. After cooling to room temperature, solids were removed by filtration and the filtrate was concentrated in vacuo. The crude residue was purified by normal phase silica gel chromatography (Isco 12 g cartridge, 0-60% EtOAc:petroleum ether) to give 5-(2-bromoethoxy)-1-(propan-2-yl)-2,3-dihydro-1H-indol-2-one (Intermediate A-14). MS=298.1/300.1 [M+H]⁺.

General Procedure for Intermediates A-15 & A-16

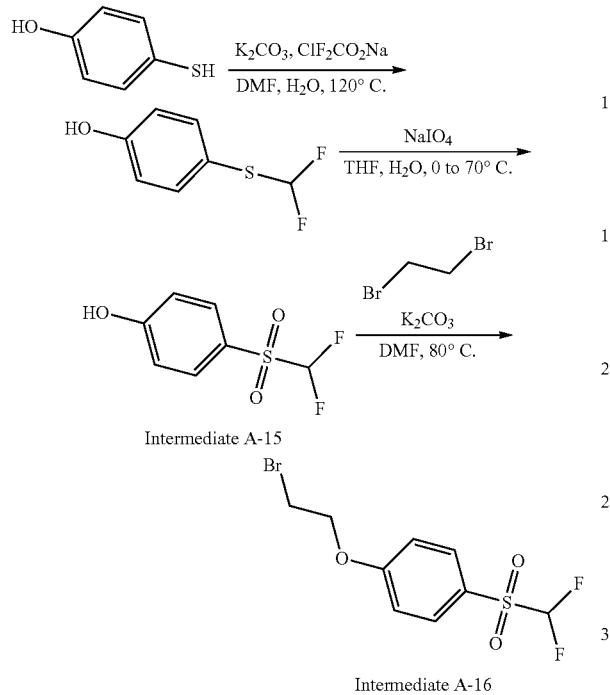

Intermediate A-15

Intermediate A-16

Step 1: 4-[(difluoromethyl)sulfanyl]phenol

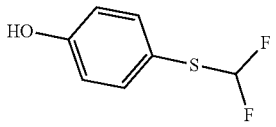

To a solution of 4-sulfanylphenol (300 mg, 2.38 mmol) in DMF (4 mL) and H$_2$O (1 mL) were added K$_2$CO$_3$ (1.97 g, 14.3 mmol) and 2-chloro-2,2-difluoro-acetic acid (302 µL, 3.57 mmol). The mixture was stirred at 120° C. for 15 h. After cooling to room temperature, the reaction mixture was quenched with H$_2$O (10 mL) and extracted with EtOAc (3×10 mL). The combined organic layers were dried over Na$_2$SO$_4$, filtered, and concentrated in vacuo. The crude residue was purified by normal phase silica gel chromatography (Biotage 12 g cartridge, 0-30% EtOAc:petroleum ether) to give 4-[(difluoromethyl)sulfanyl]phenol. MS=177.0 [M+H]⁺.

Step 2: 4-difluoromethanesulfonylphenol

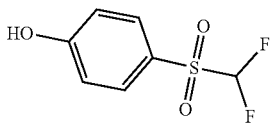 [SMILES: O=S(=O)(c1ccc(O)cc1)C(F)F]

To a 0° C. solution of 4-[(difluoromethyl)sulfanyl]phenol (100 mg, 0.568 mmol) in THF (1 mL) and H$_2$O (1 mL) was added NaIO$_4$ (94.4 µL, 1.70 mmol). The mixture was stirred at 70° C. for 15 h. After cooling to room temperature, the reaction mixture was quenched by the addition of saturated aqueous Na$_2$SO$_3$ (20 mL), and then extracted with EtOAc (3×5 mL). The combined organic layers were dried over Na$_2$SO$_4$, filtered, and concentrated in vacuo. The crude residue was purified by normal phase silica gel chromatography (Biotage 4 g cartridge, 0-30% EtOAc:petroleum ether) to give 4-difluoromethanesulfonylphenol (Intermediate A-15). MS=207.0 [M−H]⁺.

Step 3: 1-(2-bromoethoxy)-4-difluoromethanesulfonylbenzene

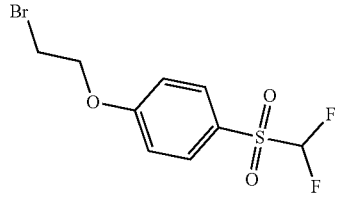 [SMILES: O=S(=O)(c1ccc(OCCBr)cc1)C(F)F]

To a mixture of 4-(difluoromethylsulfonyl)phenol (500 mg, 2.40 mmol) and 1,2-dibromoethane (906 µL, 12.0 mmol) in DMF (5 mL) was added K$_2$CO$_3$ (664 mg, 4.80 mmol). The mixture was stirred at 80° C. for 16 h. After cooling to room temperature, the reaction mixture was diluted with H$_2$O (20 mL), and then extracted with EtOAc (3×15 mL). The combined organic layers were washed with brine (20 mL), dried over Na$_2$SO$_4$, filtered, and concentrated in vacuo. The crude residue was purified by normal phase silica gel chromatography (Biotage 12 g cartridge, 0-50% EtOAc:petroleum ether) to give 1-(2-bromoethoxy)-4-difluoromethanesulfonylbenzene (Intermediate A-16). ¹H NMR (400 MHz, DMSO-d$_6$): δ 7.80 (d, J=2.8 Hz, 2H), 7.21-7.04 (m, 3H), 4.95 (t, J=7.2 Hz, 2H), 3.85 (t, J=7.2 Hz, 2H).

General Procedure for Intermediate A-17

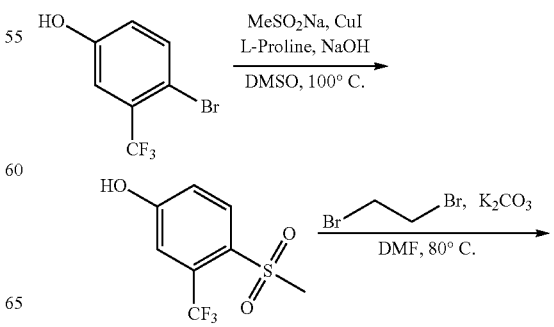

Step 1: 4-methanesulfonyl-3-(trifluoromethyl)phenol

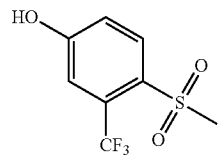

A mixture of 4-bromo-3-(trifluoromethyl)phenol (7.00 g, 29.1 mmol), sodium methanesulfinate (29.7 g, 290 mmol), CuI (2.77 g, 14.5 mmol), NaOH (581 mg, 14.5 mmol) and L-Proline (1.67 g, 14.5 mmol) in DMSO (100 mL) was degassed and purged with N2 (3×). The mixture was stirred at 100° C. for 3 d under N2 atmosphere. After cooling to room temperature, the reaction mixture was quenched with H₂O (80 mL) and extracted with EtOAc (3×150 mL). The combined organic layers were washed with brine (2×100 mL), dried over Na₂SO₄, filtered, and concentrated in vacuo. The crude residue was purified by normal phase silica gel chromatography (Biotage 80 g cartridge, 0-50% EtOAc: petroleum ether) to give 4-methanesulfonyl-3-(trifluoromethyl)phenol. MS=239.1 [M−H]⁻.

Step 2: 4-(2-bromoethoxy)-1-methanesulfonyl-2-(trifluoromethyl)benzene

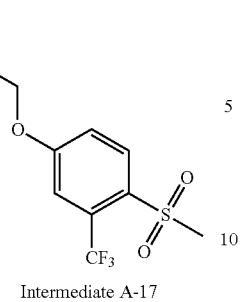

To a solution of 4-methylsulfonyl-3-(trifluoromethyl)phenol (500 mg, 2.08 mmol) in DMF (5 mL) were added 1,2-dibromoethane (2.36 mL, 31.2 mmol) and K₂CO₃ (575 mg, 4.16 mmol). The mixture was stirred at 80° C. for 2 h. After cooling to room temperature, the reaction mixture was quenched with H₂ (8 mL) and extracted with EtOAc (3×15 mL). The combined organic layers were washed with brine (2×10 mL), dried over Na₂SO₄, filtered, and concentrated in vacuo. The crude residue was purified by normal phase silica gel chromatography (Biotage 12 g cartridge, 0-25% EtOAc: petroleum ether) to give 4-(2-bromoethoxy)-1-methanesulfonyl-2-(trifluoromethyl)benzene (Intermediate A-17). MS=347.0/349.0 [M+H]⁺.

The following intermediates in Table 4 were prepared according to procedures similar those described for Intermediate A-17 using the appropriate starting materials.

General Procedure for Intermediates A-18 to A-22

TABLE 4

| Intermediate # | Structure | Name | Exact Mass [M + H]⁺ |
|---|---|---|---|
| A-18 | ![structure] | 5-(2-bromoethoxy)-1,3-difluoro-2-methanesulfonylbenzene | Calc'd 332.0/334.0 Found 332.1/334.0 [M + NH₄]⁺ |
| A-19 | ![structure] | 4-(2-bromoethoxy)-2-chloro-1-methanesulfonylbenzene | Calc'd 312.9/314.9 Found 312.9/315.0 |

TABLE 4-continued

| Intermediate # | Structure | Name | Exact Mass [M + H]+ |
|---|---|---|---|
| A-20 | 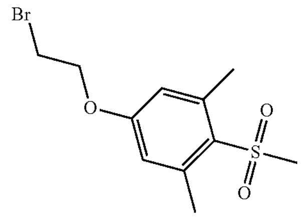 [SMILES: Cc1cc(OCCBr)cc(C)c1S(C)(=O)=O] | 5-(2-bromoethoxy)-2-methanesulfonyl-1,3-dimethylbenzene | Calc'd 307.0/ 309.0 Found 307.1/ 309.0 |
| A-21 | 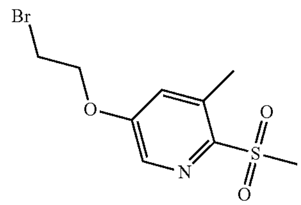 | 5-(2-bromoethoxy)-2-methanesulfonyl-3-methylpyridine | Calc'd 294.0/ 296.0 Found 294.0/ 296.0 |
| A-22 | 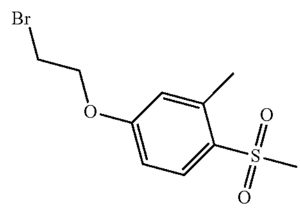 | 4-(2-bromoethoxy)-1-methanesulfonyl-2-methylbenzene | Calc'd 293.0/ 295.0 Found 293.0/ 295.0 |

General Procedure for Intermediate A-23

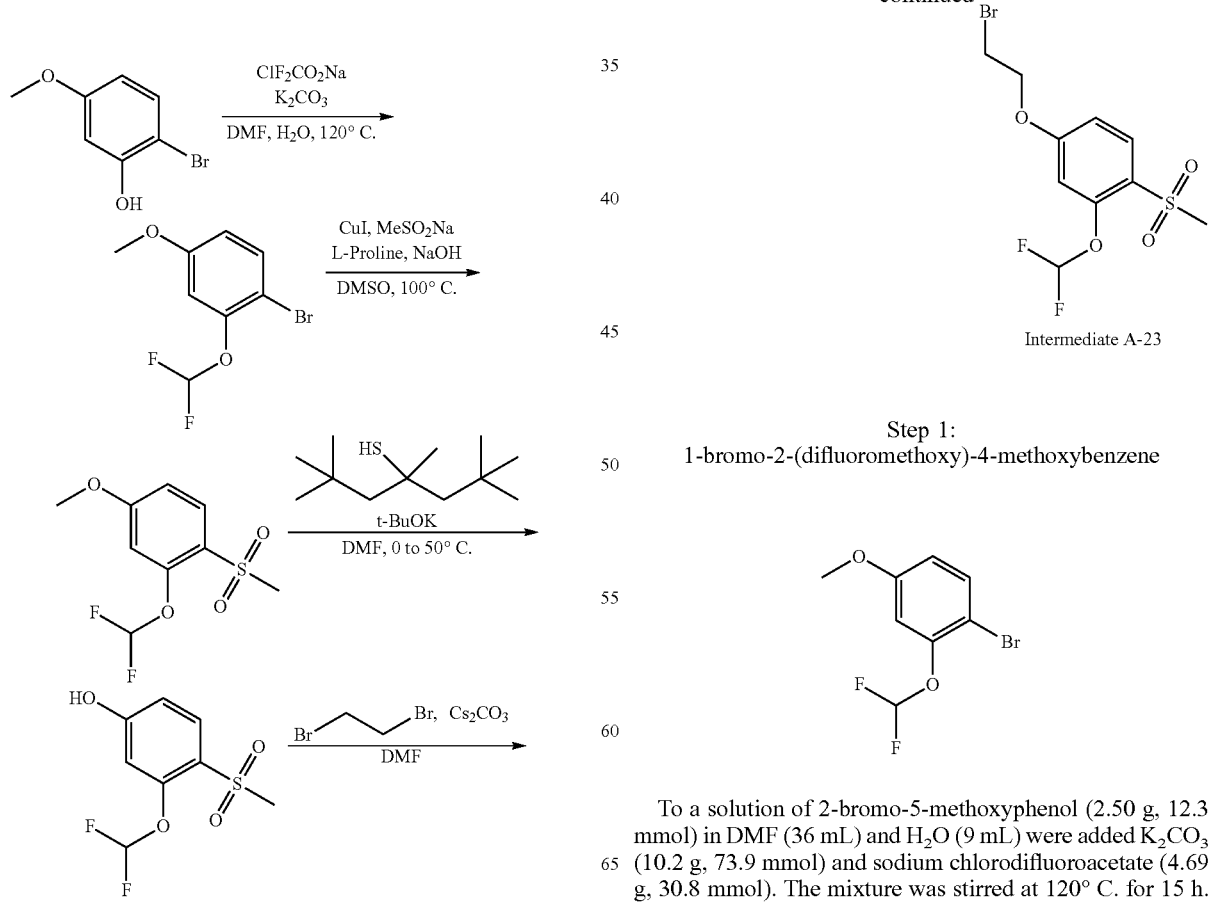

Intermediate A-23

Step 1:
1-bromo-2-(difluoromethoxy)-4-methoxybenzene

To a solution of 2-bromo-5-methoxyphenol (2.50 g, 12.3 mmol) in DMF (36 mL) and H$_2$O (9 mL) were added K$_2$CO$_3$ (10.2 g, 73.9 mmol) and sodium chlorodifluoroacetate (4.69 g, 30.8 mmol). The mixture was stirred at 120° C. for 15 h. After cooling to room temperature, the reaction mixture was Step 4: 4-(2-bromoethoxy)-2-(difluoromethoxy)-1-methanesulfonylbenzene

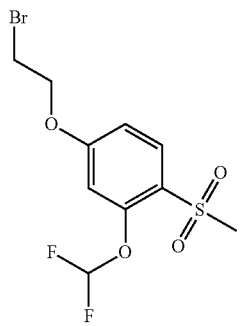

To a mixture of 3-(difluoromethoxy)-4-methanesulfonylphenol (370 mg, 1.55 mmol) and 1,2-dibromoethane (3.00 mL, 39.7 mmol) in DMF (3 mL) was added $Cs_2CO_3$ (1.01 g, 3.11 mmol). After stirring at room temperature for 12 h, the mixture was diluted with $H_2O$ (15 mL) and extracted with DCM (3×10 mL). The combined organic layers were washed with brine (5 mL), dried over $Na_2SO_4$, filtered, and concentrated in vacuo. The crude residue was purified by normal phase silica gel chromatography (Isco 4 g cartridge, 0-30% EtOAc:petroleum ether) to give 4-(2-bromoethoxy)-2-(difluoromethoxy)-1-methanesulfonylbenzene (Intermediate A-23). MS=362.1/364.0 $[M+NH_4]^+$.

General Procedure for Intermediate A-24

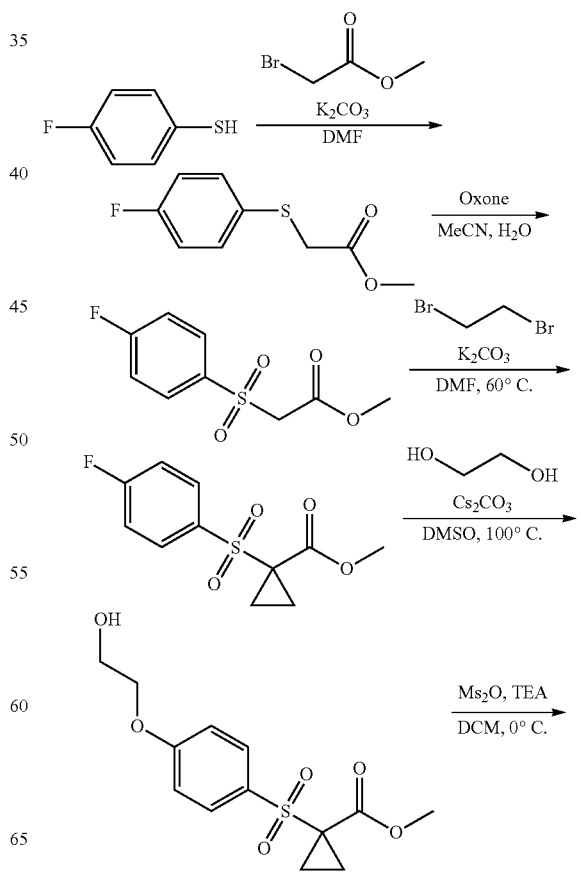

diluted with $H_2O$ (30 mL) and extracted with EtOAc (3×30 mL). The combined organic layers were washed with brine (30 mL), dried over $Na_2SO_4$, filtered, and concentrated in vacuo. The crude residue was purified by normal phase silica gel chromatography (Isco 40 g cartridge, 0-7% EtOAc:petroleum ether) to give 1-bromo-2-(difluoromethoxy)-4-methoxybenzene.

Step 2: 2-(difluoromethoxy)-1-methanesulfonyl-4-methoxybenzene

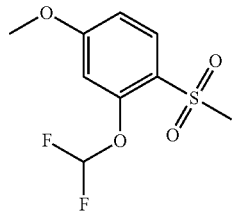

A mixture of 1-bromo-2-(difluoromethoxy)-4-methoxybenzene (3.00 g, 11.9 mmol), sodium methanesulfinate (6.05 g, 59.3 mmol), L-Proline (409 mg, 3.56 mmol), sodium hydroxide (142 mg, 3.56 mmol) and copper (I) iodide (1.13 g, 5.93 mmol) in DMSO (30 mL) was degassed and purged with $N_2$ (3×). The mixture was stirred at 100° C. for 12 h under $N_2$ atmosphere. After cooling to room temperature, the reaction mixture was quenched with $H_2O$ (80 mL) and extracted with EtOAc (2×100 mL). The combined organic layers were washed with brine (40 mL), dried over $Na_2SO_4$, filtered, and concentrated in vacuo. The crude residue was purified by normal phase silica gel chromatography (Isco 80 g cartridge, 0-23% EtOAc:petroleum ether) to give 2-(difluoromethoxy)-1-methanesulfonyl-4-methoxybenzene. MS=253.2 $[M+H]^+$.

Step 3: 3-(difluoromethoxy)-4-methanesulfonylphenol

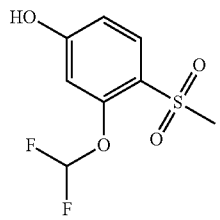

A mixture of 2,2,4,6,6-pentamethylheptane-4-thiol (2.70 g, 13.3 mmol) and t-BuOK (1.56 g, 13.9 mmol) in DMF (14 mL) was degassed and purged with $N_2$ (3×). The mixture was cooled to 0° C. and a solution of 2-(difluoromethoxy)-1-methanesulfonyl-4-methoxybenzene (1.4 g, 5.55 mmol) in DMF (14 mL) was added dropwise. The resulting mixture was stirred at 50° C. for 2 h. After cooling to room temperature, the reaction mixture was quenched with $H_2O$ (50 mL) and extracted with EtOAc (3×20 mL). The combined organic layers were washed with brine (10 mL), dried over $Na_2SO_4$, filtered, and concentrated in vacuo. The crude residue was purified by normal phase silica gel chromatography (Isco 40 g cartridge, 0-33% EtOAc:petroleum ether) to give 3-(difluoromethoxy)-4-methanesulfonylphenol. MS=239.2 $[M+H]^+$.

-continued

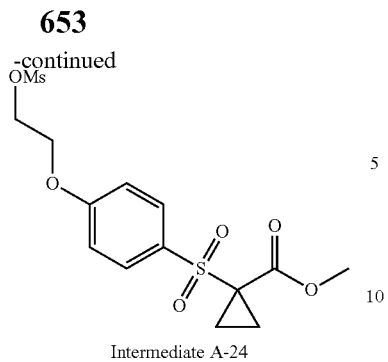

Intermediate A-24

Step 1: methyl 2-[(4-fluorophenyl)sulfanyl]acetate

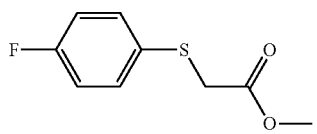

To a solution of 4-fluorobenzene-1-thiol (1.25 mL, 11.7 mmol) in DMF (15 mL) were added $K_2CO_3$ (3.23 g, 23.4 mmol) and methyl 2-bromoacetate (1.33 mL, 14.0 mmol). The mixture was stirred at room temperature for 5 h. After cooling to 0° C., the reaction mixture was quenched with $H_2O$ (15 mL) and extracted with EtOAc (2×15 mL). The combined organic layers were washed with brine (2×15 mL), dried over $Na_2SO_4$, filtered, and concentrated in vacuo. The crude residue was purified by normal phase silica gel chromatography (Biotage 25 g cartridge, 1-20% EtOAc: petroleum ether) to give methyl 2-[(4-fluorophenyl)sulfanyl]acetate. MS=201.0 $[M+H]^+$.

Step 2: methyl 2-(4-fluorobenzenesulfonyl)acetate

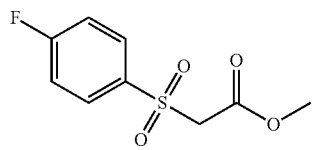

To a solution of methyl 2-[(4-fluorophenyl)sulfanyl]acetate (2.20 g, 11.0 mmol) in MeCN (30 mL) and $H_2O$ (3 mL) was added Oxone (8.11 g, 13.2 mmol). After stirring at room temperature for 16 h, the mixture cooled to 0° C. and quenched with saturated aqueous $Na_2S_2O_3$ (40 mL) and extracted with EtOAc (2×20 mL). The combined organic layers were washed with brine (2×20 mL), dried over $Na_2SO_4$, filtered, and concentrated in vacuo. The crude residue was purified by normal phase silica gel chromatography (Biotage 25 g cartridge, 15-45% EtOAc:petroleum ether) to give methyl 2-(4-fluorobenzenesulfonyl)acetate. MS=233.0 $[M+H]^+$.

Step 3: methyl 1-(4-fluorobenzenesulfonyl)cyclopropane-1-carboxylate

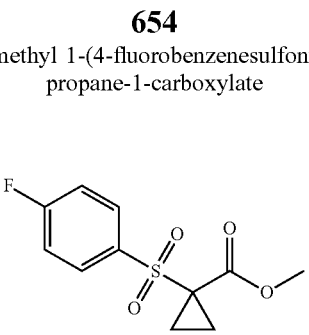

To a solution of methyl 2-(4-fluorobenzenesulfonyl)acetate (1.10 g, 4.74 mmol) in DMF (10 mL) were added $K_2CO_3$ (1.64 g, 11.8 mmol) and 1,2-dibromoethane (429 μL, 5.68 mmol). The mixture was stirred at 60° C. for 6 h. The reaction mixture was cooled to 0° C., quenched with $H_2O$ (20 mL), and extracted with EtOAc (2×15 mL). The combined organic layers were washed with brine (2×15 mL), dried over $Na_2SO_4$, filtered, and concentrated in vacuo. The crude residue was purified by normal phase silica gel chromatography (Biotage 12 g cartridge, 15-45% EtOAc: petroleum ether) to give methyl 1-(4-fluorobenzenesulfonyl) cyclopropane-1-carboxylate. MS=259.0 $[M+H]^+$.

Step 4: methyl 1-[4-(2-hydroxyethoxy)benzenesulfonyl]cyclopropane-1-carboxylate

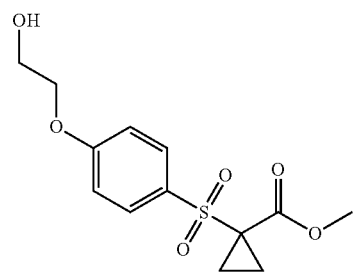 [SMILES: COC(=O)C1(S(=O)(=O)c2ccc(OCCO)cc2)CC1]

To a solution of methyl 1-(4-fluorobenzenesulfonyl)cyclopropane-1-carboxylate (1.50 g, 5.81 mmol) in DMSO (15 mL) were added $Cs_2CO_3$ (5.68 g, 17.4 mmol) and ethylene glycol (6.50 mL, 116 mmol). The mixture was stirred at 100° C. for 5 h. The hydrolysis product of the ester was detected. After cooling to room temperature, MeI (1.08 mL, 17.4 mmol) was added to the mixture. The reaction mixture was stirred at room temperature for 1 h and was then quenched with $H_2O$ (30 mL) and extracted with EtOAc (2×15 mL). The combined organic layers were washed with brine (2×15 mL), dried over $Na_2SO_4$, filtered, and concentrated in vacuo. The crude residue was purified by normal phase silica gel chromatography (Biotage 12 g cartridge, 45-80% EtOAc: petroleum ether) to give methyl 1-[4-(2-hydroxyethoxy) benzenesulfonyl]cyclopropane-1-carboxylate. MS=301.1 $[M+H]^+$.

Step 5: methyl 1-{4-[2-(methanesulfonyloxy) ethoxy]benzenesulfonyl}cyclopropane-1-carboxylate

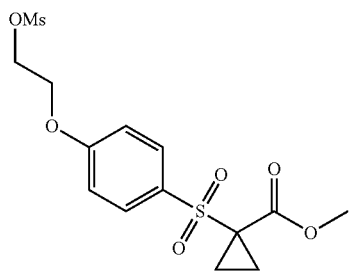 [SMILES: COC(=O)C1(S(=O)(=O)c2ccc(OCCOS(C)(=O)=O)cc2)CC1]

To a 0° C. solution of methyl 1-[4-(2-hydroxyethoxy)benzenesulfonyl]cyclopropane-1-carboxylate (570 mg, 1.90 mmol) in DCM (10 mL) were added TEA (528 µL, 3.80 mmol) and methylsulfonyl methanesulfonate (397 mg, 2.28 mmol). The mixture was stirred at 0° C. for 3 h, and then quenched with H$_2$O (10 mL). 4 M aqueous HCl (0.1 mL) was added, and the mixture was extracted with EtOAc (8 mL×2). The combined organic layers were washed with brine (2×8 mL), dried over Na$_2$SO$_4$, filtered, and concentrated in vacuo to give methyl 1-{4-[2-(methanesulfonyloxy)ethoxy]benzenesulfonyl}cyclopropane-1-carboxylate (Intermediate A-24), which was used in the subsequent step without further purification. MS=378.9 [M+H]$^+$.

General Procedure for Intermediates A-25 & A-85

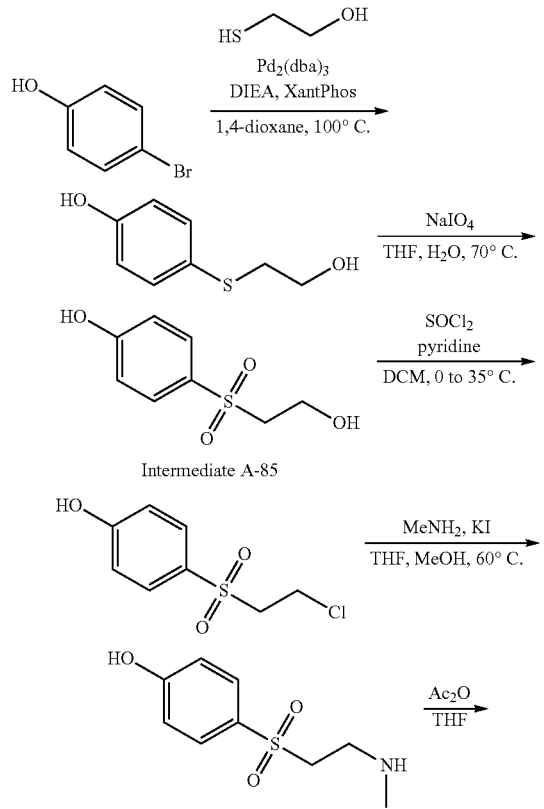

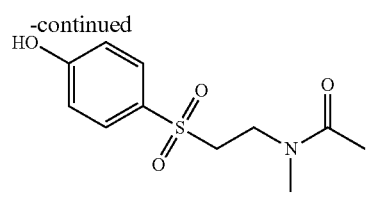

Intermediate A-25

Step 1: 4-[(2-hydroxyethyl)sulfanyl]phenol

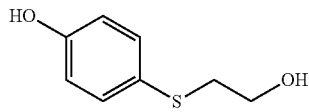 [SMILES: OCCSc1ccc(O)cc1]

A solution of 4-bromophenol (10.0 g, 57.8 mmol), 2-sulfanylethanol (5.24 mL, 75.1 mmol), XantPhos (6.69 g, 11.6 mmol), Pd$_2$(dba)$_3$ (5.29 g, 5.78 mmol) and DIEA (25.2 mL, 145 mmol) in 1,4-dioxane (10 mL) was degassed and purged with N$_2$ (3×). The mixture was stirred at 100° C. for 12 h under N$_2$ atmosphere. After cooling to room temperature, the reaction mixture was quenched with H$_2$O (20 mL) and extracted with EtOAc (2×50 mL). The combined organic layers were washed with brine (20 mL), dried over Na$_2$SO$_4$, filtered, and concentrated in vacuo. The crude residue was purified by normal phase silica gel chromatography (Biotage 20 g cartridge, 0-50% EtOAc:petroleum ether) to give 4-[(2-hydroxyethyl)sulfanyl]phenol.

Step 2: 4-(2-hydroxyethanesulfonyl)phenol

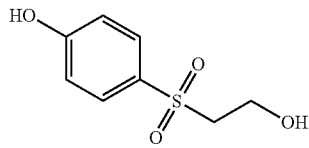 [SMILES: O=S(=O)(CCO)c1ccc(O)cc1]

A solution of 4-[(2-hydroxyethyl)sulfanyl]phenol (4.80 g, 28.2 mmol), NaIO$_4$ (4.69 mL, 84.6 mmol) in THF (50 mL) and H$_2$O (50 mL) was degassed and purged with N$_2$ (3×). The mixture was stirred at 70° C. for 12 h under N$_2$ atmosphere. After cooling to room temperature, the reaction mixture was quenched with saturated aqueous Na$_2$S2O3 (100 mL) and extracted with EtOAc (2×70 mL). The combined organic layers were washed with brine (70 mL), dried over Na$_2$SO$_4$, filtered, and concentrated in vacuo to give 4-(2-hydroxyethanesulfonyl)phenol (Intermediate A-85), which was used in the subsequent step without further purification. MS=203.0 [M+H]$^+$.

Step 3: 4-(2-chloroethanesulfonyl)phenol

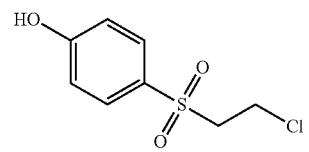 [SMILES: O=S(=O)(CCCl)c1ccc(O)cc1]

To a 0° C. mixture of 4-(2-hydroxyethanesulfonyl)phenol (600 mg, 2.97 mmol) and pyridine (478 µL, 5.93 mmol) in DCM (6 mL) was added SOCl₂ (645 µL, 8.90 mmol). The mixture was stirred at 35° C. for 16 h. After cooling to room temperature, the reaction mixture was quenched with H₂O (20 mL) and extracted with DCM (3×10 mL). The combined organic layers were washed with brine (30 mL), dried over Na₂SO₄, filtered, and concentrated in vacuo. The crude residue was purified by normal phase silica gel chromatography (Biotage 12 g cartridge, 0-100% EtOAc:petroleum ether) to give 4-(2-chloroethanesulfonyl)phenol.

Step 4: 4-[2-(methylamino)ethanesulfonyl]phenol

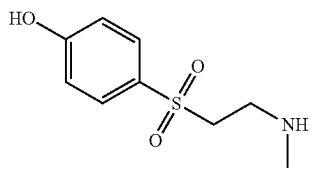

A mixture of 4-(2-chloroethanesulfonyl)phenol (250 mg, 1.13 mmol), 2.0 M methylamine in MeOH (7.93 mL, 15.9 mmol), and KI (75 mg, 0.45 mmol) in THF (2 mL) was stirred at 60° C. for 16 h under N₂ atmosphere. After cooling to room temperature, the mixture was filtered, and the filtrate was concentrated in vacuo to give 4-[2-(methylamino)ethanesulfonyl]phenol, which was used in the subsequent step without further purification. MS=216.1 [M+H]⁺.

Step 5: N-[2-(4-hydroxybenzenesulfonyl)ethyl]-N-methylacetamide

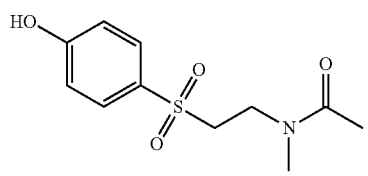 [SMILES: CC(=O)N(C)CCS(=O)(=O)c1ccc(O)cc1]

A mixture of 4-[2-(methylamino)ethanesulfonyl]phenol (340 mg, 1.58 mmol) and Ac2O (147 µL, 1.58 mmol) in THF (5 mL) was stirred for 16 h. The mixture was filtered and the filtered cake was concentrated under in vacuo to give N-[2-(4-hydroxybenzenesulfonyl)ethyl]-N-methylacetamide (Intermediate A-25), which was used in the subsequent step without further purification. MS=258.2 [M+H]⁺.

General Procedure for Intermediate A-26

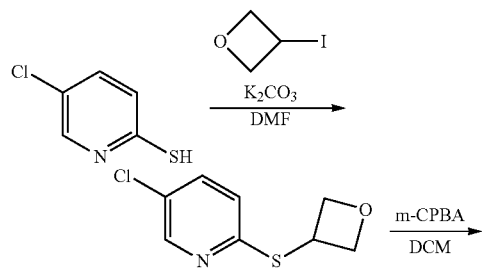

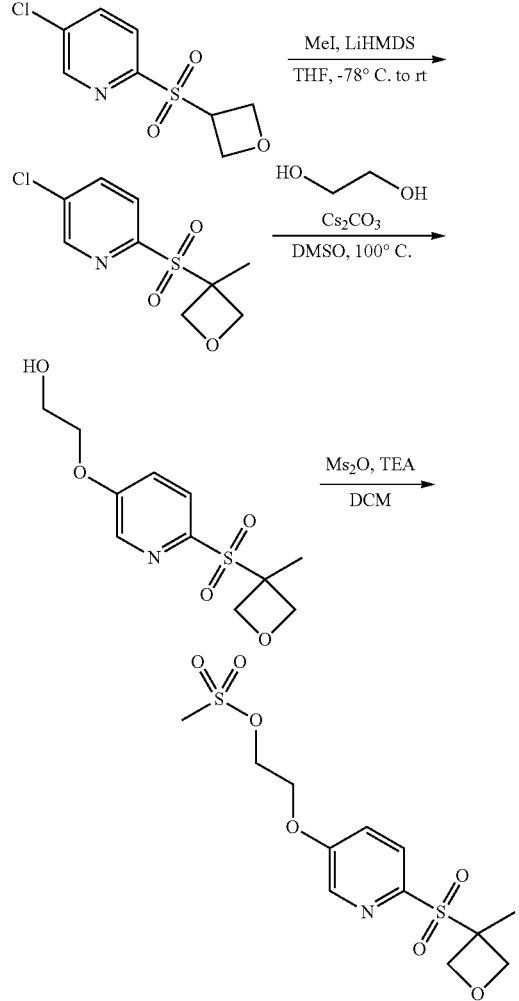

Intermediate A-26

Step 1: 5-chloro-2-(oxetan-3-ylsulfanyl)pyridine

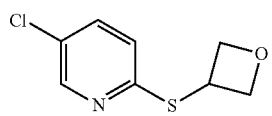

To a solution of 5-chloropyridine-2-thiol (4.50 g, 30.9 mmol) in DMF (50 mL) were added K₂CO₃ (8.54 g, 61.8 mmol) and 3-iodooxetane (6.82 g, 37.1 mmol). The mixture was stirred at room temperature for 2 h. The reaction mixture was quenched with H₂O (100 mL) and extracted with EtOAc (3×50 mL). The combined organic layers were washed with brine (3×50 mL), dried over Na₂SO₄, filtered, and concentrated in vacuo. The crude residue was purified by normal phase silica gel chromatography (Biotage 80 g cartridge, 0-15% EtOAc:petroleum ether) to give 5-chloro-2-(oxetan-3-ylsulfanyl)pyridine. MS=202.0 [M+H]⁺.

Step 2: 5-chloro-2-(oxetane-3-sulfonyl)pyridine

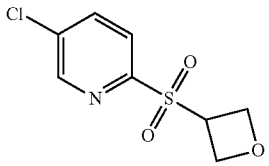 [SMILES: O=S(=O)(c1ccc(Cl)cn1)C1COC1]

To a 0° C. solution of 5-chloro-2-(oxetan-3-ylsulfanyl)pyridine (3.00 g, 14.9 mmol) in DCM (40 mL) was added m-CPBA (6.04 g, 85% purity, 29.8 mmol). The mixture was allowed to warm to room temperature and stirred for 2 h. The reaction mixture was quenched with saturated aqueous $Na_2SO_3$ (20 mL), diluted with $H_2O$ (100 mL), and extracted with DCM (3×50 mL). The combined organic layers were washed with saturated aqueous $Na_2SO_3$ (2×50 mL), dried over $Na_2SO_4$, filtered, and concentrated in vacuo. The crude product was triturated with EtOAc (5 mL) and isolated by filtration to give 5-chloro-2-(oxetane-3-sulfonyl)pyridine. MS=234.0 $[M+H]^+$.

Step 3: 5-chloro-2-[(3-methyloxetan-3-yl)sulfonyl]pyridine

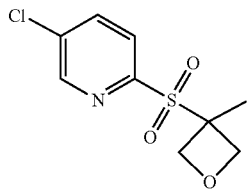

To a −78° C. solution of 5-chloro-2-(oxetane-3-sulfonyl)pyridine (500 mg, 2.14 mmol) in THF (8 mL) was added 1.0 M LiHMDS in THF (4.28 mL, 4.28 mmol). After stirring for 30 min, MeI (160 μL, 2.57 mmol) was added. The mixture was allowed to warm to room temperature and stirred for 30 min. The reaction mixture was quenched with saturated aqueous $NH_4Cl$ (20 mL) and extracted with EtOAc (3×10 mL). The combined organic layers were washed with brine (2×10 mL), dried over $Na_2SO_4$, filtered, and concentrated in vacuo. The crude residue was purified by normal phase silica gel chromatography (Biotage 12 g cartridge, 0-15% EtOAc:petroleum ether) to give 5-chloro-2-[(3-methyloxetan-3-yl)sulfonyl]pyridine. MS=248.0 $[M+H]^+$.

Step 4: 2-({6-[(3-methyloxetan-3-yl)sulfonyl]pyridin-3-yl}oxy)ethan-1-ol

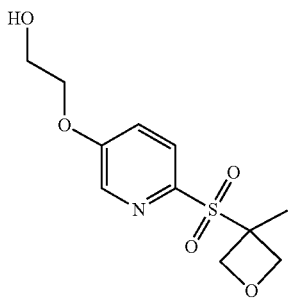 [SMILES: CC1(S(=O)(=O)c2ccc(OCCO)cn2)COC1]

To a solution of 5-chloro-2-[(3-methyloxetan-3-yl)sulfonyl]pyridine (350 mg, 1.41 mmol) in DMSO (2 mL) were added ethylene glycol (2.00 mL, 35.8 mmol) and $Cs_2CO_3$ (921 mg, 2.83 mmol). The mixture was stirred at 100° C. for 7 h. After cooling to 0° C., the reaction mixture was quenched with $H_2O$ (20 mL) and extracted with EtOAc (6×10 mL). The combined organic layers were washed with brine (2×15 mL), dried over $Na_2SO_4$, filtered, and concentrated in vacuo. The crude residue was purified by normal phase silica gel chromatography (Biotage 4 g cartridge, 0-70% EtOAc:petroleum ether) to give 2-({6-[(3-methyloxetan-3-yl)sulfonyl]pyridin-3-yl}oxy)ethan-1-ol. MS=274.1 $[M+H]^+$.

Step 5: 2-({6-[(3-methyloxetan-3-yl)sulfonyl]pyridin-3-yl}oxy)ethyl methanesulfonate

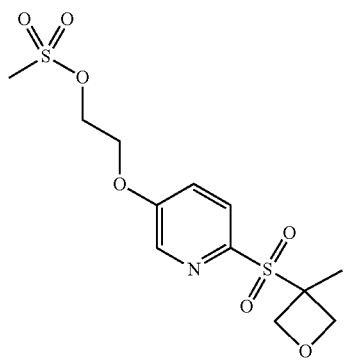

To a solution of 2-({6-[(3-methyloxetan-3-yl)sulfonyl]pyridin-3-yl}oxy)ethan-1-ol (130 mg, 0.476 mmol) in DCM (3 mL) was added TEA (199 μL, 1.43 mmol) and methanesulfonic anhydride (166 mg, 0.951 mmol). The mixture was stirred at room temperature for 5 h, and then diluted with $H_2O$ (10 mL) and extracted with DCM (3×5 mL). The combined organic layers were dried over $Na_2SO_4$, filtered and concentrated in vacuo to give 2-({6-[(3-methyloxetan-3-yl)sulfonyl]pyridin-3-yl}oxy)ethyl methanesulfonate (Intermediate A-26), which was used in the subsequent step without further purification. MS=352.1 $[M+H]^+$.

The following intermediate in Table 5 was prepared using procedures similar to those described for Intermediate A-26, using the appropriate starting materials.

General Procedure for Intermediate A-27

TABLE 5

| Intermediate # | Structure | Name | Exact Mass [M + H]+ |
|---|---|---|---|
| A-27 | 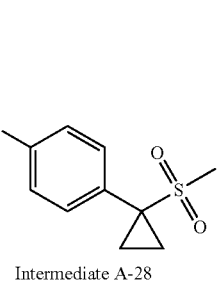 | 2-{4-[(3-methyloxetan-3-yl)sulfonyl]phenoxy}ethyl methanesulfonatele | Calc'd 351.1 Found 350.9 |

General Procedure for Intermediate A-28

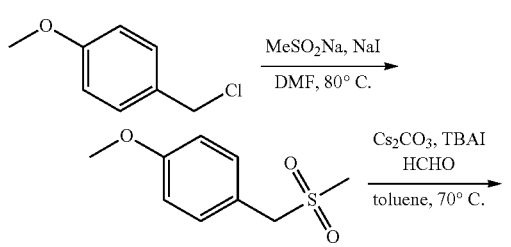

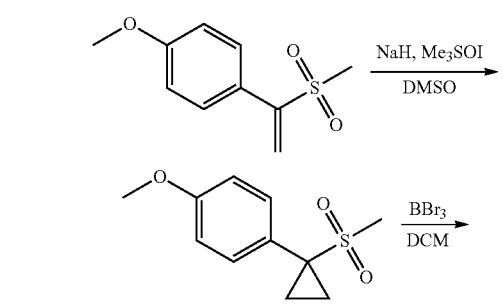

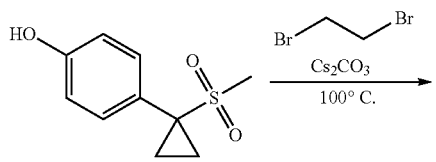

Intermediate A-28

Step 1:
1-(methanesulfonylmethyl)-4-methoxybenzene

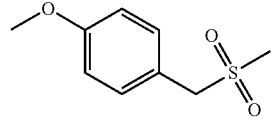

A mixture of 1-(chloromethyl)-4-methoxybenzene (8.70 mL, 63.9 mmol), sodium methanesulfinate (9.13 g, 89.4 mmol) and NaI (28.7 mg, 0.192 mmol) in DMF (80 mL) was stirred at 80° C. for 3 h. After cooling to 0° C., the reaction mixture was quenched with H₂O (200 mL) and extracted with EtOAc (3×100 mL). The combined organic layers were washed with brine (2×100 mL), dried over Na₂SO₄, filtered, and concentrated in vacuo. The crude residue was triturated with EtOAc (50 mL) to give 1-(methanesulfonylmethyl)-4-methoxybenzene, which was used in the subsequent step without further purification.

Step 2:
1-(1-methanesulfonylethenyl)-4-methoxybenzene

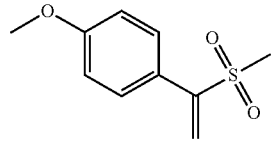

A mixture of 1-(methanesulfonylmethyl)-4-methoxybenzene (9.00 g, 44.9 mmol), Cs₂CO₃ (43.9 g, 135 mmol), TBAI (166 mg, 0.449 mmol) and HCHO (12.4 mL, 449 mmol) in toluene (150 mL) was stirred at 70° C. for 3 h. After cooling to 0° C., the reaction mixture was quenched with H₂O (200 mL) and extracted with EtOAc (2×100 mL). The combined organic layers were dried over Na₂SO₄, filtered, and concentrated in vacuo. The crude residue was purified by normal phase silica gel chromatography (Biotage 120 g cartridge, 0-30% EtOAc:petroleum ether) to give 1-(1-methanesulfonylethenyl)-4-methoxybenzene.
MS=213.1 [M+H]+.

Step 3:
1-(1-methanesulfonylcyclopropyl)-4-methoxybenzene

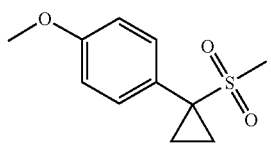

To a solution of trimethylsulfoxonium iodide (523 mg, 2.37 mmol) in DMSO (5 mL) was added NaH (84.4 mg, 60 wt % in mineral oil, 2.11 mmol). After stirring at room temperature for 1 h, 1-(1-methanesulfonylethenyl)-4-methoxybenzene (0.28 g, 1.32 mmol) was added. The mixture was stirred for 16 h, then cooled to 0° C., quenched with saturated aqueous NH$_4$Cl (10 mL), and extracted with EtOAc (3×5 mL). The combined organic layers were washed with brine (2×10 mL), dried over Na$_2$SO$_4$, filtered, and concentrated in vacuo. The crude residue was purified by normal phase silica gel chromatography (Biotage 4 g cartridge, 0-50% EtOAc:petroleum ether) to give 1-(1-methanesulfonylcyclopropyl)-4-methoxybenzene. MS=244.2 [M+NH$_4$]$^+$.

Step 4: 4-(1-methanesulfonylcyclopropyl)phenol

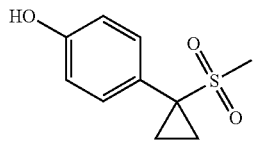

To a 0° C. solution of 1-(1-methanesulfonylcyclopropyl)-4-methoxybenzene (1.20 g, 5.30 mmol) in DCM (20 mL) was added BBr$_3$ (1.53 mL, 15.9 mmol). The mixture was allowed to warm to room temperature and stirred for 3 h. After cooling to 0° C., the reaction mixture was quenched with H$_2$O (30 mL). The pH of the 0° C. solution was adjusted to pH=7 with the dropwise addition of saturated aqueous NaHCO$_3$. The biphasic mixture was extracted with DCM (3×20 mL). The combined organic layers were dried over Na$_2$SO$_4$, filtered and concentrated in vacuo to give 4-(1-methanesulfonylcyclopropyl)phenol, which was used in the subsequent step without further purification.

Step 5: 1-(2-bromoethoxy)-4-(1-methanesulfonylcyclopropyl)benzene

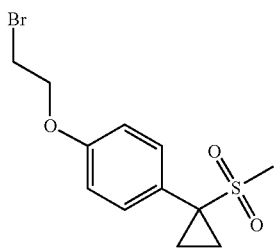 [SMILES: CS(=O)(=O)C1(c2ccc(OCCBr)cc2)CC1]

To a solution of 4-(1-methanesulfonylcyclopropyl)phenol (200 mg, 0.942 mmol) in 1,2-dibromoethane (4.27 mL, 56.5 mmol) was added Cs$_2$CO$_3$ (614 mg, 1.88 mmol). The mixture was stirred at 100° C. for 4 h. After cooling to room temperature, the reaction mixture was quenched with H$_2$O (10 mL) and extracted with DCM (3×5 mL). The combined organic layers were dried over Na$_2$SO$_4$, filtered, and concentrated in vacuo. The crude residue was purified by normal phase silica gel chromatography (Biotage 4 g cartridge, 0-30% EtOAc:petroleum ether) to give 1-(2-bromoethoxy)-4-(1-methanesulfonylcyclopropyl)benzene (Intermediate A-28). MS=336.0/338.1 [M+NH$_4$]$^+$.

General Procedure for Intermediates A-29 & A-30

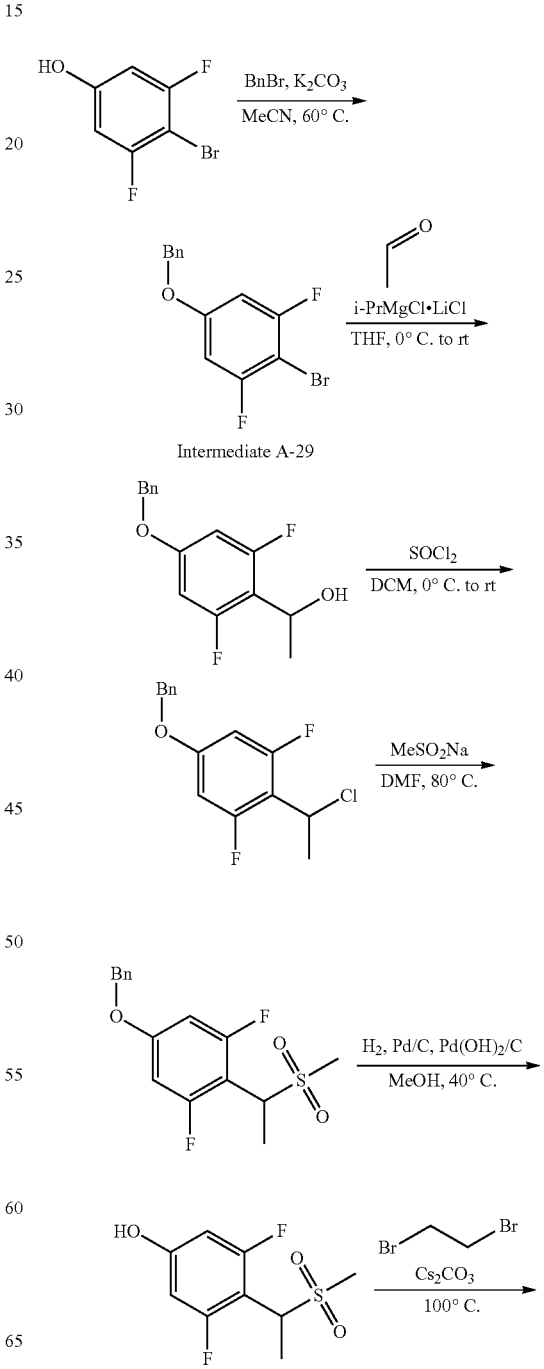

Intermediate A-29

-continued

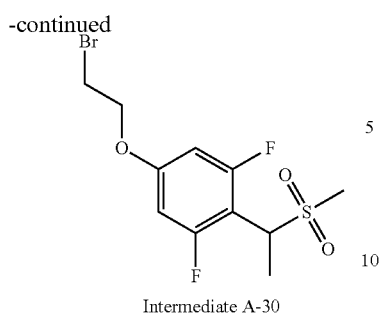

Intermediate A-30

Step 1: 5-(benzyloxy)-2-bromo-1,3-difluorobenzene

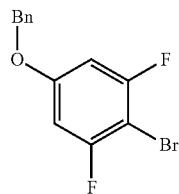 [SMILES: Fc1cc(OCc2ccccc2)cc(F)c1Br]

To a solution of 4-bromo-3,5-difluorophenol (10.0 g, 47.8 mmol) in MeCN (100 mL) were added BnBr (6.82 mL, 57.4 mmol) and K$_2$CO$_3$ (19.8 g, 144 mmol). The mixture was stirred at 60° C. for 12 h. After cooling to room temperature, the mixture was poured into saturated aqueous NaHCO$_3$ (400 mL) and extracted with EtOAc (3×200 mL). The combined organic layers were washed with brine (2×200 mL), dried over Na$_2$SO$_4$, filtered, and concentrated in vacuo. The crude residue was purified by normal phase silica gel chromatography (Biotage 80 g cartridge, 0-1% EtOAc:petroleum ether) to give 5-(benzyloxy)-2-bromo-1,3-difluorobenzene (Intermediate A-29). $^1$H NMR (400 MHz, CDCl$_3$): δ 7.42-7.35 (m, 5H), 6.64-6.60 (m, 2H), 5.04 (s, 2H).

Step 2: 1-[4-(benzyloxy)-2,6-difluorophenyl]ethan-1-ol

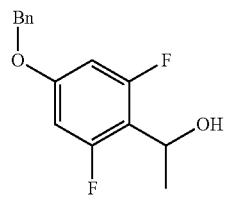 [SMILES: CC(O)c1c(F)cc(OCc2ccccc2)cc1F]

To a 0° C. solution of 5-(benzyloxy)-2-bromo-1,3-difluorobenzene (12.0 g, 40.1 mmol) in THF (24 mL) was added 1.3 M i-PrMgCl·LiCl in THF (34.0 mL, 44.1 mmol). The mixture was allowed to warm to room temperature and stirred for 1 h. The mixture was cooled to 0° C. and 5.0 M acetaldehyde in THF (8.82 mL, 44.1 mmol) was added into the reaction mixture. After stirring at 0° C. for 30 min, the mixture was warmed to room temperature and stirred for another 30 min. The reaction mixture was quenched with saturated aqueous NH$_4$Cl (300 mL) and extracted with EtOAc (3×300 mL). The combined organic layers were washed with brine (2×300 mL), dried over Na$_2$SO$_4$, filtered, and concentrated in vacuo. The crude residue was purified by normal phase silica gel chromatography (Biotage 80 g cartridge, 0-35% EtOAc:petroleum ether) to give 1-[4-(benzyloxy)-2,6-difluorophenyl]ethan-1-ol. MS=247.2 [M−OH]$^+$.

Step 3: 5-(benzyloxy)-2-(1-chloroethyl)-1,3-difluorobenzene

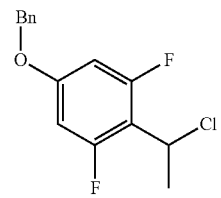 [SMILES: CC(Cl)c1c(F)cc(OCc2ccccc2)cc1F]

To a 0° C. solution of 1-[4-(benzyloxy)-2,6-difluorophenyl]ethan-1-ol (5.8 g, 21.9 mmol) in DCM (60 mL) was added SOCl$_2$ (3.18 mL, 43.9 mmol). The mixture was stirred at room temperature for 4 h, and then concentrated in vacuo to give 5-(benzyloxy)-2-(1-chloroethyl)-1,3-difluorobenzene, which was used in the subsequent step without further purification.

Step 4: 5-(benzyloxy)-1,3-difluoro-2-(1-methanesulfonylethyl)benzene

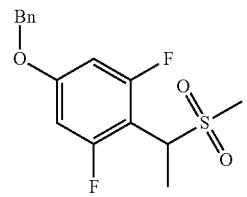 [SMILES: CC(c1c(F)cc(OCc2ccccc2)cc1F)S(C)(=O)=O]

To a solution of 5-(benzyloxy)-2-(1-chloroethyl)-1,3-difluorobenzene (6.20 g, 21.9 mmol) in DMF (60 mL) was added sodium methanesulfinate (4.48 g, 43.9 mmol). The mixture was stirred at 80° C. for 12 h. After cooling to room temperature, the reaction mixture was quenched with H$_2$O (100 mL) and extracted with EtOAc (3×100 mL). The combined organic layers were dried over Na$_2$SO$_4$, filtered, and concentrated in vacuo. The crude residue was purified by normal phase silica gel chromatography (Biotage 80 g cartridge, 0-50% EtOAc:petroleum ether) to give 5-(benzyloxy)-1,3-difluoro-2-(1-methanesulfonylethyl)benzene.

Step 5: 3,5-difluoro-4-(1-methanesulfonylethyl)phenol

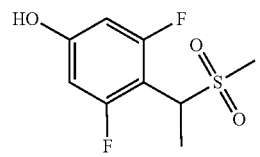

To a solution of 5-(benzyloxy)-1,3-difluoro-2-(1-methanesulfonylethyl)benzene (3.00 g, 9.19 mmol) in MeOH (30 mL) was added Pd/C (0.50 g, 10 wt %, 0.47 mmol) and Pd(OH)$_2$/C (0.50 g, 20 wt %, 0.70 mmol). The mixture was stirred at 40° C. for 16 h under an atmosphere of H$_2$ (50 psi). After cooling to room temperature, the reaction mixture was filtered through Celite and the filtrate was concentrated in vacuo. The crude residue was purified by normal phase silica gel chromatography (Biotage 80 g cartridge, 0-100% EtOAc:petroleum ether) to give 3,5-difluoro-4-(1-methanesulfonylethyl)phenol. MS=254.1 [M+NH$_4$]$^+$.

Step 6: 5-(2-bromoethoxy)-1,3-difluoro-2-(1-methanesulfonylethyl)benzene

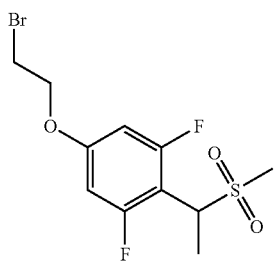 [SMILES: CC(c1c(F)cc(OCCBr)cc1F)S(C)(=O)=O]

To a solution of 3,5-difluoro-4-(1-methanesulfonylethyl)phenol (0.43 g, 1.82 mmol) in 1,2-dibromoethane (10 mL, 132 mmol) was added Cs$_2$CO$_3$ (1.19 g, 3.64 mmol). The mixture was stirred at 100° C. for 12 h. After cooling to room temperature, the reaction mixture was filtered through Celite and the filtrate was concentrated in vacuo. The crude residue was purified by normal phase silica gel chromatography (Biotage 20 g cartridge, 0-50% EtOAc:petroleum ether) to give 5-(2-bromoethoxy)-1,3-difluoro-2-(1-methanesulfonylethyl)benzene (Intermediate A-30). MS=360.1/362.1 [M+NH$_4$]$^+$.

The following intermediate in Table 6 was prepared using procedures similar to those described for Intermediate A-30, using the appropriate starting materials.

General Procedure for Intermediate A-31

General Procedure for Intermediate A-32

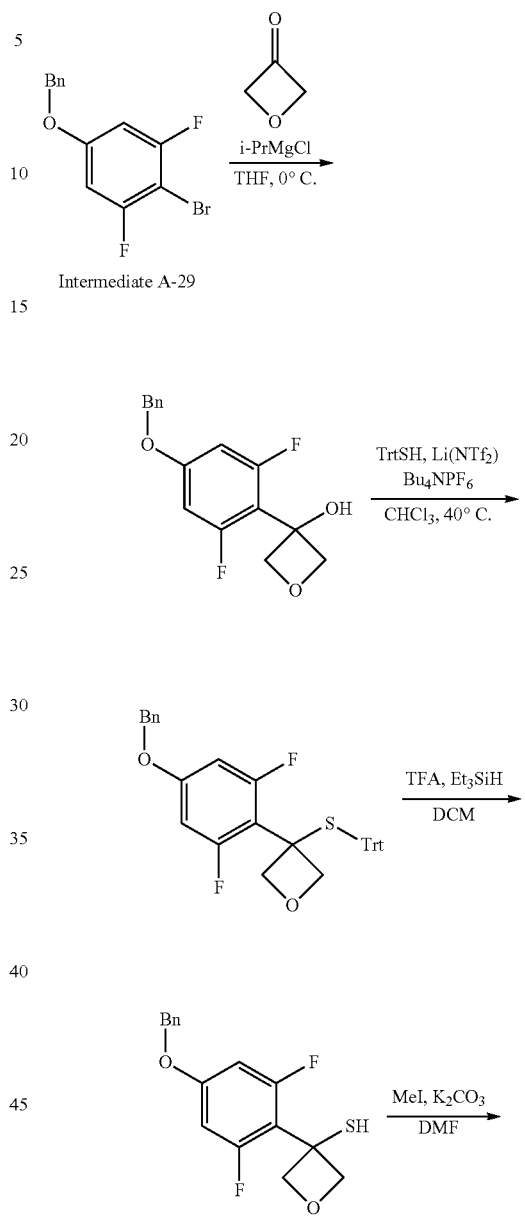

TABLE 6

| Intermediate # | Structure | Name | Exact Mass [M + H]$^+$ |
|---|---|---|---|
| A-31 | (structure shown) | 1-(2-bromoethoxy)-4-(1-methanesulfonylethyl)benzene | Calc'd 227.0/229.0 Found 227.1/229.1 [M − CH$_3$O$_2$S]$^+$ |

-continued

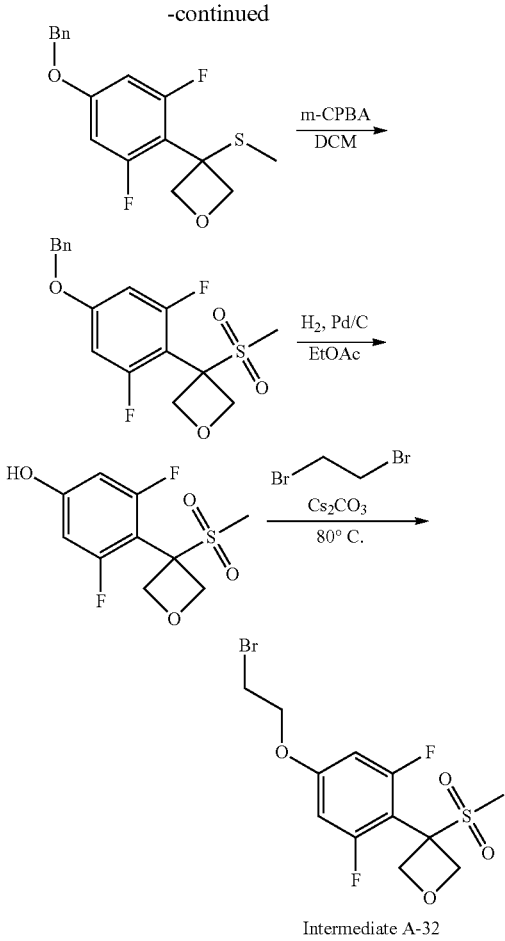

Intermediate A-32

Step 1: 3-[4-(benzyloxy)-2,6-difluorophenyl]oxetan-3-ol

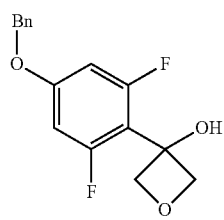 [SMILES: OC1(c2c(F)cc(OCc3ccccc3)cc2F)COC1]

To a 0° C. solution of 5-(benzyloxy)-2-bromo-1,3-difluorobenzene (Intermediate A-29, 14.0 g, 46.8 mmol) in THF (150 mL) was added 2.0 M i-PrMgCl in THF (25.7 mL, 51.4 mmol). After stirring at 0° C. for 30 min, oxetan-3-one (4.05 g, 56.2 mmol) was added. The mixture was stirred at 0° C. for another 30 min, and then quenched with H₂O (200 mL) and extracted with EtOAc (3×100 mL). The combined organic layers were dried over Na₂SO₄, filtered, and concentrated in vacuo. The crude residue was purified by normal phase silica gel chromatography (Biotage 80 g cartridge, 1:10 EtOAc:petroleum ether) to give 3-[4-(benzyloxy)-2,6-difluorophenyl]oxetan-3-ol. MS=315.2 [M+Na]f.

Step 2: 3-[4-(benzyloxy)-2,6-difluorophenyl]-3-[(triphenylmethyl)sulfanyl]oxetane

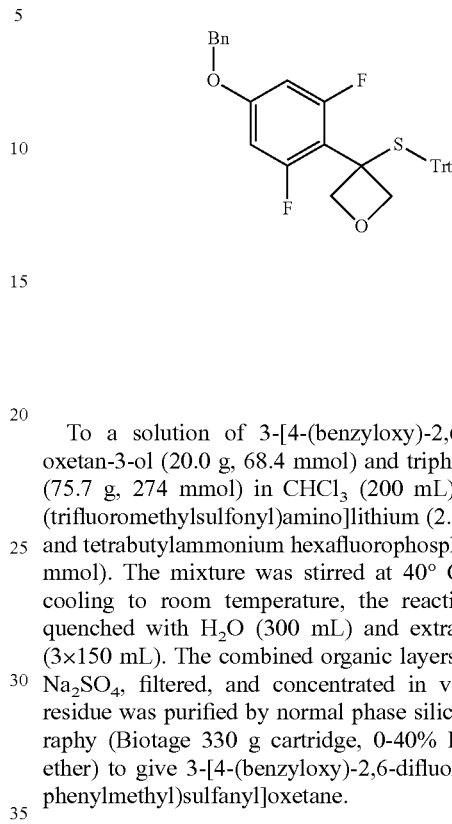

To a solution of 3-[4-(benzyloxy)-2,6-difluorophenyl]oxetan-3-ol (20.0 g, 68.4 mmol) and triphenylmethanethiol (75.7 g, 274 mmol) in CHCl₃ (200 mL) was added [bis(trifluoromethylsulfonyl)amino]lithium (2.16 g, 7.53 mmol) and tetrabutylammonium hexafluorophosphate (1.46 g, 3.76 mmol). The mixture was stirred at 40° C. for 2 h. After cooling to room temperature, the reaction mixture was quenched with H₂O (300 mL) and extracted with DCM (3×150 mL). The combined organic layers were dried over Na₂SO₄, filtered, and concentrated in vacuo. The crude residue was purified by normal phase silica gel chromatography (Biotage 330 g cartridge, 0-40% EtOAc:petroleum ether) to give 3-[4-(benzyloxy)-2,6-difluorophenyl]-3-[(triphenylmethyl)sulfanyl]oxetane.

Step 3: 3-[4-(benzyloxy)-2,6-difluorophenyl]oxetane-3-thiol

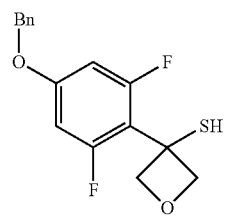

To a solution of 3-[4-(benzyloxy)-2,6-difluorophenyl]-3-[(triphenylmethyl)sulfanyl]oxetane (400 mg, 0.726 mmol) in DCM (2 mL) was added TFA (4 mL) and Et₃SiH (290 μL, 1.82 mmol). The mixture was stirred at room temperature for 2 h. The reaction mixture was quenched with H₂O (10 mL) and extracted with DCM (3×5 mL). The combined organic layers were dried over Na₂SO₄, filtered, and concentrated in vacuo. The crude residue was purified by normal phase silica gel chromatography (Biotage 12 g cartridge, 0-10% EtOAc:petroleum ether) to give 3-[4-(benzyloxy)-2,6-difluorophenyl]oxetane-3-thiol. MS=307.1 [M−H]⁻.

Step 4: 3-[4-(benzyloxy)-2,6-difluorophenyl]-3-(methylsulfonyl)oxetane

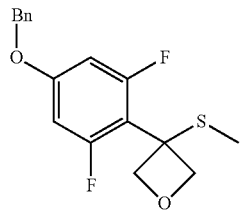 [SMILES: CSC1(c2c(F)cc(OCc3ccccc3)cc2F)COC1]

To a solution of 3-[4-(benzyloxy)-2,6-difluorophenyl]oxetane-3-thiol (2.50 g, 8.11 mmol) in DMF (25 mL) was added K$_2$CO$_3$ (1.68 g, 12.2 mmol) and MeI (2.52 mL, 40.5 mmol). The mixture was stirred at room temperature for 1 h. After cooling to 0° C., the reaction mixture was quenched with H$_2$O (50 mL) and extracted with DCM (3×30 mL). The combined organic layers were washed with brine (3×30 mL) dried over Na$_2$SO$_4$, filtered, and concentrated in vacuo. The crude residue was purified by normal phase silica gel chromatography (Biotage 80 g cartridge, 0-15% EtOAc:petroleum ether) to give 3-[4-(benzyloxy)-2,6-difluorophenyl]-3-(methylsulfonyl)oxetane. MS=321.0 [M−H]$^−$.

Step 5: 3-[4-(benzyloxy)-2,6-difluorophenyl]-3-methanesulfonyloxetane

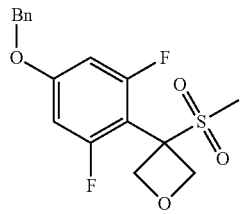 [SMILES: CS(=O)(=O)C1(c2c(F)cc(OCc3ccccc3)cc2F)COC1]

To a solution of 3-[4-(benzyloxy)-2,6-difluorophenyl]-3-(methylsulfonyl)oxetane (2.00 g, 6.20 mmol) in DCM (30 mL) was added m-CPBA (3.78 g, 85% purity, 18.6 mmol). The reaction mixture was diluted with H$_2$O (50 mL) and extracted with DCM (3×20 mL). The combined organic layers were washed with saturated aqueous Na$_2$SO$_3$ (2×20 mL) dried over Na$_2$SO$_4$, filtered, and concentrated in vacuo. The crude residue was triturated with EtOAc and then dried in vacuo to give 3-[4-(benzyloxy)-2,6-difluorophenyl]-3-methanesulfonyloxetane, which was used in the subsequent step without further purification. $^1$H NMR (400 MHz, DMSO-d$_6$): δ 7.46-7.35 (m, 5H), 6.95-6.92 (m, 2H), 5.16-5.10 (m, 6H), 3.13 (s, 3H).

Step 6: 3,5-difluoro-4-(3-methanesulfonyloxetan-3-yl)phenol

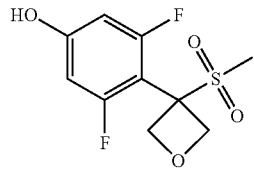 [SMILES: CS(=O)(=O)C1(c2c(F)cc(O)cc2F)COC1]

To a solution of 3-[4-(benzyloxy)-2,6-difluorophenyl]-3-methanesulfonyloxetane (600 mg, 1.69 mmol) in EtOAc (20 mL) under Argon atmosphere was added Pd/C (1.00 g, 10 wt %, 0.943 mmol). The mixture was stirred at room temperature for 3 h under an atmosphere of H$_2$ (15 psi). The reaction mixture was filtered through Celite and the filtrate was concentrated in vacuo to give 3,5-difluoro-4-(3-methanesulfonyloxetan-3-yl)phenol, which was used in the subsequent step without further purification. $^1$H NMR (400 MHz, DMSO-d$_6$, 9/10 H): δ 6.54-6.51 (m, 2H), 5.13-5.08 (m, 4H), 3.09 (s, 3H).

Step 7: 3-[4-(2-bromoethoxy)-2,6-difluorophenyl]-3-methanesulfonyloxetane

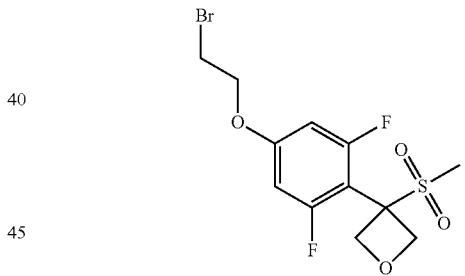

To a solution of 3,5-difluoro-4-(3-methanesulfonyloxetan-3-yl)phenol (200 mg, 0.757 mmol) in 1,2-dibromoethane (2.00 mL, 26.5 mmol) was added Cs$_2$CO$_3$ (493 mg, 1.51 mmol). The mixture was stirred at 80° C. for 3 h. After cooling to 0° C., the reaction mixture was quenched with H$_2$O (10 mL) and extracted with DCM (3×5 mL). The combined organic layers were dried over Na$_2$SO$_4$, filtered, and concentrated in vacuo. The crude residue was purified by normal phase silica gel chromatography (Biotage 4 g cartridge, 0-40% EtOAc:petroleum ether) to give 3-[4-(2-bromoethoxy)-2,6-difluorophenyl]-3-methanesulfonyloxetane (Intermediate A-32). MS=388.0/390.0 [M+NH$_4$]$^+$.

The following intermediates in Table 7 were prepared using procedures similar to those described for Intermediate A-32, using the appropriate starting materials.

General Procedure for Intermediates A-33 & A-34
TABLE 7
| Intermediate # | Structure | Name | Exact Mass [M + H]+ |
|---|---|---|---|
| A-33 | 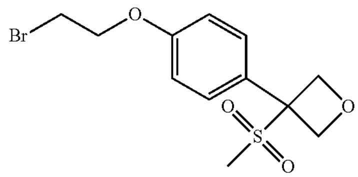 [SMILES: CS(=O)(=O)C1(c2ccc(OCCBr)cc2)COC1] | 3-[4-(2-bromoethoxy)phenyl]-3-methanesulfonyloxetane | Calc'd 352.0/354.0<br>Found 352.1/354.0<br>[M + NH$_4$]+ |
| A-34 | 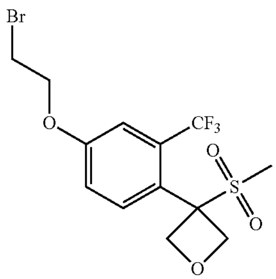 [SMILES: CS(=O)(=O)C1(c2ccc(OCCBr)cc2C(F)(F)F)COC1] | 3-[4-(2-bromoethoxy)-2-(trifluoromethyl)phenyl]-3-methanesulfonyloxetane | Calc'd 420.0/422.0<br>Found 420.0/422.0<br>[M + NH$_4$]+ |
General Procedure for Intermediates A-35, A-36, & A-84
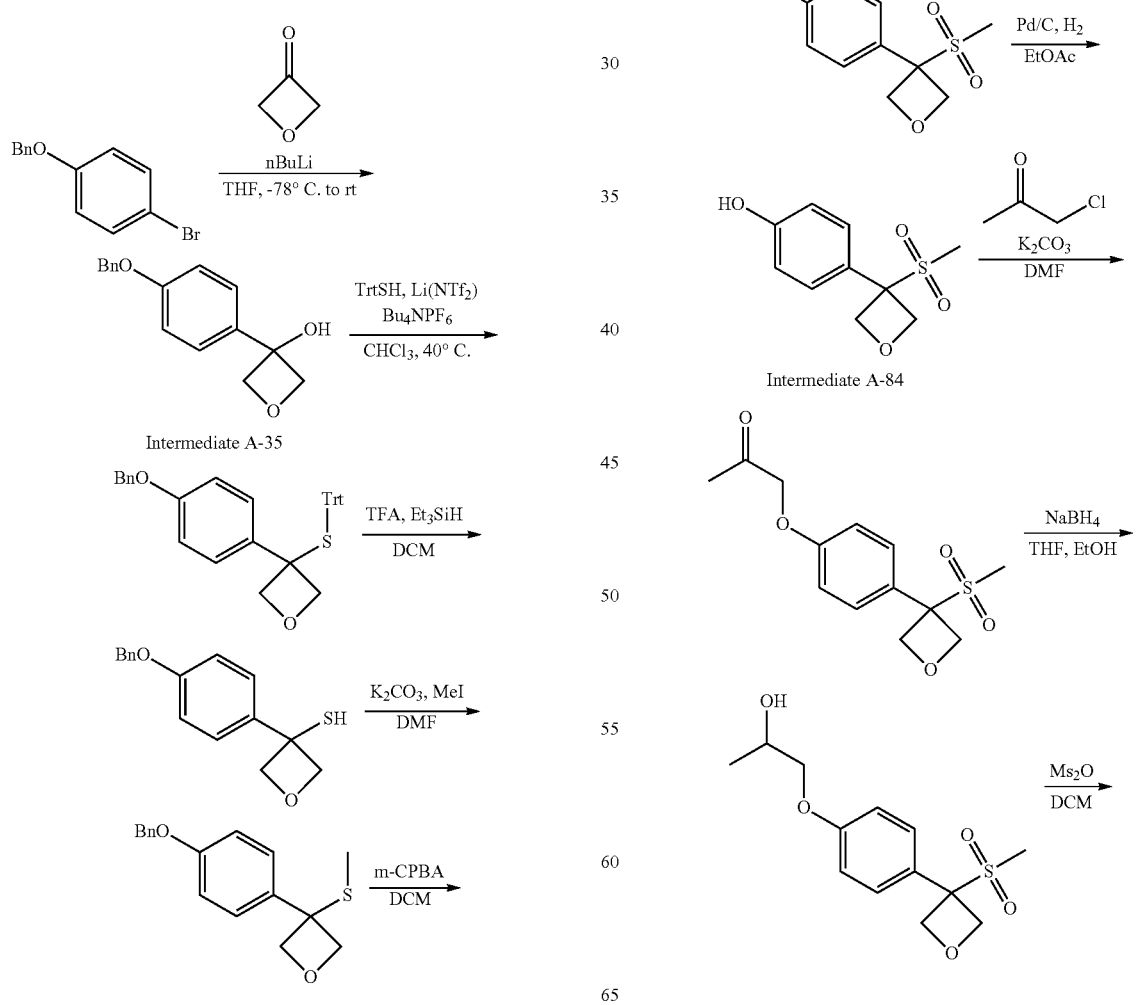

-continued

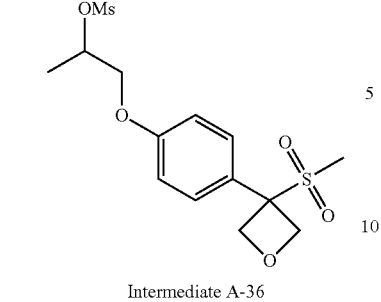

Intermediate A-36

Step 1: 3-[4-(benzyloxy)phenyl]oxetane-3-ol

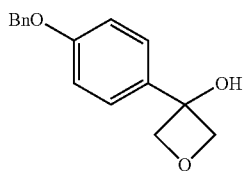

To a −78° C. solution of 1-(benzyloxy)-4-bromobenzene (3.00 g, 11.4 mmol) in THF (20 mL) was added 2.5 M n-BuLi in THF (7.30 mL, 18.3 mmol). After stirring for 1 h at −78° C., oxetan-3-one (986 mg, 13.7 mmol) was added. The mixture was warmed to room temperature and stirred for 3 h. The reaction mixture cooled to 0° C., quenched with H$_2$O (30 mL), and extracted with EtOAc (3×20 mL). The combined organic layers were washed with brine (40 mL), dried over Na$_2$SO$_4$, filtered, and concentrated in vacuo. The crude residue was purified by normal phase silica gel chromatography (Biotage 45 g cartridge, 0-50% EtOAc:petroleum ether) to give 3-[4-(benzyloxy)phenyl]oxetan-3-ol (Intermediate A-35). MS=279.1 [M+Na]$^+$.

Step 2: 3-[4-(benzyloxy)phenyl]-3-[(triphenylmethyl)sulfanyl]oxetane

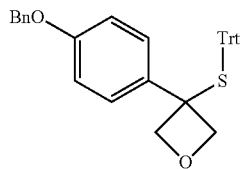

To a solution of 3-[4-(benzyloxy)phenyl]oxetan-3-ol (7.40 g, 28.9 mmol) and triphenylmethanethiol (39.9 g, 144 mmol) in CHCl$_3$ (80 mL) were added [bis(trifluoromethylsulfonyl)amino]lithium (911 mg, 3.18 mmol) and tetrabutylammonium hexafluorophosphate (615 mg, 1.59 mmol). The mixture was stirred at 40° C. for 30 min. After cooling to room temperature, the reaction mixture was quenched with H$_2$O (80 mL) and extracted with DCM (3×50 mL). The combined organic layers were washed with brine (100 mL), dried over Na$_2$SO$_4$, filtered, and concentrated in vacuo. The crude residue was purified by normal phase silica gel chromatography (Biotage 120 g cartridge, 0-40% EtOAc: petroleum ether) to give 3-[4-(benzyloxy)phenyl]-3-[(triphenylmethyl)sulfanyl]oxetane. MS=537.3 [M+Na]$^+$.

Step 3: 3-[4-(benzyloxy)phenyl]oxetane-3-thiol

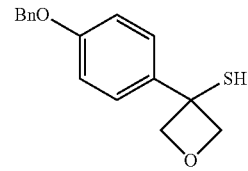 [SMILES: OC1(c2ccc(OCc3ccccc3)cc2)COC1]

To a solution of 3-[4-(benzyloxy)phenyl]-3-[(triphenylmethyl)sulfanyl]oxetane (10.0 g, 19.4 mmol) in DCM (40 mL) was added TFA (60.0 mL, 810 mmol) and Et$_3$SiH (7.76 mL, 48.6 mmol). The mixture was stirred at room temperature for 3 h. The reaction mixture was quenched with H$_2$O (80 mL) and extracted with DCM (3×50 mL). The combined organic layers were washed with brine (100 mL), dried over Na$_2$SO$_4$, filtered and concentrated under reduced pressure to give 3-(4-benzyloxyphenyl)oxetane-3-thiol, which was used in the subsequent step without further purification. MS=273.1 [M+H]$^+$.

Step 4: 3-[4-(benzyloxy)phenyl]-3-(methylsulfanyl)oxetane

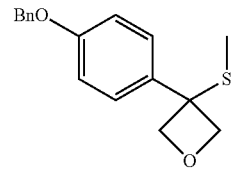 [SMILES: CSC1(c2ccc(OCc3ccccc3)cc2)COC1]

To a solution of 3-(4-benzyloxyphenyl)oxetane-3-thiol (5.00 g, 18.4 mmol) in DMF (40 mL) was added MeI (13.0 g, 91.8 mmol) and K$_2$CO$_3$ (3.81 g, 27.5 mmol). The mixture was stirred at room temperature for 1 h. The reaction mixture was quenched with H$_2$O (80 mL) and extracted with EtOAc (3×50 mL). The combined organic layers were washed with brine (2×50 mL), dried over Na$_2$SO$_4$, filtered, and concentrated in vacuo. The crude residue was purified by normal phase silica gel chromatography (Biotage 80 g cartridge, 0-30% EtOAc:petroleum ether) to give 3-[4-(benzyloxy)phenyl]-3-(methylsulfanyl)oxetane. $^1$H NMR (400 MHz, CDCl$_3$): δ 7.46-7.39 (m, 5H), 7.11 (d, J=8.8 Hz, 2H), 6.98 (d, J=8.8 Hz, 2H), 5.18 (d, J=6.4 Hz, 2H), 5.08 (s, 2H), 4.90 (d, J=6.4 Hz, 2H), 2.04 (s, 3H).

Step 5: 3-[4-(benzyloxy)phenyl]-3-methanesulfonyloxetane

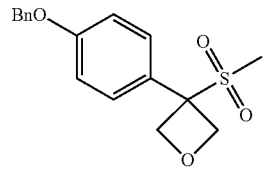 [SMILES: CS(=O)(=O)C1(c2ccc(OCc3ccccc3)cc2)COC1]

To a 0° C. solution of 3-[4-(benzyloxy)phenyl]-3-(methylsulfanyl)oxetane (3.25 g, 11.4 mmol) in DCM (40 mL) was added m-CPBA (6.91 g, 85% purity, 34.04 mmol). The mixture was stirred at room temperature for 3 h. The reaction mixture was quenched with saturated aqueous Na$_2$SO$_3$ (20 mL), diluted with H$_2$O (60 mL), and extracted with DCM (3×40 mL). The combined organic layers were with saturated aqueous NaHCO$_3$ (3×50 mL), dried over Na$_2$SO$_4$, filtered, and concentrated in vacuo. The resulting residue was triturated with EtOAc, the solids were collected via filtration, and the filter cake was dried in vacuo to give 3-[4-(benzyloxy)phenyl]-3-methanesulfonyloxetane. MS=336.2 [M+NH$_4$]$^+$.

Step 6: 4-(3-methanesulfonyloxetan-3-yl)phenol

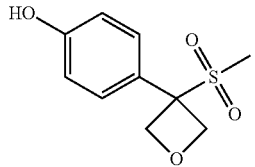

To a solution of 3-[4-(benzyloxy)phenyl]-3-methanesulfonyloxetane (1.60 g, 5.03 mmol) in EtOAc (100 mL) under N$_2$ atmosphere was added Pd/C (2.00 g, 10 wt %, 1.89 mmol). The suspension was degassed under vacuum and purged with H$_2$ several times. The mixture was stirred under H$_2$ (15 psi) at room temperature for 10 h. The reaction mixture was filtered through Celite and the filtrate was concentrated in vacuo give 4-(3-methanesulfonyloxetan-3-yl)phenol (Intermediate A-84), which was used in the subsequent step without further purification. MS=246.1 [M+NH$_4$].

Step 7: 1-[4-(3-methanesulfonyloxetan-3-yl)phenoxy]propan-2-one

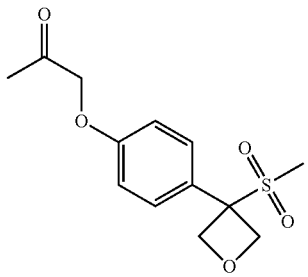 [SMILES: CC(=O)COc1ccc(C2(S(C)(=O)=O)COC2)cc1]

To a solution of 4-(3-methylsulfonyloxetan-3-yl)phenol (500 mg, 2.19 mmol) in DMF (5 mL) was added K$_2$CO$_3$ (605 mg, 4.38 mmol) and 1-chloropropan-2-one (304 mg, 3.29 mmol). The mixture was stirred at room temperature for 1 h. The reaction mixture was cooled to 0° C. and quenched with H$_2$O (15 mL), and then extracted with EtOAc (2×20 mL). The combined organic layers were washed with brine (2×30 mL), dried over Na$_2$SO$_4$, filtered and concentrated in vacuo to give 1-[4-(3-methanesulfonyloxetan-3-yl)phenoxy]propan-2-one, which was used in the subsequent step without further purification. MS=302.2 [M+NH$_4$].

Step 8: 1-[4-(3-methanesulfonyloxetan-3-yl)phenoxy]propan-2-ol

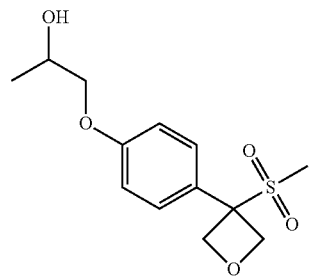

To a solution of 1-[4-(3-methanesulfonyloxetan-3-yl)phenoxy]propan-2-one (600 mg, 2.11 mmol) in THF (15 mL) and EtOH (2 mL) was added NaBH$_4$ (120 mg, 3.17 mmol). The mixture was stirred at room temperature for 30 min. The reaction mixture was cooled to 0° C., quenched with H$_2$O (15 mL), and the solution was adjusted to pH=6-7 with the dropwise addition of 4.0 M aqueous HCl. The mixture was extracted with EtOAc (2×10 mL). The combined organic layers were washed with brine (10 mL), dried over Na$_2$SO$_4$, filtered, and concentrated in vacuo to give 1-[4-(3-methanesulfonyloxetan-3-yl)phenoxy]propan-2-ol, which was used in the subsequent step without further purification. MS=304.1 [M+NH$_4$]$^+$.

Step 9: 1-[4-(3-methanesulfonyloxetan-3-yl)phenoxy]propan-2-yl methanesulfonate

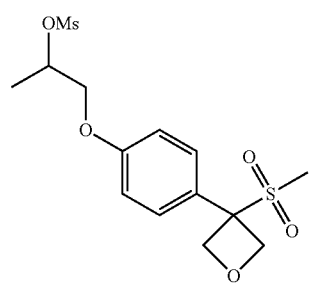 [SMILES: CC(COc1ccc(C2(S(C)(=O)=O)COC2)cc1)OS(C)(=O)=O]

To a solution of 1-[4-(3-methanesulfonyloxetan-3-yl)phenoxy]propan-2-ol (570 mg, 1.99 mmol) in DCM (15 mL) was added TEA (0.831 mL, 5.97 mmol) and methanesulfonic anhydride (694 mg, 3.98 mmol). The mixture was stirred at room temperature for 1 h. The reaction mixture was quenched with H$_2$O (15 mL), and the solution was adjusted to pH=6 with the dropwise addition of 4.0 M aqueous HCl. The mixture was extracted with DCM (3×10 mL). The combined organic layers were washed with brine (2×20 mL), dried over Na$_2$SO$_4$, filtered and concentrated in vacuo to give 1-[4-(3-methanesulfonyloxetan-3-yl)phenoxy]propan-2-yl methanesulfonate, which was used in the subsequent step without further purification (Intermediate A-36). MS=382.1 [M+NH$_4$]$^+$.

General Procedure for Intermediate A-37

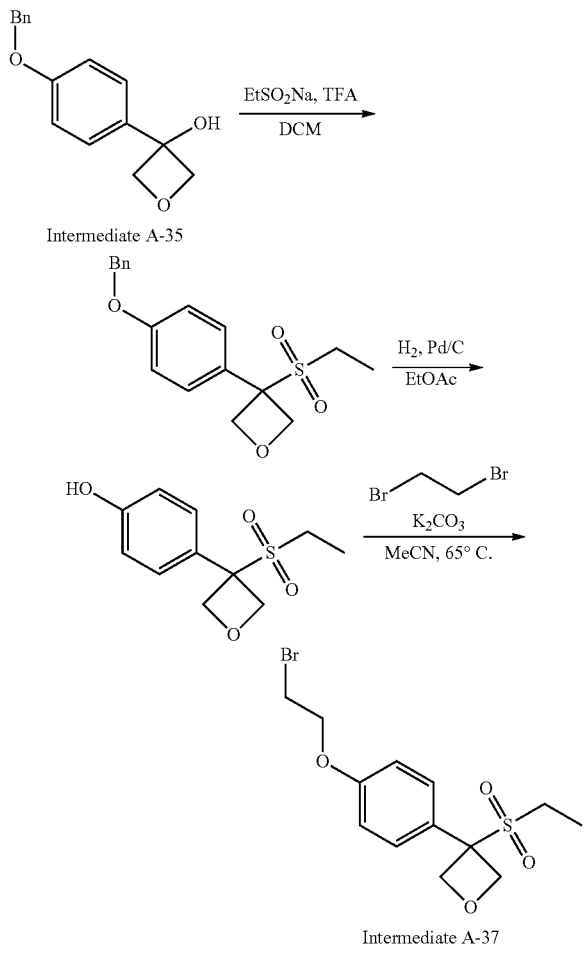

Intermediate A-35

Intermediate A-37

Step 1: 3-[4-(benzyloxy)phenyl]-3-(ethanesulfonyl)oxetane

To a 0° C. solution of 3-[4-(benzyloxy)phenyl]oxetan-3-ol (Intermediate A-35, 400 mg, 1.56 mmol) in DCM (5 mL) was added sodium ethanesulfinate (906 mg, 7.80 mmol) and TFA (2.31 mL, 31.2 mmol). The mixture was stirred at room temperature for 3 h. The reaction mixture was quenched with H$_2$O (30 mL). The resulting precipitate was collected by filtration and dried in vacuo to give 3-[4-(benzyloxy) phenyl]-3-(ethanesulfonyl)oxetane. MS=350.1 [M+NH$_4$].

Step 2: 4-[3-(ethanesulfonyl)oxetan-3-yl]phenol

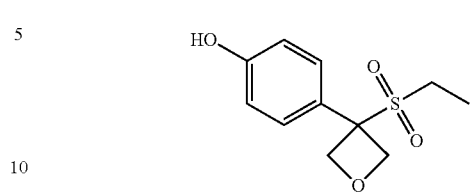

To a solution of 3-[4-(benzyloxy)phenyl]-3-(ethanesulfonyl)oxetane (400 mg, 1.20 mmol) in EtOAc (20 mL) under N$_2$ atmosphere was added Pd/C (1.00 g, 10 wt %, 0.943 mmol). The suspension was degassed under vacuum and purged with H$_2$ (3×). The mixture was stirred under H$_2$ (15 psi) at room temperature for 3 h. The reaction mixture was filtered through Celite and the filtrate was concentrated in vacuo to give 4-[3-(ethanesulfonyl)oxetan-3-yl]phenol, which was used in the subsequent step without further purification.

Step 3: 3-[4-(2-bromoethoxy)phenyl]-3-(ethanesulfonyl)oxetane

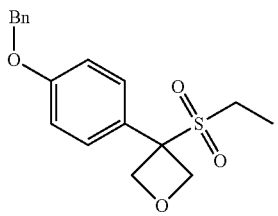 [SMILES: CCS(=O)(=O)C1(c2ccc(OCc3ccccc3)cc2)COC1]

To a solution of 4-[3-(ethanesulfonyl)oxetan-3-yl]phenol (150 mg, 0.619 mmol) in MeCN (4 mL) were added K$_2$CO$_3$ (428 mg, 3.10 mmol) and 1,2-dibromoethane (1.87 mL, 24.8 mmol). The mixture was stirred at 65° C. for 10 h. After cooling to room temperature, the reaction mixture was filtered, washed with MeCN (20 mL), and the filtrate was concentrated in vacuo. The crude residue was purified by normal phase silica gel chromatography (Biotage 4 g cartridge, 0-45% EtOAc:petroleum ether) to give 3-[4-(2-bromoethoxy)phenyl]-3-(ethanesulfonyl)oxetane (Intermediate A-37). MS=366.0/368.0 [M+NH$_4$]$^+$.

General Procedure for Intermediate A-38

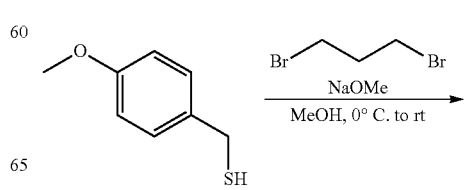

681

-continued

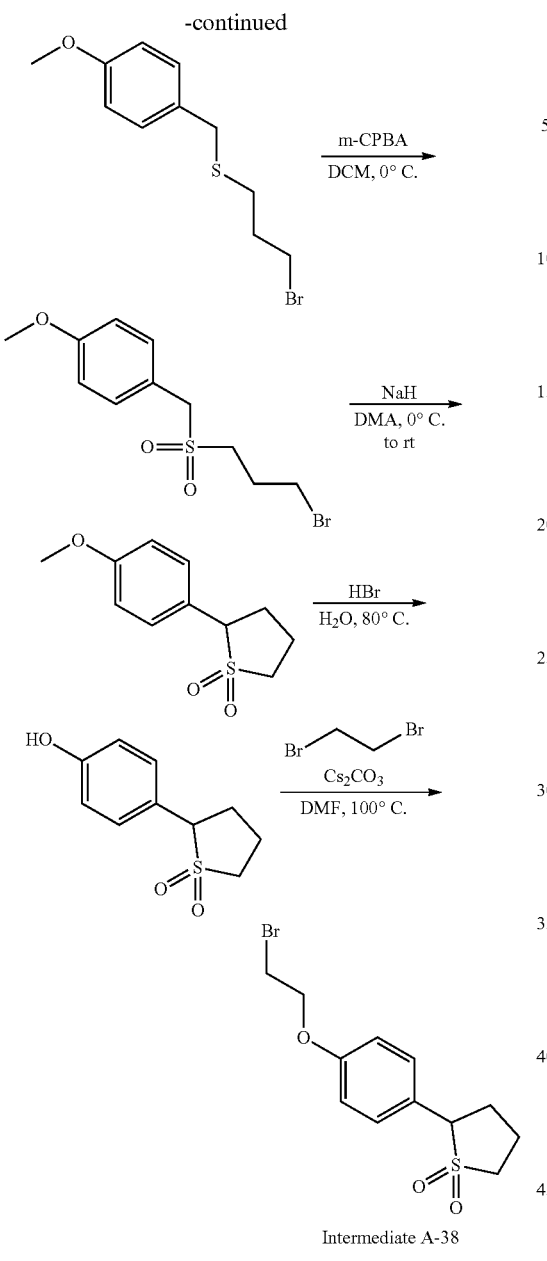

Intermediate A-38

Step 1: 1-{[(3-bromopropyl)sulfanyl]methyl}-4-methoxybenzene

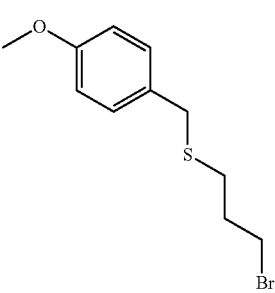

682

To a solution of (4-methoxyphenyl)methanethiol (9.01 mL, 64.8 mmol) and 1,3-dibromopropane (33.1 mL, 324 mmol) in MeOH (50 mL) was added NaOMe (5.25 g, 97.3 mmol). The reaction mixture stirred at room temperature for 16 h. After cooling to 0° C., the reaction mixture was quenched with H₂O (200 mL) and extracted with EtOAc (3×50 mL). The combined organic layers were washed with brine (100 mL), dried over (Na₂SO₄), filtered, and concentrated in vacuo. The crude residue was purified by normal phase silica gel chromatography (Biotage 120 g cartridge, 0-10% EtOAc:petroleum ether) to give 1-{[(3-bromopropyl)sulfanyl]methyl}-4-methoxybenzene.

Step 2: 1-[(3-bromopropanesulfonyl)methyl]-4-methoxybenzene

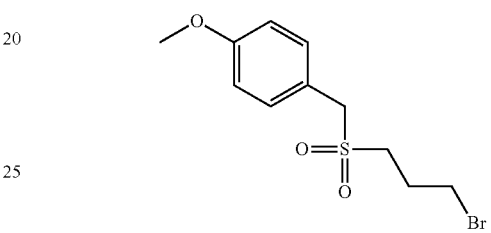

To a 0° C. solution of 1-{[(3-bromopropyl)sulfanyl]methyl}-4-methoxybenzene (5.00 g, 18.2 mmol) in DCM (100 mL) was added m-CPBA (9.22 g, 85% purity, 45.4 mmol). The mixture was stirred at 0° C. for 2 h and was then quenched with saturated Na₂SO₃ (50 mL). The organic layer was separated, washed with saturated NaHCO₃ (2×100 mL), brine (100 mL), dried over Na₂SO₄, filtered, and concentrated in vacuo. The crude residue was purified by normal phase silica gel chromatography (Biotage 120 g cartridge, 0-50% EtOAc:petroleum ether) to give 1-[(3-bromopropanesulfonyl)methyl]-4-methoxybenzene.

Step 3: 2-(4-methoxyphenyl)-1$\lambda^6$-thiolane-1,1-dione

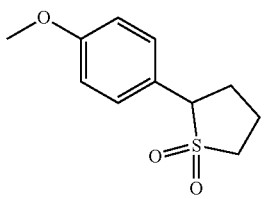

To a 0° C. solution of 1-[(3-bromopropanesulfonyl)methyl]-4-methoxybenzene (3.00 g, 9.77 mmol) in DMA (30 mL) was added NaH (898 mg, 60 wt % in mineral oil, 22.5 mmol). The mixture was allowed to warm to room temperature and stirred for 16 h. The reaction mixture was quenched with ice water (20 mL), diluted with H₂O (10 mL) and extracted with EtOAc (3×30 mL). The combined organic layers were washed with brine (30 mL), dried over Na₂SO₄, filtered, and concentrated in vacuo. The crude residue was purified by normal phase silica gel chromatography (Biotage 25 g cartridge, 0-100% EtOAc:petroleum ether) to give 2-(4-methoxyphenyl)-1$\lambda^6$-thiolane-1,1-dione. MS=227.2 [M+H]⁺.

Step 4: 2-(4-hydroxyphenyl)-1λ⁶-thiolane-1,1-dione

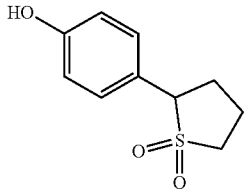 [SMILES: O=S1(=O)CCCC1c1ccc(O)cc1]

A solution of 2-(4-methoxyphenyl)-1λ⁶-thiolane-1,1-dione (1.00 g, 4.42 mmol) in HBr in H$_2$O (10 mL, 45 wt %) was stirred at 80° C. for 16 h. After cooling to room temperature, the reaction mixture was concentrated in vacuo. The residue was diluted with H$_2$O (20 mL) and extracted with EtOAc (3×10 mL). The combined organic layers were washed with brine (20 mL), dried over Na$_2$SO$_4$, filtered, and concentrated in vacuo. The crude residue was purified by normal phase silica gel chromatography (Biotage 25 g cartridge, 0-100% EtOAc:petroleum ether) to give 2-(4-hydroxyphenyl)-1λ⁶-thiolane-1,1-dione. MS=213.1 [M+H]⁺.

Step 5: 2-[4-(2-bromoethoxy)phenyl]-1λ⁶-thiolane-1,1-dione

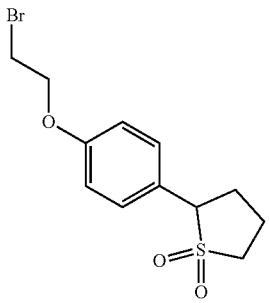 [SMILES: O=S1(=O)CCCC1c1ccc(OCCBr)cc1]

To a mixture of 2-(4-hydroxyphenyl)-1λ⁶-thiolane-1,1-dione (660 mg, 3.11 mmol) and 1,2-dibromoethane (2.35 mL, 31.1 mmol) in DMF (5 mL) was added Cs$_2$CO$_3$ (3.04 g, 9.33 mmol). The reaction mixture was stirred at 100° C. for 16 h. After cooling to room temperature, the mixture was diluted with H$_2$O (30 mL) and extracted with EtOAc (3×20 mL). The combined organic layers were washed with brine (50 mL), dried over Na$_2$SO$_4$, filtered, and concentrated in vacuo. The crude residue was purified by normal phase silica gel chromatography (Biotage 25 g cartridge, 0-100% EtOAc:petroleum ether) to give 2-(4-hydroxyphenyl)-1λ⁶-thiolane-1,1-dione (Intermediate A-38). MS=319.0/321.0 [M+H]⁺.

General Procedure for Intermediate A-39

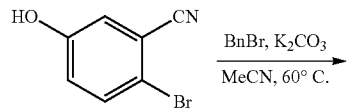

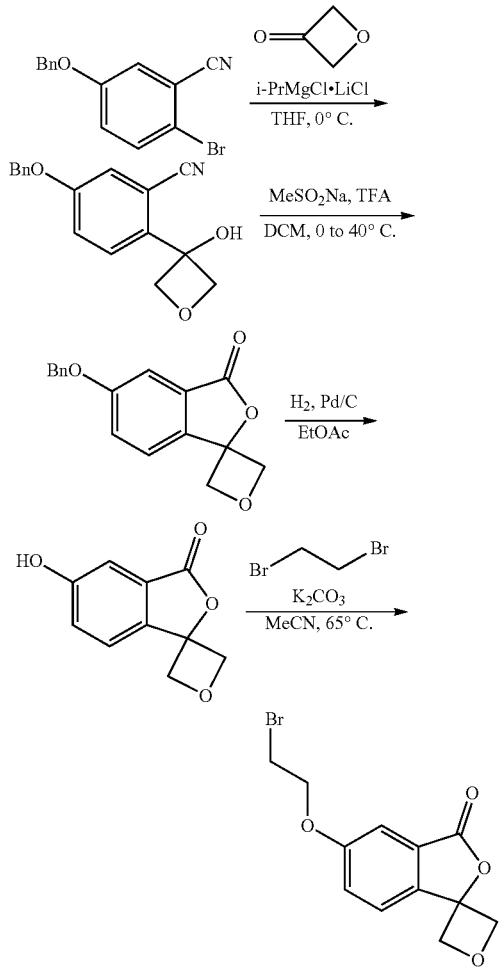

Intermediate A-39

Step 1: 5-(benzyloxy)-2-bromobenzonitrile

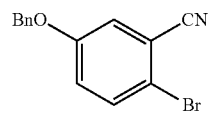

To a solution of 2-bromo-5-hydroxybenzonitrile (15.0 g, 75.8 mmol) in MeCN (160 mL) were added benzyl bromide (10.8 mL, 90.9 mmol) and K$_2$CO$_3$ (15.7 g, 114 mmol). The mixture was stirred at 60° C. for 15 h. After cooling to room temperature, the reaction mixture was filtered to remove solids. The filtrate was diluted with water (60 mL) and extracted with EtOAc (3×80 mL). The combined organic layers were washed with brine (100 mL), dried over Na$_2$SO$_4$, filtered, and concentrated in vacuo. The residue was triturated with petroleum ether and dried in vacuo to give 5-(benzyloxy)-2-bromobenzonitrile, which was used in the subsequent step without further purification.

Step 2:
5-(benzyloxy)-2-(3-hydroxyoxetan-3-yl)benzonitrile

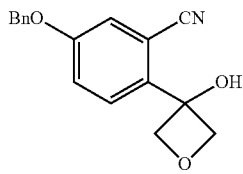 [SMILES: N#Cc1cc(OCc2ccccc2)ccc1C1(O)COC1]

To a 0° C. solution of 5-(benzyloxy)-2-bromobenzonitrile (10.0 g, 34.7 mmol) in THF (120 mL) was slowly added 1.3 M i-PrMgCl·LiCl in THE (34.71 mL, 45.1 mmol). After stirring for 10 min, oxetan-3-one (3.50 g, 48.59 mmol) was added to the mixture, and stirring was continued for another 2 h. The reaction mixture was quenched with saturated aqueous NH$_4$Cl (80 mL) and stirred for 30 min, and then was extracted with EtOAc (3×80 mL). The combined organic layers were washed with brine (100 mL), dried over Na$_2$SO$_4$, filtered, and concentrated in vacuo. The crude residue was purified by normal phase silica gel chromatography (Biotage 120 g cartridge, 0-20% EtOAc:petroleum ether) to give 5-(benzyloxy)-2-(3-hydroxyoxetan-3-yl)benzonitrile. MS=282.2 [M+H]$^+$.

Step 3: 5-(benzyloxy)-3H-spiro[2-benzofuran-1,3'-oxetan]-3-one

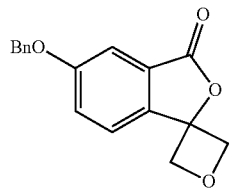 [SMILES: O=C1OC2(COC2)c2ccc(OCc3ccccc3)cc21]

To a 0° C. solution of 5-(benzyloxy)-2-(3-hydroxyoxetan-3-yl)benzonitrile (1.50 g, 5.33 mmol) in DCM (20 mL) was added sodium methanesulfinate (2.72 g, 26.7 mmol) followed by the dropwise addition of TFA (3.95 mL, 53.3 mmol). The mixture was stirred at 40° C. for 15 h. After cooling to room temperature, the reaction mixture was quenched with H$_2$O (20 mL) and extracted with EtOAc (3×15 mL). The combined organic layers were washed with brine (20 mL), dried over Na$_2$SO$_4$, filtered, and concentrated in vacuo. The crude residue was purified by normal phase silica gel chromatography (Biotage 20 g cartridge, 0-25% EtOAc:petroleum ether) to give 5-(benzyloxy)-3H-spiro[2-benzofuran-1,3'-oxetan]-3-one. MS=283.2 [M+H]$^+$.

Step 4: 5-hydroxy-3H-spiro[2-benzofuran-1,3'-oxetan]-3-one

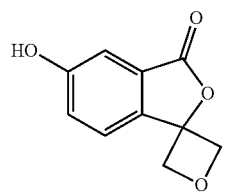 [SMILES: O=C1OC2(COC2)c2ccc(O)cc21]

To a solution of 5-(benzyloxy)-3H-spiro[2-benzofuran-1,3'-oxetan]-3-one (900 mg, 3.19 mmol) in MeOH (25 mL) was added Pd/C (200 mg, 10 wt %, 0.189 mmol). The mixture was stirred at room temperature for 15 h under H$_2$ (15 psi). The reaction mixture was filtered and concentrated in vacuo to give 5-(benzyloxy)-3H-spiro[2-benzofuran-1,3'-oxetan]-3-one, which was used in the subsequent step without further purification. MS=193.2 [M+H]$^+$.

Step 5: 5-(2-bromoethoxy)-3H-spiro[2-benzofuran-1,3'-oxetan]-3-one

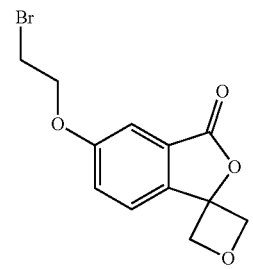 [SMILES: O=C1OC2(COC2)c2ccc(OCCBr)cc21]

To a solution of 5-(benzyloxy)-3H-spiro[2-benzofuran-1,3'-oxetan]-3-one (420 mg, 2.19 mmol) in MeCN (5 mL) were added K$_2$CO$_3$ (1.51 g, 10.9 mmol) and 1,2-dibromoethane (6.60 mL, 87.4 mmol). The mixture was stirred at 65° C. for 15 h. After cooling to room temperature, the reaction mixture was quenched with H$_2$O (20 mL) and extracted with EtOAc (3×20 mL). The combined organic layers were washed with brine (20 mL), dried over Na$_2$SO$_4$, filtered, and concentrated in vacuo. The crude residue was purified by normal phase silica gel chromatography (Biotage 12 g cartridge, 0-33% EtOAc:petroleum ether) to give 5-(2-bromoethoxy)-3H-spiro[2-benzofuran-1,3'-oxetan]-3-one (Intermediate A-39). MS=299.0/301.1 [M+H]$^+$.

General Procedure for Intermediate A-40

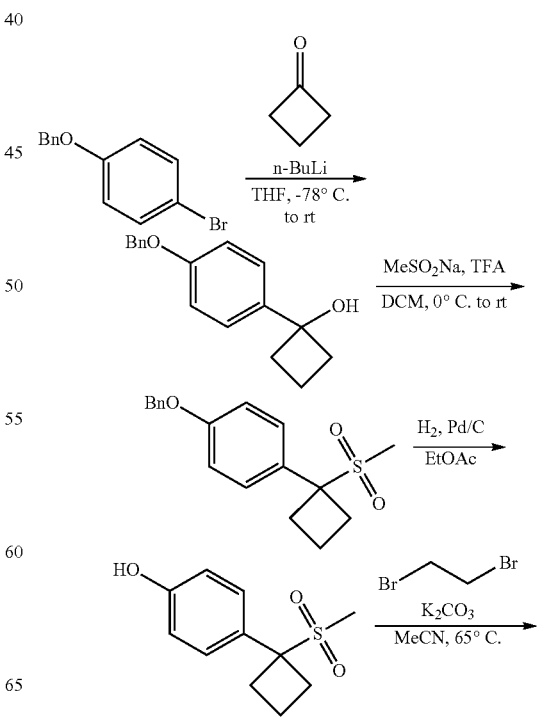

Step 1: 1-[4-(benzyloxy)phenyl]cyclobutan-1-ol

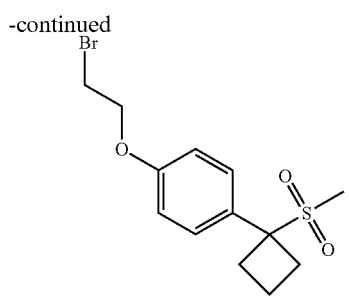

Intermediate A-40

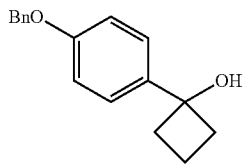 [SMILES: OC1(c2ccc(OCc3ccccc3)cc2)CCC1]

To a −78° C. solution of 1-(benzyloxy)-4-bromobenzene (5.00 g, 19.0 mmol) in THF (50 mL) was added 2.5 M n-BuLi in THF (12.16 mL, 30.4 mmol). After stirring at −78° C. for 30 min, cyclobutanone (1.70 mL, 22.8 mmol) was added. The mixture was allowed to warm to room temperature and stirred for 1 h. The reaction mixture was cooled to 0° C., quenched with saturated aqueous NH$_4$Cl (50 mL), and then extracted with EtOAc (3×70 mL). The combined organic layers were dried over Na$_2$SO$_4$, filtered, and concentrated in vacuo. The crude residue was purified by normal phase silica gel chromatography (Biotage 40 g cartridge, 0-15% EtOAc:petroleum ether) to give 1-[4-(benzyloxy)phenyl]cyclobutan-1-ol. $^1$H NMR (400 MHz, DMSO-d$_6$, 17/18 H): δ 7.46-7.38 (m, 7H), 6.99 (d, J=8.8 Hz, 2H), 5.09 (s, 2H), 2.57-2.54 (m, 2H), 2.40-2.35 (m, 2H), 2.00-1.98 (m, 1H), 1.69-1.64 (m, 1H).

Step 2: 1-(benzyloxy)-4-(1-methanesulfonylcyclobutyl)benzene

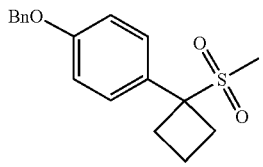 [SMILES: CS(=O)(=O)C1(c2ccc(OCc3ccccc3)cc2)CCC1]

To a 0° C. solution of 1-[4-(benzyloxy)phenyl]cyclobutan-1-ol (3.80 g, 14.9 mmol) and sodium methanesulfinate (10.7 g, 105 mmol) in DCM (40 mL) was added TFA (22.1 mL, 299 mmol). The mixture was allowed to warm to room temperature and stirred for 3 h. The reaction mixture was cooled to 0° C. and quenched with H$_2$O (50 mL). The resulting biphasic mixture was adjusted to pH=6-7 with saturated aqueous Na$_2$CO$_3$ and then extracted with DCM (3×50 mL). The combined organic layers were dried over Na$_2$SO$_4$, filtered, and concentrated in vacuo. The residue was triturated with 1:1 petroleum ether:EtOAc. The mixture was filtered, the filter cake was washed with EtOAc, and dried in vacuo to give 1-(benzyloxy)-4-(1-methanesulfonylcyclobutyl)benzene, which was used in the subsequent step without further purification. $^1$H NMR (400 MHz, DMSO-d$_6$): δ 7.46-7.34 (m, 7H), 7.04 (d, J=8.8 Hz, 2H), 5.12 (s, 2H), 2.94-2.91 (m, 2H), 2.61-2.55 (m, 5H), 2.09-2.07 (m, 1H), 1.89-1.86 (m, 1H).

Step 3: 4-(1-methanesulfonylcyclobutyl)phenol

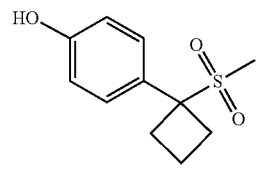

To a solution of 1-(benzyloxy)-4-(1-methanesulfonylcyclobutyl)benzene (2.60 g, 8.22 mmol) in EtOAc (100 mL) under a N$_2$ environment was added Pd/C (2.00 g, 10 wt %, 1.89 mmol). The suspension was degassed under vacuum and purged with H$_2$ (3×). The mixture was stirred under H$_2$ (15 psi) at room temperature for 5 h. The reaction mixture was filtered through Celite, the filter cake was washed with EtOAc, and the filtrate was concentrated in vacuo to give 1-(benzyloxy)-4-(1-methanesulfonylcyclobutyl)benzene, which was used in the subsequent step without further purification. $^1$H NMR (400 MHz, DMSO-d$_6$): δ 9.64 (s, 1H), 7.20 (d, J=6.8 Hz, 2H), 6.77 (d, J=6.8 Hz, 2H), 2.91-2.87 (m, 2H), 2.58 (s, 3H), 2.56-2.52 (m, 2H), 2.08-2.05 (m, 1H), 1.88-1.84 (s, 1H).

Step 4: 1-(2-bromoethoxy)-4-(1-methanesulfonylcyclobutyl)benzene

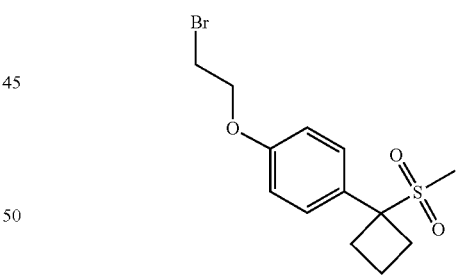

A mixture of 1-(benzyloxy)-4-(1-methanesulfonylcyclobutyl)benzene (500 mg, 2.21 mmol), 1,2-dibromoethane (6.67 mL, 88.4 mmol) and K$_2$CO$_3$ (1.53 g, 11.1 mmol) in MeCN (10 mL) was stirred at 65° C. for 16 h. After cooling to room temperature, the reaction mixture was filtered and concentrated in vacuo. The crude residue was purified by normal phase silica gel chromatography (Biotage 12 g cartridge, 0-30% EtOAc:petroleum ether) to give 1-(2-bromoethoxy)-4-(1-methanesulfonylcyclobutyl)benzene (Intermediate A-40). MS=350.1/352.1 [M+NH$_4$]$^+$.

The following intermediate in Table 8 was prepared according to procedures similar those described for Intermediate A-40 using the appropriate starting materials.

General Procedure for Intermediate A-41
TABLE 8
| Intermediate # | Structure | Name | Exact Mass [M + H]+ |
|---|---|---|---|
| A-41 | 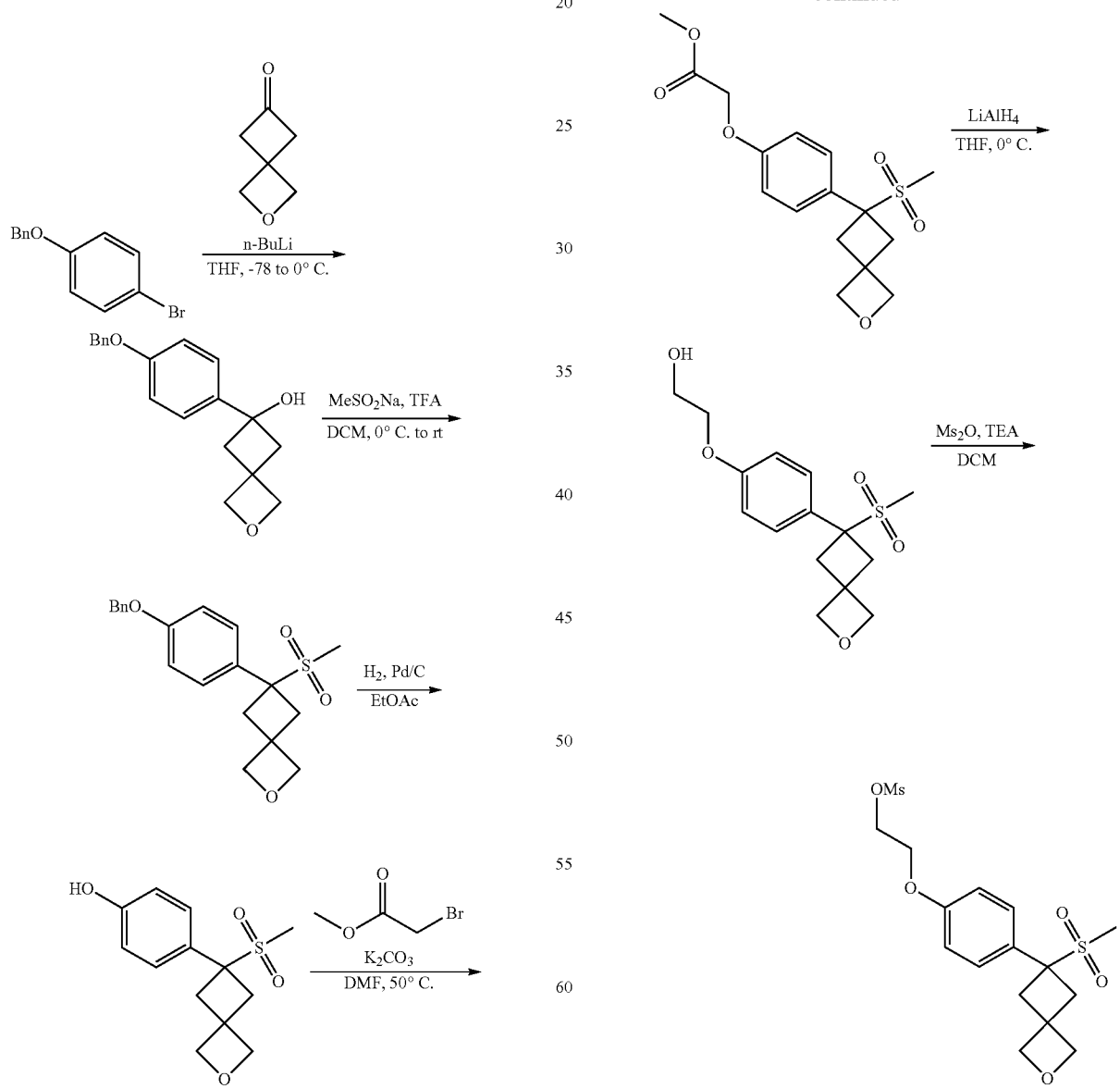 | 4-[4-(2-bromoethoxy)phenyl]-4-methanesulfonyloxane | Calc'd 380.1/382.1 Found 380.1/382.1 [M + NH4]+ |
General Procedure for Intermediate A-42

Step 1: 6-[4-(benzyloxy)phenyl]-2-oxaspiro[3.3]heptan-6-ol

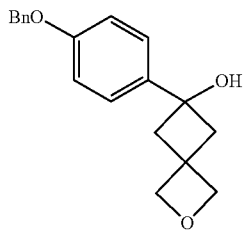 [SMILES: OC1(c2ccc(OCc3ccccc3)cc2)CC2(COC2)C1]

To a −78° C. solution of 1-(benzyloxy)-4-bromobenzene (2.68 g, 10.2 mmol) in THF (10 mL) was added 2.5 M n-BuLi in THF (4.74 mL, 11.9 mmol). After stirring for 20 min, a solution of 2-oxaspiro[3.3]heptan-6-one (950 mg, 8.47 mmol) in THF (3 mL) was added. The mixture was stirred at −78° C. for 30 min. The reaction mixture was warmed to 0° C., quenched with saturated aqueous NH$_4$Cl (15 mL), and then extracted with EtOAc (2×20 mL). The combined organic layers were washed with brine (2×30 mL), dried over Na$_2$SO$_4$, filtered and concentrated under reduced pressure to give 6-[4-(benzyloxy)phenyl]-2-oxaspiro[3.3]heptan-6-ol. MS=279.1 [M-OH]$^+$.

Step 2: 6-[4-(benzyloxy)phenyl]-6-methanesulfonyl-2-oxaspiro[3.3]heptane

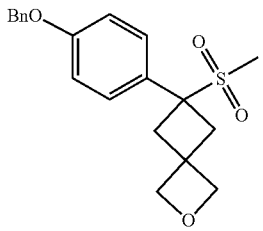 [SMILES: CS(=O)(=O)C1(c2ccc(OCc3ccccc3)cc2)CC2(COC2)C1]

To a solution of 6-[4-(benzyloxy)phenyl]-2-oxaspiro[3.3]heptan-6-ol (2.00 g, 6.75 mmol) in DCM (30 mL) were added sodium methanesulfinate (3.44 g, 33.7 mmol), and TFA (9.99 mL, 135 mmol). The mixture was stirred at room temperature for 3 h. The reaction mixture was cooled to 0° C., quenched with H$_2$O (50 mL), and then extracted with DCM (2×15 mL). The combined organic layers were washed with brine (30 mL×2), dried over Na$_2$SO$_4$, filtered, and concentrated in vacuo. The crude residue was purified by normal phase silica gel chromatography (Biotage 20 g cartridge, 0-50% EtOAc:petroleum ether) to give 6-[4-(benzyloxy)phenyl]-6-methanesulfonyl-2-oxaspiro[3.3]heptane. MS=359.1 [M+H]$^+$.

Step 3: 4-{6-methanesulfonyl-2-oxaspiro[3.3]heptan-6-yl}phenol

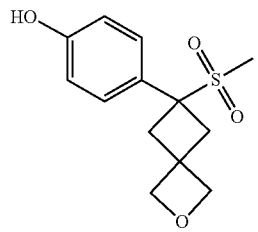 [SMILES: CS(=O)(=O)C1(c2ccc(O)cc2)CC2(COC2)C1]

To a solution of 6-[4-(benzyloxy)phenyl]-6-methanesulfonyl-2-oxaspiro[3.3]heptane (400 mg, 1.12 mmol) in EtOAc (10 mL) under N$_2$ atmosphere was added Pd/C (200 mg, 10 wt %, 1.89 mmol). The suspension was degassed under vacuum and purged with H$_2$ (3×). The mixture was stirred under H$_2$ (15 psi) at room temperature for 3 h. The mixture was filtered through Celite and the filtrate was concentrated in vacuo to give 4-{6-methanesulfonyl-2-oxaspiro[3.3]heptan-6-yl}phenol, which was used in the subsequent step without further purification.

Step 4: methyl 2-(4-{6-methanesulfonyl-2-oxaspiro[3.3]heptan-6-yl}phenoxy)acetate

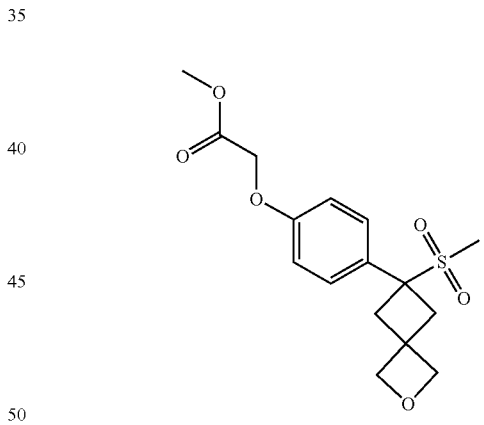

A mixture of 4-{6-methanesulfonyl-2-oxaspiro[3.3]heptan-6-yl}phenol (240 mg, 0.894 mmol), methyl 2-bromoacetate (0.169 mL, 1.79 mmol), and K$_2$CO$_3$ (309 mg, 2.24 mmol) in DMF (5 mL) was degassed and purged with N$_2$ (3×). The mixture was stirred at 50° C. for 3 h under N$_2$ atmosphere. The reaction mixture was cooled to 0° C., quenched with H$_2$O (15 mL), and extracted with EtOAc (3×10 mL). The combined organic layers were washed with brine (2×15 mL), dried over Na$_2$SO$_4$, filtered, and concentrated in vacuo to give methyl 2-(4-{6-methanesulfonyl-2-oxaspiro[3.3]heptan-6-yl}phenoxy)acetate. MS=341.1 [M+H]$^+$.

Step 5: 2-(4-{6-methanesulfonyl-2-oxaspiro[3.3]heptan-6-yl}phenoxy)ethan-1-ol

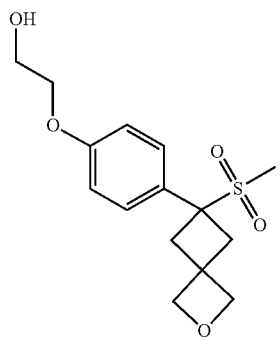 [SMILES: CS(=O)(=O)C1(c2ccc(OCCO)cc2)CC2(COC2)C1]

To a 0° C. solution of methyl 2-(4-{6-methanesulfonyl-2-oxaspiro[3.3]heptan-6-yl}phenoxy)acetate (300 mg, 0.881 mmol) in THF (10 mL) under a $N_2$ environment was added LiAlH$_4$ (66.9 mg, 1.76 mmol). The mixture was stirred at 0° C. for 30 min, and then was quenched with $H_2O$ (15 mL). The resulting biphasic mixture was adjusted to pH=6-7 with 2.0 M aqueous HCl solution, and then was extracted with EtOAc (3×15 mL). The combined organic layers were washed with brine (2×20 mL), dried over Na$_2$SO$_4$, filtered, and concentrated in vacuo to give 2-(4-{6-methanesulfonyl-2-oxaspiro[3.3]heptan-6-yl}phenoxy)ethan-1-ol, which was used in the subsequent step without further purification. MS=313.1 [M+H]$^+$.

Step 6: 2-(4-{6-methanesulfonyl-2-oxaspiro[3.3]heptan-6-yl}phenoxy)ethyl methanesulfonate

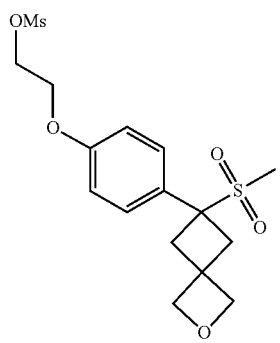 [SMILES: CS(=O)(=O)OCCOc1ccc(C2(S(C)(=O)=O)CC3(COC3)C2)cc1]

To a solution of 2-(4-{6-methanesulfonyl-2-oxaspiro[3.3]heptan-6-yl}phenoxy)ethan-1-ol (280 mg, 0.896 mmol) in DCM (5 mL) was added TEA (0.250 mL, 1.79 mmol) and methanesulfonic anhydride (234 mg, 1.34 mmol). The mixture was stirred at room temperature for 1 h, and then was quenched with $H_2O$ (10 mL). The resulting biphasic mixture was adjusted to pH=6-7 with 2.0 M aqueous HCl solution, and then was extracted with DCM (2×10 mL). The combined organic layers were washed with brine (2×20 mL), dried over Na$_2$SO$_4$, filtered, and concentrated in vacuo to give 2-(4-{6-methanesulfonyl-2-oxaspiro[3.3]heptan-6-yl}phenoxy)ethyl methanesulfonate (Intermediate A-42), which was used in the subsequent step without further purification. MS=391.1 [M+H]$^+$.

General Procedure for Intermediate A-43

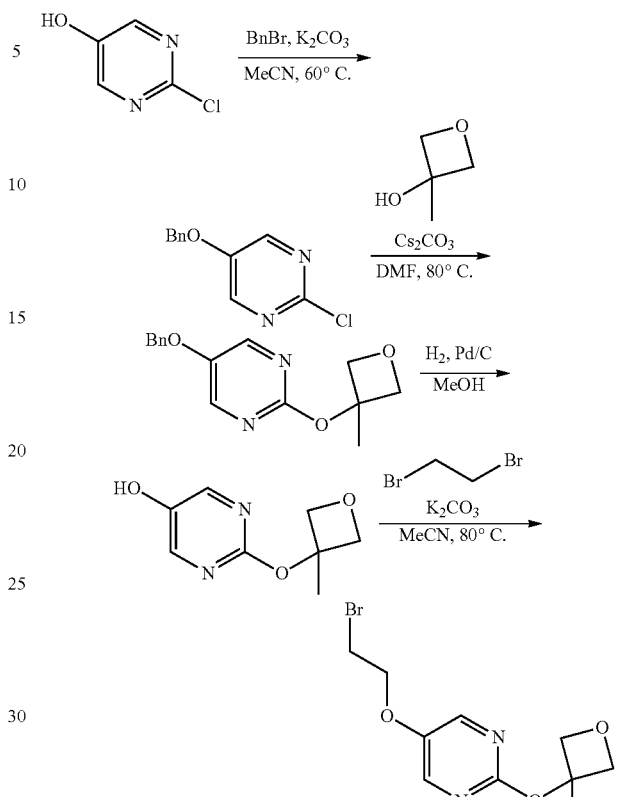

Step 1: 5-(benzyloxy)-2-chloropyrimidine

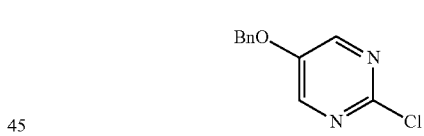

To a solution of 2-chloropyrimidin-5-ol (5.00 g, 38.3 mmol) and benzyl bromide (5.46 mL, 46.0 mmol) in MeCN (50 mL) was added K$_2$CO$_3$ (7.94 g, 57.5 mmol). The mixture was stirred at 60° C. for 2 h. After cooling to room temperature, the mixture was filtered, and the filtrate was concentrated in vacuo. The crude residue was purified by normal phase silica gel chromatography (Biotage 40 g cartridge, 0-15% EtOAc:petroleum ether) to give 5-(benzyloxy)-2-chloropyrimidine. MS=221.1 [M+H]$^+$.

Step 2: 5-(benzyloxy)-2-[(3-methyloxetan-3-yl)oxy]pyrimidine

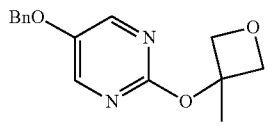 [SMILES: CC1(Oc2ncc(OCc3ccccc3)cn2)COC1]

To a solution of 3-methyloxetan-3-ol (1.20 g, 13.6 mmol) and 5-benzyloxy-2-chloro-pyrimidine (1.00 g, 4.53 mmol)

in DMF (20 mL) was added Cs₂CO₃ (4.43 g, 13.6 mmol). The mixture was stirred at room temperature for 6 h. Solids were removed by filtration, and the filtrate was concentrated under reduced pressure. The crude residue was purified by normal phase silica gel chromatography (Biotage 20 g cartridge, 0-15% EtOAc:petroleum ether) to give 5-(benzyloxy)-2-[(3-methyloxetan-3-yl)oxy]pyrimidine. MS=273.1 [M+H]⁺.

Step 3: 2-[(3-methyloxetan-3-yl)oxy]pyrimidin-5-ol

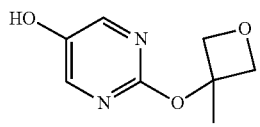

To a suspension of Pd/C (150 mg, 10 wt %, 0.14 mmol) in MeOH (15 mL) was added 5-(benzyloxy)-2-[(3-methyloxetan-3-yl)oxy]pyrimidine (600 mg, 2.20 mmol) under an atmosphere of N₂. The suspension was degassed and purged with H₂ (3×). The mixture was stirred at room temperature under H₂ (15 psi) for 3 h. The mixture was filtered through a pad of Celite, and the filter cake was washed with MeOH. The filtrate was concentrated in vacuo to give 2-[(3-methyloxetan-3-yl)oxy]pyrimidin-5-ol. MS=183.1 [M+H]⁺.

Step 4: 5-(2-bromoethoxy)-2-[(3-methyloxetan-3-yl)oxy]pyrimidine

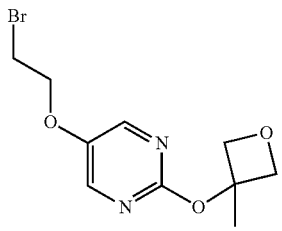 [SMILES: CC1(Oc2ncc(OCCBr)cn2)COC1]

To a solution of 2-[(3-methyloxetan-3-yl)oxy]pyrimidin-5-ol (370 mg, 2.03 mmol) and 1,2-dibromoethane (6.13 mL, 81.2 mmol) in MeCN (8 mL) was added K₂CO₃ (1.40 g, 10.2 mmol). The mixture was stirred at 80° C. for 16 h. After cooling to room temperature, the mixture was concentrated in vacuo. The residue was diluted with H₂O (30 mL) and extracted with EtOAc (2×20 mL), dried over Na₂SO₄, filtered, and concentrated in vacuo. The crude residue was purified by normal phase silica gel chromatography (Biotage 12 g cartridge, 0-15% EtOAc:petroleum ether) to give 2-[(3-methyloxetan-3-yl)oxy]pyrimidin-5-ol (Intermediate A-43). MS=289.0/291.0 [M+H]⁺.

General Procedure for Intermediate A-44

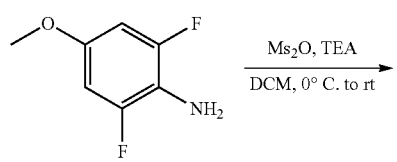

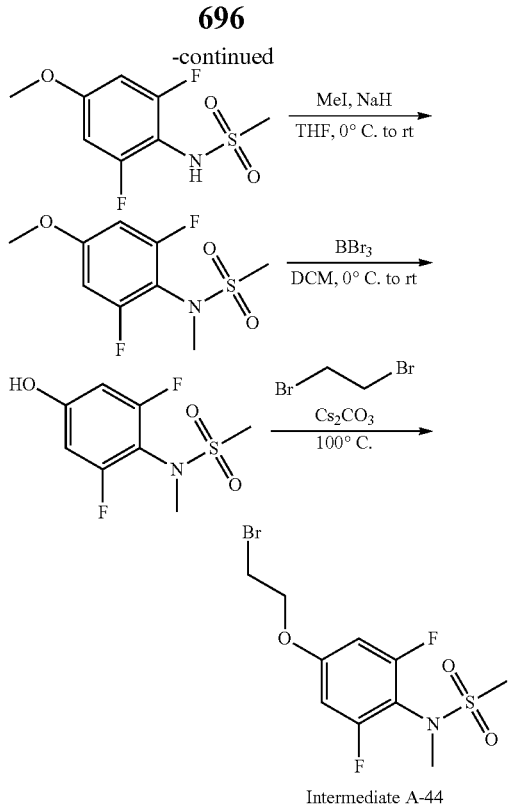

Intermediate A-44

Step 1: N-(2,6-difluoro-4-methoxyphenyl)methanesulfonamide

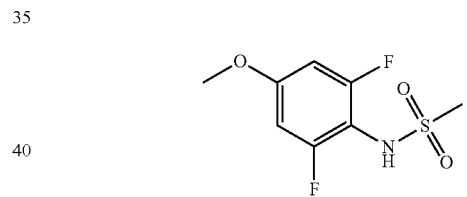

To a 0° C. mixture of 2,6-difluoro-4-methoxyaniline (3.00 g, 18.9 mmol) and TEA (3.15 mL, 22.6 mmol) in DCM (30 mL) was added methanesulfonic anhydride (8.21 g, 47.1 mmol) dropwise. The mixture was stirred at room temperature for 10 h. The reaction mixture was quenched with H₂O (30 mL) and extracted with EtOAc (3×50 mL). The combined organic layers were dried over Na₂SO₄, filtered, and concentrated in vacuo. The crude residue was purified by normal phase silica gel chromatography (Biotage 40 g cartridge, 0-50% EtOAc:petroleum ether) to give N-(2,6-difluoro-4-methoxyphenyl)methanesulfonamide. MS=236.1 [M−H]⁻.

Step 2: N-(2,6-difluoro-4-methoxyphenyl)-N-methylmethanesulfonamide

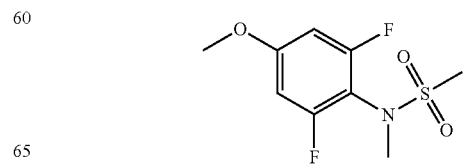

To a 0° C. solution of N-(2,6-difluoro-4-methoxyphenyl)methanesulfonamide (1.00 g, 4.22 mmol) in THF (10 mL) was added NaH (184 mg, 60 wt % in mineral oil, 4.59 mmol). After stirring at 0° C. for 15 min, MeI (2.62 mL, 42.2 mmol) was added. The mixture was stirred at room temperature for 5 h. The reaction mixture was cooled to 0° C., quenched with $H_2O$ (30 mL), and extracted with EtOAc (3×50 mL). The combined organic layers were dried over $Na_2SO_4$, filtered, and concentrated in vacuo. The crude residue was purified by normal phase silica gel chromatography (Biotage 20 g cartridge, 0-30% EtOAc:petroleum ether) to give N-(2,6-difluoro-4-methoxyphenyl)-N-methylmethanesulfonamide. MS=252.1 $[M+H]^+$.

Step 3: N-(2,6-difluoro-4-hydroxyphenyl)-N-methylmethanesulfonamide

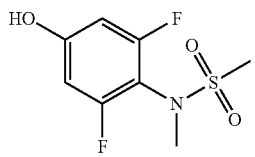

To a 0° C. solution of N-(2,6-difluoro-4-methoxyphenyl)-N-methylmethanesulfonamide (786 mg, 3.13 mmol) in DCM (8 mL) was added $BBr_3$ (0.904 mL, 9.39 mmol) dropwise. The mixture was stirred at room temperature for 6 h. The reaction mixture was cooled to 0° C. and quenched with $H_2O$ (10 mL). The resulting biphasic mixture was concentrated in vacuo to remove DCM and the remaining aqueous phase was adjusted to pH=8-9 with saturated aqueous $NaHCO_3$. The resulting solid was isolated via filtration and washed with MTBE. The filter cake was dried in vacuo to give N-(2,6-difluoro-4-hydroxyphenyl)-N-methylmethanesulfonamide. MS=238.1 $[M+H]^+$.

Step 4: N-[4-(2-bromoethoxy)-2,6-difluorophenyl]-N-methylmethanesulfonamide

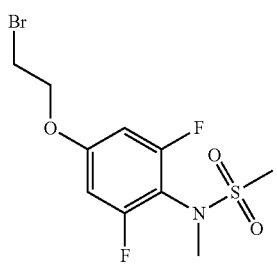 [SMILES: CN(c1c(F)cc(OCCBr)cc1F)S(C)(=O)=O]

To a solution of N-(2,6-difluoro-4-hydroxyphenyl)-N-methylmethanesulfonamide (710 mg, 2.99 mmol) in 1,2-dibromoethane (10 mL) was added $Cs_2CO_3$ (1.95 g, 5.99 mmol). The mixture was stirred at 100° C. for 4 h. The reaction mixture was cooled to 0° C., quenched with $H_2O$ (20 mL), and extracted with EtOAc (3×15 mL). The combined organic layers were dried over $Na_2SO_4$, filtered, and concentrated in vacuo. The crude residue was purified by normal phase silica gel chromatography (Biotage 20 g cartridge, 0-30% EtOAc:petroleum ether) to give N-[4-(2-bromoethoxy)-2,6-difluorophenyl]-N-methylmethanesulfonamide (Intermediate A-44). MS=361.1/363.1 $[M+NH_4]^+$.

General Procedure for Intermediate A-45

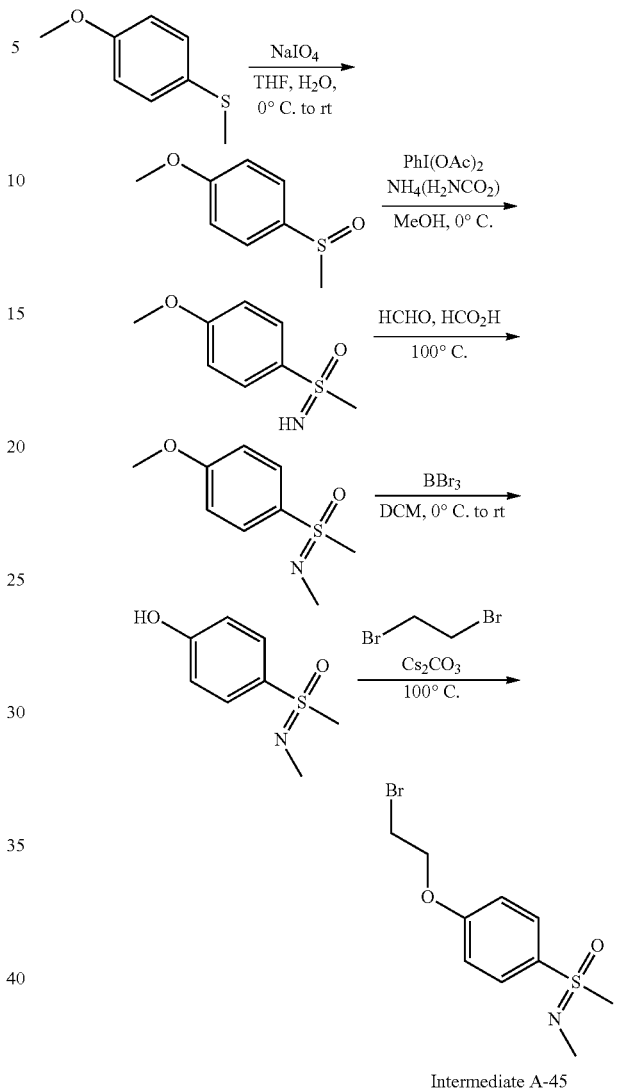

Intermediate A-45

Step 1: 1-methanesulfinyl-4-methoxybenzene

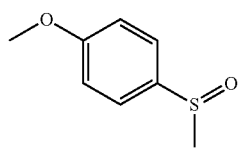

To a 0° C. solution of 1-methoxy-4-(methylsulfanyl)benzene (15.3 mL, 110 mmol) in THF (160 mL) and $H_2O$ (160 mL) was added $NaIO_4$ (12.2 mL, 220 mmol) portionwise. The mixture was allowed to warm to room temperature and stirred for 16 h, and then solids were removed by filtration. The filtrate was cooled to 0° C., quenched with saturated aqueous $Na_2SO_3$ solution (200 mL), and extracted with EtOAc (5×200 mL). The combined organic layers were washed with saturated aqueous $Na_2SO_3$ solution (2×200 mL), dried over $Na_2SO_4$, filtered, and concentrated in vacuo to give 1-methanesulfinyl-4-methoxybenzene, which was used in the subsequent step without further purification. MS=171.1 [M+H]$^+$.

Step 2: imino(4-methoxyphenyl)methyl-λ$^6$-sulfanone

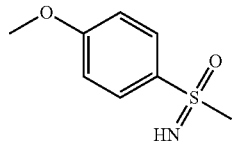

To a 0° C. solution of 1-methanesulfinyl-4-methoxybenzene (110 mmol) and PhI(OAc)$_2$ (15 g, 470 mmol) in MeOH (200 mL) was added ammonium carbamate (13.8 g, 176 mmol). The mixture was stirred at 0° C. for 1 h, and then was concentrated in vacuo. The residue was diluted with H$_2$O (100 mL) and adjusted to pH=6-7 with the dropwise addition of saturated aqueous Na$_2$CO$_3$. Solids were removed by filtration, and the filtrate was extracted with EtOAc (5×200 mL). The combined organic layers were dried over Na$_2$SO$_4$, filtered, and concentrated in vacuo. The crude residue was purified by normal phase silica gel chromatography (Biotage 330 g cartridge, 80-100% EtOAc:petroleum ether) to give imino(4-methoxyphenyl)methyl-λ$^6$-sulfanone. MS=186.1 [M+H]$^+$.

Step 3: [(4-methoxyphenyl)(methyl)oxo-λ$^6$-sulfanylidene](methyl)amine

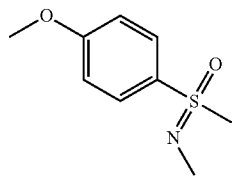

A solution of imino(4-methoxyphenyl)methyl-λ$^6$-sulfanone (10.0 g, 54.0 mmol) and formaldehyde aqueous solution (29.7 mL, 37 wt %, 1.08 mol) in formic acid (100 mL) was stirred at 100° C. for 30 h. The mixture was cooled to 0° C. and then diluted with H$_2$O (120 mL). The solution was adjusted to pH=6-7 with the dropwise addition of 5.0 M aqueous NaOH. The mixture was extracted with EtOAc (3×120 mL). The combined organic layers were washed with brine (80 mL), dried over anhydrous Na$_2$SO$_4$, filtered and concentrated in vacuo to give [(4-methoxyphenyl)(methyl)oxo-λ$^6$-sulfanylidene](methyl)amine, which was used in the subsequent step without further purification. MS=200.2 [M+H]$^+$.

Step 4: 4-[methyl(methylimino)oxo-λ$^6$-sulfanyl]phenol

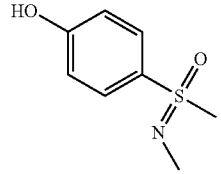

To a 0° C. solution of [(4-methoxyphenyl)(methyl)oxo-λ$^6$-sulfanylidene](methyl)amine (11.0 g, 55.2 mmol) in DCM (120 mL) was added BBr$_3$ (21.3 mL, 221 mmol). The mixture was stirred at room temperature for 2 h, then was cooled to 0° C. and quenched by the addition of H$_2$O (15 mL). The solution was adjusted to pH=6-8 with the dropwise addition of saturated aqueous NaHCO$_3$. The resulting solids were removed by filtration and the filter cake was washed with THF (3×200 mL). The resulting filtrate was concentrated in vacuo, and the resulting residue was triturated with a 1:1 mixture of petroleum ether and EtOAc, then dried in vacuo to give 4-[methyl(methylimino)oxo-λ$^6$-sulfanyl]phenol. MS=186.0 [M+H]$^+$.

Step 5: {[4-(2-bromoethoxy)phenyl](methyl)oxo-λ$^6$-sulfanylidene}(methyl)amine

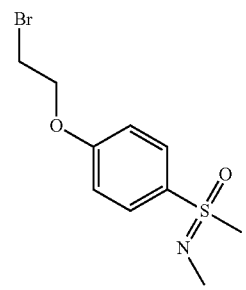

To a mixture of 4-[methyl(methylimino)oxo-λ$^6$-sulfanyl]phenol (900 mg, 4.86 mmol) and 1,2-dibromoethane (10.0 mL, 133 mmol) was added Cs$_2$CO$_3$ (3.17 g, 9.72 mmol). The mixture was stirred at 100° C. for 16 h. After cooling to room temperature, solids were removed via filtration and the filtrate was concentrated in vacuo. The crude residue was purified by normal phase silica gel chromatography (Biotage 20 g cartridge, 0-50% EtOAc:petroleum ether) to give {[4-(2-bromoethoxy)phenyl](methyl)oxo-λ$^6$-sulfanylidene}(methyl)amine (Intermediate A-45). MS=291.9/293.9 [M+H]$^+$.

General Procedure for Intermediate A-46

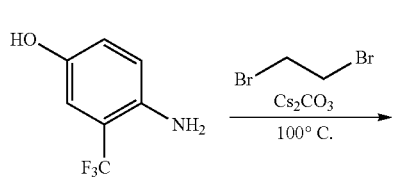

Step 2: N-[4-(2-bromoethoxy)-2-(trifluoromethyl)phenyl]-N-methanesulfonylmethanesulfonamide

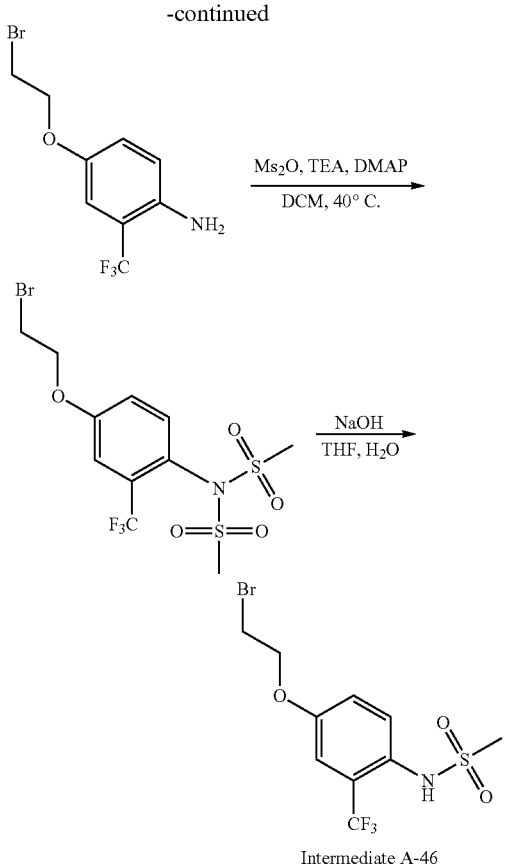

Intermediate A-46

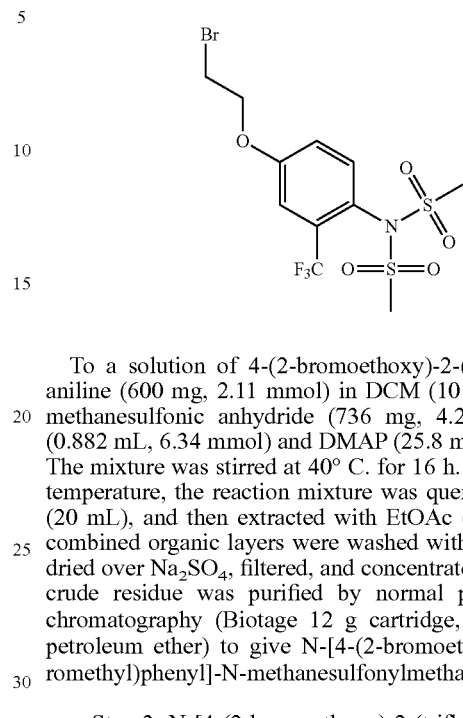

To a solution of 4-(2-bromoethoxy)-2-(trifluoromethyl) aniline (600 mg, 2.11 mmol) in DCM (10 mL) was added methanesulfonic anhydride (736 mg, 4.22 mmol), TEA (0.882 mL, 6.34 mmol) and DMAP (25.8 mg, 0.211 mmol). The mixture was stirred at 40° C. for 16 h. After cooling to temperature, the reaction mixture was quenched with $H_2O$ (20 mL), and then extracted with EtOAc (3×20 mL). The combined organic layers were washed with brine (25 mL), dried over $Na_2SO_4$, filtered, and concentrated in vacuo. The crude residue was purified by normal phase silica gel chromatography (Biotage 12 g cartridge, 0-50% EtOAc: petroleum ether) to give N-[4-(2-bromoethoxy)-2-(trifluoromethyl)phenyl]-N-methanesulfonylmethanesulfonamide.

Step 3: N-[4-(2-bromoethoxy)-2-(trifluoromethyl)phenyl]methanesulfonamide

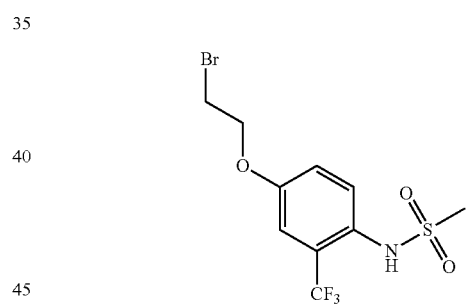

To a solution of N-[4-(2-bromoethoxy)-2-(trifluoromethyl)phenyl]-N-methanesulfonylmethanesulfonamide (521 mg, 1.18 mmol) in THF (6 mL) was added a solution of NaOH (237 mg, 5.92 mmol) in $H_2O$ (1.5 mL). The mixture was stirred at room temperature for 16 h. The reaction mixture was quenched with $H_2O$ (10 mL), and then extracted with EtOAc (3×10 mL). The combined organic layers were washed with brine (15 mL), dried over $Na_2SO_4$, filtered and concentrated in vacuo to give N-[4-(2-bromoethoxy)-2-(trifluoromethyl)phenyl]methanesulfonamide (Intermediate A-46). MS=359.9/362.0 [M−H]⁻.

General Procedure for Intermediate A-47

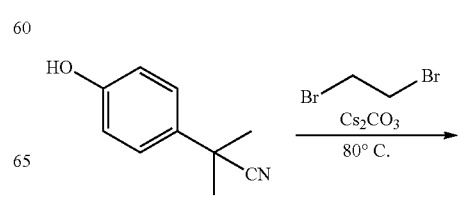

Step 1: 4-(2-bromoethoxy)-2-(trifluoromethyl)aniline

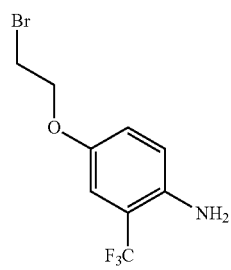 [SMILES: Nc1ccc(OCCBr)cc1C(F)(F)F]

To a solution 4-amino-3-(trifluoromethyl)phenol (3.00 g, 16.9 mmol) in 1,2-dibromoethane (30 mL, 399 mmol) was added $Cs_2CO_3$ (16.6 g, 50.8 mmol). The mixture was stirred at 100° C. for 12 h. After cooling to room temperature, the mixture was filtered and concentrated in vacuo. The crude residue was purified by normal phase silica gel chromatography (Biotage 40 g cartridge, 0-50% EtOAc:petroleum ether) to give 4-(2-bromoethoxy)-2-(trifluoromethyl) aniline. MS=284.0/286.0 [M+H]⁺.

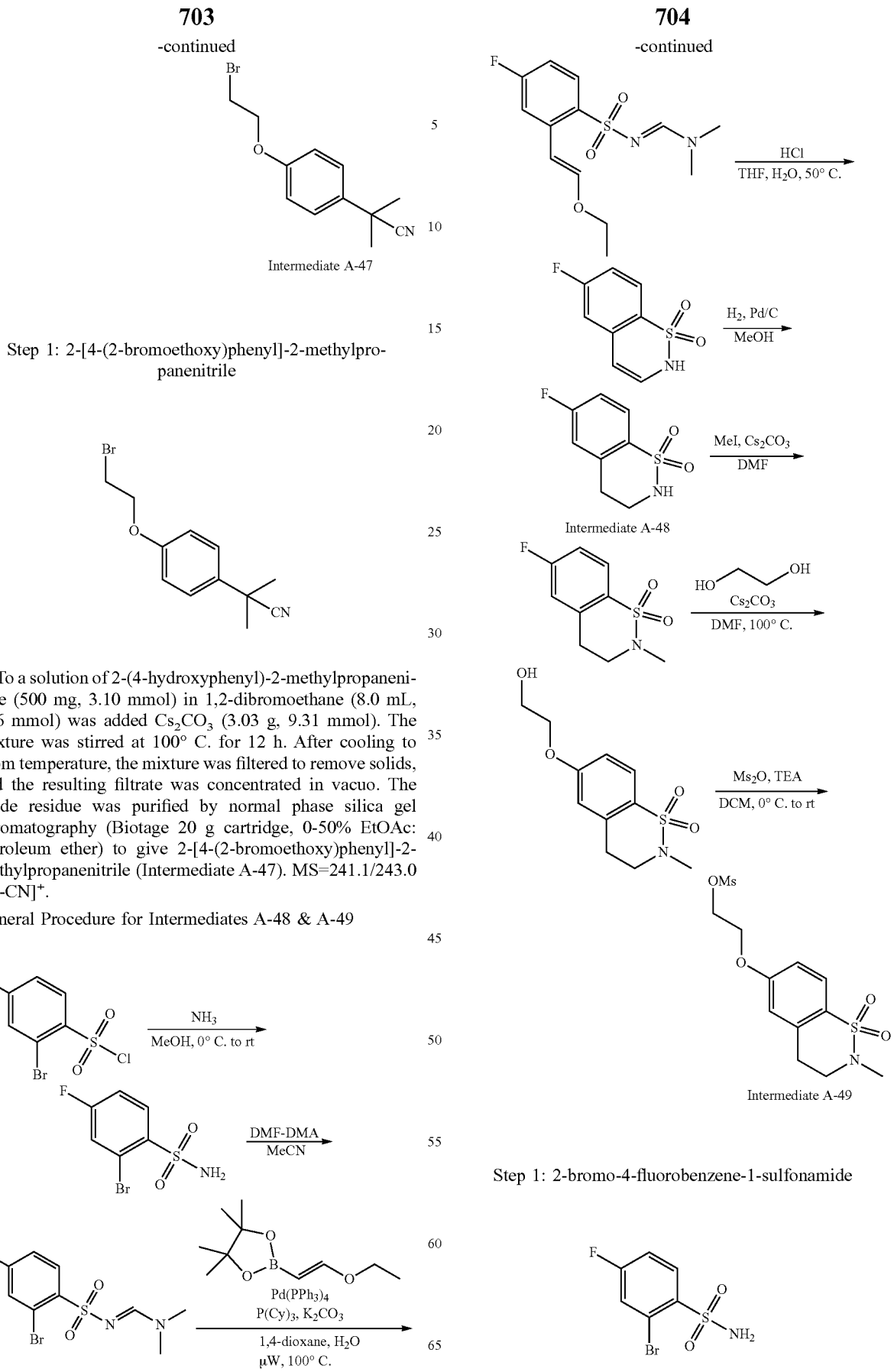

Step 1: 2-[4-(2-bromoethoxy)phenyl]-2-methylpropanenitrile

To a solution of 2-(4-hydroxyphenyl)-2-methylpropanenitrile (500 mg, 3.10 mmol) in 1,2-dibromoethane (8.0 mL, 106 mmol) was added $Cs_2CO_3$ (3.03 g, 9.31 mmol). The mixture was stirred at 100° C. for 12 h. After cooling to room temperature, the mixture was filtered to remove solids, and the resulting filtrate was concentrated in vacuo. The crude residue was purified by normal phase silica gel chromatography (Biotage 20 g cartridge, 0-50% EtOAc: petroleum ether) to give 2-[4-(2-bromoethoxy)phenyl]-2-methylpropanenitrile (Intermediate A-47). MS=241.1/243.0 [M-CN]$^+$.

General Procedure for Intermediates A-48 & A-49

Step 1: 2-bromo-4-fluorobenzene-1-sulfonamide

A solution of 2-bromo-4-fluorobenzene-1-sulfonyl chloride (1.07 mL, 7.31 mmol) in MeOH (30 mL) was cooled to 0° C. and NH$_3$ was bubbled into the reaction mixture over a period of 15 min. The reaction mixture was warmed to room temperature and stirred for 16 h. The mixture was concentrated in vacuo and diluted with H$_2$O (100 mL). The reaction mixture was extracted with EtOAc (2×100 mL). The combined organic layers were dried over Na$_2$SO$_4$, filtered, and concentrated in vacuo give 2-bromo-4-fluorobenzene-1-sulfonamide, which was used in the subsequent step without further purification.

Step 2: N'-(2-bromo-4-fluorobenzenesulfonyl)-N,N-dimethylmethanimidamide

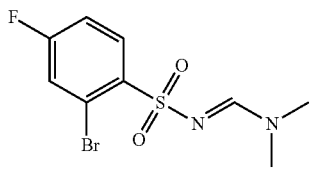 [SMILES: CN(C)/C=N/S(=O)(=O)c1ccc(F)cc1Br]

To a mixture of 2-bromo-4-fluorobenzene-1-sulfonamide (1.00 g, 3.94 mmol) in MeCN (10 mL) was added a solution N,N-dimethylformamide dimethyl acetal (0.627 mL, 4.72 mmol) in MeCN (1 mL). The mixture was stirred at room temperature for 1 h, and was then concentrated in vacuo to give N-(2-bromo-4-fluorobenzenesulfonyl)-N,N-dimethylmethanimidamide, which was used in the subsequent step without further purification. MS=309.0/311.0 [M+H]$^+$.

Step 3: N'-{2-[(1E)-2-ethoxyethenyl]-4-fluorobenzenesulfonyl}-N,N-dimethylmethanimidamide

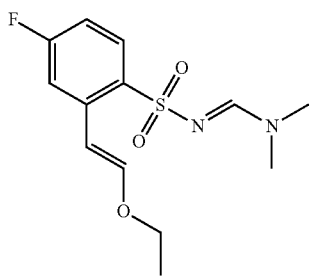 [SMILES: CCO/C=C/c1cc(F)ccc1S(=O)(=O)/N=C/N(C)C]

A solution of 2-[(1E)-2-ethoxyethenyl]-4,4,5,5-tetramethyl-1,3,2-dioxaborolane (895 mg, 4.52 mmol), N'-(2-bromo-4-fluorobenzenesulfonyl)-N,N-dimethylmethanimidamide (700 mg, 2.26 mmol), K$_2$CO$_3$ (937 mg, 6.78 mmol), Pd(PPh$_3$)$_4$ (261 mg, 0.226 mmol), and PCy$_3$ (73.3 μL, 0.226 mmol) in 1,4-dioxane (5 mL) and H$_2$O (0.5 mL) was purged with N$_2$ (2×) and heated via microwave for 1 h at 100° C. After cooling to room temperature, the mixture was extracted with EtOAc (3×10 mL). The combined organic layers were dried over Na$_2$SO$_4$, filtered, and concentrated in vacuo. The crude residue was purified by normal phase silica gel chromatography (Biotage 10 g cartridge, 0-30% EtOAc: petroleum ether) to give N-{2-[(1E)-2-ethoxyethenyl]-4-fluorobenzenesulfonyl}-N,N-dimethylmethanimidamide. MS=301.1 [M+H]$^+$.

Step 4: 6-fluoro-2H-1λ$^6$,2-benzothiazine-1,1-dione

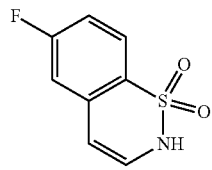 [SMILES: O=S1(=O)NC=Cc2cc(F)ccc21]

A solution of N-{2-[(1E)-2-ethoxyethenyl]-4-fluorobenzenesulfonyl}-N,N-dimethylmethanimidamide (500 mg, 1.66 mmol) in 6.0 M aqueous HCl (2.77 mL, 16.6 mmol) and THF (5 mL) was stirred at 50° C. for 16 h. After cooling to room temperature, the mixture was concentrated in vacuo. The residue was extracted with EtOAc (3×5 mL). The combined organic layers were dried over Na$_2$SO$_4$, filtered, and concentrated in vacuo to give 6-fluoro-2H-1λ$^6$,2-benzothiazine-1,1-dione, which was used in the subsequent step without further purification. MS=198.1 [M−H]$^-$.

Step 5: 6-fluoro-3,4-dihydro-2H-1λ$^6$,2-benzothiazine-1,1-dione

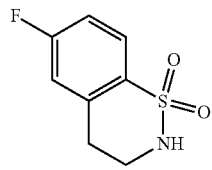 [SMILES: O=S1(=O)NCCc2cc(F)ccc21]

To a mixture of Pd/C (10.0 mg, 10 wt %, 0.0094 mmol) in MeOH (3 mL) was added 6-fluoro-2H-1λ$^6$,2-benzothiazine-1,1-dione (50.0 mg, 0.251 mmol). The mixture was purged with H$_2$ (2×). The mixture was stirred at room temperature for 16 h under an atmosphere of H$_2$ (15 psi). The reaction mixture filtered through celite, and the filtrate was concentrated in vacuo. The crude residue was purified by normal phase silica gel chromatography (Biotage 4 g cartridge, 0-50% EtOAc:petroleum ether) to give 6-fluoro-3,4-dihydro-2H-1λ$^6$,2-benzothiazine-1,1-dione (Intermediate A-48). MS=200.0 [M−H]$^-$.

Step 6: 6-fluoro-2-methyl-3,4-dihydro-21-1λ$^6$,2-benzothiazine-1,1-dione

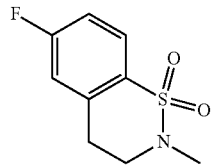

To a solution of 6-fluoro-3,4-dihydro-2H-1λ$^6$,2-benzothiazine-1,1-dione (500 mg, 2.48 mmol) and Cs$_2$CO$_3$ (891 mg, 2.73 mmol) in DMF (10 mL) was added MeI (1.55 mL, 24.9 mmol). The mixture was stirred at room temperature for 3 h and was then diluted with H$_2$O (10 mL). The mixture was extracted with EtOAc (3×5 mL). The combined organic layers were washed with brine (2×5 mL), dried over Na₂SO₄, filtered, and concentrated in vacuo to give 6-fluoro-2-methyl-3,4-dihydro-2H-1λ⁶,2-benzothiazine-1,1-dione, which was used in the subsequent step without further purification. MS=216.1 [M+H]⁺.

Step 7: 6-(2-hydroxyethoxy)-2-methyl-3,4-dihydro-2H-1λ⁶,2-benzothiazine-1,1-dione

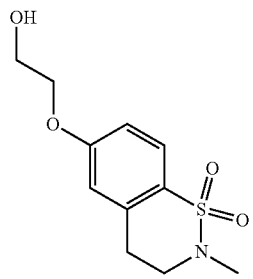 [SMILES: CN1CCc2cc(OCCO)ccc2S1(=O)=O]

A solution of 6-fluoro-2-methyl-3,4-dihydro-2H-1λ⁶,2-benzothiazine-1,1-dione (700 mg, 3.25 mmol), ethylene glycol (1.82 mL, 32.5 mmol) and Cs₂CO₃ (3.18 g, 9.76 mmol) in DMF (3 mL) was stirred at 100° C. for 5 h. After cooling to room temperature, the mixture was extracted with EtOAc (3×5 mL). The combined organic layers were washed with brine (2×5 mL), dried over Na₂SO₄, filtered, and concentrated in vacuo. The crude residue was purified by normal phase silica gel chromatography (Biotage 4 g cartridge, 0-60% EtOAc:petroleum ether) to give 6-(2-hydroxyethoxy)-2-methyl-3,4-dihydro-2H-1λ⁶,2-benzothiazine-1,1-dione. MS=258.0 [M+H]⁺.

Step 8: 2-[(2-methyl-1,1-dioxo-3,4-dihydro-2H-1λ⁶,2-benzothiazin-6-yl)oxy]ethyl methanesulfonate

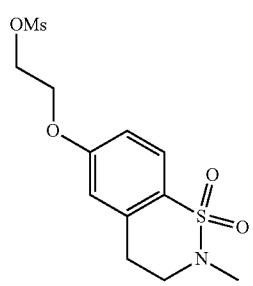 [SMILES: CN1CCc2cc(OCCOS(C)(=O)=O)ccc2S1(=O)=O]

To a 0° C. solution of 6-(2-hydroxyethoxy)-2-methyl-3,4-dihydro-2H-1λ⁶,2-benzothiazine-1,1-dione (180 mg, 0.700 mmol) and TEA (0.146 mL, 1.05 mmol) in DCM (5 mL) was added methanesulfonic anhydride (146 mg, 0.839 mmol). After stirring at 0° C. for 1 h, the reaction mixture was quenched with H₂O (3 mL). The solution was adjusted to pH=6 with the dropwise addition of 2.0 M aqueous HCl. The mixture was extracted with DCM (3×5 mL). The combined organic layers were dried over Na₂SO₄, filtered, and concentrated in vacuo to give 2-[(2-methyl-1,1-dioxo-3,4-dihydro-2H-1)⁶,2-benzothiazin-6-yl)oxy]ethyl methanesulfonate, which was used in the subsequent step without further purification (Intermediate A-49). MS=336.1 [M+H]⁺.

General Procedure for Intermediate A-50

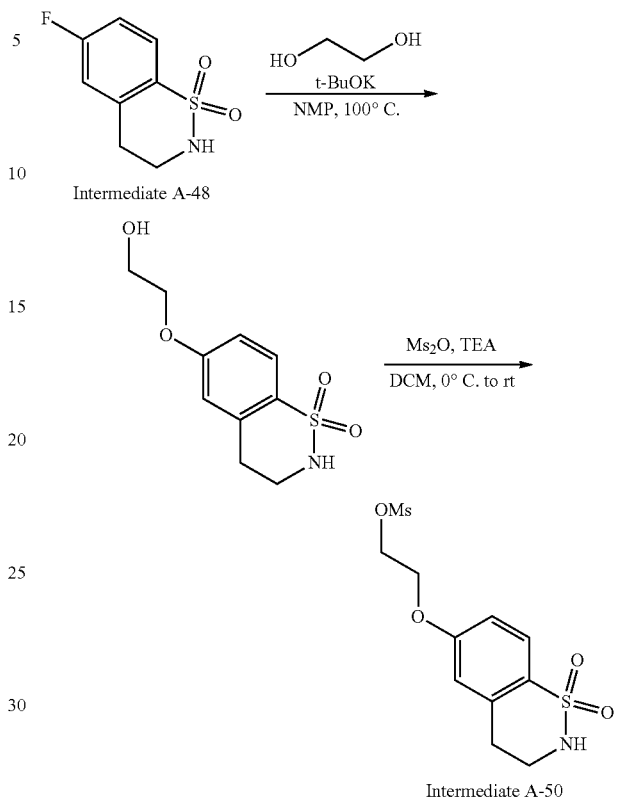

Step 1: 6-(2-hydroxyethoxy)-3,4-dihydro-2H-1λ⁶,2-benzothiazine-1,1-dione

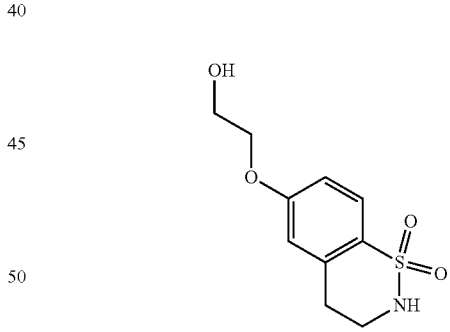

A solution of 6-fluoro-3,4-dihydro-2H-1)⁶,2-benzothiazine-1,1-dione (Intermediate A-48, 2.50 g, 12.4 mmol), ethylene glycol (3.47 mL, 62.1 mmol) and t-BuOK (6.97 g, 62.1 mmol) in NMP (15 mL) was stirred at 100° C. for 16 h. After cooling to room temperature, the reaction was quenched with H₂O (30 mL) and extracted with EtOAc (3×20 mL). The combined organic layers were washed with brine (20 mL), dried over Na₂SO₄, filtered, and concentrated in vacuo. The crude residue was purified by normal phase silica gel chromatography (Biotage 20 g cartridge, 0-100% EtOAc:petroleum ether) to give 6-(2-hydroxyethoxy)-3,4-dihydro-2H-1λ⁶,2-benzothiazine-1,1-dione. MS=242.1 [M−H]⁻.

Step 2: 2-[(1,1-dioxo-3,4-dihydro-2H-1λ⁶,2-benzo-thiazin-6-yl)oxy]ethyl methanesulfonate

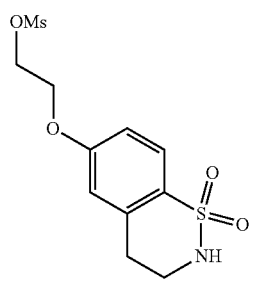 [SMILES: CS(=O)(=O)OCCOc1ccc2c(c1)CCNS2(=O)=O]

To a 0° C. solution of 6-(2-hydroxyethoxy)-3,4-dihydro-2H-1)⁶,2-benzothiazine-1,1-dione (400 mg, 1.64 mmol) and TEA (0.343 mL, 2.47 mmol) in DCM (5 mL) was added methanesulfonic anhydride (344 mg, 1.97 mmol). After stirring at 0° C. for 1 h, the reaction mixture was quenched with H₂O (3 mL). The solution was adjusted to pH=6 with the dropwise addition of 2.0 M aqueous HCl. The mixture was extracted with DCM (3×5 mL). The combined organic layers were dried over Na₂SO₄, filtered, and concentrated in vacuo. The crude residue was purified by normal phase silica gel chromatography (Biotage 4 g cartridge, 0-80% EtOAc: petroleum ether) to give 2-[(1,1-dioxo-3,4-dihydro-2H-1λ⁶, 2-benzothiazin-6-yl)oxy]ethyl methanesulfonate (Intermediate A-50). MS=320.1 [M−H]⁻.

General Procedure for Intermediate A-51

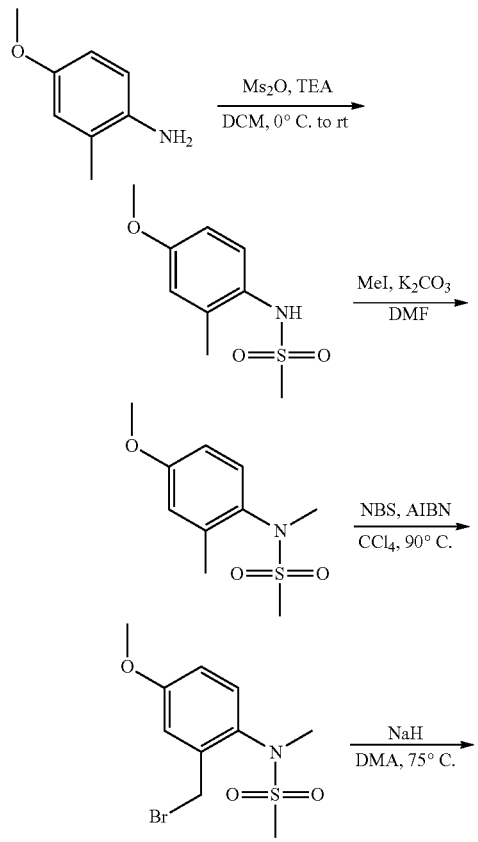

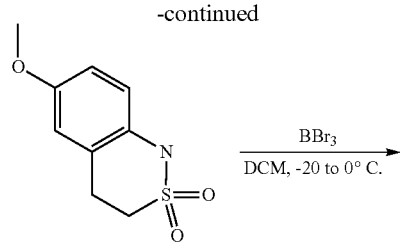

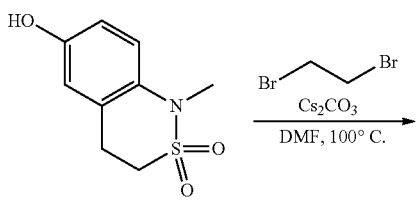

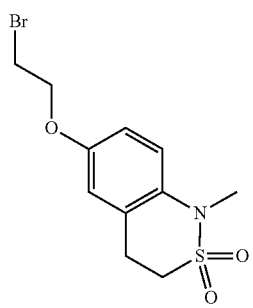

Intermediate A-51

Step 1:
N-(4-methoxy-2-methylphenyl)methanesulfonamide

To a 0° C. solution of 4-methoxy-2-methylaniline (7.41 mL, 58.3 mmol) and TEA (12.2 mL, 87.4 mmol) in DCM (50 mL) was added methanesulfonic anhydride (11.2 g, 64.2 mmol). After stirring at room temperature for 1 h, the reaction mixture was quenched with H₂O (35 mL). The solution was adjusted to pH=6 with the dropwise addition of 1.0 M aqueous HCl. The mixture was extracted with DCM (3×25 mL). The combined organic layers were dried over Na₂SO₄, filtered, and concentrated in vacuo. The crude product was triturated with EtOAc, and the solid was isolated via filtration then concentrated in vacuo to give N-(4-methoxy-2-methylphenyl)methanesulfonamide. MS=214.2 [M−H]⁻.

Step 2: N-(4-methoxy-2-methylphenyl)-N-methyl-methanesulfonamide

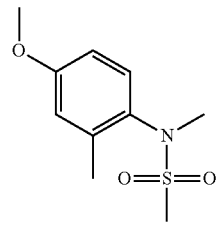

A solution of N-(4-methoxy-2-methylphenyl)methanesulfonamide (10.0 g, 46.5 mmol), MeI (4.34 mL, 69.68 mmol) and $K_2CO_3$ (12.8 g, 92.9 mmol) in DMF (30 mL) was stirred at for 2 h. The reaction mixture was quenched with $H_2O$ (15 mL) and extracted with EtOAc (3×30 mL). The combined organic layers were washed with brine (2×20 mL), dried over $Na_2SO_4$, filtered, and concentrated in vacuo to give N-(4-methoxy-2-methylphenyl)-N-methylmethanesulfonamide, which was used in the subsequent step without further purification.

Step 3: N-[2-(bromomethyl)-4-methoxyphenyl]-N-methylmethanesulfonamide

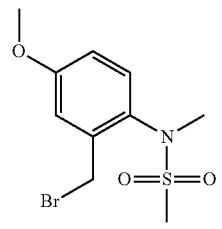 [SMILES: COc1ccc(N(C)S(C)(=O)=O)c(CBr)c1]

A solution N-(4-methoxy-2-methylphenyl)-N-methylmethanesulfonamide (5.00 g, 21.8 mmol), NBS (4.66 g, 26.2 mmol) and AIBN (71.6 mg, 0.436 mmol) in $CCl_4$ (50 mL) was stirred at 90° C. for 2 h. After cooling to room temperature, the reaction mixture was diluted with $H_2O$ (50 mL) and extracted with EtOAc (2×50 mL). The combined organic layers were dried over $Na_2SO_4$, filtered, and concentrated in vacuo. The crude residue was purified by normal phase silica gel chromatography (Biotage 40 g cartridge, 0-80% EtOAc:petroleum ether) to give N-[2-(bromomethyl)-4-methoxyphenyl]-N-methylmethanesulfonamide. MS=308.0/310.0 $[M+H]^+$.

Step 4: 6-methoxy-1-methyl-3,4-dihydro-1H-2$\lambda^6$,1-benzothiazine-2,2-dione

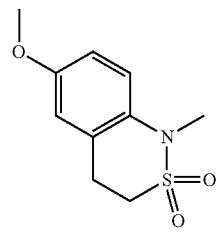

To a 0° C. solution of N-[2-(bromomethyl)-4-methoxyphenyl]-N-methylmethanesulfonamide (2.60 g, 8.44 mmol) in DMA (15 mL) was added NaH (371 mg, 60 wt % in mineral oil, 9.28 mmol) in portions. The mixture was stirred at 75° C. for 4 h. After cooling to room temperature, the reaction was quenched with $H_2O$ (20 mL). The mixture was extracted with EtOAc (3×15 mL). The combined organic layers were washed with brine (2×15 mL), dried over $Na_2SO_4$, filtered, and concentrated in vacuo. The crude residue was purified by normal phase silica gel chromatography (Biotage 12 g cartridge, 0-30% EtOAc:petroleum ether) to give 6-methoxy-1-methyl-3,4-dihydro-1H-2$\lambda^6$,1-benzothiazine-2,2-dione. MS=228.1 $[M+H]^+$.

Step 5: 6-hydroxy-1-methyl-3,4-dihydro-1H-2$^6$,1-benzothiazine-2,2-dione

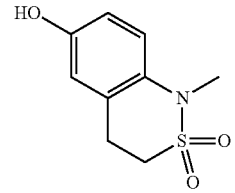

To a −20° C. solution of 6-methoxy-1-methyl-3,4-dihydro-1H-2$\lambda^6$,1-benzothiazine-2,2-dione (1.20 g, 5.28 mmol) in DCM (15 mL) was added $BBr_3$ (1.53 mL, 15.8 mmol) dropwise. The mixture was warmed to 0° C. and stirred for 1 h. The reaction mixture was quenched by the addition of $H_2O$ (15 mL), warmed to room temperature, and then adjusted to pH=8 with saturated aqueous $NaHCO_3$. The mixture was extracted with DCM (3×20 mL). The combined organic layers were washed with brine (15 mL), dried over $Na_2SO_4$, filtered, and concentrated in vacuo. The crude residue was purified by normal phase silica gel chromatography (Biotage 10 g cartridge, 0-30% EtOAc:petroleum ether) to give 6-hydroxy-1-methyl-3,4-dihydro-1H-2$\lambda^6$,1-benzothiazine-2,2-dione. MS=212.1 $[M-H]^-$.

Step 6: 6-(2-bromoethoxy)-1-methyl-3,4-dihydro-1H-2$\lambda^6$,1-benzothiazine-2,2-dione

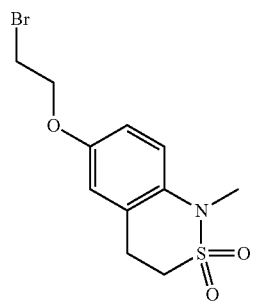 [SMILES: CN1c2ccc(OCCBr)cc2CCS1(=O)=O]

A solution of 1,2-dibromoethane (1.59 mL, 21.1 mmol), 6-hydroxy-1-methyl-3,4-dihydro-1H-2$\lambda^6$,1-benzothiazine-2,2-dione (900 mg, 4.22 mmol) and $Cs_2CO_3$ (2.06 g, 6.33 mmol) in DMF (2 mL) was stirred at 100° C. for 16 h. After cooling to room temperature, the reaction mixture was diluted with $H_2O$ (15 mL) and extracted with EtOAc (3×10 mL). The combined organic layers were washed with brine (2×10 mL), dried over Na$_2$SO$_4$, filtered, and concentrated in vacuo. The crude residue was purified by normal phase silica gel chromatography (Biotage 10 g cartridge, 0-30% EtOAc: petroleum ether) to give 6-(2-bromoethoxy)-1-methyl-3,4-dihydro-1H-2λ$^6$,1-benzothiazine-2,2-dione (Intermediate A-51). MS=319.9/321.9 [M+H]$^+$.

General Procedure for Intermediate A-52

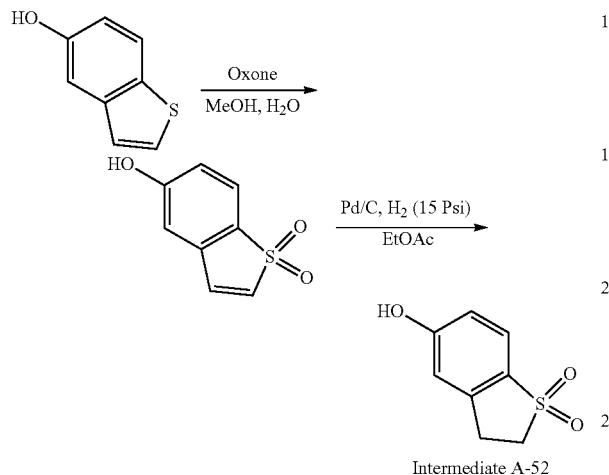

Step 1: 5-hydroxy-1λ$^6$-benzothiophene-1,1-dione

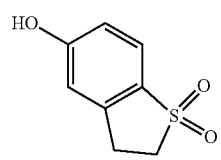

To a 0° C. solution of Oxone (1.84 g, 3.00 mmol) in H$_2$O (15 mL) was added a solution of 1-benzothiophen-5-ol (300 mg, 2.00 mmol) in MeOH (15 mL) dropwise. The mixture was stirred at room temperature for 6 h. The reaction mixture was concentrated in vacuo, diluted with H$_2$O (10 mL), and then extracted with EtOAc (3×20 mL). The combined organic layers were washed with brine (30 mL), dried over Na$_2$SO$_4$, filtered, and concentrated in vacuo. The crude residue was purified by normal phase silica gel chromatography (Biotage 12 g cartridge, 0-50% EtOAc:petroleum ether) to give 5-hydroxy-1λ$^6$-benzothiophene-1,1-dione. MS=181.1 [M−H]$^−$.

Step 2: 5-hydroxy-2,3-dihydro-1λ$^6$-benzothiophene-1,1-dione

To a solution of 5-hydroxy-1λ$^6$-benzothiophene-1,1-dione (270 mg, 1.48 mmol) in EtOAc (30 mL) was added Pd/C (27 mg, 10 wt %, 0.025 mmol) under N$_2$ atmosphere. The mixture was purged with H$_2$ (3×). The mixture was stirred at room temperature for 3 h under an atmosphere of H$_2$ (15 psi). The reaction mixture filtered through Celite, and the filtrate was concentrated in vacuo to give 5-hydroxy-2,3-dihydro-1λ$^6$-benzothiophene-1,1-dione (Intermediate A-52), which was used in the subsequent step without further purification. MS=183.1 [M−H]$^−$.

General Procedure for Intermediate A-53

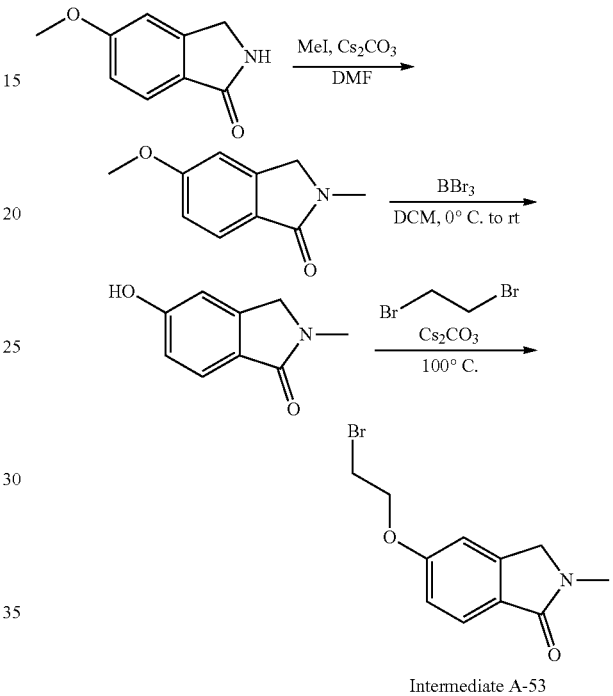

Step 1: 5-methoxy-2-methyl-2,3-dihydro-1H-isoindol-1-one

To a solution of 5-methoxy-2,3-dihydro-1H-isoindol-1-one (750 mg, 4.60 mmol,) in DMF (15 mL) were added Cs$_2$CO$_3$ (2.25 g, 6.89 mmol) and MeI (0.343 mL, 5.52 mmol). The mixture was stirred at room temperature for 16 h. The mixture was filtered to remove solids, and the resulting filtrate was concentrated in vacuo. The crude residue was purified by normal phase silica gel chromatography (Biotage 25 g cartridge, 50-100% EtOAc:petroleum ether) to give 5-methoxy-2-methyl-2,3-dihydro-1H-isoindol-1-one. MS=178.0 [M+H]$^+$.

Step 2: 5-hydroxy-2-methyl-2,3-dihydro-1H-isoindol-1-one

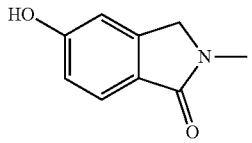

To a 0° C. solution of 5-methoxy-2-methyl-2,3-dihydro-1H-isoindol-1-one (800 mg, 4.51 mmol) in DCM (10 mL) was added BBr$_3$ (1.31 mL, 13.5 mmol). The mixture was stirred at room temperature for 2 h. The reaction mixture was cooled to 0° C. and quenched by the addition of MeOH (5 mL), and then concentrated in vacuo. The crude residue was triturated with EtOAc to give 5-hydroxy-2-methyl-2,3-dihydro-1H-isoindol-1-one, which was taken to the next step without further purification. MS=164.0 [M+H]$^+$.

Step 3: 5-(2-bromoethoxy)-2-methyl-2,3-dihydro-1H-isoindol-1-one

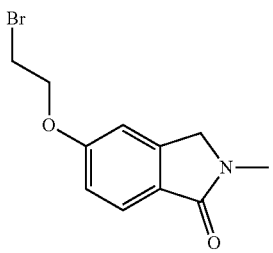

To a solution of 5-hydroxy-2-methyl-2,3-dihydro-1H-isoindol-1-one (1.25 g, 7.66 mmol) in 1,2-dibromoethane (12.5 mL, 166 mmol) was added Cs$_2$CO$_3$ (4.99 g, 15.3 mmol). The mixture was stirred at 100° C. for 16 h. After cooling to room temperature, the reaction mixture was concentrated in vacuo. The crude residue was purified by normal phase silica gel chromatography (Biotage 25 g cartridge, 70-100% EtOAc:petroleum ether) to give 5-(2-bromoethoxy)-2-methyl-2,3-dihydro-1H-isoindol-1-one (Intermediate A-53). MS=270.0/272.0 [M+H]$^+$.

General Procedure for Intermediates A-54 & A-55

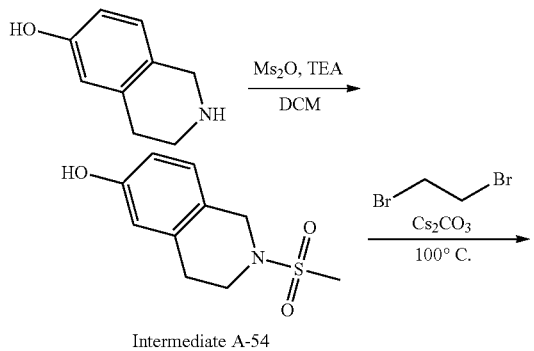

Intermediate A-54

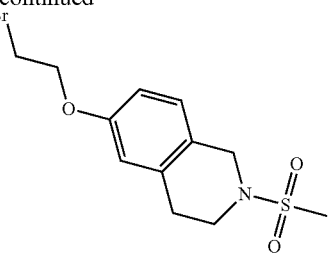

Intermediate A-55

Step 1: 2-methanesulfonyl-1,2,3,4-tetrahydroisoquinolin-6-ol

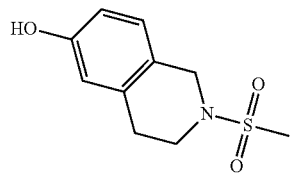

A mixture of 1,2,3,4-tetrahydroisoquinolin-6-ol (500 mg, 3.35 mmol), methanesulfonic anhydride (1.17 g, 6.70 mmol), and TEA (0.933 mL, 6.70 mmol) in DCM (10 mL) was degassed and purged with N$_2$ (3×). After stirring at room temperature for 3 h under N$_2$ atmosphere, the reaction mixture was quenched with H$_2$O (5 mL) and extracted with DCM (3×10 mL). The combined organic layers were washed with brine (2×20 mL), dried over Na$_2$SO$_4$, filtered, and concentrated in vacuo. The crude residue was purified by normal phase silica gel chromatography (Biotage 12 g cartridge, 0-50% EtOAc:petroleum ether) to give 2-methanesulfonyl-1,2,3,4-tetrahydroisoquinolin-6-ol (Intermediate A-54). MS=228.1 [M+H]$^+$.

Step 2: 6-(2-bromoethoxy)-2-methanesulfonyl-1,2,3,4-tetrahydroisoquinoline

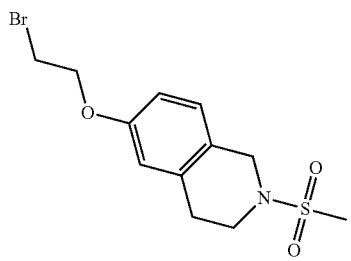 [SMILES: CS(=O)(=O)N1CCc2cc(OCCBr)ccc2C1]

To a solution of 2-methanesulfonyl-1,2,3,4-tetrahydroisoquinolin-6-ol (100 mg, 0.440 mmol) in 1,2-dibromoethane (5 mL) was added Cs$_2$CO$_3$ (430 mg, 1.32 mmol). The mixture was stirred at 100° C. for 5 h. After cooling to room temperature, solids were removed by filtration and the filtrate was concentrated in vacuo. The crude residue was purified by normal phase silica gel chromatography (Biotage 4 g cartridge, 0-100% EtOAc:petroleum ether) to give 6-(2-bromoethoxy)-2-methanesulfonyl-1,2,3,4-tetrahydroisoquinoline (Intermediate A-55). MS=334.1/336.1 [M+H]$^+$.

The following intermediate in Table 9 was prepared using procedures similar to Step 1 described for Intermediate A-54, using the appropriate starting materials.

General Procedure for Intermediate A-56

TABLE 9

| Intermediate # | Structure | Name | Exact Mass [M + H]+ |
|---|---|---|---|
| A-56 | 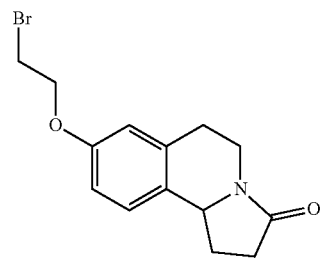 [SMILES: O=C1CCC2c3ccc(OCCBr)cc3CCN12] | 1-(6-hydroxy-1,2,3,4-tetrahydroisoquinolin-2-yl)ethan-1-one | Calc'd 192.1 Found 192.2 |

General Procedure for Intermediate A-57

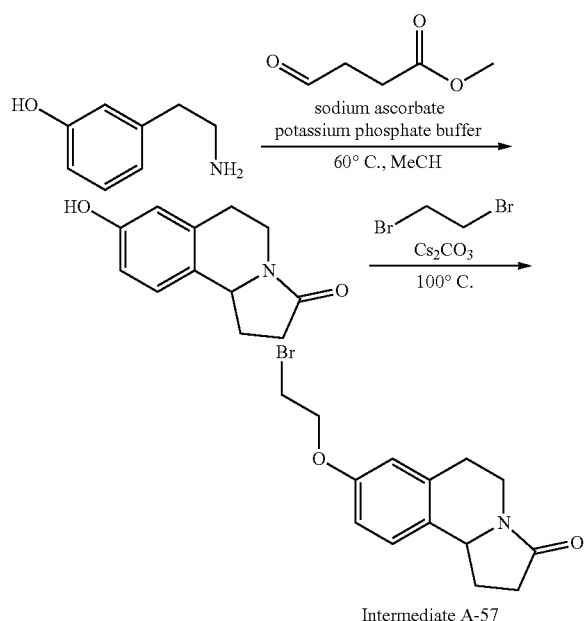

Intermediate A-57

Step 1: 8-hydroxy-1H,2H,3H,5H,6H,10bH-pyrrolo[2,1-a]isoquinolin-3-one

A mixture of 3-(2-aminoethyl)phenol (1.00 g, 5.76 mmol, HCl salt), methyl 4-oxobutanoate (1.00 g, 8.64 mmol), and sodium ascorbate (1.14 g, 5.76 mmol) in a solution of 0.3 M aqueous potassium phosphate buffer (200 mL) and MeCN (200 mL) was stirred at 60° C. for 18 h under an atmosphere of $N_2$. 1.0 M aqueous $Na_2CO_3$ (2.0 mL, 2.0 mmol) was added, and the mixture was stirred for another 4 h at 60° C. After cooling to room temperature, the mixture was extracted with EtOAc (3×300 mL). The combined organic layers were washed with brine (200 mL), dried over $Na_2SO_4$, filtered, and concentrated in vacuo. The crude residue was purified by normal phase silica gel chromatography (Biotage 40 g cartridge, 0-100% EtOAc:petroleum ether to 0-10% MeOH:EtOAc) to give 8-hydroxy-1H,2H,3H,5H,6H,10bH-pyrrolo[2,1-a]isoquinolin-3-one. MS=204.1 [M+H]+.

Step 2: 8-(2-bromoethoxy)-1H,2H,3H,5H,6H,10bH-pyrrolo[2,1-a]isoquinolin-3-one

To a solution of 8-hydroxy-1H,2H,3H,5H,6H,10bH-pyrrolo[2,1-a]isoquinolin-3-one (300 mg, 1.48 mmol) in 1,2-dibromoethane (5.00 mL, 66.3 mmol) was added $Cs_2CO_3$ (962 mg, 2.95 mmol). The mixture was stirred at 100° C. for 32 h. After cooling to room temperature, the reaction mixture was quenched with $H_2O$ (10 mL) and extracted with EtOAc (4×8 mL). The combined organic layers were washed with brine (2×8 mL), dried over $Na_2SO_4$, filtered, and concentrated in vacuo. The crude residue was purified by normal phase silica gel chromatography (Biotage 25 g cartridge, 70-100% EtOAc:petroleum ether) to give 8-(2-bromoethoxy)-1H,2H,3H,5H,6H,10bH-pyrrolo[2,1-a]isoquinolin-3-one (Intermediate A-57). MS=310.0/312.0 [M+H]+.

General Procedure for Intermediate A-58

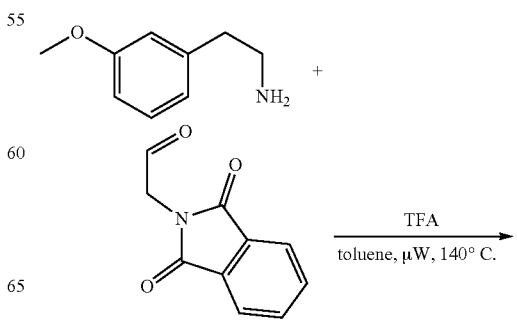

Step 1: 2-[(6-methoxy-1,2,3,4-tetrahydroisoquinolin-1-yl)methyl]-2,3-dihydro-1H-isoindole-1,3-dione

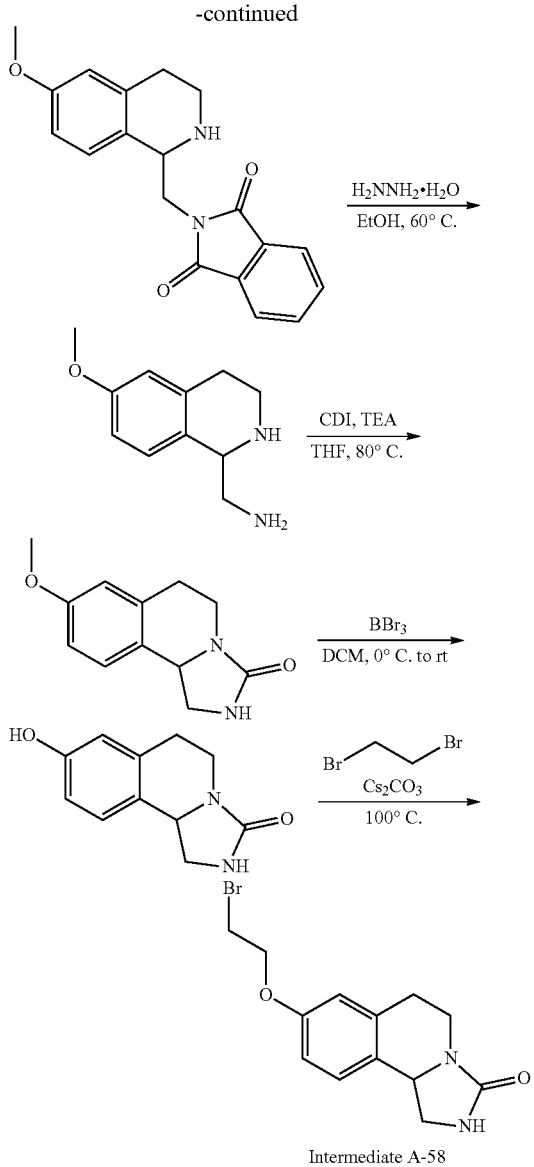

Intermediate A-58

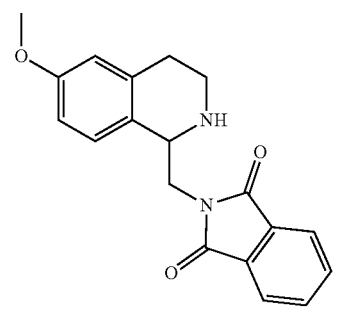 [SMILES: COc1ccc2c(c1)CCNC2CN1C(=O)c2ccccc2C1=O]

A mixture of 2-(3-methoxyphenyl)ethan-1-amine (4.85 mL, 33.1 mmol), 2-(1,3-dioxo-2,3-dihydro-1H-isoindol-2-yl)acetaldehyde (7.51 g, 39.7 mmol), and TFA (19.6 mL, 265 mmol) in toluene (50 mL) heated via microwave for 30 min at 140° C. under N₂ atmosphere. After cooling to room temperature, the mixture was diluted with H₂O (60 mL) and extracted with EtOAc (3×50 mL). The combined organic layers were washed with brine (2×50 mL), dried over Na₂SO₄, filtered, and concentrated in vacuo. The crude residue was purified by normal phase silica gel chromatography (Biotage 80 g cartridge, 0-50% EtOAc:petroleum ether) to give 2-[(6-methoxy-1,2,3,4-tetrahydroisoquinolin-1-yl)methyl]-2,3-dihydro-1H-isoindole-1,3-dione. MS=323.2 [M+H]⁺.

Step 2: 1-(6-methoxy-1,2,3,4-tetrahydroisoquinolin-1-yl)methanamine

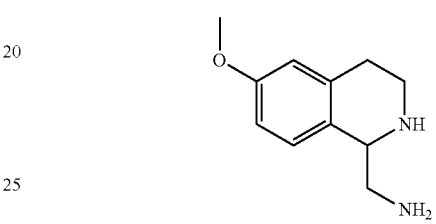

A mixture of 2-[(6-methoxy-1,2,3,4-tetrahydroisoquinolin-1-yl)methyl]-2,3-dihydro-1H-isoindole-1,3-dione (5.00 g, 15.5 mmol), H₂NNH₂·H₂O (2.66 mL, 85% purity, 46.53 mmol) in EtOH (50 mL) was degassed and purged with N₂ (3×). The mixture was stirred at 60° C. for 5 h under N₂ atmosphere. After cooling to room temperature, the mixture was filtered to remove solids, and the resulting filtrate was concentrated in vacuo to give 1-(6-methoxy-1,2,3,4-tetrahydroisoquinolin-1-yl)methanamine, which was used in the subsequent step without further purification. MS=193.2 [M+H]⁺.

Step 3: 8-methoxy-1H,2H,3H,5H,6H,10bH-imidazo[4,3-a]isoquinolin-3-one

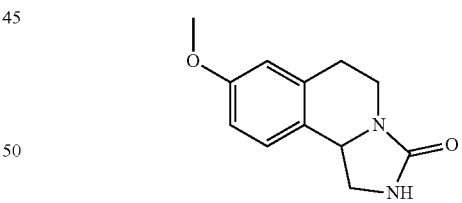

To a solution of 1-(6-methoxy-1,2,3,4-tetrahydroisoquinolin-1-yl)methanamine (1.00 g, 5.20 mmol) in THF (20 mL) were added CDI (4.22 g, 26.0 mmol) and TEA (0.724 mL, 5.20 mmol). A total of 5 identical reactions were set up using the described procedure. The mixtures were stirred at 80° C. for 12 h. After cooling to room temperature, the 5 reaction mixtures were combined into one solution and diluted with H₂O (50 mL) and extracted with EtOAc (3×50 mL). The combined organic layers were washed with brine (2×50 mL), dried over Na₂SO₄, filtered, and concentrated in vacuo. The crude residue was purified by normal phase silica gel chromatography (Biotage 80 g cartridge, 0-60% EtOAc: petroleum ether) to give 8-methoxy-1H,2H,3H,5H,6H,10bH-imidazo[4,3-a]isoquinolin-3-one. MS=219.2 [M+H]⁺.

Step 4: 8-hydroxy-1H,2H,3H,5H,6H,10bH-imidazo[4,3-a]isoquinolin-3-one

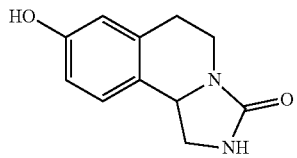

To a 0° C. solution of 8-methoxy-1H,2H,3H,5H,6H,10bH-imidazo[4,3-a]isoquinolin-3-one (1.00 g, 4.58 mmol) in DCM (10 mL) was added BBr$_3$ (0.883 mL, 9.16 mmol) dropwise. The mixture was allowed to warm to room temperature and stirred for 2 h. The mixture was quenched with H$_2$O (20 mL), then filtered, and the filtrate was concentrated in vacuo to give 8-methoxy-1H,2H,3H,5H,6H,10bH-imidazo[4,3-a]isoquinolin-3-one, which was used in the subsequent step without further purification. MS=205.1 [M+H]$^+$.

Step 5: 8-(2-bromoethoxy)-1H,2H,3H,5H,6H,10bH-imidazo[4,3-a]isoquinolin-3-one

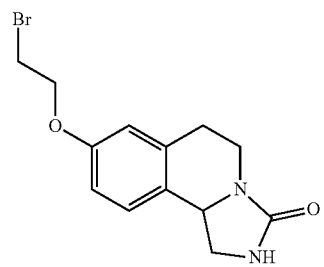 [SMILES: O=C1NCC2c3ccc(OCCBr)cc3CCN12]

A mixture of 8-methoxy-1H,2H,3H,5H,6H,10bH-imidazo[4,3-a]isoquinolin-3-one (700 mg, 3.43 mmol) and Cs$_2$CO$_3$ (3.19 g, 9.79 mmol) in 1,2-dibromoethane (15 mL, 197 mmol) was degassed and purged with N$_2$ (3×). The mixture was stirred at 100° C. for 12 h under N$_2$ atmosphere. After cooling to room temperature, solids were removed by filtration and the filtrate was concentrated in vacuo. The crude residue was purified by normal phase silica gel chromatography (Biotage 40 g cartridge, 0-100% EtOAc:petroleum ether) to give 8-(2-bromoethoxy)-1H,2H,3H,5H,6H,10bH-imidazo[4,3-a]isoquinolin-3-one (Intermediate A-58). MS=311.1/313.1 [M+H]$^+$.

General Procedure for Intermediate A-59

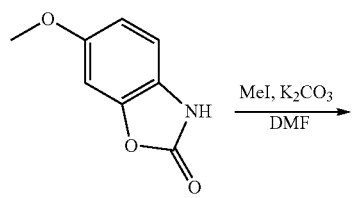

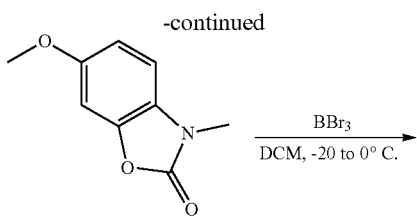

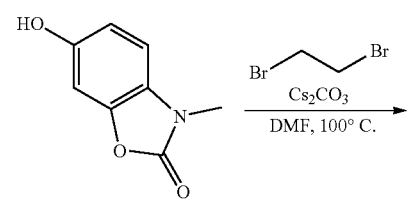

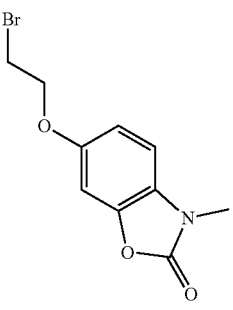

Intermediate A-59

Step 1: 6-methoxy-3-methyl-2,3-dihydro-1,3-benzoxazol-2-one

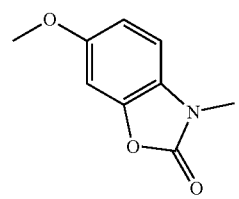

To a solution of 6-methoxy-2,3-dihydro-1,3-benzoxazol-2-one (1.80 g, 10.9 mmol) and K$_2$CO$_3$ (3.01 g, 21.8 mmol) in DMF (18 mL) was added MeI (1.36 mL, 21.8 mmol). The mixture was stirred at room temperature for 1 h and was then quenched H$_2$O (15 mL). The mixture was extracted with EtOAc (3×20 mL). The combined organic layers were washed with brine (2×20 mL), dried over Na$_2$SO$_4$, filtered, and concentrated in vacuo. The crude residue was purified by normal phase silica gel chromatography (Biotage 10 g cartridge, 0-20% EtOAc:petroleum ether) to give 6-methoxy-3-methyl-2,3-dihydro-1,3-benzoxazol-2-one. MS=180.0 [M+H]$^+$.

Step 2: 6-hydroxy-3-methyl-2,3-dihydro-1,3-benzoxazol-2-one

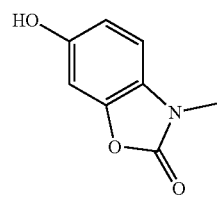

To a −20° C. solution of 6-methoxy-3-methyl-2,3-dihydro-1,3-benzoxazol-2-one (1.50 g, 8.37 mmol) in DCM (3 mL) was added BBr$_3$ (2.42 mL, 25.1 mmol) dropwise. The mixture was warmed to 0° C. and stirred for 1 h, then poured into H$_2$O (15 mL). The resulting solids were isolated by filtration. The filter cake was washed with H$_2$O and then dried in vacuo to provide the first fraction of desired product. The filtrate was extracted with DCM (3×20 mL). The combined organic layers were washed with brine (15 mL), dried over Na$_2$SO$_4$, filtered, and concentrated in vacuo. The crude residue was washed with MeCN (2 mL), isolated by filtration, and the filter cake was dried in vacuo to give the second fraction of 6-hydroxy-3-methyl-2,3-dihydro-1,3-benzoxazol-2-one, which was combined with the first fraction and used in the subsequent step without further purification. MS=166.3 [M+H]$^+$.

Step 3: 6-(2-bromoethoxy)-3-methyl-2,3-dihydro-1,3-benzoxazol-2-one

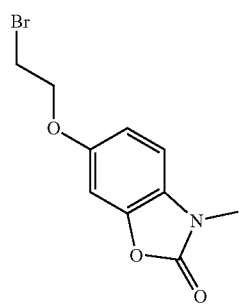

A solution of 1,2-dibromoethane (2.97 mL, 39.4 mmol), 6-hydroxy-3-methyl-2,3-dihydro-1,3-benzoxazol-2-one (1.30 g, 7.87 mmol) and Cs$_2$CO$_3$ (3.85 g, 11.8 mmol) in DMF (2 mL) was stirred at 100° C. for 16 h. After cooling to room temperature, the mixture was quenched with H$_2$O (15 mL). The mixture was extracted with EtOAc (3×15 mL). The combined organic layers were washed with brine (2×10 mL), dried over Na$_2$SO$_4$, filtered, and concentrated in vacuo. The crude residue was purified by normal phase silica gel chromatography (Biotage 20 g cartridge, 0-30% EtOAc: petroleum ether) to give 6-(2-bromoethoxy)-3-methyl-2,3-dihydro-1,3-benzoxazol-2-one (Intermediate A-59). MS=271.9/273.8 [M+H]$^+$.

General Procedure for Intermediate A-60

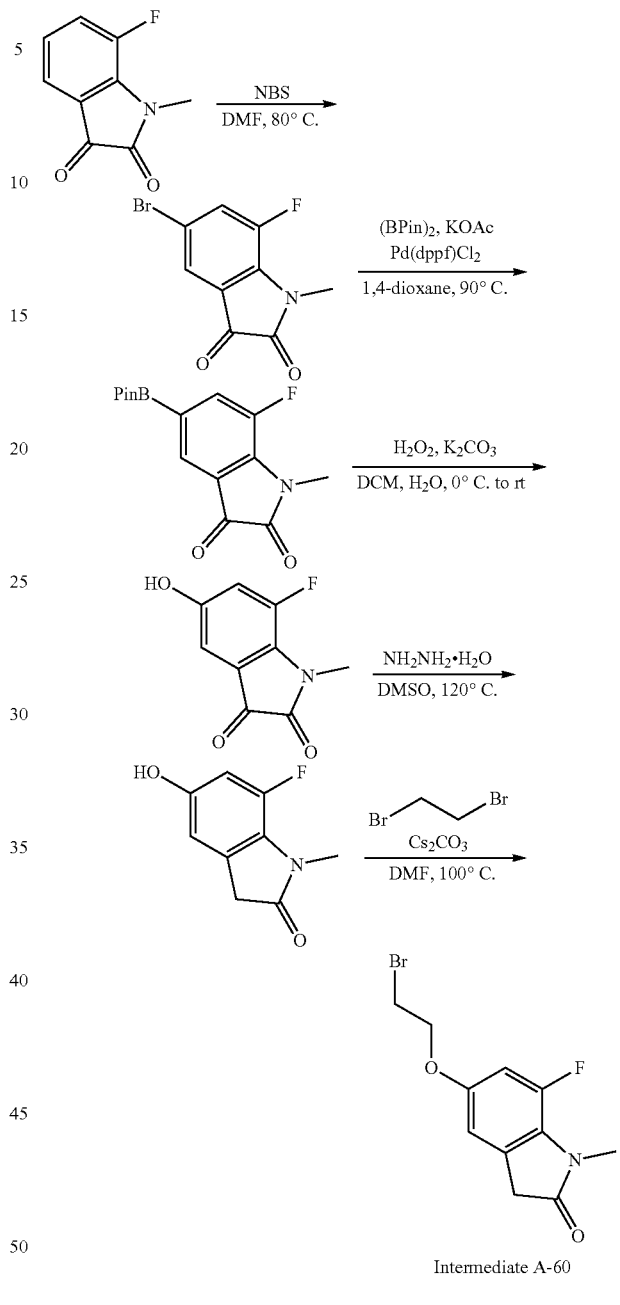

Intermediate A-60

Step 1: 5-bromo-7-fluoro-1-methyl-2,3-dihydro-1H-indole-2,3-dione

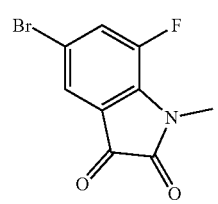

A solution of 7-fluoro-1-methyl-2,3-dihydro-1H-indole-2,3-dione (4.00 g, 22.3 mmol) and NBS (5.17 g, 29.0 mmol)

in DMF (45 mL) was stirred at 80° C. for 2 h under N₂. After cooling to room temperature, the reaction mixture was poured into H₂O (100 mL) and a solid crashed out of solution. The solid was isolated via filtration and dried in vacuo to give 5-bromo-7-fluoro-1-methyl-2,3-dihydro-1H-indole-2,3-dione, which was used in the subsequent step without further purification. MS=258.0/260.0 [M+H]⁺.

Step 2: 7-fluoro-1-methyl-5-(4,4,5,5-tetramethyl-1,3,2-dioxaborolan-2-yl)-2,3-dihydro-1H-indole-2,3-dione

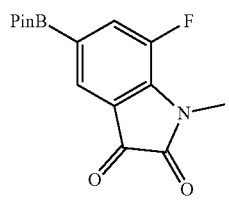

To a solution of 5-bromo-7-fluoro-1-methyl-2,3-dihydro-1H-indole-2,3-dione (3.98 g, 15.4 mmol) and bis(pinacolato)diboron (5.88 g, 23.1 mmol) in 1,4-dioxane (40 mL) was added KOAc (3.03 g, 30.9 mmol) and Pd(dppf)Cl₂ (1.13 g, 1.54 mmol). The mixture was stirred at 90° C. for 15 h under an atmosphere of N₂. After cooling to room temperature, the mixture was diluted with H₂O (50 mL). The mixture was extracted with EtOAc (3×30 mL). The combined organic layers were washed with brine (2×30 mL), dried over Na₂SO₄, filtered, and concentrated in vacuo. The crude residue was purified by normal phase silica gel chromatography (Biotage 80 g cartridge, 0-15% EtOAc:petroleum ether) to give 7-fluoro-1-methyl-5-(4,4,5,5-tetramethyl-1,3,2-dioxaborolan-2-yl)-2,3-dihydro-1H-indole-2,3-dione. MS=306.1 [M+H]⁺.

Step 3: 7-fluoro-5-hydroxy-1-methyl-2,3-dihydro-1H-indole-2,3-dione

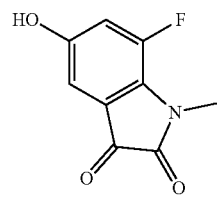

To a solution of 7-fluoro-1-methyl-5-(4,4,5,5-tetramethyl-1,3,2-dioxaborolan-2-yl)-2,3-dihydro-1H-indole-2,3-dione (2.80 g, 9.18 mmol) in DCM (35 mL) were added K₂CO₃ (2.54 g, 18.4 mmol) and H₂O₂ in H₂O (2.20 mL, 30 wt %, 22.94 mmol). The mixture was stirred at room temperature for 1 h. The reaction mixture was cooled to 0° C., quenched with saturated Na₂SO₃ (10 mL), and extracted with DCM (3×10 mL). The combined organic layers were washed with brine (5 mL), dried over Na₂SO₄, filtered, and concentrated in vacuo. The crude residue was purified by normal phase silica gel chromatography (Biotage 4 g cartridge, 0-35% EtOAc:petroleum ether) to give 7-fluoro-5-hydroxy-1-methyl-2,3-dihydro-1H-indole-2,3-dione. MS=196.1 [M+H]⁺.

Step 4: 7-fluoro-5-hydroxy-1-methyl-2,3-dihydro-1H-indol-2-one

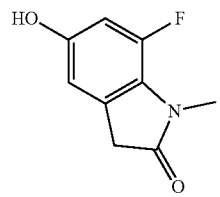

To a solution of 7-fluoro-5-hydroxy-1-methyl-2,3-dihydro-1H-indole-2,3-dione (600 mg, 3.07 mmol) in DMSO (2.5 mL) was added NH₂NH₂·H₂O (2.46 mL, 85% purity, 43.0 mmol). The mixture was stirred at 120° C. for 3 h. After cooling to 0° C., the reaction mixture was quenched with H₂O (8 mL) and extracted with EtOAc (3×7 mL). The combined organic layers were washed with brine (5 mL), dried over Na₂SO₄, filtered, and concentrated in vacuo. The crude residue was purified by normal phase silica gel chromatography (Biotage 12 g cartridge, 0-29% EtOAc:petroleum ether) to give 7-fluoro-5-hydroxy-1-methyl-2,3-dihydro-1H-indol-2-one. MS=180.1 [M−H]⁻.

Step 5: 5-(2-bromoethoxy)-7-fluoro-1-methyl-2,3-dihydro-1H-indol-2-one

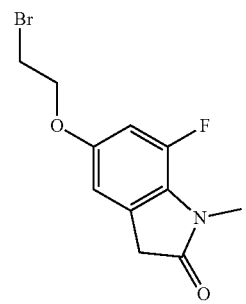 [SMILES: CN1C(=O)Cc2cc(OCCBr)cc(F)c21]

A solution of 7-fluoro-5-hydroxy-1-methyl-2,3-dihydro-1H-indol-2-one (250 mg, 1.38 mmol) and Cs₂CO₃ (1.12 g, 3.45 mmol) in 1,2-dibromoethane (6.00 mL, 79.5 mmol) was stirred at 100° C. for 15 h. After cooling to room temperature, the reaction mixture was quenched with H₂O (18 mL) and extracted with EtOAc (3×12 mL). The combined organic layers were washed with brine (5 mL), dried over Na₂SO₄, filtered, and concentrated in vacuo. The crude residue was purified by normal phase silica gel chromatography (Biotage 4 g cartridge, 0-17% EtOAc:petroleum ether) to give 5-(2-bromoethoxy)-7-fluoro-1-methyl-2,3-dihydro-1H-indol-2-one (Intermediate A-60). MS=287.9/289.9 [M+H]⁺.

General Procedure for Intermediate A-61

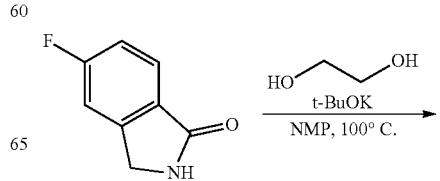

-continued

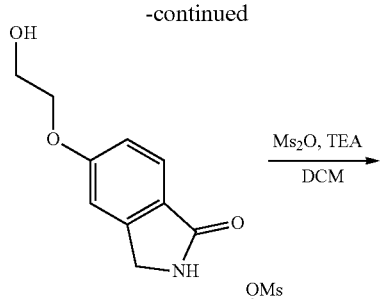

Intermediate A-61

Step 1:
5-(2-hydroxyethoxy)-2,3-dihydro-1H-isoindol-1-one

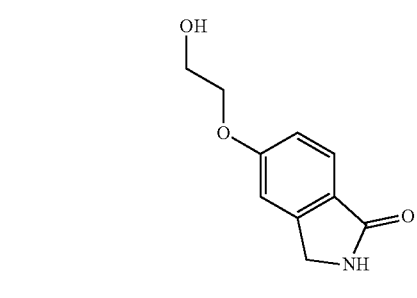 [SMILES: O=C1NCc2cc(OCCO)ccc21]

To a mixture of 5-fluoro-2,3-dihydro-1H-isoindol-1-one (750 mg, 4.96 mmol) and ethylene glycol (4.00 mL, 71.53 mmol) in NMP (4 mL) was added t-BuOK (1.67 g, 14.8 mmol). The mixture was stirred at 100° C. for 15 h. After cooling to room temperature, the reaction mixture was diluted with NMP (2 mL), and solids were removed by filtration. The filtrate was concentrated in vacuo. The crude residue was purified by reverse phase preparative HPLC (Waters Xbridge BEH $C_{18}$ column, 1-30% MeCN: 10 mM $NH_4HCO_3$ in $H_2O$) to give 5-(2-hydroxyethoxy)-2,3-dihydro-1H-isoindol-1-one. MS=194.2 $[M+H]^+$.

Step 2: 2-[(1-oxo-2,3-dihydro-1H-isoindol-5-yl)oxy]ethyl methanesulfonate

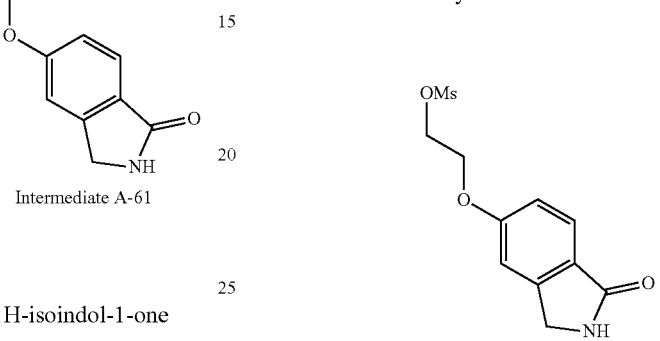

To a 0° C. mixture of 5-(2-hydroxyethoxy)-2,3-dihydro-1H-isoindol-1-one (100 mg, 0.518 mmol) and TEA (0.144 mL, 1.04 mmol) in DCM (2 mL) was added methanesulfonic anhydride (451 mg, 2.59 mmol) portionwise. The reaction mixture was warmed to room temperature and stirred for 15 h. The reaction mixture was then quenched with $H_2O$ (10 mL) and extracted with EtOAc (3×10 mL). The combined organic layers were dried over $Na_2SO_4$, filtered, and concentrated in vacuo to give 2-[(1-oxo-2,3-dihydro-1H-isoindol-5-yl)oxy]ethyl methanesulfonate (Intermediate A-61), which was used in the subsequent step without further purification. MS=272.1 $[M+H]^+$.

General Procedure for Intermediate A-62

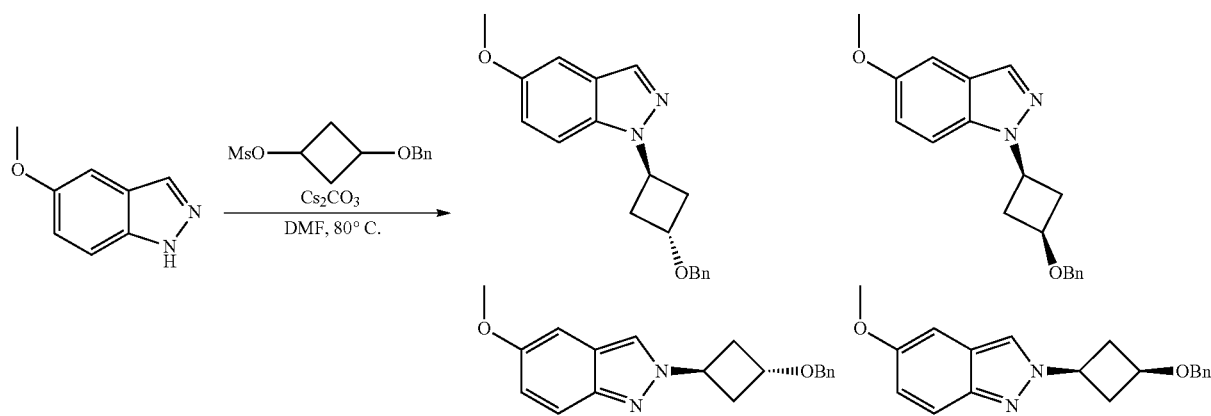

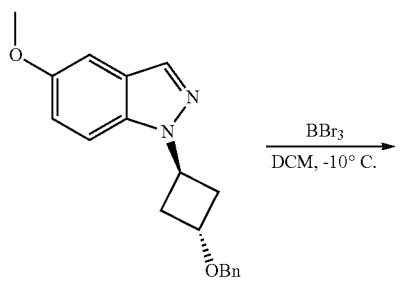

Step 1: 5-methoxy-1-[trans-3-(benzyloxy)cyclobutyl]-1H-indazole

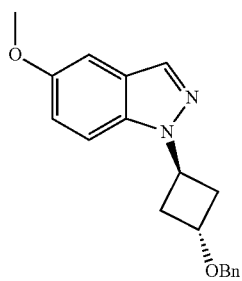 [SMILES: COc1ccc2c(cnn2[C@H]2C[C@H](OCc3ccccc3)C2)c1]

To a mixture of 5-methoxy-1H-indazole (665 mg, 4.49 mmol) and (3-benzyloxycyclobutyl) methanesulfonate (1.15 g, 4.49 mmol) in DMF (15 mL) was added Cs₂CO₃ (2.92 g, 8.98 mmol). The mixture was stirred at 80° C. for 15 h. After cooling to room temperature, the reaction mixture was quenched with H₂O (45 mL) and extracted with EtOAc (3×50 mL). The combined organic layers were dried over Na₂SO₄, filtered, and concentrated in vacuo. The crude residue was purified by normal phase silica gel chromatography (Biotage 80 g cartridge, 0-50% EtOAc:petroleum ether). The first eluting product, desired 5-methoxy-1-[trans-3-(benzyloxy)cyclobutyl]-1H-indazole: ¹H NMR (400 MHz, CDCl₃): δ 7.94 (s, 1H), 7.40-7.35 (m, 6H), 7.08-7.04 (m, 2H), 4.67-4.59 (m, 1H), 4.53 (s, 2H), 4.06-4.00 (m, 1H), 3.86 (s, 3H), 2.93-2.83 (m, 4H). MS=309.3 [M+H]⁺. The second eluting product, desired 5-methoxy-1-[cis-3-(benzyloxy)cyclobutyl]-1H-indazole: ¹H NMR (400 MHz, CDCl₃): δ 7.95 (s, 1H), 7.41-7.29 (m, 6H), 7.07-7.04 (m, 2H), 5.29-5.22 (m, 1H), 4.54-4.50 (m, 3H), 3.86 (s, 3H), 2.96-2.92 (m, 2H), 2.73-2.67 (m, 2H). The third eluting product, undesired 5-methoxy-2-[(trans)-3-(benzyloxy)cyclobutyl]-2H-indazole: ¹H NMR (400 MHz, CDCl₃): δ 7.81 (s, 1H), 7.64 (d, J=9.6 Hz, 1H), 7.39-7.37 (m, 5H), 7.00 (dd, J=9.6, 2.4 Hz, 1H), 6.87 (d, J=2.4 Hz, 1H), 5.21-5.17 (m, 1H), 4.56-4.52 (m, 1H), 4.51 (s, 2H), 3.84 (s, 3H), 2.99-2.92 (m, 2H), 2.77-2.72 (m, 2H). The fourth eluting product, undesired 5-methoxy-2-[(cis)-3-(benzyloxy)cyclobutyl]-2H-indazole: ¹H NMR (400 MHz, CDCl₃): δ 7.88 (s, 1H), 7.62 (d, J=9.2 Hz, 1H), 7.38-7.33 (m, 5H), 7.99 (dd, J=9.2, 2.4 Hz, 1H), 6.87 (d, J=2.4 Hz, 1H), 4.67-4.62 (m, 1H), 4.52 (s, 2H), 4.06-3.99 (m, 1H), 3.84 (s, 3H), 3.01-2.98 (m, 2H), 2.70-2.67 (m, 2H).

Step 2: 1-[trans-3-hydroxycyclobutyl]-1H-indazol-5-ol

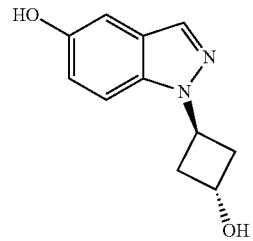 [SMILES: Oc1ccc2c(cnn2[C@H]2C[C@H](O)C2)c1]

To a −10° C. solution of 5-methoxy-1-[trans-3-(benzyloxy)cyclobutyl]-1H-indazole (250 mg, 0.811 mmol) in DCM (2.5 mL) was added BBr₃ (156 μL, 1.62 mmol). The mixture was stirred at −10° C. for 4 h, and then quenched with MeOH (10 mL). The solution was placed in a 0° C. ice bath and adjusted to pH=7-8 with the dropwise addition of saturated aqueous NaHCO₃. The biphasic mixture was concentrated in vacuo, and the remaining aqueous layer was extracted with EtOAc (3×20 mL). The combined organic layers were washed with brine (2×40 mL), dried over Na₂SO₄, filtered, and concentrated in vacuo. The crude residue was purified by normal phase silica gel chromatography (Biotage 12 g cartridge, 0-100% EtOAc:petroleum ether) to give 1-[trans-3-hydroxycyclobutyl]-1H-indazol-5-ol. MS=205.2 [M+H]⁺.

Step 3: trans-3-[5-(2-bromoethoxy)-1H-indazol-1-yl]cyclobutan-1-ol

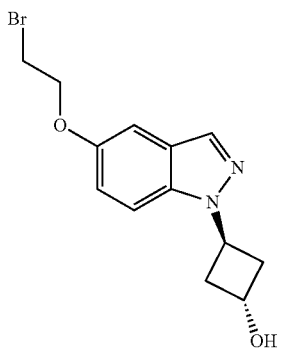 [SMILES: O[C@H]1C[C@H](n2ncc3cc(OCCBr)ccc32)C1]

To a solution of 1-[trans-3-hydroxycyclobutyl]-1H-indazol-5-ol (100 mg, 0.490 mmol) in 1,2-dibromoethane (10 mL, 133 mmol) was added Cs$_2$CO$_3$ (479 mg, 1.47 mmol). The mixture was stirred at 100° C. for 15 h. After cooling to room temperature, the reaction mixture was quenched with H$_2$O (30 mL) and extracted with EtOAc (3×15 mL). The combined organic layers were dried over Na$_2$SO$_4$, filtered, and concentrated in vacuo. The crude residue was purified by normal phase silica gel chromatography (Biotage 25 g cartridge, 0-100% EtOAc:petroleum ether) to give trans-3-[5-(2-bromoethoxy)-1H-indazol-1-yl]cyclobutan-1-ol (Intermediate A-62). MS=311.2/313.2 [M+H]$^+$.

The following intermediate in Table 10 was prepared using procedures similar to those described for Intermediate A-62, using the appropriate starting materials.

General Procedures for Intermediate A-63

TABLE 10

| Intermediate # | Structure | Name | Exact Mass [M + H]$^+$ |
|---|---|---|---|
| A-63 | 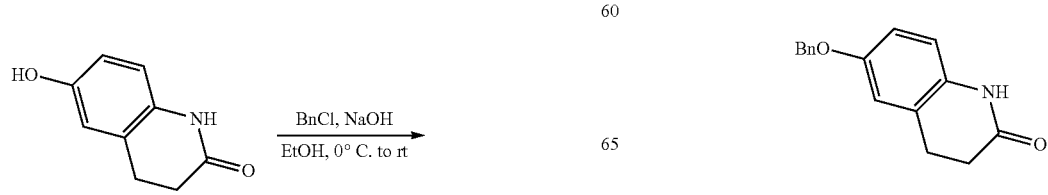 | cis-3-[5-(2-bromoethoxy)-1H-indazol-1-yl]cyclobutan-1-ol | Calc'd 311.0/313.0<br>Found 311.2/313.2 |

General Procedure for Intermediate A-64

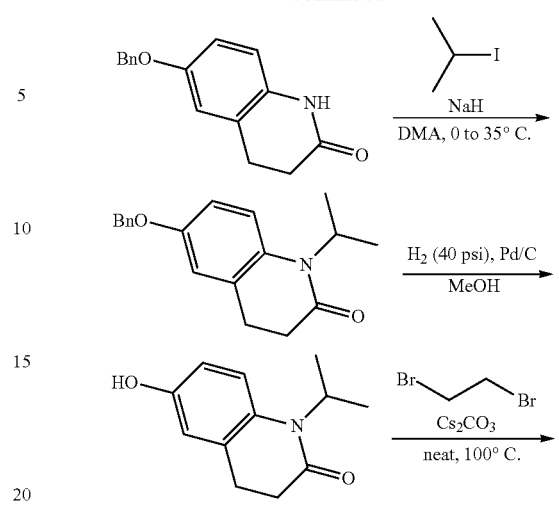

Intermediate A-64

Step 1: 6-(benzyloxy)-1,2,3,4-tetrahydroquinolin-2-one

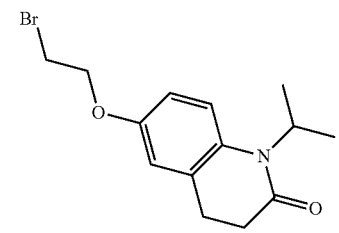

To a 0° C. solution of 6-hydroxy-1,2,3,4-tetrahydroquinolin-2-one (1.00 g, 6.13 mmol) in EtOH (10 mL) were added NaOH (490 mg, 12.3 mmol) and benzyl chloride (2.12 mL, 18.4 mmol). The mixture was stirred at room temperature for 15 h, was then poured into H₂O (20 mL), and filtered to give a filter cake. The filter cake was washed with EtOH, triturated with MTBE, then dried in vacuo to give 6-(benzyloxy)-1,2,3,4-tetrahydroquinolin-2-one, which was taken to the next step without further purification. MS=254.2 [M+H]⁺.

Step 2: 6-(benzyloxy)-1-(propan-2-yl)-1,2,3,4-tetrahydroquinolin-2-one

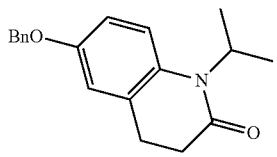 [SMILES: CC(C)N1C(=O)CCc2cc(OCc3ccccc3)ccc21]

To a 0° C. solution of 6-(benzyloxy)-1,2,3,4-tetrahydroquinolin-2-one (1.50 g, 5.92 mmol) in DMA (20 mL) under N₂ atmosphere was added NaH (616 mg, 60 wt % in mineral oil, 15.4 mmol). After 30 min, 2-iodopropane (2.37 mL, 23.7 mmol) was added. The reaction mixture was warmed to room temperature, and then heated to 35° C. and stirred for 15.5 h under an atmosphere of N₂. After cooling to 0° C., the reaction mixture was quenched with H₂O (30 mL) and extracted with EtOAc (3×20 mL). The combined organic layers were washed with brine (5 mL), dried over Na₂SO₄, filtered, and concentrated in vacuo. The crude residue was purified by normal phase silica gel chromatography (Biotage 20 g cartridge, 0-27% EtOAc:petroleum ether) to give 6-(benzyloxy)-1-(propan-2-yl)-1,2,3,4-tetrahydroquinolin-2-one. MS=296.1 [M+H]⁺.

Step 3: 6-hydroxy-1-(propan-2-yl)-1,2,3,4-tetrahydroquinolin-2-one

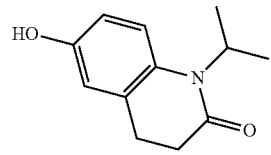

To a solution of 6-(benzyloxy)-1-(propan-2-yl)-1,2,3,4-tetrahydroquinolin-2-one (1.30 g, 4.40 mmol) in MeOH (25 mL) was added Pd/C (0.30 g, 10 wt %, 0.28 mmol). The mixture was stirred at 40° C. for 16 h under an atmosphere of H₂ (40 psi). After cooling to room temperature, the reaction mixture was filtered through Celite and the filtrate was concentrated in vacuo to give 6-hydroxy-1-(propan-2-yl)-1,2,3,4-tetrahydroquinolin-2-one, which was used in the subsequent step without further purification. MS=206.0 [M+H]⁺.

Step 4: 6-(2-bromoethoxy)-1-(propan-2-yl)-1,2,3,4-tetrahydroquinolin-2-one

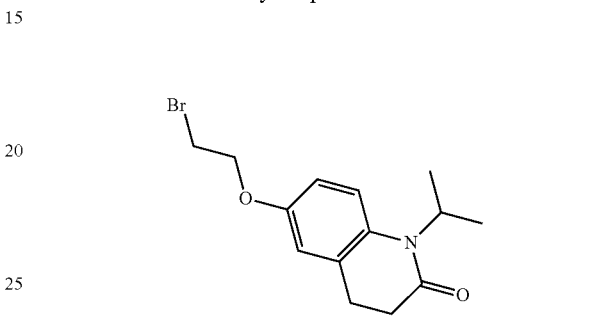

To a solution of 6-hydroxy-1-(propan-2-yl)-1,2,3,4-tetrahydroquinolin-2-one (810 mg, 3.95 mmol) in 1,2-dibromoethane (12 mL, 159 mmol) was added Cs₂CO₃ (2.57 g, 7.89 mmol). The mixture was stirred at 100° C. for 15 h. After cooling to room temperature, the reaction mixture was quenched with H₂O (20 mL) and extracted with EtOAc (3×20 mL). The combined organic layers were washed with brine (2×25 mL), dried over Na₂SO₄, filtered, and concentrated in vacuo. The crude residue was purified by normal phase silica gel chromatography (Biotage 12 g cartridge, 0-20% EtOAc:petroleum ether) to give 6-(2-bromoethoxy)-1-(propan-2-yl)-1,2,3,4-tetrahydroquinolin-2-one (Intermediate A-64). MS=312.0/314.0 [M+H]⁺.

The following intermediates in Table 11 were prepared according to procedures similar those described for Intermediate A-64 using the appropriate starting materials.

General Procedure for Intermediates A-65 to A-68

TABLE 11

| Intermediate # | Structure | Name | Exact Mass [M + H]⁺ |
| --- | --- | --- | --- |
| A-65 | ![Br-CH2CH2-O-quinolinone-N-CH2CH2-OH] | 6-(2-bromoethoxy)-1-(2-hydroxyethyl)-1,2,3,4-tetrahydroquinolin-2-one | Calc'd 314.0/316.0 Found 313.9/315.9 |

TABLE 11-continued
| Intermediate # | Structure | Name | Exact Mass [M + H]+ |
|---|---|---|---|
| A-66 | 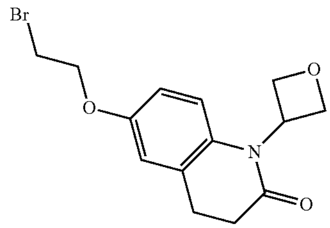 [SMILES: O=C1CCc2cc(OCCBr)ccc2N1C1COC1] | 6-(2-bromoethoxy)-1-(oxetan-3-yl)-1,2,3,4-tetrahydroquinolin-2-one | Calc'd 326.0/328.0<br>Found 326.1/328.1 |
| A-67 | 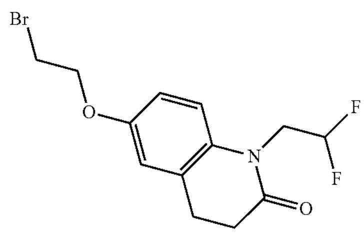 [SMILES: O=C1CCc2cc(OCCBr)ccc2N1CC(F)F] | 6-(2-bromoethoxy)-1-(2,2-difluoroethyl)-1,2,3,4-tetrahydroquinolin-2-one | Calc'd 334.0/336.0<br>Found 334.1/336.1 |
| A-68 | 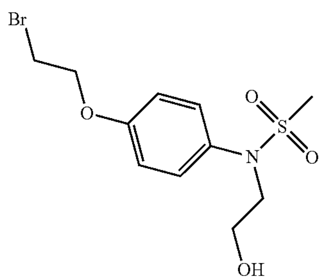 [SMILES: CS(=O)(=O)N(CCO)c1ccc(OCCBr)cc1] | N-[4-(2-bromoethoxy)phenyl]-N-(2-hydroxy-ethyl)methane-sulfonamide | Calc'd 338.0/340.0<br>Found 338.1/340.1 |
General Procedure for Intermediate A-69
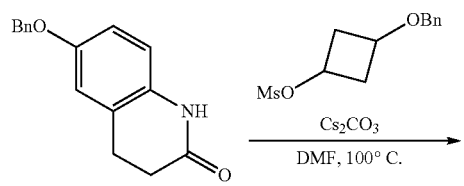
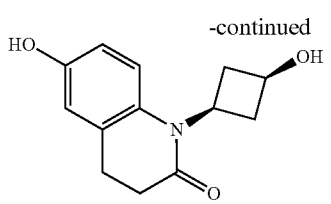 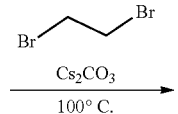
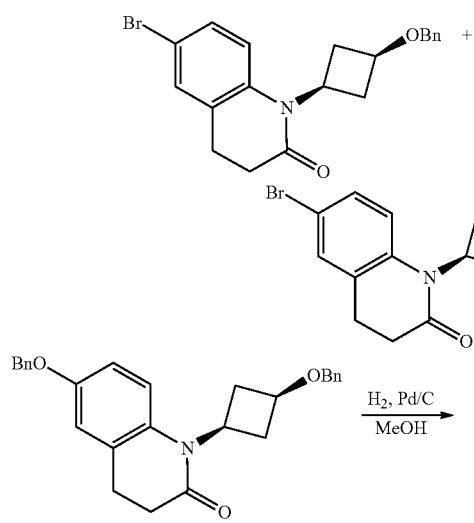
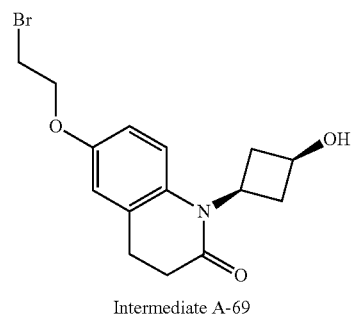
Intermediate A-69

Step 1: 6-(benzyloxy)-1-[(cis)-3-(benzyloxy)cyclobutyl]-1,2,3,4-tetrahydroquinolin-2-one

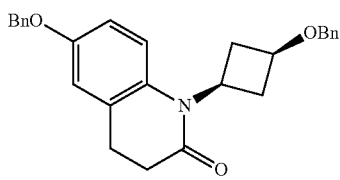 [SMILES: O=C1CCc2cc(OCc3ccccc3)ccc2N1[C@H]1C[C@@H](OCc2ccccc2)C1]

To a solution of 6-(benzyloxy)-1,2,3,4-tetrahydroquinolin-2-one (300 mg, 1.18 mmol) in DMF (4 mL) was added Cs$_2$CO$_3$ (1.54 g, 4.74 mmol) and 3-(benzyloxy)cyclobutyl methanesulfonate (910 mg, 3.55 mmol). The mixture was stirred at 100° C. for 12 h. After cooling to room temperature, the reaction mixture was poured into H$_2$O (10 mL) and extracted with EtOAc (3×10 mL). The combined organic layers were washed with brine (20 mL), filtered, dried over Na$_2$SO$_4$, and concentrated in vacuo. The crude residue was purified by normal phase silica gel chromatography (Biotage 20 g cartridge, 0-15% EtOAc:petroleum ether). The first eluting isomer, minor product 6-(benzyloxy)-1-[(trans)-3-(benzyloxy)cyclobutyl]-1,2,3,4-tetrahydroquinolin-2-one: $^1$H NMR (400 MHz, DMSO-d$_6$): δ 7.44-7.33 (m, 10H), 6.93 (d, J=2.4 Hz, 1H), 6.92-6.80 (m, 2H), 5.05 (s, 2H), 4.62-4.56 (m, 1H), 4.40 (s, 2H), 4.14-4.11 (m, 1H), 2.76-3.73 (m, 2H), 2.53-2.50 (m, 2H), 2.44-2.37 (m, 4H). The second eluting isomer, desired major product 6-(benzyloxy)-1-[(cis)-3-(benzyloxy)cyclobutyl]-1,2,3,4-tetrahydroquinolin-2-one: $^1$H NMR (400 MHz, DMSO-d$_6$): δ 7.45-7.39 (m, 4H), 7.33-7.28 (m, 6H), 6.94 (d, J=2.4 Hz, 1H), 6.93-6.77 (m, 2H), 5.06 (s, 2H), 4.36 (s, 2H), 3.93-3.88 (m, 1H), 3.80-3.77 (m, 1H), 2.88-2.86 (m, 2H), 2.77-2.73 (m, 2H), 2.40-2.37 (m, 2H), 1.95-1.89 (m, 2H).

Step 2: 6-hydroxy-1-[(cis)-3-hydroxycyclobutyl]-1,2,3,4-tetrahydroquinolin-2-one

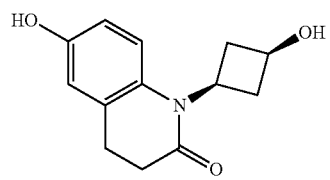 [SMILES: O=C1CCc2cc(O)ccc2N1[C@H]1C[C@@H](O)C1]

To a solution of 6-(benzyloxy)-1-[(cis)-3-(benzyloxy)cyclobutyl]-1,2,3,4-tetrahydroquinolin-2-one (400 mg, 0.967 mmol) in MeOH (20 mL) under N$_2$ atmosphere was added Pd/C (50 mg, 10 wt %, 0.47 mmol) The mixture was degassed and purged with H$_2$ (3×), then stirred under H$_2$ (50 Psi) atmosphere at room temperature for 12 h. The reaction mixture was filtered through Celeit and concentrated under in vacuo to give 6-hydroxy-1-[(cis)-3-hydroxycyclobutyl]-1,2,3,4-tetrahydroquinolin-2-one, which was used in the subsequent step without further purification. MS=234.3 [M+H]$^+$.

Step 3: 6-(2-bromoethoxy)-1-[(cis)-3-hydroxycyclobutyl]-1,2,3,4-tetrahydroquinolin-2-one

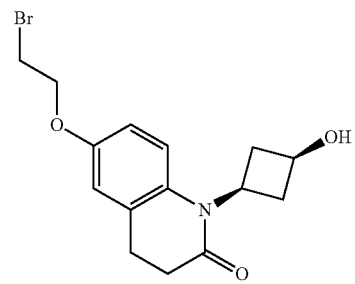 [SMILES: O=C1CCc2cc(OCCBr)ccc2N1[C@H]1C[C@@H](O)C1]

To a solution of 6-hydroxy-1-[(cis)-3-hydroxycyclobutyl]-1,2,3,4-tetrahydroquinolin-2-one (200 mg, 0.857 mmol) in 1,2-dibromoethane (5 mL, 133 mmol) was added Cs$_2$CO$_3$ (558 mg, 1.71 mmol). The mixture was stirred at 100° C. for 12 h. After cooling to room temperature, solids were removed by filtration and the filtrate was concentrated in vacuo. The residue was diluted with H$_2$O (10 mL) and extracted with DCM (3×10 mL). The combined organic layers were washed with brine (20 mL), dried over Na$_2$SO$_4$, filtered, and concentrated in vacuo. The crude residue was purified by normal phase silica gel chromatography (Isco 4 g cartridge, 0-47% EtOAc:petroleum ether) to give 6-(2-bromoethoxy)-1-[(cis)-3-hydroxycyclobutyl]-1,2,3,4-tetrahydroquinolin-2-one (Intermediate A-69). MS=340.1/342.1 [M+H]$^+$.

General Procedure for Intermediates A-70 & A-71

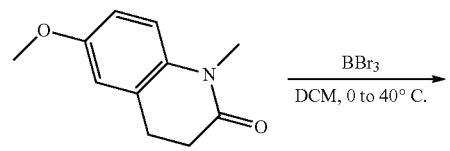

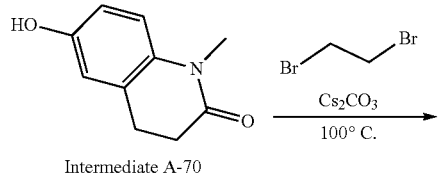

Intermediate A-70

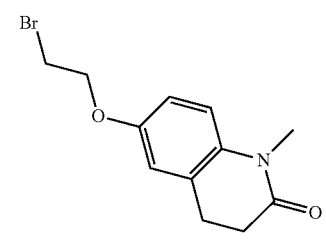

Intermediate A-71

Step 1: 6-hydroxy-1-methyl-1,2,3,4-tetrahydroquinolin-2-one

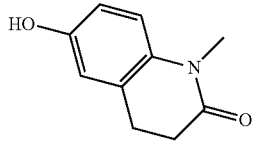

To a 0° C. solution of 6-methoxy-1-methyl-1,2,3,4-tetrahydroquinolin-2-one (150 mg, 0.784 mmol) in DCM (5 mL) was added BBr₃ (378 µL, 3.92 mmol) dropwise. The mixture was stirred at 40° C. for 4 h. After cooling to 0° C., the reaction mixture was quenched with H₂O (10 mL) and adjusted to pH=8 with saturated aqueous Na₂CO₃. The biphasic mixture was extracted with EtOAc (5×5 mL). The combined organic layers were dried over Na₂SO₄, filtered, and concentrated in vacuo. The crude residue was purified by normal phase silica gel chromatography (Biotage 20 g cartridge, 80-100% EtOAc:petroleum ether) to give 6-hydroxy-1-methyl-1,2,3,4-tetrahydroquinolin-2-one (Intermediate A-70). MS=178.1 [M+H]⁺.

Step 2: 6-(2-bromoethoxy)-1-methyl-1,2,3,4-tetrahydroquinolin-2-one

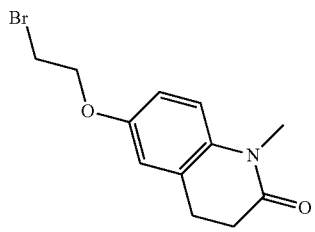 [SMILES: CN1C(=O)CCc2cc(OCCBr)ccc21]

To a solution of 6-hydroxy-1-methyl-3,4-dihydroquinolin-2-one (0.300 g, 1.69 mmol) in 1,2-dibromoethane (5.11 mL, 67.7 mmol) was added Cs₂CO₃ (1.10 g, 3.39 mmol). The mixture was stirred at 100° C. for 4 h. After cooling to 0° C., the reaction mixture was quenched with H₂O (20 mL) and extracted with DCM (3×10 mL). The combined organic layers were dried over Na₂SO₄, filtered, and concentrated in vacuo. The crude residue was purified by normal phase silica gel chromatography (Biotage 4 g cartridge, 0-25% EtOAc:petroleum ether) to give 6-(2-bromoethoxy)-1-methyl-1,2,3,4-tetrahydroquinolin-2-one (Intermediate A-71). MS=284.0/286.1 [M+H]⁺.

General Procedure for Intermediate A-72

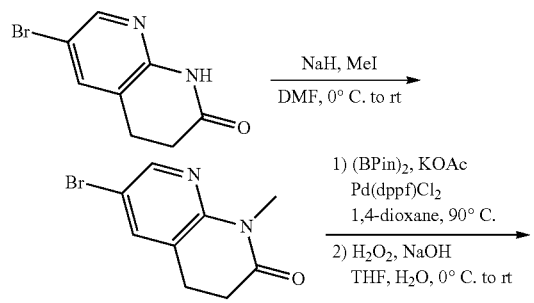

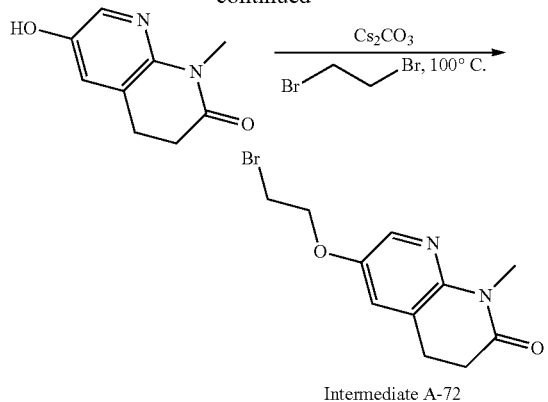

Intermediate A-72

Step 1: 6-bromo-1-methyl-1,2,3,4-tetrahydro-1,8-naphthyridin-2-one

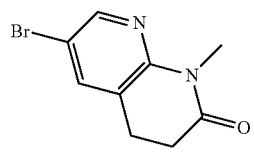

To a 0° C. solution of 6-bromo-1,2,3,4-tetrahydro-1,8-naphthyridin-2-one (739 mg, 3.26 mmol) in DMF (11 mL) was added NaH (156 mg, 60 wt %, 3.91 mmol). The mixture was stirred at for 1 h and then MeI (693 mg, 4.88 mmol) was added. The reaction mixture was warmed to room temperature and stirred for 1 h. The reaction mixture was then quenched with H₂O (30 mL) and extracted with EtOAc (3×20 mL). The combined organic layers were washed with brine (30 mL), dried over Na₂SO₄, filtered, and concentrated in vacuo. The crude residue was purified by normal phase silica gel chromatography (Biotage 25 g cartridge, 0-100% EtOAc:Hexanes) to give 6-bromo-1-methyl-1,2,3,4-tetrahydro-1,8-naphthyridin-2-one. ¹H NMR (500 MHz, CDCl₃): δ 8.31 (d, J=2.3 Hz, 1H), 7.59 (dd, J=2.3, 1.1 Hz, 1H), 3.45 (s, 3H), 2.91 (t, J=7.5 Hz, 2H), 2.72 (t, J=7.5 Hz, 2H).

Step 2: 6-hydroxy-1-methyl-1,2,3,4-tetrahydro-1,8-naphthyridin-2-one

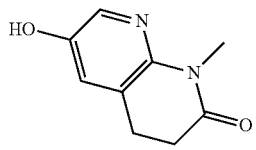

A solution of 6-bromo-1-methyl-1,2,3,4-tetrahydro-1,8-naphthyridin-2-one (450 mg, 1.87 mmol), potassium acetate (366 mg, 3.73 mmol), bis(pinacolato)diboron (569 mg 2.24 mmol) in 1,4-dioxane (9.3 mL) was sparged with nitrogen for 10 min. Pd(dppf)Cl₂ (68 mg, 0.093 mmol) was then added, and the reaction was heated to 90° C. for 2 h. The reaction mixture was cooled to room temperature, filtered over Celite, and washed with EtOAc (30 mL). The filtrate was concentrated in vacuo. The crude residue was purified by normal phase chromatography (Biotage 25 g cartridge, 10% EtOAc:hexanes). The resulting residue was dissolved in THF (25 mL) and H$_2$O (10 mL), and 1 M aqueous NaOH (5 mL) was added. The solution was cooled to 0° C. and H$_2$O$_2$ in H$_2$O (423 mg, 30 wt %, 3.7 mmol) was added dropwise over 3 min. The reaction mixture was allowed to warm room temperature and stirred for 16 h. The mixture was adjusted to pH=5 with 1.0 M aqueous HCl. The reaction mixture was extracted with EtOAc (3×50 mL). The combined organic layers were washed with brine (30 mL) and dried over Na$_2$SO$_4$, filtered, and concentrated in vacuo. The crude residue was purified by normal phase silica gel chromatography (Biotage 25 g cartridge, 10% MeOH:DCM) to give 6-hydroxy-1-methyl-1,2,3,4-tetrahydro-1,8-naphthyridin-2-one. $^1$H NMR (500 MHz, DMSO-d$_6$): δ 9.57 (s, 1H), 7.77 (d, J=2.7 Hz, 1H), 7.09 (d, J=2.8 Hz, 1H), 3.26 (s, 3H), 2.81 (t, J=7.5 Hz, 2H), 2.62-2.36 (m, 2H). MS=179.1 [M+H]$^+$.

Step 3: 6-(2-bromoethoxy)-1-methyl-1,2,3,4-tetrahydro-1,8-naphthyridin-2-one

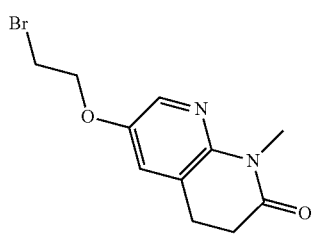 [SMILES: CN1C(=O)CCc2cc(OCCBr)cnc21]

To a solution of 6-hydroxy-1-methyl-1,2,3,4-tetrahydro-1,8-naphthyridin-2-one (221 mg, 1.24 mmol) in 1,2-dibromoethane (4.1 mL, 53 mmol) was added Cs$_2$CO$_3$ (1.2 g, 3.7 mmol) and the reaction was stirred at 100° C. for 6 h. The reaction was cooled to room temperature and diluted with EtOAc (10 mL). The reaction mixture was filtered over Celite and washed with EtOAc (30 mL). The reaction mixture was then concentrated in vacuo to afford 6-(2-bromoethoxy)-1-methyl-1,2,3,4-tetrahydro-1,8-naphthyridin-2-one (Intermediate A-72) which was used in the subsequent step without further purification. $^1$H NMR (500 MHz, CDCl$_3$): δ 7.94 (d, J=2.8 Hz, 1H), 7.11 (d, J=2.8 Hz, 1H), 4.33 (t, J=6.1 Hz, 2H), 3.65 (t, J=6.1 Hz, 2H), 3.45 (s, 3H), 2.88 (t, J=7.6 Hz, 2H), 2.69 (t, J=7.6 Hz, 2H).

General Procedure for Intermediate A-73

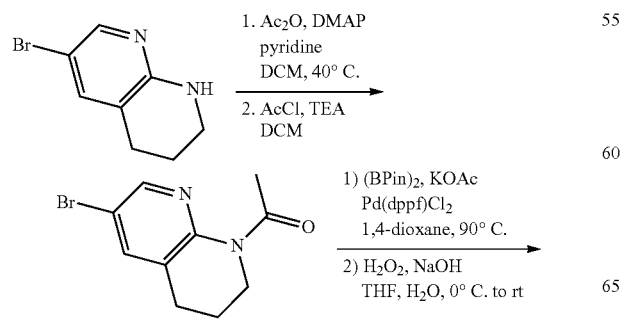

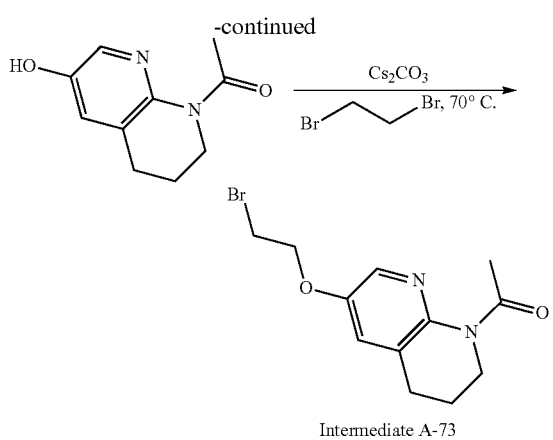

Intermediate A-73

Step 1: 1-(6-bromo-1,2,3,4-tetrahydro-1,8-naphthyridin-1-yl)ethan-1-one

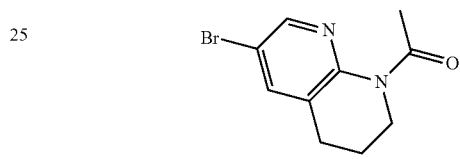

To a solution of 6-bromo-1,2,3,4-tetrahydro-1,8-naphthyridine (500 mg, 2.35 mmol) in DCM (12 mL) was added pyridine (757 μL, 9.39 mmol), acetic anhydride (660 μL, 7.05 mmol) and DMAP (5.0 mg, 0.041 mmol). The mixture was heated to 40° C. and stirred at for 16 h, and then cooled to room temperature. The reaction mixture was then quenched with H$_2$O (30 mL) and extracted with EtOAc (3×20 mL). The combined organic layers were washed with brine (30 mL), dried over Na$_2$SO$_4$, filtered, and concentrated in vacuo. The crude residue was purified by normal phase silica gel chromatography (Biotage 25 g cartridge, 0-100% EtOAc:Hexanes) to give a mixture of 1-(6-bromo-1,2,3,4-tetrahydro-1,8-naphthyridin-1-yl)ethan-1-one and unreacted 6-bromo-1,2,3,4-tetrahydro-1,8-naphthyridine. The mixture was redissolved in DCM (11.7 mL) and TEA (326 μL, 2.35 mmol) was added followed by acetyl chloride (167 μL, 2.35 mmol). After stirring for 16 h, the reaction mixture was quenched with H$_2$O (30 mL) and extracted with EtOAc (3×20 mL). The combined organic layers were washed with brine (30 mL), dried over Na$_2$SO$_4$, filtered, and concentrated in vacuo. The crude residue was purified by normal phase silica gel chromatography (Biotage 25 g cartridge, 0-100% EtOAc:Hexanes) to afford 1-(6-bromo-1,2,3,4-tetrahydro-1,8-naphthyridin-1-yl)ethan-1-one.

Step 2: 1-(6-hydroxy-1,2,3,4-tetrahydro-1,8-naphthyridin-1-yl)ethan-1-one

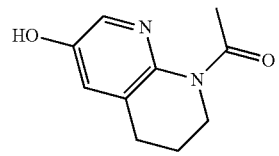

A solution of 1-(6-bromo-1,2,3,4-tetrahydro-1,8-naphthyridin-1-yl)ethan-1-one (435 mg, 1.71 mmol), potassium acetate (335 mg, 3.41 mmol), and bis(pinacolato)diboron (520 mg 2.05 mmol) in 1,4-dioxane (8.5 mL) was sparged with $N_2$ for 10 min. Pd(dppf)Cl$_2$ (62 mg, 0.085 mmol) was added, and the reaction was heated at 90° C. for 2 h. The reaction mixture was cooled to room temperature, filtered over Celite and washed with EtOAc (30 mL), then concentrated in vacuo. The crude residue was purified by normal phase silica gel chromatography (Biotage 25 g cartridge, 10% EtOAc:Hexanes). The resulting residue was dissolved in THF (25 mL) and H$_2$O (10 mL), and 1.0 M aqueous NaOH (5 mL) was added. The solution was cooled to 0° C. and H$_2$O$_2$ in H$_2$O (387 mg, 30 wt %, 3.4 mmol) was added dropwise over 3 min. The reaction mixture was allowed to warm room temperature and stirred for 16 h. The mixture was adjusted to pH=5 with 1.0 M aqueous HCl. The reaction mixture was extracted with EtOAc (3×50 mL). The combined organic layers were washed with brine (30 mL), dried over Na$_2$SO$_4$, filtered, and concentrated in vacuo. The crude residue was purified by normal phase chromatography (Biotage 25 g cartridge, 10% MeOH:DCM) to give 1-(6-hydroxy-1,2,3,4-tetrahydro-1,8-naphthyridin-1-yl)ethan-1-one. $^1$H NMR (500 MHz, CDCl$_3$, 11/12 H): δ 7.92 (d, J=2.8 Hz, 1H), 7.04 (d, J=2.8 Hz, 1H), 3.89 (t, J=6.3 Hz, 2H), 2.75 (t, J=6.6 Hz, 2H), 2.41 (s, 3H), 2.00-1.85 (m, 2H). MS=193.1 [M+H]$^+$.

Step 3: 1-[6-(2-bromoethoxy)-1,2,3,4-tetrahydro-1,8-naphthyridin-1-yl]ethan-1-one

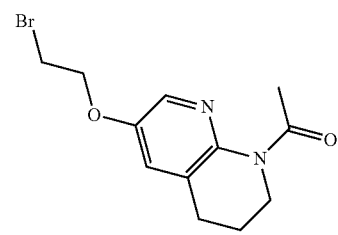 [SMILES: CC(=O)N1CCCc2cc(OCCBr)cnc21]

To a solution of 1-(6-hydroxy-1,2,3,4-tetrahydro-1,8-naphthyridin-1-yl)ethan-1-one (124 mg, 0.645 mmol) in 1,2-dibromoethane (2.1 mL, 27.8 mmol) was added Cs$_2$CO$_3$ (631 mg, 1.94 mmol), and the reaction was stirred at 70° C. for 6 h. The reaction was cooled to room temperature and diluted with EtOAc (10 mL). The reaction mixture was filtered over Celite and washed with EtOAc (30 mL). The reaction mixture was then concentrated in vacuo to afford 1-[6-(2-bromoethoxy)-1,2,3,4-tetrahydro-1,8-naphthyridin-1-yl]ethan-1-one (Intermediate A-73) which was used without further purification. $^1$H NMR (500 MHz, CDCl$_3$): δ 7.96 (d, J=2.9 Hz, 1H), 7.08 (d, J=2.9 Hz, 1H), 4.35 (t, J=6.1 Hz, 2H), 3.90 (t, J=6.2 Hz, 2H), 3.67 (t, J=6.1 Hz, 2H), 2.78 (t, J=6.7 Hz, 2H), 2.43 (s, 3H), 1.98-1.93 (m, 2H).

General Procedure for Intermediates A-74

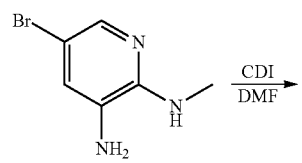

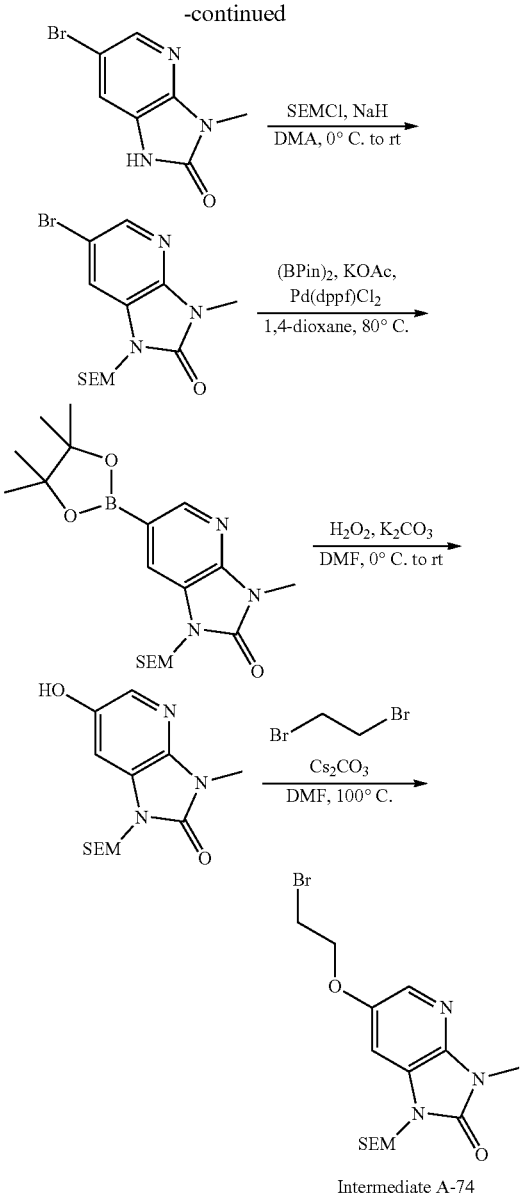

Intermediate A-74

Step 1: 6-bromo-3-methyl-1H,2H,3H-imidazo[4,5-b]pyridin-2-one

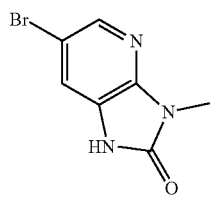

To a solution of 5-bromo-N$_2$-methylpyridine-2,3-diamine (1.00 g, 4.95 mmol) in DMF (15 mL) was added CDI (3.21 g, 19.8 mmol). The mixture was stirred at room temperature for 16 h. The reaction mixture was quenched with H$_2$O (20 mL) and extracted with EtOAc (2×20 mL). The combined organic layers were washed with brine (2×10 mL), dried over Na$_2$SO$_4$, filtered, and concentrated in vacuo. The crude residue was purified by normal phase silica gel chromatography (Biotage 20 g cartridge, 0-100% EtOAc:Hexanes) to give 6-bromo-3-methyl-1H,2H,3H-imidazo[4,5-b]pyridin-2-one. MS=228.1/230.1 [M+H]$^+$.

Step 2: 6-bromo-3-methyl-1-{[2-(trimethylsilyl)ethoxy]methyl}-1H,2H,3H-imidazo[4,5-b]pyridin-2-one

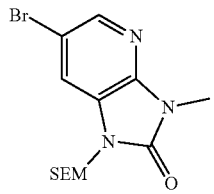 [SMILES: Cn1c(=O)n(COCC[Si](C)(C)C)c2cc(Br)cnc21]

To a 0° C. solution of 6-bromo-3-methyl-1H,2H,3H-imidazo[4,5-b]pyridin-2-one (500 mg, 2.19 mmol) in DMA (8 mL) was added NaH (263 mg, 60 wt % in mineral oil, 6.58 mmol) portionwise. The mixture was stirred at 0° C. for 30 min and then 2-(trimethylsilyl)ethoxymethyl chloride (0.582 mL, 3.29 mmol) was added dropwise. The mixture was allowed to warm to room temperature and was stirred for an additional 4.5 h. The reaction mixture was cooled to 0° C. and then quenched with saturated aqueous NH$_4$Cl (5 mL), diluted with H$_2$O (5 mL), and extracted with EtOAc (3×5 mL). The combined organic layers were washed with brine (5 mL), dried over Na$_2$SO$_4$, filtered, and concentrated in vacuo. The crude residue was purified by normal phase silica gel chromatography (Biotage 10 g cartridge, 0-100% EtOAc:Hexanes) to give 6-bromo-3-methyl-1-{[2-(trimethylsilyl)ethoxy]methyl}-1H,2H,3H-imidazo[4,5-b]pyridin-2-one. MS=358.1/360.1 [M+H]$^+$.

Step 3: 3-methyl-6-(4,4,5,5-tetramethyl-1,3,2-dioxaborolan-2-yl)-1-{[2-(trimethylsilyl)ethoxy]methyl}-1H,2H,3H-imidazo[4,5-b]pyridin-2-one

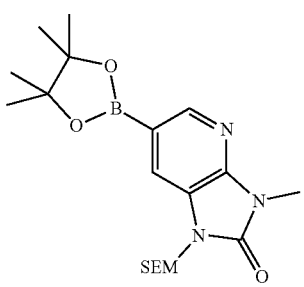

A mixture of 6-bromo-3-methyl-1-{[2-(trimethylsilyl)ethoxy]methyl}-1H,2H,3H-imidazo[4,5-b]pyridin-2-one (1.80 g, 5.02 mmol), bis(pinacolato)diboron (1.53 g, 6.03 mmol), Pd(dppf)Cl$_2$ (368 mg, 0.502 mmol), and KOAc (986 mg, 10.1 mmol) in 1,4-dioxane (25 mL) was degassed and purged with N$_2$ (3×). The mixture was heated at 80° C. for 12 h. After cooling to room temperature, the reaction mixture was quenched with H$_2$O (20 mL) and extracted with EtOAc (2×30 mL). The combined organic layers were washed with brine (2×20 mL), dried over Na$_2$SO$_4$, filtered, and concentrated in vacuo. The crude residue was purified by normal phase silica gel chromatography (Biotage 20 g cartridge, 0-100% EtOAc:petroleum ether) to give 3-methyl-6-(4,4,5,5-tetramethyl-1,3,2-dioxaborolan-2-yl)-1-{[2-(trimethylsilyl)ethoxy]methyl}-1H,2H,3H-imidazo[4,5-b]pyridin-2-one. MS=406.3 [M+H]$^+$.

Step 4: 6-hydroxy-3-methyl-1-{[2-(trimethylsilyl)ethoxy]methyl}-1H,2H,3H-imidazo[4,5-b]pyridin-2-one

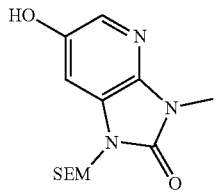 [SMILES: Cn1c(=O)n(COCC[Si](C)(C)C)c2cc(O)cnc21]

To a 0° C. mixture of 3-methyl-6-(4,4,5,5-tetramethyl-1,3,2-dioxaborolan-2-yl)-1-{[2-(trimethylsilyl)ethoxy]methyl}-1H,2H,3H-imidazo[4,5-b]pyridin-2-one (2.00 g, 4.93 mmol) in DCM (30 mL) was added H$_2$O$_2$ in H$_2$O (1.19 mL, 30 wt %, 12.3 mmol) and K$_2$CO$_3$ (1.36 g, 9.87 mmol). The mixture was stirred at room temperature for 10 h. The reaction mixture was cooled to 0° C., quenched with saturated aqueous Na$_2$SO$_3$ (40 mL), and extracted with EtOAc (2×50 mL). The combined organic layers were washed with saturated aqueous Na$_2$SO$_3$ (40 mL), dried over Na$_2$SO$_4$, filtered, and concentrated in vacuo. The crude residue was purified by normal phase silica gel chromatography (Biotage 20 g cartridge, 0-100% EtOAc:petroleum ether) to give 6-hydroxy-3-methyl-1-{[2-(trimethylsilyl)ethoxy]methyl}-1H,2H,3H-imidazo[4,5-b]pyridin-2-one. MS=296.2 [M+H]$^+$.

Step 5: 6-(2-bromoethoxy)-3-methyl-1-{[2-(trimethylsilyl)ethoxy]methyl}-1H,2H,3H-imidazo[4,5-b]pyridin-2-one

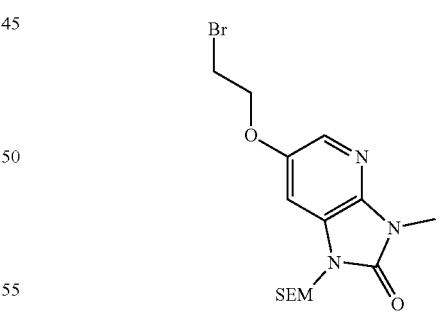

To a mixture of 6-hydroxy-3-methyl-1-{[2-(trimethylsilyl)ethoxy]methyl}-1H,2H,3H-imidazo[4,5-b]pyridin-2-one (600 mg, 2.03 mmol) and 1,2-dibromoethane (1.53 mL, 20.3 mmol) in DMF (5 mL) was added Cs$_2$CO$_3$ (1.32 g, 4.06 mmol). The mixture was stirred at 100° C. for 10 h. After cooling to room temperature, the reaction mixture was quenched by the addition of H$_2$O (10 mL) and extracted with EtOAc (2×10 mL). The combined organic layers were washed with brine (10 mL), dried over Na$_2$SO$_4$, filtered, and concentrated in vacuo. The crude residue was purified by normal phase silica gel chromatography (Biotage 10 g cartridge, 0-100% EtOAc:petroleum ether) to give 6-(2-bromoethoxy)-3-methyl-1-{[2-(trimethylsilyl)ethoxy]methyl}-1H,2H,3H-imidazo[4,5-b]pyridin-2-one (Intermediate A-74). MS=402.2/404.1 [M+H]+.

General Procedure for Intermediate A-75

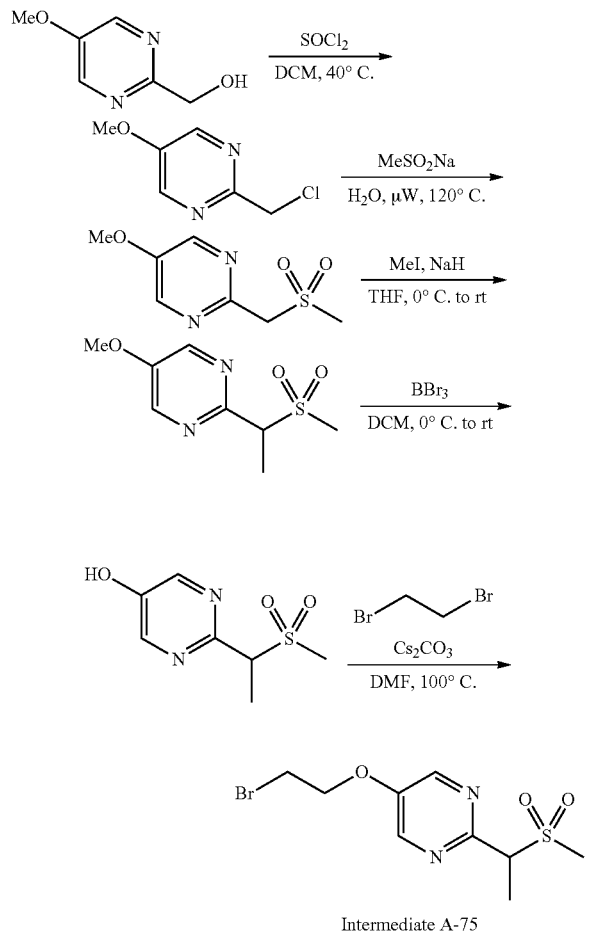

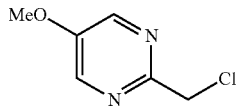

Step 1: 2-(Chloromethyl)-5-methoxypyrimidine

To a solution of (5-methoxypyrimidin-2-yl)methanol (4.00 g, 28.5 mmol) in DCM (143 mL) under $N_2$ atmosphere was added thionyl chloride (6.21 mL, 64.2 mmol). The reaction mixture was heated at 40° C. for 2 h. After cooling to room temperature, the reaction was quenched with $H_2O$ (100 mL) and extracted with EtOAc (3×100 mL). The combined organic layers were dried over $Na_2SO_4$, filtered, and concentrated in vacuo give 2-(chloromethyl)-5-methoxypyrimidine, which was used in the subsequent step without further purification.

Step 2: -(Methanesulfonylmethyl)-5-methoxypyrimidine

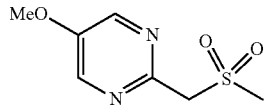

To a microwave vial equipped with a stir bar was added 2-(chloromethyl)-5-methoxypyrimidine (1.00 g, 6.31 mmol) and sodium methanesulfinate (0.837 g, 8.20 mmol) followed by $H_2O$ (12.6 mL). The vial was sealed and heated at 120° C. in a microwave at 40 psi for 30 min. The reaction mixture was cooled to 0° C. the resulting solid was isolated by filtration and dried in vacuo to give 2-(methanesulfonylmethyl)-5-methoxypyrimidine, which was used in the subsequent step without further purification. MS=203.0 [M+H]+.

Step 3: 2-(1-Methanesulfonylethyl)-5-methoxypyrimidine

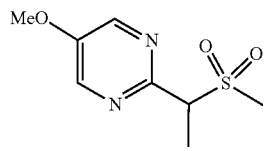

To a solution of 2-(methanesulfonylmethyl)-5-methoxypyrimidine (1.25 g, 6.18 mmol) in DMF (29.4 mL) at 0° C. was added NaH (0.494 g, 60 wt % in mineral oil, 12.4 mmol). The reaction was mixture was allowed to warm to room temperature and stirred for 10 min. MeI (0.366 mL, 5.87 mmol) was added, and the mixture was allowed to stir at room temperature for 1 h. The reaction mixture was quenched with $H_2O$ (50 mL) and extracted with EtOAc (3×50 mL). The combined organic layers were combined and washed with 5% aqueous LiCl solution (100 mL), dried over $Na_2SO_4$, and concentrated in vacuo. Purification by normal phase silica gel chromatography (0-100% EtOAc in Hexanes) provided 2-(1-methanesulfonylethyl)-5-methoxypyrimidine. MS=217.12 [M+H]+.

Step 4: 2-(1-Methanesulfonylethyl)pyrimidin-5-ol

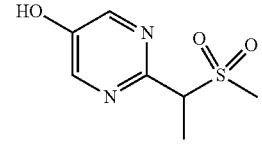

To a solution of 2-(1-methanesulfonylethyl)-5-methoxypyrimidine (500 mg, 2.31 mmol) in DCM (11.6 mL) at 0° C. was added a solution of 1.0 M $BBr_3$ in DCM (11.6 mL, 11.6 mmol). The mixture was allowed to warm to room temperature and stirred for 5 h. The reaction mixture was concentrated in vacuo, then re-dissolved in DCM and concentrated in vacuo (2×). The residue was quenched with MeOH (30 mL), and then concentrated in vacuo to provide 5-(2-bromoethoxy)-2-(1-methanesulfonylethyl)pyrimidine,

Step 5: 5-(2-Bromoethoxy)-2-(1-methanesulfonyl-ethyl)pyrimidine

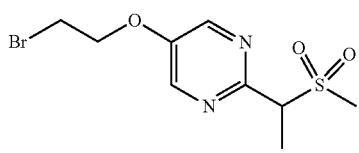 [SMILES: CC(c1ncc(OCCBr)cn1)S(C)(=O)=O]

To a solution of 2-(1-methanesulfonylethyl)pyrimidin-5-ol (500 mg, 2.47 mmol) in 1,2-dibromoethane (8.24 mL, 93.9 mmol) and DMF (0.5 mL) was added $Cs_2CO_3$ (2.42 g, 7.42 mmol). The reaction mixture was heated at 100° C. for 6 h, then allowed to cool to room temperature. The reaction mixture was then diluted with 20 mL EtOAc, filtered over Celite and concentrated in vacuo to afford crude 5-(2-bromoethoxy)-2-(1-methanesulfonylethyl)pyrimidine (Intermediate A-75), which was used in the subsequent step without further purification. MS=309.0/311.0 $[M+H]^+$.

General Procedure for Intermediate A-76

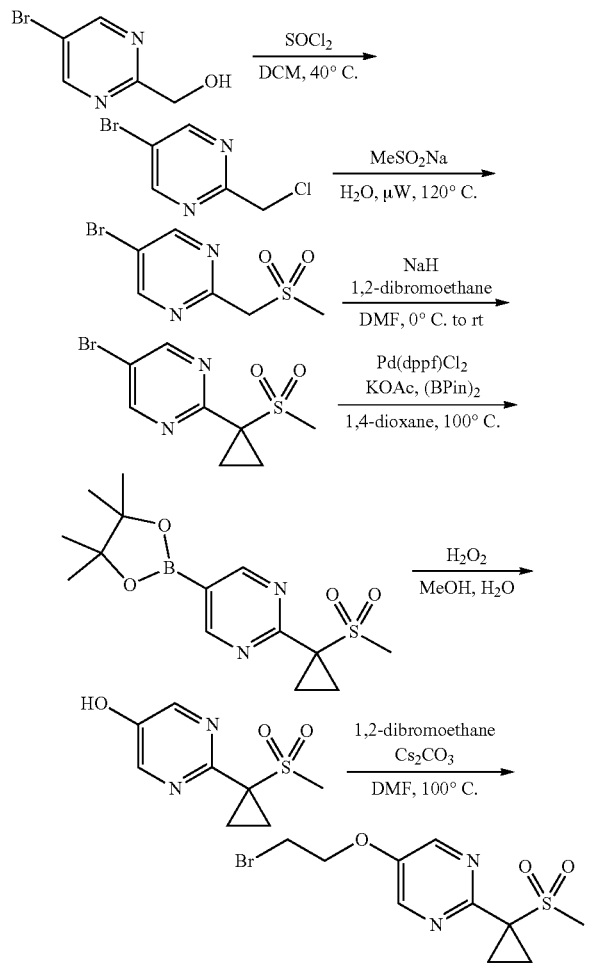

Intermediate A-76

Step 1: 5-Bromo-2-(chloromethyl)pyrimidine

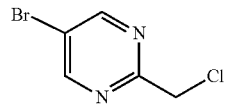

To a solution of (5-bromopyrimidin-2-yl)methanol (5.00 g, 26.5 mmol) in DCM (132 mL) under $N_2$ atmosphere was added thionyl chloride (5.76 mL, 79.4 mmol). The reaction mixture was heated at 40° C. for 2 h. After cooling to room temperature, the mixture was quenched with $H_2O$ (100 mL) and extracted with EtOAc (3×100 mL). The combined organic layers were dried over $Na_2SO_4$, filtered, then concentrated in vacuo to give 5-bromo-2-(chloromethyl)pyrimidine, which was used in the subsequent step without further purification. MS=207.0/209.0 $[M+H]^+$.

Step 2: 5-Bromo-2-(methanesulfonylmethyl)pyrimidine

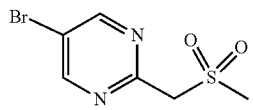

To a microwave vial equipped with a stir bar were added 5-bromo-2-(chloromethyl)pyrimidine (2.00 g, 9.64 mmol), sodium methanesulfinate (1.28 g, 12.5 mmol), and then $H_2O$ (19 mL). The vial was sealed and heated at 120° C. in a microwave at 40 psi for 30 min. The reaction mixture was then cooled to 0° C. and the resulting solid was isolated by filtration and dried in vacuo to give 2-(methanesulfonylmethyl)-5-methoxypyrimidine, which was used in the subsequent step without further purification. MS=251.0/253.0 $[M+H]^+$.

Step 3: 5-Bromo-2-(1-methanesulfonylcyclopropyl)pyrimidine

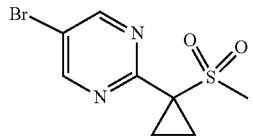

To a solution of 5-bromo-2-(methanesulfonylmethyl)pyrimidine (250 mg, 1.00 mmol) in DMF (5.0 mL) at 0° C. was added NaH (0.119 g, 60 wt % in mineral oil, 2.99 mmol). The reaction mixture was allowed to warm to room temperature for 10 min, then 1,2-dibromoethane (0.561 g, 2.99 mmol) was added. The mixture was allowed to stir for 1 h, then was diluted with $H_2O$ (20 mL). The aqueous layer was extracted with EtOAc (3×20 mL). The combined organic layers were washed with 5% aqueous LiCl solution (50 mL), dried over $Na_2SO_4$, and concentrated in vacuo. Purification by normal phase silica gel chromatography (0-100% EtOAc: hexanes) gave 5-bromo-2-(1-methanesulfonylcyclopropyl) pyrimidine. $^1H$ NMR (500 MHz, $CDCl_3$): δ 8.74 (s, 2H), 3.36 (s, 3H), 2.03-1.98 (m, 2H), 1.79-1.75 (m, 2H). MS=277.0/279.0 $[M+H]^+$.

Step 4: 2-(1-Methanesulfonylcyclopropyl)-5-(4,4,5,5-tetramethyl-1,3,2-dioxaborolan-2-yl)pyrimidine

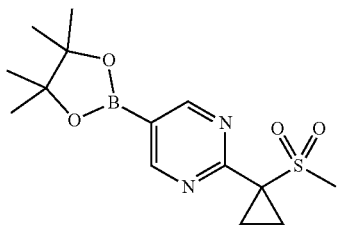

To a vial equipped with a stir bar were added 5-bromo-2-(1-methanesulfonylcyclopropyl)pyrimidine (500 mg, 1.80 mmol), bis(pinacolato)diboron (687 mg, 2.71 mmol), potassium acetate (619 mg, 6.31 mmol), 1,1'-bis(diphenylphosphino)ferrocene palladium dichloride (66 mg, 0.09 mmol), and dry 1,4-dioxane (9.0 mL). The vial was sealed and evacuated until gas evolution from the solution was observed. The vial was then filled with N$_2$ and evacuated. This process was repeated three times, and the sealed vial was then heated at 100° C. for 16 h. The reaction mixture was allowed to cool to room temperature and was then diluted with EtOAc (20 mL). The mixture was filtered through Celite, and the filtrate was concentrated in vacuo to provide 2-(1-methanesulfonylcyclopropyl)-5-(4,4,5,5-tetramethyl-1,3,2-dioxaborolan-2-yl)pyrimidine, which was used in the subsequent step without further purification.

Step 5: 2-(1-Methanesulfonylcyclopropyl)pyrimidin-5-ol

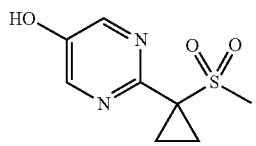

To a vial containing a solution of 2-(1-methanesulfonylcyclopropyl)-5-(4,4,5,5-tetramethyl-1,3,2-dioxaborolan-2-yl)pyrimidine (300 mg, 0.93 mmol) in MeOH (3.1 mL) was added 30% hydrogen peroxide in H$_2$O (0.284 mL, 2.78 mmol) dropwise. The mixture was allowed to stir for 2 h. The reaction mixture was concentrated in vacuo, diluted with MeOH, and concentrated in vacuo. The resulting mixture was diluted with MeOH and concentrated to give 2-(1-methanesulfonylcyclopropyl)pyrimidin-5-ol, which was used in the subsequent step without further purification. MS=215.04 [M+H]$^+$.

Step 6: 5-(2-Bromoethoxy)-2-(1-methanesulfonylcyclopropyl)pyrimidine

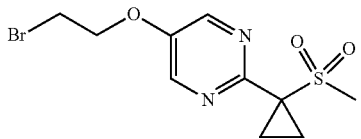 [SMILES: CS(=O)(=O)C1(c2ncc(OCCBr)cn2)CC1]

A vial was charged with 2-(1-methanesulfonylcyclopropyl)pyrimidin-5-ol (200 mg, 0.934 mmol) and dissolved in 1,2-dibromoethane (3.1 mL, 41 mmol) and DMF (0.5 mL). Cs$_2$CO$_3$ (0.912 g, 2.801 mmol) was added, and the reaction mixture was heated at 100° C. for 6 h. After cooling to room temperature, the reaction mixture was then filtered over Celite and concentrated in vacuo to afford 5-(2-bromoethoxy)-2-(1-methanesulfonylcyclopropyl)pyrimidine (Intermediate A-76), which was carried onto the next step without further purification. MS=321.1/323.1 [M+H]$^+$.

General Procedure for Intermediate A-77

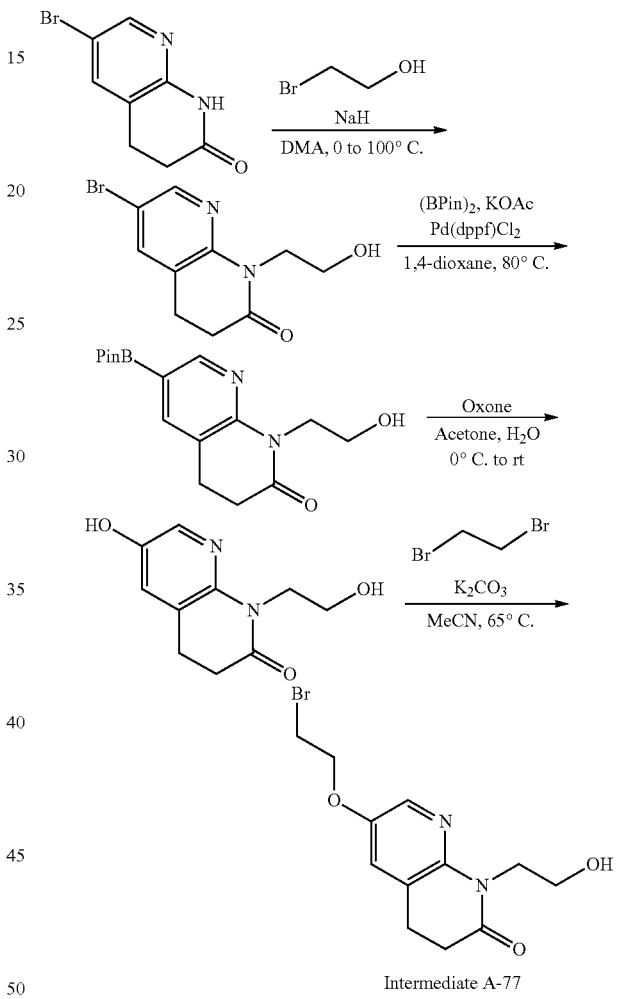

Intermediate A-77

Step 1: 6-bromo-1-(2-hydroxyethyl)-1,2,3,4-tetrahydro-1,8-naphthyridin-2-one

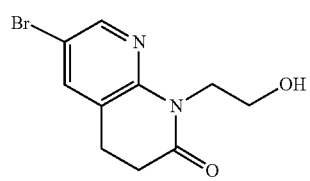 [SMILES: O=C1CCc2cc(Br)cnc2N1CCO]

To a 0° C. solution of 6-bromo-1,2,3,4-tetrahydro-1,8-naphthyridin-2-one (4.00 g, 17.6 mmol) in DMA (80 mL)

under N₂ atmosphere was added NaH (3.52 g, 60 wt % in mineral oil, 88.1 mmol). After stirring for 15 min, 2-bromoethanol (22.0 g, 176 mmol) was added dropwise. The reaction mixture was heated to 100° C. and stirred for 16 h. The reaction mixture was cooled to 0° C., quenched with H₂O (40 mL), and extracted with EtOAc (3×50 mL). The combined organic layers were washed with brine (2×40 mL), dried over Na₂SO₄, filtered, and concentrated in vacuo. The crude residue was purified by normal phase silica gel chromatography (Biotage 40 g cartridge, 0-45% EtOAc: petroleum ether) to give 6-bromo-1-(2-hydroxyethyl)-1,2,3,4-tetrahydro-1,8-naphthyridin-2-one. MS=271.0/273.0 [M+H]⁺.

Step 2: 1-(2-hydroxyethyl)-6-(4,4,5,5-tetramethyl-1,3,2-dioxaborolan-2-yl)-1,2,3,4-tetrahydro-1,8-naphthyridin-2-one

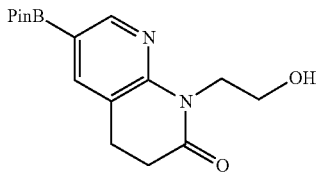

To a mixture of 6-bromo-1-(2-hydroxyethyl)-1,2,3,4-tetrahydro-1,8-naphthyridin-2-one (2.00 g, 7.38 mmol) and bis(pinacolato)diboron (2.25 g, 8.85 mmol) in 1,4-dioxane (30 mL) was added KOAc (1.45 g, 14.8 mmol). The mixture was degassed and purged with N₂ (3×). Pd(dppf)Cl₂ (540 mg, 0.738 mmol) was added, then the mixture was heated to 80° C. and stirred for 16 h under N₂ atmosphere. After cooling to room temperature, the reaction mixture was filtered, and the filtrate was concentrated in vacuo. The crude residue was purified by normal phase silica gel chromatography (Biotage 20 g cartridge, 0-30% EtOAc:petroleum ether) to give 1-(2-hydroxyethyl)-6-(4,4,5,5-tetramethyl-1,3,2-dioxaborolan-2-yl)-1,2,3,4-tetrahydro-1,8-naphthyridin-2-one. MS=319.2.0 [M+H]⁺.

Step 3: 6-hydroxy-1-(2-hydroxyethyl)-1,2,3,4-tetrahydro-1,8-naphthyridin-2-one

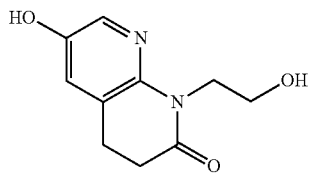 [SMILES: O=C1CCc2cc(O)cnc2N1CCO]

To a 0° C. solution of 1-(2-hydroxyethyl)-6-(4,4,5,5-tetramethyl-1,3,2-dioxaborolan-2-yl)-1,2,3,4-tetrahydro-1,8-naphthyridin-2-one (1.60 g, 5.03 mmol) in acetone (10 mL) and H₂O (10 mL) was added Oxone (3.71 g, 6.03 mmol). The mixture was stirred at room temperature for 2 h. The reaction mixture was cooled to 0° C., quenched with saturated aqueous Na₂SO₃ (40 mL), and extracted with EtOAc (2×50 mL). The combined organic layers were washed with saturated aqueous Na₂SO₃ (50 mL), dried over Na₂SO₄, filtered, and concentrated in vacuo to give 6-hydroxy-1-(2-hydroxyethyl)-1,2,3,4-tetrahydro-1,8-naphthyridin-2-one, which was used in the subsequent step without further purification. MS=209.1 [M+H]⁺.

Step 4: 6-(2-bromoethoxy)-1-(2-hydroxyethyl)-1,2,3,4-tetrahydro-1,8-naphthyridin-2-one

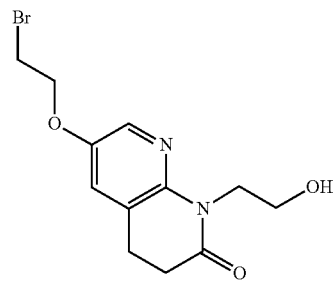 [SMILES: O=C1CCc2cc(OCCBr)cnc2N1CCO]

A mixture of 6-hydroxy-1-(2-hydroxyethyl)-1,2,3,4-tetrahydro-1,8-naphthyridin-2-one (200 mg, 0.961 mmol), 1,2-dibromoethane (1.45 mL, 19.2 mmol) and K₂CO₃ (664 mg, 4.80 mmol) in MeCN (3 mL) was stirred at 80° C. for 16 h. After cooling to room temperature, the reaction mixture was filtered, and the filtrate was concentrated in vacuo. The crude residue was purified by normal phase silica gel chromatography (Biotage 20 g cartridge, 0-30% EtOAc:petroleum ether) to give 6-(2-bromoethoxy)-1-(2-hydroxyethyl)-1,2,3,4-tetrahydro-1,8-naphthyridin-2-one (Intermediate A-77). MS=315.1/317.1 [M+H]⁺.

General Procedure for Intermediate A-78

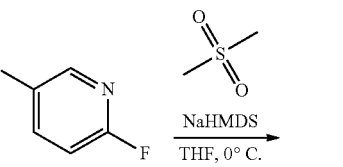

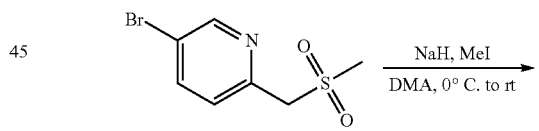

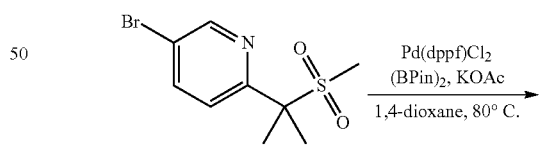

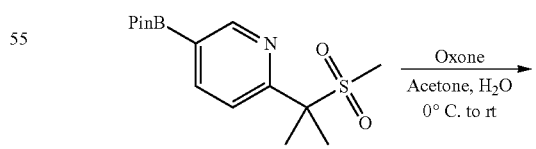

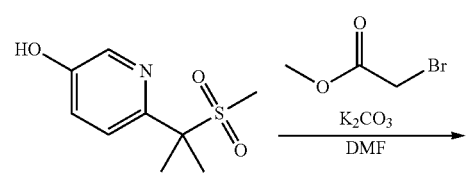

-continued

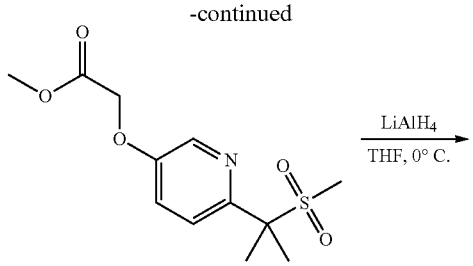

LiAlH₄
—————→
THF, 0° C.

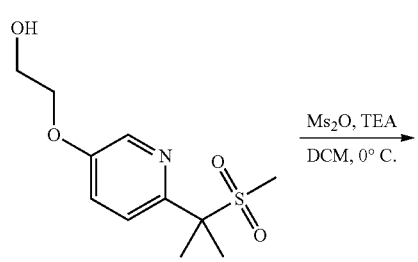

Ms₂O, TEA
—————→
DCM, 0° C.

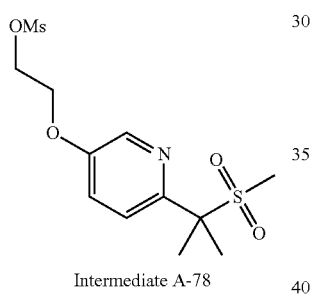

Intermediate A-78

Step 1: 5-bromo-2-(methanesulfonylmethyl)pyridine

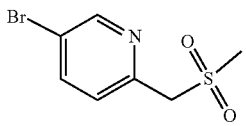

To a 0° C. solution of DMSO (11.5 mL, 142 mmol) in THF (100 mL) under N₂ atmosphere was added 1.0 M NaHMDS in THF (142 mL, 142 mmol) dropwise. The mixture was stirred at 0° C. for 1 h, then a solution of 5-bromo-2-fluoropyridine (2.92 mL, 28.4 mmol) in THF (50 mL) was added dropwise, and the mixture was stirred for another 1 h. The reaction mixture was quenched with H₂O (40 mL) and then extracted with EtOAc (3×50 mL. The combined organic layers were washed with brine (2×50 mL), dried over Na₂SO₄, filtered, and concentrated in vacuo. Purification by reverse phase preparative HPLC (Agela C₁₈ column, 20-50% MeCN in water with 0.1% NH₄OH modifier) afforded 5-bromo-2-(methanesulfonylmethyl)pyridine. MS=250.0/252.0 [M+H]⁺.

Step 2:
5-bromo-2-(2-methanesulfonylpropan-2-yl)pyridine

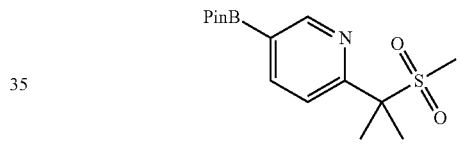

To a 0° C. solution of 5-bromo-2-(methanesulfonylmethyl)pyridine (3.00 g, 12.0 mmol) in DMA (30 mL) under N₂ atmosphere was added NaH (1.06 g, 60 wt % in mineral oil, 26.4 mmol) portionwise. After stirring at 0° C. for 1 h, a solution of MeI (2.24 mL, 36.0 mmol, 2.24 mL) in DMA (30 mL) was added dropwise. The mixture was allowed to warm to room temperature and stirred for another 12 h. The mixture was cooled to 0° C., quenched with H₂O (40 mL), and extracted with EtOAc (3×50 mL). The combined organic layers were washed with brine (2×50 mL), dried over Na₂SO₄, filtered, and concentrated in vacuo. The crude residue was purified by normal phase silica gel chromatography (Biotage 40 g cartridge, 0-40% EtOAc:petroleum ether) to give 5-bromo-2-(2-methanesulfonylpropan-2-yl)pyridine. MS=278.1/280.1 [M+H]⁺.

Step 3: 2-(2-methanesulfonylpropan-2-yl)-5-(4,4,5,5-tetramethyl-1,3,2-dioxaborolan-2-yl)pyridine

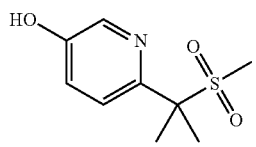

To a mixture of 5-bromo-2-(2-methanesulfonylpropan-2-yl)pyridine (2.40 g, 8.63 mmol), bis(pinacolato)diboron (3.29 g, 12.9 mmol) in 1,4-dioxane (10 mL) was added KOAc (1.69 g, 17.3 mmol). The mixture was degassed and purged with N₂ (3×), and then the Pd(dppf)Cl₂ (316 mg, 0.431 mmol) was added. The mixture was heated to 80° C. and stirred for 12 h under N₂ atmosphere. The reactions mixture was cooled to room temperature, was diluted with H₂O (40 mL), and extracted with EtOAc (3×50 mL). The combined organic layers washed with brine (2×50 mL), dried over Na₂SO₄, filtered, and concentrated in vacuo. The crude residue was purified by normal phase silica gel chromatography (Biotage 40 g cartridge, 0-40% EtOAc: petroleum ether) to give 2-(2-methanesulfonylpropan-2-yl)-5-(4,4,5,5-tetramethyl-1,3,2-dioxaborolan-2-yl)pyridine. MS=326.2 [M+H]⁺.

Step 4:
6-(2-methanesulfonylpropan-2-yl)pyridin-3-ol

To a 0° C. solution of 2-(2-methanesulfonylpropan-2-yl)-5-(4,4,5,5-tetramethyl-1,3,2-dioxaborolan-2-yl)pyridine (900 mg, 2.77 mmol) in acetone (10 mL) and H₂O (10 mL) was added Oxone (3.40 g, 5.53 mmol). The mixture was allowed to warm to room temperature and stirred for 2 h. The reaction mixture was cooled to 0° C. and quenched with saturated aqueous Na₂SO₃ (50 mL), then extracted with EtOAc (3×50 mL). The combined organic layers were washed with brine (2×50 mL), dried over Na₂SO₄, filtered, and concentrated in vacuo. The crude residue was purified by normal phase silica gel chromatography (Biotage 40 g cartridge, 0-40% EtOAc:petroleum ether) to give 6-(2-methanesulfonylpropan-2-yl)pyridin-3-ol. MS=216.1 [M+H]⁺.

Step 5: methyl 2-{[6-(2-methanesulfonylpropan-2-yl)pyridin-3-yl]oxy}acetate

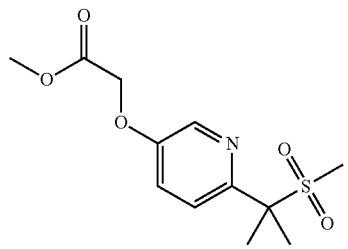

To a solution of 6-(2-methanesulfonylpropan-2-yl)pyridin-3-ol (300 mg, 1.39 mmol) in DMF (6 mL) were added K₂CO₃ (385 mg, 2.79 mmol) and methyl 2-bromoacetate (255 mg, 1.67 mmol). The mixture was stirred at room temperature. The mixture was quenched with H₂O (20 mL) and then extracted with EtOAc (2×30 mL). The combined organic layers were washed with brine (2×20 mL), dried over Na₂SO₄, filtered, and concentrated in vacuo. The crude residue was purified by normal phase silica gel chromatography (Biotage 40 g cartridge, 0-40% EtOAc:petroleum ether) to give methyl 2-{[6-(2-methanesulfonylpropan-2-yl)pyridin-3-yl]oxy}acetate. MS=288.1 [M+H]⁺.

Step 6: 2-{[6-(2-methanesulfonylpropan-2-yl)pyridin-3-yl]oxy}ethan-1-ol

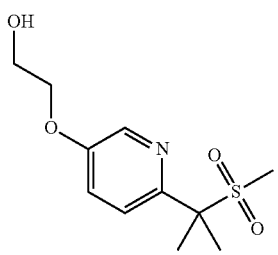 [SMILES: CC(C)(c1ccc(OCCO)cn1)S(C)(=O)=O]

To a 0° C. solution of methyl 2-{[6-(2-methanesulfonylpropan-2-yl)pyridin-3-yl]oxy}acetate (400 mg, 1.39 mmol) in THF (8 mL) under N₂ atmosphere was added LiAlH₄ (79.3 mg, 2.09 mmol). The mixture was stirred at 0° C. for 2 h. The mixture was quenched with H₂O (20 mL) and then extracted with EtOAc (3×30 mL). The combined organic layers were washed with brine (2×20 mL), dried with Na₂SO₄, filtered, and concentrated in vacuo to give methyl 2-{[6-(2-methanesulfonylpropan-2-yl)pyridin-3-yl]oxy}acetate, which was used in the subsequent step without further purification. MS=260.1 [M+H]⁺.

Step 7: 2-{[6-(2-methanesulfonylpropan-2-yl)pyridin-3-yl]oxy}ethyl methanesulfonate

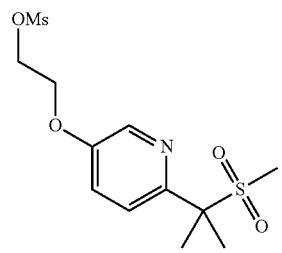 [SMILES: CC(C)(c1ccc(OCCOS(C)(=O)=O)cn1)S(C)(=O)=O]

To a 0° C. solution of methyl 2-{[6-(2-methanesulfonylpropan-2-yl)pyridin-3-yl]oxy}acetate (361 mg, 1.39 mmol) in DCM (5 mL) was added methanesulfonic anhydride (364 mg, 2.09 mmol) and TEA (388 µL, 2.78 mmol). The mixture was warmed to room temperature and stirred for 2 h. The mixture was quenched with H₂O (10 mL) and then extracted with EtOAc (3×20 mL). The combined organic layers were washed with brine (2×10 mL), dried with Na₂SO₄, filtered, and concentrated in vacuo to give 2-{[6-(2-methanesulfonylpropan-2-yl)pyridin-3-yl]oxy}ethyl methanesulfonate (Intermediate A-78). MS=338.1 [M+H]⁺

General Procedure for Intermediate A-79

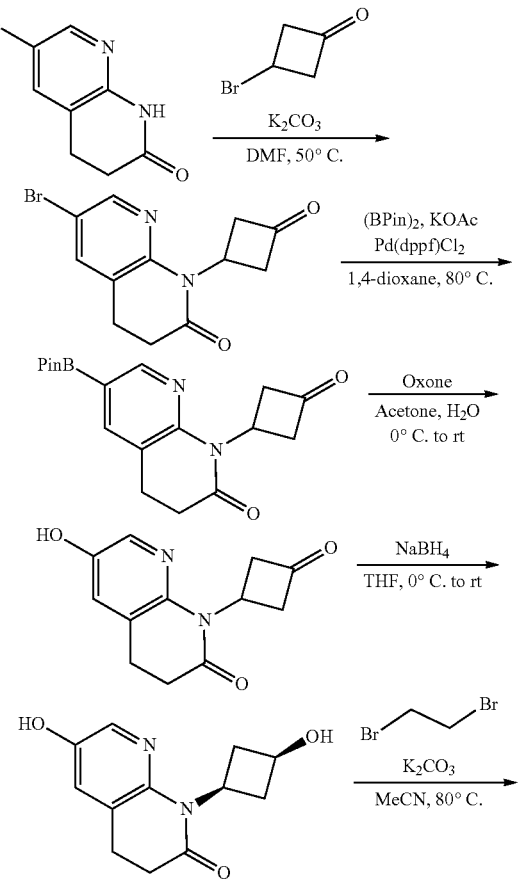

-continued

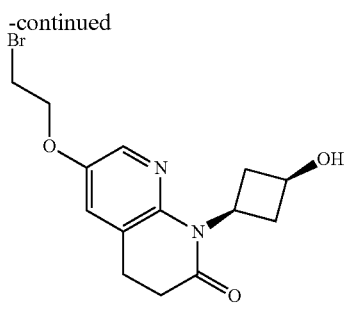

Intermediate A-79

Step 1: 6-bromo-1-(3-oxocyclobutyl)-1,2,3,4-tetrahydro-1,8-naphthyridin-2-one

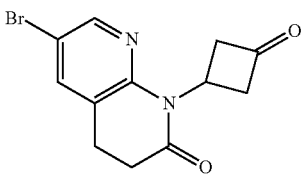 [SMILES: O=C1CC(N2C(=O)CCc3cc(Br)cnc32)C1]

To a solution of 6-bromo-1,2,3,4-tetrahydro-1,8-naphthyridin-2-one (250 mg, 1.10 mmol) in DMF (5 mL) under $N_2$ atmosphere was added $K_2CO_3$ (380 mg, 2.75 mmol). The mixture was stirred at 50° C. for 4 h, and then a solution of 3-bromocyclobutanone (197 mg, 1.32 mmol) in DMF (5 mL) was added to the reaction mixture. The mixture was stirred at 50° C. for an additional 1 h. After cooling to room temperature, the mixture was concentrated in vacuo. The crude residue was purified by normal phase silica gel chromatography (Biotage 12 g cartridge, 0-50% EtOAc:petroleum ether) to give 6-bromo-1-(3-oxocyclobutyl)-1,2,3,4-tetrahydro-1,8-naphthyridin-2-one. MS=295.1/297.1 [M+H]$^+$.

Step 2: 1-(3-oxocyclobutyl)-6-(4,4,5,5-tetramethyl-1,3,2-dioxaborolan-2-yl)-1,2,3,4-tetrahydro-1,8-naphthyridin-2-one

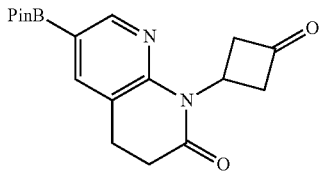

A mixture of 6-bromo-1-(3-oxocyclobutyl)-1,2,3,4-tetrahydro-1,8-naphthyridin-2-one (1.20 g, 4.07 mmol), bis(pinacolato)diboron (1.24 g, 4.88 mmol), KOAc (798 mg, 8.13 mmol) and Pd(dppf)Cl$_2$ (149 mg, 0.203 mmol) in 1,4-dioxane (60 mL) was degassed and purged with $N_2$ (3×). The mixture was stirred at 80° C. for 12 h under $N_2$ atmosphere. After cooling to room temperature, solids were removed by filtration and the filtrate was concentrated in vacuo to provide 1-(3-oxocyclobutyl)-6-(4,4,5,5-tetramethyl-1,3,2-dioxaborolan-2-yl)-1,2,3,4-tetrahydro-1,8-naphthyridin-2-one, which was used into the next step without further purification. MS=343.2 [M+H]$^+$.

Step 3: 6-hydroxy-1-(3-oxocyclobutyl)-1,2,3,4-tetrahydro-1,8-naphthyridin-2-one

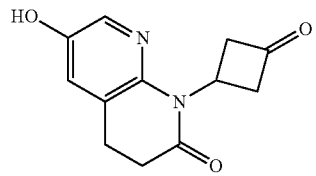

To a 0° C. solution of 1-(3-oxocyclobutyl)-6-(4,4,5,5-tetramethyl-1,3,2-dioxaborolan-2-yl)-1,2,3,4-tetrahydro-1,8-naphthyridin-2-one (1.00 g, 2.92 mmol) in acetone (30 mL) and H$_2$O (30 mL) was added Oxone (3.59 g, 5.84 mmol). The mixture was stirred at room temperature for 2 h. The mixture was quenched with H$_2$O (20 mL) and extracted with EtOAc (3×20 mL). The combined organic layers were washed with brine (30 mL), dried with Na$_2$SO$_4$, filtered, and concentrated in vacuo. The crude residue was purified by normal phase silica gel chromatography (Biotage 12 g cartridge, 0-100% EtOAc:petroleum ether) to give 6-hydroxy-1-(3-oxocyclobutyl)-1,2,3,4-tetrahydro-1,8-naphthyridin-2-one. MS=233.2 [M+H]$^+$.

Step 4: 6-hydroxy-1-[(cis)-3-hydroxycyclobutyl]-1,2,3,4-tetrahydro-1,8-naphthyridin-2-one

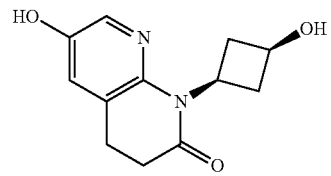 [SMILES: O=C1CCc2cc(O)cnc2N1[C@H]1C[C@@H](O)C1]

To a 0° C. solution of 6-hydroxy-1-(3-oxocyclobutyl)-1,2,3,4-tetrahydro-1,8-naphthyridin-2-one (500 mg, 2.15 mmol) in THF (15 mL) under $N_2$ atmosphere was added NaBH$_4$ (163 mg, 4.31 mmol). The mixture was stirred at room temperature for 2 h, and then was quenched with saturated aqueous NaHCO$_3$ solution (10 mL). The aqueous phase was extracted with EtOAc (3×20 mL). The combined organic layers were washed with brine (2×30 mL), dried with Na$_2$SO$_4$, filtered, and concentrated in vacuo. The crude residue was purified by normal phase silica gel chromatography (Biotage 12 g cartridge, 0-50% EtOAc:petroleum ether) to give 6-hydroxy-1-[(cis)-3-hydroxycyclobutyl]-1,2,3,4-tetrahydro-1,8-naphthyridin-2-one. MS=235.2 [M+H]$^+$.

Step 5: 6-(2-bromoethoxy)-1-[(cis)-3-hydroxycyclobutyl]-1,2,3,4-tetrahydro-1,8-naphthyridin-2-one

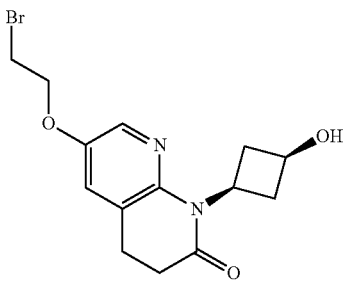

To a solution of 6-hydroxy-1-[(cis)-3-hydroxycyclobutyl]-1,2,3,4-tetrahydro-1,8-naphthyridin-2-one (300 mg, 1.28 mmol) in MeCN (4 mL) was added $K_2CO_3$ (531 mg, 3.84 mmol) and 1,2-dibromoethane (3.86 mL, 51.23 mmol). The mixture was stirred at 80° C. for 12 h. After cooling to room temperature, the reaction mixture was concentrated in vacuo. The crude residue was purified by normal phase silica gel chromatography (Biotage 12 g cartridge, 0-50% EtOAc:petroleum ether) to give 6-(2-bromoethoxy)-1-[(cis)-3-hydroxycyclobutyl]-1,2,3,4-tetrahydro-1,8-naphthyridin-2-one (Intermediate A-79). MS=341.1/343.1 [M+H]⁺.

General Procedure for Intermediate A-80

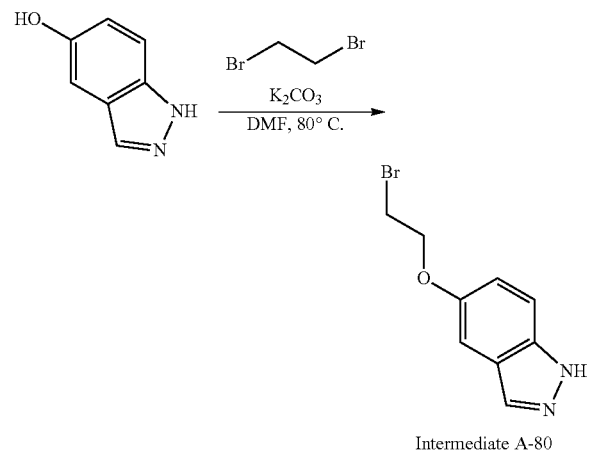

Step 1: 5-(2-bromoethoxy)-1H-indazole

A solution of 1H-indazol-5-ol (1.00 g, 7.46 mmo), 1,2-dibromoethane (11.3 mL, 149 mmol), and $K_2CO_3$ (1.24 g, 8.95 mmol) in DMF (10 mL) was stirred at 80° C. for 16 h. After cooling to room temperature, the mixture was diluted with $H_2O$ (10 mL), then extracted with EtOAc (3×10 mL). The combined organic layers were washed with brine (30 mL), dried over $Na_2SO_4$, filtered, and concentrated in vacuo. The crude residue was purified by normal phase silica gel chromatography (Biotage 10 g cartridge, 0-100% EtOAc: petroleum ether) to give 5-(2-bromoethoxy)-1H-indazole (Intermediate A-80). MS=241.1/243.1 [M+H]⁺.

General Procedure for Intermediate A-81

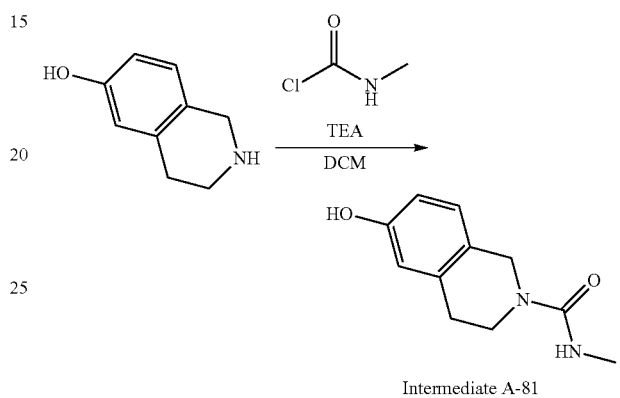

Step 1: 6-hydroxy-N-methyl-1,2,3,4-tetrahydroisoquinoline-2-carboxamide

To a solution of 1,2,3,4-tetrahydroisoquinolin-6-ol (500 mg, 3.35 mmol) in DCM (7 mL) was added TEA (847 mg, 8.38 mmol) followed by the dropwise addition of N-methylcarbamoyl chloride (783 mg, 8.38 mmol). The mixture was stirred at room temperature for 12 h. The reaction mixture was diluted with $H_2O$ (10 mL) and extracted with EtOAc (3×10 mL). The combined organic layers were washed with brine (20 mL), dried over $Na_2SO_4$, filtered, and concentrated in vacuo. The crude residue was purified by normal phase silica gel chromatography (Biotage 4 g cartridge, 0-100% EtOAc:petroleum ether) to give 6-hydroxy-N-methyl-1,2,3,4-tetrahydroisoquinoline-2-carboxamide (Intermediate A-81). MS=207.2 [M+H]⁺.

General Procedure for Intermediate A-82

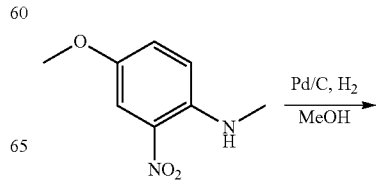

-continued

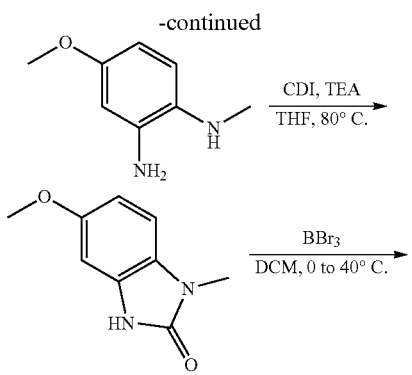

Step 2: 5-methoxy-1-methyl-2,3-dihydro-1H-1,3-benzodiazol-2-one

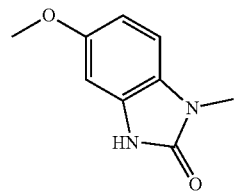

To a solution of 4-methoxy-N1-methylbenzene-1,2-diamine (150 mg, 0.986 mmol) in THF (20 mL) were added TEA (99.0 mg, 0.986 mmol) and CDI (799 mg, 4.93 mmol). The mixture was stirred at 80° C. for 12 h under $N_2$ atmosphere. After cooling to room temperature, solids were removed by filtration and the filtrate was concentrated in vacuo. The crude residue was purified by normal phase silica gel chromatography (Biotage 12 g cartridge, 0-100% EtOAc:petroleum ether) to give 5-methoxy-1-methyl-2,3-dihydro-1H-1,3-benzodiazol-2-one. $^1$H NMR (400 MHz, DMSO-$d_6$): δ 10.72 (s, 1H), 6.96 (d, J=8.4 Hz, 1H), 6.61-6.56 (m, 2H), 3.71 (s, 3H), 3.23 (s, 3H).

Step 3: 5-hydroxy-1-methyl-2,3-dihydro-1H-1,3-benzodiazol-2-one

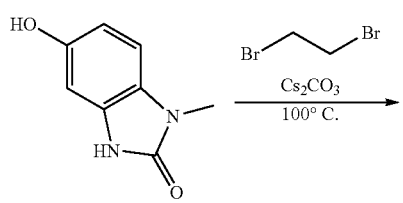

To a 0° C. solution of 5-methoxy-1-methyl-2,3-dihydro-1H-1,3-benzodiazol-2-one (216 mg, 1.21 mmol) in DCM (5 mL) was added BBr$_3$ (1.52 g, 6.06 mmol) dropwise. The mixture was stirred at 40° C. for 4 h. After cooling to room temperature, solids were removed by filtration and the filtrate was concentrated in vacuo. The crude residue was purified by normal phase silica gel chromatography (Biotage 4 g cartridge, 0-100% EtOAc:petroleum ether) to give 5-methoxy-1-methyl-2,3-dihydro-1H-1,3-benzodiazol-2-one.

Step 4: 5-(2-bromoethoxy)-1-methyl-2,3-dihydro-1H-1,3-benzodiazol-2-one

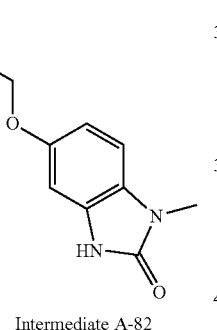

Intermediate A-82

Step 1: 4-methoxy-N1-methylbenzene-1,2-diamine

To a solution of 4-methoxy-N-methyl-2-nitroaniline (500 mg, 2.74 mmol) in MeOH (10 mL) under $N_2$ atmosphere was added Pd/C (150 mg, 10 wt %, 0.141 mmol). The suspension was degassed under vacuum and purged with $H_2$ (3×). After stirring under an atmosphere of $H_2$ (15 psi) at room temperature for 12 h, solids were removed by filtration through Celite and the filtrate was concentrated in vacuo. The crude residue was purified by normal phase silica gel chromatography (Biotage 20 g cartridge, 0-50% EtOAc: petroleum ether) to give 4-methoxy-N1-methylbenzene-1,2-diamine. MS=153.2 [M+H]$^+$.

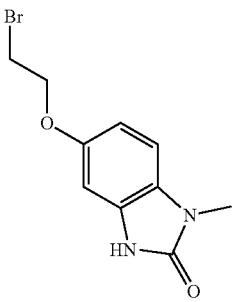

A mixture of 5-methoxy-1-methyl-2,3-dihydro-1H-1,3-benzodiazol-2-one (100 mg, 0.609 mmol) and Cs$_2$CO$_3$ (595 mg, 1.83 mmol) in 1,2-dibromoethane (5 mL, 66 mmol) under N$_2$ atmosphere was stirred at 80° C. for 12 h. After cooling to room temperature, solids were removed by filtration and the filtrate was concentrated in vacuo. The crude residue was purified by normal phase silica gel chromatography (Biotage 4 g cartridge, 0-100% EtOAc:petroleum ether) to give 5-(2-bromoethoxy)-1-methyl-2,3-dihydro-1H-1,3-benzodiazol-2-one (Intermediate A-82). MS=271.0/273.0 [M+H]$^+$.

General Procedure for Intermediate A-86

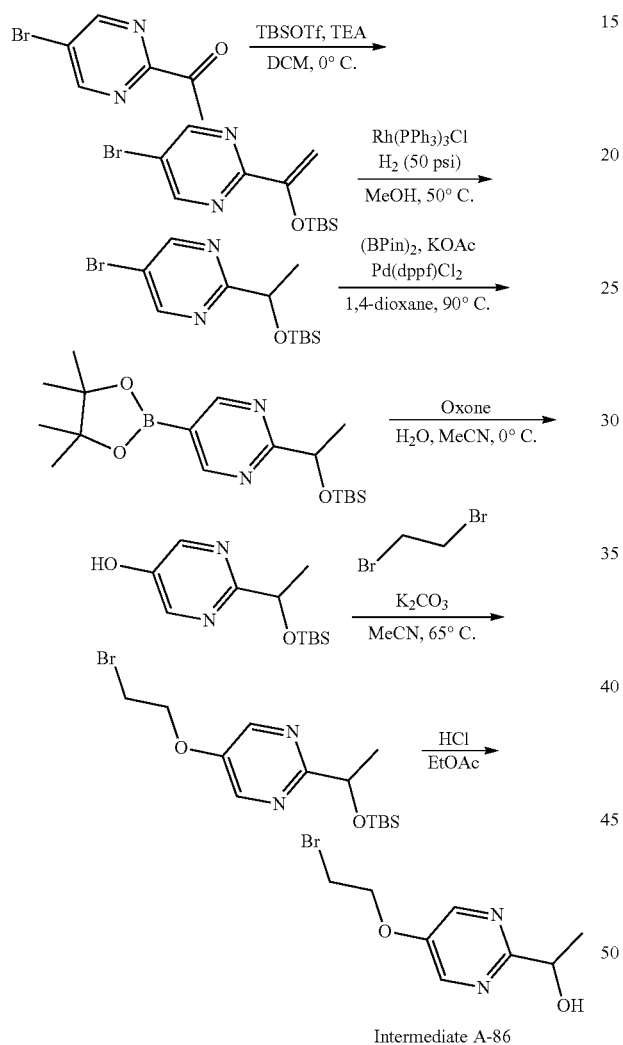

Intermediate A-86

Step 1: 5-bromo-2-{1-[(tert-butyldimethylsilyl)oxy]ethenyl}pyrimidine

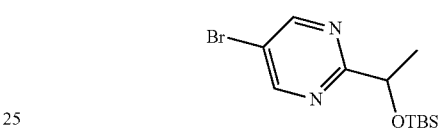

To a solution of 1-(5-bromopyrimidin-2-yl)ethan-1-one (500 mg, 2.49 mmol) in DCM (10 mL) were added TEA (378 mg, 3.73 mmol) and TBSOTf (988 mg, 3.73 mmol). The mixture was stirred at 0° C. for 0.5 h. The reaction mixture was quenched with H$_2$O (10 mL) and then extracted with DCM (3×10 mL). The combined organic layers were washed with brine (20 mL), dried over Na$_2$SO$_4$, filtered, and concentrated in vacuo. The crude residue was purified by flash silica gel chromatography (Biotage 12 g cartridge, 0-20% EtOAc:Petroleum ether) to give 5-bromo-2-{1-[(tert-butyldimethylsilyl)oxy]ethenyl}pyrimidine. $^1$H NMR (400 MHz, DMSO-d$_6$): δ 8.99 (s, 2H), 5.80 (s, 1H), 4.89 (s, 1H), 0.96 (s, 9H), 0.16 (s, 6H).

Step 2: 5-bromo-2-{1-[(tert-butyldimethylsilyl)oxy]ethyl}pyrimidine

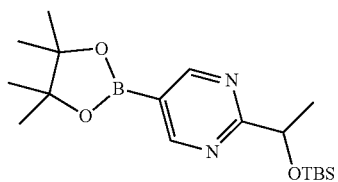 [SMILES: CC(O[Si](C)(C)C(C)(C)C)c1ncc(B2OC(C)(C)C(C)(C)O2)cn1]

To a solution of 5-bromo-2-{1-[(tert-butyldimethylsilyl)oxy]ethenyl}pyrimidine (300 mg, 0.952 mmol) in MeOH (30 mL) under N$_2$ atmosphere was added Rh(PPh$_3$)$_3$Cl (178 mg, 0.190 mmol). The suspension was degassed under vacuum and purged with H$_2$ several times. The mixture was stirred under H$_2$ (50 psi) at 50° C. for 4 h. After cooling to room temperature, solids were removed by filtration and the filtrate was concentrated in vacuo. The crude residue was purified by flash silica gel chromatography (Biotage 12 g cartridge, 0-10% EtOAc:Petroleum ether) to give 5-bromo-2-{1-[(tert-butyldimethylsilyl)oxy]ethyl}pyrimidine. MS=317.1/319.1 [M+H]$^+$.

Step 3: 2-{1-[(tert-butyldimethylsilyl)oxy]ethyl}-5-(4,4,5,5-tetramethyl-1,3,2-dioxaborolan-2-yl)pyrimidine A mixture of 5-bromo-2-{1-[(tert-butyldimethylsilyl)oxy]ethyl}pyrimidine (0.25 g, 0.788 mmol), bis(pinacolato)diboron (240 mg, 0.945 mmol), KOAc (232 mg, 2.36 mmol), and Pd(dppf)Cl$_2$ (58 mg, 78.8 μmol) in 1,4-dioxane (15 mL) was degassed and purged with N$_2$ (3×). The mixture was stirred at 90° C. for 5 h under N$_2$ atmosphere. After cooling to room temperature, solids were removed by filtration and the filtrate was concentrated in vacuo to give 2-{1-[(tert-butyldimethylsilyl)oxy]ethyl}-5-(4,4,5,5-tetramethyl-1,3,2-dioxaborolan-2-yl)pyrimidine, which was used in the subsequent step without further purification.

Step 4: 2-{1-[(tert-butyldimethylsilyl)oxy]ethyl}pyrimidin-5-ol

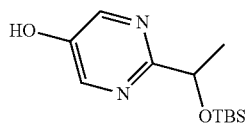 [SMILES: CC(O[Si](C)(C)C(C)(C)C)c1ncc(O)cn1]

To a 0° C. solution of 2-{1-[(tert-butyldimethylsilyl)oxy]ethyl}-5-(4,4,5,5-tetramethyl-1,3,2-dioxaborolan-2-yl)pyrimidine (300 mg, 0.823 mmol) in MeCN (10 mL) and H$_2$O (10 mL) was added Oxone (607 mg, 0.988 mmol). The mixture was stirred at 0° C. for 1 h, then was quenched with saturated aqueous Na$_2$SO$_3$ (5 mL) and extracted with DCM (3×10 mL). The combined organic layers were washed with brine (15 mL), saturated aqueous Na$_2$SO$_3$ (15 mL), dried over Na$_2$SO$_4$, filtered, and concentrated in vacuo. The crude residue was purified by flash silica gel chromatography (Biotage 12 g cartridge, 0-100% EtOAc:Petroleum ether) to give 2-{1-[(tert-butyldimethylsilyl)oxy]ethyl}pyrimidin-5-ol. MS=255.2 [M+H]$^+$.

Step 5: 5-(2-bromoethoxy)-2-{1-[(tert-butyldimethylsilyl)oxy]ethyl}pyrimidine

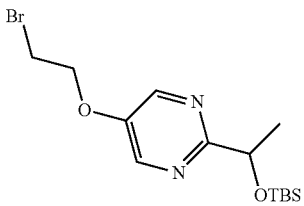 [SMILES: CC(O[Si](C)(C)C(C)(C)C)c1ncc(OCCBr)cn1]

To a solution of 2-{1-[(tert-butyldimethylsilyl)oxy]ethyl}pyrimidin-5-ol (80.0 mg, 0.314 mmol) in MeCN (3 mL) was added K$_2$CO$_3$ (218 mg, 1.57 mmol) and 1,2-dibromoethane (2.36 g, 12.6 mmol). The mixture was stirred at 65° C. for 16 h. After cooling to room temperature, solids were removed by filtration and the filtrate was concentrated in vacuo. The crude residue was purified by flash silica gel chromatography (Biotage 4 g cartridge, 0-30% EtOAc:Petroleum ether) to give 5-(2-bromoethoxy)-2-{1-[(tert-butyldimethylsilyl)oxy]ethyl}pyrimidine. 5-(2-bromoethoxy)-2-(1-((tert-butyldimethylsilyl)oxy)ethyl)pyrimidine. MS=361.1/363.1 [M+H]$^+$ Step 6: 1-[5-(2-bromoethoxy)pyrimidin-2-yl]ethan-1-ol

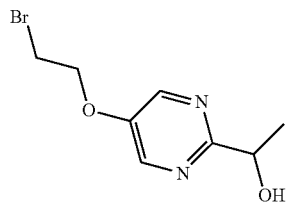

To a solution of 5-(2-bromoethoxy)-2-(1-((tert-butyldimethylsilyl)oxy)ethyl)pyrimidine (130 mg, 0.360 mmol) in EtOAc (3 mL) was added 4.0 M HCl in EtOAc (10 mL, 40.0 mmol). The mixture was stirred at room temperature for 5 h. The mixture was concentrated in vacuo to give 1-[5-(2-bromoethoxy)pyrimidin-2-yl]ethan-1-ol (Intermediate A-86), which was used in the subsequent steps without further purification. MS=247.0/249.0 [M+H]$^+$.

General Procedure for Intermediate A-87

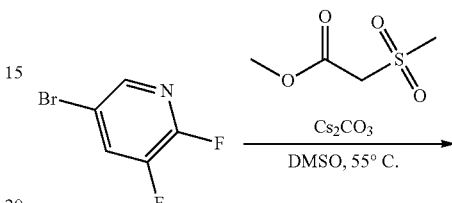

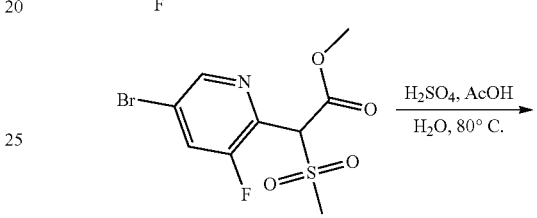

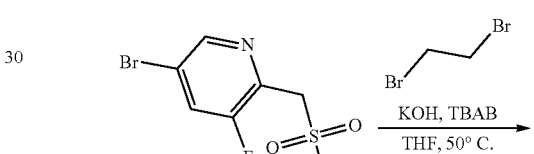

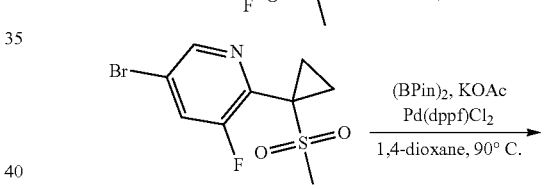

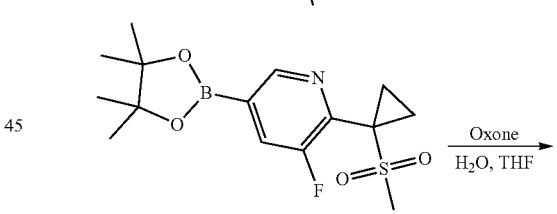

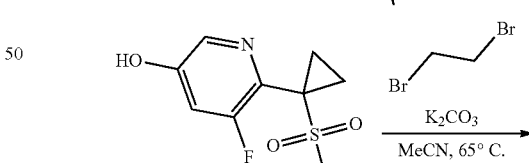

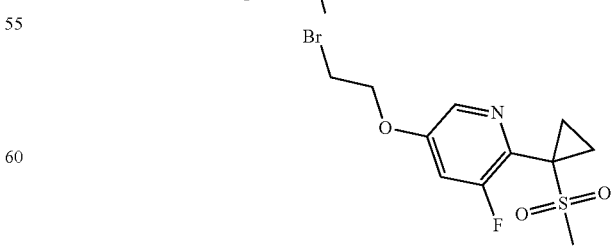

Intermediate A-87

Step 1: methyl 2-(5-bromo-3-fluoropyridin-2-yl)-2-methanesulfonylacetate

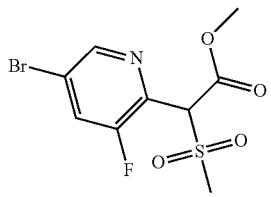 [SMILES: COC(=O)C(c1ncc(Br)cc1F)S(C)(=O)=O]

To a solution of 5-bromo-2,3-difluoropyridine (5.00 g, 25.8 mmol) in DMSO (55 mL) was added Cs$_2$CO$_3$ (16.8 g, 51.6 mmol) and methyl 2-methylsulfonylacetate (4.71 g, 30.9 mmol). The mixture was stirred at 55° C. for 30 h. After cooling to room temperature, the reaction mixture was quenched with H$_2$O (50 mL) and extracted with EtOAc (3×30 mL). The combined organic layers were washed with brine (10 mL), dried over Na$_2$SO$_4$, filtered, and concentrated in vacuo. The crude residue was purified by flash silica gel chromatography (Biotage 40 g cartridge, 0-25% EtOAc:Petroleum ether) to give methyl 2-(5-bromo-3-fluoropyridin-2-yl)-2-methanesulfonylacetate. MS=325.8/327.8 [M+H]$^+$.

Step 2: 5-bromo-3-fluoro-2-(methanesulfonylmethyl)pyridine

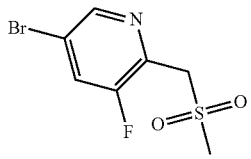

To a solution of methyl 2-(5-bromo-3-fluoropyridin-2-yl)-2-methanesulfonylacetate (5.30 g, 16.3 mmol) in H$_2$O (26 mL) and AcOH (26 mL) was added H$_2$SO$_4$ (5.10 mL, 95.8 mmol). The mixture was stirred at 80° C. for 15 h. After cooling to room temperature, the reaction mixture was adjusted to pH=4.0 with saturated aqueous Na$_2$CO$_3$. The mixture was extracted with EtOAc (3×25 mL), the combined organic layers were washed with brine (10 mL), dried over Na$_2$SO$_4$, filtered, and concentrated in vacuo to give crude 5-bromo-3-fluoro-2-(methanesulfonylmethyl)pyridine, which was used in the subsequent step without further purification. MS=267.8/269.8 [M+H]$^+$.

Step 3: 5-bromo-3-fluoro-2-(1-methanesulfonylcyclopropyl)pyridine

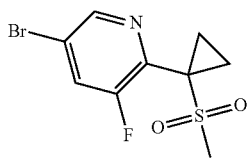

To a solution of 5-bromo-3-fluoro-2-(methanesulfonylmethyl)pyridine (3.30 g, 12.3 mmol) in THF (35 mL) were added KOH (3.45 g, 61.5 mmol), 1,2-dibromoethane (13.9 g, 73.9 mmol) and TBAB (793 mg, 2.46 mmol). The mixture was stirred at 50° C. for 24 h. After cooling to room temperature, the reaction mixture was quenched with H$_2$O (30 mL) and extracted with EtOAc (3×25 mL). The combined organic layers were washed with brine (10 mL), dried over Na$_2$SO$_4$, filtered, and concentrated in vacuo. The crude residue was purified by flash silica gel chromatography (Biotage 20 g cartridge, 0-30% EtOAc:Petroleum ether) to give 5-bromo-3-fluoro-2-(1-methanesulfonylcyclopropyl)pyridine. MS=293.9/295.9 [M+H]$^+$.

Step 4: 3-fluoro-2-(1-methanesulfonylcyclopropyl)-5-(4,4,5,5-tetramethyl-1,3,2-dioxaborolan-2-yl)pyridine

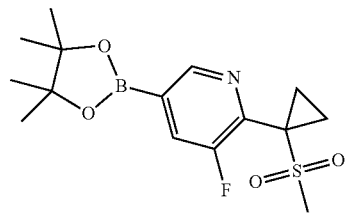 [SMILES: CC1(C)OB(c2cnc(C3(S(C)(=O)=O)CC3)c(F)c2)OC1(C)C]

To a solution of 5-bromo-3-fluoro-2-(1-methanesulfonylcyclopropyl)pyridine (500 mg, 1.70 mmol) in 1,4-dioxane (6 mL) under N$_2$ atmosphere was added bis(pinacolato)diboron (648 mg, 2.55 mmol), KOAc (334 mg, 3.40 mmol) and Pd(dppf)Cl$_2$ (125 mg, 0.170 mmol). The mixture was stirred at 90° C. for 15 h under N$_2$ atmosphere. After cooling to room temperature, solids were removed by filtration and the filtrate was concentrated in vacuo. The crude residue was purified by flash silica gel chromatography (Biotage 20 g cartridge, 0-55% EtOAc:Petroleum ether) to give 3-fluoro-2-(1-methanesulfonylcyclopropyl)-5-(4,4,5,5-tetramethyl-1,3,2-dioxaborolan-2-yl)pyridine.

Step 5: 5-fluoro-6-(1-methanesulfonylcyclopropyl)pyridin-3-ol

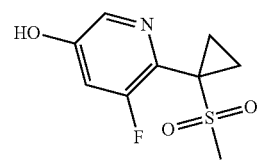

To a solution of 3-fluoro-2-(1-methanesulfonylcyclopropyl)-5-(4,4,5,5-tetramethyl-1,3,2-dioxaborolan-2-yl)pyridine (400 mg, 1.17 mmol) in H$_2$O (3 mL) and THF (3 mL) was added Oxone (721 mg, 1.17 mmol). The mixture was stirred at room temperature for 2 h. The reaction mixture was diluted with H$_2$O (15 mL) and extracted with EtOAc (3×15 mL). The combined organic layers were washed with brine (20 mL), dried over Na$_2$SO$_4$, filtered, and concentrated in vacuo. The crude residue was purified by flash silica gel chromatography (Biotage 12 g cartridge, 0-70% EtOAc:Petroleum ether) to give 5-fluoro-6-(1-methanesulfonylcyclopropyl)pyridin-3-ol. MS=232.0 [M+H]$^+$.

Step 6: 5-(2-bromoethoxy)-3-fluoro-2-(1-methanesulfonylcyclopropyl)pyridine

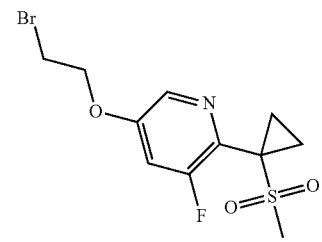 [SMILES: CS(=O)(=O)C1(c2ncc(OCCBr)cc2F)CC1]

To a solution of 5-fluoro-6-(1-methanesulfonylcyclopropyl)pyridin-3-ol (140 mg, 0.605 mmol) in MeCN (2 mL) were added 1,2-dibromoethane (4.55 g, 24.2 mmol) and $K_2CO_3$ (419 mg, 3.03 mmol). The mixture was stirred at 65° C. for 15 h. After cooling to room temperature, the reaction mixture was quenched with $H_2O$ (10 mL) and extracted with EtOAc (3×10 mL). The combined organic layers were washed with brine (20 mL), dried over $Na_2SO_4$, filtered, and concentrated in vacuo. The crude residue was purified by flash silica gel chromatography (Biotage 4 g cartridge, 0-40% EtOAc:Petroleum ether) to give 5-(2-bromoethoxy)-3-fluoro-2-(1-methanesulfonylcyclopropyl)pyridine (Intermediate A-87). MS=337.9/339.9 $[M+H]^+$.

General Procedure for Intermediate A-88

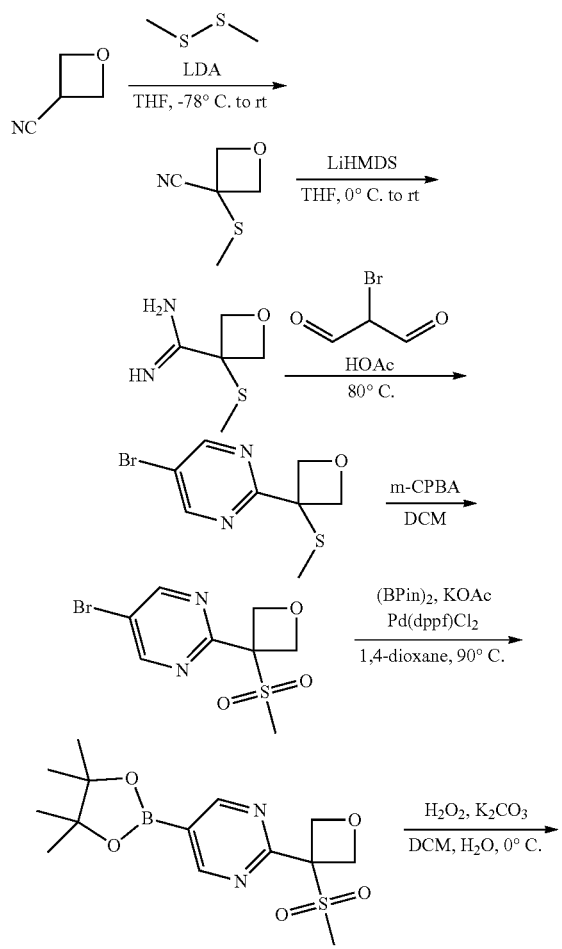

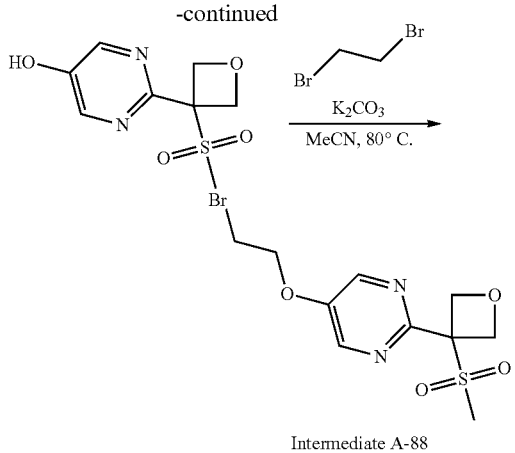

Intermediate A-88

Step 1: 3-(methylsulfanyl)oxetane-3-carbonitrile

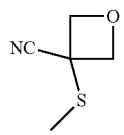

To a −78° C. solution of oxetane-3-carbonitrile (10.0 g, 12.4 mmol) and (methyldisulfanyl)methane (21.6 mL, 241 mmol) in THF (100 mL) under $N_2$ atmosphere was added 2.0 M LDA in THF (151 mL, 302 mmol) dropwise. The mixture was warmed to room temperature and stirred for 3 h. The reaction mixture was cooled to 0° C. and then quenched with $H_2O$ (200 mL) and extracted with EtOAc (3×100 mL). The combined organic layers were washed with brine (20 mL), dried over $Na_2SO_4$, filtered, and concentrated in vacuo. The crude residue was purified by flash silica gel chromatography (Biotage 120 g cartridge, 0-25% EtOAc:Petroleum ether) to give 3-(methylsulfanyl)oxetane-3-carbonitrile. $^1$H NMR (400 MHz, $CDCl_3$): δ 5.13 (d, J=6.8 Hz, 2H), 4.64 (d, J=6.8 Hz, 2H), 2.31 (s, 3H).

Step 2: 3-(methylsulfanyl)oxetane-3-carboximidamide

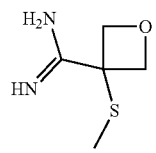

To a 0° C. solution of 3-(methylsulfanyl)oxetane-3-carbonitrile (2.50 g, 19.4 mmol) in THF (30 mL) under $N_2$ atmosphere was added 1.0 M LiHMDS in THF (96.8 mL, 96.8 mmol). The mixture was allowed to warm to room temperature and stirred for 15 h, then was quenched with AcOH (40 mL). The resulting solids were isolated by filtration and dried in vacuo to give 3-(methylsulfanyl)oxetane-3-carboximidamide, which was used in the subsequent step without further purification. MS=147.2 $[M+H]^+$.

Step 3: 5-bromo-2-[3-(methylsulfanyl)oxetan-3-yl]pyrimidine

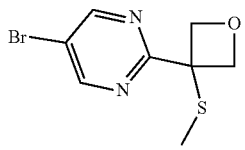

A mixture of 3-(methylsulfanyl)oxetane-3-carboximidamide (2.50 g, 17.1 mmol) and 2-bromopropanedial (5.16 g, 34.2 mmol) in AcOH (50 mL) was stirred at 80° C. for 8 h. After cooling to room temperature, the reaction mixture was quenched with H$_2$O (50 mL), and then extracted with EtOAc (2×50 mL). The combined organic layers were washed with saturated aqueous Na$_2$CO$_3$ (2×50 mL) and brine (50 mL), dried over Na$_2$SO$_4$, filtered, and concentrated in vacuo. The crude residue was purified by flash silica gel chromatography (Biotage 20 g cartridge, 0-20% EtOAc:Petroleum ether) to give 5-bromo-2-[3-(methylsulfanyl)oxetan-3-yl]pyrimidine. MS=261.1/263.1 [M+H]$^+$

Step 4: 5-bromo-2-(3-methanesulfonyloxetan-3-yl)pyrimidine

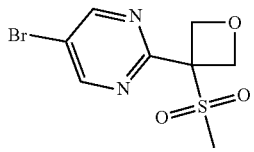

To a solution of 5-bromo-2-[3-(methylsulfanyl)oxetan-3-yl]pyrimidine (150 mg, 0.573 mmol) in DCM (15 mL) was added m-CPBA (350 mg, 1.72 mmol, 85% purity). The mixture was stirred at room temperature for 2 h. The reaction mixture was quenched with saturated aqueous Na$_2$SO$_3$ (20 mL), diluted with H$_2$O (10 mL), and extracted with DCM (3×15 mL). The combined organic layers were washed with saturated aqueous NaHCO$_3$ (2×20 mL) and brine (20 mL), dried over Na$_2$SO$_4$, filtered, and concentrated in vacuo. The crude residue was purified by flash silica gel chromatography (Biotage 12 g cartridge, 0-50% EtOAc:Petroleum ether) to give 5-bromo-2-(3-methanesulfonyloxetan-3-yl)pyrimidine. MS=293.0/295.0 [M+H]$^+$.

Step 5: 2-(3-methanesulfonyloxetan-3-yl)-5-(4,4,5,5-tetramethyl-1,3,2-dioxaborolan-2-yl)pyrimidine

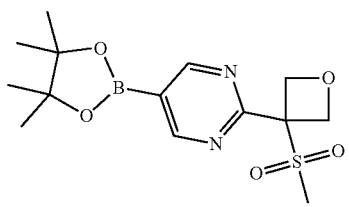 [SMILES: CC1(C)OB(c2cnc(C3(S(C)(=O)=O)COC3)nc2)OC1(C)C]

A mixture of 5-bromo-2-(3-methanesulfonyloxetan-3-yl)pyrimidine (140 mg, 0.476 mmol), bis(pinacolato)diboron (182 mg, 0.718 mmol), KOAc (141 mg, 1.43 mmol), and Pd(dppf)Cl$_2$ (35 mg, 47.8 μmol) in 1,4-dioxane (15 mL) was degassed and purged with N$_2$ (3×). The mixture was stirred at 90° C. for 15 h under N$_2$ atmosphere. After cooling to room temperature, solids were removed by filtration, and the filtrate was concentrated in vacuo to give 2-(3-methanesulfonyloxetan-3-yl)-5-(4,4,5,5-tetramethyl-1,3,2-dioxaborolan-2-yl)pyrimidine, which was used in the subsequent step without further purification. MS=341.2 [M+H]$^+$

Step 6: 2-(3-methanesulfonyloxetan-3-yl)pyrimidin-5-ol

To a 0° C. solution of 2-(3-methanesulfonyloxetan-3-yl)-5-(4,4,5,5-tetramethyl-1,3,2-dioxaborolan-2-yl)pyrimidine (220 mg, 0.646 mmol) in DCM (20 mL) were added K$_2$CO$_3$ (179 mg, 0.118 mmol) and 30% H$_2$O$_2$ in H$_2$O (0.25 mL, 2.59 mmol). The mixture was stirred at room temperature for 2 h, then was quenched with saturated aqueous Na$_2$S203 (5 mL). The mixture was extracted with DCM (2×20 mL), the combined organic layers were washed with brine (20 mL), dried over Na$_2$SO$_4$, filtered and concentrated in vacuo give 2-(3-methanesulfonyloxetan-3-yl)pyrimidin-5-ol, which was used in the subsequent step without further purification. MS=229.0 [M–H]$^+$.

Step 7: 5-(2-bromoethoxy)-2-(3-methanesulfonyloxetan-3-yl)pyrimidine

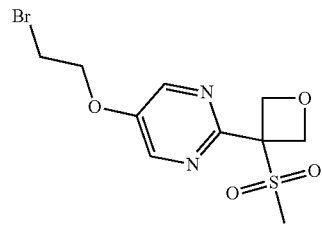 [SMILES: CS(=O)(=O)C1(c2ncc(OCCBr)cn2)COC1]

To a solution of 2-(3-methanesulfonyloxetan-3-yl)pyrimidin-5-ol (220 mg, 0.957 mmol) in MeCN (10 mL) was added K$_2$CO$_3$ (660 mg, 4.78 mmol) and 1,2-dibromoethane (7.18 g, 37.5 mmol). The mixture was stirred at 80° C. for 2 h. After cooling to room temperature, solids were removed by filtration and the filtrate was concentrated under reduced pressure. The crude residue was purified by flash silica gel chromatography (Biotage 12 g cartridge, 0-60% EtOAc: Petroleum ether) to give 5-(2-bromoethoxy)-2-(3-methanesulfonyloxetan-3-yl)pyrimidine (Intermediate A-88). MS=336.9/338.9 [M+H]$^+$ General Procedure for Intermediate A-89

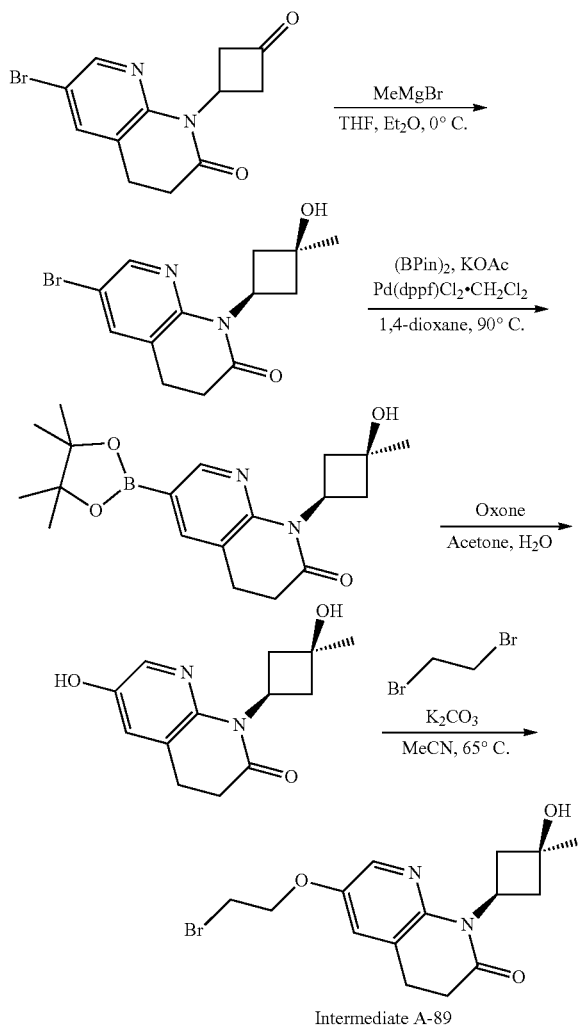

Intermediate A-89

Step 1: 6-bromo-1-[(cis)-3-hydroxy-3-methylcyclobutyl]-1,2,3,4-tetrahydro-1,8-naphthyridin-2-one

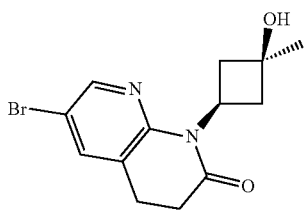 [SMILES: C[C@]1(O)C[C@@H](N2C(=O)CCc3cc(Br)cnc32)C1]

To a 0° C. solution of 6-bromo-1-(3-oxocyclobutyl)-1,2,3,4-tetrahydro-1,8-naphthyridin-2-one (Procedure for Intermediate A-79, Step 1, 1.00 g, 3.39 mmol) in THF (20 mL) was added 3.0 M MeMgBr in Et$_2$O (1.24 mL, 3.72 mmol). The mixture was stirred at 0° C. for 2 h, and then was quenched with saturated aqueous NH$_4$Cl solution (100 mL). The biphasic mixture was extracted with EtOAc (3×50 mL), and the combined organic layers were dried over Na$_2$SO$_4$, filtered, and concentrated in vacuo. The crude residue was purified by flash silica gel chromatography (Biotage 12 g cartridge, 0-48% EtOAc:Petroleum ether) to give 6-bromo-1-[(cis)-3-hydroxy-3-methylcyclobutyl]-1,2,3,4-tetrahydro-1,8-naphthyridin-2-one. $^1$H NMR (400 MHz, DMSO-d$_6$): δ 8.30 (d, J=2.4 Hz, 1H), 7.90 (d, J=2.4 Hz, 1H), 4.83 (s, 1H), 4.20-4.15 (m, 1H), 2.82 (t, J=7.2 Hz, 2H), 2.58-2.52 (m, 2H), 2.49-2.42 (m, 2H), 2.33-2.25 (m, 2H), 1.25 (s, 3H). MS=311.0/313.0 [M+H]$^+$.

Step 2: 1-[(cis)-3-hydroxy-3-methylcyclobutyl]-6-(4,4,5,5-tetramethyl-1,3,2 dioxaborolan-2-yl)-1,2,3,4-tetrahydro-1,8-naphthyridin-2-one

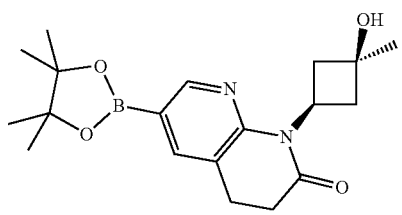

To a solution of 6-bromo-1-[(cis)-3-hydroxy-3-methylcyclobutyl]-1,2,3,4-tetrahydro-1,8-naphthyridin-2-one (1.00 g, 3.21 mmol) in 1,4-dioxane (20 mL) were added bis(pinacolato)diboron (1.06 g, 4.18 mmol), Pd(dppf)Cl$_2$·CH$_2$Cl$_2$ (210 mg, 257 μmol) and KOAc (788 mg, 8.03 mmol). The mixture was stirred at 90° C. for 12 h under N$_2$ atmosphere, and then cooled to room temperature. The mixture was diluted with H$_2$O (50 mL) and extracted with EtOAc (3×50 mL). The combined organic layers were washed with brine (50 mL), dried over Na$_2$SO$_4$, filtered, and concentrated in vacuo. The crude residue was purified by flash silica gel chromatography (Biotage 12 g cartridge, 0-58% EtOAc:Petroleum ether) to give 1-[(cis)-3-hydroxy-3-methylcyclobutyl]-6-(4,4,5,5-tetramethyl-1,3,2-dioxaborolan-2-yl)-1,2,3,4-tetrahydro-1,8-naphthyridin-2-one. MS=359.1 [M+H]$^+$.

Step 3: 6-hydroxy-1-[(cis)-3-hydroxy-3-methylcyclobutyl]-1,2,3,4-tetrahydro-1,8-naphthyridin-2-one

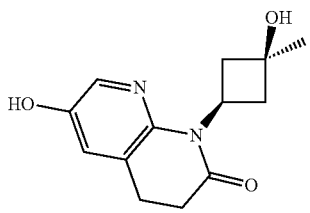 [SMILES: C[C@]1(O)C[C@@H](N2C(=O)CCc3cc(O)cnc32)C1]

To a solution of 1-[(cis)-3-hydroxy-3-methylcyclobutyl]-6-(4,4,5,5-tetramethyl-1,3,2-dioxaborolan-2-yl)-1,2,3,4-tetrahydro-1,8-naphthyridin-2-one (610 mg, 1.70 mmol) in acetone (10 mL) and H$_2$O (5 mL) was added Oxone (1.57 g, 2.55 mmol). The mixture was stirred for 2 h, and then was diluted with H$_2$O (10 mL) and extracted with EtOAc (20 mL×3). The combined organic layers were washed with brine (50 mL), dried over Na$_2$SO$_4$, filtered, and concentrated in vacuo. The crude residue was purified by flash silica gel chromatography (Biotage 12 g cartridge, 0-85% EtOAc:Petroleum ether) to give 6-hydroxy-1-[(cis)-3-hydroxy-3-methylcyclobutyl]-1,2,3,4-tetrahydro-1,8-naphthyridin-2-one. MS=249.0 [M+H]$^+$.

Step 4: 6-(2-bromoethoxy)-1-[(cis)-3-hydroxy-3-methylcyclobutyl]-1,2,3,4-tetrahydro-1,8-naphthyridin-2-one

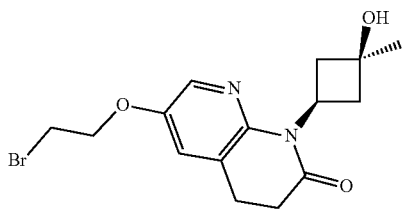 [SMILES: C[C@]1(O)C[C@@H](N2C(=O)CCc3cc(OCCBr)cnc32)C1]

To a solution of 6-hydroxy-1-[(cis)-3-hydroxy-3-methylcyclobutyl]-1,2,3,4-tetrahydro-1,8-naphthyridin-2-one (400 mg, 1.61 mmol) and 1,2-dibromoethane (1.82 mL, 24.2 mmol) in MeCN (10 mL) was added $K_2CO_3$ (1.11 g, 8.06 mmol). The mixture was stirred at 65° C. for 12 h. After cooling to room temperature, the mixture was diluted with $H_2O$ (10 mL) and extracted with EtOAc (3×10 mL). The combined organic layers were washed with brine (20 mL), dried over $Na_2SO_4$, filtered, and concentrated in vacuo. The crude residue was purified by flash silica gel chromatography (Biotage 12 g cartridge, 0-70% EtOAc:Petroleum ether) to give 6-(2-bromoethoxy)-1-[(cis)-3-hydroxy-3-methylcyclobutyl]-1,2,3,4-tetrahydro-1,8-naphthyridin-2-one (Intermediate A-89). $^1$H NMR (400 MHz, DMSO-$d_6$): δ 7.93 (d, J=2.8 Hz, 1H), 7.39 (d, J=2.8 Hz, 1H), 4.82 (s, 1H), 4.36 (t, J=5.6 Hz, 2H), 4.25-4.21 (m, 1H), 3.80 (t, J=5.6 Hz, 2H), 2.79 (t, J=6.8 Hz, 2H), 2.51-2.49 (m, 2H), 2.47-2.41 (m, 2H), 2.34-2.33 (m, 2H), 1.25 (s, 3H). MS=355.0/357.0 [M+H]$^+$.

The following intermediates in Table 11.1 were prepared according to procedures similar those described for Intermediate A-89 using the appropriate starting materials.

General Procedure for Intermediates A-90 to A-91

General Procedure for Intermediate A-92

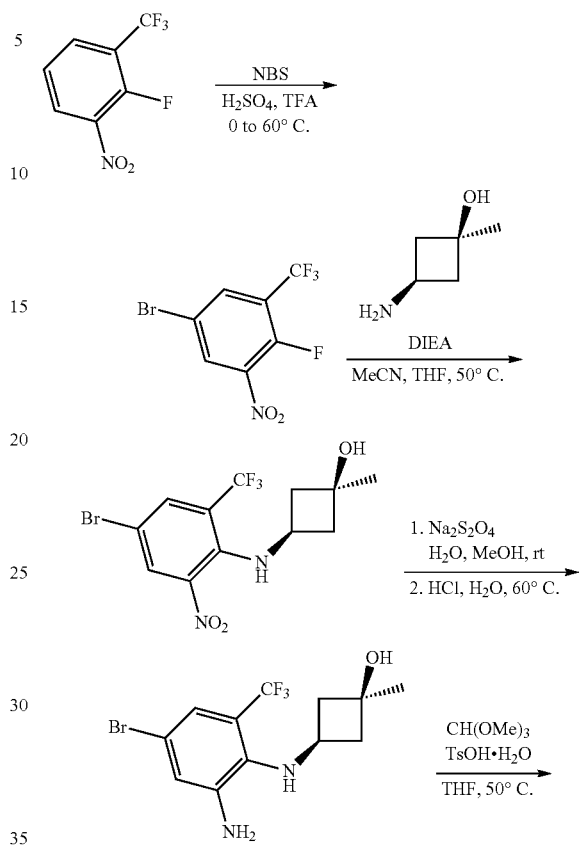

TABLE 11.1

| Intermediate # | Structure | Name | Exact Mass [M + H]$^+$ |
|---|---|---|---|
| A-90 | ![structure] | 6-(2-bromoethoxy)-1-[(cis)-3-hydroxy-3-methylcyclobutyl]-1H,2H,4H-pyrido[2,3-d][1,3]oxazin-2-one | Calc'd 357.0/357.0<br>Found 357.1/357.1 |
| A-91 | ![structure] | 6-(2-bromoethoxy)-3-[(cis)-3-hydroxy-3-methylcyclobutyl]-2H,3H-[1,3]oxazolo[4,5-b]pyridin-2-one | Calc'd 343.0/343.0<br>Found 343.0/343.0 |

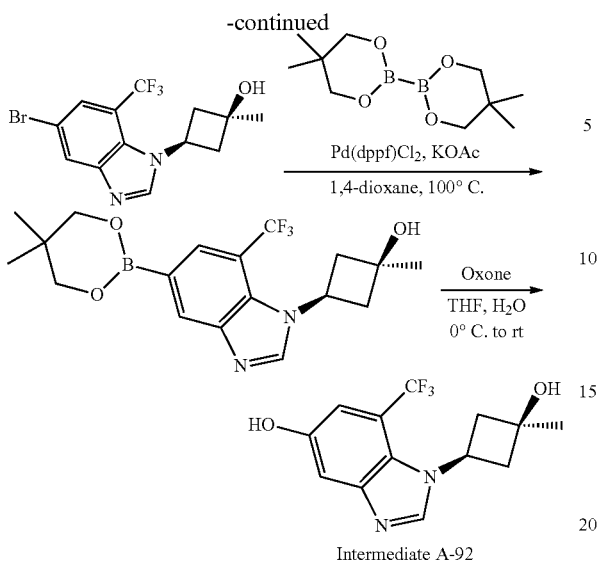

Intermediate A-92

Step 1: 5-bromo-2-fluoro-1-nitro-3-(trifluoromethyl)benzene

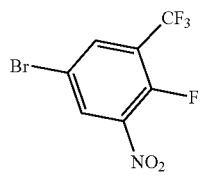

To concentrated H₂SO₄ (15 mL) at 0° C. was added a solution of 2-fluoro-1-nitro-3-(trifluoromethyl)benzene (5.00 g, 23.0 mmol) in TFA (10 mL). NBS (5.11 g, 28.7 mol) was added to the 0° C. mixture in several portions. The mixture was stirred at 60° C. for 16 h. The reaction mixture was cooled to room temperature, and then poured into ice water (200 mL). The mixture was extracted with petroleum ether (2×80 mL). The combined organic layers were washed with saturated aqueous NaHCO₃ until pH=8-9. The organic layer was separated, washed with brine (50 mL), dried over Na₂SO₄, filtered, and concentrated in vacuo to give 5-bromo-2-fluoro-1-nitro-3-(trifluoromethyl)benzene. ¹H NMR (400 MHz, DMSO-d₆): δ 8.70 (dd, J=6.0 Hz, 2.4 Hz, 1H), 8.46 (dd, J=5.6 Hz, 2.4 Hz, 1H).

Step 2: (cis)-3-{[4-bromo-2-nitro-6-(trifluoromethyl)phenyl]amino}-1-methylcyclobutan-1-ol

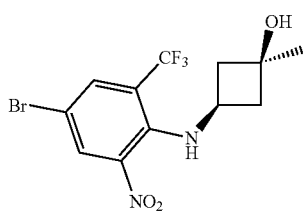 [SMILES: C[C@]1(O)C[C@@H](Nc2c(N)cc(Br)cc2C(F)(F)F)C1]

A mixture of 5-bromo-2-fluoro-1-nitro-3-(trifluoromethyl)benzene (6.50 g, 22.6 mmol), DIEA (11.2 mL, 67.7 mmol) and (cis)-3-amino-1-methylcyclobutan-1-ol (3.42 g, 24.8 mmol, HCl salt) in THF (35 mL) and MeCN (35 mL) was stirred at 50° C. for 2 h. The reaction mixture was cooled to room temperature and concentrated in vacuo. The residue was diluted with H₂O (150 mL) and extracted with MTBE (2×80 mL). The combined organic layers were washed with brine (80 mL), dried over Na₂SO₄, filtered and concentrated in vacuo to give (cis)-3-{[4-bromo-2-nitro-6-(trifluoromethyl)phenyl]amino}-1-methylcyclobutan-1-ol, which was used in the subsequent step without further purification. MS=368.9/370.9 [M+H]⁺.

Step 3: (cis)-3-{[2-amino-4-bromo-6-(trifluoromethyl)phenyl]amino}-1-methylcyclobutan-1-ol

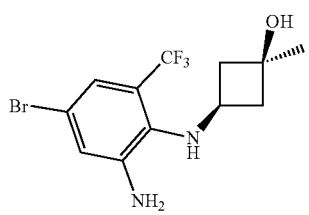

To a three-neck round-bottom flask equipped with a magnetic stir bar and a thermometer was added H₂O (170 mL) and sodium dithionite (32.1 g, 184 mmol). To the mixture was added a solution of (cis)-3-{[4-bromo-2-nitro-6-(trifluoromethyl)phenyl]amino}-1-methylcyclobutan-1-ol (17.0 g, 46.1 mmol) in MeOH (170 mL) dropwise. The mixture was stirred at room temperature for 1 h, and then 12 M aqueous HCl (35 mL) was added. The mixture was stirred at 60° C. for 1 h. After cooling to room temperature, the mixture was concentrated in vacuo to remove MeOH, and the residue was diluted with H₂O (150 mL). The aqueous layer was adjusted to pH>7 by addition of solid Na₂CO₃. The mixture was extracted with MTBE (2×200 mL). The combined organic layers were washed with brine (2×100 mL), dried over Na₂SO₄, filtered and concentrated in vacuo to give (cis)-3-{[2-amino-4-bromo-6-(trifluoromethyl)phenyl]amino}-1-methylcyclobutan-1-ol, which was used in the subsequent step without further purification. MS=339.0/341.0 [M+H]⁺.

Step 4: (cis)-3-[5-bromo-7-(trifluoromethyl)-1H-1,3-benzodiazol-1-yl]-1-methylcyclobutan-1-ol

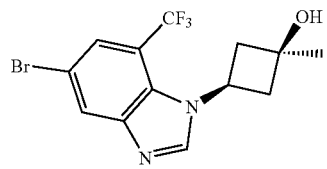 [SMILES: C[C@]1(O)C[C@@H](n2cnc3cc(Br)cc(C(F)(F)F)c32)C1]

A mixture of (cis)-3-{[2-amino-4-bromo-6-(trifluoromethyl)phenyl]amino}-1-methylcyclobutan-1-ol (13.0 g, 38.3 mmol), trimethoxymethane (6.10 g, 57.5 mmol), and TsOH·H₂O (729 mg, 3.83 mmol) in THF (130 mL) was stirred at 50° C. for 1 h. The mixture was cooled to room temperature and concentrated in vacuo to remove most of the THF. The residual solution was diluted with saturated aqueous NaHCO₃ solution (200 mL) and extracted with MTBE (2×100 mL). The combined organic layers were dried over Na₂SO₄, filtered, and concentrated in vacuo. The residue was triturated in MTBE (20 mL) for 30 min. The mixture was filtered to collect the solid to afford (cis)-3-[5-bromo-7-(trifluoromethyl)-1H-1,3-benzodiazol-1-yl]-1-methylcyclobutan-1-ol. MS=349.0/350.9 [M+H]⁺.

Step 5: (cis)-3-[5-(5,5-dimethyl-1,3,2-dioxaborinan-2-yl)-7-(trifluoromethyl)-1H-1,3-benzodiazol-1-yl]-1-methylcyclobutan-1-ol

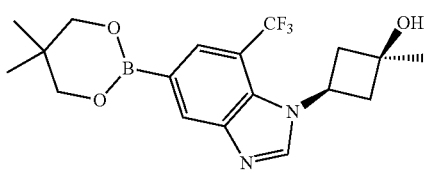

A mixture of (cis)-3-[5-bromo-7-(trifluoromethyl)-1H-1,3-benzodiazol-1-yl]-1-methylcyclobutan-1-ol (6.00 g, 17.2 mmol), 2-(5,5-dimethyl-1,3,2-dioxaborinan-2-yl)-5,5-dimethyl-1,3,2-dioxaborinane (5.82 g, 25.8 mmol), KOAc (5.06 g, 51.6 mmol) and Pd(dppf)Cl₂ (130 mg, 0.172 mmol) in 1,4-dioxane (60 mL) was purged with N₂ (3×) and then stirred at 100° C. for 16 h. After cooling to room temperature, the reaction mixture was filtered and the filtrate was concentrated in vacuo to give (cis)-3-[5-(5,5-dimethyl-1,3,2-dioxaborinan-2-yl)-7-(trifluoromethyl)-1H-1,3-benzodiazol-1-yl]-1-methylcyclobutan-1-ol, which was used in the subsequent step without further purification.

Step 6: 1-[(cis)-3-hydroxy-3-methylcyclobutyl]-7-(trifluoromethyl)-1H-1,3-benzodiazol-5-ol

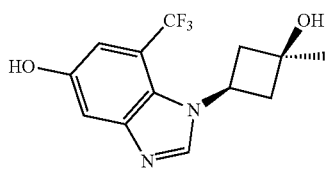 [SMILES: C[C@]1(O)C[C@@H](n2cnc3cc(O)cc(C(F)(F)F)c32)C1]

To a 0° C. solution of (cis)-3-[5-(5,5-dimethyl-1,3,2-dioxaborinan-2-yl)-7-(trifluoromethyl)-1H-1,3-benzodiazol-1-yl]-1-methylcyclobutan-1-ol (9.00 g, 23.6 mmol) in THF (50 mL) and H₂O (50 mL) was added Oxone (14.5 g, 23.6 mmol). The mixture was stirred at room temperature for 2 h. The mixture was cooled to 0° C. and quenched by addition of saturated aqueous Na₂SO₃ (60 mL). The mixture was adjusted to pH=7 by addition of saturated aqueous NaHCO₃ and extracted with EtOAc (2×60 mL). The combined organic phases were washed with brine (30 mL), dried over Na₂SO₄, filtered, and concentrated in vacuo. The residue was triturated with MTBE (20 mL) to give 1-[(cis)-3-hydroxy-3-methylcyclobutyl]-7-(trifluoromethyl)-1H-1,3-benzodiazol-5-ol (Intermediate A-92), which was used in the subsequent step without further purification. MS=287.1 [M+H]⁺.

General Procedure for Intermediate A-95

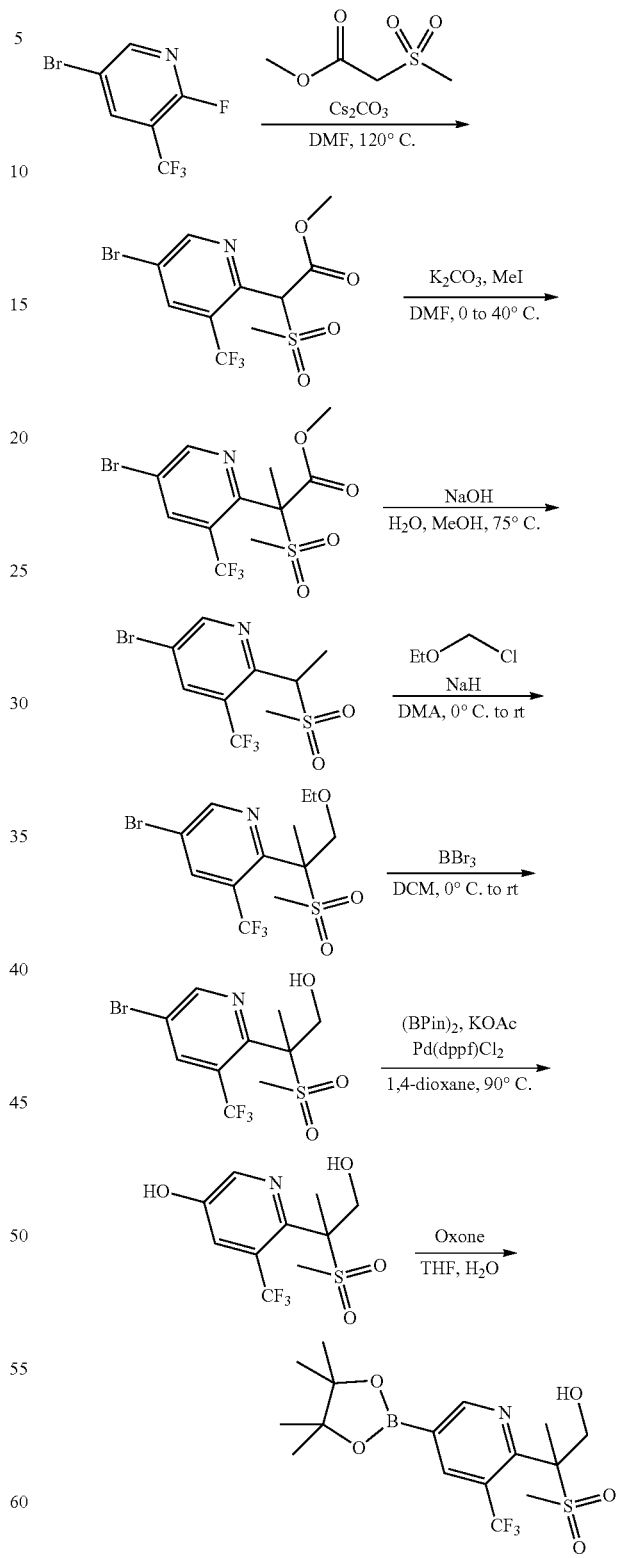

Intermediate A-95

Step 1: methyl 2-[5-bromo-3-(trifluoromethyl)pyridin-2-yl]-2-methanesulfonylacetate

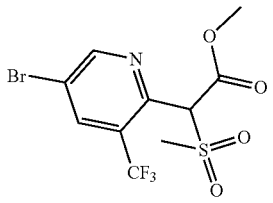 [SMILES: COC(=O)C(c1ncc(Br)cc1C(F)(F)F)S(C)(=O)=O]

To a solution of 5-bromo-2-chloro-3-(trifluoromethyl)pyridine (7.50 g, 28.8 mmol) in DMF (70 mL) was added Cs$_2$CO$_3$ (23.5 g, 72.0 mmol) and methyl 2-methylsulfonylacetate (6.57 g, 43.2 mmol). The mixture was stirred at 120° C. for 2 h. After cooling to 0° C., the reaction mixture was quenched by addition of H$_2$O (70 mL), and then extracted with EtOAc (5×50 mL). The combined organic layers were dried over Na$_2$SO$_4$, filtered, and concentrated in vacuo. The crude residue was purified by flash silica gel chromatography (Biotage 220 g cartridge, 0-20% EtOAc/Petroleum ether) to give methyl 2-[5-bromo-3-(trifluoromethyl)pyridin-2-yl]-2-methanesulfonylacetate. MS=376.1/378.0 [M+H]$^+$.

Step 2: methyl 2-[5-bromo-3-(trifluoromethyl)pyridin-2-yl]-2-methanesulfonylpropanoate

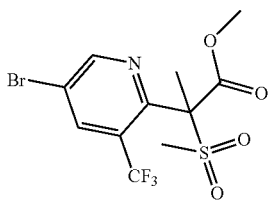

To a 0° C. solution of methyl 2-[5-bromo-3-(trifluoromethyl)pyridin-2-yl]-2-methanesulfonylacetate (14.0 g, 37.2 mmol) and K$_2$CO$_3$ (10.3 g, 74.4 mmol) in DMF (140 mL) was added MeI (10.6 g, 74.4 mmol) dropwise via syringe. The mixture was stirred at 40° C. for 4 h. The reaction mixture was quenched by addition of ice water (100 mL) and stirred below 10° C. for 10 min, and then extracted with EtOAc (3×150 mL). The combined organic layers were dried over Na$_2$SO$_4$, filtered, and concentrated in vacuo. The residue was purified by flash silica gel chromatography (Biotage 220 g cartridge, 0-30% EtOAc/Petroleum ether) to give methyl 2-[5-bromo-3-(trifluoromethyl)pyridin-2-yl]-2-methanesulfonylpropanoate. MS=390.1/392.1 [M+H]$^+$.

Step 3: 5-bromo-2-(1-methanesulfonylethyl)-3-(trifluoromethyl)pyridine

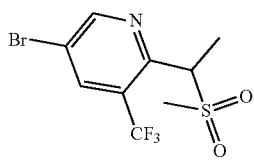 [SMILES: CC(c1ncc(Br)cc1C(F)(F)F)S(C)(=O)=O]

To a solution of methyl 2-[5-bromo-3-(trifluoromethyl)pyridin-2-yl]-2-methanesulfonylpropanoate (13.0 g, 33.3 mmol) in H$_2$O (20 mL) and MeOH (50 mL) was added a solution of NaOH (13.3 g, 333 mmol) in H$_2$O (30 mL). The mixture was stirred at 75° C. for 6 h. After cooling to room temperature, the reaction mixture was filtered, and the filter cake was washed with H$_2$O (3×30 mL). The filter cake was dried in vacuo to give 5-bromo-2-(1-methanesulfonylethyl)-3-(trifluoromethyl)pyridine, which was taken to the next step without further purification MS=332.1/334.1 [M+H]$^+$.

Step 4: 5-bromo-2-(1-ethoxy-2-methanesulfonylpropan-2-yl)-3-(trifluoromethyl)pyridine

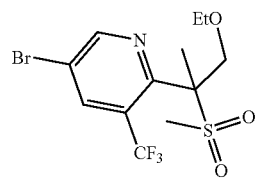 [SMILES: CCOCC(C)(c1ncc(Br)cc1C(F)(F)F)S(C)(=O)=O]

To a round-bottom flask equipped with a magnetic stir bar and thermometer under N$_2$ atmosphere was added 5-bromo-2-(1-methanesulfonylethyl)-3-(trifluoromethyl)pyridine (7.20 g, 21.7 mmol) and DMA (420 mL). The mixture was cooled to 0° C. and NaH (3.48 g, 86.7 mmol, 60% in mineral oil) was added slowly. The resulting mixture was stirred for 3 h at room temperature under N$_2$ atmosphere. Chloromethoxyethane (10.26 g, 108 mmol) was then slowly added to the reaction mixture. The reaction mixture was stirred at room temperature for 2 h, then was cooled to 10° C. and quenched by addition of saturated aqueous NH$_4$Cl solution (150 mL). The mixture was extracted with EtOAc (3×100 mL), then the combined organic layers were washed with brine (150 mL), dried over Na$_2$SO$_4$, filtered, and concentrated in vacuo. The residue was purified by flash silica gel chromatography (Biotage 80 g cartridge, 0-25% EtOAc/Petroleum ether) to give 5-bromo-2-(1-ethoxy-2-methanesulfonylpropan-2-yl)-3-(trifluoromethyl)pyridine. MS=389.9/391.9 [M+H]$^+$.

Step 5: 2-[5-bromo-3-(trifluoromethyl)pyridin-2-yl]-2-methanesulfonylpropan-1-ol

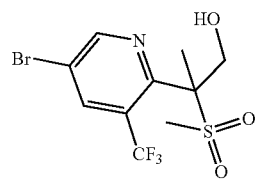

To a round-bottom flask equipped with a magnetic stir bar and thermometer were added 5-bromo-2-(1-ethoxy-2-methanesulfonylpropan-2-yl)-3-(trifluoromethyl)pyridine (3.90 g, 9.99 mmol) and DCM (150 mL). The mixture was cooled to 0° C. and BBr$_3$ (12.5 g, 50.0 mmol) was added dropwise via syringe. The resulting mixture was stirred for 6 h at room temperature. The reaction mixture was then cooled to 10° C. and quenched by addition of saturated aqueous NaHCO$_3$ solution (150 mL) and then extracted with EtOAc (3×75 mL). The combined organic layers were washed with brine (150 mL), dried over Na₂SO₄, filtered, and concentrated in vacuo. The residue was purified by flash silica gel chromatography (Biotage 40 g cartridge, 0-25% EtOAc/Petroleum ether) to give 2-[5-bromo-3-(trifluoromethyl)604pyridine-2-yl]-2-methanesulfonylpropan-1-ol. MS=361.9/363.9 [M+H]⁺.

Step 6: 2-methanesulfonyl-2-[5-(4,4,5,5-tetramethyl-1,3,2-dioxaborolan-2-yl)-3-(trifluoromethyl)pyridine-2-yl]propan-1-ol

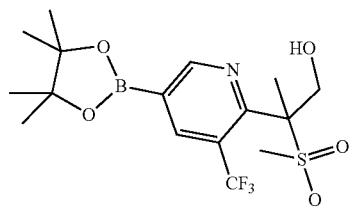

A mixture of 2-[5-bromo-3-(trifluoromethyl)pyridine-2-yl]-2-methanesulfonylpropan-1-ol (1.20 g, 3.31 mmol), bis(pinacolato)diboron (1.01 g, 3.98 mmol), KOAc (650 mg, 6.63 mmol), and Pd(dppf)Cl₂ (242 mg, 331 μmol) in 1,4-dioxane (16 mL) was degassed and purged with N₂ (3×). The mixture was then stirred at 90° C. for 16 h under N₂ atmosphere. After cooling to room temperature, the mixture was diluted with H₂O (20 mL) and extracted with EtOAc (3×20 mL). The combined organic layer was dried over Na₂SO₄, filtered and concentrated in vacuo to give 2-methanesulfonyl-2-[5-(4,4,5,5-tetramethyl-1,3,2-dioxaborolan-2-yl)-3-(trifluoromethyl)pyridin-2-yl]propan-1-ol, which was taken to the next step without further purification. MS=328.1 [M–C₆H₁₀+H]⁺.

Step 7: 6-(1-hydroxy-2-methanesulfonylpropan-2-yl)-5-(trifluoromethyl)pyridin-3-ol

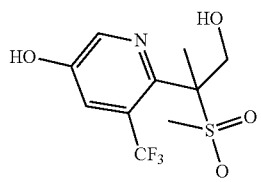

To a solution of 2-methanesulfonyl-2-[5-(4,4,5,5-tetramethyl-1,3,2-dioxaborolan-2-yl)-3-(trifluoromethyl)pyridin-2-yl]propan-1-ol (2.00 g, 4.88 mmol) in acetone (15 mL) and H₂O (15 mL) was added Oxone (6.00 g, 9.78 mmol). The mixture was stirred at room temperature for 2 h. The reaction mixture was cooled to 0° C., quenched by addition of saturated aqueous Na₂SO₃ solution (50 mL), then stirred for 30 min. The mixture was diluted with H₂O (20 mL) and extracted with EtOAc (3×50 mL). The combined organic layer was dried over Na₂SO₄, filtered, and concentrated in vacuo. The residue was purified by flash silica gel chromatography (Biotage 12 g cartridge, 0-50% EtOAc/Petroleum ether) to give 6-(1-hydroxy-2-methanesulfonylpropan-2-yl)-5-(trifluoromethyl)pyridin-3-ol (Intermediate A-95). MS=300.0 [M+H]⁺.

General Procedure for Intermediate A-96

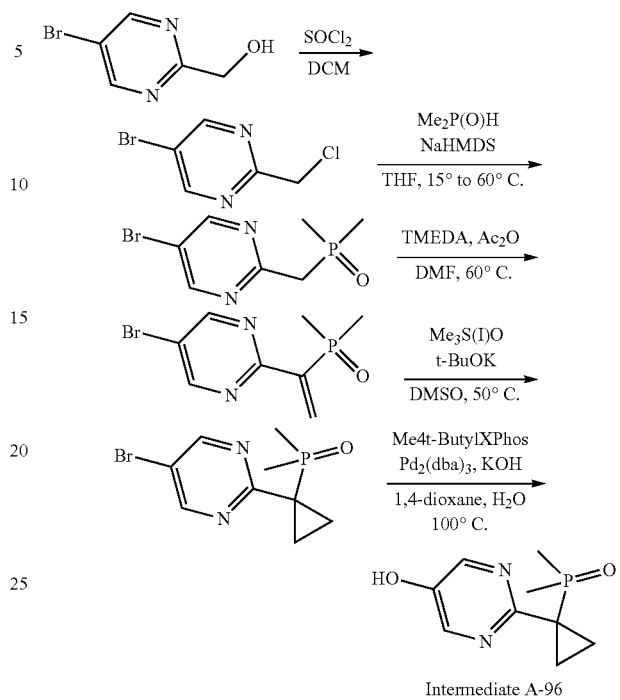

Intermediate A-96

Step 1: 5-bromo-2-(chloromethyl)pyrimidine

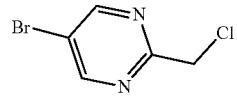

To a solution of (5-bromopyrimidin-2-yl)methanol (4.00 g, 21.2 mmol) in DCM (200 mL) was added SOCl₂ (20 mL) slowly via syringe. The mixture was stirred at room temperature for 3 h. The reaction mixture was concentrated under reduced pressure and the resulting residue was quenched with H₂O (80 mL). The mixture was adjusted to pH=8 with saturated aqueous NaHCO₃ and extracted with EtOAc (3×100 mL). The combined organic layers were dried over Na₂SO₄, filtered, and concentrated in vacuo to give 5-bromo-2-(chloromethyl)pyrimidine, which was taken to the next step without further purification. ¹H NMR (400 MHz, DMSO-d₆): δ 9.05 (s, 2H), 4.81 (s, 2H).

Step 2: 5-bromo-2-[(dimethylphosphoryl)methyl]pyrimidine

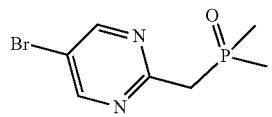

To a 250 mL three-necked round bottom flask equipped with magnetic stirrer, addition funnel, and thermometer under N₂ atmosphere were added dimethylphosphine oxide (1.66 g, 21.2 mmol) and THF (140 mL). To the mixture was added 1 M NaHMDS in THF (23.1 mL, 23.1 mmol) portionwise while keeping the temperature of the reaction mixture between 15-20° C. The mixture was stirred at 15° C. for 1 h under N₂, and then a solution of 5-bromo-2-(chloromethyl)pyrimidine (4.00 g, 19.3 mmol) in THF (30 mL) was added dropwise. The resulting mixture was heated to 60° C. and stirred for 15 h under N₂ atmosphere. The reaction mixture was cooled to 10° C. and quenched by addition of saturated NH₄Cl solution (100 mL) and stirred for 10 min, and then extracted with EtOAc (3×80 mL). The combined organic layers were washed with brine (100 mL), dried over Na₂SO₄, filtered, and concentrated in vacuo. The residue was purified by reverse phase preparative HPLC (Welch Xtimate Cis column, 0-20% MeCN: 10 mM NH₄HCO₃ in H₂O) to give 5-bromo-2-[(dimethylphosphoryl)methyl]pyrimidine. MS=248.9/250.9 [M+H]⁺.

Step 3: 5-bromo-2-[1-(dimethylphosphoryl)ethenyl] pyrimidine

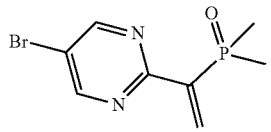

To a solution of 5-bromo-2-(dimethylphosphorylmethyl) pyrimidine (1.00 g, 4.02 mmol) and N,N,N',N'-tetramethylmethanediamine (821 mg, 8.03 mmol) in DMF (8 mL) was added Ac₂O (1.64 g, 16.1 mmol). The mixture was stirred at 60° C. for 2 h. After cooling to room temperature, the reaction was filtered. The residue was purified by reverse phase preparative HPLC (Phenomenex Luna C₁₈ column, 5-35% MeCN: 10 mM TFA in H₂O) to give 5-bromo-2-[1-(dimethylphosphoryl)ethenyl]pyrimidine. MS=260.9/262.9 [M+H]⁺.

Step 4: 5-bromo-2-[1-(dimethylphosphoryl)cyclopropyl]pyrimidine

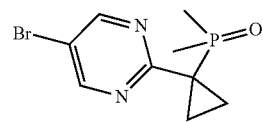

To a solution of trimethylsulfoxonium iodide (2.02 g, 9.19 mmol) in DMSO (6 mL) was added t-BuOK (904 mg, 8.04 mmol). The mixture was stirred at 50° C. for 30 min, and then a solution of 5-bromo-2-[1-(dimethylphosphoryl)ethenyl]pyrimidine (600 mg, 2.30 mmol) in DMSO (1 mL) was added dropwise. The mixture was stirred at 50° C. for 30 min. After cooling to room temperature, the reaction was filtered, and the filtrate was concentrated in vacuo. The residue was purified by reverse phase preparative HPLC (Phenomenex Luna C₁₈ column, 1-40% MeCN: 10 mM TFA in H₂O) to give 5-bromo-2-[1-(dimethylphosphoryl)cyclopropyl]pyrimidine. MS=274.9/276.9 [M+H]⁺.

Step 5: 2-[1-(dimethylphosphoryl)cyclopropyl]pyrimidin-5-ol

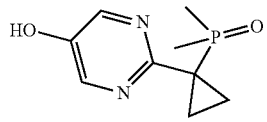

A mixture of 5-bromo-2-[1-(dimethylphosphoryl)cyclopropyl]pyrimidine (400 mg, 1.45 mmol), di-tert-butyl-[2,3,4,5-tetramethyl-6-(2,4,6-triisopropylphenyl)phenyl]phosphane (69.9 mg, 145 μmol), Pd₂(dba)₃ (26.6 mg, 29.1 μmol) and KOH (245 mg, 4.36 mmol) in 1,4-dioxane (5 mL) and H₂O (2 mL) was degassed and purged with N₂ (3×). The mixture was stirred at 100° C. for 16 h under N₂ atmosphere. After cooling to room temperature, the reaction mixture was filtered, and the filtrate was concentrated in vacuo. The residue was purified by reverse phase preparative HPLC (Phenomenex Luna C₁₈ column, 1-25% MeCN: 10 mM TFA in H₂O) to give 2-[1-(dimethylphosphoryl)cyclopropyl]pyrimidin-5-ol (Intermediate A-96). MS=213.2 [M+H]⁺.

General Procedure for Intermediate A-97

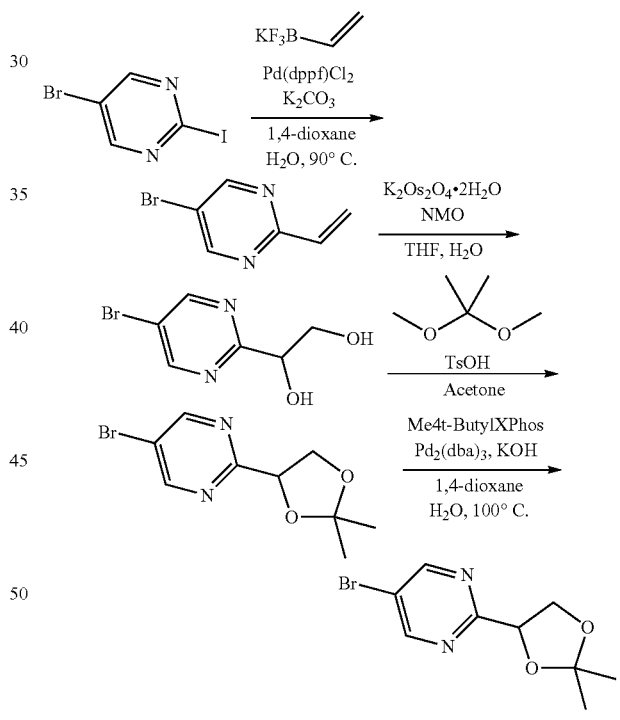

Intermediate A-97

Step 1: 5-bromo-2-vinylpyrimidine

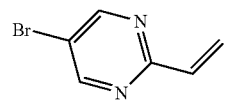

A mixture of 5-bromo-2-iodo-pyrimidine (5.00 g, 17.6 mmol), potassium vinyltrifluoroborate (2.59 g, 19.3 mmol), Pd(dppf)Cl$_2$ (1.28 g, 1.76 mmol), and K$_2$CO$_3$ (6.06 g, 43.9 mmol) in 1,4-dioxane (75 mL) and H$_2$O (25 mL) was degassed and purged with N$_2$ (3×). The mixture was stirred at 90° C. for 12 h under N$_2$ atmosphere. After cooling to room temperature, the reaction mixture was diluted with H$_2$O (60 mL) and extracted with EtOAc (3×20 mL). The combined organic layers were dried over Na$_2$SO$_4$, filtered, and concentrated in vacuo. The residue was purified by flash silica gel chromatography (Biotage 40 g cartridge, 0-15% EtOAc/Petroleum ether) to give 5-bromo-2-vinyl-pyrimidine. MS=185.1/187.1 [M+H]$^+$.

Step 2: 1-(5-bromopyrimidin-2-yl)ethane-1,2-diol

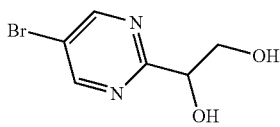 [SMILES: OCC(O)c1ncc(Br)cn1]

To a 0° C. solution of 5-bromo-2-vinyl-pyrimidine (1.80 g, 9.73 mmol) in THF (20 mL) and H$_2$O (20 mL) was added K$_2$OsO$_4$·2H$_2$O (358 mg, 97 μmol) and NMO (2.28 g, 19.5 mmol). The mixture was stirred at room temperature for 12 h. The reaction mixture was diluted with H$_2$O (30 mL) and extracted with EtOAc (3×20 mL). The combined organic layers were dried over Na$_2$SO$_4$, filtered, and concentrated in vacuo. The residue was purified by reverse phase preparative HPLC (Welch Xtimate C$_{18}$ column, 0-20% MeCN: 10 mM NH$_4$HCO$_3$ in H$_2$O) to give 1-(5-bromopyrimidin-2-yl)ethane-1,2-diol. MS=219.1/221.1 [M+H]$^+$.

Step 3: 5-bromo-2-(2,2-dimethyl-1,3-dioxolan-4-yl)pyrimidine

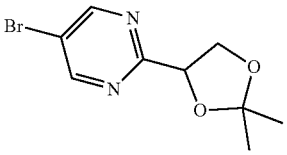

To a solution of 1-(5-bromopyrimidin-2-yl)ethane-1,2-diol (860 mg, 3.93 mmol) in acetone (9 mL) was added 2,2-dimethoxypropane (8.18 g, 78.5 mmol) and TsOH (67.6 mg, 0.393 mmol). The mixture was stirred at room temperature for 12 h. The reaction mixture was diluted with H$_2$O (50 mL) and extracted with EtOAc (4×20 mL). The combined organic layers were dried over Na$_2$SO$_4$, filtered, and concentrated in vacuo. The residue was purified by flash silica gel chromatography (Biotage 12 g cartridge, 0-70% EtOAc/Petroleum ether) to give 5-bromo-2-(2,2-dimethyl-1,3-dioxolan-4-yl)pyrimidine. MS=259.0/261.0 [M+H]$^+$.

Step 4: 2-(2,2-dimethyl-1,3-dioxolan-4-yl)pyrimidin-5-ol

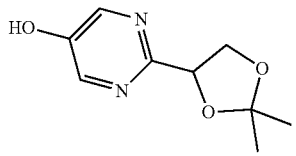

A mixture of 5-bromo-2-(2,2-dimethyl-1,3-dioxolan-4-yl)pyrimidine (200 mg, 0.772 mmol), Pd$_2$(dba)$_3$ (14.0 mg, 15.4 μmol), di-tert-butyl-[2,3,4,5-tetramethyl-6-(2,4,6-triisopropylphenyl)phenyl]phosphane (37.0 mg, 77.2 μmol) and KOH (130 mg, 2.32 mmol) in H$_2$O (2 mL) and 1,4-dioxane (5 mL) was degassed and purged with N$_2$ (3×). The mixture was stirred at 100° C. for 16 h under N$_2$ atmosphere. After cooling to room temperature, the reaction mixture was filtered and the filtrate was concentrated in vacuo to give 2-(2,2-dimethyl-1,3-dioxolan-4-yl)pyrimidin-5-ol (Intermediate A-97), which was taken to the next step without further purification. MS=197.1 [M+H]$^+$.

General Procedure for Intermediate A-98

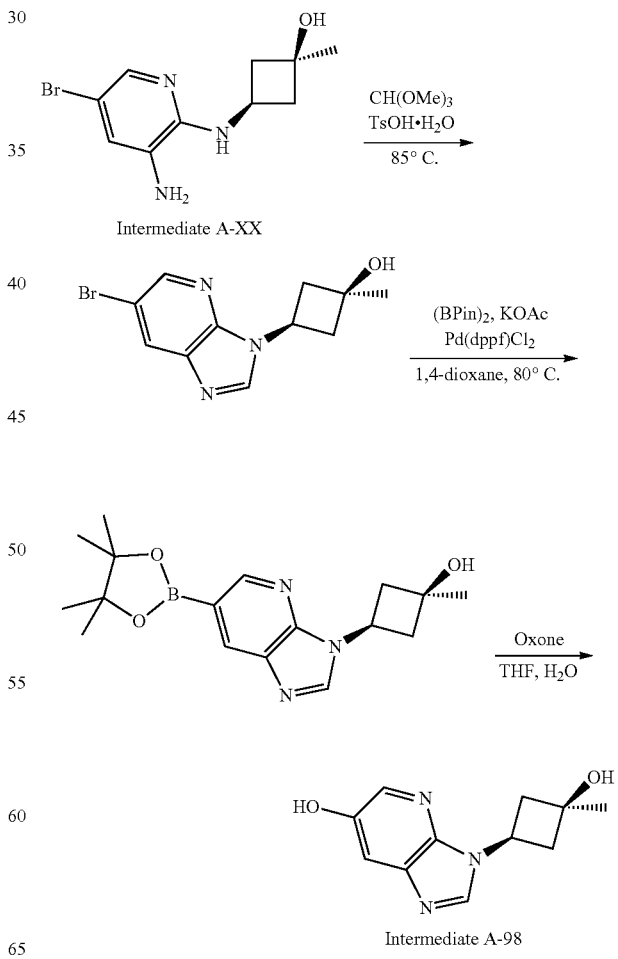

Step 1: (cis)-3-{6-bromo-3H-imidazo[4,5-b]pyridine-3-yl}-1-methylcyclobutan-1-ol

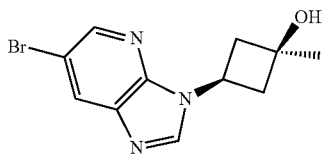 [SMILES: C[C@]1(O)C[C@@H](n2cnc3cc(Br)cnc32)C1]

To a solution of (cis)-3-[(3-amino-5-bromopyridin-2-yl)amino]-1-methylcyclobutan-1-ol (Intermediate A-93, 750 mg, 2.76 mmol) in CH(OMe)₃ (10 mL) was added TsOH·H₂O (52.4 mg, 0.276 mmol). The mixture was stirred at 85° C. for 2 h. After cooling to room temperature, the mixture was diluted with H₂O (30 mL) and extracted with EtOAc (2×20 mL). The combined organic layers were dried over Na₂SO₄, filtered, and concentrated in vacuo to give (cis)-3-{6-bromo-3H-imidazo[4,5-b]pyridin-3-yl}-1-methylcyclobutan-1-ol, which was taken to the next step without further purification. MS=282.0/284.0 [M+H]⁺.

Step 2: (cis)-1-methyl-3-[6-(4,4,5,5-tetramethyl-1,3,2-dioxaborolan-2-yl)-3H-imidazo[4,5-b]pyridin-3-yl]cyclobutan-1-ol

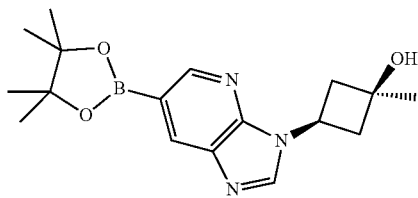

To a solution of (cis)-3-{6-bromo-3H-imidazo[4,5-b]pyridin-3-yl}-1-methylcyclobutan-1-ol (500 mg, 1.77 mmol) in 1,4-dioxane (4 mL) were added bis(pinacolato)diboron (540 mg, 2.13 mmol), KOAc (348 mg, 3.54 mmol) and Pd(dppf)Cl₂ (130 mg, 177 µmol). The mixture was degassed and purged with N₂ (3×), then stirred at 80° C. for 16 h under N₂ atmosphere. After cooling to room temperature, the mixture was filtered and concentrated in vacuo to give (cis)-1-methyl-3-[6-(4,4,5,5-tetramethyl-1,3,2-dioxaborolan-2-yl)-3H-imidazo[4,5-b]pyridin-3-yl]cyclobutan-1-ol, which was taken to the next step without further purification. MS=247.9 [M-C₆H₁₀+H]⁺.

Step 3: 3-[(cis)-3-hydroxy-3-methylcyclobutyl]-3H-imidazo[4,5-b]pyridin-6-ol

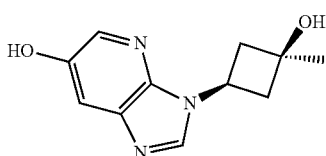

To a solution of (cis)-1-methyl-3-[6-(4,4,5,5-tetramethyl-1,3,2-dioxaborolan-2-yl)-3H-imidazo[4,5-b]pyridin-3-yl]cyclobutan-1-ol (300 mg, 0.911 mmol) in THF (2 mL) and H₂O (2 mL) was added Oxone (560 mg, 911 µmol). The mixture was stirred at room temperature for 2 h. The mixture was concentrated in vacuo to give 3-[(cis)-3-hydroxy-3-methylcyclobutyl]-3H-imidazo[4,5-b]pyridin-6-ol (Intermediate A-98), which was taken to the next step without further purification. MS=220.2 [M+H]⁺.

General Procedure for Intermediate A-99

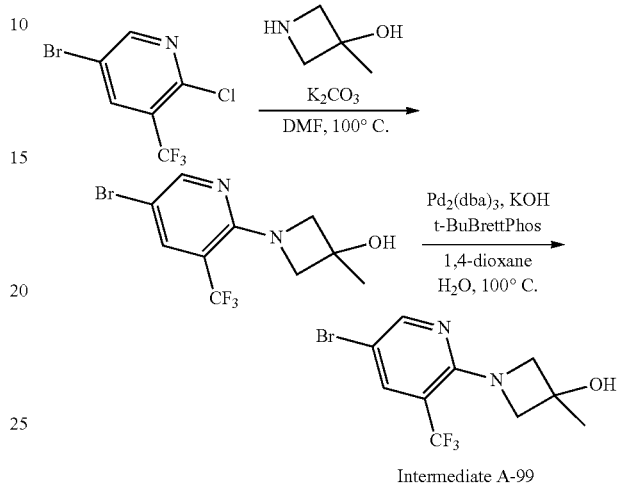

Intermediate A-99

Step 1: 1-[5-bromo-3-(trifluoromethyl)pyridin-2-yl]-3-methylazetidin-3-ol

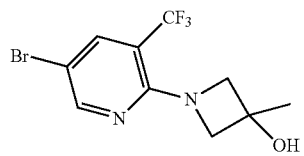 [SMILES: CC1(O)CN(c2ncc(Br)cc2C(F)(F)F)C1]

To a solution of 5-bromo-2-chloro-3-(trifluoromethyl)pyridine (1.00 g, 3.84 mmol) and 3-methylazetidin-3-ol (522 mg, 4.22 mmol, HCl salt) in DMF (10 mL) was added K₂CO₃ (1.86 g, 13.4 mmol). The mixture was stirred at 100° C. for 16 h. After cooling to room temperature, the reaction mixture was concentrated in vacuo. The residue was diluted with H₂O (20 mL) and extracted with EtOAc (3×15 mL). The combined organic layers were washed with brine (10 mL), dried over Na₂SO₄, filtered, and concentrated under reduced pressure. The residue was purified by flash silica gel chromatography (Biotage 12 g cartridge, 0-50% EtOAc/Petroleum ether) to give 1-[5-bromo-3-(trifluoromethyl)pyridin-2-yl]-3-methylazetidin-3-ol. MS=311.0/313.0 [M+H]⁺.

Step 2: 6-(3-hydroxy-3-methylazetidin-1-yl)-5-(trifluoromethyl)pyridin-3-ol

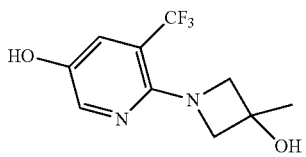 [SMILES: CC1(O)CN(c2ncc(O)cc2C(F)(F)F)C1]

A mixture of 1-[5-bromo-3-(trifluoromethyl)pyridin-2-yl]-3-methylazetidin-3-ol (900 mg, 2.89 mmol), Pd$_2$(dba)$_3$ (53.0 mg, 57.9 μmol), t-BuBrettphos (1.40 g, 2.89 mmol) and KOH (487 mg, 8.68 mmol) in 1,4-dioxane (15 mL) and H$_2$O (6 mL) was degassed and purged with N$_2$ (3×). The mixture was stirred at 100° C. for 16 h under N$_2$ atmosphere. The reaction mixture was allowed to cool to room temperature, then was concentrated in vacuo. The residue was purified by flash silica gel chromatography (Biotage 12 g cartridge, 0-100% EtOAc/Petroleum ether) to give 6-(3-hydroxy-3-methylazetidin-1-yl)-5-(trifluoromethyl)pyridin-3-ol (Intermediate A-99). MS=249.2 [M+H]$^+$.

General Procedure for Intermediate A-100

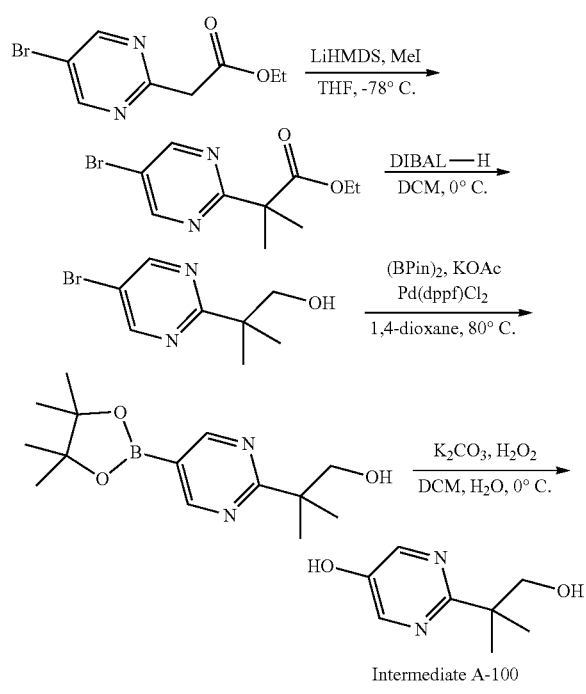

Intermediate A-100

Step 1: ethyl 2-(5-bromopyrimidin-2-yl)-2-methylpropanoate

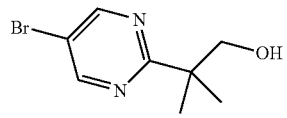

To a three-neck round-bottom flask equipped with a magnetic stir bar and thermometer under N$_2$ atmosphere was added ethyl 2-(5-bromopyrimidin-2-yl)acetate (2.00 g, 8.16 mmol) and THF (20 mL). The mixture was cooled to −78° C. and 1.0 M LiHMDS in THF (8.98 mL, 8.98 mmol) was added dropwise. After stirring at −78° C. for 1 h, MeI (2.42 g, 17.1 mmol) was added in one portion. The mixture was warmed up to room temperature and stirred for 2 h under N$_2$ atmosphere. The reaction mixture was cooled to ~0-5° C. and quenched by addition of saturated aqueous NH$_4$Cl (40 mL), then diluted with H$_2$O (20 mL) and extracted with EtOAc (3×25 mL). The combined organic layers were washed with brine (2×25 mL), dried over Na$_2$SO$_4$, filtered, and concentrated in vacuo to give ethyl 2-(5-bromopyrimidin-2-yl)-2-methylpropanoate, which was taken to the next step without further purification. MS=273.2/275.2 [M+H]$^+$.

Step 2: 2-(5-bromopyrimidin-2-yl)-2-methylpropan-1-ol

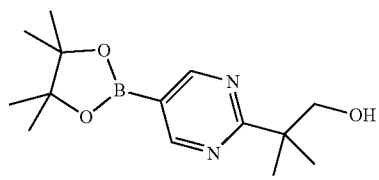 [SMILES: CC(C)(CO)c1ncc(B2OC(C)(C)C(C)(C)O2)cn1]

To a three-neck round-bottom flask equipped with a magnetic stir bar and thermometer under N$_2$ atmosphere were added ethyl 2-(5-bromopyrimidin-2-yl)-2-methylpropanoate (2.60 g, 9.52 mmol) and DCM (30 mL). The mixture was cooled to 0° C. and 1.0 M DIBAL-H in THF (19.0 mL, 19.0 mmol) was added dropwise. The mixture was stirred at 0° C. for 3 h under N$_2$ atmosphere. The reaction mixture was quenched by addition of H$_2$O (60 mL), adjusted to pH=3-4 by dropwise addition of aqueous 3.0 M HCl, then extracted with DCM (3×30 mL). The combined organic layers were washed with brine (2×30 mL), dried over Na$_2$SO$_4$, filtered, and concentrated in vacuo. The residue was purified by flash silica gel chromatography (Biotage 20 g cartridge, 20-60% EtOAc/Petroleum ether) to give 2-(5-bromopyrimidin-2-yl)-2-methylpropan-1-ol. MS=231.0/233.0 [M+H]$^+$.

Step 3: 2-methyl-2-[5-(4,4,5,5-tetramethyl-1,3,2-dioxaborolan-2-yl)pyrimidin-2-yl]propan-1-ol

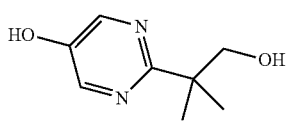

A mixture of 2-(5-bromopyrimidin-2-yl)-2-methylpropan-1-ol (800 mg, 3.46 mmol), bis(pinacolato)diboron (1.32 g, 5.19 mmol), KOAc (1.02 g, 10.4 mmol) and Pd(dppf)Cl$_2$ (253 mg, 346 μmol) in 1,4-dioxane (10 mL) was degassed and purged with N$_2$ (3×), and then the mixture was stirred at 80° C. for 16 h under N$_2$ atmosphere. After cooling to room temperature, the mixture was filtered, the filtrate was concentrated in vacuo to give 2-methyl-2-[5-(4,4,5,5-tetramethyl-1,3,2-dioxaborolan-2-yl)pyrimidin-2-yl]propan-1-ol, which was taken to the next step without further purification. MS=197.2 [M−C$_6$H$_{10}$+H]$^+$.

Step 4: 2-(1-hydroxy-2-methylpropan-2-yl)pyrimidin-5-ol

To a three-neck round-bottom flask equipped with a magnetic stir bar and thermometer under a $N_2$ atmosphere were added 2-methyl-2-[5-(4,4,5,5-tetramethyl-1,3,2-dioxaborolan-2-yl)pyrimidin-2-yl]propan-1-ol (960 mg, 3.45 mmol), $K_2CO_3$ (1.19 g, 8.63 mmol) and DCM (10 mL). The mixture was cooled to 0° C. and 30% $H_2O_2$ in $H_2O$ (1.16 mL, 12.1 mmol) was added in portions. The mixture was stirred at 0° C. for 2 h under $N_2$ atmosphere. The reaction mixture was quenched by addition of saturated aqueous $Na_2SO_3$ solution (20 mL), and then the reaction mixture was concentrated in vacuo. The crude residue was purified by reverse phase preparative HPLC (Waters Xbridge OBD $C_{18}$ column, 20% MeCN: 10 mM $NH_4HCO_3$ in $H_2O$) to give 2-(1-hydroxy-2-methylpropan-2-yl)pyrimidin-5-ol (Intermediate A-100). MS=169.2 $[M+H]^+$.

General Procedure for Intermediate A-101

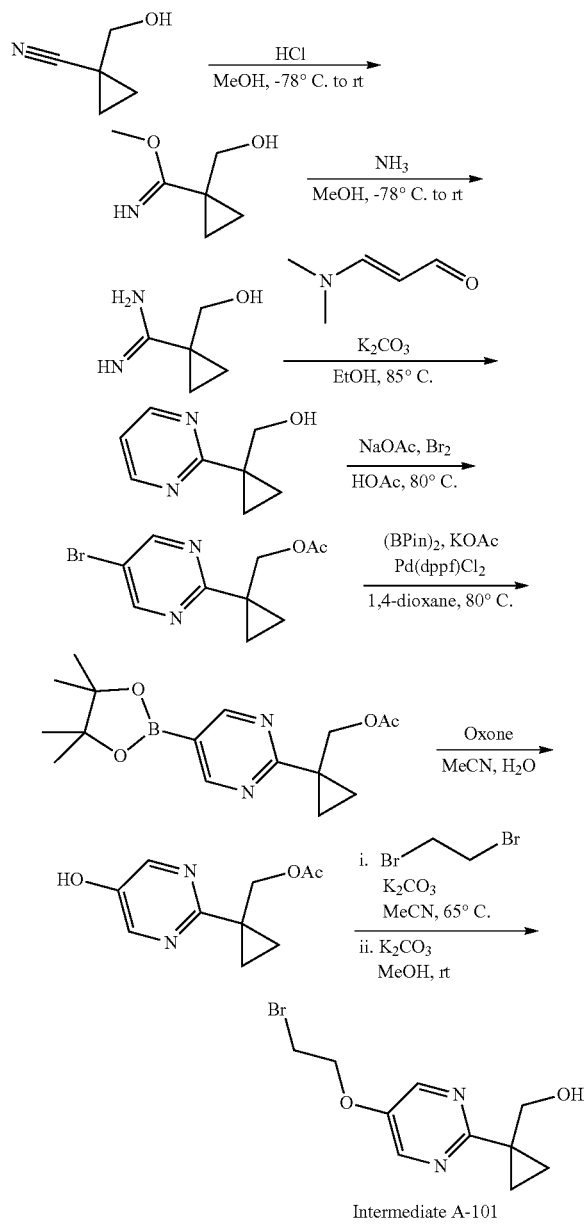

Intermediate A-101

Step 1: methyl 1-(hydroxymethyl)cyclopropanecarboximidate

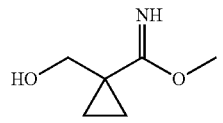

HCl gas was bubbled into a solution of 1-(hydroxymethyl)cyclopropanecarbonitrile (4.00 g, 41.2 mmol) in MeOH (40 mL) at −78° C. for 20 min. The mixture was then stirred at room temperature for 15 h. The mixture was concentrated in vacuo to give methyl 1-(hydroxymethyl)cyclopropanecarboximidate, which was taken to the next step without further purification. MS=130.0 $[M+H]^+$.

Step 2: 1-(hydroxymethyl)cyclopropanecarboxamidine

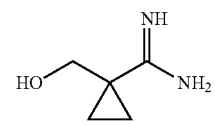

$NH_3$ gas was bubbled into a solution of methyl 1-(hydroxymethyl)cyclopropanecarboximidate (6.00 g, 46.5 mmol) in MeOH (60 mL) at −78° C. for 10 min. The mixture was then stirred at room temperature for 15 h. The mixture was concentrated in vacuo to give 1-(hydroxymethyl)cyclopropanecarboxamidine, which was taken to the next step without further purification. MS=115.2 $[M+H]^+$.

Step 3: [1-(pyrimidin-2-yl)cyclopropyl]methanol

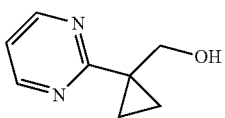 [SMILES: OCC1(c2ncccn2)CC1]

A mixture of 1-(hydroxymethyl)cyclopropanecarboxamidine (5.50 g, 48.2 mmol), (E)-3-(dimethylamino)prop-2-enal (4.54 g, 45.8 mmol) and $K_2CO_3$ (13.3 g, 96.4 mmol) in EtOH (50 mL) was stirred at 85° C. for 15 h. The mixture was concentrated in vacuo. The residue was diluted with water (60 mL) at 0° C., and then extracted with EtOAc (4×20 mL). The combined organic layers were washed with brine (50 mL×2), dried over $Na_2SO_4$, filtered, and concentrated under reduced pressure. The residue was purified by flash silica gel chromatography (Biotage 40 g cartridge, 0-50% EtOAc/Petroleum ether) to give [1-(pyrimidin-2-yl)cyclopropyl]methanol. MS=151.2 $[M+H]^+$.

Step 4: [1-(5-bromopyrimidin-2-yl)cyclopropyl] methyl acetate

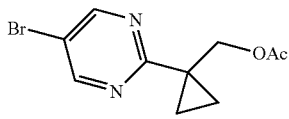 [SMILES: CC(=O)OCC1(c2ncc(Br)cn2)CC1]

To a solution of (1-pyrimidin-2-ylcyclopropyl)methanol (1.00 g, 6.66 mmol) in HOAc (10 mL) was added NaOAc (655 mg, 7.99 mmol). The mixture was heated to 80° C., Br$_2$ (1.60 g, 9.99 mmol) was added, and the reaction was stirred at 80° C. for 3 h. After cooling to 0° C., the reaction mixture was quenched by addition of H$_2$O (20 mL). The mixture was adjusted to pH=8 by slow addition of solid NaOH, and then extracted with EtOAc (3×15 mL). The combined organic layers were washed with brine (2×30 mL), dried over Na$_2$SO$_4$, filtered, and concentrated under reduced pressure. The residue was purified by flash silica gel chromatography (Biotage 12 g cartridge, 0-20% EtOAc/Petroleum ether) to give [1-(5-bromopyrimidin-2-yl)cyclopropyl]methyl acetate. MS=271.0/272.9 [M+H]$^+$.

Step 5: {1-[5-(4,4,5,5-tetramethyl-1,3,2-dioxaborolan-2-yl)pyrimidin-2-yl]cyclopropyl}methyl acetate

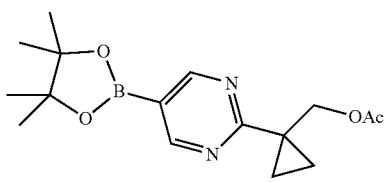 [SMILES: CC(=O)OCC1(c2ncc(B3OC(C)(C)C(C)(C)O3)cn2)CC1]

A mixture of [1-(5-bromopyrimidin-2-yl)cyclopropyl] methyl acetate (500 mg, 1.84 mmol), bis(pinacolato)diboron (609 mg, 2.40 mmol), KOAc (543 mg, 5.53 mmol), and Pd(dppf)Cl$_2$ (67.5 mg, 92.2 μmol) in 1,4-dioxane (15 mL) was degassed and purged with (N$_2$ 3×), and then the mixture was stirred at 80° C. for 15 h under N$_2$ atmosphere. The mixture was filtered, and the filtrate was concentrated in vacuo to give {1-[5-(4,4,5,5-tetramethyl-1,3,2-dioxaborolan-2-yl)pyrimidin-2-yl]cyclopropyl}methyl acetate, which was taken to the next step without further purification. MS=319.3 [M+H]$^+$.

Step 6: [1-(5-hydroxypyrimidin-2-yl)cyclopropyl] methyl acetate

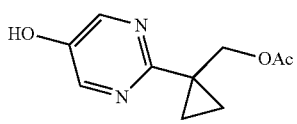 [SMILES: CC(=O)OCC1(c2ncc(O)cn2)CC1]

To a solution of {1-[5-(4,4,5,5-tetramethyl-1,3,2-dioxaborolan-2-yl)pyrimidin-2-yl]cyclopropyl}methyl acetate (800 mg, 2.51 mmol) in MeCN (10 mL) and H$_2$O (10 mL) was added Oxone (1.85 g, 3.01 mmol). The mixture was stirred at room temperature for 2 h. After cooling to 0° C., the reaction mixture was quenched by addition of saturated aqueous Na$_2$SO$_3$ solution (15 mL), and then extracted with EtOAc (3×15 mL). The combined organic layers were washed with brine (2×30 mL), dried over Na$_2$SO$_4$, filtered, and concentrated under reduced pressure. The residue was purified by flash silica gel chromatography (Biotage 12 g cartridge, 0-50% EtOAc/Petroleum ether) to give [1-(5-hydroxypyrimidin-2-yl)cyclopropyl]methyl acetate MS=209.2 [M+H]$^+$.

Step 7: {1-[5-(2-bromoethoxy)pyrimidin-2-yl] cyclopropyl}methanol

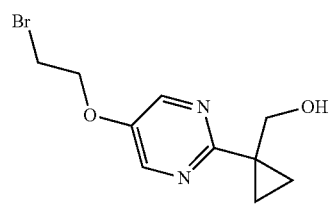

To a solution of [1-(5-hydroxypyrimidin-2-yl)cyclopropyl]methyl acetate (400 mg, 1.92 mmol) in MeCN (5 mL) was added K$_2$CO$_3$ (1.06 g, 7.68 mmol) and 1,2-dibromoethane (5.79 mL, 76.8 mmol). The mixture was stirred at 65° C. for 15 h. The mixture was cooled to room temperature and MeOH (10 mL) and additional K$_2$CO$_3$ (1.06 g, 7.68 mmol) was added, and the reaction was stirred for 2 h. The mixture was filtered, and the filtrate was concentrated to provide [{1-[5-(2-bromoethoxy)pyrimidin-2-yl] cyclopropyl}methanol (Intermediate 101), which was used in the subsequent step without further purification. MS=273.2/275.1 [M+H]$^+$.

General Procedure for Intermediate A-102

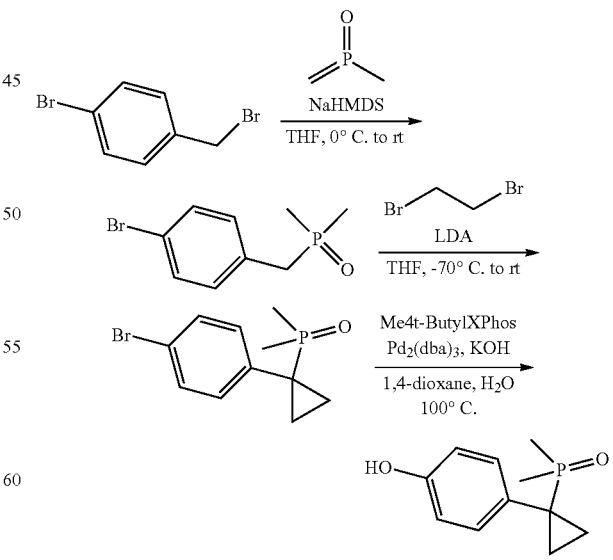

Intermediate A-102

Step 1: 1-bromo-4-[(dimethylphosphoryl)methyl]benzene

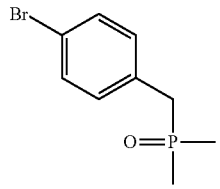

In a three-neck round-bottom flask with a magnetic stir bar and thermometer, 1.0 M NaHMDS in THF (96.0 mL, 96.0 mmol) was added dropwise to a 0° C. solution of methylphosphonoylmethane (6.87 g, 88.2 mmol) in THF (200 mL). The mixture was stirred at 0° C. for 15 min, and then a solution of 1-bromo-4-(bromomethyl)benzene (20.0 g, 80.0 mmol) in THF (25 mL) was added dropwise. The resulting mixture was stirred at room temperature for 2 h. The mixture was quenched with H$_2$O (200 mL) and extracted with DCM (5×50 mL). The combined organic layers were dried over Na$_2$SO$_4$ and filtered, and the solvent was removed in vacuo. The residue was purified by flash silica gel chromatography (Biotage 80 g cartridge, 0-10% MeOH/EtOAc) to give 1-bromo-4-[(dimethylphosphoryl)methyl]benzene. MS=247.0/249.0 [M+H]$^+$.

Step 2: 1-bromo-4-[1-(dimethylphosphoryl)cyclopropyl]benzene

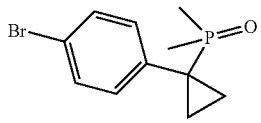

To a three-necked round-bottom flask equipped with a magnetic stir bar and thermometer under N$_2$ atmosphere were added 1-bromo-4-(dimethylphosphorylmethyl)benzene (3.00 g, 12.1 mmol) and freshly distilled THF (40 mL). The mixture was cooled to −70° C. and 2.0 M LDA in THF (13.4 mL, 13.4 mmol) was added dropwise. The mixture was stirred for 10 min at −70° C., then 1,2-dibromoethane (3.42 g, 18.1 mmol) was added, and the mixture was stirred at room temperature for 6 h. The reaction was cooled to 0° C., quenched with H$_2$O (15 mL), and then stirred at 0° C. for 10 min. The mixture was extracted with EtOAc (3×50 mL). The combined organic layers were dried over Na$_2$SO$_4$ and concentrated in vacuo. The crude residue was purified by reverse phase preparative HPLC (Phenomenex Luna C$_{18}$ column, 25-55% MeCN: 10 mM TFA in H$_2$O) to give 1-bromo-4-[1-(dimethylphosphoryl)cyclopropyl]benzene. MS=273.1/275.1 [M+H]$^+$.

Step 3: 4-[1-(dimethylphosphoryl)cyclopropyl]phenol

A mixture of 1-bromo-4-(1-dimethylphosphorylcyclopropyl)benzene (350 mg, 1.28 mmol), ditert-butyl-[2,3,4,5-tetramethyl-6-(2,4,6-triisopropylphenyl)phenyl]phosphane (61.6 mg, 128 μmol), Pd$_2$(dba)$_3$ (23.5 mg, 25.6 μmol) and KOH (216 mg, 3.84 mmol) in 1,4-dioxane (5 mL) and H$_2$O (2 mL) was degassed and purged with N$_2$ (3×). The mixture was stirred at 100° C. for 16 h. After cooling to room temperature, the reaction mixture was filtered, and the filtrate was concentrated in vacuo. The crude residue was purified by reverse phase preparative HPLC (Phenomenex Luna C$_{18}$ column, 1-45% MeCN: 10 mM TFA in H$_2$O) to give 4-[1-(dimethylphosphoryl)cyclopropyl]phenol (Intermediate A-102). MS=211.0 [M+H]$^+$.

General Procedure for Intermediate A-103

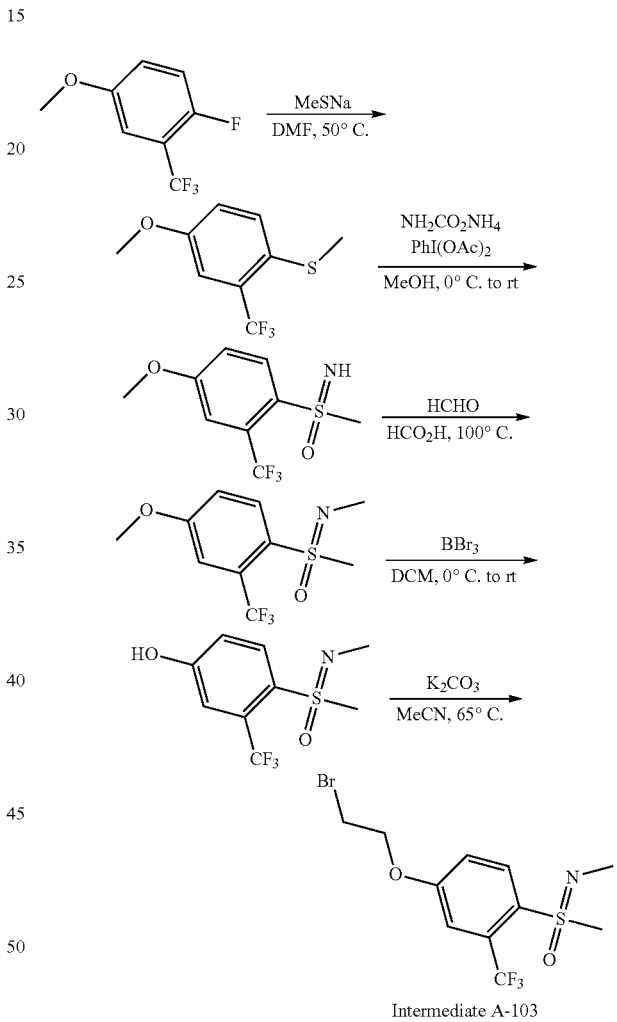

Intermediate A-103

Step 1: 4-methoxy-1-(methylsulfanyl)-2-(trifluoromethyl)benzene

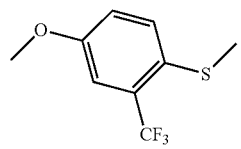

A mixture of 1-fluoro-4-methoxy-2-(trifluoromethyl)benzene (10.0 g, 51.5 mmol) and sodium methanethiolate (5.42 g, 77.3 mmol) in DMF (100 mL) was stirred at 50° C. for 16 h. After cooling to 0° C., the reaction mixture was quenched by addition of H$_2$O (150 mL) and then extracted with EtOAc (3×150 mL). The combined organic layers were washed with H$_2$O (3×150 mL), dried over Na$_2$SO$_4$, filtered, and concentrated under reduced pressure to give 4-methoxy-1-(methylsulfanyl)-2-(trifluoromethyl)benzene, which was taken to the next step without further purification. $^1$H NMR (400 MHz, CDCl$_3$): δ 7.43 (d, J=8.4 Hz, 1H), 7.20 (d, J=2.8 Hz, 1H), 7.03 (dd, J=8.4, 2.4 Hz, 1H), 3.84 (s, 3H), 2.46 (s, 3H).

Step 2: imino[4-methoxy-2-(trifluoromethyl)phenyl]methyl-λ$^6$-sulfanone

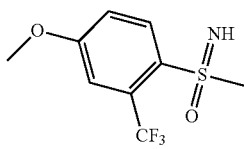

To a 0° C. solution of 4-methoxy-1-(methylsulfanyl)-2-(trifluoromethyl)benzene (10.5 g, 47.3 mmol) and NH$_2$CO$_2$NH$_4$ (14.8 g, 189 mmol) in MeOH (150 mL) was added PhI(OAc)$_2$ (38.1 g, 118 mmol). The mixture was stirred at room temperature for 16 h. The reaction mixture was quenched by addition of H$_2$O (300 mL) and then concentrated under reduced pressure to remove MeOH. The mixture was extracted with EtOAc (3×150 mL). The combined organic layers were dried over Na$_2$SO$_4$, filtered, and concentrated under reduced pressure. The residue was purified by flash silica gel chromatography (Biotage 120 g cartridge, 0-70% EtOAc/Petroleum ether) to give imino[4-methoxy-2-(trifluoromethyl)phenyl]methyl-λ$^6$-sulfanone. $^1$H NMR (400 MHz, DMSO-d$_6$): δ 8.22 (d, J=8.8 Hz, 1H), 7.47-7.36 (m, 2H), 4.43 (s, 1H), 3.91 (s, 3H), 3.07 (s, 3H).

Step 3: {[4-methoxy-2-(trifluoromethyl)phenyl](methyl)oxo-λ$^6$-sulfanylidene}(methyl)amine

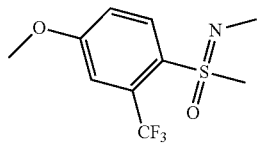

To a solution of imino[4-methoxy-2-(trifluoromethyl)phenyl]methyl-λ$^6$-sulfanone (4.00 g, 15.8 mmol) in HCOOH (40 mL) was added 37% HCHO in H$_2$O (6.41 g, 79.0 mmol). The mixture was stirred at 100° C. for 16 h. After cooling to 0° C., the reaction mixture was quenched by addition of H$_2$O (100 mL), and then adjusted to pH=7 by dropwise addition of saturated aqueous Na$_2$CO$_3$ solution. The aqueous phase was extracted with EtOAc (3×100 mL). The combined organic layers were dried over Na$_2$SO$_4$, filtered and concentrated under reduced pressure to give {[4-methoxy-2-(trifluoromethyl)phenyl](methyl)oxo-λ$^6$-sulfanylidene}(methyl)amine, which was taken to the next step without further purification. MS=268.1 [M+H]$^+$.

Step 4: 4-[methyl(methylimino)oxo-λ$^6$-sulfanyl]-3-(trifluoromethyl)phenol

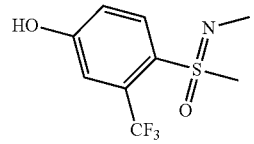 [SMILES: CN=S(C)(=O)c1ccc(O)cc1C(F)(F)F]

To a 0° C. solution of {[4-methoxy-2-(trifluoromethyl)phenyl](methyl)oxo-λ$^6$-sulfanylidene}(methyl)amine (2.50 g, 9.35 mmol) in DCM (30 mL) was added BBr$_3$ (7.21 mL, 74.8 mmol). The mixture was stirred at room temperature for 3 h, then was quenched by slow addition of MeOH (200 mL). The mixture was stirred at room temperature for 10 min, then concentrated in vacuo. The residue was diluted with H$_2$O (100 mL) and extracted with EtOAc (6×100 mL). The combined organic layers were dried over Na$_2$SO$_4$, filtered, and concentrated under reduced pressure to give 4-[methyl(methylimino)oxo-λ$^6$-sulfanyl]-3-(trifluoromethyl)phenol, which was taken to the next step without further purification. MS=254.1 [M+H]$^+$.

Step 5: {[4-(2-bromoethoxy)-2-(trifluoromethyl)phenyl](methyl)oxo-λ$^6$-sulfanylidene}(methyl)amine

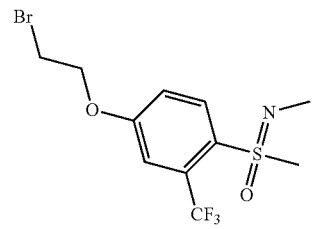 [SMILES: CN=S(C)(=O)c1ccc(OCCBr)cc1C(F)(F)F]

A mixture of 4-[methyl(methylimino)oxo-λ$^6$-sulfanyl]-3-(trifluoromethyl)phenol (2.00 g, 7.90 mmol), 1,2-dibromoethane (59.4 g, 316 mmol) and K$_2$CO$_3$ (8.73 g, 63.2 mmol) in MeCN (20 mL) was stirred at 65° C. for 16 h. After cooling to room temperature, the reaction mixture was quenched by addition of H$_2$O (30 mL) and extracted with EtOAc (3×50 mL). The combined organic layers were dried over Na$_2$SO$_4$, filtered, and concentrated under reduced pressure. The residue was purified by flash silica gel chromatography (Biotage 20 g cartridge, 0-90% EtOAc/Petroleum ether) to give {[4-(2-bromoethoxy)-2-(trifluoromethyl)phenyl](methyl)oxo-λ$^6$-sulfanylidene}(methyl)amine (Intermediate A-103). MS=360.0/362.0 [M+H]$^+$.

General Procedure for Intermediate A-104

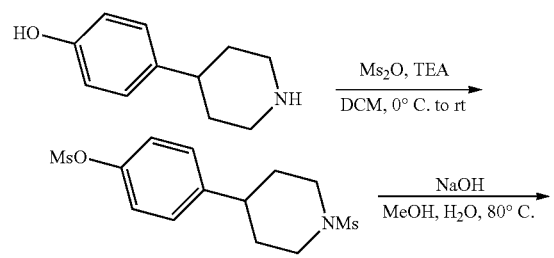

803

-continued

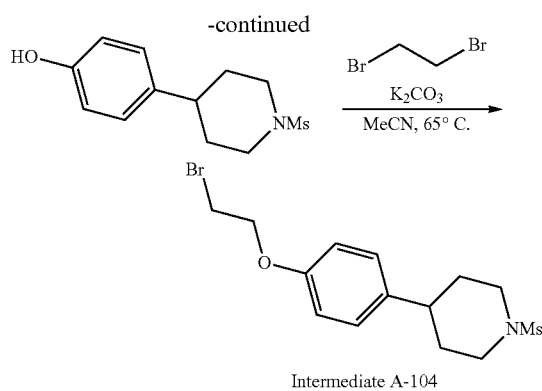

Intermediate A-104

Step 1: 4-(1-methanesulfonylpiperidin-4-yl)phenyl methanesulfonate

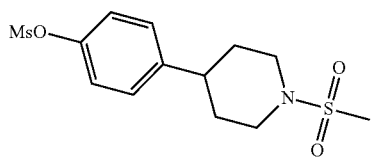 [SMILES: CS(=O)(=O)Oc1ccc(C2CCN(S(C)(=O)=O)CC2)cc1]

To a 0° C. solution of 4-(4-piperidyl)phenol hydrochloride (1.00 g, 4.68 mmol) and TEA (1.42 g, 14.0 mmol) in DCM (10 mL) was added Ms$_2$O (1.63 g, 9.36 mmol) in portions. The mixture was stirred at room temperature for 1 h. The reaction mixture was quenched by addition of H$_2$O (15 mL) and extracted with DCM (3×15 mL). The combined organic layers were dried over Na$_2$SO$_4$, filtered and concentrated under reduced pressure to give 4-(1-methanesulfonylpiperidin-4-yl)phenyl methanesulfonate, which was taken to the next step without further purification.

Step 2: 4-(1-methanesulfonylpiperidin-4-yl)phenol

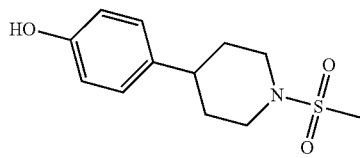 [SMILES: CS(=O)(=O)N1CCC(c2ccc(O)cc2)CC1]

To a solution of [4-(1-methylsulfonyl-4-piperidyl)phenyl] methanesulfonate (1.30 g, 3.90 mmol) in MeOH (15 mL) and H$_2$O (10 mL) was added NaOH (1.19 g, 29.6 mmol). The mixture was stirred at 80° C. for 1 h. After cooling to room temperature, the reaction mixture was concentrated under reduced pressure to remove MeOH and then adjusted to pH=1 by dropwise addition of 3.0 M aqueous HCl. The resulting precipitated solid was collected by filtration and dried in vacuo to give 4-(1-methanesulfonylpiperidin-4-yl) phenol, which was taken to the next step without further purification. MS=256.2 [M+H]$^+$.

804

Step 3: 4-[4-(2-bromoethoxy)phenyl]-1-methanesulfonylpiperidine

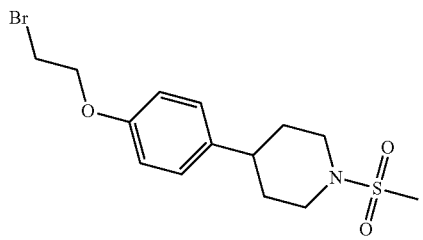 [SMILES: CS(=O)(=O)N1CCC(c2ccc(OCCBr)cc2)CC1]

A mixture of 4-(1-methanesulfonylpiperidin-4-yl)phenol (600 mg, 2.35 mmol), 1,2-dibromoethane (17.7 g, 94.0 mmol) and K$_2$CO$_3$ (1.95 g, 14.1 mmol) in MeCN (10 mL) was stirred at 65° C. for 16 h. The reaction mixture was cooled to room temperature and quenched by addition of H$_2$O (15 mL), then extracted with EtOAc (3×20 mL). The combined organic layers were dried over Na$_2$SO$_4$, filtered, and concentrated under reduced pressure. The residue was purified by flash silica gel chromatography (Biotage 12 g cartridge, 0-65% EtOAc/Petroleum ether) to give 4-[4-(2-bromoethoxy)phenyl]-1-methanesulfonylpiperidine (Intermediate A-104). MS=364.1/362.1 [M+H]$^+$.

General Procedure for Intermediates A-105 & A-106

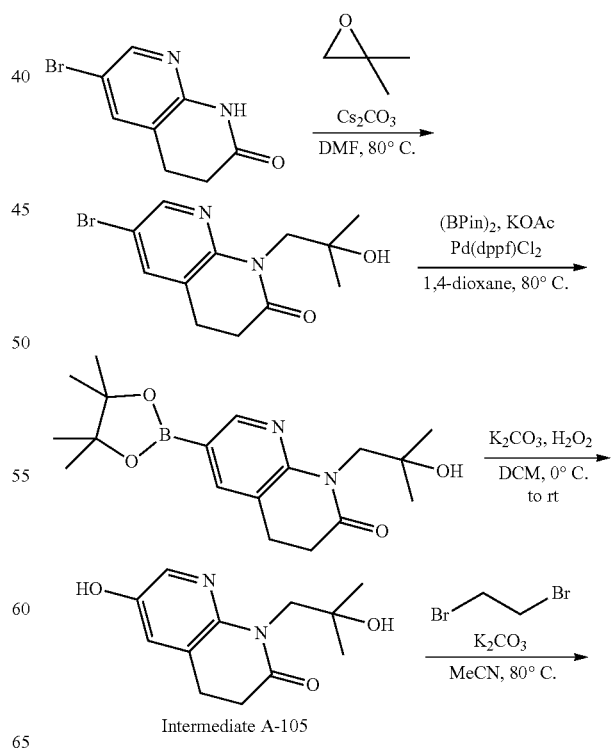

Intermediate A-105

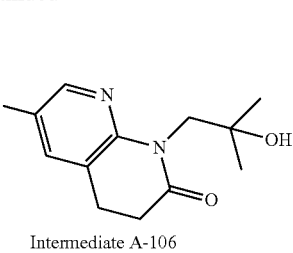

Intermediate A-106

Step 1: 6-bromo-1-(2-hydroxy-2-methylpropyl)-1,2,3,4-tetrahydro-1,8-naphthyridin-2-oneridin-2-one

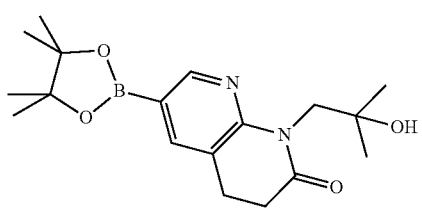 [SMILES: CC(C)(O)CN1C(=O)CCc2cc(B3OC(C)(C)C(C)(C)O3)cnc21]

A mixture of 6-bromo-3,4-dihydro-1H-1,8-naphthyridin-2-one (2.00 g, 8.81 mmol), 2,2-dimethyloxirane (1.27 g, 17.6 mmol), and Cs₂CO₃ (4.30 g, 13.2 mmol) in DMF (30 mL) was stirred at 80° C. for 16 h. After cooling to 0° C., the reaction mixture was quenched by addition of H₂O (100 mL) and extracted with EtOAc (3×50 mL). The combined organic layers were washed with saturated brine (2×50 mL), dried over Na₂SO₄, filtered, and concentrated under reduced pressure. The residue was purified by flash silica gel chromatography (Biotage 12 g cartridge, 0-30% EtOAc/Petroleum ether) to give 6-bromo-1-(2-hydroxy-2-methylpropyl)-1,2,3,4-tetrahydro-1,8-naphthyridin-2-one. MS=298.9/300.9 [M+H]⁺.

Step 2: 1-(2-hydroxy-2-methylpropyl)-6-(4,4,5,5-tetramethyl-1,3,2-dioxaborolan-2-yl)-1,2,3,4-tetrahydro-1,8-naphthyridin-2-one

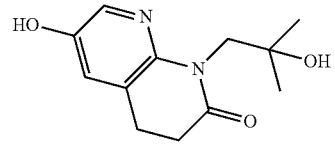 [SMILES: CC(C)(O)CN1C(=O)CCc2cc(O)cnc21]

A mixture of 6-bromo-1-(2-hydroxy-2-methylpropyl)-1,2,3,4-tetrahydro-1,8-naphthyridin-2-one (900 mg, 3.01 mmol), bis(pinacolato)diboron (917 mg, 3.61 mmol), KOAc (591 mg, 6.02 mmol) and Pd(dppf)Cl₂·CH₂Cl₂ (246 mg, 301 μmol) in 1,4-dioxane (10 mL) was degassed and purged with N₂ (3×), and then the mixture was stirred at 80° C. for 16 h under N₂ atmosphere. The reaction mixture was filtered, and the filtrate was concentrated under reduced pressure. The residue was purified by flash silica gel chromatography (Biotage 12 g cartridge, 0-50% EtOAc/Petroleum ether) to give 1-(2-hydroxy-2-methylpropyl)-6-(4,4,5,5-tetramethyl-1,3,2-dioxaborolan-2-yl)-1,2,3,4-tetrahydro-1,8-naphthyridin-2-one. MS=347.3 [M+H]⁺.

Step 3: 6-hydroxy-1-(2-hydroxy-2-methylpropyl)-1,2,3,4-tetrahydro-1,8-naphthyridin-2-one To a 0° C. solution of 1-(2-hydroxy-2-methylpropyl)-6-(4,4,5,5-tetramethyl-1,3,2-dioxaborolan-2-yl)-1,2,3,4-tetrahydro-1,8-naphthyridin-2-one (800 mg, 2.31 mmol) and K₂CO₃ (639 mg, 4.62 mmol) in DCM (10 mL) was added 30% H₂O₂ in H₂O (0.577 mL, 6.00 mmol). The mixture was stirred at room temperature for 16 h. After cooling to 0° C., the reaction mixture was quenched by addition of saturated aqueous Na₂SO₃ solution (20 mL). The mixture was diluted with H₂O (20 mL) and adjusted to pH=6 by dropwise addition of 4.0 M aqueous HCl solution. The mixture was extracted with DCM (3×10 mL), and the combined organic layers were dried over Na₂SO₄, filtered, and concentrated under reduced pressure. The residue was purified by flash silica gel chromatography (Biotage 12 g cartridge, 0-100% EtOAc/Petroleum ether) to give a crude product. The crude product was further triturated with petroleum ether (10 mL) at room temperature for 10 min and then filtered to give 6-hydroxy-1-(2-hydroxy-2-methylpropyl)-1,2,3,4-tetrahydro-1,8-naphthyridin-2-one (Intermediate A-105). MS=237.2 [M+H]⁺.

Step 4: 6-(2-bromoethoxy)-1-(2-hydroxy-2-methylpropyl)-1,2,3,4-tetrahydro-1,8-naphthyridin-2-one

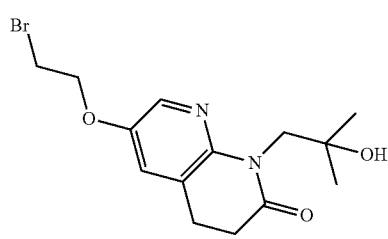 [SMILES: CC(C)(O)CN1C(=O)CCc2cc(OCCBr)cnc21]

To a solution of 6-hydroxy-1-(2-hydroxy-2-methylpropyl)-1,2,3,4-tetrahydro-1,8-naphthyridin-2-one (190 mg, 804 μmol) in MeCN (0.5 mL) was added K₂CO₃ (111 mg, 804 μmol) and 1,2-dibromoethane (6.04 g, 32.2 mmol). The mixture was stirred at 80° C. for 16 h. After cooling to room temperature, the reaction mixture was filtered, and the filtrate was concentrated under reduced pressure. The residue was purified by flash silica gel chromatography (Biotage 4 g cartridge, 0-100% EtOAc/Petroleum ether) to give 6-(2-bromoethoxy)-1-(2-hydroxy-2-methylpropyl)-1,2,3,4-tetrahydro-1,8-naphthyridin-2-one (Intermediate A-106). MS=343.1/345.1 [M+H]⁺.

General Procedure for Intermediate A-107

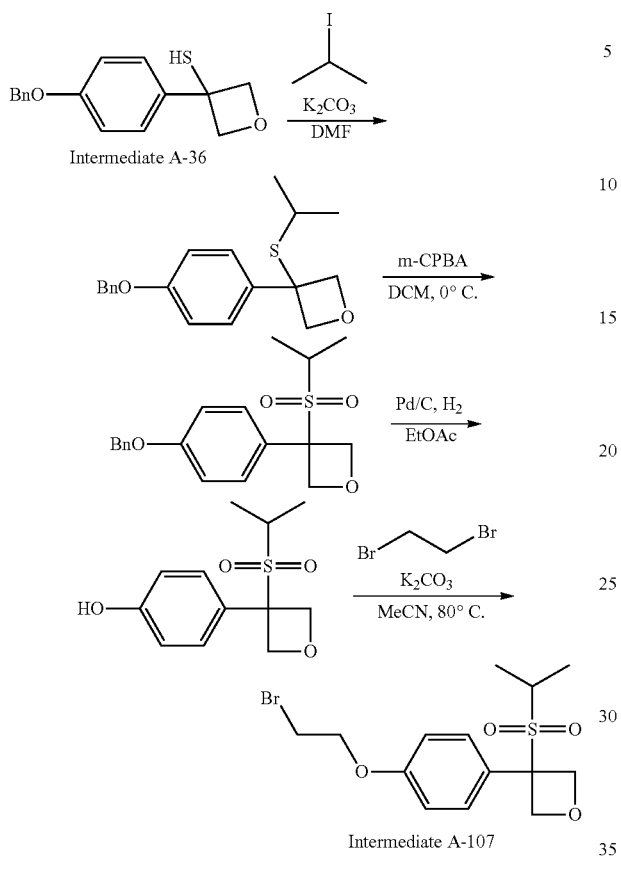

Intermediate A-107

Step 1: 3-[4-(benzyloxy)phenyl]-3-(propan-2-ylsulfanyl)oxetane

To a solution of 3-[4-(benzyloxy)phenyl]oxetane-3-thiol (Step 3, Intermediate A-36, 1.00 g, 3.67 mmol) in DMF (10 mL) was added K₂CO₃ (761 mg, 5.51 mmol) and 2-iodopropane (1.87 g, 11.0 mmol). The mixture was stirred at room temperature for 2 h. After cooling to 0° C., the reaction mixture was quenched by addition of water (10 mL) and then extracted with EtOAc (2×10 mL). The combined organic layers were washed with brine (2×15 mL), dried over Na₂SO₄, filtered, and concentrated under reduced pressure. The residue was purified by flash silica gel chromatography (Biotage 12 g cartridge, 0-20% EtOAc/Petroleum ether) to give 3-[4-(benzyloxy)phenyl]-3-(propan-2-ylsulfanyl)oxetane. $^1$H NMR (400 MHz, DMSO-d₆): δ 7.44-7.31 (m, 5H), 7.24 (d, J=8.8 Hz, 2H), 7.01 (d, J=8.4 Hz, 2H), 5.09 (s, 2H), 5.05 (d, J=6.4 Hz, 2H), 4.74 (d, J=6.4 Hz, 2H), 2.44-2.39 (m, 1H), 1.02 (d, J=6.8 Hz, 6H).

Step 2: 3-[4-(benzyloxy)phenyl]-3-(propane-2-sulfonyl)oxetane

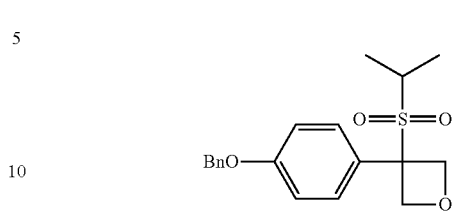

To a 0° C. solution of 3-(4-benzyloxyphenyl)-3-isopropylsulfanyl-oxetane (1.00 g, 3.18 mmol) in DCM (20 mL) was added m-CPBA (1.94 g, 85% purity, 9.54 mmol). The mixture was stirred at room temperature for 2 h. After cooling to 0° C., the reaction mixture was quenched by addition of saturated aqueous Na₂SO₃ solution (20 mL), and then diluted with H₂O (10 mL) and extracted with DCM (3×15 mL). The combined organic layers were washed with saturated aqueous NaHCO₃, dried over Na₂SO₄, filtered, and concentrated under reduced pressure to give 3-(3-[4-(benzyloxy)phenyl]-3-(propane-2-sulfonyl)oxetane, which was taken to the next step without further purification. MS=364.1 [M+NH₄]⁺.

Step 3: 4-[3-(propane-2-sulfonyl)oxetan-3-yl]phenol

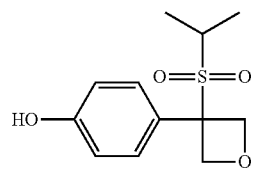 [SMILES: CC(C)S(=O)(=O)C1(c2ccc(O)cc2)COC1]

To a solution of 3-[4-(benzyloxy)phenyl]-3-(propane-2-sulfonyl)oxetane (1.00 g, 2.89 mmol) in EtOAc (20 mL) under Ar atmosphere was added Pd/C (2.00 g, 10 wt %, 1.89 mmol). The suspension was degassed in vacuo and purged with H₂. The mixture was stirred under H₂ (15 psi) at room temperature for 2 h. The mixture was filtered, and the filtrate was concentrated in vacuo to give 4-[3-(propane-2-sulfonyl)oxetan-3-yl]phenol, which was taken to the next step without further purification. MS=274.1 [M+NH₄]⁺.

Step 4: 3-[4-(2-bromoethoxy)phenyl]-3-(propane-2-sulfonyl)oxetane

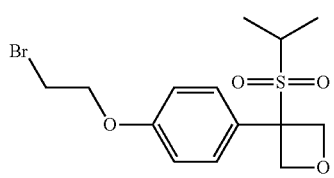 [SMILES: CC(C)S(=O)(=O)C1(c2ccc(OCCBr)cc2)COC1]

To a solution of 4-[3-(propane-2-sulfonyl)oxetan-3-yl] phenol (650 mg, 2.54 mmol) in MeCN (5 mL) was added K₂CO₃ (1.75 g, 12.7 mmol) and 1,2-dibromoethane (19.1 g, 101 mmol). The mixture was stirred at 65° C. for 15 h. After cooling to room temperature, the mixture was filtered, and the filtrate was concentrated in vacuo. The residue was purified by flash silica gel chromatography (Biotage 12 g cartridge, 0-50% EtOAc/Petroleum ether) to give 3-[4-(2-bromoethoxy)phenyl]-3-(propane-2-sulfonyl)oxetane (Intermediate A-107). MS=380.0/382.0 [M+NH$_4$]$^+$.

General Procedure for Intermediate A-108

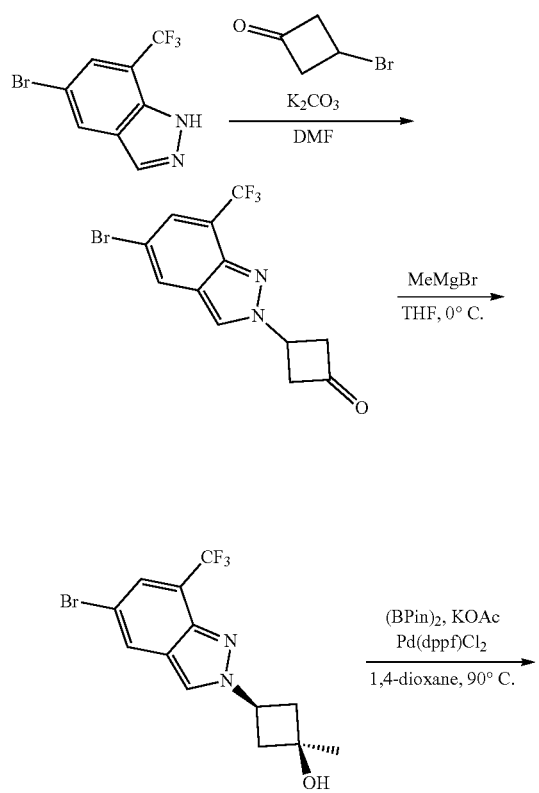

Intermediate A-108

Step 1: 3-[5-bromo-7-(trifluoromethyl)-2H-indazol-2-yl]cyclobutan-1-one

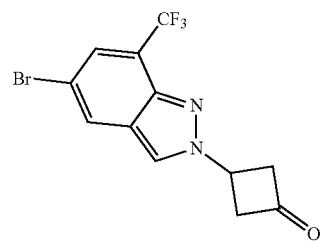 [SMILES: O=C1CC(n2cc3cc(Br)cc(C(F)(F)F)c3n2)C1]

To a mixture of 5-bromo-7-(trifluoromethyl)-1H-indazole (950 mg, 3.58 mmol) and K$_2$CO$_3$ (991 mg, 7.17 mmol) in DMF (9 mL) at room temperature was added 3-bromocyclobutan-1-one (641 mg, 4.30 mmol) dropwise. The mixture was stirred at room temperature for 1 h. The mixture was then poured into ice water (100 mL) and extracted with EtOAc (3×50 mL). The combined organic layers were dried over Na$_2$SO$_4$, filtered and concentrated. The crude product was purified by silica gel chromatography (Biotage 50 g cartridge, 0-10% EtOAc/DCM) to give 3-[5-bromo-7-(trifluoromethyl)-2H-indazol-2-yl]cyclobutan-1-one (2$^{nd}$ eluting isomer). MS=333.0/335.0 [M+H]$^+$.

Step 2: (cis)-3-[5-bromo-7-(trifluoromethyl)-2H-indazol-2-yl]-1-methylcyclobutan-1-ol

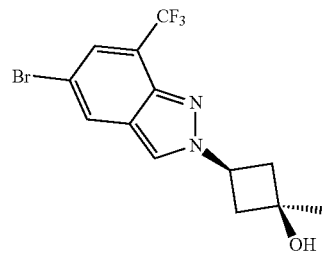 [SMILES: C[C@]1(O)C[C@@H](n2cc3cc(Br)cc(C(F)(F)F)c3n2)C1]

To a solution of 3-[5-bromo-7-(trifluoromethyl)-2H-indazol-2-yl]cyclobutan-1-one (995 mg, 2.99 mmol) in THF (10 mL) at 0° C. was added 3.0 M MeMgBr in Et$_2$O (1.29 mL, 3.88 mmol) dropwise. The resulting mixture was stirred at 0° C. for 1 h. The mixture was quenched by addition of saturated NH$_4$Cl solution (30 mL) and extracted with EtOAc (3×30 mL). The combined organic layers were dried over Na$_2$SO$_4$, filtered and concentrated. The residue was purified by flash silica gel chromatography twice (Biotage 50 g cartridge, 0-50% EtOAc/DCM) to give (cis)-3-[5-bromo-7-(trifluoromethyl)-2H-indazol-2-yl]-1-methylcyclobutan-1-ol. MS=349.1/351.1 [M+H]$^+$.

Step 3: (cis)-1-methyl-3-[5-(4,4,5,5-tetramethyl-1,3,2-dioxaborolan-2-yl)-7-(trifluoromethyl)-2H-indazol-2-yl]cyclobutan-1-ol

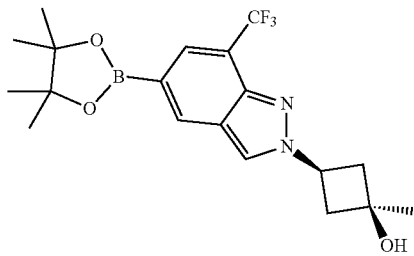

A mixture of (cis)-3-[5-bromo-7-(trifluoromethyl)-2H-indazol-2-yl]-1-methylcyclobutan-1-ol (800 mg, 2.29 mmol), bis(pinacolato)diboron (756 mg, 2.98 mmol), Pd(dppf)Cl$_2$ dichloromethane complex (93.6 mg, 0.115 mmol) and KOAc (450 mg, 4.58 mmol) in 1,4-dioxane (23 mL) was sparged with N$_2$ gas and then stirred at 90° C. for 16 h. The reaction mixture was cooled to room temperature and diluted with EtOAc, then filtered over a celite plug. The resulting filtrate was concentrated and used in the subsequent step without further purification. MS=397.3 [M+H]$^+$.

Step 4: 2-[(cis)-3-hydroxy-3-methylcyclobutyl]-7-(trifluoromethyl)-2H-indazol-5-ol

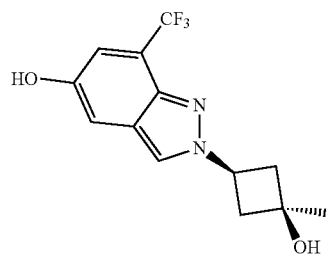 [SMILES: C[C@]1(O)C[C@@H](n2cc3cc(O)cc(C(F)(F)F)c3n2)C1]

The crude residue from the previous step was dissolved in MeOH (11 mL) and cooled to 0° C. A solution of 30% H$_2$O$_2$ in H$_2$O (0.585 mL, 5.72 mmol) was added dropwise. The mixture was then stirred at room temperature for 3 h. The mixture was concentrated under reduced pressure and purified by silica gel chromatography (Biotage 50 g cartridge, 0-50% EtOAc/DCM) to give 2-[(cis)-3-hydroxy-3-methylcyclobutyl]-7-(trifluoromethyl)-2H-indazol-5-ol (Intermediate A-108). MS=287.1 [M+H]$^+$.

General Procedure for Intermediate A-109

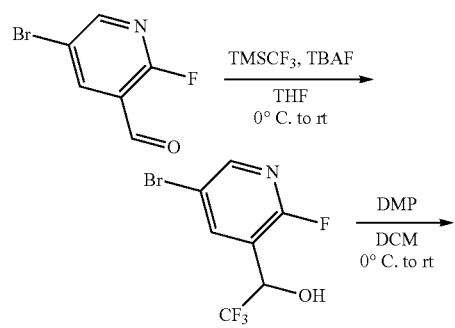

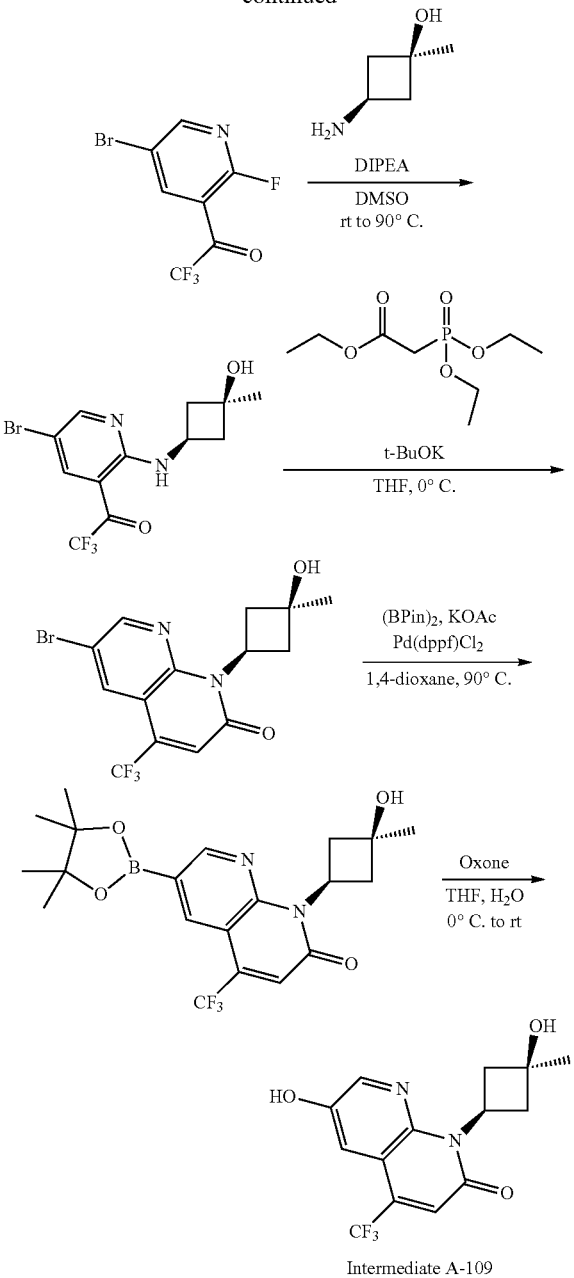

Intermediate A-109

Step 1: 1-(5-bromo-2-fluoropyridin-3-yl)-2,2,2-trifluoroethan-1-ol

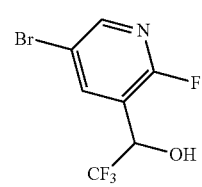 [SMILES: OC(c1cc(Br)cnc1F)C(F)(F)F]

To a 0° C. mixture of 5-bromo-2-fluoro-pyridine-3-carbaldehyde (10.0 g, 49.0 mmol) and TMSCF$_3$ (8.36 g, 58.8 mmol) in THF (100 mL) was added dropwise 1.0 M TBAF in THF (9.80 mL, 9.80 mmol). The mixture was stirred at room temperature for 1 h, then was diluted with brine (150 mL) and extracted with EtOAc (2×80 mL). The combined organic layers were dried over Na₂SO₄, filtered, and concentrated in vacuo. The residue was purified by flash silica gel chromatography (Biotage 120 g cartridge, 0-8% EtOAc/ Petroleum ether) to provide 1-(5-bromo-2-fluoropyridin-3-yl)-2,2,2-trifluoroethan-1-ol. MS=273.8/275.8 [M+H]⁺.

Step 2: 1-(5-bromo-2-fluoropyridin-3-yl)-2,2,2-trifluoroethan-1-one

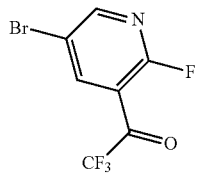

To a 0° C. mixture of 1-(5-bromo-2-fluoropyridin-3-yl)-2,2,2-trifluoroethan-1-ol (12.5 g, 45.6 mmol) in DCM (150 mL) was added Dess-Martin periodinane (23.2 g, 54.7 mmol). The mixture was stirred at room temperature for 16 h, then was quenched by addition of saturated aqueous Na₂SO₃ solution (200 mL) and extracted with DCM (2×80 mL). The combined organic layers were dried over Na₂SO₄, filtered, and concentrated in vacuo. The residue was purified by flash silica gel chromatography (Biotage 120 g cartridge, 0-25% EtOAc/Petroleum ether) to provide 1-(5-bromo-2-fluoropyridin-3-yl)-2,2,2-trifluoroethan-1-one. MS=289.8/ 291.8 [M+H₂O+H]⁺.

Step 3: 1-(5-bromo-2-{[(cis)-3-hydroxy-3-methylcyclobutyl]amino}pyridin-3-yl)-2,2,2-trifluoroethan-1-one

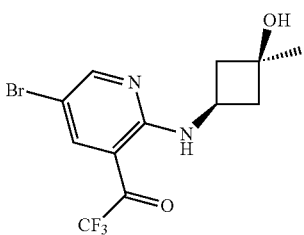 [SMILES: C[C@]1(O)C[C@@H](Nc2ncc(Br)cc2C(=O)C(F)(F)F)C1]

To a mixture of 1-(5-bromo-2-fluoropyridin-3-yl)-2,2,2-trifluoroethan-1-one (4.00 g, 14.7 mmol) and (cis)-3-amino-1-methylcyclobutan-1-ol (2.02 g, 14.7 mmol, HCl salt) in DMSO (35 mL) was added DIPEA (7.68 mL, 44.1 mmol). The mixture was stirred at 90° C. for 4 h. After cooling to room temperature, the mixture was diluted with H₂O (150 mL) and extracted with EtOAc (2×80 mL). The combined organic layers were dried over Na₂SO₄, filtered, and concentrated in vacuo. The residue was purified by flash silica gel chromatography (Biotage 80 g cartridge, 0-25% EtOAc/ Petroleum ether) to provide 1-(5-bromo-2-{[(cis)-3-hydroxy-3-methylcyclobutyl]amino}pyridin-3-yl)-2,2,2-trifluoroethan-1-one. MS=352.9/354.8 [M+H]⁺.

Step 4: 6-bromo-1-[(cis)-3-hydroxy-3-methylcyclobutyl]-4-(trifluoromethyl)-1,2-dihydro-1,8-naphthyridin-2-one

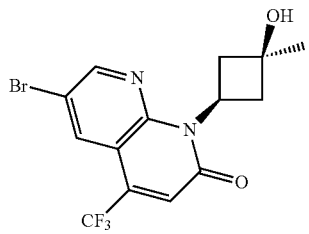 [SMILES: C[C@]1(O)C[C@@H](n2c(=O)cc(C(F)(F)F)c3cc(Br)cnc32)C1]

To a 0° C. mixture of ethyl 2-diethoxyphosphorylacetate (2.22 mL, 11.2 mmol) in THF (40 mL) was added t-BuOK (2.10 g, 18.7 mmol). The mixture was stirred at room temperature for 1 h, then cooled to 0° C. A solution of 1-(5-bromo-2-{[(cis)-3-hydroxy-3-methylcyclobutyl]amino}pyridin-3-yl)-2,2,2-trifluoroethan-1-one (3.30 g, 9.34 mmol) in THF (25 mL) was added dropwise to the 0° C. mixture. After stirring at 0° C. for 2 h, the mixture was quenched by addition of saturated aqueous NH₄Cl solution (60 mL). The organic layer was separated, and the aqueous layer was extracted with EtOAc (2×40 mL). The combined organic layers were concentrated in vacuo. The residue was purified by flash silica gel chromatography (Biotage 40 g cartridge, 0-17% EtOAc/Petroleum ether) to provide 6-bromo-1-[(cis)-3-hydroxy-3-methylcyclobutyl]-4-(trifluoromethyl)-1,2-dihydro-1,8-naphthyridin-2-one. MS=377.0/378.9 [M+H]⁺.

Step 5: 1-[(cis)-3-hydroxy-3-methylcyclobutyl]-6-(4,4,5,5-tetramethyl-1,3,2-dioxaborolan-2-yl)-4-(trifluoromethyl)-1,2-dihydro-1,8-naphthyridin-2-one

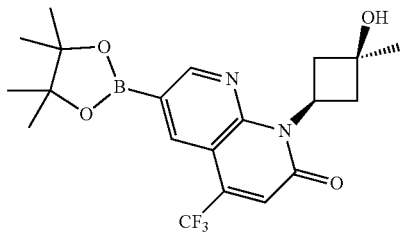

A mixture of 6-bromo-1-[(cis)-3-hydroxy-3-methylcyclobutyl]-4-(trifluoromethyl)-1,2-dihydro-1,8-naphthyridin-2-one (1.30 g, 3.45 mmol), bis(pinacolato)diboron (1.75 g, 6.89 mmol), KOAc (846 mg, 8.62 mmol) and Pd(dppf)Cl₂ (126 mg, 172 µmol) in 1,4-dioxane (20 mL) was purged with N₂ (3×) and stirred at 90° C. for 16 h. After cooling to room temperature, solids were removed by filtration and the filtrate was concentrated in vacuo to provide 1-[(cis)-3-hydroxy-3-methylcyclobutyl]-6-(4,4,5,5-tetramethyl-1,3,2-dioxaborolan-2-yl)-4-(trifluoromethyl)-1,2-dihydro-1,8-naphthyridin-2-one, which was used in the subsequent step without further purification.

Step 6: 6-hydroxy-1-[(cis)-3-hydroxy-3-methylcyclobutyl]-4-(trifluoromethyl)-1,2-dihydro-1,8-naphthyridin-2-one

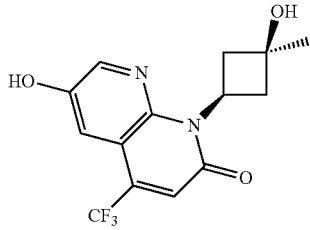 [SMILES: C[C@]1(O)C[C@@H](n2c(=O)cc(C(F)(F)F)c3cc(O)cnc32)C1]

To a 0° C. mixture of 1-[(cis)-3-hydroxy-3-methylcyclobutyl]-6-(4,4,5,5-tetramethyl-1,3,2-dioxaborolan-2-yl)-4-(trifluoromethyl)-1,2-dihydro-1,8-naphthyridin-2-one (1.50 g, 3.54 mmol) in a THF (20 mL) and H$_2$O (10 mL) was added Oxone (2.61 g, 4.24 mmol). The mixture was stirred at room temperature for 1 h. The reaction mixture was cooled to 0-10° C., quenched by addition of saturated Na$_2$SO$_3$ solution (60 mL) at 0-10° C., and stirred for 30 min. The mixture was extracted with EtOAc (2×40 mL). The combined organic layers were dried over Na$_2$SO$_4$, filtered, and concentrated in vacuo. The residue was purified by flash silica gel chromatography (Biotage 20 g cartridge, 0-15% EtOAc/Petroleum ether) to provide 6-hydroxy-1-[(cis)-3-hydroxy-3-methylcyclobutyl]-4-(trifluoromethyl)-1,2-dihydro-1,8-naphthyridin-2-one (Intermediate A-109). MS=315.0 [M+H]$^+$.

General Procedure for Intermediate A-110

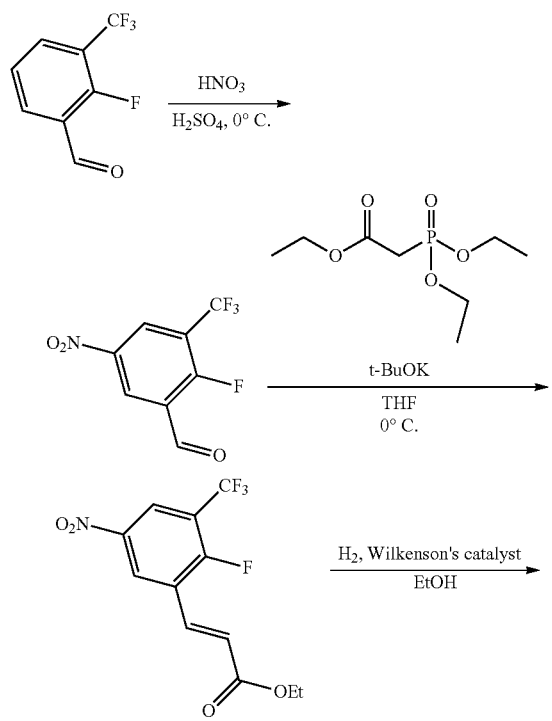

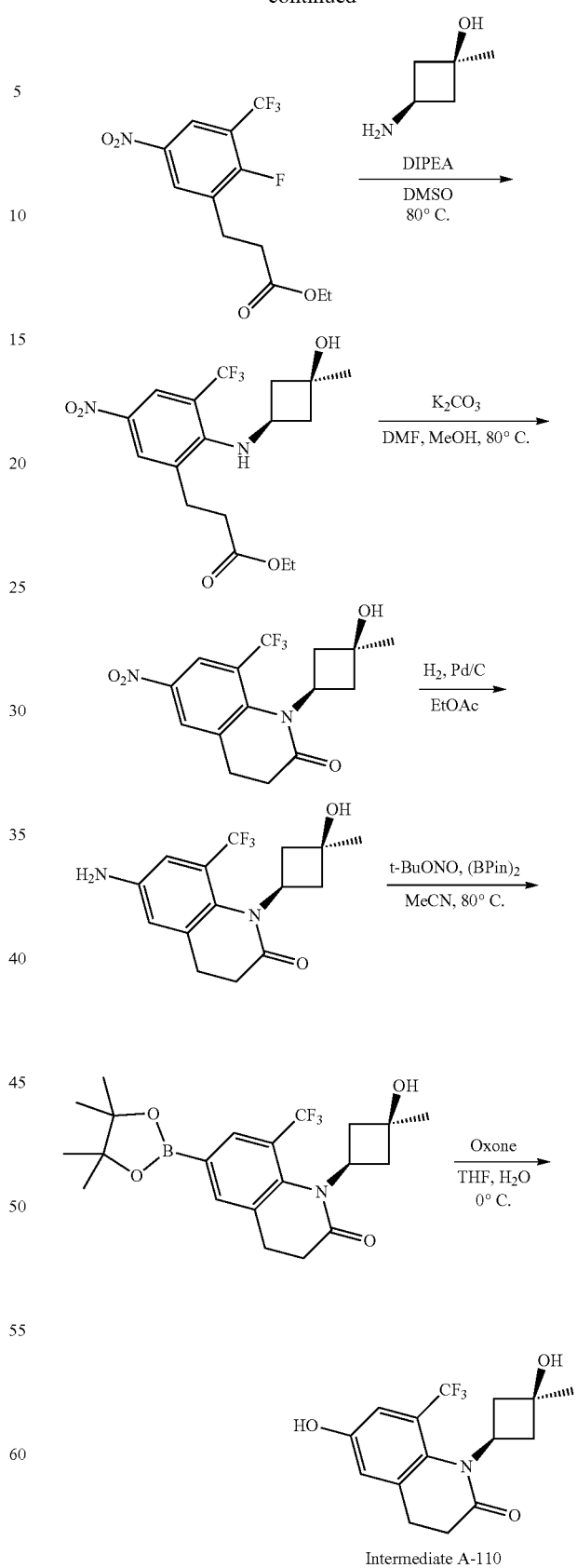

Intermediate A-110

Step 1: 2-fluoro-5-nitro-3-(trifluoromethyl)benzaldehyde

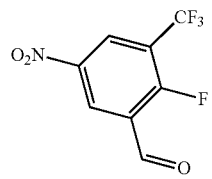 [SMILES: O=Cc1cc([N+](=O)[O-])cc(C(F)(F)F)c1F]

To a 250 mL three-neck round bottom flask equipped with a magnetic stir bar and thermometer containing a solution of 2-fluoro-3-(trifluoromethyl)benzaldehyde (7.19 mL, 52.1 mmol) in $H_2SO_4$ (50 mL) at −5-0° C. was added $HNO_3$ (21.1 mL, 468 mmol) dropwise. The mixture was stirred at 0° C. for 30 min. The reaction mixture was poured into ice water (80 mL), adjusted to pH=7 by addition of solid $NaHCO_3$, and extracted with EtOAc (3×50 mL). The combined organic layers were dried over anhydrous $Na_2SO_4$, filtered, and concentrated in vacuo. The residue was purified by flash silica gel chromatography (Biotage 40 g cartridge, 0-3% EtOAc/Petroleum ether) to provide 2-fluoro-5-nitro-3-(trifluoromethyl)benzaldehyde. $^1$H NMR (400 MHz, DMSO-$d_6$): δ 10.43 (s, 1H), 8.96 (dd, J=5.2, 2.8 Hz, 1H), 8.77 (dd, J=5.6, 2.8 Hz, 1H).

Step 2: ethyl (2E)-3-[2-fluoro-5-nitro-3-(trifluoromethyl)phenyl]prop-2-enoate

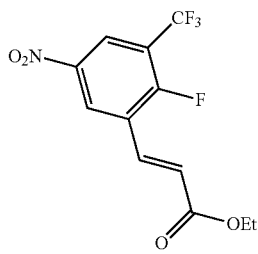 [SMILES: CCOC(=O)/C=C/c1cc([N+](=O)[O-])cc(C(F)(F)F)c1F]

To a 0° C. solution of ethyl 2-(diethoxyphosphoryl)acetate (13.8 mL, 69.6 mmol) in THF (300 mL) was added t-BuOK (8.52 g, 75.9 mmol) in portions. The mixture was stirred at 0° C. for 1 h. A solution of 2-fluoro-5-nitro-3-(trifluoromethyl)benzaldehyde (15.0 g, 63.3 mmol) in THF (30 mL) was added to the 0° C. mixture, and reaction was allowed to warm to room temperature and stirred for 2 h. The reaction mixture was quenched by addition of $H_2O$ (100 mL) and extracted with EtOAc (3×100 mL). The combined organic layers were washed with brine (80 mL), dried over anhydrous $Na_2SO_4$, filtered, and concentrated in vacuo. The residue was purified by flash silica gel chromatography (Biotage 80 g cartridge, 0-10% EtOAc/Petroleum ether) to provide ethyl (2E)-3-[2-fluoro-5-nitro-3-(trifluoromethyl)phenyl]prop-2-enoate. $^1$H NMR (400 MHz, DMSO-$d_6$): δ 8.66 (dd, J=5.6, 2.8 Hz, 1H), 8.53 (dd, J=5.6, 2.8 Hz, 1H), 7.82 (d, J=16.0 Hz, 1H), 6.72 (d, J=16.0 Hz, 1H), 4.33 (q, J=7.2 Hz, 2H), 1.37 (t, J=7.2 Hz, 3H).

Step 3: ethyl 3-[2-fluoro-5-nitro-3-(trifluoromethyl)phenyl]propanoate

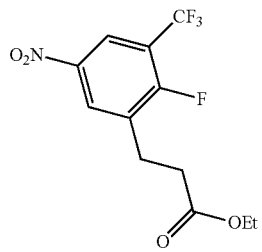 [SMILES: CCOC(=O)CCc1cc([N+](=O)[O-])cc(C(F)(F)F)c1F]

To a solution of ethyl (2E)-3-[2-fluoro-5-nitro-3-(trifluoromethyl)phenyl]prop-2-enoate (8.00 g, 26.0 mmol) in EtOH (200 mL) was added chlorotris(triphenylphosphine)rhodium(I) (1.20 g, 1.30 mmol). The suspension was degassed and purged with $H_2$ (3×). The mixture was stirred under $H_2$ (15 psi) at room temperature for 1 h. Solids were removed by filtration and the filtrate was concentrated in vacuo. The residue was purified by flash silica gel chromatography (Biotage 12 g cartridge, 0-8% EtOAc/Petroleum ether) to provide ethyl 3-[2-fluoro-5-nitro-3-(trifluoromethyl)phenyl]propanoate. $^1$H NMR (400 MHz, DMSO-$d_6$): δ 8.42 (s, 1H), 8.41 (s 1H), 4.19-4.13 (m, 2H), 3.13 (t, J=7.2 Hz, 2H), 2.73 (t, J=7.2 Hz, 2H), 1.26 (t, J=7.2 Hz, 3H).

Step 4: ethyl 3-(5-nitro-2-{[(cis)-3-hydroxy-3-methylcyclobutyl]amino}-3-(trifluoromethyl)phenyl)propanoate

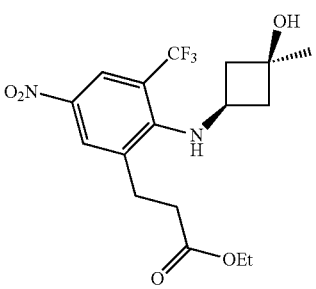 [SMILES: CCOC(=O)CCc1cc([N+](=O)[O-])cc(C(F)(F)F)c1N[C@H]1C[C@@](C)(O)C1]

To a solution of ethyl 3-[2-fluoro-5-nitro-3-(trifluoromethyl)phenyl]propanoate (7.00 g, 22.6 mmol) in DMSO (100 mL) was added (cis)-3-amino-1-methylcyclobutan-1-ol (3.43 g, 24.9 mmol, HCl salt) and DIEA (11.8 mL, 67.9 mmol). The mixture was stirred at 80° C. for 12 h. After cooling to room temperature, the reaction mixture was quenched by addition of $H_2O$ (80 mL) and extracted with EtOAc (3×80 mL). The combined organic layers were washed with brine (150 mL), dried over anhydrous $Na_2SO_4$, filtered, and concentrated in vacuo. The residue was purified by flash silica gel chromatography (Biotage 40 g cartridge, 0-10% EtOAc/Petroleum ether) to provide ethyl 3-(5-nitro-2-{[(cis)-3-hydroxy-3-methylcyclobutyl]amino}-3-(trifluoromethyl)phenyl)propanoate. MS=391.1 [M+H]$^+$.

Step 5: 6-nitro-1-[(cis)-3-hydroxy-3-methylcyclobutyl]-8-(trifluoromethyl)-1,2,3,4-tetrahydroquinolin-2-one

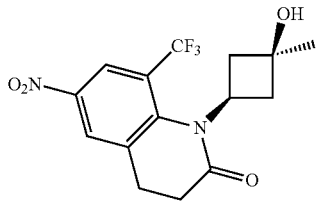 [SMILES: C[C@]1(O)C[C@@H](N2C(=O)CCc3cc([N+](=O)[O-])cc(C(F)(F)F)c32)C1]

To a solution of ethyl 3-(5-nitro-2-{[(cis)-3-hydroxy-3-methylcyclobutyl]amino}-3-(trifluoromethyl)phenyl)propanoate (7.00 g, 17.9 mmol) in DMF (80 mL) and MeOH (10 mL) was added $K_2CO_3$ (7.44 g, 53.8 mmol). The mixture was stirred at 80° C. for 12 h. After cooling to room temperature, the reaction mixture was quenched by addition of $H_2O$ (100 mL) and extracted with EtOAc (3×100 mL). The combined organic layers were washed with brine (15 mL), dried over anhydrous $Na_2SO_4$, filtered, and concentrated in vacuo. The residue was purified by flash silica gel chromatography (Biotage 40 g cartridge, 10-27% EtOAc/Petroleum ether) to provide 6-nitro-1-[(cis)-3-hydroxy-3-methylcyclobutyl]-8-(trifluoromethyl)-1,2,3,4-tetrahydroquinolin-2-one. MS=345.1 $[M+H]^+$.

Step 6: 6-amino-1-[(cis)-3-hydroxy-3-methylcyclobutyl]-8-(trifluoromethyl)-1,2,3,4-tetrahydroquinolin-2-one

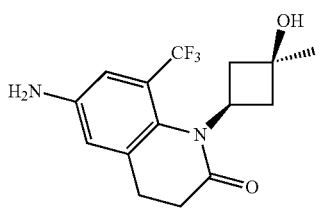

To a solution of 6-nitro-1-[(cis)-3-hydroxy-3-methylcyclobutyl]-8-(trifluoromethyl)-1,2,3,4-tetrahydroquinolin-2-one (3.00 g, 8.71 mmol) in EtOAc (60 mL) under $N_2$ atmosphere was added Pd/C (244 mg, 10 wt %, 0.231 mmol). The suspension was degassed and purged with $H_2$ (3×). The mixture was stirred under $H_2$ (15 psi) at room temperature for 12 h. Solids were removed by filtration, and the filtrate was concentrated in vacuo to provide 6-amino-1-[(cis)-3-hydroxy-3-methylcyclobutyl]-8-(trifluoromethyl)-1,2,3,4-tetrahydroquinolin-2-one, which was used in the subsequent step without further purification. MS=315.1 $[M+H]^+$.

Step 7: 1-[(cis)-3-hydroxy-3-methylcyclobutyl]-6-(4,4,5,5-tetramethyl-1,3,2-dioxaborolan-2-yl)-8-(trifluoromethyl)-1,2,3,4-tetrahydroquinolin-2-one

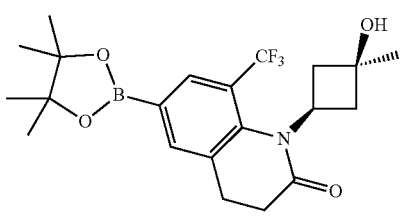

To a solution of 6-amino-1-[(cis)-3-hydroxy-3-methylcyclobutyl]-8-(trifluoromethyl)-1,2,3,4-tetrahydroquinolin-2-one (1.00 g, 3.18 mmol) in MeCN (10 mL) under $N_2$ atmosphere was added bis(pinacolato)diboron (970 mg, 3.82 mmol) and tert-butyl nitrite (492 mg, 4.77 mmol). The mixture was stirred at 80° C. for 2 h. After cooling to room temperature, the reaction mixture was quenched by addition of $H_2O$ (20 mL) and extracted with EtOAc (3×50 mL). The combined organic layers were dried over anhydrous $Na_2SO_4$, filtered, and concentrated in vacuo to give 1-[(cis)-3-hydroxy-3-methylcyclobutyl]-6-(4,4,5,5-tetramethyl-1,3,2-dioxaborolan-2-yl)-8-(trifluoromethyl)-1,2,3,4-tetrahydroquinolin-2-one, which was used in the subsequent step without further purification. MS=426.1 $[M+H]^+$.

Step 8: 6-hydroxy-1-[(cis)-3-hydroxy-3-methylcyclobutyl]-8-(trifluoromethyl)-1,2,3,4-tetrahydroquinolin-2-one

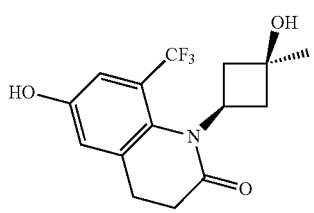 [SMILES: C[C@]1(O)C[C@@H](N2C(=O)CCc3cc(O)cc(C(F)(F)F)c32)C1]

To a solution of 1-[(cis)-3-hydroxy-3-methylcyclobutyl]-6-(4,4,5,5-tetramethyl-1,3,2-dioxaborolan-2-yl)-8-(trifluoromethyl)-1,2,3,4-tetrahydroquinolin-2-one (800 mg, 1.88 mmol) in THF (9 mL) and $H_2O$ (3 mL) was added Oxone (1.16 g, 1.88 mmol). The mixture was stirred at 0° C. for 1 h. The reaction mixture was quenched by addition of saturated aqueous $Na_2SO_3$ (20 mL) and extracted with EtOAc (3×20 mL). The combined organic layers were washed with brine (20 mL), dried over anhydrous $Na_2SO_4$, filtered, and concentrated in vacuo to give 6-hydroxy-1-[(cis)-3-hydroxy-3-methylcyclobutyl]-8-(trifluoromethyl)-1,2,3,4-tetrahydroquinolin-2-one (Intermediate A-110), which was used in the subsequent step without further purification. MS=316.0 $[M+H]^+$.

General Procedure for Intermediate A-111

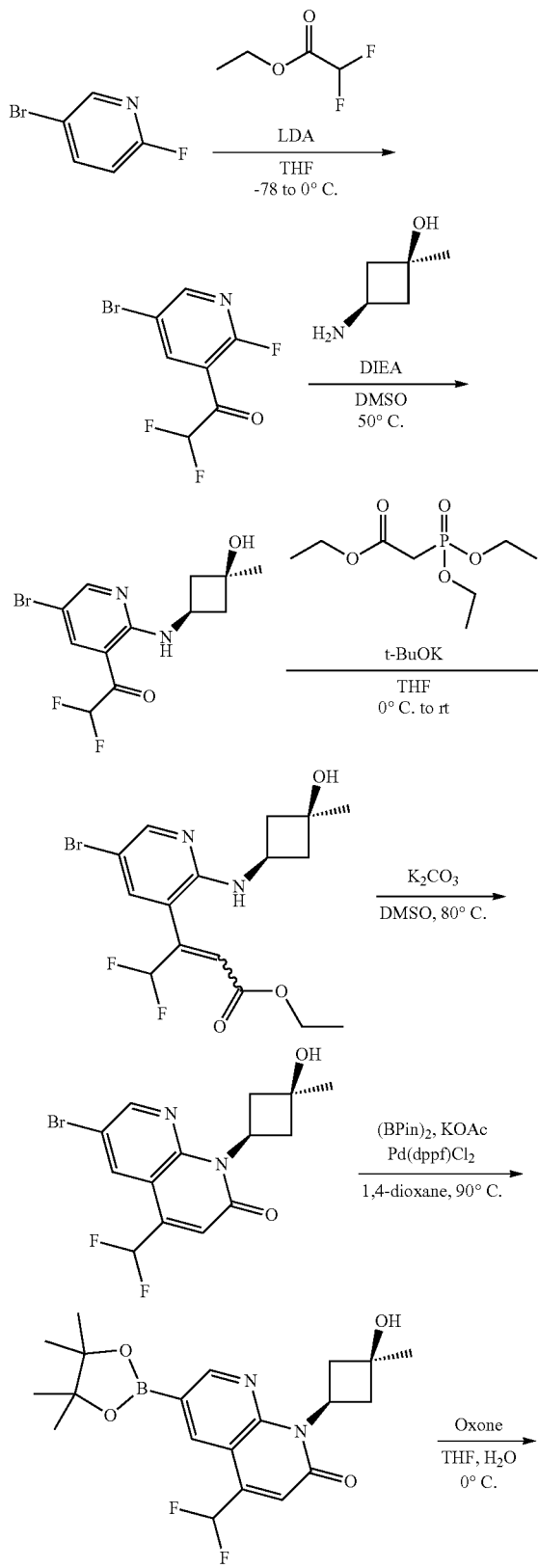

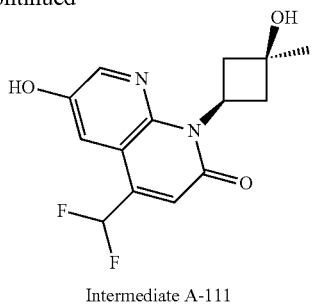

Intermediate A-111

Step 1: 1-(5-bromo-2-fluoropyridin-3-yl)-2,2-difluoroethan-1-one

To a −78° C. mixture of 5-bromo-2-fluoro-pyridine (2.92 mL, 28.4 mmol) in THF (45 mL) under $N_2$ atmosphere was added 2.0 M LDA in THF (17.1 mL, 34.1 mmol). The mixture was stirred at −78° C. for 30 min under $N_2$ atmosphere, then a solution of ethyl 2,2-difluoroacetate (5.29 g, 42.6 mmol) in THF (5 mL) was added dropwise. The mixture was stirred at −78° C. for another 2 h under $N_2$ atmosphere, then was warmed to 0° C. The reaction mixture was quenched by addition of saturated aqueous $NH_4Cl$ solution (50 mL) and then extracted with EtOAc (3×100 mL). The combined organic layers were dried over $Na_2SO_4$, filtered, and concentrated in vacuo. The residue was purified by flash silica gel chromatography (Biotage 40 g cartridge, 0-20% EtOAc/Petroleum ether) to provide 1-(5-bromo-2-fluoropyridin-3-yl)-2,2-difluoroethan-1-one. MS=272.0/273.9 $[M+H+H_2O]^+$.

Step 2: 1-(5-bromo-2-{[(cis)-3-hydroxy-3-methylcyclobutyl]amino}pyridin-3-yl)-2,2-difluoroethan-1-one To a solution of 1-(5-bromo-2-fluoropyridin-3-yl)-2,2-difluoroethan-1-one (1.80 g, 7.09 mmol) and (cis)-3-amino-1-methylcyclobutan-1-ol (1.07 g, 7.80 mmol, HCl salt) in DMSO (20 mL) was added DIEA (4.94 mL, 28.4 mmol). The mixture was stirred at 50° C. for 2 h, then was cooled to 0° C., quenched by addition of H₂O (20 mL), and extracted with EtOAc (3×20 mL). The combined organic layers were washed with brine (50 mL), dried over Na₂SO₄, filtered, and concentrated in vacuo. The residue was purified by flash silica gel chromatography (Biotage 20 g cartridge, 0-30% EtOAc/Petroleum ether) to provide 1-(5-bromo-2-{[(cis)-3-hydroxy-3-methylcyclobutyl]amino}pyridin-3-yl)-2,2-difluoroethan-1-one. MS=335.0/336.9 [M+H]⁺.

Step 3: ethyl 3-(5-bromo-2-{[(cis)-3-hydroxy-3-methylcyclobutyl]amino}pyridin-3-yl)-4,4-difluorobut-2-enoate

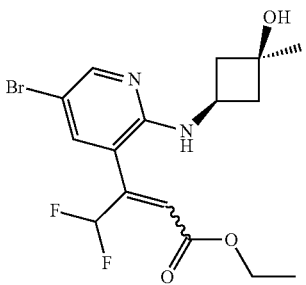 [SMILES: CCOC(=O)C=C(c1cc(Br)cnc1N[C@H]1C[C@@](C)(O)C1)C(F)F]

To a 0° C. mixture of ethyl 2-diethoxyphosphorylacetate (803 mg, 3.58 mmol) in THF (10 mL) was added t-BuOK (670 mg, 5.97 mmol). The mixture was allowed to warm to room temperature and stirred for 1 h, then cooled to 0° C. and a solution of 1-(5-bromo-2-{[(cis)-3-hydroxy-3-methylcyclobutyl]amino}pyridin-3-yl)-2,2-difluoroethan-1-one (1.00 g, 2.98 mmol) in THF (3 mL) was added dropwise. Then the mixture was stirred at 0° C. for 2 h, then was quenched by addition of H₂O (15 mL) and extracted with EtOAc (3×15 mL). The combined organic layers were washed with brine (50 mL), dried over Na₂SO₄, filtered and concentrated in vacuo. The residue was purified by flash silica gel chromatography (Biotage 20 g cartridge, 0-40% EtOAc/Petroleum ether) to provide ethyl 3-(5-bromo-2-{[(cis)-3-hydroxy-3-methylcyclobutyl]amino}pyridin-3-yl)-4,4-difluorobut-2-enoate. MS=405.0/407.0 [M+H]⁺.

Step 4: 6-bromo-4-(difluoromethyl)-1-[(cis)-3-hydroxy-3-methylcyclobutyl]-1,2-dihydro-1,8-naphthyridin-2-one

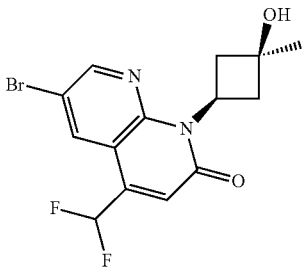 [SMILES: C[C@]1(O)C[C@@H](n2c(=O)cc(C(F)F)c3cc(Br)cnc32)C1]

To a mixture of ethyl 3-(5-bromo-2-{[(cis)-3-hydroxy-3-methylcyclobutyl]amino}pyridin-3-yl)-4,4-difluorobut-2-enoate (730 mg, 1.80 mmol) in DMSO (10 mL) was added K₂CO₃ (747 mg, 5.40 mmol). The mixture was stirred at 80° C. for 2. After cooling to room temperature, the reaction mixture was quenched by addition of H₂O (20 mL) and extracted with EtOAc (3×20 mL). The combined organic layers were dried over Na₂SO₄, filtered, and concentrated in vacuo. The residue was purified by flash silica gel chromatography (Biotage 12 g cartridge, 0-35% EtOAc/Petroleum ether) to provide 6-bromo-4-(difluoromethyl)-1-[(cis)-3-hydroxy-3-methylcyclobutyl]-1,2-dihydro-1,8-naphthyridin-2-one. MS=359.0/361.0 [M+H]⁺.

Step 5: 4-(difluoromethyl)-1-[(cis)-3-hydroxy-3-methylcyclobutyl]-6-(4,4,5,5-tetramethyl-1,3,2-dioxaborolan-2-yl)-1,2-dihydro-1,8-naphthyridin-2-one

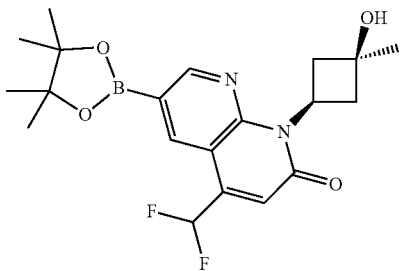

A mixture of 6-bromo-4-(difluoromethyl)-1-[(cis)-3-hydroxy-3-methylcyclobutyl]-1,2-dihydro-1,8-naphthyridin-2-one (300 mg, 835 μmol), bis(pinacolato)diboron (318 mg, 1.25 mmol), KOAc (205 mg, 2.09 mmol) and Pd(dppf)Cl₂·CH₂Cl₂ (34.1 mg, 41.8 μmol) in 1,4-dioxane (4 mL) was degassed and purged with N₂ (3×), and then stirred at 90° C. for 12 h under N₂ atmosphere. After cooling to room temperature, solids were removed by filtration and the filtrate was concentrated in vacuo to give 4-(difluoromethyl)-1-[(cis)-3-hydroxy-3-methylcyclobutyl]-6-(4,4,5,5-tetramethyl-1,3,2-dioxaborolan-2-yl)-1,2-dihydro-1,8-naphthyridin-2-one, which was used in the subsequent step without further purification.

Step 6: 4-(difluoromethyl)-6-hydroxy-1-[(cis)-3-hydroxy-3-methylcyclobutyl]-1,2-dihydro-1,8-naphthyridin-2-one

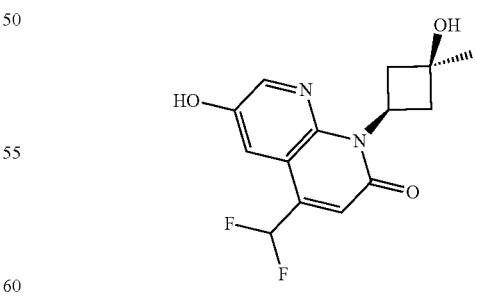

To a 0° C. solution of 4-(difluoromethyl)-1-[(cis)-3-hydroxy-3-methylcyclobutyl]-6-(4,4,5,5-tetramethyl-1,3,2-dioxaborolan-2-yl)-1,2-dihydro-1,8-naphthyridin-2-one (400 mg, 985 μmol) in THF (5 mL) and H₂O (2 mL) was added Oxone (424 mg, 689 μmol). The mixture was stirred at 0° C. for 1 h, and then was quenched with saturated aqueous Na₂SO₃ solution (20 mL) and extracted with EtOAc (3×30 mL). The combined organic layers were dried over Na₂SO₄, filtered, and concentrated in vacuo. The residue was purified by flash silica gel chromatography (Biotage 4 g cartridge, 0-40% EtOAc/Petroleum ether) to provide 4-(difluoromethyl)-6-hydroxy-1-[(cis)-3-hydroxy-3-methylcyclobutyl]-1,2-dihydro-1,8-naphthyridin-2-one (Intermediate A-111). MS=297.0 [M+H]⁺.

General Procedure for Intermediate A-112

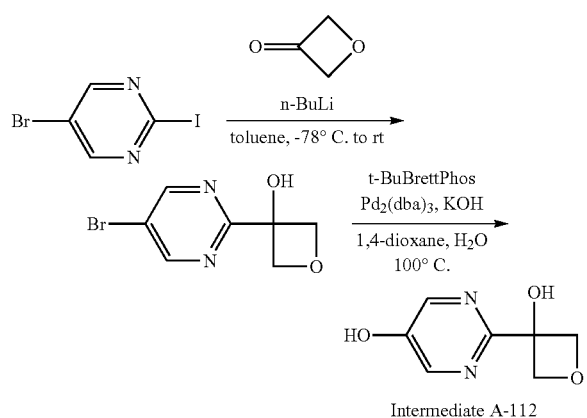

Intermediate A-112

Step 1: 3-(5-bromopyrimidin-2-yl)oxetan-3-ol

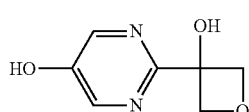

To a −78° C. mixture of 5-bromo-2-iodo-pyrimidine (5.00 g, 17.6 mmol) in toluene (40 mL) under N₂ atmosphere was added 2.5 M n-BuLi in n-hexane (7.37 mL, 18.4 mmol) dropwise. The mixture was stirred at −78° C. for 30 min under N₂ atmosphere and then a solution of oxetan-3-one (1.52 g, 21.1 mmol) in toluene (20 mL) was added dropwise. The resulting mixture was stirred at −78° C. for 30 min and then stirred at room temperature for 1 h. The reaction mixture was cooled to 0° C., quenched by addition of saturated aqueous NH₄Cl solution (50 mL), then extracted with EtOAc (3×50 mL). The combined organic layers were dried over Na₂SO₄, filtered, and concentrated in vacuo. The residue was purified by flash silica gel chromatography (Biotage 40 g cartridge, 100% EtOAc) to provide 3-(5-bromopyrimidin-2-yl)oxetan-3-ol. MS=231.0/233.0 [M+H]⁺.

Step 2: 2-(3-hydroxyoxetan-3-yl)pyrimidin-5-ol

A mixture of 3-(5-bromopyrimidin-2-yl)oxetan-3-ol (1.00 g, 4.33 mmol), Pd₂(dba)₃ (79.3 mg, 86.6 µmol), KOH (729 mg, 13.0 mmol) and ditert-butyl-[2,3,4,5-tetramethyl-6-(2,4,6-triisopropylphenyl)phenyl]phosphane (208 mg, 433 µmol) in 1,4-dioxane (10 mL) and H₂O (5 mL) was degassed and purged with N₂ (3×) and then stirred at 100° C. for 4 h under N₂ atmosphere. The reaction mixture was cooled to room temperature, quenched by addition of H₂O (20 mL), and then extracted with EtOAc (3×20 mL). The combined organic layers were dried over Na₂SO₄, filtered, and concentrated under reduced pressure. The residue was purified by flash silica gel chromatography (Biotage 25 g cartridge, 0-100% EtOAc/Petroleum ether) to provide 2-(3-hydroxyoxetan-3-yl)pyrimidin-5-ol (Intermediate A-112). MS=169.1 [M+H]⁺.

The following intermediates in Table 11.2 were prepared according to procedures analogous to those described for Intermediate A-112 using the appropriate starting materials or common intermediates.

General Procedure for Intermediate A-113

TABLE 11.2

| Intermediate | Structure | IUPAC Name | Exact Mass [M + H]⁺ |
|---|---|---|---|
| A-113 | 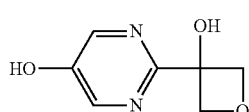 | 2-(1-hydroxycyclobutyl)pyrimidin-5-ol | Calc'd 167.1 Found 167.1 |

General Procedure for Intermediate A-114

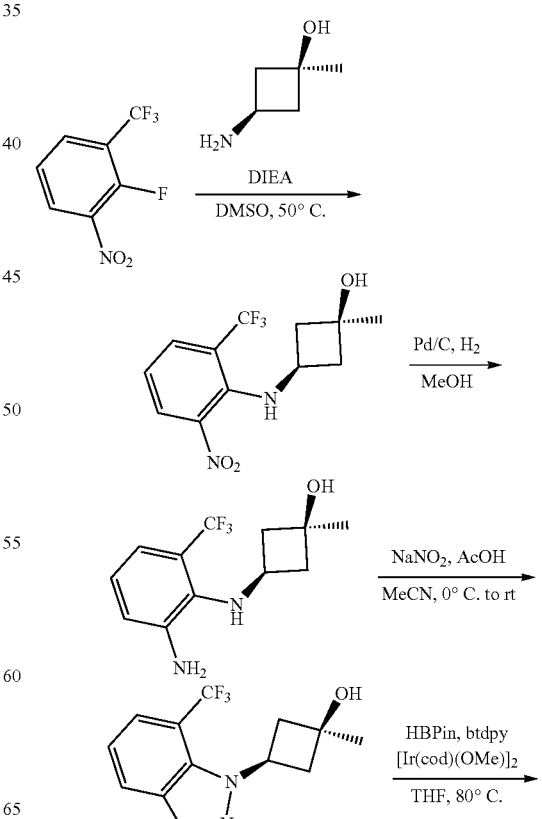

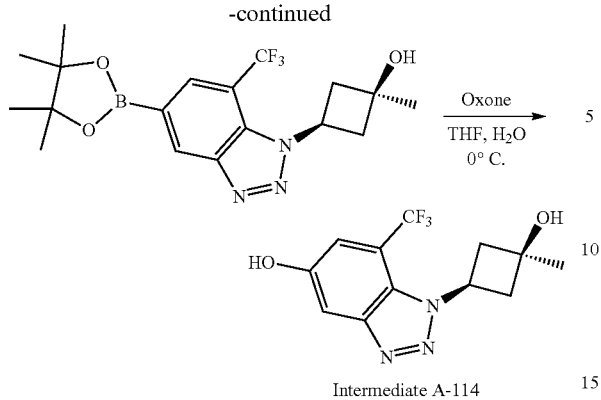

Intermediate A-114

Step 1: (cis)-1-methyl-3-{[2-nitro-6-(trifluoromethyl)phenyl]amino}cyclobutan-1-ol

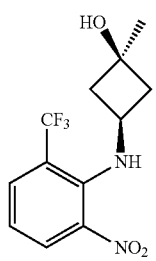 [SMILES: C[C@]1(O)C[C@@H](Nc2c([N+](=O)[O-])cccc2C(F)(F)F)C1]

A mixture of 2-fluoro-1-nitro-3-(trifluoromethyl)benzene (1.50 g, 7.17 mmol), DIEA (3.71 g, 28.7 mmol) and (cis)-3-amino-1-methylcyclobutan-1-ol (1.09 g, 7.89 mmol, HCl salt) in DMSO (15 mL) was stirred at 50° C. for 2 h. After cooling to room temperature, the reaction mixture was poured into H$_2$O (50 mL). The mixture was extracted with EtOAc (3×60 mL). The combined organic layers were washed with brine (2×40 mL), dried over Na$_2$SO$_4$, filtered and concentrated under reduced pressure to give (cis)-1-methyl-3-{[2-nitro-6-(trifluoromethyl)phenyl]amino}cyclobutan-1-ol, which was taken to the next step without further purification. MS=290.9 [M+H]$^+$.

Step 2: (cis)-3-amino-1-methylcyclobutan-1-ol

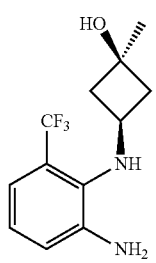 [SMILES: C[C@]1(O)C[C@@H](Nc2c(N)cccc2C(F)(F)F)C1]

To a mixture of Pd/C (4.00 g, 10 wt %, 3.78 mmol) in MeOH (100 mL) was added (cis)-1-methyl-3-{[2-nitro-6-(trifluoromethyl)phenyl]amino}cyclobutan-1-ol (6.00 g, 20.67 mmol). The mixture was stirred at room temperature for 2 h under H$_2$ (15 psi) atmosphere. The mixture was filtered and the filtrate was concentrated in vacuo to give (cis)-3-amino-1-methylcyclobutan-1-ol, which was taken to the next step without further purification MS=261.0 [M+H]$^+$.

Step 3: (cis)-1-methyl-3-[7-(trifluoromethyl)-1H-1,2,3-benzotriazol-1-yl]cyclobutan-1-ol

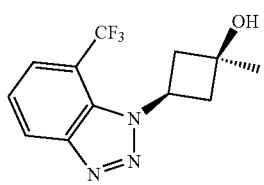 [SMILES: C[C@]1(O)C[C@@H](n2nnc3cccc(C(F)(F)F)c32)C1]

To a 0° C. mixture of 3-[2-amino-6-(trifluoromethyl)anilino]-1-methyl-cyclobutanol (2.00 g, 7.68 mmol) in AcOH (4 mL) and MeCN (20 mL) was added NaNO$_2$ (1.06 g, 15.4 mmol). The mixture was allowed to warm to room temperature and stirred for 16 h. The mixture was diluted with saturated NaHCO$_3$ solution (100 mL) and extracted with EtOAc (2×50 mL). The combined organic layers were dried over Na$_2$SO$_4$, filtered, and concentrated in vacuo to give (cis)-1-methyl-3-[7-(trifluoromethyl)-1H-1,2,3-benzotriazol-1-yl]cyclobutan-1-ol, which was used in the subsequent step without further purification. MS=272.0 [M+H]$^+$.

Step 4: (cis)-1-methyl-3-[5-(4,4,5,5-tetramethyl-1,3,2-dioxaborolan-2-yl)-7-(trifluoromethyl)-1H-1,2,3-benzotriazol-1-yl]cyclobutan-1-ol

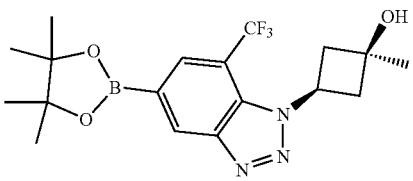

A mixture of (cis)-1-methyl-3-[7-(trifluoromethyl)-1H-1,2,3-benzotriazol-1-yl]cyclobutan-1-ol (2.30 g, 8.48 mmol), pinacolborane (12.3 mL, 84.8 mmol), 4,4-di-tert-butyl-2,2'-dipyridine (228 mg, 0.848 mmol) and (1,5-cyclooctadiene)(methoxy)iridium(I) dimer (281 mg, 0.424 mmol) in THF (30 mL) was degassed with N$_2$ for 10 min, and then stirred at 80° C. for 16 h under N$_2$ atmosphere. After cooling to room temperature, the reaction was filtered and the filtrate was concentrated in vacuo to give (cis)-1-methyl-3-[5-(4,4,5,5-tetramethyl-1,3,2-dioxaborolan-2-yl)-7-(trifluoromethyl)-1H-1,2,3-benzotriazol-1-yl]cyclobutan-1-ol, which was used in the next step without further purification.

Step 5: 1-[(cis)-3-hydroxy-3-methylcyclobutyl]-7-(trifluoromethyl)-1H-1,2,3-benzotriazol-5-ol

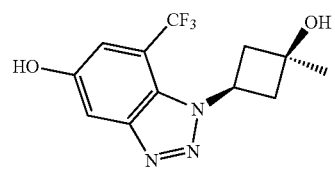 [SMILES: C[C@]1(O)C[C@@H](n2nnc3cc(O)cc(C(F)(F)F)c32)C1]

To a 0° C. solution of (cis)-1-methyl-3-[5-(4,4,5,5-tetramethyl-1,3,2-dioxaborolan-2-yl)-7-(trifluoromethyl)-1H-1,2,3-benzotriazol-1-yl]cyclobutan-1-ol (3.3 g, 8.31 mmol) in THF (20 mL) and H₂O (10 mL) was added Oxone (15.3 g, 24.9 mmol). The mixture was stirred at 0° C. for 2 h. The mixture was quenched with saturated aqueous Na₂SO₃ solution. The mixture was extracted with chloroform (3×30 mL). The combined organic layers were washed with brine (2×50 mL), dried over Na₂SO₄, filtered, and concentrated in vacuo. The residue was purified by flash silica gel chromatography (Biotage 40 g cartridge, 0-60% EtOAc/Petroleum ether) to provide 1-[(cis)-3-hydroxy-3-methylcyclobutyl]-7-(trifluoromethyl)-1H-1,2,3-benzotriazol-5-ol (Intermediate A-114). MS=288.0 [M+H]⁺.

General Procedure for Intermediate A-115

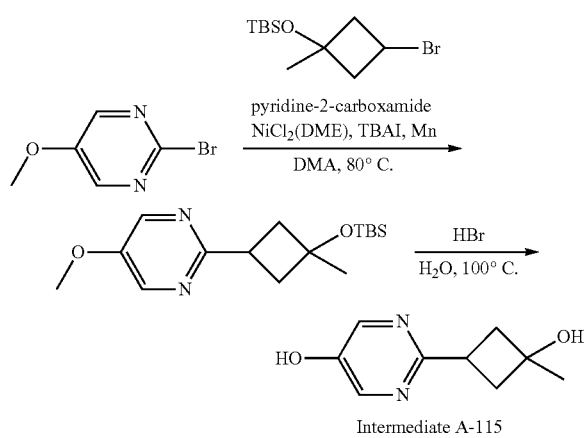

Intermediate A-115

Step 1: 2-{3-[(tert-butyldimethylsilyl)oxy]-3-methylcyclobutyl}-5-methoxypyrimidine

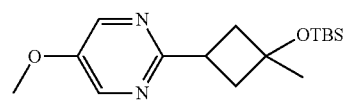

In a glove box, to a vial equipped with a magnetic stir bar was added 2-bromo-5-methoxypyrimidine (1.00 g, 5.30 mmol) and (3-bromo-1-methyl-cyclobutoxy)-tert-butyl-dimethyl-silane (7.40 g, 26.5 mmol) in DMA (80 mL). To the mixture was added manganese (3.49 g, 63.5 mmol), pyridine-2-carboxamidine hydrochloride (2.50 g, 15.9 mmol), TBAI (1.35 g, 3.65 mmol) and dichloro(dimethoxyethane) nickel (872 mg, 3.97 mmol). The reaction was purged with Ar for 10 min, and then stirred at 80° C. for 12 h. After cooling to room temperature, the reaction mixture was quenched with H₂O (50 mL) and filtered to remove solids. The filtrate was extracted with EtOAc (3×50 mL). The combined organic layers were washed with brine (50 mL), dried over Na₂SO₄, filtered, and concentrated in vacuo. The residue was purified by flash silica gel chromatography (Biotage 40 g cartridge, 0-25% EtOAc/Petroleum ether) to provide 2-{3-[(tert-butyldimethylsilyl)oxy]-3-methylcyclobutyl}-5-methoxypyrimidine. MS=309.4 [M+H]⁺.

Step 2: 2-(3-hydroxy-3-methylcyclobutyl)pyrimidin-5-ol

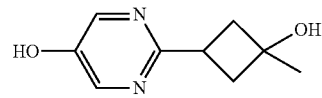

To a solution of 2-{3-[(tert-butyldimethylsilyl)oxy]-3-methylcyclobutyl}-5-methoxypyrimidine (350 mg, 1.13 mmol) in H₂O (7 mL) was added HBr (7.00 mL, 51.6 mmol). The mixture was stirred at 100° C. for 30 h. After cooling to room temperature, the reaction mixture was quenched by addition of saturated aqueous NaHCO₃ solution (15 mL), then extracted with EtOAc (3×20 mL). The combined organic layers were concentrated in vacuo. The residue was purified by reverse phase preparative HPLC (Phenomenex Luna C₁₈ column, 1-20% MeCN: 10 mM TFA in H₂O) to provide 2-(3-hydroxy-3-methylcyclobutyl)pyrimidin-5-ol (Intermediate A-115). MS=181.0 [M+H]⁺.

General Procedure for Intermediate A-116

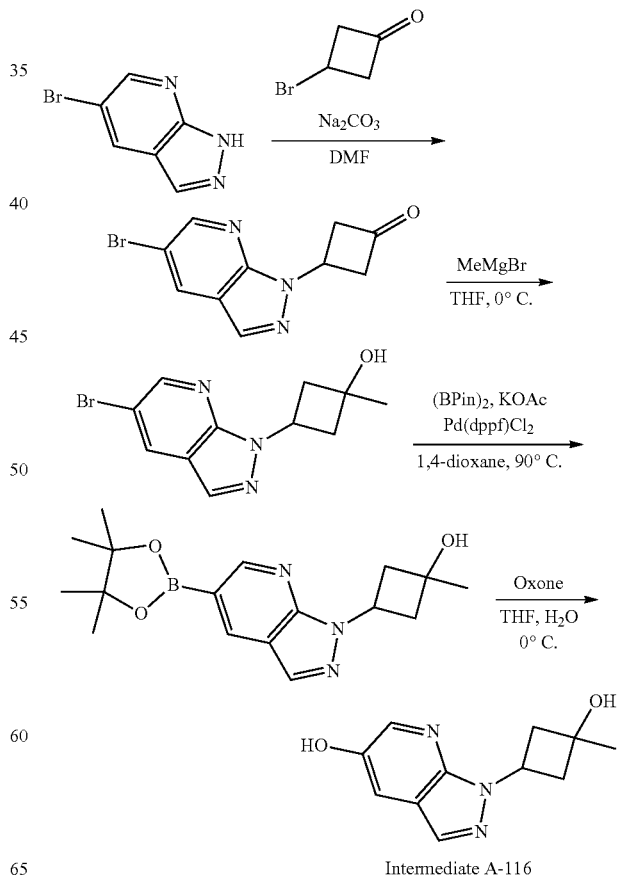

Intermediate A-116

Step 1: 3-{5-bromo-1H-pyrazolo[3,4-b]pyridin-1-yl}cyclobutan-1-one

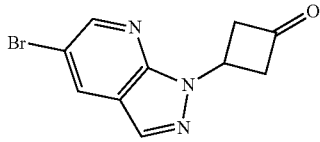 [SMILES: O=C1CC(n2ncc3cc(Br)cnc32)C1]

To a solution of 5-bromo-1H-pyrazolo[3,4-b]pyridine (5.00 g, 25.3 mmol) in DMF (45 mL) was added $Na_2CO_3$ (5.35 g, 50.5 mmol). The mixture was stirred at room temperature for 10 min, and then a solution 3-bromocyclobutanone (8.28 g, 55.6 mmol) in DMF (5 mL) was added dropwise by syringe pump over 2 h. The resulting mixture was stirred at room temperature for 3 h, then was quenched by addition of $H_2O$ (50 mL), and extracted with EtOAc (3×50 mL). The combined organic layers were washed with brine (2×50 mL), dried over $Na_2SO_4$, filtered, and concentrated in vacuo. The residue was purified by flash silica gel chromatography (Biotage 80 g cartridge, 0-100% EtOAc/Petroleum ether) to provide 3-{5-bromo-1H-pyrazolo[3,4-b]pyridin-1-yl}cyclobutan-1-one ($1^{st}$ eluting isomer). MS=266.0/268.0 $[M+H]^+$.

Step 2: 3-{5-bromo-1H-pyrazolo[3,4-b]pyridin-1-yl}-1-methylcyclobutan-1-ol

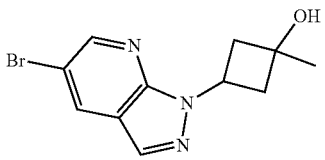 [SMILES: CC1(O)CC(n2ncc3cc(Br)cnc32)C1]

To a 0° C. solution of 3-(5-bromopyrazolo[3,4-b]pyridin-1-yl)cyclobutanone (400 mg, 1.50 mmol) in THF (4 mL) under $N_2$ atmosphere was added 3.0 M MeMgBr in THF (0.55 mL, 1.65 mmol) dropwise. The mixture was stirred at 0° C. for 3 h under $N_2$ atmosphere. The reaction mixture was quenched by addition of saturated aqueous $NH_4Cl$ solution (15 mL) and extracted with EtOAc (3×10 mL). The combined organic layers were dried over $Na_2SO_4$, filtered, and concentrated in vacuo. The residue was purified by flash silica gel chromatography (Biotage 40 g cartridge, 0-25% EtOAc/Petroleum ether) to provide 3-{5-bromo-1H-pyrazolo[3,4-b]pyridin-1-yl}-1-methylcyclobutan-1-ol. MS=282.0/284.0 $[M+H]^+$.

Step 3: 1-methyl-3-[5-(4,4,5,5-tetramethyl-1,3,2-dioxaborolan-2-yl)-1H-pyrazolo[3,4-b]pyridin-1-yl]cyclobutan-1-ol

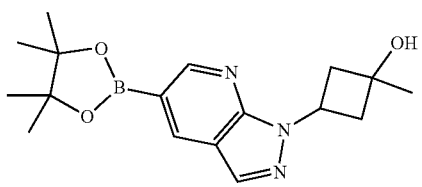

A mixture of 3-{5-bromo-1H-pyrazolo[3,4-b]pyridin-1-yl}-1-methylcyclobutan-1-ol (170 mg, 0.603 mmol), bis(pinacolato)diboron (184 mg, 0.723 mmol), KOAc (148 mg, 1.51 mmol), $Pd(dppf)Cl_2 \cdot CH_2Cl_2$ (49.1 mg, 60.3 μmol) in 1,4-dioxane (3.3 mL) was degassed and purged with $N_2$ (3×), and then the mixture was stirred at 90° C. for 12 h under $N_2$ atmosphere. The reaction mixture was allowed to cool to room temperature, then was diluted with $H_2O$ (10 mL) and extracted with EtOAc (3×10 mL). The combined organic layers were washed with brine (20 mL), dried over $Na_2SO_4$, filtered, and concentrated in vacuo to provide 1-methyl-3-[5-(4,4,5,5-tetramethyl-1,3,2-dioxaborolan-2-yl)-1H-pyrazolo[3,4-b]pyridin-1-yl]cyclobutan-1-ol, which was used in the subsequent step without further purification. MS=330.2 $[M+H]^+$.

Step 4. 1-(3-hydroxy-3-methylcyclobutyl)-1H-pyrazolo[3,4-b]pyridin-5-ol

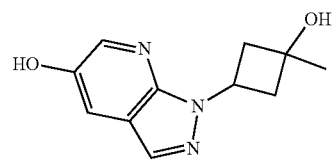

To a 0° C. solution of 1-methyl-3-[5-(4,4,5,5-tetramethyl-1,3,2-dioxaborolan-2-yl)-1H-pyrazolo[3,4-b]pyridin-1-yl]cyclobutan-1-ol (330 mg, 1.00 mmol) in THF (5 mL) and $H_2O$ (2.5 mL) was added Oxone (616 mg, 1.00 mmol). The mixture was stirred at 0° C. for 1 h, then was quenched by addition of saturated aqueous $Na_2SO_3$ solution. The mixture was extracted with chloroform (3×30 mL). The combined organic layers were washed with brine (50 mL), dried over $Na_2SO_4$, filtered, and concentrated in vacuo. The residue was purified by flash silica gel chromatography (Biotage 4 g cartridge, 0-60% EtOAc/Petroleum ether) to provide 1-(3-hydroxy-3-methylcyclobutyl)-1H-pyrazolo[3,4-b]pyridin-5-ol (Intermediate A-116). MS=220.1 $[M+H]^+$.

General Procedure for Intermediate A-117

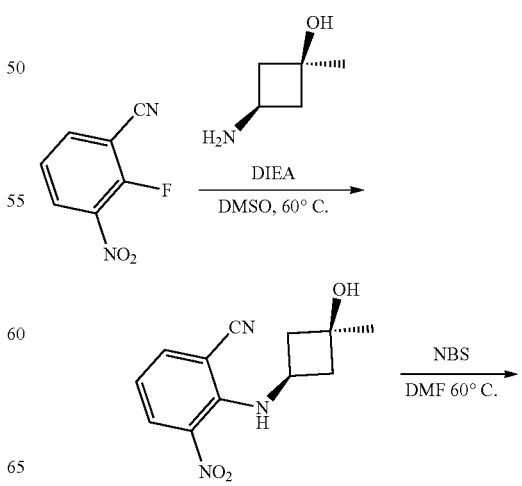

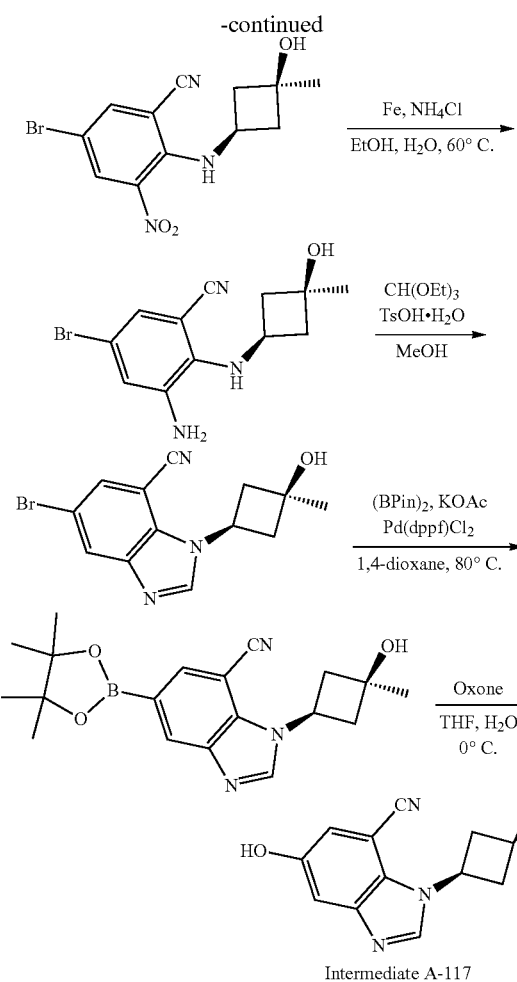

Intermediate A-117

Step 1: 3-nitro-2-{[(cis)-3-hydroxy-3-methylcyclobutyl]amino}benzonitrile

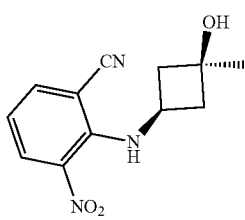 [SMILES: C[C@]1(O)C[C@@H](Nc2c(C#N)cccc2[N+](=O)[O-])C1]

To a solution of 2-fluoro-3-nitro-benzonitrile (2.50 g, 15.1 mmol) in DMSO (25 mL) was added DIEA (7.86 mL, 45.2 mmol) and (cis)-3-amino-1-methylcyclobutan-1-ol (1.67 g, 16.6 mmol). The mixture was stirred at 60° C. for 1 h. After cooling to room temperature, the mixture was diluted with H₂O (30 mL), filtered, and concentrated in vacuo to give 3-nitro-2-{[(cis)-3-hydroxy-3-methylcyclobutyl] amino}benzonitrile, which was used in the subsequent step without further purification. MS=248.3 [M+H]⁺.

Step 2: 5-bromo-3-nitro-2-{[(cis)-3-hydroxy-3-methylcyclobutyl]amino}benzonitrile

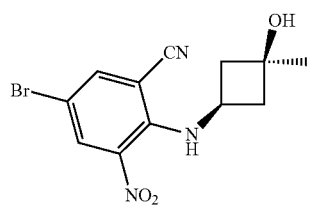

To a solution of 3-nitro-2-{[(cis)-3-hydroxy-3-methylcyclobutyl]amino}benzonitrile (2.50 g, 10.1 mmol) in DMF (25 mL) was added NBS (3.60 g, 20.2 mmol). The mixture was stirred at 60° C. for 16 h. After cooling to room temperature, the mixture was diluted with H₂O (30 mL) and extracted with EtOAc (2×20 mL). The combined organic layers were dried over Na₂SO₄, filtered, and concentrated in vacuo. The residue was purified by flash silica gel chromatography (Biotage 40 g cartridge, 0-15% EtOAc/Petroleum ether) to provide 5-bromo-3-nitro-2-{[(cis)-3-hydroxy-3-methylcyclobutyl]amino}benzonitrile.

Step 3: 5-bromo-3-nitro-2-{[(cis)-3-hydroxy-3-methylcyclobutyl]amino}benzonitrile

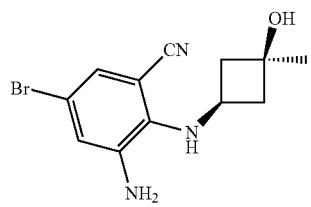 [SMILES: C[C@]1(O)C[C@@H](Nc2c(C#N)cc(Br)cc2[N+](=O)[O-])C1]

To a solution of 5-bromo-3-nitro-2-{[(cis)-3-hydroxy-3-methylcyclobutyl]amino}benzonitrile (2.00 g, 6.13 mmol) in EtOH (20 mL) and H₂O (10 mL) was added Fe (3.42 g, 61.3 mmol) and NH₄Cl (4.92 g, 92.0 mmol). The mixture was stirred at 60° C. for 2 h. After cooling to room temperature, solids were removed by filtration. The filtrate was diluted with H₂O (30 mL) and extracted with EtOAc (2×20 mL). The combined organic layers were dried over Na₂SO₄, filtered, and concentrated in vacuo to give 5-bromo-3-nitro-2-{[(cis)-3-hydroxy-3-methylcyclobutyl] amino}benzonitrile, which was used in the subsequent step without further purification. MS=295.9/297.9 [M+H]⁺.

Step 4: 5-bromo-1-[(cis)-3-hydroxy-3-methylcyclobutyl]-1H-1,3-benzodiazole-7-carbonitrile

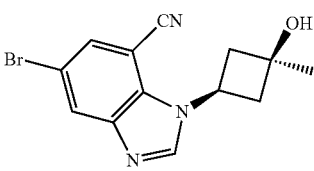 [SMILES: C[C@]1(O)C[C@@H](n2cnc3cc(Br)cc(C#N)c32)C1]

To a solution of 5-bromo-3-nitro-2-{[(cis)-3-hydroxy-3-methylcyclobutyl]amino}benzonitrile (1.80 g, 6.08 mmol)

in MeOH (15 mL) was added triethyl orthoformate (3.03 mL, 18.23 mmol) and TsOH·H₂O (116 mg, 0.608 mmol). The mixture was stirred at room temperature for 16 h. The mixture was diluted with H₂O (30 mL) and extracted with EtOAc (2×20 mL). The combined organic layers were dried over Na₂SO₄, filtered, and concentrated in vacuo. The residue was purified by flash silica gel chromatography (Biotage 40 g cartridge, 0-70% EtOAc/Petroleum ether) to provide 5-bromo-1-[(cis)-3-hydroxy-3-methylcyclobutyl]-1H-1,3-benzodiazole-7-carbonitrile. MS=305.8/307.9 [M+H]⁺.

Step 5: 1-[(cis)-3-hydroxy-3-methylcyclobutyl]-5-(4,4,5,5-tetramethyl-1,3,2-dioxaborolan-2-yl)-1H-1,3-benzodiazole-7-carbonitrile

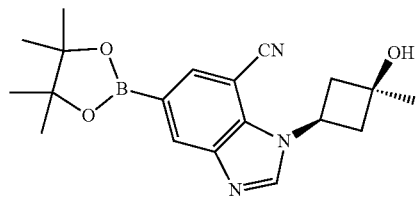

To a solution of 5-bromo-1-[(cis)-3-hydroxy-3-methylcyclobutyl]-1H-1,3-benzodiazole-7-carbonitrile (1.15 g, 3.76 mmol) in 1,4-dioxane (20 mL) was added bis(pinacolato)diboron (4.77 g, 18.8 mmol), KOAc (737 mg, 7.51 mmol), and Pd(dppf)Cl₂ (275 mg, 376 μmol). The mixture was degassed and purged with N₂ for 10 min, and then stirred at 80° C. for 16 h under N₂ atmosphere. After cooling to room temperature, solids were removed by filtration and the filtrate was concentrated in vacuo to give 1-[(cis)-3-hydroxy-3-methylcyclobutyl]-5-(4,4,5,5-tetramethyl-1,3,2-dioxaborolan-2-yl)-1H-1,3-benzodiazole-7-carbonitrile, which was used in the subsequent step without further purification.

Step 6: 5-hydroxy-1-[(cis)-3-hydroxy-3-methylcyclobutyl]-1H-1,3-benzodiazole-7-carbonitrile

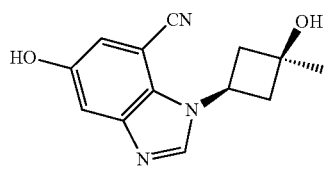 [SMILES: C[C@]1(O)C[C@@H](n2cnc3cc(O)cc(C#N)c32)C1]

To a 0° C. solution of 1-[(cis)-3-hydroxy-3-methylcyclobutyl]-5-(4,4,5,5-tetramethyl-1,3,2-dioxaborolan-2-yl)-1H-1,3-benzodiazole-7-carbonitrile (1.30 g, 3.68 mmol) in THF (10 mL) and H₂O (10 mL) was added Oxone (2.26 g, 3.68 mmol). The mixture was stirred at room temperature for 2 h, then was diluted with H₂O (30 mL) and extracted with EtOAc (2×20 mL). The combined organic layers were dried over Na₂SO₄, filtered, and concentrated in vacuo. The residue was purified by flash silica gel chromatography (Biotage 20 g cartridge, 0-80% EtOAc/Petroleum ether) to provide 5-hydroxy-1-[(cis)-3-hydroxy-3-methylcyclobutyl]-1H-1,3-benzodiazole-7-carbonitrile (Intermediate A-117). MS=244.0 [M+H]⁺.

General Procedure for Intermediate A-118

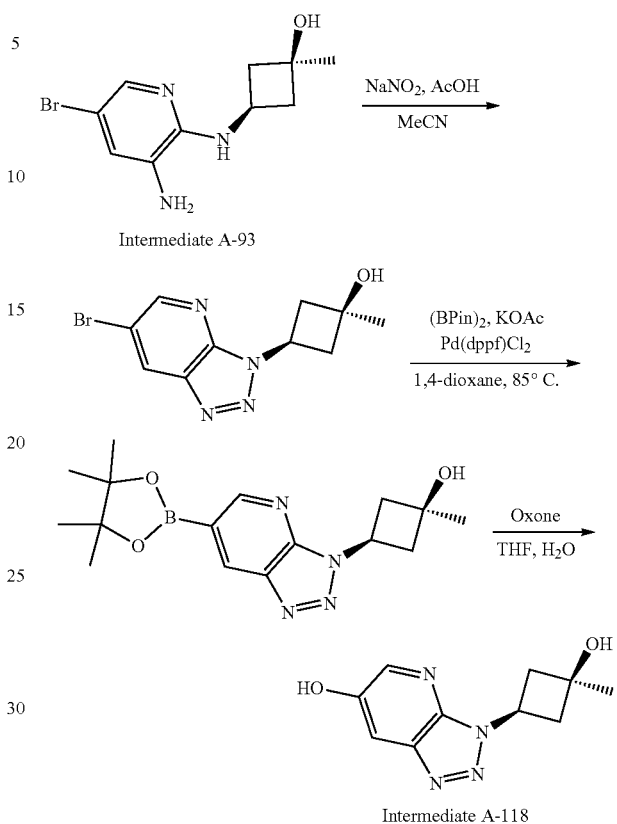

Intermediate A-118

Step 1: (cis)-3-{6-bromo-3H-[1,2,3]triazolo[4,5-b]pyridin-3-yl}-1-methylcyclobutan-1-ol

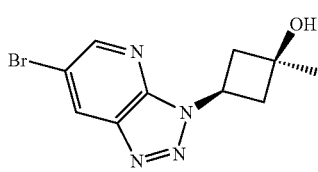 [SMILES: C[C@]1(O)C[C@@H](n2nnc3cc(Br)cnc32)C1]

To a solution of (cis)-3-[(3-amino-5-bromopyridin-2-yl)amino]-1-methylcyclobutan-1-ol (Intermediate A-93, 1.00 g, 3.67 mmol) in AcOH (10 mL) and MeCN (3 mL) was added NaNO₂ (507 mg, 7.35 mmol). The mixture was stirred at room temperature for 3 h. The mixture was diluted with H₂O (30 mL) and extracted with EtOAc (2×20 mL). The combined organic layers were dried over Na₂SO₄, filtered, and concentrated in vacuo to give (cis)-3-{6-bromo-3H-[1,2,3]triazolo[4,5-b]pyridin-3-yl}-1-methylcyclobutan-1-ol, which was used in the subsequent step without further purification. MS=282.8/284.9 [M+H]⁺.

Step 2: (cis)-1-methyl-3-[6-(4,4,5,5-tetramethyl-1,3,2-dioxaborolan-2-yl)-3H-[1,2,3]triazolo[4,5-b]pyridin-3-yl]cyclobutan-1-ol

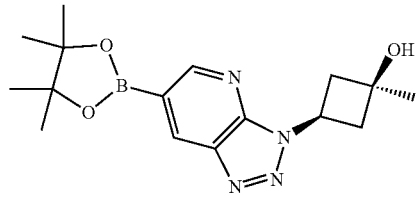

A mixture of (cis)-3-{6-bromo-3H-[1,2,3]triazolo[4,5-b]pyridin-3-yl}-1-methylcyclobutan-1-ol (400 mg, 1.41 mmol), bis(pinacolato)diboron (431 mg, 1.70 mmol), KOAc (277 mg, 2.83 mmol) and Pd(dppf)Cl$_2$ (103 mg, 141 μmol) in 1,4-dioxane (10 mL) was degassed and purged with N$_2$ for 10 min, and then stirred at 85° C. for 16 h. Solids were removed by filtration and the filtrate was concentrated in vacuo to give (cis)-1-methyl-3-[6-(4,4,5,5-tetramethyl-1,3,2-dioxaborolan-2-yl)-3H-[1,2,3]triazolo[4,5-b]pyridin-3-yl]cyclobutan-1-ol, which was taken to the next step without further purification.

Step 3: 3-[(cis)-3-hydroxy-3-methylcyclobutyl]-3H-[1,2,3]triazolo[4,5-b]pyridin-6-ol

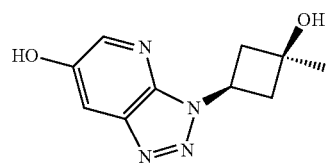 [SMILES: C[C@]1(O)C[C@@H](n2nnc3cc(O)cnc32)C1]

To a solution of (cis)-1-methyl-3-[6-(4,4,5,5-tetramethyl-1,3,2-dioxaborolan-2-yl)-3H-[1,2,3]triazolo[4,5-b]pyridin-3-yl]cyclobutan-1-ol (400 mg, 1.21 mmol) in THF (5 mL) and H$_2$O (5 mL) was added Oxone (745 mg, 1.21 mmol). The mixture was stirred at room temperature for 1 h, and then was concentrated in vacuo. The residue was purified by flash silica gel chromatography (Biotage 12 g cartridge, 0-85% EtOAc/Petroleum ether) to provide 3-[(cis)-3-hydroxy-3-methylcyclobutyl]-3H-[1,2,3]triazolo[4,5-b]pyridin-6-ol (Intermediate A-118). MS=221.2 [M+H]$^+$.

General Procedure for Intermediate A-119

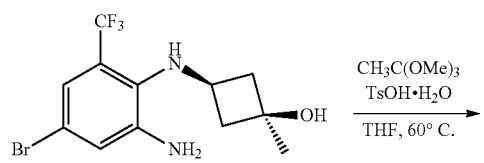

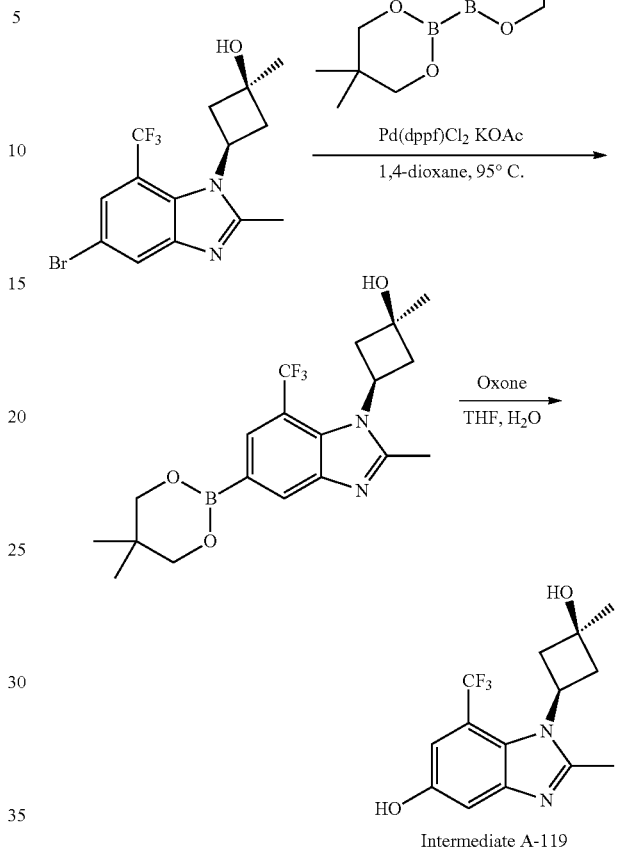

Intermediate A-119

Step 1: (cis)-3-(5-bromo-2-methyl-7-(trifluoromethyl)-1H-benzo[d]imidazol-1-yl)-1-methylcyclobutan-1-ol

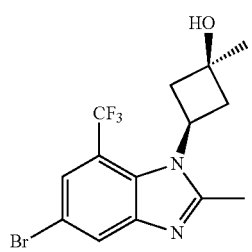 [SMILES: Cc1nc2cc(Br)cc(C(F)(F)F)c2n1[C@H]1C[C@@](C)(O)C1]

To a solution of (cis)-3-{[2-amino-4-bromo-6-(trifluoromethyl)phenyl]amino}-1-methylcyclobutan-1-ol (General procedure for Intermediate A-92, Step 3, 2.00 g, 5.90 mmol) and 1,1,1-trimethoxyethane (2.13 g, 17.7 mmol) in THF (30 mL) was added TsOH·H$_2$O (112 mg, 589 μmol). The mixture was stirred at 60° C. for 16 h. The mixture was diluted with H$_2$O (30 mL) and extracted with EtOAc (3×40 mL). The combined organic layers were washed with brine (50 mL), dried over Na$_2$SO$_4$, filtered, and concentrated under reduced pressure. The residue was purified by flash silica gel chromatography (Biotage 40 g cartridge, 0-50% EtOAc/Petroleum ether) to give (cis)-3-(5-bromo-2-methyl-7-(trifluoromethyl)-1H-benzo[d]imidazol-1-yl)-1-methylcyclobutan-1-ol. MS=363.0/365.0 [M+H]⁺.

Step 2: (cis)-3-(5-(5,5-dimethyl-1,3,2-dioxaborinan-2-yl)-2-methyl-7-(trifluoromethyl)-1H-benzo[d]imidazole-1-yl)-1-methylcyclobutan-1-ol

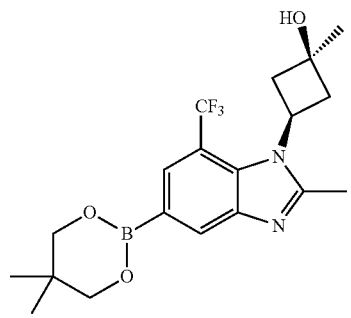

A mixture of (cis)-3-(5-bromo-2-methyl-7-(trifluoromethyl)-1H-benzo[d]imidazole-1-yl)-1-methylcyclobutan-1-ol (2.00 g, 5.51 mmol), 2-(5,5-dimethyl-1,3,2-dioxaborinan-2-yl)-5,5-dimethyl-1,3,2-dioxaborinane (2.49 g, 11.0 mmol), Pd(dppf)Cl₂ (403 mg, 551 μmol) and KOAc (1.62 g, 16.5 mmol) in 1,4-dioxane (30 mL) was degassed and purged with N₂ (3×), and then the mixture was stirred at 95° C. for 16 h under N₂ atmosphere. After cooling to room temperature, the mixture was diluted with H₂O (30 mL) and extracted with EtOAc (3×40 mL). The combined organic layers were washed with brine (50 mL), dried over Na₂SO₄, filtered, and concentrated under reduced pressure. The residue was purified by flash silica gel chromatography (Biotage 40 g cartridge, 70-85% EtOAc/Petroleum ether) to give (cis)-3-(5-(5,5-dimethyl-1,3,2-dioxaborinan-2-yl)-2-methyl-7-(trifluoromethyl)-1H-benzo[d]imidazol-1-yl)-1-methylcyclobutan-1-ol. MS=329.1 [M-C₅H₈+H]⁺.

Step 3: 1-((cis)-3-hydroxy-3-methylcyclobutyl)-2-methyl-7-(trifluoromethyl)-1H-benzo[d]imidazol-5-ol

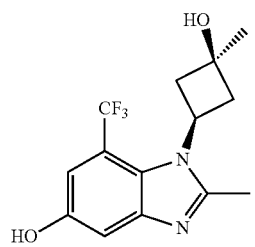 [SMILES: Cc1nc2cc(O)cc(C(F)(F)F)c2n1[C@H]1C[C@@](C)(O)C1]

To a solution of (cis)-3-(5-(5,5-dimethyl-1,3,2-dioxaborinan-2-yl)-2-methyl-7-(trifluoromethyl)-1H-benzo[d]imidazol-1-yl)-1-methylcyclobutan-1-ol (2.00 g, 6.10 mmol) in THF (30 mL) and H₂O (10 mL) was added Oxone (3.75 g, 6.10 mmol). The mixture was stirred at room temperature for 1 h. The reaction mixture was quenched with saturated aqueous Na₂SO₃ solution (30 mL) and extracted with EtOAc (3×30 mL). The combined organic layers were washed with brine (50 mL), dried over Na₂SO₄, filtered, and concentrated under reduced pressure. The residue was purified by flash silica gel chromatography (Biotage 40 g cartridge, 0-100% EtOAc/Petroleum ether) to give 1-((cis)-3-hydroxy-3-methylcyclobutyl)-2-methyl-7-(trifluoromethyl)-1H-benzo[d]imidazole-5-ol (Intermediate A-119). MS=301.1 [M+H]⁺.

General Procedure for Intermediate A-120

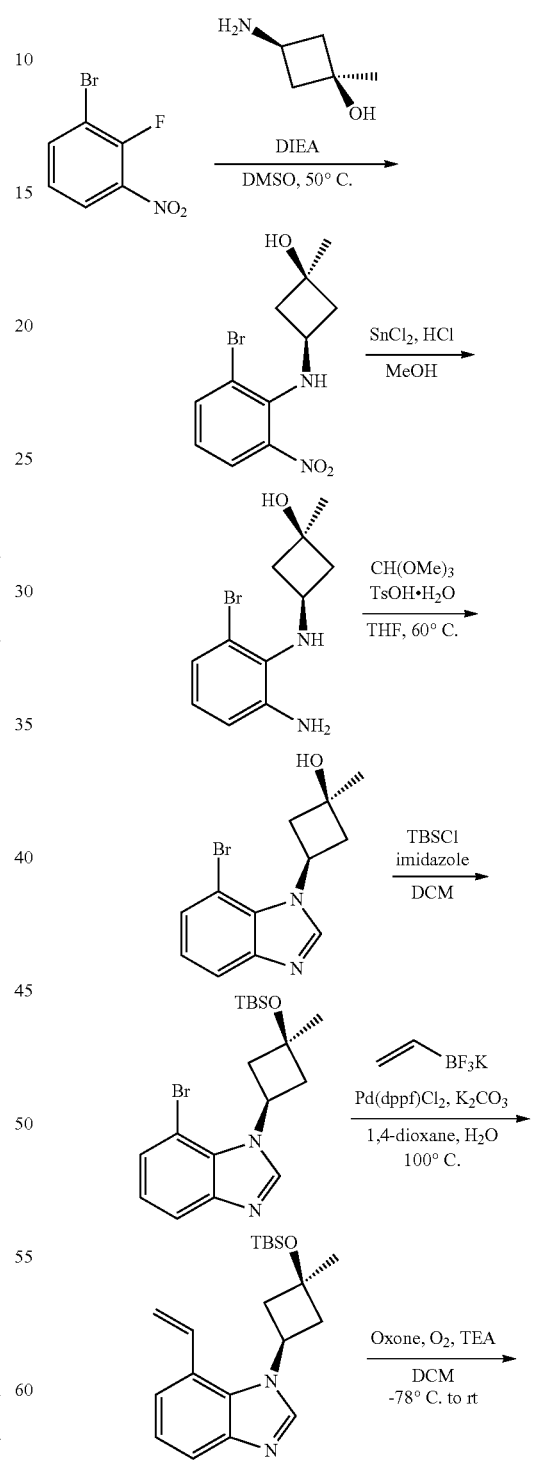

-continued

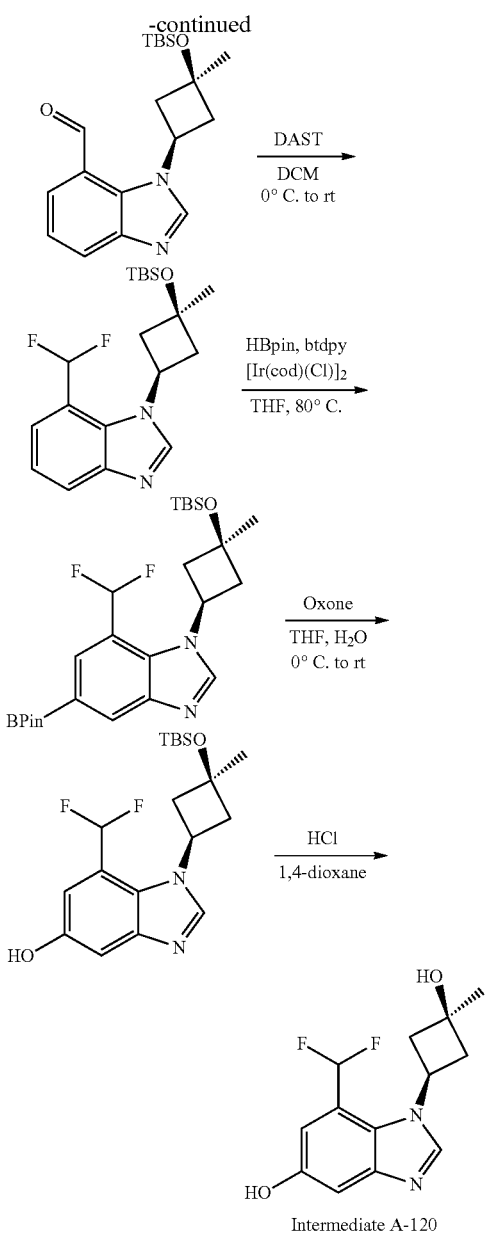

Intermediate A-120

Step 1: (cis)-3-((2-bromo-6-nitrophenyl)amino)-1-methylcyclobutan-1-ol

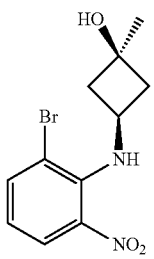

To a solution of 1-bromo-2-fluoro-3-nitro-benzene (11.0 g, 50.0 mmol) and (cis)-3-amino-1-methylcyclobutan-1-ol (8.26 g, 60.0 mmol, HCl salt) in DMSO (60 mL) was added DIEA (34.9 mL, 200 mmol). The mixture was stirred at 50° C. for 2 h. The reaction mixture was then quenched by addition of H$_2$O (150 mL) and extracted with EtOAc (3×150 mL). The combined organic layers were washed with H$_2$O (3×100 mL), dried over Na$_2$SO$_4$, filtered and concentrated under reduced pressure to give (cis)-3-[(2-bromo-6-nitrophenyl)amino]-1-methylcyclobutan-1-ol, which was taken to the next step without further purification. MS=301.1/303.1 [M+H]$^+$.

Step 2: (cis)-3-((2-amino-6-bromophenyl)amino)-1-methylcyclobutan-1-ol

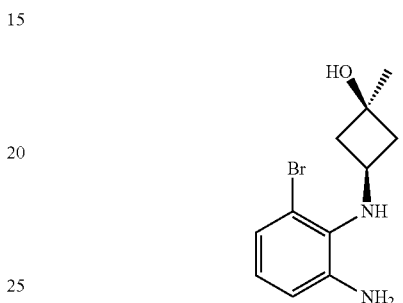

To a solution of (cis)-3-[(2-bromo-6-nitrophenyl)amino]-1-methylcyclobutan-1-ol (16.4 g, 54.5 mmol) in MeOH (120 mL) and 12 M aqueous HCl (30 mL, 360 mmol) was added SnCl$_2$ (31.0 g, 163 mmol). The mixture was stirred at room temperature for 2 h. The reaction mixture was adjusted to pH=8 with 10% aqueous NaOH solution and then extracted with EtOAc (3×250 mL). The combined organic layers were dried over Na$_2$SO$_4$, filtered, and concentrated under reduced pressure. The residue was purified by flash silica gel chromatography (Biotage 120 g cartridge, 0-45% EtOAc/Petroleum ether) to give (cis)-3-[(2-amino-6-bromophenyl)amino]-1-methylcyclobutan-1-ol. MS=271.2/273.2 [M+H]$^+$.

Step 3: (cis)-3-(7-bromo-1H-1,3-benzodiazol-1-yl)-1-methylcyclobutan-1-ol

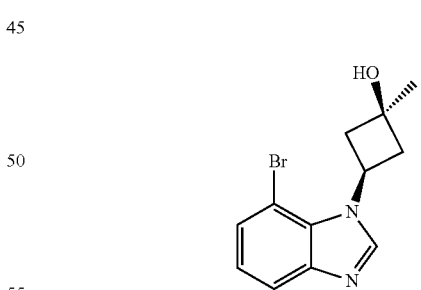

To a solution of (cis)-3-[(2-amino-6-bromophenyl)amino]-1-methylcyclobutan-1-ol (13.8 g, 50.7 mmol) in THF (130 mL) was added TsOH·H$_2$O (1.93 g, 10.1 mmol) and trimethyl orthoformate (11.0 mL, 101 mmol). The mixture was stirred at 60° C. for 2 h. After cooling to room temperature, the reaction mixture was quenched by addition of H$_2$O (300 mL) and extracted with EtOAc (3×200 mL). The combined organic layers were washed with saturated aqueous NaHCO$_3$ (2×200 mL), dried over Na$_2$SO$_4$, filtered, and concentrated in vacuo. The crude product was triturated with MTBE (40 mL), then the filter cake was isolated by Step 4: 7-bromo-1-[(cis)-3-[(tert-butyldimethylsilyl)oxy]-3-methylcyclobutyl]-1H-1,3-benzodiazole

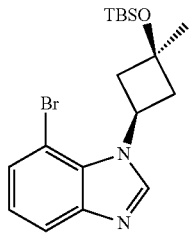 [SMILES: CC(C)(C)[Si](C)(C)O[C@]1(C)C[C@H](n2cnc3cccc(Br)c32)C1]

To a solution of (cis)-3-(7-bromo-1H-1,3-benzodiazol-1-yl)-1-methylcyclobutan-1-ol (12.5 g, 44.4 mmol) in DCM (150 mL) was added TBSCl (20.1 g, 133 mmol) and imidazole (18.2 g, 267 mmol). The mixture was stirred at room temperature for 16 h. The reaction mixture was quenched by addition of H$_2$O (200 mL), and then extracted with DCM (2×200 mL). The combined organic layers were washed with saturated aqueous NaHCO$_3$ solution (2×200 mL), dried over Na$_2$SO$_4$, filtered, and concentrated in vacuo. The residue was purified by flash silica gel chromatography (Biotage 120 g cartridge, 0-8% EtOAc/Petroleum ether) to give 7-bromo-1-[(cis)-3-[(tert-butyldimethylsilyl)oxy]-3-methylcyclobutyl]-1H-1,3-benzodiazole. MS=395.3/397.3. [M+H]$^+$.

Step 5: 7-ethenyl-1-[(cis)-3-[(tert-butyldimethylsilyl)oxy]-3-methylcyclobutyl]-1H-1,3-benzodiazole

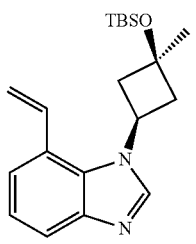 [SMILES: C=Cc1cccc2ncn([C@H]3C[C@@](C)(O[Si](C)(C)C(C)(C)C)C3)c12]

A mixture of 7-bromo-1-[(cis)-3-[(tert-butyldimethylsilyl)oxy]-3-methylcyclobutyl]-1H-1,3-benzodiazole (16.9 g, 42.7 mmol), potassium vinyltrifluoroborate (17.2 g, 128 mmol), K$_2$CO$_3$ (17.7 g, 128 mmol) and Pd(dppf)Cl$_2$ (3.13 g, 4.27 mmol) in 1,4-dioxane (140 mL) and H$_2$O (35 mL) was degassed and purged with N$_2$ (3×), and then the mixture was stirred at 100° C. for 16 h under N$_2$ atmosphere. The reaction mixture was concentrated in vacuo, then was diluted with H$_2$O (200 mL) and extracted with EtOAc (3×200 mL). The combined organic layers were washed with brine (2×200 mL), dried over Na$_2$SO$_4$, filtered, and concentrated in vacuo. The residue was purified by flash silica gel chromatography (Biotage 220 g cartridge, 0-20% EtOAc/Petroleum ether) to give 7-ethenyl-1-[(cis)-3-[(tert-butyldimethylsilyl)oxy]-3-methylcyclobutyl]-1H-1,3-benzodiazole. MS=343.2 [M+H]$^+$.

Step 6: 1-[(cis)-3-[(tert-butyldimethylsilyl)oxy]-3-methylcyclobutyl]-1H-1,3-benzodiazole-7-carbaldehyde

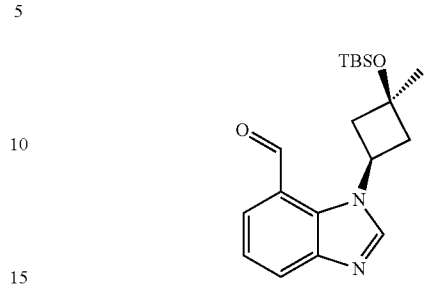

Ozone was bubbled into a −78° C. solution of 7-ethenyl-1-[(cis)-3-[(tert-butyldimethylsilyl)oxy]-3-methylcyclobutyl]-1H-1,3-benzodiazole (3.00 g, 8.76 mmol) in DCM (40 mL) for 20 min. The resulting solution was then purged with 02 for an additional 10 min before being treated with TEA (886 mg, 8.76 mmol), and then the mixture was allowed to warm to room temperature for 10 min. The reaction mixture was adjusted to pH=5 with 3.0 M aqueous HCl solution, and then extracted with DCM (3×50 mL). The combined organic layers were dried over Na$_2$SO$_4$, filtered, and concentrated in vacuo. The residue was purified by flash silica gel chromatography (Biotage 40 g cartridge, 0-15% EtOAc/Petroleum ether) to give 1-[(cis)-3-[(tert-butyldimethylsilyl)oxy]-3-methylcyclobutyl]-1H-1,3-benzodiazole-7-carbaldehyde. MS=345.3. [M+H]$^+$.

Step 7: 7-(difluoromethyl)-1-[(cis)-3-[(tert-butyldimethylsilyl)oxy]-3-methylcyclobutyl]-1H-1,3-benzodiazole

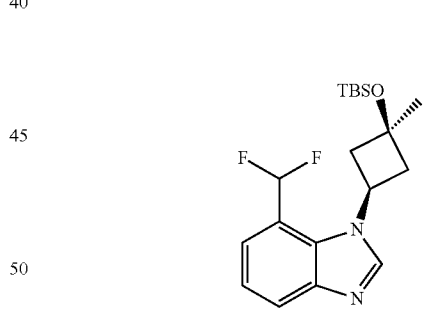

To a 0° C. solution of 1-[(cis)-3-[(tert-butyldimethylsilyl)oxy]-3-methylcyclobutyl]-1H-1,3-benzodiazole-7-carbaldehyde (2.54 g, 7.37 mmol) in DCM (30 mL) was added DAST (4.16 g, 25.8 mmol). The mixture was stirred at room temperature for 16 h. The reaction mixture was cooled to 0° C., quenched by addition of H$_2$O (50 mL), and then extracted with DCM (2×50 mL). The combined organic layers were washed with saturated aqueous NaHCO$_3$ solution (3×50 mL), dried over Na$_2$SO$_4$, filtered, and concentrated under reduced pressure. The residue was purified by flash silica gel chromatography (Biotage 40 g cartridge, 0-15% EtOAc/Petroleum ether) to give 7-(difluoromethyl)-1-[(cis)-3-[(tert-butyldimethylsilyl)oxy]-3-methylcyclobutyl]-1H-1,3-benzodiazole. MS=367.3 [M+H]$^+$.

Step 8: 7-(difluoromethyl)-1-[(cis)-3-[(tert-butyldimethylsilyl)oxy]-3-methylcyclobutyl]-5-(4,4,5,5-tetramethyl-1,3,2-dioxaborolan-2-yl)-1H-1,3-benzodiazole

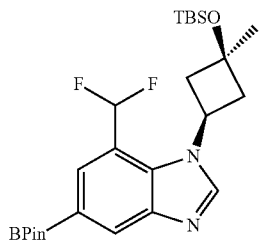

To a solution of 7-(difluoromethyl)-1-[(cis)-3-[(tert-butyldimethylsilyl)oxy]-3-methylcyclobutyl]-1H-1,3-benzodiazole (500 mg, 1.36 mmol) in THF (10 mL) was added pinacolborane (2.62 g, 20.5 mmol), 4,4'-di-tert-butyl-2,2'-dipyridyl (73.2 mg, 273 μmol) and (1,5-cyclooctadiene)(methoxy)iridium(I) dimer (91.6 mg, 136 μmol). The mixture was degassed and purged with $N_2$ (3×), and then stirred at 80° C. for 32 h. After cooling to room temperature, the reaction was filtered and the filtrate was concentrated in vacuo to give 7-(difluoromethyl)-1-[(cis)-3-[(tert-butyldimethylsilyl)oxy]-3-methylcyclobutyl]-5-(4,4,5,5-tetramethyl-1,3,2-dioxaborolan-2-yl)-1H-1,3-benzodiazole, which was taken to the next step without further purification. MS=493.2 [M+H]$^+$.

Step 9: 7-(difluoromethyl)-1-[(cis)-3-[(tert-butyldimethylsilyl)oxy]-3-methylcyclobutyl]-1H-1,3-benzodiazol-5-ol

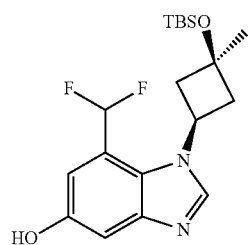 [SMILES: CC(C)(C)[Si](C)(C)O[C@]1(C)C[C@H](n2cnc3cc(O)cc(C(F)F)c32)C1]

To a 0° C. solution of 7-(difluoromethyl)-1-[(cis)-3-[(tert-butyldimethylsilyl)oxy]-3-methylcyclobutyl]-5-(4,4,5,5-tetramethyl-1,3,2-dioxaborolan-2-yl)-1H-1,3-benzodiazole (700 mg, 1.42 mmol) in $H_2O$ (5 mL) and THF (5 mL) was added Oxone (1.31 g, 2.13 mmol). The mixture was then stirred at room temperature for 2 h. The reaction mixture was quenched by addition of saturated aqueous $Na_2SO_3$ solution (100 mL) and then extracted with EtOAc (3×50 mL). The combined organic layers were dried over $Na_2SO_4$, filtered, and concentrated under reduced pressure. The residue was purified by reverse phase preparative HPLC (Phenomenex Luna $C_{18}$ column, 40-70% MeCN: 10 mM TFA in $H_2O$) to give 7-(difluoromethyl)-1-[(cis)-3-[(tert-butyldimethylsilyl)oxy]-3-methylcyclobutyl]-1H-1,3-benzodiazol-5-ol. MS=383.2 [M+H]$^+$.

Step 10: 7-(difluoromethyl)-1-[(cis)-3-hydroxy-3-methylcyclobutyl]-1H-1,3-benzodiazol-5-ol

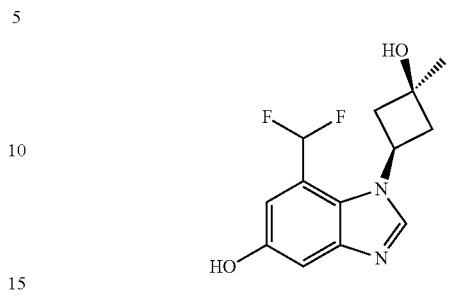

To a solution of 7-(difluoromethyl)-1-[(cis)-3-[(tert-butyldimethylsilyl)oxy]-3-methylcyclobutyl]-1H-1,3-benzodiazol-5-ol (50.0 mg, 65.4 μmol) in 1,4-dioxane (0.5 mL) was added 4.0 M HCl in 1,4-dioxane (2.0 mL, 8.0 mmol). The mixture was stirred at room temperature for 2 h, then was concentrated in vacuo to give 7-(difluoromethyl)-1-[(cis)-3-hydroxy-3-methylcyclobutyl]-1H-1,3-benzodiazol-5-ol (Intermediate A-120), which was taken to the next step without further purification. MS=269.1 [M+H]$^+$.

General Procedure for Intermediate A-121

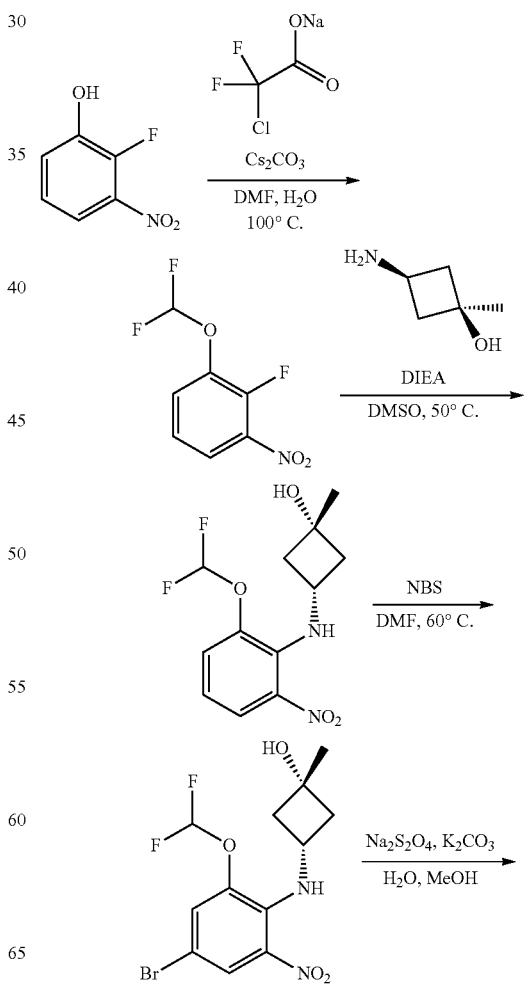

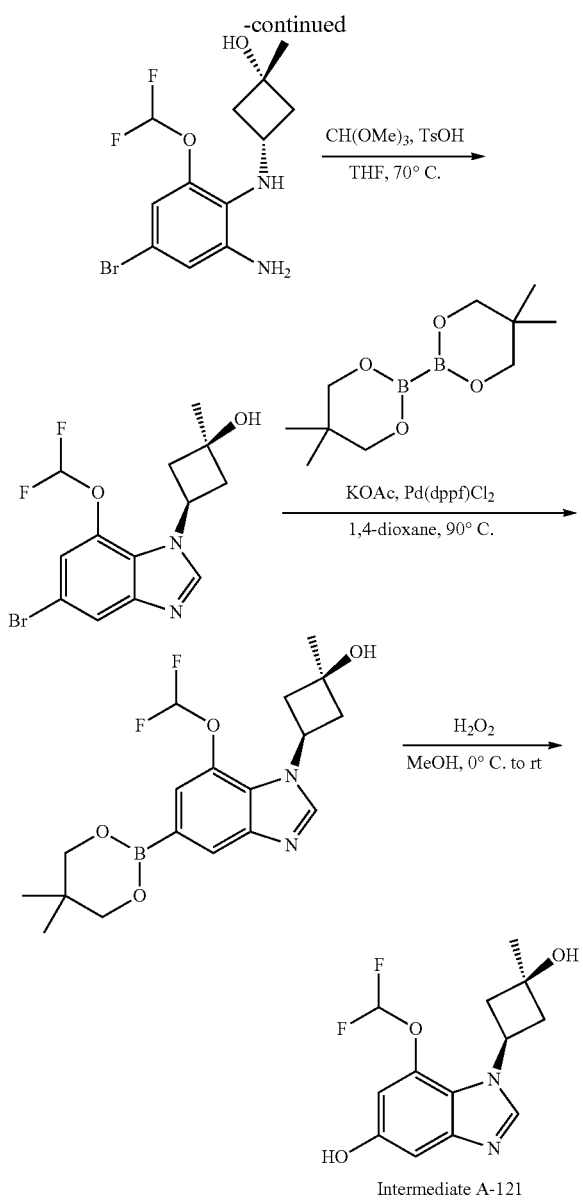


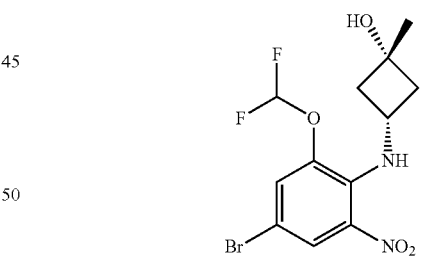

Intermediate A-121

Step 1:
1-(difluoromethoxy)-2-fluoro-3-nitro-benzene

To a mixture of 2-fluoro-3-nitro-phenol (2.00 g, 12.7 mmol) and Cs$_2$CO$_3$ (12.4 g, 38.2 mmol) in DMF (20 mL) and H$_2$O (4 mL) was added sodium chlorodifluoroacetate (19.4 g, 127 mmol). The mixture was stirred at 100° C. for 6 h. After cooling to room temperature, the reaction mixture was quenched by addition of H$_2$O (30 mL) and extracted with EtOAc (30 mL×3). The combined organic layers were washed with brine (2×30 mL), dried over Na$_2$SO$_4$, filtered, and concentrated under reduced pressure. The residue was purified by flash silica gel chromatography (Biotage 20 g cartridge, 0-15% EtOAc/Petroleum ether) to give 1-(difluoromethoxy)-2-fluoro-3-nitro-benzene. MS=208.0 [M+H]$^+$.

Step 2: (cis)-3-{[2-(difluoromethoxy)-6-nitrophenyl]amino}-1-methylcyclobutan-1-ol To a solution of 1-(difluoromethoxy)-2-fluoro-3-nitro-benzene (1.20 g, 5.79 mmol) in DMSO (12 mL) was added DIEA (3.00 g, 23.2 mmol) and (cis)-3-amino-1-methylcyclobutan-1-ol (877 mg, 6.37 mmol, HCl salt). The mixture was stirred at 50° C. for 2 h. After cooling to room temperature, the reaction mixture was diluted with H$_2$O (30 mL) and extracted with EtOAc (3×30 mL). The combined organic layers were washed with brine (3×5 mL), dried over Na$_2$SO$_4$, filtered, and concentrated under reduced pressure to give (cis)-3-{[2-(difluoromethoxy)-6-nitrophenyl]amino}-1-methylcyclobutan-1-ol, which was taken to the next step without further purification. MS=288.9 [M+H]$^+$.

Step 3: (cis)-3-{[4-bromo-2-(difluoromethoxy)-6-nitrophenyl]amino}-1-methylcyclobutan-1-ol To a solution of (cis)-3-{[2-(difluoromethoxy)-6-nitrophenyl]amino}-1-methylcyclobutan-1-ol (1.80 g, 6.24 mmol) in DMF (40 mL) was added NBS (2.22 g, 12.5 mmol). The mixture was stirred at 60° C. for 12 h. After cooling to room temperature, the reaction mixture was quenched by addition of H$_2$O (120 mL) and extracted with EtOAc (3×50 mL). The combined organic layers were washed with brine (2×50 mL), dried over Na$_2$SO$_4$, filtered, and concentrated in vacuo. The residue was purified by flash silica gel chromatography (Biotage 12 g cartridge, 0-15% EtOAc/Petroleum ether) to give (cis)-3-{[4-bromo-2-(difluoromethoxy)-6-nitrophenyl]amino}-1-methylcyclobutan-1-ol. MS=367.0/369.0 [M+H]$^+$.

Step 4: (cis)-3-{[2-amino-4-bromo-6-(difluoromethoxy)phenyl]amino}-1-methylcyclobutan-1-ol

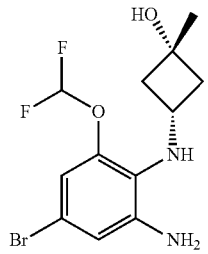 [SMILES: C[C@]1(O)C[C@@H](Nc2c(N)cc(Br)cc2OC(F)F)C1]

To a solution of K$_2$CO$_3$ (1.88 g, 13.6 mmol) in H$_2$O (5 mL) was added Na$_2$S$_2$O$_4$ (1.42 g, 8.17 mmol) followed by (cis)-3-{[4-bromo-2-(difluoromethoxy)-6-nitrophenyl]amino}-1-methylcyclobutan-1-ol (1.00 g, 2.72 mmol) in MeOH (5 mL). The mixture was stirred at room temperature for 1 h. The reaction mixture was quenched by addition of H$_2$O (50 mL) and extracted with EtOAc (3×50 mL). The combined organic layers were washed with brine (20 mL), dried over Na$_2$SO$_4$, filtered, and concentrated in vacuo to give (cis)-3-{[2-amino-4-bromo-6-(difluoromethoxy)phenyl]amino}-1-methylcyclobutan-1-ol, which was taken to the next step without further purification. MS=337.0/339.0 [M+H]$^+$.

Step 5: (cis)-3-[5-bromo-7-(difluoromethoxy)-1H-1,3-benzodiazol-1-yl]-1-methylcyclobutan-1-ol

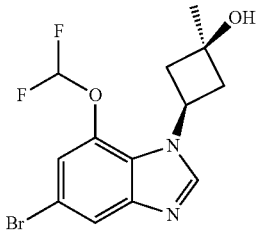 [SMILES: C[C@]1(O)C[C@@H](n2cnc3cc(Br)cc(OC(F)F)c32)C1]

To a solution of (cis)-3-{[2-amino-4-bromo-6-(difluoromethoxy)phenyl]amino}-1-methylcyclobutan-1-ol (720 mg, 2.14 mmol) in THF (11 mL) was added TsOH·H$_2$O (81.2 mg, 427 μmol) and trimethyl orthoformate (453 mg, 4.27 mmol). The mixture was stirred at 70° C. for 2 h. After cooling to room temperature, the reaction mixture was quenched by addition of H$_2$O (20 mL) and extracted with EtOAc (3×20 mL). The combined organic layers were washed with brine (10 mL), dried over Na$_2$SO$_4$, filtered, and concentrated in vacuo. The resulting solid was triturated with MTBE (20 mL) for 10 min, then the filter cake was isolated by filtration and dried in vacuo to give (cis)-3-[5-bromo-7-(difluoromethoxy)-1H-1,3-benzodiazol-1-yl]-1-methylcyclobutan-1-ol, which was taken to the next step without further purification. MS=347.0/348.9 [M+H]$^+$.

Step 6: (cis)-3-[7-(difluoromethoxy)-5-(5,5-dimethyl-1,3,2-dioxaborinan-2-yl)-1H-1,3-benzodiazol-1-yl]-1-methylcyclobutan-1-ol

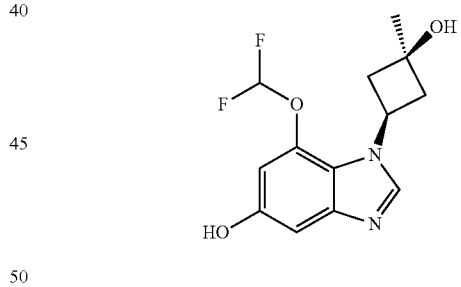

A mixture of (cis)-3-[5-bromo-7-(difluoromethoxy)-1H-1,3-benzodiazol-1-yl]-1-methylcyclobutan-1-ol (1.50 g, 4.32 mmol), 2-(5,5-dimethyl-1,3,2-dioxaborinan-2-yl)-5,5-dimethyl-1,3,2-dioxaborinane (2.93 g, 12.9 mmol), KOAc (1.06 g, 10.8 mmol) and Pd(dppf)Cl$_2$·CH$_2$Cl$_2$ (353 mg, 432 μmol) in 1,4-dioxane (25 mL) was degassed and purged with N$_2$ (3×), and then the mixture was stirred at 90° C. for 12 h under N$_2$ atmosphere. After cooling to room temperature, solids were removed by filtration and the filtrate was concentrated in vacuo to give (cis)-3-[7-(difluoromethoxy)-5-(5,5-dimethyl-1,3,2-dioxaborinan-2-yl)-1H-1,3-benzodiazol-1-yl]-1-methylcyclobutan-1-ol, which was taken to the next step without further purification. MS=313.1 [M-C$_5$H$_8$+H]$^+$.

Step 7: 7-(difluoromethoxy)-1-[(cis)-3-hydroxy-3-methylcyclobutyl]-1H-1,3-benzodiazol-5-ol To a 0° C. solution of (cis)-3-[7-(difluoromethoxy)-5-(5,5-dimethyl-1,3,2-dioxaborinan-2-yl)-1H-1,3-benzodiazol-1-yl]-1-methylcyclobutan-1-ol (2.00 g, 5.26 mmol) in MeOH (25 mL) was added dropwise 30% H$_2$O$_2$ in H$_2$O (10.2 mL, 106 mmol). The resulting mixture was then stirred at room temperature for 1 h. The mixture was quenched with saturated aqueous Na$_2$SO$_3$ solution (20 mL) and extracted with EtOAc (3×20 mL). The combined organic layers were dried over Na$_2$SO$_4$ filtered and concentrated in vacuo to give 7-(difluoromethoxy)-1-[(cis)-3-hydroxy-3-methylcyclobutyl]-1H-1,3-benzodiazol-5-ol (Intermediate A-121), which was taken to the next step without further purification. MS=285.1 [M+H]$^+$.

General Procedure for Intermediate A-122

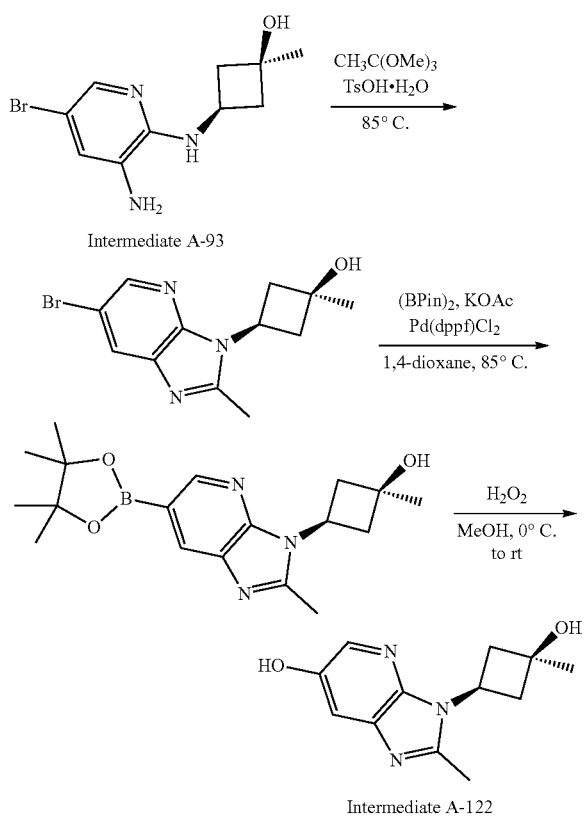

Step 1: (cis)-3-{6-bromo-2-methyl-3H-imidazo[4,5-b]pyridin-3-yl}-1-methylcyclobutan-1-ol

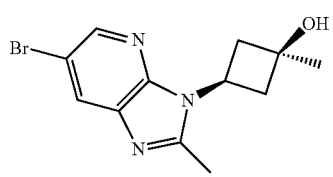 [SMILES: Cc1nc2cc(Br)cnc2n1[C@H]1C[C@@](C)(O)C1]

A mixture of (cis)-3-[(3-amino-5-bromopyridin-2-yl)amino]-1-methylcyclobutan-1-ol (Intermediate A-93, 630 mg, 2.32 mmol), pTSA·H$_2$O (220 mg, 1.16 mmol) and triethyl orthoacetate (5.89 mL, 46.3 mmol) was stirred at 85° C. for 2 h. The mixture was cooled to room temperature, then diluted with H$_2$O (20 mL), and extracted with EtOAc (3×20 mL). The combined organic layers were dried over Na$_2$SO$_4$, filtered and concentrated. The crude product was purified by silica gel chromatography (Biotage 50 g cartridge, 0-100% EtOAc/hexane) to give (cis)-3-{6-bromo-2-methylimidazo[4,5-b]pyridin-3-yl}-1-methylcyclobutan-1-ol. MS=296.2/298.2 [M+H]$^+$.

Step 2: (cis)-1-methyl-3-[2-methyl-6-(4,4,5,5-tetramethyl-1,3,2-dioxaborolan-2-yl)-3H-imidazo[4,5-b]pyridin-3-yl]cyclobutan-1-ol

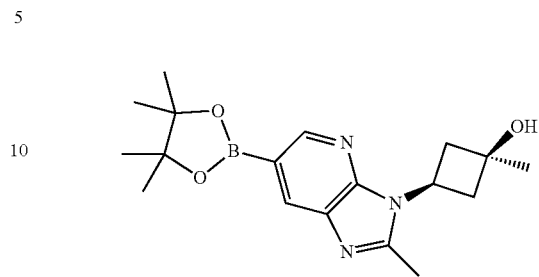

A mixture of (cis)-3-{6-bromo-2-methylimidazo[4,5-b]pyridin-3-yl}-1-methylcyclobutan-1-ol (250 mg, 0.844 mmol), bis(pinacolato)diboron (257 mg, 1.01 mmol.), Pd(dppf)Cl$_2$·CH$_2$Cl$_2$ (34 mg, 0.042 mmol) and KOAc (166 mg, 1.69 mmol) in 1,4-dioxane (8 mL) was purged with nitrogen for 10 min at room temperature, then stirred at 85° C. for 16 h. The reaction mixture was cooled to room temperature and filtered through a Celite pad. The filtrate was concentrated in vacuo to give (cis)-1-methyl-3-[2-methyl-6-(4,4,5,5-tetramethyl-1,3,2-dioxaborolan-2-yl)imidazo[4,5-b]pyridin-3-yl]cyclobutan-1-ol, which was taken to the next step without further purification. MS=344.0 [M+H]$^+$.

Step 3: 2-methyl-3-[(cis)-3-hydroxy-3-methylcyclobutyl]-3H-imidazo[4,5-b]pyridin-6-ol

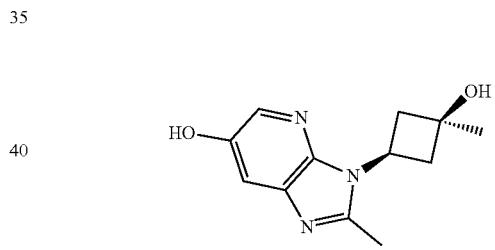

To a mixture of (cis)-1-methyl-3-[2-methyl-6-(4,4,5,5-tetramethyl-1,3,2-dioxaborolan-2-yl)imidazo[4,5-b]pyridin-3-yl]cyclobutan-1-ol (0.290 g, 0.844 mmol) in MeOH (4 mL) at 0° C. was added 30% H$_2$O$_2$ in H$_2$O (0.216 mL, 2.11 mmol) dropwise. The mixture was warmed to room temperature and stirred for 2 h. The mixture was then concentrated in vacuo to give 2-methyl-3-[(cis)-3-hydroxy-3-methylcyclobutyl]imidazo[4,5-b]pyridin-6-ol (Intermediate A-122), which was taken to the next step without further purification. MS=234.2 [M+H]$^+$.

General Procedure for Intermediate A-123

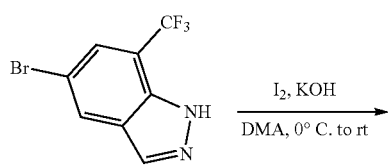

853
-continued

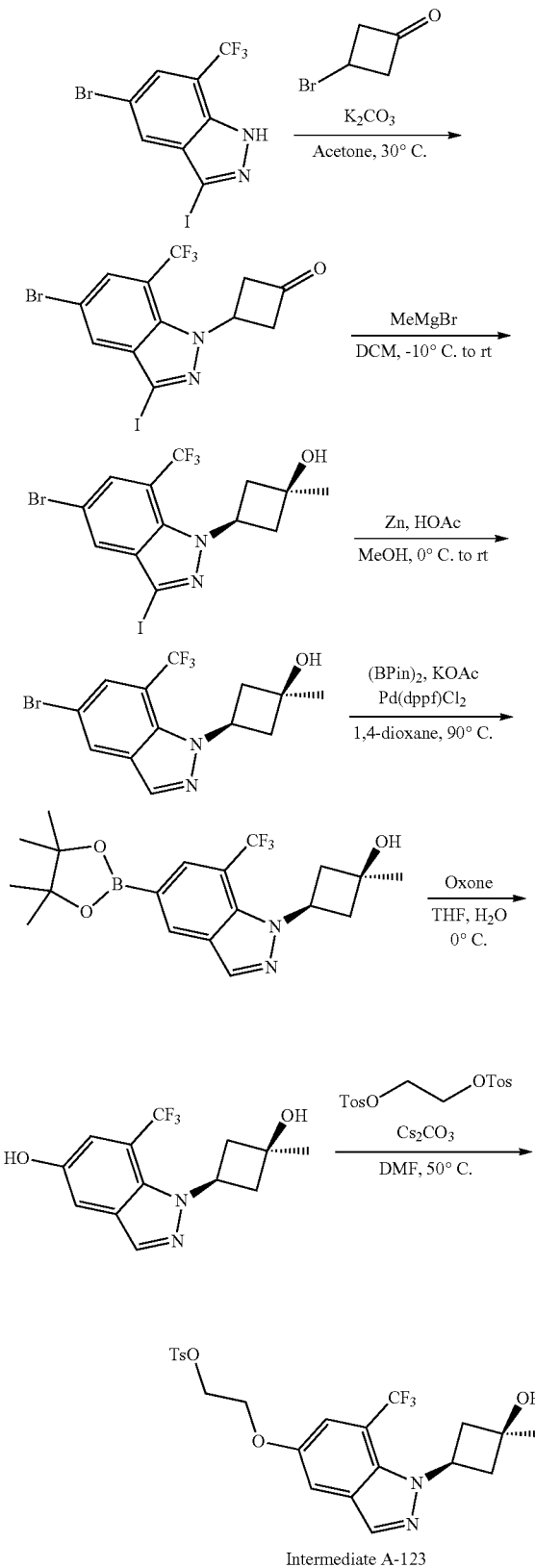

Intermediate A-123

854

Step 1:
5-bromo-3-iodo-7-(trifluoromethyl)-1H-indazole

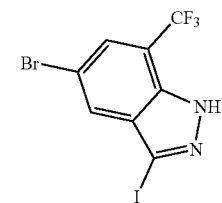 [SMILES: FC(F)(F)c1cc(Br)cc2c(I)n[nH]c12]

To a 0° C. solution of 5-bromo-7-(trifluoromethyl)-1H-indazole (4.50 g, 17.0 mmol) in DMA (40 mL) was added I2 (3.42 mL, 17.0 mmol) and KOH (2.86 g, 50.9 mmol). The mixture was stirred at room temperature for 6 h. The mixture was diluted with $H_2O$ (40 mL) and extracted with EtOAc (2×30 mL). The combined organic layers were dried over $Na_2SO_4$, filtered, and concentrated in vacuo. The residue was purified by flash silica gel chromatography (Biotage, 40 g cartridge, 0-25% EtOAc/Petroleum ether) to give 5-bromo-3-iodo-7-(trifluoromethyl)-1H-indazole. MS=390.6/392.6 $[M+H]^+$.

Step 2: 3-[5-bromo-3-iodo-7-(trifluoromethyl)-1H-indazol-1-yl]cyclobutan-1-one

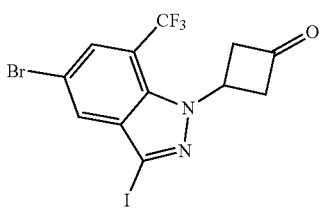 [SMILES: O=C1CC(n2nc(I)c3cc(Br)cc(C(F)(F)F)c32)C1]

To a solution of 5-bromo-3-iodo-7-(trifluoromethyl)-1H-indazole (3.40 g, 8.70 mmol) in acetone (30 mL) was added $K_2CO_3$ (3.61 g, 26.1 mmol) and 3-bromocyclobutanone (3.89 g, 26.1 mmol). The mixture was stirred at 30° C. for 12 h. The mixture was diluted with $H_2O$ (30 mL) and extracted with EtOAc (2×20 mL). The combined organic layers were dried over $Na_2SO_4$, filtered, and concentrated in vacuo. The residue was purified by flash silica gel chromatography (Biotage 20 g cartridge, 0-20% EtOAc/Petroleum ether) to provide 3-(5-bromo-3-iodo-7-(trifluoromethyl)-1H-indazol-1-yl)cyclobutan-1-one as the first eluting isomer. MS=458.7/460.6 $[M+H]^+$.

Step 3: (cis)-3-[5-bromo-3-iodo-7-(trifluoromethyl)-1H-indazol-1-yl]-1-methylcyclobutan-1-ol

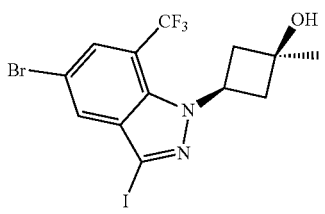 [SMILES: C[C@]1(O)C[C@@H](n2nc(I)c3cc(Br)cc(C(F)(F)F)c32)C1]

To a −10° C. solution of 3-(5-bromo-3-iodo-7-(trifluoromethyl)-1H-indazol-1-yl)cyclobutan-1-one (1.20 g, 2.62 mmol) in DCM (20 mL) under N₂ atmosphere was added 3.0 M MeMgBr in 2-Me-THF (871 µL, 2.62 mmol). The mixture was stirred at room temperature for 1 h under N₂ atmosphere. The reaction mixture was cooled to 0° C. and quenched by addition of H₂O (5 mL), and then extracted with EtOAc (3×10 mL). The combined organic layers were dried over Na₂SO₄, filtered, and concentrated in vacuo. The residue was purified by flash silica gel chromatography (Isco 20 g cartridge, 0-8% EtOAc/Petroleum ether) to provide (cis)-3-[5-bromo-3-iodo-7-(trifluoromethyl)-1H-indazol-1-yl]-1-methylcyclobutan-1-ol. MS=474.9/476.9 [M+H]⁺.

Step 4: (cis)-3-[5-bromo-7-(trifluoromethyl)-1H-indazol-1-yl]-1-methylcyclobutan-1-ol

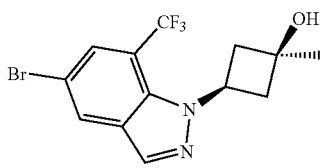 [SMILES: C[C@]1(O)C[C@@H](n2ncc3cc(Br)cc(C(F)(F)F)c32)C1]

To a 0° C. mixture of (cis)-3-(5-bromo-3-iodo-7-(trifluoromethyl)-1H-indazol-1-yl)-1-methylcyclobutan-1-ol (650 mg, 1.37 mmol) in HOAc (7 mL) and MeOH (7 mL) was added Zn (930 mg, 14.2 mmol) portion wise. The mixture was stirred at 0° C. for 30 min, then allowed to warm to room temperature and stirred for another 30 min. The mixture was filtered, and the filtrate was poured into H₂O (50 mL) and extracted with EtOAc (2×50 mL). The combined organic layers were washed with brine (50 mL), dried over Na₂SO₄, and concentrated in vacuo. The residue was purified by flash silica gel chromatography (SepaFlash 20 g cartridge, 0-20% EtOAc/Petroleum ether) to provide (cis)-3-[5-bromo-7-(trifluoromethyl)-1H-indazol-1-yl]-1-methylcyclobutan-1-ol. MS=348.9/350.9 [M+H]⁺.

Step 5: (cis)-1-methyl-3-[5-(4,4,5,5-tetramethyl-1,3,2-dioxaborolan-2-yl)-7-(trifluoromethyl)-1H-indazol-1-yl]cyclobutan-1-ol

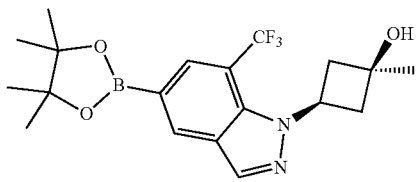

A mixture of (cis)-3-[5-bromo-7-(trifluoromethyl)-1H-indazol-1-yl]-1-methylcyclobutan-1-ol (380 mg, 1.09 mmol), bis(pinacolato)diboron (553 mg, 2.18 mmol), Pd(dppf)Cl₂ (79.6 mg, 109 µmol), and KOAc (320 mg, 3.27 mmol) in 1,4-dioxane (10 mL) was degassed and purged with N₂ (3×), and then the mixture was stirred at 90° C. for 2 h under N₂ atmosphere. After cooling to room temperature, the mixture was concentrated in vacuo. The filtrate was concentrated in vacuo to give (cis)-1-methyl-3-[5-(4,4,5,5-tetramethyl-1,3,2-dioxaborolan-2-yl)-7-(trifluoromethyl)-1H-indazol-1-yl]cyclobutan-1-ol. MS=397.1 [M+H]⁺.

Step 6: 1-[(cis)-3-hydroxy-3-methylcyclobutyl]-7-(trifluoromethyl)-1H-indazol-5-ol

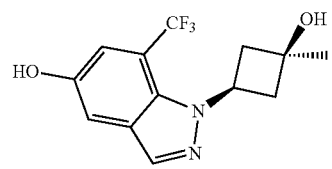 [SMILES: C[C@]1(O)C[C@@H](n2ncc3cc(O)cc(C(F)(F)F)c32)C1]

A 0° C. mixture of (cis)-1-methyl-3-[5-(4,4,5,5-tetramethyl-1,3,2-dioxaborolan-2-yl)-7-(trifluoromethyl)-1H-indazol-1-yl]cyclobutan-1-ol (431 mg, 1.09 mmol) and Oxone (1.34 g, 2.18 mmol) in THF (10 mL) and H₂O (10 mL) was stirred for 1 h. The 0° C. mixture was quenched with saturated aqueous Na₂SO₃ solution (20 mL) and extracted with EtOAc (2×20 mL). The combined organic layers were washed with brine (20 mL), dried over Na₂SO₄, filtered, and concentrated under reduced pressure to provide 1-[(cis)-3-hydroxy-3-methylcyclobutyl]-7-(trifluoromethyl)-1H-indazol-5-ol, which was used in the subsequent step without further purification. MS=287.1 [M+H]⁺.

Step 7: 2-({1-[(cis)-3-hydroxy-3-methylcyclobutyl]-7-(trifluoromethyl)-1H-indazol-5-yl}oxy)ethyl 4-methylbenzene-1-sulfonate

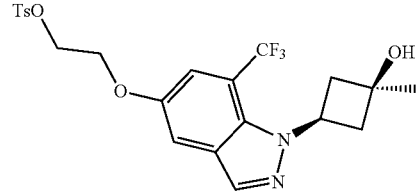 [SMILES: Cc1ccc(S(=O)(=O)OCCOc2cc(C(F)(F)F)c3c(cnn3[C@H]3C[C@@](C)(O)C3)c2)cc1]

A mixture of 1-[(cis)-3-hydroxy-3-methylcyclobutyl]-7-(trifluoromethyl)-1H-indazol-5-ol (250 mg, 873 µmol), 1,2-bis(tosyloxy)ethane (1.29 g, 3.49 mmol) and Cs₂CO₃ (854 mg, 2.62 mmol) in DMF (12 mL) was stirred at 50° C. for 4 h. After cooling to room temperature, the reaction was quenched with ice water (30 mL) and extracted with EtOAc (2×40 mL). The combined organic layers were washed with brine (100 mL), dried over Na₂SO₄, and concentrated in vacuo. The residue was purified by flash silica gel chromatography (SepaFlash 20 g cartridge, 0-60% EtOAc/Petroleum ether) to provide 2-({1-[(cis)-3-hydroxy-3-methylcyclobutyl]-7-(trifluoromethyl)-1H-indazol-5-yl}oxy)ethyl 4-methylbenzene-1-sulfonate (Intermediate A-123). MS=485.0 [M+H]⁺.

General Procedure for Intermediate A-124

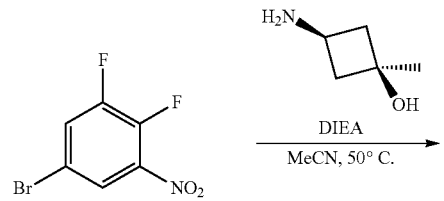

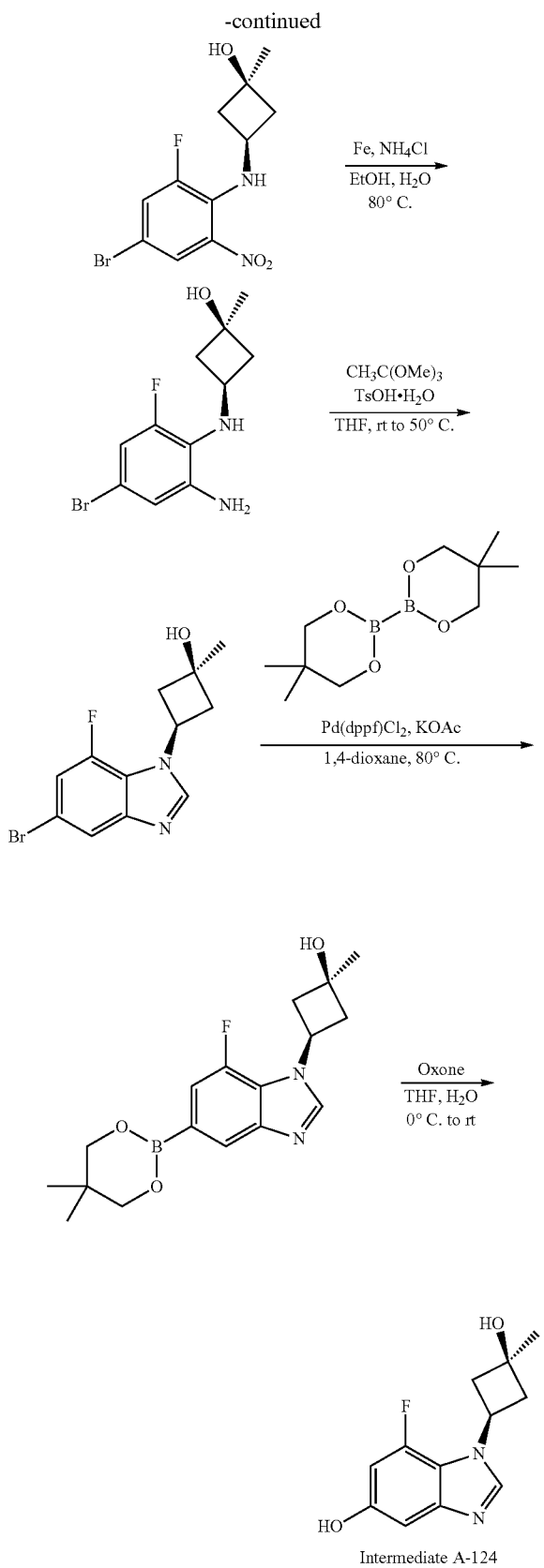

Intermediate A-124

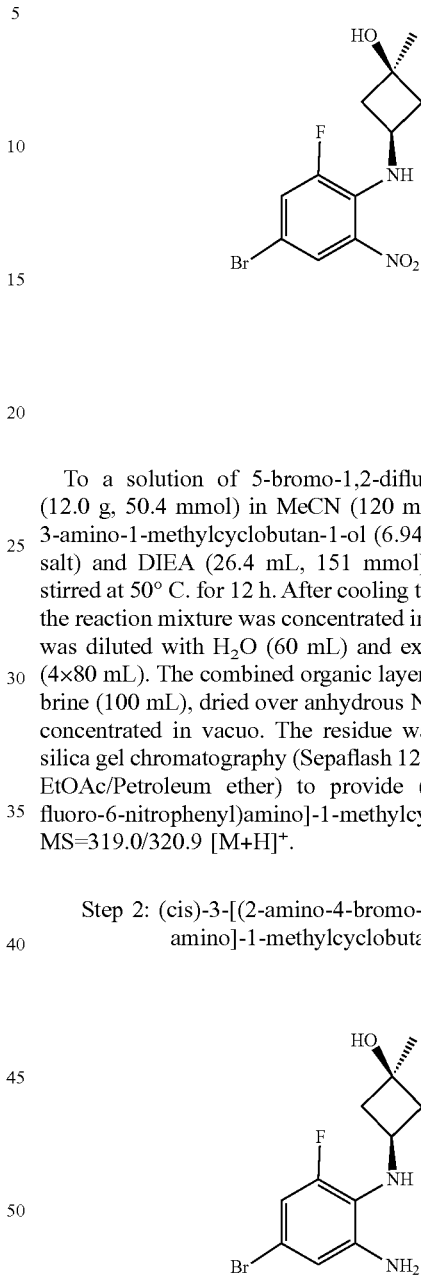

Step 1: (cis)-3-[(4-bromo-2-fluoro-6-nitrophenyl)amino]-1-methylcyclobutan-1-ol

To a solution of 5-bromo-1,2-difluoro-3-nitro-benzene (12.0 g, 50.4 mmol) in MeCN (120 mL) was added (cis)-3-amino-1-methylcyclobutan-1-ol (6.94 g, 50.4 mmol, HCl salt) and DIEA (26.4 mL, 151 mmol). The mixture was stirred at 50° C. for 12 h. After cooling to room temperature, the reaction mixture was concentrated in vacuo. The residue was diluted with $H_2O$ (60 mL) and extracted with EtOAc (4×80 mL). The combined organic layers were washed with brine (100 mL), dried over anhydrous $Na_2SO_4$, filtered, and concentrated in vacuo. The residue was purified by flash silica gel chromatography (Sepaflash 120 g cartridge, 0-15% EtOAc/Petroleum ether) to provide (cis)-3-[(4-bromo-2-fluoro-6-nitrophenyl)amino]-1-methylcyclobutan-1-ol. MS=319.0/320.9 $[M+H]^+$.

Step 2: (cis)-3-[(2-amino-4-bromo-6-fluorophenyl)amino]-1-methylcyclobutan-1-ol

To a solution of (cis)-3-[(4-bromo-2-fluoro-6-nitrophenyl)amino]-1-methylcyclobutan-1-ol (2.00 g, 6.27 mmol) in EtOH (20 mL) and $H_2O$ (10 mL) was added Fe (1.05 g, 18.8 mmol) and $NH_4Cl$ (1.68 g, 31.3 mmol). The mixture was stirred at 80° C. for 2 h. After cooling to room temperature, solids were removed by filtration and the filtrate was extracted with EtOAc (3×20 mL). The combined organic layers were washed with brine (50 mL), dried over anhydrous $Na_2SO_4$, filtered, and concentrated in vacuo. The residue was purified by flash silica gel chromatography (Sepaflash 40 g cartridge, 0-10% EtOAc/Petroleum ether) to provide (cis)-3-[(2-amino-4-bromo-6-fluorophenyl)amino]-1-methylcyclobutan-1-ol. MS=289.1/291.1 $[M+H]^+$.

Step 3: (cis)-3-(5-bromo-7-fluoro-1H-1,3-benzodiazol-1-yl)-1-methylcyclobutan-1-ol

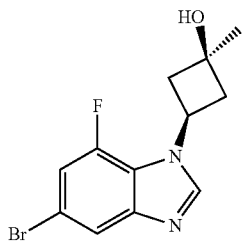 [SMILES: C[C@]1(O)C[C@@H](n2cnc3cc(Br)cc(F)c32)C1]

To a solution of trimethyl orthoformate (2.27 mL, 20.8 mmol) and (cis)-3-[(2-amino-4-bromo-6-fluorophenyl)amino]-1-methylcyclobutan-1-ol (5.00 g, 17.3 mmol) in THF (50 mL) was added TsOH·H$_2$O (329 mg, 1.73 mmol). After slowly warming to 50° C., the mixture was stirred at 50° C. for 5 h. The reaction mixture was cooled to room temperature, quenched with H$_2$O (30 mL), and adjusted to pH=8 by dropwise addition of saturated aqueous NaHCO$_3$ solution. The mixture was extracted with EtOAc (3×30 mL). The combined organic layers were washed with brine (50 mL), dried over Na$_2$SO$_4$, filtered, and concentrated under reduced pressure to give (cis)-3-(5-bromo-7-fluoro-1H-1,3-benzodiazol-1-yl)-1-methylcyclobutan-1-ol, which was used in the subsequent step without further purification. MS=299.0/301.1 [M+H]$^+$.

Step 4: (cis)-3-[5-(5,5-dimethyl-1,3,2-dioxaborinan-2-yl)-7-fluoro-1H-1,3-benzodiazol-1-yl]-1-methylcyclobutan-1-ol

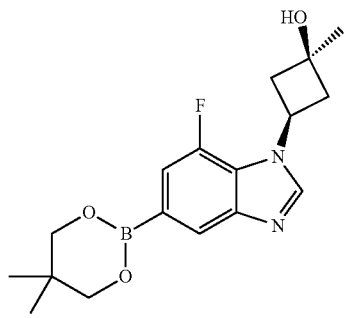

To a solution of (cis)-3-(5-bromo-7-fluoro-1H-benzo[d]imidazol-1-yl)-1-methylcyclobutan-1-ol (4.00 g, 13.4 mmol) and 2-(5,5-dimethyl-1,3,2-dioxaborinan-2-yl)-5,5-dimethyl-1,3,2-dioxaborinane (3.62 g, 16.1 mmol) in 1,4-dioxane (60 mL) under N$_2$ atmosphere was added KOAc (3.28 g, 33.4 mmol) and Pd(dppf)Cl$_2$ (978 mg, 1.34 mmol). The mixture was stirred at 80° C. for 16 h under N$_2$ atmosphere. The reaction mixture was allowed to cool to room temperature, then solids were removed by filtration and the filtrate was concentrated in vacuo to give (cis)-3-[5-(5,5-dimethyl-1,3,2-dioxaborinan-2-yl)-7-fluoro-1H-1,3-benzodiazol-1-yl]-1-methylcyclobutan-1-ol, which was used in the subsequent step without further purification. MS=333.1 [M+H]$^+$.

Step 5: 7-fluoro-1-[(cis)-3-hydroxy-3-methylcyclobutyl]-1H-1,3-benzodiazol-5-ol

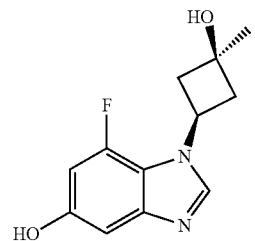 [SMILES: C[C@]1(O)C[C@@H](n2cnc3cc(O)cc(F)c32)C1]

To a 0° C. solution of (cis)-3-[5-(5,5-dimethyl-1,3,2-dioxaborinan-2-yl)-7-fluoro-1H-1,3-benzodiazol-1-yl]-1-methylcyclobutan-1-ol (3.00 g, 9.03 mmol) and H$_2$O (10 mL) in THF (30 mL) was added Oxone (2.78 g, 4.52 mmol) portion wise, and then the mixture was stirred at room temperature for 2 h. The reaction mixture was cooled to 0° C. then quenched by addition of saturated aqueous Na$_2$SO$_3$ solution (30 mL) and extracted with EtOAc (3×20 mL). The combined organic layers were washed with brine (50 mL), dried over Na$_2$SO$_4$, filtered, and concentrated in vacuo to give 7-fluoro-1-[(cis)-3-hydroxy-3-methylcyclobutyl]-1H-1,3-benzodiazol-5-ol (Intermediate A-124). MS=237.2 [M+H]$^+$.

General Procedure for Intermediate B-1

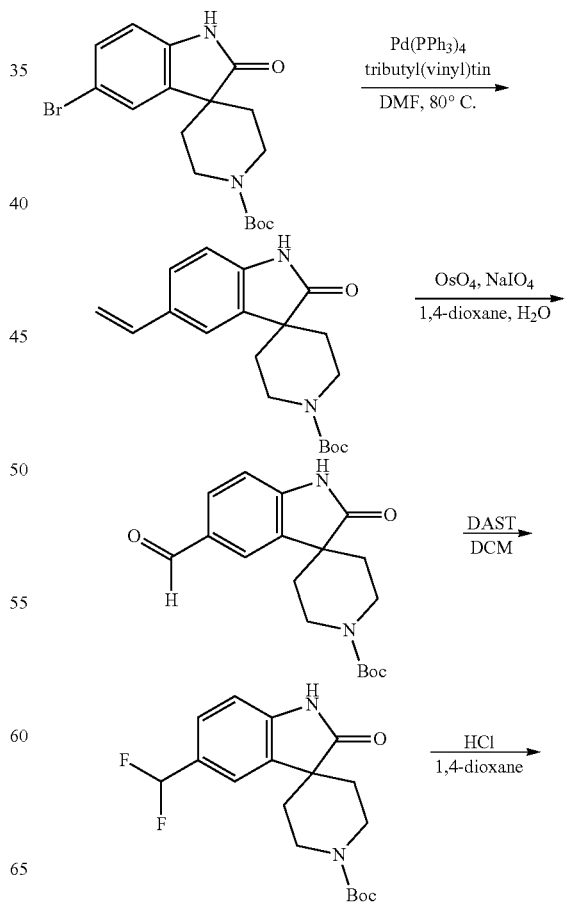

-continued

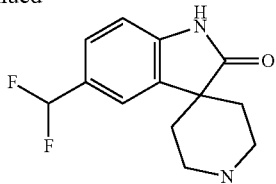

Intermediate B-1

Step 1: tert-Butyl 5-ethenyl-2-oxo-1,2-dihydrospiro[indole-3,4'-piperidine]-1'-carboxylate

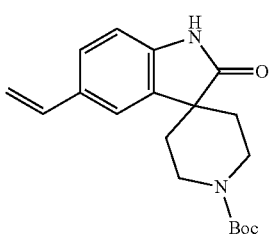 [SMILES: C=Cc1ccc2c(c1)C1(CCN(C(=O)OC(C)(C)C)CC1)C(=O)N2]

To a solution of tert-butyl 5-bromo-2-oxo-1,2-dihydrospiro[indole-3,4'-piperidine]-1'-carboxylate (555 mg, 1.45 mmol) in DMF (7.3 mL) was added tributyl(vinyl)tin (640 μL, 2.2 mmol). The mixture was sparged with $N_2$ for 10 min and tetrakis(triphenylphosphine)palladium (168 mg, 0.15 mmol) was added. The reaction mixture was flushed with $N_2$, sealed, and heated to 80° C. After 16 h the reaction mixture was removed from heat and concentrated in vacuo. The crude residue was purified by normal phase silica gel chromatography (Biotage 25 g cartridge, 0-100% EtOAc:hexanes) to afford tert-butyl 5-ethenyl-2-oxo-1,2-dihydrospiro[indole-3,4'-piperidine]-1'-carboxylate. $^1H$ NMR (500 MHz, $CDCl_3$): δ 8.93 (s, 1H), 7.39 (s, 1H), 7.31 (d, J=8.0, 1H), 6.94 (d, J=8.0 Hz, 1H), 6.72 (dd, J=17.5, 10.8 Hz, 1H), 5.69 (d, J=17.6 Hz, 1H), 5.22 (d, J=10.9 Hz, 1H), 3.98-3.74 (m, 4H), 1.99-1.78 (m, 4H), 1.56 (s, 9H).

Step 2: tert-Butyl 5-formyl-2-oxo-1,2-dihydrospiro[indole-3,4'-piperidine]-1'-carboxylate

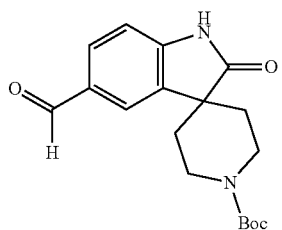 [SMILES: CC(C)(C)OC(=O)N1CCC2(CC1)C(=O)Nc1ccc(C=O)cc12]

To a solution of tert-butyl 5-ethenyl-2-oxo-1,2-dihydrospiro[indole-3,4'-piperidine]-1'-carboxylate (311 mg, 0.95 mmol) in 1,4-dioxane (8 mL) and water (4.5 mL) was added sodium periodate (405 mg, 1.89 mmol) followed by $OsO_4$ (500 μL, 2.5% w/w in t-BuOH, 0.38 mmol). The reaction mixture was stirred for 3 h at room temperature and then diluted with EtOAc (30 mL) and quenched with saturated aqueous $Na_2SO_3$ (50 mL). The aqueous layer was then extracted with EtOAc (3×30 mL). The combined organic layers were washed with brine (50 mL), dried over $Na_2SO_4$, filtered, and concentrated in vacuo. Purification by normal phase silica gel chromatography (Biotage 25 g cartridge, 80% EtOAc:hexanes) afforded tert-butyl 5-formyl-2-oxo-1,2-dihydrospiro[indole-3,4'-piperidine]-1'-carboxylate. $^1H$ NMR (500 MHz, DMSO-$d_6$): δ 9.93 (s, 1H), 8.34 (br s, 1H), 7.86 (s, 1H), 7.81 (d, J=7.9 Hz, 1H), 7.08 (d, J=8.0 Hz, 1H), 3.86 (dd, J=6.7, 4.9 Hz, 4H), 1.98-1.71 (m, 4H), 1.54 (s, 9H). MS=231.1 $[M-C_4H_8+H]^+$.

Step 3: tert-Butyl 5-(difluoromethyl)-2-oxo-1,2-dihydrospiro[indole-3,4'-piperidine]-1'-carboxylate

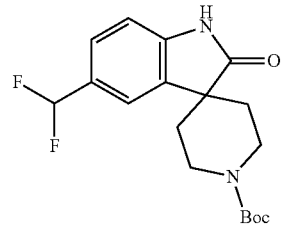 [SMILES: CC(C)(C)OC(=O)N1CCC2(CC1)C(=O)Nc1ccc(C(F)F)cc12]

To a solution of tert-butyl 5-formyl-2-oxo-1,2-dihydrospiro[indole-3,4'-piperidine]-1'-carboxylate (71.0 mg, 0.215 mmol) in DCM (1.4 mL) was added DAST (85 μL, 0.64 mmol) and the reaction was stirred at room temperature 16 h. The reaction mixture was then quenched by the addition of saturated aqueous $NaHCO_3$. The reaction mixture was extracted with EtOAc (3×30 mL). The combined organic layers were washed with brine (30 mL), dried over $Na_2SO_4$, filtered and concentrated. The crude residue was purified by normal phase silica gel chromatography (Biotage 10 g cartridge, 40% EtOAc:hexanes) to afford tert-butyl 5-(difluoromethyl)-2-oxo-1,2-dihydrospiro[indole-3,4'-piperidine]-1'-carboxylate. $^1H$ NMR (500 MHz, $CDCl_3$): δ 8.08 (s, 1H), 7.35 (s, 1H), 7.32-7.30 (m, 1H), 6.90 (d, J=8.0 Hz, 1H), 6.55 (t, J=56.6 Hz, 1H), 3.76 (dd, J=8.2, 4.3 Hz, 4H), 1.83-1.73 (m, 4H), 1.44 (s, 9H). MS=297.0 $[M-C_4H_8+H]^+$.

Step 4: 5-(Difluoromethyl)-1,2-dihydrospiro[indole-3,4'-piperidin]-2-one

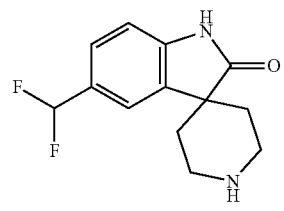 [SMILES: O=C1Nc2ccc(C(F)F)cc2C12CCNCC2]

tert-Butyl 5-(difluoromethyl)-2-oxo-1,2-dihydrospiro[indole-3,4'-piperidine]-1'-carboxylate (32 mg, 0.091 mmol) was dissolved in a 4.0 M HCl in dioxane solution (300 μL, 1.2 mmol) and stirred at room temperature for 1 h. The reaction mixture was then concentrated in vacuo to afford 5-(difluoromethyl)-1,2-dihydrospiro[indole-3,4'-piperidin]-2-one (Intermediate B-1), which was used without further purification. MS=253.1 $[M+H]^+$.

General Procedure for Intermediate B-2

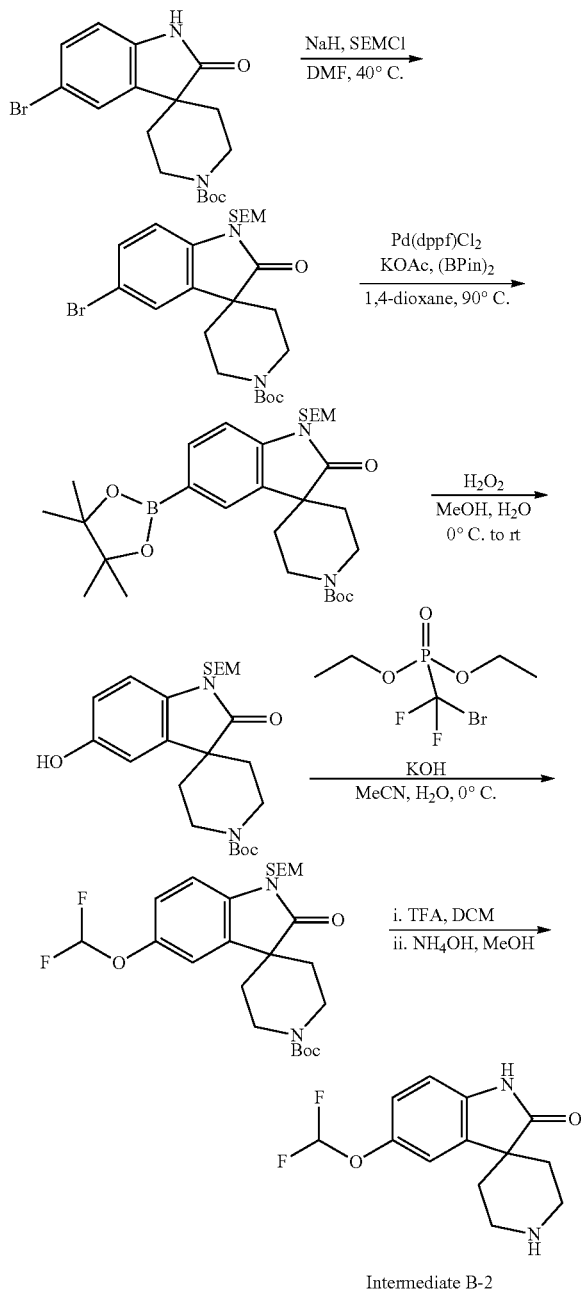

Step 1: tert-butyl 5-bromo-2-oxo-1-{[2-(trimethylsilyl)ethoxy]methyl}-1,2-dihydrospiro[indole-3,4'-piperidine]-1'-carboxylate To a solution of tert-butyl 5-bromo-2-oxo-1,2-dihydrospiro[indole-3,4'-piperidine]-1'-carboxylate (1.55 g, 4.06 mmol) in DMF (21 mL) was added sodium hydride (195 mg, 60 wt % in mineral oil, 4.9 mmol). After one hour, SEMCl (935 µL, 5.3 mmol) was added dropwise over 30 sec and the reaction mixture was heated to 40° C. After 48 h the reaction was removed from heat and diluted with EtOAc (50 mL) and quenched with H₂O (100 mL). The aqueous layer was then extracted with EtOAc (3×50 mL). The combined organic layers were then washed with brine (150 mL), dried over Na₂SO₄, filtered, and concentrated in vacuo. The crude reaction mixture was the purified by normal phase chromatography (Biotage 50 g cartridge 20% EtOAc:hexanes) to afford tert-butyl 5-bromo-2-oxo-1-{[2-(trimethylsilyl)ethoxy]methyl}-1,2-dihydrospiro[indole-3,4'-piperidine]-1'-carboxylate. $^1$H NMR (500 MHz, CDCl₃): δ 7.46 (app d, J=1.9 Hz, 2H), 7.02-6.96 (m, 1H), 5.17 (s, 2H), 3.85 (m, 4H), 3.69-3.44 (m, 2H), 2.00-1.74 (m, 4H), 1.55 (s, 9H), 1.05-0.82 (m, 2H), 0.00 (s, 9H).

Step 2: tert-butyl 2-oxo-5-(4,4,5,5-tetramethyl-1,3,2-dioxaborolan-2-yl)-1-{[2-(trimethylsilyl)ethoxy]methyl}-1,2-dihydrospiro[indole-3,4'-piperidine]-1'-carboxylate

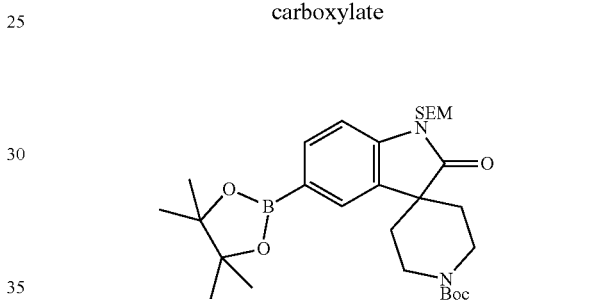

A solution tert-butyl 5-bromo-2-oxo-1-{[2-(trimethylsilyl)ethoxy]methyl}-1,2-dihydrospiro[indole-3,4'-piperidine]-1'-carboxylate (1.53 g, 3.1 mmol), KOAc (604 mg, 6.1 mmol), bis(pinacolato)diboron (937 mg, 2.2 mmol) in 1,4-dioxane (9.3 mL) was sparged with N₂ for 10 min. Pd(dppf)Cl₂ (113 mg, 0.15 mmol) was then added, and the reaction was heated to 90° C. for 2 h. The reaction mixture was then cooled to room temperature, filtered over Celite, washed with EtOAc (30 mL), and concentrated in vacuo. The crude material was then purified by normal phase chromatography (Biotage 25 g cartridge, 10% EtOAc:hexanes) to give tert-butyl 2-oxo-5-(4,4,5,5-tetramethyl-1,3,2-dioxaborolan-2-yl)-1-{[2-(trimethylsilyl)ethoxy]methyl}-1,2-dihydrospiro[indole-3,4'-piperidine]-1'-carboxylate.

Step 3. Tert-butyl 5-hydroxy-2-oxo-1-{[2-(trimethylsilyl)ethoxy]methyl}-1,2-dihydrospiro[indole-3,4'-piperidine]-1'-carboxylate

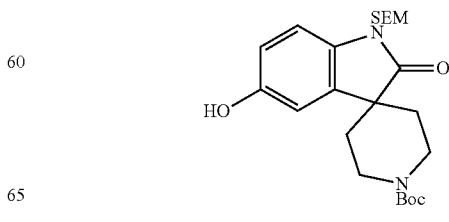

tert-Butyl 5-hydroxy-2-oxo-1-{[2-(trimethylsilyl)ethoxy]methyl}-1,2-dihydrospiro[indole-3,4'-piperidine]-1'-carboxylate (3.1 mmol) was dissolved in MeOH (20.5 mL). The solution was cooled to 0° C. and 30% aqueous hydrogen peroxide solution (1.05 mL, 9.3 mmol) was added dropwise over 3 min. The reaction mixture was then warmed to room temperature and stirred for 16 h. The reaction mixture was then extracted with EtOAc (3×50 mL). The combined organic layers were washed with brine (30 mL), dried over Na$_2$SO$_4$, filtered, and concentrated in vacuo. The crude residue was purified by normal phase chromatography (Biotage 25 g cartridge, 40% EtOAc in hexanes) to afford tert-butyl 5-hydroxy-2-oxo-1-{[2-(trimethylsilyl)ethoxy]methyl}-1,2-dihydrospiro[indole-3,4'-piperidine]-1'-carboxylate. $^1$H NMR (500 MHz, CDCl$_3$, 35/36 H): δ 6.96 (d, J=8.4 Hz, 1H), 6.91 (s, 1H), 6.82 (d, J=8.4, 1H), 5.16 (s, 2H), 3.96-3.71 (m, 4H), 3.67-3.49 (m, 2H), 1.87-1.85 (m, 2H), 1.77-1.75 (m, 2H), 1.56 (s, 9H), 1.00-0.91 (m, 2H), 0.00 (s, 9H).

Step 4: tert-Butyl 5-(difluoromethoxy)-2-oxo-1-{[2-(trimethylsilyl)ethoxy]methyl}-1,2-dihydrospiro[indole-3,4'-piperidine]-1'-carboxylate

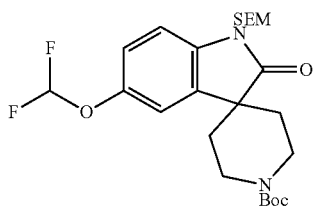 [SMILES: CC(C)(C)OC(=O)N1CCC2(CC1)C(=O)N(COCC[Si](C)(C)C)c1ccc(OC(F)F)cc12]

A solution of tert-butyl 5-hydroxy-2-oxo-1-{[2-(trimethylsilyl)ethoxy]methyl}-1,2-dihydrospiro[indole-3,4'-piperidine]-1'-carboxylate (295 mg, 0.66 mmol) in MeCN (2 mL) and H$_2$O (2 mL) was cooled to 0° C. and KOH (738 mg, 13.1 mmol) was added. The mixture was stirred at 0° C. for 20 min, then diethyl bromodifluoromethyl phosphonate (316 mg, 1.18 mmol) was added. After 2 h, the reaction mixture was acidified to pH=3 by addition of 1.0 M aqueous HCl. The reaction mixture was extracted with EtOAc (3×30 mL). The combined organic layers were washed with brine (30 mL), dried over Na$_2$SO$_4$, filtered, and concentrated in vacuo. Purification by normal phase chromatography (Biotage 10 g cartridge, 30% EtOAc:hexanes) gave tert-butyl 5-(difluoromethoxy)-2-oxo-1-{[2-(trimethylsilyl)ethoxy]methyl}-1,2-dihydrospiro[indole-3,4"-piperidine]-1"-carboxylate. $^1$H NMR (500 MHz, CDCl$_3$): δ 7.17-7.04 (m, 3H), 6.50 (t, J=73.8 Hz, 1H), 5.18 (s, 2H), 3.98-3.78 (m, 4H), 3.68-3.46 (m, 2H), 1.98-1.74 (m, 4H), 1.54 (s, 9H), 1.06-0.84 (m, 2H), 0.00 (s, 9H).

Step 5: 5-(Difluoromethoxy)-1,2-dihydrospiro[indole-3,4'-piperidin]-2-one

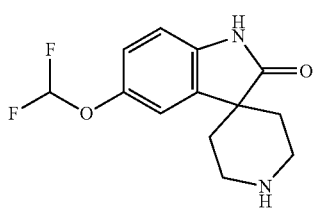 [SMILES: O=C1Nc2ccc(OC(F)F)cc2C12CCNCC2]

To a solution of tert-butyl 5-(difluoromethoxy)-2-oxo-1-{[2-(trimethylsilyl)ethoxy]methyl}-1,2-dihydrospiro[indole-3,4'-piperidine]-1'-carboxylate (139 mg, 0.28 mmol) in DCM (1.4 mL) was added TFA (530 μL, 5.6 mmol), then was stirred at room temperature for 2 h. The reaction mixture was then concentrated in vacuo and dissolved in MeOH (1.5 mL) and ammonium hydroxide (500 μL). After 5 min, the reaction mixture was concentrated and triturated with MTBE (5 mL). The solid was then filtered and dried in vacuo to afford 5-(difluoromethoxy)-1,2-dihydrospiro[indole-3,4'-piperidin]-2-one (Intermediate B-2), which was used in the subsequent step without further purification. MS=269.2 [M+H]$^+$.

General Procedure for Intermediates B-3 to B-5

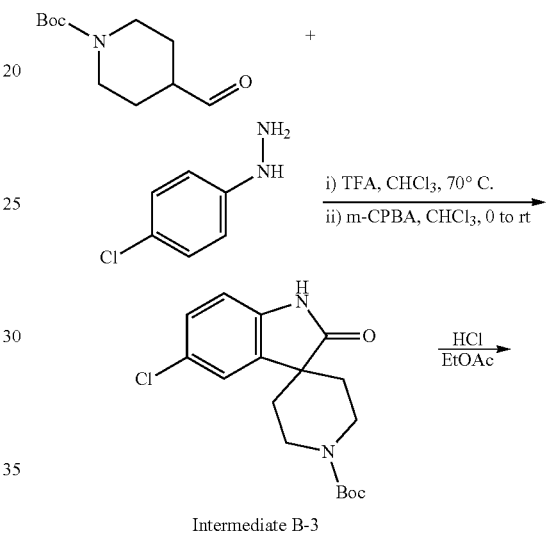

Intermediate B-3

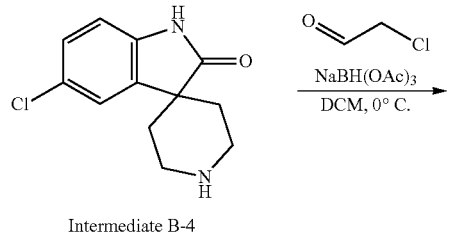

Intermediate B-4

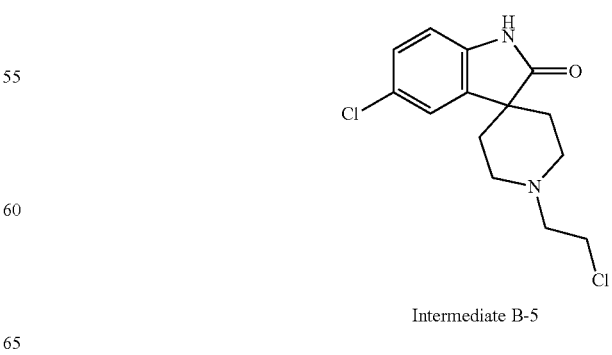

Intermediate B-5

Step 1: tert-butyl 5-chloro-2-oxo-1,2-dihydrospiro[indole-3,4'-piperidine]-1'-carboxylate

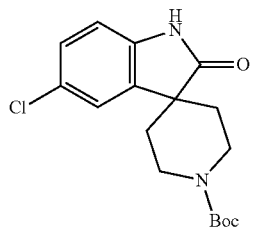 [SMILES: CC(C)(C)OC(=O)N1CCC2(CC1)C(=O)Nc1ccc(Cl)cc12]

To a solution of tert-butyl 4-formylpiperidine-1-carboxylate (15.0 g, 70.3 mmol) and (4-chlorophenyl)hydrazine (15.1 g, 84.4 mmol, HCl salt) in CHCl$_3$ (200 mL) was added TFA (15.6 mL, 211 mmol). The mixture was stirred at 70° C. for 1 h, then cooled to 0° C. and m-CPBA (35.7 g, 85% purity, 176 mmol) was added. The mixture was warmed to room temperature and stirred for 1 h. The reaction mixture was cooled to 0° C. then quenched with saturated aqueous Na$_2$CO$_3$ (300 mL) and extracted with EtOAc (3×200 mL). The combined organic layers were washed with saturated aqueous Na$_2$SO$_3$ (150 mL) and brine (3×100 mL), dried over Na$_2$SO$_4$, filtered, and concentrated in vacuo. The crude residue was purified by normal phase silica gel chromatography (Biotage 330 g cartridge, 0-100% EtOAc:petroleum ether) to give tert-butyl 5-chloro-2-oxo-1,2-dihydrospiro[indole-3,4'-piperidine]-1'-carboxylate (Intermediate B-3). MS=281.1 [M-C$_4$H$_8$+H]$^+$.

Step 2: 5-chloro-1,2-dihydrospiro[indole-3,4'-piperidin]-2-one

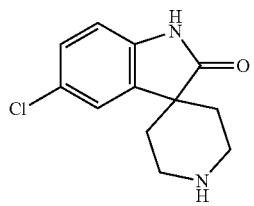 [SMILES: O=C1Nc2ccc(Cl)cc2C12CCNCC2]

A solution of tert-butyl 5-chloro-2-oxo-1,2-dihydrospiro[indole-3,4'-piperidine]-1'-carboxylate (5.00 g, 14.9 mmol) and 4.0 M HCl in EtOAc (50 mL) was stirred for 1 h. The mixture was partially concentrated under reduced pressure to give a slurry. The suspension was filtered to isolate a solid, which was triturated with EtOAc (5 mL) and dried in vacuo to give 5-chloro-1,2-dihydrospiro[indole-3,4'-piperidin]-2-one (Intermediate B-4, HCl salt). MS=237.1 [M+H]$^+$.

Step 3: 5-chloro-1'-(2-chloroethyl)-1,2-dihydrospiro[indole-3,4'-piperidin]-2-one

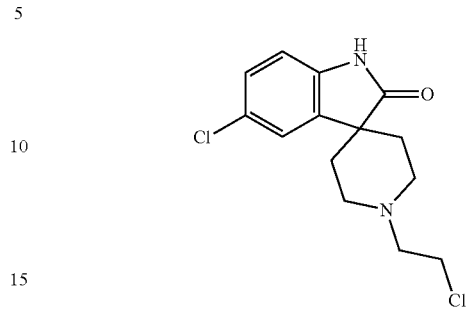

A 0° C. solution of 5-chloro-1,2-dihydrospiro[indole-3,4'-piperidin]-2-one (3.50 g, 12.8 mmol, HCl salt) and 2-chloroacetaldehyde in H$_2$O (2.68 mL, 40 wt %, 16.6 mmol) in DCM (50 mL) was stirred for 10 min, then NaBH(OAc)$_3$ (6.09 g, 28.7 mmol) was added. The mixture was stirred at 0° C. for 1 h and was then quenched with H$_2$O (30 mL). The resulting biphasic mixture was adjusted to pH=9 with saturated aqueous Na$_2$CO$_3$ and was extracted with DCM (3×15 mL). The combined organic layers were dried over Na$_2$SO$_4$, filtered and concentrated in vacuo to give 5-chloro-1'-(2-chloroethyl)-1,2-dihydrospiro[indole-3,4'-piperidin]-2-one (Intermediate B-5). $^1$H NMR (400 MHz, DMSO-d$_6$): δ 10.50 (s, 1H), 7.52 (br s, 1H), 7.25 (dd, J=8.4, 2.0 Hz, 1H), 6.84 (d, J=8.0 Hz, 1H), 3.75-3.72 (m, 2H), 2.90-2.56 (m, 6H), 1.79-1.70 (m, 4H). MS=299.1 [M+H]$^+$.

General Procedure for Intermediates B-6 & B-7

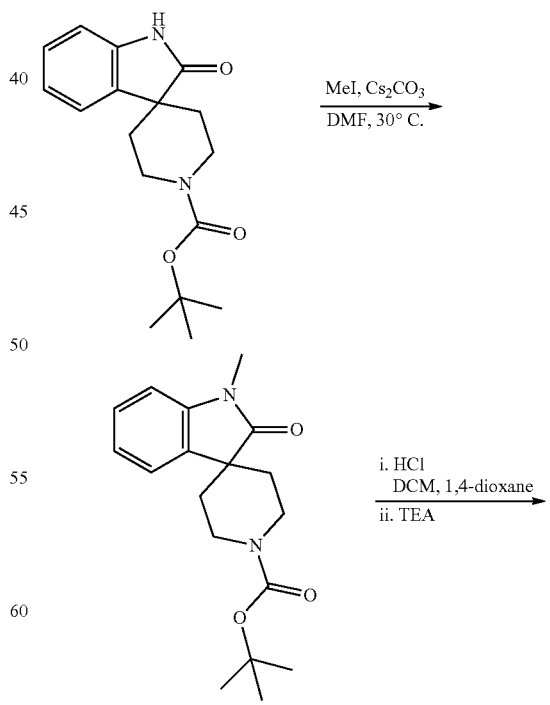

Step 1: tert-butyl 1-methyl-2-oxo-1,2-dihydrospiro[indole-3,4'-piperidine]-1'-carboxylate

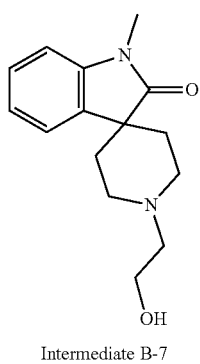

A mixture of tert-butyl 1-methyl-2-oxo-1,2-dihydrospiro[indole-3,4'-piperidine]-1'-carboxylate (10.0 g, 33.1 mmol), Cs$_2$CO$_3$ (21.6 g, 66.1 mmol), and MeI (20.6 mL, 331 mmol) in DMF (100 mL) was degassed and purged with N$_2$ (3×). The mixture was stirred at 30° C. for 12 h under N$_2$ atmosphere and was then filtered and concentrated in vacuo to give tert-butyl 1-methyl-2-oxo-1,2-dihydrospiro[indole-3,4'-piperidine]-1'-carboxylate, which was taken to the next step without further purification. MS=317.1 [M+H]$^+$.

Step 2: 1-methyl-1,2-dihydrospiro[indole-3,4'-piperidin]-2-one

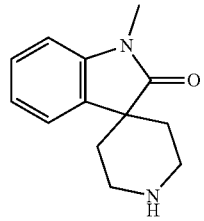 [SMILES: CN1C(=O)C2(CCNCC2)c2ccccc21]

To a solution of tert-butyl 1-methyl-2-oxo-1,2-dihydrospiro[indole-3,4'-piperidine]-1'-carboxylate (33.1 mmol) in DCM (100 mL) was added 4.0 M HCl in 1,4-dioxane (40 mL, 160 mmol). The mixture was stirred for 12 h. The reaction mixture was adjusted to pH=8 with the dropwise addition of TEA. The solution was filtered and concentrated in vacuo to give 1-methyl-1,2-dihydrospiro[indole-3,4'-piperidin]-2-one, which was taken to the next step without further purification (Intermediate B-6). MS=217.1 [M+H]$^+$.

Step 3: 1'-(2-hydroxyethyl)-1-methyl-1,2-dihydrospiro[indole-3,4'-piperidin]-2-one

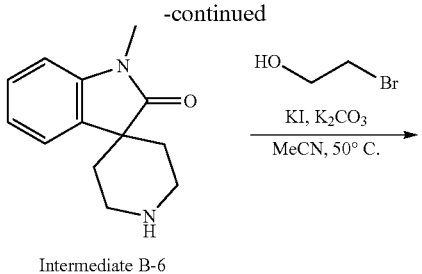
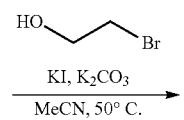

Intermediate B-6

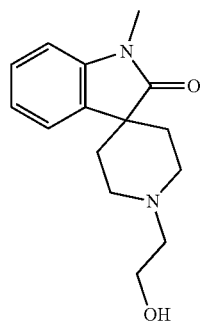 [SMILES: CN1C(=O)C2(CCN(CCO)CC2)c2ccccc21]

To a solution of 1-methyl-1,2-dihydrospiro[indole-3,4'-piperidin]-2-one (33.1 mmol) and 2-bromoethanol (3.15 mL, 44.4 mmol) in MeCN (80 mL) was added KI (614 mg, 3.70 mmol) and K$_2$CO$_3$ (10.2 g, 74.0 mmol). The mixture was stirred at 50° C. for 12 h. After cooling to room temperature, the reaction mixture was filtered and concentrated in vacuo to give 1'-(2-hydroxyethyl)-1-methyl-1,2-dihydrospiro[indole-3,4'-piperidin]-2-one (Intermediate B-7), which was taken to the next steps without purification. MS=261.2 [M+H]$^+$.

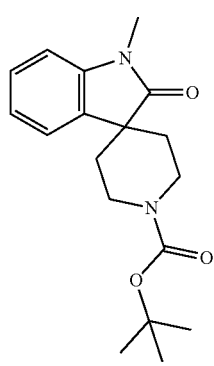

Intermediate B-7

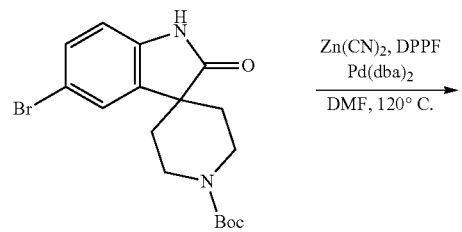

-continued

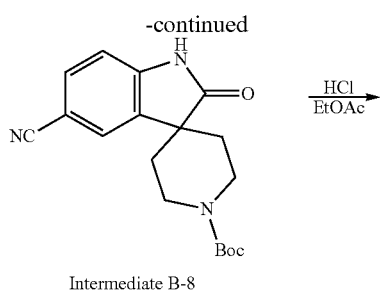

Intermediate B-8

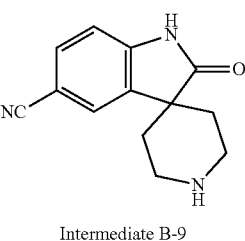

Intermediate B-9

Step 1: tert-butyl 5-cyano-2-oxo-1,2-dihydrospiro[indole-3,4'-piperidine]-1'-carboxylate

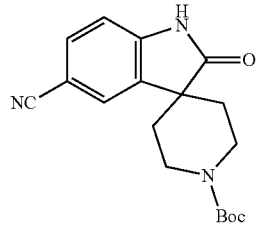 [SMILES: CC(C)(C)OC(=O)N1CCC2(CC1)C(=O)Nc1ccc(C#N)cc12]

To a solution of tert-butyl 5-bromo-2-oxo-1,2-dihydrospiro[indole-3,4'-piperidine]-1'-carboxylate (6.00 g, 15.7 mmol), Zn(CN)$_2$ (5.54 g, 47.2 mmol), DPPF (436 mg, 0.787 mmol) in DMF (120 mL) was added Pd(dba)$_2$ (905 mg, 1.57 mmol). The mixture was degassed and purged with N$_2$ (3×), and then the mixture was stirred at 120° C. for 12 h. After cooling to room temperature, the reaction mixture was quenched by the addition of H$_2$O (50 mL) and extracted with EtOAc (3×50 mL). The combined organic layers were washed with brine (3×50 mL), dried over Na$_2$SO$_4$, filtered, and concentrated in vacuo. The crude residue was purified by normal phase silica gel chromatography (Biotage 80 g cartridge, 0-50% EtOAc:petroleum ether) to give tert-butyl 5-cyano-2-oxo-1,2-dihydrospiro[indole-3,4'-piperidine]-1'-carboxylate (Intermediate B-8). MS=272.2 [M-C$_4$H$_8$+H]$^+$.

Step 2: 2-oxo-1,2-dihydrospiro[indole-3,4'-piperidine]-5-carbonitrile

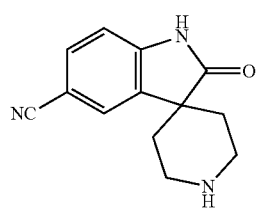 [SMILES: N#Cc1ccc2c(c1)C1(CCNCC1)C(=O)N2]

To a solution of tert-butyl 5-cyano-2-oxo-1,2-dihydrospiro[indole-3,4'-piperidine]-1'-carboxylate (3.80 g, 11.6 mmol) in EtOAc (40 mL) was added 4.0 M HCl in EtOAc (10 mL, 40 mmol). The mixture was stirred for 2 h, and the resulting solid was isolated via filtration to give 2-oxo-1,2-dihydrospiro[indole-3,4'-piperidine]-5-carbonitrile (Intermediate B-9, HCl salt), which was used in subsequent steps without further purification. $^1$H NMR (400 MHz, DMSO-d$_6$): δ 11.19 (s, 1H), 9.33 (s, 2H), 7.70 (s, 1H), 7.60 (d, J=8.4 Hz, 1H), 7.04 (d, J=8.4 Hz, 1H), 3.43-3.41 (m, 2H), 3.40-3.39 (m, 2H), 2.13-2.07 (m, 2H), 1.99-1.92 (m, 2H). MS=228.3 [M+H]$^+$.

General Procedure for Intermediate B-10

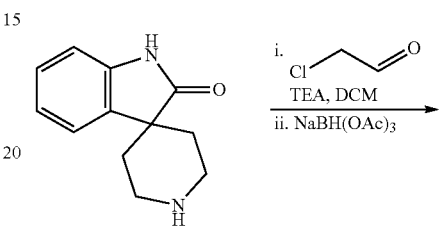

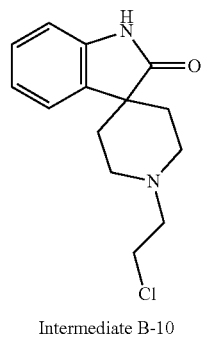

Intermediate B-10

Step 1: 1'-(2-chloroethyl)-1,2-dihydrospiro[indole-3,4'-piperidin]-2-one

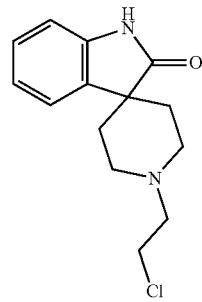 [SMILES: O=C1Nc2ccccc2C12CCN(CCCl)CC2]

A mixture of 1,2-dihydrospiro[indole-3,4'-piperidin]-2-one (1.00 g, 4.19 mmol, HCl salt), 2-chloroacetaldehyde in H$_2$O (1.35 mL, 40 wt %, 8.38 mmol) and TEA (1.75 mL, 12.8 mmol) in DCM (10 mL) was stirred for 2 h, and then NaBH(OAc)$_3$ (1.78 g, 8.38 mmol) was added. After stirring for 30 min, the reaction mixture was quenched by the addition of H$_2$O (10 mL) and extracted with DCM (3×10 mL). The combined organic layers were dried over Na$_2$SO$_4$, filtered, and concentrated in vacuo. The crude residue was purified by normal phase silica gel chromatography (Isco 10 g cartridge, 0-100% EtOAc:petroleum ether) to give 1'-(2-chloroethyl)-1,2-dihydrospiro[indole-3,4'-piperidin]-2-one (Intermediate B-10). ¹H NMR (400 MHz, DMSO-d₆): δ 10.36 (s, 1H), 7.47-7.45 (m, 1H), 7.19 (app t, J=7.6 Hz, 1H), 6.95 (app t, J=7.6 Hz, 1H), 6.85-6.83 (m, 1H), 3.77-3.74 (m, 2H), 2.97-2.67 (m, 6H), 1.79-1.64 (m, 4H). MS=265.1 [M+H]⁺.

General Procedure for Intermediate B-11

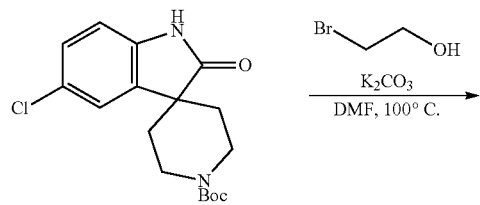

Intermediate B-3

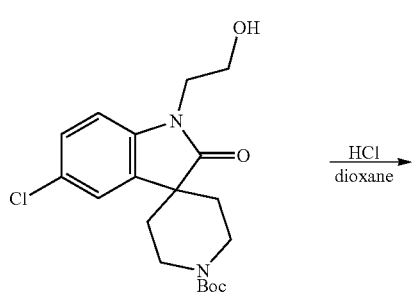

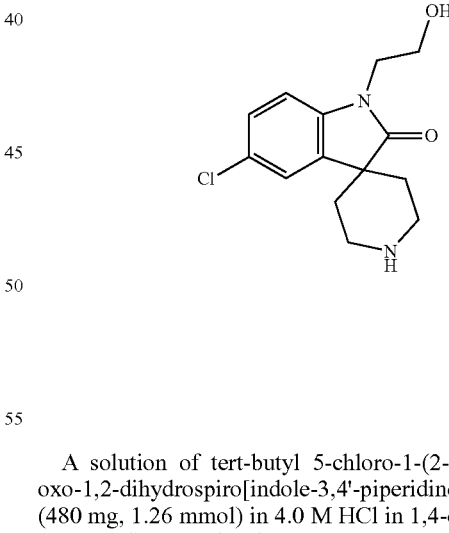

Intermediate B-11

Step 1: tert-butyl 5-chloro-1-(2-hydroxyethyl)-2-oxo-1,2-dihydrospiro[indole-3,4'-piperidine]-1'-carboxylate

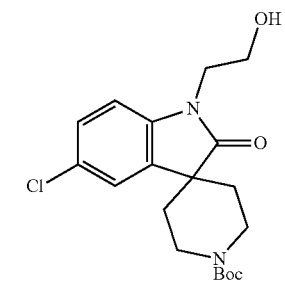 [SMILES: CC(C)(C)OC(=O)N1CCC2(CC1)C(=O)N(CCO)c1ccc(Cl)cc12]

To a solution of tert-butyl 5-chloro-2-oxo-1,2-dihydrospiro[indole-3,4'-piperidine]-1'-carboxylate (Intermediate B-3, 500 mg, 1.48 mmol) and 2-bromoethanol (0.738 mL, 10.4 mmol) in DMF (5 mL) was added K₂CO₃ (1.03 g, 7.42 mmol). The mixture was stirred at 100° C. for 12 h. After cooling to room temperature, the reaction mixture was diluted with H₂O (10 mL) and extracted with EtOAc (3×30 mL). The combined organic layers were washed with brine (40 mL), dried over Na₂SO₄, filtered, and concentrated in vacuo. The crude residue was purified by normal phase silica gel chromatography (Biotage 12 g cartridge, 0-100% EtOAc:petroleum ether) to give tert-butyl 5-chloro-1-(2-hydroxyethyl)-2-oxo-1,2-dihydrospiro[indole-3,4'-piperidine]-1'-carboxylate. MS=325.1 [M-C₄H₈+H]⁺.

Step 2: 5-chloro-1-(2-hydroxyethyl)-1,2-dihydrospiro[indole-3,4'-piperidin]-2-one

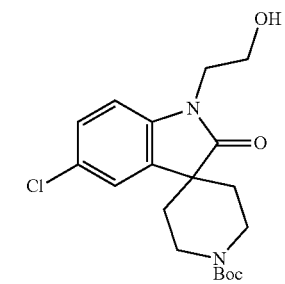

A solution of tert-butyl 5-chloro-1-(2-hydroxyethyl)-2-oxo-1,2-dihydrospiro[indole-3,4'-piperidine]-1'-carboxylate (480 mg, 1.26 mmol) in 4.0 M HCl in 1,4-dioxane (2.0 mL, 8.0 mmol) was stirred at room temperature for 1 h. The mixture was concentrated in vacuo to give 5-chloro-1-(2-hydroxyethyl)-1,2-dihydrospiro[indole-3,4'-piperidin]-2-one (Intermediate B-11), which was used in the subsequent step without further purification. MS=281.2 [M+H]⁺.

The following intermediates in Table 12 were prepared according to procedures similar those described for Intermediate B-11 using the appropriate starting materials.

General Procedure for Intermediates B-12 to B-15

TABLE 12

| Intermediate # | Structure | Name | Exact Mass [M + H]+ |
|---|---|---|---|
| B-12 | 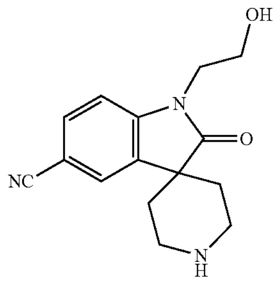 [SMILES: N#Cc1ccc2c(c1)C1(CCNCC1)C(=O)N2CCO] | 1-(2-hydroxyethyl)-2-oxo-1,2-dihydrospiro[indole-3,4'-piperidine]-5-carbonitrile | Calc'd 272.1 Found 272.2 |
| B-13 | 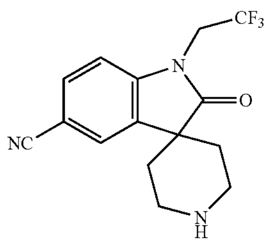 [SMILES: N#Cc1ccc2c(c1)C1(CCNCC1)C(=O)N2CC(F)(F)F] | 2-oxo-1-(2,2,2-trifluoroethyl)-1,2-dihydrospiro[indole-3,4'-piperidine]-5-carbonitrile | Calc'd 310.1 Found 310.1 |
| B-14 | 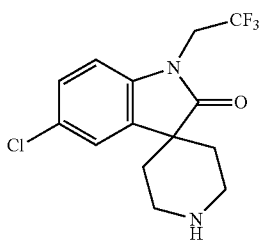 [SMILES: O=C1N(CC(F)(F)F)c2ccc(Cl)cc2C12CCNCC2] | 5-chloro-1-(2,2,2-trifluoroethyl)-1,2-dihydrospiro[indole-3,4'-piperidin]-2-one | Calc'd 319.1 Found 319.1 |
| B-15 | 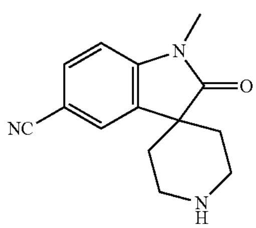 [SMILES: CN1C(=O)C2(CCNCC2)c2cc(C#N)ccc21] | 1-methyl-2-oxo-1,2-dihydrospiro[indole-3,4'-piperidine]-5-carbonitrile | Calc'd 242.1 Found 242.2 |

General Procedure for Intermediate B-16

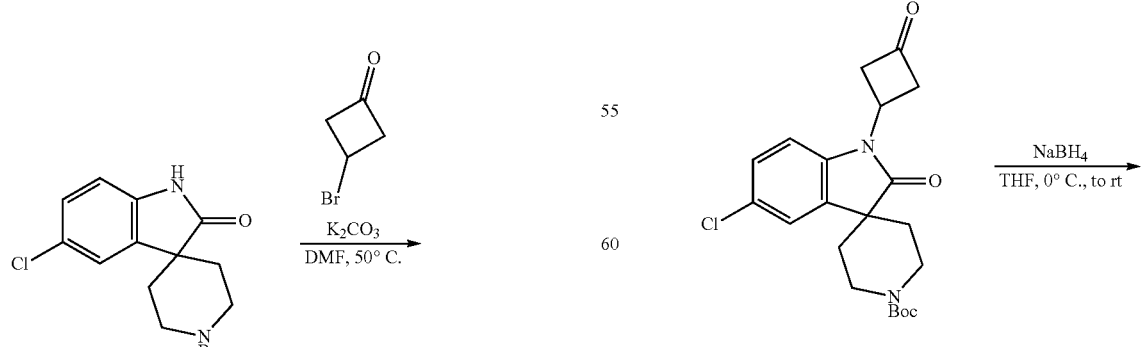

-continued

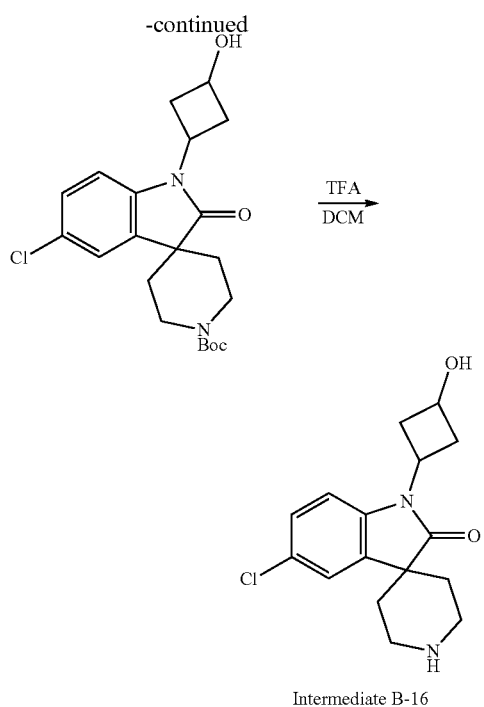

Intermediate B-16

Step 1: tert-butyl 5-chloro-2-oxo-1-(3-oxocyclobutyl)-1,2-dihydrospiro[indole-3,4'-piperidine]-1'-carboxylate

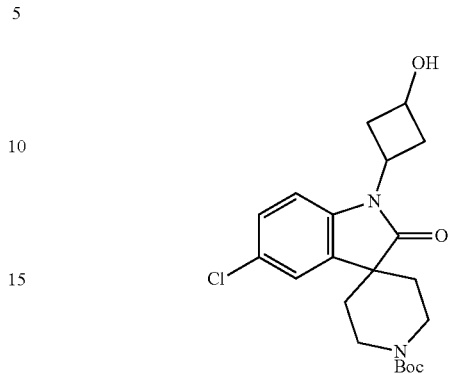

To a solution of tert-butyl 5-chloro-2-oxo-1,2-dihydrospiro[indole-3,4'-piperidine]-1'-carboxylate (Intermediate B-3, 1.00 g, 2.97 mmol) and 3-bromocyclobutanone (1.33 g, 8.91 mmol) in DMF (13 mL) was added $K_2CO_3$ (820 mg, 5.94 mmol). The mixture was stirred at 50° C. for 4 h. The reaction mixture was quenched with $H_2O$ (30 mL), and then extracted with EtOAc (2×30 mL). The combined organic layers were washed with brine (2×30 mL), dried over $Na_2SO_4$, filtered, and concentrated in vacuo. The crude residue was purified by normal phase silica gel chromatography (Biotage 40 g cartridge, 0-30% EtOAc:Petroleum ether) to give tert-butyl 5-chloro-2-oxo-1-(3-oxocyclobutyl)-1,2-dihydrospiro[indole-3,4'-piperidine]-1'-carboxylate. MS=349.0 $[M-C_4H_8+H]^+$.

Step 2: tert-butyl 5-chloro-1-(3-hydroxycyclobutyl)-2-oxo-1,2-dihydrospiro[indole-3,4'-piperidine]-1'-carboxylate

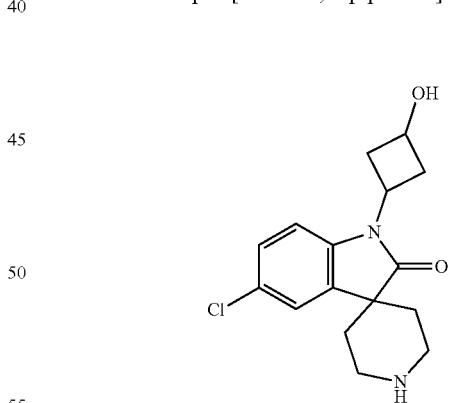

To a 0° C. solution of tert-butyl 5-chloro-2-oxo-1-(3-oxocyclobutyl)-1,2-dihydrospiro[indole-3,4'-piperidine]-1'-carboxylate (500 mg, 1.23 mmol) in THF (10 mL) was added $NaBH_4$ (160 mg, 4.23 mmol). The mixture was allowed to warm to room temperature and stirred for 30 min. The reaction mixture was quenched with $H_2O$ (20 mL) and then extracted with EtOAc (2×20 mL). The combined organic layers were washed with brine (2×20 mL), dried over $Na_2SO_4$, filtered, and concentrated in vacuo. The crude residue was purified by normal phase silica gel chromatography (Biotage 20 g cartridge, 20-30% EtOAc:petroleum ether) to give tert-butyl 5-chloro-1-(3-hydroxycyclobutyl)-2-oxo-1,2-dihydrospiro[indole-3,4'-piperidine]-1'-carboxylate. $^1$HNMR (400 MHz, DMSO-$d_6$): δ 7.60 (d, J=2.0 Hz, 1H), 7.35-7.28 (m, 2H), 5.32 (d, J=6.8 Hz, 1H), 4.22-4.14 (m, 1H), 3.99-3.91 (m, 1H), 3.72-3.63 (m, 4H), 2.66-2.52 (m, 4H), 1.77-1.62 (m, 4H), 1.44 (s, 9H).

Step 3: 5-chloro-1-(3-hydroxycyclobutyl)-1,2-dihydrospiro[indole-3,4'-piperidin]-2-one To a solution of tert-butyl 5-chloro-1-(3-hydroxycyclobutyl)-2-oxo-1,2-dihydrospiro[indole-3,4'-piperidine]-1'-carboxylate (400 mg, 0.983 mmol) in DCM (5 mL) was added TFA (1.50 g, 13.5 mmol). Then the mixture was stirred at room temperature for 1 h. The mixture was concentrated in vacuo, then diluted with $H_2O$ (5 mL), and adjusted to pH=7-8 via dropwise addition of saturated aqueous $NaHCO_3$. The mixture was extracted with EtOAc (3×15 mL). The combined organic layers were washed with brine (20 mL), dried over $Na_2SO_4$, filtered, and concentrated in vacuo to give 5-chloro-1-(3-hydroxycyclobutyl)-1,2-dihydrospiro[indole-3,4'-piperidin]-2-one (Intermediate B-16), which was used in the subsequent step without further purification. MS=307.2 [M+H]+.

General Procedure for Intermediates B-17 and B-18

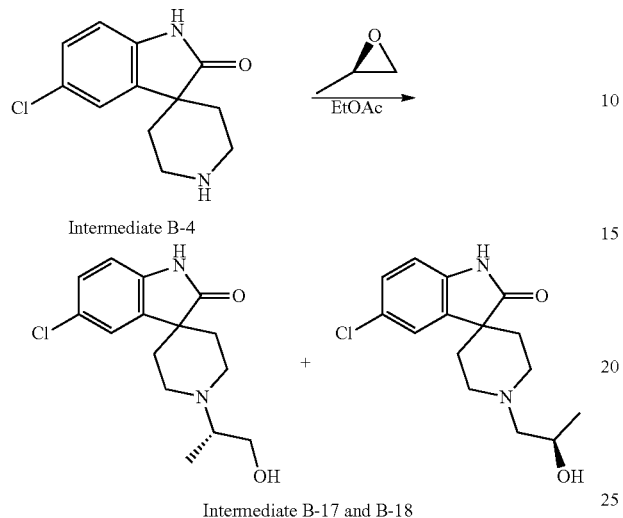

Intermediate B-17 and B-18

Step 1: 5-chloro-1'-[(2S)-1-hydroxypropan-2-yl]-1,2-dihydrospiro[indole-3,4'-piperidin]-2-one and 5-chloro-1'-[(2R)-2-hydroxypropyl]-1,2-dihydrospiro[indole-3,4'-piperidin]-2-one

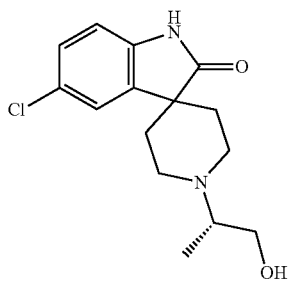

To a solution of 5-chloro-1,2-dihydrospiro[indole-3,4'-piperidin]-2-one (Intermediate B-4, 500 mg, 2.11 mmol) in EtOH (7 mL) was added (2R)-2-methyloxirane (0.592 mL, 8.45 mmol). The mixture was stirred at room temperature for 20 h. The reaction was concentrated in vacuo to give a mixture of 5-chloro-1'-[(2S)-1-hydroxypropan-2-yl]-1,2-dihydrospiro[indole-3,4'-piperidin]-2-one and 5-chloro-1'-[(2R)-2-hydroxypropyl]-1,2-dihydrospiro[indole-3,4'-piperidin]-2-one (Intermediates B-17 and B-18). MS=295.2 [M+H]+.

The following intermediates in Table 13 were prepared according to procedures similar those described for Intermediates B-17 and B-18 using the appropriate starting materials.

General Procedure for Intermediates B-19 to B-22

TABLE 13

| Intermediate # | Structure | | Name | Exact Mass [M + H]+ | Intermediate Starting Materials Used |
|---|---|---|---|---|---|
| B-19 and B-20 | ![structure] | + ![structure] | (S)-1'-(1-hydroxypropan-2-yl)-2-oxospiro[indoline-3,4'-piperidine]-5-carbonitrile and 1'-[(2R)-2-hydroxypropyl]-2-oxo-1,2-dihydrospiro[indole-3,4'-piperidine]-5-carbonitrile | Calc'd 286.1 Found 286.2 | B-9 |

TABLE 13-continued

| Intermediate # | Structure | Name | Exact Mass [M + H]+ | Intermediate Starting Materials Used |
|---|---|---|---|---|
| B-21 and B-22 | 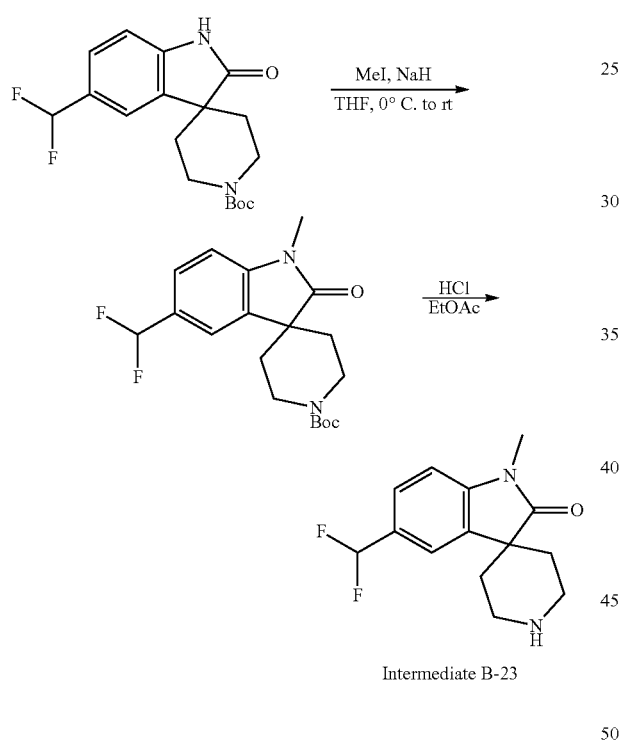 | 1'-[(2S)-1-hydroxypropan-2-yl]-1,2-dihydrospiro[indole-3,4'-piperidin]-2-one and 1'-[(2R)-2-hydroxypropyl]-1,2-dihydrospiro[indole-3,4'-piperidin]-2-one | Calc'd 261.1 Found 261.3 | n/a |

General Procedure for Intermediate B-23

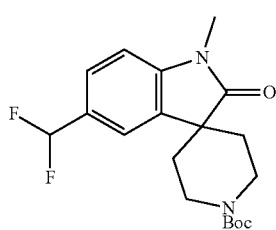

Intermediate B-23

Step 1: tert-butyl 5-(difluoromethyl)-1-methyl-2-oxo-1,2-dihydrospiro[indole-3,4'-piperidine]-1'-carboxylate To a 0° C. solution of tert-butyl 5-(difluoromethyl)-2-oxo-1,2-dihydrospiro[indole-3,4'-piperidine]-1'-carboxylate (Procedure for Intermediate B-1, Step 3, 4.50 g, 12.8 mmol) in THF (50 mL) was added sodium hydride (613 mg, 60 wt % in mineral oil, 15.3 mmol). After stirring for 30 min, iodomethane (2.18 g, 15.32 mmol) was added to the mixture. The mixture was allowed to warm to room temperature and stirred for 12 h. The reaction mixture was quenched with saturated aqueous NH$_4$Cl (50 mL) and extracted with EtOAc (3×50 mL). The combined organic layers were dried over Na$_2$SO$_4$, filtered, and concentrated under reduced pressure to give tert-butyl 5-(difluoromethyl)-1-methyl-2-oxo-1,2-dihydrospiro[indole-3,4'-piperidine]-1'-carboxylate, which was used in the subsequent step without further purification. MS=311.1 [M-C$_4$H$_8$+H]$^+$.

Step 2: 5-(difluoromethyl)-1-methyl-1,2-dihydrospiro[indole-3,4'-piperidin]-2-one To a 0° C. solution of tert-butyl 5-(difluoromethyl)-1-methyl-2-oxo-1,2-dihydrospiro[indole-3,4'-piperidine]-1'-carboxylate (4.00 g, 10.9 mmol) in EtOAc (20 mL) was added 4.0 M HCl in EtOAc (20.0 mL, 80.0 mmol). The mixture was allowed to warm to room temperature and stirred for 2 h. The resulting solids were isolated by filtration and dried in vacuo to give 5-(difluoromethyl)-1-methyl-1,2-dihydrospiro[indole-3,4'-piperidin]-2-one (Intermediate B-23, HCl salt), which was used in the subsequent steps without further purification. MS=267.1 [M+H]$^+$.

Step 1: tert-butyl 5-chloro-7-iodo-2-oxo-1,2-dihydrospiro[indole-3,4'-piperidine]-1'-carboxylate

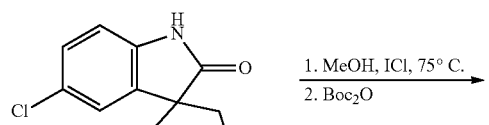

Intermediate B-4

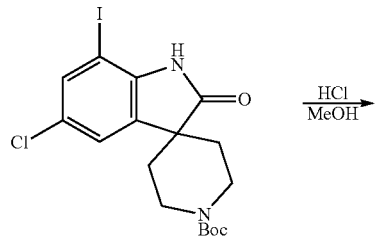

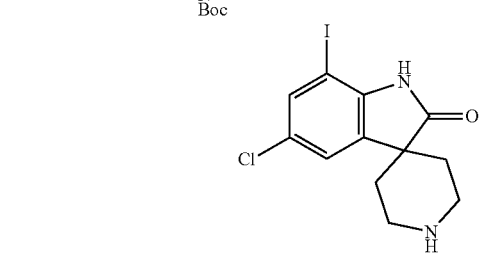

Intermediate B-24

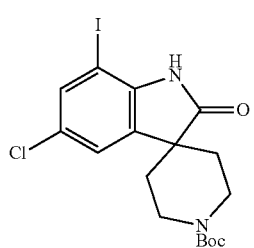 [SMILES: CC(C)(C)OC(=O)N1CCC2(CC1)C(=O)Nc1c(I)cc(Cl)cc12]

To a solution of 5-chloro-1,2-dihydrospiro[indole-3,4'-piperidin]-2-one (Intermediate B-4, 2.40 g, 10.1 mmol) in MeOH (20 mL) was added ICl (2.59 mL, 50.7 mmol). The mixture was stirred at 75° C. for 36 h. After cooling to room temperature, the reaction mixture was quenched with saturated aqueous Na$_2$S$_2$O$_3$ (20 mL). The mixture was concentrated under reduced pressure to remove MeOH. The aqueous solution was adjusted to pH=10 with saturated aqueous NaHCO$_3$, and then tert-butoxycarbonyl tert-butyl carbonate (2.21 g, 10.1 mmol) was added. The mixture was stirred at room temperature for 2 h. The reaction mixture was extracted with EtOAc (3×20 mL). The combined organic layers were washed with brine (30 mL), dried over Na$_2$SO$_4$, filtered, and concentrated in vacuo. The crude residue was purified by flash silica gel chromatography (Biotage 25 g cartridge, 0-10% MeOH:DCM) to give tert-butyl 5-chloro-7-iodo-2-oxo-1,2-dihydrospiro[indole-3,4'-piperidine]-1'-carboxylate.

Step 2: 5-chloro-7-iodo-1,2-dihydrospiro[indole-3,4'-piperidin]-2-one

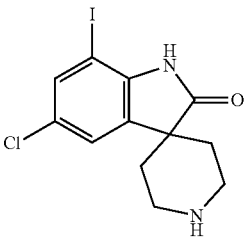

To a solution of tert-butyl 5-chloro-7-iodo-2-oxo-1,2-dihydrospiro[indole-3,4'-piperidine]-1'-carboxylate (369 mg, 0.797 mmol) in MeOH (3 mL) was added 4.0 M HCl in MeOH (15 mL, 60 mmol). The mixture was stirred at room temperature for 2 h. The reaction mixture was concentrated in vacuo to give 5-chloro-7-iodo-1,2-dihydrospiro[indole-3,4'-piperidin]-2-one (Intermediate B-24). MS=363.0 [M+H]$^+$.

General Procedure for Intermediate C-1

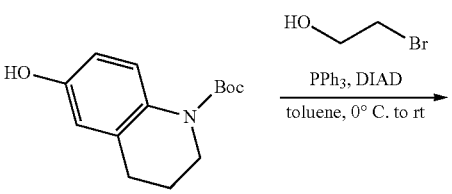

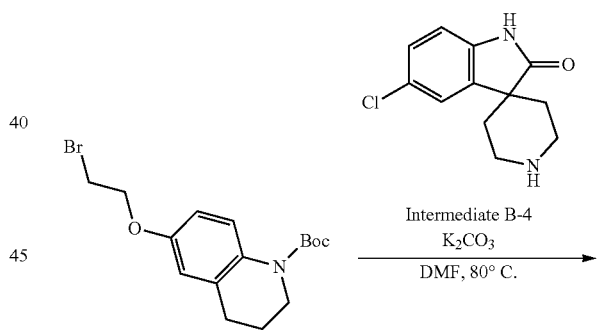

Intermediate B-4

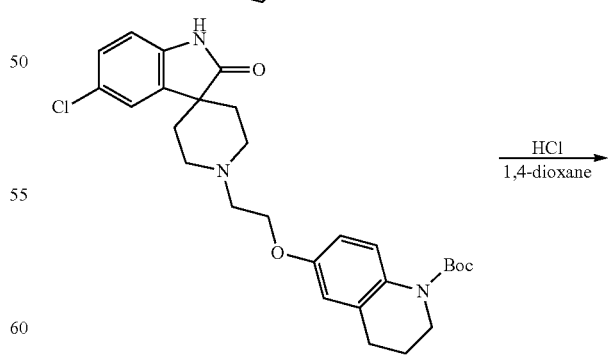

-continued

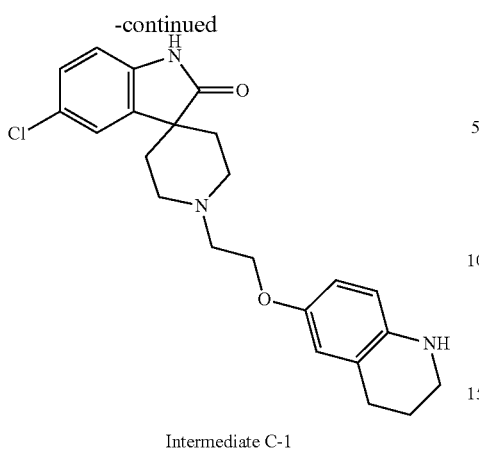

Intermediate C-1

Step 1: tert-butyl 6-(2-bromoethoxy)-1,2,3,4-tetrahydroquinoline-1-carboxylate

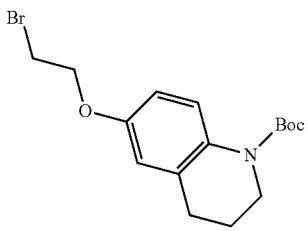 [SMILES: CC(C)(C)OC(=O)N1CCCc2cc(OCCBr)ccc21]

To a vial holding tert-butyl 6-hydroxy-1,2,3,4-tetrahydroquinoline-1-carboxylate (0.500 g, 2.01 mmol) were added toluene (20 mL), bromoethanol (0.501 g, 4.01 mmol), then polymer-bound PPh$_3$ (1.34 g, 3.00 mmol/g, 4.01 mmol). The reaction mixture was cooled to 0° C. and DIAD (0.608 g, 3.01 mmol) was added dropwise. The mixture was allowed to warm to room temperature and stirred for 16 h. The solids were removed by filtration and washed with EtOAc (25 mL). The filtrate was concentrated in vacuo. The crude residue was purified by normal phase silica gel chromatography (Biotage 25 g cartridge, 0-10% EtOAc:hexanes) to give tert-butyl 6-(2-bromoethoxy)-1,2,3,4-tetrahydroquinoline-1-carboxylate. MS=300.0 [M-C$_4$H$_8$+H]$^+$.

Step 2: tert-butyl 6-(2-{5-chloro-2-oxo-1,2-dihydrospiro[indole-3,4'-piperidin]-1'-yl}ethoxy)-1,2,3,4-tetrahydroquinoline-1-carboxylate

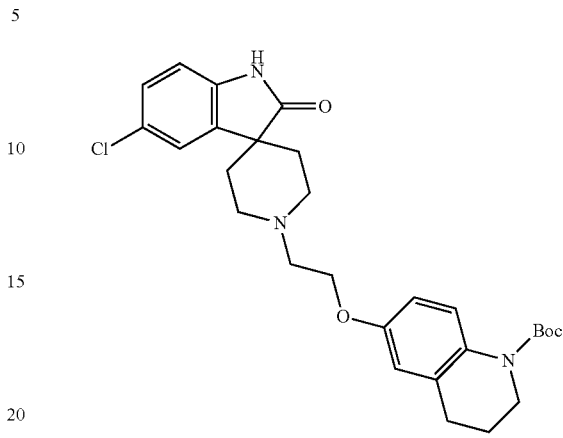

A solution of tert-butyl 6-(2-bromoethoxy)-1,2,3,4-tetrahydroquinoline-1-carboxylate (200 mg, 0.561 mmol), 5-chloro-1,2-dihydrospiro[indole-3,4'-piperidin]-2-one (Intermediate B-4, 161 mg, 0.589 mmol, HCl salt) and K$_2$CO$_3$ (0.233 g, 1.68 mmol) in DMF (5.6 mL) was heated at 80° C. for 2 h. After cooling to room temperature, the reaction mixture was diluted with H$_2$O (25 mL) and extracted with EtOAc (2×25 mL). The combined organic layers were dried over Na$_2$SO$_4$, filtered, and concentrated in vacuo. The crude residue was purified by normal phase silica gel chromatography (Biotage 25 g cartridge, 0-15% MeOH:DCM) to give tert-butyl 6-(2-{5-chloro-2-oxo-1,2-dihydrospiro[indole-3,4'-piperidin]-1'-yl}ethoxy)-1,2,3,4-tetrahydroquinoline-1-carboxylate. MS=512.2 [M+H]$^+$.

Step 3: 5-chloro-1'-[2-(1,2,3,4-tetrahydroquinolin-6-yloxy)ethyl]-1,2-dihydrospiro[indole-3,4'-piperidin]-2-one

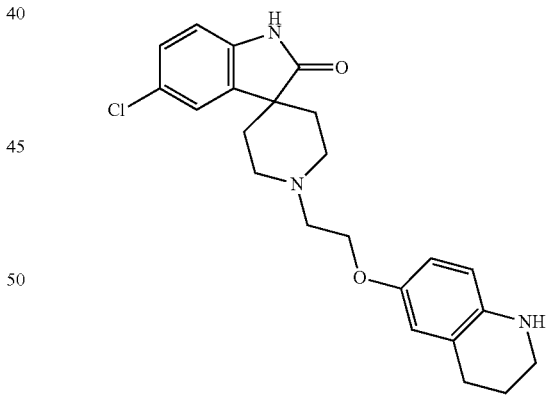

To a solution tert-butyl 6-(2-{5-chloro-2-oxo-1,2-dihydrospiro[indole-3,4'-piperidin]-1'-yl}ethoxy)-1,2,3,4-tetrahydroquinoline-1-carboxylate (177 mg, 0.346 mmol) in 1,4-dioxane (2 mL) was added 4.0 M HCl in 1,4-dioxane (2.16 mL, 8.64 mmol). The mixture was stirred for 1 h. The mixture was concentrated in vacuo to give 5-chloro-1'-[2-(1,2,3,4-tetrahydroquinolin-6-yloxy)ethyl]-1,2-dihydrospiro[indole-3,4'-piperidin]-2-one (Intermediate C-1, HCl salt), which was used in the subsequent step without further purification. MS=412.1 [M+H]$^+$ The following intermediates in Table 14 were prepared according to procedures similar to steps 1-3 described for Intermediate C-1 using the appropriate starting materials.

General Procedure for Intermediates C-2 to C-5

TABLE 14

| Intermediate # | Structure | Name | Exact Mass [M + H]⁺ | Intermediate Starting Materials Used |
|---|---|---|---|---|
| C-2 | 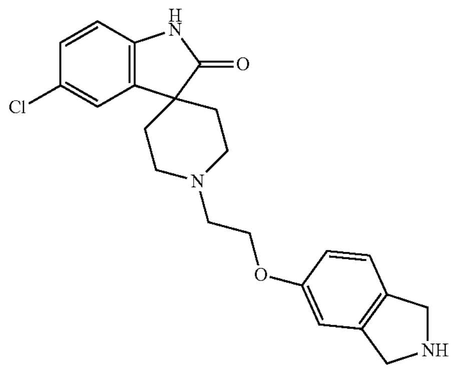 [SMILES: O=C1Nc2ccc(Cl)cc2C12CCN(CCOc1ccc3c(c1)CNC3)CC2] | 5-chloro-1'-[2-(2,3-dihydro-1H-isoindol-5-yloxy)ethyl]-1,2-dihydrospiro[indole-3,4'-piperidin]-2-one (HCl salt) | Calc'd 398.2 Found 398.1 | B-4 |
| C-3 | 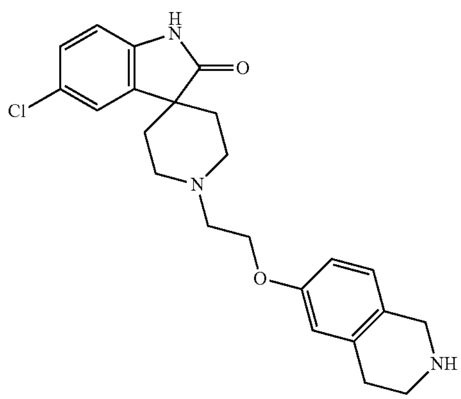 [SMILES: O=C1Nc2ccc(Cl)cc2C12CCN(CCOc1ccc3c(c1)CCNC3)CC2] | 5-chloro-1'-[2-(1,2,3,4-tetrahydroisoquinolin-6-yloxy)ethyl]-1,2-dihydrospiro[indole-3,4'-piperidin]-2-one (HCl salt) | Calc'd 412.2 Found 412.2 | B-4 |
| C-4 | 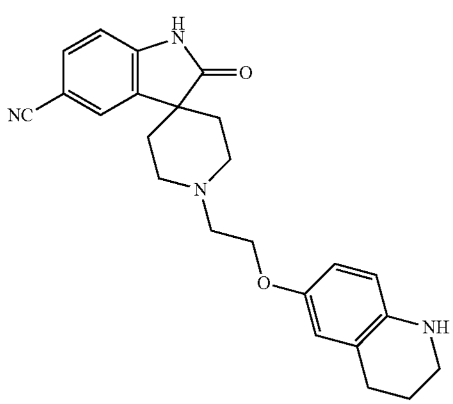 [SMILES: N#Cc1ccc2c(c1)C1(CCN(CCOc3ccc4c(c3)CCCN4)CC1)C(=O)N2] | 2-oxo-1'-[2-(1,2,3,4-tetrahydroquinolin-6-yloxy)ethyl]-1,2-dihydrospiro[indole-3,4'-piperidine]-5-carbonitrile (HCl salt) | Calc'd 403.2 Found 403.2 | B-9 |

TABLE 14-continued

| Intermediate # | Structure | Name | Exact Mass [M + H]+ | Intermediate Starting Materials Used |
|---|---|---|---|---|
| C-5 | 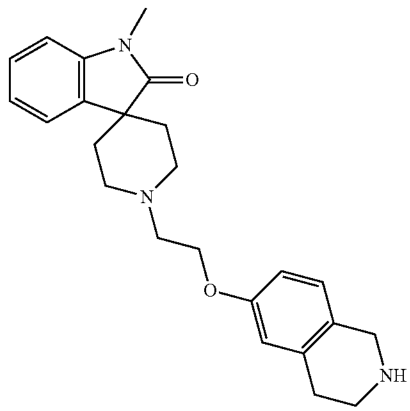 [SMILES: CN1C(=O)C2(CCN(CCOc3ccc4c(c3)CCNC4)CC2)c2ccccc21] | 1-methyl-1'-[2-(1,2,3,4-tetrahydroisoquinolin-6-yloxy)ethyl]-1,2-dihydrospiro[indole-3,4'-piperidin]-2-one (HCl salt) | Calc'd 392.2 Found 392.1 | B-6 |

General Procedure for Intermediate D-1

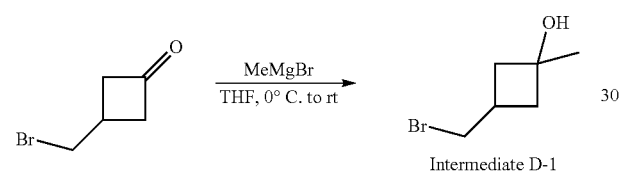

Step 1: 3-(bromomethyl)-1-methylcyclobutan-1-ol

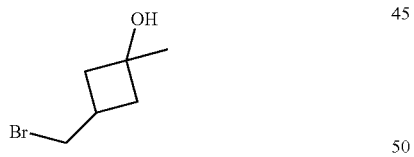

To a 0° C. solution of 3-(bromomethyl)cyclobutanone (3.00 g, 18.4 mmol) in THF (30 mL) was added 3.0 M MeMgBr in 2-MeTHF (6.8 mL, 20.4 mmol). The mixture was stirred at room temperature for 1 h. The reaction mixture was quenched by addition of saturated aqueous NH$_4$Cl (30 mL), and then extracted with 3:1 DCM/MeOH (3×50 mL). The combined organic layers were washed with brine (100 mL), dried over Na$_2$SO$_4$, filtered, and concentrated in vacuo to give 3-(bromomethyl)-1-methylcyclobutan-1-ol (Intermediate D-1), which was used in the subsequent steps without further purification. $^1$H NMR (400 MHz, DMSO-d$_6$): δ=4.13 (s, 1H), 3.52 (d, J=7.6 Hz, 2H), 2.17-2.11 (m, 1H), 2.08-1.99 (m, 2H), 1.72-1.66 (m, 2H), 1.20 (s, 3H).

Example 1

5-Chloro-1'-(2-{[2-(1-methanesulfonylethyl)pyrimidin-5-yl]oxy}ethyl)-1,2-dihydrospiro[indole-3,4'-piperidin]-2-one (Compound 1)

5-chloro-1'-[2-({2-[(1S) or (1R)-1-methanesulfonylethyl]pyrimidin-5-yl}oxy)ethyl]-1,2-dihydrospiro[indole-3,4'-piperidin]-2-one (Compound 2) and 5-chloro-1'-[2-({2-[(1R) or (1S-1-methanesulfonylethyl]pyrimidin-5-yl}oxy)ethyl]-1,2-dihydrospiro[indole-3,4'-piperidin]-2-one (Compound 3)

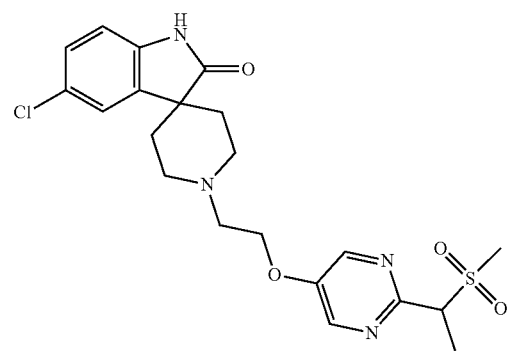 [SMILES: CC(c1ncc(OCCN2CCC3(CC2)C(=O)Nc2ccc(Cl)cc23)cn1)S(C)(=O)=O]

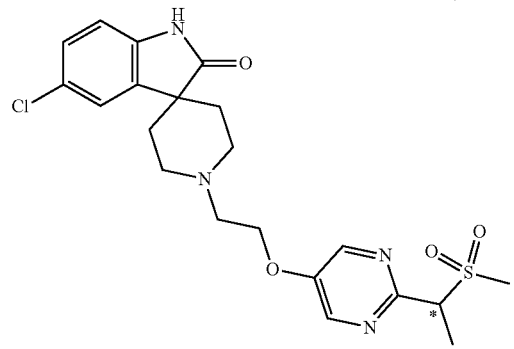

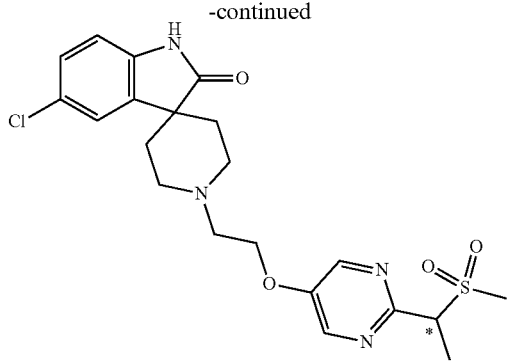

Step 1: 5-Chloro-1'-(2-{[2-(1-methanesulfonylethyl)pyrimidin-5-yl]oxy}ethyl)-1,2-dihydrospiro[indole-3,4'-piperidin]-2-one

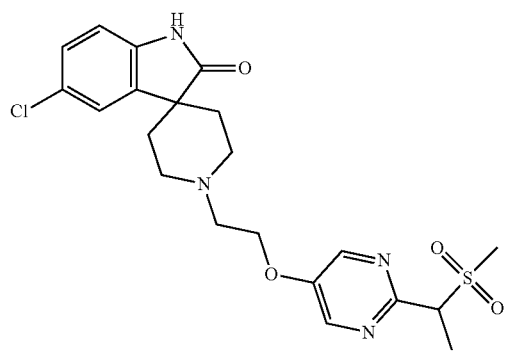

To a vial was added 5-(2-bromoethoxy)-2-(1-methanesulfonylethyl)pyrimidine (Intermediate A-75, 221 mg, 0.714 mmol), 5-chloro-1,2-dihydrospiro[indole-3,4'-piperidin]-2-one (Intermediate B-4, 150 mg, 0.55 mmol, HCl salt), followed by DMF (2.7 mL). K$_2$CO$_3$ (0.19 g, 1.37 mmol) was then added, and the reaction mixture was heated to 60° C. After 2 h, the reaction was removed from heat and diluted with EtOAc, then filtered over Celite. The filtrate was concentrated, and the residue was diluted in a 1:1 mixture of MeCN and H$_2$O (3 mL). Purification by reverse phase preparative HPLC (Phenomenex Kinetex C$_{18}$ column, 5-40% MeCN in water with 0.1% formic acid modifier) afforded 5-chloro-1'-(2-{[2-(1-methanesulfonylethyl)pyrimidin-5-yl]oxy}ethyl)-1H-spiro[indole-3,4'-piperidin]-2-one (Compound 1). $^1$H NMR (500 MHz, DMSO-d$_6$): δ 10.42 (s, 1H), 8.58 (s, 2H), 7.44 (d, J=2.1 Hz, 1H), 7.17 (dd, J=8.3, 2.1 Hz, 1H), 6.78 (d, J=8.3 Hz, 1H), 4.58 (q, J=7.2 Hz, 1H), 4.29-4.27 (m, 2H), 2.94 (s, 3H), 2.91-2.79 (m, 4H), 2.66-2.64 (m, 2H), 1.71-1.69 (m, 2H), 1.66-1.61 (m, 5H). MS=465.03 [M+H]$^+$.

Step 2: 5-chloro-1'-[2-({2-[(1S) or (1R)-1-methanesulfonylethyl]pyrimidin-5-yl}oxy)ethyl]-1,2-dihydrospiro[indole-3,4'-piperidin]-2-one (Compound 2) and 5-chloro-1'-[2-({2-[(1R) or (1S)-1-methanesulfonylethyl]pyrimidin-5-yl}oxy)ethyl]-1,2-dihydrospiro[indole-3,4'-piperidin]-2-one (Compound 3)

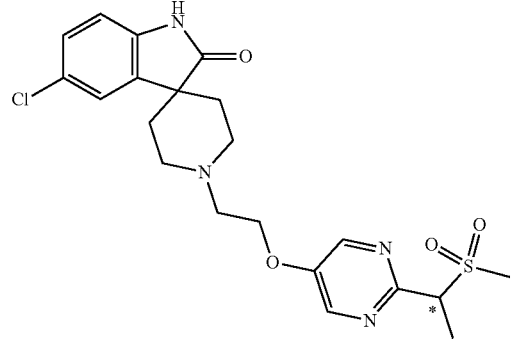

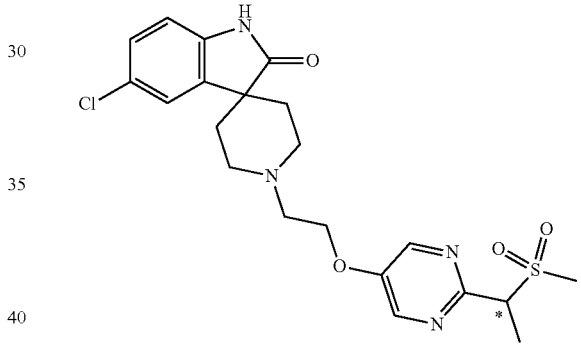

5-Chloro-1'-(2-{[2-(1-methanesulfonylethyl)pyrimidin-5-yl]oxy}ethyl)-1,2-dihydrospiro[indole-3,4'-piperidin]-2-one was separated by preparative chiral SFC (Daicel Chiralpak AD-3, 55% isopropanol with 0.1% NH$_4$OH in CO$_2$). The first eluting enantiomer of the title compound, 5-chloro-1'-[2-({2-[(1S) or (1R)-1-methanesulfonylethyl]pyrimidin-5-yl}oxy)ethyl]-1,2-dihydrospiro[indole-3,4'-piperidin]-2-one (Compound 2): $^1$H NMR (400 MHz, DMSO-d$_6$): δ 10.45 (s, 1H), 8.61 (s, 2H), 7.47 (d, J=1.6 Hz, 1H), 7.20 (dd, J=8.4, 2.0 Hz, 1H), 6.81 (d, J=8.4 Hz, 1H), 4.62 (q, J=7.2 Hz, 1H), 4.31 (t, J=5.6 Hz, 2H), 2.98 (s, 3H), 2.93-2.82 (m, 4H), 2.71-2.62 (m, 2H), 1.78-1.71 (m, 2H), 1.70-1.63 (m, 5H). MS=465.1 [M+H]$^+$. The second eluting enantiomer of the title compound, 5-chloro-1'-[2-({2-[(1R) or (1S)-1-methanesulfonylethyl]pyrimidin-5-yl}oxy)ethyl]-1,2-dihydrospiro[indole-3,4'-piperidin]-2-one (Compound 3): $^1$H NMR (400 MHz, DMSO-d$_6$): δ 10.50 (s, 1H), 8.66 (s, 2H), 7.52 (s, 1H), 7.29-7.22 (m, 1H), 6.86 (d, J=8.3 Hz, 1H), 4.67 (q, J=7.0 Hz, 1H), 4.36 (br s, 2H), 3.03 (s, 3H), 2.98-2.87 (m, 4H), 2.76-2.67 (m, 2H), 1.79-1.78 (m, 2H) 1.72-1.70 (m, 5H). MS=465.1 [M+H]$^+$.

Example 2

5-chloro-1'-(2-{[2-(1-methanesulfonylcyclopropyl)pyrimidin-5-yl]oxy}ethyl)-1,2-dihydrospiro[indole-3,4'-piperidin]-2-one (Compound 4)

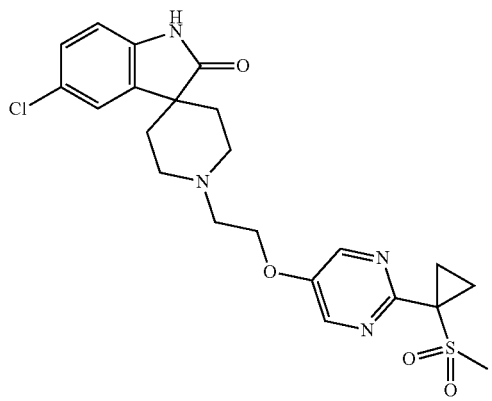 [SMILES: CS(=O)(=O)C1(c2ncc(OCCN3CCC4(CC3)C(=O)Nc3ccc(Cl)cc34)cn2)CC1]

To a solution of 5-(2-bromoethoxy)-2-(1-methanesulfonylcyclopropyl)pyrimidine (Intermediate A-76, 300 mg, 0.93 mmol) and 5-chloro-1,2-dihydrospiro[indole-3,4'-piperidin]-2-one (Intermediate B-4, 0.306 g, 1.12 mmol, HCl salt) in DMF (4.7 mL) was added $K_2CO_3$ (0.387 g, 2.80 mmol). The reaction mixture was heated to 60° C. for 2 h. The reaction was allowed to cool to room temperature, diluted in $H_2O$ (20 mL) and extracted with EtOAc (3×30 mL). The combined organic layers were dried over $Na_2SO_4$, filtered, and concentrated in vacuo. Purification by reverse phase preparative HPLC (Phenomenex Kinetex $C_{18}$ column, 5-40% MeCN in water with 0.1% formic acid modifier) gave 5-chloro-1'-(2-{[2-(1-methanesulfonylcyclopropyl)pyrimidin-5-yl]oxy}ethyl)-1,2-dihydrospiro[indole-3,4'-piperidin]-2-one (Compound 4). $^1$H NMR (500 MHz, DMSO-$d_6$): δ 10.49 (s, 1H), 8.61 (s, 2H), 7.50 (d, J=2.1 Hz, 1H), 7.23 (dd, J=8.2, 2.1 Hz, 1H), 6.84 (d, J=8.3 Hz, 1H), 4.34 (t, J=5.6 Hz, 2H), 3.36 (s, 3H), 2.96-2.85 (m, 4H), 2.73-2.68 (m, 2H), 1.80-1.67 (i, 6H), 1.60-1.58 (i, 2H). MS=477.12 [M+H].

The following compounds in Table 15 were prepared according to procedures analogous to those described for Compound 4 using the appropriate starting materials.

TABLE 15

| # | Structure | IUPAC Name | Exact Mass [M + H]⁺ | Intermediates Used | HNMR Spectra |
|---|---|---|---|---|---|
| 5 | (structure) | 5-(difluoromethyl)-1'-(2-{[2-(1-methanesulfonylcyclopropyl)pyrimidin-5-yl]oxy}ethyl)-1,2-dihydrospiro[indole-3,4'-piperidin]-2-one | Calc'd 493.2 Found 493.2 | A-76 and B-1 | $^1$H NMR (500 MHz, CDCl$_3$, 25/26 H): δ 8.34 (s, 2H), 7.69 (s, 1H), 7.39 (s, 1H), 7.34-7.25 (m, 1H), 6.87 (d, J = 8.0 Hz, 1H), 6.54 (t, J = 56.5 Hz, 1H), 4.35 (t, J = 5.1 Hz, 2H), 3.30 (t, J = 11.8 Hz, 2H), 3.26 (s, 3H), 3.14 (t, J = 5.1 Hz, 2H), 3.06 (d, J = 11.4 Hz, 1H), 2.22 (s, 2H), 1.94-1.82 (m, 4H), 1.72-1.57 (m, 2H). |
| 6 | (structure) | 5-(difluoromethoxy)-1'-(2-{[2-(1-methanesulfonylcyclopropyl)pyrimidin-5-yl]oxy}ethyl)-1,2-dihydrospiro[indole-3,4'-piperidin]-2-one | Calc'd 509.2 Found 509.1 | A-76 and B-2 | $^1$H NMR (500 MHz, DMSO-$d_6$): δ 10.39 (s, 1H), 8.55 (s, 2H), 8.07 (s, 1H), 7.03 (t, J = 74.7 Hz, 1H), 6.95 (d, J = 8.4 Hz, 1H), 6.79 (d, J = 8.4 Hz, 1H), 4.30 (t, J = 5.5 Hz, 2H), 3.29 (br s, 3H), 2.99-2.86 (m, 4H), 2.75-2.66 (m, 2H), 1.77-1.73 (m, 2H), 1.68-1.65 (m, 4H), 1.54-1.51 (m, 2H). |

Example 3

5,7-dichloro-1'-[2-(4-methanesulfonylphenoxy)ethyl]-1,2-dihydrospiro[indole-3,4'-piperidin]-2-one (Compound 7)

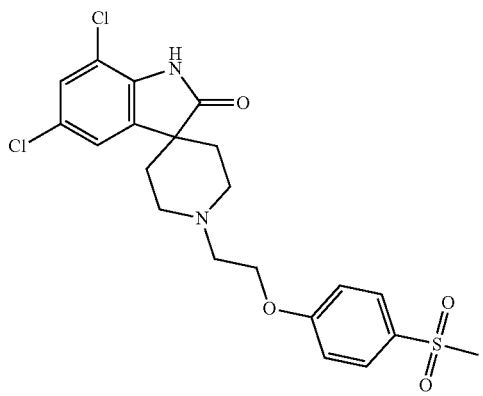 [SMILES: CS(=O)(=O)c1ccc(OCCN2CCC3(CC2)C(=O)Nc2c(Cl)cc(Cl)cc23)cc1]

Step 1: tert-butyl 5,7-dichloro-2-oxo-1,2-dihydrospiro[indole-3,4'-piperidine]-1'-carboxylate

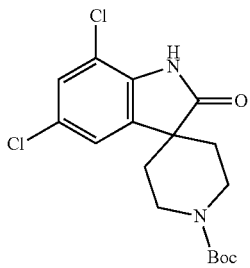 [SMILES: CC(C)(C)OC(=O)N1CCC2(CC1)C(=O)Nc1c(Cl)cc(Cl)cc12]

To a solution of (2,4-dichlorophenyl)hydrazine (2.60 g, 12.2 mmol, HCl salt) in CHCl₃ (30 mL) was added TEA (1.30 mL, 9.36 mmol), tert-butyl 4-formylpiperidine-1-carboxylate (2.00 g, 9.36 mmol) and TFA (2.80 mL, 28.1 mmol). The mixture was stirred at 70° C. for 17 h. The mixture was cooled to 0° C. and m-CPBA (1.14 g, 85% purity, 5.63 mmol) was added in portions. Then the mixture was stirred at room temperature for 1 h. The reaction mixture was quenched with saturated aqueous Na₂CO₃ (60 mL) and extracted with EtOAc (3×40 mL). The combined organic layers were washed with saturated aqueous Na₂S2O3 (50 mL) and brine (2×50 mL), dried over Na₂SO₄, filtered, and concentrated in vacuo. The crude residue was purified by normal phase silica gel chromatography (Biotage 25 g cartridge, 0-40% EtOAc:petroleum ether). The residue was further purified by reverse phase preparative HPLC (Phenomenex Luna C$_{18}$ column, 40-75% MeCN: 10 mM TFA in H₂O) to give tert-butyl 5,7-dichloro-2-oxo-1,2-dihydrospiro[indole-3,4'-piperidine]-1'-carboxylate. MS=315.0 [M-C₄H₈+H]⁺.

Step 2: 5,7-dichloro-1,2-dihydrospiro[indole-3,4'-piperidin]-2-one

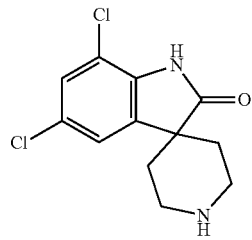

To a solution of tert-butyl 5,7-dichloro-2-oxo-1,2-dihydrospiro[indole-3,4'-piperidine]-1-carboxylate (280 mg, 0.75 mmol) in EtOAc (5 mL) was added 4.0 M HCl in EtOAc (10 mL, 40 mmol). The mixture was stirred at room temperature for 1 h. The mixture was concentrated under reduced pressure to give 5,7-dichloro-1,2-dihydrospiro[indole-3,4'-piperidin]-2-one. MS=271.0/273.0 [M+H]⁺.

Step 3: 5,7-dichloro-1'-[2-(4-methanesulfonylphenoxy)ethyl]-1,2-dihydrospiro[indole-3,4'-piperidin]-2-one (Compound 7)

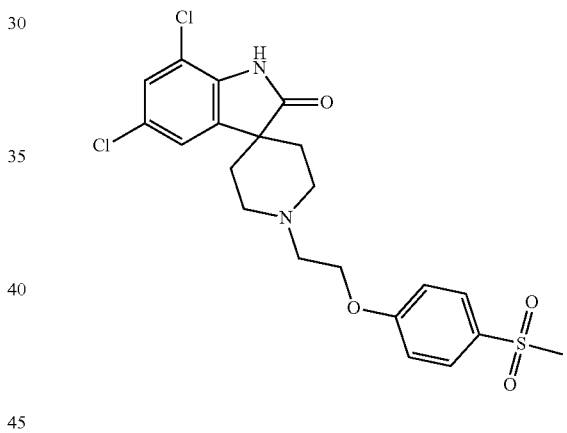

A mixture of 5,7-dichloro-1,2-dihydrospiro[indole-3,4'-piperidin]-2-one (100 mg, 0.325 mmol, HCl salt), 1-(2-bromoethoxy)-4-methylsulfonyl-benzene (Intermediate A-3, 77.1 mg, 0.276 mmol) and K₂CO₃ (89.9 mg, 650 mmol) in MeCN (4 mL) was stirred at 70° C. for 3 h. After cooling to the reaction to room temperature, the reaction mixture was diluted with H₂O (10 mL) and extracted with EtOAc (2×15 mL). The combined organic layers were washed with brine (2×15 mL), dried over Na₂SO₄, filtered, and concentrated in vacuo. The crude residue was purified by reverse phase preparative HPLC (Waters Xbridge BEH C$_{18}$ column, 30-60% MeCN: 10 mM NH₄HCO₃ in H₂O) to give 5,7-dichloro-1'-[2-(4-methanesulfonylphenoxy)ethyl]-1,2-dihydrospiro[indole-3,4'-piperidin]-2-one (Compound 7): ¹H NMR (400 MHz, DMSO-d₆): δ 10.90 (br s, 1H), 7.85-7.83 (d, J=8.8 Hz, 2H), 7.53 (s, 1H), 7.43-7.42 (m, 1H), 7.19 (d, J=8.8 Hz, 2H), 4.25 (t, J=5.6 Hz, 2H), 3.16 (s, 3H), 2.92-2.86 (m, 4H), 2.70-2.74 (m, 2H), 1.80-1.78 (m, 4H). MS=469.1 [M+H]⁺.

The following compounds in Table 16 were prepared according to procedures similar to steps 1-3 described for Compound 7 using the appropriate starting materials.

TABLE 16

| # | Structure | IUPAC Name | Exact Mass [M + H]+ | Intermediate Used |
|---|---|---|---|---|
| 8 | 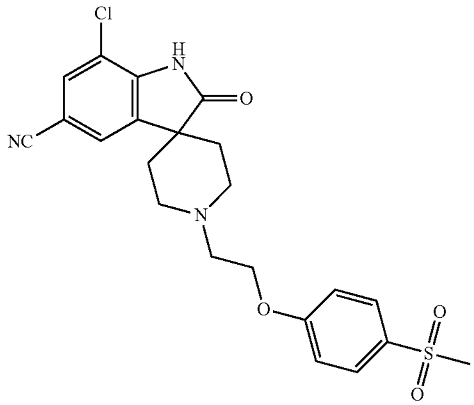 [SMILES: CS(=O)(=O)c1ccc(OCCN2CCC3(CC2)C(=O)Nc2c(Cl)cc(C#N)cc23)cc1] | 7-chloro-1'-[2-(4-methanesulfonyl-phenoxy)ethyl]-2-oxo-1,2-dihydrospiro[indole-3,4'-piperidine]-5-carbonitrile | Calc'd 460.1 Found 460.1 | A-3 |
| 9 | 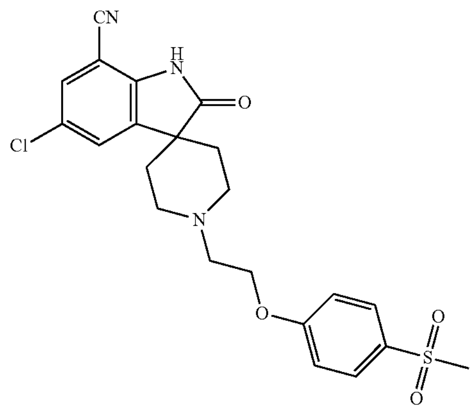 [SMILES: CS(=O)(=O)c1ccc(OCCN2CCC3(CC2)C(=O)Nc2c(C#N)cc(Cl)cc23)cc1] | 5-chloro-1'-[2-(4-methanesulfonyl-phenoxy)ethyl]-2-oxo-1,2-dihydrospiro[indole-3,4'-piperidine]-7-carbonitrile | Calc'd 460.1 Found 460.2 | A-3 |

Example 4

5-chloro-1'-[(2S)-1-(4-methanesulfonylphenoxy)propan-2-yl]-1,2-dihydrospiro[indole-3,4'-piperidin]-2-one (Compound 10) and 5-chloro-1'-[(2S)-2-(4-methanesulfonylphenoxy)propyl]-1,2-dihydrospiro[indole-3,4'-piperidin]-2-one (Compound 11)

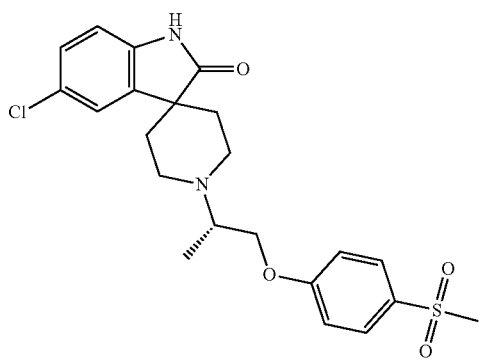

-continued

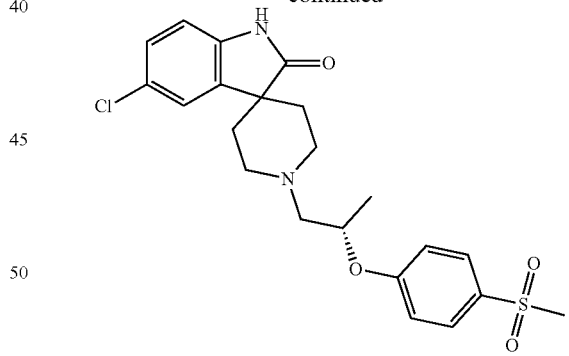

To a mixture of 5-chloro-1'-[(2S)-1-hydroxypropan-2-yl]-1,2-dihydrospiro[indole-3,4'-piperidin]-2-one and 5-chloro-1'-[(2R)-2-hydroxypropyl]-1,2-dihydrospiro[indole-3,4'-piperidin]-2-one (Intermediates B-17 and B-18, 200 mg, 0.678 mmol) and 4-methylsulfonylphenol (175 mg, 1.02 mmol) in THF (1 mL) was added PPh$_3$ (267 mg, 1.02 mmol). The mixture was cooled to 0° C., and DIAD (0.198 mL, 1.02 mmol) was added dropwise. The mixture was stirred at 25° C. for 3 h. The reaction mixture was cooled to 0° C. and quenched with H$_2$O (10 mL), then extracted with EtOAc (3×10 mL). The combined organic layers were washed with brine (8 mL), dried over Na$_2$SO$_4$, filtered, and concentrated in vacuo. The crude residue was purified by normal phase silica gel chromatography (Biotage 12 g cartridge, 0-100% EtOAc:petroleum ether). The residue was further purified by reverse phase preparative HPLC (Waters Xbridge BEH C$_{18}$ column, 30-50% MeCN: 10 mM NH$_4$HCO$_3$ in H$_2$O). The first eluting product, 5-chloro-1'-[(2S)-1-(4-methanesulfonylphenoxy)propan-2-yl]-1,2-dihydrospiro[indole-3,4'-piperidin]-2-one (Compound 10): $^1$H NMR (400 MHz, DMSO-d$_6$): δ 10.49 (s, 1H), 7.85 (d, J=8.8 Hz, 2H), 7.44 (s, 1H), 7.24-7.21 (m, 3H), 6.84 (d, J=8.0 Hz, 1H), 4.26-4.22 (m, 1H), 4.10-4.06 (m, 1H), 3.16 (s, 3H), 3.14-3.12 (m, 1H), 3.02-3.00 (m, 2H), 2.84-2.74 (m, 2H), 1.77-1.66 (m, 4H), 1.16 (d, J=6.4 Hz, 3H), MS=449.1 [M+H]$^+$. The second eluting product, 5-chloro-1'-[(2S)-2-(4-methanesulfonylphenoxy)propyl]-1,2-dihydrospiro[indole-3,4'-piperidin]-2-one (Compound 11): $^1$H NMR (400 MHz, DMSO-d$_6$): δ 10.49 (s, 1H), 7.83 (d, J=8.8 Hz, 2H), 7.47 (s, 1H), 7.24-7.19 (m, 3H), 6.83 (d, J=8.4 Hz, 1H), 4.89-4.85 (m, 1H), 3.16 (s, 3H), 2.90-2.88 (m, 2H), 2.78-2.76 (m, 1H), 2.70-2.63 (m, 3H), 1.75-1.64 (m, 4H), 1.30 (d, J=6.0 Hz, 3H). MS=449.1 [M+H]$^+$.

The following compounds in Table 17 were prepared according to procedures similar to steps described for Compound 10 and Compound 11 using the appropriate starting materials.

Example 5

5-chloro-1'-(2-{[1-(3-methanesulfonylpropyl)-1H-indazol-5-yl]oxy}ethyl)-1,2-dihydrospiro[indole-3,4'-piperidin]-2-one (Compound 14)

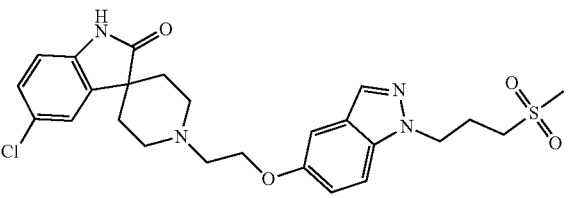

TABLE 17

| # | Structure | IUPAC Name | Exact Mass [M + H]$^+$ | Step 2 Column | Step 2 Elution Order | Intermediates Used |
|---|---|---|---|---|---|---|
| 12 | 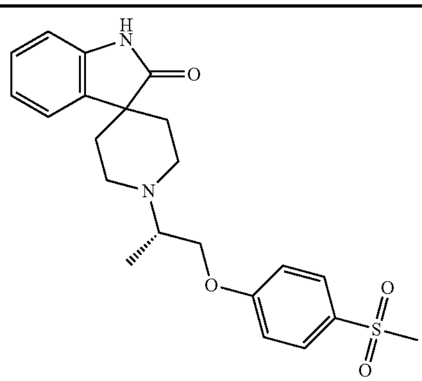 | 1'-[(2S)-1-(4-methanesulfonylphenoxy)propan-2-yl]-1,2-dihydrospiro[indole-3,4'-piperidin]-2-one | Calc'd 415.1 Found 415.2 | Waters Xbridge BEH C$_{18}$ column | 1$^{st}$ | B-21 & B-22 |
| 13 | 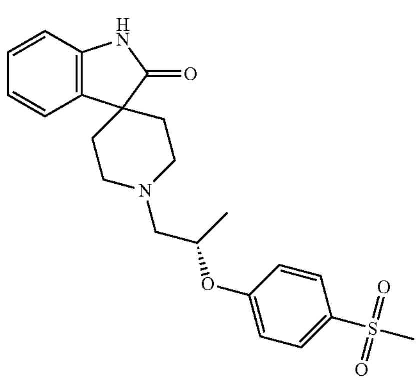 [SMILES: C[C@@H](CN1CCC2(CC1)C(=O)Nc1ccccc12)Oc1ccc(S(C)(=O)=O)cc1] | 1'-[(2S)-2-(4-methanesulfonylphenoxy)propyl]-1,2-dihydrospiro[indole-3,4'-piperidin]-2-one | Calc'd 415.1 Found 415.1 | Waters Xbridge BEH C$_{18}$ column | 2$^{nd}$ | B-21 & B-22 |

Step 1: 1-(3-methanesulfonylpropyl)-5-methoxy-1H-indazole

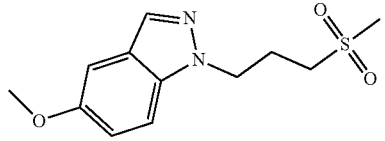

A mixture of 5-methoxy-1H-indazole (200 mg, 1.35 mmol), 3-methylsulfonylpropyl methanesulfonate (292 mg, 1.35 mmol) and $Cs_2CO_3$ (880 mg, 2.70 mmol) in DMF (5 mL) was stirred at 80° C. for 2 h. The reaction mixture was cooled to 0° C. and quenched by the addition of $H_2O$ (20 mL), then extracted with EtOAc (3×10 mL). The combined organic layers were washed with brine (2×10 mL), dried over $Na_2SO_4$, filtered, and concentrated in vacuo. The crude residue was purified by preparative TLC ($SiO_2$, 100% EtOAc). The lower polarity (higher $R_f$) product, desired 1-(3-methanesulfonylpropyl)-5-methoxy-1H-indazole: $^1$H NMR (400 MHz, DMSO-$d_6$): δ 7.96 (d, J=0.8 Hz, 1H), 7.59 (d, J=9.2 Hz, 1H), 7.18 (d, J=2.4 Hz, 1H), 7.06 (dd, J=9.2, 2.4 Hz, 1H), 4.50 (t, J=7.2 Hz, 2H), 3.78 (s, 3H), 3.08 (dd, J=10.4, 5.6 Hz, 2H), 2.96 (s, 3H), 2.26-2.18 (m, 2H). MS=269.1 [M+H]$^+$. The higher polarity product, byproduct 2-(3-methanesulfonylpropyl)-5-methoxy-2H-indazole: $^1$H NMR (400 MHz, DMSO-$d_6$): δ 8.21 (s, 1H), 7.51 (d, J=9.2 Hz, 1H), 7.00 (d, J=2.4 Hz, 1H), 6.90 (dd, J=9.2, 2.8 Hz, 1H), 4.50 (t, J=6.8 Hz, 2H), 3.75 (s, 3H), 3.11-3.07 (m, 2H), 2.98 (s, 3H), 2.36-2.28 (m, 2H). MS=269.1 [M+H]$^+$.

Step 2: 1-(3-methanesulfonylpropyl)-1H-indazol-5-ol

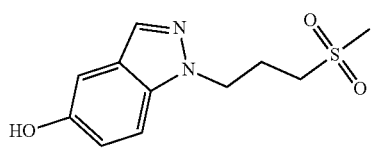 [SMILES: CS(=O)(=O)CCCn1ncc2cc(O)ccc21]

To a 0° C. solution of 1-(3-methanesulfonylpropyl)-5-methoxy-1H-indazole (150 mg, 0.559 mmol) in DCM (8 mL) was added $BBr_3$ (215 µL, 2.24 mmol) dropwise. The mixture was stirred at room temperature for 10 h. The reaction mixture was cooled to 0° C. and quenched by the addition of $H_2O$ (10 mL), then adjusted to pH=9 with saturated aqueous $NaHCO_3$ and extracted with DCM (3×5 mL). The combined organic layers were dried over $Na_2SO_4$, filtered, and concentrated in vacuo give 1-(3-methanesulfonylpropyl)-1H-indazol-5-ol. MS=255.1 [M+H]$^+$.

Step 3: 5-chloro-1'-(2-{[1-(3-methanesulfonylpropyl)-1H-indazol-5-yl]oxy}ethyl)-1,2-dihydrospiro[indole-3,4'-piperidin]-2-one (Compound 14)

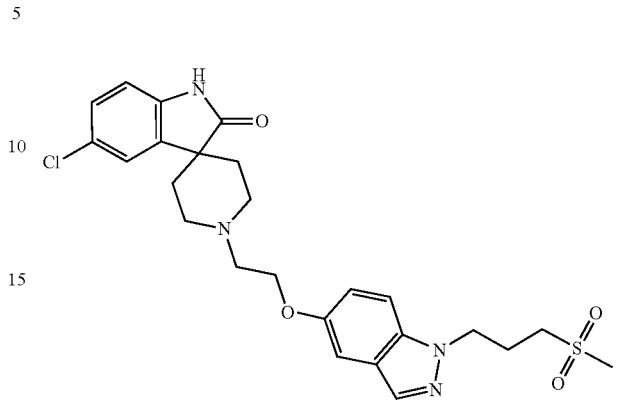

A mixture of 1-(3-methanesulfonylpropyl)-1H-indazol-5-ol (30 mg, 0.118 mmol), 5-chloro-1'-(2-chloroethyl)-1,2-dihydrospiro[indole-3,4'-piperidin]-2-one (Intermediate B-5, 52.9 mg, 0.177 mmol), NaI (0.8 mg, 5.90 umol) and $K_2CO_3$ (16.3 mg, 0.118 mmol) in acetone (1 mL) was stirred at 50° C. for 16 h. After cooling to the reaction to room temperature, the mixture was diluted with $H_2O$ (20 mL) and extracted with EtOAc (3×10 mL). The combined organic layers were dried over $Na_2SO_4$, filtered, and concentrated in vacuo. The crude residue was purified by reverse phase preparative HPLC (Waters Xbridge BEH $C_{18}$ column, 25-60% MeCN: 10 mM $NH_4HCO_3$ in $H_2O$) to give 5-chloro-1'-(2-{[1-(3-methanesulfonylpropyl)-1H-indazol-5-yl]oxy}ethyl)-1,2-dihydrospiro[indole-3,4'-piperidin]-2-one (Compound 14): $^1$H NR (400 MHz, DMSO-$d_6$): δ 10.50 (s, 1H), 7.96 (s, 1H), 7.60 (d, J=9.2 Hz, 1H), 7.51 (d, J=2.0 Hz, 1H), 7.24-7.22 (m, 2H), 7.10 (d, J=8.8 Hz, 1H), 6.84 (d, J=8.0 Hz, 1H), 4.50 (t, J=6.8 Hz, 2H), 4.16 (t, J=6.4 Hz, 2H), 3.08 (t, J=8.0 Hz, 2H), 2.96 (s, 3H), 2.94-2.87 (m, 4H), 2.72-2.70 (m, 2H), 2.22-2.20 (m, 2H), 1.79-1.70 (in, 4H). MS=517.2 [M+H]$^+$.

The following compounds in Table 18 were prepared according to procedures similar to steps 1-3 described for Compound 14 using the appropriate starting materials. Step 1 separation of indazole regiosomers was performed using normal phase $SiO_2$ column chromatography.

TABLE 18

| # | Structure | IUPAC Name | Exact Mass [M + H]+ | Step 1 Elution Order | Intermediate Used |
|---|---|---|---|---|---|
| 15 | 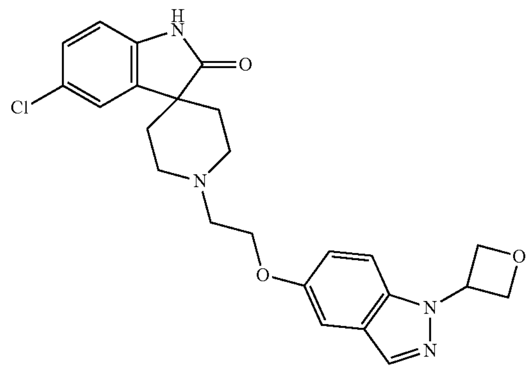 [SMILES: O=C1Nc2ccc(Cl)cc2C12CCN(CCOc1ccc3c(cnn3C3COC3)c1)CC2] | 5-chloro-1'-(2-{[1-(oxetan-3-yl)-1H-indazol-5-yl]oxy}ethyl)-1,2-dihydrospiro[indole-3,4'-piperidin]-2-one | Calc'd 453.1 Found 453.2 | First; lower polarity product | B-5 |
| 16 | 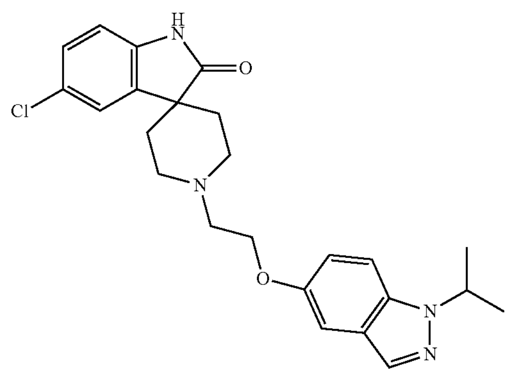 [SMILES: CC(C)n1ncc2cc(OCCN3CCC4(CC3)C(=O)Nc3ccc(Cl)cc34)ccc21] | 5-chloro-1'-(2-{[1-(propan-2-yl)-1H-indazol-5-yl]oxy}ethyl)-1,2-dihydrospiro[indole-3,4'-piperidin]-2-one | Calc'd 439.1 Found 439.3 | First; lower polarity product | B-5 |

Example 6

5-chloro-1'-[2-(4-{[(cis)-3-hydroxycyclobutyl]sulfonyl}phenoxy)ethyl]-1,2-dihydrospiro[indole-3,4'-piperidin]-2-one (Compound 17)

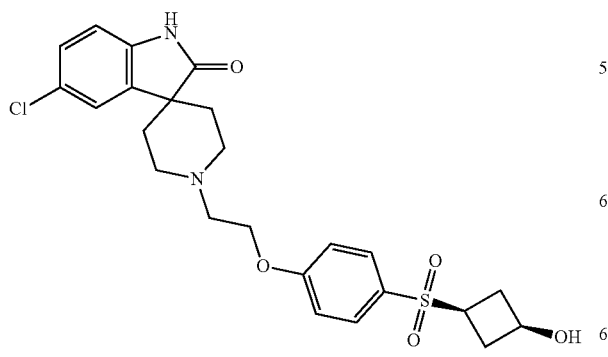

Step 1: 3-[(4-hydroxyphenyl)sulfanyl]cyclobutan-1-one

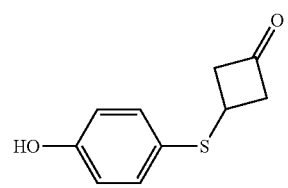 [SMILES: O=C1CC(Sc2ccc(O)cc2)C1]

To a solution of 4-sulfanylphenol (200 mg, 1.59 mmol) and 3-bromocyclobutanone (236 mg, 1.59 mmol) in acetone (2 mL) was added K$_2$CO$_3$ (219 mg, 1.59 mmol) and NaI (237 mg, 1.59 mmol). The mixture was stirred at 50° C. for 3 h. After cooling to room temperature, the reaction mixture was diluted with H$_2$O (10 mL) and extracted with EtOAc (3×5 mL). The combined organic layers were washed with brine (10 mL), dried over Na$_2$SO$_4$, filtered, and concentrated in vacuo. The crude residue was purified by preparative TLC (SiO$_2$, 1:2 EtOAc:petroleum ether) to give 3-[(4-hydroxyphenyl)sulfanyl]cyclobutan-1-one. MS=195.0 [M+H]+.

Step 2: 3-(4-hydroxybenzenesulfonyl)cyclobutan-1-one

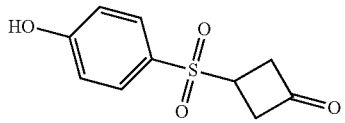 [SMILES: O=C1CC(S(=O)(=O)c2ccc(O)cc2)C1]

To a 0° C. solution of 3-[(4-hydroxyphenyl)sulfanyl] cyclobutan-1-one (50.0 mg, 0.257 mmol) in THF (2 mL) and H$_2$O (1 mL) was added Oxone (316 mg, 0.514 mmol). The mixture was stirred at room temperature for 1 h. The reaction mixture was cooled to 0° C. and quenched by the addition of saturated aqueous Na$_2$S$_2$O$_3$ (3 mL), then diluted with H$_2$O (5 mL) and extracted with EtOAc (3×5 mL). The combined organic layers were washed with brine (5 mL), dried over Na$_2$SO$_4$, filtered, and concentrated in vacuo. The crude residue was purified by preparative TLC (SiO$_2$, 1:1 EtOAc:petroleum ether) to give 3-(4-hydroxybenzenesulfonyl)cyclobutan-1-one. MS=225.0 [M−H]$^+$.

Step 3: Preparation of 4-{[(cis)-3-hydroxycyclobutyl]sulfonyl}phenol

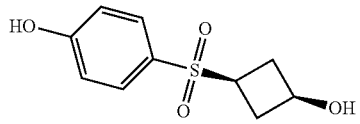 [SMILES: O=S(=O)(c1ccc(O)cc1)[C@H]1C[C@@H](O)C1]

To a 0° C. solution of 3-[(4-hydroxyphenyl)sulfanyl] cyclobutan-1-one (75.0 mg, 0.331 mmol) in THF (5 mL) was added NaBH$_4$ (25 mg, 0.662 mmol). The mixture was stirred at room temperature for 1 h. The reaction mixture was quenched with saturated aqueous NH$_4$Cl (5 mL), diluted with H$_2$O (5 mL), and extracted with EtOAc (3×5 mL). The combined organic layers were washed with brine (5 mL), dried over Na$_2$SO$_4$, filtered, and concentrated in vacuo to give crude 4-{[(cis)-3-hydroxycyclobutyl]sulfonyl}phenol, which was carried onto the next step without additional purification. MS=229.1 [M+H]$^+$.

Step 4: 5-chloro-1'-[2-(4-{[(cis)-3-hydroxycyclobutyl]sulfonyl}phenoxy)ethyl]-1,2-dihydrospiro[indole-3,4'-piperidin]-2-one (Compound 17)

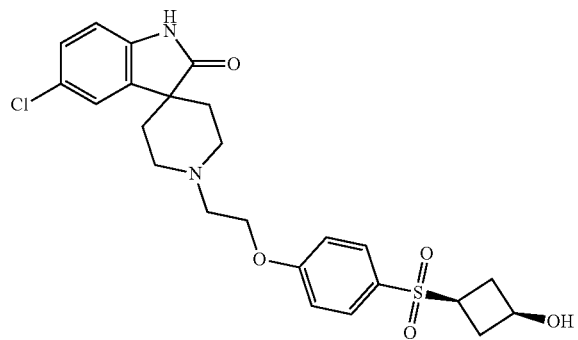 [SMILES: O=C1Nc2ccc(Cl)cc2C12CCN(CCOc1ccc(S(=O)(=O)[C@H]3C[C@@H](O)C3)cc1)CC2]

To a solution of 4-{[(cis)-3-hydroxycyclobutyl]sulfonyl}phenol (100 mg, 0.438 mmol) and 5-chloro-1'-(2-chloroethyl)-1,2-dihydrospiro[indole-3,4'-piperidin]-2-one (Intermediate B-5, 196 mg, 0.657 mmol) in DMF (3 mL) was added Ag$_2$O (203 mg, 0.876 mmol). The mixture was stirred at 50° C. for 16 h. After cooling to room temperature, the reaction mixture was diluted with H$_2$O (10 mL) and extracted with EtOAc (3×5 mL). The combined organic layers were washed with brine (5 mL), dried over Na$_2$SO$_4$, filtered, and concentrated in vacuo. The residue was purified by reverse phase preparative HPLC (Waters Xbridge BEH C$_{18}$ column, 25-55% MeCN: 10 mM NH$_4$HCO$_3$ in H$_2$O) to give 5-chloro-1'-[2-(4-{[(cis)-3-hydroxycyclobutyl] sulfonyl}phenoxy)ethyl]-1,2-dihydrospiro[indole-3,4'-piperidin]-2-one (Compound 17). $^1$H NMR (400 MHz, DMSO-d$_6$): δ 10.49 (s, 1H), 7.73 (d, J=8.8 Hz, 2H), 7.50 (d, J=1.6 Hz, 1H), 7.24-7.21 (m, 1H), 7.19 (d, J=9.2 Hz, 2H), 6.84 (d, J=8.4 Hz, 1H), 5.44 (d, J=6.4 Hz, 1H), 4.24 (t, J=6.4 Hz, 2H), 3.99-3.91 (m, 1H), 3.53-3.45 (m, 1H), 2.95-2.86 (m, 4H), 2.71-2.66 (m, 2H), 2.32-2.26 (m, 2H), 2.15-2.03 (m, 2H), 1.80-1.68 (m, 4H). MS=491.1 [M+H]$^+$.

Example 7

5-chloro-1-(2-hydroxyethyl)-1'-[2-(4-methanesulfonylphenoxy)ethyl]-1,2-dihydrospiro[indole-3,4'-piperidin]-2-one (Compound 18)

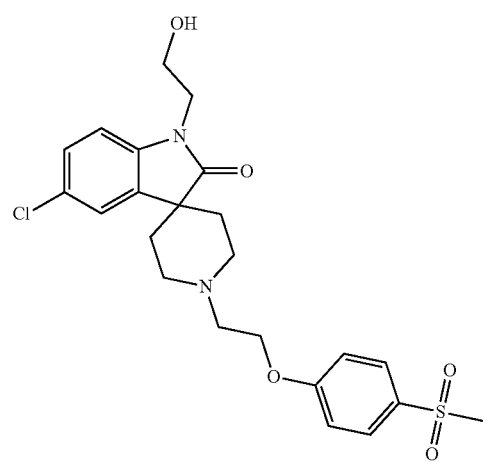 [SMILES: CS(=O)(=O)c1ccc(OCCN2CCC3(CC2)C(=O)N(CCO)c2ccc(Cl)cc23)cc1]

To a solution of 5-chloro-1'-[2-(4-methanesulfonylphenoxy)ethyl]-1,2-dihydrospiro[indole-3,4'-piperidin]-2-one (Compound 69, 100 mg, 0.230 mmol) in DMF (1.0 mL) was added K$_2$CO$_3$ (159 mg, 1.15 mmol) and 2-bromoethanol (54.6 μL, 0.768 mmol). The mixture was stirred at 80° C. for 12 h. After cooling to room temperature, the mixture was filtered and concentrated in vacuo. The residue was purified by reverse phase preparative HPLC (Waters Xbridge BEH C$_{18}$ column, 20-50% MeCN: 10 mM NH$_4$HCO$_3$ in H$_2$O) to give 5-chloro-1-(2-hydroxyethyl)-1'-[2-(4-methanesulfonylphenoxy)ethyl]-1,2-dihydrospiro[indole-3,4'-piperidin]-2-one (Compound 18). $^1$H NMR (400 MHz, DMSO-d$_6$): δ 7.84 (d, J=8.8 Hz, 2H), 7.54 (d, J=2.4 Hz, 1H), 7.32 (dd, J=8.4, 2.0 Hz, 1H), 7.20 (d, J=8.8 Hz, 2H), 7.10 (d, J=8.4 Hz, 1H), 4.82 (t, J=6.0 Hz, 1H), 4.26 (t, J=6.0 Hz, 2H), 3.73-3.68 (m, 2H), 3.57-3.54 (m, 2H), 3.16 (s, 3H), 2.98-2.86 (m, 4H), 2.76-2.69 (m, 2H), 1.77 (t, J=5.2 Hz, 4H). MS=479.1 [M+H]$^+$.

The following compounds in Table 19 were prepared according to procedures similar to steps described for Compound 18 using the appropriate starting materials.

TABLE 19

| # | Structure | IUPAC Name | Exact Mass [M + H]+ | Intermediated Used |
|---|---|---|---|---|
| 19 | 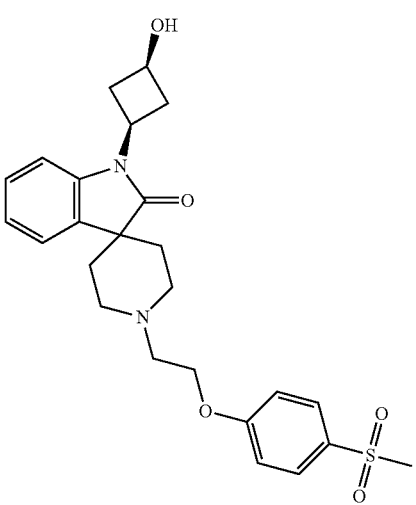 [SMILES: CS(=O)(=O)c1ccc(OCCN2CCC3(CC2)C(=O)N([C@H]2C[C@@H](O)C2)c2ccccc23)cc1] | 1'-[2-(4-methanesulfonyl-phenoxy)ethyl]-1-[(cis)-3-hydroxycyclobutyl]-1,2-dihydrospiro[indole-3,4'-piperidin]-2-one | Calc'd 471.1 Found 471.2 | Compound 73 |
| 20 | 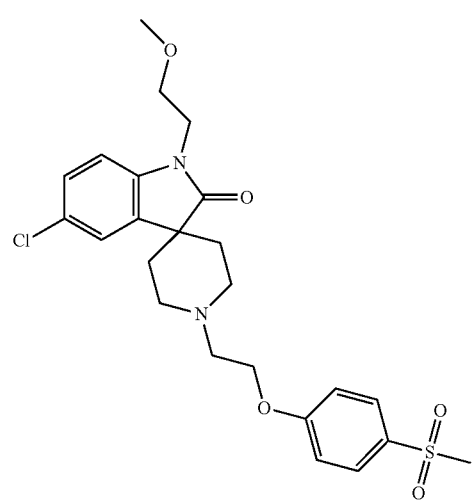 [SMILES: COCCN1C(=O)C2(CCN(CCOc3ccc(S(C)(=O)=O)cc3)CC2)c2cc(Cl)ccc21] | 5-chloro-1'-[2-(4-methanesulfonyl-phenoxy)ethyl]-1-(2-methoxyethyl)-1,2-dihydrospiro[indole-3,4'-piperidin]-2-one | Calc'd 493.2 Found 493.2 | Compound 69 |

TABLE 19-continued

| # | Structure | IUPAC Name | Exact Mass [M + H]+ | Intermediated Used |
|---|---|---|---|---|
| 21 | 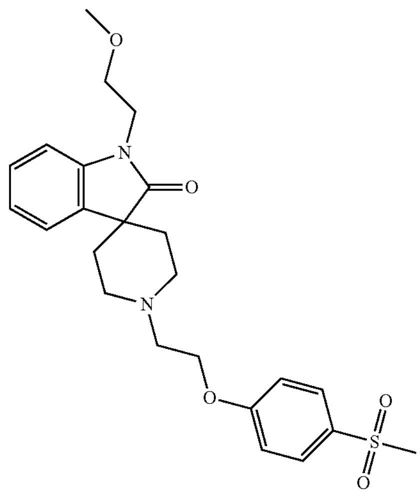 [SMILES: COCCN1C(=O)C2(CCN(CCOc3ccc(S(C)(=O)=O)cc3)CC2)c2ccccc21] | 1'-[2-(4-methanesulfonyl-phenoxy)ethyl]-1-(2-methoxyethyl)-1,2-dihydrospiro[indole-3,4'-piperidin]-2-one | Calc'd 459.2 Found 459.2 | Compound 73 |

Example 8

5-chloro-1'-(2-(4-(methylsulfonyl)phenoxy)ethyl)-1-(oxetan-3-yl)spiro[indoline-3,4'-piperidin]-2-one (Compound 22)

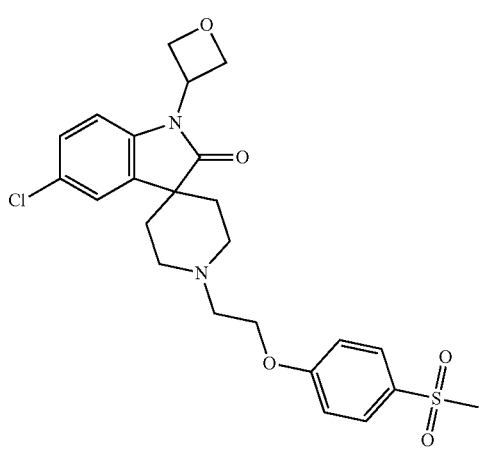 [SMILES: CS(=O)(=O)c1ccc(OCCN2CCC3(CC2)C(=O)N(C2COC2)c2ccc(Cl)cc23)cc1]

Step 1: tert-butyl 5-chloro-1-(oxetan-3-yl)-2-oxo-1,2-dihydrospiro[indole-3,4'-piperidine]-1'-carboxylate

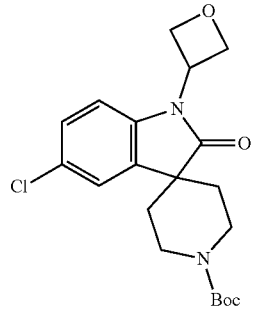 [SMILES: CC(C)(C)OC(=O)N1CCC2(CC1)C(=O)N(C1COC1)c1ccc(Cl)cc12]

To a solution of tert-butyl 5-chloro-2-oxo-1,2-dihydrospiro[indole-3,4'-piperidine]-1'-carboxylate (Intermediate B-3, 300 mg, 0.891 mmol) in DMF (5 mL) were added K₂CO₃ (369 mg, 2.67 mmol) and 3-iodooxetane (655 mg, 3.56 mmol). The mixture was stirred at 100° C. for 12 h. After cooling to room temperature, the reaction mixture was diluted with H₂O (10 mL) and extracted with EtOAc (3×15 mL). The combined organic layers were washed with brine (10 mL), dried over Na₂SO₄, filtered, and concentrated in vacuo. The crude residue was purified by normal phase silica gel chromatography (Biotage 12 g cartridge, 0-18% EtOAc: petroleum ether) to give tert-butyl 5-chloro-1-(oxetan-3-yl)-2-oxo-1,2-dihydrospiro[indole-3,4'-piperidine]-1'-carboxylate. MS=393.2 [M+H]+.

911

Step 2: 5-chloro-1-(oxetan-3-yl)-1,2-dihydrospiro[indole-3,4'-piperidin]-2-one

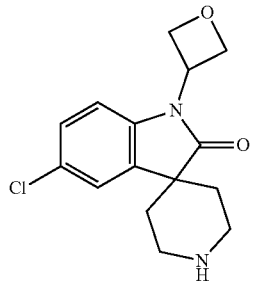 [SMILES: O=C1N(C2COC2)c2ccc(Cl)cc2C12CCNCC2]

A solution of tert-butyl 5-chloro-1-(oxetan-3-yl)-2-oxo-1,2-dihydrospiro[indole-3,4'-piperidine]-1'-carboxylate (200 mg, 509 mmol) in DCM (4 mL) and TFA (0.5 mL) was stirred at room temperature for 1 h. The reaction mixture was concentrated under reduced pressure to give 5-chloro-1-(oxetan-3-yl)-1,2-dihydrospiro[indole-3,4'-piperidin]-2-one. MS=293.1 [M+H]$^+$.

912

Step 3: 5-chloro-1'-(2-(4-(methylsulfonyl)phenoxy)ethyl)-1-(oxetan-3-yl)spiro[indoline-3,4'-piperidin]-2-one (Compound 22)

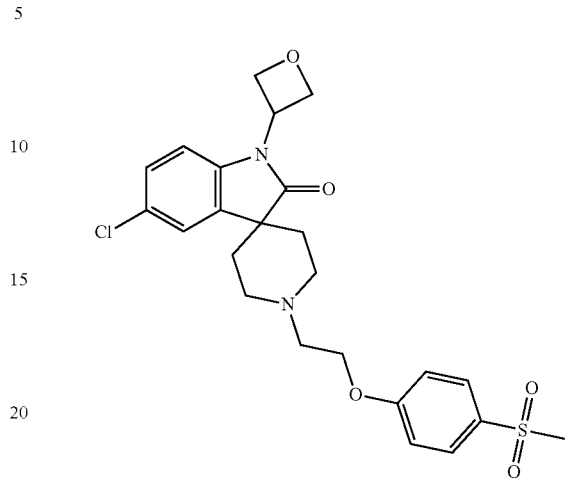

To a solution of 5-chloro-1-(oxetan-3-yl)-1,2-dihydrospiro[indole-3,4'-piperidin]-2-one (150 mg, 0.369 mmol, TFA salt) in MeCN (3 mL) were added $K_2CO_3$ (102 mg, 0.737 mmol) and 1-(2-bromoethoxy)-4-methanesulfonylbenzene (Intermediate A-3, 154 mg, 0.553 mmol). The mixture was stirred at 80° C. for 12 h. After cooling to room temperature, the reaction mixture was filtered and concentrated in vacuo. The crude residue was purified by reverse phase preparative HPLC (Waters Xbridge BEH $C_{18}$ column, 30-55% MeCN: 10 mM $NH_4HCO_3$ in $H_2O$) to give 5-chloro-1'-(2-(4-(methylsulfonyl)phenoxy)ethyl)-1-(oxetan-3-yl)spiro[indoline-3,4'-piperidin]-2-one (Compound 22). $^1$H NMR (400 MHz, DMSO-d$_6$): δ 7.84 (d, J=8.8 Hz, 2H), 7.61 (s, 1H), 7.42-7.34 (m, 2H), 7.19 (d, J=8.8 Hz, 2H), 5.43-5.35 (m, 1H), 5.00-4.87 (m, 4H), 4.25 (t, J=5.6 Hz, 2H), 3.16 (s, 3H), 2.94-2.88 (m, 4H), 2.75-2.19 (m, 2H), 1.85-1.75 (m, 4H). MS=491.1 [M+H]$^+$.

The following compounds in Table 20 were prepared according to procedures similar to steps 1-3 described for Compound 22 using the appropriate starting materials.

TABLE 20

| # | Structure | IUPAC Name | Exact Mass [M + H]$^+$ | Intermediate Used |
|---|---|---|---|---|
| 23 | 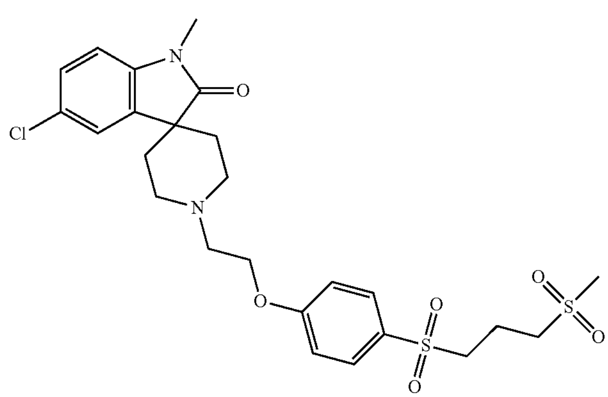 [SMILES: CN1C(=O)C2(CCN(CCOc3ccc(S(=O)(=O)CCCS(C)(=O)=O)cc3)CC2)c2cc(Cl)ccc21] | 5-chloro-1'-{2-[4-(3-methanesulfonylpropanesulfonyl)phenoxy]ethyl}-1-methyl-1,2-dihydrospiro[indole-3,4'-piperidin]-2-one | Calc'd 555.1 Found 555.2 | A-10 and B-3 |

TABLE 20-continued

| # | Structure | IUPAC Name | Exact Mass [M + H]+ | Intermediate Used |
|---|-----------|------------|---------------------|-------------------|
| 24 | 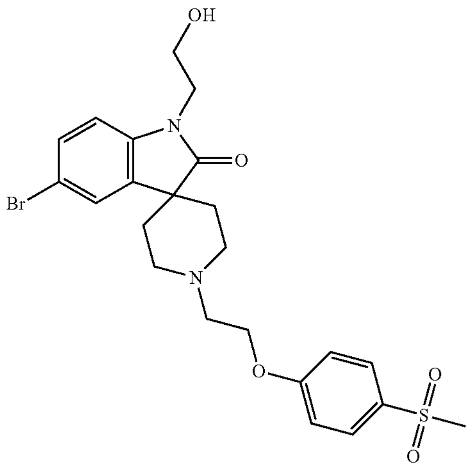 [SMILES: CS(=O)(=O)c1ccc(OCCN2CCC3(CC2)C(=O)N(CCO)c2ccc(Br)cc23)cc1] | 5-bromo-1-(2-hydroxyethyl)-1'-[2-(4-methanesulfonyl-phenoxy)ethyl]-1,2-dihydrospiro[indole-3,4'-piperidin]-2-one | Calc'd 523.1 Found 523.0 | A-3 |
| 25 | 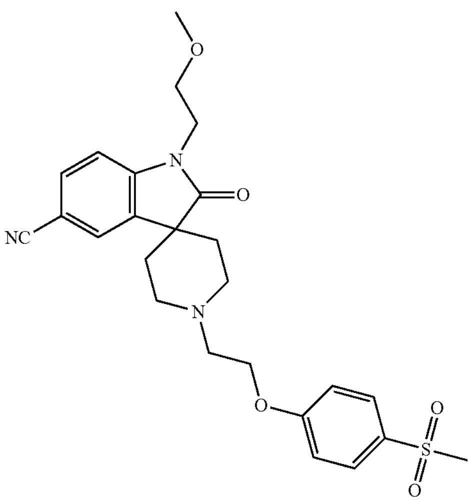 [SMILES: COCCN1C(=O)C2(CCN(CCOc3ccc(S(C)(=O)=O)cc3)CC2)c2cc(C#N)ccc21] | 1'-[2-(4-methanesulfonyl-phenoxy)ethyl]-1-(2-methoxyethyl)-2-oxo-1,2-dihydrospiro[indole-3,4'-piperidine]-5-carbonitrile | Calc'd 484.2 Found 484.2 | A-3 and B-8 |

Example 9

1-(2-(4-(methylsulfonyl)phenoxy)ethyl)spiro[azepane-4,3'-indolin]-2'-one (Compound 26)

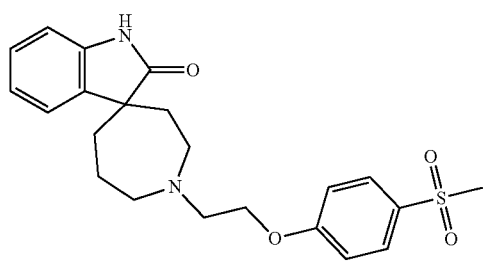 [SMILES: CS(=O)(=O)c1ccc(OCCN2CCCC3(CC2)C(=O)Nc2ccccc23)cc1]

Step 1: tert-butyl N-[2-(2-oxo-2,3-dihydro-1H-indol-3-yl)ethyl]carbamate

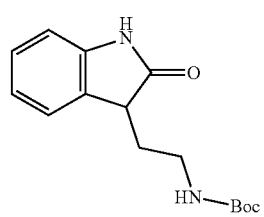 [SMILES: CC(C)(C)OC(=O)NCCC1C(=O)Nc2ccccc21]

To a solution of 2-(1H-indol-3-yl)ethan-1-amine (15 g, 93.6 mmol) in AcOH (90 mL) was added a solution of 12.0 M aqueous HCl (45 mL, 540 mmol) in DMSO (15 mL) dropwise. The mixture was stirred at room temperature for 3 h. The reaction mixture was diluted with H₂O (200 mL) and adjusted to pH=8 with the addition of solid Na₂CO₃. Boc₂O (21.8 g, 99.9 mmol) was added, and the mixture was stirred at room temperature for 16 h. The reaction mixture was filtered to give a crude product, which was isolated as a solid. The crude product was triturated with 4:1 petroleum ether:EtOAc and filtered to give tert-butyl N-[2-(2-oxo-2,3-dihydro-1H-indol-3-yl)ethyl]carbamate. MS=177.1 [M-C$_5$H$_8$O$_2$+H]$^+$.

Step 2: tert-butyl N-{2-[2-oxo-3-(prop-2-en-1-yl)-2,3-dihydro-1H-indol-3-yl]ethyl}carbamate

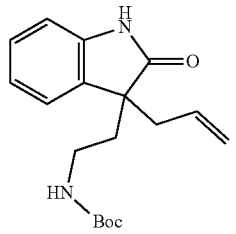 [SMILES: C=CCC1(CCNC(=O)OC(C)(C)C)C(=O)Nc2ccccc21]

To a 0° C. solution of tert-butyl N-[2-(2-oxo-2,3-dihydro-1H-indol-3-yl)ethyl]carbamate (4.50 g, 16.3 mmol) in DMA (60 mL) was added NaH (782 mg, 60 wt % in mineral oil, 19.5 mmol). After stirring for 30 min, 3-bromoprop-1-ene (1.97 g, 16.3 mmol) was added dropwise. The mixture was stirred at room temperature for 2.5 h. The reaction mixture was cooled to 0° C. and quenched by the addition of H$_2$O (20 mL), and then was extracted with EtOAc (3×20 mL). The combined organic layers were washed with brine (2×20 mL), dried over Na$_2$SO$_4$, filtered, and concentrated in vacuo. The crude residue was purified by normal phase silica gel chromatography (Biotage 40 g cartridge, 0-18% EtOAc: petroleum ether) to give tert-butyl N-{2-[2-oxo-3-(prop-2-en-1-yl)-2,3-dihydro-1H-indol-3-yl]ethyl}carbamate. MS=217.1 [M-C$_5$H$_8$O$_2$+H]$^+$.

Step 3: tert-butyl N-{2-[3-(3-hydroxypropyl)-2-oxo-2,3-dihydro-1H-indol-3-yl]ethyl}carbamate

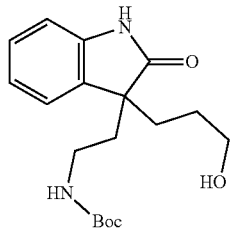 [SMILES: CC(C)(C)OC(=O)NCCC1(CCCO)C(=O)Nc2ccccc21]

To a 0° C. solution of tert-butyl N-{2-[2-oxo-3-(prop-2-en-1-yl)-2,3-dihydro-1H-indol-3-yl]ethyl}carbamate (4.10 g, 13.0 mmol) in THF (50 mL) was added 1.0 M BH$_3$·THF in THF (38.9 mL, 38.9 mmol) dropwise. The mixture was stirred at 0° C. for 2 h under N$_2$ atmosphere. The reaction mixture was quenched by the addition of H$_2$O (30 mL) at 0° C., and then NaOH (1.04 g, 25.9 mmol) and H$_2$O$_2$ in H$_2$O (5.27 mL, 30 wt %, 54.9 mmol) was added. The mixture was stirred at room temperature for 14 h. The reaction mixture was cooled to 0° C. and quenched by the addition of saturated aqueous Na$_2$SO$_3$ (20 mL) and extracted with EtOAc (3×30 mL). The combined organic layers were washed with saturated aqueous Na$_2$SO$_3$ (2×20 mL), dried over Na$_2$SO$_4$, filtered, and concentrated in vacuo. The crude residue was purified by normal phase silica gel chromatography (Biotage 40 g cartridge, 0-100% EtOAc:petroleum ether) to give tert-butyl N-{2-[3-(3-hydroxypropyl)-2-oxo-2,3-dihydro-1H-indol-3-yl]ethyl}carbamate. MS=235.2 [M-C$_5$H$_8$O$_2$+H]$^+$.

Step 4: tert-butyl N-{2-[2-oxo-3-(3-oxopropyl)-2,3-dihydro-1H-indol-3-yl]ethyl}carbamate

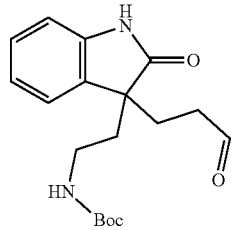 [SMILES: CC(C)(C)OC(=O)NCCC1(CCC=O)C(=O)Nc2ccccc21]

To a −78° C. solution of (COCl)$_2$ (825 µL, 9.42 mmol) in DCM (50 mL) was added DMSO (981 µL, 12.6 mmol) dropwise followed by tert-butyl N-{2-[3-(3-hydroxypropyl)-2-oxo-2,3-dihydro-1H-indol-3-yl]ethyl}carbamate (2.10 g, 6.28 mmol). After 30 min, TEA (2.62 mL, 18.8 mmol) was added. The mixture was warmed up to room temperature and stirred for 30 min. The reaction mixture was diluted with H$_2$O (20 mL) and extracted with DCM (3×10 mL). The combined organic layers were dried over Na$_2$SO$_4$, filtered and concentrated in vacuo to give crude tert-butyl N-{2-[2-oxo-3-(3-oxopropyl)-2,3-dihydro-1H-indol-3-yl]ethyl}carbamate, which was used in the subsequent step without further purification. MS=233.1 [M-C$_5$H$_8$O$_2$+H]$^+$.

Step 5: 3-[3-(2-aminoethyl)-2-oxo-2,3-dihydro-1H-indol-3-yl]propanal

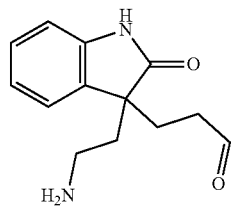 [SMILES: NCCC1(CCC=O)C(=O)Nc2ccccc21]

To a solution of tert-butyl N-{2-[2-oxo-3-(3-oxopropyl)-2,3-dihydro-1H-indol-3-yl]ethyl}carbamate (600 mg, 1.81 mmol) in DCM (20 mL) was added TFA (10.0 mL, 135 mmol). The mixture was stirred at room temperature for 3 h. The reaction mixture was concentrated in vacuo to give 3-[3-(2-aminoethyl)-2-oxo-2,3-dihydro-1H-indol-3-yl]propanal, which was used in the subsequent step without further purification. MS=233.1 [M+H]$^+$.

Step 6: 1',2'-dihydrospiro[azepane-4,3'-indol]-2'-one

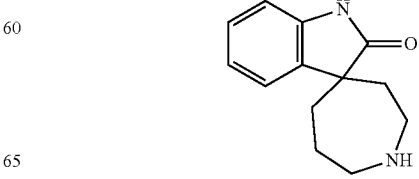

A solution of 3-[3-(2-aminoethyl)-2-oxo-2,3-dihydro-1H-indol-3-yl]propanal (1.81 mmol, TFA salt) in MeOH (20 mL) was adjusted to pH=6 by the dropwise addition of TEA. Then NaBH₃CN (210 mg, 3.35 mmol) was added, and the mixture was stirred at room temperature for 16 h. The reaction mixture cooled to 0° C. and was quenched by the addition H₂O (10 mL) and was then concentrated in vacuo. The crude residue was purified by reverse phase preparative HPLC (Waters Xbridge BEH C₁₈ column, 1-30% MeCN: 10 mM NH₄HCO₃ in H₂O) to give 1',2'-dihydrospiro[azepane-4,3'-indol]-2'-one. MS=217.1 [M+H]⁺.

Step 7: 1-(2-(4-(methylsulfonyl)phenoxy)ethyl)spiro[azepane-4,3'-indolin]-2'-one (Compound 26)

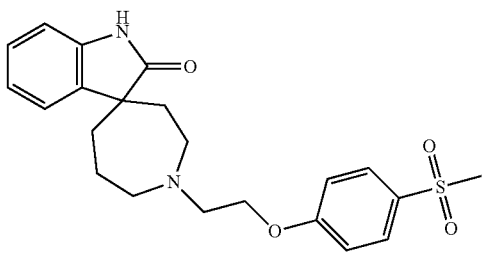 [SMILES: CS(=O)(=O)c1ccc(OCCN2CCCC3(CC2)C(=O)Nc2ccccc23)cc1]

A 70° C. solution of spiro[azepane-4,3'-indoline]-2'-one (50.0 mg, 0.231 mmol), 1-(2-bromoethoxy)-4-methanesulfonylbenzene (Intermediate A-3, 64.5 mg, 0.231 mmol) and K₂CO₃ (63.9 mg, 0.462 mmol) in MeCN (5 mL) was stirred for 10 h. After cooling to room temperature, the reaction mixture was concentrated in vacuo. The crude residue was purified by reverse phase preparative HPLC (Waters Welch Xtimate C₁₈ column, 5-25% MeCN: 0.04% HCl in H₂O) to give 1-(2-(4-(methylsulfonyl)phenoxy)ethyl)spiro[azepane-4,3'-indolin]-2'-one (Compound 26, HCl salt). ¹H NMR (400 MHz, DMSO-d₆): δ 11.08 (s, 1H), 10.52-10.46 (m, 1H), 7.91-7.88 (m, 2H), 7.52-7.40 (m, 1H), 7.25 (d, J=8.8 Hz, 2H), 7.23-7.18 (m, 1H), 7.00 (t, J=7.6 Hz, 1H), 6.86 (d, J=7.6 Hz, 1H), 4.59-4.54 (m, 2H), 3.92-3.80 (m, 1H), 3.67-3.60 (m, 4H), 3.36-3.34 (m, 1H), 3.17 (s, 3H), 2.43-2.38 (m, 1H), 2.22-1.88 (m, 5H). MS=415.2 [M+H]⁺.

Example 10

5-chloro-1'-[2-[(1-methyl-2-oxo-3,4-dihydroquinolin-6-yl)oxy]ethyl]spiro[indoline-3,4'-piperidine]-2-one (Compound 27)

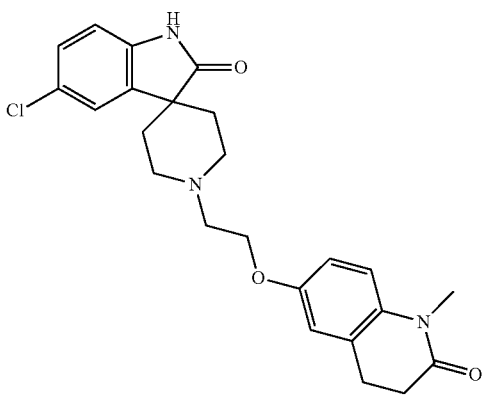 [SMILES: CN1C(=O)CCc2cc(OCCN3CCC4(CC3)C(=O)Nc3ccc(Cl)cc34)ccc21]

To a solution of 6-hydroxy-1-methyl-1,2,3,4-tetrahydroquinolin-2-one (Intermediate A-70, 50.0 mg, 0.282 mmol) and 5-chloro-1'-(2-chloroethyl)-1,2-dihydrospiro[indole-3,4'-piperidin]-2-one (Intermediate B-5, 169 mg, 0.564 mmol) in DMF (1 mL) was added K₂CO₃ (78.9 mg, 0.564 mmol). The mixture was stirred at 50° C. for 12 h under N₂ atmosphere, cooled to room temperature, and then filtered. The filtrate was purified by reverse phase preparative HPLC (Phenomenex Luna C₁₈ column, 5-25% MeCN: 0.04% HCl in H₂O) to give 5-chloro-1'-[2-[(1-methyl-2-oxo-3,4-dihydroquinolin-6-yl)oxy]ethyl]spiro[indoline-3,4'-piperidine]-2-one (Compound 27). ¹H NMR (400 MHz, DMSO-d₆): δ 10.53-10.49 (m, 1H), 7.50 (s, 1H), 7.23 (d, J=8.4 Hz, 1H), 7.00 (d, J=8.8 Hz, 1H), 6.88-6.83 (m, 3H), 4.10 (t, J=5.6 Hz, 2H), 3.22 (s, 3H), 2.91-2.78 (m, 6H), 2.67-2.64 (m, 2H), 2.44-2.42 (m, 2H), 1.83-1.66 (m, 4H). MS=440.3 [M+H]⁺.

Example 11

1'-(1-(4-(methylsulfonyl)phenoxy)propan-2-yl)spiro[indoline-3,4'-piperidin]-2-one (Compound 28)

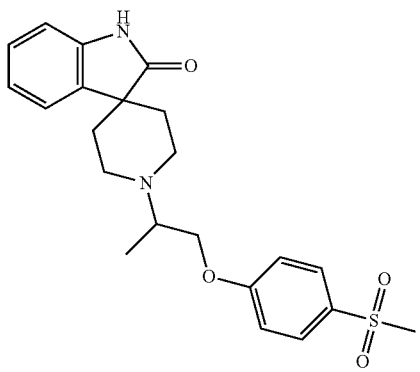 [SMILES: CC(COc1ccc(S(C)(=O)=O)cc1)N1CCC2(CC1)C(=O)Nc1ccccc12]

A 50° C. mixture of 1,2-dihydrospiro[indole-3,4'-piperidin]-2-one (150 mg, 0.742 mmol), 1-(4-methanesulfonylphenoxy)propan-2-one (Intermediate A-1, 169 mg, 0.742 mmol), Ti(i-PrO)₄ (211 mg, 0.742 mmol) and HOAc (4.0 mg, 0.074 mmol) in DCE (5 mL) was stirred for 30 min. After cooling to 0° C., NaBH(OAc)₃ (236 mg, 1.11 mmol) was added. The mixture was stirred at 50° C. for 16 h. After cooling to room temperature, the reaction mixture was quenched with addition of H₂O (10 mL). The mixture was filtered, and the filtrate was extracted with EtOAc (3×20 mL). The combined organic layers were washed with brine (30 mL), dried over Na₂SO₄, filtered, and concentrated in vacuo. The crude residue was purified by reverse phase preparative HPLC (Phenomenex Gemini NX—C₁₈, 10-50% MeCN: 10 mM NH₄HCO₃ in H₂O) to give 1'-(1-(4-(methylsulfonyl)phenoxy)propan-2-yl)spiro[indoline-3,4'-piperidin]-2-one (Compound 28). ¹H NMR (400 MHz, DMSO-d₆): δ 10.34 (s, 1H), 7.87-7.84 (m, 2H), 7.43-7.41 (m, 1H), 7.23-7.15 (m, 3H), 6.94-6.92 (m, 1H), 6.85-6.83 (m, 1H), 4.27-4.23 (m, 1H), 4.09-4.05 (m, 1H), 3.16 (s, 3H), 3.15-3.13 (m, 1H), 3.00-2.97 (m, 2H), 2.86-2.78 (m, 2H), 1.79-1.77 (m, 2H), 1.61-1.58 (m, 2H), 1.16 (d, J=6.4 Hz, 3H). MS=415.0 [M+H]⁺.

Example 12

1-methyl-1'-{2-[(3-methyl-4-oxo-3,4-dihydroquinazolin-6-yl)oxy]ethyl}-1,2-dihydrospiro[indole-3,4'-piperidin]-2-one (Compound 29)

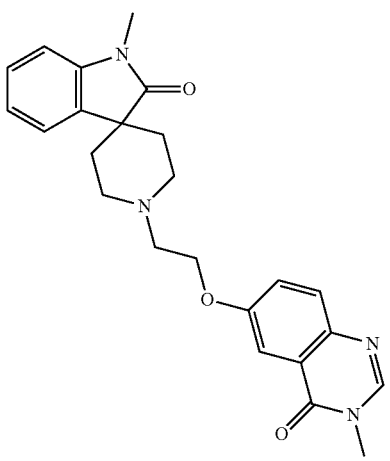 [SMILES: CN1C(=O)C2(CCN(CCOc3ccc4ncn(C)c(=O)c4c3)CC2)c2ccccc21]

1'-(2-hydroxyethyl)-1-methyl-1,2-dihydrospiro[indole-3,4'-piperidin]-2-one (Intermediate B-7, 130 mg, 0.50 mmol) and 6-hydroxy-3-methyl-3,4-dihydroquinazolin-4-one (88 mg, 0.50 mmol) were added to a 40 mL vial, followed by toluene (2.00 mL), polymer-bound PPh$_3$ (167 mg, 78.6% PPh$_3$ loading by weight, 0.500 mmol) and DIAD (120 mg, 0.600 mmol). The mixture was stirred at room temperature for 12 h, then was filtered and concentrated in vacuo. The crude residue was purified by reverse phase preparative HPLC (Phenomenex Gemini NX—C$_{18}$, 0-50% MeCN: 10 mM NH$_4$OH in H$_2$O) to give 1'-(1-(4-(methylsulfonyl)phenoxy)propan-2-yl)spiro[indoline-3,4'-piperidin]-2-one (Compound 29). $^1$H NMR (400 MHz, CDCl$_3$): δ 7.96 (s, 1H), 7.71 (d, J=2.85 Hz, 1H), 7.65 (d, J=8.99 Hz, 1H), 7.39 (dd, J=8.88, 2.74 Hz, 2H), 7.27-7.31 (m, 1H), 7.00-7.12 (m, 1H), 6.84 (d, J=7.67 Hz, 1H), 4.23-4.42 (m, 2H), 3.60 (s, 3H), 3.20 (s, 3H), 3.00-3.19 (m, 4H), 2.81-3.00 (m, 2H), 1.81-2.06 (m, 4H). MS=419.2 [M+H]$^+$.

The following compounds in Table 21 were prepared according to procedures similar to those described for Compound 29 using the appropriate starting materials.

TABLE 21

| # | Structure | IUPAC Name | Exact Mass [M + H]$^+$ | Intermediate Used |
|---|---|---|---|---|
| 30 | 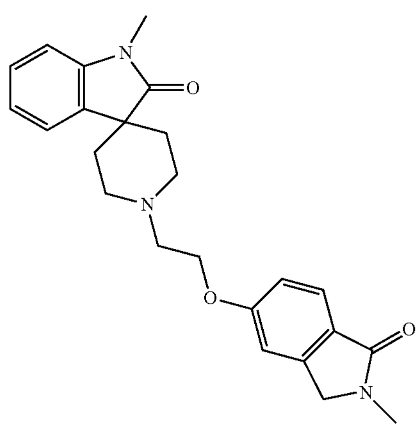 [SMILES: CN1Cc2cc(OCCN3CCC4(CC3)C(=O)N(C)c3ccccc34)ccc2C1=O] | 1-methyl-1'-{2-[(2-methyl-1-oxo-2,3-dihydro-1H-isoindol-5-yl)oxy]ethyl}-1,2-dihydrospiro[indole-3,4'-piperidin]-2-one | Calc'd 406.2 Found 406.2 | B-7 |
| 31 | 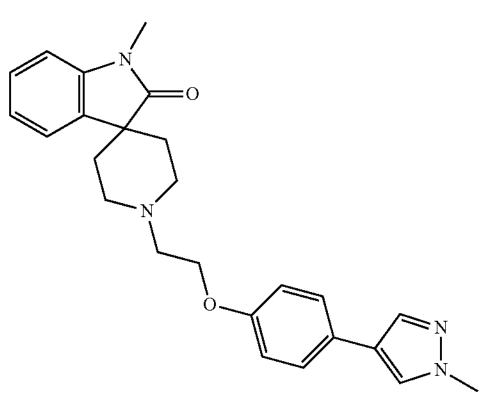 [SMILES: CN1C(=O)C2(CCN(CCOc3ccc(-c4cnn(C)c4)cc3)CC2)c2ccccc21] | 1-methyl-1'-{2-[4-(1-methyl-1H-pyrazol-4-yl)phenoxy]ethyl}-1,2-dihydrospiro[indole-3,4'-piperidin]-2-one | Calc'd 417.2 Found 417.2 | B-7 |

TABLE 21-continued

| # | Structure | IUPAC Name | Exact Mass [M + H]⁺ | Intermediate Used |
|---|---|---|---|---|
| 32 | 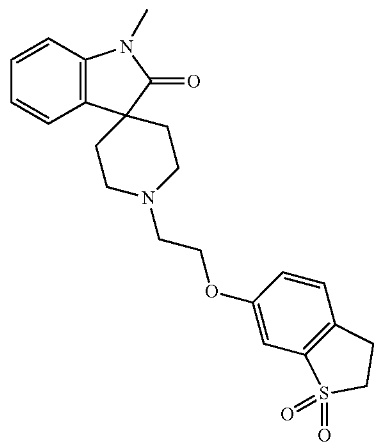 [SMILES: CN1C(=O)C2(CCN(CCOc3ccc4c(c3)S(=O)(=O)CC4)CC2)c2ccccc21] | 5-(2-{1-methyl-2-oxo-1,2-dihydrospiro[indole-3,4'-piperidin]-1'-yl}ethoxy)-2,3-dihydro-1$\lambda^6$-benzothiophene-1,1-dione | Calc'd 427.1 Found 427.2 | B-7 |
| 33 | 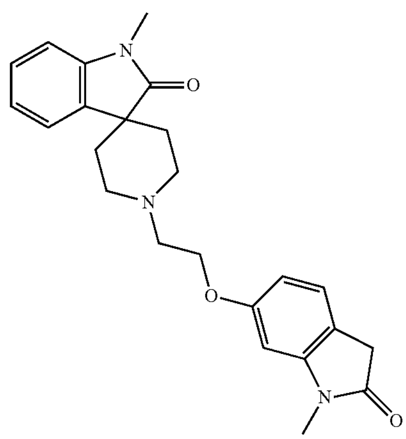 [SMILES: CN1C(=O)Cc2ccc(OCCN3CCC4(CC3)C(=O)N(C)c3ccccc34)cc21] | 1-methyl-1'-{2-[(1-methyl-2-oxo-2,3-dihydro-1H-indol-5-yl)oxy]ethyl}-1,2-dihydrospiro[indole-3,4'-piperidin]-2-one | Calc'd 406.2 Found 406.2 | B-7 |
| 34 | 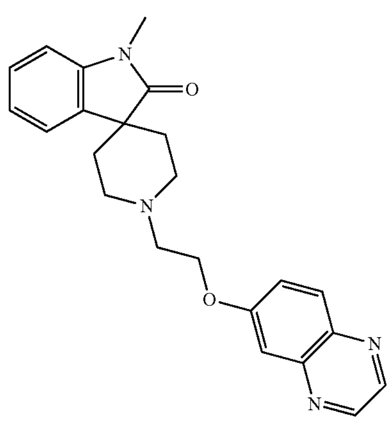 [SMILES: CN1C(=O)C2(CCN(CCOc3ccc4nccnc4c3)CC2)c2ccccc21] | 1-methyl-1'-[2-(quinoxalin-6-yloxy)ethyl]-1,2-dihydrospiro[indole-3,4'-piperidin]-2-one | Calc'd 389.1 Found 389.2 | B-7 |

TABLE 21-continued

| # | Structure | IUPAC Name | Exact Mass [M + H]+ | Intermediate Used |
|---|---|---|---|---|
| 35 | 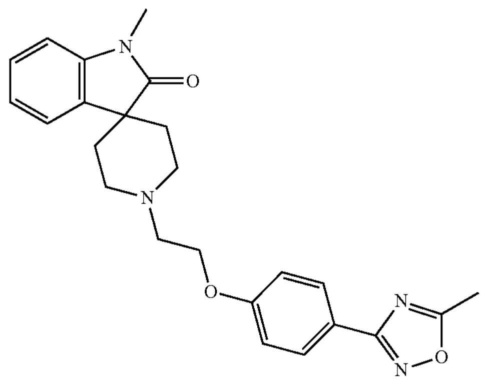 [SMILES: Cc1nc(-c2ccc(OCCN3CCC4(CC3)C(=O)N(C)c3ccccc34)cc2)no1] | 1-methyl-1'-{2-[4-(5-methyl-1,2,4-oxadiazol-3-yl)phenoxy]ethyl}-1,2-dihydrospiro[indole-3,4'-piperidin]-2-one | Calc'd 419.2 Found 419.2 | B-7 |
| 36 | 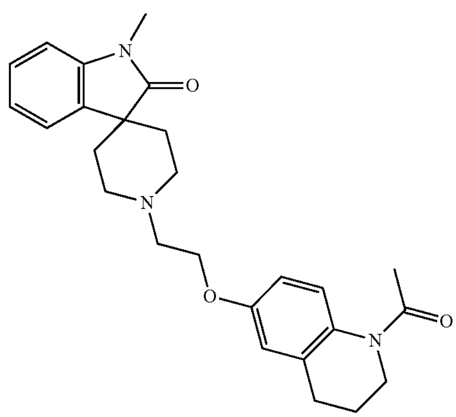 [SMILES: CC(=O)N1CCCc2cc(OCCN3CCC4(CC3)C(=O)N(C)c3ccccc34)ccc21] | 1'-{2-[(1-acetyl-1,2,3,4-tetrahydroquinolin-6-yl)oxy]ethyl}-1-methyl-1,2-dihydrospiro[indole-3,4'-piperidin]-2-one | Calc'd 434.2 Found 434.3 | B-7 |
| 37 | 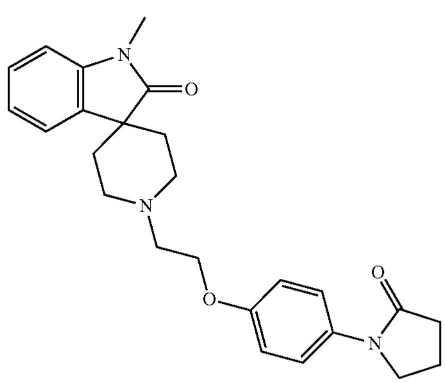 [SMILES: CN1C(=O)C2(CCN(CCOc3ccc(N4CCCC4=O)cc3)CC2)c2ccccc21] | 1-methyl-1'-{2-[4-(2-oxopyrrolidin-1-yl)phenoxy]ethyl}-1,2-dihydrospiro[indole-3,4'-piperidin]-2-one | Calc'd 420.2 Found 420.2 | B-7 |

Example 13

5-chloro-1'-{2-[4-(1-methanesulfonylethyl)phenoxy]ethyl}-1,2-dihydrospiro[indole-3,4'-piperidin]-2-one (Compound 38), 5-chloro-1'-(2-{4-[(1S) or (1R)-1-methanesulfonylethyl]phenoxy}ethyl)-1,2-dihydrospiro[indole-3,4'-piperidin]-2-one (Compound 39), and 5-chloro-1'-(2-{4-[(1R) or (1S)-1-methanesulfonylethyl]phenoxy}ethyl)-1,2-dihydrospiro[indole-3,4'-piperidin]-2-one (Compound 40)

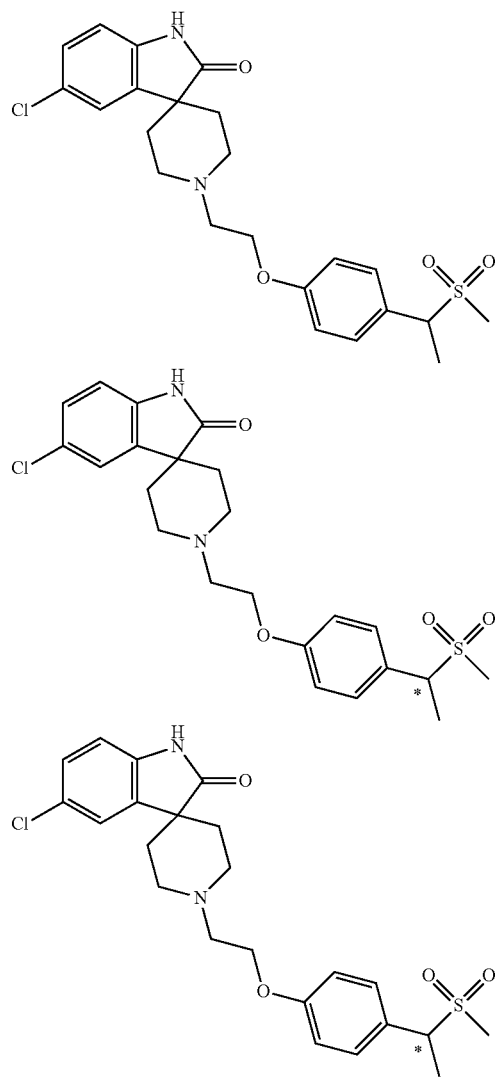

Step 1: 1-(1-chloroethyl)-4-methoxybenzene

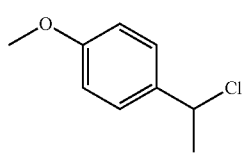

To a 0° C. solution of 1-(4-methoxyphenyl)ethan-1-ol (5.00 g, 32.9 mmol) in DCM (50 mL) was added SOCl$_2$ (2.86 mL, 39.4 mmol). The mixture was allowed to warm to room temperature and stirred for 3 h. The reaction mixture was concentrated in vacuo to give 1-(1-chloroethyl)-4-methoxybenzene, which was used in the next step without further purification.

Step 2:
1-(1-methanesulfonylethyl)-4-methoxybenzene

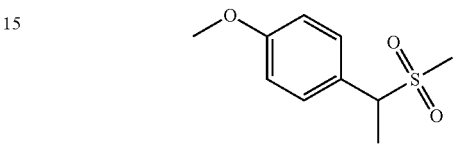

A mixture of 1-(1-chloroethyl)-4-methoxybenzene (6.00 g, 35.1 mmol) and sodium methanesulfinate (7.18 g, 70.3 mmol) in DMF (60 mL) was stirred at 80° C. for 16 h. The mixture was cooled to 0° C. and quenched by the addition of H$_2$O (50 mL) and extracted with EtOAc (3×50 mL). The combined organic layers were washed with H$_2$O (50 mL), brine (50 mL), dried over Na$_2$SO$_4$, filtered, and concentrated in vacuo. The crude residue was purified by normal phase silica gel chromatography (Biotage 80 g cartridge, 0-50% EtOAc:petroleum ether) to give 1-(1-methanesulfonylethyl)-4-methoxybenzene. MS=135.1 [M-CH$_3$SO$_2$]$^+$.

Step 3: 4-(1-methanesulfonylethyl)phenol

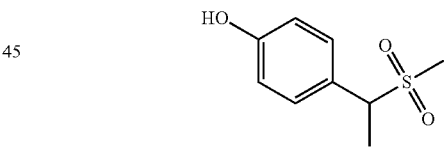

To a solution of 1-(1-methanesulfonylethyl)-4-methoxybenzene (500 mg, 2.33 mmol) in MeCN (5 mL) was added NaI (1.40 g, 9.33 mmol) and TMSCl (1.18 mL, 9.33 mmol). The mixture was stirred at 80° C. for 16 h. After cooling to room temperature, the reaction mixture was quenched by the addition of H$_2$O (20 mL) and extracted with EtOAc (3×20 mL). The combined organic layers were washed with saturated aqueous Na$_2$S2O3 (60 mL), brine (60 mL), dried over Na$_2$SO$_4$, filtered, and concentrated in vacuo. The crude residue was purified by normal phase silica gel chromatography (Biotage 12 g cartridge, 25-50% EtOAc:petroleum ether) to give 4-(1-methanesulfonylethyl)phenol. MS=218.2 [M+NH$_4$]$^+$.

Step 4: 5-chloro-1'-{2-[4-(1-methanesulfonylethyl)phenoxy]ethyl}-1,2-dihydrospiro[indole-3,4'-piperidin]-2-one (Compound 38)

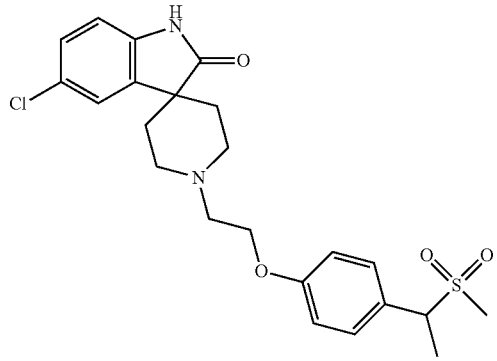

To a mixture of 5-chloro-1'-(2-chloroethyl)-1,2-dihydrospiro[indole-3,4'-piperidin]-2-one (Intermediate B-5, 269 mg, 0.899 mmol) in acetone (10 mL) was added NaI (4.5 mg, 0.030 mmol), $K_2CO_3$ (82.8 mg, 0.599 mmol) and 4-(1-methanesulfonylethyl)phenol (120 mg, 0.599 mmol). The mixture was stirred at 50° C. for 12 h. After cooling to room temperature, the reaction mixture was diluted with $H_2O$ (10 mL) and extracted with EtOAc (3×10 mL). The combined organic layers were washed with brine (10 mL), dried over $Na_2SO_4$, filtered, and concentrated in vacuo. The crude residue was purified by reverse phase preparative HPLC (Phenomenex Gemini NX—$C_{18}$, 20-50% MeCN: 10 mM $NH_4HCO_3$ in $H_2O$) to give 5-chloro-1'-{2-[4-(1-methanesulfonylethyl)phenoxy]ethyl}-1,2-dihydrospiro[indole-3,4'-piperidin]-2-one (Compound 38). $^1$H NMR (400 MHz, DMSO-$d_6$): δ 10.49 (s, 1H), 7.51 (s, 1H), 7.36 (d, J=8.8 Hz, 2H), 7.23 (m, 1H), 6.99 (d, J=8.8 Hz, 2H), 6.84 (d, J=8.4 Hz, 1H), 4.47 (m 1H), 4.14 (t, J=5.4 Hz, 2H), 2.91-2.84 (m, 4H), 2.77 (s, 3H), 2.73-2.65 (m, 1H), 1.83-1.67 (m, 5H), 1.59 (d, J=7.2 Hz, 3H). MS=463.3 [M+H]$^+$.

Step 5: 5-chloro-1'-(2-{4-[(1S) or (1R)-1-methanesulfonylethyl]phenoxy}ethyl)-1,2-dihydrospiro[indole-3,4'-piperidin]-2-one (Compound 39) and 5-chloro-1'-(2-{4-[(1R) or (1S)-1-methanesulfonylethyl]phenoxy}ethyl)-1,2-dihydrospiro[indole-3,4'-piperidin]-2-one (Compound 40)

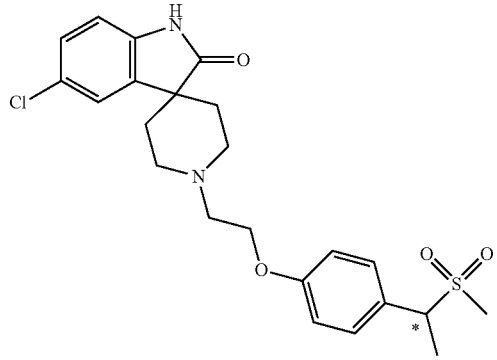 [SMILES: CC(c1ccc(OCCN2CCC3(CC2)C(=O)Nc2ccc(Cl)cc23)cc1)S(C)(=O)=O]

-continued

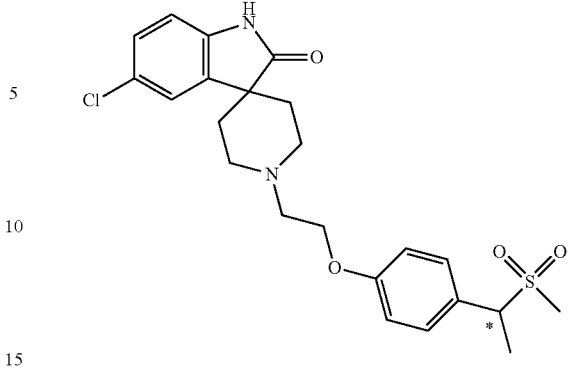

5-chloro-1'-{2-[4-(1-methanesulfonylethyl)phenoxy]ethyl}-1,2-dihydrospiro[indole-3,4'-piperidin]-2-one (Compound 38, 45 mg, 0.060 mmol) was separated by preparative chiral SFC (Chiralcel OD-3 column, 60% ethanol with 0.1% $NH_4OH$ in $CO_2$). The first eluting enantiomer of the title compound, 5-chloro-1'-(2-{4-[(1S) or (1R)-1-methanesulfonylethyl]phenoxy}ethyl)-1,2-dihydrospiro[indole-3,4'-piperidin]-2-one (Compound 39): $^1$H NMR (400 MHz, DMSO-$d_6$): δ 10.50 (s, 1H), 7.51 (d, J=2.0 Hz, 1H), 7.36 (d, J=8.8 Hz, 2H), 7.23 (dd, J=8.4, 2.2 Hz, 1H), 6.99 (d, J=8.8 Hz, 2H), 6.84 (d, J=8.4 Hz, 1H), 4.47 (q, J=7.2 Hz, 1H), 4.14 (t, J=5.6 Hz, 2H), 2.92-2.89 (m, 2H), 2.86-2.83 (m, 2H), 2.77 (s, 3H), 2.71-2.68 (m, 2H), 1.82-1.67 (m, 4H), 1.59 (d, J=7.2 Hz, 3H). MS=463.2 [M+H]$^+$. The second eluting enantiomer of the title compound, 5-chloro-1'-(2-{4-[(1R) or (1S)-1-methanesulfonylethyl]phenoxy}ethyl)-1,2-dihydrospiro[indole-3,4'-piperidin]-2-one (Compound 40): $^1$H NMR (400 MHz, DMSO-$d_6$): δ 10.49 (s, 1H), 7.51 (d, J=2.0 Hz, 1H), 7.36 (d, J=8.8 Hz, 2H), 7.23 (dd, J=8.4, 2.2 Hz, 1H), 6.99 (d, J=9.0 Hz, 2H), 6.84 (d, J=8.0 Hz, 1H), 4.47 (q, J=7.2 Hz, 1H), 4.14 (t, J=5.6 Hz, 2H), 2.95-2.88 (m, 2H), 2.85 (t, J=5.6 Hz, 2H), 2.77 (s, 3H), 2.74-2.68 (m, 2H), 1.82-1.68 (m, 4H), 1.60 (d, J=7.2 Hz, 3H). MS=463.2 [M+H]$^+$.

Example 14

5-chloro-1'-{2-[4-(3-methanesulfonylpropanesulfonyl)phenoxy]ethyl}-1,2-dihydrospiro[indole-3,4'-piperidin]-2-one (Compound 41)

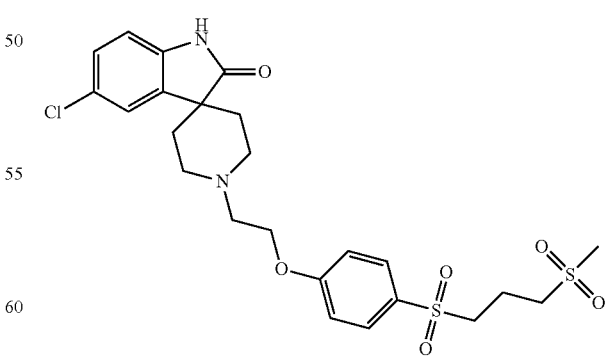

To a solution of 4-(3-methanesulfonylpropanesulfonyl)phenol (Intermediate A-9, 60.0 mg, 0.216 mmol) in DMF (2 mL) was added $K_2CO_3$ (59.6 mg, 0.431 mmol) and 5-chloro-1'-(2-chloroethyl)-1,2-dihydrospiro[indole-3,4'-piperidin]-

2-one (Intermediate B-5, 129 mg, 0.431 mmol). The mixture was stirred at 50° C. for 12 h. The reaction mixture was filtered and the filtrate was purified by reverse phase preparative HPLC (Waters Xbridge BEH $C_{18}$ column, 20-55% MeCN: 10 mM $NH_4HCO_3$ in $H_2O$) to give 5-chloro-1'-{2-[4-(3-methanesulfonylpropanesulfonyl)phenoxy]ethyl}-1,2-dihydrospiro[indole-3,4'-piperidin]-2-one (Compound 41). $^1$H NMR (400 MHz, DMSO-$d_6$): δ 10.48 (s, 1H), 7.82 (d, J=8.8 Hz, 2H), 7.51 (d, J=2.0 Hz, 1H), 7.25-7.21 (m, 3H), 6.84 (d, J=8.4 Hz, 1H), 4.26 (t, J=5.6 Hz, 2H), 3.44-3.37 (m, 2H), 3.24-3.18 (m, 2H), 2.97 (s, 3H), 2.94-2.84 (m, 4H), 2.75-2.70 (m, 2H), 1.99-1.94 (m, 2H), 1.77-1.73 (in, 4H). MS=541.2 [M+H]$^+$.

The following compounds in Table 22 were prepared according to procedures similar to those described for Compound 41 using the appropriate starting materials

TABLE 22

| # | Structure | IUPAC Name | Exact Mass [M + H]$^+$ | Intermediates Used |
|---|---|---|---|---|
| 42 | 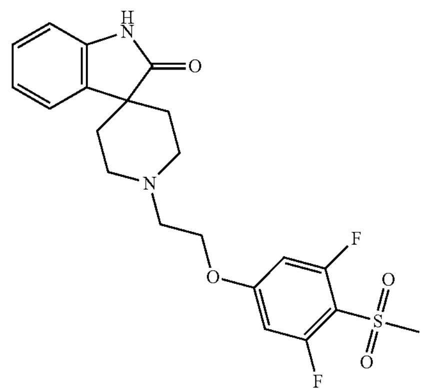 [SMILES: CS(=O)(=O)c1c(F)cc(OCCN2CCC3(CC2)C(=O)Nc2ccccc23)cc1F] | 1'-[2-(3,5-difluoro-4-methanesulfonyl-phenoxy)ethyl]-1,2-dihydrospiro[indole-3,4'-piperidin]-2-one | Calc'd 437.1 Found 437.0 | A-11 and B-10 |
| 43 | 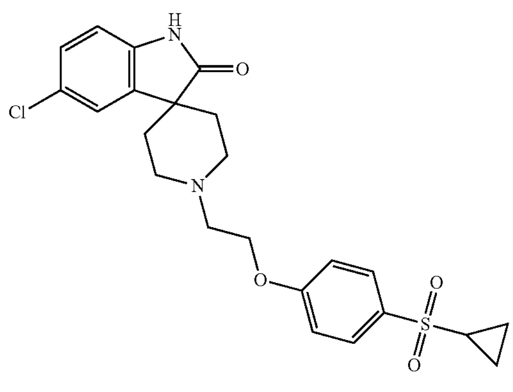 [SMILES: O=C1Nc2ccc(Cl)cc2C12CCN(CCOc1ccc(S(=O)(=O)C3CC3)cc1)CC2] | 5-chloro-1'-{2-[4-(cyclopropane-sulfonyl)phenoxy]ethyl}-1,2-dihydrospiro[indole-3,4'-piperidin]-2-one | Calc'd 461.1 Found 461.1 | B-5 |
| 44 | 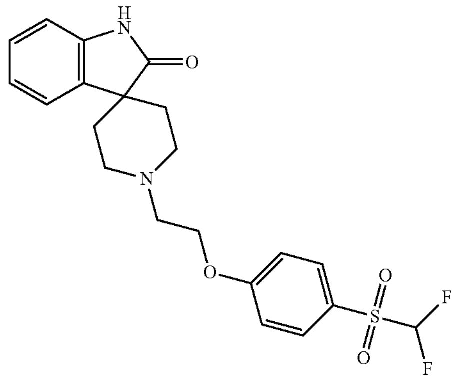 [SMILES: O=C1Nc2ccccc2C12CCN(CCOc1ccc(S(=O)(=O)C(F)F)cc1)CC2] | 1'-[2-(4-difluoromethanesulfo-nylphenoxy)ethyl]-1,2-dihydrospiro[indole-3,4'-piperidin]-2-one | Calc'd 437.1 Found 437.2 | A-15 and B-10 |

Example 15

4-(2-{5-chloro-2-oxo-1,2-dihydrospiro[indole-3,4'-piperidin]-1'-yl}ethoxy)benzamide (Compound 45)

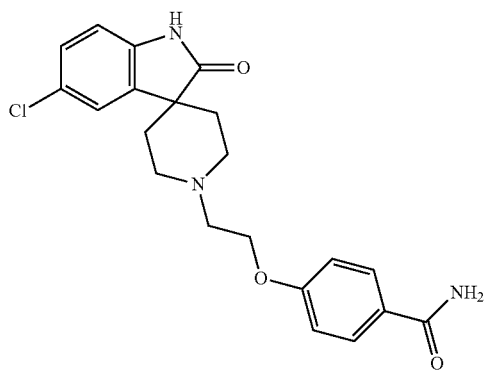 [SMILES: NC(=O)c1ccc(OCCN2CCC3(CC2)C(=O)Nc2ccc(Cl)cc23)cc1]

Step 1: 4-(2-bromoethoxy)benzamide

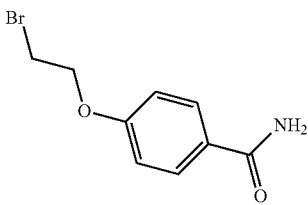 [SMILES: NC(=O)c1ccc(OCCBr)cc1]

A mixture of 4-hydroxybenzamide (200 mg, 1.46 mmol), Cs₂CO₃ (950 mg, 2.92 mmol), and 1,2-dibromoethane (2.01 mL, 23.3 mmol) was stirred at 110° C. for 18 h in a sealed vial. After cooling to room temperature, the reaction mixture was diluted with DCM and filtered. The filter cake was then washed with acetone (3×5 mL) and the filtrate was concentrated in vacuo to give 4-(2-bromoethoxy)benzamide, which was taken to the next step without further purification. ¹H NMR (500 MHz, CDCl₃): δ 7.81-7.76 (m, 2H), 6.95 (dd, J=8.8, 2.2 Hz, 2H), 6.17-5.19 (m, 2H), 4.34 (t, J=2.0 Hz, 2H), 3.66 (t, J=2.1 Hz, 2H). MS=243.9 [M+H]⁺.

Step 2: 4-(2-{5-chloro-2-oxo-1,2-dihydrospiro[indole-3,4'-piperidin]-1'-yl}ethoxy)benzamide (Compound 45)

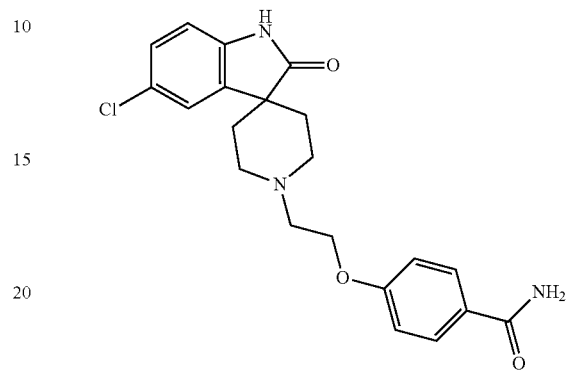

A mixture of 4-(2-bromoethoxy)benzamide, (36.0 mg, 0.15 mmol), 5-chloro-1,2-dihydrospiro[indole-3,4'-piperidin]-2-one (Intermediate B-4, 40 mg, 0.15 mmol, HCl salt), and potassium carbonate (61 mg, 0.44 mmol) was taken up in DMF (0.6 mL). The mixture was stirred at 80° C. for 3 h. After cooling to room temperature, the reaction mixture was diluted with H₂O (0.15 mL) and formic acid (3 drops) was added. The mixture was stirred at room temperature for an additional 10 min and solids were removed by filtration. The filtrate was purified reverse phase preparative HPLC (Phenomenex Kinetex C₁₈ column, 5-30% MeCN:H₂O with 0.1% formic acid modifier) to give 4-(2-{5-chloro-2-oxo-1,2-dihydrospiro[indole-3,4'-piperidin]-1'-yl}ethoxy)benzamide (Compound 45). ¹H NMR (500 MHz, DMSO-d₆): δ 10.52 (s, 1H), 7.84-7.78 (m, 3H), 7.51 (s, 1H), 7.25 (d, J=8.3 Hz, 1H), 7.17 (s, 1H), 7.02 (d, J=8.3 Hz, 2H), 6.85 (d, J=8.3 Hz, 1H), 4.23 (s, 2H), 3.15-2.66 (m, 6H), 2.13-1.60 (m, 4H). MS=400.1 [M+H]⁺.

The following compounds in Table 23 were prepared according to procedures analogous to steps 1-2 described for Compound 45 using the appropriate starting materials.

TABLE 23

| # | Structure | IUPAC Name | Exact Mass [M + H]⁺ | Intermediate Used |
|---|---|---|---|---|
| 46 | ![structure] | 4-(2-{5-chloro-2-oxo-1,2-dihydrospiro[indole-3,4'-piperidin]-1'-yl}ethoxy)-2-fluorobenzamide | Calc'd 418.1 Found 418.1 | B-4 |

TABLE 23-continued

| # | Structure | IUPAC Name | Exact Mass [M + H]+ | Intermediate Used |
|---|---|---|---|---|
| 47 | 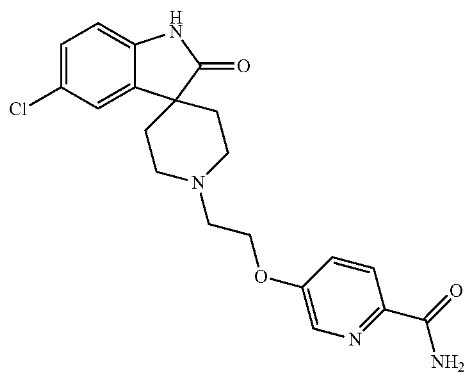 [SMILES: NC(=O)c1ccc(OCCN2CCC3(CC2)C(=O)Nc2ccc(Cl)cc23)cn1] | 5-(2-{5-chloro-2-oxo-1,2-dihydrospiro[indole-3,4'-piperidin]-1'-yl}ethoxy)pyridine-2-carboxamide | Calc'd 401.1 Found 401.2 | B-4 |
| 48 | 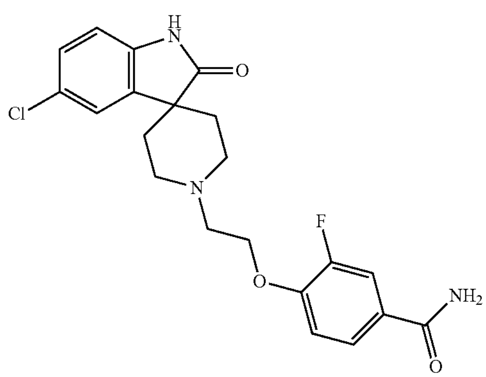 [SMILES: NC(=O)c1ccc(OCCN2CCC3(CC2)C(=O)Nc2ccc(Cl)cc23)c(F)c1] | 5-chloro-1'-[2-(2-fluoro-4-methanesulfonyl-phenoxy)ethyl]-1,2-dihydrospiro[indole-3,4'-piperidin]-2-one | Calc'd 453.1 Found 453.0 | B-4 |
| 49 | 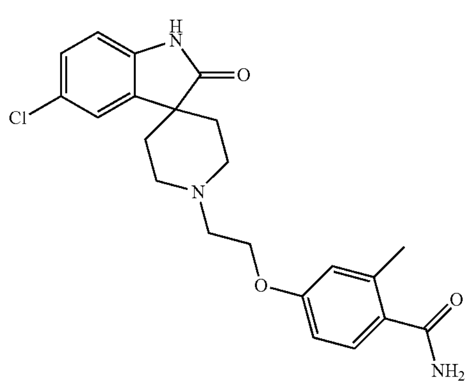 [SMILES: Cc1cc(OCCN2CCC3(CC2)C(=O)Nc2ccc(Cl)cc23)ccc1C(N)=O] | 4-(2-{5-chloro-2-oxo-1,2-dihydrospiro[indole-3,4'-piperidin]-1'-yl}ethoxy)-2-methylbenzamide | Calc'd 414.2 Found 414.2 | B-4 |

Example 16

5-(2-{5-chloro-2-oxo-1,2-dihydrospiro[indole-3,4'-piperidin]-1'-yl}ethoxy)-2-methanesulfonylbenzonitrile (Compound 50)

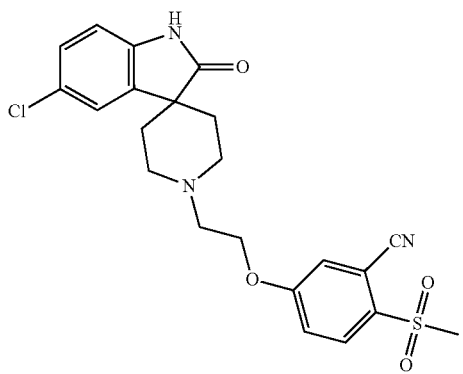 [SMILES: CS(=O)(=O)c1ccc(OCCN2CCC3(CC2)C(=O)Nc2ccc(Cl)cc23)cc1C#N]

Step 1: 2-fluoro-5-(2-hydroxyethoxy)benzonitrile

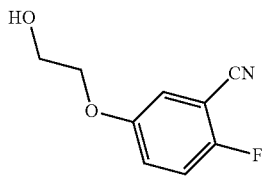 [SMILES: N#Cc1cc(OCCO)ccc1F]

A mixture of 2-fluoro-5-hydroxybenzonitrile (1.00 g, 7.29 mmol), K$_2$CO$_3$ (3.02 g, 21.9 mmol), and ethylene carbonate (20.6 mL, 24.1 mmol) was taken up in DMF (10 mL). The mixture was stirred at 110° C. for 18 hours. After cooling to room temperature, the reaction mixture was filtered to remove solids and concentrated in vacuo. The residue was taken up in EtOAc (15 mL), and then washed with H$_2$O (5 mL) and brine (5 mL). The organic layer was dried over Na$_2$SO$_4$, filtered, and concentrated to give 2-fluoro-5-(2-hydroxyethoxy)benzonitrile, which was taken to the next step without further purification. $^1$H NMR (500 MHz, CDCl$_3$): δ 7.18-7.11 (m, 2H), 7.10 (dd, J=5.2, 2.5 Hz, 1H), 4.10-4.04 (m, 2H), 3.98 (t, J=4.4 Hz, 2H), 1.98 (s, 1H).

Step 2: 5-(2-hydroxyethoxy)-2-(methylsulfanyl)benzonitrile

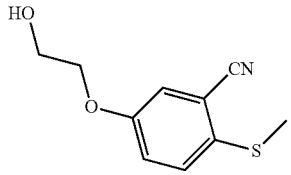

A mixture of 2-fluoro-5-(2-hydroxyethoxy)benzonitrile (875 mg, 4.83 mmol), aqueous sodium methanethiolate (6.77 g, 15 wt %, 14.5 mmol), and DMF (6.7 mL) was stirred at 60° C. for 18 h. After cooling to room temperature, the reaction mixture was diluted with brine (10 mL) and extracted EtOAc (3×10 mL). The combined organic layers were dried over Na$_2$SO$_4$, filtered, and concentrated in vacuo to give 5-(2-hydroxyethoxy)-2-(methylsulfanyl)benzonitrile, which was taken to the next step without further purification. $^1$H NMR (500 MHz, CDCl$_3$, 10/11 H): δ 7.36 (d, J=8.8 Hz, 1H), 7.15 (d, J=2.8 Hz, 1H), 7.11 (dd, J=8.8, 2.8 Hz, 1H), 4.08 (dd, J=5.1, 3.8 Hz, 2H), 3.98 (t, J=4.4 Hz, 2H), 2.52 (s, 3H).

Step 3: 5-(2-hydroxyethoxy)-2-methanesulfonylbenzonitrile

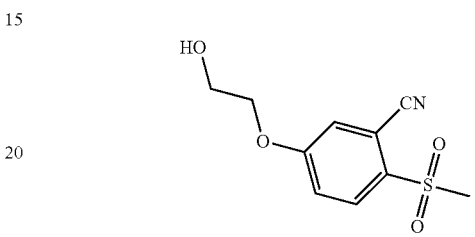

To a 0° C. suspension of 5-(2-hydroxyethoxy)-2-(methylsulfanyl)benzonitrile (169 mg, 0.808 mmol) in DCM (3 mL) was added m-CPBA (432 mg, 2.50 mmol) in a single portion. The mixture was allowed to slowly warm to room temperature and stirred for 18 h. The reaction mixture was diluted with saturated aqueous NaHCO$_3$ (10 mL) and allowed to stir for an additional 15 min. The organic layer was separated, and the aqueous layer was extracted with EtOAc (3×10 mL). The combined organic layers were dried over Na$_2$SO$_4$, filtered, and concentrated in vacuo. The crude residue was purified by normal phase silica gel chromatography (Biotage 10 g cartridge, 0-100% EtOAc:Hexanes) to give 5-(2-hydroxyethoxy)-2-methanesulfonylbenzonitrile. $^1$H NMR (500 MHz, CDCl$_3$, 10/11 H): δ 8.12 (d, J=8.9 Hz, 1H), 7.43 (s, 1H), 7.30 (dd, J=9.0, 2.6 Hz, 1H), 4.24 (t, J=4.4 Hz, 2H), 4.07 (t, J=4.5 Hz, 2H), 3.27 (s, 3H).

Step 4: 2-(3-cyano-4-methanesulfonylphenoxy)ethyl methanesulfonate

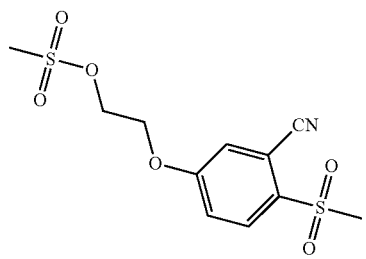

Methanesulfonyl chloride (70 μL, 0.82 mmol) was added dropwise via syringe to a 0° C. solution of 5-(2-hydroxyethoxy)-2-methanesulfonylbenzonitrile (132 mg, 0.548 mmol) and DIEA (0.19 mL, 0.82 mmol) in DCM (2 mL). The mixture was allowed to slowly warm to room temperature and stirred for 3 h. The reaction mixture was diluted with saturated aqueous NH$_4$Cl (5 mL) and stirred for an additional 15 min. The organic layer was separated, and the aqueous layer was extracted with DCM (3×2 mL). The combined organic layers were dried over Na$_2$SO$_4$, filtered, and concentrated in vacuo to give 2-(3-cyano-4-methanesulfonylphenoxy)ethyl methanesulfonate, which was taken to the next step without further purification.

Step 5: 5-(2-{5-chloro-2-oxo-1,2-dihydrospiro[indole-3,4'-piperidin]-1'-yl}ethoxy)-2-methanesulfonylbenzonitrile (Compound 50)

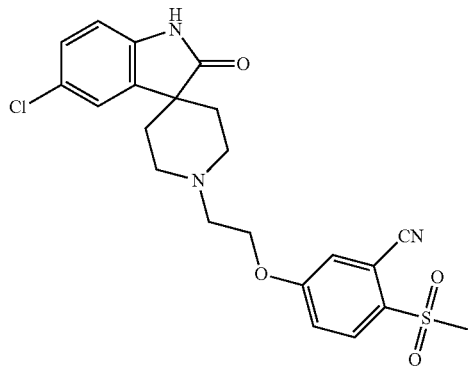 [SMILES: CS(=O)(=O)c1ccc(OCCN2CCC3(CC2)C(=O)Nc2ccc(Cl)cc23)cc1C#N]

A mixture of 2-(3-cyano-4-methanesulfonylphenoxy)ethyl methanesulfonate (51.0 mg, 0.16 mmol), 5-chloro-1,2-dihydrospiro[indole-3,4'-piperidin]-2-one (Intermediate B-4, 40.0 mg, 0.146 mmol, HCl salt) and $K_2CO_3$ (50.6 mg, 0.366 mmol), in DMF (0.6 mL) was stirred at 80° C. for 3 h. After cooling to room temperature, the reaction mixture was diluted with $H_2O$ (0.15 mL) and purified by reverse phase preparative HPLC (Phenomenex Kinetex $C_{18}$ column, 10-30% MeCN:$H_2O$ with 0.1% formic acid modifier) to give 5-(2-{5-chloro-2-oxo-1,2-dihydrospiro[indole-3,4'-piperidin]-1'-yl}ethoxy)-2-methanesulfonylbenzonitrile (Compound 50). $^1$H NMR (500 MHz, DMSO-$d_6$): δ 10.49 (s, 1H), 8.02 (d, J=8.9 Hz, 1H), 7.83 (d, J=2.6 Hz, 1H), 7.58-7.44 (m, 2H), 7.23 (dd, J=8.2, 2.0 Hz, 1H), 6.84 (d, J=8.2 Hz, 1H), 4.34 (t, J=5.6 Hz, 2H), 3.11 (br s, 3H), 2.97-2.83 (m, 4H), 2.74-2.65 (m, 2H), 1.83-1.74 (m, 2H), 1.74-1.61 (m, 2H). MS=460.0 [M+H]$^+$.

Example 17

4-(2-{5-chloro-2-oxo-1,2-dihydrospiro[indole-3,4'-piperidin]-1'-yl}ethoxy)-2-methylbenzamide (Compound 51)

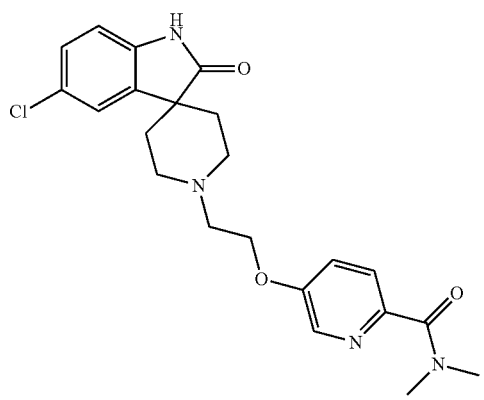 [SMILES: CN(C)C(=O)c1ccc(OCCN2CCC3(CC2)C(=O)Nc2ccc(Cl)cc23)cn1]

Step 1:
5-hydroxy-N,N-dimethylpyridine-2-carboxamide

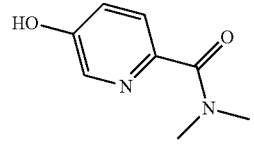

To a mixture of 5-hydroxypyridine-2-carboxylic acid (500 mg, 3.59 mmol) and dimethylamine hydrochloride (440 mg, 5.40 mmol) in DMF (2.5 mL) was added DIEA (1.88 mL, 10.8 mmol). The mixture was stirred for 10 min, then HATU (1.64 g, 4.3 mmol) was added in a single portion. After stirring for 18 h, the reaction mixture was diluted with brine (5 mL) and filtered to remove solids. The filtrate was extracted with EtOAc (3×5 mL). The combined organic layers were dried over $Na_2SO_4$, filtered, and concentrated in vacuo. The crude residue was purified by normal phase silica gel chromatography (Biotage 10 g cartridge, 0-20% MeOH:DCM) to give 5-hydroxy-N,N-dimethylpyridine-2-carboxamide. $^1$H NMR (500 MHz, CDCl$_3$, 9/10 H): δ 8.07 (d, J=2.8 Hz, 1H), 7.41 (d, J=8.5 Hz, 1H), 7.08 (dd, J=8.5, 2.8 Hz, 1H), 3.14-3.07 (m, 6H).

Step 2: 5-(2-bromoethoxy)-N,N-dimethylpyridine-2-carboxamide

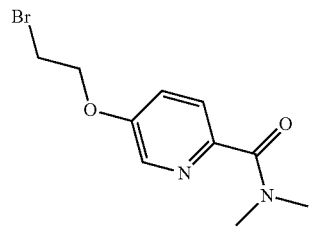

A mixture of 5-hydroxy-N,N-dimethylpyridine-2-carboxamide (158 mg, 0.951 mmol) and $Cs_2CO_3$ (620 mg, 1.90 mmol) in 1,2-dibromoethane (1.24 mL, 14.3 mmol) was stirred at 110° C. for 18 h in a sealed vial. After cooling to room temperature, the reaction mixture was diluted with DCM and filtered to remove solids. The filter cake was then washed with DCM (3×5 mL) and concentrated under reduced pressure to give 5-(2-bromoethoxy)-N,N-dimethylpyridine-2-carboxamide, which was taken to the next step without further purification. $^1$H NMR (500 MHz, DMSO-$d_6$): δ 8.30 (s, 1H), 7.60-7.53 (m, 1H), 7.53-7.48 (m, 1H), 4.46 (t, J=4.5 Hz, 2H), 3.84 (t, J=4.3 Hz, 2H), 2.99 (s, 6H).

939

Step 3: 4-(2-{5-chloro-2-oxo-1,2-dihydrospiro[indole-3,4'-piperidin]-1'-yl}ethoxy)-2-methylbenzamide (Compound 51)

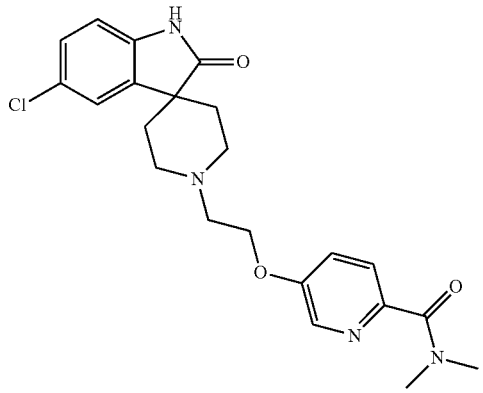 [SMILES: CN(C)C(=O)c1ccc(OCCN2CCC3(CC2)C(=O)Nc2ccc(Cl)cc23)cn1]

A mixture of 5-(2-bromoethoxy)-N,N-dimethylpyridine-2-carboxamide (25.0 mg, 0.0915 mmol), 5-chloro-1,2-dihydrospiro[indole-3,4'-piperidin]-2-one (Intermediate B-4, 25.0 mg, 0.0915 mmol, HCl salt), K$_2$CO$_3$ (31.6 mg, 0.229 mmol), and KI (15.0 mg, 0.0904 mmol) in DMF (0.6 mL) was stirred at 75° C. for 3 h. After cooling to room temperature, the reaction mixture was diluted with H$_2$O (0.15 mL) and purified by reverse phase preparative HPLC (Phenomenex Kinetex C$_{18}$ column, 10-30% MeCN:H$_2$O with 0.1% formic acid modifier) to give 4-(2-{5-chloro-2-oxo-1,2-dihydrospiro[indole-3,4'-piperidin]-1'-yl}ethoxy)-2-methylbenzamide (Compound 51). $^1$H NMR (500 MHz, DMSO-d$_6$): δ 10.49 (s, 1H), 8.29 (d, J=2.7 Hz, 1H), 7.57 (d, J=8.6 Hz, 1H), 7.54-7.48 (m, 2H), 7.23 (dd, J=8.2, 2.1 Hz, 1H), 6.84 (d, J=8.3 Hz, 1H), 4.27 (t, J=5.7 Hz, 2H), 3.00 (s, 3H), 2.99 (s, 3H), 2.97-2.90 (m, 2H), 2.88 (t, J=5.7 Hz, 2H), 2.75-2.66 (m, 2H), 1.86-1.75 (m, 2H), 1.75-1.64 (m, 2H). MS=429.1 [M+H]$^+$.

Example 18

4-(2-{5-chloro-2-oxo-1,2-dihydrospiro[indole-3,4'-piperidin]-1'-yl}ethoxy)-N-methylbenzamide (Compound 52)

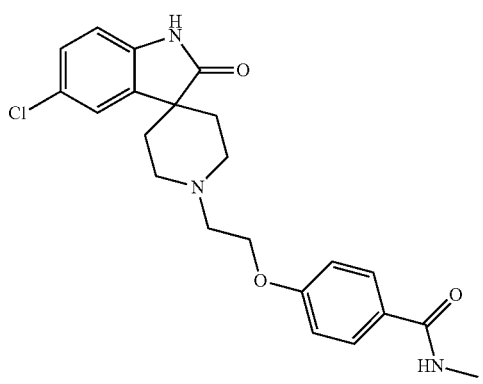 [SMILES: CNC(=O)c1ccc(OCCN2CCC3(CC2)C(=O)Nc2ccc(Cl)cc23)cc1]

940

Step 1: 4-(2-hydroxyethoxy)-N-methylbenzamide

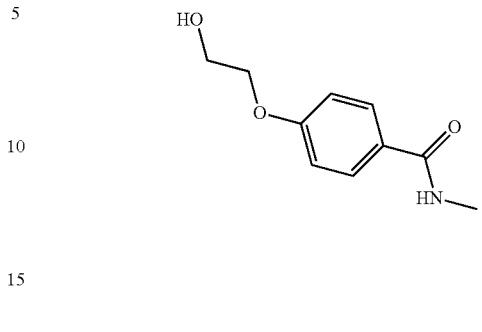

To a mixture of 4-(2-hydroxyethoxy)benzoic acid (500 mg, 2.75 mmol) and methylamine hydrochloride (278 mg, 4.12 mmol) in a solution of 10:1 THF/DMF (5.5 mL) was added DIEA (1.43 mL, 8.2 mmol). The mixture was stirred at room temperature for 10 min. HATU (1.25 g, 3.3 mmol) was added in a single portion and stirring was continued for 18 h. The reaction mixture was diluted with brine (5 mL) and extracted with EtOAc (3×5 mL). The combined organic layers were dried over Na$_2$SO$_4$, filtered, and concentrated in vacuo. The crude residue was purified by normal phase silica gel chromatography (Biotage 10 g cartridge, 0-10% MeOH:DCM) to give 4-(2-hydroxyethoxy)-N-methylbenzamide. MS=196.1 [M+H]$^+$.

Step 2: 2-[4-(methylcarbamoyl)phenoxy]ethyl methanesulfonate

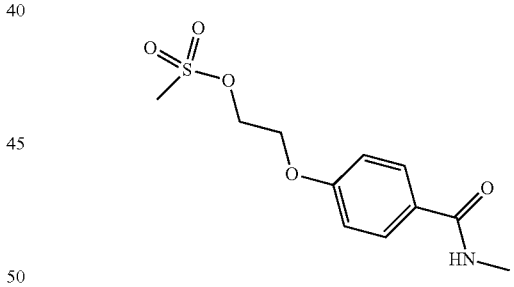

Methanesulfonyl chloride (0.45 mL, 2.9 mmol) was added dropwise to a 0° C. solution of 4-(2-hydroxyethoxy)-N-methylbenzamide (380 mg, 1.95 mmol) and DIEA (0.300 mL, 3.41 mmol) in DCM (4 mL). The mixture was allowed to slowly warm to room temperature and stirring was continued 16 h. The reaction mixture was diluted with saturated aqueous NH$_4$Cl (5 mL) and allowed to stir an additional 15 min. The organic layer was separated, and the aqueous layer was extracted with DCM (3×2 mL). The combined organic layers were dried over Na$_2$SO$_4$, filtered, and concentrated in vacuo. The crude residue was purified by normal phase silica gel chromatography (Biotage 10 g cartridge, 0-10% MeOH:DCM) to give 2-[4-(methylcarbamoyl)phenoxy]ethyl methanesulfonate. MS=274.1 [M+H]$^+$.

941

Step 3: 4-(2-{5-chloro-2-oxo-1,2-dihydrospiro[indole-3,4'-piperidin]-1'-yl}ethoxy)-N-methylbenzamide (Compound 52)

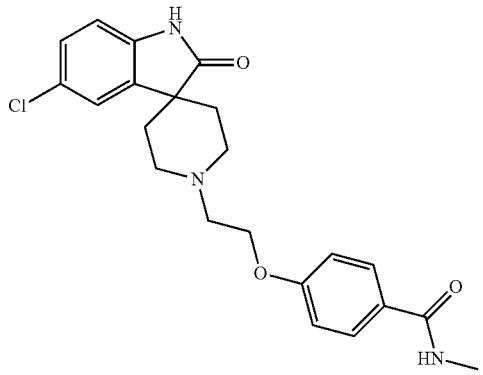 [SMILES: CNC(=O)c1ccc(OCCN2CCC3(CC2)C(=O)Nc2ccc(Cl)cc23)cc1]

A mixture of 2-[4-(methylcarbamoyl)phenoxy]ethyl methanesulfonate (30.0 mg, 0.110 mmol), 5-chloro-1,2-dihydrospiro[indole-3,4'-piperidin]-2-one (Intermediate B-4, 30.0 mg, 0.110 mmol, HCl salt), K$_2$CO$_3$ (37.9 mg, 0.274 mmol), and KI (18.2 mg, 0.110 mmol) in DMF (0.6 mL) was stirred at 75° C. for 5 h. After cooling to room temperature, the reaction mixture was diluted with H$_2$O (0.2 mL) and 5 drops of formic acid was added. The mixture was purified by reverse phase preparative HPLC (Phenomenex Kinetex C$_{18}$ column, 10-30% MeCN:H$_2$O with 0.1% formic acid modifier) to give 4-(2-{5-chloro-2-oxo-1,2-dihydrospiro[indole-3,4'-piperidin]-1'-yl}ethoxy)-N-methylbenzamide (Compound 52). $^1$H NMR (500 MHz, DMSO-d$_6$): δ 10.53 (s, 1H), 8.35-8.19 (m, 1H), 7.80 (d, J=10.0, 2H), 7.52 (s, 1H), 7.24 (dd, J=8.3, 2.1 Hz, 1H), 7.02 (d, J=10.0, 2H), 6.85 (d, J=8.3 Hz, 1H), 4.23 (t, J=5.6 Hz, 2H), 3.04-3.00 (m, 4H) 2.83 (br s, 2H), 2.76 (d, J=4.4 Hz, 3H), 1.99-1.58 (m, 4H). MS=414.2 [M+H]$^+$.

942

Example 19

5-chloro-1'-{2-[(1-methanesulfonyl-1,2,3,4-tetrahydroquinolin-6-yl)oxy]ethyl}-1,2-dihydrospiro[indole-3,4'-piperidin]-2-one (Compound 53)

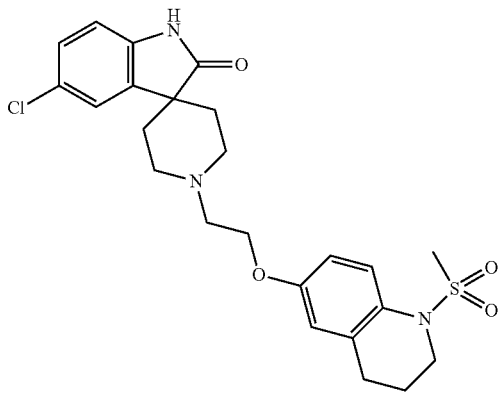 [SMILES: CS(=O)(=O)N1CCCc2cc(OCCN3CCC4(CC3)C(=O)Nc3ccc(Cl)cc34)ccc21]

To a 0° C. solution of tert-butyl 6-(2-{5-chloro-2-oxo-1,2-dihydrospiro[indole-3,4'-piperidin]-1'-yl}ethoxy)-1,2,3,4-tetrahydroquinoline-1-carboxylate (Intermediate C-1, 84.0 g, 0.173 mmol, HCl salt) in DCM (1.73 mL) was added TEA (0.121 mL, 0.865 mmol), followed by methanesulfonyl chloride (20.1 µL, 0.260 mmol) dropwise. The mixture was allowed to warm to room temperature and stirred for 2 h. The reaction mixture was diluted with H$_2$O (10 mL) and extracted with DCM (2×20 mL). The combined organic layers were dried over Na$_2$SO$_4$, filtered, and concentrated in vacuo. The crude residue was purified by reverse phase preparative HPLC (Phenomenex Kinetex C$_{18}$ column, 0-50% MeCN:H$_2$O with 0.1% formic acid modifier) to give 5-chloro-1'-{2-[(1-methanesulfonyl-1,2,3,4-tetrahydroquinolin-6-yl)oxy]ethyl}-1,2-dihydrospiro[indole-3,4'-piperidin]-2-one (Compound 53). $^1$H NMR (500 MHz, DMSO-d$_6$): δ 10.49 (s, 1H), 7.51 (d, J=2.0 Hz, 1H), 7.43 (d, J=8.6 Hz, 1H), 7.24 (d, J=8.2 Hz, 1H), 6.85 (d, J=8.3 Hz, 1H), 6.80 (d, J=8.9 Hz, 2H), 4.11 (t, J=5.7 Hz, 2H), 3.66 (t, J=4.9 Hz, 2H), 2.97-2.89 (m, 5H), 2.86 (t, J=5.8 Hz, 2H), 2.78 (t, J=6.7 Hz, 2H), 2.75-2.67 (m, 2H), 1.96-1.86 (m, 2H), 1.83-1.70 (m, 4H). MS=490.2 [M+H]$^+$.

The following compounds in Table 24 were prepared according to procedures analogous to those described for Compound 53 using the appropriate starting materials.

TABLE 24

| # | Structure | IUPAC Name | Exact Mass [M + H]+ | Intermediates Used |
|---|---|---|---|---|
| 54 | 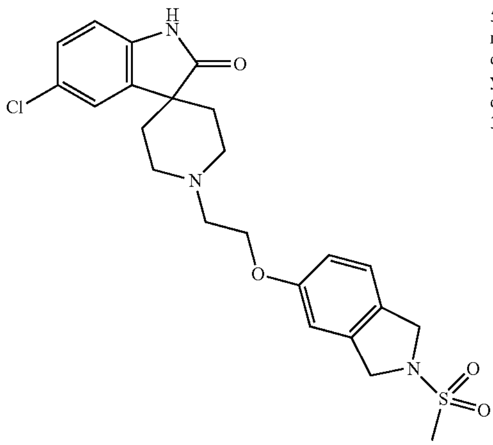 [SMILES: CS(=O)(=O)N1Cc2ccc(OCCN3CCC4(CC3)C(=O)Nc3ccc(Cl)cc34)cc2C1] | 5-chloro-1'-{2-[(2-methanesulfonyl-2,3-dihydro-1H-isoindol-5-yl)oxy]ethyl}-1,2-dihydrospiro[indole-3,4'-piperidin]-2-one | Calc'd 476.1 Found 476.1 | C-2 |
| 55 | 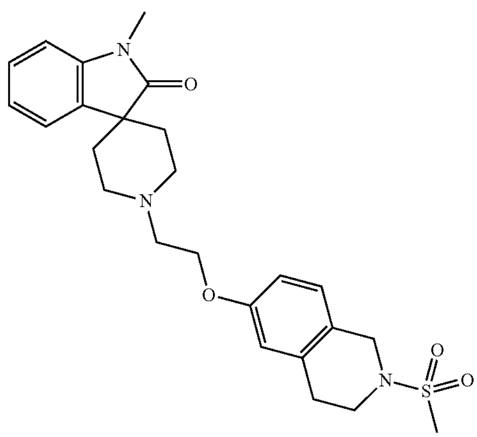 [SMILES: CN1C(=O)C2(CCN(CCOc3ccc4c(c3)CCN(S(C)(=O)=O)C4)CC2)c2ccccc21] | 1'-{2-[(2-methanesulfonyl-1,2,3,4-tetrahydroisoquinolin-6-yl)oxy]ethyl}-1-methyl-1,2-dihydrospiro[indole-3,4'-piperidin]-2-one | Calc'd 470.2 Found 470.2 | C-5 |

Example 20

1'-{2-[(1-acetyl-1,2,3,4-tetrahydroquinolin-6-yl)oxy]ethyl}-5-chloro-1,2-dihydrospiro[indole-3,4'-piperidin]-2-one (Compound 56)

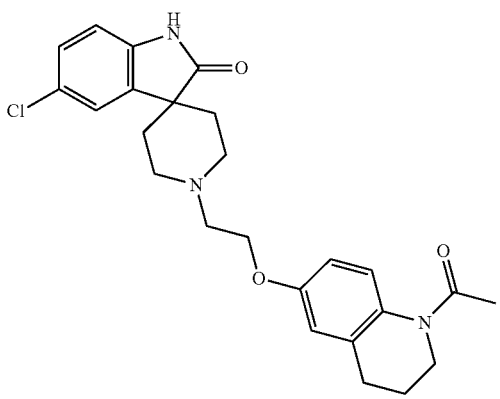 [SMILES: CC(=O)N1CCCc2cc(OCCN3CCC4(CC3)C(=O)Nc3ccc(Cl)cc34)ccc21]

To a 0° C. solution of tert-butyl 6-(2-{5-chloro-2-oxo-1,2-dihydrospiro[indole-3,4'-piperidin]-1'-yl}ethoxy)-1,2,3,4-tetrahydroquinoline-1-carboxylate (Intermediate C-1, 84.0 mg, 0.173 mmol, HCl salt) in DCM (1.73 mL) was added TEA (0.121 mL, 0.865 mmol), followed by acetic anhydride (23.9 µL, 0.260 mmol) dropwise. The mixture was stirred for 30 min and was then diluted with H₂ (10 mL) and extracted with DCM (2×20 mL). The combined organic layers were dried over Na₂SO₄, filtered, and concentrated in vacuo. The crude residue was purified by reverse phase preparative HPLC (Phenomenex Kinetex $C_{18}$ column, 0-40% MeCN:H₂O with 0.100 formic acid modifier) to give 1-{2-[(1-acetyl-1,2,3,4-tetrahydroquinolin-6-yl)oxy]ethyl}-5-chloro-1,2-dihydrospiro[indole-3,4'-piperidin]-2-one (Compound 56). ¹H NMR (500 MHz, DMSO-d₆): δ 10.49 (s, 1H), 8.15 (s, 1H), 7.51 (d, J=2.1 Hz, 1H), 7.24 (dd, J=8.2, 2.1 Hz, 1H), 6.85 (d, J=8.3 Hz, 1H), 6.83-6.75 (m, 2H), 4.12 (t, J=5.8 Hz, 2H), 3.64 (t, J=6.4 Hz, 2H), 2.98-2.89 (m, 2H), 2.86 (t, J=5.8 Hz, 2H), 2.75-2.66 (m, 4H), 2.11 (s, 3H), 1.88-1.68 (in, 6H). MS=454.1 [M+H]+.

The following compounds in Table 25 were prepared according to procedures analogous to those described for Compound 56 using the appropriate starting materials.

TABLE 25

| # | Structure | IUPAC Name | Exact Mass [M + H]⁺ | Intermediates Used |
|---|---|---|---|---|
| 57 | 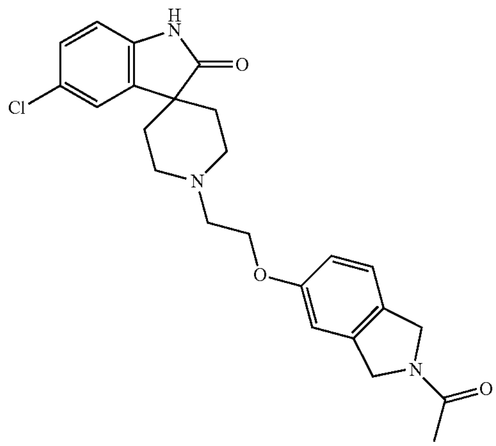 [SMILES: CC(=O)N1Cc2ccc(OCCN3CCC4(CC3)C(=O)Nc3ccc(Cl)cc34)cc2C1] | 1'-{2-[(2-acetyl-2,3-dihydro-1H-isoindol-5-yl)oxy]ethyl}-5-chloro-1,2-dihydrospiro[indole-3,4'-piperidin]-2-one | Calc'd 440.2 Found 440.1 | C-2 |
| 58 | 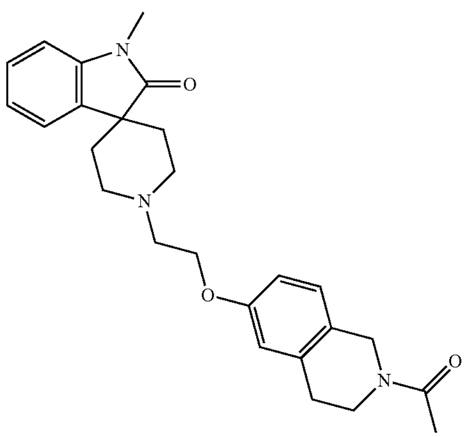 [SMILES: CC(=O)N1CCc2cc(OCCN3CCC4(CC3)C(=O)N(C)c3ccccc34)ccc2C1] | 1'-{2-[(2-acetyl-1,2,3,4-tetrahydroisoquinolin-6-yl)oxy]ethyl}-1-methyl-1,2-dihydrospiro[indole-3,4'-piperidin]-2-one | Calc'd 434.2 Found 434.1 | C-5 |
| 59 | 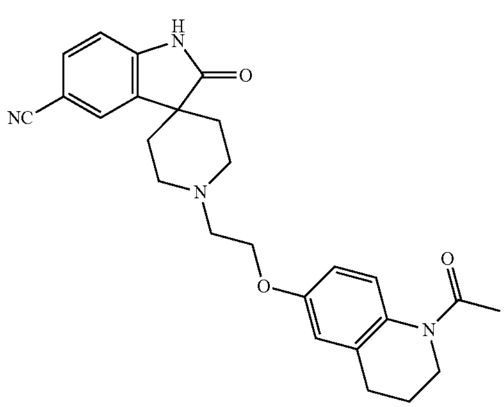 [SMILES: CC(=O)N1CCCc2cc(OCCN3CCC4(CC3)C(=O)Nc3ccc(C#N)cc34)ccc21] | 1'-{2-[(1-acetyl-1,2,3,4-tetrahydroquinolin-6-yl)oxy]ethyl}-2-oxo-1,2-dihydrospiro[indole-3,4'-piperidine]-5-carbonitrile | Calc'd 445.2 Found 445.2 | C-4 |

Example 21

6-(2-{5-chloro-2-oxo-1,2-dihydrospiro[indole-3,4'-piperidin]-1'-yl}ethoxy)-N-methyl-1,2,3,4-tetrahydroquinoline-1-carboxamide (Compound 60)

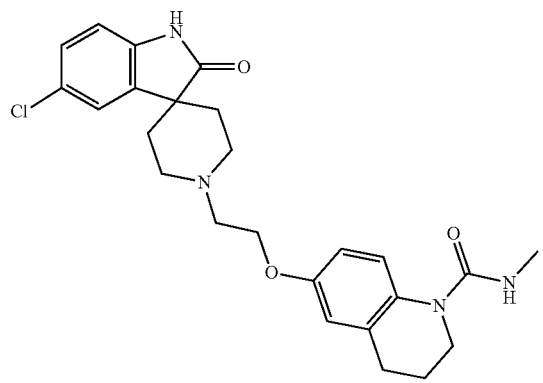 [SMILES: CNC(=O)N1CCCc2cc(OCCN3CCC4(CC3)C(=O)Nc3ccc(Cl)cc34)ccc21]

To a 0° C. mixture of 5-chloro-1'-[2-(1,2,3,4-tetrahydroquinolin-6-yloxy)ethyl]-1H-spiro[indole-3,4'-piperidin]-2-one (Intermediate C-1, 0.118 g, 0.244 mmol) in DCM (1.6 mL) was added TEA (0.134 mL, 0.976 mmol), followed by N-methylcarbamoyl chloride (0.034 g, 0.366 mmol). The mixture was allowed to warm to room temperature and stirred for 2 h. The reaction was quenched with saturated aqueous $NaHCO_3$ (20 mL) and extracted with DCM (2×20 mL). The combined organic layers were dried over $Na_2SO_4$, filtered, and concentrated in vacuo. The crude residue was purified by reverse phase preparative HPLC (Phenomenex Kinetex $C_{18}$ column, 0-40% MeCN:$H_2O$ with 0.1% formic acid modifier) to give 6-(2-{5-chloro-2-oxo-1,2-dihydrospiro[indole-3,4'-piperidin]-1'-yl}ethoxy)-N-methyl-1,2,3,4-tetrahydroquinoline-1-carboxamide (Compound 60). $^1$H NMR (500 MHz, DMSO-$d_6$): δ 10.49 (s, 1H), 7.52 (s, 1H), 7.30 (d, J=8.6 Hz, 1H), 7.27-7.21 (m, 1H), 6.85 (dd, J=8.3, 1.5 Hz, 1H), 6.73 (d, J=8.2 Hz, 2H), 6.40 (q, J=4.6 Hz, 1H), 4.09 (t, J=5.8 Hz, 2H), 3.52 (t, J=6.2 Hz, 2H), 2.98-2.89 (m, 2H), 2.85 (t, J=5.8 Hz, 2H), 2.75-2.68 (m, 2H), 2.66 (t, J=6.6 Hz, 2H), 2.62 (d, J=1.5 Hz, 3H), 1.86-1.76 (m, 4H), 1.75-1.68 (m, 2H). MS=469.1 [M+H]$^+$.

The following compound in Table 26 was prepared according to procedures analogous to those described for Compound 60 using the appropriate starting materials.

TABLE 26

| # | Structure | IUPAC Name | Exact Mass [M + H]$^+$ | Intermediates Used |
|---|---|---|---|---|
| 61 | 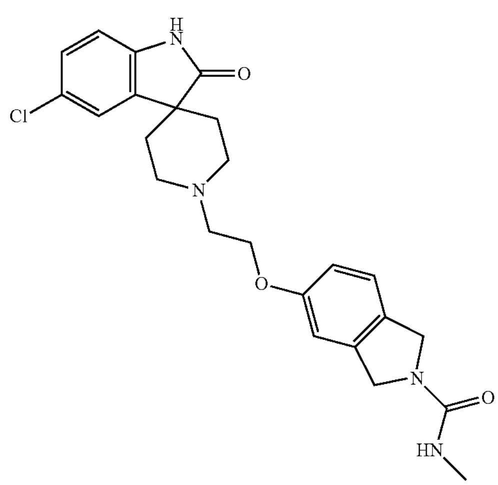 [SMILES: CNC(=O)N1Cc2ccc(OCCN3CCC4(CC3)C(=O)Nc3ccc(Cl)cc34)cc2C1] | 5-(2-{5-chloro-2-oxo-1,2-dihydrospiro[indole-3,4'-piperidin]-1'-yl}ethoxy)-N-methyl-2,3-dihydro-1H-isoindole-2-carboxamide | Calc'd 455.2 Found 455.2 | C-2 |

Example 22

5-chloro-1'-[2-(quinoxalin-6-yloxy)ethyl]-1,2-dihydrospiro[indole-3,4'-piperidin]-2-one (Compound 62)

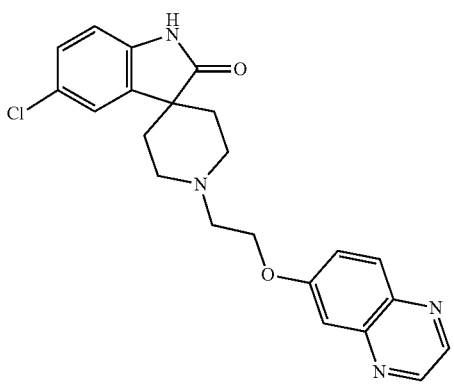 [SMILES: O=C1Nc2ccc(Cl)cc2C12CCN(CCOc1ccc3nccnc3c1)CC2]

A mixture of 5-chloro-1'-(2-chloroethyl)-1,2-dihydrospiro[indole-3,4'-piperidin]-2-one (Intermediate B-5, 40.0 mg, 0.134 mmol), quinoxalin-6-ol (23.4 mg, 0.161 mmol) and $K_2CO_3$ (27.7 mg, 0.201 mmol) in DMF (1.3 mL) was heated at 80° C. for 1 h. After cooling to room temperature, the mixture was diluted with $H_2O$ (10 mL) and extracted with EtOAc (2×20 mL). The combined organic layers were dried over $Na_2SO_4$, filtered, and concentrated in vacuo. The crude residue was purified by reverse phase preparative HPLC (Phenomenex Kinetex $C_{18}$ column, 0-30% MeCN:$H_2O$ with 0.1% formic acid modifier) to give 5-chloro-1'-[2-(quinoxalin-6-yloxy)ethyl]-1,2-dihydrospiro[indole-3,4'-piperidin]-2-one (Compound 62). $^1$H NMR (500 MHz, DMSO-$d_6$): δ 10.50 (s, 1H), 8.87 (d, J=2.4 Hz, 1H), 8.78 (d, J=2.4 Hz, 1H), 8.00 (dd, J=9.2, 2.5 Hz, 1H), 7.58-7.49 (m, 3H), 7.23 (d, J=8.3 Hz, 1H), 6.85 (dd, J=8.3, 2.4 Hz, 1H), 4.37 (t, J=5.3 Hz, 2H), 2.98-2.91 (m, 4H), 2.78 (t, J=9.2 Hz, 2H), 1.93-1.67 (m, 4H). MS=409.1 [M+H]$^+$.

The following compound in Table 27 was prepared according to procedures analogous to those described for Compound 62 using the appropriate starting materials.

TABLE 27

| # | Structure | IUPAC Name | Exact Mass [M + H]$^+$ | Intermediates Used |
|---|---|---|---|---|
| 63 | 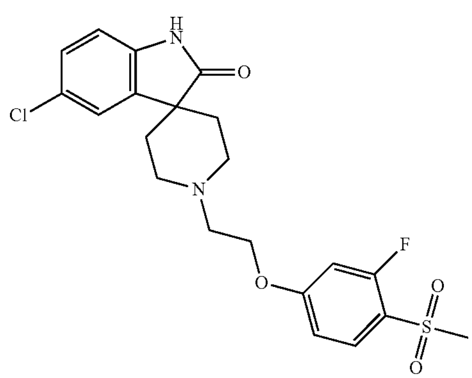 [SMILES: CS(=O)(=O)c1ccc(OCCN2CCC3(CC2)C(=O)Nc2ccc(Cl)cc23)cc1F] | 5-chloro-1'-[2-(3-fluoro-4-methanesulfonylphenoxy)ethyl]-1,2-dihydrospiro[indole-3,4'-piperidin]-2-one | Calc'd 453.1 Found 453.1 | B-5 |
| 64 | 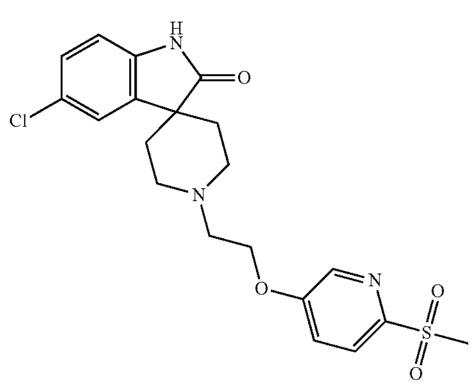 [SMILES: CS(=O)(=O)c1ccc(OCCN2CCC3(CC2)C(=O)Nc2ccc(Cl)cc23)cn1] | 5-chloro-1'-{2-[(6-methanesulfonylpyridin-3-yl)oxy]ethyl}-1,2-dihydrospiro[indole-3,4'-piperidin]-2-one | Calc'd 436.1 Found 436.1 | B-5 |

Example 23

5-chloro-1'-{2-[(1-methyl-2-oxo-2,3-dihydro-1H-indol-5-yl)oxy]ethyl}-1,2-dihydrospiro[indole-3,4'-piperidin]-2-one (Compound 65)

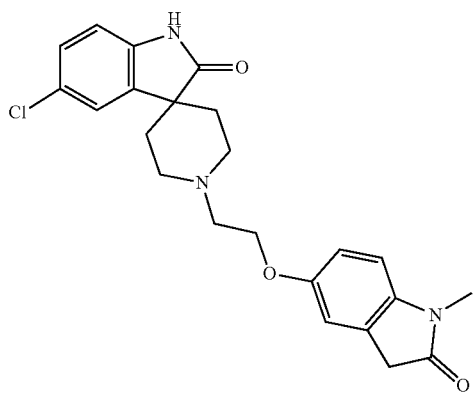 [SMILES: CN1C(=O)Cc2cc(OCCN3CCC4(CC3)C(=O)Nc3ccc(Cl)cc34)ccc21]

A mixture of 5-(2-bromoethoxy)-1-methyl-2,3-dihydro-1H-indol-2-one (Intermediate A-4, 20 mg, 0.074 mmol), 5-chloro-1,2-dihydrospiro[indole-3,4'-piperidin]-2-one (Intermediate B-4, 22 mg, 0.081 mmol) and $K_2CO_3$ (31 mg, 0.22 mmol) in DMF (0.5 mL) was heated at 60° C. for 3 h. After cooling to room temperature, the mixture was diluted with $H_2O$ (5 mL) and extracted with EtOAc (2×10 mL). The combined organic layers were dried over $Na_2SO_4$, filtered, and concentrated in vacuo. The crude residue was purified by reverse phase preparative HPLC (Phenomenex Kinetex $C_{18}$ column, 0-40% MeCN:$H_2O$ with 0.1% formic acid modifier) to give 5-chloro-1'-{2-[(1-methyl-2-oxo-2,3-dihydro-1H-indol-5-yl)oxy]ethyl}-1,2-dihydrospiro[indole-3,4'-piperidin]-2-one (Compound 65). $^1$H NMR (500 MHz, $CD_3CN$): δ 8.34 (s, 1H), 7.36 (d, J=2.2 Hz, 1H), 7.12 (dd, J=8.3, 2.1 Hz, 1H), 6.87-6.83 (m, 1H), 6.82-6.75 (m, 2H), 6.70 (d, J=8.5 Hz, 1H), 4.04 (t, J=5.6 Hz, 2H), 3.34 (s, 2H), 3.02 (s, 3H), 3.00-2.91 (m, 2H), 2.85 (t, J=5.6 Hz, 2H), 2.78-2.70 (m, 4H), 1.82-1.70 (m, 4H). MS=426.1 $[M+H]^+$.

The following compound in Table 28 was prepared according to procedures analogous to those described for Compound 65 using the appropriate starting materials.

TABLE 28

| # | Structure | IUPAC Name | Exact Mass $[M + H]^+$ | Intermediates Used |
|---|-----------|------------|------------------------|--------------------|
| 66 | 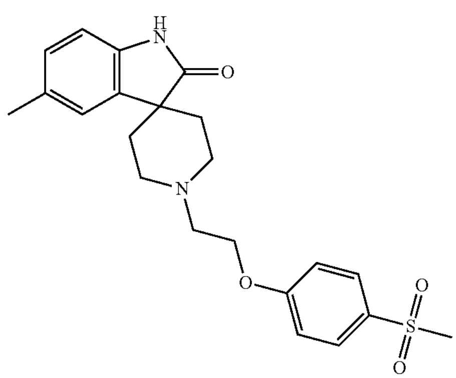 | 1'-[2-(4-methanesulfonylphenoxy)ethyl]-5-methyl-1,2-dihydrospiro[indole-3,4'-piperidin]-2-one | Calc'd 415.2 Found 415.1 | A-3 |
| 67 | 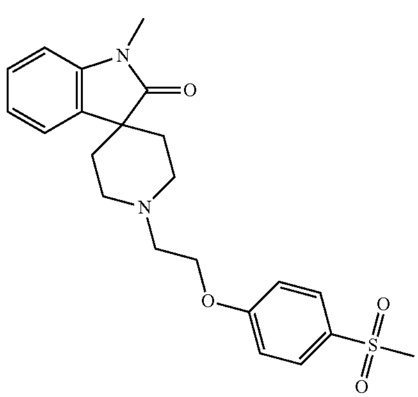 [SMILES: CN1C(=O)C2(CCN(CCOc3ccc(S(C)(=O)=O)cc3)CC2)c2ccccc21] | 1'-[2-(4-methanesulfonylphenoxy)ethyl]-1-methyl-1,2-dihydrospiro[indole-3,4'-piperidin]-2-one | Calc'd 415.2 Found 415.1 | A-3 and B-6 |

| # | Structure | IUPAC Name | Exact Mass [M + H]+ | Intermediates Used |
|---|---|---|---|---|
| 68 | 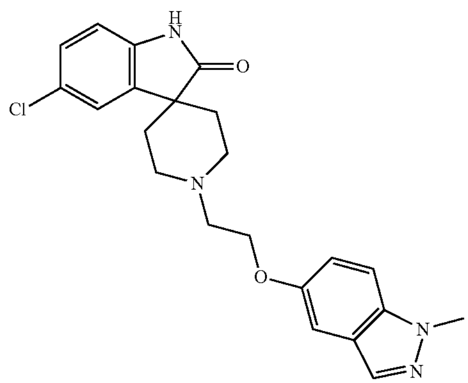 [SMILES: Cn1ncc2cc(OCCN3CCC4(CC3)C(=O)Nc3ccc(Cl)cc34)ccc21] | 5-chloro-1'-{2-[(1-methyl-1H-indazol-5-yl)oxy]ethyl}-1,2-dihydrospiro[indole-3,4'-piperidin]-2-one | Calc'd 411.2 Found 411.1 | A-5 and B-4 |
| 69 | 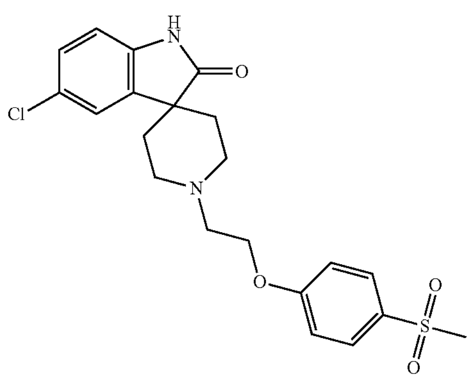 [SMILES: CS(=O)(=O)c1ccc(OCCN2CCC3(CC2)C(=O)Nc2ccc(Cl)cc23)cc1] | 5-chloro-1'-[2-(4-methanesulfonyl-phenoxy)ethyl]-1,2-dihydrospiro[indole-3,4'-piperidin]-2-one | Calc'd 435.1 Found 435.0 | A-3 and B-4 |
| 70 | 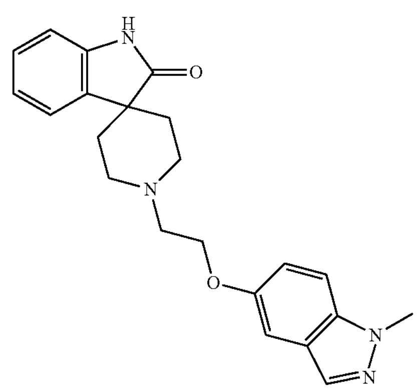 [SMILES: Cn1ncc2cc(OCCN3CCC4(CC3)C(=O)Nc3ccccc34)ccc21] | 1'-{2-[(1-methyl-1H-indazol-5-yl)oxy]ethyl}-1,2-dihydrospiro[indole-3,4'-piperidin]-2-one | Calc'd 377.2 Found 377.1 | A-5 |
| 71 | 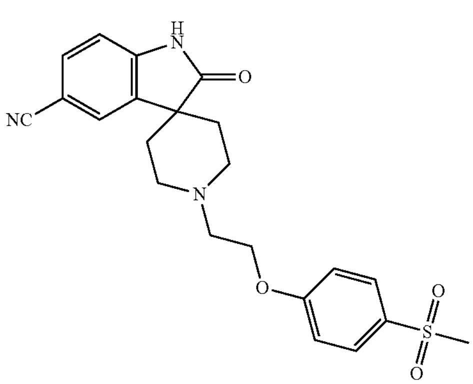 [SMILES: CS(=O)(=O)c1ccc(OCCN2CCC3(CC2)C(=O)Nc2ccc(C#N)cc23)cc1] | 1'-[2-(4-methanesulfonyl-phenoxy)ethyl]-2-oxo-1,2-dihydrospiro[indole-3,4'-piperidine]-5-carbonitrile | Calc'd 426.1 Found 426.1 | A-3 and B-9 |

TABLE 28-continued

| # | Structure | IUPAC Name | Exact Mass [M + H]+ | Intermediates Used |
|---|---|---|---|---|
| 72 | 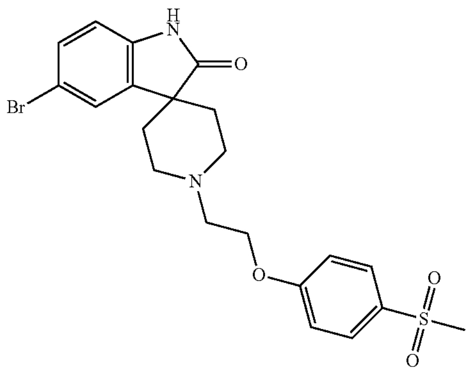 | 5-bromo-1'-[2-(4-methanesulfonyl-phenoxy)ethyl]-1,2-dihydrospiro[indole-3,4'-piperidin]-2-one | Calc'd 479.1 Found 479.1 | A-3 |
| 73 | 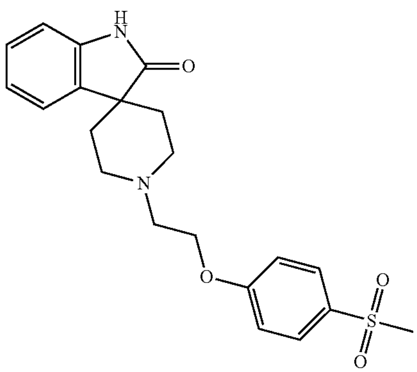 [SMILES: CS(=O)(=O)c1ccc(OCCN2CCC3(CC2)C(=O)Nc2ccccc23)cc1] | 1'-[2-(4-methanesulfonyl-phenoxy)ethyl]-1,2-dihydrospiro[indole-3,4'-piperidin]-2-one | Calc'd 401.2 Found 401.2 | A-3 |
| 74 | 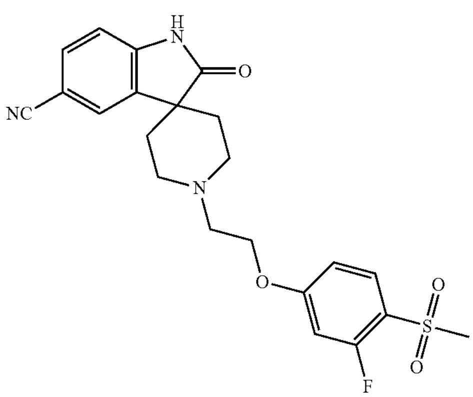 [SMILES: CS(=O)(=O)c1ccc(OCCN2CCC3(CC2)C(=O)Nc2ccc(C#N)cc23)cc1F] | 1'-[2-(3-fluoro-4-methanesulfonyl-phenoxy)ethyl]-2-oxo-1,2-dihydrospiro[indole-3,4'-piperidine]-5-carbonitrile | Calc'd 444.1 Found 444.1 | A-6 and B-9 |
| 75 | 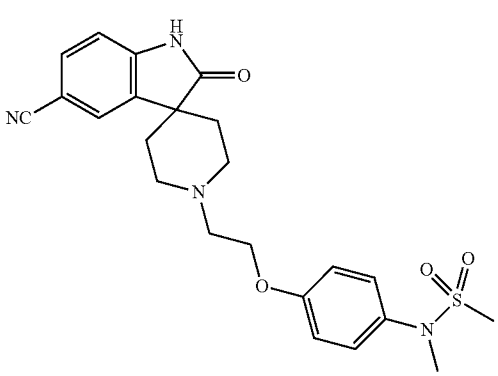 [SMILES: CN(c1ccc(OCCN2CCC3(CC2)C(=O)Nc2ccc(C#N)cc23)cc1)S(C)(=O)=O] | N-[4-(2-{5-cyano-2-oxo-1,2-dihydrospiro[indole-3,4'-piperidin]-1'-yl}ethoxy)phenyl]-N-methylmethanesulfona-mide | Calc'd 455.2 Found 455.2 | A-7 and B-9 |

TABLE 28-continued

| # | Structure | IUPAC Name | Exact Mass [M + H]+ | Intermediates Used |
|---|---|---|---|---|
| 76 | 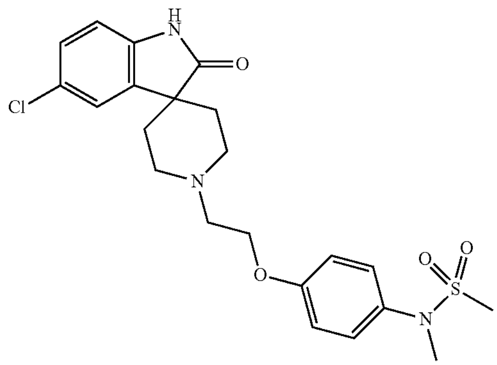 [SMILES: CN(c1ccc(OCCN2CCC3(CC2)C(=O)Nc2ccc(Cl)cc23)cc1)S(C)(=O)=O] | N-[4-(2-{5-chloro-2-oxo-1,2-dihydrospiro[indole-3,4'-piperidin]-1'-yl}ethoxy)phenyl]-N-methylmethanesulfonamide | Calc'd 464.1 Found 464.2 | A-7 and B-4 |
| 77 | 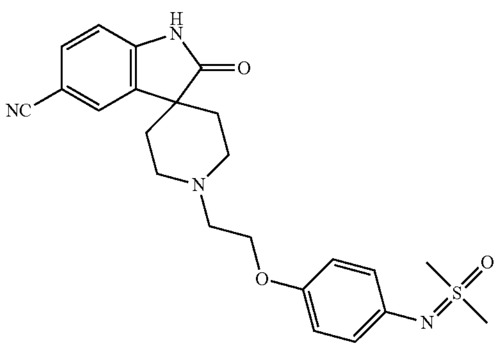 [SMILES: CS(C)(=O)=Nc1ccc(OCCN2CCC3(CC2)C(=O)Nc2ccc(C#N)cc23)cc1] | 1'-[2-(4-{[dimethyl(oxo)-λ⁶-sulfanylidene]amino}phenoxy)ethyl]-2-oxo-1,2-dihydrospiro[indole-3,4'-piperidine]-5-carbonitrile | Calc'd 439.2 Found 439.2 | A-8 and B-9 |
| 78 | 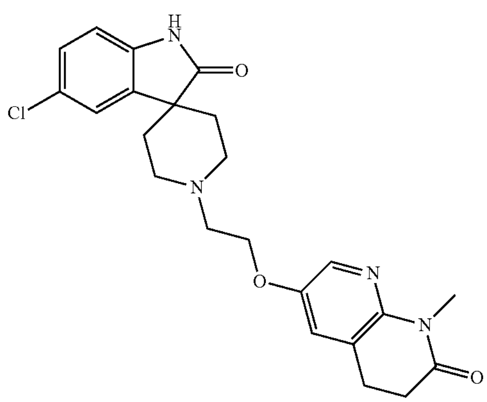 [SMILES: CN1C(=O)CCc2cc(OCCN3CCC4(CC3)C(=O)Nc3ccc(Cl)cc34)cnc21] | 5-chloro-1'-{2-[(8-methyl-7-oxo-5,6,7,8-tetrahydro-1,8-naphthyridin-3-yl)oxy]ethyl}-1,2-dihydrospiro[indole-3,4'-piperidin]-2-one | Calc'd 441.2 Found 441.1 | A-72 and B-4 |
| 79 | 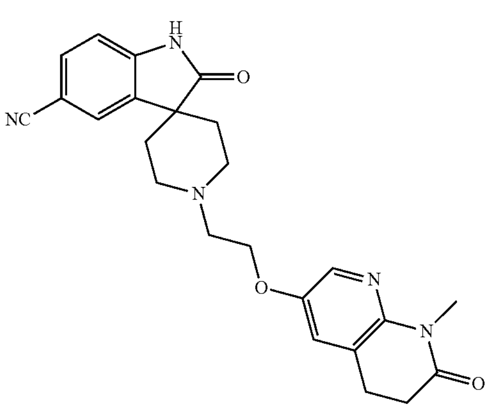 [SMILES: CN1C(=O)CCc2cc(OCCN3CCC4(CC3)C(=O)Nc3ccc(C#N)cc34)cnc21] | 1'-{2-[(8-methyl-7-oxo-5,6,7,8-tetrahydro-1,8-naphthyridin-3-yl)oxy]ethyl}-2-oxo-1,2-dihydrospiro[indole-3,4'-piperidine]-5-carbonitrile | Calc'd 432.2 Found 432.2 | A-72 and B-9 |

TABLE 28-continued

| # | Structure | IUPAC Name | Exact Mass [M + H]+ | Intermediates Used |
|---|---|---|---|---|
| 80 | 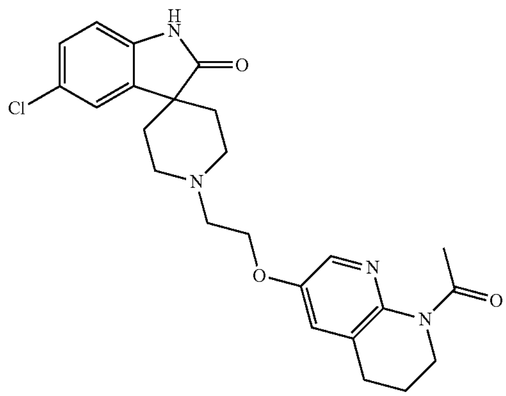 [SMILES: CC(=O)N1CCCc2cc(OCCN3CCC4(CC3)C(=O)Nc3ccc(Cl)cc34)cnc21] | 1'-{2-[(8-acetyl-5,6,7,8-tetrahydro-1,8-naphthyridin-3-yl)oxy]ethyl}-5-chloro-1,2-dihydrospiro[indole-3,4'-piperidin]-2-one | Calc'd 455.2 Found 455.1 | A-73 and B-4 |
| 81 | 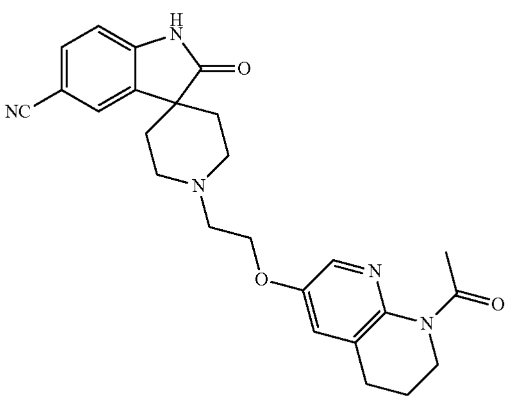 [SMILES: CC(=O)N1CCCc2cc(OCCN3CCC4(CC3)C(=O)Nc3ccc(C#N)cc34)cnc21] | 1'-{2-[(8-acetyl-5,6,7,8-tetrahydro-1,8-naphthyridin-3-yl)oxy]ethyl}-2-oxo-1,2-dihydrospiro[indole-3,4'-piperidine]-5-carbonitrile | Calc'd 446.2 Found 446.2 | A-73 and B-9 |
| 82 | 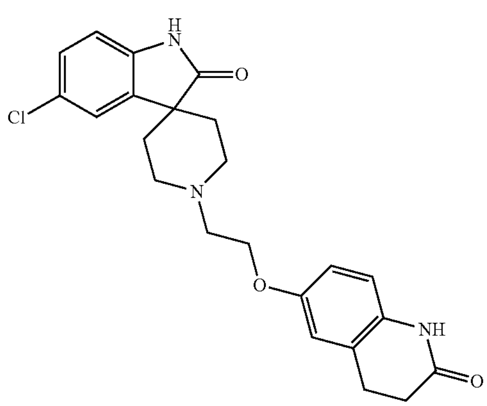 [SMILES: O=C1CCc2cc(OCCN3CCC4(CC3)C(=O)Nc3ccc(Cl)cc34)ccc2N1] | 5-chloro-1'-{2-[(2-oxo-1,2,3,4-tetrahydroquinolin-6-yl)oxy]ethyl}-1,2-dihydrospiro[indole-3,4'-piperidin]-2-one | Calc'd 426.2 Found 426.2 | A-83 and B-4 |

Example 24

2-oxo-1'-{2-[(1,3,3-trimethyl-2-oxo-2,3-dihydro-1H-indol-5-yl)oxy]ethyl}-1,2-dihydrospiro[indole-3,4'-piperidine]-5-carbonitrile (Compound 83)

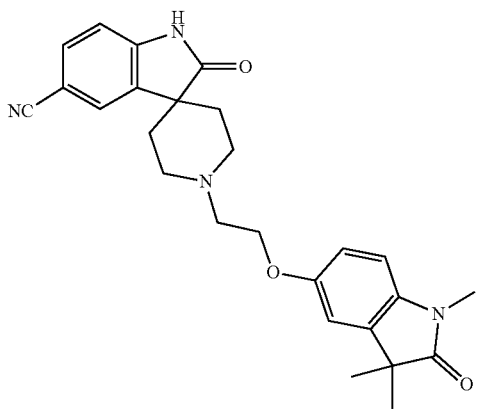 [SMILES: CN1C(=O)C(C)(C)c2cc(OCCN3CCC4(CC3)C(=O)Nc3ccc(C#N)cc34)ccc21]

Step 1: 5-(2-hydroxyethoxy)-1,3,3-trimethyl-2,3-dihydro-1H-indol-2-one

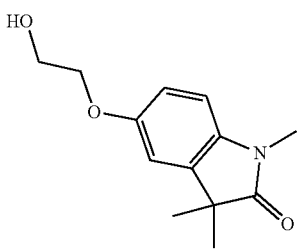 [SMILES: CN1C(=O)C(C)(C)c2cc(OCCO)ccc21]

A mixture of 5-hydroxy-1,3,3-trimethyl-2,3-dihydro-1H-indol-2-one (100 mg, 0.523 mmol), ethylene carbonate (69.7 µL, 1.05 mmol) and $K_2CO_3$ (0.145 g, 1.05 mmol) in DMF (5 mL) was heated at 90° C. for 3 h. After cooling to room temperature, the mixture was diluted with $H_2O$ (10 mL) and extracted with EtOAc (2×20 mL). The combined organic layers were dried over $Na_2SO_4$, filtered, and concentrated in vacuo. The crude residue was purified by normal phase silica gel chromatography (Biotage 10 g cartridge, 0-100% EtOAc:hexanes) to give 5-(2-hydroxyethoxy)-1,3,3-trimethyl-2,3-dihydro-1H-indol-2-one. MS=236.1 [M+H]$^+$.

Step 2: 2-[(1,3,3-trimethyl-2-oxo-2,3-dihydro-1H-indol-5-yl)oxy]ethyl methanesulfonate

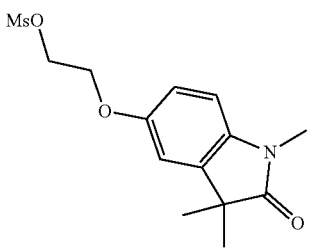 [SMILES: CN1C(=O)C(C)(C)c2cc(OCCOS(C)(=O)=O)ccc21]

To a solution of 5-(2-hydroxyethoxy)-1,3,3-trimethyl-2,3-dihydro-1H-indol-2-one (65.0 mg, 0.276 mmol) and TEA (57.9 µL, 0.414 mmol) in DCM (2 mL) was added methanesulfonyl chloride (25.6 µL, 0.332 mmol). The mixture was stirred for 30 min, then quenched with $H_2O$ (5 mL) and extracted with DCM (2×10 mL). The combined organic layers were dried over $Na_2SO_4$, filtered, and concentrated in vacuo and used in the subsequent step without further purification. MS=314.1 [M+H]$^+$.

Step 3: 2-oxo-1'-{2-[(1,3,3-trimethyl-2-oxo-2,3-dihydro-1H-indol-5-yl)oxy]ethyl}-1,2-dihydrospiro[indole-3,4'-piperidine]-5-carbonitrile (Compound 83)

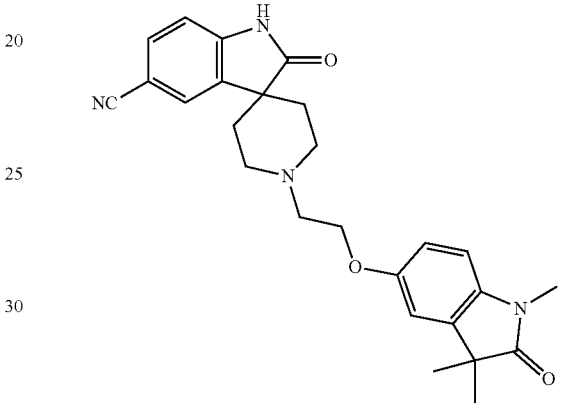

A mixture of 2-[(1,3,3-trimethyl-2-oxo-2,3-dihydro-1H-indol-5-yl)oxy]ethyl methanesulfonate (84.0 mg, 0.268 mmol), 2-oxo-1,2-dihydrospiro[indole-3,4'-piperidine]-5-carbonitrile (Intermediate B-9, 64.0 mg, 0.241 mmol, HCl salt) and $K_2CO_3$ (93.0 mg, 0.670 mmol) in DMF (1.2 mL) was heated at 60° C. for 3 h. After cooling to room temperature, the mixture was diluted with $H_2O$ (10 mL) and extracted with EtOAc (2×20 mL). The combined organic layers were dried over $Na_2SO_4$, filtered, and concentrated in vacuo. The crude residue was purified by reverse phase preparative HPLC (Phenomenex Kinetex $C_{18}$ column, 0-30% MeCN:$H_2O$ with 0.1% formic acid modifier) to give 2-oxo-1'-{2-[(1,3,3-trimethyl-2-oxoindol-5-yl)oxy]ethyl}-1H-spiro[indole-3,4'-piperidine]-5-carbonitrile (Compound 83). $^1$H NMR (500 MHz, DMSO-d$_6$): δ 10.87 (s, 1H), 7.96 (s, 1H), 7.68 (d, J=8.1 Hz, 1H), 7.09 (d, J=2.5 Hz, 1H), 7.00 (d, J=8.1 Hz, 1H), 6.94-6.84 (m, 2H), 4.11 (t, J=5.8 Hz, 2H), 3.10 (s, 3H), 2.96-2.83 (m, 4H), 2.81-2.70 (m, 2H), 1.85-1.71 (m, 4H), 1.26 (s, 6H). MS=445.2 [M+H]$^+$.

Example 25

1'-{2-[3,5-difluoro-4-(3-methanesulfonyloxetan-3-yl)phenoxy]ethyl}-2-oxo-1,2-dihydrospiro[indole-3,4'-piperidine]-5-carbonitrile (Compound 84)

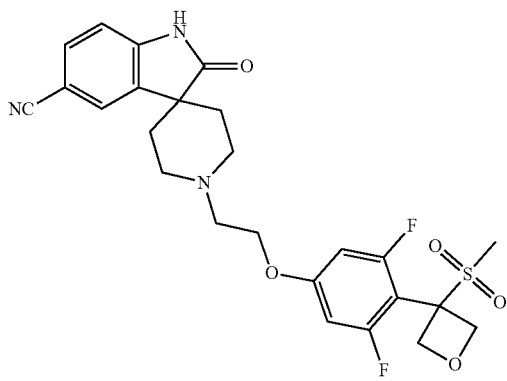 [SMILES: CS(=O)(=O)C1(c2c(F)cc(OCCN3CCC4(CC3)C(=O)Nc3ccc(C#N)cc34)cc2F)COC1]

To a solution of 3-[4-(2-bromoethoxy)-2,6-difluorophenyl]-3-methanesulfonyloxetane (Intermediate A-32, 60.0 mg, 0.162 mmol) in MeCN (1.00 mL) was added NaHCO$_3$ (40.7 mg, 0.485 mmol) and 2-oxospiro[indoline-3,4'-piperidine]-5-carbonitrile (Intermediate B-9, 46.89 mg, 177.8 μmol, HCl salt). The mixture was stirred at 80° C. for 16 h. After cooling to room temperature, the reaction mixture was filtered and washed with MeCN. The filtrate was concentrated in vacuo. The crude residue was purified by reverse phase preparative HPLC (Waters Xbridge BEH C$_{18}$ column, 25-55% MeCN:H$_2$O with 10 mM NH$_4$HCO$_3$ modifier) to give 1'-{2-[3,5-difluoro-4-(3-methanesulfonyloxetan-3-yl)phenoxy]ethyl}-2-oxo-1,2-dihydrospiro[indole-3,4'-piperidine]-5-carbonitrile (Compound 84). $^1$H NMR (400 MHz, DMSO-d$_6$): δ 10.86 (s, 1H), 7.96 (s, 1H), 7.67 (d, J=8.4 Hz, 1H), 6.98 (d, J=8.4 Hz, 1H), 6.90 (d, J=10.8 Hz, 2H), 5.14 (dd, J=14.4, 8.0 Hz, 4H), 4.21 (t, J=5.2 Hz, 2H), 3.13 (s, 3H), 2.89-2.85 (m, 4H), 2.74-2.71 (m, 2H), 1.81-1.72 (m, 4H). MS=518.2 [M+H]$^+$.

The following compounds in Table 29 were prepared according to procedures analogous to those described for Compound 84 using the appropriate starting materials. In cases where step 1 was followed by chiral SFC purification to separate isomers, chiral column conditions and elution order are specified.

TABLE 29

| # | Structure | IUPAC Name | Exact Mass [M + H]$^+$ | Intermediates Used | Chiral Column, If Applicable | Elution Order |
|---|---|---|---|---|---|---|
| 85 | 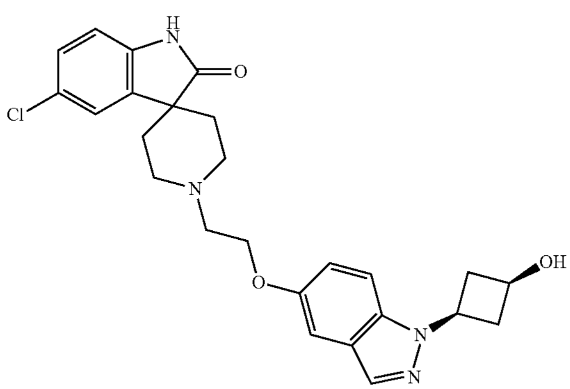 [SMILES: O=C1Nc2ccc(Cl)cc2C12CCN(CCOc1ccc3c(cnn3[C@H]3C[C@@H](O)C3)c1)CC2] | 5-chloro-1'-[2-({1-[(cis)-3-hydroxycyclobutyl]-1H-indazol-5-yl}oxy)ethyl]-1,2-dihydrospiro[indole-3,4'-piperidin]-2-one | Calc'd 467.2 Found 467.3 | A-63 and B-4 | n/a | n/a |
| 86 | 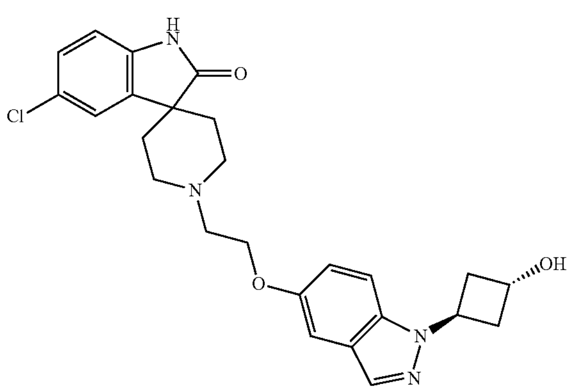 [SMILES: O=C1Nc2ccc(Cl)cc2C12CCN(CCOc1ccc3c(cnn3[C@H]3C[C@H](O)C3)c1)CC2] | 5-chloro-1'-[2-({1-[(trans)-3-hydroxycyclobutyl]-1H-indazol-5-yl}oxy)ethyl]-1,2-dihydrospiro[indole-3,4'-piperidin]-2-one | Calc'd 467.2 Found 467.3 | A-62 and B-4 | n/a | n/a |

TABLE 29-continued

| # | Structure | IUPAC Name | Exact Mass [M + H]+ | Intermediates Used | Chiral Column, If Applicable | Elution Order |
|---|---|---|---|---|---|---|
| 87 | 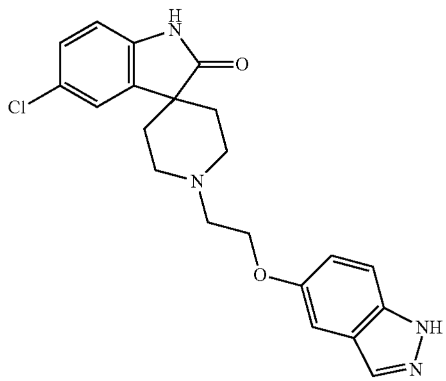 [SMILES: O=C1Nc2ccc(Cl)cc2C12CCN(CCOc1ccc3[nH]ncc3c1)CC2] | 5-chloro-1'-[2-(2H-indazol-5-yloxy)ethyl]-1,2-dihydrospiro[indole-3,4'-piperidin]-2-one | Calc'd 397.1 Found 397.1 | A-80 and B-4 | n/a | n/a |
| 88 | 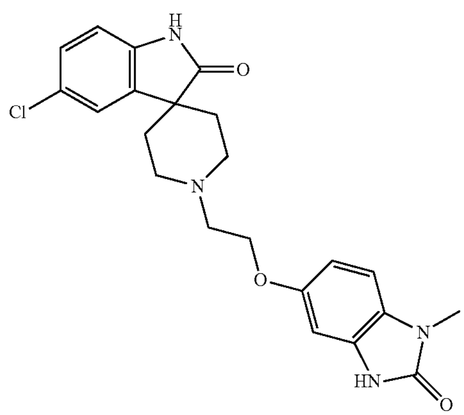 [SMILES: Cn1c(=O)[nH]c2cc(OCCN3CCC4(CC3)C(=O)Nc3ccc(Cl)cc34)ccc21] | 5-chloro-1'-{2-[(1-methyl-2-oxo-2,3-dihydro-1H-1,3-benzodiazol-5-yl)oxy]ethyl}-1,2-dihydrospiro[indole-3,4'-piperidin]-2-one | Calc'd 427.1 Found 427.2 | A-82 and B-4 | n/a | n/a |
| 89 | 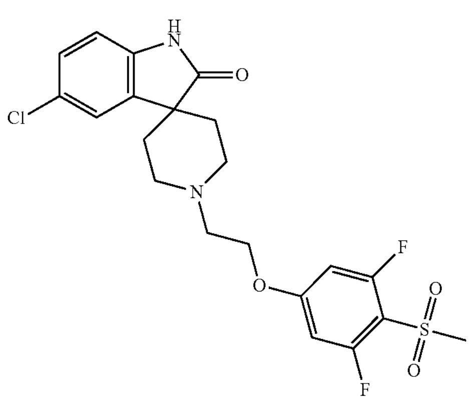 [SMILES: CS(=O)(=O)c1c(F)cc(OCCN2CCC3(CC2)C(=O)Nc2ccc(Cl)cc23)cc1F] | 5-chloro-1'-[2-(3,5-difluoro-4-methanesulfonyl-phenoxy)ethyl]-1,2-dihydrospiro[indole-3,4'-piperidin]-2-one | Calc'd 471.1 Found 471.1 | A-18 and B-4 | n/a | n/a |

TABLE 29-continued

| # | Structure | IUPAC Name | Exact Mass [M + H]⁺ | Intermediates Used | Chiral Column, If Applicable | Elution Order |
|---|---|---|---|---|---|---|
| 90 | 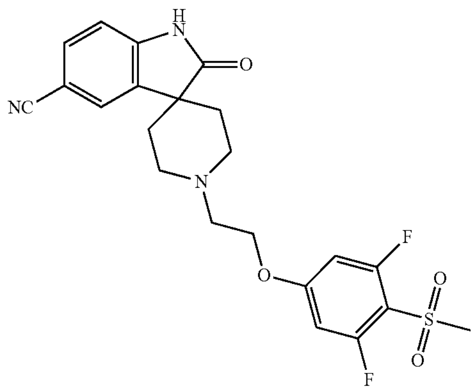 [SMILES: CS(=O)(=O)c1c(F)cc(OCCN2CCC3(CC2)C(=O)Nc2ccc(C#N)cc23)cc1F] | 1'-[2-(3,5-difluoro-4-methanesulfonyl-phenoxy)ethyl]-2-oxo-1,2-dihydrospiro[indole-3,4'-piperidine]-5-carbonitrile | Calc'd 462.1 Found 462.0 | A-18 and B-9 | n/a | n/a |
| 91 | 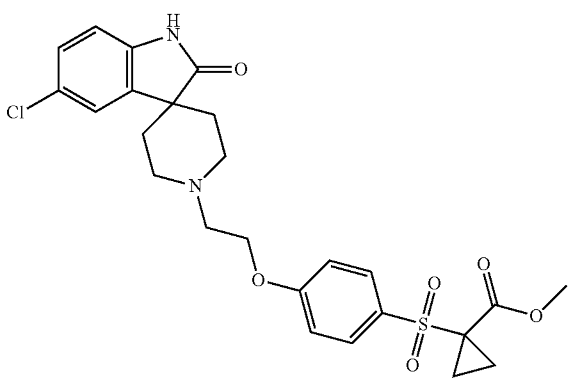 [SMILES: COC(=O)C1(S(=O)(=O)c2ccc(OCCN3CCC4(CC3)C(=O)Nc3ccc(Cl)cc34)cc2)CC1] | methyl 1-[4-(2-{5-chloro-2-oxo-1,2-dihydrospiro[indole-3,4'-piperidin]-1'-yl}ethoxy)benzene-sulfonyl]cyclopropane-1-carboxylate | Calc'd 519.1 Found 519.1 | A-24 and B-4 | n/a | n/a |
| 92 | 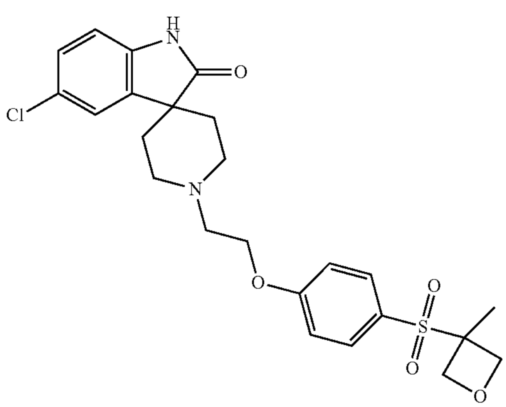 [SMILES: CC1(S(=O)(=O)c2ccc(OCCN3CCC4(CC3)C(=O)Nc3ccc(Cl)cc34)cc2)COC1] | 5-chloro-1'-(2-{4-[(3-methyloxetan-3-yl)sulfonyl]phenoxy}ethyl)-1,2-dihydrospiro[indole-3,4'-piperidin]-2-one | Calc'd 491.1 Found 491.2 | A-27 and B-4 | n/a | n/a |

TABLE 29-continued

| # | Structure | IUPAC Name | Exact Mass [M + H]+ | Intermediates Used | Chiral Column, If Applicable | Elution Order |
|---|---|---|---|---|---|---|
| 93 | 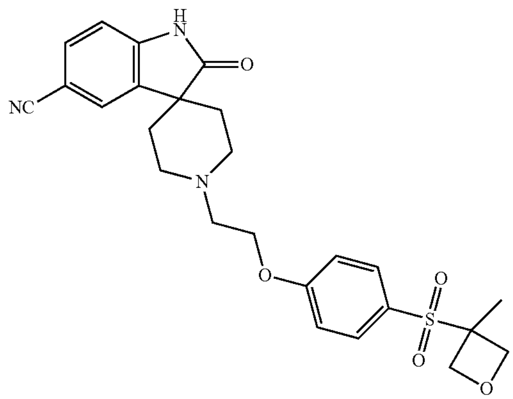 [SMILES: CC1(S(=O)(=O)c2ccc(OCCN3CCC4(CC3)C(=O)Nc3ccc(C#N)cc34)cc2)COC1] | 1'-(2-{4-[(3-methyloxetan-3-yl)sulfonyl]phenoxy}ethyl)-2-oxo-1,2-dihydrospiro[indole-3,4'-piperidine]-5-carbonitrile | Calc'd 482.2 Found 482.2 | A-27 and B-9 | n/a | n/a |
| 94 | 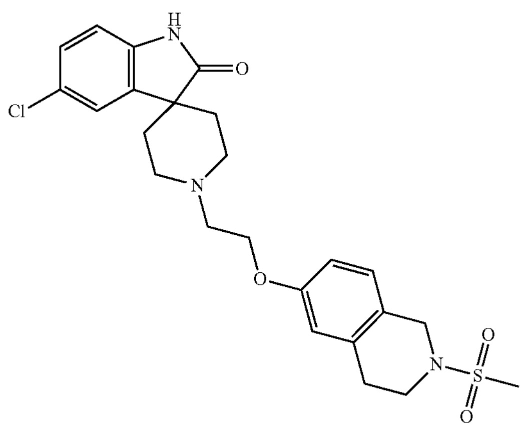 [SMILES: CS(=O)(=O)N1CCc2cc(OCCN3CCC4(CC3)C(=O)Nc3ccc(Cl)cc34)ccc2C1] | 5-chloro-1'-{2-[(2-methanesulfonyl-1,2,3,4-tetrahydroisoquinolin-6-yl)oxy]ethyl}-1,2-dihydrospiro[indole-3,4'-piperidin]-2-one | Calc'd 490.1 Found 490.2 | A-55 and B-4 | n/a | n/a |
| 95 | 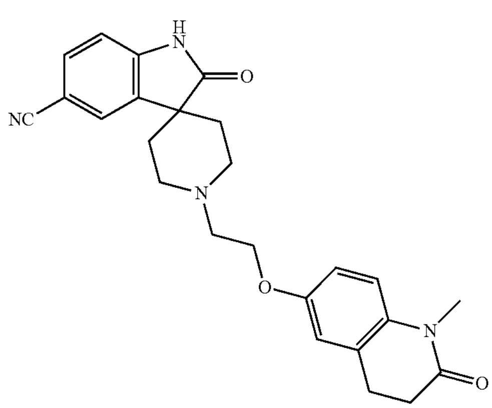 [SMILES: CN1C(=O)CCc2cc(OCCN3CCC4(CC3)C(=O)Nc3ccc(C#N)cc34)ccc21] | 1'-{2-[(1-methyl-2-oxo-1,2,3,4-tetrahydroquinolin-6-yl)oxy]ethyl}-2-oxo-1,2-dihydrospiro[indole-3,4'-piperidine]-5-carbonitrile | Calc'd 431.2 Found 431.3 | A-71 and B-9 | n/a | n/a |

TABLE 29-continued

| # | Structure | IUPAC Name | Exact Mass [M + H]⁺ | Intermediates Used | Chiral Column, If Applicable | Elution Order |
|---|---|---|---|---|---|---|
| 96 | 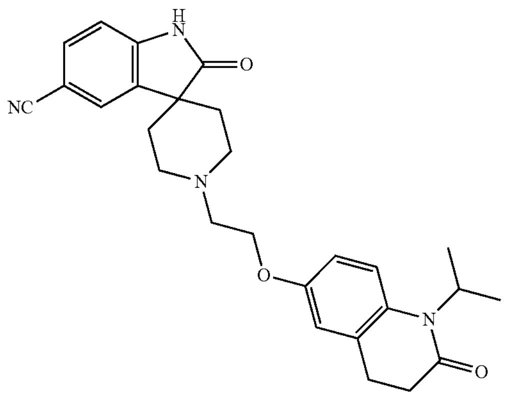 [SMILES: CC(C)N1C(=O)CCc2cc(OCCN3CCC4(CC3)C(=O)Nc3ccc(C#N)cc34)ccc21] | 2-oxo-1'-(2-{[2-oxo-1-(propan-2-yl)-1,2,3,4-tetrahydroquinolin-6-yl]oxy}ethyl)-1,2-dihydrospiro[indole-3,4'-piperidine]-5-carbonitrile | Calc'd 459.2 Found 459.1 | A-64 and B-9 | n/a | n/a |
| 97 | 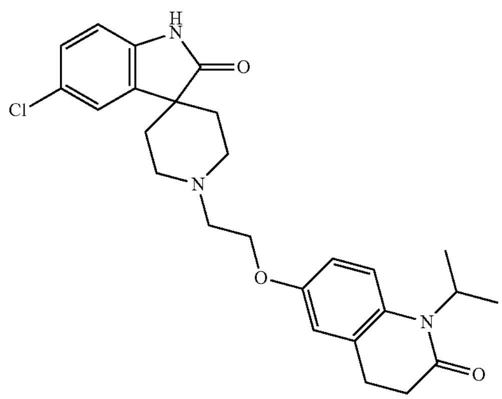 [SMILES: CC(C)N1C(=O)CCc2cc(OCCN3CCC4(CC3)C(=O)Nc3ccc(Cl)cc34)ccc21] | 5-chloro-1'-(2-{[2-oxo-1-(propan-2-yl)-1,2,3,4-tetrahydroquinolin-6-yl]oxy}ethyl)-1,2-dihydrospiro[indole-3,4'-piperidin]-2-one | Calc'd 468.2 Found 468.2 | A-64 and B-4 | n/a | n/a |
| 98 | 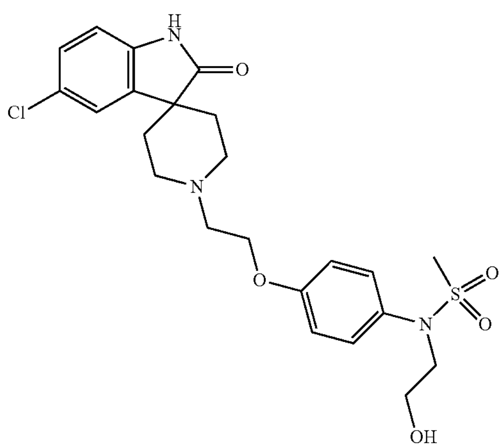 [SMILES: CS(=O)(=O)N(CCO)c1ccc(OCCN2CCC3(CC2)C(=O)Nc2ccc(Cl)cc23)cc1] | N-[4-(2-{5-chloro-2-oxo-1,2-dihydrospiro[indole-3,4'-piperidin]-1'-yl}ethoxy)phenyl]-N-(2-hydroxyethyl)methanesulfonamide | Calc'd 494.1 Found 494.1 | A-68 and B-4 | n/a | n/a |

TABLE 29-continued

| # | Structure | IUPAC Name | Exact Mass [M + H]+ | Intermediates Used | Chiral Column, If Applicable | Elution Order |
|---|---|---|---|---|---|---|
| 99 | 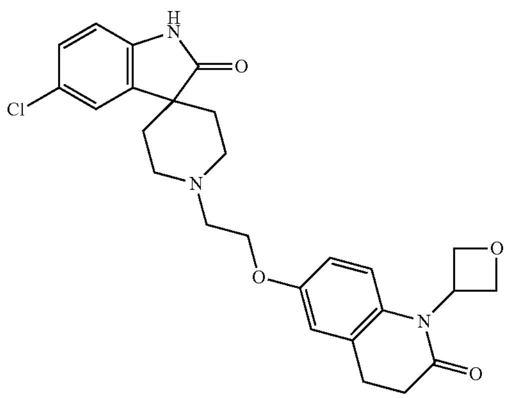 [SMILES: O=C1CCc2cc(OCCN3CCC4(CC3)C(=O)Nc3ccc(Cl)cc34)ccc2N1C1COC1] | 5-chloro-1'-(2-{[1-(oxetan-3-yl)-2-oxo-1,2,3,4-tetrahydroquinolin-6-yl]oxy}ethyl)-1,2-dihydrospiro[indole-3,4'-piperidin]-2-one | Calc'd 482.2 Found 482.2 | A-66 and B-4 | n/a | n/a |
| 100 | 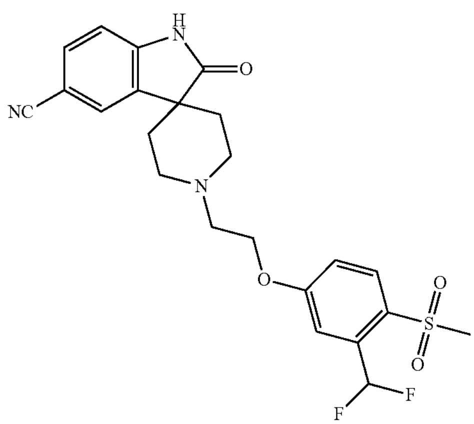 [SMILES: CS(=O)(=O)c1ccc(OCCN2CCC3(CC2)C(=O)Nc2ccc(C#N)cc23)cc1C(F)F] | 1'-{2-[3-(difluoromethyl)-4-methanesulfonylphenoxy]ethyl}-2-oxo-1,2-dihydrospiro[indole-3,4'-piperidine]-5-carbonitrile | Calc'd 476.1 Found 476.2 | A-13 and B-9 | n/a | n/a |
| 101 | 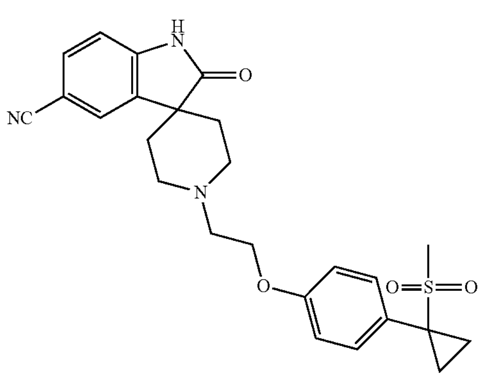 [SMILES: CS(=O)(=O)C1(c2ccc(OCCN3CCC4(CC3)C(=O)Nc3ccc(C#N)cc34)cc2)CC1] | 1'-{2-[4-(1-methanesulfonylcyclopropyl)phenoxy]ethyl}-2-oxo-1,2-dihydrospiro[indole-3,4'-piperidine]-5-carbonitrile | Calc'd 466.2 Found 466.2 | A-28 and B-9 | n/a | n/a |

TABLE 29-continued

| # | Structure | IUPAC Name | Exact Mass [M + H]+ | Intermediates Used | Chiral Column, If Applicable | Elution Order |
|---|---|---|---|---|---|---|
| 102 | 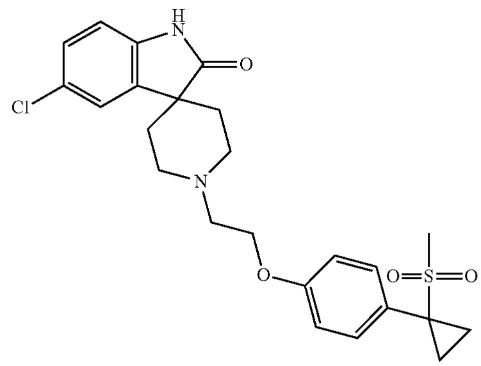 [SMILES: CS(=O)(=O)C1(c2ccc(OCCN3CCC4(CC3)C(=O)Nc3ccc(Cl)cc34)cc2)CC1] | 5-chloro-1'-{2-[4-(1-methanesulfonyl-cyclopropyl)phenoxy]ethyl}-1,2-dihydrospiro[indole-3,4'-piperidin]-2-one | Calc'd 475.1 Found 475.2 | A-28 and B-4 | n/a | n/a |
| 103 | 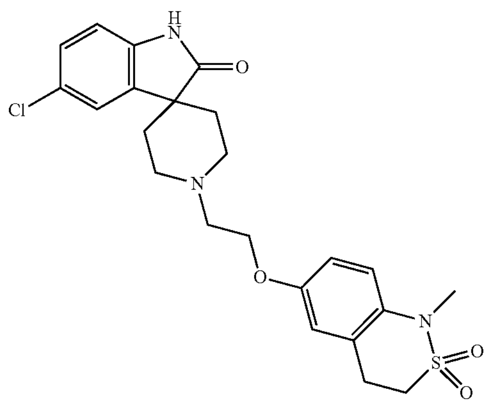 [SMILES: CN1c2ccc(OCCN3CCC4(CC3)C(=O)Nc3ccc(Cl)cc34)cc2CCS1(=O)=O] | 6-(2-{5-chloro-2-oxo-1,2-dihydrospiro[indole-3,4'-piperidin]-1'-yl}ethoxy)-1-methyl-3,4-dihydro-1H-2$\lambda^6$,1-benzothiazine-2,2-dione | Calc'd 476.1 Found 476.2 | A-51 and B-4 | n/a | n/a |
| 104 | 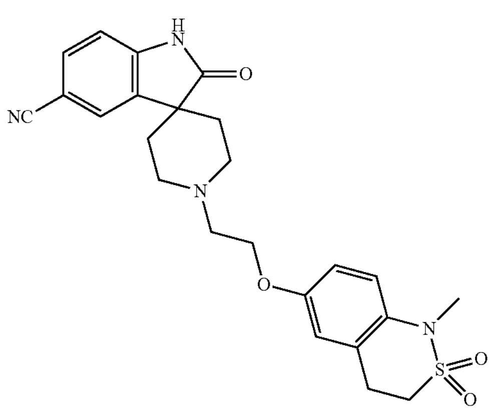 [SMILES: CN1c2ccc(OCCN3CCC4(CC3)C(=O)Nc3ccc(C#N)cc34)cc2CCS1(=O)=O] | 1'-{2-[(1-methyl-2,2-dioxo-3,4-dihydro-1H-2$\lambda^6$,1-benzothiazin-6-yl)oxy]ethyl}-2-oxo-1,2-dihydrospiro[indole-3,4'-piperidine]-5-carbonitrile | Calc'd 467.2 Found 467.2 | A-51 and B-9 | n/a | n/a |

TABLE 29-continued

| # | Structure | IUPAC Name | Exact Mass [M + H]+ | Intermediates Used | Chiral Column, If Applicable | Elution Order |
|---|---|---|---|---|---|---|
| 105 | 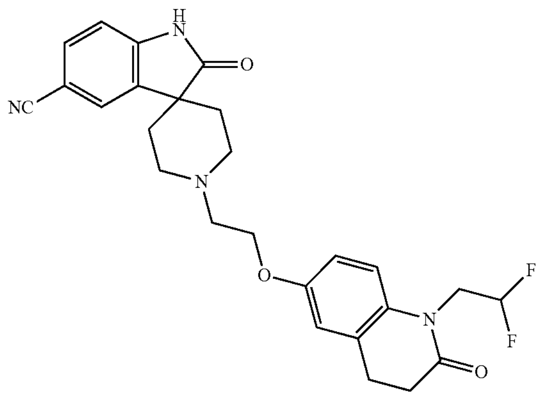 [SMILES: N#Cc1ccc2c(c1)C1(CCN(CCOc3ccc4c(c3)CCC(=O)N4CC(F)F)CC1)C(=O)N2] | 1'-(2-{[1-(2,2-difluoroethyl)-2-oxo-1,2,3,4-tetrahydroquinolin-6-yl]oxy}ethyl)-2-oxo-1,2-dihydrospiro[indole-3,4'-piperidine]-5-carbonitrile | Calc'd 481.2 Found 481.3 | A-67 and B-9 | n/a | n/a |
| 106 | 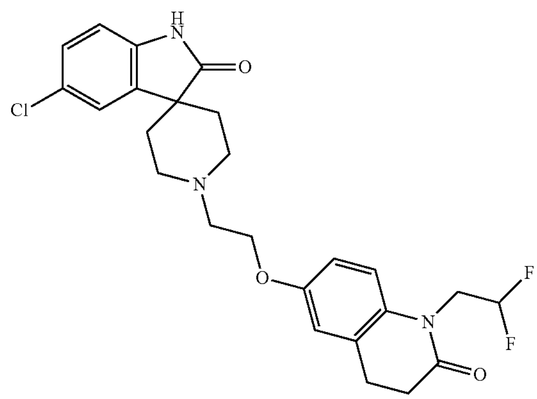 [SMILES: O=C1CCc2cc(OCCN3CCC4(CC3)C(=O)Nc3ccc(Cl)cc34)ccc2N1CC(F)F] | 5-chloro-1'-(2-{[1-(2,2-difluoroethyl)-2-oxo-1,2,3,4-tetrahydroquinolin-6-yl]oxy}ethyl)-1,2-dihydrospiro[indole-3,4'-piperidin]-2-one | Calc'd 490.2 Found 490.3 | A-67 and B-4 | n/a | n/a |
| 107 | 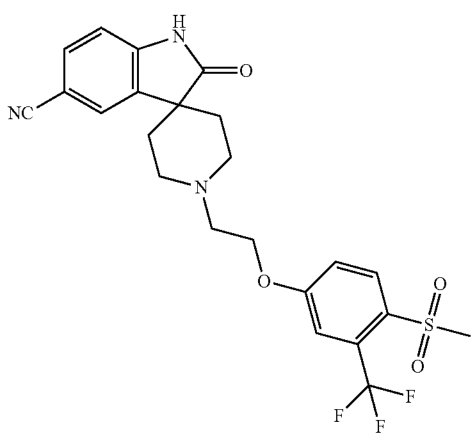 [SMILES: CS(=O)(=O)c1ccc(OCCN2CCC3(CC2)C(=O)Nc2ccc(C#N)cc23)cc1C(F)(F)F] | 1'-{2-[4-methanesulfonyl-3-(trifluoromethyl)phenoxy]ethyl}-2-oxo-1,2-dihydrospiro[indole-3,4'-piperidine]-5-carbonitrile | Calc'd 494.1 Found 494.1 | A-17 and B-9 | n/a | n/a |

TABLE 29-continued

| # | Structure | IUPAC Name | Exact Mass [M + H]+ | Intermediates Used | Chiral Column, If Applicable | Elution Order |
|---|---|---|---|---|---|---|
| 108 | 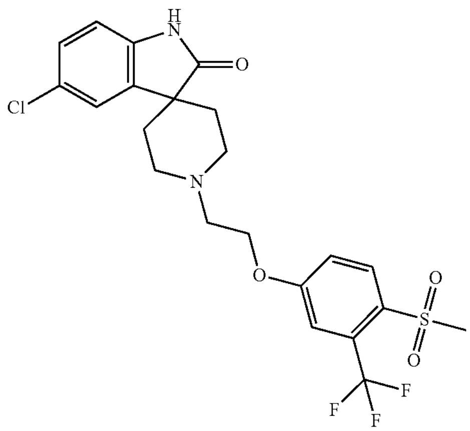 [SMILES: CS(=O)(=O)c1ccc(OCCN2CCC3(CC2)C(=O)Nc2ccc(Cl)cc23)cc1C(F)(F)F] | 5-chloro-1'-{2-[4-methanesulfonyl-3-(trifluoromethyl)phenoxy]ethyl}-1,2-dihydrospiro[indole-3,4'-piperidin]-2-one | Calc'd 503.1 Found 503.1 | A-17 and B-4 | n/a | n/a |
| 109 | 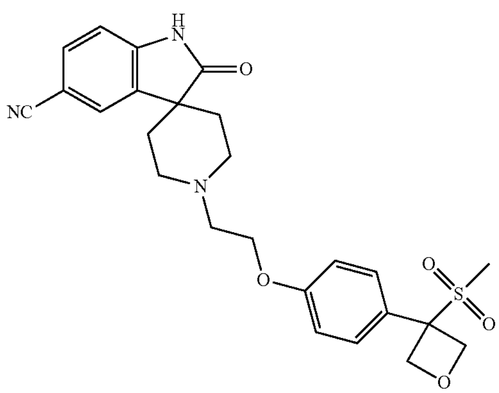 [SMILES: CS(=O)(=O)C1(c2ccc(OCCN3CCC4(CC3)C(=O)Nc3ccc(C#N)cc34)cc2)COC1] | 1'-{2-[4-(3-methanesulfonyloxetan-3-yl)phenoxy]ethyl}-2-oxo-1,2-dihydrospiro[indole-3,4'-piperidine]-5-carbonitrile | Calc'd 482.2 Found 482.1 | A-33 and B-9 | n/a | n/a |
| 110 | 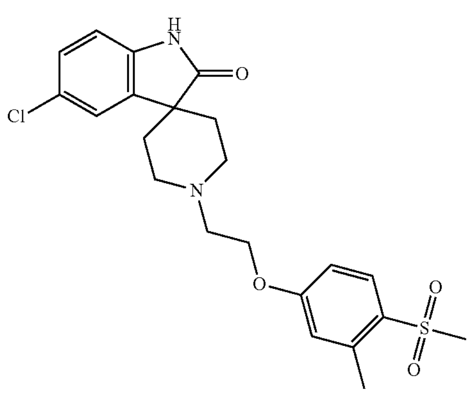 [SMILES: Cc1cc(OCCN2CCC3(CC2)C(=O)Nc2ccc(Cl)cc23)ccc1S(C)(=O)=O] | 5-chloro-1'-[2-(4-methanesulfonyl-3-methylphenoxy)ethyl]-1,2-dihydrospiro[indole-3,4'-piperidin]-2-one | Calc'd 449.1 Found 449.1 | A-22 and B-4 | n/a | n/a |

TABLE 29-continued

| # | Structure | IUPAC Name | Exact Mass [M + H]+ | Intermediates Used | Chiral Column, If Applicable | Elution Order |
|---|---|---|---|---|---|---|
| 111 | 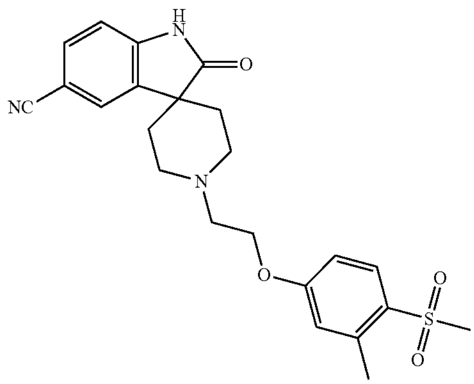 [SMILES: Cc1cc(OCCN2CCC3(CC2)C(=O)Nc2ccc(C#N)cc23)ccc1S(C)(=O)=O] | 1'-[2-(4-methanesulfonyl-3-methylphenoxy)ethyl]-2-oxo-1,2-dihydrospiro[indole-3,4'-piperidine]-5-carbonitrile | Calc'd 440.2 Found 440.2 | A-22 and B-9 | n/a | n/a |
| 112 | 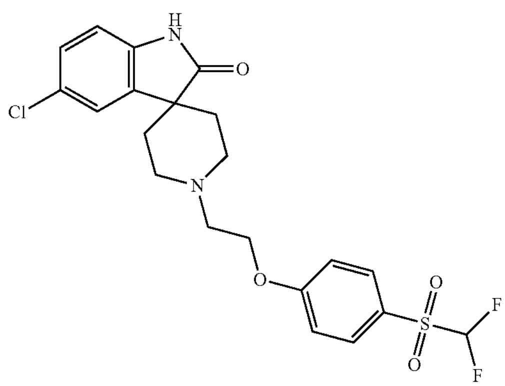 [SMILES: O=C1Nc2ccc(Cl)cc2C12CCN(CCOc1ccc(S(=O)(=O)C(F)F)cc1)CC2] | 5-chloro-1'-[2-(4-difluoromethanesulfonylphenoxy)ethyl]-1,2-dihydrospiro[indole-3,4'-piperidin]-2-one | Calc'd 471.1 Found 471.1 | A-16 and B-4 | n/a | n/a |
| 113 | 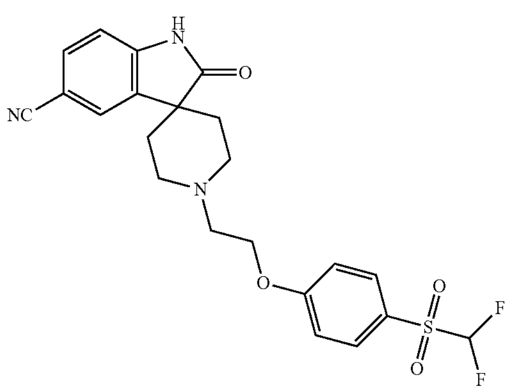 [SMILES: N#Cc1ccc2c(c1)C1(CCN(CCOc3ccc(S(=O)(=O)C(F)F)cc3)CC1)C(=O)N2] | 1'-[2-(4-difluoromethanesulfonylphenoxy)ethyl]-2-oxo-1,2-dihydrospiro[indole-3,4'-piperidine]-5-carbonitrile | Calc'd 462.1 Found 462.2 | A-16 and B-9 | n/a | n/a |

TABLE 29-continued

| # | Structure | IUPAC Name | Exact Mass [M + H]+ | Intermediates Used | Chiral Column, If Applicable | Elution Order |
|---|---|---|---|---|---|---|
| 114 | 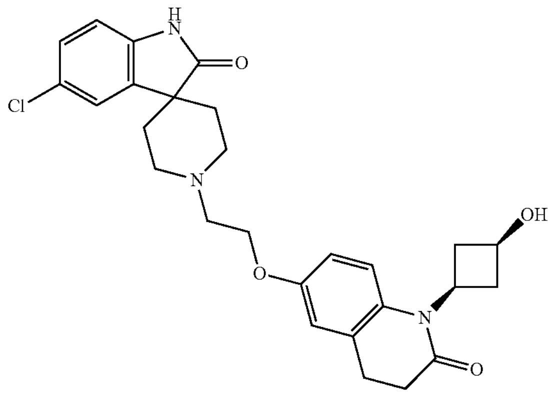 [SMILES: O=C1CCc2cc(OCCN3CCC4(CC3)C(=O)Nc3ccc(Cl)cc34)ccc2N1[C@H]1C[C@@H](O)C1] | 5-chloro-1'-[2-({2-oxo-1-[(cis)-3-hydroxycyclobutyl]-1,2,3,4-tetrahydroquinolin-6-yl}oxy)ethyl]-1,2-dihydrospiro[indole-3,4'-piperidin]-2-one | Calc'd 496.2 Found 496.2 | A-69 and B-4 | n/a | n/a |
| 115 | 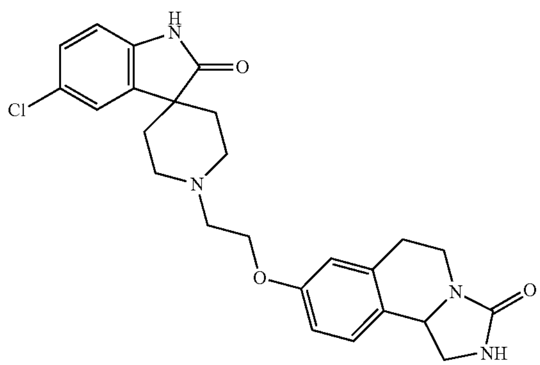 [SMILES: O=C1NCC2c3ccc(OCCN4CCC5(CC4)C(=O)Nc4ccc(Cl)cc45)cc3CCN12] | 5-chloro-1'-[2-({3-oxo-1H,2H,3H,5H,6H,10bH-imidazo[4,3-a]isoquinolin-8-yl}oxy)ethyl]-1,2-dihydrospiro[indole-3,4'-piperidin]-2-one | Calc'd 467.2 Found 467.2 | A-58 and B-4 | n/a | n/a |
| 116 | 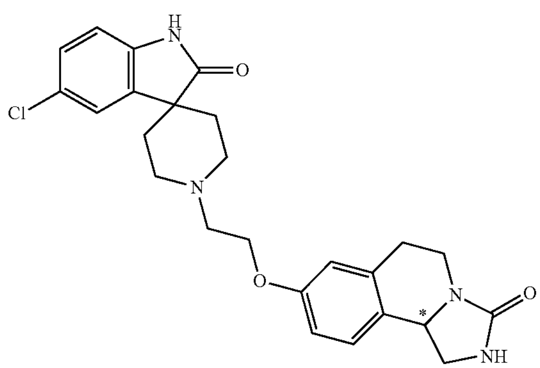 [SMILES: O=C1NCC2c3ccc(OCCN4CCC5(CC4)C(=O)Nc4ccc(Cl)cc45)cc3CCN12] | (S) or (R)-5-chloro-1'-[2-({3-oxo-1H,2H,3H,5H,6H,10bH-imidazo[4,3-a]isoquinolin-8-yl}oxy)ethyl]-1,2-dihydrospiro[indole-3,4'-piperidin]-2-one | Calc'd 467.2 Found 467.2 | A-58 and B-4 | Daicel Chiralpak AD-3 | Second |
| 117 | 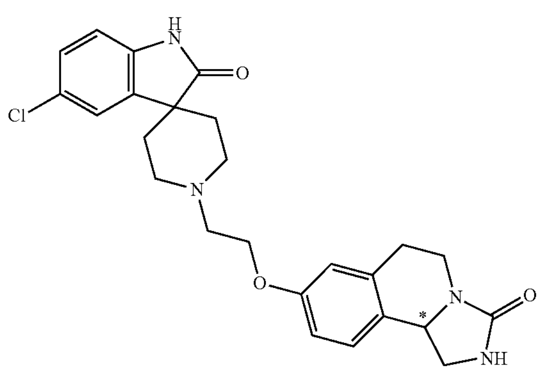 [SMILES: O=C1NCC2c3ccc(OCCN4CCC5(CC4)C(=O)Nc4ccc(Cl)cc45)cc3CCN12] | (R) or (S)-5-chloro-1'-[2-({3-oxo-1H,2H,3H,5H,6H,10bH-imidazo[4,3-a]isoquinolin-8-yl}oxy)ethyl]-1,2-dihydrospiro[indole-3,4'-piperidin]-2-one | Calc'd 467.2 Found 467.2 | A-58 and B-4 | Daicel Chiralpak AD-3 | First |

TABLE 29-continued

| # | Structure | IUPAC Name | Exact Mass [M + H]+ | Intermediates Used | Chiral Column, If Applicable | Elution Order |
|---|---|---|---|---|---|---|
| 118 | 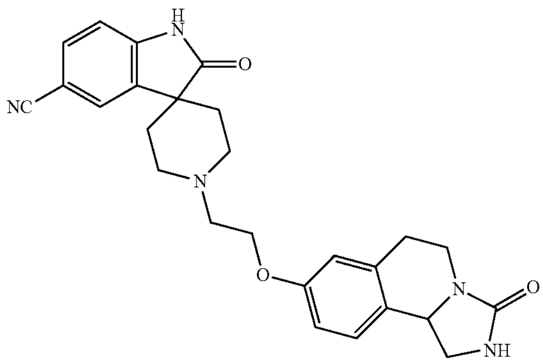 [SMILES: N#Cc1ccc2c(c1)C1(CCN(CCOc3ccc4c(c3)CCN3C(=O)NCC43)CC1)C(=O)N2] | 2-oxo-1'-[2-({3-oxo-1H,2H,3H,5H,6H,10bH-imidazo[4,3-a]isoquinolin-8-yl}oxy)ethyl]-1,2-dihydrospiro[indole-3,4'-piperidine]-5-carbonitrile | Calc'd 458.2 Found 458.3 | A-58 and B-9 | n/a | n/a |
| 119 | 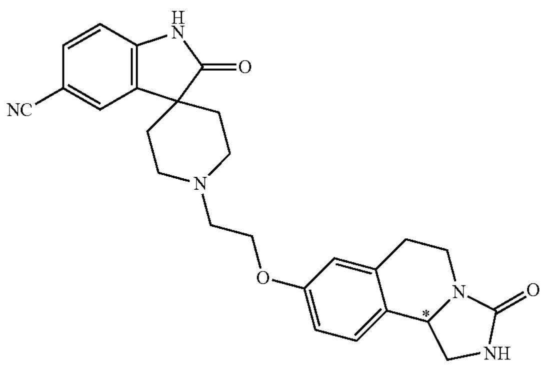 [SMILES: N#Cc1ccc2c(c1)C1(CCN(CCOc3ccc4c(c3)CCN3C(=O)NCC43)CC1)C(=O)N2] | (S) or (R)-2-oxo-1'-[2-({3-oxo-1H,2H,3H,5H,6H,10bH-imidazo[4,3-a]isoquinolin-8-yl}oxy)ethyl]-1,2-dihydrospiro[indole-3,4'-piperidine]-5-carbonitrile | Calc'd 458.2 Found 458.3 | A-58 and B-9 | Daicel Chiralpak AD-3 | First |
| 120 | 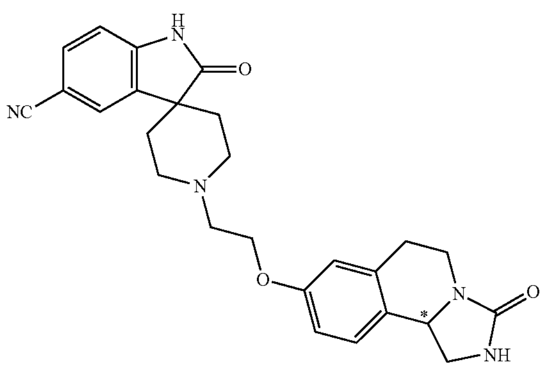 [SMILES: N#Cc1ccc2c(c1)C1(CCN(CCOc3ccc4c(c3)CCN3C(=O)NCC43)CC1)C(=O)N2] | (R) or (S)-2-oxo-1'-[2-({3-oxo-1H,2H,3H,5H,6H,10bH-imidazo[4,3-a]isoquinolin-8-yl}oxy)ethyl]-1,2-dihydrospiro[indole-3,4'-piperidine]-5-carbonitrile | Calc'd 458.2 Found 458.3 | A-58 and B-9 | Daicel Chiralpak AD-3 | Second |
| 121 | 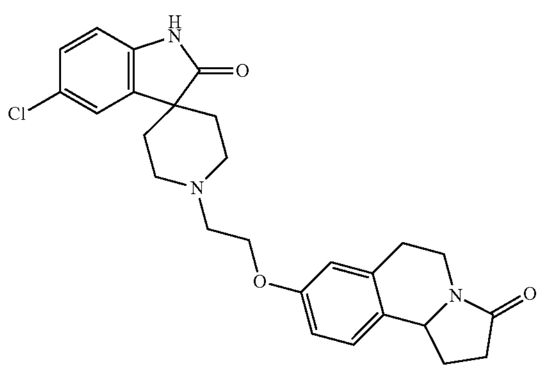 [SMILES: O=C1CCC2c3ccc(OCCN4CCC5(CC4)C(=O)Nc4ccc(Cl)cc45)cc3CCN12] | 5-chloro-1'-[2-({3-oxo-1H,2H,3H,5H,6H,10bH-pyrrolo[2,1-a]isoquinolin-8-yl}oxy)ethyl]-1,2-dihydrospiro[indole-3,4'-piperidin]-2-one | Calc'd 466.2 Found 466.1 | A-57 and B-4 | n/a | n/a |

TABLE 29-continued

| # | Structure | IUPAC Name | Exact Mass [M + H]+ | Intermediates Used | Chiral Column, If Applicable | Elution Order |
|---|---|---|---|---|---|---|
| 122 | 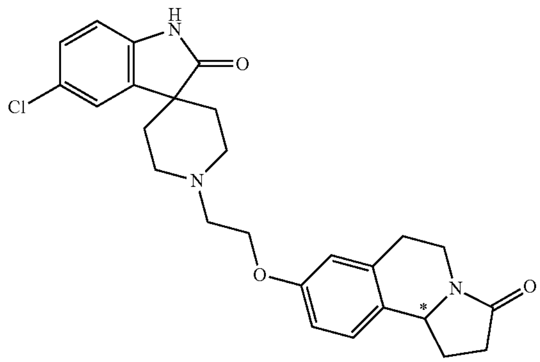 [SMILES: O=C1CCC2c3ccc(OCCN4CCC5(CC4)C(=O)Nc4ccc(Cl)cc45)cc3CCN12] | (S) or (R)-5-chloro-1'-[2-({3-oxo-1H,2H,3H,5H,6H,10bH-pyrrolo[2,1-a]isoquinolin-8-yl}oxy)ethyl]-1,2-dihydrospiro[indole-3,4'-piperidin]-2-one | Calc'd 466.2 Found 466.1 | A-57 and B-4 | Daicel Chiralpak AD-3 | First |
| 123 | 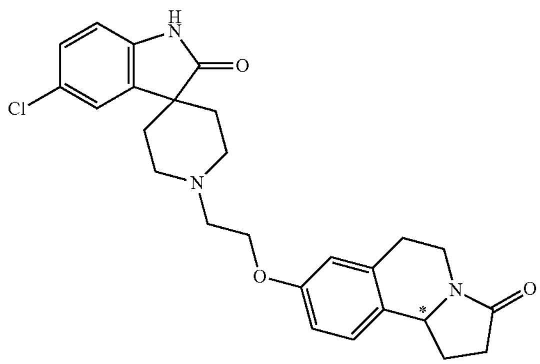 [SMILES: O=C1CCC2c3ccc(OCCN4CCC5(CC4)C(=O)Nc4ccc(Cl)cc45)cc3CCN12] | (R) or (S)-5-chloro-1'-[2-({3-oxo-1H,2H,3H,5H,6H,10bH-pyrrolo[2,1-a]isoquinolin-8-yl}oxy)ethyl]-1,2-dihydrospiro[indole-3,4'-piperidin]-2-one | Calc'd 466.2 Found 466.1 | A-57 and B-4 | Daicel Chiralpak AD-3 | Second |
| 124 | 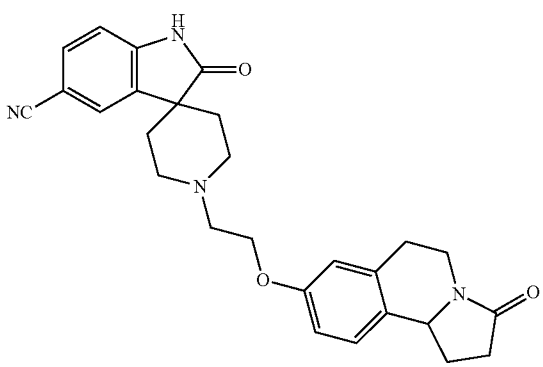 [SMILES: N#Cc1ccc2c(c1)C1(CCN(CCOc3ccc4c(c3)CCN3C(=O)CCC43)CC1)C(=O)N2] | 2-oxo-1'-[2-({3-oxo-1H,2H,3H,5H,6H,10bH-pyrrolo[2,1-a]isoquinolin-8-yl}oxy)ethyl]-1,2-dihydrospiro[indole-3,4'-piperidine]-5-carbonitrile | Calc'd 457.2 Found 457.1 | A-57 and B-9 | n/a | n/a |
| 125 | 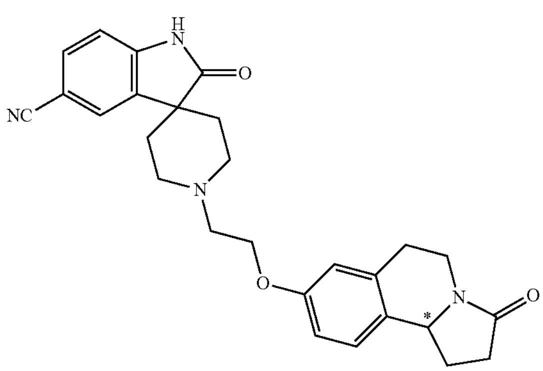 [SMILES: N#Cc1ccc2c(c1)C1(CCN(CCOc3ccc4c(c3)CCN3C(=O)CCC43)CC1)C(=O)N2] | (S) or (R)-2-oxo-1'-[2-({3-oxo-1H,2H,3H,5H,6H,10bH-pyrrolo[2,1-a]isoquinolin-8-yl}oxy)ethyl]-1,2-dihydrospiro[indole-3,4'-piperidine]-5-carbonitrile | Calc'd 457.2 Found 457.1 | A-57 and B-9 | Daicel Chiralpak AD-3 | n/a |

TABLE 29-continued

| # | Structure | IUPAC Name | Exact Mass [M + H]+ | Intermediates Used | Chiral Column, If Applicable | Elution Order |
|---|---|---|---|---|---|---|
| 126 | 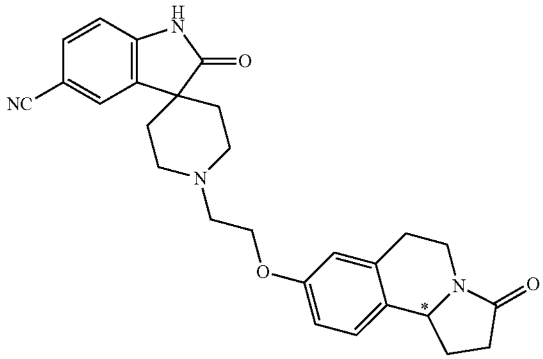 [SMILES: N#Cc1ccc2c(c1)C1(CCN(CCOc3ccc4c(c3)CCN3C(=O)CCC43)CC1)C(=O)N2] | (R) or (S)-2-oxo-1'-[2-({3-oxo-1H,2H,3H,5H,6H,10bH-pyrrolo[2,1-a]isoquinolin-8-yl}oxy)ethyl]-1,2-dihydrospiro[indole-3,4'-piperidine]-5-carbonitrile | Calc'd 457.2 Found 457.1 | A-57 and B-9 | Daicel Chiralpak AD-3 | n/a |
| 127 | 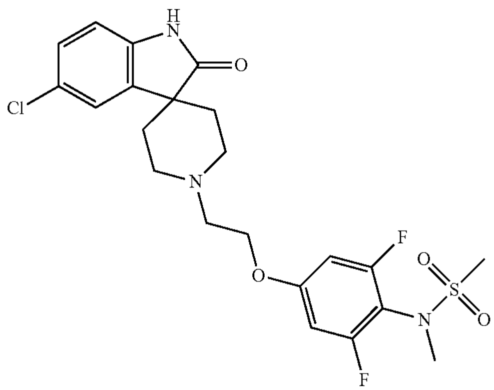 | N-[4-(2-{5-chloro-2-oxo-1,2-dihydrospiro[indole-3,4'-piperidin]-1'-yl}ethoxy)-2,6-difluorophenyl]-N-methylmethanesulfonamide | Calc'd 500.1 Found 500.2 | A-44 and B-4 | n/a | n/a |
| 128 | 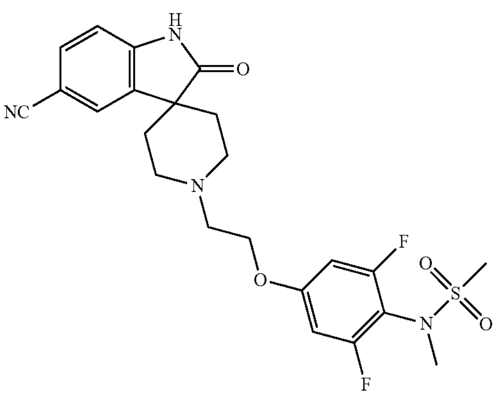 [SMILES: CN(c1c(F)cc(OCCN2CCC3(CC2)C(=O)Nc2ccc(C#N)cc23)cc1F)S(C)(=O)=O] | N-[4-(2-{5-cyano-2-oxo-1,2-dihydrospiro[indole-3,4'-piperidin]-1'-yl}ethoxy)-2,6-difluorophenyl]-N-methylmethanesulfonamide | Calc'd 491.1 Found 491.2 | A-44 and B-9 | n/a | n/a |
| 129 | 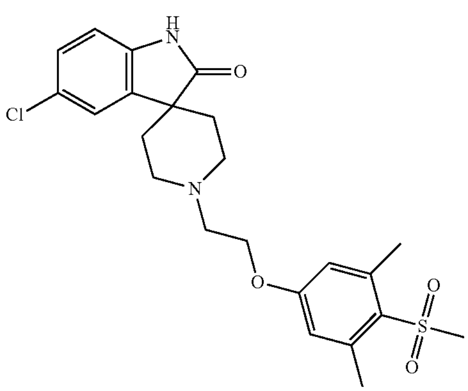 [SMILES: Cc1cc(OCCN2CCC3(CC2)C(=O)Nc2ccc(Cl)cc23)cc(C)c1S(C)(=O)=O] | 5-chloro-1'-[2-(4-methanesulfonyl-3,5-dimethyl-phenoxy)ethyl]-1,2-dihydrospiro[indole-3,4'-piperidin]-2-one | Calc'd 463.1 Found 463.1 | A-20 and B-4 | n/a | n/a |

TABLE 29-continued

| # | Structure | IUPAC Name | Exact Mass [M + H]+ | Intermediates Used | Chiral Column, If Applicable | Elution Order |
|---|---|---|---|---|---|---|
| 130 | 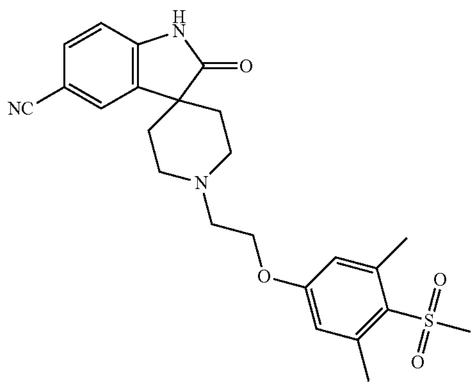 [SMILES: Cc1cc(OCCN2CCC3(CC2)C(=O)Nc2ccc(C#N)cc23)cc(C)c1S(C)(=O)=O] | 1'-[2-(4-methanesulfonyl-3,5-dimethyl-phenoxy)ethyl]-2-oxo-1,2-dihydrospiro[indole-3,4'-piperidine]-5-carbonitrile | Calc'd 454.2 Found 454.2 | A-20 and B-9 | n/a | n/a |
| 131 | 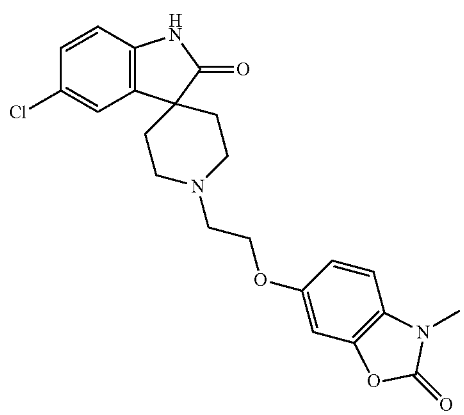 [SMILES: Cn1c(=O)oc2cc(OCCN3CCC4(CC3)C(=O)Nc3ccc(Cl)cc34)ccc21] | 5-chloro-1'-{2-[(3-methyl-2-oxo-2,3-dihydro-1,3-benzoxazol-6-yl)oxy]ethyl}-1,2-dihydrospiro[indole-3,4'-piperidin]-2-one | Calc'd 428.1 Found 428.1 | A-59 and B-4 | n/a | n/a |
| 132 | 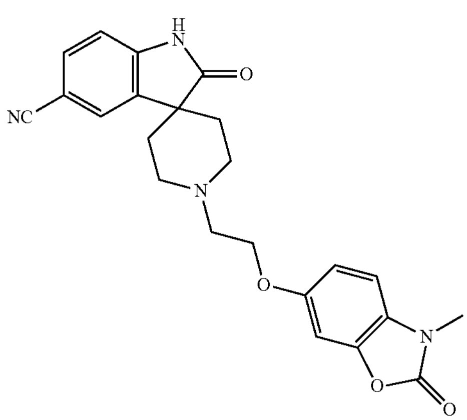 [SMILES: Cn1c(=O)oc2cc(OCCN3CCC4(CC3)C(=O)Nc3ccc(C#N)cc34)ccc21] | 1'-{2-[(3-methyl-2-oxo-2,3-dihydro-1,3-benzoxazol-6-yl)oxy]ethyl}-2-oxo-1,2-dihydrospiro[indole-3,4'-piperidine]-5-carbonitrile | Calc'd 419.2 Found 419.2 | A-59 and B-9 | n/a | n/a |

TABLE 29-continued

| # | Structure | IUPAC Name | Exact Mass [M + H]+ | Intermediates Used | Chiral Column, If Applicable | Elution Order |
|---|---|---|---|---|---|---|
| 133 | 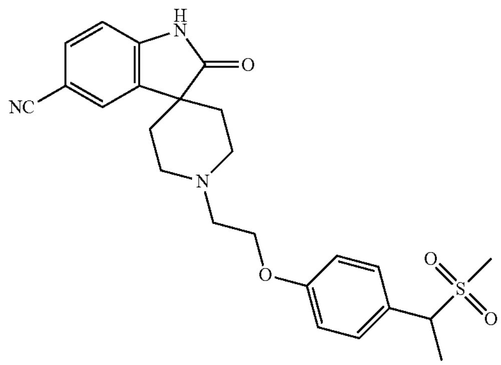 [SMILES: CC(c1ccc(OCCN2CCC3(CC2)C(=O)Nc2ccc(C#N)cc23)cc1)S(C)(=O)=O] | 1'-{2-[4-(1-methanesulfonyl-ethyl)phenoxy]ethyl}-2-oxo-1,2-dihydrospiro[indole-3,4'-piperidine]-5-carbonitrile | Calc'd 454.2 Found 454.2 | A-31 and B-9 | n/a | n/a |
| 134 | 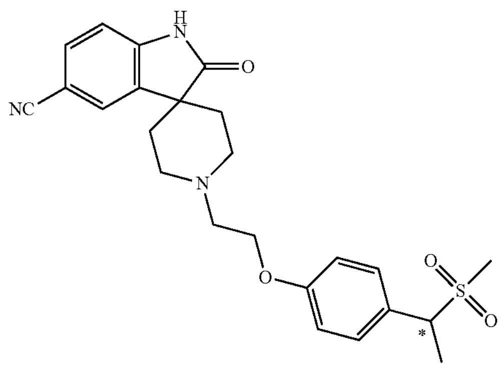 [SMILES: CC(c1ccc(OCCN2CCC3(CC2)C(=O)Nc2ccc(C#N)cc23)cc1)S(C)(=O)=O] | (S) or (R)-1'-{2-[4-(1-methanesulfonyl-ethyl)phenoxy]ethyl}-2-oxo-1,2-dihydrospiro[indole-3,4'-piperidine]-5-carbonitrile | Calc'd 454.2 Found 454.2 | A-31 and B-9 | Daicel Chiralpak OD-3 | First |
| 135 | 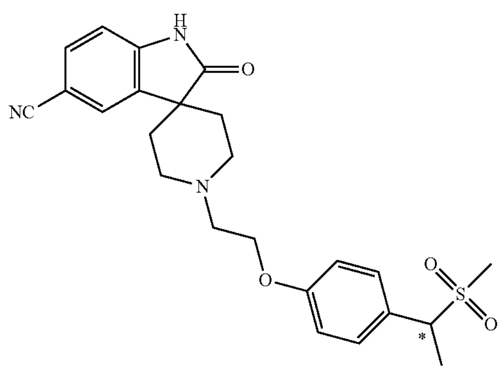 [SMILES: CC(c1ccc(OCCN2CCC3(CC2)C(=O)Nc2ccc(C#N)cc23)cc1)S(C)(=O)=O] | (R) or (S)-1'-{2-[4-(1-methanesulfonyl-ethyl)phenoxy]ethyl}-2-oxo-1,2-dihydrospiro[indole-3,4'-piperidine]-5-carbonitrile | Calc'd 454.2 Found 454.2 | A-31 and B-9 | Daicel Chiralpak OD-3 | Second |
| 136 | 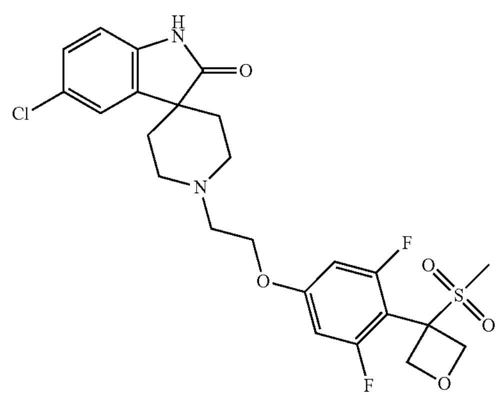 [SMILES: CS(=O)(=O)C1(c2c(F)cc(OCCN3CCC4(CC3)C(=O)Nc3ccc(Cl)cc34)cc2F)COC1] | 5-chloro-1'-{2-[3,5-difluoro-4-(3-methanesulfonyl-oxetan-3-yl)phenoxy]ethyl}-1,2-dihydrospiro[indole-3,4'-piperidin]-2-one | Calc'd 527.1 Found 527.2 | A-32 and B-4 | n/a | n/a |

TABLE 29-continued

| # | Structure | IUPAC Name | Exact Mass [M + H]+ | Intermediates Used | Chiral Column, If Applicable | Elution Order |
|---|---|---|---|---|---|---|
| 137 | 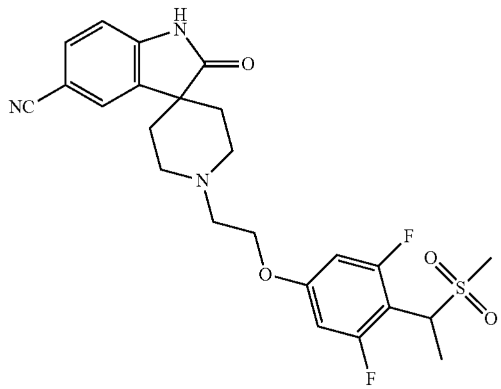 | 1'-{2-[3,5-difluoro-4-(1-methanesulfonyl-ethyl)phenoxy]ethyl}-2-oxo-1,2-dihydrospiro[indole-3,4'-piperidine]-5-carbonitrile | Calc'd 490.2 Found 490.2 | A-30 and B-9 | n/a | n/a |
| 138 | 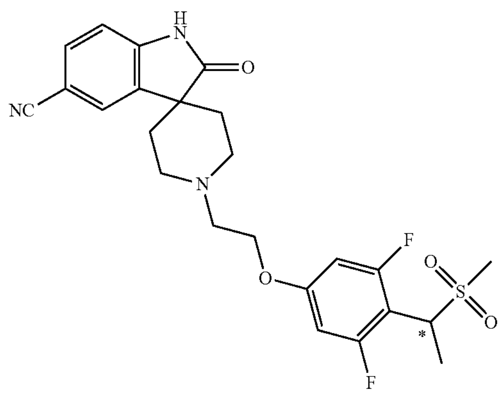 | (S) or (R)-1'-{2-[3,5-difluoro-4-(1-methanesulfonyl-ethyl)phenoxy]ethyl}-2-oxo-1,2-dihydrospiro[indole-3,4'-piperidine]-5-carbonitrile | Calc'd 490.2 Found 490.2 | A-30 and B-9 | Daicel Chiralpak OD-3 | First |
| 139 | 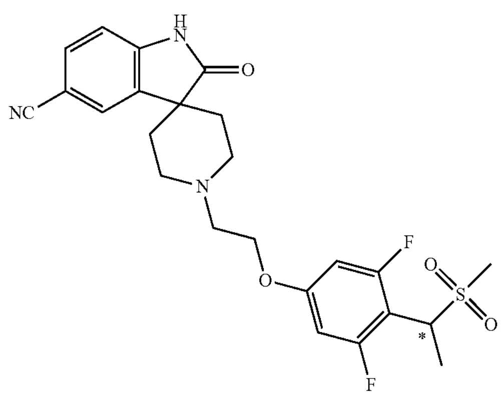 [SMILES: CC(c1c(F)cc(OCCN2CCC3(CC2)C(=O)Nc2ccc(C#N)cc23)cc1F)S(C)(=O)=O] | (R) or (S)-1'-{2-[3,5-difluoro-4-(1-methanesulfonyl-ethyl)phenoxy]ethyl}-2-oxo-1,2-dihydrospiro[indole-3,4'-piperidine]-5-carbonitrile | Calc'd 490.2 Found 490.2 | A-30 and B-9 | Daicel Chiralpak OD-3 | Second |
| 140 | 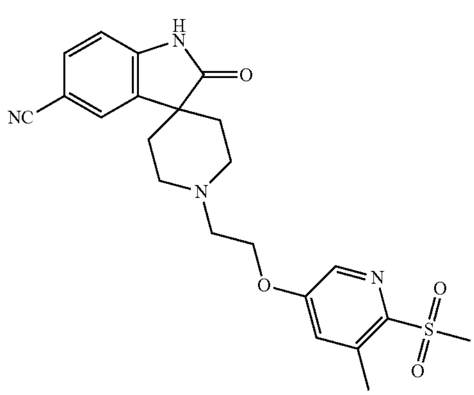 [SMILES: Cc1cc(OCCN2CCC3(CC2)C(=O)Nc2ccc(C#N)cc23)cnc1S(C)(=O)=O] | 1'-{2-[(6-methanesulfonyl-5-methylpyridin-3-yl)oxy]ethyl}-2-oxo-1,2-dihydrospiro[indole-3,4'-piperidine]-5-carbonitrile | Calc'd 441.2 Found 441.1 | A-21 and B-9 | n/a | n/a |

TABLE 29-continued

| # | Structure | IUPAC Name | Exact Mass [M + H]+ | Intermediates Used | Chiral Column, If Applicable | Elution Order |
|---|---|---|---|---|---|---|
| 141 | 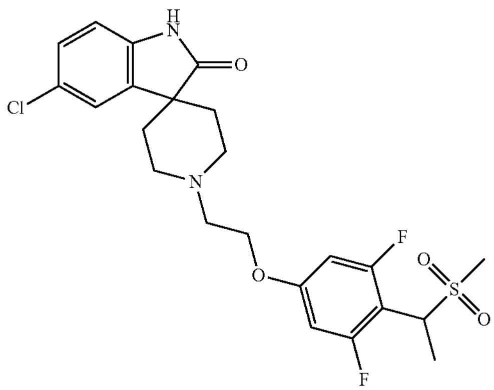 [SMILES: CC(c1c(F)cc(OCCN2CCC3(CC2)C(=O)Nc2ccc(Cl)cc23)cc1F)S(C)(=O)=O] | 5-chloro-1'-{2-[3,5-difluoro-4-(1-methanesulfonyl-ethyl)phenoxy]ethyl}-1,2-dihydrospiro[indole-3,4'-piperidin]-2-one | Calc'd 499.1 Found 499.2 | A-30 and B-4 | n/a | n/a |
| 142 | 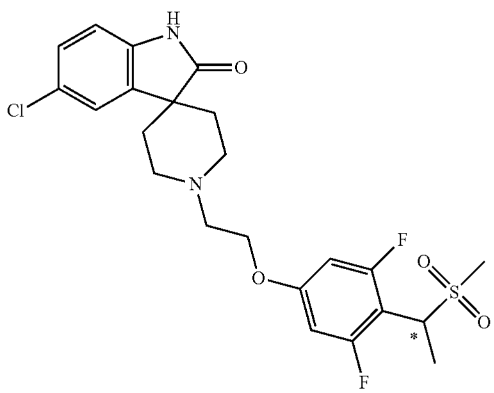 [SMILES: CC(c1c(F)cc(OCCN2CCC3(CC2)C(=O)Nc2ccc(Cl)cc23)cc1F)S(C)(=O)=O] | (S) or (R)-5-chloro-1'-{2-[3,5-difluoro-4-(1-methanesulfonyl-ethyl)phenoxy]ethyl}-1,2-dihydrospiro[indole-3,4'-piperidin]-2-one | Calc'd 499.1 Found 499.2 | A-30 and B-4 | Daicel Chiralpak OD-3 | First |
| 143 | 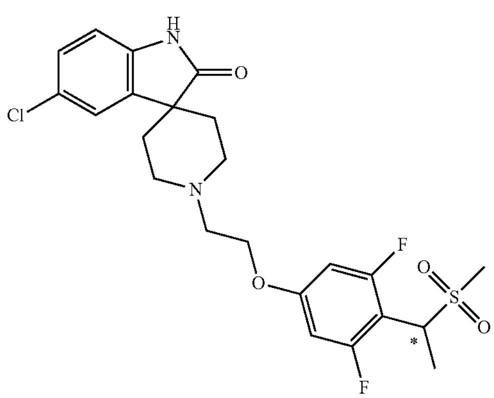 [SMILES: CC(c1c(F)cc(OCCN2CCC3(CC2)C(=O)Nc2ccc(Cl)cc23)cc1F)S(C)(=O)=O] | (R) or (S)-5-chloro-1'-{2-[3,5-difluoro-4-(1-methanesulfonyl-ethyl)phenoxy]ethyl}-1,2-dihydrospiro[indole-3,4'-piperidin]-2-one | Calc'd 499.1 Found 499.2 | A-30 and B-4 | Daicel Chiralpak OD-3 | Second |

TABLE 29-continued

| # | Structure | IUPAC Name | Exact Mass [M + H]⁺ | Intermediates Used | Chiral Column, If Applicable | Elution Order |
|---|---|---|---|---|---|---|
| 144 | 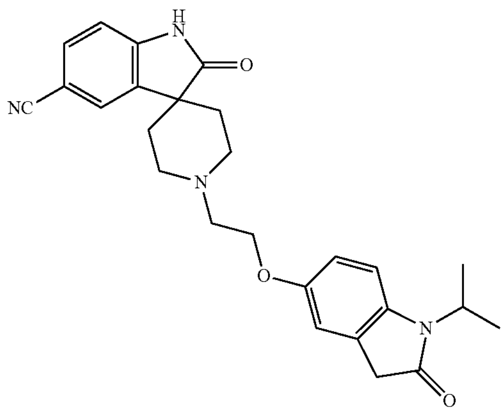 [SMILES: CC(C)N1C(=O)Cc2cc(OCCN3CCC4(CC3)C(=O)Nc3ccc(C#N)cc34)ccc21] | 2-oxo-1'-(2-{[2-oxo-1-(propan-2-yl)-2,3-dihydro-1H-indol-5-yl]oxy}ethyl)-1,2-dihydrospiro[indole-3,4'-piperidine]-5-carbonitrile | Calc'd 445.2 Found 445.3 | A-14 and B-9 | n/a | n/a |
| 145 | 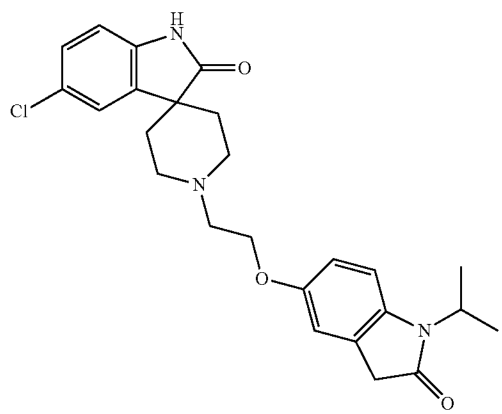 [SMILES: CC(C)N1C(=O)Cc2cc(OCCN3CCC4(CC3)C(=O)Nc3ccc(Cl)cc34)ccc21] | 5-chloro-1'-(2-{[2-oxo-1-(propan-2-yl)-2,3-dihydro-1H-indol-5-yl]oxy}ethyl)-1,2-dihydrospiro[indole-3,4'-piperidin]-2-one | Calc'd 454.2 Found 454.2 | A-14 and B-4 | n/a | n/a |
| 146 | 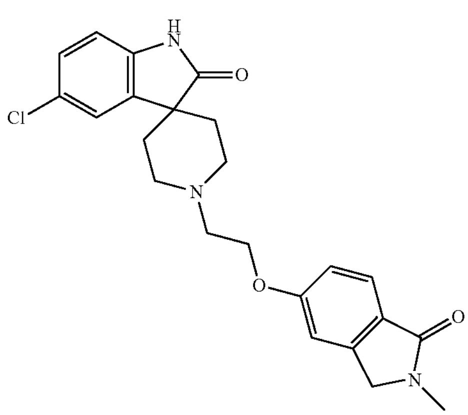 [SMILES: CN1Cc2cc(OCCN3CCC4(CC3)C(=O)Nc3ccc(Cl)cc34)ccc2C1=O] | 5-chloro-1'-{2-[(2-methyl-1-oxo-2,3-dihydro-1H-isoindol-5-yl)oxy]ethyl}-1,2-dihydrospiro[indole-3,4'-piperidin]-2-one | Calc'd 426.2 Found 426.1 | A-53 and B-4 | n/a | n/a |

TABLE 29-continued

| # | Structure | IUPAC Name | Exact Mass [M + H]+ | Intermediates Used | Chiral Column, If Applicable | Elution Order |
|---|---|---|---|---|---|---|
| 147 | 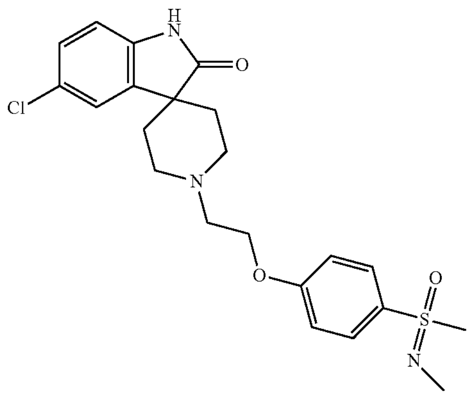 [SMILES: CN=S(C)(=O)c1ccc(OCCN2CCC3(CC2)C(=O)Nc2ccc(Cl)cc23)cc1] | 5-chloro-1'-(2-{4-[methyl(methylimino)oxo-λ⁶-sulfanyl]phenoxy}ethyl)-1,2-dihydrospiro[indole-3,4'-piperidin]-2-one | Calc'd 448.1 Found 448.0 | A-45 and B-4 | n/a | n/a |
| 148 | 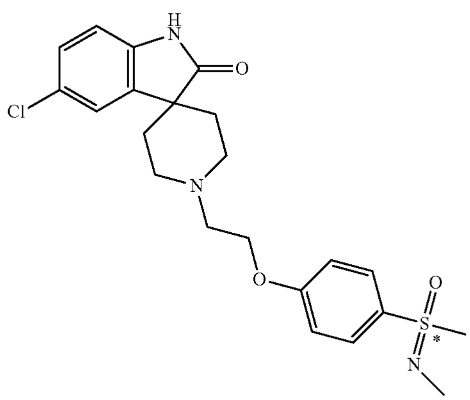 [SMILES: CN=S(C)(=O)c1ccc(OCCN2CCC3(CC2)C(=O)Nc2ccc(Cl)cc23)cc1] | (S) or (R)-5-chloro-1'-(2-{4-[methyl(methylimino)oxo-λ⁶-sulfanyl]phenoxy}ethyl)-1,2-dihydrospiro[indole-3,4'-piperidin]-2-one | Calc'd 448.1 Found 448.0 | A-45 and B-4 | Daicel Chiralpak ID-3 | First |
| 149 | 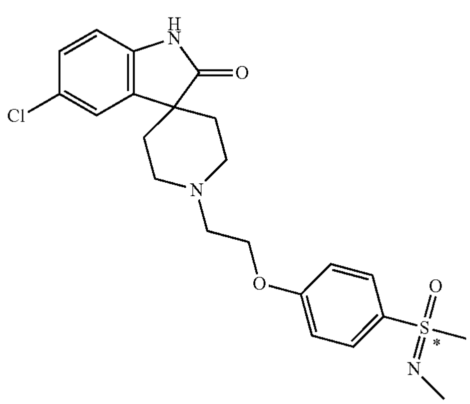 [SMILES: CN=S(C)(=O)c1ccc(OCCN2CCC3(CC2)C(=O)Nc2ccc(Cl)cc23)cc1] | (R) or (S)-5-chloro-1'-(2-{4-[methyl(methylimino)oxo-λ⁶-sulfanyl]phenoxy}ethyl)-1,2-dihydrospiro[indole-3,4'-piperidin]-2-one | Calc'd 448.1 Found 448.0 | A-45 and B-4 | Daicel Chiralpak ID-3 | Second |

TABLE 29-continued

| # | Structure | IUPAC Name | Exact Mass [M + H]+ | Intermediates Used | Chiral Column, If Applicable | Elution Order |
|---|---|---|---|---|---|---|
| 150 | 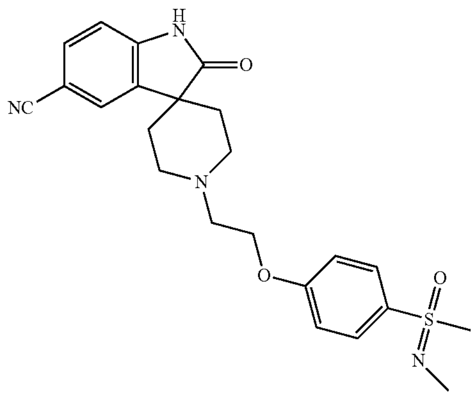 [SMILES: CN=S(C)(=O)c1ccc(OCCN2CCC3(CC2)C(=O)Nc2ccc(C#N)cc23)cc1] | 1'-(2-{4-[methyl(methyl-imino)oxo-$\lambda^6$-sulfanyl]phenoxy}ethyl)-2-oxo-1,2-dihydrospiro[indole-3,4'-piperidine]-5-carbonitrile | Calc'd 439.2 Found 439.0 | A-45 and B-9 | n/a | n/a |
| 151 | 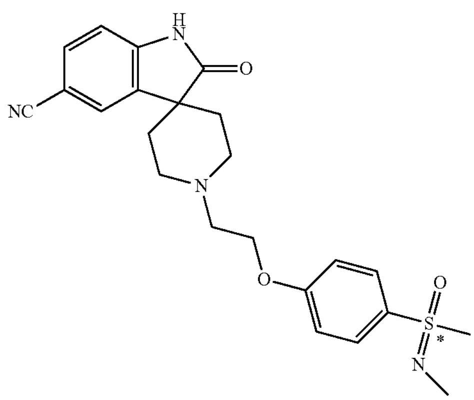 [SMILES: CN=S(C)(=O)c1ccc(OCCN2CCC3(CC2)C(=O)Nc2ccc(C#N)cc23)cc1] | (S) or (R)-1'-(2-{4-[methyl(methyl-imino)oxo-$\lambda^6$-sulfanyl]phenoxy}ethyl)-2-oxo-1,2-dihydrospiro[indole-3,4'-piperidine]-5-carbonitrile | Calc'd 439.2 Found 439.0 | A-45 and B-9 | Daicel Chiralpak ID-3 | Second |
| 152 | 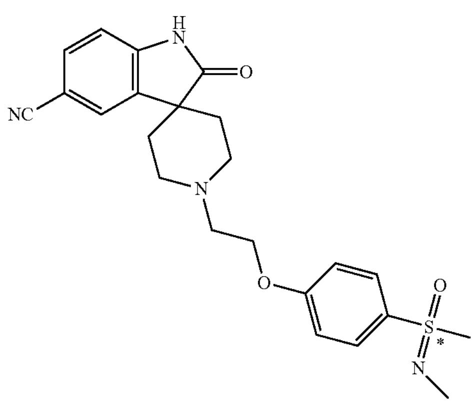 [SMILES: CN=S(C)(=O)c1ccc(OCCN2CCC3(CC2)C(=O)Nc2ccc(C#N)cc23)cc1] | (R) or (S)-1'-(2-{4-[methyl(methyl-imino)oxo-$\lambda^6$-sulfanyl]phenoxy}ethyl)-2-oxo-1,2-dihydrospiro[indole-3,4'-piperidine]-5-carbonitrile | Calc'd 439.2 Found 439.0 | A-45 and B-9 | Daicel Chiralpak ID-3 | First |

| # | Structure | IUPAC Name | Exact Mass [M + H]+ | Intermediates Used | Chiral Column, If Applicable | Elution Order |
|---|---|---|---|---|---|---|
| 153 | 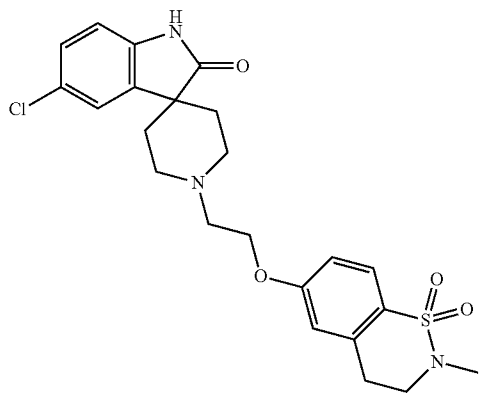 [SMILES: CN1CCc2cc(OCCN3CCC4(CC3)C(=O)Nc3ccc(Cl)cc34)ccc2S1(=O)=O] | 6-(2-{5-chloro-2-oxo-1,2-dihydrospiro[indole-3,4'-piperidin]-1'-yl}ethoxy)-2-methyl-3,4-dihydro-2H-1λ⁶,2-benzothiazine-1,1-dione | Calc'd 476.1 Found 476.1 | A-49 and B-4 | n/a | n/a |
| 154 | 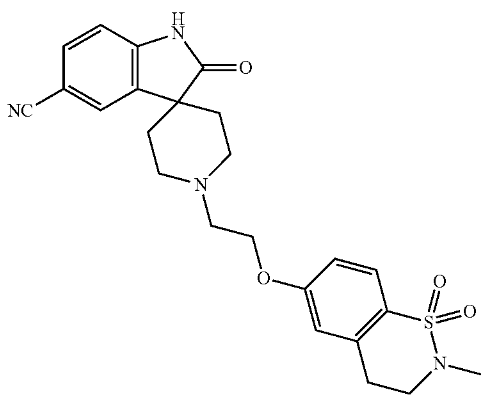 [SMILES: CN1CCc2cc(OCCN3CCC4(CC3)C(=O)Nc3ccc(C#N)cc34)ccc2S1(=O)=O] | 1'-{2-[(2-methyl-1,1-dioxo-3,4-dihydro-2H-1λ⁶,2-benzothiazin-6-yl)oxy]ethyl}-2-oxo-1,2-dihydrospiro[indole-3,4'-piperidine]-5-carbonitrile | Calc'd 467.2 Found 467.2 | A-49 and B-9 | n/a | n/a |
| 155 | 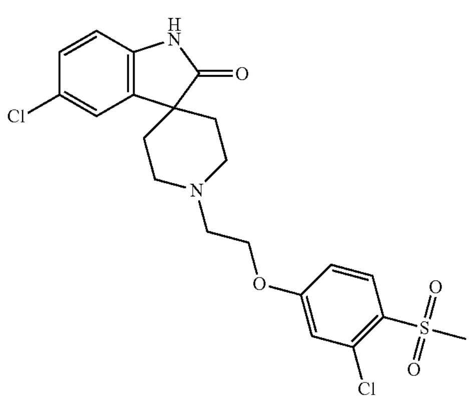 [SMILES: CS(=O)(=O)c1ccc(OCCN2CCC3(CC2)C(=O)Nc2ccc(Cl)cc23)cc1Cl] | 5-chloro-1'-[2-(3-chloro-4-methanesulfonyl-phenoxy)ethyl]-1,2-dihydrospiro[indole-3,4'-piperidin]-2-one | Calc'd 469.1 Found 469.2 | A-19 and B-4 | n/a | n/a |

TABLE 29-continued

| # | Structure | IUPAC Name | Exact Mass [M + H]+ | Intermediates Used | Chiral Column, If Applicable | Elution Order |
|---|---|---|---|---|---|---|
| 156 | 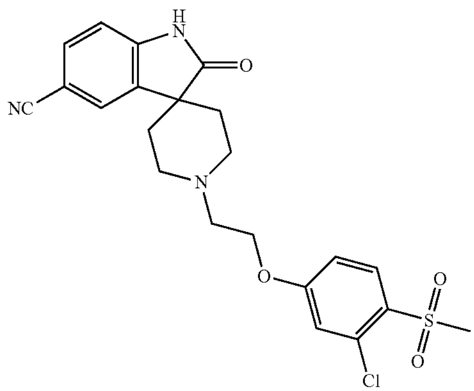 [SMILES: CS(=O)(=O)c1ccc(OCCN2CCC3(CC2)C(=O)Nc2ccc(C#N)cc23)cc1Cl] | 1'-[2-(3-chloro-4-methanesulfonyl-phenoxy)ethyl]-2-oxo-1,2-dihydrospiro[indole-3,4'-piperidine]-5-carbonitrile | Calc'd 460.1 Found 460.2 | A-19 and B-9 | n/a | n/a |
| 157 | 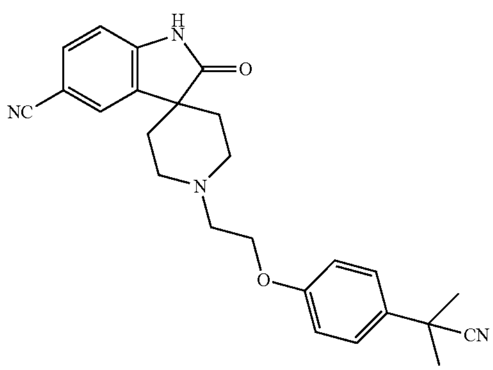 [SMILES: CC(C)(C#N)c1ccc(OCCN2CCC3(CC2)C(=O)Nc2ccc(C#N)cc23)cc1] | 1'-{2-[4-(1-cyano-1-methyl-ethyl)phenoxy]ethyl}-2-oxo-1,2-dihydrospiro[indole-3,4'-piperidine]-5-carbonitrile | Calc'd 415.2 Found 415.2 | A-47 and B-9 | n/a | n/a |
| 158 | 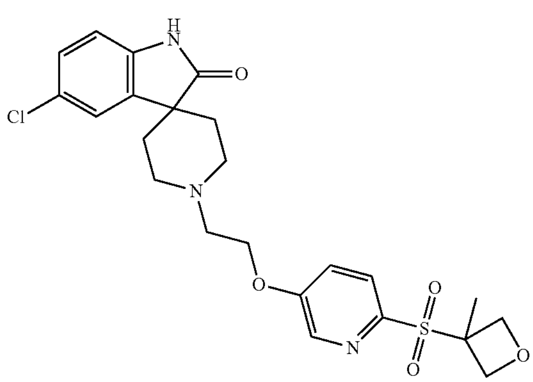 [SMILES: CC1(S(=O)(=O)c2ccc(OCCN3CCC4(CC3)C(=O)Nc3ccc(Cl)cc34)cn2)COC1] | 5-chloro-1'-[2-({6-[(3-methyloxetan-3-yl)sulfonyl]pyridin-3-yl}oxy)ethyl]-1,2-dihydrospiro[indole-3,4'-piperidin]-2-one | Calc'd 492.1 Found 492.1 | A-26 and B-4 | n/a | n/a |

TABLE 29-continued

| # | Structure | IUPAC Name | Exact Mass [M + H]+ | Intermediates Used | Chiral Column, If Applicable | Elution Order |
|---|-----------|------------|---------------------|--------------------|-----------------------------|---------------|
| 159 | 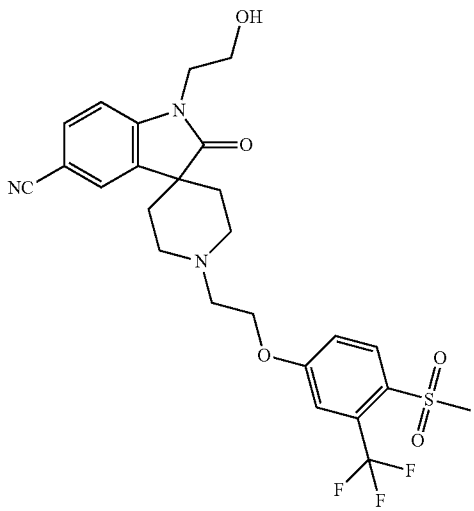 [SMILES: CS(=O)(=O)c1ccc(OCCN2CCC3(CC2)C(=O)N(CCO)c2ccc(C#N)cc23)cc1C(F)(F)F] | 1-(2-hydroxyethyl)-1'-{2-[4-methanesulfonyl-3-(trifluoromethyl)phenoxy]ethyl}-2-oxo-1,2-dihydrospiro[indole-3,4'-piperidine]-5-carbonitrile | Calc'd 538.2 Found 538.2 | A-17 and B-12 | n/a | n/a |
| 160 | 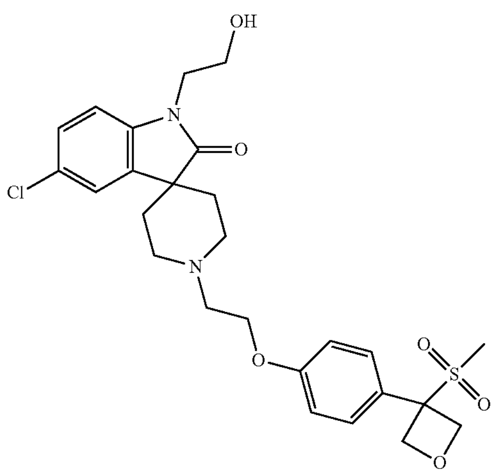 [SMILES: CS(=O)(=O)C1(c2ccc(OCCN3CCC4(CC3)C(=O)N(CCO)c3ccc(Cl)cc34)cc2)COC1] | 5-chloro-1-(2-hydroxyethyl)-1'-{2-[4-(3-methanesulfonyloxetan-3-yl)phenoxy]ethyl}-1,2-dihydrospiro[indole-3,4'-piperidin]-2-one | Calc'd 535.2 Found 535.2 | A-33 and B-11 | n/a | n/a |
| 161 | 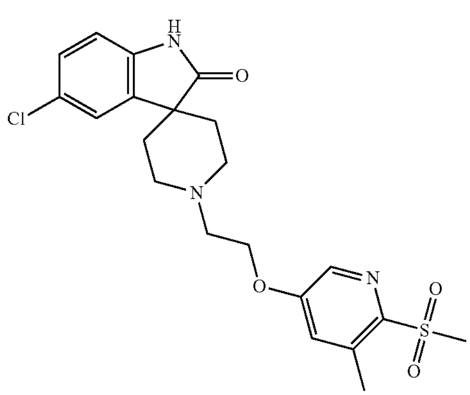 [SMILES: Cc1cc(OCCN2CCC3(CC2)C(=O)Nc2ccc(Cl)cc23)cnc1S(C)(=O)=O] | 5-chloro-1'-{2-[(6-methanesulfonyl-5-methylpyridin-3-yl)oxy]ethyl}-1,2-dihydrospiro[indole-3,4'-piperidin]-2-one | Calc'd 450.1 Found 450.1 | A-21 and B-4 | n/a | n/a |

TABLE 29-continued

| # | Structure | IUPAC Name | Exact Mass [M + H]+ | Intermediates Used | Chiral Column, If Applicable | Elution Order |
|---|---|---|---|---|---|---|
| 162 | 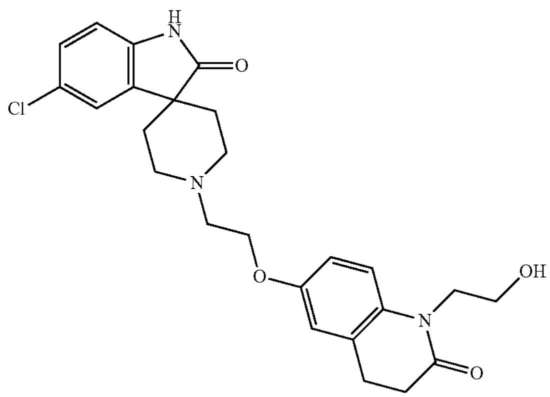 [SMILES: O=C1CCc2cc(OCCN3CCC4(CC3)C(=O)Nc3ccc(Cl)cc34)ccc2N1CCO] | 5-chloro-1'-(2-{[1-(2-hydroxyethyl)-2-oxo-1,2,3,4-tetrahydroquinolin-6-yl]oxy}ethyl)-1,2-dihydrospiro[indole-3,4'-piperidin]-2-one | Calc'd 470.2 Found 470.1 | A-65 and B-4 | n/a | n/a |
| 163 | 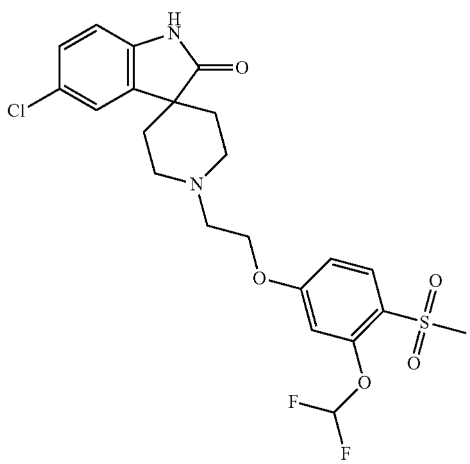 [SMILES: CS(=O)(=O)c1ccc(OCCN2CCC3(CC2)C(=O)Nc2ccc(Cl)cc23)cc1OC(F)F] | 5-chloro-1'-{2-[3-(difluoromethoxy)-4-methanesulfonyl-phenoxy]ethyl}-1,2-dihydrospiro[indole-3,4'-piperidin]-2-one | Calc'd 501.1 Found 501.2 | A-23 and B-4 | n/a | n/a |
| 164 | 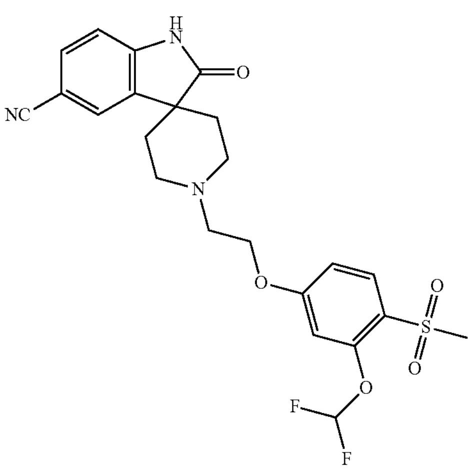 [SMILES: CS(=O)(=O)c1ccc(OCCN2CCC3(CC2)C(=O)Nc2ccc(C#N)cc23)cc1OC(F)F] | 1'-{2-[3-(difluoromethoxy)-4-methanesulfonyl-phenoxy]ethyl}-2-oxo-1,2-dihydrospiro[indole-3,4'-piperidine]-5-carbonitrile | Calc'd 492.1 Found 492.2 | A-23 and B-9 | n/a | n/a |

TABLE 29-continued

| # | Structure | IUPAC Name | Exact Mass [M + H]+ | Intermediates Used | Chiral Column, If Applicable | Elution Order |
|---|---|---|---|---|---|---|
| 165 | 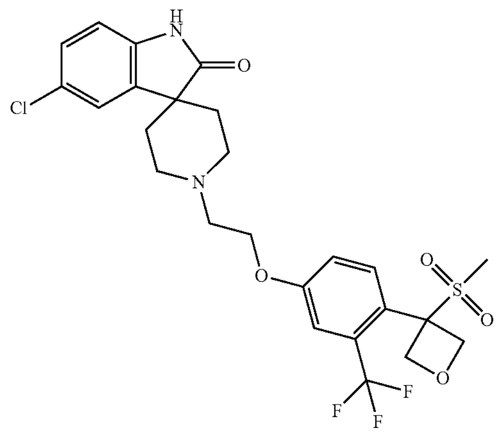 [SMILES: CS(=O)(=O)C1(c2ccc(OCCN3CCC4(CC3)C(=O)Nc3ccc(Cl)cc34)cc2C(F)(F)F)COC1] | 5-chloro-1'-{2-[4-(3-methanesulfonyl-oxetan-3-yl)-3-(trifluoro-methyl)phenoxy]ethyl}-1,2-dihydrospiro[indole-3,4'-piperidin]-2-one | Calc'd 559.1 Found 559.2 | A-34 and B-4 | n/a | n/a |
| 166 | 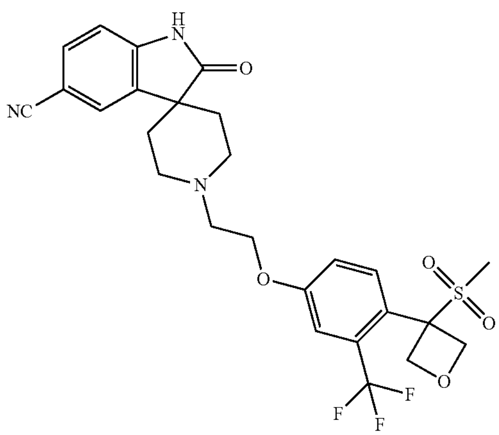 [SMILES: CS(=O)(=O)C1(c2ccc(OCCN3CCC4(CC3)C(=O)Nc3ccc(C#N)cc34)cc2C(F)(F)F)COC1] | 1'-{2-[4-(3-methanesulfonyl-oxetan-3-yl)-3-(trifluoro-methyl)phenoxy]ethyl}-2-oxo-1,2-dihydrospiro[indole-3,4'-piperidine]-5-carbonitrile | Calc'd 550.2 Found 550.2 | A-34 and B-9 | n/a | n/a |
| 167 | 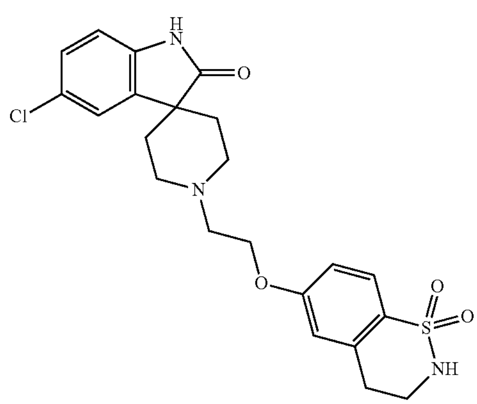 [SMILES: O=C1Nc2ccc(Cl)cc2C12CCN(CCOc1ccc3c(c1)CCNS3(=O)=O)CC2] | 6-(2-{5-chloro-2-oxo-1,2-dihydrospiro[indole-3,4'-piperidin]-1'-yl}ethoxy)-3,4-dihydro-2H-1λ$^6$,2-benzothiazine-1,1-dione | Calc'd 462.1 Found 462.0 | A-50 and B-4 | n/a | n/a |

TABLE 29-continued

| # | Structure | IUPAC Name | Exact Mass [M + H]+ | Intermediates Used | Chiral Column, If Applicable | Elution Order |
|---|---|---|---|---|---|---|
| 168 | 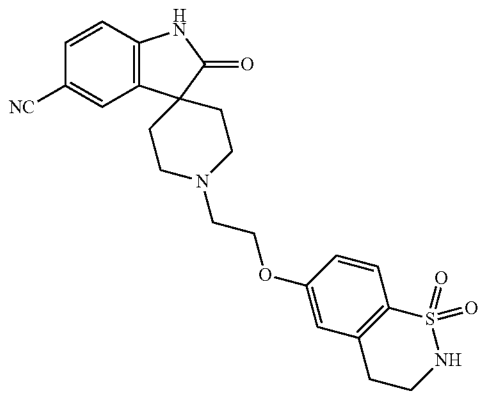 [SMILES: N#Cc1ccc2c(c1)C1(CCN(CCOc3ccc4c(c3)CCNS4(=O)=O)CC1)C(=O)N2] | 1'-{2-[(1,1-dioxo-3,4-dihydro-2H-1λ⁶,2-benzothiazin-6-yl)oxy]ethyl}-2-oxo-1,2-dihydrospiro[indole-3,4'-piperidine]-5-carbonitrile | Calc'd 453.2 Found 453.2 | A-50 and B-9 | n/a | n/a |
| 169 | 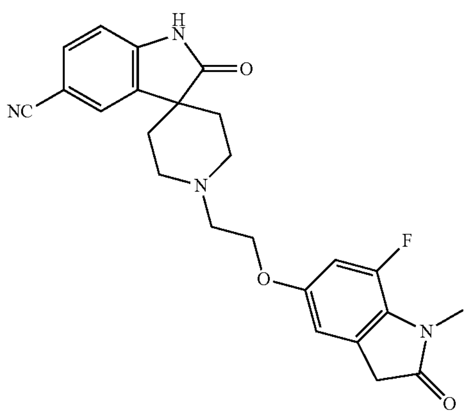 [SMILES: CN1C(=O)Cc2cc(OCCN3CCC4(CC3)C(=O)Nc3ccc(C#N)cc34)cc(F)c21] | 1'-{2-[(7-fluoro-1-methyl-2-oxo-2,3-dihydro-1H-indol-5-yl)oxy]ethyl}-2-oxo-1,2-dihydrospiro[indole-3,4'-piperidine]-5-carbonitrile | Calc'd 435.2 Found 435.1 | A-60 and B-9 | n/a | n/a |
| 170 | 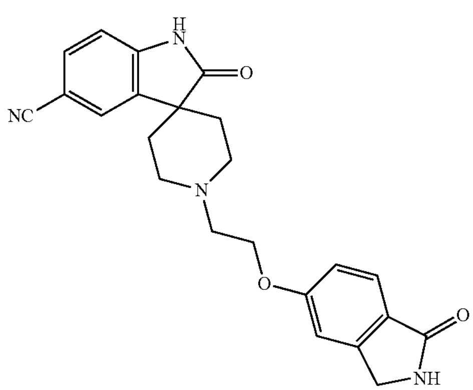 [SMILES: N#Cc1ccc2c(c1)C1(CCN(CCOc3ccc4c(c3)CNC4=O)CC1)C(=O)N2] | 2-oxo-1'-{2-[(1-oxo-2,3-dihydro-1H-isoindol-5-yl)oxy]ethyl}-1,2-dihydrospiro[indole-3,4'-piperidine]-5-carbonitrile | Calc'd 403.2 Found 403.3 | A-61 and B-9 | n/a | n/a |

TABLE 29-continued

| # | Structure | IUPAC Name | Exact Mass [M + H]+ | Intermediates Used | Chiral Column, If Applicable | Elution Order |
|---|---|---|---|---|---|---|
| 171 | 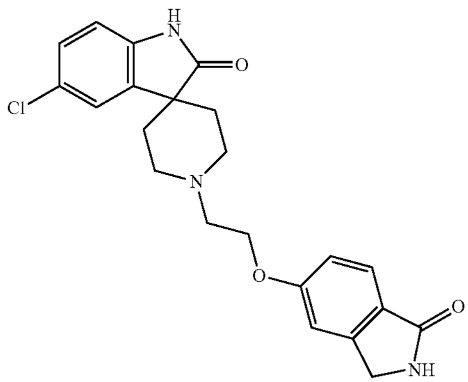 [SMILES: O=C1NCc2cc(OCCN3CCC4(CC3)C(=O)Nc3ccc(Cl)cc34)ccc21] | 5-chloro-1'-{2-[(1-oxo-2,3-dihydro-1H-isoindol-5-yl)oxy]ethyl}-1,2-dihydrospiro[indole-3,4'-piperidin]-2-one | Calc'd 412.1 Found 412.2 | A-61 and B-4 | n/a | n/a |
| 172 | 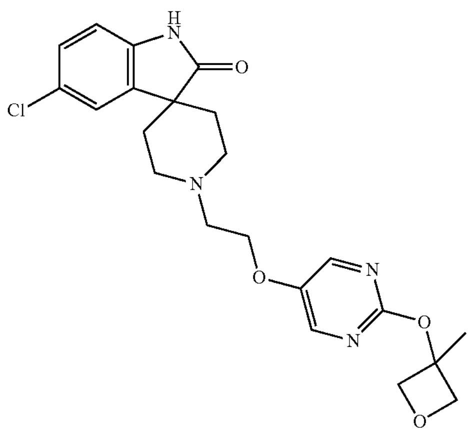 [SMILES: CC1(Oc2ncc(OCCN3CCC4(CC3)C(=O)Nc3ccc(Cl)cc34)cn2)COC1] | 5-chloro-1'-[2-({2-[(3-methyloxetan-3-yl)oxy]pyrimidin-5-yl}oxy)ethyl]-1,2-dihydrospiro[indole-3,4'-piperidin]-2-one | Calc'd 445.2 Found 445.2 | A-43 and B-4 | n/a | n/a |
| 173 | 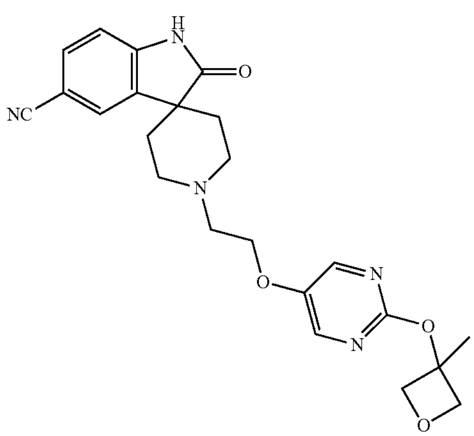 [SMILES: CC1(Oc2ncc(OCCN3CCC4(CC3)C(=O)Nc3ccc(C#N)cc34)cn2)COC1] | 1'-[2-({2-[(3-methyloxetan-3-yl)oxy]pyrimidin-5-yl}oxy)ethyl]-2-oxo-1,2-dihydrospiro[indole-3,4'-piperidine]-5-carbonitrile | Calc'd 436.2 Found 436.2 | A-43 and B-9 | n/a | n/a |

TABLE 29-continued

| # | Structure | IUPAC Name | Exact Mass [M + H]+ | Intermediates Used | Chiral Column, If Applicable | Elution Order |
|---|---|---|---|---|---|---|
| 174 | 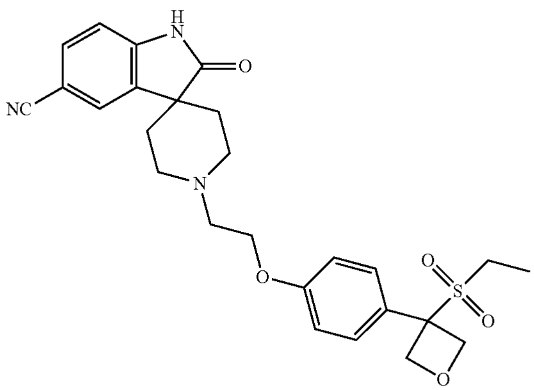 [SMILES: CCS(=O)(=O)C1(c2ccc(OCCN3CCC4(CC3)C(=O)Nc3ccc(C#N)cc34)cc2)COC1] | 1'-(2-{4-[3-(ethanesulfonyl)oxetan-3-yl]phenoxy}ethyl)-2-oxo-1,2-dihydrospiro[indole-3,4'-piperidine]-5-carbonitrile | Calc'd 496.2 Found 496.0 | A-37 and B-9 | n/a | n/a |
| 175 | 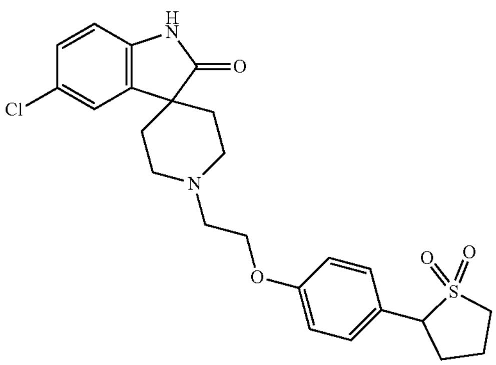 [SMILES: O=C1Nc2ccc(Cl)cc2C12CCN(CCOc1ccc(C3CCCS3(=O)=O)cc1)CC2] | 2-[4-(2-{5-chloro-2-oxo-1,2-dihydrospiro[indole-3,4'-piperidin]-1'-yl}ethoxy)phenyl]-1λ⁶-thiolane-1,1-dione | Calc'd 475.1 Found 475.2 | A-38 and B-4 | n/a | n/a |
| 176 | 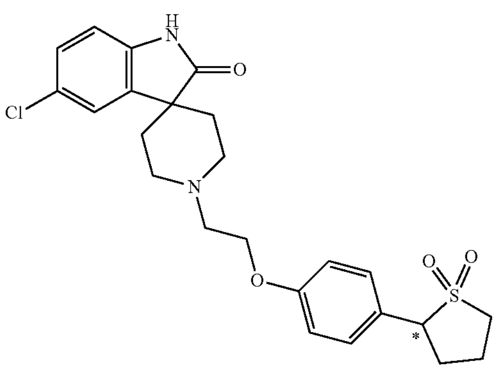 [SMILES: O=C1Nc2ccc(Cl)cc2C12CCN(CCOc1ccc(C3CCCS3(=O)=O)cc1)CC2] | (S) or (R)-2-[4-(2-{5-chloro-2-oxo-1,2-dihydrospiro[indole-3,4'-piperidin]-1'-yl}ethoxy)phenyl]-1λ⁶-thiolane-1,1-dione | Calc'd 475.1 Found 475.2 | A-38 and B-4 | Regis(S,S) Whelk-O1 | First |
| 177 | 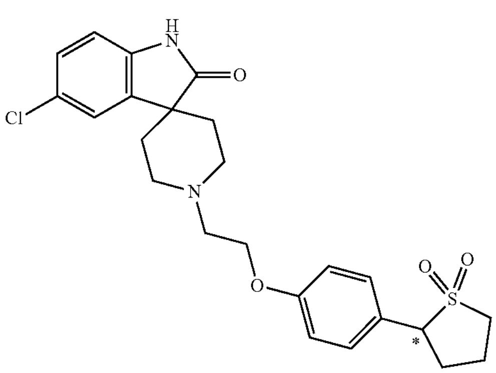 [SMILES: O=C1Nc2ccc(Cl)cc2C12CCN(CCOc1ccc(C3CCCS3(=O)=O)cc1)CC2] | (R) or (S)-2-[4-(2-{5-chloro-2-oxo-1,2-dihydrospiro[indole-3,4'-piperidin]-1'-yl}ethoxy)phenyl]-1λ⁶-thiolane-1,1-dione | Calc'd 475.1 Found 475.2 | A-38 and B-4 | Regis(S,S) Whelk-O1 | Second |

TABLE 29-continued

| # | Structure | IUPAC Name | Exact Mass [M + H]+ | Intermediates Used | Chiral Column, If Applicable | Elution Order |
|---|---|---|---|---|---|---|
| 178 | 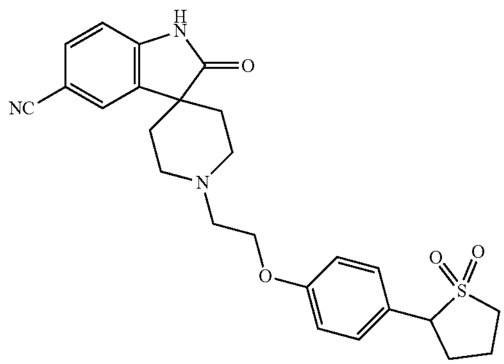 [SMILES: N#Cc1ccc2c(c1)C1(CCN(CCOc3ccc(C4CCCS4(=O)=O)cc3)CC1)C(=O)N2] | 1'-{2-[4-(1,1-dioxo-1λ⁶-thiolan-2-yl)phenoxy]ethyl}-2-oxo-1,2-dihydrospiro[indole-3,4'-piperidine]-5-carbonitrile | Calc'd 466.2 Found 466.2 | A-38 and B-9 | n/a | n/a |
| 179 | 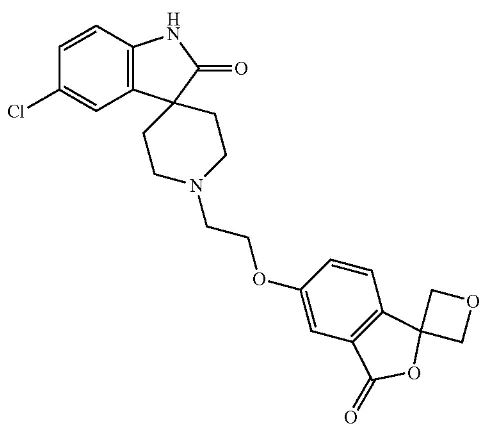 [SMILES: O=C1OC2(COC2)c2ccc(OCCN3CCC4(CC3)C(=O)Nc3ccc(Cl)cc34)cc21] | 5-chloro-1'-(2-{3-oxo-3H-spiro[2-benzofuran-1,3'-oxetan]-5-yloxy}ethyl)-1,2-dihydrospiro[indole-3,4'-piperidin]-2-one | Calc'd 455.1 Found 455.0 | A-38 and B-9 | n/a | n/a |
| 180 | 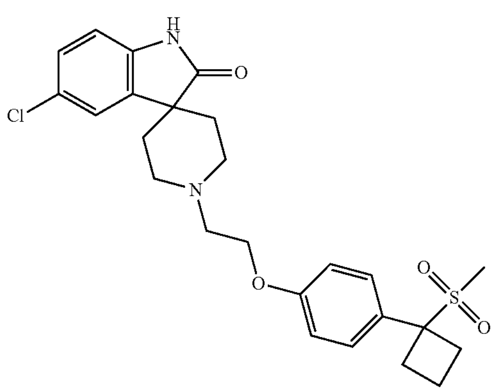 [SMILES: CS(=O)(=O)C1(c2ccc(OCCN3CCC4(CC3)C(=O)Nc3ccc(Cl)cc34)cc2)CCC1] | 5-chloro-1'-{2-[4-(1-methanesulfonylcyclobutyl)phenoxy]ethyl}-1,2-dihydrospiro[indole-3,4'-piperidin]-2-one | Calc'd 489.2 Found 489.1 | A-40 and B-4 | n/a | n/a |
| 181 | 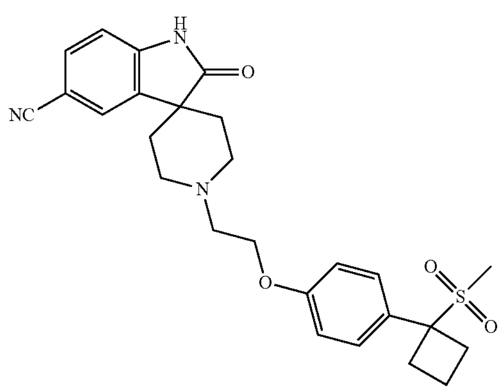 [SMILES: CS(=O)(=O)C1(c2ccc(OCCN3CCC4(CC3)C(=O)Nc3ccc(C#N)cc34)cc2)CCC1] | 1'-{2-[4-(1-methanesulfonylcyclobutyl)phenoxy]ethyl}-2-oxo-1,2-dihydrospiro[indole-3,4'-piperidine]-5-carbonitrile | Calc'd 480.2 Found 480.2 | A-40 and B-9 | n/a | n/a |

TABLE 29-continued

| # | Structure | IUPAC Name | Exact Mass [M + H]+ | Intermediates Used | Chiral Column, If Applicable | Elution Order |
|---|---|---|---|---|---|---|
| 182 | 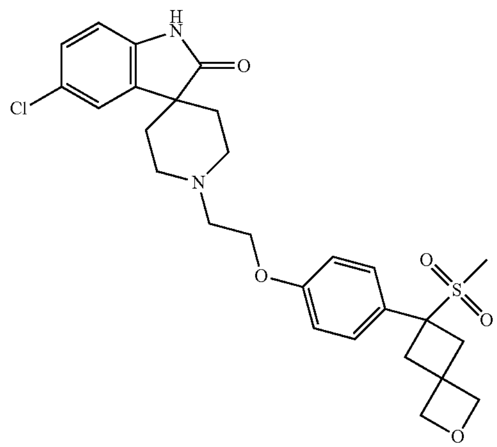 [SMILES: CS(=O)(=O)C1(c2ccc(OCCN3CCC4(CC3)C(=O)Nc3ccc(Cl)cc34)cc2)CC2(COC2)C1] | 5-chloro-1'-[2-(4-{6-methanesulfonyl-2-oxaspiro[3.3]heptan-6-yl}phenoxy)ethyl]-1,2-dihydrospiro[indole-3,4'-piperidin]-2-one | Calc'd 531.2 Found 531.1 | A-42 and B-4 | n/a | n/a |
| 183 | 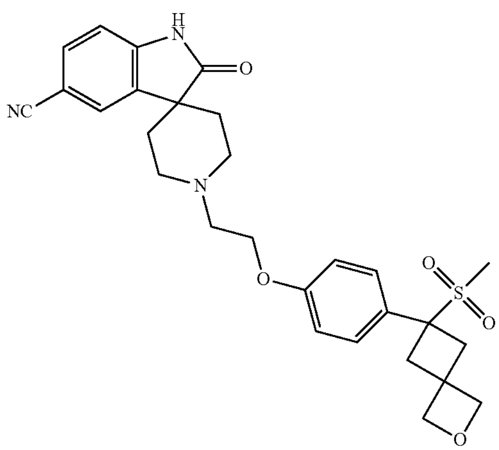 [SMILES: CS(=O)(=O)C1(c2ccc(OCCN3CCC4(CC3)C(=O)Nc3ccc(C#N)cc34)cc2)CC2(COC2)C1] | 1'-[2-(4-{6-methanesulfonyl-2-oxaspiro[3.3]heptan-6-yl}phenoxy)ethyl]-2-oxo-1,2-dihydrospiro[indole-3,4'-piperidine]-5-carbonitrile | Calc'd 522.2 Found 522.1 | A-42 and B-9 | n/a | n/a |
| 184 | 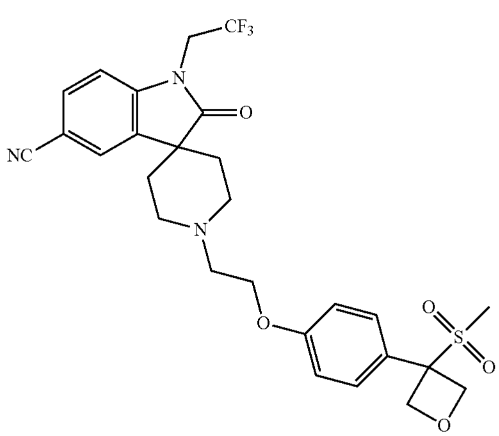 [SMILES: CS(=O)(=O)C1(c2ccc(OCCN3CCC4(CC3)C(=O)N(CC(F)(F)F)c3ccc(C#N)cc34)cc2)COC1] | 1'-{2-[4-(3-methanesulfonyl-oxetan-3-yl)phenoxy]ethyl}-2-oxo-1-(2,2,2-trifluoroethyl)-1,2-dihydrospiro[indole-3,4'-piperidine]-5-carbonitrile | Calc'd 564.2 Found 564.2 | A-33 and B-13 | n/a | n/a |

TABLE 29-continued

| # | Structure | IUPAC Name | Exact Mass [M + H]+ | Intermediates Used | Chiral Column, If Applicable | Elution Order |
|---|---|---|---|---|---|---|
| 185 | 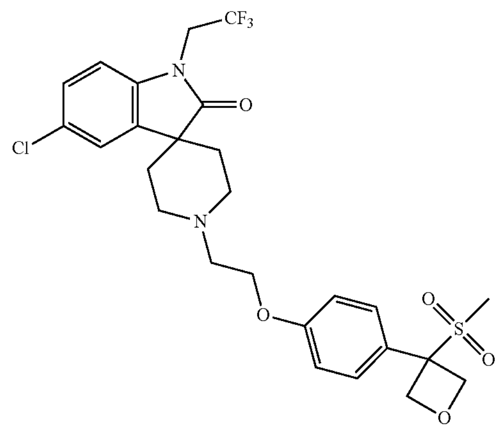 [SMILES: CS(=O)(=O)C1(c2ccc(OCCN3CCC4(CC3)C(=O)N(CC(F)(F)F)c3ccc(Cl)cc34)cc2)COC1] | 5-chloro-1'-{2-[4-(3-methanesulfonyl-oxetan-3-yl)phenoxy]ethyl}-1-(2,2,2-trifluoroethyl)-1,2-dihydrospiro[indole-3,4'-piperidin]-2-one | Calc'd 573.1 Found 573.2 | A-33 and B-14 | n/a | n/a |
| 186 | 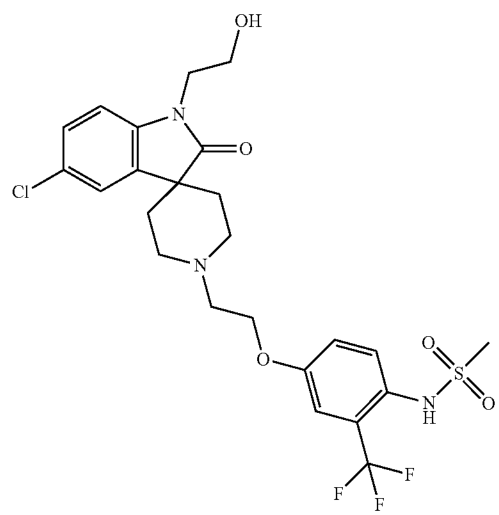 [SMILES: CS(=O)(=O)Nc1ccc(OCCN2CCC3(CC2)C(=O)N(CCO)c2ccc(Cl)cc23)cc1C(F)(F)F] | N-(4-{2-[5-chloro-1-(2-hydroxyethyl)-2-oxo-1,2-dihydrospiro[indole-3,4'-piperidin]-1'-yl]ethoxy}-2-(trifluoromethyl)phenyl)methanesulfonamide | Calc'd 562.1 Found 562.1 | A-46 and B-11 | n/a | n/a |
| 187 | 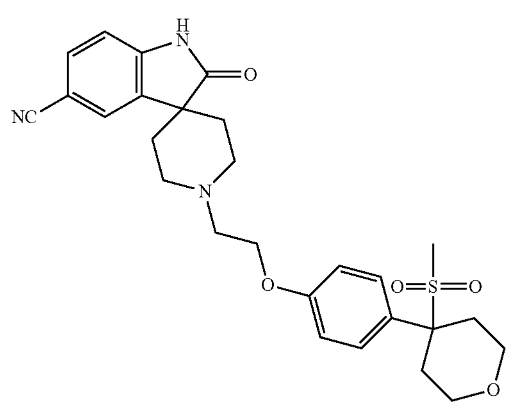 [SMILES: CS(=O)(=O)C1(c2ccc(OCCN3CCC4(CC3)C(=O)Nc3ccc(C#N)cc34)cc2)CCOCC1] | 1'-{2-[4-(4-methanesulfonyl-oxan-4-yl)phenoxy]ethyl}-2-oxo-1,2-dihydrospiro[indole-3,4'-piperidine]-5-carbonitrile | Calc'd 510.2 Found 510.2 | A-41 and B-9 | n/a | n/a |

TABLE 29-continued

| # | Structure | IUPAC Name | Exact Mass [M + H]⁺ | Intermediates Used | Chiral Column, If Applicable | Elution Order |
|---|---|---|---|---|---|---|
| 188 | 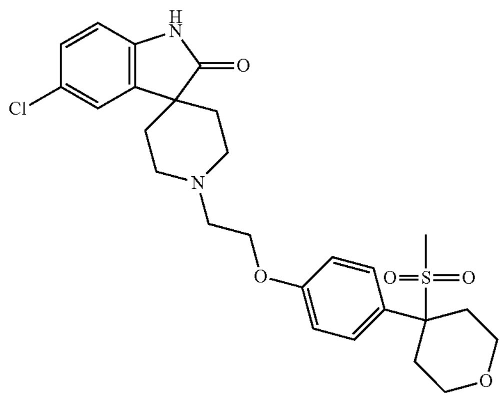 [SMILES: CS(=O)(=O)C1(c2ccc(OCCN3CCC4(CC3)C(=O)Nc3ccc(Cl)cc34)cc2)CCOCC1] | 5-chloro-1'-{2-[4-(4-methanesulfonyl-oxan-4-yl)phenoxy]ethyl}-1,2-dihydrospiro[indole-3,4'-piperidin]-2-one | Calc'd 519.2 Found 519.2 | A-41 and B-4 | n/a | n/a |
| 189 | 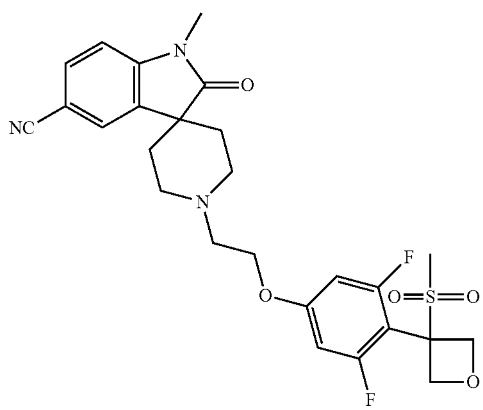 [SMILES: CN1C(=O)C2(CCN(CCOc3cc(F)c(C4(S(C)(=O)=O)COC4)c(F)c3)CC2)c2cc(C#N)ccc21] | 1'-{2-[3,5-difluoro-4-(3-methanesulfonyl-oxetan-3-yl)phenoxy]ethyl}-1-methyl-2-oxo-1,2-dihydrospiro[indole-3,4'-piperidine]-5-carbonitrile | Calc'd 532.1 Found 532.2 | A-32 and B-15 | n/a | n/a |
| 190 | 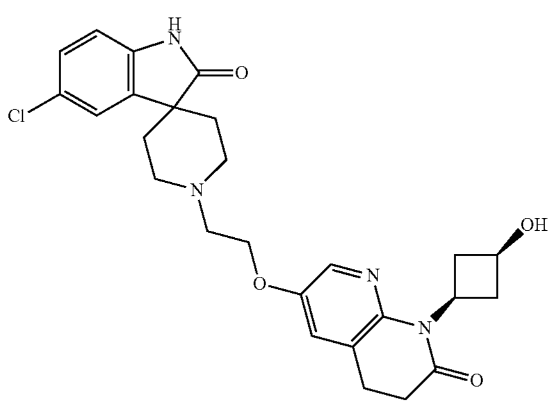 [SMILES: O=C1CCc2cc(OCCN3CCC4(CC3)C(=O)Nc3ccc(Cl)cc34)cnc2N1[C@H]1C[C@@H](O)C1] | 5-chloro-1'-[2-({7-oxo-8-[(cis)-3-hydroxycyclobutyl]-5,6,7,8-tetrahydro-1,8-naphthyridin-3-yl}oxy)ethyl]-1,2-dihydrospiro[indole-3,4'-piperidin]-2-one | Calc'd 497.2 Found 497.2 | A-79 and B-4 | n/a | n/a |

TABLE 29-continued

| # | Structure | IUPAC Name | Exact Mass [M + H]+ | Intermediates Used | Chiral Column, If Applicable | Elution Order |
|---|---|---|---|---|---|---|
| 191 | 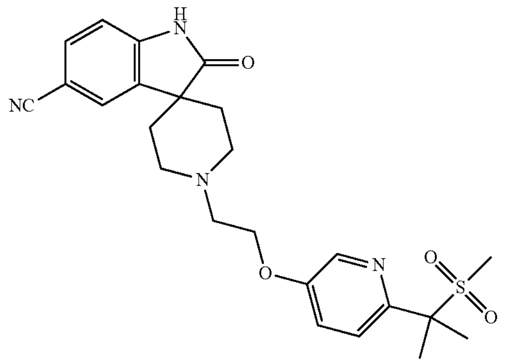 [SMILES: CC(C)(c1ccc(OCCN2CCC3(CC2)C(=O)Nc2ccc(C#N)cc23)cn1)S(C)(=O)=O] | 1'-(2-{[6-(2-methanesulfonylpropan-2-yl)pyridin-3-yl]oxy}ethyl)-2-oxo-1,2-dihydrospiro[indole-3,4'-piperidine]-5-carbonitrile | Calc'd 469.2 Found 469.2 | A-78 and B-9 | n/a | n/a |
| 192 | 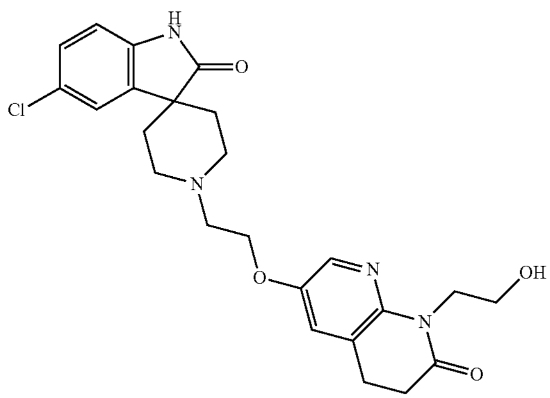 [SMILES: O=C1CCc2cc(OCCN3CCC4(CC3)C(=O)Nc3ccc(Cl)cc34)cnc2N1CCO] | 5-chloro-1'-(2-{[8-(2-hydroxyethyl)-7-oxo-5,6,7,8-tetrahydro-1,8-naphthyridin-3-yl]oxy}ethyl)-1,2-dihydrospiro[indole-3,4'-piperidin]-2-one | Calc'd 471.2 Found 471.2 | A-77 and B-4 | n/a | n/a |

Example 26

N-{2-[4-(2-{5-chloro-2-oxo-1,2-dihydrosiro[indole-3,4'-piperidin]-1'-yl}ethoxy)benzenesulfonyl]ethyl}-N-methylacetamide (Compound 193)

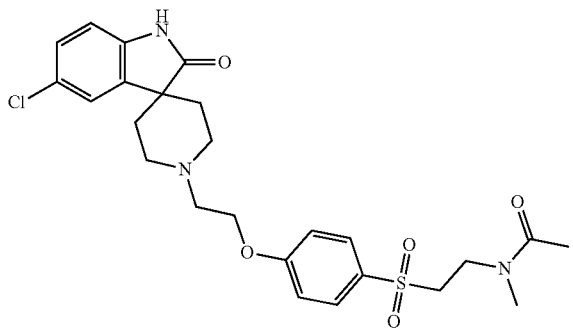 [SMILES: CC(=O)N(C)CCS(=O)(=O)c1ccc(OCCN2CCC3(CC2)C(=O)Nc2ccc(Cl)cc23)cc1]

A mixture of 5-chloro-1'-(2-chloroethyl)-1,2-dihydrospiro[indole-3,4'-piperidin]-2-one (Intermediate B-5, 211 mg, 0.707 mmol), N-[2-(4-hydroxybenzenesulfonyl)ethyl]-N-methylacetamide (Intermediate A-25, 140 mg, 0.544 mmol) and $K_2CO_3$ (150 mg, 1.09 mmol) in DMF (4 mL) was stirred at 50° C. for 16 h. After cooling to room temperature, the mixture was filtered to remove solids. The filtrate was purified by reverse phase preparative HPLC (Phenomenex Gemini-NX $C_{18}$ column, 20-50% o MeCN: 10 mM $NH_4HCO_3$ in $H_2O$) to give N-{2-[4-(2-{5-chloro-2-oxo-1,2-dihydrosiro[indole-3,4'-piperidin]-1'-yl}ethoxy)benzenesulfonyl]ethyl}-N-methylacetamide (Compound 193). $^1$H NMR (400 MHz, DMSO-$d_6$): δ 10.48 (s, 1H), 7.84-7.80 (m, 2H), 7.51 (s, 1H), 7.24-7.20 (m, 3H), 6.84 (d, J=8.0, 1H), 4.26 (t, J=5.6 Hz, 2H), 3.65-3.46 (m, 4H), 2.93-2.87 (m, 6H), 2.70-2.67 (m, 3H), 1.93 (s, 1H), 1.86 (s, 2H), 1.77-1.74 (in, 4H). MS=520.2 [M+H]+.

The following compounds in Table 30 were prepared according to procedures analogous to those described for Compound 193 using the appropriate starting materials.

TABLE 30

| # | Structure | IUPAC Name | Exact Mass [M + H]+ | Intermediates Used |
|---|---|---|---|---|
| 194 | 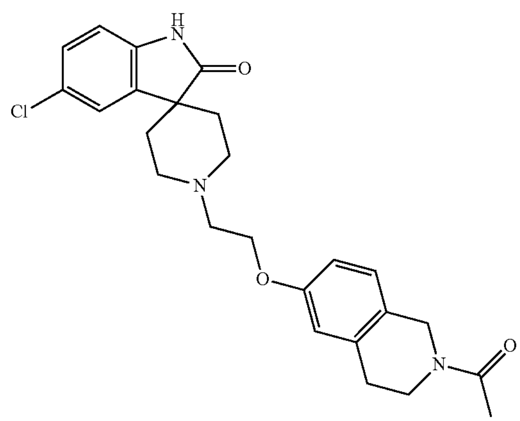 [SMILES: CC(=O)N1CCc2cc(OCCN3CCC4(CC3)C(=O)Nc3ccc(Cl)cc34)ccc2C1] | 1'-{2-[(2-acetyl-1,2,3,4-tetrahydroisoquinolin-6-yl)oxy]ethyl}-5-chloro-1,2-dihydrospiro[indole-3,4'-piperidin]-2-one | Calc'd 454.2 Found 454.2 | A-56 and B-5 |
| 195 | 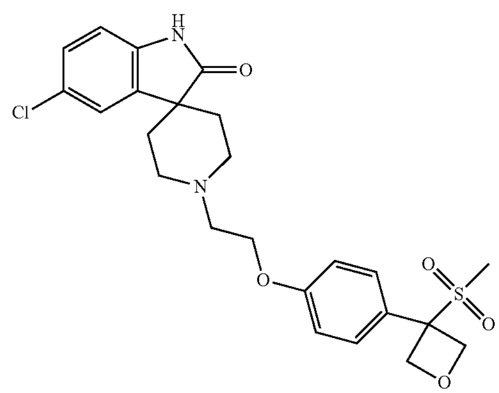 [SMILES: CS(=O)(=O)C1(c2ccc(OCCN3CCC4(CC3)C(=O)Nc3ccc(Cl)cc34)cc2)COC1] | 5-chloro-1'-{2-[4-(3-methanesulfonyl-oxetan-3-yl)phenoxy]ethyl}-1,2-dihydrospiro[indole-3,4'-piperidin]-2-one | Calc'd 491.1 Found 491.1 | A-84 and B-5 |
| 196 | 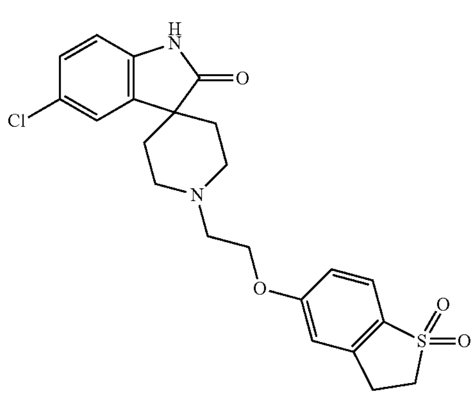 [SMILES: O=C1Nc2ccc(Cl)cc2C12CCN(CCOc1ccc3c(c1)CCS3(=O)=O)CC2] | 5-(2-{5-chloro-2-oxo-1,2-dihydrospiro[indole-3,4'-piperidin]-1'-yl}ethoxy)-2,3-dihydro-1λ6-benzothiophene-1,1-dione | Calc'd 447.1 Found 447.2 | A-52 and B-5 |

TABLE 30-continued

| # | Structure | IUPAC Name | Exact Mass [M + H]+ | Intermediates Used |
|---|---|---|---|---|
| 197 | 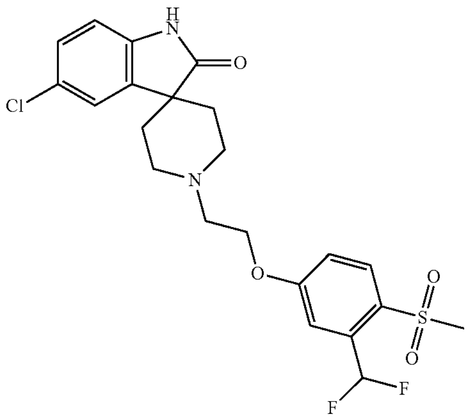 [SMILES: CS(=O)(=O)c1ccc(OCCN2CCC3(CC2)C(=O)Nc2ccc(Cl)cc23)cc1C(F)F] | 5-chloro-1'-{2-[3-(difluoromethyl)-4-methane-sulfonylphenoxy]ethyl}-1,2-dihydrospiro[indole-3,4'-piperidin]-2-one | Calc'd 485.1 Found 485.1 | A-12 and B-5 |
| 198 | 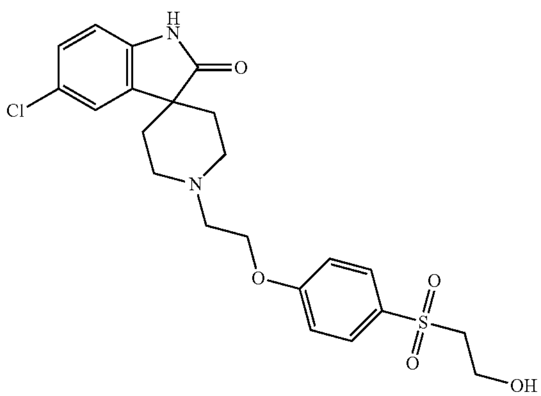 [SMILES: O=C1Nc2ccc(Cl)cc2C12CCN(CCOc1ccc(S(=O)(=O)CCO)cc1)CC2] | 5-chloro-1'-{2-[4-(2-hydroxyethane-sulfonyl)phenoxy)ethyl}-1,2-dihydrospiro[indole-3,4'-piperidin]-2-one | Calc'd 465.1 Found 465.1 | A-85 and B-5 |

Example 27

5-chloro-1'-{1-[(1-methyl-2-oxo-1,2,3,4-tetrahydro-quinolin-6-yl)oxy]propan-2-yl}-1,2-dihydrospiro[indole-3,4'-piperidin]-2-one (Compound 199), chloro-1'-[(2S) or (2R)-1-[(1-methyl-2-oxo-1,2,3,4-tetrahydroquinolin-6-yl)oxy]propan-2-yl]-1,2-dihydrospiro[indole-3,4'-piperidin]-2-one (Compound 200), and chloro-1'-[(2R) or (2S)-1-[(1-methyl-2-oxo-1,2,3,4-tetrahydroquinolin-6-yl)oxy]propan-2-yl]-1,2-dihydrospiro[indole-3,4'-piperidin]-2-one (Compound 201)

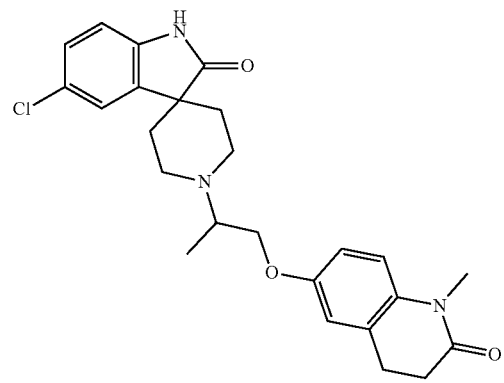 [SMILES: CC(COc1ccc2c(c1)CCC(=O)N2C)N1CCC2(CC1)C(=O)Nc1ccc(Cl)cc12]

-continued

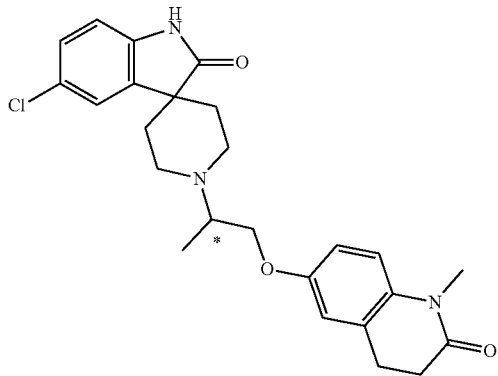

-continued

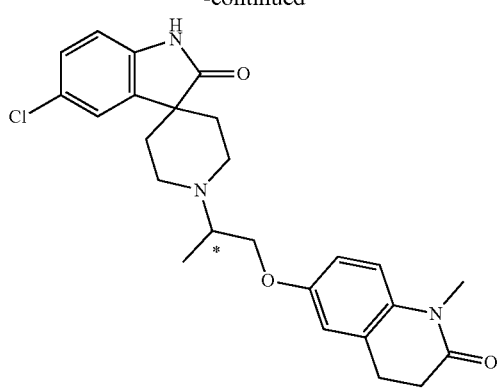

Step 1: 5-choro-1'-{1-[(1-methyl-2-oxo-1,2,3,4-tetrahydroquinolin-6-yl)oxy]propan-2-yl}-1,2-dihydrospiro[indole-3,4'-piperidin]-2-one (Compound 199)

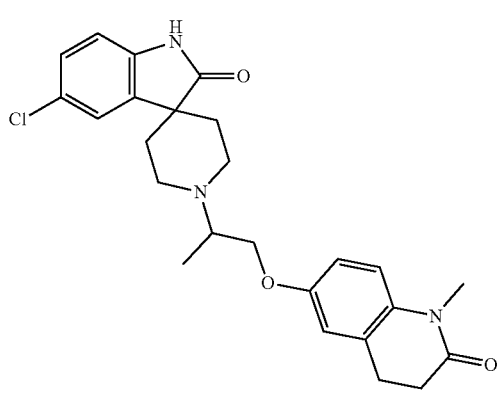

A solution of 1-methyl-6-(2-oxopropoxy)-1,2,3,4-tetrahydroquinolin-2-one (Intermediate A-2, 400 mg, 1.71 mmol), 5-chloro-1,2-dihydrospiro[indole-3,4'-piperidin]-2-one (Intermediate B-4, 406 mg, 1.71 mmol), Ti(i-PrO)$_4$ (506 μL, 1.71 mmol) and AcOH (9.81 μL, 0.171 mmol) in 1,2-dichloroethane (5 mL) was stirred at 50° C. for 2 h. The mixture was cooled to 0° C. and NaBH(OAc)$_3$ (545 mg, 2.57 mmol) was added in portionwise. The mixture was stirred at 50° C. for 12 hours. After cooling to 0° C., the reaction mixture was quenched with H$_2$O (5 mL), and then filtered. The filtrate was extracted with EtOAc (3×10 mL). The combined organic layers were washed with brine (8 mL), dried over Na$_2$SO$_4$, filtered, and concentrated in vacuo. The residue was purified by reverse phase preparative HPLC (Waters Xbridge Prep OBD C$_{18}$ column, 30-60% MeCN: 10 mM NH$_4$HCO$_3$ in H$_2$O) to give 5-chloro-1'-{1-[(1-methyl-2-oxo-1,2,3,4-tetrahydroquinolin-6-yl)oxy]propan-2-yl}-1,2-dihydrospiro[indole-3,4'-piperidin]-2-one (Compound 199). $^1$H NMR (400 MHz, DMSO-d$_6$): δ 10.48 (s, 1H), 7.45 (s, 1H), 7.23 (d, J=6.0 Hz, 1H), 7.01 (d, J=8.8 Hz, 1H), 6.91-6.83 (m, 3H), 4.12-4.08 (m, 1H), 3.96-3.93 (m, 1H), 3.22 (s, 3H), 3.10-2.98 (m, 3H), 2.85-2.81 (m, 3H), 2.79-2.77 (m, 1H), 2.53-2.51 (m, 2H), 1.80-1.76 (m, 2H), 1.68-1.65 (m, 2H), 1.14 (d, J=6.8 Hz, 3H). MS=454.2 [M+H]$^+$.

Step 2: chloro-1'-[(2S) or (2R)-1-[(1-methyl-2-oxo-1,2,3,4-tetrahydroquinolin-6-yl)oxy]propan-2-yl]-1,2-dihydrospiro[indole-3,4'-piperidin]-2-one (Compound 200) and chloro-1'-[(2R) or (2S)-1-[(1-methyl-2-oxo-1,2,3,4-tetrahydroquinolin-6-yl)oxy]propan-2-yl]-1,2-dihydrospiro[indole-3,4'-piperidin]-2-one (Compound 201)

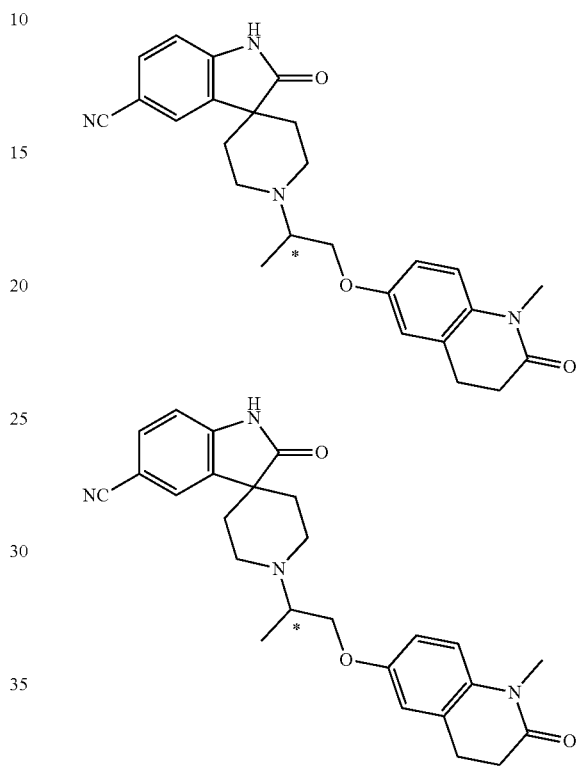

5-chloro-1'-{1-[(1-methyl-2-oxo-1,2,3,4-tetrahydroquinolin-6-yl)oxy]propan-2-yl}-1,2-dihydrospiro[indole-3,4'-piperidin]-2-one was separated by preparative chiral SFC (Daicel Chiralpak AD-3, 42% ethanol with 0.1% NH$_4$OH in CO$_2$). The first eluting enantiomer of the title compound, chloro-1'-[(2S) or (2R)-1-[(1-methyl-2-oxo-1,2,3,4-tetrahydroquinolin-6-yl)oxy]propan-2-yl]-1,2-dihydrospiro[indole-3,4'-piperidin]-2-one (Compound 200): $^1$H NMR (400 MHz, DMSO-d$_6$): δ 10.49 (s, 1H), 7.45 (s, 1H), 7.23 (d, J=8.0 Hz, 1H), 7.01 (d, J=8.8 Hz, 1H), 6.90-6.83 (m, 3H), 4.12-4.08 (m, 1H), 3.96-3.92 (m, 1H), 3.22 (s, 3H), 3.10-2.98 (m, 3H), 2.85-2.81 (m, 3H), 2.77-2.73 (m, 1H), 2.53-2.51 (m, 2H), 1.80-1.76 (m, 2H), 1.68-1.65 (m, 2H), 1.14 (d, J=6.8 Hz, 3H). MS=454.2 [M+H]$^+$. The second eluting enantiomer of the title compound, chloro-1'-[(2R) or (2S)-1-[(1-methyl-2-oxo-1,2,3,4-tetrahydroquinolin-6-yl)oxy]propan-2-yl]-1,2-dihydrospiro[indole-3,4'-piperidin]-2-one (Compound 201): $^1$H NMR (400 MHz, DMSO-d$_6$): δ 10.49 (s, 1H), 7.45 (s, 1H), 7.23 (d, J=8.4 Hz, 1H), 7.01 (d, J=8.8 Hz, 1H), 6.91-6.83 (m, 3H), 4.12-4.08 (m, 1H), 3.95-3.93 (m, 1H), 3.22 (s, 3H), 3.10-2.98 (m, 3H), 2.85-2.81 (m, 3H), 2.77-2.73 (m, 1H), 2.53-2.51 (m, 2H), 1.78-1.76 (m, 2H), 1.68-1.65 (m, 2H), 1.14 (d, J=6.8 Hz, 3H). MS=454.2 [M+H]$^+$.

The following compounds in Table 31 were prepared according to procedures analogous to those described for Compounds 199-201 using the appropriate starting materials.

TABLE 31

| # | Structure | IUPAC Name | Exact Mass [M + H]+ | Intermediates Used | Chiral Column, If Applicable | Elution Order |
|---|---|---|---|---|---|---|
| 202 | 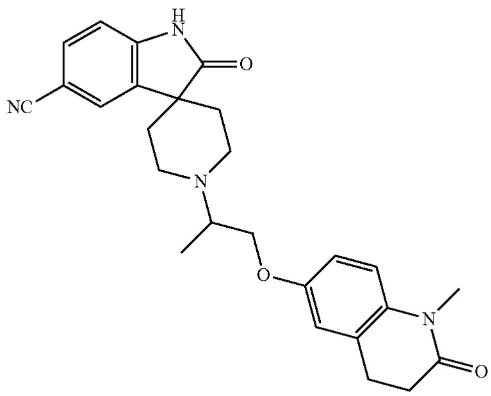 [SMILES: CC(COc1ccc2c(c1)CCC(=O)N2C)N1CCC2(CC1)C(=O)Nc1ccc(C#N)cc12] | 1'-{1-[(1-methyl-2-oxo-1,2,3,4-tetrahydroquinolin-6-yl)oxy]propan-2-yl}-2-oxo-1,2-dihydrospiro[indole-3,4'-piperidine]-5-carbonitrile | Calc'd 445.2 Found 445.2 | A-2 and B-9 | n/a | n/a |
| 203 | 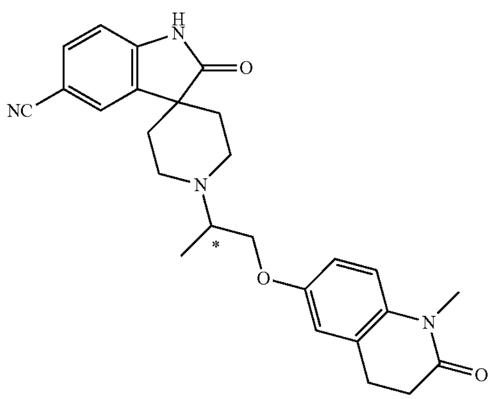 [SMILES: CC(COc1ccc2c(c1)CCC(=O)N2C)N1CCC2(CC1)C(=O)Nc1ccc(C#N)cc12] | (S) or (R)-1'-{1-[(1-methyl-2-oxo-1,2,3,4-tetrahydroquinolin-6-yl)oxy]propan-2-yl}-2-oxo-1,2-dihydrospiro[indole-3,4'-piperidine]-5-carbonitrile | Calc'd 445.2 Found 445.2 | A-2 and B-9 | Daicel Chiralpak AD-2 | First |
| 204 | 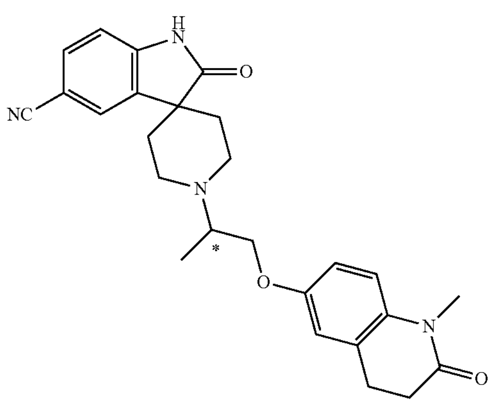 [SMILES: CC(COc1ccc2c(c1)CCC(=O)N2C)N1CCC2(CC1)C(=O)Nc1ccc(C#N)cc12] | (R) or (S)-1'-{1-[(1-methyl-2-oxo-1,2,3,4-tetrahydroquinolin-6-yl)oxy]propan-2-yl}-2-oxo-1,2-dihydrospiro[indole-3,4'-piperidine]-5-carbonitrile | Calc'd 445.2 Found 445.2 | A-2 and B-9 | Daicel Chiralpak AD-3 | Second |

Example 28

5-chloro-1'-[1-(4-methanesulfonylphenoxy)propan-2-yl]-1-[3-hydroxycyclobutyl]-1,2-dihydrospiro[indole-3,4'-piperidin]-2-one (Compound 205), 5-chloro-1'-[(2S) or (2R)-1-(4-methanesulfonylphenoxy)propan-2-yl]-1-[(cis) or (trans)-3-hydroxycyclobutyl]-1,2-dihydrospiro[indole-3,4'-piperidin]-2-one (Compound 206), 5-chloro-1'-[(2S) or (2R)-1-(4-methanesulfonylphenoxy)propan-2-yl]-1-[(trans) or (cis)-3-hydroxycyclobutyl]-1,2-dihydrospiro[indole-3,4'-piperidin]-2-one (Compound 207), 5-chloro-1'-[(2R) or (2S)-1-(4-methanesulfonylphenoxy)propan-2-yl]-1-[(cis) or (trans)-3-hydroxycyclobutyl]-1,2-dihydrospiro[indole-3,4'-piperidin]-2-one (Compound 208), and 5-chloro-1'-[(2R) or (2S)-1-(4-methanesulfonylphenoxy)propan-2-yl]-1-[(trans) or (cis)-3-hydroxycyclobutyl]-1,2-dihydrospiro[indole-3,4'-piperidin]-2-one (Compound 209)

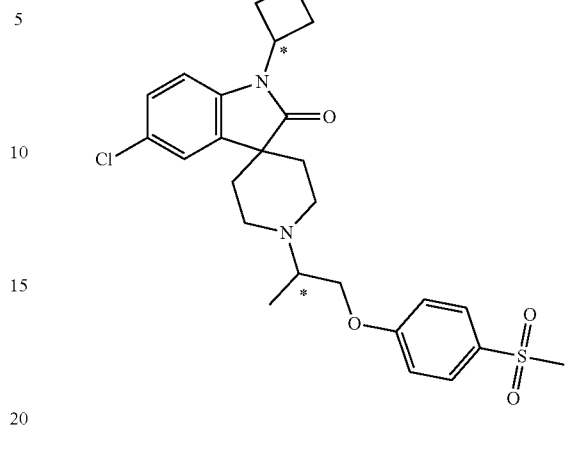

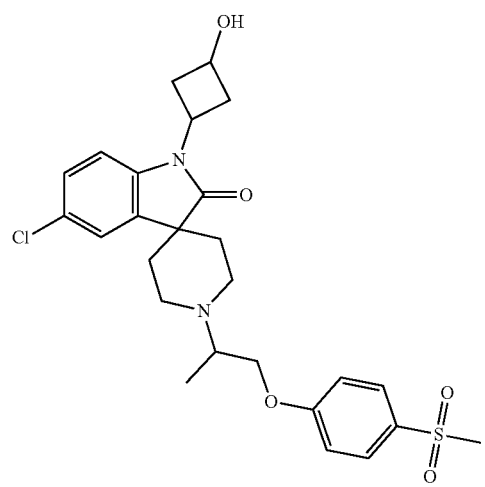 [SMILES: CC(COc1ccc(S(C)(=O)=O)cc1)N1CCC2(CC1)C(=O)N(C1CC(O)C1)c1ccc(Cl)cc12]

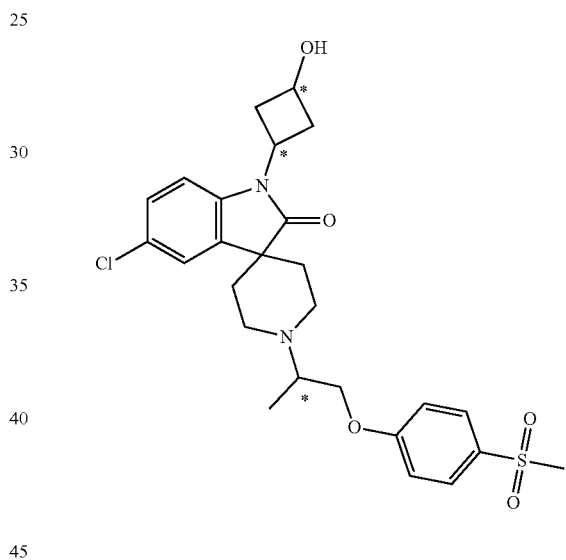

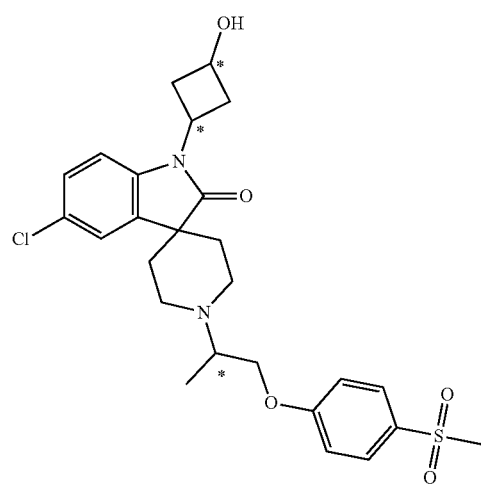

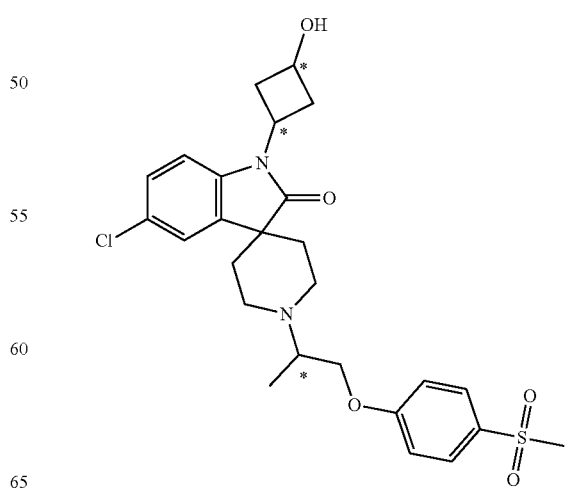

1041

Step 1: 5-chloro-1'-[1-(4-methanesulfonylphenoxy) propan-2-yl]-1-[3-hydroxycyclobutyl]-1,2-dihydrospiro[indole-3,4'-piperidin]-2-one (Compound 205)

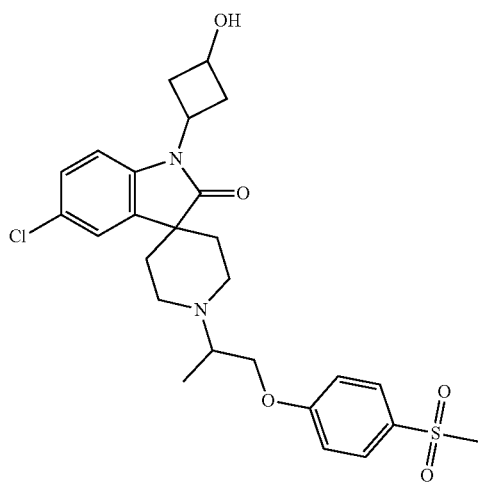

A mixture of 5-chloro-1-(3-hydroxycyclobutyl)-1,2-dihydrospiro[indole-3,4'-piperidin]-2-one (Intermediate B-16, 250 mg, 0.815 mmol), 1-(4-methanesulfonylphenoxy)propan-2-one (Intermediate A-1, 465 mg, 2.04 mmol), tetraisopropoxytitanium (231 mg, 0.815 mmol) and AcOH (3.0 mg, 40.7 µmol) in DCE (5 mL) was stirred at room temperature for 1 h. NaBH(OAc)$_3$ (259 mg, 1.22 mmol) was added into the mixture, which was then stirred at 50° C. for 16 h. The reaction mixture was cooled to 0° C. and then quenched with H$_2$O (20 mL). The mixture was extracted with EtOAc (3×15 mL). The combined organic layers were washed with brine (20 mL), dried over Na$_2$SO$_4$, filtered, and concentrated in vacuo. The residue was purified by reverse phase preparative HPLC (Waters Xbridge BEH C$_{18}$ column, 25-55% MeCN: 10 mM NH$_4$HCO$_3$ in H$_2$O) to give 5-chloro-1'-[1-(4-methanesulfonylphenoxy)propan-2-yl]-1-[3-hydroxycyclobutyl]-1,2-dihydrospiro[indole-3,4'-piperidin]-2-one as a mixture of diastereomers (Compound 205). $^1$HNMR (400 MHz, DMSO-d$_6$, 30/31 H): δ 7.85 (d, J=8.8 Hz, 2H), 7.49 (d, J=2.0 Hz, 1H), 7.35-7.21 (m, 4H), 5.31 (d, J=6.8 Hz, 1H), 4.26-4.06 (m, 3H), 3.95-3.90 (m, 1H), 3.16-3.12 (m, 4H), 3.06-2.99 (m, 2H), 2.87-2.71 (m, 2H), 2.64-2.58 (m, 3H), 1.77-1.66 (m, 4H), 1.16 (d, J=6.8 Hz, 3H). MS=519.1 [M+H]$^+$.

1042

Step 2: 5-chloro-1'-[(2S) or (2R)-1-(4-methanesulfonylphenoxy)propan-2-yl]-1-[(cis) or (trans)-3-hydroxycyclobutyl]-1,2-dihydrospiro[indole-3,4'-piperidin]-2-one (Compound 206) and 5-chloro-1'-[(2R) or (2S)-1-(4-methanesulfonylphenoxy)propan-2-yl]-1-[(cis) or (trans)-3-hydroxycyclobutyl]-1,2-dihydrospiro[indole-3,4'-piperidin]-2-one (Compound 208)

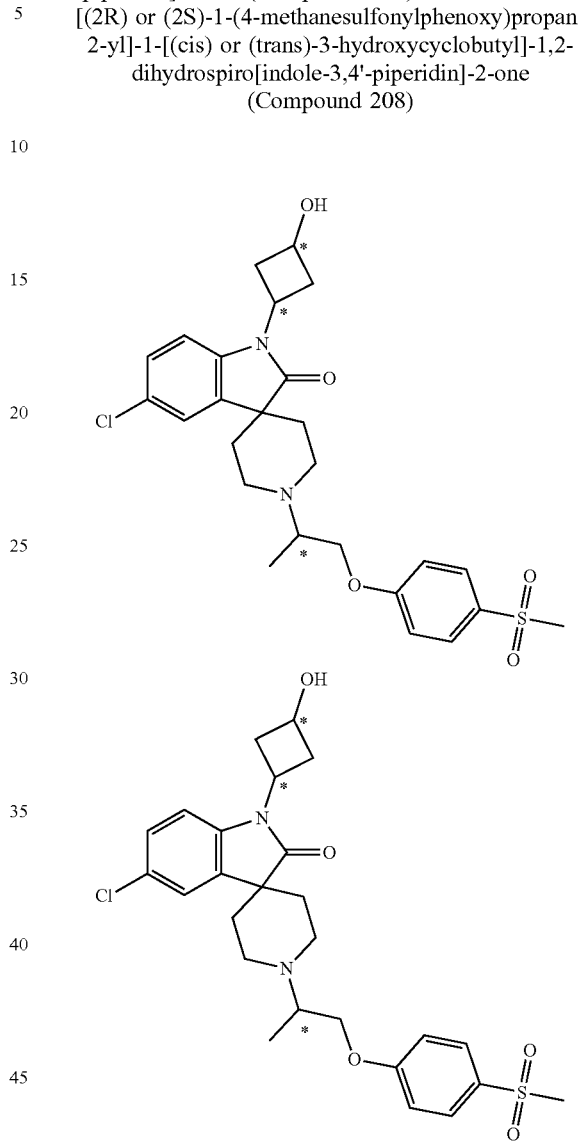

5-chloro-1'-[1-(4-methanesulfonylphenoxy)propan-2-yl]-1-[3-hydroxycyclobutyl]-1,2-dihydrospiro[indole-3,4'-piperidin]-2-one (Compound 205) was separated by preparative chiral SFC (Daicel Chiralcel IG-3, 60% EtOH with 0.1% NH$_4$OH in CO$_2$). The first eluting peak contained a mixture of isomers that underwent further chiral separation as described in step 3. The second eluting peak, 5-chloro-1'-[(2S) or (2R)-1-(4-methanesulfonylphenoxy)propan-2-yl]-1-[(cis) or (trans)-3-hydroxycyclobutyl]-1,2-dihydrospiro[indole-3,4'-piperidin]-2-one (Compound 206): $^1$HNMR (400 MHz, DMSO-d$_6$): δ 7.85 (d, J=8.8 Hz, 2H), 7.48 (d, J=2.0 Hz, 1H), 7.30 (dd, J=8.4, 2.4 Hz, 1H), 7.22 (d, J=8.8 Hz, 2H), 7.12 (d, J=8.8 Hz, 1H), 4.93-4.85 (m, 1H), 4.44-4.41 (m, 1H), 4.27-4.22 (m, 1H), 4.10-4.06 (m, 1H), 3.16-3.12 (m, 4H), 3.06-3.00 (m, 2H), 2.92-2.88 (m, 2H), 2.84-2.70 (m, 3H), 2.22-2.15 (m, 2H), 1.77-1.65 (m, 4H), 1.16 (d, J=6.8 Hz, 3H). MS=519.1 [M+H]$^+$. The third eluting peak, 5-chloro-1'-[(2R) or (2S)-1-(4-methanesulfonylphenoxy)

propan-2-yl]-1-[(cis) or (trans)-3-hydroxycyclobutyl]-1,2-dihydrospiro[indole-3,4'-piperidin]-2-one (Compound 208): $^1$HNMR (400 MHz, DMSO-d$_6$, 30/31 H): δ 7.85 (d, J=8.8 Hz, 2H), 7.49 (d, J=2.0 Hz, 1H), 7.34-7.21 (m, 4H), 5.30 (d, J=6.4 Hz, 1H), 4.26-4.06 (m, 3H), 3.97-3.89 (m, 1H), 3.16-3.12 (m, 4H), 3.06-3.00 (m, 2H), 2.84-2.72 (m, 2H), 2.65-2.55 (m, 3H), 1.77-1.66 (m, 4H), 1.17-1.15 (m, 3H). MS=519.1 [M+H]$^+$.

Step 3: 5-chloro-1'-[(2R) or (2S)-1-(4-methanesulfonylphenoxy)propan-2-yl]-1-[(trans) or (cis)-3-hydroxycyclobutyl]-1,2-dihydrospiro[indole-3,4'-piperidin]-2-one (Compound 209) and 5-chloro-1'-[(2S) or (2R)-1-(4-methanesulfonylphenoxy)propan-2-yl]-1-[(trans) or (cis)-3-hydroxycyclobutyl]-1,2-dihydrospiro[indole-3,4'-piperidin]-2-one (Compound 207)

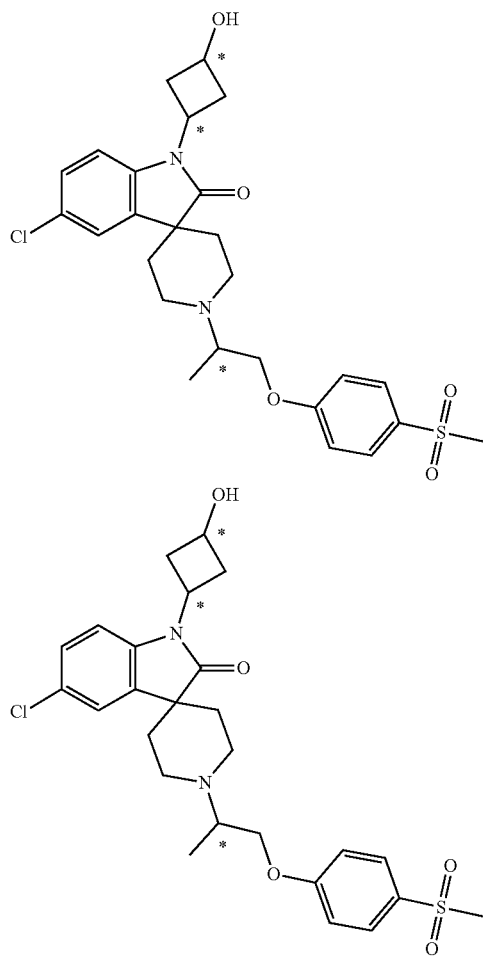

The second eluting peak from Step 2 was further separated by preparative chiral SFC (Daicel Chiralcel OJ-3, 30% MeOH with 0.1% NH$_4$OH in CO$_2$). The first eluting isomer, 5-chloro-1'-[(2R) or (2S)-1-(4-methanesulfonylphenoxy)propan-2-yl]-1-[(trans) or (cis)-3-hydroxycyclobutyl]-1,2-dihydrospiro[indole-3,4'-piperidin]-2-one (Compound 209): $^1$HNMR (400 MHz, DMSO-d$_6$, 30/31 H): δ 7.85 (d, J=9.2 Hz, 2H), 7.49 (s, 1H), 7.34-7.21 (m, 4H), 5.30 (d, J=6.8 Hz, 1H), 4.26-4.06 (m, 3H), 3.98-3.89 (m, 1H), 3.16-3.11 (m, 4H), 3.04-3.02 (m, 2H), 2.84-2.72 (m, 2H), 2.67-2.60 (m, 3H), 1.84-1.64 (m, 4H), 1.17-1.15 (m, 3H). MS=519.1 [M+H]$^+$. The second eluting isomer, 5-chloro-1'-[(2S) or (2R)-1-(4-methanesulfonylphenoxy)propan-2-yl]-1-[(trans) or (cis)-3-hydroxycyclobutyl]-1,2-dihydrospiro[indole-3,4'-piperidin]-2-one (Compound 207), $^1$HNMR (400 MHz, DMSO-d$_6$): δ 7.85 (d, J=8.8 Hz, 2H), 7.49 (d, J=2.0 Hz, 1H), 7.30 (dd, J=8.4, 2.0 Hz, 1H), 7.22 (d, J=8.8 Hz, 2H), 7.12 (d, J=8.4 Hz, 1H), 5.16 (d, J=4.4 Hz, 1H), 4.93-4.85 (m, 1H), 4.44-4.42 (m, 1H), 4.26-4.22 (m, 1H), 4.10-4.06 (m, 1H), 3.16-3.12 (m, 4H), 3.06-3.00 (m, 2H), 2.92-2.72 (m, 4H), 2.22-2.16 (m, 2H), 1.77-1.66 (m, 4H), 1.16 (d, J=6.8 Hz, 3H). MS=519.1 [M+H]$^+$.

Example 29A 5-chloro-1'-[(2S)-1-[3-(difluoromethyl)-4-methanesulfonylphenoxy]propan-2-yl]-1,2-dihydrospiro[indole-3,4'-piperidin]-2-one (Compound 210)

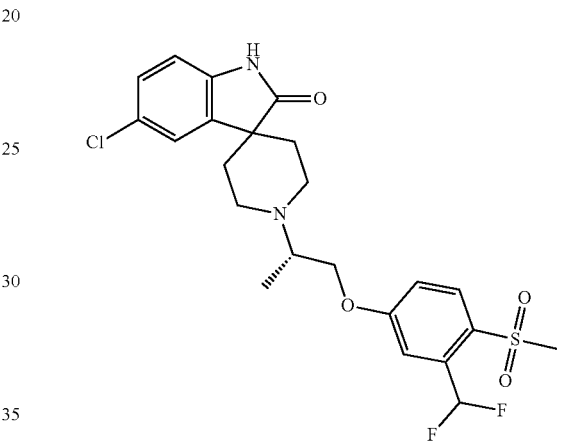

To a solution containing a mixture of 5-chloro-1'-[(2S)-1-hydroxypropan-2-yl]-1,2-dihydrospiro[indole-3,4'-piperidin]-2-one and 5-chloro-1'-[(2R)-2-hydroxypropyl]-1,2-dihydrospiro[indole-3,4'-piperidin]-2-one (Intermediates B-17 and B-18, 136 mg, 0.461 mmol), 3-(difluoromethyl)-4-methanesulfonylphenol (Intermediate A-12, 154 mg, 0.692 mmol) in THF (4 mL) was added PPh$_3$ (242 mg, 0.923 mmol). The mixture was cooled to 0° C. and DIAD (179 μL, 0.923 mmol) was added dropwise. The mixture was warmed to room temperature and stirred for 15 h. The reaction mixture was quenched with H$_2$O (8 mL) and extracted with EtOAc (3×10 mL). The combined organic layers were washed with brine (5 mL), dried over Na$_2$SO$_4$, filtered, and concentrated in vacuo. The crude residue was purified by normal phase silica gel chromatography (Biotage 4 g cartridge, 0-90% EtOAc:petroleum ether). The crude product was further purified by reverse phase preparative HPLC (Waters Xbridge BEH C$_{18}$ column, 25-55% MeCN: 10 mM NH$_4$HCO$_3$ in H$_2$O) to give the desired product 5-chloro-1'-[(2S)-1-[3-(difluoromethyl)-4-methanesulfonylphenoxy]propan-2-yl]-1,2-dihydrospiro[indole-3,4'-piperidin]-2-one (Compound 210) as the first eluting isomer. $^1$H NMR (400 MHz, DMSO-d$_6$): δ 10.49 (s, 1H), 8.00 (d, J=8.8 Hz, 1H), 7.59 (t, J=54.4 Hz, 1H), 7.44-7.37 (m, 3H), 7.23 (dd, J=8.0, 2.0 Hz, 1H), 6.84 (d, J=8.4 Hz, 1H), 4.31 (dd, J=10.0, 6.4 Hz, 1H), 4.16 (dd, J=10.0, 5.6 Hz, 1H), 3.26 (s, 3H), 3.18-3.13 (m, 1H), 3.03-3.01 (m, 2H), 2.85-2.73 (m, 2H), 1.80-1.75 (m, 2H), 1.67-1.63 (m, 2H), 1.16 (d, J=6.8 Hz, 3H). MS=499.1 [M+H]$^+$.

The following compounds in Table 32 were prepared according to procedures analogous to those described for Compound 210 using the appropriate starting materials.

TABLE 32

| # | Structure | IUPAC Name | Exact Mass [M + H]+ | Intermediates Used | Elution on Order |
|---|---|---|---|---|---|
| 211 | 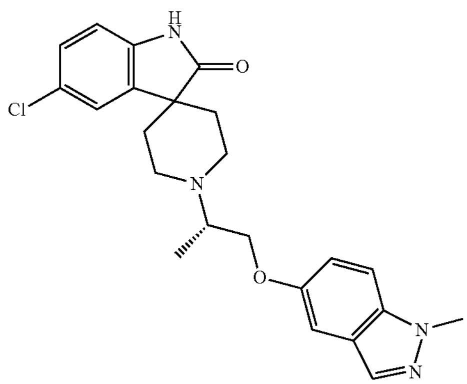 [SMILES: C[C@@H](COc1ccc2c(cnn2C)c1)N1CCC2(CC1)C(=O)Nc1ccc(Cl)cc12] | 5-chloro-1'-[(2S)-1-[(1-methyl-1H-indazol-5-yl)oxy]propan-2-yl]-1,2-dihydrospiro[indole-3,4'-piperidin]-2-one | Calc'd 425.2 Found 425.2 | B-17 and B-18 | First eluting isomer |
| 212 | 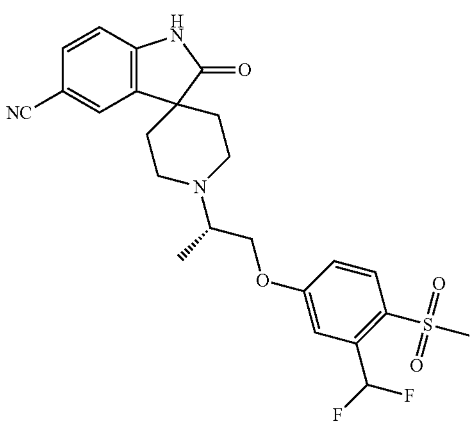 [SMILES: C[C@@H](COc1ccc(S(C)(=O)=O)c(C(F)F)c1)N1CCC2(CC1)C(=O)Nc1ccc(C#N)cc12] | 1'-[(2S)-1-[3-(difluoromethyl)-4-methanesulfonyl-phenoxy]propan-2-yl]-2-oxo-1,2-dihydrospiro[indole-3,4'-piperidine]-5-carbonitrile | Calc'd 490.2 Found 490.2 | A-13, B-19, and B-20 | First eluting isomer |
| 213 | 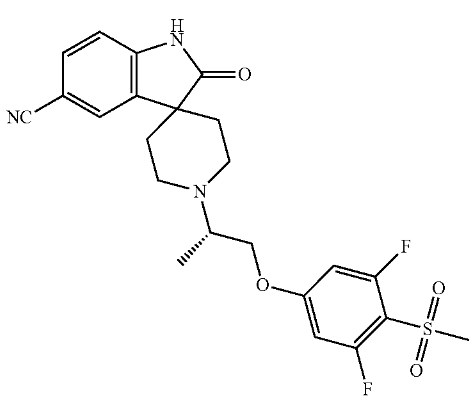 [SMILES: C[C@@H](COc1cc(F)c(S(C)(=O)=O)c(F)c1)N1CCC2(CC1)C(=O)Nc1ccc(C#N)cc12] | 1'-[(2S)-1-(3,5-difluoro-4-methanesulfonyl-phenoxy)propan-2-yl]-2-oxo-1,2-dihydrospiro[indole-3,4'-piperidine]-5-carbonitrile | Calc'd 476.1 Found 476.1 | A-11, B-19, and B-20 | First eluting isomer |

Example 29B

N-[4-(2-{5-chloro-2-oxo-1,2-dihydrospiro[indole-3,4'-piperidin]-1'-yl}ethoxy)phenyl]methanesulfonamide (Compound 214)

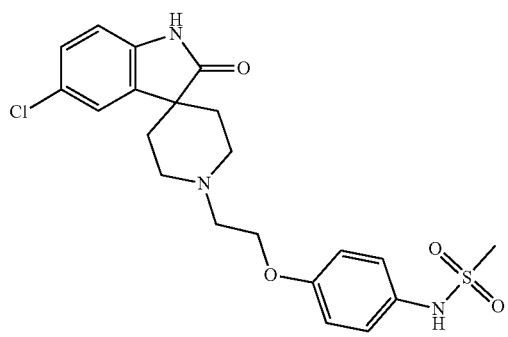 [SMILES: CS(=O)(=O)Nc1ccc(OCCN2CCC3(CC2)C(=O)Nc2ccc(Cl)cc23)cc1]

Step 1: 1-(2-bromoethoxy)-4-nitrobenzene

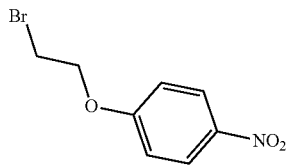 [SMILES: O=[N+]([O-])c1ccc(OCCBr)cc1]

To a solution of 4-nitrophenol (5.00 g, 35.9 mmol) in 1,2-dibromoethane (30 mL) was added Cs₂CO₃ (35.1 g, 108 mmol). The mixture was stirred at 100° C. for 12 h. After cooling to room temperature, solids were removed by filtration and the filtrate was concentrated in vacuo. The crude residue was purified by normal phase silica gel chromatography (Biotage 12 g cartridge, 0-50% EtOAc:petroleum ether) to give 1-(2-bromoethoxy)-4-nitrobenzene. MS=246.0/248.0 [M+H]⁺.

Step 2: 5-chloro-1'-[2-(4-nitrophenoxy)ethyl]-1,2-dihydrospiro[indole-3,4'-piperidin]-2-one

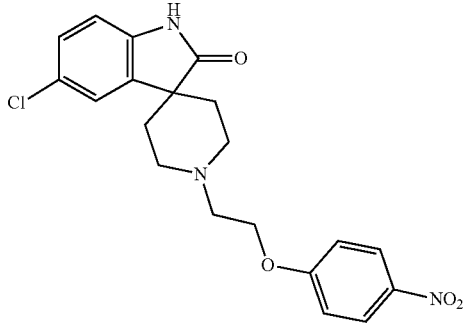 [SMILES: O=C1Nc2ccc(Cl)cc2C12CCN(CCOc1ccc([N+](=O)[O-])cc1)CC2]

To a solution of 1-(2-bromoethoxy)-4-nitrobenzene (300 mg, 1.22 mmol) in MeCN (3 mL) was added NaHCO₃ (307 mg, 3.66 mmol) and 5-chloro-1,2-dihydrospiro[indole-3,4'-piperidin]-2-one (Intermediate B-4, 433 mg, 1.58 mmol, HCl salt). The mixture was stirred at 80° C. for 12 h. After cooling to room temperature, the reaction mixture was diluted with H₂O (8 mL) and extracted with EtOAc (3×8 mL). The combined organic layers were washed with brine (10 mL), dried over Na₂SO₄, filtered, and concentrated in vacuo. The crude residue was purified by normal phase silica gel chromatography (Biotage 12 g cartridge, 0-30% EtOAc: petroleum ether) to give 5-chloro-1'-[2-(4-nitrophenoxy)ethyl]-1,2-dihydrospiro[indole-3,4'-piperidin]-2-one. MS=402.2 [M+H]⁺.

Step 3: 1'-[2-(4-aminophenoxy)ethyl]-5-chloro-1,2-dihydrospiro[indole-3,4'-piperidin]-2-one

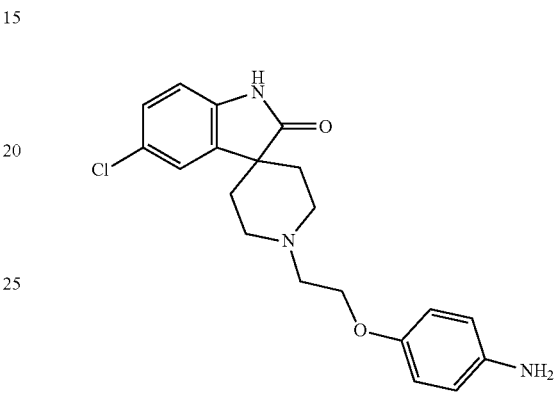

A mixture of 5-chloro-1'-[2-(4-nitrophenoxy)ethyl]-1,2-dihydrospiro[indole-3,4'-piperidin]-2-one (200 mg, 498 µmol), Fe (139 mg, 2.49 mmol), and NH₄Cl (79.9 mg, 1.49 mmol) in EtOH (6 mL) and H₂O (2 mL) was stirred at 70° C. for 2 h under a N₂ atmosphere. After cooling to room temperature, solids were removed by filtration and the filtrate was concentrated in vacuo to give 1'-[2-(4-aminophenoxy)ethyl]-5-chloro-1,2-dihydrospiro[indole-3,4'-piperidin]-2-one, which was used in the subsequent step without further purification. MS=372.2 [M+H]⁺.

Step 4: N-[4-(2-{5-chloro-2-oxo-1,2-dihydrospiro[indole-3,4'-piperidin]-1'-yl}ethoxy)phenyl]methanesulfonamide (Compound 214)

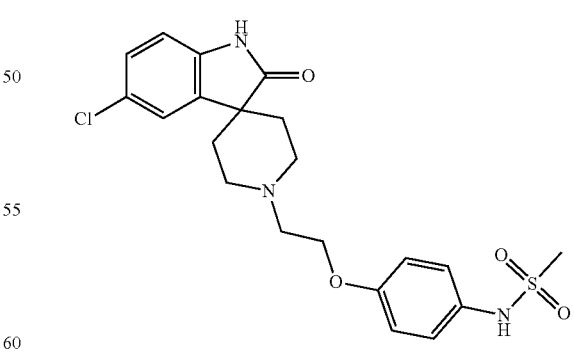

To a solution of 1'-[2-(4-aminophenoxy)ethyl]-5-chloro-1,2-dihydrospiro[indole-3,4'-piperidin]-2-one (110 mg, 296 mmol), and TEA (82.4 µL, 0.52 mmol) in DCM (3 mL) was added methanesulfonic anhydride (103. mg, 0.592 mmol). The mixture was stirred at room temperature for 2 h under N₂ atmosphere. The reaction mixture was quenched with saturated aqueous NaHCO₃ (10 mL) and extracted with EtOAc (3×15 mL). The combined organic layers were washed with brine (20 mL), dried over Na₂SO₄, filtered, and concentrated in vacuo. The residue was purified by reverse phase preparative HPLC (Phenomenex C₁₈ column, 20-50% MeCN: 10 mM NH₄HCO₃ in H₂O) to give N-[4-(2-{5-chloro-2-oxo-1,2-dihydrospiro[indole-3,4'-piperidin]-1'-yl}ethoxy)phenyl]methanesulfonamide (Compound 214). MS=450.2 [M+H]⁺.

Example 30

5-chloro-1'-[2-(4-{[(trans)-3-hydroxycyclobutyl]sulfonyl}phenoxy)ethyl]-1,2-dihydrospiro[indole-3, 4'-piperidin]-2-one (Compound 215)

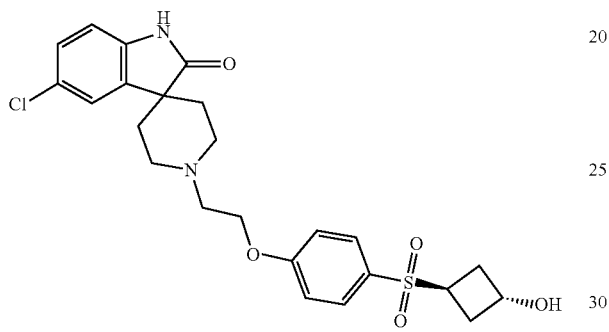

Step 1: (trans)-3-[4-(2-{5-chloro-2-oxo-1,2-dihydrospiro[indole-3,4'-piperidin]-1'-yl}ethoxy)benzenesulfonyl]cyclobutyl 4-nitrobenzoate

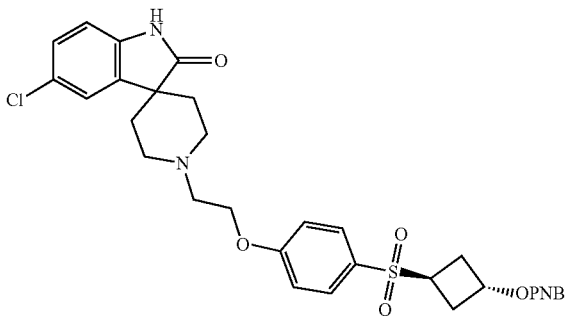

To a 0° C. solution of 5-chloro-1'-[2-(4-{[(cis)-3-hydroxycyclobutyl]sulfonyl}phenoxy)ethyl]-1,2-dihydrospiro[indole-3,4'-piperidin]-2-one (Compound 17, 13 mg, 26.5 µmol), 4-nitrobenzoic acid (5.00 mg, 31.8 µmol) and PPh₃ (27 mg, 106 µmol) in THF (2 mL) was added DIAD (20.6 µL, 0.106 mmol). The mixture was stirred at 40° C. for 16 h. After cooling to room temperature, the reaction mixture was diluted with H₂O (10 mL) and extracted with EtOAc (3×5 mL). The combined organic layers were washed with brine (5 mL), dried over Na₂SO₄, filtered, and concentrated in vacuo. The crude residue was purified by preparative TLC (SiO₂, DCM:MeOH=10:1) to give (trans)-3-[4-(2-{5-chloro-2-oxo-1,2-dihydrospiro[indole-3,4'-piperidin]-1'-yl}ethoxy)benzenesulfonyl]cyclobutyl 4-nitrobenzoate. MS=640.3 [M+H]⁺.

Step 2: 5-chloro-1'-[2-(4-{[(trans)-3-hydroxycyclobutyl]sulfonyl}phenoxy)ethyl]-1,2-dihydrospiro[indole-3,4'-piperidin]-2-one (Compound 215)

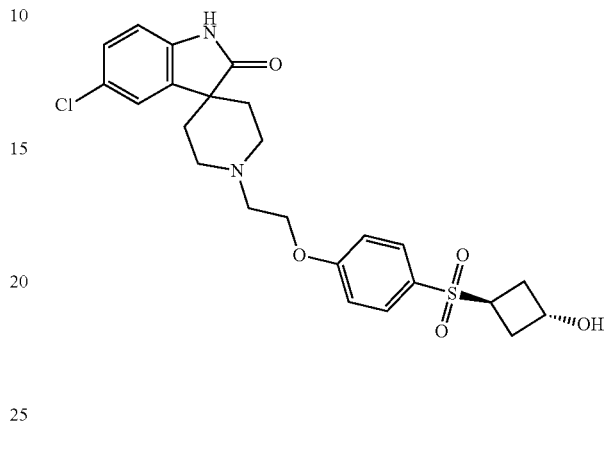

To a 0° C. solution of (trans)-3-[4-(2-{5-chloro-2-oxo-1,2-dihydrospiro[indole-3,4'-piperidin]-1'-yl}ethoxy)benzenesulfonyl]cyclobutyl 4-nitrobenzoate (10.0 mg, 15.6 µmol) in THF (2 mL) was added a solution of LiOH—H₂O (1.97 mg, 46.9 µmol) in H₂O (0.5 mL). The mixture was stirred at room temperature for 2 h. The reaction mixture was diluted with H₂O (10 mL) and extracted with EtOAc (3×5 mL). The combined organic layers were washed with brine (5 mL), dried over Na₂SO₄, filtered, and concentrated in vacuo. The residue was purified by reverse phase preparative HPLC (Waters Xbridge BEH C₁₈ column, 20-50% MeCN: 10 mM NH₄HCO₃ in H₂O) to give 5-chloro-1'-[2-(4-{[(trans)-3-hydroxycyclobutyl]sulfonyl}phenoxy)ethyl]-1,2-dihydrospiro[indole-3,4'-piperidin]-2-one (Compound 215). ¹H NMR (400 MHz, DMSO-d₆): δ 10.50 (s, 1H), 7.80 (d, J=8.8 Hz, 2H), 7.51 (d, J=2.0 Hz, 1H), 7.25-7.22 (m, 1H), 7.20 (d, J=8.8 Hz, 2H), 6.84 (d, J=8.4 Hz, 1H), 5.36-5.33 (m, 1H), 4.27-4.21 (m, 3H), 3.89-3.81 (m, 1H), 2.95-2.87 (m, 4H), 2.72-2.67 (m, 4H), 2.18-2.11 (m, 2H), 1.81-1.68 (m, 4H). MS=491.1 [M+H]⁺.

Example 31

5-chloro-1'-{2-[3-(1,2-dihydroxyethyl)-4-methanesulfonylphenoxy]ethyl}-1,2-dihydrospiro[indole-3,4'-piperidin]-2-one (Compound 216)

5-chloro-1'-{2-[3-(1,2-difluoroethyl)-4-methanesulfonylphenoxy]ethyl}-1,2-dihydrospiro[indole-3,4'-piperidin]-2-one (Compound 217)

5-chloro-1'-(2-{3-[(1S or 1R)-1,2-difluoroethyl]-4-methanesulfonylphenoxy}ethyl)-1,2-dihydrospiro[indole-3,4'-piperidin]-2-one (Compound 218) and 5-chloro-1'-(2-{3-[(1R or 1S)-1,2-difluoroethyl]-4-methanesulfonylphenoxy}ethyl)-1,2-dihydrospiro[indole-3,4'-piperidin]-2-one (Compound 219)

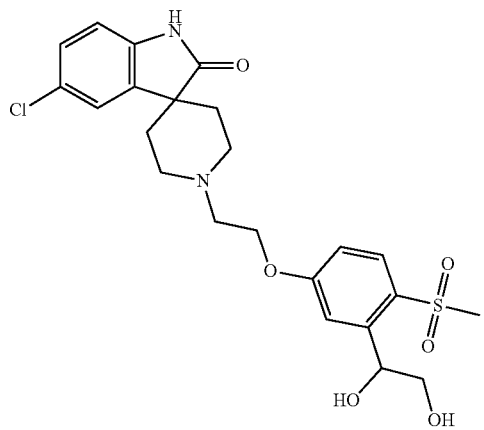

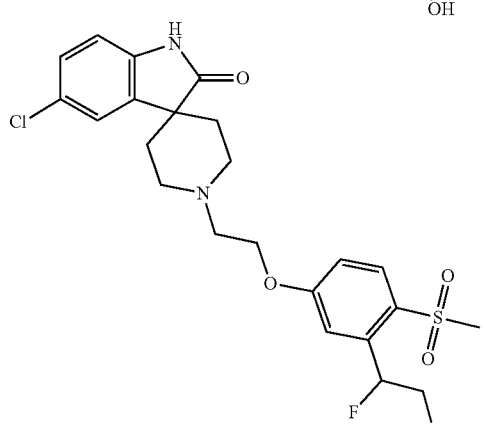

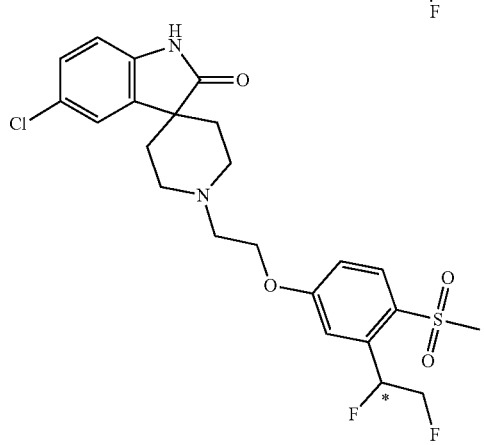

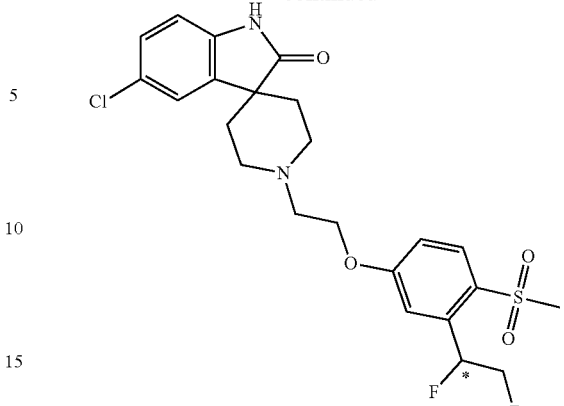

Step 1: 3-iodo-4-methanesulfonylphenol

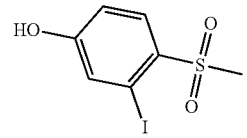

To a −20° C. solution of 2-iodo-1-methanesulfonyl-4-methoxybenzene (2.00 g, 6.41 mmol) in DCM (30 mL) under N₂ atmosphere was added BBr₃ (1.85 mL, 19.2 mmol) dropwise. The mixture was stirred at room temperature for 6 h. The reaction mixture was cooled to 0° C., quenched with H₂O (30 mL), and extracted with DCM (3×20 mL). The combined organic layers were washed with brine (15 mL), dried over Na₂SO₄, filtered, and concentrated in vacuo to give 3-iodo-4-methanesulfonylphenol, which was used in the subsequent step without further purification. MS=299.0 [M+H]⁺.

Step 2: 4-(2-bromoethoxy)-2-iodo-1-methanesulfonylbenzene

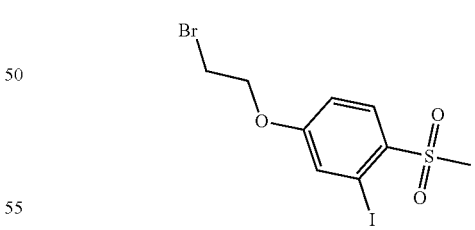

To a solution of 3-iodo-4-methanesulfonylphenol (1.90 g, 6.37 mmol) in DMF (5 mL) were added 1,2-dibromoethane (7.21 mL, 95.6 mmol) and K₂CO₃ (2.20 g, 15.9 mmol). The mixture was stirred at 80° C. for 5 h. After cooling to room temperature, the reaction mixture was quenched with H₂O (15 mL) and extracted with EtOAc (3×20 mL). The combined organic layers were washed with brine (2×15 mL), dried over Na₂SO₄, filtered, and concentrated in vacuo. The crude residue was purified by normal phase silica gel chromatography (Biotage 20 g cartridge, 0-35% EtOAc:

petroleum ether) to give 4-(2-bromoethoxy)-2-iodo-1-methanesulfonylbenzene. MS=404.9/406.9 [M+H]⁺.

Step 3: 5-chloro-1'-[2-(3-iodo-4-methanesulfonylphenoxy)ethyl]-1,2-dihydrospiro[indole-3,4'-piperidin]-2-one

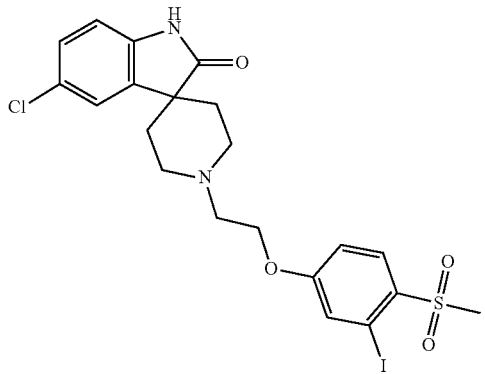 [SMILES: CS(=O)(=O)c1ccc(OCCN2CCC3(CC2)C(=O)Nc2ccc(Cl)cc23)cc1I]

To a solution of 5-chloro-1,2-dihydrospiro[indole-3,4'-piperidin]-2-one (Intermediate B-4, 1.38 g, 5.04 mmol, HCl salt) in MeCN (20 mL) was added NaHCO₃ (705 mg, 8.39 mmol) and 4-(2-bromoethoxy)-2-iodo-1-methanesulfonylbenzene (1.70 g, 4.20 mmol). The mixture was stirred at 80° C. for 12 h. After cooling to room temperature, solids were removed by filtration and the filtrate was concentrated in vacuo. The crude residue was purified by normal phase silica gel chromatography (Biotage 20 g cartridge, 0-100% EtOAc:petroleum ether) to give 5-chloro-1'-[2-(3-iodo-4-methanesulfonylphenoxy)ethyl]-1,2-dihydrospiro[indole-3,4'-piperidin]-2-one. MS=561.1 [M+H]⁺.

Step 4: 5-chloro-1'-[2-(3-ethenyl-4-methanesulfonylphenoxy)ethyl]-1,2-dihydrospiro[indole-3,4'-piperidin]-2-one

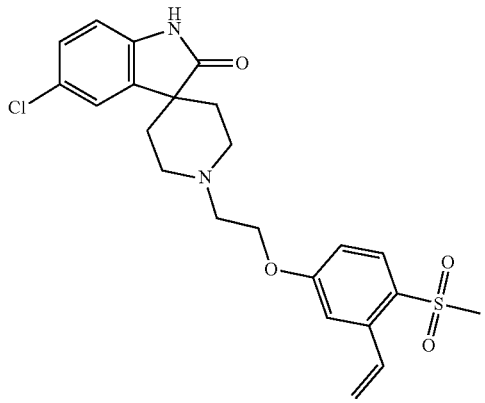 [SMILES: C=Cc1cc(OCCN2CCC3(CC2)C(=O)Nc2ccc(Cl)cc23)ccc1S(C)(=O)=O]

A solution of potassium vinyltrifluoroborate (1.15 g, 8.56 mmol), 5-chloro-1'-[2-(3-iodo-4-methanesulfonylphenoxy)ethyl]-1,2-dihydrospiro[indole-3,4'-piperidin]-2-one (1.60 g, 2.85 mmol), K₂CO₃ (1.18 g, 8.56 mmol), and Pd(dppf)Cl₂—CH₂Cl₂ (233 mg, 0.286 mmol) in 1,4-dioxane (15 mL) and H₂O (2 mL) was degassed and purged with N₂ (3×). The mixture was stirred at 100° C. for 12 h under N₂ atmosphere. After cooling to room temperature, solids were removed by filtration and the filtrate was concentrated in vacuo. The crude residue was purified by normal phase silica gel chromatography (Biotage 12 g cartridge, 0-100% EtOAc:petroleum ether) to give 5-chloro-1'-[2-(3-ethenyl-4-methanesulfonylphenoxy)ethyl]-1,2-dihydrospiro[indole-3,4'-piperidin]-2-one. MS=461.2 [M+H]⁺.

Step 5: 5-chloro-1'-{2-[3-(1,2-dihydroxyethyl)-4-methanesulfonylphenoxy]ethyl}-1,2-dihydrospiro[indole-3,4'-piperidin]-2-one (Compound 216)

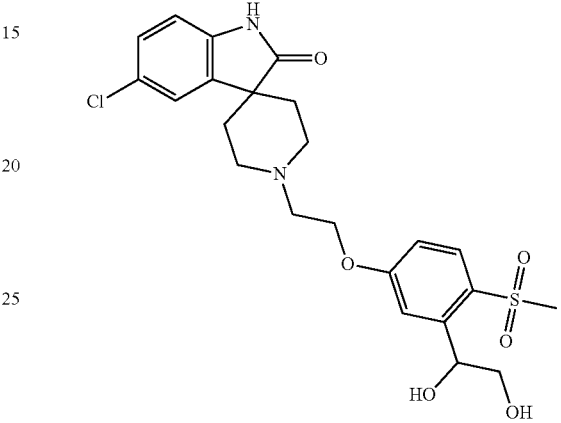

To a 0° C. solution of 5-chloro-1'-[2-(3-ethenyl-4-methanesulfonylphenoxy)ethyl]-1,2-dihydrospiro[indole-3,4'-piperidin]-2-one (1.10 g, 2.39 mmol) in THF (8 mL) and H₂O (2 mL) was added NMO (756 μL, 7.16 mmol) and K₂OsO₄·2H₂O (87.9 mg, 0.238 mmol) dropwise. The mixture was stirred at room temperature for 12 h. The reaction mixture was cooled to 0° C., quenched with H₂O (15 mL), and then extracted with EtOAc (3×15 mL). The combined organic layers were washed with brine (15 mL), dried over Na₂SO₄, filtered, and concentrated in vacuo. The crude residue was purified by normal phase silica gel chromatography (Biotage 20 g cartridge, 0-100% EtOAc:petroleum ether). The crude product was further purified by reverse phase preparative HPLC (Waters Xbridge BEH C₁₈ column, 15-45% MeCN: 10 mM NH₄HCO₃ in H₂O) to give 5-chloro-1'-{2-[3-(1,2-dihydroxyethyl)-4-methanesulfonylphenoxy]ethyl}-1,2-dihydrospiro[indole-3,4'-piperidin]-2-one (Compound 216). ¹H NMR (400 MHz, DMSO-d₆): δ 10.49 (s, 1H), 7.82 (d, J=8.8 Hz, 1H), 7.51 (s, 1H), 7.27-7.22 (m, 2H), 7.09 (d, J=8.8 Hz, 1H), 6.84 (d, J=8.4 Hz, 1H), 5.50 (d, J=4.8 Hz, 1H), 5.41-5.38 (m, 1H), 4.85 (t, J=5.6 Hz, 1H), 4.25-4.21 (m, 2H), 3.55-3.53 (m, 1H), 3.49-3.46 (m, 1H), 3.20 (s, 3H), 2.95-2.87 (m, 4H), 2.72-2.70 (m, 2H), 1.81-1.73 (m, 4H). MS=495.1 [M+H]⁺.

Step 6: 5-chloro-1'-{2-[3-(1,2-difluoroethyl)-4-methanesulfonylphenoxy]ethyl}-1,2-dihydrospiro[indole-3,4'-piperidin]-2-one (Compound 217)

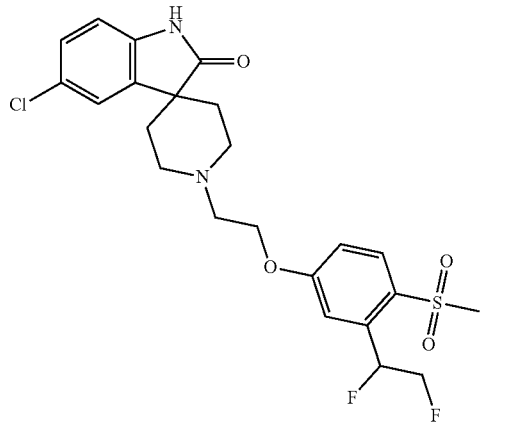 [SMILES: CS(=O)(=O)c1ccc(OCCN2CCC3(CC2)C(=O)Nc2ccc(Cl)cc23)cc1C(F)CF]

To a −30° C. solution of 5-chloro-1'-{2-[3-(1,2-dihydroxyethyl)-4-methanesulfonylphenoxy]ethyl}-1,2-dihydrospiro[indole-3,4'-piperidin]-2-one (Compound 216, 300 mg, 0.606 mmol) in THF (5 mL) was added DAST (400 μL, 3.03 mmol). The mixture was allowed to warm to room temperature and stirred for 10 h. The reaction mixture was cooled to 0° C. and quenched with H$_2$O (10 mL) at 0° C., and then extracted with DCM (2×15 mL). The combined organic layers were washed with brine (10 mL), dried over Na$_2$SO$_4$, filtered, and concentrated in vacuo. The crude residue was purified by reverse phase preparative HPLC (Waters Xbridge BEH C$_{18}$ column, 15-65% MeCN: 10 mM NH$_4$HCO$_3$ in H$_2$O) to give 5-chloro-1'-{2-[3-(1,2-difluoroethyl)-4-methanesulfonylphenoxy]ethyl}-1,2-dihydrospiro[indole-3,4'-piperidin]-2-one (Compound 217). $^1$H NMR (400 MHz, DMSO-d$_6$): δ 10.49 (s, 1H), 7.93 (d, J=8.8 Hz, 1H), 7.50 (s, 1H), 7.29-7.22 (m, 3H), 6.84 (d, J=8.4 Hz, 1H), 6.62-6.45 (m, 1H), 4.87-4.75 (m, 2H), 4.32-4.27 (m, 2H), 3.29 (s, 3H), 2.93-2.87 (m, 4H), 2.70-2.67 (m, 2H), 1.78-1.72 (m, 4H). MS=499.1 [M+H]$^+$.

Step 7: 5-chloro-1'-(2-{3-[(1R or 1S)-1,2-difluoroethyl]-4-methanesulfonylphenoxy}ethyl)-1,2-dihydrospiro[indole-3,4'-piperidin]-2-one (Compound 218) and

5-chloro-1'-(2-{3-[(1S or 1R)-1,2-difluoroethyl]-4-methanesulfonylphenoxy}ethyl)-1,2-dihydrospiro[indole-3,4'-piperidin]-2-one (Compound 219)

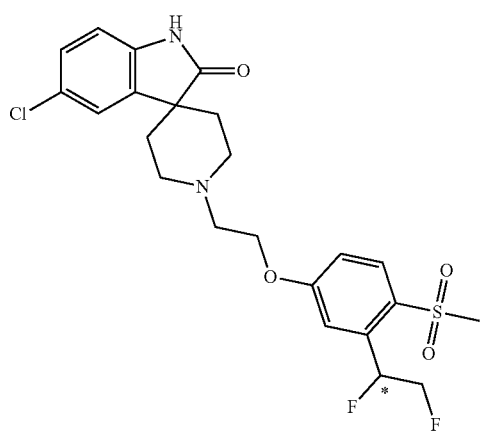

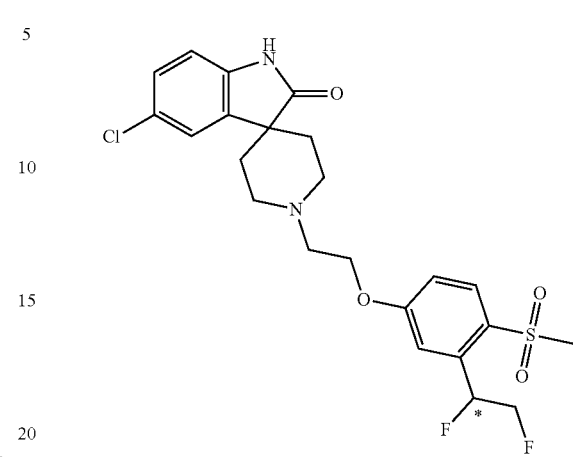

5-chloro-1'-{2-[3-(1,2-difluoroethyl)-4-methanesulfonylphenoxy]ethyl}-1,2-dihydrospiro[indole-3,4'-piperidin]-2-one (Compound 217, 110 mg, 0.216 mmol) was separated by preparative chiral SFC (Daicel Chiralcel OJ-3, 25% EtOH with 0.1% NH$_4$OH in CO$_2$). 42% ethanol with 0.1% NH$_4$OH in CO$_2$). The second eluting enantiomer of the title compound, Compound 218: $^1$H NMR (400 MHz, DMSO-d$_6$): δ 10.49 (s, 1H), 7.93 (d, J=8.8 Hz, 1H), 7.50 (s, 1H), 7.29-7.23 (m, 3H), 6.84 (d, J=8.0 Hz, 1H), 6.62-6.45 (m, 1H), 4.87-4.75 (m, 2H), 4.32-4.27 (m, 2H), 3.29 (s, 3H), 2.93-2.87 (m, 4H), 2.70-2.67 (m, 2H), 1.78-1.68 (m, 4H). MS=499.1 [M+H]$^+$. The first eluting enantiomer of the title compound, Compound 219: $^1$H NMR (400 MHz, DMSO-d$_6$): δ 10.49 (s, 1H), 7.93 (d, J=8.8 Hz, 1H), 7.50 (s, 1H), 7.29-7.22 (m, 3H), 6.84 (d, J=8.4 Hz, 1H), 6.62-6.50 (m, 1H), 4.87-4.75 (m, 2H), 4.31-4.27 (m, 2H), 3.29 (s, 3H), 2.93-2.87 (m, 4H), 2.70-2.67 (m, 2H), 1.78-1.72 (m, 4H). MS=499.1 [M+H]$^+$.

The following compounds in Table 33 were prepared according to procedures analogous to those described for Compounds 217-219 using the appropriate starting materials.

TABLE 33

| # | Structure | Name | Exact Mass [M + H]+ | Intermediates Used | Elution Order | Chiral Column |
|---|---|---|---|---|---|---|
| 220 | 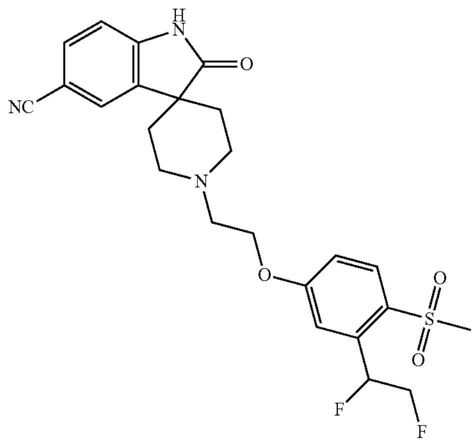 [SMILES: CS(=O)(=O)c1ccc(OCCN2CCC3(CC2)C(=O)Nc2ccc(C#N)cc23)cc1C(F)CF] | 1'-{2-[3-(1,2-difluoroethyl)-4-methanesulfonyl-phenoxy]ethyl}-2-oxo-1,2-dihydrospiro[indole-3,4'-piperidine]-5-carbonitrile | Calc'd 490.2 Found 490.0 | B-9 | n/a | n/a |
| 221 | 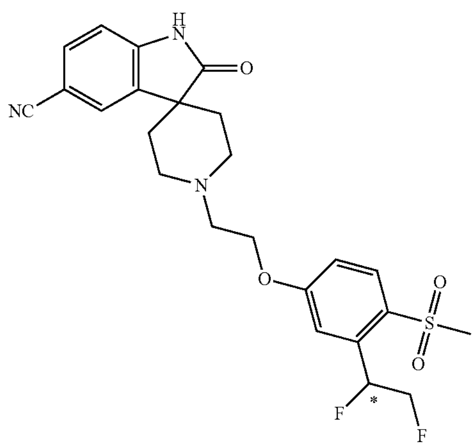 [SMILES: CS(=O)(=O)c1ccc(OCCN2CCC3(CC2)C(=O)Nc2ccc(C#N)cc23)cc1C(F)CF] | 1'-(2-{3-[(1S or 1R)-1,2-difluoroethyl]-4-methanesulfonyl-phenoxy}ethyl)-2-oxo-1,2-dihydrospiro[indole-3,4'-piperidine]-5-carbonitrile | Calc'd 490.2 Found | B-9 | Second | Daicel chiralcel OD-3 |
| 222 | 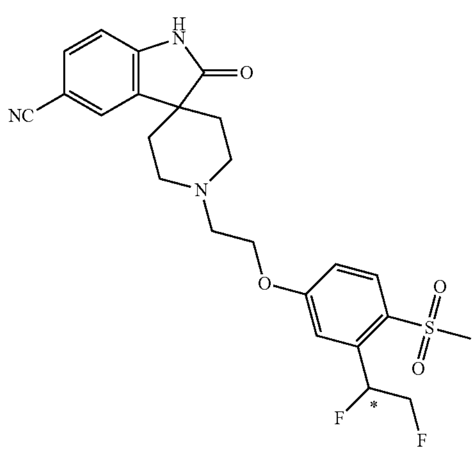 [SMILES: CS(=O)(=O)c1ccc(OCCN2CCC3(CC2)C(=O)Nc2ccc(C#N)cc23)cc1C(F)CF] | 1'-(2-{3-[(1R or 1S)-1,2-difluoroethyl]-4-methanesulfonyl-phenoxy}ethyl)-2-oxo-1,2-dihydrospiro[indole-3,4'-piperidine]-5-carbonitrile | Calc'd 490.2 Found | B-9 | First | Daicel Chiralcel OD-3 |

Example 32

5-chloro-1'-{2-[4-methanesulfonyl-3-(oxetan-3-yl)phenoxy]ethyl}-1,2-dihydrospiro[indole-3,4'-piperidin]-2-one (Compound 223)

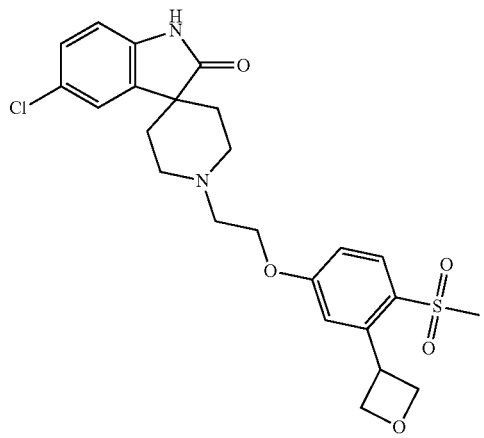 [SMILES: CS(=O)(=O)c1ccc(OCCN2CCC3(CC2)C(=O)Nc2ccc(Cl)cc23)cc1C1COC1]

To a solution of 5-chloro-1'-[2-(3-iodo-4-methanesulfonylphenoxy)ethyl]-1,2-dihydrospiro[indole-3,4'-piperidin]-2-one (Example 31: Step 3, 100 mg, 0.178 mmol) and 3-iodooxetane (328 mg, 1.78 mmol) in DME (3 mL) under $N_2$ atmosphere was added nickel(II) chloride ethylene glycol dimethyl ether complex (0.20 mg, 0.91 μmol), 4,4'-di-tert-butyl-2,2'-dipyridyl (0.24 mg, 0.89 μmol), (Ir[dF(CF$_3$)ppy]2(dtbpy))PF$_6$ (2.0 mg, 1.8 μmol), bis(trimethylsilyl)silyltrimethyl-silane (55.0 μL, 0.178 mmol) and Na$_2$CO$_3$ (37.8 mg, 0.357 mmol). The mixture was stirred at room temperature under 35 W blue LED lights for 15 h. Solids were removed by filtration, and the filtrate was concentrated in vacuo. The crude residue was purified by reverse phase preparative HPLC (Phenomenex C$_{18}$ column, 20-50% MeCN: 10 mM NH$_4$HCO$_3$ in H$_2$O) to give 5-chloro-1'-{2-[4-methanesulfonyl-3-(oxetan-3-yl)phenoxy]ethyl}-1,2-dihydrospiro[indole-3,4'-piperidin]-2-one (Compound 223). $^1$H NMR (400 MHz, DMSO-d$_6$): δ 10.49 (s, 1H), 7.88 (d, J=8.8 Hz, 1H), 7.51-7.47 (m, 2H), 7.24 (dd, J=8.0, 2.0 Hz, 1H), 7.13 (dd, J=8.8, 2.4 Hz, 1H), 6.85 (d, J=8.4 Hz, 1H), 4.93-4.92 (m, 3H), 4.72-4.69 (m, 2H), 4.32 (t, J=5.6 Hz, 2H), 3.16 (s, 3H), 2.95-2.89 (m, 4H), 2.74-2.70 (m, 2H), 1.82-1.70 (m, 4H). MS=491.0 [M+H]$^+$.

Example 33

5-chloro-1'-[2-({2-oxo-1-[(trans)-3-hydroxycyclobutyl]-1,2,3,4-tetrahydroquinolin-6-yl}oxy)ethyl]-1,2-dihydrospiro[indole-3,4'-piperidin]-2-one (Compound 224)

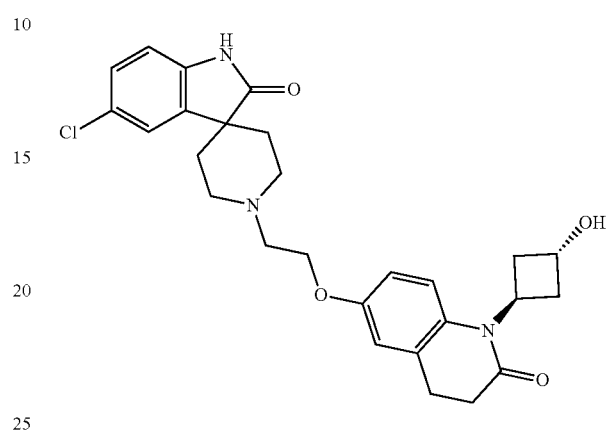

Step 1: (cis)-3-[6-(2-{5-chloro-2-oxo-1,2-dihydrospiro[indole-3,4'-piperidin]-1'-yl}ethoxy)-2-oxo-1,2,3,4-tetrahydroquinolin-1-yl]cyclobutyl methanesulfonate

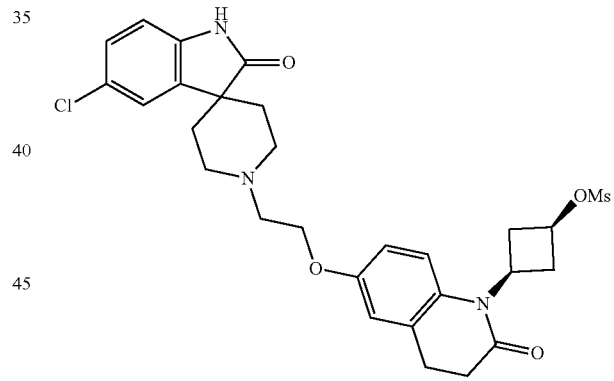

To a solution of 5-chloro-1'-[2-({2-oxo-1-[(cis)-3-hydroxycyclobutyl]-1,2,3,4-tetrahydroquinolin-6-yl}oxy)ethyl]-1,2-dihydrospiro[indole-3,4'-piperidin]-2-one (Compound 114, 50.0 mg, 0.101 mmol) in DCM (1 mL) was added TEA (28.1 μL, 0.202 mmol). The mixture was cooled to 0° C. and methanesulfonic anhydride (26.3 mg, 0.151 mmol) was added dropwise. The mixture was allowed to warm to room temperature and stirred for 2 h. The reaction mixture was cooled to 0° C., quenched with H$_2$O (8 mL), and then extracted with EtOAc (2×10 mL). The combined organic layers were washed with brine (10 mL), dried over Na$_2$SO$_4$, filtered, and concentrated in vacuo to give (cis)-3-[6-(2-{5-chloro-2-oxo-1,2-dihydrospiro[indole-3,4'-piperidin]-1'-yl}ethoxy)-2-oxo-1,2,3,4-tetrahydroquinolin-1-yl]cyclobutyl methanesulfonate, which was used in the subsequent step without further purification. MS=574.2 [M+H]$^+$.

Step 2: (trans)-3-[6-(2-{5-chloro-2-oxo-1,2-dihydrospiro[indole-3,4'-piperidin]-1'-yl}ethoxy)-2-oxo-1,2,3,4-tetrahydroquinolin-1-yl]cyclobutyl acetate

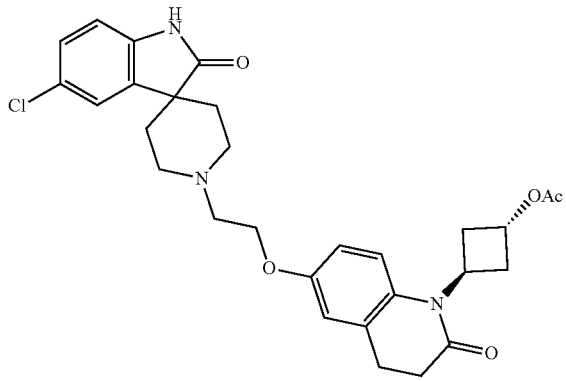 [SMILES: CC(=O)O[C@H]1C[C@H](N2C(=O)CCc3cc(OCCN4CCC5(CC4)C(=O)Nc4ccc(Cl)cc45)ccc32)C1]

To a solution of (cis)-3-[6-(2-{5-chloro-2-oxo-1,2-dihydrospiro[indole-3,4'-piperidin]-1'-yl}ethoxy)-2-oxo-1,2,3,4-tetrahydroquinolin-1-yl]cyclobutyl methanesulfonate (40.0 mg, 69.9 μmol) in DMF (1 mL) was added KOAc (68.4 mg, 0.697 mmol). The mixture was stirred at 100° C. for 12 h. After cooling to 0° C., the reaction mixture was quenched with H$_2$O (10 mL), solids were removed by filtration, and the filtrate was extracted with EtOAc (2×10 mL). The combined organic layers were washed with brine (10 mL), dried over Na$_2$SO$_4$, filtered, and concentrated in vacuo to give (trans)-3-[6-(2-{5-chloro-2-oxo-1,2-dihydrospiro[indole-3,4'-piperidin]-1'-yl}ethoxy)-2-oxo-1,2,3,4-tetrahydroquinolin-1-yl]cyclobutyl acetate, which was used in the subsequent step without further purification. MS=538.3 [M+H]$^+$.

Step 3: 5-chloro-1'-[2-({2-oxo-1-[(trans)-3-hydroxycyclobutyl]-1,2,3,4-tetrahydroquinolin-6-yl}oxy)ethyl]-1,2-dihydrospiro[indole-3,4'-piperidin]-2-one (Compound 224)

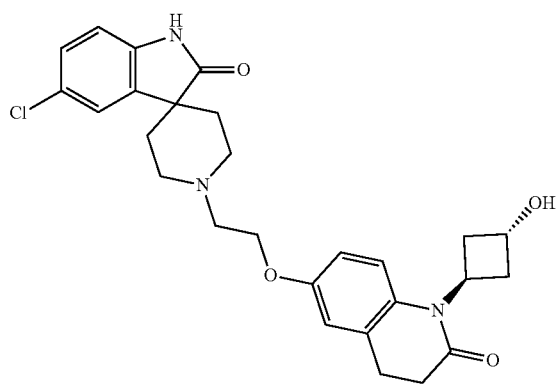 [SMILES: O=C1CCc2cc(OCCN3CCC4(CC3)C(=O)Nc3ccc(Cl)cc34)ccc2N1[C@H]1C[C@H](O)C1]

To a solution of [(trans)-3-[6-(2-{5-chloro-2-oxo-1,2-dihydrospiro[indole-3,4'-piperidin]-1'-yl}ethoxy)-2-oxo-1,2,3,4-tetrahydroquinolin-1-yl]cyclobutyl acetate (40.0 mg, 74.3 μmol) in MeOH (1 mL) was added K$_2$CO$_3$ (20.6 mg, 0.149 mmol). The mixture was stirred at room temperature for 6 h. The reaction mixture was filtered to remove solids, and the filtrate was concentrated in vacuo. The crude residue was purified by reverse phase preparative HPLC (Waters Xbridge BEH C$_{18}$ column, 20-50% MeCN: 10 mM NH$_4$HCO$_3$ in H$_2$O) to give 5-chloro-1'-[2-({2-oxo-1-[(trans)-3-hydroxycyclobutyl]-1,2,3,4-tetrahydroquinolin-6-yl}oxy)ethyl]-1,2-dihydrospiro[indole-3,4'-piperidin]-2-one (Compound 224). MS=496.2 [M+H]$^+$.

Example 34

5-chloro-1'-[2-(4-{[1-(hydroxymethyl)cyclopropyl]sulfonyl}phenoxy)ethyl]-1,2-dihydrospiro[indole-3,4'-piperidin]-2-one (Compound 225)

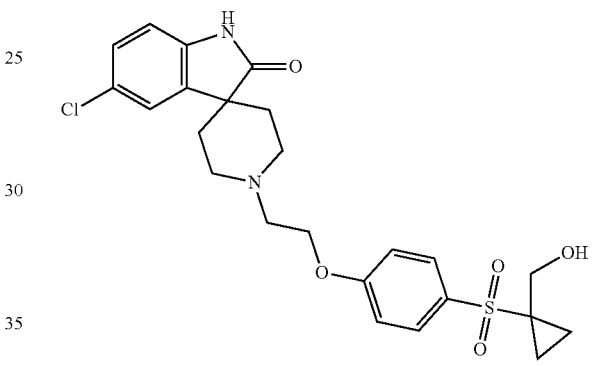

A solution of methyl 1-[4-(2-{5-chloro-2-oxo-1,2-dihydrospiro[indole-3,4'-piperidin]-1'-yl}ethoxy)benzenesulfonyl]cyclopropane-1-carboxylate (Compound 91, 180 mg, 0.347 mmol) in THF (3 mL) was degassed and purged with N$_2$ (3×). The mixture was cooled to 0° C. and 2.0 M LiBH$_4$ in THF (21.4 mL, 42.8 mmol) was added. After stirring at 0° C. for 3 h, the mixture was allowed to warm to room temperature and stirred for another 13 h. The reaction mixture was cooled to 0° C., quenched with H$_2$O (5 mL), and then adjusted to pH=6 with 4.0 M aqueous HCl. The combined organic layers were washed with brine (2×6 mL), dried over Na$_2$SO$_4$, filtered, and concentrated in vacuo. The crude residue was purified by reverse phase preparative HPLC (Waters Xbridge BEH C$_{18}$ column, 25-55% MeCN: 10 mM NH$_4$HCO$_3$ in H$_2$O) to give 5-chloro-1'-[2-(4-{[1-(hydroxymethyl)cyclopropyl]sulfonyl}phenoxy)ethyl]-1,2-dihydrospiro[indole-3,4'-piperidin]-2-one (Compound 225). $^1$H NMR (400 MHz, DMSO-d$_6$): δ 10.48 (s, 1H), 7.77 (d, J=8.8 Hz, 2H), 7.50 (d, J=2 Hz, 1H), 7.23 (d, J=8.4 Hz, 1H), 7.17 (d, J=8.8 Hz, 2H), 6.84 (d, J=8.4 Hz, 1H), 4.85 (t, J=6.4 Hz, 1H), 4.25 (t, J=5.6 Hz, 2H), 3.61 (d, J=6.4 Hz, 2H), 2.93-2.87 (m, 4H), 2.72-2.70 (m, 2H), 1.78-1.72 (m, 4H), 1.30 (t, J=4.4 Hz, 2H), 1.01 (t, J=4.8 Hz, 2H). MS=491.1 [M+H]$^+$.

Example 35

1-[4-(2-{5-chloro-2-oxo-1,2-dihydrospiro[indole-3,4'-piperidin]-1'-yl}ethoxy)benzenesulfonyl]-N-methylcyclopropane-1-carboxamide (Compound 226)

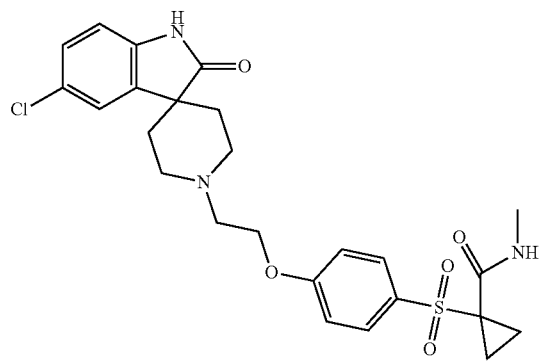

Step 1: 1-[4-(2-{5-chloro-2-oxo-1,2-dihydrospiro[indole-3,4'-piperidin]-1'-yl}ethoxy)benzenesulfonyl]cyclopropane-1-carboxylic acid

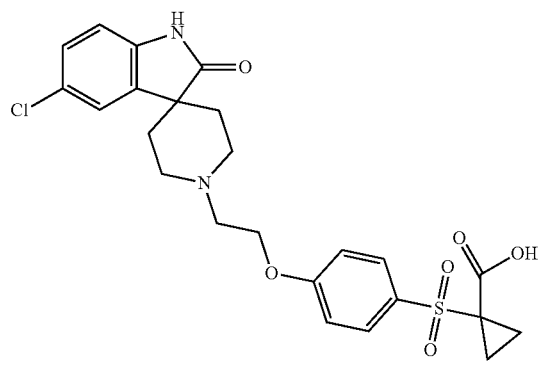 [SMILES: O=C1Nc2ccc(Cl)cc2C12CCN(CCOc1ccc(S(=O)(=O)C3(C(=O)O)CC3)cc1)CC2]

To a solution of methyl 1-[4-(2-{5-chloro-2-oxo-1,2-dihydrospiro[indole-3,4'-piperidin]-1'-yl}ethoxy)benzenesulfonyl]cyclopropane-1-carboxylate (Compound 91, 1.30 g, 2.50 mmol) in MeOH (8 mL) and H$_2$O (8 mL) was added LiOH·H$_2$O (210 mg, 5.01 mmol). The mixture was stirred at room temperature for 3 h. The reaction mixture was concentrated in vacuo, and the residue was adjusted to pH=4 with 1.0 M aqueous HCl. The resulting solid was collected via filtration and dried in vacuo to give 1-[4-(2-{5-chloro-2-oxo-1,2-dihydrospiro[indole-3,4'-piperidin]-1'-yl}ethoxy)benzenesulfonyl]cyclopropane-1-carboxylic acid, which was used in the subsequent step without further purification. $^1$H NMR (400 MHz, DMSO-d$_6$, 24/25 H): δ 10.55 (s, 1H), 7.90 (d, J=8.8 Hz, 2H), 7.51 (d, J=1.6 Hz, 1H), 7.26 (dd, J=8.4, 3.0 Hz, 1H), 7.10 (d, J=8.8 Hz, 2H), 6.85 (d, J=8.4 Hz, 1H), 4.28 (t, J=5.2 Hz, 2H), 3.13-3.10 (m, 4H), 2.93-2.90 (m, 2H), 1.86-1.84 (m, 4H), 1.70-1.68 (m, 2H), 1.51-1.49 (m, 2H). MS=505.0 [M+H]$^+$.

Step 2: 1-[4-(2-{5-chloro-2-oxo-1,2-dihydrospiro[indole-3,4'-piperidin]-1'-yl}ethoxy)benzenesulfonyl]-N-methylcyclopropane-1-carboxamide (Compound 226)

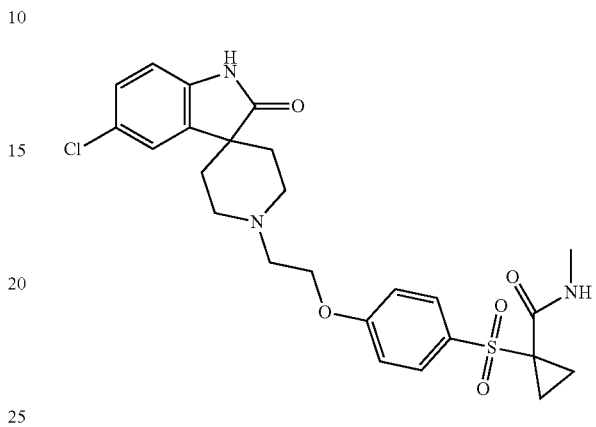

To a 0° C. solution of 1-[4-(2-{5-chloro-2-oxo-1,2-dihydrospiro[indole-3,4'-piperidin]-1'-yl}ethoxy)benzenesulfonyl]cyclopropane-1-carboxylic acid (120 mg, 0.238 mmol) in DCM (2 mL) was added methylamine hydrochloride (160 mg, 2.38 mmol), TEA (198 μL, 1.43 mmol), and then 60% T3P in EtOAc (252 mg, 0.475 mmol). The mixture was allowed to warm to room temperature and stirred for 16 h. The reaction mixture was quenched with H$_2$O (8 mL) and extracted with EtOAc (2×10 mL). The combined organic layers were washed with brine (2×10 mL), dried over anhydrous Na$_2$SO$_4$, filtered and concentrated in vacuo. The crude residue was purified by reverse phase preparative HPLC (Phenomenex C$_{18}$ column, 20-60% MeCN: 10 mM NH$_4$HCO$_3$ in H$_2$O) to give 1-[4-(2-{5-chloro-2-oxo-1,2-dihydrospiro[indole-3,4'-piperidin]-1'-yl}ethoxy)benzenesulfonyl]-N-methylcyclopropane-1-carboxamide (Compound 226). $^1$H NMR (400 MHz, DMSO-d$_6$): δ 10.48 (s, 1H), 7.94 (d, J=4.4 Hz, 1H), 7.82-7.80 (m, 2H), 7.51 (d, J=2.4 Hz, 1H), 7.24 (dd, J=8.4, 2.0 Hz, 1H), 7.18-7.16 (m, 2H), 6.85 (d, J=8.0 Hz, 1H), 4.28 (t, J=5.6 Hz, 2H), 2.93-2.87 (m, 4H), 2.72-2.69 (m, 2H), 2.59 (d, J=4.4 Hz, 3H), 1.79-1.74 (m, 4H), 1.59-1.57 (m, 2H), 1.43-1.41 (m, 2H). MS=518.1 [M+H]$^+$.

The following compounds in Table 34 were prepared according to procedures similar to step 2 described for Compound 226 using the appropriate starting materials.

TABLE 34

| # | Structure | Name | Exact Mass [M + H]⁺ |
|---|---|---|---|
| 227 | 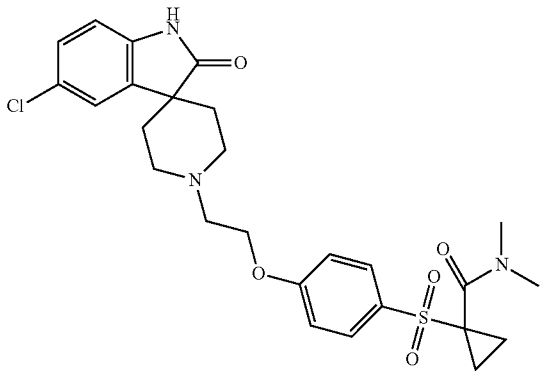 [SMILES: CN(C)C(=O)C1(S(=O)(=O)c2ccc(OCCN3CCC4(CC3)C(=O)Nc3ccc(Cl)cc34)cc2)CC1] | 1-[4-(2-{5-chloro-2-oxo-1,2-dihydrospiro[indole-3,4'-piperidin]-1'-yl}ethoxy)benzenesulfonyl]-N,N-dimethylcyclopropane-1-carboxamide | Calc'd 532.2 Found 532.1 |
| 228 | 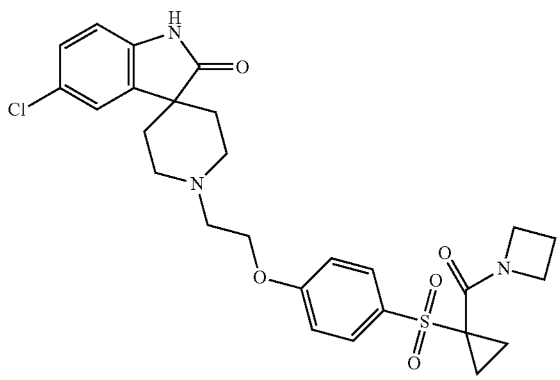 [SMILES: O=C1Nc2ccc(Cl)cc2C12CCN(CCOc1ccc(S(=O)(=O)C3(C(=O)N4CCC4)CC3)cc1)CC2] | 1'-[2-(4-{[1-(azetidine-1-carbonyl)cyclopropyl]sulfonyl}phenoxy)ethyl]-5-chloro-1,2-dihydrospiro[indole-3,4'-piperidin]-2-one | Calc'd 544.2 Found 544.0 |

Example 36

4-(2-{5-chloro-2-oxo-1,2-dihydrospiro[indole-3,4'-piperidin]-1'-yl}ethoxy)-2-fluoro-N-methylbenzamide (Compound 229)

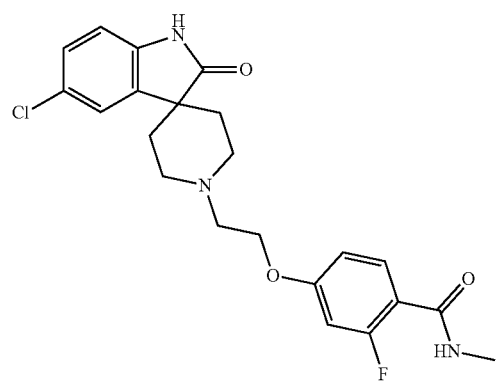 [SMILES: CNC(=O)c1ccc(OCCN2CCC3(CC2)C(=O)Nc2ccc(Cl)cc23)cc1F]

Step 1: methyl 4-(2-bromoethoxy)-2-fluorobenzoate

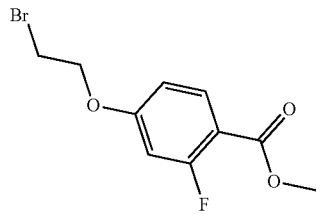

To a mixture of methyl 2-fluoro-4-hydroxybenzoate (3.00 g, 17.6 mmol) and 1,2-dibromoethane (6.65 mL, 88.2 mmol) in DMF (20 mL) was added $Cs_2CO_3$ (11.5 g, 35.3 mmol). The mixture was stirred at 100° C. for 12 h. After cooling to room temperature, the reaction mixture was quenched with $H_2O$ (20 mL) and extracted with EtOAc (3×20 mL). The combined organic layers were washed with brine (2×20 mL), dried over $Na_2SO_4$, filtered, and concentrated in vacuo. The crude residue was purified by normal phase silica gel chromatography (Biotage 40 g cartridge, 0-100% EtOAc: petroleum ether) to give methyl 4-(2-bromoethoxy)-2-fluorobenzoate. MS=277.1/279.1 [M+H]⁺.

Step 2: methyl 4-(2-{5-chloro-2-oxo-1,2-dihydrospiro[indole-3,4'-piperidin]-1'-yl}ethoxy)-2-fluorobenzoate

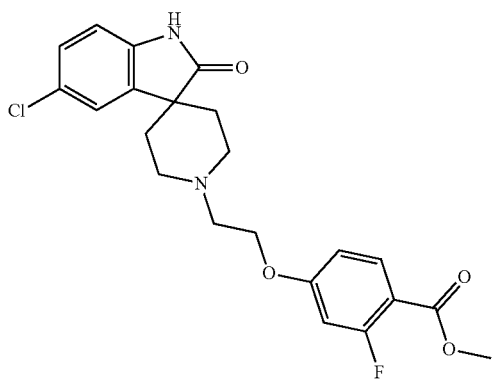 [SMILES: COC(=O)c1ccc(OCCN2CCC3(CC2)C(=O)Nc2ccc(Cl)cc23)cc1F]

To a mixture of 5-chloro-1,2-dihydrospiro[indole-3,4'-piperidin]-2-one (Intermediate B-4, 2.00 g, 7.32 mmol, HCl salt) and methyl 4-(2-bromoethoxy)-2-fluorobenzoate (2.23 g, 8.05 mmol) in MeCN (30 mL) was added NaHCO$_3$ (923 mg, 11.0 mmol). The mixture was stirred at 80° C. for 16 h. After cooling to room temperature, the reaction mixture was quenched with H$_2$O (20 mL) and extracted with EtOAc (3×20 mL). The combined organic layers were washed with brine (2×20 mL), dried over Na$_2$SO$_4$, filtered, and concentrated in vacuo. The crude residue was purified by normal phase silica gel chromatography (Biotage 20 g cartridge, 0-100% EtOAc:petroleum ether) to give methyl 4-(2-{5-chloro-2-oxo-1,2-dihydrospiro[indole-3,4'-piperidin]-1'-yl}ethoxy)-2-fluorobenzoate. MS=433.2 [M+H]$^+$.

Step 3: 4-(2-{5-chloro-2-oxo-1,2-dihydrospiro[indole-3,4'-piperidin]-1'-yl}ethoxy)-2-fluorobenzoic acid

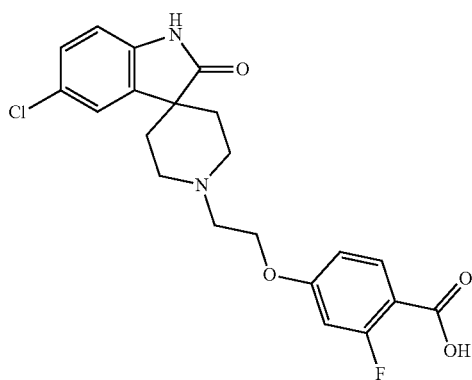 [SMILES: O=C(O)c1ccc(OCCN2CCC3(CC2)C(=O)Nc2ccc(Cl)cc23)cc1F]

To a solution of methyl 4-(2-{5-chloro-2-oxo-1,2-dihydrospiro[indole-3,4'-piperidin]-1'-yl}ethoxy)-2-fluorobenzoate (1.90 g, 4.39 mmol) in THF (15 mL) and H$_2$O (5 mL) was added LiOH—H$_2$O (315 mg, 13.2 mmol). The mixture was stirred at room temperature for 5 h. The reaction mixture was concentrated in vacuo and adjusted to pH=4 with 1.0 M aqueous HCl. The resulting solids were collected via filtration and dried in vacuo to give 4-(2-{5-chloro-2-oxo-1,2-dihydrospiro[indole-3,4'-piperidin]-1'-yl}ethoxy)-2-fluorobenzoic acid, which was used in the subsequent step without further purification. MS=419.1 [M+H]$^+$.

Step 4: 4-(2-{5-chloro-2-oxo-1,2-dihydrospiro[indole-3,4'-piperidin]-1'-yl}ethoxy)-2-fluoro-N-methylbenzamide (Compound 229)

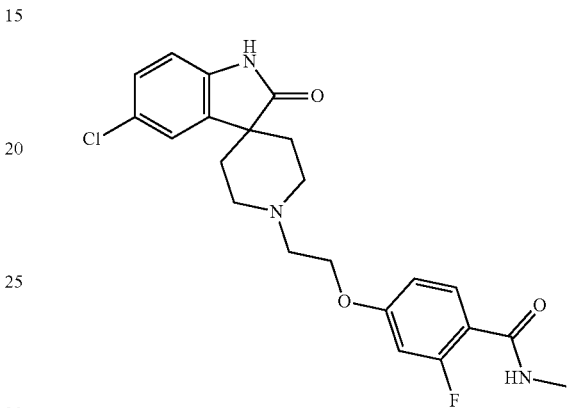

To a 0° C. solution of 4-(2-{5-chloro-2-oxo-1,2-dihydrospiro[indole-3,4'-piperidin]-1'-yl}ethoxy)-2-fluorobenzoic acid (150 mg, 0.358 mmol) in DCM (2 mL) was added TEA (150 µL, 1.07 mmol), methylamine hydrochloride (96.7 mg, 1.43 mmol), and then 60% T3P in EtOAc (380 mg, 0.716 mmol) dropwise. The mixture was allowed to warm to room temperature and stirred for 12 h. The reaction mixture was cooled to 0° C., quenched with H$_2$O (8 mL), and then extracted with EtOAc (2×10 mL). The combined organic layers were washed with brine (10 mL), dried over Na$_2$SO$_4$, filtered, and in vacuo. The crude residue was purified by reverse phase preparative HPLC (Waters Xbridge BEH C$_{18}$ column, 15-55% MeCN: 10 mM NH$_4$HCO$_3$ in H$_2$O) to give 4-(2-{5-chloro-2-oxo-1,2-dihydrospiro[indole-3,4'-piperidin]-1'-yl}ethoxy)-2-fluorobenzoic acid (Compound 229). $^1$H NMR (400 MHz, DMSO-d$_6$): δ 10.48 (s, 1H), 7.99-7.98 (m, 1H), 7.65-7.63 (m, 1H), 7.51 (s, 1H), 7.23 (dd, J=8.4, 2.0 Hz, 1H), 6.91-6.83 (m, 3H), 4.20 (t, J=5.6 Hz, 2H), 2.87-2.84 (m, 2H), 2.75 (t, J=4.4 Hz, 2H), 2.70 (d, J=4.0 Hz, 3H), 2.69-2.67 (m, 2H), 1.80-1.68 (m, 4H). MS=432.1 [M+H]$^+$.

The following compounds in Table 35 were prepared according to procedures similar to steps 1-4 described for Compound 229 using the appropriate starting materials. In cases where step 1 was followed by chiral SFC purification to separate isomers, chiral column conditions and elution order are specified.

TABLE 35

| # | Structure | Name | Exact Mass [M + H]+ | Elution Order | Chiral Column |
|---|---|---|---|---|---|
| 230 | 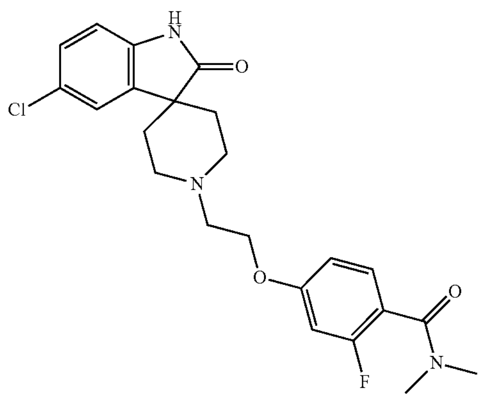 [SMILES: CN(C)C(=O)c1ccc(OCCN2CCC3(CC2)C(=O)Nc2ccc(Cl)cc23)cc1F] | 4-(2-{5-chloro-2-oxo-1,2-dihydrospiro[indole-3,4'-piperidin]-1'-yl}ethoxy)-2-fluoro-N,N-dimethylbenzamide | Calc'd 446.2 Found 446.1 | n/a | n/a |
| 231 | 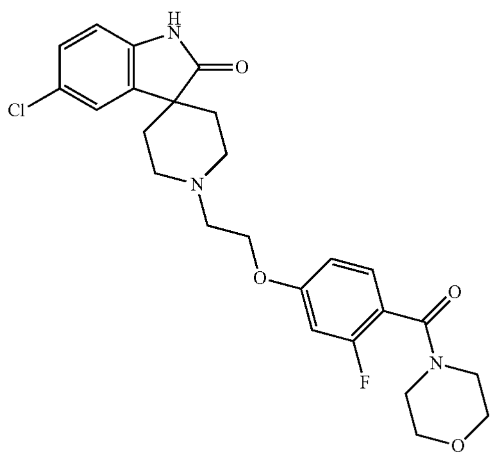 [SMILES: O=C(c1ccc(OCCN2CCC3(CC2)C(=O)Nc2ccc(Cl)cc23)cc1F)N1CCOCC1] | 5-chloro-1'-{2-[3-fluoro-4-(morpholine-4-carbonyl)phenoxy]ethyl}-1,2-dihydrospiro[indole-3,4'-piperidin]-2-one | Calc'd 488.2 Found 488.2 | n/a | n/a |
| 232 | 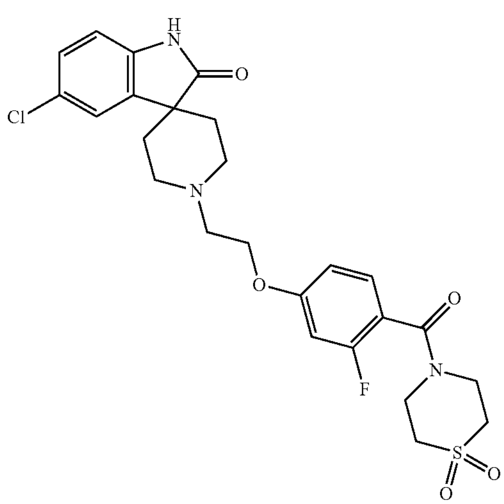 [SMILES: O=C(c1ccc(OCCN2CCC3(CC2)C(=O)Nc2ccc(Cl)cc23)cc1F)N1CCS(=O)(=O)CC1] | 4-[4-(2-{5-chloro-2-oxo-1,2-dihydrospiro[indole-3,4'-piperidin]-1'-yl}ethoxy)-2-fluorobenzoyl]-1$\lambda^6$-thiomorpholine-1,1-dione | Calc'd 536.1 Found 536.1 | n/a | n/a |

TABLE 35-continued

| # | Structure | Name | Exact Mass [M + H]+ | Elution Order | Chiral Column |
|---|-----------|------|---------------------|---------------|---------------|
| 233 | 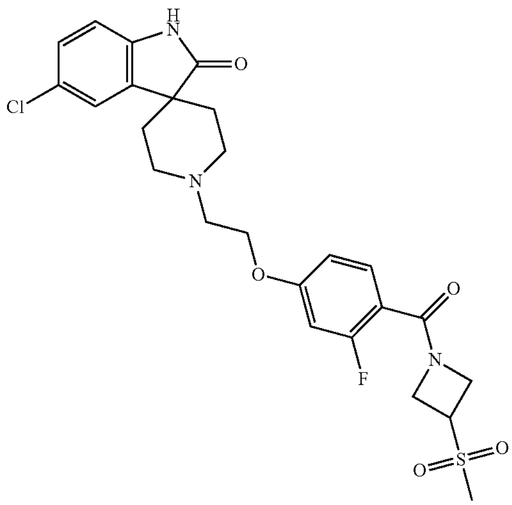 [SMILES: CS(=O)(=O)C1CN(C(=O)c2ccc(OCCN3CCC4(CC3)C(=O)Nc3ccc(Cl)cc34)cc2F)C1] | 5-chloro-1'-{2-[3-fluoro-4-(3-methanesulfonyl-azetidine-1-carbonyl)phenoxy]ethyl}-1,2-dihydrospiro[indole-3,4'-piperidin]-2-one | Calc'd 536.1 Found 536.1 | n/a | n/a |
| 234 | 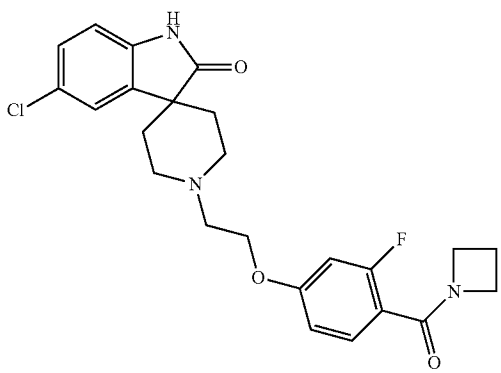 [SMILES: O=C(c1ccc(OCCN2CCC3(CC2)C(=O)Nc2ccc(Cl)cc23)cc1F)N1CCC1] | 1'-{2-[4-(azetidine-1-carbonyl)-3-fluorophenoxy]ethyl}-5-chloro-1,2-dihydrospiro[indole-3,4'-piperidin]-2-one | Calc'd 458.2 Found 458.1 | n/a | n/a |
| 235 | 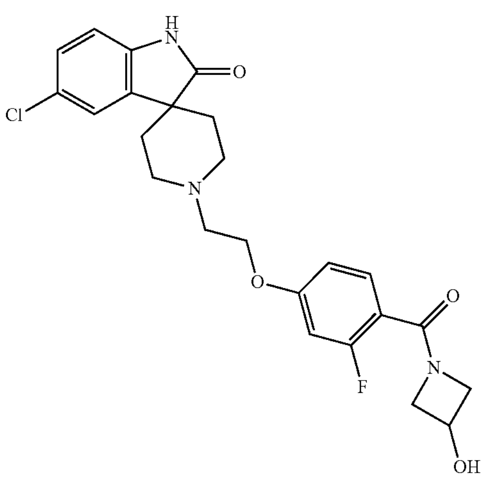 [SMILES: O=C(c1ccc(OCCN2CCC3(CC2)C(=O)Nc2ccc(Cl)cc23)cc1F)N1CC(O)C1] | 5-chloro-1'-{2-[3-fluoro-4-(3-hydroxyazetidine-1-carbonyl)phenoxy]ethyl}-1,2-dihydrospiro[indole-3,4'-piperidin]-2-one | Calc'd 474.2 Found 474.1 | n/a | n/a |

TABLE 35-continued

| # | Structure | Name | Exact Mass [M + H]+ | Elution Order | Chiral Column |
|---|---|---|---|---|---|
| 236 | 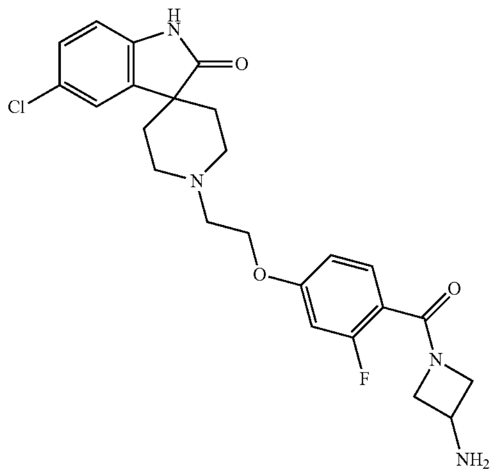 [SMILES: NC1CN(C(=O)c2ccc(OCCN3CCC4(CC3)C(=O)Nc3ccc(Cl)cc34)cc2F)C1] | 1'-{2-[4-(3-aminoazetidine-1-carbonyl)-3-fluorophenoxy]ethyl}-5-chloro-1,2-dihydrospiro[indole-3,4'-piperidin]-2-one | Calc'd 473.2 Found 473.1 | n/a | n/a |
| 237 | 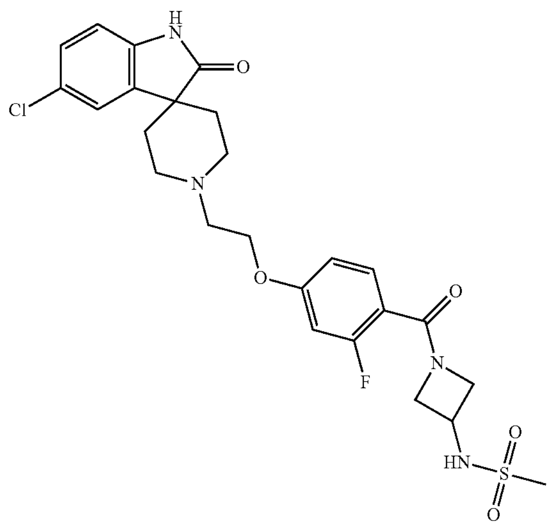 [SMILES: CS(=O)(=O)NC1CN(C(=O)c2ccc(OCCN3CCC4(CC3)C(=O)Nc3ccc(Cl)cc34)cc2F)C1] | N-{1-[4-(2-{5-chloro-2-oxo-1,2-dihydrospiro[indole-3,4'-piperidin]-1'-yl}ethoxy)-2-fluorobenzoyl]azetidin-3-yl}methanesulfonamide | Calc'd 551.1 Found 551.2 | n/a | n/a |
| 238 | 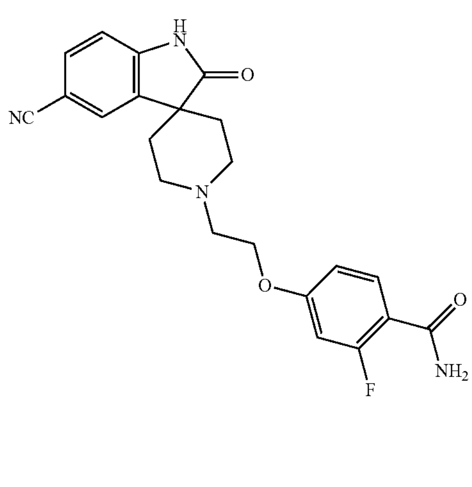 [SMILES: N#Cc1ccc2c(c1)C1(CCN(CCOc3ccc(C(N)=O)c(F)c3)CC1)C(=O)N2] | 4-(2-{5-cyano-2-oxo-1,2-dihydrospiro[indole-3,4'-piperidin]-1'-yl}ethoxy)-2-fluorobenzamide | Calc'd 409.2 Found 409.2 | n/a | n/a |

TABLE 35-continued

| # | Structure | Name | Exact Mass [M + H]+ | Elution Order | Chiral Column |
|---|---|---|---|---|---|
| 239 | 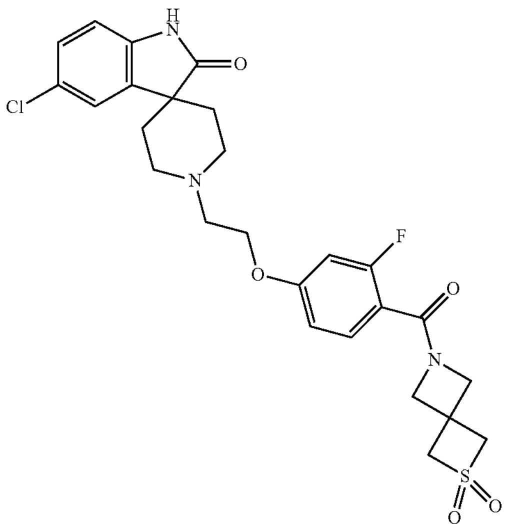 [SMILES: O=C(c1ccc(OCCN2CCC3(CC2)C(=O)Nc2ccc(Cl)cc23)cc1F)N1CC2(C1)CS(=O)(=O)C2] | 6-[4-(2-{5-chloro-2-oxo-1,2-dihydrospiro[indole-3,4'-piperidin]-1'-yl}ethoxy)-2-fluorobenzoyl]-2λ6-thia-6-azaspiro[3.3]heptane-2,2-dione | Calc'd 548.1 Found 548.2 | n/a | n/a |
| 240 | 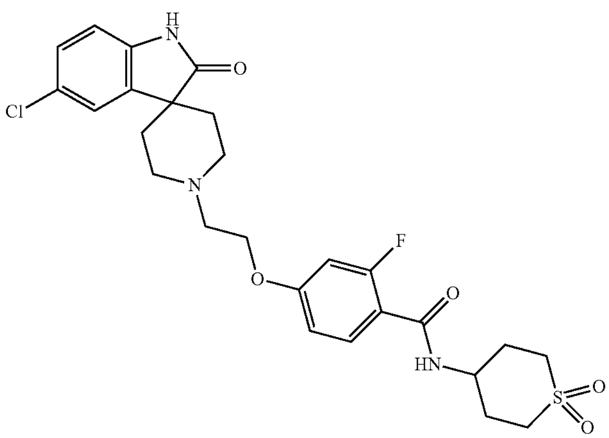 [SMILES: O=C(NC1CCS(=O)(=O)CC1)c1ccc(OCCN2CCC3(CC2)C(=O)Nc2ccc(Cl)cc23)cc1F] | 4-(2-{5-chloro-2-oxo-1,2-dihydrospiro[indole-3,4'-piperidin]-1'-yl}ethoxy)-N-(1,1-dioxo-1λ6-thian-4-yl)-2-fluorobenzamide | Calc'd 550.2 Found 550.1 | n/a | n/a |
| 241 | 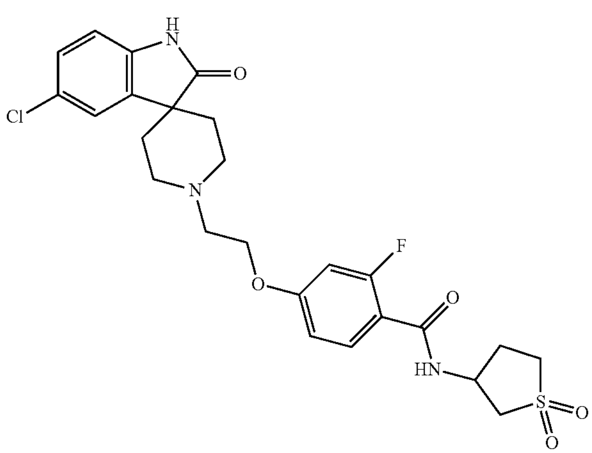 [SMILES: O=C(NC1CCS(=O)(=O)C1)c1ccc(OCCN2CCC3(CC2)C(=O)Nc2ccc(Cl)cc23)cc1F] | 4-(2-{5-chloro-2-oxo-1,2-dihydrospiro[indole-3,4'-piperidin]-1'-yl}ethoxy)-N-(1,1-dioxo-1λ6-thiolan-3-yl)-2-fluorobenzamide | Calc'd 536.1 Found 536.2 | n/a | n/a |

TABLE 35-continued

| # | Structure | Name | Exact Mass [M + H]⁺ | Elution Order | Chiral Column |
|---|---|---|---|---|---|
| 242 | 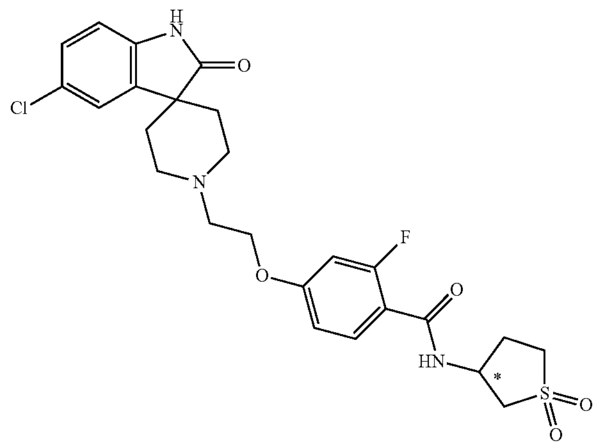 [SMILES: O=C(NC1CCS(=O)(=O)C1)c1ccc(OCCN2CCC3(CC2)C(=O)Nc2ccc(Cl)cc23)cc1F] | 4-(2-{5-chloro-2-oxo-1,2-dihydrospiro[indole-3,4'-piperidin]-1'-yl}ethoxy)-N-[(3S) or (3R)-1,1-dioxo-1λ⁶-thiolan-3-yl]-2-fluorobenzamide | Calc'd 536.1 Found 536.2 | Daicel Chiralpak OD-3 | First |
| 243 | 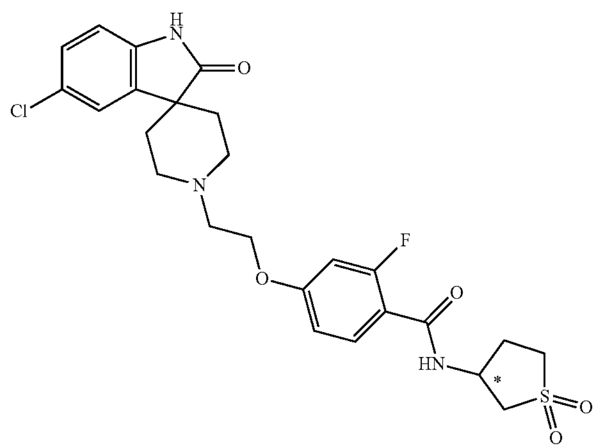 [SMILES: O=C(NC1CCS(=O)(=O)C1)c1ccc(OCCN2CCC3(CC2)C(=O)Nc2ccc(Cl)cc23)cc1F] | 4-(2-{5-chloro-2-oxo-1,2-dihydrospiro[indole-3,4'-piperidin]-1'-yl}ethoxy)-N-[(3R) or (3S)-1,1-dioxo-1λ⁶-thiolan-3-yl]-2-fluorobenzamide | Calc'd 536.1 Found 536.2 | Daicel Chiralpak OD-3 | Second |

Example 37

5-chloro-1'-{2-[4-(5-methyl-1H-pyrazol-4-yl)phenoxy]ethyl}-1,2-dihydrospiro[indole-3,4'-piperidin]-2-one (Compound 244)

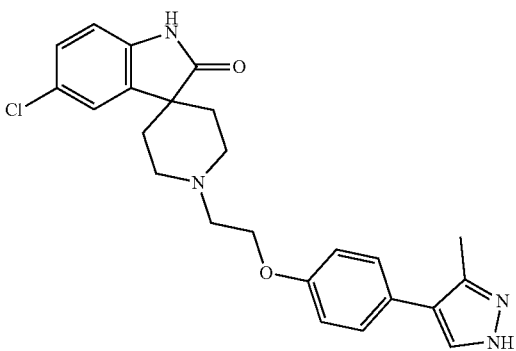 [SMILES: Cc1n[nH]cc1-c1ccc(OCCN2CCC3(CC2)C(=O)Nc2ccc(Cl)cc23)cc1]

Step 1: 1'-[2-(4-bromophenoxy)ethyl]-5-chloro-1,2-dihydrospiro[indole-3,4'-piperidin]-2-one

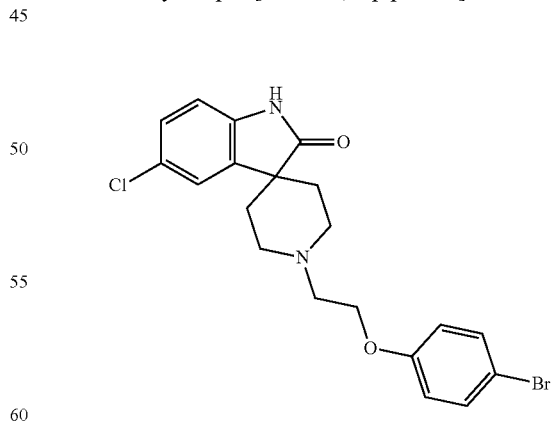

To a solution of 4-bromophenol (300 mg, 1.73 mmol) in acetone (5 mL) was added K₂CO₃ (240 mg, 1.73 mmol), 5-chloro-1'-(2-chloroethyl)-1,2-dihydrospiro[indole-3,4'-piperidin]-2-one (Intermediate B-5, 778 mg, 2.60 mmol) and NaI (13.0 mg, 86.7 μmol). The mixture was stirred at 50° C. for 16 h. After cooling to room temperature, solids were Step 2: 5-chloro-1'-{2-[4-(5-methyl-1H-pyrazol-4-yl)phenoxy]ethyl}-1,2-dihydrospiro[indole-3,4'-piperidin]-2-one (Compound 244)

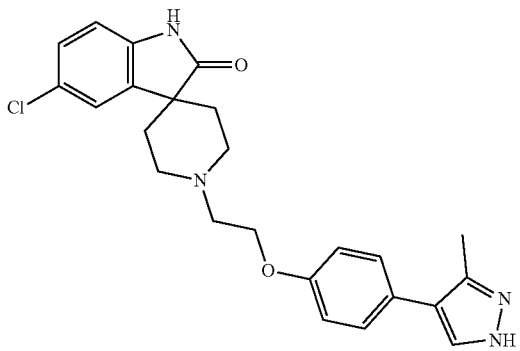 [SMILES: Cc1n[nH]cc1-c1ccc(OCCN2CCC3(CC2)C(=O)Nc2ccc(Cl)cc23)cc1]

To a solution of 1'-[2-(4-bromophenoxy)ethyl]-5-chloro-1,2-dihydrospiro[indole-3,4'-piperidin]-2-one (200 mg, 0.459 mmol) in n-butanol (4 mL) and H$_2$O (1 mL) was added 3-methyl-4-(4,4,5,5-tetramethyl-1,3,2-dioxaborolan-2-yl)-1H-pyrazole (287 mg, 1.38 mmol), KOAc (135 mg, 1.38 mmol), and bis(4-(di-tert-butylphosphanyl)-N,N-dimethylaniline) dichloropalladium (6.50 mg, 9.18 μmol). The mixture was degassed and purged with N$_2$ (3×), and heated via microwave for 2 h at 120° C. After cooling to room temperature, the mixture was filtered through Celite and the filtrate was concentrated in vacuo. The crude residue was purified by reverse phase preparative HPLC (Waters Xbridge Prep OBD C$_{18}$ column, 20-50% MeCN: 10 mM NH$_4$HCO$_3$ in H$_2$O) to give 5-chloro-1'-{2-[4-(5-methyl-1H-pyrazol-4-yl)phenoxy]ethyl}-1,2-dihydrospiro[indole-3,4'-piperidin]-2-one (Compound 244). $^1$H NMR (400 MHz, DMSO-d$_6$): δ 12.52 (s, 1H), 10.49 (s, 1H), 7.82-7.59 (m, 1H), 7.52 (s, 1H), 7.34 (d, J=8.0 Hz, 2H), 7.23 (d, J=6.4 Hz, 1H), 6.98 (d, J=8.8 Hz, 2H), 6.84 (d, J=8.4 Hz, 1H), 4.16-4.13 (m, 2H), 2.87-2.84 (m, 4H), 2.67-2.66 (m, 2H), 2.34-2.29 (m, 3H), 1.79-1.74 (m, 4H). MS=437.2 [M+H]$^+$.

Example 38

6-(2-{5-chloro-2-oxo-1,2-dihydrospiro[indole-3,4'-piperidin]-1'-yl}ethoxy)-N-methyl-1,2,3,4-tetrahydroisoquinoline-2-carboxamide (Compound 245)

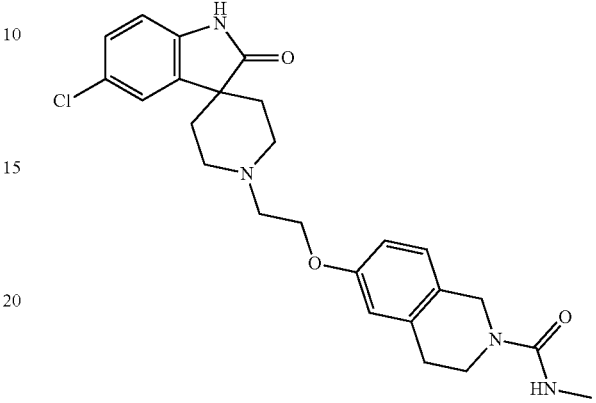

Step 1: 5-chloro-1'-(2-chloroethyl)-1-{[2-(trimethylsilyl)ethoxy]methyl}-1,2-dihydrospiro[indole-3,4'-piperidin]-2-one

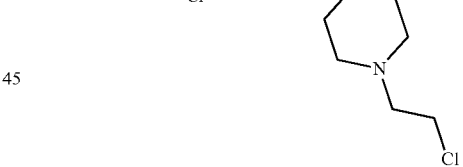

To a 0° C. solution of 5-chloro-1'-(2-chloroethyl)-1,2-dihydrospiro[indole-3,4'-piperidin]-2-one (Intermediate B-5, 400 mg, 1.34 mmol) in THF (3 mL) was added NaH (160 mg, 60 wt % in mineral oil, 4.01 mmol). The mixture was stirred at 0° C. for 30 min, and then SEM-Cl (355 μL, 2.01 mmol) was added dropwise. The mixture was allowed to warm to room temperature and stirred for another 3 h. The reaction mixture was cooled to 0° C., quenched with saturated aqueous NH$_4$Cl (10 mL), and then extracted with EtOAc (3×15 mL). The combined organic layers were washed with brine (10 mL), dried over Na$_2$SO$_4$, filtered, and concentrated in vacuo. The crude residue was purified by normal phase silica gel chromatography (Biotage 12 g cartridge, 0-20% EtOAc:petroleum ether) to give 5-chloro-1'-(2-chloroethyl)-1-{[2-(trimethylsilyl)ethoxy]methyl}-1,2-dihydrospiro[indole-3,4'-piperidin]-2-one. MS=429.2 [M+H]$^+$.

Step 2: 6-[2-(5-chloro-2-oxo-1-{[2-(trimethylsilyl)ethoxy]methyl}-1,2-dihydrospiro[indole-3,4'-piperidin]-1'-yl)ethoxy]-N-methyl-1,2,3,4-tetrahydroisoquinoline-2-carboxamide

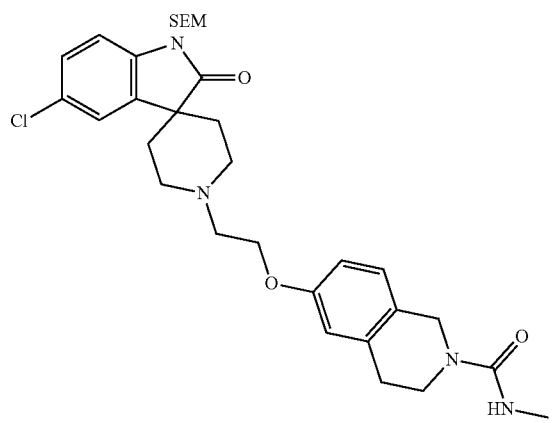 [SMILES: CNC(=O)N1CCc2cc(OCCN3CCC4(CC3)C(=O)Nc3ccc(Cl)cc34)ccc2C1]

To a solution of 6-hydroxy-N-methyl-1,2,3,4-tetrahydroisoquinoline-2-carboxamide (Intermediate A-81, 130 mg, 0.630 mmol) in acetone (4 mL) were added K₂CO₃ (87.1 mg, 0.630 mmol), 5-chloro-1'-(2-chloroethyl)-1-{[2-(trimethylsilyl)ethoxy]methyl}-1,2-dihydrospiro[indole-3,4'-piperidin]-2-one (406 mg, 0.946 mmol), and NaI (4.72 mg, 31.5 µmol). The mixture was stirred at 50° C. for 16 h. Solids were removed by filtration, and the filtrate was concentrated in vacuo. The crude residue was purified by normal phase silica gel chromatography (Biotage 4 g cartridge, 0-100% EtOAc:petroleum ether) to give 6-[2-(5-chloro-2-oxo-1-{[2-(trimethylsilyl)ethoxy]methyl}-1,2-dihydrospiro[indole-3,4'-piperidin]-1'-yl)ethoxy]-N-methyl-1,2,3,4-tetrahydroisoquinoline-2-carboxamide. MS=599.4 [M+H].

Step 3: 6-(2-{5-chloro-2-oxo-1,2-dihydrospiro[indole-3,4'-piperidin]-1'-yl}ethoxy)-N-methyl-1,2,3,4-tetrahydroisoquinoline-2-carboxamide (Compound 245)

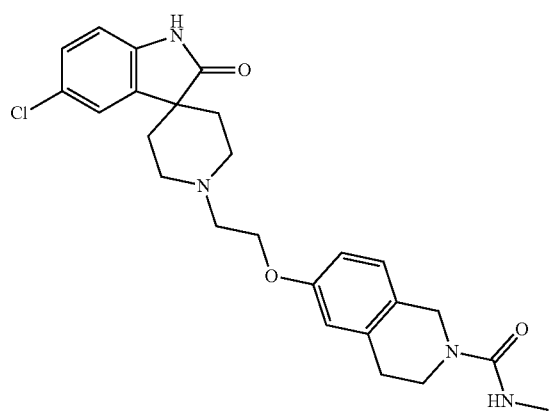 [SMILES: CNC(=O)N1CCc2cc(OCCN3CCC4(CC3)C(=O)Nc3ccc(Cl)cc34)ccc2C1]

To a solution of 6-[2-(5-chloro-2-oxo-1-{[2-(trimethylsilyl)ethoxy]methyl}-1,2-dihydrospiro[indole-3,4'-piperidin]-1'-yl)ethoxy]-N-methyl-1,2,3,4-tetrahydroisoquinoline-2-carboxamide (230 mg, 0.384 mmol) in DCM (3 mL) was added TFA (1.50 mL, 20.3 mmol). The mixture was stirred at room temperature for 2 h and was then concentrated in vacuo. The residue was dissolved into MeOH (1.5 mL) and 30% NH₄OH solution in H₂O (1.50 mL) was added. Then the mixture was stirred at room temperature for 2 h and was then concentrated in vacuo. The crude residue was purified by reverse phase preparative HPLC (Phenomenex C₁₈ column, 15-45% MeCN: 10 mM NH₄HCO₃ in H₂O) to give 6-(2-{5-chloro-2-oxo-1,2-dihydrospiro[indole-3,4'-piperidin]-1'-yl}ethoxy)-N-methyl-1,2,3,4-tetrahydroisoquinoline-2-carboxamide (Compound 245). ¹H NMR (400 MHz, DMSO-d₆): δ 10.48 (s, 1H), 7.51 (s, 1H), 7.23 (d, J=10.4 Hz, 1H), 7.02 (d, J=8.4 Hz, 1H), 6.84 (d, J=8.4 Hz, 1H), 6.77 (d, J=7.6 Hz, 2H), 6.43 (s, 1H), 4.38 (s, 2H), 4.11-4.10 (m, 2H), 3.49 (t, J=5.6 Hz, 2H), 2.91-2.85 (m, 2H), 2.84-2.82 (m, 2H), 2.72-2.68 (m, 4H), 2.59 (d, J=4.4 Hz, 3H), 1.78-1.76 (m, 2H), 1.73-1.71 (m, 2H). MS=469.2 [M+H]⁺.

Example 39

6-(2-{5-cyano-2-oxo-1,2-dihydrospiro[indole-3,4'-piperidin]-1'-yl}ethoxy)-N-methyl-1,2,3,4-tetrahydroisoquinoline-2-carboxamide (Compound 246)

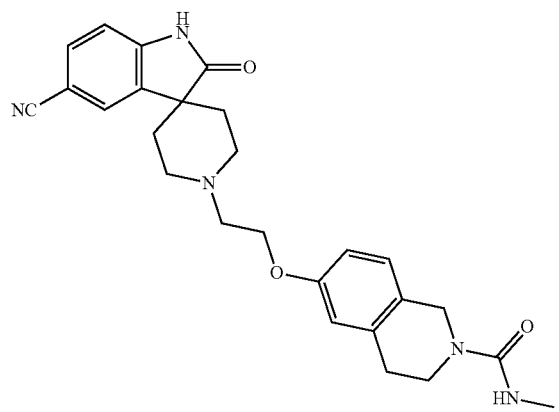 [SMILES: CNC(=O)N1CCc2cc(OCCN3CCC4(CC3)C(=O)Nc3ccc(C#N)cc34)ccc2C1]

Step 1: tert-butyl 6-(2-bromoethoxy)-1,2,3,4-tetrahydroisoquinoline-2-carboxylate

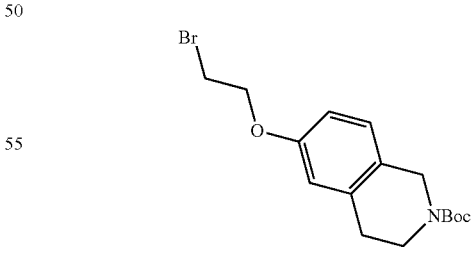

To a solution of tert-butyl 6-hydroxy-1,2,3,4-tetrahydroisoquinoline-2-carboxylate (500 mg, 2.01 mmol) in 1,2-dibromoethane (15 mL) was added Cs₂CO₃ (1.96 g, 6.02 mmol). The mixture was stirred at 80° C. for 12 h. The reaction mixture was diluted with H₂O (20 mL) and extracted with EtOAc (3×20 mL). The combined organic layers were washed with brine (30 mL), dried over Na₂SO₄, filtered, and concentrated in vacuo. The crude residue was purified by normal phase silica gel chromatography (Isco 12 g cartridge, 0-40% EtOAc:petroleum ether) to give tert-butyl 6-(2-bromoethoxy)-1,2,3,4-tetrahydroisoquinoline-2-carboxylate. MS=302.1 [M-C$_4$H$_8$+H]$^+$.

Step 2: tert-butyl 6-(2-{5-cyano-2-oxo-1,2-dihydrospiro[indole-3,4'-piperidin]-1'-yl}ethoxy)-1,2,3,4-tetrahydroisoquinoline-2-carboxylate

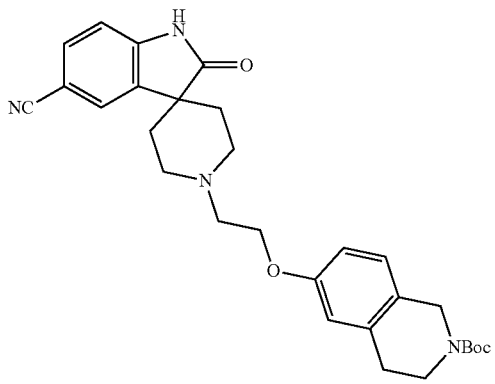 [SMILES: CC(C)(C)OC(=O)N1CCc2cc(OCCN3CCC4(CC3)C(=O)Nc3ccc(C#N)cc34)ccc2C1]

A mixture of tert-butyl 6-(2-bromoethoxy)-1,2,3,4-tetrahydroisoquinoline-2-carboxylate (100 mg, 0.281 mmol), 2-oxo-1,2-dihydrospiro[indole-3,4'-piperidine]-5-carbonitrile (Intermediate B-9, 74.0 mg, 0.281 mmol, HCl salt) and NaHCO$_3$ (47.0 mg, 0.561 mmol) in MeCN (5 mL) was stirred at 80° C. for 12 h. The reaction mixture was diluted with H$_2$O (10 mL) and extracted with EtOAc (3×10 mL). The combined organic layers were washed with brine (20 mL), dried over Na$_2$SO$_4$, filtered, and concentrated under reduced pressure to give tert-butyl 6-(2-{5-cyano-2-oxo-1,2-dihydrospiro[indole-3,4'-piperidin]-1'-yl}ethoxy)-1,2,3,4-tetrahydroisoquinoline-2-carboxylate, which was taken to the next step without further purification. MS=448.1 [M-C$_4$H$_8$+H]$^+$.

Step 3: 2-oxo-1'-[2-(1,2,3,4-tetrahydroisoquinolin-6-yloxy)ethyl]-1,2-dihydrospiro[indole-3,4'-piperidine]-5-carbonitrile

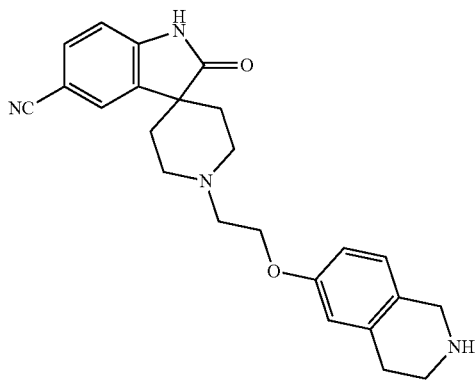 [SMILES: N#Cc1ccc2c(c1)C1(CCN(CCOc3ccc4c(c3)CCNC4)CC1)C(=O)N2]

A solution of tert-butyl 6-(2-{5-cyano-2-oxo-1,2-dihydrospiro[indole-3,4'-piperidin]-1'-yl}ethoxy)-1,2,3,4-tetrahydroisoquinoline-2-carboxylate (120 mg, 0.239 mmol) in 4.0 M HCl in MeOH (3 mL, 12 mmol) was stirred at room temperature for 2 h. The residue was concentrated in vacuo to give 2-oxo-1'-[2-(1,2,3,4-tetrahydroisoquinolin-6-yloxy)ethyl]-1,2-dihydrospiro[indole-3,4'-piperidine]-5-carbonitrile, which was used in the subsequent step without further purification. MS=403.1 [M+H]$^+$.

Step 4: 6-(2-{5-cyano-2-oxo-1,2-dihydrospiro[indole-3,4'-piperidin]-1'-yl}ethoxy)-N-methyl-1,2,3,4-tetrahydroisoquinoline-2-carboxamide (Compound 246)

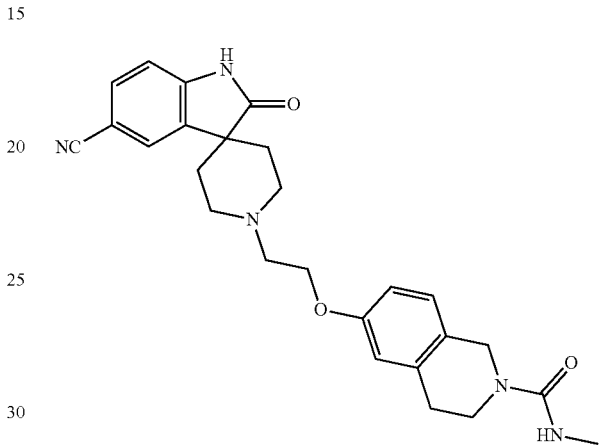

To a 0° C. solution of 1'-{2-[(2-acetyl-1,2,3,4-tetrahydroisoquinolin-6-yl)oxy]ethyl}-2-oxo-1,2-dihydrospiro[indole-3,4'-piperidine]-5-carbonitrile (140 mg, 0.348 mmol) in DCM (5 mL) was added TEA (96.8 µL, 0.696 mmol) and N-methylcarbamoyl chloride (97.6 mg, 1.04 mmol). The mixture was stirred at 0° C. for 2 h, was quenched with H$_2$O (1 mL), and then extracted with DCM (3×5 mL). The combined organic layers were dried over Na$_2$SO$_4$ and concentrated in vacuo. The crude residue was purified by reverse phase preparative HPLC (Phenomenex C$_{18}$ column, 15-45% MeCN: 10 mM NH$_4$HCO$_3$ in H$_2$O) to give 6-(2-{5-cyano-2-oxo-1,2-dihydrospiro[indole-3,4'-piperidin]-1'-yl}ethoxy)-N-methyl-1,2,3,4-tetrahydroisoquinoline-2-carboxamide (Compound 246). $^1$H NMR (400 MHz, DMSO-d$_6$): δ 10.87 (s, 1H), 7.95 (s, 1H), 7.67 (d, J=8.0 Hz, 1H), 7.03-6.98 (m, 2H), 6.79-6.77 (m, 2H), 6.45-6.44 (m, 1H), 4.38 (s, 2H), 4.10-4.08 (m, 2H), 3.49 (t, J=6.0 Hz, 2H), 2.74-2.72 (m, 4H), 2.70-2.65 (m, 4H), 2.59 (d, J=4.4 Hz, 3H), 1.78-1.76 (m, 4H). MS=460.3 [M+H]$^+$.

Example 40

5-chloro-1'-[2-({3-methyl-2-oxo-1H,2H,3H-imidazo[4,5-b]pyridin-6-yl}oxy)ethyl]-1,2-dihydrospiro[indole-3,4'-piperidin]-2-one (Compound 247)

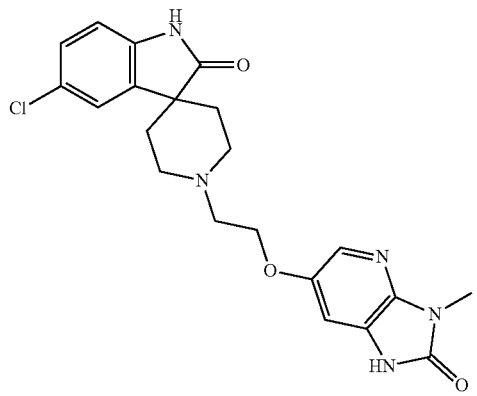 [SMILES: Cn1c(=O)[nH]c2cc(OCCN3CCC4(CC3)C(=O)Nc3ccc(Cl)cc34)cnc21]

Step 1: 5-chloro-1'-{2-[(3-methyl-2-oxo-1-{[2-(trimethylsilyl)ethoxy]methyl}-1H,2H,3H-imidazo[4,5-b]pyridin-6-yl)oxy]ethyl}-1,2-dihydrospiro[indole-3,4'-piperidin]-2-one

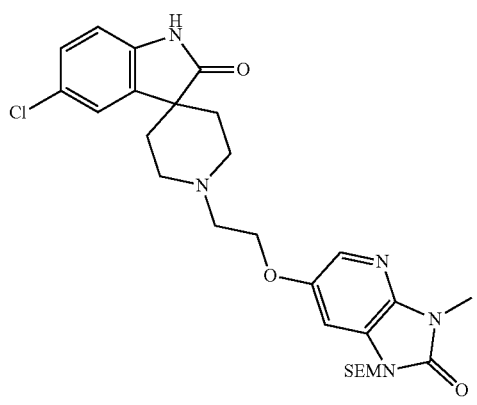 [SMILES: Cn1c(=O)n(COCC[Si](C)(C)C)c2cc(OCCN3CCC4(CC3)C(=O)Nc3ccc(Cl)cc34)cnc21]

To a mixture of 6-(2-bromoethoxy)-3-methyl-1-{[2-(trimethylsilyl)ethoxy]methyl}-1H,2H,3H-imidazo[4,5-b]pyridin-2-one (Intermediate A-74, 150 mg, 0.373 mmol) and 5-chloro-1,2-dihydrospiro[indole-3,4'-piperidin]-2-one (Intermediate B-4, 112 mg, 0.410 mmol, HCl salt) in MeCN (3 mL) was added NaHCO₃ (47.0 mg, 0.559 mmol). The mixture was stirred at 80° C. for 12 h. After cooling to room temperature, the reaction mixture was poured into H₂O (5 mL) and extracted with EtOAc (2×10 mL). The combined organic layers were washed with brine (10 mL), dried over Na₂SO₄, filtered, and concentrated in vacuo. The crude residue was purified by normal phase silica gel chromatography (Biotage 4 g cartridge, 0-100% EtOAc:petroleum ether) to give 5-chloro-1'-{2-[(3-methyl-2-oxo-1-{[2-(trimethylsilyl)ethoxy]methyl}-1H,2H,3H-imidazo[4,5-b]pyridin-6-yl)oxy]ethyl}-1,2-dihydrospiro[indole-3,4'-piperidin]-2-one. MS=558.3 [M+H]⁺.

Step 2: 5-chloro-1'-[2-({3-methyl-2-oxo-1H,2H,3H-imidazo[4,5-b]pyridin-6-yl}oxy)ethyl]-1,2-dihydrospiro[indole-3,4'-piperidin]-2-one (Compound 247)

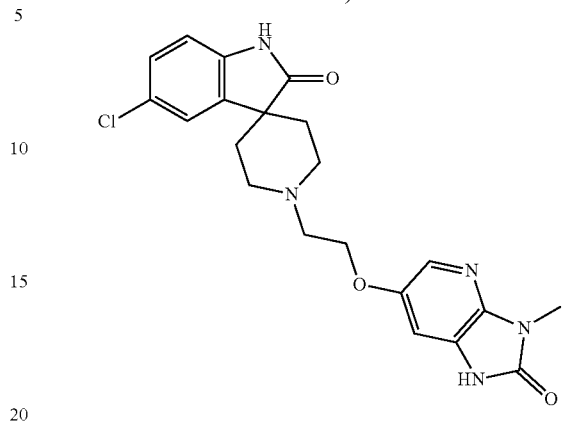

A solution of 5-chloro-1'-{2-[(3-methyl-2-oxo-1-{[2-(trimethylsilyl)ethoxy]methyl}-1H,2H,3H-imidazo[4,5-b]pyridin-6-yl)oxy]ethyl}-1,2-dihydrospiro[indole-3,4'-piperidin]-2-one (100 mg, 0.179 mmol) in DCM (2 mL) and TFA (0.5 mL) was stirred at room temperature for 1 h. The reaction mixture was concentrated in vacuo, then dissolved in MeOH (3 mL) and 25% NH₄OH solution in H₂O (1 mL) was added. The mixture was stirred at room temperature for 1 h, was diluted with H₂O (5 mL), and then extracted with EtOAc (2×10 mL). The combined organic layers were dried with Na₂SO₄ and concentrated in vacuo. The crude residue was purified by reverse phase preparative HPLC (Phenomenex C₁₈ column, 15-45% MeCN: 10 mM NH₄HCO₃ in H₂O) to give 5-chloro-1'-[2-({3-methyl-2-oxo-1H,2H,3H-imidazo[4,5-b]pyridin-6-yl}oxy)ethyl]-1,2-dihydrospiro[indole-3,4'-piperidin]-2-one (Compound 247). ¹H NMR (400 MHz, DMSO-d₆): δ 11.03 (s, 1H), 10.48 (s, 1H), 7.71 (d, J=2.4 Hz, 1H), 7.50 (d, J=2.0 Hz, 1H), 7.23 (dd, J=8.0, 2.0 Hz, 1H), 7.04 (d, J=2.4 Hz, 1H), 6.84 (d, J=8.4 Hz, 1H), 4.16 (t, J=5.6 Hz, 2H), 3.26 (s, 3H), 2.95-2.87 (m, 2H), 2.84 (t, J=5.6 Hz, 2H), 2.72-2.65 (m, 2H), 1.84-1.75 (m, 2H), 1.74-1.66 (m, 2H). MS=428.1 [M+H]⁺.

Example 41

5-chloro-1'-{2-[(6-{[1-(hydroxymethyl)cyclopropyl]sulfonyl}pyridin-3-yl)oxy]ethyl}-1,2-dihydrospiro[indole-3,4'-piperidin]-2-one_(Compound 248)

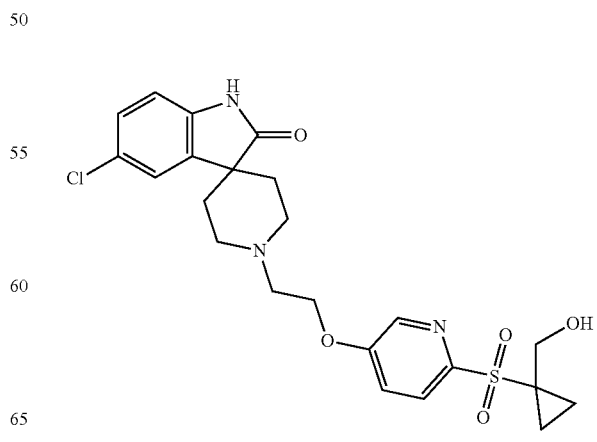

Step 1: methyl 2-[(5-chloropyridin-2-yl)sulfanyl]acetate

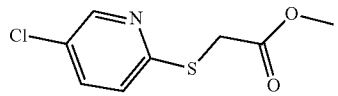

A mixture of 5-chloropyridine-2-thiol (3.00 g, 20.6 mmol), methyl 2-bromoacetate (2.92 mL, 30.9 mmol), and $K_2CO_3$ (5.69 g, 41.2 mmol) in DMF (50 mL) was degassed and purged with $N_2$ (3×). The mixture was stirred at room temperature for 2 h under $N_2$ atmosphere. The reaction mixture was quenched with $H_2O$ (30 mL) and then extracted with EtOAc (3×50 mL). The combined organic layers were washed with brine (2×20 mL), dried over $Na_2SO_4$, filtered, and concentrated in vacuo. The crude residue was purified by normal phase silica gel chromatography (Biotage 40 g cartridge, 0-5% EtOAc:petroleum ether) to give methyl 2-[(5-chloropyridin-2-yl)sulfanyl]acetate. MS=218.0 $[M+H]^+$.

Step 2: methyl 2-[(5-chloropyridin-2-yl)sulfonyl]acetate

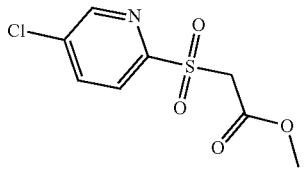

A mixture of methyl 2-[(5-chloropyridin-2-yl)sulfanyl]acetate (5.70 g, 26.2 mmol), m-CPBA (10.6 g, 85% purity, 52.4 mmol) in DCM (2 mL) was degassed and purged with $N_2$ (3×). The mixture was stirred at 0° C. for 2 h under $N_2$ atmosphere. The reaction mixture was quenched with saturated $Na_2SO_3$ (50 mL) and extracted with EtOAc (3×50 mL). The combined organic layers were washed with brine (2×50 mL), dried over $Na_2SO_4$, filtered, and concentrated in vacuo. The crude residue was purified by normal phase silica gel chromatography (Biotage 40 g cartridge, 0-13% EtOAc:petroleum ether) to give methyl 2-[(5-chloropyridin-2-yl)sulfonyl]acetate. MS=250.0 $[M+H]^+$.

Step 3: methyl 1-[(5-chloropyridin-2-yl)sulfonyl]cyclopropane-1-carboxylate

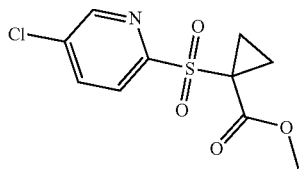 [SMILES: COC(=O)C1(S(=O)(=O)c2ccc(Cl)cn2)CC1]

A mixture of methyl 2-[(5-chloropyridin-2-yl)sulfonyl]acetate (5.00 g, 20.0 mmol), 1,2-dibromoethane (1.81 mL, 24.0 mmol), and $K_2CO_3$ (6.92 g, 50.1 mmol) in DMF (50 mL) was degassed and purged with $N_2$ (3×). The mixture was stirred at 60° C. for 10 h under $N_2$ atmosphere. After cooling to room temperature, the mixture was diluted with $H_2O$ (50 mL) and extracted with EtOAc (3×50 mL). The combined organic layers were washed with brine (2×50 mL), dried over $Na_2SO_4$, filtered, and concentrated in vacuo. The crude residue was purified by normal phase silica gel chromatography (Biotage 40 g cartridge, 0-60% EtOAc:petroleum ether) to give methyl 1-[(5-chloropyridin-2-yl)sulfonyl]cyclopropane-1-carboxylate. MS=276.0 $[M+H]^+$.

Step 4: methyl 1-{[5-(2-hydroxyethoxy)pyridin-2-yl]sulfonyl}cyclopropane-1-carboxylate

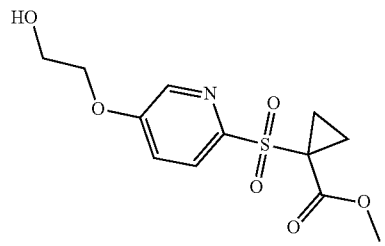 [SMILES: COC(=O)C1(S(=O)(=O)c2ccc(OCCO)cn2)CC1]

A mixture of methyl 1-[(5-chloropyridin-2-yl)sulfonyl]cyclopropane-1-carboxylate (5.00 g, 18.1 mmol), ethylene glycol (20.3 mL, 363 mmol), and $Cs_2CO_3$ (17.7 g, 54.4 mmol) in DMSO (2 mL) was degassed and purged with $N_2$ (3×). The mixture was stirred at 100° C. for 12 h under $N_2$ atmosphere. After cooling to room temperature, MeI (3.39 mL, 54.4 mmol) was added, and the mixture was stirred for 12 h. The mixture was quenched with $H_2O$ (50 mL) and extracted with EtOAc (3×50 mL). The combined organic layers were washed with brine (2×30 mL), dried over $Na_2SO_4$, filtered, and concentrated in vacuo. The crude residue was purified by normal phase silica gel chromatography (Biotage 40 g cartridge, 0-60% EtOAc:petroleum ether) to give methyl 1-{[5-(2-hydroxyethoxy)pyridin-2-yl]sulfonyl}cyclopropane-1-carboxylate. MS=302.2 $[M+H]^+$.

Step 5: methyl 1-({5-[2-(methanesulfonyloxy)ethoxy]pyridin-2-yl}sulfonyl)cyclopropane-1-carboxylate

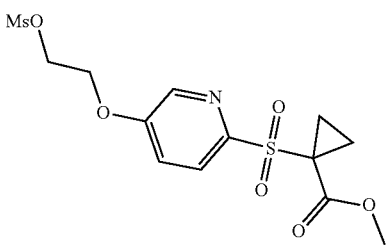 [SMILES: COC(=O)C1(S(=O)(=O)c2ccc(OCCOS(C)(=O)=O)cn2)CC1]

To a 0° C. mixture of methyl 1-{[5-(2-hydroxyethoxy)pyridin-2-yl]sulfonyl}cyclopropane-1-carboxylate (500 mg, 1.66 mmol) and TEA (0.693 mL, 4.98 mmol) in DCM (2 mL) was added methanesulfonic anhydride (578 mg, 3.32 mmol). The mixture was stirred at 0° C. for 2 h. The mixture was quenched with $H_2O$ (50 mL) and extracted with EtOAc (3×50 mL). The combined organic layers were washed with brine (2×50 mL), dried over $Na_2SO_4$, filtered, and concentrated in vacuo. The crude residue was purified by normal phase silica gel chromatography (Biotage 40 g cartridge, 0-60% EtOAc:petroleum ether) to give methyl 1-({5-[2-(methanesulfonyloxy)ethoxy]pyridin-2-yl}sulfonyl)cyclopropane-1-carboxylate. MS=380.1 [M+H]+.

Step 6: methyl 1-{[5-(2-{5-chloro-2-oxo-1,2-dihydrospiro[indole-3,4'-piperidin]-1'-yl}ethoxy)pyridin-2-yl]sulfonyl}cyclopropane-1-carboxylate

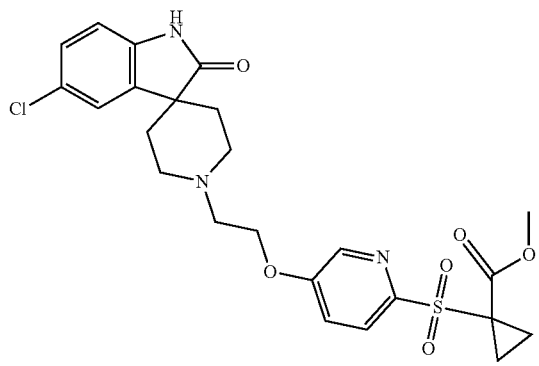

A mixture of methyl 1-({5-[2-(methanesulfonyloxy)ethoxy]pyridin-2-yl}sulfonyl)cyclopropane-1-carboxylate (700 mg, 1.84 mmol), 5-chloro-1,2-dihydrospiro[indole-3,4'-piperidin]-2-one (Intermediate B-4, 605 mg, 2.21 mmol, HCl salt), and NaHCO$_3$ (310 mg, 3.69 mmol) in MeCN (10 mL) was degassed and purged with N$_2$ (3×). The mixture was stirred at 80° C. for 12 h under N$_2$ atmosphere. After cooling to room temperature, the mixture was quenched with H$_2$O (50 mL) and then extracted with EtOAc (3×50 mL). The combined organic layers were washed with brine (2×50 mL), dried over Na$_2$SO$_4$, filtered, and concentrated in vacuo. The crude residue was purified by normal phase silica gel chromatography (Biotage 12 g cartridge, 0-80% EtOAc: petroleum ether) to give methyl 1-{[5-(2-{5-chloro-2-oxo-1,2-dihydrospiro[indole-3,4'-piperidin]-1'-yl}ethoxy)pyridin-2-yl]sulfonyl}cyclopropane-1-carboxylate. MS=520.2 [M+H]+.

Step 7: 5-chloro-1'-{2-[(6-{[1-(hydroxymethyl)cyclopropyl]sulfonyl}pyridin-3-yl)oxy]ethyl}-1,2-dihydrospiro[indole-3,4'-piperidin]-2-one (Compound 248)

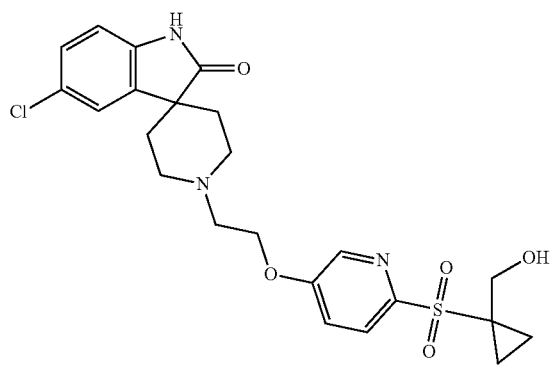 [SMILES: O=C1Nc2ccc(Cl)cc2C12CCN(CCOc1ccc(S(=O)(=O)C3(CO)CC3)nc1)CC2]

To a 0° C. solution of methyl 1-{[5-(2-{5-chloro-2-oxo-1,2-dihydrospiro[indole-3,4'-piperidin]-1'-yl}ethoxy)pyridin-2-yl]sulfonyl}cyclopropane-1-carboxylate (100 mg, 0.192 mmol) in THF (2 mL) was added LiAlH$_4$ (14.6 mg, 385 mmol). The reaction mixture allowed to warm to room temperature and stirred for 2 h under N$_2$ atmosphere. The mixture was quenched with H$_2$O (50 mL) and extracted with EtOAc (3×50 mL). The combined organic layers were washed with brine (2×50 mL), dried over anhydrous Na$_2$SO$_4$, filtered, and concentrated in vacuo. The crude residue was purified by reverse phase preparative HPLC (Waters Xbridge BEH C$_{18}$ column, 25-55% MeCN: 10 mM NH$_4$HCO$_3$ in H$_2$O) to give 5-chloro-1'-{2-[(6-{[1-(hydroxymethyl)cyclopropyl]sulfonyl}pyridin-3-yl)oxy]ethyl}-1,2-dihydrospiro[indole-3,4'-piperidin]-2-one (Compound 248). $^1$H NMR (400 MHz, DMSO-d$_6$): δ 10.48 (s, 1H), 8.48 (d, J=2.8 Hz, 1H), 7.97 (d, J=8.8 Hz, 1H), 7.68 (dd, J=8.8, 2.8 Hz, 1H), 7.50 (s, 1H), 7.24-7.22 (m, 1H), 6.84 (d, J=8.4 Hz, 1H), 4.82 (t, J=6 Hz, 1H), 4.33 (t, J=6 Hz, 2H), 3.70 (d, J=6 Hz, 2H), 2.98-2.85 (m, 4H), 2.79-2.68 (m, 2H), 1.83-1.67 (m, 4H), 1.39-1.30 (m, 2H), 1.09-1.02 (m, 2H). MS=492.2 [M+H]+.

Example 42

4-(2-{5-chloro-2-oxo-1,2-dihydrospiro[indole-3,4'-piperidin]-1'-yl}ethoxy)-2-(difluoromethyl)benzamide (Compound 249)

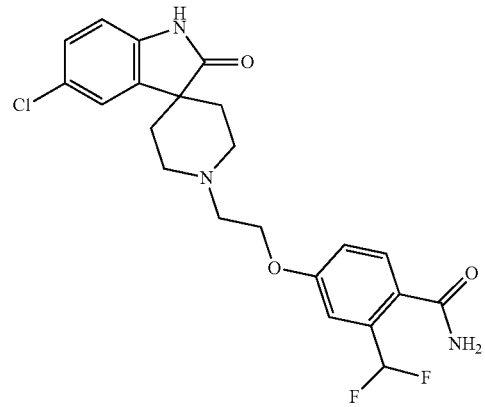 [SMILES: NC(=O)c1ccc(OCCN2CCC3(CC2)C(=O)Nc2ccc(Cl)cc23)cc1C(F)F]

Step 1:
4-(benzyloxy)-1-bromo-2-(difluoromethyl)benzene

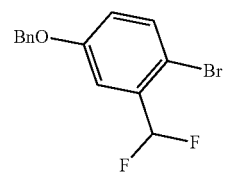 [SMILES: FC(F)c1cc(OCc2ccccc2)ccc1Br]

To a 0° C. solution of 5-(benzyloxy)-2-bromobenzaldehyde (3.00 g, 10.3 mmol) in DCM (30 mL) was added DAST (2.72 mL, 20.6 mmol). The reaction was allowed to warm to room temperature and stirred for 12 h. The reaction mixture was cooled to 0° C., quenched with saturated NaHCO₃ aqueous solution (20 mL), diluted with H₂O (10 mL), and then extracted with EtOAc (3×20 mL). The combined organic layers were washed with brine (30 mL), dried with Na₂SO₄, filtered, and concentrated in vacuo. The crude residue was purified by normal phase silica gel chromatography (Biotage 20 g cartridge, 0-20% EtOAc: petroleum ether) to give 4-(benzyloxy)-1-bromo-2-(difluoromethyl)benzene.

Step 2: methyl 4-(benzyloxy)-2-(difluoromethyl)benzoate

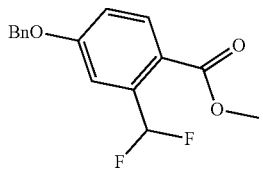 [SMILES: COC(=O)c1ccc(OCc2ccccc2)cc1C(F)F]

A mixture of 4-(benzyloxy)-1-bromo-2-(difluoromethyl)benzene (2.20 g, 7.03 mmol), Pd(OAc)₂ (315 mg, 1.41 mmol), and 1,1'-bis(diphenylphosphino)ferrocene (1.56 g, 2.81 mmol) in MeOH (15 mL) and toluene (15 mL) was degassed and purged with N₂ (3×). The suspension was then degassed under vacuum and purged with CO. The mixture was stirred under CO (50 psi) at 80° C. for 12 h. After cooling to room temperature, solids were removed by filtration, and the filtrate was concentrated in vacuo. The residue was taken up in H₂O (40 mL) and extracted with EtOAc (3×30 mL). The combined organic layers were washed with brine (2×12 mL), dried over Na₂SO₄, filtered, and concentrated in vacuo. The crude residue was purified by normal phase silica gel chromatography (Isco 20 g cartridge, 0-23% EtOAc:petroleum ether) to give methyl 4-(benzyloxy)-2-(difluoromethyl)benzoate. MS=293.1 [M+H]⁺.

Step 3: methyl 2-(difluoromethyl)-4-hydroxybenzoate

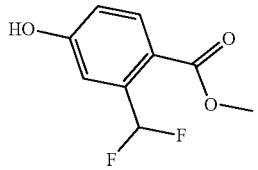

To a solution of methyl 4-(benzyloxy)-2-(difluoromethyl)benzoate (420 mg, 1.44 mmol) in MeOH (10 mL) under N₂ atmosphere was added Pd/C (100 mg, 10 wt %, 0.0940 mmol) and Pd(OH)₂/C (100 mg, 20 wt %, 0.140 mmol). The mixture was stirred at 50° C. for 12 h under H₂ (50 Psi) atmosphere. After cooling to room temperature, the reaction mixture was filtered through Celite and the filtrate was concentrated in vacuo. The crude residue was purified by normal phase silica gel chromatography (Isco 12 g cartridge, 0-30% EtOAc:petroleum ether) to give methyl 2-(difluoromethyl)-4-hydroxybenzoate. MS=203.1 [M+H]⁺.

Step 4: methyl 4-(2-bromoethoxy)-2-(difluoromethyl)benzoate

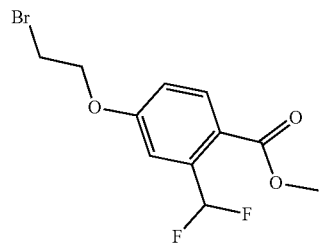 [SMILES: COC(=O)c1ccc(OCCBr)cc1C(F)F]

To a solution of methyl 2-(difluoromethyl)-4-hydroxybenzoate (300 mg, 1.48 mmol) in 1,2-dibromoethane (5 mL) was added Cs₂CO₃ (1.45 g, 4.45 mmol). The mixture was stirred at 100° C. for 12 h. After cooling to room temperature, the mixture was filtered, and the filtrate was concentrated in vacuo. The crude residue was purified by normal phase silica gel chromatography (Isco 4 g cartridge, 0-50% EtOAc:petroleum ether) to give methyl 4-(2-bromoethoxy)-2-(difluoromethyl)benzoate.

Step 5: methyl 4-(2-{5-chloro-2-oxo-1,2-dihydrospiro[indole-3,4'-piperidin]-1'-yl}ethoxy)-2-(difluoromethyl)benzoate

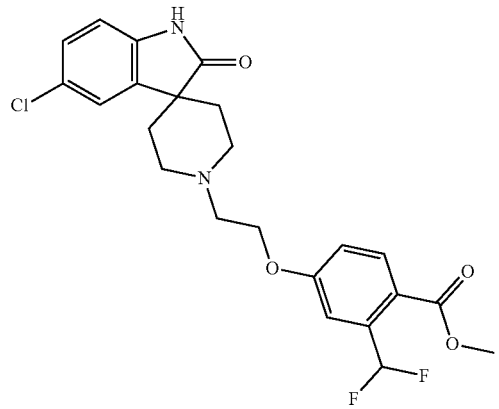 [SMILES: COC(=O)c1ccc(OCCN2CCC3(CC2)C(=O)Nc2ccc(Cl)cc23)cc1C(F)F]

A mixture of methyl 4-(2-bromoethoxy)-2-(difluoromethyl)benzoate (200 mg, 0.647 mmol), 5-chloro-1,2-dihydrospiro[indole-3,4'-piperidin]-2-one (Intermediate B-4, 177 mg, 0.647 mmol, HCl salt) and NaHCO₃ (163 mg, 1.94 mmol) in MeCN (4 mL) was degassed and purged with N₂ (3 times). The mixture was stirred at 80° C. for 12 h under N₂ atmosphere. After cooling to room temperature, solids were removed by filtration and the filtrate was concentrated in vacuo. The crude residue was purified by normal phase silica gel chromatography (Isco 12 g cartridge, 0-50% EtOAc:petroleum ether) to give methyl 4-(2-{5-chloro-2-oxo-1,2-dihydrospiro[indole-3,4'-piperidin]-1'-yl}ethoxy)-2-(difluoromethyl)benzoate. MS=465.1 [M+H]⁺.

Step 6: 4-(2-{5-chloro-2-oxo-1,2-dihydrospiro[indole-3,4'-piperidin]-1'-yl}ethoxy)-2-(difluoromethyl)benzoic acid

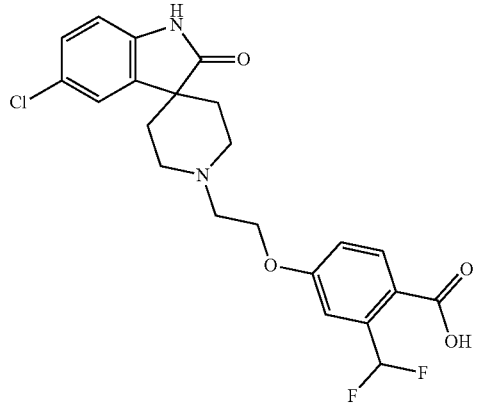 [SMILES: O=C(O)c1ccc(OCCN2CCC3(CC2)C(=O)Nc2ccc(Cl)cc23)cc1C(F)F]

Step 7: 4-(2-{5-chloro-2-oxo-1,2-dihydrospiro[indole-3,4'-piperidin]-1'-yl}ethoxy)-2-(difluoromethyl)benzamide (Compound 249)

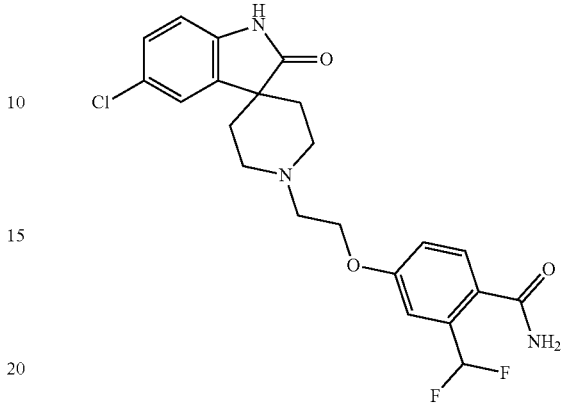

To a solution of methyl 4-(2-{5-chloro-2-oxo-1,2-dihydrospiro[indole-3,4'-piperidin]-1'-yl}ethoxy)-2-(difluoromethyl)benzoate (200 g, 430 mmol) in MeOH (4 mL) was added a solution of LiOH H$_2$O (144 mg, 3.44 mmol) in H$_2$O (4 mL). The mixture was stirred at 50° C. for 2 h. After cooling to room temperature, the reaction mixture was concentrated in vacuo to remove MeOH. The residue was adjusted to pH=2-3 with 1.0 M aqueous HCl solution. The resulting solids were isolated by filtration, and then dried in vacuo. The crude product was triturated with H$_2$O and then dried again in vacuo to give 4-(2-{5-chloro-2-oxo-1,2-dihydrospiro[indole-3,4'-piperidin]-1'-yl}ethoxy)-2-(difluoromethyl)benzoic acid, which was used in the subsequent step without further purification. MS=451.1 [M+H]$^+$.

To a 0° C. solution of 4-(2-{5-chloro-2-oxo-1,2-dihydrospiro[indole-3,4'-piperidin]-1'-yl}ethoxy)-2-(difluoromethyl)benzoic acid (200 mg, 0.444 mmol) in DMF (20 mL) was added NH$_4$Cl (71.2 mg, 1.33 mmol), TEA (216 µL, 1.55 mmol), and then HATU (202 mg, 0.532 mmol). The mixture was allowed to warm to room temperature, stirred for 12 h, and then quenched with H$_2$O (15 mL). Solids were removed by filtration, and the filtrate was concentrated in vacuo. The crude residue was purified by reverse phase preparative HPLC (Waters Xbridge Prep OBD C$_{18}$ column, 25-55% MeCN: 10 mM NH$_4$HCO$_3$ in H$_2$O) to give 4-(2-{5-chloro-2-oxo-1,2-dihydrospiro[indole-3,4'-piperidin]-1'-yl}ethoxy)-2-(difluoromethyl)benzamide (Compound 249). $^1$H NMR (400 MHz, DMSO-d$_6$): δ 10.48 (s, 1H), 7.96 (s, 1H), 7.71-7.61 (m, 1H), 7.52-7.32 (m, 3H), 7.25-7.14 (m, 3H), 6.84 (d, J=8.4 Hz, 1H), 4.24 (t, J=5.6 Hz, 2H), 2.97-2.83 (m, 4H), 2.74-2.68 (m, 2H), 1.83-1.66 (m, 4H). MS=450.1 [M+H]$^+$.

The following compounds in Table 36 were prepared according to procedures similar to steps 1-7 described for Compound 249 using the appropriate starting materials.

TABLE 36

| # | Structure | Name | Exact Mass [M + H]$^+$ | Intermediate Used |
|---|---|---|---|---|
| 250 | 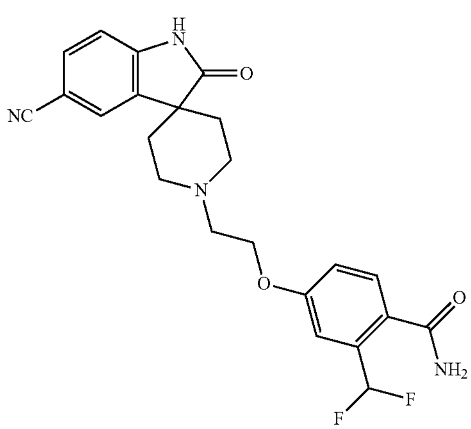 [SMILES: N#Cc1ccc2c(c1)C1(CCN(CCOc3ccc(C(N)=O)c(C(F)F)c3)CC1)C(=O)N2] | 4-(2-{5-cyano-2-oxo-1,2-dihydrospiro[indole-3,4'-piperidin]-1'-yl}ethoxy)-2-(difluoromethyl)benzamide | Calc'd 441.2 Found 441.1 | B-9 |

Example 43

1'-{2-[4-(3-methanesulfonyloxetan-3-yl)phenoxy]ethyl}-1-methyl-2-oxo-1,2-dihydrospiro[indole-3,4'-piperidine]-5-carbonitrile (Compound 251)

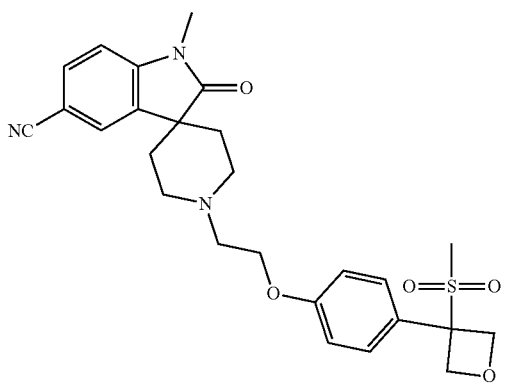 [SMILES: CN1C(=O)C2(CCN(CCOc3ccc(C4(S(C)(=O)=O)COC4)cc3)CC2)c2cc(C#N)ccc21]

To a 0° C. solution of 1'-{2-[4-(3-methanesulfonyloxetan-3-yl)phenoxy]ethyl}-2-oxo-1,2-dihydrospiro[indole-3,4'-piperidine]-5-carbonitrile (Compound 109, 78.0 mg, 0.162 mmol) in DMA (1 mL) was added NaH (13.0 mg, 60 wt % in mineral oil, 0.324 mmol) portionwise. The mixture was stirred at 0° C. for 30 min, and then MeI (11.1 μL, 0.178 mmol) was added dropwise. The mixture was allowed to warm to room temperature and stirred for 3 h. The reaction mixture was quenched with H$_2$O (10 mL) and then extracted with EtOAc (3×10 mL). The combined organic layers were washed with brine (10 mL), dried over Na$_2$SO$_4$, filtered, and concentrated in vacuo. The crude residue was purified by reverse phase preparative HPLC (Phenomenex C$_{18}$ column, 20-50% MeCN: 10 mM NH$_4$HCO$_3$ in H$_2$O) to give 1'-{2-[4-(3-methanesulfonyloxetan-3-yl)phenoxy]ethyl}-1-methyl-2-oxo-1,2-dihydrospiro[indole-3,4'-piperidine]-5-carbonitrile (Compound 251). $^1$H NMR (400 MHz, DMSO-d$_6$): δ 7.99 (d, J=1.2 Hz, 1H), 7.80 (dd, J=8.0, 1.6 Hz, 1H), 7.26 (d, J=8.8 Hz, 2H), 7.20 (d, J=8.0 Hz, 1H), 7.05 (d, J=8.8 Hz, 2H), 5.21 (d, J=7.6 Hz, 2H), 5.01 (d, J=7.6 Hz, 2H), 4.18 (t, J=5.6 Hz, 2H) 3.16 (s, 3H), 2.96-2.88 (m, 4H), 2.86 (s, 3H), 2.79-2.76 (m, 2H), 1.82-1.77 (m, 4H). MS=496.2 [M+H]$^+$.

Example 44

1'-(2-{4-[3-(3-fluoroazetidine-1-carbonyl)oxetan-3-yl]phenoxy}ethyl)-2-oxo-1,2-dihydrospiro[indole-3,4'-piperidine]-5-carbonitrile (Compound 252)

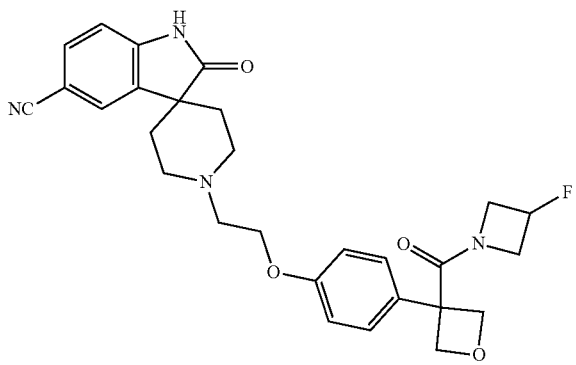 [SMILES: N#Cc1ccc2c(c1)C1(CCN(CCOc3ccc(C4(C(=O)N5CC(F)C5)COC4)cc3)CC1)C(=O)N2]

Step 1: 2-{3-[4-(benzyloxy)phenyl]oxetan-3-yl}-5-methylfuran

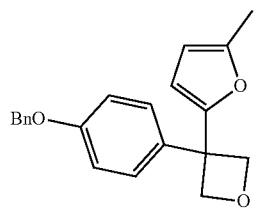 [SMILES: Cc1ccc(C2(c3ccc(OCc4ccccc4)cc3)COC2)o1]

To a solution 3-[4-(benzyloxy)phenyl]oxetan-3-ol (Intermediate A-35, 20.0 g, 78.0 mmol) in CHCl$_3$ (200 mL) was added tetrabutylammonium hexafluorophosphate (1.66 g, 4.29 mmol), [bis(trifluoromethylsulfonyl)amino]lithium (2.46 g, 8.58 mmol), and 2-methylfuran (35.1 mL, 390 mmol). The mixture was stirred at 50° C. for 4 h. After cooling to 0° C., the reaction mixture was quenched with H$_2$O (200 mL) and extracted with DCM (3×200 mL). The combined organic layers were dried over Na$_2$SO$_4$, filtered, and concentrated in vacuo. The crude residue was purified by normal phase silica gel chromatography (Biotage 220 g cartridge, 0-15% EtOAc:petroleum ether) to give 2-{3-[4-(benzyloxy)phenyl]oxetan-3-yl}-5-methylfuran. MS=321.2 [M+H]$^+$.

Step 2: 3-[4-(benzyloxy)phenyl]oxetane-3-carboxylic acid

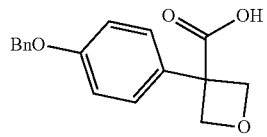 [SMILES: O=C(O)C1(c2ccc(OCc3ccccc3)cc2)COC1]

To a solution of 2-{3-[4-(benzyloxy)phenyl]oxetan-3-yl}-5-methylfuran (11.0 g, 34.3 mmol) in heptane (200 mL), EtOAc (200 mL) and H$_2$O (400 mL) was added NaIO$_4$ (51.4 g, 240 mmol) and RuCl$_3$ (178 mg, 0.858 mmol). The mixture was stirred at room temperature for 16 h. The reaction mixture was cooled to 0° C. and quenched with saturated Na$_2$SO$_3$ (200 mL). The mixture was adjusted to pH=8 with saturated NaHCO$_3$ and washed with EtOAc (3×400 mL). The aqueous layer was adjusted to pH=2-3 with 2.0 M aqueous HCl solution and extracted with EtOAc (3×400 mL). The combined organic layers were dried over Na$_2$SO$_4$, filtered, and concentrated in vacuo to give 3-[4-(benzyloxy)phenyl]oxetane-3-carboxylic acid, which was used in the subsequent step without further purification. MS=283.0 [M−H]$^−$.

Step 3: methyl 3-[4-(benzyloxy)phenyl]oxetane-3-carboxylate

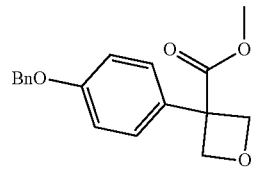 [SMILES: COC(=O)C1(c2ccc(OCc3ccccc3)cc2)COC1]

To a solution of 3-[4-(benzyloxy)phenyl]oxetane-3-carboxylic acid (4.00 g, 14.1 mmol) in DMF (50 mL) was added K₂CO₃ (2.92 g, 21.1 mmol) and MeI (4.38 mL, 70.5 mmol). The mixture was stirred at room temperature for 3 h. The reaction mixture was cooled to 0° C., quenched with H₂O (100 mL), and the resulting precipitate was collected by filtration and washed with H₂O to give methyl 3-[4-(benzyloxy)phenyl]oxetane-3-carboxylate, which was used in the subsequent step without further purification. MS=316.2 [M+NH₄]⁺.

Step 4: methyl 3-(4-hydroxyphenyl)oxetane-3-carboxylate

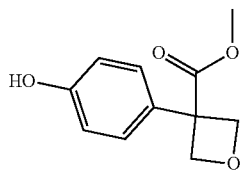

To a solution of methyl 3-[4-(benzyloxy)phenyl]oxetane-3-carboxylate (4.00 g, 13.4 mmol) in EtOAc (100 mL) under N₂ atmosphere was added Pd/C (5.00 g, 10 wt %, 4.70 mmol). The suspension was degassed under vacuum and purged with H₂ (3×). After stirring under an atmosphere of H₂ (15 psi) at room temperature for 4 h, solids were removed by filtration through Celite and the filtrate was concentrated in vacuo to give methyl 3-(4-hydroxyphenyl)oxetane-3-carboxylate, which was used in the subsequent step without further purification. MS=231.1 [M+Na]⁺.

Step 5: methyl 3-[4-(2-bromoethoxy)phenyl]oxetane-3-carboxylate

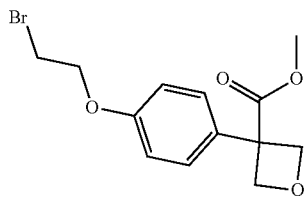 [SMILES: COC(=O)C1(c2ccc(OCCBr)cc2)COC1]

To a solution of methyl 3-(4-hydroxyphenyl)oxetane-3-carboxylate (2.20 g, 10.6 mmol) in DMF (3 mL) was added 1,2-dibromoethane (17.0 mL, 225 mmol) and Cs₂CO₃ (6.89 g, 21.1 mmol). The mixture was stirred at 100° C. for 6 h. After cooling to 0° C., the reaction mixture was quenched with H₂O (30 mL) and extracted with DCM (3×15 mL). The combined organic layers were dried over Na₂SO₄, filtered, and concentrated in vacuo. The crude residue was purified by normal phase silica gel chromatography (Biotage 45 g cartridge, 0-40% EtOAc:petroleum ether) to give methyl 3-[4-(2-bromoethoxy)phenyl]oxetane-3-carboxylate. MS=332.1/334.1 [M+NH₄]⁺.

Step 6: methyl 3-[4-(2-{5-cyano-2-oxo-1,2-dihydrospiro[indole-3,4'-piperidin]-1'-yl}ethoxy)phenyl]oxetane-3-carboxylate

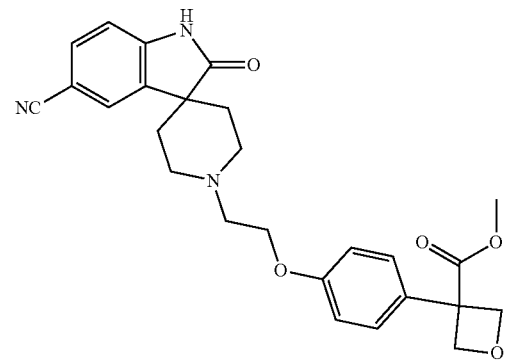 [SMILES: COC(=O)C1(c2ccc(OCCN3CCC4(CC3)C(=O)Nc3ccc(C#N)cc34)cc2)COC1]

To a solution of methyl 3-[4-(2-bromoethoxy)phenyl]oxetane-3-carboxylate (2.50 g, 7.93 mmol) in MeCN (30 mL) was added NaHCO₃ (2.00 g, 23.8 mmol) and 2-oxo-1,2-dihydrospiro[indole-3,4'-piperidine]-5-carbonitrile (Intermediate B-9, 2.09 g, 7.93 mmol, HCl salt). The mixture was stirred at 80° C. for 16 h. After cooling to room temperature, the reaction mixture was filtered and washed with MeCN (40 mL) and EtOAc (20 mL). The filtrate was concentrated in vacuo to give methyl 3-[4-(2-{5-cyano-2-oxo-1,2-dihydrospiro[indole-3,4'-piperidin]-1'-yl}ethoxy)phenyl]oxetane-3-carboxylate, which was used in the subsequent step without further purification. MS=462.2 [M+H]⁺.

Step 7: 3-[4-(2-{5-cyano-2-oxo-1,2-dihydrospiro[indole-3,4'-piperidin]-1'-yl}ethoxy)phenyl]oxetane-3-carboxylic acid

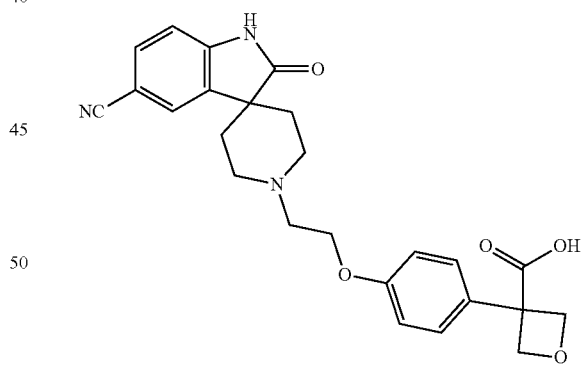

To a solution of methyl 3-[4-(2-{5-cyano-2-oxo-1,2-dihydrospiro[indole-3,4'-piperidin]-1'-yl}ethoxy)phenyl]oxetane-3-carboxylate (3.00 g, 6.50 mmol) in THF (30 mL) and H₂O (10 mL) was added LiOH (467 mg, 19.5 mmol). The mixture was stirred at room temperature for 6 h, and was then concentrated in vacuo to remove THF. The residue was adjusted to pH=2-3 with 2 M aqueous HCl solution. The resulting precipitate was collected by filtration and washed with H₂O (100 mL) to give 3-[4-(2-{5-cyano-2-oxo-1,2-dihydrospiro[indole-3,4'-piperidin]-1'-yl}ethoxy)phenyl]oxetane-3-carboxylic acid, which was used in the subsequent step without further purification. MS=448.3 [M+H]⁺.

Step 8: 1'-(2-{4-[3-(3-fluoroazetidine-1-carbonyl)oxetan-3-yl]phenoxy}ethyl)-2-oxo-1,2-dihydrospiro[indole-3,4'-piperidine]-5-carbonitrile (Compound 252)

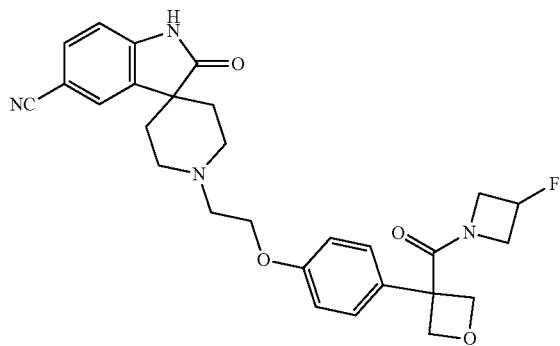 [SMILES: N#Cc1ccc2c(c1)C1(CCN(CCOc3ccc(C4(C(=O)N5CC(F)C5)COC4)cc3)CC1)C(=O)N2]

To a solution of 3-[4-(2-{5-cyano-2-oxo-1,2-dihydrospiro[indole-3,4'-piperidin-1'-yl}ethoxy)phenyl]oxetane-3-carboxylic acid (100 mg, 0.223 mmol) and 3-fluoroazetidine hydrochloride (125 mg, 1.12 mmol) in DCM (2 mL) was added TEA (249 μL, 1.79 mmol). After stirring for 10 min, the reaction was cooled to 0° C. and T3P (199 μL, 0.670 mmol) was added. The mixture was allowed to warm to room temperature and stirred for 16 h. The reaction mixture was diluted with $H_2O$ (10 mL) and extracted with DCM (3×5 mL). The combined organic layers were dried over $Na_2SO_4$, filtered, and concentrated in vacuo. The resulting solid was triturated with MeCN to give 1'-(2-{4-[3-(3-fluoroazetidine-1-carbonyl)oxetan-3-yl]phenoxy}ethyl)-2-oxo-1,2-dihydrospiro[indole-3,4'-piperidine]-5-carbonitrile (Compound 252). $^1$H NMR (400 MHz, DMSO-$d_6$): δ 10.86 (s, 1H), 7.95 (s, 1H), 7.67 (d, J=7.6 Hz, 1H), 7.30 (d, J=8.4 Hz, 2H), 7.03 (d, J=8.4 Hz, 2H), 6.99 (d, J=8.0 Hz, 1H), 5.35-5.22 (m, 1H), 5.10-5.06 (m, 2H), 4.72-4.67 (m, 2H), 4.31-4.22 (m, 1H), 4.15 (s, 2H), 4.00-3.92 (m, 2H), 3.66-3.64 (m, 1H), 2.93-2.87 (m, 4H), 2.78-2.72 (m, 2H), 1.78-1.75 (m, 4H). MS=505.2 [M+H]$^+$.

The following compounds in Table 37 were prepared according to procedures similar to those described for Compound 252 using the appropriate starting materials.

TABLE 37

| # | Structure | Name | Exact Mass [M + H]$^+$ |
|---|---|---|---|
| 253 | 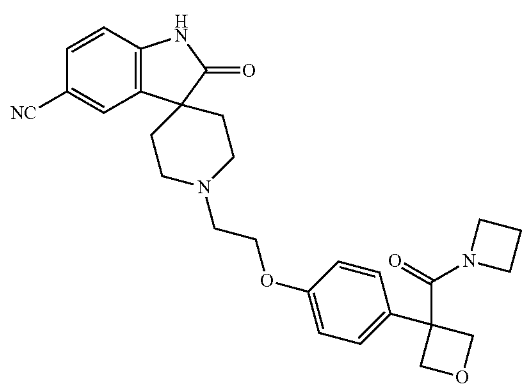 [SMILES: N#Cc1ccc2c(c1)C1(CCN(CCOc3ccc(C4(C(=O)N5CCC5)COC4)cc3)CC1)C(=O)N2] | 1'-(2-{4-[3-(azetidine-1-carbonyl)oxetan-3-yl]phenoxy}ethyl)-2-oxo-1,2-dihydrospiro[indole-3,4'-piperidine]-5-carbonitrile | Calc'd 487.2 Found 487.2 |
| 254 | 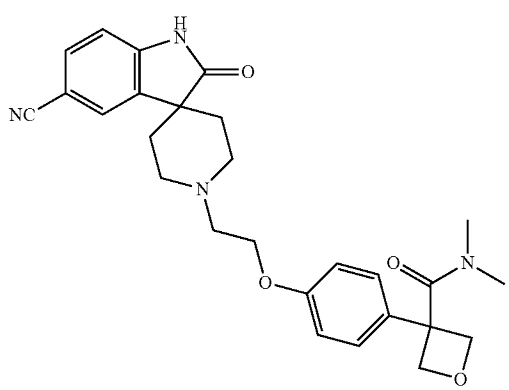 [SMILES: CN(C)C(=O)C1(c2ccc(OCCN3CCC4(CC3)C(=O)Nc3ccc(C#N)cc34)cc2)COC1] | 3-[4-(2-{5-cyano-2-oxo-1,2-dihydrospiro[indole-3,4'-piperidin]-1'-yl}ethoxy)phenyl]-N,N-dimethyloxetane-3-carboxamide | Calc'd 475.2 Found 475.3 |

TABLE 37-continued

| # | Structure | Name | Exact Mass [M + H]+ |
|---|---|---|---|
| 255 | 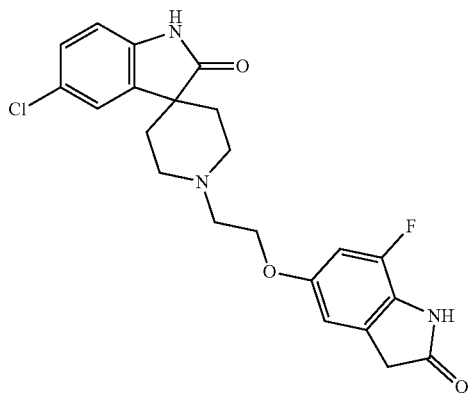 [SMILES: O=C1Cc2cc(OCCN3CCC4(CC3)C(=O)Nc3ccc(Cl)cc34)cc(F)c2N1] | 3-[4-(2-{5-cyano-2-oxo-1,2-dihydrospiro[indole-3,4'-piperidin]-1'-yl}ethoxy)phenyl]-N-methyloxetane-3-carboxamide | Calc'd 461.2 Found 461.3 |

Example 45

5-chloro-1'-{2-[(7-fluoro-2-oxo-2,3-dihydro-1H-indol-5-yl)oxy]ethyl}-1,2-dihydrospiro[indole-3,4'-piperidin]-2-one (Compound 256)

Step 1:
5-bromo-7-fluoro-2,3-dihydro-1H-indole-2,3-dione

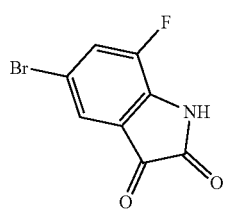 [SMILES: O=C1Nc2c(F)cc(Br)cc2C1=O]

A mixture of 7-fluoro-2,3-dihydro-1H-indole-2,3-dione (5.00 g, 30.3 mmol) and NBS (7.01 g, 39.4 mmol) in DMF (35 mL) was stirred at 80° C. for 2 h. After cooling to room temperature, the mixture was poured into H₂O (150 mL) and filtered to collect the solid. The filter cake was washed with H₂O (3×50 mL). The crude product was triturated with MTBE and dried in vacuo to give 5-bromo-7-fluoro-2,3-dihydro-1H-indole-2,3-dione, which was used in the subsequent step without further purification. MS=243.9/245.9 [M+H]+.

Step 2: 5-bromo-7-fluoro-1-{[2-(trimethylsilyl)ethoxy]methyl}-2,3-dihydro-1H-indole-2,3-dione

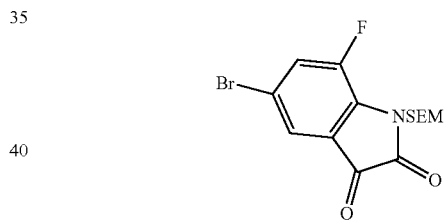

To a 0° C. solution of 5-bromo-7-fluoro-2,3-dihydro-1H-indole-2,3-dione (5.00 g, 20.5 mmol) in DMA (50 mL) under N₂ atmosphere was added NaH (983 mg, 60 wt % in mineral oil, 24.6 mmol). The mixture was allowed to warm to room temperature and stirred for 30 min. After cooling to 0° C., 2-(trimethylsilyl)ethoxymethyl chloride (4.71 mL, 26.6 mmol) was added. The mixture was warmed to room temperature and stirred for another 2 h. The mixture was quenched with saturated aqueous NH₄Cl solution (200 mL), and the mixture was extracted with EtOAc (3×70 mL). The combined organic layers were dried over Na₂SO₄, filtered, and concentrated in vacuo. The crude residue was purified by normal phase silica gel chromatography (Biotage 80 g cartridge, 0-15% EtOAc:petroleum ether) to give 5-bromo-7-fluoro-1-{[2-(trimethylsilyl)ethoxy]methyl}-2,3-dihydro-1H-indole-2,3-dione. MS=391.1/393.1 [M+NH₄]+.

Step 3: 7-fluoro-5-(4,4,5,5-tetramethyl-1,3,2-dioxaborolan-2-yl)-1-{[2-(trimethylsilyl)ethoxy]methyl}-2,3-dihydro-1H-indole-2,3-dione

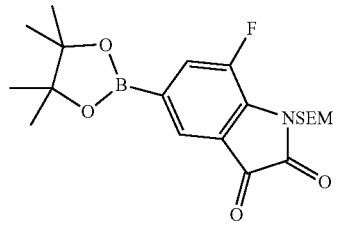 [SMILES: CC1(C)OB(c2cc(F)c3c(c2)C(=O)C(=O)N3COCC[Si](C)(C)C)OC1(C)C]

A mixture of 5-bromo-7-fluoro-1-{[2-(trimethylsilyl)ethoxy]methyl}-2,3-dihydro-1H-indole-2,3-dione (7.00 g, 18.7 mmol), bis(pinacolato)diboron (5.70 g, 22.4 mmol), KOAc (4.59 g, 46.8 mmol) and Pd(dppf)Cl$_2$·CH$_2$Cl$_2$ (1.22 g, 1.50 mmol) in 1,4-dioxane (70 mL) was stirred at 95° C. for 16 h under N$_2$ atmosphere. After cooling to room temperature, the mixture was poured into H$_2$O (200 mL) and extracted with EtOAc (2×100 mL). The combined organic layers were washed with brine (80 mL), dried over Na$_2$SO$_4$, filtered, and concentrated in vacuo. The crude residue was purified by normal phase silica gel chromatography (Biotage 120 g cartridge, 0-8% EtOAc:petroleum ether) to give 7-fluoro-5-(4,4,5,5-tetramethyl-1,3,2-dioxaborolan-2-yl)-1-{[2-(trimethylsilyl)ethoxy]methyl}-2,3-dihydro-1H-indole-2,3-dione. MS=439.3 [M+NH$_4$]$^+$.

Step 4: 7-fluoro-5-hydroxy-1-{[2-(trimethylsilyl)ethoxy]methyl}-2,3-dihydro-1H-indole-2,3-dione

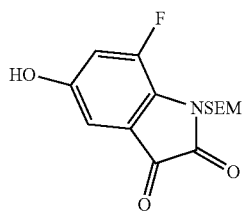 [SMILES: C[Si](C)(C)CCOCN1C(=O)C(=O)c2cc(O)cc(F)c21]

To a 0° C. mixture of 7-fluoro-5-(4,4,5,5-tetramethyl-1,3,2-dioxaborolan-2-yl)-1-{[2-(trimethylsilyl)ethoxy]methyl}-2,3-dihydro-1H-indole-2,3-dione (7.80 g, 18.5 mmol) in acetone (70 mL) and H$_2$O (70 mL) was added Oxone (17.1 g, 27.8 mmol) portionwise. The mixture was allowed to warm to room temperature and stirred for 1 h. The mixture was poured into saturated Na$_2$SO$_3$ solution (200 mL) and extracted with EtOAc (2×80 mL). The combined organic layers were washed with brine (60 mL), dried over Na$_2$SO$_4$, filtered, and concentrated in vacuum. The crude residue was purified by normal phase silica gel chromatography (Biotage 80 g cartridge, 0-25% EtOAc:petroleum ether) to give 7-fluoro-5-hydroxy-1-{[2-(trimethylsilyl)ethoxy]methyl}-2,3-dihydro-1H-indole-2,3-dione.

Step 5: 7-fluoro-5-hydroxy-1-{[2-(trimethylsilyl)ethoxy]methyl}-2,3-dihydro-1H-indol-2-one

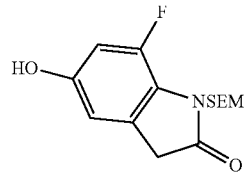 [SMILES: C[Si](C)(C)CCOCN1C(=O)Cc2cc(O)cc(F)c21]

To a solution of 7-fluoro-5-hydroxy-1-{[2-(trimethylsilyl)ethoxy]methyl}-2,3-dihydro-1H-indole-2,3-dione (4.30 g, 13.8 mmol) in DMSO (43 mL) was added N$_2$H$_4$·H$_2$O (11.8 mL, 207 mmol). The mixture was stirred at 120° C. for 3 h. The mixture was diluted with H$_2$O (150 mL) and extracted with EtOAc (2×80 mL). The combined organic layers were washed with brine (60 mL), dried over Na$_2$SO$_4$, filtered, and concentrated in vacuo. The crude residue was purified by normal phase silica gel chromatography (Biotage 40 g cartridge, 0-20% EtOAc:petroleum ether) to give 7-fluoro-5-hydroxy-1-{[2-(trimethylsilyl)ethoxy]methyl}-2,3-dihydro-1H-indol-2-one. MS=296.1 [M−H]$^-$.

Step 6: 5-(2-bromoethoxy)-7-fluoro-1-{[2-(trimethylsilyl)ethoxy]methyl}-2,3-dihydro-1H-indol-2-one

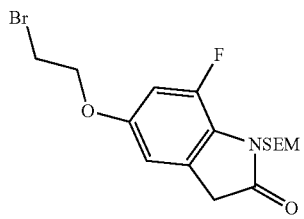 [SMILES: C[Si](C)(C)CCOCN1C(=O)Cc2cc(OCCBr)cc(F)c21]

To a 0° C. mixture of 7-fluoro-5-hydroxy-1-{[2-(trimethylsilyl)ethoxy]methyl}-2,3-dihydro-1H-indol-2-one (500 mg, 1.68 mmol), 2-bromoethanol (477 μL, 6.73 mmol), and PPh$_3$ (882 mg, 3.36 mmol) in THF (10 mL) was added DIAD (654 μL, 3.36 mmol). The mixture was allowed to warm to room temperature and stirred for 16 h. The mixture was diluted with EtOAc (25 mL) and H$_2$O (10 mL). The organic layer was separated, and washed with brine (40 mL), dried over Na$_2$SO$_4$, filtered, and concentrated in vacuo. The crude residue was purified by normal phase silica gel chromatography (Biotage 20 g cartridge, 0-10% EtOAc: petroleum ether) to give 5-(2-bromoethoxy)-7-fluoro-1-{[2-(trimethylsilyl)ethoxy]methyl}-2,3-dihydro-1H-indol-2-one.

Step 7: 5-chloro-1'-{2-[(7-fluoro-2-oxo-1-{[2-(trimethylsilyl)ethoxy]methyl}-2,3-dihydro-1H-indol-5-yl)oxy]ethyl}-1,2-dihydrospiro[indole-3,4'-piperidin]-2-one

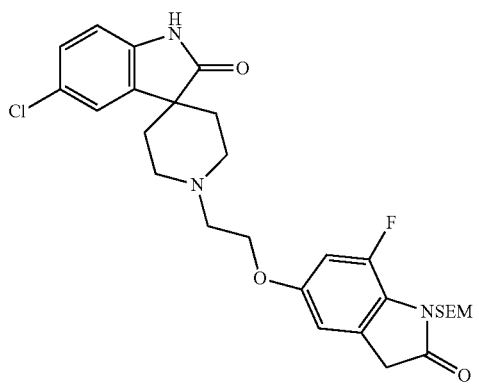 [SMILES: C[Si](C)(C)CCOCN1C(=O)Cc2cc(OCCN3CCC4(CC3)C(=O)Nc3ccc(Cl)cc34)cc(F)c21]

A mixture of 5-(2-bromoethoxy)-7-fluoro-1-{[2-(trimethylsilyl)ethoxy]methyl}-2,3-dihydro-1H-indol-2-one (170 mg, 0.420 mmol), 5-chloro-1,2-dihydrospiro[indole-3,4'-piperidin]-2-one (Intermediate B-4, 79.6 mg, 0.291 mmol), and NaHCO₃ (106 mg, 1.26 mmol) in MeCN (2 mL) was stirred at 80° C. for 16 h. After cooling to room temperature, the mixture was diluted with EtOAc (25 mL) and H₂O (10 mL). The organic layer was separated, washed with brine (20 mL), dried over Na₂SO₄, filtered, and concentrated in vacuo. The crude residue was purified by normal phase silica gel chromatography (Biotage 12 g cartridge, 0-100% EtOAc:petroleum ether) to give 5-chloro-1'-{2-[(7-fluoro-2-oxo-1-{[2-(trimethylsilyl)ethoxy]methyl}-2,3-dihydro-1H-indol-5-yl)oxy]ethyl}-1,2-dihydrospiro[indole-3,4'-piperidin]-2-one. MS=560.2 [M+H]⁺.

Step 8: 5-chloro-1'-{2-[(7-fluoro-2-oxo-2,3-dihydro-1H-indol-5-yl)oxy]ethyl}-1,2-dihydrospiro[indole-3, 4'-piperidin]-2-one (Compound 256)

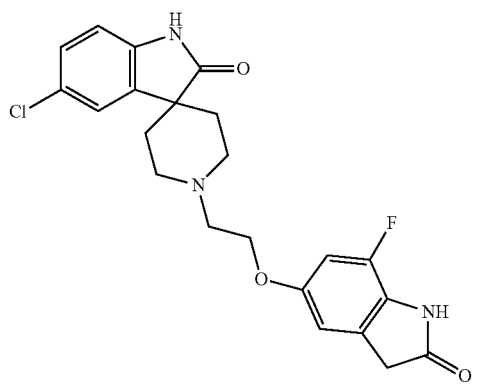 [SMILES: O=C1Cc2cc(OCCN3CCC4(CC3)C(=O)Nc3ccc(Cl)cc34)cc(F)c2N1]

A solution of 5-chloro-1'-{2-[(7-fluoro-2-oxo-1-{[2-(trimethylsilyl)ethoxy]methyl}-2,3-dihydro-1H-indol-5-yl) oxy]ethyl}-1,2-dihydrospiro[indole-3,4'-piperidin]-2-one (80.0 mg, 0.143 mmol) in 4.0 M HCl in 1,4-dioxane (2.0 mL, 8.0 mmol) was stirred at room temperature for 1 h. The mixture was concentrated in vacuo, and then NH₃·H₂O (0.5 mL) was added dropwise. The mixture was stirred at room temperature for 30 min, and then diluted with H₂O (5 mL). The mixture was extracted with EtOAc (2×5 mL). The combined organic layers were dried over Na₂SO₄, filtered, and concentrated in vacuo. The crude residue was purified by reverse phase preparative HPLC (Phenomenex C₁₈ column, 20-50% MeCN: 10 mM NH₄HCO₃ in H₂O) to give 5-chloro-1'-{2-[(7-fluoro-2-oxo-2,3-dihydro-1H-indol-5-yl) oxy]ethyl}-1,2-dihydrospiro[indole-3,4'-piperidin]-2-one (Compound 256). ¹H NMR (400 MHz, DMSO-d₆): δ 10.67 (s, 1H), 10.51 (s, 1H), 7.53 (s, 1H), 7.26 (d, J=8.0 Hz, 1H), 6.87 (d, J=8.4 Hz, 1H), 6.82-6.80 (m, 2H), 4.11 (t, J=5.6 Hz, 2H), 3.54 (s, 2H), 2.93-2.86 (m, 2H), 2.85-2.82 (m, 2H), 2.73-2.70 (m, 2H), 1.81-1.73 (m, 4H). MS=430.2 [M+H]⁺.

Example 46

2-[4-(2-{5-cyano-2-oxo-1,2-dihydrospiro[indole-3, 4'-piperidin]-1'-yl}ethoxy)phenyl]-2-methylpropanamide (Compound 257)

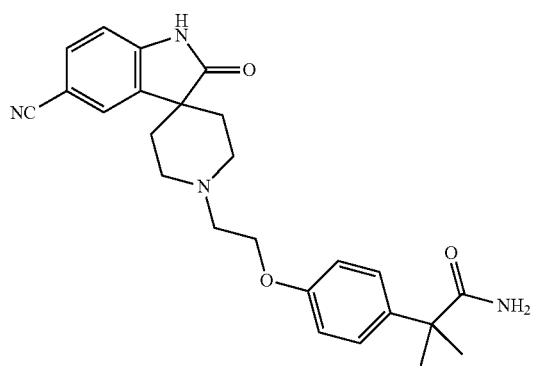 [SMILES: CC(C)(C(N)=O)c1ccc(OCCN2CCC3(CC2)C(=O)Nc2ccc(C#N)cc23)cc1]

Step 1: methyl 2-(4-hydroxyphenyl)-2-methylpropanoate

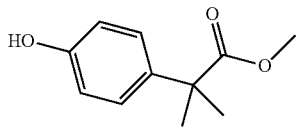

To a 0° C. solution of 2-(4-hydroxyphenyl)-2-methylpropanoic acid (900 mg, 4.99 mmol) in MeOH (18 mL) was added SOCl₂ (471 μL, 6.49 mmol). The mixture was stirred at 70° C. for 2 h. After cooling to room temperature, the mixture was concentrated in vacuo. The residue was diluted with H₂O (30 mL), extracted with EtOAc (2×20 mL), dried over Na₂SO₄, filtered, and concentrated to give methyl 2-(4-hydroxyphenyl)-2-methylpropanoate, which was used in the subsequent step without further purification. MS=193.1 [M−H]⁻.

Step 2: methyl 2-[4-(2-bromoethoxy)phenyl]-2-methylpropanoate

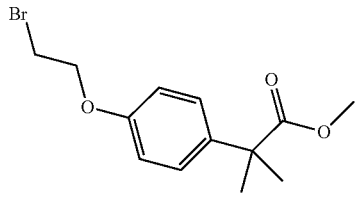 [SMILES: COC(=O)C(C)(C)c1ccc(OCCBr)cc1]

To a solution of methyl 2-(4-hydroxyphenyl)-2-methylpropanoate (820 mg, 4.22 mmol) and 1,2-dibromoethane (12.7 mL, 169 mmol) in MeCN (16 mL) was added K$_2$CO$_3$ (2.92 g, 21.1 mmol). After stirring at 80° C. for 16 h, the mixture was concentrated in vacuum. The residue was diluted with H$_2$O (30 mL), extracted with EtOAc (2×20 mL), dried over Na$_2$S04, filtered, and concentrated in vacuo. The crude residue was purified by normal phase silica gel chromatography (Biotage 40 g cartridge, 0-20% EtOAc: petroleum ether) to give methyl 2-[4-(2-bromoethoxy)phenyl]-2-methylpropanoate. MS=301.0 [M+H]$^+$.

Step 3: methyl 2-[4-(2-{5-cyano-2-oxo-1,2-dihydrospiro[indole-3,4'-piperidin]-1'-yl}ethoxy)phenyl]-2-methylpropanoate

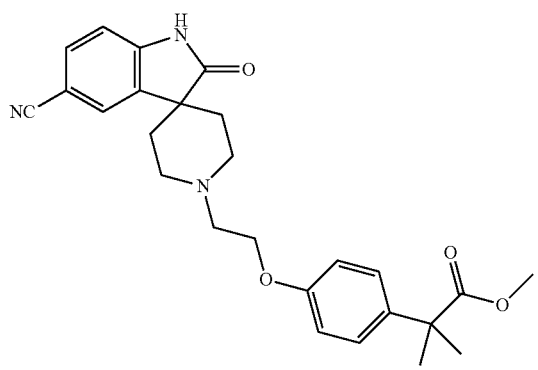 [SMILES: COC(=O)C(C)(C)c1ccc(OCCN2CCC3(CC2)C(=O)Nc2ccc(C#N)cc23)cc1]

To a solution of methyl 2-[4-(2-bromoethoxy)phenyl]-2-methylpropanoate (300 mg, 0.996 mmol) and 2-oxo-1,2-dihydrospiro[indole-3,4'-piperidine]-5-carbonitrile (Intermediate B-9, 272 mg, 1.03 mmol, HCl salt) in MeCN (3 mL) was added NaHCO$_3$ (251 mg, 2.99 mmol). The mixture was stirred at 80° C. for 16 h. After cooling to room temperature, the residue was diluted with H$_2$O (50 mL), extracted with EtOAc (2×30 mL), dried over Na$_2$SO$_4$, filtered, and concentrated in vacuo. The crude residue was purified by normal phase silica gel chromatography (Biotage 12 g cartridge, 0-75% EtOAc:petroleum ether) to give methyl 2-[4-(2-{5-cyano-2-oxo-1,2-dihydrospiro[indole-3,4'-piperidin]-1'-yl}ethoxy)phenyl]-2-methylpropanoate. MS=448.2 [M+H]$^+$.

Step 4: 2-[4-(2-{5-cyano-2-oxo-1,2-dihydrospiro[indole-3,4'-piperidin]-1'-yl}ethoxy)phenyl]-2-methylpropanoic acid

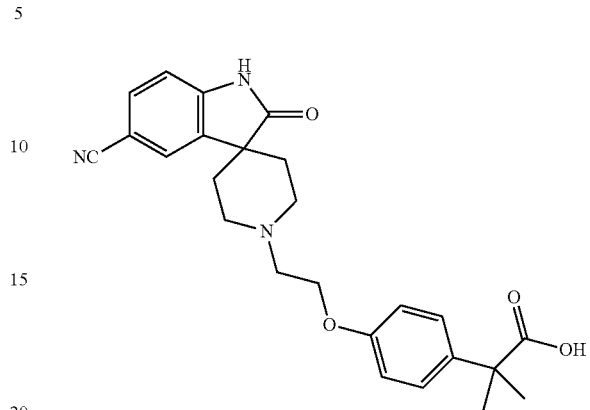

To a solution of methyl 2-[4-(2-{5-cyano-2-oxo-1,2-dihydrospiro[indole-3,4'-piperidin]-1'-yl}ethoxy)phenyl]-2-methylpropanoate (120 mg, 0.268 mmol) in THF (2 mL) was added a solution of NaOH (26.8 mg, 0.670 mmol) in H$_2$O (1 mL). The mixture was stirred at room temperature for 3 h. The reaction mixture was diluted with H$_2$O (5 mL) and then adjusted pH=3-4 with 4.0 M aqueous HCl solution. The residue was extracted with EtOAc (2×20 mL) and washed with brine (10 mL). The organic combined organic layers were dried over Na$_2$SO$_4$, filtered, and concentrated in vacuo to give 2-[4-(2-{5-cyano-2-oxo-1,2-dihydrospiro[indole-3,4'-piperidin]-1'-yl}ethoxy)phenyl]-2-methylpropanoic acid, which was used in the subsequent step without further purification. MS=434.2 [M+H]$^+$.

Step 5: 2-[4-(2-{5-cyano-2-oxo-1,2-dihydrospiro[indole-3,4'-piperidin]-1'-yl}ethoxy)phenyl]-2-methylpropanamide (Compound 257)

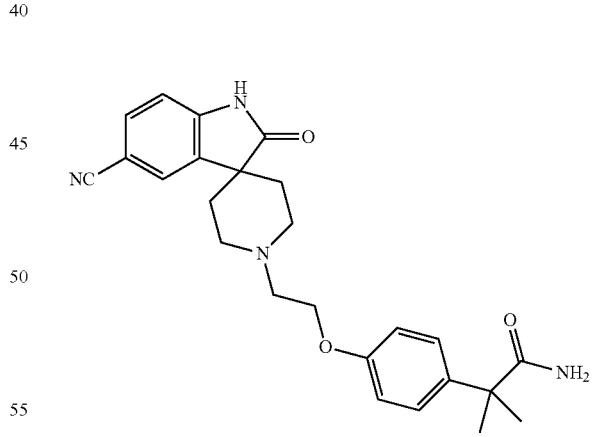

To a solution of 2-[4-(2-{5-cyano-2-oxo-1,2-dihydrospiro[indole-3,4'-piperidin]-1'-yl}ethoxy)phenyl]-2-methylpropanoic acid (80.0 mg, 0.186 mmol) and NH$_4$Cl (11.9 mg, 0.221 mmol) in THF (0.5 mL) was added DIEA (77.2 µL, 0.443 mmol) and HATU (84.2 mg, 0.221 mmol). The mixture was stirred at room temperature for 1 h. The reaction mixture was diluted with H$_2$O (5 mL) and extracted with EtOAc (2×10 mL). The combined organic layers were washed with brine (10 mL), dried over Na$_2$SO$_4$, filtered, and concentrated in vacuo. The crude residue was purified by reverse phase preparative HPLC (Waters Xbridge Prep OBD C$_{18}$ column, 20-50% MeCN: 10 mM NH$_4$HCO$_3$ in H$_2$O) to give 2-[4-(2-{5-cyano-2-oxo-1,2-dihydrospiro[indole-3,4'-piperidin]-1'-yl}ethoxy)phenyl]-2-methylpropanamide (Compound 257). $^1$H NMR (400 MHz, DMSO-d$_6$): δ 10.83 (br s, J=1.2 Hz, 1H) 7.93 (d, J=1.2 Hz, 1H) 7.65 (dd, J=8.0, 1.5 Hz, 1H) 7.19-7.25 (m, 2H) 6.96 (d, J=8.0 Hz, 1H) 6.88 (d, J=8.8 Hz, 2H), 6.78 (br d, J=6.4 Hz, 2H), 4.09 (t, J=6.0 Hz, 2H), 2.90-2.82 (m, 4H), 2.73-2.71 (m, 2H), 1.84-1.66 (m, 4H), 1.38 (s, 6H). MS=433.2 [M+H]$^+$.

Example 47

5-(2-{5-chloro-2-oxo-1,2-dihydrospiro[indole-3,4'-piperidin]-1'-yl}ethoxy)pyrimidine-2-carboxamide (Compound 258)

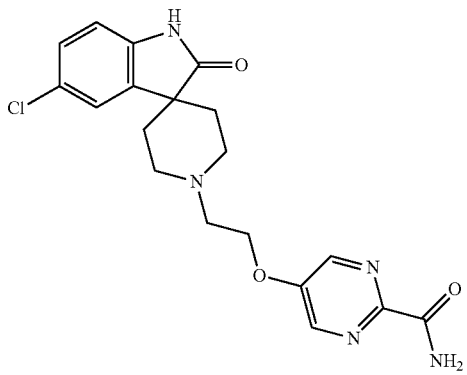 [SMILES: NC(=O)c1ncc(OCCN2CCC3(CC2)C(=O)Nc2ccc(Cl)cc23)cn1]

Step 1: 5-(4,4,5,5-tetramethyl-1,3,2-dioxaborolan-2-yl)pyrimidine-2-carbonitrile

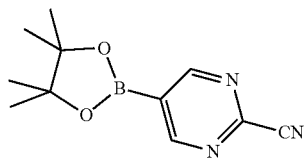 [SMILES: CC1(C)OB(c2cnc(C#N)nc2)OC1(C)C]

To a mixture of 5-bromopyrimidine-2-carbonitrile (1.00 g, 5.43 mmol) and bis(pinacolato)diboron (1.56 g, 6.52 mmol) in dioxane (10 mL) under N$_2$ atmosphere was added KOAc (1.07 g, 10.9 mmol) and Pd(dppf)Cl$_2$ (199 mg, 0.272 mmol). The mixture was degassed and purged with N$_2$ (3×), and then stirred at 80° C. for 12 h. After cooling to room temperature, the reaction mixture was concentrated in vacuo. The residue was diluted with H$_2$O (20 mL) and extracted with EtOAc (3×30 mL). The combined organic layers were washed with brine (10 mL), dried over Na$_2$SO$_4$, filtered, and concentrated in vacuo. The crude residue was purified by normal phase silica gel chromatography (Biotage 12 g cartridge, 0-35% EtOAc:petroleum ether) to give 5-(4,4,5,5-tetramethyl-1,3,2-dioxaborolan-2-yl)pyrimidine-2-carbonitrile. MS=232.2 [M+H]$^+$.

Step 2: 5-hydroxypyrimidine-2-carbonitrile

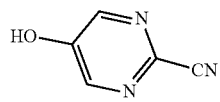

To a 0° C. solution of 5-(4,4,5,5-tetramethyl-1,3,2-dioxaborolan-2-yl)pyrimidine-2-carbonitrile (15.0 g, 64.9 mmol) in acetone (100 mL) and H$_2$O (100 mL) was added Oxone (47.9 g, 77.9 mmol). The mixture was stirred at room temperature for 1 h and was then quenched with saturated Na$_2$SO$_3$ (100 mL) and extracted with EtOAc (3×100 mL). The combined organic layers were washed with brine (100 mL), dried over Na$_2$SO$_4$, filtered, and concentrated in vacuo. The crude residue was purified by normal phase silica gel chromatography (Biotage 100 g cartridge, 0-65% EtOAc: petroleum ether) to give 5-hydroxypyrimidine-2-carbonitrile. MS=122.0 [M+H]$^+$.

Step 3: 5-(2-bromoethoxy)pyrimidine-2-carbonitrile

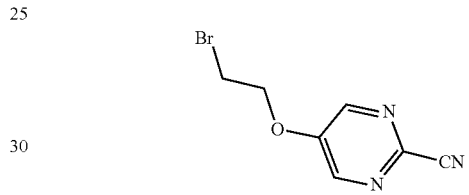

To a mixture of 5-hydroxypyrimidine-2-carbonitrile (300 mg, 2.48 mmol) and 1,2-dibromoethane (7.48 mL, 99.1 mmol) in MeCN (6 mL) was added K$_2$CO$_3$ (1.03 g, 7.43 mmol). The mixture was stirred at 60° C. for 12 h. After cooling to room temperature, the reaction mixture was concentrated in vacuo to remove MeCN. The residue was diluted with H$_2$O (10 mL) and extracted with EtOAc (3×30 mL). The combined organic layers were washed with brine (10 mL), dried over Na$_2$SO$_4$, filtered, and concentrated in vacuo. The crude residue was purified by normal phase silica gel chromatography (Biotage 4 g cartridge, 0-60% EtOAc: petroleum ether) to give 5-(2-bromoethoxy)pyrimidine-2-carbonitrile. MS=228.1/230.1 [M+H]$^+$.

Step 4: 5-(2-{5-chloro-2-oxo-1,2-dihydrospiro[indole-3,4'-piperidin]-1'-yl}ethoxy)pyrimidine-2-carbonitrile

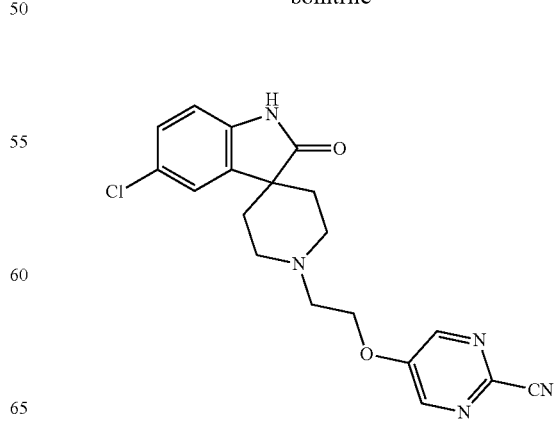

1111

To a mixture of 5-(2-bromoethoxy)pyrimidine-2-carbonitrile (165 mg, 0.724 mmol) and 5-chloro-1,2-dihydrospiro[indole-3,4'-piperidin]-2-one (Intermediate B-4, 206 mg, 0.868 mmol,) in MeCN (2 ml) was added NaHCO$_3$ (122 mg, 1.45 mmol). The mixture was stirred at 80° C. for 12 h. After cooling to room temperature, the reaction mixture was concentrated in vacuo to remove MeCN. The residue was diluted with H$_2$O (10 mL) and extracted with EtOAc (3×30 mL). The combined organic layers were washed with brine (10 mL), dried over Na$_2$SO$_4$, filtered, and concentrated 5-(2-{5-chloro-2-oxo-1,2-dihydrospiro[indole-3,4'-piperidin]-1'-yl}ethoxy)pyrimidine-2-carbonitrile, which was used in the subsequent step without further purification. MS=384.2 [M+H]$^+$.

Step 5: 5-(2-{5-chloro-2-oxo-1,2-dihydrospiro[indole-3,4'-piperidin]-1'-yl}ethoxy)pyrimidine-2-carboxamide (Compound 258)

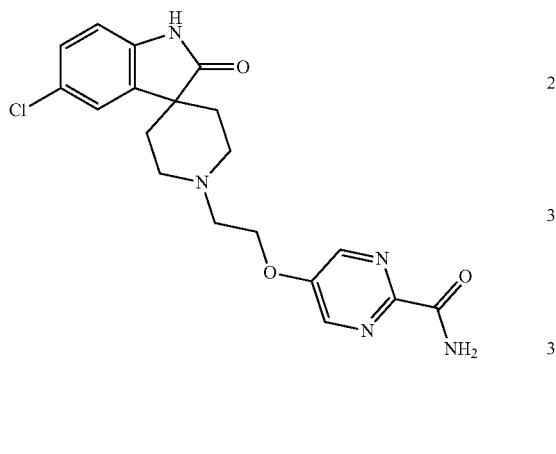

To a 0° C. mixture of 5-(2-{5-chloro-2-oxo-1,2-dihydrospiro[indole-3,4'-piperidin]-1'-yl}ethoxy)pyrimidine-2-carbonitrile (160 mg, 0.417 mmol) and K$_2$CO$_3$ (115 mg, 0.834 mmol) in DMSO (2 mL) was added H$_2$O$_2$ in H$_2$O (120 µL, 30 wt % 1.25 mmol) dropwise. The mixture was stirred at room temperature for 2 h. The reaction mixture was cooled to 0° C., quenched with saturated aqueous Na$_2$SO$_3$ solution (5 mL), diluted with H$_2$O (5 mL), and then extracted with EtOAc (3×10 mL). The combined organic layers were washed with brine (5 mL), dried over Na$_2$SO$_4$, filtered, and concentrated in vacuo. The crude residue was purified by reverse phase preparative HPLC (Waters Xbridge Prep OBD C$_{18}$ column, 15-40% MeCN: 10 mM NH$_4$HCO$_3$ in H$_2$O) to give 5-(2-{5-chloro-2-oxo-1,2-dihydrospiro[indole-3,4'-piperidin]-1'-yl}ethoxy)pyrimidine-2-carboxamide (Compound 258). $^1$H NMR (400 MHz, DMSO-d$_6$): δ 10.50 (s, 1H), 8.68 (s, 2H), 8.05 (s, 1H), 7.65 (s, 1H), 7.52 (d, J=2.00 Hz, 1H), 7.25 (dd, J=10.40, 6.00 Hz, 1H), 6.87 (d, J=8.40 Hz, 1H), 4.41 (t, J=5.60 Hz, 2H), 2.99-2.88 (m, 4H), 2.76-2.70 (m, 2H), 1.84-1.68 (m, 4H). MS=402.2 [M+H]$^+$.

1112

Example 48

4-[4-(2-{5-chloro-2-oxo-1,2-dihydrospiro[indole-3,4'-piperidin]-1'-yl}ethoxy)-2,6-difluorobenzoyl]-1λ$^6$-thiomorpholine-1,1-dione (Compound 259)

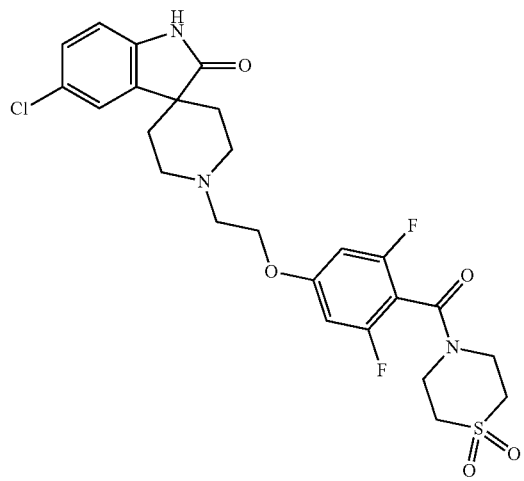 [SMILES: O=C(c1c(F)cc(OCCN2CCC3(CC2)C(=O)Nc2ccc(Cl)cc23)cc1F)N1CCS(=O)(=O)CC1]

Step 1: methyl 2,6-difluoro-4-hydroxybenzoate

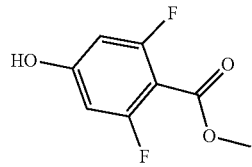

To a 0° C. solution of 2,6-difluoro-4-hydroxybenzoic acid (4.50 g, 25.9 mmol) in MeOH (45 mL) and MTBE (45 mL) was added 2.0 M diazomethyl(trimethyl)silane in DCM (14.2 mL, 28.4 mmol) dropwise. The mixture was warmed to room temperature and stirred for 16 h. The reaction mixture was concentrated in vacuo to provide methyl 2,6-difluoro-4-hydroxybenzoate, which was used in the subsequent step without further purification. MS=187.1 [M–H]$^+$.

Step 2: methyl 4-(2-bromoethoxy)-2,6-difluorobenzoate

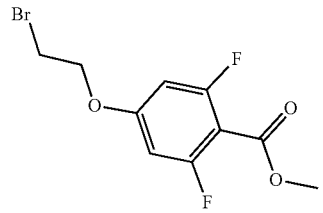 [SMILES: COC(=O)c1c(F)cc(OCCBr)cc1F]

To a solution of methyl 2,6-difluoro-4-hydroxybenzoate (4.38 g, 23.3 mmol) in MeCN (15 mL) was added K$_2$CO$_3$ (16.1 g, 116 mmol) and 1,2-dibromoethane (70.3 mL, 931 mmol). The mixture was heated to 80° C. and stirred for 16 h. After cooling room temperature, solids were removed by filtration and the filtrate was concentrated in vacuo to provide methyl 4-(2-bromoethoxy)-2,6-difluorobenzoate, which was used in the subsequent step without further purification. MS=295.2/296.8 [M+H]$^+$.

Step 3: methyl 4-(2-{5-chloro-2-oxo-1,2-dihydrospiro[indole-3,4'-piperidin]-1'-yl}ethoxy)-2,6-difluorobenzoate

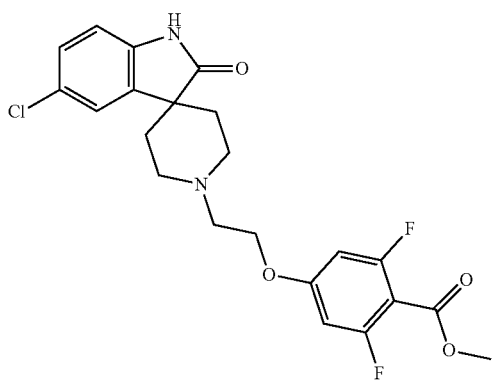 [SMILES: COC(=O)c1c(F)cc(OCCN2CCC3(CC2)C(=O)Nc2ccc(Cl)cc23)cc1F]

To a solution of methyl 4-(2-bromoethoxy)-2,6-difluorobenzoate (3.00 g, 10.2 mmol) in MeCN (60 mL) was added NaHCO$_3$ (2.56 g, 30.5 mmol) and 5-chloro-1,2-dihydrospiro[indole-3,4'-piperidin]-2-one (Intermediate B-4, 2.41 g, 8.82 mmol, HCl salt). The mixture was heated to 80° C. and stirred for 16 h. After cooling to room temperature, solids were removed by filtration and the filtrate was concentrated in vacuo. The filtrate was diluted with H$_2$O and then extracted with a 10:1 solution of DCM: MeOH (3×40 mL). The combined organic layers were washed with brine (40 mL), dried over Na$_2$SO$_4$, filtered, and concentrated in vacuo. The crude residue was purified by reverse phase preparative HPLC (Phenomenex Luna C$_{18}$ column, 20-50% MeCN: 10 mM TFA in H$_2$O) to give methyl 4-(2-{5-chloro-2-oxo-1,2-dihydrospiro[indole-3,4'-piperidin]-1'-yl}ethoxy)-2,6-difluorobenzoate. MS=451.1 [M+H]$^+$.

Step 4: 4-(2-{5-chloro-2-oxo-1,2-dihydrospiro[indole-3,4'-piperidin]-1'-yl}ethoxy)-2,6-difluorobenzoic acid

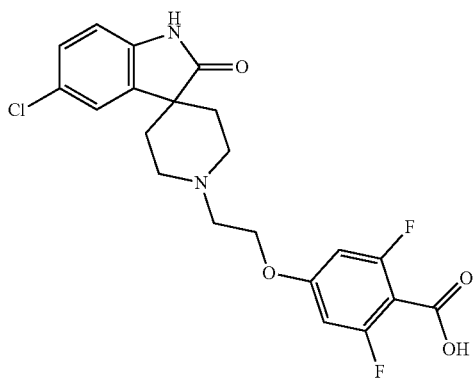 [SMILES: O=C(O)c1c(F)cc(OCCN2CCC3(CC2)C(=O)Nc2ccc(Cl)cc23)cc1F]

To a solution of methyl 4-(2-{5-chloro-2-oxo-1,2-dihydrospiro[indole-3,4'-piperidin]-1'-yl}ethoxy)-2,6-difluorobenzoate (1.60 g, 3.55 mmol) in THF (32 mL) and H$_2$O (64 mL) was added LiOH H$_2$O (596 mg, 14.2 mmol). The mixture was stirred at room temperature for 16 h, and then was concentrated in vacuo. The residue was diluted with EtOAc (50 mL) and H$_2$O (10 mL) and was adjusted to pH=5-6 with dropwise addition of 1.0 M aqueous HCl. The organic layer was separated, and aqueous phase was extracted with EtOAc (2×40 mL). The combined organic layers were washed with brine (40 mL), dried over Na$_2$SO$_4$, filtered, and concentrated in vacuo to give 4-(2-{5-chloro-2-oxo-1,2-dihydrospiro[indole-3,4'-piperidin]-1'-yl}ethoxy)-2,6-difluorobenzoic acid, which was used in the subsequent step without further purification. MS=437.0 [M+H]$^+$.

Step 5: 4-[4-(2-{5-chloro-2-oxo-1,2-dihydrospiro[indole-3,4'-piperidin]-1'-yl}ethoxy)-2,6-difluorobenzoyl]-1$\lambda^6$-thiomorpholine-1,1-dione (Compound 259)

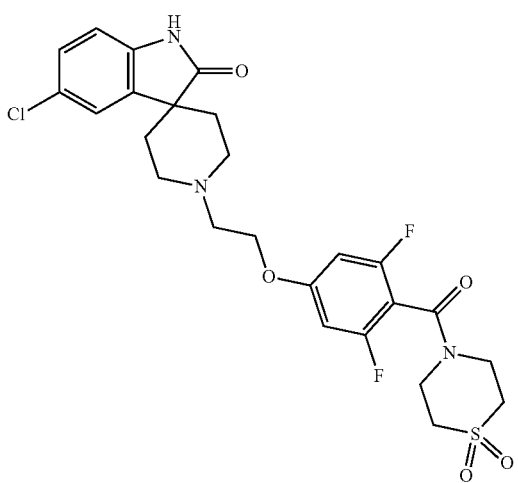 [SMILES: O=C(c1c(F)cc(OCCN2CCC3(CC2)C(=O)Nc2ccc(Cl)cc23)cc1F)N1CCS(=O)(=O)CC1]

To a 0° C. solution of 4-(2-{5-chloro-2-oxo-1,2-dihydrospiro[indole-3,4'-piperidin]-1'-yl}ethoxy)-2,6-difluorobenzoic acid (1.00 g, 2.29 mmol) in DMF (5 mL) was added 1-methylimidazole (0.547 mL, 6.87 mmol) and 1$\lambda^6$-thiomorpholine-1,1-dione (464 mg, 3.43 mmol). After stirring for 10 min, [chloro(dimethylamino)methylene]-dimethyl-ammonium hexafluorophosphate (963 mg, 3.43 mmol) was added. The mixture was allowed to warm to room temperature and stirred for 2 h. The reaction mixture was poured into the H$_2$O (30 mL) and then extracted with EtOAc (3×40 mL). The combined organic layers were washed with brine (30 mL), dried over Na$_2$SO$_4$, filtered, and concentrated in vacuo. The crude residue was purified by reverse phase preparative HPLC (Kromasil C$_{18}$ column, 20-60% MeCN: 10 mM NH$_4$HCO$_3$ in H$_2$O) to give 4-[4-(2-{5-chloro-2-oxo-1,2-dihydrospiro[indole-3,4'-piperidin]-1'-yl}ethoxy)-2,6-difluorobenzoyl]-1$\lambda^6$-thiomorpholine-1,1-dione (Compound 259). $^1$H NMR (400 MHz, DMSO-d$_6$): δ 10.49 (s, 1H), 7.51 (d, J=1.6 Hz, 1H), 7.24 (d, J=8.4, 2.0 Hz, 1H), 6.94 (d, J=9.6 Hz, 2H), 6.85 (d, J=8.4 Hz, 1H), 4.22 (t, J=5.2 Hz, 2H), 4.11-4.05 (m, 2H), 3.79-3.69 (m, 2H), 3.29-3.28 (m, 2H), 3.11-3.10 (m, 2H), 2.91-2.84 (m, 4H), 2.68-2.67 (m, 2H), 1.78-1.70 (m, 4H). MS=554.2 [M+H]$^+$.

Example 49

1'-{2-[4-(1,1-dioxo-1λ⁶-thiomorpholine-4-carbonyl)-3,5-difluorophenoxy]ethyl}-1-methyl-2-oxo-1,2-dihydrospiro[indole-3,4'-piperidine]-5-carbonitrile (Compound 260)

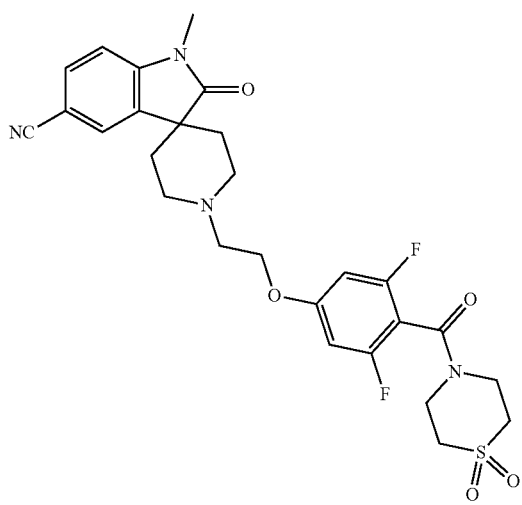 [SMILES: CN1C(=O)C2(CCN(CCOc3cc(F)c(C(=O)N4CCS(=O)(=O)CC4)c(F)c3)CC2)c2cc(C#N)ccc21]

Step 1: methyl 4-(2-{5-cyano-1-methyl-2-oxo-1,2-dihydrospiro[indole-3,4'-piperidin]-1'-yl}ethoxy)-2,6-difluorobenzoate

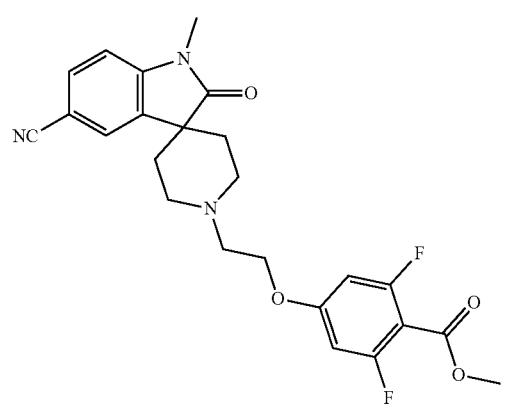 [SMILES: COC(=O)c1c(F)cc(OCCN2CCC3(CC2)C(=O)N(C)c2ccc(C#N)cc23)cc1F]

To a solution of methyl 4-(2-bromoethoxy)-2,6-difluorobenzoate (Example 48: Step 2, 300 mg, 1.02 mmol) in MeCN (4 mL) was added NaHCO₃ (256 mg, 3.05 mmol) and 1-methyl-2-oxo-1,2-dihydrospiro[indole-3,4'-piperidine]-5-carbonitrile (Intermediate B-15, 245 mg, 1.02 mmol). The mixture was heated to 80° C. and stirred for 16 h. After cooling to room temperature, solids were removed by filtration and the filtrate was concentrated in vacuo. The crude residue was purified by preparative TLC (SiO₂, 10:1 DCM:MeOH) to give methyl 4-(2-{5-cyano-1-methyl-2-oxo-1,2-dihydrospiro[indole-3,4'-piperidin]-1'-yl}ethoxy)-2,6-difluorobenzoate. MS=456.2 [M+H]⁺.

Step 2: 4-(2-{5-cyano-1-methyl-2-oxo-1,2-dihydrospiro[indole-3,4'-piperidin]-1'-yl}ethoxy)-2,6-difluorobenzoic acid

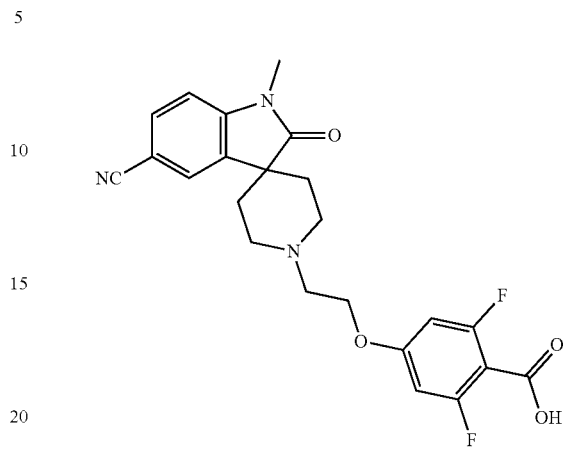

To a solution of methyl 4-(2-{5-cyano-1-methyl-2-oxo-1,2-dihydrospiro[indole-3,4'-piperidin]-1'-yl}ethoxy)-2,6-difluorobenzoate (290 mg, 0.637 mmol) in THF (3.6 mL) and H₂O (2.0 mL) was added LiOH H₂O (53.4 mg, 1.42 mmol). The mixture was stirred at room temperature for 16 h. The reaction mixture was poured into H₂O (10 mL) and adjusted to pH=4-6 via the dropwise addition of 1.0 M aqueous HCl. The mixture was extracted with EtOAc (3×15 mL). The combined organic layers were washed with brine (20 mL), dried over Na₂SO₄, filtered, and concentrated in vacuo to give 4-(2-{5-cyano-1-methyl-2-oxo-1,2-dihydrospiro[indole-3,4'-piperidin]-1'-yl}ethoxy)-2,6-difluorobenzoic acid, which was used in the subsequent step without further purification. MS=442.2 [M+H]⁺.

Step 3: 1'-{2-[4-(1,1-dioxo-1λ⁶-thiomorpholine-4-carbonyl)-3,5-difluorophenoxy]ethyl}-1-methyl-2-oxo-1,2-dihydrospiro[indole-3,4'-piperidine]-5-carbonitrile (Compound 260)

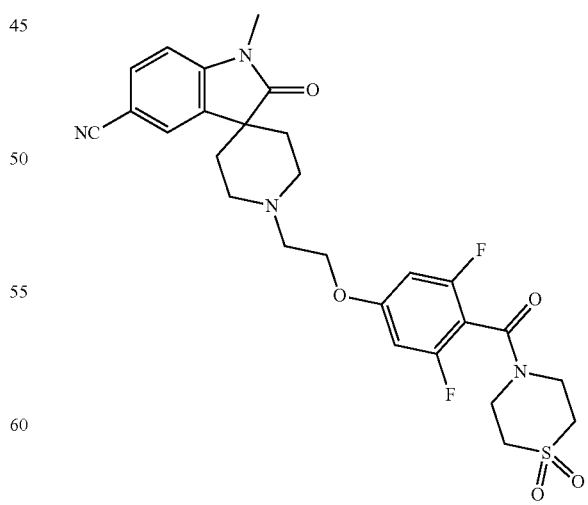

To a solution of 1λ⁶-thiomorpholine-1,1-dione (62.2 mg, 0.362 mmol, HCl salt) and 4-(2-{5-cyano-1-methyl-2-oxo-1,2-dihydrospiro[indole-3,4'-piperidin]-1'-yl}ethoxy)-2,6- difluorobenzoic acid (80.0 mg, 0.181 mmol) in DMF (2 mL) was added 1-methylimidazole (72.2 µL, 0.906 mmol). After stirring for 10 min, [chloro(dimethylamino)methylene]-dimethyl-ammonium hexafluorophosphate (102 mg, 0.363 mmol) was added and the mixture was stirred at room temperature for 2 h. The reaction mixture was quenched with H$_2$O (1 mL), solids were removed by filtration, and the filtrate was concentrated in vacuo. The residue was diluted with H$_2$O (10 mL) and extracted with EtOAc (3×10 mL). The combined organic layers were washed with brine (20 mL), dried over Na$_2$SO$_4$, filtered, and concentrated in vacuo. The crude residue was purified by reverse phase preparative HPLC (Phenomenex C$_{18}$ column, 15-45% MeCN: 10 mM NH$_4$HCO$_3$ in H$_2$O) to give 1'-{2-[4-(1,1-dioxo-1λ$^6$-thiomorpholine-4-carbonyl)-3,5-difluorophenoxy]ethyl}-1-methyl-2-oxo-1,2-dihydrospiro[indole-3,4'-piperidine]-5-carbonitrile (Compound 260). $^1$H NMR (400 MHz, DMSO-d$_6$): δ 7.99 (s, 1H), 7.80 (dd, J=8.0, 1.6, 1H), 7.20 (d, J=8.4 Hz, 1H), 6.94 (d, J=10 Hz, 2H), 4.22 (t, J=5.4 Hz, 2H), 4.08-4.05 (m, 2H), 3.74-3.71 (m, 2H), 3.35-3.27 (m, 2H), 3.14 (s, 3H), 3.09 (br s, 2H), 2.90-2.87 (m, 4H), 2.85-2.74 (m, 2H), 1.78-1.74 (m, 4H). MS=559.2 [M+H]$^+$.

Example 50

1'-{2-[4-(1,1-dioxo-1λ$^6$-thiomorpholine-4-carbonyl)-3-(trifluoromethyl)phenoxy]ethyl}-1-methyl-2-oxo-1,2-dihydrospiro[indole-3,4'-piperidine]-5-carbonitrile (Compound 261)

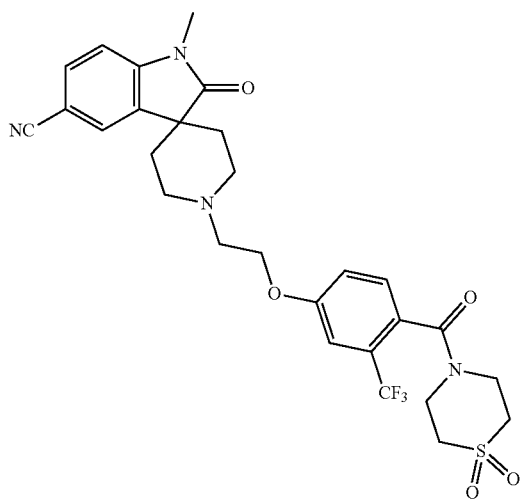 [SMILES: CN1C(=O)C2(CCN(CCOc3ccc(C(=O)N4CCS(=O)(=O)CC4)c(C(F)(F)F)c3)CC2)c2cc(C#N)ccc21]

Step 1: methyl 4-hydroxy-2-(trifluoromethyl)benzoate

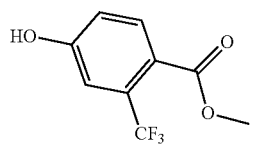

To a 0° C. solution of 4 4-hydroxy-2-(trifluoromethyl)benzoic acid (3.30 g, 16.0 mmol) in MeOH (50 mL) was added SOCl$_2$ (11.0 mL, 152 mmol) dropwise. The mixture was heated to 50° C. and stirred for 12 h. The mixture was cooled to 0° C. and quenched with saturated NH$_4$Cl aqueous solution (100 mL). The aqueous phase was extracted with EtOAc (3×100 mL). The combined organic layers were washed with brine (100 mL), dried over Na$_2$SO$_4$, filtered, and concentrated in vacuo. The crude residue was purified by normal phase silica gel chromatography (Biotage 40 g cartridge, 0-50% EtOAc:petroleum ether) to give methyl 4-hydroxy-2-(trifluoromethyl)benzoate. MS=221.1 [M+H]$^+$ Step 2: methyl 4-(2-bromoethoxy)-2-(trifluoromethyl)benzoate

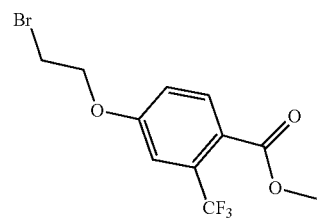 [SMILES: COC(=O)c1ccc(OCCBr)cc1C(F)(F)F]

To a solution of methyl 4-hydroxy-2-(trifluoromethyl)benzoate (2.50 g, 11.4 mmol) and 1,2-dibromoethane (34.3 mL, 454 mmol) in MeCN (35 mL) was added K$_2$CO$_3$ (7.85 g, 56.8 mmol). The mixture was heated to 65° C. and then stirred for 12 h. After cooling to room temperature, the mixture was concentrated in vacuo. The crude residue was purified by normal phase silica gel chromatography (Biotage 40 g cartridge, 0-50% EtOAc:petroleum ether) to give methyl 4-(2-bromoethoxy)-2-(trifluoromethyl)benzoate. MS=327.1/329.1 [M+H]$^+$.

Step 3: methyl 4-(2-{5-cyano-1-methyl-2-oxo-1,2-dihydrospiro[indole-3,4'-piperidin]-1'-yl}ethoxy)-2-(trifluoromethyl)benzoate

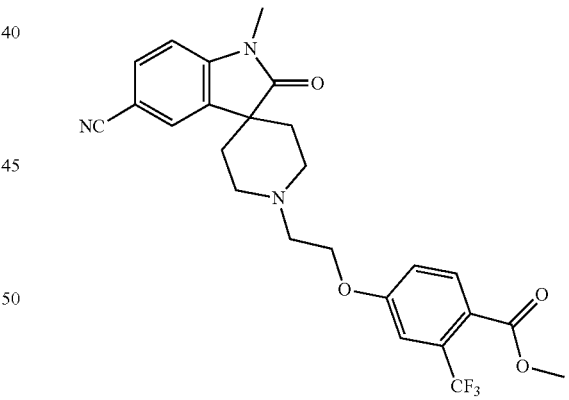

To a solution of 1-methyl-2-oxo-1,2-dihydrospiro[indole-3,4'-piperidine]-5-carbonitrile (Intermediate B-15, 154 mg, 0.556 mmol, HCl salt) and methyl 4-(2-bromoethoxy)-2-(trifluoromethyl)benzoate (200 mg, 0.611 mmol) in MeCN (8 mL) was added NaHCO$_3$ (140 mg, 1.67 mmol). The mixture was heated to 80° C. and stirred for 12 h. After cooling to room temperature, solids were removed by filtration and the filtrate was concentrated in vacuo. The crude residue was purified by normal phase silica gel chromatography (Biotage 12 g cartridge, 0-50% EtOAc:petroleum ether) to give methyl 4-(2-{5-cyano-1-methyl-2-oxo-1,2-dihydrospiro[indole-3,4'-piperidin]-1'-yl}ethoxy)-2-(trifluoromethyl)benzoate. MS=488.3 [M+H]$^+$ Step 4: 4-(2-{5-cyano-1-methyl-2-oxo-1,2-dihydrospiro[indole-3,4'-piperidin]-1'-yl}ethoxy)-2-(trifluoromethyl)benzoic acid

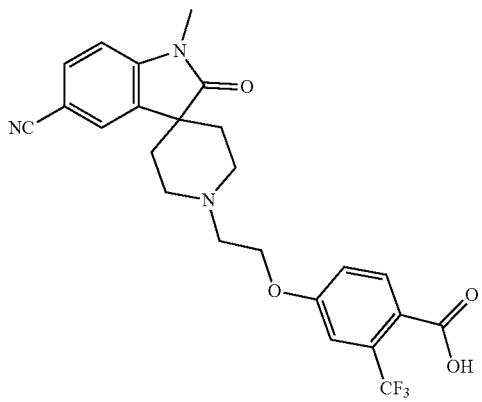 [SMILES: CN1C(=O)C2(CCN(CCOc3ccc(C(=O)O)c(C(F)(F)F)c3)CC2)c2cc(C#N)ccc21]

To a solution of methyl 4-(2-{5-cyano-1-methyl-2-oxo-1,2-dihydrospiro[indole-3,4'-piperidin]-1'-yl}ethoxy)-2-(trifluoromethyl)benzoate (250 mg, 0.513 mmol) in MeOH (5 mL) and H₂O (5 mL) was added LiOH H₂O (172 mg, 4.10 mmol). The mixture was stirred at room temperature for 2 h. The reaction mixture was concentrated in vacuo to remove MeOH, and the resulting aqueous phase was adjusted to pH=4-6 via dropwise addition of 1.0 M aqueous HCl. The resulting solid was isolated by filtration, washed with MTBE, and dried in vacuo to give 4-(2-{5-cyano-1-methyl-2-oxo-1,2-dihydrospiro[indole-3,4'-piperidin]-1'-yl}ethoxy)-2-(trifluoromethyl)benzoic acid, which was taken to the subsequent step without further purification. MS=474.2 [M+H]⁺.

Step 5: 1'-{2-[4-(1,1-dioxo-1λ⁶-thiomorpholine-4-carbonyl)-3-(trifluoromethyl)phenoxy]ethyl}-1-methyl-2-oxo-1,2-dihydrospiro[indole-3,4'-piperidine]-5-carbonitrile (Compound 261)

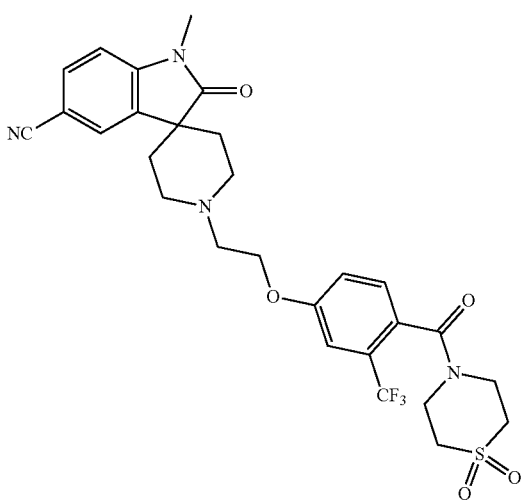 [SMILES: CN1C(=O)C2(CCN(CCOc3ccc(C(=O)N4CCS(=O)(=O)CC4)c(C(F)(F)F)c3)CC2)c2cc(C#N)ccc21]

To a 0° C. solution of 4-(2-{5-cyano-1-methyl-2-oxo-1,2-dihydrospiro[indole-3,4'-piperidin]-1'-yl}ethoxy)-2-(trifluoromethyl)benzoic acid (100 mg, 0.211 mmol), 1λ6-thiomorpholine-1,1-dione (39.9 mg, 0.232 mmol, HCl salt) and DIEA (92.0 μL, 0.528 mmol) in DMF (2 mL) was added HATU (120 mg, 0.317 mmol). The mixture was allowed to warm to room temperature and stirred for 16 h. The reaction mixture was poured into H₂O (5 mL) and then extracted with EtOAc (3×10 mL). The combined organic layers were washed with brine (20 mL), dried over Na₂SO₄, filtered, and concentrated in vacuo. The crude residue was purified by reverse phase preparative HPLC (Waters Xbridge Prep OBD C₁₈ column, 15-45% MeCN: 10 mM NH₄HCO₃ in H₂O) to give 1'-{2-[4-(1,1-dioxo-1λ⁶-thiomorpholine-4-carbonyl)-3-(trifluoromethyl)phenoxy]ethyl}-1-methyl-2-oxo-1,2-dihydrospiro[indole-3,4'-piperidine]-5-carbonitrile (Compound 261). ¹H NMR (400 MHz, DMSO-d₆): δ 8.00 (s, 1H), 7.80 (d, J=9.6 Hz, 1H), 7.68 (d, J=8.4, 1H), 7.38-7.35 (m, 2H), 7.21 (d, J=8.0, 1H), 4.47 (br d, J=13.2, 1H), 4.29-4.26 (m, 2H), 3.59-3.56 (m, 2H), 3.46-3.41 (m, 2H), 3.29-3.28 (m, 1H), 3.20-3.16 (m, 4H), 2.95-2.88 (m, 5H), 3.77-3.74 (m, 2H), 1.84-1.68 (m, 4H). MS=591.3 [M+H]⁺.

Example 51

1'-{1-[4-(3-methanesulfonyloxetan-3-yl)phenoxy]propan-2-yl}-2-oxo-1,2-dihydrospiro[indole-3,4'-piperidine]-5-carbonitrile (Compound 262), (S) or (R)-1'-{1-[4-(3-methanesulfonyloxetan-3-yl)phenoxy]propan-2-yl}-2-oxo-1,2-dihydrospiro[indole-3,4'-piperidine]-5-carbonitrile (Compound 263), and (R) or (S)-1'-{1-[4-(3-methanesulfonyloxetan-3-yl)phenoxy]propan-2-yl}-2-oxo-1,2-dihydrospiro[indole-3,4'-piperidine]-5-carbonitrile (Compound 264)

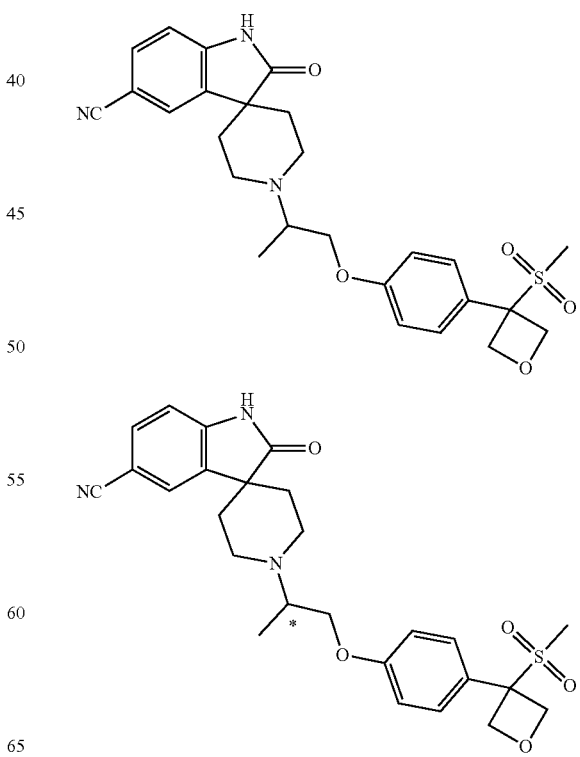

-continued

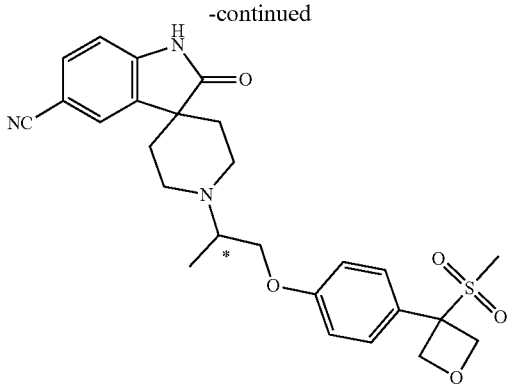

Step 1: 1'-{1-[4-(3-methanesulfonyloxetan-3-yl)phenoxy]propan-2-yl}-2-oxo-1,2-dihydrospiro[indole-3,4'-piperidine]-5-carbonitrile (Compound 262)

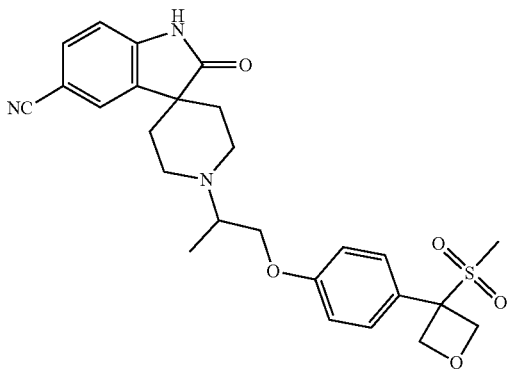 [SMILES: CC(COc1ccc(C2(S(C)(=O)=O)COC2)cc1)N1CCC2(CC1)C(=O)Nc1ccc(C#N)cc12]

A mixture of 1-[4-(3-methanesulfonyloxetan-3-yl)phenoxy]propan-2-yl methanesulfonate (Intermediate A-36, 385 mg, 1.06 mmol), 2-oxo-1,2-dihydrospiro[indole-3,4'-piperidine]-5-carbonitrile (Intermediate B-9, 200 mg, 0.880 mmol), NaHCO$_3$ (296 mg, 3.52 mmol) and KI (292 mg, 1.76 mmol) in DMF (1 mL) was degassed and purged with N$_2$ (3×). The mixture was stirred at 90° C. for 15 h under N$_2$ atmosphere. After cooling to room temperature, the reaction mixture was quenched with H$_2$O (15 mL) and extracted with EtOAc (3×10 mL). The combined organic layers were washed with brine (20 mL), dried over Na$_2$SO$_4$, filtered, and concentrated in vacuo. The crude residue was purified by reverse phase preparative HPLC (Phenomenex C$_{18}$ column, 20-40% MeCN: 10 mM NH$_4$HCO$_3$ in H$_2$O) to give 1'-{1-[4-(3-methanesulfonyloxetan-3-yl)phenoxy]propan-2-yl}-2-oxo-1,2-dihydrospiro[indole-3,4'-piperidine]-5-carbonitrile (Compound 262). MS=496.1 [M+H]$^+$.

Step 2: (S) or (R)-1'-{1-[4-(3-methanesulfonyloxetan-3-yl)phenoxy]propan-2-yl}-2-oxo-1,2-dihydrospiro[indole-3,4'-piperidine]-5-carbonitrile (Compound 263), and (R) or (S)-1'-{1-[4-(3-methanesulfonyloxetan-3-yl)phenoxy]propan-2-yl}-2-oxo-1,2-dihydrospiro[indole-3,4'-piperidine]-5-carbonitrile (Compound 264)

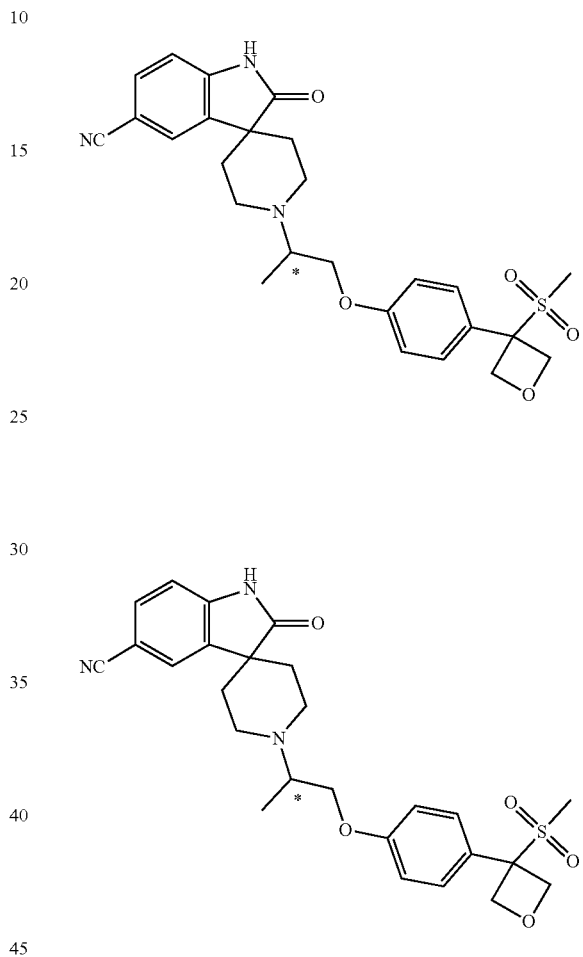

1'-{1-[4-(3-methanesulfonyloxetan-3-yl)phenoxy]propan-2-yl}-2-oxo-1,2-dihydrospiro[indole-3,4'-piperidine]-5-carbonitrile (110 mg, 0.222 mmol) was purified by preparative chiral SFC (Dailcel Chiralpak AD-3, 60% ethanol with 0.1% NH$_4$OH in CO$_2$). The first eluting enantiomer of the title compound, Compound 263: $^1$H NMR (400 MHz, DMSO-d$_6$): δ 10.86 (s, 1H), 7.87 (s, 1H), 7.68 (dd, J=8.4, 1.6 Hz, 1H), 7.26 (d, J=8.8 Hz, 2H), 7.05 (d, J=8.8 Hz, 2H), 6.97 (d, J=8.0 Hz, 1H), 5.21 (d, J=7.6 Hz, 2H), 5.00 (d, J=7.6 Hz, 2H), 4.50-4.20 (m, 1H), 4.01-3.98 (m, 1H), 3.14-3.09 (m, 1H), 3.03-3.01 (m, 2H), 2.89-2.84 (m, 4H), 2.79-2.74 (m, 1H), 1.81-1.68 (m, 4H), 1.16 (d, J=7.2 Hz, 3H). MS=496.1 [M+H]$^+$. The second eluting enantiomer of the title compound, Compound 264: $^1$H NMR (400 MHz, DMSO-d$_6$): δ 10.87 (s, 1H), 7.87 (s, 1H), 7.68 (dd, J=8.0, 1.6 Hz, 1H), 7.26 (d, J=8.8 Hz, 2H), 7.06 (d, J=8.4 Hz, 2H), 6.98 (d, J=8.0 Hz, 1H), 5.19 (d, J=7.2 Hz, 2H), 5.00 (d, J=7.6 Hz, 2H), 4.21-4.13 (m, 1H), 4.05-3.98 (m, 1H), 3.15-3.13 (m, 1H), 3.04-3.03 (m, 2H), 2.89-2.84 (m, 4H), 2.81-2.77 (m, 1H), 1.82-1.72 (m, 4H), 1.18 (d, J=6.8 Hz, 3H). MS=496.1 [M+H]$^+$.

Example 52

5-chloro-1'-{2-[3-(difluoromethyl)-4-methanesulfonylphenoxy]ethyl}-1-(2-hydroxyethyl)-1,2-dihydrospiro[indole-3,4'-piperidin]-2-one (Compound 265)

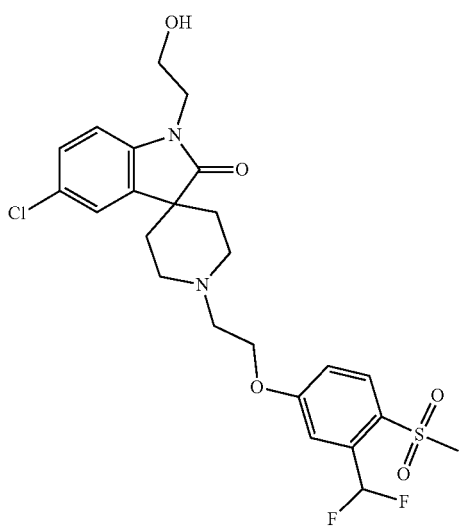 [SMILES: CS(=O)(=O)c1ccc(OCCN2CCC3(CC2)C(=O)N(CCO)c2ccc(Cl)cc23)cc1C(F)F]

To a solution of 5-chloro-1'-{2-[3-(difluoromethyl)-4-methanesulfonylphenoxy]ethyl}-1,2-dihydrospiro[indole-3,4'-piperidin]-2-one (Compound 197, 100 mg, 0.206 mmol) in DMF (1 mL) was added $K_2CO_3$ (142 mg, 1.03 mmol) and 2-bromoethanol (155 mg, 1.24 mmol). The mixture was stirred at 80° C. for 12 h. The reaction mixture was diluted with $H_2O$ (10 mL) and extracted with EtOAc (3×10 mL). The combined organic layers were washed with brine (10 mL), dried over $Na_2SO_4$, filtered, and concentrated in vacuo. The crude residue was purified by reverse phase preparative HPLC (Phenomenex $C_{18}$ column, 30-65% MeCN: 10 mM $NH_4HCO_3$ in $H_2O$) to give 5-chloro-1'-{2-[3-(difluoromethyl)-4-methanesulfonylphenoxy]ethyl}-1-(2-hydroxyethyl)-1,2-dihydrospiro[indole-3,4'-piperidin]-2-one (Compound 265). $^1H$ NMR (400 MHz, DMSO-$d_6$): δ 7.99 (d, J=8.8 Hz, 1H), 7.59-7.52 (m, 2H), 7.33-7.30 (m, 3H), 7.09 (d, J=8.4 Hz, 1H), 4.82 (t, J=5.6 Hz, 1H), 4.32 (t, J=5.6 Hz, 2H), 3.70 (t, J=5.6 Hz, 2H), 3.59-3.52 (m, 2H), 3.26 (s, 3H), 2.99-2.86 (m, 4H), 2.77-2.69 (m, 2H), 1.76 (s, 4H). MS=529.1 $[M+H]^+$.

The following compound in Table 38 was prepared according to procedures similar to those described for Compound 265 using the appropriate starting materials.

TABLE 38

| # | Structure | Name | Exact Mass $[M + H]^+$ | Starting Material |
|---|---|---|---|---|
| 266 | 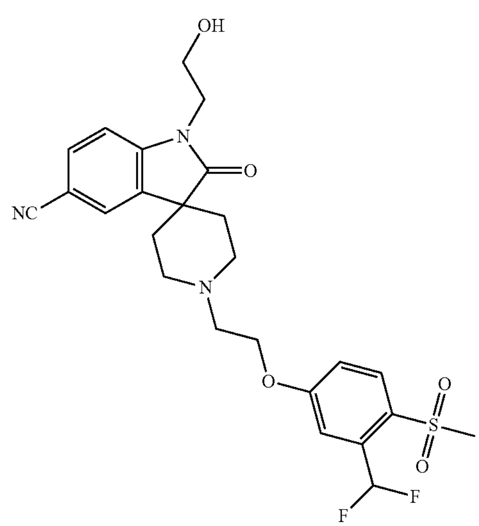 [SMILES: CS(=O)(=O)c1ccc(OCCN2CCC3(CC2)C(=O)N(CCO)c2ccc(C#N)cc23)cc1C(F)F] | 1'-(2-3-(difluoromethyl)-4-methanesulfonylphenoxy]ethyl}-1-(2-hydroxyethyl)-2-oxo-1,2-dihydrospiro[indole-3,4'-piperidine]-5-carbonitrile | Calc'd 520.2 Found 520.3 | Compound 100 |

Example 53

5-chloro-1'-[2-({7-oxo-8-[(trans)-3-hydroxycyclobutyl]-5,6,7,8-tetrahydro-1,8-naphthyridin-3-yl}oxy)ethyl]-1,2-dihydrospiro[indole-3,4'-piperidin]-2-one (Compound 267)

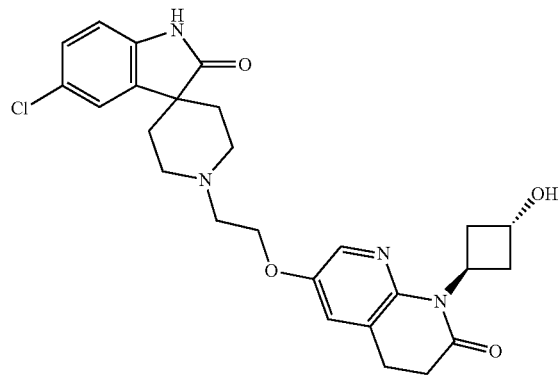 [SMILES: O=C1CCc2cc(OCCN3CCC4(CC3)C(=O)Nc3ccc(Cl)cc34)cnc2N1[C@H]1C[C@H](O)C1]

Step 1: (cis)-3-[6-(2-{5-chloro-2-oxo-1,2-dihydrospiro[indole-3,4'-piperidin]-1'-yl}ethoxy)-2-oxo-1,2,3,4-tetrahydro-1,8-naphthyridin-1-yl]cyclobutyl methanesulfonate

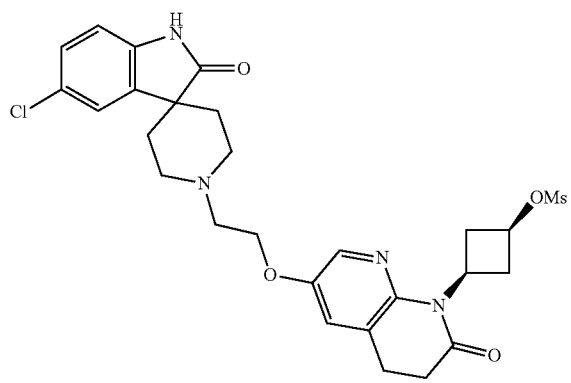 [SMILES: CS(=O)(=O)O[C@H]1C[C@@H](N2C(=O)CCc3cc(OCCN4CCC5(CC4)C(=O)Nc4ccc(Cl)cc45)cnc32)C1]

To a 0° C. solution of 5-chloro-1'-[2-({7-oxo-8-[(cis)-3-hydroxycyclobutyl]-5,6,7,8-tetrahydro-1,8-naphthyridin-3-yl}oxy)ethyl]-1,2-dihydrospiro[indole-3,4'-piperidin]-2-one (Compound 190, 150 mg, 0.302 mmol) in DCM (5 mL) was added TEA (61.0 mg, 0.604 mmol) and methanesulfonic anhydride (79 mg, 0.453 mmol). The mixture was allowed to warm to room temperature and stirred for 12 h. The mixture was quenched with H$_2$O (10 mL) and extracted with DCM (3×10 mL). The combined organic layers were washed with brine (30 mL), dried over Na$_2$SO$_4$, filtered, and concentrated in vacuo to give (cis)-3-[6-(2-{5-chloro-2-oxo-1,2-dihydrospiro[indole-3,4'-piperidin]-1'-yl}ethoxy)-2-oxo-1,2,3,4-tetrahydro-1,8-naphthyridin-1-yl]cyclobutyl methanesulfonate, which was taken onto the next step without further purification. MS=575.2 [M+H]$^+$.

Step 2: (trans)-3-[6-(2-{5-chloro-2-oxo-1,2-dihydrospiro[indole-3,4'-piperidin]-1'-yl}ethoxy)-2-oxo-1,2,3,4-tetrahydro-1,8-naphthyridin-1-yl]cyclobutyl acetate

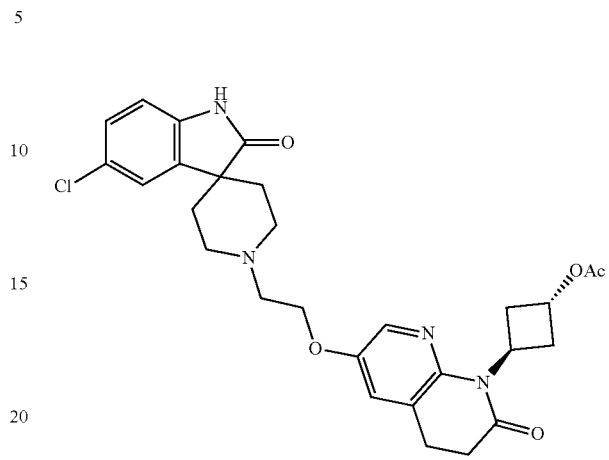

To a solution of (cis)-3-[6-(2-{5-chloro-2-oxo-1,2-dihydrospiro[indole-3,4'-piperidin]-1'-yl}ethoxy)-2-oxo-1,2,3,4-tetrahydro-1,8-naphthyridin-1-yl]cyclobutyl methanesulfonate (200 mg, 0.348 mmol) in DMF (5 mL) was added KOAc (341 mg, 3.48 mmol). The mixture was heated to 100° C. and stirred for 12 h. After cooling to room temperature, solids were removed by filtration and the filtrate was concentrated in vacuo. The crude residue was purified by reverse phase preparative HPLC (Waters Xbridge Prep OBD C$_{18}$ column, 25-55% MeCN: 10 mM NH$_4$HCO$_3$ in H$_2$O) to give (trans)-3-[6-(2-{5-chloro-2-oxo-1,2-dihydrospiro[indole-3,4'-piperidin]-1'-yl}ethoxy)-2-oxo-1,2,3,4-tetrahydro-1,8-naphthyridin-1-yl]cyclobutyl acetate. MS=539.3 [M+H]$^+$.

Step 3: 5-chloro-1'-[2-({7-oxo-8-[(trans)-3-hydroxycyclobutyl]-5,6,7,8-tetrahydro-1,8-naphthyridin-3-yl}oxy)ethyl]-1,2-dihydrospiro[indole-3,4'-piperidin]-2-one (Compound 267)

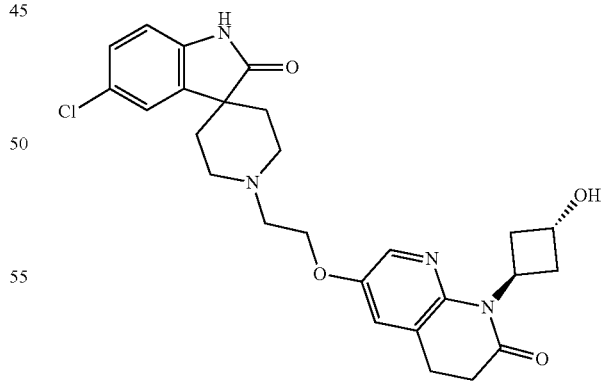

To a mixture of [(trans)-3-[6-(2-{5-chloro-2-oxo-1,2-dihydrospiro[indole-3,4'-piperidin]-1'-yl}ethoxy)-2-oxo-1,2,3,4-tetrahydro-1,8-naphthyridin-1-yl]cyclobutyl acetate (40.0 mg, 0.0742 mmol) in MeOH (2 mL) was added K$_2$CO$_3$ (20.5 mg, 0.148 mmol). The mixture was stirred at room temperature for 6 h. Solids were removed by filtration and the filtrate was concentrated in vacuo. The crude residue was purified by reverse phase preparative HPLC (Waters Xbridge BEH C₁₈ column, 25-55% MeCN: 10 mM NH₄HCO₃ in H₂O) to give 5-chloro-1'-[2-({7-oxo-8-[(trans)-3-hydroxycyclobutyl]-5,6,7,8-tetrahydro-1,8-naphthyridin-3-yl}oxy)ethyl]-1,2-dihydrospiro[indole-3,4'-piperidin]-2-one (Compound 267). ¹HNMR (400 MHz, CD₃CN): δ 8.40 (br s, 1H), 7.90 (d, J=2.8 Hz, 1H), 7.45 (d, J=2.0 Hz, 1H), 7.24-7.16 (m, 2H), 6.87 (d, J=8.4 Hz, 1H), 5.46 (q, J=8.6 Hz, 1H), 4.47 (br s, 1H), 4.17 (t, J=5.6 Hz, 2H), 3.04-2.84 (m, 7H), 2.83-2.77 (m, 2H), 2.77-2.67 (m, 2H), 2.56-2.48 (m, 2H), 2.27-2.18 (m, 2H), 1.91-1.82 (m, 2H), 1.79-1.70 (m, 2H). MS=497.2 [M+H]⁺.

Example 54

5-chloro-1'-{2-[4-(3-hydroxy-1-methanesulfonylcyclobutyl)phenoxy]ethyl}-1,2-dihydrospiro[indole-3,4'-piperidin]-2-one (Compound 268)

5-chloro-1'-(2-{4-[(cis) or (trans)-3-hydroxy-1-methanesulfonylcyclobutyl]phenoxy}ethyl)-1,2-dihydrospiro[indole-3,4'-piperidin]-2-one (Compound 269)

5-chloro-1'-(2-{4-[(trans) or (cis)-3-hydroxy-1-methanesulfonylcyclobutyl]phenoxy}ethyl)-1,2-dihydrospiro[indole-3,4'-piperidin]-2-one (Compound 270)

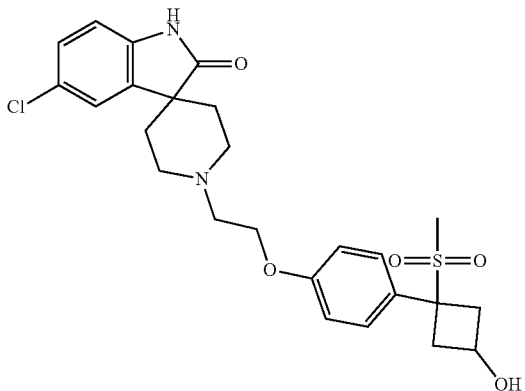

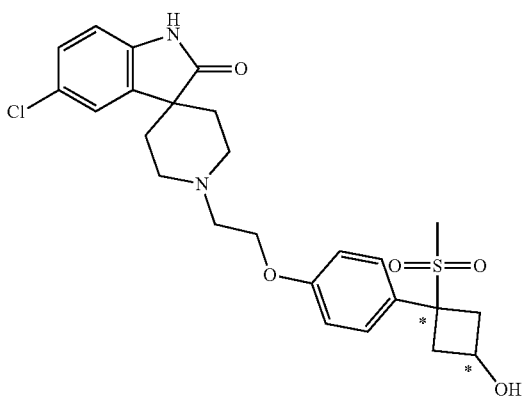

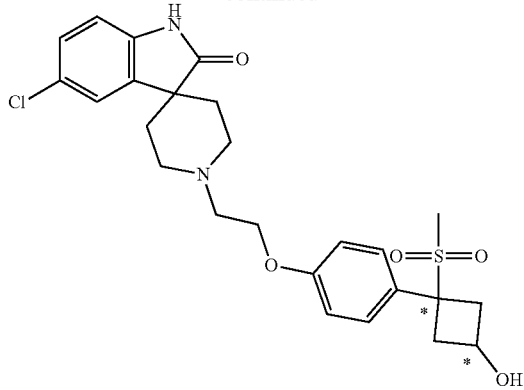

Step 1: 3-(benzyloxy)-1-[4-(benzyloxy)phenyl]cyclobutan-1-ol

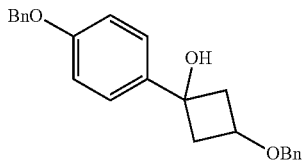 [SMILES: OC1(c2ccc(OCc3ccccc3)cc2)CC(OCc2ccccc2)C1]

To a −78° C. mixture of 1-(benzyloxy)-4-bromobenzene (34.0 g, 129 mmol) in THF (250 mL) was added 2.5 M n-BuLi in THF (62.0 mL, 155 mmol) dropwise. After stirring for 30 min, 3-benzyloxycyclobutanone (25.1 g, 142 mmol) in THF (50 mL) was added. The mixture was stirred at −78° C. for 1 h. The reaction mixture was allowed to warm to 0° C. and then quenched with H₂O (200 mL) and saturated aqueous NH₄Cl (200 mL). The mixture was extracted with EtOAc (3×250 mL). The combined organic layers were dried over Na₂SO₄, filtered, and concentrated in vacuo. The crude residue was purified by normal phase silica gel chromatography (Biotage 330 g cartridge, 0-50% EtOAc:petroleum ether) to give 3-(benzyloxy)-1-[4-(benzyloxy)phenyl]cyclobutan-1-ol as a mixture of diastereomers. ¹H NMR (400 MHz, DMSO-d₆): δ 7.48-7.22 (m, 13H), 6.95-6.91 (m, 1H), 5.54 (s, 1H), 5.08 (s, 2H), 4.37 (s, 2H), 3.78-3.67 (m, 1H), 2.78-2.68 (m, 2H), 2.30-2.22 (m, 2H).

Step 2: 1-(benzyloxy)-4-[3-(benzyloxy)-1-methanesulfonylcyclobutyl]benzene

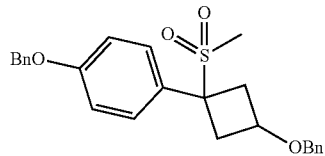 [SMILES: CS(=O)(=O)C1(c2ccc(OCc3ccccc3)cc2)CC(OCc2ccccc2)C1]

To a 0° C. solution of 3-(benzyloxy)-1-[4-(benzyloxy)phenyl]cyclobutan-1-ol (25.0 g, 69.4 mmol) and sodium methanesulfinate (35.4 g, 347 mmol) in DCM (300 mL) was added TFA (39.5 g, 347 mmol). The mixture was stirred at 0° C. for 2 h. The reaction mixture was then quenched with H₂O (300 mL) and extracted with EtOAc (3×150 mL). The combined organic layers were washed with brine (3×300 mL), dried over MgSO$_4$, filtered, and concentrated in vacuo. The crude residue was purified by normal phase silica gel chromatography (Biotage 12 g cartridge, 0-45% EtOAc: petroleum ether) to give 1-(benzyloxy)-4-[3-(benzyloxy)-1-methanesulfonylcyclobutyl]benzene. MS=440.3 [M+NH$_4$]$^+$.

Step 3: 4-(3-hydroxy-1-methanesulfonylcyclobutyl)phenol

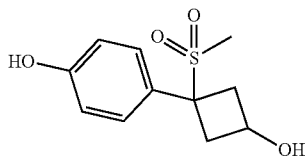 [SMILES: CS(=O)(=O)C1(c2ccc(O)cc2)CC(O)C1]

To a mixture of Pd/C (8.00 g, 10 wt %, 7.55 mmol) in MeOH (200 mL) was added 1-(benzyloxy)-4-[3-(benzyloxy)-1-methanesulfonylcyclobutyl]benzene (5.00 g, 11.8 mmol). The suspension was degassed under vacuum and purged with H$_2$ (3×). After allowing the mixture to stir at room temperature for 16 h under a H$_2$ atmosphere, the mixture was filtered through Celite. The filtrate was concentrated in vacuo to give 4-(3-hydroxy-1-methanesulfonylcyclobutyl)phenol, which was taken to the next step without further purification. MS=260.2 [M+NH$_4$]$^+$.

Step 4: methyl 2-[4-(3-hydroxy-1-methanesulfonylcyclobutyl)phenoxy]acetate

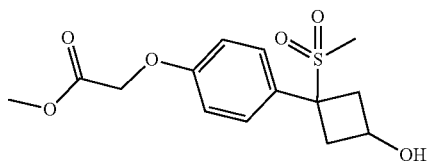 [SMILES: COC(=O)COc1ccc(C2(S(C)(=O)=O)CC(O)C2)cc1]

To a solution 4-(3-hydroxy-1-methanesulfonylcyclobutyl)phenol (3.80 g, 15.7 mmol) and K$_2$CO$_3$ (3.25 g, 23.5 mmol) in DMF (30 mL) was added methyl 2-bromoacetate (2.88 g, 18.8 mmol). The mixture was stirred at room temperature for 16 h, and then quenched with H$_2$O (30 mL). The mixture was extracted with EtOAc (3×15 mL). The combined organic phase was washed with brine (50 mL), dried over Na$_2$SO$_4$, filtered, and concentrated in vacuo. The crude residue was purified by normal phase silica gel chromatography (Biotage 10 g cartridge, 0-100% EtOAc: petroleum ether) to give methyl 2-[4-(3-hydroxy-1-methanesulfonylcyclobutyl)phenoxy]acetate as a mixture of diastereomers. MS=332.2 [M+NH$_4$]$^+$.

Step 5: 3-[4-(2-hydroxyethoxy)phenyl]-3-methanesulfonylcyclobutan-1-ol

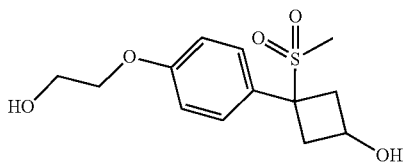 [SMILES: CS(=O)(=O)C1(c2ccc(OCCO)cc2)CC(O)C1]

To a 0° C. solution of methyl 2-[4-(3-hydroxy-1-methanesulfonylcyclobutyl)phenoxy]acetate (500 mg, 1.59 mmol) in THF (25 mL) was added LiAlH$_4$ (151 mg, 3.98 mmol). The mixture was allowed to warm to room temperature and was stirred for 12 h. The mixture was quenched with saturated aqueous NH$_4$Cl (5 mL) and then extracted with EtOAc (3×20 mL). The combined organic layers were washed with brine (50 mL), dried over Na$_2$SO$_4$, filtered, and concentrated in vacuo. The crude residue was purified by normal phase silica gel chromatography (Biotage 10 g cartridge, 0-100% EtOAc:petroleum ether) to give 3-[4-(2-hydroxyethoxy)phenyl]-3-methanesulfonylcyclobutan-1-ol. MS=304.2 [M+NH$_4$]$^+$.

Step 6: 2-[4-(3-hydroxy-1-methanesulfonylcyclobutyl)phenoxy]ethyl methanesulfonate

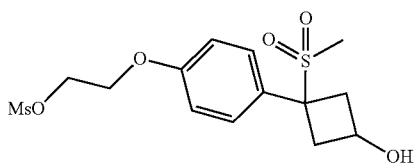 [SMILES: CS(=O)(=O)OCCOc1ccc(C2(S(C)(=O)=O)CC(O)C2)cc1]

To a solution of 3-[4-(2-hydroxyethoxy)phenyl]-3-methanesulfonylcyclobutan-1-ol (220 mg, 0.77 mmol) in DCM (15 mL) was added TEA (233 mg, 2.30 mmol) and methanesulfonic anhydride (161 mg, 0.92 mmol). The resulting mixture was stirred at room temperature for 12 h. The mixture was quenched with H$_2$O (20 mL) and extracted with EtOAc (3×20 mL). The combined organic layers were washed with brine (2×20 mL), dried with Na$_2$SO$_4$, filtered, and concentrated in vacuo. The crude residue was purified by preparative TLC (SiO$_2$, 1:1 petroleum ether/EtOAc) to give 2-[4-(3-hydroxy-1-methanesulfonylcyclobutyl)phenoxy]ethyl methanesulfonate as a mixture of diastereomers. MS=382.1 [M+NH$_4$]$^+$.

Step 7: 5-chloro-1'-{2-[4-(3-hydroxy-1-methanesulfonylcyclobutyl)phenoxy]ethyl}-1,2-dihydrospiro[indole-3,4'-piperidin]-2-one (Compound 268)

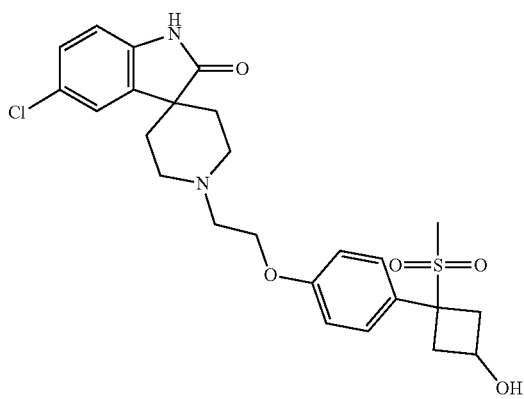 [SMILES: CS(=O)(=O)C1(c2ccc(OCCN3CCC4(CC3)C(=O)Nc3ccc(Cl)cc34)cc2)CC(O)C1]

To a solution of 2-[4-(3-hydroxy-1-methanesulfonylcyclobutyl)phenoxy]ethyl methanesulfonate (85.0 mg, 0.23 mmol) in MeCN (5 mL) was added NaHCO$_3$ (58.0 mg, 0.700 mmol) and 5-chloro-1'-(2-chloroethyl)-1,2-dihydrospiro[indole-3,4'-piperidin]-2-one (Intermediate B-4, 63.7 mg, 0.23 mmol, HCl salt). The mixture was stirred at 80° C. for 12 h. After allowing to cool to room temperature, solids were removed by filtration and the filtrate was concentrated in vacuo. The crude residue was purified by reverse phase preparative HPLC (Waters Xbridge BEH C$_{18}$ column, 20-50% MeCN: 10 mM NH$_4$HCO$_3$ in H$_2$O) to give 5-chloro-1'-{2-[4-(3-hydroxy-1-methanesulfonylcyclobutyl)phenoxy]ethyl}-1,2-dihydrospiro[indole-3,4'-piperidin]-2-one (Compound 268). $^1$H NMR (400 MHz, DMSO-d$_6$): δ 10.48 (s, 1H), 7.51-7.47 (m, 2H), 7.24 (dd, J=7.6, 2.0 Hz, 2H), 7.00 (t, J=8.0 Hz, 2H), 6.84 (d, J=8.4 Hz, 1H), 5.49-5.32 (m, 1H), 4.36-4.14 (m, 1H), 4.18-4.17 (m, 2H), 3.28-3.27 (m, 1H), 2.92-2.84 (m, 5H), 2.72-2.68 (m, 3H), 2.63-2.54 (m, 3H), 2.35-2.45 (m, 1H), 1.79-1.71 (m, 4H). MS=505.2 [M+H]$^+$.

Step 8: 5-chloro-1'-(2-{4-[(cis) or (trans)-3-hydroxy-1-methanesulfonylcyclobutyl]phenoxy}ethyl)-1,2-dihydrospiro[indole-3,4'-piperidin]-2-one (Compound 269) and 5-chloro-1'-(2-{4-[(trans) or (cis)-3-hydroxy-1-methanesulfonylcyclobutyl]phenoxy}ethyl)-1,2-dihydrospiro[indole-3,4'-piperidin]-2-one (Compound 270)

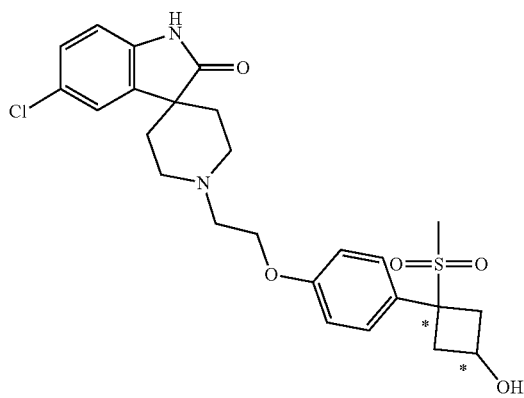

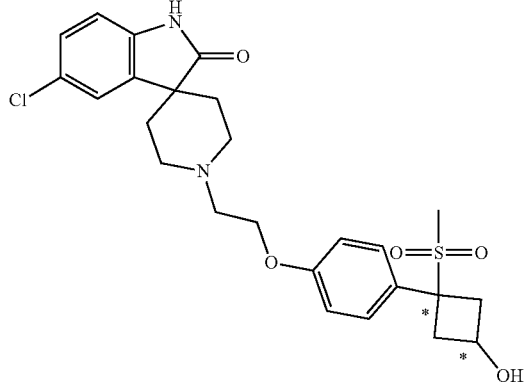

5-chloro-1'-{2-[4-(3-hydroxy-1-methanesulfonylcyclobutyl)phenoxy]ethyl}-1,2-dihydrospiro[indole-3,4'-piperidin]-2-one (Compound 268) was separated by preparative chiral SFC (Chiralpak AD-3 column, 50% isopropanol with 0.1% NH$_4$OH in CO$_2$). The first eluting isomer of the title compound, 5-chloro-1'-(2-{4-[(trans) or (cis)-3-hydroxy-1-methanesulfonylcyclobutyl]phenoxy}ethyl)-1,2-dihydrospiro[indole-3,4'-piperidin]-2-one (Compound 270): $^1$H NMR (400 MHz, DMSO-d$_6$): δ 10.49 (s, 1H), 7.55-7.44 (m, 3H), 7.23 (dd, J=8.4, 2.0 Hz, 1H), 7.01 (d, J=8.8 Hz, 2H), 6.84 (d, J=8.4 Hz, 1H), 5.49 (d, J=6.4 Hz, 1H), 4.17 (t, J=5.2 Hz, 2H), 3.90-3.75 (m, 1H), 2.98-2.79 (m, 6H), 2.76-2.66 (m, 4H), 2.54 (s, 3H), 1.86-1.64 (m, 4H). MS=505.2 [M+H]$^+$. The second eluting isomer of the title compound, 5-chloro-1'-(2-{4-[(cis) or (trans)-3-hydroxy-1-methanesulfonylcyclobutyl]phenoxy}ethyl)-1,2-dihydrospiro[indole-3,4'-piperidin]-2-one (Compound 269): $^1$H NMR (400 MHz, DMSO-d$_6$): δ 10.49 (s, 1H), 7.55-7.44 (m, 3H), 7.23 (dd, J=8.4, 2.0 Hz, 1H), 7.01 (d, J=8.8 Hz, 2H), 6.84 (d, J=8.4 Hz, 1H), 5.49 (d, J=6.4 Hz, 1H), 4.17 (t, J=5.2 Hz, 2H), 3.90-3.75 (m, 1H), 2.98-2.79 (m, 6H), 2.76-2.66 (m, 4H), 2.54 (s, 3H), 1.86-1.64 (m, 4H). MS=505.2 [M+H]$^+$.

Example 55

4-(4-{2-[5-chloro-1-(2-hydroxyethyl)-2-oxo-1,2-dihydrospiro[indole-3,4'-piperidin]-1'-yl]ethoxy}-2-(trifluoromethyl)benzoyl)-1λ$^6$-thiomorpholine-1,1-dione (Compound 271)

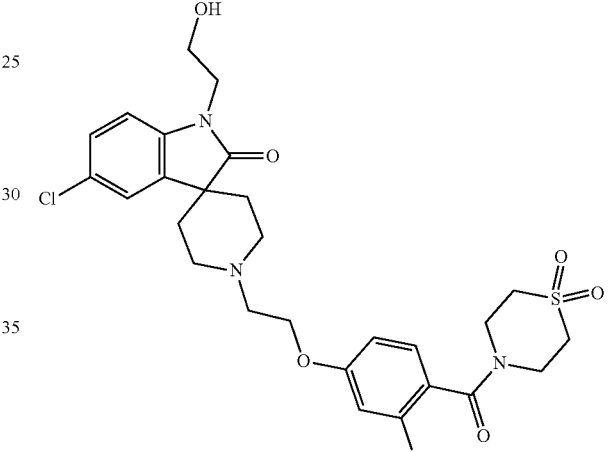

Step 1: methyl 4-{2-[5-chloro-1-(2-hydroxyethyl)-2-oxo-1,2-dihydrospiro[indole-3,4'-piperidin]-1'-yl]ethoxy}-2-(trifluoromethyl)benzoate

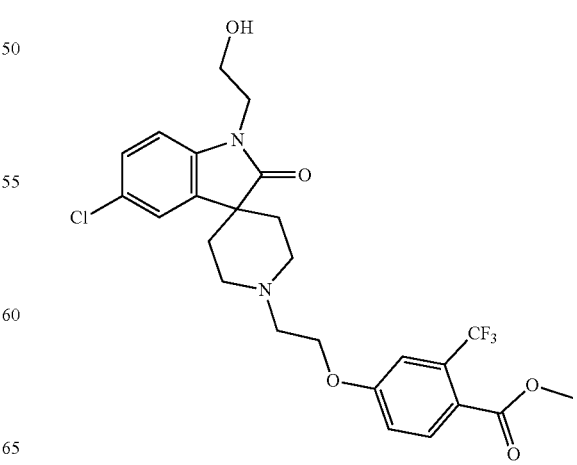

1133

To a room temperature solution of methyl 4-(2-bromoethoxy)-2-(trifluoromethyl)benzoate (Example 50, Step 2, 450 mg, 1.38 mmol) in MeCN (5 mL) was added NaHCO$_3$ (462 mg, 5.50 mmol) and 5-chloro-1-(2-hydroxyethyl)-1,2-dihydrospiro[indole-3,4'-piperidin]-2-one (Intermediate B-11, 524 mg, 1.65 mmol). The mixture was heated to 80° C. and stirred for 16 h. The mixture was allowed to cool to room temperature, then was diluted with H$_2$O (30 mL), and extracted with EtOAc (2×20 mL). The combined organic layers were washed with brine (30 mL), dried over Na$_2$SO$_4$, filtered, and concentrated in vacuo. The crude residue was purified by normal phase silica gel chromatography (Biotage 4 g cartridge, 0-35% EtOAc:petroleum ether) to give methyl 4-{2-[5-chloro-1-(2-hydroxyethyl)-2-oxo-1,2-dihydrospiro[indole-3,4'-piperidin]-1'-yl]ethoxy}-2-(trifluoromethyl)benzoate. MS=527.2. [M+H]$^+$.

Step 2: 4-{2-[5-chloro-1-(2-hydroxyethyl)-2-oxo-1,2-dihydrospiro[indole-3,4'-piperidin]-1'-yl]ethoxy}-2-(trifluoromethyl)benzoic acid

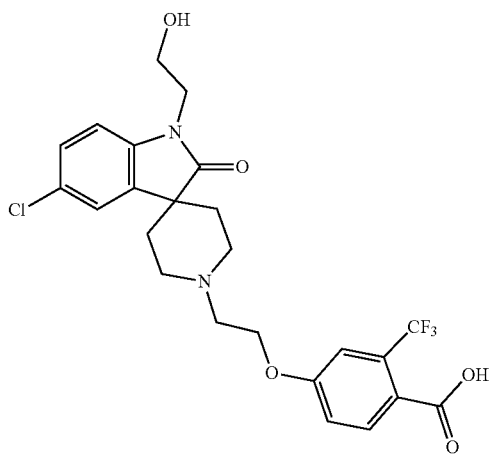 [SMILES: O=C(O)c1ccc(OCCN2CCC3(CC2)C(=O)N(CCO)c2ccc(Cl)cc23)cc1C(F)(F)F]

To a solution of methyl 4-{2-[5-chloro-1-(2-hydroxyethyl)-2-oxo-1,2-dihydrospiro[indole-3,4'-piperidin]-1'-yl]ethoxy}-2-(trifluoromethyl)benzoate (750 mg, 1.42 mmol) in MeOH (5 mL) was added LiOH H$_2$O (478 mg, 11.4 mmol) in H$_2$O (1 mL). The mixture was stirred at 50° C. for 12 h, then was concentrated in vacuo. The resulting mixture was adjusted to pH=4 via dropwise addition of 4.0 M aqueous HCl. The resulting solid was isolated by filtration and concentrated in vacuo to give 4-{2-[5-chloro-1-(2-hydroxyethyl)-2-oxo-1,2-dihydrospiro[indole-3,4'-piperidin]-1'-yl]ethoxy}-2-(trifluoromethyl)benzoic acid, which was taken onto the subsequent step without further purification. MS=513.1 [M+H]$^+$.

1134

Step 3: 4-(4-{2-[5-chloro-1-(2-hydroxyethyl)-2-oxo-1,2-dihydrospiro[indole-3,4'-piperidin]-1'-yl]ethoxy}-2-(trifluoromethyl)benzoyl)-1λ$^6$-thiomorpholine-1,1-dione (Compound 271)

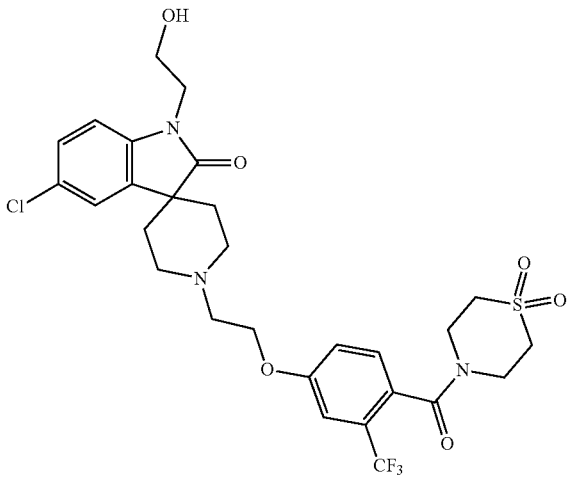 [SMILES: O=C(c1ccc(OCCN2CCC3(CC2)C(=O)N(CCO)c2ccc(Cl)cc23)cc1C(F)(F)F)N1CCS(=O)(=O)CC1]

To a solution of 1λ$^6$-thiomorpholine-1,1-dione (31 mg, 0.23 mmol) and 4-{2-[5-chloro-1-(2-hydroxyethyl)-2-oxo-1,2-dihydrospiro[indole-3,4'-piperidin]-1'-yl]ethoxy}-2-(trifluoromethyl)benzoic acid (100 mg, 0.19 mmol) in DCM (2 mL) was added HOBt (8.0 mg, 0.058 mmol), EDCI (56.0 mg, 0.292.45 mmol) and TEA (79 mg, 0.78 mmol). The mixture was stirred at room temperature for 12 h, then was concentrated in vacuo. The crude residue was purified by reverse phase preparative HPLC (Phenomenex C$_{18}$ column, 20-55% MeCN: 10 mM NH$_4$HCO$_3$ in H$_2$O) to give 4-(4-{2-[5-chloro-1-(2-hydroxyethyl)-2-oxo-1,2-dihydrospiro[indole-3,4'-piperidin]-1'-yl]ethoxy}-2-(trifluoromethyl)benzoyl)-1λ$^6$-thiomorpholine-1,1-dione (Compound 271). $^1$H NMR (400 MHz, DMSO-d$_6$): δ 7.68 (d, J=8.0 Hz, 1H), 7.53 (d, J=2.0 Hz, 1H), 7.42-7.26 (m, 3H), 7.10 (d, J=8.4 Hz, 1H), 4.83 (t, J=6.0 Hz, 1H), 4.48 (d, J=13.6 Hz, 1H), 4.27 (t, J=6.0 Hz, 2H), 3.69 (t, J=6.0 Hz, 2H), 3.63-3.49 (m, 4H), 3.49-3.39 (m, 2H), 3.29-3.11 (m, 2H), 3.02-2.82 (m, 5H), 2.77-2.68 (m, 2H), 1.90-1.56 (m, 4H). MS=630.2 [M+H]$^+$.

Example 56

4-[4-(2-{5-chloro-2-oxo-1,2-dihydrospiro[indole-3,4'-piperidin]-1'-yl}ethoxy)-2-(trifluoromethyl)benzoyl]-1λ$^6$-thiomorpholine-1,1-dione (Compound 272)

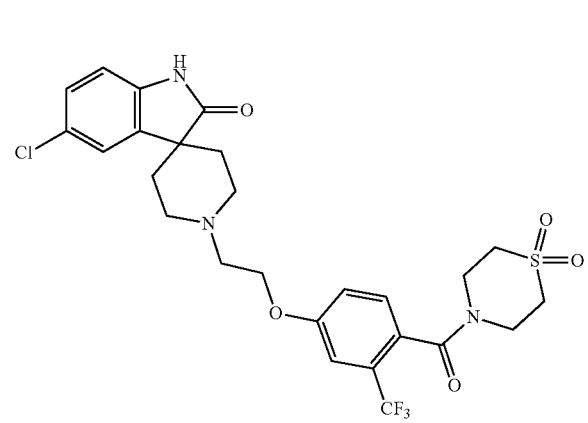 [SMILES: O=C(c1ccc(OCCN2CCC3(CC2)C(=O)Nc2ccc(Cl)cc23)cc1C(F)(F)F)N1CCS(=O)(=O)CC1]

Step 1: Methyl 4-(2-{5-chloro-2-oxo-1,2-dihydrospiro[indole-3,4'-piperidin]-1'-yl}ethoxy)-2-(trifluoromethyl)benzoate

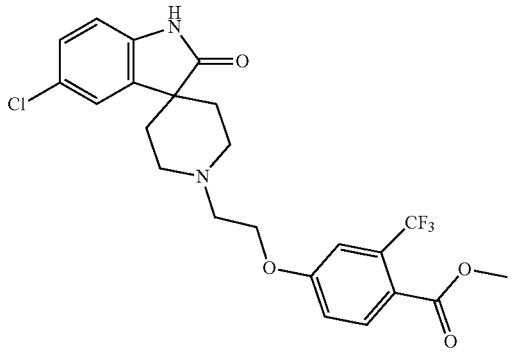 [SMILES: COC(=O)c1ccc(OCCN2CCC3(CC2)C(=O)Nc2ccc(Cl)cc23)cc1C(F)(F)F]

To a solution of methyl 4-(2-bromoethoxy)-2-(trifluoromethyl)benzoate (Example 50, Step 2, 1.0 g, 3.06 mmol) and 5-chlorospiro[indoline-3,4'-piperidine]-2-one (Intermediate B-4, 759 mg, 2.78 mmol, HCl salt) in MeCN (40 mL) was added NaHCO$_3$ (700 mg, 8.34 mmol). The mixture was heated to 80° C. and stirred for 12 h. The reaction mixture was allowed to cool to room temperature, then was filtered and concentrated in vacuo. The crude residue was purified by normal phase silica gel chromatography (Biotage 20 g cartridge, 0-100% EtOAc:petroleum ether) to give methyl 4-(2-{5-chloro-2-oxo-1,2-dihydrospiro[indole-3,4'-piperidin]-1'-yl}ethoxy)-2-(trifluoromethyl)benzoate. MS=483.1 [M+H]$^+$.

Step 2: 4-(2-{5-chloro-2-oxo-1,2-dihydrospiro[indole-3,4'-piperidin]-1'-yl}ethoxy)-2-(trifluoromethyl)benzoic acid

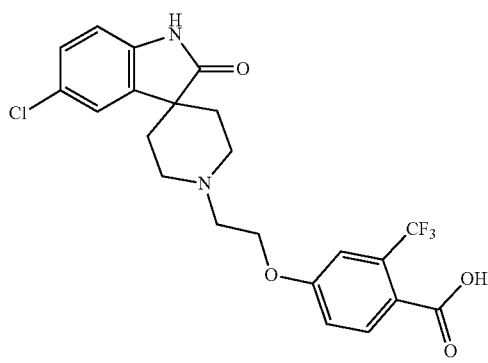 [SMILES: O=C(O)c1ccc(OCCN2CCC3(CC2)C(=O)Nc2ccc(Cl)cc23)cc1C(F)(F)F]

To a solution of methyl 4-(2-{5-chloro-2-oxo-1,2-dihydrospiro[indole-3,4'-piperidin]-1'-yl}ethoxy)-2-(trifluoromethyl)benzoate (300 mg, 0.62 mmol) in MeOH (6 mL) and H$_2$O (6 mL) was added LiOH·H$_2$O (208 mg, 4.97 mmol). The mixture was stirred at room temperature for 2 h. The reaction mixture was concentrated in vacuo, and the aqueous phase was adjusted to pH=4 via dropwise addition of 1.0 M aqueous HCl. The resulting solid was collected by filtration, washed with MTBE, and dried in vacuo to give 4-(2-{5-chloro-2-oxo-1,2-dihydrospiro[indole-3,4'-piperidin]-1'-yl}ethoxy)-2-(trifluoromethyl)benzoic acid which was taken to the next step without further purification. MS=469.2 [M+H]$^+$.

Step 3: 4-[4-(2-{5-chloro-2-oxo-1,2-dihydrospiro[indole-3,4'-piperidin]-1'-yl}ethoxy)-2-(trifluoromethyl)benzoyl]-1λ$^6$-thiomorpholine-1,1-dione (Compound 272)

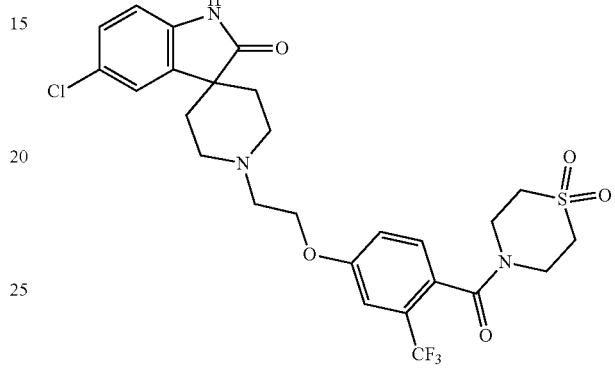

To a 0° C. solution of 4-(2-{5-chloro-2-oxo-1,2-dihydrospiro[indole-3,4'-piperidin]-1'-yl}ethoxy)-2-(trifluoromethyl)benzoic acid (100 mg, 0.21 mmol) and 1,4-thiazinane 1,1-dioxide (34.60 mg, 0.26 mmol) in DMF (2 mL) was added TEA (64.8 mg, 0.64 mmol), EDCI (61.3 mg, 0.32 mmol) and HOBt (5.8 mg, 0.043 mmol). The mixture was allowed to warm to room temperature and stirred for 12 h. The reaction mixture was poured into the H$_2$O (5 mL) and extracted with EtOAc (3×10 mL). The combined organic layers were washed with brine (20 mL), dried over Na$_2$SO$_4$, filtered, and concentrated in vacuo. The crude residue was purified by reverse phase preparative HPLC (Phenomenex C$_{18}$ column, 10-55% MeCN: 10 mM NH$_4$HCO$_3$ in H$_2$O) to give 4-[4-(2-{5-chloro-2-oxo-1,2-dihydrospiro[indole-3,4'-piperidin]-1'-yl}ethoxy)-2-(trifluoromethyl)benzoyl]-1λ$^6$-thiomorpholine-1,1-dione (Compound 272). $^1$H NMR (400 MHz, DMSO-d$_6$): δ 10.49 (s, 1H), 7.67 (d, J=8.4 Hz, 1H), 7.50 (s, 1H), 7.38-7.35 (m, 2H), 7.24 (dd, J=8.0, 2.4 Hz, 1H), 6.85 (d, J=8.4 Hz, 1H), 4.49-4.45 (m, 1H), 4.27 (t, J=5.6 Hz, 2H), 3.59-3.56 (m, 2H), 3.46-3.33 (m, 2H), 3.21-3.18 (m, 2H), 2.95-2.86 (m, 5H), 2.70-2.60 (m, 2H), 1.81-1.70 (m, 4H). MS=586.2 [M+H]$^+$.

Example 57

5-chloro-1'-[2-(3-fluoro-4-{6-methanesulfonyl-2,6-diazaspiro[3.3]heptane-2-carbonyl}phenoxy)ethyl]-1,2-dihydrospiro[indole-3,4'-piperidin]-2-one (Compound 273)

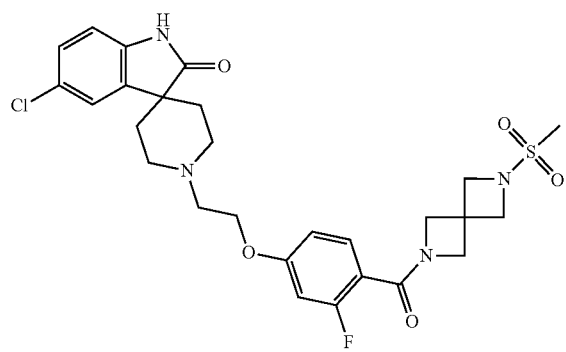 [SMILES: CS(=O)(=O)N1CC2(CN(C(=O)c3ccc(OCCN4CCC5(CC4)C(=O)Nc4ccc(Cl)cc45)cc3F)C2)C1]

Step 1: tert-butyl 6-[4-(2-{5-chloro-2-oxo-1,2-dihydrospiro[indole-3,4'-piperidin]-1'-yl}ethoxy)-2-fluorobenzoyl]-2,6-diazaspiro[3.3]heptane-2-carboxylate

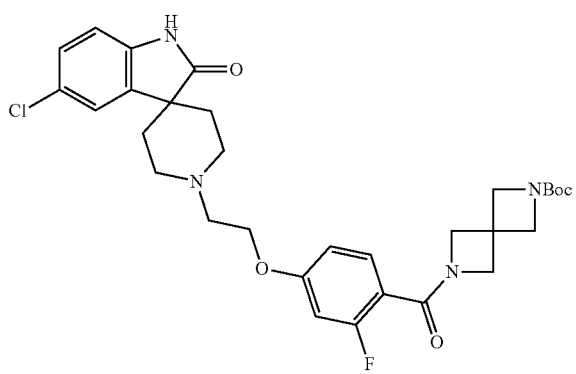 [SMILES: CC(C)(C)OC(=O)N1CC2(C1)CN(C(=O)c1ccc(OCCN3CCC4(CC3)C(=O)Nc3ccc(Cl)cc34)cc1F)C2]

To a solution of 4-(2-{5-chloro-2-oxo-1,2-dihydrospiro[indole-3,4'-piperidin]-1'-yl}ethoxy)-2-fluorobenzoic acid (Example 36, Step 3, 1.15 g, 2.75 mmol) and tert-butyl 2,6-diazaspiro[3.3]heptane-2-carboxylate (950 mg, 3.29 mmol) in DMF (12 mL) was added TEA (1.11 g, 11.0 mmol), HOBt (74.2 mg, 0.549 mmol), then EDCI (1.05 g, 5.49 mmol). The mixture was stirred at room temperature for 16 h. The reaction mixture was quenched with H₂O (30 mL) and then extracted with EtOAc (3×15 mL). The combined organic layers were washed with brine (3×10 mL), dried over Na₂SO₄, filtered, and concentrated in vacuo. The crude residue was purified by normal phase silica gel chromatography (Biotage 20 g cartridge, 50-100% EtOAc:petroleum ether) to give tert-butyl 6-[4-(2-{5-chloro-2-oxo-1,2-dihydrospiro[indole-3,4'-piperidin]-1'-yl}ethoxy)-2-fluorobenzoyl]-2,6-diazaspiro[3.3]heptane-2-carboxylate. MS=599.2 [M+H]⁺.

Step 2: 5-chloro-1'-[2-(4-{2,6-diazaspiro[3.3]heptane-2-carbonyl}-3-fluorophenoxy)ethyl]-1,2-dihydrospiro[indole-3,4'-piperidin]-2-one

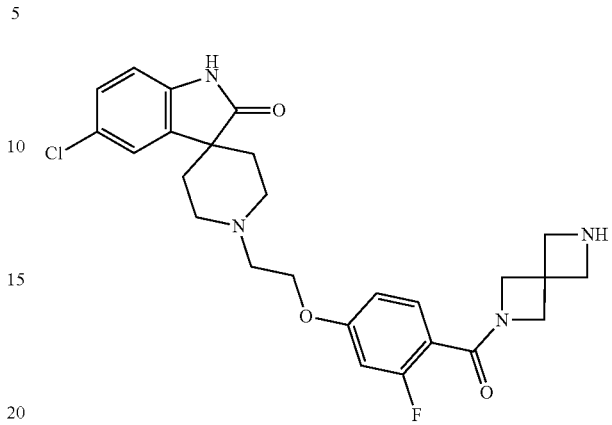

To a solution of tert-butyl 6-[4-(2-{5-chloro-2-oxo-1,2-dihydrospiro[indole-3,4'-piperidin]-1'-yl}ethoxy)-2-fluorobenzoyl]-2,6-diazaspiro[3.3]heptane-2-carboxylate (1.40 g, 2.34 mmol) in DCM (20 mL) was added TFA (4.31 g, 37.8 mmol). The mixture was stirred at room temperature for 3 h. The mixture was concentrated in vacuo to give 5-chloro-1'-[2-(4-{2,6-diazaspiro[3.3]heptane-2-carbonyl}-3-fluorophenoxy)ethyl]-1,2-dihydrospiro[indole-3,4'-piperidin]-2-one. MS=499.1 [M+H]⁺.

Step 3: 5-chloro-1'-[2-(3-fluoro-4-{6-methanesulfonyl-2,6-diazaspiro[3.3]heptane-2-carbonyl}phenoxy)ethyl]-1,2-dihydrospiro[indole-3,4'-piperidin]-2-one (Compound 273)

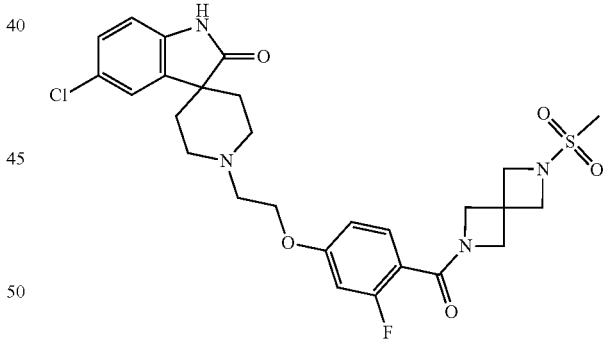

To a 0° C. solution of 5-chloro-1'-[2-(4-{2,6-diazaspiro[3.3]heptane-2-carbonyl}-3-fluorophenoxy)ethyl]-1,2-dihydrospiro[indole-3,4'-piperidin]-2-one (1.25 g, 2.51 mmol) in DCM (15 mL) was added TEA (1.74 mL, 12.5 mmol) and methanesulfonic anhydride (655 mg, 3.76 mmol). The mixture was stirred at room temperature for 3 h, and then was concentrated in vacuo. The crude residue was purified by reverse phase preparative HPLC (Kromasil C₁₈ column, 25-55% MeCN: 10 mM NH₄HCO₃ in H₂O) to give 5-chloro-1'-[2-(3-fluoro-4-{6-methanesulfonyl-2,6-diazaspiro[3.3]heptane-2-carbonyl}phenoxy)ethyl]-1,2-dihydrospiro[indole-3,4'-piperidin]-2-one (Compound 273). ¹H NMR (400 MHz, DMSO-d₆): δ=10.49 (s, 1H), 7.50 (d, J=2.0 Hz, 1H), 7.44 (app t, J=8.4 Hz, 1H), 7.23 (dd, J=8.4, 2.0 Hz, 1H), 6.93 (dd, J=12.4, 2.4 Hz, 1H), 6.89-6.83 (m, 2H), 4.20-4.18 (m, 6H), 4.03 (q, J=8.8 Hz, 4H), 2.97 (s, 3H), 2.95-2.84 (m, 4H), 2.72-2.67 (m, 2H), 1.82-1.66 (m, 4H). MS=577.2 [M+H]$^+$.

Example 58

5-(difluoromethyl)-1'-[2-({7-oxo-8-[(cis)-3-hydroxy-3-methylcyclobutyl]-5,6,7,8-tetrahydro-1,8-naphthyridin-3-yl}oxy)ethyl]-1,2-dihydrospiro[indole-3,4'-piperidin]-2-one (Compound 274)

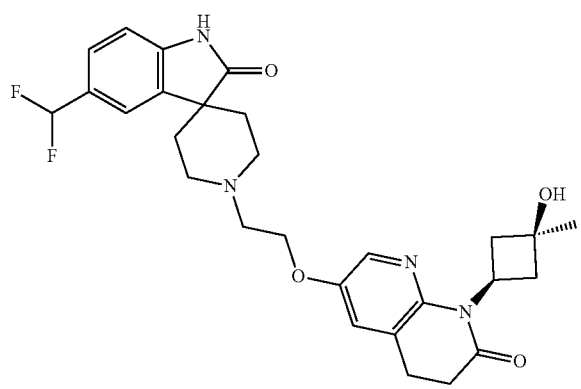 [SMILES: C[C@]1(O)C[C@@H](N2C(=O)CCc3cc(OCCN4CCC5(CC4)C(=O)Nc4ccc(C(F)F)cc45)cnc32)C1]

To a solution of 6-(2-bromoethoxy)-1-[(cis)-3-hydroxy-3-methylcyclobutyl]-1,2,3,4-tetrahydro-1,8-naphthyridin-2-one (Intermediate A-89, 100 mg, 0.281 mmol) and 5-(difluoromethyl)-1,2-dihydrospiro[indole-3,4'-piperidin]-2-one (Intermediate B-1, 89.4 mg, 0.309 mmol, HCl salt) in MeCN (3 mL) was added NaHCO$_3$ (94.5 mg, 1.13 mmol). The mixture was stirred at 80° C. for 16 h. After cooling to room temperature, solids were removed by filtration and the filtrate was concentrated in vacuo. The crude residue was purified by reverse phase preparative HPLC (Waters Xbridge BEH C$_{18}$ column, 25-55% MeCN: 10 mM NH$_4$HCO$_3$ in H$_2$O) to give 5-(difluoromethyl)-1'-[2-({7-oxo-8-[(cis)-3-hydroxy-3-methylcyclobutyl]-5,6,7,8-tetrahydro-1,8-naphthyridin-3-yl}oxy)ethyl]-1,2-dihydrospiro[indole-3,4'-piperidin]-2-one (Compound 274). $^1$H NMR (400 MHz, DMSO-d$_6$): δ 10.62 (s, 1H), 7.94 (d, J=2.4 Hz, 1H), 7.66 (s 1H), 7.43-7.39 (m, 2H), 7.10-6.82 (m, 2H), 4.82 (s, 1H), 4.24 (t, J=8.0 Hz, 1H), 4.19 (t, J=5.6 Hz, 2H), 2.96-2.94 (m, 2H), 2.86 (t, J=5.6 Hz, 2H), 2.80 (t, J=7.2 Hz, 2H), 2.72-2.67 (m, 2H), 2.44-2.42 (m, 4H), 2.34 (t, J=7.2 Hz, 2H), 1.85-1.80 (m, 2H), 1.71-1.66 (m, 2H), 1.25 (s, 3H). MS=527.3 [M+H]$^+$.

The following compound in Table 38.1 was prepared according to the procedures similar to those described for Compound 274 using the appropriate starting materials.

TABLE 38.1

| No. | Structure | IUPAC Name | Exact Mass [M + H]$^+$ | Intermediate Used |
|---|---|---|---|---|
| 325 | 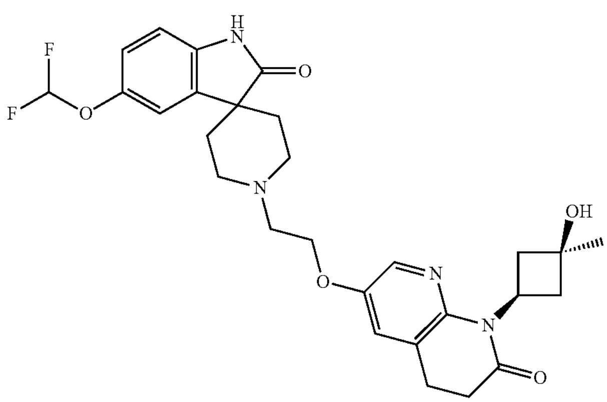 | 5-(difluoromethoxy)-1'-[2-({7-oxo-8-[(cis)-3-hydroxy-3-methylcyclobutyl]-5,6,7,8-tetrahydro-1,8-naphthyridin-3-yl}oxy)ethyl]-1,2-dihydrospiro[indole-3,4'-piperidin]-2-one | Calc'd 543.2 Found 543.1 | A-89 & B-2 |

TABLE 38.1-continued

| No. | Structure | IUPAC Name | Exact Mass [M + H]+ | Intermediate Used |
|---|---|---|---|---|
| 329 | 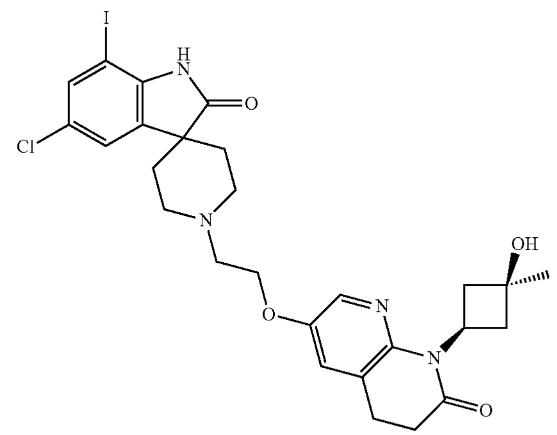 [SMILES: C[C@]1(O)C[C@@H](N2C(=O)CCc3cc(OCCN4CCC5(CC4)C(=O)Nc4c(I)cc(Cl)cc45)cnc32)C1] | 5-chloro-7-iodo-1'-[2-({7-oxo-8-[(cis)-3-hydroxy-3-methylcyclobutyl]-5,6,7,8-tetrahydro-1,8-naphthyridin-3-yl}oxy)ethyl]-1,2-dihydrospiro[indole-3,4'-piperidin]-2-one | Calc'd 637.1 Found 637.0 | A-89 & B-24 |
| 289 | 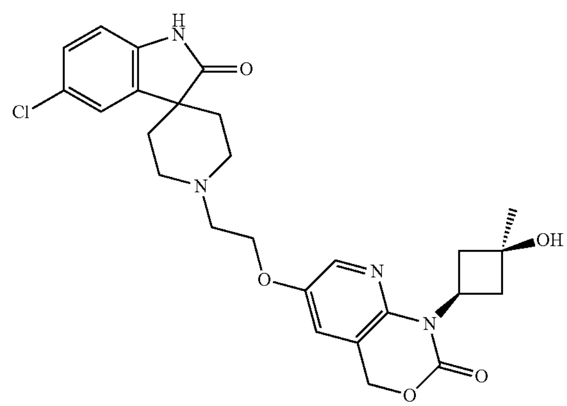 [SMILES: C[C@]1(O)C[C@@H](N2C(=O)OCc3cc(OCCN4CCC5(CC4)C(=O)Nc4ccc(Cl)cc45)cnc32)C1] | 5-chloro-1'-[2-({2-oxo-1-[(cis)-3-hydroxy-3-methylcyclobutyl]-1H,2H,4H-pyrido[2,3-d][1,3]oxazin-6-yl}oxy)ethyl]-1,2-dihydrospiro[indole-3,4'-piperidin]-2-one | Calc'd 513.2 Found 513.2 | A-90 & B-4 |
| 394 | 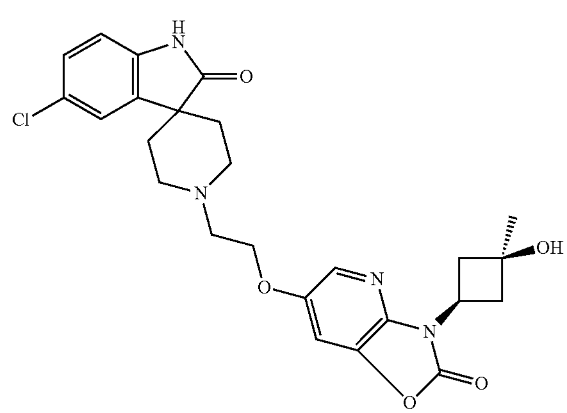 [SMILES: C[C@]1(O)C[C@@H](n2c(=O)oc3cc(OCCN4CCC5(CC4)C(=O)Nc4ccc(Cl)cc45)cnc32)C1] | 5-chloro-1'-[2-({2-oxo-3-[(cis)-3-hydroxy-3-methylcyclobutyl]-2H,3H-[1,3]oxazolo[4,5-b]pyridin-6-yl}oxy)ethyl]-1,2-dihydrospiro[indole-3,4'-piperidin]-2-one | Calc'd 499.2 Found 499.2 | A-91 & B-4 |

Example 59

5-chloro-1'-[2-({7-oxo-8-[(cis)-3-hydroxy-3-methyl-cyclobutyl]-5,6,7,8-tetrahydro-1,8-naphthyridin-3-yl}oxy)ethyl]-1,2-dihydrospiro[indole-3,4'-piperidin]-2-one (Compound 275)

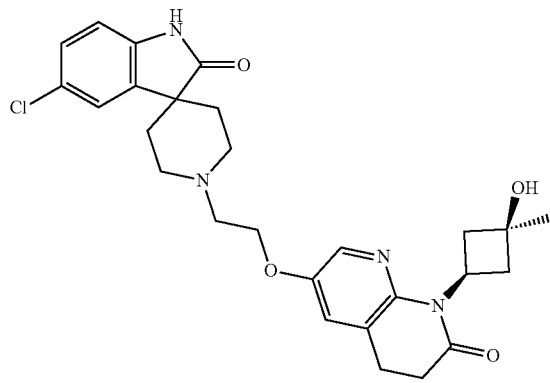 [SMILES: C[C@]1(O)C[C@@H](N2C(=O)CCc3cc(OCCN4CCC5(CC4)C(=O)Nc4ccc(Cl)cc45)cnc32)C1]

To a solution of 6-(2-bromoethoxy)-1-[(cis)-3-hydroxy-3-methylcyclobutyl]-1,2,3,4-tetrahydro-1,8-naphthyridin-2-one (Intermediate A-89, 330 mg, 0.929 mmol) and 5-chloro-1,2-dihydrospiro[indole-3,4'-piperidin]-2-one (Intermediate B-4, 279 mg, 1.02 mmol, HCl salt) in MeCN (10 mL) was added NaHCO$_3$ (234 mg, 2.79 mmol). The mixture was stirred at 80° C. for 12 h. After cooling to room temperature, the mixture was diluted with H$_2$O (20 mL) and extracted with EtOAc (3×10 mL). The combined organic layers were washed with brine (20 mL), dried over Na$_2$SO$_4$, filtered, and concentrated in vacuo. The crude residue was purified by reverse phase preparative HPLC (Waters Xbridge BEH C$_{18}$ column, 20-50% MeCN: 10 mM NH$_4$HCO$_3$ in H$_2$O) to give 5-chloro-1'-[2-({7-oxo-8-[(cis)-3-hydroxy-3-methylcyclobutyl]-5,6,7,8-tetrahydro-1,8-naphthyridin-3-yl}oxy)ethyl]-1,2-dihydrospiro[indole-3,4'-piperidin]-2-one (Compound 275). $^1$H NMR (400 MHz, DMSO-d$_6$): δ 10.48 (s, 1H), 7.94 (d, J=2.8 Hz, 1H), 7.50 (d, J=2.0 Hz, 1H), 7.39 (d, J=2.8 Hz, 1H), 7.23 (dd, J=8.0 Hz, 2.0 Hz, 1H), 6.84 (d, J=8.4 Hz, 1H), 4.82 (s, 1H), 4.30-4.22 (m, 1H), 4.18 (t, J=5.6 Hz, 2H), 2.95-2.89 (m, 2H), 2.87-2.77 (m, 4H), 2.72-2.67 (m, 2H), 2.48-2.46 (m, 2H), 2.46-2.41 (m, 2H), 2.38-2.32 (m, 2H), 1.82-1.67 (m, 4H), 1.25 (s, 3H). MS=511.1 [M+H]$^+$.

Example 60

5-chloro-1'-(2-{[2-(3-methanesulfonyloxetan-3-yl)pyrimidin-5-yl]oxy}ethyl)-1,2-dihydrospiro[indole-3,4'-piperidin]-2-one (Compound 276)

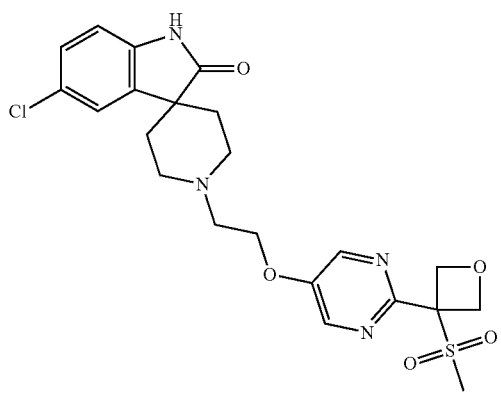 [SMILES: CS(=O)(=O)C1(c2ncc(OCCN3CCC4(CC3)C(=O)Nc3ccc(Cl)cc34)cn2)COC1]

To a solution of 5-(2-bromoethoxy)-2-(3-methanesulfonyloxetan-3-yl)pyrimidine (Intermediate A-88, 50.0 mg, 0.148 mmol) and 5-chloro-1,2-dihydrospiro[indole-3,4'-piperidin]-2-one (Intermediate B-4, 38.6 mg, 0.163 mmol) in MeCN (4 mL) was added NaHCO$_3$ (62.3 mg, 0.744 mmol). The mixture was stirred at 80° C. for 15 h. After cooling to room temperature, solids were removed by filtration and the filtrate was concentrated in vacuo. The crude residue was purified by reverse phase preparative HPLC (Phenomenex C$_{18}$ column, 15-45% MeCN: 10 mM NH$_4$HCO$_3$ in H$_2$O) to give 5-chloro-1'-(2-{[2-(3-methanesulfonyloxetan-3-yl)pyrimidin-5-yl]oxy}ethyl)-1,2-dihydrospiro[indole-3,4'-piperidin]-2-one (Compound 276). $^1$H NMR (400 MHz, DMSO-d$_6$): δ 10.49 (s, 1H), 8.71 (s, 2H), 7.50 (d, J=2.0 Hz, 1H), 7.25-7.22 (m, 1H), 6.84 (d, J=8.4 Hz, 1H), 5.20 (d, J=7.6 Hz, 2H), 5.09 (d, J=7.6 Hz, 2H), 4.38 (t, J=5.6 Hz, 2H), 3.02 (s, 3H), 2.94-2.89 (m, 4H), 2.72-2.70 (m, 2H), 1.78-1.71 (m, 4H). MS=493.1 [M+H]$^+$.

Example 61

5-(difluoromethyl)-1'-{2-[4-(3-hydroxy-1-methanesulfonylcyclobutyl)phenoxy]ethyl}-1-methyl-1,2-dihydrospiro[indole-3,4'-piperidin]-2-one (Compound 277), 5-(difluoromethyl)-1-methyl-1'-(2-{4-[(cis) or (trans)-3-hydroxy-1-methanesulfonylcyclobutyl]phenoxy}ethyl)-1,2-dihydrospiro[indole-3,4'-piperidin]-2-one (Compound 278), and 5-(difluoromethyl)-1-methyl-1'-(2-{4-[(trans) or (cis)-3-hydroxy-1-methanesulfonylcyclobutyl]phenoxy}ethyl)-1,2-dihydrospiro[indole-3,4'-piperidin]-2-one (Compound 279)

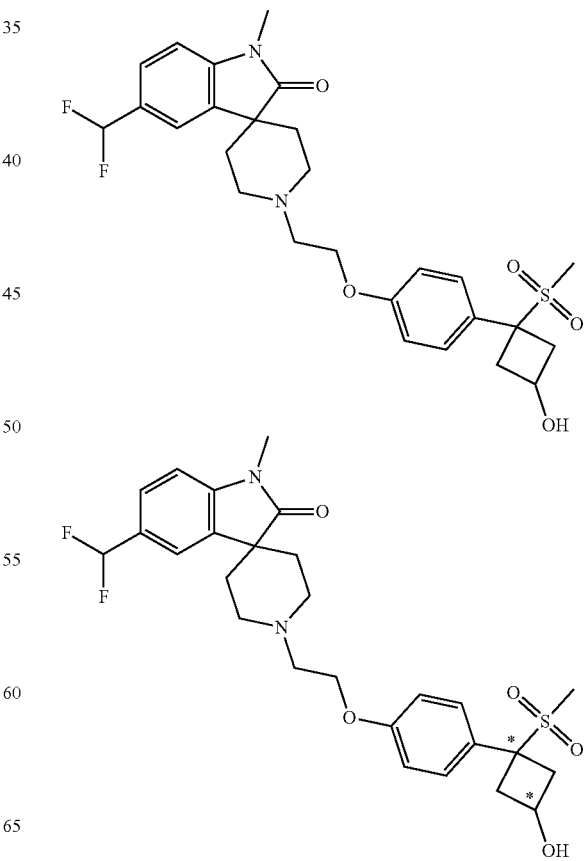

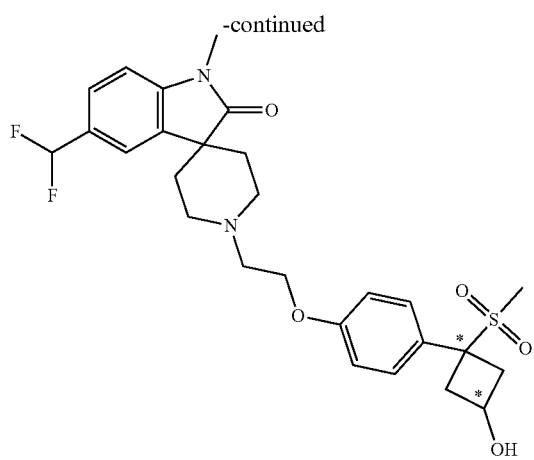

Step 1: 5-(difluoromethyl)-1'-{2-[4-(3-hydroxy-1-methanesulfonylcyclobutyl)phenoxy]ethyl}-1-methyl-1,2-dihydrospiro[indole-3,4'-piperidin]-2-one (Compound 277)

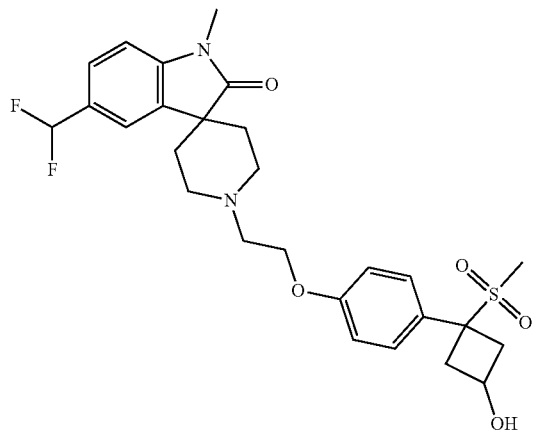 [SMILES: CN1C(=O)C2(CCN(CCOc3ccc(C4(S(C)(=O)=O)CC(O)C4)cc3)CC2)c2cc(C(F)F)ccc21]

To a solution of 2-[4-(3-hydroxy-1-methanesulfonylcyclobutyl)phenoxy]ethyl methanesulfonate (Example 54, Step 6, 100 mg, 0.274 mmol) and 5-(difluoromethyl)-1-methyl-1,2-dihydrospiro[indole-3,4'-piperidin]-2-one (Intermediate B-23, 100 mg, 0.329 mmol, HCl salt) in MeCN (4 mL) was added NaHCO$_3$ (92.0 mg, 1.10 mmol). The mixture was stirred at 80° C. for 12 h. After cooling to room temperature, solids were removed by filtration and the filtrate was concentrated in vacuo. The crude residue was purified by reverse phase preparative HPLC (Phenomenex C$_{18}$ column, 20-50% MeCN: 10 mM NH$_4$HCO$_3$ in H$_2$O) to give 5-(difluoromethyl)-1'-{2-[4-(3-hydroxy-1-methanesulfonylcyclobutyl)phenoxy]ethyl}-1-methyl-1,2-dihydrospiro[indole-3,4'-piperidin]-2-one (Compound 277). MS=535.2 [M+H]$^+$.

Step 2: 5-(difluoromethyl)-1-methyl-1'-(2-{4-[(cis) or (trans)-3-hydroxy-1-methanesulfonylcyclobutyl]phenoxy}ethyl)-1,2-dihydrospiro[indole-3,4'-piperidin]-2-one (Compound 278) and 5-(difluoromethyl)-1-methyl-1'-(2-{4-[(trans) or (cis)-3-hydroxy-1-methanesulfonylcyclobutyl]phenoxy}ethyl)-1,2-dihydrospiro[indole-3,4'-piperidin]-2-one (Compound 279)

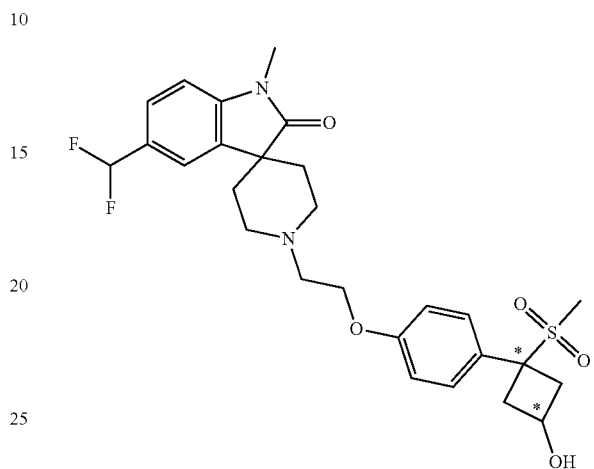

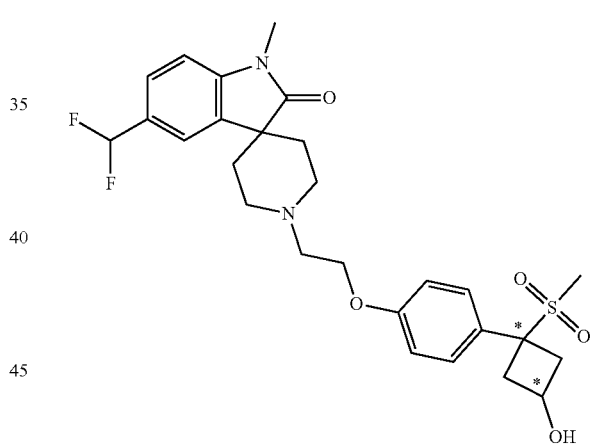

5-(difluoromethyl)-1'-{2-[4-(3-hydroxy-1-methanesulfonylcyclobutyl)phenoxy]ethyl}-1-methyl-1,2-dihydrospiro[indole-3,4'-piperidin]-2-one was purified by preparative chiral SFC (Daicel Chiralpak AD-3, 25-47% isopropanol with 0.1% NH$_4$OH in CO$_2$). The first eluting isomer of the title compound, Compound 278: $^1$H NMR (400 MHz, DMSO-d$_6$): δ 7.71 (s, 1H), 7.53 (d, J=7.6 Hz, 1H), 7.48 (d, J=8.8 Hz, 2H), 7.14 (d, J=8.0 Hz, 1H), 7.04-6.99 (m, 2H), 7.16-6.82 (m, 1H), 5.48 (d, J=6.4 Hz, 1H), 4.18 (s, 2H), 3.89-3.79 (m, 1H), 3.15 (s, 3H), 2.97 (s, 2H), 2.91-2.80 (m, 4H), 2.77-2.67 (m, 4H), 2.54 (s, 3H), 1.88-1.67 (m, 4H). MS=535.2 [M+H]$^+$. The second eluting isomer of the title compound, Compound 279: $^1$H NMR (400 MHz, DMSO-d$_6$): δ 7.71 (s, 1H), 7.53 (d, J=7.6 Hz, 1H), 7.24 (d, J=8.8 Hz, 2H), 7.14 (d, J=8.0 Hz, 1H), 7.01-6.98 (m, 2H), 7.16-6.84 (m, 1H), 5.33 (d, J=6.8 Hz, 1H), 4.39-4.30 (m, 1H), 4.17 (t, J=8.0 Hz, 2H), 3.29-3.23 (m, 2H), 3.15 (s, 3H), 3.00-2.93 (m, 2H), 2.90-2.84 (m, 2H), 2.75-2.68 (m, 2H), 2.64 (s, 3H), 2.44-2.37 (m, 2H), 1.86-1.68 (m, 4H). MS=535.2 [M+H]$^+$.

Example 62

5-(difluoromethyl)-1'-{2-[4-(3-hydroxy-1-methane-sulfonylcyclobutyl)phenoxy]ethyl}-1,2-dihydrospiro[indole-3,4'-piperidin]-2-one (Compound 280), 5-(difluoromethyl)-1'-(2-{4-[(cis) or (trans)-3-hydroxy-1-methanesulfonylcyclobutyl]phenoxy}ethyl)-1,2-dihydrospiro[indole-3,4'-piperidin]-2-one (Compound 281), and 5-(difluoromethyl)-1'-(2-{4-[(trans) or (cis)-3-hydroxy-1-methanesulfonylcyclobutyl]phenoxy}ethyl)-1,2-dihydrospiro[indole-3,4'-piperidin]-2-one (Compound 282)

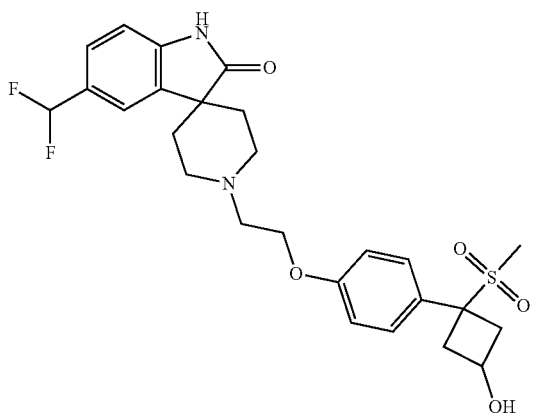 [SMILES: CS(=O)(=O)C1(c2ccc(OCCN3CCC4(CC3)C(=O)Nc3ccc(C(F)F)cc34)cc2)CC(O)C1]

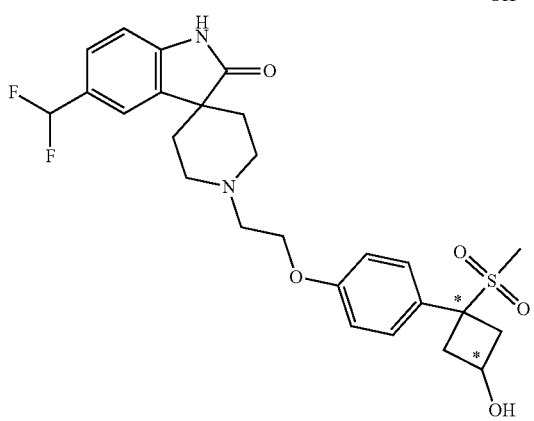

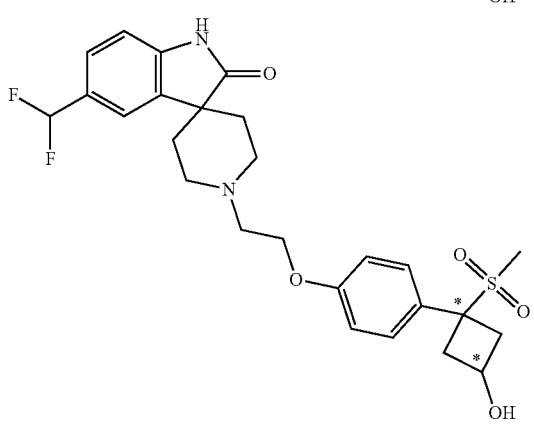

Step 1: 5-(difluoromethyl)-1'-{2-[4-(3-hydroxy-1-methanesulfonylcyclobutyl)phenoxy]ethyl}-1,2-dihydrospiro[indole-3,4'-piperidin]-2-one (Compound 280)

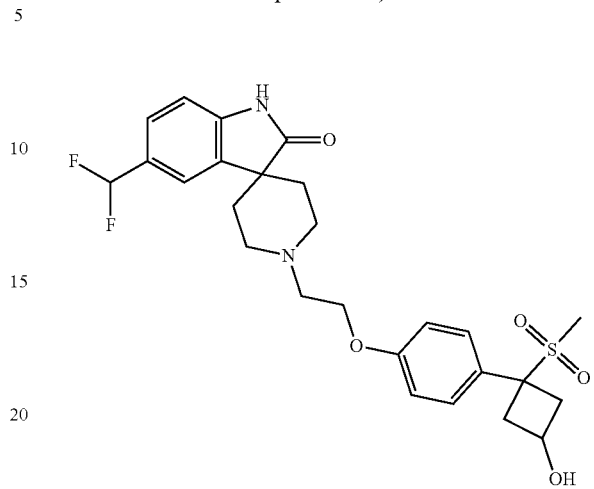

To a solution of 2-[4-(3-hydroxy-1-methanesulfonylcyclobutyl)phenoxy]ethyl methanesulfonate (Example 54, Step 6, 202 mg, 0.554 mmol) and 5-(difluoromethyl)-1,2-dihydrospiro[indole-3,4'-piperidin]-2-one (Intermediate B-1, 160 mg, 554 mmol, HCl salt) in MeCN (3 mL) was added NaHCO$_3$ (94.0 mg, 1.11 mmol). The mixture was stirred at 80° C. for 16 h. After cooling to room temperature, solids were removed by filtration and the filtrate was concentrated in vacuo. The crude residue was purified by reverse phase preparative HPLC (Waters XBridge C$_{18}$ column, 20-50% MeCN: 10 mM NH$_4$HCO$_3$ in H$_2$O) to give 5-(difluoromethyl)-1'-{2-[4-(3-hydroxy-1-methanesulfonylcyclobutyl)phenoxy]ethyl}-1,2-dihydrospiro[indole-3,4'-piperidin]-2-one (Compound 280). MS=521.2 [M+H]$^+$.

Step 2: 5-(difluoromethyl)-1'-(2-{4-[(cis) or (trans)-3-hydroxy-1-methanesulfonylcyclobutyl]phenoxy}ethyl)-1,2-dihydrospiro[indole-3,4'-piperidin]-2-one (Compound 281), and 5-(difluoromethyl)-1'-(2-{4-[(trans) or (cis)-3-hydroxy-1-methanesulfonylcyclobutyl]phenoxy}ethyl)-1,2-dihydrospiro[indole-3,4'-piperidin]-2-one (Compound 282)

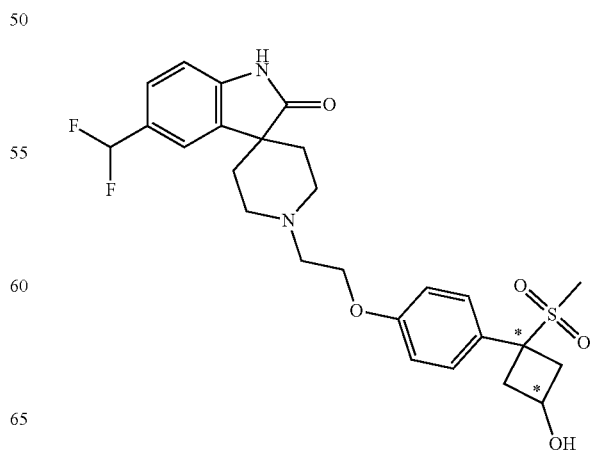

-continued

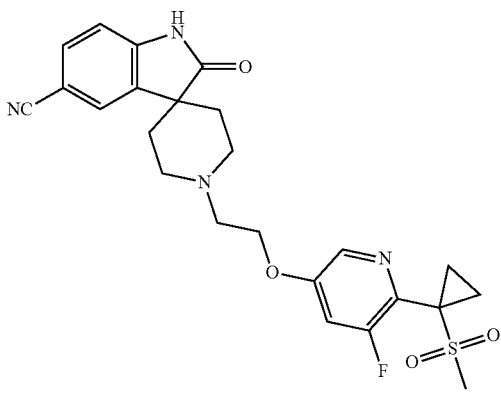 [SMILES: CS(=O)(=O)C1(c2ncc(OCCN3CCC4(CC3)C(=O)Nc3ccc(C#N)cc34)cc2F)CC1]

5-(Difluoromethyl)-1'-(2-{4-[(cis) or (trans)-3-hydroxy-1-methanesulfonylcyclobutyl]phenoxy}ethyl)-1,2-dihydrospiro[indole-3,4'-piperidin]-2-one was purified by preparative chiral SFC (Daicel Chiralpak AD-3, 40% isopropanol with 0.1% NH₄OH in CO₂). The first eluting isomer of the title compound, Compound 281: ¹H NMR (400 MHz, DMSO-d₆): 10.63 (s, 1H), 7.67 (s, 1H), 7.48 (d, J=8.4 Hz, 2H), 7.42 (d, J=8.0 Hz, 1H), 7.09-6.81 (m, 4H), 5.49 (d, J=6.4 Hz, 1H), 4.18 (t, J=4.8 Hz, 2H), 3.90-3.76 (m, 1H), 2.95 (s, 2H), 2.89-2.81 (m, 4H), 2.75-2.67 (m, 2H), 2.54 (s, 3H), 1.87-1.77 (m, 2H), 1.75-1.62 (m, 2H). MS=521.2 [M+H]⁺. The second eluting isomer of the title compound, Compound 282): ¹H NMR (400 MHz, DMSO-d₆): δ 10.63 (s, 1H), 7.67 (s, 1H), 7.42 (d, J=8.0 Hz, 1H), 7.24 (d, J=8.8 Hz, 2H), 7.10-6.82 (m, 4H), 5.33 (d, J=6.8 Hz, 1H), 4.38-4.28 (m, 1H), 4.16 (t, J=5.6 Hz, 2H), 3.32-3.23 (m, 2H), 2.99-2.90 (m, 2H), 2.86 (t, J=4.8 Hz, 2H), 2.70 (t, J=7.6 Hz, 2H), 2.64 (s, 3H), 2.45-2.37 (m, 2H), 1.87-1.78 (m, 2H), 1.70 (s, 2H). MS=521.2 [M+H]⁺.

Example 63

1'-(2-{[5-fluoro-6-(1-methanesulfonylcyclopropyl)pyridin-3-yl]oxy}ethyl)-2-oxo-1,2-dihydrospiro[indole-3,4'-piperidine]-5-carbonitrile (Compound 283)

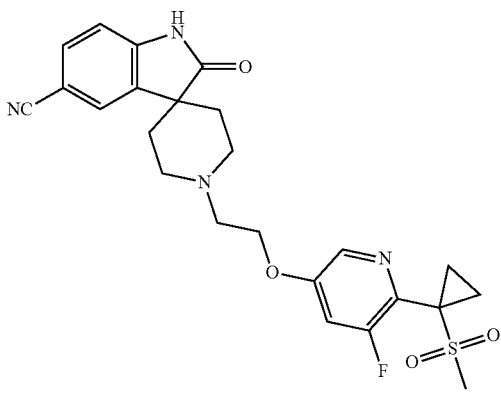 [SMILES: CS(=O)(=O)C1(c2ncc(OCCN3CCC4(CC3)C(=O)Nc3ccc(C#N)cc34)cc2F)CC1]

To a solution of 5-(2-bromoethoxy)-3-fluoro-2-(1-methanesulfonylcyclopropyl)pyridine (Intermediate A-87, 90.0 mg, 0.266 mmol) and 2-oxo-1,2-dihydrospiro[indole-3,4'-piperidine]-5-carbonitrile (Intermediate B-9, 78.0 mg, 0.293 mmol, HCl salt) in MeCN (1.5 mL) was added NaHCO₃ (112 mg, 1.33 mmol). The mixture was stirred at 80° C. for 15 h. After cooling to room temperature, solids were removed by filtration and the filtrate was purified by normal phase preparative TLC (SiO₂, EtOAc:MeOH=10:1) to give 1'-(2-{[5-fluoro-6-(1-methanesulfonylcyclopropyl)pyridin-3-yl]oxy}ethyl)-2-oxo-1,2-dihydrospiro[indole-3,4'-piperidine]-5-carbonitrile (Compound 283). ¹H NMR (400 MHz, DMSO-d₆): δ 10.87 (s, 1H), 8.24 (d, J=2.0 Hz, 1H), 7.96 (s, 1H), 7.68-7.54 (m, 2H), 7.00 (d, J=8.0 Hz, 1H), 4.28 (s, 2H), 2.95 (s, 3H), 2.93-2.83 (m, 4H), 2.74 (d, J=6.8 Hz, 2H), 1.84-1.69 (m, 6H), 1.39-1.36 (m, 2H). MS=485.1 [M+H]⁺.

Example 64

5-chloro-1'-(2-{[2-(1-hydroxyethyl)pyrimidin-5-yl]oxy}ethyl)-1,2-dihydrospiro[indole-3,4'-piperidin]-2-one (Compound 284), 5-chloro-1'-[2-({2-[(1S) or (1R)-1-hydroxyethyl]pyrimidin-5-yl}oxy)ethyl]-1,2-dihydrospiro[indole-3,4'-piperidin]-2-one (Compound 285) and 5-chloro-1'-[2-({2-[(1R) or (1S)-1-hydroxyethyl]pyrimidin-5-yl}oxy)ethyl]-1,2-dihydrospiro[indole-3,4'-piperidin]-2-one (Compound 286)

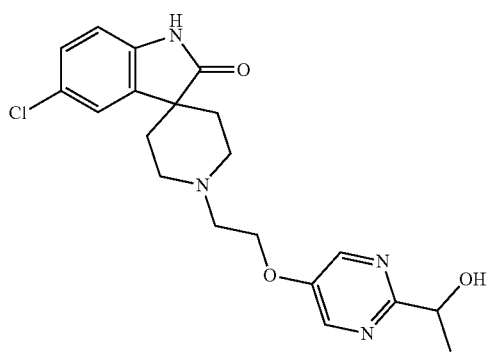 [SMILES: CC(O)c1ncc(OCCN2CCC3(CC2)C(=O)Nc2ccc(Cl)cc23)cn1]

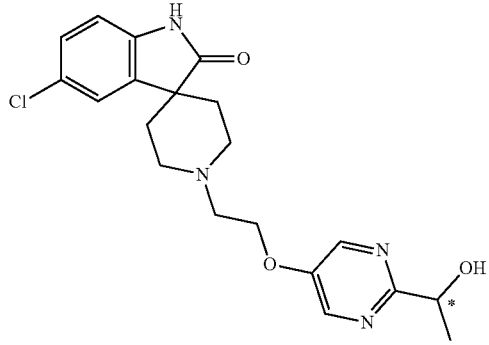

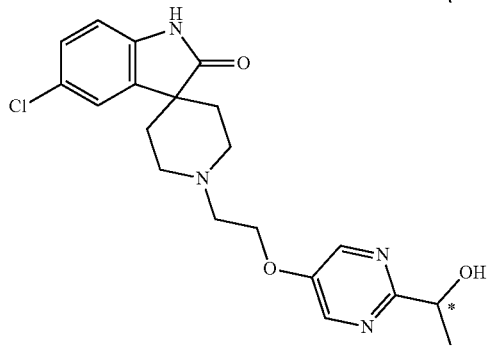

1151

Step 1: 5-chloro-1'-(2-{[2-(1-hydroxyethyl)pyrimidin-5-yl]oxy}ethyl)-1,2-dihydrospiro[indole-3,4'-piperidin]-2-one

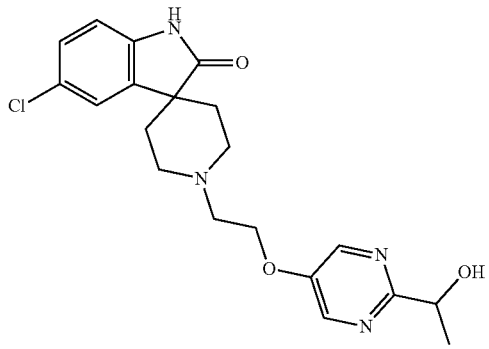

A mixture of 1-[5-(2-bromoethoxy)pyrimidin-2-yl]ethan-1-ol (Intermediate A-86, 90.0 mg, 0.364 mmol), 5-chloro-1,2-dihydrospiro[indole-3,4'-piperidin]-2-one (Intermediate B-4, 91.0 mg, 0.382 mmol, HCl salt), and NaHCO₃ (153 mg, 1.82 mmol) in MeCN (5 mL) under N₂ atmosphere was stirred at 80° C. for 15 h. After cooling to room temperature, solids were removed by filtration and the filtrate was concentrated in vacuo. The crude residue was purified by flash silica gel chromatography (Biotage 4 g cartridge, 0-20% MeOH:EtOAc) to give 5-chloro-1'-(2-{[2-(1-hydroxyethyl)pyrimidin-5-yl]oxy}ethyl)-1,2-dihydrospiro[indole-3,4'-piperidin]-2-one (Compound 284). ¹H NMR (400 MHz, DMSO-d₆): δ 10.49 (s, 1H), 8.55 (s, 2H), 7.50 (d, J=2.0 Hz, 1H), 7.23 (dd, J=8.0 Hz, 2.0 Hz, 1H), 6.84 (d, J=8.0 Hz, 1H), 5.10 (d, J=5.6 Hz, 1H), 4.78-4.72 (m, 1H), 4.30 (t, J=5.6 Hz, 2H), 2.92-2.65 (m, 4H), 2.71-2.69 (m, 2H), 1.78-1.70 (m, 4H), 1.38 (d, J=6.8 Hz, 3H). MS=403.2 [M+H]⁺.

Step 2: 5-chloro-1'-[2-({2-[(1S) or (1R)-1-hydroxyethyl]pyrimidin-5-yl}oxy)ethyl]-1,2-dihydrospiro[indole-3,4'-piperidin]-2-one (Compound 285) and 5-chloro-1'-[2-({2-[(1R) or (1S)-1-hydroxyethyl]pyrimidin-5-yl}oxy)ethyl]-1,2-dihydrospiro[indole-3,4'-piperidin]-2-one (Compound 286)

1152

-continued

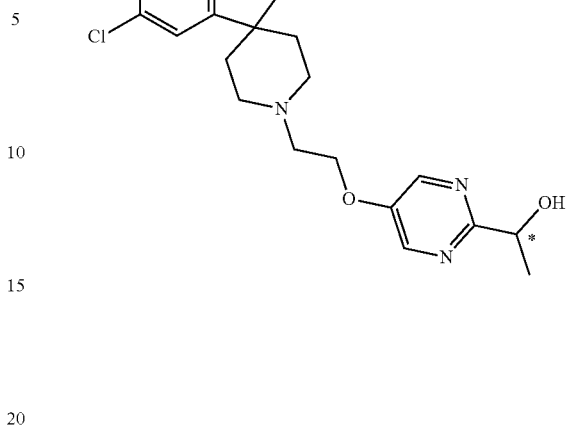

5-chloro-1'-(2-{[2-(1-hydroxyethyl)pyrimidin-5-yl]oxy}ethyl)-1,2-dihydrospiro[indole-3,4'-piperidin]-2-one (100 mg, 0.248 mmol) was purified by preparative chiral SFC (Daicel Chiralpak IC-3, 55% MeOH with 0.1% NH₄OH in CO₂). The first eluting enantiomer of the title compound, Compound 285: ¹H NMR (400 MHz, DMSO-d₆): δ 10.48 (s, 1H), 8.55 (s, 2H), 7.50 (d, J=2.4 Hz, 1H), 7.23 (dd, J=8.4 Hz, 2.0 Hz, 1H), 6.84 (d, J=8.4 Hz, 1H), 5.10 (d, J=5.6 Hz, 1H), 4.80-4.71 (m, 1H), 4.30 (t, J=5.6 Hz, 2H), 2.95-2.85 (m, 4H), 2.72-2.66 (m, 2H), 1.82-1.75 (m, 2H), 1.73-1.66 (m, 2H), 1.39 (d, J=6.4 Hz, 3H). MS=403.2 [M+H]⁺. The second eluting enantiomer of the title compound, Compound 286: ¹H NMR (400 MHz, DMSO-d₆): δ 10.48 (s, 1H), 8.55 (d, J=2.4 Hz, 2H), 7.50 (s, 1H), 7.23 (d, J=8.4 Hz, 1H), 6.84 (dd, J=8.4 Hz, 2.0 Hz, 1H), 5.10 (dd, J=5.6 Hz, 2.0 Hz, 1H), 4.80-4.71 (m, 1H), 4.30 (t, J=4.0 Hz, 2H), 2.94-2.84 (m, 4H), 2.73-2.67 (m, 2H), 1.81-1.66 (m, 4H), 1.39 (d, J=6.8 Hz, 3H). MS=403.2 [M+H]⁺.

Example 65

5-chloro-1'-(2-{[8-(3-hydroxyazetidin-1-yl)-1,7-naphthyridin-3-yl]oxy}ethyl)-1,2-dihydrospiro[indole-3,4'-piperidin]-2-one (Compound 314)

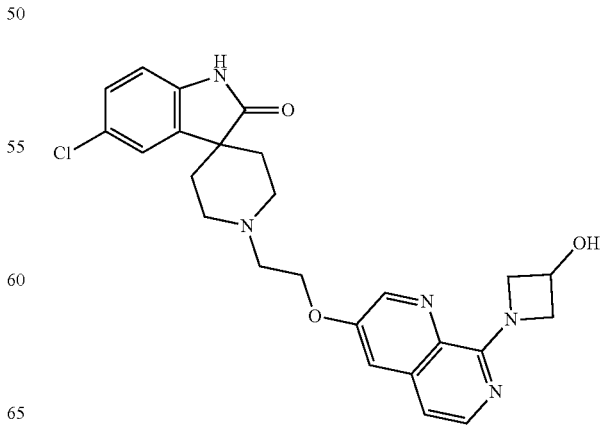

Step 1: 1-(3-bromo-1,7-naphthyridin-8-yl)azetidin-3-ol

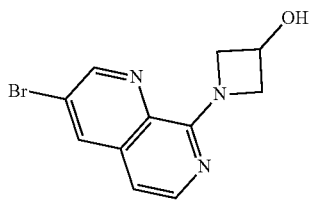 [SMILES: OC1CN(c2nccc3cc(Br)cnc23)C1]

A mixture of 3-bromo-8-chloro-1,7-naphthyridine (500 mg, 2.05 mmol), azetidin-3-ol (270 mg, 2.46 mmol), and diisopropylethylamine (663 mg, 5.13 mmol) in DMF (5 mL) was stirred at 50° C. for 16 h. After cooling to room temperature, the mixture was diluted with EtOAc (10 mL), and H₂O (20 mL) was then added. A precipitated solid was collected by filtration, and dried in vacuo to give 1-(3-bromo-1,7-naphthyridin-8-yl)azetidin-3-ol, which was used in the next step without further purification. MS=280.0/282.0 [M+H]⁺.

Step 2: [8-(3-hydroxyazetidin-1-yl)-1,7-naphthyridin-3-yl]boronic acid

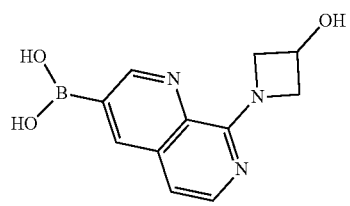 [SMILES: OB(O)c1cnc2c(N3CC(O)C3)nccc2c1]

A mixture of 1-(3-bromo-1,7-naphthyridin-8-yl)azetidin-3-ol (250 mg, 0.892 mmol), bis(pinacolato)diboron (272 mg, 1.07 mmol), Pd(dppf)Cl₂·CH₂Cl₂ (36.0 mg, 0.045 mmol) and KOAc (219 mg, 2.21 mmol) in 1,4-dioxane (15 mL) was purged with N₂ for 10 min, then stirred at 90° C. under N₂ for 16 h. The mixture was cooled to room temperature, filtered over a celite pad, and then washed with EtOAc (30 mL). The filtrate was concentrated in vacuo to give [8-(3-hydroxyazetidin-1-yl)-1,7-naphthyridin-3-yl]boronic acid, which was used in the next step without further purification. MS=246.2 [M+H]⁺.

Step 3: 8-(3-hydroxyazetidin-1-yl)-1,7-naphthyridin-3-ol

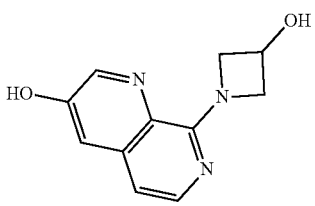 [SMILES: Oc1cnc2c(N3CC(O)C3)nccc2c1]

[8-(3-Hydroxyazetidin-1-yl)-1,7-naphthyridin-3-yl]boronic acid (0.892 mmol) was dissolved in MeOH (5 mL) and cooled to 0° C. 30% H₂O₂ in H₂O (0.228 mL, 2.23 mmol) was then added dropwise. The resulting mixture was stirred at room temperature for 3 h, then concentrated in vacuo to give 8-(3-hydroxyazetidin-1-yl)-1,7-naphthyridin-3-ol, which was used in the next step without further purification. MS=218.1 [M+H]⁺.

Step 4: 1-(3-(2-bromoethoxy)-1,7-naphthyridin-8-yl)azetidin-3-ol

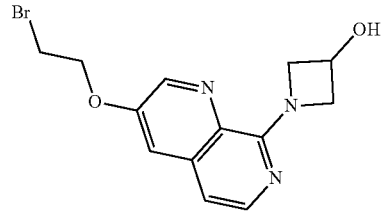 [SMILES: OC1CN(c2nccc3cc(OCCBr)cnc23)C1]

A mixture of 8-(3-hydroxyazetidin-1-yl)-1,7-naphthyridin-3-ol (220 mg, 1.01 mmol) and Cs₂CO₃ (660 mg, 2.03 mmol) in 1,2-dibromoethane (3.50 mL, 40.5 mmol) and DMF (1 mL) was stirred at 90° C. for 3 h. The mixture was cooled to room temperature and filtered over a celite pad. The filtrate was concentrated in vacuo. The crude residue was purified by flash silica gel chromatography (Biotage 25 g cartridge, 0-10% MeOH/DCM) to give 1-[3-(2-bromoethoxy)-1,7-naphthyridin-8-yl]azetidin-3-ol. MS=324.1/326.1 [M+H]⁺.

Step 5: 5-chloro-1'-(2-{[8-(3-hydroxyazetidin-1-yl)-1,7-naphthyridin-3-yl]oxy}ethyl)-1,2-dihydrospiro[indole-3,4'-piperidin]-2-one (Compound 314)

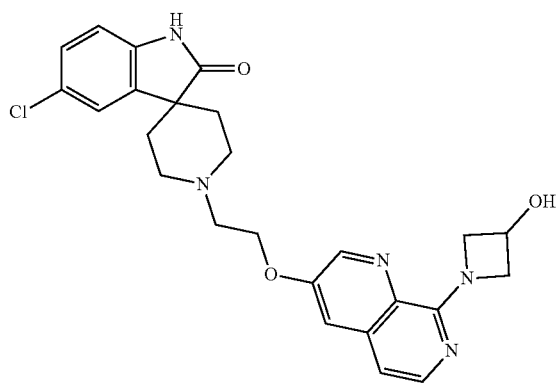 [SMILES: O=C1Nc2ccc(Cl)cc2C12CCN(CCOc1cnc3c(N4CC(O)C4)nccc3c1)CC2]

A mixture of 1-[3-(2-bromoethoxy)-1,7-naphthyridin-8-yl]azetidin-3-ol (45.0 mg, 0.139 mmol), 5-chloro-1,2-dihydrospiro[indole-3,4'-piperidin]-2-one (Intermediate B-4, 39.8 mg, 0.146 mmol, HCl salt), K₂CO₃ (48.0 mg, 0.347 mmol) and KI (12.0 mg, 0.069 mmol) in DMF (1.0 mL) was stirred at 60° C. for 16 h. The mixture was then cooled to room temperature and filtered over a celite pad. The filtrate was concentrated in vacuo. The crude residue was purified by reverse phase preparative HPLC (Phenomenex Kinetex C₁₈ column, 5-50% MeCN in H₂O with 0.1% NH₄OH modifier) to give 5-chloro-1'-(2-{[8-(3-hydroxyazetidin-1-yl)-1,7-naphthyridin-3-yl]oxy}ethyl)-1,2-dihydrospiro[indole-3,4'-piperidin]-2-one (Compound 314). ¹H NMR (500 MHz, DMSO-d₆): δ 10.42 (s, 1H), 8.40 (d, J=2.9 Hz, 1H), 7.82 (d, J=5.6 Hz, 1H), 7.54 (d, J=2.9 Hz, 1H), 7.44 (d, J=2.2 Hz, 1H), 7.17 (dd, J=8.2 Hz, 2.1 Hz, 1H), 6.82 (d, J=5.6 Hz, 1H), 6.78 (d, J=8.3 Hz, 1H), 5.53 (d, J=5.6 Hz, 1H), 4.54-4.49 (m, 3H), 4.24 (t, J=5.7 Hz, 2H), 4.03-3.99 (m, 2H), 2.92-2.83 (m, 4H), 2.70-2.61 (m, 2H), 1.78-1.60 (m, 4H). MS=480.2 [M+H]$^+$.

The following compound in Table 38.2 was prepared according to the procedures similar to those described for Compound 314 using the appropriate starting materials.

TABLE 38.2

| No. | Structure | IUPAC Name | Exact Mass [M + H]$^+$ |
|---|---|---|---|
| 306 | 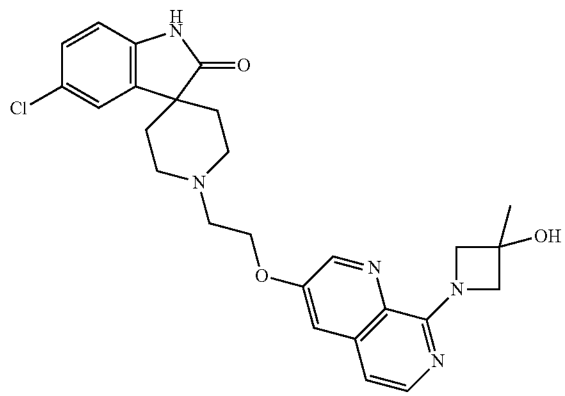 [SMILES: CC1(O)CN(c2nccc3cc(OCCN4CCC5(CC4)C(=O)Nc4ccc(Cl)cc45)cnc23)C1] | 5-chloro-1'-(2-{[8-(3-hydroxy-3-methylazetidin-1-yl)-1,7-naphthyridin-3-yl]oxy}ethyl)-1,2-dihydrospiro[indole-3,4'-piperidin]-2-one | Calc'd 494.2 Found 494.2 |
| 364 | 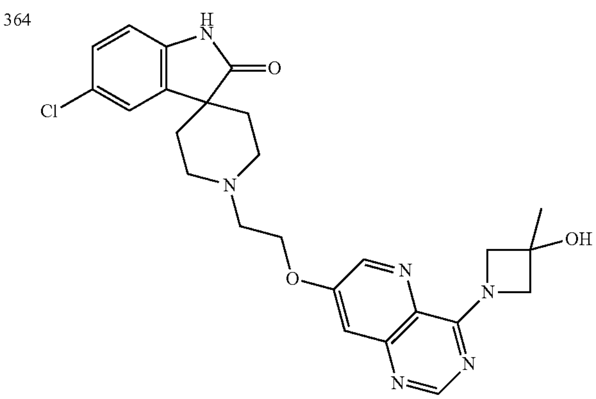 | 5-chloro-1'-(2-{[4-(3-hydroxy-3-methylazetidin-1-yl)pyrido[3,2-d]pyrimidin-7-yl]oxy}ethyl)-1,2-dihydrospiro[indole-3,4'-piperidin]-2-one | Calc'd 495.2 Found 495.2 |
| 366 | 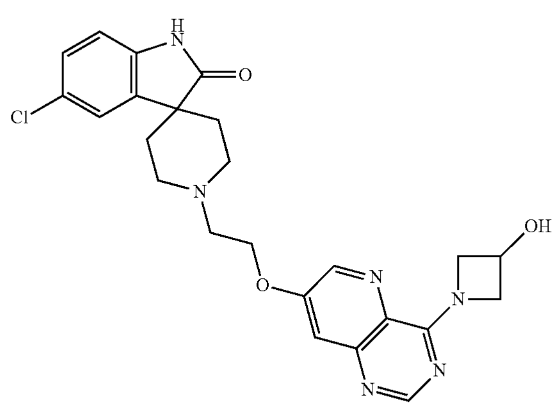 [SMILES: O=C1Nc2ccc(Cl)cc2C12CCN(CCOc1cnc3c(N4CC(O)C4)ncnc3c1)CC2] | 5-chloro-1'-(2-{[4-(3-hydroxyazetidin-1-yl)pyrido[3,2-d]pyrimidin-7-yl]oxy}ethyl)-1,2-dihydrospiro[indole-3,4'-piperidin]-2-one | Calc'd 481.2 Found 481.2 |

Example 66

5-chloro-1'-(2-{[2-(2-hydroxypropan-2-yl)pyrimidin-5-yl]oxy}ethyl)-1,2-dihydrospiro[indole-3,4'-piperidin]-2-one (Compound 305)

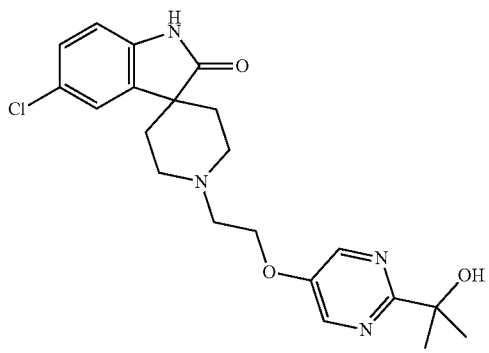 [SMILES: CC(C)(O)c1ncc(OCCN2CCC3(CC2)C(=O)Nc2ccc(Cl)cc23)cn1]

Step 1: 2-(5-(2-bromoethoxy)pyrimidin-2-yl)propan-2-ol

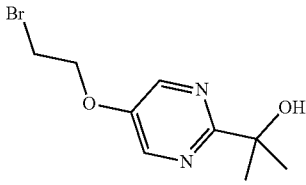

A mixture of 2-(2-hydroxypropan-2-yl)pyrimidin-5-ol (120 mg, 0.778 mmol) and Cs$_2$CO$_3$ (507 mg, 1.56 mmol) in 1,2-dibromoethane (2.7 mL, 31.5 mmol) and DMF (0.3 mL) was stirred at 90° C. for 3 h. The mixture was cooled to room temperature and filtered over a celite pad, and the filtrate was concentrated in vacuo. The crude residue was purified by flash silica gel chromatography (Biotage 25 g cartridge, 0-70% EtOAc/Hexane) to give 2-[5-(2-bromoethoxy)pyrimidin-2-yl]propan-2-ol. MS=261.1/263.1 [M+H]$^+$.

Step 2: 5-chloro-1'-(2-{[2-(2-hydroxypropan-2-yl)pyrimidin-5-yl]oxy}ethyl)-1,2-dihydrospiro[indole-3,4'-piperidin]-2-one (Compound 305)

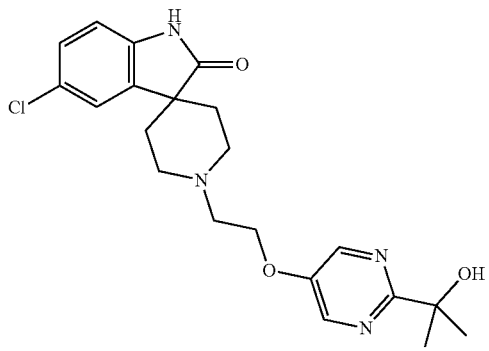 [SMILES: CC(C)(O)c1ncc(OCCN2CCC3(CC2)C(=O)Nc2ccc(Cl)cc23)cn1]

A mixture of 2-[5-(2-bromoethoxy)pyrimidin-2-yl]propan-2-ol (51.0 mg, 0.195 mmol), 5-chloro-1H-spiro[indole-3,4'-piperidin]-2-one (Intermediate B-4, 58.7 mg, 0.215 mmol, HCl salt), K$_2$CO$_3$ (67.0 mg, 0.488 mmol), and KI (16 mg, 0.098 mmol) in DMF (2.0 mL) was stirred at 60° C. for 16 h. The mixture was cooled to room temperature and filtered over a celite pad. The filtrate was concentrated in vacuo, and the residue was purified by reverse phase preparative HPLC (5-40% MeCN in H$_2$O with 0.1% formic acid modifier) to give 5-chloro-1'-(2-{[2-(2-hydroxypropan-2-yl)pyrimidin-5-yl]oxy}ethyl)-1,2-dihydrospiro[indole-3,4'-piperidin]-2-one (Compound 305). $^1$H NMR (500 MHz, DMSO-d$_6$): δ 10.47 (s, 1H), 8.50 (s, 2H), 7.45-7.41 (m, 1H), 7.19 (dd, J=8.3 Hz, 2.1 Hz, 1H), 6.79 (d, J=8.3 Hz, 1H), 4.88 (s, 1H), 4.32-4.28 (m, 2H), 3.11-2.47 (m, 6H), 2.00-1.48 (m, 4H), 1.41 (s, 6H). MS=417.2 [M+H]$^+$.

Example 67

5-chloro-1'-(2-{[2-(3-hydroxyazetidin-1-yl)pyrimidin-5-yl]oxy}ethyl)-1,2-dihydrospiro[indole-3,4'-piperidin]-2-one (Compound 301)

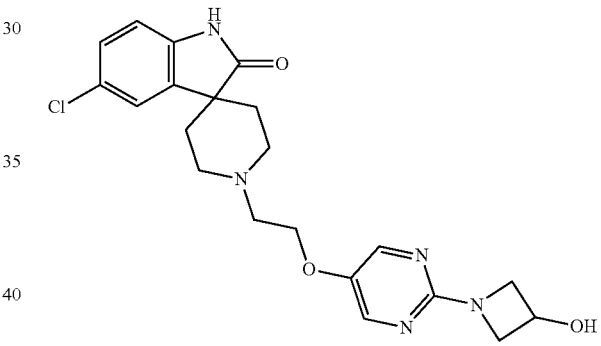

Step 1: 5-(2-bromoethoxy)-2-chloropyrimidine

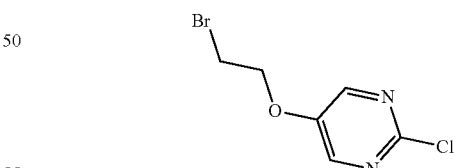

To a solution of 2-chloropyrimidin-5-ol (1.00 g, 7.66 mmol) in DMF (7.7 mL) was added 1,2-dibromoethane (15.3 mL, 194 mmol) and Cs$_2$CO$_3$ (7.49 g, 23.0 mmol). The mixture was stirred at 90° C. for 16 h. The mixture was cooled to room temperature and filtered over a celite pad, and the filtrate was concentrated in vacuo. The crude residue was purified by flash silica gel chromatography (Biotage 50 g cartridge, 0-100% EtOAc/Hexanes) to give 5-(2-bromoethoxy)-2-chloropyrimidine as a yellow oil. MS=237.0 [M+H]$^+$.

Step 2: 5-chloro-1'-{2-[(2-chloropyrimidin-5-yl)oxy]ethyl}-1,2-dihydrospiro[indole-3,4'-piperidin]-2-one Step 3: 5-chloro-1'-(2-{[2-(3-hydroxyazetidin-1-yl)pyrimidin-5-yl]oxy}ethyl)-1,2-dihydrospiro[indole-3,4'-piperidin]-2-one (Compound 301)

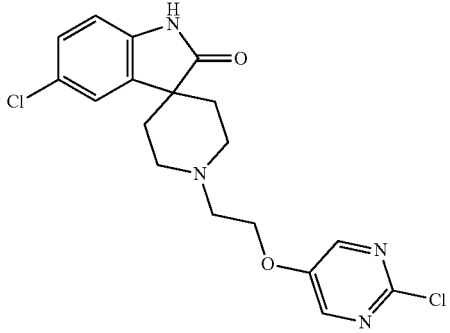 [SMILES: O=C1Nc2ccc(Cl)cc2C12CCN(CCOc1cnc(Cl)nc1)CC2]

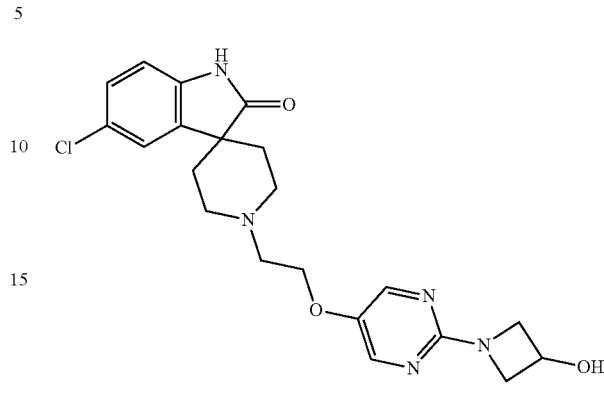

To a vial was added 5-(2-bromoethoxy)-2-chloropyrimidine (1.23 g, 3.13 mmol), 5-chloro-1H-spiro[indole-3,4'-piperidin]-2-one (Intermediate B-4, 1.34 g, 4.92 mmol, HCl salt), K₂CO₃ (2.15 g, 15.5 mmol), KI (860 mg, 5.18 mmol), and DMF (17.3 mL). The mixture was stirred at 65° C. for 4 h. After cooling to room temperature, the mixture was diluted with H₂O (100 mL). The resulting solids were isolated by filtration and dried in vacuo to give 5-chloro-1'-{2-[(2-chloropyrimidin-5-yl)oxy]ethyl}-1,2-dihydrospiro[indole-3,4'-piperidin]-2-one, which was used in the subsequent step without further purification. MS=393.2 [M+H]⁺.

To a microwave vial was added azetidin-3-ol (63.0 mg, 0.575 mmol, HCl salt), 5-chloro-1'-{2-[(2-chloropyrimidin-5-yl)oxy]ethyl}-1,2-dihydrospiro[indole-3,4'-piperidin]-2-one (75.0 mg, 0.191 mmol), DMSO (0.38 mL), and TEA (0.058 g, 0.572 mmol). The reaction stirred at 100° C. for 1 h under microwave irradiation (normal absorption). The reaction was cooled to room temperature and diluted with H₂O (1 mL) and MeCN (1 mL). The mixture was purified by reverse phase C₁₈ chromatography (Biotage SFär C₁₈ Duo cartridge, 5-50% MeCN in H₂O with 0.1% NH₄OH modifier) to give 5-chloro-1'-(2-{[2-(3-hydroxyazetidin-1-yl)pyrimidin-5-yl]oxy}ethyl)-1,2-dihydrospiro[indole-3,4'-piperidin]-2-one (Compound 301). $^1$H NMR (500 MHz, DMSO-d₆): δ 10.48 (s, 1H), 8.21 (s, 2H), 7.50 (d, J=2.2 Hz, 1H), 7.23 (dd, J=8.3 Hz, 2.1 Hz, 1H), 6.84 (d, J=8.2 Hz, 1H), 5.61 (d, J=5.7 Hz, 1H), 4.56-4.49 (m, 1H), 4.18-4.08 (m, 4H), 3.74-3.68 (m, 2H), 2.93-2.86 (m, 2H), 2.80 (t, J=5.7 Hz, 2H), 2.70-2.62 (m, 2H), 1.80-1.66 (m, 4H). MS=430.2 [M+H]⁺.

The following compounds in Table 38.4 were prepared according to the procedures similar to those described for Compound 301 using the appropriate starting materials.

TABLE 38.4

| No. | Structure | IUPAC Name | Exact Mass [M + H]⁺ | Intermediate Used |
|---|---|---|---|---|
| 304 | 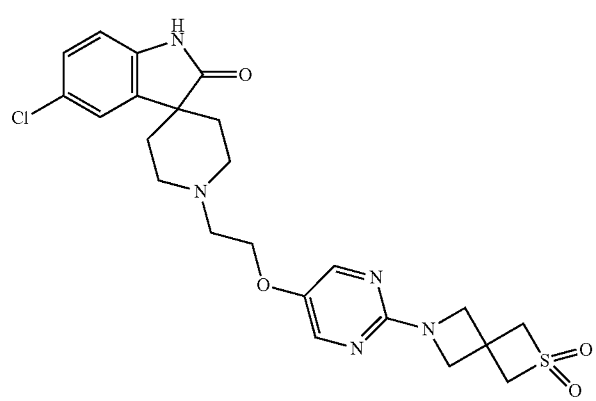 [SMILES: O=C1Nc2ccc(Cl)cc2C12CCN(CCOc1cnc(N3CC4(C3)CS(=O)(=O)C4)nc1)CC2] | 6-[5-(2-{5-chloro-2-oxo-1,2-dihydrospiro[indole-3,4'-piperidin]-1'-yl}ethoxy)pyrimidin-2-yl]-2λ⁶-thia-6-azaspiro[3.3]heptane-2,2-dione | Calc'd 504.1 Found 504.2 | B-4 |

TABLE 38.4-continued

| No. | Structure | IUPAC Name | Exact Mass [M + H]+ | Intermediate Used |
|---|---|---|---|---|
| 303 | 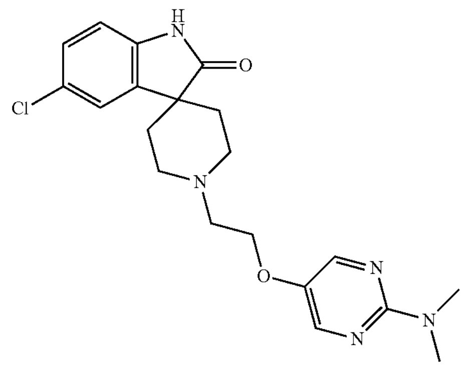 [SMILES: CN(C)c1ncc(OCCN2CCC3(CC2)C(=O)Nc2ccc(Cl)cc23)cn1] | 5-chloro-1'-(2-{[2-(dimethylamino)pyrimidin-5-yl]oxy}ethyl)-1,2-dihydrospiro[indole-3,4'-piperidin]-2-one | Calc'd 402.2 Found 402.2 | B-4 |
| 302 | 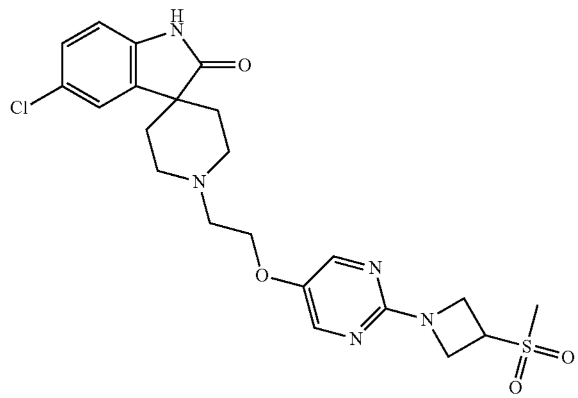 [SMILES: CS(=O)(=O)C1CN(c2ncc(OCCN3CCC4(CC3)C(=O)Nc3ccc(Cl)cc34)cn2)C1] | 5-chloro-1'-(2-{[2-(3-methanesulfonylazetidin-1-yl)pyrimidin-5-yl]oxy}ethyl)-1,2-dihydrospiro[indole-3,4'-piperidin]-2-one | Calc'd 492.1 Found 492.1 | B-4 |
| 300 | 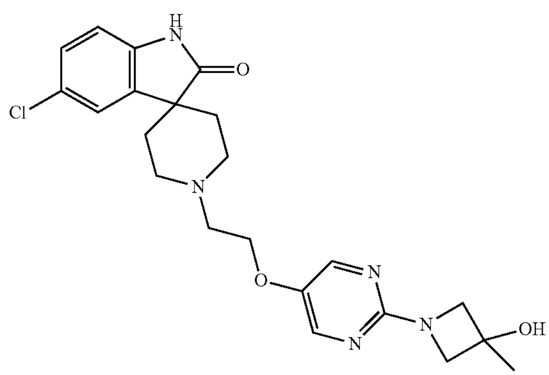 [SMILES: CC1(O)CN(c2ncc(OCCN3CCC4(CC3)C(=O)Nc3ccc(Cl)cc34)cn2)C1] | 5-chloro-1'-(2-{[2-(3-hydroxy-3-methylazetidin-1-yl)pyrimidin-5-yl]oxy}ethyl)-1,2-dihydrospiro[indole-3,4'-piperidin]-2-one | Calc'd 444.2 Found 444.2 | B-4 |
| 395 | 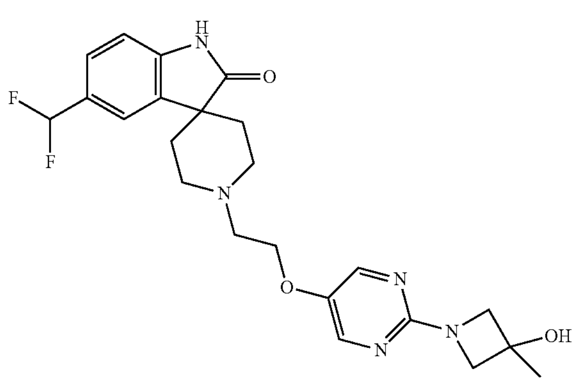 [SMILES: CC1(O)CN(c2ncc(OCCN3CCC4(CC3)C(=O)Nc3ccc(C(F)F)cc34)cn2)C1] | 5-(difluoromethyl)-1'-(2-{[2-(3-hydroxy-3-methylazetidin-1-yl)pyrimidin-5-yl]oxy}ethyl)-1,2-dihydrospiro[indole-3,4'-piperidin]-2-one | Calc'd 460.2 Found 460.2 | B-1 |

TABLE 38.4-continued

| No. | Structure | IUPAC Name | Exact Mass [M + H]+ | Intermediate Used |
|---|---|---|---|---|
| 396 | 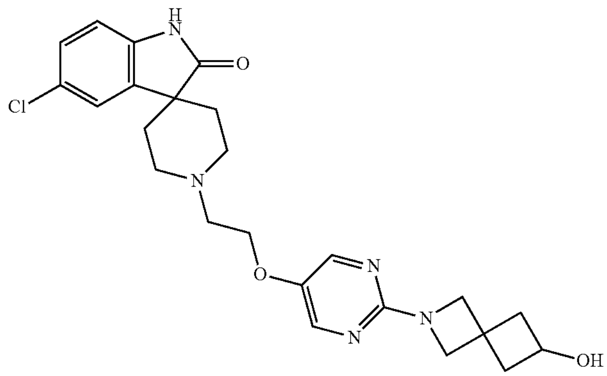 [SMILES: O=C1Nc2ccc(Cl)cc2C12CCN(CCOc1cnc(N3CC4(CC(O)C4)C3)nc1)CC2] | 5-chloro-1'-{2-[(2-{6-hydroxy-2-azaspiro[3.3]heptan-2-yl}pyrimidin-5-yl)oxy]ethyl}-1,2-dihydrospiro[indole-3,4'-piperidin]-2-one | Calc'd 470.0 Found 470.2 | B-4 |
| 397 | 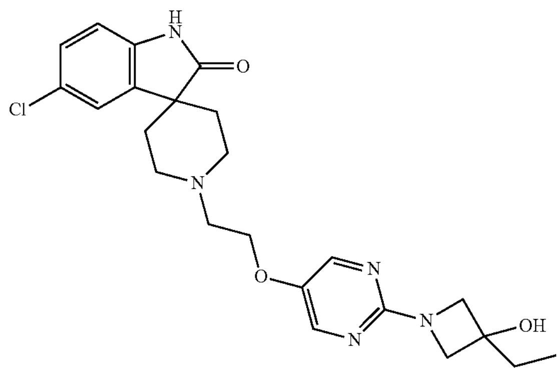 [SMILES: CCC1(O)CN(c2ncc(OCCN3CCC4(CC3)C(=O)Nc3ccc(Cl)cc34)cn2)C1] | 5-chloro-1'-(2-{[2-(3-ethyl-3-hydroxyazetidin-1-yl)pyrinlidin-5-yl]oxy}ethyl)-1,2-dihydrospiro[indole-3,4'-piperidin]-2-one | Calc'd 458.2 Found 458.2 | B-4 |

Example 68

5-chloro-1'-[2-({7-oxo-8-[(cis)-3-hydroxy-3-methyl-cyclobutyl]-7,8-dihydro-1,8-naphthyridin-3-yl}oxy)ethyl]-1,2-dihydrospiro[indole-3,4'-piperidin]-2-one (Compound 323)

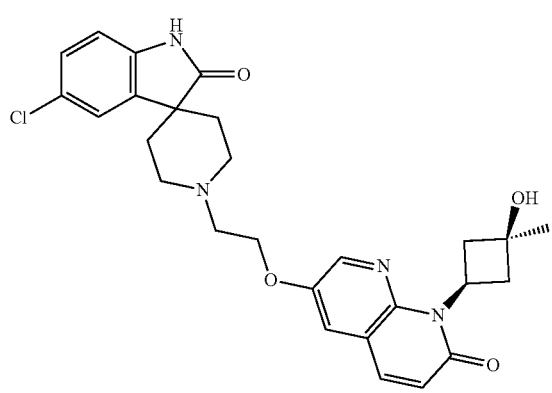 [SMILES: C[C@]1(O)C[C@@H](n2c(=O)ccc3cc(OCCN4CCC5(CC4)C(=O)Nc4ccc(Cl)cc45)cnc32)C1]

Step 1: 6-bromo-1-(3-oxocyclobutyl)-1,2-dihydro-1,8-naphthyridin-2-one

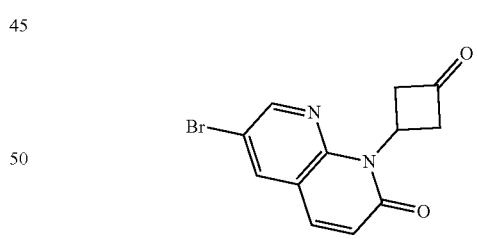

A mixture of 6-bromo-1-(3-oxocyclobutyl)-1,2-dihydro-1,8-naphthyridin-2-one (5.00 g, 22.2 mmol) and $K_2CO_3$ (4.61 g, 33.3 mmol) in DMF (50 mL) was stirred at 50° C. for 1 h under $N_2$ atmosphere. 3-Bromocyclobutanone (4.63 g, 31.1 mmol) was added to the mixture, which was stirred for an additional 13 h. After cooling to 0° C., the reaction mixture was quenched with $H_2O$ (100 mL) and extracted with EtOAc (3×60 mL). The combined organic layers were washed with brine (3×60 mL), dried over $Na_2SO_4$, filtered, and concentrated in vacuo to give 6-bromo-1-(3-oxocyclobutyl)-1,2-dihydro-1,8-naphthyridin-2-one, which was taken on to the subsequent step without further purification. MS=293.0/295.0 [M+H]+.

Step 2: 6-bromo-1-[(cis)-3-hydroxy-3-methylcyclobutyl]-1,2-dihydro-1,8-naphthyridin-2-one

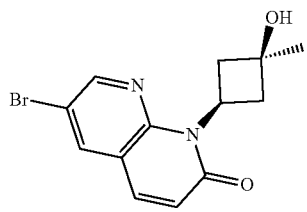 [SMILES: C[C@]1(O)C[C@@H](n2c(=O)ccc3cc(Br)cnc32)C1]

To a three-neck round-bottom flask equipped with a magnetic stir bar and thermometer was added 6-bromo-1-(3-oxocyclobutyl)-1,8-naphthyridin-2-one (6.30 g, 21.5 mmol) and THF (65 mL). The mixture was cooled to 0° C. and 3.0 M MeMgBr in 2-MeTHF (7.88 mL, 23.6 mmol) was added dropwise. After stirring at 0° C. for 2 h, the reaction mixture was quenched by the addition of saturated aqueous NH$_4$Cl solution (100 mL) and extracted with EtOAc (3×50 mL). The combined organic layers were washed with brine (2×50 mL), dried over Na$_2$SO$_4$, filtered, and concentrated in vacuo. The crude residue was purified by flash silica gel chromatography (Biotage 40 g cartridge, 0-100% EtOAc/Petroleum ether). The resulting crude product was triturated with 1:5 EtOAc/Petroleum ether to give 6-bromo-1-[(cis)-3-hydroxy-3-methylcyclobutyl]-1,2-dihydro-1,8-naphthyridin-2-one. MS=309.1/311.1 [M+H]$^+$.

Step 3: 1-[(cis)-3-hydroxy-3-methylcyclobutyl]-6-(4,4,5,5-tetramethyl-1,3,2-dioxaborolan-2-yl)-1,2-dihydro-1,8-naphthyridin-2-one

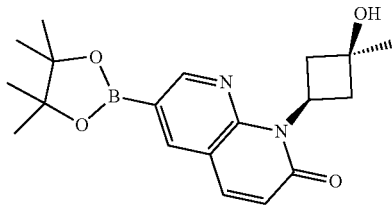

To a solution of 6-bromo-1-[(cis)-3-hydroxy-3-methylcyclobutyl]-1,2-dihydro-1,8-naphthyridin-2-one (3.48 g, 11.3 mmol) in 1,4-dioxane (40 mL) was added bis(pinacolato)diboron (4.29 g, 16.9 mmol), KOAc (2.76 g, 28.1 mmol) and Pd(dppf)Cl$_2$ (412 mg, 0.563 mmol). The mixture was degassed and purged with N$_2$ (3×), and then the mixture was stirred at 80° C. for 16 h under N$_2$ atmosphere. After cooling to room temperature, the mixture was filtered, and the filtrate was concentrated in vacuo. The crude residue was purified by flash silica gel chromatography (Biotage 40 g cartridge, 0-100% EtOAc/Petroleum ether) to give 1-[(cis)-3-hydroxy-3-methylcyclobutyl]-6-(4,4,5,5-tetramethyl-1,3,2-dioxaborolan-2-yl)-1,2-dihydro-1,8-naphthyridin-2-one.

Step 4: 6-hydroxy-1-[(cis)-3-hydroxy-3-methylcyclobutyl]-1,2-dihydro-1,8-naphthyridin-2-one To a solution of 1-[(cis)-3-hydroxy-3-methylcyclobutyl]-6-(4,4,5,5-tetramethyl-1,3,2-dioxaborolan-2-yl)-1,2-dihydro-1,8-naphthyridin-2-one (3.10 g, 8.70 mmol) in THF (15 mL) and H$_2$O (15 mL) was added Oxone (3.74 g, 6.09 mmol). The mixture was stirred at 0° C. for 2 h. The 0° C. reaction mixture was quenched by addition of saturated aqueous Na$_2$SO$_3$ (30 mL) and extracted with EtOAc (3×25 mL). The combined organic layers were washed with brine (2×50 mL), dried over Na$_2$SO$_4$, filtered, and concentrated in vacuo to give 6-hydroxy-1-[(cis)-3-hydroxy-3-methylcyclobutyl]-1,2-dihydro-1,8-naphthyridin-2-one, which was used in the subsequent step without further purification. MS=247.2 [M+H]$^+$.

Step 5: 6-(2-bromoethoxy)-1-[(cis)-3-hydroxy-3-methylcyclobutyl]-1,2-dihydro-1,8-naphthyridin-2-one

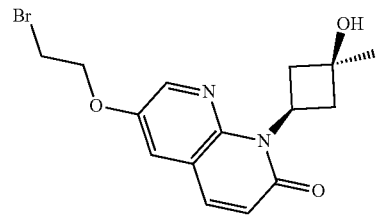 [SMILES: C[C@]1(O)C[C@@H](n2c(=O)ccc3cc(OCCBr)cnc32)C1]

To a solution of 6-hydroxy-1-[(cis)-3-hydroxy-3-methylcyclobutyl]-1,2-dihydro-1,8-naphthyridin-2-one (2.40 g, 9.75 mmol) in MeCN (25 mL) was added K$_2$CO$_3$ (5.39 g, 39.0 mmol) and 1,2-dibromoethane (29.4 mL, 390 mmol). The mixture was stirred at 65° C. for 16 h. After cooling to room temperature, the mixture was filtered, and the filtrate was concentrated in vacuo. The crude residue was purified by flash silica gel chromatography (Biotage 40 g cartridge, 0-100% EtOAc/Petroleum ether) to give 6-(2-bromoethoxy)-1-[(cis)-3-hydroxy-3-methylcyclobutyl]-1,2-dihydro-1,8-naphthyridin-2-one. MS=353.1/355.1 [M+H]$^+$.

Step 6: 5-chloro-1'-[2-({7-oxo-8-[(cis)-3-hydroxy-3-methylcyclobutyl]-7,8-dihydro-1,8-naphthyridin-3-yl}oxy)ethyl]-1,2-dihydrospiro[indole-3,4'-piperidin]-2-one (Compound 323)

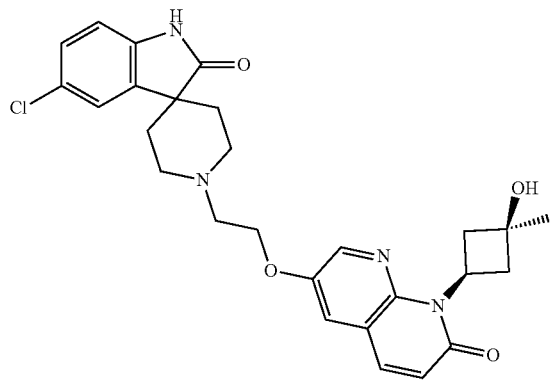 [SMILES: C[C@]1(O)C[C@@H](n2c(=O)ccc3cc(OCCN4CCC5(CC4)C(=O)Nc4ccc(Cl)cc45)cnc32)C1]

To a solution of 6-(2-bromoethoxy)-1-[(cis)-3-hydroxy-3-methylcyclobutyl]-1,2-dihydro-1,8-naphthyridin-2-one (1.00 g, 2.83 mmol) in MeCN (12 mL) was added NaHCO$_3$ (951 mg, 11.3 mmol) and 5-chloro-1H-spiro[indole-3,4'-piperidin]-2-one (Intermediate B-4, 851 mg, 3.11 mmol, HCl salt). The mixture was stirred at 80° C. for 16 h. After cooling to room temperature, the mixture was filtered, and the filter cake was triturated with H$_2$O (10 mL). The filter cake was dried in vacuo to give 5-chloro-1'-[2-({7-oxo-8-[(cis)-3-hydroxy-3-methylcyclobutyl]-7,8-dihydro-1,8-naphthyridin-3-yl}oxy)ethyl]-1,2-dihydrospiro[indole-3,4'-piperidin]-2-one (Compound 323). $^1$H NMR (400 MHz, DMSO-d$_6$): δ 10.48 (s, 1H), 8.40 (d, J=3.2 Hz, 1H), 7.88-7.82 (m, 2H), 7.49 (d, J=2.0 Hz, 1H), 7.23 (dd, J=8.4 Hz, 2.0 Hz, 1H), 6.84 (d, J=8.4 Hz, 1H), 6.64 (d, J=9.6 Hz, 1H), 5.35-5.24 (m, 1H), 4.94 (s, 1H), 4.26 (t, J=5.6 Hz, 2H), 3.00-2.88 (m, 6H), 2.74-2.65 (m, 2H), 2.43-2.36 (m, 2H), 1.82-1.67 (m, 4H), 1.33 (s, 3H). MS=509.1 [M+H]$^+$.

The following compounds in Table 38.5 were prepared according to the procedures similar to those described for Compound 323 using the appropriate starting materials.

TABLE 38.5

| No. | Structure | IUPAC Name | Exact Mass [M + H]$^+$ | Intermediate used |
|---|---|---|---|---|
| 324 | 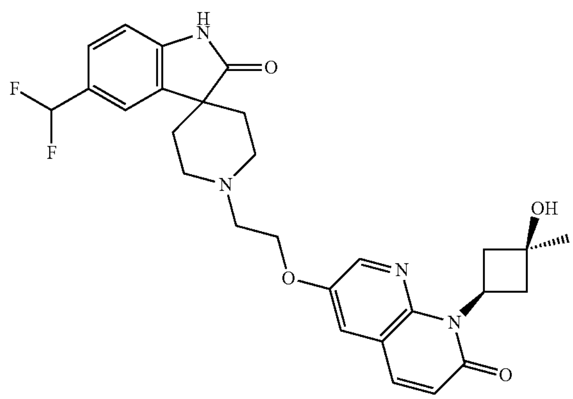 [SMILES: C[C@]1(O)C[C@@H](n2c(=O)ccc3cc(OCCN4CCC5(CC4)C(=O)Nc4ccc(C(F)F)cc45)cnc32)C1] | 5-(difluoromethyl)-1'-[2-({7-oxo-8-[(cis)-3-hydroxy-3-methylcyclobutyl]-7,8-dihydro-1,8-naphthyridin-3-yl}oxy)ethyl]-1,2-dihydrospiro[indole-3,4'-piperidin]-2-one | Calc'd 525.2 Found 525.2 | B-1 |
| 325 | 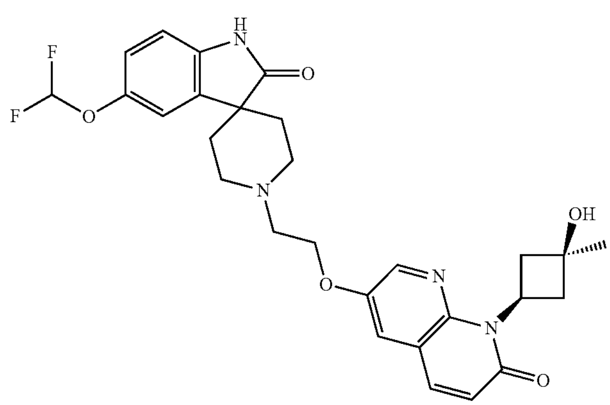 [SMILES: C[C@]1(O)C[C@@H](n2c(=O)ccc3cc(OCCN4CCC5(CC4)C(=O)Nc4ccc(OC(F)F)cc45)cnc32)C1] | 5-(difluoromethoxy)-1'-[2-({7-oxo-8-[(cis)-3-hydroxy-3-methylcyclobutyl]-7,8-dihydro-1,8-naphthyridin-3-yl}oxy)ethyl]-1,2-dihydrospiro[indole-3,4'-piperidin]-2-one | Calc'd 541.2 Found 541.3 | B-2 |

1169

Example 69

5-chloro-1'-[2-({7-oxo-8-[(cis)-3-ethyl-3-hydroxycyclobutyl]-5,6,7,8-tetrahydro-1,8-naphthyridin-3-yl}oxy)ethyl]-1,2-dihydrospiro[indole-3,4'-piperidin]-2-one (Compound 321), 5-chloro-1'-[2-({7-oxo-8-[(3-ethyl-3-hydroxycyclobutyl]-5,6,7,8-tetrahydro-1,8-naphthyridin-3-yl}oxy)ethyl]-1,2-dihydrospiro[indole-3,4'-piperidin]-2-one (Compound 318), and 5-chloro-1'-[2-({7-oxo-8-[(trans)-3-ethyl-3-hydroxycyclobutyl]-5,6,7,8-tetrahydro-1,8-naphthyridin-3-yl}oxy)ethyl]-1,2-dihydrospiro[indole-3,4'-piperidin]-2-one (Compound 290)

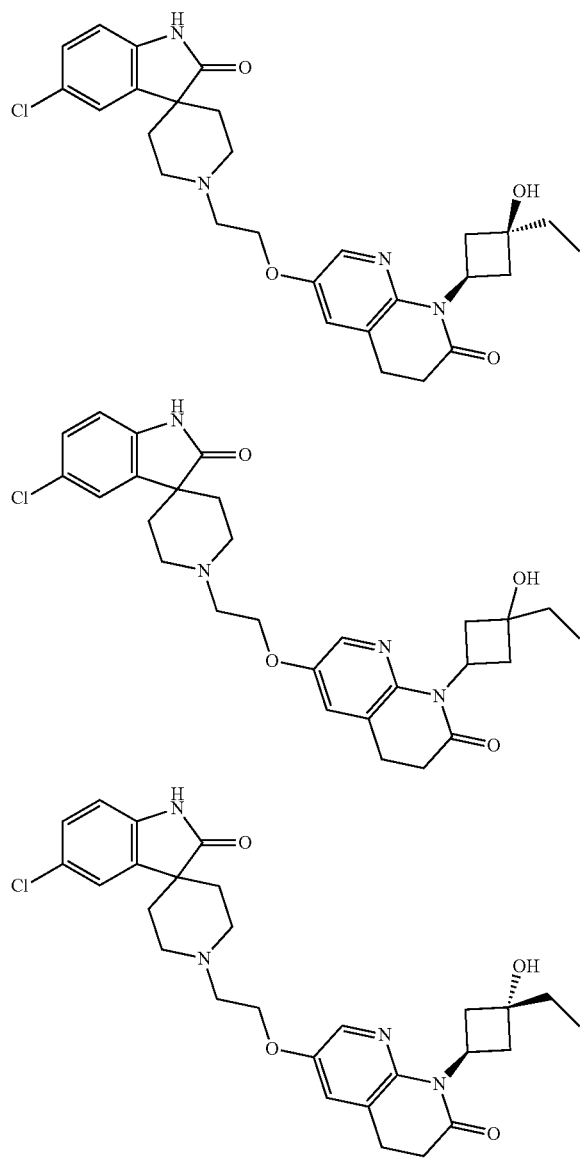

1170

Step 1: 6-bromo-1-(3-ethyl-3-hydroxycyclobutyl)-1,2,3,4-tetrahydro-1,8-naphthyridin-2-one

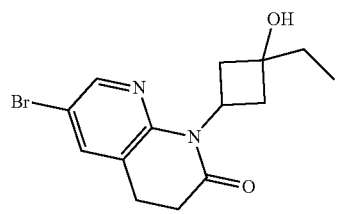 [SMILES: CCC1(O)CC(N2C(=O)CCc3cc(Br)cnc32)C1]

To a 0° C. solution of 6-bromo-1-(3-oxocyclobutyl)-1,2,3,4-tetrahydro-1,8-naphthyridin-2-one (Procedure for Intermediate A-79, Step 1, 5.00 g, 16.9 mmol) in THF (100 mL) under $N_2$ atmosphere was added 3.0 M EtMgBr in 2-MeTHF (8.47 mL, 25.4 mmol). The mixture was stirred at room temperature for 1 h. The reaction mixture was quenched with saturated aqueous $NH_4Cl$ solution (80 mL) and extracted with EtOAc (3×50 mL). The combined organic layers were washed with brine (50 mL), dried over $Na_2SO_4$, filtered, and concentrated in vacuo. The crude residue was purified by flash silica gel chromatography (Biotage 12 g cartridge, 0-80% EtOAc/Petroleum ether) to give 6-bromo-1-(3-ethyl-3-hydroxycyclobutyl)-1,2,3,4-tetrahydro-1,8-naphthyridin-2-one. MS=325.1/327.1 $[M+H]^+$.

Step 2: 1-(3-ethyl-3-hydroxycyclobutyl)-6-(4,4,5,5-tetramethyl-1,3,2-dioxaborolan-2-yl)-1,2,3,4-tetrahydro-1,8-naphthyridin-2-one

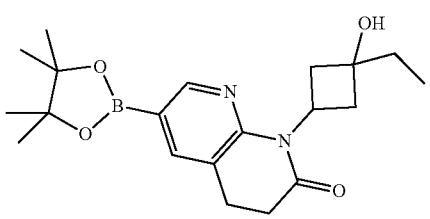 [SMILES: CCC1(O)CC(N2C(=O)CCc3cc(B4OC(C)(C)C(C)(C)O4)cnc32)C1]

To a solution of 6-bromo-1-(3-ethyl-3-hydroxycyclobutyl)-1,2,3,4-tetrahydro-1,8-naphthyridin-2-one (1.40 g, 4.31 mmol) and bis(pinacolato)diboron (1.20 g, 4.74 mmol) in 1,4-dioxane (30 mL) was added KOAc (1.27 g, 12.9 mmol) and Pd(dppf)Cl$_2$ (352 mg, 0.431 mmol). The mixture was purged with $N_2$ (3×), and then the mixture was stirred at 80° C. for 16 h under $N_2$ atmosphere. After cooling to room temperature, the reaction mixture was filtered, and the filtrate was concentrated in vacuo to give 1-(3-ethyl-3-hydroxycyclobutyl)-6-(4,4,5,5-tetramethyl-1,3,2-dioxaborolan-2-yl)-1,2,3,4-tetrahydro-1,8-naphthyridin-2-one, which was used in the subsequent step without further purification. MS=373.2 $[M+H]^+$.

Step 3: 1-(3-ethyl-3-hydroxycyclobutyl)-6-hydroxy-1,2,3,4-tetrahydro-1,8-naphthyridin-2-one

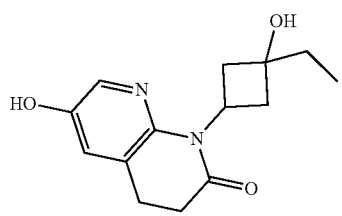 [SMILES: CCC1(O)CC(N2C(=O)CCc3cc(O)cnc32)C1]

To a 0° C. solution of 1-(3-ethyl-3-hydroxycyclobutyl)-6-(4,4,5,5-tetramethyl-1,3,2-dioxaborolan-2-yl)-1,2,3,4-tetrahydro-1,8-naphthyridin-2-one (1.60 g, 4.30 mmol) in acetone (40 mL) and H$_2$O (5 mL) was added Oxone (2.91 g, 4.73 mmol), and then the mixture was stirred at room temperature for 1 h. The reaction mixture was filtered, and the filtrate was diluted with H$_2$O (40 mL) and extracted with EtOAc (4×20 mL). The combined organic layers were washed with brine (20 mL), dried over Na$_2$SO$_4$, filtered, and concentrated in vacuo. The crude residue was purified by flash silica gel chromatography (Isco 12 g cartridge, 0-100% EtOAc/Petroleum ether) to give 1-(3-ethyl-3-hydroxycyclobutyl)-6-hydroxy-1,2,3,4-tetrahydro-1,8-naphthyridin-2-one. MS=263.2 [M+H]$^+$.

Step 4: 6-(2-bromoethoxy)-1-(3-ethyl-3-hydroxycyclobutyl)-1,2,3,4-tetrahydro-1,8-naphthyridin-2-one

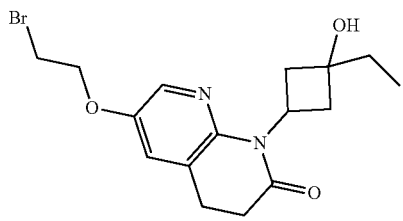 [SMILES: CCC1(O)CC(N2C(=O)CCc3cc(OCCBr)cnc32)C1]

To a solution of 1-(3-ethyl-3-hydroxycyclobutyl)-6-hydroxy-1,2,3,4-tetrahydro-1,8-naphthyridin-2-one (400 mg, 1.52 mmol) in MeCN (0.5 mL) and 1,2-dibromoethane (4.60 mL, 61.0 mmol) was added K$_2$CO$_3$ (422 mg, 3.05 mmol). The mixture was then stirred at 80° C. for 16 h. After cooling to room temperature, the reaction mixture was filtered, and the filtrate was concentrated in vacuo. The crude residue was purified by flash silica gel chromatography (Biotage 8 g cartridge, 0-100% EtOAc/Petroleum ether) to give 6-(2-bromoethoxy)-1-(3-ethyl-3-hydroxycyclobutyl)-1,2,3,4-tetrahydro-1,8-naphthyridin-2-one. MS=369.1/371.1 [M+H]$^+$.

Step 5: 5-chloro-1'-[2-({7-oxo-8-[(cis)-3-ethyl-3-hydroxycyclobutyl]-5,6,7,8-tetrahydro-1,8-naphthyridin-3-yl}oxy)ethyl]-1,2-dihydrospiro[indole-3,4'-piperidin]-2-one (Compound 321) and 5-chloro-1'-[2-({7-oxo-8-[(3-ethyl-3-hydroxycyclobutyl]-5,6,7,8-tetrahydro-1,8-naphthyridin-3-yl}oxy)ethyl]-1,2-dihydrospiro[indole-3,4'-piperidin]-2-one (Compound 318)

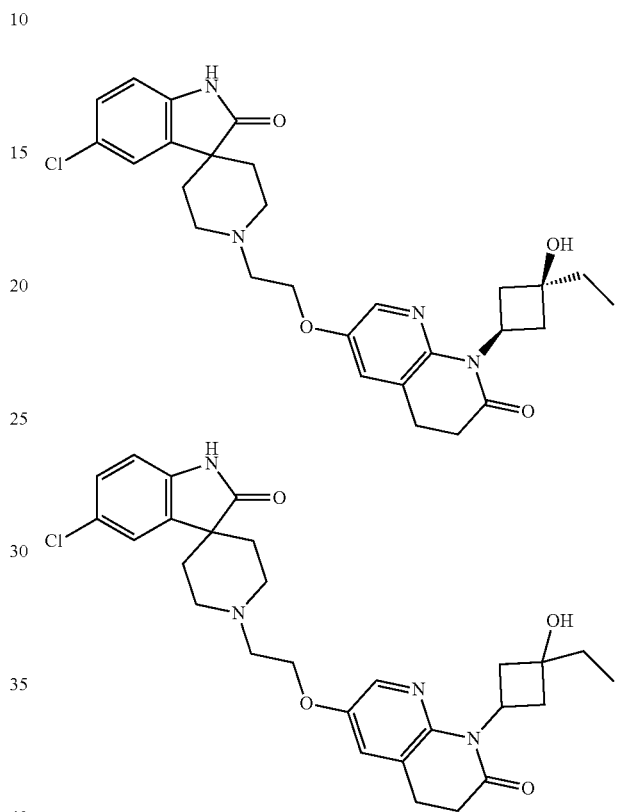

To a solution of 6-(2-bromoethoxy)-1-(3-ethyl-3-hydroxycyclobutyl)-1,2,3,4-tetrahydro-1,8-naphthyridin-2-one (250 mg, 0.677 mmol) and 5-chloro-1H-spiro[indole-3,4'-piperidin]-2-one (Intermediate B-4, 203 mg, 0.745 mmol, HCl salt) in MeCN (5 mL) was added NaHCO$_3$ (228 mg, 2.71 mmol). The mixture was stirred at 80° C. for 16 h. After cooling to room temperature, the reaction mixture was filtered, and the filtrate was concentrated in vacuo. The crude residue was purified by reverse phase preparative HPLC (Waters Xbridge OBD C$_{18}$ column, 25-55% MeCN: 10 mM NH$_4$HCO$_3$ in H$_2$O). Baseline separation of the major (cis) and minor (trans) products was not obtained. The first eluting fractions of product provided 5-chloro-1'-[2-({7-oxo-8-[(cis)-3-ethyl-3-hydroxycyclobutyl]-5,6,7,8-tetrahydro-1,8-naphthyridin-3-yl}oxy)ethyl]-1,2-dihydrospiro[indole-3,4'-piperidin]-2-one (Compound 321): $^1$H NMR (400 MHz, DMSO-d$_6$): δ 10.48 (s, 1H), 7.94 (t, J=2.8 Hz, 1H), 7.50 (d, J=2.0 Hz, 1H), 7.40 (d, J=2.8 Hz, 1H), 7.25-7.22 (m, 1H), 6.84 (d, J=8.0 Hz, 1H), 4.66 (s, 1H), 4.22-4.16 (m, 3H), 2.92-2.78 (m, 6H), 2.69-2.65 (m, 2H), 2.50-2.49 (m, 4H), 2.27-2.26 (m, 2H), 1.78-1.72 (m, 4H), 1.51-1.49 (m, 2H), 0.87 (t, J=7.2 Hz, 3H). MS=525.2 [M+H]$^+$. Remaining fractions were a mixture of cis and trans products, providing 5-chloro-1'-[2-({7-oxo-8-[(3-ethyl-3-hydroxycyclobutyl]-5,6,7,8-tetrahydro-1,8-naphthyridin-3-yl}oxy)ethyl]-1,2-dihydrospiro[indole-3,4'-piperidin]-2-one (Compound 318): $^1$H NMR (400 MHz, DMSO-d$_6$): δ 10.48 (s, 1H), 7.95-7.94 (m, 1H), 7.51 (s, 1H), 7.50-7.38 (m, 1H), 7.25-7.22 (m, 1H), 6.84 (d, J=8.4 Hz, 1H), 5.39-5.28 (m, 0.3H), 4.67-4.61 (m, 1H), 4.24-4.16 (m, 2.6H), 2.92-2.78 (m, 6H), 2.69-2.54 (m, 6H), 2.27-2.12 (m, 2H), 1.78-1.72 (m, 4H), 1.51-1.49 (m, 2H), 0.88-0.81 (m, 3H). MS=525.2 [M+H]$^+$.

Step 6: 5-chloro-1'-[2-({7-oxo-8-[(cis)-3-ethyl-3-hydroxycyclobutyl]-5,6,7,8-tetrahydro-1,8-naphthyridin-3-yl}oxy)ethyl]-1,2-dihydrospiro[indole-3,4'-piperidin]-2-one (Compound 321) and 5-chloro-1'-[2-({7-oxo-8-[(trans)-3-ethyl-3-hydroxycyclobutyl]-5,6,7,8-tetrahydro-1,8-naphthyridin-3-yl}oxy)ethyl]-1,2-dihydrospiro[indole-3,4'-piperidin]-2-one (Compound 290)

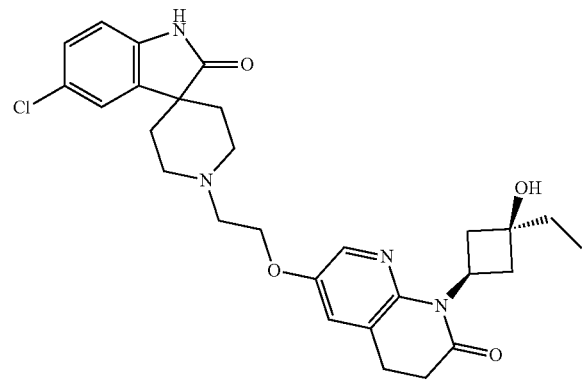

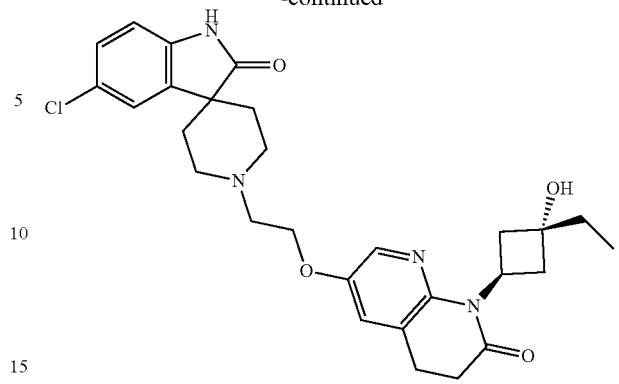

5-chloro-1'-[2-({7-oxo-8-[(3-ethyl-3-hydroxycyclobutyl]-5,6,7,8-tetrahydro-1,8-naphthyridin-3-yl}oxy)ethyl]-1,2-dihydrospiro[indole-3,4'-piperidin]-2-one (Compound 318, 220 mg, 0.419 mmol) was separated by preparative chiral SFC (Daicel Chiralpak AD-3 column, 60% IPA with 0.1% NH$_4$OH in CO$_2$). The first eluting diastereomer of the title compound, 5-chloro-1'-[2-({7-oxo-8-[(cis)-3-ethyl-3-hydroxycyclobutyl]-5,6,7,8-tetrahydro-1,8-naphthyridin-3-yl}oxy)ethyl]-1,2-dihydrospiro[indole-3,4'-piperidin]-2-one (Compound 321). The second eluting diastereomer of the title compound, 5-chloro-1'-[2-({7-oxo-8-[(trans)-3-ethyl-3-hydroxycyclobutyl]-5,6,7,8-tetrahydro-1,8-naphthyridin-3-yl}oxy)ethyl]-1,2-dihydrospiro[indole-3,4'-piperidin]-2-one (Compound 290): $^1$H NMR (400 MHz, DMSO-d$_6$): δ 10.48 (s, 1H), 7.95 (d, J=2.8 Hz, 1H), 7.50 (s, 1H), 7.38 (d, J=2.4 Hz, 1H), 7.25-7.22 (m, 1H), 6.84 (d, J=8.0 Hz, 1H), 5.37-5.28 (m, 1H), 4.61 (s, 1H), 4.18 (t, J=5.2 Hz, 2H), 2.92-2.78 (m, 6H), 2.69-2.62 (m, 6H), 2.13-2.12 (m, 2H), 1.76-1.72 (m, 4H), 1.56-1.55 (m, 2H), 0.81 (t, J=7.2 Hz, 3H). MS=525.2 [M+H]$^+$.

The following compounds in Table 38.6 were prepared according to the procedures similar to those described for Compounds 290, 318, & 321 using the appropriate starting materials.

TABLE 38.6

| No. | Structure | IUPAC Name | Exact Mass [M + H]$^+$ | Comments | Elution Order | Chiral Column |
|---|---|---|---|---|---|---|
| 317 | 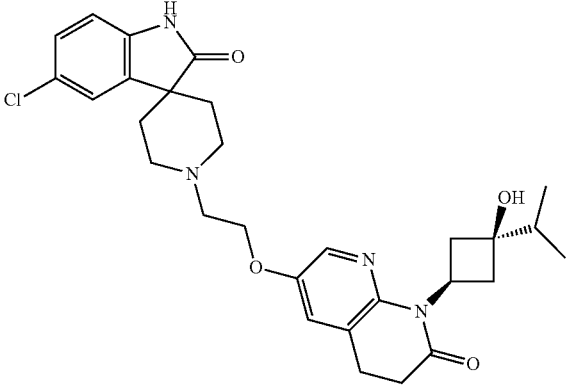 [SMILES: CC(C)[C@]1(O)C[C@@H](N2C(=O)CCc3cc(OCCN4CCC5(CC4)C(=O)Nc4ccc(Cl)cc45)cnc32)C1] | 5-chloro-1'-[2-({7-oxo-8-[(cis)-3-hydroxy-3-(propan-2-yl)cyclobutyl]-5,6,7,8-tetrahydro-1,8-naphthyridin-3-yl}oxy)ethyl]-1,2-dihydrospiro[indole-3,4'-piperidin]-2-one | Calc'd 539.2 Found 539.3 | Route only provided cis isomer | n/a | n/a |

TABLE 38.6-continued

| No. | Structure | IUPAC Name | Exact Mass [M + H]+ | Comments | Elution Order | Chiral Column |
|---|---|---|---|---|---|---|
| 299 | 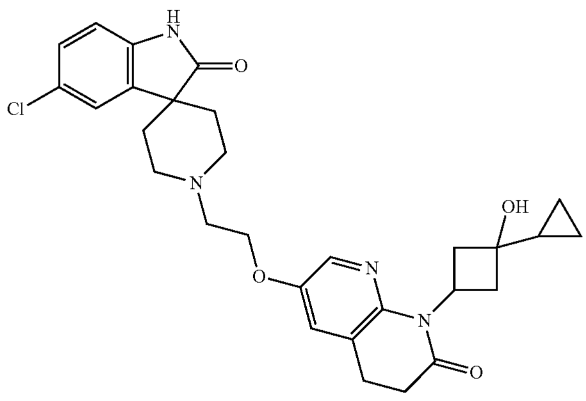 [SMILES: O=C1CCc2cc(OCCN3CCC4(CC3)C(=O)Nc3ccc(Cl)cc34)cnc2N1C1CC(O)(C2CC2)C1] | 5-chloro-1'-(2-{[8-(3-cyclopropyl-3-hydroxycyclobutyl)-7-oxo-5,6,7,8-tetrahydro-1,8-naphthyridin-3-yl]oxy}ethyl)-1,2-dihydrospiro[indole-3,4'-piperidin]-2-one | Calc'd 537.2 Found 537.4 | Step 5 provided a mixture of isomers | n/a | n/a |
| 398 | 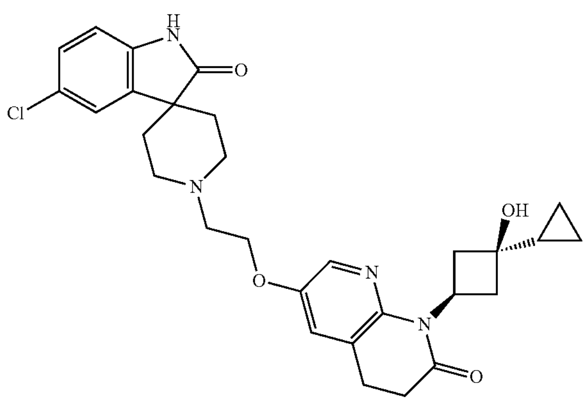 [SMILES: O=C1CCc2cc(OCCN3CCC4(CC3)C(=O)Nc3ccc(Cl)cc34)cnc2N1[C@H]1C[C@](O)(C2CC2)C1] | 5-chloro-1'-[2-({7-oxo-8-[(cis)-3-cyclopropyl-3-hydroxycyclobutyl]-5,6,7,8-tetrahydro-1,8-naphthyridin-3-yl}oxy)ethyl]-1,2-dihydrospiro[indole-3,4'-piperidin]-2-one | Calc'd 537.2 Found 537.3 | n/a | 2nd | Daicel Chiralpak IF |
| 297 | 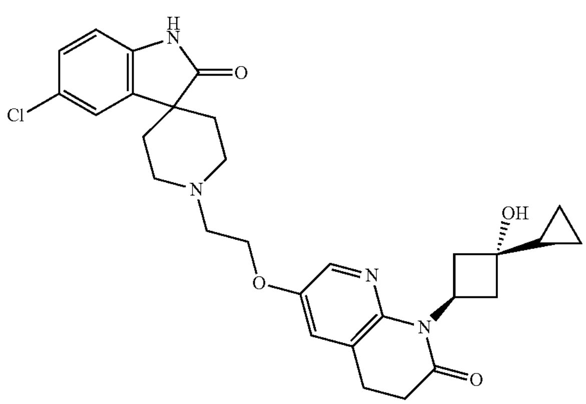 [SMILES: O=C1CCc2cc(OCCN3CCC4(CC3)C(=O)Nc3ccc(Cl)cc34)cnc2N1[C@H]1C[C@@](O)(C2CC2)C1] | 5-chloro-1'-[2-({7-oxo-8-[(trans)-3-cyclopropyl-3-hydroxycyclobutyl]-5,6,7,8-tetrahydro-1,8-naphthyridin-3-yl}oxy)ethyl]-1,2-dihydrospiro[indole-3,4'-piperidin]-2-one | Calc'd 537.2 Found 537.1 | n/a | 1st | Daicel Chiralpak IF |

Example 70

5-chloro-1'-[2-({8-[3-(hydroxymethyl)cyclobutyl]-7-oxo-5,6,7,8-tetrahydro-1,8-naphthyridin-3-yl}oxy)ethyl]-1,2-dihydrospiro[indole-3,4'-piperidin]-2-one and (Compound 326)

5-chloro-1'-[2-({7-oxo-8-[(cis)-3-(hydroxymethyl)cyclobutyl]-5,6,7,8-tetrahydro-1,8-naphthyridin-3-yl}oxy)ethyl]-1,2-dihydrospiro[indole-3,4'-piperidin]-2-one (Compound 319)

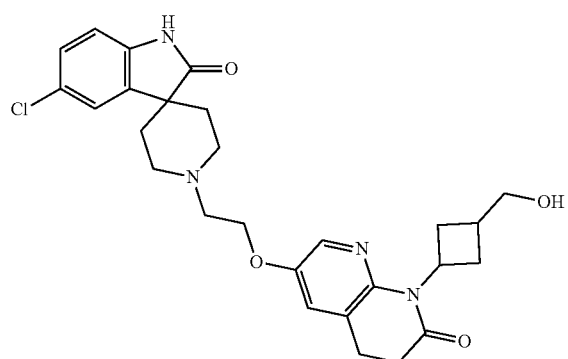

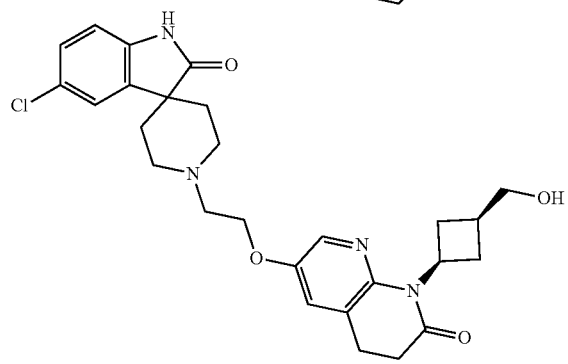

Step 1: (3-bromocyclobutyl)methanol

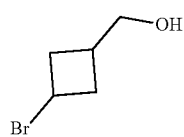

To a 0° C. solution of methyl 3-bromocyclobutane-1-carboxylate (5.00 g, 25.9 mmol) in THF (50 mL) under $N_2$ atmosphere was added 4.0 M $LiBH_4$ in THF (9.71 mL, 38.8 mmol). The mixture was stirred at room temperature for 2 h. The mixture was diluted with saturated aqueous $NH_4Cl$ (150 mL) and extracted with EtOAc (3×100 mL), dried over $Na_2SO_4$, filtered and concentrated in vacuo. The crude residue was purified by flash silica gel chromatography (Biotage 20 g cartridge, 0-100% EtOAc/Petroleum ether) to give (3-bromocyclobutyl)methanol. $^1H$ NMR (400 MHz, $CDCl_3$, 8/9 H): δ 4.60-4.52 (m, 1H) 3.66 (d, J=6.4 Hz, 2H) 2.79-2.76 (m, 1H) 2.61-2.53 (m, 4H)

Step 2: 6-bromo-1-[3-(hydroxymethyl)cyclobutyl]-1,2,3,4-tetrahydro-1,8-naphthyridin-2-one

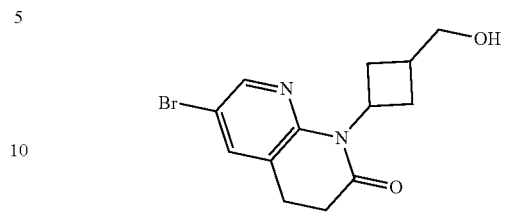

To a solution of 6-bromo-1,2,3,4-tetrahydro-1,8-naphthyridin-2-one (2.00 g, 8.81 mmol) in DMF (25 mL) was added $Cs_2CO_3$ (5.74 g, 17.6 mmol), NaI (2.64 g, 17.6 mmol) and (3-bromocyclobutyl)methanol (2.91 g, 17.6 mmol). The mixture was stirred at 130° C. for 16 h. After cooling to room temperature, the residue was diluted with $H_2O$ (50 mL), extracted with EtOAc (3×30 mL), dried over $Na_2SO_4$, filtered, and concentrated in vacuo. The crude residue was purified by flash silica gel chromatography (Biotage 20 g cartridge, 0-100% EtOAc/Petroleum ether) to give 6-bromo-1-[3-(hydroxymethyl)cyclobutyl]-1,2,3,4-tetrahydro-1,8-naphthyridin-2-one. MS=311.0/313.0 $[M+H]^+$.

Step 3: 1-[3-(hydroxymethyl)cyclobutyl]-6-(4,4,5,5-tetramethyl-1,3,2-dioxaborolan-2-yl)-1,2,3,4-tetrahydro-1,8-naphthyridin-2-one

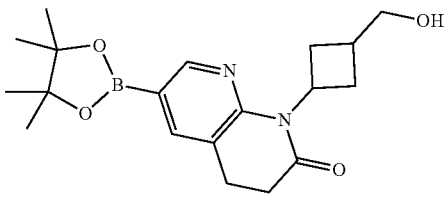

A mixture of 6-bromo-1-[3-(hydroxymethyl)cyclobutyl]-1,2,3,4-tetrahydro-1,8-naphthyridin-2-one (900 mg, 2.89 mmol), KOAc (568 mg, 5.78 mmol), bis(pinacolato)diboron (808 mg, 3.18 mmol) and $Pd(dppf)Cl_2$ (236 mg, 0.289 mmol) in 1,4-dioxane (10 mL) was degassed and purged with $N_2$ (3×), and then stirred at 100° C. for 16 h under $N_2$ atmosphere. After cooling to room temperature, the reaction mixture was filtered and concentrated under in vacuo to give 1-[3-(hydroxymethyl)cyclobutyl]-6-(4,4,5,5-tetramethyl-1,3,2-dioxaborolan-2-yl)-1,2,3,4-tetrahydro-1,8-naphthyridin-2-one, which was taken onto the subsequent step without further purification. MS=359.3 $[M+H]^+$.

Step 4: 6-hydroxy-1-[3-(hydroxymethyl)cyclobutyl]-1,2,3,4-tetrahydro-1,8-naphthyridin-2-one

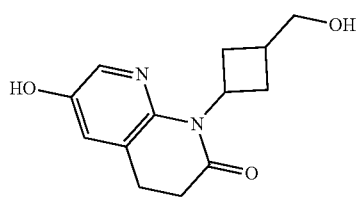 [SMILES: O=C1CCc2cc(Br)cnc2N1C1CC(CO)C1]

To a 0° C. solution of 1-[3-(hydroxymethyl)cyclobutyl]-6-(4,4,5,5-tetramethyl-1,3,2-dioxaborolan-2-yl)-1,2,3,4-tetrahydro-1,8-naphthyridin-2-one (800 mg, 1.67 mmol, 75% purity) in THF (10 mL) and H₂O (3 mL) was added Oxone (2.06 g, 3.35 mmol). The mixture was stirred at room temperature for 1 h. The reaction was quenched with saturated aqueous Na₂SO₃ solution (10 mL) and extracted with EtOAc (3×10 mL), dried over Na₂SO₄, filtered, and concentrated in vacuo. The crude residue was purified by flash silica gel chromatography (Biotage 12 g cartridge, 0-100% EtOAc/Petroleum ether) to give 6-hydroxy-1-[3-(hydroxymethyl)cyclobutyl]-1,2,3,4-tetrahydro-1,8-naphthyridin-2-one. MS=249.0 [M+H]⁺.

Step 5: 6-(2-bromoethoxy)-1-[3-(hydroxymethyl)cyclobutyl]-1,2,3,4-tetrahydro-1,8-naphthyridin-2-one

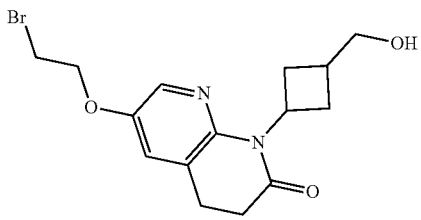 [SMILES: O=C1CCc2cc(OCCBr)cnc2N1C1CC(CO)C1]

To a solution of 6-hydroxy-1-[3-(hydroxymethyl)cyclobutyl]-1,2,3,4-tetrahydro-1,8-naphthyridin-2-one (300 mg, 1.21 mmol) in MeCN (2 mL) was added K₂CO₃ (334 mg, 2.42 mmol) and 1,2-dibromoethane (2.73 mL, 36.3 mmol). The mixture was stirred at 80° C. for 4 h. After cooling to room temperature, the reaction mixture was concentrated in vacuo to remove MeCN. The residue was diluted with H₂O (10 mL) and extracted with EtOAc (3×10 mL), dried over Na₂SO₄, filtered, and concentrated in vacuo. The crude residue was purified by flash silica gel chromatography (Biotage 4 g cartridge, 0-100% EtOAc/Petroleum ether) to give 6-(2-bromoethoxy)-1-[3-(hydroxymethyl)cyclobutyl]-1,2,3,4-tetrahydro-1,8-naphthyridin-2-one. MS=354.9/356.9 [M+H]⁺.

Step 6: 5-chloro-1'-[2-({8-[3-(hydroxymethyl)cyclobutyl]-7-oxo-5,6,7,8-tetrahydro-1,8-naphthyridin-3-yl}oxy)ethyl]-1,2-dihydrospiro[indole-3,4'-piperidin]-2-one and (Compound 326)

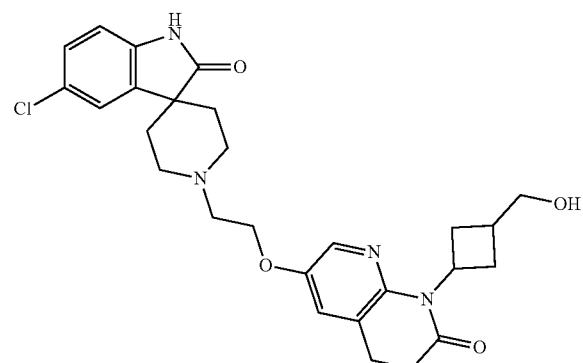

To a solution of 6-(2-bromoethoxy)-1-[3-(hydroxymethyl)cyclobutyl]-1,2,3,4-tetrahydro-1,8-naphthyridin-2-one (140 mg, 0.394 mmol) in MeCN (3 mL) was added NaHCO₃ (66.2 mg, 0.788 mmol) and 5-chloro-1H-spiro[indole-3,4'-piperidin]-2-one (Intermediate B-4, 129 mg, 0.473 mmol, HCl salt). The mixture was stirred at 80° C. for 4 h. After cooling to room temperature, the reaction mixture was filtered and concentrated in vacuo. The crude residue was purified by reverse phase preparative HPLC (Phenomenex C₁₈ column, 25-45% MeCN with H₂O with 10 mM NH₄HCO₃ modifier) to give 5-chloro-1'-[2-({8-[3-(hydroxymethyl)cyclobutyl]-7-oxo-5,6,7,8-tetrahydro-1,8-naphthyridin-3-yl}oxy)ethyl]-1,2-dihydrospiro[indole-3,4'-piperidin]-2-one and (Compound 326). ¹H NMR (400 MHz, DMSO-d₆): δ 10.49 (s, 1H), 7.99-7.90 (m, 1H), 7.50 (d, J=2.0 Hz, 1H), 7.38 (d, J=2.8 Hz, 1H), 7.23 (d, J=8.4 Hz, 1H), 6.84 (d, J=8.4 Hz, 1H), 4.82 (t, J=8.8 Hz, 1H), 4.55-4.28 (m, 1H), 4.18 (t, J=5.6 Hz, 2H), 3.41 (d, J=6.3 Hz, 2H), 2.92 (t, J=11.2 Hz, 2H), 2.86 (t, J=5.6 Hz, 2H), 2.80 (t, J=7.2 Hz, 2H), 2.73-2.67 (m, 2H), 2.48 (s, 2H), 2.36-2.24 (m, 4H), 2.15-2.02 (m, 1H), 1.83-1.67 (m, 4H). MS=511.1 [M+H]⁺.

Step 7: 5-chloro-1'-[2-({7-oxo-8-[(cis)-3-(hydroxymethyl)cyclobutyl]-5,6,7,8-tetrahydro-1,8-naphthyridin-3-yl}oxy)ethyl]-1,2-dihydrospiro[indole-3,4'-piperidin]-2-one (Compound 327)

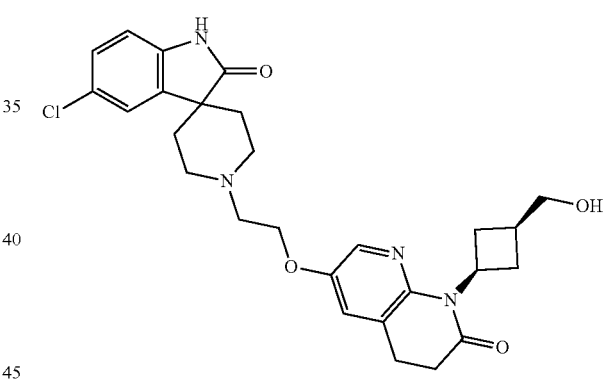

5-chloro-1'-[2-({8-[3-(hydroxymethyl)cyclobutyl]-7-oxo-5,6,7,8-tetrahydro-1,8-naphthyridin-3-yl}oxy)ethyl]-1,2-dihydrospiro[indole-3,4'-piperidin]-2-one was separated by preparative chiral SFC (Daicel Chiralcel OX column, 6000 MeOH with 0.1% NH₄OH in CO₂) to remove trace trans impurity. The first eluting diastereomer of the title compound, 5-chloro-1'-[2-({7-oxo-8-[(cis)-3-(hydroxymethyl)cyclobutyl]-5,6,7,8-tetrahydro-1,8-naphthyridin-3-yl}oxy)ethyl]-1,2-dihydrospiro[indole-3,4'-piperidin]-2-one (Compound 319): ¹H NMR (400 MHz, DMSO-d₆): δ 10.48 (s, 1H), 7.94 (d, J=2.8 Hz, 1H), 7.50 (s, 1H), 7.38 (d, J=2.4 Hz, 1H), 7.24 (d, J=8.4 Hz, 1H), 6.84 (d, J=8.4 Hz, 1H), 4.83 (t, J=8.8 Hz, 1H), 4.40 (t, J=5.2 Hz, 1H), 4.18 (t, J=5.6 Hz, 2H), 3.41 (t, J=5.6 Hz, 2H), 2.92 (t, J=7.2 Hz, 3H), 2.87-2.77 (m, 4H), 2.74-2.63 (m, 3H), 2.37-2.23 (m, 4H), 2.15-2.04 (m, 1H), 1.86-1.64 (in, 4H). MS=511.2 [M+H]⁺.

The following compounds in Table 38.7 were prepared according to the procedures similar to those described for Compounds 326 & 319 using the appropriate starting materials.

TABLE 38.7

| No. | Structure | IUPAC Name | Exact Mass [M + H]+ | Intermediate Used | Elution Order | Chiral Column |
|---|---|---|---|---|---|---|
| 316 | 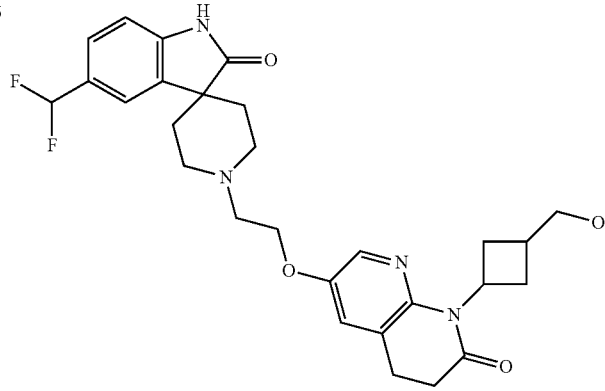 | 5-(difluoromethyl)-1'-[2-({8-[3-(hydroxymethyl)cyclobutyl]-7-oxo-5,6,7,8-tetrahydro-1,8-naphthyridin-3-yl}oxy)ethyl]-1,2-dihydrospiro[indole-3,4'-piperidin]-2-one | Calc'd 527.2 Found 527.2 | B-1 | n/a | n/a |
| 309 | 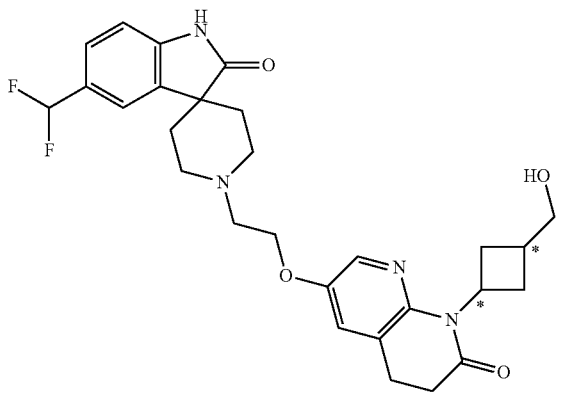 [SMILES: O=C1CCc2cc(OCCN3CCC4(CC3)C(=O)Nc3ccc(C(F)F)cc34)cnc2N1C1CC(CO)C1] | 5-(difluoromethyl)-1'-[2-({7-oxo-8-[(cis) or (trans)-3-(hydroxymethyl)cyclobutyl]-5,6,7,8-tetrahydro-1,8-naphthyridin-3-yl}oxy)ethyl]-1,2-dihydrospiro[indole-3,4'-piperidin]-2-one | Calc'd 527.2 Found 527.3 | B-1 | 1st | Daicel Chiralpak IG |
| 310 | 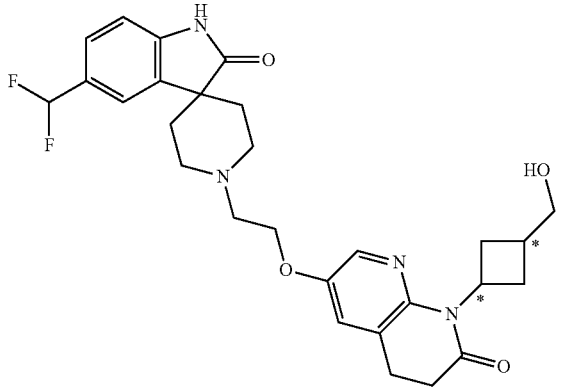 [SMILES: O=C1CCc2cc(OCCN3CCC4(CC3)C(=O)Nc3ccc(C(F)F)cc34)cnc2N1C1CC(CO)C1] | 5-(difluoromethyl)-1'-[2-({7-oxo-8-[(trans) or (cis)-3-(hydroxymethyl)cyclobutyl]-5,6,7,8-tetrahydro-1,8-naphthyridin-3-yl}oxy)ethyl]-1,2-dihydrospiro[indole-3,4'-piperidin]-2-one | Calc'd 527.2 Found 527.3 | B-1 | 2nd | Daicel Chiralpak IG |

TABLE 38.7-continued

| No. | Structure | IUPAC Name | Exact Mass [M + H]⁺ | Intermediate Used | Elution Order | Chiral Column |
|---|---|---|---|---|---|---|
| 327 | 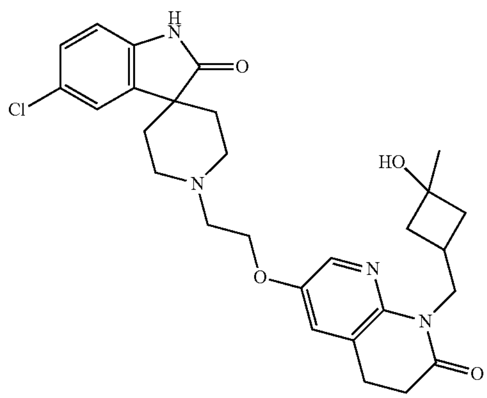 [SMILES: CC1(O)CC(CN2C(=O)CCc3cc(OCCN4CCC5(CC4)C(=O)Nc4ccc(Cl)cc45)cnc32)C1] | 5-chloro-1'-[2-({8-[(3-hydroxy-3-methylcyclobutyl)methyl]-7-oxo-5,6,7,8-tetrahydro-1,8-naphthyridin-3-yl}oxy)ethyl]-1,2-dihydrospiro[indole-3,4'-piperidin]-2-one | Calc'd 525.2 Found 525.1 | B-4 & D-1 | n/a | n/a |
| 313 | 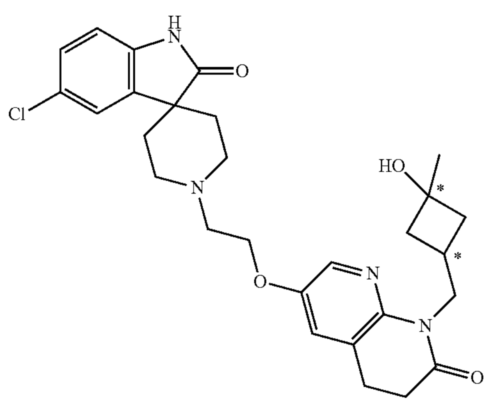 [SMILES: CC1(O)CC(CN2C(=O)CCc3cc(OCCN4CCC5(CC4)C(=O)Nc4ccc(Cl)cc45)cnc32)C1] | 5-chloro-1'-{2-[(7-oxo-8-{[(cis) or (trans)-3-hydroxy-3-methylcyclobutyl]methyl}-5,6,7,8-tetrahydro-1,8-naphthyridin-3-yl)oxy]ethyl}-1,2-dihydrospiro[indole-3,4'-piperidin]-2-one | Calc'd 525.2 Found 525.3 | B-4 & D-1 | 1st | Chiralpak IE-3 |
| 322 | 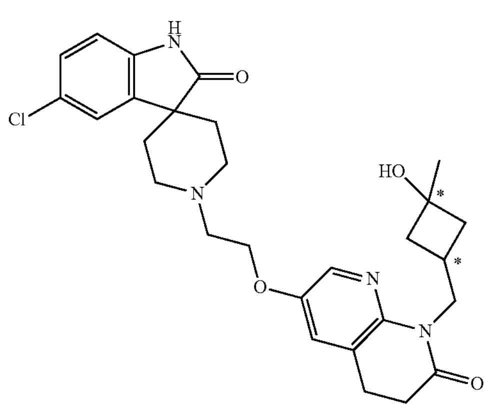 [SMILES: CC1(O)CC(CN2C(=O)CCc3cc(OCCN4CCC5(CC4)C(=O)Nc4ccc(Cl)cc45)cnc32)C1] | 5-chloro-1'-{2-[(7-oxo-8-{[(trans) or (cis)-3-hydroxy-3-methylcyclobutyl]methyl}-5,6,7,8-tetrahydro-1,8-naphthyridin-3-yl)oxy]ethyl}-1,2-dihydrospiro[indole-3,4'-piperidin]-2-one | Calc'd 525.2 Found 525.3 | B-4 & D-1 | 2nd | Chiralpak IE-3 |

TABLE 38.7-continued

| No. | Structure | IUPAC Name | Exact Mass [M + H]+ | Intermediate Used | Elution Order | Chiral Column |
|---|---|---|---|---|---|---|
| 320 | 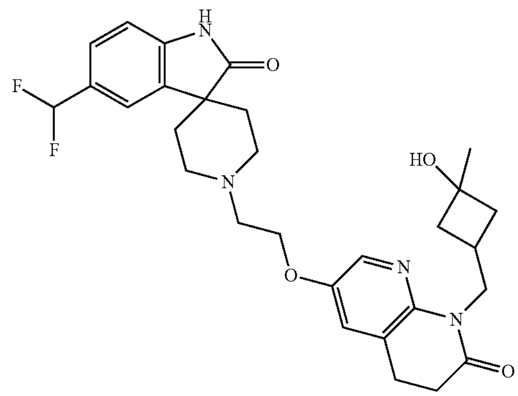 [SMILES: CC1(O)CC(CN2C(=O)CCc3cc(OCCN4CCC5(CC4)C(=O)Nc4ccc(C(F)F)cc45)cnc32)C1] | 5-(difluoromethyl)-1'-[2-({8-[(3-hydroxy-3-methylcyclobutyl)methyl]-7-oxo-5,6,7,8-tetrahydro-1,8-naphthyridin-3-yl}oxy)ethyl]-1,2-dihydrospiro[indole-3,4'-piperidin]-2-one | Calc'd 541.3 Found 541.3 | B-1 & D-1 | n/a | n/a |
| 311 | 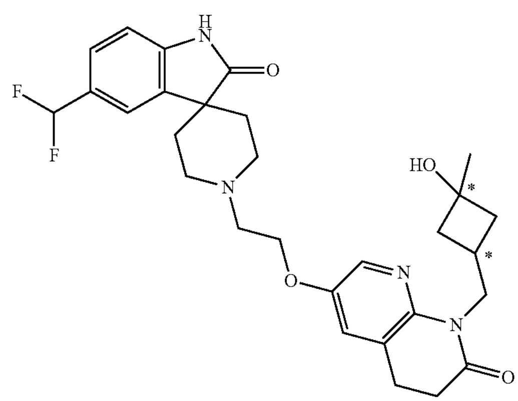 [SMILES: CC1(O)CC(CN2C(=O)CCc3cc(OCCN4CCC5(CC4)C(=O)Nc4ccc(C(F)F)cc45)cnc32)C1] | 5-(difluoromethyl)-1'-{2-[(7-oxo-8-{[(cis) or (trans)-3-hydroxy-3-methylcyclobutyl]methyl}-5,6,7,8-tetrahydro-1,8-naphthyridin-3-yl)oxy]ethyl}-1,2-dihydrospiro[indole-3,4'-piperidin]-2-one | Calc'd 541.3 Found 541.1 | B-1 & D-1 | 1st | Chiralpak IE-3 |
| 312 | 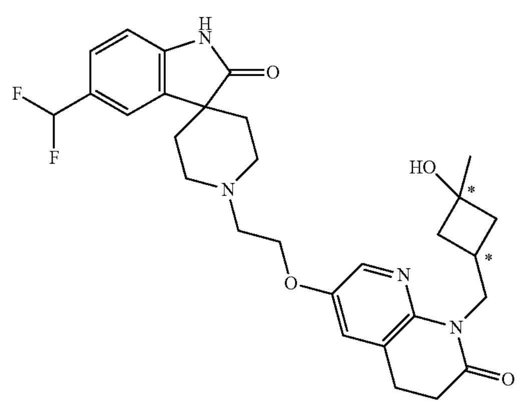 [SMILES: CC1(O)CC(CN2C(=O)CCc3cc(OCCN4CCC5(CC4)C(=O)Nc4ccc(C(F)F)cc45)cnc32)C1] | 5-(difluoromethyl)-1'-{2-[(7-oxo-8-{[(trans) or (cis)-3-hydroxy-3-methylcyclobutyl]methyl}-5,6,7,8-tetrahydro-1,8-naphthyridin-3-yl)oxy]ethyl}-1,2-dihydrospiro[indole-3,4'-piperidin]-2-one | Calc'd 541.3 Found 541.1 | B-1 & D-1 | 2nd | Chiralpak IE-3 |

Example 71

1'-(2-{[6-acetyl-5-(trifluoromethyl)pyridin-3-yl]oxy}ethyl)-5-(difluoromethyl)-1,2-dihydrospiro[indole-3,4'-piperidin]-2-one (Compound 295), 5-(difluoromethyl)-1'-(2-{[6-(1-hydroxyethyl)-5-(trifluoromethyl)pyridin-3-yl]oxy}ethyl)-1,2-dihydrospiro[indole-3,4'-piperidin]-2-one (Compound 296), 5-(difluoromethyl)-1'-[2-({6-[(1R) or (1S)-1-hydroxyethyl]-5-(trifluoromethyl)pyridin-3-yl}oxy)ethyl]-1,2-dihydrospiro[indole-3,4'-piperidin]-2-one (Compound 288), and 5-(difluoromethyl)-1'-[2-({6-[(1S) or (1R)-1-hydroxyethyl]-5-(trifluoromethyl)pyridin-3-yl}oxy)ethyl]-1,2-dihydrospiro[indole-3,4'-piperidin]-2-one (Compound 287)

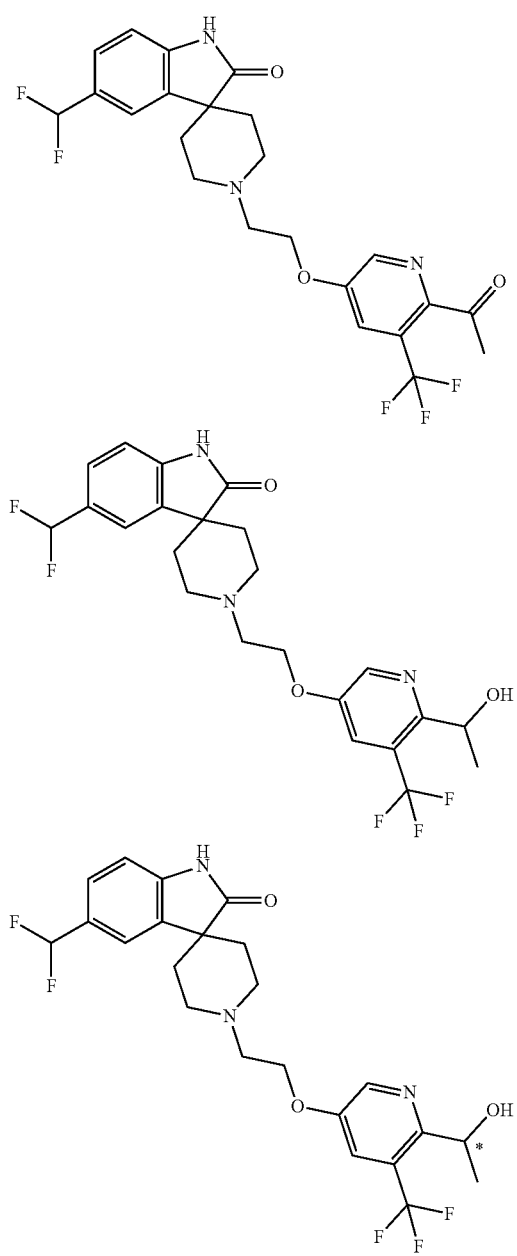

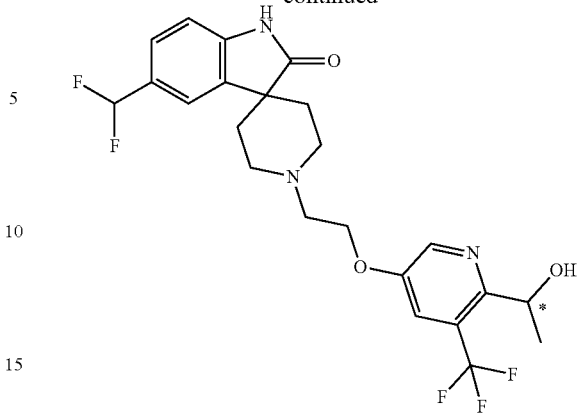

Step 1: 2-chloro-5-(4,4,5,5-tetramethyl-1,3,2-dioxaborolan-2-yl)-3-(trifluoromethyl)pyridine

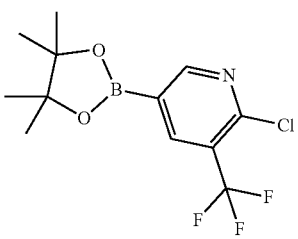 [SMILES: CC1(C)OB(c2cnc(Cl)c(C(F)(F)F)c2)OC1(C)C]

To a solution of 5-bromo-2-chloro-3-(trifluoromethyl)pyridine (5.00 g, 19.2 mmol) in 1,4-dioxane (70 mL) was added bis(pinacolato)diboron (6.83 g, 26.88 mmol), KOAc (4.71 g, 48.0 mmol), and Pd(dppf)Cl$_2$ (1.40 g, 1.92 mmol). The mixture was purged with N$_2$ (3×), and the mixture was stirred at 95° C. for 16 h under N$_2$ atmosphere. After cooling to room temperature, the reaction mixture was filtered, and the filter cake was washed with EtOAc. The filtrate was concentrated in vacuo to give 2-chloro-5-(4,4,5,5-tetramethyl-1,3,2-dioxaborolan-2-yl)-3-(trifluoromethyl)pyridine, which was used in the subsequent step without further purification.

Step 2: 6-chloro-5-(trifluoromethyl)pyridin-3-ol

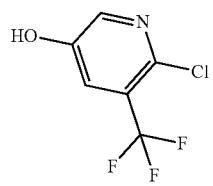 [SMILES: Oc1cnc(Cl)c(C(F)(F)F)c1]

To a solution of 2-chloro-5-(4,4,5,5-tetramethyl-1,3,2-dioxaborolan-2-yl)-3-(trifluoromethyl)pyridine (5.00 g, 16.3 mmol) in THF (45 mL) and H$_2$O (15 mL) was added Oxone (10.00 g, 16.3 mmol). The mixture was stirred at 0° C. for 1 h. The reaction mixture was quenched with saturated aqueous Na$_2$SO$_3$ solution (50 mL) and extracted with EtOAc (3×50 mL). The combined organic layers were washed with brine (40 mL), dried over Na$_2$SO$_4$, filtered, and concentrated

1189 in vacuo. The crude residue was purified by flash silica gel chromatography (Biotage 80 g cartridge, 0-30% EtOAc/Petroleum ether) to give 6-chloro-5-(trifluoromethyl)pyridin-3-ol. MS=197.9 [M+H]$^+$.

Step 3: 5-(2-bromoethoxy)-2-chloro-3-(trifluoromethyl)pyridine

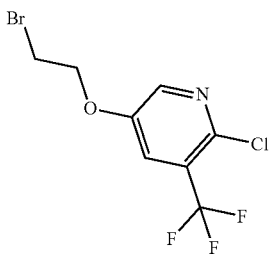 [SMILES: FC(F)(F)c1cc(OCCBr)cnc1Cl]

To a solution of 6-chloro-5-(trifluoromethyl)pyridin-3-ol (4.00 g, 20.3 mmol) in MeCN (20 mL) was added K$_2$CO$_3$ (14.0 g, 101 mmol) and 1,2-dibromoethane (15.3 mL, 202 mmol). The mixture was stirred at 70° C. for 10 h. After cooling to 0° C., the reaction mixture was quenched with H$_2$O (50 mL) and extracted with DCM (3×50 mL). The combined organic layers were washed with brine (80 mL), dried over Na$_2$SO$_4$, filtered, and concentrated in vacuo. The crude residue was purified by flash silica gel chromatography (Biotage 80 g cartridge, 0-12% EtOAc/Petroleum ether) to give 5-(2-bromoethoxy)-2-chloro-3-(trifluoromethyl)pyridine. MS=303.8/305.8 [M+H]$^+$.

Step 4: 5-(2-bromoethoxy)-2-(1-ethoxyethenyl)-3-(trifluoromethyl)pyridine

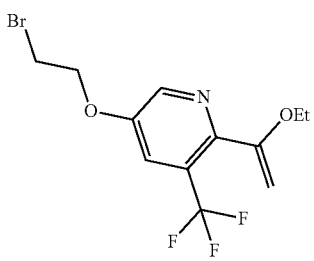 [SMILES: C=C(OCC)c1ncc(OCCBr)cc1C(F)(F)F]

To a solution of 5-(2-bromoethoxy)-2-chloro-3-(trifluoromethyl)pyridine (3.00 g, 9.85 mmol) in 1,4-dioxane (30 mL) was added tributyl(1-ethoxyvinyl)stannane (4.49 mL, 13.3 mmol) and Pd(PPh$_3$)$_2$Cl$_2$ (691 mg, 0.985 mmol). The mixture was degassed and purged with N$_2$ (3×) and stirred at 100° C. for 16 h. After cooling to room temperature, the mixture was quenched with saturated aqueous KF (50 mL) and stirred for 1 h. The mixture was filtered, and the filtrate was extracted with EtOAc (3×50 mL). The combined organic layers were dried over Na$_2$SO$_4$, filtered, and concentrated in vacuo. The crude residue was purified by flash silica gel chromatography (Biotage 80 g cartridge, 0-30% EtOAc/Petroleum ether) to give 5-(2-bromoethoxy)-2-(1-ethoxyethenyl)-3-(trifluoromethyl)pyridine. MS=340.1/342.0 [M+H]$^+$.

Step 5: 1-[5-(2-bromoethoxy)-3-(trifluoromethyl)pyridin-2-yl]ethan-1-one

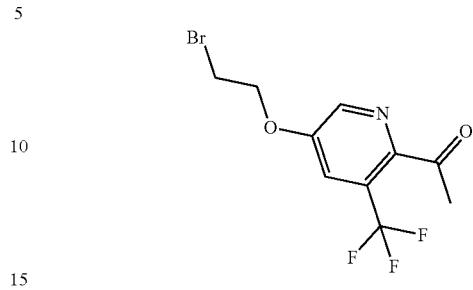

To a 0° C. solution of 5-(2-bromoethoxy)-2-(1-ethoxyethenyl)-3-(trifluoromethyl)pyridine (3.00 g, 8.82 mmol) in THF (30 mL) was added 3.0 M aqueous HCl (30 mL, 90 mmol). The mixture was stirred at room temperature for 4 h. The mixture was adjusted to pH=7-8 with saturated NaHCO$_3$ solution and extracted with EtOAc (3×30 mL). The combined organic layers were washed with brine (3×100 mL), dried over Na$_2$SO$_4$, and concentrated in vacuo. The crude residue was purified by flash silica gel chromatography (Biotage 40 g cartridge, 0-80% EtOAc/Petroleum ether) to give 1-[5-(2-bromoethoxy)-3-(trifluoromethyl)pyridin-2-yl]ethan-1-one. MS=312.0/314.0 [M+H]$^+$.

Step 6: 1'-(2-{[6-acetyl-5-(trifluoromethyl)pyridin-3-yl]oxy}ethyl)-5-(difluoromethyl)-1,2-dihydrospiro[indole-3,4'-piperidin]-2-one (Compound 295)

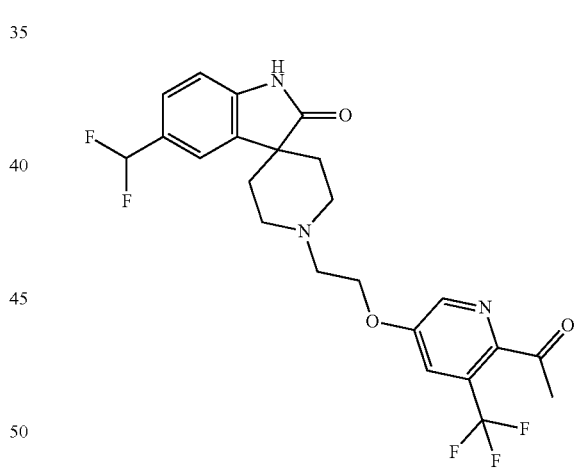

To a solution of 1-[5-(2-bromoethoxy)-3-(trifluoromethyl)pyridin-2-yl]ethan-1-one (500 mg, 1.60 mmol) and 5-(difluoromethyl)spiro[indoline-3,4'-piperidine]-2-one (Intermediate B-1, 509 mg, 1.76 mmol, HCl salt) in MeCN (10 mL) was added NaHCO$_3$ (673 mg, 8.01 mmol). The mixture was stirred at 80° C. for 16 h. After cooling to room temperature, the mixture was filtered, and filtrate was concentrated in vacuo. The crude residue was purified by reverse phase preparative HPLC (Phenomenex Luna C$_{18}$ column, 5-40% MeCN with H$_2$O with 0.04% HCl modifier) to give 1'-(2-{[6-acetyl-5-(trifluoromethyl)pyridin-3-yl]oxy}ethyl)-5-(difluoromethyl)-1,2-dihydrospiro[indole-3,4'-piperidin]-2-one (Compound 295, HCl salt). MS=484.1 [M+H]$^+$.

Step 7: 5-(difluoromethyl)-1'-(2-{[6-(1-hydroxyethyl)-5-(trifluoromethyl)pyridin-3-yl]oxy}ethyl)-1,2-dihydrospiro[indole-3,4'-piperidin]-2-one (Compound 296)

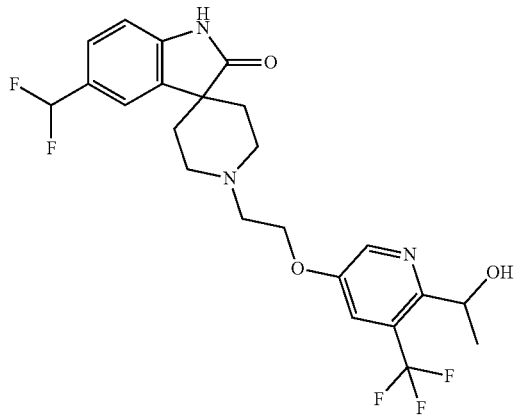 [SMILES: CC(O)c1ncc(OCCN2CCC3(CC2)C(=O)Nc2ccc(C(F)F)cc23)cc1C(F)(F)F]

To a 0° C. solution of 1'-(2-{[6-acetyl-5-(trifluoromethyl)pyridin-3-yl]oxy}ethyl)-5-(difluoromethyl)-1,2-dihydrospiro[indole-3,4'-piperidin]-2-one (Compound 295, 700 mg, 1.45 mmol) in THF (10 mL) was added NaBH$_4$ (110 mg, 2.91 mmol). The mixture was stirred at room temperature for 3 h. The mixture was quenched with the dropwise addition of H$_2$O (10 mL) and extracted with EtOAc (3×10 mL). The combined organic layers were dried over Na$_2$SO$_4$, filtered, and concentrated in vacuo. The crude residue was purified by reverse phase preparative HPLC (Waters Xbridge OBD C$_{18}$ column, 30-70% MeCN: 10 mM NH$_4$HCO$_3$ in H$_2$O) to give 5-(difluoromethyl)-1'-(2-{[6-(1-hydroxyethyl)-5-(trifluoromethyl)pyridin-3-yl]oxy}ethyl)-1,2-dihydrospiro[indole-3,4'-piperidin]-2-one (Compound 296). $^1$H NMR (400 MHz, DMSO-d$_6$): δ 10.62 (s, 1H), 8.61-8.60 (m, 1H), 7.69-7.65 (m, 2H), 7.42 (d, J=8.0 Hz, 1H), 7.09-7.81 (m, 2H), 5.12 (d, J=6.8 Hz, 1H), 4.98-4.95 (m, 1H), 4.34 (t, J=5.6 Hz, 2H), 2.96-2.93 (m, 2H), 2.90-2.87 (m, 2H), 2.72-2.70 (m, 2H), 1.82-1.80 (m, 2H), 1.69-1.67 (m, 2H), 1.38 (d, J=6.4 Hz, 3H). MS=486.1 [M+H]$^+$.

Step 8: 5-(difluoromethyl)-1'-[2-({6-[(1R) or (1S)-1-hydroxyethyl]-5-(trifluoromethyl)pyridin-3-yl}oxy)ethyl]-1,2-dihydrospiro[indole-3,4'-piperidin]-2-one (Compound 288) and 5-(difluoromethyl)-1'-[2-({6-[(1S) or (1R)-1-hydroxyethyl]-5-(trifluoromethyl)pyridin-3-yl}oxy)ethyl]-1,2-dihydrospiro[indole-3,4'-piperidin]-2-one (Compound 287)

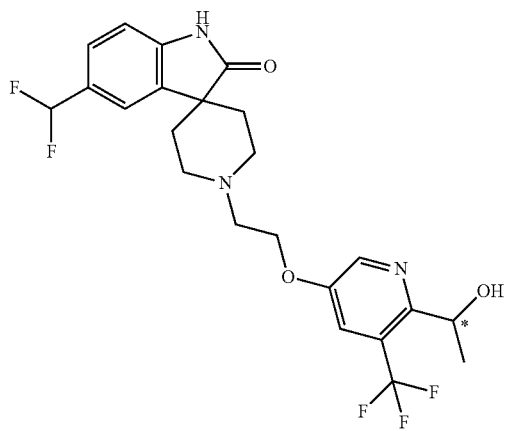

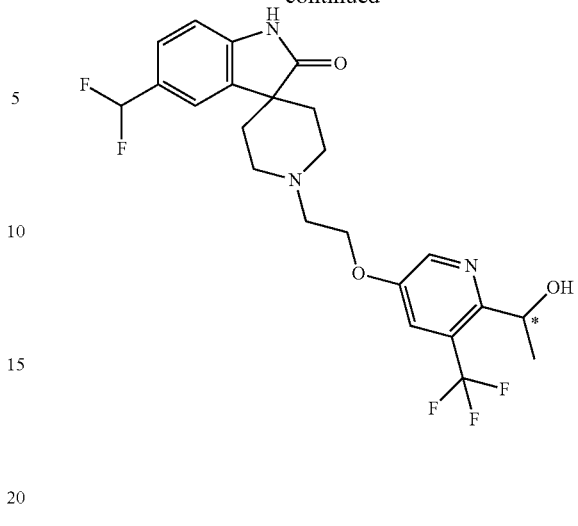

5-(difluoromethyl)-1'-(2-{[6-(1-hydroxyethyl)-5-(trifluoromethyl)pyridin-3-yl]oxy}ethyl)-1,2-dihydrospiro[indole-3,4'-piperidin]-2-one (Compound 296) was separated by preparative chiral SFC (Daicel Chiralpak IG-3 column, 50% EtOH with 0.1% NH$_4$OH in CO$_2$). The first eluting enantiomer of the title compound, 5-(difluoromethyl)-1'-[2-({6-[(1R) or (1S)-1-hydroxyethyl]-5-(trifluoromethyl)pyridin-3-yl}oxy)ethyl]-1,2-dihydrospiro[indole-3,4'-piperidin]-2-one (Compound 288). The second eluting enantiomer of the title compound, 5-(difluoromethyl)-1'-[2-({6-[(1S) or (1R)-1-hydroxyethyl]-5-(trifluoromethyl)pyridin-3-yl}oxy)ethyl]-1,2-dihydrospiro[indole-3,4'-piperidin]-2-one (Compound 287).

5-(difluoromethyl)-1'-[2-({6-[(1R) or (1S)-1-hydroxyethyl]-5-(trifluoromethyl)pyridin-3-yl}oxy)ethyl]-1,2-dihydrospiro[indole-3,4'-piperidin]-2-one (Compound 288): $^1$H NMR (400 MHz, DMSO-d$_6$): δ 10.62 (s, 1H), 8.61-8.60 (m, 1H), 7.68 (s, 1H), 7.65 (s, 1H), 7.43-7.41 (m, 1H), 7.09-6.81 (m, 2H), 5.12 (d, J=7.6 Hz, 1H), 4.96 (t, J=6.4 Hz, 1H), 4.34 (t, J=5.6 Hz, 2H), 2.95-2.93 (m, 2H), 2.90-2.87 (m, 2H), 2.72-2.70 (m, 2H), 1.82-1.80 (m, 2H), 1.69-1.67 (m, 2H), 1.38 (d, J=6.8 Hz, 3H). MS=486.1 [M+H]$^+$. 5-(difluoromethyl)-1'-[2-({6-[(1S) or (1R)-1-hydroxyethyl]-5-(trifluoromethyl)pyridin-3-yl}oxy)ethyl]-1,2-dihydrospiro[indole-3,4'-piperidin]-2-one (Compound 287): $^1$H NMR (400 MHz, DMSO-d$_6$): δ 10.62 (s, 1H), 8.61-8.60 (m, 1H), 7.68 (s, 1H), 7.65 (s, 1H), 7.43-7.41 (m, 1H), 6.97-6.81 (m, 2H), 5.12 (d, J=6.8 Hz, 1H), 4.96-4.95 (m, 1H), 4.34 (t, J=5.6 Hz, 2H), 2.95-2.93 (m, 2H), 2.90-2.87 (m, 2H), 2.72-2.70 (m, 2H), 1.82-1.80 (m, 2H), 1.69-1.67 (m, 2H), 1.38 (d, J=6.8 Hz, 3H). MS=486.1 [M+H]$^+$.

The following compounds in Table 38.8 were prepared according to the procedures similar to those described for Compounds 295, 296, 287, & 288 using the appropriate starting materials.

TABLE 38.8

| No. | Structure | IUPAC Name | Exact Mass [M + H]+ | Intermediate Used | Elution Order | Chiral Column |
|---|---|---|---|---|---|---|
| 294 | 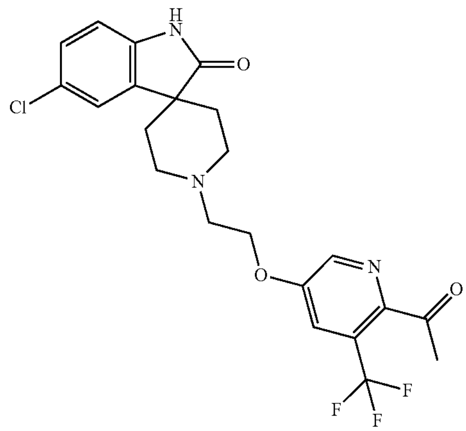 [SMILES: CC(=O)c1ncc(OCCN2CCC3(CC2)C(=O)Nc2ccc(Cl)cc23)cc1C(F)(F)F] | 1'-(2-{[6-acetyl-5-(trifluoromethyl)pyridin-3-yl]oxy}ethyl)-5-chloro-1,2-dihydrospiro[indole-3,4'-piperidin]-2-one | Calc'd 468.1 Found 468.1 | B-4 | n/a | n/a |
| 399 | 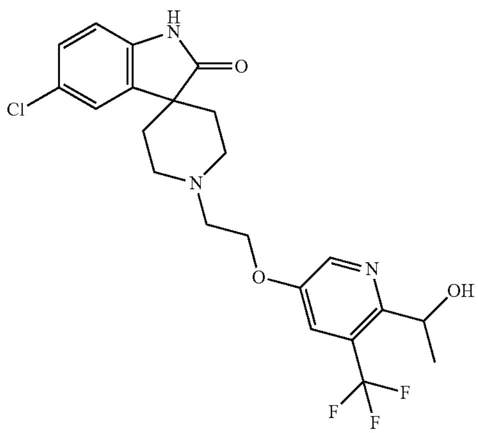 [SMILES: CC(O)c1ncc(OCCN2CCC3(CC2)C(=O)Nc2ccc(Cl)cc23)cc1C(F)(F)F] | 5-chloro-1'-(2-{[6-(1-hydroxyethyl)-5-(trifluoromethyl)pyridin-3-yl]oxy}ethyl)-1,2-dihydrospiro[indole-3,4'-piperidin]-2-one | Calc'd 470.1 Found 470.2 | B-4 | n/a | n/a |
| 292 | 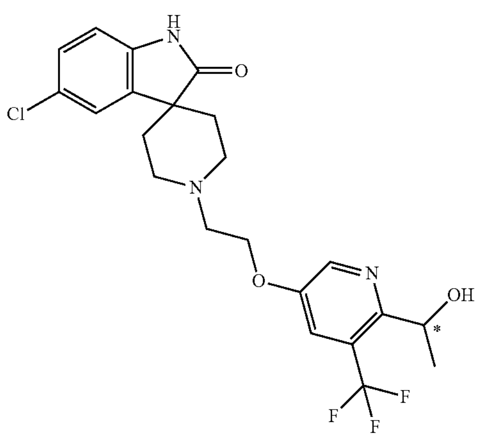 [SMILES: CC(O)c1ncc(OCCN2CCC3(CC2)C(=O)Nc2ccc(Cl)cc23)cc1C(F)(F)F] | 5-chloro-1'-[2-({6-[(1S) or (1R)-1-hydroxyethyl]-5-(trifluoromethyl)pyridin-3-yl}oxy)ethyl]-1,2-dihydrospiro[indole-3,4'-piperidin]-2-one | Calc'd 470.1 Found 470.1 | B-4 | 1st | Daicel Chiralpak IG-3 |

TABLE 38.8-continued

| No. | Structure | IUPAC Name | Exact Mass [M + H]+ | Intermediate Used | Elution Order | Chiral Column |
|---|---|---|---|---|---|---|
| 291 | 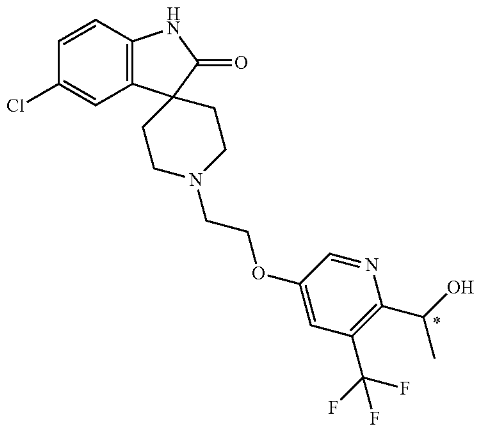 [SMILES: CC(O)c1ncc(OCCN2CCC3(CC2)C(=O)Nc2ccc(Cl)cc23)cc1C(F)(F)F] | 5-chloro-1'-[2-({6-[(1R) or (1S)-1-hydroxyethyl]-5-(trifluoromethyl)pyridin-3-yl}oxy)ethyl]-1,2-dihydrospiro[indole-3,4'-piperidin]-2-one | Calc'd 470.1 Found 470.1 | B-4 | 2nd | Daicel Chiralpak IG-3 |
| 298 | 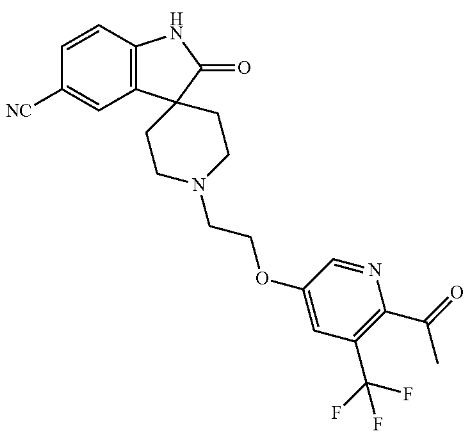 [SMILES: CC(=O)c1ncc(OCCN2CCC3(CC2)C(=O)Nc2ccc(C#N)cc23)cc1C(F)(F)F] | 1'-(2-{[6-acetyl-5-(trifluoromethyl)pyridin-3-yl]oxy}ethyl)-2-oxo-1,2-dihydrospiro[indole-3,4'-piperidine]-5-carbonitrile | Calc'd 459.2 Found 459.2 | B-9 | n/a | n/a |
| 338 | 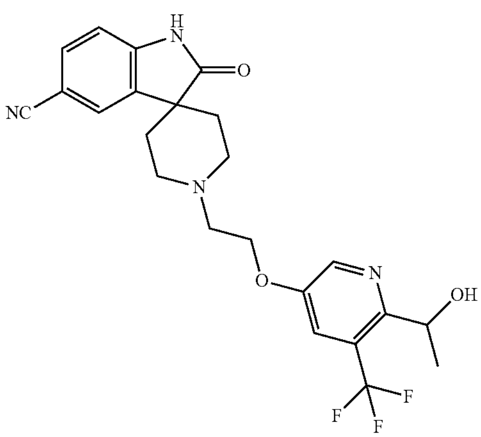 [SMILES: CC(O)c1ncc(OCCN2CCC3(CC2)C(=O)Nc2ccc(C#N)cc23)cc1C(F)(F)F] | 1'-(2-{[6-(1-hydroxyethyl)-5-(trifluoromethyl)pyridin-3-yl]oxy}ethyl)-2-oxo-1,2-dihydrospiro[indole-3,4'-piperidine]-5-carbonitrile | Calc'd 461.2 Found 461.3 | B-9 | n/a | n/a |

TABLE 38.8-continued

| No. | Structure | IUPAC Name | Exact Mass [M + H]+ | Intermediate Used | Elution Order | Chiral Column |
|---|---|---|---|---|---|---|
| 376 | 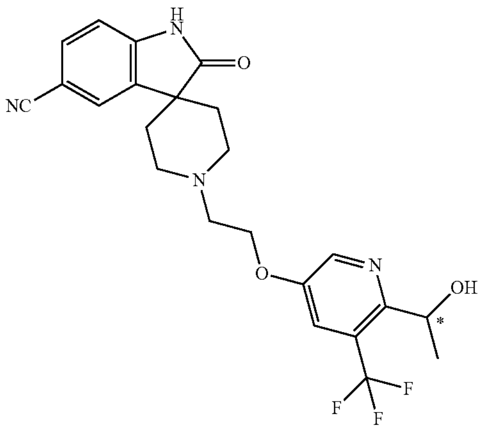 [SMILES: CC(O)c1ncc(OCCN2CCC3(CC2)C(=O)Nc2ccc(C#N)cc23)cc1C(F)(F)F] | 1'-[2-({6-[(1S) or (1R)-1-hydroxyethyl]-5-(trifluoromethyl)pyridin-3-yl}oxy)ethyl]-2-oxo-1,2-dihydrospiro[indole-3,4'-piperidine]-5-carbonitrile | Calc'd 461.2 Found 461.1 | B-9 | 1st | Daicel Chiralpak IG-3 |
| 377 | 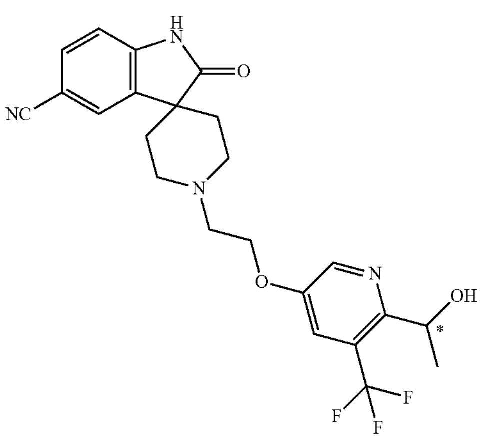 [SMILES: CC(O)c1ncc(OCCN2CCC3(CC2)C(=O)Nc2ccc(C#N)cc23)cc1C(F)(F)F] | 1'-[2-({6-(1S) or (1R)-1-hydroxyethyl]-5-(trifluoromethyl)pyridin-3-yl}oxy)ethyl]-2-oxo-1,2-dihydrospiro[indole-3,4'-piperidine]-5-carbonitrile | Calc'd 461.2 Found 461.1 | B-9 | 2nd | Daicel Chiralpak IG-3 |

Example 72

5-chloro-1'-(2-{[8-(3-hydroxy-3-methylcyclobutyl)-7-oxo-5,6,7,8-tetrahydro-1,8-naphthyridin-3-yl]oxy}ethyl)-1,2-dihydrospiro[indole-3,4'-piperidin]-2-one (Compound 315), 5-chloro-1'-[2-({7-oxo-8-[(cis)-3-hydroxy-3-methylcyclobutyl]-5,6,7,8-tetrahydro-1,8-naphthyridin-3-yl}oxy)ethyl]-1,2-dihydrospiro[indole-3,4'-piperidin]-2-one (Compound 275), and 5-chloro-1'-[2-({7-oxo-8-[(trans)-3-hydroxy-3-methylcyclobutyl]-5,6,7,8-tetrahydro-1,8-naphthyridin-3-yl}oxy)ethyl]-1,2-dihydrospiro[indole-3,4'-piperidin]-2-one (Compound 307)

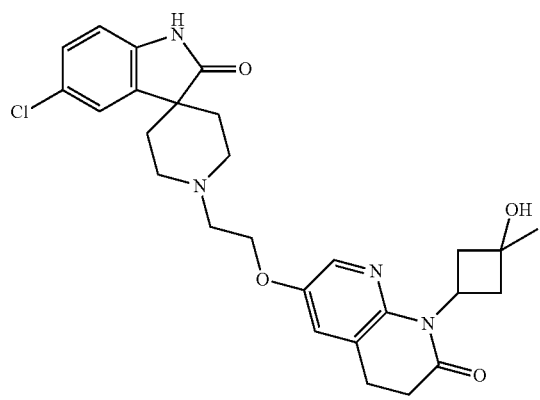

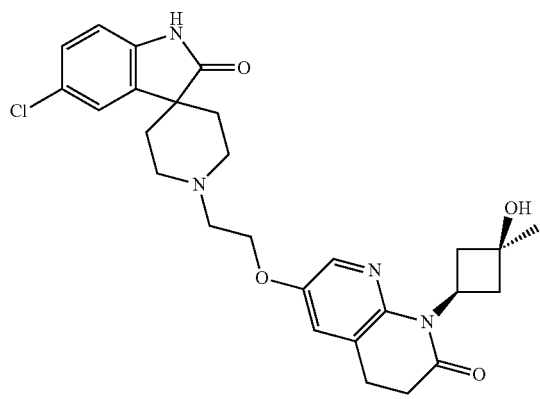

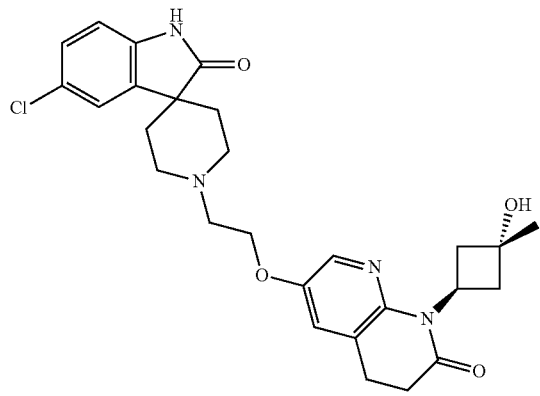

Step 1: 3-(benzyloxy)-1-methylcyclobutan-1-ol

To a −20° C. solution of 3.0 M MeMgBr in 2-MeTHF (94 mL, 282 mmol) in THF (1.0 L) under $N_2$ atmosphere was added a solution of 3-(benzyloxy)cyclobutan-1-one (25.0 g, 142 mmol) in THF (200 mL) dropwise. The mixture was stirred at −20° C. for 30 min. The mixture was warmed to 0° C., quenched with $H_2O$ (300 mL), and stirred at 0° C. for 15 min. The mixture was extracted with EtOAc (3×100 mL). The combined organic layers were washed with brine (300 mL), dried over $Na_2SO_4$, filtered, and concentrated in vacuo to give 3-(benzyloxy)-1-methylcyclobutan-1-ol, which was used in the subsequent step without further purification. $^1$H NMR (400 MHz, $CDCl_3$): δ 7.36-7.31 (m, 5H), 4.45 (s, 3H), 3.75-3.72 (m, 1H), 2.48-2.43 (m, 2H), 2.13-2.09 (m, 2H), 1.32 (s, 3H).

Step 2: [3-(benzyloxy)-1-methylcyclobutoxy](tert-butyl)dimethylsilane

To a solution of 3-benzyloxy-1-methyl-cyclobutanol (30 g, 156 mmol) in DCM (300 mL) was added imidazole (32.0 g, 468 mmol) and TBSCl (28.7 mL, 234 mmol). The mixture was stirred at room temperature for 16 h. The mixture was filtered, and filtrate was in vacuo. The crude residue was purified by flash silica gel chromatography (Biotage 330 g cartridge, 0-5% EtOAc/Petroleum ether) to give [3-(benzyloxy)-1-methylcyclobutoxy](tert-butyl)dimethylsilane. $^1$H NMR (400 MHz, DMSO-$d_6$): δ 7.34-7.29 (m, 5H), 4.42 (s, 2H), 3.70-3.65 (m, 1H), 2.42-2.38 (m, 2H), 2.19-2.17 (m, 2H), 1.30 (s, 3H), 0.90 (s, 9H), 0.09 (s, 6H).

Step 3: 3-[(tert-butyldimethylsilyl)oxy]-3-methylcyclobutan-1-ol

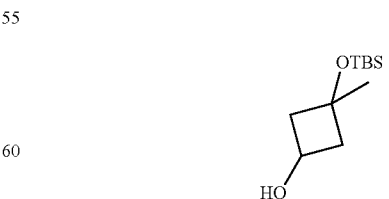

To a solution of [3-(benzyloxy)-1-methylcyclobutoxy](tert-butyl)dimethylsilane (49.0 g, 160 mmol) in MeOH (1.5 L) under $N_2$ atmosphere was added Pd/C (20.0 g, 10 wt %, 18.9 mmol). The mixture was degassed and purged with $H_2$ (3×). The mixture was stirred at 40° C. for 16 h under H₂ (15 psi). After cooling to room temperature, the mixture was filtered, and filtrate was concentrated in vacuo. The crude residue was purified by flash silica gel chromatography (Biotage 330 g cartridge, 0-30% EtOAc/Petroleum ether) to give 3-[(tert-butyldimethylsilyl)oxy]-3-methylcyclobutan-1-ol.

Step 4: 3-[(tert-butyldimethylsilyl)oxy]-3-methylcyclobutyl methanesulfonate

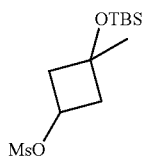

To a 0° C. solution of 3-[(tert-butyldimethylsilyl)oxy]-3-methylcyclobutan-1-ol (10.0 g, 46.2 mmol) in DCM (100 mL) was added TEA (12.9 mL, 92.4 mmol). Methanesulfonic anhydride (12.1 g, 69.3 mmol) was added, and the mixture was stirred at room temperature for 16 h. The mixture was poured into ice water (100 ml) and extracted with DCM (3×100 mL). The combined organic layers were washed with brine (200 mL), dried over Na₂SO₄, filtered, and concentrated in vacuo to provide 3-[(tert-butyldimethylsilyl)oxy]-3-methylcyclobutyl methanesulfonate, which was used in the subsequent step without further purification. ¹H NMR (400 MHz, DMSO-d₆): δ 4.75-4.68 (m, 1H), 3.33 (s, 3H), 2.59-2.54 (m, 2H), 2.25-2.24 (m, 2H), 1.30 (s, 3H), 0.85 (s, 9H), 0.07 (s, 6H).

Step 5: 6-bromo-1-{3-[(tert-butyldimethylsilyl)oxy]-3-methylcyclobutyl}-1,2,3,4-tetrahydro-1,8-naphthyridin-2-one

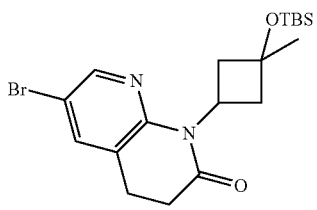 [SMILES: CC1(O[Si](C)(C)C(C)(C)C)CC(N2C(=O)CCc3cc(Br)cnc32)C1]

To a solution of 6-bromo-1,2,3,4-tetrahydro-1,8-naphthyridin-2-one (1.20 g, 5.29 mmol) and 3-[(tert-butyldimethylsilyl)oxy]-3-methylcyclobutyl methanesulfonate (6.23 g, 21.1 mmol) in DMSO (100 mL) was added Cs₂CO₃ (5.17 g, 15.9 mmol). The mixture was stirred at 130° C. for 16 h. The mixture was poured into H₂O (100 ml) and extracted with EtOAc (3×100 mL). The combined organic layers were washed with brine (200 mL), dried over Na₂SO₄, filtered, and concentrated in vacuo. The crude residue was purified by flash silica gel chromatography (Biotage 120 g cartridge, 0-30% EtOAc/Petroleum ether) to give 6-bromo-1-{3-[(tert-butyldimethylsilyl)oxy]-3-methylcyclobutyl}-1,2,3,4-tetrahydro-1,8-naphthyridin-2-one. MS=425.1/427.1 [M+H]⁺.

Step 6: 1-{3-[(tert-butyldimethylsilyl)oxy]-3-methylcyclobutyl}-6-(4,4,5,5-tetramethyl-1,3,2-dioxaborolan-2-yl)-1,2,3,4-tetrahydro-1,8-naphthyridin-2-one

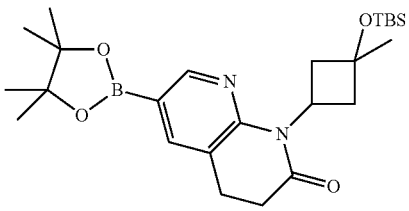

To a solution of 6-bromo-1-{3-[(tert-butyldimethylsilyl)oxy]-3-methylcyclobutyl}-1,2,3,4-tetrahydro-1,8-naphthyridin-2-one (5.00 g, 11.8 mmol) in 1,4-dioxane (100 mL) was added AcOK (2.31 g, 23.5 mmol) and bis(pinacolato)diboron (3.58 g, 14.1 mmol). Pd(dppf)Cl₂ (860 mg, 1.18 mmol) was added, and the mixture was degassed and purged with N₂ (3×). The mixture was stirred at 80° C. for 16 h. After cooling to room temperature, the mixture was filtered, and the filtrate was concentrated in vacuo. The crude residue was purified by flash silica gel chromatography (Biotage 80 g cartridge, 0-40% EtOAc/Petroleum ether) to give 1-{3-[(tert-butyldimethylsilyl)oxy]-3-methylcyclobutyl}-6-(4,4,5,5-tetramethyl-1,3,2-dioxaborolan-2-yl)-1,2,3,4-tetrahydro-1,8-naphthyridin-2-one. MS=473.4 [M+H]⁺.

Step 7: 1-{3-[(tert-butyldimethylsilyl)oxy]-3-methylcyclobutyl}-6-hydroxy-1,2,3,4-tetrahydro-1,8-naphthyridin-2-one

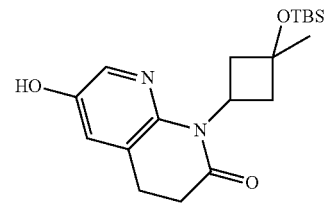 [SMILES: CC1(O[Si](C)(C)C(C)(C)C)CC(N2C(=O)CCc3cc(O)cnc32)C1]

To a 0° C. solution of 1-{3-[(tert-butyldimethylsilyl)oxy]-3-methylcyclobutyl}-6-(4,4,5,5-tetramethyl-1,3,2-dioxaborolan-2-yl)-1,2,3,4-tetrahydro-1,8-naphthyridin-2-one (7.00 g, 14.8 mmol) in THF (90 mL) and H₂O (30 mL) was added Oxone (13.7 g, 22.2 mmol). The mixture was stirred at room temperature for 3 h. The mixture was poured into ice water (100 mL) and extracted with EtOAc (3×100 mL). The combined organic layers were washed with brine (200 mL), dried over Na₂SO₄, filtered, and concentrated in vacuo. The crude residue was purified by flash silica gel chromatography (Biotage 80 g cartridge, 0-40% EtOAc/Petroleum ether) to give 1-{3-[(tert-butyldimethylsilyl)oxy]-3-methylcyclobutyl}-6-hydroxy-1,2,3,4-tetrahydro-1,8-naphthyridin-2-one. MS=363.2 [M+H]⁺.

Step 8: 6-(2-bromoethoxy)-1-{3-[(tert-butyldimethylsilyl)oxy]-3-methylcyclobutyl}-1,2,3,4-tetrahydro-1,8-naphthyridin-2-one

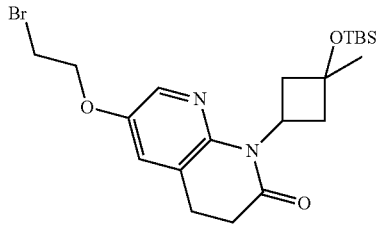 [SMILES: CC1(O[Si](C)(C)C(C)(C)C)CC(N2C(=O)CCc3cc(OCCBr)cnc32)C1]

To a solution of 1-{3-[(tert-butyldimethylsilyl)oxy]-3-methylcyclobutyl}-6-hydroxy-1,2,3,4-tetrahydro-1,8-naphthyridin-2-one (1.30 g, 3.59 mmol) and 1,2-dibromoethane (8.12 mL, 108 mmol) in MeCN (1.0 mL) was added K$_2$CO$_3$ (1.49 g, 10.8 mmol). The mixture was stirred at 80° C. for 16 h. After cooling to room temperature, the mixture was filtered, and the filtrate was concentrated in vacuo. The crude residue was purified by flash silica gel chromatography (Biotage 12 g cartridge, 0-80% EtOAc/Petroleum ether) to give 6-(2-bromoethoxy)-1-{3-[(tert-butyldimethylsilyl)oxy]-3-methylcyclobutyl}-1,2,3,4-tetrahydro-1,8-naphthyridin-2-one. MS=469.2/471.2 [M+H]$^+$.

Step 9: 6-(2-bromoethoxy)-1-(3-hydroxy-3-methylcyclobutyl)-1,2,3,4-tetrahydro-1,8-naphthyridin-2-one

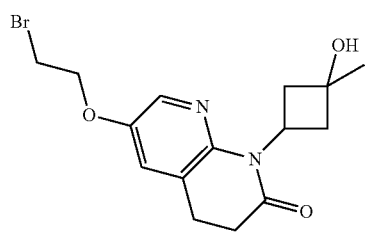 [SMILES: CC1(O)CC(N2C(=O)CCc3cc(OCCBr)cnc32)C1]

To a 0° C. solution of 6-(2-bromoethoxy)-1-{3-[(tert-butyldimethylsilyl)oxy]-3-methylcyclobutyl}-1,2,3,4-tetrahydro-1,8-naphthyridin-2-one (1.00 g, 2.13 mmol) in THF (2 mL) was added 6.0 M HCl in H$_2$O (8 mL, 48 mmol). The mixture was stirred at room temperature for 2 h, then was concentrated under reduced pressure. The crude residue was purified by flash silica gel chromatography (Biotage 12 g cartridge, 0-80% EtOAc/Petroleum ether) to give 6-(2-bromoethoxy)-1-(3-hydroxy-3-methylcyclobutyl)-1,2,3,4-tetrahydro-1,8-naphthyridin-2-one. MS=355.1/357.1 [M+H]$^+$.

Step 10: 5-chloro-1'-(2-{[8-(3-hydroxy-3-methylcyclobutyl)-7-oxo-5,6,7,8-tetrahydro-1,8-naphthyridin-3-yl]oxy}ethyl)-1,2-dihydrospiro[indole-3,4'-piperidin]-2-one (Compound 315)

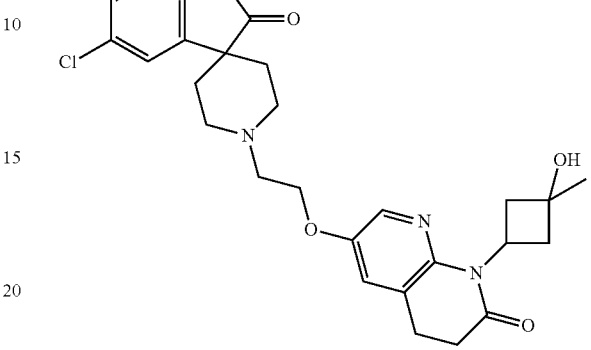

To a solution of 6-(2-bromoethoxy)-1-(3-hydroxy-3-methylcyclobutyl)-1,2,3,4-tetrahydro-1,8-naphthyridin-2-one (200 mg, 0.563 mmol) and 5-chloro-1H-spiro[indole-3,4'-piperidin]-2-one (Intermediate B-4, 231 mg, 0.845 mmol, HCl salt) in MeCN (5.0 mL) was added NaHCO$_3$ (331 mg, 3.94 mmol). The mixture was stirred at 80° C. for 16 h. The mixture was filtered, and filtrate was concentrated in vacuo. The crude residue was purified by reverse phase preparative HPLC (Phenomenex Luna C$_{18}$ column, 5-35% MeCN with H$_2$O with 0.04% HCl modifier) to give 5-chloro-1'-(2-{[8-(3-hydroxy-3-methylcyclobutyl)-7-oxo-5,6,7,8-tetrahydro-1,8-naphthyridin-3-yl]oxy}ethyl)-1,2-dihydrospiro[indole-3,4'-piperidin]-2-one (Compound 315, HCl salt). $^1$H NMR (400 MHz, DMSO-d$_6$): δ 11.20-11.17 (m, 0.5H), 10.81-10.73 (m, 1H), 10.63 (s, 0.5H), 8.03-8.00 (m, 1.5H), 7.45 (s, 1H), 7.30-7.28 (m, 1H), 7.15 (s, 0.5H), 6.94-6.89 (m, 1H), 5.34-5.25 (m, 1H), 4.51 (s, 2H), 3.83 (s, 1H), 3.82-3.66 (m, 4H), 3.64 (s, 1H), 2.84-2.80 (m, 2H), 2.66-2.65 (m, 2H), 2.64-2.53 (m, 3H), 2.24-2.18 (m, 3H), 2.18-1.94 (m, 2H), 1.31 (s, 3H). MS=511.2 [M+H]$^+$.

Step 11: 5-chloro-1'-[2-({7-oxo-8-[(cis)-3-hydroxy-3-methylcyclobutyl]-5,6,7,8-tetrahydro-1,8-naphthyridin-3-yl}oxy)ethyl]-1,2-dihydrospiro[indole-3,4'-piperidin]-2-one (Compound 275) and 5-chloro-1'-[2-({7-oxo-8-[(trans)-3-hydroxy-3-methylcyclobutyl]-5,6,7,8-tetrahydro-1,8-naphthyridin-3-yl}oxy)ethyl]-1,2-dihydrospiro[indole-3,4'-piperidin]-2-one (Compound 307)

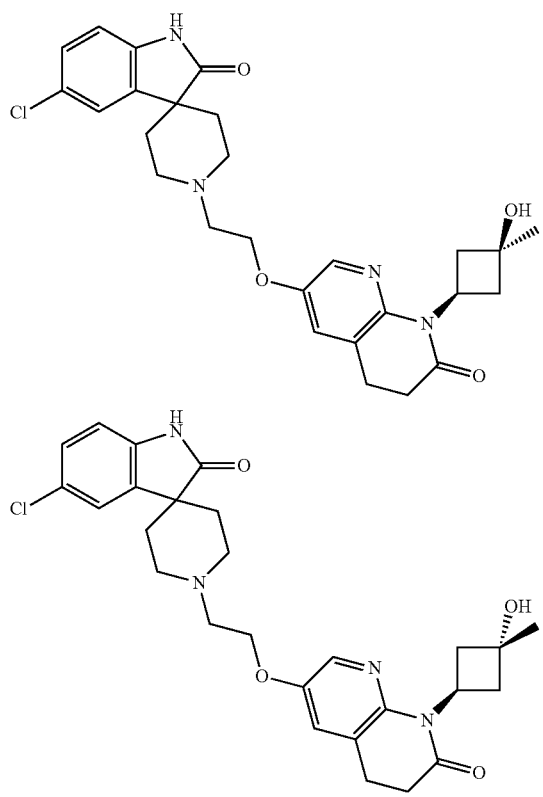

5-chloro-1'-(2-{[8-(3-hydroxy-3-methylcyclobutyl)-7-oxo-5,6,7,8-tetrahydro-1,8-naphthyridin-3-yl]oxy}ethyl)-1,2-dihydrospiro[indole-3,4'-piperidin]-2-one (Compound 315) was separated by preparative chiral SFC (Daicel Chiralpak AD-3 column, 50% IPA with 0.1% NH₄OH in C$_{O2}$). The first eluting diastereomer of the title compound, 5-chloro-1'-[2-({7-oxo-8-[(trans)-3-hydroxy-3-methylcyclobutyl]-5,6,7,8-tetrahydro-1,8-naphthyridin-3-yl}oxy)ethyl]-1,2-dihydrospiro[indole-3,4'-piperidin]-2-one (Compound 307). The second eluting diastereomer of the title compound, 5-chloro-1'-[2-({7-oxo-8-[(cis)-3-hydroxy-3-methylcyclobutyl]-5,6,7,8-tetrahydro-1,8-naphthyridin-3-yl}oxy)ethyl]-1,2-dihydrospiro[indole-3,4'-piperidin]-2-one (Compound 275, Example 59). 5-chloro-1'-[2-({7-oxo-8-[(trans)-3-hydroxy-3-methylcyclobutyl]-5,6,7,8-tetrahydro-1,8-naphthyridin-3-yl}oxy)ethyl]-1,2-dihydrospiro[indole-3,4'-piperidin]-2-one (Compound 307): ¹H NMR (400 MHz, DMSO-d₆): δ 10.48 (s, 1H), 7.96 (s, 1H), 7.50-7.49 (m, 1H), 7.38-7.37 (m, 1H), 7.25-7.22 (m, 1H), 6.85-6.83 (m, 1H), 5.32-5.27 (m, 1H), 4.78 (s, 1H), 4.19-4.17 (m, 2H), 2.92-2.78 (m, 2H), 2.69-2.67 (m, 4H), 2.66-2.52 (m, 4H), 2.40-2.20 (m, 2H), 2.19-2.18 (m, 2H), 1.78-1.72 (m, 4H), 1.30 (s, 3H). MS=511.2 [M+H]⁺.

Example 73

5-chloro-1'-(2-{[2-(1-hydroxycyclopropyl)pyrimidin-5-yl]oxy}ethyl)-1,2-dihydrospiro[indole-3,4'-piperidin]-2-one (Compound 308)

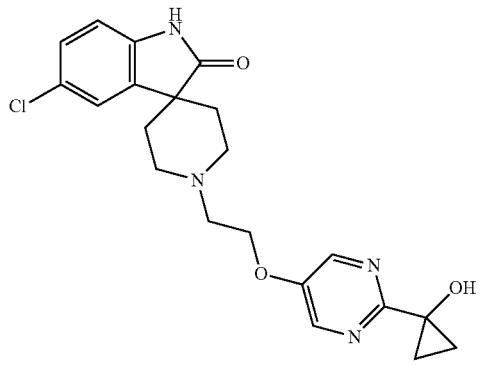 [SMILES: O=C1Nc2ccc(Cl)cc2C12CCN(CCOc1cnc(C3(O)CC3)nc1)CC2]

Step 1: 5-bromo-2-[1-(ethoxymethoxy)ethenyl]pyrimidine

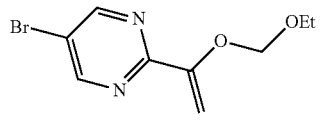

To a three-neck round-bottom flask equipped with a magnetic stir bar and thermometer under N₂ atmosphere was added 1-(5-bromopyrimidin-2-yl)ethan-1-one (5.00 g, 24.9 mmol) and THF (80 mL). The mixture was cooled to −78° C. and then 1.0 M LiHMDS in hexane (37.3 mL, 37.3 mmol) was added dropwise over 5 min. After stirring for 10 min, chloromethoxyethane (2.77 mL, 29.9 mmol) was added dropwise. The mixture was slowly warmed to room temperature and stirred for another 5 h. After cooling to 0° C., the reaction mixture was quenched with saturated aqueous NH₄Cl (80 mL), and then extracted with EtOAc (3×50 mL). The combined organic layers were washed with brine (100 mL), dried over Na₂SO₄, filtered, and concentrated in vacuo. The crude residue was purified by flash silica gel chromatography (Biotage 80 g cartridge, 0-20% EtOAc/Petroleum ether) to give 5-bromo-2-[1-(ethoxymethoxy)ethenyl]pyrimidine. MS=259.1/261.0 [M+H]⁺.

Step 2: 5-bromo-2-[1-(ethoxymethoxy)cyclopropyl]pyrimidine

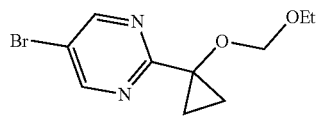 [SMILES: CCOCOC1(c2ncc(Br)cn2)CC1]

To a solution of trimethylsulfoxonium iodide (4.08 g, 18.5 mmol) in DMSO (10 mL) was added t-BuOK (1.82 g, 16.2 mmol). The mixture was stirred at 50° C. for 30 min, and then a solution of 5-bromo-2-[1-(ethoxymethoxy)vinyl]pyrimidine (1.20 g, 4.63 mmol) in DMSO (10 mL) was added dropwise. The mixture was stirred at 50° C. for 30 min. After cooling to 0° C., the reaction mixture was quenched with H₂O (20 mL), and then extracted with EtOAc (2×15 mL). The combined organic layers were washed with brine (2×30 mL), dried over Na₂SO₄, filtered, and concentrated in vacuo. The crude residue was purified by flash silica gel chromatography (Biotage 20 g cartridge, 0-20% EtOAc/Petroleum ether) to give 5-bromo-2-[1-(ethoxymethoxy)cyclopropyl]pyrimidine, MS=273.1/275.1 [M+H]⁺.

Step 3: 2-[1-(ethoxymethoxy)cyclopropyl]-5-(4,4,5,5-tetramethyl-1,3,2-dioxaborolan-2-yl)pyrimidine

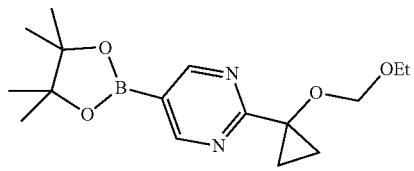 [SMILES: CCOCOC1(c2ncc(B3OC(C)(C)C(C)(C)O3)cn2)CC1]

A mixture of 5-bromo-2-[1-(ethoxymethoxy)cyclopropyl]pyrimidine (570 mg, 2.09 mmol), bis(pinacolato)diboron (795 mg, 3.13 mmol), KOAc (614 mg, 6.26 mmol), and Pd(dppf)Cl₂ (76.4 mg, 0.104 mmol) in 1,4-dioxane (15 mL) was degassed and purged with N₂ (3×), and then the mixture was stirred at 80° C. for 15 h under N₂ atmosphere. After cooling to room temperature, the mixture was filtered and the filtrate was concentrated in vacuo to give 2-[1-(ethoxymethoxy)cyclopropyl]-5-(4,4,5,5-tetramethyl-1,3,2-dioxaborolan-2-yl)pyrimidine, which was used in the subsequent step without further purification.

Step 4: 2-[1-(ethoxymethoxy)cyclopropyl]pyrimidin-5-ol

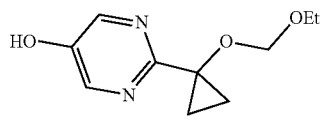 [SMILES: CCOCOC1(c2ncc(O)cn2)CC1]

To a solution of 2-[1-(ethoxymethoxy)cyclopropyl]-5-(4,4,5,5-tetramethyl-1,3,2-dioxaborolan-2-yl)pyrimidine (700 mg, 2.19 mmol) in MeCN (15 mL) and H₂O (15 mL) was added Oxone (2.02 g, 3.28 mmol). The mixture was stirred for 2 h. The reaction mixture was quenched with saturated aqueous Na₂SO₃ (10 mL) at 0° C., and then extracted with EtOAc (3×15 mL). The combined organic layers were washed with brine (2×20 mL), dried over Na₂SO₄, filtered, and concentrated in vacuo. The crude residue was purified by flash silica gel chromatography (Biotage 12 g cartridge, 0-50% EtOAc/Petroleum ether) to give 2-[1-(ethoxymethoxy)cyclopropyl]pyrimidin-5-ol. MS=211.3 [M+H]⁺.

Step 5: 5-(2-bromoethoxy)-2-[1-(ethoxymethoxy)cyclopropyl]pyrimidine

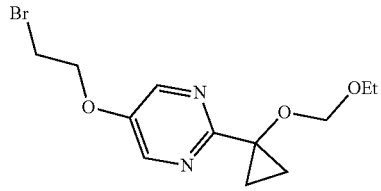 [SMILES: CCOCOC1(c2ncc(OCCBr)cn2)CC1]

To a solution of 2-[1-(ethoxymethoxy)cyclopropyl]pyrimidin-5-ol (600 mg, 2.85 mmol) and 1,2-dibromoethane (8.61 mL, 114 mmol) in MeCN (10 mL) was added K₂CO₃ (1.97 g, 14.3 mmol). The mixture was stirred at 65° C. for 5 h. After cooling to room temperature, the mixture was filtered, and the filtrate was concentrated in vacuo. The crude residue was purified by flash silica gel chromatography (Biotage 12 g cartridge, 0-35% EtOAc/Petroleum ether) to give 5-(2-bromoethoxy)-2-[1-(ethoxymethoxy)cyclopropyl]pyrimidine. MS=317.2/319.1 [M+H]⁺.

Step 6: 1-[5-(2-bromoethoxy)pyrimidin-2-yl]cyclopropan-1-ol

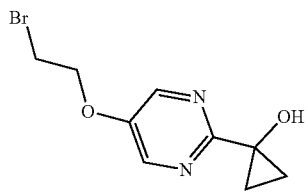 [SMILES: OC1(c2ncc(OCCBr)cn2)CC1]

To a solution of 5-(2-bromoethoxy)-2-[1-(ethoxymethoxy)cyclopropyl]pyrimidine (300 mg, 0.946 mmol) in DCM (15 mL) was added TFA (1.0 mL). The mixture was stirred for 1 h, then was concentrated in vacuo. The residue was cooled to 0° C. and quenched with H₂O (15 mL), and then adjusted to pH=8 with saturated aqueous NaHCO₃. The biphasic mixture was extracted with EtOAc (3×10 mL). The combined organic layers were washed with brine (2×20 mL), dried over Na₂SO₄, filtered, and concentrated in vacuo to give 5-(2-bromoethoxy)-2-[1-(ethoxymethoxy)cyclopropyl]pyrimidine. MS=259.0/261.0 [M+H]⁺.

Step 7: 5-chloro-1'-(2-{[2-(1-hydroxycyclopropyl)pyrimidin-5-yl]oxy}ethyl)-1,2-dihydrospiro[indole-3,4'-piperidin]-2-one (Compound 308)

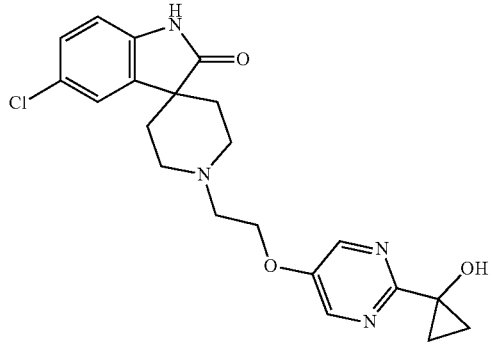 [SMILES: O=C1Nc2ccc(Cl)cc2C12CCN(CCOc1cnc(C3(O)CC3)nc1)CC2]

A mixture of 1-[5-(2-bromoethoxy)pyrimidin-2-yl]cyclopropanol (100 mg, 0.386 mmol), 5-chloro-1H-spiro[indole-3,4'-piperidin]-2-one (Intermediate B-4, 111 mg, 0.405 mmol, HCl salt), and NaHCO₃ (162 mg, 1.93 mmol) in MeCN (4 mL) was degassed and purged with N₂ (3×), and then the mixture was stirred at 80° C. for 15 h under N₂ atmosphere. After cooling to room temperature, the mixture was filtered, and the filtrate was concentrated in vacuo. The crude residue was purified by reverse phase preparative HPLC (Phenomenex Kinetex $C_{18}$ column, 15-45% MeCN with H₂O with 0.1% NH₄OH modifier) to give 5-chloro-1'-(2-{[2-(1-hydroxycyclopropyl)pyrimidin-5-yl]oxy}ethyl)-1,2-dihydrospiro[indole-3,4'-piperidin]-2-one (Compound 308). ¹H NMR (400 MHz, DMSO-d₆): δ 10.48 (s, 1H), 8.49 (s, 2H), 7.50 (d, J=2.0 Hz, 1H), 7.23 (dd, J=8.4 Hz, 2.0 Hz, 1H), 6.84 (d, J=8.4 Hz, 1H), 5.90 (s, 1H), 4.28 (t, J=5.6 Hz, 2H), 2.93-2.85 (m, 4H), 2.71-2.69 (m, 2H), 1.78-1.72 (m, 4H), 1.21-1.18 (m, 2H), 1.09-1.06 (m, 2H). MS=415.1 [M+H]⁺.

Example 74

5-chloro-1'-{2-[(7-oxo-5,6,7,8-tetrahydro-1,8-naphthyridin-3-yl)oxy]ethyl}-1,2-dihydrospiro[indole-3,4'-piperidin]-2-one (Compound 293)

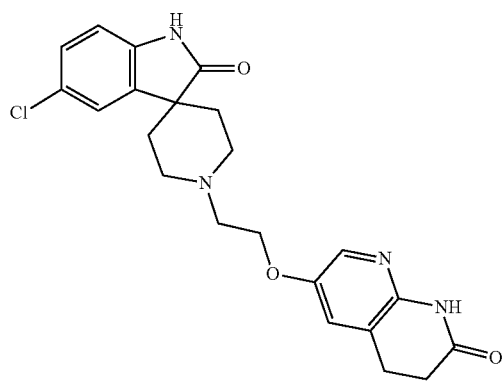 [SMILES: O=C1CCc2cc(OCCN3CCC4(CC3)C(=O)Nc3ccc(Cl)cc34)cnc2N1]

Step 1: tert-butyl 6-bromo-2-oxo-1,2,3,4-tetrahydro-1,8-naphthyridine-1-carboxylate

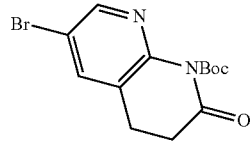 [SMILES: CC(C)(C)OC(=O)N1C(=O)CCc2cc(Br)cnc21]

To a solution of 6-bromo-1,2,3,4-tetrahydro-1,8-naphthyridin-2-one (10.0 g, 44.0 mmol) in DCM (70 mL) was added Boc₂O (12.1 mL, 52.9 mmol), DIEA (11.5 mL, 66.1 mmol) and DMAP (538 mg, 4.40 mmol). The mixture was stirred for 4 h, then solids were removed by filtration. The filtrate was diluted with H₂O (80 mL) and extracted with EtOAc (2×60 mL). The combined organic layers were dried over Na₂SO₄, filtered, and concentrated in vacuo. The crude residue was purified by flash silica gel chromatography (Biotage 80 g cartridge, 0-35% EtOAc/Petroleum ether) to give tert-butyl 6-bromo-2-oxo-1,2,3,4-tetrahydro-1,8-naphthyridine-1-carboxylate.

Step 2: tert-butyl 2-oxo-6-(4,4,5,5-tetramethyl-1,3,2-dioxaborolan-2-yl)-1,2,3,4-tetrahydro-1,8-naphthyridine-1-carboxylate

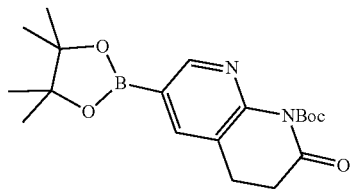 [SMILES: CC(C)(C)OC(=O)N1C(=O)CCc2cc(B3OC(C)(C)C(C)(C)O3)cnc21]

A mixture of tert-butyl 6-bromo-2-oxo-1,2,3,4-tetrahydro-1,8-naphthyridine-1-carboxylate (3.00 g, 9.17 mmol), bis(pinacolato)diboron (2.79 g, 11.0 mmol), KOAc (2.25 g, 22.9 mmol), and Pd(dppf)Cl₂ (67.1 mg, 91.7 μmol) in 1,4-dioxane (30 mL) was degassed and purged with N₂ (3×), and then the mixture was stirred at 90° C. for 12 h under N₂ atmosphere. After cooling to room temperature, the mixture was filtered, and the filtrate was concentrated in vacuo. The crude residue was purified by flash silica gel chromatography (Biotage 25 g cartridge, 0-100% EtOAc/Petroleum ether) to give tert-butyl 2-oxo-6-(4,4,5,5-tetramethyl-1,3,2-dioxaborolan-2-yl)-1,2,3,4-tetrahydro-1,8-naphthyridine-1-carboxylate. MS=375.3 [M+H]⁺.

Step 3: tert-butyl 6-hydroxy-2-oxo-1,2,3,4-tetrahydro-1,8-naphthyridine-1-carboxylate

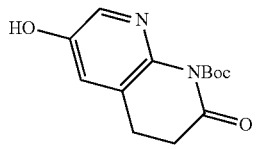 [SMILES: CC(C)(C)OC(=O)N1C(=O)CCc2cc(O)cnc21]

To a solution of tert-butyl 2-oxo-6-(4,4,5,5-tetramethyl-1,3,2-dioxaborolan-2-yl)-1,2,3,4-tetrahydro-1,8-naphthyridine-1-carboxylate (1.00 g, 2.67 mmol) in H₂O (2 mL) and THF (10 mL) was added Oxone (1.15 g, 1.87 mmol). The mixture was stirred at 0° C. for 1 h, and then was quenched with saturated aqueous Na₂SO₃ (10 mL). The mixture was extracted with EtOAc (3×10 mL). The combined organic layers were dried over Na₂SO₄, filtered, and concentrated in vacuo to give tert-butyl 6-hydroxy-2-oxo-1,2,3,4-tetrahydro-1,8-naphthyridine-1-carboxylate, which was used in the subsequent step without further purification. MS=265.1 [M+H]⁺.

Step 4: tert-butyl 6-(2-bromoethoxy)-2-oxo-1,2,3,4-tetrahydro-1,8-naphthyridine-1-carboxylate

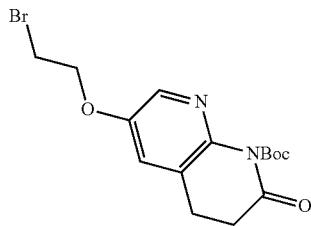 [SMILES: CC(C)(C)OC(=O)N1C(=O)CCc2cc(OCCBr)cnc21]

To a solution of tert-butyl 6-hydroxy-2-oxo-1,2,3,4-tetrahydro-1,8-naphthyridine-1-carboxylate (900 mg, 3.41 mmol) in MeCN (7 mL) and 1,2-dibromoethane (16 mL) was added K₂CO₃ (2.35 g, 17.0 mmol). The mixture was stirred at 80° C. for 16 h. After cooling to room temperature, the reaction mixture was concentrated in vacuo. The crude residue was purified by flash silica gel chromatography (Biotage 4 g cartridge, 0-50% EtOAc/Petroleum ether) to give tert-butyl 6-(2-bromoethoxy)-2-oxo-1,2,3,4-tetrahydro-1,8-naphthyridine-1-carboxylate. MS=371.1/373.1 [M+H]⁺.

Step 5: tert-butyl 6-(2-{5-chloro-2-oxo-1,2-dihydrospiro[indole-3,4'-piperidin]-1'-yl}ethoxy)-2-oxo-1,2,3,4-tetrahydro-1,8-naphthyridine-1-carboxylate

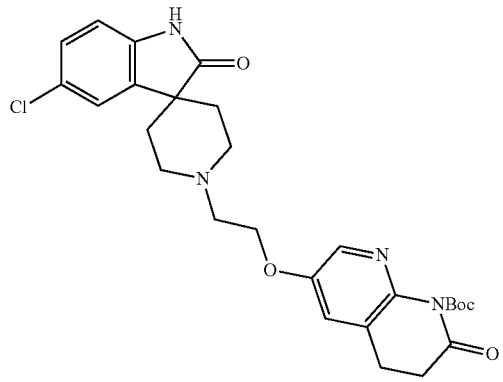 [SMILES: CC(C)(C)OC(=O)N1C(=O)CCc2cc(OCCN3CCC4(CC3)C(=O)Nc3ccc(Cl)cc34)cnc21]

To a solution of 5-chloro-1H-spiro[indole-3,4'-piperidin]-2-one (Intermediate B-4, 515 mg, 1.89 mmol, HCl salt) in MeCN (10 mL) was added NaHCO₃ (634 mg, 7.54 mmol) and tert-butyl 6-(2-bromoethoxy)-2-oxo-1,2,3,4-tetrahydro-1,8-naphthyridine-1-carboxylate (700 mg, 1.89 mmol). The mixture was stirred at 80° C. for 12 h. After cooling to room temperature, the reaction mixture was filtered and concentrated in vacuo. The residue was purified by preparative TLC (SiO₂, 100% EtOAc) to give tert-butyl 6-(2-{5-chloro-2-oxo-1,2-dihydrospiro[indole-3,4'-piperidin]-1'-yl}ethoxy)-2-oxo-1,2,3,4-tetrahydro-1,8-naphthyridine-1-carboxylate. MS=527.0 [M+H]⁺.

Step 6: 5-chloro-1'-{2-[(7-oxo-5,6,7,8-tetrahydro-1,8-naphthyridin-3-yl)oxy]ethyl}-1,2-dihydrospiro[indole-3,4'-piperidin]-2-one (Compound 293)

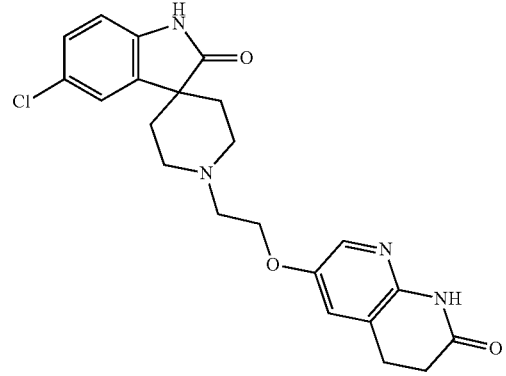 [SMILES: O=C1CCc2cc(OCCN3CCC4(CC3)C(=O)Nc3ccc(Cl)cc34)cnc2N1]

A mixture of tert-butyl 6-(2-{5-chloro-2-oxo-1,2-dihydrospiro[indole-3,4'-piperidin]-1'-yl}ethoxy)-2-oxo-1,2,3,4-tetrahydro-1,8-naphthyridine-1-carboxylate (330 mg, 0.626 mmol) in 4.0 M HCl in EtOAc (10 mL, 40 mmol) was stirred at room temperature for 2 h. The reaction mixture was concentrated under reduced pressure. The crude residue was purified by reverse phase preparative HPLC (Waters Xbridge BEH C₁₈ column, 20-50% MeCN: 10 mM NH₄HCO₃ in H₂O) to give 5-chloro-1'-{2-[(7-oxo-5,6,7,8-tetrahydro-1,8-naphthyridin-3-yl)oxy]ethyl}-1,2-dihydrospiro[indole-3,4'-piperidin]-2-one (Compound 293). ¹H NMR (400 MHz, DMSO-d₆): δ 9.67 (s, 1H), 9.46 (s, 1H), 7.02 (d, J=2.8 Hz, 1H), 6.69 (d, J=2.0 Hz, 1H), 6.53 (d, J=2.6 Hz, 1H), 6.42 (dd, J=8.0 Hz, 2.0 Hz, 1H), 6.03 (d, J=8.4 Hz, 1H), 3.33 (t, J=5.6 Hz, 2H), 1.98-2.17 (m, 6H), 1.87-1.82 (m, 2H), 1.66-1.57 (m, 2H), 0.99-0.90 (m, 4H). MS=427.2 [M+H]⁺.

Example 75

5,7-dichloro-1'-(2-{[2-(1-methanesulfonylcyclopropyl)pyrimidin-5-yl]oxy}ethyl)-1,2-dihydrospiro[indole-3,4'-piperidin]-2-one (Compound 400)

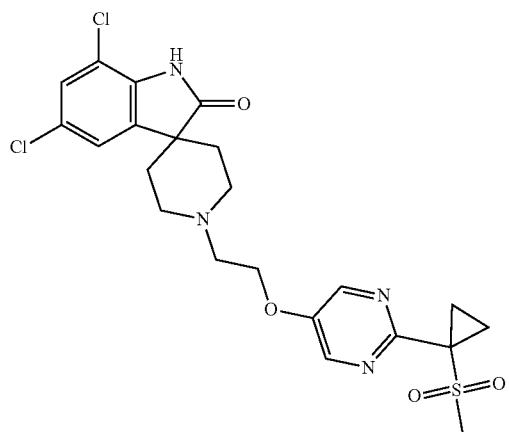 [SMILES: CS(=O)(=O)C1(c2ncc(OCCN3CCC4(CC3)C(=O)Nc3c(Cl)cc(Cl)cc34)cn2)CC1]

To a solution of 5-chloro-1'-(2-{[2-(1-methanesulfonyl-cyclopropyl)pyrimidin-5-yl]oxy}ethyl)-1,2-dihydrospiro[indole-3,4'-piperidin]-2-one (Compound 4, 100 mg, 0.21 mmol) and NCS (0.056 g, 0.419 mmol) in MeCN (0.5 mL) was added TMSCl (0.023 g, 0.21 mmol). The reaction was allowed to stir at room temperature overnight. The reaction was diluted with H₂O (1 mL) and DMSO (1 mL), and then purified by reverse phase C18 chromatography (5-50% MeCN in H₂O with 0.1% NH₄OH modifier) to give 5,7-dichloro-1'-(2-{[2-(1-methanesulfonylcyclopropyl)pyrimidin-5-yl]oxy}ethyl)-1H-spiro[indole-3,4'-piperidin]-2-one (Compound 400). ¹H NMR (500 MHz, DMSO): δ 10.87 (s, 1H), 8.54 (s, 2H), 7.45 (s, 1H), 7.36 (s, 1H), 4.26 (t, J=5.6 Hz, 2H), 3.29 (s, 3H), 2.86-2.78 (m, 4H), 2.66-2.61 (m, 2H), 1.72-1.65 (m, 6H), 1.54-1.51 (m, 2H). MS=511.1 [M+H]⁺.

Example 76

5-chloro-1'-[2-({1-[(cis)-3-hydroxy-3-methylcyclobutyl]-7-(trifluoromethyl)-1H-1,3-benzodiazol-5-yl}oxy)ethyl]-1,2-dihydrospiro[indole-3,4'-piperidin]-2-one (Compound 352)

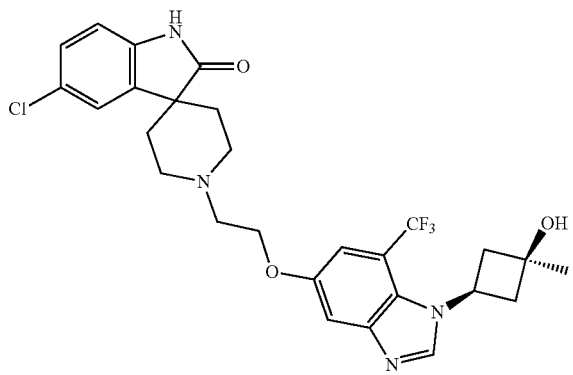 [SMILES: C[C@]1(O)C[C@@H](n2cnc3cc(OCCN4CCC5(CC4)C(=O)Nc4ccc(Cl)cc45)cc(C(F)(F)F)c32)C1]

Step 1: (cis)-3-[5-(2-bromoethoxy)-7-(trifluoromethyl)-1H-1,3-benzodiazol-1-yl]-1-methylcyclobutan-1-ol

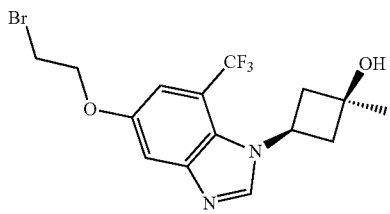

To a solution of 1-[(cis)-3-hydroxy-3-methylcyclobutyl]-7-(trifluoromethyl)-1H-1,3-benzodiazol-5-ol (Intermediate A-92, 610 mg, 2.13 mmol) in MeCN (12.2 mL) was added K₂CO₃ (1.47 g, 10.7 mmol) and 1,2-dibromoethane (16.0 g, 85.2 mmol). The mixture was stirred at 80° C. for 16 h. After cooling to room temperature, the reaction mixture was quenched by addition of H₂O (50 mL) and extracted with EtOAc (3×50 mL). The combined organic layers were washed with brine (2×20 mL), dried over Na₂SO₄, filtered, and concentrated under reduced pressure. The residue was purified by flash silica gel chromatography (Biotage 12 g cartridge, 0-30% MeOH/EtOAc) to give (cis)-3-[5-(2-bromoethoxy)-7-(trifluoromethyl)-1H-1,3-benzodiazol-1-yl]-1-methylcyclobutan-1-ol. MS=393.0/395.0 [M+H]⁺.

Alternative Conditions for Step 1: (cis)-3-[5-(2-bromoethoxy)-7-(trifluoromethyl)-1H-1,3-benzodiazol-1-yl]-1-methylcyclobutan-1-ol

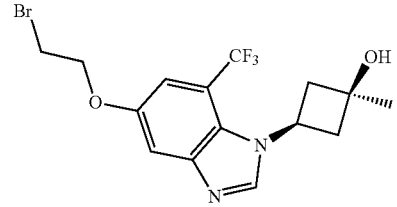 [SMILES: C[C@]1(O)C[C@@H](n2cnc3cc(OCCBr)cc(C(F)(F)F)c32)C1]

A solution of 1-[(cis)-3-hydroxy-3-methylcyclobutyl]-7-(trifluoromethyl)-1H-1,3-benzodiazol-5-ol (Intermediate A-92, 1.00 g, 3.49 mmol), 1,2-dibromoethane (5.27 mL, 69.9 mmol) and Cs₂CO₃ (2.85 g, 8.73 mmol) in i-PrOH (5 mL) was stirred at 60° C. for 16 h. After cooling to room temperature, solids were removed by filtration and the filtrate was concentrated in vacuo. The residue was purified by flash silica gel chromatography (Biotage 20 g cartridge, 50-90% EtOAc/Petroleum ether) to give (cis)-3-[5-(2-bromoethoxy)-7-(trifluoromethyl)-1H-1,3-benzodiazol-1-yl]-1-methylcyclobutan-1-ol. MS=393.0/394.9 [M+H]⁺.

Step 2: 5-chloro-1'-[2-({1-[(cis)-3-hydroxy-3-methylcyclobutyl]-7-(trifluoromethyl)-1H-1,3-benzodiazol-5-yl}oxy)ethyl]-1,2-dihydrospiro[indole-3,4'-piperidin]-2-one

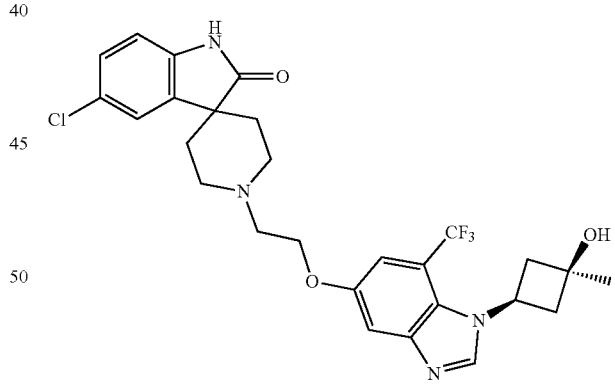

To a solution of (cis)-3-[5-(2-bromoethoxy)-7-(trifluoromethyl)-1H-1,3-benzodiazol-1-yl]-1-methylcyclobutan-1-ol (420 mg, 1.07 mmol) in MeCN (7 mL) was added NaHCO₃ (449 mg, 5.34 mmol) and 5-chloro-1,2-dihydrospiro[indole-3,4'-piperidin]-2-one (Intermediate B-4, 321 mg, 1.17 mmol, HCl salt). The mixture was stirred at 80° C. for 12 h. After cooling to room temperature, the reaction mixture was quenched by addition of H₂O (20 mL) and extracted with EtOAc (3×40 mL). The combined organic layers were washed with brine (40 mL), dried over Na₂SO₄, filtered, and concentrated under reduced pressure. The residue was suspended in MeCN (10 mL) and the mixture was stirred at 80° C. for 1 h. The mixture was cooled to room temperature and filtered to collect the solid. The filter cake was dried in vacuo to give 5-chloro-1'-[2-({1-[(cis)-3-hydroxy-3-methylcyclobutyl]-7-(trifluoromethyl)-1H-1,3-benzodiazol-5-yl}oxy)ethyl]-1,2-dihydrospiro[indole-3,4'-piperidin]-2-one (Compound 352). $^1$H NMR (400 MHz, DMSO-d$_6$): δ 10.48 (s, 1H), 8.67 (s, 1H), 7.60 (d, J=2.0 Hz, 1H), 7.49 (d, J=2.0 Hz, 1H), 7.26-7.21 (m, 2H), 6.83 (d, J=8.4 Hz, 1H), 5.30 (s, 1H), 4.57 (pent, J=8.0 Hz, 1H), 4.26-4.23 (m, 2H), 2.93-2.87 (m, 4H), 2.72-2.62 (m, 2H), 2.60-2.50 (m, 4H), 1.79-1.68 (m, 4H), 1.33 (s, 3H). MS=549.0 [M+H]$^+$.

Example 77

5-chloro-1'-[2-({3-oxo-4-[(cis)-3-hydroxy-3-methyl-cyclobutyl]-3H,4H-pyrido[2,3-b]pyrazin-7-yl}oxy)ethyl]-1,2-dihydrospiro[indole-3,4'-piperidin]-2-one (Compound 358)

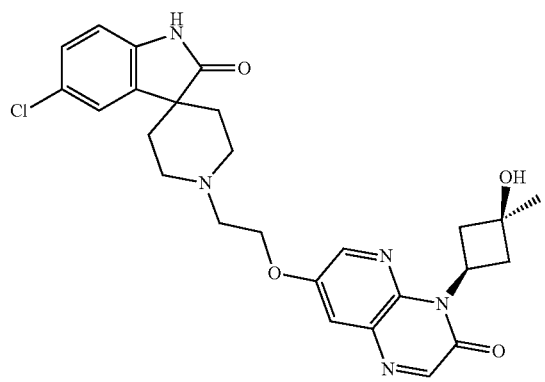 [SMILES: C[C@]1(O)C[C@@H](n2c(=O)cnc3cc(OCCN4CCC5(CC4)C(=O)Nc4ccc(Cl)cc45)cnc32)C1]

Step 1: 7-(2-bromoethoxy)-4-[(cis)-3-hydroxy-3-methylcyclobutyl]-3H,4H-pyrido[2,3-b]pyrazin-3-one

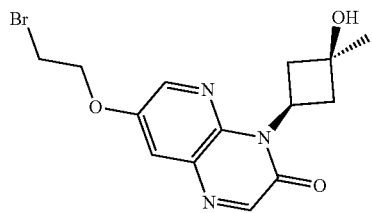 [SMILES: C[C@]1(O)C[C@@H](n2c(=O)cnc3cc(OCCBr)cnc32)C1]

To a solution of 7-hydroxy-4-[(cis)-3-hydroxy-3-methylcyclobutyl]-3H,4H-pyrido[2,3-b]pyrazin-3-one (Intermediate A-94, 140 mg, 0.388 mmol, TFA salt) and 1,2-dibromoethane (1.17 mL, 15.5 mmol) in MeCN (4 mL) was added K$_2$CO$_3$ (321 mg, 2.33 mmol). The mixture was stirred at 65° C. for 12 h. After cooling to room temperature, the mixture was diluted with H$_2$O (30 mL) and extracted with EtOAc (2×50 mL). The combined organic layers were washed with brine (50 mL), dried over Na$_2$SO$_4$, filtered, and concentrated in vacuo. The crude residue was purified by flash silica gel chromatography (Biotage 4 g cartridge, 0-72% EtOAc/Petroleum ether) to give 7-(2-bromoethoxy)-4-[(cis)-3-hydroxy-3-methylcyclobutyl]-3H,4H-pyrido[2,3-b]pyrazin-3-one. MS=354.2/356.1 [M+H]$^+$.

Step 2: 5-chloro-1'-[2-({3-oxo-4-[(cis)-3-hydroxy-3-methylcyclobutyl]-3H,4H-pyrido[2,3-b]pyrazin-7-yl}oxy)ethyl]-1,2-dihydrospiro[indole-3,4'-piperidin]-2-one (Compound 358)

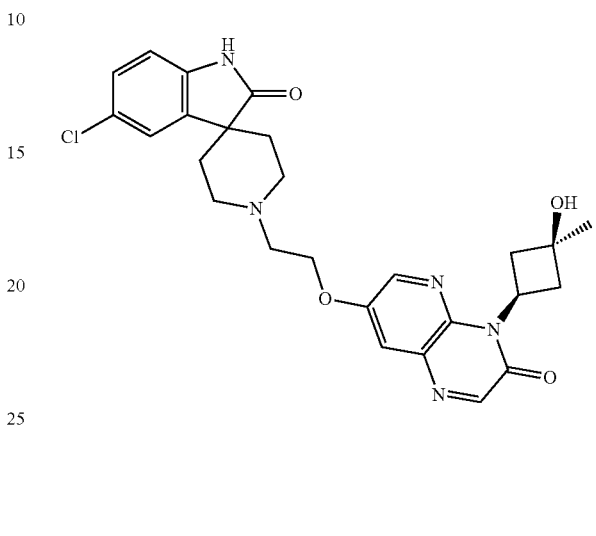

To a solution of 5-chloro-1'-[2-({3-oxo-4-[(cis)-3-hydroxy-3-methylcyclobutyl]-3H,4H-pyrido[2,3-b]pyrazin-7-yl}oxy)ethyl]-1,2-dihydrospiro[indole-3,4'-piperidin]-2-one (130 mg, 0.367 mmol) and 5-chloro-1,2-dihydrospiro[indole-3,4'-piperidin]-2-one (Intermediate B-4, 95.6 mg, 0.404 mmol, HCl salt) in MeCN (5 mL) was added NaHCO$_3$ (93.3 mg, 1.10 mmol). The mixture was stirred at 80° C. for 12 h. After cooling to room temperature, the mixture was diluted with H$_2$O (10 mL) and extracted with EtOAc (3×15 mL). The combined organic layers were washed with brine (15 mL), dried over Na$_2$SO$_4$, filtered, and concentrated in vacuo. The crude residue was purified by reverse phase preparative HPLC (Waters Xbridge OBD C$_{18}$ column, 25-55% MeCN: 10 mM NH$_4$HCO$_3$ in H$_2$O) to give 5-chloro-1'-[2-({3-oxo-4-[(cis)-3-hydroxy-3-methylcyclobutyl]-3H,4H-pyrido[2,3-b]pyrazin-7-yl}oxy)ethyl]-1,2-dihydrospiro[indole-3,4'-piperidin]-2-one (Compound 358). $^1$H NMR (400 MHz, DMSO-d$_6$): δ 10.54-10.45 (m, 1H), 8.44 (d, J=2.8 Hz, 1H), 8.23 (s, 1H), 7.93 (d, J=3.2 Hz, 1H), 7.50 (d, J=2.0 Hz, 1H), 7.23 (dd, J=8.4, 2.0 Hz, 1H), 6.84 (d, J=8.0 Hz, 1H), 5.21-5.11 (m, 1H), 5.02 (s, 1H), 4.34-4.29 (m, 2H), 3.02-2.96 (m, 2H), 2.95-2.91 (m, 2H), 2.91-2.88 (m, 2H), 2.74-2.68 (m, 2H), 2.44-2.40 (m, 2H), 1.81-1.75 (m, 2H), 1.74-1.67 (m, 2H), 1.33 (s, 3H). MS=510.1 [M+H]$^+$.

The following compounds in Table 38.9 were prepared according to procedures analogous to those described for Compound 358 using the appropriate starting materials or common intermediates.

TABLE 38.9

| No. | Structure | IUPAC Name | Exact Mass [M + H]+ | Intermediates Used | Chiral separation column | Chiral elution order |
|---|---|---|---|---|---|---|
| 401 | 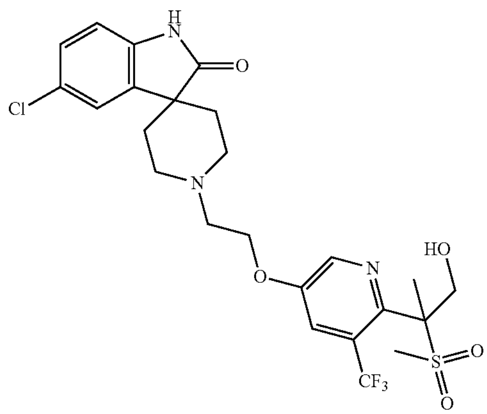 [SMILES: CC(CO)(c1ncc(OCCN2CCC3(CC2)C(=O)Nc2ccc(Cl)cc23)cc1C(F)(F)F)S(C)(=O)=O] | 5-chloro-1'-(2-{[6-(1-hydroxy-2-methanesulfonyl-propan-2-yl)-5-(trifluoro-methyl)pyridin-3-yl]oxy}ethyl)-1,2-dihydrospiro[indole-3,4'-piperidin]-2-one | Calc'd 562.1 Found 562.0 | A-95 and B-4 | n/a | n/a |
| 402 | 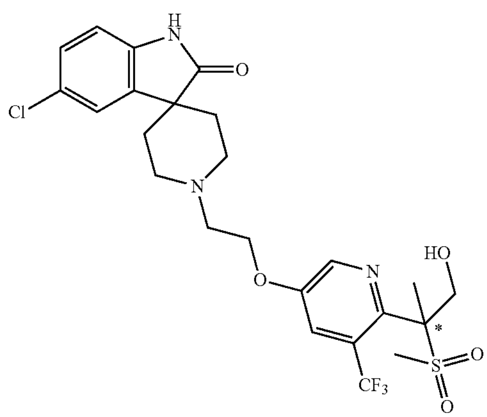 [SMILES: CC(CO)(c1ncc(OCCN2CCC3(CC2)C(=O)Nc2ccc(Cl)cc23)cc1C(F)(F)F)S(C)(=O)=O] | 5-chloro-1'-[2-({6-[(2S or 2R)-1-hydroxy-2-methanesulfonyl-propan-2-yl]-5-(trifluoro-methyl)pyridin-3-yl}oxy)ethyl]-1,2-dihydrospiro[indole-3,4'-piperidin]-2-one | Calc'd 562.1 Found 561.9 | A-95 and B-4 | Daicel Chiralpak AD-3 | 1st |
| 403 | 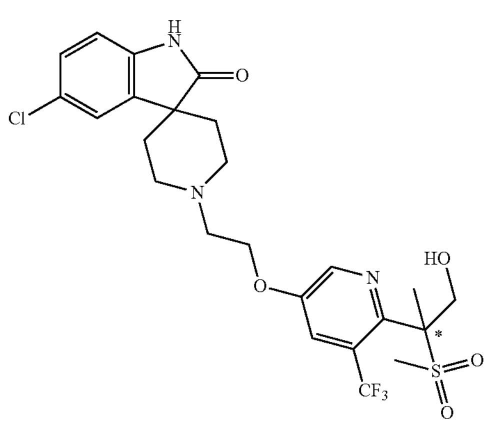 [SMILES: CC(CO)(c1ncc(OCCN2CCC3(CC2)C(=O)Nc2ccc(Cl)cc23)cc1C(F)(F)F)S(C)(=O)=O] | 5-chloro-1'-[2-({6-[(2R or 2S)-1-hydroxy-2-methanesulfonyl-propan-2-yl]-5-(trifluoro-methyl)pyridin-3-yl}oxy)ethyl]-1,2-dihydrospiro[indole-3,4'-piperidin]-2-one | Calc'd 562.1 Found 562.0 | A-95 and B-4 | Daicel Chiralpak AD-3 | 2nd |

TABLE 38.9-continued

| No. | Structure | IUPAC Name | Exact Mass [M + H]+ | Intermediates Used | Chiral separation column | Chiral elution order |
|---|---|---|---|---|---|---|
| 344 | 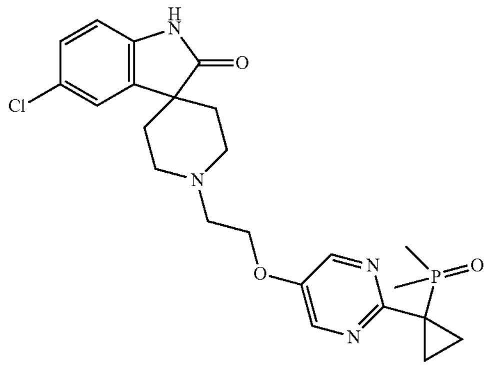 [SMILES: CP(C)(=O)C1(c2ncc(OCCN3CCC4(CC3)C(=O)Nc3ccc(Cl)cc34)cn2)CC1] | 5-chloro-1'-[2-({2-[1-(dimethylphosphoryl)cyclopropyl]pyrimidin-5-yl}oxy)ethyl]-1,2-dihydrospiro[indole-3,4'-piperidin]-2-one | Calc'd 475.2 Found 475.2 | A-96 and B-4 | n/a | n/a |
| 404 | 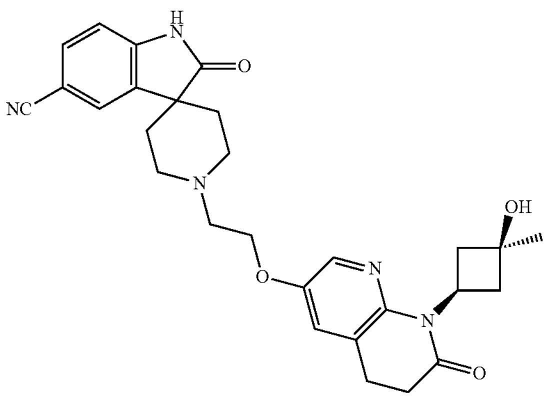 [SMILES: C[C@]1(O)C[C@@H](N2C(=O)CCc3cc(OCCN4CCC5(CC4)C(=O)Nc4ccc(C#N)cc45)cnc32)C1] | 2-oxo-1'-[2-({7-oxo-8-[(cis)-3-hydroxy-3-methylcyclobutyl]-5,6,7,8-tetrahydro-1,8-naphthyridin-3-yl}oxy)ethyl]-1,2-dihydrospiro[indole-3,4'-piperidine]-5-carbonitrile | Calc'd 502.2 Found 502.2 | A-89 and B-9 | n/a | n/a |
| 367 | 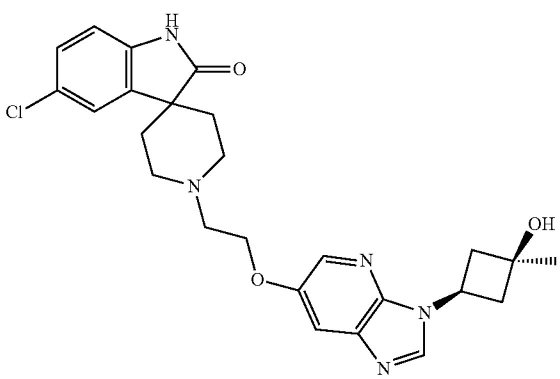 [SMILES: C[C@]1(O)C[C@@H](n2cnc3cc(OCCN4CCC5(CC4)C(=O)Nc4ccc(Cl)cc45)cnc32)C1] | 5-chloro-1'-[2-({3-[(cis)-3-hydroxy-3-methylcyclobutyl]-3H-imidazo[4,5-b]pyridin-6-yl}oxy)ethyl]-1,2-dihydrospiro[indole-3,4'-piperidin]-2-one | Calc'd 482.2 Found 482.2 | A-98 and B-4 | n/a | n/a |
| 405 | 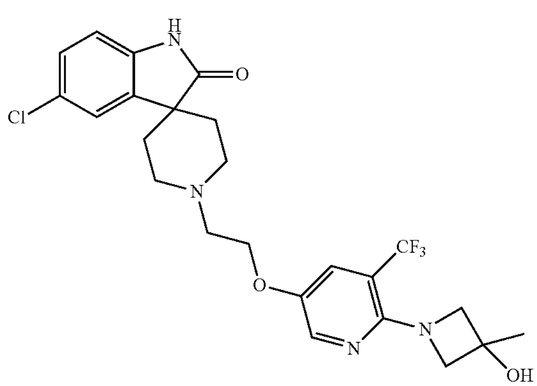 [SMILES: CC1(O)CN(c2ncc(OCCN3CCC4(CC3)C(=O)Nc3ccc(Cl)cc34)cc2C(F)(F)F)C1] | 5-chloro-1'-(2-{[6-(3-hydroxy-3-methylazetidin-1-yl)-5-(trifluoromethyl)pyridin-3-yl]oxy}ethyl)-1,2-dihydrospiro[indole-3,4'-piperidin]-2-one | Calc'd 511.2 Found 511.2 | A-99 and B-4 | n/a | n/a |

TABLE 38.9-continued

| No. | Structure | IUPAC Name | Exact Mass [M + H]+ | Intermediates Used | Chiral separation column | Chiral elution order |
|---|---|---|---|---|---|---|
| 406 | 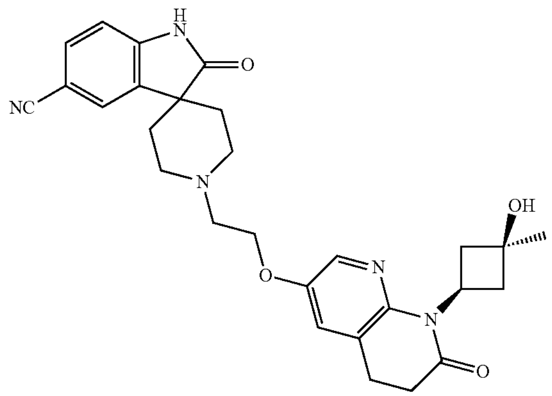 [SMILES: C[C@]1(O)C[C@@H](N2C(=O)CCc3cc(OCCN4CCC5(CC4)C(=O)Nc4ccc(C#N)cc45)cnc32)C1] | 2-oxo-1'-[2-({7-oxo-8-[(cis)-3-hydroxy-3-methylcyclobutyl]-7,8-dihydro-1,8-naphthyridin-3-yl}oxy)ethyl]-1,2-dihydrospiro[indole-3,4'-piperidine]-5-carbonitrile | Calc'd 500.2 Found 500.3 | Example 68, Step 4 and B-9 | n/a | n/a |
| 357 | 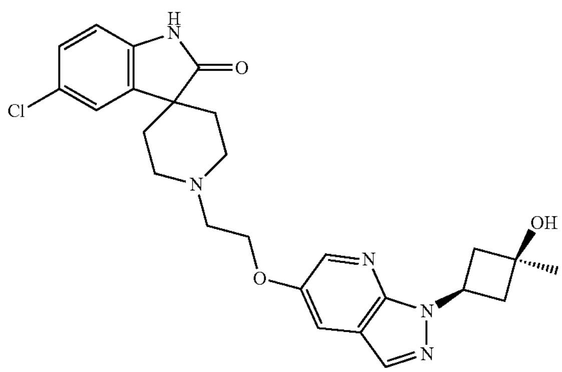 [SMILES: C[C@]1(O)C[C@@H](n2ncc3cc(OCCN4CCC5(CC4)C(=O)Nc4ccc(Cl)cc45)cnc32)C1] | 5-chloro-1'-[2-({1-[(cis)-3-hydroxy-3-methylcyclobutyl]-1H-pyrazolo[3,4-b]pyridin-5-yl}oxy)ethyl]-1,2-dihydrospiro[indole-3,4'-piperidin]-2-one | Calc'd 482.2 Found 482.3 | A-116 and B-4 | Daicel Chiralpak AD | 2nd |
| 407 | 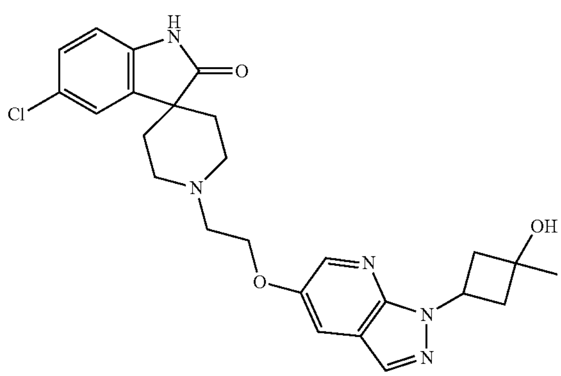 [SMILES: CC1(O)CC(n2ncc3cc(OCCN4CCC5(CC4)C(=O)Nc4ccc(Cl)cc45)cnc32)C1] | 5-chloro-1'-(2-{[1-(3-hydroxy-3-methylcyclobutyl)-1H-pyrazolo[3,4-b]pyridin-5-yl]oxy}ethyl)-1,2-dihydrospiro[indole-3,4'-piperidin]-2-one | Calc'd 482.2 Found 482.1 | A-116 and B-4 | n/a | n/a |
| 408 | 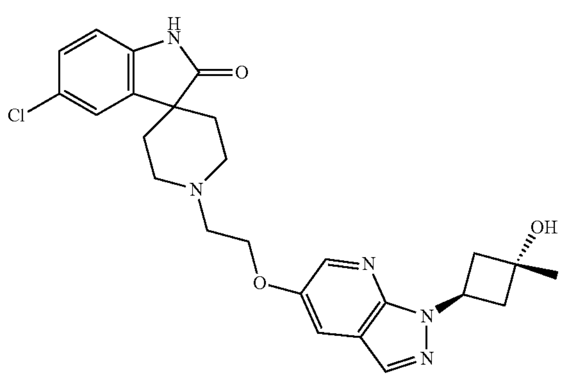 [SMILES: C[C@]1(O)C[C@H](n2ncc3cc(OCCN4CCC5(CC4)C(=O)Nc4ccc(Cl)cc45)cnc32)C1] | 5-chloro-1'-[2-({1-[(trans)-3-hydroxy-3-methylcyclobutyl]-1H-pyrazolo[3,4-b]pyridin-5-yl}oxy)ethyl]-1,2-dihydrospiro[indole-3,4'-piperidin]-2-one | Calc'd 482.2 Found 482.1 | A-116 and B-4 | Daicel Chiralpak AD | 1st |

TABLE 38.9-continued

| No. | Structure | IUPAC Name | Exact Mass [M + H]+ | Intermediates Used | Chiral separation column | Chiral elution order |
|---|---|---|---|---|---|---|
| 334 | 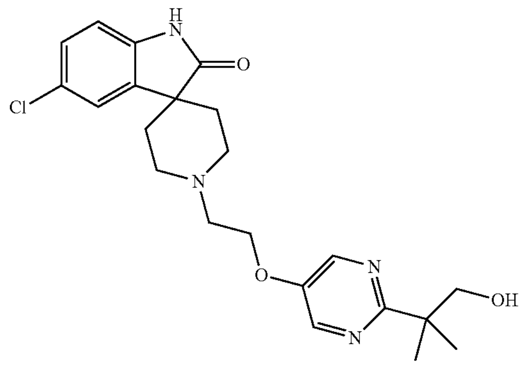 [SMILES: CC(C)(CO)c1ncc(OCCN2CCC3(CC2)C(=O)Nc2ccc(Cl)cc23)cn1] | 5-chloro-1'-(2-{[2-(1-hydroxy-2-methylpropan-2-yl)pyrimidin-5-yl]oxy}ethyl)-1,2-dihydrospiro[indole-3,4'-piperidin]-2-one | Calc'd 431.2 Found 431.2 | A-100 and B-4 | n/a | n/a |
| 409 | 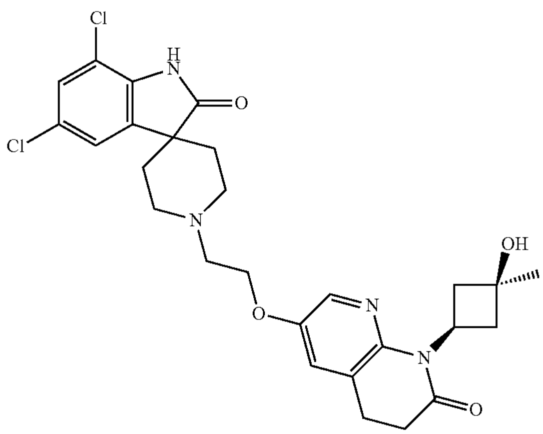 [SMILES: C[C@]1(O)C[C@@H](N2C(=O)CCc3cc(OCCN4CCC5(CC4)C(=O)Nc4c(Cl)cc(Cl)cc45)cnc32)C1] | 5,7-dichloro-1'-[2-({7-oxo-8-[(cis)-3-hydroxy-3-methylcyclobutyl]-5,6,7,8-tetrahydro-1,8-naphthyridin-3-yl}oxy)ethyl]-1,2-dihydrospiro[indole-3,4'-piperidin]-2-one | Calc'd 545.2 Found 545.2 | General Procedure for Intermediate A-89, Step 3 and Example 3, Step 2 | n/a | n/a |
| 333* | 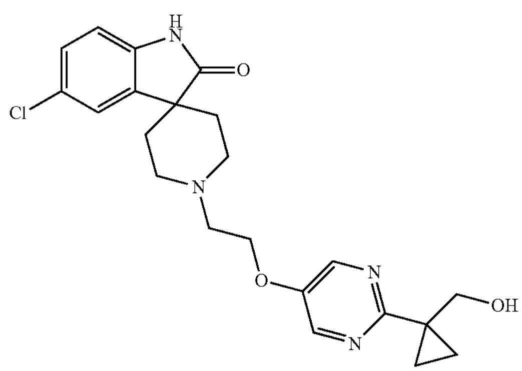 [SMILES: O=C1Nc2ccc(Cl)cc2C12CCN(CCOc1cnc(C3(CO)CC3)nc1)CC2] | 5-chloro-1'-[2-({2-[1-(hydroxymethyl)cyclopropyl]pyrimidin-5-yl}oxy)ethyl]-1,2-dihydrospiro[indole-3,4'-piperidin]-2-one | Calc'd 429.2 Found 429.1 | A-101 and B-4 | n/a | n/a |
| 343 | 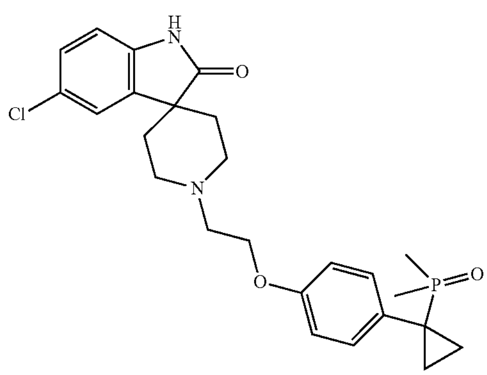 [SMILES: CP(C)(=O)C1(c2ccc(OCCN3CCC4(CC3)C(=O)Nc3ccc(Cl)cc34)cc2)CC1] | 5-chloro-1'-(2-{4-[1-(dimethylphosphoryl)cyclopropyl]phenoxy}ethyl)-1,2-dihydrospiro[indole-3,4'-piperidin]-2-one | Calc'd 473.2 Found 473.3 | A-102 and B-4 | n/a | n/a |

*Prepared according to procedures analogous to Step 2 in procedure for synthesis of Compound 358

Example 78

5-chloro-1'-[2-({1-[(cis)-3-hydroxy-3-methylcyclobutyl]-1H-pyrrolo[2,3-b]pyridin-5-yl}oxy)ethyl]-1,2-dihydrospiro[indole-3,4'-piperidin]-2-one (Compound 349)

Step 1: [5-bromo-1-[(cis)-3-[(tert-butyldimethylsilyl)oxy]-3-methylcyclobutyl]-1H-pyrrolo[2,3-b]pyridine

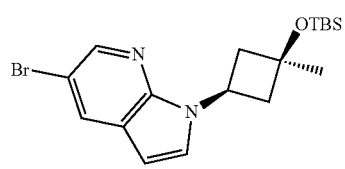 [SMILES: CC(C)(C)[Si](C)(C)O[C@]1(C)C[C@H](n2ccc3cc(Br)cnc32)C1]

To a mixture of 5-bromo-1H-pyrrolo[2,3-b]pyridine (5.00 g, 25.4 mmol) and tert-butyldimethyl[(cis)-3-bromo-1-methylcyclobutoxy]silane (10.6 g, 38.1 mmol) in DMF (80 mL) was added Cs$_2$CO$_3$ (20.7 g, 63.4 mmol). The mixture was stirred at 90° C. for 30 h. After cooling to room temperature, the reaction mixture was diluted with H$_2$O (200 mL) and extracted with EtOAc (3×50 mL). The combined organic layers were dried over Na$_2$SO$_4$, filtered, and concentrated under reduced pressure. The residue was purified by flash silica gel chromatography (Biotage 120 g cartridge, 0-10% EtOAc/Petroleum ether), and then further purified by reverse phase preparative HPLC (Phenomenex C$_{18}$ column, 75-99% MeCN: 10 mM NH$_4$HCO$_3$ in H$_2$O) to give tert-butyldimethyl[(cis)-3-bromo-1-methylcyclobutoxy]silane. MS=395.0/397.0 [M+H]$^+$.

Step 2: 1-[(cis)-3-[(tert-butyldimethylsilyl)oxy]-3-methylcyclobutyl]-5-(4,4,5,5-tetramethyl-1,3,2-dioxaborolan-2-yl)-1H-pyrrolo[2,3-b]pyridine

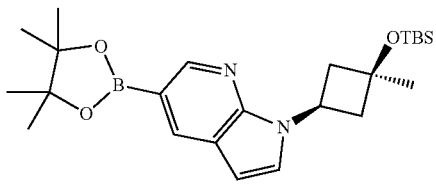

A mixture of bis(pinacolato)diboron (1.41 g, 5.55 mmol), tert-butyldimethyl[(cis)-3-bromo-1-methylcyclobutoxy]silane (1.83 g, 4.63 mmol), KOAc (908 mg, 9.26 mmol) and Pd(dppf)Cl$_2$ (169 mg, 231 µmol) in 1,4-dioxane (20 mL) was degassed and purged with N$_2$ (3×), and then the mixture was stirred at 80° C. for 15 h under N$_2$ atmosphere. After cooling to room temperature, the reaction mixture was filtered through a pad of celite and the filtrate was concentrated under reduced pressure to give 1-[(cis)-3-[(tert-butyldimethylsilyl)oxy]-3-methylcyclobutyl]-5-(4,4,5,5-tetramethyl-1,3,2-dioxaborolan-2-yl)-1H-pyrrolo[2,3-b]pyridine, which was taken to the next step without further purification. MS=443.2 [M+H]$^+$.

Step 3: 1-[(cis)-3-[(tert-butyldimethylsilyl)oxy]-3-methylcyclobutyl]-1H-pyrrolo[2,3-b]pyridin-5-ol

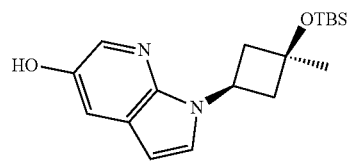 [SMILES: CC(C)(C)[Si](C)(C)O[C@]1(C)C[C@H](n2ccc3cc(O)cnc32)C1]

To a 0° C. solution of 1-[(cis)-3-[(tert-butyldimethylsilyl)oxy]-3-methylcyclobutyl]-5-(4,4,5,5-tetramethyl-1,3,2-dioxaborolan-2-yl)-1H-pyrrolo[2,3-b]pyridine (2.05 g, 4.63 mmol) in acetone (20 mL) and H$_2$O (20 mL) was added Oxone (1.42 g, 2.32 mmol). The mixture was stirred at room temperature for 2 h. The reaction mixture was diluted with H$_2$O (50 mL) and extracted with EtOAc (3×40 mL). The combined organic layers were dried over Na$_2$SO$_4$, filtered, and concentrated under reduced pressure. The residue was purified by flash silica gel chromatography (Biotage 40 g cartridge, 0-50% EtOAc/Petroleum ether) to give 1-[(cis)-3-[(tert-butyldimethylsilyl)oxy]-3-methylcyclobutyl]-1H-pyrrolo[2,3-b]pyridin-5-ol. MS=333.1 [M+H]$^+$.

Step 4: 5-(2-bromoethoxy)-1-[(cis)-3-[(tert-butyldimethylsilyl)oxy]-3-methylcyclobutyl]-1H-pyrrolo[2,3-b]pyridine

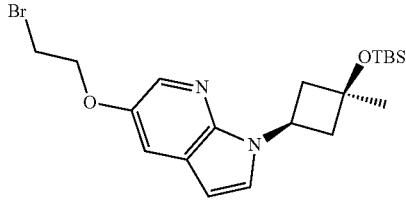 [SMILES: CC(C)(C)[Si](C)(C)O[C@]1(C)C[C@H](n2ccc3cc(OCCBr)cnc32)C1]

To a mixture of 1,2-dibromoethane (7.68 g, 40.9 mmol) and 1-[(cis)-3-[(tert-butyldimethylsilyl)oxy]-3-methylcyclobutyl]-1H-pyrrolo[2,3-b]pyridin-5-ol (340 mg, 1.02 mmol) in MeCN (5 mL) was added K$_2$CO$_3$ (707 mg, 5.11 mmol). The mixture was stirred at 85° C. for 63 h. After cooling to room temperature, the reaction mixture was diluted with H$_2$O (10 mL) and extracted with DCM (3×10 mL). The combined organic layers were dried over Na$_2$SO$_4$, filtered, and concentrated under reduced pressure. The residue was purified by flash silica gel chromatography (Biotage 20 g cartridge, 0-100% EtOAc/Petroleum ether) to give 5-(2-bromoethoxy)-1-[(cis)-3-[(tert-butyldimethylsilyl)oxy]-3-methylcyclobutyl]-1H-pyrrolo[2,3-b]pyridine. MS=439.0/441.0 [M+H]$^+$.

Step 5: (cis)-3-[5-(2-bromoethoxy)-1H-pyrrolo[2,3-b]pyridin-1-yl]-1-methylcyclobutan-1-ol

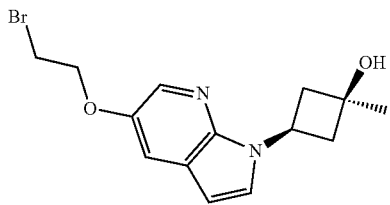 [SMILES: C[C@]1(O)C[C@@H](n2ccc3cc(OCCBr)cnc32)C1]

A solution of 5-(2-bromoethoxy)-1-[(cis)-3-[(tert-butyldimethylsilyl)oxy]-3-methylcyclobutyl]-1H-pyrrolo[2,3-b]pyridine (485 mg, 1.10 mmol) in 4.0 M HCl in EtOAc (5.0 mL, 20 mmol) was stirred at room temperature for 2 h. The reaction mixture was filtered and the filter cake was washed with Petroleum ether (3×1 mL) and dried under reduced pressure to give (cis)-3-[5-(2-bromoethoxy)-1H-pyrrolo[2,3-b]pyridin-1-yl]-1-methylcyclobutan-1-ol (HCl salt), which was taken to the next step without further purification. MS=325.0/327.0 [M+H]$^+$.

Step 6: 5-chloro-1'-[2-({1-[(cis)-3-hydroxy-3-methylcyclobutyl]-1H-pyrrolo[2,3-b]pyridin-5-yl}oxy)ethyl]-1,2-dihydrospiro[indole-3,4'-piperidin]-2-one (Compound 349)

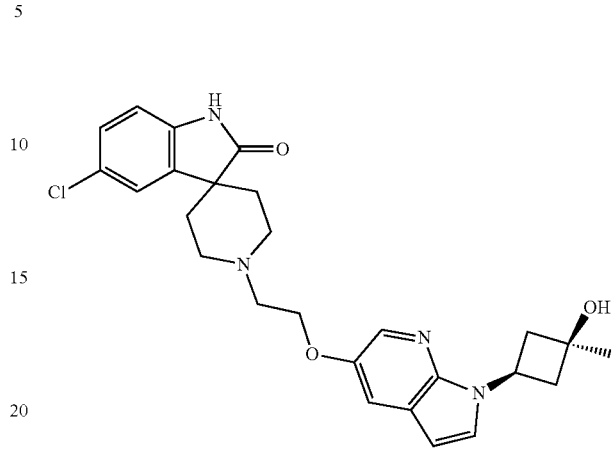

To a mixture of (cis)-3-[5-(2-bromoethoxy)-1H-pyrrolo[2,3-b]pyridin-1-yl]-1-methylcyclobutan-1-ol (100 mg, 277 μmol, HCl salt) and 5-chloro-1,2-dihydrospiro[indole-3,4'-piperidin]-2-one (Intermediate B-4, 98.2 mg, 359 μmol, HCl salt) in MeCN (2 mL) was added NaHCO$_3$ (116 mg, 1.38 mmol). The mixture was stirred at 80° C. for 15 h. After cooling to room temperature, the reaction mixture was concentrated. The residue was purified by reverse phase preparative HPLC (Waters Xbridge BEH C$_{18}$ column, 30-60% MeCN: 10 mM NH$_4$HCO$_3$ in H$_2$O) to give 5-chloro-1'-[2-({1-[(cis)-3-hydroxy-3-methylcyclobutyl]-1H-pyrrolo[2,3-b]pyridin-5-yl}oxy)ethyl]-1,2-dihydrospiro[indole-3,4'-piperidin]-2-one (Compound 349). MS=481.0 [M+H]$^+$.

The following compounds in Table 38.10 were prepared according to procedures analogous to those described for Compound 349 using the appropriate starting materials or common intermediates.

TABLE 38.10

| No. | Structure | IUPAC Name | Exact Mass [M + H]$^+$ | Intermediate Used |
|---|---|---|---|---|
| 410 | 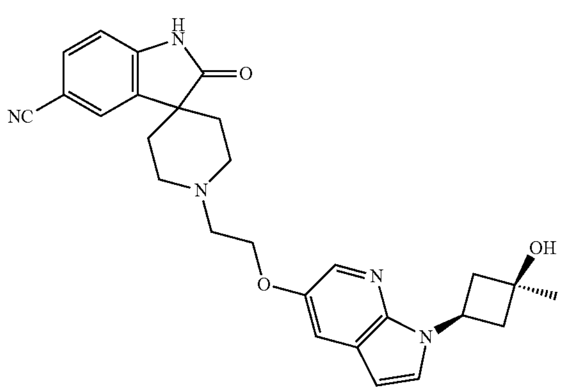 [SMILES: C[C@]1(O)C[C@@H](n2ccc3cc(OCCN4CCC5(CC4)C(=O)Nc4ccc(C#N)cc45)cnc32)C1] | 2-oxo-1'-[2-({1-[(cis)-3-hydroxy-3-methylcyclobutyl]-1H-pyrrolo[2,3-b]pyridin-5-yl}oxy)ethyl]-1,2-dihydrospiro[indole-3,4'-piperidine]-5-carbonitrile | Calc'd 472.2 Found 472.2 | B-9 |

Example 79

5-chloro-1'-[2-({2-oxo-1-[(cis)-3-hydroxy-3-methyl-cyclobutyl]-1H,2H,3H-pyrrolo[2,3-b]pyridin-5-yl}oxy)ethyl]-1,2-dihydrospiro[indole-3,4'-piperidin]-2-one (Compound 347)

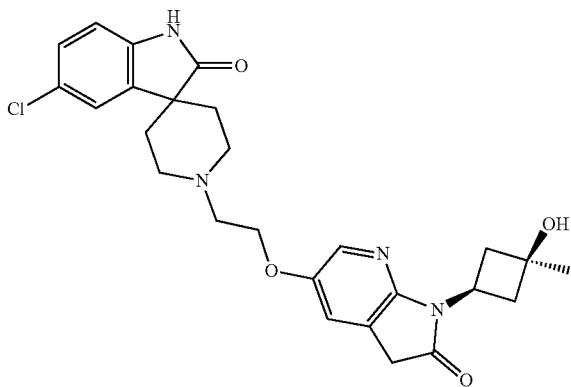 [SMILES: C[C@]1(O)C[C@@H](N2C(=O)Cc3cc(OCCN4CCC5(CC4)C(=O)Nc4ccc(Cl)cc45)cnc32)C1]

To a round-bottom flask equipped with a magnetic stir bar were added 5-chloro-1'-[2-({1-[(cis)-3-hydroxy-3-methyl-cyclobutyl]-1H-pyrrolo[2,3-b]pyridin-5-yl}oxy)ethyl]-1,2-dihydrospiro[indole-3,4'-piperidin]-2-one (Compound 349, 64.0 mg, 133 μmol), t-BuOH (2 mL), H$_2$O (0.2 mL) and then Py·Br$_3$ (128 mg, 399 μmol). The mixture was stirred at room temperature for 3 h. The mixture was diluted with H$_2$O (3 mL) and extracted with EtOAc (3×5 mL). The combined organic layers were dried over anhydrous Na$_2$SO$_4$, filtered, and concentrated under reduced pressure. The residue was dissolved in AcOH (1 mL) and then Zinc (8.70 mg, 133 μmol) was added. The mixture was stirred at room temperature for 4 h. The reaction mixture was cooled to 0° C. and quenched with H$_2$O (10 mL), and then adjusted to pH=7 by addition of saturated aqueous NaHCO$_3$ solution. The mixture was extracted with EtOAc (3×5 mL). The combined organic layers were dried over Na$_2$SO$_4$, filtered, and concentrated under reduced pressure. The residue was purified by reverse phase preparative HPLC (Waters Xbridge Prep OBD C$_{18}$ column, 20-55% MeCN: 10 mM NH$_4$HCO$_3$ in H$_2$O) to give 5-chloro-1'-[2-({2-oxo-1-[(cis)-3-hydroxy-3-methylcyclobutyl]-1H,2H,3H-pyrrolo[2,3-b]pyridin-5-yl}oxy)ethyl]-1,2-dihydrospiro[indole-3,4'-piperidin]-2-one (Compound 347). $^1$H NMR (400 MHz, DMSO-d$_6$): δ 10.48 (s, 1H), 7.89 (d, J=2.8 Hz, 1H), 7.50 (d, J=2.0 Hz, 1H), 7.42 (d, J=2.8 Hz, 1H), 7.24 (dd, J=8.0, 2.0 Hz, 1H), 6.84 (d, J=8.0 Hz, 1H), 5.12 (s, 1H), 4.39-4.37 (m, 1H), 4.16 (t, J=5.6 Hz, 2H), 3.56 (s, 2H), 3.01-2.91 (m, 2H), 2.85-2.84 (m, 2H), 2.82-2.83 (m, 2H), 2.68-2.69 (m, 2H), 2.23-2.20 (m, 2H), 1.78-1.72 (m, 4H), 1.30 (s, 3H). MS=497.2 [M+H]$^+$.

The following compounds in Table 38.11 were prepared according to procedures analogous to those described for Compound 347 using the appropriate starting materials or common intermediates.

TABLE 38.11

| # | Structure | IUPAC Name | Exact Mass [M + H]$^+$ | Intermediate used |
|---|-----------|------------|------------------------|-------------------|
| 348 | 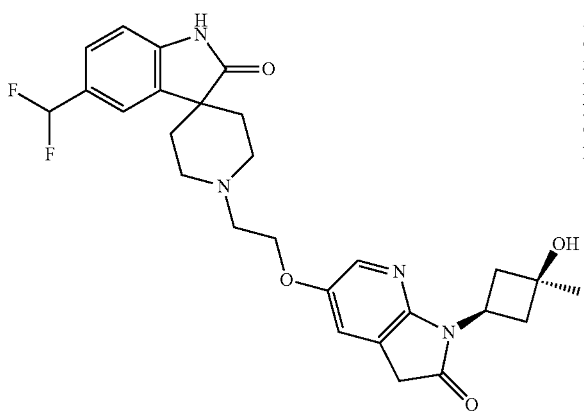 [SMILES: C[C@]1(O)C[C@@H](N2C(=O)Cc3cc(OCCN4CCC5(CC4)C(=O)Nc4ccc(C(F)F)cc45)cnc32)C1] | 5-(difluoromethyl)-1'-[2-({2-oxo-1-[(cis)-3-hydroxy-3-methylcyclobutyl]-1H,2H,3H-pyrrolo[2,3-b]pyridin-5-yl}oxy)ethyl]-1,2-dihydrospiro[indole-3,4'-piperidin]-2-one | Calc'd 513.2 Found 513.2 | B-1 |

Example 80

5-chloro-1'-(2-{[6-(2-hydroxypropan-2-yl)-5-(trifluoromethyl)pyridin-3-yl]oxy}ethyl)-1,2-dihydrospiro[indole-3,4'-piperidin]-2-one (Compound 371)

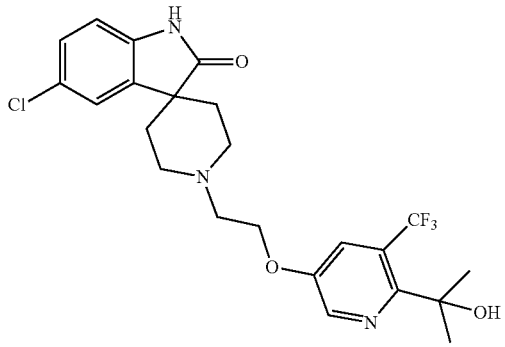 [SMILES: CC(C)(O)c1ncc(OCCN2CCC3(CC2)C(=O)Nc2ccc(Cl)cc23)cc1C(F)(F)F]

Step 1: 2-[5-(2-bromoethoxy)-3-(trifluoromethyl)pyridin-2-yl]propan-2-ol

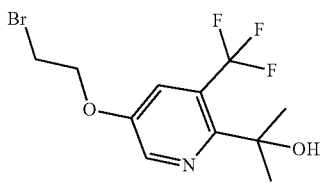 [SMILES: CC(C)(O)c1ncc(OCCBr)cc1C(F)(F)F]

To a solution of 1-[5-(2-bromoethoxy)-3-(trifluoromethyl)pyridin-2-yl]ethan-1-one (Example 71, Step 5, 100 mg, 320 μmol) in THF (2 mL) at 0° C. was added 3.0 M MeMgBr in THF (160 μL, 480 μmmol). The mixture was stirred at 0° C. for 2 h, then was quenched by addition of H₂O (1 mL) and extracted with EtOAc (3×1 mL). The combined organic layers were dried over Na₂SO₄, filtered and concentrated under reduced pressure to give 2-[5-(2-bromoethoxy)-3-(trifluoromethyl)pyridin-2-yl]propan-2-ol, which was taken to the next step without further purification. MS=328.0/330.0 [M+H]⁺.

Step 2: 5-chloro-1'-(2-{[6-(2-hydroxypropan-2-yl)-5-(trifluoromethyl)pyridin-3-yl]oxy}ethyl)-1,2-dihydrospiro[indole-3,4'-piperidin]-2-one

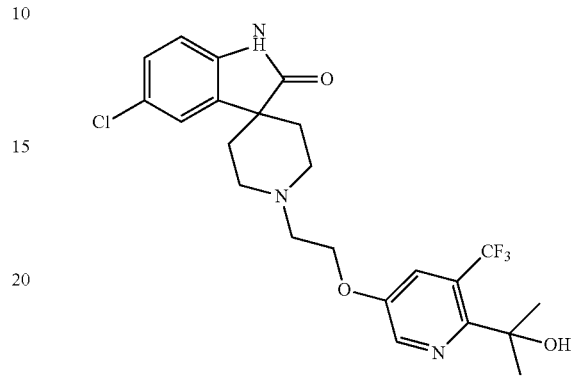

To a solution of 5-chloro-1,2-dihydrospiro[indole-3,4'-piperidin]-2-one (Intermediate B-4, 93.7 mg, 305 μmol, HCl salt) in MeCN (5 mL) was added NaHCO₃ (154 mg, 1.83 mmol) and 2-[5-(2-bromoethoxy)-3-(trifluoromethyl)pyridin-2-yl]propan-2-ol (100 mg, 305 μmol). The mixture was stirred at 80° C. for 16 h. After cooling to room temperature, the mixture was concentrated in vacuo. The residue was purified by reverse phase preparative HPLC (Phenomenex Luna C₁₈ column, 10-50% MeCN: 10 mM TFA in H₂O) to give 5-chloro-1'-(2-{[6-(2-hydroxypropan-2-yl)-5-(trifluoromethyl)pyridin-3-yl]oxy}ethyl)-1,2-dihydrospiro[indole-3,4'-piperidin]-2-one (Compound 371). ¹H NMR (400 MHz, DMSO-d₆): δ 10.66-10.20 (m, 1H), 8.49 (d, J=2.4 Hz, 1H), 7.69 (d, J=2.4 Hz, 1H), 7.49 (d, J=2.0 Hz, 1H), 7.30-7.18 (m, 1H), 6.85 (d, J=8.4 Hz, 1H), 5.15 (br d, J=1.2 Hz, 1H), 4.31 (t, J=5.6 Hz, 2H), 3.05-2.82 (m, 4H), 2.77-2.64 (m, 2H), 1.86-1.62 (m, 4H), 1.51 (s, 6H). MS=484.3 [M+H]⁺.

The following compounds in Table 38.12 were prepared according to procedures analogous to those described for Compound 371 using the appropriate starting materials or common intermediates.

TABLE 38.12

| # | Structure | IUPAC Name | Exact Mass [M + H]⁺ | Intermediate used |
|---|---|---|---|---|
| 411 | ![structure] | 1'-(2-{[6-(2-hydroxypropan-2-yl)-5-(trifluoromethyl)pyridin-3-yl]oxy}ethyl)-2-oxo-1,2-dihydrospiro[indole-3,4'-piperidine]-5-carbonitrile | Calc'd 475.2 Found 475.1 | B-9 |

Example 81

5-chloro-1'-{2-[4-(1-methanesulfonylpiperidin-4-yl)phenoxy]ethyl}-1-($^2$H$_3$)methyl-1,2-dihydrospiro[indole-3,4'-piperidin]-2-one (Compound 412)

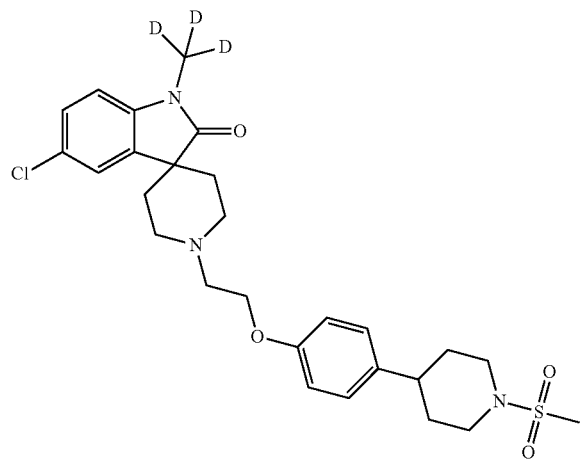 [SMILES: [2H]C([2H])([2H])N1C(=O)C2(CCN(CCOc3ccc(C4CCN(S(C)(=O)=O)CC4)cc3)CC2)c2cc(Cl)ccc21]

Step 1: tert-butyl 5-chloro-1-($^2$H$_3$)methyl-2-oxo-1,2-dihydrospiro[indole-3,4'-piperidine]-1'-carboxylate To a three-neck round-bottom flask equipped with a thermometer under N$_2$ atmosphere were added tert-butyl 5-chloro-2-oxo-1,2-dihydrospiro[indole-3,4'-piperidine]-1'-carboxylate (Intermediate B-3, 8.67 g, 25.8 mmol), CD$_3$I (5.60 g, 38.6 mmol) and THF (100 mL). The mixture was cooled to 0° C. and sodium hydride (3.09 g, 60% in mineral oil, 77.3 mmol) was added in portions. The mixture was stirred at 0° C. for 3 h under N$_2$ atmosphere. The reaction mixture was maintained at 0-5° C. and quenched by addition of saturated aqueous NH$_4$Cl (100 mL), and then extracted with EtOAc (3×150 mL). The combined organic layers were dried over Na$_2$SO$_4$, filtered, and concentrated in vacuo. The residue was purified by flash silica gel chromatography (Biotage 120 g cartridge, 0-40% EtOAc/Petroleum ether) to give tert-butyl 5-chloro-1-($^2$H$_3$)methyl-2-oxo-1,2-dihydrospiro[indole-3,4'-piperidine]-1'-carboxylate. MS=297.9 [M-C$_4$H$_8$+H]$^+$.

Step 2: 5-chloro-1-(trideuteriomethyl)spiro[indoline-3,4'-piperidine]-2-one

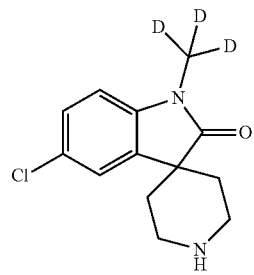 [SMILES: [2H]C([2H])([2H])N1C(=O)C2(CCNCC2)c2cc(Cl)ccc21]

To a mixture of tert-butyl 5-chloro-1-($^2$H$_3$)methyl-2-oxo-1,2-dihydrospiro[indole-3,4'-piperidine]-1'-carboxylate (8.60 g, 24.3 mmol) in EtOAc (10 mL) was added 4.0 M HCl in EtOAc (90 mL, 360 mmol). The mixture was stirred at room temperature for 2 h, then concentrated in vacuo. The residue was triturated with MTBE (45 mL) at room temperature for 1 h, and solids were collected by filtration. The filter cake was dried in vacuo to give 5-chloro-1-($^2$H$_3$)methyl-1,2-dihydrospiro[indole-3,4'-piperidin]-2-one (HCl salt), which was taken to the next step without further purification. MS=254.2 [M+H].

Step 3: 5-chloro-1'-{2-[4-(1-methanesulfonylpiperidin-4-yl)phenoxy]ethyl}-1-($^2$H$_3$)methyl-1,2-dihydrospiro[indole-3,4'-piperidin]-2-one

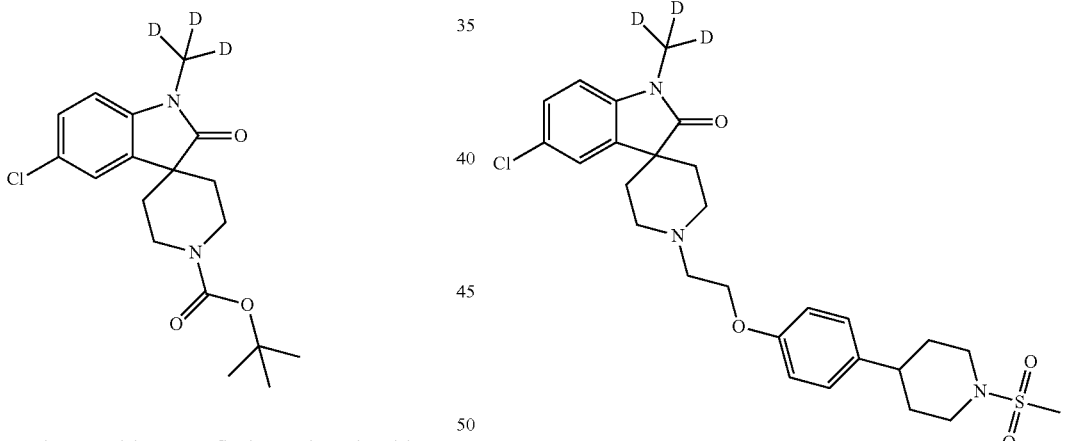

To a solution of 5-chloro-1-($^2$H$_3$)methyl-1,2-dihydrospiro[indole-3,4'-piperidin]-2-one (88.1 mg, 304 µmol, HCl salt) in MeCN (3 mL) was added NaHCO$_3$ (92.8 mg, 1.10 mmol) and 4-[4-(2-bromoethoxy)phenyl]-1-methanesulfonylpiperidine (Intermediate A-104, 100 mg, 276 µmol). The mixture was stirred at 80° C. for 16 h. After cooling to room temperature, the reaction mixture was filtered to remove NaHCO$_3$. The filtrate was purified by reverse phase preparative HPLC (Waters Xbridge Prep OBD C$_{18}$ column, 35-65% MeCN: 10 mM NH$_4$HCO$_3$ in H$_2$O) to give 5-chloro-1'-{2-[4-(1-methanesulfonylpiperidin-4-yl)phenoxy]ethyl}-1-($^2$H$_3$)methyl-1,2-dihydrospiro[indole-3,4'-piperidin]-2-one (Compound 412). $^1$H NMR (400 MHz, DMSO-d$_6$): δ 7.56 (d, J=2.0 Hz, 1H), 7.35 (dd, J=8.0, 2.0 Hz, 1H), 7.18 (d, J=8.8 Hz, 2H), 7.03 (d, J=8.4 Hz, 1H), 6.90

(d, J=8.4 Hz, 2H), 4.11 (t, J=5.6 Hz, 2H), 3.66 (d, J=12.0 Hz, 2H), 2.97-2.90 (m, 2H), 2.89 (s, 3H), 2.84 (t, J=5.6 Hz, 2H), 2.82-2.75 (m, 2H), 2.74-2.67 (m, 2H), 2.60-2.54 (m, 1H), 1.86-1.70 (m, 6H), 1.68-1.57 (m, 2H). MS=535.3 [M+H]$^+$.

The following compounds in Table 38.13 were prepared according to procedures analogous to those described for Compound 412 using the appropriate starting materials or common intermediates.

TABLE 38.13

| # | Structure | IUPAC Name | Exact Mass [M + H]$^+$ | Intermediate used |
|---|---|---|---|---|
| 413 | 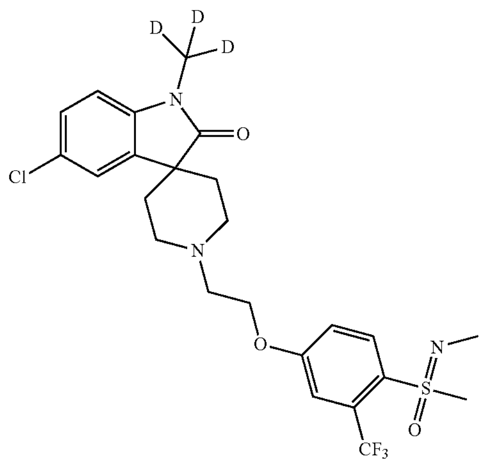 [SMILES: [2H]C([2H])([2H])N1C(=O)C2(CCN(CCOc3ccc(S(C)(=O)=NC)c(C(F)(F)F)c3)CC2)c2cc(Cl)ccc21] | 5-chloro-1-($^2$H$_3$)methyl-1'-(2-{4-[methyl(methylimino)oxo-λ$^6$-sulfanyl]-3-(trifluoromethyl)phenoxy)ethyl)-1,2-dihydrospiro[indole-3,4'-piperidin]-2-one | Calc'd 533.2 Found 533.3 | A-103 |
| 414 | 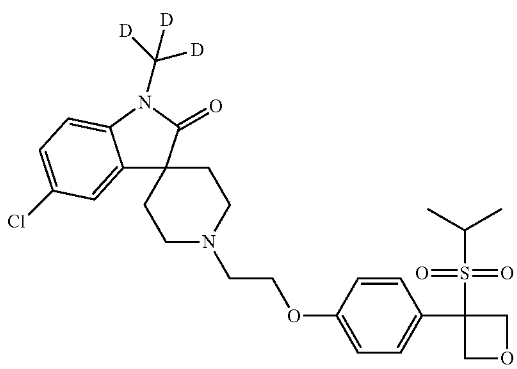 [SMILES: [2H]C([2H])([2H])N1C(=O)C2(CCN(CCOc3ccc(C4(S(=O)(=O)C(C)C)COC4)cc3)CC2)c2cc(Cl)ccc21] | 5-chloro-1-($^2$H$_3$)methyl-1'-(2-{4-[3-(propane-2-sulfonyl)oxetan-3-yl]phenoxy}ethyl)-1,2-dihydrospiro[indole-3,4'-piperidin]-2-one | Calc'd 536.2 Found 536.2 | A-107 |
| 415 | 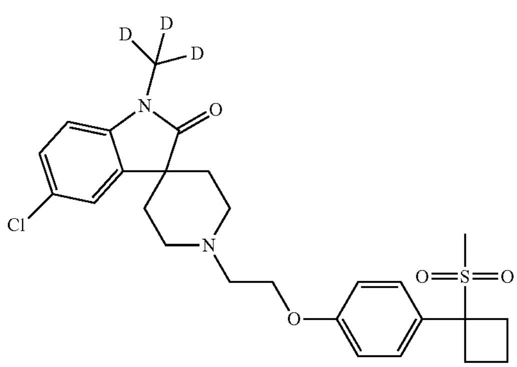 [SMILES: [2H]C([2H])([2H])N1C(=O)C2(CCN(CCOc3ccc(C4(S(C)(=O)=O)CCC4)cc3)CC2)c2cc(Cl)ccc21] | 5-chloro-1'-{2-[4-(1-methanesulfonylcyclobutyl)phenoxy]ethyl}-1-($^2$H$_3$)methyl-1,2-dihydrospiro[indole-3,4'-piperidin]-2-one | Calc'd 506.2 Found 506.3 | A-40 |

TABLE 38.13-continued

| # | Structure | IUPAC Name | Exact Mass [M + H]+ | Intermediate used |
|---|---|---|---|---|
| 416 | 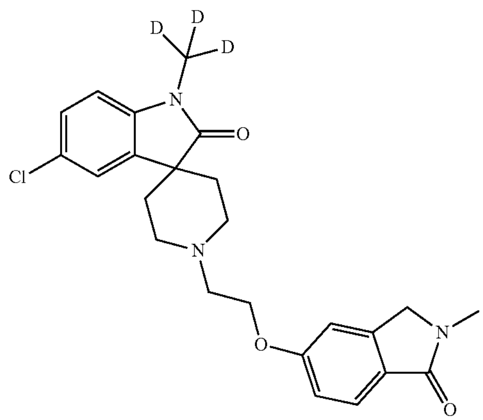 [SMILES: [2H]C([2H])([2H])N1C(=O)C2(CCN(CCOc3ccc4c(c3)CN(C)C4=O)CC2)c2cc(Cl)ccc21] | 5-chloro-1-(²H₃)methyl-1'-{2-[(2-methyl-1-oxo-2,3-dihydro-1H-isoindol-5-yl)oxy]ethyl}-1,2-dihydrospiro[indole-3,4'-piperidin]-2-one | Calc'd 443.2 Found 443.2 | A-53 |
| 417 | 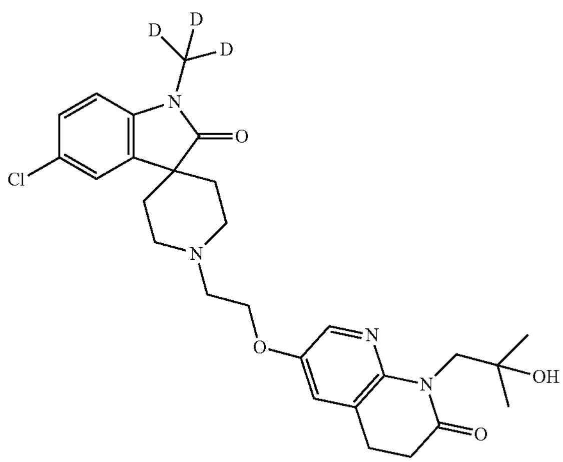 [SMILES: [2H]C([2H])([2H])N1C(=O)C2(CCN(CCOc3cnc4c(c3)CCC(=O)N4CC(C)(C)O)CC2)c2cc(Cl)ccc21] | 5-chloro-1'-(2-{[8-(2-hydroxy-2-methylpropyl)-7-oxo-5,6,7,8-tetrahydro-1,8-naphthyridin-3-yl]oxy}ethyl)-1-(²H₃)methyl-1,2-dihydrospiro[indole-3,4'-piperidin]-2-one | Calc'd 516.2 Found 516.3 | A-106 |
| 418 | 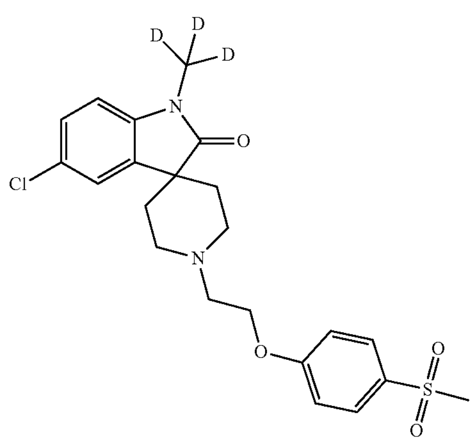 [SMILES: [2H]C([2H])([2H])N1C(=O)C2(CCN(CCOc3ccc(S(C)(=O)=O)cc3)CC2)c2cc(Cl)ccc21] | 5-chlro-1'-[2-(4-methanesulfonyl)phenoxy)ethyl]-1-(²H₃)methyl-1,2-dihydrospiro[indole-3,4'-piperidin]-2-one | Calc'd 452.1 Found 452.2 | A-3 |

TABLE 38.13-continued

| # | Structure | IUPAC Name | Exact Mass [M + H]+ | Intermediate used |
|---|---|---|---|---|
| 419 | 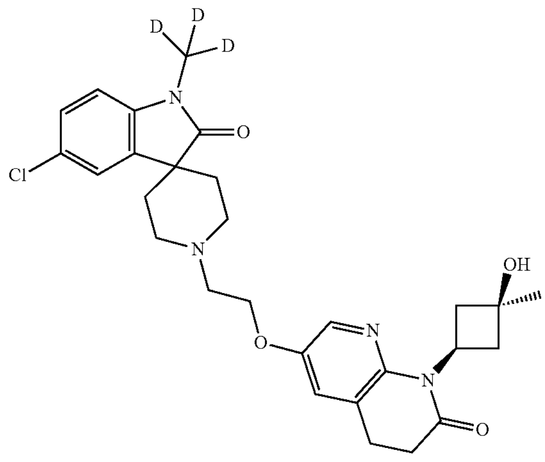 [SMILES: [2H]C([2H])([2H])N1C(=O)C2(CCN(CCOc3cnc4c(c3)CCC(=O)N4[C@H]3C[C@@](C)(O)C3)CC2)c2cc(Cl)ccc21] | 5-chloro-1-(²H₃)methyl-1'-[2-({7-oxo-8-[(1r,3s)-3-hydroxy-3-methylcyclobutyl]-5,6,7,8-tetrahydro-1,8-naphthyridin-3-yl}oxy)ethyl]-1,2-dihydrospiro[indole-3,4'-piperidin]-2-one | Calc'd 528.2 Found 528.2 | A-89 |
| 420 | 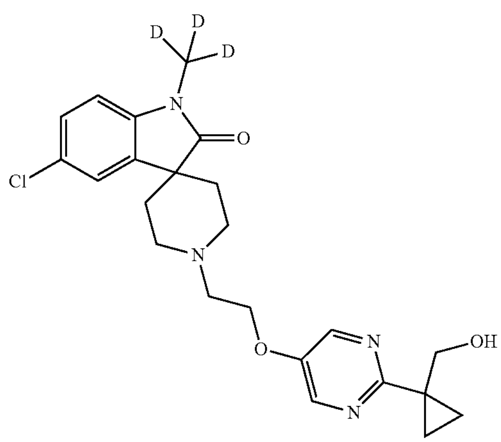 [SMILES: [2H]C([2H])([2H])N1C(=O)C2(CCN(CCOc3cnc(C4(CO)CC4)nc3)CC2)c2cc(Cl)ccc21] | 5-chloro-1'-[2-({2-[1-(hydroxymethyl)cyclopropyl]pyrimidin-5-yl}oxy)ethyl]-1-(²H₃)methyl-1,2-dihydrospiro[indole-3,4'-piperidin]-2-one | Calc'd 446.2 Found 446.1 | A-101 |
| 421 | 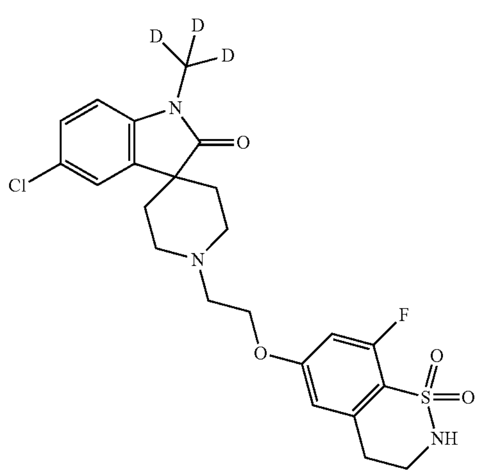 [SMILES: [2H]C([2H])([2H])N1C(=O)C2(CCN(CCOc3cc(F)c4c(c3)CCNS4(=O)=O)CC2)c2cc(Cl)ccc21] | 6-{2-[5-chloro-1-(²H₃)methyl-2-oxo-1,2-dihydrospiro[indole-3,4'-piperidin]-1'-yl]ethoxy}-8-fluoro-3,4-dihydro-2H-1λ⁶,2-benzothiazine-1,1-dione | Calc'd 497.1 Found 497.2 | |

TABLE 38.13-continued

| # | Structure | IUPAC Name | Exact Mass [M + H]+ | Intermediate used |
|---|---|---|---|---|
| 422 | 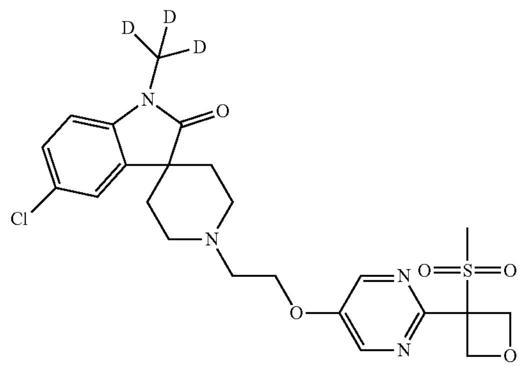 [SMILES: [2H]C([2H])([2H])N1C(=O)C2(CCN(CCOc3cnc(C4(S(C)(=O)=O)COC4)nc3)CC2)c2cc(Cl)ccc21] | 5-chloro-1'-(2-{[2-(3-methanesulfonyloxetan-3-yl)pyrimidin-5-yl]oxy}ethyl)-1-($^2$H$_3$)methyl-1,2-dihydrospiro[indole-3,4'-piperidin]-2-one | Calc'd 510.2 Found 510.3 | A-88 |
| 423 | 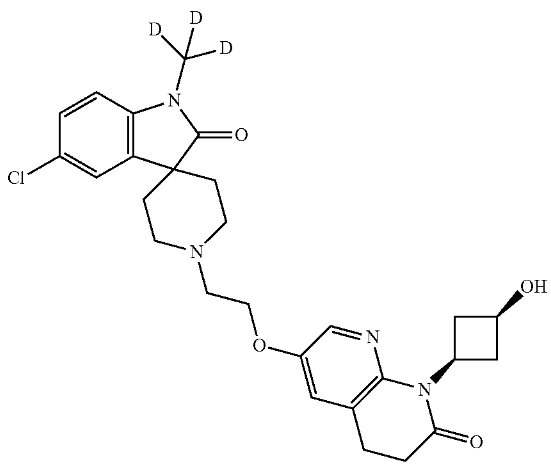 [SMILES: [2H]C([2H])([2H])N1C(=O)C2(CCN(CCOc3cnc4c(c3)CCC(=O)N4[C@H]3C[C@@H](O)C3)CC2)c2cc(Cl)ccc21] | 5-chloro-1'-($^2$H$_3$)methyl-1'-[2-({7-oxo-8-[(cis)-3-hydroxycyclobutyl]-5,6,7,8-tetrahydro-1,8-naphthyridin-3-yl}oxy)ethyl]-1,2-dihydrospiro[indole-3,4'-piperidin]-2-one | Calc'd 514.2 Found 514.1 | A-79 |
| 424 | 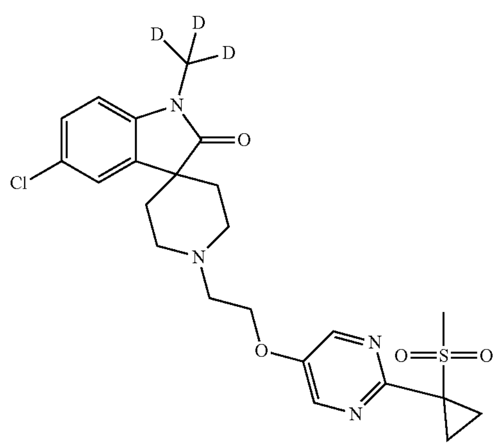 [SMILES: [2H]C([2H])([2H])N1C(=O)C2(CCN(CCOc3cnc(C4(S(C)(=O)=O)CC4)nc3)CC2)c2cc(Cl)ccc21] | 5-chloro-1'-(2-{[2-(1-methanesulfonylcyclopropyl)pyrimidin-5-yl]oxy}ethyl)-1-($^2$H$_3$)methyl-1,2-dihydrospiro[indole-3,4'-piperidin]-2-one | Calc'd 494.2 Found 494.1 | A-76 |

TABLE 38.13-continued

| # | Structure | IUPAC Name | Exact Mass [M + H]+ | Intermediate used |
|---|---|---|---|---|
| 425 | 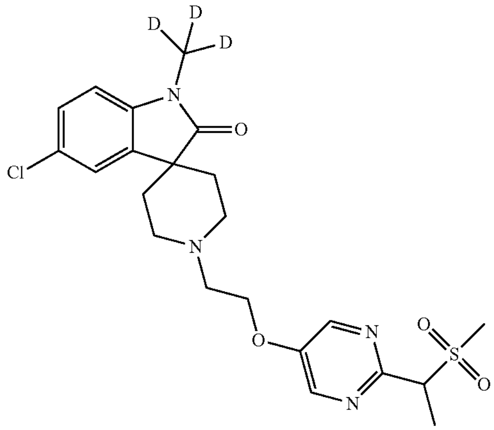 [SMILES: [2H]C([2H])([2H])N1C(=O)C2(CCN(CCOc3cnc(C(C)S(C)(=O)=O)nc3)CC2)c2cc(Cl)ccc21] | 5-chloro-1'-(2-{[2-(1-methanesulfonyl-ethyl)pyrimidin-5-yl]oxy}ethyl)-1-(²H₃)methyl-1,2-dihydrospiro[indole-3,4'-piperidin]-2-one | Calc'd 482.2 Found 482.1 | A-75 |

Example 82

5-chloro-1'-[2-({7-oxo-8-[(cis)-3-hydroxy-3-methylcyclobutyl]-5,6,7,8-tetrahydro-1,8-naphthyridin-3-yl}oxy)(1,1,2,2-²H₄)ethyl]-1,2-dihydrospiro[indole-3,4'-piperidin]-2-one (Compound 426)

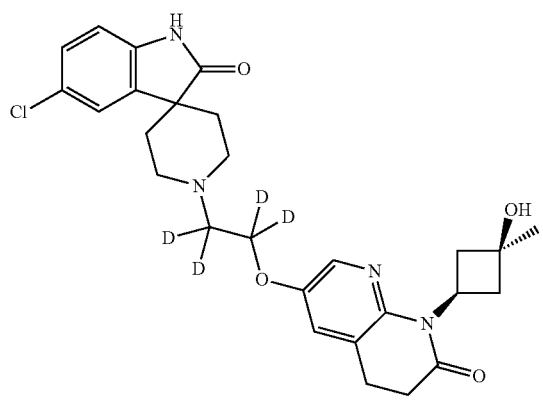 [SMILES: [2H]C([2H])(Oc1cnc2c(c1)CCC(=O)N2[C@H]1C[C@@](C)(O)C1)C([2H])([2H])N1CCC2(CC1)C(=O)Nc1ccc(Cl)cc12]

Step 1: 6-[2-bromo(1,1,2,2-²H₄)ethoxy]-1-[(cis)-3-hydroxy-3-methylcyclobutyl]-1,2,3,4-tetrahydro-1,8-naphthyridin-2-one

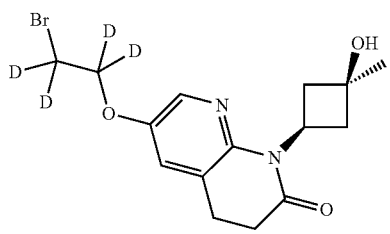 [SMILES: [2H]C([2H])(Br)C([2H])([2H])Oc1cnc2c(c1)CCC(=O)N2[C@H]1C[C@@](C)(O)C1]

A mixture of 6-hydroxy-1-[(cis)-3-hydroxy-3-methylcyclobutyl]-3,4-dihydro-1,8-naphthyridin-2-one (General Procedure for Intermediate A-89, Step 3, 100 mg, 0.403 mmol) and Cs₂CO₃ (262 mg, 0.806 mmol) in dibromo(²H₄)ethane (1.55 g, 8.05 mmol) and DMF (0.5 mL) was stirred at 90° C. for 3 h. The mixture was cooled to room temperature and filtered. The filtrate was concentrated under reduced pressure. The crude product was purified by flash silica gel chromatography (Biotage 10 g cartridge, 0-100% EtOAc/hexane) to give 6-[2-bromo(1,1,2,2-²H₄)ethoxy]-1-[(cis)-3-hydroxy-3-methylcyclobutyl]-3,4-dihydro-1,8-naphthyridin-2-one. MS=359.2/361.2 [M+H]⁺.

Step 2: 5-chloro-1'-[2-({7-oxo-8-[(cis)-3-hydroxy-3-methylcyclobutyl]-5,6,7,8-tetrahydro-1,8-naphthyridin-3-yl}oxy)(1,1,2,2-²H₄)ethyl]-1,2-dihydrospiro[indole-3,4'-piperidin]-2-one

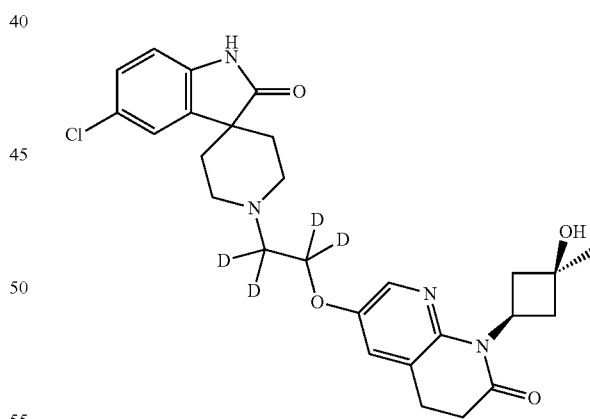

A mixture of 6-[2-bromo(1,1,2,2-²H₄)ethoxy]-1-[(cis)-3-hydroxy-3-methylcyclobutyl]-3,4-dihydro-1,8-naphthyridin-2-one (60.0 mg, 0.167 mmol), 5-chloro-1,2-dihydrospiro[indole-3,4'-piperidin]-2-one (Intermediate B-4, 50.2 mg, 0.184 mmol), K₂CO₃ (57.7 mg, 0.418 mmol) and KI (14 mg, 0.084 mmol) in DMF (1 mL) was stirred at 60° C. for 3 h. The mixture was cooled to room temperature and filtered. The filtrate was concentrated under reduced pressure. The crude product was purified by reverse phase silica gel chromatography (Biotage 60 g C₁₈ cartridge, 5-50% MeCN/H₂O with 0.1% NH₄OH) to give 5-chloro-1'-[2-({7- oxo-8-[(cis)-3-hydroxy-3-methylcyclobutyl]-5,6-dihydro-1,8-naphthyridin-3-yl}oxy)(1,1,2,2-²H₄)ethyl]-1H-spiro[indole-3,4'-piperidin]-2-one (Compound 426). ¹H NMR (500 MHz, DMSO-d₆): δ 10.54 (s, 1H), 7.95 (d, J=2.9 Hz, 1H), 7.52 (s, 1H), 7.40 (d, J=2.9 Hz, 1H), 7.25 (dd, J=8.3, 2.1 Hz, 1H), 6.86 (d, J=8.2 Hz, 1H), 4.82 (s, 1H), 4.24 (pent, J=8.3 Hz, 1H), 3.20-2.67 (m, 4H), 2.54-2.50 (m, 4H), 2.48-2.40 (m, 2H), 2.38-2.30 (m, 2H), 2.00-1.61 (m, 4H), 1.25 (s, 3H). MS=515.2 [M+H]⁺.

Example 83

5-chloro-1'-[2-({2-[(cis)-3-hydroxy-3-methylcyclobutyl]-7-(trifluoromethyl)-2H-indazol-5-yl}oxy)ethyl]-1,2-dihydrospiro[indole-3,4'-piperidin]-2-one (Compound 427)

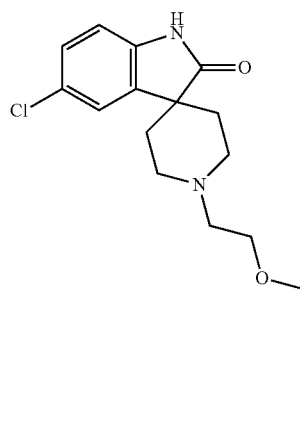

Step 1: (cis)-3-[5-(2-bromoethoxy)-7-(trifluoromethyl)-2H-indazol-2-yl]-1-methylcyclobutan-1-ol

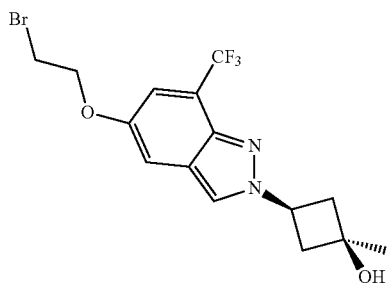 [SMILES: C[C@]1(O)C[C@@H](n2cc3cc(OCCBr)cc(C(F)(F)F)c3n2)C1]

A mixture of 2-[(cis)-3-hydroxy-3-methylcyclobutyl]-7-(trifluoromethyl)-2H-indazol-5-ol (Intermediate A-108, 365 mg, 1.27 mmol) and Cs₂CO₃ (831 mg, 2.55 mmol) in 1,2-dibromoethane (3.3 mL, 38.2 mmol) and DMF (0.5 mL) was stirred at 90° C. for 19 h. The mixture was cooled to room temperature and filtered. The filtrate was concentrated under reduced pressure. The crude product was purified by flash silica gel chromatography (Biotage 25 g cartridge, 0-100% EtOAc/hexane) to give (cis)-3-[5-(2-bromoethoxy)-7-(trifluoromethyl)-2H-indazol-2-yl]-1-methylcyclobutan-1-ol. MS=393.1/395.1 [M+H]⁺.

Step 2: 5-chloro-1'-[2-({2-[(cis)-3-hydroxy-3-methylcyclobutyl]-7-(trifluoromethyl)-2H-indazol-5-yl}oxy)ethyl]-1,2-dihydrospiro[indole-3,4'-piperidin]-2-one (Compound 427)

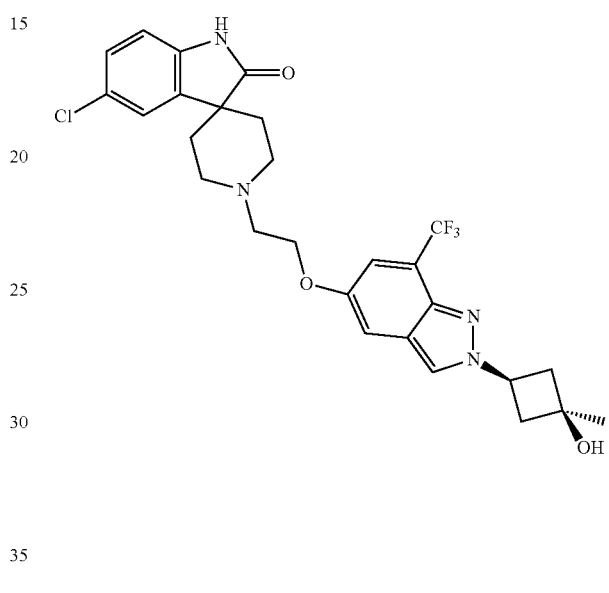

A mixture of (cis)-3-[5-(2-bromoethoxy)-7-(trifluoromethyl)indazol-2-yl]-1-methylcyclobutan-1-ol (85 mg, 0.216 mmol), 5-chloro-1,2-dihydrospiro[indole-3,4'-piperidin]-2-one (Intermediate B-4, 65 mg, 0.238 mmol, HCl salt), K₂CO₃ (75 mg, 0.54 mmol) and KI (18 mg, 0.108 mmol) in DMF (1 mL) was stirred at 60° C. for 4 h. The mixture was cooled to room temperature, filtered, washed with EtOAc (3×20 mL). The filtrate was concentrated under reduced pressure. The crude residue was purified by reverse phase preparative HPLC (Phenomenex Kinetex C₁₈ column, 5-40% MeCN in H₂O with 0.1% formic acid) to give 5-chloro-1'-[2-({2-[(cis)-3-hydroxy-3-methylcyclobutyl]-7-(trifluoromethyl)-2H-indazol-5-yl}oxy)ethyl]-1,2-dihydrospiro[indole-3,4'-piperidin]-2-one (Compound 427). ¹H NMR (500 MHz, DMSO-d₆): δ 10.47 (s, 1H), 8.43 (s, 1H), 7.45 (s, 1H), 7.38 (d, J=2.3 Hz, 1H), 7.27 (s, 1H), 7.18 (dd, J=8.3, 2.1 Hz, 1H), 6.79 (d, J=8.2 Hz, 1H), 5.27 (s, 1H), 4.80 (pent, J=8.3 Hz, 1H), 4.19-4.16 (m, 2H), 3.13-2.68 (m, 6H), 2.61-2.48 (m, 4H), 1.90-1.61 (m, 4H), 1.30 (s, 3H). MS=549.1 [M+H]⁺.

The following compound in Table 38.14 was prepared according to the procedures analogous to those described for Compound 427 using the appropriate starting materials.

TABLE 38.14

| No. | Structure | IUPAC Name | Exact Mass [M + H]+ | Intermediate used |
|---|---|---|---|---|
| 428 | 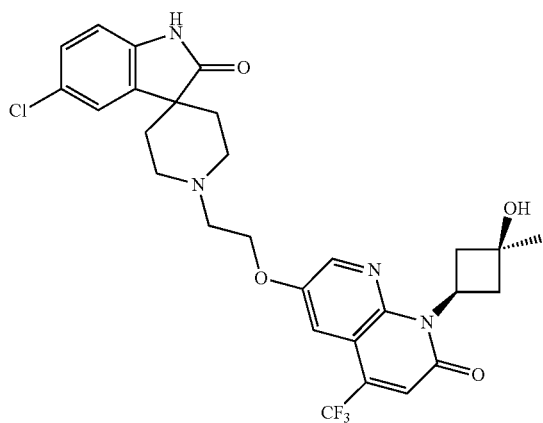 [SMILES: C[C@]1(O)C[C@@H](n2c(=O)cc(C(F)(F)F)c3cc(OCCN4CCC5(CC4)C(=O)Nc4ccc(Cl)cc45)cnc32)C1] | 2-oxo-1'-[2-({2-[(cis)-3-hydroxy-3-methylcyclobutyl]-7-(trifluoromethyl)-2H-indazol-5-yl}oxy)ethyl]-1,2-dihydrospiro[indole-3,4'-piperidine]-5-carbonitrile | Calc'd 540.2 Found 540.2 | A-108 and B-9 |

Example 84

5-chloro-1'-[2-({7-oxo-8-[(cis)-3-hydroxy-3-methyl-cyclobutyl]-5-(trifluoromethyl)-7,8-dihydro-1,8-naphthyridin-3-yl}oxy)ethyl]-1,2-dihydrospiro[indole-3,4'-piperidin]-2-one (Compound 341)

To a mixture of 6-hydroxy-1-((cis)-3-hydroxy-3-methyl-cyclobutyl)-4-(trifluoromethyl)-1,8-naphthyridin-2(1H)-one (Intermediate A-109, 400 mg, 1.27 mmol) and 1,2-dibromoethane (2.88 mL, 38.2 mmol) in MeCN (5 mL) was added $K_2CO_3$ (704 mg, 5.09 mmol). The mixture was stirred at 65° C. for 16 h. After cooling to room temperature, the reaction mixture was diluted with $H_2O$ (20 mL) and extracted with EtOAc (2×20 mL). The combined organic layers were dried over $Na_2SO_4$, filtered, and concentrated under reduced pressure. The residue was purified by flash silica gel chromatography (Biotage 12 g cartridge, 0-15% EtOAc/Petroleum ether) to give 6-(2-bromoethoxy)-1-((cis)-3-hydroxy-3-methylcyclobutyl)-4-(trifluoromethyl)-1,8-naphthyridin-2(1H)-one. MS=420.9/422.8 [M+H]+.

Step 2: 5-chloro-1'-[2-({7-oxo-8-[(cis)-3-hydroxy-3-methylcyclobutyl]-5-(trifluoromethyl)-7,8-dihydro-1,8-naphthyridin-3-yl}oxy)ethyl]-1,2-dihydrospiro[indole-3,4'-piperidin]-2-one

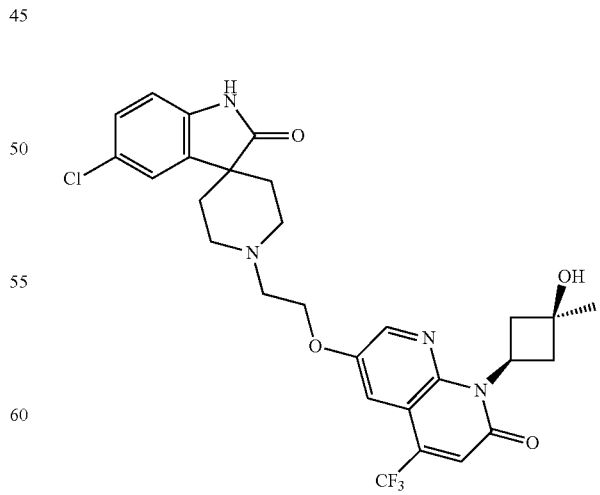

Step 1: 6-(2-bromoethoxy)-1-((cis)-3-hydroxy-3-methylcyclobutyl)-4-(trifluoromethyl)-1,8-naphthyridin-2(1H)-one

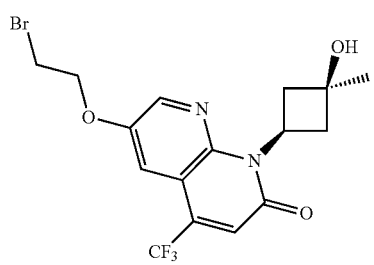 [SMILES: C[C@]1(O)C[C@@H](n2c(=O)cc(C(F)(F)F)c3cc(OCCBr)cnc32)C1]

To a mixture of 6-(2-bromoethoxy)-1-((cis)-3-hydroxy-3-methylcyclobutyl)-4-(trifluoromethyl)-1,8-naphthyridin-2(1H)-one (120 mg, 285 μmol) and 5-chloro-1,2-dihydrospiro

[indole-3,4'-piperidin]-2-one (Intermediate B-4, 77.82 mg, 285 µmol, HCl salt) in MeCN (3 mL) was added NaHCO₃ (120 mg, 1.42 mmol). The mixture was stirred at 65° C. for 16 h. After cooling to room temperature, the reaction was diluted with H₂O (10 mL) and extracted with EtOAc (2×10 mL). The combined organic layers were washed with brine (10 mL), dried over Na₂SO₄, filtered, and concentrated in vacuo. The crude residue was purified by reverse phase preparative HPLC (Waters Xbridge OBD C₁₈ column, 30-60% MeCN: 10 mM NH₄HCO₃ in H₂O) to give 5-chloro-1'-[2-({7-oxo-8-[(cis)-3-hydroxy-3-methylcyclobutyl]-5-(trifluoromethyl)-7,8-dihydro-1,8-naphthyridin-3-yl}oxy)ethyl]-1,2-dihydrospiro[indole-3,4'-piperidin]-2-one (Compound 341). ¹H NMR (400 MHz, MeCN-d₃): δ 8.48 (d, J=2.8 Hz, 1H), 8.39 (br s, 1H), 7.66-7.59 (m, 1H), 7.43 (d, J=2.0 Hz, 1H), 7.20 (dd, J=8.4, 2.0 Hz, 1H), 7.08 (s, 1H), 6.87 (d, J=8.4 Hz, 1H), 5.77-5.65 (m, 1H), 4.28 (t, J=5.6 Hz, 2H), 3.87 (s, 1H), 3.08-2.86 (m, 6H), 2.80-2.67 (m, 2H), 2.61-2.49 (m, 2H), 1.91-1.81 (m, 2H), 1.79-1.69 (m, 2H), 1.37 (s, 3H). MS=577.3 [M+H]⁺.

The following compounds in Table 38.15 were prepared according to procedures analogous to those described for Compound 341 using the appropriate starting materials or common intermediates.

TABLE 38.15

| # | Structure | IUPAC Name | Exact Mass [M + H]⁺ | Intermediates Used | Chiral separation column | Chiral elution order |
|---|---|---|---|---|---|---|
| 342 | 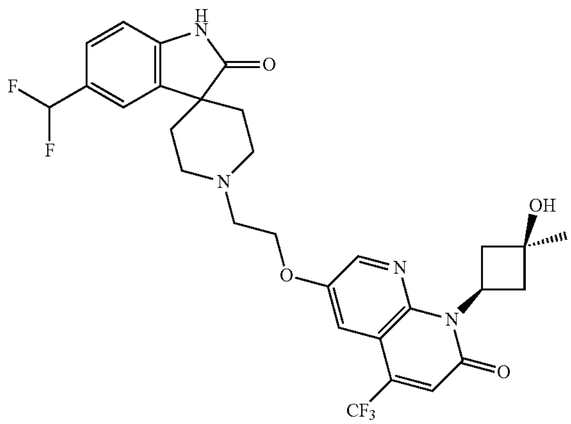 [SMILES: C[C@]1(O)C[C@@H](n2c(=O)cc(C(F)(F)F)c3cc(OCCN4CCC5(CC4)C(=O)Nc4ccc(C(F)F)cc45)cnc32)C1] | 5-(difluoromethyl)-1'-[2-({7-oxo-8-[(cis)-3-hydroxy-3-methylcyclobutyl]-5-(trifluoromethyl)-7,8-dihydro-1,8-naphthyridin-3-yl}oxy)ethyl]-1,2-dihydrospiro[indole-3,4'-piperidin]-2-one | Calc'd 593.2 Found 593.3 | A-109 and B-1 | n/a | n/a |
| 354 | 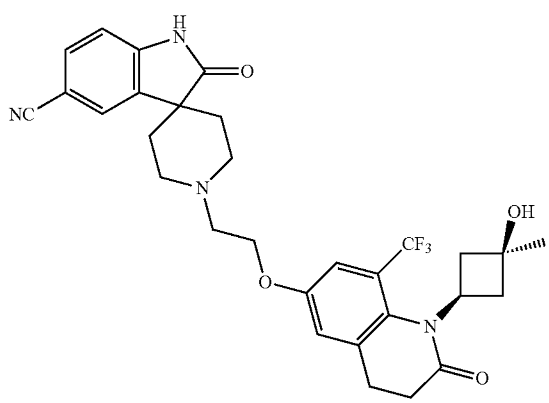 [SMILES: C[C@]1(O)C[C@@H](N2C(=O)CCc3cc(OCCN4CCC5(CC4)C(=O)Nc4ccc(C#N)cc45)cc(C(F)(F)F)c32)C1] | 2-oxo-1'-[2-({2-oxo-1-[(cis)-3-hydroxy-3-methylcyclobutyl]-8-(trifluoromethyl)-1,2,3,4-tetrahydroquinolin-6-yl}oxy)ethyl]-1,2-dihydrospiro[indole-3,4'-piperidine]-5-carbonitrile | Calc'd 569.2 Found 569.2 | A-110 and B-9 | n/a | n/a |
| 353 | 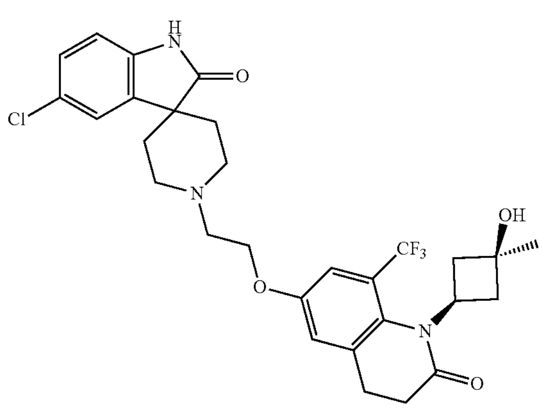 [SMILES: C[C@]1(O)C[C@@H](N2C(=O)CCc3cc(OCCN4CCC5(CC4)C(=O)Nc4ccc(Cl)cc45)cc(C(F)(F)F)c32)C1] | 5-chloro-1'-[2-({2-oxo-1-[(cis)-3-hydroxy-3-methylcyclobutyl]-8-(trifluoromethyl)-1,2,3,4-tetrahydroquinolin-6-yl}oxy)ethyl]-1,2-dihydrospiro[indole-3,4'-piperidin]-2-one | Calc'd 578.2 Found 578.2 | A-110 and B-4 | n/a | n/a |

TABLE 38.15-continued

| # | Structure | IUPAC Name | Exact Mass [M + H]⁺ | Intermediates Used | Chiral separation column | Chiral elution order |
|---|---|---|---|---|---|---|
| 339 | 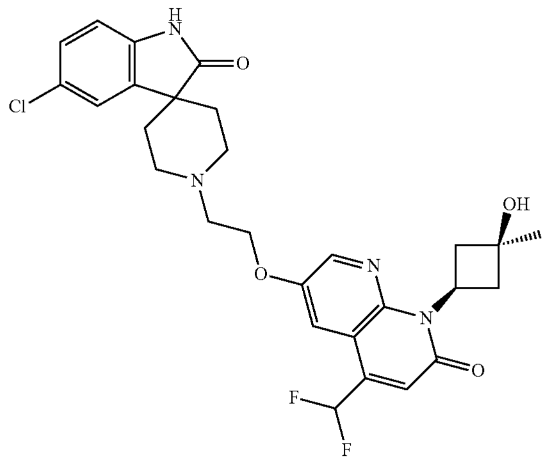 [SMILES: C[C@]1(O)C[C@@H](n2c(=O)cc(C(F)F)c3cc(OCCN4CCC5(CC4)C(=O)Nc4ccc(Cl)cc45)cnc32)C1] | 5-chloro-1'-(2-{[5-(difluoromethyl)-7-oxo-8-[(cis)-3-hydroxy-3-methylcyclobutyl]-7,8-dihydro-1,8-naphthyridin-3-yl]oxy}ethyl)-1,2-dihydrospiro[indole-3,4'-piperidin]-2-one | Calc'd 559.2 Found 559.4 | A-111 and B-4 | n/a | n/a |
| 340 | 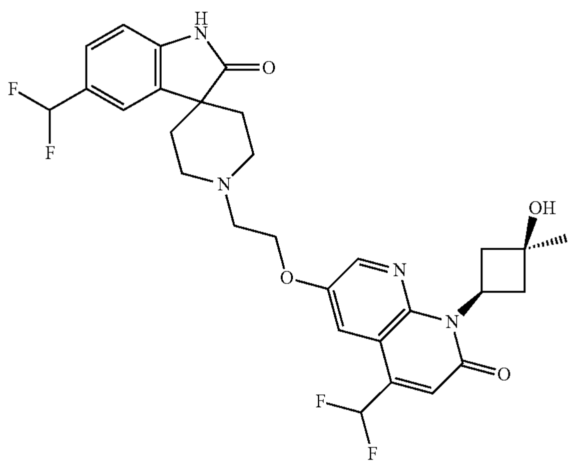 [SMILES: C[C@]1(O)C[C@@H](n2c(=O)cc(C(F)F)c3cc(OCCN4CCC5(CC4)C(=O)Nc4ccc(C(F)F)cc45)cnc32)C1] | 5-(difluoromethyl)-1'-(2-{[5-(difluoromethyl)-7-oxo-8-[(cis)-3-hydroxy-3-methylcyclobutyl]-7,8-dihydro-1,8-naphthyridin-3-yl]oxy}ethyl)-1,2-dihydrospiro[indole-3,4'-piperidin]-2-one | Calc'd 575.2 Found 575.4 | A-111 and B-1 | n/a | n/a |
| 429 | 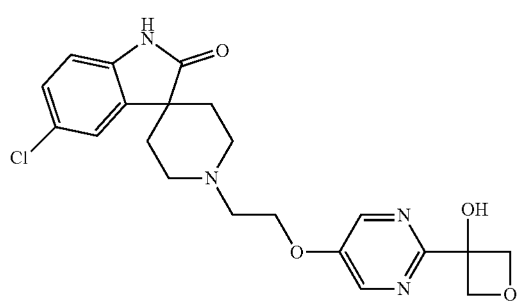 [SMILES: O=C1Nc2ccc(Cl)cc2C12CCN(CCOc1cnc(C3(O)COC3)nc1)CC2] | 5-chloro-1'-(2-{[2-(3-hydroxyoxetan-3-yl)pyrimidin-5-yl]oxy}ethyl)-1,2-dihydrospiro[indole-3,4'-piperidin]-2-one | Calc'd 431.1 Found 431.2 | A-112 and B-4 | n/a | n/a |
| 430 | 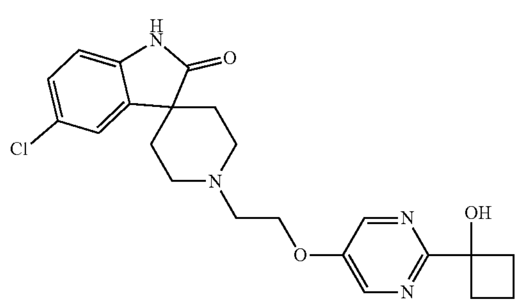 [SMILES: O=C1Nc2ccc(Cl)cc2C12CCN(CCOc1cnc(C3(O)CCC3)nc1)CC2] | 5-chloro-1'-(2-{[2-(1-hydroxycyclobutyl)pyrimidin-5-yl]oxy}ethyl)-1,2-dihydrospiro[indole-3,4'-piperidin]-2-one | Calc'd 429.1 Found 429.1 | A-113 and B-4 | n/a | n/a |

TABLE 38.15-continued

| # | Structure | IUPAC Name | Exact Mass [M + H]+ | Intermediates Used | Chiral separation column | Chiral elution order |
|---|---|---|---|---|---|---|
| 431 | 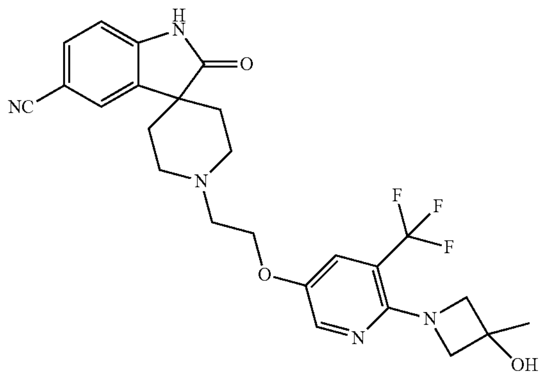 [SMILES: CC1(O)CN(c2ncc(OCCN3CCC4(CC3)C(=O)Nc3ccc(C#N)cc34)cc2C(F)(F)F)C1] | 1'-(2-{[6-(3-hydroxy-3-methylazetidin-1-yl)-5-(trifluoromethyl)pyridin-3-yl]oxy}ethyl)-2-oxo-1,2-dihydrospiro[indole-3,4'-piperidine]-5-carbonitrile | Calc'd 502.2 Found 502.3 | A-99 and B-9 | n/a | n/a |
| 432 | 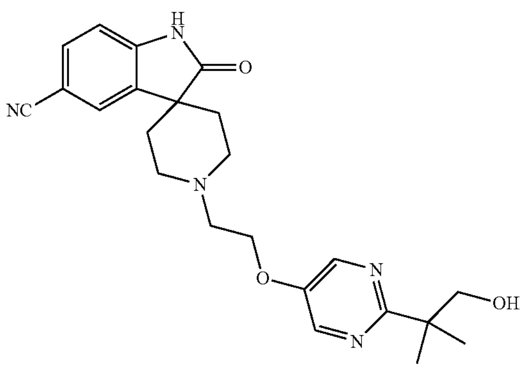 [SMILES: CC(C)(CO)c1ncc(OCCN2CCC3(CC2)C(=O)Nc2ccc(C#N)cc23)cn1] | 1'-(2-{[2-(1-hydroxy-2-methylpropan-2-yl)pyrimidin-5-yl]oxy}ethyl)-2-oxo-1,2-dihydrospiro[indole-3,4'-piperidine]-5-carbonitrile | Calc'd 422.2 Found 422.2 | A-100 and B-9 | n/a | n/a |
| 433 | 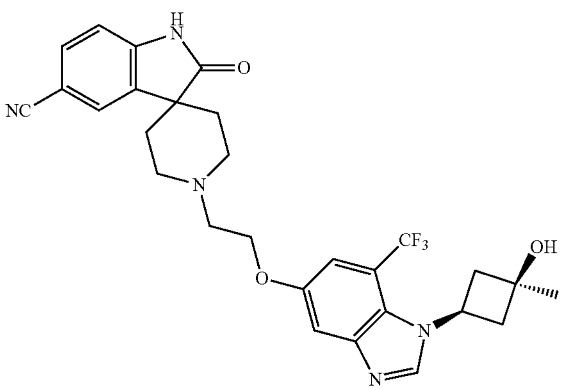 [SMILES: C[C@]1(O)C[C@@H](n2cnc3cc(OCCN4CCC5(CC4)C(=O)Nc4ccc(C#N)cc45)cc(C(F)(F)F)c32)C1] | 1'-(2-((1-((cis)-3-hydroxy-3-methylcyclobutyl)-7-(trifluoromethyl)-1H-benzo[d]imidazol-5-yl)oxy)ethyl)-2-oxospiro[indoline-3,4'-piperidine]-5-carbonitrile | Calc'd 540.2 Found 540.1 | A-92 and B-9 | n/a | n/a |
| 434 | 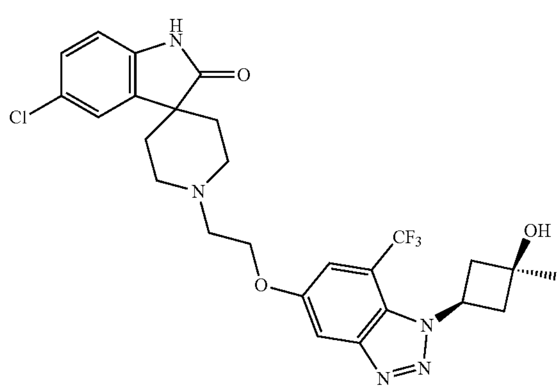 [SMILES: C[C@]1(O)C[C@@H](n2nnc3cc(OCCN4CCC5(CC4)C(=O)Nc4ccc(Cl)cc45)cc(C(F)(F)F)c32)C1] | 5-chloro-1'-[2-({1-[(cis)-3-hydroxy-3-methylcyclobutyl]-7-(trifluoromethyl)-1H-1,2,3-benzotriazol-5-yl}oxy)ethyl]-1,2-dihydrospiro[indole-3,4'-piperidin]-2-one | Calc'd 550.2 Found 550.0 | A-114 and B-4 | n/a | n/a |

TABLE 38.15-continued

| # | Structure | IUPAC Name | Exact Mass [M + H]+ | Intermediates Used | Chiral separation column | Chiral elution order |
|---|---|---|---|---|---|---|
| 435 | 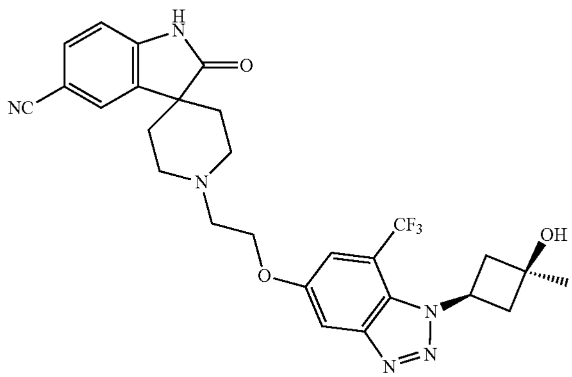 [SMILES: C[C@]1(O)C[C@@H](n2nnc3cc(OCCN4CCC5(CC4)C(=O)Nc4ccc(C#N)cc45)cc(C(F)(F)F)c32)C1] | 2-oxo-1'-[2-({1-[(cis)-3-hydroxy-3-methylcyclobutyl]-7-(trifluoromethyl)-1H-1,2,3-benzotriazol-5-yl}oxy)ethyl]-1,2-dihydrospiro[indole-3,4'-piperidine]-5-carbonitrile | Calc'd 541.2 Found 541.0 | A-114 and B-9 | n/a | n/a |
| 373 | 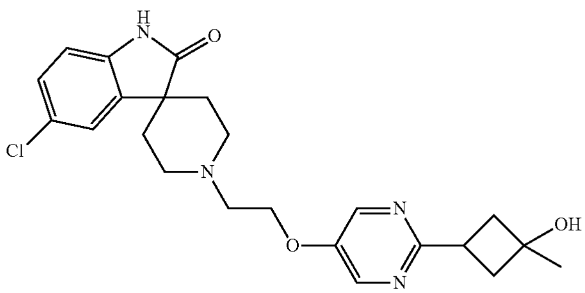 [SMILES: CC1(O)CC(c2ncc(OCCN3CCC4(CC3)C(=O)Nc3ccc(Cl)cc34)cn2)C1] | 5-chloro-1'-(2-{[2-(3-hydroxy-3-methylcyclobutyl)pyrimidin-5-yl]oxy}ethyl)-1,2-dihydrospiro[indole-3,4'-piperidin]-2-one | Calc'd 443.2 Found 443.0 | A-115 and B-4 | n/a | n/a |
| 393 | 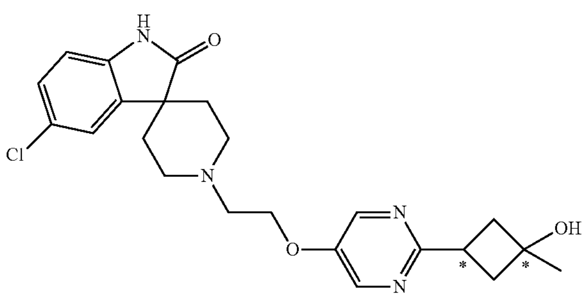 [SMILES: CC1(O)CC(c2ncc(OCCN3CCC4(CC3)C(=O)Nc3ccc(Cl)cc34)cn2)C1] | 5-chloro-1'-[2-({2-[(cis) or (trans)-3-hydroxy-3-methylcyclobutyl]pyrimidin-5-yl}oxy)ethyl]-1,2-dihydrospiro[indole-3,4'-piperidin]-2-one | Calc'd 443.2 Found 443.0 | A-115 and B-4 | Daicel Chiralpak AD-3 | 1st |
| 392 | 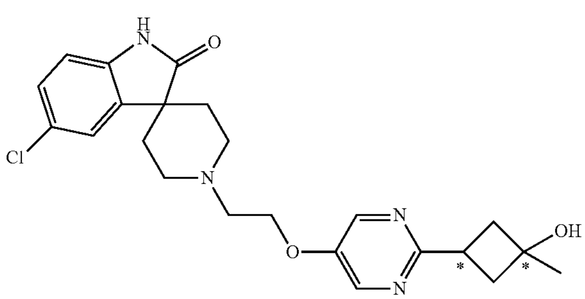 [SMILES: CC1(O)CC(c2ncc(OCCN3CCC4(CC3)C(=O)Nc3ccc(Cl)cc34)cn2)C1] | 5-chloro-1'-[2-({2-[(trans) or (cis)-3-hydroxy-3-methylcyclobutyl]pyrimidin-5-yl}oxy)ethyl]-1,2-dihydrospiro[indole-3,4'-piperidin]-2-one | Calc'd 443.2 Found 443.0 | A-115 and B-4 | Daicel Chiralpak AD-3 | 2nd |

TABLE 38.15-continued

| # | Structure | IUPAC Name | Exact Mass [M + H]+ | Intermediates Used | Chiral separation column | Chiral elution order |
|---|---|---|---|---|---|---|
| 436 | 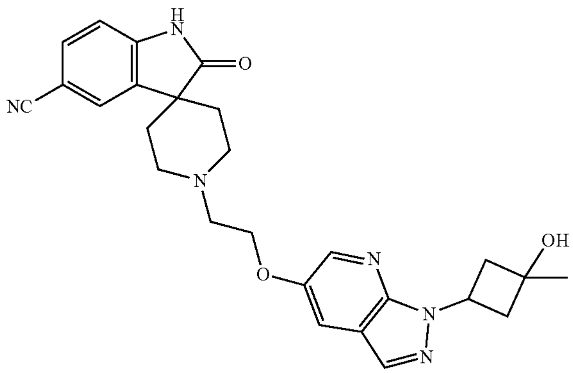 [SMILES: CC1(O)CC(n2ncc3cc(OCCN4CCC5(CC4)C(=O)Nc4ccc(C#N)cc45)cnc32)C1] | 1'-(2-{[1-(3-hydroxy-3-methylcyclobutyl)-1H-pyrazolo[3,4-b]pyridin-5-yl]oxy}ethyl)-2-oxo-1,2-dihydrospiro[indole-3,4'-piperidine]-5-carbonitrile | Calc'd 473.2 Found 473.1 | A-116 & B-9 | n/a | n/a |
| 437 | 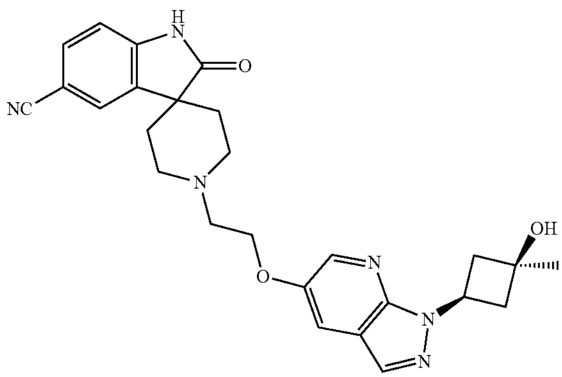 [SMILES: C[C@]1(O)C[C@@H](n2ncc3cc(OCCN4CCC5(CC4)C(=O)Nc4ccc(C#N)cc45)cnc32)C1] | 2-oxo-1'-[2-({1-[(cis)-3-hydroxy-3-methylcyclobutyl]-1H-pyrazolo[3,4-b]pyridin-5-yl}oxy)ethyl]-1,2-dihydrospiro[indole-3,4'-piperidine]-5-carbonitrile | Calc'd 473.2 Found 473.1 | A-116 & B-9 | Daicel Chiralpak OJ-3 | 1st |
| 438 | 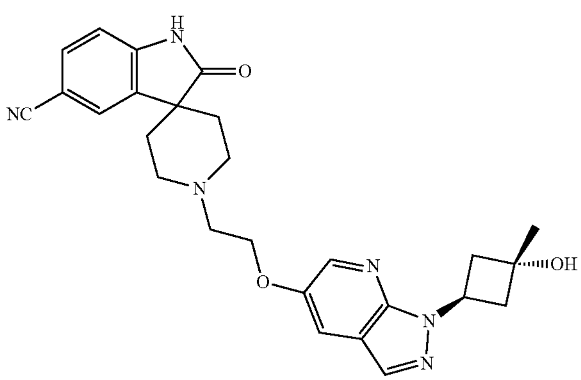 [SMILES: C[C@]1(O)C[C@H](n2ncc3cc(OCCN4CCC5(CC4)C(=O)Nc4ccc(C#N)cc45)cnc32)C1] | 2-oxo-1'-[2-({1-[(trans)-3-hydroxy-3-methylcyclobutyl]-1H-pyrazolo[3,4-b]pyridin-5-yl}oxy)ethyl]-1,2-dihydrospiro[indole-3,4'-piperidine]-5-carbonitrile | Calc'd 473.2 Found 473.1 | A-116 & B-9 | Daicel Chiralpak OJ-3 | 2nd |
| 439 | 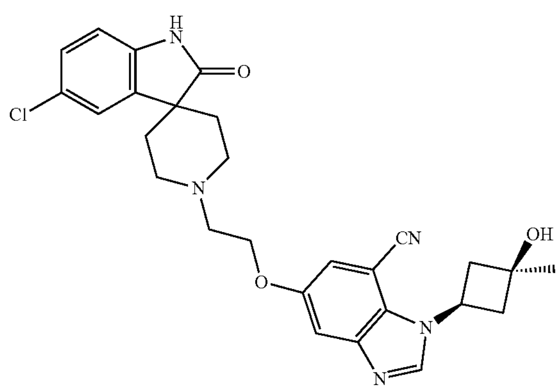 [SMILES: C[C@]1(O)C[C@@H](n2cnc3cc(OCCN4CCC5(CC4)C(=O)Nc4ccc(Cl)cc45)cc(C#N)c32)C1] | 5-(2-{5-chloro-2-oxo-1,2-dihydrospiro[indole-3,4'-piperidin]-1'-yl}ethoxy)-1-[(cis)-3-hydroxy-3-methylcyclobutyl]-1H-1,3-benzodiazole-7-carbonitrile | Calc'd 506.2 Found 506.2 | A-117 & B-4 | n/a | n/a |

TABLE 38.15-continued

| # | Structure | IUPAC Name | Exact Mass [M + H]+ | Intermediates Used | Chiral separation column | Chiral elution order |
|---|-----------|------------|---------------------|--------------------|--------------------------|----------------------|
| 440 | 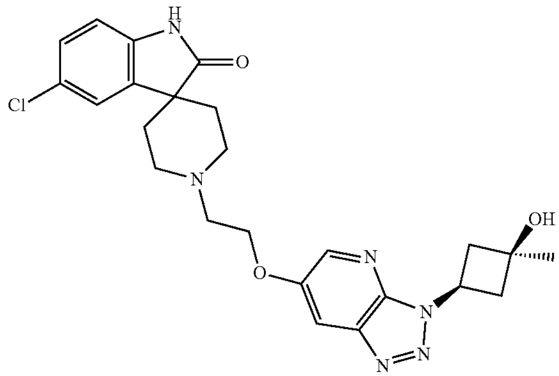 [SMILES: C[C@]1(O)C[C@@H](n2nnc3cc(OCCN4CCC5(CC4)C(=O)Nc4ccc(Cl)cc45)cnc32)C1] | 5-chloro-1'-[2-({3-[(cis)-3-hydroxy-3-methylcyclobutyl]-3H-[1,2,3]triazolo[4,5-b]pyridin-6-yl}oxy)ethyl]-1,2-dihydrospiro[indole-3,4'-piperidin]-2-one | Calc'd 483.2 Found 483.2 | A-118 & B-4 | n/a | n/a |

Example 85

5-chloro-1'-[2-({2-oxo-3-[(cis)-3-hydroxy-3-methylcyclobutyl]-1H,2H,3H-imidazo[4,5-b]pyridin-6-yl}oxy)ethyl]-1,2-dihydrospiro[indole-3,4'-piperidin]-2-one (Compound 374)

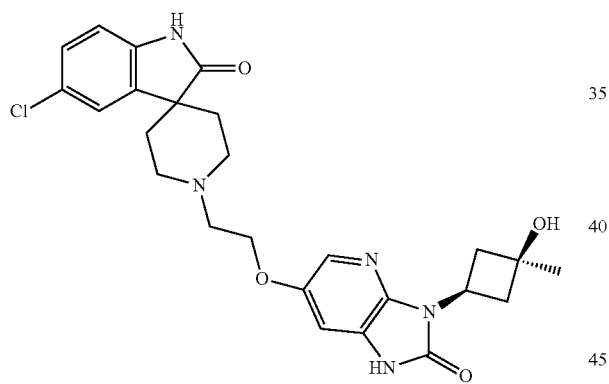

Step 1: (cis)-1-methyl-3-((3-nitro-5-(4,4,5,5-tetramethyl-1,3,2-dioxaborolan-2-yl)pyridin-2-yl)amino)cyclobutan-1-ol

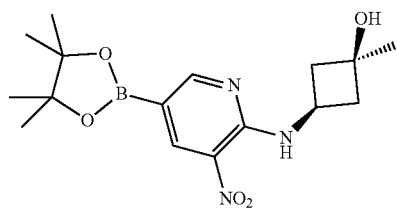

A mixture of (cis)-3-((5-bromo-3-nitropyridin-2-yl)amino)-1-methylcyclobutan-1-ol (General procedure for Intermediate A-92, Step 2, 1.00 g, 3.31 mmol), bis(pinacolato)diboron (1.68 g, 6.62 mmol), KOAc (650 mg, 6.62 mmol) and Pd(dppf)Cl$_2$ (121 mg, 165 µmol) in 1,4-dioxane (15 mL) was degassed and purged with N$_2$ for 10 min, and then stirred at 85° C. for 16 h under N$_2$ atmosphere. After cooling to room temperature, the mixture was filtered, and the filtrate was concentrated in vacuo to give (cis)-1-methyl-3-((3-nitro-5-(4,4,5,5-tetramethyl-1,3,2-dioxaborolan-2-yl)pyridin-2-yl)amino)cyclobutan-1-ol, which was used in the subsequent step without further purification. MS=267.9 [M-C$_6$H$_{10}$+H]$^+$.

Step 2: 6-(((cis)-3-hydroxy-3-methylcyclobutyl)amino)-5-nitropyridin-3-ol

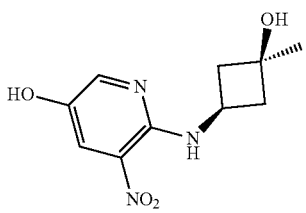 [SMILES: C[C@]1(O)C[C@@H](Nc2ncc(O)cc2[N+](=O)[O-])C1]

To a solution of 1(cis)-1-methyl-3-((3-nitro-5-(4,4,5,5-tetramethyl-1,3,2-dioxaborolan-2-yl)pyridin-2-yl)amino)cyclobutan-1-ol (1.00 g, 2.86 mmol) in THF (10 mL) and H$_2$O (10 mL) was added Oxone (1.76 g, 2.86 mmol). The mixture was stirred at room temperature for 2 h, then was diluted with H$_2$O (30 mL) and extracted with EtOAc (2×20 mL). The combined organic layers were dried over Na$_2$SO$_4$, filtered, and concentrated in vacuo. The residue was purified by flash silica gel chromatography (Biotage 12 g cartridge, 0-85% EtOAc/Petroleum ether) to give 6-(((cis)-3-hydroxy-3-methylcyclobutyl)amino)-5-nitropyridin-3-ol. MS=239.9 [M+H]$^+$.

Step 3: (cis)-3-((5-(2-bromoethoxy)-3-nitropyridin-2-yl)amino)-1-methylcyclobutan-1-ol

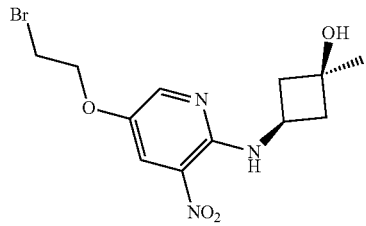 [SMILES: C[C@]1(O)C[C@@H](Nc2ncc(OCCBr)cc2[N+](=O)[O-])C1]

To a solution of 6-(((cis)-3-hydroxy-3-methylcyclobutyl)amino)-5-nitropyridin-3-ol (1.00 g, 4.18 mmol) in MeCN (20 mL) was added $K_2CO_3$ (2.31 g, 16.7 mmol) and 1,2-dibromoethane (6.31 mL, 83.6 mmol). The mixture was stirred at 65° C. for 12 h. After cooling to room temperature, the mixture was diluted with $H_2O$ (10 mL) and extracted with DCM (3×20 mL). The combined organic layers were dried over $Na_2SO_4$, filtered, and concentrated in vacuo. The residue was purified by flash silica gel chromatography (Biotage 20 g cartridge, 0-65% EtOAc/Petroleum ether) to give (cis)-3-((5-(2-bromoethoxy)-3-nitropyridin-2-yl)amino)-1-methylcyclobutan-1-ol. MS=346.1/348.1 [M+H]$^+$.

Step 4: (cis)-3-((3-amino-5-(2-bromoethoxy)pyridin-2-yl)amino)-1-methylcyclobutan-1-ol

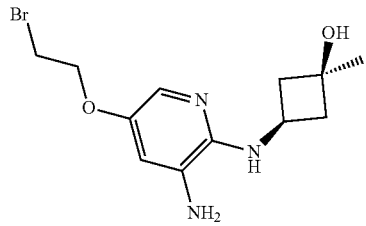 [SMILES: C[C@]1(O)C[C@@H](Nc2ncc(OCCBr)cc2N)C1]

To a solution of (cis)-3-((5-(2-bromoethoxy)-3-nitropyridin-2-yl)amino)-1-methylcyclobutan-1-ol (300 mg, 867 μmol) in EtOH (5 mL) and $H_2O$ (2.5 mL) was added Fe (484 mg, 8.67 mmol) and $NH_4Cl$ (695 mg, 13.0 mmol). The mixture was stirred at 60° C. for 4 h. After cooling to room temperature, the mixture was filtered. The filtrate was diluted with $H_2O$ (20 mL) and extracted with EtOAc (3×20 mL). The combined organic layers were dried over $Na_2SO_4$, filtered, and concentrated in vacuo to provide (cis)-3-((3-amino-5-(2-bromoethoxy)pyridin-2-yl)amino)-1-methylcyclobutan-1-ol, which was used in the subsequent step without further purification. MS=315.9/317.9 [M+H]$^+$.

Step 5: 6-(2-bromoethoxy)-3-((cis)-3-hydroxy-3-methylcyclobutyl)-1,3-dihydro-2H-imidazo[4,5-b]pyridin-2-one

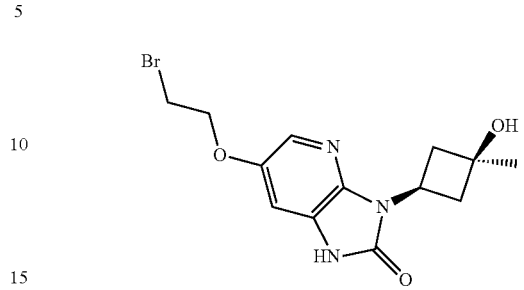

To a solution of (cis)-3-((3-amino-5-(2-bromoethoxy)pyridin-2-yl)amino)-1-methylcyclobutan-1-ol (100 mg, 316 μmol) in THF (4 mL) was added CDI (103 mg, 633 μmol). The mixture was stirred at 60° C. for 16 h. After cooling to room temperature, the mixture was diluted with $H_2O$ (10 mL) and extracted with EtOAc (2×50 mL). The combined organic layers were dried over $Na_2SO_4$, filtered, and concentrated in vacuo to provide 6-(2-bromoethoxy)-3-((cis)-3-hydroxy-3-methylcyclobutyl)-1,3-dihydro-2H-imidazo[4,5-b]pyridin-2-one, which was used in the subsequent step without further purification. MS=341.9/343.9 [M+H]$^+$.

Step 6: 5-chloro-1'-[2-({2-oxo-3-[(cis)-3-hydroxy-3-methylcyclobutyl]-1H,2H,3H-imidazo[4,5-b]pyridin-6-yl}oxy)ethyl]-1,2-dihydrospiro[indole-3,4'-piperidin]-2-one (Compound 374)

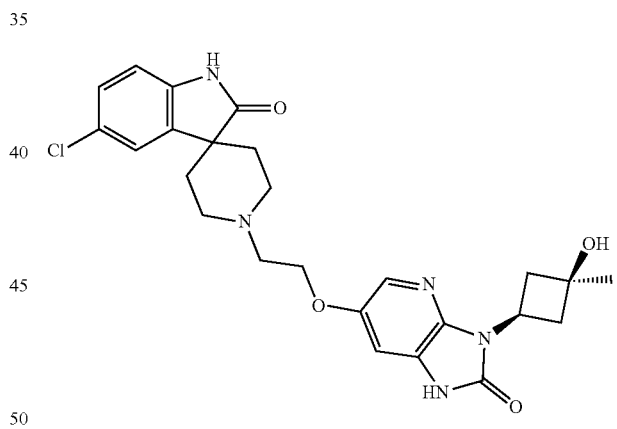

To a solution of 6-(2-bromoethoxy)-3-((cis)-3-hydroxy-3-methylcyclobutyl)-1,3-dihydro-2H-imidazo[4,5-b]pyridin-2-one (100 mg, 292 μmol) in MeCN (3 mL) was added $NaHCO_3$ (98.2 mg, 1.17 mmol) and 5-chloro-1,2-dihydrospiro[indole-3,4'-piperidin]-2-one (Intermediate B-4, 79.8 mg, 292 μmol, HCl salt). The mixture was stirred at 80° C. for 16 h. After cooling to room temperature, the mixture was concentrated in vacuo to remove MeCN. The residue was dissolved in DMF (1.5 mL) and was filtered to remove solids. The filtrate was purified by reverse phase preparative HPLC (Waters Xbridge OBD $C_{18}$ column, 20-50% MeCN: 10 mM $NH_4HCO_3$ in $H_2O$) to give 5-chloro-1'-[2-({2-oxo-3-[(cis)-3-hydroxy-3-methylcyclobutyl]-1H,2H,3H-imidazo[4,5-b]pyridin-6-yl}oxy)ethyl]-1,2-dihydrospiro[indole-3,4'-piperidin]-2-one (Compound 374). $^1$H NMR (400 MHz, DMSO-d$_6$): δ 11.04 (br s, 1H), 10.48 (s, 1H), 7.72 (d, J=2.4

Hz, 1H), 7.49 (d, J=1.8 Hz, 1H), 7.27-7.18 (m, 1H), 7.03 (d, J=2.6 Hz, 1H), 6.84 (d, J=8.4 Hz, 1H), 5.16 (s, 1H), 4.48-4.33 (m, 1H), 4.17 (t, J=6.0 Hz, 2H), 3.08-2.98 (m, 2H), 2.96-2.88 (m, 2H), 2.84 (t, J=6.0 Hz, 2H), 2.75-2.62 (m, 2H), 2.32-2.21 (m, 2H), 1.86-1.64 (m, 4H), 1.32 (s, 3H). MS=498.1 [M+H]$^+$.

Example 86

(5-chloro-1'-[2-({2-oxo-1-[(cis)-3-hydroxy-3-methylcyclobutyl]-1H,2H,3H,4H-pyrido[2,3-d]pyrimidin-6-yl}oxy)ethyl]-1,2-dihydrospiro[indole-3,4'-piperidin]-2-one, Compound 356)

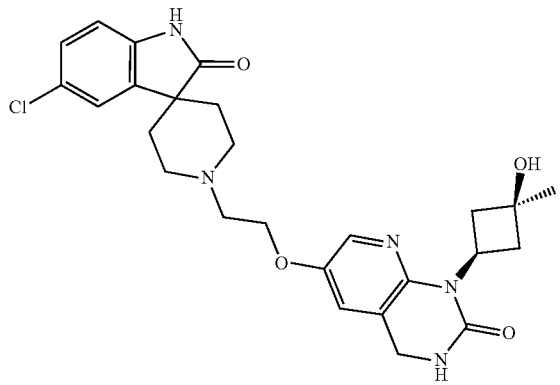 [SMILES: C[C@]1(O)C[C@@H](N2C(=O)NCc3cc(OCCN4CCC5(CC4)C(=O)Nc4ccc(Cl)cc45)cnc32)C1]

Step 1: tert-butyl N-[(5-bromo-2-fluoro-3-pyridyl)methyl]carbamate

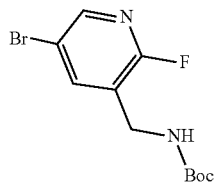

To a mixture of 5-bromo-2-fluoro-pyridine-3-carbaldehyde (5.00 g, 24.5 mmol) and tert-butyl carbamate (5.74 g, 49.0 mmol) in DCM (50 mL) under N$_2$ atmosphere was added TFA (5.44 mL, 73.5 mmol) and Et$_3$SiH (19.6 mL, 123 mmol). The mixture was stirred at room temperature for 16 h under N$_2$. The mixture was quenched by addition of saturated aqueous NaHCO$_3$ solution (130 mL) and extracted with DCM (2×100 mL). The combined organic layers were concentrated in vacuo. The residue was purified by flash silica gel chromatography (Biotage 80 g cartridge 0-8% EtOAc/Petroleum ether) to provide tert-butyl N-[(5-bromo-2-fluoro-3-pyridyl)methyl]carbamate. MS=304.9/306.9 [M+H]$^+$.

Step 2: tert-butyl N-[(5-bromo-2-{[(cis)-3-hydroxy-3-methylcyclobutyl]amino}pyridin-3-yl)methyl]carbamate

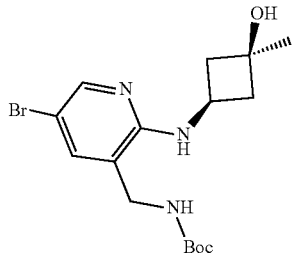 [SMILES: CC(C)(C)OC(=O)NCc1cc(Br)cnc1N[C@H]1C[C@@](C)(O)C1]

A mixture of tert-butyl N-[(5-bromo-2-fluoro-3-pyridyl)methyl]carbamate (3.80 g, 12.5 mmol), (cis)-3-amino-1-methylcyclobutanol (1.89 g, 13.7 mmol, HCl salt) and DIEA (41 mL, 249 mmol) in DMSO (20 mL) was stirred at 90° C. for 16 h under N$_2$ atmosphere. After cooling to room temperature, the mixture was diluted with H$_2$O (150 mL), and extracted with EtOAc (80 mL×2). The combined organic layers were concentrated in vacuo. The residue was purified by flash silica gel chromatography (Biotage 40 g cartridge, 0-25% EtOAc/Petroleum ether) to provide tert-butyl N-[(5-bromo-2-{[(cis)-3-hydroxy-3-methylcyclobutyl]amino}pyridin-3-yl)methyl]carbamate. MS=386.0/387.9 [M+H]$^+$.

Step 3: (cis)-3-{[3-(aminomethyl)-5-bromopyridin-2-yl]amino}-1-methylcyclobutan-1-ol

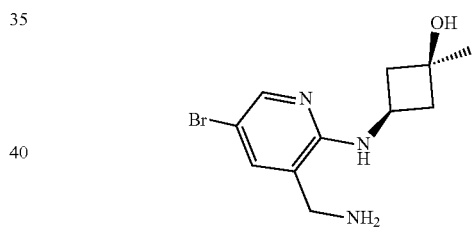

A solution of tert-butyl N-[(5-bromo-2-{[(cis)-3-hydroxy-3-methylcyclobutyl]amino}pyridin-3-yl)methyl]carbamate (1.50 g, 3.88 mmol) in 4.0 M HCl in EtOAc (15 mL, 60 mmol) was stirred at room temperature for 1 h. The mixture was concentrated in vacuo to give (cis)-3-{[3-(aminomethyl)-5-bromopyridin-2-yl]amino}-1-methylcyclobutan-1-ol, which was used in the subsequent step without further purification. MS=285.9/287.8 [M+H]$^+$.

Step 4: 6-bromo-1-[(cis)-3-hydroxy-3-methylcyclobutyl]-1H,2H,3H,4H-pyrido[2,3-d]pyrimidin-2-one

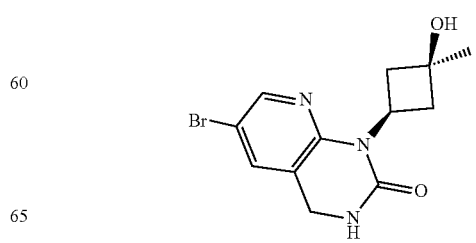

To a mixture of (cis)-3-{[3-(aminomethyl)-5-bromopyridin-2-yl]amino}-1-methylcyclobutan-1-ol (1.20 g, 4.19 mmol) in THF (15 mL) was added CDI (1.02 g, 6.29 mmol). The mixture was stirred at room temperature for 1 h, then was diluted with brine (15 mL) and extracted with EtOAc (2×20 mL). The combined organic layers were dried over Na$_2$SO$_4$, filtered and concentrated in vacuo to give 6-bromo-1-[(cis)-3-hydroxy-3-methylcyclobutyl]-1H,2H,3H,4H-pyrido[2,3-d]pyrimidin-2-one, which was used in the subsequent step without further purification. MS=312.0/313.9 [M+H]$^+$.

Step 5: 6-(2-hydroxyethoxy)-1-[(cis)-3-hydroxy-3-methylcyclobutyl]-1H,2H,3H,4H-pyrido[2,3-d]pyrimidin-2-one

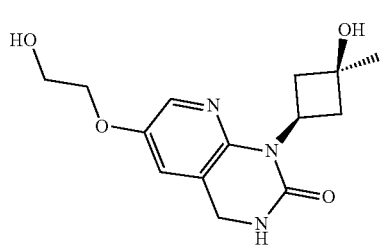 [SMILES: C[C@]1(O)C[C@@H](N2C(=O)NCc3cc(OCCO)cnc32)C1]

A mixture of 6-bromo-1-[(cis)-3-hydroxy-3-methylcyclobutyl]-1H,2H,3H,4H-pyrido[2,3-d]pyrimidin-2-one (350 mg, 1.12 mmol), CuI (85.4 mg, 0.448 mmol), t-BuOLi (359 mg, 4.48 mmol) and ethylene glycol (4.17 mL, 74.5 mmol) was degassed and purged with N$_2$ for 10 min, and then stirred at 120° C. for 16 h under N$_2$ atmosphere. After cooling to room temperature, the mixture was filtered and the filtrate was concentrated in vacuo. The filtrate was purified by reverse phase preparative HPLC (Waters Xbridge OBD C$_{18}$ column, 1-30% MeCN: 10 mM NH$_4$HCO$_3$ in H$_2$O) to give 6-(2-hydroxyethoxy)-1-[(cis)-3-hydroxy-3-methylcyclobutyl]-1H,2H,3H,4H-pyrido[2,3-d]pyrimidin-2-one. MS=294.0 [M+H]$^+$.

Step 6: 6-(2-bromoethoxy)-1-[(cis)-3-hydroxy-3-methylcyclobutyl]-1H,2H,3H,4H-pyrido[2,3-d]pyrimidin-2-one

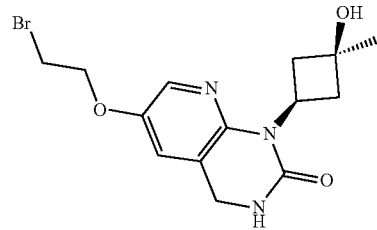 [SMILES: C[C@]1(O)C[C@@H](N2C(=O)NCc3cc(OCCBr)cnc32)C1]

To a mixture of 6-(2-hydroxyethoxy)-1-[(cis)-3-hydroxy-3-methylcyclobutyl]-1H,2H,3H,4H-pyrido[2,3-d]pyrimidin-2-one (180 mg, 0.614 mmol) in DCM (8 mL) at 0° C. under N$_2$ atmosphere was added PPh$_3$ (805 mg, 3.07 mmol), followed by CBr$_4$ (1.02 g, 3.07 mmol). The mixture was stirred at room temperature for 16 h under N$_2$ atmosphere, them was concentrated in vacuo. The residue was purified by flash silica gel chromatography (Biotage 4 g cartridge, 0-100% EtOAc/Petroleum ether) to give 6-(2-bromoethoxy)-1-[(cis)-3-hydroxy-3-methylcyclobutyl]-1H,2H,3H,4H-pyrido[2,3-d]pyrimidin-2-one. MS=356.0/357.9 [M+H]$^+$.

Step 7: 5-chloro-1'-[2-({2-oxo-1-[(cis)-3-hydroxy-3-methylcyclobutyl]-1H,2H,3H,4H-pyrido[2,3-d]pyrimidin-6-yl}oxy)ethyl]-1,2-dihydrospiro[indole-3,4'-piperidin]-2-one

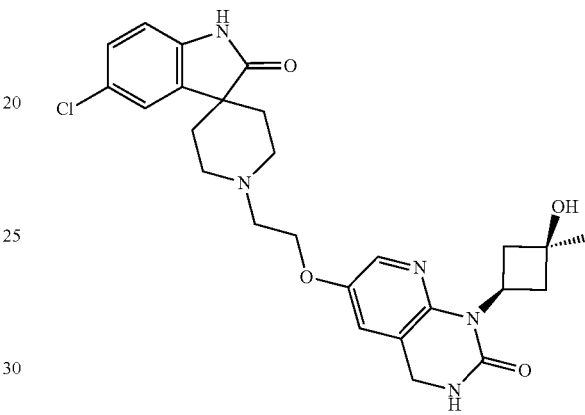

To a solution of 6-(2-bromoethoxy)-1-[(cis)-3-hydroxy-3-methylcyclobutyl]-1H,2H,3H,4H-pyrido[2,3-d]pyrimidin-2-one (50.0 mg, 0.140 mmol) in MeCN (4 mL) was added NaHCO$_3$ (47.2 mg, 0.561 mmol) and 5-chloro-1,2-dihydrospiro[indole-3,4'-piperidin]-2-one (Intermediate B-4, 38.3 mg, 0.140 mmol, HCl salt). The mixture was stirred at 80° C. for 16 h. After cooling to room temperature, the mixture was concentrated in vacuo. The residue was purified by reverse phase preparative HPLC (Waters Xbridge OBD C$_{18}$ column, 20-50% MeCN: 10 mM NH$_4$HCO$_3$ in H$_2$O) to give 5-chloro-1'-[2-({2-oxo-1-[(cis)-3-hydroxy-3-methylcyclobutyl]-1H,2H,3H,4H-pyrido[2,3-d]pyrimidin-6-yl}oxy)ethyl]-1,2-dihydrospiro[indole-3,4'-piperidin]-2-one (Compound 356). $^1$H NMR (400 MHz, DMSO-d$_6$): δ 10.48 (br s, 1H), 7.90 (d, J=2.8 Hz, 1H), 7.50 (d, J=2.0 Hz, 1H), 7.34 (d, J=2.8 Hz, 1H), 7.23 (dd, J=8.4, 2.0 Hz, 1H), 7.11 (s, 1H), 6.84 (d, J=8.4 Hz, 1H), 4.81 (s, 1H), 4.19-4.11 (m, 4H), 4.06 (t, J=7.6 Hz, 1H), 2.96-2.87 (m, 2H), 2.83 (t, J=5.6 Hz, 2H), 2.75-2.64 (m, 2H), 2.47-2.40 (m, 2H), 2.34-2.23 (m, 2H), 1.84-1.65 (m, 4H), 1.25 (s, 3H). MS=512.4 [M+H]$^+$.

Example 87

5-chloro-1'-(2-{[2-(2,2-dimethyl-1,3-dioxolan-4-yl)pyrimidin-5-yl]oxy}ethyl)-1,2-dihydrospiro[indole-3,4'-piperidin]-2-one 5-chloro-1'-(2-{[2-(1,2-dihydroxyethyl)pyrimidin-5-yl]oxy}ethyl)-1,2-dihydrospiro[indole-3,4'-piperidin]-2-one 5-chloro-1'-[2-({2-[(1R or 1S)-1,2-dihydroxyethyl]pyrimidin-5-yl}oxy)ethyl]-1,2-dihydrospiro[indole-3,4'-piperidin]-2-one & 5-chloro-1'-[2-({2-[(1S or 1R)-1,2-dihydroxyethyl]pyrimidin-5-yl}oxy)ethyl]-1,2-dihydrospiro[indole-3,4'-piperidin]-2-one (Compounds 441, 330, 378, & 379)

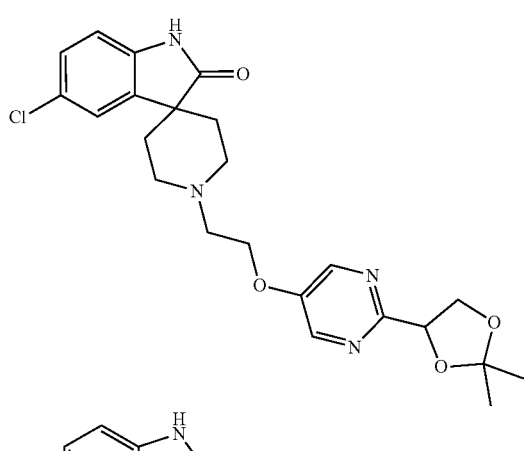

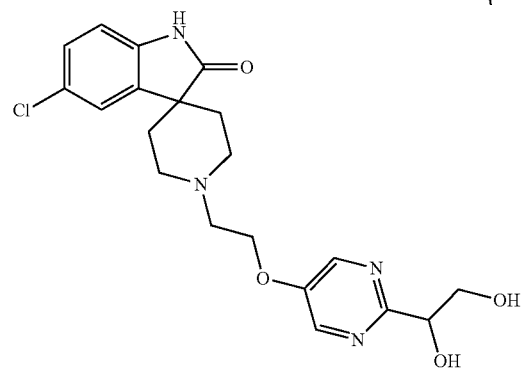

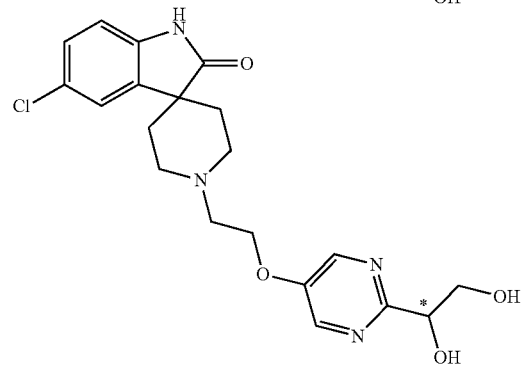

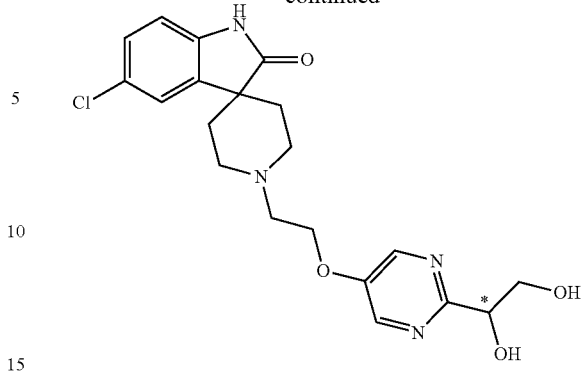

Step 1: 5-bromo-2-vinylpyrimidine

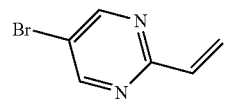

A mixture of 5-bromo-2-iodopyrimidine (5.00 g, 17.6 mmol), vinyl potassium trifluoroborate (2.59 g, 19.3 mmol), Pd(dppf)Cl$_2$ (1.28 g, 1.76 mmol), and K$_2$CO$_3$ (6.06 g, 43.9 mmol) in 1,4-dioxane (75 mL) and H$_2$O (25 mL) was degassed and purged with N$_2$ (3×), and then the mixture was stirred at 90° C. for 12 h under N$_2$ atmosphere. After cooling to room temperature, the reaction mixture was diluted with H$_2$O (60 mL) and extracted with EtOAc (3×50 mL). The combined organic layers were dried over Na$_2$SO$_4$, filtered, and concentrated in vacuo. The residue was purified by flash silica gel chromatography (Biotage 40 g cartridge, 0-15% EtOAc/Petroleum ether) to give 5-bromo-2-vinylpyrimidine. MS=185.10 [M+H]$^+$.

Step 2: 1-(5-bromopyrimidin-2-yl)ethane-1,2-diol

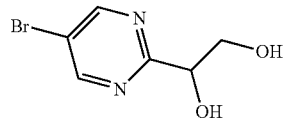 [SMILES: OCC(O)c1ncc(Br)cn1]

To a 0° C. solution of 5-bromo-2-vinyl-pyrimidine (1.80 g, 9.73 mmol) in THF (20 mL) and H$_2$O (20 mL) was added K$_2$OsO$_4$·2H$_2$O (358 mg, 0.973 mmol) and NMO (2.05 mL, 19.5 mmol). The mixture was allowed to warm to room temperature and stirred for 12 h. The reaction mixture was diluted with H$_2$O (30 mL) and extracted with EtOAc (3×50 mL). The combined organic layers were dried over Na$_2$SO$_4$, filtered, and concentrated in vacuo. The residue was purified by reverse phase preparative HPLC (Waters Xbridge OBD C$_{18}$ column, 25-55% MeCN: 10 mM NH$_4$HCO$_3$ in H$_2$O) to give 1-(5-bromopyrimidin-2-yl)ethane-1,2-diol. MS=219.10 [M+H]$^+$.

Step 3: 5-bromo-2-(2,2-dimethyl-1,3-dioxolan-4-yl)pyrimidine

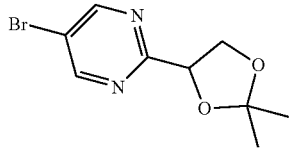

To a solution of 1-(5-bromopyrimidin-2-yl)ethane-1,2-diol (860 mg, 3.93 mmol) in acetone (9 mL) was added 2,2-dimethoxypropane (9.62 mL, 78.53 mmol) and TsOH (67.6 mg, 0.393 mmol). The mixture was stirred at room temperature for 16 h. The reaction mixture was with H$_2$O (20 mL) and extracted with EtOAc (4×20 mL). The combined organic layers were dried over Na$_2$SO$_4$, filtered, and concentrated under reduced pressure. The residue was purified by flash silica gel chromatography (Biotage 12 g cartridge, 0-70% EtOAc/Petroleum ether) to give 5-bromo-2-(2,2-dimethyl-1,3-dioxolan-4-yl)pyrimidine. MS=259.0 [M+H]$^+$.

Step 4: 2-(2,2-dimethyl-1,3-dioxolan-4-yl)pyrimidin-5-ol

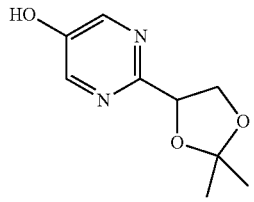

A mixture of 5-bromo-2-(2,2-dimethyl-1,3-dioxolan-4-yl)pyrimidine (200 mg, 0.772 mmol), Pd(dba)$_2$ (8.88 mg, 15.4 µmol), ditert-butyl-[2,3,4,5-tetramethyl-6-(2,4,6-triisopropylphenyl)phenyl]phosphane (37.1 mg, 77.2 µmol) and KOH (129.92 mg, 2.32 mmol) in H$_2$O (2 mL) and 1,4-dioxane (5 mL) was degassed and purged with N$_2$ (3×), and then the mixture was stirred at 100° C. for 16 h under N$_2$ atmosphere. After cooling to room temperature, the mixture was extracted with EtOAc (3×10 mL). The combined organic layers were washed with brine (2×10 mL), dried over Na$_2$SO$_4$, filtered and concentrated in vacuo to give 2-(2,2-dimethyl-1,3-dioxolan-4-yl)pyrimidin-5-ol), which was used in the subsequent step without further purification. MS=197.1 [M+H]$^+$.

Step 5: 5-(2-bromoethoxy)-2-(2,2-dimethyl-1,3-dioxolan-4-yl)pyrimidine

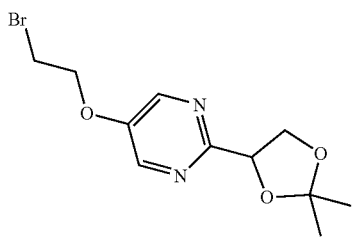 [SMILES: CC1(C)OCC(c2ncc(OCCBr)cn2)O1]

To a solution of 2-(2,2-dimethyl-1,3-dioxolan-4-yl)pyrimidin-5-ol (260 mg, 1.33 mmol) in MeCN (3 mL) and 1,2-dibromoethane (5 mL) under N$_2$ atmosphere was added K$_2$CO$_3$ (916 mg, 6.63 mmol). The mixture was stirred at 80° C. for 16 h under N$_2$ atmosphere. The reaction mixture was diluted with H$_2$O (30 mL) and extracted with DCM (3×20 mL). The combined organic layers were dried over Na$_2$SO$_4$, filtered and concentrated in vacuo to give 5-(2-bromoethoxy)-2-(2,2-dimethyl-1,3-dioxolan-4-yl)pyrimidine, which was used in the subsequent step without further purification. MS=303.2/305.2 [M+H]$^+$.

Step 6: 5-chloro-1'-(2-{[2-(2,2-dimethyl-1,3-dioxolan-4-yl)pyrimidin-5-yl]oxy}ethyl)-1,2-dihydrospiro[indole-3,4'-piperidin]-2-one (Compound 441)

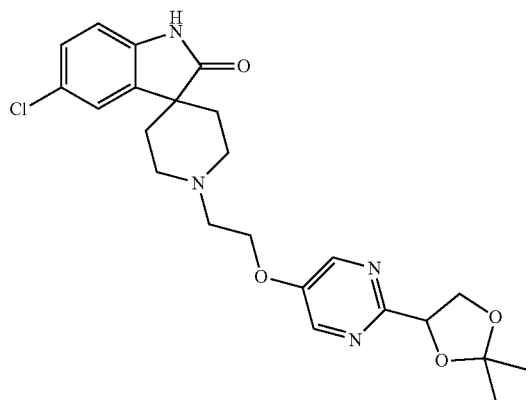 [SMILES: CC1(C)OCC(c2ncc(OCCN3CCC4(CC3)C(=O)Nc3ccc(Cl)cc34)cn2)O1]

To a solution of 5-(2-bromoethoxy)-2-(2,2-dimethyl-1,3-dioxolan-4-yl)pyrimidine (120 mg, 396 µmol) in MeCN (2 mL) under N$_2$ atmosphere was added NaHCO$_3$ (166 mg, 1.98 mmol) and 5-chloro-1,2-dihydrospiro[indole-3,4'-piperidin]-2-one (Intermediate B-4, 112 mg, 475 µmol, HCl salt). The mixture was stirred at 80° C. for 12 h under N$_2$ atmosphere. After cooling to room temperature, the reaction mixture was filtered and the filtrate was concentrated in vacuo to afford 5-chloro-1'-(2-{[2-(2,2-dimethyl-1,3-dioxolan-4-yl)pyrimidin-5-yl]oxy}ethyl)-1,2-dihydrospiro[indole-3,4'-piperidin]-2-one (Compound 441), which was used in the subsequent step without further purification. MS=459.2 [M+H]$^+$.

Step 7: 5-chloro-1'-(2-{[2-(1,2-dihydroxyethyl)pyrimidin-5-yl]oxy}ethyl)-1,2-dihydrospiro[indole-3,4'-piperidin]-2-one (Compound 330)

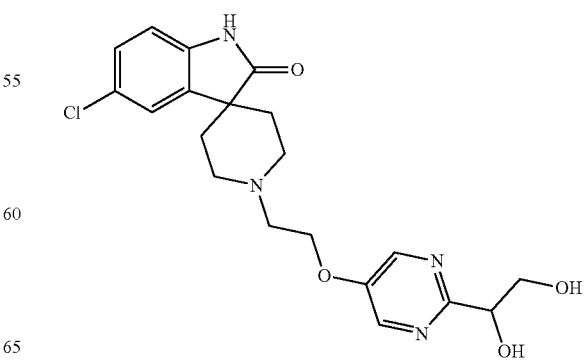

To a 0° C. solution of 5-chloro-1'-(2-{[2-(2,2-dimethyl-1,3-dioxolan-4-yl)pyrimidin-5-yl]oxy}ethyl)-1,2-dihydrospiro[indole-3,4'-piperidin]-2-one (Compound 441, 160 mg, 349 μmol) in THF (0.5 mL) was added 12 M aqueous HCl (0.20 mL, 2.4 mmol). The mixture was stirred at 0° C. for 2 h. The reaction mixture was filtered, and the filtrate was concentrated in vacuo. The residue was purified by reverse phase preparative HPLC (Waters Xbridge BEH $C_{18}$ column, 15-40% MeCN: 10 mM $NH_4HCO_3$ in $H_2O$) to give 5-chloro-1'-(2-{[2-(1,2-dihydroxyethyl)pyrimidin-5-yl]oxy}ethyl)-1,2-dihydrospiro[indole-3,4'-piperidin]-2-one (Compound 330). MS=419.3 [M+H]$^+$.

Step 8: 5-chloro-1'-[2-({2-[(1R or 1S)-1,2-dihydroxyethyl]pyrimidin-5-yl}oxy)ethyl]-1,2-dihydrospiro[indole-3,4'-piperidin]-2-one & 5-chloro-1'-[2-({2-[(1S or 1R)-1,2-dihydroxyethyl]pyrimidin-5-yl}oxy)ethyl]-1,2-dihydrospiro[indole-3,4'-piperidin]-2-one (Compounds 378 & 379)

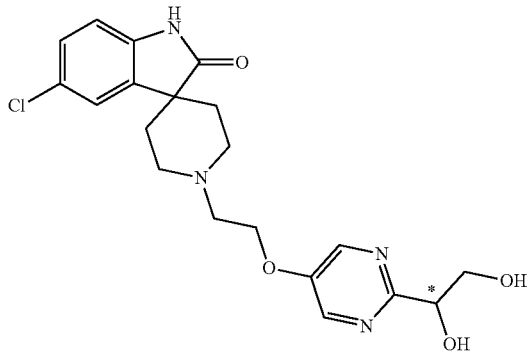

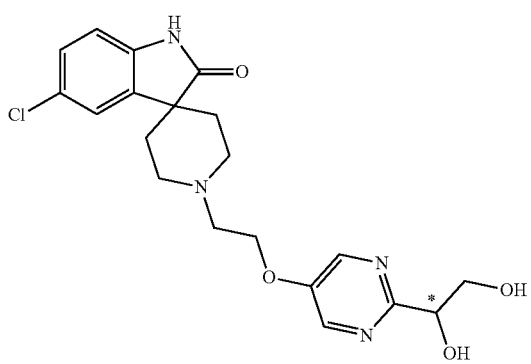 [SMILES: O=C1Nc2ccc(Cl)cc2C12CCN(CCOc1cnc(C(O)CO)nc1)CC2]

5-chloro-1'-(2-{[2-(1,2-dihydroxyethyl)pyrimidin-5-yl]oxy}ethyl)-1,2-dihydrospiro[indole-3,4'-piperidin]-2-one (Compound 330) was separated by preparative chiral SFC (Chiralcel IF column, 30-80% Heptane:(4:1 EtOH:MeCN) with 0.1% $NH_4OH$ in $CO_2$). The first eluting enantiomer of the title compound, 5-chloro-1'-[2-({2-[(1R or 1S)-1,2-dihydroxyethyl]pyrimidin-5-yl}oxy)ethyl]-1,2-dihydrospiro[indole-3,4'-piperidin]-2-one (Compound 379): $^1$H NMR (400 MHz, DMSO-$d_6$): δ 10.50 (s, 1H), 8.56 (s, 2H), 7.51 (s, 1H), 7.24 (dd, J=7.6, 2.0 Hz, 1H), 6.85 (d, J=8.4 Hz, 1H), 5.14 (d, J=2.0 Hz, 1H), 4.62-4.59 (m, 2H), 4.30 (t, J=5.6 Hz, 2H), 3.71-3.70 (m, 1H), 3.64-3.63 (m, 1H), 2.92-2.86 (m, 4H), 2.70-2.67 (m, 2H), 1.78-1.72 (m, 4H). MS=419.30 [M+H]$^+$. The second eluting enantiomer of the title compound, 5-chloro-1'-[2-({2-[(1S or 1R)-1,2-dihydroxyethyl]pyrimidin-5-yl}oxy)ethyl]-1,2-dihydrospiro[indole-3,4'-piperidin]-2-one (Compound 378): $^1$H NMR (400 MHz, DMSO-$d_6$): δ 10.50 (s, 1H), 8.56 (s, 2H), 7.51 (s, 1H), 7.24 (dd, J=8.0, 2.0 Hz, 1H), 6.85 (d, J=8.4 Hz, 1H), 5.14 (d, J=2.0 Hz, 1H), 4.62-4.59 (m, 2H), 4.30 (t, J=5.6 Hz, 2H), 3.71-3.70 (m, 1H), 3.64-3.63 (m, 1H), 2.92-2.86 (m, 4H), 2.70-2.67 (m, 2H), 1.78-1.72 (m, 4H). MS=419.30 [M+H]$^+$.

Example 88

5-chloro-1'-[2-({1-[(cis)-3-hydroxy-3-methylcyclobutyl]-1H-1,3-benzodiazol-5-yl}oxy)ethyl]-1,2-dihydrospiro[indole-3,4'-piperidin]-2-one (Compound 351)

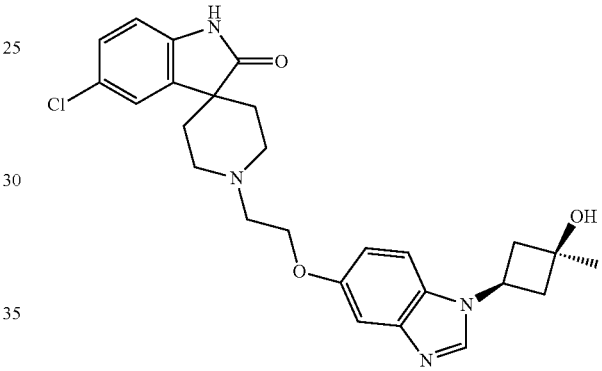

Step 1: (cis)-3-[(4-bromo-2-nitrophenyl)amino]-1-methylcyclobutan-1-ol

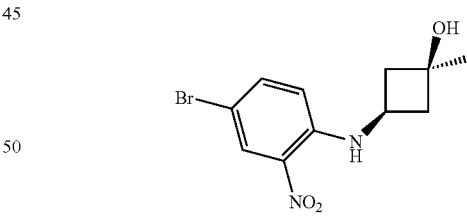

A mixture of 4-bromo-1-fluoro-2-nitro-benzene (1.96 mL, 15.9 mmol), (cis)-3-amino-1-methylcyclobutan-1-ol (2.41 g, 17.5 mmol, HCl salt) and DIEA (8.31 mL, 47.7 mmol) in DMSO (25 mL) under $N_2$ atmosphere was stirred at 90° C. for 1 h. After cooling to room temperature, the reaction mixture was quenched by addition of saturated aqueous $NH_4Cl$ solution (150 mL). The mixture was extracted with EtOAc (3×100 mL). The combined organic layers were washed with brine (2×50 mL), dried over $Na_2SO_4$, filtered, and concentrated in vacuo to give (cis)-3-[(4-bromo-2-nitrophenyl)amino]-1-methylcyclobutan-1-ol, which was used in the subsequent step without further purification. MS=300.9/302.9 [M+H]$^+$.

Step 2: (cis)-3-[(2-amino-4-bromophenyl)amino]-1-methylcyclobutan-1-ol

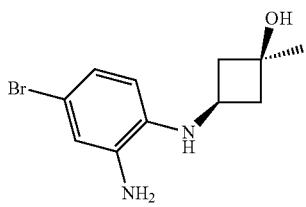

To a solution of (cis)-3-[(4-bromo-2-nitrophenyl)amino]-1-methylcyclobutan-1-ol (300 mg, 996 μmol) in EtOH (5 mL) and $H_2O$ (2.5 mL) was added Fe (556 mg, 9.96 mmol) and $NH_4Cl$ (799 mg, 14.9 mmol. The mixture was stirred at 60° C. for 2 h. After cooling to room temperature, the reaction mixture was filtered and the filtrate was concentrated in vacuo to afford (cis)-3-[(2-amino-4-bromophenyl)amino]-1-methylcyclobutan-1-ol, which was used in the subsequent step without further purification. MS=270.9/272.9 $[M+H]^+$.

Step 3: (cis)-3-(5-bromo-1H-1,3-benzodiazol-1-yl)-1-methylcyclobutan-1-ol

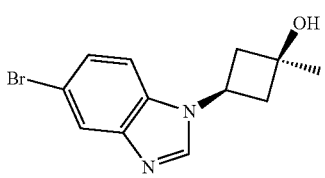 [SMILES: C[C@]1(O)C[C@@H](n2cnc3cc(Br)ccc32)C1]

To a solution of (cis)-3-[(2-amino-4-bromophenyl)amino]-1-methylcyclobutan-1-ol (1.00 g, 3.69 mmol) in triethoxymethane (6.13 mL, 36.9 mmol) was added TsOH (63.5 mg, 369 μmol). The mixture was stirred at 80° C. for 4 h. After cooling to room temperature, the reaction was filtered and the filtrate was concentrated in vacuo to give (cis)-3-(5-bromo-1H-1,3-benzodiazol-1-yl)-1-methylcyclobutan-1-ol, which was used in the subsequent step without further purification. MS=281.0/283.0 $[M+H]^+$.

Step 4: (cis)-3-[5-(2-hydroxyethoxy)-1H-1,3-benzodiazol-1-yl]-1-methylcyclobutan-1-ol

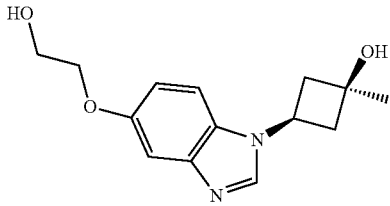 [SMILES: C[C@]1(O)C[C@@H](n2cnc3cc(OCCO)ccc32)C1]

To a solution of (cis)-3-(5-bromo-1H-1,3-benzodiazol-1-yl)-1-methylcyclobutan-1-ol (1.30 g, 4.62 mmol) in ethylene glycol (15 mL) was added $CuCl_2$ (124 mg, 925 μmol) and $K_2CO_3$ (1.92 g, 13.9 mmol). The mixture was degassed and purged with $N_2$ for 10 min, and then stirred at 130° C. for 6 h. After cooling to room temperature, the reaction mixture was filtered and the filtrate was concentrated in vacuo. The residue was purified by reverse phase preparative HPLC (Phenomenex Luna $C_{18}$ column, 1-30% MeCN: 10 mM $NH_4HCO_3$ in $H_2O$) to give (cis)-3-[5-(2-hydroxyethoxy)-1H-1,3-benzodiazol-1-yl]-1-methylcyclobutan-1-ol. MS=263.1 $[M+H]^+$.

Step 5: (cis)-3-[5-(2-iodoethoxy)-1H-1,3-benzodiazol-1-yl]-1-methylcyclobutan-1-ol

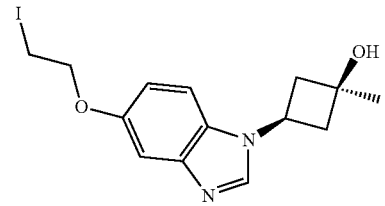 [SMILES: C[C@]1(O)C[C@@H](n2cnc3cc(OCCI)ccc32)C1]

To a solution of (cis)-3-[5-(2-hydroxyethoxy)-1H-1,3-benzodiazol-1-yl]-1-methylcyclobutan-1-ol (200 mg, 762 μmol) in DCM (5 mL) was added $I_2$ (169 μL, 839 μmol), imidazole (104 mg, 1.52 mmol), and $PPh_3$ (220 mg, 839 μmol). The mixture was stirred at room temperature for 4 h. The mixture was filtered, and the filtrate was concentrated in vacuo. The residue was purified by preparative TLC ($SiO_2$, DCM:MeOH=10:1) to give (cis)-3-[5-(2-iodoethoxy)-1H-1,3-benzodiazol-1-yl]-1-methylcyclobutan-1-ol. MS=373.0 $[M+H]^+$.

Step 6: 5-chloro-1'-[2-({1-[(cis)-3-hydroxy-3-methylcyclobutyl]-1H-1,3-benzodiazol-5-yl}oxy)ethyl]-1,2-dihydrospiro[indole-3,4'-piperidin]-2-one (Compound 351)

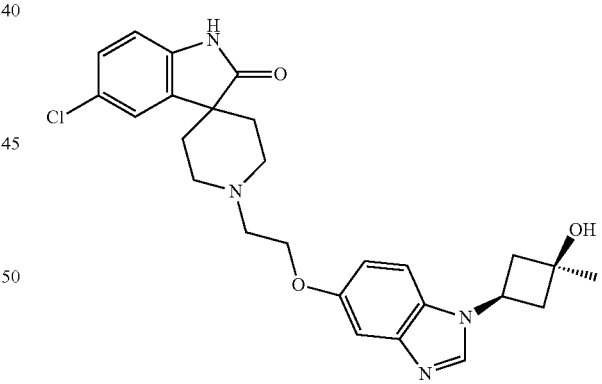

To a solution of (cis)-3-[5-(2-iodoethoxy)-1H-1,3-benzodiazol-1-yl]-1-methylcyclobutan-1-ol (40.0 mg, 107 μmol) in MeCN (2 mL) was added 5-chloro-1,2-dihydrospiro[indole-3,4'-piperidin]-2-one (Intermediate B-4, 32.3 mg, 118 μmol, HCl salt) and $NaHCO_3$ (36.1 mg, 430 μmol). The mixture was stirred at 80° C. for 12 h. After cooling to room temperature, the reaction mixture was quenched by addition of $H_2O$ (10 mL) and extracted with EtOAc (3×20 mL). The combined organic layers were washed with brine (30 mL), dried over $Na_2SO_4$, filtered and concentrated in vacuo. The crude residue was purified by reverse phase preparative HPLC (Phenomenex Luna $C_{18}$, 5-20% MeCN in $H_2O$ with 0.2% formic acid modifier) to give 5-chloro-1'-[2-({1-[(cis)-3-hydroxy-3-methylcyclobutyl]-1H-1,3-benzodiazol-5-yl}oxy)ethyl]-1,2-dihydrospiro[indole-3,4'-piperidin]-2-one (Compound 351, formic acid salt). $^1$H NMR (400 MHz, DMSO-$d_6$): δ 10.49 (s, 1H), 8.22 (s, 1H), 8.18 (s, 1H), 7.69-7.46 (m, 2H), 7.32-7.13 (m, 2H), 7.01-6.77 (m, 2H), 4.58 (t, J=8.4 Hz, 1H), 4.16 (t, J=5.6 Hz, 2H), 3.00-2.84 (m, 4H), 2.77-2.58 (m, 4H), 2.56-2.51 (m, 2H), 1.90-1.67 (m, 4H), 1.37 (s, 3H). MS=481.3 [M+H]$^+$.

Example 89

5-chloro-1'-[2-({2-methyl-1-[(cis)-3-hydroxy-3-methylcyclobutyl]-7-(trifluoromethyl)-1H-1,3-benzodiazol-5-yl}oxy)ethyl]-1,2-dihydrospiro[indole-3,4'-piperidin]-2-one (Compound 442)

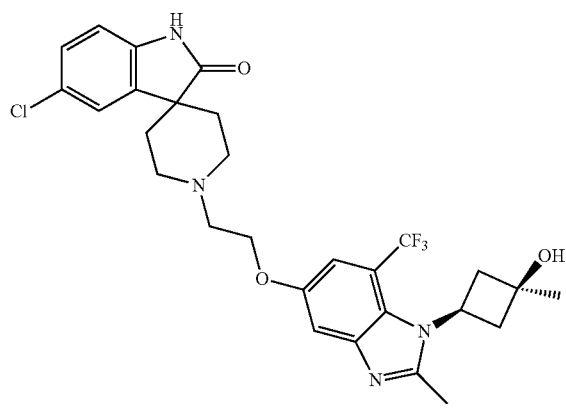 [SMILES: Cc1nc2cc(OCCN3CCC4(CC3)C(=O)Nc3ccc(Cl)cc34)cc(C(F)(F)F)c2n1[C@H]1C[C@@](C)(O)C1]

Step 1: (cis)-3-[5-(2-bromoethoxy)-2-methyl-7-(trifluoromethyl)-1H-1,3-benzodiazol-1-yl]-1-methylcyclobutan-1-ol

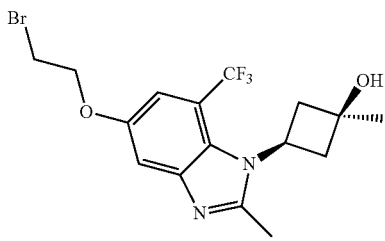 [SMILES: Cc1nc2cc(OCCBr)cc(C(F)(F)F)c2n1[C@H]1C[C@@](C)(O)C1]

To a mixture of 2-methyl-1-[(cis)-3-hydroxy-3-methylcyclobutyl]-7-(trifluoromethyl)-1H-1,3-benzodiazol-5-ol (Intermediate A-119, 1.40 g, 4.66 mmol) and 1,2-dibromoethane (17.5 g, 93.2 mmol) in i-PrOH (10 mL) was added Cs$_2$CO$_3$ (3.80 g, 11.7 mmol). The mixture was stirred at 60° C. for 2 h. After cooling to room temperature, the reaction mixture was filtered, and the filtrate was concentrated under reduced pressure. The residue was purified by flash silica gel chromatography (Biotage 20 g cartridge, 0-100% EtOAc/Petroleum ether) to give (cis)-3-[5-(2-bromoethoxy)-2-methyl-7-(trifluoromethyl)-1H-1,3-benzodiazol-1-yl]-1-methylcyclobutan-1-ol. MS=407.1/409.1 [M+H]$^+$.

Step 2: 5-chloro-1'-[2-({2-methyl-1-[(cis)-3-hydroxy-3-methylcyclobutyl]-7-(trifluoromethyl)-1H-1,3-benzodiazol-5-yl}oxy)ethyl]-1,2-dihydrospiro[indole-3,4'-piperidin]-2-one

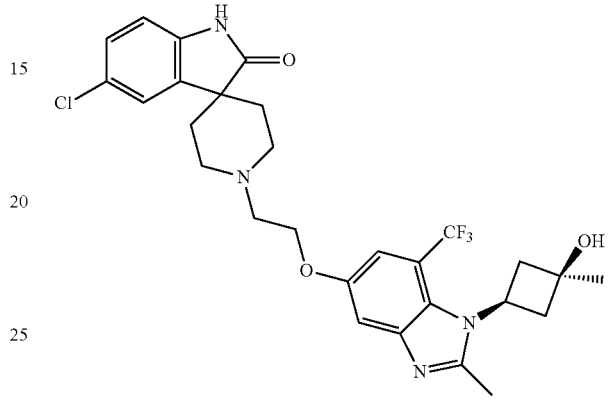

To a mixture of (cis)-3-[5-(2-bromoethoxy)-2-methyl-7-(trifluoromethyl)-1H-1,3-benzodiazol-1-yl]-1-methylcyclobutan-1-ol (150 mg, 368 mmol) and 5-chloro-1,2-dihydrospiro[indole-3,4'-piperidin]-2-one (Intermediate B-4, 121 mg, 442 mmol, HCl salt) in MeCN (4 mL) was added NaHCO$_3$ (92.8 mg, 1.11 mmol). The mixture was stirred at 80° C. for 16 h. After cooling to room temperature, the reaction mixture was filtered, and the filtrate was concentrated under reduced pressure. The residue was purified by reverse phase preparative HPLC (Waters Xbridge OBD C$_{18}$ column, 30-60% MeCN: 10 mM NH$_4$HCO$_3$ in H$_2$O) to give 5-chloro-1'-[2-({2-methyl-1-[(cis)-3-hydroxy-3-methylcyclobutyl]-7-(trifluoromethyl)-1H-1,3-benzodiazol-5-yl}oxy)ethyl]-1,2-dihydrospiro[indole-3,4'-piperidin]-2-one (Compound 442). $^1$H NMR (400 MHz, DMSO-$d_6$): δ 10.48 (s, 1H), 7.51-7.48 (m, 1H), 7.47-7.43 (m, 1H), 7.23 (dd, J=8.0, 2.0 Hz, 1H), 7.18 (d, J=2.0 Hz, 1H), 6.84 (d, J=8.0 Hz, 1H), 5.43 (s, 1H), 4.81-4.69 (m, 1H), 4.22 (t, J=5.6 Hz, 2H), 2.97-2.90 (m, 2H), 2.90-2.86 (m, 2H), 2.85 (s, 3H), 2.83-2.76 (m, 2H), 2.73-2.70 (m, 2H), 2.46-2.45 (m, 2H), 1.83-1.75 (m, 2H), 1.74-1.66 (m, 2H), 1.34 (s, 3H). MS=563.1 [M+H]$^+$.

The following intermediates in Table 38.16 were prepared according to procedures analogous to those described for Compound 442 using the appropriate starting materials or common intermediates.

TABLE 38.16

| # | Structure | IUPAC Name | Exact Mass [M + H]+ | Intermediates Used |
|---|---|---|---|---|
| 443 | 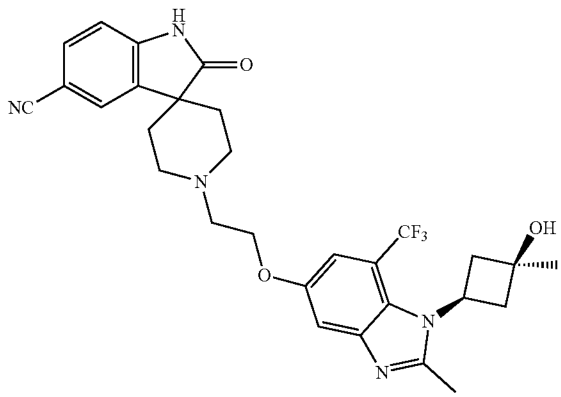 [SMILES: Cc1nc2cc(OCCN3CCC4(CC3)C(=O)Nc3ccc(C#N)cc34)cc(C(F)(F)F)c2n1[C@H]1C[C@@](C)(O)C1] | 1'-[2-({2-methyl-1-[(cis)-3-hydroxy-3-methylcyclobutyl]-7-(trifluoromethyl)-1H-1,3-benzodiazol-5-yl}oxy)ethyl]-2-oxo-1,2-dihydrospiro[indole-3,4'-piperidine]-5-carbonitrile | Calc'd 554.2 Found 554.2 | A-119 and B-9 |
| 444 | 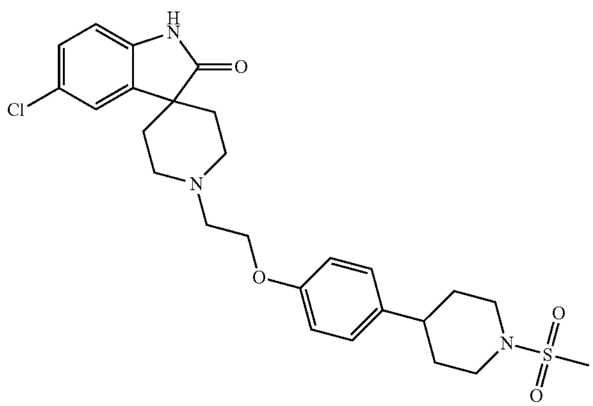 [SMILES: CS(=O)(=O)N1CCC(c2ccc(OCCN3CCC4(CC3)C(=O)Nc3ccc(Cl)cc34)cc2)CC1] | 5-chloro-1'-{2-[4-(1-methanesulfonylpiperidin-4-yl)phenoxy]ethyl}-1,2-dihydrospiro[indole-3,4'-piperidin]-2-one | Calc'd 518.2 Found 518.2 | General Procedure for Intermediate A-104, Step 2 and B-4 |
| 445 | 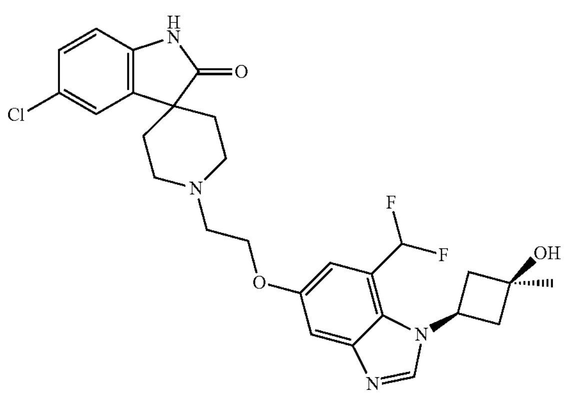 [SMILES: C[C@]1(O)C[C@@H](n2cnc3cc(OCCN4CCC5(CC4)C(=O)Nc4ccc(Cl)cc45)cc(C(F)F)c32)C1] | 5-chloro-1'-(2-{[7-(difluoromethyl)-1-[(cis)-3-hydroxy-3-methylcyclobutyl]-1H-1,3-benzodiazol-5-yl]oxy}ethyl)-1,2-dihydrospiro[indole-3,4'-piperidin]-2-one | Calc'd 431.2 Found 531.2 | A-120 and B-4 |
| 446 | 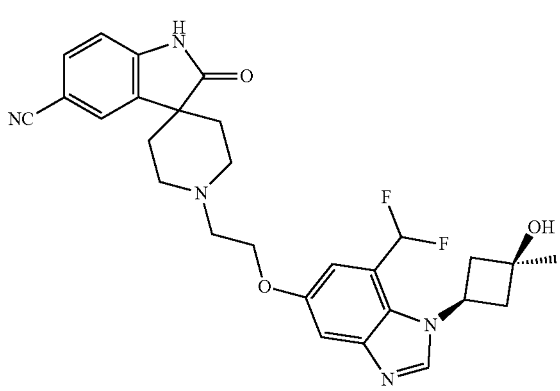 [SMILES: C[C@]1(O)C[C@@H](n2cnc3cc(OCCN4CCC5(CC4)C(=O)Nc4ccc(C#N)cc45)cc(C(F)F)c32)C1] | 1'-(2-{[7-(difluoromethyl)-1-[(cis)-3-hydroxy-3-methylcyclobutyl]-1H-1,3-benzodiazol-5-yl]oxy}ethyl)-2-oxo-1,2-dihydrospiro[indole-3,4'-piperidine]-5-carbonitrile | Calc'd 522.2 Found 522.2 | A-120 and B-9 |

TABLE 38.16-continued

| # | Structure | IUPAC Name | Exact Mass [M + H]+ | Intermediates Used |
|---|---|---|---|---|
| 447 | 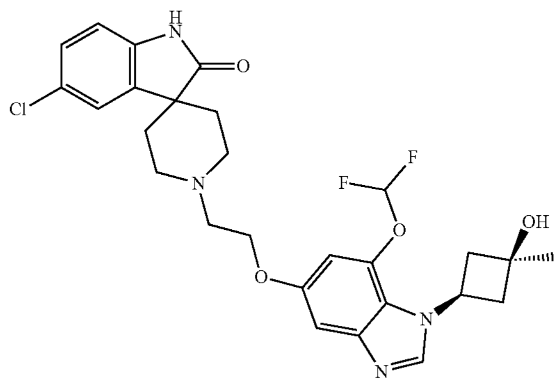 [SMILES: C[C@]1(O)C[C@@H](n2cnc3cc(OCCN4CCC5(CC4)C(=O)Nc4ccc(Cl)cc45)cc(OC(F)F)c32)C1] | 5-chloro-1'-(2-{[7-(difluoromethoxy)-1-[(cis)-3-hydroxy-3-methylcyclobutyl]-1H-1,3-benzodiazol-5-yl]oxy}ethyl)-1,2-dihydrospiro[indole-3,4'-piperidin]-2-one | Calc'd 547.2 Found 547.3 | A-121 and B-4 |
| 448 | 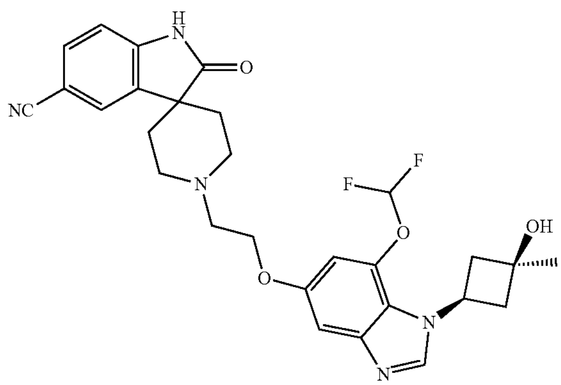 [SMILES: C[C@]1(O)C[C@@H](n2cnc3cc(OCCN4CCC5(CC4)C(=O)Nc4ccc(C#N)cc45)cc(OC(F)F)c32)C1] | 1'-(2-{[7-(difluoromethoxy)-1-[(cis)-3-hydroxy-3-methylcyclobutyl]-1H-1,3-benzodiazol-5-yl]oxy}ethyl)-2-oxo-1,2-dihydrospiro[indole-3,4'-piperidine]-5-carbonitrile | Calc'd 538.2 Found 538.3 | A-121 and B-9 |
| 449 | 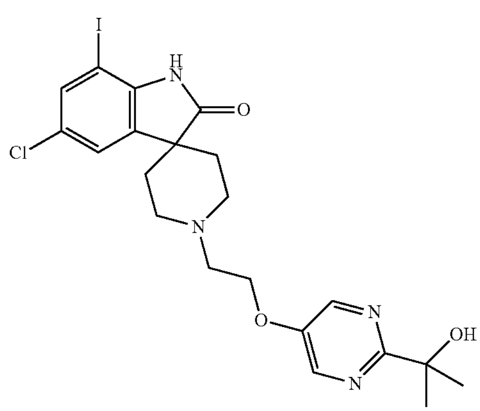 [SMILES: CC(C)(O)c1ncc(OCCN2CCC3(CC2)C(=O)Nc2c(I)cc(Cl)cc23)cn1] | 5-chloro-1'-(2-((2-(2-hydroxypropan-2-yl)pyrimidin-5-yl)oxy)ethyl)-7-iodospiro[indoline-3,4'-piperidin]-2-one | Calc'd 543.1 Found 543.2 | A-100 and B-24 |
| 450 | 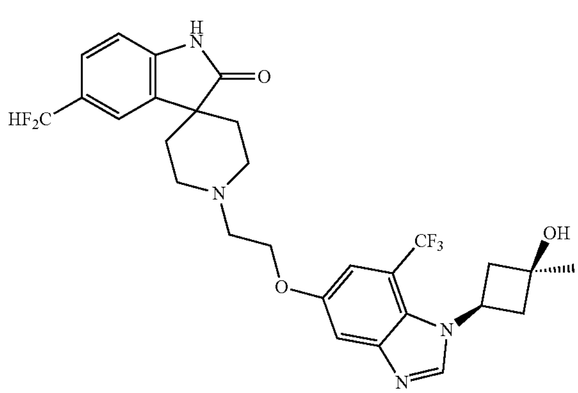 | 5-(difluoromethyl)-1'-[2-({1-[(cis)-3-hydroxy-3-methylcyclobutyl]-7-(trifluoromethyl)-1H-1,3-benzodiazol-5-yl}oxy)ethyl]-1,2-dihydrospiro[indole-3,4'-piperidin]-2-one | Calc'd 565.2 Found 565.2 | A-92 and B-1 |

TABLE 38.16-continued

| # | Structure | IUPAC Name | Exact Mass [M + H]+ | Intermediates Used |
|---|---|---|---|---|
| 451 | 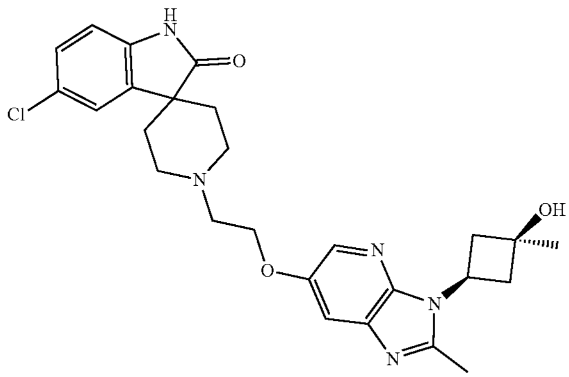 [SMILES: Cc1nc2cc(OCCN3CCC4(CC3)C(=O)Nc3ccc(Cl)cc34)cnc2n1[C@H]1C[C@@](C)(O)C1] | 5-chloro-1'-[2-({2-methyl-3-[(cis)-3-hydroxy-3-methylcyclobutyl]-3H-imidazo[4,5-b]pyridin-6-yl}oxy)ethyl]-1,2-dihydrospiro[indole-3,4'-piperidin]-2-one | Calc'd 496.2 Found 496.2 | A-122 and B-4 |
| 452 | 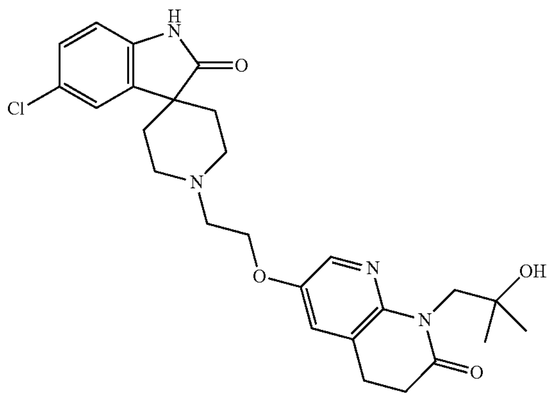 [SMILES: CC(C)(O)CN1C(=O)CCc2cc(OCCN3CCC4(CC3)C(=O)Nc3ccc(Cl)cc34)cnc21] | 5-chloro-1'-(2-{[8-(2-hydroxy-2-methylpropyl)-7-oxo-5,6,7,8-tetrahydro-1,8-naphthyridin-3-yl]oxy}ethyl)-1,2-dihydrospiro[indole-3,4'-piperidin]-2-one | Calc'd 499.2 Found 499.2 | A-105 and B-4 |
| 453 | 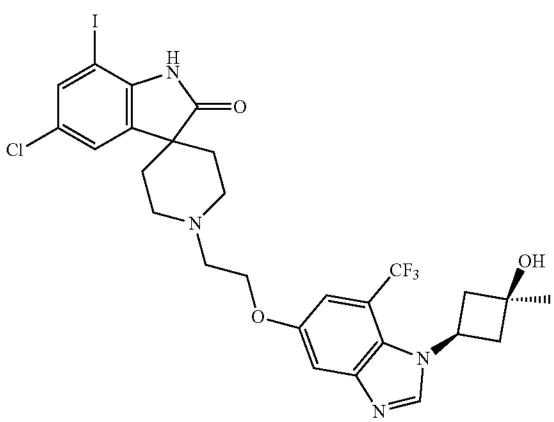 [SMILES: C[C@]1(O)C[C@@H](n2cnc3cc(OCCN4CCC5(CC4)C(=O)Nc4c(I)cc(Cl)cc45)cc(C(F)(F)F)c32)C1] | 5-chloro-7-iodo-1'-[2-({1-[(cis)-3-hydroxy-3-methylcyclobutyl]-7-(trifluoromethyl)-1H-1,3-benzodiazol-5-yl}oxy)ethyl]-1,2-dihydrospiro[indole-3,4'-piperidin]-2-one | Calc'd 675.1 Found 675.0 | A-92 and B-24 |
| 454 | 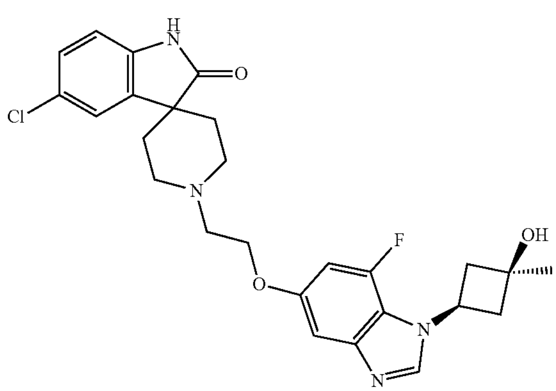 [SMILES: C[C@]1(O)C[C@@H](n2cnc3cc(OCCN4CCC5(CC4)C(=O)Nc4ccc(Cl)cc45)cc(F)c32)C1] | 5-chloro-1'-(2-((7-fluoro-1-((cis)-3-hydroxy-3-methylcyclobutyl)-1H-benzo[d]imidazol-5-yl)oxy)ethyl)spiro[indoline-3,4'-piperidin]-2-one | Calc'd 499.2 Found 499.2 | A-124 and B-4 |

| # | Structure | IUPAC Name | Exact Mass [M + H]+ | Intermediates Used |
|---|---|---|---|---|
| 455 | 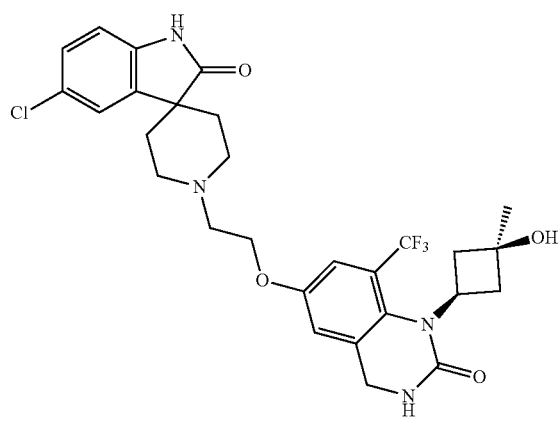 [SMILES: C[C@]1(O)C[C@@H](N2C(=O)NCc3cc(OCCN4CCC5(CC4)C(=O)Nc4ccc(Cl)cc45)cc(C(F)(F)F)c32)C1] | 1'-(2-((7-fluoro-1-((cis)-3-hydroxy-3-methylcyclobutyl)-1H-benzo[d]imidazol-5-yl)oxy)ethyl)-2-oxospiro[indoline-3,4'-piperidine]-5-carbonitrile | Calc'd 490.2<br>Found 490.2 | A-124 and B-9 |

Example 90

5-chloro-1'-[2-({2-oxo-1-[(cis)-3-hydroxy-3-methylcyclobutyl]-8-(trifluoromethyl)-1,2,3,4-tetrahydroquinazolin-6-yl}oxy)ethyl]-1,2-dihydrospiro[indole-3,4'-piperidin]-2-one (Compound 456)

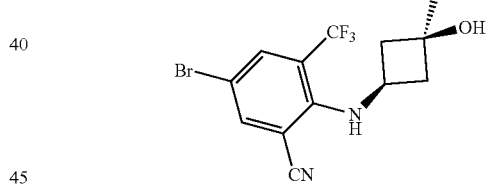

Step 1: 2-{[(cis)-3-hydroxy-3-methylcyclobutyl]amino}-3-(trifluoromethyl)benzonitrile

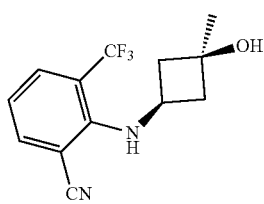 [SMILES: C[C@]1(O)C[C@@H](Nc2c(C#N)cccc2C(F)(F)F)C1]

To a solution of (cis)-3-amino-1-methylcyclobutanol (12.0 g, 87.3 mmol, HCl salt) in DMSO (150 mL) was added 2-fluoro-3-(trifluoromethyl)benzonitrile (15.0 g, 79.3 mmol) and DIEA (30.8 g, 238 mmol). The mixture was stirred at 60° C. for 6 h. After cooling to room temperature, the reaction mixture was quenched by addition of H$_2$O (200 mL) and extracted with EtOAc (3×80 mL). The combined organic layers were washed with brine (150 mL), dried over anhydrous Na$_2$SO$_4$, filtered, and concentrated in vacuo. The residue was purified by flash silica gel chromatography (Biotage 40 g cartridge, 0-10% EtOAc/Petroleum ether) to give 2-{[(cis)-3-hydroxy-3-methylcyclobutyl]amino}-3-(trifluoromethyl)benzonitrile. MS=271.1 [M+H]+.

Step 2: 5-bromo-2-{[(cis)-3-hydroxy-3-methylcyclobutyl]amino}-3-(trifluoromethyl)benzonitrile To a solution of 2-{[(cis)-3-hydroxy-3-methylcyclobutyl]amino}-3-(trifluoromethyl)benzonitrile (12.0 g, 44.4 mmol) in DMF (150 mL) was added NBS (10.3 g, 57.7 mmol). The mixture was stirred at 80° C. for 16 h. After cooling to room temperature, the reaction mixture was quenched by addition of H$_2$O (100 mL) and extracted with EtOAc (3×100 mL). The combined organic layers were washed with brine (300 mL), dried over Na$_2$SO$_4$, filtered, and concentrated under reduced pressure. The residue was purified by flash silica gel chromatography (Biotage 80 g cartridge, 0-15% EtOAc/Petroleum ether) to give 5-bromo-2-{[(cis)-3-hydroxy-3-methylcyclobutyl]amino}-3-(trifluoromethyl)benzonitrile. MS=349.0/351.0 [M+H]+.

Step 3: 2-{[(cis)-3-hydroxy-3-methylcyclobutyl]amino}-5-(4,4,5,5-tetramethyl-1,3,2-dioxaborolan-2-yl)-3-(trifluoromethyl)benzonitrile

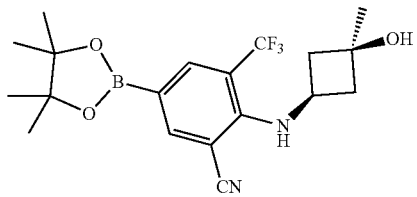 [SMILES: CC1(C)OB(c2cc(C#N)c(N[C@H]3C[C@@](C)(O)C3)c(C(F)(F)F)c2)OC1(C)C]

To a solution of 5-bromo-2-{[(cis)-3-hydroxy-3-methylcyclobutyl]amino}-3-(trifluoromethyl)benzonitrile (9.00 g, 25.8 mmol) in 1,4-dioxane (150 mL) was added KOAc (6.32 g, 64.4 mmol), bis(pinacolato)diboron (6.55 g, 25.8 mmol) and Pd(dppf)Cl$_2$ (1.89 g, 2.58 mmol). The mixture was degassed and purged with N$_2$ (3×), then stirred at 80° C. for 16 h. After cooling to room temperature, the reaction mixture was filtered, and the filtrate was concentrated under reduced pressure to give 2-{[(cis)-3-hydroxy-3-methylcyclobutyl]amino}-5-(4,4,5,5-tetramethyl-1,3,2-dioxaborolan-2-yl)-3-(trifluoromethyl)benzonitrile, which was taken to the next step without further purification. MS=397.1 [M+H]$^+$.

Step 4: 5-hydroxy-2-{[(cis)-3-hydroxy-3-methylcyclobutyl]amino}-3-(trifluoromethyl)benzonitrile

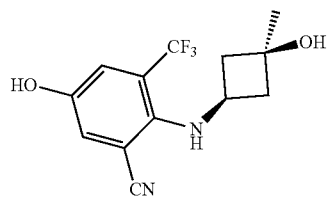 [SMILES: C[C@]1(O)C[C@@H](Nc2c(C#N)cc(O)cc2C(F)(F)F)C1]

To a solution of 2-{[(cis)-3-hydroxy-3-methylcyclobutyl]amino}-5-(4,4,5,5-tetramethyl-1,3,2-dioxaborolan-2-yl)-3-(trifluoromethyl)benzonitrile (15.0 g, 22.7 mmol, 60% purity) in THF (90 mL) and H$_2$O (30 mL) was added Oxone (13.9 g, 22.7 mmol). The mixture was stirred at room temperature for 2 h. The reaction mixture was quenched by addition of saturated aqueous Na$_2$SO$_3$ (100 ml) and extracted with EtOAc (3×200 mL). The combined organic layers were washed with brine (200 mL), dried over Na$_2$SO$_4$, filtered, and concentrated under reduced pressure. The residue was purified by flash silica gel chromatography (Biotage 80 g cartridge, 0-37% EtOAc/Petroleum ether) to give 5-hydroxy-2-{[(cis)-3-hydroxy-3-methylcyclobutyl]amino}-3-(trifluoromethyl)benzonitrile. MS=287.1 [M+H]$^+$ Step 5: 5-(2-bromoethoxy)-2-{[(cis)-3-hydroxy-3-methylcyclobutyl]amino}-3-(trifluoromethyl)benzonitrile

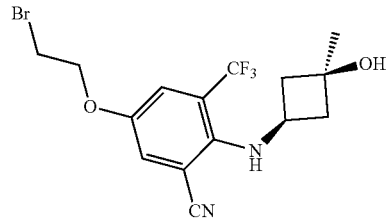 [SMILES: C[C@]1(O)C[C@@H](Nc2c(C#N)cc(OCCBr)cc2C(F)(F)F)C1]

To a solution of 5-hydroxy-2-{[(cis)-3-hydroxy-3-methylcyclobutyl]amino}-3-(trifluoromethyl)benzonitrile (6.00 g, 20.9 mmol) in 1,2-dibromoethane (63.3 mL, 838 mmol) and MeCN (20 mL) was added K$_2$CO$_3$ (14.5 g, 105 mmol). The mixture was stirred at 80° C. for 12 h. After cooling to room temperature, solids were removed by filtration. H$_2$O (80 mL) was then added to the filtrate, and the mixture was extracted with DCM (3×60 mL). The combined organic layers were dried over Na$_2$SO$_4$, filtered, and concentrated under reduced pressure. The residue was purified by flash silica gel chromatography (Biotage 40 g cartridge, 0-15% EtOAc/Petroleum ether) to give 5-(2-bromoethoxy)-2-{[(cis)-3-hydroxy-3-methylcyclobutyl]amino}-3-(trifluoromethyl)benzonitrile. MS=393.0/395.0 [M+H]$^+$.

Step 6: (cis)-3-{[2-(aminomethyl)-4-(2-bromoethoxy)-6-(trifluoromethyl)phenyl]amino}-1-methylcyclobutan-1-ol

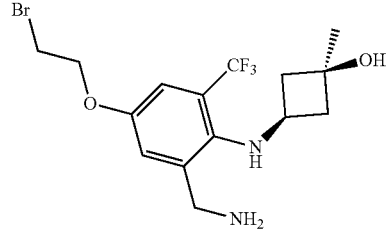 [SMILES: C[C@]1(O)C[C@@H](Nc2c(CN)cc(OCCBr)cc2C(F)(F)F)C1]

To a mixture of 5-(2-bromoethoxy)-2-{[(cis)-3-hydroxy-3-methylcyclobutyl]amino}-3-(trifluoromethyl)benzonitrile (3.00 g, 7.63 mmol) in THF (50 mL) at 0° C. was added 10 M BH$_3$·Me$_2$S in Me$_2$S (2.29 mL. 22.9 mmol). The mixture was then stirred at 60° C. for 5 h. After cooling to room temperature, the reaction mixture was quenched by addition of MeOH (30 mL) and H$_2$O (20 mL), then extracted with EtOAc (3×100 mL). The combined organic phases were dried over Na$_2$SO$_4$, filtered, and concentrated under reduced pressure to give (cis)-3-{[2-(aminomethyl)-4-(2-bromoethoxy)-6-(trifluoromethyl)phenyl]amino}-1-methylcyclobutan-1-ol, which was taken to the next step without further purification. MS=397.0/399.0 [M+H]$^+$.

Step 7: 6-(2-bromoethoxy)-1-[(cis)-3-hydroxy-3-methylcyclobutyl]-8-(trifluoromethyl)-1,2,3,4-tetrahydroquinazolin-2-one

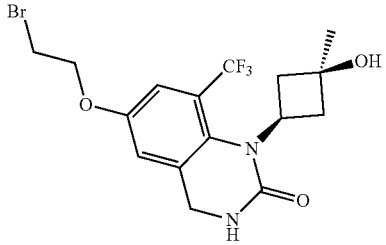 [SMILES: C[C@]1(O)C[C@@H](N2C(=O)NCc3cc(OCCBr)cc(C(F)(F)F)c32)C1]

To a solution of (cis)-3-{[2-(aminomethyl)-4-(2-bromoethoxy)-6-(trifluoromethyl)phenyl]amino}-1-methylcyclobutan-1-ol (200 mg, 503 μmol) in THF (5 mL) was added CDI (245 mg, 1.51 mmol). The mixture was stirred at 60° C. for 5 h. After cooling to room temperature, the reaction mixture was quenched with H$_2$O (10 mL) and extracted with EtOAc (3×10 mL). The combined organic phases were dried over Na$_2$SO$_4$, filtered, and concentrated under reduced pressure. The residue was purified by preparative TLC (SiO$_2$, 100% EtOAc) to give 6-(2-bromoethoxy)-1-[(cis)-3-hydroxy-3-methylcyclobutyl]-8-(trifluoromethyl)-1,2,3,4-tetrahydroquinazolin-2-one. MS=423.0/425.0 [M+H]$^+$.

Step 8: 5-chloro-1'-[2-({2-oxo-1-[(cis)-3-hydroxy-3-methylcyclobutyl]-8-(trifluoromethyl)-1,2,3,4-tetrahydroquinazolin-6-yl}oxy)ethyl]-1,2-dihydrospiro[indole-3,4'-piperidin]-2-one

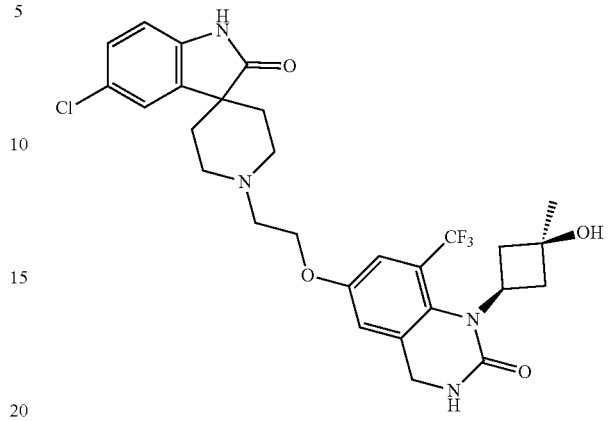

To a solution of 5-chloro-1,2-dihydrospiro[indole-3,4'-piperidin]-2-one (Intermediate B-4, 51.6 mg, 189 μmol, HCl salt) in MeCN (2 mL) was added 6-(2-bromoethoxy)-1-(3-hydroxy-3-methyl-cyclobutyl)-8-(trifluoromethyl)-3,4-dihydroquinazolin-2-one (80.0 mg, 189 μmol) and NaHCO$_3$ (63.5 mg, 756 μmol). The mixture was stirred at 80° C. for 5 h under N$_2$ atmosphere. The mixture was then diluted with H$_2$O (10 mL) and extracted with EtOAc (3×10 mL). The combined organic layers were dried over Na$_2$SO$_4$, filtered, and concentrated under reduced pressure. The filtrate was purified by reverse phase preparative HPLC (Phenomenex Luna C$_{18}$ column, 10-30% MeCN: 0.04% HCl in H$_2$O) to give 5-chloro-1'-[2-({2-oxo-1-[(cis)-3-hydroxy-3-methylcyclobutyl]-8-(trifluoromethyl)-1,2,3,4-tetrahydroquinazolin-6-yl}oxy)ethyl]-1,2-dihydrospiro[indole-3,4'-piperidin]-2-one (Compound 456). $^1$H NMR (400 MHz, DMSO-d$_6$, HCl salt): δ 10.96-10.66 (m, 1.5H), 10.30 (s, 0.5H), 7.99 (s, 1H), 7.35-7.31 (m, 1H), 7.30-7.27 (m, 1H), 7.26-7.15 (m, 2H), 6.91 (dd, J=8.0, 14.0 Hz, 1H), 5.32-4.67 (m, 1H), 4.49 (d, J=4.0 Hz, 2H), 4.13 (s, 2H), 3.87-3.55 (m, 7H), 2.55-2.51 (m, 1H), 2.39-2.28 (m, 2H), 2.24-2.12 (m, 1H), 2.06-1.86 (m, 4H), 1.16 (s, 3H). MS=579.1 [M+H]$^+$.

The following compounds in Table 38.17 were prepared according to procedures similar to steps described for Example 90 using the appropriate starting materials or common intermediates.

TABLE 38.17

| # | Structure | IUPAC Name | Exact Mass [M + H]$^+$ | Intermediates used |
|---|---|---|---|---|
| 457 | 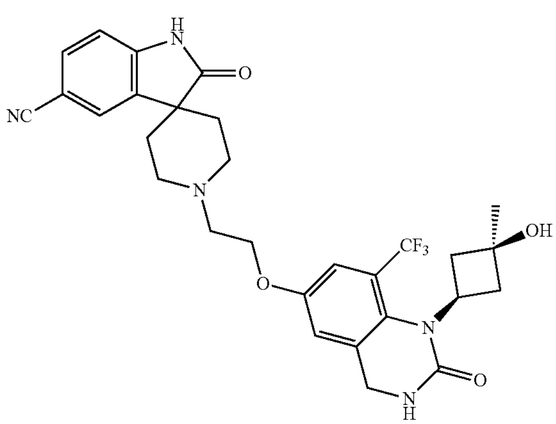 [SMILES: C[C@]1(O)C[C@@H](N2C(=O)NCc3cc(OCCN4CCC5(CC4)C(=O)Nc4ccc(C#N)cc45)cc(C(F)(F)F)c32)C1] | 2-oxo-1'-[2-({2-oxo-1-[(cis)-3-hydroxy-3-methylcyclobutyl]-8-(trifluoromethyl)-1,2,3,4-tetrahydroquinazolin-6-yl}oxy)ethyl]-1,2-dihydrospiro[indole-3,4'-piperidine]-5-carbonitrile | Calc'd 570.2 Found 570.1 | B-9 |

Example 91

5-chloro-1'-[2-({7,7-dimethyl-5-oxo-5H,7H-furo[3,4-b]pyridin-3-yl}oxy)ethyl]-1,2-dihydrospiro[indole-3,4'-piperidin]-2-one (Compound 458)

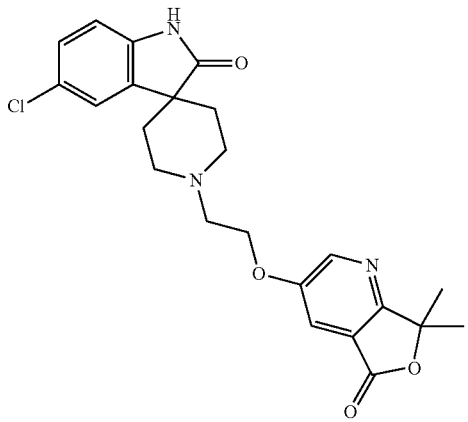 [SMILES: CC1(C)OC(=O)c2cc(OCCN3CCC4(CC3)C(=O)Nc3ccc(Cl)cc34)cnc21]

Step 1: 2-chloro-5-(4,4,5,5-tetramethyl-1,3,2-dioxaborolan-2-yl)pyridine-3-carbonitrile

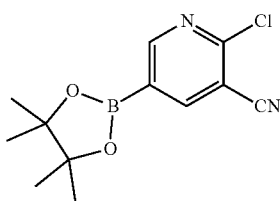 [SMILES: CC1(C)OB(c2cnc(Cl)c(C#N)c2)OC1(C)C]

A mixture of 5-bromo-2-chloro-pyridine-3-carbonitrile (10.0 g, 46.0 mmol), bis(pinacolato)diboron (17.5 g, 69.0 mmol), KOAc (11.3 g, 115 mmol) and Pd(dppf)Cl$_2$CH$_2$Cl$_2$ (1.88 g, 2.30 mmol) in 1,4-dioxane (100 mL) was degassed and purged with N$_2$ (3×), and then the mixture was stirred at 90° C. for 12 h under N$_2$ atmosphere. After cooling to room temperature, solids were removed by filtration, and then the mixture concentrated in vacuo give 2-chloro-5-(4,4,5,5-tetramethyl-1,3,2-dioxaborolan-2-yl)pyridine-3-carbonitrile, which was taken to the next step without further purification.

Step 2: 2-chloro-5-hydroxypyridine-3-carbonitrile

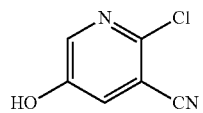

To a solution of 2-chloro-5-(4,4,5,5-tetramethyl-1,3,2-dioxaborolan-2-yl)pyridine-3-carbonitrile (1.30 g, 4.91 mmol) in THF (10 mL) and H$_2$O (4 mL) was added Oxone (2.42 g, 3.93 mmol). The mixture was stirred at 0° C. for 1 h, then was quenched with saturated aqueous Na$_2$SO$_3$ solution (10 mL) and extracted with EtOAc (3×10 mL). The combined organic phases were dried over Na$_2$SO$_4$, filtered, and concentrated in vacuo. The residue was purified by flash silica gel chromatography (Biotage 12 g cartridge, 0-30% EtOAc/Petroleum ether) to provide 2-chloro-5-hydroxypyridine-3-carbonitrile. MS=155.1 [M+H]$^+$.

Step 3: 5-(2-bromoethoxy)-2-chloropyridine-3-carbonitrile

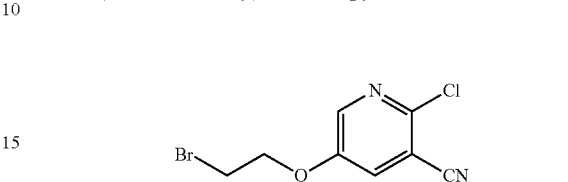

To a solution of 2-chloro-5-hydroxypyridine-3-carbonitrile (550 mg, 3.56 mmol) in MeCN (7 mL) was added K$_2$CO$_3$ (2.46 g, 17.8 mmol) and 1,2-dibromoethane (20.1 g, 107 mmol). The mixture was stirred at 80° C. for 12 h. After cooling to room temperature, the solids were removed by filtration and the filtrate was concentrated in vacuo. The residue was purified by flash silica gel chromatography (Biotage 12 g cartridge, 0-30% EtOAc/Petroleum ether) to provide 5-(2-bromoethoxy)-2-chloropyridine-3-carbonitrile. MS=260.9/262.9 [M+H]$^+$.

Step 4: 5-(2-bromoethoxy)-2-(prop-1-en-2-yl)pyridine-3-carbonitrile

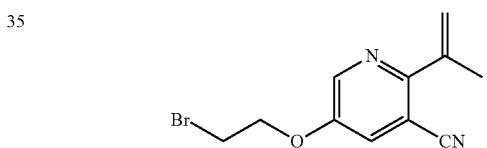

A mixture of 5-(2-bromoethoxy)-2-chloropyridine-3-carbonitrile (300 mg, 1.15 mmol), 2-isopropenyl-4,4,5,5-tetramethyl-1,3,2-dioxaborolane (386 mg, 2.29 mmol), Cs$_2$CO$_3$ (1.87 g, 5.74 mmol) and Pd(PPh$_3$)Cl$_2$ (8.05 mg, 11.5 µmol) in 1,4-dioxane (3 mL) and H$_2$O (0.5 mL) was degassed and purged with N$_2$ (3×), and then the mixture was stirred at 100° C. for 2 h under N$_2$ atmosphere. After cooling to room temperature, the reaction mixture was filtered, and the filtrate was concentrated under reduced pressure. The residue was purified by flash silica gel chromatography (Biotage 12 g cartridge, 0-20% EtOAc/Petroleum ether) to give 5-(2-bromoethoxy)-2-(prop-1-en-2-yl)pyridine-3-carbonitrile. MS=267.0/269.0 [M+H]$^+$.

Step 5: 5-(2-bromoethoxy)-2-(2-hydroxypropan-2-yl)pyridine-3-carbonitrile

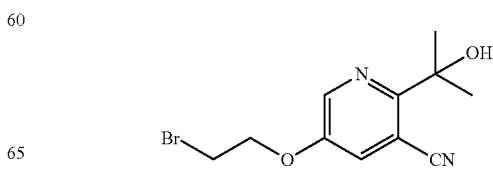

A mixture of 5-(2-bromoethoxy)-2-(prop-1-en-2-yl)pyridine-3-carbonitrile (100 mg, 374 μmol), tris(2,2,6,6-tetramethyl-3,5-heptanedionato)manganese(III) (22.6 mg, 37.4 μmol), and phenylsilane (81.0 mg, 749 μmol) in DCM (0.5 mL) and i-PrOH (10 mL) was degassed and purged with O2 (3×), and then the mixture was stirred at 0° C. for 2 h under O2 atmosphere. The reaction mixture was filtered, and the filtrate was concentrated under reduced pressure. The residue was purified by flash silica gel chromatography (Biotage 4 g cartridge, 0-40% EtOAc/Petroleum ether) to give 5-(2-bromoethoxy)-2-(2-hydroxypropan-2-yl)pyridine-3-carbonitrile. MS=285.0/286.9 [M+H]+.

Step 6: 5-chloro-1'-[2-({7,7-dimethyl-5-oxo-5H,7H-furo[3,4-b]pyridin-3-yl}oxy)ethyl]-1,2-dihydrospiro[indole-3,4'-piperidin]-2-one

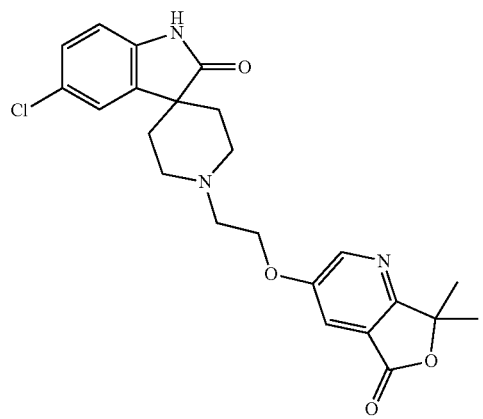 [SMILES: CC1(C)OC(=O)c2cc(OCCN3CCC4(CC3)C(=O)Nc3ccc(Cl)cc34)cnc21]

To a solution of 5-(2-bromoethoxy)-2-(2-hydroxypropan-2-yl)pyridine-3-carbonitrile (100 mg, 351 μmol) and 5-chloro-1,2-dihydrospiro[indole-3,4'-piperidin]-2-one (Intermediate B-4, 105 mg, 386 μmol, HCl salt) in MeCN (3 mL) was added NaHCO₃ (88.4 mg, 1.05 mmol). The mixture was stirred at 80° C. for 12 h. After cooling to room temperature, the reaction mixture was filtered, and the filtrate was concentrated under reduced pressure. The filtrate was purified by reverse phase preparative HPLC (Phenomenex Luna C₁₈ column, 20-50% MeCN: 10 mM NH₄HCO₃ in H₂O) to give 5-chloro-1'-[2-({7,7-dimethyl-5-oxo-5H,7H-furo[3,4-b]pyridin-3-yl}oxy)ethyl]-1,2-dihydrospiro[indole-3,4'-piperidin]-2-one (Compound 458). ¹H NMR (400 MHz, DMSO-d₆): δ 10.49 (s, 1H), 8.64 (d, J=2.8 Hz, 1H), 7.78 (d, J=2.4 Hz, 1H), 7.50 (d, J=1.6 Hz, 1H), 7.24 (dd, J=8.0, 2.0 Hz, 1H), 6.85 (d, J=8.4 Hz, 1H), 4.33 (t, J=5.6 Hz, 2H), 2.96-2.86 (m, 4H), 2.74-2.67 (m, 2H), 1.82-1.67 (m, 4H), 1.61 (s, 6H). MS=442.3 [M+H]+.

Example 92

5-chloro-1'-{2-[(2-{6-hydroxy-6-methyl-2-azaspiro[3.3]heptan-2-yl}pyrimidin-5-yl)oxy]ethyl}-1,2-dihydrospiro[indole-3,4'-piperidin]-2-one (Compound 459)

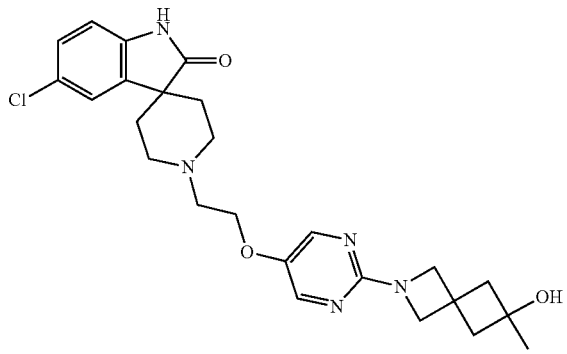 [SMILES: CC1(O)CC2(CN(c3ncc(OCCN4CCC5(CC4)C(=O)Nc4ccc(Cl)cc45)cn3)C2)C1]

Step 1: 5-(2-bromoethoxy)-2-chloropyrimidine

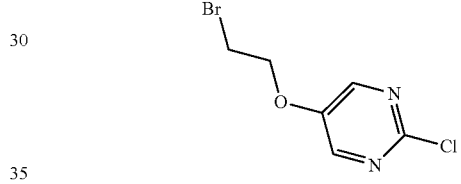

To a solution of 2-chloropyrimidin-5-ol (1.00 g, 7.66 mmol) in DMF (7.661 mL) was added 1,2-dibromoethane (15.3 mL) and Cs₂CO₃ (7.49 g, 23.0 mmol). The reaction was heated at 90° C. for 16 h. The reaction was cooled to room temperature, diluted with EtOAc (30 mL), and filtered through a pad of Celite. The filtrate was concentrated, and the residue was purified by flash silica gel chromatography (Biotage 50 g cartridge, 0-100% EtOAc/Hexanes) to provide 5-(2-bromoethoxy)-2-chloropyrimidine. MS=236.96 [M+H]+.

Step 2: 5-chloro-1'-{2-[(2-chloropyrimidin-5-yl)oxy]ethyl}-1,2-dihydrospiro[indole-3,4'-piperidin]-2-one

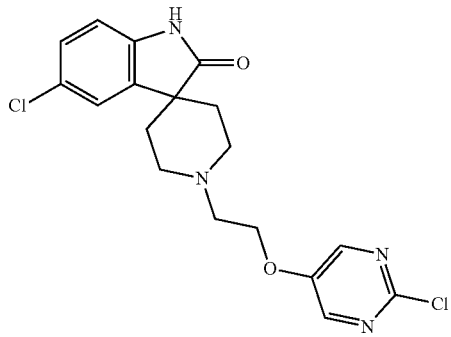 [SMILES: O=C1Nc2ccc(Cl)cc2C12CCN(CCOc1cnc(Cl)nc1)CC2]

To a vial was added 5-(2-bromoethoxy)-2-chloropyrimidine (1.23 g, 5.18 mmol), 5-chloro-1,2-dihydrospiro[indole-3,4'-piperidin]-2-one (Intermediate B-4, 1.34 g, 4.92 mmol, HCl salt), K₂CO₃ (2.15 g, 15.5 mmol), and KI (860 mg, 5.18 mmol) followed by DMF (17.3 mL). The mixture was heated at 65° C. for 4 h. The reaction was cooled to room temperature and diluted with H₂O (100 mL). The resulting precipitate was collected by filtration and dried in vacuo to provide 5-chloro-1'-{2-[(2-chloropyrimidin-5-yl)oxy]ethyl}-1,2-dihydrospiro[indole-3,4'-piperidin]-2-one, which was used in the subsequent step without further purification. MS=393.2 [M+H]⁺.

Step 3: 5-chloro-1'-{2-[(2-{6-hydroxy-6-methyl-2-azaspiro[3.3]heptan-2-yl}pyrimidin-5-yl)oxy]ethyl}-1,2-dihydrospiro[indole-3,4'-piperidin]-2-one

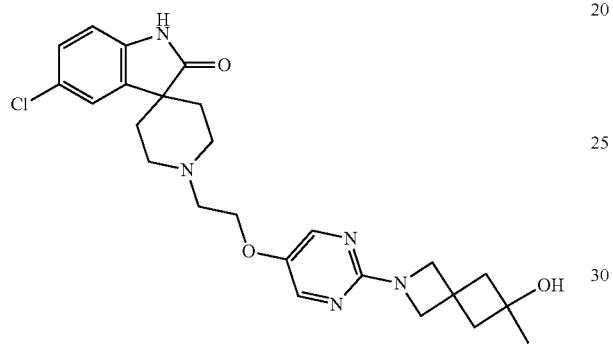

To a solution of 5-chloro-1'-{2-[(2-chloropyrimidin-5-yl)oxy]ethyl}-1,2-dihydrospiro[indole-3,4'-piperidin]-2-one (75.0 mg, 0.191 mmol) and 6-methyl-2-azaspiro[3.3]heptan-6-ol (156 mg, 0.954 mmol, HCl salt) in DMSO (0.381 mL) was added triethylamine (0.132 mL, 0.954 mmol). The reaction was heated at 100° C. under microwave irradiation for 1 h. After cooling to room temperature, the mixture was diluted with H₂O (1 mL) and MeCN (1 mL). The resulting solution was purified by reverse phase preparative HPLC (Phenomenex Kinetex C₁₈ column, 5-50% MeCN in H₂O with 0.1% NH₄OH modifier) to give 5-chloro-1'-{2-[(2-{6-hydroxy-6-methyl-2-azaspiro[3.3]heptan-2-yl}pyrimidin-5-yl)oxy]ethyl}-1,2-dihydrospiro[indole-3,4'-piperidin]-2-one (Compound 459). ¹H NMR (500 MHz, DMSO-d₆, 29/30H): δ 10.41 (s, 1H), 8.15-8.06 (m, 2H), 7.42 (d, J=2.1 Hz, 1H), 7.16 (dd, J=8.2, 2.1 Hz, 1H), 6.77 (d, J=8.2 Hz, 1H), 4.82 (s, 1H), 4.27-4.02 (m, 2H), 3.94-3.77 (m, 4H), 2.87-2.77 (m, 2H), 2.73 (t, J=5.7 Hz, 2H), 2.65-2.55 (m, 2H), 2.16-2.07 (m, 3H), 1.77-1.57 (m, 4H), 1.12 (s, 3H). MS=484.28 [M+H]⁺.

Example 93

5-chloro-1'-(2-{2'-oxo-1'-[(cis)-3-hydroxy-3-methylcyclobutyl]-1',2'-dihydrospiro[cyclopropane-1,3'-pyrrolo[2,3-b]pyridin]-5'-yloxy}ethyl)-1,2-dihydrospiro[indole-3,4'-piperidin]-2-one (Compound 460)

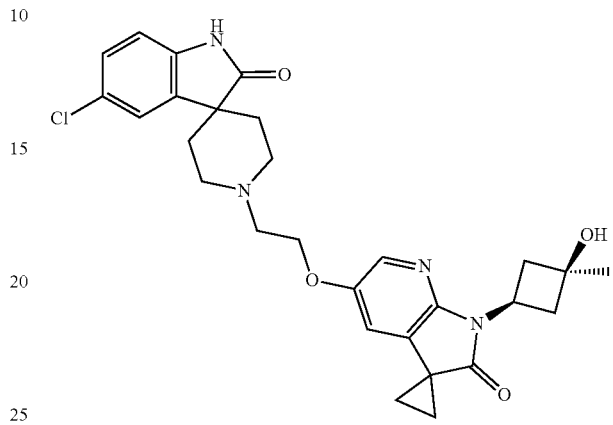

Step 1: 5'-bromo-1'-(3-oxocyclobutyl)spiro[cyclopropane-1,3'-pyrrolo[2,3-b]pyridin]-2'-one

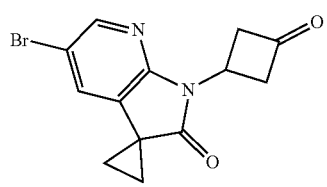 [SMILES: O=C1CC(N2C(=O)C3(CC3)c3cc(Br)cnc32)C1]

To a solution of 5'-bromo-1',2'-dihydrospiro[cyclopropane-1,3'-pyrrolo[2,3-b]pyridin]-2'-one (600 mg, 2.51 mmol) in DMF (8.37 mL) was added K₂CO₃ (1.04 g, 7.53 mmol) followed by 3-bromocyclobutan-1-one (0.56 g, 3.77 mmol). The reaction was allowed to stir at room temperature for 3 h, then was diluted with H₂O (50 mL) and extracted with EtOAc (3×50 mL). The combined organic layers were dried over Na₂SO₄, filtered, and then concentrated in vacuo to give 5'-bromo-1'-(3-oxocyclobutyl)-1',2'-dihydrospiro[cyclopropane-1,3'-pyrrolo[2,3-b]pyridin]-2'-one which was used in the subsequent step without further purification. MS=307.02 [M+H]⁺.

Step 2: 5'-bromo-1'-[(cis)-3-hydroxy-3-methylcyclobutyl]-1',2'-dihydrospiro[cyclopropane-1,3'-pyrrolo[2,3-b]pyridin]-2'-one

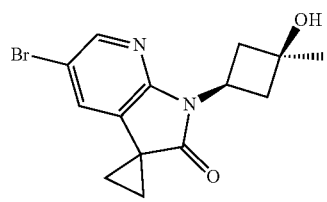 [SMILES: C[C@]1(O)C[C@@H](N2C(=O)C3(CC3)c3cc(Br)cnc32)C1]

To a solution of 5'-bromo-1'-(3-oxocyclobutyl)-1',2'-dihydrospiro[cyclopropane-1,3'-pyrrolo[2,3-b]pyridin]-2'-one (700 mg, 2.28 mmol) in THF (11.4 mL) at 0° C. was added 3.0 M methyl magnesium bromide solution in THF (0.836 mL, 2.51 mmol) dropwise. The reaction was allowed to stir at 0° C. for 1 h, then was quenched with saturated aqueous NH$_4$Cl solution (30 mL), and the mixture was extracted with EtOAc (3×30 mL). The combined organic layers were dried over Na$_2$SO$_4$, filtered, and then concentrated in vacuo. The residue was purified by flash silica gel chromatography (Biotage 50 g cartridge, 0-100% EtOAc/Hexanes) to provide 5'-bromo-1'-[(cis)-3-hydroxy-3-methylcyclobutyl]-1',2'-dihydrospiro[cyclopropane-1,3'-pyrrolo[2,3-b]pyridin]-2'-one MS=323.1 [M+H]$^+$.

Step 3: 1'-[(cis)-3-hydroxy-3-methylcyclobutyl]-5'-(4,4,5,5-tetramethyl-1,3,2-dioxaborolan-2-yl)-1',2'-dihydrospiro[cyclopropane-1,3'-pyrrolo[2,3-b]pyridin]-2'-one

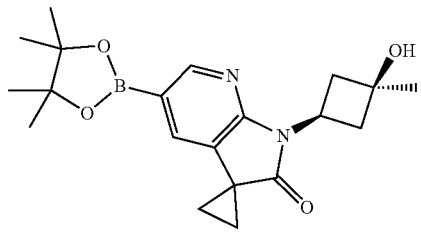

To a solution of 5'-bromo-1'-[(cis)-3-hydroxy-3-methylcyclobutyl]-1',2'-dihydrospiro[cyclopropane-1,3'-pyrrolo[2,3-b]pyridin]-2'-one (480 mg, 1.49 mmol) and bis(pinacolato)diboron (0.566 g, 2.23 mmol) in 1,4-dioxane (4.95 mL) was added Pd(dppf)Cl$_2$·CH$_2$Cl$_2$ (0.121 g, 0.149 mmol) and KOAc (0.437 g, 4.46 mmol). The mixture was sparged with N$_2$ for 5 min, and then the reaction was heated at 90° C. for 16 h. The reaction was cooled to room temperature, diluted with EtOAc (20 mL), and filtered over Celite. The resulting filtrate was concentrated in vacuo to provide 1'-[(cis)-3-hydroxy-3-methylcyclobutyl]-5'-(4,4,5,5-tetramethyl-1,3,2-dioxaborolan-2-yl)-1',2'-dihydrospiro[cyclopropane-1,3'-pyrrolo[2,3-b]pyridin]-2'-one, which was used in the subsequent step without further purification. MS=371.3 [M+H]$^+$.

Step 4: 5'-hydroxy-1'-[(cis)-3-hydroxy-3-methylcyclobutyl]-1',2'-dihydrospiro[cyclopropane-1,3'-pyrrolo[2,3-b]pyridin]-2'-one

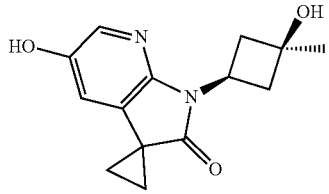 [SMILES: C[C@]1(O)C[C@@H](N2C(=O)C3(CC3)c3cc(O)cnc32)C1]

To a solution of 1'-[(cis)-3-hydroxy-3-methylcyclobutyl]-5'-(4,4,5,5-tetramethyl-1,3,2-dioxaborolan-2-yl)-1',2'-dihydrospiro[cyclopropane-1,3'-pyrrolo[2,3-b]pyridin]-2'-one (550 mg, 1.49 mmol) in MeOH (7.43 mL) was added 30% H$_2$O$_2$ in H$_2$O (0.486 mL, 4.46 mmol) dropwise. The reaction was stirred for 1 h, then was diluted with MeOH (20 mL) and concentrated in vacuo to provide 5'-hydroxy-1'-[(cis)-3-hydroxy-3-methylcyclobutyl]-1',2'-dihydrospiro[cyclopropane-1,3'-pyrrolo[2,3-b]pyridin]-2'-one, which was used in the subsequent step without further purification. MS=261.1 [M+H]$^+$.

Step 5: 5'-(2-bromoethoxy)-1'-[(cis)-3-hydroxy-3-methylcyclobutyl]-1',2'-dihydrospiro[cyclopropane-1,3'-pyrrolo[2,3-b]pyridin]-2'-one

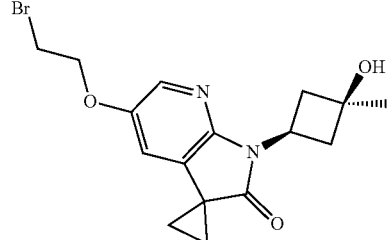

To a solution of 5'-hydroxy-1'-[(cis)-3-hydroxy-3-methylcyclobutyl]-1',2'-dihydrospiro[cyclopropane-1,3'-pyrrolo[2,3-b]pyridin]-2'-one (400 mg, 1.54 mmol) in DMF (1.54 mL) was added 1,2-dibromoethane (7.68 mL) and Cs$_2$CO$_3$ (1.502 g, 4.61 mmol). The reaction was heated at 90° C. for 4 h, then was cooled to room temperature and diluted with EtOAc (30 mL). The solution was filtered over Celite and the filtrate was concentrated in vacuo. The residue was purified by flash silica gel chromatography (Biotage 25 g cartridge, 0-70% EtOAc/Hexanes) to provide 5'-(2-bromoethoxy)-1'-[(cis)-3-hydroxy-3-methylcyclobutyl]-1',2'-dihydrospiro[cyclopropane-1,3'-pyrrolo[2,3-b]pyridin]-2'-one. MS=367.13 [M+H]$^+$.

Step 6: 5-chloro-1'-(2-{2'-oxo-1'-[(cis)-3-hydroxy-3-methylcyclobutyl]-1',2'-dihydrospiro[cyclopropane-1,3'-pyrrolo[2,3-b]pyridin]-5'-yloxy}ethyl)-1,2-dihydrospiro[indole-3,4'-piperidin]-2-one

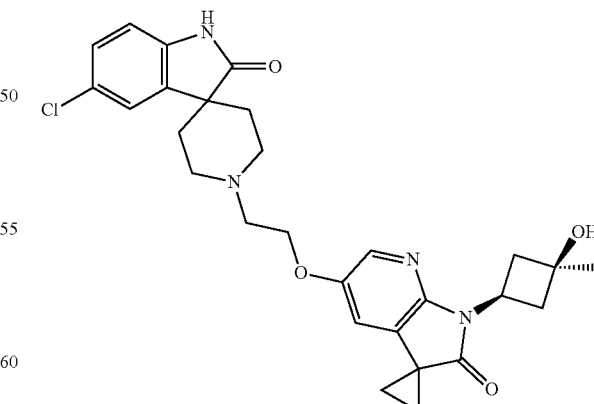

To a solution of 5'-(2-bromoethoxy)-1'-[(cis)-3-hydroxy-3-methylcyclobutyl]-1',2'-dihydrospiro[cyclopropane-1,3'-pyrrolo[2,3-b]pyridin]-2'-one (100 mg, 0.272 mmol) and 5-chloro-1,2-dihydrospiro[indole-3,4'-piperidin]-2-one (Intermediate B-4, 74.0 mg, 0.272 mmol, HCl salt) in DMF (1.361 mL) was added K₂CO₃ (113 mg, 0.817 mmol) and KI (45.0 g, 0.272 mmol). The reaction was heated to 60° C. for 3 h. After cooling to room temperature, the mixture was diluted with H₂O (1.5 mL) and MeCN (0.5 mL), and then filtered. The filtrate was purified by reverse phase preparative HPLC (Phenomenex Kinetex C$_{18}$ column, 5-50% MeCN in H₂O with 0.1% formic acid modifier) to give 5-chloro-1'-(2-{2'-oxo-1'-[(cis)-3-hydroxy-3-methylcyclobutyl]-1',2'-dihydrospiro[cyclopropane-1,3'-pyrrolo[2,3-b]pyridin]-5'-yloxy}ethyl)-1,2-dihydrospiro[indole-3,4'-piperidin]-2-one (Compound 460). ¹H NMR (500 MHz, DMSO-d₆): δ 10.50 (s, 1H), 7.88 (d, J=2.7 Hz, 1H), 7.50 (d, J=2.2 Hz, 1H), 7.28 (d, J=2.6 Hz, 1H), 7.24 (dd, J=8.3, 2.1 Hz, 1H), 6.85 (d, J=8.2 Hz, 1H), 5.13 (s, 1H), 4.48-4.38 (m, 1H), 4.16 (t, J=5.7 Hz, 2H), 3.05-2.99 (m, 2H), 2.99-2.91 (m, 2H), 2.91-2.84 (m, 2H), 2.77-2.68 (m, 2H), 2.28-2.21 (m, 2H), 1.83-1.66 (m, 6H), 1.58-1.53 (m, 2H), 1.31 (s, 3H). MS=523.17 [M+H]⁺.

Example 94

5-chloro-1'-[2-({7-oxo-8-[(cis)-3-hydroxy-3-(²H₃) methylcyclobutyl]-5,6,7,8-tetrahydro-1,8-naphthyridin-3-yl}oxy)ethyl]-1,2-dihydrospiro[indole-3,4'-piperidin]-2-one (Compound 461)

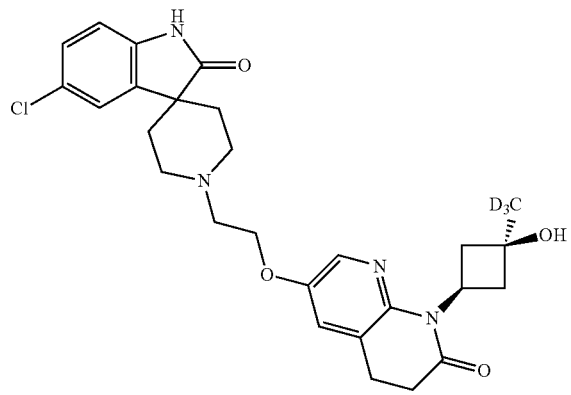 [SMILES: [2H]C([2H])([2H])[C@]1(O)C[C@@H](N2C(=O)CCc3cc(OCCN4CCC5(CC4)C(=O)Nc4ccc(Cl)cc45)cnc32)C1]

Step 1: 6-bromo-1-(3-oxocyclobutyl)-1,2,3,4-tetrahydro-1,8-naphthyridin-2-one

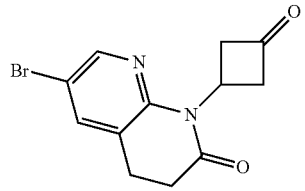 [SMILES: O=C1CC(N2C(=O)CCc3cc(Br)cnc32)C1]

To a solution of 6-bromo-3,4-dihydro-1H-1,8-naphthyridin-2-one (5.00 g, 22.0 mmol) in DMF (100 mL) was added K₂CO₃ (9.13 g, 66.1 mmol). The mixture was stirred at 60° C. for 1 h, and then 3-bromocyclobutan-1-one (4.92 g, 33.0 mmol) was added dropwise via syringe pump over 20 h. The mixture was poured into H₂O (200 mL) and a solid precipitated. The solid was isolated via filtration, and the filter cake was dried in vacuo to provide 6-bromo-1-(3-oxocyclobutyl)-1,2,3,4-tetrahydro-1,8-naphthyridin-2-one, which was used in the subsequent step without further purification. MS=295.04 [M+H]⁺.

Step 2: 6-bromo-1-[(cis)-3-hydroxy-3-(²H₃)methylcyclobutyl]-1,2,3,4-tetrahydro-1,8-naphthyridin-2-one

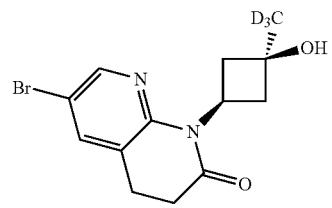 [SMILES: [2H]C([2H])([2H])[C@]1(O)C[C@@H](N2C(=O)CCc3cc(Br)cnc32)C1]

To a solution of 6-bromo-1-(3-oxocyclobutyl)-3,4-dihydro-1,8-naphthyridin-2-one (4.34 g, 14.7 mmol) in THF (73.5 mL) at 0° C. was added 1.0 M CD₃MgI in Et₂O (17.6 mL, 17.6 mmol) dropwise. The reaction was allowed to warm to room temperature and stirred for 1 h. The mixture was quenched with saturated aqueous NH₄Cl solution (100 mL) and extracted with EtOAc (3×100 mL). The combined organic layers were dried over anhydrous Na₂SO₄, then concentrated in vacuo. The residue was taken up in DCM, solids were removed by filtration, and the filtrate was concentrated in vacuo to give 6-bromo-1-[(cis)-3-hydroxy-3-(²H₃)methylcyclobutyl]-1,2,3,4-tetrahydro-1,8-naphthyridin-2-one. MS=314.1 [M+H]⁺.

Step 3: 1-[(cis)-3-hydroxy-3-(²H₃)methylcyclobutyl]-6-(4,4,5,5-tetramethyl-1,3,2-dioxaborolan-2-yl)-1,2,3,4-tetrahydro-1,8-naphthyridin-2-one

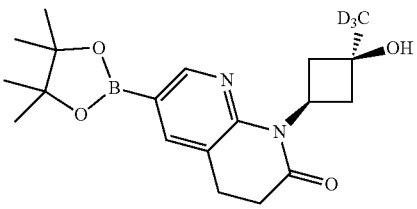 [SMILES: [2H]C([2H])([2H])[C@]1(O)C[C@@H](N2C(=O)CCc3cc(B4OC(C)(C)C(C)(C)O4)cnc32)C1]

A solution of 6-bromo-1-[(cis)-3-hydroxy-3-(²H₃)methylcyclobutyl]-1,2,3,4-tetrahydro-1,8-naphthyridin-2-one (4.13 g, 12.4 mmol), bis(pinacolato)diboron (4.71 g, 18.5 mmol), Pd(dppf)Cl₂ (0.904 g, 1.24 mmol), and KOAc (3.64 g, 37.1 mmol) in 1,4-dioxane (61.8 mL) was sparged with N₂, and then heated at 90° C. for 16 h. The reaction was cooled to room temperature and diluted with EtOAc (150 mL), then filtered over Celite. The resulting filtrate was concentrated in vacuo to give 1-[(cis)-3-hydroxy-3-(²H₃) methylcyclobutyl]-6-(4,4,5,5-tetramethyl-1,3,2-dioxaborolan-2-yl)-1,2,3,4-tetrahydro-1,8-naphthyridin-2-one, which was used in the subsequent step without further purification. MS=362.34 [M+H]⁺.

Step 4: 6-hydroxy-1-[(cis)-3-hydroxy-3-($^2$H$_3$)methylcyclobutyl]-1,2,3,4-tetrahydro-1,8-naphthyridin-2-one

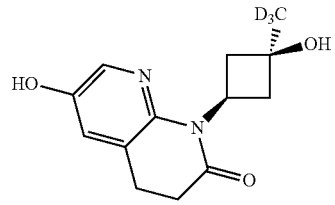 [SMILES: [2H]C([2H])([2H])[C@]1(O)C[C@@H](N2C(=O)CCc3cc(O)cnc32)C1]

To a solution of 1-[(cis)-3-hydroxy-3-($^2$H$_3$)methylcyclobutyl]-6-(4,4,5,5-tetramethyl-1,3,2-dioxaborolan-2-yl)-1,2,3,4-tetrahydro-1,8-naphthyridin-2-one (4.46 g, 12.346 mmol) in MeOH (61.7 mL) was added 30% H$_2$O$_2$ in H$_2$O (3.78 mL, 37.0 mmol) dropwise. The reaction was allowed to stir at room temperature for 2 h, then was concentrated in vacuo to give 6-hydroxy-1-[(cis)-3-hydroxy-3-($^2$H$_3$)methylcyclobutyl]-1,2,3,4-tetrahydro-1,8-naphthyridin-2-one, which was used in the subsequent step without further purification. MS=252.2 [M+H]$^+$.

Step 5: 6-(2-bromoethoxy)-1-[(cis)-3-hydroxy-3-($^2$H$_3$)methylcyclobutyl]-1,2,3,4-tetrahydro-1,8-naphthyridin-2-one

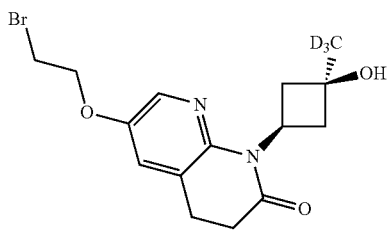 [SMILES: [2H]C([2H])([2H])[C@]1(O)C[C@@H](N2C(=O)CCc3cc(OCCBr)cnc32)C1]

6-hydroxy-1-[(cis)-3-hydroxy-3-($^2$H$_3$)methylcyclobutyl]-1,2,3,4-tetrahydro-1,8-naphthyridin-2-one (1.00 g, 3.98 mmol) was dissolved in DMF (3.98 mL), then Cs$_2$CO$_3$ (3.89 g, 11.9 mmol) and 1,2-dibromoethane (13.3 mL) were added and the reaction was heated at 90° C. for 8 h. The reaction was cooled to room temperature, filtered through a pad of Celite, and the filtrate was concentrated in vacuo. The residue was purified by flash silica gel chromatography (Biotage 50 g cartridge, 0-100% EtOAc/Hexanes) to provide 6-(2-bromoethoxy)-1-[(cis)-3-hydroxy-3-($^2$H$_3$)methylcyclobutyl]-1,2,3,4-tetrahydro-1,8-naphthyridin-2-one. MS=358.16 [M+H]$^+$.

Step 6: 5-chloro-1'-[2-({7-oxo-8-[(cis)-3-hydroxy-3-($^2$H$_3$)methylcyclobutyl]-5,6,7,8-tetrahydro-1,8-naphthyridin-3-yl}oxy)ethyl]-1,2-dihydrospiro[indole-3,4'-piperidin]-2-one

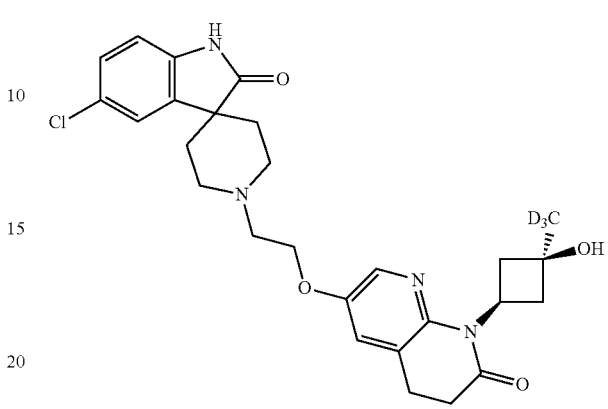

To a solution of 6-(2-bromoethoxy)-1-[(cis)-3-hydroxy-3-($^2$H$_3$)methylcyclobutyl]-1,2,3,4-tetrahydro-1,8-naphthyridin-2-one (500 mg, 1.40 mmol) and 5-chloro-1,2-dihydrospiro[indole-3,4'-piperidin]-2-one (Intermediate B-4, 0.381 g, 1.40 mmol, HCl salt) in DMF (2.79 mL) was added K$_2$CO$_3$ (0.579 g, 4.19 mmol) and KI (0.232 g, 1.40 mmol). The reaction was heated at 60° C. for 3 h. After cooling to room temperature, the reaction was poured over H$_2$O (20 mL) and extracted with EtOAc (3×20 mL). The combined organic layers were combined and washed with 5% LiCl solution in H$_2$O (50 mL). The organic phase was dried over Na$_2$SO$_4$, filtered, and concentrated in vacuo. The crude product was purified by reverse phase silica gel chromatography (Biotage 30 g C$_{18}$ cartridge, 5-50% MeCN/H$_2$O with 0.1% NH$_4$OH) to give 5-chloro-1'-[2-({7-oxo-8-[(cis)-3-hydroxy-3-($^2$H$_3$)methylcyclobutyl]-5,6,7,8-tetrahydro-1,8-naphthyridin-3-yl}oxy)ethyl]-1,2-dihydrospiro[indole-3,4'-piperidin]-2-one (Compound 461). $^1$H NMR (500 MHz, DMSO-d$_6$): δ 10.48 (s, 1H), 7.94 (d, J=2.9 Hz, 1H), 7.50 (d, J=2.2 Hz, 1H), 7.39 (d, J=2.9 Hz, 1H), 7.23 (dd, J=8.3, 2.1 Hz, 1H), 6.84 (d, J=8.3 Hz, 1H), 4.81 (s, 1H), 4.28-4.20 (m, 1H), 4.18 (t, J=5.7 Hz, 2H), 2.95-2.88 (m, 2H), 2.85 (t, J=5.7 Hz, 2H), 2.82-2.77 (m, 2H), 2.73-2.66 (m, 2H), 2.47-2.41 (m, 3H), 2.37-2.31 (m, 3H), 1.81-1.74 (m, 2H), 1.74-1.67 (m, 2H). MS=514.27 [M+H]$^+$.

Example 95

5-chloro-1'-[2-({7-oxo-8-[(cis)-3-hydroxy-3-($^2H_3$)methylcyclobutyl]-5,6,7,8-tetrahydro-1,8-naphthyridin-3-yl}oxy)(1,1,2,2-$^2H_4$)ethyl]-1,2-dihydrospiro[indole-3,4'-piperidin]-2-one (Compound 462)

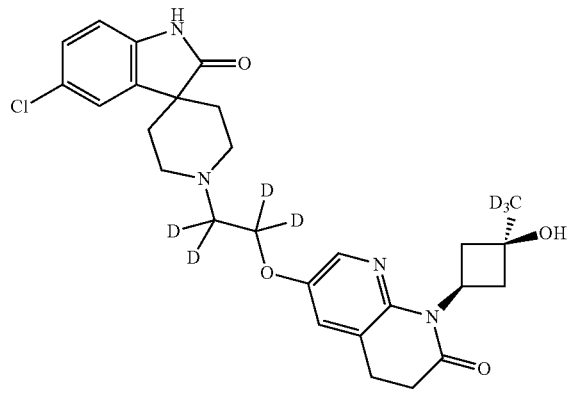 [SMILES: [2H]C([2H])(Oc1cnc2c(c1)CCC(=O)N2[C@H]1C[C@](O)(C([2H])([2H])[2H])C1)C([2H])([2H])N1CCC2(CC1)C(=O)Nc1ccc(Cl)cc12]

Step 1: 6-[2-bromo(1,1,2,2-$^2H_4$)ethoxy]-1-[(cis)-3-hydroxy-3-($^2H_3$)methylcyclobutyl]-1,2,3,4-tetrahydro-1,8-naphthyridin-2-one

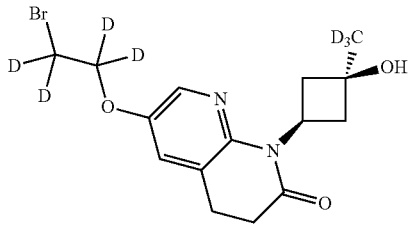 [SMILES: [2H]C([2H])(Br)C([2H])([2H])Oc1cnc2c(c1)CCC(=O)N2[C@H]1C[C@](O)(C([2H])([2H])[2H])C1]

To a solution of 6-hydroxy-1-[(cis)-3-hydroxy-3-($^2H_3$)methylcyclobutyl]-3,4-dihydro-1,8-naphthyridin-2-one (Example 94, Step 4, 3.00 g, 11.9 mmol) in DMF (23.9 mL) was added dibromo($^2H_4$)ethane (45.8 g, 239 mmol) and Cs$_2$CO$_3$ (11.7 g, 35.8 mmol). The reaction was heated at 90° C. for 8 h. The reaction was cooled to room temperature and diluted with EtOAc (100 mL), filtered through Celite, and the filtrate was concentrated in vacuo. The residue was purified by flash silica gel chromatography (Biotage 100 g cartridge, 0-80% EtOAc/Hexanes) to provide 6-[2-bromo(1,1,2,2-$^2H_4$)ethoxy]-1-[(cis)-3-hydroxy-3-($^2H_3$)methylcyclobutyl]-1,2,3,4-tetrahydro-1,8-naphthyridin-2-one. MS=362.2 [M+H]$^+$.

Step 2: 5-chloro-1'-[2-({7-oxo-8-[(cis)-3-hydroxy-3-($^2H_3$)methylcyclobutyl]-5,6,7,8-tetrahydro-1,8-naphthyridin-3-yl}oxy)(1,1,2,2-$^2H_4$)ethyl]-1,2-dihydrospiro[indole-3,4'-piperidin]-2-one

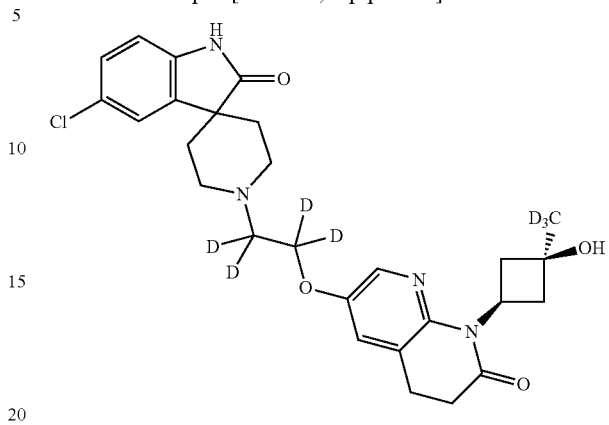

To a solution of 6-[2-bromo(1,1,2,2-$^2H_4$)ethoxy]-1-[(cis)-3-hydroxy-3-($^2H_3$)methylcyclobutyl]-3,4-dihydro-1,8-naphthyridin-2-one (1.40 g, 3.86 mmol) and 5-chloro-1,2-dihydrospiro[indole-3,4'-piperidin]-2-one (Intermediate B-4, 1.06 g, 3.86 mmol, HCl salt) in DMF (7.729 mL) was added K$_2$CO$_3$ (1.60 g, 11.6 mmol) and KI (0.642 g, 3.86 mmol). The reaction was heated at 60° C. for 3 h. The reaction was cooled to room temperature and diluted with EtOAc (50 mL). The mixture was then filtered through a pad of Celite, and the filtrate concentrated in vacuo. The crude product was purified by reverse phase silica gel chromatography (Biotage 30 g C$_{18}$ cartridge, 5-50% MeCN/H$_2$O with 0.1% NH$_4$OH) to give 5-chloro-1'-[2-({7-oxo-8-[(cis)-3-hydroxy-3-($^2H_3$)methylcyclobutyl]-5,6,7,8-tetrahydro-1,8-naphthyridin-3-yl}oxy)(1,1,2,2-$^2H_4$)ethyl]-1,2-dihydrospiro[indole-3,4'-piperidin]-2-one (Compound 462). $^1$H NMR (500 MHz, DMSO-d$_6$, 22/24 H): δ 10.43 (s, 1H), 7.87 (d, J=2.9 Hz, 1H), 7.44 (d, J=2.1 Hz, 1H), 7.32 (d, J=2.9 Hz, 1H), 7.17 (dd, J=8.2, 2.1 Hz, 1H), 6.78 (d, J=8.2 Hz, 1H), 4.76 (s, 1H), 4.17 (p, J=8.3 Hz, 1H), 2.92-2.79 (m, 2H), 2.73 (t, J=7.2 Hz, 2H), 2.67-2.58 (m, 2H), 2.41-2.34 (m, 2H), 2.31-2.22 (m, 2H), 1.75-1.59 (m, 4H). MS=518.3 [M+H]$^+$.

Example 97

5-chloro-1'-[2-({1-[(cis)-3-hydroxy-3-methylcyclobutyl]-7-(trifluoromethyl)-1H-1,3-benzodiazol-5-yl}oxy)(1,1,2,2-$^2H_4$)ethyl]-1,2-dihydrospiro[indole-3,4'-piperidin]-2-one (Compound 463)

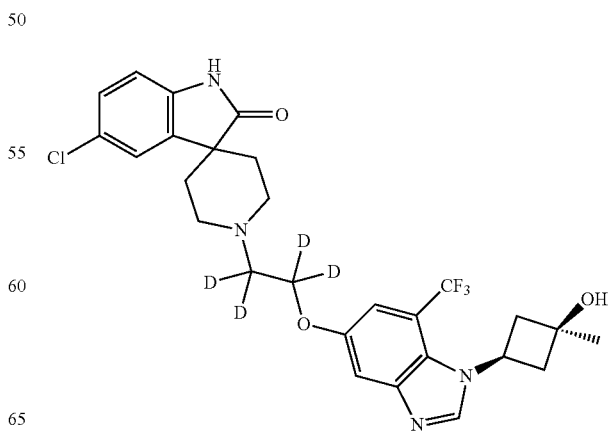

1303

Step 1: (cis)-3-{5-[2-bromo(1,1,2,2-²H₄)ethoxy]-7-(trifluoromethyl)-1,3-benzodiazol-1-yl}-1-methylcyclobutan-1-ol

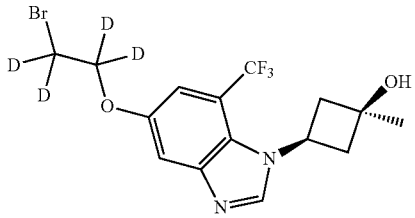 [SMILES: [2H]C([2H])(Br)C([2H])([2H])Oc1cc(C(F)(F)F)c2c(c1)ncn2[C@H]1C[C@@](C)(O)C1]

To a solution of 1-[(cis)-3-hydroxy-3-methylcyclobutyl]-7-(trifluoromethyl)-1H-1,3-benzodiazol-5-ol (Intermediate A-92, 250 mg, 0.873 mmol) and Cs₂CO₃ (0.854 g, 2.62 mmol) in DMF (1.747 mL) was added dibromo(²H₄)ethane (0.838 g, 4.367 mmol). The reaction was heated at 90° C. for 3 h. The reaction was cooled to room temperature and diluted with EtOAc (30 mL), and then filtered through a pad of Celite. The filtrate was concentrated, and the filtrate was purified by flash silica gel chromatography (Biotage 25 g cartridge, 0-10% MeOH/DCM) to provide (cis)-3-{5-[2-bromo(1,1,2,2-²H₄)ethoxy]-7-(trifluoromethyl)-1,3-benzodiazol-1-yl}-1-methylcyclobutan-1-ol. MS=397.2/399.2 [M+H]⁺.

Step 2: 5-chloro-1'-[2-({1-[(cis)-3-hydroxy-3-methylcyclobutyl]-7-(trifluoromethyl)-1H-1,3-benzodiazol-5-yl}oxy)(1,1,2,2-²H₄)ethyl]-1,2-dihydrospiro[indole-3,4'-piperidin]-2-one

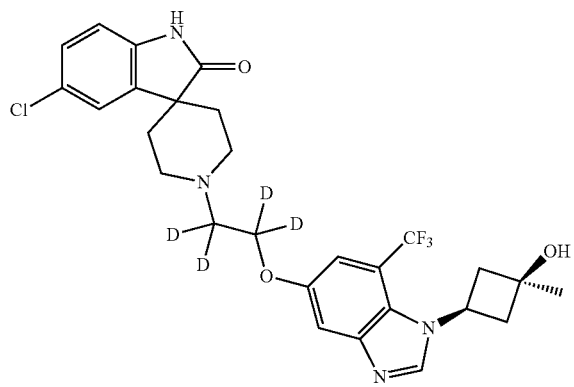 [SMILES: [2H]C([2H])(Oc1cc(C(F)(F)F)c2c(c1)ncn2[C@H]1C[C@@](C)(O)C1)C([2H])([2H])N1CCC2(CC1)C(=O)Nc1ccc(Cl)cc12]

To a solution of (cis)-3-{5-[2-bromo(1,1,2,2-²H₄)ethoxy]-7-(trifluoromethyl)-1,3-benzodiazol-1-yl}-1-methylcyclobutan-1-ol (257 mg, 0.647 mmol) and 5-chloro-1,2-dihydrospiro[indole-3,4'-piperidin]-2-one (Intermediate B-4, 0.177 g, 0.647 mmol, HCl salt) in DMF (1.29 mL) was added K₂CO₃ (0.268 g, 1.94 mmol) and KI (0.107 g, 0.647 mmol). The reaction was heated at 60° C. for 3 h, then was cooled to room temperature and the solution was diluted with H₂O 1.5 mL) and MeCN 1.5 mL). The mixture was purified by reverse phase silica gel chromatography (Biotage 30 g C₁₈ cartridge, 5-60% MeCN/H₂O with 0.1% NH₄OH) to give 5-chloro-1'-[2-({1-[(cis)-3-hydroxy-3-methylcyclobutyl]-7-(trifluoromethyl)-1H-1,3-benzodiazol-5-yl}oxy)(1,1,2,2-²H₄)ethyl]-1,2-dihydrospiro[indole-3,4'-piperidin]-2-one (Compound 463). ¹H NMR (500 MHz,

1304

DMSO-d₆): δ 10.42 (s, 1H), 8.61 (s, 1H), 7.54 (d, J=2.4 Hz, 1H), 7.43 (d, J=2.1 Hz, 1H), 7.19 (d, J=2.4 Hz, 1H), 7.16 (dd, J=8.2, 2.1 Hz, 1H), 6.78 (d, J=8.2 Hz, 1H), 5.25 (s, 1H), 4.51 (p, J=8.3 Hz, 1H), 2.92-2.83 (m, 2H), 2.70-2.60 (m, 2H), 2.59-2.48 (m, 4H), 1.78-1.69 (m, 2H), 1.68-1.59 (m, 2H), 1.27 (s, 3H). MS=553.2 [M+H]⁺.

Alternative Procedure for Example 97

5-chloro-1'-[2-({1-[(cis)-3-hydroxy-3-methylcyclobutyl]-7-(trifluoromethyl)-1H-1,3-benzodiazol-5-yl}oxy)(1,1,2,2-²H₄)ethyl]-1,2-dihydrospiro[indole-3,4'-piperidin]-2-one (Compound 463)

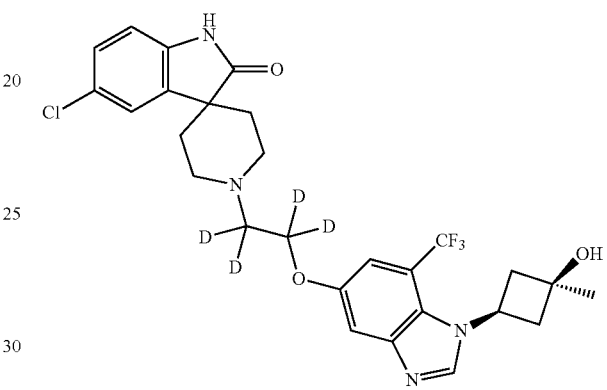

Step 1: 1-methyl-4-({2-[(4-methylbenzenesulfonyl)oxy](1,1,2,2-²H₄)ethoxy}sulfonyl)benzene

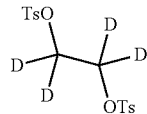

To a 0° C. mixture of (²H₄)ethane-1,2-diol (5.00 g, 75.7 mmol) and TsCl (31.7 g, 166 mmol) in DCM (150 mL) was added dropwise TEA (26.3 mL, 189 mmol). The mixture was stirred at room temperature for 16 h. The mixture was poured into ice water (300 mL) and extracted with DCM (2×100 mL). The combined organic layers were washed with 10% w/w citric acid in H₂O (200 mL) and brine (100 mL), dried over Na₂SO₄, and concentrated in vacuo. The residue was triturated in MTBE (150 mL) for 30 min. The mixture was filtered to collect the solid, which was dried in vacuo to provide 1-methyl-4-({2-[(4-methylbenzenesulfonyl)oxy](1,1,2,2-²H₄)ethoxy}sulfonyl)benzene, which was used in the subsequent step without further purification. MS=374.9 [M+H]⁺.

Step 2: 2-({1-[(cis)-3-hydroxy-3-methylcyclobutyl]-7-(trifluoromethyl)-1H-1,3-benzodiazol-5-yl}oxy)(1,1,2,2-²H₄)ethyl 4-methylbenzene-1-sulfonate

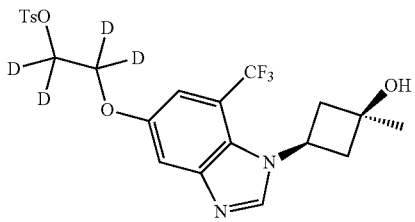 [SMILES: [2H]C([2H])(Oc1cc(C(F)(F)F)c2c(c1)ncn2[C@H]1C[C@@](C)(O)C1)C([2H])([2H])OS(=O)(=O)c1ccc(C)cc1]

A mixture of 1-[(cis)-3-hydroxy-3-methylcyclobutyl]-7-(trifluoromethyl)-1H-1,3-benzodiazol-5-ol (Intermediate A-92, 1.00 g, 3.49 mmol), 1-methyl-4-({2-[(4-methylbenzenesulfonyl)oxy](1,1,2,2-²H₄)ethoxy}sulfonyl)benzene (3.92 g, 10.5 mmol) and K₂CO₃ (1.45 g, 10.5 mmol) in DMF (60 mL) was stirred at 50° C. for 16 h. After cooling to room temperature, the mixture was poured into H₂O (100 mL) and extracted with EtOAc (3×50 mL). The combined organic layers were washed with brine (100 mL), dried over Na₂SO₄, filtered, and concentrated under reduced pressure. The residue was purified by flash silica gel chromatography (Sepaflash 20 g cartridge, 0-80% EtOAc/Petroleum ether) to provide 2-({1-[(cis)-3-hydroxy-3-methylcyclobutyl]-7-(trifluoromethyl)-1H-1,3-benzodiazol-5-yl}oxy)(1,1,2,2-²H₄)ethyl 4-methylbenzene-1-sulfonate. MS=489.1 [M+H]⁺.

Step 3: 5-chloro-1'-[2-({1-[(cis)-3-hydroxy-3-methylcyclobutyl]-7-(trifluoromethyl)-1H-1,3-benzodiazol-5-yl}oxy)(1,1,2,2-²H₄)ethyl]-1,2-dihydrospiro[indole-3,4'-piperidin]-2-one (Compound 463)

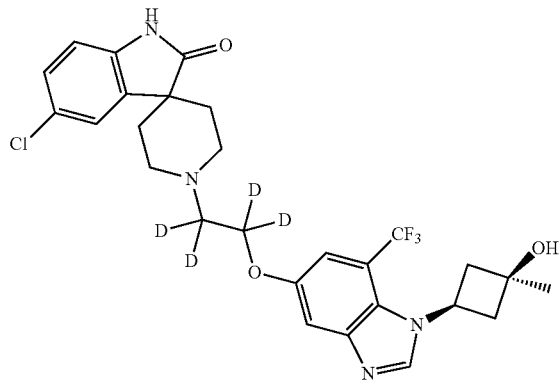 [SMILES: [2H]C([2H])(Oc1cc(C(F)(F)F)c2c(c1)ncn2[C@H]1C[C@@](C)(O)C1)C([2H])([2H])N1CCC2(CC1)C(=O)Nc1ccc(Cl)cc12]

A mixture of 2-({1-[(cis)-3-hydroxy-3-methylcyclobutyl]-7-(trifluoromethyl)-1H-1,3-benzodiazol-5-yl}oxy)(1,1,2,2-²H₄)ethyl 4-methylbenzene-1-sulfonate (700 mg, 1.43 mmol), 5-chloro-1,2-dihydrospiro[indole-3,4'-piperidin]-2-one (Intermediate B-4, 431 mg, 1.58 mmol, HCl salt) and NaHCO₃ (602 mg, 7.16 mmol) in MeCN (30 mL) was stirred at 80° C. for 16 h. After cooling to room temperature, solids precipitated out. The solids were isolated by filtration, and the filter cake was further purified by reverse phase preparative HPLC (Phenomenex Luna C₁₈ column, 5-50% MeCN: 0.04% HCl in H₂O) to give 5-chloro-1'-[2-({1-[(cis)-3-hydroxy-3-methylcyclobutyl]-7-(trifluoromethyl)-1H-1,3-benzodiazol-5-yl}oxy)(1,1,2,2-²H₄)ethyl]-1,2-dihydrospiro[indole-3,4'-piperidin]-2-one (Compound 463, HCl salt, 24/24 H). ¹H NMR (400 MHz, DMSO-d₆): δ 11.09 (br s, 0.5H), 10.81 (s, 0.5H), 10.73 (s, 0.5H), 10.49 (br s, 0.5H), 9.08-9.03 (m, 1H), 7.99 (s, 0.5H), 7.73-7.71 (m, 1H), 7.50-7.40 (m, 1H), 7.26-7.24 (m, 1H), 7.17 (s, 0.5H), 6.94-6.88 (m, 1H), 4.64-4.55 (m, 1H), 3.88-3.59 (m, 4H), 2.67-2.50 (m, 5H), 2.21-1.97 (m, 1H), 1.98-1.95 (m, 2H), 1.34 (s, 3H). MS=552.9 [M+H]⁺.

Example 98

5-chloro-1'-[2-({1-[(cis)-3-hydroxy-3-methylcyclobutyl]-7-(trifluoromethyl)-1H-indazol-5-yl}oxy)ethyl]-1,2-dihydrospiro[indole-3,4'-piperidin]-2-one (Compound 464)

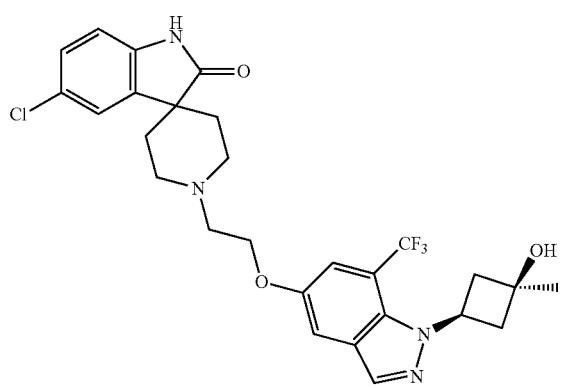 [SMILES: C[C@]1(O)C[C@@H](n2ncc3cc(OCCN4CCC5(CC4)C(=O)Nc4ccc(Cl)cc45)cc(C(F)(F)F)c32)C1]

A mixture of 2-({1-[(cis)-3-hydroxy-3-methylcyclobutyl]-7-(trifluoromethyl)-1H-indazol-5-yl}oxy)ethyl 4-methylbenzene-1-sulfonate (Intermediate A-123, 80.0 mg, 165 μmol), 5-chloro-1,2-dihydrospiro[indole-3,4'-piperidin]-2-one (Intermediate B-4, 49.6 mg, 182 μmol, HCl salt) and NaHCO₃ (69.4 mg, 826 μmol) in MeCN (4 mL) was stirred at 80° C. for 16 h. The reaction mixture was cooled to room temperature and filtered. The filtrate was concentrated under reduced pressure. The filtrate was purified by reverse phase preparative HPLC (Phenomenex Luna C₁₈ column, 5-35% MeCN: 0.04% HCl in H₂O) to give 5-chloro-1'-[2-({1-[(cis)-3-hydroxy-3-methylcyclobutyl]-7-(trifluoromethyl)-1H-indazol-5-yl}oxy)ethyl]-1,2-dihydrospiro[indole-3,4'-piperidin]-2-one (Compound 464). ¹H NMR (400 MHz, DMSO-d₆, HCl salt): δ 10.80 (s, 0.5H), 10.73 (s, 0.5H), 10.60 (br s, 0.5H), 10.09 (s, 0.5H), 8.34 (d, J=2.8 Hz, 1H), 7.99 (s, 0.5H), 7.74 (s, 1H), 7.58 (dd, J=12.0 Hz, 2.0 Hz, 1H), 7.35-7.25 (m, 1H), 7.16 (d, J=1.6 Hz, 0.5H), 6.94-6.88 (m, 1H), 5.29 (br s, 1H), 4.80-4.73 (m, 1H), 4.54-4.53 (m, 2H), 3.90-3.75 (m, 5H), 3.45-3.35 (m, 1H), 2.76 (t, J=10.8 Hz, 2H), 2.50-2.45 (m, 3H), 2.24-2.12 (m, 1H), 2.06-1.86 (m, 2H), 1.16 (s, 3H). MS=549.2 [M+H]⁺.

The following compounds in Table 38.20 were prepared according to procedures similar to steps described for Example 98 using the appropriate starting materials or common intermediates.

TABLE 38.20

| # | Structure | IUPAC Name | Exact Mass [M + H]⁺ | Intermediates Used |
|---|---|---|---|---|
| 465 | 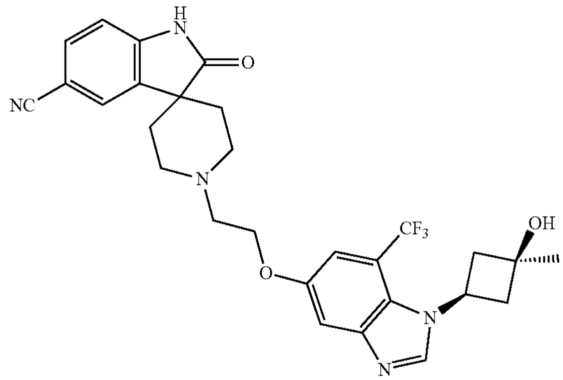 [SMILES: C[C@]1(O)C[C@@H](n2cnc3cc(OCCN4CCC5(CC4)C(=O)Nc4ccc(C#N)cc45)cc(C(F)(F)F)c32)C1] | 2-oxo-1'-[2-({1-[(cis)-3-hydroxy-3-methylcyclobutyl]-7-(trifluoromethyl)-1H-indazol-5-yl}oxy)ethyl]-1,2-dihydrospiro[indole-3,4'-piperidine]-5-carbonitrile | Calc'd 540.2 Found 540.2 | A-123 & B-9 |

Example 99

5-chloro-1'-[2-({2-[(cis)-3-hydroxy-3-methylcyclobutyl]-7-(trifluoromethyl)-1H-1,3-benzodiazol-5-yl}oxy)ethyl]-1,2-dihydrospiro[indole-3,4'-piperidin]-2-one (Compound 466)

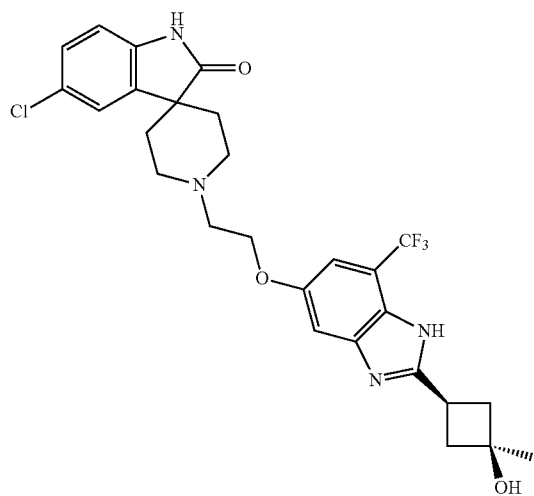 [SMILES: C[C@]1(O)C[C@@H](c2nc3cc(OCCN4CCC5(CC4)C(=O)Nc4ccc(Cl)cc45)cc(C(F)(F)F)c3[nH]2)C1]

Step 1: (cis)-N-[2-amino-5-bromo-3-(trifluoromethyl)phenyl]-3-hydroxy-3-methylcyclobutane-1-carboxamide

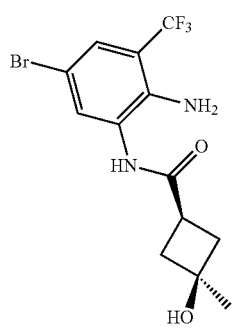 [SMILES: C[C@]1(O)C[C@@H](C(=O)Nc2cc(Br)cc(C(F)(F)F)c2N)C1]

To a solution of 3-hydroxy-3-methyl-cyclobutanecarboxylic acid (1.53 g, 11.8 mmol) in DCM (30 mL) was added DIEA (5.12 mL, 29.4 mmol) and HATU (5.37 g, 14.1 mmol). After stirring at room temperature for 20 min, 5-bromo-3-(trifluoromethyl)benzene-1,2-diamine (3.00 g, 11.76 mmol) was added. The mixture was stirred at room temperature for 2 h, then was poured into H₂O (50 mL) and extracted with EtOAc (3×30 mL). The combined organic layers were dried over anhydrous Na₂SO₄, filtered and concentrated in vacuo to give (cis)-N-[2-amino-5-bromo-3-(trifluoromethyl)phenyl]-3-hydroxy-3-methylcyclobutane-1-carboxamide. MS=367.0/369.0 [M+H]⁺.

Step 2: (cis)-3-[5-bromo-7-(trifluoromethyl)-1H-1,3-benzodiazol-2-yl]-1-methylcyclobutan-1-ol

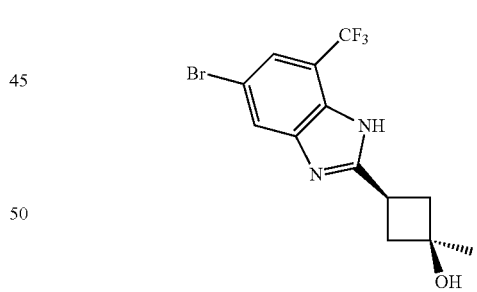

A solution of (cis)-N-[2-amino-5-bromo-3-(trifluoromethyl)phenyl]-3-hydroxy-3-methylcyclobutane-1-carboxamide (5.00 g, 13.6 mmol) in acetic acid (50 mL) was heated to 90° C. and stirred at 90° C. for 5 h. After cooling to 0° C., the reaction mixture was adjusted to pH=7 by addition of saturated aqueous Na₂CO₃ solution, then was extracted with EtOAc (3×30 mL). The combined organic layers were dried over anhydrous Na₂SO₄, filtered, and concentrated in vacuo. The residue was purified by flash silica gel chromatography (Sepaflash 40 g cartridge, 0-60% EtOAc/Petroleum ether) to provide (cis)-3-[5-bromo-7-(trifluoromethyl)-1H-1,3-benzodiazol-2-yl]-1-methylcyclobutan-1-ol. MS=349.0/350.9 [M+H]⁺.

Step 3: 5-bromo-2-[(cis)-3-methyl-3-{[2-(trimethylsilyl)ethoxy]methoxy}cyclobutyl]-7-(trifluoromethyl)-1-{[2-(trimethylsilyl)ethoxy]methyl}-1H-1,3-benzodiazole

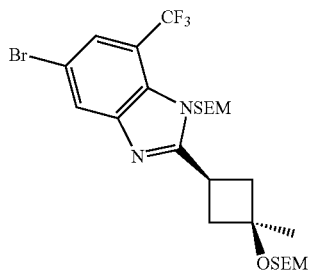

To a 0° C. solution of (cis)-3-[5-bromo-7-(trifluoromethyl)-1H-1,3-benzodiazol-2-yl]-1-methylcyclobutan-1-ol (1.50 g, 4.30 mmol) in THF (20 mL) was added NaH (309 mg, 7.73 mmol, 60% in mineral oil) portion wise. The mixture was stirred at 0° C. for 30 min, and then a solution of SEMCl (1.52 mL, 8.59 mmol) in THF (8 mL) was added dropwise. The resulting mixture was warmed to room temperature and then stirred for 16 h. The reaction was cooled to 0-10° C., quenched with saturated aqueous NH$_4$Cl solution (20 mL), and then extracted with EtOAc (3×20 mL). The combined organic layers were dried over anhydrous Na$_2$SO$_4$, filtered, and concentrated in vacuo. The residue was purified by reverse phase preparative HPLC (Welch Xtimate C$_{18}$ column, 45-65% MeCN: 10 mM NH$_4$HCO$_3$ in H$_2$O) to give 5-bromo-2-[(cis)-3-methyl-3-{[2-(trimethylsilyl)ethoxy]methoxy}cyclobutyl]-7-(trifluoromethyl)-1-{[2-(trimethylsilyl)ethoxy]methyl}-1H-1,3-benzodiazole. MS=609.0/611.0 [M+H]$^+$

Step 4: 5-(5,5-dimethyl-1,3,2-dioxaborinan-2-yl)-2-[(cis)-3-methyl-3-{[2-(trimethylsilyl)ethoxy]methoxy}cyclobutyl]-7-(trifluoromethyl)-1-{[2-(trimethylsilyl)ethoxy]methyl}-1H-1,3-benzodiazole

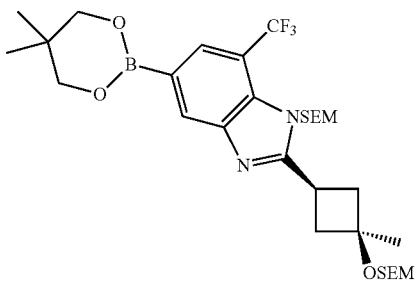

A mixture of 5-bromo-2-[(cis)-3-methyl-3-{[2-(trimethylsilyl)ethoxy]methoxy}cyclobutyl]-7-(trifluoromethyl)-1-{[2-(trimethylsilyl)ethoxy]methyl}-1H-1,3-benzodiazole (300 mg, 492 µmol), KOAc (72.4 mg, 738 mol), Pd(dppf)Cl$_2$ (18.0 mg, 24.6 µmol), and bis(neopentyl glycolato)diboron (222 mg, 984 µmol) in 1,4-dioxane (5 mL) was degassed and purged with N$_2$ (3×), and then the mixture was heated to 90° C. and stirred at 90° C. for 3 h under N$_2$ atmosphere. After cooling to room temperature, the reaction mixture was filtered, and the filtrate was concentrated in vacuo to give 5-(5,5-dimethyl-1,3,2-dioxaborinan-2-yl)-2-[(cis)-3-methyl-3-f{[2-(trimethylsilyl)ethoxy]methoxy}cyclobutyl]-7-(trifluoromethyl)-1-{[2-(trimethylsilyl)ethoxy]methyl}-1H-1,3-benzodiazole, which was used in the subsequent step without further purification. MS=575.3 [M-C$_5$H$_8$+H]$^+$

Step 5: 2-[(cis)-3-methyl-3-{[2-(trimethylsilyl)ethoxy]methoxy}cyclobutyl]-7-(trifluoromethyl)-1-{[2-(trimethylsilyl)ethoxy]methyl}-1H-1,3-benzodiazol-5-ol

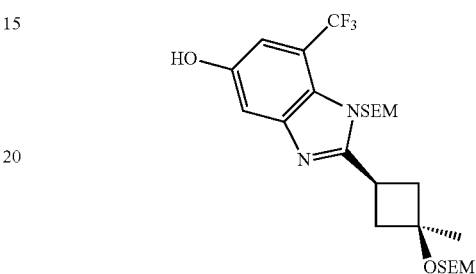

To a solution of 5-(5,5-dimethyl-1,3,2-dioxaborinan-2-yl)-2-[(cis)-3-methyl-3-{[2-(trimethylsilyl)ethoxy]methoxy}cyclobutyl]-7-(trifluoromethyl)-1-{[2-(trimethylsilyl)ethoxy]methyl}-1H-1,3-benzodiazole (600 mg, 934 µmol) in THF (6 mL) and H$_2$O (2 mL) was added Oxone (861 mg, 1.40 mmol). The mixture was stirred at room temperature for 2 h, then was quenched with saturated aqueous Na$_2$SO$_3$ solution (30 mL), and extracted with EtOAc (2×50 mL). The combined organic layers were dried over anhydrous Na$_2$SO$_4$, filtered, and concentrated in vacuo. The residue was purified by flash silica gel chromatography (Biotage 12 g cartridge, 0-19% EtOAc/Petroleum ether) to provide 2-[(cis)-3-methyl-3-{[2-(trimethylsilyl)ethoxy]methoxy}cyclobutyl]-7-(trifluoromethyl)-1-{[2-(trimethylsilyl)ethoxy]methyl}-1H-1,3-benzodiazol-5-ol. MS=547.2 [M+H]$^+$.

Step 6: 5-(2-bromoethoxy)-2-[(cis)-3-methyl-3-{[2-(trimethylsilyl)ethoxy]methoxy}cyclobutyl]-7-(trifluoromethyl)-1-{[2-(trimethylsilyl)ethoxy]methyl}-1H-1,3-benzodiazole

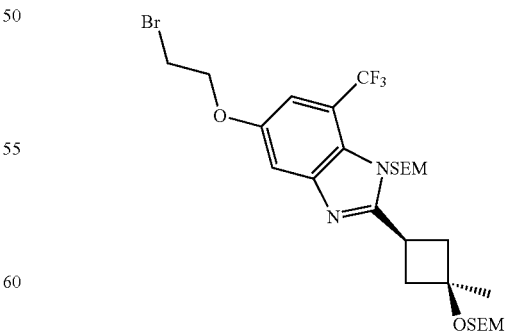

To a solution of 2-[(cis)-3-methyl-3-{[2-(trimethylsilyl)ethoxy]methoxy}cyclobutyl]-7-(trifluoromethyl)-1-{[2-(trimethylsilyl)ethoxy]methyl}-1H-1,3-benzodiazol-5-ol (130 mg, 238 mol) and 1,2-dibromoethane (206 µL, 2.38 mmol) in i-PrOH (5 mL) was added $Cs_2CO_3$ (232 mg, 713 μmol). The mixture was heated to 60° C. and stirred at 60° C. for 12 h. After cooling to room temperature, the reaction mixture was filtered, and the filtrate was concentrated in vacuo. The residue was purified by flash silica gel chromatography (Sepaflash 4 g cartridge, 0-15% EtOAc/Petroleum ether) to provide 5-(2-bromoethoxy)-2-[(cis)-3-methyl-3-{[2-(trimethylsilyl)ethoxy]methoxy}cyclobutyl]-7-(trifluoromethyl)-1-{[2-(trimethylsilyl)ethoxy]methyl}-1H-1,3-benzodiazole. $MS=653.1/655.1 [M+H]^+$ Step 7: 5-chloro-1'-[2-({2-[(cis)-3-methyl-3-{[2-(trimethylsilyl)ethoxy]methoxy}cyclobutyl]-7-(trifluoromethyl)-1-{[2-(trimethylsilyl)ethoxy]methyl}-1H-1,3-benzodiazol-5-yl}oxy)ethyl]-1,2-dihydrospiro[indole-3,4'-piperidin]-2-one Step 8: 5-chloro-1'-[2-({2-[(cis)-3-hydroxy-3-methylcyclobutyl]-7-(trifluoromethyl)-1H-1,3-benzodiazol-5-yl}oxy)ethyl]-1,2-dihydrospiro[indole-3,4'-piperidin]-2-one (Compound 466)

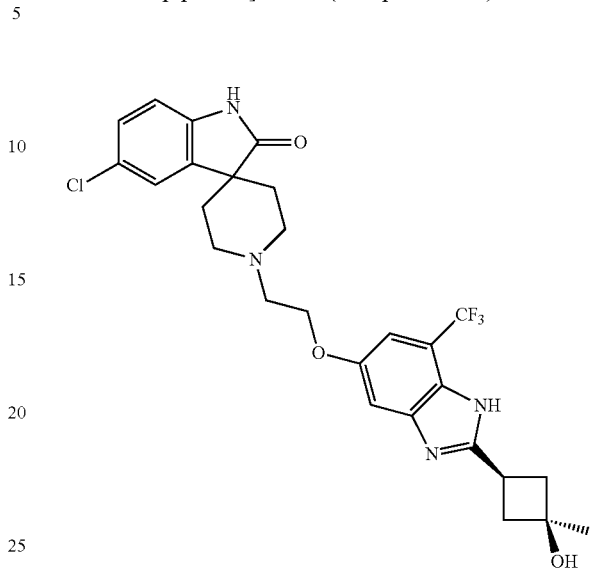

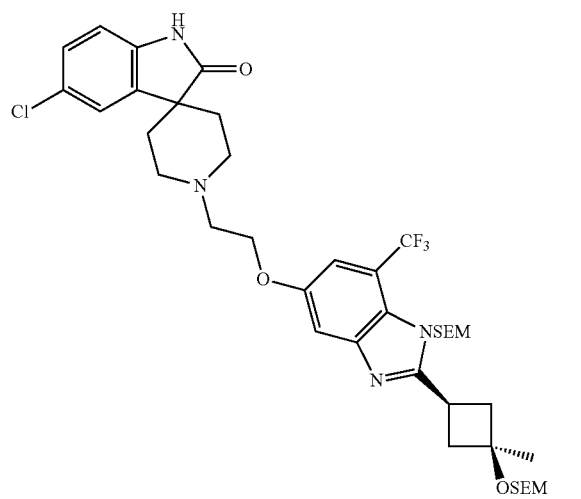

To a solution of 5-(2-bromoethoxy)-2-[(cis)-3-methyl-3-{[2-(trimethylsilyl)ethoxy]methoxy}cyclobutyl]-7-(trifluoromethyl)-1-{[2-(trimethylsilyl)ethoxy]methyl}-1H-1,3-benzodiazole (60.0 mg, 91.78 μmol) and 5-chloro-1,2-dihydrospiro[indole-3,4'-piperidin]-2-one (Intermediate B-4, 30.1 mg, 110 μmol, HCl salt) in MeCN (3 mL) was added $NaHCO_3$ (38.6 mg, 459 μmol). The mixture was heated to 80° C. and stirred at 80° C. for 16 h. After cooling to room temperature, the reaction mixture was filtered and the filtrate was concentrated in vacuo to give 5-chloro-1'-[2-({2-[(cis)-3-methyl-3-{[2-(trimethylsilyl)ethoxy]methoxy}cyclobutyl]-7-(trifluoromethyl)-1-{[2-(trimethylsilyl)ethoxy]methyl}-1H-1,3-benzodiazol-5-yl}oxy)ethyl]-1,2-dihydrospiro[indole-3,4'-piperidin]-2-one, which was used in the subsequent step without further purification. $MS=809.3 [M+H]^+$.

To a mixture of 5-chloro-1'-[2-({2-[(cis)-3-methyl-3-{[2-(trimethylsilyl)ethoxy]methoxy}cyclobutyl]-7-(trifluoromethyl)-1-{[2-(trimethylsilyl)ethoxy]methyl}-1H-1,3-benzodiazol-5-yl}oxy)ethyl]-1,2-dihydrospiro[indole-3,4'-piperidin]-2-one (90.0 mg, 111 μmol) in DCM (2 mL) was added TFA (165 μL, 2.22 mmol). The mixture was stirred at room temperature for 16 h, and then DCM was removed under reduced pressure. The residue was dissolved in THF (2 mL) and then 30% $NH_3·H_2O$ in $H_2O$ (285 μL, 2.22 mmol) was added. The mixture was stirred at room temperature for 1 h, then was concentrated under reduced pressure to remove THF. The residual mixture was purified by reverse phase preparative HPLC (Waters Xbridge BEH $C_{18}$ column, 30-60% MeCN: 10 mM $NH_4HCO_3$ in $H_2O$) to give 5-chloro-1'-[2-({2-[(cis)-3-hydroxy-3-methylcyclobutyl]-7-(trifluoromethyl)-1H-1,3-benzodiazol-5-yl}oxy)ethyl]-1,2-dihydrospiro[indole-3,4'-piperidin]-2-one (Compound 466). $^1$H NMR (400 MHz, DMSO-$d_6$): δ 12.43 (br s, 1H), 10.49 (s, 1H), 7.50 (s, 1H), 7.29-7.20 (m, 2H), 7.06 (s, 1H), 6.84 (d, J=8.4 Hz, 1H), 5.15 (br s, 1H), 4.21 (t, J=5.6 Hz, 2H), 3.32-3.20 (m, 1H), 2.90-2.85 (m, 4H), 2.73-2.68 (m, 2H), 2.40-2.30 (m, 4H), 1.80-1.70 (m, 4H), 1.19 (s, 3H). $MS=549.1 [M+H]^+$.

Example 100

5-chloro-1'-(2-{[3-(hydroxymethyl)-2-oxo-1-[(cis)-3-hydroxy-3-methylcyclobutyl]-7-(trifluoromethyl)-2,3-dihydro-1H-1,3-benzodiazol-5-yl]oxy}ethyl)-1,2-dihydrospiro[indole-3,4'-piperidin]-2-one (Compound 467) and 5-chloro-1'-[2-({2-oxo-1-[(cis)-3-hydroxy-3-methylcyclobutyl]-7-(trifluoromethyl)-2,3-dihydro-1H-1,3-benzodiazol-5-yl}oxy)ethyl]-1,2-dihydrospiro[indole-3,4'-piperidin]-2-one (Compound 468)

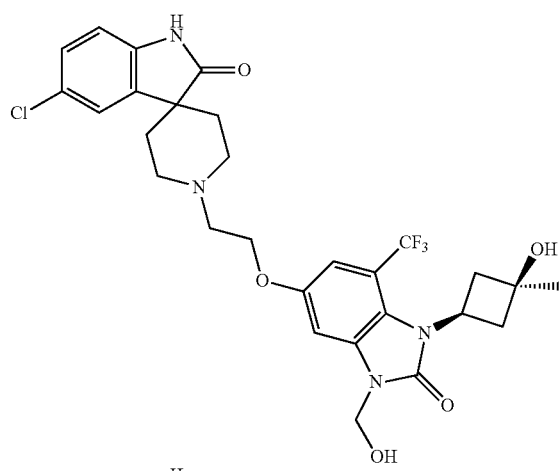

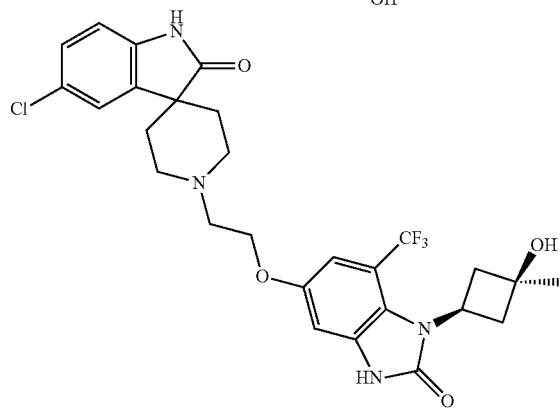

Step 1: 5-bromo-1-[(cis)-3-hydroxy-3-methylcyclobutyl]-7-(trifluoromethyl)-2,3-dihydro-1H-1,3-benzodiazol-2-one

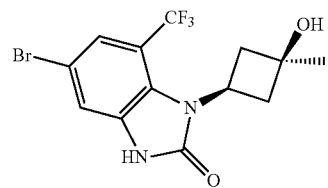 [SMILES: C[C@]1(O)C[C@@H](n2c(=O)[nH]c3cc(Br)cc(C(F)(F)F)c32)C1]

A solution of (cis)-3-{[2-amino-4-bromo-6-(trifluoromethyl)phenyl]amino}-1-methylcyclobutan-1-ol (General procedure for Intermediate A-92, Step 3, 2.00 g, 5.90 mmol) and carbonyl diimidazole (1.43 g, 8.85 mmol) in THF (20 mL) was warmed to 50° C. and stirred at 50° C. for 16 h. After cooling to room temperature, the reaction mixture was poured into H$_2$O (20 mL) and extracted with EtOAc (2×20 mL). The combined organic layers were concentrated in vacuo. The residue was dissolved into THF (30 mL) and H$_2$O (10 mL) and LiOH·H$_2$O (1.01 g, 24.2 mmol) was added. The mixture was stirred at 50° C. for 2 h. After cooling to room temperature, the reaction mixture was poured into H$_2$O (100 mL) and extracted with EtOAc (2×200 mL). The combined organic layers were dried over anhydrous Na$_2$SO$_4$, filtered, and concentrated in vacuo give 5-bromo-1-[(cis)-3-hydroxy-3-methylcyclobutyl]-7-(trifluoromethyl)-2,3-dihydro-1H-1,3-benzodiazol-2-one, which was used in the subsequent step without further purification. MS=365.0/367.0 [M+H]$^+$.

Step 2: 6-bromo-3-[(cis)-3-hydroxy-3-methylcyclobutyl]-4-(trifluoromethyl)-1-{[2-(trimethylsilyl)ethoxy]methyl}-2,3-dihydro-1H-1,3-benzodiazol-2-one

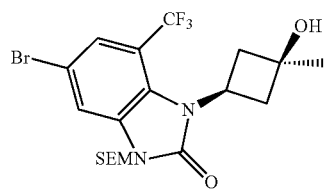 [SMILES: C[Si](C)(C)CCOCn1c(=O)n([C@H]2C[C@@](C)(O)C2)c2c(C(F)(F)F)cc(Br)cc21]

To a 0° C. mixture of 5-bromo-1-[(cis)-3-hydroxy-3-methylcyclobutyl]-7-(trifluoromethyl)-2,3-dihydro-1H-1,3-benzodiazol-2-one (2.70 g, 7.39 mmol) in THF (30 mL) was added NaH (887 mg, 22.2 mmol, 60% in mineral oil) portion wise. (2-(chloromethoxy)ethyl)trimethylsilane (2.62 mL, 14.8 mmol) was added dropwise to the 0° C. reaction mixture. The mixture was stirred at 0° C. for 2 h, then was quenched with ice water (30 mL). After stirring at 0° C. for an additional 10 min, the mixture was extracted with EtOAc (3×30 mL). The combined organic layers were washed with brine (30 mL), dried over anhydrous Na$_2$SO$_4$, filtered, and concentrated under reduced pressure. The residue was purified by flash silica gel chromatography (Sepaflash 20 g cartridge, 0-60% EtOAc/Petroleum ether) to provide 6-bromo-3-[(cis)-3-hydroxy-3-methylcyclobutyl]-4-(trifluoromethyl)-1-{[2-(trimethylsilyl)ethoxy]methyl}-2,3-dihydro-1H-1,3-benzodiazol-2-one. MS=495.0/497.0 [M+H]$^+$.

Step 3: 6-(5,5-dimethyl-1,3,2-dioxaborinan-2-yl)-3-[(cis)-3-hydroxy-3-methylcyclobutyl]-4-(trifluoromethyl)-1-{[2-(trimethylsilyl)ethoxy]methyl}-2,3-dihydro-1H-1,3-benzodiazol-2-one

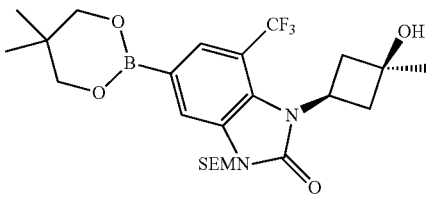

A mixture of 6-bromo-3-[(cis)-3-hydroxy-3-methylcyclobutyl]-4-(trifluoromethyl)-1-{[2-(trimethylsilyl)ethoxy]methyl}-2,3-dihydro-1H-1,3-benzodiazol-2-one (1.20 g, 2.42 mmol), Pd(dppf)Cl$_2$ (88.6 mg, 121 μmol), KOAc (357 mg, 3.63 mmol) and bis(neopentyl glycolato)diboron (1.09 g, 4.84 mmol) in 1,4-dioxane (15 mL) was degassed and purged with N$_2$ (3×), and then the mixture was stirred at 90° C. for 3 h under N$_2$ atmosphere. After cooling to room temperature, the reaction mixture was filtered and the filtrate was concentrated under reduced pressure to give 6-(5,5-dimethyl-1,3,2-dioxaborinan-2-yl)-3-[(cis)-3-hydroxy-3-methylcyclobutyl]-4-(trifluoromethyl)-1-{[2-(trimethylsilyl)ethoxy]methyl}-2,3-dihydro-1H-1,3-benzodiazol-2-one, which was used in the subsequent step without further purification. MS=461.2 [M-C$_5$H$_8$+H]$^+$.

Step 4: 6-hydroxy-3-[(cis)-3-hydroxy-3-methylcyclobutyl]-4-(trifluoromethyl)-1-{[2-(trimethylsilyl)ethoxy]methyl}-2,3-dihydro-1H-1,3-benzodiazol-2-one

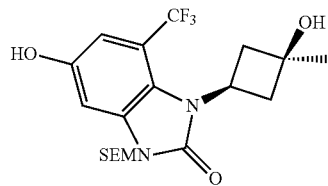 [SMILES: C[Si](C)(C)CCOCn1c(=O)n([C@H]2C[C@@](C)(O)C2)c2c(C(F)(F)F)cc(O)cc21]

To a solution of 6-(5,5-dimethyl-1,3,2-dioxaborinan-2-yl)-3-[(cis)-3-hydroxy-3-methylcyclobutyl]-4-(trifluoromethyl)-1-{[2-(trimethylsilyl)ethoxy]methyl}-2,3-dihydro-1H-1,3-benzodiazol-2-one (2.30 g, 4.35 mmol) in THF (16 mL) and H$_2$O (8 mL) was added Oxone (4.01 g, 6.53 mmol). The mixture was stirred at room temperature for 1 h. The reaction mixture was quenched with saturated aqueous Na$_2$SO$_3$ solution (20 mL) and extracted with EtOAc (2×20 mL). The combined organic layers were dried over anhydrous Na$_2$SO$_4$, filtered and concentrated under reduced pressure to give 6-hydroxy-3-[(cis)-3-hydroxy-3-methylcyclobutyl]-4-(trifluoromethyl)-1-{[2-(trimethylsilyl)ethoxy]methyl}-2,3-dihydro-1H-1,3-benzodiazol-2-one, which was used in the subsequent step without further purification. MS=433.2 [M+H]$^+$.

Step 5: 6-(2-bromoethoxy)-3-[(cis)-3-hydroxy-3-methylcyclobutyl]-4-(trifluoromethyl)-1-{[2-(trimethylsilyl)ethoxy]methyl}-2,3-dihydro-1H-1,3-benzodiazol-2-one

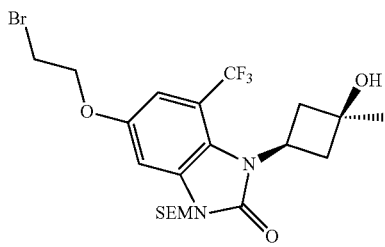 [SMILES: C[Si](C)(C)CCOCn1c(=O)n([C@H]2C[C@@](C)(O)C2)c2c(C(F)(F)F)cc(OCCBr)cc21]

To a solution of 6-hydroxy-3-[(cis)-3-hydroxy-3-methylcyclobutyl]-4-(trifluoromethyl)-1-{[2-(trimethylsilyl)ethoxy]methyl}-2,3-dihydro-1H-1,3-benzodiazol-2-one (1.60 g, 3.70 mmol) and 1,2-dibromoethane (2.79 mL, 37.0 mmol) in i-PrOH (20 mL) was added Cs$_2$CO$_3$ (3.62 g, 11.1 mmol). The mixture was stirred at 60° C. for 12 h. After cooling to room temperature, the reaction mixture was filtered, and the filtrate was concentrated in vacuo. The residue was purified by flash silica gel chromatography (Sepaflash 20 g cartridge, 0-18% EtOAc/Petroleum ether) to provide 6-(2-bromoethoxy)-3-[(cis)-3-hydroxy-3-methylcyclobutyl]-4-(trifluoromethyl)-1-{[2-(trimethylsilyl)ethoxy]methyl}-2,3-dihydro-1H-1,3-benzodiazol-2-one. MS=539.1/541.0 [M+H]$^+$.

Step 6: 5-chloro-1'-[2-({2-oxo-1-[(cis)-3-hydroxy-3-methylcyclobutyl]-7-(trifluoromethyl)-3-{[2-(trimethylsilyl)ethoxy]methyl}-2,3-dihydro-1H-1,3-benzodiazol-5-yl}oxy)ethyl]-1,2-dihydrospiro[indole-3,4'-piperidin]-2-one

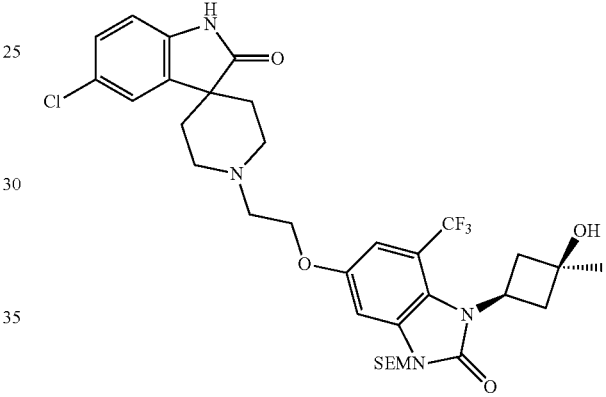

To a solution of 6-(2-bromoethoxy)-3-[(cis)-3-hydroxy-3-methylcyclobutyl]-4-(trifluoromethyl)-1-{[2-(trimethylsilyl)ethoxy]methyl}-2,3-dihydro-1H-1,3-benzodiazol-2-one (100 mg, 185 μmol) and 5-chloro-1,2-dihydrospiro[indole-3,4'-piperidin]-2-one (Intermediate B-4, 50.6 mg, 185 μmol, HCl salt) in MeCN (5 mL) was added NaHCO$_3$ (77.9 mg, 927 μmol). The mixture was warmed to 80° C. and stirred at 80° C. for 16 h. After cooling to room temperature, the reaction mixture was filtered, and the filtrate was concentrated in vacuo to give 5-chloro-1'-[2-({2-oxo-1-[(cis)-3-hydroxy-3-methylcyclobutyl]-7-(trifluoromethyl)-3-{[2-(trimethylsilyl)ethoxy]methyl}-2,3-dihydro-1H-1,3-benzodiazol-5-yl}oxy)ethyl]-1,2-dihydrospiro[indole-3,4'-piperidin]-2-one, which was used in the subsequent step without further purification. MS=695.2 [M+H]$^+$.

1317

Step 7: 5-chloro-1'-(2-{[3-(hydroxymethyl)-2-oxo-1-[(cis)-3-hydroxy-3-methylcyclobutyl]-7-(trifluoromethyl)-2,3-dihydro-1H-1,3-benzodiazol-5-yl]oxy}ethyl)-1,2-dihydrospiro[indole-3,4'-piperidin]-2-one (Compound 467)

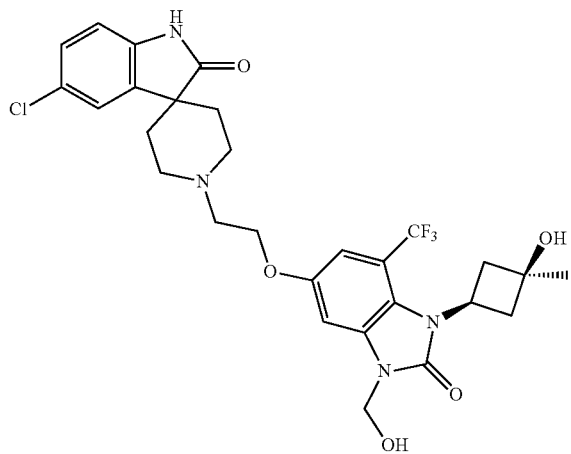 [SMILES: C[C@]1(O)C[C@@H](n2c(=O)n(CO)c3cc(OCCN4CCC5(CC4)C(=O)Nc4ccc(Cl)cc45)cc(C(F)(F)F)c32)C1]

To a mixture of 5-chloro-1'-[2-({2-oxo-1-[(cis)-3-hydroxy-3-methylcyclobutyl]-7-(trifluoromethyl)-3-{[2-(trimethylsilyl)ethoxy]methyl}-2,3-dihydro-1H-1,3-benzodiazol-5-yl}oxy)ethyl]-1,2-dihydrospiro[indole-3,4'-piperidin]-2-one (70.0 mg, 101 µmol) in DCM (1 mL) was added TFA (74.8 µL, 1.01 mmol). The mixture was stirred at room temperature for 1 h, then concentrated in vacuo. The residue was purified by reverse phase preparative HPLC (Phenomenex Luna OBD $C_{18}$ column, 5-35% MeCN: 0.04% HCl in $H_2O$) to give 5-chloro-1'-(2-{[3-(hydroxymethyl)-2-oxo-1-[(cis)-3-hydroxy-3-methylcyclobutyl]-7-(trifluoromethyl)-2,3-dihydro-1H-1,3-benzodiazol-5-yl]oxy}ethyl)-1,2-dihydrospiro[indole-3,4'-piperidin]-2-one (Compound 467, HCl salt). $^1$H NMR (400 MHz, DMSO-$d_6$): δ 10.82 (s, 0.5H), 10.74 (s, 0.5H), 10.41 (br s, 0.5H), 10.02 (br s, 0.5H), 8.00 (s, 0.5H), 7.40 (s, 1H), 7.38-7.30 (m, 1H), 7.16 (s, 0.5H), 7.06 (s, 1H), 6.94-6.90 (m, 1H), 6.62-6.50 (m, 1H), 5.28 (d, J=5.6 Hz, 2H), 5.27-5.15 (m, 1H), 4.52-4.50 (m, 2H), 4.30-4.25 (m, 1H), 3.95-3.50 (m, 6H), 3.21 (d, J=9.2 Hz, 2H), 2.50-2.40 (m, 1H), 2.20-2.17 (m, 3H), 2.18-1.90 (m, 2H), 1.23 (s, 3H). MS=595.1 [M+H]$^+$.

1318

Step 8: 5-chloro-1'-[2-({2-oxo-1-[(cis)-3-hydroxy-3-methylcyclobutyl]-7-(trifluoromethyl)-2,3-dihydro-1H-1,3-benzodiazol-5-yl}oxy)ethyl]-1,2-dihydrospiro[indole-3,4'-piperidin]-2-one (Compound 468)

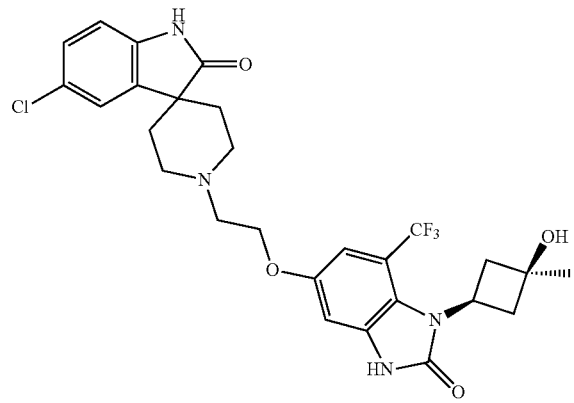 [SMILES: C[C@]1(O)C[C@@H](n2c(=O)[nH]c3cc(OCCN4CCC5(CC4)C(=O)Nc4ccc(Cl)cc45)cc(C(F)(F)F)c32)C1]

To a solution of 5-chloro-1'-(2-{[3-(hydroxymethyl)-2-oxo-1-[(cis)-3-hydroxy-3-methylcyclobutyl]-7-(trifluoromethyl)-2,3-dihydro-1H-1,3-benzodiazol-5-yl]oxy}ethyl)-1,2-dihydrospiro[indole-3,4'-piperidin]-2-one (170 mg, 286 µmol) in THF (2 mL) was added 30% $NH_3 \cdot H_2O$ in $H_2O$ (4.00 mL, 31.2 mmol). The mixture was stirred at room temperature for 2 h, then was concentrated in vacuo. The residue was purified by reverse phase preparative HPLC (Waters Xbridge OBD $C_{18}$ column, 20-55% MeCN: 10 mM $NH_4HCO_3$ in $H_2O$) to give 5-chloro-1'-[2-({2-oxo-1-[(cis)-3-hydroxy-3-methylcyclobutyl]-7-(trifluoromethyl)-2,3-dihydro-1H-1,3-benzodiazol-5-yl}oxy)ethyl]-1,2-dihydrospiro[indole-3,4'-piperidin]-2-one (Compound 468). $^1$H NMR (400 MHz, DMSO-$d_6$): δ 11.38 (s, 1H), 10.49 (s, 1H), 7.48 (d, J=2.0 Hz, 1H), 7.25-7.20 (m, 1H), 6.88 (s, 2H), 6.84 (d, J=8.0 Hz, 1H), 5.13 (s, 1H), 4.25-4.15 (m, 3H), 3.21 (t, J=9.2 Hz, 2H), 2.93-2.82 (m, 4H), 2.71-2.67 (m, 2H), 2.20-2.18 (m, 2H), 1.81-1.66 (m, 4H), 1.27 (s, 3H). MS=565.2 [M+H]$^+$.

The following compounds in Table 38.21 were prepared according to procedures similar to steps described for Example 100 using the appropriate starting materials or common intermediates.

TABLE 38.21

| # | Structure | IUPAC Name | Exact Mass [M + H]$^+$ | Intermediates Used |
|---|---|---|---|---|
| 469 | 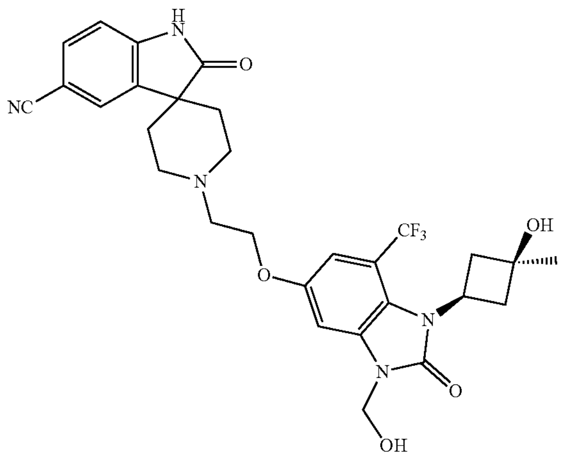 [SMILES: C[C@]1(O)C[C@@H](n2c(=O)n(CO)c3cc(OCCN4CCC5(CC4)C(=O)Nc4ccc(C#N)cc45)cc(C(F)(F)F)c32)C1] | 1'-(2-{[3-(hydroxymethyl)-2-oxo-1-[(cis)-3-hydroxy-3-methylcyclobutyl]-7-(trifluoromethyl)-2,3-dihydro-1H-1,3-benzodiazol-5-yl]oxy}ethyl)-2-oxo-1,2-dihydrospiro[indole-3,4'-piperidine]-5-carbonitrile | Calc'd 586.2 Found 586.1 | B-9 |
| 470 | 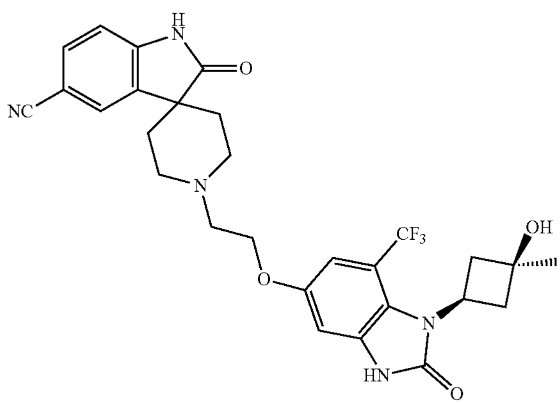 [SMILES: C[C@]1(O)C[C@@H](n2c(=O)[nH]c3cc(OCCN4CCC5(CC4)C(=O)Nc4ccc(C#N)cc45)cc(C(F)(F)F)c32)C1] | 2-oxo-1'-[2-({2-oxo-1-[(cis)-3-hydroxy-3-methylcyclobutyl]-7-(trifluoromethyl)-2,3-dihydro-1H-1,3-benzodiazol-5-yl}oxy)ethyl]-1,2-dihydrospiro[indole-3,4'-piperidine]-5-carbonitrile | Calc'd 556.2 Found 556.2 | B-9 |

BIOLOGICAL EXAMPLES

Example B1

This example shows that compounds of the present disclosure are able to inhibit calcium transport by APOL1.

A HEK293 clonal cell line was generated to stably express GCaMP6f, a genetically encoded calcium indicator, and inducibly express APOL1 G2 (HEK T-REx/GCaMP6f/APOL1 G2 K6.3). Cells were maintained in the following standard complete medium: DMEM with 4.5 g/L glucose and sodium pyruvate (BioWhittaker, Lonza, BE12-614F), supplemented with 10% FBS Performance Plus (Gibco, 16000044), 1% penicillin-streptomycin (BioWhittaker, DE17-602E), 2 mM ultraglutamine-1 (BioWhittaker cat. BE 17-605/U1), 50 µg/mL Zeocin (InvivoGen, ant-zn), 2.5 µg/mL Blasticidin (InvivoGen, ant-bl-5), and 25 µg/mL Hygromycin (InvivoGen, ant-hg). Standard propagation conditions consisted of plating 9×10$^6$, 4×10$^6$, 2×10$^6$ cells in a T225 flasks to be processed after 2, 3, or 4 days, respectively.

A source plate was generated containing 20 serially diluted compounds in DMSO (duplicate 8-point dose response). Next, 0.8 µL of compounds were transferred from the source plate to a destination plate prefilled with 79.2 µL of Ca$^{2+}$ free Tyrode's buffer (130 mM NaCl, 5 mM KCl, 1 mM MgCl$_2$, 5 mM NaHCO$_3$, 20 mM HEPES at pH 7.4). The destination plate was placed on a plate shaker (5 seconds at 2000 rpm) to mix. This process resulted in a destination plate with 2× concentrated compound solutions. All transfer and mixing steps were conducted with an CyBi®-Well dispenser.

Cells were split by gently washing with DPBS (Euroclone, ECB4004L), followed by a 5-minute incubation (humidified, 37° C. with 5% CO$_2$) with trypsin-EDTA solution (Euroclone, ECB3052D). Detached cells were diluted with standard complete medium without selective agents, counted, and plated in a 384 MTP microplate (GR4332CPL, Twin Helix) (10,000 cells/well in 25 µl/well) using a MATRIX WellMate dispenser. Plates were placed into a humidified incubator (37° C. with 5% CO$_2$) overnight. The following day, 20 µL of doxycycline (Sigma, D9891) at 20 ng/mL in standard complete medium was added to cells with a CyBi® Drop dispenser to induce APOL1 G2 expression. After a 6-hour incubation (humidified, 37° C. with 5% CO$_2$), cells were washed 3 times with Ca$^{2+}$ free Tyrode's Buffer (130 mM NaCl, 5 mM KCl, 1 mM MgCl$_2$, 5 mM NaHCO$_3$, 20 mM HEPES at pH 7.4) using a BIOTEK Microplate washer, such that 10 µL of buffer remained in each well after the final wash. Assay plates were then stored at room temperature for 10 minutes. Next, 10 µL of diluted compounds were transferred to the assay plate from the 2× compound plate using a CyBi®-Well dispenser. Compound incubation was then carried out at room temperature for 10 minutes. The assay plate was transferred to the FLIPR$^{TETRA}$ and 20 μL of 10 mM Ca$^{2+}$ (final concentration=5 mM) Tyrode's buffer was injected.

Table 39 below summarizes the data from this experiment. Unless otherwise specified, AC$_{50}$ and values are reported as the geometric mean of at least 2 assay runs on separate days. Each run represents the average of a technical replicate, where each compound was assayed twice in the same plate. A superscript t symbol indicates a value from the average of a technical replicate from a single assay run, where each compound was assayed twice in the same plate.

The AC$_{50}$ values in Table 39 below reflect the compound's ability to prevent calcium influx by inhibiting APOL1. As shown in the table, numerous compounds of the present disclosure are able to potently inhibit APOL1-mediated calcium transport at sub micromolar concentrations. Compounds in Table 39 are referred to by the corresponding Compound Number in Table 1, which is also referred to in the synthetic examples. When one or more of the numbered compounds are identified by stereochemistry (for example, (R)- or (S)-), the specific stereoisomer for which data is provided in Table 39 may be identified by the elution order of such compound as described in the synthetic examples. For example, Compounds 39 and 40 are associated with Step 5 of Example 13, where Compound 39 is the first eluting enantiomer, and Compound 40 is the second eluting enantiomer in the chiral separation of Compound 38. For Table 39 below, n/a represents "not available".

TABLE 39

| Cmpd No. | APOL1 G2 FLIPR AC$_{50}$ (μM) |
| --- | --- |
| 1 | 0.703 |
| 4 | 0.670 |
| 7 | 0.601 |
| 8 | 0.833 |
| 9 | 1.31 |
| 10 | 1.27 |
| 11 | 1.05† |
| 12 | <0.457 |
| 13 | <0.587 |
| 14 | 0.704 |
| 15 | 0.654 |
| 16 | 1.16 |
| 17 | 1.10 |
| 18 | 0.240 |
| 19 | 0.481 |
| 20 | 0.348 |
| 21 | <0.213 |
| 22 | 0.306 |
| 23 | 0.514 |
| 24 | 0.2 |
| 25 | 0.651† |
| 26 | 0.943 |
| 27 | 0.51 |
| 28 | <0.434 |
| 29 | 0.586† |
| 30 | 0.409† |
| 31 | 0.37† |
| 32 | 0.262 |
| 33 | 0.218 |
| 34 | 0.168 |
| 35 | 0.142 |
| 36 | 0.223 |
| 37 | 0.327 |
| 38 | 0.307 |
| 39 | 0.745 |
| 40 | 0.657 |
| 41 | 0.709 |
| 42 | 0.316 |
| 43 | 0.507 |
| 44 | 0.352 |

TABLE 39-continued

| Cmpd No. | APOL1 G2 FLIPR AC$_{50}$ (μM) |
| --- | --- |
| 45 | 0.746 |
| 46 | 0.434 |
| 47 | 0.641 |
| 48 | 0.567 |
| 49 | 0.875† |
| 50 | 0.622 |
| 51 | 0.953† |
| 52 | 0.615† |
| 53 | 0.838 |
| 54 | 0.804 |
| 55 | <0.284 |
| 56 | 1.01 |
| 57 | 0.706 |
| 58 | <0.320 |
| 59 | 0.879 |
| 60 | 0.652 |
| 61 | 0.686 |
| 62 | 0.958 |
| 63 | 0.461 |
| 64 | 0.455 |
| 65 | 0.639 |
| 66 | 0.461 |
| 67 | 0.351 |
| 68 | <0.249 |
| 69 | 0.216 |
| 70 | 0.124 |
| 71 | 0.626 |
| 72 | 0.252 |
| 73 | 0.161 |
| 74 | 0.781 |
| 75 | 0.689 |
| 76 | 0.678 |
| 77 | 1.60† |
| 78 | 0.522 |
| 79 | 0.687 |
| 80 | 0.375 |
| 81 | 0.549† |
| 82 | 1.05† |
| 83 | 0.718 |
| 84 | 1.45† |
| 85 | 0.564 |
| 86 | 0.539 |
| 87 | 0.375 |
| 88 | 0.698 |
| 89 | 0.463 |
| 90 | 0.973 |
| 91 | 0.739 |
| 92 | 0.761 |
| 93 | 0.951 |
| 94 | 0.794 |
| 95 | 0.655† |
| 96 | 0.552 |
| 97 | 0.823 |
| 98 | 0.6 |
| 99 | 0.643 |
| 100 | 0.503 |
| 101 | 0.634 |
| 102 | 0.671 |
| 103 | 0.591 |
| 104 | 0.408 |
| 105 | 0.392 |
| 106 | 0.756 |
| 107 | 0.712 |
| 108 | 0.86 |
| 109 | 1.19 |
| 110 | 0.772 |
| 111 | 0.919 |
| 112 | 0.746 |
| 113 | 0.524 |
| 114 | 0.529 |
| 115 | 0.472† |
| 116 | 0.466† |
| 117 | 0.396† |
| 118 | 1.04† |
| 119 | 1.01† |
| 120 | 1.19† |

TABLE 39-continued

| Cmpd No. | APOL1 G2 FLIPR AC$_{50}$ (μM) |
|---|---|
| 121 | 0.508 |
| 122 | 0.616 |
| 123 | 0.796 |
| 124 | 0.727 |
| 125 | 0.729† |
| 126 | 0.624† |
| 127 | 0.542† |
| 128 | 0.537† |
| 129 | 0.352 |
| 130 | 0.525 |
| 131 | 0.464 |
| 132 | 0.492† |
| 133 | 0.671† |
| 134 | 0.879† |
| 135 | 0.763† |
| 136 | 0.80† |
| 137 | 0.597† |
| 138 | 1.22† |
| 139 | 1.12† |
| 140 | 0.807† |
| 141 | 0.954† |
| 142 | 0.845 |
| 143 | 0.701 |
| 144 | 0.708† |
| 145 | 0.465† |
| 146 | 0.279† |
| 147 | 0.492 |
| 148 | 0.96 |
| 149 | 0.971 |
| 150 | 0.629 |
| 151 | 1.74 |
| 152 | 1.82 |
| 153 | 0.826† |
| 154 | 0.869† |
| 155 | 0.452† |
| 156 | 0.468† |
| 157 | 0.933† |
| 158 | 0.845† |
| 159 | 1.01† |
| 160 | 0.898 |
| 161 | 0.539† |
| 162 | 0.603 |
| 163 | 0.528 |
| 164 | 0.555 |
| 165 | 0.558† |
| 166 | 0.618† |
| 167 | 0.467† |
| 168 | 1.39† |
| 169 | 1.21† |
| 170 | 1.31† |
| 171 | 0.598† |
| 172 | 0.479† |
| 173 | 0.908† |
| 174 | 0.484† |
| 175 | 0.381† |
| 176 | 0.547† |
| 177 | 0.67† |
| 178 | 0.55† |
| 179 | 0.655† |
| 180 | 0.756 |
| 181 | 0.656 |
| 182 | 0.574† |
| 183 | 1.52† |
| 184 | 1.28 |
| 185 | 0.993 |
| 186 | 0.524† |
| 187 | 1.22† |
| 188 | 0.513† |
| 189 | 0.349† |
| 190 | n/a |
| 191 | 1.17 |
| 192 | 0.291† |
| 193 | 1.27 |
| 194 | 0.600† |
| 195 | 0.604 |
| 196 | 0.696 |
| 197 | 0.889 |
| 198 | 0.631 |
| 199 | 1.13 |
| 200 | 1.2 |
| 201 | 0.909† |
| 202 | 1.72† |
| 203 | 1.19 |
| 204 | 0.869† |
| 205 | 1.22† |
| 206 | n/a |
| 207 | n/a |
| 208 | 1.55 |
| 209 | 1.24† |
| 210 | 1.54 |
| 211 | 1.29 |
| 212 | 1.36 |
| 213 | 1.12† |
| 214 | 0.355 |
| 215 | 1.13 |
| 216 | 3.14† |
| 217 | 0.866† |
| 218 | 0.69† |
| 219 | 0.835 |
| 220 | 0.679† |
| 221 | 0.598 |
| 222 | 0.783 |
| 223 | 0.311† |
| 224 | 0.83 |
| 225 | 0.847 |
| 226 | 1.08† |
| 227 | 1.11† |
| 228 | 1.20† |
| 229 | 0.792† |
| 230 | 0.891† |
| 231 | 1.02† |
| 232 | 1.01 |
| 233 | 1.16 |
| 234 | 0.786† |
| 235 | 1.00† |
| 236 | 0.634 |
| 237 | 3.31 |
| 238 | 0.285† |
| 239 | 1.54 |
| 240 | n/a |
| 241 | n/a |
| 242 | n/a |
| 243 | n/a |
| 244 | 1.06 |
| 245 | 0.718 |
| 246 | 1.34 |
| 247 | 0.806† |
| 248 | 0.82 |
| 249 | 0.433† |
| 250 | 0.559 |
| 251 | 0.546† |
| 252 | 1.35† |
| 253 | 1.22† |
| 254 | 0.898† |
| 255 | 2.64† |
| 256 | 0.261† |
| 257 | 0.974† |
| 258 | 1.05† |
| 259 | 0.651 |
| 260 | 1.38 |
| 261 | 1.46 |
| 262 | 2.39† |
| 263 | 2.54 |
| 264 | 1.95† |
| 265 | 0.697 |
| 266 | 0.862 |
| 272 | 0.921 |
| 273 | 2.10 |
| 274 | 0.722 |
| 275 | 0.640 |
| 276 | 1.75 |
| 277 | n/a |

TABLE 39-continued

| Cmpd No. | APOL1 G2 FLIPR AC$_{50}$ (μM) |
|---|---|
| 278 | 0.769 |
| 279 | n/a |
| 280 | n/a |
| 281 | 1.31 |
| 282 | n/a |
| 283 | 2.00 |
| 284 | 0.756 |
| 285 | 0.714 |
| 286 | 0.917 |
| 287 | 0.303 |
| 288 | 0.369 |
| 289 | 0.552 |
| 290 | 0.253 |
| 291 | 1.19 |
| 292 | 1.30 |
| 293 | n/a |
| 294 | n/a |
| 295 | n/a |
| 296 | n/a |
| 297 | 0.937 |
| 298 | n/a |
| 299 | n/a |
| 300 | 0.674 |
| 301 | 0.586 |
| 302 | 1.03 |
| 303 | 0.822 |
| 304 | 1.01 |
| 305 | 0.649 |
| 306 | 1.40 |
| 307 | 0.320 |
| 308 | n/a |
| 309 | n/a |
| 310 | n/a |
| 311 | n/a |
| 312 | n/a |
| 313 | n/a |
| 314 | 0.968 |
| 315 | 0.330 |
| 316 | 1.15 |
| 317 | 0.792 |
| 318 | n/a |
| 319 | 0.378 |
| 320 | 0.787 |
| 321 | 0.621 |
| 322 | 0.588 |
| 323 | 0.400 |
| 324 | 0.942 |
| 325 | 0.791 |
| 326 | 0.680 |
| 327 | 0.452 |
| 328 | 0.748 |
| 329 | n/a |
| 330 | n/a |
| 331 | n/a |
| 332 | n/a |
| 333 | 0.486 |
| 334 | 2.00 |
| 335 | n/a |
| 336 | n/a |
| 338 | n/a |
| 339 | n/a |
| 340 | n/a |
| 341 | 1.06 |
| 342 | 0.780 |
| 343 | 0.437 |
| 344 | n/a |
| 345 | 0.469 |
| 346 | 0.557 |
| 347 | n/a |
| 348 | n/a |
| 349 | 0.199 |
| 350 | 0.113 |
| 351 | n/a |
| 352 | 0.597 |
| 353 | n/a |
| 354 | n/a |
| 355 | n/a |
| 356 | 2.49 |
| 357 | 0.412 |
| 358 | n/a |
| 359 | n/a |
| 360 | n/a |
| 361 | n/a |
| 362 | n/a |
| 363 | n/a |
| 364 | n/a |
| 365 | n/a |
| 366 | n/a |
| 367 | n/a |
| 368 | n/a |
| 369 | n/a |
| 370 | n/a |
| 371 | 0.504 |
| 372 | n/a |
| 373 | n/a |
| 374 | n/a |
| 375 | n/a |
| 376 | n/a |
| 377 | n/a |
| 378 | n/a |
| 379 | n/a |
| 380 | n/a |
| 381 | n/a |
| 382 | n/a |
| 383 | n/a |
| 384 | n/a |
| 385 | n/a |
| 386 | n/a |
| 387 | n/a |
| 388 | n/a |
| 389 | n/a |
| 390 | n/a |
| 391 | n/a |
| 392 | n/a |
| 393 | 1.06 |
| 394 | 0.250 |
| 395 | n/a |
| 396 | 0.531 |
| 397 | 0.416 |
| 398 | n/a |
| 399 | n/a |
| 400 | n/a |
| 401 | 0.603† |
| 402 | n/a |
| 403 | n/a |
| 404 | n/a |
| 405 | n/a |
| 406 | n/a |
| 407 | n/a |
| 408 | 0.283† |
| 409 | n/a |
| 410 | 0.623† |
| 411 | 0.436† |
| 412 | 2.9† |
| 413 | 0.251† |
| 414 | 0.347† |
| 415 | 0.319† |
| 416 | 0.449† |
| 417 | 0.343† |
| 418 | 0.309† |
| 419 | 0.383† |
| 420 | 0.892† |
| 421 | 0.564† |
| 422 | n/a |
| 423 | 0.284† |
| 424 | 0.895† |
| 425 | 1.1† |
| 426 | 0.597 |
| 427 | 0.708† |
| 428 | 1.2† |
| 429 | 0.435† |
| 430 | 0.518† |

TABLE 39-continued

| Cmpd No. | APOL1 G2 FLIPR AC$_{50}$ (μM) |
|---|---|
| 431 | 4.87† |
| 432 | 2.56† |
| 433 | 1.3† |
| 434 | 1.27† |
| 435 | 1.17 |
| 436 | n/a |
| 437 | 0.612† |
| 438 | n/a |
| 439 | 0.603 |
| 440 | 0.552 |
| 441 | n/a |
| 442 | 2.14† |
| 443 | 2.67† |
| 444 | n/a |
| 445 | 1.11 |
| 446 | 1.18† |
| 447 | 1.13 |
| 448 | 1.14† |
| 449 | 0.609† |
| 450 | 2.27† |
| 451 | 0.459† |
| 452 | n/a |
| 453 | 0.935† |
| 454 | 0.473† |
| 455 | 1.25† |
| 456 | 1.01† |
| 457 | n/a |
| 458 | 0.528† |
| 459 | 0.37† |
| 460 | 0.317† |
| 461 | 0.676† |
| 462 | 0.943† |
| 463 | 2.84† |
| 464 | 1.19† |
| 465 | 0.748† |
| 466 | n/a |
| 467 | n/a |
| 468 | 0.867 |
| 469 | n/a |
| 470 | 1.11† |
| 471 | n/a |
| 472 | n/a |

Example B2

This example shows that the compounds of the present disclosure are able to reduce cell death caused by overexpression of APOL1.

A HTEK293 clonal cell line overexpressing APOL1 G2 (HEK293/T-REx APOL1 G2/clone #2) was maintained in 1×DMEM-GlutaMax (Gibco, 10569-010) media with 1000 tetracycline-free FBS (Takara Bio USA, 631101), 5 μg/mL Blasticidin (Gibco, A1113903), and 100 μg/mL Zeocin (Invitrogen, R25001) in T75 flasks. In preparation for the assay, this media was aspirated and 2 mL of prewarmed TrypLE Express (Gibco, 12605-010) was added to a flask to detach cells. The flask was then incubated (humidified, 37° C. with 500 $CO_2$) for 3-5 minutes. Afterwards, 8 mL of prewarmed cell assay media (1×DMEM-GlutaMax media with 100% tetracycline-free FBS) was added to the trypsinized cells. The suspension was gently mixed, and cells were counted using a Countess Cell Counting Chamber (Invitrogen). The suspension was diluted using cell assay media to generate a working stock solution (166,667 cells/mL). Using a Multi-Drop Combi (Thermo Electron Corp), 30 μL (final cell density=5,000 cells/well) of the working stock solution was dispensed into each well of white 384-well assay ready plates (Nunc™ 164610) containing 6 ng/mL doxycycline, to induce APOL1 expression, and compound. All compounds were plated in a duplicate 8-point dilution series that consisted of 3-fold stepwise dilutions (0.5% DMSO final). Assay plates were incubated (humidified, 37° C. with 5% $CO_2$) for 17 hours. After the incubation, the plates were equilibrated at room temperature for 1 hour. Next, 15 μl of CellTiter-Glo® reagent (Promega, G7570) was added to each well using a MultiDrop Combi. Plates were placed on an orbital shaker (500 rpm) for 5 minutes to induce cell lysis and then incubated at room temperature for 10 minutes. Luminescence was measured on an Envision plate reader. Collaborative Drug Discovery software was utilized for graphing data. Plots were generated using a four parameter logistic curve fit.

Table 40 below provides the results from this experiment. Unless otherwise specified, EC$_{50}$ values are reported as the geometric mean of at least 2 assay runs on separate days. Each run represents the average of a technical replicate, where each compound was assayed twice in the same plate. A superscript t symbol indicates a value from the average of a technical replicate from a single assay run, where each compound was assayed twice in the same plate. Compounds in Table 40 are referred to by the corresponding Compound Number in Table 1, which is also referred to in the synthetic examples. When one or more of the numbered compounds are identified by stereochemistry (for example, (R)- or (S)-), the specific stereoisomer for which data is provided in Table 40 may be identified by the elution order of such compound as described in the synthetic examples. Absolute stereochemistry of such compounds may be identified by methods known in the art. For Table 40 below, n/a represents "not available".

Rescue EC$_{50}$ values reported in Table 40 below represent the half-maximal effective concentration for reversal of cell death caused by overexpression of APOL1. This example demonstrates that compounds of the present disclosure are able to reduce cell death caused by overexpression of APOL1 at sub micromolar concentration.

TABLE 40

| Cmpd No. | APOL1 G2 HEK293 Rescue EC$_{50}$ (μM) |
|---|---|
| 1 | 0.120† |
| 2 | 0.134† |
| 3 | 0.142† |
| 4 | 0.0719 |
| 5 | 0.213 |
| 6 | 0.121 |
| 7 | 0.279 |
| 8 | 0.598 |
| 9 | 1.76 |
| 10 | 0.0903 |
| 11 | 1.70 |
| 12 | 0.307 |
| 13 | 3.01 |
| 14 | 0.13 |
| 15 | 0.124 |
| 16 | 0.112 |
| 17 | 0.060 |
| 18 | 0.225 |
| 19 | 0.794 |
| 20 | 0.294 |
| 21 | 1.27 |
| 22 | 0.232 |
| 23 | 0.135 |
| 24 | 0.24 |
| 25 | 1.31 |
| 26 | 1.76 |
| 27 | 0.062 |

TABLE 40-continued

| Cmpd No. | APOL1 G2 HEK293 Rescue EC$_{50}$ (μM) |
|---|---|
| 28 | 0.799 |
| 29 | 1.42 |
| 30 | 1.48 |
| 31 | 0.81 |
| 32 | 0.785 |
| 33 | 1.07 |
| 34 | 1.33 |
| 35 | 0.574 |
| 36 | 0.919 |
| 37 | 1.28 |
| 38 | 0.059 |
| 39 | 0.0567 |
| 40 | 0.072 |
| 41 | 0.097 |
| 42 | 0.343 |
| 43 | 0.0331 |
| 44 | 0.116 |
| 45 | 0.122 |
| 46 | 0.0728 |
| 47 | 0.148 |
| 48 | 0.199 |
| 49 | 0.0664 |
| 50 | 0.0249 |
| 51 | 0.214 |
| 52 | 0.214 |
| 53 | 0.0529 |
| 54 | 0.0903 |
| 55 | 0.983 |
| 56 | 0.105 |
| 57 | 0.19 |
| 58 | 1.31 |
| 59 | 0.213 |
| 60 | 0.0627 |
| 61 | 0.267 |
| 62 | 0.165 |
| 63 | 0.0511 |
| 64 | 0.163 |
| 65 | 0.0875 |
| 66 | 0.108 |
| 67 | 0.802 |
| 68 | 0.148 |
| 69 | 0.0826 |
| 70 | 1.05 |
| 71 | 0.345 |
| 72 | 0.0359† |
| 73 | 0.527 |
| 74 | 0.167 |
| 75 | 0.114 |
| 76 | 0.0477 |
| 77 | 2.25 |
| 78 | 0.041 |
| 79 | 0.207 |
| 80 | 0.0657 |
| 81 | 0.28 |
| 82 | 0.0722 |
| 83 | 0.247 |
| 84 | 0.0649 |
| 85 | 0.0703 |
| 86 | 0.0465 |
| 87 | 0.103 |
| 88 | 0.121 |
| 89 | 0.0557 |
| 90 | 0.151 |
| 91 | 0.0245 |
| 92 | 0.0515 |
| 93 | 0.0909 |
| 94 | 0.14 |
| 95 | 0.246 |
| 96 | 0.0505 |
| 97 | 0.0446 |
| 98 | 0.0544† |
| 99 | 0.0865 |
| 100 | 0.0465 |
| 101 | 0.0496 |
| 102 | 0.0314 |
| 103 | 0.0494 |
| 104 | 0.139 |
| 105 | 0.0407 |
| 106 | 0.0335 |
| 107 | 0.0308 |
| 108 | 0.0169 |
| 109 | 0.0969 |
| 110 | 0.0413 |
| 111 | 0.142 |
| 112 | 0.0472 |
| 113 | 0.0836 |
| 114 | 0.0465 |
| 115 | 0.0949 |
| 116 | 0.0818 |
| 117 | 0.0815 |
| 118 | 0.431 |
| 119 | 0.435 |
| 120 | 0.324 |
| 121 | 0.0812 |
| 122 | 0.0875 |
| 123 | 0.0795 |
| 124 | 0.297 |
| 125 | 0.355 |
| 126 | 0.273 |
| 127 | 0.0208 |
| 128 | 0.0427 |
| 129 | 0.0246 |
| 130 | 0.0923 |
| 131 | 0.068 |
| 132 | 0.153 |
| 133 | 0.203 |
| 134 | 0.199 |
| 135 | 0.211 |
| 136 | 0.0224 |
| 137 | 0.114 |
| 138 | 0.0782 |
| 139 | 0.133 |
| 140 | 0.172 |
| 141 | 0.048 |
| 142 | 0.0483 |
| 143 | 0.0369 |
| 144 | 0.081 |
| 145 | 0.0504 |
| 146 | 0.121 |
| 147 | 0.0631 |
| 148 | 0.107 |
| 149 | 0.101 |
| 150 | 0.228 |
| 151 | 0.397 |
| 152 | 0.405 |
| 153 | 0.0221 |
| 154 | 0.0671 |
| 155 | 0.0262 |
| 156 | 0.0559 |
| 157 | 0.0504 |
| 158 | 0.0657 |
| 159 | 0.168 |
| 160 | 0.0754 |
| 161 | 0.0464 |
| 162 | 0.0571 |
| 163 | 0.0246 |
| 164 | 0.103 |
| 165 | 0.0212† |
| 166 | 0.0561† |
| 167 | 0.0427† |
| 168 | 0.343† |
| 169 | 0.247 |
| 170 | 0.803† |
| 171 | 0.100† |
| 172 | 0.0991† |
| 173 | 0.289† |
| 174 | 0.104† |
| 175 | 0.0631† |
| 176 | 0.0469† |
| 177 | 0.0782† |

TABLE 40-continued

| Cmpd No. | APOL1 G2 HEK293 Rescue EC$_{50}$ (µM) |
|---|---|
| 178 | 0.256† |
| 179 | 0.164† |
| 180 | 0.0221 |
| 181 | 0.0445 |
| 182 | 0.0996† |
| 183 | 0.702† |
| 184 | 0.498 |
| 185 | 0.113 |
| 186 | 0.0359† |
| 187 | 0.268† |
| 188 | 0.0392† |
| 189 | 0.0591† |
| 190 | 0.0547 |
| 191 | 0.13 |
| 192 | 0.0411 |
| 193 | 0.155 |
| 194 | 0.246 |
| 195 | 0.0394 |
| 196 | 0.0919 |
| 197 | 0.0323 |
| 198 | 0.0631 |
| 199 | 0.148 |
| 200 | 0.0872 |
| 201 | 0.609 |
| 202 | 0.315 |
| 203 | 0.187 |
| 204 | 1.55 |
| 205 | 0.472 |
| 206 | >9.54 |
| 207 | >10.0 |
| 208 | 0.238 |
| 209 | 3.07 |
| 210 | 0.0633 |
| 211 | 0.138 |
| 212 | 0.0814 |
| 213 | 0.189 |
| 214 | 0.079 |
| 215 | 0.0798 |
| 216 | 0.281 |
| 217 | 0.0326 |
| 218 | 0.0256 |
| 219 | 0.0263 |
| 220 | 0.053 |
| 221 | 0.0474 |
| 222 | 0.141 |
| 223 | 0.0978 |
| 224 | 0.0386 |
| 225 | 0.0326 |
| 226 | 0.043 |
| 227 | 0.047 |
| 228 | 0.101 |
| 229 | 0.128 |
| 230 | 0.0987 |
| 231 | 0.042 |
| 232 | 0.0392 |
| 233 | 0.0577 |
| 234 | 0.0803 |
| 235 | 0.0598 |
| 236 | 0.045 |
| 237 | 0.238 |
| 238 | 0.0852 |
| 239 | 0.0779 |
| 240 | 0.0526 |
| 241 | 0.0721 |
| 242 | 0.074 |
| 243 | 0.046 |
| 244 | 0.0704 |
| 245 | 0.139 |
| 246 | 0.562 |
| 247 | 0.092 |
| 248 | 0.0584 |
| 249 | 0.0268† |
| 250 | 0.0492† |
| 251 | 0.125† |
| 252 | 0.471† |
| 253 | 0.608† |
| 254 | 0.175† |
| 255 | 0.353† |
| 256 | 0.0446† |
| 257 | 0.256† |
| 258 | 0.444† |
| 259 | 0.0375 |
| 260 | 0.119 |
| 261 | 0.089 |
| 262 | 0.299 |
| 263 | 0.198 |
| 264 | 2.25 |
| 265 | 0.030 |
| 266 | 0.104 |
| 267 | 0.0378 |
| 268 | 0.0534 |
| 269 | 0.102 |
| 270 | 0.0256 |
| 271 | 0.152 |
| 272 | 0.0934 |
| 273 | 0.0885 |
| 274 | 0.034 |
| 275 | 0.027 |
| 276 | 0.101 |
| 277 | 0.034 |
| 278 | 0.023 |
| 279 | 0.060 |
| 280 | 0.080 |
| 281 | 0.056 |
| 282 | 0.130 |
| 283 | 0.099 |
| 284 | 0.199 |
| 285 | 0.200 |
| 286 | 0.181 |
| 287 | 0.0335 |
| 288 | 0.0341 |
| 289 | 0.0167 |
| 290 | 0.0182 |
| 291 | 0.0264 |
| 292 | 0.0232 |
| 293 | 0.294 |
| 294 | 0.0233 |
| 295 | 0.0436 |
| 296 | 0.0773 |
| 297 | 0.0318 |
| 298 | 0.0818 |
| 299 | 0.0213 |
| 300 | 0.10 |
| 301 | 0.086 |
| 302 | 0.0981 |
| 303 | 0.156 |
| 304 | 0.134 |
| 305 | 0.0854 |
| 306 | 0.110 |
| 307 | 0.0204 |
| 308 | 0.112 |
| 309 | 0.0559 |
| 310 | 0.103 |
| 311 | 0.0383 |
| 312 | 0.0243 |
| 313 | 0.0633 |
| 314 | 0.0243 |
| 315 | 0.0257 |
| 316 | 0.0327 |
| 317 | 0.0239 |
| 318 | 0.0232 |
| 319 | 0.0419 |
| 320 | 0.0221 |
| 321 | 0.0241 |
| 322 | 0.0185 |
| 323 | 0.0173 |
| 324 | 0.0256 |
| 325 | 0.0864 |
| 326 | 0.0312 |
| 327 | 0.0289 |

TABLE 40-continued

| Cmpd No. | APOL1 G2 HEK293 Rescue EC$_{50}$ (μM) |
|---|---|
| 328 | 0.0341 |
| 329 | 0.0569 |
| 330 | 0.668 |
| 331 | 0.166 |
| 332 | n/a |
| 333 | 0.043 |
| 334 | 0.110 |
| 335 | n/a |
| 336 | n/a |
| 338 | 0.0994 |
| 339 | 0.0366 |
| 340 | 0.0302 |
| 341 | 0.0415 |
| 342 | 0.0902 |
| 343 | 0.162 |
| 344 | 0.194 |
| 345 | 0.0364 |
| 346 | 0.0343 |
| 347 | n/a |
| 348 | n/a |
| 349 | 0.0254 |
| 350 | 0.0188 |
| 351 | 0.166 |
| 352 | 0.0086 |
| 353 | 0.0123 |
| 354 | 0.0146 |
| 355 | n/a |
| 356 | 0.0506 |
| 357 | 0.0223 |
| 358 | 0.065 |
| 359 | n/a |
| 360 | n/a |
| 361 | n/a |
| 362 | n/a |
| 363 | n/a |
| 364 | 0.112 |
| 365 | n/a |
| 366 | 0.080 |
| 367 | 0.0877 |
| 368 | n/a |
| 369 | n/a |
| 370 | n/a |
| 371 | 0.0172 |
| 372 | n/a |
| 373 | 0.0534 |
| 374 | 0.101 |
| 375 | n/a |
| 376 | 0.0469 |
| 377 | 0.0859 |
| 378 | 0.388 |
| 379 | 0.842 |
| 380 | n/a |
| 381 | n/a |
| 382 | n/a |
| 383 | n/a |
| 384 | n/a |
| 385 | n/a |
| 386 | n/a |
| 387 | n/a |
| 388 | n/a |
| 389 | n/a |
| 390 | n/a |
| 391 | n/a |
| 392 | 0.0271 |
| 393 | 0.0805 |
| 394 | 0.024 |
| 395 | 0.0868 |
| 396 | 0.0405 |
| 397 | 0.0459 |
| 398 | 0.0201 |
| 399 | 0.0498 |
| 400 | 0.224 |
| 401 | 0.0367 |
| 402 | 0.0238 |
| 403 | 0.0957 |
| 404 | 0.129 |
| 405 | 0.00959 |
| 406 | 0.0583 |
| 407 | 0.0241 |
| 408 | 0.0231 |
| 409 | 0.0702 |
| 410 | 0.0641 |
| 411 | 0.0226 |
| 412 | 0.0453 |
| 413 | 0.0603 |
| 414 | 0.0367 |
| 415 | 0.0203 |
| 416 | 0.169 |
| 417 | 0.0492 |
| 418 | 0.0785 |
| 419 | 0.0309 |
| 420 | 0.0647 |
| 421 | 0.0345 |
| 422 | 0.0635 |
| 423 | 0.0593 |
| 424 | 0.0502 |
| 425 | 0.0906 |
| 426 | 0.0378 |
| 427 | 0.0185 |
| 428 | 0.0543 |
| 429 | 0.13 |
| 430 | 0.0729 |
| 431 | 0.0187 |
| 432 | 0.161 |
| 433 | 0.0148 |
| 434 | 0.0112 |
| 435 | 0.0129 |
| 436 | 0.0801 |
| 437 | 0.112 |
| 438 | 0.204 |
| 439 | 0.0149 |
| 440 | 0.0544 |
| 441 | 0.0574 |
| 442 | <3.08E−03 |
| 443 | 0.0102 |
| 444 | 0.0224 |
| 445 | 0.00815 |
| 446 | 0.0332 |
| 447 | 0.0341† |
| 448 | 0.112† |
| 449 | 0.102 |
| 450 | 0.0055 |
| 451 | 0.0321 |
| 452 | 0.0282 |
| 453 | 0.0191 |
| 454 | 0.0241 |
| 455 | 0.0753 |
| 456 | 0.0282 |
| 457 | 0.278 |
| 458 | 0.0165 |
| 459 | 0.029 |
| 460 | 0.0541 |
| 461 | 0.0281 |
| 462 | 0.0178 |
| 463 | 0.00584 |
| 464 | 0.00502 |
| 465 | 0.00886 |
| 466 | 0.00426 |
| 467 | 0.00474 |
| 468 | 0.00645 |
| 469 | 0.0199 |
| 470 | 0.179 |
| 471 | >3.30 |
| 472 | n/a |

Example B3

This example shows that the compounds of the present disclosure are able to reduce cell death caused by overexpression of APOL1.

Compounds were also assayed in a HEK293 clonal cell line overexpressing APOL1 G1 by a method similar to that shown in Example B2 above.

Table 41 below provides the results from this experiment. Unless otherwise specified, $EC_{50}$ values are reported as the geometric mean of at least 2 assay runs on separate days. Each run represents the average of a technical replicate, where each compound was assayed twice in the same plate. A superscript † symbol indicates a value from the average of a technical replicate from a single assay run, where each compound was assayed twice in the same plate. A ¥ symbol represents compound concentration at 50% rescue estimated due to lack of sigmoidal curve preventing curve fitting. Compounds in Table 41 are referred to by the corresponding Compound Number in Table 1, which is also referred to in the synthetic examples. When one or more of the numbered compounds are identified by stereochemistry (for example, (R)- or (S)-), the specific stereoisomer for which data is provided in Table 41 may be identified by the elution order of such compound as described in the synthetic examples. Absolute stereochemistry of such compounds may be identified by methods known in the art. For Table 41 below, n/a represents "not available".

Rescue $EC_{50}$ values reported in Table 41 below represent the half-maximal effective concentration for reversal of cell death caused by overexpression of APOL1. This example demonstrates that compounds of the present disclosure are able to reduce cell death caused by overexpression of APOL1 at sub micromolar concentration.

TABLE 41

| Cmpd No. | APOL1 G1 HEK293 Rescue $EC_{50}$ (μM) |
|---|---|
| 1 | 0.302 |
| 2 | 0.346 |
| 3 | 0.257 |
| 4 | 0.177 |
| 5 | 0.295 |
| 6 | 0.252 |
| 7 | 0.764 |
| 8 | 1.44 |
| 9 | 11.5¥ |
| 10 | 0.444 |
| 11 | 2.3 |
| 12 | 1.14 |
| 13 | >30.0 |
| 14 | 0.476 |
| 15 | 0.279 |
| 16 | 0.295 |
| 17 | 0.16 |
| 18 | 0.663 |
| 19 | 4.81 |
| 20 | 0.815 |
| 21 | >14.4 |
| 22 | 0.58 |
| 23 | 0.449 |
| 24 | 0.609 |
| 25 | 8.3¥ |
| 26 | 10.9¥ |
| 27 | 0.186 |
| 28 | 0.655 |
| 29 | 5.56 |
| 30 | >22.5 |
| 31 | 1.57 |
| 32 | 1.86 |
| 33 | >3.47 |
| 34 | >1.96 |
| 35 | 0.488 |
| 36 | >2.15 |
| 37 | 0.692 |
| 38 | 0.222 |
| 39 | >0.247 |
| 40 | 0.294 |
| 41 | 0.307 |
| 42 | 1.08 |
| 43 | 0.131 |
| 44 | 0.478 |
| 45 | 0.387 |
| 46 | 0.253 |
| 47 | 0.399 |
| 48 | 0.445 |
| 49 | 0.26 |
| 50 | 0.0911 |
| 51 | 1.25 |
| 52 | 1.06 |
| 53 | 0.219 |
| 54 | 0.386 |
| 55 | 1.21 |
| 56 | 0.33 |
| 57 | 0.39 |
| 58 | 2.12 |
| 59 | 0.422 |
| 60 | 0.183 |
| 61 | 0.632 |
| 62 | 0.433 |
| 63 | 0.16 |
| 64 | 0.516 |
| 65 | 0.351 |
| 66 | 0.323 |
| 67 | 2.86 |
| 68 | 0.368 |
| 69 | 0.311 |
| 70 | >2.53 |
| 71 | 1.34 |
| 72 | 0.161 |
| 73 | 3.52 |
| 74 | 0.471 |
| 75 | 0.406 |
| 76 | 0.19 |
| 77 | >4.76 |
| 78 | 0.128 |
| 79 | 0.533 |
| 80 | 0.178 |
| 81 | 0.948 |
| 82 | 0.252 |
| 83 | 0.788 |
| 84 | 0.233 |
| 85 | 0.157 |
| 86 | 0.126 |
| 87 | 0.281 |
| 88 | 0.438 |
| 89 | 0.138 |
| 90 | 0.594 |
| 91 | 0.099 |
| 92 | 0.101 |
| 93 | 0.23 |
| 94 | 0.21 |
| 95 | 0.457 |
| 96 | 0.148 |
| 97 | 0.143 |
| 98 | 0.183 |
| 99 | 0.205 |
| 100 | 0.134 |
| 101 | 0.248 |
| 102 | 0.111 |
| 103 | 0.124 |
| 104 | 0.356 |
| 105 | 0.175 |
| 106 | 0.122 |

TABLE 41-continued

| Cmpd No. | APOL1 G1 HEK293 Rescue EC$_{50}$ (μM) |
|---|---|
| 107 | 0.12 |
| 108 | 0.0497 |
| 109 | 0.321 |
| 110 | 0.1 |
| 111 | 0.246 |
| 112 | 0.0775 |
| 113 | 0.176 |
| 114 | 0.128 |
| 115 | 0.199 |
| 116 | 0.234 |
| 117 | 0.174 |
| 118 | 2.1¥ |
| 119 | 3.4¥ |
| 120 | >5.23 |
| 121 | 0.249 |
| 122 | 0.188 |
| 123 | 0.232 |
| 124 | 0.92 |
| 125 | >4.86 |
| 126 | 1.01 |
| 127 | 0.061 |
| 128 | 0.158 |
| 129 | 0.0728 |
| 130 | 0.253 |
| 131 | 0.186 |
| 132 | 0.685 |
| 133 | 0.885 |
| 134 | 0.991 |
| 135 | 1.14 |
| 136 | 0.0494 |
| 137 | 0.249 |
| 138 | 0.253 |
| 139 | 0.383 |
| 140 | 0.6 |
| 141 | 0.204 |
| 142 | 0.192 |
| 143 | 0.125 |
| 144 | 0.246 |
| 145 | 0.0985 |
| 146 | 0.221 |
| 147 | 0.183 |
| 148 | 0.282 |
| 149 | 0.246 |
| 150 | 1.54 |
| 151 | 2.5¥ |
| 152 | >4.17 |
| 153 | 0.0962 |
| 154 | 0.252 |
| 155 | 0.067 |
| 156 | 0.153 |
| 157 | 0.152 |
| 158 | 0.252 |
| 159 | 0.588 |
| 160 | 0.244 |
| 161 | 0.135 |
| 162 | 0.174 |
| 163 | 0.113 |
| 164 | 0.316 |
| 165 | 0.059 |
| 166 | 0.163 |
| 167 | 0.138 |
| 168 | >7.84 |
| 169 | 1.03 |
| 170 | 2.3¥ |
| 171 | 0.228 |
| 172 | 0.188 |
| 173 | 1.16† |
| 174 | 0.253 |
| 175 | 0.153 |
| 176 | 0.157 |
| 177 | 0.132 |
| 178 | 1.19† |
| 179 | 0.484 |
| 180 | 0.0749 |
| 181 | 0.194 |
| 182 | 0.225 |
| 183 | 5.8¥ |
| 184 | 2.5¥ |
| 185 | 0.231 |
| 186 | 0.0988 |
| 187 | 1.26 |
| 188 | 0.122 |
| 189 | 0.148 |
| 190 | 0.105 |
| 191 | 0.283 |
| 192 | 0.126 |
| 193 | 0.377 |
| 194 | 0.414 |
| 195 | 0.072 |
| 196 | 0.207 |
| 197 | 0.0695 |
| 198 | 0.203 |
| 199 | 0.312 |
| 200 | 0.203 |
| 201 | 4.92 |
| 202 | 2.55 |
| 203 | 0.457 |
| 204 | 1.27 |
| 205 | 1.76 |
| 206 | 4.31 |
| 207 | >10.0 |
| 208 | 0.554 |
| 209 | >2.84 |
| 210 | 0.153 |
| 211 | 0.38 |
| 212 | 0.192 |
| 213 | 0.497 |
| 214 | 0.169 |
| 215 | 0.122 |
| 216 | 1¥ |
| 217 | 0.108 |
| 218 | 0.125 |
| 219 | 0.116 |
| 220 | 0.301 |
| 221 | 0.217 |
| 222 | 0.605 |
| 223 | 0.326 |
| 224 | 0.155 |
| 225 | 0.0517 |
| 226 | 0.138 |
| 227 | 0.21 |
| 228 | 0.426 |
| 229 | 0.396 |
| 230 | 0.325 |
| 231 | 0.169 |
| 232 | 0.137 |
| 233 | 0.244 |
| 234 | 0.233 |
| 235 | 0.268 |
| 236 | 0.134 |
| 237 | >3.25 |
| 238 | 0.244 |
| 239 | 0.191 |
| 240 | 0.282 |
| 241 | 0.217 |
| 242 | 0.316 |
| 243 | 0.208 |
| 244 | 0.189 |
| 245 | 0.301 |
| 246 | 4.86 |
| 247 | 0.27 |
| 248 | 0.219 |
| 249 | 0.0706 |
| 250 | 0.192 |
| 251 | 0.323¥ |
| 252 | 1.8¥ |
| 253 | 4.4¥ |
| 254 | 2.04 |
| 255 | 2.9¥ |
| 256 | 0.116 |

TABLE 41-continued

| Cmpd No. | APOL1 G1 HEK293 Rescue EC$_{50}$ (μM) |
|---|---|
| 257 | 1$^¥$ |
| 258 | 1.3$^¥$ |
| 259 | 0.0925 |
| 260 | 0.248 |
| 261 | 0.167 |
| 262 | 1.78 |
| 263 | 0.462 |
| 264 | 10$^¥$ |
| 265 | 0.132 |
| 266 | 0.353 |
| 267 | 0.137 |
| 268 | 0.211 |
| 269 | 0.325 |
| 270 | 0.0607 |
| 271 | 0.34 |
| 272 | 0.148 |
| 273 | 0.206 |
| 274 | 0.0999 |
| 275 | 0.0627 |
| 276 | 0.228 |
| 277 | 0.117 |
| 278 | 0.0926 |
| 279 | 0.234 |
| 280 | 0.235 |
| 281 | 0.164 |
| 282 | 0.383 |
| 283 | 0.211 |
| 284 | 0.775 |
| 285 | 0.292 |
| 286 | 0.272 |
| 287 | 0.0858 |
| 288 | 0.0621 |
| 289 | 0.0506 |
| 290 | 0.0639 |
| 291 | 0.104 |
| 292 | 0.0515 |
| 293 | 0.193$^†$ |
| 294 | 0.0656 |
| 295 | 0.112 |
| 296 | 0.159 |
| 297 | 0.119 |
| 298 | 0.218 |
| 299 | 0.0636 |
| 300 | 0.183 |
| 301 | 0.19 |
| 302 | 0.236 |
| 303 | 0.351 |
| 304 | 0.286 |
| 305 | 0.172 |
| 306 | 0.245 |
| 307 | 0.07 |
| 308 | 0.196 |
| 309 | 0.134 |
| 310 | 0.267 |
| 311 | 0.1 |
| 312 | 0.0665 |
| 313 | 0.135 |
| 314 | 0.0532 |
| 315 | 0.086 |
| 316 | 0.0994 |
| 317 | 0.0456 |
| 318 | 0.0659 |
| 319 | 0.118 |
| 320 | 0.0539 |
| 321 | 0.0477 |
| 322 | 0.0386 |
| 323 | 0.0364 |
| 324 | 0.0408 |
| 325 | 0.197 |
| 326 | 0.104 |
| 327 | 0.0844 |
| 328 | 0.0982 |
| 329 | 0.0961 |
| 330 | 1.5$^¥$ |
| 331 | 0.44 |
| 332 | 10$^¥$ |
| 333 | 0.0986 |
| 334 | 0.269 |
| 335 | n/a |
| 336 | n/a |
| 338 | 0.213 |
| 339 | n/a |
| 340 | n/a |
| 341 | n/a |
| 342 | n/a |
| 343 | 0.431 |
| 344 | 0.254 |
| 345 | 0.079 |
| 346 | 0.0837 |
| 347 | n/a |
| 348 | n/a |
| 349 | 0.0735 |
| 350 | 0.0439 |
| 351 | 0.299 |
| 352 | 0.00995 |
| 353 | 0.0345 |
| 354 | 0.0401 |
| 355 | n/a |
| 356 | 0.162$^†$ |
| 357 | 0.0353 |
| 358 | 0.111 |
| 359 | n/a |
| 360 | n/a |
| 361 | n/a |
| 362 | n/a |
| 363 | n/a |
| 364 | 0.239 |
| 365 | n/a |
| 366 | 0.136 |
| 367 | 0.145 |
| 368 | n/a |
| 369 | n/a |
| 370 | n/a |
| 371 | 0.0288 |
| 372 | n/a |
| 373 | 0.133 |
| 374 | 0.216 |
| 375 | n/a |
| 376 | 0.129 |
| 377 | 0.172 |
| 378 | 1$^¥$ |
| 379 | >10 |
| 380 | n/a |
| 381 | n/a |
| 382 | n/a |
| 383 | n/a |
| 384 | n/a |
| 385 | n/a |
| 386 | n/a |
| 387 | n/a |
| 388 | n/a |
| 389 | n/a |
| 390 | n/a |
| 391 | n/a |
| 392 | 0.0899 |
| 393 | 0.159 |
| 394 | 0.0777 |
| 395 | 0.157 |
| 396 | 0.085 |
| 397 | 0.105 |
| 398 | 0.374 |
| 399 | 0.117 |
| 400 | 0.678 |
| 401 | 0.0682 |
| 402 | 0.0357 |
| 403 | 0.144 |
| 404 | 0.247 |
| 405 | 0.0192 |
| 406 | 0.109 |
| 407 | 0.0463 |

TABLE 41-continued

| Cmpd No. | APOL1 G1 HEK293 Rescue EC$_{50}$ (μM) |
|---|---|
| 408 | 0.056 |
| 409 | 0.136 |
| 410 | 0.0933 |
| 411 | 0.0556 |
| 412 | 0.0707 |
| 413 | 0.208 |
| 414 | 0.11 |
| 415 | 0.0692 |
| 416 | 0.382 |
| 417 | 0.104 |
| 418 | 0.215 |
| 419 | 0.108 |
| 420 | 0.144 |
| 421 | 0.0833 |
| 422 | 0.165 |
| 423 | 0.116 |
| 424 | 0.112 |
| 425 | 0.271 |
| 426 | 0.0803 |
| 427 | 0.0358 |
| 428 | 0.0896 |
| 429 | 0.2 |
| 430 | 0.123 |
| 431 | 0.037 |
| 432 | 0.288 |
| 433 | 0.0296 |
| 434 | 0.0148 |
| 435 | 0.0384 |
| 436 | 0.114 |
| 437 | 0.186 |
| 438 | 0.242 |
| 439 | 0.0455 |
| 440 | 0.139 |
| 441 | 0.0961 |
| 442 | 0.0156 |
| 443 | 0.0308 |
| 444 | 0.0723 |
| 445 | 0.0294 |
| 446 | 0.0825 |
| 447 | 0.0643 |
| 448 | 0.687 |
| 449 | 0.247 |
| 450 | 0.0149 |
| 451 | 0.115 |
| 452 | 0.0844 |
| 453 | n/a |
| 454 | n/a |
| 455 | n/a |
| 456 | 0.0982 |
| 457 | >3.30 |
| 458 | 0.0757 |
| 459 | 0.0955 |
| 460 | 0.0977 |
| 461 | 0.0809 |
| 462 | 0.0534 |
| 463 | 0.0132 |
| 464 | n/a |
| 465 | n/a |
| 466 | 0.00871 |
| 467 | 0.0143 |
| 468 | 0.0145 |
| 469 | 0.0487 |
| 470 | 0.0476 |
| 471 | >3.30 |
| 472 | n/a |

Example B4

APOL1 G2 human immortalized podocyte viability assay for measurement of cytotoxicity reversal by compound (APOL1 G2 podocyte cell rescue assay). This example shows that the compounds of the present disclosure are able to reverse cytotoxicity in human immortalized podocytes.

Cell Handling. The hTERT-immortalized kidney podocyte cell line was procured from the laboratory of Dr. Moin Saleem at the University of Bristol, UK (Nephrology 17 (2012) 525-531; doi:10.1111/j.1440-1797.2012.01619.x; herein incorporated by reference in its entirety). Parental and engineered cell lines were cultured in RPMI 1640 media (Gibco, 11875093) with 10% Tet System Approved FBS (Takara, 631101). The engineered cell line was maintained under selection (2.5 μg/mL puromycin). Cell lines were maintained and engineered at 33° C. Cell cultures were transferred to 37° C. for 10 to 14 days to initiate differentiation (Nephrology 17 (2012) 525-531; doi:10.1111/j.1440-1797.2012.01619.x; herein incorporated by reference in its entirety). During this time, media was refreshed every 3 days. After differentiation, cells engineered to inducibly express APOL1 G2 were used in the podocyte cell rescue assay.

Cell Line Engineering. The APOL1 G2 coding sequence was cloned into the pLVX-TetOne-Puro vector and verified by sequencing (Genscript Biotech). This construct was designed to have a C-terminal HiBiT tag. Lentiviral packaging of the vector was conducted using the Lenti-X Packaging Single Shots (VSVG) system according to manufacturer instructions (Takara Bio, 631275). A stable cell line was generated by transfecting the parental podocyte cell line with the concentrated virus in media with 5 μg/mL polybrene (Sigma, TR-1003-G). Media was changed the following day. 72 hours post transfection, 2.5 μg/mL puromycin (Gibco, A1113803) was added to the cells and cells were maintained in selection media thereafter. This APOL1 G2 stable cellular pool was subjected to a stringent limiting dilution to generate a pure stable clone (Podocyte/pLVX-TetOne APOL1 G2/clone D10) capable of inducible expression of APOL1 G2.

Assay Setup. T175 flasks containing differentiated podocytes engineered to inducibly express APOL1 G2 (Podocyte/pLVX-TetOne APOL1 G2/clone D10) were washed once with 15 mL of DPBS (Thermo Fisher, 14190-144). These flasks were each trypsinized with 3 mL of prewarmed TrypLE Express (Gibco, 12605-010) and incubated at 37° C. with 5% CO$_2$ until cells detached and neutralized with 7 mL of prewarmed assay media (RPMI 1640 media with 10% Tet System Approved FBS, no selection agent). Cells were pooled and the resulting suspension was gently mixed. The cell suspension was counted using a Countess Cell Counting Chamber (Invitrogen) and the cell concentration was adjusted to 240,000 cells/mL using assay media. Next, 25 μL of a 480 ng/mL working stock of doxycycline diluted in assay media was added to an assay ready plate. All experiments were performed in 384-well, white, solid bottom, tissue culture treated plates (Greiner, 781080). The assay ready compound plates were generated with duplicate 8-point compound dilution series that consisted of 3-fold stepwise dilutions (0.4% DMSO final). The plates were centrifuged at 1000 rpm for 1 minute. 25 μL of diluted cell suspension (final cell density=6,000 cells/well) was added to each well. The plates were centrifuged again at 1000 rpm for 1 minute and then incubated in a humidified incubator (37° C. with 5% CO$_2$). After 95 hours, the assay plates were removed from the incubator and allowed to equilibrate to room temperature for 1 hour. CellTiter-Glo® reagent (Promega, G7570) was prepared according to the manufacturer's instructions. 25 μL of CellTiter-Glo® reagent was added to each well. Assay plates were sealed with foil and mixed for 5 minutes on an orbital shaker (500 rpm) to induce cell lysis. Plates were centrifuged at 1000 rpm for 1 minute. 10 minutes after CellTiter-Glo® reagent addition, an Envision plate reader (Perkin Elmer) was used to measure the luminescent signal of each assay plate. Collaborative Drug Discovery software was utilized for graphing data.

Table 42 below provides the results from this experiment. Unless otherwise specified, $EC_{50}$ values are reported as the geometric mean of at least 2 assay runs on separate days. Each run represents the average of a technical replicate, where each compound was assayed twice in the same plate. A superscript t symbol indicates a value from the average of a technical replicate from a single assay run, where each compound was assayed twice in the same plate. Compounds in Table 42 are referred to by the corresponding Compound Number in Table 1, which is also referred to in the synthetic examples. When one or more of the numbered compounds are identified by stereochemistry (for example, (R)- or (S)-), the specific stereoisomer for which data is provided in Table 42 may be identified by the elution order of such compound as described in the synthetic examples. Absolute stereochemistry of such compounds may be identified by methods known in the art. For Table 42 below, n/a represents "not available".

Rescue $EC_{50}$ values reported in Table 42 below represent the half-maximal effective concentration for reversal of cell death caused by overexpression of APOL1. This example demonstrates that compounds of the present disclosure are able to reduce cell death caused by overexpression of APOL1 at sub micromolar concentration.

TABLE 42

| Cmpd No. | APOL1 G2 Podocyte Rescue $EC_{50}$ (µM) |
|---|---|
| 1 | 0.0188 |
| 2 | 0.0107 |
| 3 | 0.0235 |
| 4 | 0.00916 |
| 5 | >0.330 |
| 6 | 0.0477 |
| 7 | n/a |
| 8 | n/a |
| 9 | n/a |
| 10 | n/a |
| 11 | n/a |
| 12 | n/a |
| 13 | n/a |
| 14 | n/a |
| 15 | n/a |
| 16 | n/a |
| 17 | n/a |
| 18 | n/a |
| 19 | n/a |
| 20 | n/a |
| 21 | n/a |
| 22 | n/a |
| 23 | n/a |
| 24 | 0.0374 |
| 25 | n/a |
| 26 | n/a |
| 27 | n/a |
| 28 | n/a |
| 29 | n/a |
| 30 | n/a |
| 31 | n/a |
| 32 | n/a |
| 33 | n/a |
| 34 | n/a |
| 35 | n/a |
| 36 | n/a |
| 37 | n/a |
| 38 | n/a |
| 39 | n/a |
| 40 | n/a |
| 41 | n/a |
| 42 | n/a |
| 43 | n/a |
| 44 | n/a |
| 45 | n/a |
| 46 | n/a |
| 47 | n/a |
| 48 | n/a |
| 49 | n/a |
| 50 | n/a |
| 51 | n/a |
| 52 | n/a |
| 53 | n/a |
| 54 | n/a |
| 55 | n/a |
| 56 | n/a |
| 57 | n/a |
| 58 | n/a |
| 59 | n/a |
| 60 | n/a |
| 61 | n/a |
| 62 | n/a |
| 63 | n/a |
| 64 | n/a |
| 65 | n/a |
| 66 | n/a |
| 67 | n/a |
| 68 | n/a |
| 69 | n/a |
| 70 | n/a |
| 71 | n/a |
| 72 | n/a |
| 73 | n/a |
| 74 | n/a |
| 75 | n/a |
| 76 | n/a |
| 77 | n/a |
| 78 | n/a |
| 79 | n/a |
| 80 | n/a |
| 81 | n/a |
| 82 | n/a |
| 83 | n/a |
| 84 | n/a |
| 85 | n/a |
| 86 | n/a |
| 87 | n/a |
| 88 | n/a |
| 89 | n/a |
| 90 | n/a |
| 91 | n/a |
| 92 | n/a |
| 93 | n/a |
| 94 | n/a |
| 95 | n/a |
| 96 | n/a |
| 97 | n/a |
| 98 | n/a |
| 99 | n/a |
| 100 | n/a |
| 101 | n/a |
| 102 | n/a |
| 103 | n/a |
| 104 | n/a |
| 105 | n/a |
| 106 | n/a |
| 107 | n/a |
| 108 | n/a |
| 109 | n/a |
| 110 | n/a |
| 111 | n/a |
| 112 | n/a |
| 113 | n/a |
| 114 | n/a |
| 115 | n/a |
| 116 | n/a |
| 117 | n/a |
| 118 | n/a |
| 119 | n/a |
| 120 | n/a |
| 121 | n/a |

TABLE 42-continued

| Cmpd No. | APOL1 G2 Podocyte Rescue EC$_{50}$ (μM) |
|---|---|
| 122 | n/a |
| 123 | n/a |
| 124 | n/a |
| 125 | n/a |
| 126 | n/a |
| 127 | 0.00539 |
| 128 | n/a |
| 129 | n/a |
| 130 | n/a |
| 131 | n/a |
| 132 | n/a |
| 133 | n/a |
| 134 | n/a |
| 135 | n/a |
| 136 | n/a |
| 137 | n/a |
| 138 | n/a |
| 139 | n/a |
| 140 | n/a |
| 141 | n/a |
| 142 | n/a |
| 143 | n/a |
| 144 | n/a |
| 145 | n/a |
| 146 | n/a |
| 147 | n/a |
| 148 | n/a |
| 149 | n/a |
| 150 | n/a |
| 151 | n/a |
| 152 | n/a |
| 153 | n/a |
| 154 | n/a |
| 155 | n/a |
| 156 | n/a |
| 157 | n/a |
| 158 | n/a |
| 159 | n/a |
| 160 | n/a |
| 161 | n/a |
| 162 | n/a |
| 163 | n/a |
| 164 | n/a |
| 165 | n/a |
| 166 | n/a |
| 167 | n/a |
| 168 | n/a |
| 169 | n/a |
| 170 | n/a |
| 171 | n/a |
| 172 | n/a |
| 173 | n/a |
| 174 | n/a |
| 175 | n/a |
| 176 | n/a |
| 177 | n/a |
| 178 | n/a |
| 179 | n/a |
| 180 | n/a |
| 181 | n/a |
| 182 | n/a |
| 183 | n/a |
| 184 | n/a |
| 185 | n/a |
| 186 | n/a |
| 187 | n/a |
| 188 | n/a |
| 189 | n/a |
| 190 | n/a |
| 191 | n/a |
| 192 | n/a |
| 193 | n/a |
| 194 | n/a |
| 195 | n/a |
| 196 | n/a |
| 197 | n/a |
| 198 | n/a |
| 199 | n/a |
| 200 | n/a |
| 201 | n/a |
| 202 | n/a |
| 203 | n/a |
| 204 | n/a |
| 205 | n/a |
| 206 | n/a |
| 207 | n/a |
| 208 | n/a |
| 209 | n/a |
| 210 | n/a |
| 211 | n/a |
| 212 | n/a |
| 213 | n/a |
| 214 | n/a |
| 215 | n/a |
| 216 | n/a |
| 217 | n/a |
| 218 | n/a |
| 219 | n/a |
| 220 | n/a |
| 221 | n/a |
| 222 | n/a |
| 223 | n/a |
| 224 | n/a |
| 225 | n/a |
| 226 | n/a |
| 227 | n/a |
| 228 | n/a |
| 229 | n/a |
| 230 | n/a |
| 231 | n/a |
| 232 | 0.00217 |
| 233 | 0.00425 |
| 234 | n/a |
| 235 | n/a |
| 236 | n/a |
| 237 | n/a |
| 238 | n/a |
| 239 | 0.0021 |
| 240 | 0.0139 |
| 241 | n/a |
| 242 | 0.0197 |
| 243 | 0.00411 |
| 244 | n/a |
| 245 | n/a |
| 246 | n/a |
| 247 | n/a |
| 248 | n/a |
| 249 | n/a |
| 250 | n/a |
| 251 | n/a |
| 252 | n/a |
| 253 | n/a |
| 254 | n/a |
| 255 | n/a |
| 256 | n/a |
| 257 | n/a |
| 258 | n/a |
| 259 | 0.00121 |
| 260 | 0.0103 |
| 261 | 0.00229† |
| 262 | n/a |
| 263 | n/a |
| 264 | n/a |
| 265 | n/a |
| 266 | n/a |
| 267 | 0.00663 |
| 268 | n/a |
| 269 | 0.0304 |
| 270 | 0.00292 |
| 271 | n/a |
| 272 | 0.001† |
| 273 | 0.0052 |
| 274 | 0.0188 |
| 275 | 0.00389 |
| 276 | 0.0104 |
| 277 | n/a |

TABLE 42-continued

| Cmpd No. | APOL1 G2 Podocyte Rescue EC$_{50}$ (μM) |
|---|---|
| 278 | n/a |
| 279 | n/a |
| 280 | n/a |
| 281 | n/a |
| 282 | n/a |
| 283 | 0.00508 |
| 284 | 0.105 |
| 285 | n/a |
| 286 | n/a |
| 287 | 0.0177 |
| 288 | 0.0195† |
| 289 | 0.00222 |
| 290 | 0.00276† |
| 291 | n/a |
| 292 | n/a |
| 293 | n/a |
| 294 | n/a |
| 295 | n/a |
| 296 | n/a |
| 297 | n/a |
| 298 | n/a |
| 299 | n/a |
| 300 | 0.0333 |
| 301 | 0.0669 |
| 302 | n/a |
| 303 | n/a |
| 304 | n/a |
| 305 | 0.015 |
| 306 | 0.00194 |
| 307 | 0.00261† |
| 308 | n/a |
| 309 | n/a |
| 310 | n/a |
| 311 | n/a |
| 312 | n/a |
| 313 | n/a |
| 314 | 0.00457† |
| 315 | n/a |
| 316 | n/a |
| 317 | 0.00292 |
| 318 | n/a |
| 319 | n/a |
| 320 | n/a |
| 321 | 0.00765 |
| 322 | n/a |
| 323 | 0.00202 |
| 324 | n/a |
| 325 | n/a |
| 326 | n/a |
| 327 | n/a |
| 328 | n/a |
| 329 | n/a |
| 330 | n/a |
| 331 | 0.0857† |
| 332 | n/a |
| 333 | n/a |
| 334 | 0.00958† |
| 335 | n/a |
| 336 | n/a |
| 338 | n/a |
| 339 | n/a |
| 340 | n/a |
| 341 | n/a |
| 342 | n/a |
| 343 | n/a |
| 344 | n/a |
| 345 | 0.0158 |
| 346 | 0.0388 |
| 347 | n/a |
| 348 | n/a |
| 349 | 0.00681 |
| 350 | 0.0103 |
| 351 | n/a |
| 352 | 0.00112 |
| 353 | n/a |
| 354 | n/a |
| 355 | n/a |
| 356 | 0.0215 |
| 357 | 0.00404 |
| 358 | 0.024 |
| 359 | n/a |
| 360 | n/a |
| 361 | n/a |
| 362 | n/a |
| 363 | n/a |
| 364 | n/a |
| 365 | n/a |
| 366 | n/a |
| 367 | n/a |
| 368 | n/a |
| 369 | n/a |
| 370 | n/a |
| 371 | 0.0011 |
| 372 | n/a |
| 373 | n/a |
| 374 | n/a |
| 375 | n/a |
| 376 | 0.00621 |
| 377 | 0.0244 |
| 378 | n/a |
| 379 | n/a |
| 380 | n/a |
| 381 | n/a |
| 382 | n/a |
| 383 | n/a |
| 384 | n/a |
| 385 | n/a |
| 386 | n/a |
| 387 | n/a |
| 388 | n/a |
| 389 | n/a |
| 390 | n/a |
| 391 | n/a |
| 392 | n/a |
| 393 | 0.023 |
| 394 | 0.0169 |
| 395 | 0.137 |
| 396 | 0.0186 |
| 397 | 0.0143 |
| 398 | n/a |
| 399 | n/a |
| 400 | n/a |
| 401 | 0.00462 |
| 402 | n/a |
| 403 | n/a |
| 404 | n/a |
| 405 | n/a |
| 406 | n/a |
| 407 | n/a |
| 408 | 0.00705 |
| 409 | n/a |
| 410 | n/a |
| 411 | 0.00145 |
| 412 | n/a |
| 413 | n/a |
| 414 | n/a |
| 415 | n/a |
| 416 | n/a |
| 417 | n/a |
| 418 | n/a |
| 419 | n/a |
| 420 | n/a |
| 421 | n/a |
| 422 | n/a |
| 423 | n/a |
| 424 | n/a |
| 425 | n/a |
| 426 | 0.0041 |
| 427 | 0.00195 |
| 428 | 0.0122 |
| 429 | n/a |
| 430 | n/a |
| 431 | n/a |
| 432 | n/a |
| 433 | 0.00213 |
| 434 | 0.0015 |

TABLE 42-continued

| Cmpd No. | APOL1 G2 Podocyte Rescue $EC_{50}$ (µM) |
|---|---|
| 435 | 0.00294 |
| 436 | n/a |
| 437 | n/a |
| 438 | n/a |
| 439 | 0.00392 |
| 440 | 0.015 |
| 441 | n/a |
| 442 | 0.00116 |
| 443 | 0.0025 |
| 444 | n/a |
| 445 | n/a |
| 446 | n/a |
| 447 | n/a |
| 448 | n/a |
| 449 | n/a |
| 450 | 0.000846 |
| 451 | n/a |
| 452 | n/a |
| 453 | 0.00181 |
| 454 | 0.00434 |
| 455 | n/a |
| 456 | n/a |
| 457 | n/a |
| 458 | n/a |
| 459 | n/a |
| 460 | n/a |
| 461 | n/a |
| 462 | n/a |
| 463 | n/a |
| 464 | 0.000659 |
| 465 | 0.00122 |
| 466 | n/a |
| 467 | n/a |
| 468 | n/a |
| 469 | n/a |
| 470 | n/a |
| 471 | n/a |
| 472 | n/a |

Example B5

APOL1 G0/G1/G2 viability assay for measurement of cytotoxicity reversal by compound in trypanosomes (APOL1 G0/G1/G2 trypanosome cell rescue assay). This example shows that the compounds of the present disclosure are able to reverse cytotoxicity in trypanosomes.

APOL1 protein expression and purification. The mature from of APOL1 proteins, residues 28-398, were expressed from a pET28a vector with an N-terminal His-tag and TEV cleavage site. Proteins were expressed in *Escherichia coli* BL21-CodonPlus (DE3)-RIPL cells. Liter cultures of terrific broth were grown at 37° C. until an OD600 of ~0.8 was reached and then induced with isopropyl β-D-1-thiogalactopyranoside (IPTG; final concentration of 500 µM). Afterwards, cultures were grown for 3 hours at 37° C. For protein purification, cell pellets were resuspended in lysis buffer (50 mM Tris, pH 8.5, 5 mM EDTA, 0.5 mM DTT, 0.5 mM PMSF) supplemented with a cocktail of protease inhibitors. Cells were lysed by sonication, centrifuged, and the resulting pellet was collected. The homogenized pellet was resuspended in wash buffer (50 mM Tris, pH 8.5, 0.5 M NaCl, 5 mM EDTA, 0.5 mM DTT, 0.5 mM PMSF, protease inhibitor cocktail) and collected by centrifugation. Inclusion body dissolution was then conducted as previously reported (PNAS 112(9) (2015) 2894-2899; www.pnas.org/cgi/doi/10.1073/pnas.1421953112; herein incorporated by reference in its entirety). The solubilized APOL1 protein was applied to a nickel column (HisTrap, GE Life Sciences) preequilibrated in buffer A (50 mM Tris, pH 8.5, 0.15 M NaCl, 1% zwittergent 3-14, protease inhibitor cocktail). The resin was washed with buffer B (50 mM Tris, pH 8.5, 0.15 M NaCl, 0.1% DDM) and TEV cleavage was conducted on column overnight. Afterwards, the column was washed with buffer B, followed by His-washing buffer (50 mM Tris, pH 8.5, 0.15 M NaCl, 0.1% DDM, 10 mM imidazole). The protein was then removed from the resin using His-elution buffer (50 mM Tris, pH 8.5, 0.15 M NaCl, 0.1% DDM, 250 mM imidazole). The sample was further purified by size exclusion chromatography using a Superdex 200 Increase column (GE Life Sciences) in 50 mM Tris, pH 8.5, 0.15 M NaCl, and 0.1% DDM buffer. All APOL1 proteins (G0, G1, and G2) were generated at Viva Biotech (Shanghai) Ltd.

Modified HMI-9 media preparation (https://tryps.rockefeller.edu/trypsru2_culture_media_preparation.html; herein incorporated by reference in its entirety). Trypanosomes were cultured in modified HMI-9 media consisting of IMDM (ThermoFisher, 12440053), 10% heat-inactivated FBS (Gibco, 10082-147), 10% Serum Plus (Sigma-Aldrich, 14008C), 1×HMI-9 supplement stock, and 1% hypoxanthine stock. The 10×HMI-9 supplement stock was made by dissolving 280 mg bathocuproine disulfonic acid (Sigma-Aldrich, 146625), 1820 mg cysteine (add after bathocuproine) (Sigma-Aldrich, 30089), 1100 mg pyruvic acid (Sigma-Aldrich, 107360), 100 mg uracil (Sigma-Aldrich, U0750), 100 mg cytosine (Sigma-Aldrich, C3506) and 140 µL 2-mercaptoethanol (Sigma-Aldrich, M3148) in 1000 mL of water. The resulting solution was aliquoted and stored at −20° C. The hypoxanthine stock was made by dissolving 4 g of NaOH into 1000 mL of water. Afterwards, 13.6 g hypoxanthine (Sigma-Aldrich, H9377) was added to this mixture. The resulting solution was aliquoted and stored at −20° C.

Assay Setup. *Trypanosoma brucei* Lister 427 VSG221 (ATCC, PRA-382) cells were cultured in modified HMI-9 media. All experiments were performed in 384-well, white, solid bottom, tissue culture treated plates (Greiner, 781080). Assay ready plates were generated with duplicate 11-point compound dilution series that consisted of 2-fold stepwise dilutions (0.4% DMSO final). To each well, was added 20 µL of 2 µg/mL of APOL1 G0, G1, or G2 recombinant protein in modified HMI-9 media using a MultiDrop Combi (final APOL1 protein concentration=1 g/mL). Trypanosomes were counted using a hemacytometer and diluted in modified HMI-9 media to a concentration of $1.25×10^4$ cell/mL. 20 µL of this trypanosome suspension was added to each well to give a total assay volume of 40 µL and a final cell count of 250 trypanosomes/well. Plates were centrifuged at 1000 rpm for 1 minute and then incubated for 20 hours (humidified, 37° C. with 5% $CO_2$). After incubation, the plates were equilibrated at room temperature for 1 hour. Next, 20 µL of CellTiter-Glo® reagent (Promega, G7570) was added to each well. Plates were sealed and placed on an orbital shaker (500 rpm) for 5 minutes to induce cell lysis. The plates were centrifuged at 1000 rpm for 1 minute and then incubated at room temperature for an additional 10 minutes. Luminescence signal was measured on an Envision plate reader. Collaborative Drug Discovery software was utilized for graphing data.

Table 43 below provides the results from this experiment. Unless otherwise specified, $EC_{50}$ values are reported as the geometric mean of at least 2 assay runs on separate days. Each run represents the average of a technical replicate, where each compound was assayed twice in the same plate. A superscript t symbol indicates a value from the average of a technical replicate from a single assay run, where each compound was assayed twice in the same plate. Compounds in Table 43 are referred to by the corresponding Compound Number in Table 1, which is also referred to in the synthetic examples. When one or more of the numbered compounds are identified by stereochemistry (for example, (R)- or (S)-), the specific stereoisomer for which data is provided in Table 43 may be identified by the elution order of such compound as described in the synthetic examples. Absolute stereochemistry of such compounds may be identified by methods known in the art. For Table 43 below, n/a represents "not available".

Rescue $EC_{50}$ values reported in Table 43 below represent the half-maximal effective concentration for reversal of cell death caused by overexpression of APOL1. This example demonstrates that compounds of the present disclosure are able to reduce cell death caused by overexpression of APOL1 at sub micromolar concentration.

TABLE 43

| Cmpd No. | APOL1 G1 Trypanosome Rescue $EC_{50}$ (μM) | APOL1 G2 Trypanosome Rescue $EC_{50}$ (μM) | APOL1 G0 Trypanosome Rescue $EC_{50}$ (μM) |
|---|---|---|---|
| 1 | 0.293 | 0.0896 | 0.225 |
| 2 | 0.191 | 0.0563 | 0.192 |
| 3 | 0.323 | 0.092 | 0.248 |
| 4 | 0.171 | 0.0519 | 0.116 |
| 5 | 0.171 | 0.052 | 0.15 |
| 6 | 0.47 | 0.137 | 0.381 |
| 7 | n/a | n/a | n/a |
| 8 | n/a | n/a | n/a |
| 9 | >4.00 | 1.32 | >4.00 |
| 10 | 0.352† | 0.0933 | 0.351† |
| 11 | n/a | n/a | n/a |
| 12 | 1.95 | 0.494 | 1.93 |
| 13 | >4.00 | >4.00 | >4.00 |
| 14 | 0.488 | 0.127 | 0.378 |
| 15 | 0.342 | 0.124† | 0.336† |
| 16 | 0.312 | 0.11 | 0.267 |
| 17 | 0.148 | 0.0367 | 0.108 |
| 18 | 1.54 | 0.234 | 0.69 |
| 19 | n/a | n/a | n/a |
| 20 | 0.949 | 0.263 | 0.798 |
| 21 | n/a | n/a | n/a |
| 22 | n/a | n/a | n/a |
| 23 | 0.612† | 0.113† | 0.321 |
| 24 | 0.759† | 0.163† | 0.513† |
| 25 | >4.00 | 1.23 | >4.00 |
| 26 | >4.00 | >4.00 | >4.00 |
| 27 | 0.269† | 0.0663† | 0.201 |
| 28 | n/a | n/a | n/a |
| 29 | n/a | n/a | n/a |
| 30 | n/a | n/a | n/a |
| 31 | n/a | n/a | n/a |
| 32 | n/a | n/a | n/a |
| 33 | n/a | n/a | n/a |
| 34 | n/a | n/a | n/a |
| 35 | >4.00 | >4.00† | >4.00† |
| 36 | >4.00 | 1.71 | >4.00 |
| 37 | n/a | n/a | n/a |
| 38 | n/a | n/a | n/a |
| 39 | 0.206 | 0.053 | 0.156 |
| 40 | n/a | n/a | n/a |
| 41 | n/a | n/a | n/a |
| 42 | 1.88 | 0.406 | 1.26 |
| 43 | 0.0866 | 0.0194 | 0.0522 |
| 44 | 0.429 | 0.119 | 0.331 |
| 45 | 0.747 | 0.162 | 0.476 |
| 46 | 0.215 | 0.0505 | 0.156 |
| 47 | n/a | n/a | n/a |
| 48 | n/a | n/a | n/a |
| 49 | 0.304 | 0.109 | 0.213 |
| 50 | 0.0449 | 0.0102 | 0.03 |
| 51 | n/a | n/a | n/a |
| 52 | n/a | n/a | n/a |
| 53 | 0.157 | 0.0478 | 0.156 |
| 54 | n/a | n/a | n/a |
| 55 | n/a | n/a | n/a |
| 56 | 0.319 | 0.119 | 0.296 |
| 57 | 0.672 | 0.183 | 0.673 |
| 58 | n/a | n/a | n/a |
| 59 | n/a | n/a | n/a |
| 60 | 0.228 | 0.066 | 0.189 |
| 61 | n/a | n/a | n/a |
| 62 | 0.39 | 0.12 | 0.407 |
| 63 | 0.164† | 0.0409† | 0.118 |
| 64 | 0.712 | 0.167 | 0.503 |

TABLE 43-continued

| Cmpd No. | APOL1 G1 Trypanosome Rescue EC$_{50}$ (μM) | APOL1 G2 Trypanosome Rescue EC$_{50}$ (μM) | APOL1 G0 Trypanosome Rescue EC$_{50}$ (μM) |
|---|---|---|---|
| 65 | 0.294 | 0.0968 | 0.318 |
| 66 | 0.322 | 0.0976 | 0.246 |
| 67 | n/a | n/a | n/a |
| 68 | 0.441 | 0.115 | 0.358 |
| 69 | 0.184† | 0.0465† | 0.153† |
| 70 | >4.00† | 0.918† | >4.00† |
| 71 | 1.36† | 0.205† | 0.814† |
| 72 | 0.177 | 0.0457 | 0.128 |
| 73 | n/a | n/a | n/a |
| 74 | n/a | n/a | n/a |
| 75 | 0.578 | 0.146 | 0.383 |
| 76 | 0.126 | 0.0355 | 0.106 |
| 77 | >4.00 | 1.45 | >4.00 |
| 78 | 0.0976 | 0.0326 | 0.0952 |
| 79 | 0.952 | 0.293 | 0.846 |
| 80 | n/a | n/a | n/a |
| 81 | n/a | n/a | n/a |
| 82 | 0.344 | 0.113 | 0.254 |
| 83 | n/a | n/a | n/a |
| 84 | 0.144 | 0.05 | 0.101 |
| 85 | 0.19 | 0.0485 | 0.115 |
| 86 | 0.137 | 0.0384 | 0.0964 |
| 87 | 0.383 | 0.0958 | 0.268 |
| 88 | 0.561 | 0.138 | 0.451 |
| 89 | 0.114 | 0.0327 | 0.101 |
| 90 | 0.679 | 0.163 | 0.546 |
| 91 | 0.0827 | 0.0204 | 0.0546 |
| 92 | 0.0993 | 0.0285 | 0.0844 |
| 93 | 0.264 | 0.0569 | 0.156 |
| 94 | 0.424 | 0.129 | 0.403 |
| 95 | 0.703 | 0.222 | 0.592 |
| 96 | 0.143 | 0.053 | 0.122 |
| 97 | 0.0984 | 0.0406 | 0.099 |
| 98 | 0.259 | 0.0722 | 0.207 |
| 99 | 0.346 | 0.0901 | 0.216 |
| 100 | 0.113 | 0.0259 | 0.0635 |
| 101 | 0.2 | 0.0694 | 0.195 |
| 102 | 0.0505 | 0.018 | 0.0473 |
| 103 | 0.17 | 0.0437 | 0.113 |
| 104 | 0.726 | 0.184 | 0.583 |
| 105 | 0.274 | 0.0752 | 0.217 |
| 106 | 0.0918 | 0.0234 | 0.069 |
| 107 | 0.0935 | 0.023 | 0.0572 |
| 108 | 0.0307 | 0.00922 | 0.0233 |
| 109 | 0.385 | 0.098 | 0.32 |
| 110 | 0.0877 | 0.0261 | 0.0714 |
| 111 | 0.362 | 0.105 | 0.282 |
| 112 | 0.0696 | 0.0183 | 0.0582 |
| 113 | 0.154 | 0.0467 | 0.124 |
| 114 | 0.104 | 0.038 | 0.108 |
| 115 | n/a | n/a | n/a |
| 116 | 0.209 | 0.0692 | 0.149 |
| 117 | 0.423 | 0.117 | 0.309 |
| 118 | n/a | n/a | n/a |
| 119 | n/a | n/a | n/a |
| 120 | 1.25 | 0.346 | 0.807 |
| 121 | n/a | n/a | n/a |
| 122 | 0.337 | 0.108 | 0.252 |
| 123 | 0.258 | 0.0769 | 0.178 |
| 124 | n/a | n/a | n/a |
| 125 | n/a | n/a | n/a |
| 126 | n/a | n/a | n/a |
| 127 | 0.0839 | 0.0294 | 0.0649 |
| 128 | 0.383 | 0.133 | 0.269 |
| 129 | 0.0695 | 0.0222 | 0.0652 |
| 130 | n/a | n/a | n/a |
| 131 | 0.176 | 0.0478 | 0.132 |
| 132 | 0.731 | 0.18 | 0.525 |
| 133 | n/a | n/a | n/a |
| 134 | 0.991 | 0.277 | 0.851 |
| 135 | 1.2 | 0.303 | 1.08 |
| 136 | 0.0371 | 0.0143 | 0.0315 |
| 137 | 0.454 | 0.119 | 0.322 |
| 138 | 0.585 | 0.165 | 0.326 |
| 139 | 0.537 | 0.147 | 0.335 |
| 140 | 0.653 | 0.164 | 0.408 |

TABLE 43-continued

| Cmpd No. | APOL1 G1 Trypanosome Rescue EC$_{50}$ (μM) | APOL1 G2 Trypanosome Rescue EC$_{50}$ (μM) | APOL1 G0 Trypanosome Rescue EC$_{50}$ (μM) |
| --- | --- | --- | --- |
| 141 | n/a | n/a | n/a |
| 142 | 0.0983 | 0.0353 | 0.0635 |
| 143 | 0.0641 | 0.0211 | 0.0411 |
| 144 | 0.358 | 0.101 | 0.224 |
| 145 | 0.118 | 0.0355 | 0.0865 |
| 146 | 0.427 | 0.119 | 0.346 |
| 147 | 0.231 | 0.0654 | 0.155 |
| 148 | 0.201 | 0.0618 | 0.14 |
| 149 | 0.174 | 0.0518 | 0.117 |
| 150 | 2.29 | 0.519 | 1.44 |
| 151 | 1.33 | 0.347 | 1.04 |
| 152 | 1.53 | 0.416 | 1.05 |
| 153 | 0.0667 | 0.0256 | 0.0522 |
| 154 | 0.569 | 0.16 | 0.328 |
| 155 | 0.0361 | 0.00965 | 0.0259 |
| 156 | 0.154 | 0.0448 | 0.0966 |
| 157 | 0.142 | 0.0451 | 0.109 |
| 158 | 0.142 | 0.0459 | 0.0942 |
| 159 | n/a | n/a | n/a |
| 160 | 0.156 | 0.0423 | 0.109 |
| 161 | 0.107 | 0.0333 | 0.0763 |
| 162 | 0.142 | 0.0509 | 0.143 |
| 163 | 0.09 | 0.0212 | 0.0559 |
| 164 | 0.349 | 0.0871 | 0.211 |
| 165 | 0.0338 | 0.0111 | 0.0287 |
| 166 | 0.112 | 0.0338 | 0.094 |
| 167 | 0.148 | 0.035 | 0.0984 |
| 168 | 0.638 | 0.191 | 0.496 |
| 169 | 0.918 | 0.295 | 0.619 |
| 170 | n/a | n/a | n/a |
| 171 | n/a | n/a | n/a |
| 172 | 0.353 | 0.108 | 0.246 |
| 173 | n/a | n/a | n/a |
| 174 | 0.481 | 0.137 | 0.401 |
| 175 | n/a | n/a | n/a |
| 176 | 0.177 | 0.0446 | 0.12 |
| 177 | 0.314 | 0.0844 | 0.26 |
| 178 | n/a | n/a | n/a |
| 179 | n/a | n/a | n/a |
| 180 | 0.0477 | 0.0133 | 0.0352 |
| 181 | 0.232 | 0.0707 | 0.158 |
| 182 | 0.481 | 0.138 | 0.401 |
| 183 | n/a | n/a | n/a |
| 184 | 2.08 | 0.585 | 1.6 |
| 185 | 0.479 | 0.14 | 0.31 |
| 186 | n/a | n/a | n/a |
| 187 | n/a | n/a | n/a |
| 188 | 0.0965 | 0.0267 | 0.071 |
| 189 | 0.246 | 0.0614 | 0.167 |
| 190 | 0.104 | 0.0357 | 0.0921 |
| 191 | 0.304 | 0.104 | 0.251 |
| 192 | 0.142 | 0.0491 | 0.108 |
| 193 | 0.288 | 0.0702 | 0.2 |
| 194 | n/a | n/a | n/a |
| 195 | 0.0744 | 0.0198 | 0.0482 |
| 196 | 0.185 | 0.0603 | 0.16 |
| 197 | 0.193 | 0.0106 | 0.0303 |
| 198 | 0.142 | 0.0419 | 0.107 |
| 199 | n/a | n/a | n/a |
| 200 | 0.192 | 0.0724 | 0.185 |
| 201 | n/a | n/a | n/a |
| 202 | n/a | n/a | n/a |
| 203 | 0.583 | 0.227 | 0.565 |
| 204 | n/a | n/a | n/a |
| 205 | n/a | n/a | n/a |
| 206 | n/a | n/a | n/a |
| 207 | n/a | n/a | n/a |
| 208 | n/a | n/a | n/a |
| 209 | n/a | n/a | n/a |
| 210 | 0.0711 | 0.0218 | 0.0638 |
| 211 | 0.527 | 0.159 | 0.48 |
| 212 | 0.103 | 0.0321 | 0.0696 |
| 213 | n/a | n/a | n/a |
| 214 | 0.43 | 0.0887 | 0.25 |
| 215 | 0.097 | 0.0224 | 0.0701 |
| 216 | 0.912 | 0.231 | 0.629 |

TABLE 43-continued

| Cmpd No. | APOL1 G1 Trypanosome Rescue EC$_{50}$ (μM) | APOL1 G2 Trypanosome Rescue EC$_{50}$ (μM) | APOL1 G0 Trypanosome Rescue EC$_{50}$ (μM) |
|---|---|---|---|
| 217 | n/a | n/a | n/a |
| 218 | 0.108 | 0.0316 | 0.0651 |
| 219 | 0.039 | 0.0105 | 0.0223 |
| 220 | n/a | n/a | n/a |
| 221 | 0.129 | 0.0295 | 0.075 |
| 222 | n/a | n/a | n/a |
| 223 | n/a | n/a | n/a |
| 224 | 0.0928 | 0.0327 | 0.066 |
| 225 | 0.0508 | 0.0129 | 0.0352 |
| 226 | 0.112 | 0.036 | 0.08 |
| 227 | 0.248 | 0.0616 | 0.142 |
| 228 | 0.363 | 0.0862 | 0.196 |
| 229 | 0.778 | 0.186 | 0.417 |
| 230 | 0.801 | 0.209 | 0.427 |
| 231 | 0.231 | 0.0667 | 0.135 |
| 232 | 0.157 | 0.0416 | 0.0976 |
| 233 | 0.134 | 0.0411 | 0.0817 |
| 234 | 0.475 | 0.146 | 0.272 |
| 235 | 0.452 | 0.132 | 0.27 |
| 236 | 0.866 | 0.397 | 0.766 |
| 237 | 0.196 | 0.0572 | 0.132 |
| 238 | >4.00 | 0.763 | 1.59 |
| 239 | 0.0488 | 0.0148 | 0.04 |
| 240 | n/a | n/a | n/a |
| 241 | 0.258 | 0.0633 | 0.177 |
| 242 | n/a | n/a | n/a |
| 243 | n/a | n/a | n/a |
| 244 | 0.151 | 0.0493 | 0.141 |
| 245 | 0.379 | 0.102 | 0.265 |
| 246 | n/a | n/a | n/a |
| 247 | 0.246 | 0.081 | 0.186 |
| 248 | 0.126 | 0.0379 | 0.0862 |
| 249 | 0.0738 | 0.0221 | 0.0538 |
| 250 | 0.678 | 0.194 | 0.445 |
| 251 | 1.12 | 0.24 | 0.903 |
| 252 | n/a | n/a | n/a |
| 253 | n/a | n/a | n/a |
| 254 | 0.951 | 0.252 | 0.695 |
| 255 | 2.92 | 0.575 | 1.38 |
| 256 | n/a | n/a | n/a |
| 257 | n/a | n/a | n/a |
| 258 | n/a | n/a | n/a |
| 259 | 0.0922 | 0.0255 | 0.068 |
| 260 | 0.397 | 0.11 | 0.274 |
| 261 | 0.1 | 0.0296 | 0.084 |
| 262 | n/a | n/a | n/a |
| 263 | 0.32 | 0.0953 | 0.226 |
| 264 | n/a | n/a | n/a |
| 265 | 0.105 | 0.0231 | 0.0676 |
| 266 | 0.407 | 0.0771 | 0.236 |
| 267 | 0.115 | 0.0337 | 0.0954 |
| 268 | 0.121 | 0.0327 | 0.108 |
| 269 | 0.277 | 0.0797 | 0.207 |
| 270 | 0.0822 | 0.0253 | 0.0725 |
| 271 | 0.0507 | 0.0159 | 0.051 |
| 272 | 0.0732 | 0.0189 | 0.0589 |
| 273 | 0.0716 | 0.0258 | 0.0649 |
| 274 | 0.0584 | 0.0172 | 0.0593 |
| 275 | 0.0736 | 0.0214 | 0.0612 |
| 276 | 0.185 | 0.055 | 0.178 |
| 277 | n/a | n/a | n/a |
| 278 | 0.111 | 0.0255 | 0.114 |
| 279 | 0.283 | 0.0831 | 0.213 |
| 280 | n/a | n/a | n/a |
| 281 | 0.101 | 0.0281 | 0.0959 |
| 282 | 0.23 | 0.0598 | 0.181 |
| 283 | 0.235 | 0.0711 | 0.216 |
| 284 | 0.943 | 0.235 | 0.808 |
| 285 | 0.749 | 0.212 | 0.547 |
| 286 | 0.629 | 0.175 | 0.505 |
| 287 | 0.05[†] | 0.0139[†] | 0.0376[†] |
| 288 | 0.0361[†] | 0.00975[†] | 0.0262[†] |
| 289 | 0.0519 | 0.0157 | 0.0382 |
| 290 | 0.0692 | 0.024 | 0.0555 |
| 291 | 0.0797 | 0.0265 | 0.0631 |
| 292 | 0.0396 | 0.0108 | 0.0316 |

TABLE 43-continued

| Cmpd No. | APOL1 G1 Trypanosome Rescue EC$_{50}$ (μM) | APOL1 G2 Trypanosome Rescue EC$_{50}$ (μM) | APOL1 G0 Trypanosome Rescue EC$_{50}$ (μM) |
| --- | --- | --- | --- |
| 293 | n/a | n/a | n/a |
| 294 | 0.089 | 0.0214 | 0.0619 |
| 295 | 0.0402 | 0.0111 | 0.0326 |
| 296 | n/a | n/a | n/a |
| 297 | 0.0854 | 0.0315 | 0.0726 |
| 298 | 0.156 | 0.0566 | 0.119 |
| 299 | n/a | n/a | n/a |
| 300 | 0.543 | 0.16 | 0.375 |
| 301 | 0.447 | 0.134 | 0.327 |
| 302 | 0.498 | 0.142 | 0.356 |
| 303 | n/a | n/a | n/a |
| 304 | n/a | n/a | n/a |
| 305 | 0.265 | 0.0804 | 0.187 |
| 306 | 0.0508 | 0.015 | 0.037 |
| 307 | 0.0797 | 0.0272 | 0.0657 |
| 308 | 0.435 | 0.15 | 0.335 |
| 309 | 0.0706 | 0.0234 | 0.0582 |
| 310 | n/a | n/a | n/a |
| 311 | 0.0503 | 0.0138 | 0.0374 |
| 312 | 0.0344 | 0.0101 | 0.0282 |
| 313 | 0.0718 | 0.0202 | 0.0545 |
| 314 | 0.0349 | 0.0115 | 0.0254 |
| 315 | n/a | n/a | n/a |
| 316 | n/a | n/a | n/a |
| 317 | 0.0335 | 0.0115 | 0.033 |
| 318 | n/a | n/a | n/a |
| 319 | 0.0811 | 0.027 | 0.0697 |
| 320 | n/a | n/a | n/a |
| 321 | 0.0459 | 0.0143 | 0.0396 |
| 322 | 0.0349 | 0.0117 | 0.0293 |
| 323 | 0.0359 | 0.0118 | 0.032 |
| 324 | 0.035 | 0.00831 | 0.0289 |
| 325 | 0.269 | 0.0775 | 0.213 |
| 326 | 0.0944 | 0.0327 | 0.0886 |
| 327 | 0.0466 | 0.0134 | 0.0399 |
| 328 | 0.0921 | 0.0239 | 0.0799 |
| 329 | 0.24 | 0.0673 | 0.199 |
| 330 | n/a | n/a | n/a |
| 331 | n/a | n/a | n/a |
| 332 | n/a | n/a | n/a |
| 333 | 0.205† | 0.074† | 0.152† |
| 334 | n/a | n/a | n/a |
| 335 | n/a | n/a | n/a |
| 336 | n/a | n/a | n/a |
| 338 | n/a | n/a | n/a |
| 339 | n/a | n/a | n/a |
| 340 | n/a | n/a | n/a |
| 341 | n/a | n/a | n/a |
| 342 | n/a | n/a | n/a |
| 343 | 0.203† | 0.0642† | 0.174† |
| 344 | n/a | n/a | n/a |
| 345 | 0.242† | 0.0802† | 0.161† |
| 346 | 0.116† | 0.0377† | 0.0836† |
| 347 | n/a | n/a | n/a |
| 348 | n/a | n/a | n/a |
| 349 | 0.0898† | 0.0331† | 0.0646† |
| 350 | n/a | n/a | n/a |
| 351 | n/a | n/a | n/a |
| 352 | 0.0188 | 0.00822 | 0.0187 |
| 353 | n/a | n/a | n/a |
| 354 | n/a | n/a | n/a |
| 355 | n/a | n/a | n/a |
| 356 | 0.113† | 0.0374† | 0.101† |
| 357 | 0.0916 | 0.0281 | 0.0612 |
| 358 | 0.0752 | 0.0313 | 0.0621 |
| 359 | n/a | n/a | n/a |
| 360 | n/a | n/a | n/a |
| 361 | n/a | n/a | n/a |
| 362 | n/a | n/a | n/a |
| 363 | n/a | n/a | n/a |
| 364 | 0.203 | 0.0923 | 0.155 |
| 365 | n/a | n/a | n/a |
| 366 | 0.0873 | 0.0324 | 0.0664 |
| 367 | 0.323 | 0.106 | 0.231 |
| 368 | n/a | n/a | n/a |
| 369 | n/a | n/a | n/a |

TABLE 43-continued

| Cmpd No. | APOL1 G1 Trypanosome Rescue EC$_{50}$ (μM) | APOL1 G2 Trypanosome Rescue EC$_{50}$ (μM) | APOL1 G0 Trypanosome Rescue EC$_{50}$ (μM) |
| --- | --- | --- | --- |
| 370 | n/a | n/a | n/a |
| 371 | 0.0219 | 0.00916 | 0.0188 |
| 372 | n/a | n/a | n/a |
| 373 | n/a | n/a | n/a |
| 374 | n/a | n/a | n/a |
| 375 | n/a | n/a | n/a |
| 376 | 0.115† | 0.0399† | 0.0956† |
| 377 | 0.271† | 0.0978† | 0.205† |
| 378 | n/a | n/a | n/a |
| 379 | n/a | n/a | n/a |
| 380 | n/a | n/a | n/a |
| 381 | n/a | n/a | n/a |
| 382 | n/a | n/a | n/a |
| 383 | n/a | n/a | n/a |
| 384 | n/a | n/a | n/a |
| 385 | n/a | n/a | n/a |
| 386 | n/a | n/a | n/a |
| 387 | n/a | n/a | n/a |
| 388 | n/a | n/a | n/a |
| 389 | n/a | n/a | n/a |
| 390 | n/a | n/a | n/a |
| 391 | n/a | n/a | n/a |
| 392 | 0.0794† | 0.0285† | 0.07† |
| 393 | 0.36† | 0.12† | 0.3† |
| 394 | n/a | n/a | n/a |
| 395 | 0.312 | 0.106 | 0.24 |
| 396 | n/a | n/a | n/a |
| 397 | 0.269 | 0.0852 | 0.226 |
| 398 | 0.0522 | 0.018 | 0.0536 |
| 399 | n/a | n/a | n/a |
| 400 | n/a | n/a | n/a |
| 401 | n/a | n/a | n/a |
| 402 | 0.0427 | 0.0165 | 0.0336 |
| 403 | n/a | n/a | n/a |
| 404 | 0.554 | 0.21 | 0.425 |
| 405 | 0.0216 | 0.00806 | 0.02 |
| 406 | 0.128 | 0.0511 | 0.107 |
| 407 | 0.0997† | 0.033† | 0.0724 |
| 408 | 0.121 | 0.0436 | 0.0848† |
| 409 | n/a | n/a | n/a |
| 410 | 0.269 | 0.0924 | 0.206 |
| 411 | n/a | n/a | n/a |
| 412 | n/a | n/a | n/a |
| 413 | n/a | n/a | n/a |
| 414 | n/a | n/a | n/a |
| 415 | n/a | n/a | n/a |
| 416 | n/a | n/a | n/a |
| 417 | n/a | n/a | n/a |
| 418 | n/a | n/a | n/a |
| 419 | n/a | n/a | n/a |
| 420 | n/a | n/a | n/a |
| 421 | n/a | n/a | n/a |
| 422 | n/a | n/a | n/a |
| 423 | n/a | n/a | n/a |
| 424 | n/a | n/a | n/a |
| 425 | n/a | n/a | n/a |
| 426 | 0.0888 | 0.0367 | 0.071 |
| 427 | 0.0181 | 0.00662 | 0.0156 |
| 428 | 0.0719 | 0.0323 | 0.0633 |
| 429 | n/a | n/a | n/a |
| 430 | n/a | n/a | n/a |
| 431 | n/a | n/a | n/a |
| 432 | n/a | n/a | n/a |
| 433 | n/a | n/a | n/a |
| 434 | n/a | n/a | n/a |
| 435 | 0.0272† | 0.0145† | 0.0271† |
| 436 | n/a | n/a | n/a |
| 437 | n/a | n/a | n/a |
| 438 | n/a | n/a | n/a |
| 439 | 0.051† | 0.0202† | 0.0505† |
| 440 | 0.205 | 0.0705 | 0.16 |
| 441 | 0.215 | 0.0783 | 0.144 |
| 442 | n/a | n/a | n/a |
| 443 | n/a | n/a | n/a |
| 444 | n/a | n/a | n/a |
| 445 | n/a | n/a | n/a |

TABLE 43-continued

| Cmpd No. | APOL1 G1 Trypanosome Rescue EC$_{50}$ (μM) | APOL1 G2 Trypanosome Rescue EC$_{50}$ (μM) | APOL1 G0 Trypanosome Rescue EC$_{50}$ (μM) |
|---|---|---|---|
| 446 | n/a | n/a | n/a |
| 447 | n/a | n/a | n/a |
| 448 | n/a | n/a | n/a |
| 449 | n/a | n/a | n/a |
| 450 | n/a | n/a | n/a |
| 451 | n/a | n/a | n/a |
| 452 | n/a | n/a | n/a |
| 453 | n/a | n/a | n/a |
| 454 | n/a | n/a | n/a |
| 455 | n/a | n/a | n/a |
| 456 | n/a | n/a | n/a |
| 457 | n/a | n/a | n/a |
| 458 | n/a | n/a | n/a |
| 459 | 0.133 | 0.0498 | 0.101 |
| 460 | 0.118 | 0.0537 | 0.104 |
| 461 | 0.0755† | 0.0288† | 0.0692† |
| 462 | n/a | n/a | n/a |
| 463 | n/a | n/a | n/a |
| 464 | n/a | n/a | n/a |
| 465 | n/a | n/a | n/a |
| 466 | 0.0306 | 0.0119 | 0.0194 |
| 467 | 0.00603 | 0.00224 | 0.00374 |
| 468 | 0.00559 | 0.0024 | 0.00372 |
| 469 | 0.0155 | 0.00533 | 0.00976 |
| 470 | 0.0124 | 0.00441 | 0.00882 |
| 471 | n/a | n/a | n/a |
| 472 | n/a | n/a | n/a |

Example B6

APOL1 G2 mouse renal model for measurement of albuminuria prevention by compound. This example shows that the compounds of the present disclosure are able to prevent albuminuria.

APOL1 transgenic (Tg) mice with a bacterial artificial chromosome (BAC) containing APOL1 G2 and its upstream and downstream genomic regions (Taconic, Model #13022) were bred to homozygosity. APOL1 G2 homozygous (G2 HOM) male mice, greater than 6 weeks of age were utilized in experiments. All studies were conducted under a protocol approved by the Institutional Animal Care and Use Committee (IACUC).

Baseline urine samples were collected over a 24-hour period 7 days prior to the start of the experiment. Urine volume was determined by weight and stored at −80° C. until use. Afterwards, baseline blood samples were collected via submandibular bleed into serum separate (SS) tubes (BD Microtainer). Serum samples were allowed to clot at room temperature for 30 minutes prior to centrifugation at 12000 rpm, 4° C. for 5 minutes. The concentration of APOL1 was determined in these samples using an APOL1 ELISA kit (Proteintech, KE00047) according to the manufacturer's instructions.

On the day of the experiment (0 hour), mice were individually identified, weighed, and assigned to one of the treatment groups. Treatment groups had similar average levels of serum APOL1. Mice were administered with two doses of compound test article and one dose of recombinant mouse interferon gamma (mIFNγ) (MilliporeSigma, Catalog #IF005) per day for 2 days. Compound test article was administered via oral gavage at 10 mL/kg body weight dose volume at 0, approximately 10, 24, and 34 hours. mIFNγ ($1.5 \times 10^{11}$ unit/kg body weight) was administered via intraperitoneal injection at 10 mL/kg body weigh dose volume at 0 and 24 hours. Urine collection was immediately initiated after the second dose of mIFNγ. Specifically, mice were individually placed in a metabolic cage (Lab Products) for 24 hours where urine and feces were collected into separate tubes. During this time, mice had access to an enrichment toy, gel diet (Bio-serve), and drinking water (Innovive). At the end of the experiment, mice were anesthetized under isoflurane and blood was collected via cardiac puncture followed with a cervical dislocation to ensure death.

Urine samples were analyzed for urine albumin and urine creatinine levels. The concentration of urine albumin was determined using a mouse albumin immunoperoxidase assay kit (Immunology Consultants Laboratory, E-90AL) according to the manufacturer's instructions. Urine creatinine was analyzed using LC-MS methodology at WuXi App Tec (DMPK, New Jersey, USA).

Selected compounds from Table 1 described by formula (I-E) were tested in this APOL1 G2 mouse renal model for measurement of albuminuria. The results are shown in Table 44.

TABLE 44

| Compound Tested | Dose (route of administration) | Reduction in urine albumin/creatinine ratio (uACR) |
|---|---|---|
| Compound A | 0.3 mg/kg (PO, BID) | 50% |
| Compound A | 1 mg/kg (PO, BID) | 58% |
| Compound A | 3 mg/kg (PO, BID) | 75% |
| Compound B | 10 mg/kg (PO, BID) | 67% |
| Compound B | 50 mg/kg (PO, BID) | 89% |

All publications, patent applications, patents, and other references mentioned herein are expressly incorporated by reference in their entireties, to the same extent as if each were incorporated by reference individually.

It is to be understood that, while the disclosure has been described in conjunction with the above embodiments, the foregoing description and examples are intended to illustrate and not limit the scope of the disclosure. Other aspects, advantages and modifications within the scope of the disclosure will be apparent to those skilled in the art to which the disclosure pertains.

What is claimed is:
1. A compound of formula (I-E):

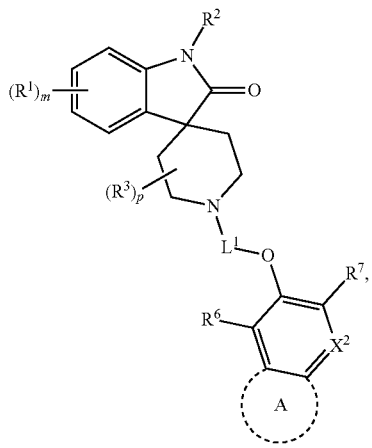

(I-E)

or a stereoisomer or tautomer thereof, or a pharmaceutically acceptable salt of any of the foregoing, wherein:
ring A is a 5-10 membered heterocyclyl or a 5-10 membered heteroaryl, wherein the 5-10 membered heterocyclyl of ring A is optionally substituted with one or more $R^b$, and
the 5-10 membered heteroaryl of ring A is optionally substituted with one or more $R^c$;
m is an integer from 0 to 4;
p is an integer from 0 to 10;
$R^1$, if present is, independently at each occurrence selected from the group consisting of halo, —CN, $C_{1-6}$alkoxy, and $C_{1-6}$alkyl, wherein
the $C_{1-6}$alkoxy of $R^1$ is optionally substituted with one or more halo, and
the $C_{1-6}$alkyl of $R^1$ is optionally substituted with one or more halo;
$R^2$ is H, $C_{1-6}$alkyl, $C_{3-10}$cycloalkyl, or 3-15 membered heterocyclyl, wherein
the $C_{1-6}$alkyl of $R^2$ is optionally substituted with one or more deuterium, halo, —OH, —NH$_2$, or $C_{1-6}$alkoxy, and
the $C_{3-10}$cycloalkyl of $R^2$ is optionally substituted with one or more —OH;
$R^3$, if present, is $C_{1-6}$alkyl;
$L^1$ is $C_{1-6}$alkylene, wherein
the $C_{1-6}$alkylene of $L^1$ is optionally substituted with one or more deuterium or $C_{1-6}$alkyl, and wherein
the $C_{1-6}$alkyl is further optionally substituted with one or more —OH or $C_{1-6}$alkoxy;
$X^2$ is N or C ($R^5$);
$R^b$ is, independently at each occurrence, selected from the group consisting of —OH, halo, oxo, $C_{1-6}$alkyl, —C(O)—$C_{1-6}$alkyl, —C(O)—NH$_2$, —C(O)—NH($C_{1-6}$alkyl), —C(O)—N($C_{1-6}$alkyl)$_2$, —S(O)$_2$—$R^a$, $C_{3-10}$cycloalkyl, and 3-10 membered heterocyclyl, wherein
the $C_{1-6}$alkyl of $R^b$ is optionally substituted with one or more halo, OH, —S(O)$_2$—$C_{1-6}$alkyl, or $C_{3-10}$cycloalkyl, and wherein the $C_{3-10}$cycloalkyl of the $C_{1-6}$alkyl of $R^b$ is further optionally substituted with one or more $C_{1-6}$alkyl or —OH and
the $C_{3-10}$cycloalkyl of $R^b$ is optionally substituted with one or more —OH, $C_{3-10}$-cycloalkyl, or $C_{1-6}$alkyl, and wherein
the $C_{1-6}$alkyl of the $C_{3-10}$cycloalkyl of $R^b$ is further optionally substituted with one or more —OH, deuterium, or halo;
$R^c$ is, independently at each occurrence, selected from the group consisting of halo, $C_{1-6}$alkyl, —C(O)—$C_{1-6}$alkyl, —C(O)—NH$_2$, —C(O)—NH($C_{1-6}$alkyl), —C(O)—N($C_{1-6}$alkyl)$_2$, —S(O)$_2$—$R^a$, $C_{3-10}$cycloalkyl, and 3-10 membered heterocyclyl, wherein
the $C_{1-6}$alkyl of $R^c$ is optionally substituted with one or more —S(O)$_2$—$C_{1-6}$alkyl,
the $C_{3-10}$cycloalkyl of $R^c$ is optionally substituted with one or more —OH or $C_{1-6}$alkyl, and
the 3-10 membered heterocyclyl of $R^c$ is optionally substituted with one or more —OH or $C_{1-6}$alkyl, and wherein
the $C_{1-6}$alkyl of the 3-10 membered heterocyclyl of $R^c$ is further optionally substituted with one or more —OH;
$R^a$ is, independently at each occurrence:
(i) $C_{1-6}$alkyl optionally substituted with one or more halo, —OH, —S(O)$_2$—$C_{1-6}$alkyl, or —N($C_{1-6}$alkyl)-C(O)—$C_{1-6}$alkyl,
(ii) $C_{3-10}$cycloalkyl optionally substituted with one or more —OH, —C(O)$_2$—$C_{1-6}$alkyl, —C(O)—NH($C_{1-6}$alkyl), —C(O)—N($C_{1-6}$alkyl)$_2$, or —C(O)—$C_{3-10}$heterocyclyl, or $C_{1-6}$alkyl, wherein
the $C_{1-6}$alkyl is optionally substituted with one or more —OH,
(iii) 3-10 membered heterocyclyl optionally substituted with one or more $C_{1-6}$alkyl, or
(iv) NH($C_{1-6}$alkyl);
$R^5$ is, independently at each occurrence, H, halo, —CN, 3-10 membered heterocyclyl, $C_{1-6}$alkyl, or $C_{1-6}$alkoxy, wherein
the $C_{1-6}$alkyl of $R^5$ is optionally substituted with one or more halo or —OH, and
the $C_{1-6}$alkoxy of $R^5$ is optionally substituted with one or more halo; and
$R^6$ and $R^7$ are each independently H or halo.
2. The compound of claim 1, or a stereoisomer or tautomer thereof, or a pharmaceutically acceptable salt of any of the foregoing, wherein the compound is a compound of formula (I-E4):

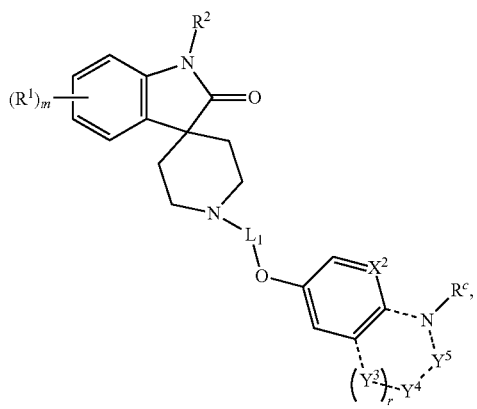

(I-E4)

or a stereoisomer or tautomer thereof, or a pharmaceutically acceptable salt of any of the foregoing, wherein:
r is an integer from 0-1; and
$Y^3$, $Y^4$, and $Y^5$ are each independently C or N, optionally substituted by one or more H or $R^c$, and wherein the dashed line represents a single or double bond.

3. The compound of claim 1, or a stereoisomer or tautomer thereof, or a pharmaceutically acceptable salt of any of the foregoing, wherein $R^2$ is H, $C_{1-3}$alkyl, $C_{3-6}$cycloalkyl, or 3-10 membered heterocyclyl, wherein the $C_{1-3}$alkyl of $R^2$ is optionally substituted with one or more deuterium, halo, —OH, —$NH_2$, or $C_{1-3}$alkoxy, and the $C_{3-6}$cycloalkyl of $R^2$ is optionally substituted with one or more —OH.

4. The compound of claim 1, or a stereoisomer or tautomer thereof, or a pharmaceutically acceptable salt of any of the foregoing, wherein m is 0, 1, or 2.

5. The compound of claim 1, or a stereoisomer or tautomer thereof, or a pharmaceutically acceptable salt of any of the foregoing, wherein $R^1$ is halo, —CN, —$C_{1-3}$alkoxy, or —$C_{1-3}$alkyl, wherein
the $C_{1-3}$alkoxy of $R^1$ is optionally substituted with one or more halo, and
the $C_{1-3}$alkyl of $R^1$ is optionally substituted with one or more halo.

6. The compound of claim 1, or a stereoisomer or tautomer thereof, or a pharmaceutically acceptable salt of any of the foregoing, wherein p is 0 or 1.

7. The compound of claim 1, or a stereoisomer or tautomer thereof, or a pharmaceutically acceptable salt of any of the foregoing, wherein $L^1$ is selected from the group consisting of

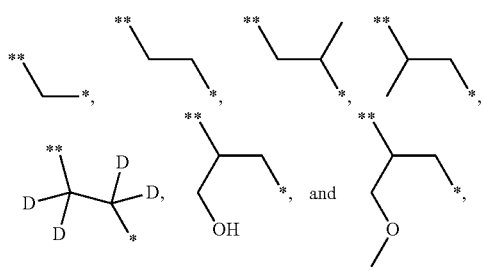

wherein, for each $L^1$, * denotes the point of attachment to —O— and ** denotes the point of attachment to the remainder of the molecule.

8. The compound of claim 1, or a stereoisomer or tautomer thereof, or a pharmaceutically acceptable salt of any of the foregoing, wherein $X^2$ is $C(R^5)$.

9. The compound of claim 1, or a stereoisomer or tautomer thereof, or a pharmaceutically acceptable salt of any of the foregoing, wherein $X^2$ is N.

10. The compound of claim 1, or a stereoisomer or tautomer thereof, or a pharmaceutically acceptable salt of any of the foregoing, wherein ring A is a 5-10 membered heterocyclyl optionally substituted with one or more $R^b$.

11. The compound of claim 10, or a stereoisomer or tautomer thereof, or a pharmaceutically acceptable salt of any of the foregoing, wherein ring A is selected from the group consisting of

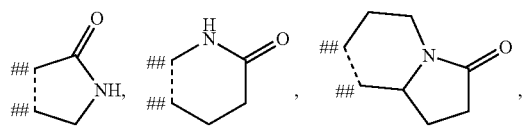

-continued

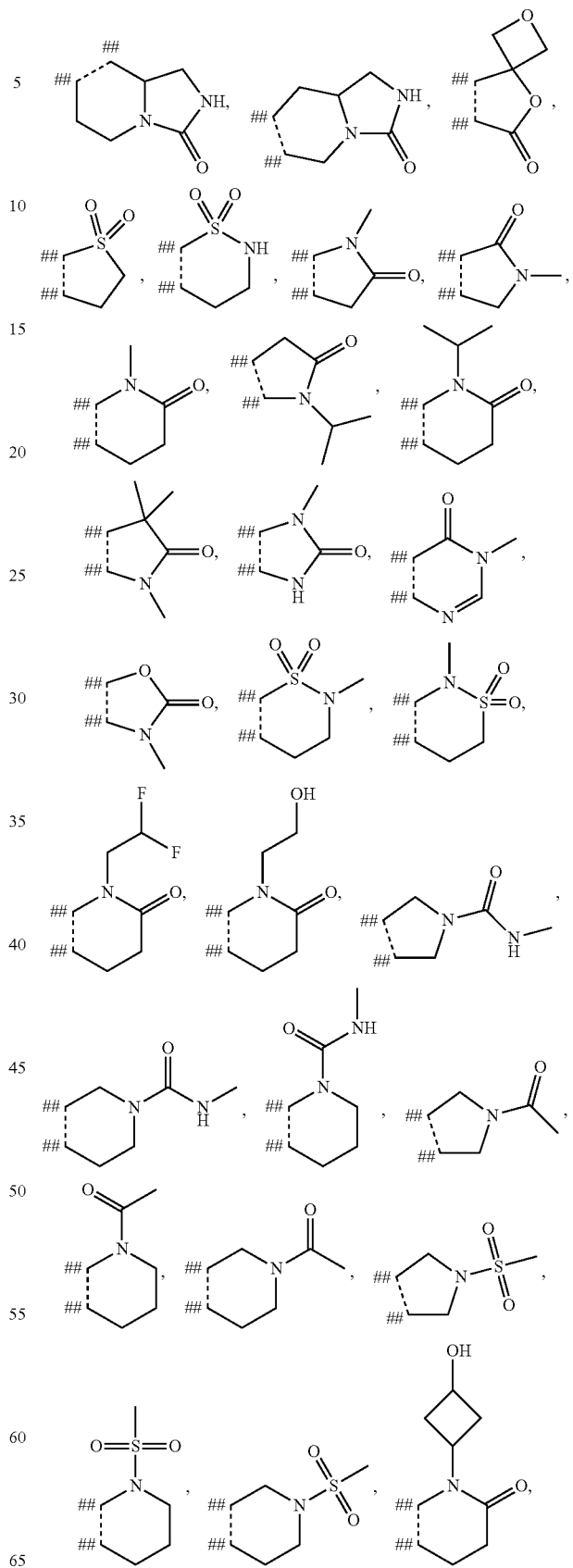

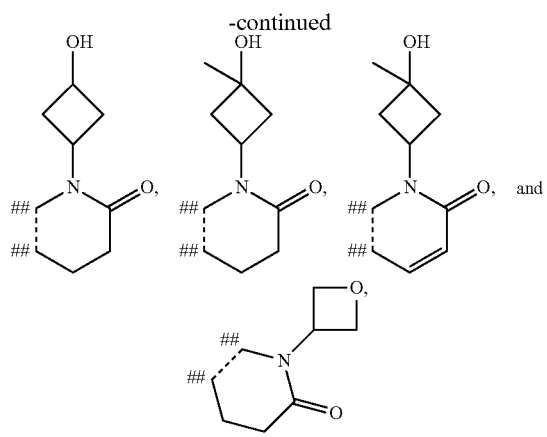

wherein ## represents a point of attachment to the remainder of the molecule and the dashed line represents a single or double bond.

12. The compound of claim 1, or a stereoisomer or tautomer thereof, or a pharmaceutically acceptable salt of any of the foregoing, wherein ring A is a 5-10 membered heteroaryl optionally substituted with one or more $R^c$.

13. The compound of claim 12, or a stereoisomer or tautomer thereof, or a pharmaceutically acceptable salt of any of the foregoing, wherein ring A is selected from the group consisting of

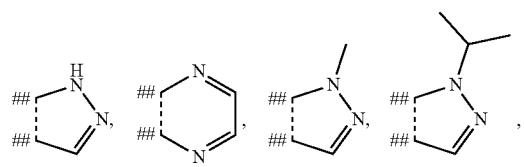

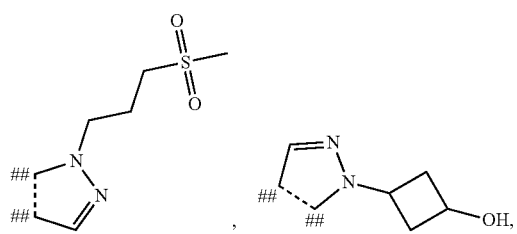

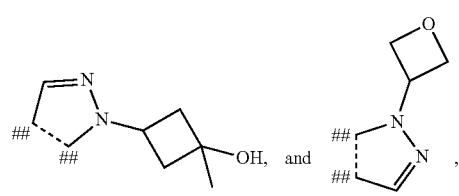

wherein ## represents a point of attachment to the remainder of the molecule and the dashed line represents a single or double bond.

14. The compound of claim 1, or a stereoisomer or tautomer thereof, or a pharmaceutically acceptable salt of any of the foregoing, wherein the compound is

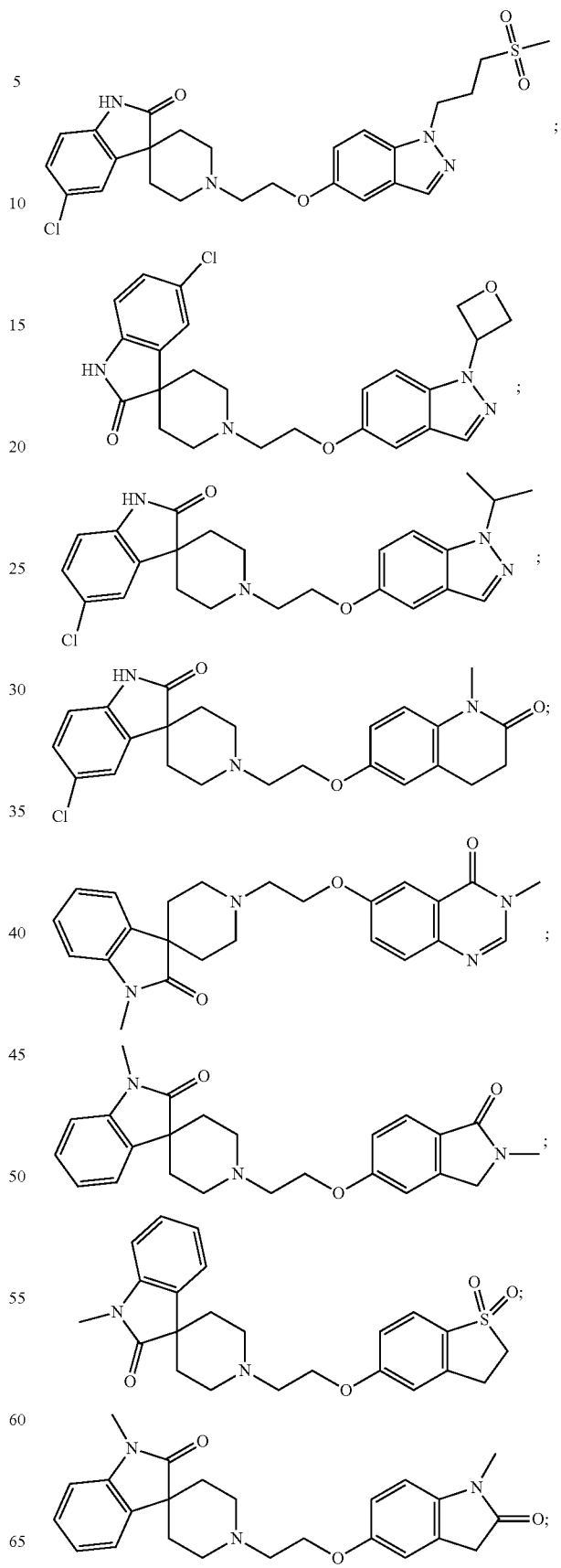

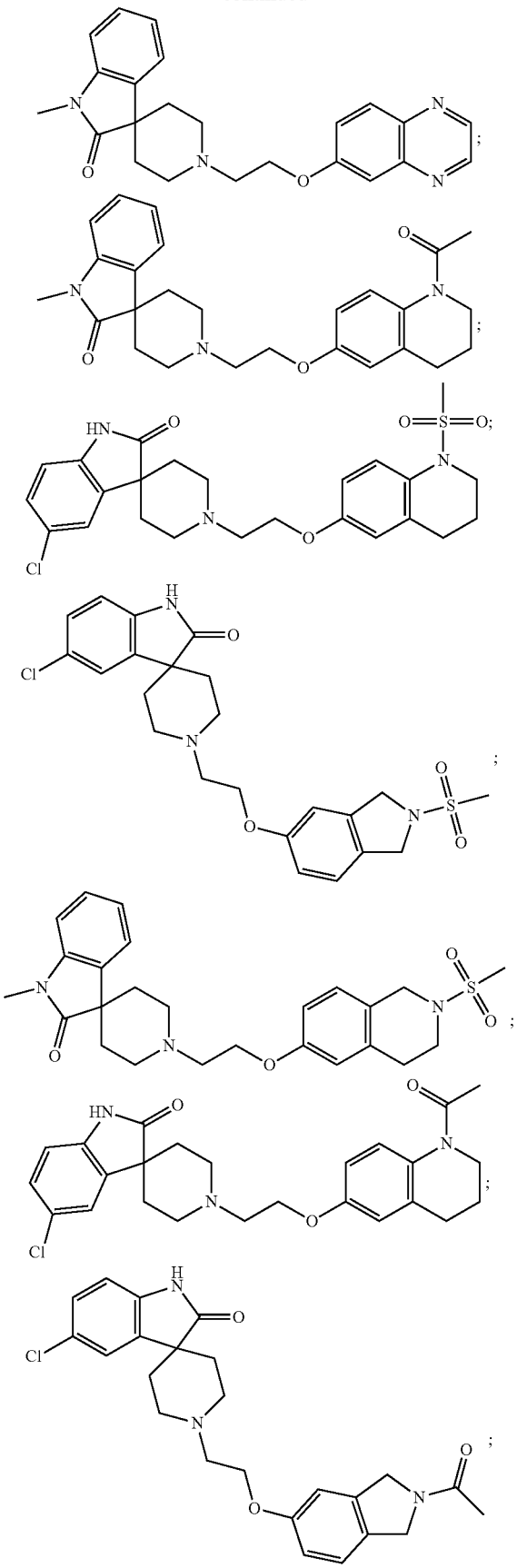
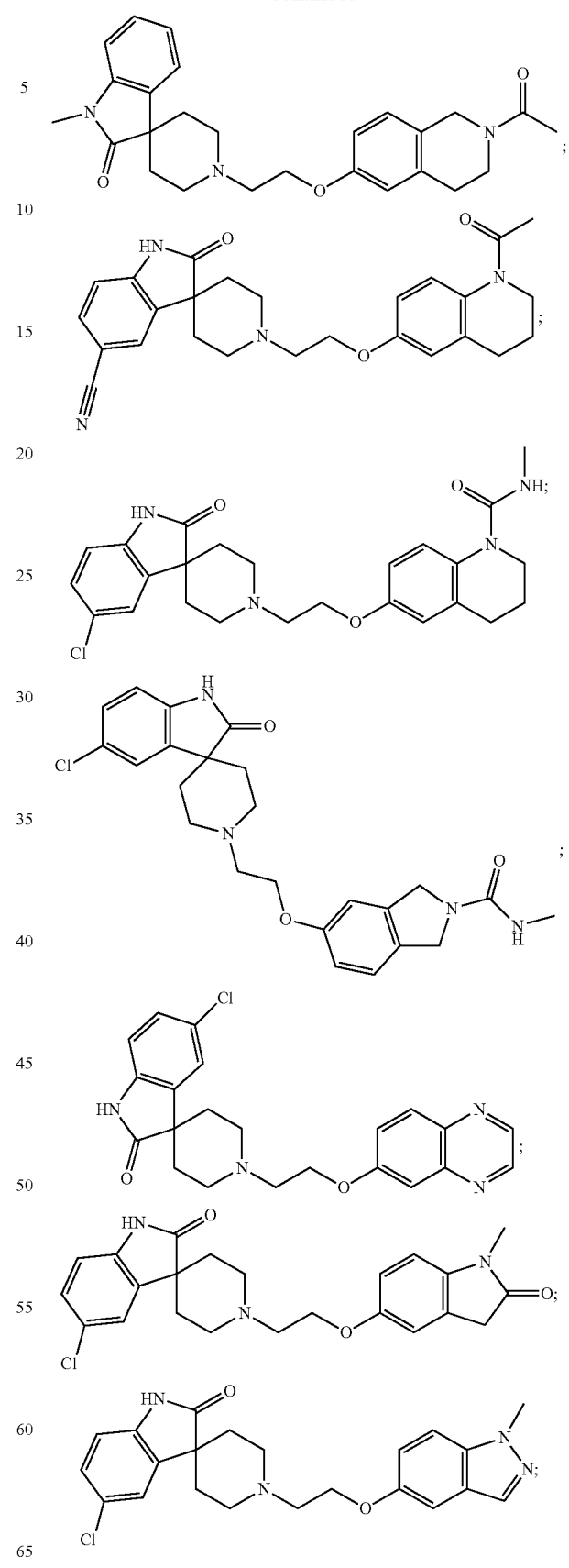

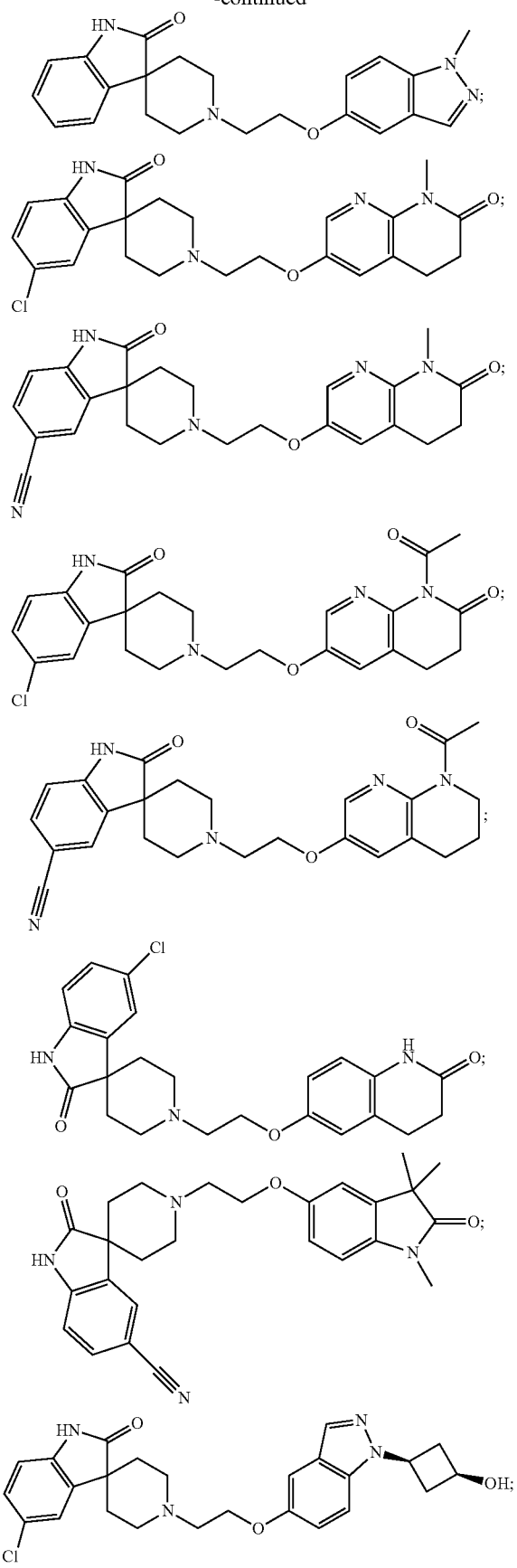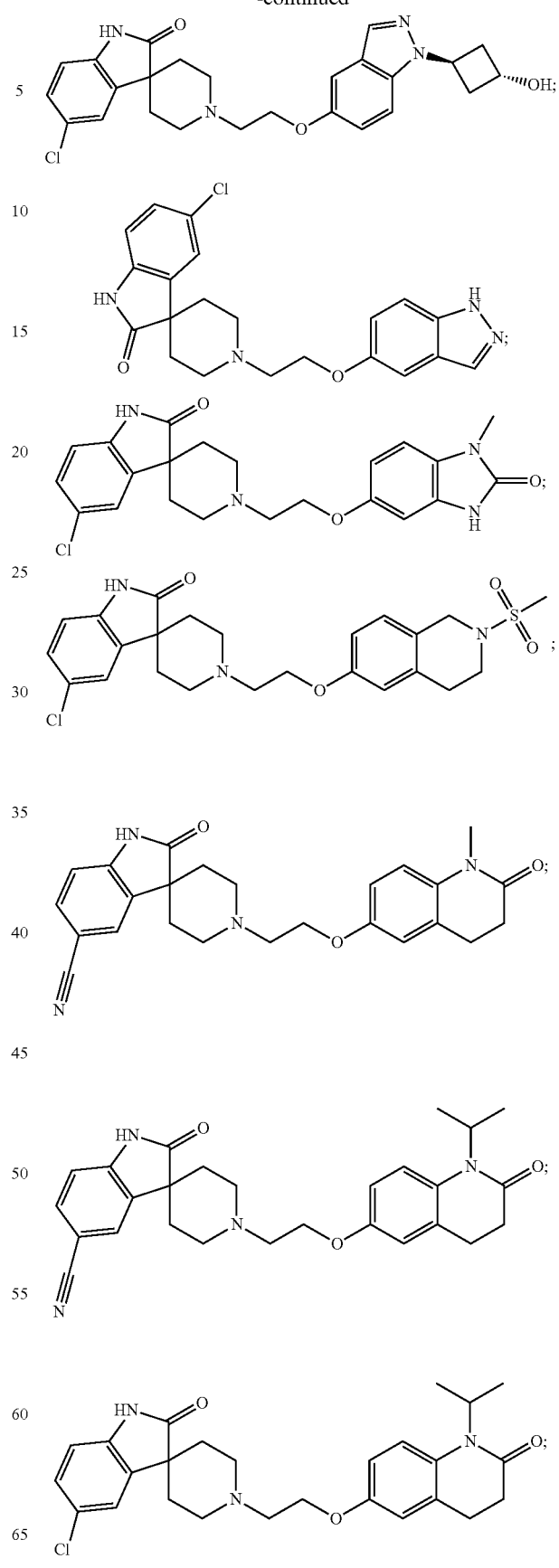

1375
-continued
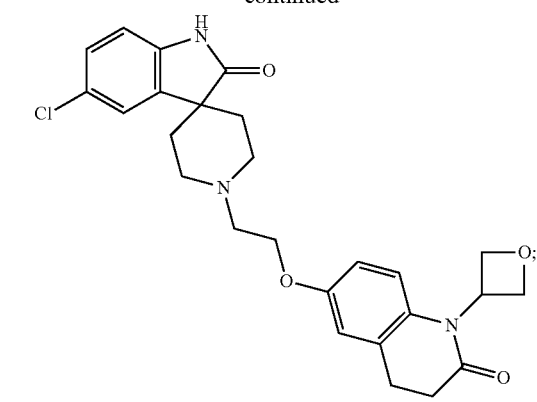
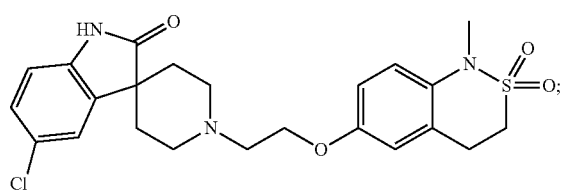
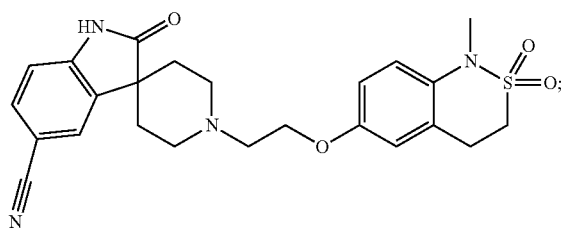
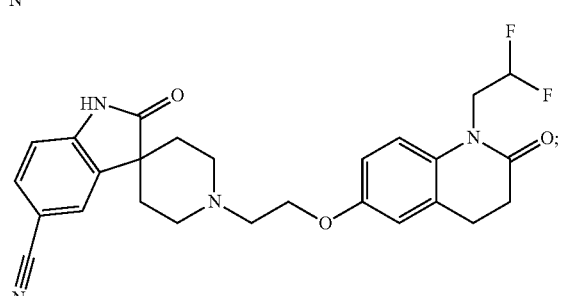
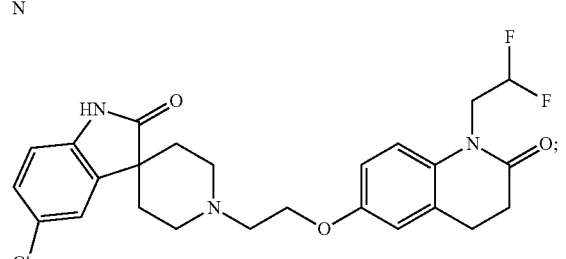
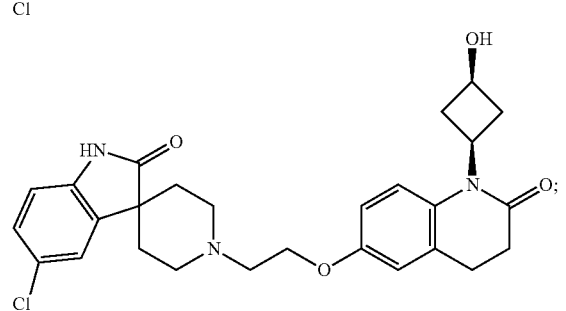
1376
-continued
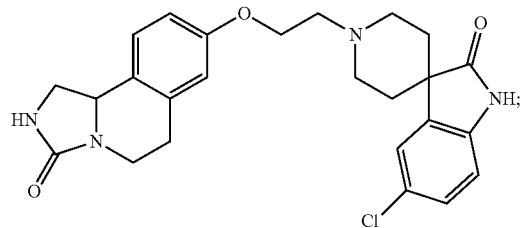
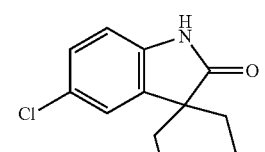
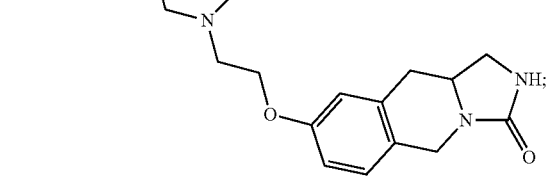
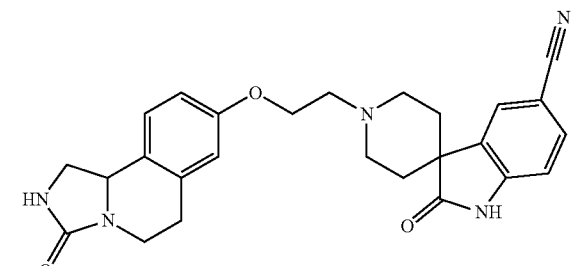
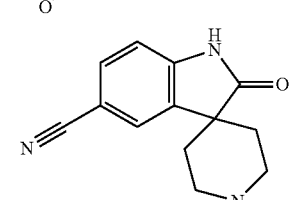
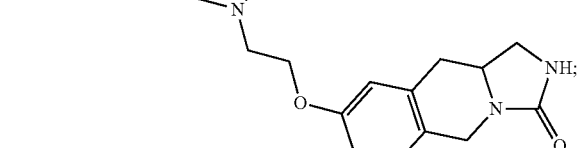
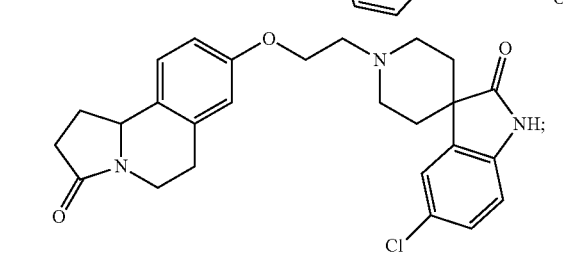
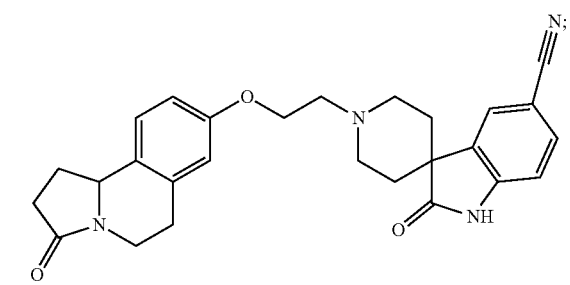

1377
-continued
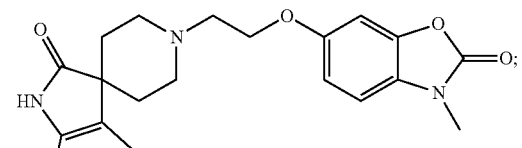
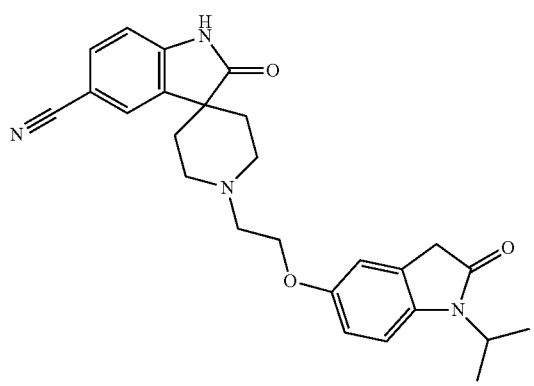
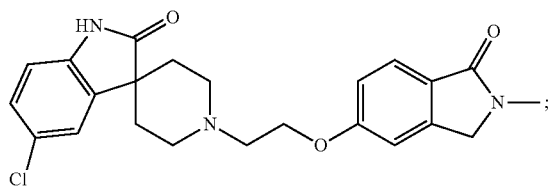
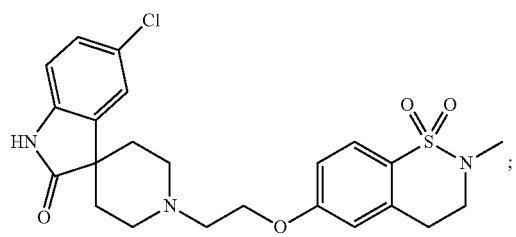
1378
-continued
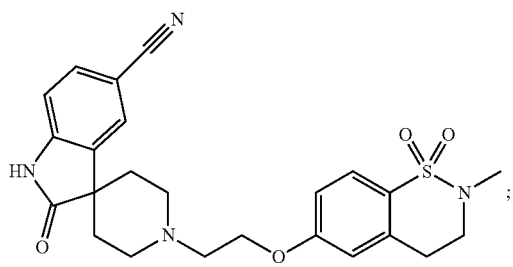
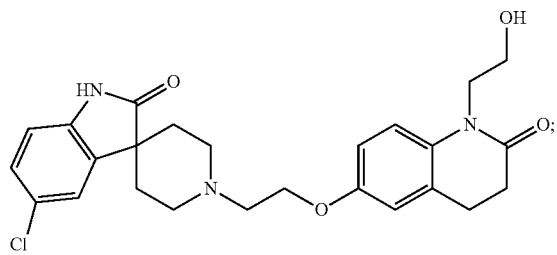
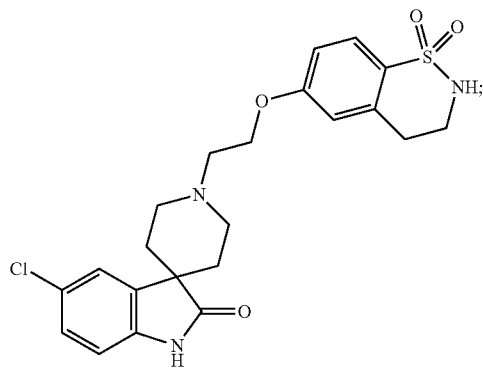
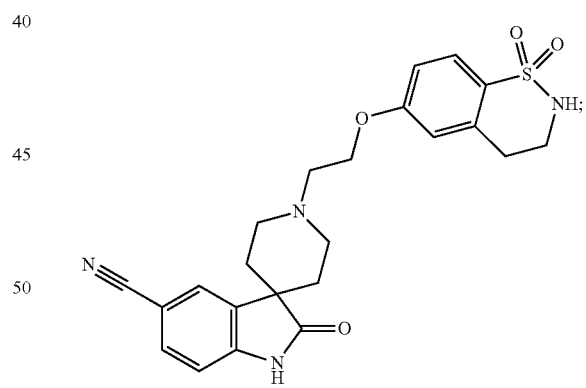
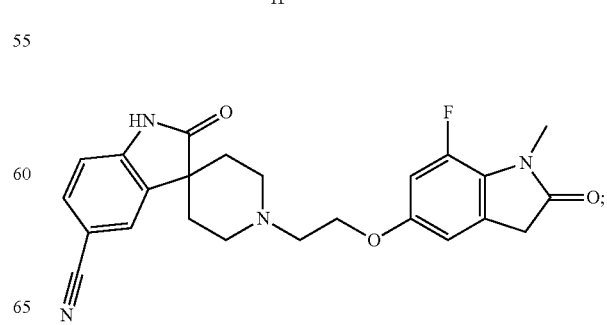

1379
-continued
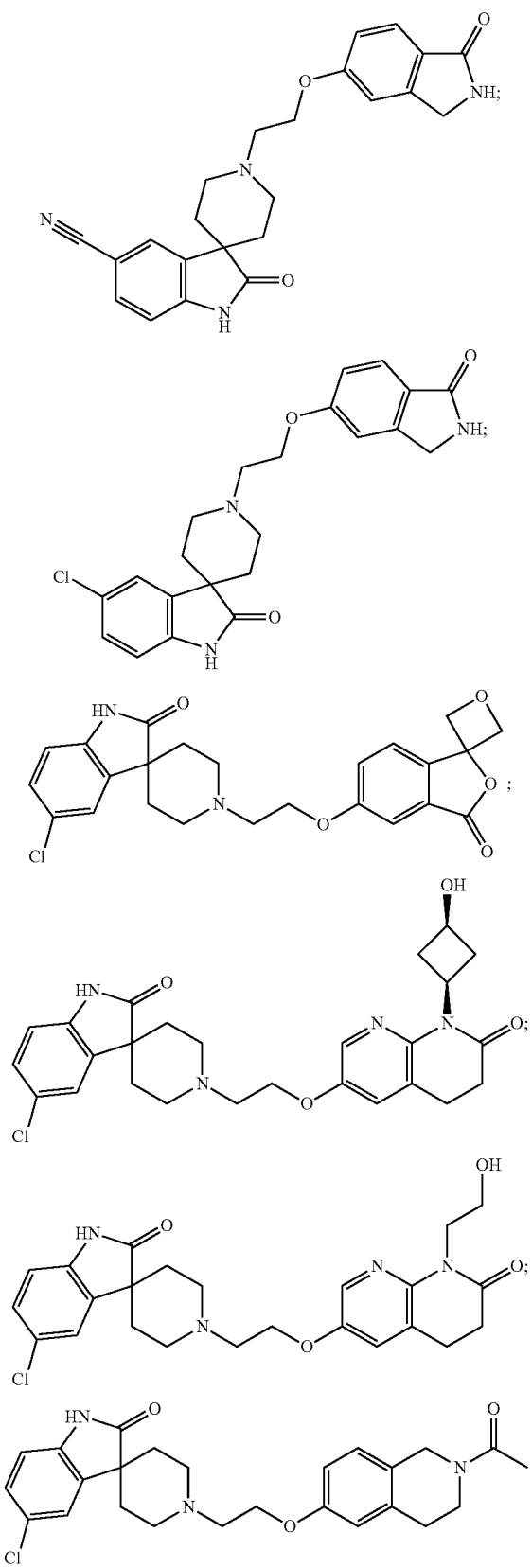
1380
-continued
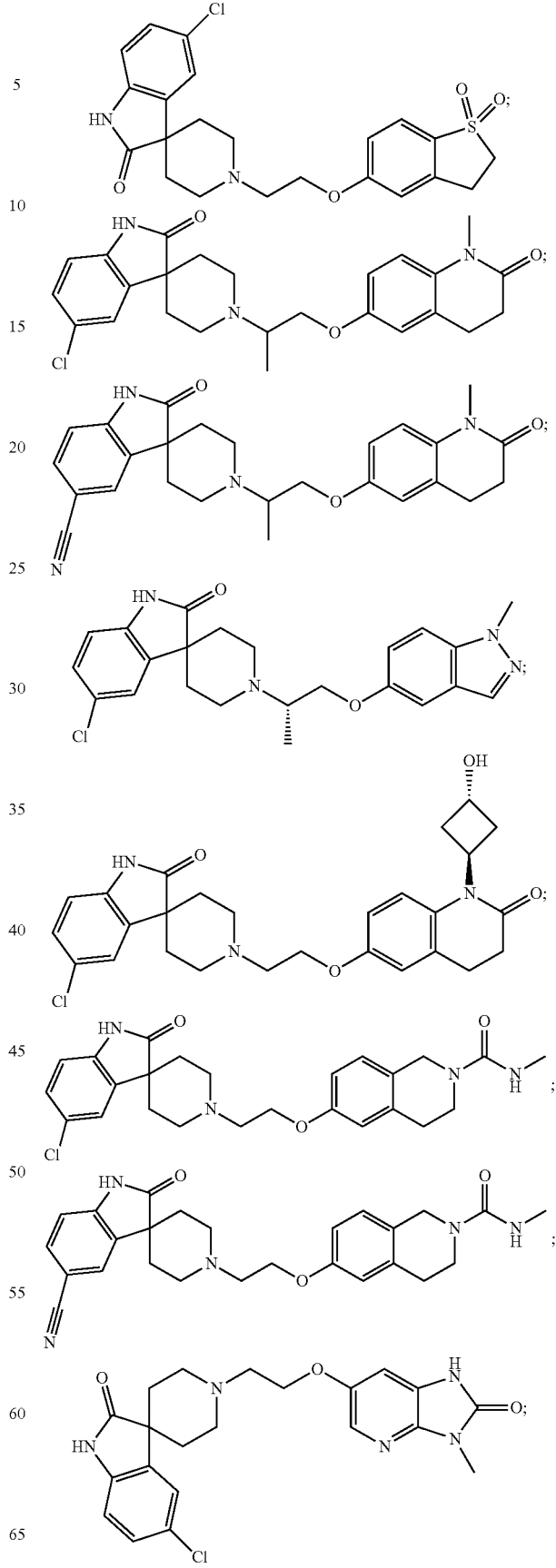

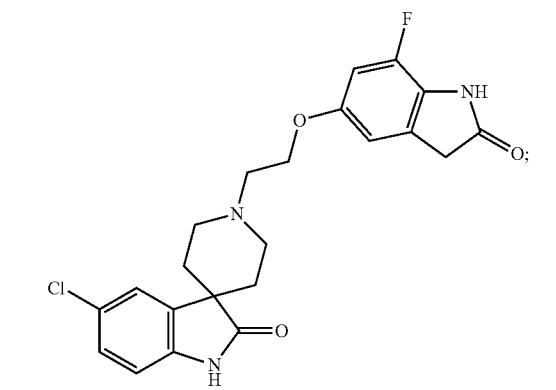
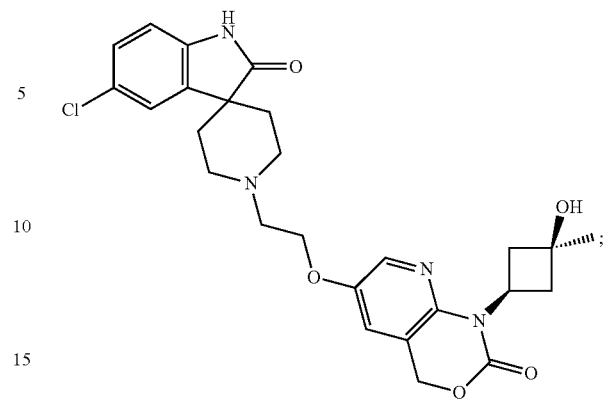
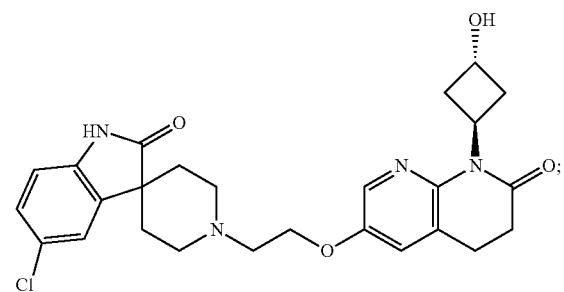
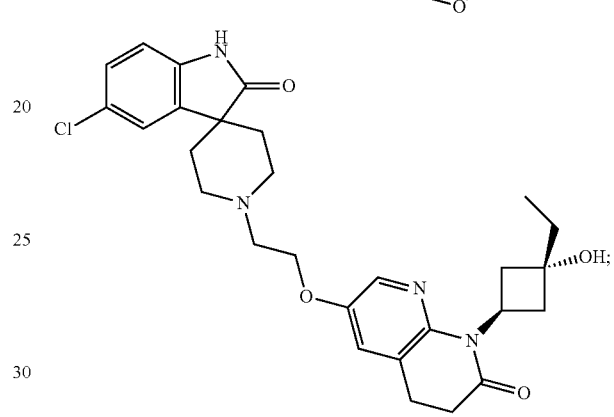
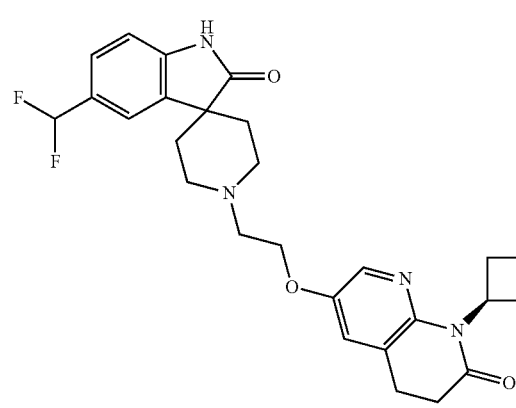
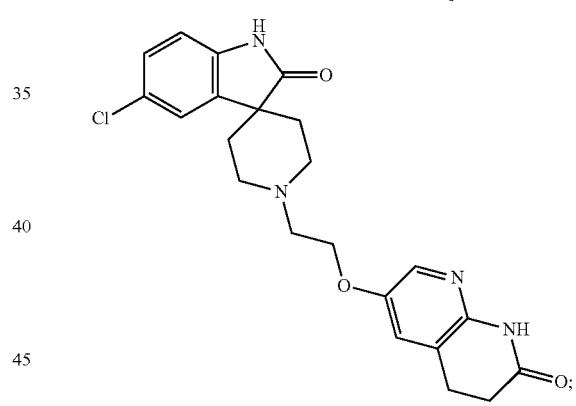
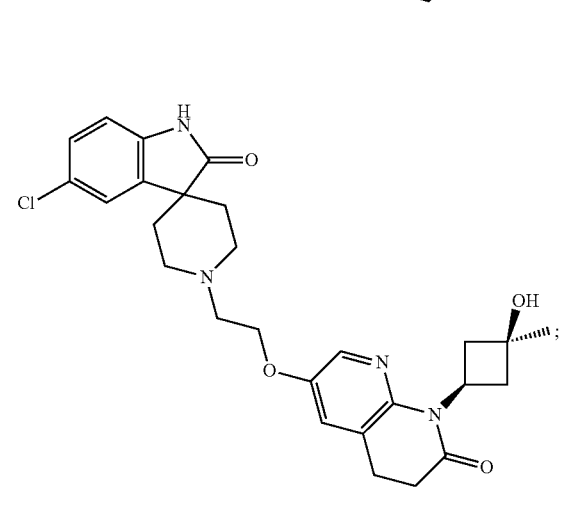
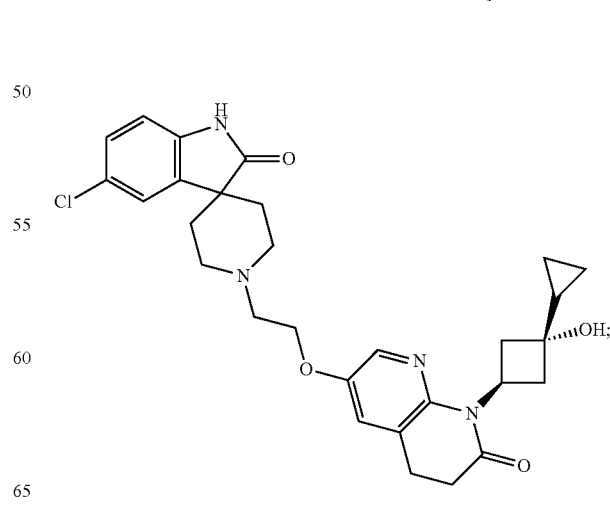

1383
-continued
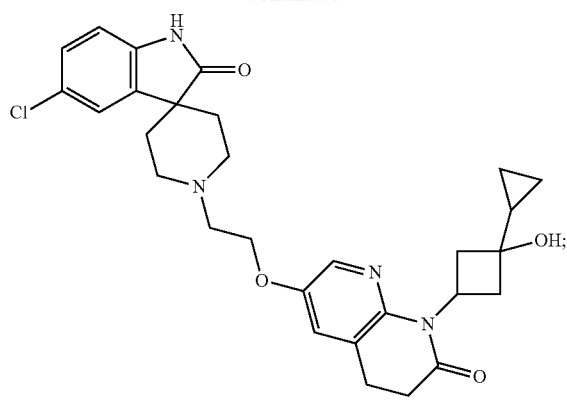
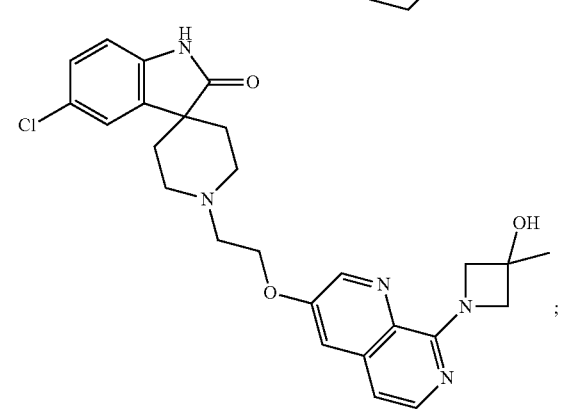
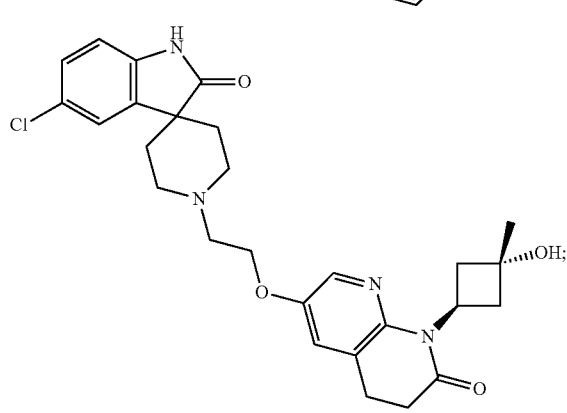
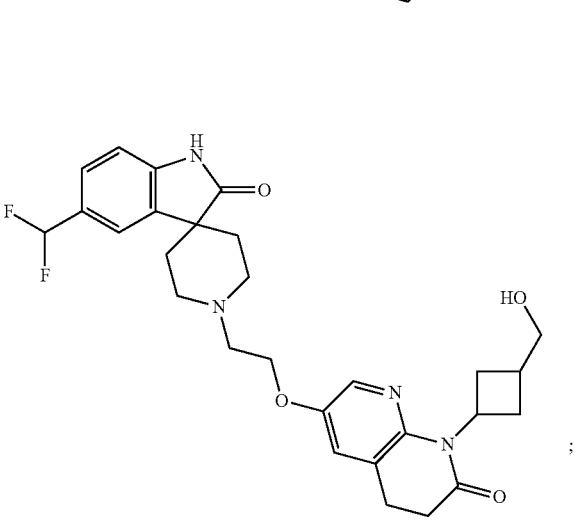
1384
-continued
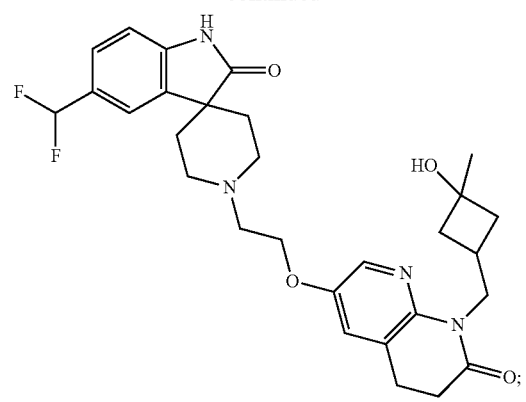
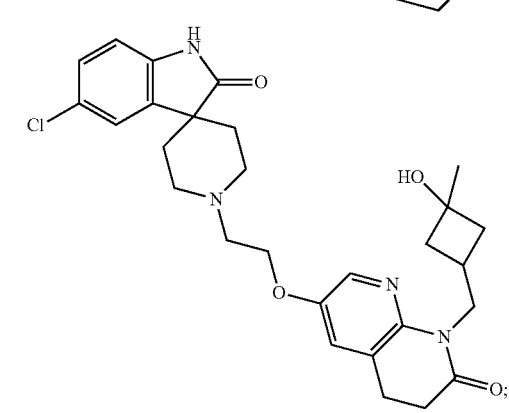
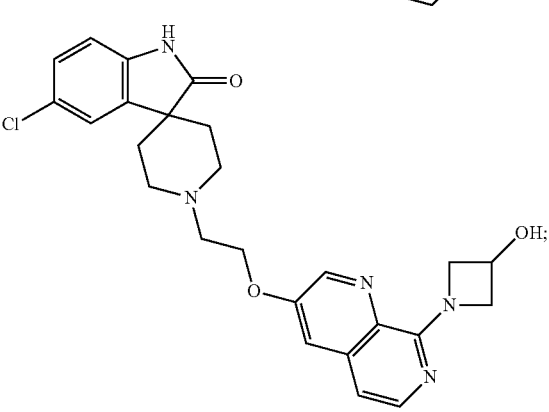
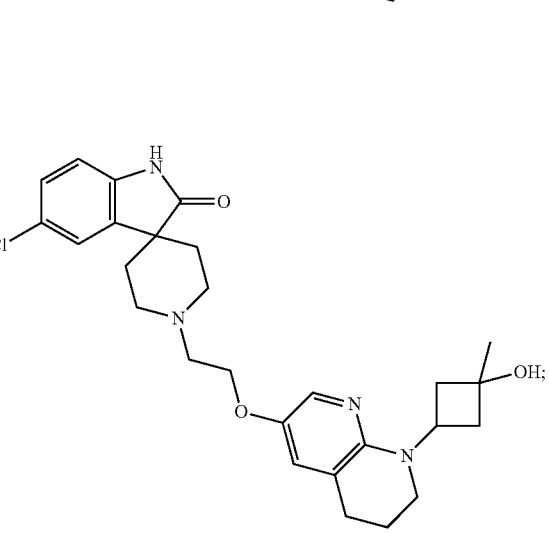

1385
-continued
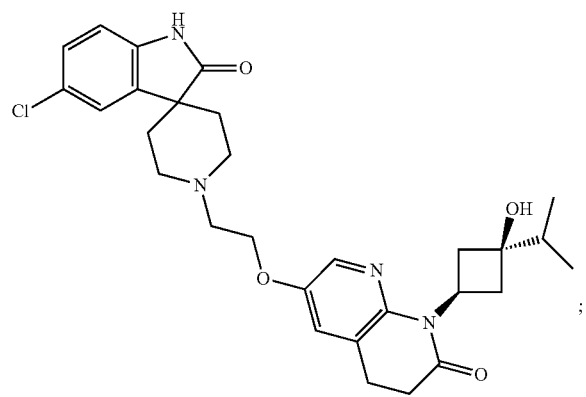
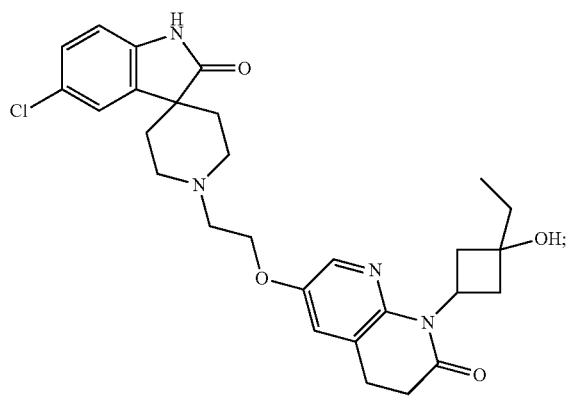
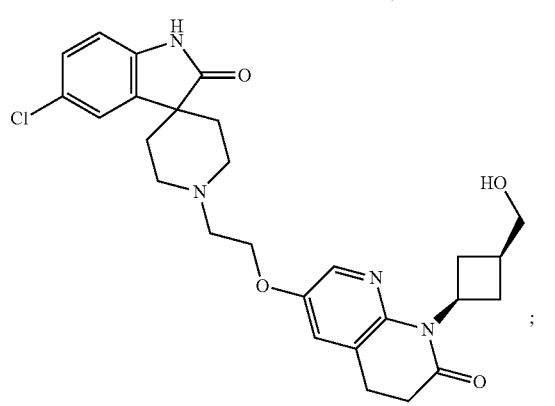
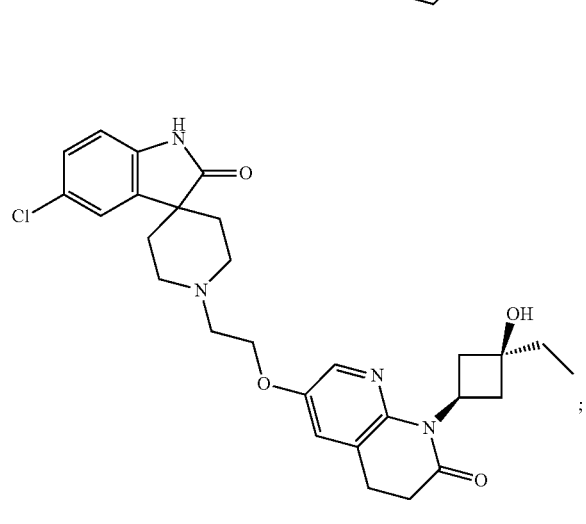
1386
-continued
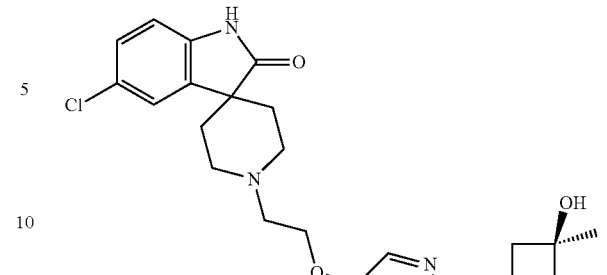
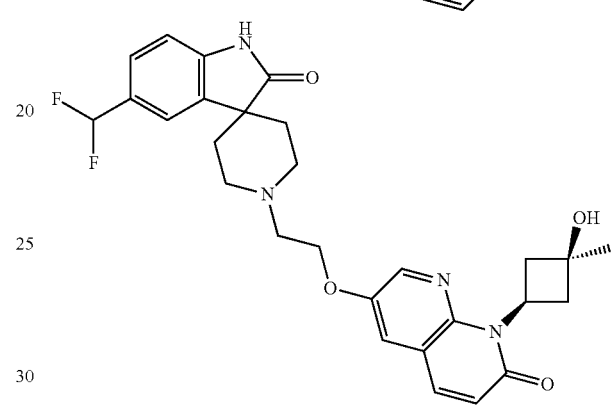
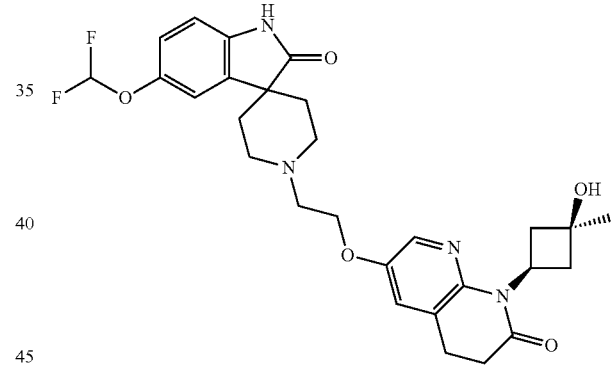
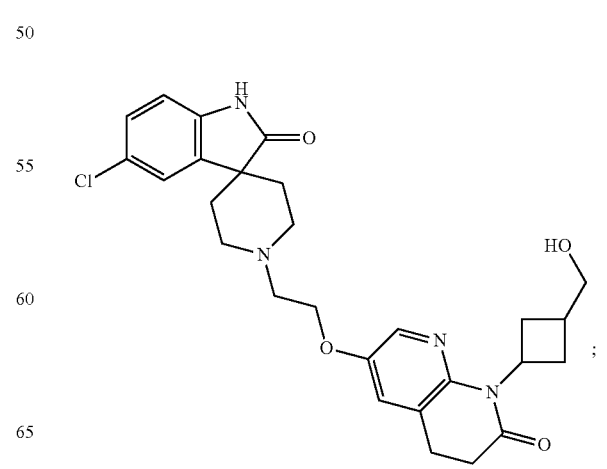

1387
-continued
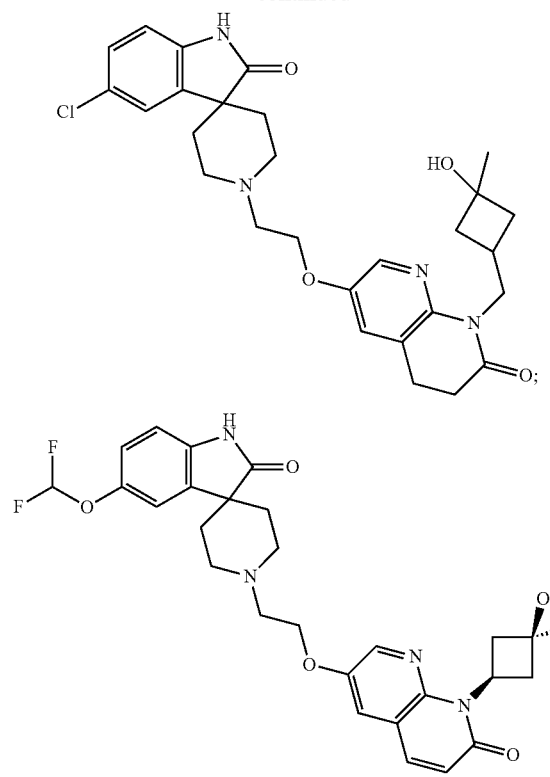
1388
-continued
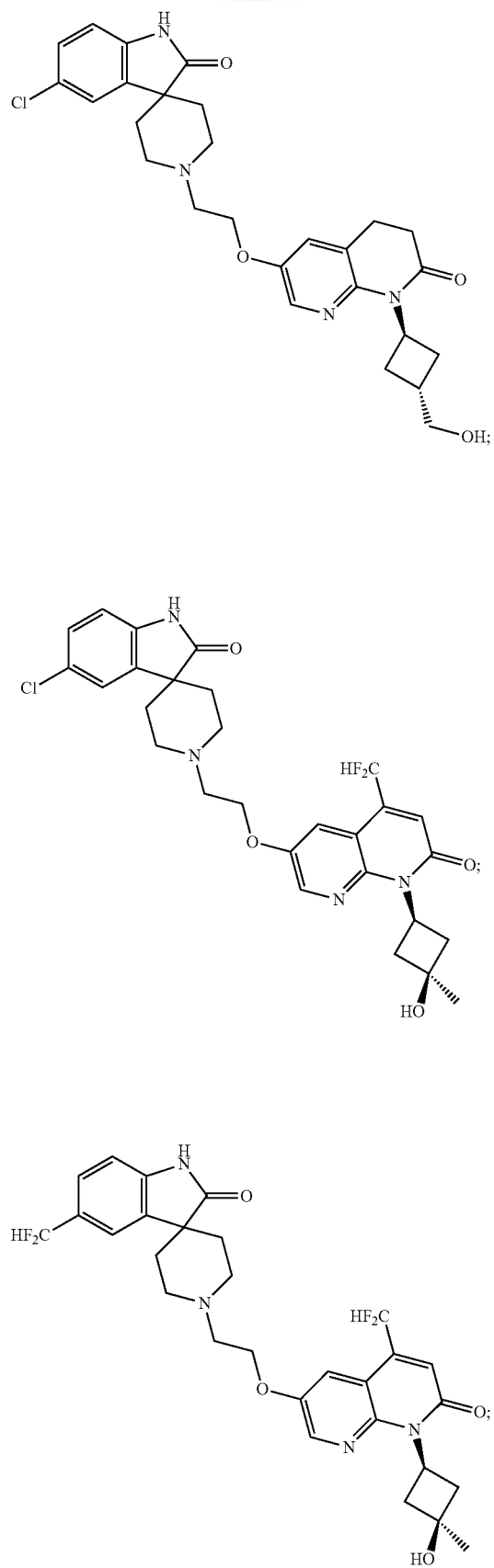

1389
-continued
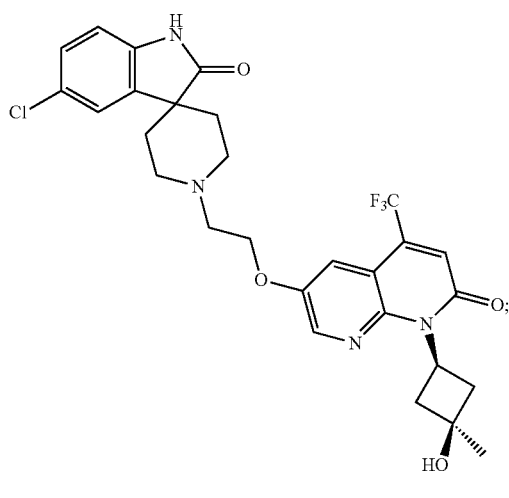
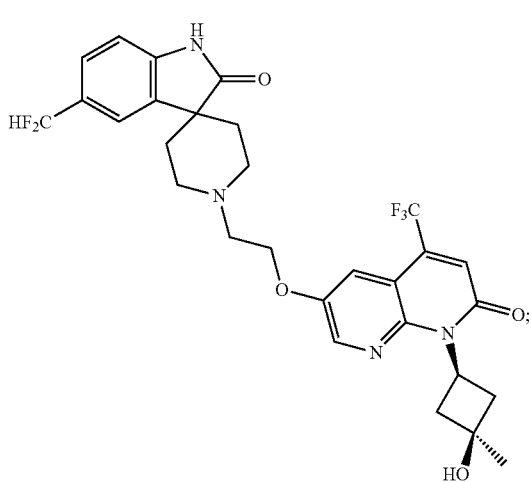
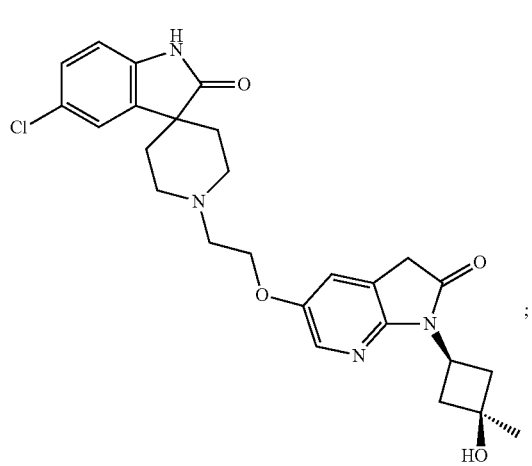
1390
-continued
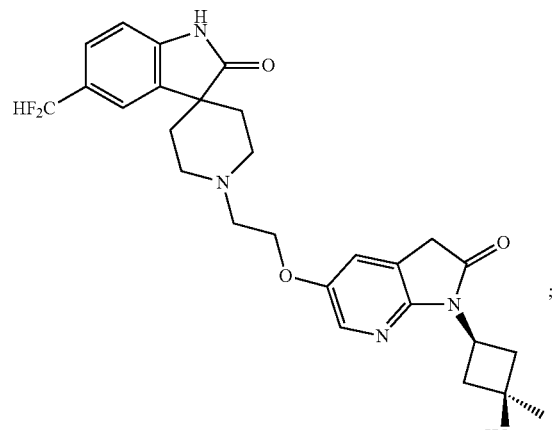
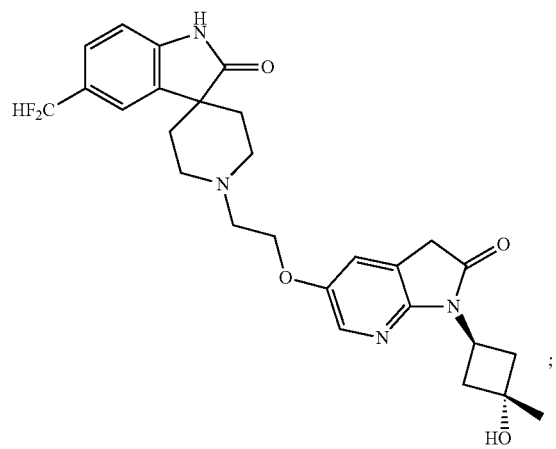

1391
-continued
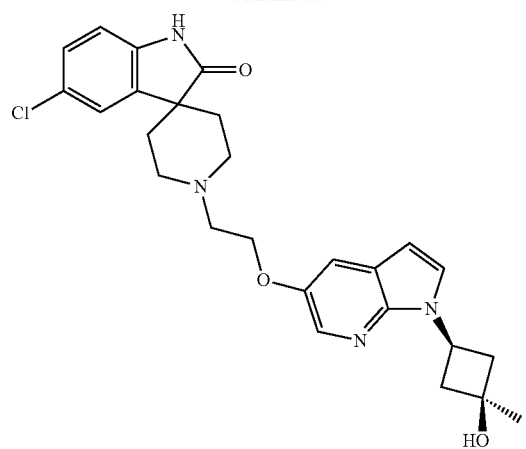
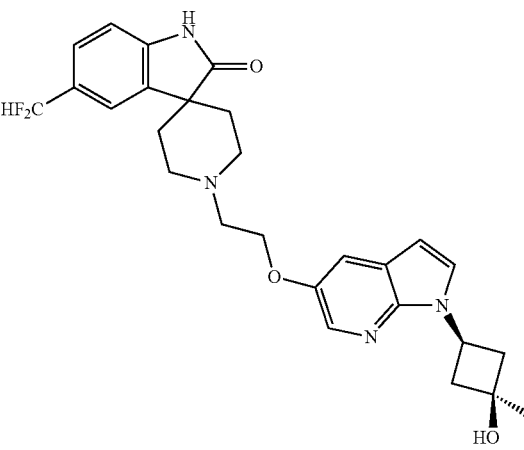
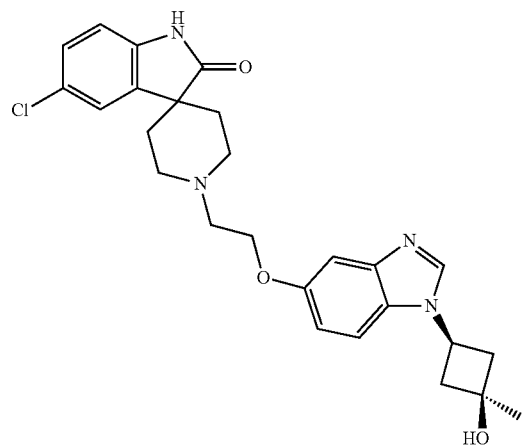
1392
-continued
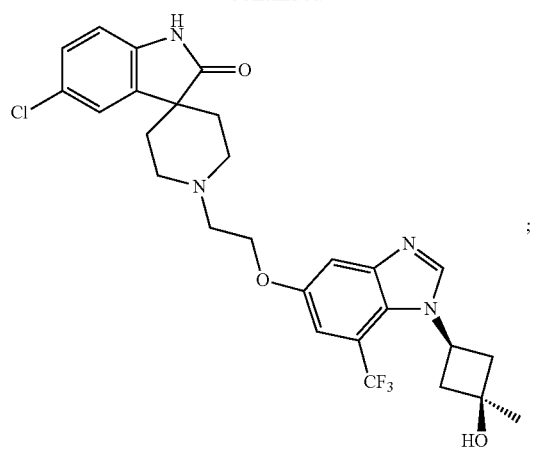
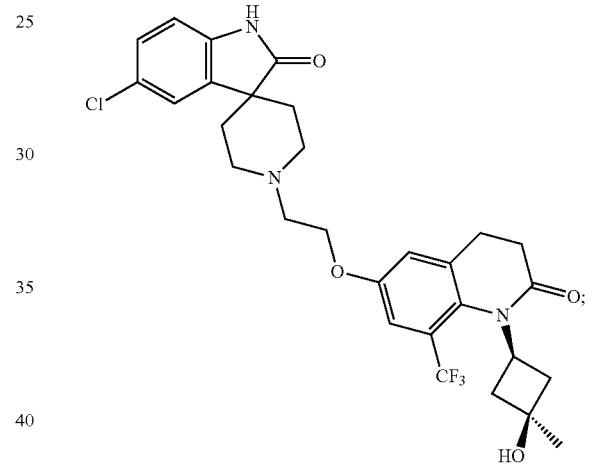
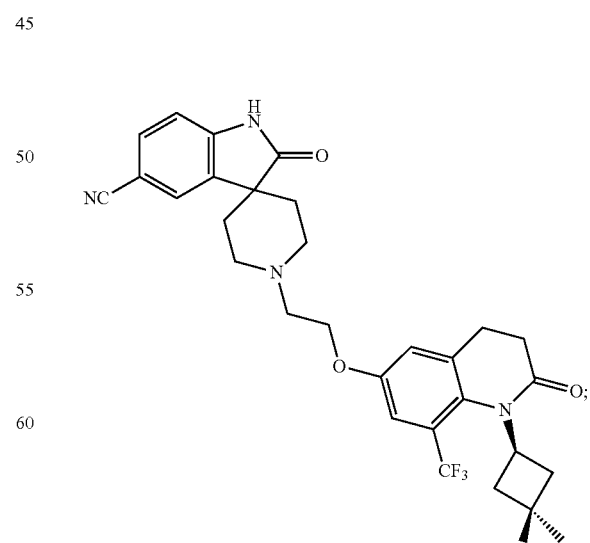

1393
-continued
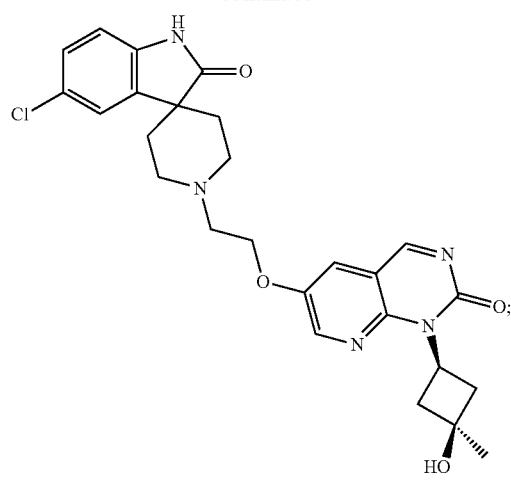
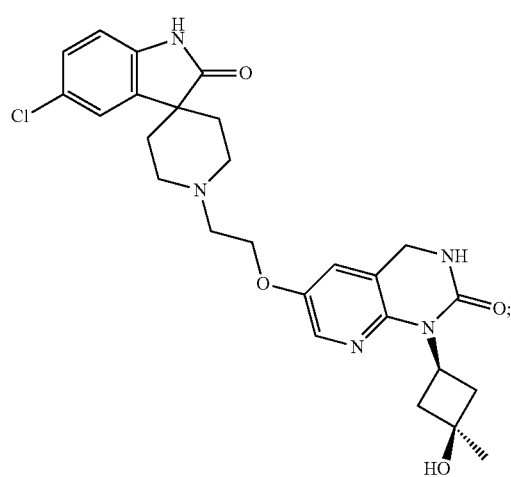
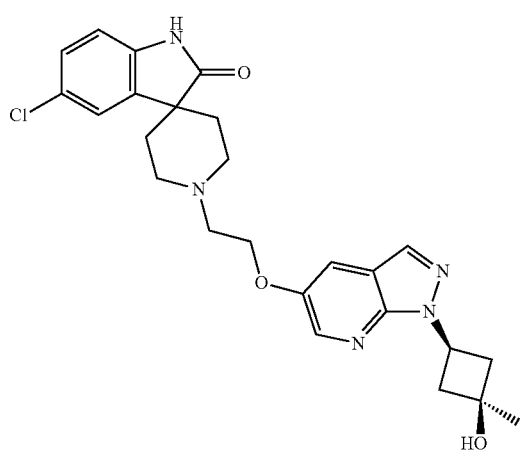
1394
-continued
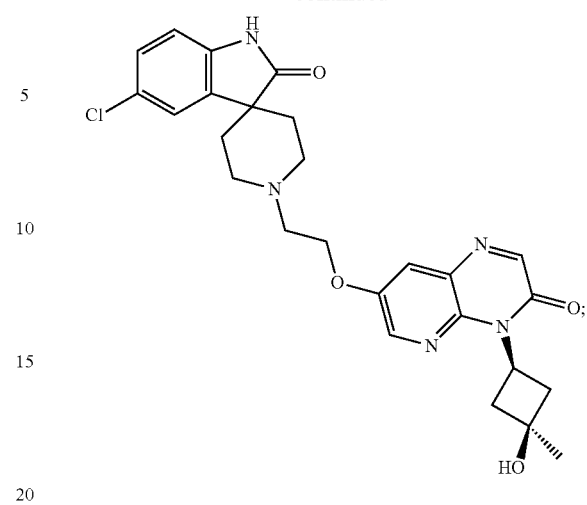
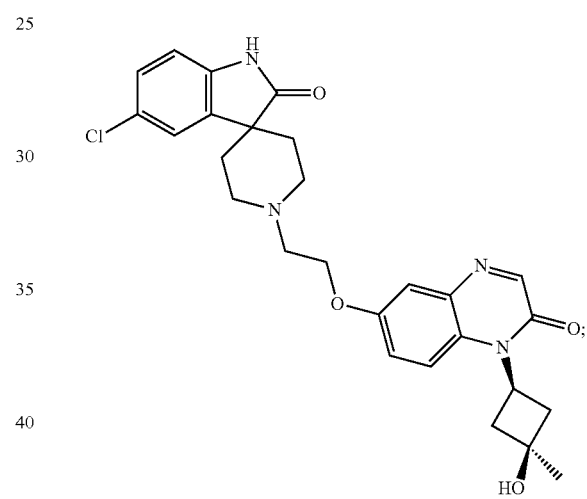
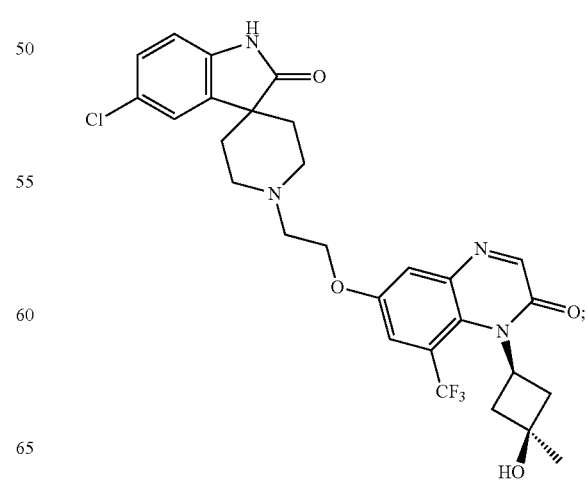

1395
-continued
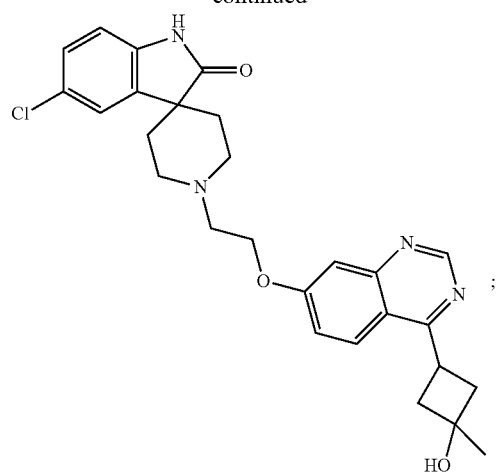
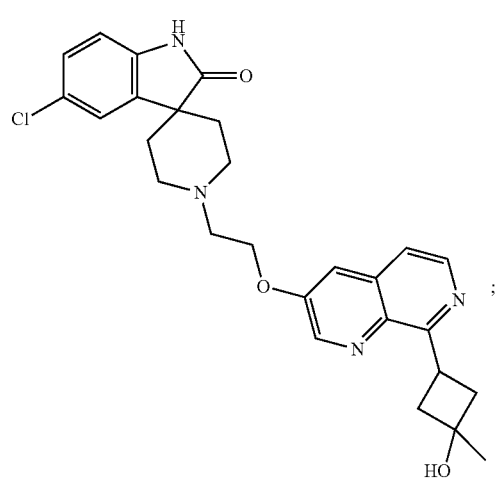
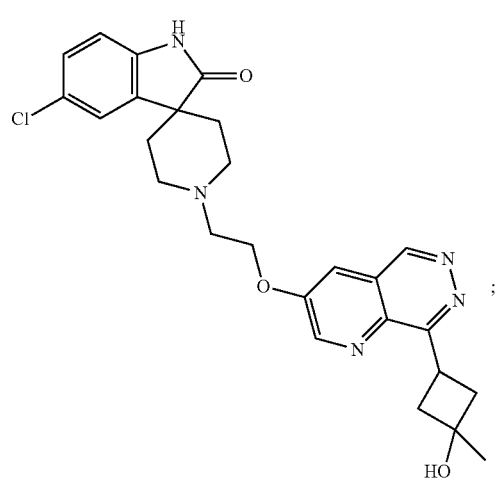
1396
-continued
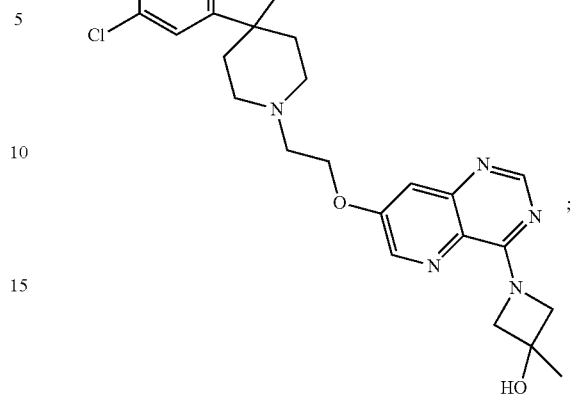
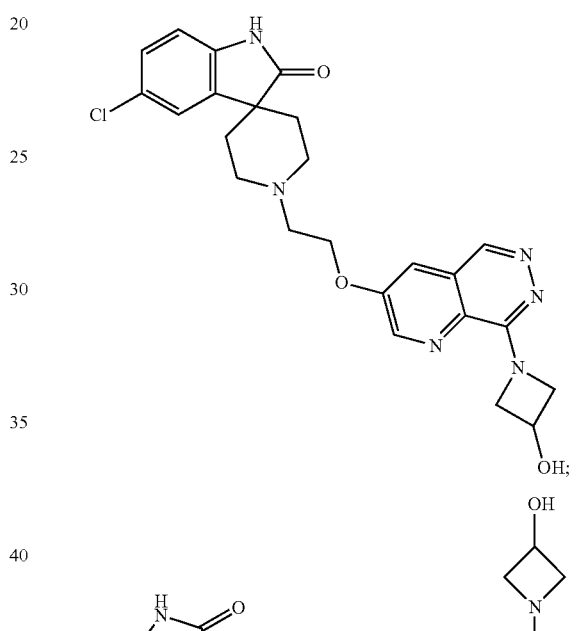
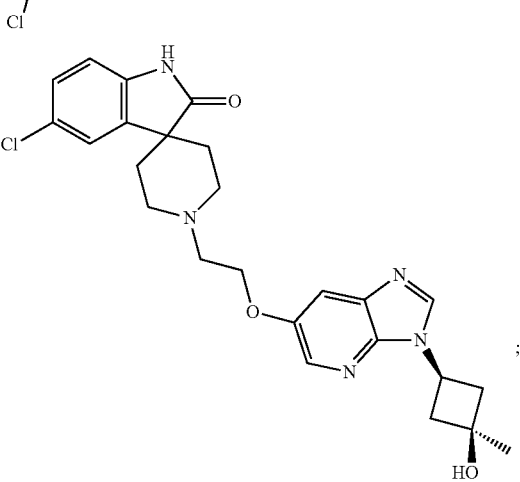

1397
-continued
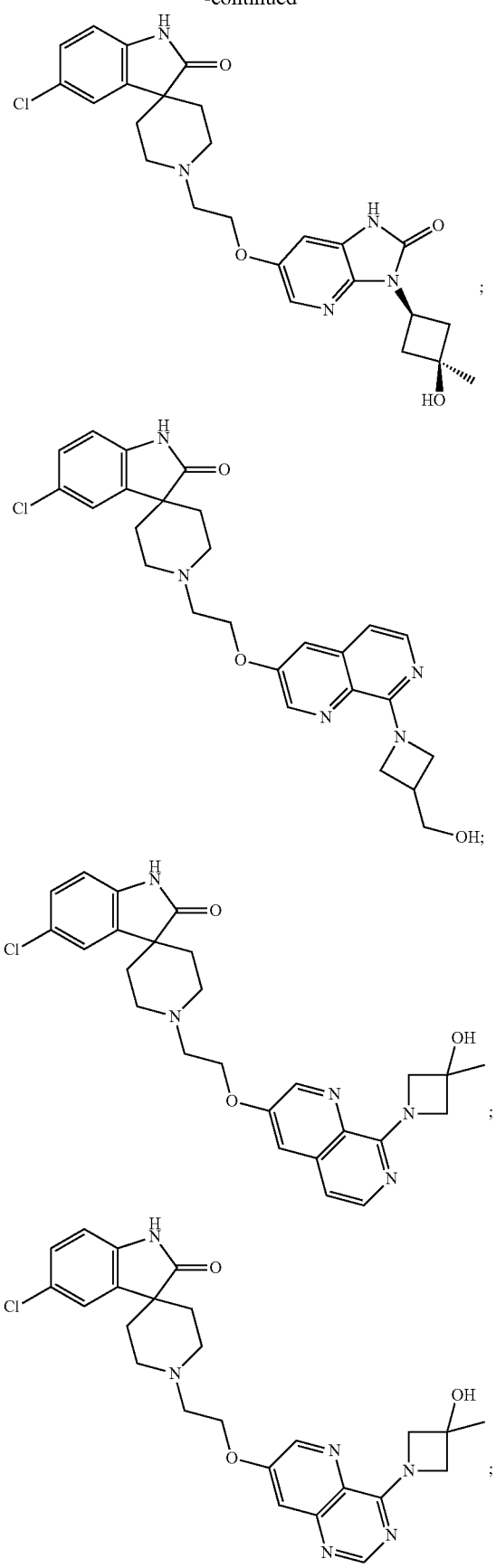
1398
-continued
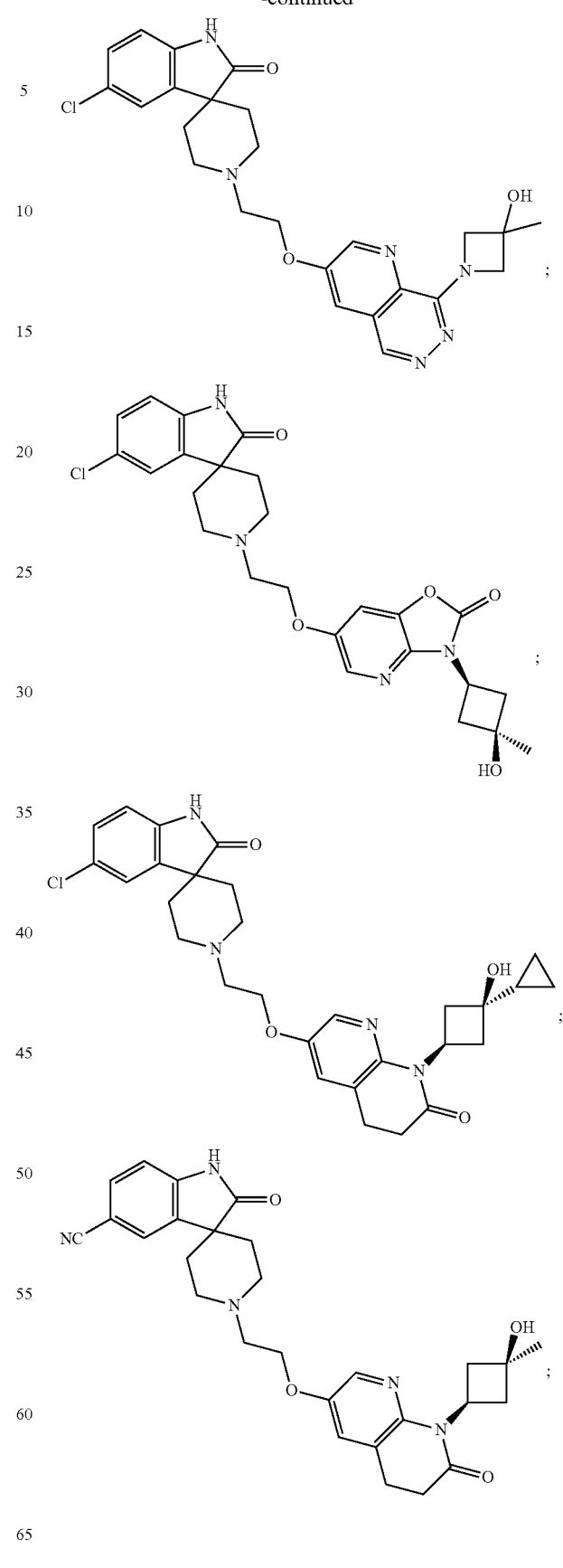

1399
-continued
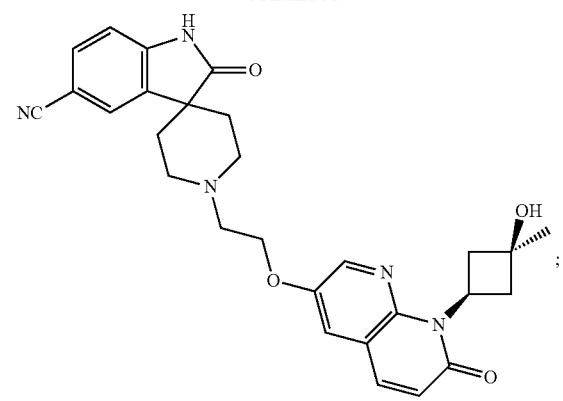
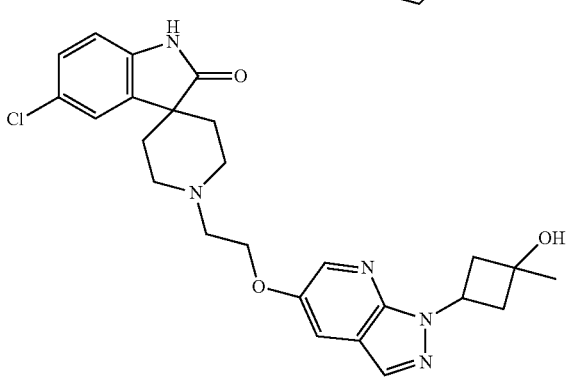
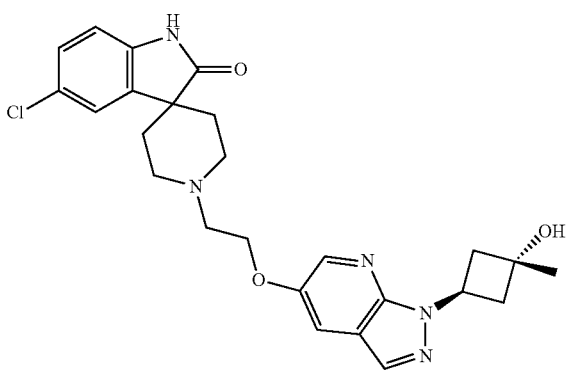
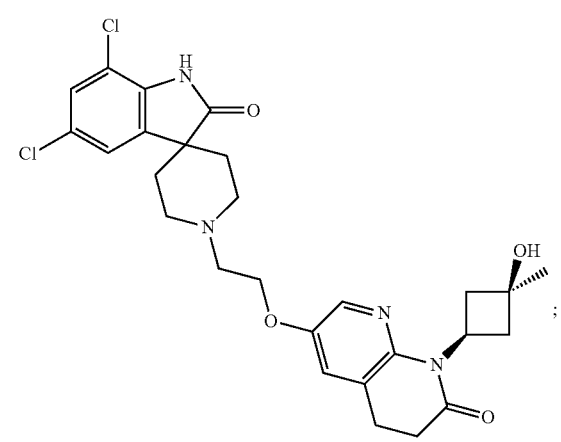
1400
-continued
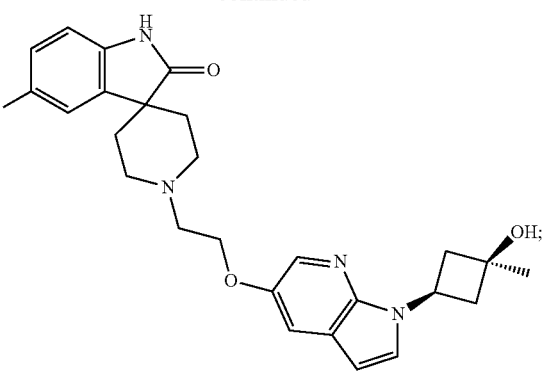
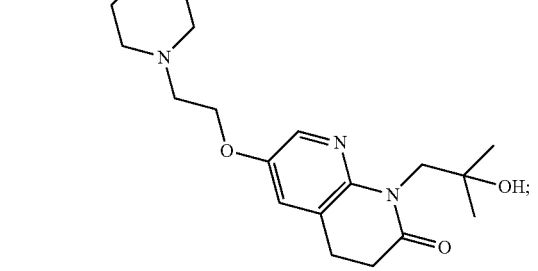

1401
-continued
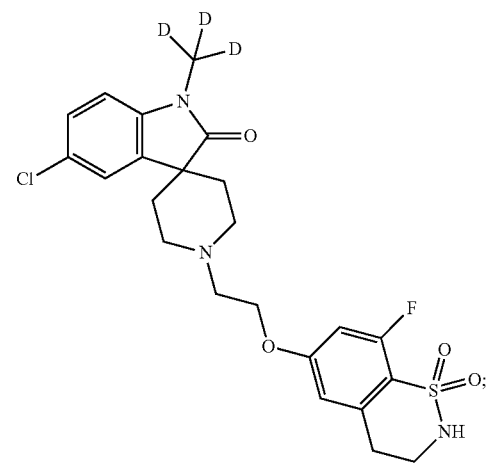
1402
-continued
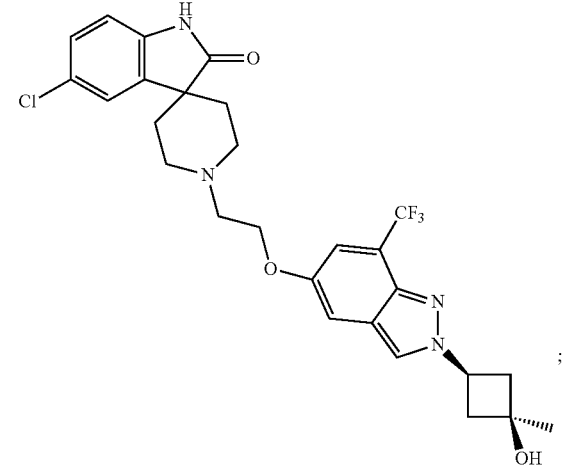
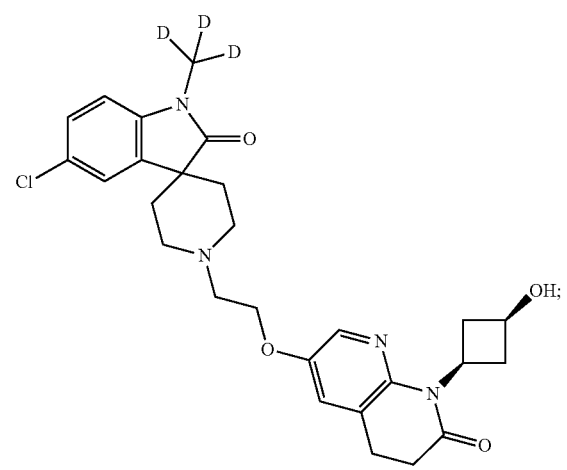
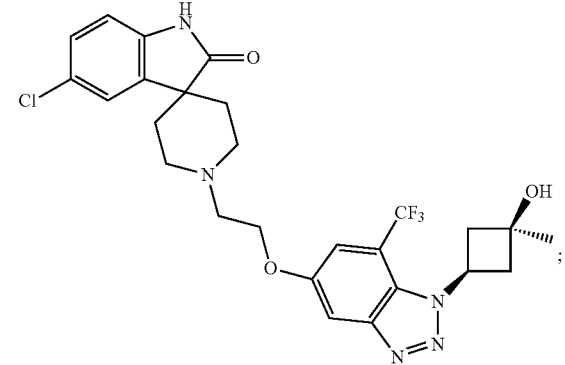
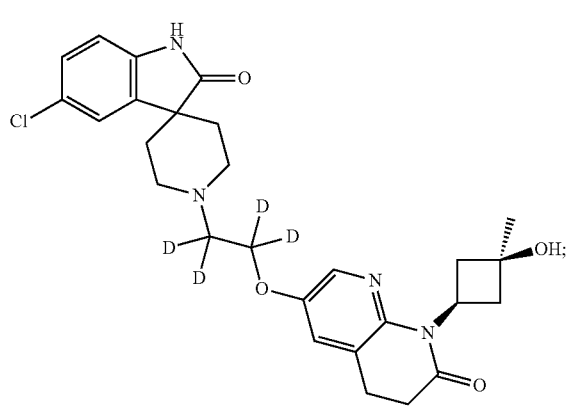

1403
-continued
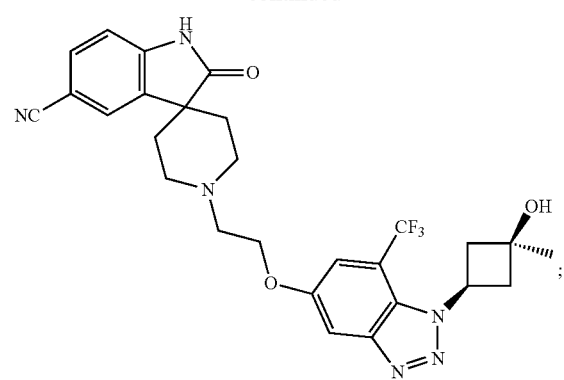
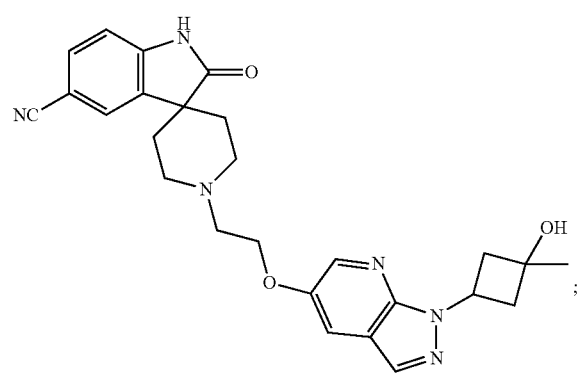
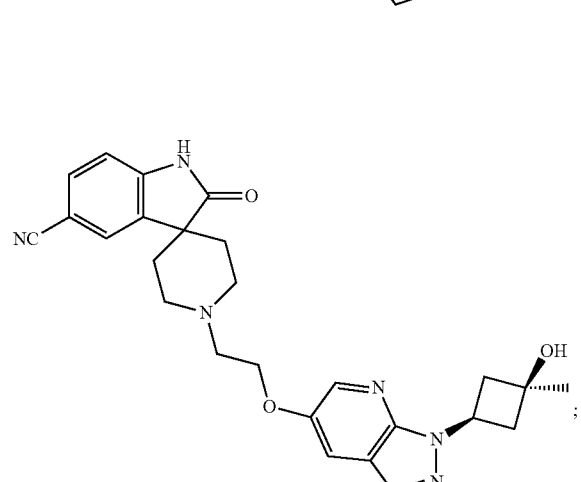
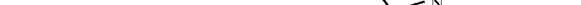
1404
-continued
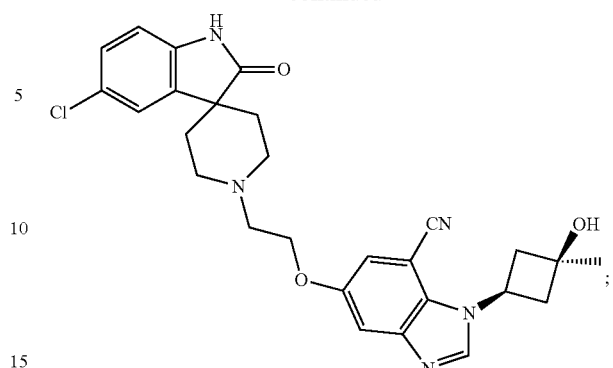
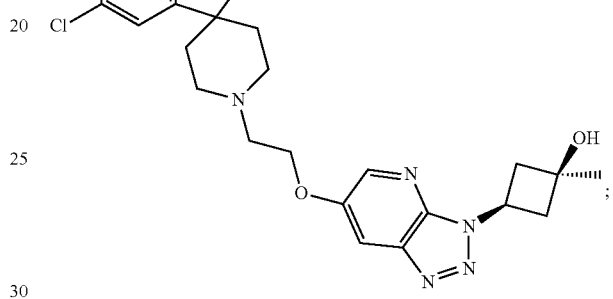
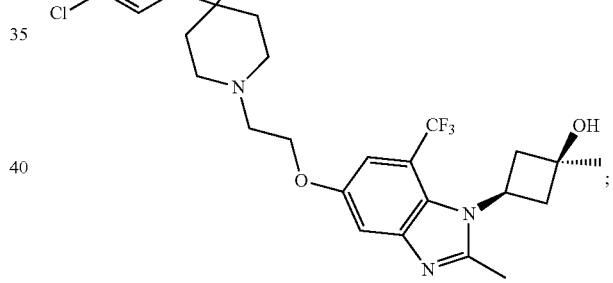
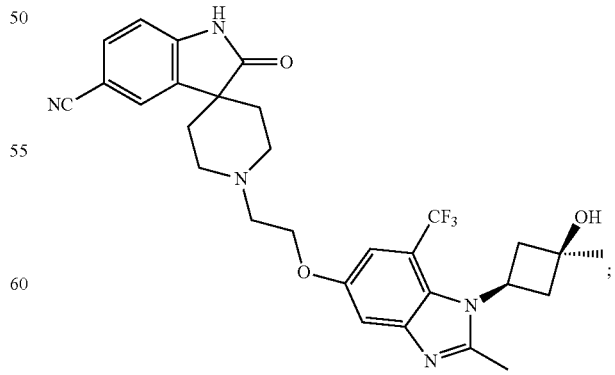

1405
-continued
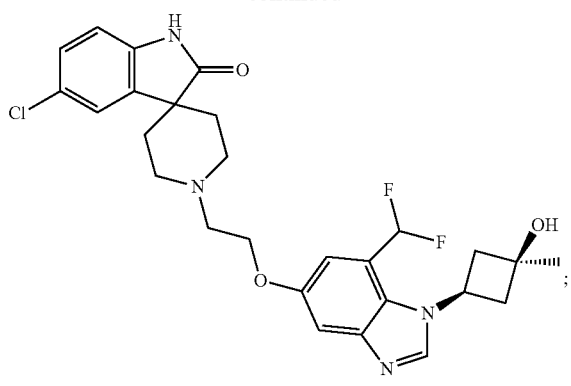
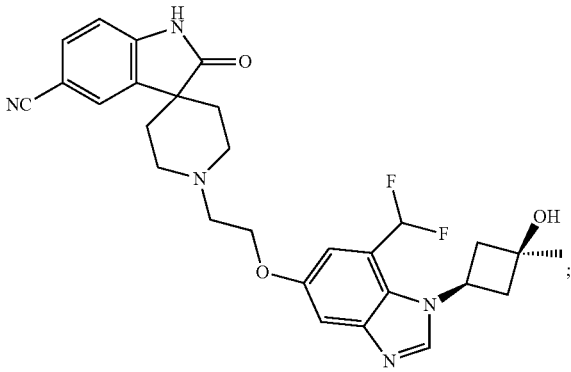
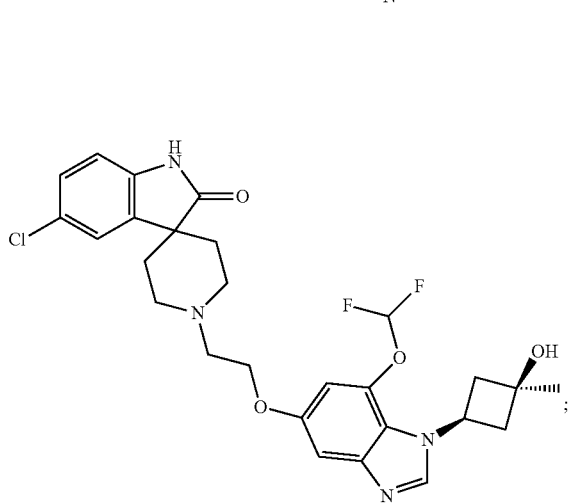
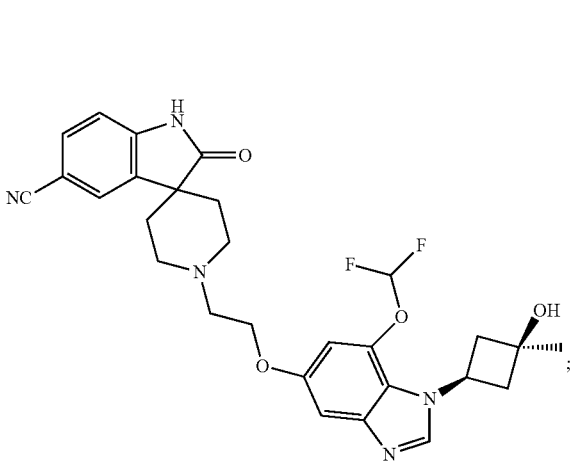
1406
-continued
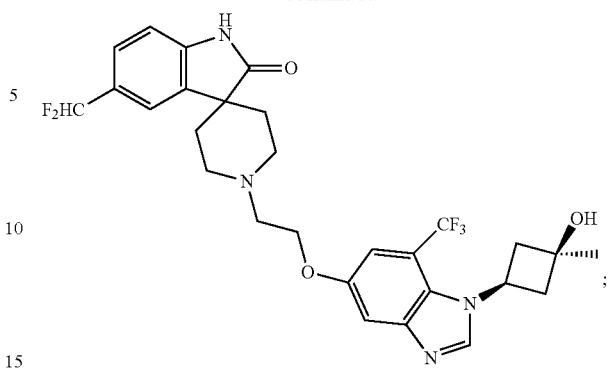
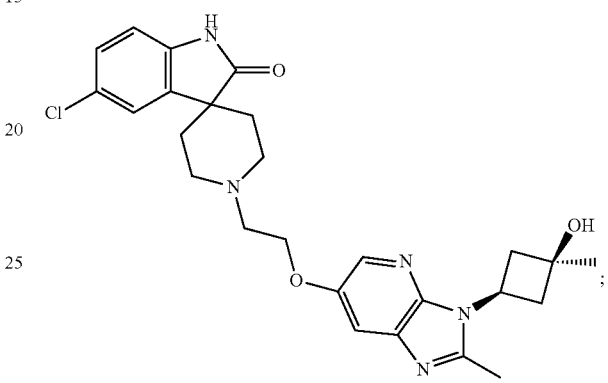
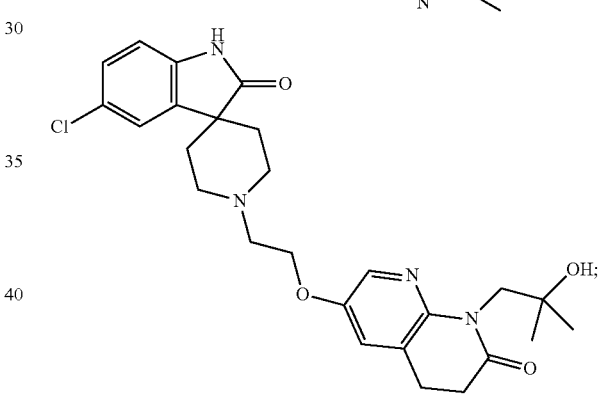
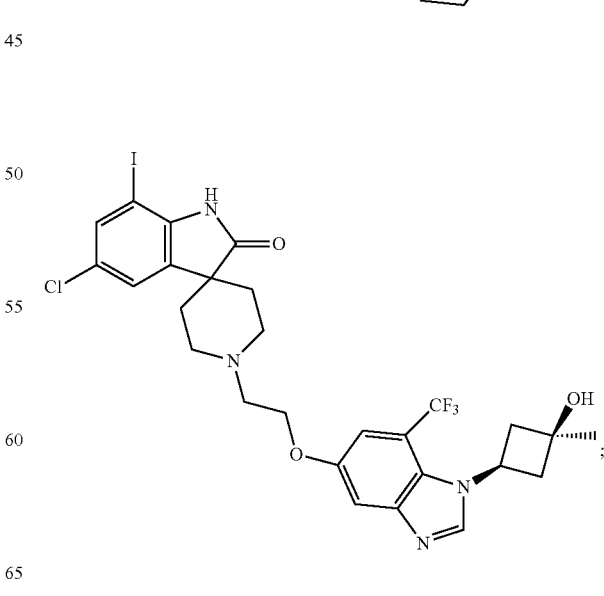

1407
-continued
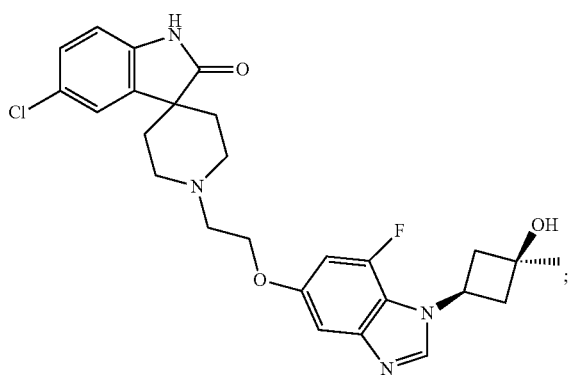
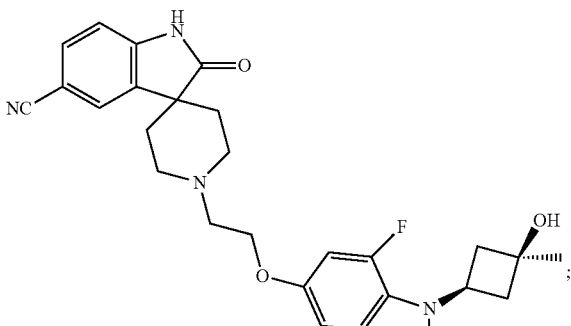
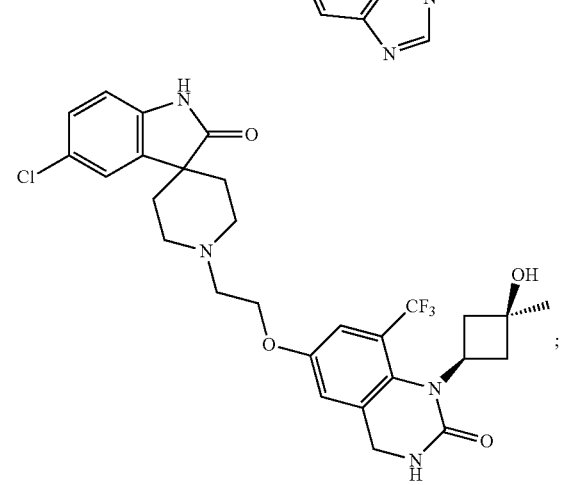
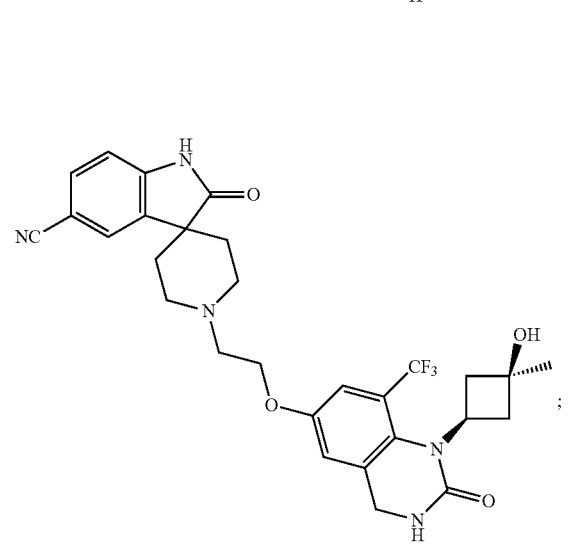
1408
-continued
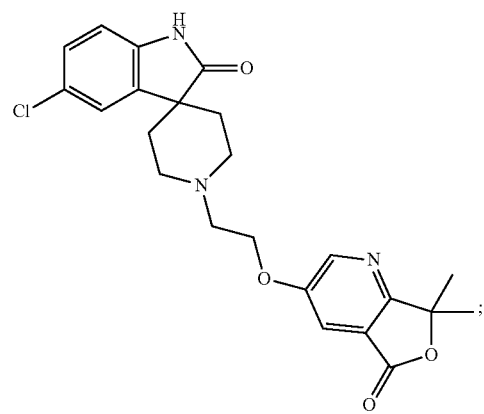
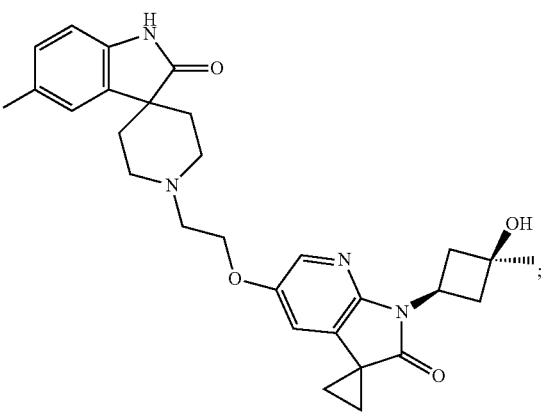
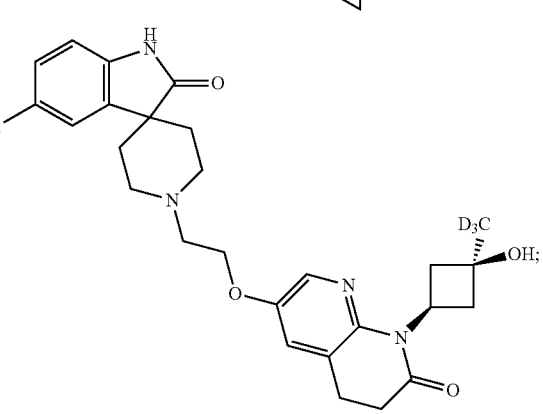
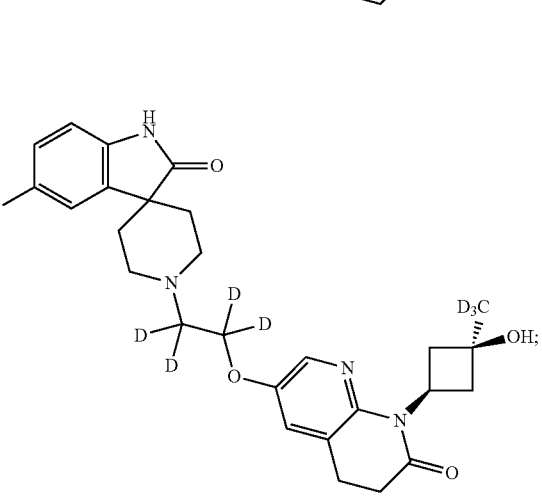

1409
-continued
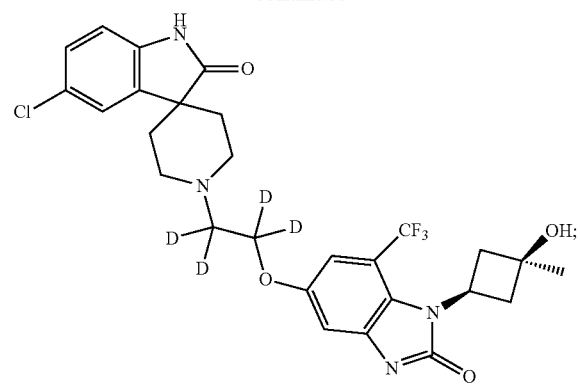
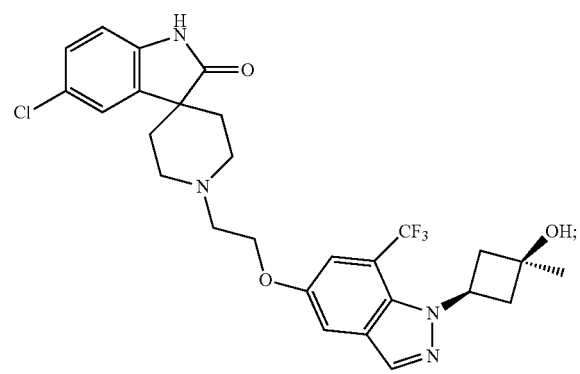
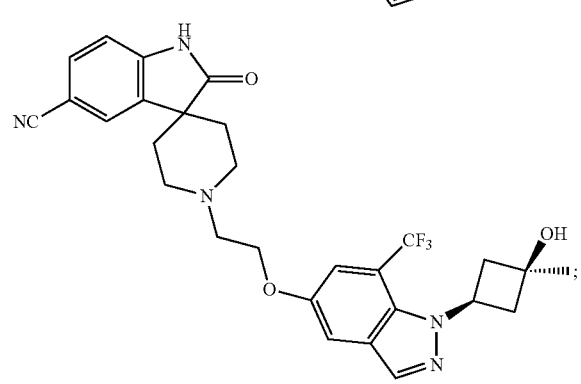
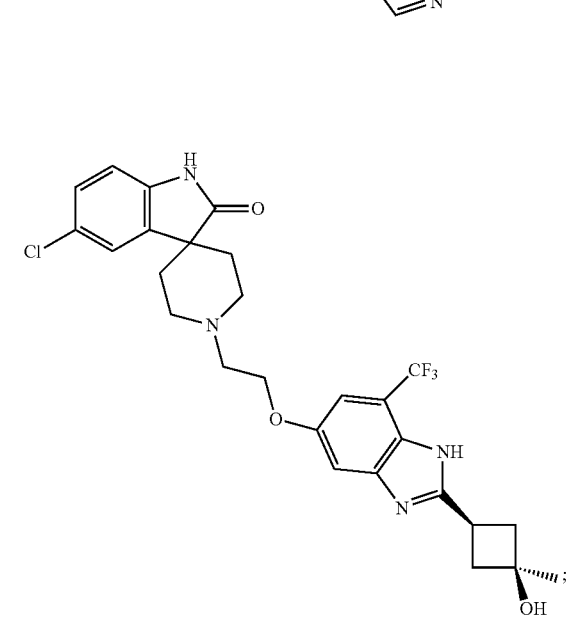
1410
-continued
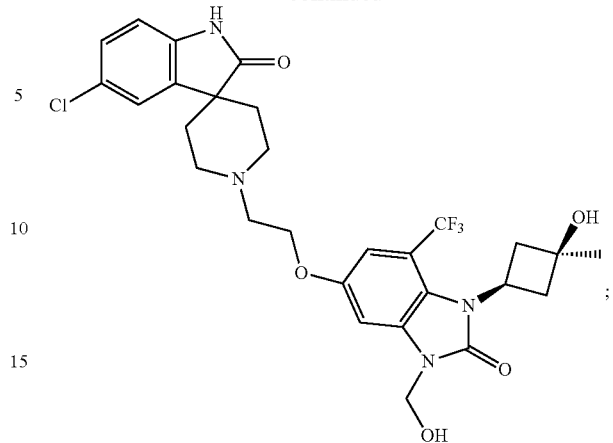
or a pharmaceutically acceptable salt of any of the foregoing.

15. A pharmaceutical composition, comprising (i) a compound of claim 1, or a stereoisomer or tautomer thereof, or a pharmaceutically acceptable salt of any of the foregoing, and (ii) one or more pharmaceutically acceptable excipients.

16. A method of inhibiting APOL1 in a cell, comprising exposing the cell to
   a) an effective amount of a compound of claim 1, or a stereoisomer or tautomer thereof, or a pharmaceutically acceptable salt of any of the foregoing, or
   b) a pharmaceutical composition comprising (i) an effective amount of a compound of claim 1, or a stereoisomer or tautomer thereof, or a pharmaceutically acceptable salt of any of the foregoing, and (ii) one or more pharmaceutically acceptable excipients.

17. A method of treating an APOL1-mediated disease, disorder, or condition in an individual in need thereof, comprising administering to the individual
   a) a compound of claim 1, or a stereoisomer or tautomer thereof, or a pharmaceutically acceptable salt of any of the foregoing, or
   b) a pharmaceutical composition comprising (i) a compound of claim 1, or a stereoisomer or tautomer thereof, or a pharmaceutically acceptable salt of any of the foregoing, and (ii) one or more pharmaceutically acceptable excipients;
   wherein the disease, disorder, or condition is selected from the group consisting of chronic kidney disease (CKD), focal segmental glomerulosclerosis (FSGS), hypertension-attributed kidney disease, human immunodeficiency virus-associated nephropathy (HIVAN), sickle-cell nephropathy, lupus nephritis, diabetic kidney disease, APOL1-associated nephropathy, viral nephropathy, COVID-19 associated nephropathy, preeclampsia, and sepsis.

18. The method of claim 17, wherein the disease, disorder, or condition is selected from the group consisting of chronic kidney disease (CKD), focal segmental glomerulosclerosis (FSGS), hypertension-attributed kidney disease, human immunodeficiency virus-associated nephropathy (HIVAN), sickle-cell nephropathy, lupus nephritis, diabetic kidney disease, APOL1-associated nephropathy, viral nephropathy, and COVID-19 associated nephropathy.

19. The method of claim 17, wherein the disease, disorder, or condition is chronic kidney disease (CKD).

20. A kit, comprising:
   (i) a compound of claim 1, or a stereoisomer or tautomer thereof, or a pharmaceutically acceptable salt of any of the foregoing, or a pharmaceutical composition comprising a compound of claim 1, or a stereoisomer or tautomer thereof, or a pharmaceutically acceptable salt of any of the foregoing, and one or more pharmaceutically acceptable excipients; and
   (ii) instructions for use in treating an APOL1-mediated disease, disorder, or condition in an individual in need thereof,
   wherein the disease, disorder, or condition is selected from the group consisting of chronic kidney disease (CKD), focal segmental glomerulosclerosis (FSGS), hypertension-attributed kidney disease, human immunodeficiency virus-associated nephropathy (HIVAN), sickle-cell nephropathy, lupus nephritis, diabetic kidney disease, APOL1-associated nephropathy, viral nephropathy, COVID-19 associated nephropathy, preeclampsia, and sepsis.

\* \* \* \* \*